US010988459B2

(12) United States Patent
Patel et al.

(10) Patent No.: US 10,988,459 B2

(45) Date of Patent: Apr. 27, 2021

(54) BICYCLIC LACTAMS AND METHODS OF USE THEREOF

(71) Applicant: Genentech, Inc., South San Francisco, CA (US)

(72) Inventors: Snahel Patel, Foster City, CA (US); Gregory Hamilton, San Mateo, CA (US); Craig Stivala, Atherton, CA (US); Huifen Chen, Burlingame, CA (US); Guiling Zhao, Palo Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/200,058

(22) Filed: Jul. 1, 2016

(65) Prior Publication Data

US 2017/0008877 A1 Jan. 12, 2017

Related U.S. Application Data

(60) Provisional application No. 62/188,153, filed on Jul. 2, 2015, provisional application No. 62/387,295, filed on Dec. 23, 2015.

(51) Int. Cl.

| | |
|---|---|
| ***A61K 31/551*** | (2006.01) |
| ***C07D 487/04*** | (2006.01) |
| ***C07D 403/12*** | (2006.01) |
| ***C07D 413/12*** | (2006.01) |
| ***C07D 471/04*** | (2006.01) |
| ***C07D 498/04*** | (2006.01) |
| ***C07D 495/04*** | (2006.01) |
| ***C07D 491/04*** | (2006.01) |
| ***C07D 491/10*** | (2006.01) |
| ***C07D 413/14*** | (2006.01) |
| ***C07D 491/044*** | (2006.01) |
| ***C07D 491/048*** | (2006.01) |
| ***C07D 491/052*** | (2006.01) |
| ***C07D 519/00*** | (2006.01) |

(52) U.S. Cl.

CPC ......... *C07D 403/12* (2013.01); *C07D 413/12* (2013.01); *C07D 413/14* (2013.01); *C07D 471/04* (2013.01); *C07D 487/04* (2013.01); *C07D 491/04* (2013.01); *C07D 491/044* (2013.01); *C07D 491/048* (2013.01); *C07D 491/052* (2013.01); *C07D 491/10* (2013.01); *C07D 495/04* (2013.01); *C07D 498/04* (2013.01); *C07D 519/00* (2013.01)

(58) Field of Classification Search

CPC ............................ A61K 31/551; C07D 487/04

USPC .......................... 514/220, 221; 540/498, 502

See application file for complete search history.

(56) References Cited

U.S. PATENT DOCUMENTS

| | | | |
|---|---|---|---|
| 5,206,234 | A | 4/1993 | Bock et al. |
| 6,350,741 | B1 | 2/2002 | Golec et al. |
| 7,057,046 | B2 | 6/2006 | Sher et al. |
| 7,425,550 | B2 | 9/2008 | Sher et al. |
| 9,815,850 | B2 | 11/2017 | Estrada et al. |
| 2004/0002495 | A1 | 1/2004 | Sher et al. |
| 2011/0038877 | A1 | 2/2011 | Way et al. |
| 2018/0170927 | A1 | 6/2018 | Patel et al. |
| 2019/0241565 | A1 | 8/2019 | Patel |

FOREIGN PATENT DOCUMENTS

| | | | |
|---|---|---|---|
| EP | 3318267 | A1 | 5/2018 |
| WO | 02/20530 | A1 | 3/2002 |
| WO | 03/046222 | A1 | 6/2003 |
| WO | 2004/037986 | A2 | 5/2004 |
| WO | 2006/031606 | A2 | 3/2006 |
| WO | 2008/011190 | A1 | 1/2008 |
| WO | 2009/140128 | A2 | 11/2009 |
| WO | 2013/059791 | A2 | 4/2013 |
| WO | 2014/009495 | A1 | 1/2014 |
| WO | 2014/023708 | A1 | 2/2014 |
| WO | 2014/125444 | A1 | 8/2014 |
| WO | 2014/145022 | A1 | 9/2014 |
| WO | 2014/170892 | A1 | 10/2014 |
| WO | 2016/027253 | A1 | 2/2016 |
| WO | 2017/001645 | A1 | 1/2017 |
| WO | 2017/001655 | A1 | 1/2017 |

(Continued)

OTHER PUBLICATIONS

Wikipedia, Spiro Compounds, https://en.wikipedia.org/wiki/Spiro_compound, Jul. 30, 2018.*

International Search Report on Patentability for International Patent Application PCT/US2016/040659, dated Sep. 20, 2016.

Written Opinion of the International Searching Authority for International Patent Application No. PCT/US2016/040659, dated Jan. 5. 2017.

(International Search Report and Written Opinion for PCT/EP2017/076385), dated Dec. 7, 2017.

(International Search Report and Written Opinion for PCT/US2019/028011), dated Jul. 9, 2019.

(Continued)

*Primary Examiner* — Brenda L Coleman

(74) *Attorney, Agent, or Firm* — Andre T. Krammer

(57) ABSTRACT

The invention provides novel compounds having the general formula I:

(I)

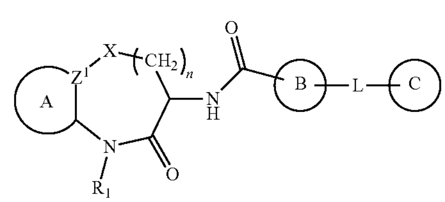

wherein $R^1$, X, $Z^1$, L, n, the A ring, the B ring, and the C ring are as described herein, pharmaceutical compositions including the compounds and methods of using the compounds.

31 Claims, No Drawings

(56) References Cited

FOREIGN PATENT DOCUMENTS

| | | | |
|---|---|---|---|
| WO | 2017/001660 | A1 | 1/2017 |
| WO | 2017/004500 | A1 | 1/2017 |
| WO | 2017/096301 | A1 | 6/2017 |
| WO | 2017/103851 | A1 | 6/2017 |
| WO | 2017/109724 | A1 | 6/2017 |
| WO | 2017/112815 | A1 | 6/2017 |
| WO | 2017136727 | A2 | 8/2017 |
| WO | 2018/073193 | A1 | 4/2018 |
| WO | 2018/109097 | A1 | 6/2018 |
| WO | 2019/204537 | A1 | 10/2019 |

OTHER PUBLICATIONS (Non-Final Office Action for U.S. Appl. No. 15/839,788 dated Jan. 22, 2019).

(Notice of Allowance for U.S. Appl. No. 15/839,788 dated Dec. 4, 2019).

(Written Opinion of the International Searching Authority for PCT/EP2017/082851), dated Feb. 18, 2018.

Bertrand et al., "cIAP1 and cIAP2 facilitate cancer cell survival by functioning as E3 ligases that promote RIP1 ubiquitination" Mol Cell 30(6):689-700 (Jun. 2008).

Chen, "Ubiquitination in signaling to and activation of IKK" Immunol Rev. 246(1):95-106 (2012).

Cho et al., "Phosphorylation-driven assembly of the RIP1-RIP3 complex regulates programmed necrosis and virus-induced inflammation" CELL 137(6):1112-1123 (Jun. 12, 2009).

de Almagro, "Necroptosis: Pathway diversity and characteristics" Semin Cell Dev Biol. 39:56-62 (Mar. 2015).

Degterev et al., "Chemical inhibitor of nonapoptotic cell death with therapeutic potential for ischemic brain injury" NAT CHEM BIOL. 1(2):112-119 (Jul. 2005).

Degterev et al., "Identification of RIP1 kinase as a specific cellular target of necrostatins" Nat Chem Biol. 4(5):313-321 (May 1, 2008).

Feoktistova et al., "cIAPs block Ripoptosome formation, a RIP1/caspase-8 containing intracellular cell death complex differentially regulated by cFLIP isoforms" MOL CELL 43(3):449-463 (Aug. 5, 2011).

Harris et al., "Discovery of Small Molecule RIP1 Kinase Inhibitors for the Treatment of Pathologies Associated with Necroptosis" ACS CHEM LETT 4(12):1238-1243 (Nov. 4, 2013).

Harris, P., et al., "Discovery of a First-in-Class Receptor Interacting Protein 1 (RIP1) Kinase Specific Clinical Candidate (GSK2982772) for the Treatment of Inflammatory Diseases" J MED CHEM 60(4):1247-1261 (Feb. 7, 2017).

He et al., "Receptor interacting protein kinase-3 determines cellular necrotic response to TNF-alpha" CELL 137(6):1100-1111 (Jun. 12, 2009).

ISR for PCT/EP2017/082851, dated Feb. 20, 2018.

Kaiser et al., "Toll-like receptor 3-mediated necrosis via TRIF, RIP3, and MLKL" J Biol Chem. 288(43):31268-31279 (Oct. 25, 2013).

Linkermann et al., "Necroptosis" NEW ENGL J MED 370(5):455-465 (Jan. 30, 2014).

Najjar et al., "Structure Guided Design of Potent and Selective Ponatinib-Based Hybrid Inhibitors for RIPKI" Cell Rep. 10(11):1850-60 (Mar. 24, 2015).

Newton et al., "Activity of protein kinase RIPK3 determines whether cells die by necroptosis or apoptosis" Science 343(6177):1357-1360 (Mar. 21, 2014).

Newton, "RIPK1 and RIPK3: critical regulators of inflammation and cell death" Trends Cell Biol. 25(6):347-353 (Jun. 1, 2015).

O'Donnell et al., "Ubiquitination of RIP1 regulated an NF-kappaB-independent cell-death switch in TNF signaling" CURR BIOL 17(5):418-424 (Mar. 6, 2007).

Sun et al., "Mixed lineage kinase domain-like protein mediates necrosis signaling downstream of RIP3 kinase" CELL 148(1-2):213-227 (Jan. 20, 2012).

Takahashi et al., "Necrostain-1 analogues: critical issues on the specificity, activity and in vivo use in experimental disease models" Cell Death Dis. (Send to), 3:e43 (Nov. 2012).

Van den Berghe et al., "Regulated necrosis: the expanding network of non-apoptotic cell death pathways" NAT REV MOL CELL BIO 15:135-147 (Feb. 1, 2014).

Wang et al., "TNF-alpha induces two distinct caspase-8 activation pathways" Cell 133(4):693-703 (May 2008).

Zhao et al., "Mixed lineage kinase domain-like is a key receptor interacting protein 3 downstream component of TNF-induced necrosis" PNAS 109(14):5322-5327 (Apr. 3, 2012).

Hamilton, G.L. et al., "Potent and selective inhibitors of receptor-interacting protein kinase 1 that lack an aromatic back pocket group" Bioorg. Med. Chem. Lett. 29(12):1497-1501 (2019).

* cited by examiner

BICYCLIC LACTAMS AND METHODS OF USE THEREOF

CROSS-REFERENCE TO RELATED APPLICATIONS

This application claims priority under 35 U.S.C. 119(e) to U.S. Provisional Patent Application No. 62/188,153, filed Jul. 2, 2015, and 62/387,295, filed Dec. 23, 2015. The entire contents of the above-referenced applications are hereby incorporated by reference herein.

FIELD OF THE INVENTION

The present invention relates to organic compounds useful for therapy and/or prophylaxis in a mammal, and in particular to inhibitors of RIP1 kinase useful for treating diseases and disorders associated with inflammation, cell death and others.

BACKGROUND OF THE INVENTION

Receptor-interacting protein-1 ("RIP1") kinase is a serine/threonine protein kinase. RIP1 is a regulator of cell signaling that is involved, among other things, in the mediation of programmed cell death pathways, e.g., necroptosis. The best studied form of necroptotic cell death is initiated by TNFα (tumor necrosis factor), but necroptosis can also be induced by other members of the TNFα death ligand family (Fas and TRAIL/Apo2L), interferons, Toll-like receptors (TLRs) signaling and viral infection via the DNA sensor DAI (DNA-dependent activator of interferon regulatory factor) [1-3]. Binding of TNFα to the TNFR1 (TNF receptor 1) prompts TNFR1 trimerization and formation of an intracellular complex, Complex-I. TRADD (TNF receptor associated death domain protein) binds to the intracellular death domain of TNFR1 and recruits the protein kinase RIP1 (receptor-interacting protein 1) through the death domain present in both proteins [4]. Following initial recruitment into TNFR1-associated signaling complex, RIP1 translocates to a secondary cytoplasmatic complex, Complex-II [5-7]. Complex-II is formed by the death domain containing protein FADD (Fas-associated Protein), RIP1, caspase-8 and cFLIP. If caspase-8 is not fully activated or its activity is blocked, the protein kinase RIP3 gets recruited to the complex, forming a necrosome, which will lead to necroptotic cell death initiation [8-10]. Once the necrosome is formed, RIP1 and RIP3 engage in a series of auto and cross phosphorylation events that are essential for necroptotic cell death. Necroptosis can be completely blocked either by the kinase inactivating mutation in any of the two kinases, or chemically by RIP1 kinase inhibitors (necrostatins), or RIP3 kinase inhibitors [11-13]. Phosphorylation of RIP3 allows the binding and phosphorylation of pseudokinase MLKL (mixed lineage kinase domain-like), a key component of necroptotic cell death [14, 15].

Necroptosis has crucial pathophysiological relevance in myocardial infarction, stroke, atherosclerosis, ischemia-reperfusion injury, inflammatory bowel diseases, retinal degeneration and a number of other common clinical disorders [16]. Therefore, selective inhibitors of RIP1 kinase activity are therefore desired as a potential treatment of diseases mediated by this pathway and associated with inflammation and/or necroptotic cell death.

Inhibitors of RIP1 kinase have been previously described. The first published inhibitor of RIP1 kinase activity was necrostatin 1 (Nec-1) [17]. This initial discovery was followed by modified versions of Nec-1 with various abilities to block RIP1 kinase activity [11, 18]. Recently, additional RIP1 kinase inhibitors have been described that differ structurally from necrostatin class of compounds [19, 20, 21].

References cited above, each of which is hereby incorporated by reference in its entirety:

1) Vanden Berghe, T., Linkermann, A., Jouan-Lanhouet, S., Walczak, H. and Vandenabeele, P. (2014) Regulated necrosis: the expanding network of non-apoptotic cell death pathways. Nature reviews. Molecular cell biology. 15, 135-147.

2) Newton, K. (2015) RIPK1 and RIPK3: critical regulators of inflammation and cell death. Trends in cell biology. 25, 347-353.

3) de Almagro, M. C. and Vucic, D. (2015) Necroptosis: Pathway diversity and characteristics. Semin Cell Dev Biol. 39, 56-62.

4) Chen, Z. J. (2012) Ubiquitination in signaling to and activation of IKK. Immunological reviews. 246, 95-106.

5) O'Donnell, M. A., Legarda-Addison, D., Skountzos, P., Yeh, W. C. and Ting, A. T. (2007) Ubiquitination of RIP1 regulates an NF-kappaB-independent cell-death switch in TNF signaling. Curr Biol. 17, 418-424.

6) Feoktistova, M., Geserick, P., Kellert, B., Dimitrova, D. P., Langlais, C., Hupe, M., Cain, K., MacFarlane, M., Hacker, G. and Leverkus, M. (2011) cIAPs block Ripoptosome formation, a RIP1/caspase-8 containing intracellular cell death complex differentially regulated by cFLIP isoforms. Molecular cell. 43, 449-463.

7) Bertrand, M. J., Milutinovic, S., Dickson, K. M., Ho, W. C., Boudreault, A., Durkin, J., Gillard, J. W., Jaquith, J. B., Morris, S. J. and Barker, P. A. (2008) cIAP1 and cIAP2 facilitate cancer cell survival by functioning as E3 ligases that promote RIP1 ubiquitination. Mol Cell. 30, 689-700.

8) Wang, L., Du, F. and Wang, X. (2008) TNF-alpha induces two distinct caspase-8 activation pathways. Cell. 133, 693-703.

9) He, S., Wang, L., Miao, L., Wang, T., Du, F., Zhao, L. and Wang, X. (2009) Receptor interacting protein kinase-3 determines cellular necrotic response to TNF-alpha. Cell. 137, 1100-1111.

10) Cho, Y. S., Challa, S., Moquin, D., Genga, R., Ray, T. D., Guildford, M. and Chan, F. K. (2009) Phosphorylation-driven assembly of the RIP1-RIP3 complex regulates programmed necrosis and virus-induced inflammation. Cell. 137, 1112-1123.

11) Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem Biol. 4, 313-321.

12) Newton, K., Dugger, D. L., Wickliffe, K. E., Kapoor, N., de Almagro, M. C., Vucic, D., Komuves, L., Ferrando, R. E., French, D. M., Webster, J., Roose-Girma, M., Warming, S. and Dixit, V. M. (2014) Activity of protein kinase RIPK3 determines whether cells die by necroptosis or apoptosis. Science. 343, 1357-1360.

13) Kaiser, W. J., Sridharan, H., Huang, C., Mandal, P., Upton, J. W., Gough, P. J., Sehon, C. A., Marquis, R. W., Bertin, J. and Mocarski, E. S. (2013) Toll-like receptor 3-mediated necrosis via TRIF, RIP3, and MLKL. The Journal of biological chemistry. 288, 31268-31279.

14) Zhao, J., Jitkaew, S., Cai, Z., Choksi, S., Li, Q., Luo, J. and Liu, Z. G. (2012) Mixed lineage kinase domain-like is a key receptor interacting protein 3 downstream component of TNF-induced necrosis. Proceedings of the National Academy of Sciences of the United States of America. 109, 5322-5327.

15) Sun, L., Wang, H., Wang, Z., He, S., Chen, S., Liao, D., Wang, L., Yan, J., Liu, W., Lei, X. and Wang, X. (2012) Mixed Lineage Kinase Domain-like Protein Mediates Necrosis Signaling Downstream of RIP3 Kinase. Cell. 148, 213-227.

16) Linkermann, A. and Green, D. R. (2014) Necroptosis. The New England journal of medicine. 370, 455-465.

17) Degterev, A., Huang, Z., Boyce, M., Li, Y., Jagtap, P., Mizushima, N., Cuny, G. D., Mitchison, T. J., Moskowitz, M. A. and Yuan, J. (2005) Chemical inhibitor of nonapoptotic cell death with therapeutic potential for ischemic brain injury. Nat Chem Biol. 1, 112-119.

18) Takahashi, N., Duprez, L., Grootjans, S., Cauwels, A., Nerinckx, W., DuHadaway, J. B., Goossens, V., Roelandt, R., Van Hauwermeiren, F., Libert, C., Declercq, W., Callewaert, N., Prendergast, G. C., Degterev, A., Yuan, J. and Vandenabeele, P. (2012) Necrostatin-1 analogues: critical issues on the specificity, activity and in vivo use in experimental disease models. Cell Death Dis. 3, e437.

19) Harris, P. A., Bandyopadhyay, D., Berger, S. B., Campobasso, N., Capriotti, C. A., Cox, J. A., Dare, L., Finger, J. N., Hoffman, S. J., Kahler, K. M., Lehr, R., Lich, J. D., Nagilla, R., Nolte, R. T., Ouellette, M. T., Pao, C. S., Schaeffer, M. C., Smallwood, A., Sun, H. H., Swift, B. A., Totoritis, R. D., Ward, P., Marquis, R. W., Bertin, J. and Gough, P. J. (2013) Discovery of Small Molecule RIP1 Kinase Inhibitors for the Treatment of Pathologies Associated with Necroptosis. ACS medicinal chemistry letters. 4, 1238-1243.

20) Najjar, M., Suebsuwong, C., Ray, S. S., Thapa, R. J., Maki, J. L., Nogusa, S., Shah, S., Saleh, D., Gough, P. J., Bertin, J., Yuan, J., Balachandran, S., Cuny, G. D. and Degterev, A. (2015) Structure Guided Design of Potent and Selective Ponatinib-Based Hybrid Inhibitors for RIPK1. Cell Rep.

21) International Patent Publication No. WO 2014/125444.

SUMMARY OF THE INVENTION

Provided herein are compounds of formula I:

(I)

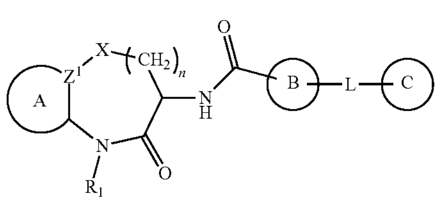

or pharmaceutically acceptable salts thereof, wherein $R^1$ is selected from the group consisting of H, $C_1$-$C_4$ alkyl and $C_1$-$C_4$ haloalkyl;

the A ring is selected from the group consisting of cyclopropyl, 6 membered aryl, and 5 to 6 membered heteroaryl having 1 to 3 heteroatoms selected from the group consisting of nitrogen, oxygen and sulfur; wherein the A ring is optionally substituted with:

(a) 1 to 3 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl); wherein if a nitrogen atom in the A ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

(b) 1 substituent selected from the group consisting of $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2CH_2CH_2$—($C_4$-$C_6$ heterocyclyl), $CH_2$—($C_5$-$C_6$ heteroaryl), $CH_2CH_2$—($C_5$-$C_6$ heteroaryl); $CH_2CH_2CH_2$—($C_5$-$C_6$ heteroaryl); and optionally a second substituent selected from the group consisting of $C_1$-$C_6$ alkyl, $C_1$-$C_6$ haloalkyl, $C_1$-$C_6$ alkoxy, and $C_1$-$C_6$ haloalkoxy; or (c) two adjacent substituents which together form phenyl, $C_5$-$C_6$ heteroaryl, $C_4$-$C_6$ heterocyclyl or $C_4$-$C_6$ cycloalkyl;

the B ring is tetrazolyl or a 5 to 6 membered heteroaryl having 1 to 3 heteroatoms selected from the group consisting of nitrogen, oxygen and sulfur; wherein the B ring is optionally substituted with 1 to 2 substituents selected from the group consisting of halogen, $C_1$-$C_4$ alkyl, $C_3$-$C_4$ cycloalkyl, $C_1$-$C_4$ haloalkyl, $C_1$-$C_4$ alkoxy, $C_1$-$C_4$ haloalkoxy and cyano; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

the C ring is selected from the group consisting of phenyl, 5 to 6 membered heteroaryl, 4 to 7 membered cycloalkyl, and 4 to 7 membered heterocyclyl; wherein the C ring is optionally substituted with:

(a) 1 to 4 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl); wherein if a nitrogen atom in the C ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

(b) 1 to 2 substituents selected from the group consisting of $C_1$-$C_6$ alkyl, $C_1$-$C_6$ haloalkyl, $C_1$-$C_6$ alkoxy, $C_1$-$C_6$ haloalkoxy, $CH_2$—($C_4$-$C_6$ heterocyclyl), $CH_2CH_2$—($C_4$-$C_6$ heterocyclyl), and unsubstituted $C_5$-$C_6$ heteroaryl; or (c) two adjacent substituents which together form phenyl, $C_5$-$C_6$ heteroaryl, $C_4$-$C_6$ heterocyclyl or $C_4$-$C_6$ cycloalkyl;

L is selected from the group consisting of a bond, O, S, NH, $NCH_3$, $(CH_2)_m$, $CH(CH_3)$, $C(CH_3)_2$, $CF_2$, $CH_2O$, $CH_2S$, $CH(OH)$, $CH_2NH$, and $CH_2N(CH_3)$, or L is absent such that the B ring and the C ring are fused;

X is selected from the group consisting of O, S, SO, $SO_2$, $CH_2$, $C(CH_3)_2$, $CF_2$ and $CHCF_3$;

$Z^1$ is selected from the group consisting of:

(i) C and N when the A ring is a 5 or 6 membered heteroaryl, (ii) C when the A ring is a 6 membered aryl, and (iii) CH when the A ring is cyclopropyl;

m is 1 or 4; and n is 1 or 2;

provided that if the A ring is 6 membered aryl or 6 membered heteroaryl, L is absent such that the B ring and the C ring are fused;

further provided that if the A ring is a 5 to 6 membered heteroaryl having 3 heteroatoms, two of said heteroatoms must be nitrogen;

further provided that if the A ring is unsubstituted 6 membered aryl and L is absent, the fused B and C rings are not unsubstituted indolyl or indolyl substituted by one or two halogen atoms; and further provided that if the B ring is tetrazolyl, L is selected from the group consisting of $CH_2$, $CH(CH_3)$, $C(CH_3)_2$, $CF_2$; and the C ring is phenyl.

In the following description, all references to formula I also include subembodiments of formula I (i.e., formulae 1a, 1b, etc.).

Also provided herein are pharmaceutical compositions comprising a compound of formula I, or a pharmaceutically acceptable salt thereof, and one or more pharmaceutically acceptable carriers or excipients. Specific embodiments include pharmaceutical compositions suitable for intravenous or oral delivery.

Also provided herein are oral formulations of a compound of formula I, or a pharmaceutically acceptable salt thereof, and one or more pharmaceutically acceptable carriers or excipients suitable for oral delivery.

Also provided herein are parenteral formulations of a compound of formula I, or a pharmaceutically acceptable salt thereof, and one or more pharmaceutically acceptable carriers or excipients suitable for parenenteral delivery.

In some embodiments, provided herein are uses of a compound of formula I, or a pharmaceutically acceptable salt thereof, for the treatment of diseases and disorders. In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCKI) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa and retinal degeneration.

In some embodiments, provided herein are methods for the treatment or prevention of a disease or disorder with a therapeutically effective amount of a compound of formula I, or a pharmaceutically acceptable salt thereof, wherein the disease or disorder is associated with inflammation and/or necroptosis. In some embodiments said disease or disorder is selected from the specific diseases and disorders recited herein.

In some embodiments, provided herein are methods of inhibiting RIP1 kinase activity by contacting a cell with a compound of formula I or a pharmaceutically acceptable salt thereof.

DETAILED DESCRIPTION OF THE INVENTION

Definitions

As provided herein, all chemical formulae and generic chemical structures should be interpreted to provide proper valence and chemically stable bonds between atoms as understood by one of ordinary skill in the art. Where appropriate, substituents may be bonded to more than one adjacent atom (e.g., alkyl includes methylene where two bonds are present).

In the chemical formulae provided herein, "halogen" or "halo" refers to flurorine, chlorine, and bromine (i.e., F, Cl, Br).

Alkyl, unless otherwise specifically defined, refers to an optionally substituted, straight-chain or branched $C_1$-$C_{12}$ alkyl group. In some embodiments, alkyl refers to a $C_1$-$C_6$ alkyl group. Exemplary alkyl groups include methyl, ethyl, propyl, iso-propyl, n-butyl, iso-butyl, tert-butyl, sec-butyl, n-pentyl, n-hexyl, n-heptyl, and n-oxtyl. Substituted alkyl groups provided herein are substituted by one or more substituents selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl$)_2$, $NH(C{=}O)C_1$-$C_4$ alkyl, $(C{=}O)NH(C_1$-$C_4$ alkyl), $(C{=}O)N(C_1$-$C_4$ alkyl$)_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl$)_2$, and $NHSO_2(C_1$-$C_4$ alkyl). In some embodiments, the substituted alkyl group has 1 or 2 substituents. In some embodiments, the alkyl group is unsubstituted.

Cycloalkyl, unless otherwise specifically defined, refers to an optionally substituted $C_3$-$C_{12}$ cycloalkyl group and includes fused, spirocyclic, and bridged bicyclic groups, wherein the substituents are selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl$)_2$, $NH(C{=}O)C_1$-$C_4$ alkyl, $(C{=}O)NH(C_1$-$C_4$ alkyl), $(C{=}O)N(C_1$-$C_4$ alkyl$)_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl$)_2$, and $NHSO_2(C_1$-$C_4$ alkyl). In some embodiments, cycloalkyl refers to a $C_3$-$C_6$ cycloalkyl group. In some embodiments, the $C_3$-$C_6$ cycloalkyl group is optionally substituted with 1 to three halogen atoms. In some embodiments, the $C_3$-$C_6$ cycloalkyl group is optionally substituted with 1 to three fluorine atoms. Exemplary $C_3$-$C_6$ cycloalkyl groups include cyclopropyl, cyclobutyl, cyclopentyl and cyclohexyl. Exemplary $C_3$-$C_{12}$ cycloalkyl groups further include bicyclo[3.1.0]hexyl, bicyclo[2.1.1]hexyl, cycloheptyl, bicycle[4.1.0]heptyl, spiro[4.2]heptyl, cyclooctyl, spiro[4.3]octyl, spiro[5.2]octyl, bicyclo[2.2.1]heptanyl, bicycle[2.2.2]octanyl, adamantanyl, decalinyl, and spiro[5.4]decanyl. Where appropriate, cycloalkyl groups may be fused to other groups such that more than one chemical bond exists between the cycloalkyl group and another ring system (e.g., the C ring of formula I). In some embodiments, the cycloalkyl group is unsubstituted.

Haloalkyl, unless otherwise specifically defined, refers to a straight-chain or branched $C_1$-$C_{12}$ alkyl group, wherein one or more hydrogen atoms are replaced by a halogen. In some embodiments, haloalkyl refers to a $C_1$-$C_6$ haloalkyl group. In some embodiments, 1 to 3 hydrogen atoms of the haloalkyl group are replaced by a halogen. In some embodiments, every hydrogen atom of the haloalkyl group is replaced by a halogen (e.g, trifluoromethyl). In some embodiments, the haloalkyl is as defined herein wherein the halogen in each instance is fluorine. Exemplary haloalkyl groups include fluoromethyl, difluoromethyl, trifluromethyl, trifluoroethyl, and pentafluoroethyl.

Alkoxy, unless otherwise specifically defined, refers to a straight-chain or branched $C_1$-$C_{12}$ alkyl group, wherein one or more oxygen atoms are present, in each instance between two carbon atoms. In some embodiments, alkoxy refers to a $C_1$-$C_6$ alkoxy group. In some embodiments, $C_1$-$C_6$ alkoxy groups provided herein have one oxygen atom. Exemplary alkoxy groups include methoxy, ethoxy, $CH_2OCH_3$, $CH_2CH_2OCH_3$, $CH_2OCH_2CH_3$, $CH_2CH_2OCH_2CH_3$, $CH_2OCH_2CH_2CH_3$, $CH_2CH_2CH_2OCH_3$, $CH_2OCH(CH_3)_2$, $CH_2OC(CH_3)_3$, $CH(CH_3)OCH_3$, $CH_2CH(CH_3)OCH_3$, $CH(CH_3)OCH_2CH_3$, $CH_2OCH_2OCH_3$, $CH_2CH_2OCH_2CH_2OCH_3$, and $CH_2OCH_2OCH_2OCH_3$.

Cycloalkoxy, unless otherwise specifically defined, refers to a $C_4$-$C_{10}$ or a $C_4$-$C_6$ alkoxy group as defined above wherein the group is cyclic and contains one oxygen atom. Exemplary cycloalkoxy groups include oxetanyl, tetrahydrofuranyl, and tetrahydropyranyl.

Haloalkoxy, unless otherwise specifically defined, refers to a $C_1$-$C_6$ haloalkyl group as defined above, wherein one or two oxygen atoms are present, in each instance between two carbon atoms. In some embodiments, $C_1$-$C_6$ haloalkoxy groups provided herein have one oxygen atom. Exemplary haloalkoxy groups include $OCF_3$, $OCHF_2$ and $CH_2OCF_3$.

Thioalkyl, unless otherwise specifically defined, refers to a $C_1$-$C_{12}$ or a $C_1$-$C_6$ alkoxy group as defined above wherein the oxygen atom is replaced by a sulfur atom. In some embodiments, thioalkyl groups may include sulfur atoms substituted by one or two oxygen atoms (i.e., alkylsulfones and alkylsulfoxides). Exemplary thioalkyl groups are those exemplified in the definition of alkoxy above, wherein each oxygen atom is replaced by a sulfur atom in each instance.

Thiocycloalkyl, unless otherwise specifically defined, refers to a $C_4$-$C_{10}$ or a $C_4$-$C_6$ thioalkyl group as defined above wherein the group is cyclic and contains one sulfur atom. In some embodiments, the sulfur atom of the thiocycloalkyl group is substituted by one or two oxygen atoms (i.e., a cyclic sulfone or sulfoxide). Exemplary thiocycloalkyl groups include thietanyl, thiolanyl, thianyl, 1,1-dioxothiolanyl, and 1,1-dioxothianyl.

Heterocyclyl, unless otherwise specifically defined, refers to a single saturated or partially unsaturated 4 to 8 membered ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems have from 7 to 12 atoms and are further described below. Thus, the term includes single saturated or partially unsaturated rings (e.g., 3, 4, 5, 6, 7 or 8 membered rings) from about 1 to 7 carbon atoms and from about 1 to 4 heteroatoms selected from the group consisting of oxygen, nitrogen and sulfur in the ring.

The ring may be C-branched (i.e., substituted by $C_1$-$C_4$ alkyl). The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system. It is also to be understood that the point of attachment for a heterocycle or heterocycle multiple condensed ring system can be at any suitable atom of the heterocyclyl group including a carbon atom and a nitrogen atom. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one.

In some embodiments, the heterocyclyl is a $C_4$-$C_{10}$ heterocyclyl having 1 to 3 heteroatoms selected from the group consisting of nitrogen, oxygen and sulfur. In some embodiments, the heterocyclyl group is neither bicyclic nor spirocyclic. In some embodiments, the heterocyclyl is a $C_5$-$C_6$ heterocyclyl having 1 to 3 heteroatoms, wherein at least 2 are nitrogen if 3 heteroatoms are present.

Aryl, unless otherwise specifically defined, refers to a single all carbon aromatic ring or a multiple condensed all carbon ring system wherein at least one of the rings is aromatic and wherein the aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Exemplary aryl groups include phenyl, indenyl, naphthyl, 1,2,3,4-tetrahydronaphthyl, anthracenyl, and the like.

Heteroaryl, unless otherwise specifically defined, refers to a 5 to 6 membered aromatic ring that has at least one atom other than carbon in the ring, wherein the atom is selected from the group consisting of oxygen, nitrogen and sulfur; "heteroaryl" also includes multiple condensed ring systems having 8 to 16 atoms that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2 or 3 rings) wherein a heteroaryl group, as defined above, is condensed with one or more rings selected from heteroaryls (to form for example a naphthyridinyl such as 1,8-naphthyridinyl), heterocycles, (to form for example a 1,2,3,4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1 to 15 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "∿∿∿" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenyl sulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis $4^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenedi amine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, $—P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Inhibitors of RIP1 Kinase

The present invention provides novel compounds having the general formula I:

(I)

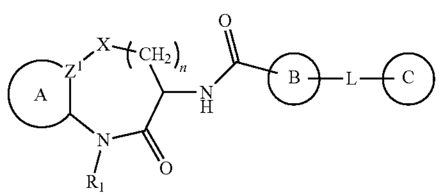

wherein $R^1$, X, $Z^1$, L, n, the A ring, the B ring, and the C ring are as described herein.

In some embodiments of formula (I), the A ring is selected from the group consisting of cyclopropyl, 6 membered aryl, and 5 to 6 membered heteroaryl having 1 to 3 heteroatoms selected from the group consisting of nitrogen, oxygen and sulfur; wherein the A ring is optionally substituted with:

(a) 1 to 3 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl); wherein if a nitrogen atom in the A ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

(b) 1 substituent selected from the group consisting of $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2$—($C_5$-$C_6$ heteroaryl), $CH_2CH_2$—($C_5$-$C_6$ heteroaryl); and optionally a second substituent selected from the group consisting of $C_1$-$C_6$ alkyl, $C_1$-$C_6$ haloalkyl, $C_1$-$C_6$ alkoxy, and $C_1$-$C_6$ haloalkoxy; or (c) two adjacent substituents which together form phenyl, $C_5$-$C_6$ heteroaryl, $C_4$-$C_6$ heterocyclyl or $C_4$-$C_6$ cycloalkyl; and the C ring is selected from the group consisting of phenyl, 5 to 6 membered heteroaryl, 5 to 7 membered cycloalkyl, and 5 to 7 membered heterocyclyl; wherein the C ring is optionally substituted with:

(d) 1 to 4 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl); wherein if a nitrogen atom in the C ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

(e) 1 to 2 substituents selected from the group consisting of $C_1$-$C_6$ alkyl, $C_1$-$C_6$ haloalkyl, $C_1$-$C_6$ alkoxy, $C_1$-$C_6$ haloalkoxy, $CH_2$—($C_4$-$C_6$ heterocyclyl), $CH_2CH_2$—($C_4$-$C_6$ heterocyclyl), and unsubstituted $C_5$-$C_6$ heteroaryl; or (f) two adjacent substituents which together form phenyl, $C_5$-$C_6$ heteroaryl, $C_4$-$C_6$ heterocyclyl or $C_4$-$C_6$ cycloalkyl.

In some embodiments, $R^1$ is selected from the group consisting of H, methyl, ethyl and isopropyl. In some embodiments, $R^1$ is H. In other embodiments, $R^1$ is methyl.

In some embodiments, X is $CH_2$. In some embodiments, X is $CF_2$. In some embodiments, X is O and $Z^1$ is C. In some embodiments, X is S and $Z^1$ is C.

In some embodiments, X is O, $Z^1$ is CH and the A ring is cyclopropyl.

In some embodiments, L is $(CH_2)_m$ and m is 1 or 2. In some embodiments, L is $(CH_2)_m$ and m is 1. In other embodiments, L is absent such that the B ring and the C ring are fused.

In some embodiments, n is 1.

In some embodiments, the A ring is cyclopropyl. In some embodiments, the A ring is unsubstituted cyclopropyl. In some embodiments, the A ring is cyclopropyl substituted by 1 to 2 $C_1$-$C_4$ alkyl groups. In some embodiments, the A ring is cyclopropyl substituted by one substituent selected from the group consisting of $C_1$-$C_4$ alkyl, phenyl or benzyl. In some embodiments, the A ring is cyclopropyl substituted by one or two halogens. In some embodiments, the A ring is as defined in this paragraph and n is 1. In some embodiments, the A ring is as defined in this paragraph, and X is selected from the group consisting of $CH_2$, $C(CH_3)_2$, $CF_2$ and $CHCF_3$.

In some embodiments, the A ring is a 5 membered heteroaryl having 1 to 2 nitrogen atoms and 0 to 1 oxygen or sulfur atoms as the only heteroatoms. In some embodiments, the A ring is a 5 membered heteroaryl having 1 to 2 nitrogen atoms and 0 to 1 oxygen or sulfur atoms as the only heteroatoms, wherein the 5 membered heteroaryl is unsubstituted or is substituted by $C_1$-$C_4$ alkyl. In some embodiments, the A ring is a 5 membered heteroaryl having 2 nitrogen atoms as the only heteroatoms, wherein the 5 membered heteroaryl is unsubstituted or is substituted by $C_1$-$C_4$ alkyl. In some embodiments wherein the A ring is as defined in this paragraph, X is $CH_2$ or O.

In some embodiments, the A ring is an unsubstituted 6 membered aryl. In some embodiments, the A ring is a 6 membered aryl substituted by one or two substituents selected from the group consisting of halogen and $C_1$-$C_4$ alkyl. In some embodiments, the A ring is a 6 membered aryl substituted by one or two substituents selected from the group consisting of halogen and methyl. In some embodiments, the A ring is a 6 membered aryl substituted by one or two substituents selected from the group consisting of fluoro and methyl.

In some embodiments, the B ring is a 5 or 6 membered heteroaryl having from 1 to 3 nitrogen atoms in the ring. In other embodiments, the B ring is a 5 or 6 membered heteroaryl having from 1 to 2 nitrogen atoms and from 0 to 1 oxygen or sulfur atoms in the ring. In some embodiments, the B ring is selected from the group consisting of furanyl, pyrroyl, thiopheneyl, pyrazolyl, imidazolyl, oxazolyl, isoxazolyl, thiazolyl, isothiazolyl and triazolyl. In some embodiments, the B ring is pyrazolyl. In some embodiments, the B ring is imidazolyl. In some embodiments, the B ring is oxazolyl. In some embodiments, the B ring is thiazolyl. In some embodiments, the B ring is triazolyl. In some embodiments, the B ring is oxadiazolyl. In some embodiments, the B ring is pyridinyl or pyrimidinyl. In some embodiments of this paragraph, the B ring is unsubstituted.

In some embodiments wherein L is absent such that the B and C rings are fused, the C ring is a 5 to 7 membered heterocyclyl containing 1 to 2 heteroatoms selected from the group consisting of nitrogen, oxygen and sulfur. In one embodiment wherein L is absent such that the B and C rings are fused, the C ring is a 5 to 7 membered heterocyclyl containing 1 heteroatom selected from the group consisting of nitrogen, oxygen and sulfur. In other embodiments wherein L is absent such that the B and C rings are fused, the C ring is a 5 to 7 membered cycloalkyl. In other embodiments wherein L is absent such that the B and C rings are fused, the C ring is phenyl. In some embodiments of this paragraph, the C ring is unsubstituted.

In some embodiments wherein L is present, the C ring is phenyl substituted by 1 or 2 substituents selected from the group consisting of halogen, $C_1$-$C_4$ alkyl, and $C_1$-$C_4$ alkoxy. In other embodiments wherein L is present, the C ring is unsubstituted phenyl.

In some embodiments, provided herein is a compound of formula I(a):

(I(a))

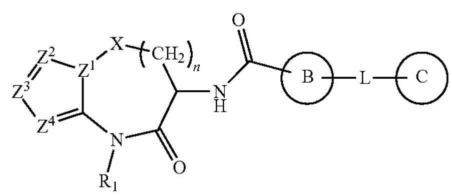

or a pharmaceutically acceptable salt thereof, wherein $R^1$, X, $Z^1$, L, n, the A ring, the B ring, and the C ring are as described herein, wherein $Z^2$, $Z^3$, and $Z^4$ are each independently selected from the group consisting of $CR^Z$ and $NR^8$;

each $R^Z$ is independently selected from the group consisting of H, halogen, $C_1$-$C_6$ alkyl, $C_3$-$C_6$ cycloalkyl, $CH_2$($C_3$-$C_6$ cycloalkyl), $C_1$-$C_6$ haloalkyl, $C_1$-$C_6$ alkoxy, $C_1$-$C_6$ thioalkyl, $CH_2$($C_4$-$C_6$ cycloalkoxy), $CH_2$($C_4$-$C_6$ thiocycloalkyl), phenyl, benzyl, 4 to 6 membered heterocyclyl; and 5 to 6 membered heteroaryl;

each $R^8$ is either absent if the nitrogen atom to which it is attached has three bonds to other atoms, or $R^8$ is selected from the group consisting of H, $C_1$-$C_6$ alkyl, $C_3$-$C_6$ cycloalkyl, $CH_2$($C_3$-$C_6$ cycloalkyl), $C_1$-$C_6$ haloalkyl, $CH_2$($C_4$-$C_6$ cycloalkoxy), $CH_2$($C_4$-$C_6$ thiocycloalkyl), phenyl, and benzyl;

wherein $Z^1$ is N only if X is $CH_2$, $CF_2$, $CH(CH_3)$, $CH(CF_3)$, $C(CH_3)_2$, or CH(OH);

wherein if $Z^1$ is N, at least one of $Z^2$, $Z^3$ or $Z^4$ is $CR^Z$;

wherein, when $Z^2$ and $Z^3$ are each independently selected from $CR^Z$ and $NR^8$, $Z^2$ and $Z^3$ together with their respective $R^Z$ and $R^8$ substituents may form a 6 membered aryl, 6 membered heteroaryl, 5 to 6 membered cycloalkyl or 5 to 6 membered heterocyclyl group;

wherein, when $Z^3$ and $Z^4$ are each independently selected from $CR^Z$ and $NR^8$, $Z^3$ and $Z^4$ together with their respective $R^Z$ and $R^8$ substituents may form a 6 membered aryl, 6 membered heteroaryl, 5 to 6 membered cycloalkyl or 5 to 6 membered heterocyclyl group;

In some embodiments of formula I(a), $R^1$ is selected from H and $CH_3$. In some embodiments, $R^1$ is H. In other embodiments, $R^1$ is $CH_3$.

In some embodiments of formula I(a), X is $CH_2$ or O; $Z^1$ is C; and $Z^2$, $Z^3$, and $Z^4$ are each independently selected from the group consisting of $CR^Z$, NH, $NCH_3$. In some embodiments of formula I(b), X is $CH_2$ or O; $Z^1$ is C; and $Z^2$, $Z^3$, and $Z^4$ are each independently selected from the group consisting of CH and NH.

In some embodiments of formula I(a), X is $CH_2$; $Z^1$ is N; and $Z^2$, $Z^3$, and $Z^4$ are each independently selected from the group consisting of $CR^Z$, NH, $NCH_3$, wherein at least one of $Z^2$, $Z^3$, and $Z^4$ is $CR^Z$. In some embodiments of formula I(a), X is $CH_2$; $Z^1$ is N; and $Z^2$, $Z^3$, and $Z^4$ are each independently selected from the group consisting of CH and NH, wherein at least one of $Z^2$, $Z^3$, and $Z^4$ is CH.

In some embodiments of formula I(a), n is 1.

In some embodiments of formula I(a), the compound is of a formula selected from the group consisting of:

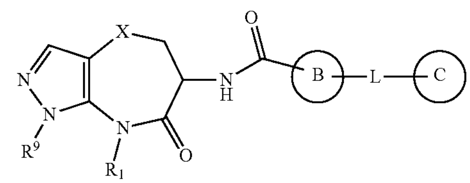,

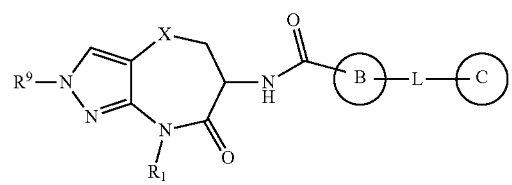,

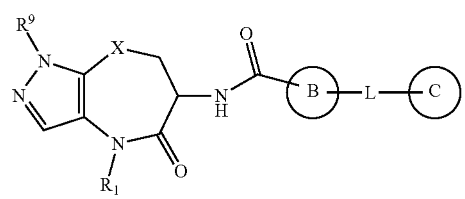,

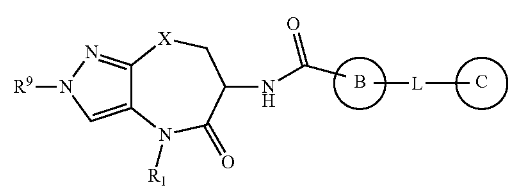,

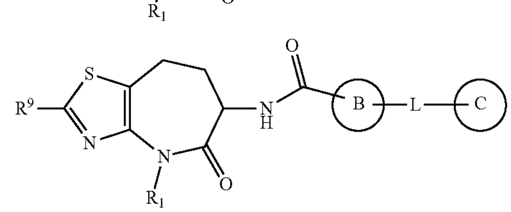,

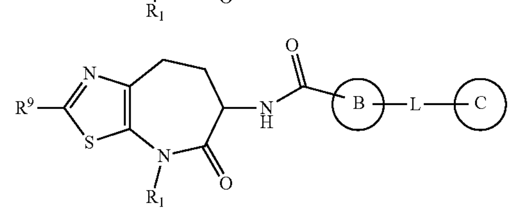,

-continued

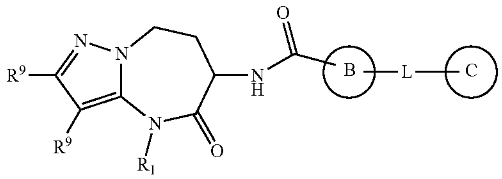
,

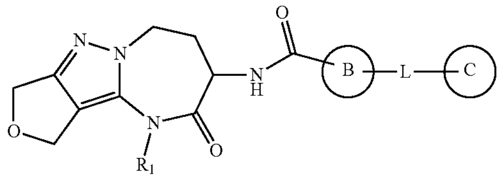
,

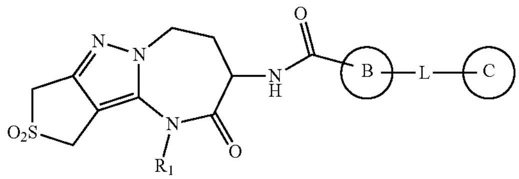
,

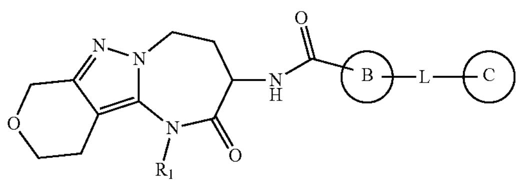
,

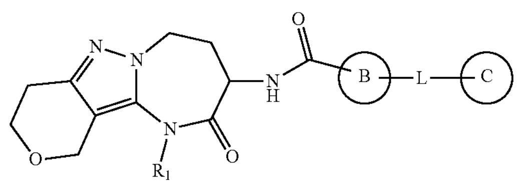
,

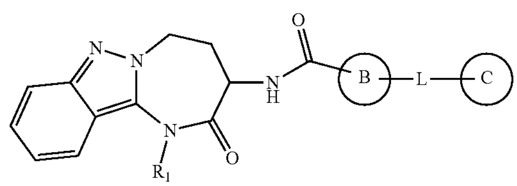
,

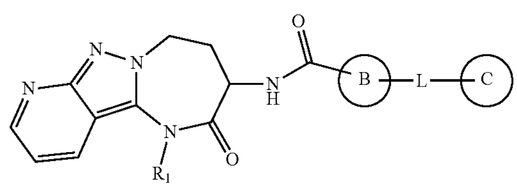
,

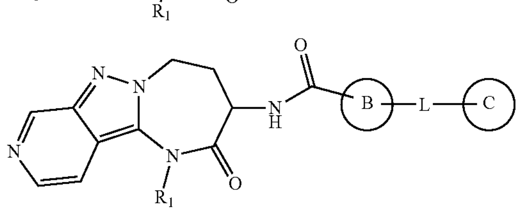
,

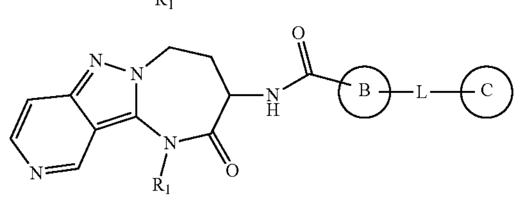
,

-continued

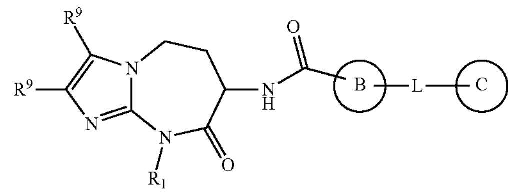
,

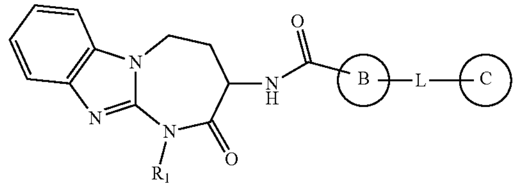
,

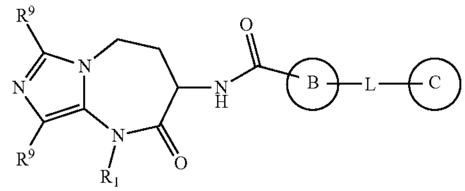
,

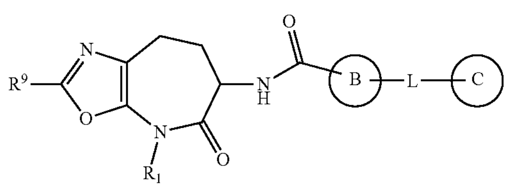
, and

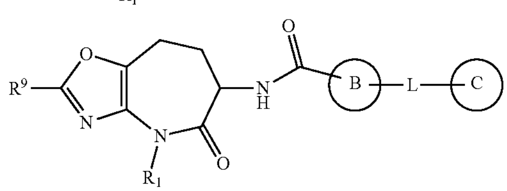
;

wherein each $R^9$ is independently selected from the group consisting of hydrogen, $C_1$-$C_6$ alkyl, $C_3$-$C_6$ cycloalkyl, $C_3$-$C_6$ cycloalkyl substituted by 1 to 2 fluorine atoms, $C_1$-$C_6$ haloalkyl, ($C_1$-$C_4$ alkoxy)-$C_1$-$C_2$ alkyl, phenyl, benzyl, $C_4$-$C_6$ heterocyclyl, $CH_2$—($C_3$-$C_6$ cycloalkyl), $CH_2$—($C_3$-$C_6$ cycloalkyl substituted by 1 to 2 fluorine atoms), and $CH_2$—($C_4$-$C_6$ heterocyclyl).

In some embodiments, each $R^9$ is selected from the group consisting of hydrogen, $C_1$-$C_4$ alkyl, $C_1$-$C_4$ haloalkyl, $CH_2CH_2OCH_3$, $C_3$-$C_4$ cycloalkyl, $C_3$-$C_4$ cycloalkyl substituted by 1 to 2 fluorine atoms, $CH_2$—($C_3$-$C_4$ cycloalkyl), $CH_2$—($C_3$-$C_4$ cycloalkyl substituted by 1 to 2 fluorine atoms), and $CH_2$—($C_4$ heterocyclyl).

In some embodiments of formula I(a), the compound is of a formula selected from the group consisting of:

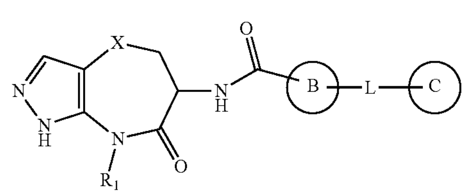
,

-continued
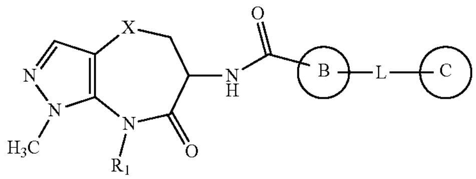,
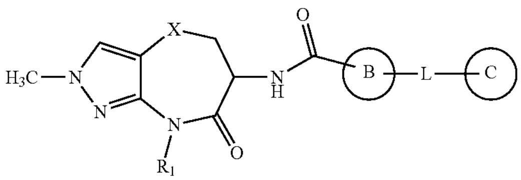,
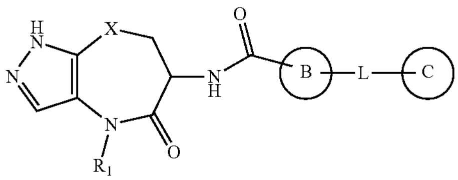,
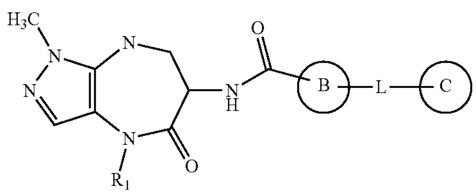,
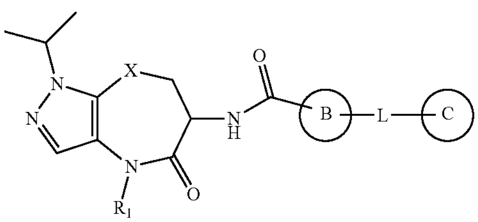,
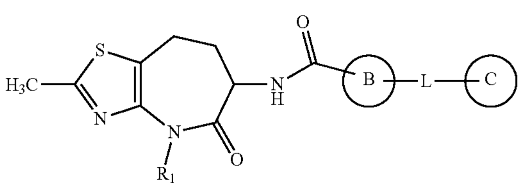,
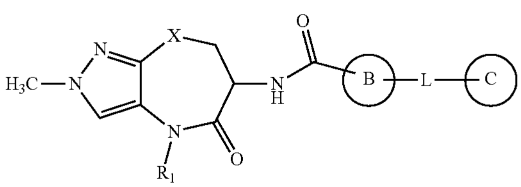,
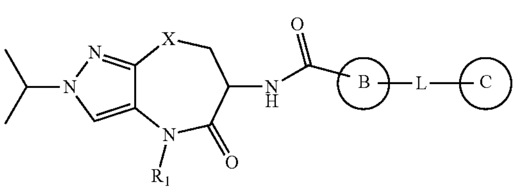,
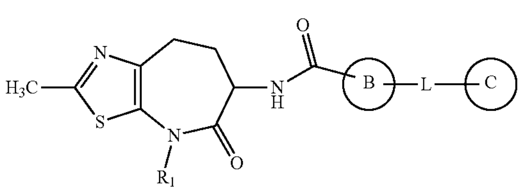,
-continued
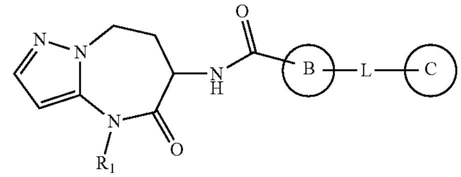,
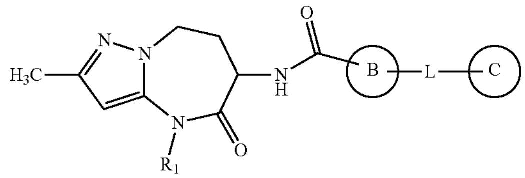,
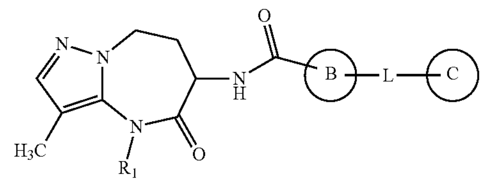,
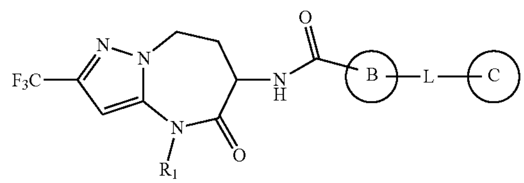,
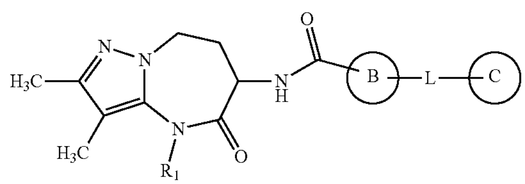,
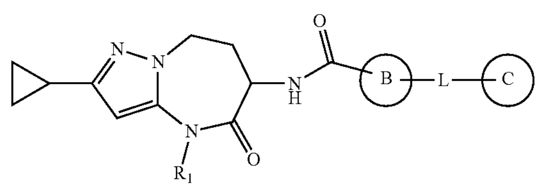,
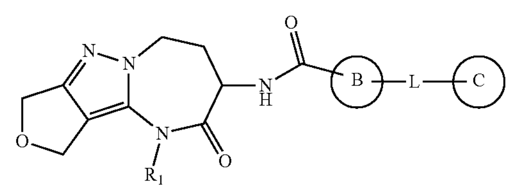,
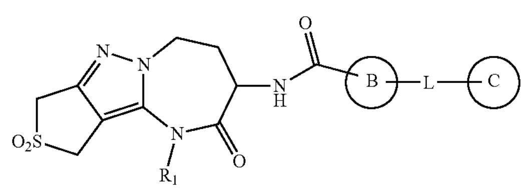,
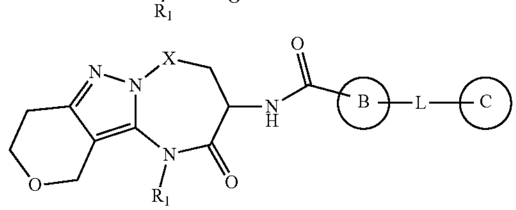, -continued
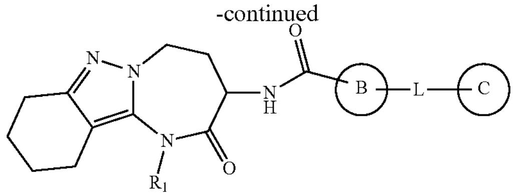,
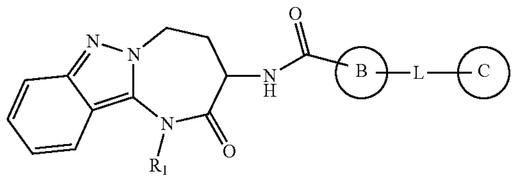,
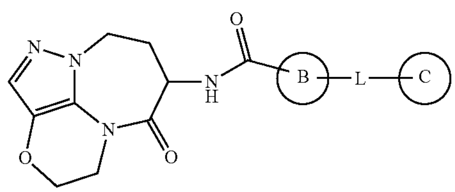,
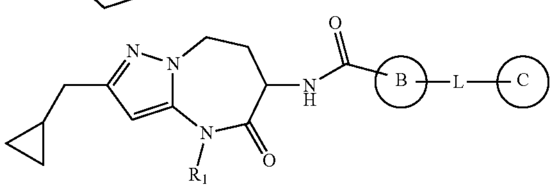,
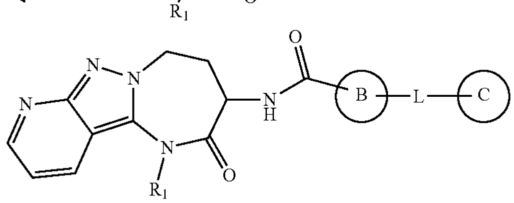,
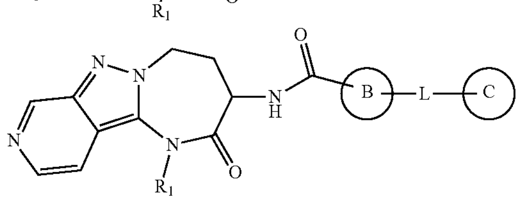,
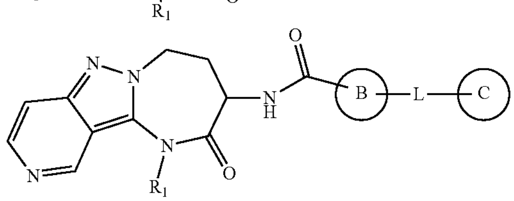,
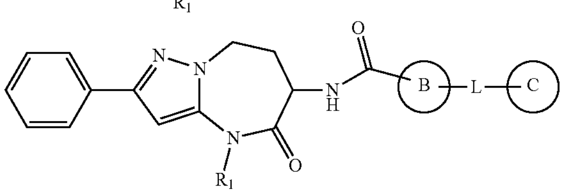,
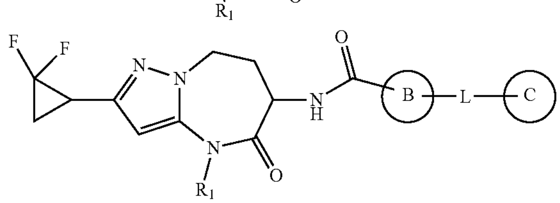,
-continued
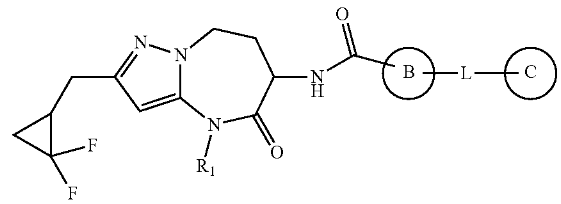,
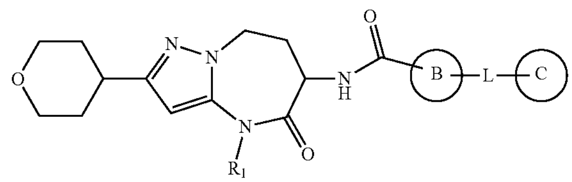,
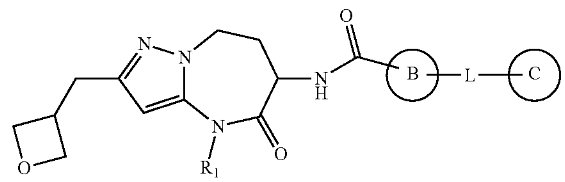,
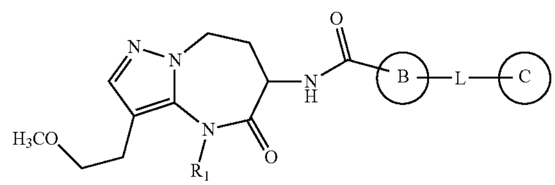,
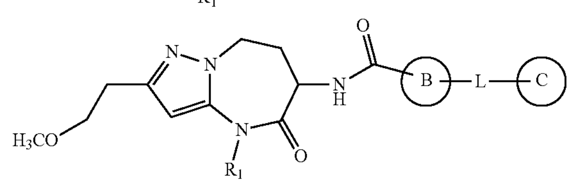,
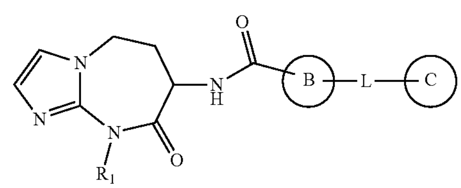,
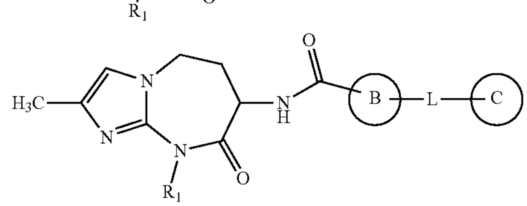,
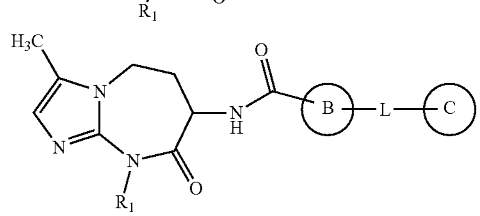,
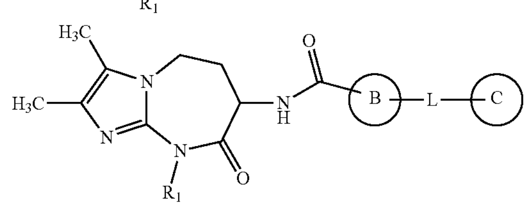, -continued

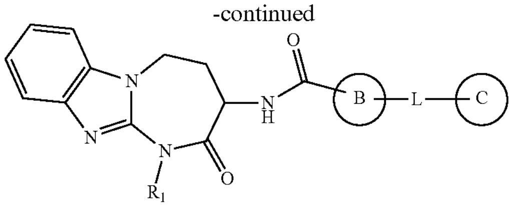
,

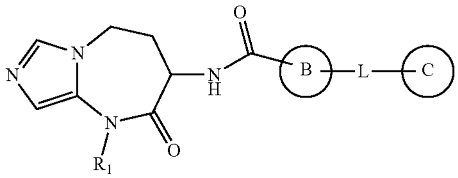
,

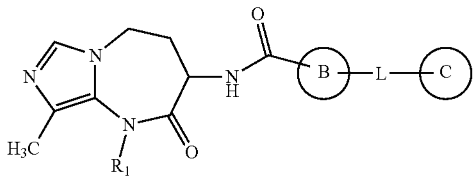
,

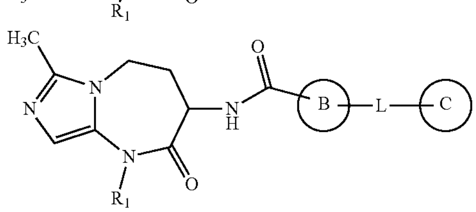
,

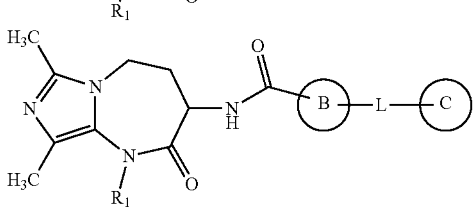
,

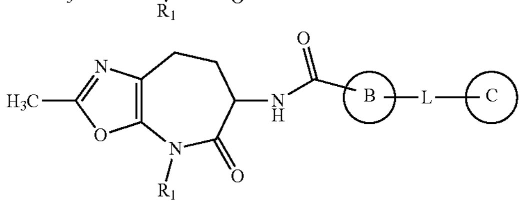
and

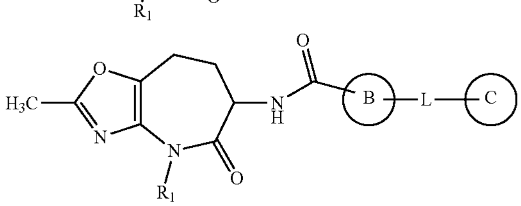
.

In some of the above embodiments of formula I(a), $R^1$ is H or methyl.

In some embodiments, provided herein is a compound of formula I(b):

(I(b))

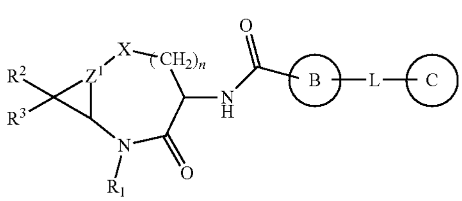

or a pharmaceutically acceptable salt thereof, wherein $R^1$, X, L, n, the A ring, the B ring, and the C ring are as described herein, wherein $Z^1$ is CH; and $R^2$ and $R^3$ are each independently selected from the group consisting of H, halo, $C_1$-$C_6$ alkyl, $C_3$-$C_6$ cycloalkyl, $CO_2$($C_1$-$C_6$ alkyl), phenyl, benzyl, 5 to 6 membered heterocyclyl, 5 to 6 membered heteroaryl, —$CH_2$($C_3$-$C_6$ cycloalkyl), and —$CH_2$($C_4$-$C_6$ heterocyclyl); provided that when each of $R^2$ and $R^3$ are other than H or halo, one must be $C_1$-$C_4$ alkyl.

In some embodiments of formula I(b), $R^2$ and $R^3$ are each independently selected from the group consisting of H, fluoro, $C_1$-$C_6$ alkyl, $C_3$-$C_6$ cycloalkyl, $CO_2$($C_1$-$C_6$ alkyl), phenyl, benzyl, 5 to 6 membered heterocyclyl, 5 to 6 membered heteroaryl, —$CH_2$($C_3$-$C_6$ cycloalkyl), and —$CH_2$($C_4$-$C_6$ heterocyclyl); provided that when each of $R^2$ and $R^3$ are other than H or fluoro, one must be $C_1$-$C_4$ alkyl.

In some embodiments of formula I(b), $R^2$ and $R^3$ are each independently H or $C_1$-$C_6$ alkyl.

In some embodiments of formula I(b), $R^1$ is H or methyl.

In some embodiments, provided herein is a compound of formula I, I(a) and I(b) wherein

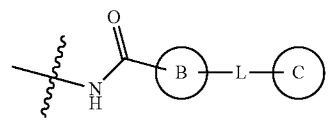

is selected from the group consisting of:

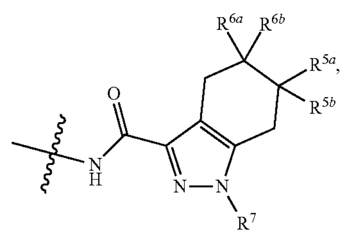

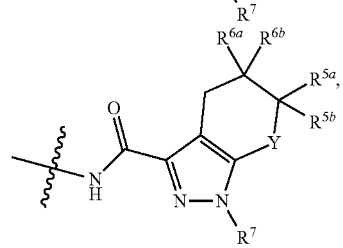

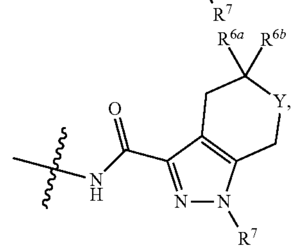

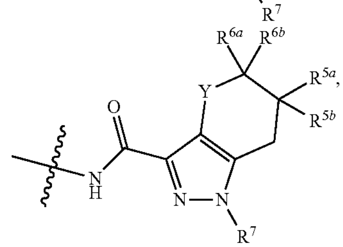

-continued
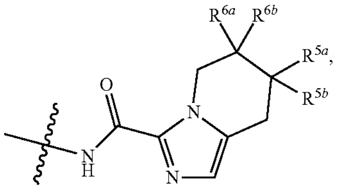
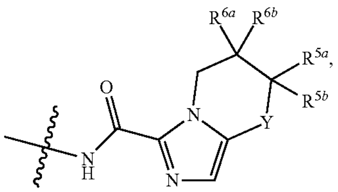
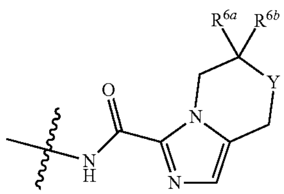
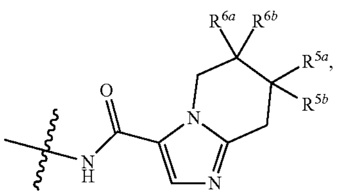
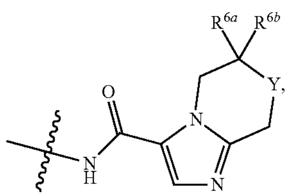
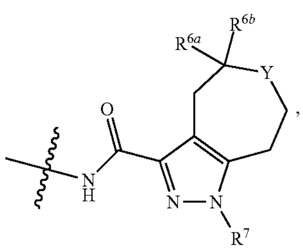
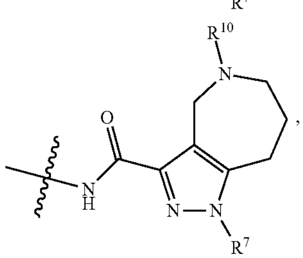
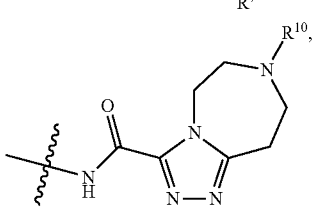
-continued
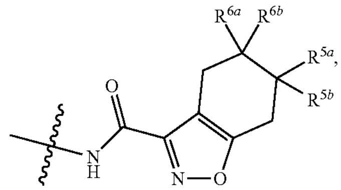
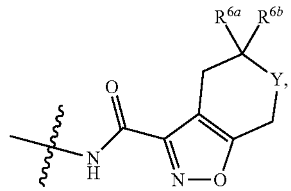
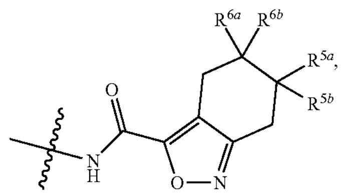
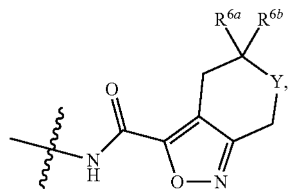
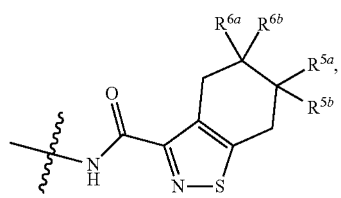
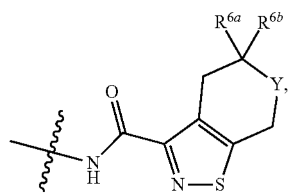
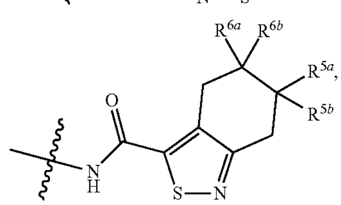
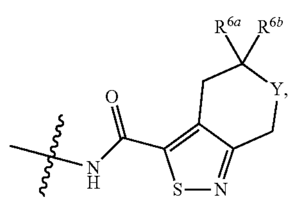
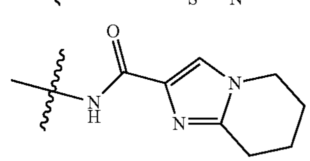

-continued
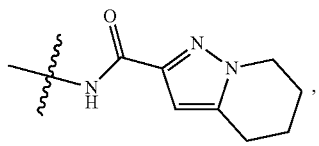
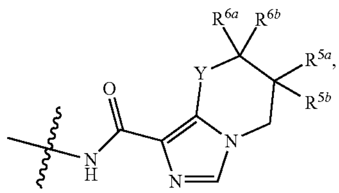
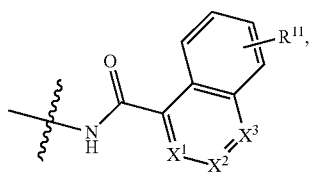
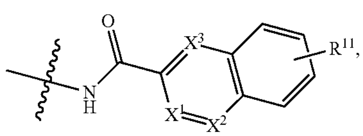
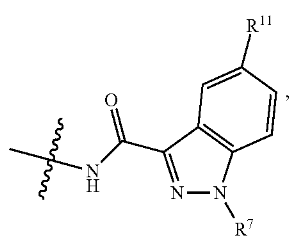
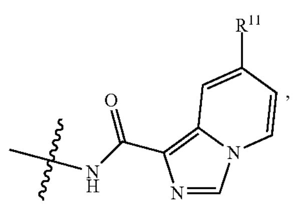
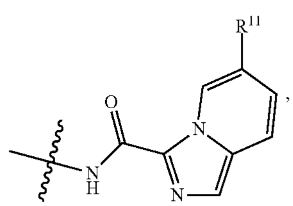
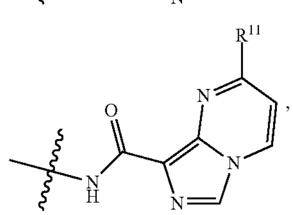
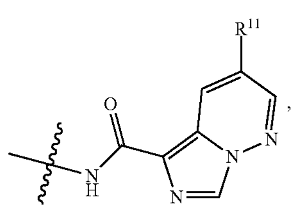
-continued
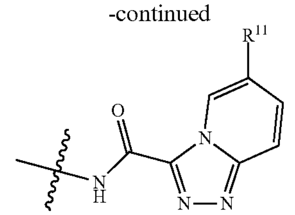
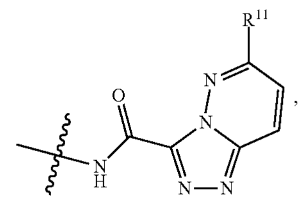
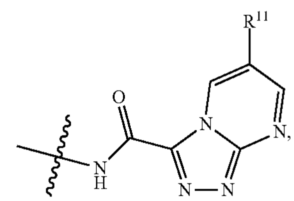
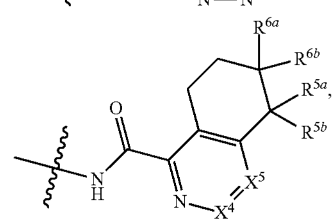
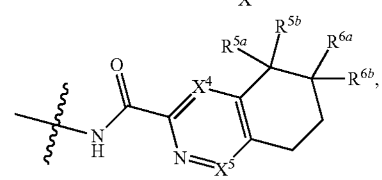
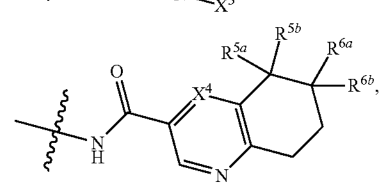
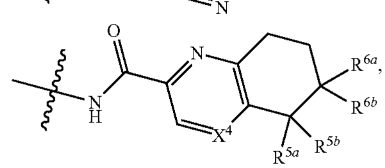
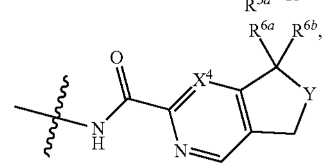
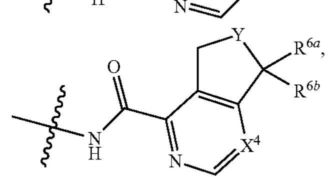

-continued
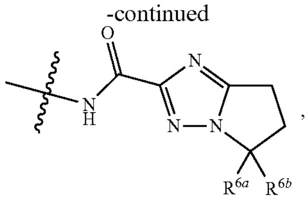
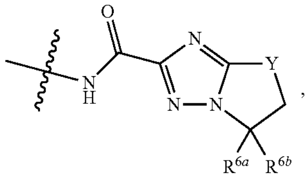
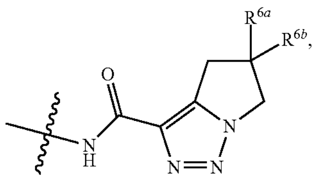
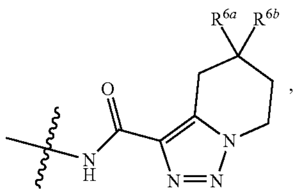
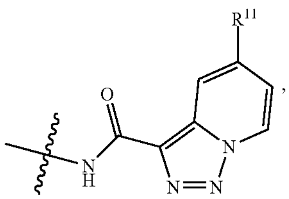
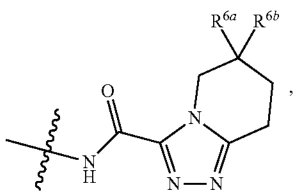
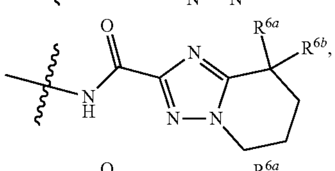
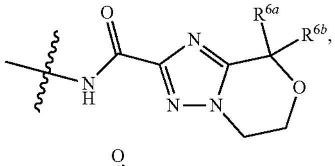
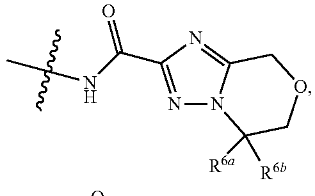
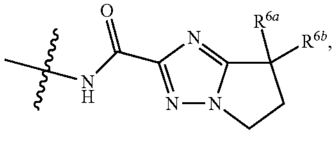
-continued
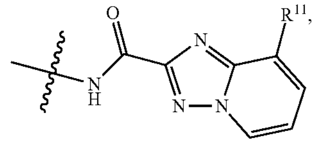
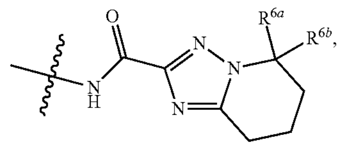
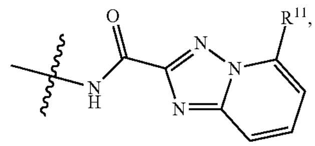
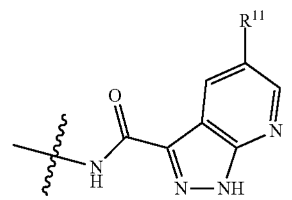
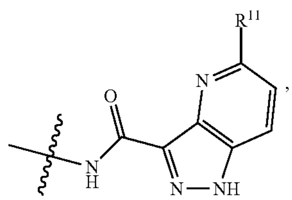
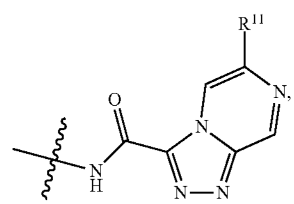
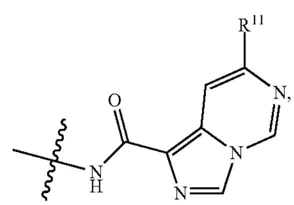
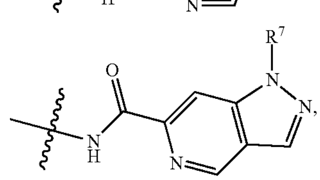
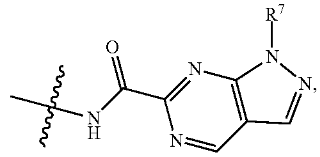
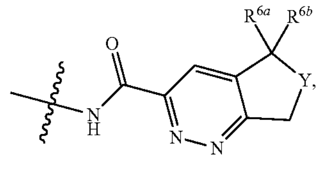

-continued

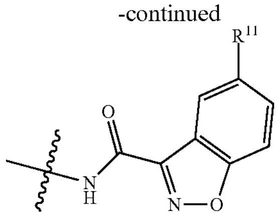

and

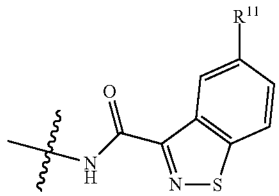

;

Y is selected from the group consisting of O, S, SO and $SO_2$;

$X^1$, $X^2$ and $X^3$ are each independently N or CH, wherein 1 or 2 of $X^1$, $X^2$ and $X^3$ is N;

$X^4$ and $X^5$ are each independently N or CH;

$R^{5a}$ and $R^{5b}$, are each independently selected from the group consisting of H, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, phenyl, benzyl, —$CH_2$($C_3$-$C_6$ cycloalkyl); and 5 to 6 membered heteroaryl; wherein $R^{5a}$ and $R^{5b}$ together with the carbon to which they are attached may form a 3 to 5 membered cycloalkyl optionally substituted by one or two fluoro, or a 4 to 5 membered cycloalkoxy;

$R^{6a}$ and $R^{6b}$ are each independently selected from the group consisting of H, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, phenyl, mono- or di-fluorophenyl, benzyl, —$CH_2$($C_3$-$C_6$ cycloalkyl), and 5 to 6 membered heteroaryl; wherein $R^{6a}$ and $R^{6b}$ together with the carbon to which they are attached may form a 3 to 5 membered cycloalkyl optionally substituted by one or two fluoro, or a 4 to 5 membered cycloalkoxy;

wherein when $R^{5a}$ and $R^{6a}$ are each H, $R^{5b}$ and $R^{6b}$ may together form a 3 or 4 membered cycloalkyl;

and wherein only two of $R^{5a}$, $R^{5b}$, $R^{6a}$ and $R^{6b}$ may be other than H in each instance;

$R^7$ is selected from the group consisting of H, unsubstituted $C_1$-$C_4$ alkyl, $C_3$-$C_6$ cycloalkyl, and $C_4$-$C_6$ cycloalkoxy;

$R^{10}$ is selected from the group consisting of H, $C_1$-$C_6$ alkyl, $C_3$-$C_6$ cycloalkyl, $C_1$-$C_6$ haloalkyl, phenyl, and benzyl; and $R^{11}$ is selected from the group consisting of H, halogen, cyano, $C_1$-$C_4$ alkyl, and $C_1$-$C_4$ haloalkyl.

In some embodiments, Y is O.

In some embodiments, $R^{5a}$ and $R^{5b}$ are each H.

In some embodiments, $R^{5a}$ and $R^{5b}$ are each H; and $R^{6a}$ and $R^{6b}$ are each independently $C_1$-$C_4$ alkyl. In some embodiments, $R^{5a}$ and $R^{5b}$ are each H; $R^{6a}$ is H; and $R^{6b}$ is $C_1$-$C_4$ alkyl, $C_1$-$C_4$ haloalkyl or phenyl. In some embodiments, $R^{5a}$ and $R^{5b}$ are each H; $R^{6a}$ is H; and $R^{6b}$ is $C_1$-$C_4$ alkyl or $C_1$-$C_4$ haloalkyl. In some embodiments, $R^{5a}$ and $R^{5b}$ are each H; $R^{6a}$ is methyl; and $R^{6b}$ is $C_1$-$C_4$ alkyl or $C_3$-$C_4$ cycloalkyl. In some embodiments, $R^{5a}$ and $R^{5b}$ are each H; $R^{6a}$ is methyl; and $R^{6b}$ is phenyl.

In some embodiments, $R^{5a}$ and $R^{6a}$ are each H, and $R^{5b}$ and $R^{6b}$ together form cyclopropyl or cyclobutyl; and Y is O.

In some embodiments, $R^7$ is H or methyl.

In some embodiments, $R^{10}$ is selected from the group consisting of H, $C_1$-$C_4$ alkyl, $C_3$-$C_4$ cycloalkyl, phenyl, and benzyl.

In some embodiments, $R^{11}$ is selected from the group consisting of H, halogen, methyl, and trifluromethyl.

In some embodiments, provided herein is a compound of formula I, I(a) and I(b) wherein

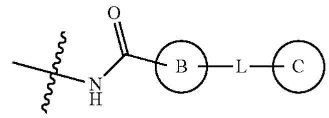

is selected from the group consisting of:

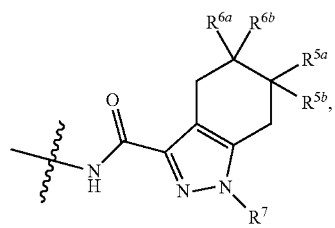

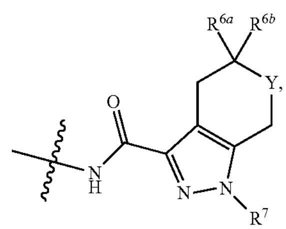

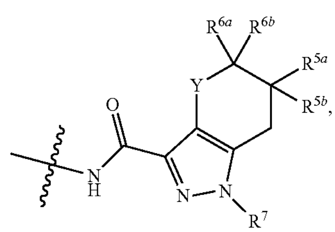

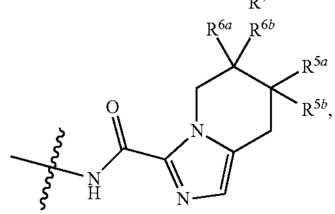

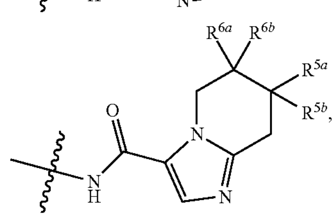

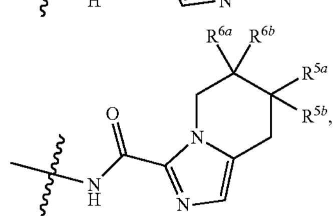

-continued

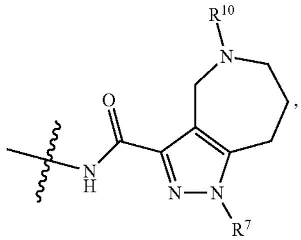

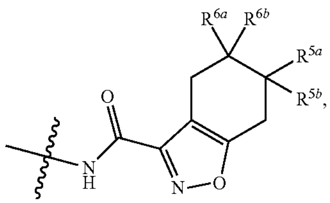

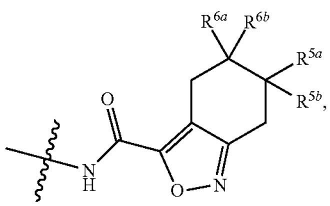

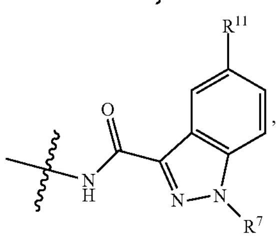

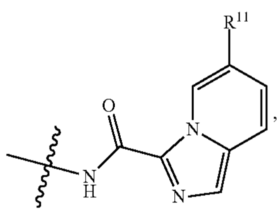

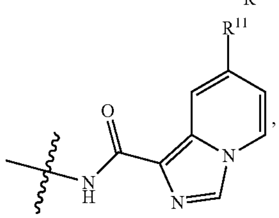

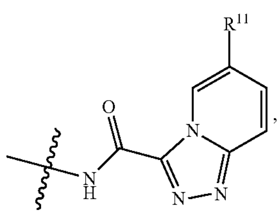

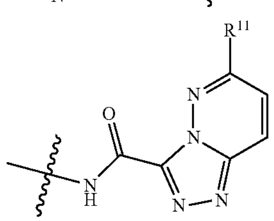

and

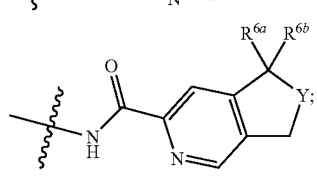

wherein $R^{5b}$, $R^{5b}$, $R^{6a}$, $R^{6b}$, $R^7$, $R^{10}$ and $R^{11}$ are as defined above; and Y is O.

In some embodiments, provided herein is a compound of formula I, I(a) and I(b) wherein

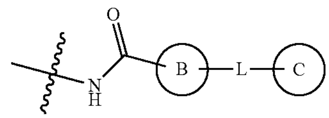

is selected from the group consisting of:

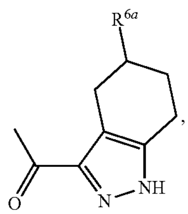

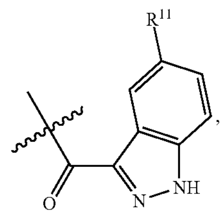

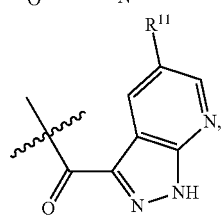

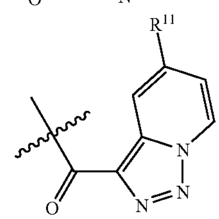

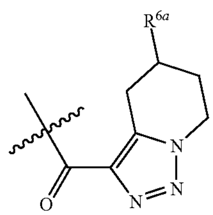

and

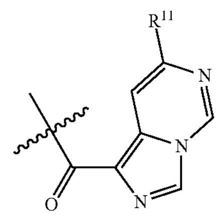

wherein $R^{6a}$ and $R^{11}$ are as defined above. In some embodiments, $R^{6a}$ is $C_1$-$C_6$ alkyl, $C_3$-$C_6$ cycloalkyl, $C_1$-$C_6$ haloalkyl or phenyl. In some embodiments, $R^{11}$ is $C_1$-$C_6$ alkyl, $C_3$-$C_6$ cycloalkyl, $C_1$-$C_6$ haloalkyl or phenyl.

In some embodiments, provided herein is a compound of formula I, I(a) or I(b) wherein

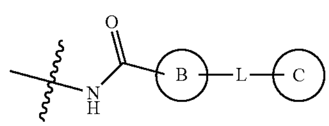

is

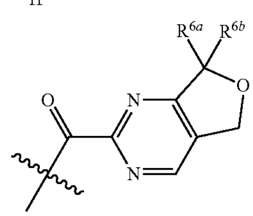

wherein $R^{6a}$ and $R^{6b}$ are as defined above. In some embodiments, $R^{6a}$ and $R^{6b}$ are each independently selected from the group consisting of H, $C_1$-$C_6$ alkyl, $C_3$-$C_6$ cycloalkyl, $C_1$-$C_6$ haloalkyl or phenyl; provided that if one of $R^{6a}$ and $R^{6b}$ is phenyl, the other is H. In some embodiments, $R^{6a}$ and $R^{6b}$ together form $C_3$-$C_6$ cycloalkyl.

In some embodiments, provided herein is a compound of formula I, I(a) or I(b) wherein

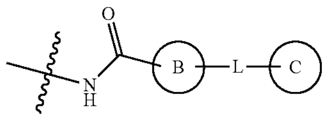 is

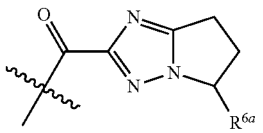

wherein $R^{6a}$ is as defined above. In some embodiments, $R^{6a}$ is selected from the group consisting of H, $C_1$-$C_6$ alkyl, $C_3$-$C_6$ cycloalkyl, $C_1$-$C_6$ haloalkyl or phenyl. In some embodiments, $R^{6a}$ is phenyl.

In some embodiments, provided herein is a compound of formula I(a) or I(b), wherein

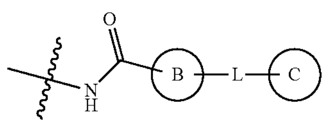

is selected from the group consisting of:

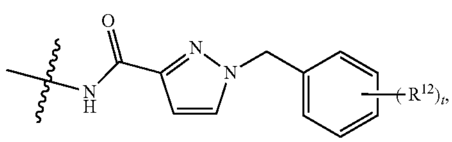

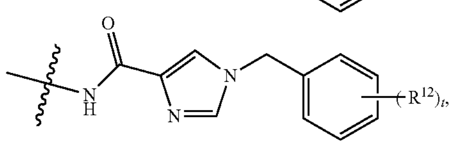

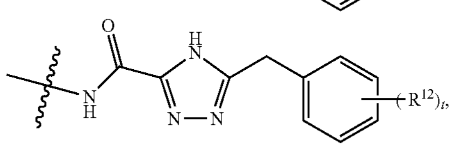

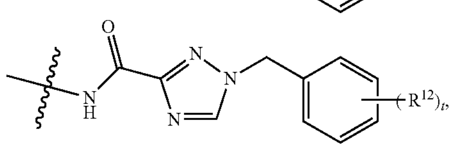

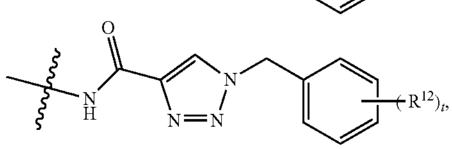

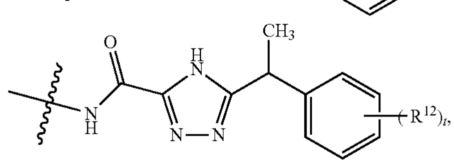 and

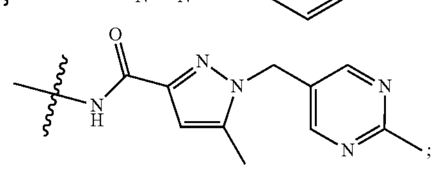

wherein $R^{12}$ is selected from the group consisting of halogen and methyl; and t is 0, 1 or 2.

In some embodiments, $R^{12}$ is fluoro and t is 1 or 2. In some embodiments, t is 0.

In some embodiments, provided herein is a compound of formula I(a) or I(b), wherein

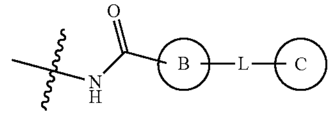 is

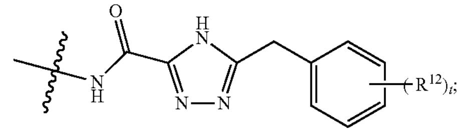

wherein $R^{12}$ and t are as defined above. In some embodiments, each $R^{12}$ is selected from fluoro and chloro. In some embodiments, each $R^{12}$ is F and t is 1 or 2.

In some embodiments, provided herein is a compound of formula I(a) or I(b), wherein

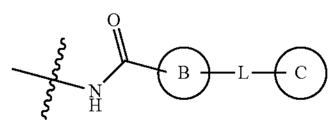 is

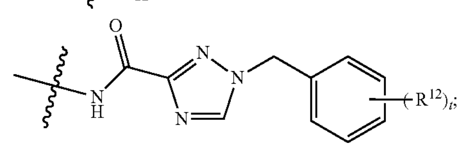

wherein $R^{12}$ and t are as defined above. In some embodiments, each $R^{12}$ is selected from fluoro and chloro. In some embodiments, each $R^{12}$ is F and t is 1 or 2.

Also provided herein are specific stereoisomers of the compounds of each of the above embodiments of formulae I, I(a) and I(b):

(I)

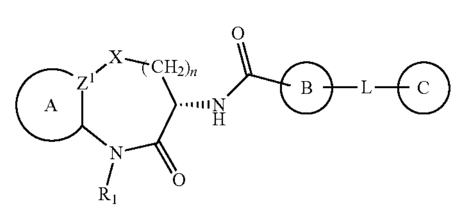

(I(a))

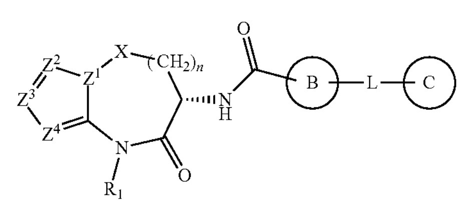

-continued (I(b))

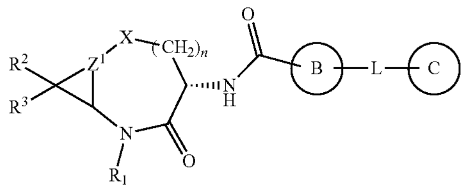

and each of the substituents are as defined above.

In some embodiments, provided herein is a compound of formula I(a) of the formula:

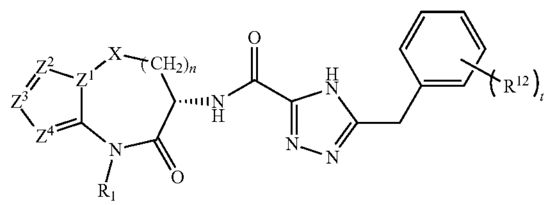

wherein each of the substituents are as defined above.

In some embodiments provided herein is a compound of formula I(a) of the formula:

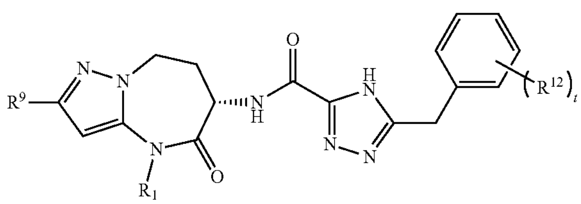

wherein $R^1$ is H, methyl or ethyl; $R^9$ is selected from the group consisting of hydrogen, $C_1$-$C_6$ alkyl, $C_3$-$C_6$ cycloalkyl, $C_3$-$C_6$ cycloalkyl substituted by 1 to 2 fluorine atoms, $C_1$-$C_6$ haloalkyl, ($C_1$-$C_4$ alkoxy)-$C_1$-$C_2$ alkyl, phenyl and benzyl; $R^{12}$ is F or Cl; and t is 0, 1, 2 or 3. In some embodiments, $R^1$ is methyl; $R^9$ is selected from the group consisting of hydrogen, $C_1$-$C_6$ alkyl, $C_3$-$C_6$ cycloalkyl, and $C_3$-$C_6$ cycloalkyl substituted by 1 to 2 fluorine atoms; $R^{12}$ is F; and t is 0, 1 or 2.

In some embodiments, provided herein is a compound of formula I(a) of the formula:

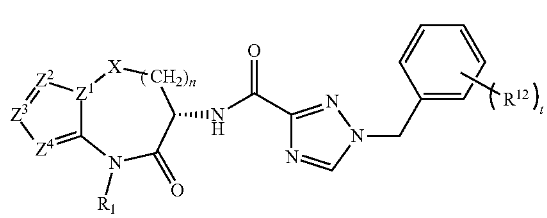

wherein each of the substituents are as defined above.

In some embodiments, provided herein is a compound of formula I(a)(i) of the formula:

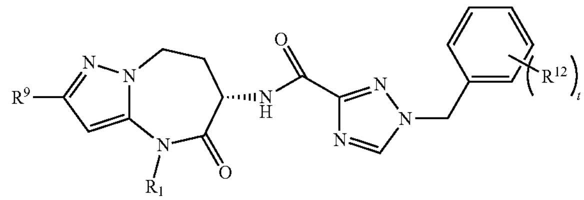

wherein $R^1$ is H, methyl or ethyl; $R^9$ is selected from the group consisting of hydrogen, $C_1$-$C_6$ alkyl, $C_3$-$C_6$ cycloalkyl, $C_3$-$C_6$ cycloalkyl substituted by 1 to 2 fluorine atoms, $C_1$-$C_6$ haloalkyl, ($C_1$-$C_4$ alkoxy)-$C_1$-$C_2$ alkyl, phenyl and benzyl; $R^{12}$ is F or Cl; and t is 0, 1, 2 or 3. In some embodiments, $R^1$ is methyl; $R^9$ is selected from the group consisting of hydrogen, $C_1$-$C_6$ alkyl, $C_3$-$C_6$ cycloalkyl, and $C_3$-$C_6$ cycloalkyl substituted by 1 to 2 fluorine atoms; $R^{12}$ is F; and t is 0, 1 or 2.

In some embodiments, provided herein is a compound of formula I(a) of the formula:

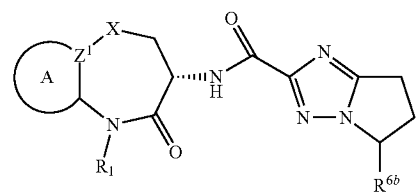

or

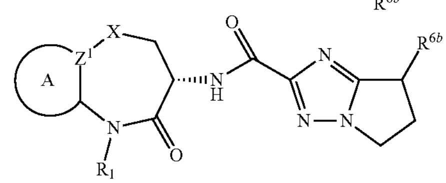

wherein $R^1$, the A ring, $Z^1$, X, and $R^{6b}$ are as defined herein. In some embodiments, $R^1$ is H, methyl or ethyl. In some embodiments, $R^1$ is H or methyl; the A ring is 6 membered aryl or 5 membered heteroaryl; $Z^1$ is C or N; X is $CH_2$ or O; and $R^{6b}$ is as defined herein. In some embodiments, $R^1$ is H or methyl; the A ring is 6 membered aryl or 5 membered heteroaryl; $Z^1$ is C or N; X is $CH_2$ or O; and $R^{6b}$ is $C_1$-$C_4$ alkyl, $C_1$-$C_4$ haloalkyl or phenyl.

In some embodiments, provided herein is a compound of formula I(a) of the formula:

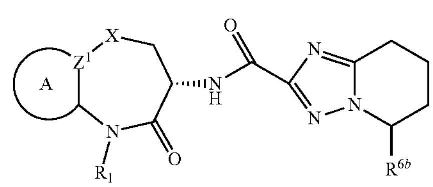

or

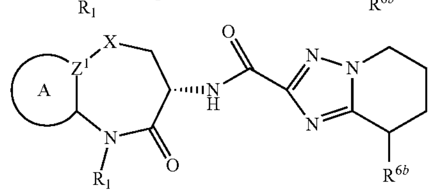

wherein $R^1$, the A ring, $Z^1$, X, and $R^{6b}$ are as defined herein. In some embodiments, $R^1$ is H, methyl or ethyl. In some embodiments, $R^1$ is H or methyl; the A ring is 6 membered aryl or 5 membered heteroaryl; $Z^1$ is C or N; X is $CH_2$ or O; and $R^{6b}$ is as defined herein. In some embodiments, $R^1$ is H or methyl; the A ring is 6 membered aryl or 5 membered heteroaryl; $Z^1$ is C or N; X is $CH_2$ or O; and $R^{6b}$ is $C_1$-$C_4$ alkyl, $C_1$-$C_4$ haloalkyl or phenyl.

In some embodiments, provided herein is a compound of formula I(a) of the formula:

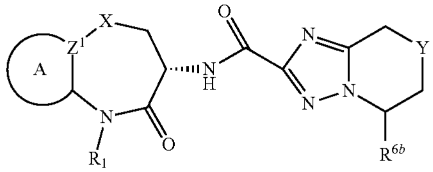

or

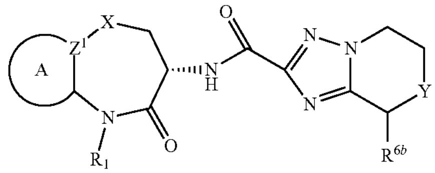

wherein $R^1$, the A ring, $Z^1$, X, and $R^{6b}$ are as defined herein, and Y is NH or O. In some embodiments, $R^1$ is H, methyl or ethyl. In some embodiments, $R^1$ is H or methyl; the A ring is 6 membered aryl or 5 membered heteroaryl; $Z^1$ is C or N; X is $CH_2$ or O; and $R^{6b}$ is as defined herein. In some embodiments, $R^1$ is H or methyl; the A ring is 6 membered aryl or 5 membered heteroaryl; $Z^1$ is C or N; X is $CH_2$ or O; and $R^{6b}$ is $C_1$-$C_4$ alkyl, $C_1$-$C_4$ haloalkyl or phenyl.

In some embodiments, provided herein is a compound of formula I(a) of the formula:

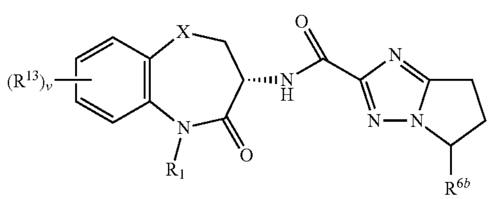

or

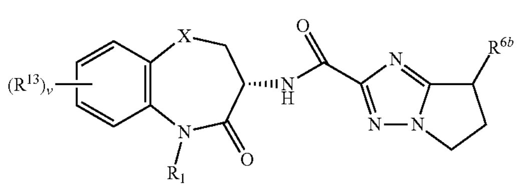

wherein each $R^{13}$ is halo or $C_1$-$C_4$ alkyl, v is 0 to 2; and $R^1$, X, and $R^{6b}$ are as defined herein. In some embodiments, $R^1$ is H, methyl or ethyl. In some embodiments, $R^1$ is H or methyl; X is $CH_2$ or O; and $R^{6b}$ is as defined herein. In some embodiments, $R^1$ is H or methyl; the A ring is 6 membered aryl or 5 membered heteroaryl; $Z^1$ is C or N; X is $CH_2$ or O; and $R^{6b}$ is $C_1$-$C_4$ alkyl, $C_1$-$C_4$ haloalkyl or phenyl. In some embodiments, each $R^{13}$ is F or methyl.

In some embodiments, provided herein is a compound of formula I(a) of the formula:

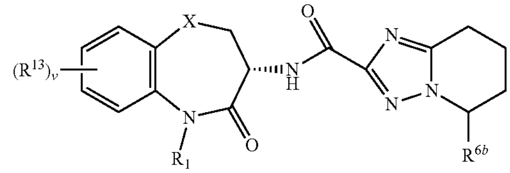

or

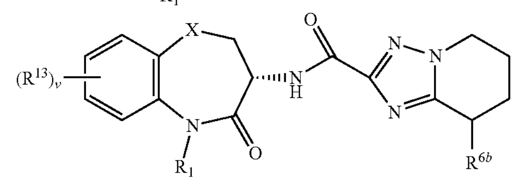

wherein each $R^{13}$ is halo or $C_1$-$C_4$ alkyl, v is 0 to 2; and $R^1$, X, and $R^{6b}$ are as defined herein. In some embodiments, $R^1$ is H, methyl or ethyl. In some embodiments, $R^1$ is H or methyl; X is $CH_2$ or O; and $R^{6b}$ is as defined herein. In some embodiments, $R^1$ is H or methyl; the A ring is 6 membered aryl or 5 membered heteroaryl; $Z^1$ is C or N; X is $CH_2$ or O; and $R^{6b}$ is $C_1$-$C_4$ alkyl, $C_1$-$C_4$ haloalkyl or phenyl. In some embodiments, each $R^{13}$ is F or methyl.

In some embodiments, provided herein is a compound of formula I(a) of the formula:

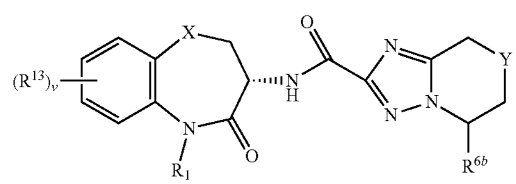

or

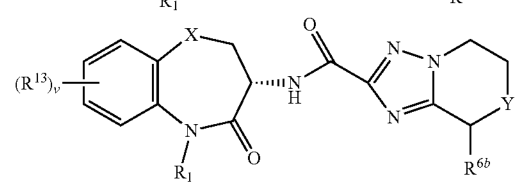

wherein each $R^{13}$ is halo or $C_1$-$C_4$ alkyl, v is 0 to 2; Y is NH or O; and $R^1$, X, and $R^{6b}$ are as defined herein. In some embodiments, $R^1$ is H, methyl or ethyl. In some embodiments, $R^1$ is H or methyl; X is $CH_2$ or O; and $R^{6b}$ is as defined herein. In some embodiments, $R^1$ is H or methyl; the A ring is 6 membered aryl or 5 membered heteroaryl; $Z^1$ is C or N; X is $CH_2$ or O; and $R^{6b}$ is $C_1$-$C_4$ alkyl, $C_1$-$C_4$ haloalkyl or phenyl. In some embodiments, each $R^{13}$ is F or methyl.

In some embodiments, provided herein is a compound of formula I(a) of the formula:

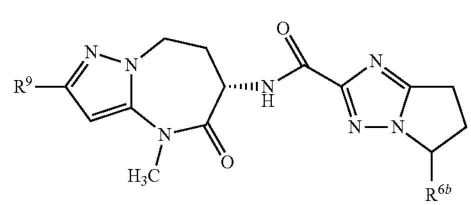

or

-continued

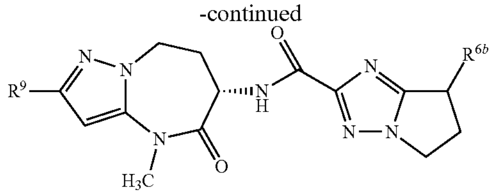

wherein $R^9$ is selected from the group consisting of hydrogen, $C_1$-$C_6$ alkyl, $C_3$-$C_6$ cycloalkyl, $C_3$-$C_6$ cycloalkyl substituted by 1 to 2 fluorine atoms, $C_1$-$C_6$ haloalkyl, ($C_1$-$C_4$ alkoxy)-$C_1$-$C_2$ alkyl, phenyl and benzyl; and $R^{6b}$ is as defined herein. In some embodiments, $R^9$ is H, $C_1$-$C_4$ alkyl, or $C_3$-$C_6$ cycloalkyl; and $R^{6b}$ is $C_1$-$C_4$ alkyl, $C_1$-$C_4$ haloalkyl or phenyl optionally substituted by 1 to 4 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl). In some embodiments, $R^9$ is H, $C_1$-$C_4$ alkyl, $C_3$-$C_6$ cycloalkyl; and $R^{6b}$ is $C_1$-$C_4$ alkyl, $C_1$-$C_4$ haloalkyl, phenyl, fluorophenyl or di-fluorophenyl.

In some embodiments, provided herein is a compound of formula I(a) of the formula:

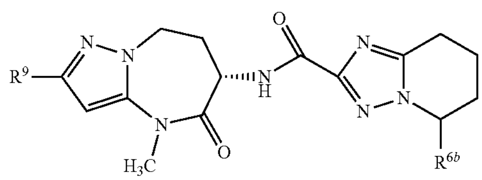

or

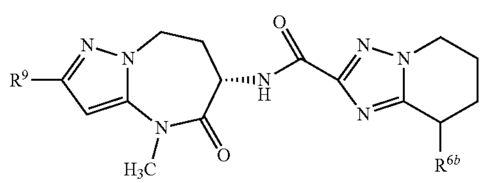

wherein $R^9$ is selected from the group consisting of hydrogen, $C_1$-$C_6$ alkyl, $C_3$-$C_6$ cycloalkyl, $C_3$-$C_6$ cycloalkyl substituted by 1 to 2 fluorine atoms, $C_1$-$C_6$ haloalkyl, ($C_1$-$C_4$ alkoxy)-$C_1$-$C_2$ alkyl, phenyl and benzyl; and $R^{6b}$ is as defined herein. In some embodiments, $R^9$ is H, $C_1$-$C_4$ alkyl, or $C_3$-$C_6$ cycloalkyl; and $R^{6b}$ is $C_1$-$C_4$ alkyl, $C_1$-$C_4$ haloalkyl or phenyl optionally substituted by 1 to 4 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl). In some embodiments, $R^9$ is H, $C_1$-$C_4$ alkyl, $C_3$-$C_6$ cycloalkyl; and $R^{6b}$ is $C_1$-$C_4$ alkyl, $C_1$-$C_4$ haloalkyl, phenyl, fluorophenyl or di-fluorophenyl.

In some embodiments, provided herein is a compound of formula I(a) of the formula:

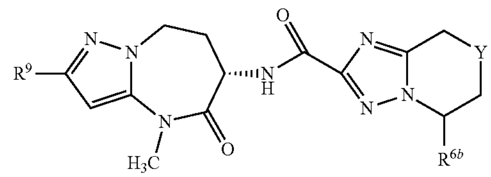

or

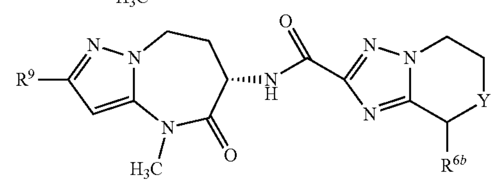

wherein Y is NH or O; $R^9$ is selected from the group consisting of hydrogen, $C_1$-$C_6$ alkyl, $C_3$-$C_6$ cycloalkyl, $C_3$-$C_6$ cycloalkyl substituted by 1 to 2 fluorine atoms, $C_1$-$C_6$ haloalkyl, ($C_1$-$C_4$ alkoxy)-$C_1$-$C_2$ alkyl, phenyl and benzyl; and $R^{6b}$ is as defined herein. In some embodiments, $R^9$ is H, $C_1$-$C_4$ alkyl, or $C_3$-$C_6$ cycloalkyl; and $R^{6b}$ is $C_1$-$C_4$ alkyl, $C_1$-$C_4$ haloalkyl or phenyl optionally substituted by 1 to 4 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), and $CH_2CH_2$—($C_3$-$C_6$ cycloalkyl). In some embodiments, $R^9$ is H, $C_1$-$C_4$ alkyl, $C_3$-$C_6$ cycloalkyl; and $R^{6b}$ is $C_1$-$C_4$ alkyl, $C_1$-$C_4$ haloalkyl, phenyl, fluorophenyl or di-fluorophenyl.

Also provided herein are embodiments corresponding to each of those described above, wherein each substituent is unsubstituted unless explicity provided in the embodiment.

Particular compounds of formulae I, I(a), I(b) and II (hereafter referred to collectively as "formula I") include the following, wherein each compound is the result of a condensation between a "left-hand side" amine (LHS Amine) of Table A, and a "right-hand side" carboxylic acid (RHS Acid) of Table A to form an amide of formula I. For simplicity, hydrogens are not shown. All possible combinations of a LHS Amine with a RHS Acid are contemplated and within the scope of the invention.

TABLE A

| | LHS Amine | RHS Acid | |
|---|---|---|---|
| 1 | 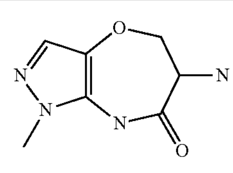 | 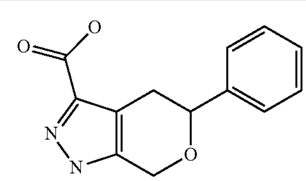 [SMILES: O=C(O)c1n[nH]c2c1CC(c1ccccc1)OC2] | 1 |

TABLE A-continued
| | LHS Amine | RHS Acid | |
|---|---|---|---|
| 2 | 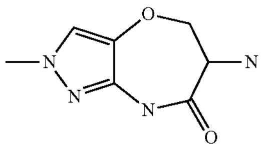 | 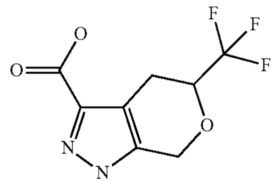 [SMILES: O=C(O)c1n[nH]c2c1CC(C(F)(F)F)OC2] | 2 |
| 3 | 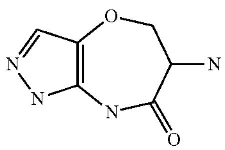 [SMILES: NC1COc2cn[nH]c2NC1=O] | 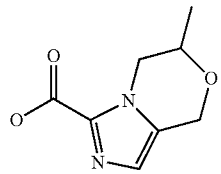 | 3 |
| 4 | 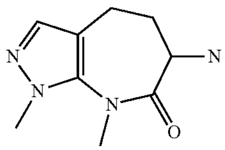 | 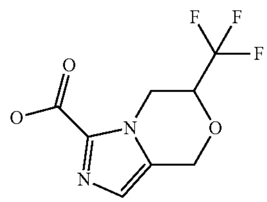 | 4 |
| 5 | 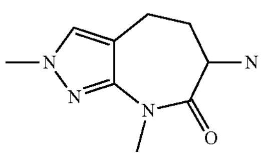 | 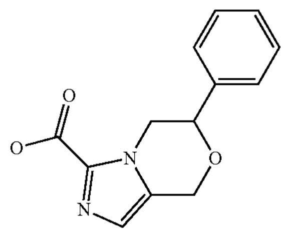 [SMILES: O=C(O)c1ncc2n1CC(c1ccccc1)OC2] | 5 |
| 6 | 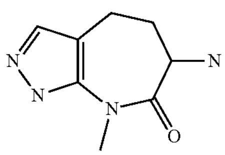 | 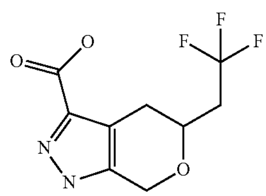 [SMILES: O=C(O)c1n[nH]c2c1CC(CC(F)(F)F)OC2] | 6 |
| 7 | 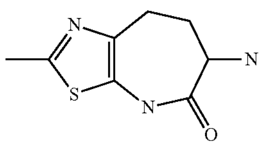 | 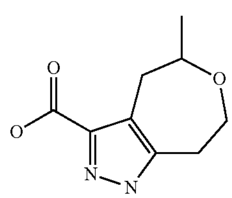 | 7 |
| 8 | 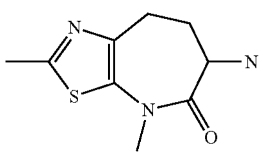 | 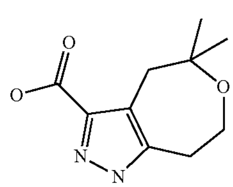 | 8 |
| 9 | 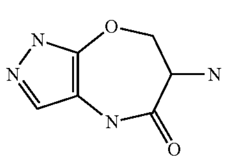 [SMILES: NC1COc2[nH]ncc2NC1=O] | 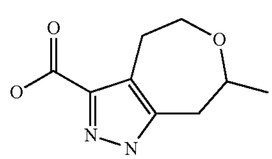 | 9 |

TABLE A-continued
| | LHS Amine | RHS Acid | |
|---|---|---|---|
| 10 | 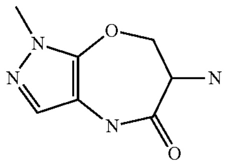 | 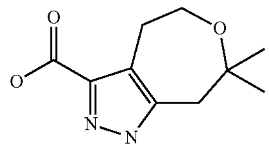 | 10 |
| 11 | 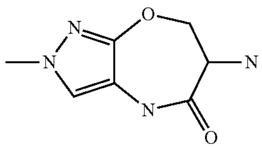 | 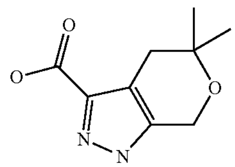 | 11 |
| 12 | 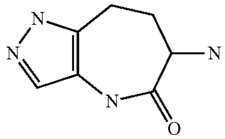 [SMILES: NC1CCc2[nH]ncc2NC1=O] | 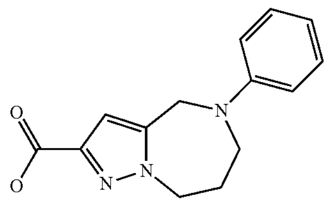 [SMILES: O=C(O)c1cc2n(n1)CCCN(c1ccccc1)C2] | 12 |
| 13 | 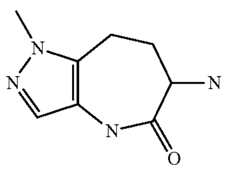 | 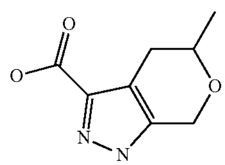 | 13 |
| 14 | 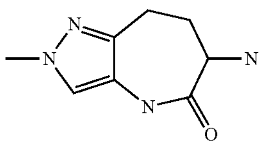 | 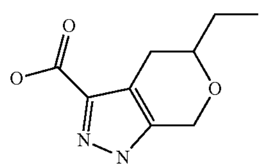 | 14 |
| 15 | 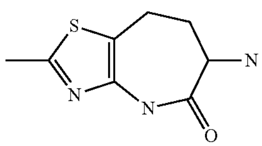 | 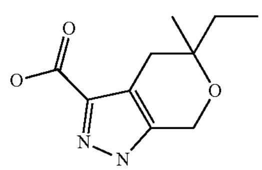 | 15 |
| 16 | 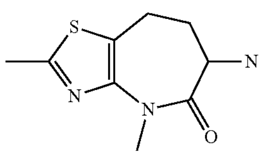 | 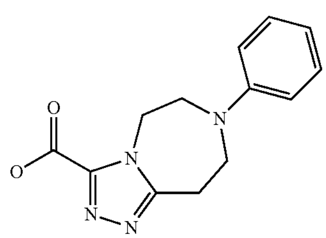 [SMILES: O=C(O)c1nnc2n1CCN(c1ccccc1)CC2] | 16 |
| 17 | 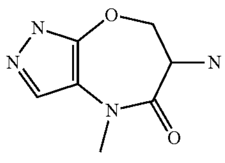 | 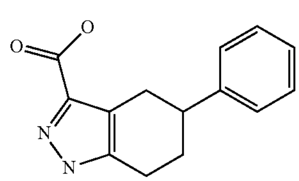 | 17 |

TABLE A-continued
| | LHS Amine | RHS Acid | |
|---|---|---|---|
| 18 | 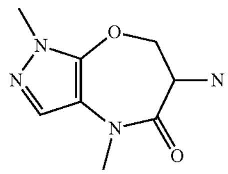 | 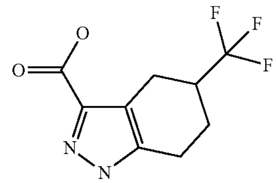 [SMILES: O=C(O)c1n[nH]c2c1CC(C(F)(F)F)CC2] | 18 |
| 19 | 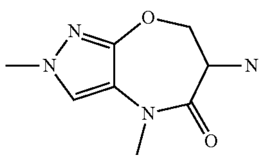 | 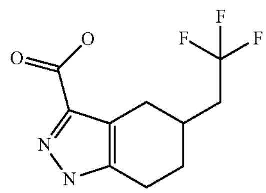 | 19 |
| 20 | 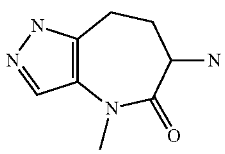 | 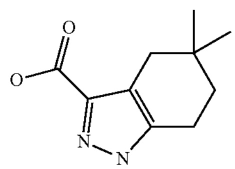 | 20 |
| 21 | 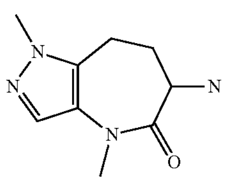 | 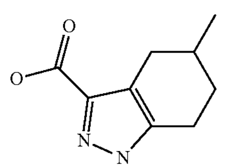 | 21 |
| 22 | 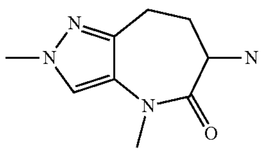 | 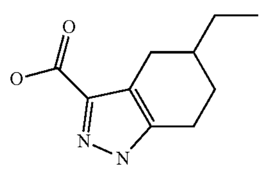 | 22 |
| 23 | 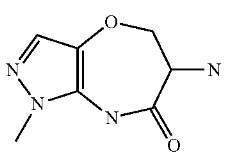 | 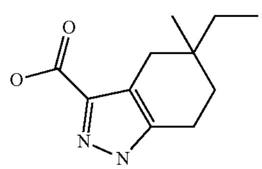 | 23 |
| 24 | 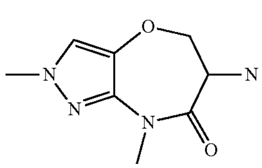 | 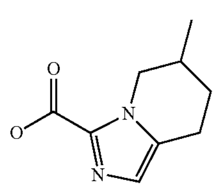 | 24 |
| 25 | 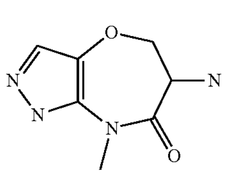 | 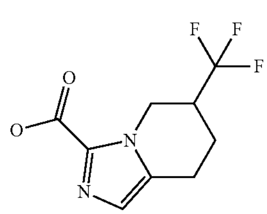 [SMILES: O=C(O)c1ncc2n1CC(C(F)(F)F)CC2] | 25 |

TABLE A-continued
| | LHS Amine | RHS Acid | |
|---|---|---|---|
| 26 | 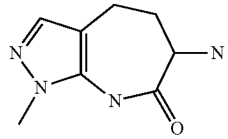 | 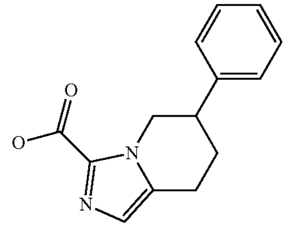 [SMILES: O=C(O)c1ncc2n1CC(c1ccccc1)CC2] | 26 |
| 27 | 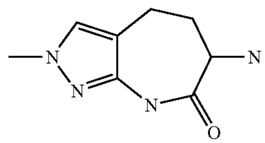 | 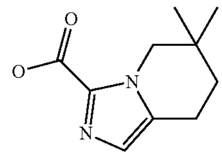 | 27 |
| 28 | 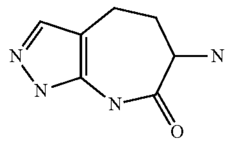 [SMILES: NC1CCc2cn[nH]c2NC1=O] | 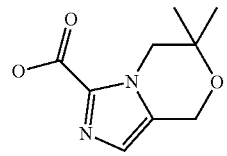 | 28 |
| 29 | 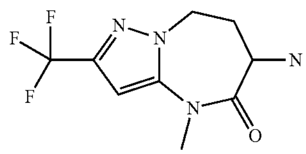 [SMILES: CN1C(=O)C(N)CCn2nc(C(F)(F)F)cc21] | 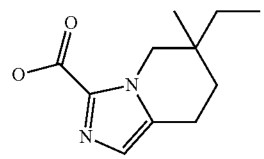 | 29 |
| 30 | 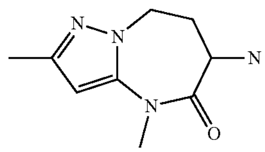 | 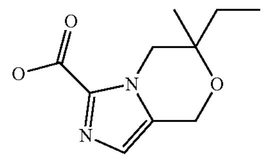 | 30 |
| 31 | 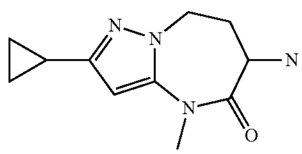 [SMILES: CN1C(=O)C(N)CCn2nc(C3CC3)cc21] | 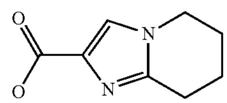 [SMILES: O=C(O)c1cn2c(n1)CCCC2] | 31 |
| 32 | 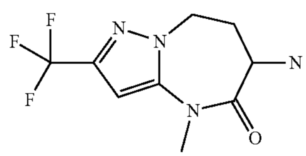 | 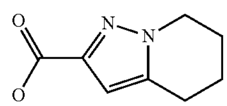 [SMILES: O=C(O)c1cc2n(n1)CCCC2] | 32 |
| 33 | 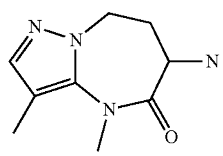 | 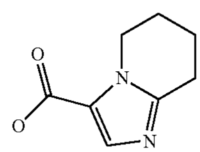 [SMILES: O=C(O)c1cnc2n1CCCC2] | 33 |
| 34 | 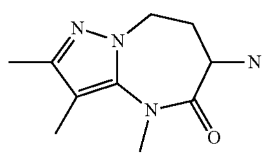 | 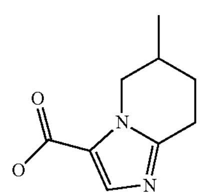 | 34 |

TABLE A-continued
| | LHS Amine | RHS Acid | |
|---|---|---|---|
| 35 | 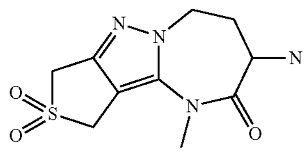 [SMILES: CN1C(=O)C(N)CCn2nc3c(c21)CS(=O)(=O)C3] | 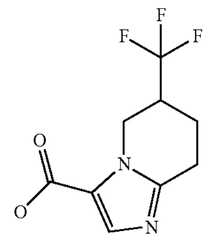 [SMILES: O=C(O)c1cnc2n1CC(C(F)(F)F)CC2] | 35 |
| 36 | 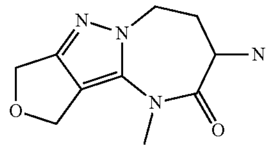 [SMILES: CN1C(=O)C(N)CCn2nc3c(c21)COC3] | 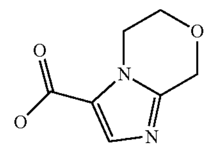 [SMILES: O=C(O)c1cnc2n1CCOC2] | 36 |
| 37 | 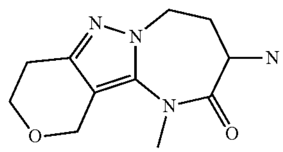 [SMILES: CN1C(=O)C(N)CCn2nc3c(c21)COCC3] | 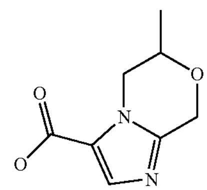 | 37 |
| 38 | 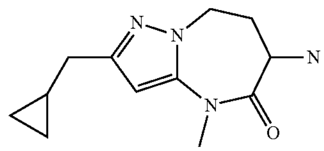 [SMILES: CN1C(=O)C(N)CCn2nc(CC3CC3)cc21] | 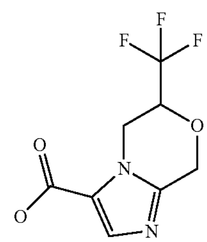 [SMILES: O=C(O)c1cnc2n1CC(C(F)(F)F)OC2] | 38 |
| 39 | 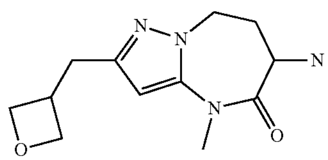 [SMILES: CN1C(=O)C(N)CCn2nc(CC3COC3)cc21] | 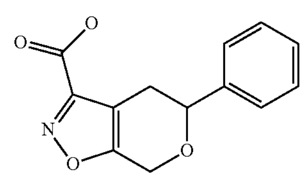 [SMILES: O=C(O)c1noc2c1CC(c1ccccc1)OC2] | 39 |
| 40 | 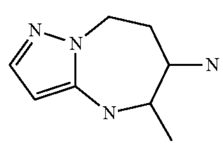 | 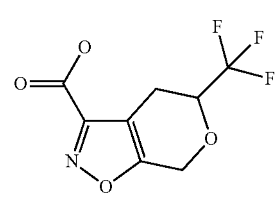 [SMILES: O=C(O)c1noc2c1CC(C(F)(F)F)OC2] | 40 |
| 41 | 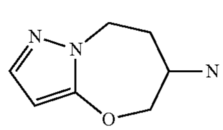 [SMILES: NC1CCn2nccc2OC1] | 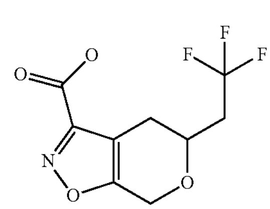 [SMILES: O=C(O)c1noc2c1CC(CC(F)(F)F)OC2] | 41 |
| 42 | 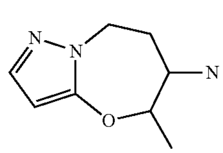 | 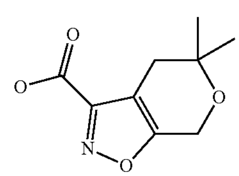 | 42 |

TABLE A-continued
| | LHS Amine | RHS Acid | |
|---|---|---|---|
| 43 | 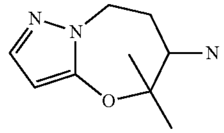 | 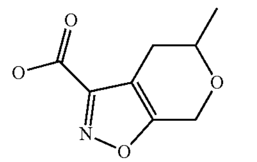 | 43 |
| 44 | 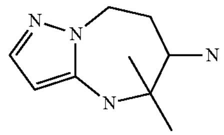 | 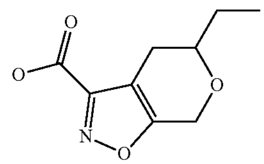 | 44 |
| 45 | 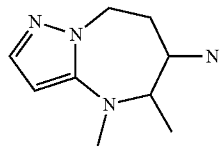 | 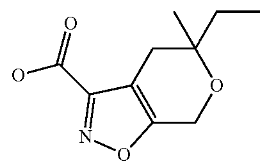 | 45 |
| 46 | 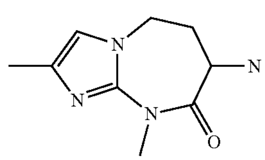 | 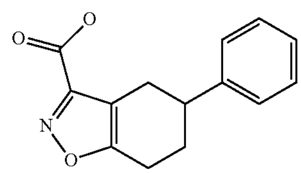 | 46 |
| 47 | 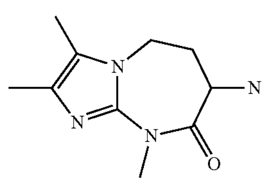 | 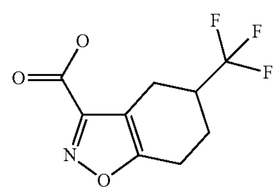 [SMILES: O=C(O)c1noc2c1CC(C(F)(F)F)CC2] | 47 |
| 48 | 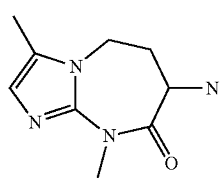 | 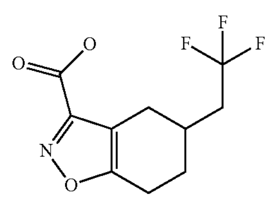 [SMILES: O=C(O)c1noc2c1CC(CC(F)(F)F)CC2] | 48 |
| 49 | 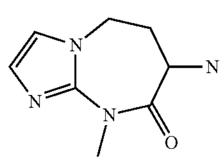 | 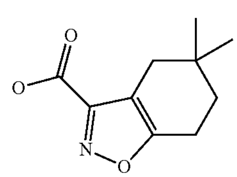 | 49 |
| 50 | 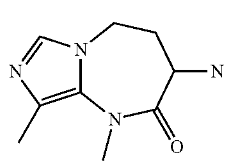 | 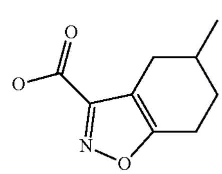 | 50 |
| 51 | 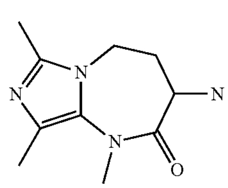 | 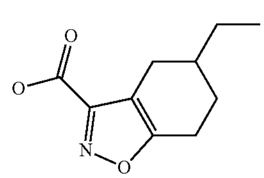 | 51 |

TABLE A-continued
| | LHS Amine | RHS Acid | |
|---|---|---|---|
| 52 | 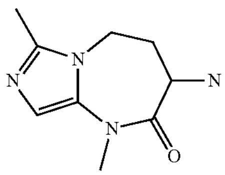 | 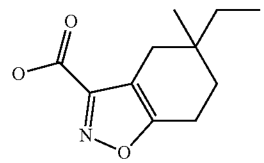 | 52 |
| 53 | 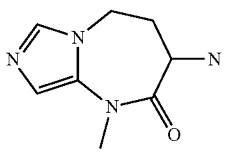 | 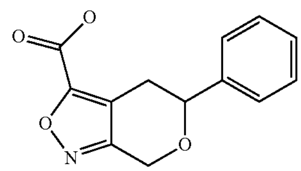 | 53 |
| 54 | 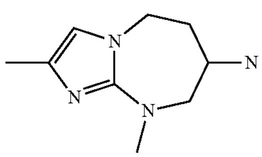 | 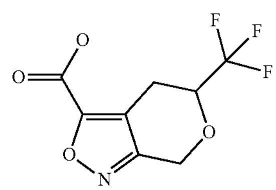 [SMILES: O=C(O)c1onc2c1CC(C(F)(F)F)OC2] | 54 |
| 55 | 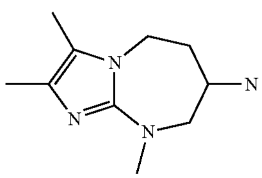 | 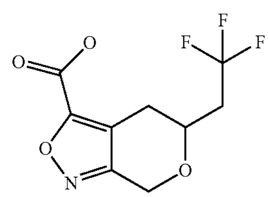 | 55 |
| 56 | 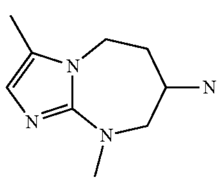 | 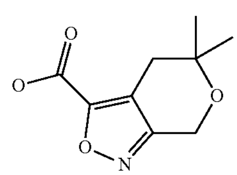 | 56 |
| 57 | 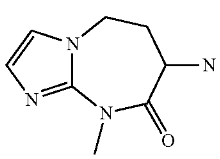 | 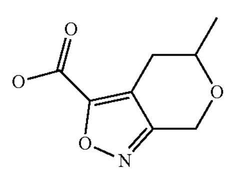 | 57 |
| 58 | 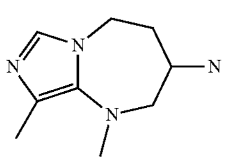 | 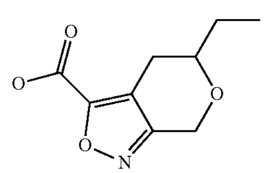 | 58 |
| 59 | 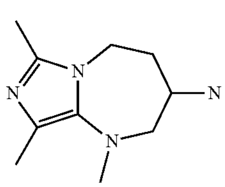 | 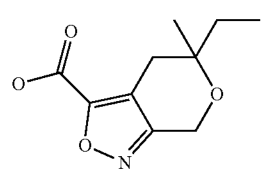 | 59 |

TABLE A-continued
| | LHS Amine | RHS Acid | |
|---|---|---|---|
| 60 | 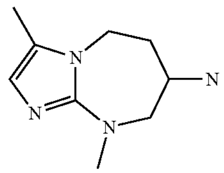 | 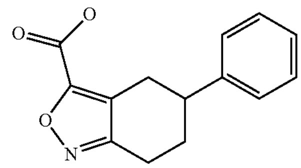 [SMILES: O=C(O)c1onc2c1CC(c1ccccc1)CC2] | 60 |
| 61 | 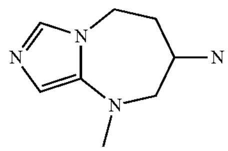 | 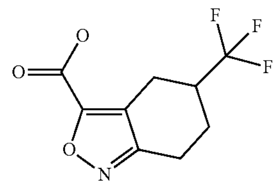 [SMILES: O=C(O)c1onc2c1CC(C(F)(F)F)CC2] | 61 |
| 62 | 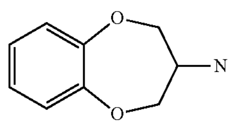 [SMILES: NC1COc2ccccc2OC1] | 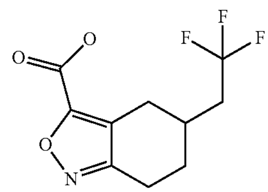 [SMILES: O=C(O)c1onc2c1CC(CC(F)(F)F)CC2] | 62 |
| 63 | 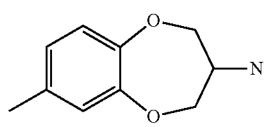 | 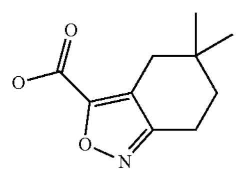 | 63 |
| 64 | 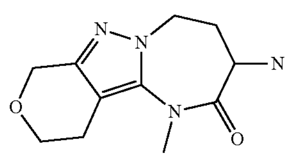 [SMILES: CN1C(=O)C(N)CCn2nc3c(c21)CCOC3] | 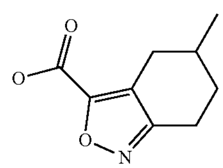 | 64 |
| 65 | 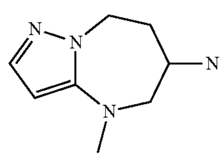 | 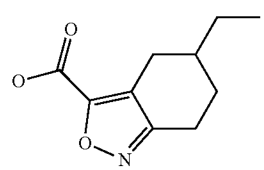 | 65 |
| 66 | 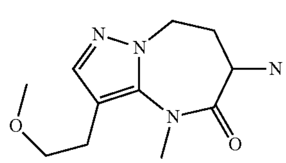 [SMILES: COCCc1cnn2c1N(C)C(=O)C(N)CC2] | 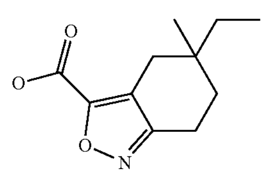 | 66 |
| 67 | 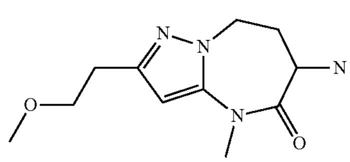 [SMILES: COCCc1cc2n(n1)CCC(N)C(=O)N2C] | 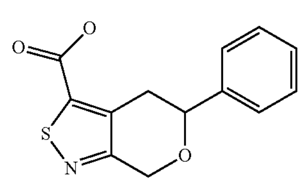 [SMILES: O=C(O)c1snc2c1CC(c1ccccc1)OC2] | 67 |

TABLE A-continued
| | LHS Amine | RHS Acid | |
|---|---|---|---|
| 68 | 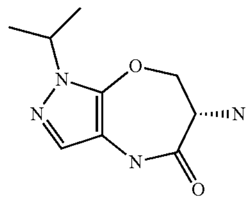 | 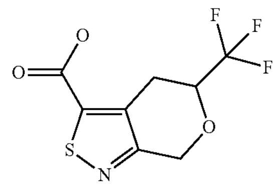 | 68 |
| 69 | 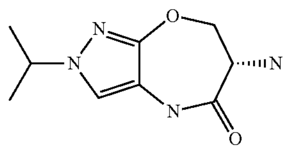 | 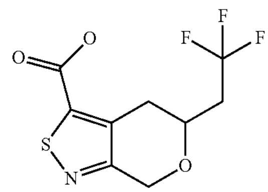 [SMILES: O=C(O)c1snc2c1CC(CC(F)(F)F)OC2] | 69 |
| 70 | 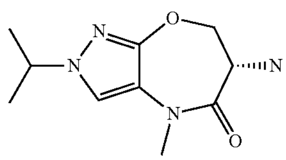 [SMILES: CC(C)n1cc2c(n1)OC[C@H](N)C(=O)N2C] | 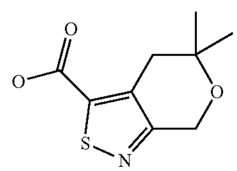 | 70 |
| 71 | 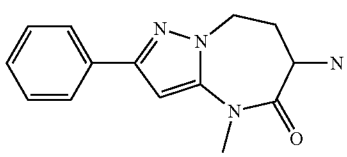 [SMILES: CN1C(=O)C(N)CCn2nc(-c3ccccc3)cc21] | 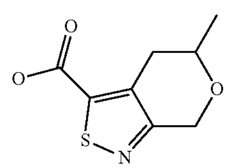 | 71 |
| 72 | 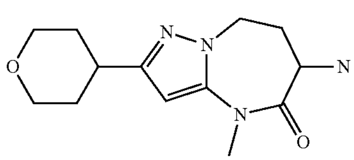 [SMILES: CN1C(=O)C(N)CCn2nc(C3CCOCC3)cc21] | 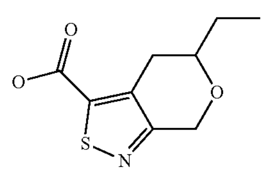 | 72 |
| 73 | 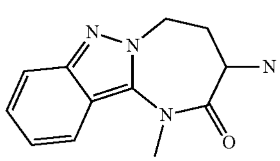 [SMILES: CN1C(=O)C(N)CCn2nc3ccccc3c21] | 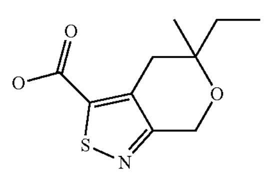 | 73 |
| 74 | 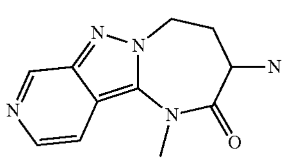 [SMILES: CN1C(=O)C(N)CCn2nc3cnccc3c21] | 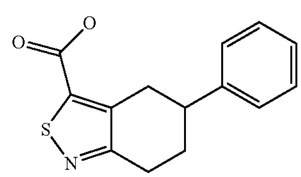 [SMILES: O=C(O)c1snc2c1CC(c1ccccc1)CC2] | 74 |
| 75 | 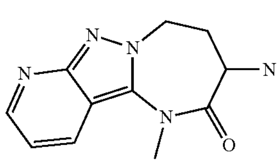 [SMILES: CN1C(=O)C(N)CCn2nc3ncccc3c21] | 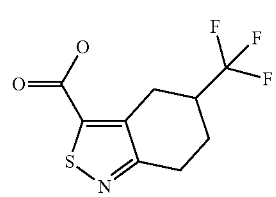 [SMILES: O=C(O)c1snc2c1CC(C(F)(F)F)CC2] | 75 |

TABLE A-continued
| | LHS Amine | RHS Acid | |
|---|---|---|---|
| 76 | 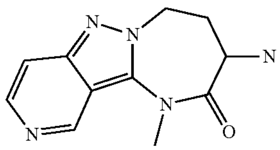 [SMILES: CN1C(=O)C(N)CCn2nc3ccncc3c21] | 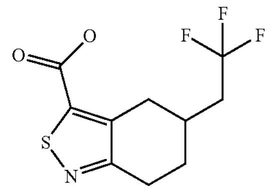 [SMILES: O=C(O)c1snc2c1CC(CC(F)(F)F)CC2] | 76 |
| 77 | 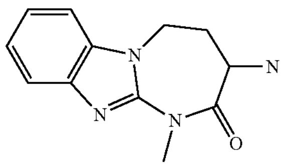 [SMILES: CN1C(=O)C(N)CCn2c1nc1ccccc12] | 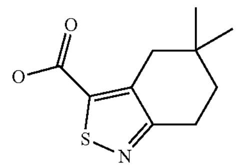 | 77 |
| 78 | 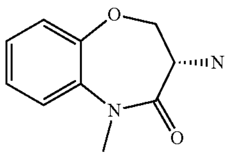 | 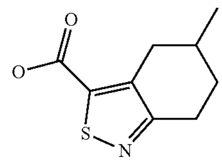 | 78 |
| 79 | 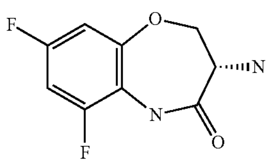 [SMILES: N[C@H]1COc2cc(F)cc(F)c2NC1=O] | 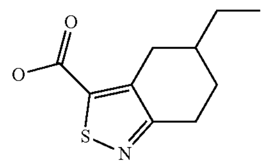 | 79 |
| 80 | 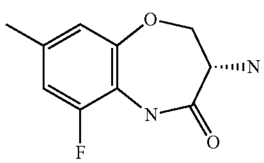 | 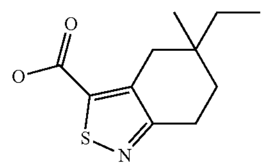 | 80 |
| 81 | 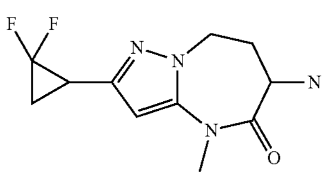 [SMILES: CN1C(=O)C(N)CCn2nc(C3CC3(F)F)cc21] | 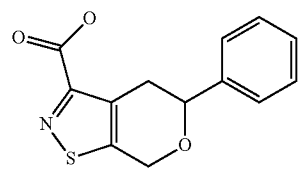 [SMILES: O=C(O)c1nsc2c1CC(c1ccccc1)OC2] | 81 |
| 82 | 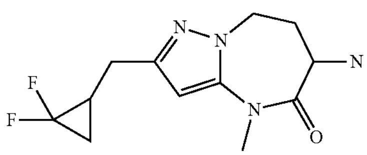 [SMILES: CN1C(=O)C(N)CCn2nc(CC3CC3(F)F)cc21] | 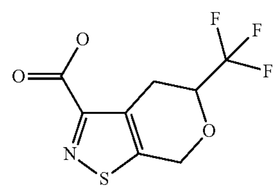 [SMILES: O=C(O)c1nsc2c1CC(C(F)(F)F)OC2] | 82 |
| 83 | 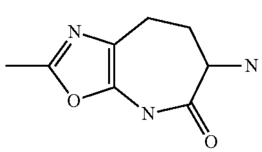 | 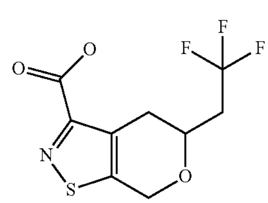 [SMILES: O=C(O)c1nsc2c1CC(CC(F)(F)F)OC2] | 83 |

TABLE A-continued
| | LHS Amine | RHS Acid | |
|---|---|---|---|
| 84 | 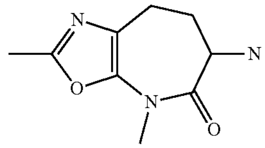 | 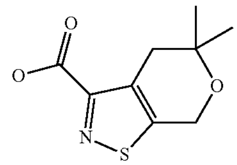 | 84 |
| 85 | 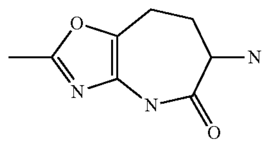 | 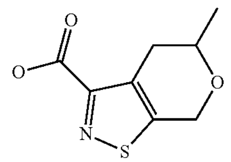 | 85 |
| 86 | 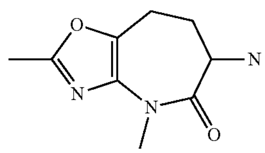 | 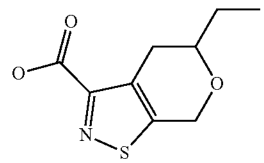 | 86 |
| 87 | 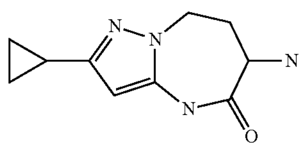 [SMILES: NC1CCn2nc(C3CC3)cc2NC1=O] | 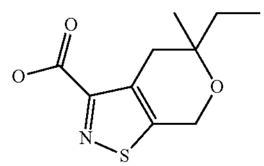 | 87 |
| 88 | 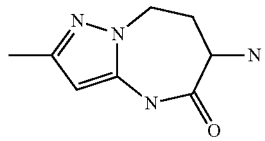 | 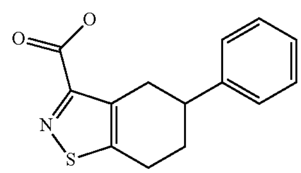 | 88 |
| 89 | 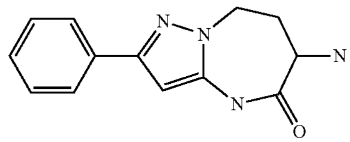 [SMILES: NC1CCn2nc(-c3ccccc3)cc2NC1=O] | 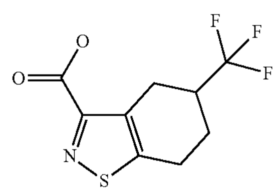 | 89 |
| 90 | 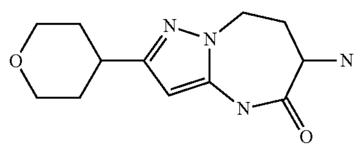 [SMILES: NC1CCn2nc(C3CCOCC3)cc2NC1=O] | 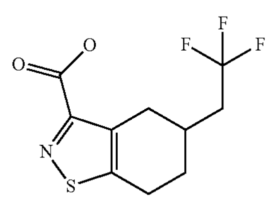 [SMILES: O=C(O)c1nsc2c1CC(CC(F)(F)F)CC2] | 90 |
| 91 | 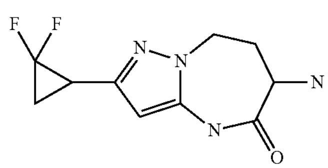 [SMILES: NC1CCn2nc(C3CC3(F)F)cc2NC1=O] | 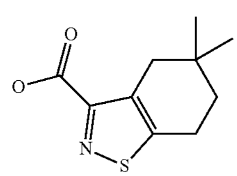 | 91 |
| | | 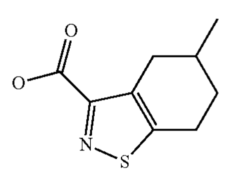 | 92 |

TABLE A-continued
| LHS Amine | RHS Acid | |
|---|---|---|
| | 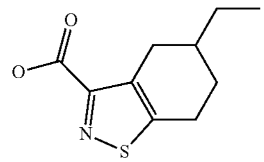 | 93 |
| | 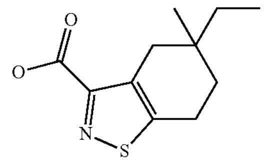 | 94 |
| | 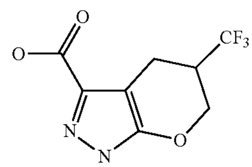 [SMILES: O=C(O)c1n[nH]c2c1CC(C(F)(F)F)CO2] | 95 |
| | 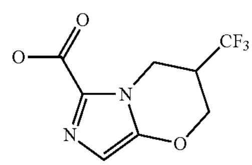 [SMILES: O=C(O)c1ncc2n1CC(C(F)(F)F)CO2] | 96 |
| | 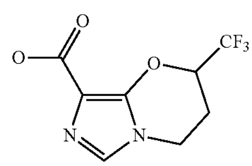 [SMILES: O=C(O)c1ncn2c1OC(C(F)(F)F)CC2] | 97 |
| | 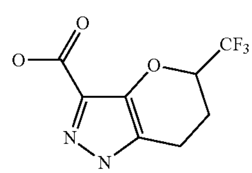 [SMILES: O=C(O)c1n[nH]c2c1OC(C(F)(F)F)CC2] | 98 |
| | 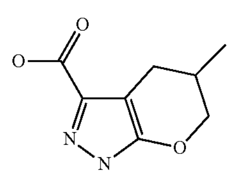 | 99 |
| | 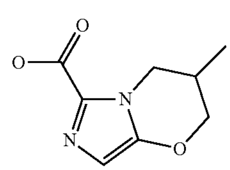 | 100 |
| | 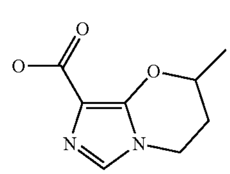 | 101 |

TABLE A-continued
| LHS Amine | RHS Acid | |
|---|---|---|
| | 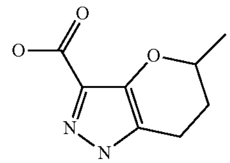 | 102 |
| | 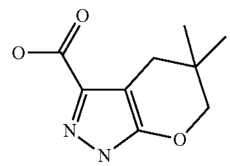 | 103 |
| | 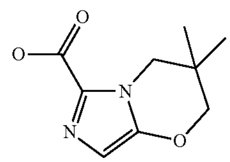 | 104 |
| | 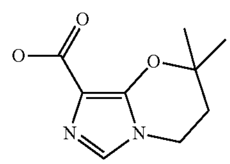 | 105 |
| | 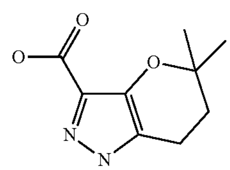 | 106 |
| | 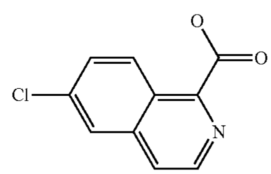 [SMILES: O=C(O)c1nccc2cc(Cl)ccc12] | 107 |
| | 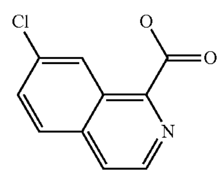 [SMILES: O=C(O)c1nccc2ccc(Cl)cc12] | 108 |
| | 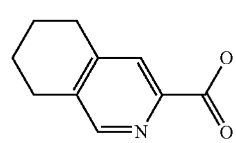 [SMILES: O=C(O)c1cc2c(cn1)CCCC2] | 109 |
| | 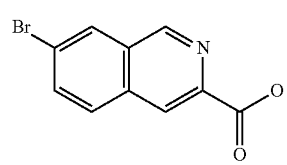 [SMILES: O=C(O)c1cc2ccc(Br)cc2cn1] | 110 |

TABLE A-continued
| LHS Amine | RHS Acid | |
|---|---|---|
| | 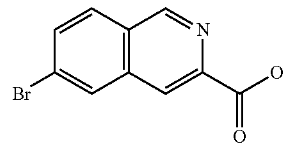 [SMILES: O=C(O)c1cc2cc(Br)ccc2cn1] | 111 |
| | 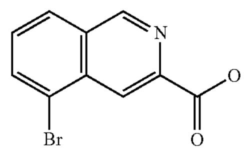 [SMILES: O=C(O)c1cc2c(Br)cccc2cn1] | 112 |
| | 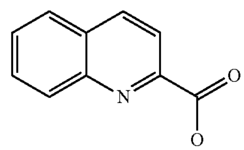 [SMILES: O=C(O)c1ccc2ccccc2n1] | 113 |
| | 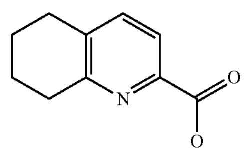 [SMILES: O=C(O)c1ccc2c(n1)CCCC2] | 114 |
| | 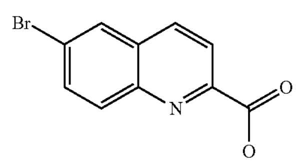 [SMILES: O=C(O)c1ccc2cc(Br)ccc2n1] | 115 |
| | 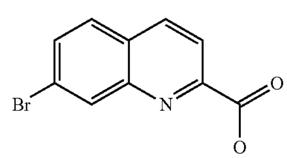 [SMILES: O=C(O)c1ccc2ccc(Br)cc2n1] | 116 |
| | 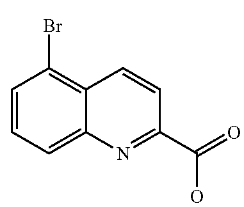 [SMILES: O=C(O)c1ccc2c(Br)cccc2n1] | 117 |
| | 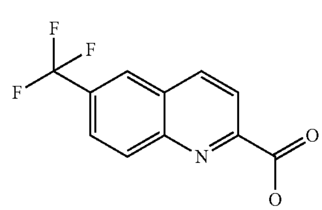 [SMILES: O=C(O)c1ccc2cc(C(F)(F)F)ccc2n1] | 118 |
| | 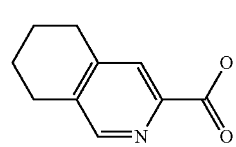 [SMILES: O=C(O)c1cc2c(cn1)CCCC2] | 119 |

TABLE A-continued
| LHS Amine | RHS Acid | |
|---|---|---|
| | 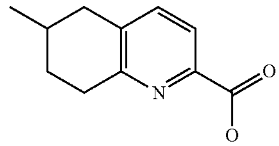 | 120 |
| | 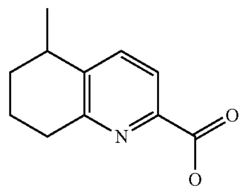 | 121 |
| | 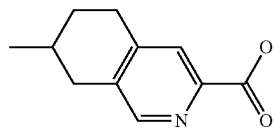 | 122 |
| | 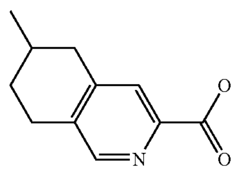 | 123 |
| | 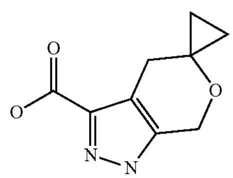 [SMILES: O=C(O)c1n[nH]c2c1CC1(CC1)OC2] | 124 |
| | 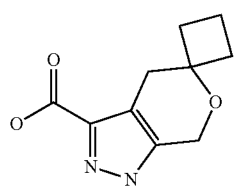 [SMILES: O=C(O)c1n[nH]c2c1CC1(CCC1)OC2] | 125 |
| | 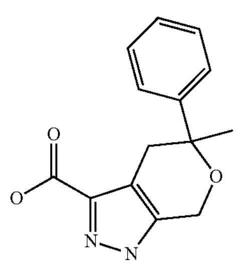 [SMILES: CC1(c2ccccc2)Cc2c(C(=O)O)n[nH]c2CO1] | 126 |
| | 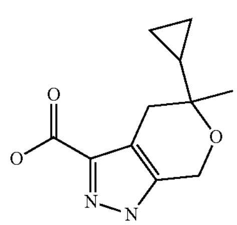 [SMILES: CC1(C2CC2)Cc2c(C(=O)O)n[nH]c2CO1] | 127 |

TABLE A-continued
| LHS Amine | RHS Acid | |
|---|---|---|
| | 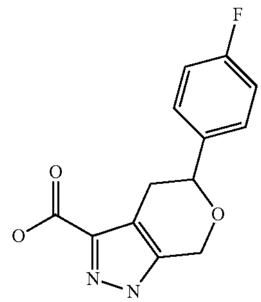 [SMILES: O=C(O)c1n[nH]c2c1CC(c1ccc(F)cc1)OC2] | 128 |
| | 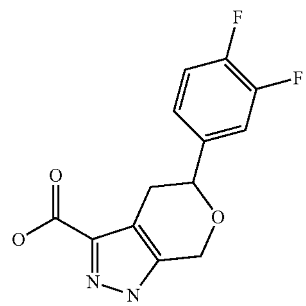 [SMILES: O=C(O)c1n[nH]c2c1CC(c1ccc(F)c(F)c1)OC2] | 129 |
| | 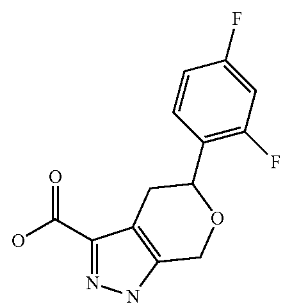 [SMILES: O=C(O)c1n[nH]c2c1CC(c1ccc(F)cc1F)OC2] | 130 |
| | 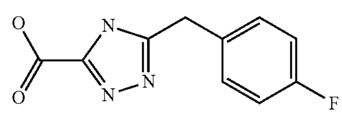 [SMILES: O=C(O)c1nnc(Cc2ccc(F)cc2)[nH]1] | 131 |
| | 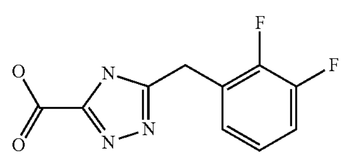 [SMILES: O=C(O)c1nnc(Cc2cccc(F)c2F)[nH]1] | 132 |
| | 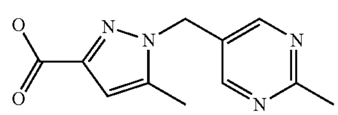 [SMILES: Cc1ncc(Cn2nc(C(=O)O)cc2C)cn1] | 133 |
| | 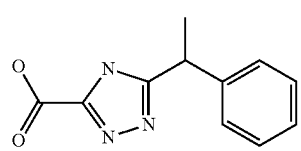 [SMILES: CC(c1ccccc1)c1nnc(C(=O)O)[nH]1] | 134 |
| | 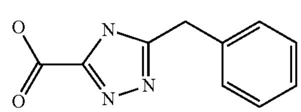 [SMILES: O=C(O)c1nnc(Cc2ccccc2)[nH]1] | 135 |

TABLE A-continued
| LHS Amine | RHS Acid | |
|---|---|---|
| | 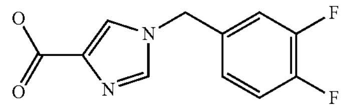 [SMILES: O=C(O)c1cn(Cc2ccc(F)c(F)c2)cn1] | 136 |
| | 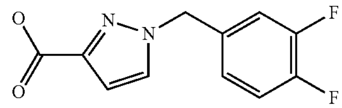 [SMILES: O=C(O)c1ccn(Cc2ccc(F)c(F)c2)n1] | 137 |
| | 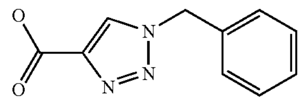 [SMILES: O=C(O)c1cn(Cc2ccccc2)nn1] | 138 |
| | 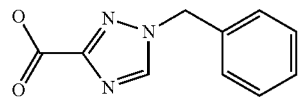 [SMILES: O=C(O)c1ncn(Cc2ccccc2)n1] | 139 |
| | 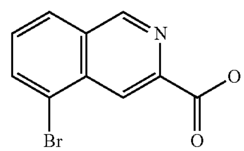 [SMILES: O=C(O)c1cc2c(Br)cccc2cn1] | 140 |
| | 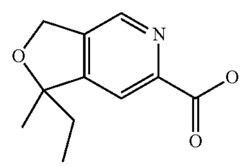 | 141 |
| | 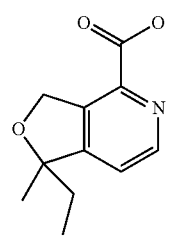 | 142 |
| | 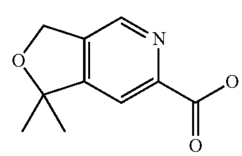 | 143 |
| | 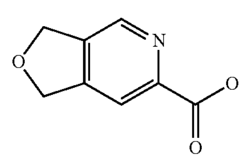 | 144 |
| | 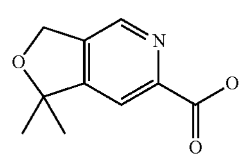 | 145 |

TABLE A-continued
| LHS Amine | RHS Acid | |
|---|---|---|
| | 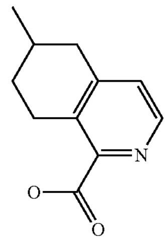 | 146 |
| | 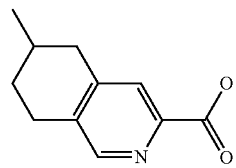 | 147 |
| | 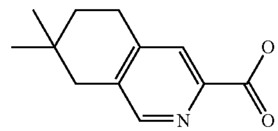 | 148 |
| | 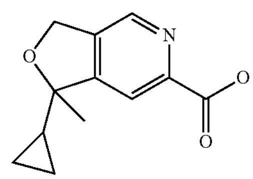 [SMILES: CC1(C2CC2)OCc2cnc(C(=O)O)cc21] | 149 |
| | 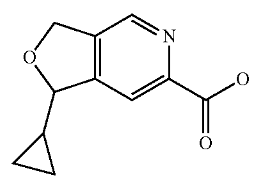 [SMILES: O=C(O)c1cc2c(cn1)COC2C1CC1] | 150 |
| | 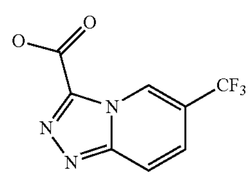 [SMILES: O=C(O)c1nnc2ccc(C(F)(F)F)cn12] | 151 |
| | 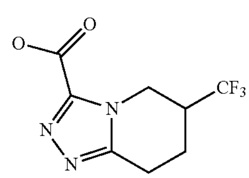 [SMILES: O=C(O)c1nnc2n1CC(C(F)(F)F)CC2] | 152 |
| | 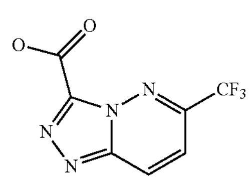 [SMILES: O=C(O)c1nnc2ccc(C(F)(F)F)nn12] | 153 |

TABLE A-continued
| LHS Amine | RHS Acid | |
|---|---|---|
| | 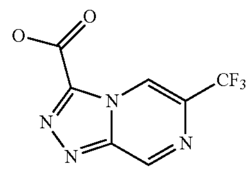 [SMILES: O=C(O)c1nnc2cnc(C(F)(F)F)cn12] | 154 |
| | 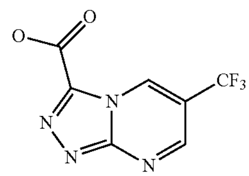 [SMILES: O=C(O)c1nnc2ncc(C(F)(F)F)cn12] | 155 |
| | 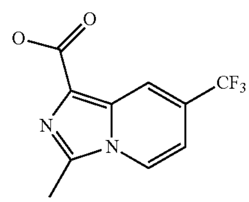 [SMILES: Cc1nc(C(=O)O)c2cc(C(F)(F)F)ccn12] | 156 |
| | 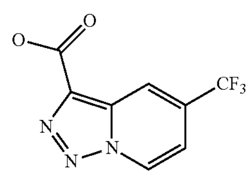 [SMILES: O=C(O)c1nnn2ccc(C(F)(F)F)cc12] | 157 |
| | 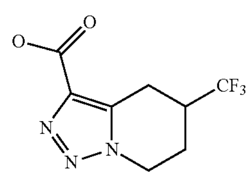 [SMILES: O=C(O)c1nnn2c1CC(C(F)(F)F)CC2] | 158 |
| | 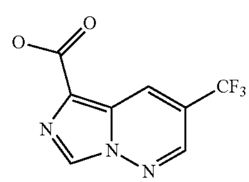 [SMILES: O=C(O)c1ncn2ncc(C(F)(F)F)cc12] | 159 |
| | 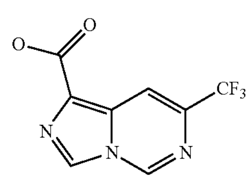 [SMILES: O=C(O)c1ncn2cnc(C(F)(F)F)cc12] | 160 |
| | 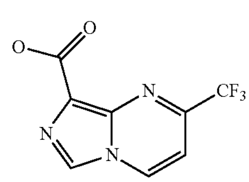 [SMILES: O=C(O)c1ncn2ccc(C(F)(F)F)nc12] | 161 |

TABLE A-continued

| LHS Amine | RHS Acid | |
|---|---|---|
| | 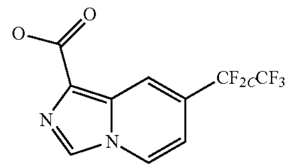 | 162 |
| | 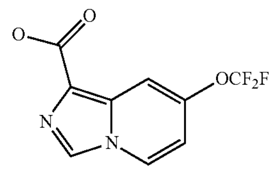 | 163 |
| | 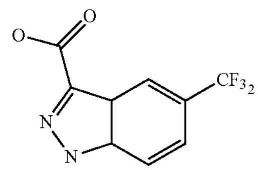 [SMILES: O=C(O)C1=NNC2C=CC(C(F)(F)F)=CC12] | 164 |
| | 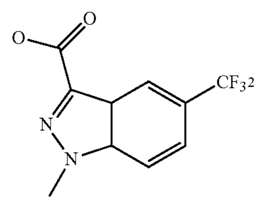 [SMILES: CN1N=C(C(=O)O)C2C=C(C(F)(F)F)C=CC21] | 165 |

In one embodiment, provided herein is a compound of formula I selected from the group consisting of:

5a-methyl-N—((S)-5-methyl-4-oxo-2,3,4,5-tetrahydrobenzo[b][1,4]oxazepin-3-yl)-1,4,4a,5,5a, 6-hexahydrocyclopropa[f]indazole-3-carboxamide;

(S)—N-(5-methyl-4-oxo-2,3,4,5-tetrahydrobenzo[b][1,4]oxazepin-3-yl)-1',4',5',7'-tetrahydrospiro[cyclopropane-1,6'-indazole]-3'-carboxamide;

5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide;

N—((S)-4-oxo-2,3,4,5-tetrahydrobenzo[b][1,4]oxazepin-3-yl)-1,4,4a,5,5a,6-hexahydrocyclopropa[f]indazole-3-carboxamide;

(S)—N-(5-methyl-4-oxo-2,3,4,5-tetrahydrobenzo[b][1,4]oxazepin-3-yl)-5-(2,2,2-trifluoroethyl)-4,5,6,7-tetrahydro-1H-pyrazolo[4,3-c]pyridine-3-carboxamide;

N-[(3S)-5-methyl-4-oxo-2,3-dihydro-1,5-benzoxazepin-3-yl]-5-phenyl-4,6,7,8-tetrahydropyrazolo[1,5-a][1,4]diazepine-2-carboxamide;

5-methyl-N—((S)-5-methyl-4-oxo-2,3-dihydro-1,5-benzoxazepin-3-yl)-1,4,5,7-tetrahydropyrano[3,4-c]pyrazole-3-carboxamide;

5,5-dimethyl-N-[(3S)-5-methyl-4-oxo-2,3-dihydro-1,5-benzoxazepin-3-yl]-4,7-dihydro-1H-pyrano[3,4-c]pyrazole-3-carboxamide;

N—((S)-5-methyl-4-oxo-2,3-dihydro-1,5-benzoxazepin-3-yl)-5-phenyl-1,4,5,7-tetrahydropyrano[3,4-c]pyrazole-3-carboxamide;

6-methyl-N—((S)-5-methyl-4-oxo-2,3-dihydro-1,5-benzoxazepin-3-yl)-6,8-dihydro-5H-imidazo[5,1-c][1,4]oxazine-3-carboxamide;

6-methyl-N—((S)-5-methyl-4-oxo-2,3-dihydro-1,5-benzoxazepin-3-yl)-5,6,7,8-tetrahydroimidazo[1,5-a]pyridine-3-carboxamide;

(R)-1-methyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)-1-methyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)-2-methyl-N—((S)-5-methyl-4-oxo-2,3,4,5-tetrahydrobenzo[b][1,4]oxazepin-3-yl)-5-(trifluoromethyl)-4,5,6,7-tetrahydro-2H-indazole-3-carboxamide;

5,5-dimethyl-N-[(3S)-5-methyl-4-oxo-2,3-dihydro-1,5-benzoxazepin-3-yl]-1,4,6,7-tetrahydroindazole-3-carboxamide;

5-methyl-N—((S)-5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide;

6-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide;

N—((S)-5-methyl-4-oxo-2,3,4,5-tetrahydrobenzo[b][1,4]oxazepin-3-yl)-5-(1H-pyrazol-1-yl)-4,5,6,7-tetrahydro-1H-indazole-3-carboxamide;

1-ethyl-1-methyl-N—((S)-5-methyl-4-oxo-2,3,4,5-tetrahydrobenzo[b][1,4]oxazepin-3-yl)-1,3-dihydrofuro[3,4-c]pyridine-4-carboxamide;

1-ethyl-1-methyl-N—((S)-5-methyl-4-oxo-2,3,4,5-tetrahydrobenzo[b][1,4]oxazepin-3-yl)-1,3-dihydrofuro[3,4-c]pyridine-6-carboxamide;

(S)-1,1-dimethyl-N-(5-methyl-4-oxo-2,3,4,5-tetrahydrobenzo[b][1,4]oxazepin-3-yl)-1,3-dihydrofuro[3,4-c]pyridine-6-carboxamide;

(S)—N-(5-methyl-4-oxo-2,3,4,5-tetrahydrobenzo[b][1,4]oxazepin-3-yl)-5,6,7,8-tetrahydroisoquinoline-3-carboxamide;

N—((S)-5-methyl-4-oxo-2,3,4,5-tetrahydrobenzo[b][1,4]oxazepin-3-yl)-5-phenyl-4,5,6,7-tetrahydro-1H-indazole-3-carboxamide;

(S)-5,5-dimethyl-N-(5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide;

(S)-6,6-dimethyl-N-(5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide;

5-benzyl-N-(4-methyl-5-oxo-5,6,7,8-tetrahydro-4H-pyrazolo[1,5-a][1,3]diazepin-6-yl)-4H-1,2,4-triazole-3-carboxamide;

(S)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide;

5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide;

5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide;

5-benzyl-N-(4-methyl-5-oxo-2-(trifluoromethyl)-5,6,7,8-tetrahydro-4H-pyrazolo[1,5-a][1,3]diazepin-6-yl)-4H-1,2,4-triazole-3-carboxamide;

5-benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide;

(S)—N-(5-methyl-4-oxo-2,3,4,5-tetrahydrobenzo[b][1,4]oxazepin-3-yl)-4,5,6,7-tetrahydro-1H-indazole-3-carboxamide;

(S)—N-(5-methyl-4-oxo-2,3,4,5-tetrahydrobenzo[b][1,4]oxazepin-3-yl)-1H-indazole-3-carboxamide;

N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(R)—N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)—N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)—N-(5-methyl-4-oxo-2,3,4,5-tetrahydrobenzo[b][1,4]oxazepin-3-yl)-6-(trifluoromethyl)imidazo[1,5-a]pyridine-3-carboxamide;

N—((S)-5-methyl-4-oxo-2,3,4,5-tetrahydrobenzo[b][1,4]oxazepin-3-yl)-6-(trifluoromethyl)-5,6,7,8-tetrahydroimidazo[1,5-a]pyridine-3-carboxamide;

(S)—N-(5-methyl-4-oxo-2,3,4,5-tetrahydrobenzo[b][1,4]oxazepin-3-yl)-7-(trifluoromethyl)imidazo[1,5-a]pyridine-1-carboxamide;

N—((S)-5-methyl-4-oxo-2,3,4,5-tetrahydrobenzo[b][1,4]oxazepin-3-yl)-7-(trifluoromethyl)-5,6,7,8-tetrahydroimidazo[1,5-a]pyridine-1-carboxamide;

(S)—N—((S)-4-methyl-5-oxo-5,6,7,8-tetrahydro-4H-pyrazolo[1,5-a][1,3]diazepin-6-yl)-5-(trifluoromethyl)-4,5,6,7-tetrahydro-1H-indazole-3-carboxamide;

(R)—N—((S)-4-methyl-5-oxo-5,6,7,8-tetrahydro-4H-pyrazolo[1,5-a][1,3]diazepin-6-yl)-5-(trifluoromethyl)-4,5,6,7-tetrahydro-1H-indazole-3-carboxamide;

(S)—N-(5-methyl-4-oxo-2,3,4,5-tetrahydrobenzo[b][1,4]oxazepin-3-yl)-1,4,5,6,7,8-hexahydrocyclohepta[c]pyrazole-3-carboxamide;

5-methyl-N—((S)-5-methyl-4-oxo-2,3,4,5-tetrahydrobenzo[b][1,4]oxazepin-3-yl)-4,5,6,7-tetrahydro-2H-indazole-3-carboxamide;

N—((S)-7-chloro-2-oxo-2,3,4,5-tetrahydro-1H-benzo[b]azepin-3-yl)-5-methyl-4,5,6,7-tetrahydro-2H-indazole-3-carboxamide;

5-(tert-butyl)-N—((S)-7-chloro-2-oxo-2,3,4,5-tetrahydro-1H-benzo[b]azepin-3-yl)-4,5,6,7-tetrahydro-1H-indazole-3-carboxamide;

(S)—N-(5-methyl-4-oxo-2,3,4,5-tetrahydrobenzo[b][1,4]oxazepin-3-yl)-1,4,5,6-tetrahydrocyclopenta[c]pyrazole-3-carboxamide;

(S)—N-(7-chloro-2-oxo-2,3,4,5-tetrahydro-1H-benzo[b]azepin-3-yl)-1,4,5,6-tetrahydrocyclopenta[c]pyrazole-3-carboxamide;

N—((S)-7-chloro-2-oxo-2,3,4,5-tetrahydro-1H-benzo[b]azepin-3-yl)-5a-methyl-1,4,4a,5,5a,6-hexahydrocyclopropa[f]indazole-3-carboxamide;

(S)—N-(5-methyl-4-oxo-2,3,4,5-tetrahydrobenzo[b][1,4]oxazepin-3-yl)-5,6,7,8-tetrahydroquinoline-2-carboxamide;

(S)-6-chloro-N-(5-methyl-4-oxo-2,3,4,5-tetrahydrobenzo[b][1,4]oxazepin-3-yl)-[1,2,4]triazolo[4,3-b]pyridazine-3-carboxamide;

(S)—N-(7-chloro-2-oxo-2,3,4,5-tetrahydro-1H-benzo[b]azepin-3-yl)-6,6-dimethyl-4,5,6,7-tetrahydro-1H-indazole-3-carboxamide;

N—((S)-4-oxo-2,3,4,5-tetrahydrobenzo[b][1,4]oxazepin-3-yl)-3,4,5,5a,6,6a-hexahydrocyclopropa[e]indazole-1-carboxamide;

(S)-5-methyl-N—((S)-5-methyl-4-oxo-2,3,4,5-tetrahydrobenzo[b][1,4]oxazepin-3-yl)-4,5,6,7-tetrahydro-1H-indazole-3-carboxamide;

N—((S)-5-methyl-4-oxo-2,3,4,5-tetrahydrobenzo[b][1,4]oxazepin-3-yl)-1,4,4a,5,5a,6-hexahydrocyclopropa[f]indazole-3-carboxamide;

5-methyl-N—((S)-4-oxo-2,3,4,5-tetrahydrobenzo[b][1,4]oxazepin-3-yl)-4,5,6,7-tetrahydro-1H-indazole-3-carboxamide;

(S)-5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide;

N—((S)-5-methyl-4-oxo-2,3,4,5-tetrahydrobenzo[b][1,4]oxazepin-3-yl)-3,4,5,5a,6,6a-hexahydrocyclopropa[e]indazole-1-carboxamide;

(R)-5-methyl-N—((S)-5-methyl-4-oxo-2,3,4,5-tetrahydrobenzo[b][1,4]oxazepin-3-yl)-4,5,6,7-tetrahydro-1H-indazole-3-carboxamide;

(R)-5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide;

5-methyl-N—((S)-4-oxo-2,3,4,5-tetrahydrobenzo[b][1,4]oxazepin-3-yl)-4,5,6,7-tetrahydrobenzo[c]isoxazole-3-carboxamide;

5-methyl-N—((S)-4-oxo-2,3,4,5-tetrahydrobenzo[b][1,4]oxazepin-3-yl)-4,5,6,7-tetrahydrobenzo[d]isoxazole-3-carboxamide;

5-(tert-butyl)-N—((S)-5-methyl-4-oxo-2,3,4,5-tetrahydrobenzo[b][1,4]oxazepin-3-yl)-4,5,6,7-tetrahydrobenzo[d]isoxazole-3-carboxamide;

5-(tert-butyl)-N—((S)-4-oxo-2,3,4,5-tetrahydrobenzo[b][1,4]oxazepin-3-yl)-4,5,6,7-tetrahydrobenzo[d]isoxazole-3-carboxamide;

5-methyl-N—((S)-5-methyl-4-oxo-2,3,4,5-tetrahydrobenzo[b][1,4]oxazepin-3-yl)-4,5,6,7-tetrahydrobenzo[c]isoxazole-3-carboxamide;

5-methyl-N—((S)-5-methyl-4-oxo-2,3,4,5-tetrahydrobenzo[b][1,4]oxazepin-3-yl)-4,5,6,7-tetrahydrobenzo[d]isoxazole-3-carboxamide;

(S)-5-methyl-N—((S)-5-methyl-4-oxo-2,3,4,5-tetrahydrobenzo[b][1,4]oxazepin-3-yl)-4,5,6,7-tetrahydrobenzo[d]isoxazole-3-carboxamide;

(S)-5-methyl-N—((S)-5-methyl-4-oxo-2,3,4,5-tetrahydrobenzo[b][1,4]oxazepin-3-yl)-4,5,6,7-tetrahydrobenzo[c]isoxazole-3-carboxamide;

(R)-5-methyl-N—((S)-5-methyl-4-oxo-2,3,4,5-tetrahydrobenzo[b][1,4]oxazepin-3-yl)-4,5,6,7-tetrahydrobenzo[d]isoxazole-3-carboxamide;

(R)-5-methyl-N—((S)-5-methyl-4-oxo-2,3,4,5-tetrahydrobenzo[b][1,4]oxazepin-3-yl)-4,5,6,7-tetrahydrobenzo[c]isoxazole-3-carboxamide:

1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide;

5-ethyl-N—((S)-5-methyl-4-oxo-2,3,4,5-tetrahydrobenzo[b][1,4]oxazepin-3-yl)-4,5,6,7-tetrahydro-2H-indazole-3-carboxamide;

(S)—N-(4-methyl-5-oxo-5,6,7,8-tetrahydro-4H-pyrazolo[1,5-a][1,3]diazepin-6-yl)-7-(trifluoromethyl) imidazo[1,5-a]pyridine-1-carboxamide;

N-(2,4-dimethyl-5-oxo-5,6,7,8-tetrahydro-4H-pyrazolo[1,5-a][1,3]diazepin-6-yl)-7-(trifluoromethyl) imidazo[1,5-a]pyridine-1-carboxamide;

(S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide;

(S)-5-chloro-N-(5-methyl-4-oxo-2,3,4,5-tetrahydrobenzo[b][1,4]oxazepin-3-yl)-1H-indazole-3-carboxamide;

(S)-5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide;

(S)-5-benzyl-N-(4-methyl-5-oxo-2-(trifluoromethyl)-5,6,7,8-tetrahydro-4H-pyrazolo[1,5-a][1,3]diazepin-6-yl)-4H-1,2,4-triazole-3-carboxamide;

(S)—N-(5-methyl-4-oxo-2,3,4,5-tetrahydrobenzo[b][1,4]oxazepin-3-yl)-6-(trifluoromethyl)-[1,2,4]triazolo[4,3-b]pyridazine-3-carboxamide; and (S)—N-(5-methyl-4-oxo-2,3,4,5-tetrahydrobenzo[b][1,4]oxazepin-3-yl)-6-(trifluoromethyl)-[1,2,4]triazolo[4,3-a]pyridine-3-carboxamide.

In one embodiment, provided herein is a compound of formula I selected from the group consisting of:

5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide;

N-[(3S)-5-methyl-4-oxo-2,3-dihydro-1,5-benzoxazepin-3-yl]-5-phenyl-4,6,7,8-tetrahydropyrazolo[1,5-a][1,4]diazepine-2-carboxamide;

5,5-dimethyl-N-[(3S)-5-methyl-4-oxo-2,3-dihydro-1,5-benzoxazepin-3-yl]-4,7-dihydro-1H-pyrano[3,4-c]pyrazole-3-carboxamide;

N—((S)-5-methyl-4-oxo-2,3-dihydro-1,5-benzoxazepin-3-yl)-5-phenyl-1,4,5,7-tetrahydropyrano[3,4-c]pyrazole-3-carboxamide;

6-methyl-N—((S)-5-methyl-4-oxo-2,3-dihydro-1,5-benzoxazepin-3-yl)-5,6,7,8-tetrahydroimidazo[1,5-a]pyridine-3-carboxamide;

(R)-1-methyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)-1-methyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

5,5-dimethyl-N-[(3S)-5-methyl-4-oxo-2,3-dihydro-1,5-benzoxazepin-3-yl]-1,4,6,7-tetrahydroindazole-3-carboxamide;

N—((S)-5-methyl-4-oxo-2,3,4,5-tetrahydrobenzo[b][1,4]oxazepin-3-yl)-5-(1H-pyrazol-1-yl)-4,5,6,7-tetrahydro-1H-indazole-3-carboxamide;

1-ethyl-1-methyl-N—((S)-5-methyl-4-oxo-2,3,4,5-tetrahydrobenzo[b][1,4]oxazepin-3-yl)-1,3-dihydrofuro[3,4-c]pyridine-6-carboxamide;

(S)-1,1-dimethyl-N-(5-methyl-4-oxo-2,3,4,5-tetrahydrobenzo[b][1,4]oxazepin-3-yl)-1,3-dihydrofuro[3,4-c]pyridine-6-carboxamide;

N—((S)-5-methyl-4-oxo-2,3,4,5-tetrahydrobenzo[b][1,4]oxazepin-3-yl)-5-phenyl-4,5,6,7-tetrahydro-1H-indazole-3-carboxamide;

5-benzyl-N-(4-methyl-5-oxo-5,6,7,8-tetrahydro-4H-pyrazolo[1,5-a][1,3]diazepin-6-yl)-4H-1,2,4-triazole-3-carboxamide;

(S)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide;

5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide;

5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide;

5-benzyl-N-(4-methyl-5-oxo-2-(trifluoromethyl)-5,6,7,8-tetrahydro-4H-pyrazolo[1,5-a][1,3]diazepin-6-yl)-4H-1,2,4-triazole-3-carboxamide;

5-benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide;

N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(R)—N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)—N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)—N-(5-methyl-4-oxo-2,3,4,5-tetrahydrobenzo[b][1,4]oxazepin-3-yl)-6-(trifluoromethyl)imidazo[1,5-a]pyridine-3-carboxamide;

N—((S)-5-methyl-4-oxo-2,3,4,5-tetrahydrobenzo[b][1,4]oxazepin-3-yl)-6-(trifluoromethyl)-5,6,7,8-tetrahydroimidazo[1,5-a]pyridine-3-carboxamide;

(S)—N-(5-methyl-4-oxo-2,3,4,5-tetrahydrobenzo[b][1,4]oxazepin-3-yl)-7-(trifluoromethyl)imidazo[1,5-a]pyridine-1-carboxamide;

N—((S)-5-methyl-4-oxo-2,3,4,5-tetrahydrobenzo[b][1,4]oxazepin-3-yl)-7-(trifluoromethyl)-5,6,7,8-tetrahydroimidazo[1,5-a]pyridine-1-carboxamide;

(R)—N—((S)-4-methyl-5-oxo-5,6,7,8-tetrahydro-4H-pyrazolo[1,5-a][1,3]diazepin-6-yl)-5-(trifluoromethyl)-4,5,6,7-tetrahydro-1H-indazole-3-carboxamide;

5-methyl-N—((S)-5-methyl-4-oxo-2,3,4,5-tetrahydrobenzo[b][1,4]oxazepin-3-yl)-4,5,6,7-tetra hydro-2H-indazole-3-carboxamide;

N—((S)-7-chloro-2-oxo-2,3,4,5-tetrahydro-1H-benzo[b]azepin-3-yl)-5-methyl-4,5,6,7-tetrahydro-2H-indazole-3-carboxamide;

5-(tert-butyl)-N—((S)-7-chloro-2-oxo-2,3,4,5-tetrahydro-1H-benzo[b]azepin-3-yl)-4,5,6,7-tetra hydro-1H-indazole-3-carboxamide;

(S)-5-methyl-N—((S)-5-methyl-4-oxo-2,3,4,5-tetrahydrobenzo[b][1,4]oxazepin-3-yl)-4,5,6,7-tetrahydro-1H-indazole-3-carboxamide;

N—((S)-5-methyl-4-oxo-2,3,4,5-tetrahydrobenzo[b][1,4]oxazepin-3-yl)-1,4,4a,5,5a,6-hexahydrocyclopropa[f]indazole-3-carboxamide;

5-methyl-N—((S)-4-oxo-2,3,4,5-tetrahydrobenzo[b][1,4]oxazepin-3-yl)-4,5,6,7-tetrahydro-1H-indazole-3-carboxamide;

(S)-5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide;

(R)-5-methyl-N—((S)-5-methyl-4-oxo-2,3,4,5-tetrahydrobenzo[b][1,4]oxazepin-3-yl)-4,5,6,7-tetrahydro-1H-indazole-3-carboxamide;

(R)-5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide;

5-methyl-N—((S)-4-oxo-2,3,4,5-tetrahydrobenzo[b][1,4]oxazepin-3-yl)-4,5,6,7-tetrahydrobenzo[c]isoxazole-3-carboxamide;

5-methyl-N—((S)-4-oxo-2,3,4,5-tetrahydrobenzo[b][1,4]oxazepin-3-yl)-4,5,6,7-tetrahydrobenzo[d]isoxazole-3-carboxamide;

5-(tert-butyl)-N—((S)-5-methyl-4-oxo-2,3,4,5-tetrahydrobenzo[b][1,4]oxazepin-3-yl)-4,5,6,7-tetrahydrobenzo[d]isoxazole-3-carboxamide;

5-(tert-butyl)-N—((S)-4-oxo-2,3,4,5-tetrahydrobenzo[b][1,4]oxazepin-3-yl)-4,5,6,7-tetrahydrobenzo[d]isoxazole-3-carboxamide;

5-methyl-N—((S)-5-methyl-4-oxo-2,3,4,5-tetrahydrobenzo[b][1,4]oxazepin-3-yl)-4,5,6,7-tetrahydrobenzo[c]isoxazole-3-carboxamide;

5-methyl-N—((S)-5-methyl-4-oxo-2,3,4,5-tetrahydrobenzo[b][1,4]oxazepin-3-yl)-4,5,6,7-tetrahydrobenzo[d]isoxazole-3-carboxamide;

(S)-5-methyl-N—((S)-5-methyl-4-oxo-2,3,4,5-tetrahydrobenzo[b][1,4]oxazepin-3-yl)-4,5,6,7-tetrahydrobenzo[d]isoxazole-3-carboxamide;

(S)-5-methyl-N—((S)-5-methyl-4-oxo-2,3,4,5-tetrahydrobenzo[b][1,4]oxazepin-3-yl)-4,5,6,7-tetrahydrobenzo[c]isoxazole-3-carboxamide;

(R)-5-methyl-N—((S)-5-methyl-4-oxo-2,3,4,5-tetrahydrobenzo[b][1,4]oxazepin-3-yl)-4,5,6,7-tetrahydrobenzo[d]isoxazole-3-carboxamide;

(R)-5-methyl-N—((S)-5-methyl-4-oxo-2,3,4,5-tetrahydrobenzo[b][1,4]oxazepin-3-yl)-4,5,6,7-tetrahydrobenzo[c]isoxazole-3-carboxamide;

1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide;

5-ethyl-N—((S)-5-methyl-4-oxo-2,3,4,5-tetrahydrobenzo[b][1,4]oxazepin-3-yl)-4,5,6,7-tetrahydro-2H-indazole-3-carboxamide;

(S)—N-(4-methyl-5-oxo-5,6,7,8-tetrahydro-4H-pyrazolo[1,5-a][1,3]diazepin-6-yl)-7-(trifluoromethyl) imidazo[1,5-a]pyridine-1-carboxamide;

N-(2,4-dimethyl-5-oxo-5,6,7,8-tetrahydro-4H-pyrazolo[1,5-a][1,3]diazepin-6-yl)-7-(trifluoromethyl) imidazo[1,5-a]pyridine-1-carboxamide;

(S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide;

(S)-5-chloro-N-(5-methyl-4-oxo-2,3,4,5-tetrahydrobenzo[b][1,4]oxazepin-3-yl)-1H-indazole-3-carboxamide;

(S)-5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide;

(S)-5-benzyl-N-(4-methyl-5-oxo-2-(trifluoromethyl)-5,6,7,8-tetrahydro-4H-pyrazolo[1,5-a][1,3]diazepin-6-yl)-4H-1,2,4-triazole-3-carboxamide;

(S)—N-(5-methyl-4-oxo-2,3,4,5-tetrahydrobenzo[b][1,4]oxazepin-3-yl)-6-(trifluoromethyl)-[1,2,4]triazolo[4,3-b]pyridazine-3-carboxamide; and (S)—N-(5-methyl-4-oxo-2,3,4,5-tetrahydrobenzo[b][1,4]oxazepin-3-yl)-6-(trifluoromethyl)-[1,2,4]triazolo[4,3-a]pyridine-3-carboxamide.

In another embodiment, provided herein is a compound selected from the compounds of Tables 1, 2, 3, 4 and 5 below. In one embodiment, the compound is a compound of Table 1. In another embodiment, the compound is a compound of Table 2.

In one embodiment, provided herein is a compound selected from the group consisting of:

(S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide;

5-ethyl-N—((S)-5-methyl-4-oxo-2,3,4,5-tetrahydrobenzo[b][1,4]oxazepin-3-yl)-4,5,6,7-tetrahydro-2H-indazole-3-carboxamide;

(S)-5-chloro-N-(5-methyl-4-oxo-2,3,4,5-tetrahydrobenzo[b][1,4]oxazepin-3-yl)-1H-indazole-3-carboxamide;

(S)-5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide;

(S)-5-benzyl-N-(4-methyl-5-oxo-2-(trifluoromethyl)-5,6,7,8-tetrahydro-4H-pyrazolo[1,5-a][1,3]diazepin-6-yl)-4H-1,2,4-triazole-3-carboxamide;

(S)—N—((S)-6,8-difluoro-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)—N—((S)-6-fluoro-8-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(R)—N—((S)-6-fluoro-8-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide;

(S)-5-methyl-N-(5-methyl-4-oxo-2,3,4,5-tetrahydrobenzo[b][1,4]oxazepin-3-yl)benzo[d]isothiazole-3-carboxamide;

(S)-1-benzyl-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide;

(S)-5-cyclopropyl-N-(5-methyl-4-oxo-2,3,4,5-tetrahydrobenzo[b][1,4]oxazepin-3-yl)-1H-indazole-3-carboxamide;

(S)-5-(4-fluorobenzyl)-N-(4-methyl-5-oxo-5,6,7,8-tetrahydro-4H-pyrazolo[1,5-a][1,3]diazepin-6-yl)-4H-1,2,4-triazole-3-carboxamide;

(S)-5-(2,3-difluorobenzyl)-N-(4-methyl-5-oxo-5,6,7,8-tetrahydro-4H-pyrazolo[1,5-a][1,3]diazepin-6-yl)-4H-1,2,4-triazole-3-carboxamide;

1-benzyl-N-(3,4-dimethyl-5-oxo-5,6,7,8-tetrahydro-4H-pyrazolo[1,5-a][1,3]diazepin-6-yl)-1H-1,2,4-triazole-3-carboxamide;

1-benzyl-N-(1-methyl-2-oxo-2,3,4,5-tetrahydro-1H-[1,3]diazepino[1,2-b]indazol-3-yl)-1H-1,2,4-triazole-3-carboxamide;

(S)—N-(5-methyl-4-oxo-2,3,4,5-tetrahydrobenzo[b][1,4]oxazepin-3-yl)-6-(perfluoroethyl)-[1,2,4]triazolo[4,3-b]pyridazine-3-carboxamide;

(S)—N-(5-methyl-4-oxo-2,3,4,5-tetrahydrobenzo[b][1,4]oxazepin-3-yl)-5-(trifluoromethyl)-1H-indazole-3-carboxamide;

(S)—N-(5-methyl-4-oxo-2,3,4,5-tetrahydrobenzo[b][1,4]oxazepin-3-yl)-5-(perfluoroethyl)-1H-pyrazolo[3,4-b]pyridine-3-carboxamide;

(S)—N-(5-methyl-4-oxo-2,3,4,5-tetrahydrobenzo[b][1,4]oxazepin-3-yl)-4'H,6'H-spiro[cyclopentane-1,5'-pyrrolo[1,2-c][1,2,3]triazole]-3'-carboxamide;

(S)-1-isopropyl-N-(5-methyl-4-oxo-2,3,4,5-tetrahydrobenzo[b][1,4]oxazepin-3-yl)-1H-pyrazolo[3,4-d]pyrimidine-6-carboxamide;

(S)—N—((S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide;

N—((S)-5-methyl-4-oxo-2,3,4,5-tetrahydrobenzo[b][1,4]oxazepin-3-yl)-1-(tetrahydrofuran-3-yl)-1H-pyrazolo[4,3-c]pyridine-6-carboxamide;

(S)-5-isopropyl-N-(5-methyl-4-oxo-2,3,4,5-tetrahydrobenzo[b][1,4]oxazepin-3-yl)-1H-pyrazolo[4,3-b]pyridine-3-carboxamide;

1-benzyl-N-(1-methyl-2-oxo-1,2,3,4,5,10-hexahydro-8H-thieno[3',4':3,4]pyrazolo[1,5-a][1,3]diazepin-3-yl)-1H-1,2,4-triazole-3-carboxamide;

(S)-5-chloro-N-(5-methyl-4-oxo-2,3,4,5-tetrahydrobenzo[b][1,4]oxazepin-3-yl)-1H-pyrazolo[4,3-b]pyridine-3-carboxamide;

1-benzyl-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

(R)—N—((S)-5-methyl-4-oxo-2,3,4,5-tetrahydrobenzo[b][1,4]oxazepin-3-yl)-5-(trifluoromethyl)-4,5,6,7-tetrahydro-[1,2,3]triazolo[1,5-a]pyridine-3-carboxamide;

(S)-1-benzyl-N-(9-methyl-8-oxo-6,7,8,9-tetrahydro-5H-imidazo[1,2-a][1,3]diazepin-7-yl)-1H-1,2,4-triazole-3-carboxamide;

N-(5-methyl-4-oxo-2,3,4,5-tetrahydrobenzo[b][1,4]oxazepin-3-yl)-1-((R)-tetrahydrofuran-3-yl)-1H-pyrazolo[4,3-c]pyridine-6-carboxamide;

(S)-1-benzyl-N-(4-methyl-5-oxo-4,5,6,7,8,9-hexahydropyrazolo[1,5-a][1,3]diazocin-6-yl)-1H-1,2,4-triazole-3-carboxamide;

(S)-1-benzyl-N-(1-methyl-2-oxo-1,2,3,4,5,6-hexahydroimidazo[1,5-a][1,3]diazocin-3-yl)-1H-1,2,4-triazole-3-carboxamide;

(S)-1-(cyclopentylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide;

(R)-1-methyl-N—((S)-5-methyl-4-oxo-2,3,4,5-tetrahydrobenzo[b][1,4]oxazepin-3-yl)-1-(2,2,2-trifluoroethyl)-1,3-dihydrofuro[3,4-c]pyridine-6-carboxamide;

(S)-1-(cyclopentylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-(cyclohexylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)—N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-((S)-1-phenylethyl)-1H-1,2,4-triazole-3-carboxamide;

(S)-1-benzyl-N-(3,4-dimethyl-5-oxo-5,6,7,8-tetrahydro-4H-pyrazolo[1,5-a][1,3]diazepin-6-yl)-1H-1,2,4-triazole-3-carboxamide;

(R)—N—((S)-5-methyl-4-oxo-2,3,4,5-tetrahydrobenzo[b][1,4]oxazepin-3-yl)-4,5-dihydro-2H,3'H-spiro[furan-3,1'-furo[3,4-c]pyridine]-6'-carboxamide;

(S)-1-(4-chlorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide;

6-isopropyl-N—((S)-5-methyl-4-oxo-2,3,4,5-tetrahydrobenzo[b][1,4]oxazepin-3-yl)-5,6,7,8-tetrahydroimidazo[1,5-a]pyridine-3-carboxamide;

(S)—N-(5-methyl-4-oxo-2,3,4,5-tetrahydrobenzo[b][1,4]oxazepin-3-yl)-5-(trifluoromethyl)-[1,2,3]triazolo[1,5-a]pyridine-3-carboxamide;

(S)—N-(5-methyl-4-oxo-2,3,4,5-tetrahydrobenzo[b][1,4]oxazepin-3-yl)-2-(trifluoromethyl)imidazo[1,5-a]pyrimidine-8-carboxamide;

(S)-1-ethyl-N-(5-methyl-4-oxo-2,3,4,5-tetrahydrobenzo[b][1,4]oxazepin-3-yl)-1H-pyrazolo[4,3-c]pyridine-6-carboxamide;

5-(2,4-difluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide;

5-(2,4-difluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide;

(S)-7,7-dimethyl-N-(5-methyl-4-oxo-2,3,4,5-tetrahydrobenzo[b][1,4]oxazepin-3-yl)-5,7-dihydrofuro[3,4-d]pyrimidine-2-carboxamide;

(S)-7,7-dimethyl-N-(5-methyl-4-oxo-2,3,4,5-tetrahydrobenzo[b][1,4]oxazepin-3-yl)-5,7-dihydrothieno[3,4-d]pyrimidine-2-carboxamide;

(S)-1-(2,3-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-(3,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-(2,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)—N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(3,4-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

(S)-5-isopropyl-N-(5-methyl-4-oxo-2,3,4,5-tetrahydrobenzo[b][1,4]oxazepin-3-yl)-1H-indazole-3-carboxamide;

1-methyl-N—((S)-5-methyl-4-oxo-2,3,4,5-tetrahydrobenzo[b][1,4]oxazepin-3-yl)-1-(2,2,2-trifluoroethyl)-1,3-dihydrofuro[3,4-c]pyridine-6-carboxamide;

(S)—N-(5-methyl-4-oxo-2,3,4,5-tetrahydrobenzo[b][1,4]oxazepin-3-yl)-7-(trifluoromethyl)imidazo[1,5-c]pyrimidine-1-carboxamide;

(S)-5-isopropyl-N-(5-methyl-4-oxo-2,3,4,5-tetrahydrobenzo[b][1,4]oxazepin-3-yl)-1H-pyrazolo[3,4-b]pyridine-3-carboxamide;

(S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide;

(R)—N—((S)-6,8-difluoro-4-oxo-2,3,4,5-tetrahydrobenzo[b][1,4]oxazepin-3-yl)-1-ethyl-1-meth yl-1,3-dihydrofuro[3,4-c]pyridine-6-carboxamide;

N—((S)-5-methyl-4-oxo-2,3,4,5-tetrahydrobenzo[b][1,4]oxazepin-3-yl)-5-(1,1,1-trifluoropropan-2-yl)-4,5,6,7-tetrahydro-[1,2,3]triazolo[1,5-a]pyridine-3-carboxamide;

1-cyclopropyl-1-methyl-N—((S)-5-methyl-4-oxo-2,3,4,5-tetrahydrobenzo[b][1,4]oxazepin-3-yl)-1,3-dihydrofuro[3,4-c]pyridine-6-carboxamide;

N—((S)-2,4-dimethyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide;

(S)-1-(2,3-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

(S)-1-(3,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

N—((S)-5-methyl-4-oxo-2,3,4,5-tetrahydrobenzo[b][1,4]oxazepin-3-yl)-5-(perfluoroethyl)-4,5,6,7-tetrahydro-[1,2,3]triazolo[1,5-a]pyridine-3-carboxamide;

(S)-1-(2,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

(S)-1-(4-fluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

1-(4-chlorobenzyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide;

N—((S)-5-methyl-4-oxo-2,3,4,5-tetrahydrobenzo[b][1,4]oxazepin-3-yl)-5-(1,1,1-trifluoropropan-2-yl)-1H-pyrazolo[3,4-b]pyridine-3-carboxamide;

(S)-1-benzyl-N-(1-methyl-2-oxo-2,3,4,5-tetrahydro-1H-imidazo[1,5-a][1,3]diazepin-3-yl)-1H-1,2,4-triazole-3-carboxamide;

(S)—N-(5-methyl-4-oxo-2,3,4,5-tetrahydrobenzo[b][1,4]oxazepin-3-yl)-2',3',5',6'-tetrahydro-3H-spiro[furo[3,4-c]pyridine-1,4'-pyran]-6-carboxamide;

(S)-5-benzyl-N-(2,3,4-trimethyl-5-oxo-5,6,7,8-tetrahydro-4H-pyrazolo[1,5-a][1,3]diazepin-6-yl)-4H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,6-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(3,5-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,5-difluorobenzyl)-1H-1,2,4-triazole-3-carboxamide;

(S)-1-(2,5-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,3-dichlorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,4-dichlorobenzyl)-1H-1,2,4-triazole-3-carboxamide;

7-methyl-N—((S)-5-methyl-4-oxo-2,3,4,5-tetrahydrobenzo[b][1,4]oxazepin-3-yl)-7-propyl-5,7-dihydrofuro[3,4-d]pyrimidine-2-carboxamide;

7-ethyl-7-methyl-N—((S)-5-methyl-4-oxo-2,3,4,5-tetrahydrobenzo[b][1,4]oxazepin-3-yl)-5,7-dihydrofuro[3,4-d]pyrimidine-2-carboxamide;

1-(2,3-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(2,4-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(2,4-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

(S)—N—((S)-2-((R)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide;

1-(2,3-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(3,4-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(2,4-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

N—((S)-2-((S)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,3-difluorobenzyl)-1H-1,2,4-triazole-3-carboxamide; and (S)—N-(2-cyclopropyl-4-methyl-5-oxo-5,6,7,8-tetrahydro-4H-pyrazolo[1,5-a][1,3]diazepin-6-yl)-5-(4-fluorobenzyl)-4H-1,2,4-triazole-3-carboxamide.

Synthesis

Compounds of formula I may be prepared by the processes illustrated in the schemes below or by methods known to those of ordinary skill in the art. Scheme 1 below is an example of a method of preparing a compound of formula I, wherein "R" represent the "right-hand side" building block derived from the carboxylic acid intermediates of exemplary Schemes 2-14 and 26-35 (when L of formula I is absent) or is as prepared according to the procedures described in WO 2014/125444 (wherein L is present). Schemes 15-25 show illustrative methods for making the "left-hand side" lactam building blocks of compounds of formulae I, I(a) and I(b).
Scheme 1
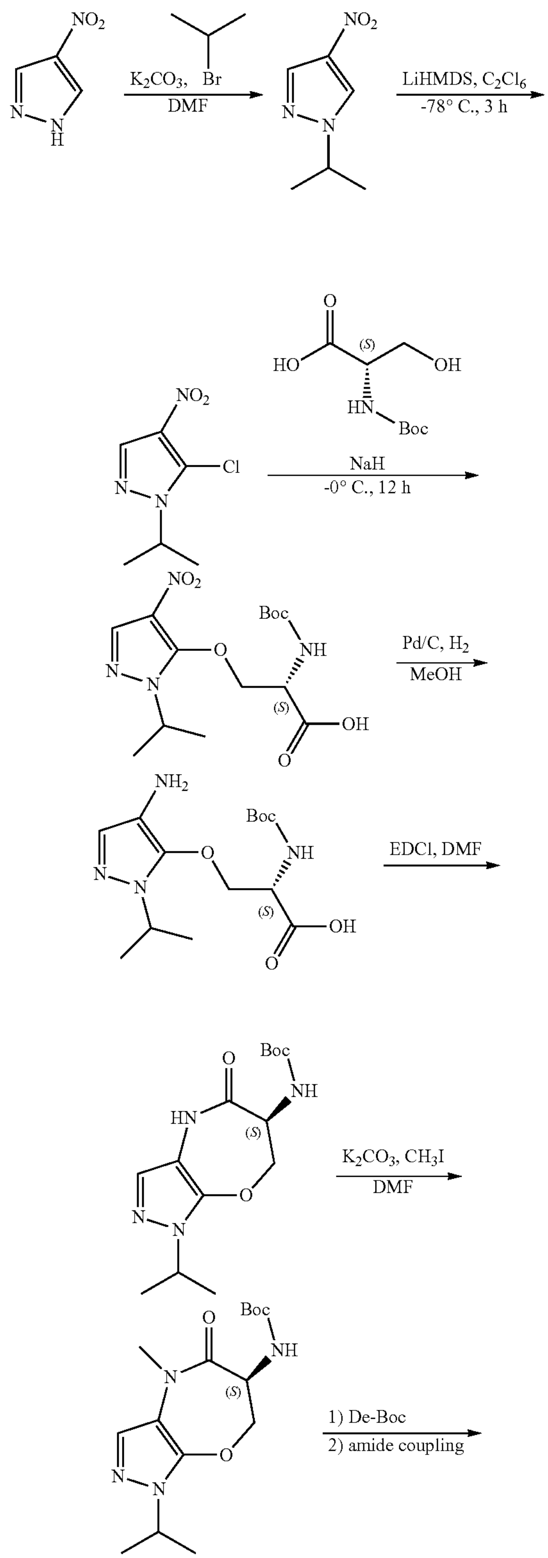
-continued
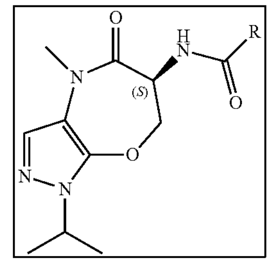
Scheme 2
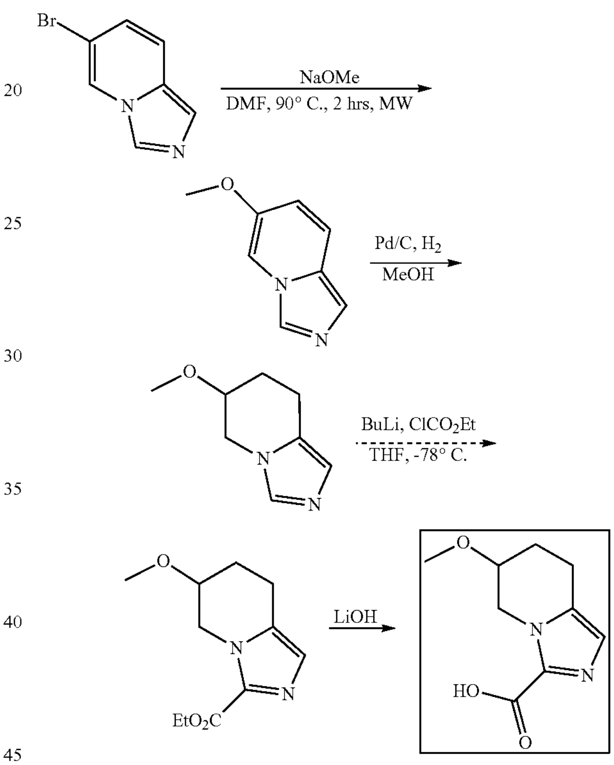
Scheme 3
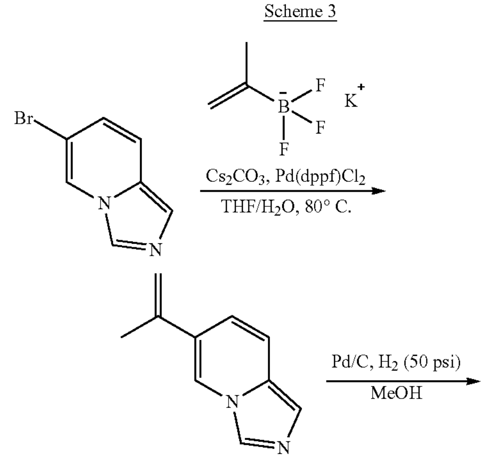

-continued
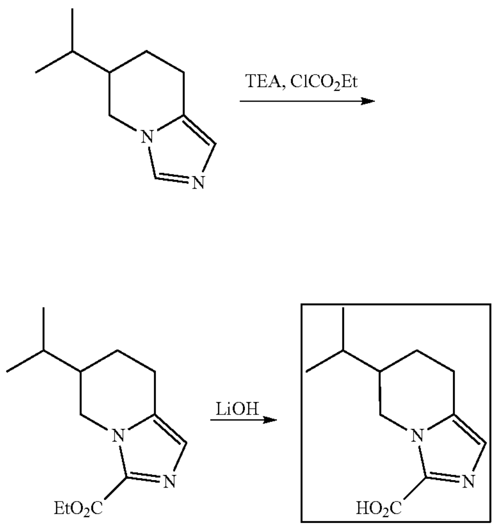
Scheme 4
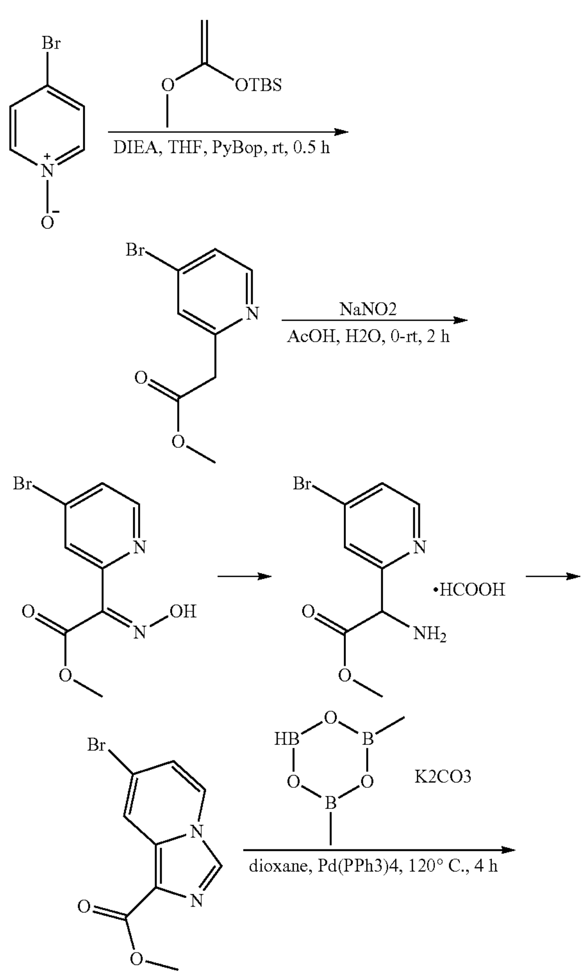
-continued
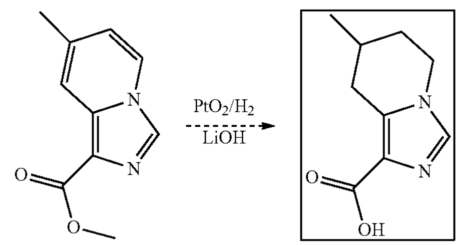
Scheme 5
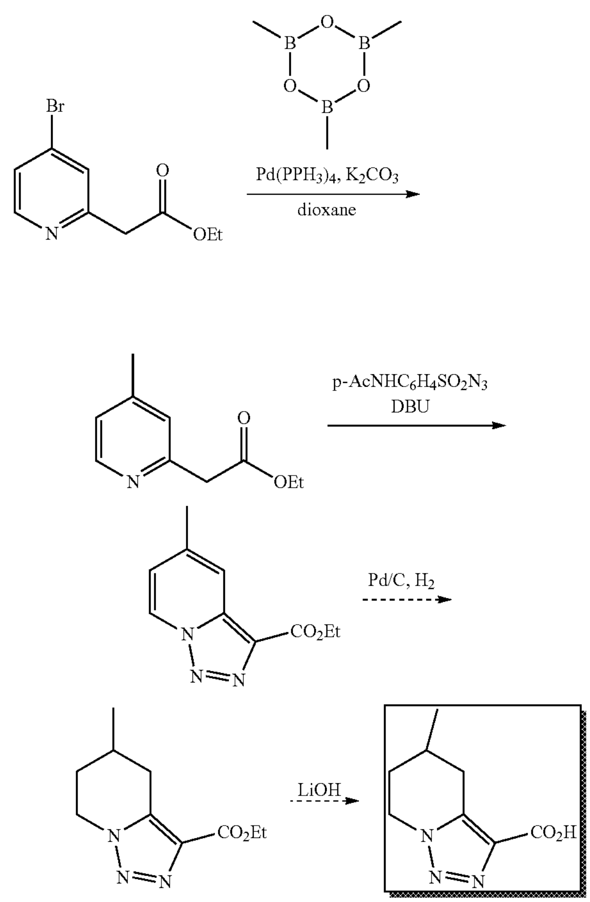
Scheme 6
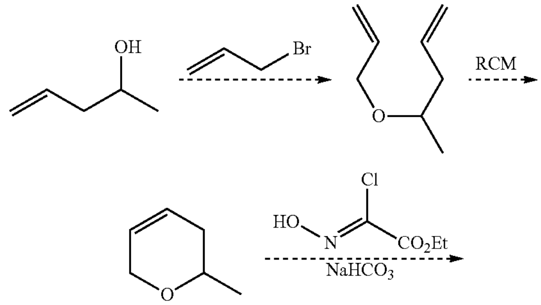

-continued
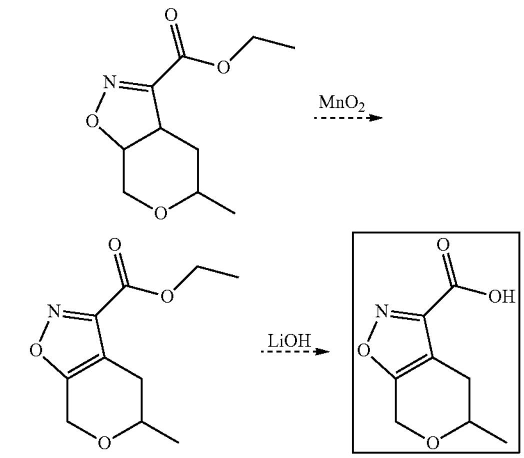
Scheme 7
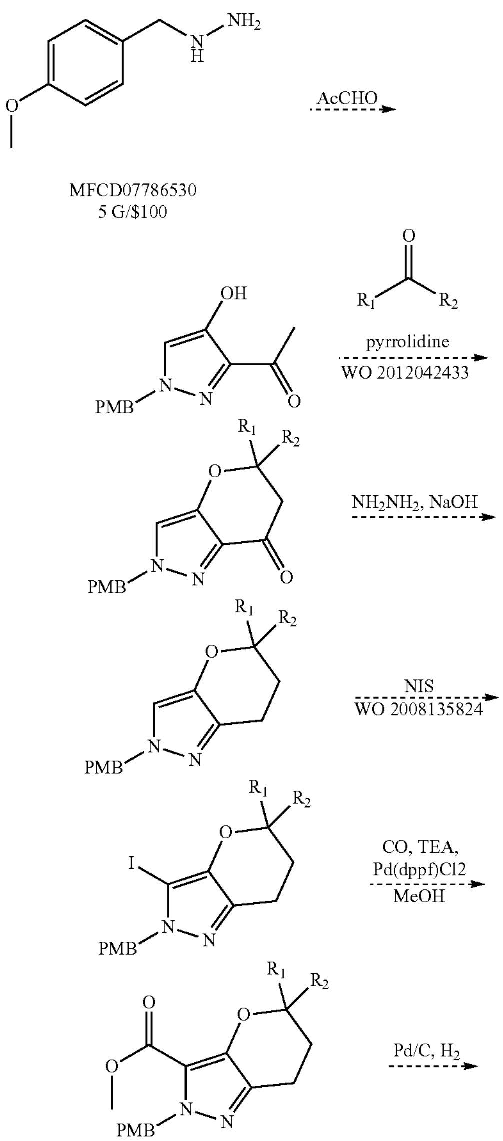
-continued
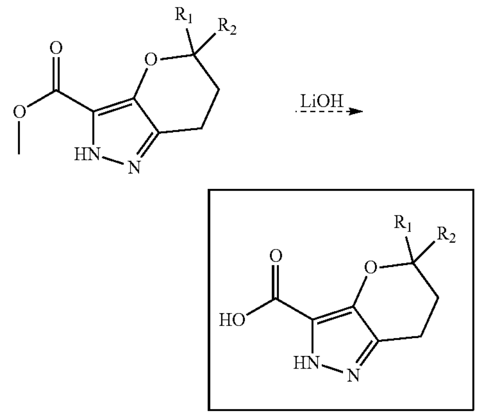
Scheme 8
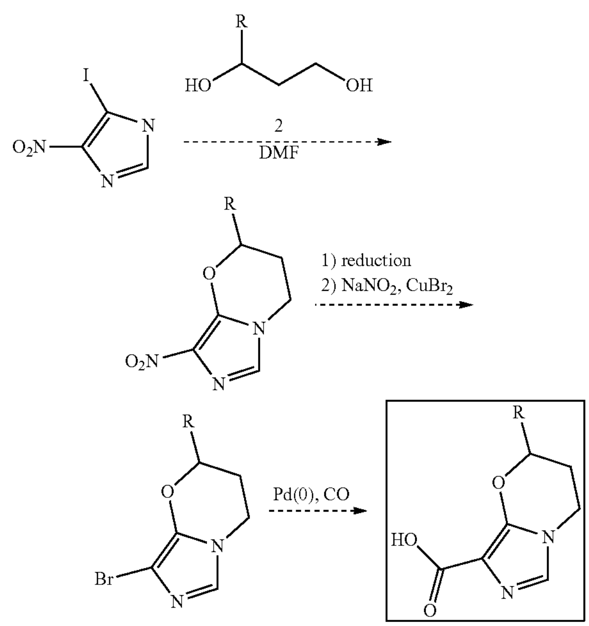
Scheme 9
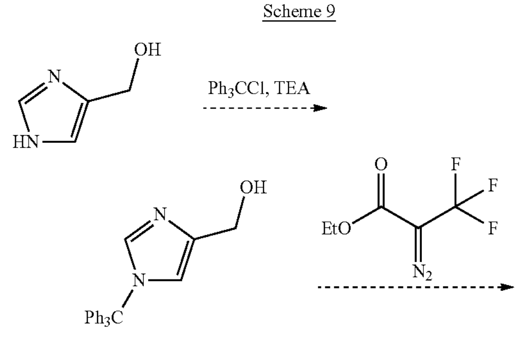

-continued
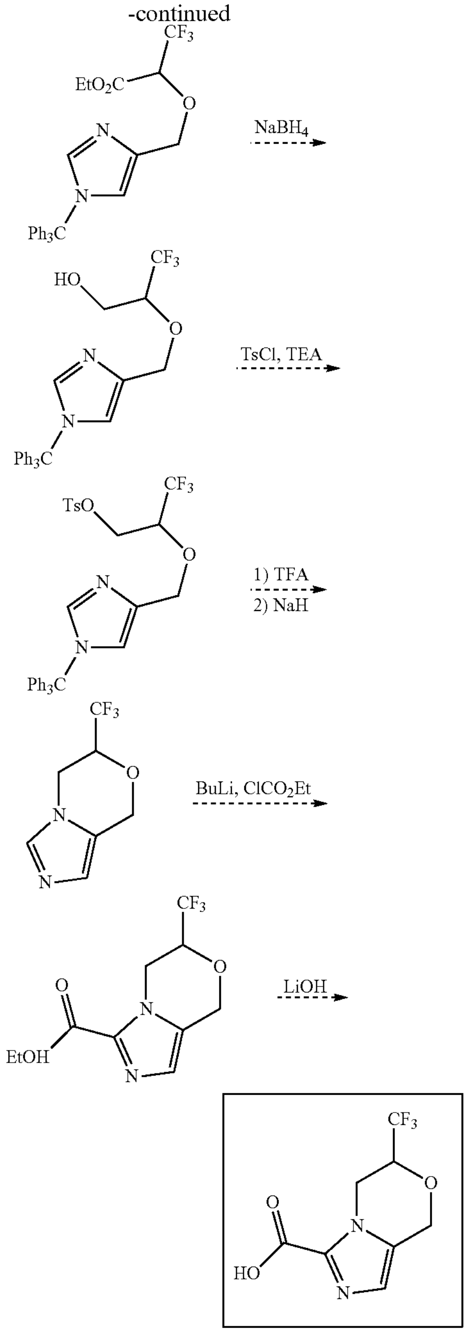
Scheme 10
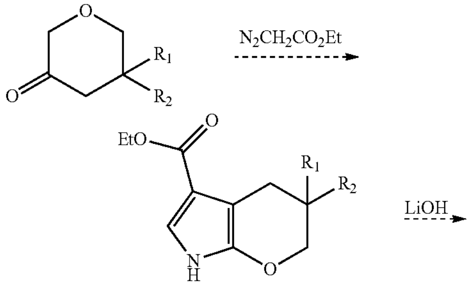
-continued
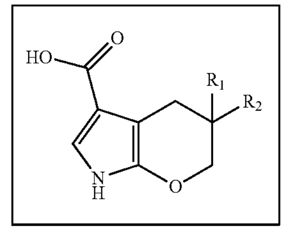
Scheme 11
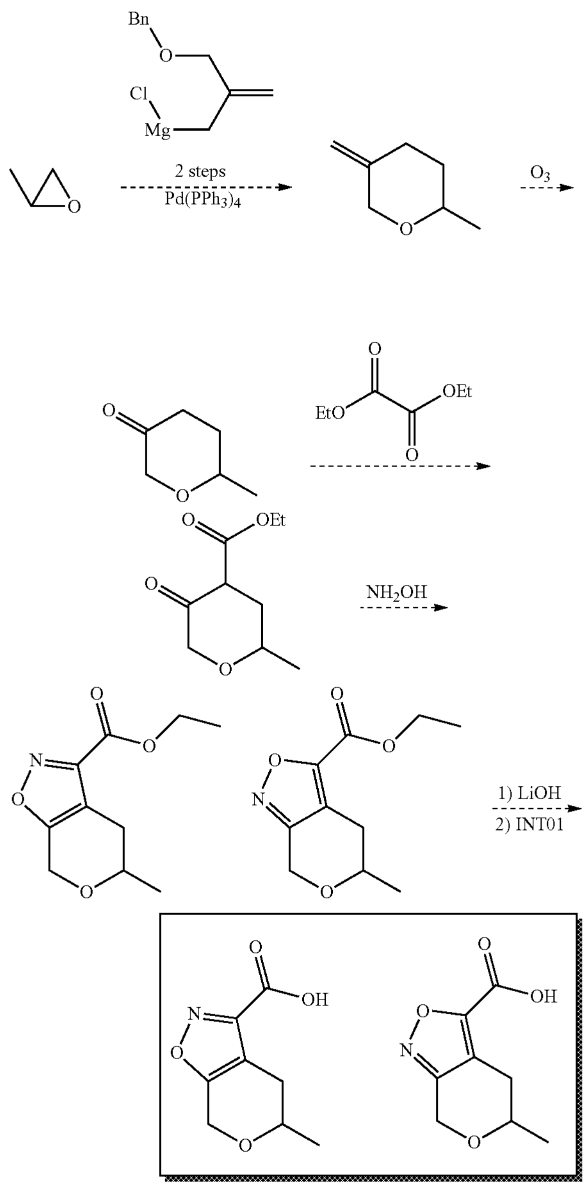
Isothiazoles are prepared in the same way shown in Scheme 11 by substituting $NH_2$—OH for $NH_2$—SH.

Scheme 12
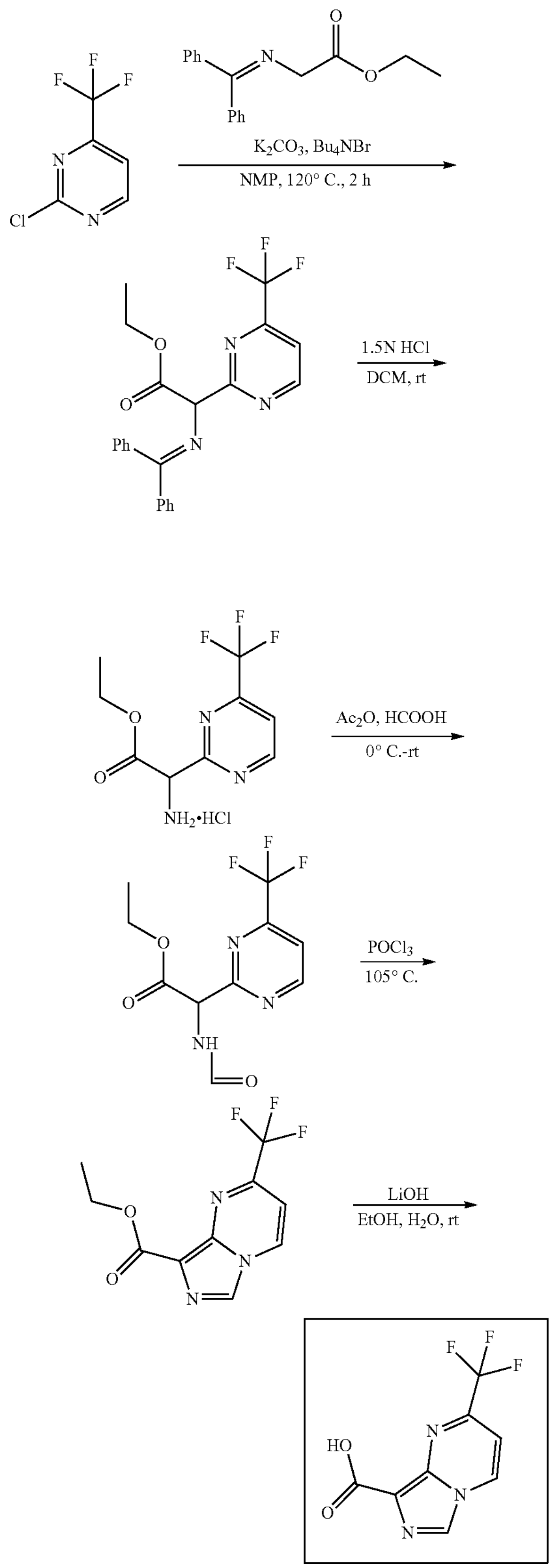
Scheme 13
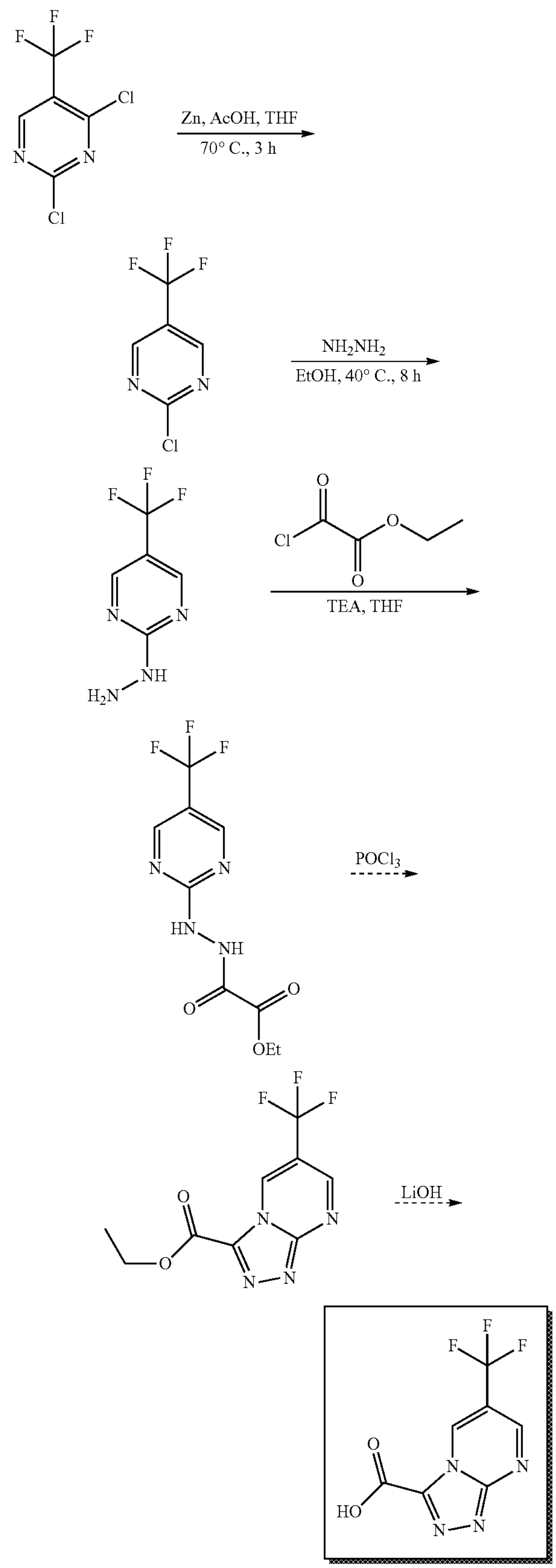

Scheme 14
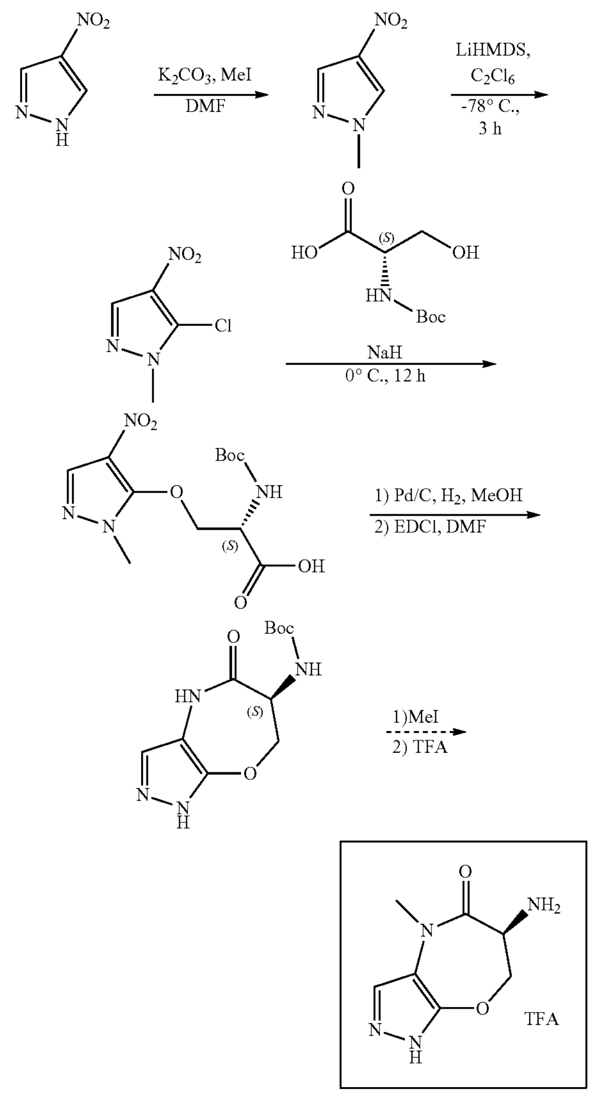
Scheme 15
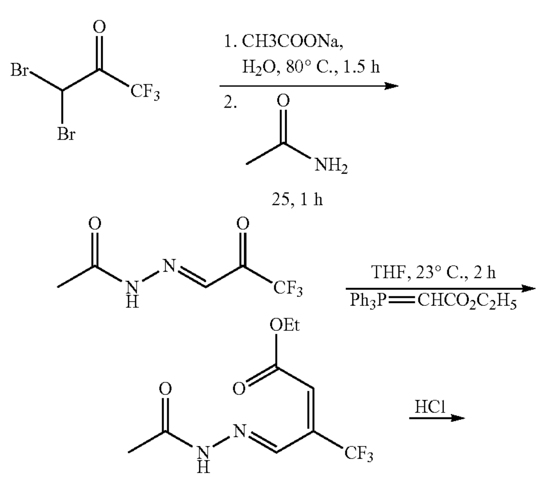
-continued
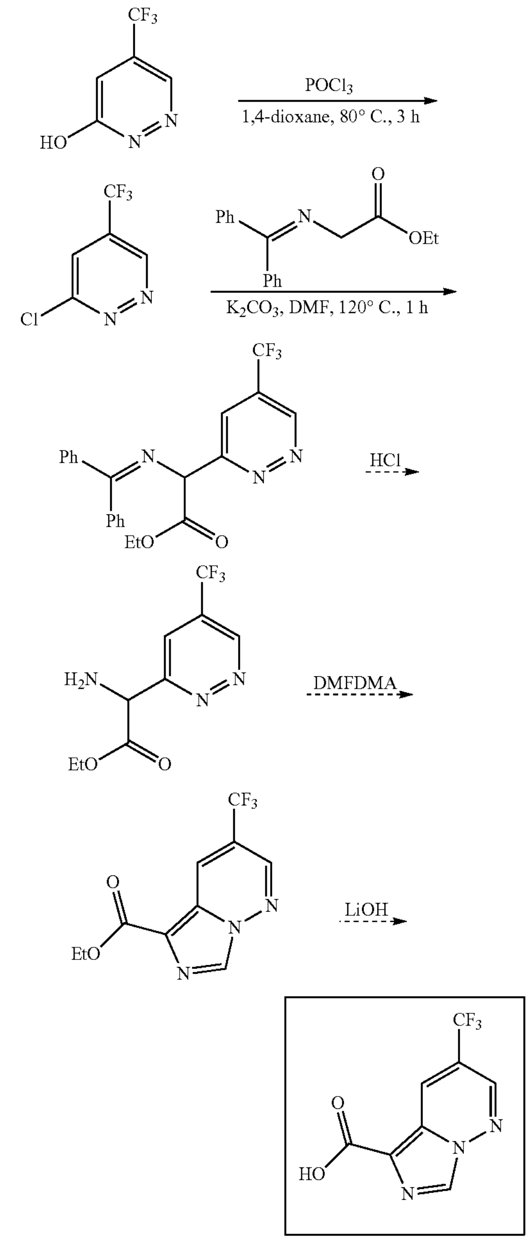
Scheme 16
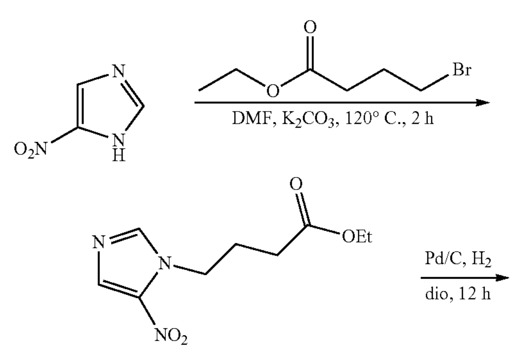

-continued
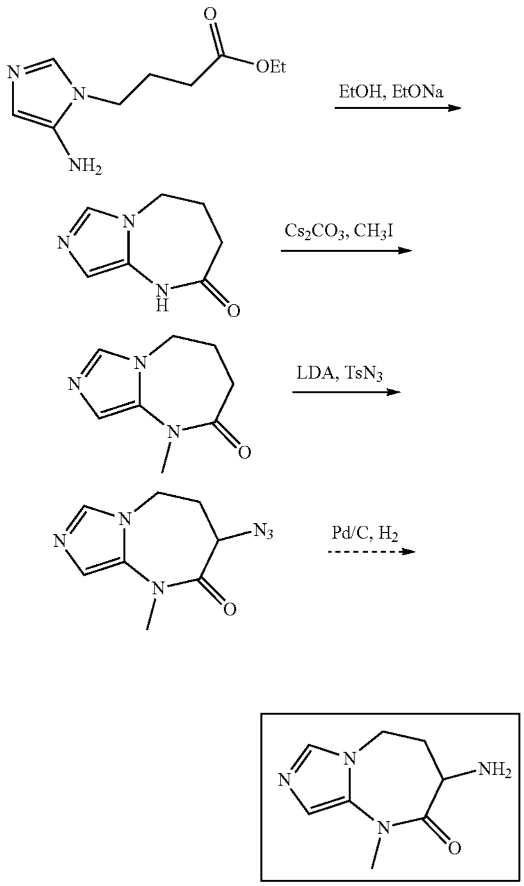
Scheme 17
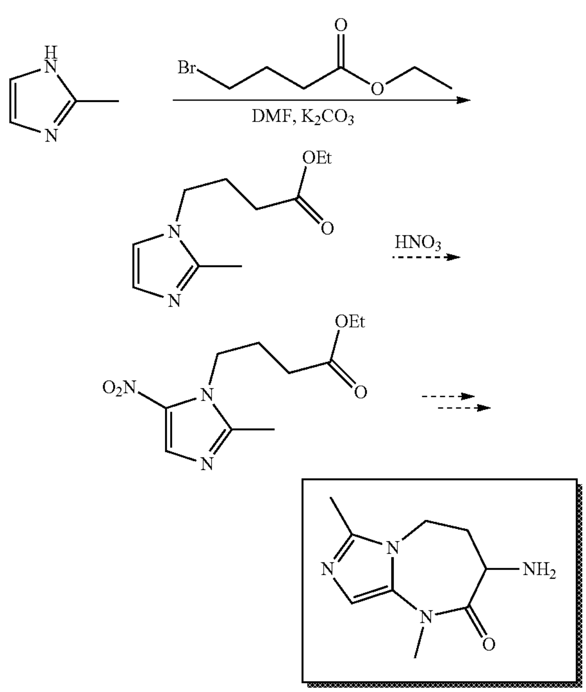
Scheme 18
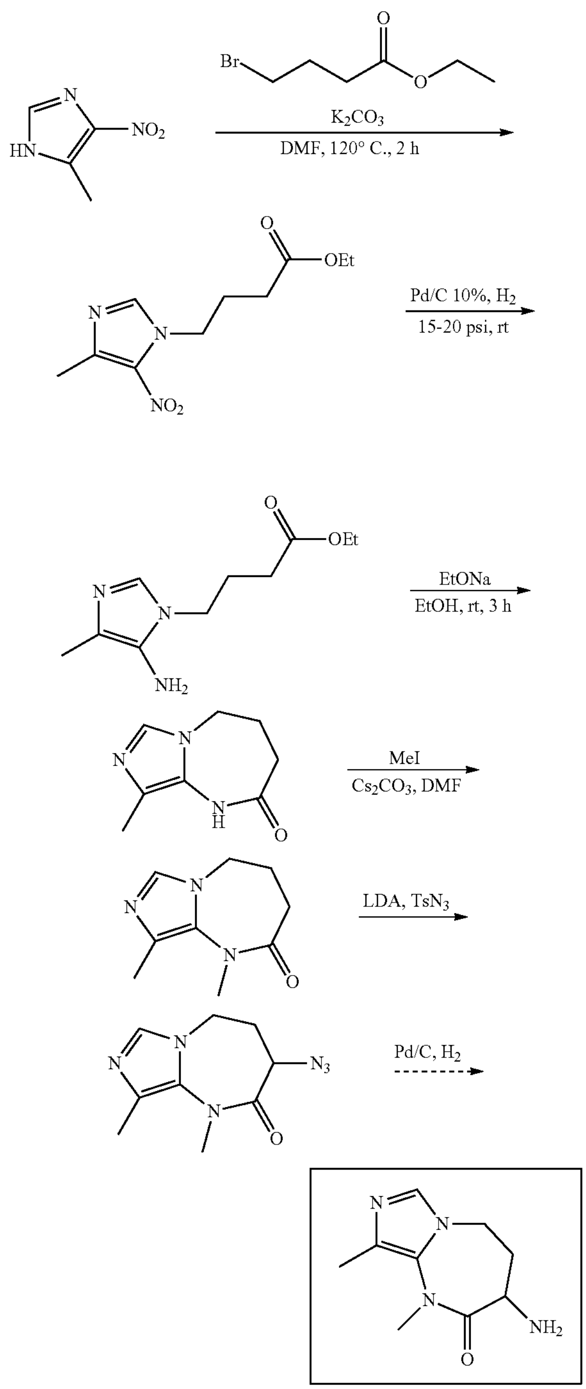
Scheme 19
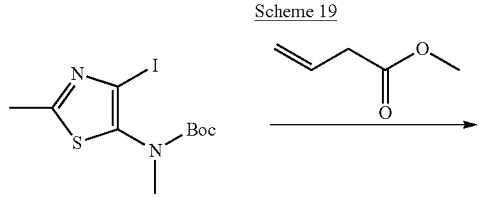

-continued
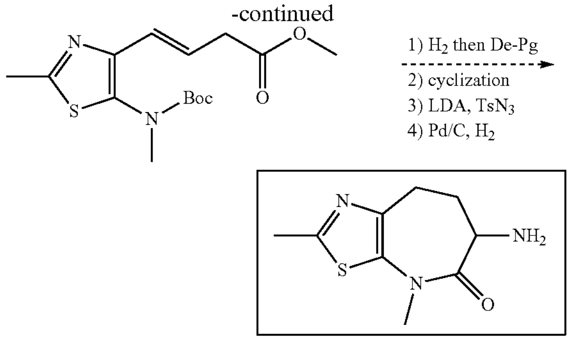
-continued
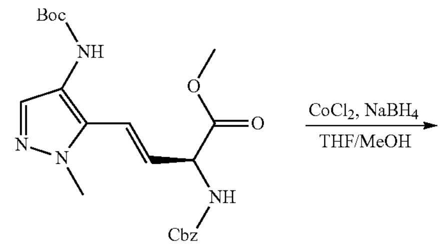
Scheme 20
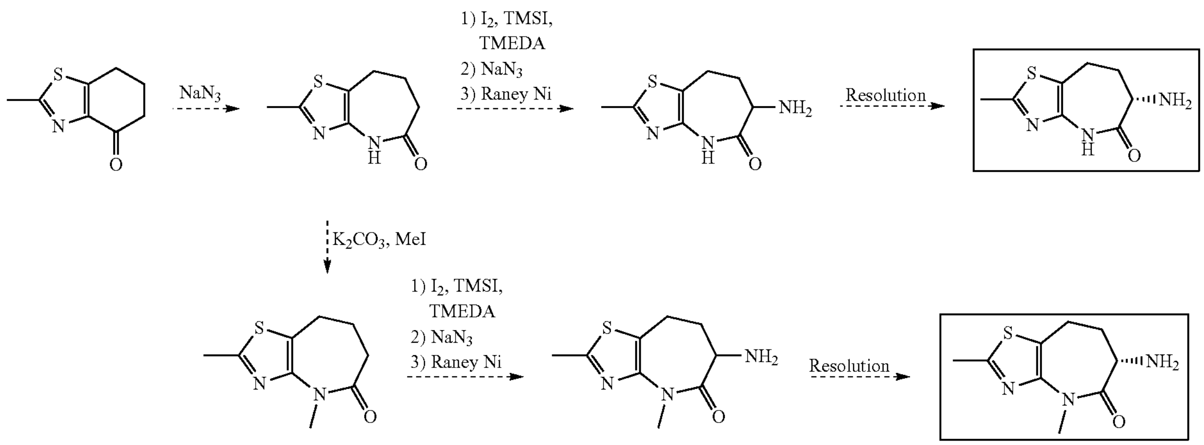
Scheme 21
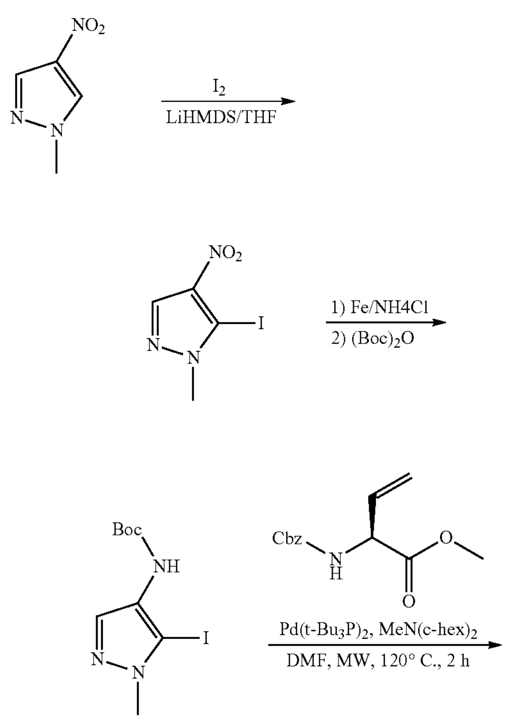
-continued
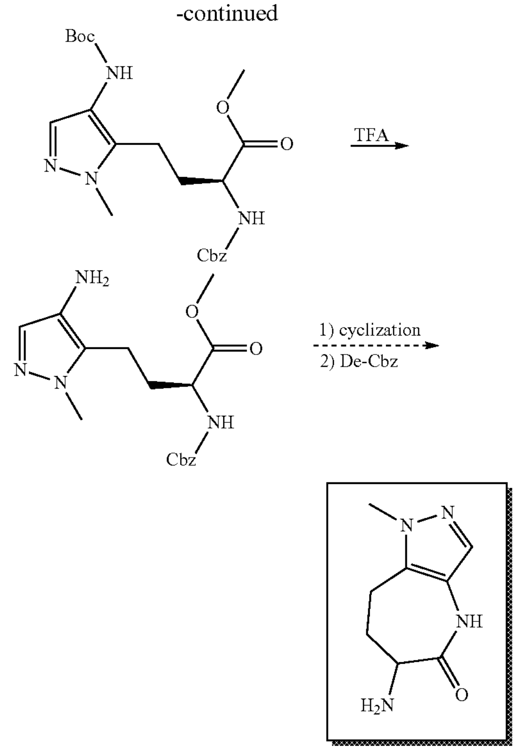

Scheme 22
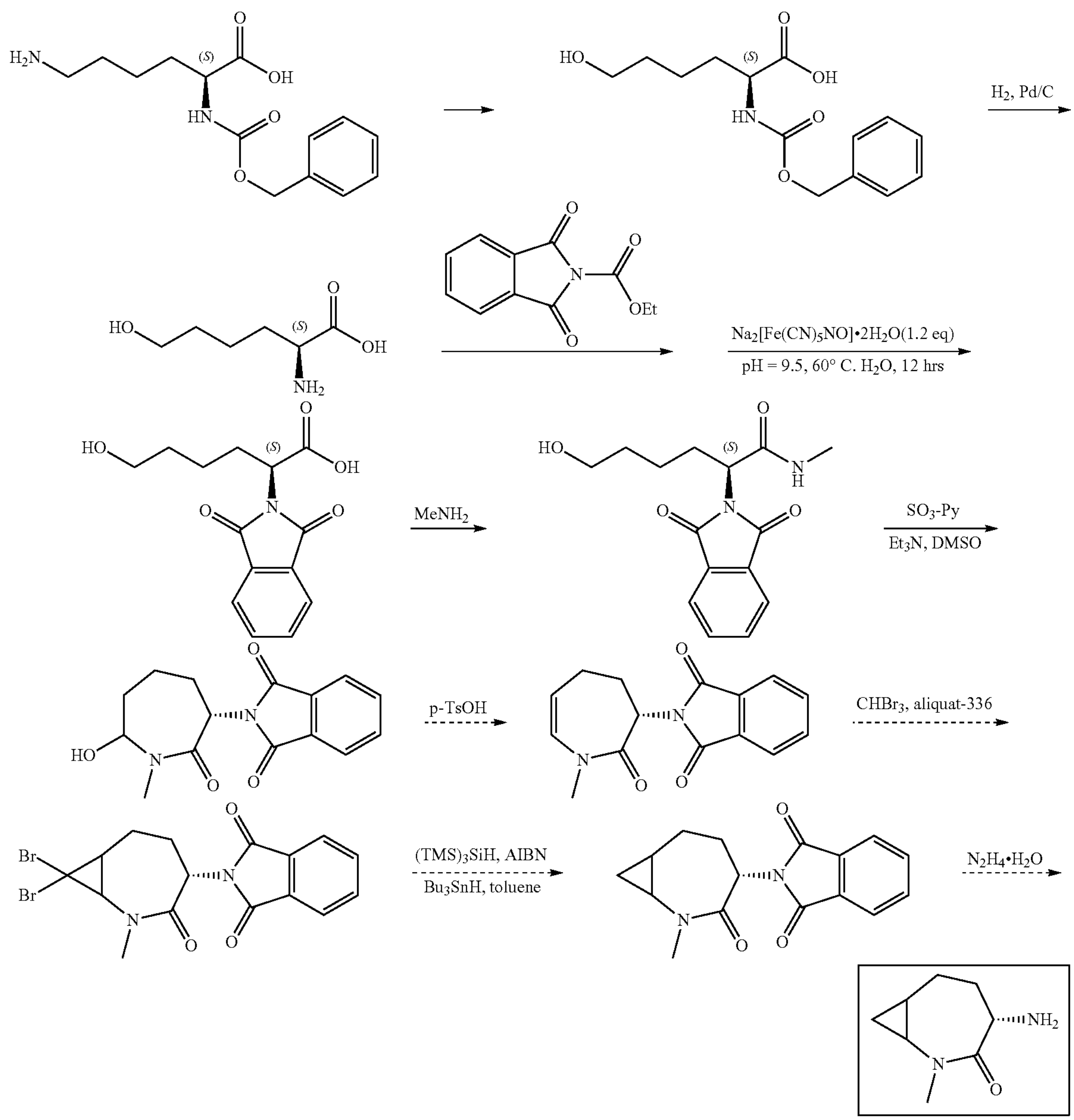
Scheme 23
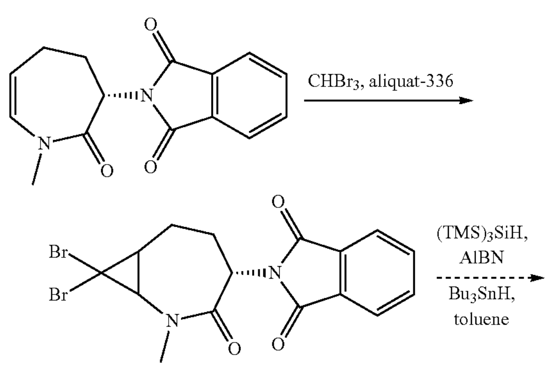
-continued
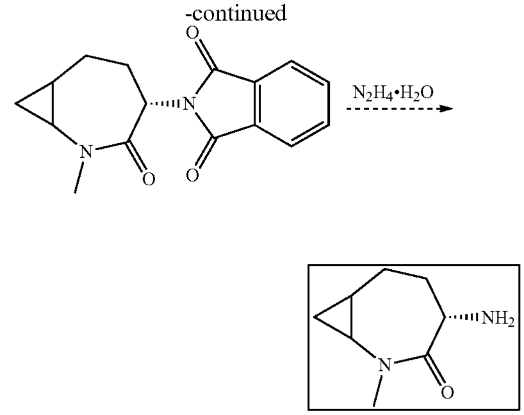

Scheme 24
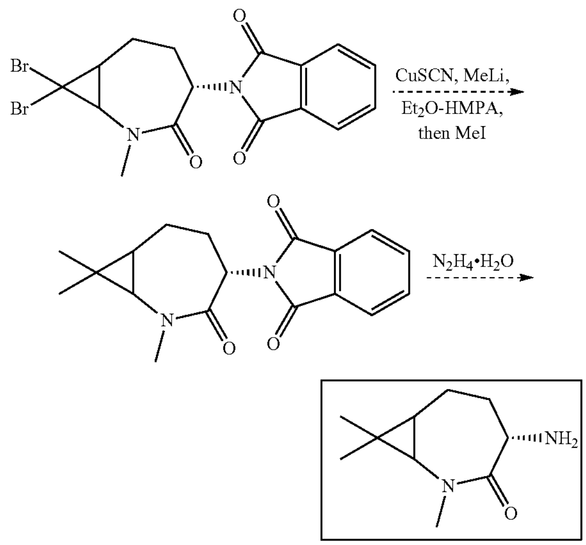
Scheme 25
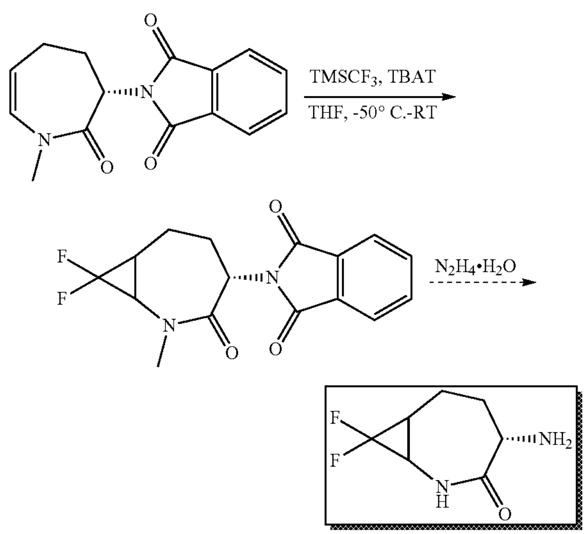
SchemE 26
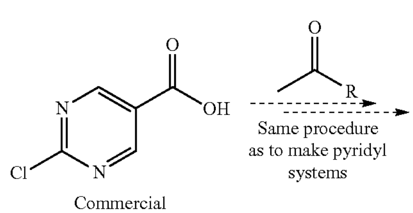
Commercial
-continued
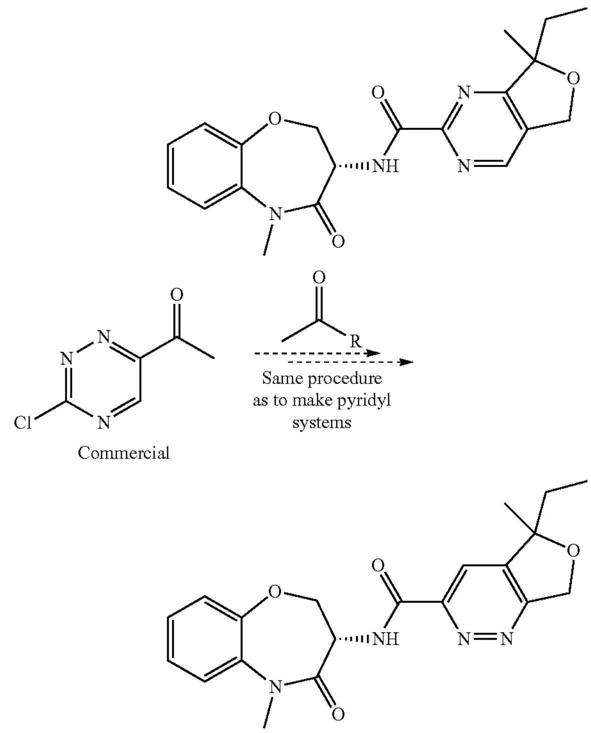
Scheme 27
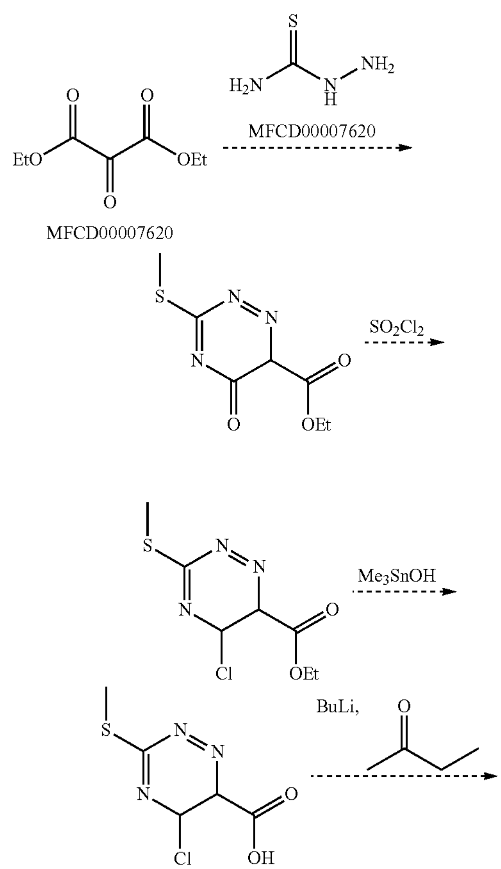

-continued
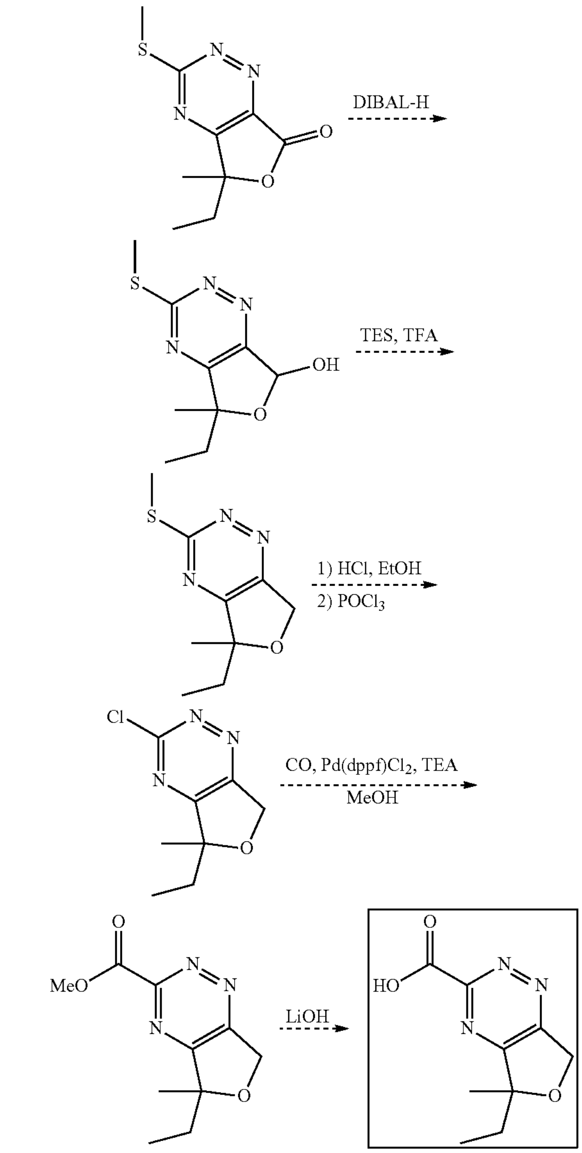
Scheme 28
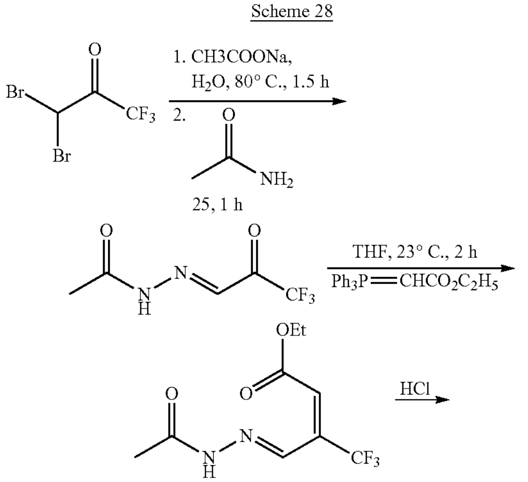
-continued
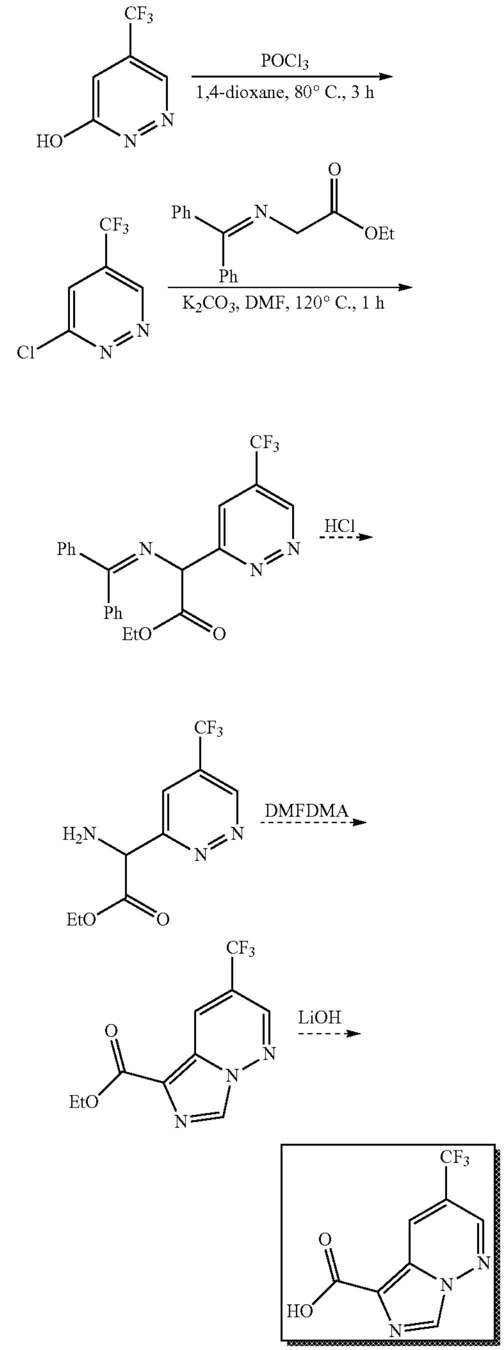
Scheme 29
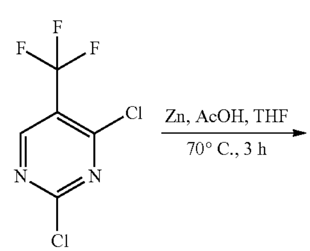

-continued
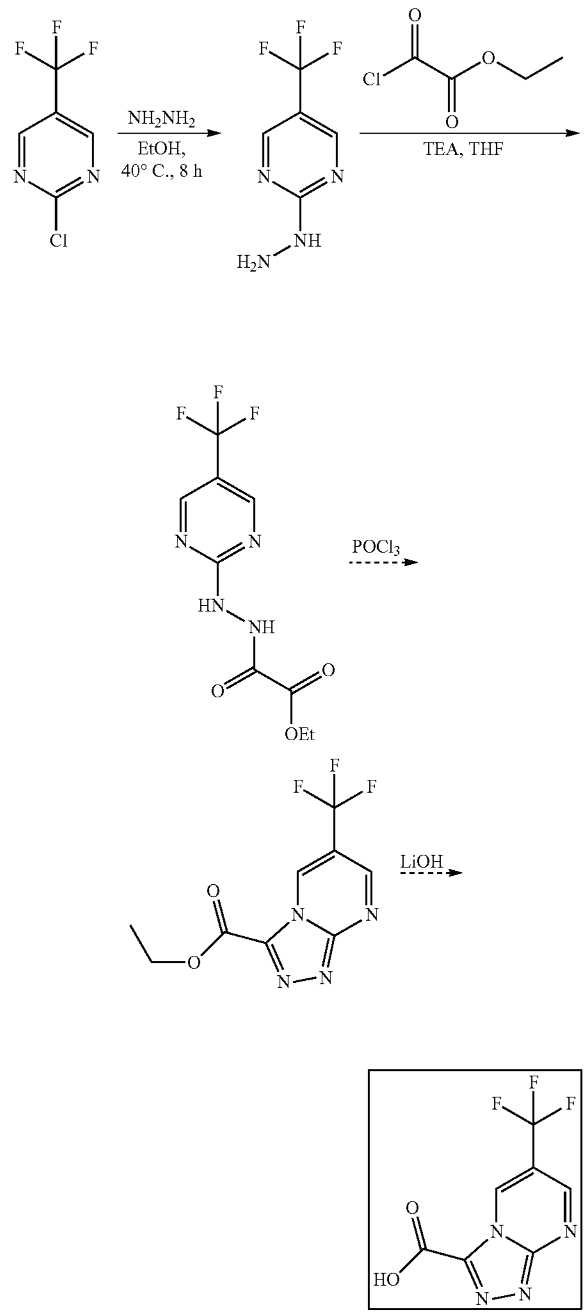
-continued
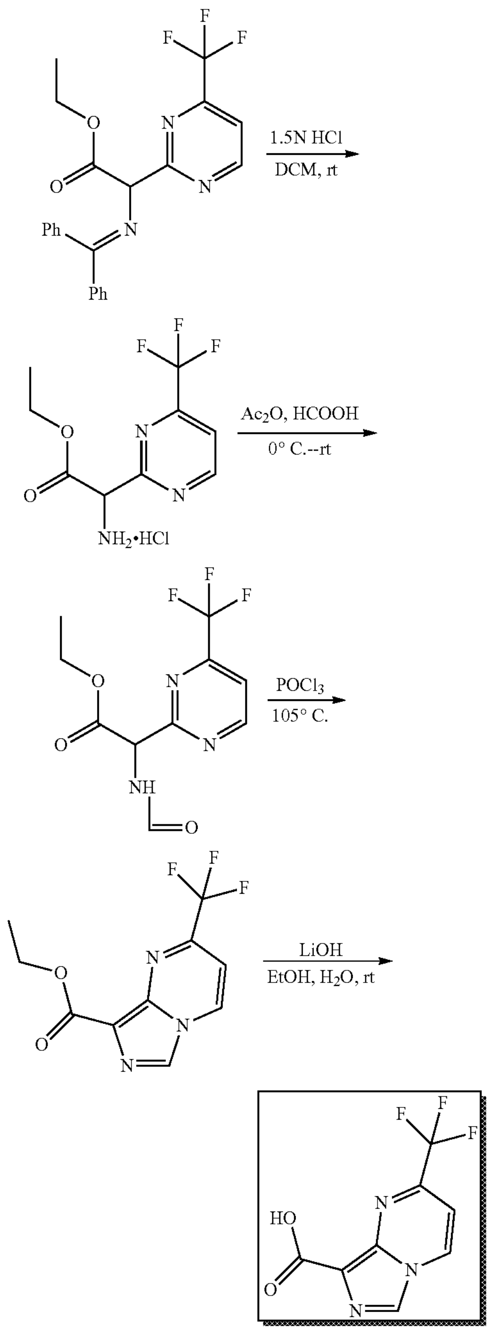
Scheme 30
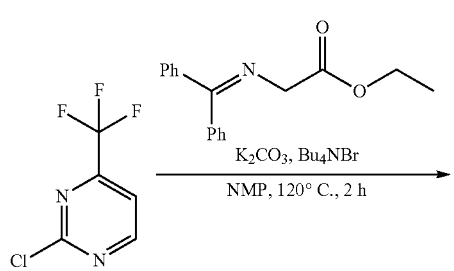
Scheme 31
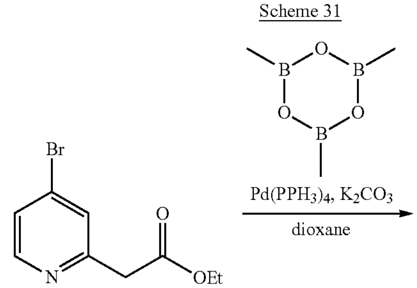

-continued
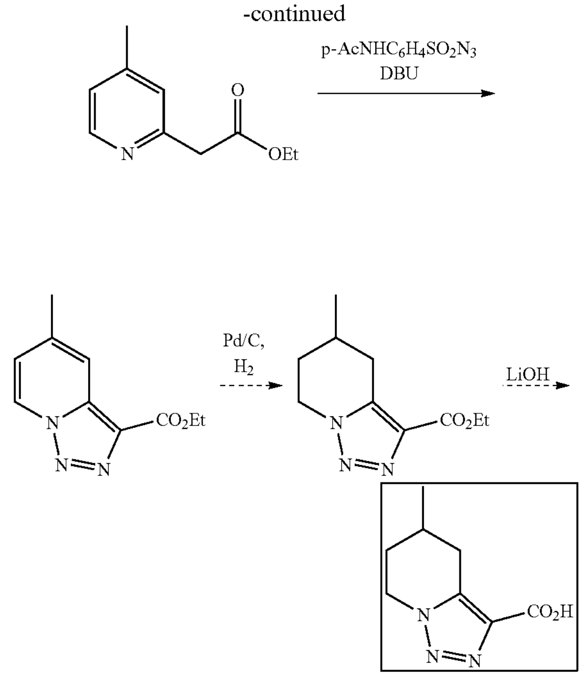
Scheme 32
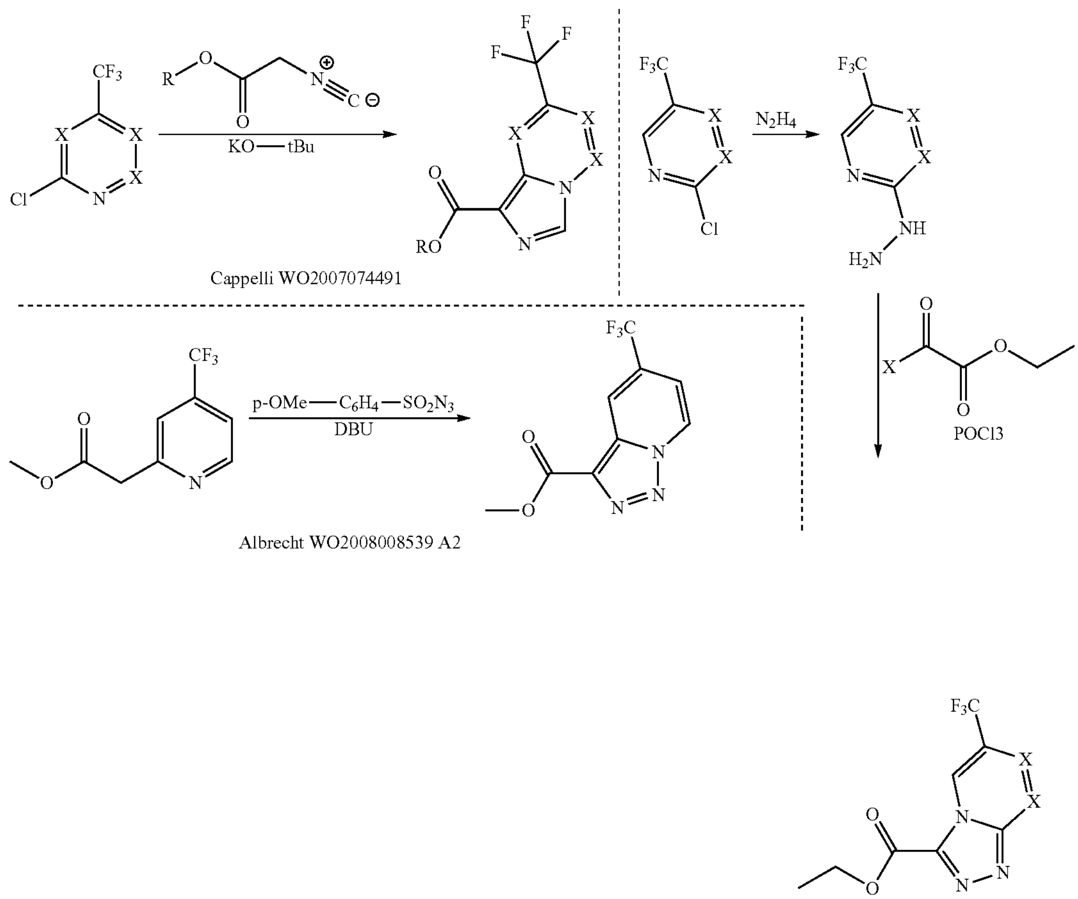

Scheme 33

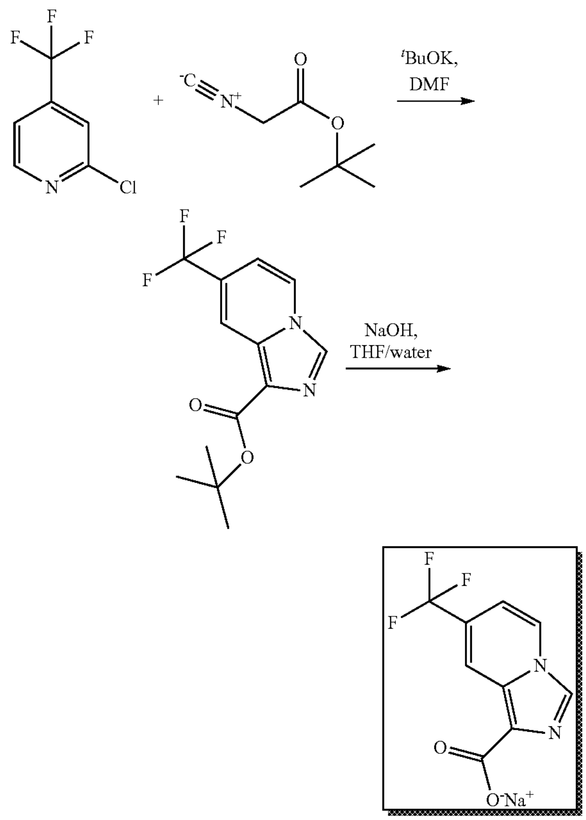

Scheme 34

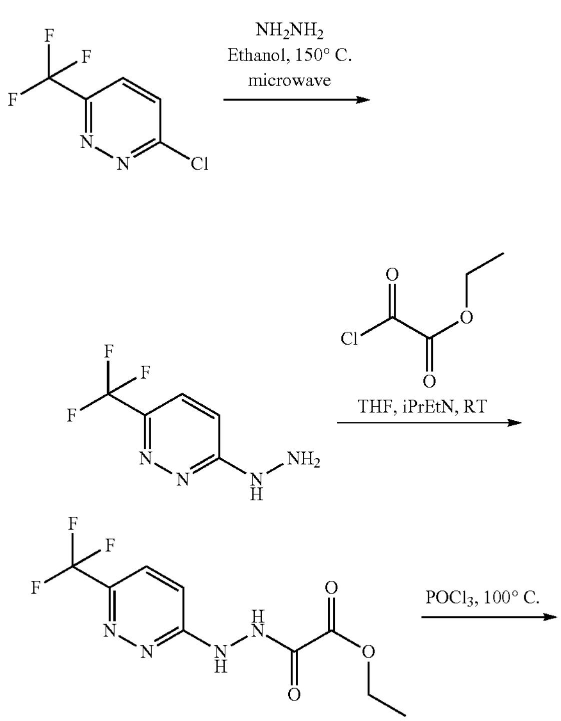

-continued

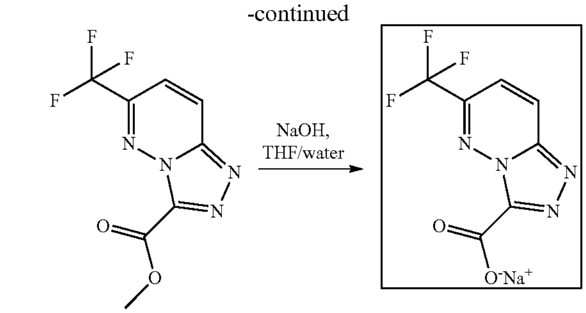

Scheme 35

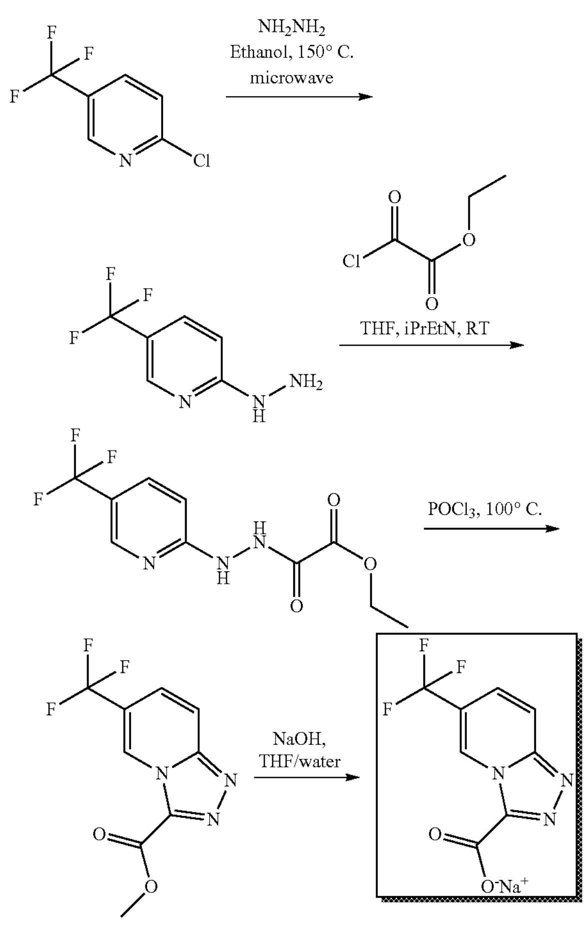

Pharmaceutical Compositions and Administration

Provided herein are pharmaceutical compositions or medicaments containing the compounds of the invention (or stereoisomers, geometric isomers, tautomers, solvates, metabolites, isotopes, pharmaceutically acceptable salts, or prodrugs thereof), and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In some embodiments, the "effective amount" of the compound to be administered will be governed by such considerations, and is the minimum amount necessary to inhibit RIP1 kinase activity in order to provide a therapeutic effect in the mammal being treated. In addition, such an effective amount may be below the amount that is toxic to normal cells, or the mammal as a whole.

In one example, the pharmaceutically effective amount of the compound of the invention administered intravenously or parenterally will be in the per dose range of about 0.1 to 100 mg/kg, alternatively about 0.1 to 20 mg/kg of patient body weight per day, or alternatively about 0.3 to 15 mg/kg/day.

In another embodiment, oral unit dosage forms, such as tablets and capsules, preferably contain from about 1 to about 1000 mg (e.g., 1 mg, 5 mg, 10 mg, 15 mg, 20 mg, 25 mg, 30 mg, 40 mg, 50 mg, 100 mg, 200 mg, 250 mg, 400 mg, 500 mg, 600 mg, 700 mg, 800 mg, 900 mg, or 1000 mg) of the compound of the invention. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

In some embodiments, a low dose of the compound of the invention is administered in order to provide therapeutic benefit while minimizing or preventing adverse effects.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In specific embodiments, the compound of formula I is administered orally. In other specific embodiments, the compound of formula I is administered intravenously.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

An example of a suitable oral dosage form provided herein is a tablet containing about 1 to about 500 mg (e.g., about 1 mg, 5 mg, 10 mg, 25 mg, 30 mg, 50 mg, 80 mg, 100 mg, 150 mg, 250 mg, 300 mg and 500 mg) of the compound of the invention compounded with suitable amounts of anhydrous lactose, sodium croscarmellose, polyvinylpyrrolidone (PVP) K30, and magnesium stearate. The powdered ingredients are first mixed together and then mixed with a solution of the PVP. The resulting composition can be dried, granulated, mixed with the magnesium stearate and compressed to tablet form using conventional equipment.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

An embodiment, therefore, includes a pharmaceutical composition comprising a compound of formula I, or pharmaceutically acceptable salt thereof. In a further embodiment includes a pharmaceutical composition comprising a compound of formula I, or a pharmaceutically acceptable salt thereof, together with a pharmaceutically acceptable carrier or excipient.

When the binding target is located in the brain, certain embodiments of the invention provide for a compound of formula I (or an embodiment thereof) to traverse the blood-brain barrier. In these embodiments, the compounds provided herein exhibit sufficient brain penetration as potential therapeutics in neurological diseases. In some embodiments, brain penetration is assessed by evaluating free brain/plasma ratio ($B_u/P_u$) as measured in vivo pharmacokinetic studies in rodents or by other methods known to persons skilled in the art (see, e.g., Liu, X. et al., J. Pharmacol. Exp. Therap., 325:349-56, 2008).

Certain neurological diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods. Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Publication No. 2002/0025313), and coating a compound of formula I (or an embodiment thereof) in low-density lipoprotein particles (see, e.g., U.S. Patent Publication No. 2004/0204354) or apolipoprotein E (see, e.g., U.S. Patent Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Publication Nos. 2002/0065259, 2003/0162695, and 2005/0124533); activating potassium channels (see, e.g., U.S. Patent Publication No. 2005/0089473), inhibiting ABC drug transporters (see, e.g., U.S. Patent Publication No. 2003/0073713); coating a compound of formula I or I-I (or an embodiment thereof) with a transferrin and modulating activity of the one or more transferrin receptors (see, e.g., U.S. Patent Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

The compounds of the invention inhibit RIP1 kinase activity. Accordingly, the compounds of the invention are useful for the treatment of diseases and disorders mediated by this pathway and associated with inflammation and/or necroptotic cell death. Compounds of the invention are therefore useful for the treatment or prevention of a disease or disorder selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD).

In another embodiment, compounds of the invention are useful for the treatment of one or more symptoms of the above diseases and disorders. In some embodiments, the disease or disorder is an irritable bowel disorder. In some embodiments, the disease or disorder is irritable bowel syndrome (IBS), Crohn's disease, or ulcerative colitis. In some embodiments, the disease or disorder is an ischemia-reperfusion injury of kidneys, liver and lungs. In some embodiments, the disease or disorder is a chronic kidney disease. In some embodiments, the disease or disorder is acute respiratory distress syndrome (ARDS). In some embodiments, the disease or disorder is chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCKI) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

Also provided herein is the use of a compound of the invention in therapy. In some embodiments, provided herein is the use of a compound of the invention for the treatment or prevention of the above diseases and disorders. Also provided herein is the use of a compound of the invention in the manufacture of a medicament for the treatment or prevention of the above diseases and disorders.

Also provided herein is a method of treating a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a symptom of a disease or disorder in a mammal in need of such treatment, said disease or disorder being selected from the group consisting of irritable bowel disorders (IBD), irritable bowel syndrome (B S), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a disease or disorder in a mammal in need of such treatment, said disease or disorder being selected from the group consisting of irritable bowel disorders (IBD), irritable bowel syndrome (B S), Crohn's disease, and ulcerative colitis, wherein the method comprises orally administering to said mammal a therapeutically effective amount of a compound of formula I, or a pharmaceutically acceptable salt thereof, as an orally acceptable pharmaceutical composition.

Combination Therapy

Compounds of the invention may be combined with one or more other compounds of the invention or one or more other therapeutic agent as any combination thereof, in the treatment of the diseases and disorders provided herein. For example, a compound of the invention may be administered simultaneously, sequentially or separately in combination with other therapeutic agents known to be useful for the treatment of a disease or disorder selected from those recited above.

In some embodiments, a compound provided herein may be combined with another therapeutically active agent as recited in WO 2016/027253, the contents of which are hereby incorporated by reference in their entirety. In such embodiments, the compound that inhibits RIP1 kinase in the combinations recited in WO 2016/027253 is replaced by a compound of formula I of the present disclosure.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

EXAMPLES

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe.

Glassware was oven dried and/or heat dried. $^1$H NMR spectra were obtained in deuterated $CDCl_3$, $d_6$-DMSO, $CH_3OD$ or $d_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, are reported in Hz (Hertz).

In the examples below, LCMS methods were performed for 10 or 30 minutes according to the following conditions:

Agilent 10 min LCMS Method: Experiments performed on an Agilent 1290 UHPLC coupled with Agilent MSD (6140) mass spectrometer using ESI as ionization source. The LC separation was using a Phenomenex XB-C18, 1.7 mm, 50×2.1 mm column with a 0.4 ml/minute flow rate. Solvent A is water with 0.1% FA and solvent B is acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiment.

Agilent 30 min LCMS Method: Experiments performed on an Agilent 1100 HPLC coupled with Agilent MSD mass spectrometer using ESI as ionization source. The LC separation was using an Agilent Eclipse XDB-C18, 3.5 mm, 100×3.0 mm column with a 0.7 ml/minute flow rate. Solvent A is water with 0.1% FA and solvent B is acetonitrile with 0.1% FA. The gradient consisted with 2-98% solvent B over 25.5 min and hold 98% B for 2.5 min following equilibration for 1.5 min. UV absorbance were collected at 220 nm and 254 nm and mass spec full scan was applied to all experiment.

All abbreviations used to describe reagents, reaction conditions or equipment are intended to be consistent with the definitions set forth in the following list of Abbreviations.

The chemical names of discrete compounds of the invention were typically obtained using the structure naming feature of ChemDraw naming program.

ABBREVIATIONS

ACN Acetonitrile
Boc tert-Butoxycarbonyl
DMF N,N-Dimethylformamide
DMSO Dimethyl sulfoxide
HPLC High Pressure Liquid Chromatography
LCMS Liquid Chromatography Mass Spectrometry
RP Reverse phase
RT or $R_T$ Retention time
SEM 2-(Trimethylsilyl)ethoxymethyl
THF Tetrahydrofuran

Preparative Examples

Example 1: Synthetic Method A

According to synthetic Method A, 5a-methyl-1,4,4a,5,5a,6-hexahydrocyclopropa[f]indazole-3-carboxylic acid and similar carboxylic acid systems are prepared according to the paragraph below or from procedures described in *J. Med. Chem.* (2014), 57(13), 5714-5727; *J Med. Chem.* (2015), 58(9), 3806-3816; and WO 2014023258 A1.

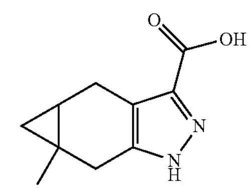

Step 1: 5a-methyl-1,4,4a,5,5a,6-hexahydrocyclopropa[f]indazole-3-carboxylic acid To a stirred solution of ethyl 5a-methyl-1,4,4a,5,5a,6-hexahydrocyclopropa[f]indazole-3-carboxylate (200 mg, 0.907 mmol) in tetrahydrofuran (10 mL) and methanol (10 mL) was added a solution of 2M LiOH (0.69 mL, 1.36 mmol), and stirred at RT for 16 h. The reaction mixture was concentrated to dryness in vacuo, redissolved in water and neutralized with 1N HCl. The resulting crashed out solid was filtered, wash with water and dried affording 5a-methyl-1,4,4a,5,5a,6-hexahydrocyclopropa[f]indazole-3-carboxylic acid (120 mg, 69% yield) used in the next step without any further purification.

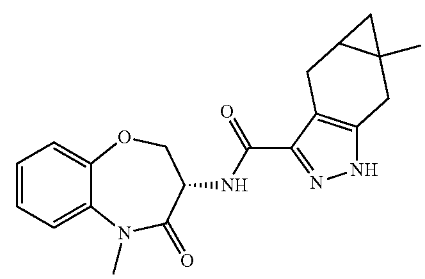 [SMILES: CN1C(=O)[C@@H](NC(=O)c2n[nH]c3c2CC2CC2(C)C3)COc2ccccc21]

Step 2: 5a-methyl-N—((S)-5-methyl-4-oxo-2,3,4,5-tetrahydrobenzo[b][1,4]oxazepin-3-yl)-1,4,4a,5,5a,6-hexahydrocyclopropa[f]indazole-3-carboxamide To a screw cap vial 5a-methyl-4,4a,5,6-tetrahydro-1H-cyclopropa[f]indazole-3-carboxylic acid (20 mg, 0.104 mmol), 1-[bis(dimethylamino)methylene]-1H-1,2,3-triazolo [4,5-b]pyridinium 3-oxide hexafluorophosphate (51 mg, 0.1357), (3S)-3-amino-5-methyl-2,3-dihydro-1,5-benzoxazepin-4-one hydrochloride (26 mg, 0.115 mmols) was added and dissolved in N,N-dimethylformamide (3 mL). To the reaction mixture was added trimethylamine (0.101 mL, 0.728 mmol), the vial was capped and stirred at RT for 16 h. The mixture was concentrated to dryness in vacuo and the residue was purified by RP-HPLC affording 5a-methyl-N—((S)-5-methyl-4-oxo-2,3,4,5-tetrahydrobenzo[b][1,4]oxazepin-3-yl)-1,4,4a,5,5a, 6-hexahydrocyclopropa[f]indazole-3-carboxamide (12 mg, 31%): $^1$H NMR (400 MHz, DMSO-d6) δ 12.88 (s, 1H), 7.96-7.87 (m, 1H), 7.52-7.44 (m, 1H), 7.35-7.26 (m, 2H), 7.25-7.21 (m, 1H), 4.88-4.75 (m, 1H), 4.53-4.44 (m, 1H), 4.43-4.36 (m, 1H), 3.11-3.02 (m, 1H), 2.98-2.90 (m, 1H), 2.79-2.70 (m, 1H), 2.70-2.60 (m, 1H), 1.19 (s, 3H), 1.03-0.93 (m, 1H), 0.35-0.26 (m, 1H), 0.09-0.00 (m, 1H). LC-MS $R_T$=4.98 min, m/z=367.2 (M+H)$^+$.

Example 2: Method A'

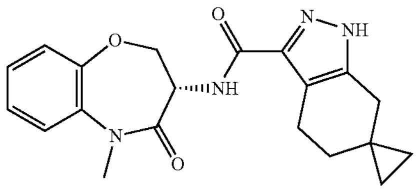 [SMILES: CN1C(=O)[C@@H](NC(=O)c2n[nH]c3c2CCC2(CC2)C3)COc2ccccc21]

Step 1: (S)—N-(5-methyl-4-oxo-2,3,4,5-tetrahydrobenzo[b][1,4]oxazepin-3-yl)-1',4',5',7'-tetrahydrospiro[cyclopropane-1,6'-indazole]-3'-carboxamide To a solution of 1'-((2-(trimethylsilyl)ethoxy)methyl)-1',4',5',7'-tetrahydrospiro[cyclopropane-1,6'-indazole]-3'-carboxylic acid (68 mg, 0.21 mmol) in N,N-dimethylformamide (0.350 mL) was added (3S)-3-amino-5-methyl-2,3-dihydro-1,5-benzoxazepin-4-one (40 mg, 0.21 mmol), 1-[bis(dimethylamino)methylene]-1H-1,2,3-triazolo[4,5-b]pyridinium 3-oxide hexafluorophosphate (86 mg, 1.3527 mmol) and triethylamine (0.171 mL, 0.0012 mmol) and stirred at RT for 16 h. The residue was dissolved in methanol (2 mL) and a 4M solution of HCl in dioxane (0.135 mL, 3.66 mmol,). The reaction mixture was stirred at RT for 16 h, concentrated to dryness in vacuo and the residue was purified by RP-HPLC affording (S)—N-(5-methyl-4-oxo-2,3,4,5-tetrahydrobenzo[b][1,4]oxazepin-3-yl)-1',4',5',7'-tetrahydrospiro[cyclopropane-1,6'-indazole]-3'-carboxamide (9 mg, 12% yield): $^1$H NMR (400 MHz, DMSO-d6) δ 12.84 (s, 1H), 7.91 (d, J=8.0 Hz, 1H), 7.52-7.45 (m, 1H), 7.35-7.26 (m, 2H), 7.25-7.21 (m, 1H), 4.90-4.76 (m, 1H), 4.56-4.32 (m, 2H), 2.68-2.55 (m, 2H), 2.48-2.42 (m, 2H), 1.53-1.37 (m, 2H), 0.42-0.33 (m, 4H). LC-MS $R_T$=4.64 min, m/z=367.2 $(M+H)^+$.

Example 3: Method B

According to synthetic Method B, 5-(tert-butyl)-4,5,6,7-tetrahydro-1H-indazole-3-carboxylic acid and similar carboxylic acid systems are prepared according to the paragraph below or from procedures described in *J. Med. Chem.* (2014), 57(13), 5714-5727; *J. Med. Chem.* (2015), 58(9), 3806-3816; and WO 2014023258 A1.

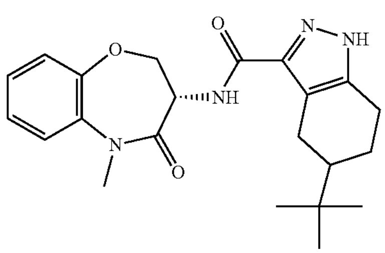 [SMILES: CN1C(=O)[C@@H](NC(=O)c2n[nH]c3c2CC(C(C)(C)C)CC3)COc2ccccc21]

5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide To a screw cap vial (3S)-3-amino-5-methyl-2,3-dihydro-1,5-benzoxazepin-4-one hydrochloride (30 mg, 0.131 mmol), 1-[bis(dimethylamino)methylene]-1H-1,2,3-triazolo[4,5-b]pyridinium 3-oxide hexafluorophosphate (75 mg, 0.197 mmol), 5-(tert-butyl)-4,5,6,7-tetrahydro-1H-indazole-3-carboxylic acid (35 mg, 0.157 mmols) was added and dissolved in N,N-dimethylformamide (5 mL). To the reaction mixture was added trimethylamine (0.127 mL, 0.918 mmol), the vial was capped and stirred at RT for 16 h. The mixture was concentrated to dryness in vacuo and the residue was purified by RP-HPLC affording 5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide (9 mg, 14%): $^1$H NMR (400 MHz, DMSO-d6) δ 12.88-12.77 (m, 1H), 7.91 (d, J=7.9 Hz, 1H), 7.51-7.46 (m, 1H), 7.35-7.26 (m, 2H), 7.27-7.19 (m, 1H), 4.88-4.77 (m, 1H), 4.55-4.35 (m, 2H), 2.86-2.65 (m, 2H), 2.19-2.05 (m, 1H), 2.01-1.91 (m, 1H), 1.37-1.17 (m, 2H), 0.89 (s, 9H). LCMS $R_T$=5.52 min, m/z=397.2 $[M+H]^+$.

Example 4: Method B'

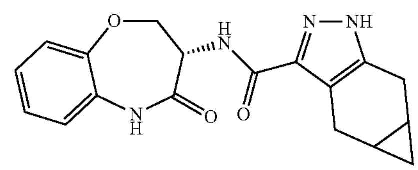 [SMILES: O=C(N[C@H]1COc2ccccc2NC1=O)c1n[nH]c2c1CC1CC1C2]

Step 1: N—((S)-4-oxo-2,3,4,5-tetrahydrobenzo[b][1,4]oxazepin-3-yl)-1,4,4a,5,5a,6-hexahydrocyclopropa[f]indazole-3-carboxamide To a screw cap vial 1,4,4a,5,5a,6-hexahydrocyclopropa[f]indazole-3-carboxylic acid (44 mg, 0.247 mmol), 3-[bis(dimethylamino)methyliumyl]-3H-benzotriazol-1-oxide hexafluorophosphate (127 mg, 0.3367 mmol), 3S)-3-amino-3,5-dihydro-2H-1,5-benzoxazepin-4-one (40 mg, 0.225 mmol) was added and dissolved in N,N-dimethylformamide (3 mL). To the reaction mixture was added trimethylamine (0.094 mL, 0.673 mmol), the vial was capped and stirred at RT for 16 h. The mixture was concentrated to dryness in vacuo and the residue was purified by RP-HPLC affording N—((S)-4-oxo-2,3,4,5-tetrahydrobenzo[b][1,4]oxazepin-3-yl)-1,4,4a,5,5a,6-hexahydrocyclopropa[f]indazole-3-carboxamide (10.4 mg, 14%) as a white solid: $^1$H NMR (400 MHz, DMSO-d6) δ 12.87 (s, 1H), 10.12 (s, 1H), 8.02-7.87 (m, 1H), 7.22-7.05 (m, 4H), 4.87-4.66 (m, 1H), 4.55-4.32 (m, 2H), 3.23-3.09 (m, 1H), 3.00-2.62 (m, 4H), 2.15-2.01 (m, 1H), 1.32-1.09 (m, 2H), 0.62-0.40 (m, 1H), −0.05-−0.14 (m, 1H). LCMS $R_T$=4.21 min, m/z=339.1 $[M+H]^+$.

Example 5: Method C

According to synthetic Method C, 5-tert-butoxycarbonyl-1-(2-trimethylsilylethoxymethyl)-6,7-dihydro-4H-pyrazolo[4,3-c]pyridine-3-carboxylic acid and similar carboxylic acid systems are prepared according to the paragraph below or from procedures described in *J. Med. Chem.* (2014), 57(13), 5714-5727; *J. Med. Chem.* (2015), 58(9), 3806-3816; and WO 2014023258 A1.

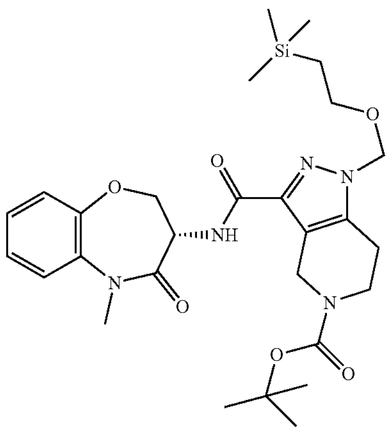 [SMILES: CN1C(=O)[C@@H](NC(=O)c2nn(COCC[Si](C)(C)C)c3c2CN(C(=O)OC(C)(C)C)CC3)COc2ccccc21]

Step 1: tert-butyl (S)-3-((5-methyl-4-oxo-2,3,4,5-tetrahydrobenzo[b][1,4]oxazepin-3-yl)carbamoyl)-1-((2-(trimethylsilyl) ethoxy)methyl)-1,4,6,7-tetrahydro-5H-pyrazolo[4,3-c]pyridine-5-carboxylate To a solution of 5-tert-butoxycarbonyl-1-(2-trimethylsilylethoxymethyl)-6,7-dihydro-4H-pyrazolo[4,3-c]pyridine-3-carboxylic acid (455 mg, 1.15 mmol) in N,N-dimethylformamide (5 mL) was added (3S)-3-amino-5-methyl-2,3-dihydro-1,5-benzoxazepin-4-one (200 mg, 1.0405 mmol), 1-[bis(dimethylamino)methylene]-1H-1,2,3-triazolo[4,5-b] pyridinium 3-oxide hexafluorophosphate (524.83 mg, 1.3527 mmol) and N,N-diisopropylethylamine (1.27 mL, 7.2837 mmol) and stirred at RT for 16 h. To the reaction mixture was concentrated to dryness in vacuo and the residue was purified by flash column chromatography (silica gel, 100-200 mesh, 0 to 20% methanol in dichloromethane) to afford tert-butyl (S)-3-((5-methyl-4-oxo-2,3,4,5-tetrahydrobenzo[b][1,4]oxazepin-3-yl)carbamoyl)-1-((2-(trimethylsilyl) ethoxy)methyl)-1,4,6,7-tetrahydro-5H-pyrazolo[4,3-c]pyridine-5-carboxylate (523 mg, 88%) as a colorless oil: LCMS $R_T$=1.62 min, m/z=572.1 [M+H]$^+$.

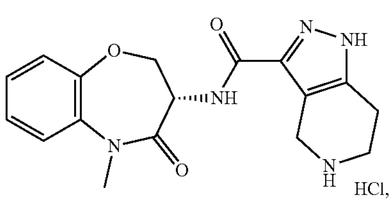 [SMILES: CN1C(=O)[C@@H](NC(=O)c2n[nH]c3c2CNCC3)COc2ccccc21]

HCl,

Step 2: (S)—N-(5-methyl-4-oxo-2,3,4,5-tetrahydrobenzo[b][1,4]oxazepin-3-yl)-4,5,6,7-tetrahydro-1H-pyrazolo[4,3-c]pyridine-3-carboxamide hydrochloride To a stirred solution of tert-butyl 3-[[(3S)-5-methyl-4-oxo-2,3-dihydro-1,5-benzoxazepin-3-yl]carbamoyl]-1-(2-trimethylsilylethoxymethyl)-6,7-dihydro-4H-pyrazolo[4,3-c]pyridine-5-carboxylate (523 mg, 0.915 mmol) in methanol was added a 4M solution of HCl in dioxane (0.915 mL, 3.66 mmol). The reaction mixture was stirred at RT for 16 h and concentrated to dryness in vacuo to afford crude (S)—N-(5-methyl-4-oxo-2,3,4,5-tetrahydrobenzo[b][1,4]oxazepin-3-yl)-4,5,6,7-tetrahydro-1H-pyrazolo[4,3-c]pyridine-3-carboxamide hydrochloride (317 mg, 92%) used in the next step without further purification: LCMS $R_T$=0.77 min, m/z=342.1 [M+H]$^+$.

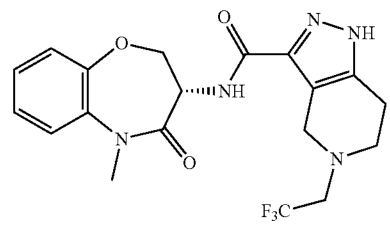 [SMILES: CN1C(=O)[C@@H](NC(=O)c2n[nH]c3c2CN(CC(F)(F)F)CC3)COc2ccccc21]

Step 3: (S)—N-(5-methyl-4-oxo-2,3,4,5-tetrahydrobenzo[b][1,4]oxazepin-3-yl)-5-(2,2,2-trifluoroethyl)-4,5,6,7-tetrahydro-1H-pyrazolo[4,3-c]pyridine-3-carboxamide To a stirred solution of N-[(3S)-5-methyl-4-oxo-2,3-dihydro-1,5-benzoxazepin-3-yl]-4,5,6,7-tetrahydro-1H-pyrazolo[4,3-c]pyridine-3-carboxamide hydrochloride (30 mg, 0.07941 mmol) in dichloromethane was added N,N-diisopropylethylamine (0.0416 mL., 0.2382 mmol). To the reaction mixture was added 2,2,2-trifluoroethyltrifluoromethanesulphonate (24.70 mg, 0.1032 mmol) and was stirred at 35° C. for 16 h. The reaction mixture was concentrated to dryness in vacuo and the residue was purified by RP-HPLC to afford (S)—N-(5-methyl-4-oxo-2,3,4,5-tetrahydrobenzo[b][1,4]oxazepin-3-yl)-5-(2,2,2-trifluoroethyl)-4,5,6,7-tetrahydro-1H-pyrazolo[4,3-c]pyridine-3-carboxamide (13 mg, 38%) as a white solid: $^1$H NMR (400 MHz, DMSO-d6) δ 13.03 (s, 1H), 8.01 (d, J=8.0 Hz, 1H), 7.48 (dd, J=7.7, 1.8 Hz, 1H), 7.35-7.26 (m, 2H), 7.23 (dd, J=7.7, 1.8 Hz, 1H), 4.87-4.75 (m, 1H), 4.58-4.47 (m, 1H), 4.44-4.35 (m, 1H), 3.74 (s, 2H), 2.89 (t, J=5.7 Hz, 2H), 2.69 (t, J=5.6 Hz, 2H).

Example 6: Method D

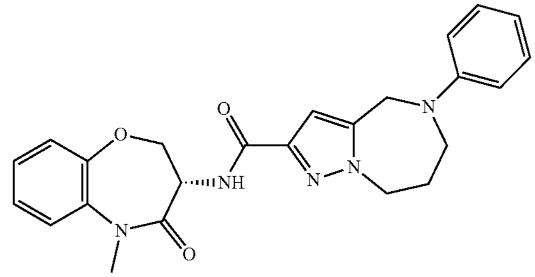 [SMILES: CN1C(=O)[C@@H](NC(=O)c2cc3n(n2)CCCN(c2ccccc2)C3)COc2ccccc21]

N-[(3S)-5-methyl-4-oxo-2,3-dihydro-1,5-benzoxazepin-3-yl]-5-phenyl-4,6,7,8-tetrahydro pyrazolo[1,5-a][1,4]diazepine-2-carboxamide

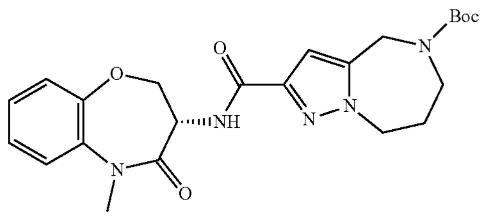 [SMILES: CN1C(=O)[C@@H](NC(=O)c2cc3n(n2)CCCN(C(=O)OC(C)(C)C)C3)COc2ccccc21]

Step 1: tert-butyl 2-[[(3S)-5-methyl-4-oxo-2,3-dihydro-1,5-benzoxazepin-3-yl]carbamoyl]-4,6,7,8-tetrahydropyrazolo[1,5-a][1,4]diazepine-5-carboxylate To a solution of 5-tert-butoxycarbonyl-4,6,7,8-tetrahydropyrazolo[1,5-a][1,4]diazepine-2-carboxylic acid (500 mg, 1.78 mmol) in N,N-dimethylformamide (5 mL) was added (3S)-3-amino-5-methyl-2,3-dihydro-1,5-benzoxazepin-4-one (376 mg, 1.96 mmol) 1-hydroxybenzotriazole (288 mg, 2.13 mmol), 1-(3-dimethylaminopropyl)-3-ethylcarbodimide hydrochloride (409 mg, 2.13 mmol). The reaction mixture was stirred at RT for 2 h and then diluted with ethyl acetate (15 mL). The solution was washed with water (3×15 mL), brine (3×15 mL), dried over anhydrous sodium sulfate and concentrated to dryness in vacuo. The residue was purified by flash column chromatography (silica gel, 100-200 mesh, 0 to 50% ethyl acetate in petroleum ether) to afford tert-butyl 2-[[(3S)-5-methyl-4-oxo-2,3-dihydro-1,5-benzoxazepin-3-yl]carbamoyl]-4,6,7,8-tetrahydropyrazolo[1,5-a][1,4]diazepine-5-carboxylate (800 mg, 99% yield) as a light yellow oil: LCMS (5 to 95% acetonitrile in water+0.03% trifluoacetic acid over 1.5 mins) retention time 0.72 min, ESI+ found [M+H]=456.

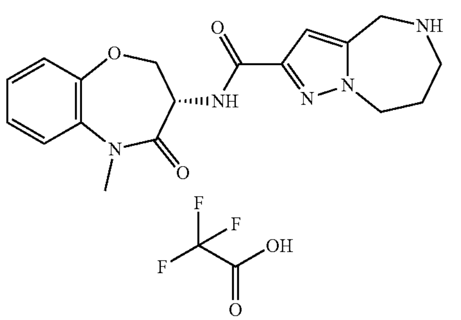

Step 2: N-[(3S)-5-methyl-4-oxo-2,3-dihydro-1,5-benzoxazepin-3-yl]-5,6,7,8-tetrahydro-4H-pyrazolo[1,5-a][1,4]diazepine-2-carboxamide 2,2,2-trifluoroacetate To a solution of tert-butyl 2-[[(3S)-5-methyl-4-oxo-2,3-dihydro-1,5-benzoxazepin-3-yl]carbamoyl]-4,6,7,8-tetrahydropyrazolo[1,5-a][1,4]diazepine-5-carboxylate (780 mg, 1.71 mmol) in dichloromethane (5 mL) was added trifluoroacetic acid (1 mL). The reaction mixture was stirred at RT for 2 h and then concentrated to dryness in vacuo affording N-[(3S)-5-methyl-4-oxo-2,3-dihydro-1,5-benzoxazepin-3-yl]-5,6,7,8-tetrahydro-4H-pyrazolo[1,5-a][1,4]diazepine-2-carboxamide 2,2,2-trifluoroacetate (802 mg, 100% yield) as a yellow solid used as is in the next step: LCMS (5 to 95% acetonitrile in water+0.03% trifluoacetic acid over 1.5 mins) retention time 0.29 min, ESI+ found [M+H]=356.

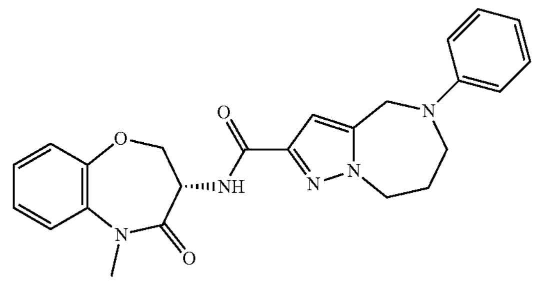 [SMILES: CN1C(=O)[C@@H](NC(=O)c2cc3n(n2)CCCN(c2ccccc2)C3)COc2ccccc21]

Step 3: N-[(3S)-5-methyl-4-oxo-2,3-dihydro-1,5-benzoxazepin-3-yl]-5-phenyl-4,6,7,8-tetrahydro pyrazolo[1,5-a][1,4]diazepine-2-carboxamide To a mixture of N-[(3S)-5-methyl-4-oxo-2,3-dihydro-1,5-benzoxazepin-3-yl]-5,6,7,8-tetrahydro-4H-pyrazolo[1,5-a][1,4]diazepine-2-carboxamide 2,2,2-trifluoroacetate (197 mg, 0.42 mmol) in toluene (5 mL) was added copper(II) acetate (8 mg, 0.04 mmol), tetradecanoic acid (19 mg, 0.08 mmol), 2,6-lutidine (45 mg, 0.42 mmol) and phenylboronic acid (77 mg, 0.63 mmol) under oxygen (15 Psi). The reaction mixture was stirred at 25° C. for 12 h and concentrated to dryness in vacuo. The residue was purified by RP-HPLC (0-40% acetonitrile in water and 0.1% ammonium hydroxide) affording N-[(3S)-5-methyl-4-oxo-2,3-dihydro-1,5-benzoxazepin-3-yl]-5-phenyl-4,6,7,8-tetrahydropyrazolo[1,5-a][1,4]diazepine-2-carboxamide (2.5 mg, 1.4% yield) as white solid: $^1$H NMR (400 MHz, DMSO-d6) δ 7.93 (d, J=8.0 Hz, 1H), 7.51-7.44 (m, 1H), 7.35-7.18 (m, 3H), 7.10 (t, J=8.0 Hz, 2H), 6.86 (d, J=8.4 Hz, 2H), 6.73 (s, 1H), 6.58 (t, J=7.2 Hz, 1H), 4.83-4.64 (m, 3H), 4.54-4.40 (m, 3H), 4.37-434 (m, 1H), 3.93-3.79 (m, 2H), 3.29 (s, 3H), 1.84-1.82 (m, 2H). LCMS $R_T$=2.45 min, m/z=432.2 $[M+H]^+$.

LCMS (0 to 60% acetonitrile in water+0.05% ammonium bicarbonate over 3 mins) retention time 2.45 min, ESI+ found [M+H]=432.2.

Example 7: Method E

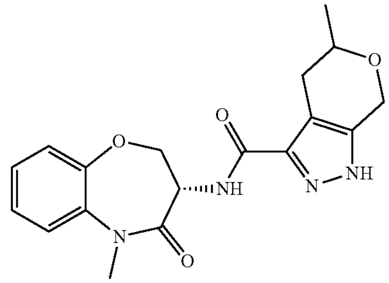

and

-continued

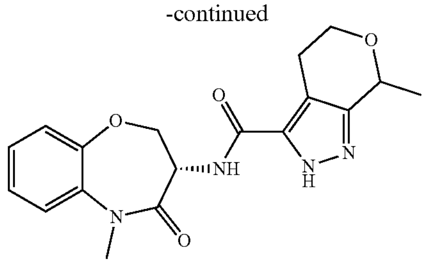

5-methyl-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide and 7-methyl-N—((S)-5-methyl-4-oxo-2,3,4,5-tetrahydrobenzo[b][1,4]oxazepin-3-yl)-2,4,5,7-tetrahydropyrano[3,4-c]pyrazole-3-carboxamide Step 1

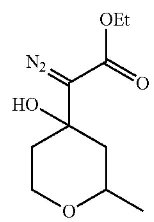

Ethyl 2-diazo-2-(4-hydroxy-2-methyltetrahydro-2H-pyran-4-yl) acetate

To a solution of ethyl 2-diazoacetate (8.0 g, 70.1 mmol) and 2-methyldihydro-2H-pyran-4(3H)-one (5.0 g, 43.8 mmol) in tetrahydrofuran (100 mL) was added lithium diisopropylamide (2 M in tetrahydrofuran, 39.5 mL, 79.0 mmol) at −78° C. under nitrogen. After addition, the reaction mixture was stirred at −78° C. for 1 h and then quenched by addition of saturated aqueous ammonium chloride (60 mL). The resulting mixture was extracted with ethyl acetate (3×100 mL). The combined organic layers were dried over anhydrous sodium sulfate and concentrated to dryness in vacuo. The residue was purified by column chromatography (silica gel, 100-200 mesh, 0 to 20% ethyl acetate in petroleum ether) to afford ethyl 2-diazo-2-(4-hydroxy-2-methyltetrahydropyran-4-yl)acetate (4.0 g, 40% yield).

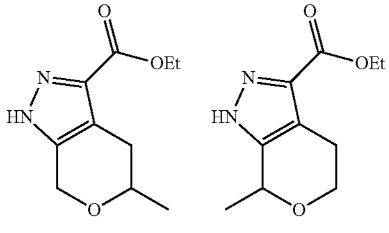

Step 2: Ethyl 5-methyl-1,4,5,7-tetrahydropyrano[3,4-c]pyrazole-3-carboxylate and ethyl 7-methyl-1,4,5,7-tetrahydropyrano[3,4-c]pyrazole-3-carboxylate To a solution of ethyl 2-diazo-2-(4-hydroxy-2-methyltetrahydropyran-4-yl)acetate (3.0 g, 13.1 mmol) in pyridine (20 mL) was added phosphorus oxychloride (8.06 g, 52.6 mmol). The resulting mixture was stirred at 15° C. for 3 h and then poured into water (20 mL). The mixture was extracted with dichloromethane (3×20 mL). The combined organic layer was dried over anhydrous sodium sulfate and concentrated to dryness in vacuo. The residue was purified by column chromatography (silica gel, 100-200 mesh, 0 to 25% ethyl acetate in petroleum ether) to afford a mixture of regio-isomer, which was further purified by RP-HPLC (15-45% acetonitrile in water and 0.05% ammonia) to afford ethyl 5-methyl-1,4,5,7-tetrahydropyrano[3,4-c]pyrazole-3-carboxylate (300 mg, 10.9% yield) and ethyl 7-methyl-1,4,5,7-tetrahydropyrano[3,4-c]pyrazole-3-carboxylate (300 mg, 1.427 mmol, 10.9% yield) as white solids.

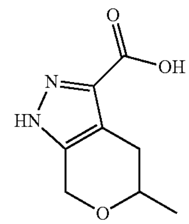

Step 3: 5-methyl-1,4,5,7-tetrahydropyrano[3,4-c]pyrazole-3-carboxylic acid

To a solution of ethyl 5-methyl-2,4,5,7-tetrahydropyrano[3,4-c]pyrazole-3-carboxylate (100 mg, 0.48 mmol) in tetrahydrofuran (3 mL) and water (3 mL) was added lithium hydroxide monohydrate (320 mg, 7.61 mmol). The reaction mixture was stirred at 15° C. for 15 h and then concentrated to dryness in vacuo. The residue was diluted with water (5 mL) and then adjusted to pH=3 by adding 1 N hydrochloric acid. The mixture was extracted with dichloromethane (3×15 mL). The combined layers were dried over anhydrous sodium sulfate and concentrated to afford 5-methyl-1,4,5,7-tetrahydropyrano[3,4-c]pyrazole-3-carboxylic acid (80 mg, 92.3% yield) as a white solid, which was used into next step without further purification.

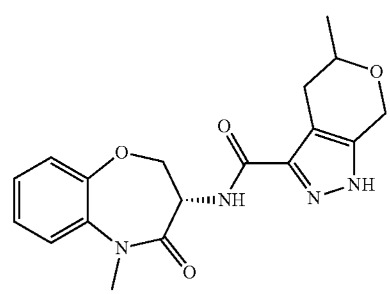 [SMILES: CC1Cc2c(C(=O)N[C@H]3COc4ccccc4N(C)C3=O)n[nH]c2CO1]

Step 4: 5-methyl-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide To a solution of (3S)-3-amino-5-methyl-2,3-dihydro-1,5-benzoxazepin-4-one (60 mg, 0.31 mmol) in N,N-dimethylformamide (5 mL) was added 1H-benzo[d][1,2,3]triazol-1-ol (50 mg, 0.37 mmol), $N^1$-((ethylimino)methylene)-$N^3$,$N^3$-dimethylpropane-1,3-diamine hydrochloride (72 mg, 0.37 mmol) and 5-methyl-1,4,5,7-tetrahydropyrano[3,4-c]pyrazole-3-carboxylic acid (63 mg, 0.34 mmol). The reaction mixture was stirred at 15° C. for 1 h and then concentrated to dryness in vacuo. The residue was purified by RP-HPLC (28-58% acetonitrile in water and 0.05% hydrochloric acid) to afford 5-methyl-N-[(3S)-5-methyl-4-oxo-2,3-dihydro-1,5-benzoxazepin-3-yl]-1,4,5,7-tetrahydropyrano[3,4-c]pyrazole-3-carboxamide (55.7 mg, 49% yield) as a white solid: $^1$H NMR (400 MHz, Methanol-d4) δ 7.44-7.40 (m, 1H), 7.35-7.26 (m, 2H), 7.25-7.20 (m, 1H), 5.01-4.97 (m, 1H), 4.82-4.77 (m, 1H), 4.72-4.70 (m, 1H), 4.61-4.57 (m, 1H), 4.41-4.33 (m, 1H), 3.70-3.66 (m, 1H), 3.41 (s, 3H), 2.87-2.82 (m, 1H), 2.50-2.44 (m, 1H), 1.32 (d, J=6.0 Hz, 3H). LCMS (2 to 98% acetonitrile in water+0.1% formic acid over 2 mins) retention time 0.77 min, ESI+ found [M+H]=357.0.

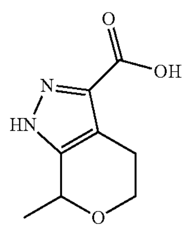

Step 5: 7-methyl-1,4,5,7-tetrahydropyrano[3,4-c]pyrazole-3-carboxylic acid

To a solution of ethyl 7-methyl-1,4,5,7-tetrahydropyrano[3,4-c]hpyrazole-3-carboxylate (100 mg, 0.48 mmol) in tetrahydrofuran (3 mL) and water (3 mL) was added lithium hydroxide monohydrate (320 mg, 7.61 mmol). The reaction mixture was stirred at 15° C. for 15 h and then concentrated to dryness in vacuo. The residue was diluted with water (5 mL) and then adjusted to pH=3 by adding 1 N hydrochloric acid. The mixture was extracted with dichloromethane (3×15 mL). The combined layers were dried over anhydrous sodium sulfate and concentrated to afford 7-methyl-1,4,5,7-tetrahydropyrano[3,4-c]hpyrazole-3-carboxylic acid (~80 mg, 92.3% yield) as a white solid used in the next step without further purification.

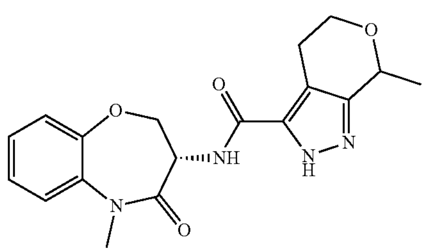 [SMILES: CC1OCCc2c1n[nH]c2C(=O)N[C@H]1COc2ccccc2N(C)C1=O]

Step 6: 7-methyl-N—((S)-5-methyl-4-oxo-2,3,4,5-tetrahydrobenzo[b][1,4]oxazepin-3-yl)-2,4,5,7-tetrahydropyrano[3,4-c]pyrazole-3-carboxamide To a solution of (3S)-3-amino-5-methyl-2,3-dihydro-1,5-benzoxazepin-4-one (60 mg, 0.31 mmol) in N,N-dimethylformamide (5 mL) was added 1H-benzo[d][1,2,3]triazol-1-ol (50 mg, 0.37 mmol), $N^1$-((ethylimino)methylene)-$N^3$,$N^3$-dimethylpropane-1,3-diamine hydrochloride (72 mg, 0.37 mmol) and 7-methyl-2,4,5,7-tetrahydropyrano[3,4-c]pyrazole-3-carboxylic acid (63 mg, 0.34 mmol). The reaction mixture was stirred at 15° C. for 1 h and concentrated to dryness in vacuo. The residue was purified by RP-HPLC (25-48% acetonitrile in water and 0.05% hydrochloric acid) to afford 7-methyl-N-[(3S)-5-methyl-4-oxo-2,3-dihydro-1,5-benzoxazepin-3-yl]-2,4,5,7-tetrahydropyrano[3,4-c]pyrazole-3-carboxamide (39.8 mg, 35% yield) as a white solid: $^1$H NMR (400 MHz, Methanol-d4) δ 7.44-7.40 (m, 1H), 7.35-7.26 (m, 2H), 7.25-7.20 (m, 1H), 4.99-4.91 (m, 1H), 4.77-4.75 (m, 1H), 4.62-4.56 (m, 1H), 4.41-4.33 (m, 1H), 4.19-4.12 (m, 1H), 3.62-3.60 (m, 1H), 3.41 (s, 3H), 2.80-2.73 (m, 1H), 1.47 (d, J=6.8 Hz, 3H). LCMS (2 to 98% acetonitrile in water+0.1% formic acid over 2 mins) retention time 0.76 min, ESI+ found [M+H]=357.0.

Example 8: Method F

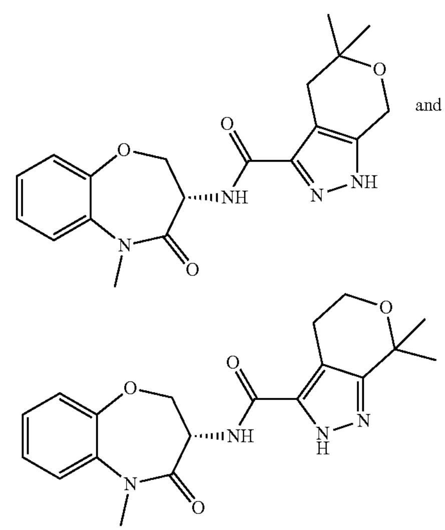

(S)-5,5-dimethyl-N-(5-methyl-4-oxo-2,3,4,5-tetrahydrobenzo[b][1,4]oxazepin-3-yl)-1,4,5,7-tetrahydropyrano[3,4-c]pyrazole-3-carboxamide and (S)-7,7-dimethyl-N-(5-methyl-4-oxo-2,3,4,5-tetrahydrobenzo[b][1,4]oxazepin-3-yl)-2,4,5,7-tetrahydropyrano[3,4-c]pyrazole-3-carboxamide

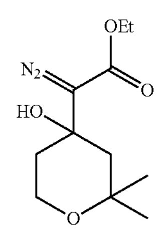

Step 1: Ethyl 2-diazo-2-(4-hydroxy-2,2-dimethyltetrahydro-2H-pyran-4-yl) acetate To a solution of 2,2-dimethyl tetrehydropyran-4-one (5.0 g, 39.0 mmol) and ethyl diazoacetate (7.1 g, 62.4 mmol) in tetrahydrofuran (100 mL) was added lithium diisopropylamide (2 M in tetrahydrofuran, 35.1 mL, 70.2 mmol) at −78° C. under nitrogen. After addition, the reaction mixture was stirred at −78° C. for 1 h and then quenched by addition of saturated aqueous ammonium chloride (60 mL). The mixture was extracted with ethyl acetate (3×100 mL). The combined organic layers were dried over anhydrous sodium sulfate and concentrated to dryness in vacuo. The residue was purified by column chromatography (silica gel, 100-200 mesh, 0 to 20% ethyl acetate in petroleum ether) to afford ethyl 2-diazo-2-(4-hydroxy-2,2-dimethyl-tetrahydropyran-4-yl) acetate (6.0 g, 63.5% yield) as a yellow oil use as is in the next step.

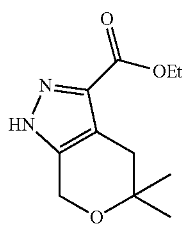

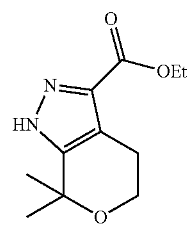

Step 2: ethyl 5,5-dimethyl-1,4,5,7-tetrahydropyrano[3,4-c]pyrazole-3-carboxylate and ethyl 7,7-dimethyl-1,4,5,7-tetrahydropyrano[3,4-c]pyrazole-3-carboxylate To a solution of ethyl 2-diazo-2-(4-hydroxy-2,2-dimethyl-tetrahydropyran-4-yl) acetate (3.0 g, 12.38 mmol) in pyridine (60 mL) was added phosphorus oxychloride (7.6 g, 49.53 mmol). The reaction mixture was stirred at 15° C. for 3 h and then poured into water (30 mL). The mixture was extracted with dichloromethane (3×50 mL). The combined organic layers were dried over anhydrous sodium sulfate and concentrated to dryness in vacuo. The residue was purified by column chromatography (silica gel, 100-200 mesh, 0 to 25% ethyl acetate in petroleum ether) to afford a mixture of ethyl 7,7-dimethyl-4,5-dihydro-1H-pyrano[3,4-c]pyrazole-3-carboxylate and ethyl 7,7-dimethyl-4,5-dihydro-1H-pyrano[3,4-c]pyrazole-3-carboxylate (1.0 g, 36% yield, 1:1 mixture) as light yellow oil used as is in the next step: LCMS $R_T$=0.62 min, m/z=224.8 [M+H]$^+$. LCMS (2 to 98% acetonitrile in water+0.1% formic acid over 2 mins) retention time 0.615 min, ESI+ found [M+H]=224.8.

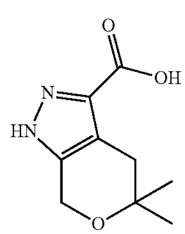

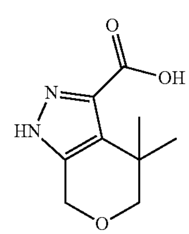

Step 3: 5,5-dimethyl-1,4,5,7-tetrahydropyrano[3,4-c]pyrazole-3-carboxylic acid and 4,4-dimethyl-1,4,6,7-tetrahydropyrano[4,3-c]pyrazole-3-carboxylic acid To a solution of ethyl 5,5-dimethyl-4,7-dihydro-2H-pyrano[3,4-c]pyrazole-3-carboxylate and ethyl 7,7-dimethyl-4,5-dihydro-1H-pyrano[3,4-c]pyrazole-3-carboxylate (200 mg, 0.9 mmol) in tetrahydrofuran (10 mL) and water (10 mL) was added lithium hydroxide monohydrate (299 mg, 7.1 mmol). The reaction mixture was stirred at 15° C. for 15 h and concentrated to dryness in vacuo. The residue was diluted with water (5 mL) and adjusted to pH=3 with 1M hydrochloric acid. The resulting mixture was extracted with dichloromethane (3×15 mL). The combined organic layers were dried over anhydrous sodium sulfate and concentrated to dryness in vacuo to afford a crude mixture of 5,5-dimethyl-4,7-dihydro-1H-pyrano[3,4-c]pyrazole-3-carboxylic acid and 7,7-dimethyl-4,5-dihydro-1H-pyrano[3,4-c]pyrazole-3-carboxylic acid (120 mg, 68.6% yield) as a yellow oil used in the next step without any further purification.

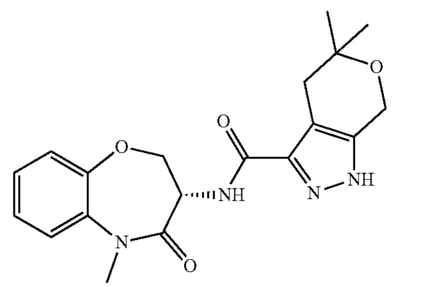

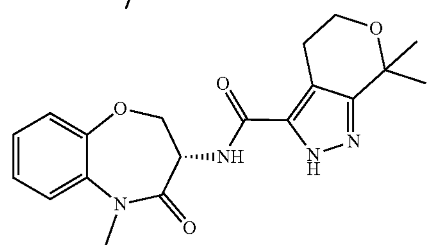

Step 4: (S)-5,5-dimethyl-N-(5-methyl-4-oxo-2,3,4,5-tetrahydrobenzo[b][1,4]oxazepin-3-yl)-1,4,5,7-tetrahydropyrano[3,4-c]pyrazole-3-carboxamide To a solution of (3S)-3-amino-5-methyl-2,3-dihydro-1,5-benzoxazepin-4-one (100 mg, 0.52 mmol) in N,N-dimethylformamide (5 mL) was added a mixture of 5,5-dimethyl-4,7-dihydro-1H-pyrano[3,4-c]pyrazole-3-carboxylic acid and 7,7-dimethyl-4,5-dihydro-2H-pyrano[3,4-c]pyrazole-3-carboxylic acid (118 mg, 0.60 mmol), 1H-benzo[d][1,2,3]triazol-1-ol (83 mg, 0.62 mmol) and $N^1$-((ethylimino)methylene)-$N^3$,$N^3$-dimethylpropane-1,3-diamine hydrochloride (99 mg, 0.52 mmol). The reaction mixture was stirred at 15° C. for 1 h and concentrated to dryness in vacuo. The residue was purified by RP-HPLC (17-37% acetonitrile in water and 0.05% ammonia hydroxide) to afford:

5,5-dimethyl-N-[(3S)-5-methyl-4-oxo-2,3-dihydro-1,5-benzoxazepin-3-yl]-4,7-dihydro-1H-pyrano[3,4-c]pyrazole-3-carboxamide (59 mg, 30.7% yield) as white solid: $^1$H NMR (400 MHz, Methanol-d4) δ 7.44-7.40 (m, 1H), 7.35-7.26 (m, 2H), 7.25-7.20 (m, 1H), 5.01-4.97 (m, 1H), 4.71 (s, 2H), 4.62-4.57 (m, 1H), 4.39-4.36 (m, 1H), 3.42 (s, 3H), 2.68 (s, 2H), 1.25 (s, 6H). LCMS (2 to 98% acetonitrile in water+0.1% formic acid over 2 mins) retention time 0.79 min, ESI+ found [M+H]=371.0.

7,7-dimethyl-N-[(3S)-5-methyl-4-oxo-2,3-dihydro-1,5-benzoxazepin-3-yl]-4,5-dihydro-2H-pyrano[3,4-c]pyrazole-3-carboxamide (20 mg, 10.4% yield) as white solid: $^1$H NMR (400 MHz, METHANOL-d4) δ 13.10 (s, 1H), 7.99 (d, J=7.6 Hz, 1H), 7.49 (d, J=7.6 Hz, 1H), 7.34-7.22 (m, 3H), 4.87-4.80 (m, 1H), 4.55-4.49 (m, 1H), 4.42-4.37 (m, 1H), 3.73 (s, 2H), 3.31 (s, 3H), 2.58-2.20 (m, 2H), 1.39 (s, 6H). LCMS (2 to 98% acetonitrile in water+0.1% formic acid over 2 mins) retention time 0.78 min, ESI+ found [M+H]=371.0.

Example 9: Method G

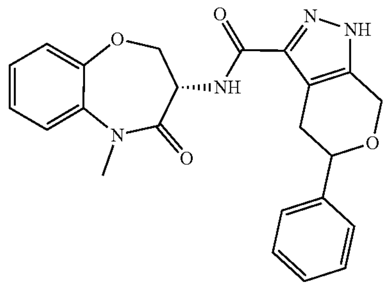 [SMILES: CN1C(=O)[C@@H](NC(=O)c2n[nH]c3c2CC(c2ccccc2)OC3)COc2ccccc21]

N—((S)-5-methyl-4-oxo-2,3,4,5-tetrahydrobenzo[b][1,4]oxazepin-3-yl)-5-phenyl-1,4,5,7-tetrahydropyrano[3,4-c]pyrazole-3-carboxamide

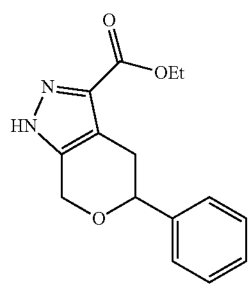 [SMILES: CCOC(=O)c1n[nH]c2c1CC(c1ccccc1)OC2]

Step 1: Ethyl 5-phenyl-1,4,5,7-tetrahydropyrano[3,4-c]pyrazole-3-carboxylate

To a solution of 2-phenyltetrahydropyran-4-one (1.00 g, 5.68 mmol) in dimethyl sulfoxide (10 mL) was added ethyl diazoacetate (0.32 g, 2.84 mmol) and pyrrolidine (40.3 mg, 0.57 mmol) under nitrogen protection. The reaction mixture was stirred at RT for 12 h and diluted with ethyl acetate (100 mL). The resulting mixture was washed with water (3×50 mL), brine (3×50 mL), dried over anhydrous sodium sulfate and concentrated to dryness in vacuo. The residue was purified by column chromatography (silica gel, 100-200 mesh, 0 to 50% ethyl acetate in petroleum ether) to afford ethyl 5-phenyl-1,4,5,7-tetrahydropyrano[3,4-c]pyrazole-3-carboxylate (180 mg, 12% yield) as a light yellow oil: LCMS (5 to 95% acetonitrile in water+0.03% trifluoacetic acid over 1.5 mins) retention time 0.70 min, ESI+ found [M+H]=273.

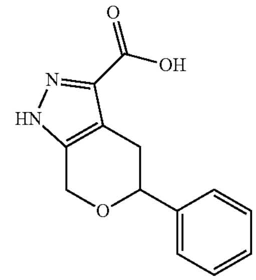 [SMILES: O=C(O)c1n[nH]c2c1CC(c1ccccc1)OC2]

Step 2: 5-phenyl-1,4,5,7-tetrahydropyrano[3,4-c]pyrazole-3-carboxylic acid

To a solution of ethyl 5-phenyl-1,4,5,7-tetrahydropyrano[3,4-c]pyrazole-3-carboxylate (100 mg, 0.37 mmol) in ethanol (4 mL) and water (4 mL) was added lithium hydroxide monohydrate (154 mg, 3.67 mmol). The reaction mixture was stirred at RT for 12 h and concentrated to dryness in vacuo. The residue was diluted with water (5 mL) and adjusted to pH=5 with 1M hydrochloric acid. The mixture was extracted with dichloromethane (3×30 mL). The combined organic layers were dried over anhydrous sodium sulfate and concentrated to dryness in vacuo to afford 5-phenyl-1,4,5,7-tetrahydropyrano[3,4-c]pyrazole-3-carboxylic acid (89 mg, 99% yield) as yellow oil used in the next step without any further purification: LCMS (5 to 95% acetonitrile in water+0.03% trifluoacetic acid over 1.5 mins) retention time 0.62 min, ESI+ found [M+H]=245.

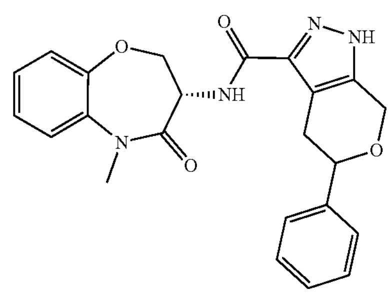 [SMILES: CN1C(=O)[C@@H](NC(=O)c2n[nH]c3c2CC(c2ccccc2)OC3)COc2ccccc21]

Step 3: N—((S)-5-methyl-4-oxo-2,3,4,5-tetrahydrobenzo[b][1,4]oxazepin-3-yl)-5-phenyl-1,4,5,7-tetrahydropyrano[3,4-c]pyrazole-3-carboxamide To a solution of 5-phenyl-1,4,5,7-tetrahydropyrano[3,4-c]pyrazole-3-carboxylic acid (88.0 mg, 0.36 mmol) in N,N-dimethylformamide (5 mL) was added 1H-benzo[d][1,2,3]triazol-1-ol (58 mg, 0.43 mmol), $N^1$-((ethylimino)methylene)-$N^3$,$N^3$-dimethylpropane-1,3-diamine hydrochloride (83 mg, 0.43 mmol) and (3S)-3-amino-5-methyl-2,3-dihydro-1,5-benzoxazepin-4-one (76 mg, 0.40 mmol). The reaction mixture was stirred at RT for 1 h and concentrated to dryness in vacuo. The residue was purified by RP-HPLC (0-40% acetonitrile in water and 0.1% ammonia hydroxide) to afford N-[(3S)-5-methyl-4-oxo-2,3-dihydro-1,5-benzoxazepin-3-yl]-5-phenyl-1,4,5,7-tetrahydropyrano[3,4-c]pyrazole-3-carboxamide (24 mg, 16% yield) as a white solid: $^1$H NMR (400 MHz, DMSO-d6) δ 13.10 (br. s, 1H), 8.04 (br. s, 1H), 7.47-7.23 (m, 9H), 4.97-4.92 (m, 1H), 4.85-4.82 (m, 2H), 4.60-4.54 (m, 2H), 4.46-4.35 (m, 1H), 3.33 (s, 3H), 3.05-3.01 (m, 1H), 2.68-2.56 (m, 1H). LCMS $R_T$=1.88 min, m/z=419 $[M+H]^+$. LCMS (10-80% acetonitrile in water+0.05% ammonium bicarbonate over 3 mins) retention time 1.88/min, ESI+ found [M+H]=419.

Example 10: Method H

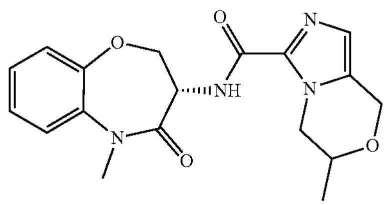 [SMILES: CC1Cn2c(cnc2C(=O)N[C@H]2COc3ccccc3N(C)C2=O)CO1]

6-methyl-N—((S)-5-methyl-4-oxo-2,3,4,5-tetrahydrobenzo[b][1,4]oxazepin-3-yl)-6,8-dihydro-5H-imidazo[5,1-c][1,4]oxazine-3-carboxamide

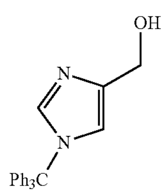

Step 1: (1-trityl-1H-imidazol-4-yl) methanol

To a solution of (1H-imidazol-4-yl) methanol (5.0 g, 51.0 mmol) and triethylamine (15.5 g, 152.9 mmol) in N,N-dimethylformamide (100 mL) was slowly added (chloromethanetriyl)tribenzene (15.6 g, 56.1 mmol). After addition, the reaction mixture was stirred at RT for 3 h and then poured into water (300 mL). The resulting solid was collected by filtration, washed with water (2×100 mL) and recrystallized with dioxane (300 mL) to afford (1-trityl-1H-imidazol-4-yl)methanol (9.8 g, 56% yield) as a white solid: $^1$H NMR (400 MHz, DMSO-d6): δ7.43-7.39 (m, 9H), 7.29 (s, 1H), 7.10-7.08 (m, 6H), 6.72 (s, 1H), 4.89-4.86 (m, 1H), 4.33-4.32 (d, J=5.6 Hz, 2H).

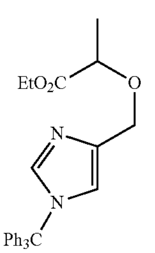

Step 2: ethyl 2-((1-trityl-1H-imidazol-4-yl)methoxy)propanoate

To a solution of (1-trityl-1H-imidazol-4-yl)methanol (6.0 g, 17.6 mmol) in N,N-dimethylformamide (400 mL) was added sodium hydride (60%, 1.4 g, 35.2 mmol) portionwise. After addition, the reaction mixture was stirred at RT for 2 h and ethyl 2-bromopropanoate (6.4 g, 35.2 mmol) was added. The resulting mixture was stirred at RT for another 15 h and quenched by addition of aqueous saturated ammonium chloride (300 mL). The mixture was extracted with ethyl acetate (3×100 mL). The combined organic layers were dried over sodium sulfate and concentrated to dryness in vacuo. The residue was purified by column chromatography (silica gel, 100-200 mesh, 0 to 50% ethyl acetate in petroleum ether) to afford ethyl 2-((1-trityl-1H-imidazol-4-yl)methoxy)propanoate (2.0 g, 26% yield) as an orange oil: LCMS (5 to 95% acetonitrile in water+0.03% trifluoacetic acid over 1.5 mins) $R_T$=0.81 min, m/z=449.1 $[M-C_2H_5+CH_3+Na]^+$.

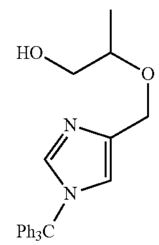

Step 3: 2-((1-trityl-1H-imidazol-4-yl)methoxy)propan-1-ol

To a solution of ethyl 2-((1-trityl-1H-imidazol-4-yl)methoxy)propanoate (2.00 g, 4.54 mmol) in methanol (40 mL) was added sodium borohydride (0.86 g, 22.70 mmol) in small portions. After addition, the reaction mixture was stirred at 25° C. for 16 h and then quenched by addition of saturated aqueous ammonium chloride (40 mL). The resulting mixture was extracted with ethyl acetate (3×30 mL). The combined organic layers were dried over sodium sulfate and concentrated to dryness in vacuo to afford crude 2-((1-trityl-1H-imidazol-4-yl)methoxy)propan-1-ol (1.30 g, 72% yield) as colorless oil used in the next step without any further purification:

LCMS (5 to 95% acetonitrile in water+0.03% trifluoacetic acid over 1.5 mins) retention time 0.80 min, ESI+ found [M+Na]=421.1.

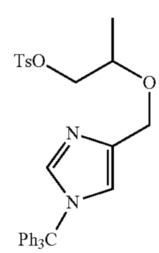

Step 4: 2-((1-trityl-1H-imidazol-4-yl)methoxy)propyl 4-methylbenzenesulfonate

To a solution of 2-((1-trityl-1H-imidazol-4-yl)methoxy)propan-1-ol (1.3 g, 3.26 mmol) and triethylamine (1.0 g, 9.79 mmol) in dichloromethane (20 mL) was added 4-methylbenzene-1-sulfonyl chloride (0.8 g, 3.91 mmol) in small portions. After addition, the mixture was stirred at RT for 15 h. The reaction was washed with saturated sodium bicarbonate (2×15 mL), dried over sodium sulfate and concentrated to dryness in vacuo to afford crude 2-((1-trityl-1H-imidazol-4-yl)methoxy)propyl 4-methylbenzenesulfonate (1.8 g, 99% yield) as a colourless oil used in the next step without any further purification: LCMS (5 to 95% acetonitrile in water+0.03% trifluoacetic acid over 1.5 mins) retention time 0.86 min, ESI+ found [M+H]=553.1.

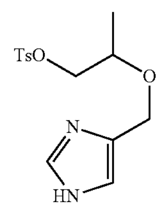 [SMILES: Cc1ccc(S(=O)(=O)OCC(C)OCc2c[nH]cn2)cc1]

Step 5: 2-((1H-imidazol-4-yl)methoxy)propyl 4-methylbenzenesulfonate 2,2,2-trifluoroacetate A mixture of 2-((1-trityl-1H-imidazol-4-yl)methoxy)propyl 4-methylbenzenesulfonate (1.8 g, 3.26 mmol) in 2,2,2-trifluoroacetic acid (20 mL) was stirred at RT for 3 h and concentrated to dryness in vacuo to afford crude 2-((1H-imidazol-4-yl)methoxy)propyl 4-methylbenzenesulfonate (1.0 g, 99% yield) as a red oil used in the next step without any further purification: LCMS (5 to 95% acetonitrile in water+0.03% trifluoacetic acid over 1.5 mins) retention time 0.64 min, ESI+ found [M+H]=310.9.

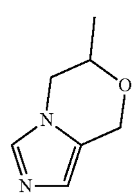

Step 6: 6-methyl-6,8-dihydro-5H-imidazo[5,1-c][1,4]oxazine

A mixture of 2-((1H-imidazol-4-yl)methoxy)propyl 4-methylbenzenesulfonate (1.0 g, 3.22 mmol) and cesium carbonate (3.2 g, 9.67 mmol) in N,N-dimethylformamide (20 mL) was heated at 80° C. for 15 h. After cooled, the mixture was poured into water (40 mL) and extracted with ethyl acetate (3×20 mL). The combined organic layers were dried over sodium sulfate and concentrated to dryness in vacuo. The residue was purified by column chromatography (silica gel, 100-200 mesh, 0 to 100% ethyl acetate in petroleum ether) to afford 6-methyl-6,8-dihydro-5H-imidazo[5,1-c][1,4]oxazine (0.2 g, 46% yield) as a white solid: LCMS (0 to 60% acetonitrile in water+0.05% ammonium bicarbonate over 3 mins) retention time 1.19 min, ESI+ found [M+H]=139.1.

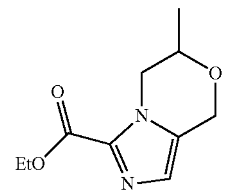

Step 7: ethyl 6-methyl-6,8-dihydro-5H-imidazo[5,1-c][1,4]oxazine-3-carboxylate

To a solution of 6-methyl-6,8-dihydro-5H-imidazo[5,1-c][1,4]oxazine (0.20 g, 1.45 mmol) and N-ethyl-N-isopropylpropan-2-amine (0.70 g, 5.79 mmol) in acetonitrile (2 mL) at −40° C. was added ethyl chloroformate (0.24 g, 2.17 mmol). After addition, the reaction mixture was stirred at RT for 15 h and then concentrated to dryness in vacuo. The residue was purified by column chromatography (silica gel, 100-200 mesh, 0 to 30% ethyl acetate in petroleum ether) to afford ethyl 6-methyl-6,8-dihydro-5H-imidazo[5,1-c][1,4]oxazine-3-carboxylate (0.09 g, 30% yield) as a colorless oil: LCMS $R_T$=1.52 min, m/z=211.2 $[M+H]^+$. LCMS (0 to 60% acetonitrile in water+0.05% ammonium bicarbonate over 3 mins) retention time 1.52 min, ESI+ found [M+H]=211.2.

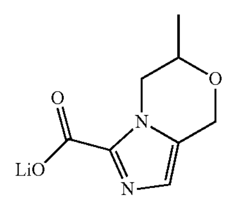

Step 8: lithium 6-methyl-6,8-dihydro-5H-imidazo[5,1-c][1,4]oxazine-3-carboxylate To a solution of ethyl 6-methyl-6,8-dihydro-5H-imidazo[5,1-c][1,4]oxazine-3-carboxylate (90 mg, 0.43 mmol) in ethanol (8 mL) and water (4 mL) was added lithium hydroxide hydrate (180 mg, 4.28 mmol). The mixture was stirred at RT for 1 h and concentrated to dryness in vacuo to afford lithium 6-methyl-6,8-dihydro-5H-imidazo[5,1-c][1,4]oxazine-3-carboxylate (71 mg, 90.7% yield) as white solid used in the next step without further purification.

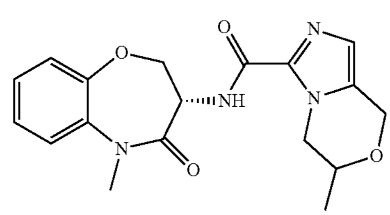

Step 9: 6-methyl-N—((S)-5-methyl-4-oxo-2,3,4,5-tetrahydrobenzo[b][1,4]oxazepin-3-yl)-6,8-dihydro-5H-imidazo[5,1-c][1,4]oxazine-3-carboxamide To a solution of lithium 6-methyl-6,8-dihydro-5H-imidazo[5,1-c][1,4]oxazine-3-carboxylate (71 mg, 0.39 mmol)

in N,N-dimethylformamide (5 mL) was added 1H-benzo[d][1,2,3]triazol-1-ol (53 mg, 0.39 mmol), (3S)-3-amino-5-methyl-2,3-dihydro-1,5-benzoxazepin-4-one (50 mg, 0.26 mmol) and $N^1$-((ethylimino)methylene)-$N^3$,$N^3$-dimethyl-propane-1,3-diamine hydrochloride (75 mg, 0.39 mmol). The mixture was stirred at 20° C. for 2 h and concentrated to dryness in vacuo. The residue was purified by RP-HPLC (30-60% acetonitrile in water and 0.05% ammonium hydroxide) to afford 6-methyl-N—((S)-5-methyl-4-oxo-2,3,4,5-tetrahydrobenzo[b][1,4]oxazepin-3-yl)-6,8-dihydro-5H-imidazo[5,1-c][1,4]oxazine-3-carboxamide (37 mg, 39% yield) as a white solid: $^1$H NMR (400 MHz, DMSO-d6): δ 8.39-8.36 (m, 1H), 7.50-7.48 (m, 1H), 7.32-7.30 (m, 2H), 7.29-7.24 (m, 1H), 6.89 (s, 1H), 4.99-4.95 (m, 1H), 4.78-4.73 (m, 2H), 4.60-4.56 (m, 2H), 4.52-4.39 (m, 1H), 3.84-3.83 (m, 1H), 3.65-3.62 (m, 1H), 3.31 (s, 3H), 1.23 (d, J=6.4 Hz, 3H). LCMS $R_T$=1.21 min, m/z=357.2 [M+H]$^+$. LCMS (10 to 80% acetonitrile in water+0.03% trifluoacetic acid 2 mins) retention time 1.21 min, ESI+ found [M+H]=357.2.

Example 11: Method I

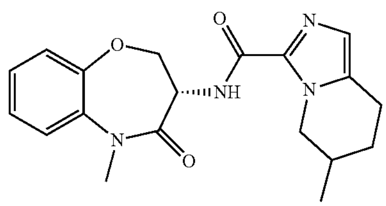

6-methyl-N—((S)-5-methyl-4-oxo-2,3,4,5-tetrahydrobenzo[b][1,4]oxazepin-3-yl)-5,6,7,8-tetrahydroimidazo[1,5-a]pyridine-3-carboxamide

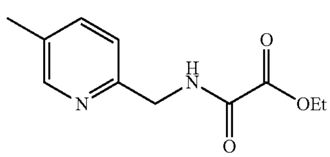 [SMILES: CCOC(=O)C(=O)NCc1ccc(C)cn1]

Step 1: ethyl 2-(((5-methylpyridin-2-yl)methyl)amino)-2-oxoacetate

A solution of (5-methylpyridin-2-yl)methanamine (1.00 g, 8.19 mmol) and triethylamine (1.24 g, 12.28 mmol) in tetrahydrofuran (10 mL) was added ethyl oxalyl chloride (1.23 g, 9.00 mmol) at 0° C. After addition, the reaction mixture was stirred at 20° C. for 10 h and then quenched with saturated aqueous sodium carbonate (20 mL). The solution was extracted with ethyl acetate (3×30 mL). The combined organic layers were dried over sodium sulfate and concentrated to dryness in vacuo. The residue was purified by column chromatography (silica gel, 100-200 mesh, 0 to 50% ethyl acetate in petroleum ether) to afford ethyl 2-[(5-methyl-2-pyridyl)methylamino]-2-oxo-acetate (1.20 mg, 66% yield) as brown oil: $^1$H NMR (400 MHz, $CDCl_3$) δ 8.36 (s, 1H), 8.19 (br., s, 1H), 7.46-7.44 (m, 1H), 7.14 (d, J=8.0 Hz, 1H), 4.56 (d, J=5.2 Hz, 2H), 4.35 (q, J=7.2 Hz, 2H), 2.30 (s, 3H), 1.36 (t, J=7.2 Hz, 3H).

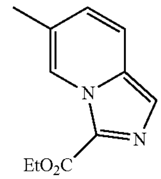

Step 2: ethyl 6-methylimidazo[1,5-a]pyridine-3-carboxylate

A mixture of ethyl 2-[(5-methyl-2-pyridyl)methylamino]-2-oxo-acetate (1.0 g, 4.5 mmol) and phosphorus oxychloride (28.0 g, 182.6 mmol) was heated at 100° C. for 10 h and concentrated to dryness in vacuo. The residue was poured into water (20 mL) and adjusted to pH=8 by adding aqueous saturated sodium bicarbonate (20 mL). The resulting solution was extracted with ethyl acetate (3×50 mL). The combined organic layers were dried over sodium sulfate and concentrated to dryness in vacuo. The residue was purified by column chromatography (silica gel, 100-200 mesh, 0 to 70% ethyl acetate in petroleum ether) to afford ethyl 6-methylimidazo[1,5a]pyridine-3-carboxylate (250 mg, 27.2% yield) as brown solid: LCMS (2 to 98% acetonitrile in water+0.1% formic acid over 1.5 mins) retention time: 0.74 min, ESI+ found [M+H]=204.8.

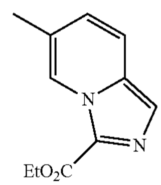

Step 3: ethyl 6-methyl-5,6,7,8-tetrahydroimidazo[1,5-a]pyridine-3-carboxylate

A solution of ethyl 6-methylimidazo[1,5-a]pyridine-3-carboxylate (200 mg, 0.98 mmol) in methanol (5 mL) was treated with 10% palladium on carbon (200 mg, 0.19 mmol). The mixture was hydrogenated (50 psi) at 20° C. for 24 h and then filtered through Celite. The filtrate was concentrated to dryness in vacuo to afford the crude ethyl 6-methyl-5,6,7,8-tetrahydroimidazo[1,5-a]pyridine-3-carboxylate (200 mg, 98.1% yield) as colorless oil used in the next step without any further purification: $^1$H NMR (400 MHz, $CDCl_3$) δ 6.93 (s, 1H), 4.75-4.70 (m, 1H), 4.38 (q, J=7.2 Hz, 2H), 3.68-3.62 (m, 1H), 2.99-2.94 (m, 1H), 2.77-2.75 (m, 1H), 1.96-1.93 (m, 2H), 1.47-1.40 (m, 4H), 1.13 (d, J=6.8 Hz, 3H).

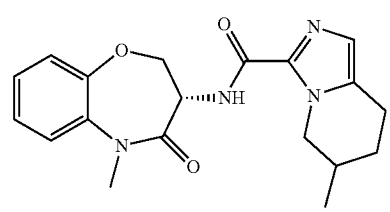 [SMILES: CC1CCc2cnc(C(=O)N[C@H]3COc4ccccc4N(C)C3=O)n2C1]

Step 4: 6-methyl-N—((S)-5-methyl-4-oxo-2,3,4,5-tetrahydrobenzo[b][1,4]oxazepin-3-yl)-5,6,7,8-tetrahydroimidazo[1,5-a]pyridine-3-carboxamide To a stirred solution of ethyl 6-methyl-5,6,7,8-tetrahydroimidazo[1,5-a]pyridine-3-carboxylate (300 mg, 1.4 mmol) in ethanol (10 mL) and water (5 mL) was added lithium hydroxide (345 mg, 14.4 mmol). The mixture was stirred at 20° C. for 1 h and concentrated to dryness in vacuo pressure to afford crude lithium 6-methyl-5,6,7,8-tetrahydroimidazo[1,5-a]pyridine-3-carboxylate.

To a solution of crude lithium 6-methyl-5,6,7,8-tetrahydroimidazo[1,5-a]pyridine-3-carboxylate (70 mg, 0.39 mmol) in N,N-dimethylformamide (5 mL) was added (3S)-3-amino-5-methyl-2,3-dihydro-1,5-benzoxazepin-4-one (50 mg, 0.26 mmol), 1H-benzo[d][1,2,3]triazol-1-ol (53 mg, 0.39 mmol) and N-1-((ethylamine)ethylene)-$N_3$,$N_3$-dimethylpropane-1,3-diamine hydrochloride (75 mg, 0.39 mmol). The mixture was stirred at 25° C. for 1 h and concentrated to dryness in vacuo. The residue was purified by RP-HPLC (49% acetonitrile in water and 0.05% ammonia hydroxide) to afford 6-methyl-N—((S)-5-methyl-4-oxo-2,3,4,5-tetrahydrobenzo[b][1,4]oxazepin-3-yl)-5,6,7,8-tetrahydroimidazo[1,5-a]pyridine-3-carboxamide (29 mg, 31.4% yield) as a white solid: $^1$H NMR (400 MHz, DMSO-d6) δ 8.28-8.25 (m, 1H), 7.50-7.47 (m, 1H), 7.34-7.29 (m, 2H), 7.24-7.23 (m, 1H), 6.82 (s, 1H), 4.82-4.75 (m, 1H), 4.58-4.51 (m, 2H), 4.42-4.40 (m, 1H), 3.55-3.49 (m, 1H), 3.31 (s, 3H), 2.86-2.85 (m, 1H), 2.72-2.64 (m, 1H), 2.53-2.51 (m, 1H), 1.83-1.80 (m, 1H), 1.38-1.32 (m, 1H), 0.99 (d, J=6.4 Hz, 3H). LCMS (10 to 80% acetonitrile in water+0.1% NH4OH over 3 mins) retention time 1.90 min, ESI+ found [M+H]=355.2.

Example 12: Method J

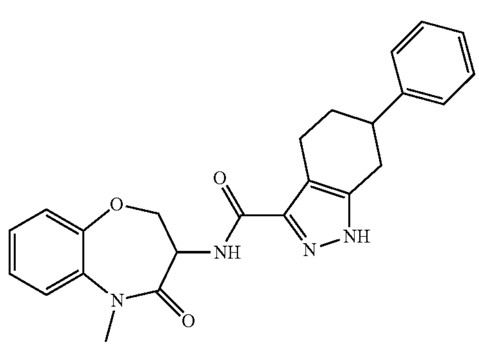 [SMILES: CN1C(=O)C(NC(=O)c2n[nH]c3c2CCC(c2ccccc2)C3)COc2ccccc21]

N-(5-methyl-4-oxo-2,3,4,5-tetrahydrobenzo[b][1,4]oxazepin-3-yl)-6-phenyl-4,5,6,7-tetrahydro-1H-indazole-3-carboxamide

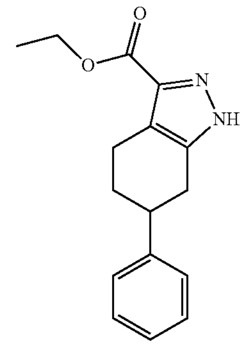 [SMILES: CCOC(=O)c1n[nH]c2c1CCC(c1ccccc1)C2]

Step 1: ethyl 6-phenyl-4,5,6,7-tetrahydro-1H-indazole-3-carboxylate

To a solution of 4-phenylcyclohexanone (2.0 g, 11.48 mmol) in dimethyl sulfoxide (20 mL) was added pyrrolidine (40.8 mg, 0.57 mmol). The mixture was stirred at 20° C. for 15 min, and ethyl 2-diazoacetate (654.8 mg, 5.74 mmol) was added. The resulting mixture was stirred at 20° C. for 15 h and then diluted with water (20 mL). The mixture was extracted with ethyl acetate (3×50 mL). The combined organic layers were dried over anhydrous sodium sulfate and concentrated to dryness in vacuo. The residue was purified by column chromatography (silica gel, 100-200 mesh, 25% ethyl acetate in petroleum ether) to afford ethyl 6-phenyl-4,5,6,7-tetrahydro-1H-indazole-3-carboxylate (830 mg, 53% yield) as a brown oil: $^1$H NMR (400 MHz, $CDCl_3$) δ 7.35-7.32 (m, 2H), 7.27-7.22 (m, 3H), 4.39-4.33 (m, 2H), 3.08-2.97 (m, 3H), 2.81-2.72 (m, 2H), 2.15-2.12 (m, 1H), 1.95-1.89 (m, 1H), 1.38-1.34 (m, 3H). LCMS (10 to 80% acetonitrile in water+0.05% ammonium bicarbonate over 3 mins) retention time 1.99 min, ESI+ found [M+H]=271.2.

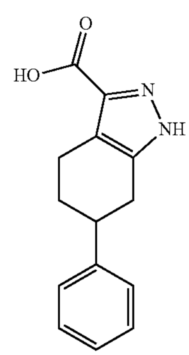 [SMILES: O=C(O)c1n[nH]c2c1CCC(c1ccccc1)C2]

Step 2: 6-phenyl-4,5,6,7-tetrahydro-1H-indazole-3-carboxylic acid

To a solution of ethyl 6-phenyl-4,5,6,7-tetrahydro-1H-indazole-3-carboxylate (400 mg, 1.5 mmol) in tetrahydrofuran (8 mL) and water (8 mL) was added lithium hydroxide monohydrate (354 mg, 14.8 mmol). The mixture was stirred at 20° C. for 22 h and concentrated to dryness in vacuo. The residue was diluted with water (10 mL) and adjusted to the pH=3 with of 1M hydrochloric acid. The resulting solid was collected by filtration to afford crude 6-phenyl-4,5,6,7-tetrahydro-1H-indazole-3-carboxylic acid (320 mg, 89.3% yield) as yellow solid used in the next step without further purification: LCMS (5 to 95% acetonitrile in water+0.03% trifluoacetic acid over 1.5 mins) retention time 0.67 min, ESI+ found [M+H]=242.9.

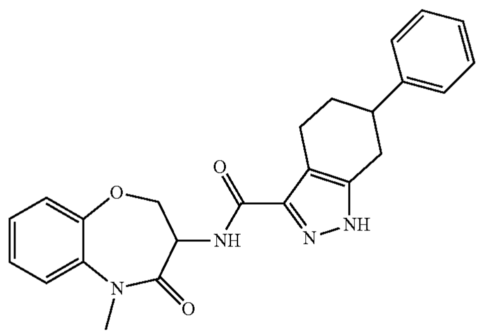 [SMILES: CN1C(=O)C(NC(=O)c2n[nH]c3c2CCC(c2ccccc2)C3)COc2ccccc21]

Step 3: N-(5-methyl-4-oxo-2,3,4,5-tetrahydrobenzo[b][1,4]oxazepin-3-yl)-6-phenyl-4,5,6,7-tetra hydro-1H-indazole-3-carboxamide To a solution of 6-phenyl-4,5,6,7-tetrahydro-1H-indazole-3-carboxylic acid (189 mg, 0.78 mmol) in N,N-dimethylformamide (5 mL) was added 1H-benzo[d][1,2,3]triazol-1-ol (105 mg, 0.78 mmol), (3S)-3-amino-5-methyl-2,3-dihydro-1,5-benzoxazepin-4-one (100 mg, 0.52 mmol) and N1-((ethylimino)methylene)-N3,N3-dimethylpropane-1,3-diamine hydrochloride (150 mg, 0.78 mmol). The mixture was stirred at 20° C. for 1 h and then concentrated to dryness in vacuo. The residue was purified by RP-HPLC (40-70% acetonitrile in water and 0.05% ammonia hydrate) to afford N-(5-methyl-4-oxo-2,3,4,5-tetrahydrobenzo[b][1,4]oxazepin-3-yl)-6-phenyl-4,5,6,7-tetrahydro-1H-indazole-3-carboxamide (77 mg, 34% yield as a white solid: $^1$H NMR (400 MHz, DMSO-d6) δ 12.94 (s, 1H), 7.96 (d, J=8.0, 1H), 7.49 (d, J 7.6 Hz, 1H), 7.34-7.27 (m, 6H), 7.25-7.22 (m, 2H), 4.88-4.83 (m, 1H), 4.52-4.48 (m, 1H), 4.44-4.41 (m, 1H), 3.32 (s, 3H), 2.93-2.69 (m, 4H), 2.58-2.55 (m, 1H), 1.93-1.90 (m, 1H), 1.81-1.78 (m, 1H). LCMS (10 to 80% acetonitrile in water+0.05% ammonium hydroxide over 3 mins) retention time 2.03 min, ESI+ found [M+H]=417.2.

Example 13: Method K

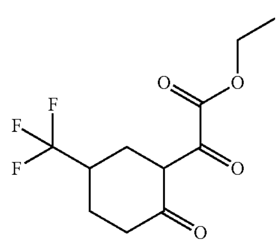 [SMILES: CCOC(=O)C(=O)C1CC(C(F)(F)F)CCC1=O]

Step 1: ethyl 2-oxo-2-[2-oxo-5-(trifluoromethyl)cyclohexyl]acetate

To a solution of 4-(trifluoromethyl)cyclohexanone (15.0 g, 90.3 mmol) in ethanol (45 mL) was added a solution of sodium ethoxide (6.8 g, 100.0 mmol) in ethanol (36 mL), following by diethyl oxalate (13.19 g, 90.29 mmol) at 0° C. After addition, the mixture was allowed to warm to 25° C. and stirred for 15 h. The reaction mixture was concentrated to dryness in vacuo to afford crude ethyl 2-oxo-2-[2-oxo-5-(trifluoromethyl)cyclohexyl]acetate (33.0 g, 138% yield) as a yellow solid use in the next step without any further purification: LCMS (5 to 95% acetonitrile in water+0.04% formic acid over 1.5 mins) retention time 0.861 min, ESI+ found [M+H]=266.9.

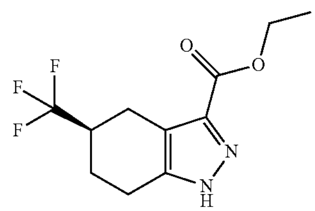

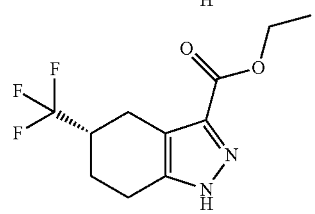

Step 2: (R)-ethyl 5-(trifluoromethyl)-4,5,6,7-tetrahydro-1H-indazole-3-carboxylate and (S)-ethyl 5-(trifluoromethyl)-4,5,6,7-tetrahydro-1H-indazole-3-carboxylate To a solution of ethyl 2-oxo-2-[2-oxo-5-(trifluoromethyl)cyclohexyl]acetate (33.0 g, 90.3 mmol) in glacial acetic acid (33 mL) was added hydrazine hydrate (6.2 g, 124.0 mmol) at 0° C. The mixture was stirred for 1 h at 25° C., and then adjusted to pH=8 with aqueous sodium bicarbonate. The resulting mixture was extracted with methanol and dichloromethane (3×300 mL, methanol/dichloromethane=5:95). The combined organic extracts were washed with water (20 mL), brine (20 mL), dried over sodium sulfate and concentrated to dryness in vacuo. The residue was purified by column chromatography (silica gel, 100-200 mesh, 0 to 50% ethyl acetate in petroleum ether) to afford racemic ethyl 5-(trifluoromethyl)-4,5,6,7-tetrahydro-1H-indazole-3-carboxylate (5.0 g, 21% yield) as a white solid. In a 500 mg batch, the enantiomers were separated by SFC to afford arbitrarily assigned enantiomers:

Peak 1 (Retention time: 3.36 min):

(R)-ethyl 5-(trifluoromethyl)-4,5,6,7-tetrahydro-1H-indazole-3-carboxylate (180 mg, 36% yield); Peak 2 (Retention time 3.66 min):

(S)-ethyl-5-(trifluoromethyl)-4,5,6,7-tetrahydro-1H-indazole-3-carboxylate (132 mg, 26% yield)

SFC condition: Column: Lux Cellulose-2 150×4.6 mm I.D., 3 μm Mobile phase: A: $CO_2$ B: ethanol (0.05% DEA) Gradient: from 5% to 40% of B in 5.5 min and hold 40% for 3 min, then 5% of B for 2.5 min Flow rate: 2.5 mL/min Column temperature: 40° C.

Example 14: Method L

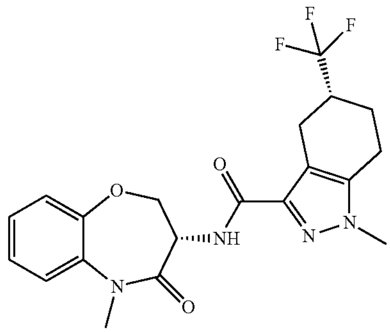

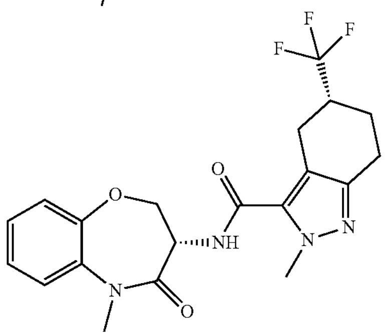

(5R)-1-methyl-N-[(3S)-5-methyl-4-oxo-2,3,4,5-tetrahydrobenzo[b][1,4]oxazepin-3-yl]-5-(trifluoromethyl)-4,5,6,7-tetrahydro-1H-indazole-3-carboxamide and (5R)-2-methyl-N-[(3S)-5-methyl-4-oxo-2,3-dihydro-1,5-benzoxazepin-3-yl]-5-(trifluoromethyl)-4,5,6,7-tetrahydroindazole-3-carboxamide Step 3: (R)-ethyl 1-methyl-5-(trifluoromethyl)-4,5,6,7-tetrahydro-1H-indazole-3-carboxylate and (R)-ethyl 2-methyl-5-(trifluoromethyl)-4,5,6,7-tetrahydro-2H-indazole-3-carboxylate

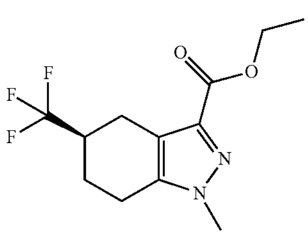

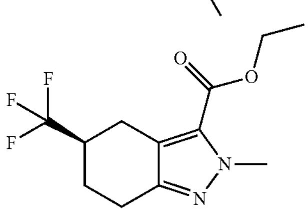

To a solution of arbitrarily assigned ethyl (R)-5-(trifluoromethyl)-4,5,6,7-tetrahydro-1H-indazole-3-carboxylate (180 mg, 0.69 mmol) in N,N-dimethylformamide (10 mL) was added potassium carbonate (104 mg, 0.76 mmol). After stirred for 30 min, methyl iodide (86 mg, 0.60 mmol) was added and stirring was continued for 15 h. The reaction was diluted with water (50 mL) and extracted with ethyl acetate (3×50 mL). The combined organic extracts were washed with water (50 mL), brine (50 mL), dried over anhydrous sodium sulfate and concentrated to dryness in vacuo. The residue which was purified by prep-TLC (30% ethyl acetate in petroleum ether) to afford (R)-ethyl 1-methyl-5-(trifluoromethyl)-4,5,6,7-tetrahydro-1H-indazole-3-carboxylate (Rf=0.2, 72 mg, 37% yield) and (R)-ethyl 2-methyl-5-(trifluoromethyl)-4,5,6,7-tetrahydro-2H-indazole-3-carboxylate (Rf=0.5, 53 mg, 28% yield): $^1$H NMR (400 MHz, $CDCl_3$) δ 4.40-4.35 (m, 2H), 3.80 (s, 3H), 3.22-3.15 (m, 1H), 2.81-2.50 (m, 3H), 2.38-2.40 (m, 1H), 2.31-2.19 (m, 1H), 1.82-1.67 (m, 1H), 1.38 (t, J=7.2 Hz, 3H). LCMS $R_T$=0.835 min, m/z=276.9 $[M+H]^+$; $^1$H NMR (400 MHz, $CDCl_3$) δ 4.37-4.32 (m, 2H), 4.10 (s, 3H), 3.15-3.09 (m, 1H), 2.88-2.83 (m, 1H), 2.72-2.63 (m, 2H), 2.49-2.30 (m, 1H), 2.27-2.13 (m, 1H), 1.76-1.61 (m, 1H), 1.37 (t, J=7.2 Hz, 3H). LCMS (5 to 95% acetonitrile in water+0.03% trifluoroacetic acid over 1.5 mins) retention time 0.835 min, ESI+ found [M+H]=276.9 and retention time 0.895 min, ESI+ found [M+H]=276.9.

Step 4: (R)-1-methyl-5-(trifluoromethyl)-4, 5, 6, 7-tetrahydroindazole-3-carboxylic acid

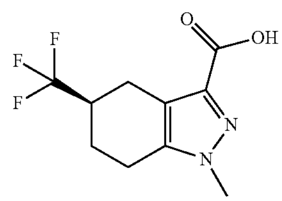 [SMILES: Cn1nc(C(=O)O)c2c1CC[C@@H](C(F)(F)F)C2]

To a solution of arbitrarily assigned ethyl (R)-1-methyl-5-(trifluoromethyl)-4,5,6,7-tetrahydroindazole-3-carboxylate (72 mg, 0.26 mmol) in ethanol (5 mL) and water (2 mL) was added potassium hydroxide (73 mg, 1.3 mmol). The mixture was stirred at 25° C. for 15 h and concentrated to dryness in vacuo. The residue was dissolved in water (5 mL) and adjusted the pH=3 with 1 M hydrochloric acid. The solution was extracted with ethyl acetate (3×10 mL). The combined organic layer were washed with water (20 mL), brine (20 mL), dried over anhydrous sodium sulfate and concentrated to afford (R)-1-methyl-5-(trifluoromethyl)-4,5,6,7-tetrahydroindazole-3-carboxylic acid (52 mg, 80% yield) as a white solid used without further purification in the next step: LCMS (0 to 60% acetonitrile in water+0.04% formic acid over 2 mins) retention time 1.10 min, ESI+ found [M+H]=249.0.

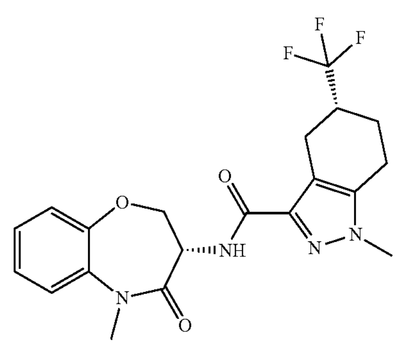 [SMILES: CN1C(=O)[C@@H](NC(=O)c2nn(C)c3c2C[C@H](C(F)(F)F)CC3)COc2ccccc21]

Step 5: (5R)-1-methyl-N-[(3S)-5-methyl-4-oxo-2,3,4,5-tetrahydrobenzo[b][1,4]oxazepin-3-yl]-5-(trifluoromethyl)-4,5,6,7-tetrahydro-1H-indazole-3-carboxamide To a solution of (R)-1-methyl-5-(trifluoromethyl)-4,5,6,7-tetrahydroindazole-3-carboxylic acid (52 mg, 0.20 mmol) in N,N-dimethylformamide (4 mL) was added 1-1H-benzo[d][1,2,3]triazol-1-ol (62 mg, 0.46 mmol), (3S)-3-amino-5-methyl-2,3-dihydro-1,5-benzoxazepin-4-one (88 mg, 0.46 mmol), and $N^1$-((ethylimino)methylene)-$N^3$,$N^3$-dimethyl-propane-1,3-diamine hydrochloride (88 mg, 0.46 mmol). The reaction mixture was stirred at 25° C. for 12 h and concentrated to dryness in vacuo. The residue was purified by RP-HPLC (25-55% acetonitrile in water and 0.225% formic acid) to afford (5R)-1-methyl-N-[(3S)-5-methyl-4-oxo-2,3-dihydro-1,5-benzoxazepin-3-yl]-5-(trifluoromethyl)-4,5,6,7-tetrahydroindazole-3-carboxamide (21 mg, 25% yield) as a white solid: $^1$H NMR (400 MHz, Methanol-d4) δ 7.44-7.41 (m, 1H), 7.33-7.22 (m, 3H), 4.97-4.94 (m, 1H), 4.60-4.56 (m, 1H), 4.37-4.31 (m, 1H), 3.77 (s, 3H), 3.42 (s, 3H), 3.12-3.07 (m, 1H), 2.85-2.81 (m, 1H), 2.68-2.45 (m, 3H), 2.26-2.21 (m, 1H), 1.76-1.63 (m, 1H). LCMS (0 to 60% acetonitrile in water+0.03% trifluoroacetic acid over 2 mins) retention time 1.64 min, ESI+ found [M+H]=423.2.

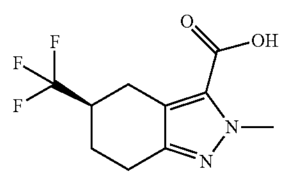 [SMILES: Cn1nc2c(c1C(=O)O)C[C@H](C(F)(F)F)CC2]

Step 6: (R)-2-methyl-5-(trifluoromethyl)-4,5,6,7-tetrahydro-2H-indazole-3-carboxylic acid To a solution of ethyl (R)-2-methyl-5-(trifluoromethyl)-4,5,6,7-tetrahydroindazole-3-carboxylate (53 mg, 0.19 mmol) in ethanol (5 mL) and water (2 mL) was added potassium hydroxide (62 mg, 1.1 mmol). The mixture was stirred at 25° C. for 15 h and concentrated to dryness in vacuo. The residue was dissolved in water (5 mL) and adjusted the pH=3 with 1 M hydrochloric acid. The resulting mixture was extracted with ethyl acetate (3×10 mL). The combined organic layers were washed with water (20 mL), brine (20 mL), dried over anhydrous sodium sulfate and concentrated to dryness in vacuo to afford (R)-2-methyl-5-(trifluoromethyl)-4,5,6,7-tetrahydroindazole-3-carboxylic acid (53 mg, 99% yield) as a white solid used without further purification in the next step: LCMS (0 to 60% acetonitrile in water+0.03% trifluoroacetic acid over 2 mins) retention time 1.16 min, ESI+ found [M+H]=249.0.

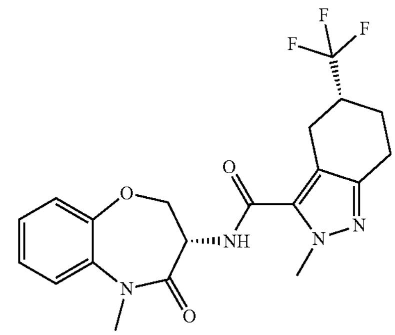 [SMILES: CN1C(=O)[C@@H](NC(=O)c2c3c(nn2C)CC[C@@H](C(F)(F)F)C3)COc2ccccc21]

Step 7: (5R)-2-methyl-N-[(3S)-5-methyl-4-oxo-2,3-dihydro-1,5-benzoxazepin-3-yl]-5-(trifluoromethyl)-4,5,6,7-tetrahydroindazole-3-carboxamide To a solution of (5R)-2-methyl-5-(trifluoromethyl)-4,5,6,7-tetrahydroindazole-3-carboxylic acid (53 mg, 0.21 mmol) in N,N-dimethylformamide (4 mL) was added methyl (3S)-3-amino-5-methyl-2,3-dihydro-1,5-benzoxazepin-4-one (121 mg, 0.64 mmol), 1-1H-benzo[d][1,2,3]triazol-1-ol (86 mg, 0.64 mmol) and $N^1$-((ethylimino)methylene)-$N^3$,$N^3$-dimethylpropane-1,3-diamine hydrochloride (122 mg, 0.64 mmol). The reaction mixture was stirred at 25° C. for 12 h and concentrated to dryness in vacuo. The residue was purified by RP-HPLC (25-55% acetonitrile in water and 0.225% formic acid) to afford (5R)-1-methyl-N-[(3S)-5-methyl-4-oxo-2,3-dihydro-1,5-benzoxazepin-3-yl]-5-(trifluoromethyl)-4,5,6,7-tetrahydroindazole-3-carboxamide (33 mg, 37% yield) as white solid: $^1$H NMR (400 MHz, $CD_3OD$) δ7.45-7.41 (m, 1H), 7.35-7.18 (m, 3H), 5.03-4.97 (m, 1H), 4.60-4.55 (m, 1H), 4.43-4.37 (m, 1H), 3.91 (s, 3H), 3.42 (s, 3H), 3.12-3.05 (m, 1H), 2.87-2.30 (m, 4H), 2.26-2.22 (m, 1H), 1.77-1.71 (m, 1H). LCMS (0 to 60% acetonitrile in water+0.03% trifluoroacetic acid over 7 mins) retention time 6.00 min, ESI+ found [M+H]=423.1.

Example 15: Method M

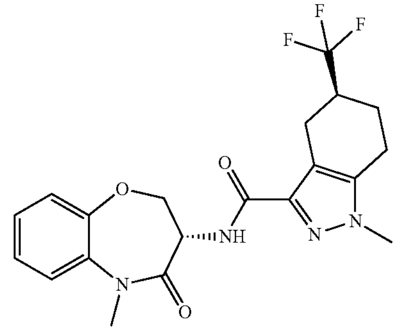

-continued

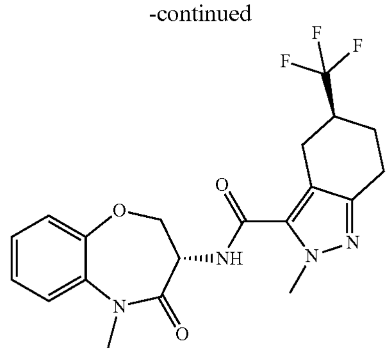

(5S)-1-methyl-N-[(3S)-5-methyl-4-oxo-2,3,4,5-tetrahydrobenzo[b][1,4]oxazepin-3-yl]-5-(trifluoromethyl)-4,5,6,7-tetrahydro-1H-indazole-3-carboxamide and (5S)-2-methyl-N-[(3S)-5-methyl-4-oxo-2,3-dihydro-1,5-benzoxazepin-3-yl]-5-(trifluoromethyl)-4,5,6,7-tetrahydroindazole-3-carboxamide

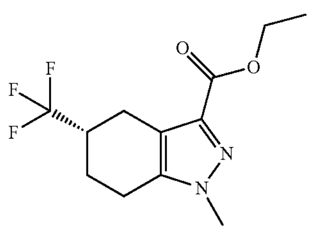

and

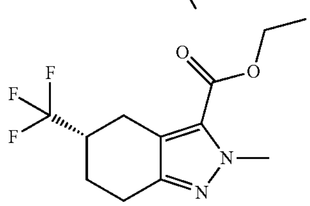

Step 1: (S)-ethyl 1-methyl-5-(trifluoromethyl)-4,5,6,7-tetrahydro-1H-indazole-3-carboxylate and (S)-ethyl 2-methyl-5-(trifluoromethyl)-4,5,6,7-tetrahydro-2H-indazole-3-carboxylate To a solution of ethyl (S)-5-(trifluoromethyl)-4,5,6,7-tetrahydro-1H-indazole-3-carboxylate (132 mg, 0.50 mmol) in N,N-dimethylformamide (10 mL) was added potassium carbonate (104 mg, 0.76 mmol). After stirred for 30 min, methyl iodide (86 mg, 0.60 mmol) was added and stirring was continued for 15 h. The reaction was diluted with water (50 mL) and extracted with ethyl acetate (3×50 mL). The combined organic layers were washed with water (50 mL), brine (50 mL), dried over anhydrous sodium sulfate and concentrated to dryness in vacuo. The residue which was purified by prep-TLC (30% ethyl acetate in petroleum ether) to afford (S)-ethyl 1-methyl-5-(trifluoromethyl)-4,5,6,7-tetrahydro-1H-indazole-3-carboxylate (Rf=0.2, 38 mg, 27.5% yield) and (S)-ethyl 2-methyl-5-(trifluoromethyl)-4,5,6,7-tetrahydro-1H-indazole-3-carboxylate (Rf=0.5, 86 mg, 62.3% yield) as a white solid: LCMS (5 to 95% acetonitrile in water+0.03% trifluoroacetic acid over 1.5 mins) retention time 0.83 min, ESI+ found [M+H]=276.9 and $R_T$=0.89 min, m/z=276.9 $[M+H]^+$.

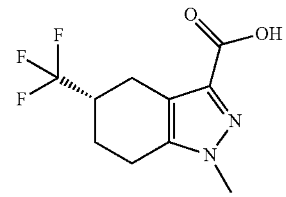 [SMILES: Cn1nc(C(=O)O)c2c1CC[C@H](C(F)(F)F)C2]

Step 2: (S)-1-methyl-5-(trifluoromethyl)-4, 5, 6, 7-tetrahydroindazole-3-carboxylic acid To a solution of (S)-ethyl 1-methyl-5-(trifluoromethyl)-4,5,6,7-tetrahydro-1H-indazole-3-carboxylate (38 mg, 0.14 mmol) in ethanol (5 mL) and water (2 mL) was added potassium hydroxide (38 mg, 0.69 mmol). The mixture was stirred at 25° C. for 15 h and concentrated to dryness in vacuo. The residue was dissolved in water (5 mL) and adjusted the pH=3 with 1 M hydrochloric acid. The resulting mixture was extracted with ethyl acetate (3×10 mL). The combined organic layers were washed with water (20 mL), brine (20 mL), dried over sodium sulfate and concentrated to dryness in vacuo to afford the product (R)-1-methyl-5-(trifluoromethyl)-4,5,6,7-tetrahydroindazole-3-carboxylic acid (38 mg, 100% yield) as a white solid: LCMS (0 to 60% acetonitrile in water+0.03% trifluoroacetic acid over 2 mins) retention time 1.12 min, ESI+ found [M+H]=249.0.

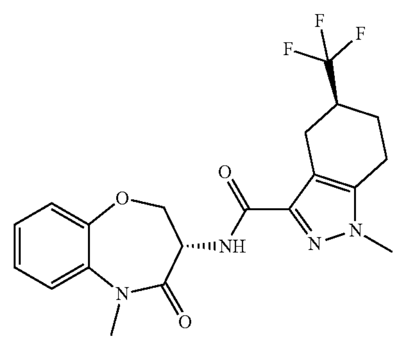 [SMILES: CN1C(=O)[C@@H](NC(=O)c2nn(C)c3c2C[C@@H](C(F)(F)F)CC3)COc2ccccc21]

Step 3: (5S)-1-methyl-N-[(3S)-5-methyl-4-oxo-2,3-dihydro-1,5-benzoxazepin-3-yl]-5-(trifluoromethyl)-4,5,6,7-tetrahydroindazole-3-carboxamide To a solution of (S)-1-methyl-5-(trifluoromethyl)-4,5,6,7-tetrahydroindazole-3-carboxylic acid (38 mg, 0.14 mmol) in N,N-dimethylformamide (4 mL) was added methyl (3S)-3-amino-5-methyl-2,3-dihydro-1,5-benzoxazepin-4-one (88 mg, 0.46 mmol), 1-1H-benzo[d][1,2,3]triazol-1-ol (62 mg, 0.46 mmol) and $N^1$-((ethylimino)methylene)-$N^3$,$N^3$-dimethyl propane-1,3-diamine hydrochloride (88 mg, 0.46 mmol). The reaction mixture was stirred at 25° C. for 12 h and concentrated to dryness in vacuo. The residue was purified by RP-HPLC (25-55% acetonitrile in water and 0.225% formic acid) to afford (5S)-1-methyl-N-[(3S)-5-methyl-4-oxo-2,3-dihydro-1,5-benzoxazepin-3-yl]-5-(trifluoromethyl)-4,5,6,7-tetrahydroindazole-3-carboxamide (31 mg, 52% yield) as a white solid: $^1H$ NMR (400 MHz, Methanol-d4) δ 7.46-7.40 (m, 1H), 7.36-7.20 (m, 3H), 4.99-4.94 (m, 1H), 4.60-4.56 (m, 1H), 4.38-4.33 (m, 1H), 3.79 (s, 3H), 3.41 (s, 3H), 3.11-3.06 (m, 1H), 2.85-2.81 (m, 1H), 2.67-2.46 (m, 3H), 2.25-2.21 (m, 1H), 1.75-1.67 (m, 1H). LCMS (0 to 60% acetonitrile in water+0.03% trifluoroacetic acid over 7 mins) retention time 6.20 min, ESI+ found [M+H]=423.2.

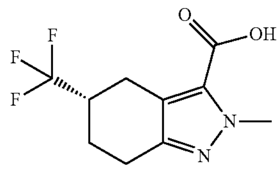 [SMILES: Cn1nc2c(c1C(=O)O)C[C@@H](C(F)(F)F)CC2]

Step 4: (S)-2-methyl-5-(trifluoromethyl)-4,5,6,7-tetrahydroindazole-3-carboxylic acid To a solution of (S)-ethyl 2-methyl-5-(trifluoromethyl)-4,5,6,7-tetrahydro-1H-indazole-3-carboxylate (86 mg, 0.31 mmol) in ethanol (5 mL) and water (2 mL) was added potassium hydroxide (91 mg, 1.60 mmol). The mixture was stirred at 25° C. for 15 h and concentrated to dryness in vacuo. The residue was dissolved in water (5 mL) and adjusted the pH=3 with 1 M hydrochloric acid. The resulting mixture was extracted with ethyl acetate (3×10 mL). The combined organic layers were washed with water (20 mL), brine (20 mL), dried over sodium sulfate and concentrated to dryness in vacuo to afford (R)-2-methyl-5-(trifluoromethyl)-4,5,6,7-tetrahydroindazole-3-carboxylic acid (74 mg, 92% yield) as a white solid. LCMS (0 to 60% acetonitrile in water+0.03% trifluoroacetic acid over 2 mins) retention time 1.17 min, ESI+ found [M+H]=249.0.

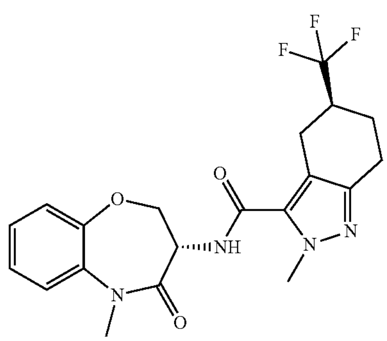 [SMILES: CN1C(=O)[C@@H](NC(=O)c2c3c(nn2C)CC[C@H](C(F)(F)F)C3)COc2ccccc21]

Step 5: (5S)-2-methyl-N—((S)-5-methyl-4-oxo-2,3,4,5-tetrahydrobenzo[b][1,4]oxazepin-3-yl)-5-(trifluoromethyl)-4,5,6,7-tetrahydro-2H-indazole-3-carboxamide To a solution of (S)-2-methyl-5-(trifluoromethyl)-4,5,6,7-tetrahydroindazole-3-carboxylic acid (74 mg, 0.30 mmol) in N,N-dimethylformamide (4 mL) was added methyl (3S)-3-amino-5-methyl-2,3-dihydro-1,5-benzoxazepin-4-one (121 mg, 0.64 mmol), 1-1H-benzo[d][1,2,3]triazol-1-ol (86 mg, 0.64 mmol) and $N^1$-((ethylimino)methylene)-$N^3$,$N^3$-dimethyl propane-1,3-diamine hydrochloride (122 mg, 0.64 mmol). The reaction mixture was stirred at 25° C. for 12 h and concentrated to dryness in vacuo. The residue was purified by RP-HPLC (25-55% acetonitrile in water and 0.225% formic acid) to afford (5S)-2-methyl-N-[(3S)-5-methyl-4-oxo-2,3-dihydro-1,5-benzoxazepin-3-yl]-5-(trifluoromethyl)-4,5,6,7-tetrahydroindazole-3-carboxamide (33 mg, 26% yield) as a white solid: $^1$H NMR (400 MHz, Methanol-d4) δ 7.45-7.41 (m, 1H), 7.36-7.17 (m, 3H), 4.98-4.94 (m, 1H), 4.60-4.55 (m, 1H), 4.44-4.37 (m, 1H), 3.90 (s, 3H), 3.42 (s, 3H), 3.09-3.04 (m, 1H), 2.83-2.60 (m, 4H), 2.28-2.19 (m, 1H), 1.75-1.65 (m, 1H). LCMS (0 to 60% acetonitrile in water+0.03% trifluoroacetic acid over 7 mins) retention time 6.00 min, ESI+ found [M+H]=423.2.

Example 16: Method N

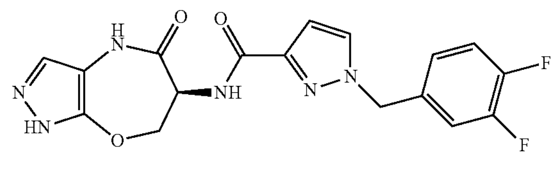 [SMILES: O=C(N[C@H]1COc2[nH]ncc2NC1=O)c1ccn(Cc2ccc(F)c(F)c2)n1]

(S)-1-(3,4-difluorobenzyl)-N-(5-oxo-4,5,6,7-tetrahydro-1H-pyrazolo[3, 4-b][1,4]oxazepin-6-yl)-1H-pyrazole-3-carboxamide

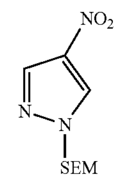 [SMILES: C[Si](C)(C)CCOCn1cc([N+](=O)[O-])cn1]

Step 1: 4-nitro-1-((2-(trimethylsilyl)ethoxy)methyl)-1H-pyrazole

To a solution of 4-nitro-1H-pyrazole (30.0 g, 265 mmol) in tetrahydrofuran (400 mL) was added sodium hydride (60%, 15.9 g, 398 mmol) at 0° C. The reaction mixture was stirred for 30 min, and (2-(chloromethoxy)ethyl)trimethylsilane (66.3 g, 398 mmol) was added at 0° C. After addition, the mixture was stirred at 25° C. for 2 h and then quenched by addition of water (100 mL). The resulting mixture was extracted with ethyl acetate (3×200 mL). The combined organic layers were washed with water (100 mL), brine (100 mL), dried over anhydrous sodium sulfate and concentrated to dryness in vacuo. The residue was purified by column chromatography (silica gel, 100-200 mesh, 0 to 10% ethyl acetate in petroleum ether) to afford 4-nitro-1-((2-(trimethylsilyl)ethoxy)methyl)-1H-pyrazole (60.0 g, 93% yield) used in the next step without further purification.

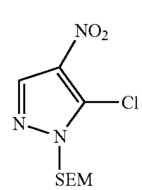 [SMILES: C[Si](C)(C)CCOCn1ncc([N+](=O)[O-])c1Cl]

Step 2: 5-chloro-4-nitro-1-((2-(trimethylsilyl) ethoxy)methyl)-1H-pyrazole

To a solution of 4-nitro-1-((2-(trimethylsilyl)ethoxy) methyl)-1H-pyrazole (20.0 g, 82.2 mmol) in tetrahydrofuran (300 mL) was added with lithium bis(trimethylsilyl)azanide (1M in tetrahydrofuran, 89.0 mL, 89.0 mmol) at −78° C. The mixture was stirred for 30 min, and hexachloroethane (21.3 g, 90.1 mmol) was added dropwise. After addition, the mixture was allowed to warm to RT and stirred for 16 h. The reaction mixture was quenched by addition of saturated aqueous ammonium chloride (80 mL) and extracted with ethyl acetate (3×80 mL). The combined organic layers were washed with water (100 mL), brine (100 mL), dried over anhydrous sodium sulfate and concentrated to dryness in vacuo. The residue was purified by column chromatography (silica gel, 100-200 mesh, 0 to 10% ethyl acetate in petroleum ether) to afford 5-chloro-4-nitro-1-((2-(trimethylsilyl) ethoxy)methyl)-1H-pyrazole (15.0 g, 66% yield) as colorless oil: $^1$H NMR (400 MHz, DMSO-d6) δ 8.53 (s, 1H), 5.56 (s, 2H), 3.61 (t, J=8.2 Hz, 2H), 0.86 (t, J=8.2 Hz, 2H), 0.05 (s, 9H).

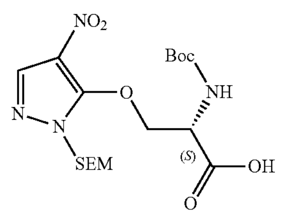

Step 3: (S)-2-((tert-butoxycarbonyl)amino)-3-((4-nitro-1-((2-(trimethylsilyl)ethoxy)methyl)-1H-pyrazol-5-yl)oxy)propanoic acid To a solution of (S)-2-((tert-butoxycarbonyl)amino)-3-hydroxypropanoic acid (1.77 g, 8.64 mmol) in N, N-dimethylformamide (50 mL) was added sodium hydride (60%, 691 mg, 17.28 mmol) at 0° C. The mixture was stirred at 0° C. for 1 h, and then 5-chloro-4-nitro-1-((2-(trimethylsilyl) ethoxy)methyl)-1H-pyrazole (2.40 g, 8.64 mmol) was added. The resulting mixture was stirred at 20° C. for 3 h and quenched by addition of 1M hydrochloric acid (30 mL). The mixture was extracted with ethyl acetate (3×30 mL). The combined organic layers were dried over anhydrous sodium sulfate and concentrated to dryness in vacuo. The residue was purified by column chromatography (silica gel, 100-200 mesh, 0 to 30% ethyl acetate in petroleum ether) to afford (S)-2-((tert-butoxycarbonyl)amino)-3-((4-nitro-1-((2-(trimethylsilyl)ethoxy)methyl)-1H-pyrazol-5-yl)oxy)propanoic acid (1.00 g, 26% yield) as yellow oil. LCMS (5 to 95% acetonitrile in water+0.03% trifluoroacetic acid over 1.5 mins) retention time 0.99 min, ESI+ found [M+H]=469.1.

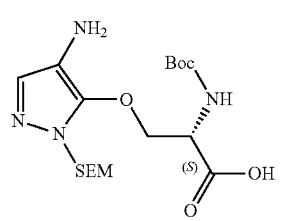

Step 4: (S)-3-((4-amino-1-((2-(trimethylsilyl) ethoxy)methyl)-1H-pyrazol-5-yl)oxy)-2-((tert-butoxycarbonyl)amino)propanoic acid To a solution of (S)-2-((tert-butoxycarbonyl)amino)-3-((4-nitro-1-((2-(trimethylsilyl) ethoxy)methyl)-1H-pyrazol-5-yl)oxy)propanoic acid (600 mg, 1.34 mmol) in methanol (50 mL) was added 10% palladium on carbon (212 mg, 2.00 mmol). The resulting mixture was hydrogenated (50 psi) at 20° C. for 2 h and then filtered through Celite. The filtrate was concentrated to dryness in vacuo to afford crude (S)-3-((4-amino-1-((2-(trimethyl silyl)ethoxy)methyl)-1H-pyrazol-5-yl)oxy)-2-((tert-butoxycarbonyl)amino)propanoic acid (500 mg, 89% yield) as yellow oil: LCMS (5 to 95% acetonitrile in water+0.03% trifluoroacetic acid over 1.5 mins) retention time 0.831 min, ESI+ found [M+H]=417.2.

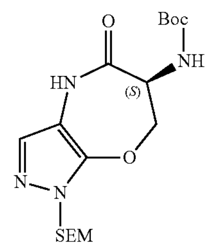

Step 5: (S)-tert-butyl (5-oxo-1-((2-(trimethylsilyl) ethoxy)methyl)-4,5,6,7-tetrahydro-1H-pyrazolo[3,4-b][1,4]oxazepin-6-yl)carbamate To a solution of (S)-3-((4-amino-1-((2-(trimethylsilyl) ethoxy)methyl)-1H-pyrazol-5-yl)oxy)-2-((tert-butoxycarbonyl)amino)propanoic acid (500 mg, 1.20 mmol) in N,N-dimethylformamide (10 mL) was added $N^1$-((ethylimino) methylene)-$N^3$,$N^3$-dimethylpropane-1,3-diamine hydrochloride (275 mg, 1.44 mmol). The reaction mixture was stirred at 20° C. for 2 h and then concentrated to dryness in vacuo. The residue was purified by column chromatography (silica gel, 100-200 mesh, 0-50% ethyl acetate in petroleum ether) to afford (S)-tert-butyl (5-oxo-1-((2-(trimethyl silyl)ethoxy)methyl)-4,5,6,7-tetrahydro-1H-pyrazol o[3,4-b][1,4]oxazepin-6-yl)carbamate (300 mg, 63% yield) as yellow oil: $^1$H NMR (400 MHz, $CDCl_3$) δ 7.68 (s, 1H), 7.22 (s, 1H), 5.79 (s, 1H), 5.35 (d, J=11.2 Hz, 1H), 5.22 (d, J=11.2 Hz, 1H), 4.63 (d, J=11.2 Hz, 1H), 4.53 (s, 1H), 4.24-4.20 (m, 1H), 3.62 (t, J=8.2 Hz, 2H), 1.48 (s, 9H), 0.93 (t, J=8.2 Hz, 2H), 0.01 (s, 9H).

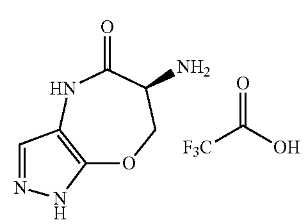

Step 6: (S)-6-amino-6,7-dihydro-1H-pyrazolo[3,4-b][1,4]oxazepin-5(4H)-one 2,2,2-trifluoroacetate To a solution of (S)-tert-butyl (5-oxo-1-((2-(trimethylsilyl)ethoxy)methyl)-4,5,6,7-tetrahydro-1H-pyrazolo[3,4-b]

[1,4]oxazepin-6-yl)carbamate (100 mg, 0.25 mmol) in dichloromethane (10 mL) was added 2,2,2-trifluoroacetic acid (565 mg, 5.00 mmol). The reaction mixture was stirred at 20° C. for 2 h and concentrated to dryness in vacuo to afford (S)-6-amino-6,7-dihydro-1H-pyrazolo[3,4-b][1,4] oxazepin-5(4H)-one 2,2,2-trifluoroacetate (70 mg, 99% yield) as a yellow solid used without further purification in the next step.

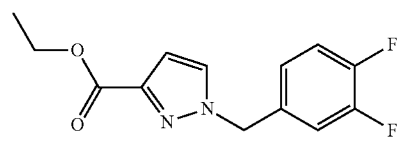 [SMILES: CCOC(=O)c1ccn(Cc2ccc(F)c(F)c2)n1]

Step 7: ethyl 1-(3,4-difluorobenzyl)-1H-pyrazole-3-carboxylate

A mixture of ethyl 1H-pyrazole-3-carboxylate (1.4 g, 9.66 mmol), 4-(bromomethyl)-1,2-difluorobenzene (1.0 g, 4.83 mmol) and potassium hydroxide (0.27 g, 4.83 mmol) in tetrahydrofuran (100 mL) was stirred at 70° C. for 12 h. After cooling to RT, the mixture was filtered and the filtrate was concentrated to dryness in vacuo. The resulting residue was purified by column chromatography (silica gel, 100-200 mesh, 0 to 100% ethyl acetate in petroleum ether) to afford ethyl 1-(3,4-difluorobenzyl)-1H-imidazole-4-carboxylate (1.2 g, 93% yield) as white solid: LCMS (0 to 60% acetonitrile in water+0.03% trifluoroacetic acid over 2 mins) retention time 1.25 min, ESI+ found [M+H]=266.9.

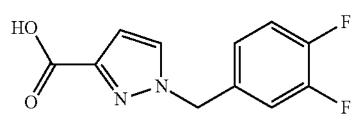 [SMILES: O=C(O)c1ccn(Cc2ccc(F)c(F)c2)n1]

Step 8: 1-(3,4-difluorobenzyl)-1H-pyrazole-3-carboxylic acid

A mixture of ethyl methyl 1-(3,4-difluorobenzyl)-1H-imidazole-4-carboxylate (1.2 g, 4.51 mmol) in ethanol (40 mL) and water (5 mL) was potassium hydroxide (2.5 g, 45.07 mmol) was stirred at 25° C. for 13 h and concentrated to dryness in vacuo. The residue was dissolved with water (5 mL) and adjusted the pH=3 by addition of 1M hydrochloric acid. The resulting solid was collected by filtration and dried under reduced pressure to afford 1-(3,4-difluorobenzyl)-1H-pyrazole-3-carboxylic acid (0.73 g, 68% yield) as a white solid: LCMS (0 to 60% acetonitrile in water+0.03% trifluoroacetic acid over 2 mins) retention time 1.07 min, ESI+ found [M+H]=238.9.

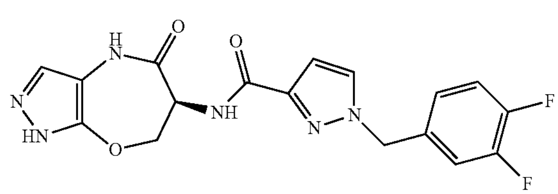 [SMILES: O=C(N[C@H]1COc2[nH]ncc2NC1=O)c1ccn(Cc2ccc(F)c(F)c2)n1]

Step 9: (S)-1-(3,4-difluorobenzyl)-N-(5-oxo-4,5,6,7-tetrahydro-1H-pyrazolo[3, 4-b][1,4]oxazepin-6-yl)-1H-pyrazole-3-carboxamide To a solution of (S)-6-amino-6,7-dihydro-1H-pyrazolo[3,4-b][1,4]oxazepin-5(4H)-one 2,2,2-trifluoroacetate (70.0 mg, 0.25 mmol) in N,N-dimethylformamide (5 mL) was added 1-(3,4-difluorobenzyl)-1H-pyrazole-3-carboxylic acid (71.4 mg, 0.30 mmol), 1H-benzo[d][1,2,3]triazol-1-ol (40.5 mg, 0.30 mmol) and $N^1$-((ethylimino)methylene)-$N^3$,$N^3$-dimethylpropane-1,3-diamine hydrochloride (57.3 mg, 0.30 mmol). The reaction mixture was heated to 50° C. for 16 h and concentrated to dryness in vacuo. The residue was purified by RP-HPLC (18-48% acetonitrile in water and 0.05% ammonia hydroxide) to afford (S)-1-(3,4-difluorobenzyl)-N-(5-oxo-4,5,6,7-tetrahydro-1H-pyrazolo[3,4-b][1,4]oxazepin-6-yl)-1H-pyrazole-3-carboxamide (5.9 mg, 6.1% yield) as a white solid: $^1$H NMR (400 MHz, $CD_3OD$) δ 7.78 (d, J=2.4 Hz, 1H), 7.36 (s, 1H), 7.10 (d, J=7.6 Hz, 1H), 7.26-7.20 (m, 2H), 7.14-7.10 (m, 1H), 6.80 (d, J=2.0 Hz, 1H), 5.41 (s, 2H), 4.89-4.85 (m, 1H), 4.53-4.50 (m, 1H), 4.33-4.28 (m, 1H). LCMS (5 to 95% acetonitrile in water+0.03% trifluoroacetic acid over 1.5 mins) retention time 0.74 min, ESI+ found [M+H]=389.0.

Example 17: Method O

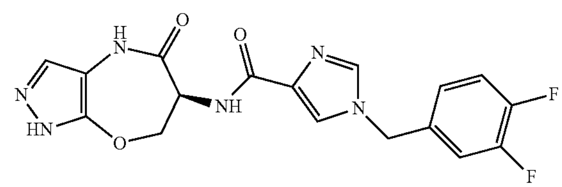 [SMILES: O=C(N[C@H]1COc2[nH]ncc2NC1=O)c1cn(Cc2ccc(F)c(F)c2)cn1]

1-[(3,4-difluorophenyl)methyl]-N-[(6S)-5-oxo-1,4,6,7-tetrahydropyrazolo[3,4-b][1,4]oxazepin-6-yl]imidazole-4-carboxamide

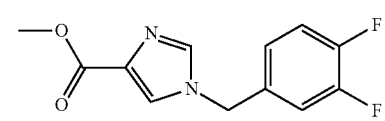 [SMILES: COC(=O)c1cn(Cc2ccc(F)c(F)c2)cn1]

Step 1: methyl 1-(3,4-difluorobenzyl)-1H-imidazole-4-carboxylate

A mixture of 4-(bromomethyl)-1,2-difluorobenzene (10.0 g, 48.3 mmol), 1H-imidazole-4-carboxylate (12.2 g, 96.6 mmol) and potassium hydroxide (5.4 g, 96.6 mmol) in tetrahydrofuran (100 mL) was heated at 70° C. for 12 h. After cooled, the mixture was filtered and the filtrate was concentrated to dryness in vacuo. The residue was purified by column chromatography (silica gel, 100-200 mesh, 0 to 100% ethyl acetate in petroleum ether) to afford methyl 1-(3,4-difluorobenzyl)-1H-imidazole-4-carboxylate (5.0 g, 41% yield) as a white solid: LCMS (5 to 95% acetonitrile in water+0.03% trifluoroacetic acid over 1.5 mins) retention time 0.70 min, ESI+ found [M+H]=252.8.

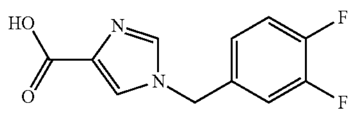 [SMILES: O=C(O)c1cn(Cc2ccc(F)c(F)c2)cn1]

Step 2: 1-(3,4-difluorobenzyl)-1H-imidazole-4-carboxylic acid

A mixture of methyl 1-(3,4-difluorobenzyl)-1H-imidazole-4-carboxylate (5.0 g, 19.07 mmol) in ethanol (50 mL) and water (5 mL) was added potassium hydroxide (5.4 g, 95.34 mmol). The mixture was stirred at 25° C. for 13 h and concentrated to dryness in vacuo. The residue was diluted with water (5 mL) and adjusted the pH=3 by addition of 1M hydrochloric acid. The resulting solid was collected by filtration and dried under reduced pressure to afford 1-(3,4-difluorobenzyl)-1H-imidazole-4-carboxylic acid (4.5 g, 99.1% yield) as a white solid:

LCMS (5 to 95% acetonitrile in water+0.03% trifluoroacetic acid over 1.5 mins) retention time 0.22 min, ESI+ found [M+H]=238.8.

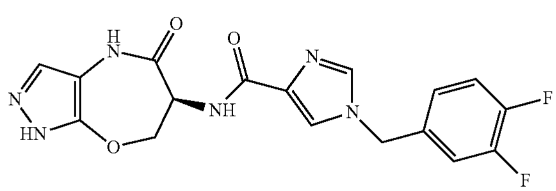 [SMILES: O=C(N[C@H]1COc2[nH]ncc2NC1=O)c1cn(Cc2ccc(F)c(F)c2)cn1]

Step 3: 1-[(3,4-difluorophenyl)methyl]-N-[(6S)-5-oxo-1,4,6,7-tetrahydropyrazolo[3,4-b][1,4]oxazepin-6-yl]imidazole-4-carboxamide To a solution of (S)-6-amino-6,7-dihydro-1H-pyrazolo[3,4-b][1,4]oxazepin-5(4H)-one 2,2,2-trifluoroacetate (70 mg, 0.25 mmol) in N,N-dimethylformamide (5 mL) was added 1-(3,4-difluorobenzyl)-1H-imidazole-4-carboxylic acid (71 mg, 0.30 mmol), 1H-benzo[d][1,2,3]triazol-1-ol (41 mg, 0.30 mmol) and $N^1$-((ethylimino)methylene)-$N^3$,$N^3$-dimethylpropane-1,3-diamine hydrochloride (57 mg, 0.30 mmol). The mixture was heated at 50° C. for 16 h and concentrated to dryness in vacuo. The residue was purified by RP-HPLC (17-47% acetonitrile in water and 0.05% ammonia hydroxide) to afford (S)-1-(3,4-difluorobenzyl)-N-(5-oxo-4,5,6,7-tetrahydro-1H-pyrazolo[3,4-b][1,4]oxazepin-6-yl)-1H-imidazole-4-carboxamide (4.9 mg, 5.1% yield) as a white solid: $^1$H NMR (400 MHz, $CD_3OD$) δ7.79 (s, 1H), 7.74 (s, 1H), 7.36 (s, 1H), 7.32-7.24 (m, 2H), 7.14-7.05 (m, 1H), 5.26 (s, 2H), 4.82-4.50 (m, 1H), 4.51-4.48 (m, 1H), 4.31-4.26 (m, 1H). LCMS (10 to 80% acetonitrile in water+0.05% ammonium hydroxide over 3 mins) retention time 1.36 min, ESI+ found [M+H]=389.1.

Example 18: Method P

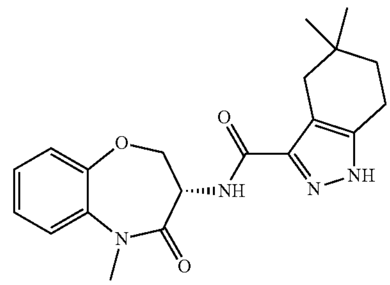 [SMILES: CN1C(=O)[C@@H](NC(=O)c2n[nH]c3c2CC(C)(C)CC3)COc2ccccc21]

5,5-dimethyl-N-[(3S)-5-methyl-4-oxo-2,3-dihydro-1,5-benzoxazepin-3-yl]-1,4,6,7-tetrahydroindazole-3-carboxamide

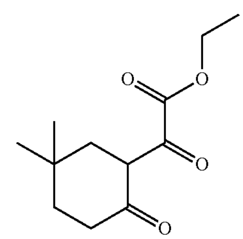 [SMILES: CCOC(=O)C(=O)C1CC(C)(C)CCC1=O]

Step 1: ethyl 2-(5,5-dimethyl-2-oxocyclohexyl)-2-oxoacetate

To a solution of 4,4-dimethylcyclohexanone (2.5 g, 19.8 mmol) in ethanol (30 mL) was added a solution of sodium ethoxide (1.5 g, 21.8 mmol) in ethanol (30 mL), followed by diethyl oxalate (2.9 g, 19.8 mmol) at 0° C. After addition, the mixture was stirred at 25° C. for 15 h and concentrated to dryness in vacuo to afford crude ethyl 2-(5,5-dimethyl-2-oxocyclohexyl)-2-oxoacetate (4.5 g, 100% yield) as a yellow solid used in the next step without further purification.

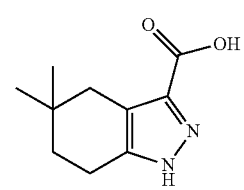

Step 2: 5,5-dimethyl-4,5,6,7-tetrahydro-1H-indazole-3-carboxylic acid

To a solution of ethyl 2-(5,5-dimethyl-2-oxocyclohexyl)-2-oxoacetate (4.47 g, 21.8 mmol) in glacial acetic acid (5 mL) was added hydrazine hydrate (0.18 g, 21.8 mmol) at 0° C. The mixture was stirred at 25° C. for 1 h and then adjusted to pH=8 by addition of aqueous sodium bicarbonate. The resulting mixture was extracted with methanol and dichloromethane (3×300 mL, methanol/dichloromethane=5:95). The combined organic extracts were washed with water (50 mL), brine (50 mL), dried over anhydrous sodium sulfate and concentrated to dryness in vacuo. The residue was purified by column chromatography (silica gel, 100-200 mesh, 0 to 30% ethyl acetate in petroleum ether) to afford ethyl 5,5-dimethyl-4,5,6,7-tetrahydro-1H-indazole-3-carboxylate (700 mg). The above material was dissolved in THF (10 mL) and water (2 mL), and added lithium hydroxide monohydrate (500 mg, 11.9 mmol). The mixture was stirred at 25° C. for 12 h and concentrated to dryness in vacuo. The residue was diluted with water (10 mL) and washed with ethyl acetate (2×20 mL). The aqueous layer was then adjust to pH=3 by addition of 1M HCl. The solution was extracted with ethyl acetate (3×20 mL). The combined organic extracts were dried over anhydrous sodium sulfate and concentrated to dryness in vacuo to afford 5,5-dimethyl-4,5,6,7-tetrahydro-1H-indazole-3-carboxylic acid (100 mg, 2.5% yield over 2 steps) as a white solid: LCMS (5 to 95% acetonitrile in water+0.04% formic acid over 1.5 mins) retention time 0.66 min, ESI+ found [M+H]=195.1.

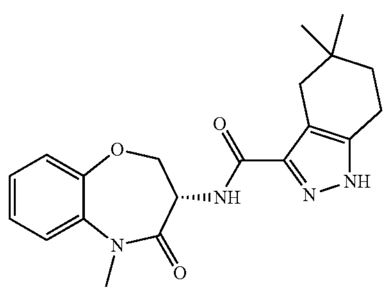 [SMILES: CN1C(=O)[C@@H](NC(=O)c2n[nH]c3c2CC(C)(C)CC3)COc2ccccc21]

Step 3: 5,5-dimethyl-N-[(3S)-5-methyl-4-oxo-2,3-dihydro-1,5-benzoxazepin-3-yl]-1,4,6,7-tetrahydroindazole-3-carboxamide To a solution of 5,5-dimethyl-4,5,6,7-tetrahydro-1H-indazole-3-carboxylic acid (100 mg, 0.51 mmol) in N,N-dimethylformamide (5 mL) was added 1H-benzo[d][1,2,3]triazol-1-ol (76 mg, 0.56 mmol), (3S)-3-amino-5-methyl-2,3-dihydro-1,5-benzoxazepin-4-one (108 mg, 0.56 mmol) and N-1-((ethylamine)ethylene)-$N_3$,$N_3$-dimethylpropane-1,3-diamine hydrochloride (108 mg, 0.56 mmol). The mixture was stirred at 25° C. for 1 h and concentrated to dryness in vacuo. The residue was purified by RP-HPLC (45-75% acetonitrile in water and 0.05% hydrochloric acid) to afford 5,5-dimethyl-N-[(3S)-5-methyl-4-oxo-2,3-dihydro-1,5-benzoxazepin-3-yl]-1,4,6,7-tetrahydroindazole-3-carboxamide (30 mg, 15.8% yield) as white solid: $^1$H NMR (400 MHz, DMSO-d6) δ 7.90 (d, J=8.0 Hz, 1H), 7.49-7.45 (m, 1H), 7.31-7.19 (m, 3H), 4.82-4.77 (m, 1H), 4.51-4.34 (m, 2H), 3.29 (s, 3H), 2.57-2.52 (m, 2H), 2.32 (s, 2H), 1.45 (t, J=6.4 Hz, 2H), 0.88 (s, 6H). LCMS (5 to 95% acetonitrile in water+0.04% formic acid over 1.5 mins) retention time 0.86 min, ESI+ found [M+H]=369.0.

Example 19: Method Q

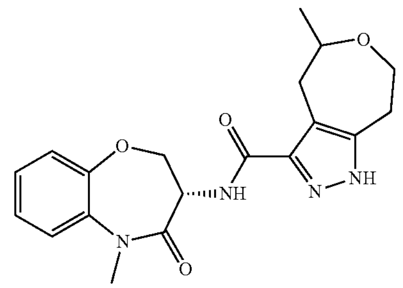 [SMILES: CC1Cc2c(C(=O)N[C@H]3COc4ccccc4N(C)C3=O)n[nH]c2CCO1]

5-methyl-N—((S)-5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide

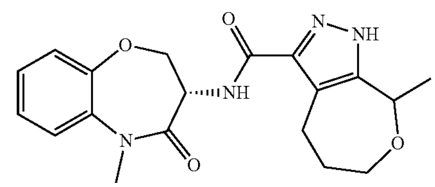 [SMILES: CC1OCCCc2c(C(=O)N[C@H]3COc4ccccc4N(C)C3=O)n[nH]c21]

8-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide

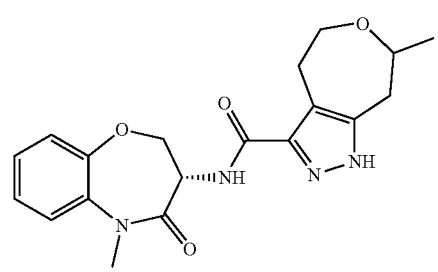 [SMILES: CC1Cc2[nH]nc(C(=O)N[C@H]3COc4ccccc4N(C)C3=O)c2CCO1]

7-methyl-N—((S)-5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide

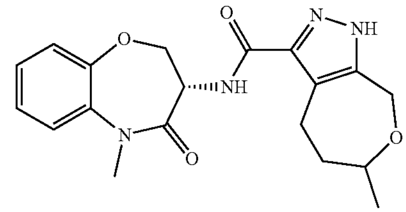 [SMILES: CC1CCc2c(C(=O)N[C@H]3COc4ccccc4N(C)C3=O)n[nH]c2CO1]

6-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide

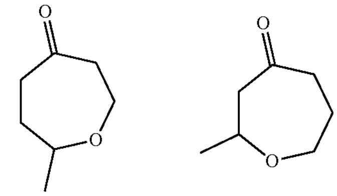

Step 1: 7-methyloxepan-4-one and 2-methyloxepan-4-one

To a solution of 2-methyldihydro-2H-pyran-4(3H)-one (3.0 g, 26.68 mmol) in dichloromethane (60 mL) and boron fluoride ethyl ether (8.1 mL, 48% ethyl ether) was added trimethylsilyldiazomethane (14.5 mL, 28.91 mmol, 2 M in hexane) dropwise at −30° C. After addition, the resulting solution was stirred for 1 h at −30° C. and quenched by addition of saturated sodium bicarbonate (30 mL). The resulting mixture was extracted with dichloromethane (3×100 mL). The combined organic layers were dried over anhydrous sodium sulfate and concentrated to dryness in vacuo. The residue was purified by column chromatography (silica gel, 100-200 mesh, 0 to 30% ethyl acetate in petroleum ether) to afford a mixture of 7-methyloxepan-4-one and 2-methyloxepan-4-one (1.2 g, 35.1% yield) as a yellow oil used in the next step without further purification.

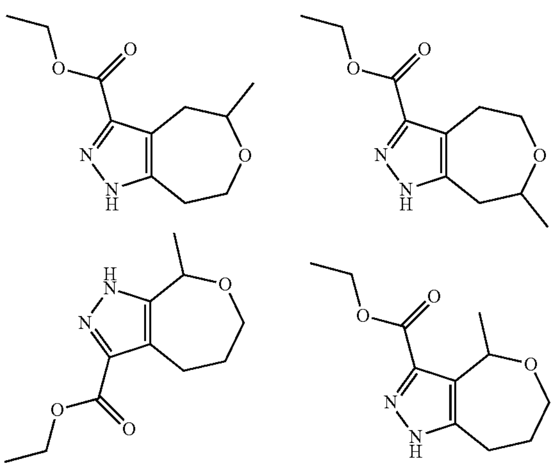

Step 2: ethyl 5-methyl-4,5,7,8-tetrahydro-1H-oxepino[4,5-c]pyrazole-3-carboxylate; ethyl 7-methyl-4,5,7,8-tetrahydro-1H-oxepino[4,5-c]pyrazole-3-carboxylate; ethyl 8-methyl-4,5,6,8-tetrahydro-1H-oxepino[3,4-c]pyrazole-3-carboxylate and ethyl 6-methyl-4,5,6,8-tetrahydro-1H-oxepino[3,4-c]pyrazole-3-carboxylate To a solution of 7-methyloxepan-4-one and 2-methyloxepan-4-one (1.00 g, 7.8 mmol) in dimethyl sulfoxide (30 mL) was added ethyl diazoacetate (1.07 g, 9.4 mmol), pyrrolidine (0.11 g, 1.56 mmol). The mixture was stirred at 20° C. for 16 h and diluted with water (20 mL). The solution was extracted with ethyl acetate (3×25 mL). The combined organic layers were washed with water (3×25 mL), dried over sodium sulfate and concentrated to dryness in vacuo. The residue was purified by column chromatography (silica gel, 100-200 mesh, 0 to 100% ethyl acetate in petroleum ether) to afford:

ethyl 5-methyl-4,5,7,8-tetrahydro-1H-oxepino[4,5-c]pyrazole-3-carboxylate (120 mg, 6.9% yield) as a yellow solid: $^1$H NMR (400 MHz, $CDCl_3$) δ 4.38 (q, J=6.8 Hz, 2H), 4.24-4.20 (m, 1H), 3.63-3.55 (m, 2H), 3.45-3.41 (m, 1H), 3.06-3.05 (m, 1H), 2.97-2.89 (m, 1H), 2.70-2.63 (m, 1H), 1.40 (t, J=7.2 Hz, 3H), 1.33 (d, J=6.4 Hz, 3H); ethyl 7-methyl-4,5,7,8-tetrahydro-1H-oxepino[4,5-c]pyrazole-3-carboxylate (120 mg, 6.9% yield) as yellow solid: $^1$H NMR (400 MHz, $CDCl_3$) δ 4.38 (q, J=7.2 Hz, 2H), 4.26-4.22 (m, 1H), 3.67-3.56 (m, 1H), 3.54-3.49 (m, 1H), 3.37-3.32 (m, 1H), 3.04-2.90 (m, 1H), 2.90-2.83 (m, 2H), 1.40 (t, J=7.2 Hz, 3H), 1.32 (d, J=6.0 Hz, 3H); ethyl 8-methyl-4,5,6,8-tetrahydro-1H-oxepino[3,4-c]pyrazole-3-carboxylate (250 mg, 14.3% yield) as yellow solid: $^1$H NMR (400 MHz, $CDCl_3$) δ 4.60-4.55 (m, 1H), 4.44-4.35 (m, 2H), 4.33-4.28 (m, 1H), 3.86-3.79 (m, 1H), 3.39-3.34 (m, 1H), 2.80-2.76 (m, 1H), 1.90-1.83 (m, 2H), 1.65 (d, J=6.4 Hz, 3H), 1.39 (t, J=7.2 Hz, 3H) and ethyl 6-methyl-4,5,6,8-tetrahydro-1H-oxepino[3,4-c]pyrazole-3-carboxylate (250 mg, 14.3% yield) as a yellow solid: $^1$H NMR (400 MHz, $CDCl_3$) δ 4.92 (d, J=14.4 Hz, 1H), 4.52 (d, J=14.4 Hz, 1H), 4.41-4.35 (m, 2H), 3.86-3.82 (m, 1H), 3.43-3.37 (m, 1H), 2.70-2.65 (m, 1H), 2.00-1.92 (m, 1H), 1.64-1.61 (m, 1H), 1.39 (t, J=7.2 Hz, 3H), 1.29 (d, J=6.4 Hz, 3H).

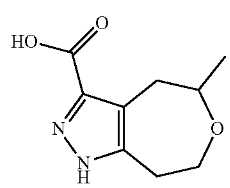

Step 3: 5-methyl-4,5,7,8-tetrahydro-1H-oxepino[4,5-c]pyrazole-3-carboxylic acid

To a solution of ethyl 5-methyl-4,5,7,8-tetrahydro-1H-oxepino[4,5-c]pyrazole-3-carboxylate (110 mg, 0.49 mmol) in tetrahydrofuran (5 mL) and water (1 mL) was added lithium hydroxide (118 mg, 4.91 mmol). The mixture was stirred at 20° C. for 20 h and then concentrated to dryness in vacuo. The residue was diluted with water (30 mL) and adjusted pH=3 by addition of 1 M hydrochloric acid. The resulting solution was extracted with ethyl acetate (3×50 mL). The combined organic layers were dried over sodium sulfate and concentrated to dryness in vacuo to afford the crude 5-methyl-4,5,7,8-tetrahydro-1H-oxepino[4,5-c]pyrazole-3-carboxylic acid (100 mg, 100% yield) as a white solid: LCMS (5 to 95% acetonitrile in water+0.03% trifluoroacetic acid over 1.5 mins) retention time 0.86 min, ESI+ found [M+H]=196.9.

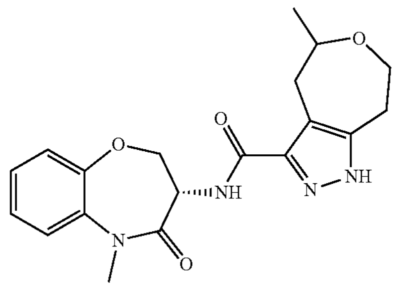 [SMILES: CC1Cc2c(C(=O)N[C@H]3COc4ccccc4N(C)C3=O)n[nH]c2CCO1]

Step 4: 5-methyl-N—((S)-5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide To a solution of 5-methyl-4,5,7,8-tetrahydro-1H-oxepino[4,5-c]pyrazole-3-carboxylic acid (50.0 mg, 0.25 mmol) in N,N-dimethylformamide (5 mL) was added 1H-benzo[d][1,2,3]triazol-1-ol (41.3 mg, 0.31 mmol), $N^1$-((ethylimino)methylene)-$N^3$,$N^3$-dimethylpropane-1,3-diamine hydrochloride (58.6 mg, 0.31 mmol) and (3S)-3-amino-5-methyl-2,3-dihydro-1,5-benzoxazepin-4-one (53.9 mg, 0.28 mmol). The reaction mixture was stirred at 25° C. for 1 h and concentrated to dryness in vacuo. The residue was purified by RP-HPLC (50-80% methanol in water and 0.05% ammonia) to afford 5-methyl-N-[(3S)-5-methyl-4-oxo-2,3-dihydro-1,5-benzoxazepin-3-yl]-4,5,7,8-tetrahydro-1H-oxepino[4,5-c]pyrazole-3-carboxamide (30.0 mg, 32% yield) as a white solid: $^1$H NMR (400 MHz, DMSO-d6) δ 12.94 (s, 1H), 8.01-7.99 (m, 1H), 7.49-7.47 (m, 1H), 7.32-7.28 (m, 2H), 7.24-7.21 (m, 1H), 4.82-4.79 (m, 1H), 4.42-4.39 (m, 1H), 4.37-4.35 (m, 1H), 4.07-4.04 (m, 1H), 3.49-3.45 (m, 3H), 3.31 (s, 3H), 2.87-2.80 (m, 2H), 2.49-2.35 (m, 1H), 1.13 (d, J=6.0 Hz, 3H). LCMS (5 to 95% acetonitrile in water+0.03% trifluoroacetic acid over 1.5 mins) retention time 0.78 min, ESI+ found [M+H]=371.0.

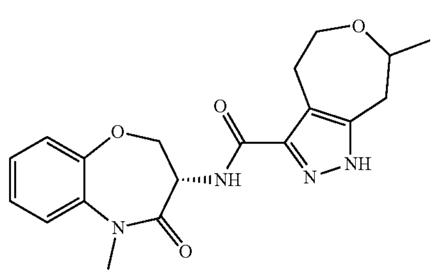 [SMILES: CC1Cc2[nH]nc(C(=O)N[C@H]3COc4ccccc4N(C)C3=O)c2CCO1]

7-methyl-N—((S)-5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide

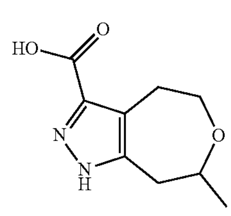

Step 5: 7-methyl-4,5,7,8-tetrahydro-1H-oxepino[4,5-c]pyrazole-3-carboxylic acid

To a solution of ethyl 7-methyl-4,5,7,8-tetrahydro-1H-oxepino[4,5-c]pyrazole-3-carboxylate (120 mg, 0.54 mmol) in tetrahydrofuran (5 mL) and water (1 mL) was added lithium hydroxide (128 mg, 5.35 mmol). The mixture was stirred at 20° C. for 20 h and then concentrated to dryness in vacuo. The residue was diluted with water (30 mL) and adjusted pH=3 by addition of 1 M hydrochloric acid. The resulting solution was extracted with ethyl acetate (3×50 mL). The combined organic layers were dried over sodium sulfate and concentrated to dryness in vacuo to afford crude 7-methyl-4,5,7,8-tetrahydro-1H-oxepino[4,5-c]pyrazole-3-carboxylic acid (100 mg, 95% yield) as a white solid used without further purification in the next step: LCMS (5 to 95% acetonitrile in water+0.03% trifluoroacetic acid over 1.5 mins) retention time 0.85 min, ESI+ found [M+H]=197.0.

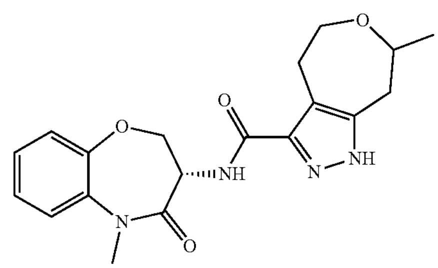 [SMILES: CC1Cc2[nH]nc(C(=O)N[C@H]3COc4ccccc4N(C)C3=O)c2CCO1]

Step 6: 7-methyl-N—((S)-5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide To a solution of 7-methyl-4,5,7,8-tetrahydro-1H-oxepino[4,5-c]pyrazole-3-carboxylic acid (50.0 mg, 0.25 mmol) in N,N-dimethylformamide (5 mL) was added 1H-benzo[d][1,2,3]triazol-1-ol (41.3 mg, 0.31 mmol), $N^1$-((ethylimino)methylene)-$N^3$,$N^3$-dimethylpropane-1,3-diamine hydrochloride (58.6 mg, 0.31 mmol) and (3S)-3-amino-5-methyl-2,3-dihydro-1,5-benzoxazepin-4-one (53.9 mg, 0.28 mmol). The reaction mixture was stirred at 25° C. for 1 h and concentrated to dryness in vacuo. The residue was purified by RP-HPLC (50-80% methanol in water and 0.05% ammonia) to afford 7-methyl-N-[(3S)-5-methyl-4-oxo-2,3-dihydro-1,5-benzoxazepin-3-yl]-4,5,7,8-tetrahydro-1H-oxepino[4,5-c]pyrazole-3-carboxamide (20 mg, 21% yield) as a white solid: $^1$H NMR (400 MHz, DMSO-d6) δ 12.92 (s, 1H), 8.00-7.97 (m, 1H), 7.49-7.47 (m, 1H), 7.32-7.28 (m, 2H), 7.24-7.23 (m, 1H), 4.84-4.79 (m, 1H), 4.50-4.44 (m, 1H), 4.42-4.39 (m, 1H), 4.05-4.01 (m, 1H), 3.61-3.58 (m, 1H), 3.38-3.36 (m, 1H), 3.31 (s, 3H), 3.30-3.26 (m, 1H), 2.87-2.83 (m, 1H), 2.71-2.65 (m, 1H), 2.61-2.50 (m, 1H), 1.19 (d, J=6.4 Hz, 3H).

LCMS (5 to 95% acetonitrile in water+0.03% trifluoroacetic acid over 1.5 mins) retention time 0.78 min, ESI+ found [M+H]=371.0.

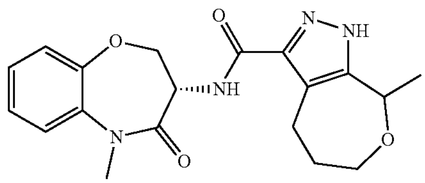 [SMILES: CC1OCCCc2c(C(=O)N[C@H]3COc4ccccc4N(C)C3=O)n[nH]c21]

8-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide

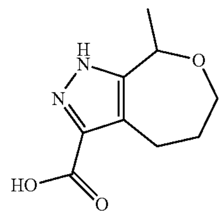

Step 7: 8-methyl-4,5,6,8-tetrahydro-1H-oxepino[3,4-c]pyrazole-3-carboxylic acid

To a solution of ethyl 8-methyl-4,5,6,8-tetrahydro-1H-oxepino[3,4-c]pyrazole-3-carboxylate (250 mg, 1.11 mmol) in tetrahydrofuran (5 mL) and water (1 mL) was added lithium hydroxide (267 mg, 11.15 mmol). The mixture was stirred at 20° C. for 20 h and concentrated to dryness in vacuo. The residue was diluted with water (30 mL) and adjusted pH=3 by addition of 1 M hydrochloric acid. The resulting solution was extracted with ethyl acetate (3×50 mL). The combined organic layers were dried over sodium sulfate and concentrated to dryness in vacuo to afford crude 8-methyl-4,5,6,8-tetrahydro-1H-oxepino[3,4-c]pyrazole-3-carboxylic acid (200 mg, 91% yield) as a white solid: LCMS (0 to 60% acetonitrile in water+0.03% trifluoroacetic acid over 2.0 mins) retention time 1.26 min, ESI+ found [M+H]=197.2.

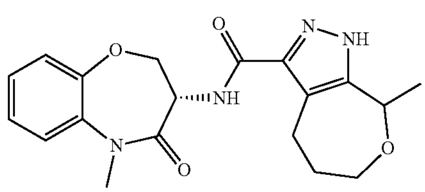 [SMILES: CC1OCCCc2c(C(=O)N[C@H]3COc4ccccc4N(C)C3=O)n[nH]c21]

Step 8: 8-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide To a solution of 8-methyl-4,5,6,8-tetrahydro-1H-oxepino[3,4-c]pyrazole-3-carboxylic acid (70.0 mg, 0.35 mol) in N,N-dimethylformamide (5 mL) was added 1H-benzo[d][1,2,3]triazol-1-ol (57.9 mg, 0.43 mmol), $N^1$-((ethylimino)methylene)-$N^3$,$N^3$-dimethylpropane-1,3-diamine hydrochloride (82.1 mg, 0.43 mmol), and (3S)-3-amino-5-methyl-2,3-dihydro-1,5-benzoxazepin-4-one (75.4 mg, 0.39 mmol). The reaction mixture was stirred at 25° C. for 1 h and concentrated to dryness in vacuo. The residue was purified by RP-HPLC (21-51% acetonitrile in water and 0.05% ammonia) to afford 8-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide (65 mg, 49% yield) as a white solid: $^1$H NMR (400 MHz, DMSO-d6) δ 12.90 (s, 1H), 8.00 (br. s, 1H), 7.50-7.47 (m, 1H), 7.33-7.28 (m, 2H), 7.26-7.24 (m, 1H), 4.84-4.81 (m, 1H), 4.63-4.60 (m, 1H), 4.48-4.39 (m, 2H), 4.09-4.07 (m, 1H), 3.73-3.70 (m, 1H), 3.32 (s, 3H), 3.20-3.17 (m, 1H), 2.70-2.65 (m, 1H), 1.78-1.70 (m, 1H), 1.62-1.59 (m, 1H), 1.48 (d, J=6.8 Hz, 3H). LCMS (5 to 95% acetonitrile in water+0.03% trifluoroacetic acid over 1.5 mins) retention time 0.78 min, ESI+ found [M+H]=371.0.

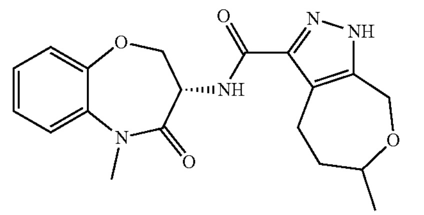 [SMILES: CC1CCc2c(C(=O)N[C@H]3COc4ccccc4N(C)C3=O)n[nH]c2CO1]

6-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide

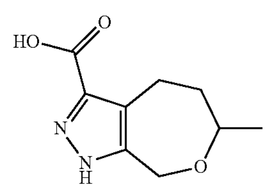

Step 9: 6-methyl-4,5,6,8-tetrahydro-1H-oxepino[3,4-c]pyrazole-3-carboxylic acid

To a solution of ethyl 6-methyl-4,5,6,8-tetrahydro-1H-oxepino[3,4-c]pyrazole-3-carboxylate (250 mg, 1.1 mmol) in tetrahydrofuran (5 mL) and water (1 mL) was added lithium hydroxide (267 mg, 11.15 mmol). The mixture was stirred at 20° C. for 20 h and concentrated to dryness in vacuo. The residue was diluted with water (30 mL) and adjusted pH=3 by addition of 1 M hydrochloric acid. The resulting solution was extracted with ethyl acetate (3×50 mL). The combined organic layers were dried over sodium sulfate and concentrated to dryness in vacuo to afford the crude 6-methyl-4,5,6,8-tetrahydro-1H-oxepino[3,4-c]pyrazole-3-carboxylic acid (200 mg, 91% yield) as a white solid: LCMS (0 to 60% acetonitrile in water+0.03% trifluoroacetic acid over 2.0 mins) retention time 1.27 min, ESI+ found [M+H]=197.2.

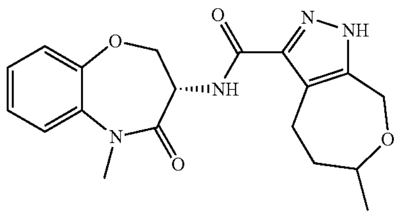 [SMILES: CC1CCc2c(C(=O)N[C@H]3COc4ccccc4N(C)C3=O)n[nH]c2CO1]

Step 10: 6-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide To a solution of 6-methyl-4,5,6,8-tetrahydro-1H-oxepino[3,4-c]pyrazole-3-carboxylic acid (70.0 mg, 0.35 mmol) in N,N-dimethylformamide (5 mL) was added 1H-benzo[d][1,2,3]triazol-1-ol (57.9 mg, 0.43 mmol), $N^1$-((ethylimino)methylene)-$N^3$,$N^3$-dimethylpropane-1,3-diamine hydrochloride (82.1 mg, 0.43 mmol) and (3S)-3-amino-5-methyl-2,3-dihydro-1,5-benzoxazepin-4-one (75.4 mg, 0.39 mmol), The reaction mixture was stirred at 25° C. for 1 h and concentrated to dryness in vacuo. The residue was purified by RP-HPLC (23-53% acetonitrile in water and 0.05% ammonia) to afford 6-methyl-N—((S)-5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide (62 mg, 47% yield) as a white solid: $^1$H NMR (400 MHz, DMSO-d6) δ 8.05-8.03 (m, 1H), 7.50-7.47 (m, 1H), 7.33-7.23 (m, 3H), 4.84-4.80 (m, 1H), 4.70 (d, J=14.8 Hz, 1H), 4.49-4.40 (m, 3H), 3.78-3.74 (m, 1H), 3.31 (s, 3H), 3.30-3.24 (m, 1H), 2.49-2.47 (m, 1H), 1.83-1.78 (m, 1H), 1.41-1.32 (m, 1H), 1.15 (d, J=6.0 Hz, 3H). LCMS (5 to 95% acetonitrile in water+0.03% trifluoroacetic acid over 1.5 mins) retention time 0.79 min, ESI+ found [M+H]=371.1.

Example 20: Method R

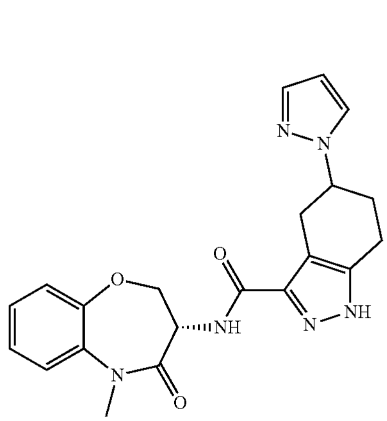 [SMILES: CN1C(=O)[C@@H](NC(=O)c2n[nH]c3c2CC(n2cccn2)CC3)COc2ccccc21]

N—((S)-5-methyl-4-oxo-2,3,4,5-tetrahydrobenzo[b][1,4]oxazepin-3-yl)-5-(1H-pyrazol-1-yl)-4,5,6,7-tetrahydro-1H-indazole-3-carboxamide

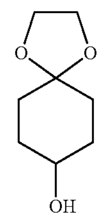

Step 1: 1,4-dioxaspiro[4.5]decan-8-ol

To a solution of 1,4-dioxaspiro[4.5]decan-8-one (10.0 g, 64.0 mmol) in methanol (150 mL) was added sodium borohydride (2.5 g, 66.1 mmol) at 0° C. The mixture was warmed to 20° C. for 3 h and then poured into water (150 mL). The resulting mixture was extracted with dichloromethane (3×200 mL). The combined organic phases were filtered through a cotton plug, and the filtrate was concentrated to dryness in vacuo to afford 1,4-dioxaspiro[4.5]decan-8-ol (7.0 g, 69% yield) used without further purification in the next step: $^1$H NMR (400 MHz, $CDCl_3$) δ 3.95-3.91 (m, 4H), 3.80-3.77 (m, 1H), 1.87-1.80 (m, 4H), 1.69-1.56 (m, 5H).

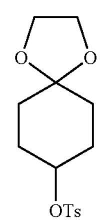

Step 2: 1,4-dioxaspiro[4.5]decan-8-yl 4-methylbenzenesulfonate

A solution of 1,4-dioxaspiro[4.5]decan-8-ol (7.0 g, 44.25 mmol) in pyridine (70 mL) was treated with 4-methylbenzenesulfonyl chloride (10.1 g, 53.1 mmol). The reaction mixture was stirred at 20° C. for 16 h and then quenched by addition of brine (50 mL). The resulting mixture was extracted with ethyl acetate (3×100 mL). The combined organics were washed with 0.5 M HCl (100 mL), saturated aqueous sodium bicarbonate (100 mL), brine (100 mL), dried over sodium sulfate and concentrated to dryness in vacuo to afford 1,4-dioxaspiro[4.5]decan-8-yl 4-methylbenzenesulfonate (10.0 g, 72.3% yield) as a clear liquid used without further purification in the next step: $^1$H NMR (400 MHz, $CDCl_3$) δ 7.77 (d, J=8.4 Hz, 2H), 7.31 (d, J=8.4 Hz, 2H), 4.63-4.60 (m, 1H), 3.93-3.86 (m, 4H), 2.42 (s, 3H), 1.84-1.76 (m, 6H), 1.54-1.50 (m, 2H).

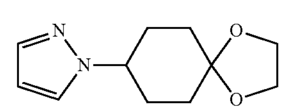

Step 3: 1-(1,4-dioxaspiro[4.5]decan-8-yl)-1H-pyrazole

To a mixture of sodium hydride (60%, 0.97 g, 24.24 mmol) in N,N-dimethylformamide (5 mL) was slowly added 1H-pyrazole (1.65 g, 24.24 mmol) at 0° C. The reaction mixture stirred for 30 min, and 1,4-dioxaspiro[4.5]decan-8-yl 4-methylbenzenesulfonate (6.26 g, 20.03 mmol) was added. After addition, the reaction mixture was stirred at 0° C. for 10 min and at 60° C. for 5 h. The reaction mixture was cooled and quenched by addition of water (30 mL). The mixture was extracted with ethyl acetate (3×50 mL). The combined organic layers were washed with brine (30 mL), dried over sodium sulfate and concentrated to dryness in vacuo. The residue was purified by column chromatography (silica gel, 100-200 mesh, 0 to 50% ethyl acetate in petroleum ether) to afford 1-(1,4-dioxaspiro[4.5]dec-8-yl)-1H-pyrazole (2.0 g, 48% yield) as a white solid: $^1$H NMR (400 MHz, DMSO-d6) δ 7.73 (d, J=2.0 Hz, 1H), 7.41 (d, J=1.6 Hz, 1H), 6.20 (t, J=2.0 Hz, 1H), 4.29-4.21 (m, 1H), 3.87-3.90 (m, 4H), 1.98-1.93 (m, 4H), 1.75-1.65 (m, 4H).

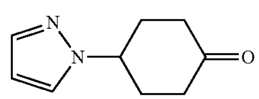 [SMILES: O=C1CCC(n2cccn2)CC1]

Step 4: 4-(1H-pyrazol-1-yl)cyclohexanone

A solution of 1-(1,4-dioxaspiro[4.5]decan-8-yl)-1H-pyrazole (2.0 g, 9.60 mmol) and 36% HCl (4.9 g, 48.02 mmol) in THF (20 ml) was stirred at ambient temperature for 20 h. The mixture was diluted with water (30 mL) and then extracted with ethyl acetate (3×50 mL). The combined organic layers were dried over sodium sulfate and concentrated to dryness in vacuo to afford crude 4-(1H-pyrazol-1-yl)cyclohexanone (1.5 g, 95% yield) as a white solid: $^1$H NMR (400 MHz, DMSO-d6) δ 7.81 (d, J=2.4 Hz, 1H), 7.45 (d, J=1.6 Hz, 1H), 6.26 (t, J=1.8 Hz, 1H), 4.74-4.67 (m, 1H), 2.59-2.52 (m, 2H), 2.33-2.17 (m, 6H).

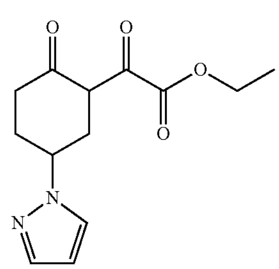 [SMILES: CCOC(=O)C(=O)C1CC(n2cccn2)CCC1=O]

Step 5: ethyl 2-oxo-2-(2-oxo-5-(1H-pyrazol-1-yl)cyclohexyl)acetate

To a solution of 4-pyrazol-1-ylcyclohexanone (1.2 g, 7.31 mmol) in ethanol (15 mL) was added a solution of sodium ethanoxide in ethanol (10 mL) at 0° C. The reaction mixture was stirred for further 10 min and diethyl oxalate (1.1 g, 7.31 mmol) was added. The resulting mixture was stirred at RT for 20 h and concentrated to dryness in vacuo to afford ethyl 2-oxo-2-(2-oxo-5-pyrazol-1-yl-cyclohexyl)acetate (2.0 g, over 100% yield) as a yellow solid use in the next step without further purification.

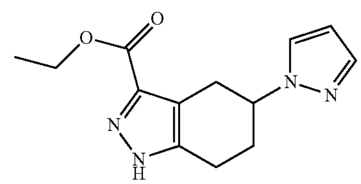 [SMILES: CCOC(=O)c1n[nH]c2c1CC(n1cccn1)CC2]

Step 6: ethyl 5-(1H-pyrazol-1-yl)-4,5,6,7-tetrahydro-1H-indazole-3-carboxylate

To a solution of ethyl 2-oxo-2-(2-oxo-5-pyrazol-1-yl-cyclohexyl)acetate (1.90 g, 7.19 mmol) in acetic acid (10 mL) was added 50% hydrazine in water (0.52 g, 8.04 mmol) at 0° C. The mixture was stirred at 25° C. for 1 h and then quenched by addition of saturated aqueous sodium bicarbonate. The mixture was extracted with methanol/dichloromethane (3×50 mL, 1:10). The combined organic layers were dried over sodium sulfate and concentrated to dryness in vacuo. The residue was purified by column chromatography (silica gel, 100-200 mesh, 0 to 100% ethyl acetate in petroleum ether) to afford ethyl 5-pyrazol-1-yl-4,5,6,7-tetrahydro-1H-indazole-3-carboxylate (1.0 g, 53% yield) as a yellow solid: LCMS (5 to 95% acetonitrile in water+0.03% trifluoroacetic acid over 1.5 mins) retention time 0.61 min, ESI+ found [M+H]=260.9.

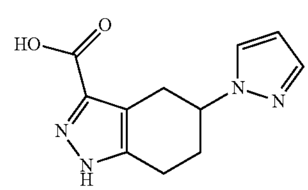 [SMILES: O=C(O)c1n[nH]c2c1CC(n1cccn1)CC2]

Step 7: 5-(1H-pyrazol-1-yl)-4,5,6,7-tetrahydro-1H-indazole-3-carboxylic acid

To a solution of ethyl 5-(1H-pyrazol-1-yl)-4,5,6,7-tetrahydro-1H-indazole-3-carboxylate (200 mg, 0.77 mmol) in tetrahydrofuran (5 mL) and water (1 mL) was added lithium hydroxide (92 mg, 3.83 mmol). The mixture was stirred at RT for 20 h and concentrated to dryness in vacuo. The residue was diluted with water (10 mL) and then adjusted to pH=3 by addition of 1 N hydrochloric acid. The solution was extracted with ethyl acetate (3×25 mL). The combined organic layers were dried over sodium sulfate and concentrated to dryness in vacuo to afford 5-(1H-pyrazol-1-yl)-4,5,6,7-tetrahydro-1H-indazole-3-carboxylic acid (100 mg, 56% yield) as a white solid: LCMS (0 to 60% acetonitrile in water+0.03% trifluoroacetic acid over 3 mins) retention time 1.36 min, ESI+ found [M+H]=233.2.

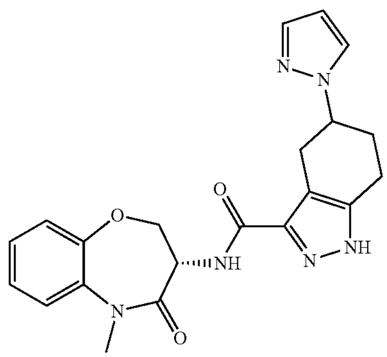 [SMILES: CN1C(=O)[C@@H](NC(=O)c2n[nH]c3c2CC(n2cccn2)CC3)COc2ccccc21]

Step 8: N—((S)-5-methyl-4-oxo-2,3,4,5-tetrahydrobenzo[b][1,4]oxazepin-3-yl)-5-(1H-pyrazol-1-yl)-4,5,6,7-tetrahydro-1H-indazole-3-carboxamide To a solution of 1H-benzo[d][1,2,3]triazol-1-ol (49 mg, 0.36 mmol) in N,N-dimethylformamide (5 mL) was added $N^1$-((ethylimino)methylene)-$N^3$,$N^3$-dimethylpropane-1,3-diamine hydrochloride (69 mg, 0.36 mmol), 6,6-dimethyl-1,4,5,8-tetrahydrooxepino[3,4-c]pyrazole-3-carboxylic acid (63 mg, 0.30 mmol) and (3S)-3-amino-5-methyl-2,3-dihydro-1,5-benzoxazepin-4-one (64 mg, 0.33 mmol). The reaction mixture was stirred at RT for 1 h and concentrated to dryness in vacuo. The residue was purified by RP-HPLC (28-58% acetonitrile in water and 0.05% ammonia) to afford N—((S)-5-methyl-4-oxo-2,3,4,5-tetrahydrobenzo[b][1,4]oxazepin-3-yl)-5-(1H-pyrazol-1-yl)-4,5,6,7-tetrahydro-1H-indazole-3-carboxamide (60 mg, 49% yield) as a white solid: $^1$H NMR (400 MHz, DMSO-d6) δ 13.00 (br. s, 1H), 7.99 (d, J=8.4 Hz, 1H), 7.73 (d, J=2.0 Hz, 1H), 7.50-7.42 (m, 2H), 7.35-7.19 (m, 3H), 6.26-6.18 (m, 1H), 4.87-4.77 (m, 1H), 4.62-4.46 (m, 2H), 4.44-4.36 (m, 1H), 3.31 (s, 3H), 3.20-3.10 (m, 1H), 2.98-2.65 (m, 3H), 2.25-2.09 (m, 2H). LCMS (5 to 95% acetonitrile in water+0.03% trifluoroacetic acid over 1.5 mins) retention time 0.78 min, ESI+ found [M+H]=407.1.

Example 21: Method S

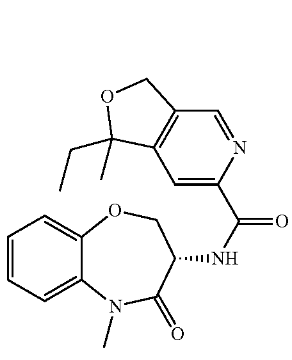

-continued

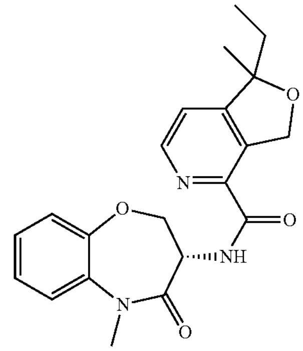

1-ethyl-1-methyl-N—((S)-5-methyl-4-oxo-2,3,4,5-tetrahydrobenzo[b][1,4]oxazepin-3-yl)-1, 3-dihydrofuro[3,4-c]pyridine-6-carboxamide and 1-ethyl-1-methyl-N—((S)-5-methyl-4-oxo-2,3,4,5-tetrahydrobenzo[b][1,4]oxazepin-3-yl)-1,3-dihydrofuro[3,4-c]pyridine-4-carboxamide

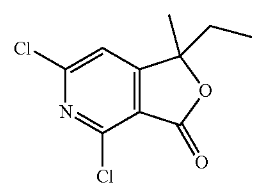

Step 1: 4,6-dichloro-1-ethyl-1-methylfuro[3,4-c]pyridin-3(1H)-one n-BuLi (2.5 M in hexane, 16 mL, 40 mmol) was added dropwise to a solution of diisopropylamine (4.7 g, 46.5 mmol) at −78° C. The mixture was stirred at −78° C. for 40 min and a solution of 2,6-dichloronicotinic acid (3 g, 15.6 mmol) in tetrahydrofuran (30 mL) was added dropwise to the reaction mixture at −78° C. and the resultant mixture was stirred at −78° C. for 3 h. Butanone (10 g, 139 mmol) was added dropwise to the reaction mixture at −78° C. and the reaction mixture was warmed slowly to RT and stirred for 16 h. The reaction mixture was cooled to 0° C., quenched with sat. ammonium chloride to pH 7 and acidified with 3 N HCl to pH 4. The mixture was extracted with ethyl acetate (30 mL×4). The combined organic layers were combined, dried over sodium sulphate and concentrated to dryness in vacuo. The residue was purified by column chromatography (silica gel, 100-200 mesh, 8:1 to 6:1 to 4:1 ethyl acetate:petroleum ether) to afford 4,6-dichloro-1-ethyl-1-methylfuro[3,4-c]pyridin-3(1H)-one as a brown solid (1.3 g, Yield 34%). LCMS: m/z=246.0/248.1 [M+1]. Column: MERCK RP18 (50-3). Mobile phase: $H_2O$ (0.01% TFA) (A)/ACN (0.01% TFA)(B) Elution program: Gradient from 10 to 95% of B in 1.8 min at 2.0 ml/min. Temperature: 45° C. 3 min gradient.

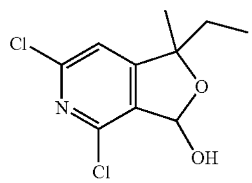

Step 2: 4,6-dichloro-1-ethyl-1-methyl-1,3-dihydrofuro[3,4-c]pyridin-3-ol

To a stirred suspension of 4,6-dichloro-1-ethyl-1-methylfuro[3,4-c]pyridin-3(1H)-one (1.3 g, 5.28 mmol) in toluene (30 mL) was added diisobutyl aluminium hydride (1 M in toluene, 12 mL, 12 mmol) at −78° C. The reaction mixture was stirred at −78° C. for 1.5 h and quenched with saturated ammonium chloride (50 ml) dropwise at −78° C. The mixture was warmed slowly to RT and stirred for 30 min. The reaction mixture was filtered and the filtrate was extracted with ethyl acetate (30 mL×3). The combined organic layers were combined, dried over sodium sulfate and concentrated to dryness in vacuo. The residue was purified by column chromatography (silica gel, 100-200 mesh, 4:1 to 2:1 ethyl acetate:petroleum ether) to afford 4,6-dichloro-1-ethyl-1-methyl-1,3-dihydrofuro[3,4-c]pyridin-3-ol (1 g, Yield 76%) as a colorless oil: LCMS: m/z=248.0/250.1 [M+1]. Column: MERCK RP18 (50-3). Mobile phase: $H_2O$ (0.01% TFA) (A)/ACN (0.01% TFA)(B) Elution program: Gradient from 10 to 95% of B in 1.8 min at 2.0 ml/min. Temperature: 45° C. 3 min gradient.

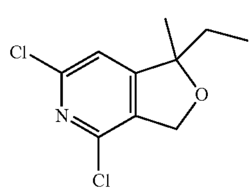

Step 3: 4,6-dichloro-1-ethyl-1-methyl-1,3-dihydrofuro[3,4-c]pyridine

To a stirred solution of 4,6-dichloro-1-ethyl-1-methyl-1,3-dihydrofuro[3,4-c]pyridin-3-ol (1 g, 4.06 mmol) in dichloromethane (10 ml) was added dropwise trifluoroacetic acid (1.5 mL, 20.1 mmol) at 0° C. and the mixture was stirred at 0° C. for 30 min. Triethylsilane (2 mL, 12.55 mmol) was added dropwise to the reaction mixture at 0° C. and the reaction mixture was warmed slowly to RT and stirred at RT for 2 h. The reaction mixture was concentrated to dryness in vacuo. The residue was dissolved in ethyl acetate (50 mL) and adjusted to pH=7 by addition of saturated sodium bicarbonate. The ethyl acetate layer was separated, dried over sodium sulphate and concentrated to dryness in vacuo. The residue was purified by column chromatography (silica gel, 100-200 mesh, 8:1 ethyl acetate:petroleum ether) to afford 4,6-dichloro-1-ethyl-1-methyl-1,3-dihydrofuro[3,4-c]pyridine (0.83 g, Yield 88%) was got as a white solid. LCMS: m/z=232.1/234.1 [M+1]. Column: MERCK RP18 (50-3). Mobile phase: $H_2O$ (0.01% TFA) (A)/ACN (0.01% TFA)(B) Elution program: Gradient from 10 to 95% of B in 1.8 min at 2.0 ml/min. Temperature: 45° C. 3 min gradient.

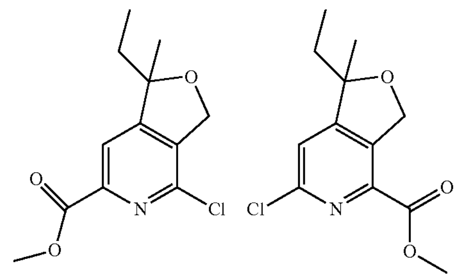

Step 1: methyl 4-chloro-1-ethyl-1-methyl-1,3-dihydrofuro[3,4-c]pyridine-6-carboxylate and methyl 6-chloro-1-ethyl-1-methyl-1,3-dihydrofuro[3,4-c]pyridine-4-carboxylate To a solution of 4,6-dichloro-1-ethyl-1-methyl-3H-furo[3,4-c]pyridine (0.50 g, 2.15 mmol) in methanol (10 mL) was added [1,1'-Bis(diphenylphosphino)ferrocene]palladium(II) dichloride (0.16 g, 0.22 mmol) and triethylamine (2.18 g, 21.54 mmol). The reaction mixture was stirred at 80° C. for 15 h under the carbon monoxide (25 psi). After cooling to RT the reaction mixture was concentrated to dryness in vacuo. The residue was purified by column chromatography (silica gel, 100-200 mesh, 0 to 30% ethyl acetate in petroleum ether) to afford methyl 4-chloro-1-ethyl-1-methyl-3H-furo[3,4-c]pyridine-6-carboxylate and methyl 6-chloro-1-ethyl-1-methyl-3H-furo[3,4-c]pyridine-4-carboxylate (140 mg (3:1 mixture), 0.55 mmol, 25.5% yield mixture) as a light yellow oil used as is in the next step without further purification.

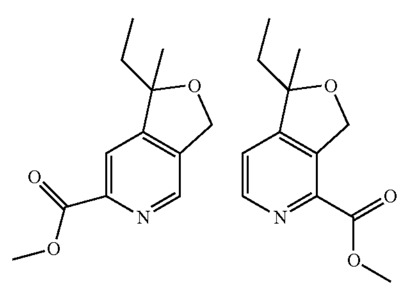

Step 2: methyl 1-ethyl-1-methyl-1,3-dihydrofuro[3,4-c]pyridine-6-carboxylate and methyl 1-ethyl-1-methyl-1,3-dihydrofuro[3,4-c]pyridine-4-carboxylate To a solution of methyl 4-chloro-1-ethyl-1-methyl-3H-furo[3,4-c]pyridine-6-carboxylate and methyl 6-chloro-1-ethyl-1-methyl-3H-furo[3,4-c]pyridine-4-carboxylate (140 mg, 0.55 mmol) in methanol (10 mL) was added 10% palladium (437 mg, 0.41 mmol) on carbon. The reaction mixture was hydrogenated (15 psi) at 20° C. for 1 h and then filtered through Celite. The filtrate was concentrated to dryness in vacuo to afford methyl 1-ethyl-1-methyl-3H-furo[3,4-c]pyridine-4-carboxylate and methyl 1-ethyl-1-methyl-3H-furo[3,4-c]pyridine-6-carboxylate (100 mg, 82.6% yield) as a yellow oil: LCMS (5 to 95% acetonitrile in water+0.03% trifluoacetic acid over 1.5 mins) retention time 0.65 min, ESI+ found [M+H]=222.

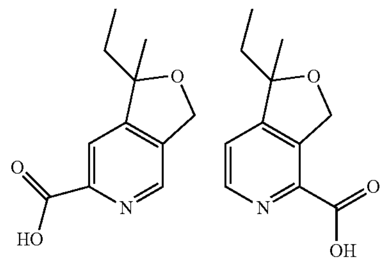

Step 3: 1-ethyl-1-methyl-1,3-dihydrofuro[3,4-c]pyridine-6-carboxylic acid and 1-ethyl-1-methyl-1,3-dihydrofuro[3,4-c]pyridine-4-carboxylic acid To a solution of methyl 1-ethyl-1-methyl-1,3-dihydrofuro[3,4-c]pyridine-6-carboxylate and methyl 1-ethyl-1-methyl-1,3-dihydrofuro[3,4-c]pyridine-4-carboxylate (100 mg, 0.46 mmol) in tetrahydrofuran (5 mL) and water (5 mL) was added lithium hydroxide monohydrate (202 mg, 4.81 mmol). The reaction mixture was stirred at 15° C. for 15 h and concentrated to dryness in vacuo. The residue was diluted with water (5 mL) and adjusted to pH=3 by addition of 1 M hydrochloric acid. The mixture was extracted with dichloromethane (3×15 mL). The combined organic layers were dried over sodium sulfate and concentrated to dryness in vacuo to afford 1-ethyl-1-methyl-1,3-dihydrofuro[3,4-c]pyridine-6-carboxylic acid and 1-ethyl-1-methyl-1,3-dihydrofuro[3,4-c]pyridine-4-carboxylic acid (50 mg, 50.5% yield) as a yellow oil used in the next step without further purification.

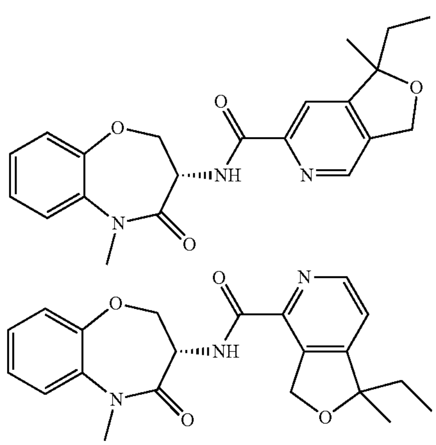

Step 4: 1-ethyl-1-methyl-N—((S)-5-methyl-4-oxo-2,3,4,5-tetrahydrobenzo[b][1,4]oxazepin-3-yl)-1, 3-dihydrofuro[3,4-c]pyridine-6-carboxamide and 1-ethyl-1-methyl-N—((S)-5-methyl-4-oxo-2,3,4,5-tetrahydrobenzo[b][1,4]oxazepin-3-yl)-1, 3-dihydrofuro[3,4-c]pyridine-4-carboxamide To a solution of 1-ethyl-1-methyl-3H-furo[3,4-c]pyridine-6-carboxylic acid and 1-ethyl-1-methyl-3H-furo[3,4-c]pyridine-4-carboxylic acid (3:1 mixture, 41 mg, 0.20 mmol) in N,N-dimethylformamide (5 mL) was added $N^1$-((ethylimino)methylene)-$N^3$,$N^3$-dimethylpropane-1,3-diamine hydrochloride (59 mg, 0.31 mmol), (3S)-3-amino-5-methyl-2,3-dihydro-1,5-benzoxazepin-4-one (50 mg, 0.26 mmol) and 1H-benzo[d][1,2,3]triazol-1-ol (35 mg, 0.26 mmol). The reaction mixture was stirred at 15° C. for 1 h and concentrated to dryness in vacuo. The residue was purified by RP-HPLC (40-70% acetonitrile in water and 0.05% ammonia hydroxide) to afford:

1-ethyl-1-methyl-N-[(3S)-5-methyl-4-oxo-2,3-dihydro-1,5-benzoxazepin-3-yl]-3H-furo[3,4-c]pyridine-6-carboxamide (15 mg, 20.7% yield) as white solid and 1-ethyl-1-methyl-N-[(3S)-5-methyl-4-oxo-2,3-dihydro-1,5-benzoxazepin-3-yl]-3H-furo[3,4-c]pyridine-4-carboxamide (7 mg, 9.6% yield) as a white solid: $^1$H NMR (400 MHz, $CD_3OD$) δ 8.57 (s, 1H), 7.86 (s, 1H), 7.45-7.43 (m, 1H), 7.39-7.29 (m, 2H), 7.26-7.25 (m, 1H), 5.16 (d, J=3.6 Hz, 2H), 5.05-5.00 (m, 1H), 4.67-4.62 (m, 1H), 4.41 (t, J=9.6, 1H), 3.43 (s, 3H), 1.88-1.82 (m, 2H), 1.46 (s, 3H), 0.77 (t, J=7.2, 3H); LCMS (5 to 95% acetonitrile in water+0.03% trifluoroacetic acid over 1.5 mins) $R_T$=0.87 min, m/z=382.0 $[M+H]^+$ and $^1$H NMR (400 MHz, $CD_3OD$) δ 8.60 (d, J=5.6 Hz, 1H), 7.45-7.42 (m, 2H), 7.34-7.24 (m, 3H), 5.33-5.28 (m, 2H), 5.02-4.97 (m, 1H), 5.16 (d, J=3.6 Hz, 2H), 5.05-5.00 (m, 1H), 4.63 (t, J=10.0 Hz, 1H), 4.41 (t, J=9.6 Hz, 1H), 3.43 (s, 3H), 1.87-1.81 (m, 2H), 1.45 (s, 3H), 0.75 (t, J=7.6 Hz, 3H); LCMS (10 to 80% acetonitrile in water+0.03% trifluoroacetic acid over 2.0 mins) $R_T$=1.17 min, m/z=382.3 $[M+H]^+$.

Example 22: Method T

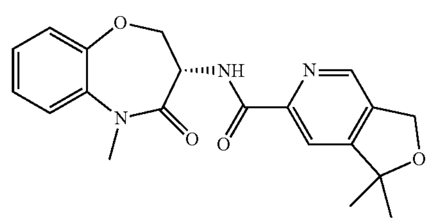 [SMILES: CN1C(=O)[C@@H](NC(=O)c2cc3c(cn2)COC3(C)C)COc2ccccc21]

(S)-1,1-dimethyl-N-(5-methyl-4-oxo-2,3,4,5-tetrahydrobenzo[b][1,4]oxazepin-3-yl)-1,3-dihydrofuro[3,4-c]pyridine-6-carboxamide 6-chloro-1,1-dimethylfuro[3,4-c]pyridin-3(1H)-one and similar starting materials for Method T are commercially purchased or prepared according to exemplary procedures shown in: WO 2005080342 A1; WO 2005074939 A1; and WO 2004029026 A1.

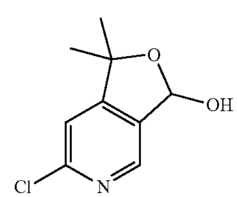

Step 1: 6-chloro-1,1-dimethyl-1,3-dihydrofuro[3,4-c]pyridin-3-ol

A stirred solution of 6-chloro-1,1-dimethylfuro[3,4-c]pyridin-3(1H)-one (18.5 g, 0.09362 mol) in dry toluene (300 mL) at RT under nitrogen was cooled to −70° C. was added dropwise diisobutylaluminum hydride (197.24 mL, 0.18724 mol, 1M in Toluene) and the reaction mixture and allowed to stir at −70° C. for 3 h. The reaction mixture was quenched with saturated ammonium chloride solution and filtered. The filtrate was extracted with ethyl acetate (2×200 mL) and the combined organic layer was washed the water, brine, dried over anhydrous sodium sulphate and concentrated to dryness in vacuo. The residue was purified by column chromatography (silica gel, 100-200 mesh, 0 to 30% ethyl acetate: petroleum ether) to afford 6-chloro-1,1-dimethyl-1,3-dihydrofuro[3,4-c]pyridin-3-ol (17.5 g, 94%): $^{1}H$ NMR (400 MHz, DMSO-d6) δ 8.4 (s, 1H), 7.65 (s, 1H), 7.2-6.40 br., s, 1H), 6.35 (s, 1H), 1.35 (s, 3H), 1.23 (s, 3H).

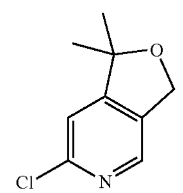

Step 2: 6-chloro-1,1-dimethyl-1,3-dihydrofuro[3,4-c]pyridine 6-chloro-1,1-dimethyl-1,3-dihydrofuro[3,4-c]pyridin-3-ol (17.5 g, 0.0877 mol) was dissolved in dry dichloromethane and cooled to 0° C. under nitrogen. To the stirred solution was added dropwise trifluoroacetic acid (32.66 ml 0.438 mol.) and stirred for 30 min at 0° C. Triethyl silane (42.47 ml, 0.263 mol) was added to the reaction mixture at 0° C. at and stirred at RT for 3 h. The reaction mixture was quenched with saturated sodium bicarbonate solution and extracted with dichloromethane (2×200 mL). The combined organic layer was washed with water, brine solution, dried over anhydrous sodium sulphate and concentrated to dryness in vacuo. The residue was purified by column chromatography (silica gel, 100-200 mesh, 0 to 30% ethyl acetate: petroleum ether) to afford 6-chloro-1,1-dimethyl-1,3-dihydrofuro[3,4-c]pyridine (15.2 g, 94%): LCMS $R_T$=1.55 min, m/z=184.04 $[M+H]^+$. Column: Acquity UPLC BEH C-18 (2.1×50 mm) 1.7u; MP:A: 0.05% FA in Water, B: 0.05% FA in Acetonitrile; T/% B: 0/10, 0.5/10, 1/35, 1.5/45, 2.3/90, 3.2/90, 3.6/10, 4/10; Flow: 0.55 mL; Diluent: ACN+WATER (70:30); Column temp: 35° C.

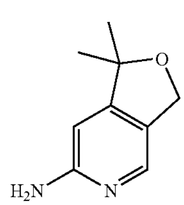

Step 3: 1,1-dimethyl-1,3-dihydrofuro[3,4-c]pyridin-6-amine

To a stirred solution of 6-chloro-1,1-dimethyl-1,3-dihydrofuro[3,4-c]pyridine (15.0 g, 0.082 mol) in dry tetrahydrofuran was added benzophenone imine (15.39 g, 0.085 mol.) and cesium carbonate (39.92 g, 0.12254) under a nitrogen atmosphere. The resulting solution was degassed with nitrogen for 10 min and 2,2'-bis(diphenylphosphino)-1,1'-binaphthyl (1.88 g, 0.003 mol) and palladium(II) acetate (0.440 g, 0.002 mol.) were added under a nitrogen atmosphere. Reaction mixture was heated at reflux for 11 h. Reaction was cooled to RT, filtered through Celite and washed with ethyl acetate. The filtrate was washed with water, brine solution, dried over anhydrous sodium sulphate and concentrated to dryness in vacuo. The residue was dissolved in tetrahydrofuran, cooled to 0° C. and 2N HCl (30 mL) was added to reaction mixture and stirred at to RT for 3 h. The reaction mixture was poured into water, extracted with ether and the aqueous layer was adjusted to pH=8 by addition of sodium bicarbonate. The mixture was extracted with ethyl acetate (2×200 mL), dried over anhydrous sodium sulphate and concentrated to dryness in vacuo. The residue was purified by column chromatography (silica gel, 100-200 mesh, 0 to 5% methanol in dichloromethane) to afford 1,1-dimethyl-1,3-dihydrofuro[3,4-c]pyridin-6-amine (3 g, 29%) as a white solid: LCMS $R_T$=1.09 min, m/z=165.11 $[M+H]^+$.

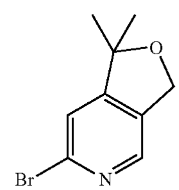

Step 4: 6-bromo-1,1-dimethyl-1,3-dihydrofuro[3,4-c]pyridine

To a solution of 1,1-dimethyl-3H-furo[3,4-c]pyridin-6-amine (200 mg, 1.22 mmol) in hydrobromic acid (0.06 mL, 1.22 mmol) was added sodium nitrite (210 mg, 3.05 mmol) in water (0.2 mL) and bromine (0.12 mL, 2.44 mmol) at −25° C. The reaction was stirred at −25° C. for 1 h and warmed to 15° C. over 30 min. The solution was diluted with 5 M sodium hydroxide (20 mL) and extracted with dichloromethane (3×20 mL). The combined organic layer were dried over sodium sulfate and concentrated to dryness in vacuo. The residue was purified by column chromatography (silica gel, 100-200 mesh, 0 to 50% ethyl acetate in petroleum ether) to afford 6-bromo-1,1-dimethyl-3H-furo[3,4-c]pyridine (150 mg, 54% yield) as a colorless oil use in the next step without further purification.

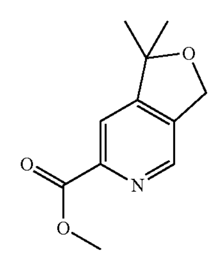

Step 5: methyl 1,1-dimethyl-1,3-dihydrofuro[3,4-c]pyridine-6-carboxylate

To a solution of 6-bromo-1,1-dimethyl-3H-furo[3,4-c]pyridine (150 mg, 0.66 mmol) in methanol (10 mL) was added [1,1'-bis(diphenylphosphino)ferrocene]palladium(II) dichloride (48 mg, 0.07 mmol) and triethylamine (665 mg, 6.58 mmol). The reaction mixture was stirred at 80° C. for 15 h under the carbon monoxide (25 psi). The reaction mixture was concentrated to dryness in vacuo. The residue was purified by column chromatography (silica gel, 100-200 mesh, 0 to 50% ethyl acetate in petroleum ether) to afford methyl 1,1-dimethyl-3H-furo[3,4-c]pyridine-6-carboxylate (100 mg, 73.4% yield) as a pale yellow oil: LCMS (10 to 80% acetonitrile in water+0.03% trifluoacetic acid over 2.0 mins) retention time 0.97 min, ESI+ found [M+H]=208.2.

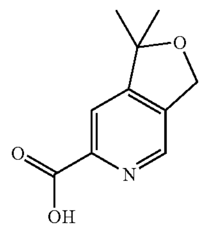

Step 6: 1,1-dimethyl-1,3-dihydrofuro[3,4-c]pyridine-6-carboxylic acid

To a solution of methyl 1,1-dimethyl-3H-furo[3,4-c]pyridine-6-carboxylate (100 mg, 0.48 mmol) in tetrahydrofuran (5 mL) and water (5 mL) was added lithium hydroxide monohydrate (202 mg, 4.83 mmol). The reaction mixture was stirred at 15° C. for 15 h and then concentrated to dryness in vacuo. The residue was diluted with water (5 mL) and then adjusted to pH=3 by addition of 1 M hydrochloric acid. The mixture was extracted with dichloromethane (3×15 mL). The combined layers were dried over sodium sulfate and concentrated to afford crude 1,1-dimethyl-3H-furo[3,4-c]pyridine-6-carboxylic acid (50 mg, 53.9% yield) as a yellow oil used in the next step without further purification.

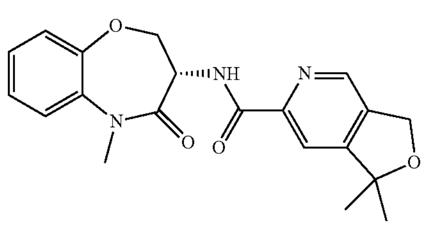 [SMILES: CN1C(=O)[C@@H](NC(=O)c2cc3c(cn2)COC3(C)C)COc2ccccc21]

Step 7: S)-1,1-dimethyl-N-(5-methyl-4-oxo-2,3,4,5-tetrahydrobenzo[b][1,4]oxazepin-3-yl)-1,3-dihydrofuro[3,4-c]pyridine-6-carboxamide To a solution of (3S)-3-amino-5-methyl-2,3-dihydro-1,5-benzoxazepin-4-one (50 mg, 0.26 mmol) in N,N-dimethylformamide (5 mL) was added 1,1-dimethyl-3H-furo[3,4-c]pyridine-6-carboxylic acid (56 mg, 0.29 mmol), $N^1$-((ethylimino)methylene)-$N^3$,$N^3$-dimethylpropane-1,3-diamine hydrochloride (60 mg, 0.31 mmol) and 1H-benzo[d][1,2,3]triazol-1-ol (42 mg, 0.31 mmol). The reaction mixture was stirred at 15° C. for 1 h and concentrated to dryness in vacuo. The residue was purified by RP-HPLC (35-65% acetonitrile in water and 0.05% ammonia hydroxide) to afford 1,1-dimethyl-N-[(3S)-5-methyl-4-oxo-2,3-dihydro-1,5-benzoxazepin-3-yl]-3H-furo[3,4-c]pyridine-6-carboxamide (18 mg, 18.8% yield) as a white solid: $^1$H NMR (400 MHz, $CD_3OD$) δ 8.57 (s, 1H), 7.91 (s, 1H), 7.44-7.43 (m, 1H), 7.34-7.31 (m, 2H), 7.26-7.25 (m, 1H), 5.15 (s, 2H), 5.05-5.00 (m, 1H), 4.65-4.62 (m 1H), 4.43-3.98 (m, 1H), 3.43 (s, 3H), 1.49 (s, 6H). LCMS (5 to 95% acetonitrile in water+0.03% trifluoroacetic acid over 1.5 mins) retention time 0.84 min, ESI+ found [M+H]=368.0.

Example 23: Method U

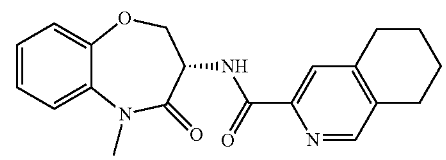 [SMILES: CN1C(=O)[C@@H](NC(=O)c2cc3c(cn2)CCCC3)COc2ccccc21]

(S)—N-(5-methyl-4-oxo-2,3,4,5-tetrahydrobenzo[b][1,4]oxazepin-3-yl)-5,6,7,8-tetrahydroisoquinoline-3-carboxamide

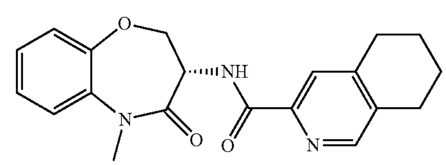 [SMILES: CN1C(=O)[C@@H](NC(=O)c2cc3c(cn2)CCCC3)COc2ccccc21]

Step 1: (S)—N-(5-methyl-4-oxo-2,3,4,5-tetrahydrobenzo[b][1,4]oxazepin-3-yl)-5,6,7,8-tetrahydroisoquinoline-3-carboxamide To a solution of 5,6,7,8-tetrahydroisoquinoline-3-carboxylic acid (80 mg, 0.45 mmol) in N,N-dimethylformamide (5 mL) was added (3S)-3-amino-5-methyl-2,3-dihydro-1,5-benzoxazepin-4-one (96 mg, 0.50 mmol), $N^1$-((ethylimino)methylene)-$N^3$,$N^3$-dimethylpropane-1,3-diamine hydrochloride (104 mg, 0.54 mmol) and 1-hydroxybenzotriazole (73 mg, 0.54 mmol). The reaction mixture was stirred at RT for 12 h and concentrated to dryness in vacuo. The residue was purified by RP-HPLC (0-40% acetonitrile in water and 0.1% ammonia hydroxide) to afford (S)—N-(5-methyl-4-oxo-2,3,4,5-tetrahydrobenzo[b][1,4]oxazepin-3-yl)-5,6,7,8-tetrahydroisoquinoline-3-carboxamide (26 mg, 16.5% yield) as white solid: $^1$H NMR (400 MHz, $CD_3OD$) δ 8.32 (s, 1H), 7.71 (s, 1H), 7.43 (d, J=6.0 Hz, 1H), 7.37-7.19 (m, 3H), 5.02-4.97 (m, 1H), 4.64-4.60 (m, 1H), 4.37 (t, J=10.8 Hz, 1H), 3.42 (s, 3H), 2.83-2.81 (m, 4H), 1.87-1.82 (m, 4H). LCMS (10-80% acetonitrile in water+0.03% trifluoroacetic over 2 mins) retention time 1.15 min, ESI+ found [M+H]=352.2.

Example 24: Method V

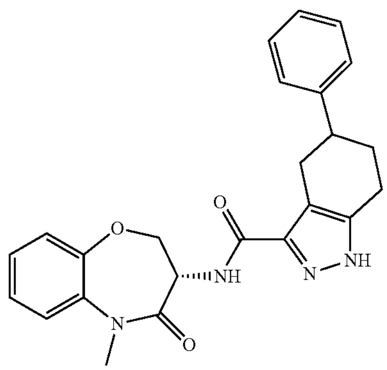 [SMILES: CN1C(=O)[C@@H](NC(=O)c2n[nH]c3c2CC(c2ccccc2)CC3)COc2ccccc21]

N—((S)-5-methyl-4-oxo-2,3,4,5-tetrahydrobenzo[b][1,4]oxazepin-3-yl)-5-phenyl-4,5,6,7-tetrahydro-1H-indazole-3-carboxamide

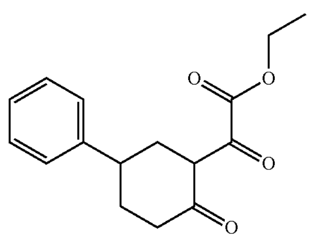 [SMILES: CCOC(=O)C(=O)C1CC(c2ccccc2)CCC1=O]

Step 1: ethyl 2-oxo-2-(2-oxo-5-phenylcyclohexyl)acetate

To a solution of 4,4-dimethylcyclohexanone (2.50 g, 19.8 mmol) in ethanol (30 mL) was added a solution of sodium ethoxide (1.48 g, 21.8 mmol) in ethanol (30 mL), followed by diethyl oxalate (2.9 g, 19.8 mmol) at 0° C. After addition, the mixture was stirred at 25° C. for 15 h and concentrated to dryness in vacuo to afford crude ethyl 2-oxo-2-(2-oxo-5-phenylcyclohexyl)acetate (5.4 g, 99.4% yield) as a yellow solid used in the next step without further purification.

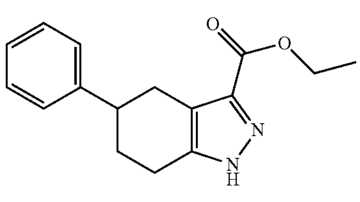 [SMILES: CCOC(=O)c1n[nH]c2c1CC(c1ccccc1)CC2]

Step 2: ethyl 5-phenyl-4,5,6,7-tetrahydro-1H-indazole-3-carboxylate

To a solution of ethyl 2-oxo-2-(2-oxo-5-phenylcyclohexyl)acetate (5.4 g, 19.7 mmol) in glacial acetic acid (5 mL) was added hydrazine hydrate (1.09 g, 21.8 mmol) at 0° C. The mixture was stirred at 25° C. for 1 h and then adjusted to pH=8 by addition of aqueous sodium bicarbonate. The resulting solid was collected by filtration and dried to afford crude ethyl 5-phenyl-4,5,6,7-tetrahydro-1H-indazole-3-carboxylate (1.5 g, 28% yield) use in the next step without further purification.

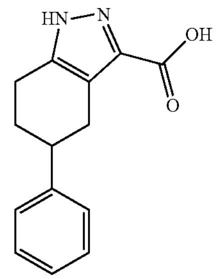 [SMILES: O=C(O)c1n[nH]c2c1CC(c1ccccc1)CC2]

Step 3: 5-phenyl-4,5,6,7-tetrahydro-1H-indazole-3-carboxylic acid

To a solution of ethyl 5-phenyl-4,5,6,7-tetrahydro-1H-indazole-3-carboxylate (405 mg, 1.5 mmol) in tetrahydrofuran (8 mL) and water (4 mL) was added lithium hydroxide hydrate (621 mg, 14.8 mmol). The mixture was stirred at 25° C. for 25 h and concentrated to dryness in vacuo. The residue was diluted with water (5 mL) and adjusted the pH=3 by addition of 1 N hydrochloric acid. The resulting solid was collected by filtration and dried to afford crude 5-phenyl-4,5,6,7-tetrahydro-1H-indazole-3-carboxylic acid (330 mg, 90.9% yield) as white solid: LCMS (5 to 95% acetonitrile in water+0.03% formic acid over 1.5 mins) retention time 0.77 min, ESI+ found [M+H]=242.9.

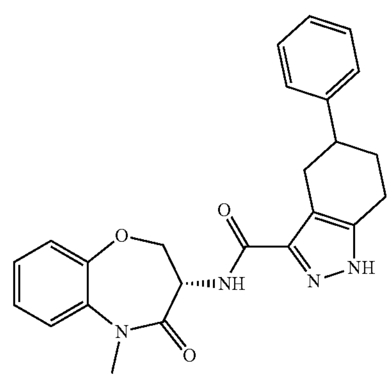 [SMILES: CN1C(=O)[C@@H](NC(=O)c2n[nH]c3c2CC(c2ccccc2)CC3)COc2ccccc21]

Step 4: N—((S)-5-methyl-4-oxo-2,3,4,5-tetrahydrobenzo[b][1,4]oxazepin-3-yl)-5-phenyl-4,5,6,7-tetrahydro-1H-indazole-3-carboxamide To a stirred solution of 5-phenyl-4,5,6,7-tetrahydro-1H-indazole-3-carboxylic acid (94 mg, 0.39 mmol) in N,N-dimethylformamide (5 mL) was added (3S)-3-amino-5-methyl-2,3-dihydro-1,5-benzoxazepin-4-one (50 mg, 0.26 mmol), 1-hydroxybenzotriazole (53 mg, 0.39 mmol) and 1-(3-dimethylaminopropyl)-3-ethylcarbodiimidehydrochloride (75 mg, 0.39 mmol). The mixture was stirred at 20° C. for 1 h and then concentrated to dryness in vacuo. The residue was purified by RP-HPLC (42-72% actonitrile in water and 0.05% ammonia hydroxide) to afford N—((S)-5-methyl-4-oxo-2,3,4,5-tetrahydrobenzo[b][1,4]oxazepin-3-yl)-5-phenyl-4,5,6,7-tetra hydro-1H-indazole-3-carboxamide (73 mg, 67.6% yield) as white solid: $^1$H NMR (400 MHz, DMSO-d6) δ12.95 (s, 1H), 7.97-7.95 (m, 1H), 7.48-7.45 (m, 1H), 7.33-7.25 (m, 6H), 7.23-7.17 (m, 2H), 4.85-4.78 (m, 1H), 4.54-4.47 (m, 1H), 4.42-4.37 (m, 1H), 3.31 (s, 3H), 2.98-2.92 (m, 1H), 2.88-2.83 (m, 1H), 2.72-2.67 (m, 2H), 2.56-2.53 (m, 1H), 1.98-1.89 (m, 2H). LCMS (10 to 80% acetonitrile in water+0.03% trifluoroacetic acid over 3 mins) retention time 1.19 min, ESI+ found [M+H]=417.3.

Example 25: Method W

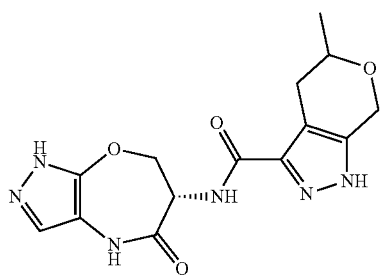 [SMILES: CC1Cc2c(C(=O)N[C@H]3COc4[nH]ncc4NC3=O)n[nH]c2CO1]

5-methyl-N—((S)-5-oxo-4,5,6,7-tetrahydro-1H-pyrazolo[3,4-b][1,4]oxazepin-6-yl)-1,4,5,7-tetrahydropyrano[3,4-c]pyrazole-3-carboxamide To a solution of (S)-6-amino-6,7-dihydro-1H-pyrazolo[3,4-b][1,4]oxazepin-5(4H)-one 2,2,2-trifluoroacetate (70 mg, 0.25 mmol) in N,N-dimethylformamide (5 mL) was added 1H-benzo[d][1,2,3]triazol-1-ol (41 mg, 0.30 mmol), 5-methyl-1,4,5,7-tetrahydropyrano[3,4-c]pyrazole-3-carboxylic acid (55 mg, 0.30 mmol), and $N^1$-((ethylimino)methylene)-$N^3$,$N^3$-dimethylpropane-1,3-diamine hydrochloride (57 mg, 0.30 mmol). The reaction mixture was heated at 50° C. for 16 h and concentrated to dryness in vacuo. The residue was purified by RP-HPLC (0 to 27% acetonitrile in water and 0.05% hydrochloric acid) to afford 5-methyl-N—((S)-5-oxo-4,5,6,7-tetrahydro-1H-pyrazolo[3,4-b][1,4]oxazepin-6-yl)-1,4,5,7-tetrahydropyrano[3,4-c]pyrazole-3-carboxamide (3.3 mg, 4%) as a white solid: $^1$H NMR (400 MHz, $CD_3OD$) δ 7.52 (s, 1H), 4.91-4.74 (m, 3H), 4.58-4.54 (m, 1H), 4.39-4.35 (m, 1H), 3.75-3.71 (m, 1H), 3.00-2.88 (m, 1H), 2.55-2.51 (m, 1H), 1.36 (d, J=3.2 Hz, 3H). LCMS (5 to 95% acetonitrile in water+0.03% trifluoroacetic acid over 1.5 mins) retention time 0.35 min, ESI+ found [M+H]=333.0.

Example 26: Method X (S)-5,5-dimethyl-N-(5-methyl-4-oxo-2,3,4,5-tetrahydrobenzo[b][1,4]oxazepin-3-yl)-4,5,7, 8-tetrahydro-1H-oxepino[4,5-c]pyrazole-3-carboxamide

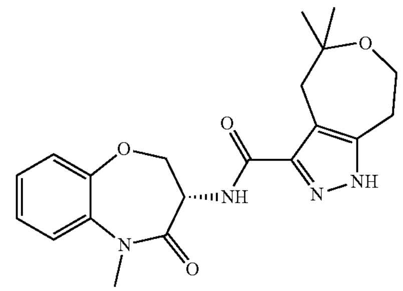 [SMILES: CN1C(=O)[C@@H](NC(=O)c2n[nH]c3c2CC(C)(C)OCC3)COc2ccccc21]

(S)-7,7-dimethyl-N-(5-methyl-4-oxo-2,3,4,5-tetrahydrobenzo[b][1,4]oxazepin-3-yl)-4,5,7, 8-tetrahydro-1H-oxepino[4,5-c]pyrazole-3-carboxamide

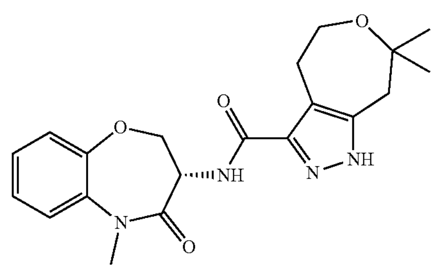 [SMILES: CN1C(=O)[C@@H](NC(=O)c2n[nH]c3c2CCOC(C)(C)C3)COc2ccccc21]

(S)-6,6-dimethyl-N-(5-methyl-4-oxo-2,3,4,5-tetrahydrobenzo[b][1,4]oxazepin-3-yl)-4,5,6, 8-tetrahydro-1H-oxepino[3,4-c]pyrazole-3-carboxamide

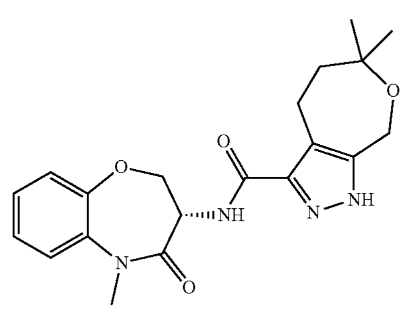

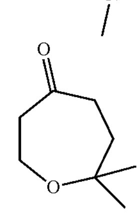

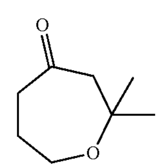

Step 1: 7, 7-dimethyloxepan-4-one and 2, 2-dimethyloxepan-4-one

To a solution of 2, 2-dimethyltetrahydropyran-4-one (10.4 g, 81.14 mmol) in dichloromethane (40 mL) and boron fluoride ethyl ether (11.2 mL, 48% ethyl ether) was added (diazomethyl)trimethylsilane (48.0 mL, 96.0 mmol, 2 M in hexane) dropwise at −30° C. After addition, the resulting solution was stirred for 1 h at −30° C. and then quenched by addition of saturated sodium bicarbonate (30 mL). The resulting mixture was extracted with dichloromethane (3×100 mL). The combined organic layers were dried over anhydrous sodium sulfate and concentrated to dryness in vacuo. The residue was purified by column chromatography (silica gel, 100-200 mesh, 0 to 18% ethyl acetate in petroleum ether) to afford a mixture of 7,7-dimethyloxepan-4-one and 2,2-dimethyloxepan-4-one (2.6 g, 22.5% yield, ratio 1:1) as a pale yellow oil.

Step 2: ethyl 5,5-dimethyl-4,5,7,8-tetrahydro-1H-oxepino[4,5-c]pyrazole-3-carboxylate; ethyl 7,7-dimethyl-4,5,7,8-tetrahydro-1H-oxepino[4,5-c]pyrazole-3-carboxylate; ethyl 6,6-dimethyl-4,5,6,8-tetrahydro-1H-oxepino[3,4-c]pyrazole-3-carboxylate

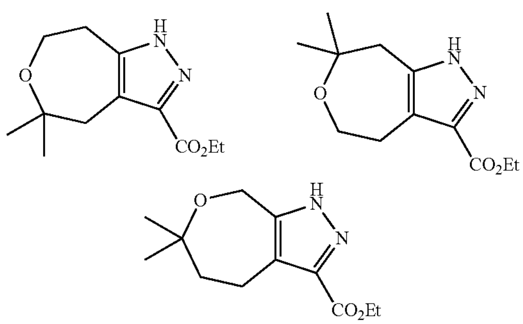

To a solution of 7,7-dimethyloxepan-4-one and 2,2-dimethyloxepan-4-one (2.6 g, 18.3 mmol) and pyrrolidine (85 mg, 1.2 mmol) in dimethyl sulfoxide (20 mL) was slowly added ethyl diazoacetate (1.39 g, 12.2 mmol). After addition, the reaction was stirred at 22° C. for 16 h and poured into water (30 mL). The mixture was then extracted with ethyl acetate (3×30 mL). The combined organic layers were washed with water (2×30 mL) and brine (30 mL), dried over sodium sulfate and concentrated to dryness in vacuo. The residue was purified by column chromatography (silica gel, 100-200 mesh, 0 to 18% ethyl acetate in petroleum ether) to afford a mixture of three regio-isomers (900 mg, 20.6% yield) as yellow oil. The regio-isomers were separated by SFC to afford:

Peak 1 (Retention time 3.31 min), ethyl 5,5-dimethyl-4,5,7,8-tetrahydro-1H-oxepino[4,5-c]pyrazole-3-carboxylate (200 mg): $^1$H NMR (400 MHz, $CDCl_3$) δ 4.38-4.33 (m, 2H), 3.88 (t, J=6.0 Hz, 2H), 3.11 (s, 2H), 2.97 (t, J=6.00 Hz, 2H), 1.37 (t, J=6.00 Hz, 2H), 1.21 (s, 6H)

Peak 2 (Retention time 3.37 min), ethyl 7,7-dimethyl-4,5,7,8-tetrahydro-1H-oxepino[4,5-c]pyrazole-3-carboxylate (150 mg) as a yellow oil: $^1$H NMR (400 MHz, CDCl3) δ 4.39-4.34 (m, 2H), 3.92-3.87 (m, 2H), 3.08-3.03 (m, 2H), 2.98 (s, 2H), 1.38 (t, J=6.0 Hz, 3H), 1.23 (s, 6H)

Peak 3 (Retention time 6.30 min), ethyl 6,6-dimethyl-4,5,6,8-tetrahydro-1H-oxepino[3,4-c]pyrazole-3-carboxylate (150 mg) as a yellow oil: $^1$H NMR (400 MHz, CDCl3) δ 4.68 (s, 2H), 4.40-4.35 (m, 2H), 3.00-2.92 (m, 2H), 1.95-1.88 (m, 2H), 1.39 (t, J=6.0 Hz, 3H), 1.33 (s, 6H).

SFC Conditions:

Column: Chiralpak AD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Column: Chiralpak AY 150×4.6 mm I.D., 3 um Mobile phase: A: CO2 B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.

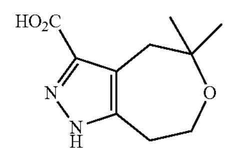

Step 3: 5,5-dimethyl-4,5,7,8-tetrahydro-1H-oxepino[4,5-c]pyrazole-3-carboxylic acid To a solution of ethyl 5,5-dimethyl-4,5,7,8-tetrahydro-1H-oxepino[4,5-c]pyrazole-3-carboxylate (200 mg, 0.84 mmol) in tetrahydrofuran (5 mL) and water (1 mL) was added lithium hydroxide (100 mg, 4.20 mmol). The mixture was stirred at 20° C. for 20 h and concentrated to dryness in vacuo. The residue was diluted with water (30 mL) and adjusted to pH=3 by addition of 1 N hydrochloric acid. The solution was extracted with ethyl acetate (3×50 mL). The combined organic layers were dried over sodium sulfate and concentrated to dryness in vacuo to afford 5,5-dimethyl-4,5,7,8-tetrahydro-1H-oxepino[4,5-c]pyrazole-3-carboxylic acid (160 mg, 90.7% yield) as a white solid: LCMS (0 to 60% acetonitrile in water+0.03% trifluoroacetic acid over 3 mins) retention time 1.76 min, ESI+ found [M+H]=211.2.

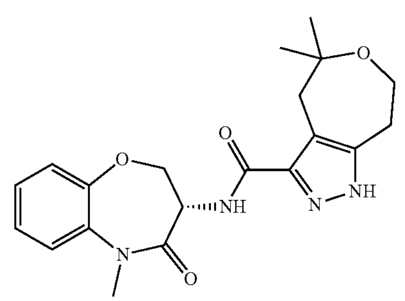 [SMILES: CN1C(=O)[C@@H](NC(=O)c2n[nH]c3c2CC(C)(C)OCC3)COc2ccccc21]

Step 4: (S)-5,5-dimethyl-N-(5-methyl-4-oxo-2,3,4,5-tetrahydrobenzo[b][1,4]oxazepin-3-yl)-4,5,7, 8-tetrahydro-1H-oxepino[4,5-c]pyrazole-3-carboxamide To a solution of 1-hydroxybenzotriazole (54 mg, 0.40 mmol) in N,N-dimethylformamide (5 mL) was added 1-(3-dimethylaminopropyl)-3-ethylcarbodiimidehydrochloride (77 mg, 0.40 mmol) 5,5-dimethyl-1,4,7,8-tetrahydrooxepino[4,5-c]pyrazole-3-carboxylic acid (70 mg, 0.33 mmol) and (3S)-3-amino-5-methyl-2,3-dihydro-1,5-benzoxazepin-4-one (70 mg, 0.37 mmol). The reaction mixture was stirred at 25° C. for 1 h and concentrated to dryness in vacuo. The residue was purified by RP-HPLC (26-56% acetonitrile in water and 0.05% ammonia) to afford (S)-5,5-dimethyl-N-(5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide (95 mg, 74.9% yield) as a white solid: $^1$H NMR (400 MHz, DMSO-d6) δ 12.93 (s, 1H), 8.00 (d, J=8.0 Hz, 1H), 7.49-7.47 (m, 1H), 7.35-7.19 (m, 3H), 4.85-4.78 (m, 1H), 4.52-4.46 (m, 1H), 4.41-4.37 (m, 1H), 3.77-3.75 (m, 2H), 3.31 (s, 3H), 3.01 (s, 2H), 2.82-2.79 (m, 2H), 1.04 (s, 6H). LCMS $R_T$=0.80 min, m/z=385.1 [M+H]$^+$. LCMS (5 to 95% acetonitrile in water+0.03% trifluoroacetic acid over 1.5 mins) retention time 0.80 min, ESI+ found [M+H]=385.1.

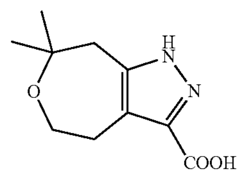

Step 5: 7,7-dimethyl-4,5,7,8-tetrahydro-1H-oxepino[4,5-c]pyrazole-3-carboxylic acid To a solution of ethyl 7,7-dimethyl-4,5,7,8-tetrahydro-1H-oxepino[4,5-c]pyrazole-3-carboxylate (150 mg, 0.63 mmol) in tetrahydrofuran (5 mL) and water (1 mL) was added lithium hydroxide (75 mg, 3.15 mmol). The mixture was stirred at 20° C. for 20 h and concentrated to dryness in vacuo. The residue was diluted with water (20 mL) and adjusted to pH=3 by addition of 1 N hydrochloric acid. The solution was extracted with ethyl acetate (3×25 mL). The combined organic layers were dried over sodium sulfate and concentrated to dryness in vacuo to afford 7,7-dimethyl-4,5,7,8-tetrahydro-1H-oxepino[4,5-c]pyrazole-3-carboxylic acid (95 mg, 71.8% yield) as a white solid: LCMS $R_T$=1.80 min, m/z=211.2 [M+H]$^+$. LCMS (0 to 60% acetonitrile in water+0.03% trifluoroacetic acid over 3 mins) retention time 1.80 min, ESI+ found [M+H]=211.2.

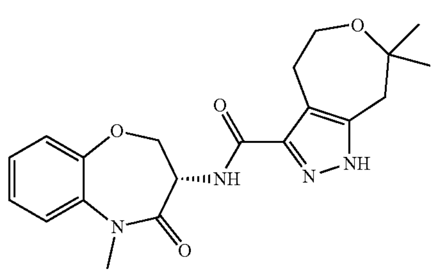 [SMILES: CN1C(=O)[C@@H](NC(=O)c2n[nH]c3c2CCOC(C)(C)C3)COc2ccccc21]

Step 6: (S)-7,7-dimethyl-N-(5-methyl-4-oxo-2,3,4,5-tetrahydrobenzo[b][1,4]oxazepin-3-yl)-4,5,7, 8-tetrahydro-1H-oxepino[4,5-c]pyrazole-3-carboxamide To a solution of 1-hydroxybenzotriazole (39.2 mg, 0.29 mmol) in N,N-dimethylformamide (5 mL) was added 1-(3-dimethylaminopropyl)-3-ethylcarbodiimidehydrochloride (55.6 mg, 0.29 mmol), 7,7-dimethyl-1,4,5,8-tetrahydrooxepino[4,5-c]pyrazole-3-carboxylic acid (50.0 mg, 0.24 mmol) and (3S)-3-amino-5-methyl-2,3-dihydro-1,5-benzoxazepin-4-one (50.3 mg, 0.26 mmol). The reaction mixture was stirred at 25° C. for 1 h and concentrated to dryness in vacuo. The residue was purified by RP-HPLC (26-56% acetonitrile in water and 0.05% ammonia) to afford (S)-7,7-dimethyl-N-(5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide (65 mg, 70.5% yield) as a white solid: $^1$H NMR (400 MHz, DMSO-d6) δ 12.91 (s, 1H), 7.98 (d, J=8.0 Hz, 1H), 7.50-7.48 (m, 1H), 7.36-7.19 (m, 3H), 4.85-4.78 (m, 1H), 4.54-4.37 (m, 2H), 3.73-3.71 (m, 2H), 3.31 (s, 3H), 2.89-2.79 (m, 4H), 1.12 (s, 3H), 1.11 (s, 3H). LCMS $R_T$=0.79 min, m/z=385.1 [M+H]$^+$.

LCMS (5 to 95% acetonitrile in water+0.03% trifluoroacetic acid over 1.5 mins) retention time 0.79 min, ESI+ found [M+H]=385.1.

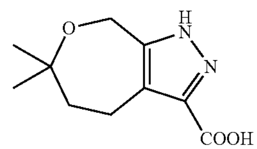

Step 7: 6,6-dimethyl-4,5,6,8-tetrahydro-1H-oxepino[3,4-c]pyrazole-3-carboxylic acid To a solution of ethyl 6,6-dimethyl-4,5,6,8-tetrahydro-1H-oxepino[3,4-c]pyrazole-3-carboxylate (100 mg, 0.42 mmol) in tetrahydrofuran (5 mL) and water (1 mL) was added lithium hydroxide (50 mg, 2.10 mmol). The mixture was stirred at 23° C. for 20 h and concentrated to dryness in vacuo. The residue was diluted with water (20 mL) and adjusted to pH=3 by addition of 1 N hydrochloric acid. The solution was extracted with ethyl acetate (3×25 mL). The combined organic layers were dried over sodium sulfate and concentrated to dryness in vacuo to afford crude 6,6-dimethyl-4,5,6,8-tetrahydro-1H-oxepino[3,4-c]pyrazole-3-carboxylic acid (70 mg, 79.3% yield) as a white solid: LCMS $R_T$=1.86 min, m/z=211.2 [M+H]$^+$.

LCMS (0 to 60% acetonitrile in water+0.03% trifluoroacetic acid over 3 mins) retention time 1.86 min, ESI+ found [M+H]=211.2.

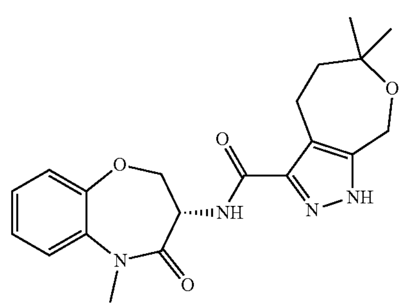 [SMILES: CN1C(=O)[C@@H](NC(=O)c2n[nH]c3c2CCC(C)(C)OC3)COc2ccccc21]

Step 8: (S)-6,6-dimethyl-N-(5-methyl-4-oxo-2,3,4,5-tetrahydrobenzo[b][1,4]oxazepin-3-yl)-4,5,6, 8-tetrahydro-1H-oxepino[3,4-c]pyrazole-3-carboxamide To a solution of 1-hydroxybenzotriazole (54 mg, 0.40 mmol) in N,N-dimethylformamide (5 mL) was added 1-(3-dimethylaminopropyl)-3-ethylcarbodiimidehydrochloride (77 mg, 0.40 mmol), 6,6-dimethyl-1,4,5,8-tetrahydrooxepino[3,4-c]pyrazole-3-carboxylic acid (70 mg, 0.33 mmol) and (3S)-3-amino-5-methyl-2,3-dihydro-1,5-benzoxazepin-4-one (70 mg, 0.37 mmol). The reaction mixture was stirred at 25° C. for 1 h and concentrated to dryness in vacuo. The residue was purified by RP-HPLC (55-85% methanol in water and 0.05% ammonia) to afford (S)-6,6-dimethyl-N-(5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide (95 mg, 74.9% yield) as a white solid: $^1$H NMR (400 MHz, DMSO-d6) δ12.93 (br. s, 1H), 7.97 (d, J=7.2 Hz, 1H), 7.48 (d, J=7.2 Hz, 1H), 7.39-7.16 (m, 3H), 4.83-4.81 (m, 1H), 4.61-4.33 (m, 4H), 3.31 (s, 3H), 2.80-2.70 (m, 2H), 1.85-1.70 (m, 2H), 1.20 (s, 6H). LCMS $R_T$=0.81 min, m/z=385.1 [M+H]$^+$.

LCMS (5 to 95% acetonitrile in water+0.03% trifluoroacetic acid over 1.5 mins) retention time 0.81 min, ESI+ found [M+H]=385.1.

Example 27: Method Y

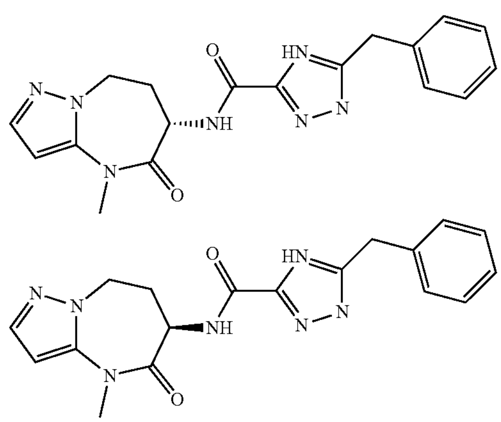

(S)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide and (R)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide

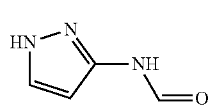

Step 1: N-(1H-pyrazol-3-yl)formamide

A solution of 1H-pyrazol-3-amine (2.5 g, 30.09 mmol) in formic acid (10 mL) was heated to 110° C. for 2 h in a sealed vessel. After this time, the reaction mixture was concentrated in vacuo and purified by column chromatography (silica gel, 100-200 mesh, 0 to 100% 3:1 isopropyl acetate: methanol in heptane) affording N-(1H-pyrazol-3-yl)formamide (2.75 g, 82%) as a white solid used as is in the next step: LCMS $R_T$=0.25 min, m/z=112 [M+H]$^+$.

Step 2: N-methyl 1-H-pyrazol-3-amine

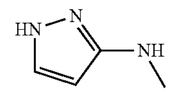

To a solution of N-(1H-pyrazol-3-yl)formamide (2.75 g, 24.8 mmol) in anhydrous tetrahydrofuran (100 mL) cooled to 0° C. under nitrogen was slowly added a solution of lithium aluminum hydride (2 M in tetrahydrofuran, 37.1 mL, 74.3 mmol) under nitrogen. The reaction mixture was allowed to warm to RT and was stirred for 16 h. After this time, the reaction was quenched with solid sodium sulfate decahydrate and stirred at RT for 30 mins. The resulting mixture was diluted with isopropyl acetate, filtered through Celite, and concentrated in vacuo to afford N-methyl-1H-pyrazol-3-amine (1.97 g, 82% yield) as an orange oil used as in the next step without further purification.

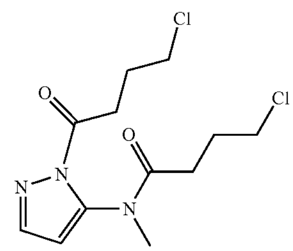 [SMILES: CN(C(=O)CCCCl)c1ccnn1C(=O)CCCCl]

Step 3: 4-chloro-N-(1-(4-chlorobutanoyl)-1H-pyrazol-5-yl)-N-methylbutanamide

To a stirred solution of N-methyl-1H-pyrazol-5-amine (200 mg, 2.06 mmol) in anhydrous dichloromethane (10 mL) cooled to 0° C. was added N,N-diisopropylethylamine (1.08 mL, 6.18 mmol) followed by dropwise addition of 4-chlorobutanoyl chloride (0.697 g. 4.94 mmol) under nitrogen. To the resulting mixture was added 4-dimethylaminopyridine (0.025 g, 0.21 mmol), and the reaction mixture was stirred at RT for 16 h. The reaction mixture was partially concentrated in vacuo and purified by column chromatography (silica gel, 100-200 mesh, 0 to 50% isopropyl acetate in heptane) affording 4-chloro-N-(1-(4-chlorobutanoyl)-1H-pyrazol-5-yl)-N-methylbutanamide as a colorless oil (0.450 g, 71%) used as is in the next step: LCMS $R_T$=1.35 min, m/z=306 [M+H]$^+$.

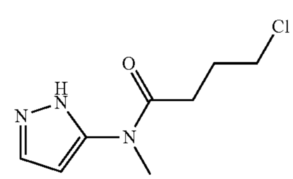

Step 4: 4-chloro-N-methyl-N-(1H-pyrazol-5-yl)butanamide

To a stirred solution of 4-chloro-N-(1-(4-chlorobutanoyl)-1H-pyrazol-5-yl)-N-methylbutanamide (0.338 g, 1.10 mmol) in ethanol (2 mL) was added sodium hydroxide (1 mol/L) in water (1.10 mL, 1.10 mmol) and the mixture was left to stand at RT for 5 min. The reaction mixture was concentrated to dryness in vacuo and purified by column chromatography (silica gel, 100-200 mesh, 0 to 100% isopropyl acetate in heptane) affording 4-chloro-N-methyl-N-(1H-pyrazol-5-yl)butanamide as a white solid (0.185 g, 83%) used in the next step without further purification: LCMS $R_T$=0.86 min, m/z=202 $[M+H]^+$.

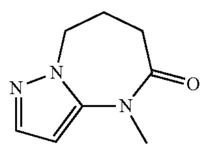

Step 5: 4-methyl-7,8-dihydro-4H-pyrazolo[1,5-a][1,3]diazepin-5(6H)-one

To a solution of 4-chloro-N-methyl-N-(1H-pyrazol-5-yl)butanamide (0.185 g, 0.92 mmol) in N,N-dimethylformamide (4 mL) was added cesium carbonate (0.597 g, 1.83 mmol) and stirred at RT for 16 h. The reaction mixture was filtered through Celite and concentrated to dryness in vacuo. The resulting residue was purified by column chromatography (silica gel, 100-200 mesh, 0 to 100% isopropyl acetate in heptane) affording 4-methyl-7,8-dihydro-4H-pyrazolo[1,5-a][1,3]diazepin-5(6H)-one as a viscous colorless oil (0.123 g, 81%) used as is in the next step: LCMS $R_T$=0.76 min, m/z=166 $[M+H]^+$.

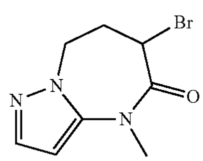

Step 6: 6-bromo-4-methyl-7,8-dihydro-4H-pyrazolo[1,5-a][1,3]diazepin-5(6H)-one

To a solution of 4-methyl-7,8-dihydro-4H-pyrazolo[1,5-a][1,3]diazepin-5(6H)-one (0.123 g, 0.745 mmol) cooled to −78° C. in dry tetrahydrofuran (5 mL) was added dropwise a solution of lithium bis(trimethylsilyl)amide (1 mol/L) in dry tetrahydrofuran (2.23 mL, 2.23 mmol) under nitrogen. The resulting solution was stirred at −78° C. for 30 min and N-bromosuccinimide (0.265, 1.49 mmol) was added and stirred at −78° C. for 2 h. The reaction mixture was quenched with saturated sodium bisulfite (50 mL) and extracted with isopropyl acetate (3×50 mL), dried over sodium sulfate and concentrated to dryness in vacuo. The resulting residue was purified by column chromatography (silica gel, 100-200 mesh, 0 to 100% isopropyl acetate in heptane) affording 6-bromo-4-methyl-7,8-dihydro-4H-pyrazolo[1,5-a][1,3]diazepin-5(6H)-one as a pale yellow oil (0.083 g, 460) use as is in the next step: LCMS $R_T$=0.83 min, m/z=244 $[M+H]^+$.

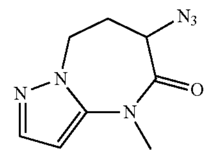

Step 7: 6-azido-4-methyl-7,8-dihydro-4H-pyrazolo[1,5-a][1,3]diazepin-5(6H)-one

To a solution of 6-bromo-4-methyl-7,8-dihydro-4H-pyrazolo[1,5-a][1,3]diazepin-5(6H)-one (0.083 g, 0.30 mmol) in N, N-dimethylformamide (1 mL) was added sodium azide (0.026 g, 0.41 mmol) and the reaction mixture was stirred at RT for 2 h. The reaction mixture was diluted with isopropyl acetate, filtered through Celite, and concentrated to dryness in vacuo. The resulting residue was purified by column chromatography (silica gel, 100-200 mesh, 0 to 100% isopropyl acetate in heptane) affording 6-azido-4-methyl-7,8-dihydro-4H-pyrazolo[1,5-a][1,3]diazepin-5(6H)-one as a pale orange oil (0.067 g, 96%) used as is in the next step: LCMS $R_T$=0.93 min, m/z=207 $[M+H]^+$.

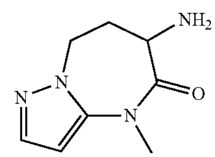

Step 8: 6-amino-4-methyl-7,8-dihydro-4H-pyrazolo[1,5-a][1,3]diazepin-5(6H)-one

To a solution of 6-azido-4-methyl-7,8-dihydro-4H-pyrazolo[1,5-a][1,3]diazepin-5(6H)-one (0.067 g, 0.32 mmol) in methanol (2 mL) was added 10% Pd/C (0.069 g, 0.065 mmol), a balloon of hydrogen, and the mixture was stirred at RT for 16 h. The reaction mixture was filtered through Celite and concentrated to dryness in vacuo affording 6-amino-4-methyl-7,8-dihydro-4H-pyrazolo[1,5-a][1,3]diazepin-5(6H)-one as a viscous oil (0.055 g, 94%) used in the next step without further purification: LCMS $R_T$=0.25 min, m/z=181 $[M+H]^+$.

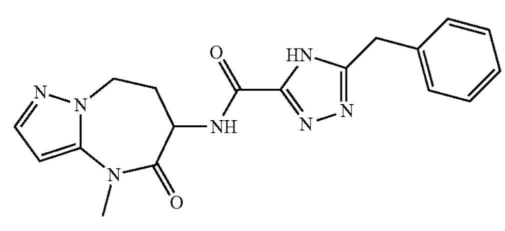 [SMILES: CN1C(=O)C(NC(=O)c2nnc(Cc3ccccc3)[nH]2)CCn2nccc21]

Step 9: 5-benzyl-N-(4-methyl-5-oxo-5,6,7,8-tetrahydro-4H-pyrazolo[1,5-a][1,3]diazepin-6-yl)-4H-1,2,4-triazole-3-carboxamide To a stirred solution of 6-amino-4-methyl-7,8-dihydro-4H-pyrazolo[1,5-a][1,3]diazepin-5(6H)-one (0.055 g, 0.31 mmol) in N,N-dimethylformamide (2 mL) was added 5-benzyl-4H-1,2,4-triazole-3-carboxylic acid (0.074 g, 0.37 mmol), ((3H-[1,2,3]triazolo[4,5-b]pyridin-3-yl)oxy)tri(pyrrolidin-1-yl)phosphonium hexafluorophosphate(V) (0.182 g, 0.34 mmol) and N,N-diisopropylethylamine (0.160 mL, 0.92 mmol). After stirring at RT for 16 h the reaction mixture was loaded directly for purification by RP-HPLC (0 to 35% acetonitrile in water and 0.1% formic acid) affording 5-benzyl-N-(4-methyl-5-oxo-5,6,7,8-tetrahydro-4H-pyrazolo[1,5-a][1,3]diazepin-6-yl)-4H-1, 2,4-triazole-3-carboxamide as a white solid (0.029 mg, 26%): $^1$H NMR (400 MHz, DMSO-d6) δ 14.42 (s, 1H), 8.56 (s, 1H), 7.49 (d, J=2.0 Hz, 1H), 7.38-7.16 (m, 5H), 6.34 (d, J=2.0 Hz, 1H), 4.42-4.13 (m, 3H), 4.11 (s, 2H), 3.24 (s, 3H), 2.69-2.53 (m, 1H), 2.47-2.32 (m, 1H). LCMS $R_T$=3.35 min, m/z=366.2 $[M+H]^+$.

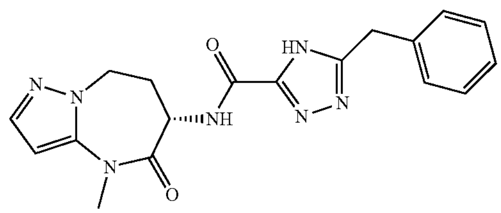

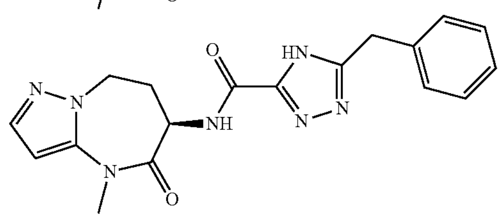

Step 10: (S)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide and (R)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide 5-benzyl-N-(4-methyl-5-oxo-5,6,7,8-tetrahydro-4H-pyrazolo[1,5-a][1,3]diazepin-6-yl)-4H-1, 2,4-triazole-3-carboxamide was further purified by chiral SFC (ID column, 30% methanol+0.1% ammonium hydroxide isocratic elution) affording arbitrarily assigned enantiomers (S)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide (0.012 g, 11%) and (R)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide (0.012 g, 11%) as white solids:

Analytical data for the first eluting enantiomer (arbitrarily assigned S configuration): SFC $R_T$(ID column, 30% methanol+0.1% ammonium hydroxide isocratic elution, 2.5 min method): 0.545 min, 100% ee: $^1$H NMR (400 MHz, DMSO-d6) δ 14.44 (s, 1H), 8.54 (s, 1H), 7.49 (d, J=2.0 Hz, 1H), 7.35-7.20 (m, 5H), 6.34 (d, J=2.0 Hz, 1H), 4.42-4.13 (m, 3H), 4.10 (s, 2H), 3.24 (s, 3H), 2.65-2.53 (m, 1H), 2.44-2.30 (m, 1H). LCMS $R_T$=3.35 min, m/z=366.1 $[M+H]^+$.

Analytical data for the second eluting enantiomer (arbitrarily assigned R configuration): SFC $R_T$: 0.908 min, 99% ee: $^1$H NMR (400 MHz, DMSO-d6) δ 14.43 (s, 1H), 8.54 (s, 1H), 7.49 (d, J=2.0 Hz, 1H), 7.43-7.13 (m, 5H), 6.34 (d, J=2.0 Hz, 1H), 4.42-4.13 (m, 3H), 4.10 (s, 2H), 2.67-2.52 (m, 1H), 2.46-2.29 (m, 1H). LCMS $R_T$=3.35 min, m/z=366.2 $[M+H]^+$.

Example 28: Method Z

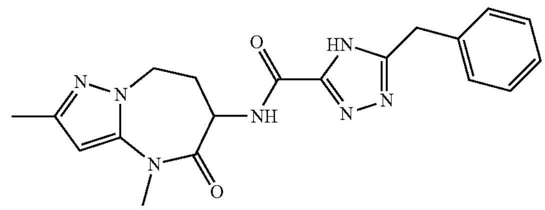 [SMILES: Cc1cc2n(n1)CCC(NC(=O)c1nnc(Cc3ccccc3)[nH]1)C(=O)N2C]

3: 5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide

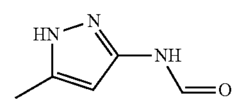

Step 1: N-(5-methyl-1H-pyrazol-3-yl)formamide

A solution of 5-methyl-1H-pyrazol-3-amine (1.8 g, 18.5 mmol) in formic acid (10 mL) was heated to 110° C. for 3 h in a sealed vessel. After this time, the reaction mixture was concentrated in vacuo and purified by column chromatography (silica gel, 100-200 mesh, 0 to 15% methanol in dichloromethane) affording N-(5-methyl-1H-pyrazol-3-yl)formamide (1.96 g, 85%) as an off-white solid used as is in the next step: LCMS $R_T$=0.50 min, m/z=126 $[M+H]^+$.

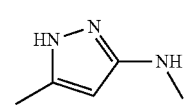

Step 2: N,5-dimethyl-1H-pyrazol-3-amine

To a solution of N-(5-methyl-1H-pyrazol-3-yl)formamide (1.96 g, 15.7 mmol) in anhydrous tetrahydrofuran (50 mL) cooled to 0° C. under nitrogen was slowly added a solution of lithium aluminum hydride (2 M in tetrahydrofuran, 23.5 mL, 47.0 mmol) under nitrogen. The reaction mixture was allowed to warm to RT and was stirred for 16 h. After this time, the reaction was quenched with solid sodium sulfate decahydrate and stirred at RT for 30 mins. The resulting mixture was diluted with isopropyl acetate, filtered through Celite, and concentrated in vacuo to afford N,5-dimethyl-1H-pyrazol-3-amine (1.79 g, 103% yield) as a yellow oil used in the next step without further purification.

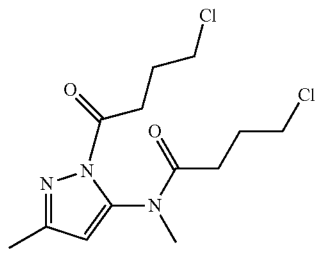 [SMILES: Cc1cc(N(C)C(=O)CCCCl)n(C(=O)CCCCl)n1]

Step 3: 4-chloro-N-[1-(4-chlorobutanoyl)-5-methyl-pyrazol-3-yl]-N-methyl-butanamide To a stirred solution of N,5-dimethyl-1H-pyrazol-3-amine (1.74 g, 15.7 mmol) in anhydrous dichloromethane (50 mL) cooled to 0° C. was added N,N-diisopropylethylamine (8.19 mL, 47.0 mmol) followed by dropwise addition of 4-chlorobutanoyl chloride (5.3 g, 37.6 mmol) under nitrogen. To the resulting mixture was added 4-dimethylaminopyridine (0.191 g, 1.57 mmol), and the reaction mixture was stirred at RT for 16 h. The reaction mixture was partially concentrated in vacuo and purified by column chromatography (silica gel, 100-200 mesh, 0 to 50% isopropyl acetate in heptane) affording 4-chloro-N-[1-(4-chlorobutanoyl)-5-methyl-pyrazol-3-yl]-N-methyl-butanamide (2.37 g, 47%) as an orange oil used as is in the next step: LCMS $R_T$=1.43 min, m/z=320 $[M+H]^+$.

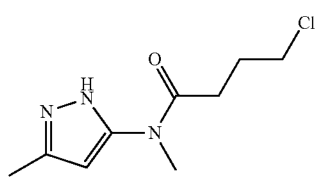

Step 4: 4-chloro-N-methyl-N-(5-methyl-1H-pyrazol-3-yl)butanamide

To a stirred solution of 4-chloro-N-[1-(4-chlorobutanoyl)-5-methyl-pyrazol-3-yl]-N-methyl-butanamide (2.37 g, 7.4 mmol) in ethanol (20 mL) was added sodium hydroxide (1 mol/L) in water (7.4 mL, 7.4 mmol) and the mixture was left to stand at RT for 5 min. The reaction mixture was concentrated to dryness in vacuo and purified by column chromatography (silica gel, 100-200 mesh, 0 to 100% isopropyl acetate in heptane) affording 4-chloro-N-methyl-N-(5-methyl-1H-pyrazol-3-yl)butanamide (1.4 g, 88%) as a yellow oil used in the next step without further purification: LCMS $R_T$=0.99 min, m/z=216 $[M+H]^+$.

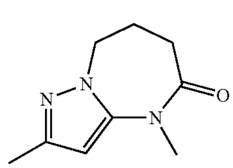

Step 5: 2,4-dimethyl-7,8-dihydro-6H-pyrazolo[1,5-a][1,3]diazepin-5-one

To a solution of 4-chloro-N-methyl-N-(5-methyl-1H-pyrazol-3-yl)butanamide (1.4 g, 6.5 mmol) in acetonitrile (10 mL) was added cesium carbonate (3.2 g, 13.0 mmol), and the resulting suspension was stirred at RT for 16 h. The reaction mixture was filtered through Celite and concentrated to dryness in vacuo. The resulting residue was purified by column chromatography (silica gel, 100-200 mesh, 0 to 100% isopropyl acetate in heptane) affording 2,4-dimethyl-7,8-dihydro-6H-pyrazolo[1,5-a][1,3]diazepin-5-one (0.655 g, 56%) as a viscous colorless oil used as is in the next step: LCMS $R_T$=0.91 min, m/z=180 $[M+H]^+$.

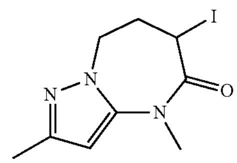

Step 6: 6-iodo-2,4-dimethyl-7,8-dihydro-6H-pyrazolo[1,5-a][1,3]diazepin-5-one

To a solution of 2,4-dimethyl-7,8-dihydro-6H-pyrazolo[1,5-a][1,3]diazepin-5-one (0.655 g, 3.65 mmol) in dry dichloromethane (20 mL) under nitrogen cooled to ~−10° C. in a salt/ice bath was added N,N,N',N'-tetramethylethylenediamine (2.55 g, 22 mmol) followed by iodotrimethylsilane (4.4 g, 22 mmol). The resulting solution was stirred in the salt/ice bath for 1.5 h, after which time was added iodine (2.8 g, 11 mmol). The mixture continued to stir in the salt/ice bath for another 2 h, after which time the reaction mixture was quenched with saturated sodium bisulfite (50 mL). The layers were separated, and the aqueous was extracted with dichloromethane (2×50 mL). The combined organic extracts were dried over anhydrous sodium sulfate and concentrated to dryness in vacuo. The resulting residue was purified by column chromatography (silica gel, 100-200 mesh, 0 to 100% isopropyl acetate in heptane) affording 6-iodo-2,4-dimethyl-7,8-dihydro-6H-pyrazolo[1,5-a][1,3]diazepin-5-one as a brown solid (0.874 g, 78%) used as is in the next step: LCMS $R_T$=1.03 min, m/z=306 $[M+H]^+$.

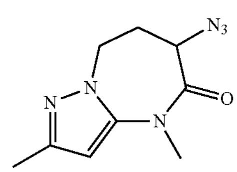 [SMILES: Cc1cc2n(n1)CCC(N=[N+]=[N-])C(=O)N2C]

Step 7: 6-azido-2,4-dimethyl-7,8-dihydro-6H-pyrazolo[1,5-a][1,3]diazepin-5-one

To a solution of 6-iodo-2,4-dimethyl-7,8-dihydro-6H-pyrazolo[1,5-a][1,3]diazepin-5-one (0.874 g, 2.86 mmol) in N,N-dimethylformamide (2 mL) was added sodium azide (0.223 g, 3.44 mmol), and the reaction mixture was stirred at RT for 2 h. The reaction mixture was diluted with isopropyl acetate, filtered through Celite, and concentrated to dryness in vacuo. The resulting residue was purified by column chromatography (silica gel, 100-200 mesh, 0 to 100% isopropyl acetate in heptane) affording 6-azido-2,4-dimethyl-7,8-dihydro-4H-pyrazolo[1,5-a][1,3]diazepin-5(6H)-one as a pale orange oil (0.606 g, 96%) used as is in the next step: LCMS $R_T$=0.99 min, m/z=221 $[M+H]^+$.

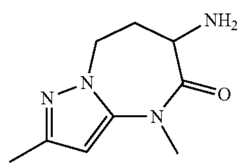

Step 8: 6-amino-2,4-dimethyl-7,8-dihydro-6H-pyrazolo[1,5-a][1,3]diazepin-5-one

To a solution of 6-azido-2,4-dimethyl-7,8-dihydro-6H-pyrazolo[1,5-a][1,3]diazepin-5-one (0.606 g, 2.75 mmol) in tetrahydrofuran (5 mL) was added water (1 mL) followed by polymer-bound triphenylphosphine (2.75 g, ~3 mmol/g loading). The mixture was shaken at RT for 16 h, filtered through Celite and concentrated to dryness in vacuo. The resulting residue was purified by column chromatography (silica gel, 100-200 mesh, 0 to 20% methanol in dichloromethane) affording 6-amino-2,4-dimethyl-7,8-dihydro-6H-pyrazolo[1,5-a][1,3]diazepin-5-one as a colorless oil (0.500 g, 94%) used as is in the next step: LCMS $R_T$=0.54 min, m/z=195 $[M+H]^+$.

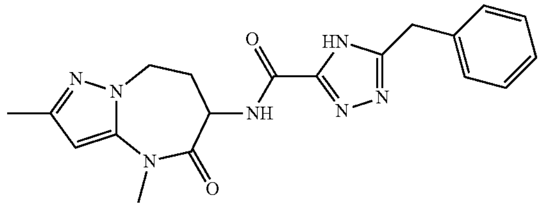 [SMILES: Cc1cc2n(n1)CCC(NC(=O)c1nnc(Cc3ccccc3)[nH]1)C(=O)N2C]

Step 9: 5-benzyl-N-(2,4-dimethyl-5-oxo-7,8-dihydro-6H-pyrazolo[1,5-a][1,3]diazepin-6-yl)-4H-1,2,4-triazole-3-carboxamide To a stirred solution of 6-amino-2,4-dimethyl-7,8-dihydro-6H-pyrazolo[1,5-a][1,3]diazepin-5-one (0.029 g, 0.15 mmol) in N,N-dimethylformamide (2 mL) was added 5-benzyl-4H-1,2,4-triazole-3-carboxylic acid (0.037 g, 0.18 mmol), ((3H-[1,2,3]triazolo[4,5-b]pyridin-3-yl)oxy)tri(pyrrolidin-1-yl)phosphonium hexafluorophosphate(V) (0.095 g, 0.18 mmol) and N,N-diisopropylethylamine (0.078 mL, 0.45 mmol). After stirring at RT for 16 h the reaction mixture was loaded directly for purification by RP-HPLC (5 to 50% acetonitrile in water and 0.1% formic acid) affording 6-amino-2,4-dimethyl-7,8-dihydro-6H-pyrazolo[1,5-a][1,3]diazepin-5-one as a white solid (0.029 g, 51%): 1H NMR (400 MHz, DMSO-d6) δ 14.39 (s, 1H), 8.53 (s, 1H), 7.36-7.21 (m, 6H), 6.13 (s, 1H), 4.39-4.21 (m, 2H), 4.18-4.01 (m, 4H), 3.22 (s, 3H), 2.57 (ddd, J=12.8, 8.0, 4.9 Hz, 1H), 2.41-2.29 (m, 1H), 2.17 (s, 3H). LCMS $R_T$=3.58 min, m/z=380.2 $[M+H]^+$.

Example 29: Method AA

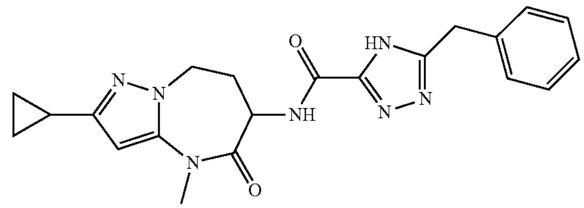 [SMILES: CN1C(=O)C(NC(=O)c2nnc(Cc3ccccc3)[nH]2)CCn2nc(C3CC3)cc21]

5-benzyl-N-(2-cyclopropyl-4-methyl-5-oxo-7,8-dihydro-6H-pyrazolo[1,5-a][1,3]diazepin-6-yl)-4H-1,2,4-triazole-3-carboxamide

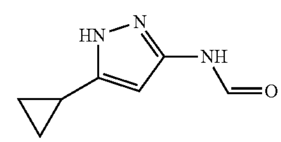 [SMILES: O=CNc1cc(C2CC2)[nH]n1]

Step 1: N-(5-cyclopropyl-1H-pyrazol-3-yl)formamide

A solution of 5-cyclopropyl-1H-pyrazol-3-amine (2.0 g, 16.2 mmol) in formic acid (10 mL) was heated to 110° C. for 3 h in a sealed vessel. After this time, the reaction mixture was concentrated in vacuo and purified by column chromatography (silica gel, 100-200 mesh, 0 to 15% methanol in dichloromethane) affording N-(5-cyclopropyl-1H-pyrazol-3-yl)formamide (1.74 g, 71%) as an off-white solid used as is in the next step: LCMS $R_T$=0.86 min, m/z=152 $[M+H]^+$.

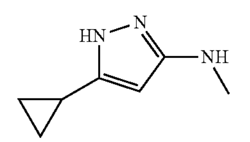

Step 2: 5-cyclopropyl-N-methyl-1H-pyrazol-3-amine

To a solution of N-(5-cyclopropyl-1H-pyrazol-3-yl)formamide (1.74 g, 11.5 mmol) in anhydrous tetrahydrofuran (50 mL) cooled to 0° C. was slowly added a solution of lithium aluminum hydride (2 M in tetrahydrofuran, 17.3 mL, 34.5 mmol) under nitrogen. The reaction mixture was allowed to warm to RT and was stirred for 16 h. After this time, the reaction was quenched with solid sodium sulfate decahydrate and stirred at RT for 30 mins. The resulting mixture was diluted with isopropyl acetate, filtered through Celite, and concentrated in vacuo to afford 5-cyclopropyl-N-methyl-1H-pyrazol-3-amine (1.70 g, 110% yield) as an orange oil used in the next step without further purification.

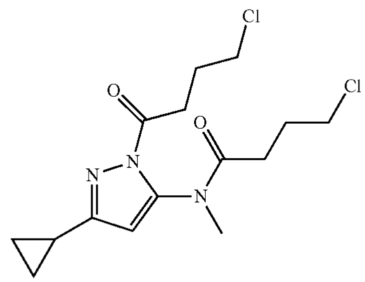 [SMILES: CN(C(=O)CCCCl)c1cc(C2CC2)nn1C(=O)CCCCl]

Step 3: 4-chloro-N-[1-(4-chlorobutanoyl)-5-cyclopropyl-pyrazol-3-yl]-N-methyl-butanamide To a stirred solution of 5-cyclopropyl-N-methyl-1H-pyrazol-3-amine (0.760 g, 5.5 mmol) in anhydrous dichloromethane (50 mL) cooled to 0° C. was added N,N-diisopropylethylamine (2.90 mL, 16.6 mmol) followed by dropwise addition of 4-chlorobutanoyl chloride (1.87 g, 13.3 mmol) under nitrogen. To the resulting mixture was added 4-dimethylaminopyridine (0.068 g, 0.55 mmol), and the reaction mixture was stirred at RT for 16 h. The reaction mixture was partially concentrated in vacuo and purified by column chromatography (silica gel, 100-200 mesh, 0 to 50% isopropyl acetate in heptane) affording 4-chloro-N-[1-(4-chlorobutanoyl)-5-cyclopropyl-pyrazol-3-yl]-N-methyl-butanamide (1.18 g, 62%) as an orange oil used as is in the next step: LCMS $R_T$=1.50 min, m/z=346 $[M+H]^+$.

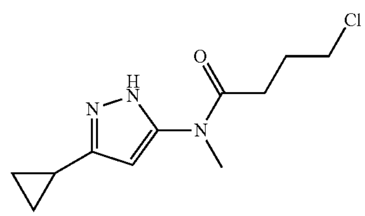 [SMILES: CN(C(=O)CCCCl)c1cc(C2CC2)n[nH]1]

Step 4: 4-chloro-N-(5-cyclopropyl-1H-pyrazol-3-yl)-N-methyl-butanamide

To a stirred solution of 4-chloro-N-[1-(4-chlorobutanoyl)-5-cyclopropyl-pyrazol-3-yl]-N-methyl-butanamide (1.18 g, 3.4 mmol) in ethanol (5 mL) was added sodium hydroxide (1 mol/L) in water (3.4 mL, 3.4 mmol) and the mixture was left to stand at RT for 5 min. The reaction mixture was concentrated to dryness in vacuo and purified by column chromatography (silica gel, 100-200 mesh, 0 to 100% isopropyl acetate in heptane) affording 4-chloro-N-(5-cyclopropyl-1H-pyrazol-3-yl)-N-methyl-butanamide (0.540 g, 66%) as a colorless oil used as is in the next step: LCMS $R_T$=1.08 min, m/z=242 $[M+H]^+$.

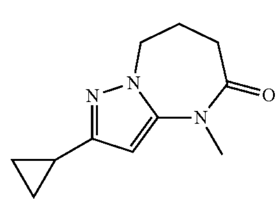

Step 5: 2-cyclopropyl-4-methyl-7,8-dihydro-6H-pyrazolo[1,5-a][1,3]diazepin-5-one To a solution of 4-chloro-N-(5-cyclopropyl-1H-pyrazol-3-yl)-N-methyl-butanamide (0.540 g, 2.2 mmol) in acetonitrile (10 mL) was added cesium carbonate (1.46 g, 4.5 mmol), and the resulting suspension was stirred at RT for 16 h. The reaction mixture was filtered through Celite and concentrated to dryness in vacuo. The resulting residue was purified by column chromatography (silica gel, 100-200 mesh, 0 to 100% isopropyl acetate in heptane) affording 2-cyclopropyl-4-methyl-7,8-dihydro-6H-pyrazolo[1,5-a][1,3]diazepin-5-one (0.332 g, 72%) as a pink oil used as is in the next step: LCMS $R_T$=0.98 min, m/z=206 $[M+H]^+$.

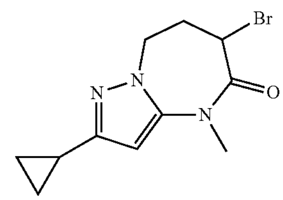 [SMILES: CN1C(=O)C(Br)CCn2nc(C3CC3)cc21]

Step 6: 6-bromo-2-cyclopropyl-4-methyl-7,8-dihydro-6H-pyrazolo[1,5-a][1,3]diazepin-5-one To a solution of 2-cyclopropyl-4-methyl-7,8-dihydro-6H-pyrazolo[1,5-a][1,3]diazepin-5-one (0.332 g, 1.6 mmol) cooled to −78° C. in dry tetrahydrofuran (8 mL) was added dropwise a solution of lithium bis(trimethylsilyl)amide (1 mol/L) in anhydrous tetrahydrofuran (3.23 mL, 3.23 mmol) under nitrogen. The resulting solution was stirred at −78° C. for 30 min and N-bromosuccinimide (0.432, 2.42 mmol) was added and stirred at −78° C. for 2 h. The reaction mixture was quenched with saturated sodium bisulfite (50 mL) and extracted with isopropyl acetate (3×50 mL), dried over sodium sulfate and concentrated to dryness in vacuo. The resulting residue was purified by column chromatography (silica gel, 100-200 mesh, 0 to 4% methanol in dichloromethane) affording 6-bromo-2-cyclopropyl-4-methyl-7,8-dihydro-6H-pyrazolo[1,5-a][1,3]diazepin-5-one as a pale yellow oil (0.210 g, 46%) used as is in the next step: LCMS $R_T$=1.06 min, m/z=284 $[M+H]^+$.

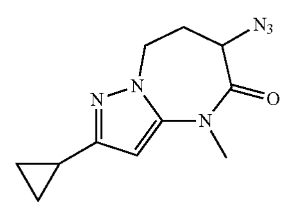 [SMILES: CN1C(=O)C(N=[N+]=[N-])CCn2nc(C3CC3)cc21]

Step 7: 6-azido-2-cyclopropyl-4-methyl-7,8-dihydro-6H-pyrazolo[1,5-a][1,3]diazepin-5-one To a solution of 6-bromo-2-cyclopropyl-4-methyl-7,8-dihydro-6H-pyrazolo[1,5-a][1,3]diazepin-5-one (0.210 g, 0.74 mmol) in N,N-dimethylformamide (1.5 mL) was added sodium azide (0.058 g, 0.89 mmol), and the reaction mixture was stirred at RT for 2 h. The reaction mixture was diluted with isopropyl acetate, filtered through Celite, and concentrated to dryness in vacuo. The resulting residue was purified by column chromatography (silica gel, 100-200 mesh, 0 to 100% isopropyl acetate in heptane) affording 6-azido-2-cyclopropyl-4-methyl-7,8-dihydro-6H-pyrazolo[1,5-a][1,3]diazepin-5-one as a yellow oil (0.109 g, 60%) used as is in the next step: LCMS $R_T$=1.05 min, m/z=247 $[M+H]^+$.

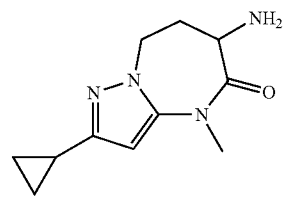 [SMILES: CN1C(=O)C(N)CCn2nc(C3CC3)cc21]

Step 8: 6-amino-2-cyclopropyl-4-methyl-7,8-dihydro-6H-pyrazolo[1,5-a][1,3]diazepin-5-one To a solution of 6-azido-2-cyclopropyl-4-methyl-7,8-dihydro-6H-pyrazolo[1,5-a][1,3]diazepin-5-one (0.109 g, 0.44 mmol) in tetrahydrofuran (2 mL) was added water (0.4 mL) followed by polymer-bound triphenylphosphine (0.44 g, ~3 mmol/g loading). The mixture was shaken at RT for 16 h, filtered through Celite and concentrated to dryness in vacuo. The resulting residue was purified by column chromatography (silica gel, 100-200 mesh, 0 to 20% methanol in dichloromethane) affording 6-amino-2-cyclopropyl-4-methyl-7,8-dihydro-6H-pyrazolo[1,5-a][1,3]diazepin-5-one as a colorless oil (0.096 g, 99%) used as is in the next step: LCMS $R_T$=0.73 min, m/z=221 $[M+H]^+$.

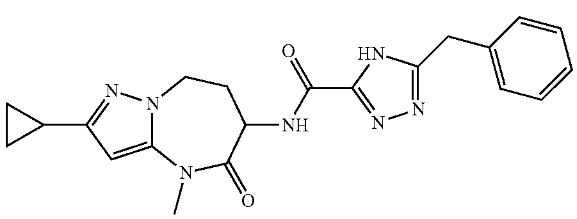 [SMILES: CN1C(=O)C(NC(=O)c2nnc(Cc3ccccc3)[nH]2)CCn2nc(C3CC3)cc21]

Step 9: 5-benzyl-N-(2-cyclopropyl-4-methyl-5-oxo-7,8-dihydro-6H-pyrazolo[1,5-a][1,3]diazepin-6-yl)-4H-1,2,4-triazole-3-carboxamide To a stirred solution of 6-amino-2-cyclopropyl-4-methyl-7,8-dihydro-6H-pyrazolo[1,5-a][1,3]diazepin-5-one (0.033 g, 0.15 mmol) in N,N-dimethylformamide (2 mL) was added 5-benzyl-4H-1,2,4-triazole-3-carboxylic acid (0.037 g, 0.18 mmol), ((3H-[1,2,3]triazolo[4,5-b]pyridin-3-yl)oxy) tri(pyrrolidin-1-yl)phosphonium hexafluorophosphate(V) (0.095 g, 0.18 mmol) and N,N-diisopropylethylamine (0.078 mL, 0.45 mmol). After stirring at RT for 16 h the reaction mixture was loaded directly for purification by RP-HPLC (5 to 50% acetonitrile in water and 0.1% formic acid) affording 5-benzyl-N-(2-cyclopropyl-4-methyl-5-oxo-7,8-dihydro-6H-pyrazolo[1,5-a][1,3]diazepin-6-yl)-4H-1,2,4-triazole-3-carboxamide as a white solid (0.038 g, 62%): 1H NMR (400 MHz, DMSO-d6) δ 8.51 (d, J=7.8 Hz, 1H), 7.36-7.19 (m, 5H), 6.06 (s, 1H), 4.37-4.20 (m, 2H), 4.16-4.02 (m, 3H), 3.20 (s, 3H), 2.65-2.53 (m, 1H), 2.40-2.27 (m, 1H), 1.91-1.80 (m, 1H), 0.92-0.81 (m, 2H), 0.73-0.60 (m, 2H). LCMS $R_T$=3.95 min, m/z=406.2 $[M+H]^+$.

Example 30: Method BB

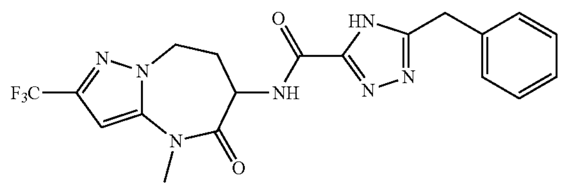 [SMILES: CN1C(=O)C(NC(=O)c2nnc(Cc3ccccc3)[nH]2)CCn2nc(C(F)(F)F)cc21]

5-benzyl-N-[4-methyl-5-oxo-2-(trifluoromethyl)-7,8-dihydro-6H-pyrazolo[1,5-a][1,3]diazepin-6-yl]-4H-1,2,4-triazole-3-carboxamide

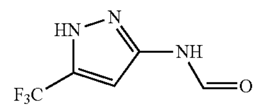

Step 1: N-[5-(trifluoromethyl)-1H-pyrazol-3-yl]formamide

A solution of 5-(trifluoromethyl)-1H-pyrazol-3-amine (2.3 g, 15.2 mmol) in formic acid (10 mL) was heated to 110° C. for 3 h in a sealed vessel. After this time, the reaction mixture was concentrated in vacuo and purified by column chromatography (silica gel, 100-200 mesh, 0 to 15% methanol in dichloromethane) affording N-[5-(trifluoromethyl)-1H-pyrazol-3-yl]formamide (2.15 g, 79%) as an off-white solid used as is in the next step: LCMS $R_T$=0.85 min, m/z=180 $[M+H]^+$.

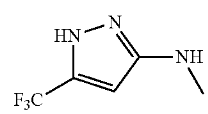

Step 2: N-methyl-5-(trifluoromethyl)-1H-pyrazol-3-amine

To a solution of N-[5-(trifluoromethyl)-1H-pyrazol-3-yl]formamide (2.15 g, 12.0 mmol) in anhydrous tetrahydrofuran (50 mL) cooled to 0° C. under nitrogen was slowly added a solution of lithium aluminum hydride (2 M in tetrahydrofuran, 18.0 mL, 36.0 mmol) under nitrogen. The reaction mixture was allowed to warm to RT gradually and was stirred for 16 h. After this time, the reaction was quenched with solid sodium sulfate decahydrate and stirred at RT for 30 min. The resulting mixture was diluted with isopropyl acetate, filtered through Celite, and concentrated in vacuo to afford N-methyl-5-(trifluoromethyl)-1H-pyrazol-3-amine (2.3 g, 120% yield) as an orange oil used in the next step without further purification.

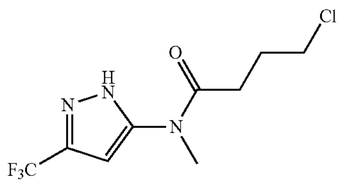 [SMILES: CN(C(=O)CCCCl)c1cc(C(F)(F)F)n[nH]1]

Step 3: 4-chloro-N-methyl-N-[5-(trifluoromethyl)-1H-pyrazol-3-yl]butanamide

To a stirred solution of N-methyl-5-(trifluoromethyl)-1H-pyrazol-3-amine (2.3 g, 14 mmol) in anhydrous dichloromethane (50 mL) cooled to 0° C. was added N,N-diisopropylethylamine (7.3 mL, 42.0 mmol) followed by dropwise addition of 4-chlorobutanoyl chloride (4.7 g, 33 mmol) under nitrogen. To the resulting mixture was added 4-dimethylaminopyridine (0.170 g, 1.4 mmol), and the reaction mixture was stirred at RT 16 h. The reaction mixture was partially concentrated in vacuo and purified by column chromatography (silica gel, 100-200 mesh, 0 to 100% isopropyl acetate in heptane) affording 4-chloro-N-methyl-N-[5-(trifluoromethyl)-1H-pyrazol-3-yl]butanamide (1.03 g, 27%) as an orange solid used as is in the next step: LCMS $R_T$=1.18 min, m/z=270 [M+H]$^+$.

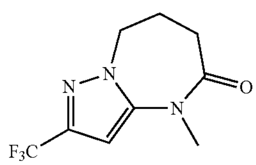 [SMILES: CN1C(=O)CCCn2nc(C(F)(F)F)cc21]

Step 4: 4-methyl-2-(trifluoromethyl)-7,8-dihydro-6H-pyrazolo[1,5-a][1,3]diazepin-5-one To a solution of 4-chloro-N-methyl-N-[5-(trifluoromethyl)-1H-pyrazol-3-yl]butanamide (1.0 g, 3.8 mmol) in acetonitrile (10 mL) was added cesium carbonate (2.5 g, 7.7 mmol), and the resulting suspension was stirred at RT for 16 h. The reaction mixture was filtered through Celite and concentrated to dryness in vacuo. The resulting residue was purified by column chromatography (silica gel, 100-200 mesh, 0 to 70% isopropyl acetate in heptane) affording 4-methyl-2-(trifluoromethyl)-7,8-dihydro-6H-pyrazolo[1,5-a][1,3]diazepin-5-one (0.420 g, 47%) as a yellow solid used as is in the next step: LCMS $R_T$=1.05 min, m/z=234 [M+H]$^+$.

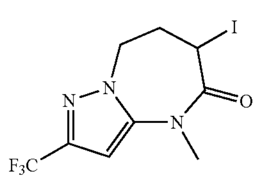 [SMILES: CN1C(=O)C(I)CCn2nc(C(F)(F)F)cc21]

Step 5: 6-iodo-4-methyl-2-(trifluoromethyl)-7,8-dihydro-6H-pyrazolo[1,5-a][1,3]diazepin-5-one To a solution of 4-methyl-2-(trifluoromethyl)-7,8-dihydro-6H-pyrazolo[1,5-a][1,3]diazepin-5-one (0.420 g, 1.80 mmol) in dry dichloromethane (20 mL) under nitrogen cooled to ~−10° C. in a salt/ice bath was added N,N,N',N'-tetramethylethylenediamine (1.26 g, 10.8 mmol) followed by iodotrimethylsilane (2.2 g, 10.8 mmol). The resulting solution was stirred in the salt/ice bath for 1.5 h, after which time was added iodine (1.4 g, 5.4 mmol). The mixture continued to stir in the salt/ice bath for another 2 h, after which time the reaction mixture was quenched with saturated sodium bisulfite (50 mL). The layers were separated, and the aqueous was extracted with dichloromethane (2×50 mL). The combined organic extracts were dried over sodium sulfate and concentrated to dryness in vacuo. The resulting residue was purified by column chromatography (silica gel, 100-200 mesh, 0 to 60% isopropyl acetate in heptane) affording 6-iodo-4-methyl-2-(trifluoromethyl)-7,8-dihydro-6H-pyrazolo[1,5-a][1,3]diazepin-5-one as a white solid (0.470 g, 73%) used as is in the next step: LCMS $R_T$=1.25 min, m/z=360 [M+H]$^+$.

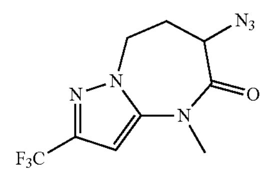 [SMILES: CN1C(=O)C(N=[N+]=[N-])CCn2nc(C(F)(F)F)cc21]

Step 6: 6-azido-4-methyl-2-(trifluoromethyl)-7,8-dihydro-6H-pyrazolo[1,5-a][1,3]diazepin-5-one To a solution of 6-iodo-4-methyl-2-(trifluoromethyl)-7,8-dihydro-6H-pyrazolo[1,5-a][1,3]diazepin-5-one (0.470 g, 1.3 mmol) in N,N-dimethylformamide (2 mL) was added sodium azide (0.102 g, 1.57 mmol), and the reaction mixture was stirred at RT for 2 h. The reaction mixture was diluted with isopropyl acetate, filtered through Celite, and concentrated to dryness in vacuo. The resulting residue was purified by column chromatography (silica gel, 100-200 mesh, 0 to 70% isopropyl acetate in heptane) 6-azido-4-methyl-2-(trifluoromethyl)-7,8-dihydro-6H-pyrazolo[1,5-a][1,3]diazepin-5-one as a white solid (0.330 g, 92%) used as is in the next step: LCMS $R_T$=1.21 min, m/z=275 [M+H]$^+$.

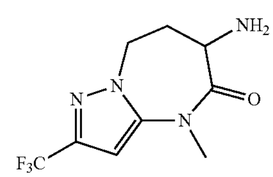 [SMILES: CN1C(=O)C(N)CCn2nc(C(F)(F)F)cc21]

Step 7: 6-amino-4-methyl-2-(trifluoromethyl)-7,8-dihydro-6H-pyrazolo[1,5-a][1,3]diazepin-5-one To a solution of 6-azido-4-methyl-2-(trifluoromethyl)-7,8-dihydro-6H-pyrazolo[1,5-a][1,3]diazepin-5-one (0.330 g, 1.2 mmol) in tetrahydrofuran (5 mL) was added water (1 mL) followed by polymer-bound triphenylphosphine (1.2 g, ~3 mmol/g loading). The mixture was shaken at RT for 16 h, filtered through Celite and concentrated to dryness in vacuo. The resulting residue was purified by column chromatography (silica gel, 100-200 mesh, 0 to 20% methanol in dichloromethane) affording 6-amino-4-methyl-2-(trifluoromethyl)-7,8-dihydro-6H-pyrazolo[1,5-a][1,3]diazepin-5- one as a colorless oil (0.260 g, 87%) used as is in the next step: LCMS $R_T$=0.89 min, m/z=249 [M+H]$^+$.

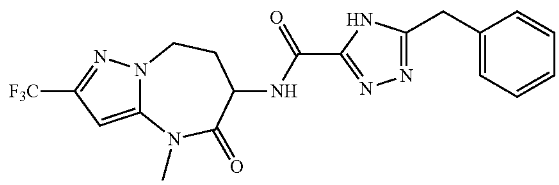 [SMILES: CN1C(=O)C(NC(=O)c2nnc(Cc3ccccc3)[nH]2)CCn2nc(C(F)(F)F)cc21]

Step 8: 5-benzyl-N-[4-methyl-5-oxo-2-(trifluoromethyl)-7,8-dihydro-6H-pyrazolo[1,5-a][1,3]diazepin-6-yl]-4H-1,2,4-triazole-3-carboxamide To a stirred solution of 6-amino-2,4-dimethyl-7,8-dihydro-6H-pyrazolo[1,5-a][1,3]diazepin-5-one (0.037 g, 0.15 mmol) in N,N-dimethylformamide (2 mL) was added 5-benzyl-4H-1,2,4-triazole-3-carboxylic acid (0.037 g, 0.18 mmol), ((3H-[1,2,3]triazolo[4,5-b]pyridin-3-yl)oxy)tri(pyrrolidin-1-yl)phosphonium hexafluorophosphate(V) (0.095 g, 0.18 mmol) and N,N-diisopropylethylamine (0.078 mL, 0.45 mmol). After stirring at RT for 16 h the reaction mixture was loaded directly for purification by RP-HPLC (5 to 50% acetonitrile in water and 0.1% formic acid) affording 5-benzyl-N-[4-methyl-5-oxo-2-(trifluoromethyl)-7,8-dihydro-6H-pyrazolo[1,5-a][1,3]diazepin-6-yl]-4H-1,2,4-triazole-3-carboxamide as a white solid (0.039 g, 60%): 1H NMR (400 MHz, DMSO-d6) δ 14.42 (s, 1H), 8.64 (s, 1H), 7.47-7.13 (m, 5H), 6.93 (s, 1H), 4.53-4.41 (m, 1H), 4.41-4.26 (m, 2H), 4.11 (s, 2H), 3.27 (s, 3H), 2.74-2.57 (m, 1H). LCMS $R_T$=4.33 min, m/z=434.1 [M+H]$^+$.

Example 31: Method CC

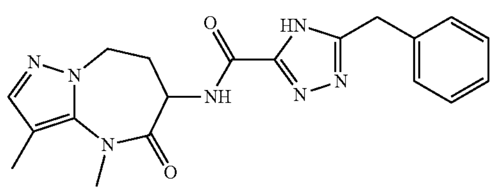 [SMILES: Cc1cnn2c1N(C)C(=O)C(NC(=O)c1nnc(Cc3ccccc3)[nH]1)CC2]

5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide

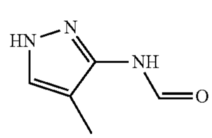

Step 1: N-(4-methyl-1H-pyrazol-3-yl)formamide

A solution of 4-methyl-1H-pyrazol-3-amine (1.3 g, 13.4 mmol) in formic acid (10 mL) was heated to 110° C. for 3 h in a sealed vessel. After this time, the reaction mixture was concentrated in vacuo and purified by column chromatography (silica gel, 100-200 mesh, 0 to 15% methanol in dichloromethane) affording N-(4-methyl-1H-pyrazol-3-yl)formamide (1.44 g, 86%) as an off-white solid used as is in the next step: LCMS $R_T$=0.37 min, m/z=126 [M+H]$^+$.

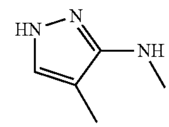

Step 2: N,4-dimethyl-1H-pyrazol-3-amine

To a solution of N-(4-methyl-1H-pyrazol-3-yl)formamide (1.44 g, 11.5 mmol) in anhydrous tetrahydrofuran (50 mL) cooled to 0° C. under nitrogen was slowly added a solution of lithium aluminum hydride (2 M in tetrahydrofuran, 17.3 mL, 34.5 mmol) under nitrogen. The reaction mixture was allowed to warm to RT and was stirred for 16 h. After this time, the reaction was quenched with solid sodium sulfate decahydrate and stirred at RT for 30 mins. The resulting mixture was diluted with isopropyl acetate, filtered through Celite, and concentrated in vacuo to afford N,4-dimethyl-1H-pyrazol-3-amine (1.29 g, 101% yield) as a yellow oil used in the next step without further purification.

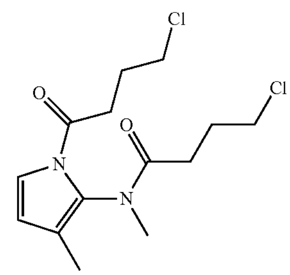 [SMILES: Cc1ccn(C(=O)CCCCl)c1N(C)C(=O)CCCCl]

Step 3: 4-chloro-N-[1-(4-chlorobutanoyl)-4-methyl-pyrazol-3-yl]-N-methyl-butanamide To a stirred solution of N,4-dimethyl-1H-pyrazol-3-amine (1.28 g, 11.5 mmol) in anhydrous dichloromethane (50 mL) cooled to 0° C. was added N,N-diisopropylethylamine (6.03 mL, 34.6 mmol) followed by dropwise addition of 4-chlorobutanoyl chloride (3.9 g, 27.6 mmol) under nitrogen. To the resulting mixture was added 4-dimethylaminopyridine (0.141 g, 1.15 mmol), and the reaction mixture was stirred at RT 16 h. The reaction mixture was partially concentrated in vacuo and purified by column chromatography (silica gel, 100-200 mesh, 0 to 100% isopropyl acetate in heptane) affording 4-chloro-N-[1-(4-chlorobutanoyl)-4-methyl-pyrazol-3-yl]-N-methyl-butanamide (2.2 g, 60%) as an orange oil used as is in the next step: LCMS $R_T$=1.32 min, m/z=320 [M+H]$^+$.

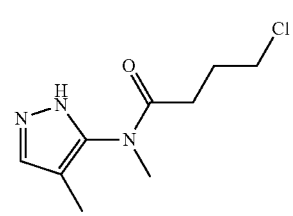

Step 4: 4-chloro-N-methyl-N-(4-methyl-1H-pyrazol-3-yl)butanamide

To a stirred solution of 4-chloro-N-[1-(4-chlorobutanoyl)-4-methyl-pyrazol-3-yl]-N-methyl-butanamide (2.2 g, 6.9 mmol) in ethanol (20 mL) was added sodium hydroxide (1 mol/L) in water (6.9 mL, 6.9 mmol) and the mixture was left to stand at RT for 5 min. The reaction mixture was concentrated to dryness in vacuo and purified by column chromatography (silica gel, 100-200 mesh, 0 to 100% isopropyl acetate in heptane) affording 4-chloro-N-methyl-N-(4-methyl-1H-pyrazol-3-yl)butanamide (1.18 g, 80%) as a yellow oil used as is in the next step: LCMS $R_T$=0.99 min, m/z=216 [M+H]$^+$.

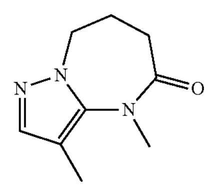

Step 5: 3,4-dimethyl-7,8-dihydro-6H-pyrazolo[1,5-a][1,3]diazepin-5-one

To a solution of 4-chloro-N-methyl-N-(4-methyl-1H-pyrazol-3-yl)butanamide (1.47 g, 6.8 mmol) in acetonitrile (20 mL) was added cesium carbonate (8.9 g, 27.2 mmol), and the resulting suspension was stirred at RT for 48 h. The reaction mixture was filtered through Celite and concentrated to dryness in vacuo. The resulting residue was purified by column chromatography (silica gel, 100-200 mesh, 0 to 100% isopropyl acetate in heptane) affording 3,4-dimethyl-7,8-dihydro-6H-pyrazolo[1,5-a][1,3]diazepin-5-one (0.510 g, 42%) as a viscous white solid used as is in the next step: LCMS $R_T$=0.86 min, m/z=180 [M+H]$^+$.

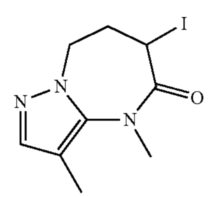

Step 6: 6-iodo-3,4-dimethyl-7,8-dihydro-6H-pyrazolo[1,5-a][1,3]diazepin-5-one

To a solution of 3,4-dimethyl-7,8-dihydro-6H-pyrazolo[1,5-a][1,3]diazepin-5-one (0.450 g, 2.51 mmol) in dry dichloromethane (20 mL) under nitrogen cooled to ~−10° C. in a salt/ice bath was added N,N,N',N'-tetramethylethylenediamine (1.75 g, 15.1 mmol) followed by iodotrimethylsilane (3.0 g, 15.1 mmol). The resulting solution was stirred in the salt/ice bath for 1.5 h, after which time was added iodine (1.91 g, 7.5 mmol). The mixture continued to stir in the salt/ice bath for another 2 h, after which time the reaction mixture was quenched with saturated sodium bisulfite (50 mL). The layers were separated, and the aqueous was extracted with dichloromethane (2×50 mL). The combined organic extracts were dried over sodium sulfate and concentrated to dryness in vacuo. The resulting residue was purified by column chromatography (silica gel, 100-200 mesh, 0 to 100% isopropyl acetate in heptane) affording 6-iodo-3,4-dimethyl-7,8-dihydro-6H-pyrazolo[1,5-a][1,3]diazepin-5-one as a brown solid (0.420 g, 55%) used as is in the next step: LCMS $R_T$=0.99 min, m/z=306 [M+H]$^+$.

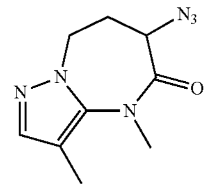 [SMILES: Cc1cnn2c1N(C)C(=O)C(N=[N+]=[N-])CC2]

Step 7: 6-azido-3,4-dimethyl-7,8-dihydro-6H-pyrazolo[1,5-a][1,3]diazepin-5-one

To a solution of 6-iodo-3,4-dimethyl-7,8-dihydro-6H-pyrazolo[1,5-a][1,3]diazepin-5-one (0.420 g, 1.4 mmol) in N,N-dimethylformamide (2 mL) was added sodium azide (0.107 g, 1.65 mmol), and the reaction mixture was stirred at RT for 2 h. The reaction mixture was diluted with isopropyl acetate, filtered through Celite, and concentrated to dryness in vacuo. The resulting residue was purified by column chromatography (silica gel, 100-200 mesh, 0 to 100% isopropyl acetate in heptane) affording 6-azido-3,4-methyl-7,8-dihydro-4H-pyrazolo[1,5-a][1,3]diazepin-5(6H)-one as a pale orange oil (0.289 g, 95%) used as is in the next step: LCMS $R_T$=0.80 min, m/z=221 [M+H]$^+$.

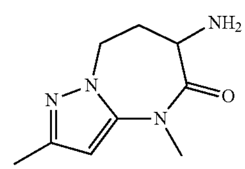

Step 8: 6-amino-3,4-dimethyl-7,8-dihydro-6H-pyrazolo[1,5-a][1,3]diazepin-5-one

To a solution of 6-azido-3,4-dimethyl-7,8-dihydro-6H-pyrazolo[1,5-a][1,3]diazepin-5-one (0.289 g, 1.31 mmol) in tetrahydrofuran (5 mL) was added water (1 mL) followed by polymer-bound triphenylphosphine (1.31 g, ~3 mmol/g loading). The mixture was shaken at RT for 16 h, filtered through Celite and concentrated to dryness in vacuo. The resulting residue was purified by column chromatography (silica gel, 100-200 mesh, 0 to 20% methanol in dichloromethane) affording 6-amino-3,4-dimethyl-7,8-dihydro-6H-pyrazolo[1,5-a][1,3]diazepin-5-one as a colorless oil (0.146 g, 57%) used as is in the next step: LCMS $R_T$=0.65 min, m/z=195 [M+H]$^+$.

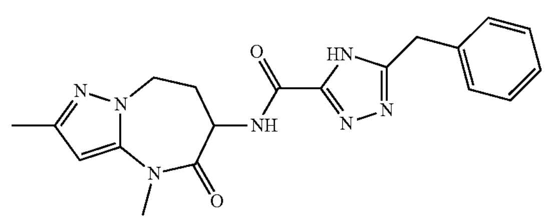 [SMILES: Cc1cc2n(n1)CCC(NC(=O)c1nnc(Cc3ccccc3)[nH]1)C(=O)N2C]

Step 9: 5-benzyl-N-(3,4-dimethyl-5-oxo-7,8-dihydro-6H-pyrazolo[1,5-a][1,3]diazepin-6-yl)-4H-1,2,4-triazole-3-carboxamide To a stirred solution of 6-amino-3,4-dimethyl-7,8-dihydro-6H-pyrazolo[1,5-a][1,3]diazepin-5-one (0.029 g, 0.15 mmol) in N,N-dimethylformamide (2 mL) was added 5-benzyl-4H-1,2,4-triazole-3-carboxylic acid (0.037 g, 0.18 mmol), ((3H-[1,2,3]triazolo[4,5-b]pyridin-3-yl)oxy)tri(pyrrolidin-1-yl)phosphonium hexafluorophosphate(V) (0.095 g, 0.18 mmol) and N,N-diisopropylethylamine (0.078 mL, 0.45 mmol). After stirring at RT for 16 h the reaction mixture was loaded directly for purification by RP-HPLC (5 to 50% acetonitrile in water and 0.1% formic acid) affording 5-benzyl-N-(3,4-dimethyl-5-oxo-7,8-dihydro-6H-pyrazolo[1,5-a][1,3]diazepin-6-yl)-4H-1,2,4-triazole-3-carboxamide as a white solid (0.036 g, 63%): 1H NMR (400 MHz, DMSO-d6) δ 14.41 (s, 1H), 8.45 (d, J=7.6 Hz, 1H), 7.39-7.12 (m, 6H), 4.40-3.99 (m, 5H), 3.21 (s, 3H), 2.62-2.51 (m, 1H), 2.36-2.21 (m, 1H), 2.01 (s, 3H). LCMS $R_T$=3.61 min, m/z=380.2 $[M+H]^+$.

Example 32: Method DD

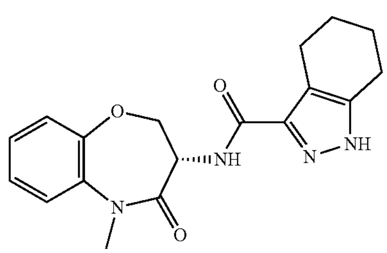 [SMILES: CN1C(=O)[C@@H](NC(=O)c2n[nH]c3c2CCCC3)COc2ccccc21]

Step 1: (S)—N-(5-methyl-4-oxo-2,3,4,5-tetrahydrobenzo[b][1,4]oxazepin-3-yl)-4,5,6,7-tetrahydro-1H-indazole-3-carboxamide To a stirred solution of (3S)-3-amino-5-methyl-2,3-dihydro-1,5-benzoxazepin-4-one (0.025 g, 0.13 mmol) in N,N-dimethylformamide (1 mL) was added 4,5,6,7-tetrahydro-1H-indazole-3-carboxylic acid (0.026 g, 0.16 mmol), ((3H-[1,2,3]triazolo[4,5-b]pyridin-3-yl)oxy)tri(pyrrolidin-1-yl)phosphonium hexafluorophosphate(V) (0.078 g, 0.14 mmol) and N,N-diisopropylethylamine (0.045 mL, 0.26 mmol). After stirring at RT for 16 h the reaction mixture was loaded directly for purification by RP-HPLC (5 to 60% acetonitrile in water and 0.1% formic acid) affording (S)—N-(5-methyl-4-oxo-2,3,4,5-tetrahydrobenzo[b][1,4]oxazepin-3-yl)-4,5,6,7-tetrahydro-1H-indazole-3-carboxamide as a white solid (0.017 g, 38%): $^1$H NMR (400 MHz, DMSO-d6) δ 12.83 (s, 1H), 7.90 (d, J=8.0 Hz, 1H), 7.52-7.46 (m, 1H), 7.37-7.20 (m, 3H), 4.82 (dt, J=11.3, 7.8 Hz, 1H), 4.49 (dd, J=11.4, 9.8 Hz, 1H), 4.40 (dd, J=9.8, 7.7 Hz, 1H), 3.31 (s, 3H), 2.62-2.53 (m, 4H), 1.75-1.57 (m, 4H). LCMS $R_T$=4.21 min, m/z=341.2 $[M+H]^+$.

Example 33: Method EE

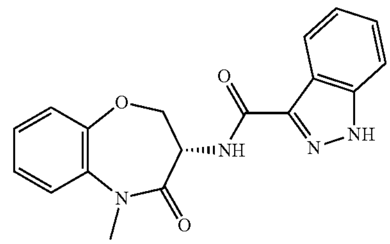 [SMILES: CN1C(=O)[C@@H](NC(=O)c2n[nH]c3ccccc23)COc2ccccc21]

(S)—N-(5-methyl-4-oxo-2,3,4,5-tetrahydrobenzo[b][1,4]oxazepin-3-yl)-1H-indazole-3-carboxamide To a stirred solution of (3S)-3-amino-5-methyl-2,3-dihydro-1,5-benzoxazepin-4-one (0.025 g, 0.13 mmol) in N,N-dimethylformamide (1 mL) was added 1H-indazole-3-carboxylic acid (0.026 g, 0.16 mmol), ((3H-[1,2,3]triazolo[4,5-b]pyridin-3-yl)oxy)tri(pyrrolidin-1-yl)phosphonium hexafluorophosphate(V) (0.078 g, 0.14 mmol) and N,N-diisopropylethylamine (0.045 mL, 0.26 mmol). After stirring at RT for 16 h the reaction mixture was loaded directly for purification by RP-HPLC (5 to 60% acetonitrile in water and 0.1% formic acid) affording (S)—N-(5-methyl-4-oxo-2,3,4,5-tetrahydrobenzo[b][1,4]oxazepin-3-yl)-1H-indazole-3-carboxamide as a white solid (0.015 g, 34%): $^1$H NMR (400 MHz, DMSO-d6) δ 13.71 (s, 1H), 8.39 (d, J=8.1 Hz, 1H), 8.06 (dt, J=8.2, 1.0 Hz, 1H), 7.63 (dt, J=8.5, 0.9 Hz, 1H), 7.56-7.49 (m, 1H), 7.42 (ddd, J=8.4, 6.9, 1.1 Hz, 1H), 7.38-7.19 (m, 4H), 4.95 (dt, J=11.6, 7.9 Hz, 1H), 4.63 (dd, J=11.6, 9.9 Hz, 1H), 4.47 (dd, J=9.9, 7.7 Hz, 1H), 3.34 (s, 3H). LCMS $R_T$=4.32 min, m/z=337.1 $[M+H]^+$.

Example 34: Method FF

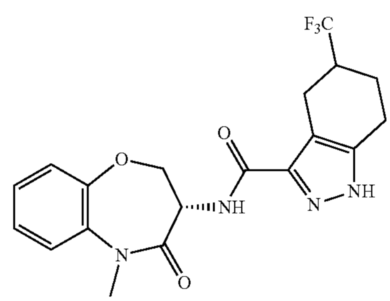 [SMILES: CN1C(=O)[C@@H](NC(=O)c2n[nH]c3c2CC(C(F)(F)F)CC3)COc2ccccc21]

N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide

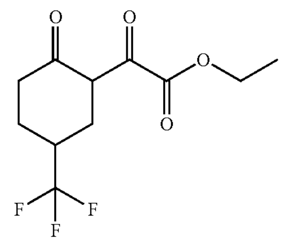 [SMILES: CCOC(=O)C(=O)C1CC(C(F)(F)F)CCC1=O]

Step 1: ethyl 2-oxo-2-(2-oxo-5-(trifluoromethyl)cyclohexyl)acetate

To a stirred solution of sodium ethoxide (2.68 mol/L) in ethanol (2.7 mL, 7.2 mmol) cooled to 0° C. was added dropwise a solution of 4-(trifluoromethyl)cyclohexanone (1 g, 6 mmol) in diethyl oxalate (1 g, 7.2 mmol). The reaction mixture was warmed to RT and stirred for 4 h. The reaction was then quenched with an aqueous solution of 5% citric acid (75 mL) and extracted with isopropyl acetate (3×75 mL). The combined organic extracts were dried over sodium sulfate and concentrated to dryness in vacuo. The resulting residue was purified by column chromatography (silica gel, 100-200 mesh, 0 to 50% isopropyl acetate in heptane) affording ethyl 2-oxo-2-(2-oxo-5-(trifluoromethyl)cyclohexyl)acetate as a yellow oil (0.623 g, 39%) used as is in the next step: LCMS $R_T$=1.34 min, m/z=267 $[M+H]^+$.

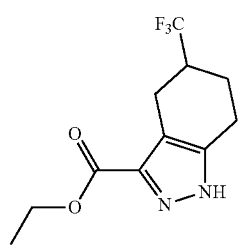 [SMILES: CCOC(=O)c1n[nH]c2c1CC(C(F)(F)F)CC2]

Step 2: ethyl 5-(trifluoromethyl)-4,5,6,7-tetrahydro-1H-indazole-3-carboxylate

To a solution of ethyl 2-oxo-2-(2-oxo-5-(trifluoromethyl)cyclohexyl)acetate (0.623 g, 2.34 mmol) in acetic acid (5 mL) was added hydrazine hydrate (300 mg, 4.68 mmol). The reaction mixture was heated to 80° C. for 16 h. The reaction mixture was concentrated to dryness in vacuo and purified by column chromatography (silica gel, 100-200 mesh, 0 to 100% isopropyl acetate in heptane) affording ethyl 5-(trifluoromethyl)-4,5,6,7-tetrahydro-H-indazole-3-carboxylate (0.425 g, 69%) as a white solid used as in the next step: LCMS $R_T$=1.23 min, m/z=263 $[M+H]^+$.

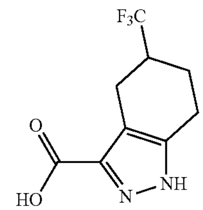 [SMILES: O=C(O)c1n[nH]c2c1CC(C(F)(F)F)CC2]

Step 3: 5-(trifluoromethyl)-4,5,6,7-tetrahydro-1H-indazole-3-carboxylic acid

To a solution of ethyl 5-(trifluoromethyl)-4,5,6,7-tetrahydro-1H-indazole-3-carboxylate (0.425 g, 1.62 mmol) in methanol (4 mL) was added sodium hydroxide (1 mol/L) in water (4.05 mL, 4.05 mmol). The reaction mixture was stirred at RT for 16 h. After this time, the mixture was concentrated in vacuo to remove methanol. The remaining solution was added to hydrochloric acid (1 mol/L) in water (50 mL). The resulting precipitate was collected, washed with 1 M hydrochloric acid, and dried thoroughly to afford 5-(trifluoromethyl)-4,5,6,7-tetrahydro-1H-indazole-3-carboxylic acid (0.164 g, 42% yield) as a white solid used in the next step without further purification: LCMS $R_T$=1.03 min, m/z=235 $[M+H]^+$.

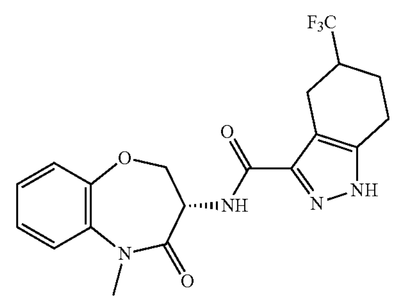 [SMILES: CN1C(=O)[C@@H](NC(=O)c2n[nH]c3c2CC(C(F)(F)F)CC3)COc2ccccc21]

Step 4: N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide To a stirred solution of (3S)-3-amino-5-methyl-2,3-dihydro-1,5-benzoxazepin-4-one (0.035 g, 0.18 mmol) in N,N-dimethylformamide (2 mL) was added 5-(trifluoromethyl)-4,5,6,7-tetrahydro-1H-indazole-3-carboxylic acid (0.051 g, 0.22 mmol), ((3H-[1,2,3]triazolo[4,5-b]pyridin-3-yl)oxy)tri(pyrrolidin-1-yl)phosphonium hexafluorophosphate(V) (0.109 g, 0.2 mmol) and N,N-diisopropylethylamine (0.095 mL, 0.55 mmol). After stirring at RT for 16 h the reaction mixture was loaded directly for purification by RP-HPLC (20 to 60% acetonitrile in water and 0.1% formic acid) affording N—((S)-5-methyl-4-oxo-2,3,4,5-tetrahydrobenzo[b][1,4]oxazepin-3-yl)-5-(trifluoromethyl)-4, 5,6,7-tetrahydro-1H-indazole-3-carboxamide (0.037 g, 50%) as a white solid: $^1H$ NMR (400 MHz, DMSO-d6) δ 13.01 (s, 1H), 8.00 (d, J=8.0 Hz, 1H), 7.53-7.45 (m, 1H), 7.37-7.20 (m, 3H), 4.83 (dt, J=11.5, 8.1 Hz, 1H), 4.52 (ddd, J=11.3, 10.7, 3.9 Hz, 1H), 4.40 (ddd, J=10.0, 7.7, 2.5 Hz, 1H), 3.31 (s, 3H), 2.98 (dt, J=16.0, 4.4 Hz, 1H), 2.85-2.54 (m, 3H), 2.49-2.38 (m, 1H), 2.15-2.01 (m, 1H), 1.71-1.53 (m, 1H). LCMS $R_T$=4.95 min, m/z=409.1 $[M+H]^+$.

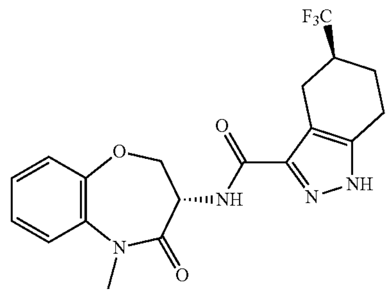

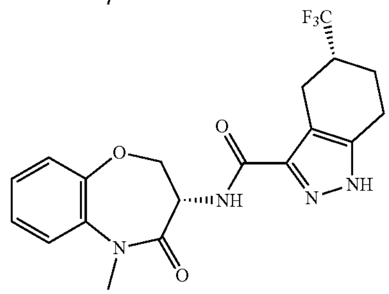

Step 5: (5S)—N-[(3S)-5-methyl-4-oxo-2,3-dihydro-1,5-benzoxazepin-3-yl]-5-(trifluoromethyl)-4,5, 6,7-tetrahydro-1H-indazole-3-carboxamide and (5R)—N-[(3S)-5-methyl-4-oxo-2,3-dihydro-1,5-benzoxazepin-3-yl]-5-(trifluoromethyl)-4,5,6,7-tetrahydro-1H-indazole-3-carboxamide N—((S)-5-methyl-4-oxo-2,3,4,5-tetrahydrobenzo[b][1,4]oxazepin-3-yl)-5-(trifluoromethyl)-4, 5,6,7-tetrahydro-1H-indazole-3-carboxamide was further purified by chiral SFC (SFC conditions: Column: Regis Whelk O-1 (s,s)50×4.6 mm I.D., 3 μm Mobile phase: A: CO2 B: Methanol (0.1% NH4OH) Isocratic: 25% B in 2.5 min Flow rate: 4 mL/min Column temperature: 40° C., BPR: 120 bar) affording arbitrarily assigned diastereomers (5S)—N-[(3S)-5-methyl-4-oxo-2,3-dihydro-1,5-benzoxazepin-3-yl]-5-(trifluoromethyl)-4,5,6,7-tetrahydro-1H-indazole-3-carboxamide (0.015 g, 20%) and (5R)—N-[(3S)-5-methyl-4-oxo-2,3-dihydro-1,5-benzoxazepin-3-yl]-5-(trifluoromethyl)-4,5,6,7-tetrahydro-1H-indazole-3-carboxamide (0.013 g, 17%) as white solids:

Analytical data for the first eluting diastereomer (arbitrarily assigned S,S configuration): SFC $R_T$ (Whelk O-1 (S,S) column, 25% methanol+0.1% ammonium hydroxide isocratic elution, 2.5 min method): 1.01 min, 100% ee: $^1H$ NMR (400 MHz, DMSO-d6) δ 12.97 (s, 1H), 8.00 (d, J=8.0 Hz, 1H), 7.68-7.41 (m, 1H), 7.41-7.06 (m, 3H), 4.83 (dt, J=11.4, 7.7 Hz, 1H), 4.51 (dd, J=11.5, 9.8 Hz, 1H), 4.40 (dd, J=9.8, 7.7 Hz, 1H), 3.31 (s, 3H), 2.98 (dd, J=16.0, 5.1 Hz, 1H), 2.86-2.74 (m, 1H), 2.74-2.57 (m, 2H), 2.47-2.37 (m, 1H), 2.16-2.02 (m, 1H), 1.72-1.51 (m, 1H). LCMS $R_T$=4.95 min, m/z=409.1 $[M+H]^+$.

Analytical data for the second eluting diastereomer (arbitrarily assigned R,S configuration): SFC $R_T$ 1.13 min, 98% ee: $^1H$ NMR (400 MHz, DMSO-d6) δ 13.00 (s, 1H), 8.01 (d, J=8.0 Hz, 1H), 7.63-7.39 (m, 1H), 7.43-7.11 (m, 3H), 4.83 (dt, J=11.4, 7.8 Hz, 1H), 4.52 (dd, J=11.5, 9.8 Hz, 1H), 4.41 (dd, J=9.9, 7.7 Hz, 1H), 3.31 (s, 3H), 2.99 (dd, J=16.0, 5.1 Hz, 1H), 2.85-2.74 (m, 1H), 2.74-2.58 (m, 2H), 2.48-2.38 (m, 1H), 2.16-2.03 (m, 1H), 1.71-1.53 (m, 1H). LCMS $R_T$=4.95 min, m/z=409.1 $[M+H]^+$.

Example 35: Method GG

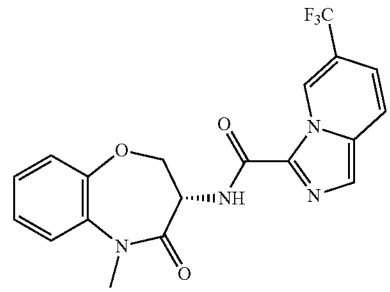 [SMILES: CN1C(=O)[C@@H](NC(=O)c2ncc3ccc(C(F)(F)F)cn23)COc2ccccc21]

N-[(3S)-5-methyl-4-oxo-2,3-dihydro-1,5-benzoxazepin-3-yl]-6-(trifluoromethyl)imidazo[1,5-a]pyridine-3-carboxamide

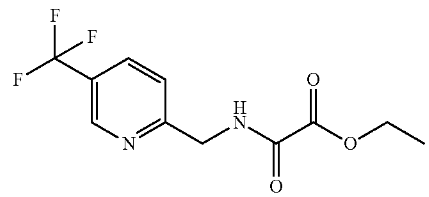 [SMILES: CCOC(=O)C(=O)NCc1ccc(C(F)(F)F)cn1]

Step 1: ethyl 2-oxo-2-[[5-(trifluoromethyl)-2-pyridyl]methylamino]acetate

To a solution of [5-(trifluoromethyl)-2-pyridyl]methanamine (1.0 g, 5.7 mmol) in anhydrous tetrahydrofuran cooled to 0° C. under nitrogen was added triethylamine (1.19 mL, 8.5 mmol) followed by ethyl 2-chloro-2-oxo-acetate (0.85 g, 6.25 mmol). The reaction mixture warmed to RT slowly and stirred for 16 h. The reaction mixture was concentrated to dryness in vacuo and partitioned between isopropyl acetate (100 mL) and saturated aqueous sodium bicarbonate (50 mL). The organic layer was washed with brine (50 mL), dried over sodium sulfate, and concentrated to dryness in vacuo affording ethyl 2-oxo-2-[[5-(trifluoromethyl)-2-pyridyl]methylamino]acetate (1.2 g, 77%) as an orange solid used in the next step without further purification: LCMS $R_T$=1.05 min, m/z=277 $[M+H]^+$.

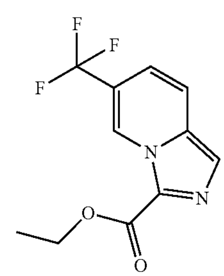 [SMILES: CCOC(=O)c1ncc2ccc(C(F)(F)F)cn12]

Step 2: ethyl 6-(trifluoromethyl)imidazo[1,5-a]pyridine-3-carboxylate

A suspension of ethyl 2-oxo-2-[[5-(trifluoromethyl)-2-pyridyl]methylamino]acetate (1.2 g, 4.3 mmol) in phosphoryl chloride (12 mL, 129 mmol) was heated to 100° C. for 16 h. The reaction mixture was concentrated to dryness in vacuo, diluted with dichloromethane/methanol/trimethylamine (85:5:10) and purified by column chromatography (silica gel, 100-200 mesh, 0 to 100% isopropyl acetate in heptane) affording ethyl 6-(trifluoromethyl)imidazo[1,5-a]pyridine-3-carboxylate as a brown solid (0.460 g, 32%) used as is in the next step: LCMS $R_T$=1.26 min, m/z=259 $[M+H]^+$.

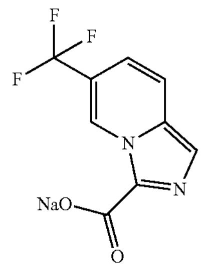

Step 3: sodium 6-(trifluoromethyl)imidazo[1,5-a]pyridine-3-carboxylate

To a solution of ethyl 6-(trifluoromethyl)imidazo[1,5-a]pyridine-3-carboxylate (0.100 g, 0.39 mmol) in tetrahydrofuran (2 mL) was added sodium hydroxide (1 mol/L) in water (0.47 mL. 0.47 mmol). The reaction mixture stirred at RT for 16 h, concentrated to dryness in vacuo affording sodium 6-(trifluoromethyl)imidazo[1,5-a]pyridine-3-carboxylate as a brown solid used in the next step without further purification: LCMS $R_T$=0.93 min, m/z=231 $[M+H]^+$.

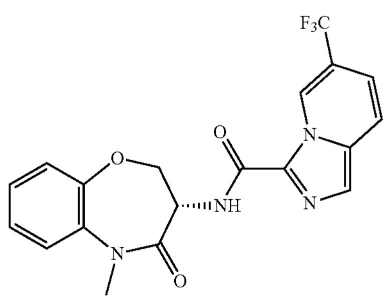 [SMILES: CN1C(=O)[C@@H](NC(=O)c2ncc3ccc(C(F)(F)F)cn23)COc2ccccc21]

Step 4: N-[(3S)-5-methyl-4-oxo-2,3-dihydro-1,5-benzoxazepin-3-yl]-6-(trifluoromethyl)imidazo[1,5-a]pyridine-3-carboxamide To a stirred solution of [(3S)-5-methyl-4-oxo-2,3-dihydro-1,5-benzoxazepin-3-yl]ammonium chloride (0.074 g, 0.32 mmol) in N,N-dimethylformamide (1.5 mL) was added sodium 6-(trifluoromethyl)imidazo[1,5-a]pyridine-3-carboxylate (0.097 g, 0.39 mmol), ((3H-[1,2,3]triazolo[4,5-b]pyridin-3-yl)oxy)tri(pyrrolidin-1-yl)phosphonium hexafluorophosphate(V) (0.210 g, 0.39 mmol) and N,N-diisopropylethylamine (0.17 mL, 0.97 mmol). After stirring at RT for 16 h the reaction mixture was loaded directly for purification by column chromatography (silica gel, 100-200 mesh, 0 to 70% isopropyl acetate in heptane) affording N-[(3S)-5-methyl-4-oxo-2,3-dihydro-1,5-benzoxazepin-3-yl]-6-(trifluoromethyl)imidazo[1,5-a]pyridine-3-carboxamide as a yellow solid (0.118 g, 91%): $^1H$ NMR (400 MHz, DMSO-d6) δ 9.66 (p, J=1.2 Hz, 1H), 8.78 (d, J=8.0 Hz, 1H), 8.03 (dt, J=9.6, 0.9 Hz, 1H), 7.81 (d, J=0.8 Hz, 1H), 7.58-7.46 (m, 1H), 7.41-7.19 (m, 4H), 4.91 (dt, J=11.6, 7.8 Hz, 1H), 4.69 (dd, J=11.6, 9.9 Hz, 1H), 4.46 (dd, J=9.9, 7.7 Hz, 1H), 3.33 (s, 3H). LCMS $R_T$=5.64 min, m/z=405.1 $[M+H]^+$.

Example 36: Method HH

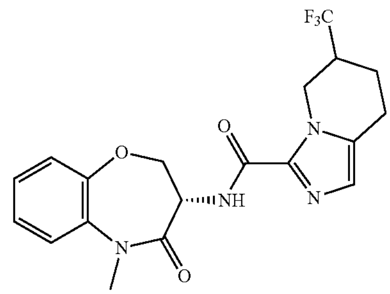 [SMILES: CN1C(=O)[C@@H](NC(=O)c2ncc3n2CC(C(F)(F)F)CC3)COc2ccccc21]

N—((S)-5-methyl-4-oxo-2,3,4,5-tetrahydrobenzo[b][1,4]oxazepin-3-yl)-6-(trifluoromethyl)-5,6,7,8-tetrahydroimidazo[1,5-a]pyridine-3-carboxamide To a solution of N-[(3S)-5-methyl-4-oxo-2,3-dihydro-1,5-benzoxazepin-3-yl]-6-(trifluoromethyl)imidazo[1,5-a]pyridine-3-carboxamide (0.034 g, 0.084 mmol) in methanol (2 mL) was added palladium hydroxide (10 wt % loading, 0.020 g) followed by a balloon of hydrogen. The reaction mixture was stirred at RT for 16 h, filtered through Celite and concentrated to dryness in vacuo affording N—((S)-5-methyl-4-oxo-2,3,4,5-tetrahydrobenzo[b][1,4]oxazepin-3-yl)-6-(trifluoromethyl)-5, 6,7,8-tetrahydroimidazo[1,5-a]pyridine-3-carboxamide (34 mg, 99%) as a yellow oil: $^1H$ NMR (400 MHz, DMSO-d6) δ 8.35 (d, J=8.0 Hz, 1H), 7.54-7.45 (m, 1H), 7.37-7.19 (m, 3H), 6.89 (d, J=0.8 Hz, 1H), 4.91-4.69 (m, 2H), 4.57 (ddd, J=11.6, 9.8, 3.6 Hz, 1H), 4.40 (ddd, J=9.8, 7.6, 2.0 Hz, 1H), 4.12-4.01 (m, 2H), 3.31 (s, 3H), 3.04-2.92 (m, 1H), 2.84-2.69 (m, 1H), 2.15-2.04 (m, 1H), 1.83-1.67 (m, 1H). LCMS $R_T$=5.07 min, m/z=409.1 $[M+H]^+$.

Example 37: Method II

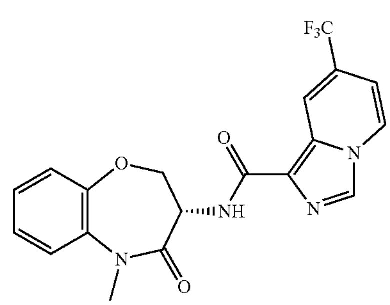 [SMILES: CN1C(=O)[C@@H](NC(=O)c2ncn3ccc(C(F)(F)F)cc23)COc2ccccc21]

N-[(3S)-5-methyl-4-oxo-2,3-dihydro-1,5-benzoxazepin-3-yl]-7-(trifluoromethyl)imidazo[1,5-a]pyridine-1-carboxamide

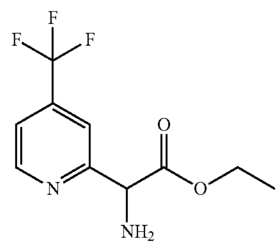

Step 1: ethyl 2-amino-2-[4-(trifluoromethyl)-2-pyridyl]acetate

To a stirred suspension of sodium hydride (95%, 0.631 g, 25 mmol) in N,N-dimethylformamide (50 mL) cooled to 0° C. was added ethyl 2-(benzhydrylideneamino)acetate (5.35 g, 20 mmol). After stirring the reaction for 30 min at 0° C., 2-chloro-4-(trifluoromethyl)pyridine (4 g, 22 mmol) was added. The reaction mixture was warmed to RT and stirred for 4 h. Hydrochloric acid (1 mol/L) in water (50 mL) was added, and the resulting mixture stirred at RT for 3 h. The mixture was diluted with isopropyl acetate (100 mL) and neutralized with saturated aqueous sodium bicarbonate (50 mL). The layers were separated, and the aqueous was extracted with isopropyl acetate (2×100 mL). The combined organics were dried over sodium sulfate, concentrated to dryness in vacuo, and purified by column chromatography (silica gel, 100-200 mesh, 0 to 10% methanol in dichloromethane) affording ethyl 2-amino-2-[4-(trifluoromethyl)-2-pyridyl]acetate (0.630 g, 13%) used as is in the next step: LCMS $R_T$=0.93 min, m/z=249 $[M+H]^+$.

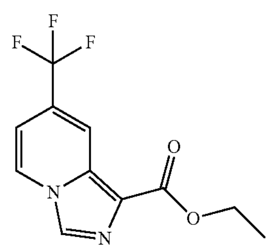 [SMILES: CCOC(=O)c1ncn2ccc(C(F)(F)F)cc12]

Step 2: ethyl 7-(trifluoromethyl)imidazo[1,5-a]pyridine-1-carboxylate

To a solution of ethyl 2-amino-2-[4-(trifluoromethyl)-2-pyridyl]acetate (0.630 g, 0.254 mmol) in toluene (5 mL) was added N,N-dimethylformamide dimethyl acetal (0.44 mL, 3.3 mmol), and the resulting mixture was heated to 80° C. in a sealed vessel for 16 h. The reaction mixture was then concentrated to dryness in vacuo and purified by column chromatography (silica gel, 100-200 mesh, 0 to 5% methanol in dichloromethane) affording ethyl 7-(trifluoromethyl)imidazo[1,5-a]pyridine-1-carboxylate (0.147 g, 22%) as a white solid used as is in the next step: LCMS $R_T$=1.19 min, m/z=259 $[M+H]^+$.

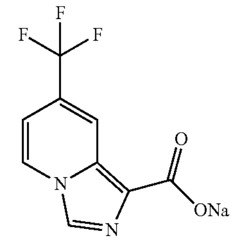

Step 3: sodium 7-(trifluoromethyl)imidazo[1,5-a]pyridine-1-carboxylate

To a stirred solution of ethyl 7-(trifluoromethyl)imidazo[1,5-a]pyridine-1-carboxylate (0.147 g, 0.57 mmol) in tetrahydrofuran (2 mL) was added sodium hydroxide (1 mol/L) in water (1.4 mL, 1.4 mmol). The resulting mixture was heated to 50° C. for 6 h, concentrated to dryness in vacuo affording sodium 7-(trifluoromethyl)imidazo[1,5-a]pyridine-1-carboxylate as a white solid used as is in the next step: LCMS $R_T$=0.95 min, m/z=231 $[M+H]^+$.

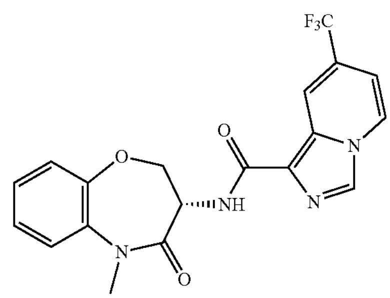 [SMILES: CN1C(=O)[C@@H](NC(=O)c2ncn3ccc(C(F)(F)F)cc23)COc2ccccc21]

Step 4: N-[(3S)-5-methyl-4-oxo-2,3-dihydro-1,5-benzoxazepin-3-yl]-7-(trifluoromethyl)imidazo[1,5-a]pyridine-1-carboxamide To a stirred solution of [(3S)-5-methyl-4-oxo-2,3-dihydro-1,5-benzoxazepin-3-yl]ammonium chloride (0.052 g, 0.23 mmol) in N,N-dimethylformamide (1.5 mL) was added sodium 7-(trifluoromethyl)imidazo[1,5-a]pyridine-1-carboxylate (0.069 g, 0.27 mmol), ((3H-[1,2,3]triazolo[4,5-b]pyridin-3-yl)oxy)tri(pyrrolidin-1-yl)phosphonium hexafluorophosphate(V) (0.148 g, 0.27 mmol) and N,N-diisopropylethylamine (0.12 mL, 0.68 mmol). After stirring at RT for 16 h the reaction mixture was loaded directly for purification by RP-HPLC (30 to 70% acetonitrile in water and 0.1% formic acid) affording N-[(3S)-5-methyl-4-oxo-2,3-dihydro-1,5-benzoxazepin-3-yl]-7-(trifluoromethyl)imidazo[1,5-a]pyridine-1-carboxamide (0.067 g, 73%) as a white solid: $^1H$ NMR (400 MHz, DMSO-d6) δ 8.71-8.66 (m, 2H), 8.36-8.25 (m, 2H), 7.55-7.47 (m, 1H), 7.39-7.21 (m, 3H), 7.12 (dd, J=7.4, 1.9 Hz, 1H), 4.92 (dt, J=11.5, 7.8 Hz, 1H), 4.60 (dd, J=11.5, 9.8 Hz, 1H), 4.47 (dd, J=9.8, 7.7 Hz, 1H), 3.33 (s, 3H). LCMS $R_T$=5.03 min, m/z=405.1 $[M+H]^+$.

Example 38: Method JJ

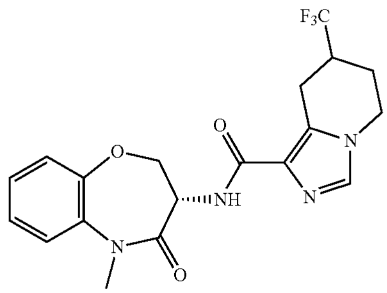 [SMILES: CN1C(=O)[C@@H](NC(=O)c2ncn3c2CC(C(F)(F)F)CC3)COc2ccccc21]

N-[(3S)-5-methyl-4-oxo-2,3-dihydro-1,5-benzoxazepin-3-yl]-7-(trifluoromethyl)imidazo[1,5-a]pyridine-1-carboxamide To a solution of N-[(3S)-5-methyl-4-oxo-2,3-dihydro-1,5-benzoxazepin-3-yl]-7-(trifluoromethyl)imidazo[1,5-a]pyridine-1-carboxamide (0.050 g, 0.12 mmol) in methanol (2 mL) was added palladium hydroxide (10 wt % loading, 0.030 g) followed by a balloon of hydrogen. The reaction mixture was stirred at RT for 16 h, filtered through Celite and concentrated to dryness in vacuo affording N-[(3S)-5-methyl-4-oxo-2,3-dihydro-1,5-benzoxazepin-3-yl]-7-(trifluoromethyl)-5,6,7,8-tetrahydroimidazo[1,5-a]pyridine-1-carboxamide (31 mg, 61%) as a yellow oil: $^1H$ NMR (400 MHz, DMSO-d6) δ 7.88 (d, J=8.0 Hz, 1H), 7.69 (s, 1H), 7.53-7.45 (m, 1H), 7.36-7.20 (m, 3H), 4.81 (dt, J=11.2, 7.9 Hz, 1H), 4.54-4.36 (m, 2H), 4.33-4.23 (m, 1H), 3.95 (tt, J=12.4, 4.4 Hz, 1H), 3.39-3.33 (m, 1H), 3.31 (s, 3H), 3.05-2.86 (m, 1H), 2.80-2.64 (m, 1H), 2.26-2.12 (m, 1H), 1.95-1.78 (m, 1H). LCMS $R_T$=4.46 min, m/z=409.1 $[M+H]^+$.

Example 39: Method KK

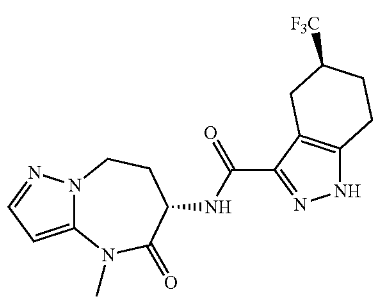

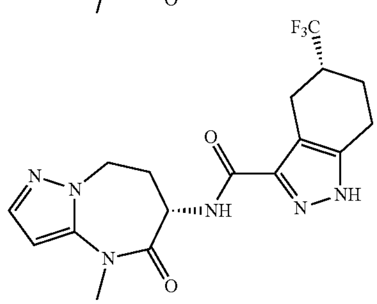

(5S)—N-[(6S)-4-methyl-5-oxo-7,8-dihydro-6H-pyrazolo[1,5-a][1,3]diazepin-6-yl]-5-(trifluoromethyl)-4,5,6,7-tetrahydro-1H-indazole-3-carboxamide and (5R)—N-[(6S)-4-methyl-5-oxo-7,8-dihydro-6H-pyrazolo[1,5-a][1,3]diazepin-6-yl]-5-(trifluoromethyl)-4,5,6,7-tetrahydro-1H-indazole-3-carboxamide

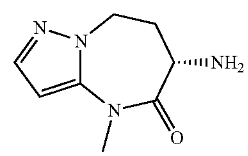

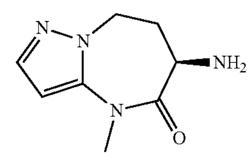

Step 1: (6S)-6-amino-4-methyl-7,8-dihydro-6H-pyrazolo[1,5-a][1,3]diazepin-5-one and (6R)-6-amino-4-methyl-7,8-dihydro-6H-pyrazolo[1,5-a][1,3]diazepin-5-one To a solution of 6-azido-4-methyl-7,8-dihydro-4H-pyrazolo[1,5-a][1,3]diazepin-5(6H)-one (0.500 g, 2.42 mmol) in methanol (10 mL) was added 10% Pd/C (0.258 g, 0.242 mmol), a balloon of hydrogen, and the mixture was stirred at RT for 16 h. The reaction mixture was filtered through Celite, concentrated to dryness in vacuo, and purified by column chromatography (silica gel, 100-200 mesh, 0 to 20% methanol in dichloromethane) affording 6-amino-4-methyl-7,8-dihydro-4H-pyrazolo[1,5-a][1,3]diazepin-5(6H)-one (0.210 g, 48%) as a viscous oil. The resulting compound was further purified by chiral SFC (Chiralpak AD 150×21.2 mm I.D column, 5 μm Mobile phase: A: CO2 B: Methanol (0.1% NH4OH) Isocratic 25% B for 6.0 min. Flow rate: 70 mL/min Column temperature: 40° C. BPR: 100 bar) affording arbitrarily assigned diastereomers (6S)-6-amino-4-methyl-7,8-dihydro-6H-pyrazolo[1,5-a][1,3]diazepin-5-one (0.074 g, 17%) and (6R)-6-amino-4-methyl-7,8-dihydro-6H-pyrazolo[1,5-a][1,3]diazepin-5-one (0.074 g, 17%) as viscous oils used as is in the next step.

Analytical data for the first eluting enantiomer (arbitrarily assigned S configuration): SFC $R_T$(AD column, 25% methanol+0.1% ammonium hydroxide isocratic elution, 2.5 min method): 0.42 min, 98% ee; Analytical data for the second eluting enantiomer (arbitrarily assigned R configuration): SFC $R_T$=0.69 min, 97% ee.

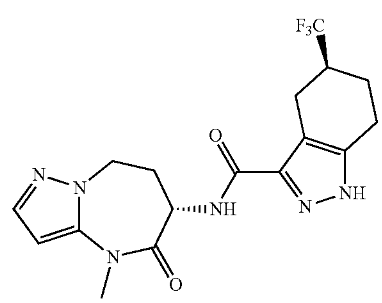

-continued

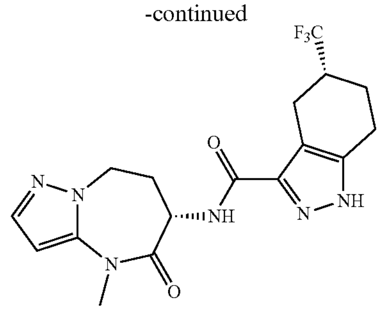

Step 2: (5S)—N-[(6S)-4-methyl-5-oxo-7,8-dihydro-6H-pyrazolo[1,5-a][1,3]diazepin-6-yl]-5-(trifluoromethyl)-4,5,6,7-tetrahydro-1H-indazole-3-carboxamide and (5R)—N-[(6S)-4-methyl-5-oxo-7,8-dihydro-6H-pyrazolo[1,5-a][1,3]diazepin-6-yl]-5-(trifluoromethyl)-4,5,6,7-tetrahydro-1H-indazole-3-carboxamide To a stirred solution of (6S)-6-amino-4-methyl-7,8-dihydro-6H-pyrazolo[1,5-a][1,3]diazepin-5-one (0.022 g, 0.12 mmol) in N,N-dimethylformamide (2 mL) was added 5-(trifluoromethyl)-4,5,6,7-tetrahydro-1H-indazole-3-carboxylic acid (0.034 g, 0.15 mmol), ((3H-[1,2,3]triazolo[4,5-b]pyridin-3-yl)oxy)tri(pyrrolidin-1-yl)phosphonium hexafluorophosphate(V) (0.080 g, 0.15 mmol) and N,N-diisopropylethylamine (0.064 mL, 0.37 mmol). After stirring at RT for 16 h the reaction mixture was loaded directly for purification by RP-HPLC (20 to 60% acetonitrile in water and 0.1% formic acid) affording N-[(6S)-4-methyl-5-oxo-7,8-dihydro-6H-pyrazolo[1,5-a][1,3]diazepin-6-yl]-5-(trifluoromethyl)-4,5,6,7-tetrahydro-1H-indazole-3-carboxamide (0.040 g, 83%) as a white solid.

The resulting compound was further purified by chiral SFC (SFC conditions: Column: Lux Cellulose-1 50×4.6 mm I.D., 3 m Mobile phase: A: CO2 B: Methanol (0.1% NH4OH) Isocratic: 20% B in 2.5 min Flow rate: 4 mL/min Column temperature: 40° C., BPR: 120 bar) affording arbitrarily assigned diastereomers (5R)—N-[(6S)-4-methyl-5-oxo-7,8-dihydro-6H-pyrazolo[1,5-a][1,3]diazepin-6-yl]-5-(trifluoro methyl)-4,5,6,7-tetrahydro-1H-indazole-3-carboxamide (0.019 g, 38%) and (5S)—N-[(6S)-4-methyl-5-oxo-7,8-dihydro-6H-pyrazolo[1,5-a][1,3]diazepin-6-yl]-5-(trifluoro methyl)-4,5,6,7-tetrahydro-1H-indazole-3-carboxamide (0.019 g, 38%) as white solids:

Analytical data for the first eluting diastereomer (arbitrarily assigned R, S configuration): SFC $R_T$ (Lux Cellulose-1 column, 25% methanol+0.1% ammonium hydroxide isocratic elution, 2.5 min method): 1.23 min, 100% ee: $^1$H NMR (400 MHz, DMSO-d6) δ 12.97 (s, 1H), 8.07 (d, J=7.9 Hz, 1H), 7.49 (d, J=2.1 Hz, 1H), 6.32 (d, J=2.0 Hz, 1H), 4.42-4.24 (m, 2H), 4.23-4.12 (m, 1H), 3.25 (s, 3H), 3.05-2.93 (m, 2H), 2.84-2.74 (m, 1H), 2.74-2.54 (m, 3H), 2.39-2.25 (m, 1H), 2.15-2.04 (m, 1H), 1.72-1.55 (m, 1H). LCMS $R_T$=3.97 min, m/z=397.1 $[M+H]^+$.

Analytical data for the second eluting diastereomer (arbitrarily assigned S,S configuration): SFC $R_T$ 1.59 min, 100% ee: $^1$H NMR (400 MHz, DMSO-d6) δ 12.98 (s, 1H), 8.08 (d, J=7.9 Hz, 1H), 7.50 (d, J=2.0 Hz, 1H), 6.33 (d, J=2.0 Hz, 1H), 4.45-4.09 (m, 3H), 3.25 (s, 3H), 3.01 (dd, J=16.0, 5.1 Hz, 1H), 2.87-2.56 (m, 4H), 2.47-2.25 (m, 2H), 2.18-2.02 (m, 1H), 1.74-1.52 (m, 1H). LCMS $R_T$=3.95 min, m/z=397.1 $[M+H]^+$.

Examples 40-43

Chiral Separation of Compounds

Supercritical fluid chromatography (SFC) was performed on select compounds of the invention in order to obtain chiral separation of stereoisomers. SFC chiral conditions are as follows. All isolated peaks were arbitrarily assigned.

Example 40

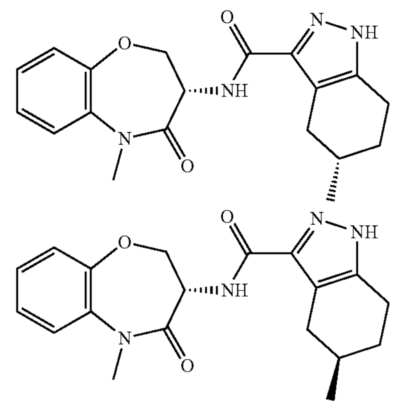

(S)-5-methyl-N—((S)-5-methyl-4-oxo-2,3,4,5-tetrahydrobenzo[b][1,4]oxazepin-3-yl)-4,5,6, 7-tetrahydro-1H-indazole-3-carboxamide and R)-5-methyl-N—((S)-5-methyl-4-oxo-2,3,4,5-tetrahydrobenzo[b][1,4]oxazepin-3-yl)-4,5,6, 7-tetrahydro-1H-indazole-3-carboxamide Prep:

SFC condition: Column: Chiralcel OX 150×21.2 mm I.D., 5 μm Mobile phase: A: $CO_2$ B: Methanol (0.1% $NH_4OH$) Isocratic: 45% B in 6 min Flow rate: 70 mL/min Column temperature: 40° C., BPR: 100 bar (Peak 2: 4.5 min) and SFC condition: Column: Chiralcel OX 150×21.2 mm I.D., 5 μm Mobile phase: A: $CO_2$ B: Methanol (0.1% $NH_4OH$) Isocratic: 45% B in 6 min Flow rate: 70 mL/min Column temperature: 40° C., BPR: 100 bar (Peak 1: 4.0 min).

Analytical:

SFC condition: Column: Chiralcel OX 50×4.6 mm I.D., 3 μm Mobile phase: A: $CO_2$ B: Methanol (0.1% $NH_4OH$) Isocratic: 40% B in 2.5 min Flow rate: 4 mL/min Column temperature: 40° C., BPR: 120 bar (Peak 2: 1.200 min) and SFC condition: Column: Chiralcel OX 50×4.6 mm I.D., 3 μm Mobile phase: A: $CO_2$ B: Methanol (0.1% $NH_4OH$) Isocratic: 40% B in 2.5 min Flow rate: 4 mL/min Column temperature: 40° C., BPR: 120 bar (Peak 1: 1.031 min).

Example 41

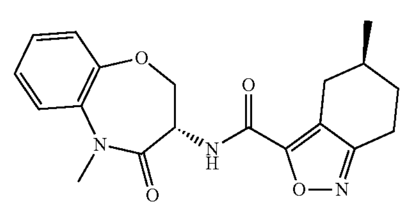

-continued

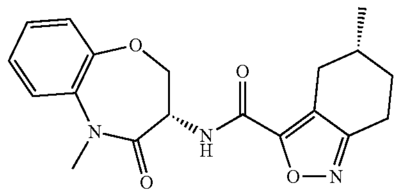

(S)-5-methyl-N—((S)-5-methyl-4-oxo-2,3,4,5-tetrahydrobenzo[b][1,4]oxazepin-3-yl)-4,5,6,7-tetrahydrobenzo[c]isoxazole-3-carboxamide and (R)-5-methyl-N—((S)-5-methyl-4-oxo-2,3,4,5-tetrahydrobenzo[b][1,4]oxazepin-3-yl)-4,5,6,7-tetrahydrobenzo[c]isoxazole-3-carboxamide Prep:

SFC condition: Column: Chiralpak AD 150×21.2 mm I.D., 5 μm Mobile phase: A: $CO_2$ B: Ethanol (0.1% $NH_4OH$) Isocratic: 25% B in 6.0 min Flow rate: 70 mL/min Column temperature: 40° C., BPR: 100 bar (Peak 1: 2.6 min) and SFC condition: Column: Chiralpak AD 150×21.2 mm I.D., 5 μm Mobile phase: A: $CO_2$ B: Ethanol (0.1% $NH_4OH$) Isocratic: 25% B in 6.0 min Flow rate: 70 mL/min Column temperature: 40° C., BPR: 100 bar (Peak 2: 3.0 min).

Analytical:

SFC condition: Column: Chiralpak AD 50×4.6 mm I.D., 3 μm Mobile phase: A: $CO_2$ B: Ethanol (0.1% $NH_4OH$) Isocratic: 20% B in 2.5 min Flow rate: 4 mL/min Column temperature: 40° C., BPR: 120 bar (Peak 1: 0.862 min) and SFC condition: Column: Chiralpak AD 50×4.6 mm I.D., 3 μm Mobile phase: A: $CO_2$ B: Ethanol (0.1% $NH_4OH$) Isocratic: 20% B in 2.5 min Flow rate: 4 mL/min Column temperature: 40° C., BPR: 120 bar (Peak 2: 0.957 min).

Example 42

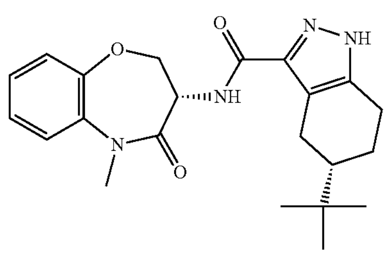

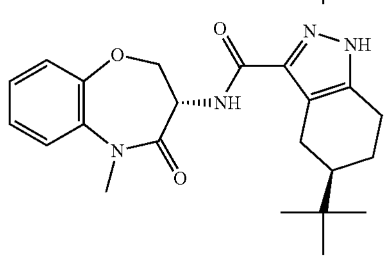

(S)-5-(tert-butyl)-N—((S)-5-methyl-4-oxo-2,3,4,5-tetrahydrobenzo[b][1,4]oxazepin-3-yl)-4,5,6,7-tetrahydro-1H-indazole-3-carboxamide and (R)-5-(tert-butyl)-N—((S)-5-methyl-4-oxo-2,3,4,5-tetrahydrobenzo[b][1,4]oxazepin-3-yl)-4,5, 6,7-tetrahydro-1H-indazole-3-carboxamide Prep:

SFC condition: Column: Lux Cellulose-3 150×21.2 mm I.D., 5 m Mobile phase: A: $CO_2$ B: Methanol (0.1% $NH_4OH$) Isocratic: 15% B in 6 min Flow rate: 70 mL/min Column temperature: 40° C., BPR: 100 bar (Peak 2: 2.5 min) and SFC condition: Column: Lux Cellulose-3 150×21.2 mm I.D., 5 μm Mobile phase: A: $CO_2$ B: Methanol (0.1% $NH_4OH$) Isocratic: 15% B in 6 min Flow rate: 70 mL/min Column temperature: 40° C., BPR: 100 bar (Peak 1: 2.0 min).

Analytical:

SFC condition: Column: Lux Cellulose-3 50×4.6 mm I.D., 3 μm Mobile phase: A: $CO_2$ B: Methanol (0.1% $NH_4OH$) Isocratic: 15% B in 2.5 min Flow rate: 4 mL/min Column temperature: 40° C., BPR: 120 bar (Peak 2: 0.551 min) and SFC condition: Column: Lux Cellulose-3 50×4.6 mm I.D., 3 μm Mobile phase: A: $CO_2$ B: Methanol (0.1% $NH_4OH$) Isocratic: 15% B in 2.5 min Flow rate: 4 mL/min Column temperature: 40° C., BPR: 120 bar (Peak 1: 0.0.470 min).

Example 43

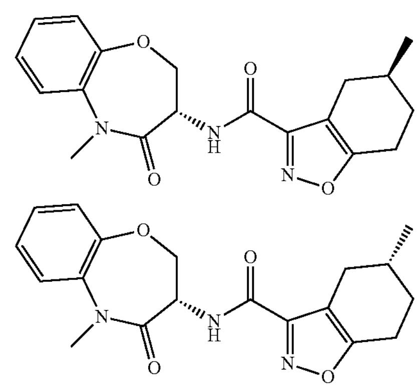

Prep:

SFC condition: Column: Chiralpak ID 150×21.2 mm I.D., 5 μm Mobile phase: A: $CO_2$ B: Ethanol (0.1% $NH_4OH$) Isocratic: 40% B in 6 min Flow rate: 70 mL/min Column temperature: 40° C., BPR: 100 bar (Peak 1: 2.0 min) and SFC condition: Column: Chiralpak ID 150×21.2 mm I.D., 5 μm Mobile phase: A: $CO_2$ B: Ethanol (0.1% $NH_4OH$) Isocratic: 40% B in 6 min Flow rate: 70 mL/min Column temperature: 40° C., BPR: 100 bar (Peak 2: 3.25 min).

Analytical:

SFC condition: Column: Chiralpak ID 50×4.6 mm I.D., 3 μm Mobile phase: A: $CO_2$ B: Ethanol (0.1% $NH_4OH$) Isocratic: 30% B in 2.5 min Flow rate: 4 mL/min Column temperature: 40° C., BPR: 120 bar (Peak 1: 0.888 min) and SFC condition: Column: Chiralpak ID 50×4.6 mm I.D., 3 μm Mobile phase: A: $CO_2$ B: Ethanol (0.1% $NH_4OH$) Isocratic: 30% B in 2.5 min Flow rate: 4 mL/min Column temperature: 40° C., BPR: 120 bar (Peak 2: 1.424 min).

Examples 44-82 were prepared according to the above procedures and synthetic schemes as shown in Table 1 below.

Example 83

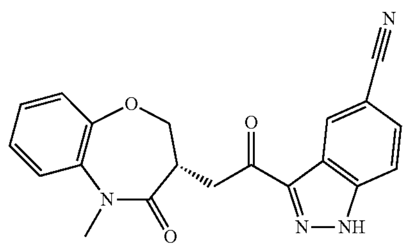 [SMILES: CN1C(=O)[C@@H](CC(=O)c2n[nH]c3ccc(C#N)cc23)COc2ccccc21]

(S)-5-cyano-N-(5-methyl-4-oxo-2,3,4,5-tetrahydrobenzo[b][1,4]oxazepin-3-yl)-1H-indazole-3-carboxamide Method B (33 mg, 59% yield)

$^1$H NMR (400 MHz, DMSO-$d_6$) δ 14.23 (s, 1H), 8.68-8.59 (m, 1H), 8.52-8.43 (m, 1H), 7.87-7.74 (m, 2H), 7.58-7.48 (m, 1H), 7.42-7.18 (m, 3H), 5.00-4.88 (m, 1H), 4.73-4.60 (m, 1H), 4.53-4.41 (m, 1H), 3.33 (s, 3H). LC-MS $R_T$=4.57 min, m/z=362.1 $(M+H)^+$.

LCMS (2 to 98% acetonitrile in water+0.1% formic acid over 10 mins) retention time 4.57 min, ESI+ found [M+H]=362.1.

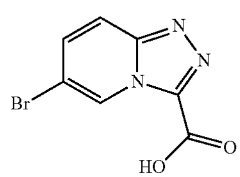 [SMILES: O=C(O)c1nnc2ccc(Br)cn12]

Step 1: 6-bromo-[1,2,4]triazolo[4,3-a]pyridine-3-carboxylic acid

In a screw cap vial, ethyl 6-bromo-[1,2,4]triazolo[4,3-a]pyridine-3-carboxylate (70 mg, 0.259 mmol) was dissolved in tetrahydrofuran (1 mL) and methanol (0.2 mL). To the reaction was then added lithium hydroxide (0.20 mL, 0.388 mmol) and stirred at RT for 18 h. Upon completion, reaction was concentrated to dryness in vacuo to afford crude 6-bromo-[1,2,4]triazolo[4,3-a]pyridine-3-carboxylic acid (62 mg, 98% yield) used as is in the next step.

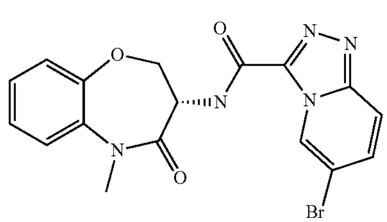 [SMILES: CN1C(=O)[C@@H](NC(=O)c2nnc3ccc(Br)cn23)COc2ccccc21]

Step 2: (S)-6-bromo-N-(5-methyl-4-oxo-2,3,4,5-tetrahydrobenzo[b][1,4]oxazepin-3-yl)-[1,2,4]triazolo[4,3-a]pyridine-3-carboxamide To a screw cap vial (S)-3-amino-5-methyl-2,3-dihydrobenzo[b][1,4]oxazepin-4(5H)-one hydrochloride (58 mg, 0.255 mmol), 1-[bis(dimethylamino)methylene]-1H-1,2,3-triazolo[4,5-b]pyridinium 3-oxide hexafluorophosphate (120 mg, 0.316 mmol), and 6-bromo-[1,2,4]triazolo[4,3-a]pyridine-3-carboxylic acid (62 mg, 0.243 mmol) was added and dissolved in N,N-dimethylformamide (5 mL). To the reaction mixture was added trimethylamine (0.136 mL, 0.973 mmol), the vial was capped and stirred at RT for 16 h. The mixture was concentrated to dryness in vacuo and the residue was purified by RP-HPLC affording (S)-6-bromo-N-(5-methyl-4-oxo-2,3,4,5-tetrahydrobenzo[b][1,4]oxazepin-3-yl)-[1,2,4]triazol o[4,3-a]pyridine-3-carboxamide (92 mg, 90% yield), used as is in the next step.

Example 84

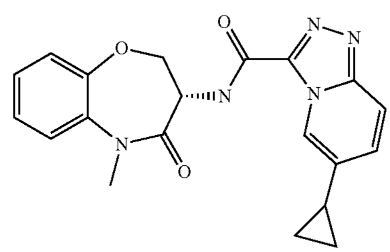 [SMILES: CN1C(=O)[C@@H](NC(=O)c2nnc3ccc(C4CC4)cn23)COc2ccccc21]

Step 3: (S)-6-cyclopropyl-N-(5-methyl-4-oxo-2,3,4,5-tetrahydrobenzo[b][1,4]oxazepin-3-yl)-[1,2, 4]triazolo[4,3-a]pyridine-3-carboxamide In a microwave vial, (S)-6-bromo-N-(5-methyl-4-oxo-2,3,4,5-tetrahydrobenzo[b][1,4]oxazepin-3-yl)-[1,2,4]triazol o[4,3-a]pyridine-3-carboxamide (92 mg, 0.221 mmol), potassium cyclopropyltrifluoroborate (68.9 mg, 0.442 mmol), palladium(II) acetate (4.96 mg, 0.022 mmol), di(adamantan-1-yl)(butyl)phosphine (12.51 mg, 0.0332 mmol), and cesium carbonate (288.1 mg, 0.884 mmol) were added and purged with N2 for 2 min. To the vial was then added toluene (4.42 ml, 41.8 mmol) and water (0.442 ml, 24.54 mmol) and the reaction was allowed to stir 110° C. for 18 h. The mixture was concentrated to dryness in vacuo and the residue was purified by RP-HPLC affording (S)-6-cyclopropyl-N-(5-methyl-4-oxo-2,3,4,5-tetrahydrobenzo[b][1,4]oxazepin-3-yl)-[1,2,4]triazolo[4,3-a]pyridine-3-carboxamide (18 mg, 21% yield): $^1$H NMR (400 MHz, DMSO-$d_6$) δ 9.31 (d, J=8.0 Hz, 1H), 9.25-9.20 (m, 1H), 7.99 (dd, J=9.7, 1.0 Hz, 1H), 7.72 (dd, J=9.7, 1.8 Hz, 1H), 7.59-7.49 (m, 1H), 7.42-7.22 (m, 3H), 5.02-4.87 (m, 1H), 4.81-4.67 (m, 1H), 4.54-4.41 (m, 1H), 1.79-1.69 (m, 1H), 1.03-0.93 (m, 2H), 0.80-0.69 (m, 2H). LC-MS $R_T$=4.66 min, m/z=378.1 $(M+H)^+$.

LCMS (2 to 98% acetonitrile in water+0.1% formic acid over 10 mins) retention time 4.66 min, ESI+ found [M+H]=378.1.

Example 85

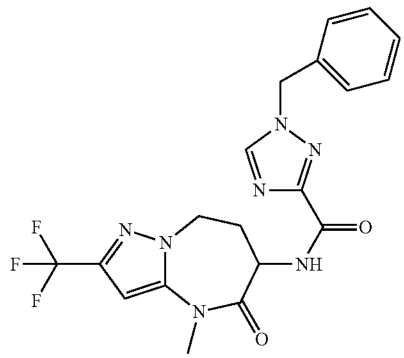 [SMILES: CN1C(=O)C(NC(=O)c2ncn(Cc3ccccc3)n2)CCn2nc(C(F)(F)F)cc21]

Step 1: 1-benzyl-N-(4-methyl-5-oxo-2-(trifluoromethyl)-5,6,7,8-tetrahydro-4H-pyrazolo[1,5-a][,3]diazepin-6-yl)-1H-1,2,4-triazole-3-carboxamide Method B To a screw cap vial 6-amino-4-methyl-2-(trifluoromethyl)-7,8-dihydro-4H-pyrazolo[1,5-a][1,3]diazepin-5 (6H)-one (74 mg, 0.298 mmol), 1-[bis(dimethylamino)methylene]-1H-1,2,3-triazolo[4,5-b]pyridinium 3-oxide hexafluorophosphate (158 mg, 0.417 mmol), 1-benzyl-1H-1,2,4-triazole-3-carboxylic acid (76 mg, 0.358 mmol) was added and dissolved in N,N-dimethylformamide (5 mL). To the reaction mixture was added trimethylamine (0.166 mL, 1.19 mmol), the vial was capped and stirred at RT for 16 h. The mixture was concentrated to dryness in vacuo and the residue was purified by RP-HPLC affording 1-benzyl-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide (77 mg, 59% yield): $^1$H NMR (400 MHz, DMSO-d6) δ 8.82 (s, 1H), 8.63 (d, J=7.6 Hz, 1H), 7.49-7.19 (m, 5H), 6.93 (s, 1H), 5.49 (s, 2H), 4.51-4.42 (m, 1H), 4.39-4.27 (m, 2H), 3.27 (s, 3H), 2.72-2.59 (m, 1H), 2.48-2.42 (m, 1H). LC-MS $R_T$=4.34 min, m/z=434.1 $(M+H)^+$.

LCMS (2 to 98% acetonitrile in water+0.1% formic acid over 10 mins) retention time 4.34 min, ESI+ found [M+H]=434.1.

Example 86

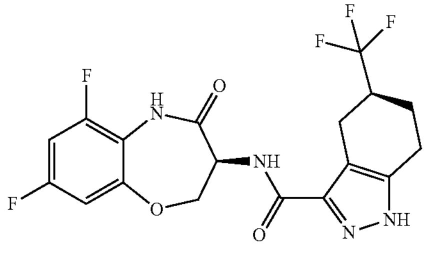 [SMILES: O=C(N[C@H]1COc2cc(F)cc(F)c2NC1=O)c1n[nH]c2c1C[C@@H](C(F)(F)F)CC2]

(S)—N—((S)-6,8-difluoro-4-oxo-2,3,4,5-tetrahydrobenzo[b][1,4]oxazepin-3-yl)-5-(trifluoro methyl)-4,5,6,7-tetrahydro-1H-indazole-3-carboxamide Method B (20 mg, 29% yield)

$^1$H NMR (400 MHz, DMSO-$d_6$) δ 13.02 (s, 1H), 10.03 (s, 1H), 8.03 (d, J=7.6 Hz, 1H), 7.31-7.16 (m, 1H), 7.12-6.96 (m, 1H), 4.95-4.81 (m, 1H), 4.69-4.56 (m, 1H), 4.56-4.44 (m, 1H), 3.10-2.95 (m, 1H), 2.87-2.58 (m, 3H), 2.17-2.03 (m, 1H), 1.72-1.55 (m, 1H). LC-MS $R_T$=5.03 min, m/z=434.1 $(M+H)^+$.

LCMS (2 to 98% acetonitrile in water+0.1% formic acid over 10 mins) retention time 5.03 min, ESI+ found [M+H]=434.1.

Example 87

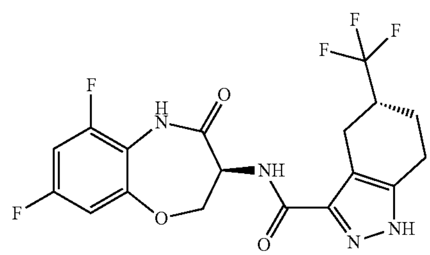 [SMILES: O=C(N[C@H]1COc2cc(F)cc(F)c2NC1=O)c1n[nH]c2c1C[C@H](C(F)(F)F)CC2]

(R)—N—((S)-6,8-difluoro-4-oxo-2,3,4,5-tetrahydrobenzo[b][1,4]oxazepin-3-yl)-5-(trifluoro methyl)-4,5,6,7-tetrahydro-1H-indazole-3-carboxamide Method B (12 mg, 17% yield)

$^1$H NMR (400 MHz, DMSO-$d_6$) δ 13.02 (s, 1H), 10.03 (s, 1H), 8.02 (d, J=7.7 Hz, 1H), 7.49-7.12 (m, 1H), 7.12-6.87 (m, 1H), 5.06-4.81 (m, 1H), 4.67-4.55 (m, 1H), 4.55-4.45 (m, 1H), 3.08-2.95 (m, 1H), 2.87-2.59 (m, 3H), 2.20-2.02 (m, 1H), 1.76-1.56 (m, 1H). LC-MS $R_T$=5.01 min, m/z=434.1 $(M+H)^+$.

LCMS (2 to 98% acetonitrile in water+0.1% formic acid over 10 mins) retention time 5.01 min, ESI+ found [M+H]=434.1.

Example 88

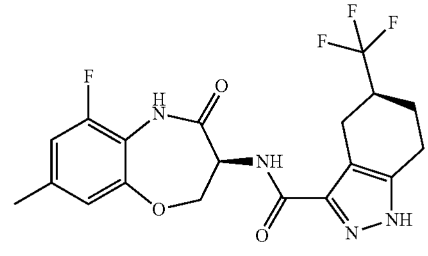 [SMILES: Cc1cc(F)c2c(c1)OC[C@H](NC(=O)c1n[nH]c3c1C[C@@H](C(F)(F)F)CC3)C(=O)N2]

(S)—N—((S)-6-fluoro-8-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide Method B (29 mg, 42% yield)

$^1$H NMR (400 MHz, DMSO-$d_6$) δ 13.01 (s, 1H), 9.95 (s, 1H), 8.00 (d, J=7.8 Hz, 1H), 7.05-6.93 (m, 1H), 6.93-6.83 (m, 1H), 4.90-4.77 (m, 1H), 4.60-4.51 (m, 1H), 4.49-4.41 (m, 1H), 3.06-2.95 (m, 1H), 2.85-2.74 (m, 1H), 2.74-2.58 (m, 2H), 2.47-2.42 (m, 1H), 2.30 (s, 3H), 2.14-2.09 (m, 1H), 1.70-1.56 (m, 1H). LC-MS $R_T$=5.20 min, m/z=427.1 $(M+H)^+$.

LCMS (2 to 98% acetonitrile in water+0.1% formic acid over 10 mins) retention time 5.20 min, ESI+ found [M+H]=427.1.

Example 89

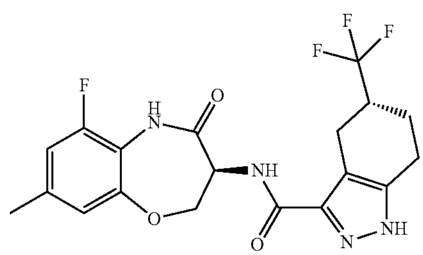 [SMILES: Cc1cc(F)c2c(c1)OC[C@H](NC(=O)c1n[nH]c3c1C[C@H](C(F)(F)F)CC3)C(=O)N2]

(R)—N—((S)-6-fluoro-8-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide Method B (19 mg, 27% yield)

$^1$H NMR (400 MHz, DMSO-$d_6$) δ 13.01 (s, 1H), 9.95 (s, 1H), 7.99 (d, J=7.8 Hz, 1H), 7.07-6.92 (m, 1H), 6.92-6.80 (m, 1H), 4.97-4.74 (m, 1H), 4.63-4.49 (m, 1H), 4.49-4.37 (m, 1H), 3.07-2.94 (m, 1H), 2.87-2.74 (m, 1H), 2.74-2.59 (m, 2H), 2.48-2.42 (m, 1H), 2.30 (s, 3H), 2.18-2.02 (m, 1H), 1.72-1.55 (m, 1H). LC-MS $R_T$=5.19 min, m/z=427.1 $(M+H)^+$.

LCMS (2 to 98% acetonitrile in water+0.1% formic acid over 10 mins) retention time 5.19 min, ESI+ found [M+H]=427.1.

Example 90

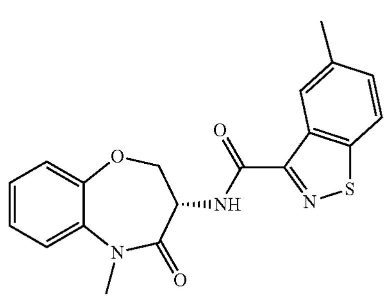 [SMILES: Cc1ccc2snc(C(=O)N[C@H]3COc4ccccc4N(C)C3=O)c2c1]

(S)-5-methyl-N-(5-methyl-4-oxo-2,3,4,5-tetrahydrobenzo[b][1,4]oxazepin-3-yl)benzo[d]isothiazole-3-carboxamide Method B (24 mg, 24% yield)

$^1$H NMR (400 MHz, DMSO-$d_6$) δ 8.89 (d, J=8.0 Hz, 1H), 8.48-8.40 (m, 1H), 8.23-8.14 (m, 1H), 7.59-7.46 (m, 2H), 7.40-7.20 (m, 3H), 4.99-4.86 (m, 1H), 4.72-4.62 (m, 1H), 4.54-4.42 (m, 1H), 3.34 (s, 3H), 2.46 (s, 3H). LC-MS $R_T$=5.97 min, m/z=368.1 $(M+H)^+$.

LCMS (2 to 98% acetonitrile in water+0.1% formic acid over 10 mins) retention time 5.97 min, ESI+ found [M+H]=368.1.

Example 91

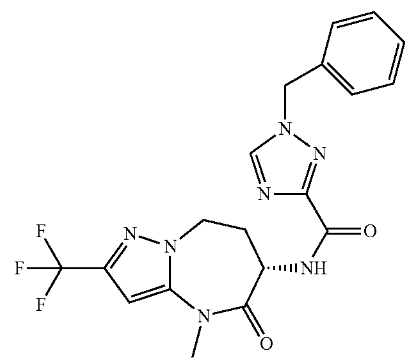

(S)-1-benzyl-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide Method B (35 mg, 27% yield)

$^1$H NMR (400 MHz, DMSO-$d_6$) δ 8.82 (s, 1H), 8.63 (d, J=7.6 Hz, 1H), 7.46-7.17 (m, 5H), 6.93 (s, 1H), 5.49 (s, 2H), 4.52-4.43 (m, 1H), 4.39-4.27 (m, 2H), 3.27 (s, 3H), 2.70-2.58 (m, 1H), 2.47-2.42 (m, 1H). LC-MS $R_T$=4.63 min, m/z=434.1 $(M+H)^+$.

LCMS (2 to 98% acetonitrile in water+0.1% formic acid over 10 mins) retention time 4.63 min, ESI+ found [M+H]=434.1.

Example 92

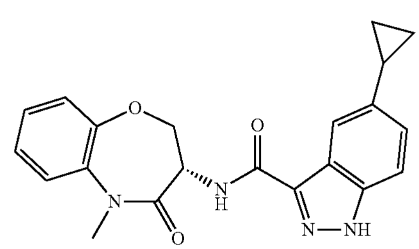 [SMILES: CN1C(=O)[C@@H](NC(=O)c2n[nH]c3ccc(C4CC4)cc23)COc2ccccc21]

(S)-5-cyclopropyl-N-(5-methyl-4-oxo-2,3,4,5-tetrahydrobenzo[b][1,4]oxazepin-3-yl)-1H-indazole-3-carboxamide Method B (13.8 mg, 25% yield)

$^{1}H$ NMR (400 MHz, DMSO-$d_6$) δ 13.58 (s, 1H), 8.34 (d, J=8.0 Hz, 1H), 7.78-7.70 (m, 1H), 7.58-7.46 (m, 2H), 7.39-7.22 (m, 3H), 7.16 (dd, J=8.7, 1.7 Hz, 1H), 5.03-4.83 (m, 1H), 4.67-4.57 (m, 1H), 4.52-4.42 (m, 1H), 2.10-1.96 (m, 1H), 1.00-0.91 (m, 2H), 0.68-0.59 (m, 2H). LC-MS $R_T$=5.36 min, m/z=377.1 $(M+H)^+$.

LCMS (2 to 98% acetonitrile in water+0.1% formic acid over 10 mins) retention time 5.36 min, ESI+ found [M+H]=377.1.

Example 93: General for all 8 Membered Lactams

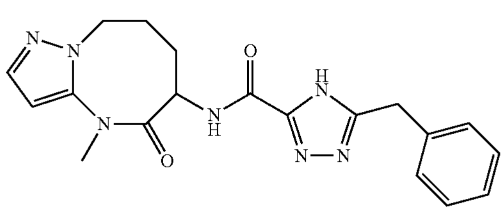 [SMILES: CN1C(=O)C(NC(=O)c2nnc(Cc3ccccc3)[nH]2)CCCn2nccc21]

5-benzyl-N-(4-methyl-5-oxo-4,5,6,7,8,9-hexahydropyrazolo[1,5-a][1,3]diazocin-6-yl)-4H-1,2,4-triazole-3-carboxamide All NMR spectra were recorded in DMSO-$d_6$/$CD_3OD$/$CDCl_3$ solution in 5 mm o.d. tubes [Wilmad NMR tubes (Sigma-Aldrich), 5 mm Thin Wall, 7" Length] at 300.0 K and were collected on Bruker Avance NMRS-400 at 400 MHz for $^{1}H$. The chemical shifts (δ) are relative to $CDCl_3$ ($CDCl_3$=7.26 ppm), $d_6$-DMSO ($d_6$-DMSO=2.5 ppm), $CD_3OD$ ($CD_3OD$=3.3 ppm) and expressed in ppm. The chemical shifts in $CDCl_3$, $d_6$-DMSO and $CD_3OD$ are relative to tetramethylsilane (TMS, =0.00 ppm) and expressed in ppm.

All LC-MS were done using following methods;

Column—ZORBAX EXT (4.6×50 mm, 5u), (mobile phase: from 90% [10 mM NH4OAc in water] and 10% [CH3CN] to 70% [10 mM NH4OAc in water] and 30% [CH3CN] in 1.5 min, further to 10% [10 mM NH4OAc in water] and 90% [CH3CN] in 3.0 min, held this mobile phase composition up to 4.0 min and finally back to initial condition in 5.0 min). Flow=1.2 ml/min.

Column—Restek Ultra AQ C18 (30×2.1 mm, 3u), (mobile phase: 98% [0.05% HCOOH in water] and 2% [CH3CN] held for 0.75 min, then to 90% [0.05% HCOOH in water] and 10% [CH3CN] in 1.0 min, further to 2% [0.05% HCOOH in water] and 98% [CH3CN] in 2.0 min, held this mobile phase composition up to 2.25 min and finally back to initial condition in 3.0 min). Flow=1.5 ml/min

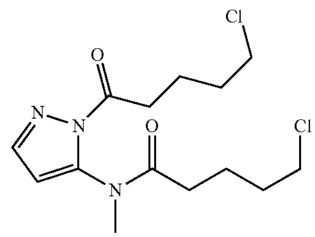 [SMILES: CN(C(=O)CCCCCl)c1ccnn1C(=O)CCCCCl]

Step 1: 5-chloro-N-(1-(5-chloropentanoyl)-1H-pyrazol-5-yl)-N-methylpentanamide

To a stirred solution of N,5-dimethyl-1H-pyrazol-3-amine (0.500 g, 5.15 mmol) in anhydrous dichloromethane (25 mL) cooled to 0° C. was added N,N-diisopropylethylamine (2.0 mL, 15.4 mmol) followed by dropwise addition of 5-chloropentanoyl chloride (1.65 mL, 12.9 mmol) under nitrogen. To the resulting mixture was added 4-dimethylaminopyridine (33.0 mg, 0.515 mmol), and the reaction mixture was stirred at RT for 6 h. The mixture was diluted with dichloromethane (2×125 mL), and washed with saturated sodium bicarbonate (1×100 mL), water (1×100 mL), brine (1×100 mL), dried over sodium sulphate and concentrated to dryness in vacuo. The residue was purified by column chromatography (silica gel, 100-200 mesh, 20 to 30% ethyl acetate in hexane) to afford 5-chloro-N-(1-(5-chloropentanoyl)-1H-pyrazol-5-yl)-N-methylpentanamide (1.3 g, 76%) as a yellow oil: $^{1}H$ NMR (400 MHz, DMSO-$d_6$) D 8.36 (s, 1H); 6.8 (br. s, 1H); 3.69-3.64 (m, 5H); 3.31 (s, 3H); 3.10-3.07 (m, 2H); 2.55 (br. s, 1H); 1.80-1.62 (m, 8H). LCMS $R_T$=3.46 min, m/z=334 $(M+H)^+$.

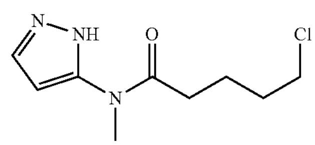

Step 2: 5-chloro-N-methyl-N-(1H-pyrazol-5-yl)pentanamide

To a stirred solution of 5-chloro-N-(1-(5-chloropentanoyl)-1H-pyrazol-5-yl)-N-methylpentanamide (12.5 g, 37.4 mmol) in ethanol (70 mL) was added sodium hydroxide (1.5 g, 37.4 mmol) in water (37 mL) and the mixture was left to stand at RT for 5 min. The reaction mixture was concentrated to dryness in vacuo, diluted with water (200 mL) and extracted with ethyl acetate (3×150 mL). The filtrate was washed with water, brine, dried over sodium sulphate and concentrated to dryness in vacuo. The residue was purified by column chromatography (silica gel, 100-200 mesh, 50 to 60% ethyl acetate in hexane) to afford 5-chloro-N-methyl-N-(1H-pyrazol-5-yl)pentanamide (6 g, 74%) as a yellow sticky solid: $^{1}H$ NMR (400 MHz, DMSO-$d_6$) δ 12.76 (br. s, 1H); 7.75 (s, 1H); 6.22 (s, 1H); 3.55 (br. s, 2H); 3.09 (s, 3H); 2.17 (br. s, 2H); 1.60 (br. s, 4H). LCMS $R_T$=2.45 min, m/z=216.3 $(M+H)^+$.

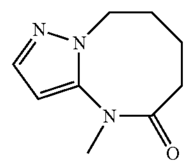

Step 3: 4-methyl-6,7,8,9-tetrahydropyrazolo[1,5-a][1,3]diazocin-5(4H)-one

To a solution of 5-chloro-N-methyl-N-(1H-pyrazol-5-yl) pentanamide (5.0 g, 23.2 mmol) in anhydrous acetonitrile (200 mL) was added cesium carbonate (15.11 g, 46.4 mmol) and stirred at RT for 16 h. The reaction mixture was concentrated to dryness in vacuo and the residue was diluted with ethyl acetate (200 mL) and washed with water (2×200 mL), brine (1×100 mL), dried over sodium sulphate and concentrated to dryness in vacuo. The residue was purified by column chromatography (silica gel, 100-200 mesh, 40 to 50% ethyl acetate in hexane) to afford 4-methyl-6,7,8,9-tetrahydropyrazolo[1,5-a][1,3]diazocin-5(4H)-one (3.4 g, 82%) as a yellow solid: 1H NMR (400 MHz, DMSO-$d_6$) D 7.49 (s, 1H); 6.28 (s, 1H); 4.33-4.28 (m, 1H); 3.78-3.71 (m, 1H); 3.15 (s, 3H); 2.30-2.24 (m, 1H); 1.93-1.88 (m, 2H); 1.67-1.57 (m, 2H); 1.38-1.42 (m, 1H). LCMS $R_T$=1.64 min, m/z=180 $(M+H)^+$.

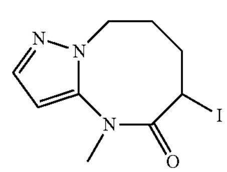

Step 4: 6-iodo-4-methyl-6,7,8,9-tetrahydropyrazolo[1,5-a][1,3]diazocin-5(4H)-one To a solution of 5-chloro-N-methyl-N-(1H-pyrazol-5-yl) pentanamide (3.4 g, 19.0 mmol) in dry dichloromethane (100 mL) under nitrogen cooled to ~−10° C. in a salt/ice bath was added N,N,N',N'-tetramethylethylenediamine (17.1 mL, 113.8 mmol) followed by iodotrimethylsilane (15.8 mL, 113.8 mmol). The resulting solution was stirred in the salt/ice bath for 1.5 h, after which time was added iodine (14.44 g, 56.9 mmol). The mixture continued to stir in the salt/ice bath for another 2 h, after which time the reaction mixture was diluted with water (100 mL). The layers were separated, and the aqueous was extracted with ethyl acetate (2×100 mL). The combined organic extracts were washed with sodium bisulfite (1×150 mL), water (1×100 mL), brine (1×100 mL) and dried over anhydrous sodium sulfate and concentrated to dryness in vacuo to afford 6-iodo-4-methyl-6,7,8,9-tetrahydropyrazolo[1,5-a][1,3]diazocin-5(4H)-one (5.5 g, 95%) as a light yellow oil, used as is in the next step: $^1$H NMR (400 MHz, DMSO-$d_6$) Q 7.54 (s, 1H); 6.39 (s, 1H); 4.33-4.26 (m, 1H); 4.04-4.00 (m, 1H); 3.78-3.71 (m, 1H); 3.17 (s, 3H); 2.32-2.27 (m, 2H); 1.93-1.61 (m, 2H). LCMS $R_T$=2.63 min, m/z=306 $(M+H)^+$.

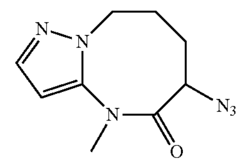 [SMILES: CN1C(=O)C(N=[N+]=[N-])CCCn2nccc21]

Step 5: 6-azido-4-methyl-6,7,8,9-tetrahydropyrazolo[1,5-a][1,3]diazocin-5(4H)-one To a solution of 6-iodo-4-methyl-6,7,8,9-tetrahydropyrazolo[1,5-a][1,3]diazocin-5(4H)-one (1.3 g, 4.26 mmol) in N,N-dimethylformamide (15 mL) was added sodium azide (1.10 g, 17.0 mmol), and the reaction mixture was stirred at RT for 17 h. The reaction mixture was diluted with ethyl acetate (200 mL), washed with water (3×100 mL), brine (1×100 mL), dried over sodium sulfate and concentrated to dryness in vacuo. The resulting residue was purified by column chromatography (silica gel, 100-200 mesh, 30 to 50% ethyl acetate in heptane) affording azido-6-azido-4-methyl-6,7,8,9-tetrahydropyrazolo[1,5-a][1,3]diazocin-5(4H)-one (0.500 g, 53%) as a yellow solid (0.606 g, 96%): $^1$H NMR (400 MHz, DMSO-$d_6$) δ 7.53 (s, 1H); 6.37 (s, 1H); 4.34-4.29 (m, 1H); 3.87-3.80 (m, 1H); 3.18 (s, 3H); 3.17-3.15 (m, 1H); 2.05-1.95 (m, 3H); 1.68-1.57 (m, 1H). LCMS $R_T$=2.72 min, m/z=221.2 $(M+H)^+$.

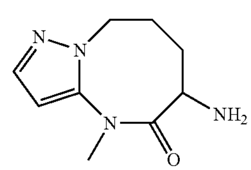

Step 6: 6-amino-4-methyl-6,7,8,9-tetrahydropyrazolo[1,5-a][1,3]diazocin-5(4H)-one To a solution of 6-azido-4-methyl-6,7,8,9-tetrahydropyrazolo[1,5-a][1,3]diazocin-5(4H)-one (2.2 g, 9.98 mmol) in methanol (50 mL) was added 10% palladium on carbon (1.0 g) under argon. The reaction mixture was stirred under hydrogen (balloon pressure) at RT for 17 h. The reaction mixture was filtered through Celite, the cake washed with 5% methanol in dichloromethane and the combined filtrate was concentrated to dryness in vacuo affording 6-amino-4-methyl-6,7,8,9-tetrahydropyrazolo[1,5-a][1,3]diazocin-5(4H)-one (1.65 g, 85%) as a vicious brown liquid used as is in the next step: $^1$H NMR (400 MHz, DMSO-$d_6$) D 7.51 (s, 1H); 6.29 (s, 1H); 4.29-4.24 (m, 1H); 3.78-3.71 (m, 1H); 3.17 (s, 3H); 2.74-2.70 (m, 1H); 1.96-1.88 (m, 3H); 1.66-1.60 (m, 3H). LCMS $R_T$=1.42 min, m/z=195.2 $(M+H)^+$.

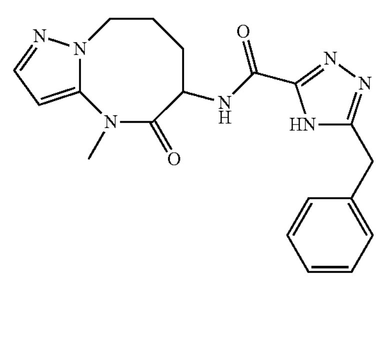 [SMILES: CN1C(=O)C(NC(=O)c2nnc(Cc3ccccc3)[nH]2)CCCn2nccc21]

5-benzyl-N-(4-methyl-5-oxo-4,5,6,7,8,9-hexahydro-pyrazolo[1,5-a][1,3]diazocin-6-yl)-4H-1,2,4-triazole-3-carboxamide Method B (58 mg, 75% yield)

$^1$H NMR (400 MHz, DMSO-$d_6$) δ 8.27 (s, 1H), 7.56 (d, J=2.0 Hz, 1H), 7.36-7.28 (m, 2H), 7.29-7.21 (m, 3H), 6.36 (d, J=2.0 Hz, 1H), 4.42-4.29 (m, 1H), 4.09 (s, 2H), 3.97-3.80 (m, 2H), 3.21 (s, 3H), 2.07-1.96 (m, 1H), 1.93-1.77 (m, 2H), 1.66-1.53 (m, 1H). LCMS $R_T$=3.61 min, m/z=380.2=(M+H)$^+$.

LCMS (2 to 98% acetonitrile in water+0.1% formic acid over 10 mins) retention time 3.61 min, ESI+ found [M+H]=380.2.

Example 94

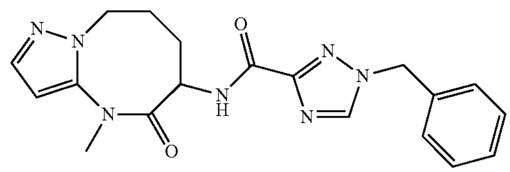 [SMILES: CN1C(=O)C(NC(=O)c2ncn(Cc3ccccc3)n2)CCCn2nccc21]

1-benzyl-N-(4-methyl-5-oxo-4,5,6,7,8,9-hexahydro-pyrazolo[1,5-a][1,3]diazocin-6-yl)-1H-1,2,4-triazole-3-carboxamide Method B (104 mg, 80% yield)

$^1$H NMR (400 MHz, DMSO-$d_6$) δ 8.80 (s, 1H), 8.24 (d, J=7.0 Hz, 1H), 7.56 (d, J=2.0 Hz, 1H), 7.39-7.27 (m, 5H), 6.36 (d, J=2.0 Hz, 1H), 5.47 (s, 2H), 4.42-4.28 (m, 1H), 3.98-3.77 (m, 2H), 3.21 (s, 3H), 2.08-1.95 (m, 1H), 1.92-1.76 (m, 2H), 1.67-1.54 (m, 1H). LCMS $R_T$=3.72 min, m/z=380.2=(M+H)$^+$.

LCMS (2 to 98% acetonitrile in water+0.1% formic acid over 10 mins) retention time 3.72 min, ESI+ found (M+H]=380.2.

Example 95

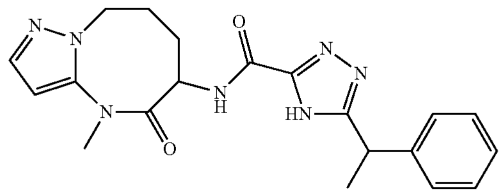 [SMILES: CC(c1ccccc1)c1nnc(C(=O)NC2CCCn3nccc3N(C)C2=O)[nH]1]

N-(4-methyl-5-oxo-4,5,6,7,8,9-hexahydropyrazolo[1,5-a][1,3]diazocin-6-yl)-5-(1-phenylethyl)-4H-1,2,4-triazole-3-carboxamide Method B (34 mg, 56% yield)

$^1$H NMR (400 MHz, DMSO-$d_6$) δ 8.31-8.20 (m, 1H), 7.59-7.54 (m, 1H), 7.36-7.17 (m, 6H), 6.41-6.32 (m, 1H), 4.47-4.24 (m, 2H), 4.02-3.76 (m, 2H), 3.22 (s, J=2.4 Hz, 3H), 2.05-1.97 (m, 1H), 1.92-1.76 (m, 2H), 1.64-1.58 (m, 4H). LCMS $R_T$=3.85 min, m/z=394.2=(M+H)$^+$.

LCMS (2 to 98% acetonitrile in water+0.1% formic acid over 10 mins) retention time 3.85 min, ESI+ found [M+H]=394.2.

Example 96

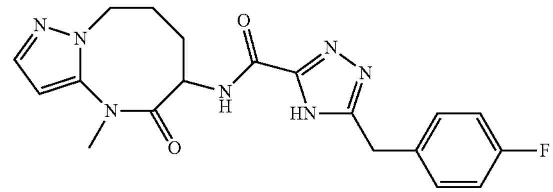 [SMILES: CN1C(=O)C(NC(=O)c2nnc(Cc3ccc(F)cc3)[nH]2)CCCn2nccc21]

5-(4-fluorobenzyl)-N-(4-methyl-5-oxo-4,5,6,7,8,9-hexahydropyrazolo[1,5-a][1,3]diazocin-6-yl)-4H-1,2,4-triazole-3-carboxamide Method B (24 mg, 40% yield)

$^1$H NMR (400 MHz, DMSO-$d_6$) δ 8.32-8.22 (m, 1H), 7.61-7.49 (m, 1H), 7.34-7.25 (m, 2H), 7.18-7.09 (m, 2H), 6.41-6.31 (m, 1H), 4.41-4.28 (m, 1H), 4.09 (s, 2H), 3.98-3.79 (m, 2H), 3.21 (s, 3H), 2.08-1.96 (m, 1H), 1.94-1.77 (m, 2H), 1.68-1.52 (m, 1H). LCMS $R_T$=3.72 min, m/z=398.1=(M+H)$^+$.

LCMS (2 to 98% acetonitrile in water+0.1% formic acid over 10 mins) retention time 3.72 min, ESI+ found [M+H]=398.1

Example 97

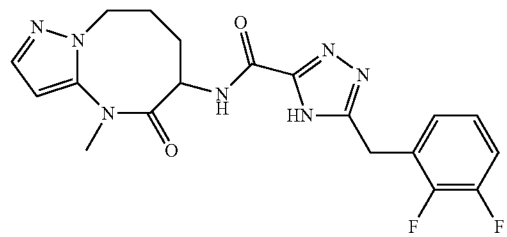 [SMILES: CN1C(=O)C(NC(=O)c2nnc(Cc3cccc(F)c3F)[nH]2)CCCn2nccc21]

5-(2,3-difluorobenzyl)-N-(4-methyl-5-oxo-4,5,6,7,8,9-hexahydropyrazolo[1,5-a][1,3]diazocin-6-yl)-4H-1,2,4-triazole-3-carboxamide Method B (41 mg, 60% yield)

$^1$H NMR (400 MHz, DMSO-$d_6$) δ 8.34-8.25 (m, 1H), 7.56 (d, J=2.0 Hz, 1H), 7.39-7.27 (m, 1H), 7.23-7.10 (m, 2H), 6.35 (d, J=2.0 Hz, 1H), 4.41-4.29 (m, 1H), 4.17 (s, 2H), 3.97-3.78 (m, 2H), 3.21 (s, 3H), 2.07-1.97 (m, 1H), 1.96-1.77 (m, 2H), 1.67-1.53 (m, 1H). LCMS $R_T$=3.81 min, m/z=4.16.2 (M+H)$^+$.

LCMS (2 to 98% acetonitrile in water+0.1% formic acid over 10 mins) retention time 3.81 min, ESI+ found [M+H]=416.2

Example 98

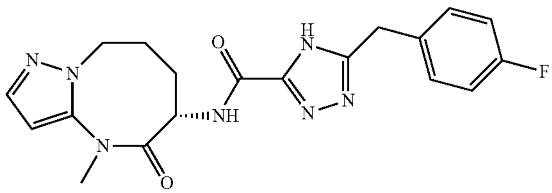 [SMILES: CN1C(=O)[C@@H](NC(=O)c2nnc(Cc3ccc(F)cc3)[nH]2)CCCn2nccc21]

(S)-5-(4-fluorobenzyl)-N-(4-methyl-5-oxo-5,6,7,8-tetrahydro-4H-pyrazolo[1,5-a][1,3]diazepin-6-yl)-4H-1,2,4-triazole-3-carboxamide Method B (55 mg, 94% yield)

$^1$H NMR (400 MHz, DMSO-$d_6$) δ 8.57-8.50 (m, 1H), 7.49 (d, J=2.0 Hz, 1H), 7.38-7.24 (m, 2H), 7.20-7.08 (m, 2H), 6.34 (d, J=2.1 Hz, 1H), 4.42-4.25 (m, 2H), 4.24-4.13 (m, 1H), 4.09 (s, 2H), 3.25 (s, 3H), 2.67-2.53 (m, 1H), 2.44-2.29 (m, 1H). LCMS $R_T$=3.63 min, m/z=384.1 $(M+H])^+$.

LCMS (2 to 98% acetonitrile in water+0.1% formic acid over 10 mins) retention time 3.63 min, ESI+ found [M+H]=384.1.

Example 99

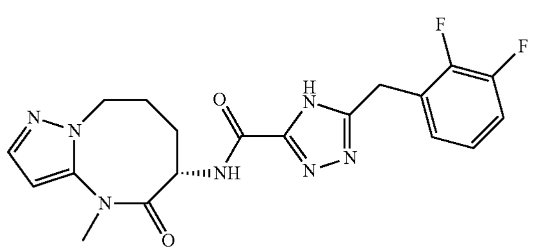 [SMILES: CN1C(=O)[C@@H](NC(=O)c2nnc(Cc3cccc(F)c3F)[nH]2)CCCn2nccc21]

(S)-5-(2,3-difluorobenzyl)-N-(4-methyl-5-oxo-5,6,7,8-tetrahydro-4H-pyrazolo[1,5-a][1,3]diazepin-6-yl)-4H-1,2,4-triazole-3-carboxamide Method B (42 mg, 80% yield)

$^1$H NMR (400 MHz, DMSO-$d_6$) δ 8.62-8.51 (m, 1H), 7.49 (d, J=2.0 Hz, 1H), 7.39-7.28 (m, 1H), 7.23-7.09 (m, 2H), 6.34 (d, J=2.0 Hz, 1H), 4.41-4.26 (m, 2H), 4.23-4.14 (m, 3H), 3.24 (s, 3H), 2.62-2.55 (m, 1H), 2.44-2.33 (m, 1H). LCMS $R_T$=3.71 min, m/z=402.1 $(M+H])^+$.

LCMS (2 to 98% acetonitrile in water+0.1% formic acid over 10 mins) retention time 3.71 min, ESI+ found [M+H]=402.1.

Example 100

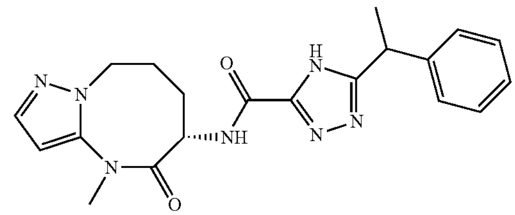 [SMILES: CC(c1ccccc1)c1nnc(C(=O)N[C@H]2CCCn3nccc3N(C)C2=O)[nH]1]

N—((S)-4-methyl-5-oxo-5,6,7,8-tetrahydro-4H-pyrazolo[1,5-a][1,3]diazepin-6-yl)-5-(1-phenylethyl)-4H-1,2,4-triazole-3-carboxamide Method B (54 mg, 74% yield)

$^1$H NMR (400 MHz, DMSO-$d_6$) δ 8.52 (s, 1H), 7.49 (d, J=2.0 Hz, 1H), 7.36-7.18 (m, 6H), 6.34 (d, J=2.0 Hz, 1H), 4.42-4.26 (m, 4H), 4.24-4.13 (m, 1H), 3.25 (s, 3H), 1.63 (d, J=7.3 Hz, 3H). LCMS $R_T$=3.75 min, m/z=380.2 $(M+H])^+$.

LCMS (2 to 98% acetonitrile in water+0.1% formic acid over 10 mins) retention time 3.75 min, ESI+ found [M+H]=380.2.

Example 101

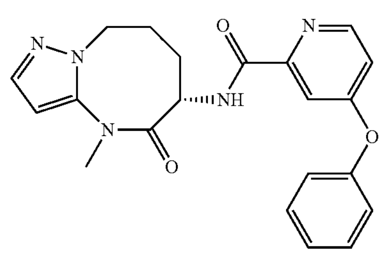 [SMILES: CN1C(=O)[C@@H](NC(=O)c2cc(Oc3ccccc3)ccn2)CCCn2nccc21]

(S)—N-(4-methyl-5-oxo-5,6,7,8-tetrahydro-4H-pyrazolo[1,5-a][1,3]diazepin-6-yl)-4-phenoxypicolinamide Method B (22 mg, 35% yield)

$^1$H NMR (400 MHz, DMSO-$d_6$) δ 8.92 (d, J=7.8 Hz, 1H), 8.62-8.54 (m, 1H), 7.57-7.45 (m, 3H), 7.39-7.30 (m, 2H), 7.27-7.17 (m, 3H), 6.33 (d, J=2.0 Hz, 1H), 4.44-4.14 (m, 3H), 3.25 (s, 3H), 2.74-2.61 (m, 1H), 2.41-2.27 (m, 1H). LCMS $R_T$=4.59 min, m/z=378.2 $(M+H])^+$.

LCMS (2 to 98% acetonitrile in water+0.1% formic acid over 10 mins) retention time 4.59 min, ESI+ found [M+H]=378.2.

Example 102

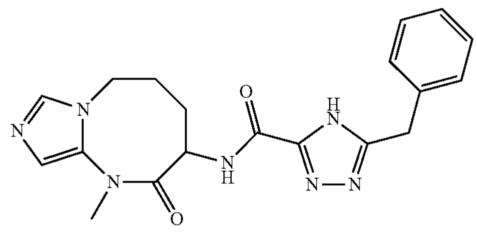 [SMILES: CN1C(=O)C(NC(=O)c2nnc(Cc3ccccc3)[nH]2)CCCn2cncc21]

5-benzyl-N-(1-methyl-2-oxo-1,2,3,4,5,6-hexahydro-imidazo[1,5-a][1,3]diazocin-3-yl)-4H-1,2,4-triazole-3-carboxamide

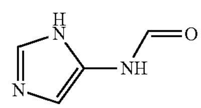

Step 1: N-(1H-imidazol-5-yl)formamide

A solution of 3H-imidazol-4-ylamine (7.9 g, 96.2 mmol) in formic acid (32 ml) was heated at 110° C. for 2 h in a sealed vessel. Reaction mass was cooled to RT and concentrated to dryness in vacuo. The residue was co-distillated with methanol (3×60 ml) affording N-(3H-imidazol-4-yl)-formamide (9.0 g, 84.18%) as white solid: $^1$H NMR (400 MHz, DMSO-$d_6$) δ 12.38 (s, 1H), 10.51 (s, 1H), 8.16 (s, 1H), 7.61 (d, J=8.6 Hz, 1H), 6.47 (s, 1H).

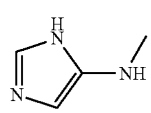

Step 2: N-methyl-1H-imidazol-5-amine

To a stirred solution of N-(3H-imidazol-4-yl)-formamide (4.5 g, 40.5 mmol) in tetrahydrofuran (170 mL) at ice cooled condition was added lithium aluminum hydride (2M solution in tetrahydrofuran, 61 mL, 121.6 mmol) very slowly under nitrogen and the reaction mixture was allowed to warm at RT gradually and stirred for 6 h. The reaction was quenched with solid sodium sulfate and stirred at RT for 30 min. The reaction mixture was diluted with ethyl acetate and filtered through Celite bed and the filtrate was concentrated to dryness in vacuo to afford crude N-methyl-1H-imidazol-5-amine (3.17 g, 81%) as colorless liquid, use as is in the next step.

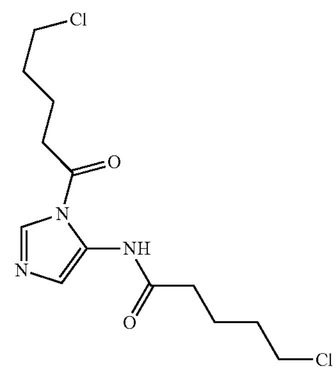 [SMILES: O=C(CCCCCl)Nc1cncn1C(=O)CCCCCl]

Step 3: 5-chloro-N-(1-(5-chloropentanoyl)-1H-imidazol-5-yl)pentanamide

To a stirred solution of N-methyl-1H-imidazol-5-amine (6.1 g, 62.1 mmol) in anhydrous dichloromethane (300 mL) cooled to 0° C. was added N,N-diisopropylethylamine (32.8 mL, 188.4 mmol) followed by dropwise addition of 5-chloropentanoyl chloride (19.5 mL, 150.7 mmol) under nitrogen. To the resulting mixture was added 4-dimethylaminopyridine (0.767 mg, 6.28 mmol), and the reaction mixture was stirred at RT for 16 h. The reaction mixture was concentrated to dryness in vacuo and the resulting residue was purified by column chromatography (silica gel, 100-200 mesh, 20 to 25% ethyl acetate in hexane) affording 5-chloro-N-(1-(5-chloropentanoyl)-1H-imidazol-5-yl)pentanamide (17.5 g, 83%) as a yellow oil: LCMS $R_T$=1.67 min, m/z=334.3 $[M]^+$, 336.3 $[M+2]^+$.

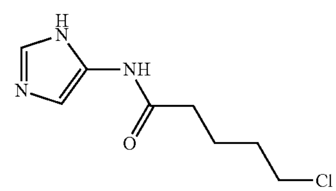 [SMILES: O=C(CCCCCl)Nc1cnc[nH]1]

Step 4: 5-chloro-N-(1H-imidazol-5-yl)pentanamide

To a stirred solution of 5-chloro-N-(1-(5-chloropentanoyl)-1H-imidazol-5-yl)pentanamide (17.5 g, 52.4 mmol) in ethanol (105 mL) was added sodium hydroxide (2.1 g, 52.4 mmol) in water (52.5 mL) and the mixture was left to stand at RT for 5 min. The reaction mixture was concentrated to dryness in vacuo, diluted with water (200 mL) and extracted with ethyl acetate (3×150 mL). The filtrate was washed with water, brine, dried over sodium sulphate and concentrated to dryness in vacuo. The residue was purified by column chromatography (silica gel, 100-200 mesh, 45 to 50% ethyl acetate in hexane) to afford 5-chloro-N-(1H-imidazol-5-yl)pentanamide (8.8 g, 78%) as a yellow oil: $^1$H NMR (400 MHz, DMSO-$d_6$) δ 12.77 (s, 1H), 7.75 (s, 1H), 6.22 (s, 1H), 3.56 (br. s, 2H), 3.09 (s, 3H), 2.17 (s, 1H), 1.99 (br. s, 2H), 1.60 (br. s, 4H). LCMS $R_T$=2.57 min, m/z=216.1 $(M+H)^+$.

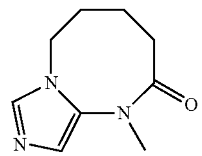

Step 5: 1-methyl-3,4,5,6-tetrahydroimidazo[1,5-a][1,3]diazocin-2(1H)-one

To a solution of 5-chloro-N-(1H-imidazol-5-yl)pentanamide (8.8 g, 40.8 mmol) in anhydrous acetonitrile (350 mL) was added cesium carbonate (26.6 g, 81.6 mmol) and stirred at RT for 16 h. The reaction mixture was concentrated to dryness in vacuo and the residue was purified by column chromatography (silica gel, 100-200 mesh, 45 to 50% ethyl acetate in hexane) to afford 1-methyl-3,4,5,6-tetrahydroimidazo[1,5-a][1,3]diazocin-2(1H)-one (5.6 g, 77%) as yellow solid: $^1$H NMR (400 MHz, DMSO-$d_6$) δ 7.49 (s, 1H), 6.28 (s, 1H), 4.30 (br. d, J=14.09 Hz), 3.75 (t, J=12.1 Hz, 1H), 3.15 (s, 3H), 2.29-2.25 (m, 1H), 1.93-1.89 (m, 2H), 1.67-1.55 (m, 2H), 1.44-1.38 (m, 1H). LCMS $R_T$=1.90 min, m/z=180.2 (M+H)$^+$.

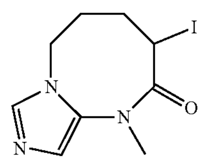

Step 6: 3-iodo-1-methyl-3,4,5,6-tetrahydroimidazo[1,5-a][1,3]diazocin-2(1H)-one

To a solution of 1-methyl-3,4,5,6-tetrahydroimidazo[1,5-a][1,3]diazocin-2(1H)-one (0.730 mg, 4.1 mmol) in dry dichloromethane (65 mL) under nitrogen cooled to ~−10° C. in a salt/ice bath was added N,N,N',N'-tetramethylethylenediamine (6.5 mL, 24.4 mmol) followed by iodotrimethylsilane (3.5 mL, 24.4 mmol). The resulting solution was stirred in the salt/ice bath for 1.5 h, after which time was added iodine (3.1 g, 12.2 mmol). The mixture continued to stir in the salt/ice bath for another 2 h, after which time the reaction mixture was diluted with water (100 mL). The layers were separated, and the aqueous was extracted with ethyl acetate (2×100 mL). The combined organic extracts were washed with sodium bisulfite (1×150 mL), water (1×100 mL), brine (1×100 mL) and dried over anhydrous sodium sulfate and concentrated to dryness in vacuo to afford 3-iodo-1-methyl-3,4,5,6-tetrahydroimidazo[1,5-a][1,3]diazocin-2(1H)-one (1.15 g, 93% crude yield) as a light yellow solid, used as is in the next step: $^1$H NMR (400 MHz, DMSO-$d_6$) δ 7.54 (s, 1H), 6.42-6.39 (s, 1H), 4.29 (dd, J=14.6, 3.9 Hz, 1H), 4.06-3.98 (m, 1H), 3.78-3.71 (m, 2H), 3.16 (s, 3H), 2.31-2.26 (s, 2H), 1.84-1.81 (m, 1H), 1.72-1.61 (m, 1H). LCMS $R_T$=2.54 min, m/z=306.1 (M+H)$^+$.

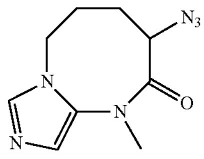 [SMILES: CN1C(=O)C(N=[N+]=[N-])CCCn2cncc21]

Step 7: 3-azido-1-methyl-3,4,5,6-tetrahydroimidazo[1,5-a][1,3]diazocin-2(1H)-one To a solution of 3-iodo-1-methyl-3,4,5,6-tetrahydroimidazo[1,5-a][1,3]diazocin-2(1H)-one (1.1 g, 3.61 mmoL crude) in N,N-dimethylformamide (15 mL) was added sodium azide (0.94 g, 14.4 mmol), and the reaction mixture was stirred at RT for 17 h. The reaction mixture was diluted with ethyl acetate (200 mL), washed with water (3×100 mL), brine (1×100 mL), dried over sodium sulfate and concentrated to dryness in vacuo. The resulting residue was purified by column chromatography (silica gel, 100-200 mesh, 25 to 30% ethyl acetate in hexane) affording 3-azido-1-methyl-3,4,5,6-tetrahydroimidazo[1,5-a][1,3]diazocin-2(1H)-one (0.600 g, 76%) as a yellow solid: $^1$H NMR (400 MHz, DMSO-$d_6$) δ 7.53 (s, 1H), 6.38 (s, 1H), 4.32 (d, J=14.7 Hz, 1H), 3.84 (t, J=12.2 Hz, 1H), 3.22 (s, 3H), 3.21-3.17 (m, 1H), 2.05-1.98 (m, 3H), 1.26-1.23 (m, 1H). LCMS $R_T$=1.33 min, m/z=221.3 (M+H)$^+$.

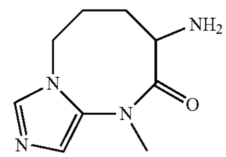

Step 8: 3-amino-1-methyl-3,4,5,6-tetrahydroimidazo[1,5-a][1,3]diazocin-2(1H)-one To a solution of 3-azido-1-methyl-3,4,5,6-tetrahydroimidazo[1,5-a][1,3]diazocin-2(1H)-one (0.400 mg, 1.82 mmol) in methanol (12 mL) was added 10% palladium on carbon (0.200 g) under argon. The reaction mixture was stirred under hydrogen (balloon pressure) at RT for 3 h. The reaction mixture was filtered through Celite, the cake washed with methanol and the combined filtrate was concentrated to dryness in vacuo affording 3-amino-1-methyl-3,4,5,6-tetrahydroimidazo[1,5-a][1,3]diazocin-2(1H)-one (0.27 mg, 77%) as a light yellow liquid used as is in the next step: $^1$H NMR (400 MHz, DMSO-$d_6$) δ 7.51 (s, 1H), 6.30 (s, 1H), 4.27 (dd, J=14.4, 5.3 Hz, 1H), 3.75 (t, J=11.3 Hz, 1H), 3.17 (s, 3H), 2.73-2.67 (m, 1H), 1.99-1.87 (m, 2H), 1.661.47 (m, 3H). LCMS $R_T$=3.64 min, m/z=195.1 (M+H)$^+$.

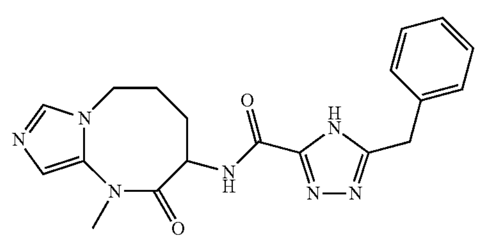 [SMILES: CN1C(=O)C(NC(=O)c2nnc(Cc3ccccc3)[nH]2)CCCn2cncc21]

Step 9: 5-benzyl-N-(1-methyl-2-oxo-1,2,3,4,5,6-hexahydroimidazo[1,5-a][1,3]diazocin-3-yl)-4H-1,2,4-triazole-3-carboxamide Method B (19.6 mg, 25% yield)

$^1$H NMR (400 MHz, DMSO-$d_6$) δ 8.31-8.21 (m, 1H), 7.56 (d, J=2.0 Hz, 1H), 7.37-7.18 (m, 5H), 6.59 (s, OH), 6.36

(d, J=2.0 Hz, 1H), 4.41-4.29 (m, 1H), 4.09 (s, 2H), 3.98-3.76 (m, 2H), 3.21 (s, 3H), 2.06-1.98 (m, 1H), 1.93-1.79 (m, 2H), 1.68-1.52 (m, 1H). LCMS $R_T$=3.46 min, m/z=380.2 $(M+H)^+$.

LCMS (2 to 98% acetonitrile in water+0.1% formic acid over 10 mins) retention time 3.46 min, ESI+ found [M+H]=380.2.

Example 103

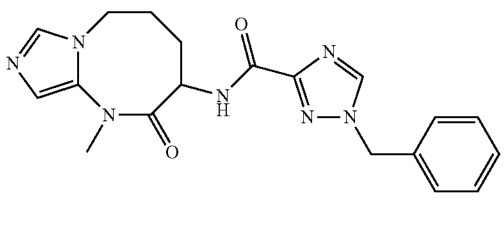 [SMILES: CN1C(=O)C(NC(=O)c2ncn(Cc3ccccc3)n2)CCCn2cncc21]

1-benzyl-N-(1-methyl-2-oxo-1,2,3,4,5,6-hexahydroimidazo[1,5-a][1,3]diazocin-3-yl)-1H-1,2,4-triazole-3-carboxamide Method B (44 mg, 56% yield)

$^1$H NMR (400 MHz, DMSO-$d_6$) δ 8.80 (s, 1H), 8.24 (d, J=7.1 Hz, 1H), 7.56 (d, J=2.0 Hz, 1H), 7.42-7.26 (m, 6H), 6.36 (d, J=2.0 Hz, 1H), 5.47 (s, 2H), 4.42-4.29 (m, 1H), 3.97-3.76 (m, 2H), 3.21 (s, 3H), 2.07-1.97 (m, 1H), 1.92-1.77 (m, 2H), 1.68-1.53 (m, 1H). LCMS $R_T$=3.55 min, m/z=380.2 $(M+H)^+$.

LCMS (2 to 98% acetonitrile in water+0.1% formic acid over 10 mins) retention time 3.55 min, ESI+ found [M+H]=380.2.

Example 104

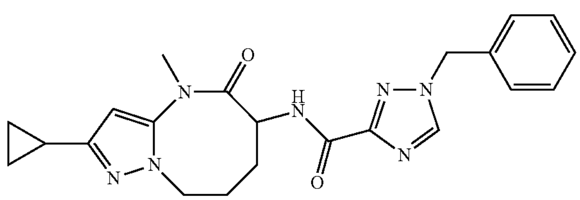 [SMILES: CN1C(=O)C(NC(=O)c2ncn(Cc3ccccc3)n2)CCCn2nc(C3CC3)cc21]

1-benzyl-N-(2-cyclopropyl-4-methyl-5-oxo-4,5,6,7,8,9-hexahydropyrazolo[1,5-a][1,3]diazocin-6-yl)-1H-1,2,4-triazole-3-carboxamide

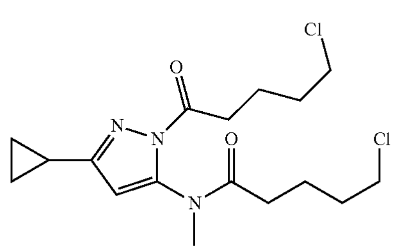 [SMILES: CN(C(=O)CCCCCl)c1cc(C2CC2)nn1C(=O)CCCCCl]

Step 1: 5-chloro-N-(1-(5-chloropentanoyl)-3-cyclopropyl-1H-pyrazol-5-yl)-N-methylpentanamide To a stirred solution of N,5-dimethyl-1H-pyrazol-3-amine (6 g, 43.7 mmol) in anhydrous dichloromethane (300 mL) cooled to 0° C. was added N,N-diisopropylethylamine (22.8 mL, 131.2 mmol) followed by dropwise addition of 5-chloropentanoyl chloride (13.5 mL, 104.96 mmol) under nitrogen. To the resulting mixture was added 4-dimethylaminopyridine (0.534 mg, 4.37 mmol), and the reaction mixture was stirred at RT for 16 h. The reaction mixture was concentrated to dryness in vacuo to afford 5-chloro-N-(1-(5-chloropentanoyl)-3-cyclopropyl-1H-pyrazol-5-yl)-N-methylpentanamide (1.3 g, 76%) as a yellow oil used as is in the next step: LCMS $R_T$=1.79 min, m/z=374.1 $(M)^+$, 376.1 $(M+2)^+$.

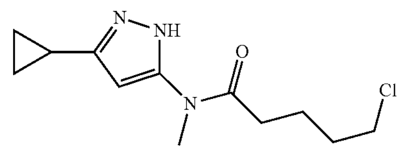 [SMILES: CN(C(=O)CCCCCl)c1cc(C2CC2)n[nH]1]

Step 2: 5-chloro-N-(3-cyclopropyl-1H-pyrazol-5-yl)-N-methylpentanamide

To a stirred solution of 5-chloro-N-(1-(5-chloropentanoyl)-3-cyclopropyl-1H-pyrazol-5-yl)-N-methylpentanamide (21.5 g, crude) in ethanol (115 mL) was added sodium hydroxide (2.29 g, 57.4 mmol) in water (57.6 mL) and the mixture was left to stand at RT for 5 min. The reaction mixture was concentrated to dryness in vacuo, and the residue was purified by column chromatography (silica gel, 100-200 mesh, 45 to 50% ethyl acetate in hexane) to afford 5-chloro-N-(3-cyclopropyl-1H-pyrazol-5-yl)-N-methylpentanamide (4.2 g, 34%) as a yellow oil, used as is in the next step: $^1$H NMR (400 MHz, DMSO-$d_6$) δ 12.47 (s, 1H), 5.89 (s, 1H), 3.56 (br. s, 2H), 3.04 (s, 3H), 2.18 (br. s, 2H), 1.87 (br.s, 1H), 1.61-1.57 (m, 4H), 0.92 (d, J=6 Hz, 2H), 0.69 (br. s, 2H). LCMS $R_T$=1.49 min, m/z=256 $(M)^+$, 258 $(M+2)^+$.

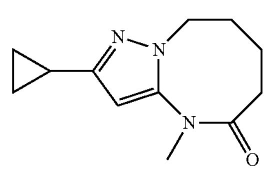 [SMILES: CN1C(=O)CCCCn2nc(C3CC3)cc21]

Step 3: 2-cyclopropyl-4-methyl-6,7,8,9-tetrahydropyrazolo[1,5-a][1,3]diazocin-5(4H)-one To a solution of 5-chloro-N-(3-cyclopropyl-1H-pyrazol-5-yl)-N-methylpentanamide (4.2 g, 19.47 mmol) in anhydrous acetonitrile (200 mL) was added cesium carbonate (12.69 g, 38.95 mmol) and stirred at RT for 16 h. The reaction mixture was concentrated to dryness in vacuo and the residue was purified by column chromatography (silica gel, 100-200 mesh, 45 to 50% ethyl acetate in hexane) to afford 2-cyclopropyl-4-methyl-6,7,8,9-tetrahydropyrazolo[1,5-a][1,3]diazocin-5(4H)-one (3.5 g, 82%) as an off white solid: $^1$H NMR (400 MHz, DMSO-$d_6$) δ 5.99 (s, 1H), 4.30 (br. d, J=10.04 Hz), 3.64 (t, J=12.32 Hz, 1H), 3.11 (s, 3H), 2.27-2.22 (m, 1H), 1.87-1.78 (m, 3H), 1.69 (t, J=11.8 Hz), 1.54-1.51 (m, 1H), 1.39-1.33 (m, 1H) 0.85-0.82 (m, 2H), 0.63 (br. S, 2H). LCMS $R_T$=1.39 min, m/z=220.0 (M+H)$^+$.

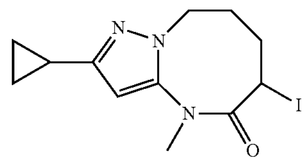 [SMILES: CN1C(=O)C(I)CCCn2nc(C3CC3)cc21]

Step 4: 2-cyclopropyl-6-iodo-4-methyl-6,7,8,9-tetrahydropyrazolo[1,5-a][1,3]diazocin-5(4H)-one To a solution of 2-cyclopropyl-4-methyl-6,7,8,9-tetrahydropyrazolo[1,5-a][1,3]diazocin-5(4H)-one (2.5 g, 11.4 mmol) in dry dichloromethane (65 mL) under nitrogen cooled to ~−10° C. in a salt/ice bath was added N,N,N',N'-tetramethylethylenediamine (18.2 mL, 68.4 mmol) followed by iodotrimethylsilane (9.7 mL, 68.4 mmol). The resulting solution was stirred in the salt/ice bath for 1.5 h, after which time was added iodine (8.6 g, 34.2 mmol). The mixture continued to stir in the salt/ice bath for another 2 h, after which time the reaction mixture was diluted with water (100 mL). The layers were separated, and the aqueous was extracted with ethyl acetate (2×100 mL). The combined organic extracts were washed with sodium bisulfite (1×150 mL), water (1×100 mL), brine (1×100 mL) and dried over anhydrous sodium sulfate and concentrated to dryness in vacuo to afford 2-cyclopropyl-6-iodo-4-methyl-6,7,8,9-tetrahydropyrazolo[1,5-a][1,3]diazocin-5(4H)-one (4 g, crude yield) as a light yellow oil, used as is in the next step.

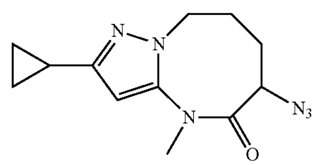 [SMILES: CN1C(=O)C(N=[N+]=[N-])CCCn2nc(C3CC3)cc21]

Step 4: 6-azido-2-cyclopropyl-4-methyl-6,7,8,9-tetrahydropyrazolo[1,5-a][1,3]diazocin-5(4H)-one To a solution of 2-cyclopropyl-6-iodo-4-methyl-6,7,8,9-tetrahydropyrazolo[1,5-a][1,3]diazocin-5(4H)-one (4 g, 15.4 mmoL crude) in N,N-dimethylformamide (60 mL) was added sodium azide (3 g, 65.0 mmol), and the reaction mixture was stirred at RT for 17 h. The reaction mixture was diluted with ethyl acetate (200 mL), washed with water (3×100 mL), brine (1×100 mL), dried over sodium sulfate and concentrated to dryness in vacuo. The resulting residue was purified by column chromatography (silica gel, 100-200 mesh, 25 to 30% ethyl acetate in hexane) affording 6-azido-2-cyclopropyl-4-methyl-6,7,8,9-tetrahydropyrazolo[1,5-a][1,3]diazocin-5(4H)-one (2 g, 66% over two steps) as a yellow solid (0.606 g, 96%): $^1$H NMR (400 MHz, DMSO-d$_6$) δ 6.08 (s, 1H), 4.20 (dd, J=14.8, 5.2 Hz, 1H), 3.72 (dd, J=14.8, 11.5 Hz, 1H), 3.30-3.17 (m, 1H), 3.18 (s, 3H), 1.99-1.92 (m, 3H), 1.95 (s, 2H), 1.85-1.80 (m, 1H), 1.65-1.60 (m, 1H), 0.85 (dd, J=8.4, 2.4 Hz, 3H), 0.64 (dd, J=7.4, 5.1 Hz, 2H). LCMS $R_T$=1.51 min, m/z=261.1 (M+H)$^+$.

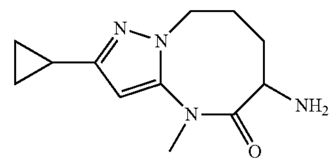 [SMILES: CN1C(=O)C(N)CCCn2nc(C3CC3)cc21]

Step 5: 6-amino-2-cyclopropyl-4-methyl-6,7,8,9-tetrahydropyrazolo[1,5-a][1,3]diazocin-5(4H)-one To a solution of 6-azido-2-cyclopropyl-4-methyl-6,7,8,9-tetrahydropyrazolo[1,5-a][1,3]diazocin-5(4H)-one (3 g, 11.5 mmol) in methanol (50 mL) was added 10% palladium on carbon (1.5 g) under argon. The reaction mixture was stirred under hydrogen (balloon pressure) at RT for 3 h. The reaction mixture was filtered through Celite, the cake washed with methanol and the combined filtrate was concentrated to dryness in vacuo affording 6-amino-2-cyclopropyl-4-methyl-6,7,8,9-tetrahydropyrazolo[1,5-a][1,3]diazocin-5(4H)-one (2.2 g, 82%) as a viscous yellow liquid used as is in the next step: $^1$H NMR (400 MHz, DMSO-d$_6$) δ 6.00 (s, 1H), 4.15 (dd, J=14.2, 4.9 Hz, 1H), 3.64 (dd, J=14.2, 11.4 Hz, 1H), 3.13 (s, 3H), 2.74 (d, J=7.3 Hz, 1H), 1.95 (s, 1H), 1.83-1.82 (m, 2H), 1.63-1.52 (m, 3H), 0.85 (d, J=6.5 Hz, 2H), 0.63 (s, 2H). LCMS $R_T$=2.12 min, m/z=235.2 (M+H)$^+$.

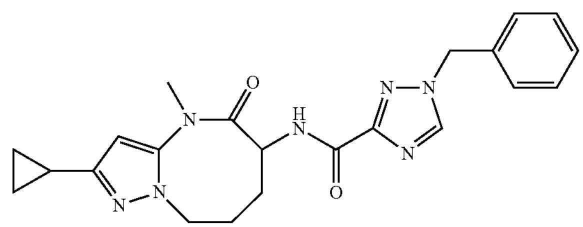 [SMILES: CN1C(=O)C(NC(=O)c2ncn(Cc3ccccc3)n2)CCCn2nc(C3CC3)cc21]

Step 6: 1-benzyl-N-(2-cyclopropyl-4-methyl-5-oxo-4,5,6,7,8,9-hexahydropyrazolo[1,5-a][1,3]diazocin-6-yl)-1H-1,2,4-triazole-3-carboxamide Method B (29 mg, 65% yield)

$^1$H NMR (400 MHz, DMSO-d$_6$) δ 8.80 (s, 1H), 8.21 (d, J=7.1 Hz, 1H), 7.39-7.24 (m, 5H), 6.07 (s, 1H), 5.47 (s, 2H), 4.32-4.15 (m, 1H), 3.98-3.67 (m, 2H), 3.17 (s, 3H), 2.03-1.72 (m, 4H), 1.67-1.50 (m, 1H), 0.93-0.79 (m, 2H), 0.77-0.53 (m, 2H). LCMS $R_T$=4.11 min, m/z=420.2 (M+H)$^+$.

LCMS (2 to 98% acetonitrile in water+0.1% formic acid over 10 mins) retention time 4.11 min, ESI+ found [M+H]=420.2.

Example 105

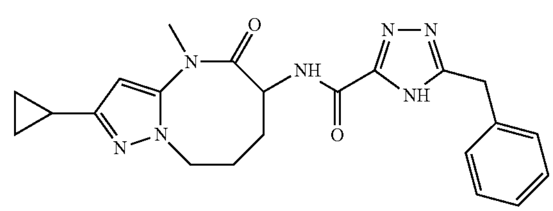 [SMILES: CN1C(=O)C(NC(=O)c2nnc(Cc3ccccc3)[nH]2)CCCn2nc(C3CC3)cc21]

5-benzyl-N-(2-cyclopropyl-4-methyl-5-oxo-4,5,6,7,8,9-hexahydropyrazolo[1,5-a][1,3]diazocin-6-yl)-4H-1,2,4-triazole-3-carboxamide Method B (8.4 mg, 19% yield)

$^1$H NMR (400 MHz, DMSO-$d_6$) δ 8.44 (s, OH), 8.28-8.17 (m, 1H), 7.42-7.18 (m, 4H), 6.68 (s, 1H), 6.07 (s, 1H), 4.29-4.18 (m, 1H), 4.09 (s, 2H), 3.93-3.72 (m, 2H), 3.17 (s, 3H), 2.03-1.74 (m, 4H), 1.65-1.50 (m, 1H), 0.91-0.81 (m, 2H), 0.71-0.56 (m, 2H). LCMS $R_T$=3.97 min, m/z=420.2 $(M+H)^+$.

LCMS (2 to 98% acetonitrile in water+0.1% formic acid over 10 mins) retention time 3.97 min, ESI+ found [M+H]=420.2.

Example 106

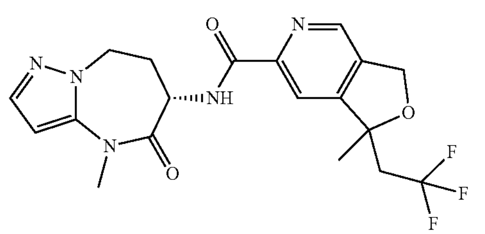 [SMILES: CN1C(=O)[C@@H](NC(=O)c2cc3c(cn2)COC3(C)CC(F)(F)F)CCn2nccc21]

1-methyl-N—((S)-4-methyl-5-oxo-5,6,7,8-tetrahydro-4H-pyrazolo[1,5-a][1,3]diazepin-6-yl)-1-(2,2,2-trifluoroethyl)-1,3-dihydrofuro[3,4-c]pyridine-6-carboxamide Method B (50 mg, 71% yield)

$^1$H NMR (400 MHz, DMSO-$d_6$) δ 8.94-8.88 (m, 1H), 8.67 (s, 1H), 8.14 (s, 1H), 7.51 (d, J=2.0 Hz, 1H), 6.35 (d, J=2.0 Hz, 1H), 5.19-5.11 (m, 2H), 4.45-4.33 (m, 2H), 4.31-4.16 (m, 1H), 3.27 (s, 3H), 3.14-3.03 (m, 1H), 2.99-2.87 (m, 1H), 2.78-2.62 (m, 1H), 2.41-2.29 (m, 1H), 1.50 (s, 3H). LCMS $R_T$=4.22 min, m/z=424.1 $(M+H)^+$.

LCMS (2 to 98% acetonitrile in water+0.1% formic acid over 10 mins) retention time 4.22 min, ESI+ found [M+H]=424.1.

Example 107

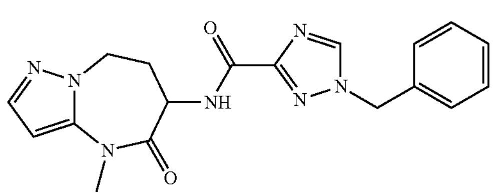 [SMILES: CN1C(=O)C(NC(=O)c2ncn(Cc3ccccc3)n2)CCn2nccc21]

1-benzyl-N-(3,4-dimethyl-5-oxo-5,6,7,8-tetrahydro-4H-pyrazolo[1,5-a][1,3]diazepin-6-yl)-1H-1,2,4-triazole-3-carboxamide Method B (50 mg, 64% yield)

$^1$H NMR (400 MHz, DMSO-$d_6$) δ 8.81 (s, 1H), 8.41 (d, J=7.7 Hz, 1H), 7.44-7.25 (m, 6H), 5.48 (s, 2H), 4.34-4.12 (m, 3H), 3.21 (s, 3H), 2.61-2.53 (m, 1H), 2.29-2.19 (m, 1H), 2.01 (s, 3H). LCMS $R_T$=3.71 min, m/z=380.2 $(M+H)^+$.

LCMS (2 to 98% acetonitrile in water+0.1% formic acid over 10 mins) retention time 3.71 min, ESI+ found [M+H]=380.2.

Example 108

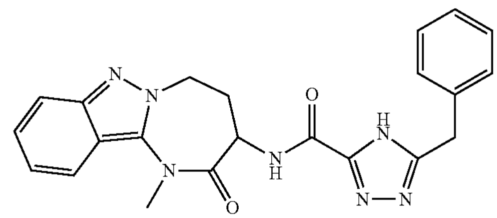 [SMILES: CN1C(=O)C(NC(=O)c2nnc(Cc3ccccc3)[nH]2)CCn2nc3ccccc3c21]

5-benzyl-N-(1-methyl-2-oxo-2,3,4,5-tetrahydro-1-[1,3]diazepino[1,2-b]indazol-3-yl)-4H-1,2,4-triazole-3-carboxamide 5-benzyl-N-(1-methyl-2-oxo-2,3,4,5-tetrahydro-1H-[1,3]diazepino[1,2-b]indazol-3-yl)-4H-1, 2,4-triazole-3-carboxamide was prepared from 1H-indazole-3-amine according to Method Z. Yield of final step: 0.057 g, 70%: $^1$H NMR (400 MHz, DMSO-d6) δ 7.76 (dt, J=8.5, 1.0 Hz, 1H), 7.62 (dt, J=8.8, 0.9 Hz, 1H), 7.38-7.18 (m, 6H), 7.12 (ddd, J=8.5, 6.6, 0.9 Hz, 1H), 4.61 (dd, J=10.7, 4.1 Hz, 2H), 4.22 (dt, J=11.4, 8.0 Hz, 1H), 4.11 (s, 2H), 3.47 (s, 3H), 2.18 (t, J=7.4 Hz, 1H), 1.47 (d, J=7.5 Hz, 1H). LC-MS $R_T$=4.08 min, m/z=416.2 $(M+H)^+$.

LCMS (5 to 95% acetonitrile in water+0.1% formic acid over 10 mins) retention time 4.08 min, ESI+ found [M+H]=416.2.

Example 109

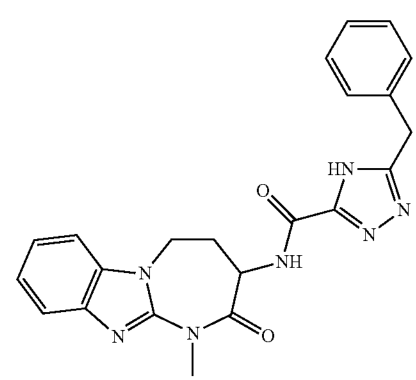 [SMILES: CN1C(=O)C(NC(=O)c2nnc(Cc3ccccc3)[nH]2)CCn2c1nc1ccccc12]

Method G2

5-benzyl-N-(1-methyl-2-oxo-2,3,4,5-tetrahydro-1H-benzo[4,5]imidazo[1,2-a][1,3]diazepin-3-yl)-4H-1,2,4-triazole-3-carboxamide

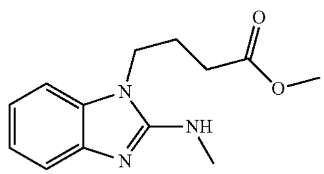 [SMILES: CNc1nc2ccccc2n1CCCC(=O)OC]

Step 1: methyl 4-[2-(methylamino)benzimidazol-1-yl]butanoate

To a solution of N-methyl-1H-benzimidazol-2-amine (1.36 g, 9.24 mmol, 1.00) in acetonitrile (40 mL) was added cesium carbonate (12 g, 37.0 mmol, 4 equiv) followed by methyl 4-bromobutanoate (1.40 mL, 2.01 g, 11.1 mmol, 1.0 equiv). The reaction mixture was stirred overnight at RT, then was filtered through Celite and concentrated to dryness in vacuo. The residue was purified by flash column chromatography (silica gel, 100-200 mesh, 0 to 10% methanol in dichloromethane) to afford methyl 4-[2-(methylamino)benzimidazol-1-yl]butanoate (0.65 g, 28%) as an orange oil.

LCMS (5 to 95% acetonitrile in water+0.1% formic acid over 2 mins) retention time 0.88 min, ESI+ found [M+H]=248.

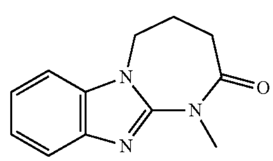 [SMILES: CN1C(=O)CCCn2c1nc1ccccc12]

Step 2: 1-methyl-4,5-dihydro-3H-[1,3]diazepino[1,2-a]benzimidazol-2-one

To a solution of methyl 4-[2-(methylamino)benzimidazol-1-yl]butanoate (0.650 g, 2.63 mmol) in methanol (3 mL) was added a solution of 1M aqueous sodium hydroxide (2.89 mL, 2.891 mmol, 1.100 equiv). The reaction mixture stirred at RT for 1 h. The mixture was concentrated to dryness in vacuo and resuspended in N,N-dimethylformamide (5 mL), and to it was added N,N-diisopropylethylamine (1.38 mL, 7.89 mmol, 3 equiv) followed by (7-Azabenzotriazol-1-yloxy)tripyrrolidinophosphonium hexafluorophosphate (1.71 g, 3.15 mmol, 1.2 equiv). The reaction stirred 4 h at RT. The reaction mixture was diluted with isopropyl acetate (50 mL), then washed with water (50 mL) and brine (50 mL). The organic layer was dried over sodium sulfate, filtered, and concentrated to dryness in vacuo. The residue was purified by flash column chromatography (silica gel, 100-200 mesh, 0 to 100% isopropyl acetate in heptane) to afford the product 1-methyl-4,5-dihydro-3H-[1,3]diazepino[1,2-a]benzimidazol-2-one (0.41 g, 72%) as a yellow solid.

LCMS (5 to 95% acetonitrile in water+0.1% formic acid over 2 mins) retention time 0.96 min, ESI+ found [M+H]=216.

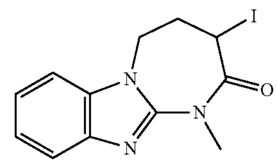 [SMILES: CN1C(=O)C(I)CCn2c1nc1ccccc12]

Step 3: 3-iodo-1-methyl-4,5-dihydro-3H-[1,3]diazepino[1,2-a]benzimidazol-2-one

To a solution of 1-methyl-4,5-dihydro-3H-[1,3]diazepino[1,2-a]benzimidazol-2-one (0.375 g, 1.74 mmol) in dichloromethane (10 mL) cooled in a salt/ice bath was added N,N,N',N'-tetramethylethylenediamine (1.58 mL, 10.45 mmol, 6 equiv) followed by iodotrimethylsilane (1.491 mL, 10.45 mmol, 6 equiv). The reaction mixture was stirred for 1.5 h in the salt/ice bath, then was added iodine (1.33 g, 5.23 mmol, 3 equiv), and the mixture was stirred in the cooling bath for another 2 h. The reaction was then quenched by the addition of a saturated sodium sulfite solution (50 mL). The layers were separated, and the aqueous was extracted two more times with dichloromethane (2×50 mL). The combined organics were dried over sodium sulfate, filtered and concentrated to dryness in vacuo. The residue was purified by flash column chromatography (silica gel, 100-200 mesh, 0 to 50% isopropyl acetate in heptane) to afford 3-iodo-1-methyl-4,5-dihydro-3H-[1,3]diazepino[1,2-a]benzimidazol-2-one (0.445 g, 75% yield) as a white solid.

LCMS (5 to 95% acetonitrile in water+0.1% formic acid over 2 mins) retention time 1.06 min, ESI+ found [M+H]=342.

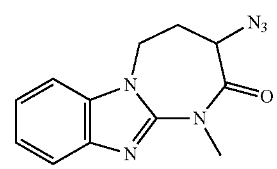 [SMILES: CN1C(=O)C(N=[N+]=[N-])CCn2c1nc1ccccc12]

Step 4: 3-azido-1-methyl-4,5-dihydro-3H-[1,3]diazepino[1,2-a]benzimidazol-2-one

To a solution of 3-iodo-1-methyl-4,5-dihydro-3H-[1,3]diazepino[1,2-a]benzimidazol-2-one (0.45 mg, 1.30 mmol) in N,N-dimethylformamide (2 mL) was added sodium azide (0.101 g, 1.57 mmol, 1.2 equiv). The reaction mixture was stirred for 2 h at RT, filtered through Celite, and concentrated to dryness in vacuo. The residue was purified by flash column chromatography (silica gel, 100-200 mesh, 0 to 100% isopropyl acetate in heptane) to afford 3-azido-1-methyl-4,5-dihydro-3H-[1,3]diazepino[1,2-a]benzimidazol-2-one (0.315 g, 94%) as a white solid.

LCMS (5 to 95% acetonitrile in water+0.1% formic acid over 2 mins) retention time 1.04 min, ESI+ found [M+H]=257.

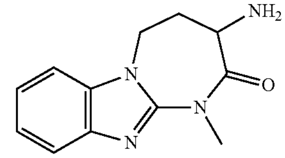 [SMILES: CN1C(=O)C(N)CCn2c1nc1ccccc12]

Step 5: 3-amino-1-methyl-4,5-dihydro-3H-[1,3]diazepino[1,2-a]benzimidazol-2-one

To a solution of 3-azido-1-methyl-4,5-dihydro-3H-[1,3]diazepino[1,2-a]benzimidazol-2-one (0.315 g, 1.23 mmol, 1 equiv) in tetrahydrofuran (5 mL) was added water (1 mL) and polystyrene-bound triphenylphosphine resin (1.23 g, ~3 mmol/g loading, 3.69 mmol, 3 equiv). The reaction mixture was shaken for 16 h at RT, then was filtered through Celite and concentrated to dryness in vacuo. The residue was purified by flash column chromatography (silica gel, 100-200 mesh, 0 to 15% methanol in dichloromethane) to afford 3-amino-1-methyl-4,5-dihydro-3H-[1,3]diazepino[1,2-a]benzimidazol-2-one (0.197 g, 70%) as a colorless oil.

LCMS (5 to 95% acetonitrile in water+0.1% formic acid over 2 mins) retention time 0.76 min, ESI+ found [M+H]=231.

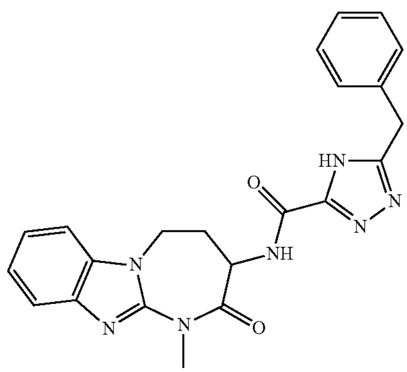 [SMILES: CN1C(=O)C(NC(=O)c2nnc(Cc3ccccc3)[nH]2)CCn2c1nc1ccccc12]

Step 6: 5-benzyl-N-(1-methyl-2-oxo-2,3,4,5-tetrahydro-1H-benzo[4,5]imidazo[1,2-a][1,3]diazepin-3-yl)-4H-1,2,4-triazole-3-carboxamide To a solution of 3-amino-1-methyl-4,5-dihydro-3H-[1,3]diazepino[1,2-a]benzimidazol-2-one (0.028 g, 0.12 mmol) in N,N-dimethylformamide (2 mL) was added 5-benzyl-4H-1,2,4-triazole-3-carboxylic acid (0.037 g, 0.18 mmol, 1.5 equiv), N,N-diisopropylamine (0.064 mL, 0.047 g, 0.36 mmol, 3 equiv), and (7-Azabenzotriazol-1-yloxy)tripyrrolidinophosphonium hexafluorophosphate (0.076 mg, 0.14 mmol, 1.15 equiv). The reaction mixture was stirred for 16 h at RT, diluted with isopropyl acetate (25 mL), washed with water (25 mL) and brine (25 mL). The organic layer was dried over sodium sulfate, filtered, and concentrated to dryness in vacuo. The residue was purified by preparative RP-HPLC (5 to 50% acetonitrile in H2O+0.1% formic acid) to afford 5-benzyl-N-(1-methyl-2-oxo-2,3,4,5-tetrahydro-1H-benzo[4,5]imidazo[1,2-a][1,3]diazepin-3-yl)-4H-1,2,4-triazole-3-carboxamide (0.014 g, 27%) as a white solid: $^1$H NMR (400 MHz, DMSO-d6) δ 14.32 (s, 1H), 8.61 (s, 1H), 7.67-7.58 (m, 2H), 7.36-7.19 (m, 7H), 4.72-4.61 (m, 1H), 4.49 (dt, J=11.5, 7.8 Hz, 1H), 4.19-3.98 (m, 3H), 3.42 (s, 3H), 2.76-2.60 (m, 1H), 2.61-2.51 (m, 1H). LC-MS $R_T$=3.97 min, m/z=416.2 $(M+H)^+$.

LCMS (5 to 95% acetonitrile in water+0.1% formic acid over 10 mins) retention time 3.97 min, ESI+ found [M+H]=416.2.

Example 110

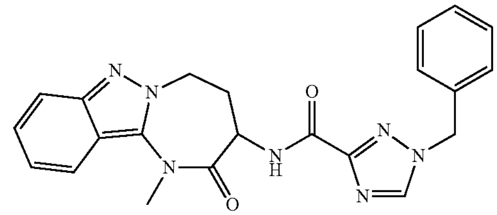 [SMILES: CN1C(=O)C(NC(=O)c2ncn(Cc3ccccc3)n2)CCn2nc3ccccc3c21]

1-benzyl-N-(1-methyl-2-oxo-2,3,4,5-tetrahydro-1H-[1,3]diazepino[1,2-b]indazol-3-yl)-1H-1,2,4-triazole-3-carboxamide 1-benzyl-N-(1-methyl-2-oxo-2,3,4,5-tetrahydro-1H-[1,3]diazepino[1,2-b]indazol-3-yl)-1H-1, 2,4-triazole-3-carboxamide was prepared from 1H-indazole-3-amine according to Methods Z and G1. Yield of final step: 0.033 g, 52%: $^1$H NMR (400 MHz, DMSO-d6) δ 8.81 (s, 1H), 8.57 (d, J=7.7 Hz, 1H), 7.76 (dt, J=8.5, 1.0 Hz, 1H), 7.62 (dt, J=8.8, 0.9 Hz, 1H), 7.43-7.25 (m, 6H), 7.12 (ddd, J=8.5, 6.6, 0.9 Hz, 1H), 5.47 (s, 2H), 4.65-4.56 (m, 2H), 4.22 (dt, J=11.5, 7.9 Hz, 1H), 3.47 (s, 3H), 2.79-2.65 (m, 1H), 2.61-2.51 (m, 1H). LC-MS $R_T$=4.26 min, m/z=416.2 $(M+H)^+$.

LCMS (5 to 95% acetonitrile in water+0.1% formic acid over 10 mins) retention time 4.26 min, ESI+ found [M+H]=416.2.

Example 111

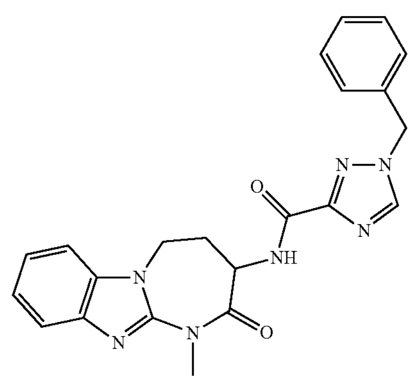 [SMILES: CN1C(=O)C(NC(=O)c2ncn(Cc3ccccc3)n2)CCn2c1nc1ccccc12]

1-benzyl-N-(1-methyl-2-oxo-2,3,4,5-tetrahydro-1H-benzo[4,5]imidazo[1,2-a][1,3]diazepin-3-yl)-1H-1,2,4-triazole-3-carboxamide was prepared from 3-amino-1-methyl-4,5-dihydro-3H-[1,3]diazepino[1,2-a]benzimidazol-2-one according to Method G1. Yield: 0.011 g, 22%: $^1$H NMR (400 MHz, DMSO-d6) δ 8.83 (s, 1H), 8.69 (d, J=7.6 Hz, 1H), 7.68-7.56 (m, 2H), 7.43-7.17 (m, 8H), 5.49 (s, 2H), 4.71-4.60 (m, 1H), 4.48 (dt, J=11.5, 7.7 Hz, 1H), 4.05 (ddd, J=14.6, 12.8, 6.5 Hz, 1H), 3.42 (s, 3H), 2.76-2.62 (m, 1H), 2.56-2.45 (m, 1H). LC-MS $R_T$=4.08 min, m/z=416.2 $(M+H)^+$.

LCMS (5 to 95% acetonitrile in water+0.1% formic acid over 10 mins) retention time 4.08 min, ESI+ found [M+H]=416.2.

Example 112: Method G3

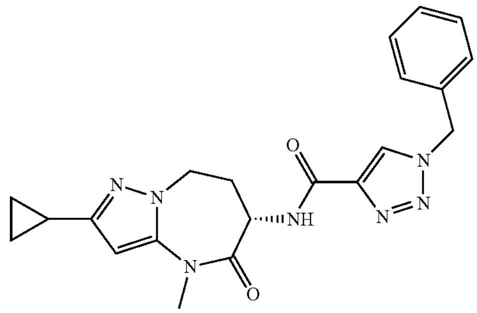

(S)-1-benzyl-N-(2-cyclopropyl-4-methyl-5-oxo-5,6,7,8-tetrahydro-4H-pyrazolo[1,5-a][1,3]diazepin-6-yl)-1H-1,2,3-triazole-4-carboxamide

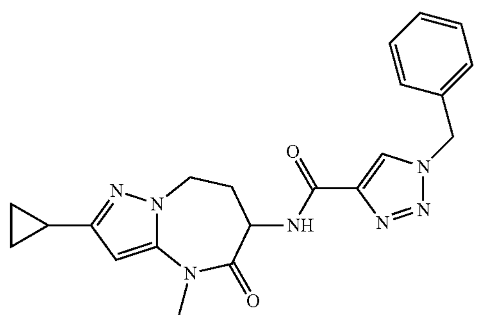 [SMILES: CN1C(=O)C(NC(=O)c2cn(Cc3ccccc3)nn2)CCn2nc(C3CC3)cc21]

Step 1: 1-benzyl-N-(2-cyclopropyl-4-methyl-5-oxo-5,6,7,8-tetrahydro-4H-pyrazolo[1,5-a][1,3]diazepin-6-yl)-1H-1,2,3-triazole-4-carboxamide To a solution of 6-amino-2-cyclopropyl-4-methyl-7,8-dihydro-6H-pyrazolo[1,5-a][1,3]diazepin-5-one (0.029 g, 0.13 mmol, 1 equiv) in N,N-dimethylformamide (2 mL) was added 1-benzyltriazole-4-carboxylic acid (0.040 g, 0.20 mmol, 1.5 equiv), N,N-diisopropylethylamine (0.069 mL, 0.40 mmol, 3 equiv), and (7-Azabenzotriazol-1-yloxy) tripyrrolidinophosphonium hexafluorophosphate (0.082 g, 0.15 mmol, 1.15 equiv). The reaction mixture was stirred overnight, then was diluted with isopropyl acetate (25 mL), washed with water (25 mL) and brine (25 mL). The organic layer was dried over sodium sulfate, filtered, and concentrated to dryness in vacuo. The residue was purified by preparative RP-HPLC (5 to 50% acetonitrile in H2O+0.1% formic acid) to afford 1-benzyl-N-(2-cyclopropyl-4-methyl-5-oxo-5,6,7,8-tetrahydro-4H-pyrazolo[1,5-a][1,3]diazepin-6-yl)-1H-1,2,3-triazole-4-carboxamide (0.030 g, 56% yield) as a white solid.

LCMS (5 to 95% acetonitrile in water+0.1% formic acid over 10 mins) retention time 4.46 min, ESI+ found [M+H]=406.2

1-benzyl-N-(2-cyclopropyl-4-methyl-5-oxo-5,6,7,8-tetrahydro-4H-pyrazolo[1,5-a][1,3]diazepin-6-yl)-1H-1,2,3-triazole-4-carboxamide was further purified by chiral SFC (Whelk O-1 column, 40% methanol+0.1% ammonium hydroxide isocratic elution) affording arbitrarily assigned enantiomers (R)-1-benzyl-N-(2-cyclopropyl-4-methyl-5-oxo-5,6,7,8-tetrahydro-4H-pyrazolo[1,5-a][1,3]diazepin-6-yl)-1H-1,2,3-triazole-4-carboxamide (0.014 g, 26%) and (S)-5-1-benzyl-N-(2-cyclopropyl-4-methyl-5-oxo-5,6,7,8-tetrahydro-4H-pyrazolo[1,5-a][1,3]diazepin-6-yl)-1H-1,2,3-triazole-4-carboxamide (0.013 g, 24%) as white solids:

Analytical data for the first eluting enantiomer (arbitrarily assigned R configuration): SFC $R_T$(Whelk O-1 column, 40% methanol+0.1% ammonium hydroxide isocratic elution, 2.5 min method): 0.773 min, 100% ee: $^1$H NMR (400 MHz, DMSO-d6) δ 8.66 (s, 1H), 8.60 (d, J=7.9 Hz, 1H), 7.54-7.15 (m, 5H), 6.05 (s, 1H), 5.65 (s, 2H), 4.39-4.19 (m, 3H), 4.09 (ddd, J=14.6, 12.6, 6.5 Hz, 1H), 3.19 (s, 3H), 2.62-2.52 (m, 1H), 2.40-2.28 (m, 1H), 1.85 (tt, J=8.4, 5.0 Hz, 1H), 0.89-0.81 (m, 2H), 0.75-0.58 (m, 2H) LCMS $R_T$=4.46 min, m/z=406.2 $(M+H)^+$.

Analytical data for the second eluting enantiomer (arbitrarily assigned S configuration): SFC $R_T$: 0.960 min, 100% ee: $^1$H NMR (400 MHz, DMSO-d6) δ 8.66 (s, 1H), 8.60 (d, J=7.9 Hz, 1H), 7.56-7.18 (m, 5H), 6.05 (s, 1H), 5.65 (s, 2H), 4.46-4.16 (m, 2H), 4.16-3.97 (m, 1H), 3.19 (s, 3H), 2.62-2.52 (m, 1H), 2.42-2.28 (m, 1H), 1.85 (tt, J=8.4, 5.0 Hz, 1H), 0.91-0.80 (m, 2H), 0.73-0.59 (m, 2H). LCMS $R_T$=4.42 min, m/z=406.2 $(M+H)^+$.

Example 113: Method G4

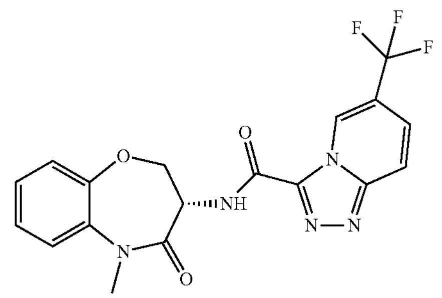 [SMILES: CN1C(=O)[C@@H](NC(=O)c2nnc3ccc(C(F)(F)F)cn23)COc2ccccc21]

(S)—N-(5-methyl-4-oxo-2,3,4,5-tetrahydrobenzo[b][1,4]oxazepin-3-yl)-6-(trifluoromethyl)-[1,2,4]triazolo[4,3-a]pyridine-3-carboxamide

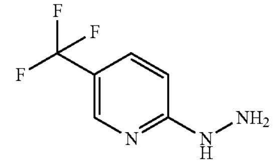 [SMILES: NNc1ccc(C(F)(F)F)cn1]

Step 1: [5-(trifluoromethyl)-2-pyridyl]hydrazine

To a solution of 2-chloro-5-(trifluoromethyl)pyridine (1.0 g, 5.5 mmol) in ethanol (10 mL) in a large microwave vial was added hydrazine hydrate (1.25 mL, 22 mmol, 4 equiv). The vial was capped and heated in a microwave to 150° C. for 1 h. The reaction mixture was diluted with saturated aqueous sodium bicarbonate (50 mL) and extracted with isopropyl acetate (3×75 mL). The combined organics were dried over sodium sulfate, filtered, and concentrated to dryness in vacuo to afford [5-(trifluoromethyl)-2-pyridyl] hydrazine (0.95 g, 97%) as a tan solid, which was used in the next step without further purification.

LCMS (5 to 95% acetonitrile in water+0.1% formic acid over 2 mins) retention time 0.77 min, ESI+ found [M+H]=178.

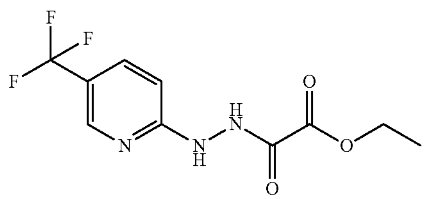 [SMILES: CCOC(=O)C(=O)NNc1ccc(C(F)(F)F)cn1]

Step 2: ethyl 2-oxo-2-[2-[5-(trifluoromethyl)-2-pyridyl]hydrazino]acetate

To a solution of [5-(trifluoromethyl)-2-pyridyl]hydrazine (0.95 mg, 5.4 mmol) in tetrahydrofuran (25 mL) cooled to 0° C. was added N,N-diisopropylethylamine (1.87 mL, 10.7 mmol, 2 equiv) followed by ethyl 2-chloro-2-oxo-acetate (0.66 mL, 5.9 mmol, 1.1 equiv). The reaction mixture was allowed to slowly warm to RT with stirring for 16 h. The mixture was concentrated to dryness in vacuo and purified by flash column chromatography (silica gel, 100-200 mesh, 0 to 100% isopropyl acetate in heptane) affording ethyl 2-oxo-2-[2-[5-(trifluoromethyl)-2-pyridyl]hydrazino]acetate (0.63 g, 42%) as an orange solid.

LCMS (5 to 95% acetonitrile in water+0.1% formic acid over 2 mins) retention time 1.15 min, ESI+ found [M+H]=278.

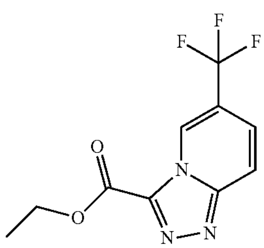 [SMILES: CCOC(=O)c1nnc2ccc(C(F)(F)F)cn12]

Step 3: ethyl 6-(trifluoromethyl)-[1,2,4]triazolo[4,3-a]pyridine-3-carboxylate

A suspension of ethyl 2-oxo-2-[2-[5-(trifluoromethyl)-2-pyridyl]hydrazino]acetate (0.63 g, 2.27 mmol) in phosphoryl chloride (6 mL, 64.6 mmol, 28.4 equiv) was heated to 100° C. for 16 h. The reaction mixture was cooled to RT and concentrated to dryness in vacuo. The residue was purified by column chromatography (silica gel, 100-200 mesh, 0 to 100% iPrOAc in heptane) affording ethyl 6-(trifluoromethyl)-[1,2,4]triazolo[4,3-a]pyridine-3-carboxylate (0.266 g, 45%) as an off-white solid.

LCMS (5 to 95% acetonitrile in water+0.1% formic acid over 2 mins) retention time 1.23 min, ESI+ found [M+H]=260.

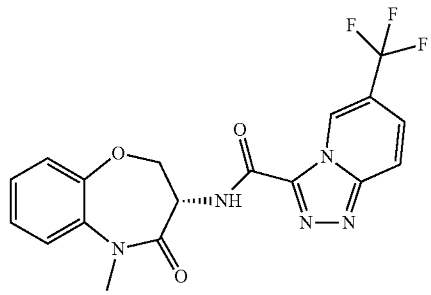 [SMILES: CN1C(=O)[C@@H](NC(=O)c2nnc3ccc(C(F)(F)F)cn23)COc2ccccc21]

Step 4: (S)—N-(5-methyl-4-oxo-2,3,4,5-tetrahydrobenzo[b][1,4]oxazepin-3-yl)-6-(trifluoromethyl)-[1,2,4]triazolo[4,3-a]pyridine-3-carboxamide To a solution of ethyl 6-(trifluoromethyl)-[1,2,4]triazolo[4,3-a]pyridine-3-carboxylate (0.266 g, 1.02 mmol) dissolved in tetrahydrofuran (4 mL) was added 1M aqueous sodium hydroxide (1.23 mL). The reaction mixture was stirred for 1 h at RT, then concentrated to dryness in vacuo. The residue was resuspended in N,N-dimethylformamide (2 mL), and to it was added [(3S)-5-methyl-4-oxo-2,3-dihydro-1,5-benzoxazepin-3-yl]ammonium chloride (0.040 g, 0.18 mmol), N,N-diisopropylethylamine (0.092 mL, 0.067 g, 0.52 mmol), and (7-Azabenzotriazol-1-yloxy)tripyrrolidinophosphonium hexafluorophosphate (0.114 g, 0.21 mmol). The reaction mixture was stirred for 16 h at RT, then was purified directly by preparative RP-HPLC (20-60% acetonitrile in water+0.1% formic acid) affording (S)—N-(5-methyl-4-oxo-2,3,4,5-tetrahydrobenzo[b][1,4]oxazepin-3-yl)-6-(trifluoromethyl)-[1, 2,4]triazolo[4,3-a]pyridine-3-carboxamide (0.035 g, 49%) as a white solid: $^1$H NMR (400 MHz, DMSO-d6) δ 9.49-9.40 (m, 2H), 8.25-8.14 (m, 1H), 7.83 (dd, J=9.6, 1.8 Hz, 1H), 7.58-7.49 (m, 1H), 7.40-7.19 (m, 3H), 4.95 (dt, J=11.6, 7.8 Hz, 1H), 4.76 (dd, J=11.7, 9.9 Hz, 1H), 4.47 (dd, J=9.9, 7.7 Hz, 1H), 3.34 (s, 3H). LC-MS $R_T$=4.09 min, m/z=406.1 $(M+H)^+$.

LCMS (5 to 95% acetonitrile in water+0.1% formic acid over 10 mins) retention time 4.09 min, ESI+ found [M+H]=406.1

Method G5

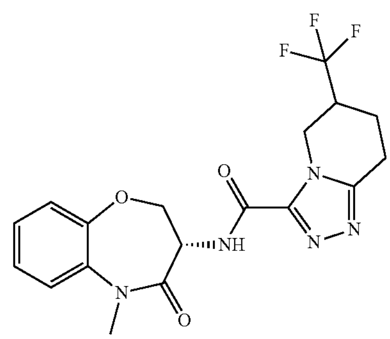 [SMILES: CN1C(=O)[C@@H](NC(=O)c2nnc3n2CC(C(F)(F)F)CC3)COc2ccccc21]

N—((S)-5-methyl-4-oxo-2,3,4,5-tetrahydrobenzo[b][1,4]oxazepin-3-yl)-6-(trifluoromethyl)-5,6,7,8-tetrahydro-[1,2,4]triazolo[4,3-a]pyridine-3-carboxamide To a solution of (S)—N-(5-methyl-4-oxo-2,3,4,5-tetrahydrobenzo[b][1,4]oxazepin-3-yl)-6-(trifluoromethyl)-[1, 2,4]

triazolo[4,3-a]pyridine-3-carboxamide (0.046 g, 0.11 mmol) in methanol (2 mL) was added palladium hydroxide (10 wt %, 0.024 g, 0.017 mmol, 0.15 equiv). The reaction mixture stirred under a balloon of hydrogen gas for 16 h at RT, then was filtered through Celite and concentrated to dryness in vacuo. The residue was purified by flash column chromatography (silica gel, 100-200 mesh, 0 to 10% methanol in dichloromethane) affording N—((S)-5-methyl-4-oxo-2,3,4,5-tetrahydrobenzo[b][1,4]oxazepin-3-yl)-6-(trifluoromethyl)-5, 6,7,8-tetrahydro-[1,2,4]triazolo[4,3-a]pyridine-3-carboxamide (0.034 g, 73%) as a white solid: 10 $^1$H NMR (400 MHz, DMSO-d6) δ 8.96 (d, J=8.0 Hz, 1H), 7.55-7.47 (m, 1H), 7.37-7.20 (m, 3H), 4.89-4.79 (m, 1H), 4.72-4.54 (m, 2H), 4.41 (ddd, J=9.8, 7.6, 3.4 Hz, 1H), 4.06 (dd, J=13.3, 10.4 Hz, 1H), 3.31 (s, 3H), 3.23-3.05 (m, 2H), 3.00-2.86 (m, 1H), 2.22-2.10 (m, 1H), 1.99-1.83 (m, 1H). LC-MS $R_T$=4.56 min, m/z=410.1 $(M+H)^+$.

LCMS (5 to 95% acetonitrile in water+0.1% formic acid over 10 mins) retention time 4.56 min, ESI+ found [M+H]=410.1

Example 114

Method G6

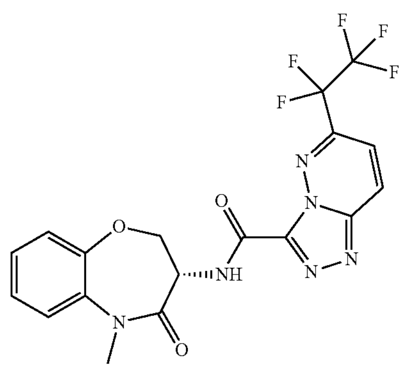 [SMILES: CN1C(=O)[C@@H](NC(=O)c2nnc3ccc(C(F)(F)C(F)(F)F)nn23)COc2ccccc21]

(S)—N-(5-methyl-4-oxo-2,3,4,5-tetrahydrobenzo[b][1,4]oxazepin-3-yl)-6-(perfluoroethyl)-[1,2,4]triazolo[4,3-b]pyridazine-3-carboxamide

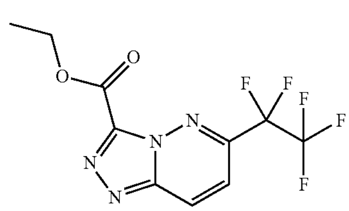 [SMILES: CCOC(=O)c1nnc2ccc(C(F)(F)C(F)(F)F)nn12]

Step 1: ethyl 6-(1,1,2,2,2-pentafluoroethyl)-[1,2,4]triazolo[4,3-b]pyridazine-3-carboxylate To a solution of ethyl 6-chloro-[1,2,4]triazolo[4,3-b]pyridazine-3-carboxylate (0.2 g, 0.88 mmol) in N,N-dimethylformamide (2 mL) was added (1,1,2,2,2-Pentafluoroethyl)(1,10-phenanthroline-κN1, κN10)copper (0.384 g, 1.06 mmol, 1.2 equiv). The reaction mixture was heated to 90° C. for 24 h, then was diluted with isopropyl acetate (25 mL) and water (25 mL). The layers were separated, and the aqueous was extracted two more times with isopropyl acetate (2×25 mL). The combined organics were washed with water and brine, dried over sodium sulfate, filtered and concentrated to dryness in vacuo. The residue was purified by column chromatography (silica gel, 100-200 mesh, 0 to 100% isopropyl acetate in heptane) affording ethyl 6-(1,1,2,2,2-pentafluoroethyl)-[1,2,4]triazolo[4,3-b]pyridazine-3-carboxylate (0.031 g, 11%) as a pale yellow solid.

LCMS (5 to 95% acetonitrile in water+0.1% formic acid over 2 mins) retention time 1.20 min, ESI+ found [M+H]=311.

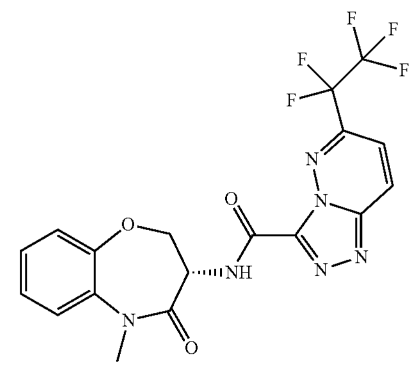 [SMILES: CN1C(=O)[C@@H](NC(=O)c2nnc3ccc(C(F)(F)C(F)(F)F)nn23)COc2ccccc21]

Step 2: (S)—N-(5-methyl-4-oxo-2,3,4,5-tetrahydrobenzo[b][1,4]oxazepin-3-yl)-6-(perfluoroethyl)-[1,2,4]triazolo[4,3-b]pyridazine-3-carboxamide To a solution of ethyl 6-(1,1,2,2,2-pentafluoroethyl)-[1,2,4]triazolo[4,3-b]pyridazine-3-carboxylate (0.031 g, 0.10 mmol) dissolved in methanol (1 mL) was added 1M aqueous sodium hydroxide (0.15 mL). The reaction mixture was stirred for 1 h at 0° C., then concentrated to dryness in vacuo. The residue was resuspended in N,N-dimethylformamide (2 mL), and to it was added [(3S)-5-methyl-4-oxo-2,3-dihydro-1,5-benzoxazepin-3-yl]ammonium chloride (0.025 g, 0.1 mmol), N,N-diisopropylethylamine (0.057 mL, 0.33 mmol), and (7-Azabenzotriazol-1-yloxy)tripyrrolidinophosphonium hexafluorophosphate (0.071 g, 0.13 mmol). The reaction mixture was stirred for 16 h at RT, then was purified directly by preparative RP-HPLC (20-60% acetonitrile in water+0.1% formic acid) affording (S)—N-(5-methyl-4-oxo-2,3,4,5-tetrahydrobenzo[b][1,4]oxazepin-3-yl)-6-(trifluoromethyl)-[1, 2,4]triazolo[4,3-a]pyridine-3-carboxamide (0.015 g, 30%) as a white solid: $^1$H NMR (400 MHz, DMSO-d6) δ 9.30 (d, J=7.8 Hz, 1H), 8.90-8.79 (m, 1H), 7.93 (d, J=9.8 Hz, 1H), 7.57-7.49 (m, 1H), 7.41-7.23 (m, 3H), 4.97 (dt, J=11.4, 7.8 Hz, 1H), 4.62 (dd, J=11.5, 9.9 Hz, 1H), 4.52 (dd, J=9.9, 7.8 Hz, 1H), 3.35 (s, 3H). LC-MS $R_T$=4.81 min, m/z=457.1 $(M+H)^+$.

LCMS (5 to 95% acetonitrile in water+0.1% formic acid over 10 mins) retention time 4.81 min, ESI+ found [M+H]=457.1

Example 115

Method G7

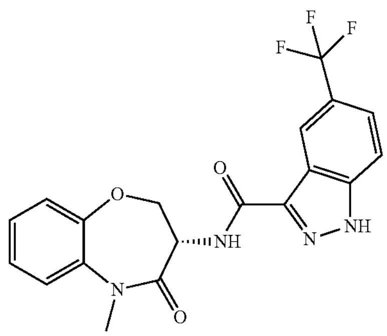 [SMILES: CN1C(=O)[C@@H](NC(=O)c2n[nH]c3ccc(C(F)(F)F)cc23)COc2ccccc21]

(S)—N-(5-methyl-4-oxo-2,3,4,5-tetrahydrobenzo[b][1,4]oxazepin-3-yl)-5-(trifluoromethyl)-1H-indazole-3-carboxamide To a solution of [(3S)-5-methyl-4-oxo-2,3-dihydro-1,5-benzoxazepin-3-yl]ammonium chloride (0.030 g, 0.13 mmol) in N,N-dimethylformamide (2 mL) was added 5-(trifluoromethyl)-1H-indazole-3-carboxylic acid (0.036 g, 0.16 mmol, 1.2 equiv, N,N-diisopropylethylamine (0.046 mL, 0.26 mmol, 2 equiv), and (7-azabenzotriazol-1-yloxy)tripyrrolidinophosphonium hexafluorophosphate (0.078 g, 0.14 mmol, 1.1 equiv). The reaction mixture was stirred overnight at RT, then was purified directly by preparative RP-HPLC (20 to 70% acetonitrile in water+0.1% formic acid) affording (S)—N-(5-methyl-4-oxo-2,3,4,5-tetrahydrobenzo[b][1,4]oxazepin-3-yl)-5-(trifluoromethyl)-1H-indazole-3-carboxamide (0.036 mg, 67%) as a light brown solid: $^{1}H$ NMR (400 MHz, DMSO-d6) δ 14.15 (s, 1H), 8.62 (d, J=8.0 Hz, 1H), 8.55-8.28 (m, 1H), 7.91-7.83 (m, 1H), 7.75-7.68 (m, 1H), 7.56-7.49 (m, 1H), 7.40-7.22 (m, 3H), 4.96 (dt, J=11.6, 7.8 Hz, 1H), 4.66 (dd, J=11.6, 9.9 Hz, 1H), 4.48 (dd, J=9.9, 7.7 Hz, 1H), 3.34 (s, 3H). LC-MS $R_T$=5.43 min, m/z=405.1 $(M+H)^+$.

LCMS (5 to 95% acetonitrile in water+0.1% formic acid over 10 mins) retention time 5.43 min, ESI+ found [M+H]=405.1

Example 116

Method G13

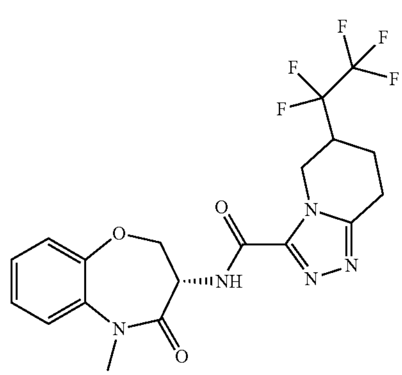 [SMILES: CN1C(=O)[C@@H](NC(=O)c2nnc3n2CC(C(F)(F)C(F)(F)F)CC3)COc2ccccc21]

N—((S)-5-methyl-4-oxo-2,3,4,5-tetrahydrobenzo[b][1,4]oxazepin-3-yl)-6-(perfluoroethyl)-5,6,7,8-tetrahydro-[1,2,4]triazolo[4,3-a]pyridine-3-carboxamide

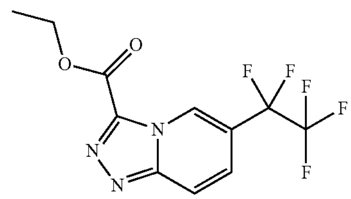 [SMILES: CCOC(=O)c1nnc2ccc(C(F)(F)C(F)(F)F)cn12]

Step 1: ethyl 6-(1,1,2,2,2-pentafluoroethyl)-[1,2,4]triazolo[4,3-a]pyridine-3-carboxylate To a solution of ethyl 6-bromo-[1,2,4]triazolo[4,3-a]pyridine-3-carboxylate (0.100 g, 0.37 mmol) in N,N-dimethylformamide (2 mL) was added (1,1,2,2,2-Pentafluoroethyl)(1,10-phenanthroline-κN1, κN10)copper (0.201 g, 0.56 mmol, 1.5 equiv). The reaction mixture was heated to 90° C. for 24 h, then was diluted with isopropyl acetate (25 mL) and water (25 mL). The layers were separated, and the aqueous was extracted two more times with isopropyl acetate (2×25 mL). The combined organics were washed with water and brine, dried over sodium sulfate, filtered and concentrated to dryness in vacuo. The residue was purified by column chromatography (silica gel, 100-200 mesh, 0 to 100% isopropyl acetate in heptane) affording ethyl 6-(1,1,2,2,2-pentafluoroethyl)-[1,2,4]triazolo[4,3-a]pyridine-3-carboxylate (0.055 mg, 0.18 mmol, 48%) as an off white solid.

LCMS (5 to 95% acetonitrile in water+0.1% formic acid over 2 mins) retention time 1.24 min, ESI+ found [M+H]=310

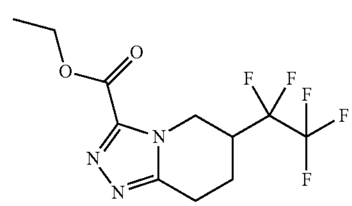 [SMILES: CCOC(=O)c1nnc2n1CC(C(F)(F)C(F)(F)F)CC2]

Step 2: ethyl 6-(1,1,2,2,2-pentafluoroethyl)-5,6,7,8-tetrahydro-[1,2,4]triazolo[4,3-a]pyridine-3-carboxylate To a solution of ethyl 6-(1,1,2,2,2-pentafluoroethyl)-[1,2,4]triazolo[4,3-a]pyridine-3-carboxylate (0.055 g, 0.18 mmol) in methanol (2 mL) was added palladium hydroxide (10 wt %, 0.037 g, 0.027 mmol, 0.15 equiv). The reaction mixture stirred for 16 h at RT under a balloon of hydrogen. The reaction mixture was then filtered through Celite and concentrated to dryness in vacuo affording ethyl 6-(1,1,2,2,2-pentafluoroethyl)-5,6,7,8-tetrahydro-[1,2,4]triazolo[4,3-a]pyridine-3-carboxylate (0.055 g, 98%) as a white solid which was used without further purification.

LCMS (5 to 95% acetonitrile in water+0.1% formic acid over 2 mins) retention time 1.14 min, ESI+ found [M+H]=314

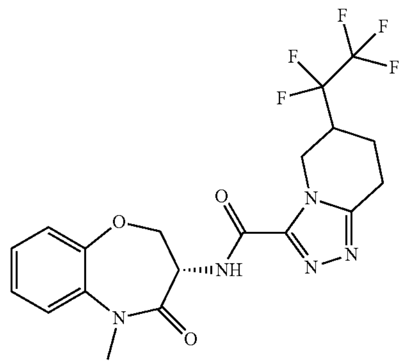 [SMILES: CN1C(=O)[C@@H](NC(=O)c2nnc3n2CC(C(F)(F)C(F)(F)F)CC3)COc2ccccc21]

Step 3: N—((S)-5-methyl-4-oxo-2,3,4,5-tetrahydrobenzo[b][1,4]oxazepin-3-yl)-6-(perfluoroethyl)-5,6,7,8-tetrahydro-[1,2,4]triazolo[4,3-a]pyridine-3-carboxamide To a solution of ethyl 6-(1,1,2,2,2-pentafluoroethyl)-5,6,7,8-tetrahydro-[1,2,4]triazolo[4,3-a]pyridine-3-carboxylate (0.055 g, 0.18 mmol) dissolved in methanol (1 mL) was added 1M aqueous sodium hydroxide (0.200 mL). The reaction mixture was stirred for 1 h at RT, then concentrated to dryness in vacuo. The residue was resuspended in N,N-dimethylformamide (2 mL), and to it was added [(3S)-5-methyl-4-oxo-2,3-dihydro-1,5-benzoxazepin-3-yl]ammonium chloride (0.030 g, 0.13 mmol), N,N-diisopropylethylamine (0.069 mL, 0.39 mmol), and (7-azabenzotriazol-1-yloxy)tripyrrolidinophosphonium hexafluorophosphate (0.086 g, 0.16 mmol). The reaction mixture was stirred for 16 h at RT, then was purified directly by preparative RP-HPLC (20-60% acetonitrile in water+0.1% formic acid) affording N—((S)-5-methyl-4-oxo-2,3,4,5-tetrahydrobenzo[b][1,4]oxazepin-3-yl)-6-(perfluoroethyl)-5,6, 7,8-tetrahydro-[1,2,4]triazolo[4,3-a]pyridine-3-carboxamide (0.049 g, 81%) as a white solid:

$^1$H NMR (400 MHz, DMSO-d6) δ 8.95 (dd, J=8.1, 1.3 Hz, 1H), 7.50 (ddd, J=7.3, 1.9, 0.9 Hz, 1H), 7.38-7.26 (m, 2H), 7.26-7.20 (m, 1H), 4.89-4.78 (m, 1H), 4.72-4.59 (m, 2H), 4.40 (ddd, J=9.8, 7.6, 3.3 Hz, 1H), 4.13-4.02 (m, 1H), 3.32 (s, 3H), 3.17-3.08 (m, 1H), 3.00-2.88 (m, 1H), 2.26-2.15 (m, 1H), 2.01-1.83 (m, 1H). LC-MS $R_T$=5.00 min, m/z=460.1 $(M+H)^+$.

LCMS (5 to 95% acetonitrile in water+0.1% formic acid over 10 mins) retention time 5.00 min, ESI+ found [M+H]=460.1

Example 117: Method G8

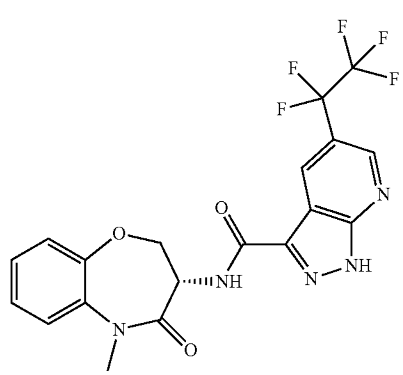 [SMILES: CN1C(=O)[C@@H](NC(=O)c2n[nH]c3ncc(C(F)(F)C(F)(F)F)cc23)COc2ccccc21]

(S)—N-(5-methyl-4-oxo-2,3,4,5-tetrahydrobenzo[b][1,4]oxazepin-3-yl)-5-(perfluoroethyl)-1H-pyrazolo[3,4-b]pyridine-3-carboxamide

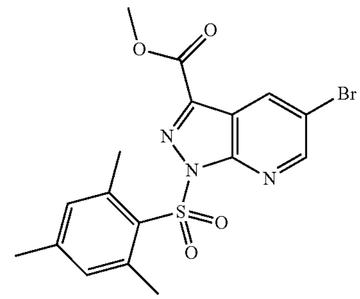 [SMILES: COC(=O)c1nn(S(=O)(=O)c2c(C)cc(C)cc2C)c2ncc(Br)cc12]

Step 1: methyl 5-bromo-1-(2,4,6-trimethylphenyl)sulfonyl-pyrazolo[3,4-b]pyridine-3-carboxylate To a suspension of methyl 5-bromo-1H-pyrazolo[3,4-b]pyridine-3-carboxylate (0.500 g, 1.95 mmol) in tetrahydrofuran (10 mL) was added triethylamine (0.544 mL, 3.93 mmol, 2 equiv), 2-mesitylenesulfonyl chloride (0.475 g, 2.15 mmol, 1.1 equiv), and 4-(dimethylamino)pyridine 0.024 mg, 0.20 mmol, 0.1 equiv). The reaction mixture was stirred at RT for 16 h, then was concentrated to dryness in vacuo affording methyl 5-bromo-1-(2,4,6-trimethylphenyl)sulfonyl-pyrazolo[3,4-b]pyridine-3-carboxylate (0.855 g, 99%) as an orange solid which was used in the next step without further purification.

LCMS (5 to 95% acetonitrile in water+0.1% formic acid over 2 mins) retention time 1.77 min, ESI+ found [M+H]=440

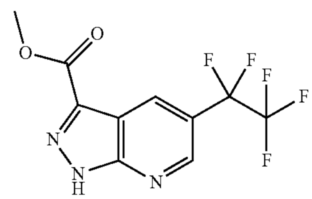 [SMILES: COC(=O)c1n[nH]c2ncc(C(F)(F)C(F)(F)F)cc12]

Step 2: methyl 5-(1,1,2,2,2-pentafluoroethyl)-1H-pyrazolo[3,4-b]pyridine-3-carboxylate To a solution of methyl 5-bromo-1-(2,4,6-trimethylphenyl)sulfonyl-pyrazolo[3,4-b]pyridine-3-carboxylate (0.855 g, 1.95 mmol) in 1-methyl-2-pyrrolidinone was added (1,1,2,2,2-pentafluoroethyl)(1,10-phenanthroline-κN1, κN10) copper (0.990 g, 2.73 mmol, 1.4 equiv). The reaction mixture was heated to 80° C. for 24 h, then was diluted with water (100 mL) and extracted with isopropyl acetate (3×50 mL). The combined organics were washed with water (75 mL) and brine (75 mL), dried over sodium sulfate, and concentrated to dryness in vacuo. The residue was purified by flash column chromatography (silica gel, 100-200 mesh, 0 to 25% isopropyl acetate in heptane) affording methyl 5-(1,1,2,2,2-pentafluoroethyl)-1H-pyrazolo[3,4-b]pyridine-3-carboxylate (0.020 g, 3%) as a pale yellow oil.

LCMS (5 to 95% acetonitrile in water+0.1% formic acid over 2 mins) retention time 1.24 min, ESI+ found [M+H]=296

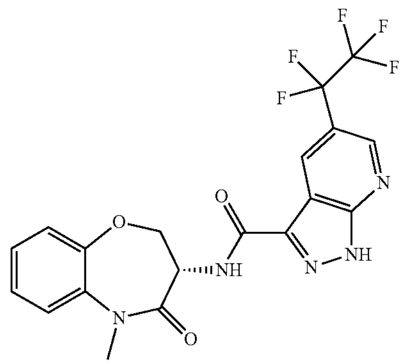 [SMILES: CN1C(=O)[C@@H](NC(=O)c2n[nH]c3ncc(C(F)(F)C(F)(F)F)cc23)COc2ccccc21]

Step 3: (S)—N-(5-methyl-4-oxo-2,3,4,5-tetrahydrobenzo[b][1,4]oxazepin-3-yl)-5-(perfluoroethyl)-1H-pyrazolo[3,4-b]pyridine-3-carboxamide To a solution of methyl 5-(1,1,2,2,2-pentafluoroethyl)-1H-pyrazolo[3,4-b]pyridine-3-carboxylate (0.020 g, 0.07 mmol) dissolved in methanol (1 mL) was added 1M aqueous sodium hydroxide (0.135 mL). The reaction mixture was stirred at 70° C. for 16 h, then concentrated to dryness in vacuo. The residue was resuspended in N,N-dimethylformamide (2 mL), and to it was added [(3S)-5-methyl-4-oxo-2,3-dihydro-1,5-benzoxazepin-3-yl]ammonium chloride (0.030 g, 0.13 mmol), N,N-diisopropylethylamine (0.069 mL, 0.39 mmol), and (7-azabenzotriazol-1-yloxy)tripyrrolidinophosphonium hexafluorophosphate (0.086 g, 0.16 mmol). The reaction mixture was stirred for 16 h at RT, then was purified directly by preparative RP-HPLC (20-70% acetonitrile in water+0.1% formic acid) affording (S)—N-(5-methyl-4-oxo-2,3,4,5-tetrahydrobenzo[b][1,4]oxazepin-3-yl)-5-(perfluoroethyl)-1H-pyrazolo[3,4-b]pyridine-3-carboxamide (0.005 g, 17%) as a white solid: $^1$H NMR (400 MHz, DMSO-$d_6$) δ 14.87 (s, 1H), 8.92 (d, J=2.2 Hz, 1H), 8.82 (d, J=8.0 Hz, 1H), 8.68 (d, J=2.2 Hz, 1H), 7.54-7.50 (m, 1H), 7.38-7.22 (m, 3H), 4.95 (dt, J=11.6, 7.9 Hz, 1H), 4.69 (dd, J=11.6, 9.9 Hz, 1H), 4.47 (dd, J=9.9, 7.7 Hz, 1H), 3.33 (s, 3H). LC-MS $R_T$=5.43 min, m/z=456.1 $(M+H)^+$.

LCMS (5 to 95% acetonitrile in water+0.1% formic acid over 10 mins) retention time 5.43 min, ESI+ found [M+H]=456.1

Example 118

Method G9

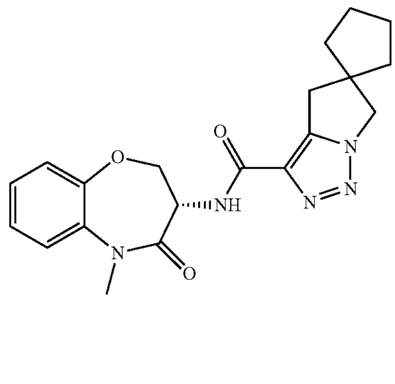 [SMILES: CN1C(=O)[C@@H](NC(=O)c2nnn3c2CC2(CCCC2)C3)COc2ccccc21]

(S)—N-(5-methyl-4-oxo-2,3,4,5-tetrahydrobenzo[b][1,4]oxazepin-3-yl)-4'H,6'H-spiro[cyclopentane-1,5'-pyrrolo[1,2-c][1,2,3]triazole]-3'-carboxamide

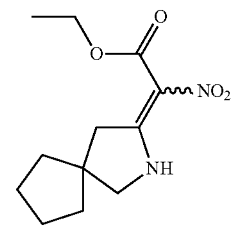 [SMILES: CCOC(=O)C(=C1CC2(CCCC2)CN1)[N+](=O)[O-]]

Step 1: ethyl 2-(8-azaspiro[4.4]nonan-7-ylidene)-2-nitro-acetate

To a solution of 8-azaspiro[4.4]nonan-7-one (1.39 g, 10 mmol) in dichloromethane (50 mL) was added potassium carbonate (4.15 g, 30 mmol, 3 equiv) and trimethyloxonium tetrafluoroborate (2.96 g, 20 mmol, 2 equiv). The reaction mixture was stirred for 16 h at RT, then was diluted with water (100 mL) and the layers separated. The aqueous was extracted two more times with dichloromethane (2×75 mL). The combined organics were washed with brine (50 mL), dried over sodium sulfate, and concentrated to dryness in vacuo. The residue was resuspended in ethyl nitroacetate (4.45 mL, 40 mmol, 4 equiv) and heated to 70° C. for 7 h. After cooling to rt, the mixture was purified directly by flash column chromatography (silica gel, 100-200 mesh, 0 to 50% isopropyl acetate in heptane) affording ethyl 2-(8-azaspiro[4.4]nonan-7-ylidene)-2-nitro-acetate (1.09 g, 43%) as a yellow oil.

LCMS (5 to 95% acetonitrile in water+0.1% formic acid over 2 mins) retention time 1.25 min, ESI+ found [M+H]=255

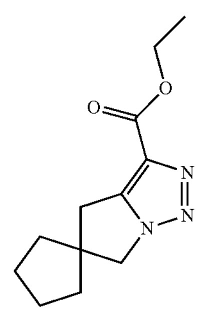 [SMILES: CCOC(=O)c1nnn2c1CC1(CCCC1)C2]

Step 2: ethyl spiro[4,6-dihydropyrrolo[1,2-c]triazole-5,1'-cyclopentane]-3-carboxylate To a solution of ethyl (2E)-2-(8-azaspiro[4.4]nonan-7-ylidene)-2-nitro-acetate (1.09 g, 4.29 mmol) in acetic acid (13.4 mL) cooled to 0° C. was added zinc dust (1.68 g, 25.7 mmol, 6 equiv). The reaction mixture was warmed to RT and stirred for 1 h. After this time, the mixture was filtered through Celite, the filtrate was cooled to 0° C., and to it was added trifluoroacetic acid (1.13 mL, 15.0 mmol, 3.5 equiv) followed by tert-butyl nitrite (1.68 mL, 14.1 mmol, 3.3 equiv). The reaction mixture was warmed to RT and stirred for 2 h. After this time, water (13.4 mL) was added, and then the entire mixture was concentrated to dryness in vacuo. The residue was purified by flash column chromatography (silica gel, 100-200 mesh, 0 to 70% isopropyl acetate in heptane) affording ethyl spiro[4,6-dihydropyrrolo[1,2-c]triazole-5,1'-cyclopentane]-3-carboxylate (0.410 g, 47%).

LCMS (5 to 95% acetonitrile in water+0.1% formic acid over 2 mins) retention time 1.18 min, ESI+ found [M+H]=236

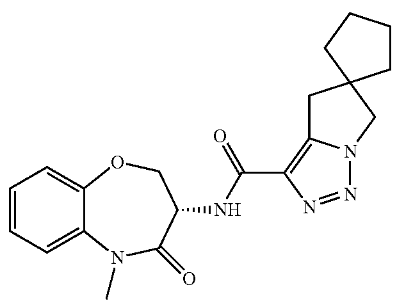 [SMILES: CN1C(=O)[C@@H](NC(=O)c2nnn3c2CC2(CCCC2)C3)COc2ccccc21]

Step 3: (S)—N-(5-methyl-4-oxo-2,3,4,5-tetrahydrobenzo[b][1,4]oxazepin-3-yl)-4'H,6'H-spiro[cyclopentane-1,5'-pyrrolo[1,2-c][1,2,3]triazole]-3'-carboxamide To a solution of ethyl spiro[4,6-dihydropyrrolo[1,2-c]triazole-5,1'-cyclopentane]-3-carboxylate (0.105 g, 0.45 mmol) dissolved in methanol (1 mL) was added 1M aqueous sodium hydroxide (0.893 mL). The reaction mixture was stirred at 50° C. for 1 h, then concentrated to dryness in vacuo. The residue was resuspended in N,N-dimethylformamide (2 mL), and to it was added [(3S)-5-methyl-4-oxo-2,3-dihydro-1,5-benzoxazepin-3-yl]ammonium chloride (0.035 g, 0.15 mmol), N,N-diisopropylethylamine (0.080 mL, 0.46 mmol), and (7-azabenzotriazol-1-yloxy)tripyrrolidinophosphonium hexafluorophosphate (0.100 g, 0.18 mmol). The reaction mixture was stirred for 16 h at RT, then was purified directly by preparative RP-HPLC (20-60% acetonitrile in water+0.1% formic acid) affording (S)—N-(5-methyl-4-oxo-2,3,4,5-tetrahydrobenzo[b][1,4]oxazepin-3-yl)-5-(perfluoroethyl)-1H-pyrazolo[3,4-b]pyridine-3-carboxamide (0.039 g, 66%) as a white solid: $^1$H NMR (400 MHz, DMSO-d6) δ 8.39 (d, J=8.0 Hz, 1H), 7.53-7.46 (m, 1H), 7.38-7.19 (m, 3H), 4.84 (dt, J=11.6, 7.9 Hz, 1H), 4.61 (dd, J=11.6, 9.9 Hz, 1H), 4.40 (dd, J=9.9, 7.7 Hz, 1H), 4.25 (d, J=0.9 Hz, 2H), 3.31 (s, 3H), 2.88 (s, 2H), 1.80-1.62 (m, 8H). LC-MS $R_T$=4.82 min, m/z=382.2 $(M+H)^+$.

LCMS (5 to 95% acetonitrile in water+0.1% formic acid over 10 mins) retention time 4.82 min, ESI+ found [M+H]=382.2

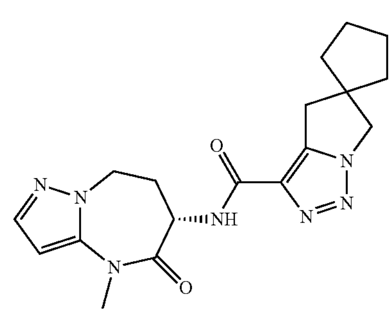 [SMILES: CN1C(=O)[C@@H](NC(=O)c2nnn3c2CC2(CCCC2)C3)CCn2nccc21]

(S)—N-(4-methyl-5-oxo-5,6,7,8-tetrahydro-4H-pyrazolo[1,5-a][1,3]diazepin-6-yl)-4'H,6'H-spiro[cyclopentane-1,5'-pyrrolo[1,2-c][1,2,3]triazole]-3'-carboxamide (S)—N-(4-methyl-5-oxo-5,6,7,8-tetrahydro-4H-pyrazolo[1,5-a][1,3]diazepin-6-yl)-4'H,6'H-spiro[cyclopentane-1,5'-pyrrolo[1,2-c][1,2,3]triazole]-3'-carboxamide was prepared from (S)-6-amino-4-methyl-7,8-dihydro-4H-pyrazolo[1,5-a][1,3]diazepin-5(6H)-one according to Method G9. Yield of final step: 0.019 g, 30%: $^1$H NMR (400 MHz, DMSO-d6) δ 8.49 (d, J=7.9 Hz, 1H), 7.49 (d, J=2.0 Hz, 1H), 6.32 (d, J=2.0 Hz, 1H), 4.43-4.27 (m, 2H), 4.25 (d, J=1.0 Hz, 2H), 4.19 (ddd, J=14.6, 12.7, 6.6 Hz, 1H), 3.25 (s, 3H), 2.89 (s, 2H), 2.58 (ddd, J=12.9, 8.0, 5.0 Hz, 1H), 2.47-2.35 (m, 1H), 1.81-1.59 (m, 8H). LC-MS $R_T$=3.80 min, m/z=370.2 $(M+H)^+$.

LCMS (5 to 95% acetonitrile in water+0.1% formic acid over 10 mins) retention time 3.80 min, ESI+ found [M+H]=370.2

Example 119

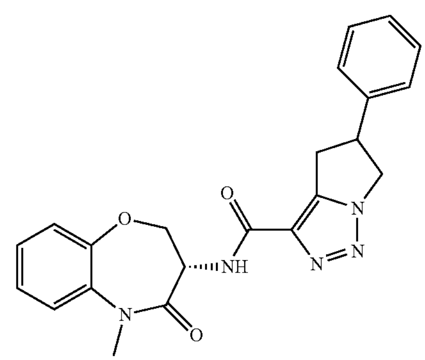 [SMILES: CN1C(=O)[C@@H](NC(=O)c2nnn3c2CC(c2ccccc2)C3)COc2ccccc21]

N—((S)-5-methyl-4-oxo-2,3,4,5-tetrahydrobenzo[b][1,4]oxazepin-3-yl)-5-phenyl-5,6-dihydro-4H-pyrrolo[1,2-c][1,2,3]triazole-3-carboxamide N—((S)-5-methyl-4-oxo-2,3,4,5-tetrahydrobenzo[b][1,4]oxazepin-3-yl)-5-phenyl-5,6-dihydro-4H-pyrrolo[1,2-c][1,2,3]triazole-3-carboxamide was prepared from 4-phenyl-2-pyrrolidinone according to Method G9. Yield of final step: 0.048 g, 78%: $^1$H NMR (400 MHz, DMSO-d6) δ 8.45 (d, J=8.1 Hz, 1H), 7.53-7.45 (m, 1H), 7.42-7.20 (m, 8H), 4.91-4.81 (m, 2H), 4.63 (ddd, J=11.6, 9.9, 1.5 Hz, 1H), 4.49-4.31 (m, 3H), 3.48-3.38 (m, 1H), 3.32 (s, 3H), 3.00 (dd, J=16.3, 8.4 Hz, 1H). LC-MS $R_T$=4.93 min, m/z=404.1 $(M+H)^+$.

LCMS (5 to 95% acetonitrile in water+0.1% formic acid over 10 mins) retention time 4.93 min, ESI+ found [M+H]=404.1

Example 120

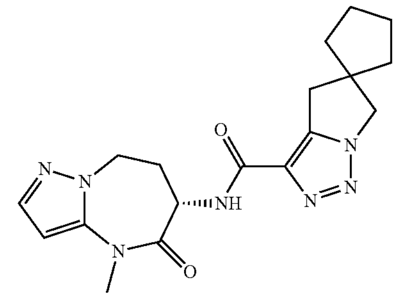 [SMILES: CN1C(=O)[C@@H](NC(=O)c2nnn3c2CC2(CCCC2)C3)CCn2nccc21]

(S)—N-(4-methyl-5-oxo-5,6,7,8-tetrahydro-4H-pyrazolo[1,5-a][1,3]diazepin-6-yl)-4'H,6'H-spiro[cyclopentane-1,5'-pyrrolo[1,2-c][1,2,3]triazole]-3'-carboxamide was prepared according to Method G9.

1H NMR (400 MHz, DMSO-d6) δ 8.55 (d, J=7.8 Hz, 1H), 7.49 (d, J=2.0 Hz, 1H), 7.42-7.32 (m, 4H), 7.32-7.24 (m, 1H), 6.32 (d, J=2.0 Hz, 1H), 4.85 (ddd, J=11.3, 8.1, 3.6 Hz, 1H), 4.50-4.27 (m, 3H), 4.20 (ddd, J=14.6, 12.6, 6.6 Hz, 1H), 3.48-3.38 (m, 1H), 3.25 (d, J=1.6 Hz, 3H), 3.01 (dd, J=16.4, 8.3 Hz, 1H), 2.66-2.54 (m, 1H), 2.48-2.37 (m, 1H).

LCMS (5 to 95% acetonitrile in water+0.1% formic acid over 10 mins) retention time 3.97 min, ESI+ found [M+H]=392.2

Example 121

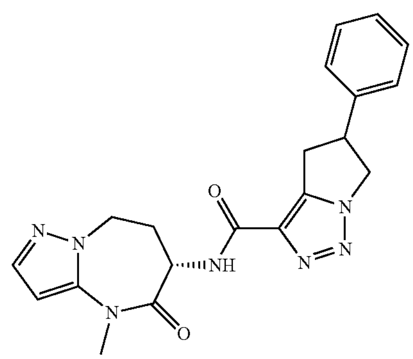 [SMILES: CN1C(=O)[C@@H](NC(=O)c2nnn3c2CC(c2ccccc2)C3)CCn2nccc21]

N—((S)-4-methyl-5-oxo-5,6,7,8-tetrahydro-4H-pyrazolo[1,5-a][1,3]diazepin-6-yl)-5-phenyl-5,6-dihydro-4H-pyrrolo[1,2-c][1,2,3]triazole-3-carboxamide N—((S)-4-methyl-5-oxo-5,6,7,8-tetrahydro-4H-pyrazolo[1,5-a][1,3]diazepin-6-yl)-5-phenyl-5, 6-dihydro-4H-pyrrolo[1,2-c][1,2,3]triazole-3-carboxamide was prepared from (S)-6-amino-4-methyl-7,8-dihydro-4H-pyrazolo[1,5-a][1,3]diazepin-5(6H)-one and 4-phenyl-2-pyrrolidinone according to Method G9. Yield of final step: 0.013 g, 19%: $^1$H NMR (400 MHz, DMSO-d6) δ 8.55 (d, J=7.8 Hz, 1H), 7.49 (d, J=2.0 Hz, 1H), 7.42-7.32 (m, 4H), 7.32-7.24 (m, 1H), 6.32 (d, J=2.0 Hz, 1H), 4.85 (ddd, J=11.3, 8.1, 3.6 Hz, 1H), 4.50-4.27 (m, 3H), 4.20 (ddd, J=14.6, 12.6, 6.6 Hz, 1H), 3.48-3.38 (m, 1H), 3.25 (d, J=1.6 Hz, 3H), 3.01 (dd, J=16.4, 8.3 Hz, 1H), 2.66-2.54 (m, 1H), 2.48-2.37 (m, 1H). LC-MS $R_T$=3.97 min, m/z=392.2 $(M+H)^+$.

LCMS (5 to 95% acetonitrile in water+0.1% formic acid over 10 mins) retention time 3.97 min, ESI+ found [M+H]=392.2.

Example 122

Method G10

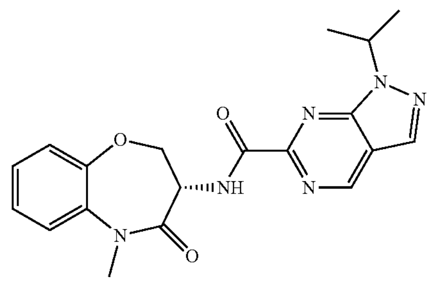 [SMILES: CC(C)n1ncc2cnc(C(=O)N[C@H]3COc4ccccc4N(C)C3=O)nc21]

(S)-1-isopropyl-N-(5-methyl-4-oxo-2,3,4,5-tetrahydrobenzo[b][1,4]oxazepin-3-yl)-1H-pyrazolo[3,4-d]pyrimidine-6-carboxamide

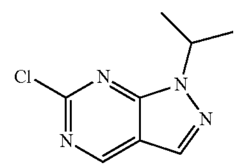

Step 1: 6-chloro-1-isopropyl-pyrazolo[3,4-d]pyrimidine

To a solution of 6-chloro-1H-pyrazolo[3,4-d]pyrimidine (0.417 g, 2.70 mmol) in 1-methyl-2-pyrrolidinone (2 mL) was added potassium carbonate (0.745 g, 5.40 mmol, 2 equiv) and 2-iodopropane (0.540 mL, 5.4 mmol, 2 equiv). The reaction mixture was stirred for 3 h at 60° C., then was diluted with dichloromethane, filtered through Celite, and concentrated to dryness in vacuo. The residue was purified by flash column chromatography (silica gel, 100-200 mesh, 0 to 50% isopropyl acetate in heptane) affording 6-chloro-1-isopropyl-pyrazolo[3,4-d]pyrimidine (0.240 g, 45%) as a white solid.

LCMS (5 to 95% acetonitrile in water+0.1% formic acid over 2 mins) retention time 1.11 min, ESI+ found [M+H]=197.

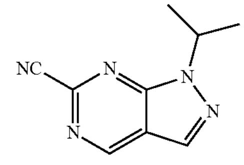

Step 2: 1-isopropylpyrazolo[3,4-d]pyrimidine-6-carbonitrile

To a solution of sodium cyanide (0.071 g, 1.46 mmol, 1.2 equiv) in water (1.5 mL) was added 1,4-diazabicyclo[2.2.2] octane (0.025 mL, 0.24 mmol, 0.20000 equiv), followed by a solution of 6-chloro-1-isopropyl-pyrazolo[3,4-d]pyrimidine (0.240 g, 1.2205 mmol, 1 equiv) in dimethyl sulfoxide (1.5 mL). The reaction mixture stirred for 16 h at RT, then was diluted with water (50 mL) and extracted with isopropyl acetate (3×50 mL). The combined organics were washed with brine (75 mL), dried over sodium sulfate, filtered and concentrated to dryness in vacuo. The residue was purified by flash column chromatography (silica gel, 100-200 mesh, 0 to 50% isopropyl acetate in heptane) affording 1-isopropylpyrazolo[3,4-d]pyrimidine-6-carbonitrile (0.036 g, 16%) as an orange solid.

LCMS (5 to 95% acetonitrile in water+0.1% formic acid over 2 mins) retention time 1.14 min, ESI+ found [M+H]=188.

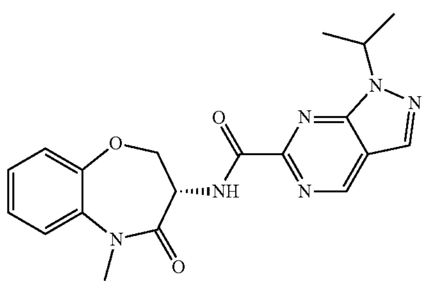 [SMILES: CC(C)n1ncc2cnc(C(=O)N[C@H]3COc4ccccc4N(C)C3=O)nc21]

Step 3: (S)-1-isopropyl-N-(5-methyl-4-oxo-2,3,4,5-tetrahydrobenzo[b][1,4]oxazepin-3-yl)-1H-pyrazolo[3,4-d]pyrimidine-6-carboxamide To a suspension of 1-isopropylpyrazolo[3,4-d]pyrimidine-6-carbonitrile (0.036 g, 0.19 mmol) in water (0.5 mL) was added 1M aqueous sodium hydroxide (0.577 mL). The reaction mixture was stirred at 50° C. for 2 h, then concentrated to dryness in vacuo. The residue was resuspended in N,N-dimethylformamide (2 mL), and to it was added [(3S)-5-methyl-4-oxo-2,3-dihydro-1,5-benzoxazepin-3-yl]ammonium chloride (0.035 g, 0.15 mmol), N,N-diisopropylethylamine (0.080 mL, 0.46 mmol), and (7-azabenzotriazol-1-yloxy)tripyrrolidinophosphonium hexafluorophosphate (0.100 g, 0.18 mmol). The reaction mixture was stirred for 16 h at RT, then was purified directly by preparative RP-HPLC (5-50% acetonitrile in water+0.1% formic acid) affording (S)-1-isopropyl-N-(5-methyl-4-oxo-2,3,4,5-tetrahydrobenzo[b][1,4]oxazepin-3-yl)-1H-pyrazolo[3,4-d]pyrimidine-6-carboxamide (0.028 g, 48%) as a white solid: $^1$H NMR (400 MHz, DMSO-d6) δ 9.46 (s, 1H), 9.13 (d, J=7.8 Hz, 1H), 8.51 (s, 1H), 7.58-7.49 (m, 1H), 7.39-7.24 (m, 3H), 5.27 (p, J=6.7 Hz, 1H), 4.92 (dt, J=11.1, 7.9 Hz, 1H), 4.65-4.49 (m, 2H), 3.35 (s, 3H), 1.53 (dd, J=6.7, 0.8 Hz, 6H). LC-MS $R_T$=4.44 min, m/z=381.1 $(M+H)^+$.

LCMS (5 to 95% acetonitrile in water+0.1% formic acid over 10 mins) retention time 4.44 min, ESI+ found [M+H]=381.1

Example 123

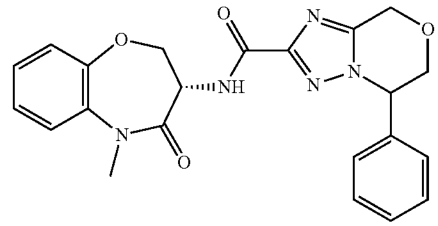 [SMILES: CN1C(=O)[C@@H](NC(=O)c2nc3n(n2)C(c2ccccc2)COC3)COc2ccccc21]

N—((S)-5-methyl-4-oxo-2,3,4,5-tetrahydrobenzo[b][1,4]oxazepin-3-yl)-5-phenyl-5,6-dihydro-8H-[1,2,4]triazolo[5,1-c][1,4]oxazine-2-carboxamide N—((S)-5-methyl-4-oxo-2,3,4,5-tetrahydrobenzo[b][1,4]oxazepin-3-yl)-5-phenyl-5,6-dihydro-8H-[1,2,4]triazolo[5,1-c][1,4]oxazine-2-carboxamide was prepared from 5-phenylmorpholin-3-one and [(3S)-5-methyl-4-oxo-2,3-dihydro-1,5-benzoxazepin-3-yl]ammonium chloride according to Method G11. Yield of final step: 0.025 g, 39%: $^1$H NMR (400 MHz, DMSO-d6) δ 8.48 (d, J=8.0 Hz, 1H), 7.54-7.46 (m, 1H), 7.43-7.16 (m, 8H), 5.65 (t, J=4.5 Hz, 1H), 5.13 (d, J=15.7 Hz, 1H), 5.04-4.96 (m, 1H), 4.81 (dt, J=11.5, 7.9 Hz, 1H), 4.59 (dd, J=11.6, 9.9 Hz, 1H), 4.44-4.31 (m, 2H), 3.30 (s, 3H). LC-MS $R_T$=4.57 min, m/z=420.1 $(M+H)^+$.

LCMS (5 to 95% acetonitrile in water+0.1% formic acid over 10 mins) retention time 4.57 min, ESI+ found [M+H]=420.1

Example 124

Method G11

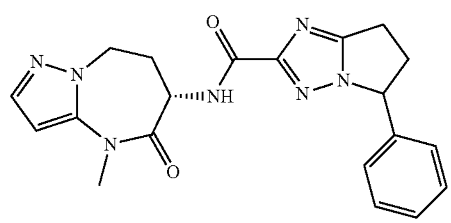

N—((S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide

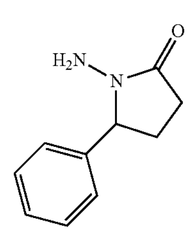 [SMILES: NN1C(=O)CCC1c1ccccc1]

Step 1: 1-amino-5-phenyl-pyrrolidin-2-one

To a solution of 5-phenylpyrrolidin-2-one (0.200 g, 1.24 mmol) in 1,2-dimethoxyethane (8 mL) was added sodium hydride (60% suspension in mineral oil, 0.099 g, 2.48 mmol, 2 equiv). The reaction mixture was stirred for 30 mins at RT, then was cooled to 0° C. To the cooled mixture was added a solution of O-mesitylenesulfonylhydroxylamine (0.610 g, 2.83 mmol, 2.3 equiv) in 1,2-dimethoxyethane (5 mL). The resulting mixture was warmed to RT and stirred for 16 h. The reaction was quenched with methanol (0.1 mL) and concentrated to dryness in vacuo. The residue was purified by flash column chromatography (silica gel, 100-200 mesh, 0 to 7.5% methanol in isopropyl acetate) affording 1-amino-5-phenyl-pyrrolidin-2-one (0.195 g, 89%) as a white solid.

LCMS (5 to 95% acetonitrile in water+0.1% formic acid over 2 mins) retention time 1.11 min, ESI+ found [M+H]=177.

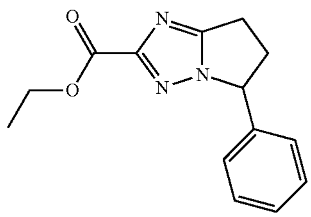 [SMILES: CCOC(=O)c1nc2n(n1)C(c1ccccc1)CC2]

Step 2: ethyl 5-phenyl-6,7-dihydro-5H-pyrrolo[1,2-b][1,2,4]triazole-2-carboxylate To a suspension of 1-amino-5-phenyl-pyrrolidin-2-one (0.150 g, 0.85 mmol) in toluene (1.5 mL) was added acetic acid (0.15 mL, 2.6 mmol, 3 equiv) followed by ethyl 2-amino-2-thioxo-acetate (0.125 g, 0.94 mmol, 1.1 equiv). The reaction mixture was heated to 90° C. and stirred for 16 h. The mixture was loaded directly onto silica gel and purified by flash column chromatography (silica gel, 100-200 mesh, 0 to 100% isopropyl acetate in heptane) affording ethyl 5-phenyl-6,7-dihydro-5H-pyrrolo[1,2-b][1,2,4]triazole-2-carboxylate (0.024 g, 11%) as a colorless oil.

LCMS (5 to 95% acetonitrile in water+0.1% formic acid over 2 mins) retention time 1.09 min, ESI+ found [M+H]=258.

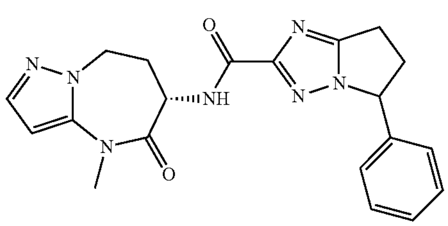 [SMILES: CN1C(=O)[C@@H](NC(=O)c2nc3n(n2)C(c2ccccc2)CC3)CCn2nccc21]

Step 3: N—((S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide To a solution of ethyl 5-phenyl-6,7-dihydro-5H-pyrrolo[1,2-b][1,2,4]triazole-2-carboxylate (0.024 g, 0.09 mmol) in tetrahydrofuran (0.5 mL) was added 1M aqueous sodium hydroxide (0.187 mL). The reaction mixture was stirred at 50° C. for 1 h, then concentrated to dryness in vacuo. The residue was resuspended in N,N-dimethylformamide (2 mL), and to it was added (S)-6-amino-4-methyl-7,8-dihydro-4H-pyrazolo[1,5-a][1,3]diazepin-5(6H)-one (0.030 g, 0.17 mmol), N,N-diisopropylethylamine (0.087 mL, 0.50 mmol), and (7-azabenzotriazol-1-yloxy)tripyrrolidinophosphonium hexafluorophosphate (0.109 g, 0.20 mmol). The reaction mixture was stirred for 16 h at RT, then was purified directly by preparative RP-HPLC (20-60% acetonitrile in water+0.1% formic acid) affording N—((S)-4-methyl-5-oxo-5,6,7,8-tetrahydro-4H-pyrazolo[1,5-a][1,3]diazepin-6-yl)-5-phenyl-6, 7-dihydro-5H-pyrrolo[1,2-b][1,2,4]triazole-2-carboxamide (0.023 g, 34%) as a white solid: $^1$H NMR (400 MHz, DMSO-d6) δ 8.50 (t, J=7.5 Hz, 1H), 7.48 (d, J=2.0 Hz, 1H), 7.44-7.32 (m, 3H), 7.27-7.20 (m, 2H), 6.33 (dd, J=2.0, 1.0 Hz, 1H), 5.57 (dd, J=8.2, 5.9 Hz, 1H), 4.41-4.24 (m, 2H), 4.24-4.12 (m, 1H), 3.24 (d, J=1.1 Hz, 3H), 3.22-3.06 (m, 2H), 3.05-2.94 (m, 1H), 2.61-2.52 (m, 2H), 2.44-2.30 (m, 1H). LC-MS $R_T$=3.73 min, m/z=392.2 $(M+H)^+$.

LCMS (5 to 95% acetonitrile in water+0.1% formic acid over 10 mins) retention time 3.73 min, ESI+ found [M+H]=392.2

Examples 125 and 126

Method G12

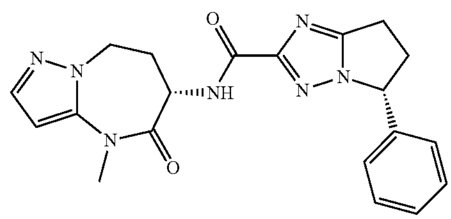

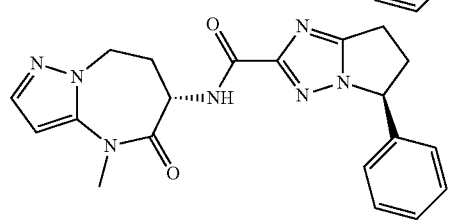

(R)—N—((S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide and (S)—N—((S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide (1:1)

N—((S)-4-methyl-5-oxo-5,6,7,8-tetrahydro-4H-pyrazolo[1,5-a][1,3]diazepin-6-yl)-5-phenyl-6, 7-dihydro-5H-pyrrolo[1,2-b][1,2,4]triazole-2-carboxamide was further purified by chiral SFC (Lux Cellulose-4 column, 50% methanol+0.1% ammonium hydroxide isocratic elution) affording arbitrarily assigned diastereomers (R)—N—((S)-4-methyl-5-oxo-5,6,7,8-tetrahydro-4H-pyrazolo[1,5-a][1,3]diazepin-6-yl)-5-phen yl-6,7-dihydro-5H-pyrrolo[1,2-b][1,2,4]triazole-2-carboxamide (0.006 g, 9%) and (S)—N—((S)-4-methyl-5-oxo-5,6,7,8-tetrahydro-4H-pyrazolo[1,5-a]

[1,3]diazepin-6-yl)-5-phenyl-6,7-dihydro-5H-pyrrolo[1,2-b][1,2,4]triazole-2-carboxamide (0.006 g, 9%) as white solids:

Analytical data for the first eluting diastereomer (arbitrarily assigned R,S configuration): SFC $R_T$ (Lux Cellulose-4 column, 50% methanol+0.1% ammonium hydroxide isocratic elution, 2.5 min method): 1.14 min, 100% ee: $^1$H NMR (400 MHz, DMSO-d6) δ 8.51 (d, J=7.8 Hz, 1H), 7.48 (d, J=2.0 Hz, 1H), 7.44-7.32 (m, 3H), 7.28-7.20 (m, 2H), 6.33 (d, J=2.0 Hz, 1H), 5.57 (dd, J=8.2, 5.9 Hz, 1H), 4.41-4.32 (m, 1H), 4.32-4.23 (m, 1H), 4.23-4.13 (m, 1H), 3.24 (s, 3H), 3.21-3.14 (m, 1H), 3.14-3.04 (m, 1H), 3.04-2.93 (m, 1H), 2.63-2.52 (m, 2H), 2.37 (td, J=12.5, 6.6 Hz, 1H). LCMS $R_T$=3.76 min, m/z=392.2 $(M+H)^+$.

Analytical data for the second eluting diastereomer (arbitrarily assigned S,S configuration): SFC $R_T$: 1.84 min, 100% ee: $^1$H NMR (400 MHz, DMSO-d6) δ 8.49 (d, J=7.7 Hz, 1H), 7.48 (d, J=2.0 Hz, 1H), 7.43-7.32 (m, 3H), 7.26-7.21 (m, 2H), 6.33 (d, J=2.0 Hz, 1H), 5.57 (dd, J=8.3, 5.8 Hz, 1H), 4.41-4.24 (m, 2H), 4.24-4.12 (m, 1H), 3.24 (s, 3H), 3.22-3.06 (m, 2H), 3.05-2.94 (m, 1H), 2.61-2.52 (m, 2H), 2.42-2.31 (m, 1H). LCMS $R_T$=3.76 min, m/z=392.2 $(M+H)^+$.

Example 127

Method C1

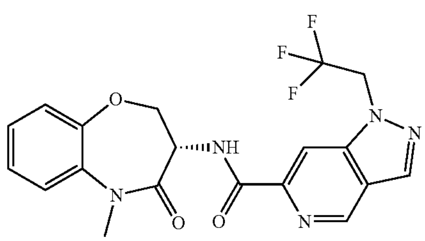 [SMILES: CN1C(=O)[C@@H](NC(=O)c2cc3c(cn2)cnn3CC(F)(F)F)COc2ccccc21]

N-[(3S)-5-methyl-4-oxo-2,3-dihydro-1,5-benzoxazepin-3-yl]-1-(2,2,2 trifluoroethyl)pyrazolo[4,3-c]pyridine-6-carboxamide

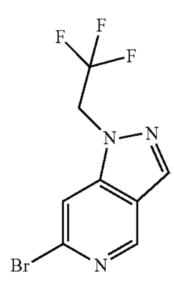 [SMILES: FC(F)(F)Cn1ncc2cnc(Br)cc21]

Step 1: 6-bromo-1-(2,2,2-trifluoroethyl)-1H-pyrazolo[4,3-c]pyridine

A solution of 6-bromo-1H-pyrazolo[4,3-c]pyridine (1.0 g, 5.05 mmol) in N,N-dimethylformamide (9.2 mL) was cooled to 0° C. and sodium hydride (60 mass % in oil, 0.460 g, 11.5 mmol) was added. After 5 min, 2,2,2-trifluoroethyl trifluoromethanesulfonate (3.0 g, 12.9 mmol) was added. The reaction stirred at 0° C. for 10 min and then was warmed to RT and stirred for an additional 18 h. The reaction mixture was sealed with a yellow cap and heated at 60° C. for 1 h. After cooling to RT, the reaction was diluted with water and isopropyl acetate. The aqueous layer was extracted with isopropyl acetate (3×100 mL). The combined organic layers were washed with brine, dried with magnesium sulfate, concentrated to dryness in vacuo, and the residue was purified by flash column chromatography (silica gel, 0% to 50% isopropyl acetate-heptane) to give 6-bromo-1-(2,2,2-trifluoroethyl)pyrazolo[4,3-c]pyridine (0.925 g, 3.30 mmol, 65% Yield): $^1$H NMR (400 MHz, DMSO-d6) δ 8.95 (s, 1H), 8.47 (s, 1H), 8.20 (s, 1H), 5.47 (q, J=8.8 Hz, 2H). LRMS $R_T$=1.25 min, m/z=281 $(M+H)^+$.

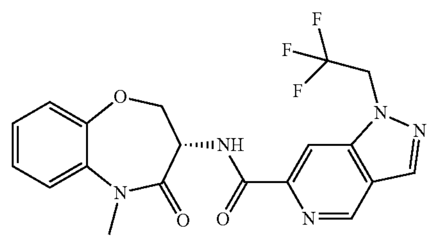 [SMILES: CN1C(=O)[C@@H](NC(=O)c2cc3c(cn2)cnn3CC(F)(F)F)COc2ccccc21]

Step 2: N-[(3S)-5-methyl-4-oxo-2,3-dihydro-1,5-benzoxazepin-3-yl]-1-(2,2,2 trifluoroethyl)pyrazolo[4,3-c]pyridine-6-carboxamide Palladium(II) acetate (3.1 mg, 0.0134 mmol), 4,5-bis(diphenylphosphino)-9,9-dimethylxanthene (7.9 mg, 0.0134 mmol), 6-bromo-1-(2,2,2-trifluoroethyl)pyrazolo[4,3-c]pyridine (75 mg, 0.268 mmol), (3S)-3-amino-5-methyl-2,3-dihydro-1,5-benzoxazepin-4-one (77.2 mg, 0.402 mmol) were added to a screw-cap vial (not dried). A septum was put on the vial and secured with electrical tape. Nitrogen was then purged through the reaction vial for 15 min. The solids were dissolved in toluene (0.53 mL), and triethylamine (0.110 mL, 0.803 mmol) was added. The reaction flask was purged with a balloon for carbon monoxide for 5 minutes. The vial, with the balloon of carbon monoxide, was placed in a 80° C. heating block and was allowed to stir for 16 h. (NOTE: no solvent remained after heating for 16 h). The crude residue was dissolved in isopropyl acetate, and filtered through Celite. The crude residue was purified by flash column chromatography (silica gel, 0% to 60% isopropyl acetate in heptane) to afford N-[(3S)-5-methyl-4-oxo-2,3-dihydro-1,5-benzoxazepin-3-yl]-1-(2,2,2-trifluoroethyl)pyrazolo[4,3-c]pyridine-6-carboxamide (102.6 mg, 0.242 mmol, 90% Yield) as a yellow solid: $^1$H NMR (400 MHz, DMSO-$d_6$) δ 9.26 (d, J=1.2 Hz, 1H), 9.06 (d, J=8.0 Hz, 1H), 8.59 (d, J=0.8 Hz, 1H), 8.52 (bs, 1H), 7.57-7.47 (m, 1H), 7.40-7.24 (m, 3H), 5.75-5.60 (m, 2H), 4.93 (dt, J=10.8, 8.0 Hz, 1H), 4.62-4.48 (m, 2H), 3.35 (s, 3H). LRMS $R_T$=5.04 min, m/z=420.1 $(M+H)^+$.

Prep HPLC Information:

Column: Phenomenex Gemini-NX C18 5 um, 110 A (50×30 mm)

Mobile Phase: 0.1% Ammonium Hydroxide in Water (A)/Acetonitrile (B)

Elution Program

Gradient: 20 to 60% B

Pressure: 900 psi

Flow Rate: 60 mL/min

Column Temperature: 25° C.

Wavelength: 220 nm

Example 128

Method C2

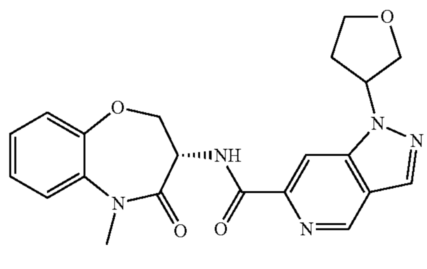 [SMILES: CN1C(=O)[C@@H](NC(=O)c2cc3c(cn2)cnn3C2CCOC2)COc2ccccc21]

N—((S)-5-methyl-4-oxo-2,3,4,5-tetrahydrobenzo[b][1,4]oxazepin-3-yl)-1-(tetrahydrofuran-3-yl)-1H-pyrazolo[4,3-c]pyridine-6-carboxamide

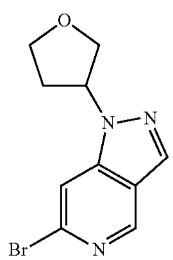 [SMILES: Brc1cc2c(cn1)cnn2C1CCOC1]

Step 1: 6-bromo-1-(tetrahydrofuran-3-yl)-1H-pyrazolo[4,3-c]pyridine

A suspension of sodium hydride (60 mass % in oil, 0.480 g, 12.0 mmol) in N,N-dimethylformamide (9.2 mL) was cooled to 0° C. and 6-bromo-1H-pyrazolo[4,3-c]pyridine (1.0 g, 5.05 mmol) was added. After 5 min, 3-bromotetrahydrofuran (1.80 g, 11.9 mmol) was added. The reaction stirred at 0° C. for 10 min, warmed to RT and stirred for an additional 18 h. Additional sodium hydride (60 mass % in oil, 0.230 g, 5.75 mmol) and 3-bromotetrahydrofuran (0.90 g, 5.96 mmol) was added. The reaction was sealed with a yellow cap and heated at 60° C. for 4 h. After cooling to RT, the reaction was diluted with water and isopropyl acetate. The aqueous layer was extracted with isopropyl acetate. The combined organic layers were washed with brine, dried with magnesium sulfate, concentrated to dryness in vacuo, and the residue was purified by flash column chromatography (silica gel, 0% to 50% isopropyl acetate in heptane) to give 6-bromo-1-tetrahydrofuran-3-yl-pyrazolo[4,3-c]pyridine (0.579 g, 2.16 mmol, 43% Yield): $^{1}$H NMR (400 MHz, DMSO-d6) δ 8.89 (s, 1H), 8.34 (s, 1H), 8.06 (s, 1H), 5.63-5.37 (m, 1H), 4.21-3.98 (m, 2H), 3.98-3.72 (m, 2H), 2.65-2.36 (m, 1H), 2.36-2.19 (m, 1H). LRMS $R_T$=1.03 min, m/z=269 $(M+H)^+$.

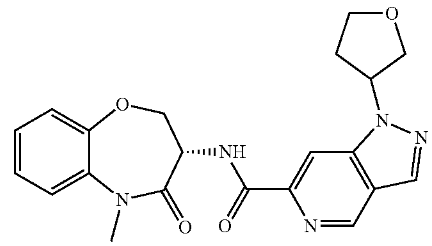 [SMILES: CN1C(=O)[C@@H](NC(=O)c2cc3c(cn2)cnn3C2CCOC2)COc2ccccc21]

Step 2: N—((S)-5-methyl-4-oxo-2,3,4,5-tetrahydrobenzo[b][1,4]oxazepin-3-yl)-1-(tetrahydrofuran-3-yl)-1H-pyrazolo[4,3-c]pyridine-6-carboxamide Palladium(II) acetate (2.6 mg, 0.0112 mmol), 4,5-bis(diphenylphosphino)-9,9-dimethylxanthene (6.6 mg, 0.0112 mmol), 6-bromo-1-tetrahydrofuran-3-yl-pyrazolo[4,3-c]pyridine (60 mg, 0.224 mmol), (3S)-3-amino-5-methyl-2,3-dihydro-1,5-benzoxazepin-4-one (64.5 mg, 0.336 mmol) were added to a screw-cap vial (not dried). A septum was put on the vial and secured with electrical tape. Nitrogen was then purged through the reaction vial for 15 min. The solids were dissolved in toluene (0.45 mL), and then triethylamine (0.095 mL, 0.671 mmol) was added. The reaction flask was purged with a balloon for carbon monoxide for 5 minutes. The vial, with the balloon of carbon monoxide, was placed in a 80° C. heating block and was allowed to stir for 17 h. (NOTE: no solvent remained after heating for 17 h). The crude residue was dissolved in isopropyl acetate, filtered through Celite and concentrated to dryness in vacuo. The residue was purified by flash column chromatography (silica gel, 0% to 75% isopropyl acetate in heptane) to give N—((S)-5-methyl-4-oxo-2,3,4,5-tetrahydrobenzo[b][1,4]oxazepin-3-yl)-1-(tetrahydrofuran-3-yl)-1H-pyrazolo[4,3-c]pyridine-6-carboxamide (55 mg, 60% Yield): $^{1}$H NMR (400 MHz, DMSO-d6) δ 9.20 (d, J=0.8 Hz, 1H), 9.02 (d, J=8.0 Hz, 1H), 8.47-8.46 (m, 1H), 8.40-8.36 (m, 1H), 7.57-7.47 (m, 1H), 7.39-7.24 (m, 3H), 5.73-5.66 (m, 1H), 4.96-4.89 (m, 1H), 4.61-4.50 (m, 2H), 4.14-4.01 (m, 2H), 3.96-3.82 (m, 2H), 3.35 (s, 3H), 2.51-2.39 (m, 1H), 2.34-2.19 (m, 1H). LRMS $R_T$=4.49 min, m/z=408.2 $(M+H)^+$.

Prep HPLC Information:

Column: Phenomenex Gemini-NX C18 5 um, 110 A (50×30 mm)

Mobile Phase: 0.1% Ammonium Hydroxide in Water (A)/Acetonitrile (B)

Elution Program

Gradient: 20 to 60% B

Pressure: 900 psi

Flow Rate: 60 mL/min

Column Temperature: 25° C.

Wavelength: 230 nm

Examples 129 and 130

Method C3

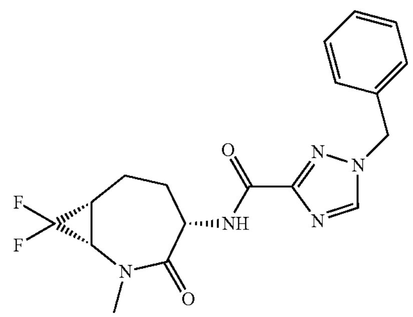

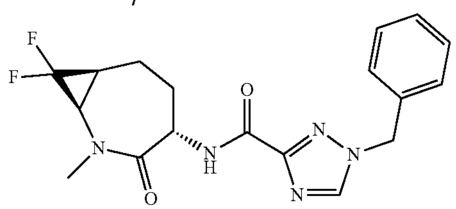

1-benzyl-N-((1S,4S,7R)-8,8-difluoro-2-methyl-3-oxo-2-azabicyclo[5.1.0]octan-4-yl)-1H-1, 2,4-triazole-3-carboxamide and 1-benzyl-N-((1R,4S,7S)-8,8-difluoro-2-methyl-3-oxo-2-azabicyclo[5.1.0]octan-4-yl)-1H-1, 2,4-triazole-3-carboxamide

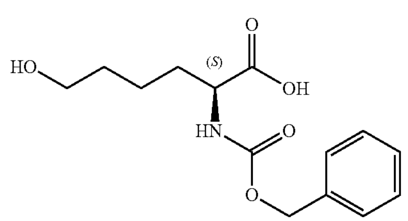

Step 1: (S)-2-(((benzyloxy)carbonyl)amino)-6-hydroxyhexanoic acid ((Benzyloxy)carbonyl)-L-lysine (150 g, 535 mmol) was dissolved in water (1.5 L), and the solution was warmed to 60° C. and adjusted to pH=9.5 with 4M NaOH, disodium pentacyano(nitroso)irondiuide (168 g, 642 mmol) was added slowly with vigorous stirring over 10 min. The reaction mixture was stirred at 60° C. for and maintained pH=9.5 with 4N NaOH for 12 h. The reaction mixture was flittered through a bed of Celite, the filtrate was cautiously acidified with hydrochloric acid to pH=1, and then extracted with ethyl acetate (3×1000 mL). The combined organic layers were washed with brine (200 mL), dried over sodium sulfate, filtered and concentrated to dryness in vacuo to afford (S)-2-(((benzyloxy)carbonyl)amino)-6-hydroxyhexanoic acid (260 g, crude) as a brown oil, use without further purification in the next step.

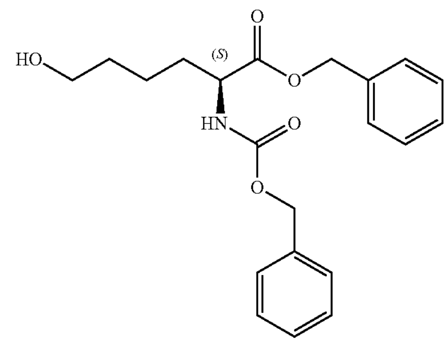

Step 2: benzyl (S)-2-(((benzyloxy)carbonyl)amino)-6-hydroxyhexanoate

A mixture of (S)-2-(((benzyloxy)carbonyl)amino)-6-hydroxyhexanoic acid (130 g, 462 mmol,), cesium carbonate (75 g, 231 mmol), bromomethylbenzene (79. g, 462 mmol) in N,N-dimethylformamide (1 L) and the mixture was stirred at 10° C. for 18 h under nitrogen atmosphere. The reaction mixture was filtered, the filtrate was diluted with water (5 L), the aqueous phase was extracted with ethyl acetate (3×1 L). The combined organic was washed with brine (200 mL), dried with anhydrous sodium sulfate, filtered and concentrated to dryness in vacuo. The resulting residue was purified by column chromatography (silica gel, 100-200 mesh, 50:1 to 0:1 ethyl acetate in petroleum ether) affording benzyl (S)-2-(((benzyloxy)carbonyl)amino)-6-hydroxyhexanoate (222 g, 65%) as a white oil, use without further purification in the next step: HPLC $R_T$=3.16 min

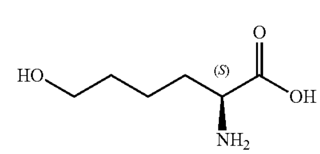

Step 3: (S)-2-amino-6-hydroxyhexanoic acid

To a solution of (S)-2-(((benzyloxy)carbonyl)amino)-6-hydroxyhexanoate (222 g, 598 mmol) in methanol (1 L) was added 10% Pd/C (20 g) under a nitrogen atmosphere. The suspension was degassed under vacuum and purged with hydrogen several times. The mixture was stirred under hydrogen (50 psi) at 50° C. for 2 hrs. The reaction mixture was filtered and the filtrate was concentrated to dryness in vacuo to give (S)-2-amino-6-hydroxyhexanoic acid (85 g, 577 mmol, 97% yield) as a white solid, used use without further purification in the next step: TLC (Petroleum ether/Ethyl acetate=2/1, Rf=0.45)

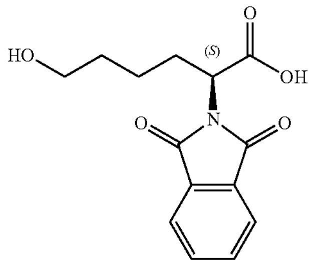

Step 4: (S)-2-(1,3-dioxoisoindolin-2-yl)-6-hydroxyhexanoic acid

To a mixture of (S)-2-amino-6-hydroxyhexanoic acid (50 g, 340 mmol), ethyl 1,3-dioxoisoindoline-2-carboxylate (74 g, 340 mmol) was added sodium carbonate (36 g, 340 mmol) in water (500 mL) was stirred at 10° C. for 2. The reaction mixture was adjust pH=1 and extracted with ethyl acetate (3×250 mL). The combined organic layers were washed with brine (100 mL), dried over sodium sulfate, filtered and concentrated to dryness in vacuo. The residue was washed with 2-methoxy-2-methylpropane (300 mL) and dried to afford (S)-2-(1,3-dioxoisoindolin-2-yl)-6-hydroxyhexanoic acid (47 g, 50%) as a white solid, use without further purification in the next step: HPLC $R_T$=1.83 min

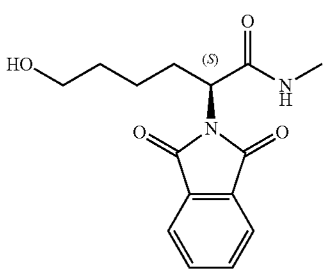

Step 5: (S)-2-(1,3-dioxoisoindolin-2-yl)-6-hydroxy-N-methylhexanamide

A mixture of (S)-2-(1,3-dioxoisoindolin-2-yl)-6-hydroxyhexanoic acid (32 g, 115 mmol), 3-(ethyliminomethyleneamino)-N,N-dimethylpropan-1-amine (33 g, 173 mmol), benzotriazol-1-ol (16 g, 115 mmol) and methanamine (2 M solution in tetrahydrofuran, 144 mL, 287.5 mmol) in tetrahydrofuran (320 mL) was degassed and purged with nitrogen, and the reaction mixture was stirred at 10° C. for 2 h under a nitrogen atmosphere. To the reaction mixture was added water (200 mL) and the mixture was extracted with ethyl acetate (3×100 mL). The combined was washed with brine (20 mL), dried over anhydrous sodium sulfate, filtered and concentrated to dryness in vacuo. The residue was purified by column chromatography (silica gel, 100-200 mesh, 200:1, 50:1 methanol in dichloromethane) to afford (S)-2-(1,3-dioxoisoindolin-2-yl)-6-hydroxy-N-methylhexanamide (16.5 g, 49% yield), used as is in the next step

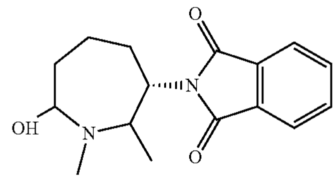 [SMILES: CC1[C@@H](N2C(=O)c3ccccc3C2=O)CCCC(O)N1C]

Step 6: 2-((3S)-7-hydroxy-1-methyl-2-oxoazepan-3-yl)isoindoline-1,3-dione

To a solution of (S)-2-(1,3-dioxoisoindolin-2-yl)-6-hydroxy-N-methylhexanamide (13.8 g, 48 mmol) in dimethylsulfoxide (84 mL) were added triethylamine (24 g, 238 mmol, 33 mL) and sulfur trioxide pyridine complex (38 g, 238 mmol) at 0° C. under an argon atmosphere and the mixture was stirred at 10-20° C. for 2.5 h. The reaction mixture was quenched with water and treated with 1N HCl, and then extracted with ethyl acetate (3×100 mL). The organic layer was washed with brine, dried over sodium sulfate and concentrated to dryness in vacuo to afford 2-((3S)-7-hydroxy-1-methyl-2-oxoazepan-3-yl)isoindoline-1,3-dione (21.2 g, crude) as off-white oil, which was used in the next step without further purification: TLC (dichloromethane/Methanol=10/1, Rf=0.43)

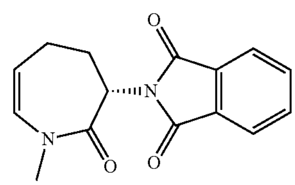 [SMILES: CN1C=CCC[C@H](N2C(=O)c3ccccc3C2=O)C1=O]

Step 7: (S)-2-(1-methyl-2-oxo-2,3,4,5-tetrahydro-1H-azepin-3-yl)isoindoline-1,3-dione A solution of (S)-2-(1,3-dioxoisoindolin-2-yl)-6-hydroxy-N-methylhexanamide (21.2 g, 73 mmol) and p-toluenesulfonic acid monohydrate (839 mg, 4.4 mmol) in toluene (200 mL) was stirred under reflux for 1.5 h. After allowing to cool to RT, the reaction mixture was diluted with ethyl acetate (500 mL) and washed with saturated aqueous sodium bicarbonate (200 mL) and brine (100 mL). The organic layer was dried over sodium sulfate and concentrated to dryness in vacuo. The residue was washed with ethyl acetate (10 mL) and dried to afford (S)-2-(1-methyl-2-oxo-2,3,4,5-tetrahydro-1H-azepin-3-yl)isoindoline-1,3-dione (4.6 g, 23%) as a white solid: $^1$H NMR (400 MHz, $CDCl_3$) δ 7.88 (dd, J=5.52, 3.01 Hz, 2H), 7.71-7.77 (m, 2H), 5.96 (dd, J=9.03, 1.51 Hz, 1H), 5.35-5.45 (m, 1H), 5.04 (dd, J=10.79, 3.26 Hz, 1H), 3.10 (s, 3H), 2.46-2.57 (m, 1H), 2.23-2.40 (m, 2H), 1.61 (s, 1H).

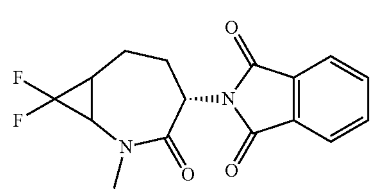 [SMILES: CN1C(=O)[C@@H](N2C(=O)c3ccccc3C2=O)CCC2C1C2(F)F]

Step 1: 2-((4S)-8,8-difluoro-2-methyl-3-oxo-2-azabicyclo[5.1.0]octan-4-yl)isoindoline-1,3-dione A solution of sodium chlorodifluoroacetate (1.42 g, 9.25 mmol) in diglyme (5.9 mL) was added dropwise to a refluxing solution of 2-[(3S)-1-methyl-2-oxo-4,5-dihydro-3H-azepin-3-yl]isoindoline-1,3-dione (0.250 g, 0.925 mmol) in diglyme (10 mL) over 25 minutes. After addition, the reaction was allowed to stir for an additional 10 minutes at reflux. After cooling to RT, the reaction mixture was concentrated to dryness in vacuo and the residue was purified by flash column chromatography (silica gel, 0% to 70% isopropyl acetate in heptane) affording 2-[(4S)-8,8-difluoro-6-methyl-5-oxo-6-azabicyclo[5.1.0]octan-4-yl] isoindoline-1,3-dione (0.270 g, 0.843 mmol, 91% yield) as an inseparable ~6.8:1 mixture of diastereomers: $^1$H NMR (400 MHz, Chloroform-d) 6 (major isomer) 7.90-7.81 (m, 2H), 7.75-7.70 (m, 2H), 5.44 (dd, J=11.6, 8.0 Hz, 1H), 3.66-3.30 (m, 1H), 3.26-3.11 (m, 1H), 3.02 (s, 3H), 2.25-2.15 (m, 1H), 2.04-1.90 (m, 2H), 1.85-1.72 (m, 1H). LRMS $R_T$=1.29 min, m/z=321 (M+H)$^+$.

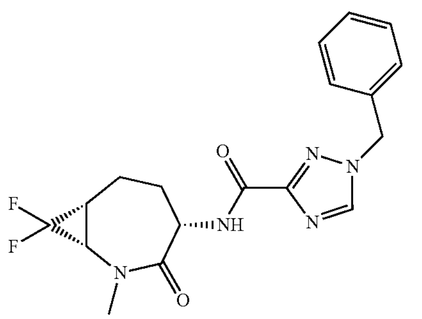

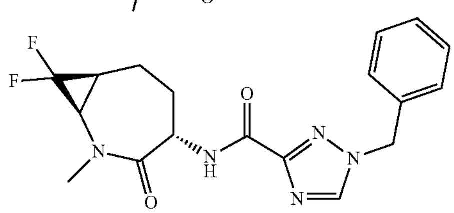

Step 2: 1-benzyl-N-((1S,4S,7R)-8,8-difluoro-2-methyl-3-oxo-2-azabicyclo[5.1.0]octan-4-yl)-1H-1,2,4-triazole-3-carboxamide and 1-benzyl-N-((1R,4S,7S)-8,8-difluoro-2-methyl-3-oxo-2-azabicyclo[5.1.0]octan-4-yl)-1H-1, 2,4-triazole-3-carboxamide Hydrazine (0.087 mL, 2.72 mmol) was added to a solution of 2-[(4S)-8,8-difluoro-6-methyl-5-oxo-6-azabicyclo[5.1.0]octan-4-yl]isoindoline-1,3-dione and (~6.8:1 dr, 0.290 g, 0.905 mmol) in ethanol (9.1 mL). The reaction was heated at 80° C. for 2 h. After cooling to RT, the reaction was filtered through a short plug of Celite using ethanol. The filtrate was concentrated to dryness in vacuo to afford (4S)-4-amino-8,8-difluoro-6-methyl-6-azabicyclo[5.1.0]octan-5-one (88.9 mg, 0.467 mmol, 51.6% Yield). The crude residue was used in the next step without further purification.

(7-Azabenzotriazol-1-yloxy)tripyrrolidinophosphonium hexafluorophosphate (0.138 g, 0.254 mmol) was added to a solution of (4S)-4-amino-8,8-difluoro-6-methyl-6-azabicyclo[5.1.0]octan-5-one (44 mg, 0.231 mmol), 1-benzyl-1,2,4-triazole-3-carboxylic acid (58 mg, 0.289 mmol), and N,N-diisopropylethylamine (0.120 mL, 0.694 mmol), in N,N-dimethylformamide (2.3 mL). The reaction was allowed to stir at RT for 18 h before being concentrated to dryness in vacuo. The crude residue was purified by preparative reverse phase HPLC affording arbitrarily assigned 1-benzyl-N-((1S,4S,7R)-8,8-difluoro-2-methyl-3-oxo-2-azabicyclo[5.1.0]octan-4-yl)-1H-1,2, 4-triazole-3-carboxamide (56.7 mg, 0.151 mmol, 65% Yield) and 1-benzyl-N-((1R,4S,7S)-8,8-difluoro-2-methyl-3-oxo-2-azabicyclo[5.1.0]octan-4-yl)-1H-1, 2, 4-triazole-3-carboxamide (5.7 mg, 6.6%): 1-benzyl-N-((1S,4S,7R)-8,8-difluoro-2-methyl-3-oxo-2-azabicyclo[5.1.0]octan-4-yl)-1H-1,2, 4-triazole-3-carboxamide (arbitrarily assigned): $^1$H NMR (400 MHz, DMSO-d6) δ 8.81 (s, 1H), 8.19 (m, 2H), 7.45-7.20 (m, 5H), 5.49 (s, 2H), 5.00 (dt, J=10.8, 7.2 Hz, 1H), 3.72-3.49 (m, 1H), 2.90 (s, 3H), 2.43-1.96 (m, 4H), 1.61 (m, 1H), 1.27 (m, 1H). LRMS $R_T$=4.18 min, m/z=376.1 (M+H)$^+$.

Prep HPLC Information:
Column: Phenomenex Gemini-NX C18 5 um, 110 A (50×30 mm)
Mobile Phase: 0.1% Ammonium Hydroxide in Water (A)/Acetonitrile (B)
Elution Program
Gradient: 20 to 60% B
Pressure: 800 psi
Flow Rate: 60 mL/min
Column Temperature: 25° C.
Wavelength: 210 nm and 1-benzyl-N-((1R,4S,7S)-8,8-difluoro-2-methyl-3-oxo-2-azabicyclo[5.1.0]octan-4-yl)-1H-1,2, 4-triazole-3-carboxamide (arbitrarily assigned): $^1$H NMR (400 MHz, DMSO-d6) δ 8.82 (s, 1H), 8.58 (d, J=4.4 Hz, 1H), 7.43-7.27 (m, 5H), 5.48 (s, 2H), 4.43-4.33 (m, 1H), 3.27-3.14 (m, 1H), 2.80 (s, 3H), 2.55-2.43 (m, 1H), 2.10-2.00 (m, 3H), 1.30-1.10 (m, 1H). LRMS $R_T$=3.90 min, m/z=376.1 (M+H)$^+$.

Prep HPLC Information:
Column: Phenomenex Gemini-NX C18 5 um, 110 A (50×30 mm)
Mobile Phase: 0.1% Ammonium Hydroxide in Water (A)/Acetonitrile (B)
Elution Program
Gradient: 20 to 60% B
Pressure: 800 psi
Flow Rate: 60 mL/min
Column Temperature: 25° C.
Wavelength: 210 nm Example 131 and 132

Method C3 & C4

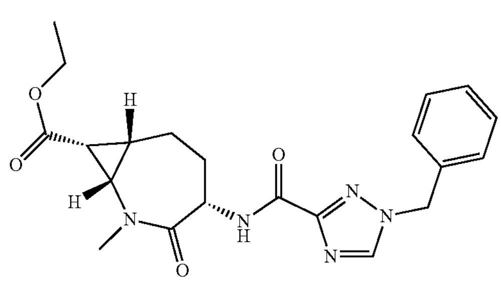

-continued

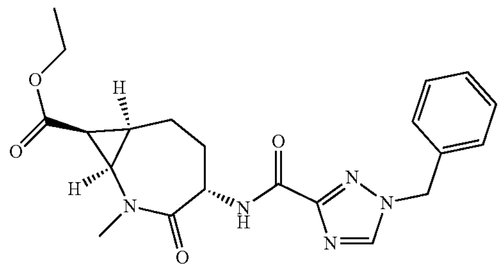

Ethyl(1S,4S,7S,8R)-4-(1-benzyl-1H-1,2,4-triazole-3-1H-triazcarboxamido)-2-methyl-3-oxo-2-aza bicyclo[5.1.0]octane-8-carboxylate and ethyl (1R,4S,7R,8S)-4-(1-benzyl-1H-1,2,4-triazole-3-carboxamido)-2-methyl-3-oxo-2-azabicyclo[5.1.0]octane-8-carboxylate

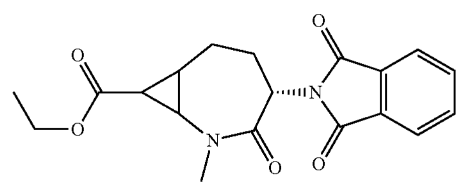 [SMILES: CCOC(=O)C1C2CC[C@H](N3C(=O)c4ccccc4C3=O)C(=O)N(C)C21]

Step 1: ethyl (4S)-4-(1,3-dioxoisoindolin-2-yl)-2-methyl-3-oxo-2-azabicyclo[5.1.0]octane-8-carboxylate A solution of ethyl diazoacetate (15 mass % in toluene, 1.3 mL, 1.5 mmol) in dichloromethane (3 mL) was added dropwise to a solution of the 2-[(3S)-1-methyl-2-oxo-4,5-dihydro-3H-azepin-3-yl]isoindoline-1,3-dione (0.20 g, 0.74 mmol) and rhodium(II) acetate (6.9 mg, 0.030 mmol) in dichloromethane (5.2 mL), over a period of 4 h. After, the reaction was allowed to stir for an additional 12 h. The reaction was then filtered through Celite using isopropyl acetate. The filtrate was concentrated to dryness in vacuo and the residue was purified by flash column chromatography (silica gel, 0% to 70% isopropyl acetate in heptane) to give ethyl (4S)-4-(1,3-dioxoisoindolin-2-yl)-6-methyl-5-oxo-6-azabicyclo[5.1.0]octane-8-carboxylate (0.145 g, 0.407 mmol, 55% Yield). LRMS $R_T$=1.28 min, m/z=357 $(M+H)^+$.

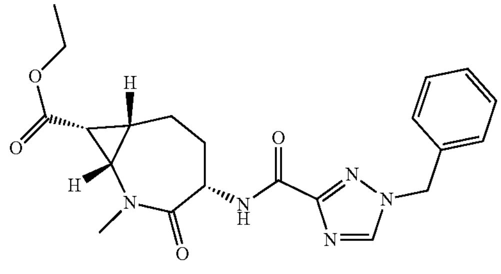

-continued

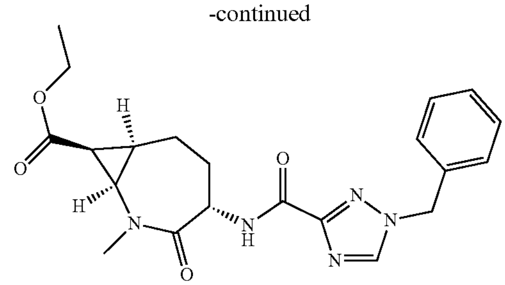

Step 2: ethyl (1S,4S,7S,8R)-4-(1-benzyl-1H-1,2,4-triazole-3-carboxamido)-2-methyl-3-oxo-2-azabicyclo[5.1.0]octane-8-carboxylate and ethyl (1R,4S,7R,8S)-4-(1-benzyl-1H-1,2,4-triazole-3-carboxamido)-2-methyl-3-oxo-2-azabicyclo[5.1.0]octane-8-carboxylate Hydrazine (0.040 mL, 1.18 mmol) was added to a solution of ethyl (4S)-4-(1,3-dioxoisoindolin-2-yl)-6-methyl-5-oxo-6-azabicyclo[5.1.0]octane-8-carboxylate (0.140 g, 0.393 mmol) in ethanol (3.9 mL). The reaction was heated at 80° C. for 2 h. After cooling to RT, the reaction was filtered through a short plug of Celite using ethanol. The filtrate was concentrated to dryness in vacuo and the residue was submitted to the next step without further purification.

(7-Azabenzotriazol-1-yloxy)tripyrrolidinophosphonium hexafluorophosphate (0.235 g, 0.432 mmol) was added to a solution of the crude residue, 1-benzyl-1,2,4-triazole-3-carboxylic acid (99.8 mg, 0.491 mmol), and N,N-diisopropylethylamine (0.21 mL, 1.18 mmol), in N,N-dimethylformamide (3.9 mL). The reaction was allowed to stir at RT for 18 h before being concentrated to dryness in vacuo. The crude residue was purified by reverse phase preparative HPLC to afford arbitrarily assigned ethyl (1S,4S,7S,8R)-4-(1-benzyl-1H-1,2,4-triazole-3-carboxamido)-2-methyl-3-oxo-2-azabicyclo[5.1.0]octane-8-carboxylate (23.5 mg, 0.057 mmol, 14.5% Yield) and ethyl (1R,4S,7R,8S)-4-(1-benzyl-1H-1,2,4-triazole-3-carboxamido)-2-methyl-3-oxo-2-azabicyclo[5.1.0]octane-8-carboxylate (15.6 mg, 0.038 mmol, 9.7% Yield).

Ethyl (1S,4S,7S,8R)-4-(1-benzyl-1H-1,2,4-triazole-3-carboxamido)-2-methyl-3-oxo-2-azabicyclo[5.1.0]octane-8-carboxylate: $^1$H NMR (400 MHz, DMSO-d6) δ 8.81 (s, 1H), 8.15 (d, J=7.6 Hz, 1H), 7.46-7.19 (m, 4H), 5.49 (s, 2H), 5.07 (dt, J=10.8, 7.2 Hz, 1H), 4.09 (m, 2H), 3.41-3.20 (m, 1H), 2.85 (s, 3H), 2.30-2.12 (m, 2H), 2.01-1.77 (m, 2H), 1.60-1.43 (m, 1H), 1.21 (t, J=7.2 Hz, 3H), 1.15-0.95 (m, 1H). LRMS $R_T$=4.19 min, m/z=412.2 $(M+H)^+$.

Prep HPLC Information:
Column: Es Industries Pyridyl Amide (150×30 mm)
Mobile Phase: Carbon Dioxide (A)/Methanol w/0.1% Ammonium Hydroxide (B)
Elution Program
Gradient: 5 to 60% B
Pressure: 2500 psi
Flow Rate: 100 mL/min
Column Temperature: 40° C.
Wavelength: 254 nm Ethyl (1R,4S,7R,8S)-4-(1-benzyl-1H-1,2,4-triazole-3-carboxamido)-2-methyl-3-oxo-2-azabicyclo[5.1.0]octane-8-carboxylate: $^1$H NMR (400 MHz, DMSO-d6) δ 8.81 (s, 1H), 8.19 (d, J=7.6 Hz, 1H), 7.43-7.27 (m, 5H), 5.49 (s, 2H), 4.98 (dt, J=11.2, 7.6 Hz, 1H), 4.16-4.02 (m, 2H), 3.38-3.27 (m, 1H), 2.74 (s, 3H), 2.30-2.22 (m, 1H), 2.16-1.94 (m, 2H), 1.97-1.83 (m, 2H), 1.80-1.74 (m, 1H), 1.68-1.61 (m, 1H), 1.20 (t, J=7.2 Hz, 3H). LRMS $R_T$=4.22 min, m/z=412.2 $(M+H)^+$.

Prep HPLC Information:
Column: Es Industries Pyridyl Amide (150×30 mm)
Mobile Phase: Carbon Dioxide (A)/Methanol w/0.1% Ammonium Hydroxide (B)
Elution Program
Gradient: 5 to 60% B
Pressure: 2500 psi
Flow Rate: 100 mL/min
Column Temperature: 40° C.
Wavelength: 254 nm Example 133

Method X1

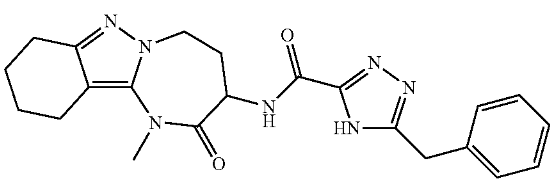 [SMILES: CN1C(=O)C(NC(=O)c2nnc(Cc3ccccc3)[nH]2)CCn2nc3c(c21)CCCC3]

5-benzyl-N-(1-methyl-2-oxo-2,3,4,5,8,9,10,11-octahydro-1H-[1,3]diazepino[1,2-b]indazol-3-yl)-4H-1,2,4-triazole-3-carboxamide

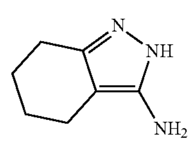

Step 1: 4,5,6,7-tetrahydro-2H-indazol-3-amine

To a solution of 2-oxocyclohexanecarbonitrile (1.71 g, 13.2 mmol) in toluene (23 mL) was added hydrazine (0.485 mL, 14.5 mmol), and the reaction was stirred at 85° C. for 5 h. The reaction mixture was concentrated to dryness in vacuo and the residue was used in the next step without further purification: LCMS $R_T$=0.80 min; m/z=138 $(M+H)^+$.

LCMS (5 to 95% acetonitrile in water+0.05% formic acid over 5 mins)

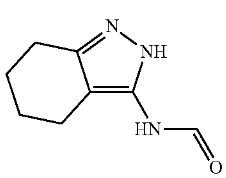 [SMILES: O=CNc1[nH]nc2c1CCCC2]

Step 2: N-(4,5,6,7-tetrahydro-2H-indazol-3-yl)formamide

3-Amino-4,5,6,7-tetrahydro-1H-indazole (1.10 g, 7.7 mmol) and formic acid (4.7 mL, 120 mmol) were mixed together, and the reaction was stirred at 110° C. for 3 h. The reaction mixture was concentrated to dryness in vacuo and the residue was purified by column chromatography (silica gel, 100-200 mesh, 0-15% methanol in dichloromethane) affording N-(4,5,6,7-tetrahydro-2H-indazol-3-yl)formamide (1.143 g, 90% yield) as yellow solid: $^1$H NMR (400 MHz, DMSO-d6) δ 11.92 (s, 1H), 9.85 (dd, J=7.9, 3.4 Hz, 1H), 8.51 (d, J=11.0 Hz, 0.55H), 8.08 (d, J=1.7 Hz, 0.35H), 2.54-2.50 (m, 2H), 2.32 (td, J=6.0, 1.9 Hz, 2H), 1.77-1.55 (m, 4H), tautomers were found in NMR; LCMS $R_T$=1.43 min; m/z=166 $(M+H)^+$.

LCMS (5 to 95% acetonitrile in water+0.05% formic acid over 5 mins)

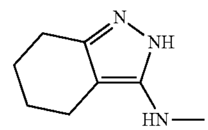

Step 3: N-methyl-4,5,6,7-tetrahydro-2H-indazol-3-amine

To a solution of N-(4,5,6,7-tetrahydro-1H-indazol-3-yl)formamide (2.08 g, 12.6 mmol) in tetrahydrofuran (120 mL) was added lithium aluminum hydride (2 mol/L) in tetrahydrofuran (20.0 mL, 40.0 mmol) at 0° C., and the reaction was stirred at 25° C. for 6 h. Sodium sulfate decahydrate was added, and the mixture was stirred for 18 h. The mixture was filtered through celite, and ethyl acetate was used to rinse the solid. The combined liquid was concentrated to dryness in vacuo to afford N-methyl-4,5,6,7-tetrahydro-1H-indazol-3-amine (2.03 g, 106% yield) as colorless oil used without further purification: $^1$H NMR (400 MHz, DMSO-d6) δ 10.83 (s, 1H), 4.54 (s, 1H), 2.64 (d, J=5.3 Hz, 3H), 2.45-2.37 (m, 2H), 2.23-2.15 (m, 2H), 1.69-1.56 (m, 4H); LCMS $R_T$=1.30 min; m/z=152 $(M+H)^+$.

LCMS (5 to 95% acetonitrile in water+0.05% formic acid over 5 mins)

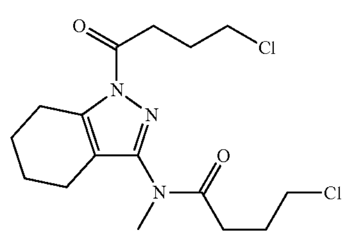 [SMILES: CN(C(=O)CCCCl)c1nn(C(=O)CCCCl)c2c1CCCC2]

Step 4: 4-chloro-N-(1-(4-chlorobutanoyl)-4,5,6,7-tetrahydro-1H-indazol-3-yl)-N-methylbutanamide To a solution of N-methyl-4,5,6,7-tetrahydro-1H-indazol-3-amine (2.03 g, 13.4 mmol) and N,N-dimethylpyridin-4-amine (163.7 mg, 1.340 mmol) in dichloromethane (53 mL) and N,N-diisopropylethylamine (5.84 mL) was added 4-chlorobutyryl chloride (3.462 mL, 30.82 mmol) at 0° C., and the reaction was stirred at 0° C. for 30 min then at 25° C. for 8 h. The reaction mixture was concentrated to dryness in vacuo and the residue was purified by column chromatography (silica gel, 100-200 mesh, 0-40% ethyl acetate in heptane) affording 4-chloro-N-[1-(4-chlorobutanoyl)-4,5,6,7-tetrahydroindazol-3-yl]-N-methyl-butanamide (3.44 g, 71% yield) as oil: LCMS $R_T$=3.11 min; m/z=360 $(M+H)^+$.

LCMS (5 to 95% acetonitrile in water+0.05% formic acid over 5 mins)

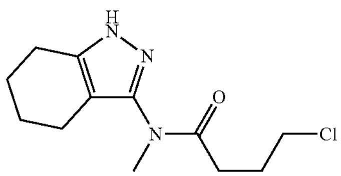 [SMILES: CN(C(=O)CCCCl)c1n[nH]c2c1CCCC2]

Step 5: 4-chloro-N-methyl-N-(4,5,6,7-tetrahydro-1H-indazol-3-yl)butanamide

To a solution of 4-chloro-N-[1-(4-chlorobutanoyl)-4,5,6,7-tetrahydroindazol-3-yl]-N-methyl-butanamide (3.44 g, 9.55 mmol) in ethanol (17 mL) was added sodium hydroxide (1 mol/L) in water (9.5 mL, 9.55 mmol,), and the reaction was stirred at 25° C. for 5 min. The reaction mixture was concentrated to dryness in vacuo and the residue was used without further purification: LCMS $R_T$=2.10 min; m/z=256 $(M+H)^+$.

LCMS (5 to 95% acetonitrile in water+0.05% formic acid over 5 mins)

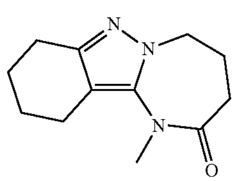 [SMILES: CN1C(=O)CCCn2nc3c(c21)CCCC3]

Step 6: 1-methyl-4,5,8,9,10,11-hexahydro-1H-[1,3]diazepino[1,2-b]indazol-2(3H)-one To a solution of 4-chloro-N-methyl-N-(4,5,6,7-tetrahydro-1H-indazol-3-yl)butanamide (2.81 g, 11.0 mmol) in N,N-dimethylformamide (49 mL) was added cesium carbonate (5.37 g, 16.5 mmol), and the reaction was stirred at 65° C. for 18 h. The reaction mixture was diluted with ethyl acetate and water, and the two layers were separated. The aqueous layer was extracted by ethyl acetate. The organic layers were combined, washed by water and brine, dried over magnesium sulfate, filtered through celite, and concentrated to dryness in vacuo. The residue was purified by column chromatography (silica gel, 100-200 mesh, 0-100% ethyl acetate in heptane) affording 1-methyl-4,5,8,9,10,11-hexahydro-3H-[1,3]diazepino[1,2-b]indazol-2-one (2.03 g, 63% yield) as a white solid: $^1H$ NMR (400 MHz, Chloroform-d) δ 4.18 (t, J=6.7 Hz, 2H), 3.24 (s, 3H), 2.65 (dd, J=6.4, 5.6 Hz, 2H), 2.53-2.42 (m, 2H), 2.42-2.25 (m, 4H), 1.90-1.74 (m, 4H); $^1H$ NMR (400 MHz, DMSO-d6) δ 4.13-4.04 (m, 2H), 2.73 (d, J=0.6 Hz, 3H), 2.56-2.47 (m, 2H), 2.43 (t, J=5.9 Hz, 2H), 2.23-2.07 (m, 4H), 1.79-1.61 (m, 4H); LCMS $R_T$=1.78 min; m/z=220 $(M+H)^+$.

LCMS (5 to 95% acetonitrile in water+0.05% formic acid over 5 mins)

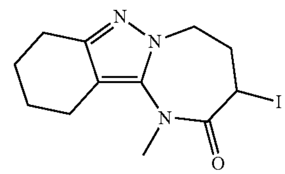 [SMILES: CN1C(=O)C(I)CCn2nc3c(c21)CCCC3]

Step 7: 3-iodo-1-methyl-4,5,8,9,10,11-hexahydro-1H-[1,3]diazepino[1,2-b]indazol-2(3H)-one To a solution of 1-methyl-4,5,8,9,10,11-hexahydro-3H-[1,3]diazepino[1,2-b]indazol-2-one (1.00 g, 3.42 mmol) in dichloromethane (29 mL) was added N,N,N',N'-tetramethylethylenediamine (3.09 mL, 20.5 mmol) at −10° C. (1/1 salt/ice bath), followed by fresh iodotrimethylsilane (2.93 mL, 20.5 mmol), and the reaction was stirred in salt/ice bath (at −10~−15° C.) for 1.5 h. Iodine (2.60 g, 10.3 mmol) was added, and the reaction was stirred in salt/ice bath (at −10~−15° C.) for 2 h. The crude mixture was diluted with ethyl acetate and sodium sulfite, and the two layers were separated. The aqueous layer was extracted by ethyl acetate. The organic layers were combined, washed by water and brine, dried over magnesium sulfate, filtered through celite, and concentrated to dryness in vacuo. The residue was purified by column chromatography (silica gel, 100-200 mesh, 0-70% ethyl acetate in dichloromethane) affording 3-iodo-1-methyl-4,5,8,9,10,11-hexahydro-3H-[1,3]diazepino[1,2-b]indazol-2-one (0.87 g, 74% yield) as white powder: $^1H$ NMR (400 MHz, Chloroform-d) δ 4.56 (dd, J=9.3, 7.7 Hz, 1H), 4.23-4.13 (m, 2H), 3.29 (s, 3H), 3.02-2.89 (m, 1H), 2.81-2.70 (m, 1H), 2.69-2.62 (m, 2H), 2.53-2.43 (m, 2H), 1.93-1.69 (m, 4H); $^1H$ NMR (400 MHz, DMSO-d6) δ 4.56 (dd, J=8.7, 7.8 Hz, 1H), 4.14-4.07 (m, 2H), 3.17 (s, 3H), 2.91-2.77 (m, 1H), 2.62-2.54 (m, 1H), 2.47-2.39 (m, 2H), 1.82-1.63 (m, 4H); LCMS $R_T$=1.25 min; m/z=346 $(M+H)^+$.

LCMS (5 to 95% acetonitrile in water+0.05% formic acid over 5 mins)

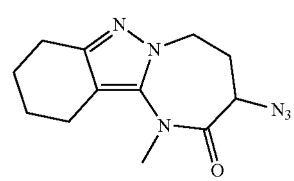 [SMILES: CN1C(=O)C(N=[N+]=[N-])CCn2nc3c(c21)CCCC3]

Step 8: 3-azido-1-methyl-4,5,8,9,10,11-hexahydro-1H-[1,3]diazepino[1,2-b]indazol-2(3H)-one To a solution of 3-iodo-1-methyl-4,5,8,9,10,11-hexahydro-3H-[1,3]diazepino[1,2-b]indazol-2-one (880 mg, 2.55 mmol) in N,N-dimethylformamide (3.0 mL) was added sodium azide (222 mg, 3.3142 mmol), and the reaction was stirred at 25° C. for 4 h. The crude mixture was diluted with ethyl acetate and water, and the two layers were separated. The aqueous layer was extracted by ethyl acetate. The organic layers were combined, washed by water and brine, dried over magnesium sulfate, filtered through celite, and concentrated to dryness in vacuo. The crude residue was used without further purification: LCMS $R_T$=2.10 min; m/z=261 $(M+H)^+$.

LCMS (5 to 95% acetonitrile in water+0.05% formic acid over 5 mins)

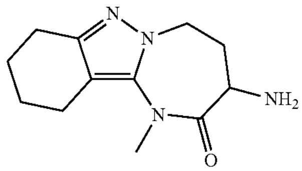 [SMILES: CN1C(=O)C(N)CCn2nc3c(c21)CCCC3]

Step 9: 3-amino-1-methyl-4,5,8,9,10,11-hexahydro-1H-[1,3]diazepino[1,2-b]indazol-2(3H)-one To a solution of 3-azido-1-methyl-4,5,8,9,10,11-hexahydro-3H-[1,3]diazepino[1,2-b]indazol-2-one (330 mg, 1.27 mmol) in tetrahydrofuran (5.3 mL) and water (1.2 mL) was added triphenylphosphine, polymer-bound (7.61 mmol), and the reaction was stirred at 25° C. for 18 h. The crude mixture was filtered through celite, and concentrated to dryness in vacuo. The crude residue was used without further purification: LCMS $R_T$=1.39 min; m/z=235 $(M+H)^+$.

LCMS (5 to 95% acetonitrile in water+0.05% formic acid over 5 mins)

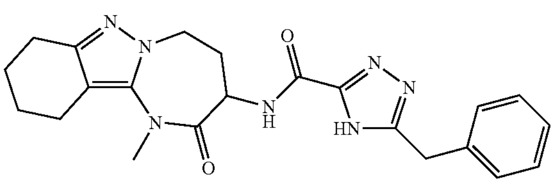 [SMILES: CN1C(=O)C(NC(=O)c2nnc(Cc3ccccc3)[nH]2)CCn2nc3c(c21)CCCC3]

Step 10: 5-benzyl-N-(1-methyl-2-oxo-2,3,4,5,8,9,10,11-octahydro-1H-[1,3]diazepino[1,2-b]indazol-3-yl)-4H-1,2,4-triazole-3-carboxamide To a solution of 5-benzyl-4H-1,2,4-triazole-3-carboxylic acid (32 mg, 0.16 mmol) in N,N-dimethylformamide (0.1 mL) and acetonitrile (0.25 mL) was added 1-[bis(dimethylamino)methylene]-1H-1,2,3-triazolo[4,5-b]pyridinium 3-oxide hexafluorophosphate (62 mg, 0.16 mmol) at 0° C., and the reaction was stirred at 0° C. for 20 min. 3-Amino-1-methyl-4,5,8,9,10,11-hexahydro-3H-[1,3]diazepino[1,2-b]indazol-2-one (25 mg, 0.11 mmol) was added. The reaction was stirred at 25° C. for 18 h. The reaction mixture was concentrated to dryness in vacuo and the residue was purified by RP-HPLC affording 5-benzyl-N-(1-methyl-2-oxo-4,5,8,9,10,11-hexahydro-3H-[1,3]diazepino[1,2-b]indazol-3-yl)-4H-1,2,4-triazole-3-carboxamide (11 mg, 25% yield) as white powder: $^1H$ NMR (400 MHz, DMSO-d6) δ 8.30 (d, J=7.7 Hz, 1H), 7.38-7.16 (m, 5H), 4.35-4.08 (m, 3H), 4.06 (s, 2H), 3.19 (s, 3H), 2.65-2.51 (m, 3H), 2.49-2.40 (m, 2H), 2.27-2.16 (m, 1H), 1.87-1.59 (m, 4H); LCMS $R_T$=4.15 min; m/z=420.2 $(M+H)^+$.

Example 134

Method X2

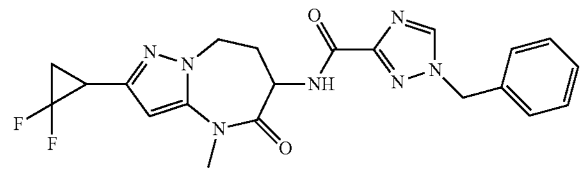 [SMILES: CN1C(=O)C(NC(=O)c2ncn(Cc3ccccc3)n2)CCn2nc(C3CC3(F)F)cc21]

1-benzyl-N-(2-(2,2-difluorocyclopropyl)-4-methyl-5-oxo-5,6,7,8-tetrahydr-4H-pyrazolo[1,5-a][1,3]diazepin-6-yl)-1H-1,2,4-triazole-3-carboxamide

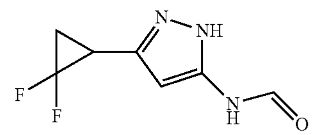 [SMILES: O=CNc1cc(C2CC2(F)F)n[nH]1]

Step 1: N-[5-(2,2-difluorocyclopropyl)-1H-pyrazol-3-yl]formamide

To a solution of 5-(2,2-difluorocyclopropyl)-1H-pyrazol-3-amine (1.01 g, 6.35 mmol) in toluene (9.40 mL) was added formic acid (3.8 mL), and the reaction was stirred at 110° C. for 3 h. The crude mixture was concentrated to dryness in vacuo, and the residue was purified by column chromatography (silica gel, 100-200 mesh, 0-100% ethyl acetate in dichloromethane) affording N-[5-(2,2-difluorocyclopropyl)-1H-pyrazol-3-yl]formamide (420 mg, 35% yield) as light brown solid: $^1H$ NMR (400 MHz, DMSO-d6) δ 12.42 (s, 1H), 10.47 (s, 0.70H), 10.10 (s, 0.30H), 8.62 (d, J=11.0 Hz, 0.30H), 8.14 (d, J=1.8 Hz, 0.80H), 6.39 (s, 0.70H), 5.90 (d, J=1.9 Hz, 0.30H), 3.04-2.85 (m, 1H), 2.15-2.00 (m, 1H), 1.96-1.81 (m, 1H); tautomers were found in NMR; LCMS $R_T$=1.18 min; m/z=188 $(M+H)^+$.

LCMS (5 to 95% acetonitrile in water+0.05% formic acid over 5 mins)

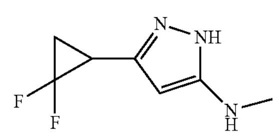

Step 2: 5-(2,2-difluorocyclopropyl)-N-methyl-1H-pyrazol-3-amine

To a solution of N-[5-(2,2-difluorocyclopropyl)-1H-pyrazol-3-yl]formamide (787 mg, 4.2 mmol) in tetrahydrofuran (37 mL) was added lithium aluminum hydride (2 mol/L) in tetrahydrofuran (6.38 mL, 12.6 mmol) at 0° C., and the reaction was stirred at 25° C. for 6 h. Sodium sulfate decahydrate was added, and the mixture was stirred for 18 h. The mixture was filtered through celite, and ethyl acetate was used to rinse the solid. The combined liquid was concentrated to dryness in vacuo affording 5-(2,2-difluorocyclopropyl)-N-methyl-1H-pyrazol-3-amine (950 mg) as colorless oil used without further purification: $^1$H NMR (400 MHz, DMSO-d6) δ 11.45 (s, 1H), 5.23 (bs, 1H), 2.81-2.66 (m, 1H), 2.61 (d, J=5.3 Hz, 3H), 1.98-1.87 (m, 1H), 1.77-1.65 (m, 1H); LCMS $R_T$=1.06 min; m/z=174 $(M+H)^+$.

LCMS (5 to 95% acetonitrile in water+0.05% formic acid over 5 mins)

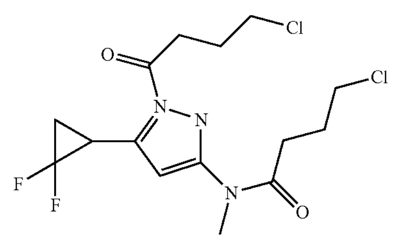

Step 3: 4-chloro-N-(1-(4-chlorobutanoyl)-5-(2,2-difluorocyclopropyl)-1H-pyrazol-3-yl)-N-methylbutanamide To a solution of 5-(2,2-difluorocyclopropyl)-N-methyl-1H-pyrazol-3-amine (810 mg, 4.7 mmol) and N,N-dimethylpyridin-4-amine (57 mg, 0.47 mmol) in dichloromethane (19 mL) and N,N-diisopropylethylamine (2.0 mL, 12 mmol) was added 4-chlorobutyryl chloride (1.2 mL, 10 mmol) at 0° C., and the reaction was stirred at 0-25° C. for 18 h. The reaction mixture was concentrated to dryness in vacuo and the crude residue was purified by column chromatography (silica gel, 100-200 mesh, 0-50% ethyl acetate in heptane) affording 4-chloro-N-(1-(4-chlorobutanoyl)-5-(2,2-difluorocyclopropyl)-1H-pyrazol-3-yl)-N-methylbutanamide (332 mg, 56% yield): $^1$H NMR (400 MHz, DMSO-d6) δ 6.86 (s, 1H), 3.74 (t, J=6.5 Hz, 2H), 3.71-3.62 (m, 2H), 3.43-3.33 (m, 2H), 3.23 (t, J=7.3 Hz, 2H), 2.73-2.62 (m, 2H), 2.18-1.87 (m, 6H), $CH_3$ was not seen in NMR, probably overlapping with HDO peak at 3.30 ppm; LCMS $R_T$=3.07 min; m/z=382 $(M+H)^+$.

LCMS (5 to 95% acetonitrile in water+0.05% formic acid over 5 mins)

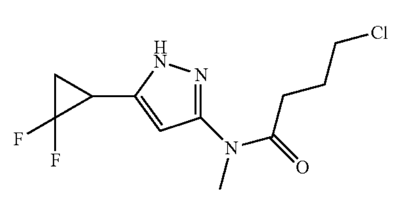 [SMILES: CN(C(=O)CCCCl)c1cc(C2CC2(F)F)[nH]n1]

Step 4: 4-chloro-N-(5-(2,2-difluorocyclopropyl)-1H-pyrazol-3-yl)-N-methylbutanamide To a solution of 4-chloro-N-[1-(4-chlorobutanoyl)-5-(2,2-difluorocyclopropyl)pyrazol-3-yl]-N-methyl-butanamide (332 mg, 0.87 mmol) in ethanol (1.4 mL) was added sodium hydroxide (1 mol/L) in water (0.87 mL), and the reaction was stirred at 25° C. for 5 min. The reaction mixture was concentrated to dryness in vacuo and the residue was used without further purification: LCMS $R_T$=2.03 min; m/z=278 $(M+H)^+$.

LCMS (5 to 95% acetonitrile in water+0.05% formic acid over 5 mins)

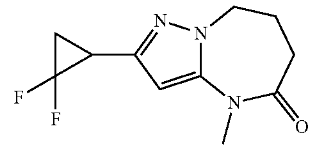 [SMILES: CN1C(=O)CCCn2nc(C3CC3(F)F)cc21]

Step 5: 2-(2,2-difluorocyclopropyl)-4-methyl-7,8-dihydro-6H-pyrazolo[1,5-a][1,3]diazepin-5-one To a solution of 4-chloro-N-[5-(2,2-difluorocyclopropyl)-1H-pyrazol-3-yl]-N-methyl-butanamide (240 mg, 0.86 mmol) in N,N-dimethylformamide (3.9 mL) was added cesium carbonate (422 mg, 1.30 mmol), and the reaction was stirred at 65° C. for 18 h. The crude mixture was diluted with ethyl acetate and citric acid solution (10% aq.), and the two layers were separated. The aqueous layer was extracted by ethyl acetate. The organic layers were combined, washed by water and brine, dried over magnesium sulfate, filtered through celite, and concentrated to dryness in vacuo. The crude residue was purified by column chromatography (silica gel, 100-200 mesh, 0-75% ethyl acetate in dichloromethane) affording 2-(2,2-difluorocyclopropyl)-4-methyl-7,8-dihydro-6H-pyrazolo[1,5-a][1,3]diazepin-5-one (118 mg, 56% yield) as colorless oil: $^1$H NMR (400 MHz, DMSO-d6) δ 6.18-6.13 (m, 1H), 4.21-4.12 (m, 2H), 3.15 (s, 3H), 2.86 (td, J=12.1, 8.0 Hz, 1H), 2.27-2.17 (m, 4H), 2.03-1.90 (m, 1H), 1.88-1.75 (m, 1H); LCMS $R_T$=1.70 min; m/z=242 $(M+H)^+$.

LCMS (5 to 95% acetonitrile in water+0.05% formic acid over 5 mins)

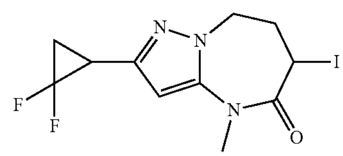 [SMILES: CN1C(=O)C(I)CCn2nc(C3CC3(F)F)cc21]

Step 6: 2-(2,2-difluorocyclopropyl)-6-iodo-4-methyl-7,8-dihydro-6H-pyrazolo[1,5-a][1,3]diazepin-5-one To a solution of 2-(2,2-difluorocyclopropyl)-4-methyl-7,8-dihydro-6H-pyrazolo[1,5-a][1,3]diazepin-5-one (118 mg, 0.49 mmol) in dichloromethane (4.0 mL) cooled to −10° C. in a salt/ice bath was added N,N,N',N'-tetramethylethylenediamine (0.44 mL, 2.9 mmol), followed by iodotrimethylsilane (0.42 mL, 2.9 mmol), and the reaction was stirred at −10° C. for 1.5 h. Iodine (372 mg, 1.47 mmol) was added, and the reaction was stirred for 2 h. The crude mixture was diluted with ethyl acetate and sodium sulfite solution, and the two layers were separated. The aqueous layer was extracted by ethyl acetate. The organic layers were combined, washed by water and brine, dried over magnesium sulfate, filtered through celite, and concentrated to dryness in vacuo. The crude residue was purified by column chromatography (silica gel, 100-200 mesh, 0-70% ethyl acetate in heptane) affording 2-(2,2-difluorocyclopropyl)-6-iodo-4-methyl-7,8-dihydro-6H-pyrazolo[1,5-a][1,3]diazepin-5-one (53 mg, 29% yield) as white solid: $^1$H NMR (400 MHz, Chloroform-d) δ 5.95 (dd, J=2.4, 1.1 Hz, 1H), 4.62 (ddd, J=9.2, 7.4, 4.7 Hz, 1H), 4.31-4.14 (m, 2H), 3.33 (s, 3H), 3.05-2.89 (m, 1H), 2.84-2.67 (m, 2H), 1.91-1.76 (m, 1H), 1.78-1.65 (m, 1H); LCMS $R_T$=2.15 min; m/z=368 $(M+H)^+$ LCMS (5 to 95% acetonitrile in water+0.05% formic acid over 5 mins)

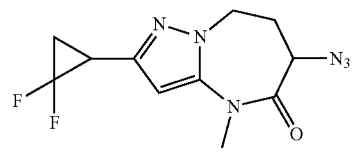 [SMILES: CN1C(=O)C(N=[N+]=[N-])CCn2nc(C3CC3(F)F)cc21]

Step 7: 6-azido-2-(2,2-difluorocyclopropyl)-4-methyl-7,8-dihydro-6H-pyrazolo[1,5-a][1,3]diazepin-5-one To a solution of 2-(2,2-difluorocyclopropyl)-6-iodo-4-methyl-7,8-dihydro-6H-pyrazolo[1,5-a][1,3]diazepin-5-one (53 mg, 0.14 mmol) in N,N-dimethylformamide (0.20 mL) was added sodium azide (11.6 mg, 0.17 mmol), and the reaction was stirred at 25° C. for 2 h. The crude mixture was used without further purification: LCMS $R_T$=2.06 min; m/z=283 $(M+H)^+$.

LCMS (5 to 95% acetonitrile in water+0.05% formic acid over 5 mins)

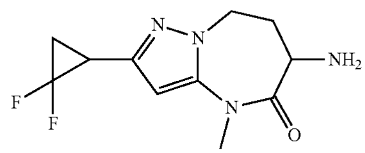 [SMILES: CN1C(=O)C(N)CCn2nc(C3CC3(F)F)cc21]

Step 8: 6-amino-2-(2,2-difluorocyclopropyl)-4-methyl-7,8-dihydro-6H-pyrazolo[1,5-a][1,3]diazepin-5-one To a solution of 6-azido-2-(2,2-difluorocyclopropyl)-4-methyl-7,8-dihydro-6H-pyrazolo[1,5-a][1,3]diazepin-5-one (41 mg, 0.14 mmol) in tetrahydrofuran (0.5 mL) and water (0.15 mL) was added polymer-bound triphenylphosphine (0.87 mmol), and the reaction was stirred at 25° C. for 18 h. The crude mixture was filtered through celite, and concentrated to dryness in vacuo. The crude material was used without further purification: LCMS $R_T$=1.19 min; m/z=257 $(M+H)^+$.

LCMS (5 to 95% acetonitrile in water+0.05% formic acid over 5 mins)

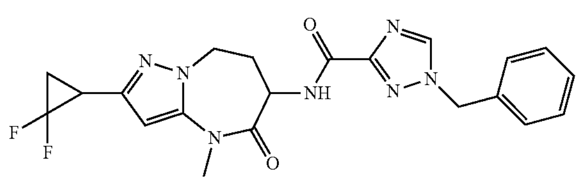 [SMILES: CN1C(=O)C(NC(=O)c2ncn(Cc3ccccc3)n2)CCn2nc(C3CC3(F)F)cc21]

Step 9: 1-benzyl-N-[2-(2,2-difluorocyclopropyl)-4-methyl-5-oxo-7,8-dihydro-6H-pyrazolo[1,5-a][1,3]diazepin-6-yl]-1,2,4-triazole-3-carboxamide To a solution of 1-benzyl-1H-1,2,4-triazole-3-carboxylic acid (62 mg, 0.29 mmol) in N,N-dimethylformamide (1.0 mL) was added 1-[bis(dimethylamino)methylene]-1H-1,2,3-triazolo[4,5-b]pyridinium 3-oxide hexafluorophosphate (112 mg, 0.29 mmol) at 0° C., and the reaction was stirred at 0° C. for 20 min. 6-Amino-2-(2,2-difluorocyclopropyl)-4-methyl-7,8-dihydro-6H-pyrazolo[1,5-a][1,3]diazepin-5-one (37 mg, 0.14 mmol, 37 mg) was added. The reaction was stirred at 25° C. for 18 h. The crude material was purified by RP-HPLC affording 1-benzyl-N-[2-(2,2-difluorocyclopropyl)-4-methyl-5-oxo-7,8-dihydro-6H-pyrazolo[1,5-a][1,3]diazepin-6-yl]-1,2,4-triazole-3-carboxamide (36.5 mg, 57%) as white powder: $^1$H NMR (400 MHz, DMSO-d6) δ 8.82 (s, 1H), 8.54 (d, J=7.8 Hz, 1H), 7.44-7.25 (m, 5H), 6.34-6.23 (m, 1H), 5.48 (s, 2H), 4.36-4.25 (m, 2H), 4.23-4.09 (m, 1H), 3.22 (d, J=2.1 Hz, 3H), 2.99-2.78 (m, 1H), 2.67-2.53 (m, 1H), 2.44-2.31 (m, 1H), 2.02-1.80 (m, 2H); LCMS $R_T$=4.36 min; m/z=442.2 $(M+H)^+$.

Example 135

Method X3

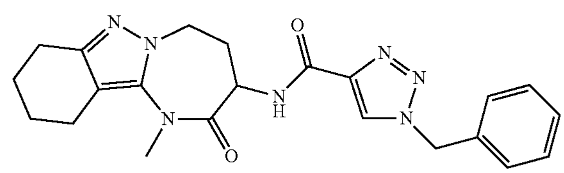 [SMILES: CN1C(=O)C(NC(=O)c2cn(Cc3ccccc3)nn2)CCn2nc3c(c21)CCCC3]

Step 1: 1-benzyl-N-(1-methyl-2-oxo-2,3,4,5,8,9,10,11-octahydro-1H-[1,3]diazepino[1,2-b]indazol-3-yl)-1H-1,2,3-triazole-4-carboxamide To a solution of 1-benzyl-1H-1,2,3-triazole-4-carboxylic acid (75 mg, 0.35 mmol) in N,N-dimethylformamide (1.0 mL) was added 1-[bis(dimethylamino)methylene]-1H-1,2,3-triazolo[4,5-b]pyridinium 3-oxide hexafluorophosphate (136 mg, 0.35 mmol) at 0° C., and the reaction was stirred at 0° C. for 20 min. 3-Amino-1-methyl-4,5,8,9,10,11-hexahydro-3H-[1,3]diazepino[1,2-b]indazol-2-one (41 mg, 0.17 mmol) was added. The reaction was stirred at 25° C. for 18 h. The crude material was purified by RP-HPLC affording 1-benzyl-N-(1-methyl-2-oxo-2,3,4,5,8,9,10,11-octahydro-1H-[1,3]diazepino[1,2-b]indazol-3-yl)-1H-1,2,3-triazole-4-carboxamide (42 mg, 57% yield) as white powder: $^1$H NMR (400 MHz, DMSO-d6) δ 8.65 (s, 1H), 8.49 (d, J=7.7 Hz, 1H), 7.46-7.25 (m, 5H), 5.65 (s, 2H), 4.41-4.03 (m, 3H), 3.18 (s, 3H), 2.59-2.51 (m, 3H), 2.48-2.40 (m, 2H), 2.35-2.22 (m, 1H), 1.86-1.57 (m, 4H); LCMS $R_T$=4.55 min; m/z=420.2 $(M+H)^+$.

Example 136

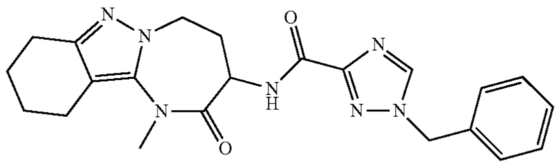 [SMILES: CN1C(=O)C(NC(=O)c2ncn(Cc3ccccc3)n2)CCn2nc3c(c21)CCCC3]

Step 1: 1-benzyl-N-(1-methyl-2-oxo-2,3,4,5,8,9,10,11-octahydro-1H-[1,3]diazepino[1,2-b]indazol-3-yl)-1H-1,2,4-triazole-3-carboxamide To a solution of 1-benzyl-1H-1,2,4-triazole-3-carboxylic acid (75 mg, 0.35 mmol) in N,N-dimethylformamide (1.0 mL) was added 1-[bis(dimethylamino)methylene]-1H-1,2,3-triazolo[4,5-b]pyridinium 3-oxide hexafluorophosphate (136 mg, 0.35 mmol) at 0° C., and the reaction was stirred at 0° C. for 20 min. 3-Amino-1-methyl-4,5,8,9,10,11-hexahydro-3H-[1,3]diazepino[1,2-b]indazol-2-one (41 mg, 0.17 mmol) was added. The reaction was stirred at 25° C. for 18 h. The crude material was purified by RP-HPLC affording 1-benzyl-N-(1-methyl-2-oxo-4,5,8,9,10,11-hexahydro-3H-[1,3]diazepino[1,2-b]indazol-3-yl)-1,2,4-triazole-3-carboxamide (40 mg, 54% yield) as white powder: $^1$H NMR (400 MHz, DMSO-d6) δ 8.82 (s, 1H), 8.38 (d, J=7.7 Hz, 1H), 7.46-7.24 (m, 5H), 5.48 (s, 2H), 4.37-4.06 (m, 3H), 3.19 (s, 3H), 2.66-2.52 (m, 3H), 2.48-2.39 (m, 2H), 2.32-2.17 (m, 1H), 1.87-1.59 (m, 4H); LCMS $R_T$=4.35 min; m/z=420.2 $(M+H)^+$.

Example 137

Method X3

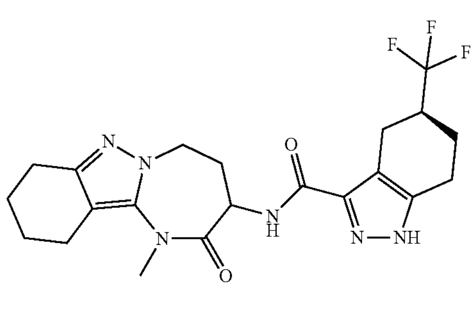 [SMILES: CN1C(=O)C(NC(=O)c2n[nH]c3c2C[C@@H](C(F)(F)F)CC3)CCn2nc3c(c21)CCCC3]

Step 1: (5S)—N-(1-methyl-2-oxo-2,3,4,5,8,9,10,11-octahydro-1H-[1,3]diazepino[1,2-b]indazol-3-yl)-5-(trifluoromethyl)-4,5,6,7-tetrahydro-1H-indazole-3-carboxamide To a solution of (S)-5-(trifluoromethyl)-4,5,6,7-tetrahydro-1H-indazole-3-carboxylic acid (61 mg, 0.26 mmol) in N,N-dimethylformamide (1.0 mL) was added 1-[bis(dimethylamino)methylene]-1H-1,2,3-triazolo[4,5-b]pyridinium 3-oxide hexafluorophosphate (136 mg, 0.35 mmol) at 0° C., and the reaction was stirred at 0° C. for 20 min. 3-Amino-1-methyl-4,5,8,9,10,11-hexahydro-3H-[1,3]diazepino[1,2-b]indazol-2-one (41 mg, 0.17 mmol) was added. The reaction was stirred at 25° C. for 18 h. The crude material was purified by RP-HPLC affording (5S)—N-(1-methyl-2-oxo-2,3,4,5,8,9,10,11-octahydro-1H-[1,3]diazepino[1,2-b]indazol-3-yl)-5-(trifluoromethyl)-4,5,6,7-tetrahydro-1H-indazole-3-carboxamide (28.3 mg, 34% yield): $^1$H NMR (400 MHz, DMSO-d6) δ 12.97 (s, 1H), 7.97 (d, J=7.8 Hz, 1H), 4.37-4.03 (m, 3H), 3.19 (s, 3H), 3.06-2.95 (m, 1H), 2.84-2.74 (m, 1H), 2.72-2.52 (m, 5H), 2.50-2.40 (m, 3H), 2.28-2.16 (m, 1H), 2.14-2.08 (m, 1H), 1.88-1.55 (m, 5H); LCMS $R_T$=4.84 min; m/z=451.2 $(M+H)^+$.

Example 138

Method X4

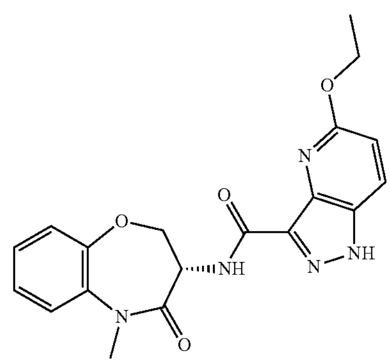 [SMILES: CCOc1ccc2[nH]nc(C(=O)N[C@H]3COc4ccccc4N(C)C3=O)c2n1]

Step 1: 5-ethoxy-N-[(3S)-5-methyl-4-oxo-2,3-dihydro-1,5-benzoxazepin-3-yl]-1H-pyrazolo[4,3-b]pyridine-3-carboxamide To a solution of 5-ethoxy-1H-pyrazolo[4,3-b]pyridine-3-carboxylic acid (40 mg, 0.19 mmol) in N,N-dimethylformamide (1.0 mL) was added 1-[bis(dimethylamino)methylene]-1H-1,2,3-triazolo[4,5-b]pyridinium 3-oxide hexafluorophosphate (76 mg, 0.19 mmol) at 0° C., and the reaction was stirred at 0° C. for 20 min. (3S)-3-Amino-5-methyl-2,3-dihydro-1,5-benzoxazepin-4-one (25 mg, 0.13 mmol) was added. The reaction was stirred at 25° C. for 18 h. The reaction mixture was purified by RP-HPLC affording 5-ethoxy-N-[(3S)-5-methyl-4-oxo-2,3-dihydro-1,5-benzoxazepin-3-yl]-1H-pyrazolo[4,3-b]pyridine-3-carboxamide (11.5 mg, 23% yield) as white powder: $^1$H NMR (400 MHz, DMSO-d6) δ 13.90 (bs, 1H), 9.15 (d, J=7.1 Hz, 1H), 8.06 (d, J=9.1 Hz, 1H), 7.54-7.46 (m, 1H), 7.40-7.23 (m, 3H), 6.92 (d, J=9.1 Hz, 1H), 5.10-4.95 (m, 1H), 4.72-4.57 (m, 3H), 4.31 (dd, J=11.3, 9.8 Hz, 1H), 3.37 (s, 3H), 1.44 (t, J=7.0 Hz, 3H); LCMS $R_T$=4.80 min; m/z=382.1 $(M+H)^+$.

Example 139

Method X5

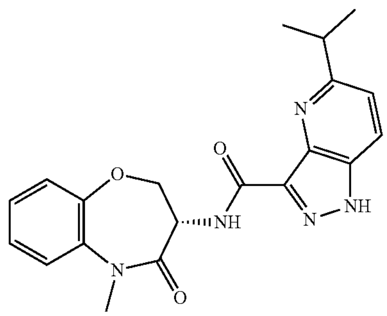 [SMILES: CC(C)c1ccc2[nH]nc(C(=O)N[C@H]3COc4ccccc4N(C)C3=O)c2n1]

5-isopropyl-N-[(3S)-5-methyl-4-oxo-2,3-dihydro-1,5-benzoxazepin-3-yl]-1H-pyrazolo[4,3-b]pyridine-3-carboxamide

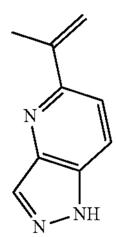

Step 1: 5-isopropenyl-1H-pyrazolo[4,3-b]pyridine

Bis(tricyclohexylphosphine)palladium(0) (129 mg, 0.19 mmol), 5-chloro-1H-pyrazolo[4,3-b]pyridine (301 mg, 1.9 mmol) and isopropenylboronic acid pinacol ester (471 mg, 2.66 mmol) were mixed in acetonitrile (6.0 mL) and sodium carbonate (2 mol/L) in water (2.9 mL, 5.7 mmol), and the reaction was microwaved at 110° C. for 2 h. The crude mixture was diluted with ethyl acetate and citric acid solution (5% in water) to pH 9, and the two layers were separated. The aqueous layer was extracted by ethyl acetate. The organic layers were combined, washed by water and brine, dried over magnesium sulfate, filtered through celite, and concentrated to dryness in vacuo. The crude residue was purified by column chromatography (silica gel, 100-200 mesh, 0-50% ethyl acetate in dichloromethane) affording 5-isopropenyl-1H-pyrazolo[4,3-b]pyridine (274 mg, 58% yield) as white powder: $^1$H NMR (400 MHz, DMSO-d6) δ 13.27 (s, 1H), 8.27 (s, 1H), 7.96 (dd, J=8.9, 1.0 Hz, 1H), 7.75 (d, J=8.9 Hz, 1H), 5.91-5.83 (m, 1H), 5.38 (d, J=1.5 Hz, 1H), 2.22 (dd, J=1.5, 0.8 Hz, 3H); LCMS $R_T$=1.44 min; m/z=160 $(M+H)^+$.

LCMS (5 to 95% acetonitrile in water+0.05% formic acid over 5 mins)

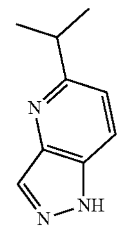

Step 2: 5-isopropyl-1H-pyrazolo[4,3-b]pyridine

To a solution of 5-isopropenyl-1H-pyrazolo[4,3-b]pyridine (201 mg, 0.82 mmol) in ethyl acetate (4.0 mL) and methanol (1.0 mL) was added palladium on activated carbon (10% wt) (86 mg), and the reaction was stirred with H2 balloon at 65° C. for 4 h. The crude mixture was filtered through celite, and the celite was washed with ethyl acetate. The organic layers were combined and concentrated to dryness in vacuo, and the crude residue (244 mg) was used without further purification: $^1$H NMR (400 MHz, DMSO-d6) δ 13.15 (s, 1H), 8.18 (s, 1H), 7.91 (dd, J=8.7, 1.1 Hz, 1H), 7.29 (d, J=8.7 Hz, 1H), 3.15 (hept, J=6.9 Hz, 1H), 1.28 (d, J=6.9 Hz, 6H); LCMS $R_T$=1.18 min; m/z=162 $(M+H)^+$.

LCMS (5 to 95% acetonitrile in water+0.05% formic acid over 5 mins)

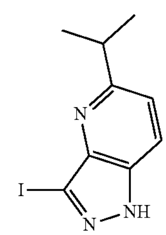

Step 3: 3-iodo-5-isopropyl-1H-pyrazolo[4,3-b]pyridine

To a solution of 5-isopropyl-1H-pyrazolo[4,3-b]pyridine (219 mg, 0.96 mmol) in N,N-dimethylformamide (4.85 mL) was added potassium hydroxide (162 mg, 2.9 mmol), followed by iodine (441 mg, 1.74 mmol), and the reaction was stirred at 50° C. for 1 h, and then at 25° C. for 1 h. The crude mixture was diluted with ethyl acetate and washed by sodium sulfite solution till color of organic layer did not change. The aqueous layers were combined and extracted by ethyl acetate. The organic layers were combined, washed by water and brine, dried over magnesium sulfate, filtered through celite, and concentrated to dryness in vacuo. The crude residue was purified by column chromatography (silica gel, 100-200 mesh, 0-40% ethyl acetate in heptane) affording 3-iodo-5-isopropyl-1H-pyrazolo[4,3-b]pyridine (192 mg, 69% yield) as white powder: $^1$H NMR (400 MHz, DMSO-d6) δ 13.60 (s, 1H), 7.93 (d, J=8.7 Hz, 1H), 7.38 (d, J=8.7 Hz, 1H), 3.18 (hept, J=6.9 Hz, 1H), 1.29 (d, J=6.9 Hz, 6H); LCMS $R_T$=1.22 min; m/z=288 $(M+H)^+$.

LCMS (5 to 95% acetonitrile in water+0.05% formic acid over 5 mins)

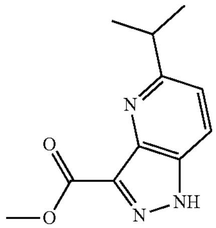 [SMILES: COC(=O)c1n[nH]c2ccc(C(C)C)nc12]

Step 4: methyl 5-isopropyl-1H-pyrazolo[4,3-b]pyridine-3-carboxylate

3-Iodo-5-isopropyl-1H-pyrazolo[4,3-b]pyridine (110 mg, 0.38 mmol), 4,5-bis(diphenylphosphino)-9,9-dimethylxanthene (44 mg, 0.076 mmol) and palladium(II) acetate (8.6 mg, 0.038 mmol) were mixed in triethylamine (0.80 mL, 5.75 mmol), methanol (1.6 mL) and N,N-dimethylformamide (1.2 mL), and the yellow solution was stirred under atmosphere of carbon monoxide at room temperature for 10 min and then at 60° C. for 2 days. The crude mixture was to dryness in vacuo and the crude residue was purified by column chromatography (silica gel, 100-200 mesh, 0-30% ethyl acetate in dichloromethane) affording methyl 5-isopropyl-1H-pyrazolo[4,3-b]pyridine-3-carboxylate (96 mg, 114% yield) as off-white powder: $^1$H NMR (400 MHz, DMSO-d6) δ 13.95 (bs, 1H), 8.04 (d, J=8.8 Hz, 1H), 7.40 (d, J=8.8 Hz, 1H), 3.90 (s, 3H), 3.20 (hept, J=6.9 Hz, 1H), 1.30 (d, J=6.9 Hz, 6H); LCMS $R_T$=1.13 min; m/z=220 $(M+H)^+$.

LCMS (5 to 95% acetonitrile in water+0.05% formic acid over 5 mins)

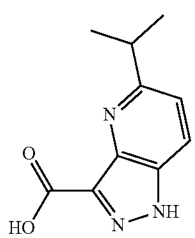

Step 5: 5-isopropyl-1H-pyrazolo[4,3-b]pyridine-3-carboxylic acid

To a solution of methyl 5-isopropyl-1H-pyrazolo[4,3-b]pyridine-3-carboxylate (83 mg, 0.38 mmol) in tetrahydrofuran (2.0 mL), water (1.0 mL) and methanol (1.0 mL) was added sodium hydroxide (150 mg, 3.8 mmol), and the reaction was stirred at 40° C. for 4 h. Hydrochloric acid solution (1.0 M) was added and the final pH was 3. The solution was concentrated to dryness in vacuo, and the crude residue was used without further purification: LCMS $R_T$=1.37 min; m/z=206 $(M+H)^+$.

LCMS (5 to 95% acetonitrile in water+0.05% formic acid over 5 mins)

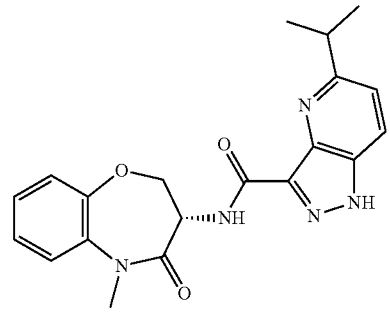 [SMILES: CC(C)c1ccc2[nH]nc(C(=O)N[C@H]3COc4ccccc4N(C)C3=O)c2n1]

Step 6: 5-isopropyl-N-[(3S)-5-methyl-4-oxo-2,3-dihydro-1,5-benzoxazepin-3-yl]-1H-pyrazolo[4,3-b]pyridine-3-carboxamide To a solution of 5-isopropyl-1H-pyrazolo[4,3-b]pyridine-3-carboxylic acid (40 mg, 0.19 mmol) in N,N-dimethylformamide (1.0 mL) was added 1-[bis(dimethylamino)methylene]-1H-1,2,3-triazolo[4,5-b]pyridinium 3-oxide hexafluorophosphate (91 mg, 0.23412 mmol) at 0° C., and the reaction was stirred at 0° C. for 20 min. (3S)-3-Amino-5-methyl-2,3-dihydro-1,5-benzoxazepin-4-one (25 mg, 0.13 mmol) was added. The reaction was stirred at 25° C. for 18 h. The crude material was purified by RP-HPLC affording 5-isopropyl-N-[(3S)-5-methyl-4-oxo-2,3-dihydro-1,5-benzoxazepin-3-yl]-1H-pyrazolo[4,3-b]pyridine-3-carboxamide (43.2 mg, 87% yield) as white powder: $^1$H NMR (400 MHz, DMSO-d6) δ 13.88 (bs, 1H), 9.65 (d, J=7.2 Hz, 1H), 8.09 (d, J=8.8 Hz, 1H), 7.55-7.48 (m, 1H), 7.46 (d, J=8.8 Hz, 1H), 7.38-7.26 (m, 3H), 5.04 (dt, J=11.3, 7.3 Hz, 1H), 4.66 (dd, J=9.8, 7.4 Hz, 1H), 4.32 (dd, J=11.3, 9.8 Hz, 1H), 3.37 (s, 3H), 3.30-3.24 (m, 1H), 1.41 (d, J=6.8 Hz, 6H); LCMS $R_T$=4.92 min; m/z=380.2 $(M+H)^+$.

Example 140

Method X6

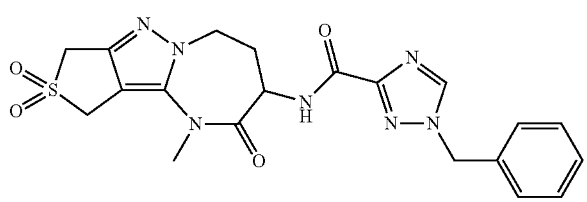 [SMILES: CN1C(=O)C(NC(=O)c2ncn(Cc3ccccc3)n2)CCn2nc3c(c21)CS(=O)(=O)C3]

1-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-1H-1,2,4-triazole-3-carboxamide

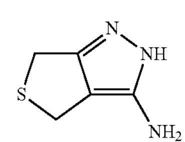

Step 1: 2,6-dihydro-4H-thieno[3,4-c]pyrazol-3-amine

To a solution of 4-cyano-3-tetrahydrothiophenone (1.01 g, 7.78 mmol) in toluene (11.5 mL) was added hydrazine (0.33 mL, 9.7 mmol), and the reaction was stirred at 90° C. for 10 h. The reaction mixture was concentrated to dryness in vacuo and the residue was used without further purification: LCMS $R_T$=1.29 min; m/z=170 (M+H)$^+$.

LCMS (5 to 95% acetonitrile in water+0.05% formic acid over 5 mins)

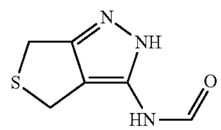 [SMILES: O=CNc1[nH]nc2c1CSC2]

Step 2: N-(4,6-dihydro-2H-thieno[3,4-c]pyrazol-3-yl)formamide 4,6-dihydro-1H-thieno[3,4-c]pyrazol-3-amine (442 mg, 2.98 mmol) and formic acid (1.3 mL) were mixed together, and the reaction was stirred at 110° C. for 3 h. The crude reaction mixture was diluted with ethyl acetate (300 mL) and water (30 mL), and sodium hydroxide solution (aq, 50% w/w) was added dropwise at 0° C. to change the pH of aqueous layer to 7. The two layers were separated. The aqueous layer was extracted by ethyl acetate (50 mL×2). The organic layers were combined, dried over magnesium sulfate, filtered through celite, and concentrated to dryness in vacuo. The crude residue (2.68 g yellow solid) was used without further purification: LCMS $R_T$=1.39 min; m/z=170 (M+H)$^+$.

LCMS (5 to 95% acetonitrile in water+0.05% formic acid over 5 mins)

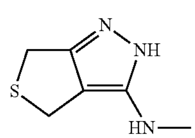

Step 3: N-methyl-4,6-dihydro-2H-thieno[3,4-c]pyrazol-3-amine

To a solution of N-(4,6-dihydro-1H-thieno[3,4-c]pyrazol-3-yl)formamide (2.68 g, 15.8 mmol) in tetrahydrofuran (201 mL) was added lithium aluminum hydride (2 mol/L) in tetrahydrofuran (23.8 mL, 47.5 mmol) at 0° C., and the reaction was stirred at 25° C. for 2.5 h, resulting in a brown solution. Sodium sulfate decahydrate was added, and the mixture was stirred for 18 h. The mixture was filtered through celite, and ethyl acetate was used to rinse the celite solid. The combined liquid was concentrated to dryness in vacuo, and the crude residue (3.43 g) was used without further purification: LCMS $R_T$=1.58 min; m/z=156 (M+H)$^+$.

LCMS (5 to 95% acetonitrile in water+0.05% formic acid over 5 mins)

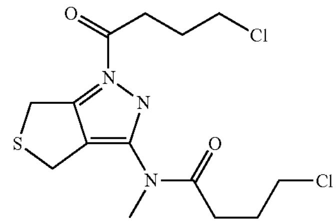

Step 4: 4-chloro-N-[1-(4-chlorobutanoyl)-4,6-dihydrothieno[3,4-c]pyrazol-3-yl]-N-methyl-butan amide To a solution of N-methyl-4,6-dihydro-1H-thieno[3,4-c]pyrazol-3-amine (3.43 g, 22.1 mmol) and N,N-dimethylpyridin-4-amine (270 mg, 2.21 mmol) in dichloromethane (88 mL) and N,N-diisopropylethylamine (7.71 mL, 44.2 mmol) was added 4-chlorobutyryl chloride (4.47 mL, 39.8 mmol) at 0° C., and the reaction was stirred at 0° C. for 30 min then at 25° C. for 2 h. The reaction solution was diluted with ethyl acetate (350 mL), and washed by water (final pH~7). The organic layer was dried over magnesium sulfate, filtered through celite, and concentrated to dryness in vacuo. The residue was purified by column chromatography (silica gel, 100-200 mesh, 0-30% ethyl acetate in heptane) affording 4-chloro-N-[1-(4-chlorobutanoyl)-4,6-dihydrothieno[3,4-c]pyrazol-3-yl]-N-methyl-butanamide (3.785 g, 47% yield) as yellow oil: LCMS $R_T$=3.46 min; m/z=364 (M+H)$^+$.

LCMS (5 to 95% acetonitrile in water+0.05% formic acid over 5 mins)

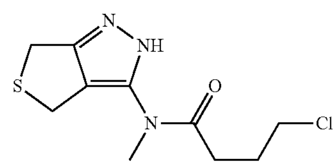 [SMILES: CN(C(=O)CCCCl)c1[nH]nc2c1CSC2]

Step 5: 4-chloro-N-(4,6-dihydro-1H-thieno[3,4-c]pyrazol-3-yl)-N-methyl-butanamide To a solution of 4-chloro-N-[1-(4-chlorobutanoyl)-4,6-dihydrothieno[3,4-c]pyrazol-3-yl]-N-methyl-butanamide (3.78 g, 10.4 mmol) in ethanol (16 mL) was added sodium hydroxide (1 mol/L) in water (10 mL, 10 mmol), and the reaction was stirred at 0° C. for 15 min. The crude mixture was diluted with ethyl acetate and water, and the two layers were separated. The aqueous layer was extracted by ethyl acetate. The organic layers were combined, washed by water and brine, dried over magnesium sulfate, filtered through celite, and concentrated to dryness in vacuo. The crude material (3.40 g white solid) was used without further purification: LCMS $R_T$=1.87 min; m/z=260 (M+H)$^+$.

LCMS (5 to 95% acetonitrile in water+0.05% formic acid over 5 mins)

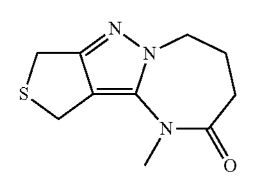

Step 6: 1-methyl-1,4,5,10-tetrahydro-8H-thieno[3',4':3,4]pyrazolo[1,5-a][1,3]diazepin-2(3H)-one To a solution of 4-chloro-N-(4,6-dihydro-1H-thieno[3,4-c]pyrazol-3-yl)-N-methyl-butanamide (2.70 g, 10.4 mmol) in N,N-dimethylformamide (47 mL) was added cesium carbonate (4.41 g, 13.5 mmol), and the reaction was stirred at 60° C. for 1.5 h. The crude mixture was diluted with ethyl acetate and citric acid to pH 8, and the two layers were separated. The aqueous layer was extracted by ethyl acetate twice. The organic layers were combined, washed by water and brine, dried over magnesium sulfate, filtered through celite, and concentrated to dryness in vacuo. The crude residue was purified by column chromatography (silica gel, 100-200 mesh, 0-10% methanol in dichloromethane) affording 1-methyl-1,4,5,10-tetrahydro-8H-thieno[3',4':3,4]pyrazolo[1,5-a][1,3]diazepin-2(3H)-one (1.91 g, 62% yield) as slightly yellow oil, which crystallized upon scratch or addition of crystal seed: $^1$H NMR (400 MHz, DMSO-d6) δ 4.14 (t, J=6.7 Hz, 2H), 3.88 (s, 4H), 3.12 (s, 3H), 2.33-2.15 (m, 4H); $^1$H NMR (400 MHz, Chloroform-d) δ 4.21 (t, J=6.8 Hz, 2H), 4.03-3.95 (m, 2H), 3.89-3.82 (m, 2H), 3.23 (s, 3H), 2.50-2.30 (m, 4H); LCMS $R_T$=1.66 min; m/z=224 $(M+H)^+$.

LCMS (5 to 95% acetonitrile in water+0.05% formic acid over 5 mins)

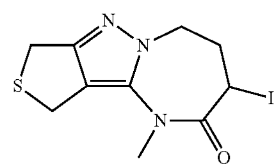 [SMILES: CN1C(=O)C(I)CCn2nc3c(c21)CSC3]

Step 7: 3-iodo-1-methyl-1,4,5,10-tetrahydro-8H-thieno[3',4':3,4]pyrazolo[1,5-a][1,3]diazepin-2(3H)-one To a solution of 1-methyl-1,4,5,10-tetrahydro-8H-thieno[3',4':3,4]pyrazolo[1,5-a][1,3]diazepin-2(3H)-one (1001 mg, 3.3621 mmol, 75% wt purity) in dichloromethane (28 mL) was added N,N,N',N'-tetramethylethylenediamine (4.05 mL, 27 mmol) at −20° C. (acetone-dry-ice bath), followed by iodotrimethylsilane (3.84 mL, 27 mmol), and the reaction was stirred in acetone-dry-ice bath (−20~−15° C.) for 3 h. Iodine (3.41 g, 13.5 mmol) was added, and the reaction was stirred in acetone-dry-ice bath (at −15~−10° C.) for 2 h. The crude mixture was diluted with ethyl acetate and sodium thiosulfate solution (10% aq., 10 mL), and the two layers were separated. The aqueous layer was extracted by ethyl acetate. The organic layers were combined, washed by water and brine, dried over magnesium sulfate, filtered through celite, and concentrated to dryness in vacuo. The crude residue was purified by column chromatography (silica gel, 100-200 mesh, 0-50% ethyl acetate in heptane) affording 3-iodo-1-methyl-1,4,5,10-tetrahydro-8H-thieno[3',4':3,4]pyrazolo[1,5-a][1,3]diazepin-2(3H)-one (0.80 g, 68% yield) as off-white solid: $^1$H NMR (400 MHz, Chloroform-d) δ 4.65 (dd, J=8.5, 7.6 Hz, 1H), 4.19 (ddd, J=8.3, 5.9, 1.5 Hz, 2H), 4.03-3.95 (m, 2H), 3.93-3.85 (m, 2H), 3.29 (s, 3H), 3.05-2.89 (m, 1H), 2.85-2.71 (m, 1H); LCMS $R_T$=1.97 min; m/z=350 $(M+H)^+$.

LCMS (5 to 95% acetonitrile in water+0.05% formic acid over 5 mins)

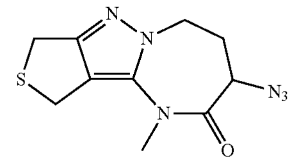 [SMILES: CN1C(=O)C(N=[N+]=[N-])CCn2nc3c(c21)CSC3]

Step 8: 3-azido-1-methyl-1,4,5,10-tetrahydro-8H-thieno[3',4':3,4]pyrazolo[1,5-a][1,3]diazepin-2(3H)-one To a solution of 3-iodo-1-methyl-1,4,5,10-tetrahydro-8H-thieno[3',4':3,4]pyrazolo[1,5-a][1,3]diazepin-2(3H)-one (310 mg, 0.89 mmol) in N,N-dimethylformamide (3.50 mL) was added sodium azide (89 mg, 1.33 mmol), and the reaction was stirred at 25° C. for 2 h. The reaction mixture was concentrated to dryness in vacuo and was diluted with ethyl acetate and water (pH-8). The two layers were separated. The aqueous layer was extracted by ethyl acetate twice. The organic layers were combined, washed by water and brine, dried over magnesium sulfate, filtered through celite, and concentrated to dryness in vacuo. The crude material (436 mg) was used without further purification: LCMS $R_T$=1.07 min; m/z=265 $(M+H)^+$.

LCMS (5 to 95% acetonitrile in water+0.05% formic acid over 5 mins)

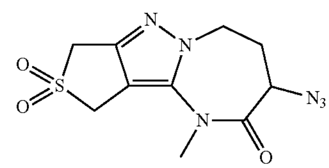 [SMILES: CN1C(=O)C(N=[N+]=[N-])CCn2nc3c(c21)CS(=O)(=O)C3]

Step 9: 3-azido-1-methyl-1,4,5,10-tetrahydro-8H-thieno[3',4':3,4]pyrazolo[1,5-a][1,3]diazepin-2(3H)-one 9,9-dioxide To a solution of 3-azido-1-methyl-1,4,5,10-tetrahydro-8H-thieno[3',4': 3,4]pyrazolo[1,5-a][1,3]diazepin-2(3H)-one (355 mg, 1.34 mmol) in acetic acid (0.081 mL, 1.41 mmol) and dichloromethane (11 mL) was added 3-chloroperoxybenzoic acid (722 mg, 3.22 mmol) at 0° C., and the reaction was stirred at 0° C. for 1 h. Second portion of 3-chloroperoxybenzoic acid (96 mg, 0.43 mmol) was added, and the reaction was stirred at 25° C. for 30 min. The crude mixture was diluted with ethyl acetate. The organic solution was washed by water and brine, dried over magnesium sulfate, filtered through celite, and concentrated to dryness in vacuo. The crude residue was purified by column chromatography (silica gel, 100-200 mesh, 0-60% ethyl acetate in heptane) affording 3-azido-1-methyl-1,4,5,10-tetrahydro-8H-thieno[3',4': 3,4]pyrazolo[1,5-a][1,3]diazepin-2(3H)-one 9,9-dioxide (360 mg, 90% yield) as white solid: $^1$H NMR (400 MHz, Chloroform-d) δ 4.55-4.39 (m, 1H), 4.33-4.16 (m, 5H), 3.91 (dd, J=10.6, 7.9 Hz, 1H), 3.32 (s, 3H), 2.88-2.74 (m, 1H), 2.30 (dddd, J=13.5, 10.7, 6.6, 1.8 Hz, 1H); $^1$H NMR (400 MHz, DMSO-d6) δ 4.53 (d, J=14.7 Hz, 1H), 4.48-4.25 (m, 5H), 4.13 (dd, J=11.3, 7.9 Hz, 1H), 3.25 (s, 3H), 2.84-2.64 (m, 1H), 2.17 (dddd, J=13.2, 11.4, 6.1, 1.7 Hz, 1H); LCMS $R_T$=1.52 min; m/z=297 $(M+H)^+$.

LCMS (5 to 95% acetonitrile in water+0.05% formic acid over 5 mins)

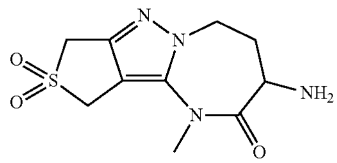 [SMILES: CN1C(=O)C(N)CCn2nc3c(c21)CS(=O)(=O)C3]

Step 10: 3-amino-1-methyl-1,4,5,10-tetrahydro-8H-thieno[3',4':3,4]pyrazolo[1,5-a][1,3]diazepin-2(3H)-one 9,9-dioxide To a suspension of 3-azido-1-methyl-1,4,5,10-tetrahydro-8H-thieno[3',4':3,4]pyrazolo[1,5-a][1,3]diazepin-2(3H)-one 9,9-dioxide (291 mg, 0.84 mmol) in tetrahydrofuran (6.9 mL) and water (0.93 mL) was added polymer-bound triphenylphosphine (5.1 mmol), and the reaction was stirred at 25° C. for 12 h. The reaction mixture was filtered through celite, and the celite solid was rinsed by a solution of methanol in dichloromethane (10% v/v) twice. The solutions were combined and concentrated to dryness in vacuo, and the crude material (284 mg) was used without further purification: LCMS $R_T$=0.52 min; m/z=271 $(M+H)^+$.

LCMS (5 to 95% acetonitrile in water+0.05% formic acid over 5 mins).

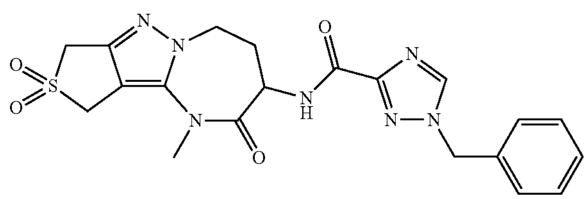 [SMILES: CN1C(=O)C(NC(=O)c2ncn(Cc3ccccc3)n2)CCn2nc3c(c21)CS(=O)(=O)C3]

Step 11: 1-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-1H-1,2,4-triazole-3-carboxamide To a suspension of 1-benzyl-1H-1,2,4-triazole-3-carboxylic acid (68 mg, 0.32 mmol) in N,N-dimethylformamide (1.0 mL) and N,N-diisopropylethylamine (0.055 mL, 0.32 mmol) was added 1-[bis(dimethylamino)methylene]-1H-1,2,3-triazolo[4,5-b]pyridinium 3-oxide hexafluorophosphate (123 mg, 0.32 mmol) at 0° C., and the reaction was stirred at 0° C. for 20 min, resulting in a yellow solution. 3-Amino-1-methyl-1,4,5,10-tetrahydro-8H-thieno[3',4':3,4]pyrazolo[1,5-a][1,3]diazepin-2(3H)-one 9,9-dioxide (57 mg, 0.21 mmol) was added. The reaction was stirred at 25° C. for 18 h. The reaction mixture was concentrated to dryness in vacuo and the residue was purified by RP-HPLC affording 1-benzyl-N-(1-methyl-9,9-dioxido-2-oxo-1,2,3,4,5,10-hexahydro-8H-thieno[3',4':3,4]pyrazol o[1,5-a][1,3]diazepin-3-yl)-1H-1,2,4-triazole-3-carboxamide (61 mg, 63% yield) as white powder: $^1$H NMR (400 MHz, DMSO-d6) δ 8.82 (s, 1H), 8.49 (d, J=7.7 Hz, 1H), 7.46-7.23 (m, 5H), 5.49 (s, 2H), 4.56-4.33 (m, 6H), 4.34-4.19 (m, 1H), 3.20 (s, 3H), 2.73-2.60 (m, 1H), 2.41-2.28 (m, 1H); LCMS $R_T$=3.47 min; m/z=456.1 $(M+H)^+$.

Example 141

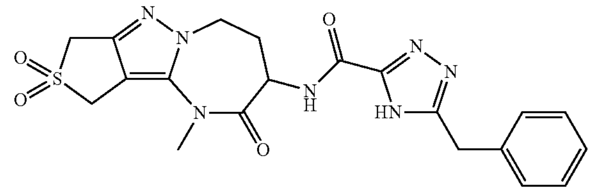 [SMILES: CN1C(=O)C(NC(=O)c2nnc(Cc3ccccc3)[nH]2)CCn2nc3c(c21)CS(=O)(=O)C3]

5-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-4H-1,2,4-triazole-3-carboxamide Step 1: 5-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-4H-1,2,4-triazole-3-carboxamide To a suspension of 5-benzyl-4H-1,2,4-triazole-3-carboxylic acid (65 mg, 0.32 mmol) in N,N-dimethylformamide (1.0 mL) and N,N-diisopropylethylamine (0.052 mL, 0.32 mmol) was added 1-[bis(dimethylamino)methylene]-1H-1,2,3-triazolo[4,5-b]pyridinium 3-oxide hexafluorophosphate (123 mg, 0.32 mmol) at 0° C., and the reaction was stirred at 0° C. for 20 min, resulting in a yellow solution. 3-Amino-1-methyl-1,4,5,10-tetrahydro-8H-thieno[3',4':3,4]pyrazolo[1,5-a][1,3]diazepin-2(3H)-one 9,9-dioxide (57 mg, 0.21 mmol) was added. The reaction was stirred at 25° C. for 18 h. The reaction mixture was concentrated to dryness in vacuo and the residue was purified by RP-HPLC affording 5-benzyl-N-(1-methyl-9,9-dioxido-2-oxo-1,2,3,4,5,10-hexahydro-8H-thieno[3',4':3,4]pyrazol o[1,5-a][1,3]diazepin-3-yl)-4H-1,2,4-triazole-3-carboxamide (8 mg, 8.3% yield) as white powder: $^1$H NMR (400 MHz, DMSO-d6) δ 8.47 (bs, 1H), 7.40-7.17 (m, 5H), 4.56-4.33 (m, 6H), 4.33-4.20 (m, 1H), 4.10 (s, 2H), 3.20 (s, 3H), 2.75-2.59 (m, 1H), 2.41-2.29 (m, 1H); LCMS $R_T$=3.42 min; m/z=456.1 $(M+H)^+$.

Example 142

Method X7

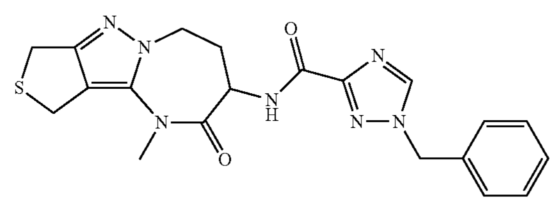 [SMILES: CN1C(=O)C(NC(=O)c2ncn(Cc3ccccc3)n2)CCn2nc3c(c21)CSC3]

1-benzyl-N-(1-methyl-2-oxo-1,2,3,4,5,10-hexahydro-8H-thieno[3',4':3,4]pyrazolo[1,5-a][1,3]diazepin-3-yl)-1H-1,2,4-triazole-3-carboxamide

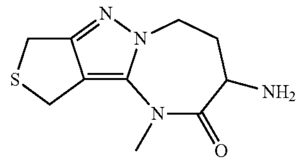 [SMILES: CN1C(=O)C(N)CCn2nc3c(c21)CSC3]

Step 1: 3-amino-1-methyl-1,4,5,10-tetrahydro-8H-thieno[3',4':3,4]pyrazolo[1,5-a][1,3]diazepin-2(3H)-one To a solution of 3-azido-1-methyl-1,4,5,10-tetrahydro-8H-thieno[3',4':3,4]pyrazolo[1,5-a][1,3]diazepin-2(3H)-one (235 mg, 0.89 mmol) in tetrahydrofuran (3.0 mL) and water (1.0 mL) was added polymer-bound triphenylphosphine, (5.4 mmol), and the reaction was stirred at 25° C. for 5 h. The reaction mixture was filtered through celite, and the celite solid was rinsed by a solution of methanol in dichloromethane (10% v/v, 3 mL) twice. The organic solutions were combined and concentrated to dryness in vacuo, and the crude material (285 mg) was used without further purification: LCMS $R_T$=1.3 min; m/z=239 $(M+H)^+$.

LCMS (5 to 95% acetonitrile in water+0.05% formic acid over 5 mins)

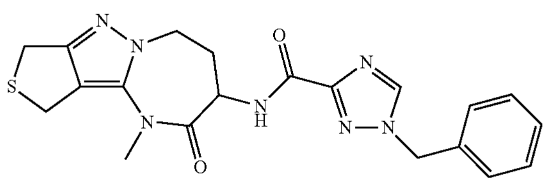 [SMILES: CN1C(=O)C(NC(=O)c2ncn(Cc3ccccc3)n2)CCn2nc3c(c21)CSC3]

Step 2: 1-benzyl-N-(1-methyl-2-oxo-1,2,3,4,5,10-hexahydro-8H-thieno[3',4':3,4]pyrazolo[1,5-a][1,3]diazepin-3-yl)-1H-1,2,4-triazole-3-carboxamide To a suspension of 1-benzyl-1H-1,2,4-triazole-3-carboxylic acid (71 mg, 0.33 mmol) in N,N-dimethylformamide (1.0 mL) and N,N-diisopropylethylamine (0.050 mL, 0.29 mmol) was added 1-[bis(dimethylamino)methylene]-1H-1,2,3-triazolo[4,5-b]pyridinium 3-oxide hexafluorophosphate (129 mg, 0.33 mmol) at 0° C., and the reaction was stirred at 0° C. for 20 min, resulting in a yellow solution. 3-Amino-1-methyl-1,4,5,10-tetrahydro-8H-thieno[3',4':3,4]pyrazolo[1,5-a][1,3]diazepin-2(3H)-one (53 mg, 0.22 mmol) was added. The reaction was stirred at 25° C. for 18 h. The crude material was purified by RP-HPLC affording 1-benzyl-N-(1-methyl-2-oxo-1,2,3,4,5,10-hexahydro-8H-thieno[3',4':3,4]pyrazolo[1,5-a][1,3]diazepin-3-yl)-1H-1,2,4-triazole-3-carboxamide (75 mg, 80% yield) as white powder: $^1$H NMR (400 MHz, DMSO-d6) δ 8.82 (s, 1H), 8.45 (d, J=7.7 Hz, 1H, NH), 7.44-7.26 (m, 5H), 5.48 (s, 2H), 4.40 (dt, J=11.4, 7.8 Hz, 1H), 4.31-4.12 (m, 2H), 3.99-3.78 (m, 4H), 3.19 (s, 3H), 2.73-2.56 (m, 1H), 2.37-2.21 (m, 1H); LCMS $R_T$=3.99 min; m/z=424.1 $(M+H)^+$.

Example 143

Method X8

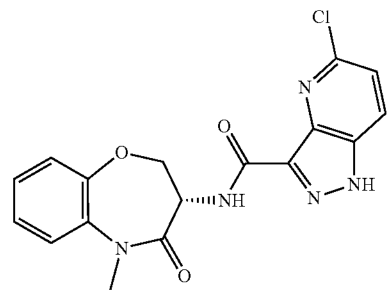 [SMILES: CN1C(=O)[C@@H](NC(=O)c2n[nH]c3ccc(Cl)nc23)COc2ccccc21]

5-chloro-N-[(3S)-5-methyl-4-oxo-2,3-dihydro-1,5-benzoxazepin-3-yl]-1H-pyrazolo[4,3-b]pyridine-3-carboxamide

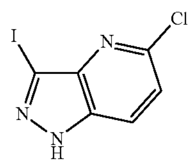 [SMILES: Clc1ccc2[nH]nc(I)c2n1]

Step 1: 5-chloro-3-iodo-1H-pyrazolo[4,3-b]pyridine

To a solution of 5-chloro-1H-pyrazolo[4,3-b]pyridine (501 mg, 3.16 mmol) in N,N-dimethylformamide (16 mL) was added potassium hydroxide (532 mg, 9.49 mmol), followed by iodine (1.45 g, 5.70 mmol) at 0° C., and the reaction was stirred at 0° C. for 30 min, then at 25° C. for 30 min, and finally at 50° C. for 1 h. The crude mixture was diluted with ethyl acetate and washed by sodium sulfite solution till color of organic layer did not change. The aqueous layers were combined and extracted by ethyl acetate. The organic layers were combined, washed by water and brine, dried over magnesium sulfate, filtered through celite, and concentrated to dryness in vacuo affording 5-chloro-3-iodo-1H-pyrazolo[4,3-b]pyridine (770 mg, 87% yield) used without further purification: $^1$H NMR (400 MHz, DMSO-d6) δ 13.89 (s, 1H), 8.10 (d, J=8.8 Hz, 1H), 7.48 (d, J=8.8 Hz, 1H); LCMS $R_T$=1.92 min; m/z=280 $(M+H)^+$.

LCMS (5 to 95% acetonitrile in water+0.05% formic acid over 5 mins)

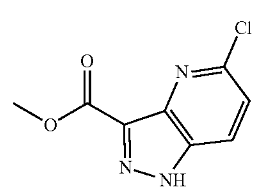

Step 2: methyl 5-chloro-1H-pyrazolo[4,3-b]pyridine-3-carboxylate 5-chloro-3-iodo-1H-pyrazolo[4,3-b]pyridine (250 mg, 0.85 mmol), 4,5-bis(diphenylphosphino)-9,9-dimethylxanthene (49 mg, 0.085 mmol,) and palladium(II) acetate (9.5 mg, 0.042 mmol) were mixed in triethylamine (2.6 mL), methanol (2.6 mL) and N,N-dimethylformamide (2.5 mL), and the yellow solution was stirred under atmosphere of carbon monoxide at room temperature for 10 min and then at 70° C. for 2 days. The crude mixture was concentrated to dryness in vacuo, and the crude residue was purified by column chromatography (silica gel, 100-200 mesh, 0-50% ethyl acetate in dichloromethane) affording methyl 5-chloro-1H-pyrazolo[4,3-b]pyridine-3-carboxylate (0.12 g, 67% yield) as off-white powder: $^1$H NMR (400 MHz, DMSO-d6) δ 14.36 (s, 1H), 8.23 (d, J=8.8 Hz, 1H), 7.53 (d, J=8.8 Hz, 1H), 3.92 (s, 3H); LCMS $R_T$=1.48 min; m/z=212 $(M+H)^+$.

LCMS (5 to 95% acetonitrile in water+0.05% formic acid over 5 mins)

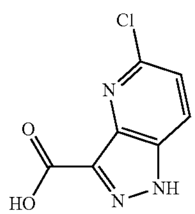 [SMILES: O=C(O)c1n[nH]c2ccc(Cl)nc12]

Step 3: 5-chloro-1H-pyrazolo[4,3-b]pyridine-3-carboxylic acid

To a solution of methyl 5-chloro-1H-pyrazolo[4,3-b]pyridine-3-carboxylate (30.0 mg, 0.142 mmol) in tetrahydrofuran (1.0 mL) and methanol (0.25 mL) was added sodium hydroxide (1 mol/L) in water (0.25 mL), and the reaction was stirred at 25° C. for 8 h. Hydrochloric acid solution (1.0 M, 0.60 mL) was added, resulting in a clear solution with pH ~6. The solution was concentrated to dryness in vacuo, and the crude material was used without further purification: LCMS $R_T$=0.91 min; m/z=198 $(M+H)^+$.

LCMS (5 to 95% acetonitrile in water+0.05% formic acid over 5 mins)

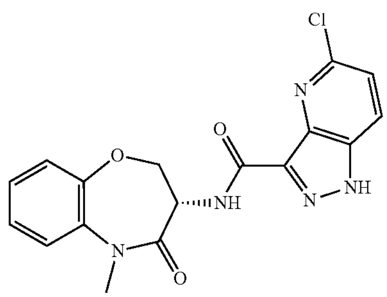 [SMILES: CN1C(=O)[C@@H](NC(=O)c2n[nH]c3ccc(Cl)nc23)COc2ccccc21]

Step 4: 5-chloro-N-[(3S)-5-methyl-4-oxo-2,3-dihydro-1,5-benzoxazepin-3-yl]-1H-pyrazolo[4,3-b]pyridine-3-carboxamide To a solution of 5-chloro-1H-pyrazolo[4,3-b]pyridine-3-carboxylic acid (35 mg, 0.18 mmol) in N,N-dimethylformamide (1.0 mL) was added 1-[bis(dimethylamino)methylene]-1H-1,2,3-triazolo[4,5-b]pyridinium 3-oxide hexafluorophosphate (70 mg, 0.18 mmol) and N,N-diisopropylethylamine (0.042 mL) at 0° C., and the reaction was stirred at 0° C. for 20 min. (3S)-3-Amino-5-methyl-2,3-dihydro-1,5-benzoxazepin-4-one (23 mg, 0.12 mmol) was added. The reaction was stirred at 25° C. for 18 h. The crude material was purified by RP-HPLC affording 5-chloro-N-[(3S)-5-methyl-4-oxo-2,3-dihydro-1,5-benzoxazepin-3-yl]-1H-pyrazolo[4,3-b]pyridine-3-carboxamide (12 mg, 27% yield) as white powder: $^1$H NMR (400 MHz, DMSO-d6) δ 14.22 (bs, 1H), 8.75 (d, J=7.3 Hz, 1H), 8.24 (d, J=8.8 Hz, 1H), 7.54 (d, J=8.8 Hz, 1H), 7.52 (dd, J=6.9, 2.5 Hz, 1H), 7.39-7.24 (m, 3H), 4.97 (dt, J=11.4, 7.4 Hz, 1H), 4.59 (dd, J=9.9, 7.5 Hz, 1H), 4.44 (dd, J=11.4, 9.9 Hz, 1H), 3.36 (s, 3H); LCMS $R_T$=4.37 min; m/z=372.1 $(M+H)^+$.

Example 144

Method X9

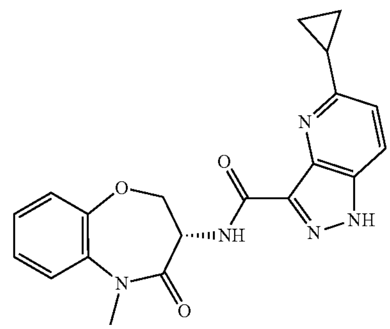 [SMILES: CN1C(=O)[C@@H](NC(=O)c2n[nH]c3ccc(C4CC4)nc23)COc2ccccc21]

5-cyclopropyl-N-[(3S)-5-methyl-4-oxo-2,3-dihydro-1,5-benzoxazepin-3-yl]-1H-pyrazolo[4,3-b]pyridine-3-carboxamide

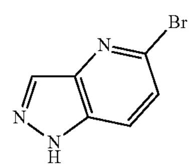

Step 1: 5-bromo-1H-pyrazolo[4,3-b]pyridine

To a suspension of 5-chloro-1H-pyrazolo[4,3-b]pyridine (81 mg, 0.51 mmol) in propionitrile (0.51 mL) was added bromotrimethylsilane (0.135 mL, 1.0 mmol), and the reaction was stirred at 100° C. for 16 h. Second portion of bromotrimethylsilane (0.14 mL, 1.0 mmol) was added, and the suspension was stirred at 110° C. for 6 h. The crude mixture was quenched with ice-water. Sodium carbonate was added to change the pH to 9. The aqueous layer was extracted by a solution of methanol in ethyl acetate (10% v/v) twice. The organic layers were combined, washed by water and brine, dried over magnesium sulfate, filtered through celite, and concentrated to dryness in vacuo. The crude material (189 mg beige solid) was used without further purification: $^1$H NMR (400 MHz, DMSO-d6) δ 13.59 (s, 1H), 8.29 (d, J=1.0 Hz, 1H), 8.02 (dd, J=8.7, 1.0 Hz, 1H), 7.52 (d, J=8.8 Hz, 1H); LCMS $R_T$=1.63 min; m/z=198 $(M+H)^+$.

LCMS (5 to 95% acetonitrile in water+0.05% formic acid over 5 mins)

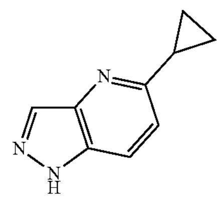 [SMILES: c1cc2[nH]ncc2nc1C1CC1]

Step 2: 5-cyclopropyl-1H-pyrazolo[4,3-b]pyridine

To a solution of 5-bromo-1H-pyrazolo[4,3-b]pyridine (77 mg, 0.37 mmol), palladium(II) acetate (8.3 mg, 0.037 mmol) and S-Phos (31 mg, 0.074 mmol) in tetrahydrofuran (1.5 mL) was added cyclopropylzinc bromide (0.5 mol/L) in tetrahydrofuran (4 mL, 2.2 mmol), and the reaction was stirred at 110° C. for 18 h. The crude mixture was diluted with ethyl acetate and citric acid solution (10% aq.) to pH 9, and the two layers were separated. The aqueous layer was extracted by ethyl acetate. The organic layers were combined, washed by water and brine, dried over magnesium sulfate, filtered through celite, and concentrated to dryness in vacuo. The crude residue was purified by column chromatography (silica gel, 100-200 mesh, 0-50% ethyl acetate in dichloromethane) to afford 5-cyclopropyl-1H-pyrazolo[4,3-b]pyridine (33 mg, 56% yield) as white powder: $^1$H NMR (400 MHz, DMSO-d6) δ 13.12 (bs, 1H), 8.10 (s, 1H), 7.93-7.82 (m, 1H), 7.28 (d, J=8.7 Hz, 1H), 2.27-2.16 (m, 1H), 0.99-0.92 (m, 4H); LCMS $R_T$=1.06 min; m/z=160 $(M+H)^+$.

LCMS (5 to 95% acetonitrile in water+0.05% formic acid over 5 mins)

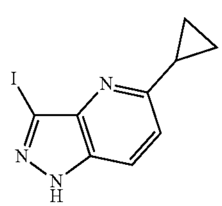 [SMILES: Ic1n[nH]c2ccc(C3CC3)nc12]

Step 3: 5-cyclopropyl-3-iodo-1H-pyrazolo[4,3-b]pyridine

To a solution of 5-cyclopropyl-1H-pyrazolo[4,3-b]pyridine (290 mg, 1.82 mmol) in N,N-dimethylformamide (9.26 mL) was added potassium hydroxide (307 mg, 5.52 mmol), followed by iodine (832 mg, 3.3 mmol) at 25° C., and the reaction was stirred at 50° C. for 1 h. The crude mixture was diluted with ethyl acetate and washed by sodium sulfide solution till color of organic layer did not change. The aqueous layers were combined and extracted by ethyl acetate. The organic layers were combined, washed by water and brine, dried over magnesium sulfate, filtered through celite, and concentrated to dryness in vacuo. The crude residue was purified by column chromatography (silica gel, 100-200 mesh, 0-30% ethyl acetate in dichloromethane) affording 5-cyclopropyl-3-iodo-1H-pyrazolo[4,3-b]pyridine (122 mg, 23% yield) as white solid: $^1$H NMR (400 MHz, DMSO-d6) δ 13.56 (s, 1H), 7.86 (d, J=8.7 Hz, 1H), 7.32 (d, J=8.7 Hz, 1H), 2.30-2.20 (m, 1H), 1.05-0.93 (m, 4H); $R_T$=1.22 min; m/z=286 $(M+H)^+$.

LCMS (5 to 95% acetonitrile in water+0.05% formic acid over 5 mins)

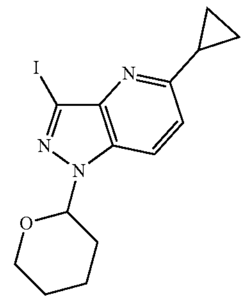

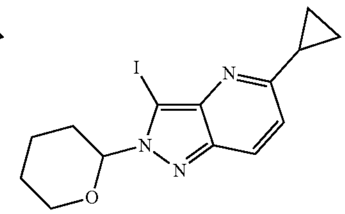

Step 4: 5-cyclopropyl-3-iodo-1-tetrahydropyran-2-yl-pyrazolo[4,3-b]pyridine and 5-cyclopropyl-3-iodo-1-(tetrahydro-2H-pyran-2-yl)-1H-pyrazolo[4,3-b]pyridine To a suspension of 5-cyclopropyl-3-iodo-1H-pyrazolo[4,3-b]pyridine (67 mg, 0.23 mmol) in dichloromethane (2.0 mL) was added 4-methylbenzenesulfonamide hydrate (4.45 mg, 0.023 mmol), followed by 3,4-dihydro-2H-pyran (59 mg, 0.70 mmol), and the reaction was stirred at 25° C. for 18 h, resulting in a colorless solution. More 3,4-dihydro-2H-pyran (59 mg, 0.705 mmol) was added, and the reaction solution was kept at 40° C. for 3.5 h. The solution was concentrated to dryness in vacuo, and the crude residue was purified by column chromatography (silica gel, 100-200 mesh, 0-30% dichloromethane in heptane) affording 5-cyclopropyl-3-iodo-1-tetrahydropyran-2-yl-pyrazolo[4,3-b]pyridine (31 mg, 36% yield) and 5-cyclopropyl-3-iodo-1-(tetrahydro-2H-pyran-2-yl)-1H-pyrazolo[4,3-b]pyridine (15 mg, 18% yield):

Analytical data for one isomer: $^1$H NMR (400 MHz, DMSO-d6) δ 7.97 (d, J=9.0 Hz, 1H), 7.23 (d, J=9.0 Hz, 1H), 5.88-5.78 (m, 1H), 4.02-3.90 (m, 1H), 3.78-3.65 (m, 1H), 2.49-2.38 (m, 1H), 2.30-2.16 (m, 1H), 2.13-1.91 (m, 1H), 1.83-1.39 (m, 3H), 1.06-0.93 (m, 4H); LCMS $R_T$=1.47 min; m/z=370 $(M+H)^+$.

Analytical data for the other isomer: $^1$H NMR (400 MHz, DMSO-d6) δ 8.08 (d, J=8.8 Hz, 1H), 7.40 (d, J=8.8 Hz, 1H), 5.83 (dd, J=9.7, 2.4 Hz, 1H), 3.91-3.83 (m, 1H), 3.78-3.65 (m, 1H), 2.38-2.21 (m, 2H), 2.07-1.91 (m, 2H), 1.79-1.40 (m, 3H), 1.07-0.91 (m, 4H); LCMS $R_T$=1.62 min; m/z=370 $(M+H)^+$.

LCMS (5 to 95% acetonitrile in water+0.05% formic acid over 5 mins)

Note: following Step 5 and 6 below, both isomers afforded 5-cyclopropyl-N-[(3S)-5-methyl-4-oxo-2,3-dihydro-1,5-benzoxazepin-3-yl]-1H-pyrazolo[4,3-b]pyridine-3-carboxamide (i.e., final product).

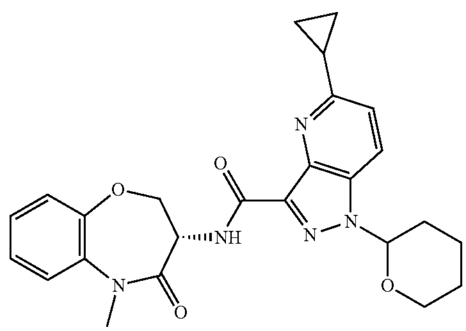 [SMILES: CN1C(=O)[C@@H](NC(=O)c2nn(C3CCCCO3)c3ccc(C4CC4)nc23)COc2ccccc21]

Step 5: 5-cyclopropyl-N—((S)-5-methyl-4-oxo-2,3,4,5-tetrahydrobenzo[b][1,4]oxazepin-3-yl)-1-(tetrahydro-2H-pyran-2-yl)-1H-pyrazolo[4,3-b]pyridine-3-carboxamide 5-cyclopropyl-3-iodo-1-tetrahydropyran-2-yl-pyrazolo[4,3-b]pyridine (31 mg, 0.084 mmol), (3S)-3-amino-5-methyl-2,3-dihydro-1,5-benzoxazepin-4-one hydrochloride (29 mg, 0.13 mmol), 4,5-bis(diphenylphosphino)-9,9-dimethylxanthene (7.3 mg, 0.013 mmol) and palladium(II) acetate (1.9 mg, 0.0084 mmol) were mixed in triethylamine (0.076 mL), N,N-dimethylformamide (0.10 mL) and toluene (5 mL), and the yellow solution was stirred under atmosphere of carbon monoxide at room temperature for 10 min and then at 80° C. for 18 h. The crude mixture was concentrated to dryness in vacuo, and the crude residue was purified by column chromatography (silica gel, 100-200 mesh, 0-40% ethyl acetate in dichloromethane) affording 5-cyclopropyl-N-[(3S)-5-methyl-4-oxo-2,3-dihydro-1,5-benzoxazepin-3-yl]-1-tetrahydropyran-2-yl-pyrazolo[4,3-b]pyridine-3-carboxamide (20 mg, 52% yield) as light brown solid: LCMS $R_T$=3.30 min; m/z=462 $(M+H)^+$.

LCMS (5 to 95% acetonitrile in water+0.05% formic acid over 5 mins)

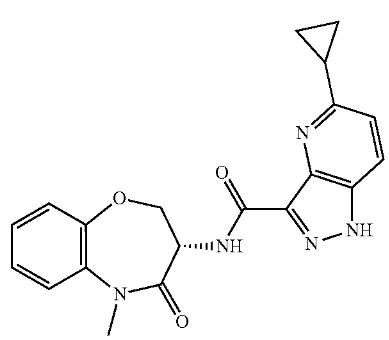 [SMILES: CN1C(=O)[C@@H](NC(=O)c2n[nH]c3ccc(C4CC4)nc23)COc2ccccc21]

Step 6: 5-cyclopropyl-N-[(3S)-5-methyl-4-oxo-2,3-dihydro-1,5-benzoxazepin-3-yl]-1H-pyrazolo[4,3-b]pyridine-3-carboxamide To a solution of 5-cyclopropyl-N-[(3S)-5-methyl-4-oxo-2,3-dihydro-1,5-benzoxazepin-3-yl]-1-tetrahydropyran-2-yl-pyrazolo[4,3-b]pyridine-3-carboxamide (20 mg, 0.043 mmol) in methanol (0.26 mL) and dichloromethane (0.50 mL) was added hydrochloride (4 mol/L) in 1,4-dioxane (0.12 mL, 0.48 mmol), and the reaction was stirred at 25° C. for 1 h. N,N-diisopropylethylamine (0.11 mL) was added. The crude mixture was concentrated to dryness in vacuo. The crude material was purified by RP-HPLC affording 5-cyclopropyl-N-[(3S)-5-methyl-4-oxo-2,3-dihydro-1,5-benzoxazepin-3-yl]-1H-pyrazolo[4,3-b]pyridine-3-carboxamide (13.2 mg, 81% yield) as white powder: $^1$H NMR (400 MHz, DMSO-d6) δ 9.50 (d, J=7.2 Hz, 1H), 8.03 (d, J=8.7 Hz, 1H), 7.55-7.48 (m, 1H), 7.48 (d, J=8.8 Hz, 1H), 7.38-7.27 (m, 3H), 5.01 (dt, J=11.3, 7.3 Hz, 1H, CHN), 4.64 (dd, J=9.8, 7.4 Hz, 1H), 4.29 (dd, J=11.3, 9.9 Hz, 1H), 3.38 (s, 3H), 2.41-2.28 (m, 1H, Ar—CH), 1.43-1.33 (m, 1H), 1.27-1.17 (m, 1H), 1.15-1.05 (m, 2H); LCMS $R_T$=4.73 min; m/z=378.2 $(M+H)^+$.

Example 145

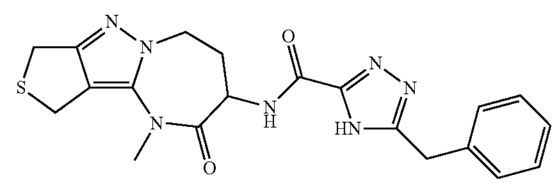 [SMILES: CN1C(=O)C(NC(=O)c2nnc(Cc3ccccc3)[nH]2)CCn2nc3c(c21)CSC3]

5-benzyl-N-(1-methyl-2-oxo-1,2,3,4,5,10-hexahydro-8H-thieno[3',4':3,4]pyrazolo[1,5-a][1,3]diazepin-3-yl)-4H-1,2,4-triazole-3-carboxamide Step 1: 5-benzyl-N-(1-methyl-2-oxo-1,2,3,4,5,10-hexahydro-8H-thieno[3',4':3,4]pyrazolo[1,5-a][1,3]diazepin-3-yl)-4H-1,2,4-triazole-3-carboxamide To a solution of 5-benzyl-4H-1,2,4-triazole-3-carboxylic acid (113 mg, 0.556 mmol) in N,N-dimethylformamide (1.5 mL) and N,N-diisopropylethylamine (0.0776 mL, 0.44 mmol) was added 1-[bis(dimethylamino)methylene]-1H-1,2,3-triazolo[4,5-b]pyridinium 3-oxide hexafluorophosphate (216 mg, 0.56 mmol,) at 0° C., and the reaction was stirred at 0° C. for 20 min, resulting in a brown solution. 3-Amino-1-methyl-1,4,5,10-tetrahydro-8H-thieno[3',4':3,4]pyrazolo[1,5-a][1,3]diazepin-2(3H)-one (53 mg, 0.22 mmol) was added. The reaction was stirred at 25° C. for 18 h. The crude material was purified by RP-HPLC affording 5-benzyl-N-(1-methyl-2-oxo-1,2,3,4,5,10-hexahydro-8H-thieno[3',4':3,4]pyrazolo[1,5-a][1,3]diazepin-3-yl)-4H-1,2,4-triazole-3-carboxamide (54 mg, 57% yield) as white powder: $^1$H NMR (400 MHz, DMSO-d6) δ 14.40 (bs, 1H), 8.48 (bs, 1H), 7.42-7.16 (m, 5H), 4.40 (dt, J=11.4, 7.8 Hz, 1H), 4.32-4.15 (m, 2H), 4.11 (s, 2H), 4.02-3.78 (m, 4H), 3.19 (s, 3H), 2.69-2.56 (m, 1H), 2.40-2.25 (m, 1H); LCMS $R_T$=3.87 min; m/z=424.1 $(M+H)^+$.

Examples 146-170 were prepared according to the Methods above and were purified according the Chiral Methods section below. Table 2 provides data for these compounds.

Chiral Methods

| Example # | SFC analytical method | SFC prep method |
|---|---|---|
| 149 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AD 150 × 21.2 mm I.D., 5 μm Mobile phase: A: CO2 B: Methanol (0.1% NH4OH) Isocratic: 25% B in 6 min Flow rate: 70 mL/min Column temperature: 40 oC, BPR: 100 bar |
| 147 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AD150 × 21.2 mm I.D., 5 μm Mobile phase: A: CO2 B: Methanol (0.1% NH4OH) Isocratic: 25% B in 6 min Flow rate: 70 mL/min Column temperature: 40 oC, BPR: 100 bar |
| 148 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AD150 × 21.2 mm I.D., 5 μm Mobile phase: A: CO2 B: Methanol (0.1% NH4OH) Isocratic: 25% B in 6 min Flow rate: 70 mL/min Column temperature: 40 oC, BPR: 100 bar |
| 150 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralcel OJ 250 × 21.1 mm I.D., 5 μm Mobile phase: A: CO2 B: Methanol (0.1% NH4OH) Isocratic: 20% in 10 min B Flow rate: 70 mL/min Column temperature: 40 oC, BPR: 100 bar |
| 149 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralcel OJ 250 × 21.1 mm I.D., 5 μm Mobile phase: A: CO2 B: Methanol (0.1% NH4OH) Isocratic: 20% B in 10 min Flow rate: 70 mL/min Column temperature: 40 oC, BPR: 100 bar |
| 153 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralcel OJ 250 × 21.1 mm I.D., 5 μm Mobile phase: A: CO2 B: Methanol (0.1% NH4OH) Isocratic: 15% B in 10 min Flow rate: 70 mL/min Column temperature: 40 oC, BPR: 100 bar |
| 152 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralcel OJ 250 × 21.1 mm I.D., 5 μm Mobile phase: A: CO2 B: Methanol (0.1% NH4OH) Isocratic: 15% B in 10 min Flow rate: 70 mL/min Column temperature: 40 oC, BPR: 100 bar |
| 154 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralcel OX 250 × 21.2 mm I.D., 5 μm Mobile phase: A: CO2 B: Methanol (0.1% NH4OH) Isocratic: 40% B in 6 min Flow rate: 70 mL/min Column temperature: 40 oC, BPR: 100 bar |
| 156 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralcel OX 250 × 21.2 mm I.D., 5 μm Mobile phase: A: CO2 B: Methanol (0.1% NH4OH) Isocratic: 40% B in 6 min Flow rate: 70 mL/min Column temperature: 40 oC, BPR: 100 bar |
| 155 | SFC condition: Column: Chiralpak AD 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralpak AD 150 × 21.2 mm I.D., 5 μm Mobile phase: A: CO2 B: Methanol (0.1% NH4OH) Isocratic: 30% B in 6 min Flow rate: 70 mL/min Column temperature: 40 oC, BPR: 100 bar |
| 161 | SFC condition: Column: Phenomenex Lux Cellulose-3 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Phenomenex Lux Cellulose-3 150 × 21.2 mm I.D., 5 μm Mobile phase: A: CO2 B: Methanol (0.1% NH4OH) Isocratic: 15% B in 6 min Flow rate: 70 mL/min Column temperature: 40 oC, BPR: 100 bar |
| 168 | SFC condition: Column: Phenomenex Lux Cellulose-3 50 × 4.6 mm I.D., 3 μm Mobile phase: A: CO2 B: | SFC condition: Column: Phenomenex Lux Cellulose-3 150 × 21.2 mm I.D., 5 μm |

-continued

| Example # | SFC analytical method | SFC prep method |
|---|---|---|
| | Methanol (0.1% NH4OH) Gradient: 5-60% B in 2.5 min Flow rate: 4 mL/min Column temperature: 40 oC, BPR: 120 bar | Mobile phase: A: CO2 B: Methanol (0.1% NH4OH) Isocratic: 15% B in 6 min Flow rate: 70 mL/min Column temperature: 40 oC, BPR: 100 bar |
| 159 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AD 150 × 30 mm I.D., 5 μm Mobile phase: A: CO2 B: Methanol (0.1% NH4OH) Gradient: 5-60% B in 6 min Flow rate: 100 mL/min Column temperature: 40 oC, BPR: 100 bar |
| 169 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AS 150 × 30 mm I.D., 5 μm Mobile phase: A: CO2 B: Methanol (0.1% NH4OH) Gradient: 5-60% B in 6 min Flow rate: 100 mL/min Column temperature: 40 oC, BPR: 100 bar |
| 170 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AD 150 × 30 mm I.D., 5 μm Mobile phase: A: CO2 B: Methanol (0.1% NH4OH) 5-60% B in 10 min Flow rate: 100 mL/min Column temperature: 40 oC, BPR: 100 bar |
| 162 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AD 150 × 30 mm I.D., 5 μm Mobile phase: A: CO2 B: Methanol (0.1% NH4OH) 5-60% B in 10 min Flow rate: 100 mL/min Column temperature: 40 oC, BPR: 100 bar |
| 157 | SFC condition: Column: Chiralpak AD 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralpak AD 150 × 30.0 mm I.D., 5 μm Mobile phase: A: CO2 B: Methanol (0.1% NH4OH) Isocratic: 35% B in 6 min Flow rate: 150 mL/min Column temperature: 25 oC, BPR: 100 bar |
| 167 | SFC condition: Column: Chiralpak AD 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Chiralpak AD 150 × 30.0 mm I.D., 5 μm Mobile phase: A: CO2 B: Methanol (0.1% NH4OH) Isocratic: 35% B in 6 min Flow rate: 150 mL/min Column temperature: 25 oC, BPR: 100 bar |
| 163 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Cellulose-1 150 × 21.1 mm I.D., 5 μm Mobile phase: A: CO2 B: Methanol (0.1% NH4OH) Isocratic: 25% B in 10 min Flow rate: 70 mL/min Column temperature: 40 oC, BPR: 100 bar |
| 160 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: Cellulose-1 150 × 21.1 mm I.D., 5 μm Mobile phase: A: CO2 B: Methanol (0.1% NH4OH) Isocratic: 30% B in 10 min Flow rate: 70 mL/min Column temperature: 40 oC, BPR: 100 bar |
| 166 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AD 150 × 30 mm I.D., 5 μm Mobile phase: A: CO2 B: Methanol (0.1% NH4OH) 5-60% B in 10 min Flow rate: 100 mL/min Column temperature: 40 oC, BPR: 100 bar |
| 158 | SFC condition: Column: Chiralcel OX 50 × 4.6 mm I.D., 3 μm Mobile phase: A: CO2 B: Methanol (0.1% NH4OH) Gradient: 5-60% B in 2.5 min Flow rate: 4 mL/min Column temperature: 40 oC, BPR: 120 bar | SFC condition: Column: ES Industries AD 150 × 30 mm ID., 5 μm Mobile phase: A: CO2 B: Methanol (0.1% NH4OH) 5-60% B in 10 min Flow rate: 100 mL/min Column temperature: 40 oC, BPR: 100 bar |
| 165 | SFC condition: Column: Chiralcel OX 50 × 4.6 mm I.D., 3 μm Mobile phase: | SFC condition: Column: ES Industries AD 150 × 30 mm I.D., |

-continued

| Example # | SFC analytical method | SFC prep method |
| --- | --- | --- |
| | A: CO2 B: Methanol (0.1% NH4OH) Gradient: 5-60% B in 2.5 min Flow rate: 4 mL/min Column temperature: 40 oC, BPR: 120 bar | 5 μm Mobile phase: A: CO2 B: Methanol (0.1% NH4OH) 5-60% B in 10 min Flow rate: 100 mL/min Column temperature: 40 oC, BPR: 100 bar |

Example 171

WX Method ZZZ

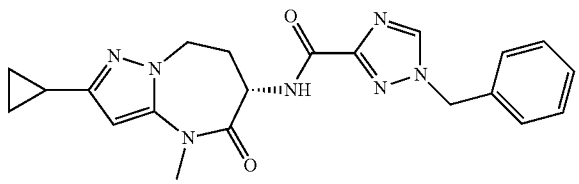 [SMILES: CN1C(=O)[C@@H](NC(=O)c2ncn(Cc3ccccc3)n2)CCn2nc(C3CC3)cc21]

(S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide

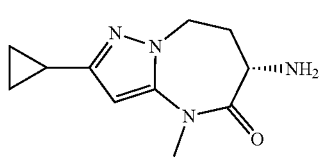

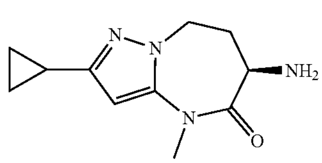

Step 1: (S)-6-amino-2-cyclopropyl-4-methyl-7,8-dihydro-4H-pyrazolo[1,5-a][1,3]diazepin-5(6H)-one and (R)-6-amino-2-cyclopropyl-4-methyl-7,8-dihydro-4H-pyrazolo[1,5-a][1,3]diazepin-5(6H)-one 6-amino-2-cyclopropyl-4-methyl-7,8-dihydro-4H-pyrazolo[1,5-a][1,3]diazepin-5(6H)-one was underwent SFC separation to get peak 1 as (S)-6-amino-2-cyclopropyl-4-methyl-7,8-dihydro-4H-pyrazolo[1,5-a][1,3]diazepin-5(6H)-one and peak 2 as (R)-6-amino-2-cyclopropyl-4-methyl-7,8-dihydro-4H-pyrazolo[1,5-a][1,3]diazepin-5(6H)-one.

SFC condition: Column: Chiralpak OD 250×30 mm I.D., 5 μm Mobile phase: A: $CO_2$ B: Ethanol (0.05% $NH_4OH$) Isocratic: 20% B in 6 min Flow rate: 50 mL/min Column temperature: 40° C., BPR: 100 bar (Peak 1: 3.11 min) (Peak 2: 3.53 min).

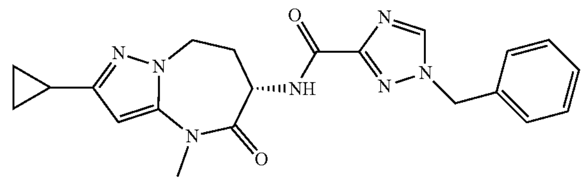 [SMILES: CN1C(=O)[C@@H](NC(=O)c2ncn(Cc3ccccc3)n2)CCn2nc(C3CC3)cc21]

Step 2: (S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide A mixture of (S)-6-amino-2-cyclopropyl-4-methyl-7,8-dihydro-4H-pyrazolo[1,5-a][1,3]diazepin-5(6H)-one (200 mg, 0.91 mmol), 1-benzyl-1H-1,2,4-triazole-3-carboxylic acid (0.19 g, 0.91 mmol), 1H-benzo[d][1,2,3]triazol-1-ol (180 mg, 1.36 mmol) and $N^1$-((ethylimino)methylene)-$N^3$,$N^3$-dimethylpropane-1,3-diamine hydrochloride (260 mg, 1.36 mmol) in N,N-dimethylformamide (5 mL) was stirred at 25° C. for 16 h. The reaction mixture was concentrated under reduced pressure and the residue was purified by RP-HPLC (acetonitrile 30-60%/0.1% HCl in water) to afford (S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (120 mg, 32%) as a white solid: $^1H$ NMR (400 MHz, DMSO-$d_6$) δ 8.83 (s, 1H), 8.54 (d, J=8.0 Hz, 1H), 7.41-7.28 (m, 5H), 6.06 (s, 1H), 5.48 (s, 2H), 4.34-4.22 (m, 2H), 4.12-4.04 (m, 1H), 3.19 (s, 3H), 2.61-2.54 (m, 1H), 2.37-2.29 (m, 1H), 1.88-1.81 (m, 1H), 0.89-0.81 (m, 2H), 0.70-0.61 (m, 2H). LCMS $R_T$=0.98 min; m/z=406.1 $(M+H)^+$.

LCMS (10 to 80% acetonitrile in water+0.03% trifluoacetic acid over 2.0 mins) retention time 0.98 min, ESI+ found [M+H]=406.2.

WX Method B

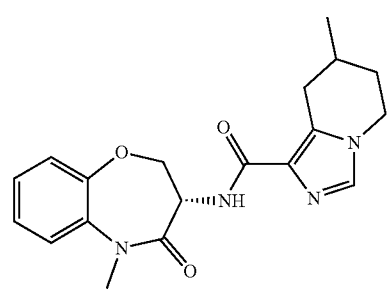 [SMILES: CC1CCn2cnc(C(=O)N[C@H]3COc4ccccc4N(C)C3=O)c2C1]

7-methyl-N—((S)-5-methyl-4-oxo-2,3,4,5-tetrahydrobenzo[b][1,4]oxazepin-3-yl)-5,6,7,8-tetrahydroimidazo[1,5-a]pyridine-1-carboxamide)

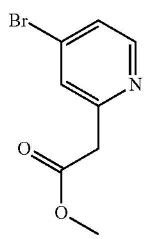

Step 1: methyl 2-(4-bromopyridin-2-yl) acetate

A mixture of 1-(tert-butyldimethylsilyloxy)-1-methoxyethene (2.2 g, 11.5 mmol), 4-bromopyridinen-oxide (1.0 g, 5.7 mmol), N,N-diisopropylethylamine (2.2 g, 17.2 mmol) and bromo[tri(1-pyrrolidinyl)]phosphonium hexafluorophosphate (3.0 g, 6.3 mmol) in tetrahydrofuran (20 mL) was stirred at 25° C. for 1 h and then diluted with ethyl acetate (30 mL). The resulting mixture was washed with water (3×30 mL), dried over sodium sulfate and concentrated under reduced pressure. The residue was purified by column chromatography (silica gel, 100-200 mesh, 0 to 10% ethyl acetate in petroleum ether) to afford methyl 2-(4-bromopyridin-2-yl) acetate (1.0 g, 75%): LCMS $R_T$=0.52 min; m/z=232.0 $(M+H)^+$.

LCMS (5 to 95% acetonitrile in water+0.03% trifluoacetic acid over 1.5 mins) retention time 0.520 min, ESI+ found [M+H]=232.0

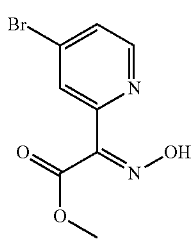

Step 2: (E)-methyl 2-(4-bromopyridin-2-yl)-2-(hydroxyimino) acetate

To a solution of methyl 2-(4-bromopyridin-2-yl) acetate (4.0 g, 17.4 mmol) in acetic acid (60 mL) was added sodium nitrite (1.2 g, 17.4 mmol) in water (30 mL) at 0° C. After addition, the mixture was stirred at 25° C. for 40 min. Water (30 mL) was added and the mixture was stirred for an additional 1 h. The reaction was concentrated to dryness under reduced pressure and the residue was taken up in ethyl acetate (100 mL), washed with water (2×50 mL), brine (50 mL), dried over sodium sulfate and concentrated under reduced pressure. The residue was then purified by column chromatography (silica gel, 100-200 mesh, 0 to 20% methanol in dichloromethane) to afford (E)-methyl 2-(4-bromopyridin-2-yl)-2-(hydroxyimino) acetate (3.6 g, 80%) as yellow oil: LCMS $R_T$=0.65 min; m/z=261.0 $(M+H)^+$.

LCMS (5 to 95% acetonitrile in water+0.03% trifluoacetic acid over 1.5 mins) retention time 0.651 min, ESI+ found [M+H]=261.0

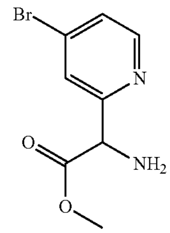

Step 3: methyl 2-amino-2-(4-bromopyridin-2-yl) acetate

A mixture of zinc (1.8 g, 27.8 mmol) and (E)-methyl 2-(4-bromopyridin-2-yl)-2-(hydroxyimino) acetate (3.6 g, 13.9 mmol) in methanol (56 mL) and water (36 mL) was slowly added formic acid (36 mL, 961.9 mmol) over 30 min at 0° C. After addition, the mixture was stirred at 25° C. for 5 h and then diluted with ethyl acetate (50 mL). The organic layer was washed with water (3×30 mL). The combined aqueous layers were concentrated under reduced pressure to afford crude methyl 2-amino-2-(4-bromopyridin-2-yl) acetate (3.0 g, 88%) as yellow oil, used as is in the next step without further purification.

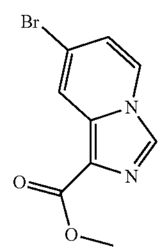

Step 4: methyl 7-bromoimidazo[1,5-a]pyridine-1-carboxylate

A mixture of methyl 2-amino-2-(4-bromo-2-pyridyl) acetate (500 mg, 2.0 mmol) and triethyl orthoformate (2 mL, 2.0 mmol) was heated at 150° C. under microwave conditions for 10 min. The mixture was concentrated under reduced pressure and purified by preparative TLC (50% ethyl acetate in petroleum ether) to afford methyl 7-bromoimidazo[1,5-a]pyridine-1-carboxylate (210 mg, 40%) as brown oil: LCMS $R_T$=0.65 min; m/z=257.0 $(M+H)^+$.

LCMS (5 to 95% acetonitrile in water+0.03% trifluoacetic acid over 1.5 mins) retention time 0.654 min, ESI+ found [M+H]=257.0

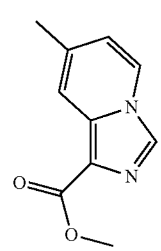

Step 5: methyl 7-methylimidazo[1,5-a]pyridine-1-carboxylate

A mixture of methyl 7-bromoimidazo[1,5-a]pyridine-1-carboxylate (210 mg, 0.8 mmol), potassiumcarbonate (227 mg, 1.7 mmol) and trimethylboroxine (310 mg, 2.5 mmol) in 1,4-dioxane (5 mL) was treated with tetrakis(triphenylphosphine) palladium(0) (47 mg, 0.04 mmol). The resulting mixture was heated to 120° C. for 4 h under nitrogen. The mixture was filtered and concentrated under reduced pressure. The residue was purified by preparative TLC (50% ethyl acetate in petroleum ether) to afford methyl 7-methylimidazo[1,5-a]pyridine-1-carboxylate (110 mg, 70%) as a yellow solid, used in the next step without further purification.

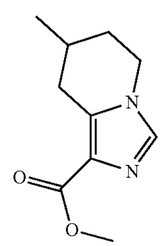

Step 6: methyl 7-methyl-5,6,7,8-tetrahydroimidazo[1,5-a]pyridine-1-carboxylate

A mixture of methyl 7-methylimidazo[1,5-a]pyridine-1-carboxylate (90 mg, 0.47 mmol) and 10% palladium on carbon (50 mg, 0.05 mmol) in methanol (10 mL) was hydrogenated (50 psi) at 25° C. for 18 h. The mixture was filtered and the filtrate was concentrated under reduced pressure. The residue was purified by preparative TLC (7% methanol in dichloromethane) affording methyl 7-methyl-5,6,7,8-tetrahydroimidazo[1,5-a]pyridine-1-carboxylate (50 mg, 54%) as yellow oil: LCMS $R_T$=1.24 min; m/z=195.1 $(M+H)^+$.

LCMS (10 to 80% acetonitrile in water+0.05% ammonium bicarbonate over 3 mins) retention time 1.239 min, ESI+ found [M+H]=195.1

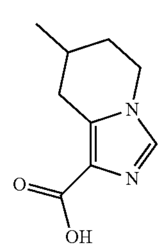

Step 7: 7-methyl-5,6,7,8-tetrahydroimidazo[1,5-a]pyridine-1-carboxylic acid

To a solution of methyl 7-methyl-5,6,7,8-tetrahydroimidazo[1,5-a]pyridine-1-carboxylate (18 mg, 0.09 mmol) in tetrahydrofuran (2 mL) and water (2 mL) was added lithium hydroxide (11 mg, 0.46 mmol). The resulting mixture was stirred at 25° C. for 12 h, adjusted to pH=4 by addition of hydrochloric acid (1.0 M) and concentrated under reduced pressure. The residue was extracted with dichloromethane (30 mL) and ethyl acetate (1×30 mL). The combined organic layers were concentrated under reduced pressure to afford 7-methyl-5,6,7,8-tetrahydroimidazo[1,5-a]pyridine-1-carboxylic acid (15 mg, 90%) as white solids, used in the next step without further purification.

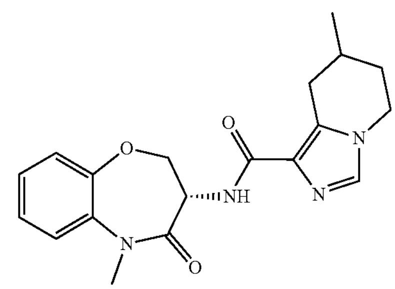 [SMILES: CC1CCn2cnc(C(=O)N[C@H]3COc4ccccc4N(C)C3=O)c2C1]

Step 8: 7-methyl-N—((S)-5-methyl-4-oxo-2,3,4,5-tetrahydrobenzo[b][1,4]oxazepin-3-yl)-5,6,7,8-tetrahydroimidazo[1,5-a]pyridine-1-carboxamide To a solution of 7-methyl-5,6,7,8-tetrahydroimidazo[1,5-a]pyridine-1-carboxylic acid (22 mg, 0.12 mmol) and (3S)-3-amino-5-methyl-2,3-dihydro-1,5-benzoxazepin-4-one (23 mg, 0.12 mmol) in N,N-dimethylformamide (2 mL) was added (7-azabenzotriazol-1-yloxy)tripyrrolidinophosphonium hexafluorophosphate (76 mg, 0.15 mmol). The resulting mixture was stirred for 12 h at 25° C. and then concentrated to dryness under reduced pressure. The residue was purified by RP-HPLC (27-57% methanol in water and 0.05% ammonia hydroxide) to afford 7-methyl-N—((S)-5-methyl-4-oxo-2,3,4,5-tetrahydrobenzo[b][1,4]oxazepin-3-yl)-5,6,7,8-tetrahydroimidazo[1,5-a]pyridine-1-carboxamide (6.6 mg, 15%) as a white solid: $^1$H NMR (400 MHz, $CD_3OD$) δ 7.55-7.53 (m, 1H), 7.43-7.41 (m, 1H), 7.32-7.29 (m, 2H), 7.11-6.92 (m, 1H), 4.97-4.96 (m, 1H), 4.59-4.55 (m, 1H), 4.35-4.21 (m, 2H), 3.94-3.93 (m, 1H), 3.42-3.41 (m, 3H), 3.31-3.24 (m, 1H), 2.41-2.34 (m, 1H), 2.01-1.98 (m, 2H), 1.63-1.59 (m, 1H), 1.12-1.09 (m, 3H). LCMS $R_T$=0.74 min; m/z=355.0 $(M+H)^+$.

LCMS (5 to 95% acetonitrile in water+0.03% trifluoacetic acid over 1.5 mins) retention time 0.740 min, ESI+ found [M+H]=355.0.

Example 172

WX Method PP

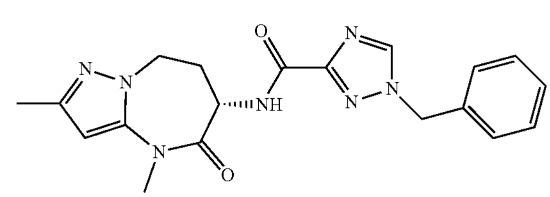 [SMILES: Cc1cc2n(n1)CC[C@H](NC(=O)c1ncn(Cc3ccccc3)n1)C(=O)N2C]

(S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of 1-benzyltriazole-4-carboxylic acid (20 mg, 0.10 mmol), (S)-6-amino-2,4-dimethyl-7,8-dihydro-4H- pyrazolo[1,5-a][1,3]diazepin-5(6H)-one (15 mg, 0.08 mmol), $N^1$-((ethylimino)methylene)-$N^3$,$N^3$-dimethyl propane-1,3-diamine hydrochloride (22 mg, 0.11 mmol) and 1H-benzo[d][1,2,3]triazol-1-ol (19 mg, 0.11 mmol) in N,N-dimethylformamide (5 mL) was stirred at 25° C. for 2 h. The reaction was concentrated under reduced pressure and the residue was purified by RP-HPLC (acetonitrile 17-47%/0.05% ammonium bicarbonate in water) to afford (S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide (12.1 mg, 39%) as white solid: $^1$H NMR (400 MHz, DMSO-$d_6$) δ 8.85 (s, 1H), 8.54 (d, J=8.0 Hz, 1H), 7.39-7.29 (m, 5H), 6.13 (s, 1H), 5.49 (s, 2H), 4.15-4.10 (m, 2H), 4.08-4.06 (m, 1H), 3.21 (s, 3H), 2.59-2.54 (m, 1H), 2.35-2.29 (m, 1H), 2.16 (s, 3H). LCMS $R_T$=0.909 min; m/z=380.4 $(M+H)^+$.

LCMS (10 to 80% acetonitrile in water+0.03% trifluoacetic acid over 2.0 mins) retention time 0.909 min, ESI+ found [M+H]=380.4.

Example 173

WX Method D

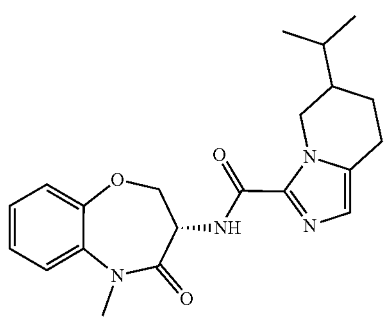 [SMILES: CC(C)C1CCc2cnc(C(=O)N[C@H]3COc4ccccc4N(C)C3=O)n2C1]

6-isopropyl-N—((S)-5-methyl-4-oxo-2,3,4,5-tetrahydrobenzo[b][1,4]oxazepin-3-yl)-5,6,7,8-tetrahydroimidazo[1,5-a]pyridine-3-carboxamide

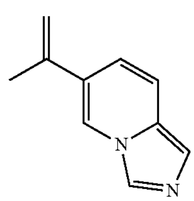

Step 1: 6-(prop-1-en-2-yl)imidazo[1,5-a]pyridine

A mixture of 6-bromoimidazo[1,5-a]pyridine (500 mg, 2.5 mmol), potassium isopropyl trifluoroborate (750 mg, 5.0 mmol), cesium carbonate (1.654 g, 5.0 mmol) and 1,1'-bis(diphenylphosphino)ferrocene-palladium(II)dichloride (185 mg, 0.1 mmol) in tetrahydrofuran (20 mL) and water (2 mL) was heated at 80° C. for 3 h under nitrogen. After cooled, the mixture was diluted with water (10 mL) and extracted with ethyl acetate (3×30 mL). The combined organic layers were dried over sodium sulfate and concentrated under reduced pressure. The residue was purified with preparative TLC (10% methanol in dichloromethane) to afford 6-(prop-1-en-2-yl)imidazo[1,5-a]pyridine (300 mg, 74%) as brown oil. LCMS $R_T$=0.26 min; m/z=158.8 $(M+H)^+$.

LCMS (5 to 95% acetonitrile in water+0.03% trifluoacetic acid over 1.5 mins) retention time 0.26 min, ESI+ found [M+H]=158.8

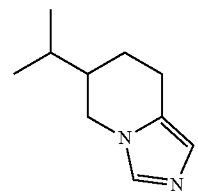

Step 2: 6-isopropyl-5,6,7,8-tetrahydroimidazo[1,5-a]pyridine

A mixture of 6-(prop-1-en-2-yl)imidazo[1,5-a]pyridine (300 mg, 1.9 mmol) and 10% palladium on carbon (202 mg, 0.2 mmol) in methanol (30 mL) was hydrogenated (50 psi) at 20° C. for 72 h. The reaction mixture was filtered and the filtrate was concentrated under reduced pressure. The residue was purified by preparative TLC (10% methanol in dichloromethane) to afford 6-isopropyl-5,6,7,8-tetrahydroimidazo[1,5-a]pyridine (150 mg, 48%) as brown oil, used in the next step without further purification.

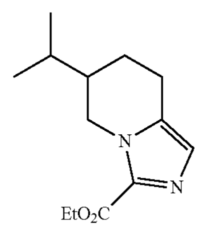 [SMILES: CCOC(=O)c1ncc2n1CC(C(C)C)CC2]

Step 3: ethyl 6-isopropyl-5,6,7,8-tetrahydroimidazo[1,5-a]pyridine-3-carboxylate To a solution of 6-isopropyl-5,6,7,8-tetrahydroimidazo[1,5-a]pyridine (300 mg, 1.8 mmol) in tetrahydrofuran (5 mL) was added n-butyllithium (2.5 M, 1.1 mL, 2.7 mmol) at −78° C. Stirring at −78° C. was continued for 1 h, then ethyl chloroformate (1300 mg, 12.3 mmol) was added dropwise. The resulting mixture was stirred at −78° C. for 1 h and quenched by addition of saturated aqueous ammonium chloride (10 mL). The mixture was extracted with ethyl acetate (3×20 mL). The combined organic layers were dried over sodium sulfate and concentrated under reduced pressure. The residue was purified by column chromatography (silica gel, 100-200 mesh, 100% dichloromethane) to afford ethyl 6-isopropyl-5,6,7,8-tetrahydroimidazo[1,5-a]pyridine-3-carboxylate (100 mg, 23%) as brown oil, used in the next step without further purification.

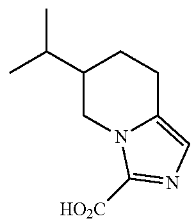

Step 4: 6-isopropyl-5,6,7,8-tetrahydroimidazo[1,5-a]pyridine-3-carboxylic acid

A mixture of 6-isopropyl-5,6,7,8-tetrahydroimidazo[1,5-a]pyridine-3-carboxylate (100 mg, 0.45 mmol) and potassium hydroxide (252 mg, 4.5 mmol) in ethanol (5 mL) and water (1 mL) was stirred at 25° C. for 12 h. The solvent was removed under reduced pressure. The residue was diluted with water (10 mL) and adjusted to pH=4 by addition of hydrochloric acid (2.0 M). The mixture was concentrated under reduced pressure to afford crude 6-isopropyl-5,6,7,8-tetrahydroimidazo[1,5-a]pyridine-3-carboxylic acid (80 mg, 85%) as a white solid, used in the next step without further purification.

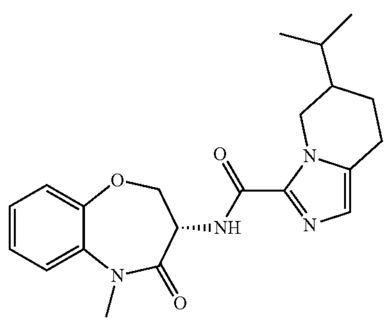 [SMILES: CC(C)C1CCc2cnc(C(=O)N[C@H]3COc4ccccc4N(C)C3=O)n2C1]

Step 5: 6-isopropyl-N—((S)-5-methyl-4-oxo-2,3,4,5-tetrahydrobenzo[b][1,4]oxazepin-3-yl)-5,6,7,8-tetrahydroimidazo[1,5-a]pyridine-3-carboxamide A mixture of (S)-3-amino-5-methyl-2,3-dihydrobenzo[b][1,4]oxazepin-4(5H)-one (40 mg, 0.2 mmol), 6-isopropyl-5,6,7,8-tetrahydroimidazo[1,5-a]pyridine-3-carboxylic acid (43 mg, 0.2 mmol), 1H-benzo[d][1,2,3]triazol-1-ol (42 mg, 0.3 mmol) and $N^1$-((ethylimino)methylene)-$N^3$,$N^3$-dimethylpropane-1,3-diamine hydrochloride (59 mg, 0.3 mmol) in N,N-dimethylformamide (5 mL) was stirred at 25° C. for 16 h. After evaporation of the solvent under reduced pressure, the residue was purified by RP-HPLC (acetonitrile 46-76%/0.05% ammonia hydroxide in water) to afford 6-isopropyl-N—((S)-5-methyl-4-oxo-2,3,4,5-tetrahydrobenzo[b][1,4]oxazepin-3-yl)-5,6,7,8-tetrahydroimidazo[1,5-a]pyridine-3-carboxamide (10 mg, 14%): $^1$H NMR (400 MHz, DMSO-$d_6$) δ 8.27 (d, J=8.0 Hz, 1H), 7.49 (d, J=6.8 Hz, 1H), 7.35-7.26 (m, 2H), 7.25-7.21 (m, 1H), 6.81 (s, 1H), 4.83-4.75 (m, 1H), 4.63-4.51 (m, 2H), 4.43-4.37 (m, 1H), 3.69-3.62 (m, 1H), 3.31 (s, 3H), 2.95-2.87 (m, 1H), 2.67-2.58 (m, 1H), 1.93-1.85 (m, 1H), 1.68-1.54 (m, 2H), 1.41-1.28 (m, 1H), 0.92-0.88 (m, 6H). LCMS $R_T$=0.84 min; m/z=393.1 $(M+H)^+$.

LCMS (5 to 95% acetonitrile in water+0.03% trifluoacetic acid over 1.5 mins) retention time 0.84 min, ESI+ found [M+H]=393.1

Example 174

WX Method FF

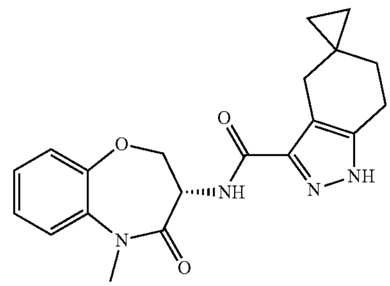 [SMILES: CN1C(=O)[C@@H](NC(=O)c2n[nH]c3c2CC2(CC3)CC2)COc2ccccc21]

(S)—N-(5-methyl-4-oxo-2,3,4,5-tetrahydrobenzo[b][1,4]oxazepin-3-yl)-1',4',6',7'-tetrahydrospiro[cyclopropane-1,5'-indazole]-3'-carboxamide

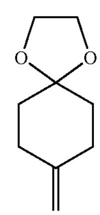

Step 1: 8-methylene-1,4-dioxaspiro[4.5]decane

To a suspension of (bromomethyl)triphenylphosphonium (34.12 g, 96.04 mmol) in tetrahydrofuran (200 mL) was added potassium tert-butoxide (10.8 g, 96.0 mmol) portion-wise at 0° C. The resulting mixture was stirred at 0° C. for 1 h and then a solution of 1,4-dioxaspiro[4.5]decan-8-one (5.0 g, 32.0 mmol) in tetrahydrofuran (20 mL) was added dropwise. After addition, the reaction mixture was slowly warmed to 23° C. and stirred for 18 h. The reaction mixture was quenched by addition of water (120 mL) and extracted with ethyl acetate (3×200 mL). The combined organic layers were washed with brine (100 mL) and concentrated under reduced pressure. The residue was purified by column chromatography (silica gel, 100-200 mesh, 0 to 5% ethyl acetate in petroleum ether) to afford 8-methylene-1,4-dioxaspiro[4.5]decane (3.9 g, 79%) as yellow oil: $^1$H NMR (400 MHz, $CDCl_3$) δ 4.67 (s, 2H), 3.98 (s, 4H), 2.37-2.30 (m, 4H), 1.73-1.70 (m, 4H).

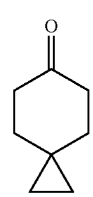

Step 2: Spiro[2.5]octan-6-one

To a solution of 8-methylene-1,4-dioxaspiro[4.5]decane (3.9 g, 25.3 mmol) in toluene (7.2 mL) was added diethylzinc (1.0 M, 63.2 mL, 63.2 mmol) at −40° C. The mixture was stirred for 10 min and then diiodomethane (33.9 g, 126.4 mmol) added dropwise. After addition, the resulting mixture was allowed to warm to 24° C. and stirred for 18 h. The reaction mixture was poured onto ice-cooled saturated aqueous ammonium chloride (30 mL) and extracted with ethyl acetate (3×60 mL). The combined organic extracts were washed with water (30 mL), dried over sodium sulfate and concentrated under reduced pressure. The residue was purified by column chromatography (silica gel, 100-200 mesh, 0 to 5% ethyl acetate in petroleum ether) affording a colorless oil. A mixture of this oil and trifluoroacetic acid (2.9 mL, 38.9 mmol) in tetrahydrofuran (8 mL) and water (7 mL) was stirred at 23° C. for 2 h. The mixture was adjusted to pH=7 by addition of aqueous sodium hydroxide (2 M) and extracted with diethyl ether (3×30 mL). The combined organic layers were washed water (20 mL), brine (20 mL), dried over sodium sulfate and concentrated under reduced pressure affording crude spiro[2.5]octan-6-one (1.4 g, 44.6% over 2 steps) as colorless oil: $^1$H NMR (400 MHz, $CDCl_3$) δ 2.40 (t, J=6.8 Hz, 4H), 1.67 (t, J=6.4 Hz, 4H), 0.47 (s, 4H).

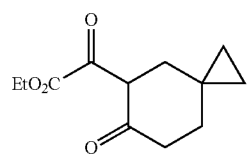 [SMILES: CCOC(=O)C(=O)C1CC2(CCC1=O)CC2]

Step 3: Ethyl 2-oxo-2-(6-oxospiro[2.5]octan-7-yl) acetate

To a solution of spiro[2.5]octan-6-one (500 mg, 4.03 mmol) in ethanol (5 mL) was added sodium ethanoxide and diethyl oxalate (588 mg, 4.0 mmol) at 0° C. After addition, the mixture was allowed to warm to 20° C. and stirred for 20 h. The solvent was removed under reduced pressure affording crude ethyl 2-oxo-2-(6-oxospiro[2.5]octan-7-yl) acetate (800 mg, 88%) as a yellow solid, used as is in the next step without further purification.

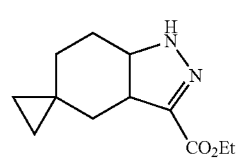 [SMILES: CCOC(=O)C1=NNC2CCC3(CC3)CC12]

Step 4: Ethyl spiro[1,3a,4,6,7,7a-hexahydroindazole-5,1'-cyclopropane]-3-carboxylate To a solution of ethyl 2-oxo-2-(6-oxospiro[2.5]octan-7-yl)acetate (800 mg, 3.57 mmol) in glacial acetic acid (3 mL) was added hydrazine (0.12 mL, 3.92 mmol) at 0° C. The mixture was stirred for 18 h at 23° C. and then extracted with ethyl acetate (3×30 mL). The combined organic layers were concentrated under reduced pressure and the residue was purified by column chromatography (silica gel, 100-200 mesh, 0 to 30% ethyl acetate in petroleum ether) affording ethyl spiro[1,3a, 1,4,6,7-tetrahydroindazole-5,1'-cyclopropane]-3-carboxylate (50 mg, 6.4%) as a pale yellow solid: $^1$H NMR (400 MHz, $CDCl_3$) δ 4.41-4.30 (m, 2H), 2.76 (t, J=6.0 Hz, 2H), 2.62 (s, 2H), 1.62 (t, J=6.2 Hz, 2H), 1.38 (t, J=7.2 Hz, 3H), 0.44 (s, 4H). LCMS $R_T$=0.817 min; m/z=220.9 $(M+H)^+$.

LCMS (5 to 95% acetonitrile in water+0.03% trifluoacetic acid over 1.5 mins) retention time 0.817 min, ESI+ found [M+H]=220.9.

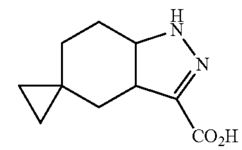 [SMILES: O=C(O)C1=NNC2CCC3(CC3)CC12]

Step 5: Spiro[1,3a,4,6,7,7a-hexahydroindazole-5,1'-cyclopropane]-3-carboxylic acid A mixture of ethyl spiro[1,3a, 1,4,6,7-tetrahydroindazole-5,1'-cyclopropane]-3-carboxylate (50 mg, 0.23 mmol) and lithium hydroxide hydrate (27 mg, 1.13 mmol) in tetrahydrofuran (5 mL) and water (2 mL) was stirred at 23° C. for 18 h. The organic solvent was removed under reduced pressure and the aqueous residue was adjusted to pH=5 by addition of hydrochloric acid (1.0 M). The solution was then extracted with ethyl acetate (3×30 mL). The combined organic layers were dried over sodium sulfate and concentrated under reduced pressure affording crude spiro[1,3a, 1,4,6,7-tetrahydro indazole-5,1'-cyclopropane]-3-carboxylic acid (40 mg, 91%) as a white solid: LCMS $R_T$=1.456 min; m/z=193.2 $(M+H)^+$.

LCMS (0 to 60% acetonitrile in water+0.04% formic acid over 3 mins) retention time 1.456 min, ESI+ found [M+H]=193.2.

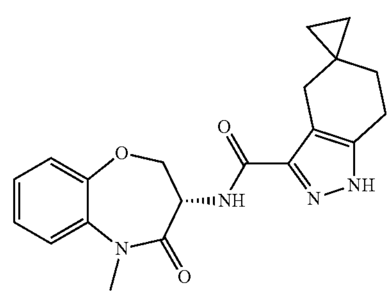 [SMILES: CN1C(=O)[C@@H](NC(=O)c2n[nH]c3c2CC2(CC3)CC2)COc2ccccc21]

Step 6 (S)—N-(5-methyl-4-oxo-2,3,4,5-tetrahydrobenzo[b][1,4]oxazepin-3-yl)-1',4',6',7'-tetrahydrospiro[cyclopropane-1,5'-indazole]-3'-carboxamide A mixture of spiro[1,3a, 1,4,6,7-tetrahydroindazole-5,1'-cyclopropane]-3-carboxylic acid (40 mg, 0.21 mmol), (3s)-3-amino-5-methyl-2,3-dihydro-1,5-benzoxazepin-4-one (44 mg, 0.23 mmol), 1H-benzo[d][1,2,3]triazol-1-ol (33 mg, 0.25 mmol) and $N^1$-((ethylimino)methylene)-$N^3$,$N^3$-dimethylpropane-1,3-diamine hydrochloride (45 mg, 0.25 mmol) in N, N-dimethylformamide (5 mL) was stirred at 25° C. for 1 h. The reaction was concentrated under reduced pressure and the residue was purified by RP-HPLC (acetonitrile 38-68%/0.05% ammonia in water) affording (S)—N-(5-methyl-4-oxo-2,3,4,5-tetrahydrobenzo[b][1,4]oxazepin-3-yl)-1',4',6',7'-tetrahydrospiro[cyclopropane-1,5'-indazole]-3'-carboxamide (18.7 mg, 24%) as a white solid: $^1H$ NMR (400 MHz, DMSO-$d_6$) δ 12.90 (s, 1H), 7.92 (d, J=7.6 Hz, 1H), 7.48 (d, J=6.0 Hz, 1H), 7.37-7.16 (m, 3H), 4.85-4.75 (m, 1H), 4.53-4.44 (m, 1H), 4.42-4.35 (m, 1H), 3.31 (s, 3H), 2.63 (t, J=5.6 Hz, 2H), 2.41 (s, 2H), 1.49 (t, J=5.6 Hz, 2H), 0.46-0.20 (m, 4H). LCMS $R_T$=0.856 min; m/z=367.1 $(M+H)^+$.

LCMS (5 to 95% acetonitrile in water+0.03% trifluoacetic acid over 1.5 mins) retention time 0.856 min, ESI+ found [M+H]=367.1.

Example 175

WX Method RRRRRR

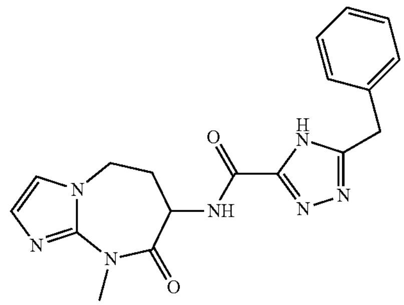 [SMILES: CN1C(=O)C(NC(=O)c2nnc(Cc3ccccc3)[nH]2)CCn2ccnc21]

5-benzyl-N-(9-methyl-8-oxo-6,7,8,9-tetrahydro-5H-imidazo[1,2-a][1,3]diazepin-7-yl)-4H-1,2,4-triazole-3-carboxamide A mixture of (5-benzyl-4H-1,2,4-triazole-3-carboxylic acid (22 mg, 0.11 mmol), 7-amino-9-methyl-6,7-dihydro-5H-imidazo[1,2-a][1,3]diazepin-8(9H)-one (20 mg, 0.11 mmol), $N^1$-((ethylimino)methylene)-$N^3$,$N^3$-dimethyl propane-1,3-diamine hydrochloride (26 mg, 0.13 mmol) and 1H-benzo[d][1,2,3]triazol-1-ol (18 mg, 0.13 mmol) in N,N-dimethylformamide (4 mL) was stirred at 25° C. for 12 h. The reaction was concentrated under reduced pressure and the residue was purified by RP-HPLC (14-24% methanol in water and 0.05% ammonia hydroxide) to afford 5-benzyl-N-(9-methyl-8-oxo-6,7,8,9-tetrahydro-5H-imidazo[1,2-a][1,3]diazepin-7-yl)-4H-1,2,4-triazole-3-carboxamide (5 mg, 12%) as white solid: $^1H$ NMR (400 MHz, $CD_3OD$) δ 7.34-7.22 (m, 5H), 7.09 (s, 1H), 6.96 (s, 1H), 4.53-4.48 (m, 1H), 4.32-4.26 (m, 1H), 4.16 (s, 2H), 4.10-4.02 (m, 1H), 3.38 (s, 3H), 2.77-2.90 (m, 1H), 2.29-2.21 (m, 1H). LCMS $R_T$=1.21 min; m/z=366.1 $(M+H)^+$.

LCMS (0 to 60% acetonitrile in water+0.05% ammonium bicarbonate over 3 mins) retention time 1.21 min, ESI+ found [M+H]=366.1.

Example 176

WX Method SSSSSS

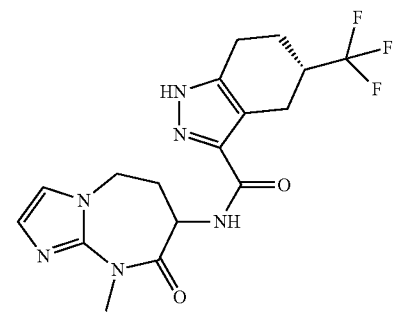 [SMILES: CN1C(=O)C(NC(=O)c2n[nH]c3c2C[C@@H](C(F)(F)F)CC3)CCn2ccnc21]

(5S)—N-(9-methyl-8-oxo-6,7,8,9-tetrahydro-5H-imidazo[1,2-a][1,3]diazepin-7-yl)-5-(trifluoromethyl)-4,5,6,7-tetrahydro-1H-indazole-3-carboxamide A mixture of (5S)-5-(trifluoromethyl)-4,5,6,7-tetrahydro-1H-indazole-3-carboxylic acid (26 mg, 0.11 mmol), 7-amino-9-methyl-6,7-dihydro-5H-imidazo[1,2-a][1,3]diazepin-8(9H)-one (20 mg, 0.11 mmol), $N^1$-((ethylimino)methylene)-$N^3$,$N^3$-dimethyl propane-1,3-diamine hydrochloride (26 mg, 0.13 mmol) and 1H-benzo[d][1,2,3]triazol-1-ol (18 mg, 0.13 mmol) in N,N-dimethylformamide (4 mL) was stirred at 25° C. for 12 h. The reaction was concentrated under reduced pressure and the residue was purified by RP-HPLC (17-47% methanol in water and 0.05% ammonia hydroxide) to afford (5S)—N-(9-methyl-8-oxo-6,7,8,9-tetrahydro-5H-imidazo[1,2-a][1,3]diazepin-7-yl)-5-(trifluoro methyl)-4,5,6,7-tetrahydro-1H-indazole-3-carboxamide (10.7 mg, 24%) as white solid: $^1H$ NMR (400 MHz, $CD_3OD$) δ 7.09 (d, J=1.2 Hz, 1H), 6.96 (d, J=1.2 Hz, 1H), 4.52-4.47 (m, 1H), 4.32-4.26 (m, 1H), 4.07-4.05 (m, 1H), 3.39 (s, 3H), 3.14-3.10 (m, 1H), 2.88-2.84 (m, 2H), 2.76-2.70 (m, 1H), 2.64-2.48 (m, 2H), 2.21-2.20 (m, 2H), 1.74-1.69 (m, 1H). LCMS $R_T$=0.69 min; m/z=397.0 $(M+H)^+$.

LCMS (5 to 95% acetonitrile in water+0.03% trifluoacetic acid over 1.5 mins) retention time 0.69 min, ESI+ found [M+H]=397.0.

Example 177

WX Method TTTTTT

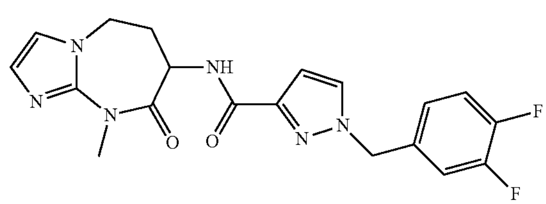 [SMILES: CN1C(=O)C(NC(=O)c2ccn(Cc3ccc(F)c(F)c3)n2)CCn2ccnc21]

1-(3,4-difluorobenzyl)-N-(9-methyl-8-oxo-6,7,8,9-tetrahydro-5H-imidazo[1,2-a][1,3]diazepin-7-yl)-1H-pyrazole-3-carboxamide A mixture of 1-[(3,4-difluorophenyl)methyl]pyrazole-3-carboxylic acid (26 mg, 0.11 mmol), 7-amino-9-methyl-6,7-dihydro-5H-imidazo[1,2-a][1,3]diazepin-8(9H)-one (20 mg, 0.11 mmol), $N^1$-((ethylimino)methylene)-$N^3$,$N^3$-dimethyl propane-1,3-diamine hydrochloride (26 mg, 0.13 mmol) and 1H-benzo[d][1,2,3]triazol-1-ol (18 mg, 0.13 mmol) in N,N-dimethylformamide (4 mL) was stirred at 25° C. for 12 h. The reaction was concentrated under reduced pressure and the residue was purified by RP-HPLC (30-40% methanol in water and 0.05% ammonia hydroxide) to afford 1-(3,4-difluorobenzyl)-N-(9-methyl-8-oxo-6,7,8,9-tetrahydro-5H-imidazo[1,2-a][1,3]diazepin-7-yl)-1H-pyrazole-3-carboxamide (10.8 mg, 24%) as white solid: $^1$H NMR (400 MHz, $CD_3OD$) δ 7.75 (d, J=2.4 Hz, 1H), 7.27-7.21 (m, 2H), 7.09-7.01 (m, 2H), 6.95 (d, J=1.2 Hz, 1H), 6.75-6.74 (m, 1H), 5.38 (s, 2H), 4.53-4.48 (m, 1H), 4.31-4.26 (m, 1H), 4.06-4.03 (m, 1H), 3.38 (s, 3H) 2.85-2.79 (m, 1H), 2.29-2.23 (m, 1H). LCMS $R_T$=1.99 min; m/z=401.1 $(M+H)^+$.

LCMS (0 to 60% acetonitrile in water+0.03% ammonium bicarbonate over 3 mins) retention time 1.99 min, ESI+ found [M+H]=401.1.

Example 178

WX Method UUUUUU

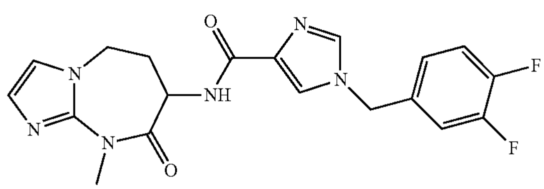 [SMILES: CN1C(=O)C(NC(=O)c2cn(Cc3ccc(F)c(F)c3)cn2)CCn2ccnc21]

1-(3,4-difluorobenzyl)-N-(9-methyl-8-oxo-6,7,8,9-tetrahydro-5H-imidazo[1,2-a][1,3]diazepin-7-yl)-1H-imidazole-4-carboxamide A mixture of 1-[(3,4-difluorophenyl)methyl]imidazole-4-carboxylic acid (26 mg, 0.11 mmol), 7-amino-9-methyl-6,7-dihydro-5H-imidazo[1,2-a][1,3]diazepin-8(9H)-one (20 mg, 0.11 mmol), $N^1$-((ethylimino)methylene)-$N^3$,$N^3$-dimethyl propane-1,3-diamine hydrochloride (26 mg, 0.13 mmol) and 1H-benzo[d][1,2,3]triazol-1-ol (18 mg, 0.13 mmol) in N,N-dimethylformamide (4 mL) was stirred at 25° C. for 12 h. The reaction was concentrated under reduced pressure and the residue was purified by RP-HPLC (13-43% methanol in water and 0.05% ammonia hydroxide) to afford 1-(3,4-difluorobenzyl)-N-(9-methyl-8-oxo-6,7,8,9-tetrahydro-5H-imidazo[1,2-a][1,3]diazepin-7-yl)-1H-imidazole-4-carboxamide (13.1 mg, 29%) as white solid: $^1$H NMR (400 MHz, $CD_3OD$) δ 7.78 (s, 1H), 7.67 (s, 1H), 7.28-7.23 (m, 2H), 7.11-7.08 (m, 2H), 6.94 (d, J=1.6 Hz, 1H), 5.23 (s, 2H), 4.50-4.46 (m, 1H), 4.31-4.26 (m, 1H), 4.07-4.02 (m, 1H), 3.38 (s, 3H), 2.86-2.80 (m, 1H), 2.25-2.19 (m, 1H). LCMS $R_T$=1.85 min; m/z=401.1 $(M+H)^+$.

LCMS (0 to 60% acetonitrile in water+0.05% ammonium bicarbonate over 3 mins) retention time 1.85 min, ESI+ found [M+H]=401.1.

Example 179

WX Method DDDDDD

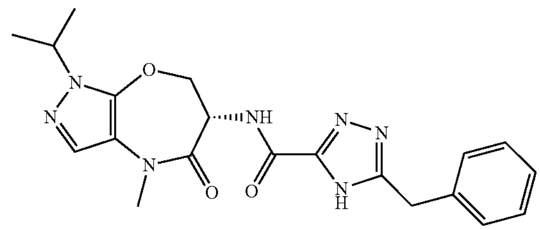 [SMILES: CC(C)n1ncc2c1OC[C@H](NC(=O)c1nnc(Cc3ccccc3)[nH]1)C(=O)N2C]

(S)-5-benzyl-N-(1-isopropyl-4-methyl-5-oxo-4,5,6,7-tetrahydro-1H-pyrazolo[3,4-b][1,4]oxazepin-6-yl)-4H-1,2,4-triazole-3-carboxamide

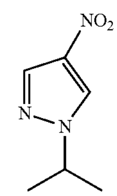

Step 1: 1-isopropyl-4-nitro-1H-pyrazole

To a solution of 4-nitro-1H-pyrazole (10.0 g, 88.4 mmol) in N, N-dimethylformamide (50 mL) was added potassium carbonate (36.7 g, 265.3 mmol) and stirred at 25° C. for 1 h, then 2-iodopropane (17.6 mL, 176.9 mmol) was added. The mixture was stirred at 25° C. for 12 h and then concentrated under reduced pressure. The residue was diluted with water (100 mL) and extracted with ethyl acetate (3×100 mL). The combined organic layers were washed with water (100 mL), brine (100 mL), dried over sodium sulfate and concentrated under reduced pressure to afford 1-isopropyl-4-nitro-pyrazole (11.0 g, 80%) as yellow solid: $^1$H NMR (400 MHz, $CD_3OD$) δ 8.58 (s, 1H), 8.09 (s, 1H), 4.61-4.54 (m, 1H), 1.52 (d, J=6.4 Hz, 6H).

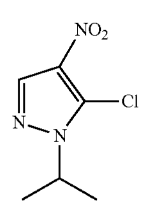

Step 2: 5-chloro-1-isopropyl-4-nitro-1H-pyrazole

To a cooled (−78° C.) solution of 1-isopropyl-4-nitro-pyrazole (5.0 g, 32.2 mmol) in tetrahydrofuran (50 mL) was added lithium bis(trimethylsilyl)azanide (1.0 M, 34.9 mL, 34.9 mmol) dropwise. The mixture was stirred at −78° C. for 30 min and then hexachloroethane (8.36 g, 35.3 mmol) was added. The mixture was stirred at 25° C. for 18 h and quenched by addition of saturated aqueous ammonium chloride (80 mL). The mixture was extracted with ethyl acetate (3×50 mL). The combined organic layers were washed with water (50 mL), brine (50 mL), dried over sodium sulfate and concentrated under reduced pressure. The residue was purified by column chromatography (silica gel, 100-200 mesh, 0 to 10% ethyl acetate in petroleum ether) to afford 5-chloro-1-isopropyl-4-nitro-pyrazole (5.0 g, 82%) as colorless solid: $^1$H NMR (400 MHz, $CD_3OD$) δ 8.26 (s, 1H), 4.85-4.80 (m, 1H), 1.49 (d, J=6.8 Hz, 6H).

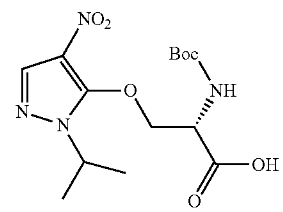

Step 3: (S)-2-((tert-butoxycarbonyl)amino)-3-((1-isopropyl-4-nitro-1H-pyrazol-5-yl)oxy)propanoic acid To a solution of (S)-2-((tert-butoxycarbonyl)amino)-3-hydroxypropanoic acid (4.38 g, 21.4 mmol) in N,N-dimethylformamide (30 mL) was added sodium hydride (1.1 g, 28.5 mmol, 60%) at 0° C. The mixture was stirred at 0° C. for 1 h. At which time 5-chloro-1-isopropyl-4-nitro-pyrazole (2.7 g, 14.2 mmol) was added. After addition, the mixture was stirred at 20° C. for another 3 h, and then quenched by addition of water (30 mL). The resulting mixture was extracted with ethyl acetate (3×30 mL). The combined organic layers were washed with water (30 mL), brine (30 mL), dried over sodium sulfate and concentrated under reduced pressure. The residue was purified by chromatography on silica (0-100% ethyl acetate in petroleum ether) to afford (S)-2-((tert-butoxycarbonyl)amino)-3-((1-isopropyl-4-nitro-1H-pyrazol-5-yl) oxy)propanoic acid (0.7 g, 14%) as yellow oil: LCMS $R_T$=0.68 min; m/z=302.9 $(M+H)^+$.

LCMS (5-95% acetonitrile in water+0.03% trifluoroacetic over 1.5 mins) retention time 0.68 min, ESI+ found [M−55]= 302.9.

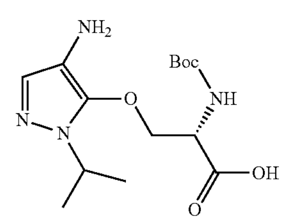 [SMILES: CC(C)n1ncc([N+](=O)[O-])c1OC[C@H](NC(=O)OC(C)(C)C)C(=O)O]

Step 4: (S)-3-((4-amino-1-isopropyl-1H-pyrazol-5-yl)oxy)-2-((tert-butoxycarbonyl)amino)propanoic acid A mixture of (S)-2-((tert-butoxycarbonyl)amino)-3-((1-isopropyl-4-nitro-1H-pyrazol-5-yl)oxy)propanoic acid (0.2 g, 0.56 mmol) and 10% palladium on carbon (59 mg, 0.06 mmol) in methanol (20 mL) was hydrogenated (50 psi) at 25° C. for 2 h. The mixture was filtered and the filtrate was concentrated under reduced pressure to afford (S)-3-((4-amino-1-isopropyl-1H-pyrazol-5-yl)oxy)-2-((tert-butoxycarbonyl)amino)propanoic acid (180 mg, 98%) as black oil: LCMS $R_T$=0.558 min; m/z=328.9 $(M+H)^+$.

LCMS (5-95% acetonitrile in water+0.03% trifluoroacetic over 1.5 mins) retention time 0.558 min, ESI+ found [M+H]= 328.9.

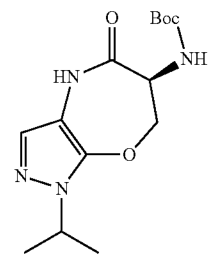 [SMILES: CC(C)n1ncc2c1OC[C@H](NC(=O)OC(C)(C)C)C(=O)N2]

Step 5: (S)-tert-butyl(1-isopropyl-5-oxo-4,5,6,7-tetrahydro-1H-pyrazolo[3,4-b][1,4]oxazepin-6-yl) carbamate To a solution of (S)-3-((4-amino-1-isopropyl-1H-pyrazol-5-yl)oxy)-2-((tert-butoxycarbonyl)amino)propanoic acid (540 mg, 1.64 mmol) in N,N-dimethylformamide (10 mL) was added $N^1$-((ethylimino)methylene)-$N^3$,$N^3$-dimethylpropane-1,3-diamine hydrochloride (378 mg, 1.97 mmol). The reaction mixture was stirred at 25° C. for 3 h and then concentrated under reduced pressure. The residue was purified by column chromatography (silica gel, 100-200 mesh, 0 to 50% ethyl acetate in petroleum ether) to afford (S)-tert-butyl (1-isopropyl-5-oxo-4,5,6,7-tetrahydro-1H-pyrazolo[3,4-b][1,4]oxazepin-6-yl)carbamate (170 mg, 33%) as brown solid: LCMS $R_T$=0.79 min; m/z=254.9 $(M-56)^+$.

LCMS (5-95% acetonitrile in water+0.03% trifluoroacetic over 1.5 mins) retention time 0.79 min, ESI+ found $[M-56]^+$= 254.9.

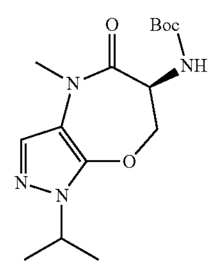 [SMILES: CC(C)n1ncc2c1OC[C@H](NC(=O)OC(C)(C)C)C(=O)N2C]

Step 6: (S)-tert-butyl(1-isopropyl-4-methyl-5-oxo-4,5,6,7-tetrahydro-1H-pyrazolo[3,4-b][1,4]oxazepin-6-yl)carbamate To a solution of (S)-tert-butyl (1-isopropyl-5-oxo-4,5,6,7-tetrahydro-1H-pyrazolo[3,4-b][1,4]oxazepin-6-yl)carbamate (170 mg, 0.55 mmol) in N,N-dimethylformamide (10 mL) was added potassium carbonate (151 mg, 1.10 mmol) and iodomethane (94 mg, 0.66 mmol). The mixture was stirred for 1 h and then concentrated under reduced pressure. The residue was purified by column chromatography (silica gel, 100-200 mesh, 0 to 50% ethyl acetate in petroleum ether) to afford (S)-tert-butyl (1-isopropyl-4-methyl-5-oxo-4,5,6,7-tetrahydro-1H-pyrazolo[3,4-b][1,4]

oxazepin-6-yl)carbamate (120 mg, 68%) as green oil. LCMS $R_T$=0.69 min; m/z=268.9 (M+H)$^+$.

LCMS (5-95% acetonitrile in water+0.03% trifluoroacetic over 1.5 mins) retention time 0.69 min, ESI+ found [M−56]$^+$= 268.9.

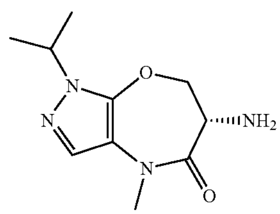 [SMILES: CC(C)n1ncc2c1OC[C@H](N)C(=O)N2C]

Step 7: (S)-6-amino-1-isopropyl-6,7-dihydro-1H-pyrazolo[3,4-b][1,4]oxazepin-5(4H)-one A mixture of (S)-tert-butyl (1-isopropyl-4-methyl-5-oxo-4,5,6,7-tetrahydro-1H-pyrazolo[3,4-b][1,4]oxazepin-6-yl) carbamate (100 mg, 0.31 mmol) and hydrochloric acid (4 M in EtOAc, 5.0 mL, 20.0 mmol) in ethyl acetate (5 mL) was stirred at 25° C. for 2 h. The reaction mixture was adjusted pH=8 by addition of ammonia hydroxide and then concentrated under reduced pressure to give crude (S)-6-amino-1-isopropyl-6,7-dihydro-1H-pyrazolo[3,4-b][1,4]oxazepin-5 (4H)-one (69 mg, 100%) as white solid, used in the next step without further purification.

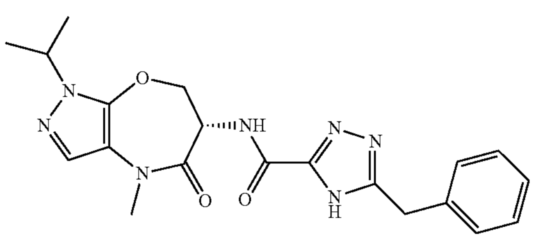 [SMILES: CC(C)n1ncc2c1OC[C@H](NC(=O)c1nnc(Cc3ccccc3)[nH]1)C(=O)N2C]

Step 8: (S)-5-benzyl-N-(1-isopropyl-4-methyl-5-oxo-4,5,6,7-tetrahydro-1H-pyrazolo[3,4-b][1,4]oxazepin-6-yl)-4H-1,2,4-triazole-3-carboxamide A mixture of (S)-6-amino-1-isopropyl-6,7-dihydro-1H-pyrazolo[3,4-b][1,4]oxazepin-5(4H)-one (13 mg, 0.06 mmol), 5-benzyl-4H-1,2,4-triazole-3-carboxylic acid (12 mg, 0.06 mmol), 1H-benzo[d][1,2,3]triazol-1-ol (9 mg, 0.07 mmol) and $N^1$-((ethylimino)methylene)-$N^3$,$N^3$-dimethylpropane-1,3-diamine hydrochloride (13 mg, 0.07 mmol) in N,N-dimethylformamide (4 mL) was stirred at 25° C. for 12 h. The reaction concentrated under reduced pressure and the residue was purified by RP-HPLC (acetonitrile 0-40%/0.1% ammonium hydroxide in water) to afford (S)-5-benzyl-N-(1-isopropyl-4-methyl-5-oxo-4,5,6,7-tetrahydro-1H-pyrazolo[3,4-b][1,4]oxazepin-6-yl)-4H-1,2,4-triazole-3-carboxamide (7 mg, 28%) as white solids: $^1$H NMR (400 MHz, $CD_3OD$) δ 7.48 (s, 1H), 7.35-7.21 (m, 5H), 4.67-4.64 (m, 1H), 4.60-4.53 (m, 2H), 4.45-4.40 (m, 1H), 4.18 (s, 2H), 3.37 (s, 3H), 1.45-1.40 (m, 6H). LCMS $R_T$=0.99 min; m/z=410.3 (M+H)$^+$.

LCMS (10-80% acetonitrile in water+0.03% trifluoroacetic over 2 mins) retention time 0.99 min, ESI+ found [M+H]=410.3.

Example 180

WX Method FFFFFF

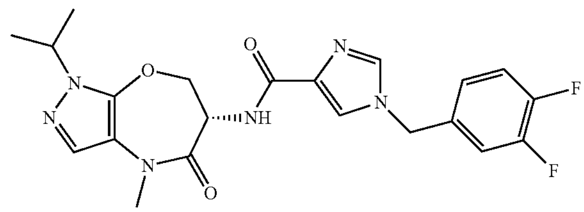 [SMILES: CC(C)n1ncc2c1OC[C@H](NC(=O)c1cn(Cc3ccc(F)c(F)c3)cn1)C(=O)N2C]

(S)-1-(3,4-difluorobenzyl)-N-(1-isopropyl-4-methyl-5-oxo-4,5,6,7-tetrahydro-1H-pyrazolo[3,4-b][1,4]oxazepin-6-yl)-1H-imidazole-4-carboxamide A mixture of (S)-6-amino-1-isopropyl-6,7-dihydro-1H-pyrazolo[3,4-b][1,4]oxazepin-5(4H)-one (17 mg, 0.08 mmol), 1-[(3,4-difluorophenyl)methyl]pyrazole-3-carboxylic acid (19 mg, 0.08 mmol), 1H-benzo[d][1,2,3]triazol-1-ol (13 mg, 0.09 mmol) and $N^1$-((ethylimino)methylene)-$N^3$,$N^3$-dimethylpropane-1,3-diamine hydrochloride (17 mg, 0.09 mmol) in N,N-dimethylformamide (4 mL) was stirred at 25° C. for 12 h. The reaction concentrated under reduced pressure and the residue was purified by RP-HPLC (acetonitrile 0-40%/0.1% ammonium hydroxide in water) to afford (S)-1-(3,4-difluorobenzyl)-N-(1-isopropyl-4-methyl-5-oxo-4,5,6,7-tetrahydro-1H-pyrazolo[3, 4-b][1,4]oxazepin-6-yl)-1H-imidazole-4-carboxamide (13 mg, 39%) as white solid. $^1$H NMR (400 MHz, $CD_3OD$) δ 7.78 (d, J=2.4 Hz, 1H), 7.48 (s, 1H), 7.29-7.18 (m, 2H), 7.12-7.10 (m, 1H), 6.80 (d, J=2.4 Hz, 1H), 5.39 (s, 2H), 4.67-4.53 (m, 3H), 4.44-4.39 (m, 1H), 3.37 (s, 3H), 1.46-1.40 (m, 6H). LCMS $R_T$ 1.117 min; m/z=445.3 (M+H)$^+$.

LCMS (10-80% acetonitrile in water+0.03% trifluoroacetic over 2 mins) retention time 1.117 min, ESI+ found [M+H]$^+$=445.3.

Example 181

WX Method IIIIII

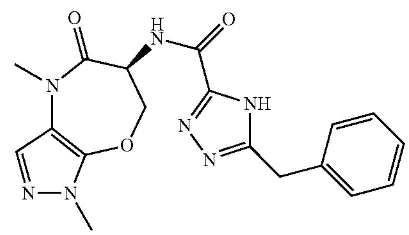 [SMILES: CN1C(=O)[C@@H](NC(=O)c2nnc(Cc3ccccc3)[nH]2)COc2c1cnn2C]

(S)-5-benzyl-N-(1,4-dimethyl-5-oxo-4,5,6,7-tetrahydro-1H-pyrazolo[3,4-b][1,4]oxazepin-6-yl)-4H-1,2,4-triazole-3-carboxamide A mixture of (S)-6-amino-1,4-dimethyl-6,7-dihydropyrazolo[3,4-b][1,4]oxazepin-5-one (24 mg, 0.12 mmol), 5-benzyl-4H-1,2,4-triazole-3-carboxylic acid (25 mg, 0.12 mmol), 1H-benzo[d][1,2,3]triazol-1-ol (19 mg, 0.15 mmol)

and $N^1$-((ethylimino)methylene)-$N^3$,$N^3$-dimethylpropane-1,3-diamine hydrochloride (21 mg, 0.15 mmol) in N,N-dimethylformamide (3 mL) was stirred at 25° C. for 12 h. The reaction was concentrated under reduced pressure and the residue was purified by RP-HPLC (13 to 43% methyl alcohol in water and 0.05% hydrochloric acid) to afford (S)-5-benzyl-N-(1,4-dimethyl-5-oxo-4,5,6,7-tetrahydro-1H-pyrazolo[3,4-b][1,4]oxazepin-6-yl)-4H-1,2,4-triazole-3-carboxamide: $^1H$ NMR (400 MHz, $CD_3OD$) δ 7.69 (s, 1H), 7.38-7.31 (m, 5H), 4.98-4.93 (m, 1H), 4.72-4.69 (m, 1H), 4.58-4.53 (m, 1H), 4.34 (s, 2H), 3.72 (s, 3H), 3.37 (s, 3H). LCMS $R_T$=0.74 min; m/z=382.1 $(M+H)^+$.

LCMS (5 to 95% acetonitrile in water+0.03% trifluoroacetic acid over 1.5 mins) retention time 0.74 min, ESI+ found [M+H]=382.1.

Example 182

WX METHOD JJJJJ

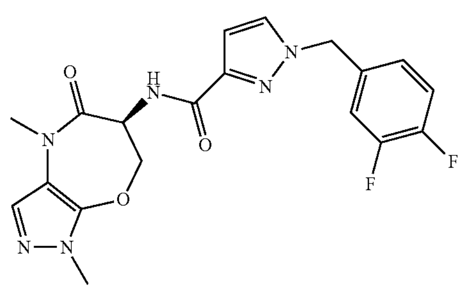

(S)-1-(3,4-difluorobenzyl)-N-(1,4-dimethyl-5-oxo-4,5,6,7-tetrahydro-1H-pyrazolo[3,4-b][1,4]oxazepin-6-yl)-1H-pyrazole-3-carboxamide A mixture of (S)-6-amino-1,4-dimethyl-6,7-dihydropyrazolo[3,4-b][1,4]oxazepin-5-one (24 mg, 0.12 mmol), 1-[(3,4-difluorophenyl)methyl]pyrazole-3-carboxylic acid (32 mg, 0.13 mmol), 1H-benzo[d][1,2,3]triazol-1-ol (19 mg, 0.15 mmol) and $N^1$-((ethylimino)methylene)-$N^3$,$N^3$-dimethylpropane-1,3-diamine hydrochloride (21 mg, 0.15 mmol) in N,N-dimethylformamide (3 mL) was stirred at 25° C. for 12 h. The reaction was concentrated under reduced pressure and the residue was purified by RP-HPLC (13 to 43% methyl alcohol in water and 0.05% hydrochloric acid) to afford (S)-1-(3,4-difluorobenzyl)-N-(1,4-dimethyl-5-oxo-4,5,6,7-tetrahydro-1H-pyrazolo[3,4-b][1,4]oxazepin-6-yl)-1H-pyrazole-3-carboxamide (14 mg, 27%) as a light yellow solid: $^1H$ NMR (400 MHz, $CD_3OD$) δ 7.79 (s, 1H), 7.65 (s, 1H), 7.26-7.21 (m, 2H), 7.12-7.10 (m, 1H), 6.79 (d, J=2.0 Hz, 1H), 5.39 (s, 2H), 4.81-4.78 (m, 1H), 4.68-4.65 (m, 1H), 4.50-4.45 (m, 1H), 3.71 (s, 3H), 3.37 (s, 3H). LCMS $R_T$=0.80 min; m/z=417.1 $(M+H)^+$.

LCMS (5 to 95% acetonitrile in water+0.03% trifluoroacetic acid over 1.5 mins) retention time 0.80 min, ESI+ found [M+H]=417.1.

Example 183

WX Method KKKKKK

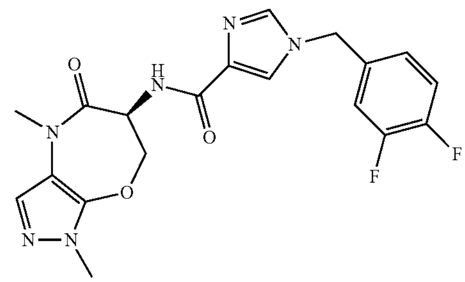 [SMILES: CN1C(=O)[C@@H](NC(=O)c2cn(Cc3ccc(F)c(F)c3)cn2)COc2c1cnn2C]

(S)-1-(3,4-difluorobenzyl)-N-(1,4-dimethyl-5-oxo-4,5,6,7-tetrahydro-1H-pyrazolo[3,4-b][1,4]oxazepin-6-yl)-1H-imidazole-4-carboxamide A mixture of (S)-6-amino-1,4-dimethyl-6,7-dihydropyrazolo[3,4-b][1,4]oxazepin-5-one (24 mg, 0.12 mmol), 1-[(3,4-difluorophenyl)methyl]imidazole-4-carboxylic acid (32 mg, 0.13 mmol), 1H-benzo[d][1,2,3]triazol-1-ol (19 mg, 0.15 mmol) and $N^1$-((ethylimino)methylene)-$N^3$,$N^3$-dimethylpropane-1,3-diamine hydrochloride (21 mg, 0.15 mmol) in N,N-dimethylformamide (3 mL) was stirred at 25° C. for 12 h. The reaction was concentrated under reduced pressure and the residue was purified by RP-HPLC (13 to 43% methyl alcohol in water and 0.05% hydrochloric acid) to afford (S)-1-(3,4-difluorobenzyl)-N-(1,4-dimethyl-5-oxo-4,5,6,7-tetrahydro-1H-pyrazolo[3,4-b][1,4]oxazepin-6-yl)-1H-imidazole-4-carboxamide (16 mg, 32%) as a white solid: $^1H$ NMR (400 MHz, $CD_3OD$) δ 9.24 (s, 1H), 8.24 (s, 1H), 7.62 (s, 1H), 7.52-7.50 (m, 1H), 7.40-7.35 (m, 2H), 5.50 (d, J=6.0 Hz, 2H), 5.00-4.93 (m, 1H), 4.65-4.57 (m, 2H), 3.70 (s, 3H), 3.35 (s, 3H). LCMS $R_T$=0.74 min; m/z=417.0 $(M+H)^+$.

LCMS (5 to 95% acetonitrile in water+0.03% trifluoroacetic acid over 1.5 mins) retention time 0.74 min, ESI+ found [M+H]=417.0.

Examples 184 and 185

Unsubstituted Acid from Method K & WX Method C

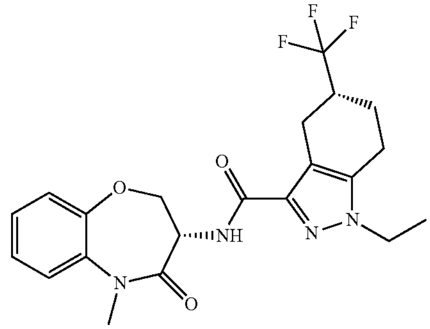

-continued

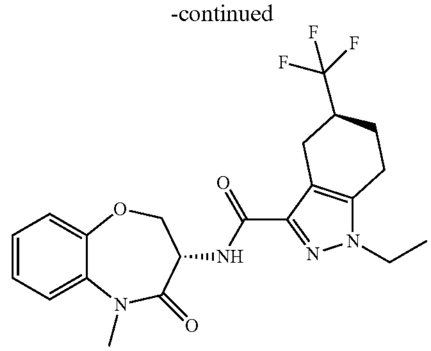

(R)-1-ethyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide and (S)-1-ethyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide

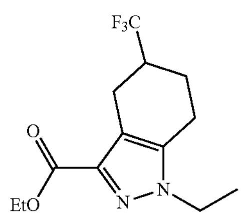 [SMILES: CCOC(=O)c1nn(CC)c2c1CC(C(F)(F)F)CC2]

Step 1: Ethyl 1-ethyl-5-(trifluoromethyl)-4,5,6,7-tetrahydro-1H-indazole-3-carboxylate To a solution of ethyl 5-(trifluoromethyl)-4,5,6,7-tetrahydro-1H-indazole-3-carboxylate (600 mg, 2.3 mmol) in N,N-dimethylformamide (15 mL) was added potassium carbonate (474 mg, 3.4 mmol) and iodoethane (426 mg, 2.8 mmol). The mixture was stirred at 25° C. for 15 h and quenched by addition of ice water (10 mL). The resulting mixture was extracted with ethyl acetate (3×20 mL). The combined organic layers were dried over sodium sulfate and concentrated under reduced pressure. The residue was purified by preparative TLC (30% ethyl acetate in petroleum ether) to afford ethyl 1-ethyl-5-(trifluoromethyl)-4,5,6,7-tetrahydro-1H-indazole-3-carboxylate (300 mg, 45%) as a white solid: $^1$H NMR (400 MHz, $CD_3OD$) δ 4.37-4.31 (m, 1H), 4.16-4.10 (m, 1H), 3.32-3.29 (m, 1H), 2.96-2.93 (m, 1H), 2.78-2.50 (m, 3H), 2.34-2.23 (m, 1H), 1.78-1.73 (m, 1H), 1.40 (q, J 7.2 Hz, 6H).

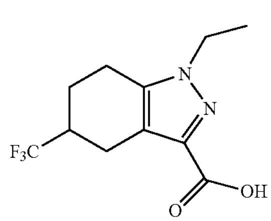 [SMILES: CCn1nc(C(=O)O)c2c1CCC(C(F)(F)F)C2]

Step 2: 1-ethyl-5-(trifluoromethyl)-4,5,6,7-tetrahydro-1H-indazole-3-carboxylic acid A mixture of ethyl 1-ethyl-5-(trifluoromethyl)-4,5,6,7-tetrahydro-1H-indazole-3-carboxylate (388 mg, 1.3 mmol) and potassium hydroxide (375 mg, 6.7 mmol) in ethanol (5 mL) and water (1 mL) was stirred at 25° C. for 15 h. The solvent was removed under reduced pressure. The residue was dissolved in water (10 mL) and adjusted to pH=3 by addition of hydrochloric acid (1.0 M). The mixture was extracted with ethyl acetate (3×10 mL). The combined organic layers were dried over sodium sulfate and concentrated under reduced pressure to afford crude 1-ethyl-5-(trifluoromethyl)-4,5,6,7-tetrahydro-1H-indazole-3-carboxylic acid (263 mg, 75%) as white solids: LCMS $R_T$=1.13 min; m/z=263.0 $(M+H)^+$.

LCMS (0 to 60% acetonitrile in water+0.1% formic acid over 2.0 mins) retention time 1.13 min, ESI+ found [M+H]=263.0.

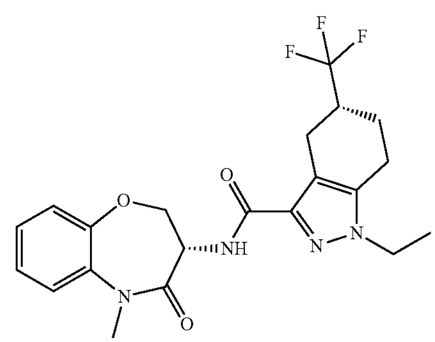

and

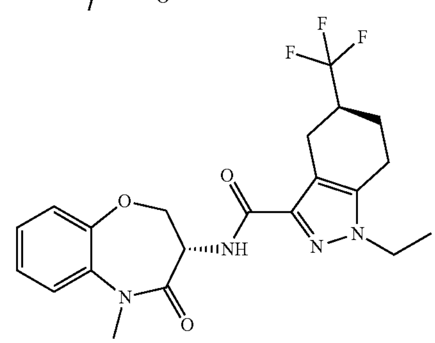

Step 3: (R)-1-ethyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide and (S)-1-ethyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide To a solution of 1-ethyl-5-(trifluoromethyl)-4,5,6,7-tetrahydro-1H-indazole-3-carboxylic acid (263 mg, 1.0 mmol) in N,N-dimethylformamide (5 mL) was added methyl (3S)-3-amino-5-methyl-2,3-dihydro-1,5-benzoxazepin-4-one (193 mg, 1.0 mmol), (E)-3-(ethyldiazenyl)-N,N-dimethylpropan-1-amine hydrochloride (8 mg, 0.04 mmol) and 1-benzo[d][1,2,3]triazol-1-ol (385 mg, 2.0 mmol). The resulting solution was stirred at 25° C. for 13 h and then concentrated under reduced pressure. The residue was purified by RP-HPLC (48-78% acetonitrile in water and 0.05% FA) to afford 1-ethyl-N—((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide (360 mg, 82.2%) as white solid.

The above racemate was separated by chiral SFC to give:

Peak 1 (retention time 0.545 min, 96.0% ee, arbitrarily assigned R configuration) (61 mg, 16.9%): $^{1}H$ NMR (400 MHz, $CD_3OD$) δ 7.46-7.41 (m, 1H), 7.35-7.23 (m, 3H), 4.96-4.89 (m, 1H), 4.62-4.56 (m, 1H), 4.39-4.36 (m, 1H), 4.12-4.08 (m, 2H), 3.41 (s, 3H), 3.11-3.06 (m, 1H), 2.92-2.86 (m, 1H), 2.72-2.46 (m, 3H), 2.23-2.13 (m, 1H), 1.74-1.71 (m, 1H), 1.41 (t, J=7.2 Hz, 3H). LCMS $R_T$=0.84 min; m/z=437.2 $(M+H)^+$.

LCMS (5 to 95% acetonitrile in water+0.1% formic acid over 1.5 mins) retention time 0.84 min, ESI+ found [M+H]=437.2.

Peak 2 (retention time 0.908 min, 93.0% ee, arbitrarily assigned S configuration) (55 mg, 13.5%): $^{1}H$ NMR (400 MHz, $CD_3OD$) δ 7.43-7.41 (m, 1H), 7.32-7.23 (m, 3H), 4.97-4.93 (m, 1H), 4.60-4.55 (m, 1H), 4.37-4.32 (m, 1H), 4.11-4.07 (m, 2H), 3.41 (s, 3H), 3.12-3.07 (m, 1H), 2.84-2.78 (m, 1H), 2.72-2.41 (m, 3H), 2.27-2.15 (m, 1H), 1.73-1.70 (m, 1H), 1.40 (t, J=7.2 Hz, 3H). LCMS $R_T$=0.84 min; m/z=437.2 $(M+H)^+$.

LCMS (5 to 95% acetonitrile in water+0.1% formic acid over 1.5 mins) retention time 0.84 min, ESI+ found [M+H]=437.2.

Example 186

WX Method BB

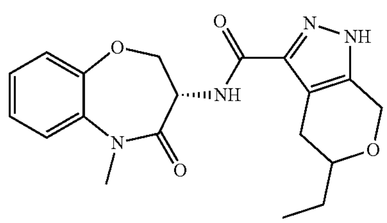 [SMILES: CCC1Cc2c(C(=O)N[C@H]3COc4ccccc4N(C)C3=O)n[nH]c2CO1]

5-ethyl-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide

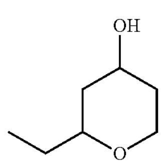

Step 1: 2-ethyltetrahydro-2H-pyran-4-ol

A mixture of propionaldehyde (5.0 g, 86.0 mmol) and but-3-en-1-ol (6.2 g, 86.0 mmol) in 20% sulfuric acid (100 mL) was stirred at 80° C. for 12 h. The mixture was cooled and then adjusted to pH=9 by slow addition of 20% aqueous sodium bicarbonate. The resulting mixture was extracted with ethyl acetate (3×100 mL). The combined organic layers were dried over sodium sulfate and concentrated under reduced pressure. The residue was purified by column chromatography (silica gel, 100-200 mesh, 20 to 30% ethyl acetate in petroleum ether) to afford 2-ethyltetrahydro-2H-pyran-4-ol (10.0 g, 91%) as light yellow oil: $^{1}H$ NMR (400 MHz, $CDCl_3$) δ 4.03-3.98 (m, 1H), 3.80-3.72 (m, 1H), 3.42-3.35 (m, 1H), 3.21-3.14 (m, 1H), 1.98-1.93 (m, 1H), 1.90-1.84 (m, 2H), 1.63-1.42 (m, 3H), 1.22-1.13 (m, 1H), 0.93 (t, J=7.6 Hz, 3H).

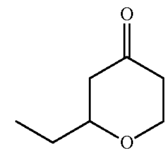

Step 2: 2-ethyldihydro-2H-pyran-4(3H)-one

To a solution of 2-ethyltetrahydro-2H-pyran-4-ol (10.0 g, 76.8 mmol) in dichloromethane (50 mL) was added pyridiniumchlorochromate (22.7 g, 105.6 mmol) portionwise over 5 min. The reaction was stirred for 18 h at 25° C. and then filtered. The filtrate was concentrated under reduced pressure. The residue was purified by column chromatography (silica gel, 100-200 mesh, 0 to 10% ethyl acetate in petroleum ether) to afford 2-ethyldihydro-2H-pyran-4(3H)-one (8.3 g, 84%) as light yellow oil, used in the next step as is: $^{1}H$ NMR (400 MHz, $CDCl_3$) δ 4.30-4.25 (m, 1H), 3.73-3.61 (m, 1H), 3.52-3.46 (m, 1H), 2.62-2.53 (m, 1H), 2.42-2.23 (m, 3H), 1.72-1.62 (m, 1H), 1.60-1.50 (m, 1H), 0.96 (t, J=7.6 Hz, 3H)

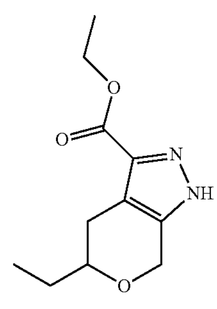 [SMILES: CCOC(=O)c1n[nH]c2c1CC(CC)OC2]

Step 3: ethyl 5-ethyl-1,4,5,7-tetrahydropyrano[3,4-c]pyrazole-3-carboxylate

To a solution of 2-ethyldihydro-2H-pyran-4(3H)-one (4.5 g, 35.1 mmol) was added pyrrolidine (125 mg, 1.75 mmol) and ethyl diazoacetate (2.0 g, 17.5 mmol). The mixture was stirred for 15 h at 25° C. and then diluted with water (30 mL). The resulting mixture was extracted with ethyl acetate (2×50 mL). The combined organic layers were concentrated and the residue was purified by column chromatography (silica gel, 100-200 mesh, 0 to 30% ethyl acetate in petroleum ether) to afford ethyl 5-ethyl-1,4,5,7-tetrahydropyrano[3,4-c]pyrazole-3-carboxylate (640 mg, 16%) as a light yellow solid: $^{1}H$ NMR (400 MHz, $CDCl_3$) δ 4.94 (d, J=14.8 Hz, 1H), 4.71 (d, J=14.4, 1H), 4.42-4.36 (m, 2H), 3.51-3.45 (m, 1H), 2.94-2.89 (m, 1H), 2.61-2.54 (m, 1H), 1.78-1.66 (m, 2H), 1.41-1.38 (m, 3H), 1.07-1.03 (m, 3H).

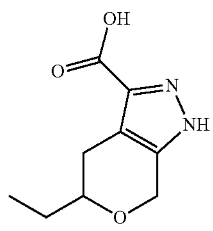

Step 4: 5-ethyl-1,4,5,7-tetrahydropyrano[3,4-c]pyrazole-3-carboxylic acid

A mixture of ethyl 5-ethyl-1,4,5,7-tetrahydropyrano[3,4-c]pyrazole-3-carboxylate (50 mg, 0.22 mmol) and lithium hydroxide hydrate (94 mg, 2.23 mmol) in tetrahydrofuran (3 mL) and water (3 mL) was stirred for 12 h at 25° C. The organic solvent was removed under reduced pressure, and the aqueous layer was adjusted to pH=3 by addition of hydrochloric acid (1.0 M). The solution was concentrated under reduced pressure to afford crude 5-ethyl-1,4,5,7-tetrahydropyrano[3,4-c]pyrazole-3-carboxylic acid (40 mg, 91.4%) as a light yellow solid, used in next step without further purification.

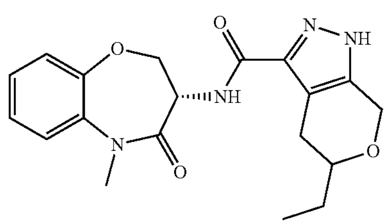 [SMILES: CCC1Cc2c(C(=O)N[C@H]3COc4ccccc4N(C)C3=O)n[nH]c2CO1]

Step 5: 5-ethyl-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide A mixture of (3S)-3-amino-5-methyl-2,3-dihydro-1,5-benzoxazepin-4-one (43 mg, 0.22 mmol), 5-ethyl-1,4,5,7-tetrahydropyrano[3,4-c]pyrazole-3-carboxylic acid (40 mg, 0.20 mmol), 1-(3-dimethylaminopropyl)-3-ethylcarbodiimidehydrochloride (47 mg, 0.24 mmol) and 1-hydroxybenzotriazole (33 mg, 0.24 mmol) in N,N-dimethylformamide (3 mL) was stirred at 25° C. for 12 h. The reaction was concentrated under reduced pressure and the residue was purified by RP-HPLC (acetonitrile 24-54 with 0.05% ammonia hydroxide in water) to afford 5-ethyl-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide (9 mg, 11%) as a white solid: $^1H$ NMR (400 MHz, $CD_3OD$) δ 7.42-7.40 (m, 1H), 7.30-7.28 (m, 2H), 7.24-7.21 (m, 1H), 5.00-4.94 (m, 1H), 4.82-4.67 (m, 1H), 4.60-4.58 (m, 2H), 4.36-4.35 (m, 1H), 3.42-3.41 (m, 4H), 2.85-2.80 (m, 1H), 2.52-2.32 (m, 1H), 1.70-1.60 (m, 2H), 1.01 (t, J=7.2 Hz, 3H). LCMS $R_T$=1.03 min; m/z=371.2 $(M+H)^+$.

LCMS (10 to 80% acetonitrile in water+0.03% trifluoacetic acid over 3 mins) retention time 1.03 min, ESI+ found [M+H]=371.2.

Example 187

WX Method F

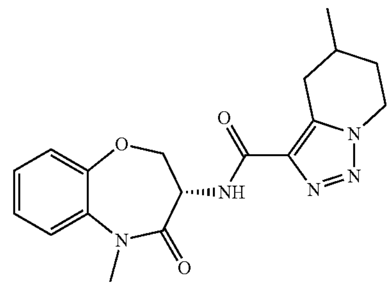 [SMILES: CC1CCn2nnc(C(=O)N[C@H]3COc4ccccc4N(C)C3=O)c2C1]

5-methyl-N—((S)-5-methyl-4-oxo-2,3,4,5-tetrahydrobenzo[b][1,4]oxazepin-3-yl)-4,5,6,7-tetrahydro-[1,2,3]triazolo[1,5-a]pyridine-3-carboxamide

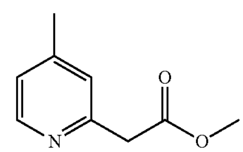

Step 1: methyl 2-(4-methylpyridin-2-yl)acetate

A mixture of methyl 2-(4-bromo-2-pyridyl)acetate (600 mg, 2.6 mmol), potassium carbonate (721 mg, 5.2 mmol), trimethylboroxine (982 mg, 7.8 mmol) and tetrakis(triphenylphosphine)palladium(0) (47 mg, 0.04 mmol) in 1,4-dioxane (5 mL) was heated to 120° C. for 4 h under nitrogen. After cooled, the reaction mixture was filtered and the filtrate was concentrated under reduced pressure. The residue was purified by column chromatography (silica gel, 100-200 mesh, 0 to 50% ethyl acetate) to afford methyl 2-(4-methylpyridin-2-yl)acetate (350 mg, 81%) as brown oil, used in the next step without further purification.

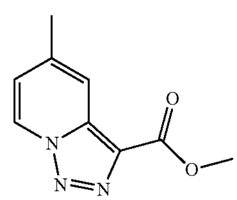

Step 2: methyl 5-methyl-[1,2,3]triazolo[1,5-a]pyridine-3-carboxylate

To a solution of methyl 2-(4-methylpyridin-2-yl)acetate (300 mg, 1.82 mmol) in acetonitrile (10 mL) was added 4-acetamidobenzenesulfonyl azide (436 mg, 1.82 mmol) and 1,8-diazabicyclo[5.4.0]undec-7-ene (415 mg, 2.72 mmol) at 0° C. The resulting mixture was stirred at 20° C. for 2 h and then concentrated under reduced pressure. The residue was purified with preparative TLC (50% ethyl acetate in petroleum ether) to afford methyl 5-methyl-[1,2,3]triazolo[1,5-a]pyridine-3-carboxylate (200 mg, 57%) as a white solid: $^1$H NMR (400 MHz, $CDCl_3$) δ 8.71 (d, J=6.8 Hz, 1H), 8.05 (s, 1H), 6.98 (d, J=6.8 Hz, 1H), 4.05 (s, 3H), 2.54 (s, 3H).

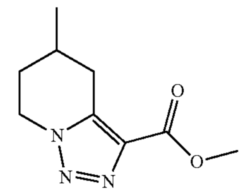

Step 3: methyl 5-methyl-4,5,6,7-tetrahydro-[1,2,3]triazolo[1,5-a]pyridine-3-carboxylate A mixture of methyl 5-methyl-[1,2,3]triazolo[1,5-a]pyridine-3-carboxylate (200 mg, 1.0 mmol) and 10% palladium on carbon (111 mg, 0.1 mmol) in methanol (5 mL) was hydrogenated (50 psi) at 25° C. for 48 h. The reaction mixture was filtered and the filtrate was concentrated under reduced pressure to afford crude methyl 5-methyl-4,5,6,7-tetrahydro-[1,2,3]triazolo[1,5-a]pyridine-3-carboxylate (200 mg, 98%) as a brown solid: LCMS $R_T$=1.22 min; m/z=196.1 (M+H)$^+$.

LCMS (10 to 80% acetonitrile in water+0.03% ammonium hydroxide over 3.0 mins) retention time 1.22 min, ESI+ found [M+H]=196.1

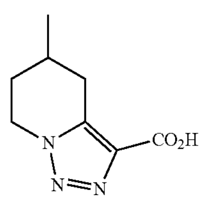

Step 4: 5-methyl-4,5,6,7-tetrahydro-[1,2,3]triazolo[1,5-a]pyridine-3-carboxylic acid A mixture of methyl 5-methyl-4,5,6,7-tetrahydro-[1,2,3]triazolo[1,5-a]pyridine-3-carboxylate (100 mg, 0.51 mmol) and potassium hydroxide (287 mg, 5.1 mmol) in ethanol (5 mL) and water (1 mL) was stirred at 25° C. for 12 h. The solvent was removed under reduced pressure. The residue was diluted with water (10 mL) and adjusted to pH=4 by addition of hydrochloric acid (2.0 M). The solution was concentrated under reduced pressure to afford crude 5-methyl-4,5,6,7-tetrahydro-[1,2,3]triazolo[1,5-a]pyridine-3-carboxylic acid (80 mg, 86%) as a white solid, used in the next step without further purification.

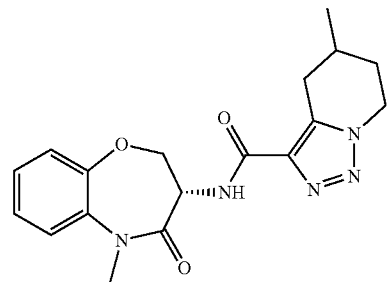 [SMILES: CC1CCn2nnc(C(=O)N[C@H]3COc4ccccc4N(C)C3=O)c2C1]

Step 6: 5-methyl-N—((S)-5-methyl-4-oxo-2,3,4,5-tetrahydrobenzo[b][1,4]oxazepin-3-yl)-4,5,6,7-tetrahydro-[1,2,3]triazolo[1,5-a]pyridine-3-carboxamide A mixture of (3S)-3-amino-5-methyl-2,3-dihydro-1,5-benzoxazepin-4-one (40 mg, 0.21 mmol), 5-methyl-4,5,6,7-tetrahydro-[1,2,3]triazolo[1,5-a]pyridine-3-carboxylic acid (38 mg, 0.21 mmol), 1H-benzo[d][1,2,3]triazol-1-ol (42 mg, 0.31 mmol) and N$^1$-((ethylimino)methylene)-N$^3$,N$^3$-dimethylpropane-1,3-diamine hydrochloride (59 mg, 0.31 mmol) in N,N-dimethylformamide (5 mL) was stirred at 25° C. for 16 h. The reaction was concentrated under reduced pressure and the residue was purified by RP-HPLC (60 to 90% acetonitrile in water and 0.05% ammonium hydroxide) affording 5-methyl-N—((S)-5-methyl-4-oxo-2,3,4,5-tetrahydrobenzo[b][1,4]oxazepin-3-yl)-4,5,6,7-tetrahydro-[1,2,3]triazolo[1,5-a]pyridine-3-carboxamide (20 mg, 27%) as a white solid: $^1$H NMR (400 MHz, DMSO-$d_6$) δ 8.42-8.39 (m, 1H), 7.51-7.47 (m, 1H), 7.33-7.26 (m, 2H), 7.25-7.21 (m, 1H), 4.88-4.81 (m, 1H), 4.65-4.57 (m, 1H), 4.55-4.47 (m, 1H), 4.42-4.36 (m, 1H), 4.24-4.20 (m, 1H), 3.31 (s, 3H), 3.15-3.07 (m, 1H), 2.44-2.31 (m, 2H), 2.01-1.95 (m, 1H), 1.72-1.63 (m, 1H), 1.04 (d, J=6.4 Hz, 3H). LCMS $R_T$=0.81 min; m/z=356.1 (M+H)$^+$.

LCMS (5 to 95% acetonitrile in water+0.03% trifluoacetic acid over 1.5 mins) retention time 0.81 min, ESI+ found [M+H]=356.1.

Example 188

WX Method HHHHHH

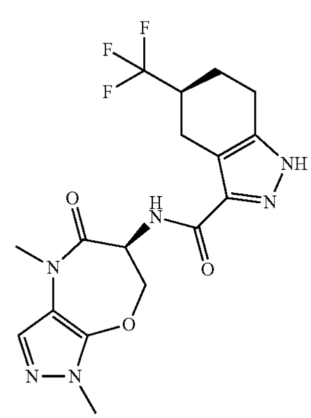 [SMILES: CN1C(=O)[C@@H](NC(=O)c2n[nH]c3c2C[C@@H](C(F)(F)F)CC3)COc2c1cnn2C]

(S)—N—((S)-1,4-dimethyl-5-oxo-4,5,6,7-tetrahydro-H-pyrazolo[3,4-b][1,4]oxazepin-6-yl)-5-(trifluoromethyl)-4,5,6,7-tetrahydro-1H-indazole-3-carboxamide

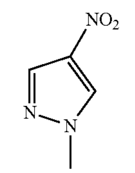

Step 1: 1-methyl-4-nitro-1H-pyrazole

To a solution of 4-nitro-1H-pyrazole (10.0 g, 88.4 mmol) in N,N-dimethylformamide (50 mL) was added potassium carbonate (36.67 g, 265.3 mmol) and iodomethane (25.1 g, 176.8 mmol). The mixture and stirred at 25° C. for 12 h and then concentrated under reduced pressure. The residue was diluted with water (100 mL) and extracted with ethyl acetate (3×100 mL). The combined organic layers were washed with water (100 mL), brine (100 mL), dried over sodium sulfate and concentrated under reduced pressure to afford 1-methyl-4-nitro-1H-pyrazole (10.0 g, 89%) as yellow solid, used next step without further purification.

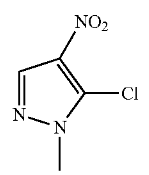

Step 2: 5-chloro-1-methyl-4-nitro-1H-pyrazole

To a cooled (−78° C.) solution of 1-methyl-4-nitro-1H-pyrazole (5.0 g, 39.4 mmol) in tetrahydrofuran (50 mL) was added lithium bis(trimethylsilyl)azanide (1.0 M, 39.4 mL, 39.4 mmol) dropwise. The mixture was stirred at −78° C. for 30 mins, and hexachloroethane (11.1 g, 47.2 mmol) was added. After addition, the mixture was stirred at 25° C. for 18 h and then quenched by addition of saturated aqueous ammonium chloride (80 mL). The mixture was extracted with ethyl acetate (3×50 mL). The combined organic layers were washed with water (50 mL), brine (50 mL), dried over sodium sulfate and concentrated under reduced pressure. The residue was purified by column chromatography (silica gel, 100-200 mesh, 0 to 10% ethyl acetate in petroleum ether) to afford 5-chloro-1-methyl-4-nitro-1H-pyrazole (5.0 g, 79%) as white solid, used in the next step as is.

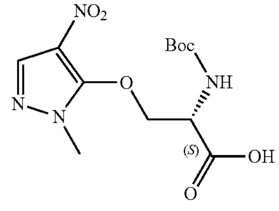

Step 3: (S)-2-((tert-butoxycarbonyl)amino)-3-((1-methyl-4-nitro-H-pyrazol-5-yl)oxy)propanoic acid To a solution of (S)-2-((tert-butoxycarbonyl)amino)-3-hydroxypropanoic acid (3.1 g, 14.9 mmol) in N,N-dimethylformamide (50 mL) was added sodium hydride (1.2 g, 29.7 mmol, 60%) at 0° C. The mixture was stirred at 0° C. for 1 h and then added 5-chloro-1-methyl-4-nitro-1H-pyrazole (2.0 g, 12.4 mmol). Stirring at 20° C. was continued for 3 h, and the reaction mixture was quenched by addition of hydrochloric acid (2.0 M, 30 mL). The resulting mixture was extracted with ethyl acetate (3×30 mL). The combined organic layers were washed with water (30 mL), brine (30 mL), dried over sodium sulfate and concentrated under reduced pressure. The residue was purified by column chromatography (silica gel, 100-200 mesh, 0 to 50% ethyl acetate in petroleum ether) to afford (S)-2-((tert-butoxycarbonyl)amino)-3-((1-methyl-4-nitro-1H-pyrazol-5-yl)oxy) propanoic acid (0.6 g, 15%) as yellow oil. LCMS $R_T$=0.77 min; m/z=352.9 $(M+Na)^+$.

LCMS (5-95% acetonitrile in water+0.03% trifluoroacetic over 1.5 mins) retention time 0.77 min, ESI+ found $[M+Na]^+$=352.9.

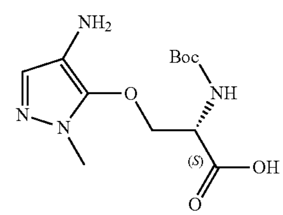

Step 4: (S)-3-((4-amino-1-methyl-1H-pyrazol-5-yl)oxy)-2-((tert-butoxycarbonyl)amino)propanoic acid A mixture of (S)-2-((tert-butoxycarbonyl)amino)-3-((1-methyl-4-nitro-1H-pyrazol-5-yl)oxy)propanoic acid (600 mg, 1.82 mmol) and 10% palladium on carbon (193 mg, 0.18 mmol) in methanol (50 mL) was hydrogenated (50 psi) at 20° C. for 2 h. The reaction mixture was filtered and the filtrate was concentrated under reduced pressure to afford (S)-3-((4-amino-1-methyl-1H-pyrazol-5-yl)oxy)-2-((tert-butoxycarbonyl)amino)propanoic acid (500 mg, 92%) as yellow oil: LCMS $R_T$=0.523 min; m/z=301.1 $(M+H)^+$.

LCMS (5-95% acetonitrile in water+0.03% trifluoroacetic over 1.5 mins) retention time 0.523 min, ESI+ found $[M+H]^+$=301.1.

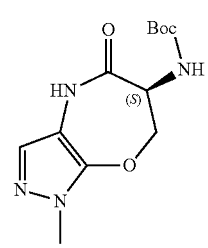

Step 5: (S)-tert-butyl(1-methyl-5-oxo-4,5,6,7-tetrahydro-1H-pyrazolo[3,4-b][1,4]oxazepin-6-yl)carbamate To a solution of (S)-3-((4-amino-1-methyl-1H-pyrazol-5-yl)oxy)-2-((tert-butoxycarbonyl)amino)propanoic acid (0.5 g, 1.66 mmol) in N,N-dimethylformamide (10 mL) was added $N^1$-((ethylimino)methylene)-$N^3$,$N^3$-dimethylpropane-1,3-diamine hydrochloride (383 mg, 2.00 mmol). The reaction mixture was stirred at 20° C. for 2 h and then concentrated under reduced pressure. The residue was purified by column chromatography (silica gel, 100-200 mesh, 0 to 50% ethyl acetate in petroleum ether) to afford (S)-tert-butyl(1-methyl-5-oxo-4,5,6,7-tetrahydro-1H-pyrazolo[3,4-b][1,4]oxazepin-6-yl)carbamate (200 mg, 43%) as yellow oil.

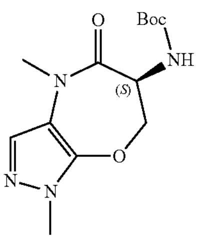

Step 6: (S)-tert-butyl(1,4-dimethyl-5-oxo-4,5,6,7-tetrahydro-1H-pyrazolo[3,4-b][1,4]oxazepin-6-yl) carbamate To a solution of (S)-tert-butyl (1-methyl-5-oxo-4,5,6,7-tetrahydro-1H-pyrazolo[3,4-b][1,4]oxazepin-6-yl)carbamate (0.2 g, 0.71 mmol) in N,N-dimethylformamide (10 mL) was added iodomethane (121 mg, 0.85 mmol) and potassium carbonate (196 mg, 1.42 mmol). The reaction mixture was stirred at 20° C. for 2 h and concentrated under reduced pressure. The residue was purified by column chromatography (silica gel, 100-200 mesh, 0 to 50% ethyl acetate in petroleum ether) to afford (S)-tert-butyl(1,4-dimethyl-5-oxo-4,5,6,7-tetrahydro-1H-pyrazolo[3,4-b][1,4]oxazepin-6-yl)carbamate (200 mg, 95%) as yellow oil. LCMS $R_T$=0.61 min; m/z=226.8 $(M-56)^+$.

LCMS (5-95% acetonitrile in water+0.03% trifluoroacetic over 1.5 mins) retention time 0.61 min, ESI+ found $[M-56]^+$= 226.8.

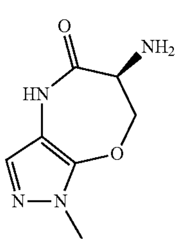

Step 7: (S)-6-amino-1-methyl-6,7-dihydro-1H-pyrazolo[3,4-b][1,4]oxazepin-5(4H)-one A mixture of (S)-tert-butyl (1,4-dimethyl-5-oxo-4,5,6,7-tetrahydro-1H-pyrazolo[3,4-b][1,4]ox azepin-6-yl)carbamate (200 mg, 0.67 mmol) and hydrochloric acid (4 M in EtOAc, 2 mL, 8 mmol) in ethyl acetate (5 mL) was stirred at 20° C. for 2 h. The reaction mixture was adjusted to pH=8 by addition of ammonia hydroxide. The mixture was then concentrated under reduced pressure to afford (S)-6-amino-1-methyl-6,7-dihydro-1H-pyrazolo[3,4-b][1,4]oxazepin-5 (4H)-one (130 mg, 101%) as yellow solid, used in the next step without further purification.

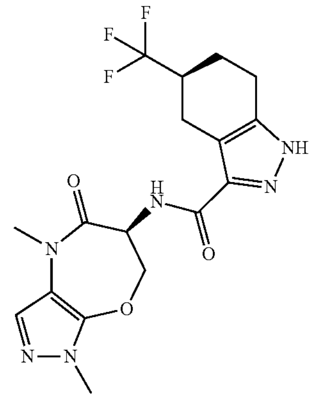 [SMILES: CN1C(=O)[C@@H](NC(=O)c2n[nH]c3c2C[C@@H](C(F)(F)F)CC3)COc2c1cnn2C]

Step 8: (S)—N—((S)-1,4-dimethyl-5-oxo-4,5,6,7-tetrahydro-1H-pyrazolo[3,4-b][1,4]oxazepin-6-yl)-5-(trifluoromethyl)-4,5,6,7-tetrahydro-1H-indazole-3-carboxamide A mixture of (S)-6-amino-1,4-dimethyl-6,7-dihydropyrazolo[3,4-b][1,4]oxazepin-5-one (24 mg, 0.12 mmol), (5S)-5-(trifluoromethyl)-4,5,6,7-tetrahydro-1H-indazole-3-carboxylic acid (32 mg, 0.13 mmol), 1H-benzo[d][1,2,3]triazol-1-ol (19 mg, 0.15 mmol) and $N^1$-((ethylimino)methylene)-$N^3$,$N^3$-dimethylpropane-1,3-diamine hydrochloride (21 mg, 0.15 mmol) in N,N-dimethylformamide (3 mL) was stirred at 25° C. for 12 h. The reaction was concentrated under reduced pressure and the residue was purified by RP-HPLC (13 to 43% methyl alcohol in water and 0.05% hydrochloric acid) to afford (S)—N—((S)-1,4-dimethyl-5-oxo-4,5,6,7-tetrahydro-1H-pyrazolo[3,4-b][1,4]oxazepin-6-yl)-5-(t rifluoromethyl)-4,5,6,7-tetrahydro-1H-indazole-3-carboxamide (10 mg, 20%) as a light yellow solid: $^1$H NMR (400 MHz, $CD_3OD$) δ 7.65 (s, 1H), 5.06-4.95 (m, 1H), 4.68-4.65 (m, 1H), 4.49-4.44 (m, 1H), 3.72 (s, 3H), 3.37 (s, 3H), 3.20-3.15 (m, 1H), 2.94-2.84 (m, 1H), 2.79-2.49 (m, 3H), 2.27-2.18 (m, 1H), 1.82-1.67 (m, 1H). LCMS $R_T$=0.79 min; m/z=413.0 $(M+H)^+$.

LCMS (5 to 95% acetonitrile in water+0.03% trifluoroacetic acid over 1.5 mins) retention time 0.79 min, ESI+ found [M+H]=413.0.

Example 189

WX Method S

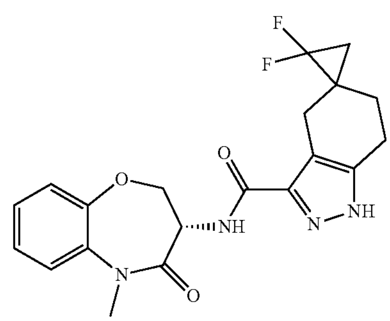 [SMILES: CN1C(=O)[C@@H](NC(=O)c2n[nH]c3c2CC2(CC3)CC2(F)F)COc2ccccc21]

2,2-difluoro-N—((S)-5-methyl-4-oxo-2,3,4,5-tetrahydrobenzo[b][1,4]oxazepin-3-yl)-1',4',6',7'-tetrahydrospiro[cyclopropane-1,5'-indazole]-3'-carboxamide

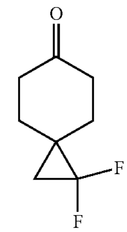 [SMILES: O=C1CCC2(CC1)CC2(F)F]

Step 1: 1,1-difluorospiro[2.5]octan-6-one

To a mixture of 8-methylene-1,4-dioxaspiro[4.5]decane (1.2 g, 7.8 mmol), sodium fluoride (33 mg, 0.78 mmol) in xylene (5 mL) was added a solution of trimethylsilyl2,2-difluoro-2-(fluorosulfonyl)acetate (4.9 g, 19.5 mmol) in xylene (4 mL) dropwise over a period 1 h at 120° C. After addition, the mixture was stirred for an additional 1 h and then cooled to 20° C. The mixture was diluted with water (20 mL) and extracted with ethyl acetate (3×20 mL). The combined organic layers were concentrated under reduced pressure and the residue was purified by column chromatography (silica gel, 100-200 mesh, 0 to 10% ethyl acetate in petroleum ether) to afford a yellow oil. The material was diluted with tetrahydrofuran (30 mL) and added hydrochloric acid (35%, 3 mL). The resulting mixture was stirred at 20° C. for 16 h and then adjusted to pH=7 by addition of saturated aqueous sodium bicarbonate. The solution was then extracted with ethyl acetate (3×20 mL). The combined organic layers were dried over sodium sulfate and concentrated under reduced pressure. The residue was purified by column chromatography (silica gel, 100-200 mesh, 0 to 10% ethyl acetate in petroleum ether) to afford 1,1-difluorospiro[2.5]octan-6-one (300 mg, 24.2% over 2 steps) as colorless oil: $^1H$ NMR (400 MHz, $CDCl_3$) δ 2.51-2.39 (m, 4H), 2.01-1.95 (m, 4H), 1.26 (t, J=8.4 Hz, 2H).

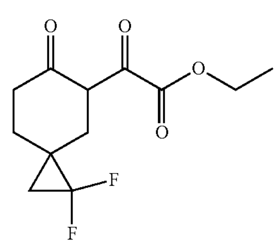 [SMILES: CCOC(=O)C(=O)C1CC2(CCC1=O)CC2(F)F]

Step 2: ethyl 2-(1,1-difluoro-6-oxospiro[2.5]octan-5-yl)-2-oxoacetate

To a solution of 1,1-difluorospiro[2.5]octan-6-one (300 mg, 1.87 mmol) in ethanol (15 mL) was added sodium ethanoxide (140 mg, 2.06 mmol) and diethyl oxalate (274 mg, 1.87 mmol) at 0° C. After addition, the mixture was allowed to warm to 20° C. for 20 h. The solution was concentrated under reduced pressure to afford crude ethyl 2-(1,1-difluoro-6-oxospiro[2.5]octan-5-yl)-2-oxoacetate (480 mg, 99%) as a yellow solid, used in the next step without further purification.

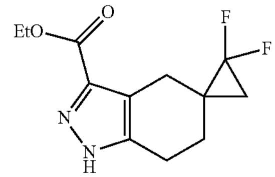 [SMILES: CCOC(=O)c1n[nH]c2c1CC1(CC2)CC1(F)F]

Step 3: ethyl 2,2-difluoro-1',4',6',7'-tetrahydrospiro[cyclopropane-1,5'-indazole]-3'-carboxylate To a solution of ethyl 2-(1,1-difluoro-6-oxospiro[2.5]octan-5-yl)-2-oxoacetate (480 mg, 1.84 mmol) in acetic acid (5 mL) was added hydrazine hydrate (130 mg, 2.03 mmol, 50%) at 0° C. The reaction was stirred at 25° C. for 1 h and then quenched by addition of saturated aqueous sodium bicarbonate. The mixture was extracted with methanol/dichloromethane (1:10) (3×15 mL). The combined organic layers were concentrated under reduced pressure. The residue was purified by column chromatography (silica gel, 100-200 mesh, 0 to 50% ethyl acetate in petroleum ether) to afford ethyl 2,2-difluoro-1',4',6',7'-tetrahydrospiro[cyclopropane-1,5'-indazole]-3'-carboxylate (150 mg, 32%) as yellow oil: LCMS $R_T$=0.688 min; m/z=256.8 $(M+H)^+$.

LCMS (5 to 95% acetonitrile in water+0.03% trifluoroacetic acid over 1.5 mins) retention time 0.688 min, ESI+ found [M+H]=256.8.

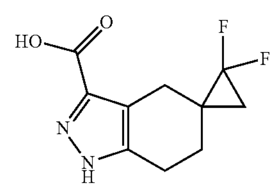 [SMILES: O=C(O)c1n[nH]c2c1CC1(CC2)CC1(F)F]

Step 4: 2,2-difluoro-1',4',6',7'-tetrahydrospiro[cyclopropane-1,5'-indazole]-3'-carboxylic acid A mixture of ethyl 2,2-difluoro-1',4',6',7'-tetrahydrospiro[cyclopropane-1,5'-indazole]-3'-carboxylate (150 mg, 0.59 mmol) and lithium hydroxide hydrate (140 mg, 5.85 mmol) in tetrahydrofuran (5 mL) and water (1 mL) was stirred for 20 h at 25° C. The organic solvent was removed under reduced pressure, and the aqueous layer was adjusted to pH=3 by addition of hydrochloric acid (1.0 M). The aqueous layer was extracted with ethyl acetate (3×25 mL). The combined organic layers were dried over sodium sulfate and concentrated under reduced pressure to afford 2,2-difluoro-1',4',6',7'-tetrahydrospiro[cyclopropane-1,5'-indazole]-3'-carboxylic acid (50 mg, 37%) as a white solid, used in the next step without further purification.

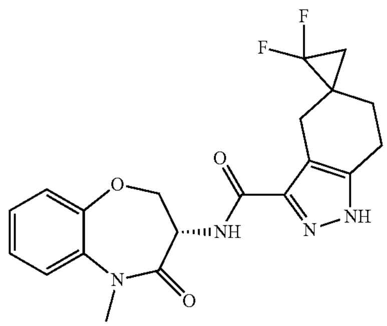 [SMILES: CN1C(=O)[C@@H](NC(=O)c2n[nH]c3c2CC2(CC3)CC2(F)F)COc2ccccc21]

Step 5: 2,2-difluoro-N—((S)-5-methyl-4-oxo-2,3,4,5-tetrahydrobenzo[b][1,4]oxazepin-3-yl)-1',4',6',7'-tetrahydrospiro[cyclopropane-1,5'-indazole]-3'-carboxamide A mixture of 2,2-difluoro-1',4',6',7'-tetrahydrospiro[cyclopropane-1,5'-indazole]-3'-carboxylic acid (50 mg, 0.22 mmol), 1H-benzo[d][1,2,3]triazol-1-ol (36 mg, 0.26 mmol), (3S)-3-amino-5-methyl-2,3-dihydro-1,5-benzoxazepin-4-one (46 mg, 0.24 mmol) and $N^1$-((ethylimino)methylene)-$N^3$,$N^3$-dimethylpropane-1,3-diamine hydrochloride (50 mg, 0.26 mmol) in N,N-dimethylformamide (5 mL) was stirred at 20° C. for 1 h. The reaction was concentrated under reduced pressure and the residue was purified by RP-HPLC (34-64% acetonitrile in water and 0.05% hydrochloric acid) to afford 2,2-difluoro-N—((S)-5-methyl-4-oxo-2,3,4,5-tetrahydrobenzo[b][1,4]oxazepin-3-yl)-1',4',6',7'-tetrahydrospiro[cyclopropane-1,5'-indazole]-3'-carboxamide (37 mg, 41%) as a white solid: $^1$H NMR (400 MHz, DMSO-$d_6$) δ 13.04 (s, 1H), 8.00 (d, J=8.0 Hz, 1H), 7.47 (d, J=7.2 Hz, 1H), 7.32-7.28 (m, 2H), 7.24-7.22 (m, 1H), 4.85-4.80 (m, 1H), 4.51-4.47 (m, 1H), 4.42-4.38 (m, 1H), 3.31 (s, 3H), 2.79-2.74 (m, 1H), 2.70-2.67 (m, 2H), 2.59-2.55 (m, 1H), 1.80-1.78 (m, 2H), 1.38-1.32 (m, 1H), 1.28-1.23 (m, 1H). LCMS $R_T$=0.836 min; m/z=403.1 $(M+H)^+$.

LCMS (5 to 95% acetonitrile in water+0.03% formic acid over 1.5 mins) retention time 0.836 min, ESI+ found [M+H]= 403.1.

Example 190 was prepared according to WX Method B (see Example 171 above). Data is provided in Table 2.

Example 191

WX Method GG

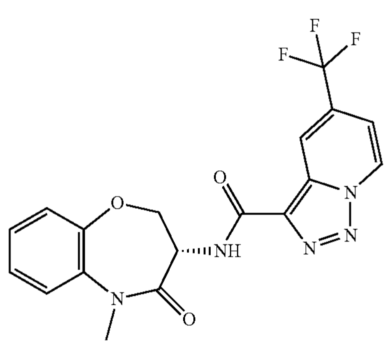 [SMILES: CN1C(=O)[C@@H](NC(=O)c2nnn3ccc(C(F)(F)F)cc23)COc2ccccc21]

(S)—N-(5-methyl-4-oxo-2,3,4,5-tetrahydrobenzo[b][1,4]oxazepin-3-yl)-5-(trifluoromethyl)-[1,2,3]triazolo[1,5-a]pyridine-3-carboxamide

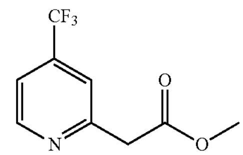

Step 1: Methyl 2-[4-(trifluoromethyl)-2-pyridyl]acetate

A mixture of 1-oxido-4-(trifluoromethyl)pyridin-1-ium (500 mg, 3.1 mmol), N, N-diisopropylethylamine (1.2 g, 9.2 mmol), 1-(tert-butyldimethylsilyloxy)-1-methoxyethene (1.1 g, 6.1 mmol) and bromo[tri(1-pyrrolidinyl)]phosphonium hexafluorophosphate (1.6 g, 3.4 mmol) in tetrahydrofuran (15 mL) was heated at 45° C. for 2 h and then poured into water (20 mL). The resulting solution was extracted with ethyl acetate (3×15 mL). The combined organic layers were washed water (20 mL), brine (20 mL), dried over sodium sulfate and concentrated under reduced pressure. The residue was purified by column chromatography (silica gel, 100-200 mesh, 0 to 30% ethyl acetate in petroleum ether) to afford crude methyl 2-[4-(trifluoromethyl)-2-pyridyl]acetate (485 mg, 72%) as yellow oil: LCMS $R_T$=0.633 min; m/z=219.9 $(M+H)^+$.

LCMS (5 to 95% acetonitrile in water+0.03% trifluoacetic acid over 1.5 mins) retention time 0.633 min, ESI+ found [M+H]=219.9.

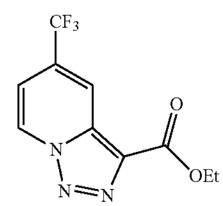 [SMILES: CCOC(=O)c1nnn2ccc(C(F)(F)F)cc12]

Step 2: Methyl 5-(trifluoromethyl)triazolo[1,5-a]pyridine-3-carboxylate

To a solution of methyl 2-[4-(trifluoromethyl)-2-pyridyl]acetate (480 mg, 2.19 mmol) in acetonitrile (12 mL) was added 1,8-diazabicyclo[5.4.0]undec-7-ene (500 mg, 3.29 mmol) and 4-acetamidobenzenesulfonylazide (526 mg, 2.19 mmol) at 0° C. The resulting mixture was allowed to warm to 25° C. and stirred for 1 h. The reaction mixture was concentrated under reduced pressure and the residue was purified by column chromatography (silica gel, 100-200 mesh, 0 to 40% ethyl acetate in petroleum ether) to afford methyl 5-(trifluoromethyl)triazolo[1,5-a]pyridine-3-carboxylate (380 mg, 71%) as a yellow solid: $^1$H NMR (400 MHz, DMSO-$d_6$) δ 9.53 (d, J=7.2 Hz, 1H), 8.48 (s, 1H), 7.71-7.68 (m, 1H), 3.98 (s, 3H). LCMS $R_T$=0.749 min; m/z=245.9 $(M+H)^+$.

LCMS (5 to 95% acetonitrile in water+0.03% trifluoacetic acid over 1.5 mins) retention time 0.749 min, ESI+ found [M+H]=245.9.

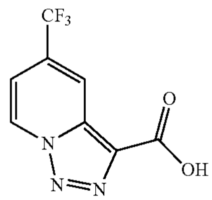 [SMILES: O=C(O)c1nnn2ccc(C(F)(F)F)cc12]

Step 3: 5-(trifluoromethyl)triazolo[1,5-a]pyridine-3-carboxylic acid

A mixture of methyl 5-(trifluoromethyl)triazolo[1,5-a] pyridine-3-carboxylate (75 mg, 0.31 mmol) and lithium hydroxide hydrate (36 mg, 1.53 mmol) in tetrahydrofuran (5 mL) was stirred at 23° C. for 18 h. The organic solvent was evaporated under reduced pressure, and the aqueous residue was adjusted to pH=5 by addition of hydrochloric acid (1.0 M). The mixture was concentrated under reduced pressure affording crude 5-(trifluoromethyl)triazolo[1,5-a]pyridine-3-carboxylic acid (40 mg, 57%) as a white solid, used in the next step without further purification.

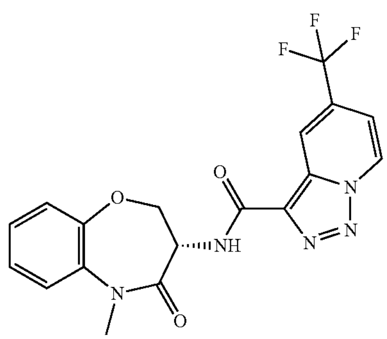 [SMILES: CN1C(=O)[C@@H](NC(=O)c2nnn3ccc(C(F)(F)F)cc23)COc2ccccc21]

Step 4: (S)—N-(5-methyl-4-oxo-2,3,4,5-tetrahydrobenzo[b][1,4]oxazepin-3-yl)-5-(trifluoromethyl)-[1,2,3]triazolo[1,5-a]pyridine-3-carboxamide A mixture of 5-(trifluoromethyl)triazolo[1,5-a]pyridine-3-carboxylic acid (40 mg, 0.17 mmol), (3 s)-3-amino-5-methyl-2,3-dihydro-1,5-benzoxazepin-4-one (37 mg, 0.19 mmol), 1H-benzo[d][1,2,3]triazol-1-ol (28 mg, 0.21 mmol) and $N^1$-((ethylimino)methylene)-$N^3$,$N^3$-dimethylpropane-1,3-diamine hydrochloride (40 mg, 0.21 mmol) in N,N-dimethylformamide (5 mL) was stirred at 25° C. for 1 h. The reaction was concentrated under reduced pressure and the residue was purified by RP-HPLC (acetonitrile 39-69%/0.05% ammonia in water) affording (S)—N-(5-methyl-4-oxo-2,3,4,5-tetrahydrobenzo[b][1,4]oxazepin-3-yl)-5-(trifluoromethyl)-[1, 2,3]triazolo[1,5-a]pyridine-3-carboxamide (37.3 mg, 53%) as a white solid: $^1$H NMR (400 MHz, DMSO-$d_6$) δ 9.47 (d, J=7.6 Hz, 1H), 9.01 (d, J=8.0 Hz, 1H), 8.43 (s, 1H), 7.67-7.61 (m, 1H), 7.56-7.49 (m, 1H), 7.38-7.22 (m, 3H), 5.00-4.91 (m, 1H), 4.77-4.70 (m, 1H), 4.48-4.43 (m, 1H), 3.33 (s, 3H). LCMS $R_T$=0.861 min; m/z=406.0 $(M+H)^+$.

LCMS (5 to 95% acetonitrile in water+0.03% trifluoacetic acid over 1.5 mins) retention time 0.861 min, ESI+ found [M+H]=406.0.

Example 192

WX Method HH

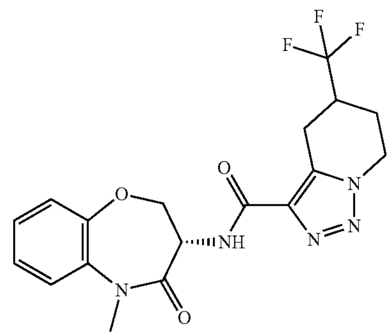 [SMILES: CN1C(=O)[C@@H](NC(=O)c2nnn3c2CC(C(F)(F)F)CC3)COc2ccccc21]

N—((S)-5-methyl-4-oxo-2,3,4,5-tetrahydrobenzo[b][1,4]oxazepin-3-yl)-5-(trifluoromethyl)-4,5,6,7-tetrahydro-[1,2,3]triazolo[1,5-a]pyridine-3-carboxamide

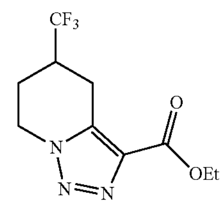 [SMILES: CCOC(=O)c1nnn2c1CC(C(F)(F)F)CC2]

Step 1: Methyl 5-(trifluoromethyl)-4,5,6,7-tetrahydrotriazolo[1,5-a]pyridine-3-carboxylate A mixture of methyl 5-(trifluoromethyl)triazolo[1,5-a] pyridine-3-carboxylate (150 mg, 0.61 mmol) and 10% palladium on carbon (65 mg, 0.06 mmol) in methanol (5 mL) was hydrogenated (50 psi) at 25° C. for 18 h. The reaction mixture was filtered and the filtrate was concentrated under reduced pressure affording crude methyl 5-(trifluoromethyl)-4,5,6,7-tetrahydrotriazolo[1,5-a]pyridine-3-carboxylate (82 mg, 54%) as yellow oil: LCMS $R_T$=0.704 min; m/z=249.9 $(M+H)^+$.

LCMS (5 to 95% acetonitrile in water+0.03% trifluoacetic acid over 1.5 mins) retention time 0.704 min, ESI+ found [M+H]=249.9.

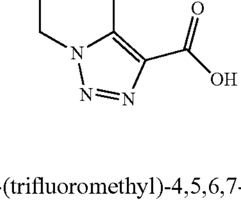

Step 2: 5-(trifluoromethyl)-4,5,6,7-tetrahydrotriazolo[1,5-a]pyridine-3-carboxylic acid A mixture of methyl 5-(trifluoromethyl)-4,5,6,7-tetrahydrotriazolo[1,5-a]pyridine-3-carboxylate (82 mg, 0.33 mmol) and lithium hydroxide hydrate (39 mg, 1.65 mmol) in tetrahydrofuran (5 mL) and water (2 mL) was stirred at 23° C. for 18 h. After evaporated of the organic solvent, the aqueous residue was adjusted to pH=5 by addition of hydrochloric acid (1.0 M). The mixture was concentrated under reduced pressure affording crude 5-(trifluoromethyl)-4,5,6,7-tetrahydrotriazolo[1,5-a]pyridine-3-carboxylic acid (60 mg, 77%) as a white solid, used in the next step without further purification.

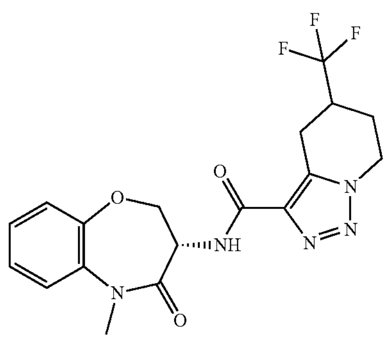 [SMILES: CN1C(=O)[C@@H](NC(=O)c2nnn3c2CC(C(F)(F)F)CC3)COc2ccccc21]

Step 3: N—((S)-5-methyl-4-oxo-2,3,4,5-tetrahydrobenzo[b][1,4]oxazepin-3-yl)-5-(trifluoromethyl)-4,5,6,7-tetrahydro-[1,2,3]triazolo[1,5-a]pyridine-3-carboxamide A mixture of 5-(trifluoromethyl)-4,5,6,7-tetrahydrotriazolo[1,5-a]pyridine-3-carboxylic acid (60 mg, 0.26 mmol), 1H-benzo[d][1,2,3]triazol-1-ol (41 mg, 0.31 mmol), (3s)-3-amino-5-methyl-2,3-dihydro-1,5-benzoxazepin-4-one (54 mg, 0.28 mmol) and $N^1$-((ethylimino)methylene)-$N^3$,$N^3$-dimethylpropane-1,3-diamine hydrochloride (59 mg, 0.31 mmol) in N, N-dimethylformamide (5 mL) was stirred at 25° C. for 1 h. The reaction was concentrated under reduced pressure and the residue was purified by RP-HPLC (acetonitrile 33-63%/0.05% ammonia in water) affording N—((S)-5-methyl-4-oxo-2,3,4,5-tetrahydrobenzo[b][1,4]oxazepin-3-yl)-5-(trifluoromethyl)-4, 5,6,7-tetrahydro-[1,2,3]triazolo[1,5-a]pyridine-3-carboxamide (45.8 mg, 44%) as a white solid: $^1$H NMR (400 MHz, DMSO-$d_6$) δ 8.56-8.49 (m, 1H), 7.53-7.46 (m, 1H), 7.40-7.15 (m, 3H), 4.91-4.80 (m, 1H), 4.68-4.60 (m, 2H), 4.44-4.23 (m, 2H), 3.31 (s, 3H), 3.15-3.02 (m, 1H), 2.89-2.79 (m, 1H), 2.53-2.51 (m, 1H), 2.34-2.26 (m, 1H), 2.13-1.99 (m, 1H). LCMS $R_T$=0.833 min; m/z=410.0 (M+H)$^+$.

LCMS (5 to 95% acetonitrile in water+0.03% trifluoacetic acid over 1.5 mins) retention time 0.833 min, ESI+ found [M+H]=410.0.

Example 193

WX Method L

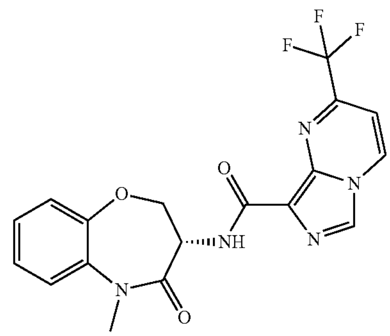 [SMILES: CN1C(=O)[C@@H](NC(=O)c2ncn3ccc(C(F)(F)F)nc23)COc2ccccc21]

(S)—N-(5-methyl-4-oxo-2,3,4,5-tetrahydrobenzo[b][1,4]oxazepin-3-yl)-2-(trifluoromethyl) imidazo[1,5-a]pyrimidine-8-carboxamide

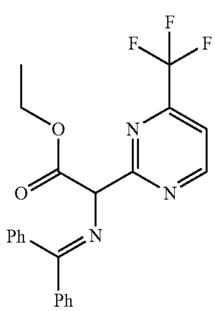 [SMILES: CCOC(=O)C(N=C(c1ccccc1)c1ccccc1)c1nccc(C(F)(F)F)n1]

Step 1: ethyl 2-((diphenylmethylene)amino)-2-(4-(trifluoromethyl)pyrimidin-2-yl)acetate A mixture of 2-chloro-4-(trifluoromethyl)pyrimidine (2.0 g, 11.0 mmol), potassium carbonate (2.3 g, 16.4 mmol), tetrabutylammonium bromide (1.8 g, 5.5 mmol) and ethyl-(diphenylmethylene)glycinate (1.5 g, 5.5 mmol) in 1-methyl-2-pyrrolidinone (20 mL) was heated at 100° C. for 12 h. After cooled, the reaction mixture was diluted with ethyl acetate (30 mL). The organic layer was washed with water (3×50 mL), dried over sodium sulfate and concentrated under reduced pressure. The residue was purified by column chromatography (silica gel, 100-200 mesh, 0 to 20% ethyl acetate in petroleum ether) to afford ethyl 2-(benzhydrylideneamino)-2-(4-(trifluoromethyl)pyrimidin-2-yl)acetate (1.9 g, 42%) as yellow oil: LCMS $R_T$=0.90 min; m/z=414.1 (M+H)$^+$.

LCMS (5 to 95% acetonitrile in water+0.03% trifluoroacetic acid over 1.5 mins) retention time 0.90 min ESI+ found [M+H]=414.1.

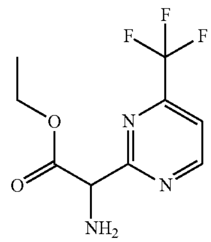 [SMILES: CCOC(=O)C(N)c1nccc(C(F)(F)F)n1]

Step 2: ethyl 2-amino-2-(4-(trifluoromethyl)pyrimidin-2-yl)acetate hydrochloride To a solution of ethyl 2-(benzhydrylideneamino)-2-(4-(trifluoromethyl)pyrimidin-2-yl)acetate (200 mg, 0.48 mmol) in dichloromethane (10 mL) was slowly added hydrochloric acid (1.0 M, 12 mL, 12 mmol). The reaction mixture was stirred for 3 h at 25° C. and the layers were separated. The aqueous layer was washed with dichloromethane (2×20 mL) and then concentrated under reduced pressure to afford crude ethyl 2-amino-2-(4-(trifluoromethyl)pyrimidin-2-yl)acetate hydrochloride (100 mg, 83%) as a light yellow solid: LCMS $R_T$=0.41 min; m/z=250.1 $(M+H)^+$.

LCMS (5 to 95% acetonitrile in water+0.03% trifluoroacetic acid over 1.5 mins) retention time 0.41 min, ESI+ found [M+H]=250.1.

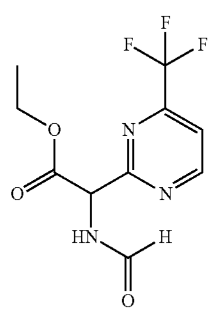 [SMILES: CCOC(=O)C(NC=O)c1nccc(C(F)(F)F)n1]

Step 3: ethyl 2-formamido-2-(4-(trifluoromethyl)pyrimidin-2-yl)acetate

Formic acid (98%, 0.8 mL) was added to acetic anhydride (2 mL) at 0° C. The resulting solution was stirred 4 h at 50° C. This anhydride solution was slowly added into a solution of ethyl 2-amino-2-(4-(trifluoromethyl)pyrimidin-2-yl)acetate hydrochloride (100 mg, 0.40 mmol) in tetrahydrofuran (5 mL) at 0° C. After addition, stirring was continued for another 6 h. The reaction mixture was quenched by addition of water (20 mL) and ethyl acetate (20 mL). The mixture was extracted with ethyl acetate (2×10 mL). The combined organic layers were washed with brine (4×20 mL), dried over sodium sulfate and concentrated under reduced pressure. The residue was purified by column chromatography (silica gel, 100-200 mesh, 0-20% methanol in dichloromethane) to afford ethyl 2-formamido-2-(4-(trifluoromethyl)pyrimidin-2-yl)acetate (70 mg, 63%) as a light yellow solid: LCMS $R_T$=0.63 min; m/z=278.1 $(M+H)^+$.

LCMS (5 to 95% acetonitrile in water+0.03% trifluoroacetic acid over 1.5 mins) retention time 0.63 min, ESI+ found [M+H]=278.1.

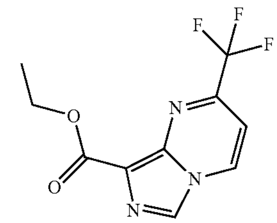 [SMILES: CCOC(=O)c1ncn2ccc(C(F)(F)F)nc12]

Step 4: ethyl 2-(trifluoromethyl)imidazo[1,5-a]pyrimidine-8-carboxylate

A solution of ethyl 2-formamido-2-(4-(trifluoromethyl)pyrimidin-2-yl)acetate (70 mg, 0.25 mmol) in phosphoryl trichloride (2 mL) was heated at 115° C. for 12 h under nitrogen. After cooled, the reaction mixture was poured onto ice water (30 mL) and extracted with ethyl acetate (2×30 mL). The combined organic layers were washed with brine (2×30 mL), dried over sodium sulfate and concentrated under reduced pressure to afford ethyl 2-(trifluoromethyl)imidazo[1,5-a]pyrimidine-8-carboxylate (55 mg, 84%) as a pale yellow solid: LCMS $R_T$=1.78 min; m/z=260.1 $(M+H)^+$.

LCMS (10 to 80% acetonitrile in water+0.03% trifluoroacetic acid over 7.0 mins) retention time 1.78 min, ESI+ found [M+H]=260.1.

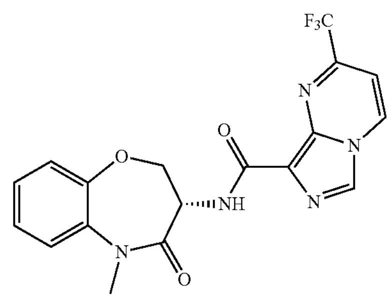 [SMILES: CN1C(=O)[C@@H](NC(=O)c2ncn3ccc(C(F)(F)F)nc23)COc2ccccc21]

Step 5: (S)—N-(5-methyl-4-oxo-2,3,4,5-tetrahydrobenzo[b][1,4]oxazepin-3-yl)-2-(trifluoromethyl)imidazo[1,5-a]pyrimidine-8-carboxamide To a mixture of (3S)-3-amino-5-methyl-2,3-dihydro-1,5-benzoxazepin-4-one (40 mg, 0.21 mmol) and ethyl 2-(trifluoromethyl)imidazo[1,5-a]pyrimidine-8-carboxylate (54 mg, 0.21 mmol) in tetrahydrofuran (20 mL) was added trimethylaluminum (2.0 M, 0.62 mL, 1.25 mmol) dropwise under nitrogen atmosphere. The mixture was stirred at 75° C. for 15 h, cooled and then quenched by addition of saturated aqueous potassium sodium tartrate (10 mL). The resulting mixture was stirred at 25° C. for 1 h and extracted with ethyl acetate (3×50 mL). The combined organic layers were dried over sodium sulfate and concentrated under reduced pressure. The residue was purified by RP-HPLC (acetonitrile 40-70%/0.05% ammonia hydroxide in water) to afford (S)—N-(5-methyl-4-oxo-2,3,4,5-tetrahydrobenzo[b][1,4]oxazepin-3-yl)-2-(trifluoromethyl)imidazo[1,5-a]pyrimidine-8-carboxamide (14 mg, 16%) as yellow solid: $^1$H NMR (400 MHz, DMSO-$d_6$) δ 9.14 (d, J=6.8 Hz, 1H), 8.68 (s, 1H), 8.38 (d, J=7.2 Hz, 1H), 7.52-7.50 (m, 1H), 7.40 (d, J=7.6 Hz, 1H), 7.36-7.25 (m, 3H), 4.95-4.88 (m, 1H), 4.55-4.44 (m, 2H), 3.34 (s, 3H). LCMS $R_T$=1.233 min; m/z=406.1 $(M+H)^+$.

LCMS (0 to 60% acetonitrile in water+0.03% trifluoacetic acid over 2 mins) retention time 1.233 min, ESI+ found [M+H]=406.1.

Example 194 was prepared according to Method GG (see Example 35). Data is provided in Table 2.

Example 195

WX Method VVVVVV

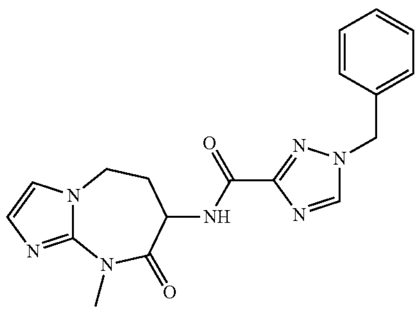 [SMILES: CN1C(=O)C(NC(=O)c2ncn(Cc3ccccc3)n2)CCn2ccnc21]

1-benzyl-N-(9-methyl-8-oxo-6,7,8,9-tetrahydro-5H-imidazo[1,2-a][1,3]diazepin-7-yl)-1H-1,2,4-triazole-3-carboxamide A mixture of 1-benzyl-1,2,4-triazole-3-carboxylic acid (41 mg, 0.20 mmol), 7-amino-9-methyl-6,7-dihydro-5H-imidazo[1,2-a][1,3]diazepin-8(9H)-one (30 mg, 0.17 mmol), $N^1$-((ethylimino)methylene)-$N^3$,$N^3$-dimethyl propane-1,3-diamine hydrochloride (45 mg, 0.25 mmol) and 1H-benzo[d][1,2,3]triazol-1-ol (34 mg, 0.25 mmol) in N,N-dimethylformamide (4 mL) was stirred at 25° C. for 12 h. The reaction was concentrated under reduced pressure and the residue was purified by RP-HPLC (acetonitrile 46-76%/0.05% ammonium in water) to afford 1-benzyl-N-(9-methyl-8-oxo-6,7,8,9-tetrahydro-5H-imidazo[1,2-a][1,3]diazepin-7-yl)-1H-1,2,4-triazole-3-carboxamide (26.6 mg, 42%) as colorless solid: $^1$H NMR (400 MHz, DMSO-$d_6$) δ 8.83 (s, 1H), 8.56 (d, J=7.6 Hz, 1H), 7.39-7.30 (m, 5H), 7.13 (s, 1H), 6.88 (s, 1H), 5.48 (s, 2H), 4.32-4.22 (m, 2H), 3.95-3.90 (m, 1H), 3.25 (s, 3H), 2.67-2.65 (m, 1H), 2.39-2.33 (m, 1H). LCMS $R_T$=1.36 min; m/z=366.1 $(M+H)^+$.

LCMS (0 to 60% acetonitrile in water+0.03% trifluoacetic acid over 3.0 mins) retention time 1.36 min, ESI+ found [M+H]=366.1.

Example 196

WX Method WWWWWW

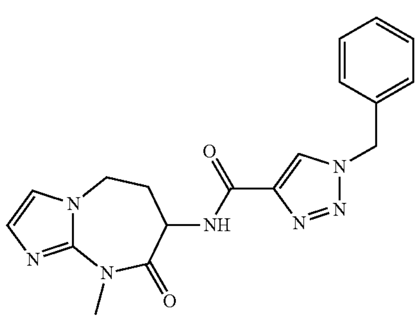 [SMILES: CN1C(=O)C(NC(=O)c2cn(Cc3ccccc3)nn2)CCn2ccnc21]

1-benzyl-N-(9-methyl-8-oxo-6,7,8,9-tetrahydro-5H-imidazo[1,2-a][1,3]diazepin-7-yl)-1H-1,2,3-triazole-4-carboxamide A mixture of 1-benzyltriazole-4-carboxylic acid (41 mg, 0.20 mmol), 7-amino-9-methyl-6,7-dihydro-5H-imidazo[1,2-a][1,3]diazepin-8(9H)-one (30 mg, 0.17 mmol), $N^1$-((ethylimino)methylene)-$N^3$,$N^3$-dimethyl propane-1,3-diamine hydrochloride (45 mg, 0.25 mmol) and 1H-benzo[d][1,2,3]triazol-1-ol (34 mg, 0.25 mmol) in N,N-dimethylformamide (4 mL) was stirred at 25° C. for 12 h. The reaction was concentrated under reduced pressure and the residue was purified by RP-HPLC (acetonitrile 46-76%/0.05% ammonium in water) to afford 1-benzyl-N-(9-methyl-8-oxo-6,7,8,9-tetrahydro-5H-imidazo[1,2-a][1,3]diazepin-7-yl)-1H-1,2,3-triazole-4-carboxamide (12 mg, 19%) as white solid: $^1$H NMR (400 MHz, DMSO-$d_6$) δ 8.68 (s, 1H), 8.66 (s, 1H), 7.38-7.33 (m, 5H), 7.12 (s, 1H), 6.88 (s, 1H), 5.65 (s, 2H), 4.32-4.23 (m, 2H), 3.94-3.90 (m, 1H), 3.25 (s, 3H), 2.67 (s, 1H), 2.37-2.33 (m, 1H). LCMS $R_T$=1.425 min; m/z=366.1 $(M+H)^+$.

LCMS (0 to 60% acetonitrile in water+0.03% trifluoacetic acid over 3.0 mins) retention time 1.425 min, ESI+ found [M+H]=366.1.

Example 197

WX Method GGGGGG

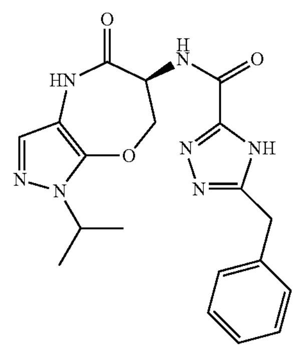 [SMILES: CC(C)n1ncc2c1OC[C@H](NC(=O)c1nnc(Cc3ccccc3)[nH]1)C(=O)N2]

(S)-5-benzyl-N-(1-isopropyl-5-oxo-4,5,6,7-tetrahydro-1H-pyrazolo [3,4-b][1,4]oxazepin-6-yl)-4H-1,2,4-triazole-3-carboxamide A mixture of (S)-6-amino-1-isopropyl-6,7-dihydro-1H-pyrazolo[3,4-b][1,4]oxazepin-5(4H)-one (15 mg, 0.07 mmol), 5-benzyl-4H-1,2,4-triazole-3-carboxylic acid (15 mg, 0.07 mmol), 1H-benzo[d][1,2,3]triazol-1-ol (13 mg, 0.09 mmol) and $N^1$-((ethylimino)methylene)-$N^3$,$N^3$-dimethylpropane-1,3-diamine hydrochloride (17 mg, 0.09 mmol) in N,N-dimethylformamide (4 mL) was stirred at 25° C. for 12 h. The reaction concentrated under reduced pressure and the residue was purified by RP-HPLC (acetonitrile 12-42%/0.05% ammonia hydroxide in water) to afford (S)-5-benzyl-N-(1-isopropyl-5-oxo-4,5,6,7-tetrahydro-H-pyrazolo[3,4-b][1,4]oxazepin-6-yl)-4H-1,2,4-triazole-3-carboxamide (8 mg, 28%) as white solid: $^1$H NMR (400 MHz, $CD_3OD$) δ 7.34-7.26 (m, 5H), 7.25-7.20 (m, 1H), 4.87-4.68 (m, 1H), 4.67-4.64 (m, 1H), 4.55-4.51 (m, 1H), 4.41-4.36 (m, 1H), 4.18 (s, 2H), 1.41 (d, J=7.2 Hz, 6H). LCMS $R_T$=0.93 min; m/z=396.2 $(M+H)^+$.

LCMS (10-80% acetonitrile in water+0.05% ammonium bicarbonate over 3 mins) retention time 0.93/min, ESI+ found [M+H]=396.2

Example 198

WX Method YYYYYY

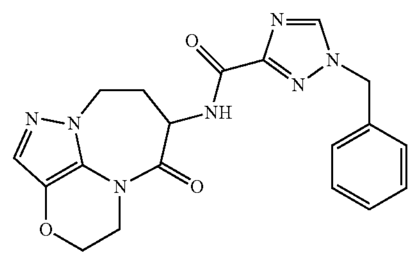 [SMILES: O=C(NC1CCn2ncc3c2N(CCO3)C1=O)c1ncn(Cc2ccccc2)n1]

1-benzyl-N-(6-oxo-4,5,6,7,8,9-hexahydro-3-oxa-1,5a,9a-triazabenzo[cd]azulen-7-yl)-1H-1,2,4-triazole-3-carboxamide

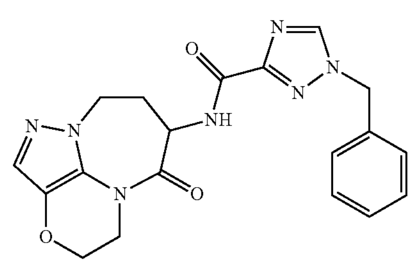 [SMILES: O=C(NC1CCn2ncc3c2N(CCO3)C1=O)c1ncn(Cc2ccccc2)n1]

A mixture of 1-benzyl-1,2,4-triazole-3-carboxylic acid (40 mg, 0.20 mmol), 7-amino-4,5,8,9-tetrahydro-3-oxa-1,5a,9a-triazabenzo[cd]azulen-6(7H)-one (40 mg, 0.19 mmol), $N^1$-((ethylimino)methylene)-$N^3$,$N^3$-dimethylpropane-1,3-diamine hydrochloride (44 mg, 0.23 mmol) and 1H-benzo[d][1,2,3]triazol-1-ol (31 mg, 0.23 mmol) in N,N-dimethylformamide (4 mL) was stirred at 25° C. for 1 h. The reaction mixture was concentrated under reduced pressure and the residue was purified by RP-HPLC (acetonitrile 25-55/0.05% ammonia hydroxide in water) to afford 1-benzyl-N-(6-oxo-4,5,6,7,8,9-hexahydro-3-oxa-1,5a,9a-triazabenzo[cd]azulen-7-yl)-1H-1,2, 4-triazole-3-carboxamide (24 mg, 31%) as white solid: $^1$H NMR (400 MHz, DMSO-$d_6$) δ 8.84 (s, 1H), 8.71 (d, J=6.8 Hz, 1H), 7.40-7.31 (m, 5H), 7.27 (s, 1H), 5.50 (s, 2H), 4.76 (t, J=8.0 Hz, 1H), 4.41-4.29 (m, 4H), 3.96 (t, J=8.0 Hz, 1H), 3.32-3.28 (m, 1H), 2.50-2.27 (m, 2H). LCMS $R_T$=1.09 min; m/z=394.2 $(M+H)^+$.

LCMS (0 to 60% acetonitrile in water+0.03% trifluoacetic acid over 2 mins) retention time 1.09 min, ESI+ found [M+H]=394.2.

Example 199

WX Method XXXXXX

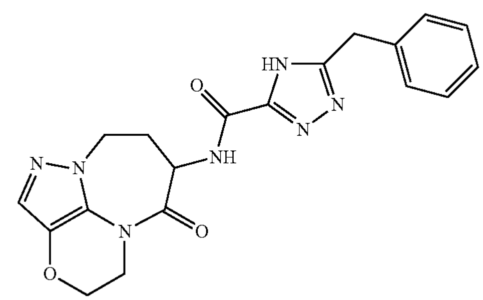 [SMILES: O=C(NC1CCn2ncc3c2N(CCO3)C1=O)c1nnc(Cc2ccccc2)[nH]1]

5-benzyl-N-(6-oxo-4,5,6,7,8,9-hexahydro-3-oxa-1,5a,9a-triazabenzo[cd]azulen-7-yl)-4H-1,2,4-triazole-3-carboxamide

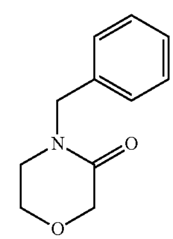 [SMILES: O=C1COCCN1Cc1ccccc1]

Step 1: 4-benzylmorpholin-3-one

To a solution of morpholin-3-one (10.0 g, 98.9 mmol) in N,N-dimethylformamide (100 mL) was added sodium hydride (3.96 g, 98.9 mmol, 60%). The reaction mixture was stirred at 0° C. for 0.5 h and then benzyl bromide (16.9 g, 98.9 mmol) was added. The reaction mixture was stirred at 20° C. for 15 h and then poured on to ice water (100 mL). The mixture was extracted with ethyl acetate (3×100 mL). The combined organic layers were washed with brine (3×30 mL), dried over sodium sulfate and concentrated under reduced pressure. The residue was purified by column chromatography (silica gel, 100-200 mesh, 0 to 75% ethyl acetate in petroleum ether) to afford 4-benzylmorpholin-3-one (10.0 g, 53%) as a colorless oil, used in the next step as is.

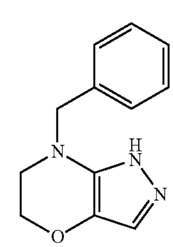 [SMILES: c1ccc(CN2CCOc3cn[nH]c32)cc1]

Step 2: 7-benzyl-1,5,6,7-tetrahydropyrazolo[4,3-b][1,4]oxazine

N,N-dimethylformamide (9.9 g, 135.4 mmol) was added dropwise to a solution of phosphoryl trichloride (16.8 g, 110.0 mmol) in 1,2-dichloroethane (40 mL) at 0° C. The mixture was allowed stirring for 10 min and then 4-benzylmorpholin-3-one (7.0 g, 36.6 mmol) in of 1,2-dichloromethane (5 mL) was added dropwise. The resulting solution was stirred at 0° C. for 30 min, at 25° C. for 3 h and at 45° C. for 1 h. The solvent was removed under reduced pressure and the residue was diluted with ethanol (80 mL). The solution was cooled to 0° C. and added hydrazine hydrate (18.3 g, 366.0 mmol, 85%) dropwise. After addition, the mixture was stirred for 1 h at −5° C., for 2 h at 25° C. and for 15 h at 60° C. to give emerged gradually dissolved and a clear, deep red colored solution. Then the reaction mixture was concentrated under reduced pressure. The residue was purified by column chromatography (silica gel, 100-200 mesh, 0 to 10% ethyl acetate in petroleum ether) to afford 7-benzyl-1,5,6,7-tetrahydropyrazolo[4,3-b][1,4]oxazine (3.0 g, 38%) as a white solid: LCMS $R_T$=0.84 min; m/z=216.2 $(M+H)^+$.

LCMS (10 to 80% acetonitrile in water+0.03% trifluoacetic acid over 2 mins) retention time 0.84 min, ESI+ found [M+H]=216.2.

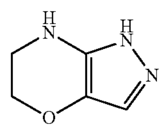

Step 3: 1,5,6,7-tetrahydropyrazolo[4,3-b][1,4]oxazine

To a solution of 7-benzyl-1,5,6,7-tetrahydropyrazolo[4,3-b][1,4]oxazine (3.0 g, 13.9 mmol) in 2-propanol (50 mL) were added 10% palladium on carbon (5.93 g, 5.57 mmol). The reaction mixture was stirred at 20° C. under the atmosphere of hydrogen (15 psi) for 15 h and then filtered. The filtrate was concentrated under reduced pressure to afford 1,5,6,7-tetrahydropyrazolo[4,3-b][1,4]oxazine (1.7 g, 98%) as a yellow oil, used in the next step without further purification.

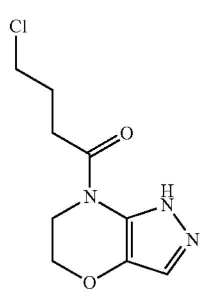 [SMILES: O=C(CCCCl)N1CCOc2cn[nH]c21]

Step 4: 4-chloro-1-(5,6-dihydropyrazolo[4,3-b][1,4]oxazin-7(1H)-yl)butan-1-one

A solution of 1,5,6,7-tetrahydropyrazolo[4,3-b][1,4]oxazine (1.8 g, 14.4 mmol) in 4-chlorobutanoyl chloride (10.1 g, 71.9 mmol) was stirred at 50° C. for 1 h. The reaction mixture was quenched by slow addition of methanol (20 mL) and then concentrated under reduced pressure. The residue was purified by column chromatography (silica gel, 100-200 mesh, 0 to 50% ethyl acetate in petroleum ether) afford 4-chloro-1-(5,6-dihydropyrazolo[4,3-b][1,4]oxazin-7(1H)-yl)butan-1-one (3.0 g, 91%) as a yellow solid: LCMS $R_T$=0.86 min; m/z=230.2 $(M+H)^+$.

LCMS (0 to 60% acetonitrile in water+0.03% trifluoacetic acid over 2 mins) retention time 0.86 min, ESI+ found [M+H]=230.2.

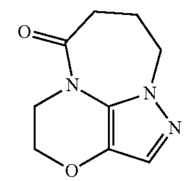 [SMILES: O=C1CCCn2ncc3c2N1CCO3]

Step 5: 4,5,8,9-tetrahydro-3-oxa-1,5a,9a-triazabenzo[cd]azulen-6(7H)-one

To a solution of 4-chloro-1-(5,6-dihydropyrazolo[4,3-b][1,4]oxazin-7(1H)-yl)butan-1-one (500 mg, 2.18 mmol) in N,N-dimethylformamide (10 mL) was added cesium carbonate (1.4 g, 4.35 mmol). The reaction mixture was stirred at 25° C. for 3 h and then concentrated under reduced pressure. The residue was purified by column chromatography (silica gel, 100-200 mesh, 0 to 50% ethyl acetate in petroleum ether) to afford 4,5,8,9-tetrahydro-3-oxa-1,5a,9a-triazabenzo[cd]azulen-6(7H)-one (300 mg, 71%) as a white solid: LCMS $R_T$=0.83 min; m/z=194.1 $(M+H)^+$.

LCMS (0 to 60% acetonitrile in water+0.03% trifluoacetic acid over 2 mins) retention time 0.83 min, ESI+ found [M+H]=194.1.

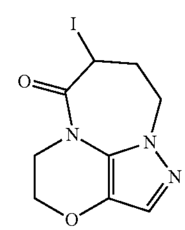 [SMILES: O=C1C(I)CCn2ncc3c2N1CCO3]

Step 6: 7-iodo-4,5,8,9-tetrahydro-3-oxa-1,5a,9a-triazabenzo[cd]azulen-6(7H)-one

To a solution of 4,5,8,9-tetrahydro-3-oxa-1,5a,9a-triazabenzo[cd]azulen-6(7H)-one (100 mg, 0.52 mmol) in dichloromethane (10 mL) was treated with iodotrimethylsilane (621 mg, 3.11 mmol) and $N^1,N^1,N^2,N^2$-tetramethylethane-1,2-diamine(360 mg, 3.11 mmol) at −15° C. The mixture was stirred at −15° C. for 1.5 h, then iodine (394 mg, 1.55 mmol) was added in one portion. After addition, the mixture was stirred at −15° C. for 2 h and then quenched by addition of saturated aqueous sodium sulfite (5%, 40 mL). The mixture was extracted with dichloromethane (3×40 mL). The combined organic layers were concentrated under reduced pressure. The residue was purified by column chromatography (silica gel, 100-200 mesh, 0 to 30% ethyl acetate in petroleum ether) to afford 7-iodo-4,5,8,9-tetrahydro-3-oxa-1,5a,9a-triazabenzo[cd]azulen-6(7H)-one (80 mg, 48%) as a light yellow solid, used as is in the next step.

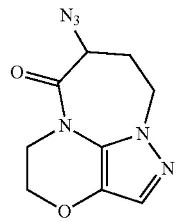 [SMILES: [N-]=[N+]=NC1CCn2ncc3c2N(CCO3)C1=O]

Step 7: 7-azido-4,5,8,9-tetrahydro-3-oxa-1,5a,9a-triazabenzo[cd]azulen-6(7H)-one To a solution of 7-iodo-4,5,8,9-tetrahydro-3-oxa-1,5a,9a-triazabenzo[cd]azulen-6(7H)-one (50 mg, 0.16 mmol) in N,N-dimethylformamide (5 mL) were added sodium azide (14 mg, 0.21 mmol). The reaction mixture was stirred at 25° C. for 2 h and then poured into ice water (5 mL). The solution was extracted with dichloromethane (2×10 mL). The combined organic layers were concentrated under reduced pressure to afford 7-azido-4,5,8,9-tetrahydro-3-oxa-1,5a,9a-triazabenzo[cd]azulen-6(7H)-one (36 mg, 98%) as a light yellow oil: LCMS $R_T$=1.39 min; m/z=235.1 $(M+H)^+$.

LCMS (0 to 60% acetonitrile in water+0.03% trifluoacetic acid over 3.0 mins) retention time 1.39 min, ESI+ found [M+H]=235.1.

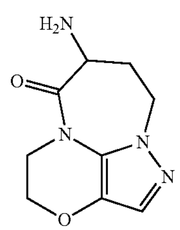 [SMILES: NC1CCn2ncc3c2N(CCO3)C1=O]

Step 8: 7-amino-4,5,8,9-tetrahydro-3-oxa-1,5a,9a-triazabenzo[cd]azulen-6(7H)-one A mixture of 7-azido-4,5,8,9-tetrahydro-3-oxa-1,5a,9a-triazabenzo[cd]azulen-6(7H)-one (36 mg, 0.15 mmol) and 10% palladium on carbon (164 mg, 0.15 mmol) in methanol (10 mL) was hydrogenated (15 psi) at 25° C. for 2 h. The reaction mixture was filtered and the filtrate was concentrated under reduced pressure to afford 7-amino-4,5,8,9-tetrahydro-3-oxa-1,5a,9a-triazabenzo[cd]azulen-6(7H)-one (30 mg, 94%) as a black oil, used in the next step without further purification.

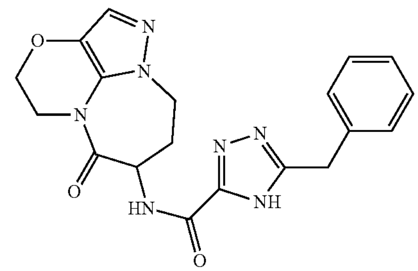 [SMILES: O=C(NC1CCn2ncc3c2N(CCO3)C1=O)c1nnc(Cc2ccccc2)[nH]1]

5-benzyl-N-(6-oxo-4,5,6,7,8,9-hexahydro-3-oxa-1,5a,9a-triazabenzo[cd]azulen-7-yl)-4H-1,2,4-triazole-3-carboxamide A mixture of 5-benzyl-4H-1,2,4-triazole-3-carboxylic acid (40 mg, 0.20 mmol), 7-amino-4,5,8,9-tetrahydro-3-oxa-1,5a,9a-triazabenzo[cd]azulen-6(7H)-one (40 mg, 0.19 mmol), $N^1$-((ethylimino)methylene)-$N^3$,$N^3$-dimethylpropane-1,3-diamine hydrochloride (44 mg, 0.23 mmol) and 1H-benzo[d][1,2,3]triazol-1-ol (31 mg, 0.23 mmol) in N,N-dimethylformamide (4 mL) was stirred at 25° C. for 1 h. The reaction mixture was concentrated under reduced pressure and the residue was purified by RP-HPLC (acetonitrile 10-40/0.05% ammonia hydroxide in water) to afford 5-benzyl-N-(6-oxo-4,5,6,7,8,9-hexahydro-3-oxa-1,5a,9a-triazabenzo[cd]azulen-7-yl)-4H-1,2, 4-triazole-3-carboxamide (13.9 mg, 18%) as white solid: $^1$H NMR (400 MHz, DMSO-$d_6$) δ 14.48 (br. s, 1H), 8.75 (s, 1H), 7.36-7.22 (m, 6H), 4.80-4.72 (m, 1H), 4.39-4.24 (m, 4H), 4.13 (s, 2H), 4.00-3.92 (m, 1H), 3.30-3.27 (m, 1H), 2.50-2.27 (m, 2H). LCMS $R_T$=1.09 min; m/z=394.2 $(M+H)^+$.

LCMS (0 to 60% acetonitrile in water+0.03% trifluoacetic acid over 2 mins) retention time 1.09 min, ESI+ found [M+H]=394.2.

Example 200

WX Method T

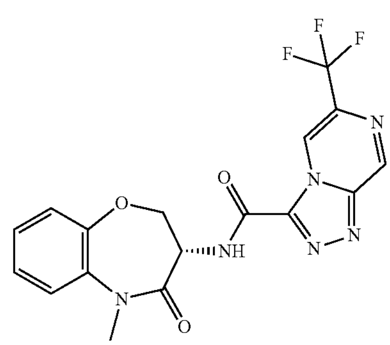 [SMILES: CN1C(=O)[C@@H](NC(=O)c2nnc3cnc(C(F)(F)F)cn23)COc2ccccc21]

(S)—N-(5-methyl-4-oxo-2,3,4,5-tetrahydrobenzo[b][1,4]oxazepin-3-yl)-6-(trifluoromethyl)-[1,2,4]triazolo[4,3-a]pyrazine-3-carboxamide

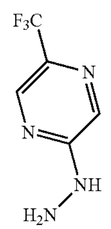

Step 1: 2-hydrazinyl-5-(trifluoromethyl)pyrazine

A mixture of 2-chloro-5-(trifluoromethyl)pyrazine (2.0 g, 11.0 mmol) in ethanol (20 mL) was added hydrazine hydrate (50%, 2.2 g, 21.9 mmol). The mixture was stirred at 45° C. for 12 h and then concentrated under reduced pressure. The residue was purified by column chromatography (silica gel, 100-200 mesh, 0 to 10% methanol in dichloromethane) to afford 2-hydrazinyl-5-(trifluoromethyl)pyrazine (1.2 g, 62%) as a yellow solid: LCMS $R_T$=1.393 min; m/z=179.1 $(M+H)^+$.

LCMS (0 to 60% acetonitrile in water+0.03% formic acid over 3 mins) retention time 1.393 min, ESI+ found [M+H]=179.1.

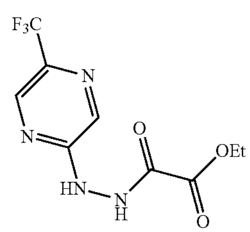 [SMILES: CCOC(=O)C(=O)NNc1cnc(C(F)(F)F)cn1]

Step 2: ethyl 2-oxo-2-(2-(5-(trifluoromethyl)pyrazin-2-yl)hydrazinyl)acetate

To a solution of 2-hydrazinyl-5-(trifluoromethyl)pyrazine (1.1 g, 6.2 mmol) and triethylamine (937 mg, 9.26 mmol) in dichloromethane (20 mL) was added ethyl oxalyl chloride (1.0 g, 7.4 mmol) at 0° C. The mixture was stirred at 25° C. for 20 h and then quenched by addition of water (30 mL). The resulting mixture was extracted with dichloromethane (3×35 mL). The combined organic layers were concentrated under reduced pressure and the residue was purified by column chromatography (silica gel, 100-200 mesh, 0 to 10% methanol in dichloromethane) to afford ethyl 2-oxo-2-(2-(5-(trifluoromethyl)pyrazin-2-yl)hydrazinyl)acetate (1.5 g, 87%) as a dark yellow solid: LCMS $R_T$=1.511 min; m/z=279.1 $(M+H)^+$.

LCMS (0 to 60% acetonitrile in water+0.03% formic acid over 3 mins) retention time 1.511 min, ESI+ found [M+H]=279.1.

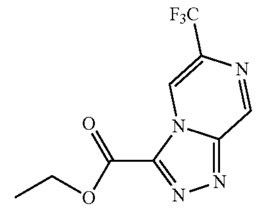 [SMILES: CCOC(=O)c1nnc2cnc(C(F)(F)F)cn12]

Step 3: ethyl 6-(trifluoromethyl)-[1,2,4]triazolo[4,3-a]pyrazine-3-carboxylate

A mixture of ethyl 2-oxo-2-(2-(5-(trifluoromethyl)pyrazin-2-yl)hydrazinyl)acetate (1.0 g, 3.6 mmol) and p-toluenesulfonic acid (310 mg, 1.8 mmol) in toluene (20 mL) was heated at 115° C. for 20 h. After cooled, the solution was diluted with water (20 mL) and extracted with dichloromethane (3×25 mL). The combined organic layers were dried over sodium sulfate and concentrated under reduced pressure to afford crude ethyl 6-(trifluoromethyl)-[1,2,4]triazolo[4,3-a]pyrazine-3-carboxylate (600 mg, 64%) as a red solid: LCMS $R_T$=0.613 min; m/z=261.1 $(M+H)^+$.

LCMS (5 to 95% acetonitrile in water+0.03% formic acid over 1.5 mins) retention time 0.613 min, ESI+ found [M+H]= 261.1.

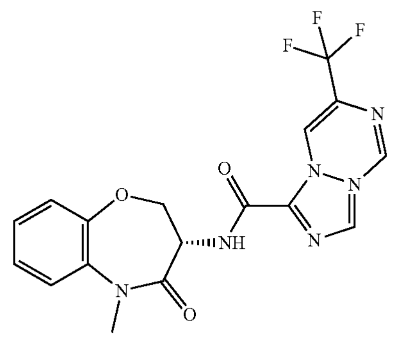

Step 4: (S)—N-(5-methyl-4-oxo-2,3,4,5-tetrahydrobenzo[b][1,4]oxazepin-3-yl)-6-(trifluoromethyl)-[1,2,4]triazolo[4,3-a]pyrazine-3-carboxamide To a mixture of (3S)-3-amino-5-methyl-2,3-dihydro-1,5-benzoxazepin-4-one (50 mg, 0.26 mmol) and ethyl 6-(trifluoromethyl)-[1,2,4]triazolo[4,3-a]pyrazine-3-carboxylate (61 mg, 0.23 mmol) in tetrahydrofuran (3 mL) was added trimethylaluminum (2.0 M, 0.78 mL, 1.56 mmol). The mixture was stirred at 50° C. for 15 h and then quenched by addition of saturated aqueous potassium sodium tartrate (10 mL). Stirring was continued for 1 h and the mixture was extracted with ethyl acetate (3×20 mL). The combined organic layers were dried over sodium sulfate and concentrated under reduced pressure. The residue was purified by RP-HPLC (30-60% acetonitrile in water and 0.05% ammonium hydroxide) to afford (S)—N-(5-methyl-4-oxo-2,3,4,5-tetrahydrobenzo[b][1,4]oxazepin-3-yl)-6-(trifluoromethyl)-[1, 2,4]triazolo[4,3-a]pyrazine-3-carboxamide (16 mg, 17%) as a white solid: $^1H$ NMR (400 MHz, DMSO-$d_6$) δ 9.74 (s, 1H), 9.67 (s, 1H), 9.31 (s, 1H), 7.55-7.52 (m, 1H), 7.35-7.26 (m, 3H), 4.96-4.92 (m, 1H), 4.81-4.74 (m, 1H), 4.49-4.44 (m, 1H), 3.33 (s, 3H). LCMS $R_T$=0.830 min; m/z=407.0 $(M+H)^+$.

LCMS (5 to 95% acetonitrile in water+0.03% formic acid over 1.5 mins) retention time 0.830 min, ESI+ found [M+H]= 407.0.

Example 201

WX Method Y

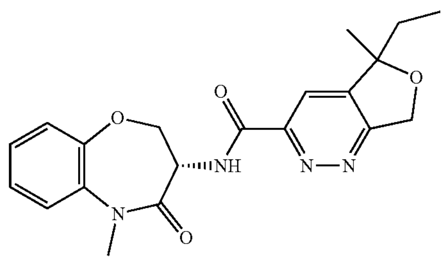 [SMILES: CCC1(C)OCc2nnc(C(=O)N[C@H]3COc4ccccc4N(C)C3=O)cc21]

5-ethyl-5-methyl-N—((S)-5-methyl-4-oxo-2,3,4,5-tetrahydrobenzo[b][1,4]oxazepin-3-yl)-5, 7-dihydro-furo[3,4-c]pyridazine-3-carboxamide

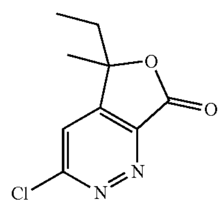

Step 1: 3-chloro-5-ethyl-5-methylfuro[3,4-c]pyridazin-7(5H)-one

To a solution of 6-chloropyridazine-3-carboxylic acid (2.5 g, 15.8 mmol) in tetrahydrofuran (100 mL) was added lithium diisopropylazanide (2.0 M, 19.7 mL, 39.4 mmol) at −78° C. The reaction mixture was stirred at −78° C. for 1 h, and then butan-2-one (10.2 g, 141.9 mmol) was added. The reaction mixture was warmed up to 25° C. and stirred for 16 h and then quenched by addition of saturated aqueous ammonium chloride. The mixture was extracted with ethyl acetate (3×50 mL). The combined organic layers were washed with water (10 mL), brine (10 mL), dried over sodium sulfate and concentrated under reduced pressure. The residue was purified by column chromatography (silica gel, 100-200 mesh, 0 to 30% ethyl acetate in petroleum ether) to afford 3-chloro-5-ethyl-5-methylfuro[3,4-c]pyridazin-7(5H)-one (300 mg, 9%) as a yellow solid: $^1$H NMR (400 MHz, $CDCl_3$) δ 7.63 (s, 1H), 2.16-2.08 (m, 1H), 2.02-1.96 (m, 1H), 1.73 (s, 3H), 0.87 (t, J=7.6 Hz, 3H).

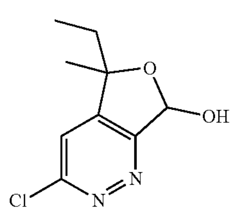

Step 2: 3-chloro-5-ethyl-5-methyl-5,7-dihydrofuro[3,4-c]pyridazin-7-ol

To a solution of 3-chloro-5-ethyl-5-methylfuro[3,4-c]pyridazin-7(5H)-one (300 mg, 1.41 mmol) in toluene (15 mL) was added diisobutylaluminum hydride (1.0 M, 2.82 mL, 2.82 mmol) dropwise at −70° C. After addition, stirring at −70° C. was continued for 2 h and the reaction mixture was quenched by addition of saturated aqueous ammonium chloride. The resulting mixture was filtered and the filtrate was extracted with ethyl acetate (3×20 mL). The combined organic layers were washed water (20 mL), brine (20 mL), dried over sodium sulfate and concentrated under reduced pressure. The residue was purified by column chromatography (silica gel, 100-200 mesh, 0 to 30% ethyl acetate in petroleum ether) to afford 3-chloro-5-ethyl-5-methyl-5,7-dihydrofuro[3,4-c]pyridazin-7-ol (250 mg, 83%) as yellow oil, used as is in the next step.

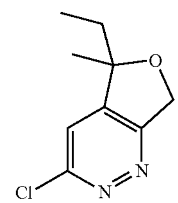

Step 3: 3-chloro-5-ethyl-5-methyl-5,7-dihydrofuro[3,4-c]pyridazine

To a solution of 3-chloro-5-ethyl-5-methyl-5,7-dihydro-furo[3,4-c]pyridazin-7-ol (250 mg, 1.16 mmol) in dichloromethane (20 mL) was added boron trifluoride diethyl etherate (826 mg, 5.82 mmol) at 0° C. Stirring was continued for 30 min at 0° C., and then triethyl silane (677 mg, 5.82 mmol) was added. The mixture was stirred for additional 3 h at 25° C. and then quenched by addition of saturated aqueous sodium bicarbonate. The resulting solution was extracted with dichloromethane (3×20 mL). The combined organic layers were washed water (20 mL), brine (20 mL), dried over sodium sulfate and concentrated under reduced pressure. The residue was purified by column chromatography (silica gel, 100-200 mesh, 0 to 15% ethyl acetate in petroleum ether) to afford 3-chloro-5-ethyl-5-methyl-5,7-dihydrofuro[3,4-c]pyridazine (100 mg, 43%) as yellow oil, used as is in the next step.

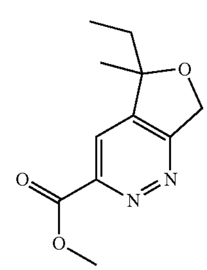 [SMILES: CCC1(C)OCc2nnc(C(=O)OC)cc21]

Step 4: methyl 5-ethyl-5-methyl-5,7-dihydrofuro[3,4-c]pyridazine-3-carboxylate

A mixture of 3-chloro-5-ethyl-5-methyl-5,7-dihydrofuro[3,4-c]pyridazine (100 mg, 0.50 mmol), 1,1'-bis(diphenylphosphino)ferrocene palladium dichloride (37 mg, 0.05 mmol) and triethylamine (255 mg, 2.52 mmol) in methanol (20 mL) was heated at 80° C. for 4 h under carbon oxide (40 psi). The solvent was removed under reduced pressure and the residue was purified by column chromatography (silica gel, 100-200 mesh, 0 to 50% ethyl acetate in petroleum ether) to afford methyl 5-ethyl-5-methyl-5,7-dihydrofuro[3,4-c]pyridazine-3-carboxylate (80 mg, 72%) as yellow oil, used as is in the next step.

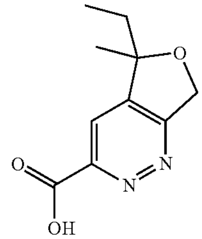

Step 5: 5-ethyl-5-methyl-5,7-dihydrofuro[3,4-c]pyridazine-3-carboxylic acid

A mixture of methyl 5-ethyl-5-methyl-5,7-dihydrofuro[3,4-c]pyridazine-3-carboxylate (80 mg, 0.36 mmol) and lithium hydroxide hydrate (75.6 mg, 1.8 mmol) in tetrahydrofuran (5 mL) and water (5 mL) was stirred at 25° C. for 2 h. After evaporation of the organic solvent under reduced pressure, the aqueous layer was acidified to pH=5 by addition of hydrochloric acid (1.0 M) and extracted with ethyl acetate (3×20 mL). The combined organic layers were washed water (20 mL), brine (20 mL), dried over sodium sulfate and concentrated under reduced pressure to afford crude 5-ethyl-5-methyl-5,7-dihydrofuro[3,4-c]pyridazine-3-carboxylic acid (60 mg, 80%) as colorless oil, used as is in the next step.

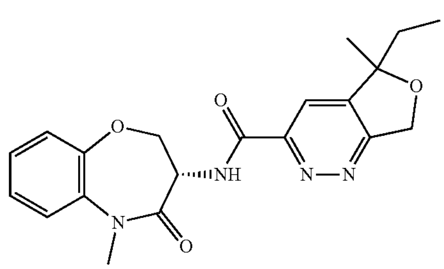 [SMILES: CCC1(C)OCc2nnc(C(=O)N[C@H]3COc4ccccc4N(C)C3=O)cc21]

Step 6: 5-ethyl-5-methyl-N—((S)-5-methyl-4-oxo-2,3,4,5-tetrahydrobenzo[b][1,4]oxazepin-3-yl)-5,7-dihydrofuro[3,4-c]pyridazine-3-carboxamide A mixture of 5-ethyl-5-methyl-5,7-dihydrofuro[3,4-c]pyridazine-3-carboxylic acid (60 mg, 0.29 mmol), (3S)-3-amino-5-methyl-2,3-dihydro-1,5-benzoxazepin-4-one (66 mg, 0.34 mmol), $N^1$-((ethylimino)methylene)-$N^3$,$N^3$-dimethylpropane-1,3-diamine hydrochloride (66 mg, 0.34 mmol) and 1H-benzo[d][1,2,3]triazol-1-ol (46 mg, 0.34 mmol) in N,N-dimethylformamide (5 mL) was stirred at 25° C. for 2 h. The reaction was concentrated under reduced pressure and the residue was purified by RP-HPLC (acetonitrile 30-60%/0.05% HCl in water) to afford 5-ethyl-5-methyl-N—((S)-5-methyl-4-oxo-2,3,4,5-tetrahydrobenzo[b][1,4]oxazepin-3-yl)-5,7-dihydrofuro[3,4-c]pyridazine-3-carboxamide (44.4 mg, 40%) as a white solid: $^1$H NMR (400 MHz, DMSO-$d_6$) δ 9.28 (d, J=4.4 Hz, 1H), 8.14 (s, 1H), 7.52 (d, J=6.8 Hz, 1H), 7.34-7.25 (m, 3H), 5.26 (s, 2H), 4.97-4.92 (m, 1H), 4.72-4.67 (m, 1H), 4.51-4.46 (m, 1H), 3.34 (s, 3H), 1.90-1.78 (s, 2H), 1.46 (s, 3H), 0.74-0.71 (m, 3H). LCMS $R_T$=0.831 min; m/z=383.1 $(M+H)^+$.

LCMS (5-95% acetonitrile in water+0.03% trifluoroacetic over 1.5 mins) retention time 0.831 min, ESI+ found $[M+H]^+$=383.1.

Example 202

WX Method II

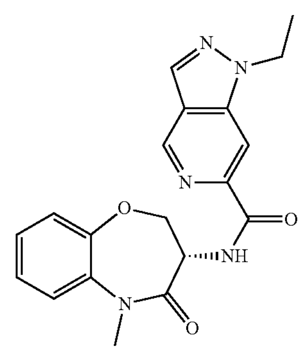 [SMILES: CCn1ncc2cnc(C(=O)N[C@H]3COc4ccccc4N(C)C3=O)cc21]

(S)-1-ethyl-N-(5-methyl-4-oxo-2,3,4,5-tetrahydrobenzo[b][1,4]oxazepin-3-yl)-1H-pyrazolo[4,3-c]pyridine-6-carboxamide

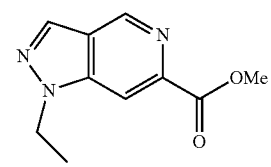

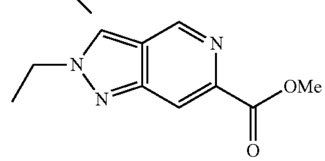

Step 1: Methyl 1-ethylpyrazolo[4,3-c]pyridine-6-carboxylate

To a solution of methyl 1H-pyrazolo[4,3-c]pyridine-6-carboxylate (300 mg, 1.70 mmol) in N,N-dimethylformamide (1.5 mL) was added potassium carbonate (702 mg, 5.06 mmol) and iodoethane (528 mg, 3.39 mmol). The reaction mixture was stirred at 45° C. for 30 min and then concentrated under reduced pressure. The residue was purified by RP-HPLC (acetonitrile 7-37/0.05% ammonia in water) to give:

Methyl 1-ethylpyrazolo[4,3-c]pyridine-6-carboxylate (175 mg, 55%) as a white solid: $^1$H NMR (400 MHz, DMSO-$d_6$) δ 9.16 (s, 1H), 8.46 (s, 1H), 8.42 (s, 1H), 4.60-4.54 (m, 2H), 3.91 (s, 3H), 1.41 (t, J=7.6 Hz, 3H). LCMS $R_T$=1.185 min; m/z=206.1 $(M+H)^+$.

Methyl 2-ethylpyrazolo[4,3-c]pyridine-6-carboxylate (110 mg, 35%) as a white solid: $^1H$ NMR (400 MHz, DMSO-$d_6$) δ 9.23 (s, 1H), 8.83 (s, 1H), 8.29 (s, 1H), 4.61-4.54 (m, 2H), 3.88 (s, 3H). 1.54 (t, J=7.6 Hz, 3H). LCMS $R_T$=1.242 min; m/z=206.1 $(M+H)^+$.

LCMS (0 to 60% acetonitrile in water+0.04% formic acid over 3 mins) retention time 1.185 min, ESI+ found [M+H]=206.1, 1.242 min, ESI+ found [M+H]=206.1

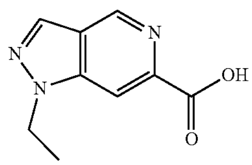

Step 2: 1-ethylpyrazolo[4,3-c]pyridine-6-carboxylic acid

A mixture of methyl 1-ethylpyrazolo[4,3-c]pyridine-6-carboxylate (50 mg, 0.24 mmol) and lithium hydroxide hydrate (29 mg, 1.22 mmol) in tetrahydrofuran (5 mL) and water (2 mL) was stirred at 25° C. for 18 h. The organic solvent was removed under reduced pressure and the aqueous residue was adjusted to pH=5 by addition of hydrochloric acid (1.0 M). The mixture was concentrated under reduced pressure affording crude 1-ethylpyrazolo[4,3-c]pyridine-6-carboxylic acid (40 mg, 86%) as a white solid, used in the next step without further purification.

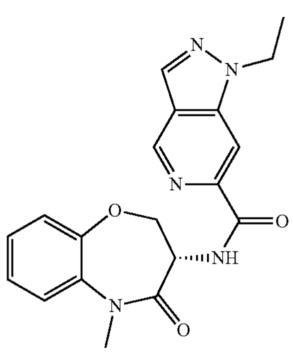 [SMILES: CCn1ncc2cnc(C(=O)N[C@H]3COc4ccccc4N(C)C3=O)cc21]

Step 3: (S)-1-ethyl-N-(5-methyl-4-oxo-2,3,4,5-tetrahydrobenzo[b][1,4]oxazepin-3-yl)-1H-pyrazolo[4,3-c]pyridine-6-carboxamide A mixture of 1-ethylpyrazolo[4,3-c]pyridine-6-carboxylic acid (40 mg, 0.21 mmol), (3 s)-3-amino-5-methyl-2,3-dihydro-1,5-benzoxazepin-4-one (44 mg, 0.23 mmol), 1H-benzo[d][1,2,3]triazol-1-ol (34 mg, 0.25 mmol) and $N^1$-((ethylimino)methylene)-$N^3$,$N^3$-dimethylpropane-1,3-diamine hydrochloride (48 mg, 0.25 mmol) in N,N-dimethylformamide (5 mL) was stirred at 25° C. for 1 h. The reaction was concentrated under reduced pressure and the residue was purified by RP-HPLC (acetonitrile 30-60%/0.05% ammonia in water) affording (S)-1-ethyl-N-(5-methyl-4-oxo-2,3,4,5-tetrahydrobenzo[b][1,4]oxazepin-3-yl)-1H-pyrazolo[4,3-c]pyridine-6-carboxamide (29.9 mg, 39.0%) as a white solid: $^1H$ NMR (400 MHz, DMSO-$d_6$) δ 9.18 (s, 1H), 9.03 (d, J=8.0 Hz, 1H), 8.44 (s, 1H), 8.31 (s, 1H), 7.57-7.47 (m, 1H), 7.41-7.23 (m, 3H), 4.97-4.88 (m, 1H), 4.61-4.49 (m, 4H), 3.34 (s, 3H), 1.39 (t, J=7.2 Hz, 3H). LCMS $R_T$=0.812 min; m/z=366.1 $(M+H)^+$.

LCMS (5 to 95% acetonitrile in water+0.03% trifluoacetic acid over 1.5 mins) retention time 0.812 min, ESI+ found [M+H]=366.1.

Example 203

WX Method EEEEEE

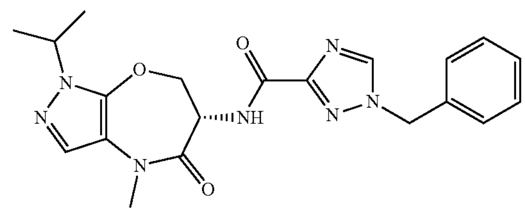 [SMILES: CC(C)n1ncc2c1OC[C@H](NC(=O)c1ncn(Cc3ccccc3)n1)C(=O)N2C]

(S)-1-benzyl-N-(1-isopropyl-5-oxo-4,5,6,7-tetrahydro-1H-pyrazolo[3,4-b][1,4]oxazepin-6-yl)-1H-1,2,4-triazole-3-carboxamide A mixture of (S)-6-amino-1-isopropyl-6,7-dihydro-1H-pyrazolo[3,4-b][1,4]oxazepin-5(4H)-one (27 mg, 0.13 mmol), 1-benzyl-1,2,4-triazole-3-carboxylic acid (27 mg, 0.13 mmol), 1H-benzo[d][1,2,3]triazol-1-ol (21 mg, 0.15 mmol) and $N^1$-((ethylimino)methylene)-$N^3$,$N^3$-dimethylpropane-1,3-diamine hydrochloride (30 mg, 0.15 mmol) in N,N-dimethylformamide (4 mL) was stirred at 25° C. for 12 h. The reaction concentrated under reduced pressure and the residue was purified by RP-HPLC (acetonitrile 0-40%/0.1% ammonium hydroxide in water) to afford (S)-1-benzyl-N-(1-isopropyl-5-oxo-4,5,6,7-tetrahydro-1H-pyrazolo[3,4-b][1,4]oxazepin-6-yl)-1H-1,2,4-triazole-3-carboxamide (7 mg, 14%) as white solid. $^1H$ NMR (400 MHz, $CD_3OD$) δ 8.60 (s, 1H), 7.37 (s, 5H), 7.20 (s, 1H), 5.49 (s, 2H), 4.83 (s, 1H), 4.67-4.64 (m, 1H), 4.56-4.48 (m, 1H), 4.40-4.36 (m, 1H), 1.43-1.40 (m, 6H). LCMS $R_T$=0.958 min; m/z=396.2 $(M+H)^+$.

LCMS (10-80% acetonitrile in water+0.03% trifluoroacetic over 2 mins) retention time 0.958 min, ESI+ found $[M+H]^+$=396.2.

Example 204

WX Method LLLLLL

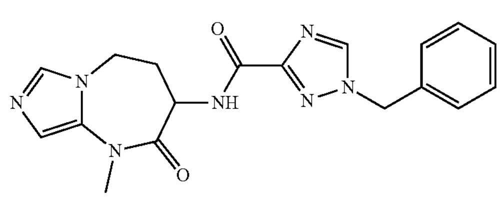 [SMILES: CN1C(=O)C(NC(=O)c2ncn(Cc3ccccc3)n2)CCn2cncc21]

benzyl-N-(1-methyl-2-oxo-2,3,4,5-tetrahydro-1H-imidazo[1,5-a][1,3]diazepin-3-yl)-1H-1, 2,4-triazole-3-carboxamide

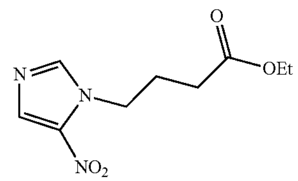 [SMILES: CCOC(=O)CCCn1cncc1N]

Step 1: ethyl 4-(5-nitro-1H-imidazol-1-yl)butanoate

A mixture of 5-nitro-1H-imidazole (60.0 g, 530.0 mmol), ethyl 4-bromobutyrate (109.0 g, 557.0 mmol) and potassium carbonate (146.0 g, 1.1 mol) in N,N-dimethylformamide (300 mL) was heated to 120° C. for 2 h. The mixture was diluted with water (400 mL) and extracted with ethyl acetate (3×300 mL). The combined organic layers were washed with water (200 mL), dried over sodium sulfate and concentrated under reduced pressure. The residue was purified by column chromatography (silica gel, 100-200 mesh, 0 to 20% ethyl acetate in petroleum ether) to give ethyl 4-(5-nitro-1H-imidazol-1-yl)butanoate (7.0 g, 6%) as a colorless oil, used in the next step without further purification.

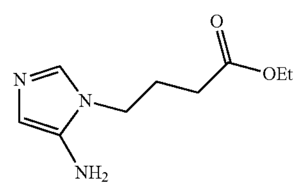

Step 2: ethyl 4-(5-amino-1H-imidazol-1-yl)butanoate

A mixture of ethyl 4-(5-nitro-1H-imidazol-1-yl)butanoate (7.0 g, 30.8 mmol) and 10% palladium on carbon (32.8 g, 30.8 mmol) in 1,4-dioxane (300 mL) was hydrogenated (15 psi) at 25° C. for 12 h. The mixture was filtered and the filtrate was concentrated under reduced pressure to afford ethyl 4-(5-amino-1H-imidazol-1-yl)butanoate (4.0 g, 65%) as a brown oil: LCMS $R_T$=1.25 min; m/z=198.2 $(M+H)^+$.

LCMS (0 to 60% acetonitrile in water+0.03% ammonium hydroxide over 3.0 mins) retention time 1.25 min, $ESI^+$ found [M+H]=198.2

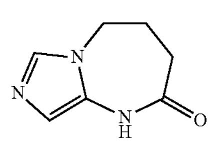 [SMILES: O=C1CCCn2cncc2N1]

Step 3: 4,5-dihydro-1H-imidazo[1,5-a][1,3]diazepin-2(3H)-one

To a solution of ethyl 4-(5-amino-1H-imidazol-1-yl)butanoate (500 mg, 2.5 mmol) in ethanol (20 mL) was added sodium ethanolate (863 mg, 12.7 mmol). The mixture was stirred at 25° C. for 4 h and then concentrated under reduced pressure. The residue was purified by column chromatography (silica gel, 100-200 mesh, 0 to 10% methanol in dichloromethane) to afford 4,5-dihydro-1H-imidazo[1,5-a][1,3]diazepin-2(3H)-one (200 mg, 52%) as a white solid. $^1H$ NMR (400 MHz, DMSO-$d_6$) δ 9.66 (s, 1H), 7.48 (s, 1H), 6.53 (s, 1H), 4.04 (t, J=6.8 Hz, 2H), 2.23-2.18 (m, 2H), 2.15-2.07 (m, 2H).

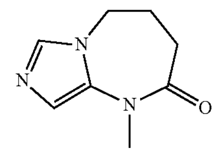

Step 4: 1-methyl-4,5-dihydro-1H-imidazo[1,5-a][1,3]diazepin-2(3H)-one

To a solution of 4,5-dihydro-1H-imidazo[1,5-a][1,3]diazepin-2(3H)-one (200 mg, 1.23 mmol) in N,N-dimethylformamide (10 mL) was added cesium carbonate (431 mg, 1.32 mmol) and iodomethane (175 mg, 1.23 mmol). The mixture was stirred at 25° C. for 3 h and then filtered. The filtrate was concentrated under reduced pressure and the residue was purified by column chromatography (silica gel, 100-200 mesh, 0 to 10% methanol in dichloromethane) to afford 1-methyl-4,5-dihydro-1H-imidazo[1,5-a][1,3]diazepin-2(3H)-one (100 mg, 46%) as a white solid, used as is in the next step.

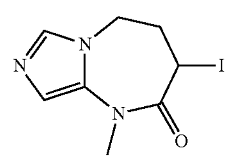

Step 5: 3-iodo-1-methyl-4,5-dihydro-1H-imidazo[1,5-a][1,3]diazepin-2(3H)-one

To a solution of 1-methyl-4,5-dihydro-3H-imidazo[1,5-a][1,3]diazepin-2-one (100 mg, 0.61 mmol) in dichloromethane (10 mL) was added $N^1,N^1,N^2,N^2$-tetramethylethane-1,2-diamine (946 mg, 7.26 mmol) and iodotrimethylsilane (1.45 g, 7.26 mmol) at −15° C. The mixture was stirred at −15° C. for 1.5 h, and then iodine (922 mg, 3.63 mmol) was added. Stirring was continued for 3 h and the reaction was quenched by addition of saturated aqueous solution sodium sulfite (5%, 5 mL). The solution was extracted with dichloromethane (2×10 mL). The combined organic layers were dried over sodium sulfate and concentrated under reduced pressure. The residue was purified by column chromatography (100-200 mesh silica gel, 0 to 10% methanol in dichloromethane) to afford 3-iodo-1-methyl-4,5-dihydro-1H-imidazo[1,5-a][1,3]diazepin-2(3H)-one (10 mg, 6%) as a light yellow solid: LCMS $R_T$=1.34 min; m/z=292.0 $(M+H)^+$.

LCMS (0 to 60% acetonitrile in water+0.05% ammonium bicarbonate over 3 mins) retention time 1.34 min, ESI+ found [M+H]=292.0.

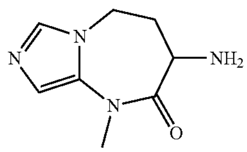

Step 6: 3-amino-1-methyl-4,5-dihydro-1H-imidazo[1,5-a][1,3]diazepin-2(3H)-one

To a solution of 3-iodo-1-methyl-4,5-dihydro-1H-imidazo[1,5-a][1,3]diazepin-2(3H)-one (10.0 mg, 0.03 mmol) in N,N-dimethylformamide (3 mL) was added ammonium hydroxide (0.01 mL, 0.34 mmol). The reaction mixture was stirred at 80° C. for 2 h and then concentrated under reduced pressure to afford 3-amino-1-methyl-4,5-dihydro-1H-imidazo[1,5-a][1,3]diazepin-2(3H)-one (6 mg, 97%) as a yellow oil, used in the next step without further purification.

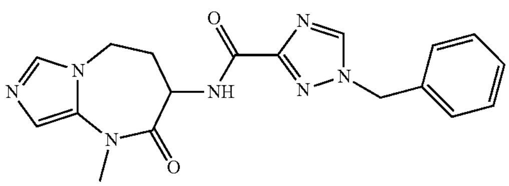 [SMILES: CN1C(=O)C(NC(=O)c2ncn(Cc3ccccc3)n2)CCn2cncc21]

Step 7: 1-benzyl-N-(1-methyl-2-oxo-2,3,4,5-tetrahydro-H-imidazo[1,5-a][1,3]diazepin-3-yl)-1H-1,2,4-triazole-3-carboxamide A mixture of 1-benzyl-1,2,4-triazole-3-carboxylic acid (6.8 mg, 0.03 mmol), 3-amino-1-methyl-4,5-dihydro-1H-imidazo[1,5-a][1,3]diazepin-2(3H)-one (6.0 mg, 0.03 mmol), $N^1$-((ethylimino)methylene)-$N^3$,$N^3$-dimethylpropane-1,3-diamine hydrochloride (7.7 mg, 0.04 mmol) and 1H-benzo[d][1,2,3]triazol-1-ol (5.4 mg, 0.04 mmol) in N,N-dimethylformamide (2 mL) was stirred at 25° C. for 1 h. The reaction was concentrated under reduced pressure and the residue was purified by RP-HPLC (acetonitrile 0-40/0.1% ammonium in water) to afford 1-benzyl-N-(1-methyl-2-oxo-2,3,4,5-tetrahydro-1H-imidazo[1,5-a][1,3]diazepin-3-yl)-1H-1,2,4-triazole-3-carboxamide (1.8 mg, 14%) as a white solid. $^1$H NMR (400 MHz, $CD_3OD$) δ 8.56 (s, 1H), 7.62 (s, 1H), 7.37-7.33 (m, 5H), 6.99 (s, 1H), 5.47 (s, 2H), 4.85-4.59 (m, 1H), 4.45-4.39 (m, 1H), 4.03-3.97 (m, 1H), 3.35 (s, 3H), 2.79-2.72 (m, 1H), 2.20-2.15 (m, 1H). LCMS $R_T$=1.67 min; m/z=366.1 $(M+H)^+$.

LCMS (0 to 60% acetonitrile in water+0.03% ammonium bicarbonate 3 mins) retention time 1.67 min, ESI+ found [M+H]=366.1.

Example 205

WX Method I

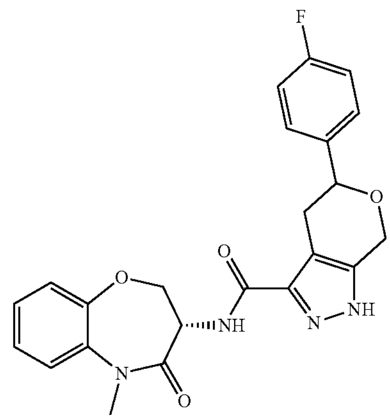 [SMILES: CN1C(=O)[C@@H](NC(=O)c2n[nH]c3c2CC(c2ccc(F)cc2)OC3)COc2ccccc21]

5-(4-fluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide

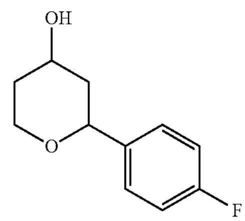 [SMILES: OC1CCOC(c2ccc(F)cc2)C1]

Step 1: 2-(4-fluorophenyl)tetrahydro-2H-pyran-4-ol

A mixture of 4-fluorobenzaldehyde (10.0 g, 86.0 mmol) and but-3-en-1-ol (11.6 g, 161.2 mmol) in 20% sulfuric acid (100 mL) was stirred at 80° C. for 12 h. The mixture was cooled and then adjusted to pH=9 by slow addition of 20% aqueous sodium bicarbonate. The resulting mixture was extracted with ethyl acetate (3×100 mL). The combined organic layers were dried over sodium sulfate and concentrated under reduced pressure. The residue was purified by column chromatography (silica gel, 100-200 mesh, 20 to 30% ethyl acetate in petroleum ether) to afford 2-(4-fluorophenyl)tetrahydro-2H-pyran-4-ol (9.5 g, 56%) as light yellow oil, used in the next step without further purification.

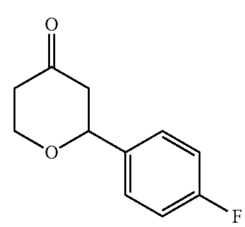 [SMILES: O=C1CCOC(c2ccc(F)cc2)C1]

Step 2: 2-(4-fluorophenyl)dihydro-2H-pyran-4(3H)-one

To a solution of 2-(4-fluorophenyl)tetrahydro-2H-pyran-4-ol (9.5 g, 48.4 mmol) in dichloromethane (50 mL) was added pyridiniumchlorochromate (12.0 g, 55.7 mmol) portionwise over 5 min. The reaction was stirred for 18 h at 25° C. and then filtered. The filtrate was concentrated under reduced pressure. The residue was purified by column chromatography (silica gel, 100-200 mesh, 0 to 10% ethyl acetate in petroleum ether) to afford 2-(4-fluorophenyl) dihydro-2H-pyran-4(3H)-one (7.2 g, 77%) as light yellow oil, used in the next step without further purification.

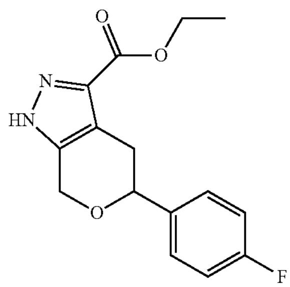 [SMILES: CCOC(=O)c1n[nH]c2c1CC(c1ccc(F)cc1)OC2]

Step 3: ethyl 5-(4-fluorophenyl)-1,4,5,7-tetrahydro-pyrano[3,4-c]pyrazole-3-carboxylate To a solution of 2-(4-fluorophenyl) dihydro-2H-pyran-4 (3H)-one (2.00 g, 10.3 mmol) was added pyrrolidine (37 mg, 0.5 mmol) and ethyl diazoacetate (0.59 g, 5.2 mmol). The mixture was stirred for 15 h at 25° C. and then diluted with water (30 mL). The resulting mixture was extracted with ethyl acetate (2×50 mL). The combined organic layers were concentrated and the residue was purified by column chromatography (silica gel, 100-200 mesh, 0 to 30% ethyl acetate in petroleum ether) to afford ethyl 5-(4-fluorophenyl)-1,4,5,7-tetrahydropyrano[3,4-c]pyrazole-3-carboxylate (130 mg, 4%) as a light yellow solid: $^1$H NMR (400 MHz, $CDCl_3$) δ 7.42-7.39 (m, 2H), 7.06 (t, J=8.6 Hz, 2H), 5.11-5.07 (m, 1H), 4.92-4.89 (m, 1H), 4.61-4.55 (m, 1H), 4.36 (q, J=7.2 Hz, 2H), 3.17-3.13 (m, 1H), 2.93-2.86 (m, 1H), 1.34 (t, J=7.1 Hz, 3H).

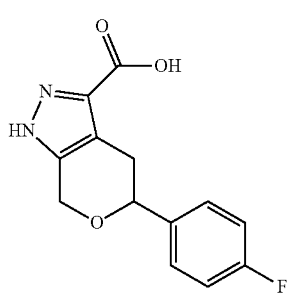 [SMILES: O=C(O)c1n[nH]c2c1CC(c1ccc(F)cc1)OC2]

Step 4: 5-(4-fluorophenyl)-1,4,5,7-tetrahydropyrano [3,4-c]pyrazole-3-carboxylic acid A mixture of ethyl 5-(4-fluorophenyl)-1,4,5,7-tetrahydro-pyrano[3,4-c]pyrazole-3-carboxylate (170 mg, 0.59 mmol) and lithium hydroxide hydrate (140 mg, 5.86 mmol) in tetrahydrofuran (3 mL) and water (3 mL) was stirred for 12 h at 25° C. The organic solvent was removed under reduced pressure, and the aqueous layer was adjusted to pH=3 by addition of hydrochloric acid (1.0 M). The solution was concentrated under reduced pressure to afford crude 5-(4-fluorophenyl)-1,4,5,7-tetrahydropyrano[3,4-c]pyrazole-3-carboxylic acid (70 mg, 46%) as a light yellow solid: $^1$H NMR (400 MHz, DMSO-$d_6$) δ 7.51-7.45 (m, 2H), 7.23-7.16 (m, 2H), 4.92-4.88 (m, 1H), 4.82-4.79 (m, 1H), 4.66-4.62 (m, 1H), 3.11-3.06 (m, 1H), 2.71-2.64 (m, 1H).

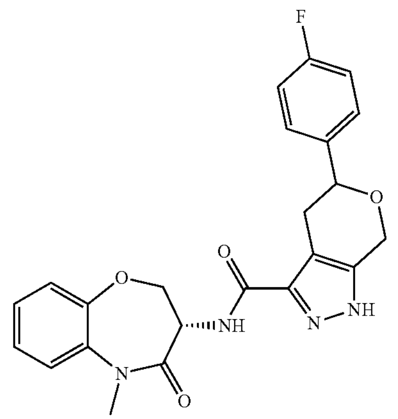 [SMILES: CN1C(=O)[C@@H](NC(=O)c2n[nH]c3c2CC(c2ccc(F)cc2)OC3)COc2ccccc21]

Step 5: 5-(4-fluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide A mixture of 5-(4-fluorophenyl)-1,4,5,7-tetrahydropyrano[3,4-c]pyrazole-3-carboxylic acid (35 mg, 0.13 mmol), 1H-benzo[d][1,2,3]triazol-1-ol (22 mg, 0.16 mmol), (3S)-3-amino-5-methyl-2,3-dihydro-1,5-benzoxazepin-4-one (26 mg, 0.13 mmol) and N$^1$-((ethylimino)methylene)-N$^3$,N$^3$-dimethylpropane-1,3-diamine hydrochloride (28 mg, 0.16 mmol) in N,N-dimethylformamide (3 mL) was stirred at 25° C. for 12 h. The reaction was concentrated to dryness under reduced pressure and the residue was purified by RP-HPLC (13 to 43% acetonitrile in water and 0.05% hydrochloric acid) to afford 5-(4-fluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide (41 mg, 70%) as a light yellow solid: $^1$H NMR (400 MHz, $CD_3OD$) δ 7.48-7.38 (m, 3H), 7.30-7.28 (m, 3H), 7.09-7.06 (m, 2H), 4.98-4.93 (m, 2H), 4.88-4.83 (m, 1H), 4.61-4.58 (m, 2H), 4.57-4.33 (m, 1H), 3.40 (s, 3H), 3.13-3.08 (m, 1H), 2.80-2.74 (m, 1H). LCMS $R_T$=1.12 min; m/z=437.2 $(M+H)^+$.

LCMS (10 to 80% acetonitrile in water+0.03% trifluoroacetic acid over 2 mins) retention time 1.12 min, ESI+ found $[M+H]^+$=437.2.

Example 206

WX Method J

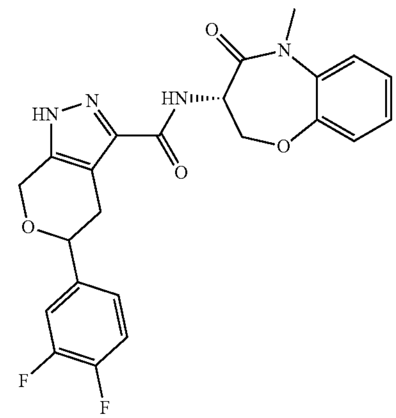 [SMILES: CN1C(=O)[C@@H](NC(=O)c2n[nH]c3c2CC(c2ccc(F)c(F)c2)OC3)COc2ccccc21]

5-(3,4-difluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide

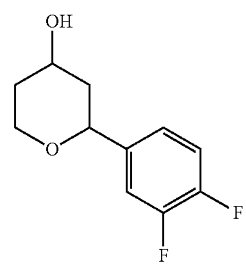 [SMILES: OC1CCOC(c2ccc(F)c(F)c2)C1]

Step 1: 2-(3,4-difluorophenyl)tetrahydro-2H-pyran-4-ol

A mixture of 3,4-difluorobenzaldehyde (10.0 g, 70.4 mmol) and but-3-en-1-ol (5.1 g, 70.4 mmol) in 20% sulfuric acid (20 mL) was stirred at 80° C. for 12 h. The mixture was cooled and then adjusted to pH=9 by slow addition of 20% aqueous sodium bicarbonate. The resulting mixture was extracted with ethyl acetate (3×100 mL). The combined organic layers were dried over sodium sulfate and concentrated under reduced pressure. The residue was purified by column chromatography (silica gel, 100-200 mesh, 0 to 10% ethyl acetate in petroleum ether) to afford 2-(3,4-difluorophenyl)tetrahydro-2H-pyran-4-ol (9.2 g, 61%) as pale yellow oil: $^1$H NMR (400 MHz, $CDCl_3$) δ 7.17-7.04 (m, 2H), 7.00 (s, 1H), 4.24-4.21 (m, 1H), 4.13-4.09 (m, 1H), 3.88-3.81 (m, 1H), 3.51 (t, J=12.0 Hz, 1H), 2.37 (br. s, 1H), 2.10-2.07 (m, H), 1.92-1.88 (m, 1H), 1.60-1.50 (m, 1H), 1.43-1.35 (m, 1H).

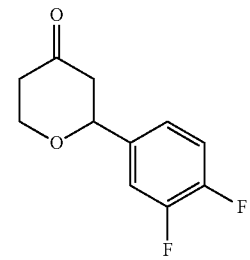 [SMILES: O=C1CCOC(c2ccc(F)c(F)c2)C1]

Step 2: 2-(3,4-difluorophenyl)dihydro-2H-pyran-4(3H)-one

To a solution of 2-(3,4-difluorophenyl)tetrahydro-2H-pyran-4-ol (9.2 g, 43.0 mmol) in dichloromethane (50 mL) was added pyridiniumchlorochromate (11.1 g, 51.5 mmol) portionwise over 5 min. The reaction was stirred for 18 h at 25° C. and then filtered. The filtrate was concentrated under reduced pressure. The crude was purified by column chromatography (silica gel, 100-200 mesh, 0 to 10% ethyl acetate in petroleum ether) affording 2-(3,4-difluorophenyl)dihydro-2H-pyran-4(3H)-one (6.5 g, 71%) as light yellow oil: $^1$H NMR (400 MHz, $CDCl_3$) δ 7.50-7.44 (m, 1H), 6.88 (t, J=8.0 Hz, 1H), 6.80-6.74 (m, 1H), 4.87-4.84 (m, 1H), 4.42-4.37 (m, 1H), 3.85-3.78 (m, 1H), 2.73-2.61 (m, 2H), 2.55-2.49 (m, 1H), 2.42-2.38 (m, 1H).

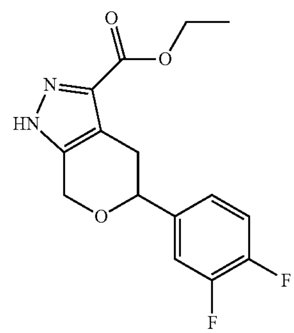 [SMILES: CCOC(=O)c1n[nH]c2c1CC(c1ccc(F)c(F)c1)OC2]

Step 3: ethyl 5-(3,4-difluorophenyl)-1,4,5,7-tetrahydropyrano[3,4-c]pyrazole-3-carboxylate To a solution of 2-(3,4-difluorophenyl)dihydro-2H-pyran-4(3H)-one (2.0 g, 9.4 mmol) in dimethyl sulfoxide (15 mL) was added pyrrolidine (34 mg, 0.5 mmol) and ethyl diazoacetate (538 mg, 4.7 mmol). The reaction was stirred for 16 h at 25° C. and then diluted with water (30 mL). The mixture was extracted with ethyl acetate (3×50 mL). The combined organic layers were concentrated under reduced pressure and the residue was purified by column chromatography (silica gel, 100-200 mesh, 0 to 35% ethyl acetate in petroleum ether) to afford ethyl 5-(3,4-difluorophenyl)-1,4,5,7-tetrahydropyrano[3,4-c]pyrazole-3-carboxylate (180 mg, 6%) as a light yellow solid: $^1$H NMR (400 MHz, $CDCl_3$) δ 7.30-7.27 (m, 1H), 7.16-7.13 (m, 2H), 5.12-5.08 (m, 1H), 4.92-4.88 (m, 1H), 4.61-4.55 (m, 1H), 4.37 (q, J=7.6 Hz, 2H), 3.17-3.12 (m, 1H), 2.91-2.80 (m, 1H), 1.34 (t, J=7.6 Hz, 3H).

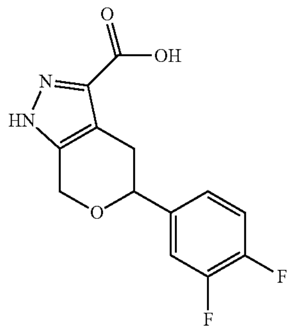 [SMILES: O=C(O)c1n[nH]c2c1CC(c1ccc(F)c(F)c1)OC2]

Step 4: 5-(3,4-difluorophenyl)-1,4,5,7-tetrahydropyrano[3,4-c]pyrazole-3-carboxylic acid A mixture of ethyl 5-(3,4-difluorophenyl)-1,4,5,7-tetrahydropyrano[3,4-c]pyrazole-3-carboxylate (180 mg, 0.58 mmol) and lithium hydroxide hydrate (139 mg, 5.80 mmol) in tetrahydrofuran (3 mL) and water (3 mL) was stirred for 12 h at 25° C. The organic solvent was removed under reduced pressure, and the aqueous layer was adjusted to pH=3 by addition of hydrochloric acid (1.0 M). The solution was concentrated under reduced pressure to afford crude 5-(3,4-difluorophenyl)-1,4,5,7-tetrahydropyrano[3,4-c]pyrazole-3-carboxylic acid (60 mg, 37%) as a light yellow solid: $^1$H NMR (400 MHz, DMSO-$d_6$) δ 7.58-7.45 (m, 2H), 7.36 (s, 1H), 5.00-4.96 (m, 1H), 4.88-4.85 (m, 1H), 4.72-4.70 (m, 1H), 3.18 (d, J=12.0 Hz, 1H), 2.75-2.68 (m, 1H).

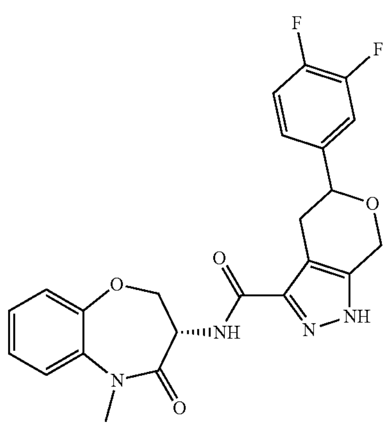 [SMILES: CN1C(=O)[C@@H](NC(=O)c2n[nH]c3c2CC(c2ccc(F)c(F)c2)OC3)COc2ccccc21]

Step 5: 5-(3,4-difluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide A mixture of (3S)-3-amino-5-methyl-2,3-dihydro-1,5-benzoxazepin-4-one (20 mg, 0.11 mmol), 5-(3,4-difluorophenyl)-1,4,5,7-tetrahydropyrano[3,4-c]pyrazole-3-carboxylic acid (30 mg, 0.11 mmol), 1H-benzo[d][1,2,3]triazol-1-ol (17 mg, 0.13 mmol) and $N^1$-((ethylimino)methylene)-$N^3$,$N^3$-dimethylpropane-1,3-diamine hydrochloride (23 mg, 0.13 mmol) in N,N-dimethylformamide (3 mL) was stirred at 25° C. for 2 h. The reaction was concentrated to dryness under reduced pressure and the residue was purified by RP-HPLC (13 to 43% acetonitrile in water and 0.05% hydrochloric acid) to afford 5-(3,4-difluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide (27 mg, 55%) as a white solid: $^1$H NMR (400 MHz, $CD_3OD$) δ 7.40-7.21 (m, 7H), 5.00-4.95 (m, 2H), 4.86-4.82 (m, 1H), 4.60-4.56 (m, 2H), 4.37-4.33 (m, 1H), 3.31 (s, 3H), 3.16-3.12 (m, 1H), 2.75-2.67 (m, 1H). LCMS $R_T$=1.15 min; m/z=455.2 $(M+H)^+$.

LCMS (10 to 80% acetonitrile in water+0.03% trifluoroacetic acid over 2 mins) retention time 1.15 min, ESI+ found $[M+H]^+$=455.2.

Example 207

WX Method K

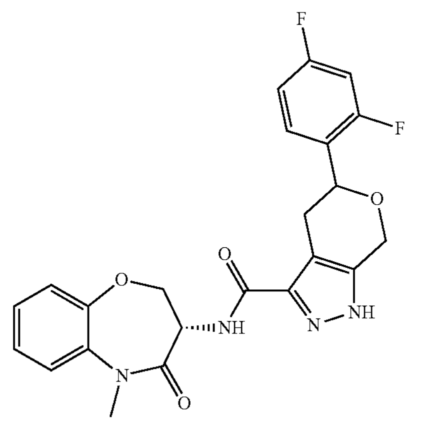 [SMILES: CN1C(=O)[C@@H](NC(=O)c2n[nH]c3c2CC(c2ccc(F)cc2F)OC3)COc2ccccc21]

5-(2,4-difluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide

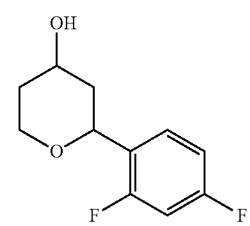 [SMILES: OC1CCOC(c2ccc(F)cc2F)C1]

Step 1: 2-(2,4-difluorophenyl)tetrahydro-2H-pyran-4-ol

A mixture of 2,4-difluorobenzaldehyde (10.0 g, 70.4 mmol) and but-3-en-1-ol (5.1 g, 70.4 mmol) in 20% sulfuric acid (20 mL) was stirred at 80° C. for 12 h. The mixture was cooled and then adjusted to pH=9 by slow addition of 20% aqueous sodium bicarbonate. The resulting mixture was extracted with ethyl acetate (3×100 mL). The combined organic layers were dried over sodium sulfate and concentrated under reduced pressure. The residue was purified by column chromatography (silica gel, 100-200 mesh, 0 to 10% ethyl acetate in petroleum ether) to afford 2-(2,4-difluorophenyl)tetrahydro-2H-pyran-4-ol (9.2 g, 61%) as pale yellow oil: $^1$H NMR (400 MHz, $CDCl_3$) δ 7.44-7.38 (m, 1H), 6.84 (t, J=8.4 Hz, 1H), 6.77-6.71 (m, 1H), 4.55 (d, J=11.0 Hz, 1H), 4.14-4.10 (m, 1H), 3.93-3.85 (m, 1H), 3.55 (t, J=12.0 Hz, 1H), 2.19 (br. s, 1H), 2.12 (m, 1H), 1.94-1.90 (m, 1H), 1.64-1.53 (m, 1H), 1.49-1.39 (m, 1H).

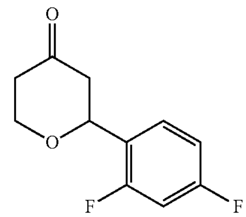 [SMILES: O=C1CCOC(c2ccc(F)cc2F)C1]

Step 2: 2-(2,4-difluorophenyl)dihydro-2H-pyran-4(3H)-one

To a solution of 2-(2,4-difluorophenyl)tetrahydro-2H-pyran-4-ol (5.0 g, 23.5 mmol) in dichloromethane (50 mL) was added pyridiniumchlorochromate (6.5 g, 28.0 mmol) portionwise over 5 min. The reaction was stirred for 18 h at 25° C. and then filtered. The filtrate was concentrated under reduced pressure. The residue was purified by column chromatography (silica gel, 100-200 mesh, 0 to 10% ethyl acetate in petroleum ether) affording 2-(2,4-difluorophenyl) dihydro-2H-pyran-4(3H)-one (3.3 g, 66%) as light yellow oil: $^1$H NMR (400 MHz, $CD_3OD$) δ 7.24-7.09 (m, 2H), 7.04 (s, 1H), 4.59-4.56 (m, 1H), 4.42-4.37 (m, 1H), 3.83-3.76 (m, 1H), 2.72-2.59 (m, 2H), 2.54-2.38 (m, 2H).

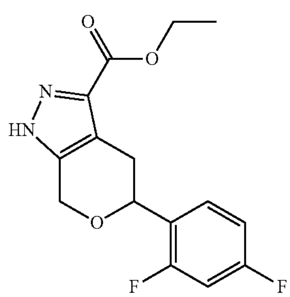 [SMILES: CCOC(=O)c1n[nH]c2c1CC(c1ccc(F)cc1F)OC2]

Step 3: ethyl 5-(2,4-difluorophenyl)-1,4,5,7-tetrahydropyrano[3,4-c]pyrazole-3-carboxylate To a solution of 2-(2,4-difluorophenyl) dihydro-2H-pyran-4(3H)-one (2.5 g, 11.8 mmol) in dimethyl sulfoxide (12 mL) was added pyrrolidine (84 mg, 1.2 mmol) and ethyl diazoacetate (1.3 g, 11.8 mmol). The mixture was stirred for 15 h at 25° C. and then diluted with water (100 mL). The resulting mixture was extracted with ethyl acetate (2×100 mL). The combined organic layers were washed with brine (60 mL), dried over sodium sulfate and evaporated under reduced pressure. The residue was purified by column chromatography (0 to 40% ethyl acetate in petroleum ether) to afford ethyl 5-(2,4-difluorophenyl)-1,4,5,7-tetrahydropyrano[3,4-c]pyrazole-3-carboxylate (185 mg, 5%) as light yellow oil: $^1$H NMR (400 MHz, $CDCl_3$) δ 7.56-7.50 (m, 1H), 6.92-6.88 (m, 1H), 6.83-6.78 (m, 1H), 5.11 (d, J=14.6 Hz, 1H), 4.93-4.85 (m, 2H), 4.36 (q, J=7.1 Hz, 2H), 3.19-3.14 (m, 1H), 2.88-2.81 (m, 1H), 1.34 (t, J=7.2 Hz, 3H).

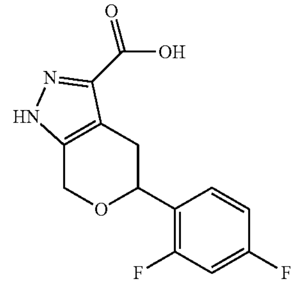 [SMILES: O=C(O)c1n[nH]c2c1CC(c1ccc(F)cc1F)OC2]

Step 4: 5-(2,4-difluorophenyl)-1,4,5,7-tetrahydropyrano[3,4-c]pyrazole-3-carboxylic acid A mixture of ethyl 5-(2,4-difluorophenyl)-1,4,5,7-tetrahydropyrano[3,4-c]pyrazole-3-carboxylate (160 mg, 0.52 mmol) and lithium hydroxide hydrate (124 mg, 5.20 mmol) in tetrahydrofuran (3 mL) and water (3 mL) was stirred for 12 h at 25° C. The organic solvent was removed under reduced pressure, and the aqueous layer was adjusted to pH=3 by addition of hydrochloric acid (1.0 M). The solution was concentrated under reduced pressure to afford crude 5-(2,4-difluorophenyl)-1,4,5,7-tetrahydropyrano[3,4-c]pyrazole-3-carboxylic acid (75 mg, 52%) as a light yellow solid, used in the next step without further purification.

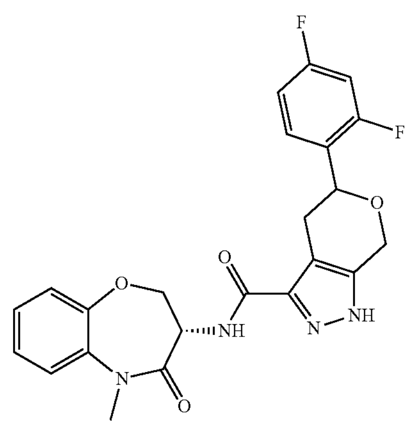 [SMILES: CN1C(=O)[C@@H](NC(=O)c2n[nH]c3c2CC(c2ccc(F)cc2F)OC3)COc2ccccc21]

Step 5: 5-(2,4-difluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide A mixture of 5-(2,4-difluorophenyl)-1,4,5,7-tetrahydropyrano[3,4-c]pyrazole-3-carboxylic acid (30 mg, 0.11 mmol), 1H-benzo[d][1,2,3]triazol-1-ol (17 mg, 0.13 mmol), (3S)-3-amino-5-methyl-2,3-dihydro-1,5-benzoxazepin-4-one (21 mg, 0.11 mmol) and $N^1$-((ethylimino)methylene)-$N^3$,$N^3$-dimethylpropane-1,3-diamine hydrochloride (23 mg, 0.13 mmol) in N,N-dimethylformamide (2 mL) was stirred at 25° C. for 12 h. The reaction was concentrated to dryness under reduced pressure and the residue was purified by RP-HPLC (13 to 43% acetonitrile in water and 0.05% hydrochloric acid) to afford 5-(2,4-difluorophenyl)-N—((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide (11 mg, 23%) as a white solid: $^1$H NMR (400

MHz, $CD_3OD$) δ 7.57-7.21 (m, 6H), 6.97-6.94 (m, 1H), 4.99-4.86 (m, 3H), 4.60-4.58 (m, 2H), 4.40-4.36 (m, 1H), 3.41 (s, 3H), 3.16-3.08 (m, 1H), 2.81-2.70 (m, 1H). LCMS $R_T$=1.14 min; m/z=455.2 $(M+H)^+$.

LCMS (10 to 80% acetonitrile in water+0.03% trifluoroacetic acid over 2 mins) retention time 1.14 min, ESI+ found $[M+H]^+$=455.2.

Example 208

WX Method RRRR

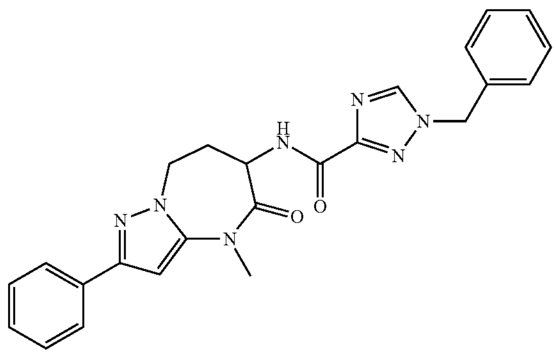 [SMILES: CN1C(=O)C(NC(=O)c2ncn(Cc3ccccc3)n2)CCn2nc(-c3ccccc3)cc21]

1-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide

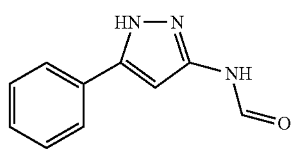 [SMILES: O=CNc1cc(-c2ccccc2)[nH]n1]

Step 1: N-(5-phenyl-1H-pyrazol-3-yl)formamide

A mixture of 5-phenyl-1H-pyrazol-3-amine (2.5 g, 15.7 mmol) and formic acid (10 mL, 15.71 mmol) was stirred at 110° C. in a sealed vessel for 2 h. The mixture was concentrated under reduced pressure and the residue was washed with water (50 mL) to give crude N-(5-phenyl-1H-pyrazol-3-yl)formamide (2.7 g, 92%) as a white solid: LCMS $R_T$=1.149 min; m/z=187.9 $(M+H)^+$.

LCMS (0 to 60% acetonitrile in water+0.03% trifluoacetic acid over 2 mins) retention time 1.149 min, ESI+ found [M+H]=187.9.

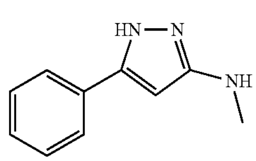

Step 2: N-methyl-5-phenyl-1H-pyrazol-3-amine

To a solution of N-(5-phenyl-1H-pyrazol-3-yl)formamide (2.1 g, 11.2 mmol) in tetrahydrofuran (100 mL) was added borane (1.0 M, 45.0 mL, 45.0 mmol). The mixture was stirred at 0° C. in for 2 h and then quenched by addition of methanol (30 mL) and hydrochloric acid (10%, 5 mL). The resulting mixture was heated at 70° C. for 30 min, and then adjusted to pH=8 by addition of aqueous sodium hydroxide (10%). The mixture was then concentrated to dryness and the residue was taken up in ethyl acetate (100 mL), washed with water (2×50 mL), brine (50 mL), dried over magnesium sulfate and concentration under reduced pressure. The residue was purified by column chromatography (silica gel, 100-200 mesh, 0 to 50% ethyl acetate in petroleum ether) to give N-methyl-5-phenyl-1H-pyrazol-3-amine (1.9 g, 95%) as a white solid: LCMS $R_T$=0.52 min; m/z=173.8 $(M+H)^+$.

LCMS (5 to 95% acetonitrile in water+0.03% trifluoacetic acid over 1.5 mins) retention time 0.52 min, ESI+ found [M+H]=173.8.

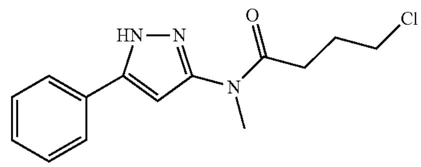 [SMILES: CN(C(=O)CCCCl)c1cc(-c2ccccc2)[nH]n1]

Step 3: 4-chloro-N-methyl-N-(5-phenyl-1H-pyrazol-3-yl)butanamide

A mixture of N-methyl-5-phenyl-1H-pyrazol-3-amine (1.9 g, 11.6 mmol) and 4-chlorobutanoyl chloride (5.2 mL, 46.2 mmol) was stirred at 60° C. for 16 h. The reaction was concentrated under reduce pressure. The residue was taken up in ethyl acetate (300 mL) and washed with water (100 mL) and brine (50 mL), dried over sodium sulfate and concentrated under reduced pressure. The residue was purified by column chromatography (silica gel, 100-200 mesh, 0 to 50% ethyl acetate in petroleum ether) to give 4-chloro-N-methyl-N-(5-phenyl-1H-pyrazol-3-yl)butanamide (2.3 g, 66%) as a white solid, use as is in the next step.

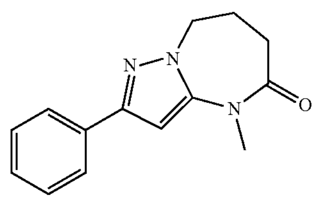 [SMILES: CN1C(=O)CCCn2nc(-c3ccccc3)cc21]

Step 4: 4-methyl-2-phenyl-7,8-dihydro-4H-pyrazolo[1,5-a][1,3]diazepin-5(6H)-one

To a solution of 4-chloro-N-methyl-N-(3-phenyl-1H-pyrazol-5-yl) butanamide (2.1 g, 7.6 mmol) in N,N-dimethylformamide (10 mL) was added cesium carbonate (4.9 g, 15.1 mmol). The mixture was stirred at 25° C. for 16 h and concentrated under reduced pressure. The residue was purified by column chromatography (silica gel, 100-200 mesh, 0 to 50% ethyl acetate in petroleum ether) to give 4-methyl-2-phenyl-7,8-dihydro-4H-pyrazolo[1,5-a][1,3]diazepin-5(6H)-one (1.8 g, 96%) as a white solid: LCMS $R_T$=0.66 min; m/z=241.8 $(M+H)^+$.

LCMS (5 to 95% acetonitrile in water+0.03% trifluoacetic acid over 1.5 mins) retention time 0.66 min, ESI+ found [M+H]=241.8.

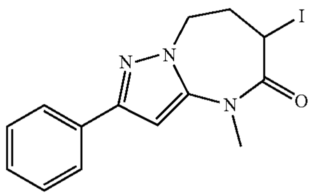 [SMILES: CN1C(=O)C(I)CCn2nc(-c3ccccc3)cc21]

Step 5: 6-iodo-4-methyl-2-phenyl-7,8-dihydro-4H-pyrazolo[1,5-a][1,3]diazepin-5(6H)-one To a solution of 4-methyl-2-phenyl-7,8-dihydro-6H-pyrazolo[1,5-a][1,3]diazepin-5-one (1.6 g, 6.6 mmol) in dry dichloromethane (20 mL) was added $N^1$,$N^1$,$N^3$,$N^3$-tetramethylpropane-1,3-diamine (10.4 g, 79.6 mmol) followed by iodotrimethylsilane (15.9 g, 79.6 mmol) at −15° C. The resulting solution was stirred 2 h at −15° C. and iodine (10 g, 39.80 mmol) was added in one portion. After stirred for 2 h at −15° C., the reaction mixture was quenched by addition of saturated sodium bisulfite (100 mL) and extracted with dichloromethane (3×100 mL). The combined organic extracts were dried over sodium sulfate and concentrated under reduced pressure. The residue was purified by column chromatography (silica gel, 100-200 mesh, silica gel, 100-200 mesh, 0 to 50% ethyl acetate in petroleum ether) to give 6-iodo-4-methyl-2-phenyl-7,8-dihydro-4H-pyrazolo[1,5-a][1,3]diazepin-5(6H)-one (1.3 g, 55.0%) as a white solid: $^1$H NMR (400 MHz, $CDCl_3$) δ 7.78 (d, J=1.6 Hz, 2H), 7.43-7.32 (m, 3H), 6.40 (s, 1H), 4.71-4.67 (m, 1H), 4.34-4.24 (m, 2H), 3.41 (s, 3H), 3.05-2.99 (m, 1H), 2.85-2.82 (m, 1H). LCMS $R_T$=0.71 min; m/z=367.8 $(M+H)^+$.

LCMS (5 to 95% acetonitrile in water+0.03% trifluoacetic acid over 1.5 mins) retention time 0.71 min, ESI+ found [M+H]=367.8.

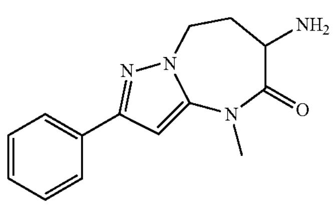 [SMILES: CN1C(=O)C(N)CCn2nc(-c3ccccc3)cc21]

Step 6: 6-amino-4-methyl-2-phenyl-7,8-dihydro-4H-pyrazolo[1,5-a][1,3]diazepin-5(6H)-one A solution of 6-iodo-4-methyl-2-phenyl-7,8-dihydro-4H-pyrazolo[1,5-a][1,3]diazepin-5(6H)-one (550 mg, 1.5 mmol) and ammonia hydroxide (2 mL, 2.25 mmol, 36%) in N,N-dimethylformamide (10 mL) was stirred at 100° C. for 2 h. The reaction was concentrated under reduced pressure and the residue was purified by column chromatography (silica gel, 100-200 mesh, 0 to 3% methanol in dichloromethane) to give 6-amino-4-methyl-2-phenyl-7,8-dihydro-4H-pyrazolo[1,5-a][1,3]diazepin-5(6H)-one (200 mg, 52%) as a white solid: $^1$H NMR (400 MHz, $CDCl_3$) δ 7.76 (d, J=2.0 Hz, 2H), 7.42-7.32 (m, 3H), 6.35 (s, 1H), 4.47-4.42 (m, 1H), 4.17-4.12 (m, 1H), 3.52-3.49 (m, 1H), 3.39 (s, 3H), 2.88-2.82 (m, 1H), 1.95-1.91 (m, 1H).

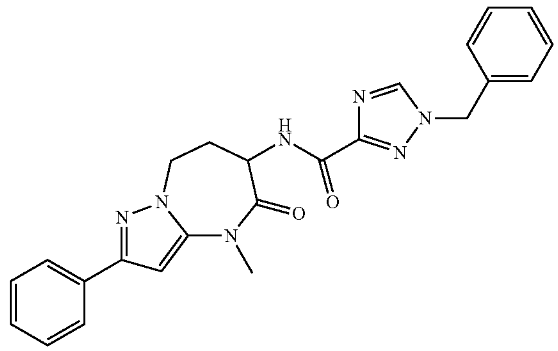 [SMILES: CN1C(=O)C(NC(=O)c2ncn(Cc3ccccc3)n2)CCn2nc(-c3ccccc3)cc21]

Step 7: 1-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide A mixture of 6-amino-4-methyl-2-phenyl-7,8-dihydro-4H-pyrazolo[1,5-a][1,3]diazepin-5(6H)-one (30 mg, 0.12 mmol), 1-benzyl-1,2,4-triazole-3-carboxylic acid (24 mg, 0.12 mmol), 1H-benzo[d][1,2,3]triazol-1-ol (24 mg, 0.18 mmol), N1-((ethylimino)methylene)-N3,N3-dimethylpropane-1,3-diamine hydrochloride (34 mg, 0.18 mmol) and N,N-diisopropylethylamine (30 mg, 0.23 mmol) in N,N-dimethylformamide (10 mL) was stirred at 25° C. for 16 h. The reaction was concentrated under reduced pressure and the residue was purified by RP-HPLC (33% to 63% acetonitrile, 0.05% ammonia hydroxide in water) to give 1-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide (16 mg, 31%) as a white solid: $^1$H NMR (400 MHz, $CD_3OD$) δ 8.57 (s, 1H), 7.82 (d, J=7.2 Hz, 2H), 7.45-7.35 (m, 8H), 6.71 (s, 1H), 5.49 (s, 2H), 4.67-4.32 (m, 3H), 3.42 (s, 3H), 2.97-2.88 (m, 1H), 2.38-2.29 (m, 1H). LCMS $R_T$=0.71 min; m/z=442.0 $(M+H)^+$.

LCMS (5 to 95% acetonitrile in water+0.03% trifluoacetic acid over 1.5 mins) retention time 0.71 min, ESI+ found [M+H]=442.0.

Example 209

WX Method SSSS

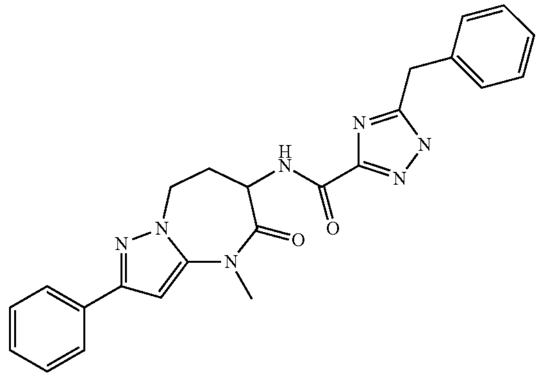 [SMILES: CN1C(=O)C(NC(=O)c2n[nH]c(Cc3ccccc3)n2)CCn2nc(-c3ccccc3)cc21]

5-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide A mixture of 6-amino-4-methyl-2-phenyl-7,8-dihydro-4H-pyrazolo[1,5-a][1,3]diazepin-5(6H)-one (30 mg, 0.12 mmol), 5-benzyl-1H-1,2,4-triazole-3-carboxylic acid (24 mg, 0.12 mmol), 1H-benzo[d][1,2,3]triazol-1-ol (24 mg, 0.18 mmol), N1-((ethylimino)methylene)-N3,N3-dimethylpropane-1,3-diamine hydrochloride (34 mg, 0.18 mmol) and N,N-diisopropylethylamine (45 mg, 0.35 mmol) in N,N-dimethylformamide (10 mL) was stirred at 25° C. for 16 h. The reaction was concentrated under reduced pressure and the residue was purified by RP-HPLC (27% to 57% acetonitrile, 0.05% ammonia hydroxide in water) to give 5-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide (4 mg, 7.3%) as a white solid: $^1H$ NMR (400 MHz, $CD_3OD$) δ 7.82 (d, J=6.8 Hz, 2H), 7.45-7.30 (m, 8H), 6.71 (s, 1H), 4.64-4.34 (m, 3H), 4.17 (s, 2H), 3.42 (s, 3H), 2.93-2.87 (m, 1H), 2.33-2.31 (m, 1H). LCMS $R_T$=0.69 min; m/z=442.0 $(M+H)^+$.

LCMS (5 to 95% acetonitrile in water+0.03% trifluoacetic acid over 1.5 mins) retention time 0.69 min, ESI+ found [M+H]=442.0.

Example 210

WX Method H

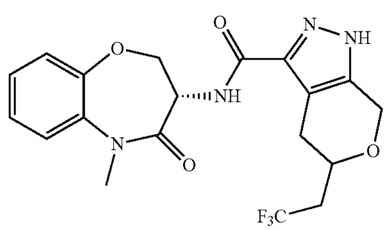 [SMILES: CN1C(=O)[C@@H](NC(=O)c2n[nH]c3c2CC(CC(F)(F)F)OC3)COc2ccccc21]

N—((S)-5-methyl-4-oxo-2,3,4,5-tetrahydrobenzo[b][1,4]oxazepin-3-yl)-5-(2,2,2-trifluoroethyl)-1,4,5,7-tetrahydropyrano[3,4-c]pyrazole-3-carboxamide

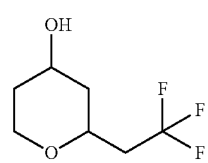 [SMILES: OC1CCOC(CC(F)(F)F)C1]

Step 1:
2-(2,2,2-trifluoroethyl)tetrahydro-2H-pyran-4-ol

To a stirred mixture of 3,3,3-trifluoropropanal (5.0 g, 44.6 mmol) and 3-buten-1-ol (4.8 g, 66.9 mmol) was added 20% sulfuric acid (5 mL) at 0° C. The mixture was stirred at 80° C. for 3 h. After cooled, the mixture was adjusted to pH=9 by slow addition of $NaHCO_3$. The resulting mixture was extracted with ethyl acetate (3×50 mL). The combined organic layers were concentrated under reduced pressure and the residue was purified by column chromatography (silica gel, 100-200 mesh, 0 to 30% ethyl acetate in petroleum ether) to afford the 2-(2,2,2-trifluoroethyl) tetrahydro-2H-pyran-4-ol (1.7 g, 20%) as yellow oil, used in the next step without further purification.

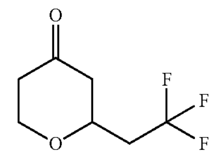 [SMILES: O=C1CCOC(CC(F)(F)F)C1]

Step 2:
2-(2,2,2-trifluoroethyl)dihydro-2H-pyran-4(3H)-one

To a suspension of the 2-(2,2,2-trifluoroethyl)tetrahydro-2H-pyran-4-ol (200 mg, 1.1 mmol) and molecular sieves (4 Å) in dichloromethane (10 mL) was added pyridiniumchlorochromate (281 mg, 1.3 mmol) portionwise over 5 min. The mixture was stirred at 25° C. for 16 h and then filtered. The filtrate was concentrated under reduced pressure affording the crude product, which was purified by column chromatography (silica gel, 100-200 mesh, 10 to 20% ethyl acetate in petroleum ether) to afford 2-(2,2,2-trifluoroethyl)dihydro-2H-pyran-4(3H)-one as colorless oil (136 mg, 64%) as a brown oil, used in the next step without further purification.

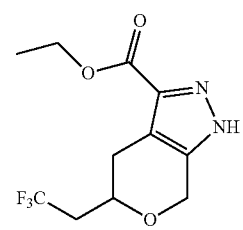 [SMILES: CCOC(=O)c1n[nH]c2c1CC(CC(F)(F)F)OC2]

Step 3: ethyl 5-(2,2,2-trifluoroethyl)-1,4,5,7-tetrahydropyrano[3,4-c]pyrazole-3-carboxylate To a stirred solution of 2-(2,2,2-trifluoroethyl)dihydro-2H-pyran-4(3H)-one (100 mg, 0.55 mmol) in dimethyl sulfoxide (6 mL) was added pyrrolidine (6 mg, 0.08 mmol). The mixture was stirred at 20° C. for 15 min, then ethyl diazoacetate (125 mg, 1.1 mmol) was added. The mixture was stirred at 20° C. for 15 h and then poured into water (20 mL). The mixture was extracted with ethyl acetate (3×50 mL). The combined organic layers were dried over anhydrous sodium sulfate, and concentrated under reduced pressure. The residue was purified by column chromatography (silica gel, 100-200 mesh, 10 to 30% ethyl acetate in petroleum ether) to afford ethyl 5-(2,2,2-trifluoroethyl)-1,4,5,7-tetrahydropyrano[3,4-c]pyrazole-3-carboxylate as a brown solid (50 mg, 31%): LCMS $R_T$=0.796 min; m/z=278.9 $(M+H)^+$.

LCMS (5 to 95% acetonitrile in water+0.03% trifluoacetic acid over 1.5 mins) retention time 0.796 min, ESI+ found [M+H]=278.9.

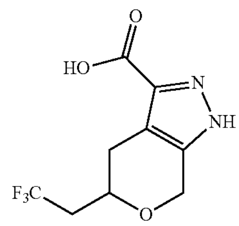 [SMILES: O=C(O)c1n[nH]c2c1CC(CC(F)(F)F)OC2]

Step 4: 5-(2,2,2-trifluoroethyl)-1,4,5,7-tetrahydro pyrano[3,4-c]pyrazole-3-carboxylic acid A mixture of ethyl 5-(2,2,2-trifluoroethyl)-1,4,5,7-tetrahydropyrano[3,4-c]pyrazole-3-carboxylate (50 mg, 0.18 mmol) and potassium hydroxide (20 mg, 0.36 mmol) in ethanol (8 mL) and water (2 mL) was stirred at 25° C. for 24 h. The reaction was concentrated to dryness under reduced pressure and the residue was adjusted to pH=2 by addition of hydrochloric acid (2.0 M). The solvent was removed, and the residue was dissolved in methanol (10 mL). The mixture was filtered and the filtrate was concentrated to dryness under reduced pressure affording 5-(2,2,2-trifluoroethyl)-1,4,5,7-tetrahydropyrano[3,4-c]pyrazole-3-carboxylic acid (40 mg, 88%) as a yellow solid: LCMS $R_T$=0.787 min; m/z=251.1 $(M+H)^+$.

LCMS (10 to 80% acetonitrile in water+0.03% trifluoacetic acid over 2.0 mins) retention time 0.787 min, ESI+ found [M+H]=251.1.

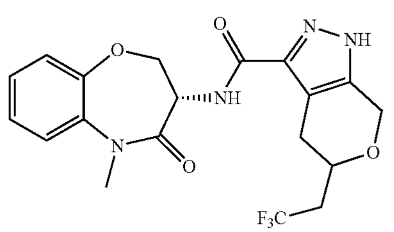 [SMILES: CN1C(=O)[C@@H](NC(=O)c2n[nH]c3c2CC(CC(F)(F)F)OC3)COc2ccccc21]

Step 5: N—((S)-5-methyl-4-oxo-2,3,4,5-tetrahydrobenzo[b][1,4]oxazepin-3-yl)-5-(2,2,2-trifluoroethyl)-1,4,5,7-tetrahydropyrano[3,4-c]pyrazole-3-carboxamide A mixture of $N^1$-((ethylimino)methylene)-$N^3$,$N^3$-dimethylpropane-1,3-diamine hydrochloride (43 mg, 0.24 mmol), 1H-benzo[d][1,2,3]triazol-1-ol (32 mg, 0.24 mmol), (3S)-3-amino-5-methyl-2,3-dihydro-1,5-benzoxazepin-4-one (31 mg, 0.16 mmol), and 5-(2,2,2-trifluoroethyl)-1,4,5,7-tetrahydropyrano[3,4-c]pyrazole-3-carboxylic acid (40 mg, 0.16 mmol) in N,N-dimethylformamide (5 mL) was stirred at 25° C. for 12 h. The reaction was concentrated to dryness under reduced pressure and the residue was purified by RP-HPLC (acetonitrile 46-76%/0.05% $NH_4OH$ in water) to afford N-[(3S)-5-methyl-4-oxo-2,3-dihydro-1,5-benzoxazepin-3-yl]-5-(2,2,2-trifluoroethyl)-1,4,5,7-tetrahydropyrano[3,4-c]pyrazole-3-carboxamide (6.2 mg, 9%) as a yellow solid: $^1H$ NMR (400 MHz, DMSO-$d_6$) δ 13.06 (s, 1H), 8.05-8.02 (m, 1H), 7.49 (d, J=7.2 Hz, 1H), 7.32-7.22 (m, 3H), 4.84 (m, 2H), 4.71-4.54 (m, 1H), 4.43-4.42 (m, 1H), 4.42-4.40 (m, 1H), 3.81 (s, 1H), 3.31 (s. 3H), 2.84-2.80 (m, 1H), 2.67-2.63 (m. 2H), 2.61-2.50 (m, 1H). LCMS $R_T$=1.063 min; m/z=425.2 $(M+H)^+$.

LCMS (10 to 80% acetonitrile in water+0.03% trifluoacetic acid over 2.0 mins) retention time 1.063 min, ESI+ found [M+H]=425.2.

Example 211

WX Method M

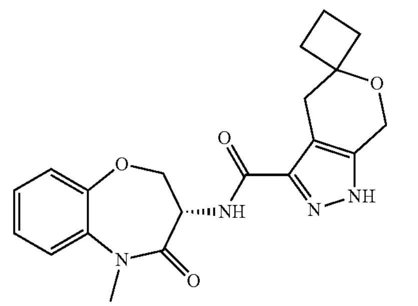 [SMILES: CN1C(=O)[C@@H](NC(=O)c2n[nH]c3c2CC2(CCC2)OC3)COc2ccccc21]

(S)—N-(5-methyl-4-oxo-2,3,4,5-tetrahydrobenzo[b][1,4]oxazepin-3-yl)-4',7'-dihydro-1'H-spiro[cyclobutane-1,5'-pyrano[3,4-c]pyrazole]-3'-carboxamide

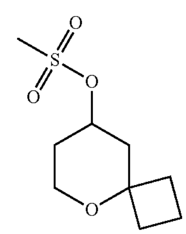

Step 1: 5-oxaspiro[3.5]nonan-8-yl methanesulfonate

To a mixture of cyclobutanone (6.0 g, 85.6 mmol) and 3-buten-1-ol (6.2 g, 85.6 mmol) was added methanesulfonic acid (17.3 g, 179.8 mmol). The mixture was stirred at 25° C. for 15 h and then adjusted to pH=9 by addition of saturated aqueous sodium bicarbonate. The resulting solution was extracted with dichloromethane (4×50 mL). The combined organic layers were dried over sodium sulfate and concentrated under reduced pressure. The residue was purified by column chromatography (silica gel, 100-200 mesh, 10-20% ethyl acetate in petroleum ether) affording 5-oxaspiro[3.5]nonan-8-yl methanesulfonate (17.4 g, 92%) as yellow oil: $^1H$ NMR (400 MHz, $CDCl_3$) δ 4.87-4.80 (m, 1H), 3.84-3.78 (m, 1H), 3.51-3.44 (m, 1H), 3.02 (s, 3H), 2.27-2.22 (m, 1H), 2.19-2.11 (m, 1H), 2.04-1.98 (m, 4H), 1.82-1.65 (m, 4H).

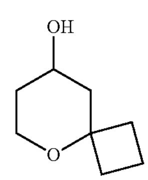

Step 2: 5-oxaspiro[3.5]nonan-8-ol

To a solution of 5-oxaspiro[3.5]nonan-8-yl methanesulfonate (22.0 g, 100 mmol) in tetrahydrofuran (180 mL) was added methylmagnesiumbromide (3.0 M, 50 mL, 150 mmol) at 0° C. After addition, the mixture was stirred at 25° C. for 20 h and then quenched by addition of saturated aqueous ammonium chloride (10 mL). The resulting mixture was extracted with ethyl acetate (5×50 mL). The combined organic layers were dried over sodium sulfate and concentrated under reduced pressure. The residue was purified by column chromatography (silica gel, 100-200 mesh, 20 to 30% ethyl acetate in petroleum ether) affording 5-oxaspiro[3.5]nonan-8-ol (12.9 g, 90%) as colorless oil: $^1$H NMR (400 MHz, $CDCl_3$) δ 3.84-3.75 (m, 2H), 3.45-3.38 (m, 1H), 2.19-2.10 (m, 2H), 2.00-1.90 (m, 4H), 1.85-1.73 (m, 2H), 1.70-1.58 (m, 1H), 1.52-1.35 (m, 2H).

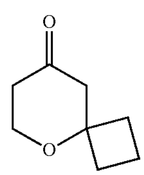

Step 3: 5-oxaspiro[3.5]nonan-8-ol

To a solution of 5-oxaspiro[3.5]nonan-8-ol (12.9 g, 90.5 mmol) in dichloromethane (240 mL) was added pyridiniumchlorochromate (23.4 g, 108.6 mmol) portionwise over 5 min. The reaction was stirred for 16 h at 25° C. and then filtered. The filtrate was concentrated under reduced pressure. The residue was purified by column chromatography (silica gel, 100-200 mesh, 0 to 20% ethyl acetate in petroleum ether) affording 5-oxaspiro[3.5]nonan-8-one (11.5 g, 91%) as colorless oil: $^1$H NMR (400 MHz, $CDCl_3$) δ 3.87-3.84 (m, 2H), 2.54 (s, 2H), 2.39-2.36 (m, 2H), 2.17-2.09 (m, 2H), 1.98-1.92 (m, 2H), 1.82-1.74 (m, 1H), 1.67-1.55 (m, 1H).

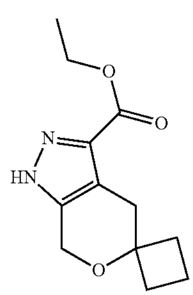 [SMILES: CCOC(=O)c1n[nH]c2c1CC1(CCC1)OC2]

Step 4: ethyl 4',7'-dihydro-1'H-spiro[cyclobutane-1,5'-pyrano[3,4-c]pyrazole]-3'-carboxylate To a stirred solution of 5-oxaspiro[3.5]nonan-8-one (4.9 g, 35.1 mmol) in dimethyl sulfoxide (40 mL) was added pyrrolidine (120 mg, 1.8 mmol), followed by ethyl diazoacetate (2.0 g, 17.5 mmol). The mixture was stirred at 25° C. for 15 h and then poured into water (60 mL). The resulting mixture was extracted with ethyl acetate (3×50 mL). The combined organic layers were dried over sodium sulfate and concentrated under reduced pressure. The residue was purified by column chromatography (silica gel, 100-200 mesh, 0 to 30% ethyl acetate in petroleum ether) to afford ethyl 4',7'-dihydro-1'H-spiro[cyclobutane-1,5'-pyrano[3,4-c]pyrazole]-3'-carboxylate (0.80 g, 19%) as brown oil. $^1$H NMR (400 MHz, $CDCl_3$) δ 4.79 (s, 2H), 4.43-4.38 (m, 2H), 2.96 (s, 2H), 2.29-2.21 (m, 2H), 1.95-1.84 (m, 3H), 1.81-1.69 (m, 1H), 1.43-1.40 (m, 3H).

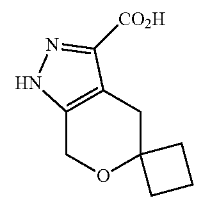 [SMILES: O=C(O)c1n[nH]c2c1CC1(CCC1)OC2]

Step 5: 4',7'-dihydro-1'H-spiro[cyclobutane-1,5'-pyrano[3,4-c]pyrazole]-3'-carboxylic acid A mixture of ethyl 4',7'-dihydro-1'H-spiro[cyclobutane-1,5'-pyrano[3,4-c]pyrazole]-3'-carboxylate (50 mg, 0.21 mmol) and lithium hydroxide hydrate (76 mg, 3.2 mmol)) in tetrahydrofuran (4 mL) and water (1 mL) was stirred for 20 h at 25° C. The organic solvent was removed under reduced pressure, and the aqueous layer was adjusted to pH=3 by addition of hydrochloric acid (1.0 M). The solution was concentrated under reduced pressure to afford crude 4',7'-dihydro-1'H-spiro[cyclobutane-1,5'-pyrano[3,4-c]pyrazole]-3'-carboxylic acid (49 mg, 100%) as a white solid: LCMS $R_T$=0.539 min; m/z=208.8 $(M+H)^+$.

LCMS (5 to 95% acetonitrile in water+0.03% trifluoacetic acid over 1.5 mins) retention time 0.539 min, ESI+ found [M+H]=208.8.

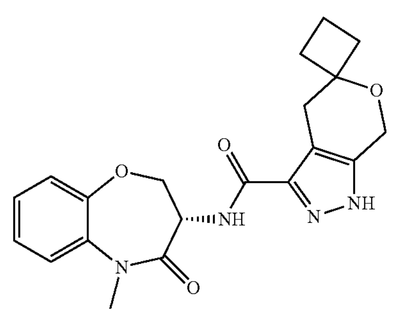 [SMILES: CN1C(=O)[C@@H](NC(=O)c2n[nH]c3c2CC2(CCC2)OC3)COc2ccccc21]

Step 6: (S)—N-(5-methyl-4-oxo-2,3,4,5-tetrahydrobenzo[b][1,4]oxazepin-3-yl)-4',7'-dihydro-1'H-spiro[cyclobutane-1,5'-pyrano[3,4-c]pyrazole]-3'-carboxamide A mixture of (3S)-3-amino-5-methyl-2,3-dihydro-1,5-benzoxazepin-4-one (30 mg, 0.16 mmol), 1H-benzo[d][1,2,3]triazol-1-ol (31 mg, 0.23 mmol), 4',7'-dihydro-1'H-spiro[cyclobutane-1,5'-pyrano[3,4-c]pyrazole]-3'-carboxylic acid (49 mg, 0.23 mmol) and $N^1$-((ethylimino)methylene)-$N^3$,$N^3$-dimethylpropane-1,3-diamine hydrochloride (44 mg, 0.23 mmol) in N,N-dimethylformamide (5 mL) was stirred at 25° C. for 1 h. The solvent was evaporated under reduced pressure and the residue was purified by RP-HPLC (acetonitrile 30-60%/0.05% ammonium hydroxide in water) affording (S)—N-(5-methyl-4-oxo-2,3,4,5-tetrahydrobenzo[b][1,4]oxazepin-3-yl)-4',7'-dihydro-1 $^1$H-spiro[cyclobutane-1,5'-pyrano[3,4-c]pyrazole]-3'-carboxamide (16.9 mg, 27%) as a white solid: $^1$H NMR (400 MHz, DMSO-$d_6$) δ 12.99 (s, 1H), 8.02 (d, J=8.0 Hz, 1H), 7.50-7.48 (m, 1H), 7.35-7.27 (m, 2H), 7.25-7.22 (m, 1H), 4.87-4.80 (m, 1H), 4.65 (s, 2H), 4.55-4.50 (m, 1H), 4.43-4.39 (m, 1H), 3.32 (s, 3H), 2.74 (s, 2H), 2.12-2.05 (m, 2H), 1.79-1.64 (m, 4H). LCMS $R_T$=1.021 min; m/z=383.2 $(M+H)^+$.

LCMS (10 to 80% acetonitrile in water+0.03% trifluoacetic acid over 2 mins) retention time 1.021 min, ESI+ found $[M+H]^+$=383.2.

Example 212

WX Method DDDDDD

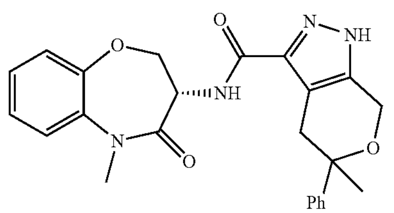 [SMILES: CN1C(=O)[C@@H](NC(=O)c2n[nH]c3c2CC(C)(c2ccccc2)OC3)COc2ccccc21]

5-methyl-N—((S)-5-methyl-4-oxo-2,3,4,5-tetrahydrobenzo[b][1,4]oxazepin-3-yl)-5-phenyl-1,4,5,7-tetrahydropyrano[3,4-c]pyrazole-3-carboxamide A mixture of 5-methyl-5-phenyl-4,7-dihydro-1H-pyrano[3,4-c]pyrazole-3-carboxylic acid (42 mg, 0.16 mmol), (3S)-3-amino-5-methyl-2,3-dihydro-1,5-benzoxazepin-4-one (31 mg, 0.16 mmol), 1H-benzo[d][1,2,3]triazol-1-ol (44 mg, 0.33 mmol). Then $N^1$-((ethylimino)methylene)-$N^3$,$N^3$-dimethylpropane-1,3-diamine hydrochloride (62 mg, 0.33 mmol) in N,N-dimethylformamide (5 mL) was stirred at 25° C. for 12 h. The reaction was concentrated under reduced pressure and the residue was purified by RP-HPLC (acetonitrile 48-78 with 0.05% formic acid in water) to afford 5-methyl-N—((S)-5-methyl-4-oxo-2,3,4,5-tetrahydrobenzo[b][1,4]oxazepin-3-yl)-5-phenyl-1,4,5,7-tetrahydropyrano[3,4-c]pyrazole-3-carboxamide (25 mg, 36%) as a white solid: $^1$H NMR (400 MHz, $CD_3OD$) δ 7.42-7.23 (m, 9H), 5.05-5.00 (m, 1H), 4.73-4.69 (m, 1H), 4.61-4.59 (m, 1H), 4.39-4.35 (m, 2H), 3.53-3.48 (m, 1H), 3.40 (s, 3H), 2.96-2.91 (m, 1H), 1.51 (s, 3H). LCMS $R_T$=3.37 min; m/z=433.4 $(M+H)^+$.

LCMS (10 to 80% acetonitrile in water+0.1% formic acid over 7.0 mins) retention time 3.37 min, ESI+ found [M+H]=433.4.

Example 213

WX Method JJ

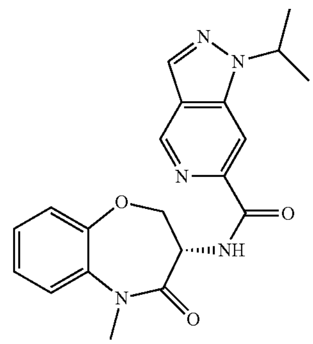 [SMILES: CC(C)n1ncc2cnc(C(=O)N[C@H]3COc4ccccc4N(C)C3=O)cc21]

(S)-1-isopropyl-N-(5-methyl-4-oxo-2,3,4,5-tetrahydrobenzo[b][1,4]oxazepin-3-yl)-1H-pyrazolo[4,3-c]pyridine-6-carboxamide

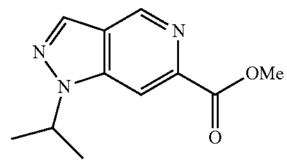

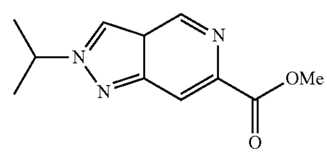

Step 1: Methyl 1-isopropylpyrazolo[4,3-c]pyridine-6-carboxylate

To a solution of methyl 1H-pyrazolo[4,3-c]pyridine-6-carboxylate (300 mg, 1.69 mmol) in N,N-dimethylformamide (5 mL) was added potassium carbonate (702 mg, 5.08 mmol) and 2-iodopropane (576 mg, 3.39 mmol). The reaction mixture was stirred at 45° C. for 3 h and then concentrated under reduced pressure. The residue was purified by RP-HPLC (acetonitrile 12-42/0.05% ammonia in water) to give:

Methyl 1-isopropylpyrazolo[4,3-c]pyridine-6-carboxylate (150 mg, 40.4%) as a white solid: $^1$H NMR (400 MHz, DMSO-$d_6$) δ 9.16 (s, 1H), 8.48-8.43 (m, 2H), 5.27-5.16 (m, 1H), 3.91 (s, 3H), 1.49 (d, J=6.4 Hz, 6H).

Methyl 2-isopropylpyrazolo[4,3-c]pyridine-6-carboxylate (70 mg, 19%) as a white solid: $^1$H NMR (400 MHz, DMSO-$d_6$) δ 9.22 (d, J=1.2 Hz, 1H), 8.86 (s, 1H), 8.30 (s, 1H), 5.02-4.91 (m, 1H), 3.88 (s, 3H), 1.58 (d, J=6.8 Hz, 6H).

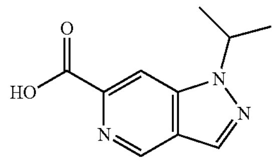

Step 2: 1-isopropylpyrazolo[4,3-c]pyridine-6-carboxylic acid

A mixture of methyl 1-isopropylpyrazolo[4,3-c]pyridine-6-carboxylate (50 mg, 0.23 mmol) and lithium hydroxide hydrate (27 mg, 1.14 mmol) in tetrahydrofuran (5 mL) and water (2 mL) was stirred at 25° C. for 18 h. The organic solvent was removed under reduced pressure and the aqueous residue was adjusted to pH=5 by addition of hydrochloric acid (1.0 M). The mixture was concentrated under reduced pressure affording 1-isopropylpyrazolo[4,3-c]pyridine-6-carboxylic acid (40 mg, 85%) as a white solid, used in the next step without further purification.

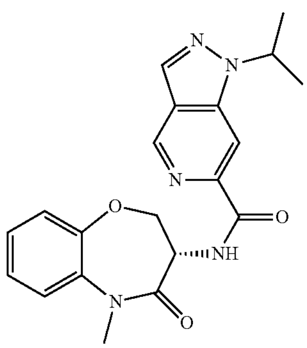 [SMILES: CC(C)n1ncc2cnc(C(=O)N[C@H]3COc4ccccc4N(C)C3=O)cc21]

Step 3: (S)-1-isopropyl-N-(5-methyl-4-oxo-2,3,4,5-tetrahydrobenzo[b][1,4]oxazepin-3-yl)-1H-pyrazolo[4,3-c]pyridine-6-carboxamide A mixture of 1-isopropylpyrazolo[4,3-c]pyridine-6-carboxylic acid (40 mg, 0.19 mmol), (3S)-3-amino-5-methyl-2,3-dihydro-1,5-benzoxazepin-4-one (41 mg, 0.21 mmol), 1H-benzo[d][1,2,3]triazol-1-ol (32 mg, 0.23 mmol) and $N^1$-((ethylimino)methylene)-$N^3$,$N^3$-dimethylpropane-1,3-diamine hydrochloride (45 mg, 0.23 mmol) in N,N-dimethylformamide (5 mL) was stirred at 25° C. for 1 h. The reaction was concentrated under reduced pressure and the residue was purified by RP-HPLC (acetonitrile 36-66%/0.05% ammonia in water) affording (S)-1-isopropyl-N-(5-methyl-4-oxo-2,3,4,5-tetrahydrobenzo[b][1,4]oxazepin-3-yl)-1H-pyrazolo[4,3-c]pyridine-6-carboxamide (32.7 mg, 43%) as a white solid: $^1$H NMR (400 MHz, DMSO-$d_6$) δ 9.17 (s, 1H), 9.02 (d, J=8.0 Hz, 1H), 8.44 (s, 1H), 8.30 (s, 1H), 7.53-7.47 (m, 1H), 7.37-7.24 (m, 3H), 5.23-5.11 (m, 1H), 4.97-4.87 (m, 1H), 4.89-4.49 (m, 2H), 3.34 (s, 3H), 1.52-1.41 (m, 6H). LCMS $R_T$=0.834 min; m/z=380.0 $(M+H)^+$.

LCMS (5 to 95% acetonitrile in water+0.03% trifluoacetic acid over 1.5 mins) retention time 0.834 min, ESI+ found [M+H]=380.0.

Example 214 is omitted.

Example 215

WX Method MMMMMM

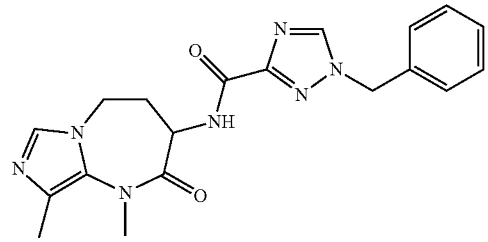 [SMILES: Cc1ncn2c1N(C)C(=O)C(NC(=O)c1ncn(Cc3ccccc3)n1)CC2]

1-benzyl-N-(1,9-dimethyl-2-oxo-2,3,4,5-tetrahydro-1H-imidazo[1,5-a][1,3]diazepin-3-yl)-1H-1,2,4-triazole-3-carboxamide

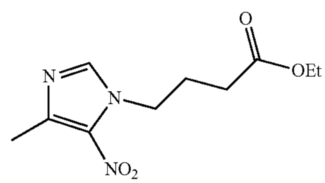

Step 1: ethyl 4-(4-methyl-5-nitro-1H-imidazol-1-yl)butanoate

A mixture of 5-methyl-4-nitro-1H-imidazole (58.0 g, 456.0 mmol), ethyl 4-bromobutyrate (107.0 g, 548.0 mmol) and potassium carbonate (75.7 g, 548.0 mmol) in N,N-dimethylformamide (250 mL) was stirred at 120° C. for 2 h. The mixture was diluted with water (200 mL) and extracted with ethyl acetate (3×300 mL). The combined organics were washed with brine (2×50 mL), dried over sodium sulfate concentrated under reduced pressure. The residue was purified by column chromatography (silica gel, 100-200 mesh, 0 to 30% ethyl acetate in petroleum ether) to afford ethyl 4-(4-methyl-5-nitro-1H-imidazol-1-yl)butanoate (33.6 g, 30%) as a yellow oil, used in the next step as is.

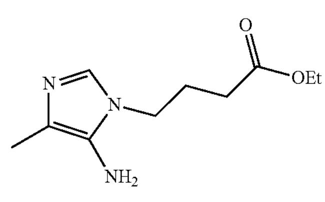

Step 2: ethyl 4-(5-amino-4-methyl-1H-imidazol-1-yl)butanoate

A mixture of ethyl 4-(4-methyl-5-nitro-1H-imidazol-1-yl) butanoate (33.6 g, 139.0 mmol) and 10% palladium on carbon (11.9 g, 11.2 mmol) in 1,4-dioxane (1.5 L) was hydrogenated (50 psi) at 25° C. for 24 h. The reaction was filtered and the filtrate was concentrated under reduced pressure to afford ethyl 4-(5-amino-4-methyl-1H-imidazol-1-yl)butanoate (33.4 g, 79%) as a black oil. LCMS $R_T$=1.366 min; m/z=212.2 $(M+H)^+$.

LCMS (0 to 60% acetonitrile in water+0.05% ammonium bicarbonate over 3.0 mins) retention time 1.366 min, ESI+ found [M+H]=212.2.

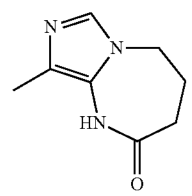

Step 3: 9-methyl-4,5-dihydro-1H-imidazo[1,5-a][1,3]diazepin-2(3H)-one

A mixture of ethyl 4-(5-amino-4-methyl-1H-imidazol-1-yl)butanoate (30.0 g, 142.0 mmol) and sodium ethoxide (48.3 g, 710.0 mmol) in ethanol (200 mL) was stirred at 25° C. for 4 h. The reaction mixture was concentrated under reduced pressure and the residue was purified by column chromatography (silica gel, 100-200 mesh, 0 to 10% methanol in dichloromethane) to afford 9-methyl-4,5-dihydro-1H-imidazo[1,5-a][1,3]diazepin-2(3H)-one (8.0 g, 34%) as a yellow oil, used as is in the next step.

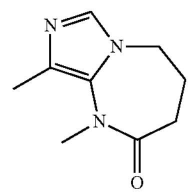

Step 4: 1,9-dimethyl-4,5-dihydro-1H-imidazo[1,5-a][1,3]diazepin-2(3H)-one

To a solution of 9-methyl-4,5-dihydro-1H-imidazo[1,5-a][1,3]diazepin-2(3H)-one (2.0 g, 12.1 mmol) and cesium carbonate (3.9 g, 12.1 mmol) in N,N-dimethylformamide (30 mL) was added methyl iodide (1.72 g, 12.1 mmol). The reaction mixture was stirred at 25° C. for 3 h and then concentrated under reduced pressure. The residue was purified by column chromatography (silica gel, 100-200 mesh, 0 to 10% methanol in dichloromethane) to afford 1,9-dimethyl-4,5-dihydro-1H-imidazo[1,5-a][1,3]diazepin-2(3H)-one (1.0 g, 46%) as a white solid, used as is in the next step.

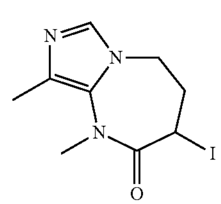

Step 5: 3-iodo-1,9-dimethyl-4,5-dihydro-1H-imidazo[1,5-a][1,3]diazepin-2(3H)-one To a solution of 1,9-dimethyl-4,5-dihydro-1H-imidazo[1,5-a][1,3]diazepin-2(3H)-one (100 mg, 0.56 mmol) in dichloromethane (10 mL) was added $N^1,N^1,N^2,N^2$-tetramethylethane-1,2-diamine (872 mg, 6.7 mmol) and iodotrimethylsilane (1.3 g, 6.7 mmol) at −15° C. The mixture was stirred at −15° C. for 1.5 h and then iodine (849 mg, 3.35 mmol) was added in one portion. The reaction mixture was stirred at 30° C. for 2 h and concentrated under reduced pressure. The residue was purified by column chromatography (silica gel, 100-200 mesh, 0 to 10% methanol in dichloromethane) to afford 3-iodo-1,9-dimethyl-4,5-dihydro-1H-imidazo[1,5-a][1,3]diazepin-2(3H)-one (120 mg, 71%) as a light yellow solid. LCMS $R_T$=1.44 min; m/z=306.0 $(M+H)^+$.

LCMS (0 to 60% acetonitrile in water+0.1% ammonium bicarbonate over 3 mins) retention time 1.44 min, ESI+ found [M+H]=306.0.

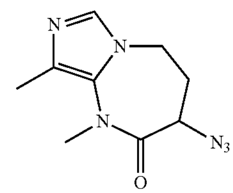 [SMILES: Cc1ncn2c1N(C)C(=O)C(N=[N+]=[N-])CC2]

Step 6: 3-azido-1,9-dimethyl-4,5-dihydro-1H-imidazo[1,5-a][1,3]diazepin-2(3H)-one To a solution of 3-iodo-1,9-dimethyl-4,5-dihydro-1H-imidazo[1,5-a][1,3]diazepin-2(3H)-one (120 mg, 0.39 mmol) in N,N-dimethylformamide (5 mL) was added sodium azide (35 mg, 0.53 mmol). The reaction mixture was stirred at 25° C. for 2 h and diluted with ice water (5 mL). The solution was extracted with ethyl acetate (3×10 mL). The combined organic layers were concentrated under reduced pressure. The residue was purified by column chromatography (silica gel, 100-200 mesh, 0 to 10% methanol in dichloromethane) to afford 3-azido-1,9-dimethyl-4,5-dihydro-1H-imidazo[1,5-a][1,3]diazepin-2(3H)-one (80 mg, 92%) as a yellow solid. LCMS $R_T$=1.29 min; m/z=221.1 $(M+H)^+$.

LCMS (0 to 60% acetonitrile in water+0.03% ammonium bicarbonate over 3 mins) retention time 1.29 min, ESI+ found [M+H]=221.1

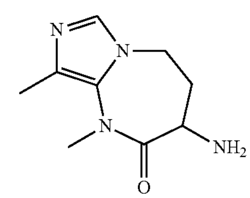

Step 7: 3-amino-1,9-dimethyl-4,5-dihydro-1H-imidazo[1,5-a][1,3]diazepin-2(3H)-one A mixture of 3-azido-1,9-dimethyl-4,5-dihydro-1H-imidazo[1,5-a][1,3]diazepin-2(3H)-one (80 mg, 0.36 mmol) and 10% palladium on carbon (386 mg, 0.36 mmol) in methanol (20 mL) was hydrogenated (15 psi) at 25° C. for 2 h. The reaction mixture was filtered and the filtrate was concentrated under reduced pressure to afford 3-amino-1,9-dimethyl-4,5-dihydro-1H-imidazo[1,5-a][1,3]diazepin-2(3H)-one (60 mg, 85%) as a yellow oil, used in the next step without further purification.

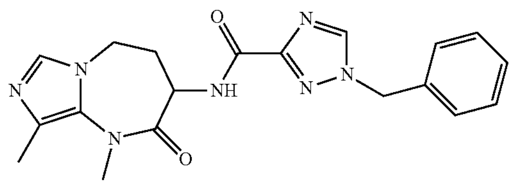 [SMILES: Cc1ncn2c1N(C)C(=O)C(NC(=O)c1ncn(Cc3ccccc3)n1)CC2]

Step 8: 1-benzyl-N-(1,9-dimethyl-2-oxo-2,3,4,5-tetrahydro-1H-imidazo[1,5-a][1,3]diazepin-3-yl)-1H-1,2,4-triazole-3-carboxamide A mixture of 1-benzyl-1,2,4-triazole-3-carboxylic acid (20 mg, 0.1 mmol), 3-amino-1,9-dimethyl-4,5-dihydro-1H-imidazo[1,5-a][1,3]diazepin-2(3H)-one (19 mg, 0.1 mmol), $N^1$-((ethylimino)methylene)-$N^3$,$N^3$-dimethylpropane-1,3-diamine hydrochloride (24 mg, 0.12 mmol) and 1H-benzo[d][1,2,3]triazol-1-ol (18 mg, 0.12 mmol) in N,N-dimethylformamide (5 mL) was stirred at 30° C. for 1 h. The reaction mixture was concentrated under reduced pressure and the residue was purified by RP-HPLC (acetonitrile 10-40/0.05% ammonia hydroxide in water) to afford 1-benzyl-N-(1,9-dimethyl-2-oxo-2,3,4,5-tetrahydro-1H-imidazo[1,5-a][1,3]diazepin-3-yl)-1H-1,2,4-triazole-3-carboxamide (7.2 mg, 19%) as a white solid: $^1$H NMR (400 MHz, $CD_3OD$) δ 8.57 (s, 1H), 7.55 (s, 1H), 7.41-7.33 (m, 5H), 5.47 (s, 2H), 4.87-4.54 (m, 1H), 4.36-4.31 (m, 1H), 3.98-3.91 (m, 1H), 3.35 (s, 3H), 2.75-2.63 (m, 1H), 2.22 (s, 3H), 2.15-2.07 (m, 1H). LCMS $R_T$=0.91 min; m/z=380.3 $(M+H)^+$.

LCMS (0 to 60% acetonitrile in water+0.03% trifluoacetic acid over 2 mins) retention time 0.91 min, ESI+ found [M+H]=380.3.

Example 216

WX Method TTTT

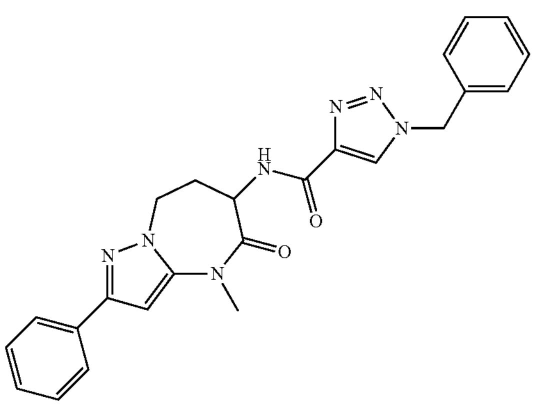 [SMILES: CN1C(=O)C(NC(=O)c2cn(Cc3ccccc3)nn2)CCn2nc(-c3ccccc3)cc21]

1-benzyl-N-(4-methyl-5-oxo-2-phenyl-5,6,7,8-tetrahydro-4H-pyrazolo[1,5-a][1,3]diazepin-6-yl)-1H-1,2,3-triazole-4-carboxamide A mixture of 6-amino-4-methyl-2-phenyl-7,8-dihydro-4H-pyrazolo[1,5-a][1,3]diazepin-5(6H)-one (30 mg, 0.12 mmol), 1-benzyltriazole-4-carboxylic acid (24 mg, 0.12 mmol), 1H-benzo[d][1,2,3]triazol-1-ol (24 mg, 0.18 mmol), N1-((ethylimino)methylene)-N3,N3-dimethylpropane-1,3-diamine hydrochloride (34 mg, 0.18 mmol) and N,N-diisopropylethylamine (45 mg, 0.35 mmol) in N,N-dimethylformamide (10 mL) was stirred at 25° C. for 16 h. The reaction was concentrated under reduced pressure and the residue was purified by RP-HPLC (35% to 65% acetonitrile, 0.05% ammonia hydroxide in water) to give 1-benzyl-N-(4-methyl-5-oxo-2-phenyl-5,6,7,8-tetrahydro-4H-pyrazolo[1,5-a][1,3]diazepin-6-yl)-1H-1,2,3-triazole-4-carboxamide (8 mg, 16%) as a white solid: $^1$H NMR (400 MHz, $CDCl_3$) δ 7.95-7.92 (m, 2H), 7.76 (d, J=7.2, 2 H), 7.44-7.28 (m, 8H), 6.41 (s, 1H), 5.58 (s, 2H), 4.81-4.76 (m, 1H), 4.55-4.49 (m, 1H), 4.25-4.20 (m, 1H), 3.42 (s, 3H), 3.16-3.09 (m, 1H), 2.16-2.08 (m, 1H). LCMS $R_T$=0.72 min; m/z=442.0 $(M+H)^+$.

LCMS (5 to 95% acetonitrile in water+0.03% trifluoacetic acid over 1.5 mins) retention time 0.72 min, ESI+ found [M+H]=442.0.

Example 217

WX Method CC

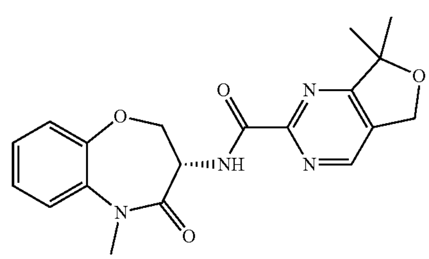 [SMILES: CN1C(=O)[C@@H](NC(=O)c2ncc3c(n2)C(C)(C)OC3)COc2ccccc21]

(S)-7,7-dimethyl-N-(5-methyl-4-oxo-2,3,4,5-tetrahydrobenzo[b][1,4]oxazepin-3-yl)-5,7-dihydrofuro[3,4-d]pyrimidine-2-carboxamide

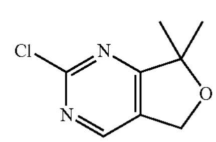

Step 1: 2-chloro-7,7-dimethyl-5H-furo[3,4-d]pyrimidine

A mixture of 2,4-dichloro-7,7-dimethyl-5H-furo[3,4-d]pyrimidine (500 mg, 2.28 mmol) and zinc (448 mg, 6.85 mmol) in water (10 mL) was heated at reflux for 3 h. After cooled, the reaction mixture was extracted with dichloromethane (3×15 mL). The combined organic layers were washed water (3×15 mL), dried over sodium sulfate and concentrated under reduced pressure. The residue was purified by column chromatography (silica gel, 100-200 mesh, 0 to 10% ethyl acetate in petroleum ether) to afford 2-chloro-7,7-dimethyl-5H-furo[3,4-d]pyrimidine (150 mg, 36%) as a white solid: LCMS $R_T$=1.54 min; m/z=185.1 $(M+H)^+$.

LCMS (5-95% acetonitrile in water+0.05% ammonium bicarbonate over 1.5 mins) retention time 1.54/min, ESI+ found [M+H]=185.1.

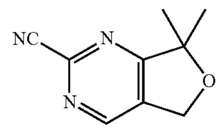

Step 2: 7,7-dimethyl-5H-furo[3,4-d]pyrimidine-2-carbonitrile

A mixture of 2-chloro-7,7-dimethyl-5H-furo[3,4-d]pyrimidine (150 mg, 0.81 mmol), 1,4-diazabicyclo[2.2.2]octane (18 mg, 0.16 mmol) and sodium cyanide (40 mg, 0.81 mmol) in dimethyl sulfoxide (8 mL) and water (8 mL) was added stirred at 25° C. for 12 h. The reaction mixture was diluted with dichloromethane (30 mL) and washed with water (3×30 mL). The organic layer was dried over sodium sulfate and concentrated under reduced pressure. The residue was purified by column chromatography (silica gel, 100-200 mesh, 0 to 30% ethyl acetate in petroleum ether) to afford 7,7-dimethyl-5H-furo[3,4-d]pyrimidine-2-carbonitrile (80 mg, 56%) as a white solid: LCMS $R_T$=0.54 min; m z=175.9 $(M+H)^+$.

LCMS (5-95% acetonitrile in water+0.05% trifluoacetic acid over 1.5 mins) retention time 0.54/min, ESI+ found [M+H]=175.9.

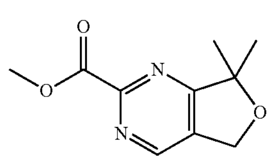

Step 3: methyl 7,7-dimethyl-5H-furo[3,4-d]pyrimidine-2-carboxylate

A solution of 7,7-dimethyl-5H-furo[3,4-d]pyrimidine-2-carbonitrile (80 mg, 0.46 mmol) in methanol (2 mL) was added acetyl chloride (72 mg, 0.91 mmol) at 0° C. The resulting mixture was stirred at 25° C. for 12 h and then concentrated under reduced pressure. The residue was purified by preparative TLC (50% ethyl acetate in petroleum ether, Rf=0.4) to afford methyl 7,7-dimethyl-5H-furo[3,4-d]pyrimidine-2-carboxylate (12 mg, 13%) as yellow oil: LCMS $R_T$=0.65 min; m/z=209.1 $(M+H)^+$.

LCMS (10-80% acetonitrile in water+0.05% ammonium bicarbonate over 3 mins) retention time 0.65/min, ESI+ found [M+H]=209.1.

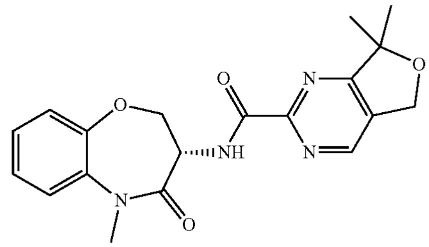 [SMILES: CN1C(=O)[C@@H](NC(=O)c2ncc3c(n2)C(C)(C)OC3)COc2ccccc21]

Step 4: (S)-7,7-dimethyl-N-(5-methyl-4-oxo-2,3,4,5-tetrahydrobenzo[b][1,4]oxazepin-3-yl)-5,7-dihydrofuro[3,4-d]pyrimidine-2-carboxamide To a solution of methyl 7,7-dimethyl-5H-furo[3,4-d]pyrimidine-2-carboxylate (12 mg, 0.06 mmol) and (3S)-3-amino-5-methyl-2,3-dihydro-1,5-benzoxazepin-4-one (12 mg, 0.06 mmol) in tetrahydrofuran (4 mL) was added trimethylaluminum (2.0 M, 0.17 mL, 0.35 mmol). The mixture was stirred at 25° C. for 12 h and then quenched by addition of saturated aqueous ammonium chloride. The reaction mixture was filtered and the filtrate was concentrated under reduced pressure. The residue was purified by RP-HPLC (acetonitrile 27-57/0.05% ammonia hydroxide in water) to afford (S)-7,7-dimethyl-N-(5-methyl-4-oxo-2,3,4,5-tetrahydrobenzo[b][1,4]oxazepin-3-yl)-5,7-dihydrofuro[3,4-d]pyrimidine-2-carboxamide (4 mg, 19%) as a white solid: $^1H$ NMR (400 MHz, $CD_3OD$) δ 8.36 (s, 1H), 7.47-7.45 (m, 1H), 7.35-7.32 (m, 2H), 7.28-7.27 (m, 1H), 5.16 (s, 2H), 5.06-5.04 (m, 1H), 4.69-4.68 (m, 1H), 4.52-4.47 (m, 1H), 3.45 (s, 3H), 1.54 (s, 6H). LCMS $R_T$=1.53 min; m/z=369.1 $(M+H)^+$.

LCMS (10-80% acetonitrile in water+0.05% ammonium bicarbonate over 3 mins) retention time 1.53/min, ESI+ found [M+H]=369.1.

Example 218

WX Method P

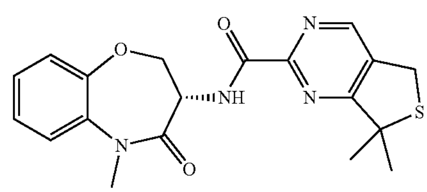 [SMILES: CN1C(=O)[C@@H](NC(=O)c2ncc3c(n2)C(C)(C)SC3)COc2ccccc21]

(S)-7,7-dimethyl-N-(5-methyl-4-oxo-2,3,4,5-tetrahydrobenzo[b][1,4]oxazepin-3-yl)-5,7-dihydrothieno[3,4-d]pyrimidine-2-carboxamide

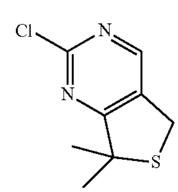

Step 1: 2-chloro-7,7-dimethyl-5,7-dihydrothieno[3,4-d]pyrimidine

A mixture of 2,4-dichloro-7,7-dimethyl-5H-thieno[3,4-d]pyrimidine (1.0 g, 4.3 mmol) and zinc (0.8 g, 12.8 mmol) in water (20 mL) was heated at 100° C. for 12 h. After cooled, the mixture was extracted with ethyl acetate (3×25 mL). The combined organic layers were washed with brine (10 mL), dried over sodium sulfate and concentrated under reduced pressure. The residue was purified by column chromatography (silica gel, 100-200 mesh, 0 to 15% ethyl acetate in petroleum ether) to afford 2-chloro-7,7-dimethyl-5,7-dihydrothieno[3,4-d]pyrimidine (400 mg, 47%) as a white solid: $^{1}H$ NMR (400 MHz, METHANOL-$d_4$) δ 8.60 (s, 1H), 4.18 (s, 2H), 1.69 (s, 6H).

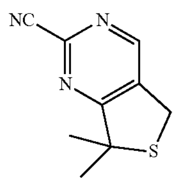

Step 2: 7,7-dimethyl-5,7-dihydrothieno[3,4-d]pyrimidine-2-carbonitrile

To a solution of 2-chloro-7,7-dimethyl-5H-thieno[3,4-d]pyrimidine (250 mg, 1.25 mmol) in dimethyl sulfoxide (10 mL) and water (10 mL) was added sodium cyanide (122 mg, 2.49 mmol) and 1,4-diazabicyclo[2.2.2]octane (28 mg, 0.25 mmol). The reaction mixture was stirred at 30° C. for 12 h and then diluted with ethyl acetate (20 mL). The organic layer was washed with water (3×50 mL), dried over sodium sulfate and concentrated under reduced pressure. The residue was purified by column chromatography (silica gel, 100-200 mesh, 0 to 30% ethyl acetate in petroleum ether) to afford 7,7-dimethyl-5,7-dihydrothieno[3,4-d]pyrimidine-2-carbonitrile (150 mg, 63%) as a white solid, used as is in the next step.

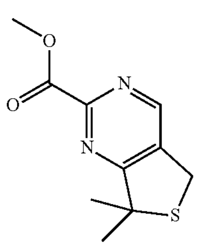

Step 3: methyl 7,7-dimethyl-5,7-dihydrothieno[3,4-d]pyrimidine-2-carboxylate

To a solution of 7,7-dimethyl-5,7-dihydrothieno[3,4-d]pyrimidine-2-carbonitrile (40 mg, 0.18 mmol) in methanol (3 mL) was added acetyl chloride (140 mg, 1.78 mmol). The reaction mixture was stirred at 25° C. for 12 h and then concentrated under reduced pressure to afford crude methyl 7,7-dimethyl-5,7-dihydrothieno[3,4-d]pyrimidine-2-carboxylate (38 mg, 95%) as a white solid: LCMS $R_T$=1.5 min; m/z=224.9 $(M+H)^+$.

LCMS (5-95% acetonitrile in water+0.1% trifluoroacetic over 1.5 mins) retention time 0.600 min, ESI+ found [M+H]+=224.9

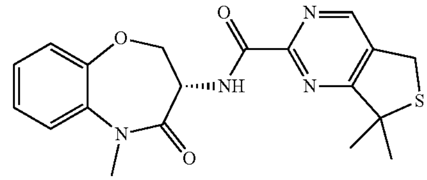 [SMILES: CN1C(=O)[C@@H](NC(=O)c2ncc3c(n2)C(C)(C)SC3)COc2ccccc21]

Step 4: (S)-7,7-dimethyl-N-(5-methyl-4-oxo-2,3,4,5-tetrahydrobenzo[b][1,4]oxazepin-3-yl)-5,7-dihydrothieno[3,4-d]pyrimidine-2-carboxamide To a solution of methyl 7,7-dimethyl-5,7-dihydrothieno[3,4-d]pyrimidine-2-carboxylate (38 mg, 0.17 mmol) in tetrahydrofuran (4 mL) and was added (3S)-3-amino-5-methyl-2,3-dihydro-1,5-benzoxazepin-4-one (36 mg, 0.19 mmol) and trimethylaluminum (2.0 M, 0.5 mL, 1.00 mmol). The reaction mixture was stirred at 30° C. for 12 h and then concentrated to dryness under reduced pressure. The residue was purified by RP-HPLC (acetonitrile 17-47/0.05% FA in water) to afford (S)-7,7-dimethyl-N-(5-methyl-4-oxo-2,3,4,5-tetrahydrobenzo[b][1,4]oxazepin-3-yl)-5,7-dihydrothieno[3,4-d]pyrimidine-2-carboxamide (2.1 mg, 3%) as a white solid: $^{1}H$ NMR (400 MHz, $CD_3OD$) δ 8.81 (s, 1H), 7.45-7.41 (m, 1H), 7.34-7.28 (m, 2H), 7.25-7.22 (m, 1H), 4.69-4.63 (m, 2H), 4.44-4.39 (m, 1H), 4.23 (s, 2H), 3.42 (s, 3H), 1.71 (s, 6H). LCMS $R_T$=1.065 min; m/z=385.2 $(M+H)^+$.

LCMS (10-80% acetonitrile in water+0.1% trifluoroacetic over 2 mins) retention time 1.065 min, ESI+ found [M+H]+= 385.2

Example 219

WX Method QQ

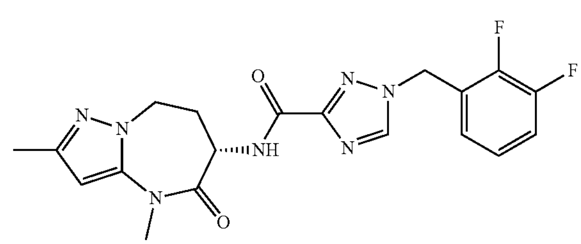 [SMILES: Cc1cc2n(n1)CC[C@H](NC(=O)c1ncn(Cc3cccc(F)c3F)n1)C(=O)N2C]

(S)-1-(2,3-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of 1-[(2,3-difluorophenyl)methyl]-1,2,4-triazole-3-carboxylic acid (37 mg, 0.15 mmol), (6S)-6-amino-2,4-dimethyl-7,8-dihydro-6H-pyrazolo[1,5-a][1,3]diazepin-5-one (20 mg, 0.10 mmol), 1H-benzo[d][1,2,3]triazol-1-ol (21 mg, 0.15 mmol) and $N^1$-((ethylimino)methylene)-$N^3$,$N^3$-dimethylpropane-1,3-diamine hydrochloride (30 mg, 0.15 mmol) in N,N-dimethylformamide (5 mL) was stirred at 25° C. for 1 h. The reaction was concentrated under reduced pressure and the residue was purified by RP-HPLC (acetonitrile 30-60%/0.05% ammonium hydroxide in water) to afford 1-[(2,3-difluorophenyl)methyl]-N-[(6S)-2,4-dimethyl-5-oxo-7,8-dihydro-6H-pyrazolo[1,5-a][1,3]diazepin-6-yl]-1,2,4-triazole-3-carboxamide (15.5 mg, 36%) as white solid: $^1$H NMR (400 MHz, DMSO-$d_6$) δ 8.83 (s, 1H), 8.52 (d, J=8.0 Hz, 1H), 7.48-7.41 (m, 1H), 7.27-7.15 (m, 2H), 6.12 (s, 1H), 5.61 (s, 2H), 4.34-4.23 (m, 2H), 4.11-4.04 (m, 1H), 3.21 (s, 3H), 2.62-2.54 (m, 1H), 2.36-2.28 (m, 1H), 2.16 (s, 3H). LCMS $R_T$=1.143 min; m/z=416.3 $(M+H)^+$.

LCMS (0 to 60% acetonitrile in water+0.03% trifluoacetic acid over 2 mins) retention time 1.143 min, ESI+ found $[M+H]^+$=416.3

Example 220

WX Method RR

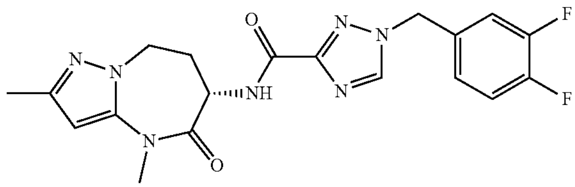 [SMILES: Cc1cc2n(n1)CC[C@H](NC(=O)c1ncn(Cc3ccc(F)c(F)c3)n1)C(=O)N2C]

(S)-1-(3,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of 1-[(3,4-difluorophenyl)methyl]-1,2,4-triazole-3-carboxylic acid (37 mg, 0.15 mmol), (6S)-6-amino-2,4-dimethyl-7,8-dihydro-6H-pyrazolo[1,5-a][1,3]diazepin-5-one (20 mg, 0.10 mmol), 1H-benzo[d][1,2,3]triazol-1-ol (21 mg, 0.15 mmol) and $N^1$-((ethylimino)methylene)-$N^3$,$N^3$-dimethylpropane-1,3-diamine hydrochloride (30 mg, 0.15 mmol) in N,N-dimethylformamide (5 mL) was stirred at 25° C. for 1 h. The reaction was concentrated under reduced pressure and the residue was purified by RP-HPLC (acetonitrile 23-53%/0.05% ammonium hydroxide in water) to afford (S)-1-(3,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (18.1 mg, 41%) as white solid: $^1$H NMR (400 MHz, DMSO-$d_6$) δ 8.80 (s, 1H), 8.52 (d, J=8.0 Hz, 1H), 7.49-7.41 (m, 2H), 7.19-7.17 (m, 1H), 6.12 (s, 1H), 5.48 (s, 2H), 4.35-4.23 (m, 2H), 4.11-4.04 (m, 1H), 3.21 (s, 3H), 2.62-2.54 (m, 1H), 2.36-2.28 (m, 1H), 2.16 (s, 3H). LCMS $R_T$=1.158 min; m/z=416.3 $(M+H)^+$.

LCMS (0 to 60% acetonitrile in water+0.03% trifluoacetic acid over 2 mins) retention time 1.158 min, ESI+ found $[M+H]^+$=416.3.

Example 221

WX Method WW

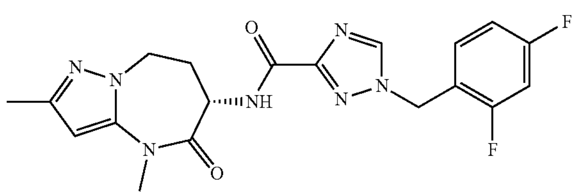 [SMILES: Cc1cc2n(n1)CC[C@H](NC(=O)c1ncn(Cc3ccc(F)cc3F)n1)C(=O)N2C]

(S)-1-(2,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of 1-[(2,4-difluorophenyl)methyl]-1,2,4-triazole-3-carboxylic acid (30 mg, 0.12 mmol), (6R)-6-amino-2,4-dimethyl-7,8-dihydro-6H-pyrazolo[1,5-a][1,3]diazepin-5-one (20 mg, 0.10 mmol), 1H-benzo[d][1,2,3]triazol-1-ol (21 mg, 0.15 mmol) and $N^1$-((ethylimino)methylene)-$N^3$,$N^3$-dimethylpropane-1,3-diamine hydrochloride (28 mg, 0.15 mmol) in N,N-dimethylformamide (5 mL) was stirred at 25° C. for 2 h. The reaction was concentrated under reduced pressure and the residue was purified by RP-HPLC (acetonitrile 20-50%/0.05% ammonia hydroxide in water) to afford (S)-1-(2,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (32 mg, 74%) as white solid: $^1$H NMR (400 MHz, $CD_3OD$) δ 8.59 (s, 1H), 7.48-7.45 (m, 1H), 7.05-7.00 (m, 2H), 6.11 (s, 1H), 5.52 (s, 2H), 4.54-4.49 (m, 1H), 4.33-4.23 (m, 2H), 3.32 (s, 3H), 2.85-2.83 (m, 1H), 2.25-2.24 (m, 4H). LCMS $R_T$=0.760 min; m/z=416.1 $(M+H)^+$.

LCMS (5 to 95% acetonitrile in water+0.03% formic acid over 1.5 mins) retention time 0.760 min, ESI+ found [M+H]= 416.1

Example 222

WX Method XX

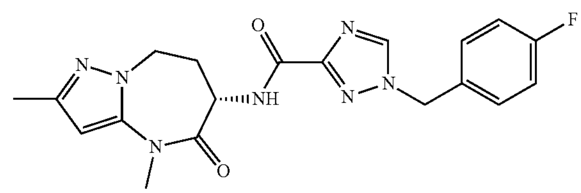 [SMILES: Cc1cc2n(n1)CC[C@H](NC(=O)c1ncn(Cc3ccc(F)cc3)n1)C(=O)N2C]

(S)—N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide A mixture of 1-[(4-fluorophenyl)methyl]-1,2,4-triazole-3-carboxylic acid (27 mg, 0.12 mmol), (6R)-6-amino-2,4-dimethyl-7,8-dihydro-6H-pyrazolo[1,5-a][1,3]diazepin-5-one (20 mg, 0.10 mmol), 1H-benzo[d][1,2,3]triazol-1-ol (21 mg, 0.15 mmol) and $N^1$-((ethylimino)methylene)-$N^3$,$N^3$-dimethylpropane-1,3-diamine hydrochloride (28 mg, 0.15 mmol) in N,N-dimethylformamide (5 mL) was stirred at 25° C. for 2 h. The reaction was concentrated under reduced pressure and the residue was purified by RP-HPLC (acetonitrile 20-50%/0.05% ammonia hydroxide in water) to afford (S)—N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide (31.4 mg, 80%) as white solid: $^1$H NMR (400 MHz, $CD_3OD$) δ 8.57 (s, 1H), 7.42-7.38 (m, 2H), 7.12-7.08 (m, 2H), 6.11 (s, 1H), 5.46 (s, 2H), 4.55-4.50 (m, 1H), 4.30-4.22 (m, 2H), 3.32 (s, 3H), 2.86-2.80 (m, 1H), 2.29-2.23 (m, 4H). LCMS $R_T$=3.87 min; m/z=424.1 $(M+H)^+$.

LCMS (5 to 95% acetonitrile in water+0.03% formic acid over 1.5 mins) retention time 0.745 min, ESI+ found [M+H]= 398.0.

Example 223

WX Method AAAA

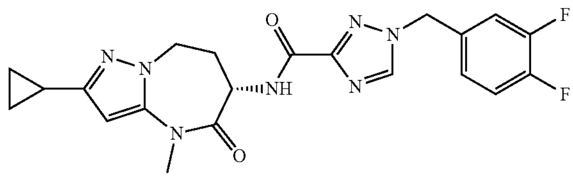 [SMILES: CN1C(=O)[C@@H](NC(=O)c2ncn(Cc3ccc(F)c(F)c3)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(3,4-difluorobenzyl)-1H-1,2,4-triazole-3-carboxamide

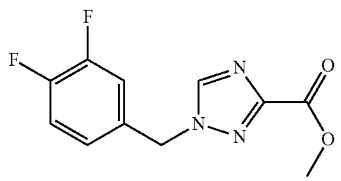 [SMILES: COC(=O)c1ncn(Cc2ccc(F)c(F)c2)n1]

Step 1: Methyl 1-[(3,4-difluorophenyl)methyl]-1,2,4-triazole-3-carboxylate

To a mixture of methyl 1H-1,2,4-triazole-3-carboxylate (10.0 g, 78.7 mmol) and potassium carbonate (21.8 g, 157.4 mmol) in N,N-dimethylformamide (200 mL) was added 3,4-difluorobenzyl chloride (19.6 g, 94.4 mmol) dropwise at 0° C. The mixture was stirred at 25° C. for 12 h and concentrated under reduced pressure. The residue was diluted with water (200 mL) and extracted with ethyl acetate (3×150 mL). The combined organic extracts were dried over sodium sulfate and concentrated under reduced pressure. The residue was purified by column chromatography (silica gel, 100-200 mesh, 0 to 100% ethyl acetate in petroleum ether) to afford methyl 1-[(3,4-difluorophenyl)methyl]-1,2,4-triazole-3-carboxylate (6.7 g, 34%) as white solid, used in the next step as is.

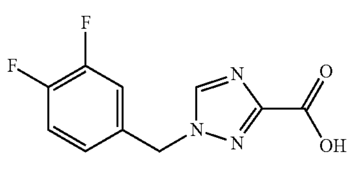 [SMILES: O=C(O)c1ncn(Cc2ccc(F)c(F)c2)n1]

Step 2: 1-[(3,4-difluorophenyl)methyl]-1,2,4-triazole-3-carboxylic acid

A mixture of methyl 1-[(3,4-difluorophenyl)methyl]-1,2,4-triazole-3-carboxylate (2.0 g, 7.9 mmol) and potassium hydroxide (886 mg, 15.8 mmol) in ethanol (40 mL) and water (5 mL) was stirred at 25° C. for 12 h. The reaction mixture was concentrated under reduced pressure and the residue was dissolved in water (20 mL). The aqueous solution was adjusted to pH=4 by addition of hydrochloric acid (1.0 M). The solid product was collected by filtration, washed with water (3×25 mL) and dried under vacuum to afford 1-[(3, 4-difluorophenyl)methyl]-1,2,4-triazole-3-carboxylic acid (1.6 g, 85%) as white solid: $^{1}H$ NMR (400 MHz, $CD_3OD$) δ 8.66 (s, 1H), 7.36-7.21 (m, 3H), 5.47 (s, 2H).

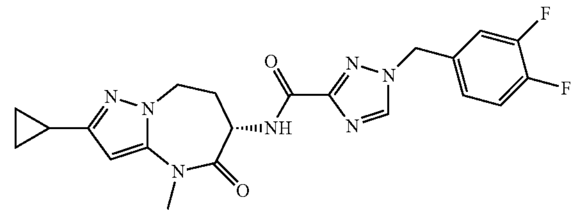 [SMILES: CN1C(=O)[C@@H](NC(=O)c2ncn(Cc3ccc(F)c(F)c3)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(3,4-difluorobenzyl)-1H-1,2,4-triazole-3-carboxamide A mixture of 1-[(3,4-difluorophenyl)methyl]-1,2,4-triazole-3-carboxylic acid (26 mg, 0.11 mmol), (6S)-6-amino-2-cyclopropyl-4-methyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol). and $N^1$-((ethylimino)methylene)-$N^3$,$N^3$-dimethylpropane-1,3-diamine hydrochloride (24 mg, 0.14 mmol) in N,N-dimethylformamide (5 mL) was stirred at 25° C. for 12 h. The reaction was concentrated under reduced pressure and the residue was purified by RP-HPLC (acetonitrile 17-47/0.05% HCl in water) to give (S)—N-(2-cyclopropyl-4-methyl-5-oxo-5,6,7,8-tetrahydro-4H-pyrazolo[1,5-a][1,3]diazepin-6-yl)-1-(3,4-difluorobenzyl)-1H-1,2,4-triazole-3-carboxamide (26 mg, 65%) as white solid: $^{1}H$ NMR (400 MHz, $CD_3OD$) δ 8.78 (s, 1H), 7.36-7.20 (m, 3H), 6.29 (s, 1H), 5.49 (s, 2H), 4.71-4.67 (m, 1H), 4.45-4.35 (m, 2H), 3.21 (s, 3H), 2.88-2.86 (m, 1H), 2.40-2.38 (m, 1H), 1.12-1.11 (m, 2H), 0.90-0.88 (m, 2H). LCMS $R_T$=1.02 min; m/z=442.2 $(M+H)^+$.

LCMS (10 to 80% acetonitrile in water+0.03% trifluoacetic acid over 2.0 mins) retention time 1.02 min, ESI+ found [M+H]=442.2.

Example 224

WX Method EEEE

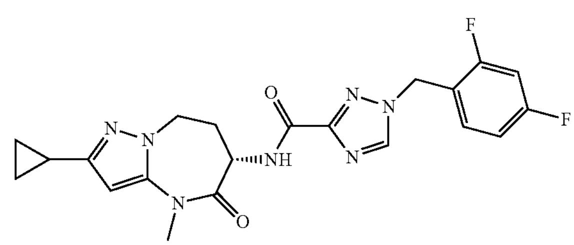 [SMILES: CN1C(=O)[C@@H](NC(=O)c2ncn(Cc3ccc(F)cc3F)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide A mixture of 1-[(2,4-difluorophenyl)methyl]-1,2,4-triazole-3-carboxylic acid (26 mg, 0.11 mmol), (6S)-6-amino-2- cyclopropyl-4-methyl-7,8-dihydro-6H-pyrazolo[1,5-a][1,3]diazepin-5-one (20 mg, 0.09 mmol), $N^1$-((ethylimino)methylene)-$N^3$,$N^3$-dimethyl propane-1,3-diamine hydrochloride (24 mg, 0.14 mmol) and 1H-benzo[d][1,2,3]triazol-1-ol (18 mg, 0.14 mmol) in N,N-dimethylformamide (3 mL) was stirred at 25° C. for 2 h. The reaction was concentrated under reduced pressure and the residue was purified by RP-HPLC (27-57% acetonitrile in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide (27.9 mg, 70%) as a white solid: $^1H$ NMR (400 MHz, $CD_3OD$) δ 8.59 (s, 1H), 7.50-7.46 (m, 1H), 7.06-6.99 (m, 2H), 6.00 (s, 1H), 5.53 (s, 2H), 4.52-4.49 (m, 1H), 4.29-4.19 (m, 2H), 3.18 (s, 3H), 2.85-2.80 (m, 1H), 2.25-2.23 (m, 1H), 1.92-1.89 (m, 1H), 0.95-0.92 (m, 2H), 0.75-0.72 (m, 2H). LCMS $R_T$=0.79 min; m/z=442.1 $(M+H)^+$.

LCMS (5 to 95% acetonitrile in water+0.03% formic acid over 1.5 mins) retention time 0.79 min, ESI+ found [M+H]=442.1.

Example 225

WX Method GGGG

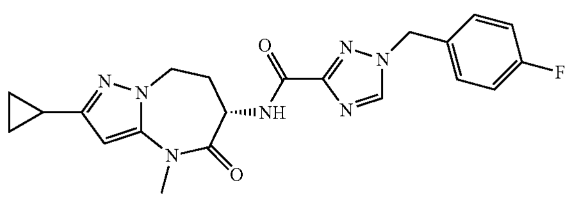 [SMILES: CN1C(=O)[C@@H](NC(=O)c2ncn(Cc3ccc(F)cc3)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide A mixture of 1-[(4-fluorophenyl)methyl]-1,2,4-triazole-3-carboxylic acid (24 mg, 0.11 mmol), (6S)-6-amino-2-cyclopropyl-4-methyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (24 mg, 0.14 mmol) in N,N-dimethylformamide (3 mL) was stirred at 25° C. for 2 h. The reaction was concentrated under reduced pressure and the residue was purified by RP-HPLC (27-57% acetonitrile in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide (29.9 mg, 78%) as a white solid: $^1H$ NMR (400 MHz, $CD_3OD$) δ 8.55 (s, 1H), 7.40-7.36 (m, 2H), 7.10-7.06 (m, 2H), 5.98 (s, 1H), 5.44 (s, 2H), 4.51-4.47 (m, 1H), 4.27-4.18 (m, 2H), 3.29 (s, 3H), 2.84-2.78 (m, 1H), 2.24-2.21 (m, 1H), 1.90-1.85 (m, 1H), 0.92-0.90 (m, 2H), 0.72-0.70 (m, 2H). LCMS $R_T$=0.78 min; m/z=424.1 $(M+H)^+$.

LCMS (5 to 95% acetonitrile in water+0.03% formic acid over 1.5 mins) retention time 0.78 min, ESI+ found [M+H]=424.1

Example 226

WX Method NNNNNN

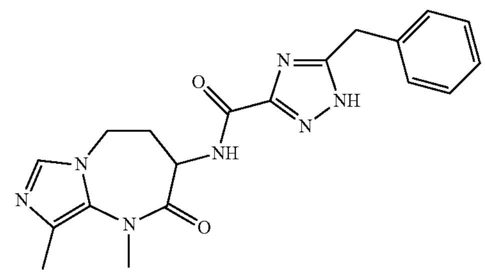 [SMILES: Cc1ncn2c1N(C)C(=O)C(NC(=O)c1n[nH]c(Cc3ccccc3)n1)CC2]

5-benzyl-N-(1,9-dimethyl-2-oxo-2,3,4,5-tetrahydro-1H-imidazo[1,5-a][1,3]diazepin-3-yl)-1H-1,2,4-triazole-3-carboxamide A mixture of 5-benzyl-1H-1,2,4-triazole-3-carboxylic acid (21 mg, 0.10 mmol), 3-amino-1,9-dimethyl-4,5-dihydro-1H-imidazo[1,5-a][1,3]diazepin-2(3H)-one (20 mg, 0.10 mmol), $N^1$-((ethylimino)methylene)-$N^3$,$N^3$-dimethylpropane-1,3-diamine hydrochloride (24 mg, 0.12 mmol) and 1H-benzo[d][1,2,3]triazol-1-ol (17 mg, 0.12 mmol) in N,N-dimethylformamide (4 mL) was stirred at 25° C. for 12 h. The reaction mixture was concentrated under reduced pressure and the residue was purified by RP-HPLC (acetonitrile 10-40/0.05% ammonia hydroxide in water) to afford 5-benzyl-N-(1,9-dimethyl-2-oxo-2,3,4,5-tetrahydro-1H-imidazo[1,5-a][1,3]diazepin-3-yl)-1H-1,2,4-triazole-3-carboxamide (2.4 mg, 6%) as a white solid: $^1H$ NMR (400 MHz, $CD_3OD$) δ 7.55 (s, 1H), 7.34-7.24 (m, 5H), 4.57-4.55 (m, 1H), 4.37-4.31 (m, 1H), 4.18-4.16 (m, 2H), 3.97-3.91 (m, 1H), 3.31 (s, 3H), 2.72-2.65 (m, 1H), 2.22 (s, 3H), 2.11-2.07 (m, 1H). LCMS $R_T$=0.84 min; m/z=380.2 $(M+H)^+$.

LCMS (0-60% acetonitrile in water+0.03% trifluoacetic acid over 2 mins) retention time 0.84/min, ESI+ found [M+H]=380.2.

Example 227

WX Method OOOOOO

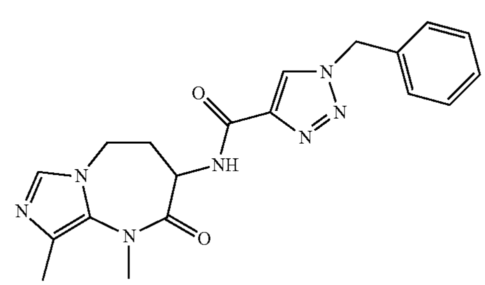 [SMILES: Cc1ncn2c1N(C)C(=O)C(NC(=O)c1cn(Cc3ccccc3)nn1)CC2]

1-benzyl-N-(1,9-dimethyl-2-oxo-2,3,4,5-tetrahydro-1H-imidazo[1,5-a][1,3]diazepin-3-yl)-1H-1,2,3-triazole-4-carboxamide A mixture of 5-benzyl-1H-1,2,4-triazole-3-carboxylic acid (21 mg, 0.10 mmol), 3-amino-1,9-dimethyl-4,5-dihydro-1H-imidazo[1,5-a][1,3]diazepin-2(3H)-one (20 mg, 0.10 mmol), $N^1$-((ethylimino)methylene)-$N^3$,$N^3$-dimethyl-propane-1,3-diamine hydrochloride (24 mg, 0.12 mmol) and 1H-benzo[d][1,2,3]triazol-1-ol (17 mg, 0.12 mmol) in N,N-dimethylformamide (4 mL) was stirred at 25° C. for 12 h. The reaction mixture was concentrated under reduced pressure and the residue was purified by RP-HPLC (acetonitrile 15-45/0.05% ammonia hydroxide in water) to afford 1-benzyl-N-(1,9-dimethyl-2-oxo-2,3,4,5-tetrahydro-1H-imidazo[1,5-a][1,3]diazepin-3-yl)-1H-1,2,3-triazole-4-carboxamide (7 mg, 18%), as a white solid: $^1H$ NMR (400 MHz, $CD_3OD$) δ 8.36 (s, 1H), 7.55 (s, 1H), 7.40-7.33 (m, 5H), 5.64 (s, 2H), 4.58-4.53 (m, 1H), 4.37-4.32 (m, 1H), 3.97-3.92 (m, 1H), 3.31 (s, 3H), 2.70-2.64 (m, 1H), 2.22 (s, 3H), 2.17-2.12 (m, 1H). LCMS $R_T$=0.94 min; m/z=380.1 $(M+H)^+$.

LCMS (0-60% acetonitrile in water+0.05% trifluoacetic acid over 2 mins) retention time 0.94/min, ESI+ found [M+H]=380.1.

Example 228

WX Method KK

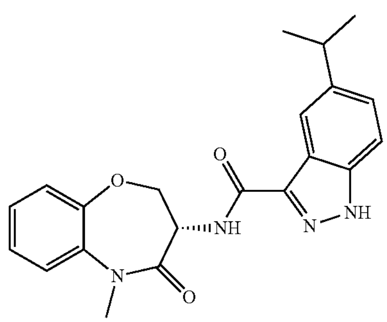 [SMILES: CC(C)c1ccc2[nH]nc(C(=O)N[C@H]3COc4ccccc4N(C)C3=O)c2c1]

(S)-5-isopropyl-N-(5-methyl-4-oxo-2,3,4,5-tetrahydrobenzo[b][1,4]oxazepin-3-yl)-1H-indazole-3-carboxamide

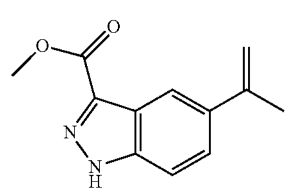 [SMILES: C=C(C)c1ccc2[nH]nc(C(=O)OC)c2c1]

Step 1: Methyl 5-isopropenyl-1h-indazole-3-carboxylate

A mixture of methyl 5-bromo-1h-indazole-3-carboxylate (400 mg, 1.56 mmol), 1,1'-bis(diphenylphosphino)ferrocene palladium dichloride (114 mg, 0.16 mmol), cesium carbonate (1000 mg, 3.14 mmol) and potassium isopropenyltrifluoroborate (348 mg, 2.36 mmol) in dioxane (5 mL) and water (1 mL) was heated at 120° C. for 1 h under microwave conditions. The reaction mixture was concentrated under reduced pressure and the residue was purified by column chromatography (silica gel, 100-200 mesh, 0 to 50% ethyl acetate in petroleum ether) to afford methyl 5-isopropenyl-1 h-indazole-3-carboxylate (175 mg, 52%) as a white solid: LCMS $R_T$=3.173 min; m/z=216.9 $(M+H)^+$.

LCMS (10 to 80% acetonitrile in water+0.03% trifluoacetic acid 7 mins) retention time 3.173 min, ESI+ found [M+H]=216.9.

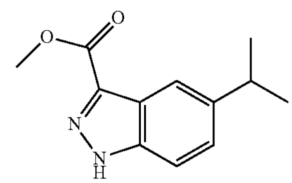 [SMILES: COC(=O)c1n[nH]c2ccc(C(C)C)cc12]

Step 2: Methyl 5-isopropyl-1h-indazole-3-carboxylate

A mixture of methyl 5-isopropenyl-1h-indazole-3-carboxylate (70 mg, 0.32 mmol) and 10% palladium on carbon (35 mg, 0.32 mmol) in methanol (5 mL) was hydrogenated (15 psi) at 25° C. for 16 h. The reaction mixture was filtered and the filtrate was concentrated under reduced pressure affording crude methyl 5-isopropyl-1h-indazole-3-carboxylate (64 mg, 91%) as a pale yellow solid: LCMS $R_T$=3.307 min; m/z=219.0 $(M+H)^+$.

LCMS (10 to 80% acetonitrile in water+0.03% trifluoacetic acid 7 mins) retention time 3.307 min, ESI+ found $[M+H]^+$=219.0.

Step 3: 5-isopropyl-1h-indazole-3-carboxylic acid

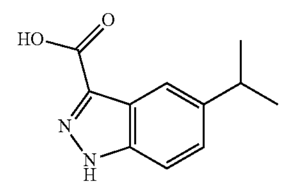

A mixture of methyl 5-isopropyl-1H-indazole-3-carboxylate (64 mg, 0.29 mmol) and lithium hydroxide hydrate (35 mg, 1.47 mmol) in tetrahydrofuran (5 mL) and water (2 mL) was stirred at 25° C. for 18 h. The organic solvent was removed under reduced pressure, and the aqueous residue was adjusted to pH=5 by addition of hydrochloric acid (1.0 M). The solid was removed by filtration and the aqueous layer was concentrated under reduced pressure affording 5-isopropyl-1H-indazole-3-carboxylic acid (40 mg, 67%) as a white solid: LCMS $R_T$=1.711 min; m/z=205.1 $(M+H)^+$.

LCMS (0 to 60% acetonitrile in water+0.04% formic acid over 3 mins) retention time 1.711 min, ESI+ found [M+H]=205.1

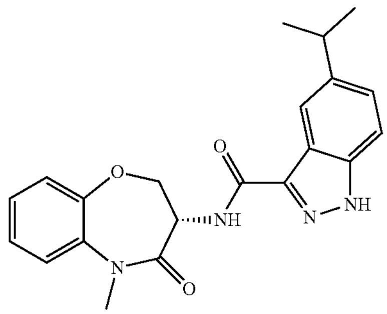 [SMILES: CC(C)c1ccc2[nH]nc(C(=O)N[C@H]3COc4ccccc4N(C)C3=O)c2c1]

Step 4: (S)-5-isopropyl-N-(5-methyl-4-oxo-2,3,4,5-tetrahydrobenzo[b][1,4]oxazepin-3-yl)-1H-indazole-3-carboxamide A mixture of (3s)-3-amino-5-methyl-2,3-dihydro-1,5-benzoxazepin-4-one (41 mg, 0.22 mmol), 5-isopropyl-h-indazole-3-carboxylic acid (40 mg, 0.20 mmol), $N^1$-((ethylimino)methylene)-$N^3$,$N^3$-dimethylpropane-1,3-diamine hydrochloride (45 mg, 0.24 mmol) and 1H-benzo[d][1,2,3]triazol-1-ol (32 mg, 0.24 mmol) in N,N-dimethylformamide (5 mL) was stirred at 25° C. for 1 h. The reaction was concentrated under reduced pressure and the residue was purified by RP-HPLC (acetonitrile 46-76%/0.05% ammonia in water) affording (S)-5-isopropyl-N-(5-methyl-4-oxo-2,3,4,5-tetrahydrobenzo[b][1,4]oxazepin-3-yl)-1H-indazole-3-carboxamide (31.5 mg, 41.5% yield) as a white solid: $^1H$ NMR (400 MHz, DMSO-$d_6$) δ 13.65 (br.s, 1H), 8.38 (d, J=8.0 Hz, 1H), 7.89 (s, 1H), 7.60-7.49 (m, 2H), 7.40-7.23 (m, 4H), 4.99-4.89 (m, 1H), 4.68-4.58 (m, 1H), 4.52-4.43 (m, 1H), 3.34 (s, 3H), 3.04-2.93 (m, 1H), 1.22 (d, J=6.8 Hz, 6H). LCMS $R_T$=1.173 min; m/z=379.1 $(M+H)^+$.

LCMS (10 to 80% acetonitrile in water+0.03% trifluoacetic acid 7 mins) retention time 1.173 min, ESI+ found [M+H]=379.1.

Example 229

WX Method Z

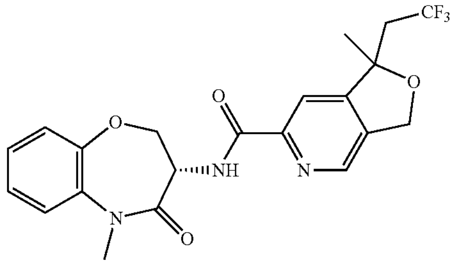 [SMILES: CN1C(=O)[C@@H](NC(=O)c2cc3c(cn2)COC3(C)CC(F)(F)F)COc2ccccc21]

1-methyl-N—((S)-5-methyl-4-oxo-2,3,4,5-tetrahydrobenzo[b][1,4]oxazepin-3-yl)-1-(2,2,2-trifluoroethyl)-1,3-dihydrofuro[3,4-c]pyridine-6-carboxamide

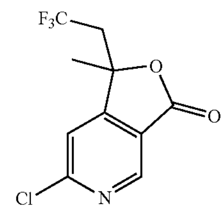 [SMILES: CC1(CC(F)(F)F)OC(=O)c2cnc(Cl)cc21]

Step 1: 6-chloro-1-methyl-1-(2,2,2-trifluoroethyl)furo[3,4-c]pyridin-3(1H)-one

To a solution of 2,2,6,6-tetramethylpiperidine (13.5 g, 95.6 mmol) in tetrahydrofuran (300 mL) was added n-butyllithium (2.5 M, 50.0 mL, 125.0 mmol) at −78° C. The reaction was stirred at −78° C. for 1 h, and 6-chloronicotinic acid (5.0 g, 31.7 mmol) in tetrahydrofuran (30 mL) was added. Stirring at −78° C. was continued for 2 h, then 4,4,4-trifluorobutan-2-one (4.0 g, 31.7 mmol) was added. After addition, the reaction mixture was warmed up to 25° C. for 16 h and then quenched by addition of saturated aqueous ammonium chloride (50 mL). The resulting mixture was extracted with ethyl acetate (3×80 mL). The combined organic layers were washed with water (20 mL), brine (20 mL), dried over sodium sulfate and concentrated under reduced pressure. The residue was purified by column chromatography (silica gel, 100-200 mesh, 0 to 50% ethyl acetate in petroleum ether) to afford 6-chloro-1-methyl-1-(2,2,2-trifluoroethyl)furo[3,4-c]pyridin-3(1H)-one (4.0 g, 47%) as yellow oil: $^1H$ NMR (400 MHz, $CDCl_3$) δ 8.96 (s, 1H), 7.48 (s, 1H), 2.95-2.88 (m, 1H), 2.82-2.76 (m, 1H), 1.77 (s, 3H).

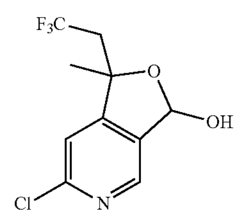 [SMILES: CC1(CC(F)(F)F)OC(O)c2cnc(Cl)cc21]

Step 2: 6-chloro-1-methyl-1-(2,2,2-trifluoroethyl)-1,3-dihydrofuro[3,4-c]pyridin-3-ol To a solution of 6-chloro-1-methyl-1-(2,2,2-trifluoroethyl)furo[3,4-c]pyridine-3(1H)-one (3.5 g, 13.2 mmol) in toluene (15 mL) was added diisobutylaluminum hydride (1.0 M, 26.4 mL, 26.4 mmol) dropwise at −70° C. After addition, stirring at −70° C. was continued for 2 h and the reaction mixture was quenched by addition of saturated aqueous ammonium chloride. The resulting mixture was filtered and the filtrate was extracted with ethyl acetate (3×50 mL). The combined organic layers were washed water (50 mL), brine (50 mL), dried over sodium sulfate and concentrated under reduced pressure. The residue was purified by column chromatography (silica gel, 100-200 mesh, 0 to 30% ethyl acetate in petroleum ether) to afford 6-chloro-1-methyl-1-(2,2,2-trifluoroethyl)-1,3-dihydrofuro[3,4-c]pyridin-3-ol (3.5 g, 99%) as yellow oil, used as is in the next step.

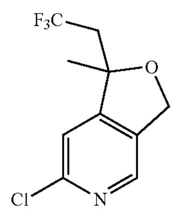 [SMILES: CC1(CC(F)(F)F)OCc2cnc(Cl)cc21]

Step 3: 6-chloro-1-methyl-1-(2,2,2-trifluoroethyl)-1,3-dihydrofuro[3,4-c]pyridine To a solution of 6-chloro-1-methyl-1-(2,2,2-trifluoroethyl)-1,3-dihydrofuro[3,4-c]pyridin-3-ol (3.4 g, 12.7 mmol) in dichloromethane (50 mL) was added trifluoroacetic acid (7.2 g, 63.5 mmol) dropwise at 0° C. The reaction was stirred for 30 min at 0° C., and triethyl silane (7.4 g, 63.5 mmol) was added. After addition, the mixture was allowed to warm to 25° C. over 3 h and then quenched by addition of saturated sodium bicarbonate. The mixture was extracted with dichloromethane (3×50 mL). The combined organic layers were washed water (20 mL), brine (20 mL), dried over sodium sulfate and concentrated under reduced pressure. The residue was purified by column chromatography (silica gel, 100-200 mesh, 0 to 15% ethyl acetate in petroleum ether) to afford 6-chloro-1-methyl-1-(2,2,2-trifluoroethyl)-1,3-dihydrofuro[3,4-c]pyridine (3.0 g, 94%) as yellow oil, used as is in the next step.

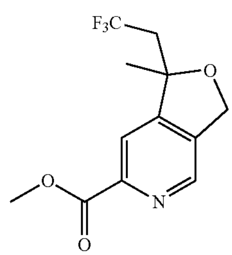 [SMILES: COC(=O)c1cc2c(cn1)COC2(C)CC(F)(F)F]

Step 4: methyl 1-methyl-1-(2,2,2-trifluoroethyl)-1,3-dihydrofuro[3,4-c]pyridine-6-carboxylate A solution of 6-chloro-1-methyl-1-(2,2,2-trifluoroethyl)-1,3-dihydrofuro[3,4-c]pyridine (3.0 g, 11.9 mmol), 1,1'-bis(diphenylphosphino)ferrocene palladium dichloride (872 mg, 1.19 mmol) and triethylamine (6.0 g, 59.6 mmol) in methanol (80 mL) was heated to 80° C. for 4 h under carbon oxide (40 psi). The mixture was concentrated under reduced pressure and the residue was purified by column chromatography (silica gel, 100-200 mesh, 0 to 50% ethyl acetate in petroleum ether) to afford methyl 1-methyl-1-(2,2,2-trifluoroethyl)-1,3-dihydrofuro[3,4-c]pyridine-6-carboxylate (2.5 g, 76%) as yellow oil, used as is in the next step.

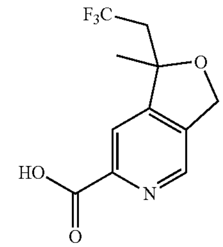 [SMILES: CC1(CC(F)(F)F)OCc2cnc(C(=O)O)cc21]

Step 5: 1-methyl-1-(2,2,2-trifluoroethyl)-1,3-dihydrofuro[3,4-c]pyridine-6-carboxylic acid A mixture of methyl 1-methyl-1-(2,2,2-trifluoroethyl)-1,3-dihydrofuro[3,4-c]pyridine-6-carboxylate (2.5 g, 9.1 mmol) and lithium hydroxide hydrate (1.9 g, 45.4 mmol) in tetrahydrofuran (15 mL) and water (5 mL) was stirred at 25° C. for 2 h. The organic solvent was evaporated under reduced pressure and the resulting aqueous layer was adjusted to pH=5 by addition of hydrochloric acid (1.0 M). The mixture was extracted with ethyl acetate (3×50 mL). The combined organic layers were washed with water (20 mL), brine (20 mL), dried over sodium sulfate and concentrated under reduced pressure to afford 1-methyl-1-(2,2,2-trifluoroethyl)-1,3-dihydrofuro[3,4-c]pyridine-6-carboxylic acid (2.3 g, 91%) as a yellow solid, used in the next step without further purification.

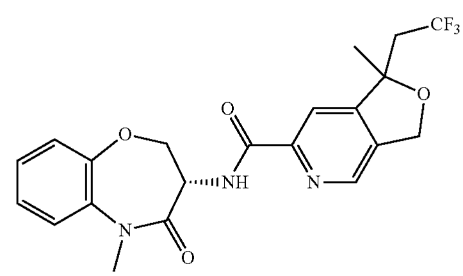 [SMILES: CN1C(=O)[C@@H](NC(=O)c2cc3c(cn2)COC3(C)CC(F)(F)F)COc2ccccc21]

Step 6: 1-methyl-N—((S)-5-methyl-4-oxo-2,3,4,5-tetrahydrobenzo[b][1,4]oxazepin-3-yl)-1-(2,2,2-trifluoroethyl)-1,3-dihydrofuro[3,4-c]pyridine-6-carboxamide A mixture of 1-methyl-1-(2,2,2-trifluoroethyl)-1,3-dihydrofuro[3,4-c]pyridine-6-carboxylic acid (49 mg, 0.19 mmol), 1H-benzo[d][1,2,3]triazol-1-ol (25 mg, 0.19 mmol), (3S)-3-amino-5-methyl-2,3-dihydro-1,5-benzoxazepin-4-one (30 mg, 0.16 mmol) and $N^1$-((ethylimino)methylene)-$N^3$,$N^3$-dimethylpropane-1,3-diamine hydrochloride (36 mg, 0.19 mmol) in N,N-dimethylformamide (5 mL) was stirred at 25° C. for 2 h. The reaction was concentrated under reduced pressure and the residue was purified by RP-HPLC (acetonitrile 43-73% with 0.05% HCl in water) to afford 1-methyl-N—((S)-5-methyl-4-oxo-2,3,4,5-tetrahydrobenzo[b][1,4]oxazepin-3-yl)-1-(2,2,2-trifluoroethyl)-1,3-dihydrofuro[3,4-c]pyridine-6-carboxamide (45.7 mg, 67%) as a white solid: $^1$H NMR (400 MHz, $CD_3OD$) δ 8.62 (s, 1H), 8.05 (s, 1H), 7.46-7.43 (m, 1H), 7.34-7.31 (m, 2H), 7.27-7.24 (m, 1H), 5.21 (s, 2H), 5.04-5.01 (m, 1H), 4.67-4.62 (m, 1H), 4.44-4.41 (m, 1H), 3.43 (s, 3H), 2.90-2.79 (m, 2H), 1.57 (s, 3H). LCMS $R_T$=0.878 min; m/z=436.1 $(M+H)^+$.

LCMS (5-95% acetonitrile in water+0.05% trifluoacetic acid over 1.5 mins) retention time 0.878 min, ESI+ found [M+H]=436.1.

Example 230

WX Method U

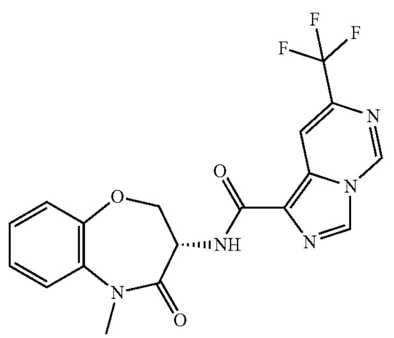 [SMILES: CN1C(=O)[C@@H](NC(=O)c2ncn3cnc(C(F)(F)F)cc23)COc2ccccc21]

(S)—N-(5-methyl-4-oxo-2,3,4,5-tetrahydrobenzo[b][1,4]oxazepin-3-yl)-7-(trifluoromethyl) imidazo[1,5-c]pyrimidine-1-carboxamide

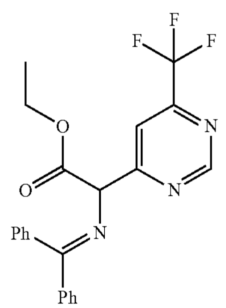 [SMILES: CCOC(=O)C(N=C(c1ccccc1)c1ccccc1)c1cc(C(F)(F)F)ncn1]

Step 1: ethyl 2-((diphenylmethylene)amino)-2-(6-(trifluoromethyl)pyrimidin-4-yl)acetate To a solution of 2-((diphenylmethylene)amino)acetate (3.0 g, 11.2 mmol) in tetrahydrofuran (60 mL) was added potassium tert-butoxide (1.0 M, 12.3 mL, 12.3 mmol) dropwise at −78° C. After stirred for 30 min at −78° C., 4-chloro-6-trifluoromethylpyrimidine (3.1 g, 16.8 mmol) was added and the resulting mixture was allowed to warm to 0° C. and stirred for another 0.5 h. The reaction was diluted with water (30 mL) and extracted with ethyl acetate (3×35 mL). The combined organic layers were dried over sodium sulfate and concentrated under reduced pressure. The residue was purified by column chromatography (silica gel, 100-200 mesh, 0 to 10% ethyl acetate in petroleum ether) to afford ethyl 2-((diphenylmethylene)amino)-2-(6-(trifluoromethyl)pyrimidin-4-yl)acetate (3.5 g, 23%) as red oil: LCMS $R_T$=1.001 min; m/z=414.0 $(M+H)^+$.

LCMS (5 to 95% acetonitrile in water+0.03% formic acid over 1.5 mins) retention time 1.001 min, ESI+ found [M+H]= 414.0.

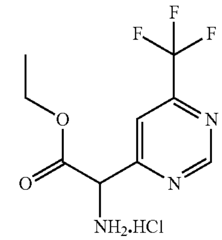

Step 2: ethyl 2-amino-2-(6-(trifluoromethyl)pyrimidin-4-yl)acetate hydrochloride A mixture of ethyl 2-((diphenylmethylene)amino)-2-(6-(trifluoromethyl)pyrimidin-4-yl)acetate (3.5 g, 2.5 mmol) and hydrochloric acid (36%, 514 mg, 5.08 mmol) in dichloromethane (25 mL) was stirred at 25° C. for 1 h. The solution was diluted with water (20 mL) and washed with dichloromethane (2×25 mL). The aqueous phase was concentrated to dryness to afford crude ethyl 2-amino-2-(6-(trifluoromethyl) pyrimidin-4-yl)acetate hydrochloride (600 mg, 95%) as yellow oil: LCMS $R_T$=0.244 min; m/z=249.8 $(M+H)^+$.

LCMS (5 to 95% acetonitrile in water+0.03% formic acid over 1.5 mins) retention time 0.244 min, ESI+ found [M+H]= 249.8.

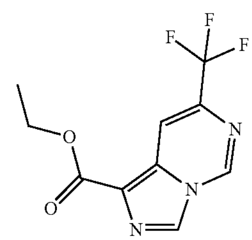 [SMILES: CCOC(=O)c1ncn2cnc(C(F)(F)F)cc12]

Step 3: ethyl 7-(trifluoromethyl)imidazo[1,5-c]pyrimidine-1-carboxylate

Formic acid (98%, 2 mL) was added dropwise to acetic anhydride (4.0 mL) at 0° C. The resulting solution was stirred for 4 h at 0° C., and then added to a solution of ethyl 2-amino-2-(6-(trifluoromethyl)pyrimidin-4-yl)acetate hydrochloride (600 mg, 2.41 mmol) in tetrahydrofuran (10 mL) at 0° C. After addition, the mixture was stirred at 25° C. for 6 h, and then diluted with water (30 mL). The mixture was extracted with ethyl acetate (3×30 mL). The combined organic layers were concentrated under reduced pressure and the residue was purified by column chromatography (silica gel, 100-200 mesh, 0 to 50% ethyl acetate in petroleum ether) to afford ethyl 7-(trifluoromethyl)imidazo[1,5-c]pyrimidine-1-carboxylate (600 mg, 96%) as a white solid: $^1H$ NMR (400 MHz, $CDCl_3$) δ 9.09 (s, 1H), 8.43 (s, 1H), 8.35 (s, 1H), 4.50-4.45 (m, 2H), 1.45 (t, J=7.2 Hz, 3H).

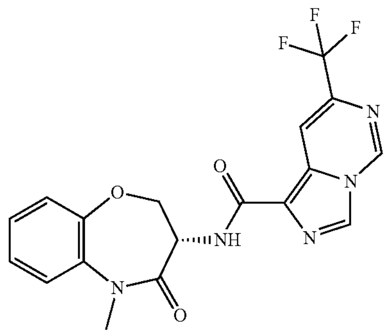 [SMILES: CN1C(=O)[C@@H](NC(=O)c2ncn3cnc(C(F)(F)F)cc23)COc2ccccc21]

Step 4: (S)—N-(5-methyl-4-oxo-2,3,4,5-tetrahydrobenzo[b][1,4]oxazepin-3-yl)-7-(trifluoromethyl)imidazo[1,5-c]pyrimidine-1-carboxamide To a mixture of (3S)-3-amino-5-methyl-2,3-dihydro-1,5-benzoxazepin-4-one (50 mg, 0.26 mmol) and ethyl 7-(trifluoromethyl)imidazo[1,5-c]pyrimidine-1-carboxylate (60.67 mg, 0.23 mmol) in tetrahydrofuran (3 mL) was added trimethylaluminum (2.0 M, 0.78 mL, 1.56 mmol). The mixture was stirred at 50° C. for 15 h and then quenched by addition of saturated aqueous potassium sodium tartrate (10 mL). The solution was stirred at 25° C. for 1 h and then extracted with ethyl acetate (3×20 mL). The combined organic layers were dried over sodium sulfate and concentrated under reduced pressure. The residue was purified by RP-HPLC (32-62% acetonitrile in water and 0.05% ammonium hydroxide) to afford (S)—N-(5-methyl-4-oxo-2,3,4,5-tetrahydrobenzo[b][1,4]oxazepin-3-yl)-7-(trifluoromethyl)imidazo[1,5-c]pyrimidine-1-carboxamide (31 mg, 27%) as a white solid: $^1$H NMR (400 MHz, DMSO-$d_6$) δ 9.51 (s, 1H), 8.82 (s, 1H), 8.47 (d, J=8.0 Hz, 1H), 8.17 (s, 1H), 7.50 (d, J=2.0 Hz, 1H), 7.34-7.25 (m, 3H), 4.95-4.89 (m, 1H), 4.66-4.61 (m, 1H), 4.47-4.29 (m, 1H), 3.33 (s, 3H): LCMS $R_T$=0.845 min; m/z=406.0 $(M+H)^+$.

LCMS (5 to 95% acetonitrile in water+0.03% formic acid over 1.5 mins) retention time 0.845 min, ESI+ found [M+H]= 406.0.

Example 231

WX Method DD

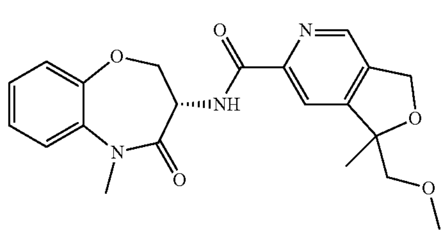 [SMILES: COCC1(C)OCc2cnc(C(=O)N[C@H]3COc4ccccc4N(C)C3=O)cc21]

1-(methoxymethyl)-1-methyl-N—((S)-5-methyl-4-oxo-2,3,4,5-tetrahydrobenzo[b][1,4]oxazepin-3-yl)-1,3-dihydrofuro[3,4-c]pyridine-6-carboxamide

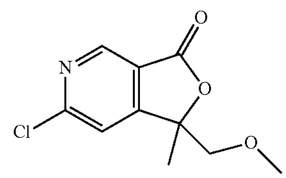

Step 1: 6-chloro-1-(methoxymethyl)-1-methyl-3H-furo[3,4-c]pyridin-3-one

To a stirred solution of 2,2,6,6-tetramethylpiperidine (4.1 g, 29.0 mmol) in tetrahydrofuran (100 mL) was added n-butyllithium (2.5 M, 15 mL, 37.5 mmol) dropwise at −78° C. The mixture was stirred at −78° C. for 40 min and then 6-chloronicotinic acid (1.5 g, 9.5 mmol) in tetrahydrofuran (20 mL) was added. The resulting mixture was stirred at −78° C. for another 2 h, and then methoxyacetone (839 mg, 9.52 mmol) was added dropwise. After addition, the reaction was warmed up to 25° C. and stirred for 16 h before quenched by addition of saturated aqueous ammonium chloride. The resulting mixture was extracted with ethyl acetate (3×50 mL). The combined organic layer was washed water (30 mL), brine (30 mL), dried over sodium sulfate and concentrated under reduced pressure. The residue was purified by column chromatography (silica gel, 100-200 mesh, 0-50% ethyl acetate/petroleum ether) to afford 6-chloro-1-(methoxymethyl)-1-methyl-3H-furo[3,4-c]pyridin-3-one (1.5 g, 69%) as yellow oil, use in the next step as is

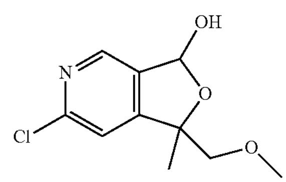

Step 2: 6-chloro-1-(methoxymethyl)-1-methyl-3H-furo[3,4-c]pyridin-3-ol

To a solution of 6-chloro-1-(methoxymethyl)-1-methyl-3H-furo[3,4-c]pyridin-3-one (1.5 g, 6.6 mmol) in toluene (40 mL) was added diisobutylaluminum hydride (1.0 M, 13.0 mL, 13.0 mmol) dropwise at −70° C. After addition, stirring at −70° C. was continued for 2 h and the reaction mixture was quenched by addition of saturated aqueous ammonium chloride. The resulting mixture was filtered and the filtrate was extracted with ethyl acetate (3×30 mL). The combined organic layers were washed water (20 mL), brine (20 mL), dried over sodium sulfate and concentrated under reduced pressure to afford crude 6-chloro-1-(methoxymethyl)-1-methyl-3H-furo[3,4-c]pyridin-3-ol (1.5 g, 99%) as yellow oil, used in the next step without further purification.

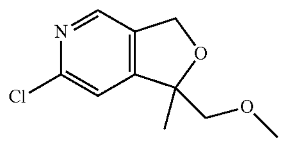

Step 3: 6-chloro-1-(methoxymethyl)-1-methyl-3H-furo[3,4-c]pyridine

To a solution of 6-chloro-1-(methoxymethyl)-1-methyl-3H-furo[3,4-c]pyridin-3-ol (280 mg, 1.22 mmol) in dichloromethane (20 mL) was added trifluoroacetic acid (695 mg, 6.10 mmol) dropwise at 0° C. The reaction was stirred for 30 min at 0° C., and triethyl silane (425 mg, 3.66 mmol) was added. After addition, the mixture was allowed to warm to 25° C. over 3 h and then quenched by addition of saturated sodium bicarbonate. The mixture was extracted with dichloromethane (3×30 mL). The combined organic layers were washed water (20 mL), brine (20 mL), dried over sodium sulfate and concentrated under reduced pressure. The residue was purified by column chromatography (silica gel, 100-200 mesh, 0-50% ethyl acetate in petroleum ether) to afford 6-chloro-1-(methoxymethyl)-1-methyl-3H-furo[3,4-c]pyridine (200 mg, 77%) as yellow oil: LCMS $R_T$=0.45 min; m/z=214.1 $(M+H)^+$.

LCMS (5-95% acetonitrile in water+0.03% trifluoacetic acid over 1.5 mins) retention time 0.45/min, ESI+ found [M+H]=214.1.

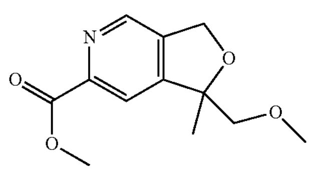 [SMILES: COCC1(C)OCc2cnc(C(=O)OC)cc21]

Step 4: methyl 1-(methoxymethyl)-1-methyl-3H-furo[3,4-c]pyridine-6-carboxylate

A solution of 6-chloro-1-(methoxymethyl)-1-methyl-3H-furo[3,4-c]pyridine (200 mg, 0.94 mmol), 1,1'-bis(diphenylphosphino)ferrocene palladium dichloride (68 mg, 0.09 mmol) and triethylamine (947 mg, 9.36 mmol) in methanol (10 mL) was heated at 80° C. for 12 h under carbon oxide (25 psi). The mixture was concentrated under reduced pressure and the residue was purified by column chromatography (silica gel, 100-200 mesh, 0-50% ethyl acetate in petroleum ether) to afford methyl 1-(methoxymethyl)-1-methyl-3H-furo[3,4-c]pyridine-6-carboxylate (160 mg, 72%) as yellow oil: LCMS $R_T$=0.52 min; m/z=238.0 $(M+H)^+$.

LCMS (5-95% acetonitrile in water+0.03% trifluoacetic acid over 1.5 mins) retention time 0.52/min, ESI+ found [M+H]=238.0

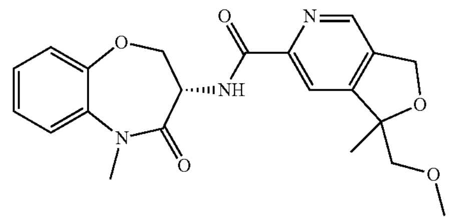 [SMILES: COCC1(C)OCc2cnc(C(=O)N[C@H]3COc4ccccc4N(C)C3=O)cc21]

Step 5: 1-(methoxymethyl)-1-methyl-N—((S)-5-methyl-4-oxo-2,3,4,5-tetrahydrobenzo[b][1,4]oxazepin-3-yl)-1,3-dihydrofuro[3,4-c]pyridine-6-carboxamide To a solution of methyl 1-(methoxymethyl)-1-methyl-3H-furo[3,4-c]pyridine-6-carboxylate (20 mg, 0.08 mmol) and (3S)-3-amino-5-methyl-2,3-dihydro-1,5-benzoxazepin-4-one (18 mg, 0.09 mmol) in tetrahydrofuran (4 mL) was added and trimethylaluminum (2.0 M, 0.25 mL, 0.51 mmol). The reaction mixture was stirred at 25° C. for 12 h and then filtered. The filtrate was concentrated under reduce pressure and the residue was purified by RP-HPLC (acetonitrile 30-60/0.05% ammonia hydroxide in water) to afford 1-(methoxymethyl)-1-methyl-N—((S)-5-methyl-4-oxo-2,3,4,5-tetrahydrobenzo[b][1,4]oxazepin-3-yl)-1,3-dihydrofuro[3,4-c]pyridine-6-carboxamide (2 mg, 7%) as a white solid: $^1$H NMR (400 MHz, $CD_3OD$) δ 8.57 (s, 1H), 7.93 (s, 1H), 7.45-7.43 (m, 1H), 7.34-7.32 (m, 2H), 7.26-7.24 (m, 1H), 5.18 (s, 2H), 5.05-5.00 (m, 1H), 4.67-4.65 (m, 2H), 4.43-4.40 (m, 1H), 3.57-3.51 (m, 2H), 3.43 (s, 3H), 3.27 (s, 3H), 1.46 (s, 3H). LCMS $R_T$=1.73 min; m/z=398.1 $(M+H)^+$.

LCMS (10-80% acetonitrile in water+0.05% ammonium bicarbonate over 3 mins) retention time 1.73/min, ESI+ found [M+H]=398.1

Example 232

WX Method Q

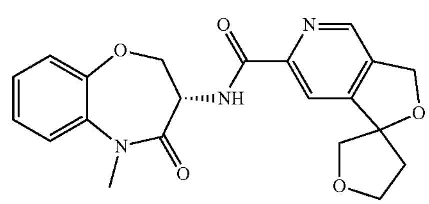 [SMILES: CN1C(=O)[C@@H](NC(=O)c2cc3c(cn2)COC32CCOC2)COc2ccccc21]

N—((S)-5-methyl-4-oxo-2,3,4,5-tetrahydrobenzo[b][1,4]oxazepin-3-yl)-4,5-dihydro-2H,3' H-spiro[furan-3,1'-furo[3,4-c]pyridine]-6'-carboxamide

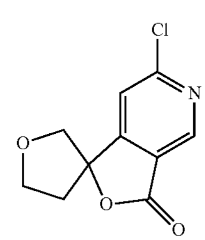 [SMILES: O=C1OC2(CCOC2)c2cc(Cl)ncc21]

Step 1: 6'-chloro-4,5-dihydro-2H,3'H-spiro[furan-3, 1'-furo[3,4-c]pyridin]-3'-one To a stirred solution of lithium diisopropylamide (2.0 M, 12.7 mL, 25.4 mmol) in tetrahydrofuran (50 mL) was added a solution of 6-chloronicotinic acid (1.0 g, 6.35 mmol) in tetrahydrofuran (10 mL) at −78° C. After addition, the mixture was stirred at −78° C. for 3 h, and then a solution of 3-oxotetrahydrofuran (5.5 g, 63.5 mmol) in tetrahydrofuran (10 mL) was added. The resulting mixture was warmed up to 25° C. and stirred for 12 h before quenched by addition of saturated aqueous ammonium chloride. The mixture was extracted with ethyl acetate (2×100 mL). The combined organic layers were washed with brine (50 mL), dried over sodium sulfate and concentrated under reduced pressure. The residue was purified by column chromatography (silica gel, 100-200 mesh, 0-40% methanol in dichloromethane) affording 6'-chloro-4,5-dihydro-2H,3'H-spiro [furan-3,1'-furo[3,4-c]pyridin]-3'-one (0.6 g, 41.8%) as a yellow solid: $^1$H NMR (400 MHz, $CD_3OD$) δ 8.71 (s, 1H), 7.90 (s, 1H), 4.29-4.13 (m, 2H), 4.09 (s, 2H), 2.70-2.38 (m, 2H). LCMS $R_T$=0.995 min; m/z=226 $(M+H)^+$.

LCMS (10 to 80% acetonitrile in water+0.05% ammonium bicarbonate over 3.0 mins) retention time 0.995 min, ESI+ found [M+H]=226

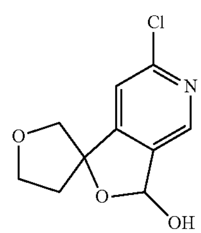 [SMILES: OC1OC2(CCOC2)c2cc(Cl)ncc21]

Step 2: 6'-chloro-4,5-dihydro-2H,3'H-spiro[furan-3, 1'-furo[3,4-c]pyridin]-3'-ol To a solution of 6'-chloro-4,5-dihydro-2H,3'H-spiro [furan-3,1'-furo[3,4-c]pyridin]-3'-one (550 mg, 2.44 mmol) in toluene (65 mL) was added diisobutylaluminumhydride (1.0 M, 7.3 mL, 7.3 mmol) dropwise at −70° C. After addition, the mixture was stirred at −60° C. for 4 h and then quenched by addition of saturated aqueous ammonium chloride (70 mL). The mixture was extracted with ethyl acetate (3×100 mL). The combined organic layers were washed with aqueous NaOH (2%, 2×50 mL) and water (20 mL). The combined aqueous layers were adjusted to pH=4 by addition of hydrochloric acid (2.0 M) and extracted with ethyl acetate (3×50 mL). The combined organic layers were dried over sodium sulfate and concentrated under reduced pressure affording crude 6'-chloro-4,5-dihydro-2H,3'H-spiro[furan-3, 1'-furo[3,4-c]pyridin]-3'-ol (450 mg, 81%) as yellow oil: LCMS $R_T$=0.521 min; m/z=228.1 $(M+H)^+$.

LCMS (10 to 80% acetonitrile in water+0.05% ammonium bicarbonate over 3.0 mins) retention time 0.521 min, ESI+ found [M+H]=228.1

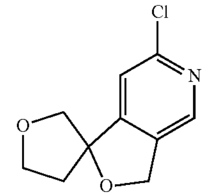 [SMILES: Clc1cc2c(cn1)COC21CCOC1]

Step 3: 6'-chloro-4,5-dihydro-2H,3'H-spiro[furan-3, 1'-furo[3,4-c]pyridine

A mixture of 6'-chloro-4,5-dihydro-2H,3'H-spiro[furan-3, 1'-furo[3,4-c]pyridin]-3'-ol (450 mg, 2.0 mmol) and trifluoroacetic acid (1.1 g, 9.9 mmol) in dichloromethane (20 mL) was stirred for 0.5 h at 0° C., and then triethylsilane (689 mg, 5.9 mmol) was added. The resulting mixture was warmed up to 25° C. and stirred for 50 h. The solvent was removed under reduced pressure and the residue was purified by column chromatography (silica gel, 100-200 mesh, 0 to 40% ethylacetae in petroleum) to afford 6'-chloro-4,5-dihydro-2H,3'H-spiro[furan-3,1'-furo[3,4-c]pyridine (140 mg, 33%) as colorless oil: LCMS $R_T$=1.119 min; m/z=212.1 $(M+H)^+$.

LCMS (10 to 80% acetonitrile in water+0.05% ammonium bicarbonate over 3.0 min) retention time 1.119 min, ESI+ found [M+H]=212.1.

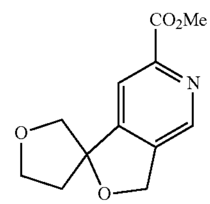 [SMILES: COC(=O)c1cc2c(cn1)COC21CCOC1]

Step 4: methyl 4,5-dihydro-2H,3'H-spiro[furan-3,1'-furo[3,4-c]pyridine]-6'-carboxylate A mixture of 6'-chloro-4,5-dihydro-2H,3'H-spiro[furan-3, 1'-furo[3,4-c]pyridine (140 mg, 0.66 mmol), 1,1'-bis(diphenylphosphino)ferrocene palladium dichloride (48 mg, 0.07 mmol) and triethylamine (669 mg, 6.6 mmol) in methanol (15 mL) was stirred at 80° C. for 12 h under carbon oxide (50 psi). The mixture was concentrated and the residue was purified by column chromatography (silica gel, 100-200 mesh, 0 to 70% ethyl acetate in petroleum ether) to afford methyl 4,5-dihydro-2H,3'H-spiro[furan-3,1'-furo[3,4-c] pyridine]-6'-carboxylate (40 mg, 25%) as brown oil, used in the next step as is.

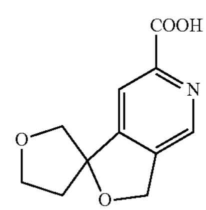 [SMILES: O=C(O)c1cc2c(cn1)COC21CCOC1]

Step 5: 4,5-dihydro-2H,3'H-spiro[furan-3,1'-furo[3,4-c]pyridine]-6'-carboxylic acid A mixture of 4,5-dihydro-2H,3'H-spiro[furan-3,1'-furo[3,4-c]pyridine]-6'-carboxylate (40 mg, 0.17 mmol) and potassium hydroxide (28 mg, 0.51 mmol) in tetrahydrofuran (5 mL) and water (2 mL) was stirred for 1 h at 25° C. The organic solvent was removed under reduced pressure, and the aqueous layer was adjusted to pH=3 by addition of hydrochloric acid (1.0 M). The aqueous layer was concentrated under reduced pressure to afford crude 4,5-dihydro-2H,3'H-spiro[furan-3,1'-furo[3,4-c]pyridine]-6'-carboxylic acid (11 mg, 30%) as a yellow solid, used in the next step as is.

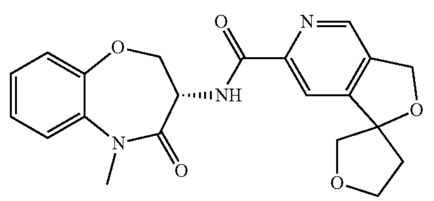 [SMILES: CN1C(=O)[C@@H](NC(=O)c2cc3c(cn2)COC32CCOC2)COc2ccccc21]

Step 6: N—((S)-5-methyl-4-oxo-2,3,4,5-tetrahydrobenzo[b][1,4]oxazepin-3-yl)-4,5-dihydro-2H,3'H-spiro[furan-3,1'-furo[3,4-c]pyridine]-6'-carboxamide A mixture of 4,5-dihydro-2H, 3'H-spiro[furan-3,1'-furo[3,4-c]pyridine]-6'-carboxylic acid (11 mg, 0.05 mmol), 1H-benzo[d][1,2,3]triazol-1-ol (11 mg, 0.08 mmol), $N^1$-((ethylimino)methylene)-$N^3$,$N^3$-dimethylpropane-1,3-diamine hydrochloride (15.0 mg, 0.08 mmol) and (3S)-3-amino-5-methyl-2,3-dihydro-1,5-benzoxazepin-4-one (10 mg, 0.05 mmol) in N,N-dimethylformamide (5 mL) was stirred at 25° C. for 12 h. The solvent was concentrated under reduced pressure and the residue was purified by RP-HPLC (acetonitrile 17-47/0.225% FA in water) to afford N—((S)-5-methyl-4-oxo-2,3,4,5-tetrahydrobenzo[b][1,4]oxazepin-3-yl)-4,5-dihydro-2H,3'H-spiro[furan-3,1'-furo[3,4-c]pyridine]-6'-carboxamide (14 mg, 70.8%) as yellow oil: $^1$H NMR (400 MHz, $CD_3OD$) δ 8.60 (s, 1H), 7.99 (s, 1H), 7.47-7.41 (m, 1H), 7.37-7.28 (m, 2H), 7.27-7.21 (m, 1H), 5.18 (s, 2H), 5.00-5.05 (m, 1H), 4.67-4.61 (m, 1H), 4.44-4.36 (m, 1H), 4.15-4.02 (m, 2H), 3.96-3.99 (m, 1H), 3.90-3.83 (m, 1H), 3.43 (s, 3H), 2.38-2.23 (m, 2H). LCMS $R_T$=0796 min; m/z=396 $(M+H)^+$.

LCMS (5 to 95% acetonitrile in water+0.03% trifluoacetic acid over 1.5 min) retention time 0.796 min, ESI+ found [M+H]+=396.

Example 233

WX Method QQQQQQ

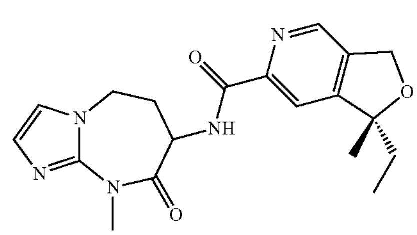 [SMILES: CC[C@@]1(C)OCc2cnc(C(=O)NC3CCn4ccnc4N(C)C3=O)cc21]

(1R)-1-ethyl-1-methyl-N-(9-methyl-8-oxo-6,7,8,9-tetrahydro-5H-imidazo [1,2-a][1,3]diazepin-7-yl)-1,3-dihydrofuro[3,4-c]pyridine-6-carboxamide

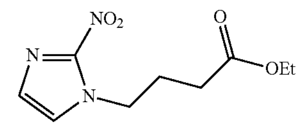 [SMILES: CCOC(=O)CCCn1ccnc1[N+](=O)[O-]]

Step 1: ethyl 4-(2-nitroimidazol-1-yl)butanoate

A mixture of 2-nitroimidazole (10.0 g, 88.4 mmol), ethyl 4-bromobutyrate (17.2 g, 88.4 mmol) and potassium carbonate (22.4 g, 176.9 mol) in N,N-dimethylformamide (20 mL) was heated to 120° C. for 2 h. The mixture was diluted with water (400 mL) and extracted with ethyl acetate (3×200 mL). The combined organic layers were washed with water (200 mL), dried over sodium sulfate and concentrated under reduced pressure. The residue was purified by column chromatography (silica gel, 100-200 mesh, 0 to 20% ethyl acetate in petroleum ether) to give ethyl 4-(2-nitroimidazol-1-yl)butanoate (9.0 g, 45%) as a colorless oil: $^1$H NMR (400 MHz, $CDCl_3$) δ 7.11 (d, J=10.4 Hz, 2H), 4.48 (t, J=7.2 Hz, 2H), 4.16-4.08 (m, 3H), 2.35 (t, J=7.2 Hz, 2H), 2.20-2.15 (m, 2H), 1.28-1.20 (m, 4H).

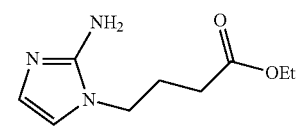

Step 2: ethyl 4-(2-amino-1H-imidazol-1-yl)butanoate

A mixture of ethyl 4-(2-nitroimidazol-1-yl)butanoate (7.0 g, 30.8 mmol) and 10% palladium on carbon (32.8 g, 30.8 mmol) in 1,4-dioxane (300 mL) was hydrogenated (15 psi) at 25° C. for 12 h. The mixture was filtered and the filtrate was concentrated under reduced pressure to afford ethyl 4-(2-amino-1H-imidazol-1-yl)butanoate (5.0 g, 81%) as a brown oil, used in the next step without further purification.

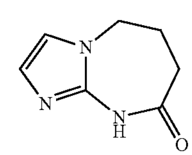 [SMILES: O=C1CCCn2ccnc2N1]

Step 3: 6,7-dihydro-5H-imidazo[1,2-a][1,3]diazepin-8(9H)-one

To a solution of ethyl 4-(2-amino-1H-imidazol-1-yl)butanoate (4.5 g, 22.8 mmol) in ethanol (50 mL) was added sodium ethoxide (7.7 g, 114.1 mmol). The mixture was stirred at 25° C. for 4 h. The solvent was removed under reduced pressure and the residue was purified by column chromatography (silica gel, 100-200 mesh, 0 to 10% methanol in dichloromethane) to give 6,7-dihydro-5H-imidazo[1,2-a][1,3]diazepin-8(9H)-one (2.0 g, 58%) as a white solid: $^1$H NMR (400 MHz, DMSO-$d_6$) δ 10.12 (br. s, 1H), 7.00 (s, 1H), 6.71 (s, 1H), 4.01 (t, J=6.8 Hz, 2H), 2.29-2.21 (m, 2H), 2.19-2.06 (m, 2H).

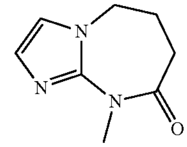

Step 4: 9-methyl-6,7-dihydro-5H-imidazo[1,2-a][1,3]diazepin-8(9H)-one

To a solution of 6,7-dihydro-5H-imidazo[1,2-a][1,3]diazepin-8(9H)-one (1.8 g, 11.9 mmol) in N,N-dimethylformamide (50 mL) was added cesium carbonate (3.9 g, 11.9 mmol) and iodomethane (1.7 g, 11.9 mmol). The mixture was stirred at 25° C. for 3 h and then concentrated under reduced pressure. The residue was purified by column chromatography (silica gel, 100-200 mesh, 0 to 10% methanol in dichloromethane) to afford 9-methyl-6,7-dihydro-5H-imidazo[1,2-a][1,3]diazepin-8(9H)-one (1.5 g, 76%) as a white solid: $^1$H NMR (400 MHz, DMSO-$d_6$) δ 7.04 (d, J=1.6 Hz, 1H), 6.79 (d, J=1.2 Hz, 1H), 3.99 (t, J=6.8 Hz, 2H), 3.17 (s, 3H), 2.23-2.13 (m, 4H).

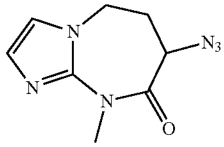

Step 5: 7-azido-9-methyl-6,7-dihydro-5H-imidazo[1,2-a][1,3]diazepin-8(9H)-one

To a mixture of 9-methyl-6,7-dihydro-5H-imidazo[1,2-a][1,3]diazepin-8(9H)-one (1.2 g, 7.3 mmol) in tetrahydrofuran (50 mL) was added lithium diisopropylamide (2.0 M, 10.9 mL, 21.7 mmol) dropwise at −78° C. After stirred at −78° C. for 30 min, p-toluenesulfonylazide (4.3 g, 21.8 mmol) in tetrahydrofuran (5 mL) was added. After addition, the mixture was stirred at −78° C. for 2 h then allowed to warm to 25° C. for another 15 h. The reaction was quenched by addition of acetic acid (0.4 mL) and stirred for 3 h at 25° C. Then the mixture was adjust to pH=8 by addition of saturated aqueous sodium carbonate. The mixture was concentrated to dryness and the residue was purified by column chromatography (silica gel, 100-200 mesh, 0 to 10% methanol in dichloromethane) to afford 7-azido-9-methyl-6,7-dihydro-5H-imidazo[1,2-a][1,3]diazepin-8(9H)-one (800 mg, 53%) as yellow oil, used as is in the next step.

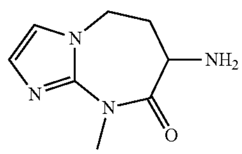

Step 6: 7-amino-9-methyl-6,7-dihydro-5H-imidazo[1,2-a][1,3]diazepin-8(9H)-one

A mixture of 7-azido-9-methyl-6,7-dihydro-5H-imidazo[1,2-a][1,3]diazepin-8(9H)-one (800 mg, 3.8 mmol) and 10% palladium on carbon (50 mg, 0.05 mmol) in methanol (10 mL) was hydrogenated (15 psi) at 25° C. for 15 h. The mixture was filtered and the filtrate was concentrated under reduced pressure to afford 7-amino-9-methyl-6,7-dihydro-5H-imidazo[1,2-a][1,3]diazepin-8(9H)-one (300 mg, 43%) as yellow oil, used in the next step without further purification.

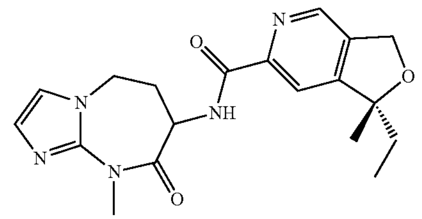 [SMILES: CC[C@@]1(C)OCc2cnc(C(=O)NC3CCn4ccnc4N(C)C3=O)cc21]

Step 7: (1R)-1-ethyl-1-methyl-N-(9-methyl-8-oxo-6,7,8,9-tetrahydro-5H-imidazo[1,2-a][1,3]diazepin-7-yl)-1,3-dihydrofuro[3,4-c]pyridine-6-carboxamide A mixture of (1R)-1-ethyl-1-methyl-3H-furo[3,4-c]pyridine-6-carboxylic acid (23 mg, 0.11 mmol), 7-amino-9-methyl-6,7-dihydro-5H-imidazo[1,2-a][1,3]diazepin-8(9H)-one (20 mg, 0.11 mmol), $N^1$-((ethylimino)methylene)-$N^3$,$N^3$-dimethyl propane-1,3-diamine hydrochloride (26 mg, 0.13 mmol) and 1H-benzo[d][1,2,3]triazol-1-ol (18 mg, 0.13 mmol) in N,N-dimethylformamide (4 mL) was stirred at 25° C. for 12 h. The reaction was concentrated under reduced pressure and the residue was purified by RP-HPLC (acetonitrile 20-50/0.05% ammonia hydroxide in water) to afford (1R)-1-ethyl-1-methyl-N-(9-methyl-8-oxo-6,7,8,9-tetrahydro-5H-imidazo[1,2-a][1,3]diazepin-7-yl)-1,3-dihydrofuro[3,4-c]pyridine-6-carboxamide (4 mg, 9.9%) as white solid: $^1$H NMR (400 MHz, $CD_3OD$) δ 8.57 (s, 1H), 7.87 (s, 1H), 7.13 (s, 1H), 7.00-6.99 (m, 1H), 5.21-5.13 (m, 2H), 4.58-4.55 (m, 1H), 4.35-4.30 (m, 1H), 4.12-4.10 (m, 1H), 3.41 (s, 3H), 2.95-2.92 (m, 1H), 2.32-2.26 (m, 1H), 1.89-1.83 (m, 2H), 1.47 (s, 3H), 0.80-0.76 (m, 3H). LCMS $R_T$=1.81 min; m/z=370.1 $(M+H)^+$.

LCMS (0-60% acetonitrile in water+0.05% ammonium bicarbonate over 3 mins) retention time 1.81 min, ESI+ found [M+H]=370.1.

Example 234

WX Method WWWW

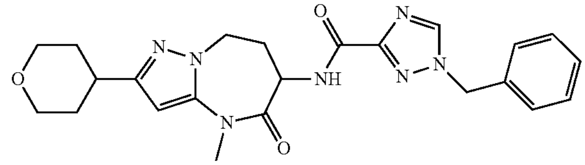 [SMILES: CN1C(=O)C(NC(=O)c2ncn(Cc3ccccc3)n2)CCn2nc(C3CCOCC3)cc21]

1-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,4-triazole-3-carboxamide

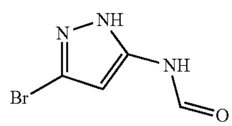

Step 1: N-(3-bromo-1H-pyrazol-5-yl)formamide

A mixture of 3-bromo-1H-pyrazol-5-amine (16.0 g, 98.8 mmol) and formic acid (50 mL, 98.8 mmol) was stirred at 110° C. in a sealed vessel for 2 h. The mixture was concentrated under reduced pressure and the residue was washed with water (50 mL) to give N-(3-bromo-1H-pyrazol-5-yl)formamide (15.0 g, 80%) as a white solid, used in the next step without further purification.

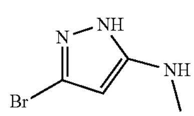

Step 2: 3-bromo-N-methyl-1H-pyrazol-5-amine

To a solution of N-(3-bromo-1H-pyrazol-5-yl)formamide (15.0 g, 79.0 mmol) in tetrahydrofuran (200 mL) was added borane (1.0 M, 315.8 mL, 315.8 mmol). The mixture was stirred at 0° C. for 2 h and then quenched by addition of methanol (30 mL) and hydrochloric acid (10%, 5 mL). The mixture was then heated at reflux for 30 min and adjusted to pH=8 by addition of aqueous sodium hydroxide (10%). The mixture was concentrated under reduced pressure and the residue was taken up in ethyl acetate (100 mL), washed with water (2×50 mL), brine (50 mL), dried over magnesium sulfate and concentration under reduced pressure. The residue was purified by column chromatography (silica gel, 100-200 mesh, 0 to 50% ethyl acetate in petroleum ether) to give 3-bromo-N-methyl-1H-pyrazol-5-amine (13.0 g, 94%) as a white solid, used as is in the next step.

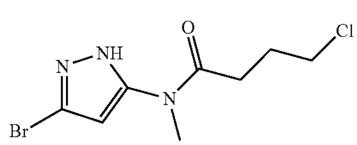

Step 3: N-(3-bromo-1H-pyrazol-5-yl)-4-chloro-N-methylbutanamide

A mixture of 3-bromo-N-methyl-1H-pyrazol-5-amine (13.5 g, 76.7 mmol) and 4-chlorobutanoyl chloride (33.5 mL, 300 mmol) was stirred at 60° C. for 3 h. After cooled, methanol (50 mL) was added into the mixture carefully and the mixture was concentrated under reduced pressure. The residue was purified by column chromatography (silica gel, 100-200 mesh, 0 to 50% ethyl acetate in petroleum ether) to give N-(3-bromo-1H-pyrazol-5-yl)-4-chloro-N-methylbutanamide (17.0 g, 79%) as a colorless oil, used in the next step without further purification.

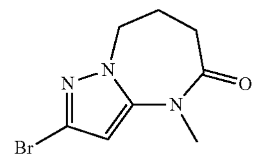

Step 4: 2-bromo-4-methyl-7,8-dihydro-4H-pyrazolo[1,5-a][1,3]diazepin-5(6H)-one

To a mixture of N-(3-bromo-1H-pyrazol-5-yl)-4-chloro-N-methylbutanamide (17.0 g, 60.6 mmol) in N,N-dimethylformamide (100 mL) was added cesium carbonate (39.5 g, 121.2 mmol) and stirred at 25° C. for 16 h. The reaction was concentrated under reduced pressure and the residue was diluted with ethyl acetate (200 mL). The mixture was washed with water (2×100 mL), brine (100 mL), dried over magnesium sulfate and concentrated under reduced pressure. The residue was then purified by column chromatography (silica gel, 100-200 mesh, 0 to 50% ethyl acetate in petroleum ether) to give 2-bromo-4-methyl-7,8-dihydro-4H-pyrazolo[1,5-a][1,3]diazepin-5(6H)-one (12.0 g, 76%) as a white solid: $^1H$ NMR (400 MHz, $CD_3OD$) δ 6.05 (s, 1H), 4.22 (t, J=6.4 Hz, 2H), 3.24 (s, 3H), 2.43-2.32 (m, 4H).

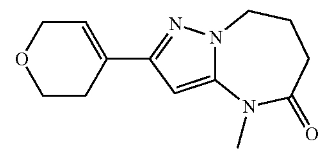 [SMILES: CN1C(=O)CCCn2nc(C3=CCOCC3)cc21]

Step 5: 2-(3,6-dihydro-2H-pyran-4-yl)-4-methyl-7,8-dihydro-4H-pyrazolo[1,5-a][1,3]diazepin-5(6H)-one A mixture of 2-bromo-4-methyl-7,8-dihydro-4H-pyrazolo[1,5-a][1,3]diazepin-5(6H)-one (500 mg, 2.1 mmol), 3,6-dihydro-2h-pyran-4-boronicacidpinacolester (646 mg, 3.1 mmol), 1,1'-bis(diphenylphosphino) ferrocene palladium dichloride (150 mg, 0.2 mmol) and potassium carbonate (566 mg, 4.1 mmol) in 1,4-dioxane (20 mL) and water (4 mL) was heated 15 to 110° C. for 30 min under microwave conditions. The mixture was concentrated under reduced pressure and the residue was purified by preparative TLC (50% ethyl acetate in petroleum ether, Rf=0.3) to afford 2-(3,6-dihydro-2H-pyran-4-yl)-4-methyl-7,8-dihydro-4H-pyrazolo[1,5-a][1,3]diazepin-5(6H)-one (400 mg, 79%) as white solid. LCMS $R_T$=1.14 min; m/z=248.1 $(M+H)^+$.

LCMS (10 to 80% acetonitrile in water+0.05% ammonium bicarbonate over 3 mins) retention time 1.14 min, ESI+ found [M+H]=248.1

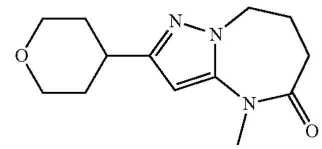 [SMILES: CN1C(=O)CCCn2nc(C3CCOCC3)cc21]

Step 6: 4-methyl-2-(tetrahydro-2H-pyran-4-yl)-7,8-dihydro-4H-pyrazolo[1,5-a][1,3]diazepin-5(6H)-one A mixture of 2-(3,6-dihydro-2H-pyran-4-yl)-4-methyl-7,8-dihydro-4H-pyrazolo[1,5-a][1,3]diazepin-5(6H)-one (650 mg, 2.6 mmol) and 10% palladium on carbon (2.8 g, 2.6 mmol) in methanol (20 mL) was hydrogenated (15 psi) at 25° C. for 12 h. The mixture was filtered and the filtrate was concentrated under reduced pressure to afford 4-methyl-2-(tetrahydro-2H-pyran-4-yl)-7,8-dihydro-4H-pyrazolo[1,5-a][1,3]diazepin-5(6H)-one (510 mg, 78%) as white solid: LCMS $R_T$=0.574 min; m/z=250.1 $(M+H)^+$.

LCMS (5 to 95% acetonitrile in water+0.03% trifluoacetic acid over 1.5 mins) retention time 0.574 min, ESI+ found [M+H]=250.1

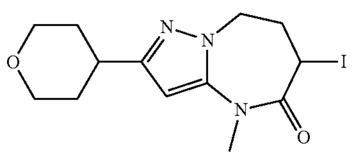 [SMILES: CN1C(=O)C(I)CCn2nc(C3CCOCC3)cc21]

Step 7: 6-iodo-4-methyl-2-(tetrahydro-2H-pyran-4-yl)-7,8-dihydro-4H-pyrazolo[1,5-a][1,3]diazepin-5(6H)-one To a solution of 4-methyl-2-(tetrahydro-2H-pyran-4-yl)-7,8-dihydro-4H-pyrazolo[1,5-a][1,3]diazepin-5(6H)-one (510 mg, 2.1 mmol) in dichloromethane (20 mL) was added N1,N1,N2,N2-tetramethylethane-1,2-diamine (1.4 g, 12.3 mmol), followed by iodotrimethylsilane (2.5 g, 12.3 mmol) at −15° C. The resulting solution was stirred 2 h at −15 OC, and iodine (1.6 g, 6.1 mmol) was added in one portion. After stirred for 2 h at −15° C., the reaction mixture was quenched by addition of saturated sodium bisulfite (30 mL). The mixture was extracted with dichloromethane (3×100 mL). The combined organic extracts were dried over sodium sulfate and concentrated under reduced pressure. The residue was purified by column chromatography (silica gel, 100-200 mesh, 0 to 50% ethyl acetate in petroleum ether) to give 6-iodo-4-methyl-2-(tetrahydro-2H-pyran-4-yl)-7,8-dihydro-4H-pyrazolo[1,5-a][1,3]diazepin-5(6H)-one (520 mg, 67.7% yield) as brown solid: LCMS $R_T$=0.65 min; m/z=376.0 $(M+H)^+$.

LCMS (5 to 95% acetonitrile in water+0.03% trifluoacetic acid over 1.5 mins) retention time 0.65 min, ESI+ found [M+H]=376.0

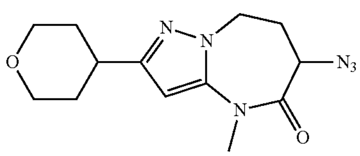 [SMILES: CN1C(=O)C(N=[N+]=[N-])CCn2nc(C3CCOCC3)cc21]

Step 8: 6-azido-4-methyl-2-(tetrahydro-2H-pyran-4-yl)-7,8-dihydro-4H-pyrazolo[1,5-a][1,3]diazepin-5(6H)-one A mixture of 6-iodo-4-methyl-2-(tetrahydro-2H-pyran-4-yl)-7,8-dihydro-4H-pyrazolo[1,5-a][1,3]diazepin-5(6H)-one (510 mg, 1.4 mmol) and sodium azide (106 mg, 1.6 mmol) in N,N-dimethylformamide (2 mL) was stirred for 2 h at 25° C. The reaction mixture was poured into ice water (20 mL) and extracted with ethyl acetate (3×20 mL). The combined organic layers were concentrated under reduced pressure and the residue was purified by column chromatography (silica gel, 100-200 mesh, 0 to 50% ethyl acetate in petroleum ether) to afford 6-azido-4-methyl-2-(tetrahydro-2H-pyran-4-yl)-7,8-dihydro-4H-pyrazolo[1,5-a][1,3]diazepin-5(6H)-one (340 mg, 86%) as a light yellow oil: LCMS $R_T$=0.63 min; m/z=291.2 $(M+H)^+$.

LCMS (5 to 95% acetonitrile in water+0.03% trifluoacetic acid over 1.5 mins) retention time 0.63 min, ESI+ found [M+H]=291.2

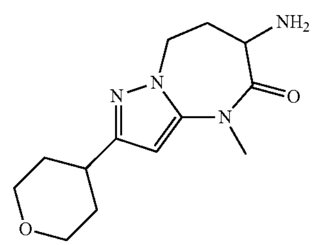 [SMILES: CN1C(=O)C(N)CCn2nc(C3CCOCC3)cc21]

Step 9: 6-amino-4-methyl-2-(tetrahydro-2H-pyran-4-yl)-7,8-dihydro-4H-pyrazolo[1,5-a][1,3]diazepin-5(6H)-one A mixture of 6-azido-4-methyl-2-(tetrahydro-2H-pyran-4-yl)-7,8-dihydro-4H-pyrazolo[1,5-a][1,3]diazepin-5(6H)-one (340 mg, 1.2 mmol) and 10% palladium on carbon (124 mg, 0.12 mmol) in methanol (30 mL) was hydrogenated (15 psi) at 25° C. for 3 h. The mixture was filtered and the filtrate was concentrated under reduced pressure to afford crude 6-amino-4-methyl-2-tetrahydropyran-4-yl-7,8-dihydro-6H-pyrazolo[1,5-a][1,3]diazepin-5-one (300 mg, 97%) as white solid, used in the next step without further purification.

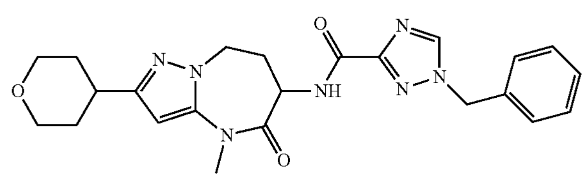 [SMILES: CN1C(=O)C(NC(=O)c2ncn(Cc3ccccc3)n2)CCn2nc(C3CCOCC3)cc21]

Step 10: 1-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,4-triazole-3-carboxamide A mixture of 6-amino-4-methyl-2-tetrahydropyran-4-yl-7,8-dihydro-6H-pyrazolo[1,5-a][1,3]diazepin-5-one (20 mg, 0.08 mmol), 1-benzyl-1,2,4-triazole-3-carboxylic acid (15.4 mg, 0.08 mmol), 1H-benzo[d][1,2,3]triazol-1-ol (15 mg, 0.11 mmol) and N1-((ethylimino)methylene)-N3,N3-dimethylpropane-1,3-diamine hydrochloride (18 mg, 0.11 mmol) in N,N-dimethylformamide (4 mL) was stirred at 25° C. for 12 h. The reaction mixture was concentrated under reduced pressure and the residue was purified by RP-HPLC (25-35% acetonitrile in water and 0.05% ammonia hydroxide) to afford 1-benzyl-N-(4-methyl-5-oxo-2-(tetrahydro-2H-pyran-4-yl)-5,6,7,8-tetrahydro-4H-pyrazolo[1,5-a][1,3]

diazepin-6-yl)-1H-1,2,4-triazole-3-carboxamide (26.3 mg, 76%) as white solid: $^1$H NMR (400 MHz, $CD_3OD$) δ 8.56 (s, 1H), 7.36-7.32 (m, 5H), 6.19 (s, 1H), 5.47 (s, 2H), 4.53-4.51 (m, 1H), 4.50-4.48 (m, 1H), 4.33-4.31 (m, 1H), 4.01-3.99 (m, 2H), 3.57-3.51 (m, 2H), 3.33 (s, 3H), 2.89-2.84 (m, 2H), 2.26-2.25 (m, 1H), 1.90-1.85 (m, 2H), 1.79-1.75 (m, 2H). LCMS $R_T$=1.67 min; m/z=450.2 $(M+H)^+$.

LCMS (0 to 60% acetonitrile in water+0.03% trifluoacetic acid over 3 mins) retention time 1.67 min, ESI+ found [M+H]=450.2.

Example 235

WX Method XXXX

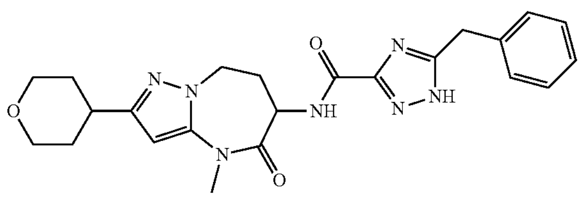 [SMILES: CN1C(=O)C(NC(=O)c2n[nH]c(Cc3ccccc3)n2)CCn2nc(C3CCOCC3)cc21]

5-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,4-triazole-3-carboxamide A mixture of 6-amino-4-methyl-2-tetrahydropyran-4-yl-7,8-dihydro-6H-pyrazolo[1,5-a][1,3]diazepin-5-one (20 mg, 0.08 mmol), 5-benzyl-1H-1,2,4-triazole-3-carboxylic acid (15 mg, 0.08 mmol), 1H-benzo[d][1,2,3]triazol-1-ol (15 mg, 0.11 mmol) and N1-((ethylimino)methylene)-N3,N3-dimethyl propane-1,3-diamine hydrochloride (18 mg, 0.11 mmol) in N,N-dimethylformamide (4 mL) was stirred at 25° C. for 12 h. The reaction mixture was concentrated under reduced pressure and the residue was purified by RP-HPLC (10-40% acetonitrile in water and 0.05% ammonia hydroxide) to afford 5-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,4-triazole-3-carboxamide (11.4 mg, 32%) as white solid: $^1$H NMR (400 MHz, DMSO-$d_6$) δ 7.30-7.20 (m, 5H), 6.19 (s, 1H), 4.30-4.28 (m, 2H), 4.25-4.22 (m, 3H), 3.87-3.84 (m, 2H), 3.30-3.26 (m, 2H), 3.18 (s, 3H), 2.78-2.73 (m, 1H), 2.42-2.40 (m, 2H), 1.80-1.56 (m, 4H). LCMS $R_T$=1.64 min; m/z=450.2 $(M+H)^+$.

LCMS (0 to 60% acetonitrile in water+0.03% trifluoacetic acid over 3 mins) retention time 1.64 min, ESI+ found [M+H]=450.2.

Example 236

WX Method ZZZZ

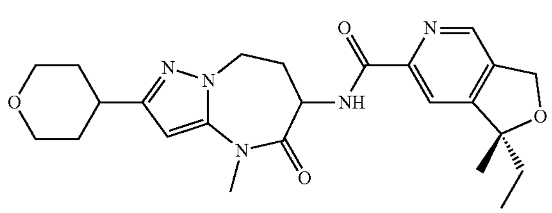 [SMILES: CC[C@@]1(C)OCc2cnc(C(=O)NC3CCn4nc(C5CCOCC5)cc4N(C)C3=O)cc21]

(1R)-1-ethyl-1-methyl-N-(4-methyl-5-oxo-2-(tetrahydro-2H-pyran-4-yl)-5,6,7,8-tetrahydro-4H-pyrazolo[1,5-a][1,3]diazepin-6-yl)-1,3-dihydrofuro[3,4-c]pyridine-6-carboxamide A mixture of 6-amino-4-methyl-2-tetrahydropyran-4-yl-7,8-dihydro-6H-pyrazolo[1,5-a][1,3]diazepin-5-one (20 mg, 0.08 mmol), (R)-1-ethyl-1-methyl-1,3-dihydrofuro[3,4-c]pyridine-6-carboxylic acid (15 mg, 0.08 mmol), 1H-benzo[d][1,2,3]triazol-1-ol (15 mg, 0.11 mmol) and N1-((ethylimino)methylene)-N3,N3-dimethylpropane-1,3-diamine hydrochloride (18 mg, 0.11 mmol) in N,N-dimethylformamide (4 mL) was stirred at 25° C. for 12 h. The reaction mixture was concentrated under reduced pressure and the residue was purified by RP-HPLC (31-61% acetonitrile in water and 0.05% ammonia hydroxide) to afford (1R)-1-ethyl-1-methyl-N-(4-methyl-5-oxo-2-(tetrahydro-2H-pyran-4-yl)-5,6,7,8-tetrahydro-4H-pyrazolo[1,5-a][1,3]diazepin-6-yl)-1,3-dihydrofuro[3,4-c]pyridine-6-carboxamide (16 mg, 46%) as white solid: $^1$H NMR (400 MHz, $CD_3OD$) δ 8.56 (s, 1H), 7.86 (s, 1H), 6.20 (s, 1H), 5.16-5.15 (m, 2H), 4.59-4.52 (m, 1H), 4.36-4.34 (m, 1H), 4.29-4.25 (m, 1H), 4.02-4.00 (m, 2H), 3.58-3.53 (m, 2H), 3.35 (s, 3H), 2.94-2.87 (m, 2H), 2.30-2.21 (m, 1H), 1.89-1.81 (m, 6H), 1.46 (s, 3H), 0.77 (t, J=7.2 Hz, 3H). LCMS $R_T$=0.79 min; m/z=454.2 $(M+H)^+$.

LCMS (5 to 95% acetonitrile in water+0.03% trifluoacetic acid over 1.5 mins) retention time 0.79 min, ESI+ found [M+H]=454.2.

Example 237

WX Method YYYY

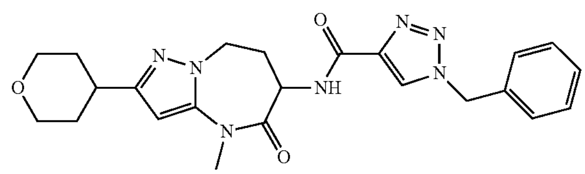 [SMILES: CN1C(=O)C(NC(=O)c2cn(Cc3ccccc3)nn2)CCn2nc(C3CCOCC3)cc21]

1-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,3-triazole-4-carboxamide A mixture of 6-amino-4-methyl-2-tetrahydropyran-4-yl-7,8-dihydro-6H-pyrazolo[1,5-a][1,3]diazepin-5-one (20 mg, 0.08 mmol), 1-benzyltriazole-4-carboxylic acid (16 mg, 0.08 mmol), 1H-benzo[d][1,2,3]triazol-1-ol (15 mg, 0.11 mmol) and N1-((ethylimino)methylene)-N3,N3-dimethyl propane-1,3-diamine hydrochloride (18 mg, 0.11 mmol) in N,N-dimethylformamide (4 mL) was stirred at 25° C. for 12 h. The reaction mixture was concentrated under reduced pressure and the residue was purified by RP-HPLC (28-38% acetonitrile in water and 0.05% ammonia hydroxide) to afford 1-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,3-triazole-4-carboxamide (17 mg, 49.3%) as white solid: $^1$H NMR (400 MHz, $CD_3OD$) δ 8.34 (s, 1H), 7.37-7.32 (m, 5H), 6.18 (s, 1H), 5.63 (s, 2H), 4.53-4.48 (m, 1H), 4.34-4.32 (m, 1H), 4.26-4.17 (m, 1H), 4.01-3.98 (m, 2H), 3.57-3.51 (m, 2H), 3.33 (s, 3H), 2.88-

2.82 (m, 2H), 2.28-2.21 (m, 1H), 1.87-1.76 (m, 4H). LCMS $R_T$=1.72 min; m/z=450.1 $(M+H)^+$.

LCMS (0 to 60% acetonitrile in water+0.03% trifluoacetic acid over 2 mins) retention time 1.72 min, ESI+ found [M+H]=450.1.

Example 238

WX Method V

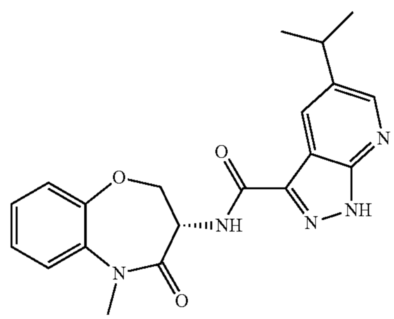 [SMILES: CC(C)c1cnc2[nH]nc(C(=O)N[C@H]3COc4ccccc4N(C)C3=O)c2c1]

(S)-5-isopropyl-N-(5-methyl-4-oxo-2,3,4,5-tetrahydrobenzo[b][1,4]oxazepin-3-yl)-1H-pyrazolo[3,4-b]pyridine-3-carboxamide

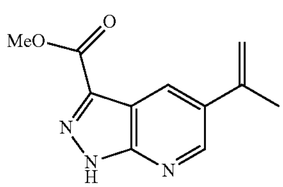 [SMILES: C=C(C)c1cnc2[nH]nc(C(=O)OC)c2c1]

Step 1: methyl 5-(prop-1-en-2-yl)-1H-pyrazolo[3,4-b]pyridine-3-carboxylate

A mixture of methyl 5-bromo-1H-pyrazolo[3,4-b]pyridine-3-carboxylate (375 mg, 1.46 mmol), 1,1'-bis(diphenylphosphino)ferrocene palladium dichloride (54 mg, 0.07 mmol), potassiumisopropenyltrifluoroborate (433 mg, 2.93 mmol) and cesium carbonate (1193 mg, 3.66 mmol) in 1,4-dioxane (5 mL) and water (1 mL) was heated at 120° C. for 45 min under microwave conditions. After cooled, the solvent was removed under reduced pressure and the residue was purified by column chromatography (silica gel, 100-200 mesh, 0 to 50% ethyl acetate in petroleum ether) to afford methyl 5-(prop-1-en-2-yl)-1H-pyrazolo[3,4-b]pyridine-3-carboxylate (130 mg, 41%) as a white solid: LCMS $R_T$=0.769 min; m/z=217.8 $(M+H)^+$.

LCMS (5 to 95% acetonitrile in water+0.03% formic acid over 1.5 mins) retention time 0.769 min, ESI+ found [M+H]= 217.8.

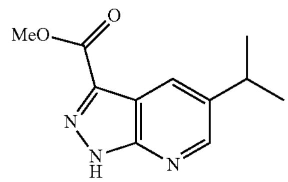 [SMILES: COC(=O)c1n[nH]c2ncc(C(C)C)cc12]

Step 2: methyl 5-isopropyl-1H-pyrazolo[3,4-b]pyridine-3-carboxylate

A mixture of methyl 5-(prop-1-en-2-yl)-1H-pyrazolo[3,4-b]pyridine-3-carboxylate (130 mg, 0.60 mmol) and 10% palladium on carbon (64 mg, 0.60 mmol) in methanol (15 mL) was hydrogenated (15 psi) at 25° C. for 16 h. The mixture was filtered and the filtrate was concentrated under reduced pressure affording crude methyl 5-isopropyl-1H-pyrazolo[3,4-b]pyridine-3-carboxylate (100 mg, 76%) as colorless oil: LCMS $R_T$=0.765 min; m/z=219.9 $(M+H)^+$.

LCMS (5 to 95% acetonitrile in water+0.03% formic acid over 1.5 mins) retention time 0.765 min, ESI+ found [M+H]= 219.9.

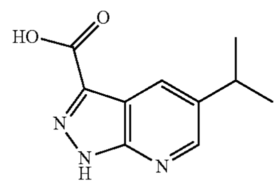

Step 3: 5-isopropyl-1H-pyrazolo[3,4-b]pyridine-3-carboxylic acid

A mixture of methyl 5-isopropyl-1H-pyrazolo[3,4-b]pyridine-3-carboxylate (50 mg, 0.23 mmol) and lithium hydroxide hydrate (96 mg, 2.28 mmol) in tetrahydrofuran (5 mL) and water (1 mL) was stirred for 20 h at 20° C. The organic solvent was removed under reduced pressure, and the aqueous layer was adjusted to pH=4 by addition of hydrochloric acid (1.0 M). The solution was extracted with ethyl acetate (3×20 mL). The combined organic layers were dried over sodium sulfate and concentrated under reduced pressure to afford crude 5-isopropyl-1H-pyrazolo[3,4-b]pyridine-3-carboxylic acid (40 mg, 85%) as a white solid: LCMS $R_T$=0.599 min; m/z=205.8 $(M+H)^+$.

LCMS (5 to 95% acetonitrile in water+0.03% formic acid over 1.5 mins) retention time 0.599 min, ESI+ found [M+H]= 205.8.

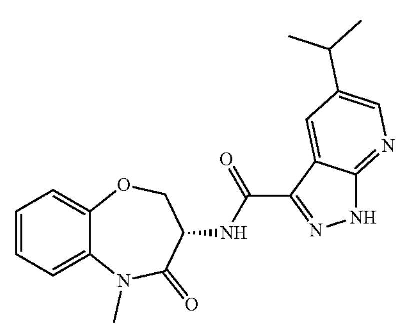 [SMILES: CC(C)c1cnc2[nH]nc(C(=O)N[C@H]3COc4ccccc4N(C)C3=O)c2c1]

Step 4: (S)-5-isopropyl-N-(5-methyl-4-oxo-2,3,4,5-tetrahydrobenzo[b][1,4]oxazepin-3-yl)-1H-pyrazolo[3,4-b]pyridine-3-carboxamide A mixture of 5-isopropyl-1H-pyrazolo[3,4-b]pyridine-3-carboxylic acid (40 mg, 0.19 mmol), (3S)-3-amino-5-methyl-2,3-dihydro-1,5-benzoxazepin-4-one (41 mg, 0.21 mmol), 1H-benzo[d][1,2,3]triazol-1-ol (32 mg, 0.23 mmol) and $N^1$-((ethylimino) methylene)-$N^3$,$N^3$-dimethylpropane-1,3-diamine hydrochloride (45 mg, 0.23 mmol) in N,N-dimethylformamide (5 mL) was stirred at 15° C. for 1 h. The reaction mixture was concentrated under reduced pressure. The residue was purified by RP-HPLC (30-60% acetonitrile in water and 0.05% hydrochloric acid) to afford (S)-5-isopropyl-N-(5-methyl-4-oxo-2,3,4,5-tetrahydrobenzo[b][1,4]oxazepin-3-yl)-1H-pyrazolo[3,4-b]pyridine-3-carboxamide (29 mg, 39%) as a white solid: $^1$H NMR (400 MHz, DMSO-$d_6$) δ 14.22 (s, 1H), 8.57-8.54 (m, 2H), 8.22 (d, J=1.6 Hz, 1H), 7.53-7.52 (m, 1H), 7.51-7.26 (m, 3H), 4.96-4.91 (m, 1H), 4.69-4.63 (m, 1H), 4.48-4.43 (m, 1H), 3.33 (s, 3H), 3.14-3.07 (m, 1H), 1.26 (d, J=7.2 Hz, 6H): LCMS $R_T$=0.840 min; m/z=380.1 $(M+H)^+$.

LCMS (5 to 95% acetonitrile in water+0.03% formic acid over 1.5 mins) retention time 0.840 min, ESI+ found [M+H]= 380.1.

Example 239

WX Method W

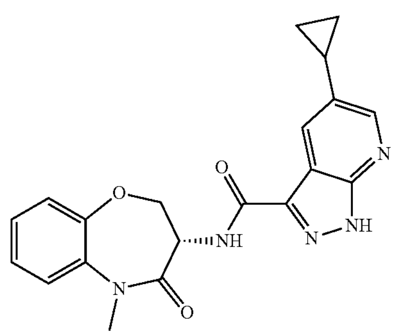 [SMILES: CN1C(=O)[C@@H](NC(=O)c2n[nH]c3ncc(C4CC4)cc23)COc2ccccc21]

(S)-5-cyclopropyl-N-(5-methyl-4-oxo-2,3,4,5-tetrahydrobenzo[b][1,4]oxazepin-3-yl)-1H-pyrazolo[3,4-b]pyridine-3-carboxamide

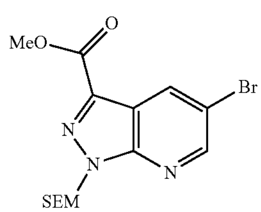 [SMILES: COC(=O)c1nn(COCC[Si](C)(C)C)c2ncc(Br)cc12]

Step 1: methyl 5-bromo-1-((2-(trimethylsilyl)ethoxy)methyl)-1H-pyrazolo[3,4-b]pyridine-3-carboxylate To a solution of methyl 5-bromo-1H-pyrazolo[3,4-b]pyridine-3-carboxylate (200 mg, 0.78 mmol) in tetrahydrofuran (5 mL) was added triethylamine (158 mg, 1.56 mmol) and 2-(trimethylsilyl)ethoxymethyl chloride (195 mg, 1.17 mmol). The reaction was stirred at 25° C. for 20 h and diluted with water (10 mL). The mixture was extracted with ethyl acetate (2×15 mL). The combined organic layers were dried over sodium sulfate and concentrated under reduced pressure to afford crude methyl 5-bromo-1-((2-(trimethyl silyl)ethoxy)methyl)-1H-pyrazolo[3,4-b]pyridine-3-carboxylate (300 mg, 99%) as yellow oil: LCMS $R_T$=0.999 min; m/z=387.8 $(M+H)^+$.

LCMS (5 to 95% acetonitrile in water+0.03% formic acid over 1.5 mins) retention time 0.999 min, ESI+ found [M+H]= 387.8.

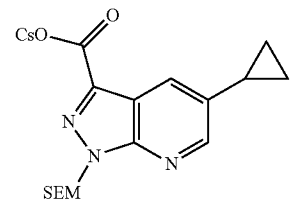

Step 2: Cesium 5-cyclopropyl-1-((2-(trimethylsilyl)ethoxy)methyl)-1H-pyrazolo[3,4-b]pyridine-3-carboxylate A mixture of methyl 5-bromo-1-((2-(trimethylsilyl)ethoxy)methyl)-1H-pyrazolo[3,4-b]pyridine-3-carboxylate (100 mg, 0.26 mmol), cesium carbonate (211 mg, 0.65 mmol), 1,1'-bis(diphenylphosphino)ferrocene palladium dichloride (9 mg, 0.01 mmol) and cyclopropylboronic acid (45 mg, 0.52 mmol) in 1,4-dioxane (2.5 mL) and water (0.5 mL) was heated at 120° C. for 60 min under microwave conditions. The mixture was filtered and the filtrate was concentrated under reduced pressure to afford crude cesium 5-cyclopropyl-1-((2-(trimethylsilyl)ethoxy)methyl)-1H-pyrazolo[3,4-b]pyridine-3-carboxylate (120 mg, 100%) as a dark solid: LCMS $R_T$=0.866 min; m/z=333.9 $(M+H)^+$.

LCMS (5 to 95% acetonitrile in water+0.03% formic acid over 1.5 mins) retention time 0.866 min, ESI+ found [M+H]= 333.9.

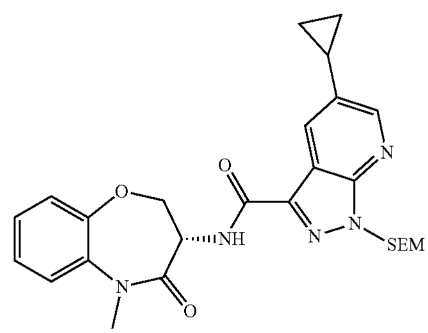 [SMILES: CN1C(=O)[C@@H](NC(=O)c2nn(COCC[Si](C)(C)C)c3ncc(C4CC4)cc23)COc2ccccc21]

Step 3: (S)-5-cyclopropyl-N-(5-methyl-4-oxo-2,3,4,5-tetrahydrobenzo[b][1,4]oxazepin-3-yl)-1-((2-(trimethylsilyl)ethoxy)methyl)-1H-pyrazolo[3,4-b]pyridine-3-carboxamide A mixture of (3S)-3-amino-5-methyl-2,3-dihydro-1,5-benzoxazepin-4-one (40 mg, 0.21 mmol), cesium 5-cyclopropyl-1-((2-(trimethylsilyl)ethoxy)methyl)-1H-pyrazolo[3,4-b]pyridine-3-carboxylate (107 mg, 0.23 mmol) and (7-azabenzotriazol-1-yloxy) tripyrrolidinophosphonium hexafluorophosphate (130 mg, 0.25 mmol) in N,N-dimethylacetamide (2 mL) was stirred at 25° C. for 20 h. The solution was diluted with water (10 mL) and extracted with ethyl acetate (2×15 mL). The combined organic layers were concentrated under reduced pressure. The residue was purified by preparative TLC (25% ethyl acetate in petroleum ether) to afford (S)-5-cyclopropyl-N-(5-methyl-4-oxo-2,3,4,5-tetrahydrobenzo[b][1,4]oxazepin-3-yl)-1-((2-(trimethylsilyl)ethoxy)methyl)-1H-pyrazolo[3,4-b]pyridine-3-carboxamide (65 mg, 61%) as a white solid: LCMS $R_T$=0.868 min; m/z=531.0 $(M+Na)^+$.

LCMS (5 to 95% acetonitrile in water+0.03% formic acid over 1.5 mins) retention time 0.868 min, ESI+ found [M+Na]=531.0.

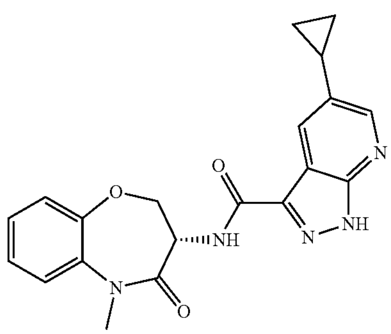 [SMILES: CN1C(=O)[C@@H](NC(=O)c2n[nH]c3ncc(C4CC4)cc23)COc2ccccc21]

Step 4: (S)-5-cyclopropyl-N-(5-methyl-4-oxo-2,3,4,5-tetrahydrobenzo[b][1,4]oxazepin-3-yl)-1H-pyrazolo[3,4-b]pyridine-3-carboxamide To a solution of (S)-5-cyclopropyl-N-(5-methyl-4-oxo-2,3,4,5-tetrahydrobenzo[b][1,4]oxazepin-3-yl)-1-((2-(trimethylsilyl)ethoxy)methyl)-1H-pyrazolo[3,4-b]pyridine-3-carboxamide (60 mg, 0.12 mmol) in dichloromethane (2 mL) was added trifluoroacetic acid (0.09 mL, 1.18 mmol). The mixture was stirred at 25° C. for 1 h and the solvent was removed under reduced pressure. The residue was purified by RP-HPLC (25-55% acetonitrile in water and 0.05% hydrochloric acid) to afford (S)-5-cyclopropyl-N-(5-methyl-4-oxo-2,3,4,5-tetrahydrobenzo[b][1,4]oxazepin-3-yl)-1H-pyrazolo[3,4-b]pyridine-3-carboxamide (29 mg, 38%) as a white solid: $^1H$ NMR (400 MHz, DMSO-$d_6$) δ 14.20 (s, 1H), 8.54 (d, J=8.0 Hz, 1H), 8.46 (s, 1H), 7.98 (s, 1H), 7.52-7.50 (m, 1H), 7.34-7.25 (m, 3H), 4.94-4.90 (m, 1H), 4.68-4.62 (m, 1H), 4.47-4.42 (m, 1H), 3.32 (s, 3H), 2.15-2.09 (m, 1H), 1.04-1.00 (m, 2H), 0.74-0.71 (m, 2H). LCMS $R_T$=0.844 min; m/z=378.1 $(M+H)^+$.

LCMS (5 to 95% acetonitrile in water+0.03% formic acid over 1.5 mins) retention time 0.844 min, ESI+ found [M+H]= 378.1.

Example 240

WX Method SS

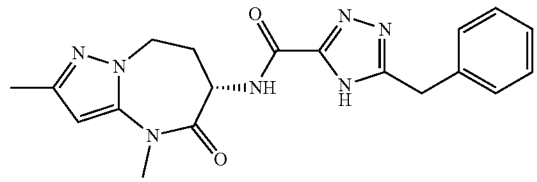 [SMILES: Cc1cc2n(n1)CC[C@H](NC(=O)c1nnc(Cc3ccccc3)[nH]1)C(=O)N2C]

(S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide A mixture of 5-benzyl-4H-1,2,4-triazole-3-carboxylic acid (47 mg, 0.23 mmol), (6S)-6-amino-2,4-dimethyl-7,8-dihydro-6H-pyrazolo[1,5-a][1,3]diazepin-5-one (30 mg, 0.15 mmol), 1H-benzo[d][1,2,3]triazol-1-ol (31 mg, 0.23 mmol) and $N^1$-((ethylimino)methylene)-$N^3$,$N^3$-dimethyl-propane-1,3-diamine hydrochloride (44 mg, 0.23 mmol) in N,N-dimethylformamide (5 mL) was stirred at 25° C. for 1 h. The reaction was concentrated under reduced pressure and the residue was purified by SFC (SFC80; Chiralpak OD (100 mm*4.6 mm, 3 um); Supercritical $CO_2$/ethanol+DEA=5/40; 2.8 ml/min) to afford (S)-5-benzyl-N-(2,4-dimethyl-5-oxo-5,6,7,8-tetrahydr-4H-pyrazolo[1,5-a][1,3]diazepin-6-yl)-4H-1,2,4-triazole-3-carboxamide (32 mg, 54%) as white solid: $^1H$ NMR (400 MHz, $CD_3OD$): δ 7.41-7.31 (m, 5H), 6.43 (s, 1H), 4.73-4.68 (m, 1H), 4.52-4.47 (m, 1H), 4.43-4.38 (m, 3H), 3.38 (s, 3H), 2.93-2.83 (m, 1H), 2.48-2.41 (m, 4H). LCMS $R_T$=1.089 min; m/z=380.1 $(M+H)^+$.

LCMS (0 to 60% acetonitrile in water+0.03% trifluoacetic acid over 2 mins) retention time 1.089 min, ESI+ found $[M+H]^+$=380.1

Example 241

WX Method TT

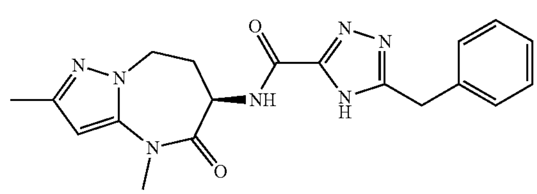 [SMILES: Cc1cc2n(n1)CC[C@@H](NC(=O)c1nnc(Cc3ccccc3)[nH]1)C(=O)N2C]

(R)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide A mixture of 5-benzyl-4H-1,2,4-triazole-3-carboxylic acid (47 mg, 0.23 mmol), (6R)-6-amino-2,4-dimethyl-7,8-dihydro-6H-pyrazolo[1,5-a][1,3]diazepin-5-one (30 mg, 0.15 mmol), 1H-benzo[d][1,2,3]triazol-1-ol (31 mg, 0.23 mmol) and $N^1$-((ethylimino)methylene)-$N^3$,$N^3$-dimethyl-propane-1,3-diamine hydrochloride (44 mg, 0.23 mmol) in N,N-dimethylformamide (5 mL) was stirred at 25° C. for 1 h. The reaction was concentrated under reduced pressure and the residue was purified by RP-HPLC (acetonitrile 20-50%/0.05% hydrogen chloride in water) to afford (R)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide (39.8 mg, 67%) as white solid: $^1$H NMR (400 MHz, $CD_3OD$): δ 7.41-7.33 (m, 5H), 6.39 (s, 1H), 4.70-4.63 (m, 1H), 4.49-4.39 (m, 2H), 4.36 (s, 2H), 3.37 (s, 3H), 2.92-2.82 (m, 1H), 2.46-2.41 (m, 1H), 2.39 (s, 3H). LCMS $R_T$=1.090 min; m/z=380.1 $(M+H)^+$.

LCMS (0 to 60% acetonitrile in water+0.03% trifluoacetic acid over 2 mins) retention time 1.090 min, ESI+ found [M+H]-=380.1

Example 242

WX Method UUU

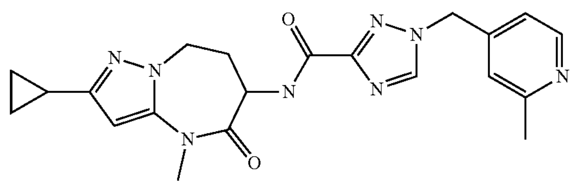 [SMILES: Cc1cc(Cn2cnc(C(=O)NC3CCn4nc(C5CC5)cc4N(C)C3=O)n2)ccn1]

N-(2-cyclopropyl-4-methyl-5-oxo-5,6,7,8-tetrahydro-4H-pyrazolo[1,5-a][1,3]diazepin-6-yl)-1-((2-methylpyridin-4-yl)methyl)-1H-1,2,4-triazole-3-carboxamide To a suspension of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (150 mg, 0.48 mmol) and potassium carbonate (197 mg, 1.43 mmol) in N,N-dimethylformamide (6 mL) was added 4-(chloromethyl)-2-methylpyridine hydrochloride (102 mg, 0.57 mmol). The mixture was stirred at 25° C. for 12 h and then filtered. The filtrate was evaporated under reduced pressure and the residue was purified by RP-HPLC (methanol 40-70%/0.05% ammonia hydroxide in water) to afford N-(2-cyclopropyl-4-methyl-5-oxo-5,6,7,8-tetrahydro-4H-pyrazolo[1,5-a][1,3]diazepin-6-yl)-1-((2-methylpyridin-4-yl)methyl)-1H-1,2,4-triazole-3-carboxamide (28 mg, 14%): $^1$H NMR (400 MHz, $CD_3OD$) δ 8.66 (s, 1H), 8.38 (d, J=5.2 Hz, 1H), 7.20 (s, 1H), 7.11 (d, J=5.2 Hz, 1H), 6.01 (s, 1H), 5.54 (s, 2H), 4.55-4.51 (m, 1H), 4.32-4.28 (m, 1H), 4.23-4.19 (m, 1H), 2.87-2.80 (m, 1H), 2.51 (s, 3H), 2.28-2.21 (m, 1H), 1.93-1.87 (m, 1H), 0.97-0.90 (m, 2H), 0.77-0.70 (m, 2H). LCMS $R_T$=1.31 min; m/z=421.2 $(M+H)^+$.

LCMS (5 to 95% acetonitrile in water+0.03% trifluoacetic acid over 3 mins) retention time 1.31 min, ESI+ found [M+H]=421.2.

Example 243

WX Method BBBB

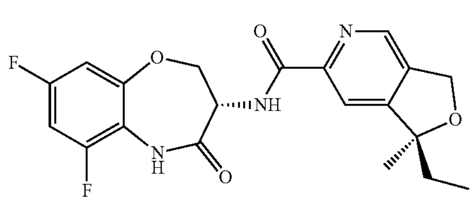 [SMILES: CC[C@]1(C)OCc2cnc(C(=O)N[C@H]3COc4cc(F)cc(F)c4NC3=O)cc21]

(S)—N—((S)-6,8-difluoro-4-oxo-2,3,4,5-tetrahydrobenzo[b][1,4]oxazepin-3-yl)-1-ethyl-1-m ethyl-1,3-dihydrofuro[3,4-c]pyridine-6-carboxamide A mixture of (1S)-1-ethyl-1-methyl-3H-furo[3,4-c]pyridine-6-carboxylic acid (19 mg, 0.09 mmol), (S)-3-amino-6,8-difluoro-2,3-dihydrobenzo[b][1,4]oxazepin-4(5H)-one hydrochloride (20 mg, 0.09 mmol), N[1]-((ethylimino)methylene)-N[3],N[3]-dimethylpropane-1,3-diamine hydrochloride (20 mg, 0.10 mmol) and 1H-benzo[d][1,2,3]triazol-1-ol (14 mg, 0.10 mmol) in N,N-dimethylformamide (4 mL) was stirred at 25° C. for 12 h. The reaction mixture was concentrated under reduced pressure and the residue was purified by RP-HPLC (acetonitrile 0-40%/0.1% ammonium hydroxide in water) to afford (S)—N—((S)-6,8-difluoro-4-oxo-2,3,4,5-tetrahydrobenzo[b][1,4]oxazepin-3-yl)-1-ethyl-1-methyl-1,3-dihydrofuro[3,4-c]pyridine-6-carboxamide (6.6 mg, 17%) as white solid: $^1$H NMR (400 MHz, $CD_3OD$) δ 8.57 (s, 1H), 7.90 (s, 1H), 6.99-6.84 (m, 2H), 5.22-5.13 (m, 2H), 5.09-5.05 (m, 1H), 4.72-4.68 (m, 1H), 4.55-4.48 (m, 1H), 1.89-1.83 (m, 2H), 1.47 (s, 3H), 0.78 (t, J=7.2 Hz, 3H). LCMS $R_T$=1.09 min; m/z=404.1 $(M+H)^+$.

LCMS (10-80% acetonitrile in water+0.03% trifluoroacetic over 2 mins) retention time 1.09 min, ESI+ found $[M+H]^+$=404.1.

Example 244

WX Method AAAAA

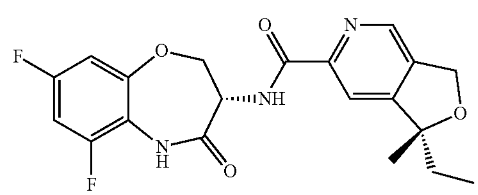 [SMILES: CC[C@@]1(C)OCc2cnc(C(=O)N[C@H]3COc4cc(F)cc(F)c4NC3=O)cc21]

(R)—N—((S)-6,8-difluoro-4-oxo-2,3,4,5-tetrahydrobenzo[b][1,4]oxazepin-3-yl)-1-ethyl-1-methyl-1,3-dihydrofuro[3,4-c]pyridine-6-carboxamide

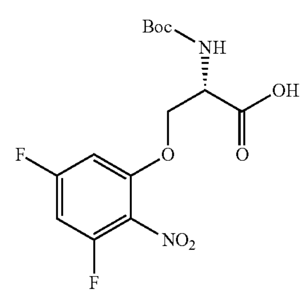 [SMILES: CC(C)(C)OC(=O)N[C@@H](COc1cc(F)cc(F)c1[N+](=O)[O-])C(=O)O]

Step 1: (S)-2-((tert-butoxycarbonyl)amino)-3-(3,5-difluoro-2-nitrophenoxy)propaneic acid To a solution of (S)-2-((tert-butoxycarbonyl)amino)-3-hydroxypropanoic acid (1.0 g, 4.87 mmol) in N,N-dimethylformamide (10 mL) was added sodium hydride (234 mg, 9.75 mmol) at 0° C. was added 1,3,5-trifluoro-2-nitrobenzene (863 mg, 4.87 mmol). The reaction mixture was stirred at 15° C. for 16 h and adjusted to pH=4 by addition of hydrochloric acid (2.0 M). The mixture was extracted with ethyl acetate (3×30 mL). The combined organic layers were washed with water (30 mL), brine (30 mL), dried over sodium sulfate and concentrated under reduced pressure to afford crude (S)-2-((tert-butoxycarbonyl)amino)-3-(3,5-difluoro-2-nitrophenoxy)propaneic acid (1.2 g, 68%) as yellow solid, used in the next step without further purification. LCMS $R_T$=0.772 min; m/z=385.1 $(M+Na)^+$.

LCMS (5-95% acetonitrile in water+0.03% trifluoroacetic over 1.5 mins) retention time 0.772 min, ESI+ found $[M+Na]^+$=385.1.

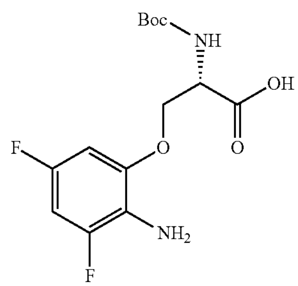

Step 2: (S)-3-(2-amino-3,5-difluorophenoxy)-2-((tert-butoxycarbonyl)amino)propanoic acid A mixture of (S)-2-((tert-butoxycarbonyl)amino)-3-(3,5-difluoro-2-nitrophenoxy) propaneic acid (1.2 g, 3.31 mmol) and 10% palladium on carbon (353 mg, 0.33 mmol) in methanol (30 mL) was hydrogenated (15 psi) at 15° C. for 3 h. After filtration, the filtrate was concentrated under reduced pressure to afford (S)-3-(2-amino-3,5-difluorophenoxy)-2-((tert-butoxycarbonyl)amino)propanoic acid (0.8 g, 73%) as a black solid, used in the next step without further purification.

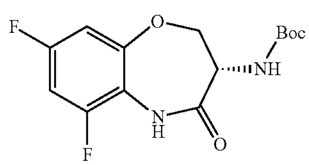 [SMILES: CC(C)(C)OC(=O)N[C@H]1COc2cc(F)cc(F)c2NC1=O]

Step 3: (S)-tert-butyl (6,8-difluoro-4-oxo-2,3,4,5-tetrahydrobenzo[b][1,4]oxazepin-3-yl)carbamate A mixture of (S)-3-(2-amino-3,5-difluorophenoxy)-2-((tert-butoxycarbonyl)amino) propanoic acid (0.8 g, 2.41 mmol) and $N^1$-((ethylimino)methylene)-$N^3$,$N^3$-dimethylpropane-1,3-diamine hydrochloride (463 mg, 2.41 mmol) in N,N-dimethylformamide (20 mL) was stirred at 15° C. for 2 h. The mixture was concentrated under reduced pressure and the residue was purified by column chromatography (silica gel, 100-200 mesh, 0 to 50% ethyl acetate in petroleum ether) to afford (S)-tert-butyl (6,8-difluoro-4-oxo-2,3,4,5-tetrahydrobenzo[b][1,4]oxazepin-3-yl)carbamate (0.4 g, 53%) as yellow solid: LCMS $R_T$=0.87 min; m/z=258.8 $(M-56)^+$.

LCMS (5-95% acetonitrile in water+0.03% trifluoroacetic over 1.5 mins) retention time 0.817 min, ESI+ found $[M-56]^+$=258.8

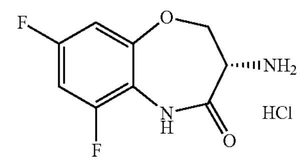 [SMILES: N[C@H]1COc2cc(F)cc(F)c2NC1=O ; Cl]

Step 4: (S)-3-amino-6,8-difluoro-2,3-dihydrobenzo[b][1,4]oxazepin-4(5H)-one hydrochloride A mixture of (S)-tert-butyl (6,8-difluoro-4-oxo-2,3,4,5-tetrahydrobenzo[b][1,4]oxazepin-3-yl)carbamate (0.4 g, 1.27 mmol) and hydrochloric acid (4M in EtOAc, 4.0 mL, 16.0 mmol) in ethyl acetate (10 mL) was stirred at 15° C. for 1 h. The mixture was concentrated under reduced pressure to afford crude (S)-3-amino-6,8-difluoro-2,3-dihydrobenzo[b][1,4]oxazepin-4(5H)-one hydrochloride (300 mg, 94%) as white solid, used in the next step without further purification.

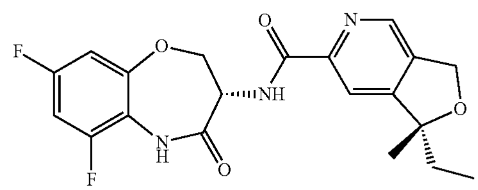 [SMILES: CC[C@@]1(C)OCc2cnc(C(=O)N[C@H]3COc4cc(F)cc(F)c4NC3=O)cc21]

Step 5: (R)—N—((S)-6,8-difluoro-4-oxo-2,3,4,5-tetrahydrobenzo[b][1,4]oxazepin-3-yl)-1-ethyl-1-methyl-1,3-dihydrofuro[3,4-c]pyridine-6-carboxamide A mixture of (1R)-1-ethyl-1-methyl-3H-furo[3,4-c]pyridine-6-carboxylic acid (19 mg, 0.09 mmol), (S)-3-amino-6,8-difluoro-2,3-dihydrobenzo[b][1,4]oxazepin-4(5H)-one hydrochloride (20 mg, 0.09 mmol), $N^1$-((ethylimino)methylene)-$N^3$,$N^3$-dimethylpropane-1,3-diamine hydrochloride (20 mg, 0.10 mmol) and 1H-benzo[d][1,2,3]triazol-1-ol (14 mg, 0.10 mmol) in N,N-dimethylformamide (4 mL) was stirred at 25° C. for 12 h. The reaction mixture was concentrated under reduced pressure and the residue was purified by RP-HPLC (acetonitrile 0-40%/0.1% ammonium hydroxide in water) to afford (R)—N—((S)-6,8-difluoro-4-oxo-2,3,4,5-tetrahydrobenzo[b][1,4]oxazepin-3-yl)-1-ethyl-1-m ethyl-1,3-dihydrofuro[3,4-c]pyridine-6-carboxamide (7.1 mg, 19%) as white solid: $^1H$ NMR (400 MHz, $CD_3OD$) δ 8.57 (s, 1H), 7.90 (s, 1H), 6.99-6.84 (m, 2H), 5.17-5.13 (m, 2H), 5.09-5.05 (m, 1H), 4.72-4.68 (m, 1H), 4.55-4.48 (m, 1H), 1.89-1.83 (m, 2H), 1.47 (s, 3H), 0.78 (t, J=7.6 Hz, 3H). LCMS $R_T$=1.09 min; m/z=404.1 $(M+H)^+$.

LCMS (10-80% acetonitrile in water+0.03% trifluoroacetic over 2 mins) retention time 1.09 min, ESI+ found $[M+H]^+$=404.1.

Example 245

WX Method BBBB

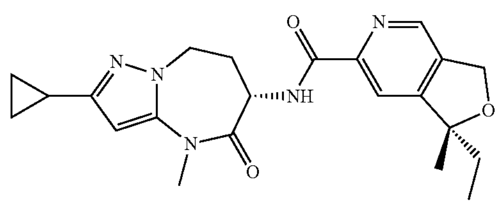 [SMILES: CC[C@@]1(C)OCc2cnc(C(=O)N[C@H]3CCn4nc(C5CC5)cc4N(C)C3=O)cc21]

(R)—N—((S)-2-cyclopropyl-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide A mixture of (1R)-1-ethyl-1-methyl-3H-furo[3,4-c]pyridine-6-carboxylic acid (23 mg, 0.11 mmol), 6S)-6-amino-2-cyclopropyl-4-methyl-7,8-dihydro-6H-pyrazolo[1,5-a][1,3]diazepin-5-one (20 mg, 0.09 mmol), $N^1$-((ethylimino) methylene)-$N^3$,$N^3$-dimethyl propane-1,3-diamine hydrochloride (24 mg, 0.14 mmol) and 1H-benzo[d][1,2,3]triazol-1-ol (18 mg, 0.14 mmol) in N,N-dimethylformamide (5 mL) was stirred at 25° C. for 12 h. The reaction was concentrated under reduced pressure and the residue was purified by RP-HPLC (17-47% acetonitrile in water and 0.05% ammonium bicarbonate) to give (R)—N—((S)-2-cyclopropyl-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide (15.3 mg, 41%) as a white solid: $^1$H NMR (400 MHz, $CD_3OD$) δ 8.61 (s, 1H), 7.92 (s, 1H), 6.06 (s, 1H), 5.25-5.21 (m, 2H), 4.63-4.59 (m, 1H), 4.38-4.23 (m, 2H), 3.38 (s, 3H), 3.02-2.93 (m, 1H), 2.31-2.30 (m, 1H), 1.96-1.88 (m, 3H), 1.51 (s, 3H), 1.00-0.98 (m, 2H), 0.84-0.79 (m, 5H). LCMS $R_T$=1.06 min; m/z=410.2 $(M+H)^+$.

LCMS (10 to 80% acetonitrile in water+0.03% trifluoacetic acid over 2.0 mins) retention time 1.06 min, ESI+ found [M+H]=410.2.

Example 246

WX Method ZZ

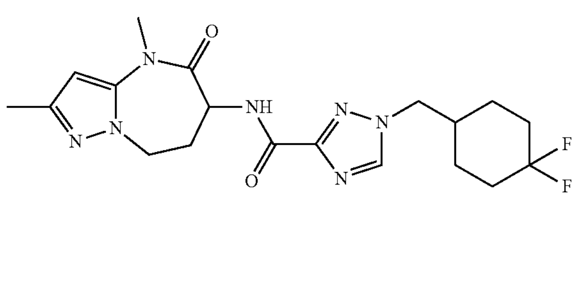 [SMILES: Cc1cc2n(n1)CCC(NC(=O)c1ncn(CC3CCC(F)(F)CC3)n1)C(=O)N2C]

1-((4,4-difluorocyclohexyl)methyl)-N-(2,4-dimethyl-5-oxo-5,6,7,8-tetrahydro-4H-pyrazolo[1,5-a][1,3]diazepin-6-yl)-1H-1,2,4-triazole-3-carboxamide

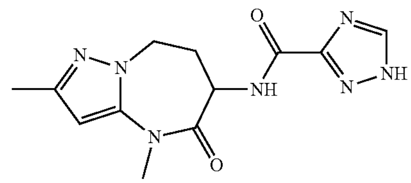 [SMILES: Cc1cc2n(n1)CCC(NC(=O)c1nc[nH]n1)C(=O)N2C]

Step 1: N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of 6-amino-2,4-dimethyl-7,8-dihydro-6H-pyrazolo[1,5-a][1,3]diazepin-5-one (2.4 g, 12.4 mmol), $N^1$-((ethylimino)methylene)-$N^3$,$N^3$-dimethyl propane-1,3-diamine hydrochloride (3.3 g, 18.5 mmol), 1H-benzo[d][1,2,3]triazol-1-ol (170 mg, 1.24 mmol) and 1H-1,2,4-triazole-3-carboxylic acid (1.7 g, 14.8 mmol) in N,N-dimethylformamide (60 mL) was stirred at 25° C. for 12 h. The reaction was concentrated under reduced pressure and the residue was purified by column chromatography (silica gel, 100-200 mesh, 0 to 3% methanol in dichloromethane) to afford N-(2,4-dimethyl-5-oxo-5,6,7,8-tetrahydro-4H-pyrazolo[1,5-a][1,3]diazepin-6-yl)-1H-1,2,4-triazole-3-carboxamide (2.8 g, 75%) as white solid, used as is in the next step.

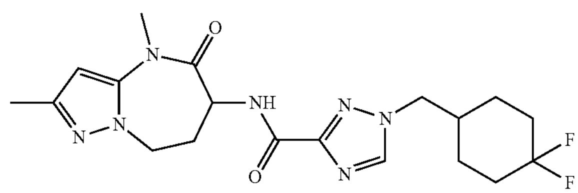 [SMILES: Cc1cc2n(n1)CCC(NC(=O)c1ncn(CC3CCC(F)(F)CC3)n1)C(=O)N2C]

Step 2: 1-((4,4-difluorocyclohexyl)methyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of N-(2,4-dimethyl-5-oxo-7,8-dihydro-6H-pyrazolo[1,5-a][1,3]diazepin-6-yl)-1H-1,2,4-triazole-3-carboxamide (250 mg, 0.86 mmol) and potassium carbonate (358 mg, 2.59 mmol) in N,N-dimethylformamide (5 mL) was added 4-(bromomethyl)-1,1-difluorocyclohexane (250 mg, 1.17 mmol). The mixture was stirred at 25° C. for 12 h and then concentrated under reduced pressure. The residue was purified by RP-HPLC (methanol 46-76%/0.05% ammonia hydroxide in water) to afford 1-((4,4-difluorocyclohexyl) methyl)-N-(2,4-dimethyl-5-oxo-5,6,7,8-tetrahydro-4H-pyrazolo[1,5-a][1,3]diazepin-6-yl)-1H-1,2,4-triazole-3-carboxam (40.2 mg, 8%) as white solid: $^1$H NMR (400 MHz, $CD_3OD$) δ 8.47 (s, 1H), 6.10 (s, 1H), 4.52-4.49 (m, 1H), 4.29-4.17 (m, 4H), 3.29 (s, 3H), 2.85-2.80 (m, 1H), 2.27-2.22 (m, 4H), 2.20-2.04 (m, 4H), 1.78-1.67 (m, 3H), 1.34-1.27 (m, 2H). LCMS $R_T$=0.751 min; m/z=422.1 $(M+H)^+$.

LCMS (5 to 95% acetonitrile in water+0.03% formic acid over 1.5 mins) retention time 0.751 min, ESI+ found [M+H]= 422.1.

Example 247

WX Method AAA

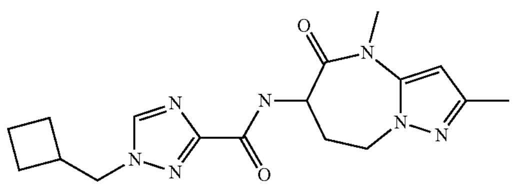 [SMILES: Cc1cc2n(n1)CCC(NC(=O)c1ncn(CC3CCC3)n1)C(=O)N2C]

1-(cyclobutylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of N-(2,4-dimethyl-5-oxo-7,8-dihydro-6H-pyrazolo[1,5-a][1,3]diazepin-6-yl)-1H-1,2,4-triazole-3-carboxamide (250 mg, 0.86 mmol) and potassium carbonate (358 mg, 2.59 mmol) in N,N-dimethylformamide (5 mL) was added (bromomethyl)cyclobutane (258 mg, 1.73 mmol). The mixture was stirred at 25° C. for 12 h and then concentrated under reduced pressure. The residue was purified by RP-HPLC (methanol 42-72%/0.05% ammonia hydroxide in water) to afford 1-(cyclobutylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (50.4 mg, 16%) as white solid: $^1H$ NMR (400 MHz, $CD_3OD$) δ 8.44 (s, 1H), 6.09 (s, 1H), 4.51-4.48 (m, 1H), 4.29-4.19 (m, 4H), 3.28 (s, 3H), 2.87-2.83 (m, 2H), 2.23-2.04 (m, 4H), 2.05-2.03 (m, 2H), 1.92-1.90 (m, 2H), 1.84-1.80 (m, 2H). LCMS $R_T$=0.736 min; m/z=358.1 $(M+H)^+$.

LCMS (5 to 95% acetonitrile in water+0.03% formic acid over 1.5 mins) retention time 0.736 min, ESI+ found [M+H]= 358.1.

Example 248

WX Method BBB

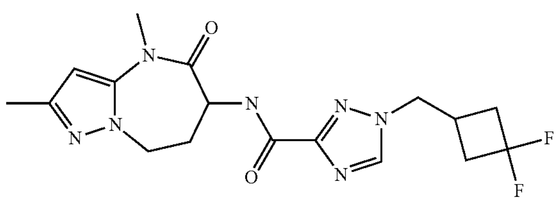 [SMILES: Cc1cc2n(n1)CCC(NC(=O)c1ncn(CC3CC(F)(F)C3)n1)C(=O)N2C]

1-((3,3-difluorocyclobutyl)methyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of N-(2,4-dimethyl-5-oxo-7,8-dihydro-6H-pyrazolo[1,5-a][1,3]diazepin-6-yl)-1H-1,2,4-triazole-3-carboxamide (250 mg, 0.86 mmol) and potassium carbonate (358 mg, 2.59 mmol) in N,N-dimethylformamide (5 mL) was added 3-(bromomethyl)-1,1-difluoro-cyclobutane (320 mg, 1.73 mmol). The mixture was stirred at 25° C. for 12 h and then concentrated under reduced pressure. The residue was purified by RP-HPLC (methanol 42-72%/0.05% ammonia hydroxide in water) to afford 1-((3,3-difluorocyclobutyl)methyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (50 mg, 15%) as white solid: $^1H$ NMR (400 MHz, $CD_3OD$) δ 8.53 (s, 1H), 6.12 (s, 1H), 4.54-4.52 (m, 1H), 4.41 (d, J=6.8 Hz, 2H), 4.32-4.22 (m, 2H), 3.31 (s, 3H), 2.85-2.68 (m, 2H), 2.66-2.64 (m, 2H), 2.48-2.44 (m, 2H), 2.30-2.26 (m, 4H). LCMS $R_T$=0.715 min; m/z=394.1 $(M+H)^+$.

LCMS (5 to 95% acetonitrile in water+0.03% formic acid over 1.5 mins) retention time 0.715 min, ESI+ found [M+H]= 394.1.

Example 249

WX Method DDD

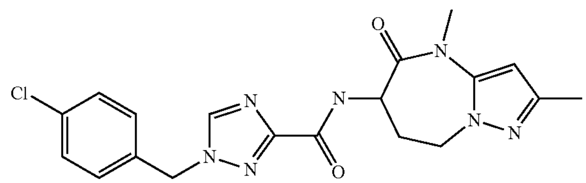 [SMILES: Cc1cc2n(n1)CCC(NC(=O)c1ncn(Cc3ccc(Cl)cc3)n1)C(=O)N2C]

1-(4-chlorobenzyl)-N-(2,4-dimethyl-5-oxo 6,7,8-tetrahydro-4H-pyrazolo[1,5-a][1,3]diazepin-6-yl)-1H-1,2,4-triazole-3-carboxamide A mixture of N-(2,4-dimethyl-5-oxo-7,8-dihydro-6H-pyrazolo[1,5-a][1,3]diazepin-6-yl)-1H-1,2,4-triazole-3-carboxamide (250 mg, 0.86 mmol) and potassium carbonate (358 mg, 2.59 mmol) in N,N-dimethylformamide (5 mL) was added 4-chlorobenzyl bromide (355 mg, 1.73 mmol). The mixture was stirred at 25° C. for 12 h and then concentrated under reduced pressure. The residue was purified by RP-HPLC (methanol 46-76%/0.05% ammonia hydroxide in water) to afford 1-(4-chlorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (60.4 mg, 17%) as white solid: $^1H$ NMR (400 MHz, $CD_3OD$) δ 8.70 (s, 1H), 7.37-7.32 (m, 4H), 6.32 (s, 1H), 5.46 (s, 2H), 4.63-4.61 (m, 1H), 4.40-4.30 (m, 2H), 3.29 (s, 3H), 2.88-2.82 (m, 1H), 2.38-2.32 (m, 4H). LCMS $R_T$=0.767 min; m/z=414.1 $(M+H)^+$.

LCMS (5 to 95% acetonitrile in water+0.03% formic acid over 1.5 mins) retention time 0.767 min, ESI+ found [M+H]= 414.1.

Example 250

WX Method EEE

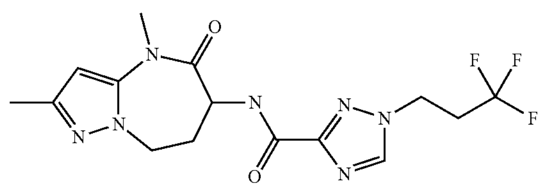 [SMILES: Cc1cc2n(n1)CCC(NC(=O)c1ncn(CCC(F)(F)F)n1)C(=O)N2C]

N-(2,4-dimethyl-5-oxo-5,6,7,8-tetrahydro-4H-pyrazolo[1,5-a][1,3]diazepin-6-yl)-1-(3,3,3-trifluoropropyl)-1H-1,2,4-triazole-3-carboxamide A mixture of N-(2,4-dimethyl-5-oxo-7,8-dihydro-6H-pyrazolo[1,5-a][1,3]diazepin-6-yl)-1H-1,2,4-triazole-3-carboxamide (250 mg, 0.86 mmol) and potassium carbonate (358 mg, 2.59 mmol) in N,N-dimethylformamide (5 mL) was added 1-iodo-3,3,3-trifluoropropane (387 mg, 1.73 mmol). The mixture was stirred at 25° C. for 12 h and then concentrated under reduced pressure. The residue was purified by RP-HPLC (methanol 25-55%/0.05% ammonia hydroxide in water) to afford N-(2,4-dimethyl-5-oxo-5,6,7,8-tetrahydro-4H-pyrazolo[1,5-a][1,3]diazepin-6-yl)-1-(3,3,3-trifluoropropyl)-1H-1,2,4-triazole-3-carboxamide (41.2 mg, 10%) as white solid: $^1$H NMR (400 MHz, $CD_3OD$) δ 8.52 (s, 1H), 6.10 (s, 1H), 4.56-4.52 (m, 3H), 4.29-4.20 (m, 2H), 3.29 (s, 3H), 2.90-2.83 (m, 3H), 2.29-2.24 (m, 4H). LCMS $R_T$=0.701 min; m/z=386.0 $(M+H)^+$.

LCMS (5 to 95% acetonitrile in water+0.03% formic acid over 1.5 mins) retention time 0.701 min, ESI+ found [M+H]= 386.0.

Example 251

WX Method GGG

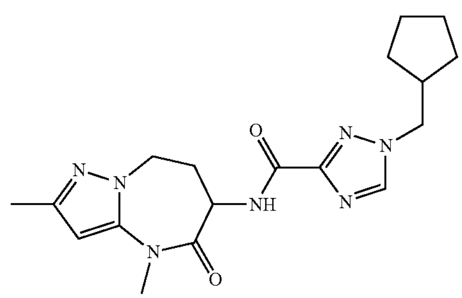 [SMILES: Cc1cc2n(n1)CCC(NC(=O)c1ncn(CC3CCCC3)n1)C(=O)N2C]

1-(cyclopentylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of N-(2,4-dimethyl-5-oxo-7,8-dihydro-6H-pyrazolo[1,5-a][1,3]diazepin-6-yl)-1H-1,2,4-triazole-3-carboxamide (250 mg, 0.86 mmol) and potassium carbonate (358 mg, 2.59 mmol) in N,N-dimethylformamide (5 mL) was added bromomethylcyclopentane (282 mg, 1.73 mmol). The mixture was stirred at 25° C. for 12 h and then concentrated under reduced pressure. The residue was purified by RP-HPLC (methanol 40-70%/0.05% ammonium hydroxide in water) to afford 1-(cyclopentylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (70.4 mg, 22%) as white solid: $^1$H NMR (400 MHz, $CD_3OD$) δ 8.50 (s, 1H), 6.12 (s, 1H), 4.57-4.52 (m, 1H), 4.35-4.15 (m, 4H), 3.34 (s, 3H), 2.91-2.81 (m, 1H), 2.53-2.44 (m, 1H), 2.30-2.23 (m, 4H), 1.70-1.58 (m, 6H), 1.34-1.28 (m, 2H). LCMS $R_T$=1.157 min; m/z=372.2 $(M+H)^+$.

LCMS (0 to 60% acetonitrile in water+0.03% trifluoacetic acid over 2 mins) retention time 1.157 min, ESI+ found $[M+H]^+$=372.2.

Example 252

WX Method LL

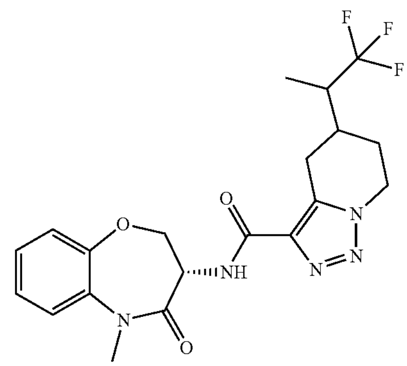 [SMILES: CC(C1CCn2nnc(C(=O)N[C@H]3COc4ccccc4N(C)C3=O)c2C1)C(F)(F)F]

N—((S)-5-methyl-4-oxo-2,3,4,5-tetrahydrobenzo[b][1,4]oxazepin-3-yl)-5-(1,1,1-trifluoropropan-2-yl)-4,5,6,7-tetrahydro-[1,2,3]triazolo[1,5-a]pyridine-3-carboxamide

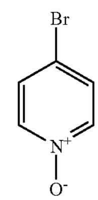

Step 1: 4-bromo-1-oxido-pyridin-1-ium

To a solution of 4-bromopyridine hydrochloride (20.0 g, 102.9 mmol) in water (200 mL) and dichloromethane (300 mL) was added sodium carbonate (16.4 g, 154.3 mmol). The mixture was extracted with dichloromethane (2×200 mL). The combined organic layers were dried over sodium sulfate, and then added 3-chloroperoxybenzoic acid (35.5 g, 205.7 mmol). After addition, the mixture was stirred at 34° C. for 2 h, and then washed with saturated aqueous sodium sulfite (200 mL), saturated aqueous sodium carbonate (200 mL), brine (200 mL), dried over sodium sulfate and concentrated under reduced pressure to afford crude 4-bromo-1-oxido-pyridin-1-ium (10.0 g, 56%) as a white solid, used in the next step without further purification.

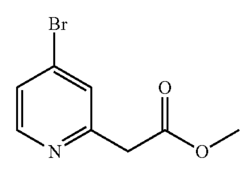

Step 2: Methyl 2-(4-bromo-2-pyridyl)acetate

To a solution of 4-bromopyridinen-oxide (5.0 g, 28.7 mmol) in tetrahydrofuran (150 mL) was added 1-(tert-butyldimethylsilyloxy)-1-methoxyethene (10.8 g, 57.5 mmol), bromo[tri(1-pyrrolidinyl)]phosphonium hexafluorophosphate (14.7 g, 31.6 mmol) and N,N-diisopropylethylamine (11.1 g, 86.2 mmol) at 25° C. The reaction was heated at 45° C. for 2 h. After cooled, the reaction was poured into water (100 mL) and extracted with ethyl acetate (3×150 mL). The combined organic layers were washed with water (100 mL), brine (100 mL), dried over sodium sulfate and concentrated under reduced pressure. The residue was purified by column chromatography (silica gel, 100-200 mesh, 0 to 20% ethyl acetate in petroleum ether) to afford methyl 2-(4-bromo-2-pyridyl)acetate (2.6 g, 39%) as yellow oil: $^1$H NMR (400 MHz, MeOD) δ 8.33 (d, J=5.6 Hz, 1H), 7.67 (s, 1H), 7.57-7.53 (m, 1H), 3.90-3.80 (m, 2H), 3.71 (s, 3H). LCMS $R_T$=0.474 min; m/z=229.8 $(M+H)^+$.

LCMS (5 to 95% acetonitrile in water+0.03% trifluoacetic acid over 1.5 mins) retention time 0.474 min, ESI+ found [M+H]=229.8

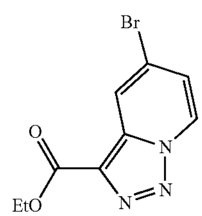 [SMILES: CCOC(=O)c1nnn2ccc(Br)cc12]

Step 3: Methyl 5-bromotriazolo[1,5-a]pyridine-3-carboxylate

To a solution of methyl 2-(4-bromo-2-pyridyl) acetate (2.7 g, 11.6 mmol) in acetonitrile (300 mL) was added 1,8-diazabicyclo[5.4.0]undec-7-ene (2.6 g, 17.3 mmol) and 4-acetamidobenzenesulfonylazide (2.8 g, 11.6 mmol) at 0° C. After addition, the mixture was allowed to warm to 25° C. and stirred for 1 h. The reaction mixture was concentrated under reduced pressure and the residue was purified by column chromatography (silica gel, 100-200 mesh, 0 to 20% ethyl acetate in petroleum ether) to afford methyl 5-bromotriazolo[1,5-a]pyridine-3-carboxylate (2.2 g, 74%) as a yellow solid: $^1$H NMR (400 MHz, $CDCl_3$) δ 9.25 (d, J=7.2 Hz, 1H), 8.36 (s, 1H), 7.56 (d, J=6.0 Hz, 1H), 3.93 (s, 3H). LCMS $R_T$=0.714 min; m/z=255.7 $(M+H)^+$.

LCMS (5 to 95% acetonitrile in water+0.03% trifluoacetic acid over 1.5 mins) retention time 0.714 min, ESI+ found [M+H]=255.7.

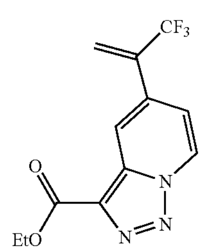 [SMILES: C=C(c1ccn2nnc(C(=O)OCC)c2c1)C(F)(F)F]

Step 4: Methyl 5-[1-(trifluoromethyl)vinyl]triazolo[1,5-a]pyridine-3-carboxylate A mixture of methyl 5-bromotriazolo[1,5-a]pyridine-3-carboxylate (100 mg, 0.40 mmol), 1,1'-bis (diphenylphosphino) ferrocene palladium dichloride (28 mg, 0.04 mmol), cesium carbonate (254 mg, 0.78 mmol) and 1-(trifluoromethyl) vinylboronic acid hexylene glycol ester (130 mg, 0.58 mmol) in 1,4-dioxane (5 mL) and water (2 mL) was heated at 110° C. for 30 min under microwave conditions. The reaction was concentrated under reduced pressure and the residue was purified by column chromatography (silica gel, 100-200 mesh, 0 to 35% ethyl acetate in petroleum ether) to afford methyl 5-[1-(trifluoromethyl)vinyl]triazolo[1,5-a]pyridine-3-carboxylate (70 mg, 66%) as a yellow solid: $^1$H NMR (400 MHz, MeOD) δ 9.08 (d, J=7.6 Hz, 1H), 8.29 (s, 1H), 7.47-7.43 (m, 1H), 6.36-6.31 (m, 2H), 4.00 (s, 3H). LCMS $R_T$=0.812 min; m/z=271.8 $(M+H)^+$.

LCMS (5 to 95% acetonitrile in water+0.03% trifluoacetic acid over 1.5 mins) retention time 0.812 min, ESI+ found [M+H]=271.8

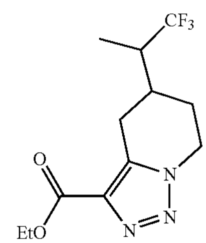 [SMILES: CCOC(=O)c1nnn2c1CC(C(C)C(F)(F)F)CC2]

Step 5: Methyl 5-(2,2,2-trifluoro-1-methyl-ethyl)-4,5,6,7-tetrahydrotriazolo[1,5-a]pyridine-3-carboxylate A mixture of methyl 5-[1-(trifluoromethyl)vinyl]triazolo[1,5-a]pyridine-3-carboxylate (60 mg, 0.22 mmol) and 10% palladium on carbon (23 mg, 0.02 mmol) in methanol (5 mL) was hydrogenated (50 psi) at 45° C. for 18 h. The reaction mixture was filtered and the filtrate was concentrated under reduced pressure affording crude methyl 5-(2,2,2-trifluoro-1-methyl-ethyl)-4,5,6,7-tetrahydrotriazolo[1,5-a]pyridine-3-carboxylate (47 mg, 77%) as a yellow solid: LCMS $R_T$=0.778 min; m/z=277.9 $(M+H)^+$.

LCMS (5 to 95% acetonitrile in water+0.03% trifluoacetic acid over 1.5 mins) retention time 0.778 min, ESI+ found [M+H]=277.9

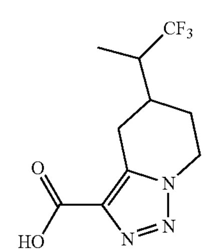 [SMILES: CC(C1CCn2nnc(C(=O)O)c2C1)C(F)(F)F]

Step 6: 5-(2,2,2-trifluoro-1-methyl-ethyl)-4,5,6,-tetrahydrotriazolo[1,5-a]pyridine-3-carboxylic acid A mixture of methyl 5-(2,2,2-trifluoro-1-methyl-ethyl)-4,5,6,7-tetrahydrotriazolo [1,5-a]pyridine-3-carboxylate (47 mg, 0.17 mmol) and lithium hydroxide hydrate (20 mg, 0.85 mmol) in tetrahydrofuran (5 mL) and water (2 mL) was stirred at 29° C. for 18 h. After evaporation of the organics under reduced pressure, the aqueous residue was adjusted to pH=5 by addition of hydrochloric acid (1.0 M). The solid was removed by filtration and the aqueous layer was concentrated under reduced pressure affording crude 5-(2,2,2-trifluoro-1-methyl-ethyl)-4,5,6,7-tetrahydrotriazolo[1,5-a]pyridine-3-carboxylic acid (25 mg, 56%) as a white solid: LCMS $R_T$=1.560 min; m/z=264.1 $(M+H)^+$.

LCMS (0 to 60% acetonitrile in water+0.04% formic acid over 3 mins) retention time 1.560 min, ESI+ found [M+H]=264.1.

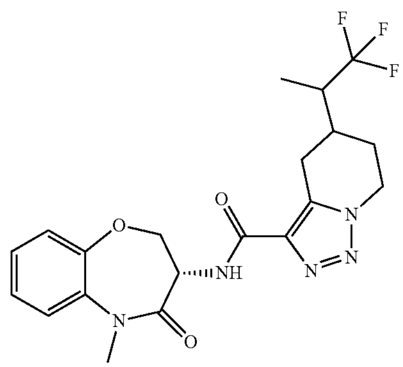 [SMILES: CC(C1CCn2nnc(C(=O)N[C@H]3COc4ccccc4N(C)C3=O)c2C1)C(F)(F)F]

Step 7: N—((S)-5-methyl-4-oxo-2,3,4,5-tetrahydrobenzo[b][1,4]oxazepin-3-yl)-5-(1,1,1-trifluoropropan-2-yl)-4,5,6,7-tetrahydro-[1,2,3]triazolo[1,5-a]pyridine-3-carboxamide A mixture of 5-(2,2,2-trifluoro-1-methyl-ethyl)-4,5,6,7-tetrahydrotriazolo[1,5-a]pyridine-3-carboxylic acid (25 mg, 0.09 mmol), (3s)-3-amino-5-methyl-2,3-dihydro-1,5-benzoxazepin-4-one (20 mg, 0.10 mmol), 1H-benzo[d][1,2,3]triazol-1-ol (15 mg, 0.11 mmol) and $N^1$-((ethylimino)methylene)-$N^3$,$N^3$-dimethylpropane-1,3-diamine hydrochloride (22 mg, 0.11 mmol) in N, N-dimethylformamide (5 mL) was stirred at 25° C. for 1 h. The reaction was concentrated under reduced pressure and the residue was purified by RP-HPLC (acetonitrile 40-70%/0.05% ammonia in water) affording N—((S)-5-methyl-4-oxo-2,3,4,5-tetrahydrobenzo[b][1,4]oxazepin-3-yl)-5-(1,1,1-trifluoropropan-2-yl)-4,5,6,7-tetrahydro-[1,2,3]triazolo[1,5-a]pyridine-3-carboxamide (11.5 mg, 27%) as a white solid: $^1H$ NMR (400 MHz, DMSO-$d_6$) δ 8.43 (d, J=6.4 Hz, 1H), 7.52-7.45 (m, 1H), 7.36-7.19 (m, 3H), 4.90-4.78 (m, 1H), 4.65-4.53 (m, 2H), 4.39 (t, J=8.4 Hz, 1H), 4.31-4.17 (m, 1H), 3.30 (s, 3H), 3.21-3.04 (m, 1H), 2.79-2.59 (m, 2H), 2.35-2.18 (m, 1H), 2.14-1.99 (m, 1H), 1.97-1.77 (m, 1H), 1.16-1.02 (m, 3H). LCMS $R_T$=0.853 min; m/z=438.1 $(M+H)^+$.

LCMS (5 to 95% acetonitrile in water+0.03% trifluoacetic acid over 1.5 mins) retention time 0.853 min, ESI+ found [M+H]=438.1.

Example 253

WX Method FFF

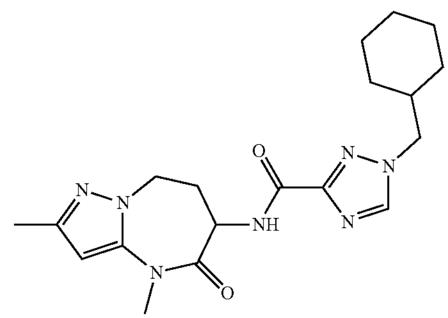 [SMILES: Cc1cc2n(n1)CCC(NC(=O)c1ncn(CC3CCCCC3)n1)C(=O)N2C]

1-(cyclohexylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of N-(2,4-dimethyl-5-oxo-7,8-dihydro-6H-pyrazolo[1,5-a][1,3]diazepin-6-yl)-1H-1,2,4-triazole-3-carboxamide (200 mg, 0.69 mmol) and potassium carbonate (287 mg, 2.07 mmol) in N,N-dimethylformamide (5 mL) was added cyclohexylmethyl bromide (245 mg, 1.38 mmol). The mixture was stirred at 25° C. for 12 h and then concentrated under reduced pressure. The residue was purified by RP-HPLC (methanol 50-80%/0.05% ammonium hydroxide in water) to afford 1-(cyclohexylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (55.5 mg, 21%) as white solid: $^1H$ NMR (400 MHz, $CD_3OD$): δ 8.46 (s, 1H), 6.12 (s, 1H), 4.57-4.52 (m, 1H), 4.35-4.18 (m, 2H), 4.11 (d, J=8.0, 2H), 3.34 (s, 3H), 2.91-2.81 (m, 1H), 2.30-2.23 (m, 4H), 1.96-1.91 (m, 1H), 1.76-1.68 (m, 3H), 1.63-1.56 (m, 2H), 1.33-1.19 (m, 3H), 1.06-0.97 (m, 2H). LCMS $R_T$=1.226 min; m/z=386.2 $(M+H)^+$.

LCMS (0 to 60% acetonitrile in water+0.03% trifluoacetic acid over 2 mins) retention time 1.226 min, ESI+ found $[M+H]^+$=386.2.

Example 254

WX Method NNN

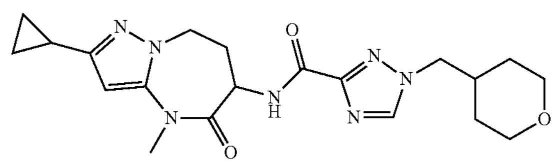 [SMILES: CN1C(=O)C(NC(=O)c2ncn(CC3CCOCC3)n2)CCn2nc(C3CC3)cc21]

N-(2-cyclopropyl-4-methyl-5-oxo-5,6,7,8-tetrahydro-4H-pyrazolo[1,5-a][1,3]diazepin-6-yl)-1-((tetrahydro-2H-pyran-4-yl)methyl)-1H-1,2,4-triazole-3-carboxamide

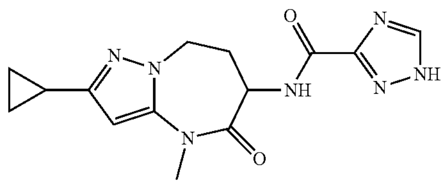 [SMILES: CN1C(=O)C(NC(=O)c2nc[nH]n2)CCn2nc(C3CC3)cc21]

Step 1: N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide A mixture of 6-amino-2-cyclopropyl-4-methyl-7,8-dihydro-6H-pyrazolo[1,5-a][1,3]diazepin-5-one (3.6 g, 16.3 mmol), 1H-1,2,4-triazole-3-carboxylic acid (2.2 g, 19.6 mmol), 1H-benzo[d][1,2,3]triazol-1-ol (220 mg, 1.6 mmol) and $N^1$-((ethylimino) methylene)-$N^3$,$N^3$-dimethylpropane-1,3-diamine hydrochloride (4.4 g, 24.5 mmol) in N,N-dimethylformamide (60 mL) was stirred at 25° C. for 12 h. After removed the solvent under reduced pressure, the residue was purified by column chromatography (silica gel, 100-200 mesh, 0 to 3% methanol in dichloromethane) to afford N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (2.6 g, 46%) as white solid: LCMS $R_T$=1.07 min, m/z=316.1 $(M+H)^+$.

LCMS (0 to 60% acetonitrile in water+0.03% ammonium bicarbonate over 3 mins) retention time 1.07 min, ESI+ found [M+H]=316.1

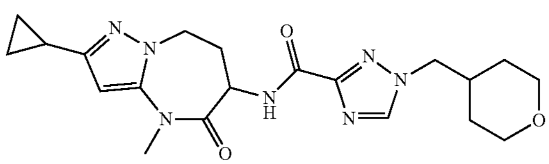 [SMILES: CN1C(=O)C(NC(=O)c2ncn(CC3CCOCC3)n2)CCn2nc(C3CC3)cc21]

Step 2: N-(2-cyclopropyl-4-methyl-5-oxo-5,6,7,8-tetrahydro-4H-pyrazolo[1,5-a][1,3]diazepin-6-yl)-1-((tetrahydro-2H-pyran-4-yl)methyl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (3 mL) was added potassium carbonate (329 mg, 2.38 mmol) and 4-(bromomethyl)tetrahydropyran (213 mg, 1.19 mmol). The mixture was stirred at 25° C. for 12 h and then filtered. The filtrate was evaporated under reduced pressure and the residue was purified by RP-HPLC (40-70% methyl alcohol in water and 0.05% ammonia hydroxide) to afford N-(2-cyclopropyl-4-methyl-5-oxo-5,6,7,8-tetrahydro-4H-pyrazolo[1,5-a][1,3]diazepin-6-yl)-1-((tetrahydro-2H-pyran-4-yl)meth yl)-1H-1,2,4-triazole-3-carboxamide (46 mg, 14%): $^1$H NMR (400 MHz, $CD_3OD$) δ 8.05 (s, 1H), 6.03 (s, 1H), 4.60-4.56 (m, 2H), 4.34-4.30 (m, 1H), 4.18-4.16 (m, 2H), 4.00-3.94 (m, 2H), 3.44-3.40 (m, 2H), 3.38-3.34 (m, 3H), 2.87-2.86 (m, 1H), 2.28-2.26 (m, 2H), 1.92-1.91 (m, 1H), 1.50-1.41 (m, 2H), 1.39-1.28 (m, 2H), 0.97-0.94 (m, 2H), 0.78-0.75 (m, 2H). LCMS $R_T$=1.57 min, m/z=414.2 $[M+H]^+$.

LCMS (0 to 60% acetonitrile in water+0.03% trifluoacetic acid over 3 mins) retention time 1.57 min, ESI+ found [M+H]=414.2.

Example 255

WX Method OOO

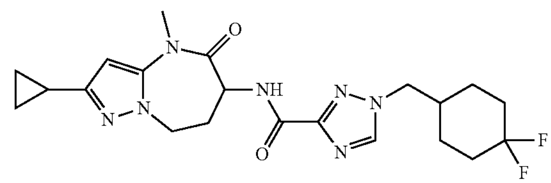 [SMILES: CN1C(=O)C(NC(=O)c2ncn(CC3CCC(F)(F)CC3)n2)CCn2nc(C3CC3)cc21]

N-(2-cyclopropyl-4-methyl-5-oxo-5,6,7,8-tetrahydro-4H-pyrazolo[1,5-a][1,3]diazepin-6-yl)-1-((4,4-difluorocyclohexyl)methyl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (3 mL) was added potassium carbonate (329 mg, 2.38 mmol) and 4-(bromomethyl)-1,1-difluorocyclohexane (253 mg, 1.19 mmol). The mixture was stirred at 25° C. for 12 h and then filtered. The filtrate was evaporated under reduced pressure and the residue was purified by RP-HPLC (55-85% methyl alcohol in water and 0.05% ammonia hydroxide) to afford N-(2-cyclopropyl-4-methyl-5-oxo-5,6,7,8-tetrahydro-4H-pyrazolo[1,5-a][1,3]diazepin-6-yl)-1-((4,4-difluorocyclohexyl)methyl)-1H-1,2,4-triazole-3-carboxamide (28.3 mg, 8%): $^1$H NMR (400 MHz, $CD_3OD$) δ 8.48 (s, 1H), 6.00 (s, 1H), 4.55-4.50 (m, 1H), 4.29-4.18 (m, 4H), 3.33 (s, 3H), 2.88-2.83 (m, 1H), 2.27-2.22 (m, 1H), 2.05-2.04 (m, 3H), 1.90-1.66 (m, 5H), 1.35-1.32 (m, 2H), 0.95-0.92 (m, 2H), 0.75-0.72 (m, 2H). LCMS $R_T$=1.79 min; m/z=448.2 $(M+H)^+$.

LCMS (0 to 60% acetonitrile in water+0.03% trifluoacetic acid over 3 mins) retention time 1.79 min, ESI+ found [M+H]=448.2.

Example 256

WX Method PPP

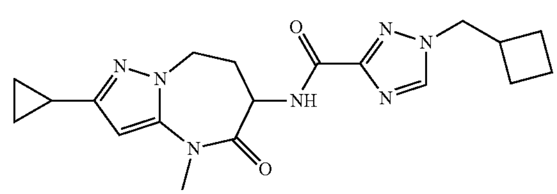 [SMILES: CN1C(=O)C(NC(=O)c2ncn(CC3CCC3)n2)CCn2nc(C3CC3)cc21]

1-(cyclobutylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (3 mL) was added potassium carbonate (329 mg, 2.38 mmol) and (bromomethyl)cyclobutane (177 mg, 1.19 mmol). The mixture was stirred at 25° C. for 12 h and then filtered. The filtrate was evaporated under reduced pressure and the residue was purified by RP-HPLC (55-85% methyl alcohol in water and 0.05% ammonia hydroxide) to afford 1-(cyclobutylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (57.2 mg, 18%): $^1H$ NMR (400 MHz, $CD_3OD$) δ 8.47 (s, 1H), 6.01 (s, 1H), 4.55-4.50 (m, 1H), 4.34-4.28 (m, 4H), 3.32 (s, 3H), 2.90-2.84 (m, 2H), 2.26-2.08 (m, 1H), 1.95-1.93 (m, 2H), 1.92-1.83 (m, 5H), 0.99-0.93 (m, 2H), 0.76-0.73 (m, 2H). LCMS $R_T$=1.73 min; m/z=384.2 $(M+H)^+$.

LCMS (0 to 60% acetonitrile in water+0.03% trifluoacetic acid over 3 mins) retention time 1.73 min, ESI+ found [M+H]=384.2.

Example 257

WX Method QQQ

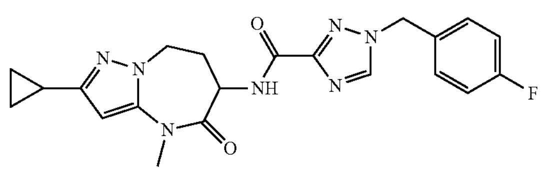 [SMILES: CN1C(=O)C(NC(=O)c2ncn(Cc3ccc(F)cc3)n2)CCn2nc(C3CC3)cc21]

N-(2-cyclopropyl-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (3 mL) was added potassium carbonate (329 mg, 2.38 mmol) and 4-fluorobenzyl chloride (172 mg, 1.19 mmol). The mixture was stirred at 25° C. for 12 h and then filtered. The filtrate was evaporated under reduced pressure and the residue was purified by RP-HPLC (50-80% methyl alcohol in water and 0.05% ammonia hydroxide) to afford N-(2-cyclopropyl-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide (52.4 mg, 15%): $^1H$ NMR (400 MHz, $CDCl_3$) δ 8.02 (s, 1H), 7.31-7.27 (m, 2H), 7.10-7.06 (m, 2H), 5.78 (s, 1H), 5.36 (s, 2H), 4.78-4.74 (m, 1H), 4.40-4.34 (m, 1H), 4.13-4.06 (m, 1H), 3.34 (s, 3H), 3.19-3.14 (m, 1H), 2.04-2.01 (m, 1H), 2.00-1.88 (m, 1H), 0.95-0.93 (m, 2H), 0.75-0.74 (m, 2H). LCMS $R_T$=1.76 min; m/z=424.2 $(M+H)^+$.

LCMS (0 to 60% acetonitrile in water+0.03% trifluoacetic acid over 3 mins) retention time 1.76 min, ESI+ found [M+H]=424.2.

Example 258

WX Method RRR

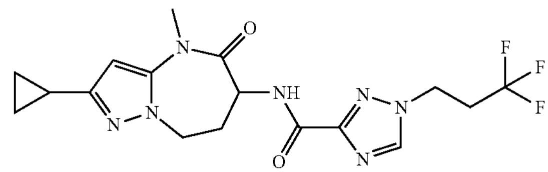 [SMILES: CN1C(=O)C(NC(=O)c2ncn(CCC(F)(F)F)n2)CCn2nc(C3CC3)cc21]

N-(2-cyclopropyl-4-methyl-5-oxo-5,6,7,8-tetrahydro-4H-pyrazolo[1,5-a][1,3]diazepin-6-yl)-1-(3,3,3-trifluoropropyl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (3 mL), was added potassium carbonate (329 mg, 2.38 mmol) and 1-iodo-3,3,3-trifluoropropane (266 mg, 1.19 mmol). The mixture was stirred at 25° C. for 12 h and then filtered. The filtrate was evaporated under reduced pressure and the residue was purified by RP-HPLC (50-70% methyl alcohol in water and 0.05% ammonia hydroxide) to afford N-(2-cyclopropyl-4-methyl-5-oxo-5,6,7,8-tetrahydro-4H-pyrazolo[1,5-a][1,3]diazepin-6-yl)-1-(3,3,3-trifluoropropyl)-1H-1,2,4-triazole-3-carboxamide (42.7 mg, 13%): $^1H$ NMR (400 MHz, DMSO-$d_6$) δ 8.72 (s, 1H), 8.55 (d, J=7.6 Hz, 1H), 6.05 (s, 1H), 4.52 (t, J=6.8 Hz, 2H), 4.31-4.22 (m, 2H), 4.20-4.07 (m, 1H), 3.18 (s, 3H), 3.00-2.90 (m, 2H), 2.57-2.55 (m, 1H), 2.33-2.30 (m, 1H), 1.85-1.81 (m, 1H), 0.85-0.82 (m, 2H), 0.66-0.63 (m, 2H). LCMS $R_T$=1.65 min; m/z=412.1 $(M+H)^+$.

LCMS (0 to 60% acetonitrile in water+0.03% trifluoacetic acid over 3 mins) retention time 1.65 min, ESI+ found [M+H]=412.1.

Example 259

WX Method SSS

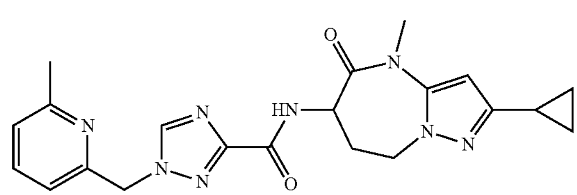 [SMILES: Cc1cccc(Cn2cnc(C(=O)NC3CCn4nc(C5CC5)cc4N(C)C3=O)n2)n1]

N-(2-cyclopropyl-4-methyl-5-oxo-5,6,7,8-tetrahydro-4H-pyrazolo[1,5-a][1,3]diazepin-6-yl)-1-((6-methylpyridin-2-yl)methyl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (3 mL) was added potassium carbonate (329 mg, 2.38 mmol) and 2-(bromomethyl)-6-methylpyridine (221 mg, 1.19 mmol). The mixture was stirred at 25° C.

for 12 h and then filtered. The filtrate was evaporated under reduced pressure and the residue was purified by RP-HPLC (45-75% methyl alcohol in water and 0.05% ammonia hydroxide) to afford N-(2-cyclopropyl-4-methyl-5-oxo-5,6,7,8-tetrahydro-4H-pyrazolo[1,5-a][1,3]diazepin-6-yl)-1-((6-methylpyridin-2-yl)methyl)-1H-1,2,4-triazole-3-carboxamide (36.6 mg, 11%): $^1$H NMR (400 MHz, DMSO-$d_6$) δ 8.79 (s, 1H), 8.52 (d, J=7.6 Hz, 1H), 7.67 (t, J=7.6 Hz, 1H), 7.18 (d, J=8.0 Hz, 1H), 7.04 (d, J=8.0 Hz, 1H), 6.03 (s, 1H), 5.51 (s, 2H), 4.34-4.19 (m, 2H), 4.12-4.07 (m, 1H), 3.17 (s, 3H), 2.54-2.52 (m, 1H), 2.40 (s, 3H), 2.35-2.30 (m, 1H), 1.88-1.80 (m, 1H), 0.84-0.82 (m, 2H), 0.65-0.62 (m, 2H). LCMS $R_T$=1.46 min; m/z=421.2 (M+H)$^+$.

LCMS (0 to 60% acetonitrile in water+0.03% trifluoacetic acid over 3 mins) retention time 1.46 min, ESI+ found [M+H]=421.2.

Example 260

WX Method XXX

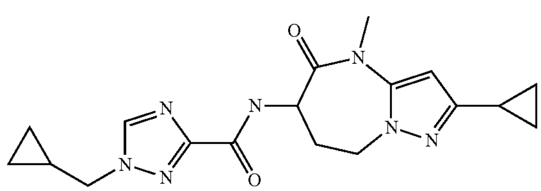 [SMILES: CN1C(=O)C(NC(=O)c2ncn(CC3CC3)n2)CCn2nc(C3CC3)cc21]

N-(2-cyclopropyl-4-methyl-5-oxo-5,6,7,8-tetrahydro-4H-pyrazolo[1,5-a][1,3]diazepin-6-yl)-1-(cyclopropylmethyl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (5 mL) was added (bromomethyl) cyclopropane (461 mg, 1.72 mmol) and potassium carbonate (358 mg, 2.59 mmol). The mixture was stirred at 25° C. for 12 h and then filtered. The filtrate was evaporated under reduced pressure and the residue was purified by RP-HPLC (methanol 40-70%/0.05% ammonia hydroxide in water) to afford N-(2-cyclopropyl-4-methyl-5-oxo-5,6,7,8-tetrahydro-4H-pyrazolo[1,5-a][1,3]diazepin-6-yl)-1-(cyclopropylmethyl)-1H-1,2,4-tri azole-3-carboxamide (95.9 mg, 33%) as white solid: $^1$H NMR (400 MHz, DMSO-$d_6$) δ 8.68 (s, 1H), 8.51 (d, J=8.0 Hz, 1H), 6.07 (s, 1H), 4.33-4.22 (m, 2H), 4.12-4.08 (m, 3H), 3.20 (s, 3H), 2.58-2.55 (m, 1H), 2.34-2.30 (m, 1H), 1.86-1.83 (m, 1H), 1.30-1.26 (m, 1H), 0.87-0.84 (m, 2H), 0.68-0.65 (m, 2H), 0.56-0.53 (m, 2H), 0.41-0.38 (m, 2H). LCMS $R_T$=0.73 min; m/z=370.1 (M+H)$^+$.

LCMS (5 to 95% acetonitrile in water+0.03% formic acid over 1.5 mins) retention time 0.73 min, ESI+ found [M+H]=370.1.

Example 261

WX Method WWW

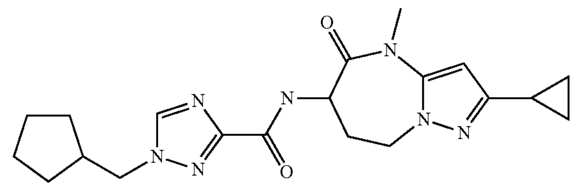 [SMILES: CN1C(=O)C(NC(=O)c2ncn(CC3CCCC3)n2)CCn2nc(C3CC3)cc21]

1-(cyclopentylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (200 mg, 0.69 mmol) in N,N-dimethylformamide (5 mL) was added bromomethylcyclopentane (135 mg, 0.83 mmol) and potassium carbonate (287 mg, 2.07 mmol). The mixture was stirred at 25° C. for 12 h and then filtered. The filtrate was evaporated under reduced pressure and the residue was purified by RP-HPLC (55-85% methanol in water and 0.05% ammonia hydroxide) to afford 1-(cyclopentylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (41.5 mg, 15%) as a white solid: $^1$H NMR (400 MHz, $CD_3OD$) δ 8.47 (s, 1H), 5.99 (s, 1H), 4.53-4.48 (m, 1H), 4.27-4.17 (m, 4H), 3.28 (s, 3H), 2.85-2.80 (m, 1H), 2.48-2.47 (m, 1H), 2.22-2.10 (m, 1H), 1.88-1.78 (m, 1H), 1.75-1.66 (m, 6H), 1.28-1.25 (m, 2H), 0.93-0.90 (m, 2H), 0.73-0.71 (m, 2H). LCMS $R_T$=0.79 min; m/z=398.1 (M+H)$^+$.

LCMS (5 to 95% acetonitrile in water+0.03% formic acid over 1.5 mins) retention time 0.79 min, ESI+ found [M+H]=398.1.

Example 262

WX Method III

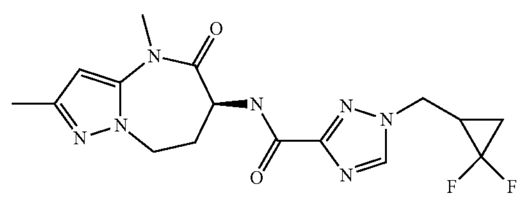 [SMILES: Cc1cc2n(n1)CC[C@H](NC(=O)c1ncn(CC3CC3(F)F)n1)C(=O)N2C]

1-((2,2-difluorocyclopropyl)methyl)-N—((S)-2,4-dimethyl-5-oxo-5,6,7,8-tetrahydro-4H-pyrazolo[1,5-a][1,3]diazepin-6-yl)-1H-1,2,4-triazole-3-carboxamide A mixture of N-[(6S)-2,4-dimethyl-5-oxo-7,8-dihydro-6H-pyrazolo[1,5-a][1,3]di azepin-6-yl]-1H-1,2,4-triazole-3-carboxamide (250 mg, 0.86 mmol) and potassium carbonate (358 mg, 2.59 mmol) in N,N-dimethylformamide (5 mL)

was added 2-(bromomethyl)-1,1-difluoro-cyclopropane (177 mg, 1.04 mmol). The mixture was stirred at 25° C. for 12 h. The reaction mixture was concentrated under reduced pressure, and the residue was purified by RP-HPLC (methanol 40-70%/0.05% ammonia hydroxide in water) to afford 1-((2,2-difluorocyclopropyl)methyl)-N—((S)-2,4-dimethyl-5-oxo-5,6,7,8-tetrahydro-4H-pyrazolo[1,5-a][1,3]diazepin-6-yl)-1H-1,2,4-triazole-3-carboxamide (62.6 mg, 19%) as white solid: $^1$H NMR (400 MHz, $CD_3OD$) δ 8.50 (s, 1H), 6.10 (s, 1H), 4.55-4.43 (m, 2H), 4.33-4.20 (m, 3H), 3.29 (s, 3H), 2.87-2.80 (m, 1H), 2.29-2.24 (m, 5H), 1.64-1.60 (m, 1H), 1.48-1.42 (m, 1H). LCMS $R_T$=0.696 min; m/z=380.1 $(M+H)^+$.

LCMS (5 to 95% acetonitrile in water+0.03% formic acid over 1.5 mins) retention time 0.696 min, ESI+ found [M+H]= 380.1.

Example 263

WX Method PPPPPP

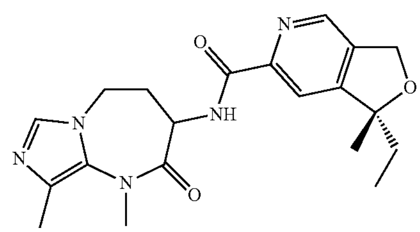 [SMILES: CC[C@@]1(C)OCc2cnc(C(=O)NC3CCn4cnc(C)c4N(C)C3=O)cc21]

(1R)—N-(1,9-dimethyl-2-oxo-2,3,4,5-tetrahydro-1H-imidazo[1,5-a][1,3]diazepin-3-yl)-1-ethyl-1-methyl-1,3-dihydrofuro[3,4-c]pyridine-6-carboxamide A mixture of (1R)-1-ethyl-1-methyl-3H-furo[3,4-c]pyridine-6-carboxylic acid (11 mg, 0.05 mmol), 3-amino-1,9-dimethyl-4,5-dihydro-1H-imidazo[1,5-a][1,3]diazepin-2(3H)-one (10 mg, 0.05 mmol), $N^1$-((ethylimino)methylene)-$N^3$,$N^3$-dimethylpropane-1,3-diamine hydrochloride (12 mg, 0.06 mmol) and 1H-benzo[d][1,2,3]triazol-1-ol (9 mg, 0.06 mmol) in N,N-dimethylformamide (4 mL) was stirred at 25° C. for 12 h. The reaction mixture was concentrated under reduced pressure and the residue was purified by RP-HPLC (acetonitrile 17-47/0.05% ammonia hydroxide in water) to afford (1R)—N-(1,9-dimethyl-2-oxo-2,3,4,5-tetrahydro-1H-imidazo[1,5-a][1,3]diazepin-3-yl)-1-ethyl-1-methyl-1,3-dihydrofuro[3,4-c]pyridine-6-carboxamide (8 mg, 38%) as white solid: $^1$H NMR (400 MHz, $CD_3OD$) δ 8.57 (s, 1H), 7.88 (s, 1H), 7.58 (s, 1H), 5.21-5.16 (m, 2H), 4.87-4.57 (m, 1H), 4.39-4.33 (m, 1H), 4.00-3.96 (m, 1H), 3.34 (s, 3H), 2.78-2.76 (m, 1H), 2.23 (s, 3H), 2.15-2.11 (m, 1H), 1.89-1.83 (m, 2H), 1.47 (s, 3H), 0.80-0.76 (m, 3H). LCMS $R_T$=1.87 min; m/z=384.2 $(M+H)^+$.

LCMS (0-60% acetonitrile in water+0.05% ammonium bicarbonate over 3 mins) retention time 1.87/min, ESI+ found [M+H]=384.2.

Example 264

WX Method UUUU

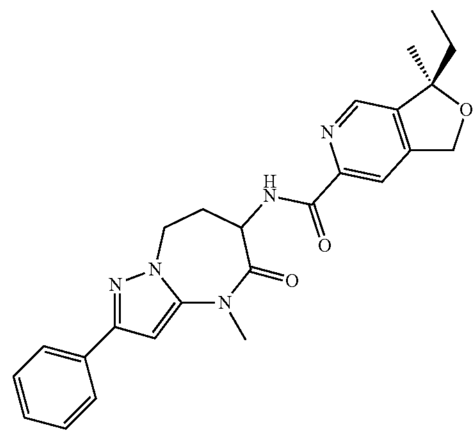 [SMILES: CC[C@@]1(C)OCc2cc(C(=O)NC3CCn4nc(-c5ccccc5)cc4N(C)C3=O)ncc21]

(3R)-3-ethyl-3-methyl-N-(4-methyl-5-oxo-2-phenyl-5,6,7,8-tetrahydro-4H-pyrazolo[1,5-a][1,3]diazepin-6-yl)-1,3-dihydrofuro[3,4-c]pyridine-6-carboxamide A mixture of 6-amino-4-methyl-2-phenyl-7,8-dihydro-4H-pyrazolo[1,5-a][1,3]diazepin-5(6H)-one (20 mg, 0.08 mmol), (1R)-1-ethyl-1-methyl-3H-furo[3,4-c]pyridine-6-carboxylic acid (16 mg, 0.08 mmol), 1H-benzo[d][1,2,3]triazol-1-ol (16 mg, 0.12 mmol) and N1-((ethylimino)methylene)-N3,N3-dimethylpropane-1,3-diamine hydrochloride (22 mg, 0.12 mmol) in N,N-dimethylformamide (5 mL) was stirred at 25° C. for 16 h. The reaction was concentrated under reduced pressure and the residue was purified by RP-HPLC (38% to 68% acetonitrile, 0.05% ammonia hydroxide in water) to give (3R)-3-ethyl-3-methyl-N-(4-methyl-5-oxo-2-phenyl-5,6,7,8-tetrahydro-4H-pyrazolo[1,5-a][1,3]diazepin-6-yl)-1,3-dihydrofuro[3,4-c]pyridine-6-carboxamide (21 mg, 60%) as a white solid: $^1$H NMR (400 MHz, $CD_3OD$) δ 8.55 (s, 1H), 7.86-7.80 (m, 3H), 7.43-7.31 (m, 3H), 6.70 (s, 1H), 5.19-5.12 (m, 2H), 4.68-4.36 (m, 3H), 3.42 (s, 3H), 3.02-2.94 (m, 1H), 2.35-2.27 (m, 1H), 1.87-1.82 (m, 2H), 1.45 (s, 3H), 0.78-0.74 (m, 3H). LCMS $R_T$=0.76 min; m/z=446.1 $(M+H)^+$.

LCMS (5 to 95% acetonitrile in water+0.03% trifluoacetic acid over 1.5 mins) retention time 0.76 min, ESI+ found [M+H]=446.1.

Example 265

WX Method VVVV

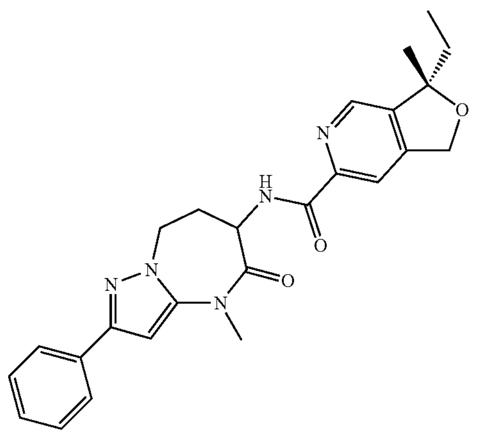 [SMILES: CC[C@]1(C)OCc2cc(C(=O)NC3CCn4nc(-c5ccccc5)cc4N(C)C3=O)ncc21]

(3S)-3-ethyl-3-methyl-N-(4-methyl-5-oxo-2-phenyl-5,6,7,8-tetrahydro-4H-pyrazolo[1,5-a][1,3]diazepin-6-yl)-1,3-dihydrofuro[3,4-c]pyridine-6-carboxamide A mixture of 6-amino-4-methyl-2-phenyl-7,8-dihydro-4H-pyrazolo[1,5-a][1,3]diazepin-5(6H)-one (30 mg, 0.12 mmol), (1S)-1-ethyl-1-methyl-3H-furo[3,4-c]pyridine-6-carboxylic acid (24 mg, 0.12 mmol), 1H-benzo[d][1,2,3]triazol-1-ol (24 mg, 0.18 mmol) and N1-((ethylimino)methylene)-N3,N3-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (38% to 68% acetonitrile, 0.05% ammonia hydroxide in water) to give (3S)-3-ethyl-3-methyl-N-(4-methyl-5-oxo-2-phenyl-5,6,7,8-tetrahydro-4H-pyrazolo[1,5-a][1,3]diazepin-6-yl)-1,3-dihydrofuro[3,4-c]pyridine-6-c arboxamide (19.2 mg, 36.2%) as a white solid: $^1$H NMR (400 MHz, $CD_3OD$) δ 8.55 (s, 1H), 7.86-7.80 (m, 3H), 7.43-7.31 (m, 3H), 6.70 (s, 1H), 5.19-5.12 (m, 2H), 4.68-4.36 (m, 3H), 3.42 (s, 3H), 3.02-2.94 (m, 1H), 2.35-2.29 (m, 1H), 1.87-1.82 (m, 2H), 1.45 (s, 3H), 0.78-0.74 (m, 3H). LCMS $R_T$=0.75 min; m/z=446.1 $(M+H)^+$.

LCMS (5 to 95% acetonitrile in water+0.03% trifluoacetic acid over 1.5 mins) retention time 0.75 min, ESI+ found [M+H]=446.1.

Example 266

WX Method UU

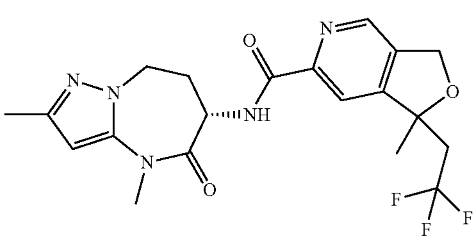 [SMILES: Cc1cc2n(n1)CC[C@H](NC(=O)c1cc3c(cn1)COC3(C)CC(F)(F)F)C(=O)N2C]

N—((S)-2,4-dimethyl-5-oxo-5,6,7,8-tetrahydro-4H-pyrazolo[1,5-a][1,3]diazepin-6-yl)-1-m ethyl-1-(2,2,2-trifluoroethyl)-1,3-dihydrofuro[3,4-c]pyridine-6-carboxamide A mixture of 1-methyl-1-(2,2,2-trifluoroethyl)-3H-furo[3,4-c]pyridine-6-carboxylic acid (48 mg, 0.19 mmol), (6R)-6-amino-2,4-dimethyl-7,8-dihydro-6H-pyrazolo[1,5-a][1,3]diazepin-5-one (30 mg, 0.15 mmol), 1H-benzo[d][1,2,3]triazol-1-ol (25 mg, 0.19 mmol) and $N^1$-((ethylimino)methylene)-$N^3$,$N^3$-dimethylpropane-1,3-diamine hydrochloride (38 mg, 0.19 mmol) in N,N-dimethylformamide (5 mL) was stirred at 25° C. for 1 h. The reaction was concentrated under reduced pressure and the residue was purified by RP-HPLC (acetonitrile 31-61%/0.05% ammonium hydroxide in water) to give N—((S)-2,4-dimethyl-5-oxo-5,6,7,8-tetrahydro-4H-pyrazolo[1,5-a][1,3]diazepin-6-yl)-1-methyl-1-(2,2,2-trifluoroethyl)-1,3-dihydrofuro[3,4-c]pyridine-6-carboxamide (57.6 mg, 84%) as light red solid: $^1$H NMR (400 MHz, $CD_3OD$): δ 8.61 (s, 1H), 8.03 (s, 1H), 6.13 (s, 1H), 5.20 (s, 2H), 4.63-4.57 (m, 1H), 4.35-4.24 (m, 2H), 3.35 (s, 3H), 2.92-2.81 (m, 3H), 2.32-2.25 (m, 4H), 1.57 (s, 3H). LCMS $R_T$=1.234 min; m/z=438.2 $(M+H)^+$.

LCMS (0 to 60% acetonitrile in water+0.03% trifluoacetic acid over 2 mins) retention time 1.234 min, ESI+ found $[M+H]^+$=438.2.

Example 267

WX Method A

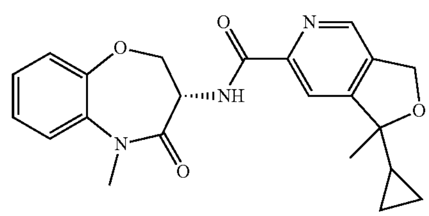 [SMILES: CN1C(=O)[C@@H](NC(=O)c2cc3c(cn2)COC3(C)C2CC2)COc2ccccc21]

1-cyclopropyl-1-methyl-N—((S)-5-methyl-4-oxo-2,3,4,5-tetrahydrobenzo[b][1,4]oxazepin-3-yl)-1,3-dihydrofuro[3,4-c]pyridine-6-carboxamide

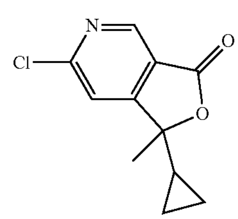

Step 1: 6-chloro-1-cyclopropyl-1-methylfuro[3,4-c]pyridin-3(1H)-one

To a mixture of 2,2,6,6-tetramethylpiperidine (54.0 g, 381 mmol) in tetrahydrofuran (500 mL) was added n-butyllithium (203 mL, 508 mmol, 2.5 M in tetrahydrofuran) at −78° C. After stirring at −78° C. for 40 min, 6-chloronicotinic acid (20.0 g, 127 mmol) in tetrahydrofuran (200 mL)

was added into the mixture and stirred for 2 h at −78° C. 1-cyclopropylethanone (107.0 g, 1269 mmol) was added dropwise into the mixture at −78° C. The reaction was allowed warm to 25° C. and stirred for 16 h. The reaction was quenched by addition of saturated aqueous ammonium chloride and acidified to pH=4 by using hydrochloric acid (2.0 M). The reaction was extracted with ethyl acetate (3×300 mL). The organics were washed with water (2×100 mL), brine (100 mL). The combined organic layers were dried with anhydrous magnesium sulfate and concentrated under reduced pressure. The residue was purified by recrystallization with ethyl acetate (60 mL) affording 6-chloro-1-cyclopropyl-1-methylfuro[3,4-c]pyridin-3(1H)-one (24.0 g, 84%) as a white solid, used as is in the next step.

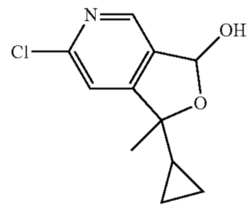

Step 2: 6-chloro-1-cyclopropyl-1-methyl-1,3-dihydrofuro[3,4-c]pyridin-3-ol

To a mixture of 6-chloro-1-cyclopropyl-1-methylfuro[3,4-c]pyridin-3(1H)-one (24.0 g, 107 mmol) in toluene (500 mL) was added diisobutylaluminum hydride (236 mL, 236 mmol, 1.0 M in toluene) and then stirred for 2 h at −78° C. The mixture was quenched by addition of saturated aqueous ammonium chloride at −78° C. and extracted with ethyl acetate (3×100 mL). The combined organic layers were washed with water (2×50 mL), brine (50 mL), dried over sodium sulfate and concentrated under reduced pressure affording crude 6-chloro-1-cyclopropyl-1,3-dihydrofuro[3,4-c]pyridin-3-ol (23.0 g, 95%) as colourless oil, used as is in the next step.

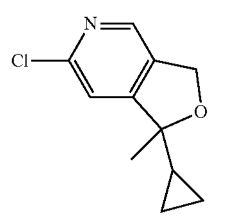

Step 3: 6-chloro-1-cyclopropyl-1-methyl-1,3-dihydrofuro[3,4-c]pyridine

To a mixture of 6-chloro-1-cyclopropyl-1,3-dihydrofuro[3,4-c]pyridin-3-ol affording (23.0 g, 102 mmol) and 2,2,2-trifluoroacetic acid (58.1 g, 510 mmol) in dichloromethane (100 mL) was added triethylsilane (59.3 g, 510 mmol) at 0° C. After addition, the mixture was stirred for 2 h and then adjusted to pH=8 by additional of 5% aqueous sodium hydroxide. The mixture was concentrated to dryness under reduced pressure. The residue was taken up in ethyl acetate (200 mL). The organics were washed with water (2×100 mL), brine (100 mL), dried over sodium sulfate and concentrated under reduced pressure. The residue was purified by flash column chromatography (silica gel, 100-200 mesh, 100% petroleum ether) affording 6-chloro-1-cyclopropyl-1-methyl-1,3-dihydrofuro[3,4-c]pyridine (17.0 g, 79.6%) as a white solid: $^{1}$H NMR (400 MHz, $CDCl_3$) δ 8.25 (s, 1H), 7.14 (s, 1H), 5.07-4.99 (m, 2H), 1.47 (s, 3H), 1.18-1.16 (m, 1H), 0.52-0.29 (m, 4H).

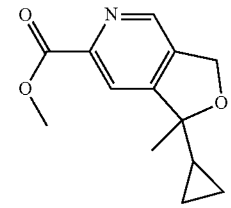 [SMILES: COC(=O)c1cc2c(cn1)COC2(C)C1CC1]

Step 4: methyl 1-cyclopropyl-1-methyl-1,3-dihydrofuro[3,4-c]pyridine-6-carboxylate A mixture of 6-chloro-1-cyclopropyl-1-methyl-1,3-dihydrofuro[3,4-c]pyridine (5.0 g, 24 mmol), 1,1'-bis(diphenylphosphino)ferrocene palladiumdichloride (1.7 g, 2.4 mmol) in methanol (100 mL) was stirred at 80° C. under carbonic oxide atmosphere (25 psi) for 16 h. The reaction was filtrated and the filtrate was concentrated to dryness under reduced pressure. The residue was purified by flash column chromatography (silica gel, 100-200 mesh, 0 to 30% ethyl acetate in petroleum ether) affording 1-cyclopropyl-1-methyl-1,3-dihydrofuro[3,4-c]pyridine-6-carboxylate (5.3 g, 95%) as colorless oil: LCMS $R_T$=0.65 min; m/z=233.8 $(M+H)^+$.

LCMS (5 to 95% acetonitrile in water+0.03% trifluoacetic acid over 1.5 mins) retention time 0.65 min, ESI+ found [M+H]=233.8.

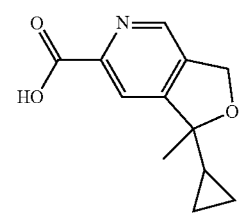 [SMILES: CC1(C2CC2)OCc2cnc(C(=O)O)cc21]

Step 5: 1-cyclopropyl-1-methyl-1,3-dihydrofuro[3,4-c]pyridine-6-carboxylic acid

A mixture of methyl 1-cyclopropyl-1-methyl-1,3-dihydrofuro[3,4-c]pyridine-6-carboxylate (5.3 g, 23.0 mmol) and lithium hydroxide (5.4 g, 227.0 mmol) in tetrahydrofuran (50 mL) and water (50 mL) was stirred at 25° C. for 16 h. The mixture was adjusted to pH=6 by addition of hydrochloric acid (1.0 M). The resulting solution was concentrated to dryness under reduced pressure. The residue was purified by column chromatography (silica gel, 100-200 mesh, 0 to 10% methanol in dichloromethane) affording 1-cyclopropyl-1-methyl-1,3-dihydrofuro[3,4-c]pyridine-6-carboxylic acid (3.6 g, 72.3%) as a white solid: $^{1}$H NMR (400 MHz, MeOD) δ 8.53 (s, 1H), 7.98 (s, 1H), 5.13-5.05 (m, 2H), 1.52 (s, 3H), 1.34-1.27 (m, 1H), 0.50-0.30 (m, 4H).

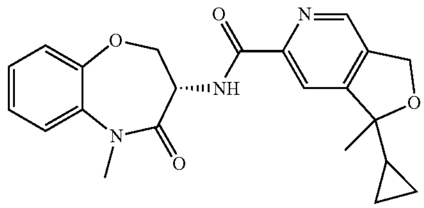 [SMILES: CN1C(=O)[C@@H](NC(=O)c2cc3c(cn2)COC3(C)C2CC2)COc2ccccc21]

Step 6: 1-cyclopropyl-1-methyl-N—((S)-5-methyl-4-oxo-2,3,4,5-tetrahydrobenzo[b][1,4]oxazepin-3-yl)-1,3-dihydrofuro[3,4-c]pyridine-6-carboxamide A mixture of (3S)-3-amino-5-methyl-2,3-dihydro-1,5-benzoxazepin-4-one (30 mg, 0.16 mmol), 1-cyclopropyl-1-methyl-1,3-dihydrofuro[3,4-c]pyridine-6-carboxylic acid (34 mg, 0.16 mmol), $N^1$-((ethylimino)methylene)-$N^3$,$N^3$-dimethylpropane-1,3-diamine hydrochloride (45 mg, 0.23 mmol), 1H-benzo[d][1,2,3]triazol-1-ol (32 mg, 0.23 mmol) in N,N-dimethylformamide (10 mL) was stirred at 25° C. for 16 h. The mixture was concentrated to dryness under reduced pressure and the residue was purified by RP-HPLC affording 1-cyclopropyl-1-methyl-N—((S)-5-methyl-4-oxo-2,3,4,5-tetrahydro benzo[b][1,4]oxazepin-3-yl)-1,3-dihydrofuro[3,4-c]pyridine-6-carboxamide (24 mg, 38%) as a white solid: $^1$H NMR (400 MHz, $CD_3OD$) δ 8.58 (s, 1H), 7.95 (s, 1H), 7.47-7.28 (m, 4H), 5.17-5.03 (m, 3H), 4.69-4.65 (m, 1H), 4.45-4.40 (m, 1H), 3.45 (s, 3H), 1.52 (s, 3H), 1.31-1.26 (m, 1H), 0.50-0.28 (m, 4H). LCMS $R_T$=0.76 min; m/z=394.0 $(M+H)^+$.

Example 268

WX Method CCC

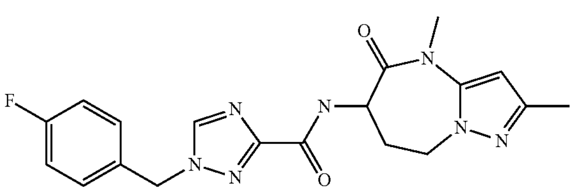 [SMILES: Cc1cc2n(n1)CCC(NC(=O)c1ncn(Cc3ccc(F)cc3)n1)C(=O)N2C]

N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide A mixture of N-(2,4-dimethyl-5-oxo-7,8-dihydro-6H-pyrazolo[1,5-a][1,3]diazepin-6-yl)-1H-1,2,4-triazole-3-carboxamide (250 mg, 0.86 mmol) and potassium carbonate (358 mg, 2.59 mmol) in N,N-dimethylformamide (5 mL) was added 4-fluorobenzyl bromide (327 mg, 1.73 mmol). The mixture was stirred at 25° C. for 12 h and then concentrated under reduced pressure. The residue was purified by RP-HPLC (methanol 46-76%/0.05% ammonia hydroxide in water) to afford N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide (43.7 mg, 13%) as white solid: $^1$H NMR (400 MHz, DMSO-$d_6$) δ 8.81 (s, 1H), 8.53 (d, J=8.0 Hz, 1H), 7.40-7.36 (m, 2H), 7.23-7.19 (m, 2H), 6.12 (s, 1H), 5.47 (s, 2H), 4.32-4.26 (m, 2H), 4.12-4.09 (m, 1H), 3.21 (s, 3H), 2.50-2.44 (m, 2H), 2.16 (s, 3H).

LCMS (5 to 95% acetonitrile in water+0.03% formic acid over 1.5 mins) retention time 0.748 min, ESI+ found [M+H]=398.1.

Example 269

WX Method VVV

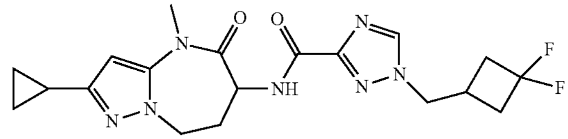 [SMILES: CN1C(=O)C(NC(=O)c2ncn(CC3CC(F)(F)C3)n2)CCn2nc(C3CC3)cc21]

N-(2-cyclopropyl-4-methyl-5-oxo-5,6,7,8-tetrahydro-4H-pyrazolo[1,5-a][1,3]diazepin-6-yl)-1-((3,3-difluorocyclobutyl)methyl)-1H-1,2,4-triazole-3-carboxamide To a suspension of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) and potassium carbonate (329 mg, 2.38 mmol) in N,N-dimethylformamide (5 mL) was added 3-(bromomethyl)-1,1-difluoro-cyclobutane (293 mg, 1.59 mmol). The mixture was stirred at 25° C. for 12 h and then filtered. The filtrate was evaporated under reduced pressure and the residue was purified by RP-HPLC (47-77% methanol in water and 0.05% ammonia) to afford N-(2-cyclopropyl-4-methyl-5-oxo-5,6,7,8-tetrahydro-4H-pyrazolo[1,5-a][1,3]diazepin-6-yl)-1-((3,3-difluorocyclobutyl)methyl)-1H-1,2,4-triazole-3-carboxamide (40 mg, 12%) as white solid. $^1$H NMR (400 MHz, $CDCl_3$) δ 8.08 (s, 1H), 8.01 (d, J=6.4 Hz, 1H), 5.76 (s, 1H), 4.76-4.73 (m, 1H), 4.39-4.30 (m, 3H), 4.11-4.05 (m, 1H), 3.33 (s, 3H), 3.20-3.12 (m, 1H), 2.78-2.70 (m, 3H), 2.39-2.33 (m, 2H), 1.90-1.87 (m, 2H), 0.94-0.91 (m, 2H), 0.75-0.72 (m, 2H). LCMS $R_T$=0.95 min; m/z=420.2 $(M+H)^+$.

LCMS (10 to 80% acetonitrile in water+0.03% trifluoacetic acid over 2.0 mins) retention time 0.95 min, ESI+ found [M+H]=420.2.

Example 270

WX Method HHH

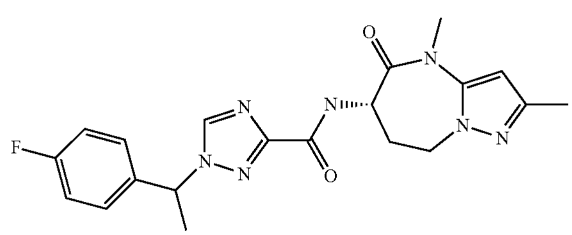 [SMILES: Cc1cc2n(n1)CC[C@H](NC(=O)c1ncn(C(C)c3ccc(F)cc3)n1)C(=O)N2C]

N—((S)-2,4-dimethyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide

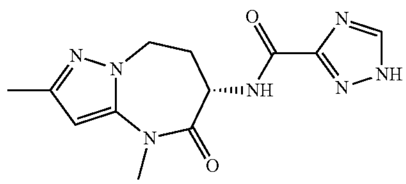

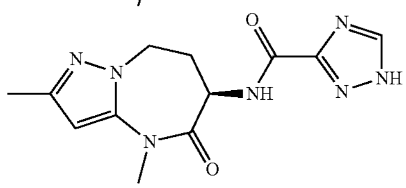

Step 1: (S)—N-(2,4-dimethyl-5-oxo-5,6,7,8-tetrahydro-4H-pyrazolo[1,5-a][1,3]diazepin-6-yl)-1H-1,2,4-triazole-3-carboxamide and (R)—N-(2,4-dimethyl-5-oxo-5,6,7,8-tetrahydro-4H-pyrazolo[1,5-a][1,3]diazepin-6-yl)-1H-1,2,4-triazole-3-carboxamide N-(2,4-dimethyl-5-oxo-7,8-dihydro-6H-pyrazolo[1,5-a][1,3]diazepin-6-yl)-1H-1,2,4-triazole-3-carboxamide (2.8 g, 9.8 mmol) was separated by chiral SFC (SFC80; Chiralpak OD (150 mm*4.6 mm, 3 um); Supercritical $CO_2$/MeOH+$NH_3.H_2O$=20/20; 2.5 ml/min) to afford:

(S)—N-(2,4-dimethyl-5-oxo-5,6,7,8-tetrahydro-4H-pyrazolo[1,5-a][1,3]diazepin-6-yl)-1H-1,2, 4-triazole-3-carboxamide (Peak 1, $R_T$=3.259 min) (1.2 g, 40%);

(R)—N-(2,4-dimethyl-5-oxo-5,6,7,8-tetrahydro-4H-pyrazolo[1,5-a][1,3]diazepin-6-yl)-1H-1,2, 4-triazole-3-carboxamide (Peak 2, $R_T$=3.846 min) (1.5 g, 54%).

Step 2: N—((S)-2,4-dimethyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide A mixture of N-[(6S)-2,4-dimethyl-5-oxo-7,8-dihydro-6H-pyrazolo[1,5-a][1,3]di azepin-6-yl]-1H-1,2,4-triazole-3-carboxamide (250 mg, 0.86 mmol) and potassium carbonate (358 mg, 2.59 mmol) in N,N-dimethylformamide (5 mL) was added 1-(1-bromomethyl)-4-fluorobenzene (263 mg, 1.30 mmol). The mixture was stirred at 25° C. for 12 h. The reaction mixture was concentrated under reduced pressure, and the residue was purified by RP-HPLC (methanol 50-80%/0.05% ammonia hydroxide in water) to afford N—((S)-2,4-dimethyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide(21.2 mg, 6%) as white solid: $^1$H NMR (400 MHz, DMSO-$d_6$) δ 8.51 (s, 1H), 8.53 (d, J=7.6 Hz, 1H), 7.40-7.37 (m, 2H), 7.22-7.18 (m, 2H), 6.13 (s, 1H), 5.86-5.81 (m, 1H), 4.32-4.25 (m, 2H), 4.12-4.07 (m, 1H), 3.21 (s, 3H), 2.67-2.50 (m, 2H), 2.16 (s, 3H), 1.84 (d, J=7.2 Hz, 3H). LCMS $R_T$=0.759 min; m/z=412.3 $(M+H)^+$.

LCMS (5 to 95% acetonitrile in water+0.03% formic acid over 1.5 mins) retention time 0.759 min, ESI+ found [M+H]= 412.3.

Example 271

WX Method KKK

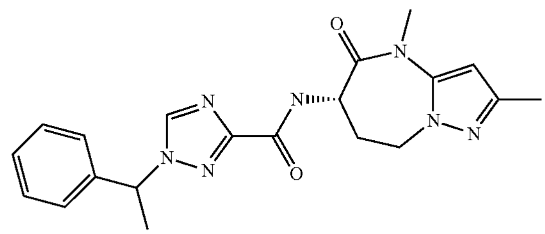 [SMILES: Cc1cc2n(n1)CC[C@H](NC(=O)c1ncn(C(C)c3ccccc3)n1)C(=O)N2C]

N—((S)-2,4-dimethyl-5-oxo-5,6,7,8-tetrahydro-4H-pyrazolo[1,5-a][1,3]diazepin-6-yl)-1-(1-phenylethyl)-1H-1,2,4-triazole-3-carboxamide A mixture of N-[(6S)-2,4-dimethyl-5-oxo-7,8-dihydro-6H-pyrazolo[1,5-a][1,3]di azepin-6-yl]-1H-1,2,4-triazole-3-carboxamide (250 mg, 0.86 mmol) and potassium carbonate (358 mg, 2.59 mmol) in N,N-dimethylformamide (5 mL) was added (1-bromoethyl)benzene (240 mg, 1.3 mmol) and. The mixture was stirred at 25° C. for 12 h. The reaction mixture was concentrated under reduced pressure, and the residue was purified by RP-HPLC (methanol 50-80%/0.05% ammonia hydroxide in water) to afford N—((S)-2,4-dimethyl-5-oxo-5, 6,7,8-tetrahydro-4H-pyrazolo[1,5-a][1,3]diazepin-6-yl)-1-(1-phenylethyl)-1H-1,2,4-triazole-3-carboxamide (24.8 mg, 7%) as white solid: $^1$H NMR (400 MHz, DMSO-$d_6$) δ 8.87 (s, 1H), 8.53 (d, J=8.0 Hz, 1H), 7.38-7.30 (m, 5H), 6.13 (s, 1H), 5.84-5.78 (m, 1H), 4.33-4.23 (m, 2H), 4.12-4.09 (m, 1H), 3.21 (s, 3H), 2.59-2.57 (m, 1H), 2.37-2.34 (m, 1H), 2.16 (s, 3H), 1.85 (d, J=7.2 Hz, 3H). LCMS $R_T$=0.758 min, m/z=394.1 $(M+H)^+$.

LCMS (5 to 95% acetonitrile in water+0.03% formic acid over 1.5 mins) retention time 0.758 min, ESI+ found [M+H]= 394.1.

Example 272

WX Method FFFFF

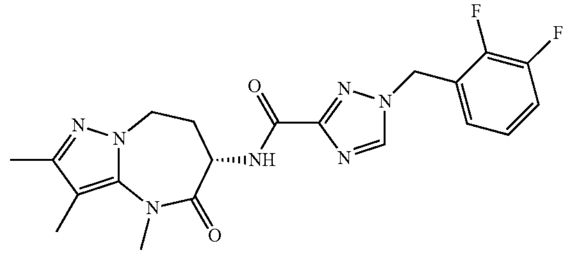 [SMILES: Cc1nn2c(c1C)N(C)C(=O)[C@@H](NC(=O)c1ncn(Cc3cccc(F)c3F)n1)CC2]

(S)-1-(2,3-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide A mixture of 1-[(2,3-difluorophenyl)methyl]-1,2,4-triazole-3-carboxylic acid (26 mg, 0.11 mmol), (6S)-6-amino-2,3,4-trimethyl-7,8-dihydro-6H-pyrazolo[1,5-a][1,3]diazepin- 5-one (20 mg, 0.09 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (25 mg, 0.14 mmol) in N,N-dimethylformamide (5 mL) was stirred at 25° C. for 12 h. The reaction was concentrated under reduced pressure and the residue was purified by RP-HPLC (acetonitrile 17-47/0.05% ammonium bicarbonate in water) to give (S)-1-(2,3-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide (27.9 mg, 71%) as white solid: $^1$H NMR (400 MHz, $CD_3OD$) δ 8.61 (s, 1H), 7.29-7.26 (m, 1H), 7.18-7.15 (m, 2H), 5.59 (s, 2H), 4.43-4.38 (m, 1H), 4.24-4.18 (m, 2H), 3.30 (s, 3H), 2.78-2.70 (m, 1H), 2.19 (m, 4H), 2.00 (s, 3H). LCMS $R_T$=0.972 min; m/z=430.2 $(M+H)^+$.

LCMS (10 to 80% acetonitrile in water+0.03% trifluoacetic acid over 2.0 mins) retention time 0.972 min, ESI+ found [M+H]=430.2.

Example 273

WX Method GGGGG

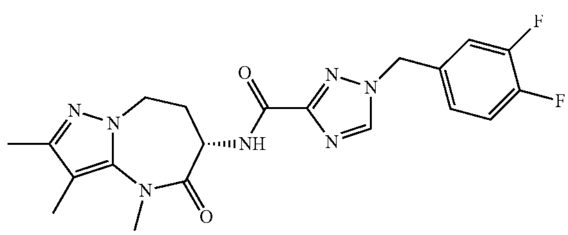 [SMILES: Cc1nn2c(c1C)N(C)C(=O)[C@@H](NC(=O)c1ncn(Cc3ccc(F)c(F)c3)n1)CC2]

(S)-1-(3,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide A mixture of 1-[(3,4-difluorophenyl)methyl]-1,2,4-triazole-3-carboxylic acid (26 mg, 0.11 mmol), (6S)-6-amino-2,3,4-trimethyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (25 mg, 0.14 mmol) in N,N-dimethylformamide (5 mL) was stirred at 25° C. for 12 h. The reaction was concentrated under reduced pressure and the residue was purified by RP-HPLC (acetonitrile 17-47/0.05% ammonium bicarbonate in water) to give (S)-1-(3,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide (31.3 mg, 80%) as white solid: $^1$H NMR (400 MHz, $CD_3OD$) δ 8.60 (s, 1H), 7.32-7.24 (m, 2H), 7.18-7.17 (m, 1H), 5.45 (s, 2H), 4.39-4.39 (m, 1H), 4.24-4.18 (m, 2H), 3.30 (s, 3H), 2.81-2.73 (m, 1H), 2.20-2.16 (m, 4H), 2.00 (s, 3H). LCMS $R_T$=0.98 min; m/z=430.2 $(M+H)^+$.

LCMS (10 to 80% acetonitrile in water+0.03% trifluoacetic acid over 2.0 mins) retention time 0.98 min, ESI+ found [M+H]=430.2.

Example 274

WX Method DDDDD

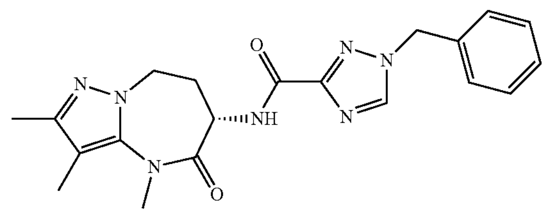 [SMILES: Cc1nn2c(c1C)N(C)C(=O)[C@@H](NC(=O)c1ncn(Cc3ccccc3)n1)CC2]

(S)-1-benzyl-N-(2,3,4-trimethyl-5-oxo-5,6,7,8-tetrahydro-4H-pyrazolo[1, 5-a][1,3]diazepin-6-yl)-1H-1,2,4-triazole-3-carboxamide A mixture of (1-benzyl-1,2,4-triazole-3-carboxylic acid (22.1 mg, 0.11 mmol), (6S)-6-amino-2,3,4-trimethyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (25 mg, 0.14 mmol) in N,N-dimethylformamide (5 mL) was stirred at 25° C. for 12 h. The reaction was concentrated under reduced pressure and the residue was purified by RP-HPLC (acetonitrile 17-47/0.05% ammonium bicarbonate in water) to give (S)-1-benzyl-N-(2,3,4-trimethyl-5-oxo-5,6,7,8-tetrahydro-4H-pyrazolo[1,5-a][1,3]diazepin-6-yl)-1H-1,2,4-triazole-3-carboxamide (23.5 mg, 65%) as white solid. $^{11}$H NMR (400 MHz, $CD_3OD$) δ 8.55 (s, 1H), 7.38-7.32 (m, 5H), 5.46 (s, 2H), 4.44-4.39 (m, 1H), 4.24-4.18 (m, 2H), 3.30 (s, 3H), 2.81-2.73 (m, 1H), 2.21-2.18 (m, 4H), 2.00 (s, 3H). LCMS $R_T$=0.94 min; m/z=394.2 $(M+H)^+$.

LCMS (10 to 80% acetonitrile in water+0.03% trifluoacetic acid over 2.0 mins) retention time 0.94 min, ESI+ found [M+H]=394.2.

Example 275

WX Method VV

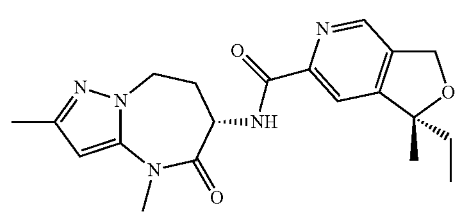 [SMILES: CC[C@@]1(C)OCc2cnc(C(=O)N[C@H]3CCn4nc(C)cc4N(C)C3=O)cc21]

(R)—N—((S)-2,4-dimethyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide A mixture of (1R)-1-ethyl-1-methyl-3H-furo[3,4-c]pyridine-6-carboxylic acid (38 mg, 0.19 mmol), (6R)-6-amino-2,4-dimethyl-7,8-dihydro-6H-pyrazolo[1,5-a][1,3]diazepin-5-one (30 mg, 0.15 mmol), 1H-benzo[d][1,2,3]triazol-1-ol (25 mg, 0.19 mmol) and $N^1$-((ethylimino)methylene)-$N^3$, $N^3$-dimethylpropane-1,3-diamine hydrochloride (38 mg, 0.19 mmol) in N,N-dimethylformamide (5 mL) was stirred at 25° C. for 1 h. The reaction was concentrated under reduced pressure and the residue was purified by RP-HPLC (acetonitrile 30-60%/0.05% ammonium hydroxide in water) to give (R)—N—((S)-2,4-dimethyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide (25.5 mg, 43%) as white solid: $^1H$ NMR (400 MHz, $CD_3OD$) δ 8.57 (s, 1H), 7.87 (s, 1H), 6.13 (s, 1H), 5.21-5.16 (m, 2H), 4.59-4.55 (m, 1H), 4.33-4.24 (m, 2H), 3.35 (s, 3H), 2.95-2.88 (m, 1H), 2.29-2.22 (m, 4H), 1.89-1.83 (m, 2H), 1.47 (s, 3H), 0.77 (t, J=7.6 Hz, 3H). LCMS $R_T$=1.197 min; m/z=384.2 $(M+H)^+$.

LCMS (0 to 60% acetonitrile in water+0.03% trifluoacetic acid over 2 mins) retention time 1.197 min, ESI+ found [M+H]-=384.2.

Example 276

WX Method CCCCC

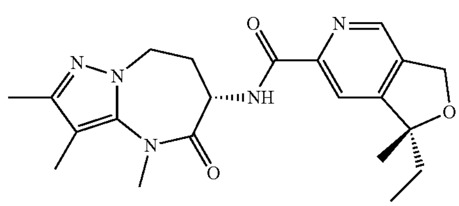 [SMILES: CC[C@@]1(C)OCc2cnc(C(=O)N[C@H]3CCn4nc(C)c(C)c4N(C)C3=O)cc21]

(R)-1-ethyl-1-methyl-N—((S)-2,3,4-trimethyl-5-oxo-5,6,7,8-tetrahydro-4H-pyrazolo[1,5-a][1,3]diazepin-6-yl)-1,3-dihydrofuro[3,4-c]pyridine-6-carboxamide

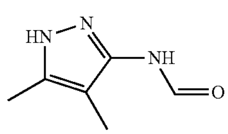

Step 1: N-(4,5-dimethyl-1H-pyrazol-3-yl)formamide

A solution of 4,5-dimethyl-1H-pyrazol-3-amine (15.0 g, 135.0 mmol) in formic acid (75 mL) was heated to 110° C. for 3 h in a sealed vessel. The reaction mixture was concentrated under reduced pressure and the residue was purified by column chromatography (silica gel, 100-200 mesh, 0 to 15% methanol in dichloromethane) to afford N-(4,5-dimethyl-1H-pyrazol-3-yl)formamide (15.0 g, 80%) as an off-white solid, used in the next step without further purification.

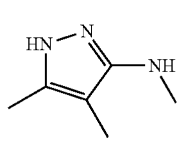

Step 2: N-4,5-trimethyl-1H-pyrazol-3-amine

To a solution of N-(5-methyl-1H-pyrazol-3-yl)formamide (15.0 g, 107.8 mmol) in tetrahydrofuran (500 mL) was slowly added lithium aluminum hydride (8.2 g, 215.2 mmol) at 0° C. After addition, the reaction mixture was allowed to warm to 25° C. and stirred for 16 h. The reaction was quenched by addition of solid sodium sulfate decahydrate and stirred at 25° C. for 30 mins. The resulting mixture was diluted with ethyl acetate (200 mL), filtered through celite, and concentrated under reduced pressure to afford N-4,5-trimethyl-1H-pyrazol-3-amine (14.0 g, 104%) as yellow oil, used as is in the next step.

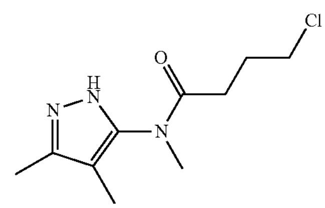

Step 3: 4-chloro-N-(3,4-dimethyl-1H-pyrazol-5-yl)-N-methylbutanamide

A solution of N-4,5-trimethyl-1H-pyrazol-3-amine (14.0 g, 111.8 mmol) in 4-chlorobutanoyl chloride (30.0 mL, 295.0 mmol) was heated to 60° C. for 2 h. After cooled, methanol (30 mL) was added carefully. The mixture was stirred at 20° C. for another 1 h and then concentrated under reduced pressure. The residue was purified by column chromatography (silica gel, 100-200 mesh, 0 to 5% methanol in dichloromethane) to afford 4-chloro-N-(3,4-dimethyl-1H-pyrazol-5-yl)-N-methylbutanamide (18.0 g, 70%) as an orange oil: LCMS $R_T$=1.08 min; m/z=230.1 $(M+H)^+$.

LCMS (0 to 60% acetonitrile in water+0.03% trifluoacetic acid over 2 mins) retention time 1.08 min, ESI+ found [M+H]=230.1.

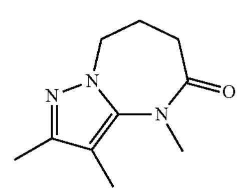

Step 4: 2,3,4-trimethyl-7,8-dihydro-4H-pyrazolo[1,5-a][1,3]diazepin-5(6H)-one

To a solution of 4-chloro-N-(3,4-dimethyl-1H-pyrazol-5-yl)-N-methylbutanamide (18.0 g, 78.4 mmol) in N,N-dimethylformamide (200 mL) was added cesium carbonate (51.1 g, 156.7 mmol), and the resulting suspension was stirred at 20° C. for 16 h. The reaction mixture was filtered through celite and concentrated under reduced pressure. The residue was purified by column chromatography (silica gel, 100-200 mesh, 0 to 10% methanol in dichloromethane) to afford 2,3,4-trimethyl-7,8-dihydro-4H-pyrazolo[1,5-a][1,3]diazepin-5(6H)-one (11.0 g, 73%) as colorless oil: LCMS $R_T$=0.57 min; m/z=193.9 $(M+H)^+$.

LCMS (5 to 95% acetonitrile in water+0.03% trifluoacetic acid over 1.5 mins) retention time 0.57 min, ESI+ found [M+H]=193.9.

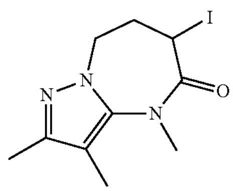

Step 5: 6-iodo-2,3,4-trimethyl-7,8-dihydro-4H-pyrazolo[1,5-a][1,3]diazepin-5(6H)-one To a solution of 2,4-dimethyl-7,8-dihydro-6H-pyrazolo[1,5-a][1,3]diazepin-5-one (2.0 g, 10.4 mmol) in dichloromethane (50 mL) was added $N^1$,$N^1$,$N^2$,$N^2$-tetramethylethane-1,2-diamine (7.2 g, 62.1 mmol) followed by iodotrimethylsilane (12.4 g, 62.1 mmol) at −15° C. The resulting solution was stirred 2 h at −15° C., and iodine (7.9 g, 31.1 mmol) was added in one portion. Stirring at −15° C. was continued for 2 h, and the reaction mixture was quenched by addition of saturated sodium bisulfite (100 mL). The mixture was extracted with dichloromethane (3×100 mL). The combined organic extracts were dried over sodium sulfate and concentrated under reduced pressure. The residue was purified by column chromatography (silica gel, 100-200 mesh, 0 to 10% methanol in dichloromethane) to give 6-iodo-2,3,4-trimethyl-7,8-dihydro-4H-pyrazolo[1,5-a][1,3]diazepin-5(6H)-one as a brown solid (230 g, 70%) as yellow oil, used in the next step as is.

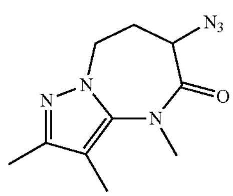 [SMILES: Cc1nn2c(c1C)N(C)C(=O)C(N=[N+]=[N-])CC2]

Step 6: 6-azido-2,3,4-trimethyl-7,8-dihydro-4H-pyrazolo[1,5-a][1,3]diazepin-5 (6H)-one To a solution of 6-iodo-2,3,4-trimethyl-7,8-dihydro-4H-pyrazolo[1,5-a][1,3]diazepin-5(6H)-one (2.0 g, 6.3 mmol) in N,N-dimethylformamide (10 mL) was added sodium azide (611.1 mg, 9.4 mmol). The reaction mixture was stirred at 20° C. for 2 hand then extracted with ethyl acetate (3×50 mL). The combined organic layers were washed with water (50 mL), brine (50 mL), dried over sodium sulfate and concentrated under reduced pressure. The residue was purified by column chromatography (silica gel, 100-200 mesh, 0 to 10% methanol in dichloromethane) to give 6-azido-2,3,4-trimethyl-7,8-dihydro-4H-pyrazolo[1,5-a][1,3]diazepin-5 (6H)-one (1.35 g, 92%) as a pale orange oil: LCMS $R_T$=0.64 min; m/z=235.1 $(M+H)^+$.

LCMS (5 to 95% acetonitrile in water+0.03% trifluoacetic acid over 1.5 mins) retention time 0.64 min, ESI+ found [M+H]=235.1.

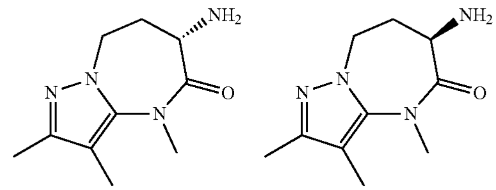

Step 7: (S)-6-amino-2,3,4-trimethyl-7,8-dihydro-4H-pyrazolo[1,5-a][1,3]diazepin-5(6H)-one and (R)-6-amino-2,3,4-trimethyl-7,8-dihydro-4H-pyrazolo[1,5-a][1,3]diazepin-5(6H)-one A mixture of 6-azido-2,3,4-trimethyl-7,8-dihydro-4H-pyrazolo[1,5-a][1,3]diazepin-5(6H)-one (1.4 g, 5.8 mmol) and 10% palladium on carbon (613 mg, 0.58 mmol) was hydrogenated (50 psi) at 25° C. for 10 h. The mixture was filtered and the filtrate was concentrated under reduced pressure to afford 6-amino-2,3,4-trimethyl-7,8-dihydro-4H-pyrazolo[1,5-a][1,3]diazepin-5(6H)-one (1.3 g, 104%) as colorless oil. Then the product was separated by chiral SFC to afford:

(S)-6-amino-2,3,4-trimethyl-7,8-dihydro-4H-pyrazolo[1,5-a][1,3]diazepin-5(6H)-one (Peak 1, Retention time: 3.19 min) (580 mg, 44.6% yield);

(R)-6-amino-2,3,4-trimethyl-7,8-dihydro-4H-pyrazolo[1,5-a][1,3]diazepin-5(6H)-one (Peak 2, Retention time: 3.66 min) (500 mg, 38% yield);

SFC condition: Column: Chiralpak AD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C. Wavelength: 220 nm.

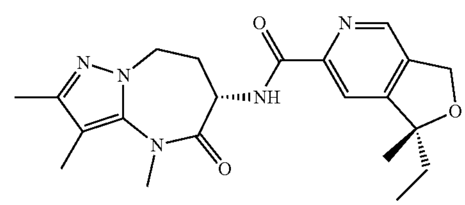 [SMILES: CC[C@@]1(C)OCc2cnc(C(=O)N[C@H]3CCn4nc(C)c(C)c4N(C)C3=O)cc21]

Step 8: (R)-1-ethyl-1-methyl-N—((S)-2,3,4-trimethyl-5-oxo-5,6,7,8-tetrahydro-4H-pyrazolo[1,5-a][1,3]diazepin-6-yl)-1,3-dihydrofuro[3,4-c]pyridine-6-carboxamide A mixture of (1R)-1-ethyl-1-methyl-3H-furo[3,4-c]pyridine-6-carboxylic acid (23 mg, 0.11 mmol), (6S)-6-amino-2,3,4-trimethyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (25 mg, 0.14 mmol) in N,N-dimethylformamide (5 mL) was stirred at 25° C. for 12 h. The reaction was concentrated under reduced pressure and the residue was purified by RP-HPLC (acetonitrile 17-47/0.05% ammonium bicarbonate in water) to give (R)-1-ethyl-1-methyl-N—((S)-2,3,4-trimethyl-5-oxo-5,6,7,8-tetrahydro-4H-pyrazolo[1,5-a][1,3]diazepin-6-yl)-1,3-dihydrofuro[3,4-c]pyridine-6-c arboxamide (16.6 mg, 45.5% yield) as white solid. $^1$H NMR (400 MHz, $CD_3OD$) δ 8.55 (s, 1H), 7.86 (s, 1H), 5.20-5.12 (m, 2H), 4.48-4.44 (m, 1H), 4.26-4.21 (m, 2H), 3.34 (s, 3H), 2.87-2.81 (m, 1H), 2.19-2.16 (m, 4H), 2.02 (s, 3H), 1.87-1.82 (m, 2H), 1.46 (s, 3H), 0.76 (t, J=7.6 Hz, 3H). LCMS $R_T$=1.022 min; m/z=398.2 $(M+H)^+$.

LCMS (10 to 80% acetonitrile in water+0.03% trifluoacetic acid over 2.0 mins) retention time 1.022 min, ESI+ found [M+H]=398.2.

Example 277

WX Method R

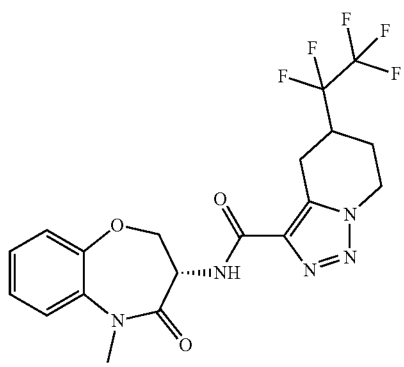 [SMILES: CN1C(=O)[C@@H](NC(=O)c2nnn3c2CC(C(F)(F)C(F)(F)F)CC3)COc2ccccc21]

N—((S)-5-methyl-4-oxo-2,3,4,5-tetrahydrobenzo[b][1,4]oxazepin-3-yl)-5-(perfluoroethyl)-4,5,6,7-tetrahydro-[1,2,3]triazolo[1,5-a]pyridine-3-carboxamide

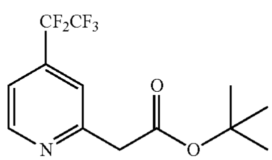

Step 1: tert-butyl 2-(4-(perfluoroethyl)pyridin-2-yl)acetate

To a stirred mixture of 2-chloro-4-(1,1,2,2,2-pentafluoroethyl)pyridine (100 mg, 0.43 mmol), tert-butyl acetate (37 mg, 0.32 mmol) and chloro(2-di-t-butylphosphino-2',4',6'-tri-1-propyl-1,1'-biphenyl)[2-(2-aminoethyl)phenyl]palladium(II) (30 mg, 0.04 mmol) in toluene (4 mL) was added lithium bis(trimethylsilyl)amide (1.0 M, 0.86 mL, 0.86 mmol) dropwise at 0° C. under nitrogen. After addition, the reaction was stirred at 0° C. for 30 min, then allowed to warm to 25° C. for 12 h. The reaction was quenched by addition of saturated aqueous ammonium chloride and extracted with ethyl acetate (2×20 mL). The combined organic layers were washed with brine (2×10 mL), dried over sodium sulfate and concentrated under reduced pressure. The residue was purified by preparative TLC (10% ethyl acetate in petroleum ether) affording tert-butyl 2-(4-(perfluoroethyl)pyridin-2-yl)acetate (10 mg, 7.4%) as yellow oil, used as is in the next step.

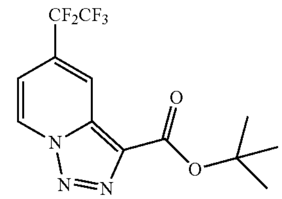

Step 2: tert-butyl 5-(1,1,2,2,2-pentafluoroethyl)triazolo[1,5-a]pyridine-3-carboxylate A mixture of tert-butyl 2-(4-(perfluoroethyl)pyridin-2-yl) acetate (80 mg, 0.26 mmol), 4-acetamidobenzene sulfonylazide (68 mg, 0.28 mmol) and 1,8-diazabicyclo[5.4.0]undec-7-ene (74 mg, 0.49 mmol) in acetonitrile (5 mL) was stirred at 25° C. for 12 h. The reaction mixture was concentrated under reduced pressure, and the residue was purified by preparative TLC (20% ethyl acetate in petroleum ether, $R_f$=0.5) to afford tert-butyl 5-(1,1,2,2,2-pentafluoroethyl)triazolo[1,5-a]pyridine-3-carboxylate (30 mg, 35%) as a white solid: LCMS $R_T$=0.916 min; m/z=281.8 $(M+H-56)^+$.

LCMS (5 to 95% acetonitrile in water+0.03% trifluoacetic acid over 1.5 min) retention time 0.916 min, ESI+ found [M+H-56]+=281.8

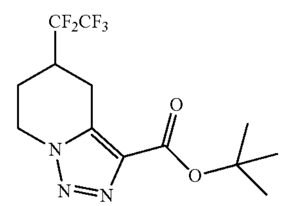

Step 3: tert-butyl 5-(1,1,2,2,2-pentafluoroethyl)-4,5,6,7-tetrahydrotriazolo[1,5-a]pyridine-3-carboxylate A mixture of tert-butyl 5-(1,1,2,2,2-pentafluoroethyl)triazolo[1,5-a]pyridine-3-carboxylate (30 mg, 0.09 mmol) and 10% palladium on carbon (10 mg, 0.09 mmol) in methanol (10 mL) was hydrogenated (35 psi) at 25° C. for 12 h. The mixture was filtered and the filtrate was concentrated under reduced pressure to afford tert-butyl 5-(1,1,2,2,2-pentafluoroethyl)-,5,6,7-tetrahydrotriazolo[1,5-a]pyridine-3-carboxylate (30 mg, 98%) as a gray solid: LCMS $R_T$=0.873 min; m/z=285.9 $(M+H-56)^+$.

LCMS (5 to 95% acetonitrile in water+0.03% trifluoacetic acid over 1.5 min) retention time 0.873 min, ESI+ found [M+H-56]+=285.9

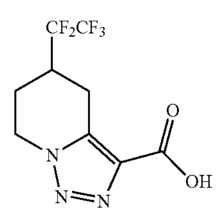

Step 4: 5-(1,1,2,2,2-pentafluoroethyl)-4,5,6,7-tetrahydrotriazolo[1,5-a]pyridine-3-carboxylic acid To a solution of tert-butyl 5-(1,1,2,2,2-pentafluoroethyl)-4,5,6,7-tetrahydrotriazolo [1,5-a]pyridine-3-carboxylate (30 mg, 0.09 mmol) in dichloromethane (6 mL) was added trifluoroacetic acid (1 mL, 13.4 mmol) at 25° C. The reaction mixture was stirred for 12 h and then concentrated under reduced pressure affording crude 5-(1,1,2,2,2-pentafluoroethyl)-4,5,6,7-tetrahydrotriazolo[1,5-a]pyridine-3-carboxylic acid (30 mg, 119%) as colorless oil: LCMS $R_T$=0.718 min; m/z=286.1 $(M+H)^+$.

LCMS (5 to 95% acetonitrile in water+0.03% trifluoacetic acid over 1.5 min) retention time 0.718 min, ESI+ found [M+H]=286.1

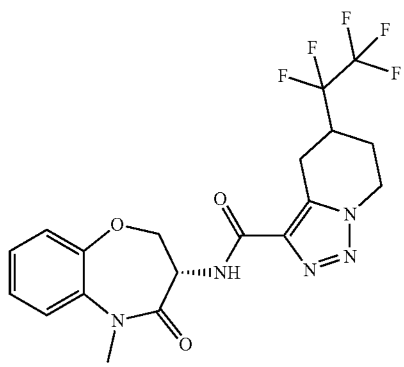 [SMILES: CN1C(=O)[C@@H](NC(=O)c2nnn3c2CC(C(F)(F)C(F)(F)F)CC3)COc2ccccc21]

Step 5: N—((S)-5-methyl-4-oxo-2,3,4,5-tetrahydrobenzo[b][1,4]oxazepin-3-yl)-5-(perfluoroethyl)-4,5,6,7-tetrahydro-[1,2,3]triazolo[1,5-a]pyridine-3-carboxamide A mixture of 5-(1,1,2,2,2-pentafluoroethyl)-4,5,6,7-tetrahydrotriazolo[1,5-a]pyridine-3-carboxylic acid (30 mg, 0.11 mmol), 1H-benzo[d][1,2,3]triazol-1-ol (32 mg, 0.23 mmol), (3S)-3-amino-5-methyl-2,3-dihydro-1,5-benzoxazepin-4-one (23 mg, 0.12 mol) and $N^1$-((ethylimino)methylene)-$N^3$,$N^3$-dimethylpropane-1,3-diamine hydrochloride (47 mg, 0.25 mmol) in N,N-dimethylformamide (3 mL) was stirred at 25° C. for 12 h. The solvent was evaporated under reduced pressure and the residue was purified by RP-HPLC (acetonitrile 17-47/0.05% FA in water) to afford N—((S)-5-methyl-4-oxo-2,3,4,5-tetrahydrobenzo[b][1,4]oxazepin-3-yl)-5-(perfluoroethyl)-4,5, 6,7-tetrahydro-[1,2,3]triazolo[1,5-a]pyridine-3-carboxamide (8.5 mg, 18%) as a white solid: $^1$H NMR (400 MHz, $CD_3OD$) δ 7.46-7.40 (m, 1H), 7.36-7.26 (m, 2H), 7.26-7.20 (m, 1H), 5.00-4.97 (m, 1H), 4.72-4.68 (m, 1H), 4.62-4.57 (m, 1H), 4.43-4.39 (m, 1H), 4.38-4.29 (m, 1H), 3.54-3.45 (m, 1H), 3.42 (s, 3H), 3.05-2.93 (m, 2H), 2.48-2.44 (m, 1H), 2.19-2.07 (m, 1H). LCMS $R_T$=0.864 min; m/z=460.1 $(M+H)^+$.

LCMS (5 to 95% acetonitrile in water+0.03% trifluoacetic acid over 1.5 min) retention time 0.864 min, ESI+ found [M+H]=460.1.

Example 278

WX Method YYY

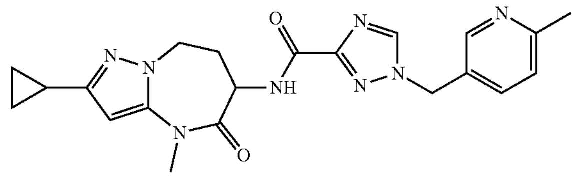 [SMILES: Cc1ccc(Cn2cnc(C(=O)NC3CCn4nc(C5CC5)cc4N(C)C3=O)n2)cn1]

N-(2-cyclopropyl-4-methyl-5-oxo-5,6,7,8-tetrahydro-4H-pyrazolo[1,5-a][1,3]diazepin-6-yl)-1-((6-methylpyridin-3-yl)methyl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (5 mL) was added 5-(bromomethyl)-2-methylpyridine (636 mg, 1.72 mmol) and potassium carbonate (358 mg, 2.59 mmol). The mixture was stirred at 25° C. for 12 h and then filtered. The filtrate was evaporated under reduced pressure and the residue was purified by RP-HPLC (methanol 40-70%/0.05% ammonia hydroxide in water) to afford N-(2-cyclopropyl-4-methyl-5-oxo-5,6,7,8-tetrahydro-4H-pyrazolo[1,5-a][1,3]diazepin-6-yl)-1-((6-methylpyridin-3-yl)methyl)-1H-1,2,4-triazole-3-carboxamide (33 mg, 10%) as white solid: $^1$H NMR (400 MHz, $CD_3OD$) δ 8.63 (s, 1H), 8.47 (d, J=1.6 Hz, 1H), 7.75-7.73 (m, 1H), 7.32 (d, J=8.8 Hz, 1H), 6.00 (s, 1H), 5.51 (s, 2H), 4.54-4.49 (m, 1H), 4.29-4.15 (m, 2H), 3.31 (s, 3H), 2.86-2.80 (m, 1H), 2.53 (s, 3H), 2.28-2.23 (m, 1H), 1.92-1.87 (m, 1H), 0.95-0.92 (m, 2H), 0.75-0.72 (m, 2H). LCMS $R_T$=0.53 min; m/z=421.1 $(M+H)^+$.

LCMS (5 to 95% acetonitrile in water+0.03% formic acid over 1.5 mins) retention time 0.53 min, ESI+ found [M+H]=421.1.

Example 279

WX Method X

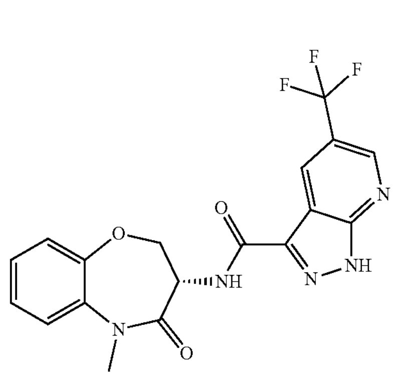 [SMILES: CN1C(=O)[C@@H](NC(=O)c2n[nH]c3ncc(C(F)(F)F)cc23)COc2ccccc21]

(S)—N-(5-methyl-4-oxo-2,3,4,5-tetrahydrobenzo[b][1,4]oxazepin-3-yl)-5-(trifluoromethyl)-1H-pyrazolo[3,4-b]pyridine-3-carboxamide

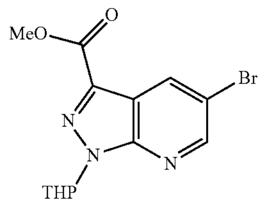

Step 1: methyl 5-bromo-1-(tetrahydro-2H-pyran-2-yl)-1H-pyrazolo[3,4-b]pyridine-3-carboxylate To a solution of methyl 5-bromo-1H-pyrazolo[3,4-b]pyridine-3-carboxylate (500 mg, 1.95 mmol) in dichloromethane (20 mL) was added pyridin-1-ium 4-methylbenzenesulfonate (49 mg, 0.20 mmol) and 3,4-dihydro-2h-pyran (329 mg, 3.91 mmol). After addition, the mixture was stirred at 60° C. for 6 h. The solvent was removed under reduced pressure and the residue was dissolved in ethyl acetate (25 mL). The separated organic layer was washed with saturated aqueous sodium bicarbonate (10 mL), dried over sodium sulfate and concentrated to afford crude methyl 5-bromo-1-(tetrahydro-2H-pyran-2-yl)-1H-pyrazolo[3,4-b]pyridine-3-carboxylate (600 mg, 90%) as a yellow solid: LCMS $R_T$=0.811 min; m/z=340.0 $(M+H)^+$.

LCMS (5 to 95% acetonitrile in water+0.03% formic acid over 1.5 mins) retention time 0.811 min, ESI+ found [M+H]= 340.0.

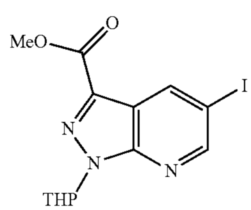

Step 2: methyl 5-iodo-1-(tetrahydro-2H-pyran-2-yl)-1H-pyrazolo[3,4-b]pyridine-3-carboxylate A mixture of methyl 5-bromo-1-(tetrahydro-2H-pyran-2-yl)-1H-pyrazolo[3,4-b]pyridine-3-carboxylate (300 mg, 0.88 mmol), cuprous iodide (8 mg, 0.04 mmol), (1R,2R)—$N^1$,$N^2$-dimethylcyclohexane-1,2-diamine (13 mg, 0.09 mmol) and sodium iodide (264 mg, 1.76 mmol) in 1,4-dioxane (3 mL) was heated at 110° C. for 20 h in a sealed tube. The solution was filtered and the filtrate was concentrated under reduced pressure. The residue was purified by column chromatography (silica gel, 100-200 mesh, 0 to 30% ethyl acetate in petroleum ether) to afford methyl 5-iodo-1-(tetrahydro-2H-pyran-2-yl)-1H-pyrazolo[3,4-b]pyridine-3-carboxylate (330 mg, 97%) as a white solid: LCMS $R_T$=0.824 min; m/z=388.0 $(M+H)^+$.

LCMS (10 to 80% acetonitrile in water+0.03% formic acid over 2.0 mins) retention time 0.824 min, ESI+ found [M+H]=388.0.

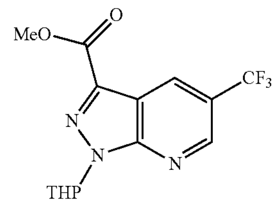

Step 3: methyl 5-trifluoromethyl-1-(tetrahydro-2H-pyran-2-yl)-1H-pyrazolo[3,4-b]pyridine-3-carboxylate A mixture of methyl 5-iodo-1-(tetrahydro-2H-pyran-2-yl)-1H-pyrazolo[3,4-b]pyridine-3-carboxylate (220 mg, 0.57 mmol), cuprous iodide (108 mg, 0.57 mmol) and methyl 2,2-difluoro-2-(fluorosulfonyl)acetate (218 mg, 1.14 mmol) in N,N-dimethylacetamide (2.5 mL) was heated at 100° C. for 2 h. The solvent was removed under reduced pressure and the residue was purified by column chromatography (silica gel, 100-200 mesh, 0 to 30% ethyl acetate in petroleum ether) to afford methyl 5-trifluoromethyl-1-(tetrahydro-2H-pyran-2-yl)-1H-pyrazolo[3,4-b]pyridine-3-carboxylate (100 mg, 53%) as a white solid: LCMS $R_T$=0.884 min, m/z=330.0$[M+H]^+$.

LCMS (5 to 95% acetonitrile in water+0.03% formic acid over 1.5 mins) retention time 0.884 min, ESI+ found [M+H]= 330.0.

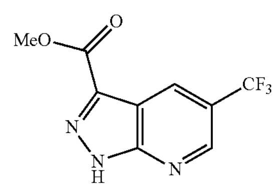 [SMILES: COC(=O)c1n[nH]c2ncc(C(F)(F)F)cc12]

Step 4: methyl 5-(trifluoromethyl)-1H-pyrazolo[3,4-b]pyridine-3-carboxylate

A mixture of methyl 5-trifluoromethyl-1-(tetrahydro-2H-pyran-2-yl)-1H-pyrazolo[3,4-b]pyridine-3-carboxylate (80 mg, 0.24 mmol) and trifluoroacetic acid (277 mg, 2.43 mmol) in dichloromethane (5 mL) was stirred at 25° C. for 2 h. The solvent was removed under reduced pressure to afford crude methyl 5-(trifluoromethyl)-1H-pyrazolo[3,4-b]pyridine-3-carboxylate (50 mg, 84%) as a yellow solid: LCMS $R_T$=0.699 min; m/z=246.0 $(M+H)^+$.

LCMS (5 to 95% acetonitrile in water+0.03% formic acid over 1.5 mins) retention time 0.699 min, ESI+ found [M+H]= 246.0.

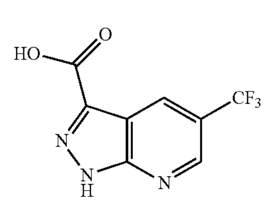 [SMILES: O=C(O)c1n[nH]c2ncc(C(F)(F)F)cc12]

Step 5: 5-(trifluoromethyl)-1H-pyrazolo[3,4-b]pyridine-3-carboxylic acid

A mixture of methyl 5-(trifluoromethyl)-1H-pyrazolo[3,4-b]pyridine-3-carboxylate (50 mg, 0.20 mmol) and lithium hydroxide hydrate (86 mg, 2.04 mmol) in tetrahydrofuran (5 mL) and water (1 mL) was stirred at 20° C. for 20 h. The solvent was removed under reduced pressure. The residue was diluted with water (10 mL) and adjusted pH=4 by addition of hydrochloric acid (1.0 M). The solution was extracted with ethyl acetate (3×15 mL). The combined organic layers were dried over sodium sulfate and concentrated under reduced pressure to afford crude 5-(trifluoromethyl)-1H-pyrazolo[3,4-b]pyridine-3-carboxylic acid (40 mg, 85%) as a white solid: LCMS $R_T$=0.612 min; m/z=232.1 $(M+H)^+$.

LCMS (5 to 95% acetonitrile in water+0.03% formic acid over 1.5 mins) retention time 0.612 min, ESI+ found [M+H]= 232.1.

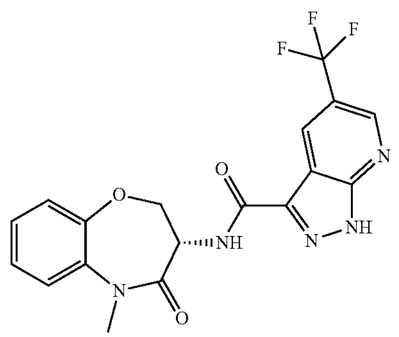 [SMILES: CN1C(=O)[C@@H](NC(=O)c2n[nH]c3ncc(C(F)(F)F)cc23)COc2ccccc21]

Step 6: (S)—N-(5-methyl-4-oxo-2,3,4,5-tetrahydrobenzo[b][1,4]oxazepin-3-yl)-5-(trifluoromethyl)-1H-pyrazolo[3,4-b]pyridine-3-carboxamide A mixture of 5-(trifluoromethyl)-1H-pyrazolo[3,4-b]pyridine-3-carboxylic acid (40 mg, 0.19 mmol), (3S)-3-amino-5-methyl-2,3-dihydro-1,5-benzoxazepin-4-one (37 mg, 0.19 mmol), $N^1$-((ethylimino)methylene)-$N^3$,$N^3$-dimethylpropane-1,3-diamine hydrochloride (40 mg, 0.21 mmol) and 1H-benzo[d][1,2,3]triazol-1-ol (28 mg, 0.21 mmol) in N,N-dimethylformamide (5 mL) was stirred at 15° C. for 1 h. The solvent was evaporated under reduced pressure and the residue was purified by RP-HPLC (40-70% acetonitrile in water and 0.05% hydrochloric acid) to afford (S)—N-(5-methyl-4-oxo-2,3,4,5-tetrahydrobenzo[b][1,4]oxazepin-3-yl)-5-(trifluoromethyl)-1H-pyrazolo[3,4-b]pyridine-3-carboxamide (19 mg, 25%) as a white solid: $^1$H NMR (400 MHz, DMSO-$d_6$) δ 8.96 (d, J=2.0 Hz, 1H), 8.80 (d, J=8.4 Hz, 1H), 8.69 (d, J=1.2 Hz, 1H), 7.53-7.51 (m, 1H), 7.35-7.26 (m, 3H), 4.98-4.93 (m, 1H), 4.71-4.66 (m, 1H), 4.48-4.44 (m, 1H), 3.33 (s, 3H). LCMS $R_T$=0.848 min; m/z=406.0 $(M+H)^+$.

LCMS (5 to 95% acetonitrile in water+0.03% formic acid over 1.5 mins) retention time 0.848 min, ESI+ found [M+H]= 406.0.

Example 280

WX Method HHHHH

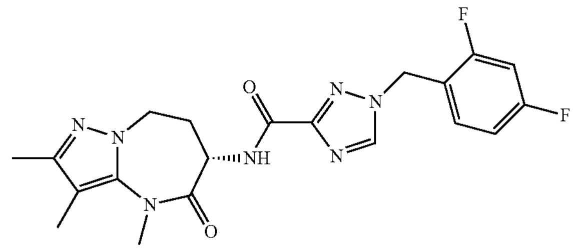 [SMILES: Cc1nn2c(c1C)N(C)C(=O)[C@@H](NC(=O)c1ncn(Cc3ccc(F)cc3F)n1)CC2]

(S)-1-(2,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide A mixture of 1-[(2,4-difluorophenyl)methyl]-1,2,4-triazole-3-carboxylic acid (28 mg, 0.12 mmol), (6S)-6-amino-2,3,4-trimethyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol) and $N^1$-((ethylimino)methylene)-$N^3$, N3-dimethylpropane-1,3-diamine hydrochloride (25 mg, 0.14 mmol) in N,N-dimethylformamide (5 mL) was stirred at 25° C. for 12 h. The reaction was concentrated under reduced pressure and the residue was purified by RP-HPLC (MeOH 50-80%/0.05% ammonia hydroxide in water) to afford (S)-1-(2,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide (30 mg, 73%) as a white solid: $^1$H NMR (400 MHz, $CD_3OD$) δ 8.59 (s, 1H), 7.49-7.43 (m, 1H), 7.05-6.98 (m, 2H), 5.52 (s, 2H), 4.44-4.40 (m, 1H), 4.24-4.19 (m, 2H), 3.31 (s, 3H), 2.81-2.73 (m, 1H), 2.22-2.19 (s, 4H), 2.01 (s, 3H). LCMS $R_T$=0.76 min; m/z=430.1 $(M+H)^+$.

LCMS (5 to 95% acetonitrile in water+0.03% formic acid over 1.5 mins) retention time 0.76 min, ESI+ found [M+H]= 430.1.

Example 281

WX Method IIIII

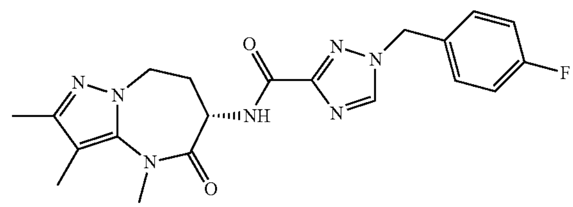 [SMILES: Cc1nn2c(c1C)N(C)C(=O)[C@@H](NC(=O)c1ncn(Cc3ccc(F)cc3)n1)CC2]

(S)-1-(4-fluorobenzyl)-N-(2,3,4-trimethyl-5-oxo-5,6,7,8-tetrahydro-4H-pyrazolo[1,5-a][1, 3]diazepin-6-yl)-1H-1,2,4-triazole-3-carboxamide A mixture of 1-[(4-fluorophenyl)methyl]-1,2,4-triazole-3-carboxylic acid (24 mg, 0.11 mmol), (6S)-6-amino-2,3,4-trimethyl-7,8-dihydro-6H-pyrazolo[1,5-a][1,3]diazepin-5- one (20 mg, 0.09 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (25 mg, 0.14 mmol) in N,N-dimethylformamide (5 mL) was stirred at 25° C. for 12 h. The reaction was concentrated under reduced pressure and the residue was purified by RP-HPLC (MeOH 20-50%/0.05% ammonia hydroxide in water) to afford (S)-1-(4-fluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide (10.2 mg, 27%) as a white solid: $^1$H NMR (400 MHz, DMSO-$d_6$) δ 8.81 (s, 1H), 8.42 (d, J=7.6 Hz, 1H), 7.40-7.36 (m, 2H), 7.23-7.19 (m, 2H), 5.47 (s, 2H), 4.25-4.09 (m, 3H), 3.19 (s, 3H), 2.50-2.49 (m, 1H), 2.25-2.10 (m, 1H), 2.09 (s, 3H), 1.93 (s, 3H). LCMS $R_T$=0.76 min; m/z=412.1 $(M+H)^+$.

LCMS (5 to 95% acetonitrile in water+0.03% formic acid over 1.5 mins) retention time 0.76 min, ESI+ found [M+H]=412.1.

Example 282

WX Method HHHH

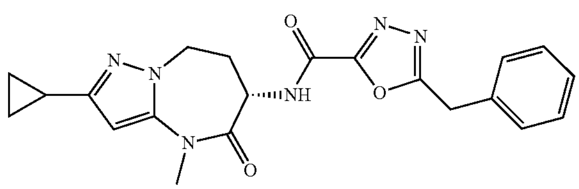 [SMILES: CN1C(=O)[C@@H](NC(=O)c2nnc(Cc3ccccc3)o2)CCn2nc(C3CC3)cc21]

(S)-5-benzyl-N-(2-cyclopropyl-4-methyl-5-oxo-5,6,7,8-tetrahydro-4H-pyrazolo[1,5-a][1,3]diazepin-6-yl)-1,3,4-oxadiazole-2-carboxamide A mixture of 5-benzyl-1,3,4-oxadiazole-2-carboxylic acid (28 mg, 0.14 mmol), (6S)-6-amino-2-cyclopropyl-4-methyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (24 mg, 0.14 mmol) in N,N-dimethylformamide (3 mL) was stirred at 25° C. for 2 h. The reaction was concentrated under reduced pressure and the residue was purified by RP-HPLC (methanol 45-75%/0.05% ammonium hydroxide in water) to afford (S)-5-benzyl-N-(2-cyclopropyl-4-methyl-5-oxo-5,6,7,8-tetrahydro-4H-pyrazolo[1,5-a][1,3]diazepin-6-yl)-1,3,4-oxadiazole-2-carboxamide (13.9 mg, 37%) as white solid: $^1$H NMR (400 MHz, $CD_3OD$) δ 7.35-7.28 (m, 5H), 6.02 (s, 1H), 4.50-4.45 (m, 1H), 4.33-4.21 (m, 4H), 3.32 (s, 3H), 2.81-2.75 (m, 1H), 2.35-2.31 (m, 1H), 1.92-1.88 (m, 1H), 0.95-0.92 (m, 2H), 0.75-0.72 (m, 2H). LCMS $R_T$=1.238 min; m/z=407.1 $(M+H)^+$.

LCMS (0 to 60% acetonitrile in water+0.03% trifluoacetic acid over 2 mins) retention time 1.238 min, ESI+ found $[M+H]^+$=407.1.

Example 283

WX Method KKKKK

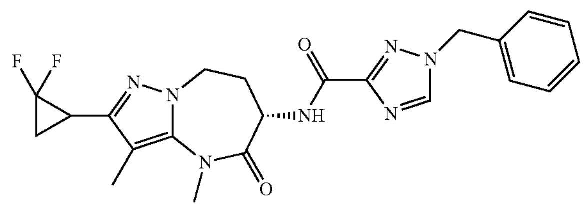 [SMILES: Cc1c(C2CC2(F)F)nn2c1N(C)C(=O)[C@@H](NC(=O)c1ncn(Cc3ccccc3)n1)CC2]

1-benzyl-N-((6S)-2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide

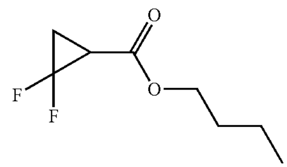

Step 1: butyl 2,2-difluorocyclopropanecarboxylate

A solution of 2,2-difluorocyclopropanecarboxylic acid (30.0 g, 245.8 mmol) in acetonitrile (300 mL) was added 1,8-diazabicyclo[5.4.0]undec-7-ene (37.4 g, 245.8 mmol) and 1-iodobutane (49.8 g, 270.3 mmol) at 0° C. The resulting mixture was stirred at 25° C. for 12 h and then quenched by addition of water (300 mL). The solution was extracted with ethyl acetate (3×200 mL). The combined organic layers were dried over sodium sulfate, concentrated under reduced pressure to give crude butyl 2, 2-difluorocyclopropanecarboxylate (30.0 g, 69%) as a yellow oil, used in the next step without further purification.

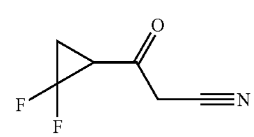

Step 2: 3-(2,2-difluorocyclopropyl)-3-oxopropanenitrile

To a solution of acetonitrile (10 mL, 185.2 mmol) in tetrahydrofuran (500 mL) was added n-butyllithium (2.5 M, 74.0 mL, 185.2 mmol) dropwise at −78° C. The resulting mixture was stirred at −78° C. for 30 minutes, then butyl 2, 2-difluorocyclopropanecarboxylate (30.0 g, 168.4 mmol) was added. The mixture was then allowed to warm to 25° C. and stirred for another 2 h. The reaction mixture was concentrated under reduced pressure to give crude 3-(2,2-difluorocyclopropyl)-3-oxopropanenitrile (20.0 g, 82%) as a yellow oil, used in the next step without further purification.

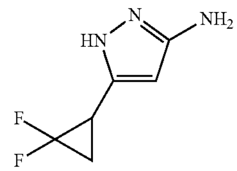 [SMILES: Nc1cc(C2CC2(F)F)[nH]n1]

Step 3: 5-(2,2-difluorocyclopropyl)-1H-pyrazol-3-amine

A mixture of 3-(2,2-difluorocyclopropyl)-3-oxo-propanenitrile (20.0 g, 137.8 mmol) and hydrazine hydrate (50 mL, 85%) in 2-methyl-1-propanol (100 mL) was heated to 80° C. for 12 h. The reaction mixture was concentrated under reduced pressure. The residue was purified by column chromatography (silica gel, 100-200 mesh, 0 to 20% methanol in dichloromethane) to give 5-(2,2-difluorocyclopropyl)-1H-pyrazol-3-amine (16.0 g, 73%) as a yellow oil. LCMS $R_T$=0.93 min; m/z=160.1 $(M+H)^+$.

LCMS (0 to 30% acetonitrile in water+0.05% ammonium hydroxide over 3 minutes) retention time 0.93 min, ESI+ found [M+H]=160.1.

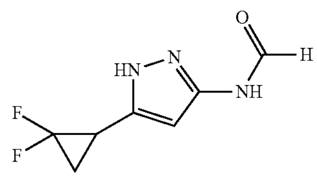 [SMILES: O=CNc1cc(C2CC2(F)F)[nH]n1]

Step 4: N-(5-(2,2-difluorocyclopropyl)-1H-pyrazol-3-yl)formamide

A solution of 5-(2,2-difluorocyclopropyl)-1H-pyrazol-3-amine (16.0 g, 100.5 mmol) in formic acid (80 mL) was heated at 110° C. for 15 h. The solvent was removed under reduced pressure and the residue was purified by column chromatography (silica gel, 100-200 mesh, 0 to 10% methanol in dichloromethane) to give N-[5-(2,2-difluorocyclopropyl)-1H-pyrazol-3-yl]formamide (14.0 g, 74%) as a yellow solid: LCMS $R_T$=1.35 min; m/z=188.1 $(M+H)^+$.

LCMS (0 to 30% acetonitrile in water+0.05% ammonium hydroxide over 3.0 mins) retention time 1.35 min, ESI+ found [M+H]=188.1.

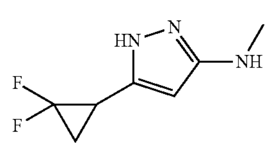

Step 5: 5-(2,2-difluorocyclopropyl)-N-methyl-1H-pyrazol-3-amine

To a solution of N-[5-(2,2-difluorocyclopropyl)-1H-pyrazol-3-yl]formamide (10.0 g, 53.4 mmol) in tetrahydrofuran (200 mL) was added lithium aluminum hydride (4.1 g, 106.9 mmol) in small portions at 0° C. The reaction mixture was stirred at 25° C. for another 12 h, and then slowly quenched by addition of water (5 mL), 10% aqueous sodium hydroxide (5 mL). The resulting mixture was filtered. The filtrate was dried over sodium sulfate and concentrated under reduced pressure to afford 5-(2,2-difluorocyclopropyl)-N-methyl-1H-pyrazol-3-amine (7.0 g, 76%) as a colorless oil, used in the next step without further purification.

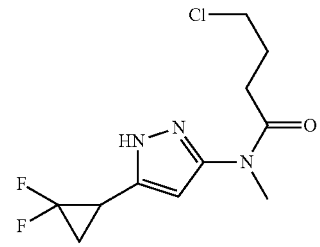 [SMILES: CN(C(=O)CCCCl)c1cc(C2CC2(F)F)[nH]n1]

Step 6: 4-chloro-N-(5-(2,2-difluorocyclopropyl)-1H-pyrazol-3-yl)-N-methylbutanamide A solution of 5-(2,2-difluorocyclopropyl)-N-methyl-1H-pyrazol-3-amine (9.0 g, 51.9 mmol) in 4-chlorobutanoyl chloride (20 mL) was stirred for 4 h at 60° C. After cooled, the reaction mixture was slowly quenched by addition of methanol (10 mL). The solvent under reduced pressure and the residue was purified by column chromatography (silica gel, 100-200 mesh, 0 to 10% methanol in dichloromethane) to afford 4-chloro-N-[5-(2,2-difluorocyclopropyl)-1H-pyrazol-3-yl]-N-methyl-butanamide (11.0 g, 76%) as a yellow oil: LCMS $R_T$=0.76 min; m/z=277.9 $(M+H)^+$.

LCMS (5 to 95% acetonitrile in water+0.03% trifluoroacetic acid over 1.5 mins) retention time 0.76 min, ESI+ found [M+H]=277.9.

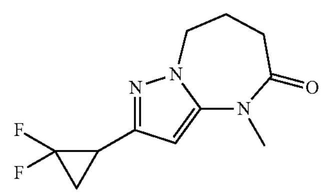 [SMILES: CN1C(=O)CCCn2nc(C3CC3(F)F)cc21]

Step 7: 2-(2,2-difluorocyclopropyl)-4-methyl-7,8-dihydro-4H-pyrazolo[1,5-a][1,3]diazepin-5(6H)-one A mixture of 4-chloro-N-[5-(2,2-difluorocyclopropyl)-1H-pyrazol-3-yl]-N-methyl-butanamide (11.0 g, 39.6 mmol) and cesium carbonate (25.8 g, 79.2 mmol) in N,N-dimethylformamide (200 mL) was stirred at 25° C. for 12 h. The mixture was filtered and the filtrate was concentrated under reduced pressure. The residue was purified by column chromatography (silica gel, 100-200 mesh, 0 to 10% methanol in dichloromethane to afford 2-(2,2-difluorocyclopropyl)-4-methyl-7,8-dihydro-6H-pyrazolo[1,5-a][1,3]diazepin-5-one (9.0 g, 94%) as a yellow oil: LCMS $R_T$=2.36 min; m/z=242.1 $(M+H)^+$.

LCMS (0 to 30% acetonitrile in water+0.05% ammonium hydroxide over 3 mins) retention time 2.36 min, ESI+ found [M+H]=242.1.

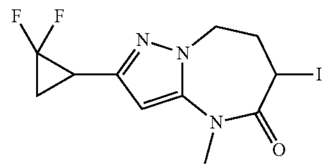 [SMILES: CN1C(=O)C(I)CCn2nc(C3CC3(F)F)cc21]

Step 8: 2-(2,2-difluorocyclopropyl)-6-iodo-4-methyl-7,8-dihydro-4H-pyrazolo[1,5-a][1,3]diazepin-5(6H)-one To a solution of 2-(2,2-difluorocyclopropyl)-4-methyl-7,8-dihydro-4H-pyrazolo[1,5-a][1,3]diazepin-5(6H)-one (3.6 g, 17.5 mmol) in dichloromethane (200 mL) was added tetramethylethylenediamine (20.4 g, 175.4 mmol) and iodotrimethylsilane (35.1 g, 175.4 mmol) at −15° C. The resulting mixture was stirred at −15° C. for 1.5 h and then iodine (22.3 g, 87.7 mmol) was added in one portion. The reaction mixture was stirred at −15° C. for 3 h and then quenched by addition of saturated sodium bisulfite solution (70 mL). The solution was extracted with dichloromethane (3×100 mL). The combined organic extracts were dried over sodium sulfate and concentrated under reduced pressure. The residue was purified by column chromatography (silica gel, 100-200 mesh, 0 to 10% methanol in dichloromethane) to give 2-(2,2-difluorocyclopropyl)-6-iodo-4-methyl-7,8-dihydro-4H-pyrazolo[1,5-a][1,3]diazepin-5(6H)-one (3.6 g, 62%) as a colorless oil, used as is in the next step.

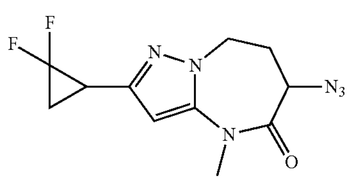 [SMILES: CN1C(=O)C(N=[N+]=[N-])CCn2nc(C3CC3(F)F)cc21]

Step 9: 6-azido-2-(2,2-difluorocyclopropyl)-4-methyl-7,8-dihydro-4H-pyrazolo[1,5-a][1,3]diazepin-5(6H)-one To a solution of 2-(2,2-difluorocyclopropyl)-6-iodo-4-methyl-7,8-dihydro-4H-pyrazolo[1,5-a][1,3]diazepin-5 (6H)-one (7.2 g, 19.6 mmol) in N,N-dimethylformamide (40 mL) was added sodium azide (1.9 g, 29.4 mmol). The reaction mixture was stirred at 25° C. for 2 h and then poured into ice water (5 mL). The solution was extracted with ethyl acetate (3×100 mL). The combined organic layers were washed with water (10 mL), brine (10 mL), dried over sodium sulfate and concentrated under reduced pressure to afford crude 6-azido-2-(2,2-difluorocyclopropyl)-4-methyl-7,8-dihydro-4H-pyrazolo[1,5-a][1,3]diazepin-5 (6H)-one (5.0 g, 90%) as a light yellow oil: LCMS $R_T$=2.86 min; m/z=283.1 $(M+H)^+$.

LCMS (0 to 30% acetonitrile in water+0.03% ammonium hydroxide over 3.0 mins) retention time 2.86 min, ESI+ found [M+H]=283.1

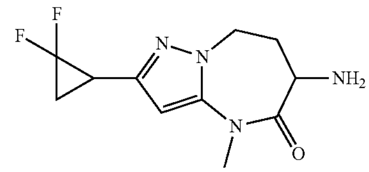 [SMILES: CN1C(=O)C(N)CCn2nc(C3CC3(F)F)cc21]

Step 10: 6-amino-2-(2,2-difluorocyclopropyl)-4-methyl-7,8-dihydro-4H-pyrazolo[1,5-a][1,3]diazepin-5(6H)-one To a solution of 6-azido-2-(2,2-difluorocyclopropyl)-4-methyl-7,8-dihydro-4H-pyrazolo[1,5-a][1,3]diazepin-5 (6H)-one (5.0 g, 17.7 mmol) in tetrahydrofuran (100 mL) and water (20 mL) was added polymer-bound triphenylphosphine (25 g, ~3 mmol/g loading). The mixture was shaken at 25° C. for 16 h and then filtered through a short pad of celite. The filtrate was concentrated under reduced pressure and the residue was purified by column chromatography (silica gel, 100-200 mesh, 0 to 10% methanol in dichloromethane) to afford 6-amino-2-(2,2-difluorocyclopropyl)-4-methyl-7,8-dihydro-4H-pyrazolo[1,5-a][1,3]diazepin-5(6H)-one as a colorless oil (4.5 g, 99%): LCMS $R_T$=1.52 min; m/z=257.1 $(M+H)^+$.

LCMS (0 to 60% acetonitrile in water+0.03% ammonium hydroxide over 3.0 mins) retention time 1.52 min, ESI+ found [M+H]=257.1

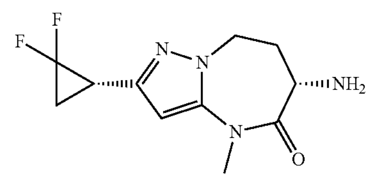

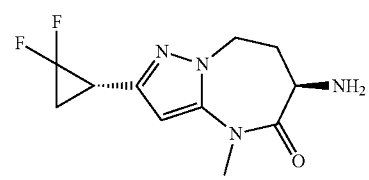

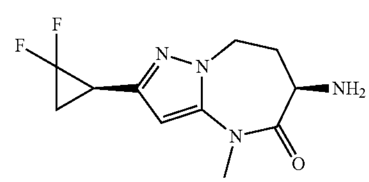

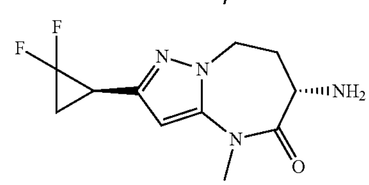

Step 11: (S)-6-amino-2-((S)-2,2-difluorocyclopropyl)-4-methyl-7,8-dihydro-4H-pyrazolo[1,5-a][1, 3]diazepin-5(6H)-one; (R)-6-amino-2-((S)-2,2-difluorocyclopropyl)-4-methyl-7,8-dihydro-4H-pyrazolo[1,5-a][1, 3]diazepin-5(6H)-one; (R)-6-amino-2-((R)-2,2-difluorocyclopropyl)-4-methyl-7,8-dihydro-4H-pyrazolo[1,5-a][1,3]diazepin-5(6H)-one and (S)-6-amino-2-((R)-2,2-difluorocyclopropyl)-4-methyl-7,8-dihydro-4H-pyrazolo[1,5-a][1, 3]diazepin-5(6H)-one 6-amino-2-(2,2-difluorocyclopropyl)-4-methyl-7,8-dihydro-4H-pyrazolo[1,5-a][1,3]diazepin-5(6H)-one (1.9 g, 7.7 mmol) was separated by SFC to afford:

Peak 1 (Retention time: 2.26 min), tentatively assigned as: (S)-6-amino-2-((S)-2,2-difluorocyclopropyl)-4-methyl-7,8-dihydro-4H-pyrazolo[1,5-a][1,3]di azepin-5(6H)-one (380 mg, 20.0% yield);

Peak 2 (Retention time: 2.46 min), tentatively assigned as: (R)-6-amino-2-((S)-2,2-difluorocyclopropyl)-4-methyl-7,8-dihydro-4H-pyrazolo[1,5-a][1,3]diazepin-5(6H)-one(400 mg, 21.0% yield);

Peak 3 (Retention time: 2.64 min), tentatively assigned as: (R)-6-amino-2-((R)-2,2-difluorocyclopropyl)-4-methyl-7,8-dihydro-4H-pyrazolo[1,5-a][1,3]diazepin-5(6H)-one (390 mg, 20.5% yield);

Peak 4 (Retention time: 3.26 min), tentatively assigned as: (S)-6-amino-2-((R)-2,2-difluorocyclopropyl)-4-methyl-7,8-dihydro-4H-pyrazolo[1,5-a][1,3]diazepin-5(6H)-one(380 mg, 20.0% yield);

SFC condition: Column: Chiralpak AD 100×4.6 mm I.D., 3 μm Mobile phase: A: $CO_2$ B: Methanol (0.05% DEA) Isocratic: from 5% to 40% of B in 4.5 min and hold 40% for 2.5 min, then 5% of B for 1 min Flow rate: 2.8 mL/min Column temperature: 40° C., BPR: 120 bar.

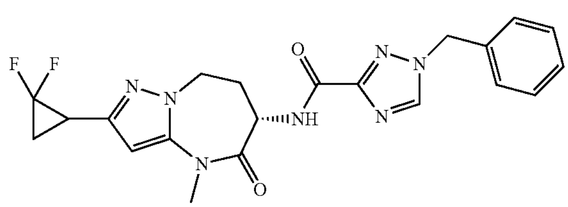 [SMILES: CN1C(=O)[C@@H](NC(=O)c2ncn(Cc3ccccc3)n2)CCn2nc(C3CC3(F)F)cc21]

1-benzyl-N-((6S)-2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (6S)-6-amino-2-(2,2-difluorocyclopropyl)-4-methyl-7,8-dihydro-4H-pyrazolo[1,5-a][1,3]diazepin-5(6H)-one (100 mg, 0.39 mmol), 1-benzyl-1H-1,2,4-triazole-3-carboxylic acid (120 mg, 0.59 mmol), 1H-benzo[d][1,2,3]triazol-1-ol (79 mg, 0.59 mmol) and $N^1$-((ethylimino)methylene)-$N^3$,$N^3$-dimethylpropane-1,3-diamine hydrochloride (110 mg, 0.59 mmol) in N,N-dimethylformamide (10 mL) was stirred at 25° C. for 16 h. The reaction was concentrated under reduced pressure and the residue was purified by RP-HPLC (acetonitrile 22-52%/0.05% ammonia hydroxide in water) to afford 1-benzyl-N-((6 S)-2-(2,2-difluorocyclopropyl)-4-methyl-5-oxo-5,6,7,8-tetrahydro-4H-pyrazol o[1,5-a][1,3]diazepin-6-yl)-1H-1,2,4-triazole-3-carboxamide as a white solid (100 mg, 57%): $^1$H NMR (400 MHz, DMSO-$d_6$) δ 8.82 (s, 1H), 8.56 (d, J=7.6 Hz, 1H), 7.41-7.28 (m, 5H), 6.29 (d, J=8.8 Hz, 1H), 5.48 (s, 2H), 4.35-4.26 (m, 2H), 4.19-4.07 (m, 1H), 3.22 (d, J=1.6 Hz, 3H), 2.94-2.87 (m, 1H), 2.41-2.32 (m, 2H), 2.00-1.93 (m, 1H), 1.89-1.81 (m, 1H). LCMS $R_T$=0.99 min; m/z=442.2 $(M+H)^+$.

LCMS (10 to 80% acetonitrile in water+0.03% trifluoacetic acid over 2.0 mins) retention time 0.99 min, ESI+ found [M+H]=442.2.

Example 284

WX Method NNNNN

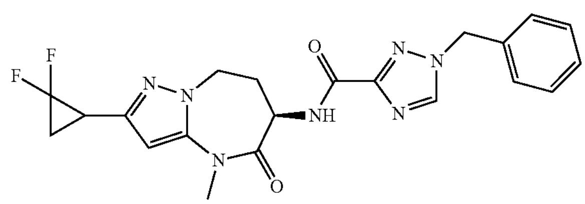 [SMILES: CN1C(=O)[C@H](NC(=O)c2ncn(Cc3ccccc3)n2)CCn2nc(C3CC3(F)F)cc21]

1-benzyl-N-((6R)-2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (6R)-6-amino-2-(2,2-difluorocyclopropyl)-4-methyl-7,8-dihydro-4H-pyrazolo[1,5-a][1,3]diazepin-5(6H)-one (106 mg, 0.41 mmol), 1-benzyl-1H-1,2,4-triazole-3-carboxylic acid (83 mg, 0.41 mmol), 1H-benzo[d][1,2,3]triazol-1-ol (79 mg, 0.59 mmol) and $N^1$-((ethylimino)methylene)-$N^3$,$N^3$-dimethylpropane-1,3-diamine hydrochloride (110 mg, 0.59 mmol) in N,N-dimethylformamide (10 mL) was stirred at 25° C. for 16 h. The reaction was concentrated under reduced pressure and the residue was purified by RP-HPLC (25-55% acetonitrile in water and 0.05% ammonia hydroxide) to afford 1-benzyl-N-[(6R)-2-(2,2-difluorocyclopropyl)-4-methyl-5-oxo-2,6,7,8-tetrahydro-1H-pyrazolo[1,5-a][1,3]diazepin-6-yl]-1,2,4-triazole-3-carboxamide (105.3 mg, 57%) as white solid: $^1$H NMR (400 MHz, DMSO-$d_6$) δ 8.82 (s, 1H), 8.55 (d, J=8.0 Hz, 1H), 7.40-7.29 (m, 5H), 6.28 (d, J=8.8 Hz, 1H), 5.48 (s, 2H), 4.33-4.29 (m, 2H), 4.17-4.16 (m, 1H), 3.321 (s, 3H), 2.93-2.88 (m, 1H), 2.59-2.50 (m, 1H), 2.37-2.36 (m, 1H), 1.96-1.84 (m, 2H). LCMS $R_T$=1.77 min; m/z=442.2 $(M+H)^+$.

LCMS (0 to 60% acetonitrile in water+0.03% trifluoacetic acid over 3 mins) retention time 1.77 min, ESI+ found [M+H]=442.2.

Example 285

WX Method LLLLL

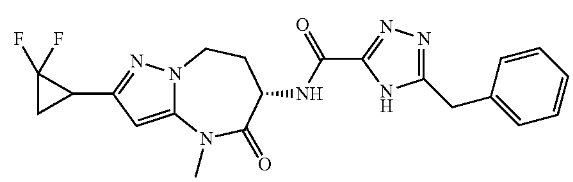 [SMILES: CN1C(=O)[C@@H](NC(=O)c2nnc(Cc3ccccc3)[nH]2)CCn2nc(C3CC3(F)F)cc21]

5-benzyl-N-((6S)-2-(2,2-difluorocyclopropyl)-4-methyl-5-oxo-5,6,7,8-tetrahydro-4H-pyrazolo[1,5-a][1,3]diazepin-6-yl)-4H-1,2,4-triazole-3-carboxamide A mixture of (6S)-6-amino-2-(2,2-difluorocyclopropyl)-4-methyl-7,8-dihydro-4H-pyrazolo[1,5-a][1,3]diazepin-5(6H)-one (100 mg, 0.39 mmol), 5-benzyl-4H-1,2,4-triazole-3-carboxylic acid (79 mg, 0.39 mmol), 1H-benzo[d][1,2,3]triazol-1-ol (79 mg, 0.59 mmol) and $N^1$-((ethylimino)methylene)-$N^3$,$N^3$-dimethylpropane-1,3-diamine hydrochloride (110 mg, 0.59 mmol) in N,N-dimethylformamide (10 mL) was stirred at 25° C. for 16 h. The reaction was concentrated under reduced pressure and the residue was purified by RP-HPLC (acetonitrile 22-52%/0.05% ammonia hydroxide in water) to afford 5-benzyl-N-((6 S)-2-(2,2-difluorocyclopropyl)-4-methyl-5-oxo-5,6,7,8-tetrahydro-4H-pyrazol o[1,5-a][1,3]diazepin-6-yl)-4H-1,2,4-triazole-3-carboxamide as a white solid (100 mg, 57%): $^1$H NMR (400 MHz, DMSO-$d_6$) δ 7.34-7.21 (m, 5H), 6.29 (d, J=8.4 Hz, 1H), 4.35-4.26 (m, 2H), 4.20-4.15 (m, 1H), 4.11 (s, 2H), 3.22 (d, J=1.6 Hz, 3H), 2.93-2.88 (m, 1H), 2.59-2.57 (m, 1H), 2.44-2.35 (m, 1H), 2.01-1.93 (m, 1H), 1.90-1.81 (m, 1H). LCMS $R_T$ 0.98=min; m/z=442.2 $(M+H)^+$.

LCMS (10 to 80% acetonitrile in water+0.03% trifluoacetic acid over 2.0 mins) retention time 0.98 min, ESI+ found [M+H]=442.2.

Example 286

WX Method MMMMM

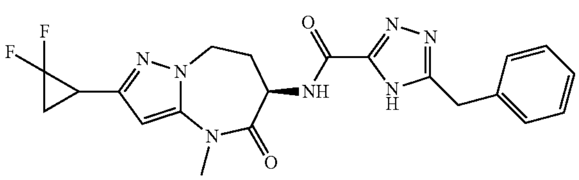 [SMILES: CN1C(=O)[C@H](NC(=O)c2nnc(Cc3ccccc3)[nH]2)CCn2nc(C3CC3(F)F)cc21]

5-benzyl-N-((6R)-2-(2,2-difluorocyclopropyl)-4-methyl-5-oxo-5,6,7,8-tetrahydro-4H-pyrazolo[1,5-a][1,3]diazepin-6-yl)-4H-1,2,4-triazole-3-carboxamide A mixture of (6R)-6-amino-2-(2,2-difluorocyclopropyl)-4-methyl-7,8-dihydro-4H-pyrazolo[1,5-a][1,3]diazepin-5(6H)-one (100 mg, 0.39 mmol), 5-benzyl-4H-1,2,4-triazole-3-carboxylic acid (79 mg, 0.39 mmol), 1H-benzo[d][1,2,3]triazol-1-ol (79 mg, 0.59 mmol) and $N^1$-((ethylimino)methylene)-$N^3$,$N^3$-dimethylpropane-1,3-diamine hydrochloride (110 mg, 0.59 mmol) in N,N-dimethylformamide (10 mL) was stirred at 25° C. for 16 h. The reaction was concentrated under reduced pressure and the residue was purified by RP-HPLC (20-50% acetonitrile in water and 0.05% ammonia hydroxide) to afford 5-benzyl-N-((6R)-2-(2,2-difluorocyclopropyl)-4-methyl-5-oxo-5,6,7,8-tetrahydro-4H-pyrazolo[1,5-a][1,3]diazepin-6-yl)-4H-1,2,4-triazole-3-carboxamide (101 mg, 58% yield) as white solid: $^1$H NMR (400 MHz, DMSO-$d_6$) δ 7.32-7.20 (m, 5H), 6.26 (d, J=8.0 Hz, 1H), 4.32-4.27 (m, 2H), 4.15-4.09 (m, 3H), 3.19 (s, 3H), 2.89-2.86 (m, 1H), 2.66-2.63 (m, 1H) 2.56-2.55 (m, 1H), 1.95-1.85 (m, 1H), 1.84-1.82 (m, 1H). LCMS $R_T$=1.74 min; m/z=442.1 $(M+H)^+$.

LCMS (0 to 60% acetonitrile in water+0.03% trifluoacetic acid over 3 mins) retention time 1.74 min, ESI+ found [M+H]=442.2.

Example 287

WX Method NN

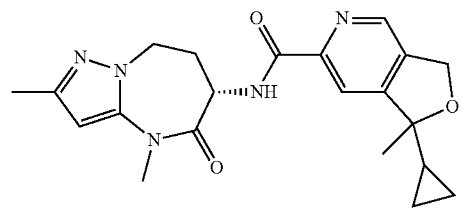 [SMILES: Cc1cc2n(n1)CC[C@H](NC(=O)c1cc3c(cn1)COC3(C)C1CC1)C(=O)N2C]

1-cyclopropyl-N—((S)-2,4-dimethyl-5-oxo-5,6,7,8-tetrahydro-4H-pyrazolo[1,5-a][1,3]diazepin-6-yl)-1-methyl-1,3-dihydrofuro[3,4-c]pyridine-6-carboxamide

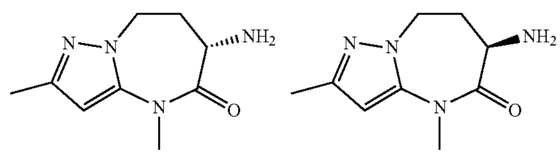

Step 1: (6S)-6-amino-2,4-dimethyl-7,8-dihydro-6H-pyrazolo[1,5-a][1,3]diazepin-5-one (6R)-6-amino-2,4-dimethyl-7,8-dihydro-6H-pyrazolo[1,5-a][1,3]diazepin-5-one 6-amino-2,4-dimethyl-7,8-dihydro-4H-pyrazolo[1,5-a][1,3]diazepin-5(6H)-one (1.5 g, 7.7 mmol) was separated by chiral SFC ($SFCl_3$; Chiralpak OD (250 mm*30 mm, 5 um); Supercritical $CO_2$/MeOH+$NH_3$*$H_2O$=20/20; 60 ml/min) to afford:

(6S)-6-amino-2,4-dimethyl-7,8-dihydro-6H-pyrazolo[1,5-a][1,3]diazepin-5-one (Peak 1, $R_T$=2.757 min) (400 mg, 27%) as white solids.

(6R)-6-amino-2,4-dimethyl-7,8-dihydro-6H-pyrazolo[1,5-a][1,3]diazepin-5-one (Peak 2, $R_T$=3.846 min) (350 mg, 23%) as white solids.

Step 2: 1-cyclopropyl-N—((S)-2,4-dimethyl-5-oxo-5,6,7,8-tetrahydro-4H-pyrazolo[1,5-a][1,3]diazepin-6-yl)-1-methyl-1,3-dihydrofuro[3,4-c]pyridine-6-carboxamide A mixture of (6S)-6-amino-2,4-dimethyl-7,8-dihydro-6H-pyrazolo[1,5-a][1,3]diazepin-5-one (20 mg, 0.10 mmol), 1-cyclopropyl-1-methyl-3H-furo[3,4-c]pyridine-6-carboxylic acid (23 mg, 0.10 mmol), $N^1$-((ethylimino)methylene)-$N^3$,$N^3$-dimethylpropane-1,3-diamine hydrochloride (30 mg, 0.16 mmol) and 1H-benzo[d][1,2,3]triazol-1-ol (21 mg, 0.16 mmol) in N,N-dimethylformamide (5 mL) was stirred at 25° C. for 16 h. The reaction was concentrated under reduced pressure and the residue was purified by RP-HPLC (25% to 55% acetonitrile, 0.05% ammonia hydroxide in water) to give 1-cyclopropyl-N—((S)-2,4-dimethyl-5-oxo-5,6,7,8-tetrahydro-4H-pyrazolo[1,5-a][1,3]diazepin-6-yl)-1-methyl-1,3-dihydrofuro[3, 4-c]pyridine-6-carboxamide (13 mg, 30%) as a white solid: $^1$H NMR (400 MHz, $CD_3OD$) δ 8.53 (s, 1H), 7.92 (s, 1H), 6.10 (s, 1H), 5.13-5.04 (m, 2H), 4.58-4.55 (m, 1H), 4.35-4.22 (m, 2H), 3.33 (s, 3H), 2.92-2.85 (m, 1H), 2.27-2.21 (m, 4H), 1.48 (s, 3H), 1.28-1.23 (m, 1H), 0.47-0.25 (m, 4H). LCMS $R_T$=0.68 min; m/z=396.0 $(M+H)^+$.

LCMS (5 to 95% acetonitrile in water+0.03% trifluoacetic acid over 1.5 mins) retention time 0.68 min, ESI+ found [M+H]=396.0.

Example 288

WX Method TTT

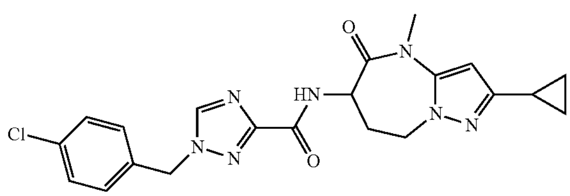 [SMILES: CN1C(=O)C(NC(=O)c2ncn(Cc3ccc(Cl)cc3)n2)CCn2nc(C3CC3)cc21]

1-(4-chlorobenzyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide To a solution of N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (3 mL) was added potassiumcarbonate (329 mg, 2.38 mmol) and 1-(bromomethyl)-4-chlorobenzene (244 mg, 1.19 mmol). The mixture was stirred at 25° C. for 12 h and then filtered. The filtrate was evaporated under reduced pressure and the residue was purified by RP-HPLC (55-85% methyl alcohol in water and 0.05% ammonia hydroxide) to afford 1-(4-chlorobenzyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (63.3 mg, 18%): $^1$H NMR (400 MHz, DMSO-$d_6$) δ 8.80 (s, 1H), 8.52 (d, J=8.0 Hz, 1H), 7.42 (d, J=8.0 Hz, 2H), 7.31 (d, J=8.0 Hz, 2H), 6.04 (s, 1H), 5.47 (s, 2H), 4.29-4.21 (m, 2H), 4.19-4.05 (m, 1H), 3.17 (s, 3H), 2.57-2.45 (m, 2H), 1.86-1.80 (m, 1H), 0.84-0.82 (m, 2H), 0.65-0.59 (m, 2H). LCMS $R_T$=1.84 min; m/z=440.1 $(M+H)^+$.

LCMS (0 to 60% acetonitrile in water+0.03% trifluoacetic acid over 3 mins) retention time 1.84 min, ESI+ found [M+H]=440.1.

Example 289

WX Method JJJ

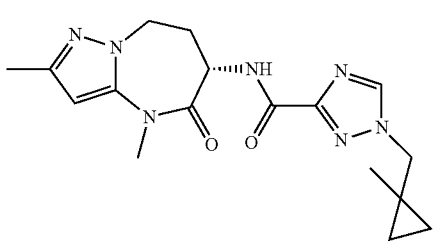 [SMILES: Cc1cc2n(n1)CC[C@H](NC(=O)c1ncn(CC3(C)CC3)n1)C(=O)N2C]

(S)—N-(2,4-dimethyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide

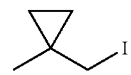

Step 1: 1-(iodomethyl)-1-methylcyclopropane

To a stirred suspension of triphenylphosphine (457 mg, 1.74 mmol) in dichloromethane (10 mL) was added imidazole (118 mg, 1.74 mmol) and iodine (442 mg, 1.74 mmol) at 0° C. The reaction mixture was stirred at 0° C. for 30 minutes, and a solution of 1-methylcyclopropanemethanol (100 mg, 1.16 mmol) in dichloromethane (5 mL) was added. The reaction mixture was allowed to warm to 25° C. and stirred for 2 h and then quenched by addition of brine (10 mL). The mixture was extracted with dichloromethane (3×10 mL). The combined organic layers were washed with water (2×10 mL), aqueous sodium thiosulfate (5%, 10 mL), dried over sodium sulfate and evaporated under reduced pressure to afford 1-(iodomethyl)-1-methylcyclopropane (200 mg, 88%) as colorless oil, used in the next step without further purification.

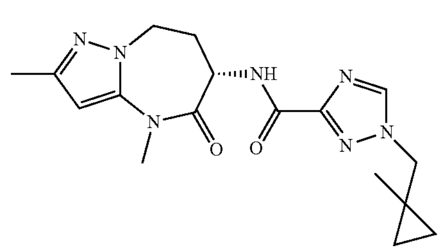 [SMILES: Cc1cc2n(n1)CC[C@H](NC(=O)c1ncn(CC3(C)CC3)n1)C(=O)N2C]

Step 2: (S)—N-(2,4-dimethyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide A mixture of (S)—N-(2,4-dimethyl-5-oxo-5,6,7,8-tetrahydro-4H-pyrazolo[1,5-a][1,3]diazepin-6-yl)-1H-1,2,4-triazole-3-carboxamide (147 mg, 0.51 mmol) and potassium carbonate (141 mg, 1.02 mmol) in N,N-dimethylformamide (3 mL) was added 1-(iodomethyl)-1-methylcyclopropane (100 mg, 0.51 mmol). The mixture was stirred at 25° C. for 12 h. The reaction mixture was concentrated under reduced pressure, and the residue was purified by RP-HPLC (acetonitrile 0-40%/0.1% ammonia hydroxide in water) to afford (S)—N-(2,4-dimethyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide (12 mg, 7%) as white solid: $^1$H NMR (400 MHz, $CD_3OD$) δ 8.55 (s, 1H), 6.14 (s, 1H), 4.88-4.54 (m, 1H), 4.34-4.32 (m, 1H), 4.27-4.24 (m, 1H), 4.15 (s, 2H), 3.35 (s, 3H), 2.92-2.85 (m, 1H), 2.32-2.26 (m, 4H), 1.05 (s, 3H), 0.76-0.73 (m, 2H), 0.50-0.47 (m, 2H). LCMS $R_T$=1.36 min, m/z=358.2 $(M+H)^+$.

LCMS (10 to 80% acetonitrile in water+0.05% ammonium hydroxide over 3 mins) retention time 1.36 min, ESI+ found $[M+H]^+$=358.2.

Example 290

WX Method JJJJ

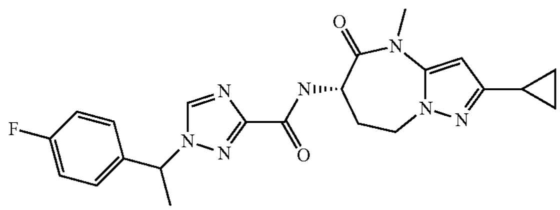 [SMILES: CC(c1ccc(F)cc1)n1cnc(C(=O)N[C@H]2CCn3nc(C4CC4)cc3N(C)C2=O)n1]

(S)—N-(2-cyclopropyl-4-methyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (3 mL) was added potassium carbonate (328 mg, 2.38 mmol) and 1-(1-bromoethyl)-4-fluorobenzene (193 mg, 0.95 mmol). The mixture was stirred at 25° C. for 12 h and then filtered. The filtrate was evaporated under reduced pressure and the residue was purified by RP-HPLC (55-85% methanol in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide (40.1 mg, 11%) as a white solid: $^1$H NMR (400 MHz, DMSO-$d_6$) δ 8.85 (s, 1H), 8.52 (d, J=7.6 Hz, 1H), 7.40-7.37 (m, 2H), 7.22-7.18 (m, 2H), 6.06 (s, 1H), 5.86-5.81 (m, 1H), 4.32-4.21 (m, 2H), 4.09-4.08 (m, 1H), 3.19 (s, 3H), 2.59-2.55 (m, 1H), 2.40-2.32 (m, 1H), 1.87-1.83 (m, 4H), 0.87-0.84 (m, 2H), 0.67-0.64 (m, 2H). LCMS $R_T$=0.80 min; m/z=438.2 $(M+H)^+$.

LCMS (5 to 95% acetonitrile in water+0.03% formic acid over 1.5 mins) retention time 0.80 min, ESI+ found [M+H]=438.2.

Example 291

WX Method KKKK

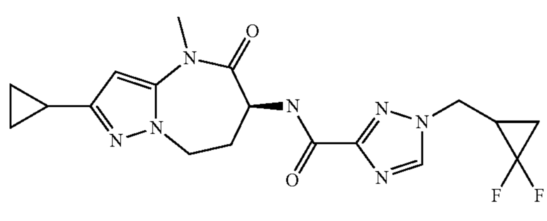 [SMILES: CN1C(=O)[C@@H](NC(=O)c2ncn(CC3CC3(F)F)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-((2,2-difluorocyclopropyl)methyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (5 mL) was added potassium carbonate (328 mg, 2.38 mmol) and 2-(bromomethyl)-1,1-difluoro-cyclopropane (163 mg, 0.95 mmol). The mixture was stirred at 25° C. for 12 h and then filtered. The filtrate was evaporated under reduced pressure and the residue was purified by RP-HPLC (47-77% methanol in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-((2,2-difluorocyclopropyl)methyl)-1H-1,2,4-triazole-3-carboxamide (57 mg, 18%) as a white solid: $^1$H NMR (400 MHz, DMSO-$d_6$) δ 8.70 (s, 1H), 8.56 (d, J=8.0 Hz, 1H), 6.07 (s, 1H), 4.45-4.30 (m, 4H), 4.24-4.09 (m, 1H), 3.20 (s, 3H), 2.61-2.58 (m, 1H), 2.34-2.32 (m, 2H), 1.87-1.85 (m, 1H), 1.83-1.80 (m, 1H), 1.77-1.67 (m, 1H), 0.86-0.84 (m, 2H), 0.69-0.64 (m, 2H). LCMS $R_T$=0.74 min; m/z=406.1 $(M+H)^+$.

LCMS (5 to 95% acetonitrile in water+0.03% formic acid over 1.5 mins) retention time 0.74 min, ESI+ found [M+H]=406.1.

Example 292

WX Method LLLL

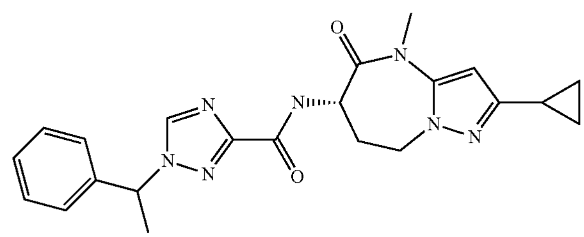 [SMILES: CC(c1ccccc1)n1cnc(C(=O)N[C@H]2CCn3nc(C4CC4)cc3N(C)C2=O)n1]

(S)—N-(2-cyclopropyl-4-methyl-5-oxo-5,6,7,8-tetrahydro-4H-pyrazolo[1,5-a][1,3]diazepin-6-yl)-1-(1-phenylethyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (250 mg, 0.79 mmol) in N,N-dimethylformamide (5 mL) was added potassium carbonate (328 mg, 2.38 mmol) and (1-bromoethyl)benzene (176 mg, 0.95 mmol). The mixture was stirred at 25° C. for 12 h and then filtered. The filtrate was evaporated under reduced pressure and the residue was purified by RP-HPLC (55-85% methanol in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(1-phenylethyl)-1H-1,2,4-triazole-3-carboxamide (34 mg, 10%) as a white solid: $^1$H NMR (400 MHz, DMSO-$d_6$) δ 8.87 (s, 1H), 8.54 (d, J=7.6 Hz, 1H), 7.36-7.32 (m, 5H), 6.06 (s, 1H), 5.82-5.80 (m, 1H), 4.32-4.21 (m, 2H), 4.12-4.08 (m, 1H), 3.19 (s, 3H), 2.57-2.50 (m, 1H), 2.37-2.33 (m, 1H), 1.86-1.84 (m, 4H), 0.86-0.84 (m, 2H), 0.67-0.65 (m, 2H). LCMS $R_T$=0.79 min; m/z=420.1 $(M+H)^+$.

LCMS (5 to 95% acetonitrile in water+0.03% formic acid over 1.5 mins) retention time 0.79 min, ESI+ found [M+H]=420.1.

Example 293

WX Method BBBBBBB

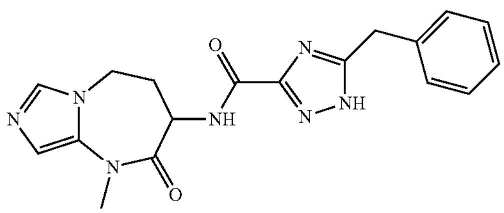 [SMILES: CN1C(=O)C(NC(=O)c2n[nH]c(Cc3ccccc3)n2)CCn2cncc21]

5-benzyl-N-(1-methyl-2-oxo-2,3,4,5-tetrahydro-1H-imidazo[1,5-a][1,3]diazepin-3-yl)-1H-1,2,4-triazole-3-carboxamide A mixture of 5-benzyl-1H-1,2,4-triazole-3-carboxylic acid (20 mg, 0.10 mmol), 3-amino-1-methyl-4,5-dihydro-3H-imidazo[1,5-a][1,3]diazepin-2-one (15 mg, 0.08 mmol), 1H-benzo[d][1,2,3]triazol-1-ol (17 mg, 0.12 mmol) and $N^1$-((ethylimino)methylene)-$N^3$,$N^3$-dimethylpropane-1,3-diamine hydrochloride (22 mg, 0.12 mmol) in N,N-dimethylformamide (5 mL) was stirred at 25° C. for 12 h. The reaction was concentrated under reduced pressure and the residue was purified by RP-HPLC (acetonitrile 17-47/0.05% $NH_4HCO_3$ in water) to give 5-benzyl-N-(1-methyl-2-oxo-2,3,4,5-tetrahydro-1H-imidazo[1,5-a][1,3]diazepin-3-yl)-1H-1,2,4-triazole-3-carboxamide (8.4 mg, 27% yield) as a white solid: $^1$H NMR (400 MHz, $CD_3OD$) δ 7.66 (s, 1H), 7.31-7.24 (m, 5H), 7.01 (s, 1H), 4.45-4.41 (m, 2H), 4.16 (s, 2H), 4.04-3.96 (m, 1H), 3.35 (s, 3H), 2.80-2.72 (m, 1H), 2.21-2.13 (m, 1H). LCMS $R_T$=1.118 min; m/z=366.1 $(M+H)^+$.

LCMS (0 to 60% acetonitrile in water+0.05% ammonium bicarbonate over 3.0 mins) retention time 1.118 min, ESI+ found [M+H]=366.1.

Example 294

WX Method ZZZZZZ

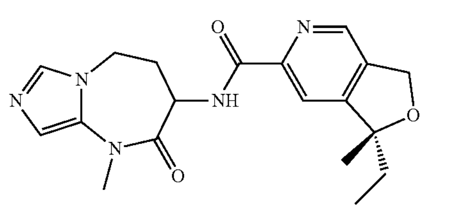 [SMILES: CC[C@@]1(C)OCc2cnc(C(=O)NC3CCn4cncc4N(C)C3=O)cc21]

(1R)-1-ethyl-1-methyl-N-(1-methyl-2-oxo-2,3,4,5-tetrahydro-1H-imidazo[1,5-a][1,3]diazepin-3-yl)-1,3-dihydrofuro[3,4-c]pyridine-6-carboxamide A mixture of (1R)-1-ethyl-1-methyl-3H-furo[3,4-c]pyridine-6-carboxylic acid (21 mg, 0.10 mmol), 3-amino-1-methyl-4,5-dihydro-3H-imidazo[1,5-a][1,3]diazepin-2-one (15 mg, 0.08 mmol), 1H-benzo[d][1,2,3]triazol-1-ol (17 mg, 0.12 mmol) and $N^1$-((ethylimino)methylene)-$N^3$,$N^3$-dimethylpropane-1,3-diamine hydrochloride (22 mg, 0.12 mmol) in N,N-dimethylformamide (5 mL) was stirred at 25° C. for 12 h. The reaction was concentrated under reduced pressure and the residue was purified by RP-HPLC (acetonitrile 17-47/0.05% $NH_4HCO_3$ in water) to give (1R)-1-ethyl-1-methyl-N-(1-methyl-2-oxo-2,3,4,5-tetrahydro-1H-imidazo[1,5-a][1,3]diazepin-3-yl)-1,3-dihydrofuro[3,4-c]pyridine-6-carboxamide (9.8 mg, 32%) as a white solid: $^1$H NMR (400 MHz, $CD_3OD$) δ 8.55 (s, 1H), 7.87 (s, 1H), 7.65 (s, 1H), 7.01 (s, 1H), 5.16-5.15 (m, 2H), 4.65-4.60 (m, 1H), 4.66-4.41 (m, 1H), 4.05-3.98 (m, 1H), 3.37 (s, 3H), 2.84-2.80 (m, 1H), 2.21-2.17 (m, 1H), 1.88-1.82 (m, 2H), 1.46 (s, 3H), 0.77 (t, J=7.2 Hz, 3H). LCMS $R_T$=1.385 min; m/z=370.2 $(M+H)^+$.

LCMS (10 to 80% acetonitrile in water+0.05% ammonium bicarbonate over 3.0 mins) retention time 1.385 min, ESI+ found [M+H]=370.2.

Example 295

WX Method AAAAAA

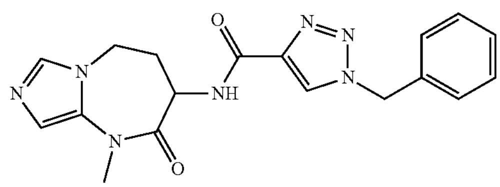 [SMILES: CN1C(=O)C(NC(=O)c2cn(Cc3ccccc3)nn2)CCn2cncc21]

1-benzyl-N-(1-methyl-2-oxo-2,3,4,5-tetrahydro-1H-imidazo[1,5-a][1,3]diazepin-3-yl)-1H-1,2,3-triazole-4-carboxamide A mixture of 1-benzyltriazole-4-carboxylic acid (20 mg, 0.10 mmol), 3-amino-1-methyl-4,5-dihydro-3H-imidazo[1,5-a][1,3]diazepin-2-one (15 mg, 0.08 mmol), 1H-benzo[d][1,2,3]triazol-1-ol (17 mg, 0.12 mmol) and $N^1$-((ethylimino)methylene)-$N^3$,$N^3$-dimethylpropane-1,3-diamine hydrochloride (22 mg, 0.12 mmol) in N,N-dimethylformamide (5 mL) was stirred at 25° C. for 12 h. The reaction was concentrated under reduced pressure and the residue was purified by RP-HPLC (acetonitrile 17-47/0.05% $NH_4HCO_3$ in water) to give 1-benzyl-N-(1-methyl-2-oxo-2,3,4,5-tetrahydro-1H-imidazo[1,5-a][1,3]diazepin-3-yl)-1H-1,2,3-triazole-4-carboxamide (12.1 mg, 39%) as a white solid: $^1$H NMR (400 MHz, $CD_3OD$) δ 8.34 (s, 1H), 7.61 (s, 1H), 7.36-7.32 (m, 5H), 6.98 (s, 1H), 5.63 (s, 2H), 4.61-4.56 (m, 1H), 4.44-4.38 (m, 1H), 4.03-3.98 (m, 1H), 3.34 (s, 3H), 2.75-2.69 (m, 1H), 2.24-2.18 (m, 1H). LCMS $R_T$=1.329 min; m/z=366.2 $(M+H)^+$.

LCMS (10 to 80% acetonitrile in water+0.05% ammonium bicarbonate over 3.0 mins) retention time 1.329 min, ESI+ found [M+H]=366.2.

Example 296

WX Method MM

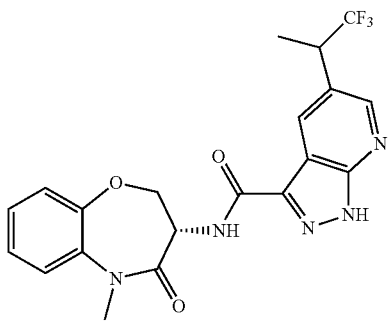 [SMILES: CC(c1cnc2[nH]nc(C(=O)N[C@H]3COc4ccccc4N(C)C3=O)c2c1)C(F)(F)F]

N—((S)-5-methyl-4-oxo-2,3,4,5-tetrahydrobenzo[b][1,4]oxazepin-3-yl)-5-(1,1,1-trifluoropropan-2-yl)-1H-pyrazolo[3,4-b]pyridine-3-carboxamide

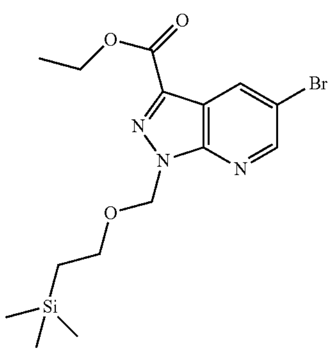 [SMILES: CCOC(=O)c1nn(COCC[Si](C)(C)C)c2ncc(Br)cc12]

Step 1: Methyl 5-bromo-1-(2-trimethylsilylethoxymethyl)pyrazolo[3,4-b]pyridine-3-carboxylate To a solution of methyl 5-bromo-1h-pyrazolo[3,4-b]pyridine-3-carboxylate (1.0 g, 3.91 mmol) in tetrahydrofuran (20 mL) was added triethylamine (790 mg, 7.81 mmol) and 2-(trimethylsilyl)ethoxymethyl chloride (977 mg, 5.86 mmol). The mixture was stirred at 25° C. for 4 h and then diluted with water (10 mL). The mixture was extracted with ethyl acetate (3×15 mL). The combined organic layers were washed water (20 mL), brine (20 mL), dried over sodium sulfate and concentrated under reduced pressure. The residue was purified by column chromatography (silica gel, 100-200 mesh, 0 to 6% ethyl acetate in petroleum ether) to afford methyl 5-bromo-1-(2-trimethylsilylethoxymethyl) pyrazolo[3,4-b]pyridine-3-carboxylate (560 mg, 37%) as colorless oil, used as is in the next step.

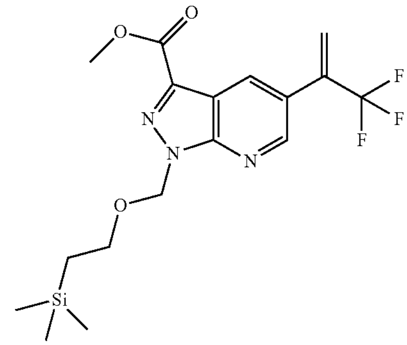 [SMILES: C=C(c1cnc2c(c1)c(C(=O)OC)nn2COCC[Si](C)(C)C)C(F)(F)F]

Step 2: Methyl 5-[1-(trifluoromethyl)vinyl]-1-(2-trimethylsilylethoxymethyl) pyrazolo[3,4-b]pyridine-3-carboxylate A mixture of methyl 5-bromo-1-(2-trimethylsilylethoxymethyl)pyrazolo[3,4-b]pyridine-3-carboxylate (560 mg, 1.45 mmol), 1-(trifluoromethyl)vinylboronic acid hexylene glycol ester (482 mg, 2.17 mmol), 1,1'-bis (diphenylphosphino)ferrocene palladium dichloride (106. mg, 0.14 mmol) and cesium carbonate (944 mg, 2.9 mmol) in 1,4-dioxane (4 mL) and water (1 mL) was heated at 110° C. for 1 h under microwave conditions. The reaction mixture was concentrated under reduced pressure and the residue was purified by column chromatography (silica gel, 100-200 mesh, 0 to 15% ethyl acetate in petroleum ether) to afford methyl 5-[1-(trifluoromethyl)vinyl]-1-(2-trimethylsilylethoxymethyl)pyrazolo[3,4-b]pyridine-3-carboxylate (450 mg, 77%) as a white solid: LCMS $R_T$=0.999 min; m/z=402.1 $(M+H)^+$.

LCMS (5 to 95% acetonitrile in water+0.03% trifluoacetic acid over 1.5 mins) retention time 0.999 min, ESI+ found [M+H]=402.1.

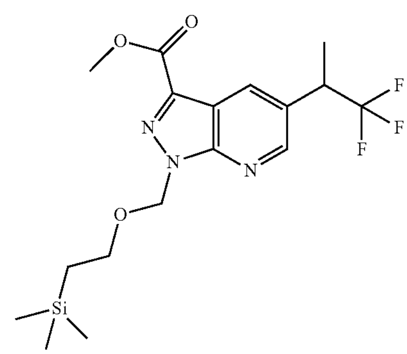 [SMILES: COC(=O)c1nn(COCC[Si](C)(C)C)c2ncc(C(C)C(F)(F)F)cc12]

Step 3: Methyl 5-(2,2,2-trifluoro-1-methyl-ethyl)-1-(2-trimethylsilylethoxymethyl)pyrazolo[3,4-b]pyridine-3-carboxylate A mixture of methyl 5-[1-(trifluoromethyl)vinyl]-1-(2-trimethyl silyl ethoxymethyl) pyrazolo[3,4-b]pyridine-3-carboxylate (150 mg, 0.37 mmol) and 10% palladium on carbon (40 mg, 0.04 mmol) in methanol (5 mL) was hydrogenated (50 psi) at 25° C. for 18 h. The reaction mixture was filtered and the filtrate was concentrated under reduced pressure affording crude methyl 5-(2,2,2-trifluoro-1-methylethyl)-1-(2-trimethyl silylethoxymethyl) pyrazolo[3,4-b]pyridine-3-carboxylate (111 mg, 74%) as a white solid: LCMS $R_T$=0.998 min; m/z=404.1 $(M+H)^+$.

LCMS (5 to 95% acetonitrile in water+0.03% trifluoacetic acid over 1.5 mins) retention time 0.998 min, ESI+ found [M+H]=404.1

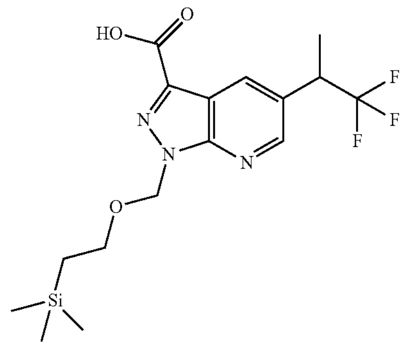 [SMILES: CC(c1cnc2c(c1)c(C(=O)O)nn2COCC[Si](C)(C)C)C(F)(F)F]

Step 4: 5-(2,2,2-trifluoro-1-methyl-ethyl)-1-(2-trimethylsilylethoxymethyl)pyrazolo[3,4-b]pyridine-3-carboxylic acid A mixture of methyl 5-(2,2,2-trifluoro-1-methyl-ethyl)-1-(2-trimethylsilyl ethoxymethyl)pyrazolo[3,4-b]pyridine-3-carboxylate (111 mg, 0.28 mmol) and lithium hydroxide hydrate (33 mg, 1.38 mmol) in tetrahydrofuran (5 mL) and water (1 mL) was stirred at 29° C. for 18 h. The organic solvent was evaporated under reduced pressure and the aqueous residue was adjusted to pH=5 by addition of hydrochloric acid (1.0 M). The solid was removed by filtration and the aqueous layer was concentrated under reduced pressure affording crude 5-(2,2,2-trifluoro-1-methyl-ethyl)-1-(2-trimethyl silylethoxymethyl)pyrazolo[3,4-b]pyridine-3-carboxylic acid (68 mg, 63%) as a white solid: LCMS $R_T$=2.077 min; m/z=390.1 $(M+H)^+$.

LCMS (0 to 60% acetonitrile in water+0.04% formic acid over 3 mins) retention time 2.077 min, ESI+ found [M+H]=390.1

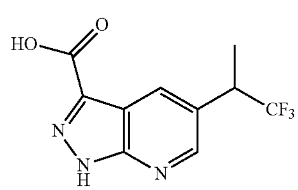 [SMILES: CC(c1cnc2[nH]nc(C(=O)O)c2c1)C(F)(F)F]

Step 5: 5-(2,2,2-trifluoro-1-methyl-ethyl)-1h-pyrazolo[3,4-b]pyridine-3-carboxylic acid To a solution of 5-(2,2,2-trifluoro-1-methyl-ethyl)-1-(2-trimethylsilylethoxymethyl) pyrazolo[3,4-b]pyridine-3-carboxylic acid (68 mg, 0.17 mmol) in water (5 mL) was added hydrochloric acid (4.0 M in dioxane, 0.2 mL, 0.80 mmol). The reaction mixture was stirred at ° C. for 18 h and then concentrated under reduced pressure affording 5-(2,2,2-trifluoro-1-methyl-ethyl)-1H-pyrazolo[3,4-b]pyridine-3-carboxylic acid (32 mg, 70%) as a white solid: LCMS $R_T$=0.716 min; m/z=259.9 $(M+H)^+$.

LCMS (5 to 95% acetonitrile in water+0.03% trifluoacetic acid over 1.5 mins) retention time 0.716 min, ESI+ found [M+H]=259.9.

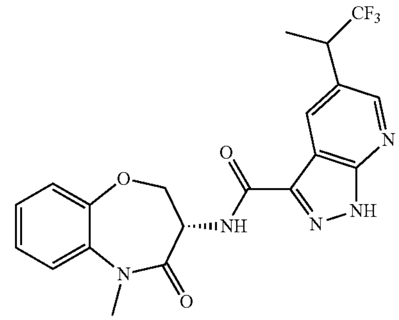 [SMILES: CC(c1cnc2[nH]nc(C(=O)N[C@H]3COc4ccccc4N(C)C3=O)c2c1)C(F)(F)F]

Step 6: N—((S)-5-methyl-4-oxo-2,3,4,5-tetrahydrobenzo[b][1,4]oxazepin-3-yl)-5-(1,1,1-trifluoropropan-2-yl)-1H-pyrazolo[3,4-b]pyridine-3-carboxamide A mixture of 5-(2,2,2-trifluoro-1-methyl-ethyl)-1h-pyrazolo[3,4-b]pyridine-3-carboxylic acid (32 mg, 0.12 mmol), (3s)-3-amino-5-methyl-2,3-dihydro-1,5-benzoxazepin-4-one (26 mg, 0.13 mmol), 1H-benzo[d][1,2,3]triazol-1-ol (20 mg, 0.15 mmol) and $N^1$-((ethylimino)methylene)-$N^3$,$N^3$-dimethylpropane-1,3-diamine hydrochloride (28 mg, 0.15 mmol) in N, N-dimethylformamide (5 mL) was stirred at 25° C. for 3 h. The reaction was concentrated under reduced pressure and the residue was purified by RP-HPLC (acetonitrile 41-51%/0.05% ammonia in water) affording N—((S)-5-methyl-4-oxo-2,3,4,5-tetrahydrobenzo[b][1,4]oxazepin-3-yl)-5-(1,1,1-trifluoropropan-2-yl)-1H-pyrazolo[3,4-b]pyridine-3-carboxamide (24 mg 45%) as a white solid: $^1H$ NMR (400 MHz, DMSO-$d_6$) δ 14.35 (br. s, 1H), 8.72-8.57 (m, 2H), 8.44 (s, 1H), 7.56-7.47 (m, 1H), 7.40-7.19 (m, 3H), 4.98-4.89 (m, 1H), 4.71-4.63 (m, 1H), 4.50-4.43 (m, 1H), 4.17-4.06 (m, 1H), 3.34 (m, 3H), 1.51 (d, J=7.2 Hz, 3H). LCMS $R_T$=0.850 min; m/z=434.4 $(M+H)^+$.

LCMS (5 to 95% acetonitrile in water+0.03% trifluoacetic acid over 1.5 mins) retention time 0.850 min, ESI+ found [M+H]=434.4.

Example 297

WX Method CCCCCCC

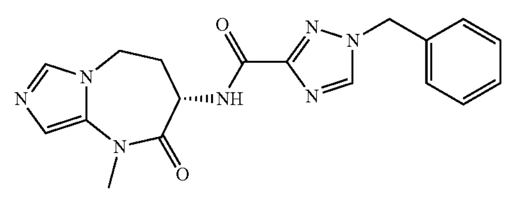 [SMILES: CN1C(=O)[C@@H](NC(=O)c2ncn(Cc3ccccc3)n2)CCn2cncc21]

(S)-1-benzyl-N-(1-methyl-2-oxo-2,3,4,5-tetrahydro-1H-imidazo[1,5-a][1,3]diazepin-3-yl)-1H-1,2,4-triazole-3-carboxamide 1-benzyl-N-(1-methyl-2-oxo-2,3,4,5-tetrahydro-1H-imidazo[1,5-a][1,3]diazepin-3-yl)-1H-1,2,4-triazole-3-carboxamide (20 mg, 0.055 mmol) was separated by chiral SFC (Column: Chiralpak AS-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.) to afford (S)-1-benzyl-N-(1-methyl-2-oxo-2,3,4,5-tetrahydro-1H-imidazo[1,5-a][1,3]diazepin-3-yl)-1H-1,2,4-triazole-3-carboxamide. ($R_T$=4.174 min, 8.3 mg, 41%) as white solid. LCMS $R_T$=1.664 min; m/z=366.1 $(M+H)^+$.

LCMS (0 to 60% acetonitrile in water+0.05% ammonium bicarbonate over 3.0 mins) retention time 1.664 min, ESI+ found [M+H]=366.1.

Example 298

WX Method FFFF

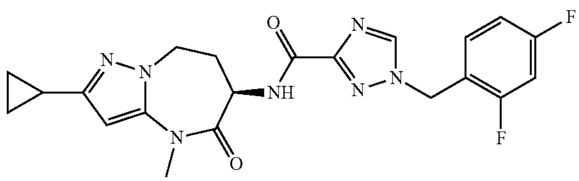 [SMILES: CN1C(=O)[C@H](NC(=O)c2ncn(Cc3ccc(F)cc3F)n2)CCn2nc(C3CC3)cc21]

(R)—N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide A mixture of (6R)-6-amino-2-cyclopropyl-4-methyl-7,8-dihydro-6H-pyrazolo[1,5-a][1,3]diazepin-5-one (20 mg, 0.09 mmol), 1-[(2,4-difluorophenyl)methyl]-1,2,4-triazole-3-carboxylic acid (26 mg, 0.11 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (24 mg, 0.14 mmol) in N,N-dimethylformamide (3 mL) was stirred at 25° C. for 2 h. The reaction was concentrated under reduced pressure and the residue was purified by RP-HPLC (26-56% acetonitrile in water and 0.05% ammonia hydroxide) to afford (R)—N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide (9.2 mg, 22%) as a white solid: $^1$H NMR (400 MHz, $CD_3OD$) δ 8.57 (s, 1H), 7.46-7.44 (m, 1H), 7.04-6.97 (m, 2H), 5.99 (s, 1H), 5.51 (s, 2H), 4.52-4.47 (m, 1H), 4.28-4.26 (m, 1H), 4.22-4.17 (m, 1H), 3.29 (s, 3H), 2.83-2.78 (m, 1H), 2.23-2.20 (m, 1H), 1.91-1.86 (m, 1H), 0.93-0.91 (m, 2H), 0.72-0.70 (m, 2H). LCMS $R_T$=0.79 min; m/z=442.1 $(M+H)^+$.

LCMS (5 to 95% acetonitrile in water+0.03% formic acid over 1.5 mins) retention time 0.79 min, ESI+ found [M+H]=442.1.

Example 299

WX Method EE

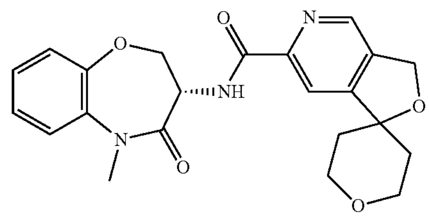 [SMILES: CN1C(=O)[C@@H](NC(=O)c2cc3c(cn2)COC32CCOCC2)COc2ccccc21]

(S)—N-(5-methyl-4-oxo-2,3,4,5-tetrahydrobenzo[b][1,4]oxazepin-3-yl)-2',3',5',6'-tetrahydro-3H-spiro[furo[3,4-c]pyridine-1,4'-pyran]-6-carboxamide

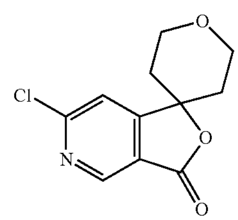 [SMILES: O=C1OC2(CCOCC2)c2cc(Cl)ncc21]

Step 1: 6-chlorospiro[furo[3,4-c]pyridine-1,4'-tetrahydropyran]-3-one

To a stirred solution of 2,2,6,6-tetramethylpiperidine (2.7 g, 19.0 mmol) in tetrahydrofuran (30 mL) was added n-butyllithium (2.5 M, 10 mL, 25.0 mmol) dropwise at −78° C. The mixture was stirred at −78° C. for 40 min and then 6-chloronicotinic acid (1.0 g, 6.4 mmol) in tetrahydrofuran (10 mL) was added. The resulting mixture was stirred at −78° C. for another 2 h, and then tetrahydro-4h-pyran-4-one (1.3 g, 12.7 mmol) was added dropwise. After addition, the reaction was warmed up to 25° C. and stirred for 16 h before quenched by addition of saturated aqueous ammonium chloride. The resulting mixture was extracted with ethyl acetate (3×50 mL). The combined organic layer was washed water (30 mL), brine (30 mL), dried over sodium sulfate and concentrated under reduced pressure.

The residue was purified by column chromatography (silica gel, 100-200 mesh, 0-20% ethyl acetate in petroleum ether) to afford 6-chlorospiro[furo[3,4-c]pyridine-1,4'-tetrahydropyran]-3-one (900 mg, 59%) as yellow oil: $^1$H NMR (400 MHz, DMSO-$d_6$) δ 8.94 (s, 1H), 8.16 (s, 1H), 4.01-3.86 (m, 2H), 3.67-3.64 (m, 2H), 2.31-2.25 (m, 2H), 1.79-1.61 (m, 2H).

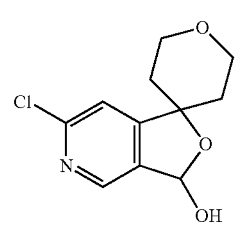 [SMILES: OC1OC2(CCOCC2)c2cc(Cl)ncc21]

Step 2: 6-chlorospiro[3H-furo[3,4-c]pyridine-1,4'-tetrahydropyran]-3-ol

To a solution of 6-chlorospiro[furo[3,4-c]pyridine-1,4'-tetrahydropyran]-3-one (900 mg, 3.76 mmol) in dichloromethane (40 mL) was added diisobutylaluminum hydride (1.0 M, 9.0 mL, 9.0 mmol) dropwise at −70° C. After addition, stirring at −70° C. was continued for 2 h and the reaction mixture was quenched by addition of saturated aqueous ammonium chloride. The resulting mixture was filtered and the filtrate was extracted with ethyl acetate (3×30 mL). The combined organic layers were washed water (20 mL), brine (20 mL), dried over sodium sulfate and concentrated under reduced pressure. The residue was purified by column chromatography (silica gel, 100-200 mesh, 0 to 50% ethyl acetate in petroleum ether) to afford 6-chlorospiro[3H-furo[3,4-c]pyridine-1,4'-tetrahydropyran]-3-ol (790 mg, 87%) as yellow oil: LCMS $R_T$=0.49 min; m/z=241.9 $(M+H)^+$.

LCMS (5-95% acetonitrile in water+0.03% trifluoacetic acid over 1.5 mins) retention time 0.49/min, ESI+ found [M+H]=241.9.

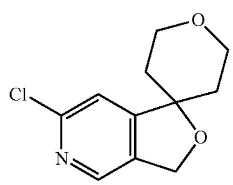 [SMILES: Clc1cc2c(cn1)COC21CCOCC1]

Step 3: 6-chlorospiro[3H-furo[3,4-c]pyridine-1,4'-tetrahydropyran]

To a solution of 6-chlorospiro[3H-furo[3,4-c]pyridine-1,4'-tetrahydropyran]-3-ol (400. mg, 1.66 mmol) in dichloromethane (10 mL) was added trifluoroacetic acid (944 mg, 8.28 mmol) dropwise at 0° C. The reaction was stirred for 30 min at 0° C., and triethyl silane (577 mg, 4.97 mmol) was added. After addition, the mixture was allowed to warm to 25° C. over 3 h and then quenched by addition of saturated sodium bicarbonate. The mixture was extracted with dichloromethane (3×20 mL). The combined organic layers were washed water (20 mL), brine (20 mL), dried over sodium sulfate and concentrated under reduced pressure. The residue was purified by column chromatography (silica gel, 100-200 mesh, 0 to 50% ethyl acetate in petroleum ether) to afford 6-chlorospiro[3H-furo[3,4-c]pyridine-1,4'-tetrahydropyran] (340 mg, 91%) as yellow oil: LCMS $R_T$=0.93 min; m/z=226.1 $(M+H)^+$.

LCMS (0-60% acetonitrile in water+0.03% trifluoacetic acid over 2 mins) retention time 0.93/min, ESI+ found [M+H]=226.1.

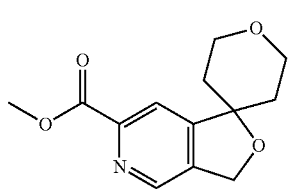 [SMILES: COC(=O)c1cc2c(cn1)COC21CCOCC1]

Step 4: methyl spiro[3H-furo[3,4-c]pyridine-1,4'-tetrahydropyran]-6-carboxylate

A solution of 6-chlorospiro[3H-furo[3,4-c]pyridine-1,4'-tetrahydropyran] (340 mg, 1.41 mmol), 1,1'-bis(diphenylphosphino)ferrocene palladium dichloride (103 mg, 0.14 mmol) and triethylamine (1.4 g, 14.1 mmol) in methanol (20 mL) was heated at 80° C. for 12 h under carbon oxide (25 psi). The mixture was filtered and the filtrate was concentrated under reduced pressure. The residue was purified by column chromatography (silica gel, 100-200 mesh, 0 to 50% ethyl acetate in petroleum ether) to afford methyl spiro[3H-furo[3,4-c]pyridine-1,4'-tetrahydropyran]-6-carboxylate (160 mg, 46%) as a yellow solid: LCMS $R_T$=0.55 min; m/z=249.8 $(M+H)^+$.

LCMS (5-95% acetonitrile in water+0.05% trifluoacetic acid over 1.5 mins) retention time 0.55/min, ESI+ found [M+H]=249.8.

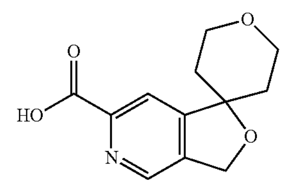 [SMILES: O=C(O)c1cc2c(cn1)COC21CCOCC1]

Step 5: spiro[3H-furo[3,4-c]pyridine-1,4'-tetrahydropyran]-6-carboxylic acid

A mixture of methyl spiro[3H-furo[3,4-c]pyridine-1,4'-tetrahydropyran]-6-carboxylate (30 mg, 0.12 mmol) and lithium hydroxide hydrate (14 mg, 0.60 mmol) in tetrahydrofuran (5 mL) and water (1 mL) was stirred at 25° C. for 2 h. The organic solvent was removed under reduced pressure and the aqueous residue was adjusted to pH=4 by addition of hydrochloric acid (1.0 M). The solution was concentrated under reduced pressure to afford crude spiro[3H-furo[3,4-c]pyri dine-1,4'-tetrahydropyran]-6-carboxylic acid (25 mg, 88%) as a white solid: LCMS $R_T$=1.07 min; m/z=236.1 $(M+H)^+$.

LCMS (0-60% acetonitrile in water+0.05% trifluoacetic acid over 3 mins) retention time 1.07/min, ESI+ found [M+H]=236.1.

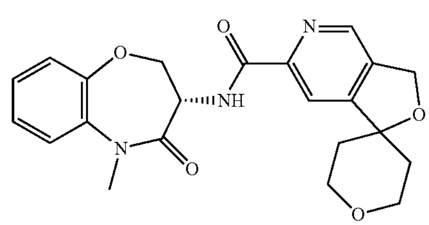 [SMILES: CN1C(=O)[C@@H](NC(=O)c2cc3c(cn2)COC32CCOCC2)COc2ccccc21]

Step 6: (S)—N-(5-methyl-4-oxo-2,3,4,5-tetrahydrobenzo[b][1,4]oxazepin-3-yl)-2',3',5',6'-tetrahydro-3H-spiro[furo[3,4-c]pyridine-1,4'-pyran]-6-carboxamide A mixture of (3S)-3-amino-5-methyl-2,3-dihydro-1,5-benzoxazepin-4-one (20 mg, 0.11 mmol), spiro[3H-furo[3,4-c]pyridine-1,4'-tetrahydropyran]-6-carboxylic acid (25 mg, 0.11 mmol), $N^1$-((ethylimino)methylene)-$N^3$,$N^3$-dimethylpropane-1,3-diamine hydrochloride (24 mg, 0.13 mmol) and 1H-benzo[d][1,2,3]triazol-1-ol (17 mg, 0.13 mmol) in N,N-dimethylformamide (4 mL) was stirred at 25° C. for 12 h. The reaction was concentrated under reduced pressure and the residue was purified by RP-HPLC (acetonitrile 27-57/0.05% ammonia hydroxide in water) to afford (S)—N-(5-methyl-4-oxo-2,3,4,5-tetrahydrobenzo[b][1,4]oxazepin-3-yl)-2',3',5',6'-tetrahydro-3H-spiro[furo[3,4-c]pyridine-1,4'-pyran]-6-carboxamide (19 mg, 44%) as a white solid: $^1$H NMR (400 MHz, $CD_3OD$) δ 8.60 (s, 1H), 7.93 (s, 1H), 7.44-7.43 (m, 1H), 7.34-7.31 (m, 2H), 7.26-7.25 (m, 1H), 5.20 (s, 2H), 5.05-5.02 (m, 1H), 4.67-4.64 (m, 1H), 4.43-4.40 (m, 1H), 3.92-3.41 (m, 4H), 3.31 (s, 3H), 2.09-2.01 (m, 2H), 1.68-1.65 (m, 2H). LCMS $R_T$=2.20 min; m/z=410.1 $(M+H)^+$.

LCMS (0-60% acetonitrile in water+0.05% ammonium bicarbonate over 3 mins) retention time 2.20/min, ESI+ found [M+H]=410.1.

Example 300

WX Method EEEEE

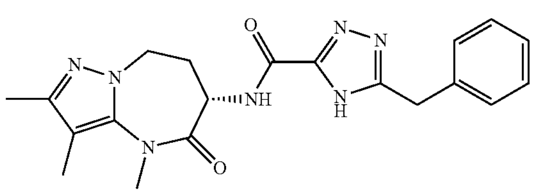 [SMILES: Cc1nn2c(c1C)N(C)C(=O)[C@@H](NC(=O)c1nnc(Cc3ccccc3)[nH]1)CC2]

(S)-5-benzyl-N-(2,3,4-trimethyl-5-oxo-5,6,7,8-tetrahydro-4H-pyrazolo[1,5-a][1,3]diazepin-6-yl)-4H-1,2,4-triazole-3-carboxamide A mixture of 5-benzyl-1H-1,2,4-triazole-3-carboxylic acid (20 mg, 0.10 mmol) (6S)-6-amino-2,3,4-trimethyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol) and $N^1$-((ethylimino)methylene)-$N^3$,$N^3$-dimethyl-propane-1,3-diamine hydrochloride (25 mg, 0.14 mmol) in N,N-dimethylformamide (5 mL) was stirred at 25° C. for 12 h. The reaction was concentrated under reduced pressure and the residue was purified by RP-HPLC (acetonitrile 17-47/0.05% ammonium bicarbonate in water) to give (S)-5-benzyl-N-(2,3,4-trimethyl-5-oxo-5,6,7,8-tetrahydro-4H-pyrazolo[1,5-a][1,3]diazepin-6-yl)-4H-1,2,4-triazole-3-carboxamide (12.2 mg, 37%) as white solid: $^1$H NMR (400 MHz, $CD_3OD$) δ 7.31-7.23 (m, 5H), 4.44-4.39 (m, 1H), 4.22-4.18 (m, 2H), 4.15 (s, 2H), 3.30 (s, 3H), 2.81-2.72 (m, 1H), 2.18-2.16 (m, 4H), 2.00 (s, 3H). LCMS $R_T$=0.74 min; m/z=394.1 $(M+H)^+$.

LCMS (5 to 95% acetonitrile in water+0.03% trifluoacetic acid over 1.5 mins) retention time 0.74 min, ESI+ found [M+H]=394.1.

Example 301

WX Method MMM

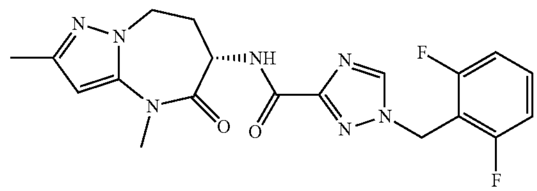 [SMILES: Cc1cc2n(n1)CC[C@H](NC(=O)c1ncn(Cc3c(F)cccc3F)n1)C(=O)N2C]

(S)-1-(2,6-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of N-[(6S)-2,4-dimethyl-5-oxo-7,8-dihydro-6H-pyrazolo[1,5-a][1,3]diazepin-6-yl]-1H-1,2,4-triazole-3-carboxamide (60 mg, 0.21 mmol) and potassium carbonate (86 mg, 0.62 mmol) in N,N-dimethylformamide (5 mL) was added 2-(bromomethyl)-1,3-difluoro-benzene (52 mg, 0.25 mmol). The mixture was stirred at 25° C. for 12 h. The reaction mixture was concentrated under reduced pressure, and the residue was purified by RP-HPLC (methanol 45-75%/0.05% ammonia hydroxide in water) to afford (S)-1-(2,6-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (23.8 mg, 27%) as white solid: $^1$H NMR (400 MHz, $CD_3OD$) δ 8.58 (s, 1H), 7.45-7.42 (m, 1H), 7.05-7.01 (m, 2H), 6.08 (s, 1H), 5.57 (s, 2H), 4.48-4.46 (m, 1H), 4.27-4.25 (m, 1H), 4.24-4.19 (m, 1H), 3.29 (s, 3H), 2.83-2.77 (m, 1H), 2.25-2.21 (m, 4H). LCMS $R_T$=0.739 min, m/z=416.1 $(M+H)^+$.

LCMS (5 to 95% acetonitrile in water+0.03% trifluoacetic acid over 1.5 mins) retention time 0.739 min, ESI+ found [M+H]=416.1.

Example 302

WX Method MMMM

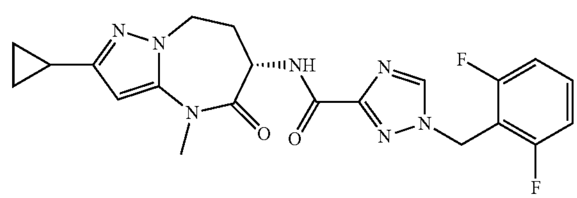 [SMILES: CN1C(=O)[C@@H](NC(=O)c2ncn(Cc3c(F)cccc3F)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(2,6-difluorobenzyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (60 mg, 0.19 mmol) in N,N-dimethylformamide (5 mL) was added potassium carbonate (79 mg, 0.57 mmol) and 2-(bromomethyl)-1,3-difluoro-benzene (47 mg, 0.23 mmol). The mixture was stirred at 25° C. for 12 h and then filtered. The filtrate was evaporated under reduced pressure and the residue was purified by RP-HPLC (52-82% methanol in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(2,6-difluorobenzyl)-1H-1,2,4-triazole-3-carboxamide (29 mg, 35%) as a white solid: $^1$H NMR (400 MHz, $CD_3OD$) δ 8.60 (s, 1H), 7.49-7.42 (m, 1H), 7.08-7.02 (m, 2H), 5.99 (s, 1H), 5.59 (s, 2H), 4.52-4.47 (m, 1H), 4.28-4.24 (m, 1H), 4.22-4.18 (m, 1H), 3.31 (s, 3H), 2.85-2.78 (m, 1H), 2.24-2.22 (m, 1H), 1.91-1.88 (m, 1H), 0.94-0.91 (m, 2H), 0.74-0.72 (m, 2H). LCMS $R_T$=0.78 min; m/z=422.2 $(M+H)^+$.

LCMS (5 to 95% acetonitrile in water+0.03% trifluoacetic acid over 1.5 mins) retention time 0.78 min, ESI+ found [M+H]=442.2

Example 303

WX Method NNNN

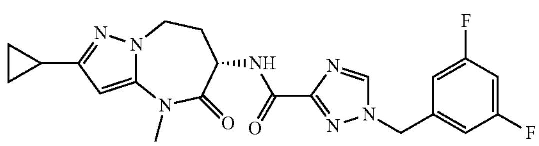 [SMILES: CN1C(=O)[C@@H](NC(=O)c2ncn(Cc3cc(F)cc(F)c3)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(3,5-difluorobenzyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (60 mg, 0.19 mmol) in N,N-dimethylformamide (5 mL) was added potassium carbonate (66 mg, 0.48 mmol) and 3,5-difluorobenzylbromide (47 mg, 0.23 mmol). The mixture was stirred at 25° C. for 12 h and then filtered. The filtrate was evaporated under reduced pressure and the residue was purified by RP-HPLC (55-85% methanol in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(3,5-difluorobenzyl)-1H-1,2,4-triazole-3-carboxamide (18.4 mg, 22%) as a white solid: $^1$H NMR (400 MHz, $CD_3OD$) δ 8.62 (s, 1H), 6.97-6.91 (m, 3H), 5.99 (s, 1H), 5.49 (s, 2H), 4.54-4.50 (m, 1H), 4.28-4.26 (m, 1H), 4.21-4.14 (m, 1H), 3.30 (s, 3H), 2.86-2.80 (m, 1H), 2.29-2.24 (m, 1H), 1.91-1.87 (m, 1H), 0.94-0.91 (m, 2H), 0.74-0.71 (m, 2H). LCMS $R_T$=0.80 min; m/z=442.1 $(M+H)^+$.

LCMS (5 to 95% acetonitrile in water+0.03% formic acid over 1.5 mins) retention time 0.80 min, ESI+ found [M+H]=442.1.

Example 304

WX Method OOOO

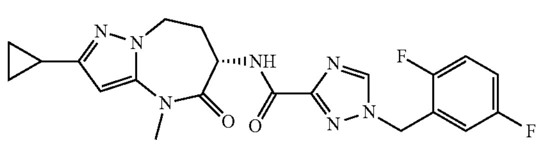 [SMILES: CN1C(=O)[C@@H](NC(=O)c2ncn(Cc3cc(F)ccc3F)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(2,5-difluorobenzyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (60 mg, 0.19 mmol) in N,N-dimethylformamide (5 mL) was added potassium carbonate (79 mg, 0.57 mmol) and 2,5-difluorobenzyl bromide (47 mg, 0.23 mmol). The mixture was stirred at 25° C. for 12 h and then filtered. The filtrate was evaporated under reduced pressure and the residue was purified by RP-HPLC (53-83% methanol in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(2,5-difluorobenzyl)-1H-1,2,4-triazole-3-carboxamide (15.5 mg, 18%) as a white solid: $^1$H NMR (400 MHz, DMSO-$d_6$) δ 8.81 (s, 1H), 8.54 (d, J=8.0 Hz, 1H), 7.31-7.25 (m, 3H), 6.06 (s, 1H), 5.54 (s, 2H), 4.30-4.26 (m, 2H), 4.25-4.21 (m, 1H), 3.19 (s, 3H), 2.54-2.52 (m, 1H), 2.50-2.33 (m, 1H), 1.85-1.83 (m, 1H), 0.86-0.84 (m, 2H), 0.68-0.64 (m, 2H). LCMS $R_T$=0.78 min; m/z=442.1 $(M+H)^+$.

LCMS (5 to 95% acetonitrile in water+0.03% formic acid over 1.5 mins) retention time 0.78 min, ESI+ found [M+H]=442.1.

Example 305

WX Method LLL

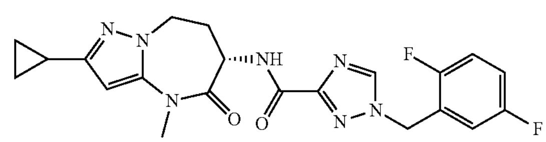 [SMILES: CN1C(=O)[C@@H](NC(=O)c2ncn(Cc3cc(F)ccc3F)n2)CCn2nc(C3CC3)cc21]

(S)-1-(2,5-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of N-[(6S)-2,4-dimethyl-5-oxo-7,8-dihydro-6H-pyrazolo[1,5-a][1,3]diazepin-6-yl]-1H-1,2,4-triazole-3-carboxamide (60 mg, 0.21 mmol) in N,N-dimethylformamide (5 mL) was added potassium carbonate (86 mg, 0.62 mmol) and 2,5-difluorobenzyl bromide (52 mg, 0.25 mmol). The mixture was stirred at 25° C. for 12 h. The reaction mixture was concentrated under reduced pressure, and the residue was purified by RP-HPLC (methanol 50-80%/0.05% ammonia hydroxide in water) to afford (S)-1-(2,5-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide (28.4 mg, 32%) as a white solid: $^1$H NMR (400 MHz, $CD_3OD$) δ 8.60 (s, 1H), 7.18-7.11 (m, 3H), 6.09 (s, 1H), 5.53 (s, 2H), 4.53-4.48 (m, 1H), 4.30-4.27 (m, 1H), 4.25-4.19 (m, 1H), 3.30 (s, 3H), 2.84-2.78 (m, 1H), 2.28-2.22 (m, 4H). LCMS $R_T$=0.751 min, m/z=416.1 $(M+H)^+$.

LCMS (5 to 95% acetonitrile in water+0.03% formic acid over 1.5 mins) retention time 0.751 min, ESI+ found [M+H]= 416.1.

Example 306

WX Method PPPP

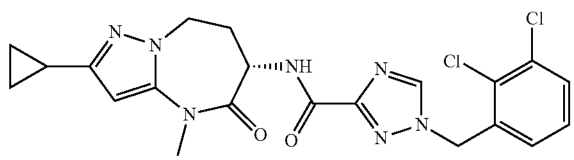 [SMILES: CN1C(=O)[C@@H](NC(=O)c2ncn(Cc3cccc(Cl)c3Cl)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(2,3-dichlorobenzyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (60 mg, 0.19 mmol) in N,N-dimethylformamide (5 mL) was added potassium carbonate (79 mg, 0.57 mmol) and 2,3-dichlorobenzyl bromide (55 mg, 0.23 mmol). The mixture was stirred at 25° C. for 12 h and then filtered. The filtrate was evaporated under reduced pressure and the residue was purified by RP-HPLC (55-85% methanol in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(2,3-dichlorobenzyl)-1H-1,2,4-triazole-3-carboxamide (13.6 mg, 15%) as a white solid: $^1$H NMR (400 MHz, DMSO-$d_6$) δ 8.84 (s, 1H), 8.55 (d, J=8.0 Hz, 1H), 7.66 (d, J=8.0 Hz, 1H), 7.42-7.38 (m, 1H), 7.21 (d, J=8.0 Hz, 1H), 6.06 (s, 1H), 5.64 (s, 2H), 4.31-4.23 (m, 2H), 4.21-4.07 (m, 1H), 3.19 (s, 3H), 2.58-2.50 (m, 1H), 2.44-2.32 (m, 1H), 1.85-1.83 (m, 1H), 0.86-0.84 (m, 2H), 0.68-0.64 (m, 2H). LCMS $R_T$=0.83 min; m/z=474.1 $(M+H)^+$.

LCMS (5 to 95% acetonitrile in water+0.03% formic acid over 1.5 mins) retention time 0.83 min, ESI+ found [M+H]=474.1.

Example 307

WX Method QQQQ

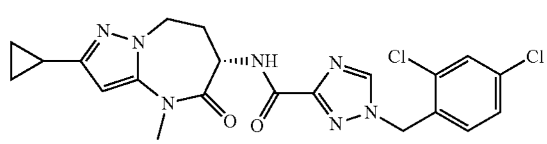 [SMILES: CN1C(=O)[C@@H](NC(=O)c2ncn(Cc3ccc(Cl)cc3Cl)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(2,4-dichlorobenzyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (60 mg, 0.19 mmol) in N,N-dimethylformamide (5 mL) was added potassium carbonate (79 mg, 0.57 mmol) and 2,4-dichlorobenzyl bromide (55 mg, 0.23 mmol). The mixture was stirred at 25° C. for 12 h and then filtered. The filtrate was evaporated under reduced pressure and the residue was purified by RP-HPLC (60-90% methanol in water and 0.05% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-(2,4-dichlorobenzyl)-1H-1,2,4-tri azole-3-carboxamide (16.7 mg, 18%) as a white solid: $^1$H NMR (400 MHz, $CD_3OD$) δ 8.59 (s, 1H), 7.52 (d, J=1.6 Hz, 1H), 7.41-7.30 (m, 2H), 5.99 (s, 1H), 5.57 (s, 2H), 4.53-4.48 (m, 1H), 4.28-4.26 (m, 1H), 4.20-4.17 (m, 1H), 3.29 (s, 3H), 2.85-2.78 (m, 1H), 2.27-2.22 (m, 1H), 1.91-1.86 (m, 1H), 0.93-0.91 (m, 2H), 0.77-0.71 (m, 2H). LCMS $R_T$=0.83 min; m/z=474.1 $(M+H)^+$.

LCMS (5 to 95% acetonitrile in water+0.03% formic acid over 1.5 mins) retention time 0.83 min, ESI+ found [M+H]=474.1.

Example 308

WX Method IIII

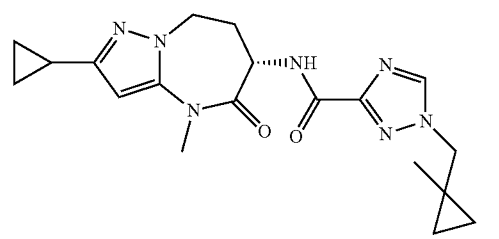 [SMILES: CN1C(=O)[C@@H](NC(=O)c2ncn(CC3(C)CC3)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide

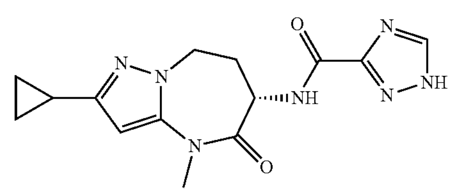

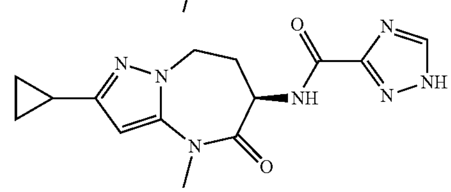

Step 1: (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide and (R)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide A mixture of 6-amino-2-cyclopropyl-4-methyl-7,8-dihydro-6H-pyrazolo[1,5-a][1,3]diazepin-5-one (3.6 g, 16.3 mmol), $N^1$-((ethylimino)methylene)-$N^3$,$N^3$-dimethyl propane-1,3-diamine hydrochloride (4.4 g, 24.5 mmol), 1H-benzo[d][1,2,3]triazol-1-ol (220 mg, 1.63 mmol) and 1H-1,2,4-triazole-3-carboxylic acid (2.2 g, 19.6 mmol) in N,N-dimethylformamide (60 mL) was stirred at 25° C. for 12 h. The solvent was evaporated under reduced pressure and the residue was purified by column chromatography (silica gel, 100-200 mesh, 0-3% methanol in dichloromethane) to afford N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (2.6 g, 46%) as white solid: LCMS $R_T$=1.068 min; m/z=316.1 $(M+H)^+$.

LCMS (0 to 30% acetonitrile in water+0.05% ammonium bicarbonate over 3.0 mins) retention time 1.068 min, ESI+ found [M+H]=316.1.

2.4 g of this material was separated by chiral SFC to afford:

(S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (peak 1, retention time: 3.657 min) (700 mg, 28%).

(R)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (peak 2, retention time: 4.150 min) (900 mg, 36%).

SFC condition: Column: Chiralcel OD-3 50×4.6 mm I.D., 3 um Mobile phase: A: $CO_2$ B: methanol (0.05% DEA) Gradient: hold 5% for 0.2 min, then from 5% to 40% of B in 1.4 min and hold 40% for 1.05 min, then 5% of B for 0.35 min Flow rate: 4 mL/min Column temp: 40° C.

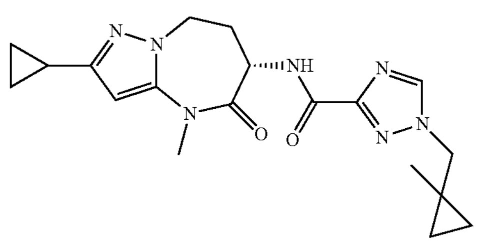 [SMILES: CN1C(=O)[C@@H](NC(=O)c2ncn(CC3(C)CC3)n2)CCn2nc(C3CC3)cc21]

Step 2: (S)—N-(2-cyclopropyl-4-methyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide To a solution of (S)—N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide (126 mg, 0.40 mmol) in N,N-dimethylformamide (3 mL) was added potassium carbonate (88 mg, 0.63 mmol) and 1-(iodomethyl)-1-methylcyclopropane (93 mg, 0.48 mmol). The mixture was stirred at 25° C. for 12 h and then filtered. The filtrate was evaporated under reduced pressure and the residue was purified by RP-HPLC (0 to 40% acetonitrile in water and 0.1% ammonia hydroxide) to afford (S)—N-(2-cyclopropyl-4-methyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide (30 mg, 20%) as a white solid: $^1H$ NMR (400 MHz, $CD_3OD$) δ 8.51 (s, 1H), 6.00 (s, 1H), 4.55-4.51 (m, 1H), 4.30-4.24 (m, 1H), 4.22-4.19 (m, 1H), 4.12 (s, 2H), 3.30 (s, 3H), 2.89-2.83 (m, 1H), 2.27-2.24 (m, 1H), 1.92-1.87 (m, 1H), 1.03 (s, 3H), 0.94-0.91 (m, 2H), 0.75-0.71 (m, 4H), 0.47-0.44 (m, 2H). LCMS $R_T$=0.96 min; m/z=384.3 $(M+H)^+$.

LCMS (10 to 80% acetonitrile in water+0.05% ammonium hydroxide over 2 mins) retention time 0.96 min, ESI+ found [M+H]=384.3.

Example 309

WX Method N

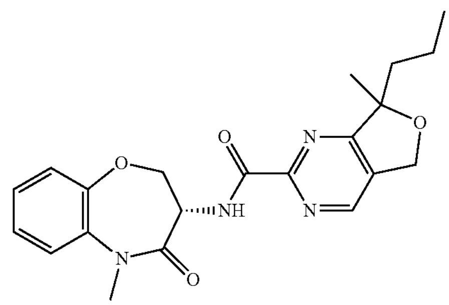 [SMILES: CCCC1(C)OCc2cnc(C(=O)N[C@H]3COc4ccccc4N(C)C3=O)nc21]

7-methyl-N—((S)-5-methyl-4-oxo-2,3,4,5-tetrahydrobenzo[b][1,4]oxazepin-3-yl)-7-propyl-5,7-dihydrofuro[3,4-d]pyrimidine-2-carboxamide

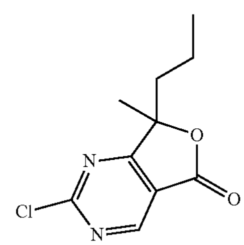

Step 1: 2-chloro-7-methyl-7-propylfuro[3,4-d]pyrimidin-5(7H)-one

To a stirred solution of 2,2,6,6-tetramethylpiperidine (13.4 g, 94.6 mmol) in tetrahydrofuran (80 mL) was added n-butyllithium (2.5 M, 50.5 mL, 126.2 mmol) dropwise at −78° C. The mixture was stirred at −78° C. for 40 min and then 2-chloropyrimidine-5-carboxylic acid (5.0 g, 31.5 mmol) in tetrahydrofuran (20 mL) was added. The resulting mixture was stirred at −78° C. for another 2 h, and then 2-pentanone (5.4 g, 63.1 mmol) was added dropwise. After addition, the reaction was warmed up to 25° C. and stirred for 16 h before quenched by addition of saturated aqueous ammonium chloride. The solution was extracted with ethyl acetate (3×50 mL). The combined organic layers were dried over sodium sulfate and concentrated under reduced pressure. The residue was purified by column chromatography (silica gel, 100-200 mesh, 0 to 10% ethyl acetate in petroleum ether) affording 2-chloro-7-methyl-7-propylfuro[3,4-d]pyrimidin-5(7H)-one (1.9 g, 26%) as yellow oil: $^1H$ NMR (400 MHz, $CDCl_3$) δ 9.06 (s, 1H), 2.06-2.04 (m, 1H), 2.00-1.96 (m, 1H), 1.68 (s, 3H), 1.39-1.36 (m, 1H), 0.99-0.95 (m, 1H), 0.90-0.86 (m, 3H).

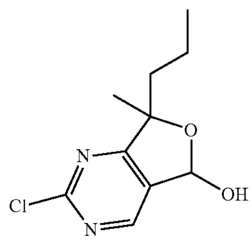

Step 2: 2-chloro-7-methyl-7-propyl-5,7-dihydrofuro[3,4-d]pyrimidin-5-ol

To a stirred solution of 2-chloro-7-methyl-7-propylfuro[3,4-d]pyrimidin-5(7H)-one (1.9 g, 8.3 mmol) in toluene (30 mL) was added diisobutylaluminumhydride (1.0 M, 20.8 mL, 20.8 mmol) dropwise at −78° C. After addition, the mixture was stirred at −78° C. for 1 h and then quenched by addition of saturated aqueous ammonium chloride (10 mL) and saturated aqueous sodium potassium tartrate (30 mL). Stirring was continued for 2 h at 25° C. and the mixture was then extracted with ethyl acetate (3×50 mL). The combined organic layers were dried over sodium sulfate and concentrated under reduced pressure. The residue was purified by column chromatography (silica gel, 100-200 mesh, 0 to 30% ethyl acetate in petroleum ether) affording 2-chloro-7-methyl-7-propyl-5,7-dihydrofuro[3,4-d]pyrimidin-5-ol (820 mg, 43%) as light yellow oil: LCMS $R_T$=0.640 min; m/z=228.7 $(M+H)^+$.

LCMS (5 to 95% acetonitrile in water+0.03% trifluoacetic acid over 1.5 mins) retention time 0.640 min, ESI+ found $[M+H]^+$=228.7.

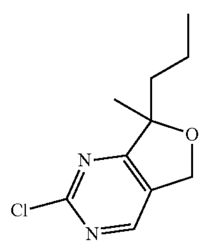

Step 3: 2-chloro-7-methyl-7-propyl-5,7-dihydrofuro[3,4-d]pyrimidine

To a stirred solution of 2-chloro-7-methyl-7-propyl-5,7-dihydrofuro[3,4-d]pyrimidin-5-ol (820 mg, 3.6 mmol) in dichloromethane (20 mL) was added trifluoroacetic acid (1.33 mL, 17.9 mmol) at 0° C. The mixture was stirred at 0° C. for 30 min, then triethylsilane (2.86 mL, 17.9 mmol) was added dropwise at 0° C. After addition, the mixture was warmed up to 25° C. and stirred for 15 h. The reaction was concentrated under reduced pressure and the residue was purified by column chromatography (silica gel, 100-200 mesh, 0 to 10% ethyl acetate in petroleum ether) affording 2-chloro-7-methyl-7-propyl-5,7-dihydrofuro[3,4-d]pyrimidine (700 mg, 92%) as light yellow oil.

LCMS (5 to 95% acetonitrile in water+0.03% trifluoacetic acid over 1.5 mins) retention time 0.707 min, ESI+ found $[M+H]^+$=212.8.

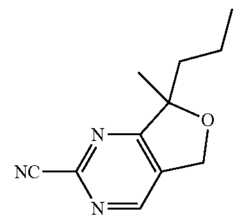

Step 4: 7-methyl-7-propyl-5,7-dihydrofuro[3,4-d]pyrimidine-2-carbonitrile

To a stirred solution of 2-chloro-7-methyl-7-propyl-5,7-dihydrofuro[3,4-d]pyrimidine (700 mg, 3.3 mmol) in dimethyl sulfoxide (5 mL) was added a solution of sodium cyanide (322 mg, 6.6 mmol) in water (5 mL) and 1,4-diazabicyclo[2.2.2]octane (74 mg, 0.66 mmol). The mixture was stirred at 25° C. for 15 h and then poured into water (10 mL). The resulting solution was extracted with ethyl acetate (3×25 mL). The combined organic layers were dried over sodium sulfate and concentrated under reduced pressure. The residue was purified by column chromatography (silica gel, 100-200 mesh, 0 to 10% ethyl acetate in petroleum ether) affording 7-methyl-7-propyl-5,7-dihydrofuro[3,4-d]pyrimidine-2-carbonitrile (200 mg, 30%) as light yellow oil: LCMS $R_T$=0.708 min; m/z=203.8 $(M+H)^+$.

LCMS (5 to 95% acetonitrile in water+0.03% trifluoacetic acid over 1.5 mins) retention time 0.708 min, ESI+ found $[M+H]^+$=203.8.

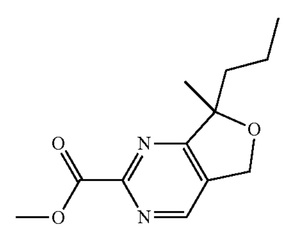 [SMILES: CCCC1(C)OCc2cnc(C(=O)OC)nc21]

Step 5: methyl 7-methyl-7-propyl-5,7-dihydrofuro[3,4-d]pyrimidine-2-carboxylate

To a stirred solution of 7-methyl-7-propyl-5,7-dihydrofuro[3,4-d]pyrimidine-2-carbonitrile (200 mg, 0.98 mmol) in methanol (4 mL) was added hydrochloric acid (4.0 M in MeOH, 2.5 mL, 10 mmol) at 0° C. The resulting mixture was warmed up to 25° C. and stirred for 15 h. The mixture was concentrated under reduced pressure affording crude methyl 7-methyl-7-propyl-5,7-dihydrofuro[3,4-d]pyrimidine-2-carboxylate (120 mg, 52%) as white solids: LCMS $R_T$=0.656 min; m/z=236.9 $(M+H)^+$.

LCMS (5 to 95% acetonitrile in water+0.03% trifluoacetic acid over 1.5 mins) retention time 0.656 min, ESI+ found $[M+H]^+$=236.9.

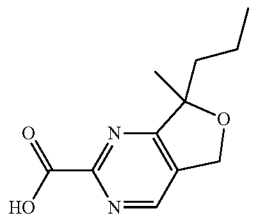 [SMILES: CCCC1(C)OCc2cnc(C(=O)O)nc21]

Step 6: 7-methyl-7-propyl-5,7-dihydrofuro[3,4-d] pyrimidine-2-carboxylic acid

A mixture of methyl 7-methyl-7-propyl-5,7-dihydrofuro [3,4-d]pyrimidine-2-carboxylate (120 mg, 0.51 mmol) and lithium hydroxide (121 mg, 5.1 mmol) in tetrahydrofuran (12 mL) and water (6 mL) was stirred for 20 h at 25° C. The organic solvent was removed under reduced pressure, and the aqueous layer was adjusted to pH=3 by addition of hydrochloric acid (1.0 M) and then extracted with ethyl acetate (3×45 mL). The combined organic layers were dried over sodium sulfate and concentrated under reduced pressure affording crude 7-methyl-7-propyl-5,7-dihydrofuro[3,4-d]pyrimidine-2-carboxylic acid (100 mg, 88%) as light yellow oil, used in the next step without further purification.

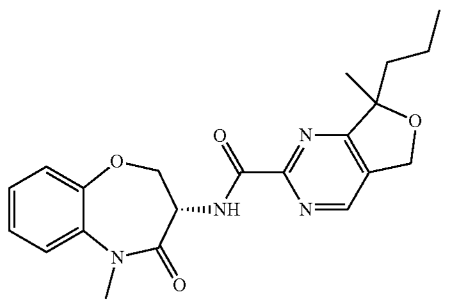 [SMILES: CCCC1(C)OCc2cnc(C(=O)N[C@H]3COc4ccccc4N(C)C3=O)nc21]

Step 7: 7-methyl-N—((S)-5-methyl-4-oxo-2,3,4,5-tetrahydrobenzo[b][1,4]oxazepin-3-yl)-7-propyl-5,7-dihydrofuro[3,4-d]pyrimidine-2-carboxamide A mixture of 7-methyl-7-propyl-5,7-dihydrofuro[3,4-d] pyrimidine-2-carboxylic acid (48 mg, 0.22 mmol), (3S)-3-amino-5-methyl-2,3-dihydro-1,5-benzoxazepin-4-one (35 mg, 0.18 mmol), $N^1$-((ethylimino)methylene)-$N^3$,$N^3$-dimethylpropane-1,3-diamine hydrochloride (42 mg, 0.22 mmol) and 1H-benzo[d][1,2,3]triazol-1-ol (29 mg, 0.22 mmol) in N,N-dimethylformamide (4 mL) was stirred at 25° C. for 1 h. The solvent was evaporated under reduced pressure and the residue purified it by RP-HPLC (acetonitrile 36-66%/0.05% ammonium hydroxide in water) affording 7-methyl-N—((S)-5-methyl-4-oxo-2,3,4,5-tetrahydrobenzo[b][1,4]oxazepin-3-yl)-7-propyl-5,7-dihydrofuro[3,4-d]pyrimidine-2-carboxamide (33.5 mg, 46%) as a white solid: $^1$H NMR (400 MHz, $CD_3OD$) δ 8.82 (s, 1H), 7.46-7.44 (m, 1H), 7.36-7.24 (m, 3H), 5.20-5.12 (m, 2H), 5.08-5.03 (m, 1H), 4.71-4.66 (m, 1H), 4.48-4.42 (m, 1H), 3.44 (s, 3H), 1.96-1.79 (m, 2H), 1.54-1.38 (m, 4H), 1.08-0.95 (m, 1H), 0.89-0.85 (m, 3H). LCMS $R_T$=1.056 min; m/z=397.2 $(M+H)^+$.

LCMS (10 to 80% acetonitrile in water+0.03% trifluoacetic acid over 2 mins) retention time 1.056 min, ESI+ found $[M+H]^+$=397.2.

Example 310

WX Method AA

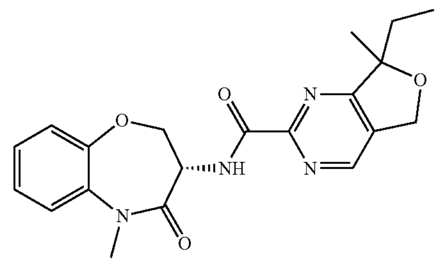 [SMILES: CCC1(C)OCc2cnc(C(=O)N[C@H]3COc4ccccc4N(C)C3=O)nc21]

7-ethyl-7-methyl-N—((S)-5-methyl-4-oxo-2,3,4,5-tetrahydrobenzo[b][1,4]oxazepin-3-yl)-5, 7-dihydrofuro[3,4-d]pyrimidine-2-carboxamide

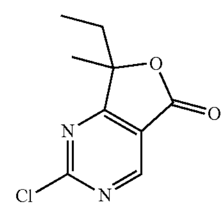

Step 1: 2-chloro-7-ethyl-7-methylfuro[3,4-d]pyrimidin-5(7H)-one

To a stirred solution of 2,2,6,6-tetramethylpiperidine (13.5 g, 95.6 mmol) in tetrahydrofuran (300 mL) was added n-butyllithium (2.5 M, 50 mL, 125.0 mmol) dropwise at −78° C. The mixture was stirred at −78° C. for 40 min and then 2-chloropyrimidine-5-carboxylic acid (5.0 g, 31.5 mmol) in tetrahydrofuran (20 mL) was added. The resulting mixture was stirred at −78° C. for another 2 h, and then butan-2-one (6.8 g, 94.6 mmol) was added dropwise. After addition, the reaction was warmed up to 25° C. and stirred for 16 h before quenched by addition of saturated aqueous ammonium chloride. The resulting mixture was extracted with ethyl acetate (3×80 mL). The combined organic layer was washed water (50 mL), brine (50 mL), dried over sodium sulfate and concentrated under reduced pressure. The residue was purified by column chromatography (silica gel, 100-200 mesh, 0 to 20% ethyl acetate in petroleum ether) to afford 2-chloro-7-ethyl-7-methylfuro[3,4-d]pyrimidin-5(7H)-one (1.0 g, 15%) as yellow oil: $^1$H NMR (400 MHz, $CDCl_3$) δ 9.07 (s, 1H), 2.15-2.03 (m, 2H), 1.69 (s, 3H), 0.81 (t, J=7.2 Hz, 3H).

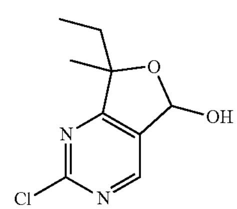

Step 2: 2-chloro-7-ethyl-7-methyl-5,7-dihydrofuro[3,4-d]pyrimidin-5-ol

To a solution of 2-chloro-7-ethyl-7-methylfuro[3,4-d]pyrimidin-5(7H)-one (1.0 g, 4.7 mmol) in toluene (30 mL) was added diisobutylaluminum hydride (1.0 M, 9.4 mL, 9.4 mmol) dropwise at −70° C. After addition, stirring at −70° C. was continued for 2 h and the reaction mixture was quenched by addition of saturated aqueous ammonium chloride. The resulting mixture was filtered and the filtrate was extracted with ethyl acetate (3×30 mL). The combined organic layers were washed water (20 mL), brine (20 mL), dried over sodium sulfate and concentrated under reduced pressure. The residue was purified by column chromatography (silica gel, 100-200 mesh, 0 to 30% ethyl acetate in petroleum ether) to afford 2-chloro-7-ethyl-7-methyl-5,7-dihydrofuro[3,4-d]pyrimidin-5-ol (0.70 g, 70%) as yellow oil used as is in the next step.

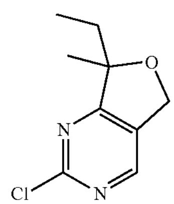

Step 3: 2-chloro-7-ethyl-7-methyl-5,7-dihydrofuro[3,4-d]pyrimidine

To a solution of 2-chloro-7-ethyl-7-methyl-5,7-dihydrofuro[3,4-d]pyrimidin-5-ol (700 mg, 3.3 mmol) in dichloromethane (20 mL) was added trifluoroacetic acid (1.86 g, 63.5 mmol) dropwise at 0° C. The reaction was stirred for 30 min at 0° C., and triethyl silane (1.9 g, 16.5 mmol) was added. After addition, the mixture was allowed to warm to 25° C. over 3 h and then quenched by addition of saturated sodium bicarbonate. The mixture was extracted with dichloromethane (3×30 mL). The combined organic layers were washed water (20 mL), brine (20 mL), dried over sodium sulfate and concentrated under reduced pressure. The residue was purified by column chromatography (silica gel, 100-200 mesh, 0 to 15% ethyl acetate in petroleum ether) to afford 2-chloro-7-ethyl-7-methyl-5,7-dihydrofuro[3,4-d]pyrimidine (450 mg, 69%) as yellow oil.

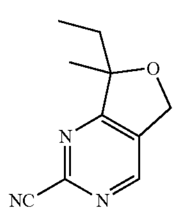

Step 4: 7-ethyl-7-methyl-5,7-dihydrofuro[3,4-d]pyrimidine-2-carbonitrile

To a stirred solution of 2-chloro-7-ethyl-7-methyl-5,7-dihydrofuro[3,4-d]pyrimidine (450 mg, 2.27 mmol) in dimethyl sulfoxide (5 mL) and water (2 mL) was added sodium cyanide (222 mg, 4.54 mmol) and 1,4-diazabicyclo[2.2.2]octane (74 mg, 0.66 mmol). The mixture was stirred at 25° C. for 16 h and then poured into water (10 mL). The resulting solution was extracted with ethyl acetate (3×20 mL). The combined organic layers were dried over sodium sulfate and concentrated under reduced pressure. The residue was purified by flash column chromatography (silica gel, 100-200 mesh, 0 to 20% ethyl acetate in petroleum ether) to afford 7-ethyl-7-methyl-5,7-dihydrofuro[3,4-d]pyrimidine-2-carbonitrile (140 mg, 33%) as yellow oil, used as is in the next step.

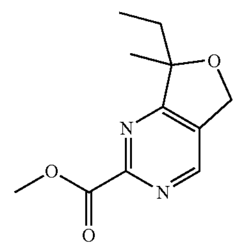 [SMILES: CCC1(C)OCc2cnc(C(=O)OC)nc21]

Step 5: methyl 7-ethyl-7-methyl-5,7-dihydrofuro[3,4-d]pyrimidine-2-carboxylate

To a solution of 7-ethyl-7-methyl-5,7-dihydrofuro[3,4-d]pyrimidine-2-carbonitrile (140 mg, 0.74 mmol) in methanol (4 mL) was added hydrochloric acid (4.0 M in MeOH, 2.0 mL, 8 mmol) at 0° C. The resulting mixture was warmed up to RT and stirred for 16 h. Then the mixture was concentrated under reduced pressure to afford crude methyl 7-ethyl-7-methyl-5,7-dihydrofuro[3,4-d]pyrimidine-2-carboxylate (120 mg, 73%) as a white solid, used in the next step without any further purification.

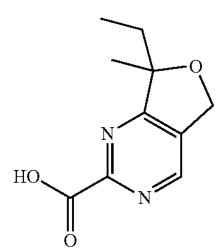

Step 6: 7-ethyl-7-methyl-5,7-dihydrofuro[3,4-d]pyrimidine-2-carboxylic acid

A mixture of methyl 7-ethyl-7-methyl-5,7-dihydrofuro[3,4-d]pyrimidine-2-carboxylate (120 mg, 0.54 mmol) and lithium hydroxide hydrate (113 mg, 2.70 mmol) in tetrahydrofuran (5 mL) and water (5 mL) was stirred at 25° C. for 2 h. After evaporation of the organic solvent under reduced pressure, the aqueous residue was adjusted to pH=5 by addition of hydrochloric acid (1.0 M). The mixture was extracted with ethyl acetate (3×20 mL). The combined organic layers were washed water (20 mL), brine (20 mL), dried over sodium sulfate and concentrated under reduced pressure to afford crude 1-methyl-1-(2,2,2-trifluoroethyl)-1,3-dihydrofuro [3,4-c]pyridine-6-carboxylic acid (90 mg, 80%) as a yellow solid, used in the next step without further purification.

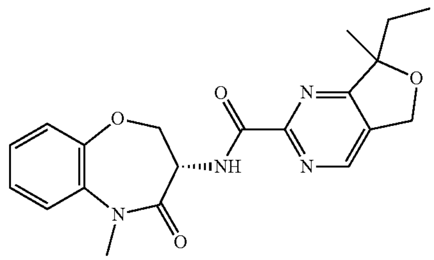 [SMILES: CCC1(C)OCc2cnc(C(=O)N[C@H]3COc4ccccc4N(C)C3=O)nc21]

Step 7: 7-ethyl-7-methyl-N—((S)-5-methyl-4-oxo-2,3,4,5-tetrahydrobenzo[b][1,4]oxazepin-3-yl)-5,7-dihydrofuro[3,4-d]pyrimidine-2-carboxamide A mixture of 7-ethyl-7-methyl-5,7-dihydrofuro[3,4-d]pyrimidine-2-carboxylic acid (20 mg, 0.10 mmol), (3S)-3-amino-5-methyl-2,3-dihydro-1,5-benzoxazepin-4-one (20 mg, 0.10 mmol), $N^1$-((ethylimino)methylene)-$N^3$,$N^3$-dimethylpropane-1,3-diamine hydrochloride (22 mg, 0.11 mmol) and 1H-benzo[d][1,2,3]triazol-1-ol (15 mg, 0.11 mmol) in N,N-dimethylformamide (5 mL) was stirred at 25° C. for 2 h. The reaction was concentrated under reduced pressure and the residue was purified by RP-HPLC (acetonitrile 31-61%/0.05% $NH_4OH$ in water) to afford 7-ethyl-7-methyl-N—((S)-5-methyl-4-oxo-2,3,4,5-tetrahydrobenzo[b][1,4]oxazepin-3-yl)-5,7-dihydrofuro[3,4-d]pyrimidine-2-carboxamide (24.20 mg, 65%) as a white solid: $^1H$ NMR (400 MHz, $CD_3OD$) δ 8.83 (s, 1H), 7.46-7.43 (m, 1H), 7.34-7.32 (m, 2H), 7.27-7.24 (m, 1H), 5.19-5.15 (m, 2H), 5.08-5.03 (m, 1H), 4.71-4.66 (m, 1H), 4.47-4.44 (m, 1H), 3.44 (s, 3H), 2.01-1.85 (m, 2H), 1.49 (s, 3H), 0.80 (t, J=7.2 Hz, 3H). LCMS $R_T$=0.793 min; m/z=383.1 $(M+H)^+$.

LCMS (5-95% acetonitrile in water+0.05% trifluoacetic acid over 1.5 mins) retention time 0.793 min, ESI+ found [M+H]=383.1.

Example 311

WX Method YYYYY

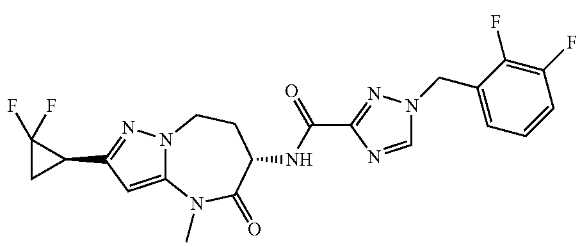 [SMILES: CN1C(=O)[C@@H](NC(=O)c2ncn(Cc3cccc(F)c3F)n2)CCn2nc([C@H]3CC3(F)F)cc21]

1-(2,3-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (S)-6-amino-2-((R)-2,2-difluorocyclopropyl)-4-methyl-7,8-dihydro-4H-pyrazolo[1,5-a][1,3]diazepin-5(6H)-one (60 mg, 0.23 mmol), (1-[(2,3-difluorophenyl)methyl]-1,2,4-triazole-3-carboxylic acid (84 mg, 0.35 mmol), 1H-benzo[d][1,2,3]triazol-1-ol (47 mg, 0.35 mmol) and $N^1$-((ethylimino)methylene)-$N^3$,$N^3$-dimethylpropane-1,3-diamine hydrochloride (63 mg, 0.35 mmol) in N,N-dimethylformamide (5 mL) was stirred at 25° C. for 16 h. The reaction was concentrated under reduced pressure and the residue was purified by RP-HPLC (acetonitrile 30-60%/0.05% ammonia hydroxide in water) to afford 1-(2,3-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide (11.9 mg, 11%) as a white solid: $^1H$ NMR (400 MHz, $CD_3OD$) δ 8.62 (s, 1H), 7.29-7.25 (m, 1H), 7.17-7.12 (m, 2H), 6.20 (s, 1H), 5.58 (s, 2H), 4.53-4.48 (m, 1H), 4.36-4.23 (m, 2H), 3.31 (s, 3H), 2.84-2.79 (m, 2H), 2.26-2.21 (m, 1H), 1.87-1.80 (m, 2H). LCMS $R_T$=0.81 min; m/z=478.2 $(M+H)^+$.

LCMS (5 to 95% acetonitrile in water+0.03% formic acid over 1.5 mins) retention time 0.81 min, ESI+ found [M+H]=478.2.

Example 312

WX Method SSSSS

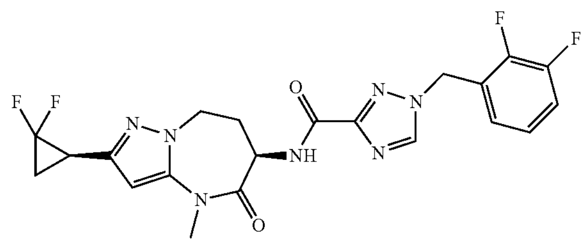 [SMILES: CN1C(=O)[C@H](NC(=O)c2ncn(Cc3cccc(F)c3F)n2)CCn2nc([C@H]3CC3(F)F)cc21]

1-(2,3-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (R)-6-amino-2-((R)-2,2-difluorocyclopropyl)-4-methyl-7,8-dihydro-4H-pyrazolo[1,5-a][1,3]diazepin-5(6H)-one (30 mg, 0.12 mmol), 1-[(2,3-difluorophenyl)methyl]-1,2,4-triazole-3-carboxylic acid (42 mg, 0.18 mmol), 1H-benzo[d][1,2,3]triazol-1-ol (24 mg, 0.18 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (25-55% acetonitrile in water and 0.05% ammonia hydroxide) to afford 1-(2,3-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide (38.8 mg, 69%) as white solid: $^1H$ NMR (400 MHz, $CD_3OD$) δ 8.63 (s, 1H), 7.32-7.27 (m, 1H), 7.19-7.16 (m, 2H), 6.21 (s, 1H), 5.60 (s, 2H), 4.55-4.50 (m, 1H), 4.36-4.34 (m, 1H), 4.27-4.24 (m, 1H), 3.33 (s, 3H), 2.88-2.80 (m, 2H), 2.28-2.26 (m, 1H), 1.90-1.78 (m, 2H). LCMS $R_T$=0.80 min; m/z=478.1 $(M+H)^+$.

LCMS (5 to 95% acetonitrile in water+0.03% trifluoacetic acid over 1.5 mins) retention time 0.80 min, ESI+ found [M+H]=478.1.

Example 313

WX Method ZZZZZ

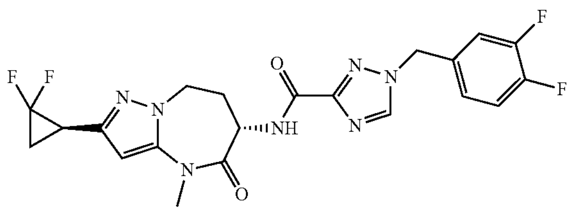 [SMILES: CN1C(=O)[C@@H](NC(=O)c2ncn(Cc3ccc(F)c(F)c3)n2)CCn2nc([C@H]3CC3(F)F)cc21]

1-(3,4-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (S)-6-amino-2-((R)-2,2-difluorocyclopropyl)-4-methyl-7,8-dihydro-4H-pyrazolo[1,5-a][1,3]diazepin-5(6H)-one (60 mg, 0.23 mmol), 1-[(3,4-difluorophenyl)methyl]-1,2,4-triazole-3-carboxylic acid (84 mg, 0.35 mmol), 1H-benzo[d][1,2,3]triazol-1-ol (47 mg, 0.35 mmol) and $N^1$-((ethylimino)methylene)-$N^3$,$N^3$-dimethylpropane-1,3-diamine hydrochloride (63 mg, 0.35 mmol) in N,N-dimethylformamide (5 mL) was stirred at 25° C. for 16 h. The reaction was concentrated under reduced pressure and the residue was purified by RP-HPLC (acetonitrile 32-62%/0.05% ammonia hydroxide in water) to afford 1-(3,4-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide (18 mg, 16%) as a white solid: $^1$H NMR (400 MHz, $CD_3OD$) δ 8.59 (s, 1H), 7.34-7.26 (m, 2H), 7.25-7.18 (m, 1H), 6.20 (s, 1H), 5.45 (s, 2H), 4.55-4.50 (m, 1H), 4.36-4.34 (m, 1H), 4.26-4.23 (m, 1H), 3.30 (s, 3H), 2.85-2.80 (m, 2H), 2.27-2.26 (m, 1H), 1.89-1.77 (m, 2H). LCMS $R_T$=0.81 min; m/z=478.1 $(M+H)^+$.

LCMS (5 to 95% acetonitrile in water+0.03% formic acid over 1.5 mins) retention time 0.81 min, ESI+ found [M+H]=478.1.

Example 314

WX Method TTTTTT

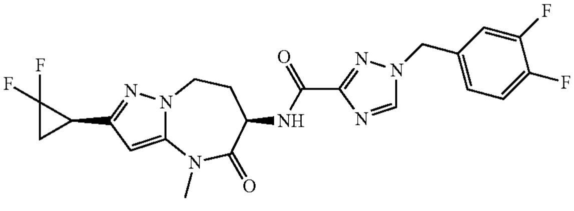 [SMILES: CN1C(=O)[C@H](NC(=O)c2ncn(Cc3ccc(F)c(F)c3)n2)CCn2nc([C@H]3CC3(F)F)cc21]

1-(3,4-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (R)-6-amino-2-((R)-2,2-difluorocyclopropyl)-4-methyl-7,8-dihydro-4H-pyrazolo[1,5-a][1,3]diazepin-5(6H)-one (30 mg, 0.12 mmol), 1-[(3,4-difluorophenyl)methyl]-1,2,4-triazole-3-carboxylic acid (42 mg, 0.18 mmol), 1H-benzo[d][1,2,3]triazol-1-ol (24 mg, 0.18 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (31-61% acetonitrile in water and 0.05% ammonia hydroxide) to afford 1-(3,4-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide (37.1 mg, 66%) as white solid: $^1$H NMR (400 MHz, $CD_3OD$) δ 8.60 (s, 1H), 7.35-7.26 (m, 2H), 7.20-7.19 (m, 1H), 6.21 (s, 1H), 5.46 (s, 2H), 4.55-4.50 (m, 1H), 4.37-4.35 (m, 1H), 4.27-4.24 (m, 1H), 3.33 (s, 3H), 2.88-2.80 (m, 2H), 2.28-2.27 (m, 1H), 1.90-1.78 (m, 2H). LCMS $R_T$=0.81 min; m/z=478.1 $(M+H)^+$.

LCMS (5 to 95% acetonitrile in water+0.03% trifluoacetic acid over 1.5 mins) retention time 0.81 min, ESI+ found [M+H]=478.1.

Example 315

WX Method AAAAAA

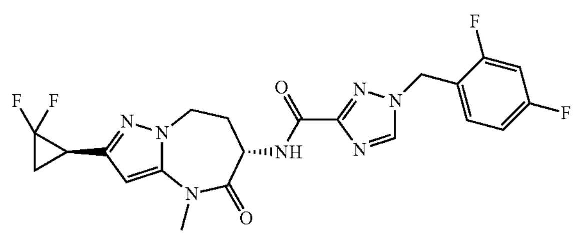 [SMILES: CN1C(=O)[C@@H](NC(=O)c2ncn(Cc3ccc(F)cc3F)n2)CCn2nc([C@H]3CC3(F)F)cc21]

1-(2,4-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (S)-6-amino-2-((R)-2,2-difluorocyclopropyl)-4-methyl-7,8-dihydro-4H-pyrazolo[1,5-a][1,3]diazepin-5(6H)-one (60 mg, 0.23 mmol), 1-[(2,4-difluorophenyl)methyl]-1,2,4-triazole-3-carboxylic acid (84 mg, 0.35 mmol), 1H-benzo[d][1,2,3]triazol-1-ol (47 mg, 0.35 mmol) and $N^1$-((ethylimino)methylene)-$N^3$,$N^3$-dimethylpropane-1,3-diamine hydrochloride (63 mg, 0.35 mmol) in N,N-dimethylformamide (5 mL) was stirred at 25° C. for 16 h. The reaction was concentrated under reduced pressure and the residue was purified by RP-HPLC (acetonitrile 30-60%/0.05% ammonia hydroxide in water) to afford 1-(2,4-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide (28.8 mg, 25%) as a white solid: $^1$H NMR (400 MHz, $CD_3OD$) δ 8.58 (s, 1H), 7.44 (s, 1H), 7.01-7.00 (m, 2H), 6.20 (s, 1H), 5.51 (s, 2H), 4.52-4.50 (m, 1H), 4.35-4.22 (m, 2H), 3.31 (s, 3H), 2.82-2.80 (m, 2H), 2.26-2.23 (m, 1H), 1.87-1.80 (m, 2H). LCMS $R_T$=0.80 min; m/z=478.1 $(M+H)^+$.

LCMS (5 to 95% acetonitrile in water+0.03% formic acid over 1.5 mins) retention time 0.80 min, ESI+ found [M+H]=478.1.

Example 316

WX Method UUUUU

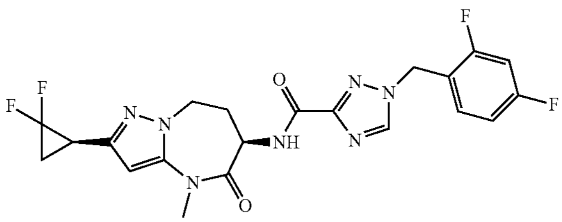 [SMILES: CN1C(=O)[C@H](NC(=O)c2ncn(Cc3ccc(F)cc3F)n2)CCn2nc([C@H]3CC3(F)F)cc21]

1-(2,4-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (R)-6-amino-2-((R)-2,2-difluorocyclopropyl)-4-methyl-7,8-dihydro-4H-pyrazolo[1,5-a][1,3]diazepin-5(6H)-one (30 mg, 0.12 mmol), 1-[(2,4-difluorophenyl)methyl]-1,2,4-triazole-3-carboxylic acid (42 mg, 0.18 mmol), 1H-benzo[d][1,2,3]triazol-1-ol (24 mg, 0.18 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (25-55% acetonitrile in water and 0.05% ammonia hydroxide) to afford 1-(2,4-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide (24.2 mg, 43%) as white solid: $^1$H NMR (400 MHz, $CD_3OD$) δ 8.59 (s, 1H), 7.49-7.43 (m, 1H), 7.06-6.98 (m, 2H), 6.21 (s, 1H), 5.53 (s, 2H), 4.54-4.49 (m, 1H), 4.38-4.34 (m, 1H), 4.27-4.24 (m, 1H), 3.33 (s, 3H), 2.87-2.77 (m, 2H), 2.27-2.26 (m, 1H), 1.90-1.78 (m, 2H). LCMS $R_T$=0.80 min; m/z=478.2 $(M+H)^+$.

LCMS (5 to 95% acetonitrile in water+0.03% trifluoacetic acid over 1.5 mins) retention time 0.80 min, ESI+ found [M+H]=478.2.

Example 317

WX Method BBBBBB

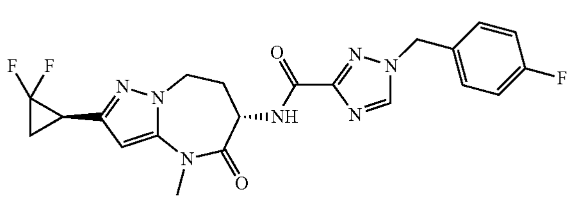 [SMILES: CN1C(=O)[C@@H](NC(=O)c2ncn(Cc3ccc(F)cc3)n2)CCn2nc([C@H]3CC3(F)F)cc21]

N—((S)-2-((R)-2,2-difluorocyclopropyl)-4-methyl-5-oxo-5,6,7,8-tetrahydro-4-pyrazolo[1,5-a][1,3]diazepin-6-yl)-1-(4-fluorobenzyl)-1H-1,2,4-triazole-3-carboxamide A mixture of (S)-6-amino-2-((R)-2,2-difluorocyclopropyl)-4-methyl-7,8-dihydro-4H-pyrazolo[1,5-a][1,3]diazepin-5(6H)-one (60 mg, 0.23 mmol), 1-[(4-fluorophenyl)methyl]-1,2,4-triazole-3-carboxylic acid (78 mg, 0.35 mmol), 1H-benzo[d][1,2,3]triazol-1-ol (47 mg, 0.35 mmol) and $N^1$-((ethylimino)methylene)-$N^3$,$N^3$-dimethylpropane-1,3-diamine hydrochloride (63 mg, 0.35 mmol) in N,N-dimethylformamide (5 mL) was stirred at 25° C. for 16 h. The reaction was concentrated under reduced pressure and the residue was purified by RP-HPLC (acetonitrile 30-60%/0.05% ammonia hydroxide in water) to afford N—((S)-2-((R)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide(18.3 mg, 17%) as a white solid: $^1$H NMR (400 MHz, $CD_3OD$) δ 8.56 (s, 1H), 7.41-7.37 (m, 2H), 7.11-7.07 (m, 2H), 6.20 (s, 1H), 5.45 (s, 2H), 4.54-4.49 (m, 1H), 4.35-4.33 (m, 1H), 4.26-4.23 (m, 1H), 3.30 (s, 3H), 2.84-2.78 (m, 2H), 2.27-2.25 (m, 1H), 1.89-1.78 (m, 2H). LCMS $R_T$=0.80 min; m/z=460.1 $(M+H)^+$.

LCMS (5 to 95% acetonitrile in water+0.03% formic acid over 1.5 mins) retention time 0.80 min, ESI+ found [M+H]=460.1.

Example 318

WX Method VVVVV

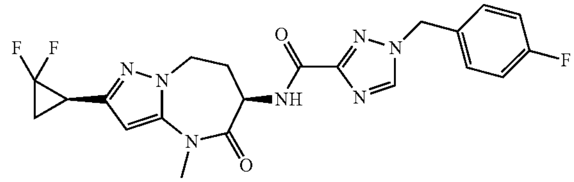 [SMILES: CN1C(=O)[C@H](NC(=O)c2ncn(Cc3ccc(F)cc3)n2)CCn2nc([C@H]3CC3(F)F)cc21]

N—((R)-2-((R)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide A mixture of (R)-6-amino-2-((R)-2,2-difluorocyclopropyl)-4-methyl-7,8-dihydro-4H-pyrazolo[1,5-a][1,3]diazepin-5(6H)-one (30 mg, 0.12 mmol), 1-[(4-fluorophenyl)methyl]-1,2,4-triazole-3-carboxylic acid (39 mg, 0.18 mmol), 1H-benzo[d][1,2,3]triazol-1-ol (24 mg, 0.18 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (31-61% acetonitrile in water and 0.05% ammonia hydroxide) to afford N—((R)-2-((R)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide (17.1 mg, 31.5% yield) as white solid: $^1$H NMR (400 MHz, $CD_3OD$) δ 8.58 (s, 1H), 7.42-7.39 (m, 2H), 7.11 (t, J=8.4 Hz, 2H), 6.21 (s, 1H), 5.46 (s, 2H), 4.55-4.51 (m, 1H), 4.37-4.35 (m, 1H), 4.27-4.24 (m, 1H), 3.33 (s, 3H), 2.88-2.80 (m, 2H), 2.28-2.27 (m, 1H), 1.97-1.80 (m, 2H). LCMS $R_T$=0.79 min; m/z=460.1 $(M+H)^+$.

LCMS (5 to 95% acetonitrile in water+0.03% trifluoacetic acid over 1.5 mins) retention time 0.79 min, ESI+ found [M+H]=460.1.

Example 319

WX Method CCCCCC

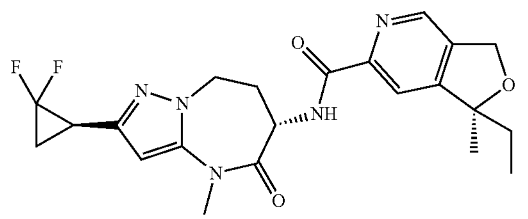 [SMILES: CC[C@]1(C)OCc2cnc(C(=O)N[C@H]3CCn4nc([C@H]5CC5(F)F)cc4N(C)C3=O)cc21]

(S)—N—((S)-2-((R)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide A mixture of (S)-6-amino-2-((R)-2,2-difluorocyclopropyl)-4-methyl-7,8-dihydro-4H-pyrazolo[1,5-a][1,3]diazepin-5(6H)-one (60 mg, 0.23 mmol), (1R)-1-ethyl-1-methyl-3H-furo[3,4-c]pyridine-6-carb oxylic acid (58 mg, 0.28 mmol), 1H-benzo[d][1,2,3]triazol-1-ol (47 mg, 0.35 mmol) and $N^1$-((ethylimino)methylene)-$N^3$,$N^3$-dimethylpropane-1,3-diamine hydrochloride (63 mg, 0.35 mmol) in N,N-dimethylformamide (5 mL) was stirred at 25° C. for 16 h. The reaction was concentrated under reduced pressure and the residue was purified by RP-HPLC (acetonitrile 35-65%/0.05% ammonia hydroxide in water) to afford (S)—N—((S)-2-((R)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide (25 mg, 24%) as a white solid: $^1$H NMR (400 MHz, $CD_3OD$) δ 8.55 (s, 1H), 7.86 (s, 1H), 6.21 (s, 1H), 5.19-5.15 (m, 2H), 4.55-4.39 (m, 1H), 4.38-4.35 (m, 1H), 4.30-4.26 (m, 1H), 3.30 (s, 3H), 2.92-2.81 (m, 2H), 2.26-2.25 (m, 1H), 1.94-1.78 (m, 4H), 1.45 (s, 3H), 0.78-0.74 (m, 3H). LCMS $R_T$=0.83 min; m/z=446.1 $(M+H)^+$.

LCMS (5 to 95% acetonitrile in water+0.03% formic acid over 1.5 mins) retention time 0.83 min, ESI+ found [M+H]=446.1.

Example 320

WX Method PPPPP

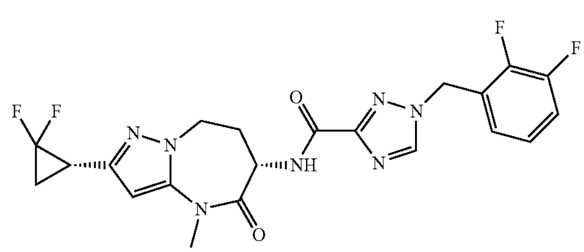 [SMILES: CN1C(=O)[C@@H](NC(=O)c2ncn(Cc3cccc(F)c3F)n2)CCn2nc([C@@H]3CC3(F)F)cc21]

1-(2,3-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (S)-6-amino-2-((S)-2,2-difluorocyclopropyl)-4-methyl-7,8-dihydro-4H-pyrazolo[1,5-a][1,3]diazepin-5(6H)-one (30 mg, 0.12 mmol), 1-(2,3-difluorobenzyl)-1H-1,2,4-triazole-3-carboxylic acid (42 mg, 0.18 mmol), 1H-benzo[d][1,2,3]triazol-1-ol (24 mg, 0.18 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (acetonitrile 30-60%/0.05% ammonia hydroxide in water) to afford 1-(2,3-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide as a white solid (13.7 mg, 24%): $^1$H NMR (400 MHz, $CD_3OD$) δ 8.62 (s, 1H), 7.33-7.24 (m, 1H), 7.22-7.13 (m, 2H), 6.19 (s, 1H), 5.60 (s, 2H), 4.54-4.49 (m, 1H), 4.42-4.33 (m, 1H), 4.30-4.19 (m, 1H), 3.33 (s, 3H), 2.90-2.75 (m, 2H), 2.28-2.24 (m, 1H), 1.94-1.85 (m, 1H), 1.82-1.74 (m, 1H). LCMS $R_T$=1.00 min; m/z=478.2 $(M+H)^+$.

LCMS (10 to 80% acetonitrile in water+0.03% trifluoacetic acid over 2.0 mins) retention time 1.00 min, ESI+ found [M+H]=478.2.

Example 321

WX Method OOOOO

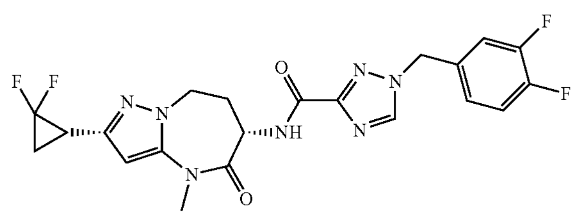

1-(3,4-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (S)-6-amino-2-((S)-2,2-difluorocyclopropyl)-4-methyl-7,8-dihydro-4H-pyrazolo[1,5-a][1,3]diazepin-5(6H)-one (30 mg, 0.12 mmol), 1-(3,4-difluorobenzyl)-1H-1,2,4-triazole-3-carboxylic acid (42 mg, 0.18 mmol), 1H-benzo[d][1,2,3]triazol-1-ol (39 mg, 0.29 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (acetonitrile 30-60%/0.05% ammonia hydroxide in water) to afford 1-(3,4-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide (16.1 mg, 28%) as a white solid: $^1$H NMR (400 MHz, $CD_3OD$) δ 8.60 (s, 1H), 7.36-7.23 (m, 2H), 7.21-7.19 (m, 1H), 6.20 (s, 1H), 5.46 (s, 2H), 4.54-4.49 (m, 1H), 4.42-4.34 (m, 1H), 4.30-4.20 (m, 1H), 3.33 (s, 3H), 2.91-2.75 (m, 2H), 2.31-2.22 (m, 1H), 1.92-1.88 (m, 1H), 1.83-1.74 (m, 1H). LCMS $R_T$=1.01 min; m/z=478.1 $(M+H)^+$.

LCMS (10 to 80% acetonitrile in water+0.03% trifluoacetic acid over 2.0 mins) retention time 1.01 min, ESI+ found [M+H]=478.2.

Example 322

WX Method QQQQQ

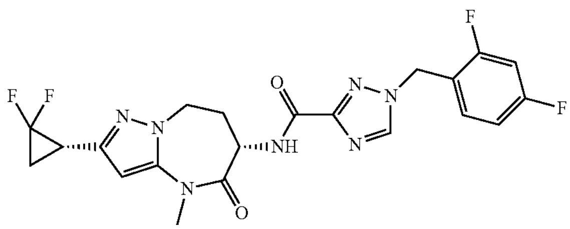 [SMILES: CN1C(=O)[C@@H](NC(=O)c2ncn(Cc3ccc(F)cc3F)n2)CCn2nc([C@@H]3CC3(F)F)cc21]

1-(2,4-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide A mixture of (S)-6-amino-2-((S)-2,2-difluorocyclopropyl)-4-methyl-7,8-dihydro-4H-pyrazolo[1,5-a][1,3]diazepin-5(6H)-one (30 mg, 0.12 mmol), 1-(2,4-difluorobenzyl)-1H-1,2,4-triazole-3-carboxylic acid (42 mg, 0.18 mmol), 1H-benzo[d][1,2,3]triazol-1-ol (24 mg, 0.18 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (acetonitrile 30-60%/0.05% ammonia hydroxide in water) to afford 1-(2,4-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide as a white solid (28.4 mg, 50%): $^1$H NMR (400 MHz, $CD_3OD$) δ 8.58 (s, 1H), 7.50-7.42 (m, 1H), 7.06-6.96 (m, 2H), 6.19 (s, 1H), 5.52 (s, 2H), 4.53-4.48 (m, 1H), 4.41-4.33 (m, 1H), 4.28-4.17 (m, 1H), 3.33 (s, 3H), 2.90-2.76 (m, 2H), 2.30-2.19 (m, 1H), 1.95-1.84 (m, 1H), 1.83-1.73 (m, 1H). LCMS $R_T$=1.00 min; m/z=478.2 $(M+H)^+$.

LCMS (10 to 80% acetonitrile in water+0.03% trifluoacetic acid over 2.0 mins) retention time 1.00 min, ESI+ found [M+H]=478.2.

Example 323

WX Method RRRRR

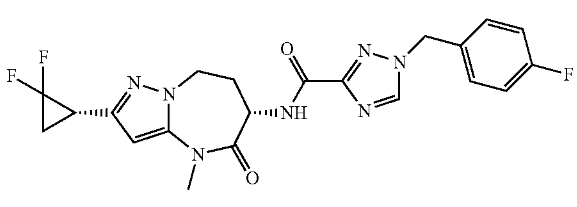 [SMILES: CN1C(=O)[C@@H](NC(=O)c2ncn(Cc3ccc(F)cc3)n2)CCn2nc([C@@H]3CC3(F)F)cc21]

N—((S)-2-((S)-2,2-difluorocyclopropyl)-4-methyl-5-oxo-5,6,7,8-tetrahydro-4H-pyrazolo[1, 5-a][1,3]diazepin-6-yl)-1-(4-fluorobenzyl)-1H-1,2,4-triazole-3-carboxamide A mixture of (S)-6-amino-2-((S)-2,2-difluorocyclopropyl)-4-methyl-7,8-dihydro-4H-pyrazolo[1,5-a][1,3]diazepin-5(6H)-one (30 mg, 0.12 mmol), 1-(4-fluorobenzyl)-1H-1,2,4-triazole-3-carboxylic acid (39 mg, 0.18 mmol), 1H-benzo[d][1,2,3]triazol-1-ol (24 mg, 0.18 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (acetonitrile 30-60%/0.05% ammonia hydroxide in water) to afford N—((S)-2-((S)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide as a white solid (23.4 mg, 43%): $^1$H NMR (400 MHz, $CD_3OD$) δ 8.57 (s, 1H), 7.40 (dd, J=6.0, 8.4 Hz, 2H), 7.10 (t, J=8.8 Hz, 2H), 6.19 (s, 1H), 5.46 (s, 2H), 4.53-4.45 (m, 1H), 4.41-4.34 (m, 1H), 4.30-4.20 (m, 1H), 3.33 (s, 3H), 2.90-2.75 (m, 2H), 2.29-2.14 (m, 1H), 1.95-1.85 (m, 1H), 1.83-1.73 (m, 1H). LCMS $R_T$=0.99 min; m/z=460.2 $(M+H)^+$.

LCMS (10 to 80% acetonitrile in water+0.03% trifluoacetic acid over 2.0 mins) retention time 0.99 min, ESI+ found [M+H]=460.2.

Example 324

WX Method WWWWW

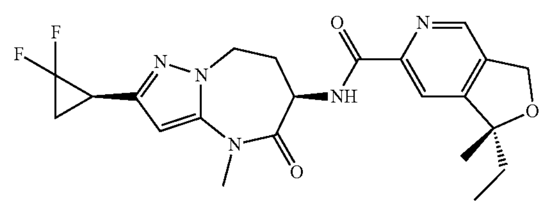 [SMILES: CC[C@@]1(C)OCc2cnc(C(=O)N[C@@H]3CCn4nc([C@H]5CC5(F)F)cc4N(C)C3=O)cc21]

(R)—N—((R)-2-((R)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide A mixture of (R)-6-amino-2-((R)-2,2-difluorocyclopropyl)-4-methyl-7,8-dihydro-4H-pyrazolo[1,5-a][1,3]diazepin-5(6H)-one (30 mg, 0.12 mmol), (1R)-1-ethyl-1-methyl-3H-furo[3,4-c]pyridine-6-carboxylic acid (24 mg, 0.12 mmol), 1H-benzo[d][1,2,3]triazol-1-ol (24 mg, 0.18 mmol) and $N^1$-((ethylimino)methylene)-$N^3$,$N^3$-dimethylpropane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (42-62% acetonitrile in water and 0.05% hydrochloric acid) to afford (R)—N—((R)-2-((R)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide (20 mg, 38%) as white solid: $^1$H NMR (400 MHz, $CD_3OD$) δ 8.57 (s, 1H), 7.87 (s, 1H), 6.23 (s, 1H), 5.21-5.16 (m, 2H), 4.59-4.55 (m, 1H), 4.39-4.37 (m, 2H), 3.36 (s, 3H), 2.94-2.79 (m, 2H), 2.28-2.26 (m, 1H), 1.92-1.78 (m, 4H), 1.47 (s, 3H), 0.78 (t, J=6.8 Hz, 3H). LCMS $R_T$=0.84 min; m/z=446.2 $(M+H)^+$.

LCMS (5 to 95% acetonitrile in water+0.03% trifluoacetic acid over 1.5 mins) retention time 0.84 min, ESI+ found [M+H]=446.2.

Example 325

WX Method XXXXX

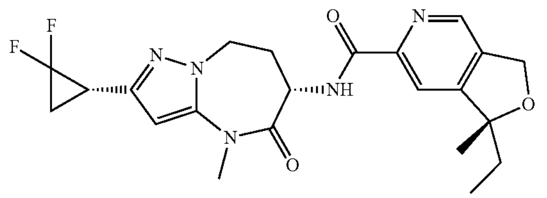 [SMILES: CC[C@@]1(C)OCc2cnc(C(=O)N[C@H]3CCn4nc([C@@H]5CC5(F)F)cc4N(C)C3=O)cc21]

(R)—N—((S)-2-((S)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide A mixture of (S)-6-amino-2-((S)-2,2-difluorocyclopropyl)-4-methyl-7,8-dihydro-4H-pyrazolo[1,5-a][1,3]diazepin-5(6H)-one (30 mg, 0.12 mmol), (1R)-1-ethyl-1-methyl-3H-furo[3,4-c]pyridine-6-carboxylic acid (29 mg, 0.14 mmol), 1H-benzo[d][1,2,3]triazol-1-ol (24 mg, 0.18 mmol) and $N^1$-((ethylimino)methylene)-$N^3$,$N^3$-dimethyl-propane-1,3-diamine hydrochloride (34 mg, 0.18 mmol) in N,N-dimethylformamide (5 mL) was stirred at 25° C. for 16 h. The reaction was concentrated under reduced pressure and the residue was purified by RP-HPLC (acetonitrile 17-47/0.05% ammonium chloride in water) to give (R)—N—((S)-2-((S)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide (20 mg, 38%) as white solid: $^1$H NMR (400 MHz, $CD_3OD$) δ 8.56 (s, 1H), 7.87 (s, 1H), 6.21 (s, 1H), 5.20-5.16 (m, 2H), 4.58-4.53 (m, 1H), 4.38-4.27 (m, 2H), 3.35 (s, 3H), 2.98-2.78 (m, 2H), 2.27-2.17 (m, 1H), 1.92-1.78 (m, 4H), 1.46 (s, 3H), 0.76 (t, J=3.6 Hz, 3H). LCMS $R_T$=1.08 min; m/z=446.3 $(M+H)^+$.

LCMS (10 to 80% acetonitrile in water+0.03% trifluoacetic acid over 2.0 mins) retention time 1.08 min, ESI+ found [M+H]=446.3.

Example 326

WX Method OO

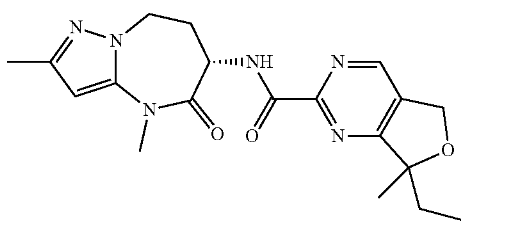 [SMILES: CCC1(C)OCc2cnc(C(=O)N[C@H]3CCn4nc(C)cc4N(C)C3=O)nc21]

N—((S)-2,4-dimethyl-5-oxo-5,6,7,8-tetrahydro-4H-pyrazolo[1,5-a][1,3]diazepin-6-yl)-7-ethyl-7-methyl-5,7-dihydrofuro[3,4-d]pyrimidine-2-carboxamide A mixture of 7-ethyl-7-methyl-5,7-dihydrofuro[3,4-d]pyrimidine-2-carboxylic acid (20 mg, 0.10 mmol), (S)-6-amino-2,4-dimethyl-7,8-dihydro-4H-pyrazolo[1,5-a][1,3]diazepin-5(6H)-one (20 mg, 0.10 mmol), $N^1$-((ethylimino)methylene)-$N^3$,$N^3$-dimethyl propane-1,3-diamine hydrochloride (22 mg, 0.11 mmol) and 1H-benzo[d][1,2,3]triazol-1-ol (16 mg, 0.11 mmol) in N,N-dimethylformamide (5 mL) was stirred at 25° C. for 2 h. The reaction was concentrated under reduced pressure and the residue was purified by RP-HPLC (acetonitrile 31-61%/0.05% $NH_4OH$ in water) to afford N—((S)-2,4-dimethyl-5-oxo-5,6,7,8-tetrahydro-4H-pyrazolo[1,5-a][1,3]diazepin-6-yl)-7-ethyl-7-methyl-5,7-dihydrofuro[3,4-d]pyrimidine-2-carboxamide (29.0 mg, 77%) as white solid: $^1$H NMR (400 MHz, $CD_3OD$) δ 8.82 (s, 1H), 6.13 (s, 1H), 5.18-5.12 (m, 2H), 4.62-4.57 (m, 1H), 4.34-4.25 (m, 2H), 3.35 (s, 3H), 2.97-2.92 (m, 1H), 2.32-2.27 (m, 4H), 1.99-1.85 (m, 2H), 1.49 (s, 3H), 0.80 (t, J=7.6 Hz, 3H). LCMS $R_T$=0.729 min; m/z=385.1 $(M+H)^+$.

LCMS (5-95% acetonitrile in water+0.05% trifluoacetic acid over 1.5 mins) retention time 0.729 min, ESI+ found [M+H]=385.1.

Example 327

WX Method O

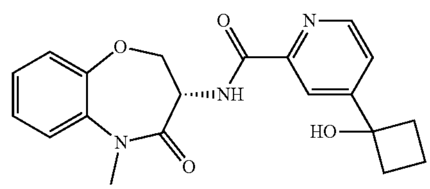 [SMILES: CN1C(=O)[C@@H](NC(=O)c2cc(C3(O)CCC3)ccn2)COc2ccccc21]

(S)-4-(1-hydroxycyclobutyl)-N-(5-methyl-4-oxo-2,3,4,5-tetrahydrobenzo[b][1,4]oxazepin-3-yl)picolinamide

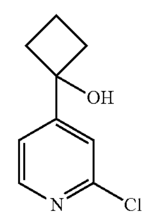 [SMILES: OC1(c2ccnc(Cl)c2)CCC1]

Step 1: 1-(2-chloro-4-pyridyl)cyclobutanol

To a solution of 2-chloro-4-iodopyridine (2.4 g, 10.0 mmol) in tetrahydrofuran (100 mL) was added isopropyl magnesium chloride (13.0 mL, 13.0 mmol, 1.0 M in tetrahydrofuran) at −45° C. over 5 mins under nitrogen. After stirred for 45 mins at −45° C., cyclobutanone (2.1 g, 30.0 mmol) was added. The mixture was allowed to warm to 25° C. and stirred for 15 h. The mixture was quenched by addition of saturated aqueous ammonium chloride solution. The mixture was extracted with ethyl acetate (2×100 mL). The organic layers were combined, washed with brine (1×50 mL), dried over sodium sulfate and concentrated under reduced pressure. The residue was purified by column chromatography (silica gel, 100-200 mesh, 0 to 10% ethyl acetate in petroleum ether) to afford 1-(2-chloro-4-pyridyl) cyclobutanol (500 mg, 27%) as colorless oil, used in the next step without further purification.

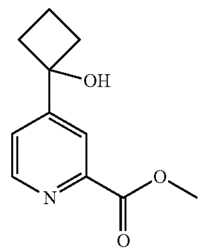

Step 2: methyl 4-(1-hydroxycyclobutyl)picolinate

A mixture of 1,1'-bis(diphenylphosphino)ferrocene palladium dichloride (80 mg, 0.11 mmol), triethylamine (331 mg, 3.27 mmol) and 1-(2-chloro-4-pyridyl)cyclobutanol (200 mg, 1.09 mmol) in methanol (10 mL) was stirred at 70° C. for 15 h under carbon oxide (35 psi). The mixture was concentrated under reduced pressure and the residue was purified by column chromatography (silica gel, 100-200 mesh, 0 to 10% ethyl acetate in petroleum ether) affording methyl 4-(1-hydroxycyclobutyl)picolinate (120 mg, 53%) as a yellow solid: LCMS $R_T$=0.554 min; m/z=207.8 $(M+H)^+$.

LCMS (5 to 95% acetonitrile in water+0.03% trifluoacetic acid over 1.5 mins) retention time 0.554 min, ESI+ found $[M+H]^+$=207.8.

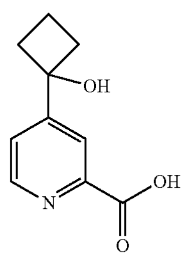 [SMILES: O=C(O)c1cc(C2(O)CCC2)ccn1]

Step 3: 4-(1-hydroxycyclobutyl)picolinic acid

A mixture of methyl 4-(1-hydroxycyclobutyl)picolinate (60 mg, 0.29 mmol) and potassium hydroxide (32 mg, 0.58 mmol) in ethanol (4 mL) and water (1 mL) was stirred for 2 h at 25° C.

The organic solvent was removed under reduced pressure, and the aqueous layer was adjusted to pH=3 by addition of hydrochloric acid (1.0 M). The aqueous layer was concentrated under reduced pressure affording crude 4-(1-hydroxycyclobutyl)picolinic acid (100 mg, 100%) as a white solid, used in the next step without further purification.

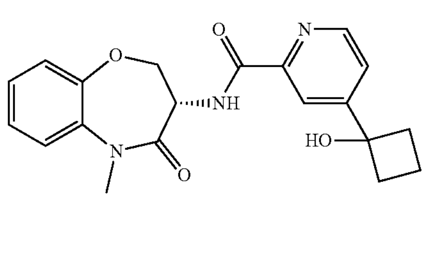 [SMILES: CN1C(=O)[C@@H](NC(=O)c2cc(C3(O)CCC3)ccn2)COc2ccccc21]

Step 4: (S)-4-(1-hydroxycyclobutyl)-N-(5-methyl-4-oxo-2,3,4,5-tetrahydrobenzo[b][1,4]oxazepin-3-yl) picolinamide A mixture of 4-(1-hydroxycyclobutyl)picolinic acid (100.0 mg, 0.52 mmol), (3S)-3-amino-5-methyl-2,3-dihydro-1,5-benzoxazepin-4-one (30.0 mg, 0.16 mmol), 1-hydroxybenzotriazole (25.0 mg, 0.19 mmol) and 1-(3-dimethylamino propyl)-3-ethylcarbodiimidehydrochloride (35.9 mg, 0.19 mmol) in N,N-dimethylformamide (3 mL) was stirred at 25° C. for 1 h. The solvent was evaporated under reduced pressure and the residue was purified by RP-HPLC (acetonitrile 30-60%/0.05% ammonium hydroxide in water) affording (S)-4-(1-hydroxycyclobutyl)-N-(5-methyl-4-oxo-2,3,4,5-tetrahydrobenzo[b][1,4]oxazepin-3-yl)picolinamide (30.0 mg, 36%) as a white solid: $^1$H NMR (400 MHz, $CD_3OD$): δ 8.63 (d, J=5.6 Hz, 1H), 8.20 (d, J=1.2 Hz, 1H), 7.72-7.70 (m, 1H), 7.46-7.44 (m, 1H), 7.35-7.24 (m, 3H), 5.06-4.99 (m, 1H), 4.67-4.63 (m, 1H), 4.43-4.38 (m, 1H), 3.43 (s, 3H), 2.52-2.36 (m, 4H), 2.14-2.01 (m, 1H), 1.89-1.78 (m, 1H). LCMS $R_T$=0.992 min; m/z=368.2 $(M+H)^+$.

LCMS (10 to 80% acetonitrile in water+0.03% trifluoacetic acid over 2 mins) retention time 0.992 min, ESI+ found $[M+H]^+$=368.2.

Example 328

WX Method E

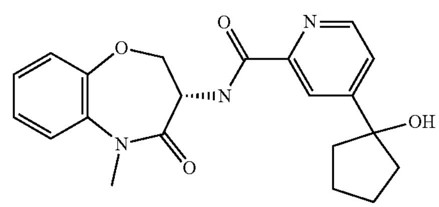 [SMILES: CN1C(=O)[C@@H](NC(=O)c2cc(C3(O)CCCC3)ccn2)COc2ccccc21]

(S)-4-(1-hydroxycyclopentyl)-N-(5-methyl-4-oxo-2,3,4,5-tetrahydrobenzo[b][1,4]oxazepin-3-yl)picolinamide

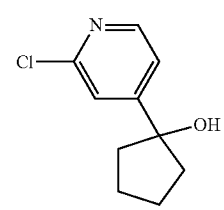 [SMILES: OC1(c2ccnc(Cl)c2)CCCC1]

Step 1: 1-(2-chloropyridin-4-yl)cyclopentanol

To a solution of 2-chloro-4-iodopyridine (5.0 g, 20.9 mmol) in tetrahydrofuran (100 mL) was added isopropylmagnesium chloride (1.0 M, 27.2 mL, 27.2 mmol) dropwise at −45° C. over 5 min. Stirring at −45° C. was continued for 45 min, cyclopentanone (5.3 g, 62.7 mmol) was added dropwise. The resulting mixture was allowed to warm to 25° C. and stirred for another 15 h before quenched by addition of saturated aqueous ammonium chloride. The mixture was extracted with ethyl acetate (3×50 mL). The combined organic layers were dried over sodium sulfate and concentrated under reduced pressure. The residue was purified by chromatography (silica gel, 100-200 mesh, 0 to 20% ethyl acetate in petroleum ether) to afford 1-(2-chloropyridin-4-yl) cyclopentanol (500 mg, 12%) as colorless oil. LCMS $R_T$=1.42 min; m/z=198.1 $(M+H)^+$.

LCMS (10 to 80% acetonitrile in water+0.03% ammonium hydroxide over 3.0 mins) retention time 1.42 min, ESI+ found [M+H]=198.1

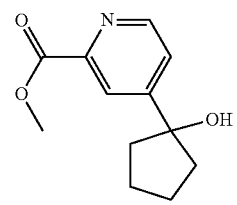 [SMILES: COC(=O)c1cc(C2(O)CCCC2)ccn1]

Step 2: methyl 4-(1-hydroxycyclopentyl)picolinate

A mixture of 1-(2-chloropyridin-4-yl) cyclopentanol (100 mg, 0.5 mmol), triethylamine (154 mg, 1.5 mmol) and 1,1'-bis(diphenylphosphino)ferrocene palladium dichloride) (37 mg, 0.05 mmol) in methanol (50 mL) was stirred at 70° C. for 15 h under the atmosphere of carbon oxide (35 psi). The reaction mixture was filtered and the filtrate was concentrated under reduce pressure. The residue was purified by column chromatography (silica gel, 100-200 mesh, 0 to 50% ethyl acetate in petroleum ether) affording methyl 4-(1-hydroxycyclopentyl)picolinate (80 mg, 71%) as light yellow oil, used in the next step without further purification.

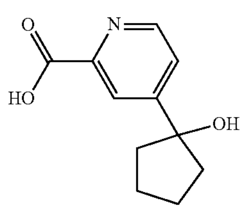 [SMILES: O=C(O)c1cc(C2(O)CCCC2)ccn1]

Step 3: 4-(1-hydroxycyclopentyl)picolinic acid

A mixture of methyl 4-(1-hydroxycyclopentyl)picolinate (80 mg, 0.36 mmol) and potassium hydroxide (40 mg, 0.72 mmol) in ethanol (5 mL) and water (1 mL) was stirred at 25° C. for 12 h. The solvent was removed under reduced pressure. The residue was diluted with water (10 mL) and adjusted to pH=4 by addition of hydrochloric acid (2.0 M). The mixture was concentrated under reduced pressure to afford crude 4-(1-hydroxycyclopentyl)picolinic acid (60 mg, 80%) as a yellow solid, used in the next step without further purification.

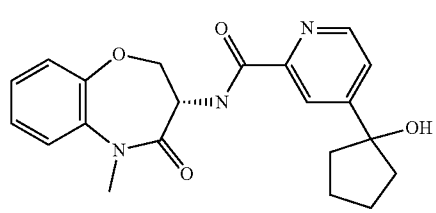 [SMILES: CN1C(=O)[C@@H](NC(=O)c2cc(C3(O)CCCC3)ccn2)COc2ccccc21]

Step 4: (S)-4-(1-hydroxycyclopentyl)-N-(5-methyl-4-oxo-2,3,4,5-tetrahydrobenzo[b][1,4]oxazepin-3-yl) picolinamide A mixture of (3S)-3-amino-5-methyl-2,3-dihydro-1,5-benzoxazepin-4-one (30.0 mg, 0.12 mmol), $N^1$-((ethylimino)methylene)-$N^3$,$N^3$-dimethylpropane-1,3-diamine hydrochloride (33.7 mg, 0.18 mmol), 1H-benzo[d][1,2,3]triazol-1-ol (23.7 mg, 0.18 mmol) and 4-(1-hydroxycyclopentyl)picolinic acid (36.0 mg, 0.18 mmol) in N,N-dimethylformamide (3 mL) was stirred at 25° C. for 16 h. The reaction was concentrated under reduced pressure and the residue was purified by RP-HPLC (acetonitrile 30-60%/0.05% ammonia hydroxide in water) affording (S)-4-(1-hydroxycyclopentyl)-N-(5-methyl-4-oxo-2,3,4,5-tetrahydrobenzo[b][1,4]oxazepin-3-yl)picolinamide (25.9 mg, 57.4%) as a white solid: $^1$H NMR (400 MHz, $CD_3OD$) δ 8.58 (d, J=5.2 Hz, 1H), 8.15 (s, 1H), 7.67-7.65 (m, 1H), 7.46-7.41 (m, 1H), 7.35-7.29 (m, 2H), 7.27-7.22 (m, 1H), 5.05-4.96 (m, 1H), 4.67-4.58 (m, 1H), 4.43-4.36 (m, 1H), 3.43 (s, 3H), 2.03-1.84 (m, 8H). LCMS $R_T$=1.03 min; m/z=382.2 $(M+H)^+$.

LCMS (10 to 80% acetonitrile in water+0.03% trifluoacetic acid over 2.0 mins) retention time 1.03 min, ESI+ found [M+H]=382.2.

Example 329

WX Method YY

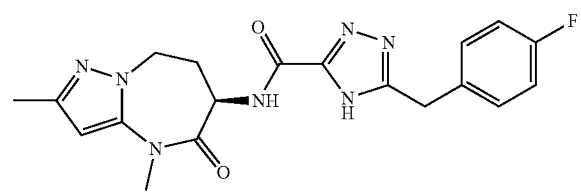 [SMILES: Cc1cc2n(n1)CC[C@@H](NC(=O)c1nnc(Cc3ccc(F)cc3)[nH]1)C(=O)N2C]

(R)—N-(2,4-dimethyl-5-oxo-5,6,7,8-tetrahydro-4H-pyrazolo[1,5-a][1,3]diazepin-6-yl)-5-(4-fluorobenzyl)-4H-1,2,4-triazole-3-carboxamide A mixture of 5-(4-fluorobenzyl)-4H-1,2,4-triazole-3-carboxylic acid (82 mg, 0.37 mmol), (6R)-6-amino-2,4-dimethyl-7,8-dihydro-6H-pyrazolo[1,5-a][1,3]diazepin-5-one (60 mg, 0.31 mmol), 1H-benzo[d][1,2,3]triazol-1-ol (63 mg, 0.46 mmol) and $N^1$-((ethylimino)methylene)-$N^3$,$N^3$-dimethylpropane-1,3-diamine hydrochloride (83 mg, 0.46 mmol) in N,N-dimethylformamide (5 mL) was stirred at 25° C. for 2 h. The reaction was concentrated under reduced pressure and the residue was purified by RP-HPLC (acetonitrile 12-42%/0.05% ammonia hydroxide in water) to afford (R)—N-(2,4-dimethyl-5-oxo-5,6,7,8-tetrahydro-4H-pyrazolo[1,5-a][1,3]diazepin-6-yl)-5-(4-fluorobenzyl)-4H-1,2,4-triazole-3-carboxamide (17.5 mg, 14%) as white solid: $^1$H NMR (400 MHz, $CD_3OD$) δ 7.31-7.27 (m, 2H), 7.06-6.99 (m, 2H), 6.10 (s, 1H), 4.54-4.49 (m, 1H), 4.30-4.28 (m, 2H), 4.13 (s, 2H), 3.30 (s, 3H), 2.86-2.80 (m, 1H), 2.27-2.21 (m, 4H). LCMS $R_T$=0.735 min; m/z=398.1 $(M+H)^+$.

LCMS (5 to 95% acetonitrile in water+0.03% formic acid over 1.5 mins) retention time 0.735 min, ESI+ found [M+H]= 398.1.

Example 330

WX Method JJJJJ

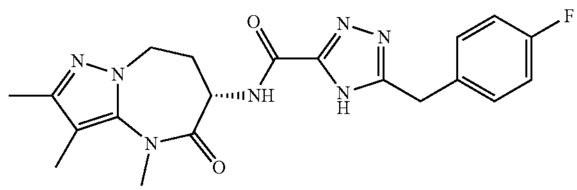 [SMILES: Cc1nn2c(c1C)N(C)C(=O)[C@@H](NC(=O)c1nnc(Cc3ccc(F)cc3)[nH]1)CC2]

(S)-5-(4-fluorobenzyl)-N-(2,3,4-trimethyl-5-oxo-5,6,7,8-tetrahydro-4H-pyrazolo[1,5-a][1, 3]diazepin-6-yl)-4H-1,2,4-triazole-3-carboxamide A mixture of 5-[(3-fluorophenyl)methyl]-4H-1,2,4-triazole-3-carboxylic acid (76 mg, 0.35 mmol), (6S)-6-amino-2,3,4-trimethyl-7,8-dihydro-6H-pyrazolo[1,5-a][1,3]diazepin-5-one (60 mg, 0.29 mmol), 1H-benzo[d][1,2,3]triazol-1-ol (58 mg, 0.43 mmol) and $N^1$-((ethylimino)methylene)-$N^3$,$N^3$-dimethylpropane-1,3-diamine hydrochloride (78 mg, 0.43 mmol) in N,N-dimethylformamide (5 mL) was stirred at 25° C. for 12 h. The reaction was concentrated under reduced pressure and the residue was purified by RP-HPLC (acetonitrile 15-45%/0.05% ammonia hydroxide in water) to afford (S)-5-(4-fluorobenzyl)-N-(2,3,4-trimethyl-5-oxo-5,6,7,8-tetrahydro-4H-pyrazolo[1,5-a][1,3]diazepin-6-yl)-4H-1,2,4-triazole-3-carboxamide (29.5 mg, 25%) as a white solid: $^1$H NMR (400 MHz, $CD_3OD$) δ 7.28-7.27 (m, 2H), 7.05-7.01 (m, 2H), 4.43-4.38 (m, 1H), 4.22-4.20 (m, 2H), 4.13 (s, 2H), 3.30 (s, 3H), 2.80-2.73 (m, 1H), 2.19-2.17 (m, 4H), 2.00 (s, 3H). LCMS $R_T$=0.754 min; m/z=412.1 $(M+H)^+$.

LCMS (5 to 95% acetonitrile in water+0.03% formic acid over 1.5 mins) retention time 0.754 min, ESI+ found [M+H]= 412.1.

Example 331

WX Method CCCC

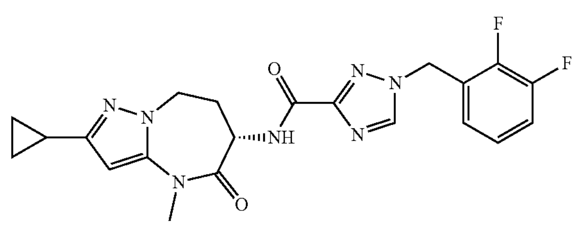 [SMILES: CN1C(=O)[C@@H](NC(=O)c2ncn(Cc3cccc(F)c3F)n2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-1-(2,3-difluorobenzyl)-1H-1,2,4-triazole-3-carboxamide A mixture of 1-[(2,3-difluorophenyl)methyl]-1,2,4-triazole-3-carboxylic acid (26 mg, 0.11 mmol), (6S)-6-amino-2-cyclopropyl-4-methyl-7,8-dihydro-6H-pyrazolo[1,5-a][1,3]diazepin-5-one (20 mg, 0.09 mmol), $N^1$-((ethylimino)methylene)-$N^3$,$N^3$-dimethyl propane-1,3-diamine hydrochloride (24 mg, 0.14 mmol) and 1H-benzo[d][1,2,3]triazol-1-ol (18 mg, 0.14 mmol) in N,N-dimethylformamide (5 mL) was stirred at 25° C. for 12 h. The reaction was concentrated under reduced pressure and the residue was purified by RP-HPLC (17-47% acetonitrile in water and 0.05% hydrogen chloride) to give (S)—N-(2-cyclopropyl-4-methyl-5-oxo-5,6,7,8-tetrahydro-4H-pyrazolo[1,5-a][1,3]diazepin-6-yl)-1-(2,3-difluorobenzyl)-1H-1,2,4-triazole-3-carboxamide (18.9 mg, 47%) as white solid: $^1$H NMR (400 MHz, $CD_3OD$) δ 8.82 (s, 1H), 7.33-7.26 (m, 1H), 7.19-7.18 (m, 2H), 6.34 (s, 1H), 5.63 (s, 2H), 4.73-4.69 (m, 1H), 4.48-4.36 (m, 2H), 3.31 (s, 3H), 2.90-2.84 (m, 1H), 2.41 (m, 1H), 2.03-2.01 (m, 1H), 1.16-1.14 (m, 2H), 0.93-0.91 (m, 2H). LCMS $R_T$=1.00 min; m/z=442.1 $(M+H)^+$.

LCMS (10 to 80% acetonitrile in water+0.03% trifluoacetic acid over 2.0 mins) retention time 1.00 min, ESI+ found [M+H]=442.1.

Example 332

WX Method DDDD

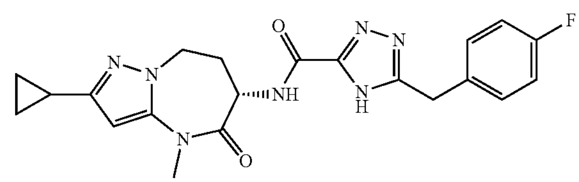 [SMILES: CN1C(=O)[C@@H](NC(=O)c2nnc(Cc3ccc(F)cc3)[nH]2)CCn2nc(C3CC3)cc21]

(S)—N-(2-cyclopropyl-4-methyl-5-oxo-5,6,7,8-tetrahydro-4H-pyrazolo[1,5-a][1,3]diazepin-6-yl)-5-(4-fluorobenzyl)-4H-1,2,4-triazole-3-carboxamide A mixture of 5-[(4-fluorophenyl)methyl]-4H-1,2,4-triazole-3-carboxylic acid (30 mg, 0.14 mmol), (6S)-6-amino-2-cyclopropyl-4-methyl-7,8-dihydro-6H-pyrazolo[1,5-a][1,3]diazepin-5-one (20 mg, 0.09 mmol), 1H-benzo[d][1,2,3]triazol-1-ol (18 mg, 0.14 mmol) and $N^1$-((ethylimino)methylene)-$N^3$,$N^3$-dimethylpropane-1,3-diamine hydrochloride (26 mg, 0.14 mmol) in N,N-dimethylformamide (5 mL) was stirred at 25° C. for 1 h. The reaction was concentrated under reduced pressure and the residue was purified by RP-HPLC (28-58% acetonitrile in water and 0.05% hydrogen chloride) to give (S)—N-(2-cyclopropyl-4-methyl-5-oxo-5,6,7,8-tetrahydro-4H-pyrazolo[1,5-a][1,3]diazepin-6-yl)-5-(4-fluorobenzyl)-4H-1,2,4-triazole-3-carboxamide (23 mg, 57%) as white solid: $^1$H NMR (400 MHz, $CD_3OD$): 7.35-7.32 (m, 2H), 7.11-7.07 (m, 2H), 6.16 (s, 1H), 4.62-4.57 (m, 1H), 4.41-4.23 (m, 4H), 3.33 (s, 3H), 2.90-2.79 (m, 1H), 2.37-2.29 (m, 1H), 1.99-1.93 (m, 1H), 1.05-1.03 (m, 2H), 0.87-0.78 (m, 2H). LCMS $R_T$=1.18 min; m/z=424.1 $(M+H)^+$.

LCMS (0 to 60% acetonitrile in water+0.03% trifluoacetic acid over 2 mins) retention time 1.18 min, ESI+ found $[M+H]^+$=424.1.

The compounds of Examples 333-338 and methods for their preparation are shown in Table 3 below.

Example 339

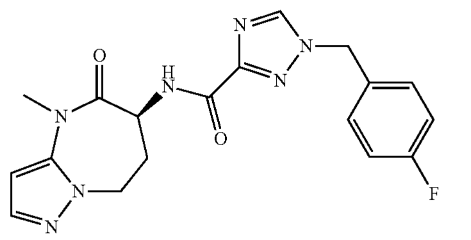 [SMILES: CN1C(=O)[C@@H](NC(=O)c2ncn(Cc3ccc(F)cc3)n2)CCn2nccc21]

1-[(4-fluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide Method B (57 mg, 89% yield)

$^1$H NMR (400 MHz, DMSO-$d_6$) δ 8.80 (s, 1H), 8.52 (d, J=7.8 Hz, 1H), 7.48 (d, J=2.0 Hz, 1H), 7.45-7.33 (m, 2H), 7.28-7.14 (m, 2H), 6.34 (d, J=2.0 Hz, 1H), 5.47 (s, 2H), 4.40-4.11 (m, 3H), 3.24 (s, 3H), 2.64-2.56 (m, 1H), 2.42-2.30 (m, 1H).

LCMS (2 to 98% acetonitrile in water+0.1% formic acid over 10 mins) retention time 3.62 min, ESI+ found [M+H]=384.2.

Example 340

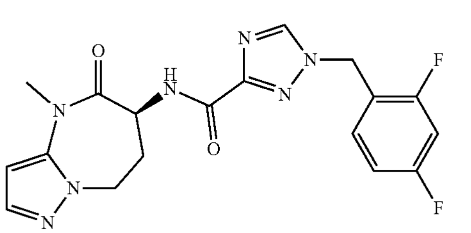 [SMILES: CN1C(=O)[C@@H](NC(=O)c2ncn(Cc3ccc(F)cc3F)n2)CCn2nccc21]

1-[(2,4-difluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide Method B (53 mg, 79% yield)

$^1$H NMR (400 MHz, DMSO-$d_6$) δ 8.79 (s, 1H), 8.52 (d, J=7.8 Hz, 1H), 7.54-7.40 (m, 2H), 7.38-7.25 (m, 1H), 7.20-7.04 (m, 1H), 6.34 (d, J=2.0 Hz, 1H), 5.52 (s, 1H), 4.46-4.09 (m, 3H), 3.24 (s, 3H), 2.66-2.54 (m, 1H), 2.43-2.30 (m, 1H).

LCMS (2 to 98% acetonitrile in water+0.1% formic acid over 10 mins) retention time 3.69 min, ESI+ found [M+H]=402.1.

Example 341

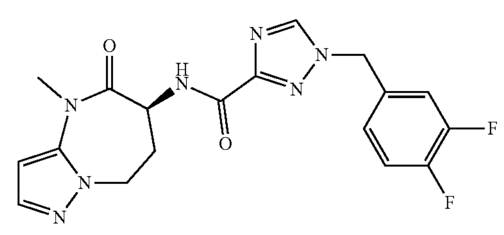 [SMILES: CN1C(=O)[C@@H](NC(=O)c2ncn(Cc3ccc(F)c(F)c3)n2)CCn2nccc21]

1-[(3,4-difluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide Method B (68 mg, 99% yield)

$^1$H NMR (400 MHz, DMSO-$d_6$) δ 8.83 (s, 1H), 8.55 (d, J=7.8 Hz, 1H), 7.53-7.39 (m, 2H), 7.30-7.11 (m, 2H), 6.34 (d, J=2.0 Hz, 1H), 5.61 (s, 2H), 4.42-4.13 (m, 3H), 3.24 (s, 3H), 2.65-2.54 (m, 1H), 2.44-2.29 (m, 1H).

LCMS (2 to 98% acetonitrile in water+0.1% formic acid over 10 mins) retention time 3.77 min, ESI+ found [M+H]=402.1.

Example 342

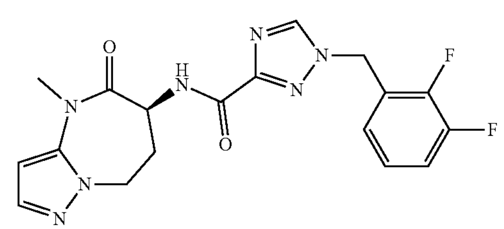 [SMILES: CN1C(=O)[C@@H](NC(=O)c2ncn(Cc3cccc(F)c3F)n2)CCn2nccc21]

1-[(2,3-difluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide Method B Method B (52 mg, 78% yield)

$^1$H NMR (400 MHz, DMSO-$d_6$) δ 8.80 (s, 1H), 8.55 (d, J=7.8 Hz, 1H), 7.58-7.35 (m, 3H), 7.30-7.04 (m, 1H), 6.34 (d, J=2.1 Hz, 1H), 5.48 (s, 2H), 4.43-4.12 (m, 3H), 3.24 (s, 3H), 2.63-2.56 (m, 1H), 2.44-2.30 (m, 1H).

LCMS (2 to 98% acetonitrile in water+0.1% formic acid over 10 mins) retention time 3.69 min, ESI+ found [M+H]=402.1.

Example 343

Method GH1

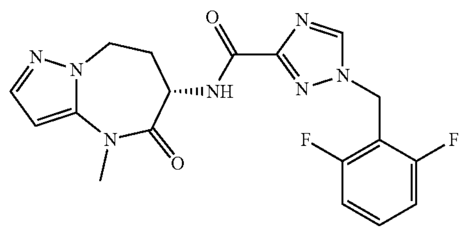 [SMILES: CN1C(=O)[C@@H](NC(=O)c2ncn(Cc3c(F)cccc3F)n2)CCn2nccc21]

1-[(2,6-difluorophenyl)methyl]-N-[(6S)-4-methyl-5-oxo-7,8-dihydro-6H-pyrazolo[1,5-a][1,3]diazepin-6-yl]-1,2,4-triazole-3-carboxamide

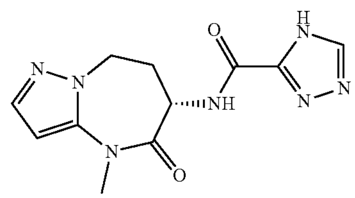 [SMILES: CN1C(=O)[C@@H](NC(=O)c2nnc[nH]2)CCn2nccc21]

Step 1: (S)—N-(4-methyl-5-oxo-5,6,7,8-tetrahydro-4H-pyrazolo[1,5-a][1,3]diazepin-6-yl)-4H-1,2,4-triazole-3-carboxamide To a solution of (6S)-6-amino-4-methyl-7,8-dihydro-6H-pyrazolo[1,5-a][1,3]diazepin-5-one (1200 mg, 6.66 mmol, 1.0 equiv) in DMF (15 mL) was added 4H-1,2,4-triazole-3-carboxylic acid (904 mg, 8.0 mmol, 1.2 equiv), N,N-diisopropylethylamine (3.48 mL, 20.0 mmol, 3.0 equiv), and PYAOP (4159 mg, 7.66 mmol, 1.15 equiv) last. The reaction mixture was stirred overnight then concentrated to dryness in vacuo. The resulting residue was purified by column chromatography (silica gel, 100-200 mesh, 0 to 15% methanol in dichloromethane) affording N(S)—N-(4-methyl-5-oxo-5,6,7,8-tetrahydro-4H-pyrazolo[1,5-a][1,3]diazepin-6-yl)-4H-1,2,4-triazole-3-carboxamide (1500 mg, 82% yield) as a white solid used as is in the next step. LCMS $R_T$=0.71 min [2 min method], m/z=256 $[M+H]^+$.

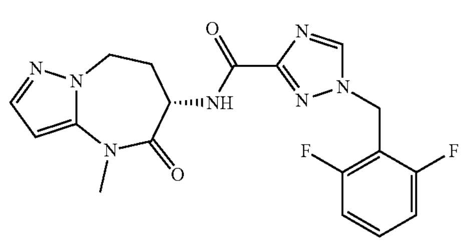 [SMILES: CN1C(=O)[C@@H](NC(=O)c2ncn(Cc3c(F)cccc3F)n2)CCn2nccc21]

Step 2: 1-[(2,6-difluorophenyl)methyl]-N-[(6S)-4-methyl-5-oxo-7,8-dihydro-6H-pyrazolo[1,5-a][1,3]diazepin-6-yl]-1,2,4-triazole-3-carboxamide To a suspension of N-[(6S)-4-methyl-5-oxo-7,8-dihydro-6H-pyrazolo[1,5-a][1,3]diazepin-6-yl]-4H-1,2,4-triazole-3-carboxamide (500 mg, 1.8 mmol, 1.0 equiv) in acetonitrile (10 mL) was added potassium carbonate (502 mg, 3.63 mmol, 2.0 equiv) followed by 2,6-difluorobenzyl bromide (465 mg, 2.18 mmol, 1.2 equiv). The reaction mixture was stirred for 16 h at RT, then was filtered through Celite and concentrated to dryness in vacuo. The residue was purified by RP-HPLC affording 1-[(2,6-difluorophenyl)methyl]-N-[(6S)-4-methyl-5-oxo-7,8-dihydro-6H-pyrazolo[1,5-a][1,3]diazepin-6-yl]-1,2,4-triazole-3-carboxamide (348 mg, 48% yield) as a white solid. 1H NMR (400 MHz, DMSO-d6) δ 8.83 (s, 1H), 8.51 (d, J=7.8 Hz, 1H), 7.57-7.44 (m, 2H), 7.23-7.10 (m, 2H), 6.33 (d, J=2.0 Hz, 1H), 5.56 (s, 2H), 4.42-4.09 (m, 3H), 3.24 (s, 3H), 2.65-2.53 (m, 1H), 2.42-2.30 (m, 1H). LCMS $R_T$=3.67 min [10 min method], m/z=402.2 $[M+H]^+$.

Example 344

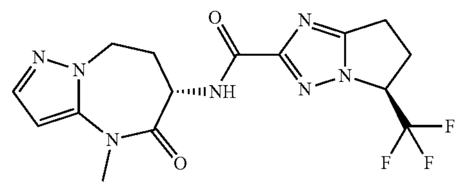 [SMILES: CN1C(=O)[C@@H](NC(=O)c2nc3n(n2)[C@H](C(F)(F)F)CC3)CCn2nccc21]

(5S)—N-[(6S)-4-methyl-5-oxo-7,8-dihydro-6H-pyrazolo[1,5-a][1,3]diazepin-6-yl]-5-(trifluoro methyl)-6,7-dihydro-5H-pyrrolo[1,2-b][1,2,4]triazole-2-carboxamide The title compound was prepared from (S)-6-amino-4-methyl-7,8-dihydro-4H-pyrazolo[1,5-a][1,3]diazepin-5(6H)-one and commercially available (S)-5-(trifluoromethyl)pyrrolidin-2-one according to Method G11. Yield of final step: 71%, obtained as a white solid. 1H NMR (400 MHz, DMSO-d6) δ 8.60 (d, J=7.9 Hz, 1H), 7.49 (d, J=2.0 Hz, 1H), 6.34 (d, J=2.0 Hz, 1H), 5.49 (td, J=7.8, 6.9, 3.4 Hz, 1H), 4.44-4.26 (m, 2H), 4.20 (ddd, J=14.5, 12.7, 6.6 Hz, 1H), 3.25 (s, 3H), 3.15-2.92 (m, 3H), 2.82-2.70 (m, 1H), 2.65-2.54 (m, 1H), 2.44-2.32 (m, 1H). LCMS $R_T$=3.38 min [10 min method], m/z=384.1 $[M+H]^+$.

Example 345

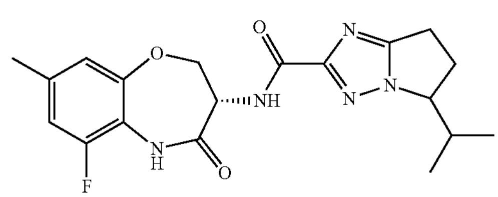 [SMILES: Cc1cc(F)c2c(c1)OC[C@H](NC(=O)c1nc3n(n1)C(C(C)C)CC3)C(=O)N2]

N-[(3S)-6-fluoro-8-methyl-4-oxo-3,5-dihydro-2H-1,5-benzoxazepin-3-yl]-5-isopropyl-6,7-di hydro-5H-pyrrolo[1,2-b][1,2,4]triazole-2-carboxamide The title compound was prepared from (S)-3-amino-6-fluoro-8-methyl-2,3-dihydrobenzo[b][1,4]oxazepin-4(5H)-one and commercially available ethyl 5-methyl-4-oxohexanoate according to Method GH2. Yield of final step:

47%, obtained as a white solid. 1H NMR (400 MHz, DMSO-d6) δ 10.00 (s, 1H), 8.35 (dd, J=7.7, 5.2 Hz, 1H), 6.99 (dd, J=10.7, 1.8 Hz, 1H), 6.89 (s, 1H), 4.90-4.80 (m, 1H), 4.63-4.53 (m, 1H), 4.47 (dd, J=10.1, 7.3 Hz, 1H), 4.34 (dt, J=9.1, 4.9 Hz, 1H), 2.92-2.83 (m, 2H), 2.79-2.65 (m, 1H), 2.48-2.35 (m, 1H), 2.30 (s, 3H), 2.23-2.09 (m, 1H), 0.95 (dd, J=6.9, 1.5 Hz, 3H), 0.81 (dd, J=6.9, 0.9 Hz, 3H). LCMS $R_T$=4.76 min [10 min method], m/z=388.1 $[M+H]^+$.

Example 346

Method GH2

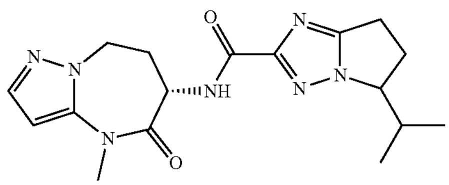 [SMILES: CC(C)C1CCc2nc(C(=O)N[C@H]3CCn4nccc4N(C)C3=O)nn21]

5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide

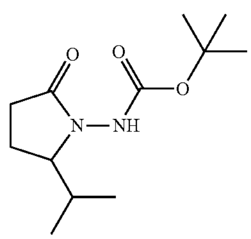 [SMILES: CC(C)C1CCC(=O)N1NC(=O)OC(C)(C)C]

Step 1: tert-butyl (2-isopropyl-5-oxopyrrolidin-1-yl)carbamate

To a solution of ethyl 5-methyl-4-oxo-hexanoate (1000 mg, 5.80 mmol, 1.0 equiv) in tetrahydrofuran (20 mL) was added acetic acid (10 mL, 174.5 mmol, 30 equiv) and tert-butyl carbazate (1151 mg, 8.71 mmol, 1.5 equiv). The reaction mixture was stirred for 16 h at 50° C. After cooling the mixture to RT, sodium cyanoborohydride was added (547 mg, 8.71 mmol, 1.5 equiv). The reaction mixture was further stirred 4 h at RT. After this time, the reaction was quenched with 10% $Na_2HPO_4$ (150 mL) and extracted with isopropyl acetate (3×100 mL). The combined organics were washed with 10% $Na_2HPO_4$ (2×150 mL), water and brine, dried over sodium sulfate, and concentrated to dryness in vacuo. The resulting residue was purified by column chromatography (silica gel, 100-200 mesh, 0 to 100% isopropyl acetate in heptane) affording tert-butyl (2-isopropyl-5-oxopyrrolidin-1-yl)carbamate as a pale yellow oil (800 mg, 57% yield) used as is in the next step. LCMS $R_T$=1.20 min [2 min method], m/z=243 $[M+H]^+$.

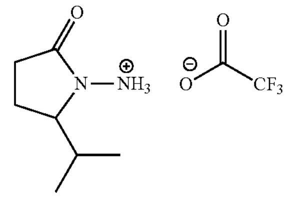

Step 2: 2-isopropyl-5-oxopyrrolidin-1-aminium 2,2,2-trifluoroacetate

To a solution of tert-butyl (2-isopropyl-5-oxopyrrolidin-1-yl)carbamate in dichloromethane (5 mL) was added trifluoroacetic acid (5 ml). The reaction mixture was stirred for 1.5 h at RT. Toluene (10 ml) was added, and the mixture was concentrated to dryness in vacuo. The residue was resuspended in toluene and concentrated to dryness two more times affording 2-isopropyl-5-oxopyrrolidin-1-aminium 2,2,2-trifluoroacetate as a colorless oil which was used immediately in the next step without purification. LCMS $R_T$=0.80 min [2 min method], m/z=143 $[M+H]^+$ for $C_7H_{15}N_2O$.

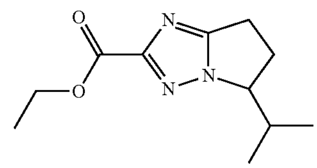 [SMILES: CCOC(=O)c1nc2n(n1)C(C(C)C)CC2]

Step 3: ethyl 5-isopropyl-6,7-dihydro-5H-pyrrolo[1,2-b][1,2,4]triazole-2-carboxylate To a solution of 2-isopropyl-5-oxopyrrolidin-1-aminium 2,2,2-trifluoroacetate (850 mg, 3.3 mmol, 1.0 equiv) in acetonitrile (10 mL) was added ethyl 2-ethoxy-2-imino-acetate (0.48 mL, 500 mg, 3.5 mmol, 1.1 equiv). The resulting mixture was stirred for 1 h at RT, and then subject to microwave irradiation at 160° C. for 50 mins. The reaction mixture was concentrated to dryness in vacuo, and the resulting residue was purified by column chromatography (silica gel, 100-200 mesh, 0 to 100% isopropyl acetate in heptane) affording ethyl 5-isopropyl-6,7-dihydro-5H-pyrrolo[1,2-b][1,2,4]triazole-2-carboxylate as a pale yellow oil (102 mg, 14% yield) used as is in the next step. LCMS $R_T$=1.08 min [2 min method], m/z=224 $[M+H]^+$.

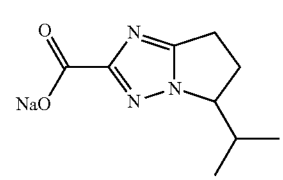

Step 4: sodium 5-isopropyl-6,7-dihydro-5H-pyrrolo[1,2-b][1,2,4]triazole-2-carboxylate To a solution of ethyl 5-isopropyl-6,7-dihydro-5H-pyrrolo[1,2-b][1,2,4]triazole-2-carboxylate (106 mg, 0.47 mmol, 1.0 equiv) in tetrahydrofuran (2 mL) was added 1M aqueous sodium hydroxide (0.5 mL, 1.0500 equiv). The reaction mixture was stirred for 1 h at 50° C., then was concentrated to dryness in vacuo affording sodium 5-isopropyl-6,7-dihydro-5H-pyrrolo[1,2-b][1,2,4]triazole-2-carboxylate as a brown solid which was used immediately in the next step without purification. LCMS $R_T$=0.90 min [2 min method], m/z=196 [M+H]$^+$ for $C_9H_{13}N_3O_2$.

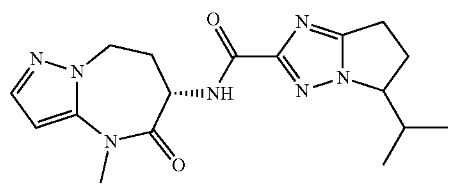 [SMILES: CC(C)C1CCc2nc(C(=O)N[C@H]3CCn4nccc4N(C)C3=O)nn21]

Step 5: 5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide To a solution of (6S)-6-amino-4-methyl-7,8-dihydro-6H-pyrazolo[1,5-a][1,3]diazepin-5-one (35 mg, 0.19 mmol, 1.0 equiv) in N,N-dimethylformamide (2 mL) was added sodium 5-isopropyl-6,7-dihydro-5H-pyrrolo[1,2-b][1,2,4]tri azole-2-carboxylate (52 mg, 0.237 mmol, 1.22 equiv), N,N-diisopropylethylamine (0.102 mL, 0.58 mmol, 3.0 equiv), and PYAOP (127 mg, 0.23 mmol, 1.2 equiv). The reaction mixture was stirred overnight then concentrated to dryness in vacuo. The residue was purified by RP-HPLC affording 5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (68 mg, 98% yield) as a white solid. 1H NMR (400 MHz, DMSO-d6) δ 8.45 (dd, J=11.1, 7.8 Hz, 1H), 7.49 (dd, J=2.0, 0.6 Hz, 1H), 6.34 (dd, J=2.0, 1.2 Hz, 1H), 4.45-4.24 (m, 3H), 4.24-4.11 (m, 1H), 3.25 (d, J=1.5 Hz, 3H), 2.92-2.81 (m, 2H), 2.78-2.54 (m, 2H), 2.46-2.28 (m, 2H), 2.15 (pd, J=6.8, 4.7 Hz, 1H), 0.94 (d, J=6.8 Hz, 3H), 0.81 (dd, J=6.8, 1.6 Hz, 3H). LCMS $R_T$=3.71 min [10 min method], m/z=358.2 [M+H]$^+$.

Example 347

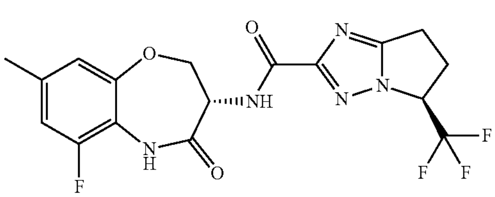 [SMILES: Cc1cc(F)c2c(c1)OC[C@H](NC(=O)c1nc3n(n1)[C@H](C(F)(F)F)CC3)C(=O)N2]

(5S)—N-[(3S)-6-fluoro-8-methyl-4-oxo-3,5-dihydro-2H-1,5-benzoxazepin-3-yl]-5-(trifluoromethyl)-6,7-dihydro-5H-pyrrolo[1,2-b][1,2,4]triazole-2-carboxamide The title compound was prepared from (S)-3-amino-6-fluoro-8-methyl-2,3-dihydrobenzo[b][1,4]oxazepin-4(5H)-one and commercially available (S)-5-(trifluoromethyl)pyrrolidin-2-one according to Method G11. Yield of final step: 57%, obtained as a white solid. 1H NMR (400 MHz, DMSO-d6) δ 10.01 (s, 1H), 8.49 (d, J=7.8 Hz, 1H), 6.99 (ddd, J=10.7, 1.8, 0.8 Hz, 1H), 6.90 (s, 1H), 5.58-5.43 (m, 1H), 4.86 (dt, J=11.1, 7.5 Hz, 1H), 4.60 (dd, J=11.2, 10.1 Hz, 1H), 4.46 (dd, J=10.1, 7.3 Hz, 1H), 3.16-2.96 (m, 3H), 2.84-2.70 (m, 1H), 2.35-2.27 (m, 3H). LCMS $R_T$=4.60 min [10 min method], m/z=414.1 [M+H]$^+$.

Example 348

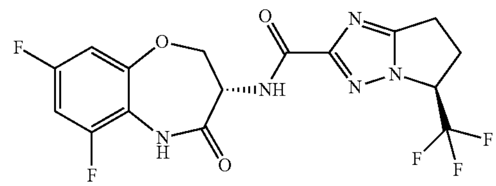 [SMILES: O=C(N[C@H]1COc2cc(F)cc(F)c2NC1=O)c1nc2n(n1)[C@H](C(F)(F)F)CC2]

(5S)—N-[(3S)-6,8-difluoro-4-oxo-3,5-dihydro-2H-1,5-benzoxazepin-3-yl]-5-(trifluoromethyl)-6,7-dihydro-5H-pyrrolo[1,2-b][1,2,4]triazole-2-carboxamide The title compound was prepared from (S)-3-amino-6,8-difluoro-2,3-dihydrobenzo[b][1,4]oxazepin-4(5H)-one and commercially available (S)-5-(trifluoromethyl)pyrrolidin-2-one according to Method G11. Yield of final step: 84%, obtained as a white solid. 1H NMR (400 MHz, DMSO-d6) δ 8.52 (d, J=7.7 Hz, 1H), 7.24 (ddd, J=10.4, 9.1, 2.9 Hz, 1H), 7.04 (ddd, J=9.4, 2.9, 1.8 Hz, 1H), 5.57-5.44 (m, 1H), 4.92 (dt, J=11.1, 7.4 Hz, 1H), 4.66 (dd, J=11.1, 10.2 Hz, 1H), 4.52 (dd, J=10.2, 7.1 Hz, 1H), 3.15-2.97 (m, 4H), 2.83-2.71 (m, 1H). LCMS $R_T$=4.34 min [10 min method], m/z=418.1 [M+H]$^+$.

Example 349

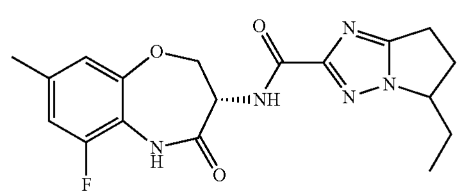 [SMILES: CCC1CCc2nc(C(=O)N[C@H]3COc4cc(C)cc(F)c4NC3=O)nn21]

5-ethyl-N-[(3S)-6-fluoro-8-methyl-4-oxo-3,5-dihydro-2H-1,5-benzoxazepin-3-yl]-6,7-dihydro-5H-pyrrolo[1,2-b][1,2,4]triazole-2-carboxamide The title compound was prepared from (S)-3-amino-6-fluoro-8-methyl-2,3-dihydrobenzo[b][1,4]oxazepin-4(5H)-one and commercially available ethyl 4-oxo-hexanoate according to Method GH2. Yield of final step: 23%, obtained as a white solid. 1H NMR (400 MHz, DMSO-d6) δ 10.00 (s, 1H), 8.35 (dd, J=7.8, 2.7 Hz, 1H), 6.98 (ddd, J=10.7, 1.8, 0.8 Hz, 1H), 6.89 (s, 1H), 4.90-4.79 (m, 1H), 4.58 (ddd, J=11.2, 10.1, 5.5 Hz, 1H), 4.46 (ddd, J=10.1, 7.3, 1.8 Hz, 1H), 4.43-4.34 (m, 1H), 2.93-2.76 (m, 3H), 2.37-2.31 (m, 1H), 2.30 (t, J=0.7 Hz, 3H), 1.96-1.83 (m, 1H), 1.78-1.64 (m, 1H), 0.91 (td, J=7.4, 1.0 Hz, 3H). LCMS $R_T$=4.44 min [10 min method], m/z=374.1 [M+H]$^+$.

Example 350

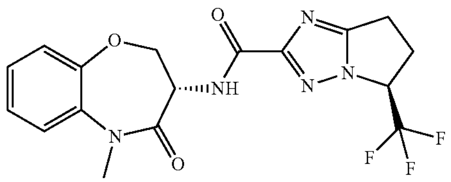 [SMILES: CN1C(=O)[C@@H](NC(=O)c2nc3n(n2)[C@H](C(F)(F)F)CC3)COc2ccccc21]

(5S)—N-[(3S)-5-methyl-4-oxo-2,3-dihydro-1,5-benzoxazepin-3-yl]-5-(trifluoromethyl)-6,7-dihydro-5H-pyrrolo[1,2-b][1,2,4]triazole-2-carboxamide The title compound was prepared from (S)-3-amino-5-methyl-2,3-dihydrobenzo[b][1,4]oxazepin-4(5H)-one and commercially available (S)-5-(trifluoromethyl)pyrrolidin-2-one according to Method G11. Yield of final step: 84%, obtained as a white solid. 1H NMR (400 MHz, DMSO-d6) δ 8.52 (d, J=8.0 Hz, 1H), 7.55-7.47 (m, 1H), 7.38-7.20 (m, 3H), 5.56-5.44 (m, 1H), 4.84 (dt, J=11.5, 7.8 Hz, 1H), 4.59 (dd, J=11.5, 9.9 Hz, 1H), 4.42 (dd, J=9.9, 7.7 Hz, 1H), 3.32 (s, 3H), 3.12-2.97 (m, 3H), 2.81-2.71 (m, 1H). LCMS $R_T$=4.86 min [10 min method], m/z=396.1 $[M+H]^+$.

Example 351

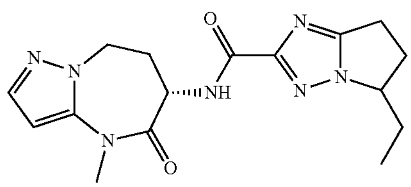 [SMILES: CCC1CCc2nc(C(=O)N[C@H]3CCn4nccc4N(C)C3=O)nn21]

5-ethyl-N-[(6S)-4-methyl-5-oxo-7,8-dihydro-6H-pyrazolo[1,5-a][1,3]diazepin-6-yl]-6,7-di hydro-5H-pyrrolo[1,2-b][1,2,4]triazole-2-carboxamide The title compound was prepared from (6S)-6-amino-4-methyl-7,8-dihydro-6H-pyrazolo[1,5-a][1,3]diazepin-5-one and commercially available ethyl 4-oxo-hexanoate according to Method GH2. Yield of final step: 77%, obtained as a white solid. 1H NMR (400 MHz, DMSO-d6) δ 8.44 (t, J=7.5 Hz, 1H), 7.49 (dd, J=2.0, 0.5 Hz, 1H), 6.34 (dd, J=2.1, 0.8 Hz, 1H), 4.43-4.12 (m, 4H), 3.25 (d, J=1.5 Hz, 3H), 2.94-2.76 (m, 3H), 2.69-2.54 (m, 1H), 2.45-2.27 (m, 2H), 1.95-1.83 (m, 1H), 1.78-1.63 (m, 1H), 0.91 (td, J=7.4, 1.0 Hz, 3H). LCMS $R_T$=3.87 min [10 min method], m/z=344.2 $[M+H]^+$.

Examples 352 and 354

Method GH_chiral_1

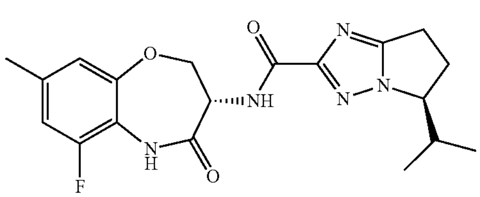

-continued

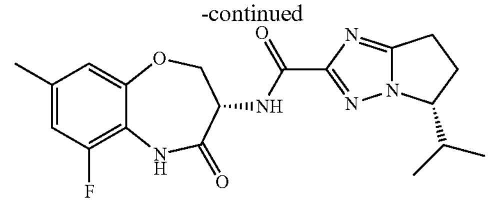

(5S)-5-isopropyl-N-[(3S)-6-fluoro-8-methyl-4-oxo-3,5-dihydro-2H-1,5-benzoxazepin-3-yl]-6,7-dihydro-5H-pyrrolo[1,2-b][1,2,4]triazole-2-carboxamide and (5R)-5-isopropyl-N-[(3S)-6-fluoro-8-methyl-4-oxo-3,5-dihydro-2H-1,5-benzoxazepin-3-yl]-6,7-dihydro-5H-pyrrolo[1,2-b][1,2,4]triazole-2-carboxamide N-[(3S)-6-fluoro-8-methyl-4-oxo-3,5-dihydro-2H-1,5-benzoxazepin-3-yl]-5-isopropyl-6,7-di hydro-5H-pyrrolo[1,2-b][1,2,4]triazole-2-carboxamide was further purified by chiral SFC (SFC conditions: Column: Regis Whelk O-1 (s,s)50×4.6 mm I.D., 3 μm Mobile phase: A: CO2 B: Methanol (0.1% NH4OH) Isocratic: 45% B in 2.5 min Flow rate: 4 mL/min Column temperature: 40° C., BPR: 120 bar) affording arbitrarily assigned diastereomers (5S)-5-isopropyl-N-[(3S)-6-fluoro-8-methyl-4-oxo-3,5-dihydro-2H-1,5-benzoxazepin-3-yl]-6,7-dihydro-5H-pyrrolo[1,2-b][1,2,4]triazole-2-carboxamide (0.008 g, 10%) and (5R)-5-isopropyl-N-[(3S)-6-fluoro-8-methyl-4-oxo-3,5-dihydro-2H-1,5-benzoxazepin-3-yl]-6,7-dihydro-5H-pyrrolo[1,2-b][1,2,4]triazole-2-carboxamide (0.008 g, 10%).

Analytical data for the first eluting diastereomer (arbitrarily assigned S,S configuration): SFC $R_T$ (Whelk O-1 (S,S) column, 45% methanol+0.1% ammonium hydroxide isocratic elution, 2.5 min method): 0.57 min, 100% ee: 1H NMR (400 MHz, DMSO-d6) δ 10.00 (s, 1H), 8.36 (d, J=7.7 Hz, 1H), 6.99 (dd, J=10.9, 1.8 Hz, 1H), 6.89 (d, J=1.8 Hz, 1H), 4.85 (dt, J=11.1, 7.5 Hz, 1H), 4.58 (t, J=10.7 Hz, 1H), 4.47 (dd, J=10.1, 7.3 Hz, 1H), 4.34 (dt, J=9.0, 4.8 Hz, 1H), 2.92-2.82 (m, 2H), 2.79-2.64 (m, 1H), 2.42 (dtd, J=15.0, 8.7, 8.2, 4.8 Hz, 1H), 2.30 (s, 3H), 2.22-2.08 (m, 1H), 0.95 (d, J=6.8 Hz, 3H), 0.81 (d, J=6.8 Hz, 3H). LCMS $R_T$=5.12 min, m/z=388.2 $[M+H]^+$.

Analytical data for the second eluting diastereomer (arbitrarily assigned S,R configuration): SFC $R_T$ 0.85 min, 99% ee. 1H NMR (400 MHz, DMSO-d6) δ 10.01 (s, 1H), 8.35 (d, J=7.7 Hz, 1H), 6.99 (ddd, J=10.8, 1.9, 0.8 Hz, 1H), 6.89 (dt, J=1.9, 1.0 Hz, 1H), 4.85 (dt, J=11.0, 7.5 Hz, 1H), 4.57 (dd, J=11.1, 10.1 Hz, 1H), 4.47 (dd, J=10.1, 7.3 Hz, 1H), 4.34 (dt, J=8.4, 4.9 Hz, 1H), 2.87 (t, J=7.5 Hz, 2H), 2.78-2.65 (m, 1H), 2.47-2.36 (m, 1H), 2.33-2.28 (m, 3H), 2.21-2.09 (m, 1H), 0.94 (d, J=6.8 Hz, 3H), 0.81 (d, J=6.8 Hz, 3H) LCMS $R_T$=5.14 min, m/z=388.2 $[M+H]^+$.

Example 353

Method GH_chiral_2

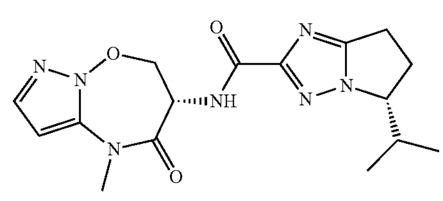

-continued

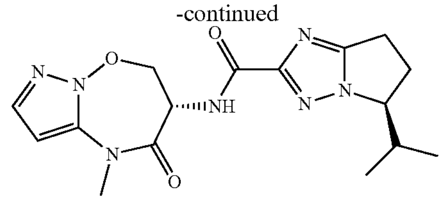

(5R)-5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide and (5S)-5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide 5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide was further purified by chiral SFC (SFC conditions: Column: Regis Whelk O-1 (s,s)50×4.6 mm I.D., 3 μm Mobile phase: A: CO2 B: Methanol (0.1% NH4OH) Isocratic: 45% B in 2.5 min Flow rate: 4 mL/min Column temperature: 40° C., BPR: 120 bar) affording arbitrarily assigned diastereomers (5R)-5-isopropyl-N-[(6S)-4-methyl-5-oxo-7,8-dihydro-6H-pyrazolo][1,5-a][1,3]diazepin-6-yl]-6,7-dihydro-5H-pyrrolo[1,2-b][1,2,4]triazole-2-carboxamide (0.018 g, 27%) and (5S)-5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (0.019 g, 28%) as white solids:

Analytical data for the first eluting diastereomer (arbitrarily assigned S,R configuration): SFC $R_T$ (Whelk O-1 (S,S) column, 45% methanol+0.1% ammonium hydroxide isocratic elution, 2.5 min method): 0.90 min, 99% ee: 1H NMR (400 MHz, DMSO-d6) δ 8.46 (d, J=7.8 Hz, 1H), 7.49 (d, J=2.0 Hz, 1H), 6.34 (d, J=2.0 Hz, 1H), 4.43-4.14 (m, 4H), 3.25 (s, 3H), 2.91-2.82 (m, 2H), 2.78-2.54 (m, 2H), 2.46-2.29 (m, 2H), 2.21-2.09 (m, 1H), 0.94 (d, J=6.9 Hz, 3H), 0.81 (d, J=6.8 Hz, 3H). LCMS $R_T$=4.18 min, m/z=358.2 $[M+H]^+$.

Analytical data for the second eluting diastereomer (arbitrarily assigned S,S configuration): SFC $R_T$ 1.02 min, 99% ee. 1H NMR (400 MHz, DMSO-d6) δ 8.43 (d, J=7.8 Hz, 1H), 7.49 (d, J=1.9 Hz, 1H), 6.34 (d, J=2.0 Hz, 1H), 4.44-4.14 (m, 4H), 3.25 (s, 3H), 2.86 (t, J=7.5 Hz, 2H), 2.77-2.56 (m, 2H), 2.46-2.30 (m, 2H), 2.22-2.09 (m, 1H), 0.94 (d, J=6.8 Hz, 3H), 0.81 (d, J=6.8 Hz, 3H). LCMS $R_T$=4.17 min, m/z=358.2 $[M+H]^+$.

Example 355

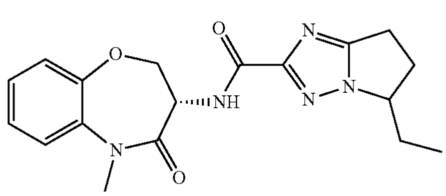 [SMILES: CCC1CCc2nc(C(=O)N[C@H]3COc4ccccc4N(C)C3=O)nn21]

5-ethyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide The title compound was prepared from (S)-3-amino-5-methyl-2,3-dihydrobenzo[b][1,4]oxazepin-4(5H)-one and commercially available ethyl 4-oxo-hexanoate according to Method GH2. Yield of final step: 13%, obtained as a white solid. 1H NMR (400 MHz, DMSO-d6) δ 8.37 (dd, J=8.0, 3.9 Hz, 1H), 7.54-7.47 (m, 1H), 7.37-7.21 (m, 3H), 4.88-4.77 (m, 1H), 4.56 (ddd, J=11.5, 9.9, 7.0 Hz, 1H), 4.46-4.34 (m, 2H), 3.31 (s, 3H), 2.93-2.75 (m, 3H), 2.39-2.27 (m, 1H), 1.96-1.82 (m, 1H), 1.77-1.63 (m, 1H), 0.91 (td, J=7.5, 1.1 Hz, 3H). LCMS $R_T$=4.28 min [10 min method], m/z=356.1 $[M+H]^+$.

Example 356

Method GH3

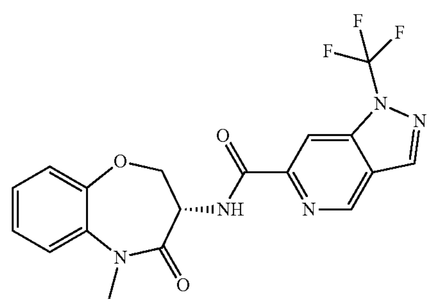

(S)—N-(5-methyl-4-oxo-2,3,4,5-tetrahydrobenzo[b][1,4]oxazepin-3-yl)-1-(trifluoromethyl)-1H-pyrazolo[4,3-c]pyridine-6-carboxamide

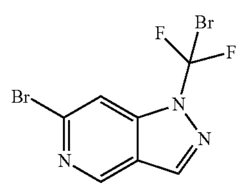 [SMILES: FC(F)(Br)n1ncc2cnc(Br)cc21]

Step 1: 6-bromo-1-(bromodifluoromethyl)-1H-pyrazolo[4,3-c]pyridine

To a suspension of 6-bromo-1H-pyrazolo[4,3-c]pyridine (2000 mg, 10.1 mmol, 1.0 equiv) in acetonitrile (40 mL) was added cesium carbonate (9872 mg, 30.3 mmol, 3.0 equiv) and dibromodifluoromethane (1.85 mL, 4238 mg, 20.2 mmol, 2.0 equiv). The vessel was capped, and the reaction mixture was heated with vigorous stirring at 50° C. for 16 h. After this time, the mixture was diluted with dichloromethane and filtered through Celite. The filtrate was concentrated to dryness in vacuo to obtain the product 6-bromo-1-(bromodifluoromethyl)-1H-pyrazolo[4,3-c]pyridine as a dark red solid that was used in the next step without further purification. LCMS $R_T$=1.45 min [2 min method], m/z=328 $[M+H]^+$.

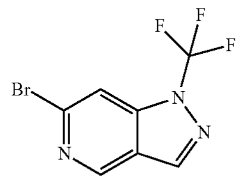 [SMILES: FC(F)(F)n1ncc2cnc(Br)cc21]

Step 2: 6-bromo-1-(trifluoromethyl)-1H-pyrazolo[4,3-c]pyridine

To a suspension of 6-bromo-1-(trifluoromethyl)-1H-pyrazolo[4,3-c]pyridine (crude from the previous step) in dichloromethane (100 mL) cooled to −78° C. was added silver tetrafluoroborate (2949 mg, 15.2 mmol, 1.5 equiv). The reaction mixture was allowed to warm to RT slowly overnight. After this time, the mixture was diluted with dichloromethane/methanol (1:1), filtered through Celite, and concentrated to dryness in vacuo affording 6-bromo-1-(trifluoromethyl)pyrazolo[4,3-c]pyridine (1700 mg, 63% yield) as a yellow solid that was used without further purification. LCMS $R_T$=1.34 min [2 min method], m/z=266 $[M]^+$.

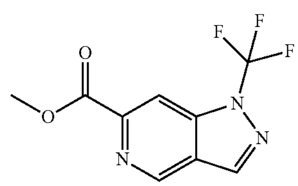 [SMILES: COC(=O)c1cc2c(cn1)cnn2C(F)(F)F]

Step 3: methyl 1-(trifluoromethyl)-1H-pyrazolo[4,3-c]pyridine-6-carboxylate

A high-pressure vessel with gas inlet was charged successively with 6-bromo-1-(trifluoromethyl)pyrazolo[4,3-c]pyridine (1700 mg, 6.4 mmol, 1.0 equiv), methanol (30 mL), triethylamine (8.9 mL, 64 mmol, 10 equiv), and [1,1'-bis(diphenylphosphino)ferrocene]dichloropalladium(II) (480 mg, 0.64 mmol, 0.10 equiv). The reactor was flushed once with carbon monoxide gas, then pressurized to 120 psi carbon monoxide. The reaction was heated to 80° C. for 16 h. After this time, the gas was released and the mixture was filtered through Celite and concentrated to dryness in vacuo. The residue was purified by column chromatography (silica gel, 100-200 mesh, 0 to 100% isopropyl acetate in heptane) affording methyl 1-(trifluoromethyl)pyrazolo[4,3-c]pyridine-6-carboxylate (263 mg, 17% yield) as an off white solid. LCMS $R_T$=1.15 min [2 min method], m/z=246 $[M+H]^+$.

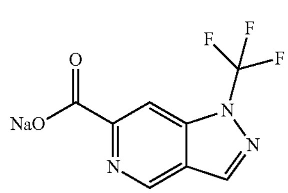

Step 4: sodium 1-(trifluoromethyl)-1H-pyrazolo[4,3-c]pyridine-6-carboxylate

To a solution of methyl 1-(trifluoromethyl)pyrazolo[4,3-c]pyridine-6-carboxylate (263 mg, 1.1 mmol, 1.0 equiv) in tetrahydrofuran (4 mL) was added 1M sodium hydroxide (1.18 mL, 1.1 equiv). The reaction mixture was stirred for 2 h at 50° C., then was concentrated to dryness in vacuo affording sodium 1-(trifluoromethyl)-1H-pyrazolo[4,3-c]pyridine-6-carboxylate as a brown residue which was used directly in the next reaction without purification. LCMS $R_T$=0.90 min [2 min method], m/z=233 $[M+H]^+$ for $C_8H_4F_3N_3O_2$.

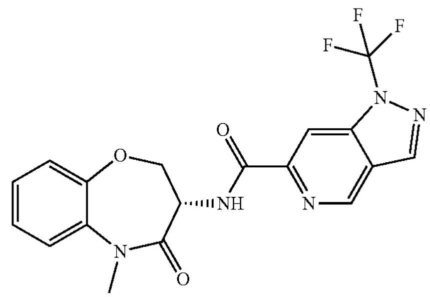

Step 5: (S)—N-(5-methyl-4-oxo-2,3,4,5-tetrahydrobenzo[b][1,4]oxazepin-3-yl)-1-(trifluoromethyl)-1H-pyrazolo[4,3-c]pyridine-6-carboxamide To a solution of (3S)-3-amino-5-methyl-2,3-dihydro-1,5-benzoxazepin-4-one (229 mg, 1 mmol) in N,N-dimethylformamide (2 mL) was added sodium 1-(trifluoromethyl)pyrazolo[4,3-c]pyridine-6-carboxylate (271 mg, 1.07 mmol, 1.07 equiv), N,N-diisopropylethylamine (0.523 mL, 3 mmol, 3 equiv), and PYAOP (651 mg, 1.2 mmol, 1.2 equiv). The reaction mixture was stirred for 16 h at RT. After this time, the mixture was concentrated to dryness in vacuo and purified by RP-HPLC affording (S)—N-(5-methyl-4-oxo-2,3,4,5-tetrahydrobenzo[b][1,4]oxazepin-3-yl)-1-(trifluoromethyl)-1H-pyrazolo[4,3-c]pyridine-6-carboxamide (303 mg, 75% yield) as a white solid. 1H NMR (400 MHz, DMSO-d6) δ 9.41 (d, J=1.1 Hz, 1H), 9.12 (d, J=7.8 Hz, 1H), 8.94 (s, 1H), 8.21 (p, J=1.3 Hz, 1H), 7.52 (dd, J=7.4, 2.1 Hz, 1H), 7.39-7.23 (m, 3H), 4.93 (dt, J=11.3, 7.8 Hz, 1H), 4.66-4.48 (m, 2H), 3.35 (s, 3H). LCMS $R_T$=5.53 min [10 min method], m/z=406.1 $[M+H]^+$.

Example 357

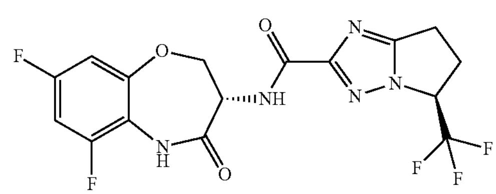 [SMILES: O=C(N[C@H]1COc2cc(F)cc(F)c2NC1=O)c1nc2n(n1)[C@H](C(F)(F)F)CC2]

(5S)—N-[(3S)-7,9-difluoro-2-oxo-1,3,4,5-tetrahydro-1-benzazepin-3-yl]-5-(trifluoromethyl)-6,7-dihydro-5H-pyrrolo[1,2-b][1,2,4]triazole-2-carboxamide The title compound was prepared from (S)-3-amino-7,9-difluoro-1,3,4,5-tetrahydro-2H-benzo[b]azepin-2-one and commercially available (S)-5-(trifluoromethyl)pyrrolidin-2-one according to Method G11. Yield of final step: 73%, obtained as a white solid. 1H NMR (400 MHz, DMSO-d6) δ 9.97 (s, 1H), 8.34 (d, J=7.5 Hz, 1H), 7.27 (ddd, J=10.1, 9.0, 2.8 Hz, 1H), 7.20-7.10 (m, 1H), 5.55-5.43 (m, 1H), 4.36 (dt, J=11.5, 7.8 Hz, 1H), 3.12-2.97 (m, 3H), 2.85-2.70 (m, 3H), 2.48-2.38 (m, 1H), 2.31-2.18 (m, 1H). LCMS $R_T$=4.30 min [10 min method], m/z=416.1 $[M+H]^+$.

Examples 358 and 359

Method GH_chiral_3

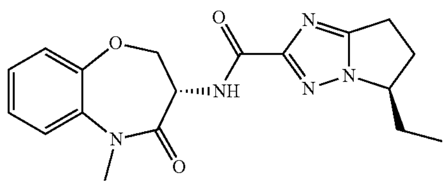

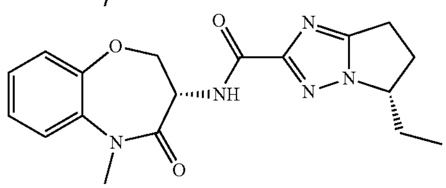

(5R)-5-ethyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide and (5S)-5-ethyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide 5-ethyl-N-[(3S)-5-methyl-4-oxo-2,3-dihydro-1,5-benzoxazepin-3-yl]-6,7-dihydro-5H-pyrrolo [1,2-b][1,2,4]triazole-2-carboxamide was further purified by chiral SFC (SFC conditions: Column: CHIRALCEL OX 50×4.6 mm I.D., 3 μm Mobile phase: A: CO2 B: Methanol (0.1% NH4OH) Isocratic: 35% B in 2.5 min Flow rate: 4 mL/min Column temperature: 40° C., BPR: 120 bar) affording arbitrarily assigned diastereomers (5R)-5-ethyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide and (5S)-5-ethyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide.

Analytical data for the first eluting diastereomer (arbitrarily assigned S,R configuration): SFC $R_T$ (CHIRALCEL-OX column, 35% methanol+0.1% ammonium hydroxide isocratic elution, 2.5 min method): 0.80 min, 100% ee: 1H NMR (400 MHz, DMSO-d6) δ 8.37 (d, J=8.0 Hz, 1H), 7.50 (dd, J=7.6, 2.0 Hz, 1H), 7.38-7.16 (m, 3H), 4.82 (dt, J=11.5, 7.8 Hz, 1H), 4.57 (dd, J=11.5, 9.9 Hz, 1H), 4.47-4.33 (m, 2H), 3.32 (s, 3H), 2.97-2.75 (m, 3H), 2.39-2.26 (m, 1H), 1.89 (ddd, J=13.9, 7.4, 5.2 Hz, 1H), 1.78-1.63 (m, 1H), 0.91 (t, J=7.4 Hz, 3H). LCMS $R_T$=4.45 min, m/z=356.1 $[M+H]^+$.

Analytical data for the second eluting diastereomer (arbitrarily assigned S,S configuration): SFC $R_T$ 1.13 min, 99% ee. 1H NMR (400 MHz, DMSO-d6) δ 8.36 (d, J=8.0 Hz, 1H), 7.54-7.46 (m, 1H), 7.38-7.20 (m, 3H), 4.83 (dt, J=11.5, 7.8 Hz, 1H), 4.55 (dd, J=11.4, 9.9 Hz, 1H), 4.46-4.33 (m, 2H), 3.32 (s, 3H), 2.92-2.76 (m, 3H), 2.38-2.25 (m, 1H), 1.88 (dtd, J=14.9, 7.4, 5.1 Hz, 1H), 1.70 (dt, J=14.0, 7.2 Hz, 1H), 0.91 (t, J=7.4 Hz, 3H). LCMS $R_T$=4.47 min, m/z=356.1 $[M+H]^+$.

Example 360

Method GH4 & Method GH3

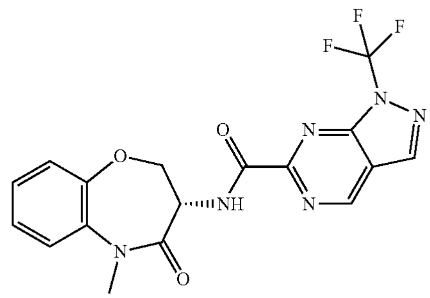 [SMILES: CN1C(=O)[C@@H](NC(=O)c2ncc3cnn(C(F)(F)F)c3n2)COc2ccccc21]

N-[(3S)-5-methyl-4-oxo-2,3-dihydro-1,5-benzoxazepin-3-yl]-1-(trifluoromethyl)pyrazolo[3,4-d]pyrimidine-6-carboxamide

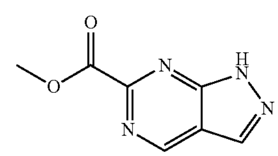

Step 1: methyl 1H-pyrazolo[3,4-d]pyrimidine-6-carboxylate

A high-pressure vessel with gas inlet was charged successively with 6-chloro-1H-pyrazolo[3,4-d]pyrimidine (1000 mg, 6.47 mmol, 1.0 equiv), 2-butanol (30 mL), triethylamine (9.0 mL, 64.7 mmol, 10.0 equiv), and [1,1'-bis(diphenylphosphino)ferrocene]dichloropalladium(II) (483 mg, 0.65 mmol, 0.10 equiv). The reactor was flushed once with carbon monoxide gas, then pressurized to 120 psi carbon monoxide. The reaction was heated to 80° C. for 16 h. After this time, the gas was released and the mixture was filtered through Celite and concentrated to dryness in vacuo. The residue was purified by column chromatography (silica gel, 100-200 mesh, 0 to 10% methanol in dichloromethane) affording methyl 1H-pyrazolo[3,4-d]pyrimidine-6-carboxylate (470 mg, 41% yield) as a yellow solid. Note that the initially formed sec-butyl ester was transesterified to the methyl ester during chromatography. LCMS $R_T$=0.84 min [2 min method], m/z=179 $[M+H]^+$.

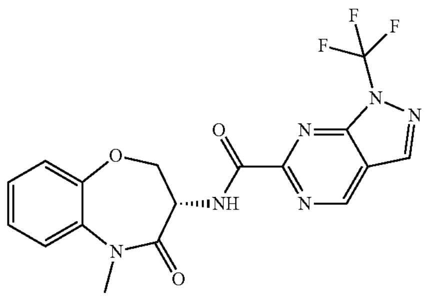 [SMILES: CN1C(=O)[C@@H](NC(=O)c2ncc3cnn(C(F)(F)F)c3n2)COc2ccccc21]

N-[(3S)-5-methyl-4-oxo-2,3-dihydro-1,5-benzoxazepin-3-yl]-1-(trifluoromethyl)pyrazolo[3,4-d]pyrimidine-6-carboxamide The remainder of the synthesis was completed using methyl 1H-pyrazolo[3,4-d]pyrimidine-6-carboxylate according to Method GH3 Steps 1,2,4, and 5. Yield of final step: 15%, obtained as a white solid. 1H NMR (400 MHz, DMSO-d6) δ 9.67 (s, 1H), 9.15 (d, J=7.7 Hz, 1H), 8.92 (s, 1H), 7.57-7.50 (m, 1H), 7.39-7.24 (m, 3H), 4.91 (dt, J=10.9, 7.9 Hz, 1H), 4.64-4.50 (m, 2H), 3.35 (s, 3H). LCMS $R_T$=4.84 min [10 min method], m/z=407.1 $[M+H]^+$.

Example 361

Method GH5 and Method GH2

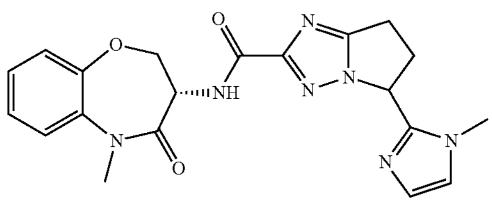 [SMILES: CN1C(=O)[C@@H](NC(=O)c2nc3n(n2)C(c2nccn2C)CC3)COc2ccccc21]

5-(1-methylimidazol-2-yl)-N-[(3S)-5-methyl-4-oxo-2,3-dihydro-1,5-benzoxazepin-3-yl]-6, 7-dihydro-5H-pyrrolo[1,2-b][1,2,4]triazole-2-carboxamide

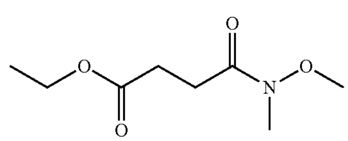

Step 1: ethyl 4-(methoxy(methyl)amino)-4-oxobutanoate

To a solution of N,O-dimethylhydroxylamine hydrochloride (4444.9 mg, 45.6 mmol, 1.5 equiv) in dichloromethane (100 mL) cooled to 0° C. was added triethylamine (12.7 mL, 91.1 mmol, 3.0 equiv) followed by ethyl 4-chloro-4-oxo-butanoate (4.329 mL, 5000 mg, 30.4 mmol, 1.0 equiv). The reaction mixture was stirred and allowed to warm to RT slowly overnight. After this time, water (100 mL) was added, the layers separated, and the aqueous extracted two more times with dichloromethane (2×100 mL). The combined organics were washed with 5% citric acid and brine, dried over sodium sulfate and concentrated to dryness in vacuo affording ethyl 4-[methoxy(methyl)amino]-4-oxo-butanoate (5100 mg, 89% yield) as a yellow oil that was used in the next step without further purification.

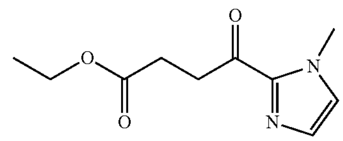

Step 2: ethyl 4-(1-methyl-1H-imidazol-2-yl)-4-oxobutanoate

To a solution of 1-methylimidazole (2200 mg, 27 mmol, 1.0 equiv) in tetrahydrofuran (100 mL) cooled to 0° C. was added N-butyllithium (2.5 M in hexanes, 11 mL, 27 mmol, 1.0 equiv) dropwise. The reaction mixture was stirred 30 mins at 0° C., then was cooled to −78° C. To the mixture was added ethyl 4-[methoxy(methyl)amino]-4-oxo-butanoate (5100 mg, 27 mmol, 1.0 equiv). The resulting mixture was stirred for 1 h at −78° C., then allowed to warm to RT. After reaching RT, the reaction was quenched with 5% citric acid (150 mL), then extracted with isopropyl acetate (3×100 mL). The combined organics were washed with water and brine, dried over sodium sulfate and concentrated to dryness in vacuo. The residue was purified by column chromatography (silica gel, 100-200 mesh, 0 to 100% isopropyl acetate in heptane) affording ethyl 4-(1-methylimidazol-2-yl)-4-oxo-butanoate (1200 mg, 21% yield) as a yellow oil.

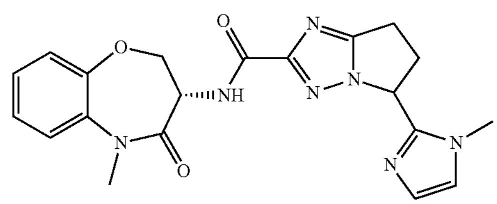 [SMILES: CN1C(=O)[C@@H](NC(=O)c2nc3n(n2)C(c2nccn2C)CC3)COc2ccccc21]

5-(1-methylimidazol-2-yl)-N-[(3S)-5-methyl-4-oxo-2,3-dihydro-1,5-benzoxazepin-3-yl]-6, 7-dihydro-5H-pyrrolo[1,2-b][1,2,4]triazole-2-carboxamide The title compound was prepared from ethyl 4-(1-methylimidazol-2-yl)-4-oxo-butanoate and dihydrobenzo[b][1,4]oxazepin-4(5H)-one according to Method GH2. Yield of final step: 53%, obtained as a white solid. 1H NMR (400 MHz, DMSO-d6) δ 8.39 (dd, J=8.0, 5.7 Hz, 1H), 7.54-7.45 (m, 1H), 7.36-7.18 (m, 4H), 6.84 (d, J=1.1 Hz, 1H), 5.91-5.80 (m, 1H), 4.80 (dt, J=11.4, 7.8 Hz, 1H), 4.55 (ddd, J=11.7, 9.9, 2.2 Hz, 1H), 4.39 (ddd, J=9.9, 7.7, 4.4 Hz, 1H), 3.79 (d, J=0.8 Hz, 3H), 3.31 (s, 3H), 3.19-2.95 (m, 4H). LCMS $R_T$=2.70 min [10 min method], m/z=408.1 $[M+H]^+$.

Example 364

Method CS1

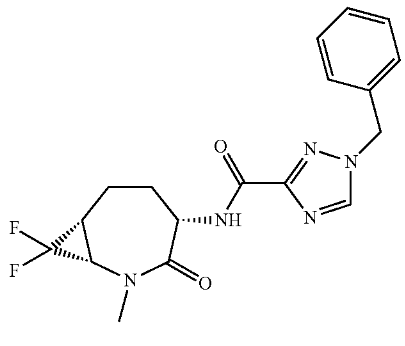 [SMILES: CN1C(=O)[C@@H](NC(=O)c2ncn(Cc3ccccc3)n2)CC[C@@H]2[C@H]1C2(F)F]

1-benzyl-N-[(1R,4S,7S)-8,8-difluoro-6-methyl-5-oxo-6-azabicyclo[5.1.0]octan-4-yl]-1,2,4-triazole-3-carboxamide

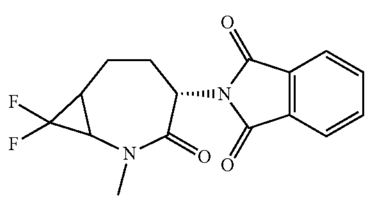 [SMILES: CN1C(=O)[C@@H](N2C(=O)c3ccccc3C2=O)CCC2C1C2(F)F]

Step 1: 2-((4S)-8,8-difluoro-2-methyl-3-oxo-2-azabicyclo[5.1.0]octan-4-yl)isoindoline-1,3-dione A solution of sodium chlorodifluoroacetate (1.42 g, 9.25 mmol) in diglyme (5.9 mL) was added dropwise to a refluxing solution of 2-[(3S)-1-methyl-2-oxo-4,5-dihydro-3H-azepin-3-yl]isoindoline-1,3-dione (0.250 g, 0.925 mmol) in diglyme (10 mL) over 25 minutes. After addition, the reaction was allowed to stir for an additional 10 minutes at reflux. After cooling to rt, the solvent was removed under reduced pressure and the residue was purified by flash column chromatography (silica, 0% to 70% isopropyl acetate-heptane) to give 2-[(4S)-8,8-difluoro-6-methyl-5-oxo-6-azabicyclo[5.1.0]octan-4-yl]isoindoline-1,3-dione (0.270 g, 0.843 mmol, 91% yield) as an inseparable ~6.8:1 mixture of diastereomers. $^1$H NMR (400 MHz, Chloroform-d) 6 (major isomer) 7.90-7.81 (m, 2H), 7.75-7.70 (m, 2H), 5.44 (dd, J=11.6, 8.0 Hz, 1H), 3.66-3.30 (m, 1H), 3.26-3.11 (m, 1H), 3.02 (s, 3H), 2.25-2.15 (m, 1H), 2.04-1.90 (m, 2H), 1.85-1.72 (m, 1H). LRMS $R_T$=1.29 min, m/z=321 [M=H]$^+$.

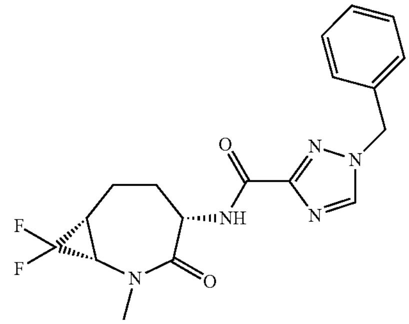 [SMILES: CN1C(=O)[C@@H](NC(=O)c2ncn(Cc3ccccc3)n2)CC[C@@H]2[C@H]1C2(F)F]

Step 2: 1-benzyl-N-[(1R,4S,7S)-8,8-difluoro-6-methyl-5-oxo-6-azabicyclo[5.1.0]octan-4-yl]-1,2,4-triazole-3-carboxamide Hydrazine (0.087 mL, 2.72 mmol) was added to a solution of 2-[(4S)-8,8-difluoro-6-methyl-5-oxo-6-azabicyclo[5.1.0]octan-4-yl]isoindoline-1,3-dione and (~6.8:1 dr, 0.290 g, 0.905 mmol) in ethanol (9.1 mL). The reaction was heated at 80° C. for 2 h. After cooling to rt, the reaction was filtered through a short plug of celite using ethanol. The filtrate was evaporated which delivered (4S)-4-amino-8,8-difluoro-6-methyl-6-azabicyclo[5.1.0]octan-5-one (88.9 mg, 0.467 mmol, 51.6% Yield). The crude residue was used in the next step without further purification. PYAOP (0.138 g, 0.254 mmol) was added to a solution of (4S)-4-amino-8,8-difluoro-6-methyl-6-azabicyclo[5.1.0]octan-5-one (44 mg, 0.231 mmol), 1-benzyl-1,2,4-triazole-3-carboxylic acid (58 mg, 0.289 mmol), and N,N-diisopropylethylamine (0.120 mL, 0.694 mmol), in N,N-dimethylformamide (2.3 mL). The reaction was allowed to stir at rt for 18 h before being concentrated under reduced pressure. The crude residue was purified by preparative HPLC (see below) to give 1-benzyl-N-((1S,4S,7R)-8,8-difluoro-2-methyl-3-oxo-2-azabicyclo[5.1.0]octan-4-yl)-1H-1,2, 4-triazole-3-carboxamide (56.7 mg, 0.151 mmol, 65% Yield).

$^1$H NMR (400 MHz, DMSO-d6) δ 8.82 (s, 1H), 8.58 (d, J=4.4 Hz, 1H), 7.43-7.27 (m, 5H), 5.48 (s, 2H), 4.43-4.33 (m, 1H), 3.27-3.14 (m, 1H), 2.80 (s, 3H), 2.55-2.43 (m, 1H), 2.10-2.00 (m, 3H), 1.30-1.10 (m, 1H).

LRMS $R_T$=3.90 min, m/z=376.1 [M+H]$^+$.

Prep HPLC Information:

Column: Phenomenex Gemini-NX C18 5 □m, 110 A (50×30 mm)

Mobile Phase: 0.1% Ammonium Hydroxide in Water (A)/Acetonitrile (B)

Elution Program

Gradient: 20 to 60% B

Pressure: 800 psi

Flow Rate: 60 mL/min

Column Temperature: 25° C.

Wavelength: 210 nm

Example 365

Method CS2

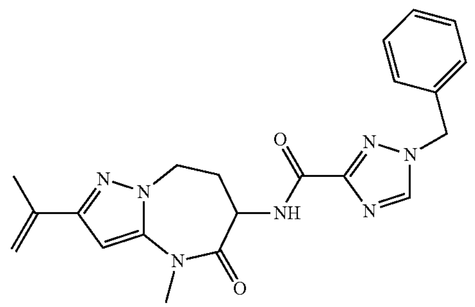 [SMILES: C=C(C)c1cc2n(n1)CCC(NC(=O)c1ncn(Cc3ccccc3)n1)C(=O)N2C]

1-benzyl-N-(2-isopropenyl-4-methyl-5-oxo-7,8-dihydro-6H-pyrazolo[1,5-a][1,3]diazepin-6-yl)-1,2,4-triazole-3-carboxamide

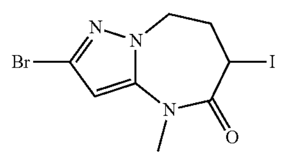

Step 1: 2-bromo-6-iodo-4-methyl-7,8-dihydro-4H-pyrazolo[1,5-a][1,3]diazepin-5(6H)-one Iodotrimetheylsilane (7.10 g, 34 mmol) was added to a solution of 2-bromo-4-methyl-7,8-dihydro-6H-pyrazolo[1,5-a][1,3]diazepin-5-one (1.4 g, 5.7 mmol) and N,N,N',N'-tetramethylethylenediamine (5.2 mL, 34 mmol) in dichloromethane (57 mL) at −15° C. After 1 h 30 minutes, iodine (4.4 g, 17 mmol) was added and the reaction was allowed to stir for an additional 2 h. Saturated aqueous sodium thiosulfate and saturated aqueous sodium bicarbonate were added to the reaction. The aqueous layer was extracted with dichloromethane (3×50 mL). The combined organic layers were dried over sodium sulfate, concentrated and the residue was purified by column chromatography (silica, 0% to 60% isopropyl acetate-heptane) to give 2-bromo-6-iodo-4-methyl-7,8-dihydro-6H-pyrazolo[1,5-a][1,3]diazepin-5-one (1.56 g, 4.22 mmol, 74% Yield).

$^1$H NMR (400.33 MHz, Chloroform-d) 66.13 (s, 1H), 4.65 (ddd, J=8.6, 7.4, 3.4 Hz, 1H), 4.36-4.14 (m, 2H), 3.33 (s, 3H), 2.95 (ddt, J=14.4, 8.7, 7.4 Hz, 1H), 2.77 (dddd, J=14.4, 8.6, 6.6, 5.0 Hz, 1H).

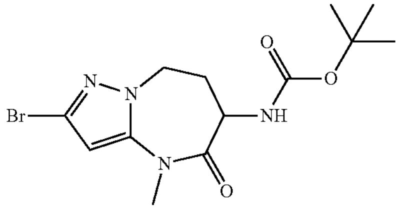 [SMILES: CN1C(=O)C(NC(=O)OC(C)(C)C)CCn2nc(Br)cc21]

Step 2: tert-butyl (2-bromo-4-methyl-5-oxo-5,6,7,8-tetrahydro-4H-pyrazolo[1,5-a][1,3]diazepin-6-yl) carbamate Sodium azide (0.319 g, 4.87 mmol) was added to a solution of 2-bromo-6-iodo-4-methyl-7,8-dihydro-6H-pyrazolo[1,5-a][1,3]diazepin-5-one (1.50 g, 4.05 mmol) in N,N-dimethylformamide (16.2 mL) at rt. The reaction was allowed to stir at rt for 1 h. The solvent was removed under vacuum and the residue was submitted to the next step immediately without any further purification.

Triphenylphosphine (2.15 g, 8.11 mmol) was added to a solution of 6-azido-2-bromo-4-methyl-7,8-dihydro-6H-pyrazolo[1,5-a][1,3]diazepin-5-one in tetrahydrofuran (40.5 mL) and water (2.0 mL). The reaction was heated at 55° C. for 1 h. After cooling to rt the volatiles were removed under vacuum. The residue was dissolved in dichloromethane (40.5 mL), then triethylamine (2.85 mL, 20.3 mmol) and di-tert-butyl dicarbonate (2.23 g, 10.1 mmol) were added sequentially. After 1 h, the volatiles were removed under vacuum and the residue was purified by column chromatography (silica, 20% to 100% isopropyl acetate-heptane) to give tert-butyl N-(2-bromo-4-methyl-5-oxo-7,8-dihydro-6H-pyrazolo[1,5-a][1,3]diazepin-6-yl)carbamate (1.29 g, 3.59 mmol, 89% yield).

LRMS $R_T$=1.34 min m/z=304 M−$C_4H_9$+H]$^+$.

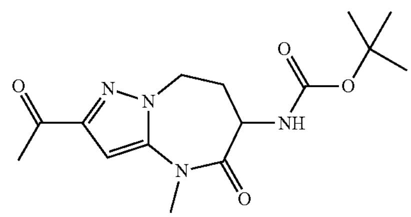 [SMILES: CC(=O)c1cc2n(n1)CCC(NC(=O)OC(C)(C)C)C(=O)N2C]

Step 3. tert-butyl (2-acetyl-4-methyl-5-oxo-5,6,7,8-tetrahydro-4H-pyrazolo[1,5-a][1,3]diazepin-6-yl) carba mate Bis(triphenylphosphine)palladium(II) dichloride (24 mg, 0.033 mmol) was added to a solution of tert-butyl N-(2-bromo-4-methyl-5-oxo-7,8-dihydro-6H-pyrazolo[1,5-a][1,3]diazepin-6-yl)carbamate (0.20 g, 0.56 mmol) and tributyl (1-ethoxyvinyl)tin (0.19 mL, 0.56 mmol) in 1,4-dioxane (10 mL). The flask was sealed with a yellow cap and heated at 100° C. for 12 h. Silica gel was added and the reaction was evaporated under reduced pressure. The crude material was purified by flash column chromatography (silica, 0% to 100% isopropyl acetate-heptane) to give tert-butyl N-(2-acetyl-4-methyl-5-oxo-7,8-dihydro-6H-pyrazolo[1,5-a][1,3]diazepin-6-yl)carbamate (0.120 g, 0.372 mmol, 100 mass %, 67% Yield).

$^1$H NMR (400.33 MHz, Chloroform-d) δ 6.58 (s, 1H), 5.43 (d, J=7.7 Hz, 1H), 4.46 (dd, J=14.4, 8.2 Hz, 1H), 4.33-4.03 (m, 2H), 3.35 (s, 3H), 3.06-2.88 (m, 1H), 2.56 (s, 3H), 2.02 (s, 1H), 1.41 (s, 9H).

LRMS $R_T$=1.34 min, m/z=267 [M−$C_4$H9+H]$^+$.

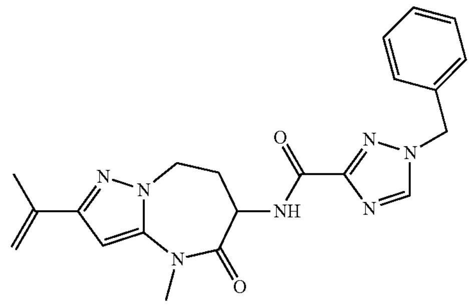 [SMILES: C=C(C)c1cc2n(n1)CCC(NC(=O)c1ncn(Cc3ccccc3)n1)C(=O)N2C]

Step 4 1-benzyl-N-(2-isopropenyl-4-methyl-5-oxo-7,8-dihydro-6-pyrazolo[1,5-a][1,3]diazepin-6-yl)-1,2,4-triazole-3-carboxamide Methylmagnesium bromide ((1.4 mol/L) in THF: toluene (1:3), 1.60 mL, 2.23 mmol) was added to a solution of tert-butyl N-(2-acetyl-4-methyl-5-oxo-7,8-dihydro-6H-pyrazolo[1,5-a][1,3]diazepin-6-yl)carbamate (0.120 g, 0.372 mmol) in tetrahydrofuran (3.7 mL) at −10° C. After 2 h, the reaction was quenched with saturated aqueous ammonium chloride. The aqueous layer was extracted with isopropyl acetate (3×30 mL). The combined organic layers were washed with brine, dried with magnesium sulfate, concentrated, and the residue was submitted to the next step without further purification.

Trifluoroacetic acid (1.0 mL, 13 mmol, 99 mass %) was added to a solution of the crude tert-butyl N-[2-(1-hydroxy-1-methyl-ethyl)-4-methyl-5-oxo-7,8-dihydro-6H-pyrazolo[[1,5-a][1,3]diazepin-6-yl]carbamate (50 mg 0.148 mmol) in dichloromethane (2.0 mL) at 0° C. After 10 min the reaction was warmed to rt and stirred for an additional 30 min. The solvent was removed under reduced pressure and the residue was submitted to the next reaction without further purification.

PYAOP (88.3 mg, 0.163 mmol) was added to a solution of the crude residue, 1-benzyl-1,2,4-triazole-3-carboxylic acid (37.5 mg, 0.185 mmol), and N,N-diisopropylethylamine (0.08 mL, 0.443 mmol), in N,N-dimethylformamide (1.5 mL, 19.1 mmol). The reaction was allowed to stir at rt for 18 h. The reaction was concentrated and the residue was purified by preparative HPLC (see below) to give 1-benzyl-N-(2-isopropenyl-4-methyl-5-oxo-7,8-dihydro-6H-pyrazolo[1,5-a][1,3]diazepin-6-yl)-1,2,4-triazole-3-carboxamide (25 mg, 0.0617 mmol, 41.7% Yield) $^1$H NMR (400.33 MHz, DMSO-d6) δ 8.82 (s, 1H), 8.54 (d, J=7.9 Hz, 1H), 7.47-7.18 (m, 5H), 6.59 (s, 1H), 5.56-5.43 (m, 3H), 5.06 (t, J=1.7 Hz, 1H), 4.42-4.28 (m, 2H), 4.28-4.09 (m, 1H), 3.25 (s, 3H), 2.72-2.53 (m, 1H), 2.38 (dd, J=12.5, 6.4 Hz, 1H), 2.04 (s, 3H).

LRMS $R_T$=4.47 min, m/z=406.2 $[M+H]^+$.

Prep HPLC Information:

Column: Phenomenex Gemini-NX C18 5 □m, 110 A (50×30 mm)

Mobile Phase: 0.1% Ammonium Hydroxide in Water (A)/Acetonitrile (B)

Elution Program

Gradient: 20-60 B

Pressure: 800 psi

Flow Rate: 20 mL/min

Column Temperature: 25° C.

Wavelength: 254 nm

Example 366

Method CS3

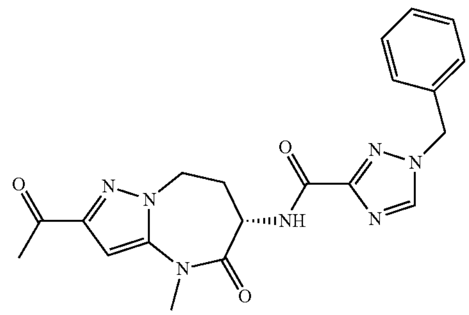 [SMILES: CC(=O)c1cc2n(n1)CC[C@H](NC(=O)c1ncn(Cc3ccccc3)n1)C(=O)N2C]

(S)—N-(2-acetyl-4-methyl-5-oxo-5,6,7,8-tetrahydro-4H-pyrazolo[1,5-a][1,3]diazepin-6-yl)-1-benzyl-1H-1,2,4-triazole-3-carboxamide

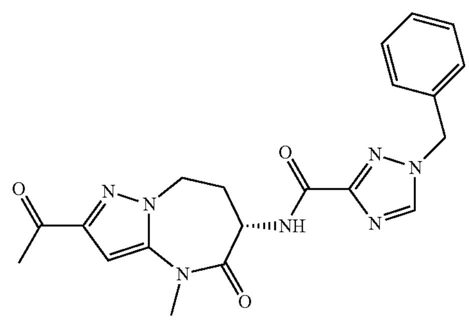 [SMILES: CC(=O)c1cc2n(n1)CC[C@H](NC(=O)c1ncn(Cc3ccccc3)n1)C(=O)N2C]

Step 1: (S)—N-(2-acetyl-4-methyl-5-oxo-5,6,7,8-tetrahydro-4H-pyrazolo[1,5-a][1,3]diazepin-6-yl)-1-benzyl-1H-1,2,4-triazole-3-carboxamide Trifluoroacetic acid (10 mL) was added to a solution of tert-butyl N-[2-(1-ethoxyvinyl)-4-methyl-5-oxo-7,8-dihydro-6H-pyrazolo[1,5-a][1,3]diazepin-6-yl]carbamate (0.550 g, 1.57 mmol) in dichloromethane (20 mL) at rt. After 2 h the solvent was removed under reduced pressure and the residue was submitted to the next reaction without further purification.

N,N-diisopropylethylamine (0.82, 4.71 mmol) was added to a solution of the crude residue, 1-benzyl-1,2,4-triazole-3-carboxylic acid (0.319 g, 1.57 mmol), and PYAOP (0.852 g, 1.57 mmol) in N,N-dimethylformamide (15.7 mL) at rt. After 3 h the solvent was removed under reduced pressure. A portion of the crude residue (200 mg) was purified by preparative HPLC (see below) to give (S)—N-(2-acetyl-4-methyl-5-oxo-5,6,7,8-tetrahydro-4H-pyrazolo[1,5-a][1,3]diazepin-6-yl)-1-benzyl-1H-1,2,4-triazole-3-carboxamide (15.7 mg, 0.0385 mmol).

$^1$H NMR (400.33 MHz, DMSO-d6) δ 8.82 (s, 1H), 8.59 (d, J=7.7 Hz, 1H), 7.43-7.26 (m, 5H), 6.83 (s, 1H), 5.48 (s, 2H), 4.48 (dd, J=14.5, 7.9 Hz, 1H), 4.41-4.26 (m, 2H), 3.26 (s, 3H), 2.72-2.57 (m, 1H), 2.48 (s, 3H), 2.52-2.40 (m, 1H).

LRMS $R_T$=3.84 min, m/z=408.2 $[M+H]^+$.

Prep HPLC Information:

Column: Phenomenex Cellulose-3, 5 □m (150×21.2 mm)

Mobile Phase: Carbon Dioxide (A)/0.1% $NH_4OH$ in Methanol (B)

Elution Program

Gradient: Isocratic @ 35%

Pressure: 100 bar

Flow Rate: 70 mL/min

Column Temperature: 40° C.

Wavelength: 220 nm

Examples 367 and 368

Method CS4

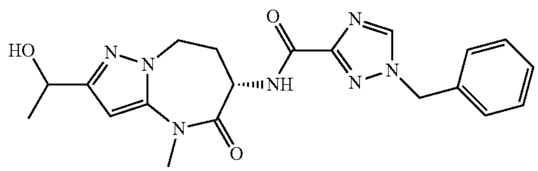

and

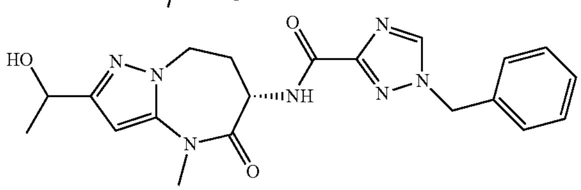

1-benzyl-N-((6S)-2-(1-hydroxyethyl)-4-methyl-5-oxo-5,6,7,8-tetrahydro-4H-pyrazolo[1,5-a][1,3]diazepin-6-yl)-1H-1,2,4-triazole-3-carboxamide

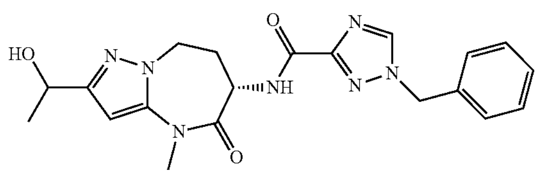

and

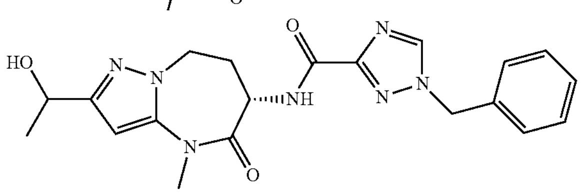

Step 1: 1-benzyl-N-((6S)-2-(1-hydroxyethyl)-4-methyl-5-oxo-5,6,7,8-tetrahydro-4H-pyrazol[1,5-a][1,3]diazepin-6-yl)-1H-1,2,4-triazole-3-carboxamide Sodium borohydride (56.9 mg, 1.47 mmol) was added to a solution of N-(2-acetyl-4-methyl-5-oxo-7,8-dihydro-6H-pyrazolo[1,5-a][1,3]diazepin-6-yl)-1-benzyl-1,2, 4-triazole-3-carboxamide (0.300 g (crude), 0.736 mmol) in methanol (4.1 mL) at 0° C. After 5 min, saturated aqueous ammonium chloride was added. The aqueous layer was extracted with isopropyl acetate (5×40 mL). The combined organic layers were washed with brine, dried with sodium sulfate, concentrated, and the residue was purified by preparative HPLC (see below) to give 1-benzyl-N-((6 S)-2-(1-hydroxyethyl)-4-methyl-5-oxo-5,6,7,8-tetrahydro-4H-pyrazolo[1,5-a][1,3]diazepin-6-yl)-1H-1,2,4-triazole-3-carboxamide (Peak 1, 9.4 mg, 0.023 mmol, 3.1% Yield) and 1-benzyl-N-((6 S)-2-(1-hydroxyethyl)-4-methyl-5-oxo-5,6,7,8-tetrahydro-4H-pyrazolo[1,5-a][1,3]diazepin-6-yl)-1H-1,2,4-triazole-3-carboxamide (Peak 2, 9.1 mg, 0.022 mmol, 3.0% yield).

Data for Example 367

$^1H$ NMR (400.33 MHz, DMSO-d6) δ 8.82 (s, 1H), 8.52 (d, J=7.8 Hz, 1H), 7.43-7.27 (m, 5H), 6.26 (s, 1H), 5.48 (s, 2H), 5.08 (d, J=5.1 Hz, 1H), 4.69-4.58 (m, 1H), 4.38-4.24 (m, 2H), 4.20-4.07 (m, 1H), 3.23 (s, 3H), 2.64-2.45 (m, 1H), 2.39-2.29 (m, 1H), 1.38 (d, J=6.5 Hz, 3H).

LRMS $R_T$=3.44 min, m/z=410.2 $[M+H]^+$.

Data for Example 368

$^1H$ NMR (400.33 MHz, DMSO-d6) δ 8.82 (s, 1H), 8.51 (d, J=7.9 Hz, 1H), 7.43-7.26 (m, 5H), 6.27 (s, 1H), 5.48 (s, 2H), 5.16 (d, J=4.5 Hz, 1H), 4.72-4.61 (m, 1H), 4.40-4.23 (m, 2H), 4.21-4.07 (m, 1H), 3.24 (s, 3H), 2.64-2.50 (m, 1H), 2.39-2.29 (m, 1H), 1.34 (d, J=6.5 Hz, 3H).

LRMS $R_T$=3.48 min, m/z=410.2 $[M+H]^+$.

Prep HPLC Information:

Stage 1:

Column: Chiralcel OX, 5 □m (150×21.2 mm)

Mobile Phase: Carbon Dioxide (A)/0.1% $NH_4OH$ in Methanol (B)

Elution Program

Gradient: Isocratic @ 50%

Pressure: 100 bar

Flow Rate: 70 mL/min

Column Temperature: 40° C.

Wavelength: 220 nm

Stage 2:

Column: Chiralpak AD, 5 □m (150×21.2 mm)

Mobile Phase: Carbon Dioxide (A)/0.1% $NH_4OH$ in Methanol (B)

Elution Program

Gradient: Isocratic @ 50%

Pressure: 100 bar

Flow Rate: 70 mL/min

Column Temperature: 40° C.

Wavelength: 220 nm

Examples 369 and 370

Method CS5

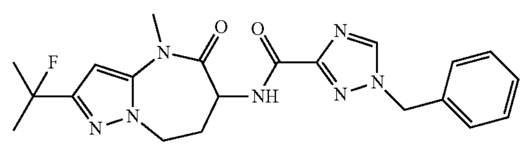

and

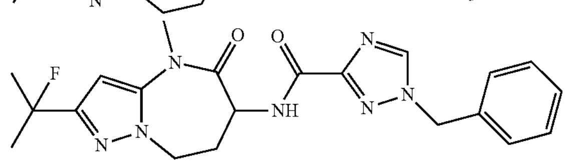

1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide and 1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide

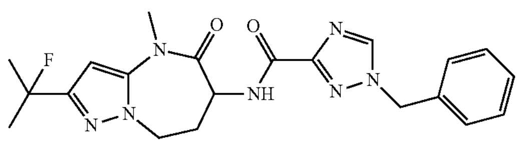

and

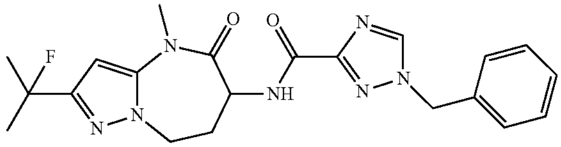

Step 1: 1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide and 1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide Bis(2-methoxyethyl)aminosulfur trifluoride (63.3 mg, 0.283 mmol) was added to a solution of 1-benzyl-N-[2-(1-hydroxy-1-methyl-ethyl)-4-methyl-5-oxo-7,8-dihydro-6H-pyrazolo[1,5-a][1,3]diazepin-6-yl]-1,2,4-triazole-3-carboxamide (30 mg, 0.071 mmol) in dichloromethane (0.71 mL) at 0° C. After 10 min the reaction was carefully quenched with saturated aqueous sodium bicarbonate. The aqueous layer was extracted with dichloromethane (3×20 mL). The combined organic layers were dried with sodium sulfate, concentrated, and the residue was purified by preparative HPLC (see below) to give 1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide (Peak 1, 10.9 mg, 0.0256 mmol, 36.2% Yield) and 1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide (Peak 2, 11.9 mg, 0.028 mmol, 39.5% Yield)

Data for G03074389:

Peak 1: $^1$H NMR (400 0.33 MHz, DMSO-d6) δ 8.82 (s, 1H), 8.55 (d, J=7.8 Hz, 1H), 7.43-7.27 (m, 5H), 6.48 (s, 1H), 5.48 (s, 2H), 4.40-4.24 (m, 2H), 4.25-4.13 (m, 1H), 3.25 (s, 3H), 2.66-2.54 (m, 1H), 2.44-2.32 (m, 1H), 1.71 (d, 7.7 Hz, 3H), 1.66 (d, 7.7 Hz, 3H).

LRMS $R_T$=4.47 min, m/z=426.3 [M+H]$^+$.

Data for G03074390:

Peak 2: $^1$H NMR (400.33 MHz, DMSO-d6) δ 8.82 (s, 1H), 8.55 (d, J=7.8 Hz, 1H), 7.43-7.27 (m, 5H), 6.48 (s, 1H), 5.48 (s, 2H), 4.40-4.27 (m, 2H), 4.25-4.13 (m, 1H), 3.25 (s, 3H), 2.66-2.53 (m, 1H), 2.44-2.32 (m, 1H), 1.71 (d, 7.7 Hz, 3H), 1.66 (d, 7.7 Hz, 3H).

LRMS $R_T$=4.47 min, m/z=426.3 [M+H]$^+$.

Column: Phenomenex Cellulose-3, 5 □m, (150×21.2 mm)

Mobile Phase: Carbon Dioxide (A)/Neat methanol (B)

Elution Program

Gradient: Isocratic @ 40%

Pressure: 100 bar

Flow Rate: 70 mL/min

Column Temperature: 40° C.

Wavelength: 220 nm

Example 371

Method CS6

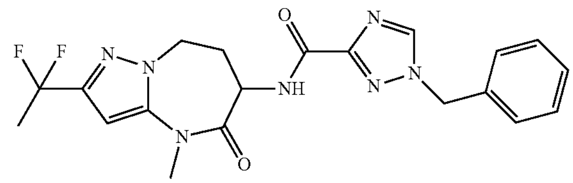 [SMILES: CN1C(=O)C(NC(=O)c2ncn(Cc3ccccc3)n2)CCn2nc(C(C)(F)F)cc21]

1-benzyl-N-[2-(1,1-difluoroethyl)-4-methyl-5-oxo-7,8-dihydro-6H-pyrazolo[1,5-a][1,3]di azepin-6-yl]-1,2,4-triazole-3-carboxamide Step 1: 1-benzyl-N-[2-(1,1-difluoroethyl)-4-methyl-5-oxo-7,8-dihydro-6H-pyrazolo[1,5-a][1,3]di azepin-6-yl]-1,2,4-triazole-3-carboxamide Diethylaminosulfur trifluoride (2.73 mL, 19.64 mmol) was added to a solution of N-(2-acetyl-4-methyl-5-oxo-7,8-dihydro-6H-pyrazolo[1,5-a][1,3]diazepin-6-yl)-1-benzyl-1,2, 4-triazole-3-carboxamide (0.400 g (crude), 0.982 mmol) in dichloromethane (2.0 mL). The reaction was heated at 40° C. for 8 h. After, the reaction was carefully poured into a solution of saturated aqueous sodium bicarbonate. The aqueous layer was extracted with isopropyl acetate (4×50 mL). The combined organic layers were washed with brine, dried with sodium sulfate, concentrated, and the residue was purified by preparative HPLC (see below) to give 1-benzyl-N-[2-(1,1-difluoroethyl)-4-methyl-5-oxo-7,8-dihydro-6H-pyrazolo[1,5-a][1,3]diazepin-6-yl]-1,2,4-triazole-3-carboxamide (16.8 mg, 0.039 mmol, 3.98% Yield)

$^1$H NMR (400.33 MHz, DMSO-d6) δ 8.82 (s, 1H), 8.59 (d, J=7.7 Hz, 1H), 7.43-7.26 (m, 5H), 6.65 (s, 1H), 5.48 (s, 2H), 4.45-4.19 (m, 3H), 3.26 (s, 3H), 2.71-2.54 (m, 1H), 2.51-2.36 (m, 1H), 2.00 (t, J=18.8 Hz, 3H).

LRMS $R_T$=4.55 min, m/z=430.2 [M+H]$^+$.

Column: Es Industries Pyridyl Amide (150×21.2 mm)

Mobile Phase: Carbon Dioxide (A)/Neat methanol (B)

Elution Program

Gradient: Isocratic @ 20%

Pressure: 100 bar

Flow Rate: 70 mL/min

Column Temperature: 40° C.

Wavelength: 220 nm

Example 372

Method CS7

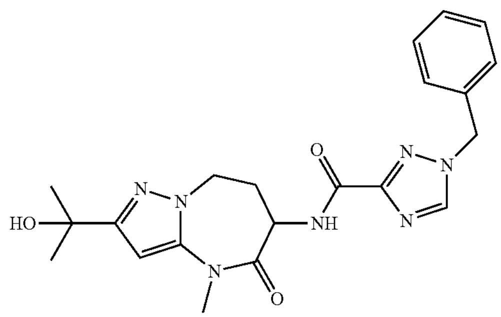 [SMILES: CN1C(=O)C(NC(=O)c2ncn(Cc3ccccc3)n2)CCn2nc(C(C)(C)O)cc21]

1-benzyl-N-[2-(1-hydroxy-1-methyl-ethyl)-4-methyl-5-oxo-7,8-dihydro-6H-pyrazolo[1,5-a][1,3]diazepin-6-yl]-1,2,4-triazole-3-carboxamide Step 1: 1-benzyl-N-[2-(1-hydroxy-1-methyl-ethyl)-4-methyl-5-oxo-7,8-dihydro-6H-pyrazolo[1,5-a][1,3]diazepin-6-yl]-1,2,4-triazole-3-carboxamide Methylmagnesium bromide ((1.4 mol/L) in THF: Toluene (1:3), 2.5 mL, 3.44 mmol) was added to a solution of N-(2-acetyl-4-methyl-5-oxo-7,8-dihydro-6H-pyrazolo[1,5-a][1,3]diazepin-6-yl)-1-benzyl-1,2,4-triazole-3-carboxamide (0.350 g (crude), 0.859 mmol) in tetrahydrofuran (4.3 mL) at −50° C. After 45 min the reaction was quenched with methanol. The solvent was removed under reduced pressure and the residue was purified by preparative HPLC (see below) to give 1-benzyl-N-[2-(1-hydroxy-1-methyl-ethyl)-4-methyl-5-oxo-7,8-dihydro-6H-pyrazolo[1,5-a][1,3]diazepin-6-yl]-1,2,4-triazole-3-carboxamide (33.2 mg, 0.0784 mmol, 9.13% Yield)

$^1$H NMR (400.33 MHz, DMSO-d6) δ 8.82 (s, 1H), 8.52 (d, J=7.9 Hz, 1H), 7.43-7.25 (m, 5H), 6.28 (s, 1H), 5.48 (s, 2H), 4.97 (s, 1H), 4.39-4.25 (m, 2H), 4.20-4.07 (m, 1H), 3.23 (s, 3H), 2.60 (ddd, J=20.6, 7.8, 5.2 Hz, 1H), 2.34 (td, J=12.6, 6.6 Hz, 1H), 1.45 (s, 3H), 1.40 (s, 3H).

LRMS $R_T$=3.56 min, m/z=406.2 $[M+H]^+$.

Column: Phenomenex Gemini-NX C18 5 □m, 110 A (50×30 mm)

Mobile Phase: 0.1% Ammonium Hydroxide in Water (A)/Acetonitrile (B)

Elution Program

Gradient: 5-50 B

Pressure: 800 psi

Flow Rate: 60 mL/min

Column Temperature: 25° C.

Wavelength: 220 nm

Example 373

Method GZ1

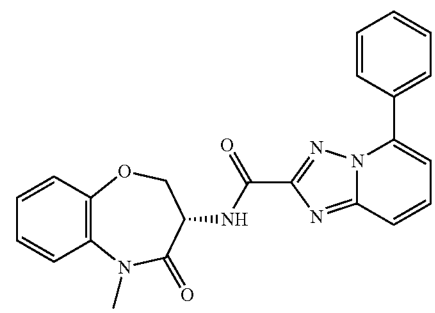 [SMILES: CN1C(=O)[C@@H](NC(=O)c2nc3cccc(-c4ccccc4)n3n2)COc2ccccc21]

(S)—N-(5-methyl-4-oxo-2,3,4,5-tetrahydrobenzo[b][1,4]oxazepin-3-yl)-5-phenyl-[1,2,4]triazolo[1,5-a]pyridine-2-carboxamide

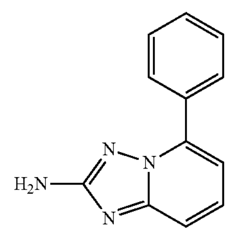 [SMILES: Nc1nc2cccc(-c3ccccc3)n2n1]

Step 1: 5-phenyl-[1,2,4]triazolo[1,5-a]pyridin-2-amine

A mixture of 5-bromo-[1,2,4]triazolo[1,5-a]pyridin-2-amine (580 mg, 2.70 mmol), phenyl boronic acid (496 mg, 4.07 mmol), 2 M of sodium carbonate in water (2.72 ml, 5 mmol) in acetonitrile (9.4 mL) was degassed, and bis(triphenylphosphine)palladium(II) chloride (190 mg, 0.27 mmol) was added under nitrogen. The vial was capped and heated in a microwave to 130° C. for 25 minutes. The reaction mixture was diluted with saturated aqueous sodium bicarbonate (50 mL) and extracted with isopropyl acetate (3×75 mL). The combined organics were dried over sodium sulfate, filtered, and concentrated to dryness in vacuo to afford 5-phenyl-[1,2,4]triazolo[1,5-a]pyridin-2-amine (389 mg, 68%) as a tan solid, used in the next step without further purification. LCMS $R_T$=1.42 min, m/z=211 $(M+H)^+$.

LCMS (5 to 95% acetonitrile in water+0.1% formic acid over 5 mins) retention time 1.42 min, ESI+ found [M+H]=211.

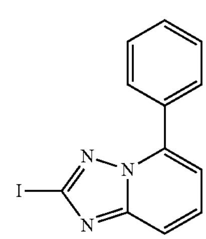 [SMILES: Ic1nc2cccc(-c3ccccc3)n2n1]

Step 2: 2-iodo-5-phenyl-[1,2,4]triazolo[1,5-a]pyridine

To a solution of 5-phenyl-[1,2,4]triazolo[1,5-a]pyridin-2-amine (1050 mg, 4.99 mmol) and p-toluene sulphonic acid (3.65 g, 19.20 mmol) in acetonitrile (45 mL) was added a solution of potassium iodide (2.70 g, 16.00 mmol) and sodium nitrite (865 mg, 12.50 mmol) in water (5 mL) at 24° C. After 18 h, isopropyl acetate was added to the reaction mixture. The resulting solution was washed with water (2×100) and saturated aqueous sodium chloride solution. The organic was dried over magnesium sulfate, filtered, and concentrated. The residue was purified by column chromatography (silica gel, 100-200 mesh, 0 to 100% isopropyl acetate in heptane) affording 2-iodo-5-phenyl-[1,2,4]triazolo[1,5-a]pyridine (780 mg, 49%) as a light yellow solid. LCMS $R_T$=2.27 min, m/z=321.9 $(M+H)^+$.

LCMS (5 to 95% acetonitrile in water+0.1% formic acid over 5 mins) retention time 2.27 min, ESI+ found [M+H]=321.9.

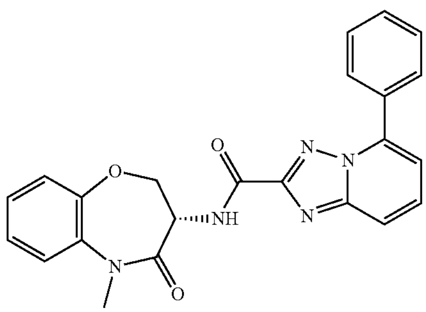 [SMILES: CN1C(=O)[C@@H](NC(=O)c2nc3cccc(-c4ccccc4)n3n2)COc2ccccc21]

Step 3: (S)—N-(5-methyl-4-oxo-2,3,4,5-tetrahydrobenzo[b][1,4]oxazepin-3-yl)-5-phenyl-[1,2,4]triazolo[1,5-a]pyridine-2-carboxamide Palladium(II) acetate (6.0 mg, 0.025 mmol), 4,5-bis(diphenylphosphino)-9,9-dimethylxanthene (21.6 mg, 0.037 mmol), 2-iodo-5-phenyl-[1,2,4]triazolo[1,5-a]pyridine (80 mg, 0.25 mmol), (3S)-3-amino-5-methyl-2,3-dihydro-1,5-benzoxazepin-4-one (47.9 mg, 0.25 mmol) were added to a screw-cap vial. Nitrogen was then purged through the reaction vial for 15 min. The solids were dissolved in toluene (5 mL), and triethylamine (0.226 mL, 1.62 mmol) was added. The reaction flask was purged with a balloon for carbon monoxide for 5 minutes. The vial with the balloon of carbon monoxide, was placed in a 80° C. heating block and was allowed to stir for 16 h. The crude residue was dissolved in isopropyl acetate, and filtered through Celite. The crude residue was purified by flash column chromatography (silica gel, 0% to 100% isopropyl acetate in heptane) to afford (S)—N-(5-methyl-4-oxo-2,3,4,5-tetrahydrobenzo[b][1,4]oxazepin-3-yl)-5-phenyl-[1,2,4]triazol o[1,5-a]pyridine-2-carboxamide (98.0 mg, 95% Yield) as a yellow solid: $^1$H NMR (400 MHz, DMSO-$d_6$) δ 8.79 (d, J=7.8 Hz, 1H), 8.03-7.91 (m, 3H), 7.88 (m, 1H), 7.65-7.55 (m, 3H), 7.50 (ddd, J=14.5, 7.3, 1.7 Hz, 2H), 7.41-7.22 (m, 3H), 4.90 (dt, J=11.4, 7.8 Hz, 1H), 4.63 (dd, J=11.5, 9.9 Hz, 1H), 4.48 (dd, J=9.9, 7.7 Hz, 1H), 3.34 (s, 3H). LCMS RT=5.10 min, m/z=414.1 $(M+H)^+$.

LCMS (5 to 95% acetonitrile in water+0.1% formic acid over 10 mins) retention time 5.10 min, ESI+ found [M+H]=414.1.

Example 374

Method GZ10

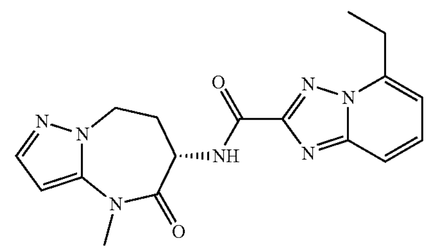 [SMILES: CCc1cccc2nc(C(=O)N[C@H]3CCn4nccc4N(C)C3=O)nn12]

(S)-5-ethyl-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide

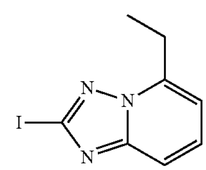

Step 1: 5-ethyl-2-iodo-[1,2,4]triazolo[1,5-a]pyridine

To a solution of 5-ethyl-[1,2,4]triazolo[1,5-a]pyridin-2-amine (800 mg, 4.93 mmol) and p-toluene sulphonic acid (3.60 g, 18.94 mmol) in acetonitrile (45 mL) was added a solution of potassium iodide (2.70 g, 16.23 mmol) and sodium nitrite (854 mg, 12.38 mmol) in water (5 mL) at 24° C. After 18 h, isopropyl acetate was added to the reaction mixture. The resulting solution was washed with water (2×120 mL) and saturated aqueous sodium chloride solution. The organic was dried over magnesium sulfate, filtered, and concentrated. The residue was purified by column chromatography (silica gel, 100-200 mesh, 0 to 100% isopropyl acetate in heptane) affording 5-ethyl-2-iodo-[1,2,4]triazolo[1,5-a]pyridine (908 mg, 67%) as a light yellow solid. LC-MS $R_T$=1.80 min, m/z=273.9 $(M+H)^+$ LCMS (5 to 95% acetonitrile in water+0.1% formic acid over 5 mins) retention time 1.80 min, ESI+ found [M+H]=273.9.

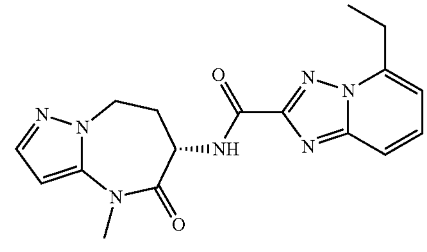 [SMILES: CCc1cccc2nc(C(=O)N[C@H]3CCn4nccc4N(C)C3=O)nn12]

Step 2: (S)-5-ethyl-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide Palladium(II) acetate (8.0 mg, 0.037 mmol), 4,5-bis(diphenylphosphino)-9,9-dimethylxanthene (31.8 mg, 0.055 mmol), 5-ethyl-2-iodo-[1,2,4]triazolo[1,5-a]pyridine (100 mg, 0.37 mmol), (S)-6-amino-4-methyl-7,8-dihydro-4H-pyrazolo[1,5-a][1,3]diazepin-5(6H)-one (66.0 mg, 0.37 mmol) were added to a screw-cap vial. Nitrogen was then purged through the reaction vial for 15 min. The solids were dissolved in toluene (5 mL), and triethylamine (0.33 mL, 2.38 mmol) was added. The reaction flask was purged with a balloon for carbon monoxide for 5 minutes. The vial, with the balloon of carbon monoxide, was placed in a 80° C. heating block and was allowed to stir for 16 h. The crude residue was dissolved in isopropyl acetate, and filtered through Celite. The crude residue was purified by flash column chromatography (silica gel, 0% to 15% dichlolormethane in methanol) to afford (S)-5-ethyl-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide (80.0 mg, 62% Yield) as a tan solid: $^1$H NMR (400 MHz, DMSO-$d_6$) δ 8.87 (d, J=7.8 Hz, 1H), 7.85-7.71 (m, 2H), 7.51 (d, J=2.0 Hz, 1H), 7.20 (dq, J=7.3, 1.2 Hz, 1H), 6.37 (d, J=2.0 Hz, 1H), 4.46-4.33 (m, 2H), 4.23 (ddd, J=14.5, 12.6, 6.6 Hz, 1H), 3.45-3.23 (m, 3H), 3.25-3.11 (m, 2H), 2.67 (tt, J=12.9, 8.1 Hz, 1H), 2.44 (td, J=12.3, 6.5 Hz, 1H), 1.37 (t, J=7.5 Hz, 3H). LC-MS $R_T$=3.51 min, m/z=354.2 $(M+H)^+$.

LCMS (5 to 95% acetonitrile in water+0.1% formic acid over 10 mins) retention time 3.51 min, ESI+ found [M+H]=354.2

Example 375

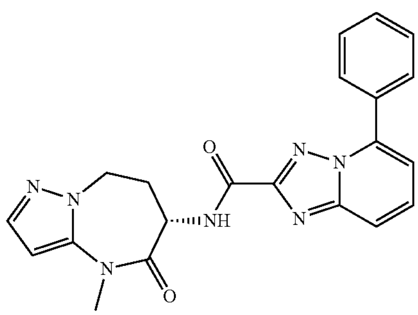 [SMILES: CN1C(=O)[C@@H](NC(=O)c2nc3cccc(-c4ccccc4)n3n2)CCn2nccc21]

(S)—N-(4-methyl-5-oxo-5,6,7,8-tetrahydro-4H-pyrazolo[1,5-a][1,3]diazepin-6-yl)-5-phenyl-[1,2,4]triazolo[1,5-a]pyridine-2-carboxamide was prepared from (S)-6-amino-4-methyl-7,8-dihydro-4H-pyrazolo[1,5-a][1,3]diazepin-5(6H)-one according to Method GZ1. The residue was purified by preparative RP-HPLC (20-60% acetonitrile in water+0.1% formic acid). Yield of final step: 52.8 mg, 42%: $^1$H NMR (400 MHz, DMSO-$d_6$) δ 8.89 (d, J=7.7 Hz, 1H), 8.04-7.83 (m, 4H), 7.65-7.54 (m, 3H), 7.53-7.44 (m, 2H), 6.36 (d, J=2.0 Hz, 1H), 4.45-4.31 (m, 2H), 4.22 (ddd, J=14.5, 12.6, 6.6 Hz, 1H), 3.39-3.19 (m, 3H), 2.76-2.59 (m, 1H), 2.42 (m, 1H). LC-MS $R_T$=4.12 min, m/z=402.1 $(M+H)^+$.

LCMS (5 to 95% acetonitrile in water+0.1% formic acid over 10 mins) retention time 4.12 min, ESI+ found [M+H]=402.1

Example 376

Method GZ2

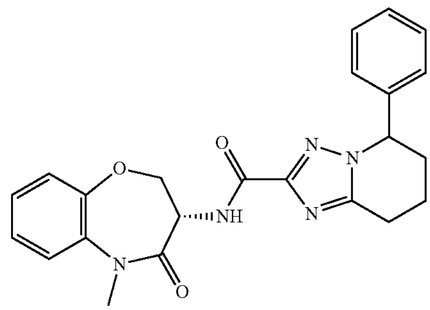 [SMILES: CN1C(=O)[C@@H](NC(=O)c2nc3n(n2)C(c2ccccc2)CCC3)COc2ccccc21]

N—((S)-5-methyl-4-oxo-2,3,4,5-tetrahydrobenzo[b][1,4]oxazepin-3-yl)-5-phenyl-5,6,7,8-tetrahydro-[1,2,4]triazolo[1,5-a]pyridine-2-carboxamide To a solution of (S)—N-(5-methyl-4-oxo-2,3,4,5-tetrahydrobenzo[b][1,4]oxazepin-3-yl)-5-phenyl-[1,2,4]triazol o[1,5-a]pyridine-2-carboxamide (40 mg, 0.097 mmol) in acetic acid (1 mL) was added platinum(iv) oxide (3 mg, 0.0096 mmol, 0.10 equiv). The reaction mixture stirred under a balloon of hydrogen gas for 16 h at RT, then was filtered through Celite and concentrated to dryness in vacuo. The residue was purified by preparative RP-HPLC (20-60% acetonitrile in water+0.1% formic acid) affording N—((S)-5-methyl-4-oxo-2,3,4,5-tetrahydrobenzo[b][1,4]oxazepin-3-yl)-5-phenyl-5,6,7,8-tetra hydro-[1,2,4]triazolo[1,5-a]pyridine-2-carboxamide (16 mg, 40%) as a white solid: $^1$H NMR (400 MHz, DMSO-$d_6$) δ 8.39 (t, J=8.0 Hz, 1H), 7.49 (dt, J=7.5, 1.7 Hz, 1H), 7.40-7.18 (m, 6H), 7.09-7.01 (m, 2H), 5.57 (t, J=5.8 Hz, 1H), 4.80 (dtd, J=11.6, 7.8, 2.3 Hz, 1H), 4.57 (ddd, J=11.5, 9.9, 8.0 Hz, 1H), 4.38 (dd, J=9.9, 7.7 Hz, 1H), 3.44-3.17 (m, 3H), 3.01 (m, 2H), 2.45-2.32 (m, 1H), 2.10-1.99 (m, 1H), 1.92-1.82 (m, 2H). LC-MS $R_T$=4.87 min, m/z=418.2 $(M+H)^+$.

LCMS (5 to 95% acetonitrile in water+0.1% formic acid over 10 mins) retention time 4.87 min, ESI+ found [M+H]=418.2.

Example 377

Method GZ3

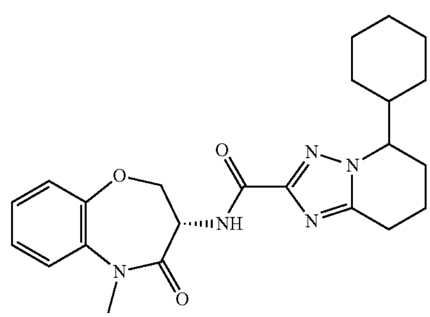 [SMILES: CN1C(=O)[C@@H](NC(=O)c2nc3n(n2)C(C2CCCCC2)CCC3)COc2ccccc21]

5-cyclohexyl-N—((S)-5-methyl-4-oxo-2,3,4,5-tetrahydrobenzo[b][1,4]oxazepin-3-yl)-5,6,7, 8-tetrahydro-[1,2,4]triazolo[1,5-a]pyridine-2-carboxamide To a solution of (S)—N-(5-methyl-4-oxo-2,3,4,5-tetrahydrobenzo[b][1,4]oxazepin-3-yl)-5-phenyl-[1,2,4]triazol o[1,5-a]pyridine-2-carboxamide (40 mg, 0.097 mmol) in acetic acid (1 mL) was added platinum(iv) oxide (3 mg, 0.0096 mmol, 0.10 equiv). The reaction mixture stirred under a balloon of hydrogen gas for 72 h at RT, then was filtered through Celite and concentrated to dryness in vacuo. The residue was purified by preparative RP-HPLC (20-60% acetonitrile in water+0.1% formic acid) affording N—((S)-5-methyl-4-oxo-2,3,4,5-tetrahydrobenzo[b][1,4]oxazepin-3-yl)-5-phenyl-5,6,7,8-tetra hydro-[1,2,4]triazolo[1,5-a]pyridine-2-carboxamide (10 mg, 25%) as a white solid. $^1$H NMR (400 MHz, DMSO-$d_6$) δ 8.37 (m, 1H), 7.55-7.47 (m, 1H), 7.37-7.20 (m, 3H), 4.83 (dtd, J=11.2, 7.9, 3.1 Hz, 1H), 4.57 (ddd, J=17.1, 11.5, 9.8 Hz, 1H), 4.42 (dd, J=9.9, 7.7 Hz, 1H), 4.14 (dt, J=9.0, 4.3 Hz, 1H), 3.42-3.23 (m, 3H), 2.94-2.72 (m, 2H), 2.26 (ms, 1H), 2.00 (m, 2H), 1.90-1.57 (m, 6H), 1.32-1.21 (m, 1H), 1.11 (m, 5H). LC-MS $R_T$=5.60 min, m/z=424.2 $(M+H)^+$.

LCMS (5 to 95% acetonitrile in water+0.1% formic acid over 10 mins) retention time 5.60 min, ESI+ found [M+H]=424.2.

Example 378

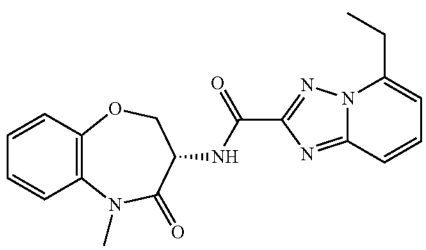 [SMILES: CCc1cccc2nc(C(=O)N[C@H]3COc4ccccc4N(C)C3=O)nn12]

(S)-5-ethyl-N-(5-methyl-4-oxo-2,3,4,5-tetrahydrobenzo[b][1,4]oxazepin-3-yl)-[1,2,4]triazolo[1,5-a]pyridine-2-carboxamide (S)-5-ethyl-N-(5-methyl-4-oxo-2,3,4,5-tetrahydrobenzo [b][1,4]oxazepin-3-yl)-[1,2,4]triazolo [1,5-a]pyridine-2-carboxamide was prepared corresponding from (3S)-3-amino-5-methyl-2,3-dihydro-1,5-benzoxazepin-4-one, and 5-ethyl-2-iodo-[1,2,4]triazolo[1,5-a]pyridine according to Method GZ10. The residue was purified by preparative RP-HPLC (20-60% acetonitrile in water+0.1% formic acid) instead. Yield of final step (35 mg, 26% yield) as a white solid: $^1$H NMR (400 MHz, DMSO-$d_6$) δ 8.78 (d, J=7.9 Hz, 1H), 7.86-7.71 (m, 2H), 7.53 (dd, J=7.5, 2.0 Hz, 1H), 7.39-7.17 (m, 4H), 4.91 (dt, J=11.5, 7.8 Hz, 1H), 4.64 (dd, J=11.5, 9.9 Hz, 1H), 4.49 (dd, J=9.9, 7.7 Hz, 1H), 3.34 (s, 3H), 3.32-3.12 (m, 2H), 1.36 (t, J=7.5 Hz, 3H). LC-MS $R_T$=4.57 min, m/z=366.1 $(M+H)^+$.

LCMS (5 to 95% acetonitrile in water+0.1% formic acid over 10 mins) retention time 4.57 min, ESI+ found [M+H]=366.1

Example 379

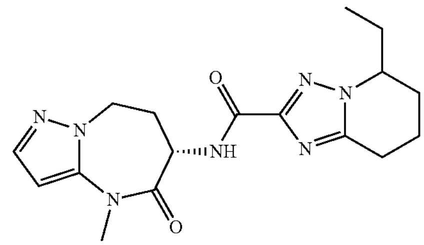 [SMILES: CCC1CCCc2nc(C(=O)N[C@H]3CCn4nccc4N(C)C3=O)nn21]

5-ethyl-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide 5-ethyl-N—((S)-4-methyl-5-oxo-5,6,7,8-tetrahydro-4H-pyrazolo[1,5-a][1,3]diazepin-6-yl)-5,6, 7,8-tetrahydro-[1,2,4]triazolo[1,5-a]pyridine-2-carboxamide was prepared from (S)-5-ethyl-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide according to Method GZ2 affording final product (20 mg, 40%) as a white. $^1$H NMR (400 MHz, DMSO-$d_6$) δ 8.43 (dd, J=10.8, 7.9 Hz, 1H), 7.49 (d, J=2.0 Hz, 1H), 6.34 (d, J=2.0 Hz, 1H), 4.42-4.12 (m, 3H), 3.25 (d, J=1.9 Hz, 3H), 2.94-2.74 (m, 2H), 2.67-2.52 (m, 1H), 2.37 (dt, J=13.3, 8.2 Hz, 1H), 2.20-1.91 (m, 3H), 1.87-1.65 (m, 4H), 1.24 (s, 2H), 0.91 (t, J=7.4 Hz, 3H). LC-MS $R_T$=3.50 min, m/z=358.2 $(M+H)^+$.

LCMS (5 to 95% acetonitrile in water+0.1% formic acid over 10 mins) retention time 3.50 min, ESI+ found [M+H]=358.2

Example 380

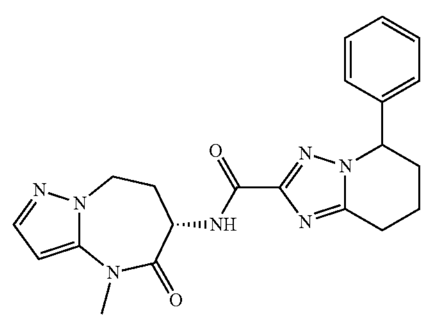 [SMILES: CN1C(=O)[C@@H](NC(=O)c2nc3n(n2)C(c2ccccc2)CCC3)CCn2nccc21]

N—((S)-4-methyl-5-oxo-5,6,7,8-tetrahydro-4H-pyrazolo[1,5-a][1,3]diazepin-6-yl)-5-phenyl-5,6,7,8-tetrahydro-[1,2,4]triazolo[1,5-a]pyridine-2-carboxamide N—((S)-4-methyl-5-oxo-5,6,7,8-tetrahydro-4H-pyrazolo[1,5-a][1,3]diazepin-6-yl)-5-phenyl-5, 6,7,8-tetrahydro-[1,2,4]triazolo[1,5-a]pyridine-2-carboxamide was prepared from (S)—N-(4-methyl-5-oxo-5,6,7,8-tetrahydro-4H-pyrazolo[1,5-a][1,3]diazepin-6-yl)-5-phenyl-[1,2,4]triazolo[1,5-a]pyridine-2-carboxamide according to Method GZ2. The residue was purified by preparative RP-HPLC (5-50% acetonitrile in water+0.1% formic acid) to afford final product (23 mg, 28%) as a white. $^1$H NMR (400 MHz, DMSO-$d_6$) δ 8.47 (m, 1H), 7.48 (s, 1H), 7.40-7.26 (m, 3H), 7.09-7.02 (m, 2H), 6.33 (t, J=1.8 Hz, 1H), 5.57 (t, J=5.8 Hz, 1H), 4.26 (m, 3H), 3.23 (s, 3H), 3.11-2.87 (m, 2H), 2.57 (ddt, J=12.5, 8.2, 4.3 Hz, 1H), 2.37 (tq, J=11.8, 5.6 Hz, 2H), 2.05 (ddd, J=14.6, 7.5, 4.8 Hz, 1H), 1.86 (p, J=6.4 Hz, 2H). LC-MS $R_T$=3.95 min, m/z=406.2 $(M+H)^+$.

LCMS (5 to 95% acetonitrile in water+0.1% formic acid over 10 mins) retention time 3.95 min, ESI+ found [M+H]=406.2

Example 381

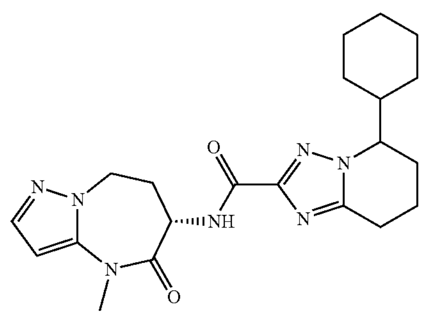 [SMILES: CN1C(=O)[C@@H](NC(=O)c2nc3n(n2)C(C2CCCCC2)CCC3)CCn2nccc21]

5-cyclohexyl-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide 5-cyclohexyl-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide was prepared from (S)—N-(4-methyl-5-oxo-5,6,7,8-tetrahydro-4H-pyrazolo[1,5-a][1,3]diazepin-6-yl)-5-phenyl-[1,2,4]triazolo[1,5-a]pyridine-2-carboxamide according to Method GZ3. The residue was purified by preparative RP-HPLC (20-60% acetonitrile in water+0.1% formic acid) to afford final product (6.1 mg, 97%) as a white. $^1$H NMR (400 MHz, DMSO-$d_6$) δ 8.55-8.35 (m, 1H), 7.50 (d, J=1.9 Hz, 1H), 6.35 (d, J=2.2 Hz, 1H), 4.41-4.31 (m, 1H), 4.26-4.10 (m, 2H), 3.45 (s, 3H), 2.94-2.84 (m, 1H), 2.00 (m, 2H), 1.76 (t, J=6.2 Hz, 2H), 1.68 (s, 10H), 1.43 (m, 2H), 1.24 (s, 4H), 1.12 (m, 4H). LC-MS $R_T$=4.71 min, m/z=412.2 $(M+H)^+$.

LCMS (5 to 95% acetonitrile in water+0.1% formic acid over 10 mins) retention time 4.71 min, ESI+ found [M+H]=412.2

Example 382

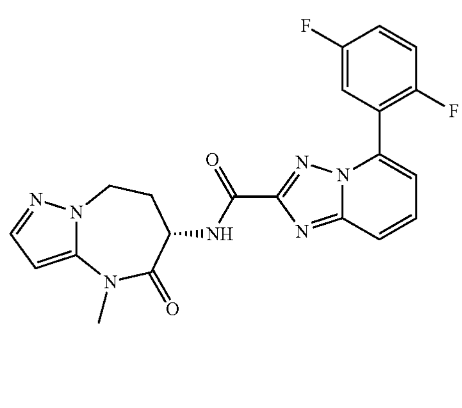 [SMILES: CN1C(=O)[C@@H](NC(=O)c2nc3cccc(-c4cc(F)ccc4F)n3n2)CCn2nccc21]

(S)-5-(2,5-difluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide (S)-5-(2,5-difluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide was prepared corresponding from (S)-6-amino-4-methyl-7,8-dihydro-4H-pyrazolo[1,5-a][1,3]diazepin-5(6H)-one, and 5-(2,5-difluorophenyl)-2-iodo-[1,2,4]triazolo[1,5-a]pyridine according to Method GZ1. The residue was purified by preparative RP-HPLC (20-60% acetonitrile in water+0.1% formic acid) instead. Yield of final step: 59 mg, 48%. $^1$H NMR (400 MHz, DMSO-$d_6$) δ 8.89 (d, J=7.7 Hz, 1H), 8.05 (dd, J=9.0, 1.2 Hz, 1H), 7.90 (dd, J=9.0, 7.1 Hz, 1H), 7.71 (tt, J=6.1, 2.1 Hz, 1H), 7.59-7.47 (m, 4H), 6.35 (d, J=2.0 Hz, 1H), 4.44-4.29 (m, 2H), 4.21 (ddd, J=14.4, 12.6, 6.6 Hz, 1H), 3.26 (s, 3H), 2.76-2.57 (m, 1H), 2.42 (m, 1H). LC-MS $R_T$=4.26 min, m/z=438.1 $(M+H)^+$.

LCMS (5 to 95% acetonitrile in water+0.1% formic acid over 10 mins) retention time 4.26 min, ESI+ found [M+H]=438.1

Example 383

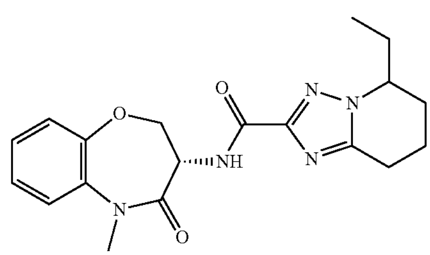 [SMILES: CCC1CCCc2nc(C(=O)N[C@H]3COc4ccccc4N(C)C3=O)nn21]

5-ethyl-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide 5-ethyl-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide was prepared from (S)-5-ethyl-N-(5-methyl-4-oxo-2,3,4,5-tetrahydrobenzo[b][1,4]oxazepin-3-yl)-[1,2,4]triazolo [1,5-a]pyridine-2-carboxamide according to Method GZ2 affording final product (11.5 mg, 44%) as a white. $^1$H NMR (400 MHz, DMSO-$d_6$) δ 8.36 (t, J=7.5 Hz, 1H), 7.50 (dd, J=7.5, 1.9 Hz, 1H), 7.37-7.20 (m, 3H), 4.83 (dtd, J=11.5, 7.8, 2.0 Hz, 1H), 4.56 (dt, J=11.4, 9.7 Hz, 1H), 4.41 (ddd, J=9.5, 7.7, 1.3 Hz, 1H), 4.17 (d, J=8.5 Hz, 1H), 2.95-2.76 (m, 2H), 2.18-1.91 (m, 3H), 1.86-1.65 (m, 3H), 0.91 (td, J=7.5, 1.4 Hz, 3H). LC-MS $R_T$=4.52 min, m/z=370.2 $(M+H)^+$.

LCMS (5 to 95% acetonitrile in water+0.1% formic acid over 10 mins) retention time 4.52 min, ESI+ found [M+H]=370.2

Examples 384 and 385

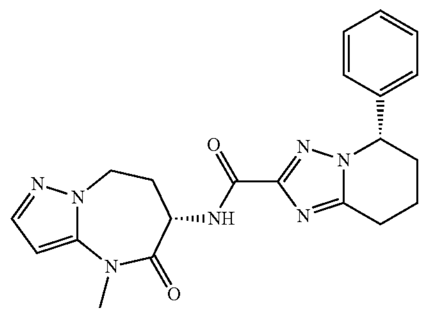

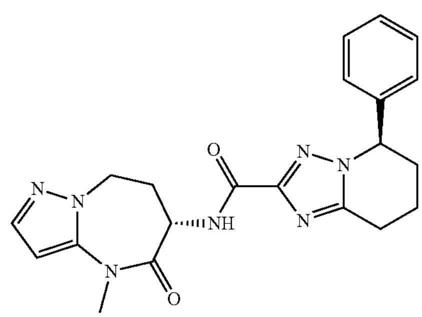

(S)—N—((S)-4-methyl-5-oxo-5,6,7,8-tetrahydro-4H-pyrazolo[1,5-a][1,3]diazepin-6-yl)-5-phenyl-5,6,7,8-tetrahydro-[1,2,4]triazolo[1,5-a]pyridine-2-carboxamide and (R)—N—((S)-4-methyl-5-oxo-5,6,7,8-tetrahydro-4H-pyrazolo[1,5-a][1,3]diazepin-6-yl)-5-phenyl-5,6,7,8-tetrahydro-[1,2,4]triazolo[1,5-a]pyridine-2-carboxamide (1:1)

N—((S)-4-methyl-5-oxo-5,6,7,8-tetrahydro-4H-pyrazolo[1,5-a][1,3]diazepin-6-yl)-5-phenyl-5, 6,7,8-tetrahydro-[1,2,4]triazolo[1,5-a]pyridine-2-carboxamide was prepared from (S)—N-(4-methyl-5-oxo-5,6,7,8-tetrahydro-4H-pyrazolo[1,5-a][1,3]diazepin-6-yl)-5-phenyl-[1,2,4]triazolo[1,5-a]pyridine-2-carboxamide according to Method GZ2. The crude residue was further purified by chiral SFC (Chiralpak AD 157×21.2 mm, 5 um, 30% methanol isocratic elution with Carbon Dioxide) affording arbitrarily assigned diastereomers (S)—N—((S)-4-methyl-5-oxo-5,6,7,8-tetrahydro-4H-pyrazolo[1,5-a][1,3]diazepin-6-yl)-5-phenyl-5,6,7,8-tetrahydro-[1,2,4]triazolo[1,5-a]pyridine-2-carboxamide (7.1 mg, 20%) and (R)—N—((S)-4-methyl-5-oxo-5,6,7,8-tetrahydro-4H-pyrazolo[1,5-a][1,3]diazepin-6-yl)-5-phen yl-5,6,7,8-tetrahydro-[1,2,4]triazolo[1,5-a]pyridine-2-carboxamide (7.5 mg, 21%) as white solids:

Analytical data for the first eluting diastereomer (arbitrarily assigned R,S configuration): SFC $R_T$ (AD column, 20% methanol isocratic elution with Carbon Dioxide, 2.5 min method): 0.94 min, 100% ee: $^1$H NMR (400 MHz, DMSO-$d_6$) δ 8.46 (d, J=7.9 Hz, 1H), 7.48 (d, J=2.0 Hz, 1H), 7.40-7.26 (m, 3H), 7.09-7.01 (m, 2H), 6.33 (d, J=2.0 Hz, 1H), 5.57 (t, J=5.8 Hz, 1H), 4.41-4.11 (m, 3H), 3.24 (s, 3H), 3.10-2.90 (m, 2H), 2.57 (ddd, J=12.9, 8.0, 5.0 Hz, 1H), 2.37 (tq, J=12.4, 5.9 Hz, 2H), 2.11-1.98 (m, 1H), 1.86 (p, J=6.3 Hz, 2H). LCMS $R_T$=4.00 min, m/z=406.2 $(M+H)^+$.

LCMS (5 to 95% acetonitrile in water+0.1% formic acid over 10 mins) retention time 4.00 min, ESI+ found [M+H]=406.2

Analytical data for the second eluting diastereomer (arbitrarily assigned S,S configuration): SFC $R_T$ (AD column, 20% methanol+0.1% ammonium hydroxide isocratic elution, 2.5 min method): 1.28 min, 100% ee: $^1$H NMR (400 MHz, DMSO-$d_6$) δ 8.49 (d, J=7.9 Hz, 1H), 7.47 (d, J=2.0 Hz, 1H), 7.41-7.26 (m, 3H), 7.05 (dd, J=7.0, 1.8 Hz, 2H), 6.33 (d, J=2.0 Hz, 1H), 5.57 (t, J=5.9 Hz, 1H), 4.41-4.11 (m, 3H), 3.23 (s, 3H), 3.00 (qt, J=17.2, 6.3 Hz, 2H), 2.56 (ddd, J=12.9, 8.0, 5.0 Hz, 1H), 2.43-2.32 (m, 2H), 2.11-1.98 (m, 1H), 1.87 (q, J=6.2 Hz, 2H). LCMS $R_T$=4.00 min, m/z=406.2 $(M+H)^+$.

LCMS (5 to 95% acetonitrile in water+0.1% formic acid over 10 mins) retention time 4.00 min, ESI+ found [M+H]=406.2

Example 386

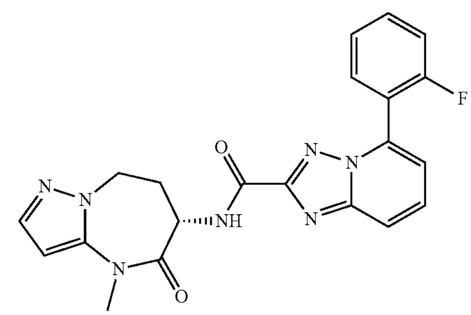 [SMILES: CN1C(=O)[C@@H](NC(=O)c2nc3cccc(-c4ccccc4F)n3n2)CCn2nccc21]

(S)-5-(2-fluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide (S)-5-(2-fluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide was prepared corresponding from (S)-6-amino-4-methyl-7,8-dihydro-4H-pyrazolo[1,5-a][1,3]diazepin-5(6H)-one, and 5-(2-fluorophenyl)-2-iodo-[1,2,4]triazolo[1,5-a]pyridine according to Method GZ1. The residue was purified by preparative RP-HPLC (20-60% acetonitrile in water+0.1% formic acid) instead. Yield of final step: 18.3 mg, 17%. $^1$H NMR (400 MHz, DMSO-$d_6$) δ 8.87 (d, J=7.7 Hz, 1H), 8.07-7.85 (m, 2H), 7.80-7.62 (m, 2H), 7.52-7.32 (m, 4H), 6.35 (d, J=2.0 Hz, 1H), 4.44-4.28 (m, 2H), 4.21 (ddd, J=14.5, 12.6, 6.6 Hz, 1H), 3.26 (s, 3H), 2.65 (tt, J=12.9, 8.1 Hz, 1H), 2.41 (td, J=12.4, 6.4 Hz, 1H). LC-MS $R_T$=4.19 min, m/z=420.1 $(M+H)^+$.

LCMS (5 to 95% acetonitrile in water+0.1% formic acid over 10 mins) retention time 4.19 min, ESI+ found [M+H]=420.1

Example 387

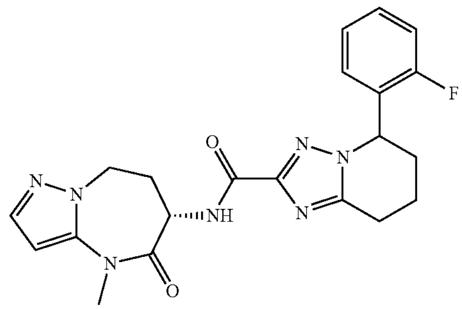 [SMILES: CN1C(=O)[C@@H](NC(=O)c2nc3n(n2)C(c2ccccc2F)CCC3)CCn2nccc21]

5-(2-fluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide 5-(2-fluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide was prepared from (S)-5-(2-fluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide according to Method GZ2. The residue was purified by preparative RP-HPLC (5-50% acetonitrile in water+0.1% formic acid) to afford final product (13.1 mg, 36%) as a white. $^1$H NMR (400 MHz, DMSO-$d_6$) δ 8.55-8.43 (m, 1H), 7.47 (d, J=2.0 Hz, 1H), 7.44-7.34 (m, 1H), 7.29-7.14 (m, 2H), 6.94 (td, J=7.7, 1.7 Hz, 1H), 6.33 (t, J=1.6 Hz, 1H), 5.74 (t, J=6.5 Hz, 1H), 4.41-4.11 (m, 3H), 3.43-3.21 (m, 4H), 3.07-2.92 (m, 2H), 2.57 (dtd, J=17.3, 8.8, 8.3, 4.4 Hz, 1H), 2.39 (tt, J=12.7, 6.0 Hz, 2H), 2.15-2.01 (m, 1H), 1.92 (p, J=6.2 Hz, 2H). LC-MS $R_T$=3.95 min, m/z=424.2 $(M+H)^+$.

LCMS (5 to 95% acetonitrile in water+0.1% formic acid over 10 mins) retention time 3.95 min, ESI+ found [M+H]=424.2

Example 388

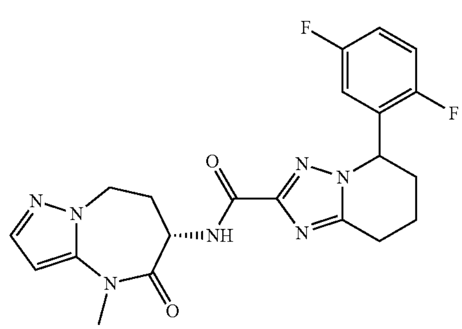 [SMILES: CN1C(=O)[C@@H](NC(=O)c2nc3n(n2)C(c2cc(F)ccc2F)CCC3)CCn2nccc21]

5-(2,5-difluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide 5-(2,5-difluorophenyl)-N—((S)-4-methyl-5-oxo-5,6,7,8-tetrahydr-4H-pyrazolo[1,5-a][1,3]diazepin-6-yl)-5,6,7,8-tetrahydro-[1,2,4]triazolo[1,5-a]pyridine-2-carboxamide was prepared from (S)-5-(2,5-difluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide according to Method GZ2. The residue was purified by preparative RP-HPLC (5-50% acetonitrile in water+0.1% formic acid) to afford final product (8 mg, 20%) as a white. $^1$H NMR (400 MHz, DMSO-$d_6$) δ 8.50 (dd, J=12.8, 7.8 Hz, 1H), 7.48 (d, J=2.0 Hz, 1H), 7.37-7.19 (m, 2H), 6.93 (dt, J=8.6, 4.2 Hz, 1H), 6.33 (t, J=1.7 Hz, 1H), 5.75-5.66 (m, 1H), 4.41-4.11 (m, 3H), 3.35 (d, J=16.9 Hz, 1H), 3.24 (d, J=1.7 Hz, 3H), 3.08-2.87 (m, 2H), 2.57 (ddt, J=16.7, 8.6, 3.8 Hz, 1H), 2.38 (dt, J=12.3, 6.2 Hz, 2H), 2.09 (q, J=11.1, 10.3 Hz, 1H), 1.95 (d, J=7.9 Hz, 2H). LC-MS $R_T$=4.19 min, m/z=442.2 $(M+H)^+$.

LCMS (5 to 95% acetonitrile in water+0.1% formic acid over 10 mins) retention time 4.19 min, ESI+ found [M+H]=442.2

Example 389

Method GZ14

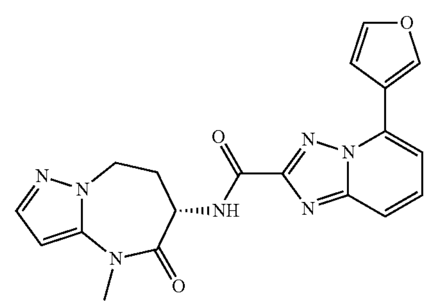 [SMILES: CN1C(=O)[C@@H](NC(=O)c2nc3cccc(-c4ccoc4)n3n2)CCn2nccc21]

(S)-5-(furan-3-yl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide

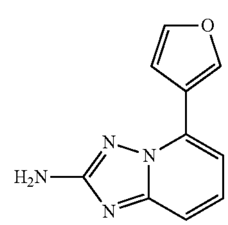 [SMILES: Nc1nc2cccc(-c3ccoc3)n2n1]

Step 1: 5-(furan-3-yl)-[1,2,4]triazolo[1,5-a]pyridin-2-amine

A mixture of 5-bromo-[1,2,4]triazolo[1,5-a]pyridin-2-amine (500 mg, 2.347 mmol), furan-3-boronic acid (394 mg, 2.520 mmol), tripotassium phosphate (1495 mg, 7.041 mmol) in tetrahydrofuran (16 mL) and water (4 mL) was degassed, then 2-Dicyclohexylphosphino-2',4',6'-triisopropylbiphenyl (67 mg, 0.141 mmol) and X-Phos aminobiphenyl palladium chloride precatalyst (XPhos-Pd-G2) (52 mg, 0.0705 mmol) was added under nitrogen. The microwave vial was capped and heated to 85° C. for 45 minutes. The reaction mixture was cooled down, diluted with saturated aqueous sodium bicarbonate (50 mL) and extracted with isopropyl acetate (3×75 mL). The combined organics were dried over sodium sulfate, filtered, and concentrated to dryness in vacuo, triturated with isopropyl acetate, filtered out the solid to afford 5-(furan-3-yl)-[1,2,4]triazolo[1,5-a]pyridin-2-amine (400 mg, 85%) as a tan solid. LC-MS $R_T$=1.61 min, m/z=201.1 $(M+H)^+$.

LCMS (5 to 95% acetonitrile in water+0.1% formic acid over 5 mins) retention time 1.61 min, ESI+ found [M+H]=201.1.

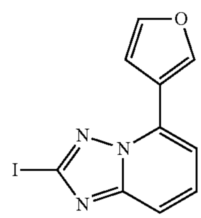 [SMILES: Ic1nc2cccc(-c3ccoc3)n2n1]

Step 2: 5-(furan-3-yl)-2-iodo-[1,2,4]triazolo[1,5-a]pyridine

To a solution of 5-(furan-3-yl)-[1,2,4]triazolo[1,5-a]pyridin-2-amine (300 mg, 1.424 mmol) and p-toluene sulphonic acid (1.04 g, 5.467 mmol) in acetonitrile (10 mL) was added a solution of potassium iodide (780 mg, 4.698 mmol) and sodium nitrite (247 mg, 3.573 mmol) in water (2 mL) at 24° C. After 18 h, isopropyl acetate was added to the reaction mixture. The resulting solution was washed with water (2×100) and saturated aqueous sodium chloride solution. The organic was dried over magnesium sulfate, filtered, and concentrated. The residue was purified by column chromatography (silica gel, 100-200 mesh, 0 to 100% isopropyl acetate in heptane) affording 5-(furan-3-yl)-2-iodo-[1,2,4]triazolo[1,5-a]pyridine (248 mg, 56%) as a light yellow solid. LC-MS $R_T$=2.48 min, m/z=312.1 $(M+H)^+$.

LCMS (5 to 95% acetonitrile in water+0.1% formic acid over 5 mins) retention time 2.48 min, ESI+ found [M+H]=312.1.

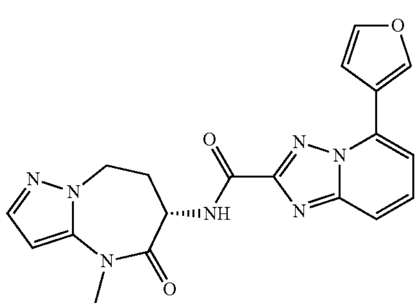 [SMILES: CN1C(=O)[C@@H](NC(=O)c2nc3cccc(-c4ccoc4)n3n2)CCn2nccc21]

Step 3: (S)-5-(furan-3-yl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide Palladium(II) acetate (7 mg, 0.032 mmol), 4,5-bis(diphenylphosphino)-9,9-dimethylxanthene (28 mg, 0.0482 mmol), 5-(furan-3-yl)-2-iodo-[1,2,4]triazolo[1,5-a]pyridine (100 mg, 0.321 mmol), (S)-6-amino-4-methyl-7,8-dihydro-4H-pyrazolo[1,5-a][1,3]diazepin-5(6H)-one (116 mg, 0.643 mmol) were added to a screw-cap vial. Nitrogen was then purged through the reaction vial for 15 min. The solids were dissolved in toluene (3 mL), and triethylamine (0.30 mL, 2.090 mmol) was added. The reaction flask was purged with a balloon for carbon monoxide for 5 minutes. The vial, with the balloon of carbon monoxide, was placed in a 80° C. heating block and was allowed to stir for 16 h. The crude residue was dissolved in isopropyl acetate, and filtered through Celite. The residue was purified by preparative RP-HPLC (5-50% acetonitrile in water+0.1% formic acid) to afford (S)-5-(furan-3-yl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide as tan solid (58 mg, 59% yield). $^1H$ NMR (400 MHz, DMSO-$d_6$) δ 9.21 (d, J=1.4 Hz, 1H), 9.11 (d, J=7.9 Hz, 1H), 7.97 (t, J=1.8 Hz, 1H), 7.94-7.77 (m, 3H), 7.52 (d, J=2.0 Hz, 1H), 7.43 (d, J=2.0 Hz, 1H), 6.38 (d, J=2.0 Hz, 1H), 4.50-4.38 (m, 2H), 4.24 (ddd, J=14.4, 12.6, 6.6 Hz, 1H), 3.29 (s, 3H), 2.76-2.50 (m, 2H). LC-MS $R_T$=3.95 min, m/z=392.1 $(M+H)^+$.

LCMS (5 to 95% acetonitrile in water+0.1% formic acid over 10 mins) retention time 3.95 min, ESI+ found [M+H]=392.1

Example 390

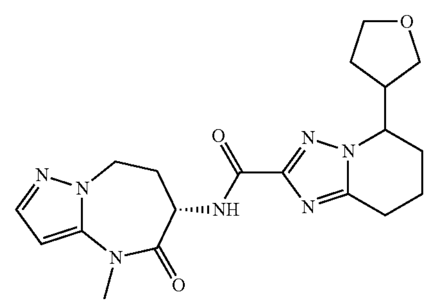 [SMILES: CN1C(=O)[C@@H](NC(=O)c2nc3n(n2)C(C2CCOC2)CCC3)CCn2nccc21]

N—((S)-4-methyl-5-oxo-5,6,7,8-tetrahydro-4H-pyrazolo[1,5-a][1,3]diazepin-6-yl)-5-(tetra hydrofuran-3-yl)-5,6,7,8-tetrahydro-[1,2,4]triazolo[1,5-a]pyridine-2-carboxamide N—((S)-4-methyl-5-oxo-5,6,7,8-tetrahydro-4H-pyrazolo[1,5-a][1,3]diazepin-6-yl)-5-(tetrahydrofuran-3-yl)-5,6,7,8-tetrahydro-[1,2,4]triazolo[1,5-a]pyridine-2-carboxamide was prepared from (S)-5-(furan-3-yl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide according to Method GZ2. The residue was purified by preparative RP-HPLC (5-50% acetonitrile in water+0.1% formic acid) to afford final product (0.8 mg, 2.5%) as a white solid. LC-MS $R_T$=3.21 min, m/z=400.2 $(M+H)^+$.

LCMS (5 to 95% acetonitrile in water+0.1% formic acid over 10 mins) retention time 3.21 min, ESI+ found [M+H]=400.2

Example 391

Method GZ9

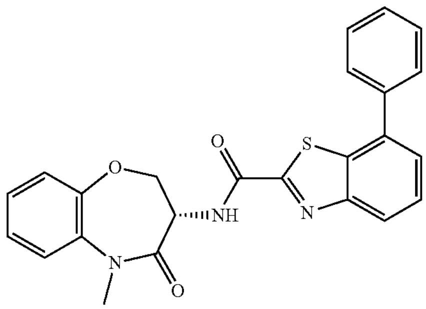 [SMILES: CN1C(=O)[C@@H](NC(=O)c2nc3cccc(-c4ccccc4)c3s2)COc2ccccc21]

(S)—N-(5-methyl-4-oxo-2,3,4,5-tetrahydrobenzo[b][1,4]oxazepin-3-yl)-7-phenylbenzo[d]thiazole-2-carboxamide

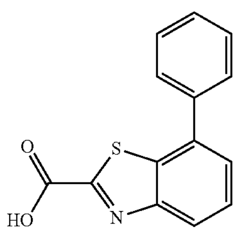 [SMILES: O=C(O)c1nc2cccc(-c3ccccc3)c2s1]

Step 1: 7-phenylbenzo[d]thiazole-2-carboxylic acid

A mixture of 7-bromobenzo[d]thiazole-2-carboxylic acid (500 mg, 1.88 mmol), phenyl boronic acid (458 mg, 3.76 mmol), potassium phosphate (1195 mg, 5.64 mmol) in Water (0.6 mL) and 1,4-dioxane (2 mL) was degassed, and bis(di-tert-butyl(4-dimethylaminophenyl)phosphine)dichloropalladium(II) (70 mg, 0.094 mmol) was added under nitrogen. The vial was capped and heated to 85° C. for 3 h. The reaction mixture was diluted with saturated aqueous sodium bicarbonate (50 mL) and extracted with isopropyl acetate (3×75 mL). The combined organics were dried over sodium sulfate, filtered, and concentrated to dryness in vacuo to afford 7-phenylbenzo[d]thiazole-2-carboxylic acid (469 mg, 98%) as a fluffy tan solid, which was used in the next step without further purification.

LCMS (5 to 95% acetonitrile in water+0.1% formic acid over 5 mins) retention time 2.06 min, ESI+ found [M+H]=255.9.

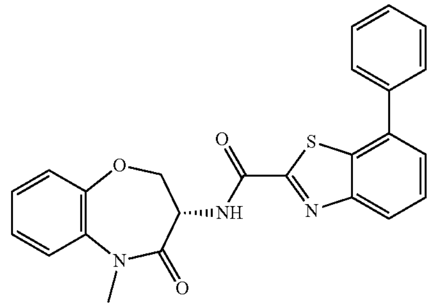 [SMILES: CN1C(=O)[C@@H](NC(=O)c2nc3cccc(-c4ccccc4)c3s2)COc2ccccc21]

Step 2: (S)—N-(5-methyl-4-oxo-2,3,4,5-tetrahydrobenzo[b][1,4]oxazepin-3-yl)-7-phenylbenzo[d]thiazole-2-carboxamide To a solution of (S)-3-amino-5-methyl-2,3-dihydrobenzo[b][1,4]oxazepin-4(5H)-one (93 mg, 0.409 mmol) and 7-phenylbenzo[d]thiazole-2-carboxylic acid (63 mg, 0.272 mmol) in N,N-dimethylformamide (2 mL) was added HATU (135 mg, 0.343 mmol), and N,N-diisopropylethylamine (0.16 mL, 0.936 mmol). The reaction mixture was stirred overnight at RT. The reaction mixture was diluted with saturated aqueous sodium bicarbonate (50 mL) and extracted with isopropyl acetate (3×75 mL). The combined organics were dried over sodium sulfate, filtered, and concentrated to dryness in vacuo. The crude residue was purified directly by preparative RP-HPLC (40-80% acetonitrile in water+0.1% formic acid) affording(S)—N-(5-methyl-4-oxo-2,3,4,5-tetrahydrobenzo[b][1,4]oxazepin-3-yl)-7-phenylbenzo[d]thiazole-2-carboxamide (77 mg, 58%) as a white solid: $^1$H NMR (400 MHz, DMSO-$d_6$) δ 9.26 (d, J=8.0 Hz, 1H), 8.22 (dd, J=8.1, 1.0 Hz, 1H), 7.83-7.68 (m, 4H), 7.62-7.45 (m, 4H), 7.30 (m, 3H), 4.89 (m, 1H), 4.75 (m, 1H), 4.48 (m, 1H), 3.33 (s, 3H). LC-MS $R_T$=6.75 min, m/z=430.1 $(M+H)^+$.

LCMS (5 to 95% acetonitrile in water+0.1% formic acid over 10 mins) retention time 6.75 min, ESI+ found [M+H]=430.1

Example 392

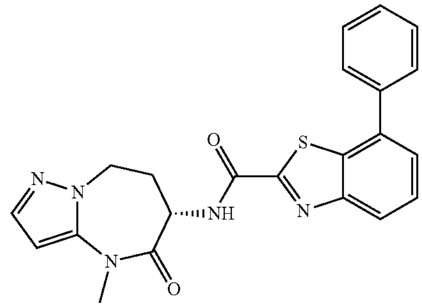 [SMILES: CN1C(=O)[C@@H](NC(=O)c2nc3cccc(-c4ccccc4)c3s2)CCn2nccc21]

(S)—N-(4-methyl-5-oxo-5,6,7,8-tetrahydro-4H-pyrazolo[1,5-a][1,3]diazepin-6-yl)-7-phenylbenzo[d]thiazole-2-carboxamide (S)—N-(4-methyl-5-oxo-5,6,7,8-tetrahydro-4H-pyrazolo[1,5-a][1,3]diazepin-6-yl)-7-phenylbenzo[d]thiazole-2-carboxamide was prepared from (S)-6-amino-4-methyl-7,8-dihydro-4H-pyrazolo[1,5-a][1,3]diazepin-5(6H)-one and 7-phenylbenzo[d]thiazole-2-carboxylic acid according to Method GZ9. The crude residue was purified directly by preparative RP-HPLC (30-70% acetonitrile in water+0.1% formic acid) to afford final product (79 mg, 57%) as a white. $^1$H NMR (400 MHz, DMSO-$d_6$) δ 9.38 (d, J=7.7 Hz, 1H), 8.21 (dd, J=8.3, 1.1 Hz, 1H), 7.83-7.67 (m, 4H), 7.62-7.45 (m, 4H), 6.36 (d, J=2.0 Hz, 1H), 4.47-4.17 (m, 3H), 3.27 (s, 3H), 2.65 (m, 2H). LC-MS $R_T$=5.70 min, m/z=418.1 $(M+H)^+$.

LCMS (5 to 95% acetonitrile in water+0.1% formic acid over 10 mins) retention time 5.70 min, ESI+ found [M+H]=418.1

Example 393

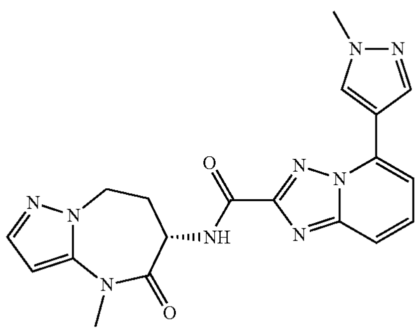 [SMILES: CN1C(=O)[C@@H](NC(=O)c2nc3cccc(-c4cnn(C)c4)n3n2)CCn2nccc21]

(S)-5-(1-methyl-1H-pyrazol-4-yl)-N-(4-methyl-5-oxo-5,6,7,8-tetrahydro-4H-pyrazol-[1,5-a][1,3]diazepin-6-yl)-[1,2,4]triazolo[1,5-a]pyridine-2-carboxamide (S)-5-(1-methyl-1H-pyrazol-4-yl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide was prepared corresponding from (S)-6-amino-4-methyl-7,8-dihydro-4H-pyrazolo[1,5-a][1,3]diazepin-5(6H)-one, and 2-iodo-5-(1-methyl-1H-pyrazol-4-yl)-[1,2,4]triazolo[1,5-a]pyridine according to Method GZ14. The residue was purified by preparative RP-HPLC (5-50% acetonitrile in water+0.1% formic acid) instead. Yield of final step: 49.3 mg, 39.5%. $^1$H NMR (400 MHz, DMSO-$d_6$) δ 9.03 (d, J=7.8 Hz, 1H), 8.94 (s, 1H), 8.51 (s, 1H), 7.87-7.72 (m, 3H), 7.52 (d, J=2.0 Hz, 1H), 6.38 (d, J=2.0 Hz, 1H), 4.49-4.36 (m, 2H), 4.24 (ddd, J=14.5, 12.6, 6.6 Hz, 1H), 4.00 (s, 3H), 3.29 (s, 3H), 2.76-2.61 (m, 1H), 2.58-2.44 (m, 1H). LC-MS $R_T$=3.49 min, m/z=406.2 $(M+H)^+$.

LCMS (5 to 95% acetonitrile in water+0.1% formic acid over 10 mins) retention time 3.49 min, ESI+ found [M+H]=406.2

Example 394

Method GZ13

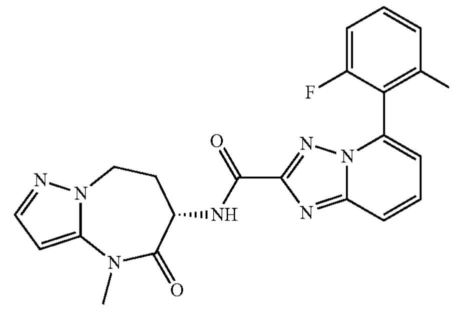

(S)-5-(2,6-difluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide

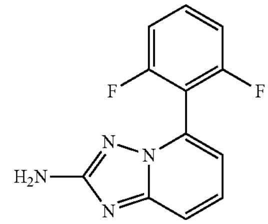 [SMILES: Nc1nc2cccc(-c3c(F)cccc3F)n2n1]

Step 1: 5-(2,6-difluorophenyl)-[1,2,4]triazolo[1,5-a]pyridin-2-amine

A mixture of 5-bromo-[1,2,4]triazolo[1,5-a]pyridin-2-amine (100 mg, 0.469 mmol), 2,6-difluorophenylboronic acid (227 mg, 1.408 mmol), potassium fluoride (82 mg, 1.408 mmol) in tetrahydrofuran (6 mL) and water (0.6 mL) was degassed, followed by adding tris(dibenzylideneacetone)dipalladium(0) (44 mg, 0.0469 mmol), tri-tert-butylphosphine (1.0 mol/l) in toluene (0.09 mL, 0.094 mmol) under nitrogen. The vial was capped and heated in a microwave to 120° C. for 15 minutes. The reaction mixture was diluted with saturated aqueous sodium bicarbonate (50 mL) and extracted with isopropyl acetate (3×75 mL). The combined organics were dried over sodium sulfate, filtered, and concentrated to dryness in vacuo to afford 5-(2,6-difluorophenyl)-[1,2,4]triazolo[1,5-a]pyridin-2-amine (102 mg, 88%) as a tan solid, which was used in the next step without further purification. LC-MS $R_T$=1.60 min, m/z=247.0 $(M+H)^+$.

LCMS (5 to 95% acetonitrile in water+0.1% formic acid over 5 mins) retention time 1.60 min, ESI+ found [M+H]=247.0.

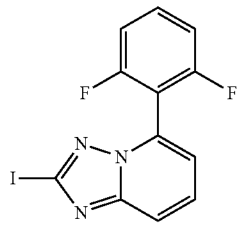 [SMILES: Fc1cccc(F)c1-c1cccc2nc(I)nn12]

Step 2: 5-(2,6-difluorophenyl)-2-iodo-[1,2,4]triazolo[1,5-a]pyridine

To a solution of 5-(2,6-difluorophenyl)-[1,2,4]triazolo[1,5-a]pyridin-2-amine (326 mg, 1.324 mmol) and p-toluene sulphonic acid (967 mg, 5.084 mmol) in acetonitrile (10 mL) was added a solution of potassium iodide (725 mg, 4.369 mmol) and sodium nitrite (229 mg, 3.323 mmol) in water (2 mL) at 24° C. After 18 h, isopropyl acetate was added to the reaction mixture. The resulting solution was washed with water (2×100 mL) and saturated aqueous sodium chloride solution. The organic was dried over magnesium sulfate, filtered, and concentrated. The residue was purified by column chromatography (silica gel, 100-200 mesh, 0 to 100% iPrOAc in heptane) affording 5-(2,6-difluorophenyl)-2-iodo-[1,2,4]triazolo[1,5-a]pyridine (339 mg, 72%) as a light yellow solid. LC-MS $R_T$=2.20 min, m/z=357.9 $(M+H)^+$.

LCMS (5 to 95% acetonitrile in water+0.1% formic acid over 5 mins) retention time 2.20 min, ESI+ found [M+H]=357.9.

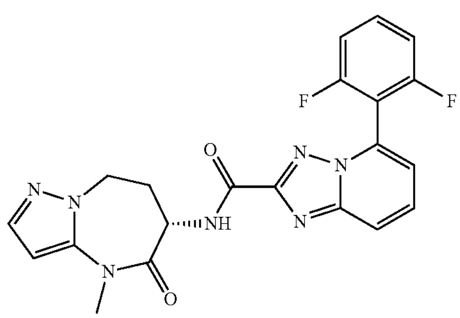 [SMILES: CN1C(=O)[C@@H](NC(=O)c2nc3cccc(-c4c(F)cccc4F)n3n2)CCn2nccc21]

Step 3: (S)-5-(2,6-difluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide Palladium(II) acetate (10 mg, 0.042 mmol), 4,5-bis(diphenylphosphino)-9,9-dimethylxanthene (37 mg, 0.063 mmol), 5-(2,6-difluorophenyl)-2-iodo-[1,2,4]triazolo[1,5-a]pyridine (150 mg, 0.420 mmol), (S)-6-amino-4-methyl-7,8-dihydro-4H-pyrazolo[1,5-a][1,3]diazepin-5(6H)-one (76 mg, 0.420 mmol) were added to a screw-cap vial. Nitrogen was then purged through the reaction vial for 15 min. The solids were dissolved in toluene (8 mL), and triethylamine (0.38 mL, 2.73 mmol) was added. The reaction flask was purged with a balloon for carbon monoxide for 5 minutes. The vial, with the balloon of carbon monoxide, was placed in a 80° C. heating block and was allowed to stir for 16 h. The crude residue was dissolved in isopropyl acetate, and filtered through Celite and concentrated down to dryness. The crude residue was purified by preparative RP-HPLC (20-60% acetonitrile in water+0.1% formic acid) to afford (S)-5-(2,6-difluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide as tan solid (141 mg, 77% yield). $^1$H NMR (400 MHz, DMSO-$d_6$) δ 8.90 (d, J=7.7 Hz, 1H), 8.10 (dd, J=9.0, 1.2 Hz, 1H), 7.93 (dd, J=9.0, 7.1 Hz, 1H), 7.76 (tt, J=8.5, 6.6 Hz, 1H), 7.59 (dd, J=7.1, 1.2 Hz, 1H), 7.49 (d, J=2.0 Hz, 1H), 7.39 (t, J=8.4 Hz, 2H), 6.35 (d, J=2.0 Hz, 1H), 4.44-4.14 (m, 3H), 3.26 (s, 3H), 2.64 (tt, J=12.9, 8.1 Hz, 1H), 2.50-2.35 (m, 1H). LC-MS $R_T$=4.29 min, m/z=438.2 (M+H)

LCMS (5 to 95% acetonitrile in water+0.1% formic acid over 10 mins) retention time 4.29 min, ESI+ found [M+H]=438.2

Example 395

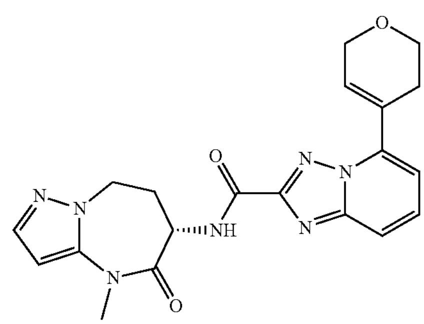 [SMILES: CN1C(=O)[C@@H](NC(=O)c2nc3cccc(C4=CCOCC4)n3n2)CCn2nccc21]

(S)-5-(3,6-dihydro-2H-pyran-4-yl)-N-(4-methyl-5-oxo-5,6,7,8-tetrahydro-4H-pyrazolo[1, 5-a][1,3]diazepin-6-yl)-[1,2,4]triazolo[1,5-a]pyridine-2-carboxamide (S)-5-(3,6-dihydro-2H-pyran-4-yl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide was prepared corresponding from (S)-6-amino-4-methyl-7,8-dihydro-4H-pyrazolo[1,5-a][1,3]diazepin-5(6H)-one, and 5-(3,6-dihydro-2H-pyran-4-yl)-2-iodo-[1,2,4]triazolo[1,5-a]pyridine according to Method GZ14. The residue was purified by SFC (5-60% methanol+0.1% ammonium hydroxide elution with Carbon Dioxide, Column HSS C18, 150×30 mm) instead. Yield of final step: 2.5 mg, 1.0%. LC-MS $R_T$=3.61 min, m/z=408.2 $(M+H)^+$.

LCMS (5 to 95% acetonitrile in water+0.1% formic acid over 10 mins) retention time 3.61 min, ESI+ found [M+H]=408.2

Example 396

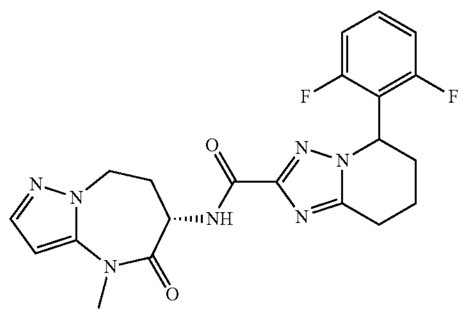 [SMILES: CN1C(=O)[C@@H](NC(=O)c2nc3n(n2)C(c2c(F)cccc2F)CCC3)CCn2nccc21]

5-(2,6-difluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide 5-(2,6-difluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide was prepared from (S)-5-(2,6-difluorophenyl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide according to Method GZ2. The residue was purified by preparative RP-HPLC (5-50% acetonitrile in water+0.1% formic acid) to afford final product (26.2 mg, 23%) as a white. $^1$H NMR (400 MHz, DMSO-$d_6$) δ 8.48 (dd, J=20.1, 7.8 Hz, 1H), 7.54-7.39 (m, 2H), 7.14 (t, J=9.2 Hz, 2H), 6.32 (t, J=1.9 Hz, 1H), 5.85-5.70 (m, 1H), 4.41-4.10 (m, 3H), 3.23 (d, J=1.9 Hz, 3H), 3.09-2.85 (m, 2H), 2.64-2.50 (m, 1H), 2.48-2.29 (m, 2H), 2.20-1.97 (m, 3H). LC-MS $R_T$=4.25 min, m/z=442.2 (M+H)$^+$.

LCMS (5 to 95% acetonitrile in water+0.1% formic acid over 10 mins) retention time 4.25 min, ESI+ found [M+H]=442.2

Example 397

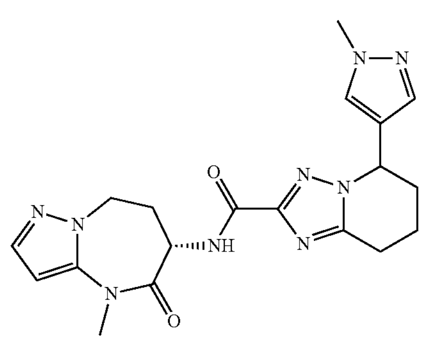 [SMILES: CN1C(=O)[C@@H](NC(=O)c2nc3n(n2)C(c2cnn(C)c2)CCC3)CCn2nccc21]

5-(1-methyl-1H-pyrazol-4-yl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide N—((S)-4-methyl-5-oxo-5,6,7,8-tetrahydro-4H-pyrazolo[1,5-a][1,3]diazepin-6-yl)-5-phenyl-5, 6,7,8-tetrahydro-[1,2,4]triazolo[1,5-a]pyridine-2-carboxamide was prepared from (S)-5-(1-methyl-1H-pyrazol-4-yl)-N-(4-methyl-5-oxo-5,6,7,8-tetrahydro-4H-pyrazolo[1,5-a][1,3]diazepin-6-yl)-[1,2,4]triazolo[1,5-a]pyridine-2-carboxamide according to Method GZ2. The residue was purified by preparative RP-HPLC (20-60% acetonitrile in water+0.1% formic acid) to afford final product (23 mg, 28%) as a white solid. $^1$H NMR (400 MHz, DMSO-$d_6$) δ 8.52-8.38 (m, 1H), 7.65-7.59 (m, 1H), 7.48 (d, J=2.0 Hz, 1H), 7.37 (s, 1H), 6.33 (d, J=2.0 Hz, 1H), 5.47 (t, J=5.8 Hz, 1H), 4.42-4.12 (m, 3H), 3.79 (s, 3H), 3.24 (d, J=2.8 Hz, 3H), 3.02-2.83 (m, 2H), 2.66-2.52 (m, 1H), 2.43-2.24 (m, 2H), 2.19-2.05 (m, 1H), 1.93 (m, 2H). LC-MS $R_T$=3.11 min, m/z=410.2 (M+H)$^+$.

LCMS (5 to 95% acetonitrile in water+0.1% formic acid over 10 mins) retention time 3.11 min, ESI+ found [M+H]=410.2

Example 398

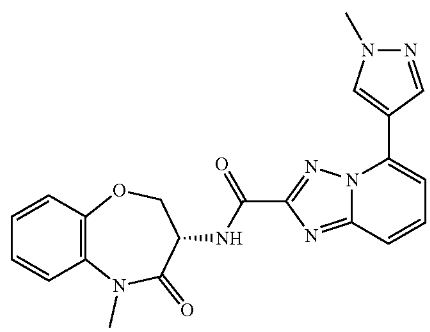 [SMILES: CN1C(=O)[C@@H](NC(=O)c2nc3cccc(-c4cnn(C)c4)n3n2)COc2ccccc21]

(S)-5-(1-methyl-1H-pyrazol-4-yl)-N-(5-methyl-4-oxo-2,3,4,5-tetrahydrobenzo[b][1,4]oxazepin-3-yl)-[1,2,4]triazolo[1,5-a]pyridine-2-carboxamide (S)-5-(1-methyl-1H-pyrazol-4-yl)-N-(5-methyl-4-oxo-2,3,4,5-tetrahydrobenzo[b][1,4]oxazepin-3-yl)-[1,2,4]triazolo[1,5-a]pyridine-2-carboxamide was prepared corresponding from (3S)-3-amino-5-methyl-2,3-dihydro-1,5-benzoxazepin-4-one, and 2-iodo-5-(1-methyl-1H-pyrazol-4-yl)-[1,2,4]triazolo[1,5-a]pyridine according to Method GZ14. The residue was purified by preparative RP-HPLC (20-60% acetonitrile in water+0.1% formic acid) instead. Yield of final step: 60.8 mg, 32.0%. $^1$H NMR (400 MHz, DMSO-$d_6$) δ 9.01-8.90 (m, 2H), 8.53 (s, 1H), 7.88-7.73 (m, 3H), 7.55 (dd, J=7.7, 1.8 Hz, 1H), 7.40-7.21 (m, 3H), 4.96 (dt, J=11.5, 7.9 Hz, 1H), 4.73 (dd, J=11.6, 9.8 Hz, 1H), 4.51 (dd, J=9.9, 7.8 Hz, 1H), 4.00 (s, 3H), 3.35 (s, 3H). LC-MS $R_T$=4.29 min, m/z=418.2 (M+H)$^+$.

LCMS (5 to 95% acetonitrile in water+0.1% formic acid over 10 mins) retention time 4.29 min, ESI+ found [M+H]=418.2

Example 399

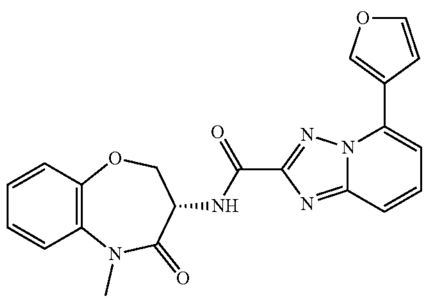 [SMILES: CN1C(=O)[C@@H](NC(=O)c2nc3cccc(-c4ccoc4)n3n2)COc2ccccc21]

(S)-5-(furan-3-yl)-N-(5-methyl-4-oxo-2,3,4,5-tetrahydrobenzo[b][1,4]oxazepin-3-yl)-[1,2, 4]triazolo[1,5-a]pyridine-2-carboxamide (S)-5-(furan-3-yl)-N-(5-methyl-4-oxo-2,3,4,5-tetrahydrobenzo[b][1,4]oxazepin-3-yl)-[1,2,4]triazolo[1,5-a]pyridine-2-carboxamide was prepared corresponding from (3S)-3-amino-5-methyl-2,3-dihydro-1,5-benzoxazepin-4-one (51.3 mg, 0.267 mmol), and 5-(furan-3-yl)-2-iodo-[1,2,4]triazolo[1,5-a]pyridine (83.0 mg, 0.267 mmol), according to Method GZ14. The residue was purified by preparative RP-HPLC (20-60% acetonitrile in water+0.1% formic acid) instead. Yield of final step: 3.3 mg, 3.0%. $^1$H NMR (400 MHz, DMSO-$d_6$) δ 9.23 (s, 1H), 9.07 (d, J=8.2 Hz, 1H), 7.99 (t, J=1.9 Hz, 1H), 7.95-7.81 (m, 3H), 7.59-7.52 (m, 1H), 7.44 (d, J=2.0 Hz, 1H), 7.40-7.24 (m, 3H), 4.99 (dt, J=11.8, 7.9 Hz, 1H), 4.74 (t, J=10.7 Hz, 1H), 4.49 (dd, J=9.9, 7.8 Hz, 1H), 3.35 (s, 3H). LC-MS $R_T$=4.93 min, m/z=404.1 $(M+H)^+$.

LCMS (5 to 95% acetonitrile in water+0.1% formic acid over 10 mins) retention time 4.93 min, ESI+ found [M+H]=404.1

Examples 400 and 401

Method GZ_chiral_1

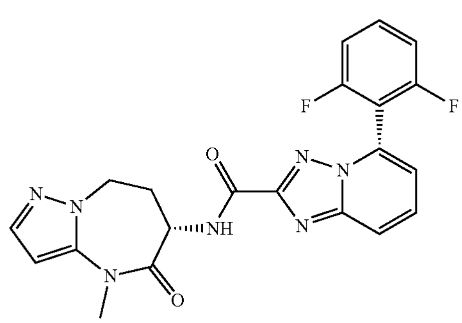

-continued

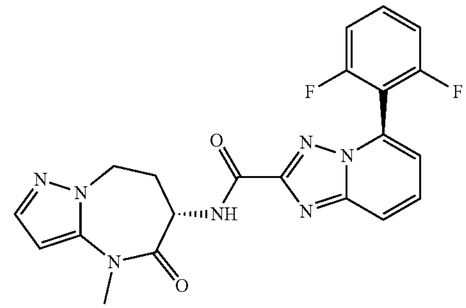

(S)-5-(2,6-difluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide and (R)-5-(2,6-difluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide (1:1)

5-(2,6-difluorophenyl)-N—((S)-4-methyl-5-oxo-5,6,7,8-tetrahydr-4H-pyrazolo[1,5-a][1,3]diazepin-6-yl)-5,6,7,8-tetrahydro-[1,2,4]triazolo[1,5-a]pyridine-2-carboxamide was further purified by chiral SFC (Whelk O-1; 156×21.2 mm, 5 um; 45% methanol isocratic elution with Carbon Dioxide) affording arbitrarily assigned diastereomers (S)-5-(2,6-difluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide (32.2 mg, 28%) and (R)-5-(2,6-difluorophenyl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide (21.2 mg, 18%) as white solids:

Analytical data for the first eluting diastereomer (arbitrarily assigned S, S configuration): SFC $R_T$ (Whelkol s,s, 50% methanol isocratic elution with Carbon Dioxide, 2.5 min method): 0.658 min, 100% ee: $^1$H NMR (400 MHz, DMSO-$d_6$) δ 8.50 (d, J=7.8 Hz, 1H), 7.54-7.41 (m, 2H), 7.14 (t, J=9.0 Hz, 2H), 6.33 (d, J=2.0 Hz, 1H), 5.81 (dd, J=9.3, 5.5 Hz, 1H), 4.41-4.10 (m, 3H), 3.23 (s, 3H), 3.09-2.86 (m, 2H), 2.56 (m, 1H), 2.49-2.32 (m, 3H), 2.21-1.94 (m, 3H). LCMS $R_T$=4.22 min, m/z=442.2 $(M+H)^+$.

LCMS (5 to 95% acetonitrile in water+0.1% formic acid over 10 mins) retention time 4.22 min, ESI+ found [M+H]=442.2

Analytical data for the second eluting diastereomer (arbitrarily assigned R, S configuration): SFC $R_T$(Whelkol s,s, 50% methanol isocratic elution, 2.5 min method): 1.397 min, 100% ee: $^1$H NMR (400 MHz, DMSO-$d_6$) δ 8.45 (d, J=7.9 Hz, 1H), 7.54-7.41 (m, 2H), 7.14 (t, J=9.2 Hz, 2H), 6.32 (d, J=2.0 Hz, 1H), 5.81 (dd, J=9.2, 5.4 Hz, 1H), 4.41-4.11 (m, 3H), 3.23 (s, 3H), 3.12-2.87 (m, 2H), 2.57 (m, 1H), 2.38 (m, 3H), 2.20-1.98 (m, 3H). LCMS $R_T$=4.23 min, m/z=442.2 $(M+H)^+$.

LCMS (5 to 95% acetonitrile in water+0.1% formic acid over 10 mins) retention time 4.23 min, ESI+ found [M+H]=442.2

Examples 402 and 403

Method GZ_chiral_2

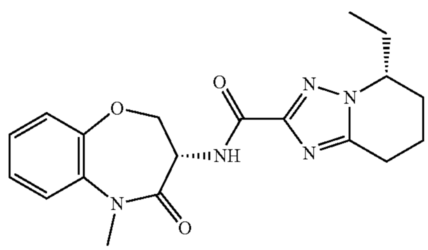

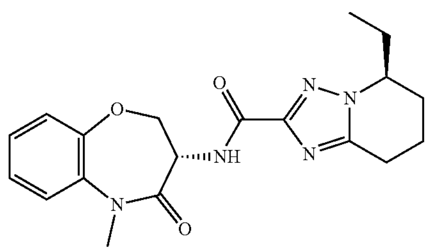

(R)-5-ethyl-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide and (S)-5-ethyl-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide (1:1)

5-ethyl-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide was further purified by chiral SFC (Chiralcel OX; 155×21.2 mm, 5 um; 40% methanol isocratic elution with Carbon Dioxide) affording arbitrarily assigned diastereomers (R)-5-ethyl-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide (17.6 mg, 16%) (S)-5-ethyl-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide (19.8 mg, 18%) as white solids:

Analytical data for the first eluting diastereomer (arbitrarily assigned S, S configuration): SFC $R_T$ (OX, 35% methanol+0.1% ammonium hydroxide isocratic elution with Carbon Dioxide, 2.5 min method): 0.763 min, 100% ee: $^1$H NMR (400 MHz, DMSO-$d_6$) δ 8.42 (d, J=8.1 Hz, 1H), 7.51 (dd, J=7.6, 1.9 Hz, 1H), 7.38-7.20 (m, 3H), 4.82 (dt, J=11.5, 7.8 Hz, 1H), 4.60 (dd, J=11.6, 9.8 Hz, 1H), 4.40 (dd, J=9.8, 7.7 Hz, 1H), 4.18 (s, 1H), 3.31 (s, 3H), 2.85 (q, J=6.9, 6.0 Hz, 2H), 2.18-1.91 (m, 3H), 1.86-1.65 (m, 3H), 0.91 (t, J=7.4 Hz, 3H). LCMS $R_T$=4.70 min, m/z=370.1 $(M+H)^+$.

LCMS (5 to 95% acetonitrile in water+0.1% formic acid over 10 mins) retention time 4.70 min, ESI+ found [M+H]=370.1

Analytical data for the second eluting diastereomer (arbitrarily assigned R, S configuration): SFC $R_T$(OX, 35% methanol+0.1% ammonium hydroxide isocratic elution with Carbon Dioxide, 2.5 min method): 1.242 min, 98.9% ee: $^1$H NMR (400 MHz, DMSO-$d_6$) δ 8.40 (d, J=8.1 Hz, 1H), 7.51 (dd, J=7.6, 1.9 Hz, 1H), 7.38-7.20 (m, 3H), 4.83 (dt, J=11.4, 7.8 Hz, 1H), 4.57 (dd, J=11.5, 9.9 Hz, 1H), 4.40 (dd, J=9.8, 7.7 Hz, 1H), 4.18 (dt, J=12.0, 5.2 Hz, 1H), 3.34 (s, 3H), 2.92-2.79 (m, 2H), 2.18-2.02 (m, 2H), 1.98 (q, J=6.9 Hz, 1H), 1.86-1.66 (m, 3H), 0.90 (t, J=7.5 Hz, 3H). LCMS $R_T$=4.72 min, m/z=370.1 $(M+H)^+$.

LCMS (5 to 95% acetonitrile in water+0.1% formic acid over 10 mins) retention time 4.72 min, ESI+ found [M+H]=370.1

Example 404

Method GZ_chiral_3

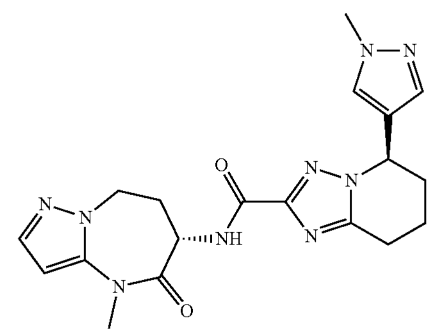 [SMILES: CN1C(=O)[C@@H](NC(=O)c2nc3n(n2)[C@@H](c2cnn(C)c2)CCC3)CCn2nccc21]

(R)-5-(1-methyl-1H-pyrazol-4-yl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide 5-(1-methyl-1H-pyrazol-4-yl)-N—((S)-4-methyl-5-oxo-5,6,7,8-tetrahydro-4H-pyrazolo[1,5-a][1,3]diazepin-6-yl)-5,6,7,8-tetrahydro-[1,2,4]triazolo[1,5-a]pyridine-2-carboxamide was purified by chiral SFC (Chiralpak AD; 153×21.2 mm, 5 um; 35% methanol isocratic elution with Carbon Dioxide) affording arbitrarily assigned diastereomers (R)-5-(1-methyl-1H-pyrazol-4-yl)-N—((S)-4-methyl-5-oxo-5,6,7,8-tetrahydro-4H-pyrazolo[1, 5-a][1,3]diazepin-6-yl)-5,6,7,8-tetrahydro-[1,2,4]triazolo[1,5-a]pyridine-2-carboxamide (5.2 mg, 4.6%) as white solids:

Analytical data: arbitrarily assigned (R, S configuration): SFC $R_T$ (AD, 30% methanol+0.1% ammonium hydroxide isocratic elution with Carbon Dioxide, 2.5 min method): 0.565 min, 97.8% purity, 95.5% ee: $^1$H NMR (400 MHz, DMSO-$d_6$) δ 8.49 (d, J=7.9 Hz, 1H), 7.63 (s, 1H), 7.49 (d, J=1.9 Hz, 1H), 7.38 (s, 1H), 6.35 (d, J=2.0 Hz, 1H), 5.47 (t, J=5.8 Hz, 1H), 4.42-4.12 (m, 3H), 3.79 (s, 3H), 3.24 (s, 3H), 2.93 (td, J=6.3, 3.2 Hz, 2H), 2.43-2.24 (m, 1H), 2.18-2.05 (m, 1H), 2.01-1.82 (m, 2H). LCMS $R_T$=3.16 min, m/z=410.2 $(M+H)^+$.

LCMS (5 to 95% acetonitrile in water+0.1% formic acid over 10 mins) retention time 3.16 min, ESI+ found [M+H]=410.2

Example 405

Method GZ4

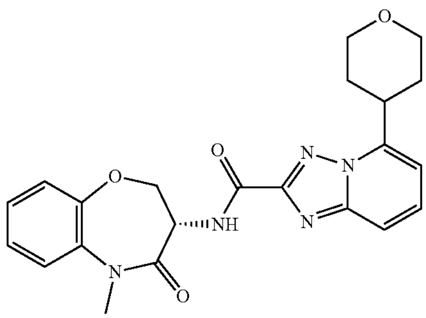 [SMILES: CN1C(=O)[C@@H](NC(=O)c2nc3cccc(C4CCOCC4)n3n2)COc2ccccc21]

(S)—N-(5-methyl-4-oxo-2,3,4,5-tetrahydrobenzo[b][1,4]oxazepin-3-yl)-5-(tetrahydro-2H-pyran-4-yl)-[1,2,4]triazolo[1,5-a]pyridine-2-carboxamide

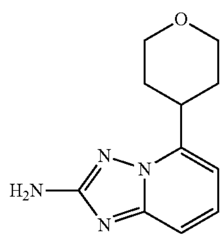 [SMILES: Nc1nc2cccc(C3CCOCC3)n2n1]

Step 1: 5-(3,6-dihydro-2H-pyran-4-yl)-[1,2,4]triazolo[1,5-a]pyridin-2-amine

A mixture of 5-bromo-[1,2,4]triazolo[1,5-a]pyridin-2-amine (600 mg, 2.82 mmol), 3,6-dihydro-2H-pyran-4-boronic acid pinacol ester (915 mg, 4.22 mmol), tripotassium phosphate (1793 mg, 8.45 mmol) in tetrahydrofuran (16 mL) and water (4 mL) was degassed, then 2-Dicyclohexylphosphino-2',4',6'-triisopropylbiphenyl (80 mg, 0.17 mmol) and X-Phos aminobiphenyl palladium chloride precatalyst, XPhos-Pd-G2 (80 mg, 0.08 mmol) was added under nitrogen. The microwave vial was capped and heated to 85° C. for 45 minutes. The reaction mixture was cooled down, diluted with saturated aqueous sodium bicarbonate (50 mL) and extracted with isopropyl acetate (3×75 mL). The combined organics were dried over sodium sulfate, filtered, and concentrated to dryness in vacuo, triturated with isopropyl acetate, filtered out the solid to afford 5-(3,6-dihydro-2H-pyran-4-yl)-[1,2,4]triazolo[1,5-a]pyridin-2-amine (502 mg, 83%) as a tan solid. 1H NMR (400 MHz, DMSO-d6) δ 7.43 (dd, J=8.7, 7.4 Hz, 1H), 7.30 (dd, J=8.7, 1.3 Hz, 1H), 7.18 (tt, J=2.9, 1.5 Hz, 1H), 6.86 (dd, J=7.4, 1.3 Hz, 1H), 6.00 (s, 2H), 4.32 (q, J=2.8 Hz, 2H), 3.85 (t, J=5.4 Hz, 2H), 2.62 (dddd, J=6.6, 5.2, 3.3, 1.9 Hz, 2H). LCMS $R_T$=1.08 min, m/z=217.2 $(M+H)^+$.

LCMS (5 to 95% acetonitrile in water+0.1% formic acid over 5 mins) retention time 1.08 min, ESI+ found [M+H]=217.2.

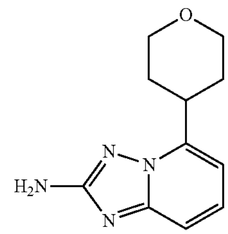 [SMILES: Nc1nc2cccc(C3CCOCC3)n2n1]

Step 2: 5-(tetrahydro-2H-pyran-4-yl)-[1,2,4]triazolo[1,5-a]pyridin-2-amine

To a solution of 5-(3,6-dihydro-2H-pyran-4-yl)-[1,2,4]triazolo[1,5-a]pyridin-2-amine (870 mg, 4.02 mmol) in ethanol (15 mL), added acetic acid (15 mL), then added platinum (iv) oxide (45 mg, 0.20 mmol). The reaction mixture stirred under a balloon of hydrogen gas for 16 h at RT, then was filtered through Celite and concentrated to dryness in vacuo. The residue was diluted with saturated aqueous sodium bicarbonate (50 mL) and extracted with isopropyl acetate (3×75 mL). The combined organics were dried over sodium sulfate, filtered, and concentrated to dryness in vacuo affording 5-(tetrahydro-2H-pyran-4-yl)-[1,2,4]triazolo[1,5-a]pyridin-2-amine (755 mg, 86%) as an off white solid. LC-MS $R_T$=1.15 min, m/z=219.1 $(M+H)^+$.

LCMS (5 to 95% acetonitrile in water+0.1% formic acid over 5 mins) retention time 1.15 min, ESI+ found [M+H]=219.1

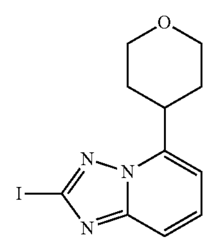 [SMILES: Ic1nc2cccc(C3CCOCC3)n2n1]

Step 3: 2-iodo-5-(tetrahydro-2H-pyran-4-yl)-[1,2,4]triazolo[1,5-a]pyridine

To a solution of 5-(tetrahydro-2H-pyran-4-yl)-[1,2,4]triazolo[1,5-a]pyridin-2-amine (750 mg, 3.44 mmol) and p-toluene sulphonic acid (2.51 g, 13.2 mmol) in acetonitrile (45 mL) was added a solution of potassium iodide (1.88 g, 11.34 mmol) and sodium nitrite (595 mg, 8.62 mmol) in water (5 mL) at 24° C. After 18 h, isopropyl acetate was added to the reaction mixture. The resulting solution was washed with water (2×100) and saturated aqueous sodium chloride solution. The organic was dried over magnesium sulfate, filtered, and concentrated. The residue was purified by column chromatography (silica gel, 100-200 mesh, 0 to 100% iPrOAc in heptane) affording 2-iodo-5-(tetrahydro-2H-pyran-4-yl)-[1,2,4]triazolo[1,5-a]pyridine (645 mg, 57%) as a light yellow solid. LC-MS $R_T$=1.76 min, m/z=330.0 $(M+H)^+$.

LCMS (5 to 95% acetonitrile in water+0.1% formic acid over 5 mins) retention time 1.76 min, ESI+ found [M+H]=330.0.

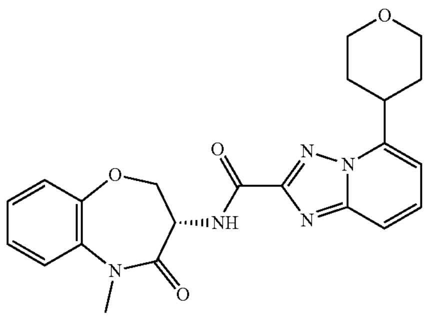 [SMILES: CN1C(=O)[C@@H](NC(=O)c2nc3cccc(C4CCOCC4)n3n2)COc2ccccc21]

Step 4: (S)—N-(5-methyl-4-oxo-2,3,4,5-tetrahydrobenzo[b][1,4]oxazepin-3-yl)-5-(tetrahydro-2H-pyran-4-yl)-[1,2,4]triazolo[1,5-a]pyridine-2-carboxamide Palladium(II) acetate (13.6 mg, 0.061 mmol), 4,5-bis(diphenylphosphino)-9,9-dimethylxanthene (52.7 mg, 0.091 mmol), 2-iodo-5-phenyl-[1,2,4]triazolo[1,5-a]pyridine (200 mg, 0.607 mmol), (3S)-3-amino-5-methyl-2,3-dihydro-1,5-benzoxazepin-4-one (125.5 mg, 0.668 mmol) were added to a screw-cap vial. Nitrogen was then purged through the reaction vial for 15 min. The solids were dissolved in toluene (10 mL), and triethylamine (0.55 mL, 3.95 mmol) was added. The reaction flask was purged with a balloon for carbon monoxide for 5 minutes. The vial, with the balloon of carbon monoxide, was placed in a 80° C. heating block and was allowed to stir for 16 h. The crude residue was dissolved in isopropyl acetate, and filtered through Celite. The crude residue was purified by flash column chromatography (silica gel, 0% to 100% isopropyl acetate in heptane) to afford (S)—N-(5-methyl-4-oxo-2,3,4,5-tetrahydrobenzo[b][1,4]oxazepin-3-yl)-5-(tetrahydro-2H-pyran-4-yl)-[1,2,4]triazolo[1,5-a]pyridine-2-carboxamide (230 mg, 90% Yield) as a yellow solid.

$^1$H NMR (400 MHz, DMSO-$d_6$) δ 8.80 (d, J=7.9 Hz, 1H), 7.88-7.74 (m, 2H), 7.53 (dd, J=7.6, 1.9 Hz, 1H), 7.46-7.13 (m, 5H), 4.91 (dt, J=11.4, 7.8 Hz, 1H), 4.64 (dd, J=11.5, 9.9 Hz, 1H), 4.49 (dd, J=9.9, 7.7 Hz, 1H), 4.05-3.96 (m, 2H), 3.73 (tt, J=11.9, 3.6 Hz, 1H), 3.57 (td, J=11.8, 2.0 Hz, 2H), 3.30 (s, 3H), 2.05-1.96 (m, 2H), 1.89-1.72 (m, 2H). LCMS $R_T$=4.37 min, m/z=422.1 $(M+H)^+$.

LCMS (5 to 95% acetonitrile in water+0.1% formic acid over 10 mins) retention time 4.37 min, ESI+ found [M+H]=422.1.

Example 406

Method GZ11

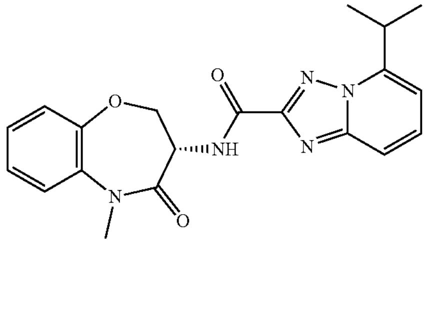 [SMILES: CC(C)c1cccc2nc(C(=O)N[C@H]3COc4ccccc4N(C)C3=O)nn12]

(S)-5-isopropyl-N-(5-methyl-4-oxo-2,3,4,5-tetrahydrobenzo[b][1,4]oxazepin-3-yl)-[1,2,4]triazolo[1,5-a]pyridine-2-carboxamide

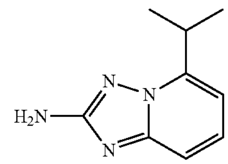

Step 1: 5-isopropyl-[1,2,4]triazolo[1,5-a]pyridin-2-amine

A suspension of 5-bromo-[1,2,4]triazolo[1,5-a]pyridin-2-amine (700 mg, 3.29 mmol) in dioxane (12 mL) was degassed, cooled to ice bath, added 1,3-bis(diphenylphosphino)propane nickel (II) chloride (178 mg, 0.329 mmol) under nitrogen, followed by diisopropyl zinc (1M solution in toluene) via syringe over 10 mins. Removed the ice bath, heated up to 95° C. for overnight. The reaction mixture was poured into isopropyl alcohol, and concentrated to dryness in vacuo. The residue was diluted with saturated Ammonium chloride (50 mL) and extracted with isopropyl acetate (3×75 mL). The combined organics were dried over sodium sulfate, filtered, and concentrated to dryness in vacuo to afford 5-isopropyl-[1,2,4]triazolo[1,5-a]pyridin-2-amine (424 mg, 73%) as a tan solid which was used in the next step without further purification. LC-MS $R_T$=0.90 min, m/z=177.2 (M+H)+.

LCMS (5 to 95% acetonitrile in water+0.1% formic acid over 2 mins) retention time 0.90 min, ESI+ found [M+H]=177.2.

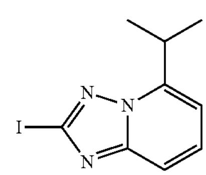

Step 2: 2-iodo-5-isopropyl-[1,2,4]triazolo[1,5-a]pyridine

To a solution of 5-isopropyl-[1,2,4]triazolo[1,5-a]pyridin-2-amine (800 mg, 4.54 mmol) and p-toluene sulphonic acid (3.32 g, 17.43 mmol) in acetonitrile (40 mL) was added a solution of potassium iodide (2.49 g, 14.98 mmol) and sodium nitrite (786 mg, 11.40 mmol) in water (5 mL) at 24° C. After 18 h, isopropyl acetate was added to the reaction mixture. The resulting solution was washed with water (2×100 mL) and saturated aqueous sodium chloride solution. The organic was dried over magnesium sulfate, filtered, and concentrated. The residue was purified by column chromatography (silica gel, 100-200 mesh, 0 to 100% iPrOAc in heptane) affording 2-iodo-5-isopropyl-[1,2,4]triazolo[1,5-a]pyridine (534 mg, 41%) as a light yellow solid. LC-MS $R_T$=1.38 min, m/z=288.0 (M+H).

LCMS (5 to 95% acetonitrile in water+0.1% formic acid over 2 mins) retention time 1.38 min, ESI+ found [M+H]=288.0.

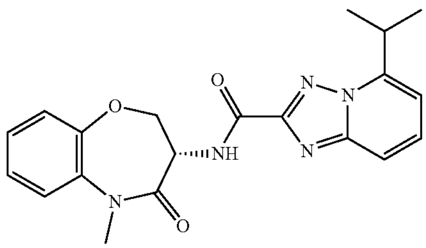 [SMILES: CC(C)c1cccc2nc(C(=O)N[C@H]3COc4ccccc4N(C)C3=O)nn12]

Step 3: (S)-5-isopropyl-N-(5-methyl-4-oxo-2,3,4,5-tetrahydrobenzo[b][1,4]oxazepin-3-yl)-[1,2,4]triazolo[1,5-a]pyridine-2-carboxamide Palladium(II) acetate (16 mg, 0.069 mmol), 4,5-bis(diphenylphosphino)-9,9-dimethylxanthene (61 mg, 0.104 mmol), 2-iodo-5-isopropyl-[1,2,4]triazolo[1,5-a]pyridine (200 mg, 0.697 mmol), (S)-3-amino-5-methyl-2,3-dihydrobenzo[b][1,4]oxazepin-4(5H)-one (147 mg, 0.766 mmol) were added to a screw-cap vial. Nitrogen was then purged through the reaction vial for 15 min. The solids were dissolved in toluene (10 mL), and triethylamine (0.63 mL, 4.53 mmol) was added. The reaction flask was purged with a balloon for carbon monoxide for 5 minutes. The vial, with the balloon of carbon monoxide, was placed in a 80° C. heating block and was allowed to stir for 16 h. The reaction mixture was purified by preparative RP-HPLC (20-60% acetonitrile in water+0.1% formic acid) to afford (S)-5-isopropyl-N-(5-methyl-4-oxo-2,3,4,5-tetrahydrobenzo[b][1,4]oxazepin-3-yl)-[1,2,4]triazolo[1,5-a]pyridine-2-carboxamide as tan solid (152.8 mg, 58.0%) which was confirmed by $^1$H NMR as 64% purity. $^1$H NMR (400 MHz, DMSO-$d_6$) δ 8.79 (d, J=3.3 Hz, 1H), 7.85-7.79 (m, 2H), 7.54 (d, J=2.0 Hz, 1H), 7.38-7.30 (m, 3H), 7.23-7.21 (s, 1H), 4.91 (m, 1H), 4.64 (m, 1H), 4.49 (m, 1H), 3.76 (p, J=6.8 Hz, 1H), 3.33 (s, 3H), 1.38 (dd, J=6.9, 0.9 Hz, 6H). LC-MS $R_T$=5.13 min, m/z=380.1 $(M+H)^+$. LC-MS $R_T$=5.13 min, m/z=380.1 $(M+H)^+$.

LCMS (5 to 95% acetonitrile in water+0.1% formic acid over 10 mins) retention time 5.13 min, ESI+ found [M+H]=380.1

Examples 407 and 411

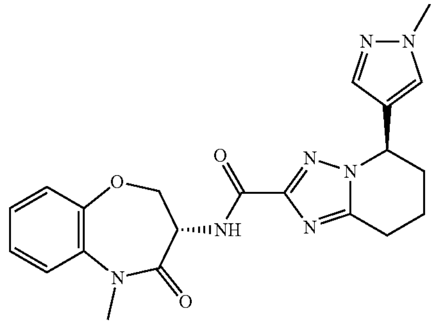

-continued

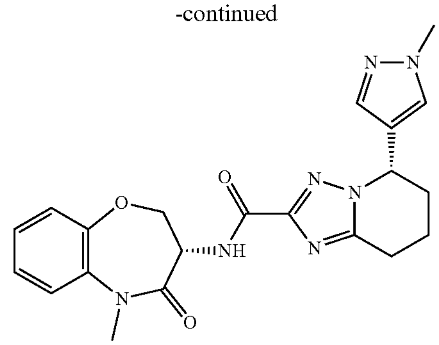

(R)-5-(1-methyl-1H-pyrazol-4-yl)-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide and (S)-5-(1-methyl-1H-pyrazol-4-yl)-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide (1:1)

5-(1-methyl-1H-pyrazol-4-yl)-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide was purified by chiral SFC (Chiralpak AD; 153×21.2 mm, 5 um; 35% methanol isocratic elution with Carbon Dioxide) affording arbitrarily assigned diastereomers (R)-5-(1-methyl-1H-pyrazol-4-yl)-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide (5.0 mg, 8.25%) as white solids, and (S)-5-(1-methyl-1H-pyrazol-4-yl)-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide (5.0 mg, 8.25%) as white solids:

Analytical data for the first eluting diastereomer (arbitrarily assigned R, S configuration): SFC $R_T$ (AD, 35% methanol+0.1% ammonium hydroxide isocratic elution with Carbon Dioxide, 2.5 min method): 0.600 min, 100% purity, 100% ee: $^1$H NMR (400 MHz, DMSO-$d_6$) δ 8.34 (d, J=7.9 Hz, 1H), 7.62 (s, 1H), 7.49 (dd, J=7.6, 2.0 Hz, 1H), 7.39-7.19 (m, 4H), 5.47 (t, J=5.8 Hz, 1H), 4.81 (dt, J=11.4, 7.7 Hz, 1H), 4.55 (dd, J=11.5, 9.9 Hz, 1H), 4.39 (dd, J=9.9, 7.7 Hz, 1H), 3.78 (s, 3H), 3.31 (s, 3H), 2.93 (td, J=6.4, 2.6 Hz, 2H), 2.29 (ddd, J=8.6, 5.2, 3.3 Hz, 1H), 2.12 (dtd, J=14.0, 7.5, 6.6, 3.0 Hz, 1H), 2.03-1.83 (m, 2H). LCMS $R_T$=3.91 min, m/z=422.1 $(M+H)^+$.

LCMS (5 to 95% acetonitrile in water+0.1% formic acid over 10 mins) retention time 3.91 min, ESI+ found [M+H]=422.1

Analytical data for the second eluting diastereomer (arbitrarily assigned S, S configuration): SFC $R_T$(AD, 35% methanol+0.1% ammonium hydroxide isocratic elution with Carbon Dioxide, 2.5 min method): 0.978 min, 100% ee: $^1$H NMR (400 MHz, DMSO-$d_6$) δ 8.34 (d, J=7.9 Hz, 1H), 7.62 (s, 1H), 7.49 (dd, J=7.6, 2.0 Hz, 1H), 7.39-7.19 (m, 4H), 5.47 (t, J=5.8 Hz, 1H), 4.81 (dt, J=11.4, 7.7 Hz, 1H), 4.55 (dd, J=11.5, 9.9 Hz, 1H), 4.39 (dd, J=9.9, 7.7 Hz, 1H), 3.78 (s, 3H), 3.31 (s, 3H), 2.93 (td, J=6.4, 2.6 Hz, 2H), 2.29 (ddd, J=8.6, 5.2, 3.3 Hz, 1H), 2.12 (dtd, J=14.0, 7.5, 6.6, 3.0 Hz, 1H), 2.03-1.83 (m, 2H). LCMS $R_T$=3.89 min, m/z=422.1 $(M+H)^+$.

LCMS (5 to 95% acetonitrile in water+0.1% formic acid over 10 mins) retention time 3.89 min, ESI+ found [M+H]=422.1

Example 408

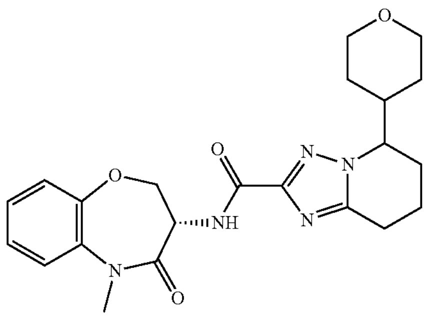 [SMILES: CN1C(=O)[C@@H](NC(=O)c2nc3n(n2)C(C2CCOCC2)CCC3)COc2ccccc21]

N—((S)-5-methyl-4-oxo-2,3,4,5-tetrahydrobenzo[b][1,4]oxazepin-3-yl)-5-(tetrahydro-2H-pyran-4-yl)-5,6,7,8-tetrahydro-[1,2,4]triazolo[1,5-a]pyridine-2-carboxamide N—((S)-5-methyl-4-oxo-2,3,4,5-tetrahydrobenzo[b][1,4]oxazepin-3-yl)-5-(tetrahydro-2H-pyran-4-yl)-5,6,7,8-tetrahydro-[1,2,4]triazolo[1,5-a]pyridine-2-carboxamide was prepared from (S)—N-(5-methyl-4-oxo-2,3,4,5-tetrahydrobenzo[b][1,4]oxazepin-3-yl)-5-(tetrahydro-2H-pyran-4-yl)-[1,2,4]triazolo[1,5-a]pyridine-2-carboxamide according to Method GZ2. The residue was purified by SFC (Whelkol s,s, 50% methanol isocratic elution with Carbon Dioxide) to afford final product (58.7 mg, 18.3%) as a white. $^1$H NMR (400 MHz, DMSO-$d_6$) δ 8.37 (dd, J=14.1, 8.0 Hz, 1H), 7.50 (dd, J=7.5, 2.0 Hz, 1H), 7.37-7.20 (m, 3H), 4.89-4.77 (m, 1H), 4.57 (ddd, J=16.0, 11.5, 9.9 Hz, 1H), 4.41 (dd, J=9.9, 7.7 Hz, 1H), 4.19 (dt, J=9.1, 4.8 Hz, 1H), 3.94-3.79 (m, 2H), 3.42-3.17 (m, 4H), 2.84 (dtt, J=21.9, 13.8, 5.0 Hz, 2H), 2.45 (m, 1H), 2.02 (dh, J=12.7, 7.2 Hz, 2H), 1.93-1.79 (m, 1H), 1.80-1.68 (m, 1H), 1.56 (d, J=13.4 Hz, 1H), 1.40 (dqd, J=16.1, 12.5, 4.2 Hz, 2H), 1.10 (d, J=13.3 Hz, 1H). LC-MS $R_T$=4.20 min, m/z=426.2 $(M+H)^+$.

LCMS (5 to 95% acetonitrile in water+0.1% formic acid over 10 mins) retention time 4.20 min, ESI+ found [M+H]=426.2

Examples 409 and 410

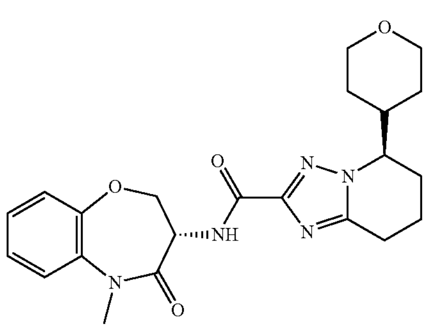

-continued

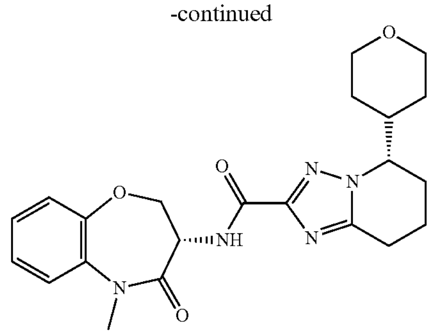

(R)—N—((S)-5-methyl-4-oxo-2,3,4,5-tetrahydrobenzo[b][1,4]oxazepin-3-yl)-5-(tetrahydro-2H-pyran-4-yl)-5,6,7,8-tetrahydro-[1,2,4]triazolo[1,5-a]pyridine-2-carboxamide and (S)—N—((S)-5-methyl-4-oxo-2,3,4,5-tetrahydrobenzo[b][1,4]oxazepin-3-yl)-5-(tetrahydro-2H-pyran-4-yl)-5,6,7,8-tetrahydro-[1,2,4]triazolo[1,5-a]pyridine-2-carboxamide (1:1)

N—((S)-5-methyl-4-oxo-2,3,4,5-tetrahydrobenzo[b][1,4]oxazepin-3-yl)-5-(tetrahydro-2H-pyran-4-yl)-5,6,7,8-tetrahydro-[1,2,4]triazolo[1,5-a]pyridine-2-carboxamide was further purified by chiral SFC (Whelk O-1; 154×21.2 mm, 5 um; 50% methanol isocratic elution with Carbon Dioxide) affording arbitrarily assigned diastereomers (R)—N—((S)-5-methyl-4-oxo-2,3,4,5-tetrahydrobenzo[b][1,4]oxazepin-3-yl)-5-(tetrahydro-2H-pyran-4-yl)-5,6,7,8-tetrahydro-[1,2,4]triazolo[1,5-a]pyridine-2-carboxamide (41.9 mg, 13.0%) and (S)—N—((S)-5-methyl-4-oxo-2,3,4,5-tetrahydrobenzo[b][1,4]oxazepin-3-yl)-5-(tetrahydro-2H-pyran-4-yl)-5,6,7,8-tetrahydro-[1,2,4]triazolo[1,5-a]pyridine-2-carboxamide (58.7 mg, 18.3%) as white solids:

Analytical data for the first eluting diastereomer (arbitrarily assigned R, S configuration): SFC $R_T$ (Whelkol s,s, 50% methanol+0.1% ammonium hydroxide isocratic elution with Carbon Dioxide, 2.5 min method): 0.852 min, 100% ee: $^1$H NMR (400 MHz, DMSO-$d_6$) δ 8.37 (dd, J=14.1, 8.0 Hz, 1H), 7.50 (dd, J=7.5, 2.0 Hz, 1H), 7.37-7.20 (m, 3H), 4.89-4.77 (m, 1H), 4.57 (ddd, J=16.0, 11.5, 9.9 Hz, 1H), 4.41 (dd, J=9.9, 7.7 Hz, 1H), 4.19 (dt, J=9.1, 4.8 Hz, 1H), 3.94-3.79 (m, 2H), 3.42-3.17 (m, 4H), 2.84 (dtt, J=21.9, 13.8, 5.0 Hz, 2H), 2.45 (m, 1H), 2.02 (dh, J=12.7, 7.2 Hz, 2H), 1.93-1.79 (m, 1H), 1.80-1.68 (m, 1H), 1.56 (d, J=13.4 Hz, 1H), 1.40 (dqd, J=16.1, 12.5, 4.2 Hz, 2H), 1.10 (d, J=13.3 Hz, 1H). LCMS $R_T$=4.18 min, m/z=426.2 $(M+H)^+$.

LCMS (5 to 95% acetonitrile in water+0.1% formic acid over 10 mins) retention time 4.18 min, ESI+ found [M+H]=426.2

Analytical data for the second eluting diastereomer (arbitrarily assigned S, S configuration): SFC $R_T$(Whelkol s,s, 50% methanol+0.1% ammonium hydroxide isocratic elution with Carbon Dioxide, 2.5 min method): 1.165 min, 100% ee: $^1$H NMR (400 MHz, DMSO-$d_6$) δ 8.37 (dd, J=14.1, 8.0 Hz, 1H), 7.50 (dd, J=7.5, 2.0 Hz, 1H), 7.37-7.20 (m, 3H), 4.89-4.77 (m, 1H), 4.57 (ddd, J=16.0, 11.5, 9.9 Hz, 1H), 4.41 (dd, J=9.9, 7.7 Hz, 1H), 4.19 (dt, J=9.1, 4.8 Hz, 1H), 3.94-3.79 (m, 2H), 3.42-3.17 (m, 4H), 2.84 (dtt, J=21.9, 13.8, 5.0 Hz, 2H), 2.45 (m, 1H), 2.02 (dh, J=12.7, 7.2 Hz, 2H), 1.93-1.79 (m, 1H), 1.80-1.68 (m, 1H), 1.56 (d, J=13.4 Hz, 1H), 1.40 (dqd, J=16.1, 12.5, 4.2 Hz, 2H), 1.10 (d, J=13.3 Hz, 1H). LCMS $R_T$=4.20 min, m/z=426.2 $(M+H)^+$.

LCMS (5 to 95% acetonitrile in water+0.1% formic acid over 10 mins) retention time 4.20 min, ESI+ found [M+H]=426.2

Example 412

Method GZ5

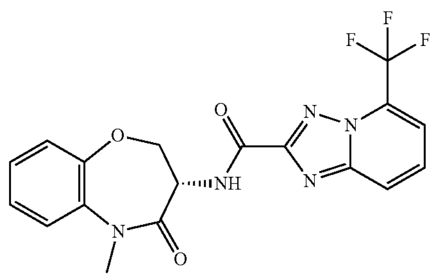 [SMILES: CN1C(=O)[C@@H](NC(=O)c2nc3cccc(C(F)(F)F)n3n2)COc2ccccc21]

(S)—N-(5-methyl-4-oxo-2,3,4,5-tetrahydrobenzo[b][1,4]oxazepin-3-yl)-5-(trifluoromethyl)-[1,2,4]triazolo[1,5-a]pyridine-2-carboxamide

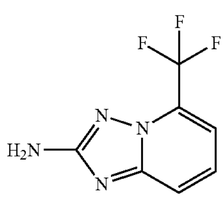 [SMILES: Nc1nc2cccc(C(F)(F)F)n2n1]

Step 1: 5-(trifluoromethyl)-[1,2,4]triazolo[1,5-a]pyridin-2-amine

To a solution of 6-(trifluoromethyl)pyridin-2-amine (960 mg, 5.92 mmol) in dioxane (40 mL) was added ethoxycarbonyl isothiocyanate (0.77 mL, 6.52 mmol). The reaction mixture was stirred at room temperature for 12 hours. The solvent was evaporated and the residue was used for the next step without purification as ethyl N-[[6-(trifluoromethyl)-2-pyridyl]carbamothioyl]carbamate.

To a solution of hydroxylamine hydrochloride (960 mg, 5.92 mmol), N,N-diisopropylethylamine (0.77 mL, 6.52 mmol) in MeOH (8 mL) and EtOH (8 mL) was added a solution of crude ethyl N-[[6-(trifluoromethyl)-2-pyridyl]carbamothioyl]carbamate in MeOH (8 mL) and EtOH (8 mL). The reaction mixture was stirred at room temperature for 1 hour, heated to 60° C. for 18 hours till reaction complete. The reaction mixture was cooled down, the solvents were evaporated. The residue was diluted with saturated aqueous sodium bicarbonate (50 mL) and extracted with isopropyl acetate (3×75 mL). The combined organics were dried over sodium sulfate, filtered, and concentrated to dryness in vacuo, triturated with isopropyl acetate, filtered out the solid to afford 5-(trifluoromethyl)-[1,2,4]triazolo[1,5-a]pyridin-2-amine (1066 mg, 89%) as a white solid. LC-MS $R_T$=1.24 min, m/z=203.1 $(M+H)^+$ LCMS (5 to 95% acetonitrile in water+0.1% formic acid over 5 mins) retention time 1.24 min, ESI+ found [M+H]=203.1.

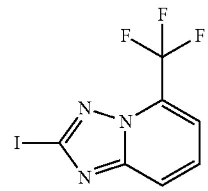 [SMILES: FC(F)(F)c1cccc2nc(I)nn12]

Step 2: 2-iodo-5-(trifluoromethyl)-[1,2,4]triazolo[1,5-a]pyridine

To a solution of 5-(trifluoromethyl)-[1,2,4]triazolo[1,5-a]pyridin-2-amine (1066 mg, 5.06 mmol) and p-toluene sulphonic acid (3.70 g, 19.44 mmol) in acetonitrile (45 mL) was added a solution of potassium iodide (2.77 g, 16.71 mmol) and sodium nitrite (877 mg, 12.71 mmol) in water (5 mL) at 24° C. After 18 h, isopropyl acetate was added to the reaction mixture. The resulting solution was washed with water (2×) and saturated aqueous sodium chloride solution. The organic was dried over magnesium sulfate, filtered, and concentrated. The residue was purified by column chromatography (silica gel, 100-200 mesh, 0 to 100% iPrOAc in heptane) affording 2-iodo-5-(trifluoromethyl)-[1,2,4]triazolo[1,5-a]pyridine (929 mg, 58.6%) as a light yellow solid. LC-MS $R_T$=1.93 min, m/z=313.9 $(M+H)^+$.

LCMS (5 to 95% acetonitrile in water+0.1% formic acid over 5 mins) retention time 1.93 min, ESI+ found [M+H]=313.9.

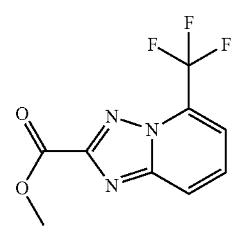 [SMILES: COC(=O)c1nc2cccc(C(F)(F)F)n2n1]

Step 3: methyl 5-(trifluoromethyl)-[1,2,4]triazolo[1,5-a]pyridine-2-carboxylate

To a solution of 2-iodo-5-(trifluoromethyl)-[1,2,4]triazolo[1,5-a]pyridine (250 mg, 0.798 mmol) in MeOH (15 mL)) in an Easy Max autoclave was added [1,1'-bis(diphenylphosphino)ferrocene]dichloropalladium(II) (60 mg, 0.08 mmol), trimethylamine (1.11 mL, 7.98 mmol). The autoclave was sealed, purged with CO twice, and pressured at 120 psi. The reaction mixture was stirred vigorously and heated at 80° C. for 15 h, concentrated to dryness in vacuo. The residue was purified by column chromatography (silica gel, 100-200 mesh, 0 to 15% methanol in dichloromethane) affording methyl 5-(trifluoromethyl)-[1,2,4]triazolo[1,5-a]pyridine-2-carboxylate (179 mg, 91.4%) as an off white solid. LC-MS $R_T$=1.10 min, m/z=246.0 $(M+H)^+$.

LCMS (5 to 95% acetonitrile in water+0.1% formic acid over 2 mins) retention time 1.10 min, ESI+ found [M+H]=246.0.

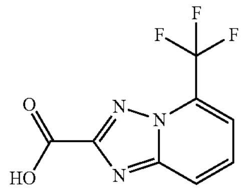 [SMILES: O=C(O)c1nc2cccc(C(F)(F)F)n2n1]

Step 4: 5-(trifluoromethyl)-[1,2,4]triazolo[1,5-a]pyridine-2-carboxylic acid

To a solution of methyl 5-(trifluoromethyl)-[1,2,4]triazolo[1,5-a]pyridine-2-carboxylate (64 mg, 0.261 mmol) in tetrahydrofuran (4 mL) and methanol (1 mL) was added lithiumhydroxide (1 mol/L) in water (1 mL, 1.0 mmol). The reaction mixture was stirred at RT for 1 h. After this time, the mixture was concentrated to dryness in vacuo. The residue was diluted with water (2 mL) and then adjusted to pH=1 by addition of 1 N hydrochloric acid. The solution was extracted with isopropyl acetate (3×25 mL). The combined organic layers were dried over sodium sulfate and concentrated to dryness in vacuo to afford 5-(trifluoromethyl)-[1,2,4]triazolo[1,5-a]pyridine-2-carboxylic acid (60 mg, 99% yield) as a white solid used in the next step without further purification. LCMS $R_T$=0.88 min, m/z=232.2 $[M+H]^+$.

LCMS (5 to 95% acetonitrile in water+0.1% formic acid over 2 mins) retention time 0.88 min, ESI+ found [M+H]=232.2.

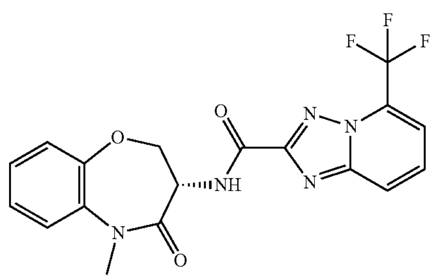

Step 5: (S)—N-(5-methyl-4-oxo-2,3,4,5-tetrahydrobenzo[b][1,4]oxazepin-3-yl)-5-(trifluoromethyl)-[1,2,4]triazolo[1,5-a]pyridine-2-carboxamide To a solution of (S)-3-amino-5-methyl-2,3-dihydrobenzo[b][1,4]oxazepin-4(5H)-one (93 mg, 0.409 mmol) and 5-(trifluoromethyl)-[1,2,4]triazolo[1,5-a]pyridine-2-carboxylic acid (63 mg, 0.272 mmol) in N,N-dimethylformamide (1.5 mL) was added HATU (120.9 mg, 0.327 mmol), and N,N-diisopropylethylamine (0.14 mL, 0.818 mmol. The reaction mixture was stirred overnight at RT, then was purified directly by preparative RP-HPLC (20-60% acetonitrile in water+0.1% formic acid) affording (S)—N-(5-methyl-4-oxo-2,3,4,5-tetrahydrobenzo[b][1,4]oxazepin-3-yl)-5-(trifluoromethyl)-[1, 2,4]triazolo[1,5-a]pyridine-2-carboxamide (65.5 mg, 58%) as a white solid: $^1$H NMR (400 MHz, DMSO-$d_6$) δ 8.88 (d, J=7.8 Hz, 1H), 8.30 (dd, J=8.3, 2.0 Hz, 1H), 8.00-7.89 (m, 2H), 7.53 (dd, J=7.6, 2.0 Hz, 1H), 7.31 (dddd, J=21.7, 14.5, 7.4, 2.0 Hz, 3H), 4.92 (dt, J=11.4, 7.8 Hz, 1H), 4.66 (dd, J=11.6, 9.9 Hz, 1H), 4.49 (dd, J=9.9, 7.7 Hz, 1H), 3.34 (s, 3H). LC-MS $R_T$=4.90 min, m/z=406.0 (M+H).

LCMS (5 to 95% acetonitrile in water+0.1% formic acid over 10 mins) retention time 4.90 min, ESI+ found [M+H]=406.0

Examples 413-416

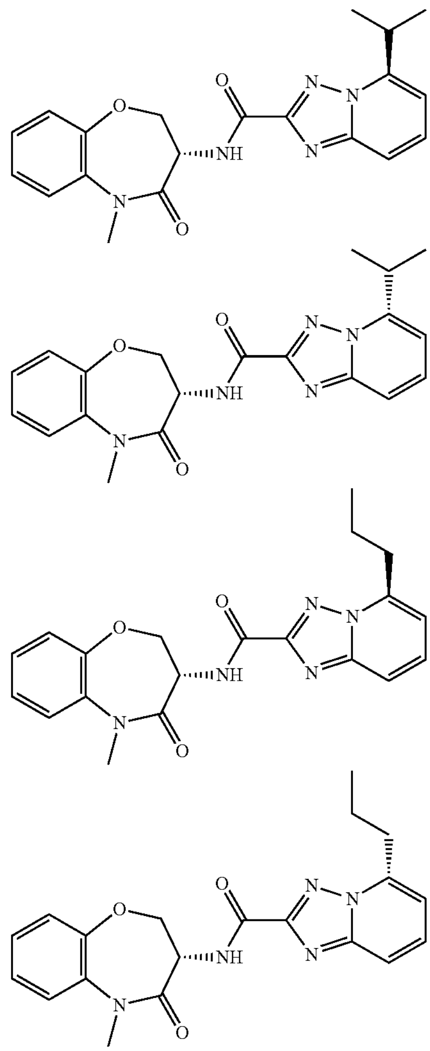

(R)-5-isopropyl-N—((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide (S)-5-isopropyl-N—((S)-5-methyl-4-oxo-2,3,4,5-tetrahydrobenzo[b][1,4]methyl-4-oxo-1,2,4]oxazepin-3-yl)-5,6,7,8-tetrahydro-[1,2,4]triazolo[1,5-a]pyridine-2-carboxamide (S)—N—((S)-5-methyl-4-oxo-2,3,4,5-tetrahydrobenzo[b][1,4]oxazepin-3-yl)-5-propyl-5,6,7, 8-tetrahydro-[1,2,4]triazolo[1,5-a]pyridine-2-carboxamide (R)—N—((S)-5-methyl-4-oxo-2,3,4,5-tetrahydrobenzo[b][1,4]oxazepin-3-yl)-5-propyl-5,6,7, 8-tetrahydro-[1,2,4]triazolo[1,5-a]pyridine-2-carboxamide Mixture of 64% (S)-5-isopropyl-N-(5-methyl-4-oxo-2,3,4,5-tetrahydrobenzo[b][1,4]oxazepin-3-yl)-[1,2,4]triazolo[1,5-a]pyridine-2-carboxamide and 36% (S)—N-(5-methyl- 4-oxo-2,3,4,5-tetrahydrobenzo[b][1,4]oxazepin-3-yl)-5-propyl-[1,2,4]triazolo[1,5-a]pyridine-2-carboxamide was reduced according to Method GZ2. The crude residue was further purified by chiral SFC (Chiralpak ID; 150×21.2 mm, 5 um; 35% methanol isocratic elution with Carbon Dioxide) affording four isomers (structural isomers were assigned based on 1H NMR; diastereomers were arbitrarily assigned):

(R)-5-isopropyl-N—((S)-5-methyl-4-oxo-2,3,4,5-tetrahydrobenzo[b][1,4]oxazepin-3-yl)-5,6,7, 8-tetrahydro-[1,2,4]triazolo[1,5-a]pyridine-2-carboxamide (26 mg, 23%) as a white solid.

(S)—N—((S)-5-methyl-4-oxo-2,3,4,5-tetrahydrobenzo[b][1,4]oxazepin-3-yl)-5-propyl-5,6,7,8-tetrahydro-[1,2,4]triazolo[1,5-a]pyridine-2-carboxamide (16.1 mg, 14%) as a white solid.

(S)-5-isopropyl-N—((S)-5-methyl-4-oxo-2,3,4,5-tetrahydrobenzo[b][1,4]oxazepin-3-yl)-5,6,7, 8-tetrahydro-[1,2,4]triazolo[1,5-a]pyridine-2-carboxamide (22.6 mg, 19.8%) as a white solid.

(R)—N—((S)-5-methyl-4-oxo-2,3,4,5-tetrahydrobenzo[b][1,4]oxazepin-3-yl)-5-propyl-5,6,7,8-tetrahydro-[1,2,4]triazolo[1,5-a]pyridine-2-carboxamide (12.7 mg, 10.5%) as a white solid.

Analytical data for the first eluting disomer (arbitrarily assigned R, S configuration): SFC $R_T$(OX, 35% methanol+0.1% ammonium hydroxide isocratic elution with Carbon Dioxide, 2.5 min method): 0.655 min, 100% purity, 100% ee: $^1$H NMR (400 MHz, DMSO-$d_6$) δ 8.34 (d, J=7.9 Hz, 1H), 7.62 (s, 1H), 7.49 (dd, J=7.6, 2.0 Hz, 1H), 7.39-7.19 (m, 4H), 5.47 (t, J=5.8 Hz, 1H), 4.81 (dt, J=11.4, 7.7 Hz, 1H), 4.55 (dd, J=11.5, 9.9 Hz, 1H), 4.39 (dd, J=9.9, 7.7 Hz, 1H), 3.78 (s, 3H), 3.31 (s, 3H), 2.93 (td, J=6.4, 2.6 Hz, 2H), 2.29 (ddd, J=8.6, 5.2, 3.3 Hz, 1H), 2.12 (dtd, J=14.0, 7.5, 6.6, 3.0 Hz, 1H), 2.03-1.83 (m, 2H). LCMS $R_T$=5.026 min, m/z=384.2 $(M+H)^+$.

LCMS (5 to 95% acetonitrile in water+0.1% formic acid over 10 mins) retention time 5.026 min, ESI+ found [M+H]= 384.2

Analytical data for the second eluting isomer (arbitrarily assigned S, S configuration): SFC $R_T$(OX, 35% methanol+0.1% ammonium hydroxide isocratic elution with Carbon Dioxide, 2.5 min method): 0.823 min, 100% purity, 100% ee: $^1$H NMR (400 MHz, DMSO-$d_6$) δ 8.36 (d, J=8.0 Hz, 1H), 7.50 (dd, J=7.5, 2.0 Hz, 1H), 7.37-7.20 (m, 3H), 4.83 (dt, J=11.4, 7.8 Hz, 1H), 4.58 (dd, J=11.5, 9.8 Hz, 1H), 4.41 (dd, J=9.9, 7.7 Hz, 1H), 4.24 (d, J=13.1 Hz, 1H), 3.31 (s, 3H), 2.84 (q, J=6.1, 5.5 Hz, 2H), 2.19-1.91 (m, 3H), 1.85-1.57 (m, 3H), 1.48-1.29 (m, 2H), 0.92 (t, J=7.3 Hz, 3H). LCMS $R_T$=5.12 min, m/z=384.2 $(M+H)^+$.

LCMS (5 to 95% acetonitrile in water+0.1% formic acid over 10 mins) retention time 5.12 min, ESI+ found [M+H]= 384.2

Analytical data for the third eluting isomer (arbitrarily assigned S, S configuration): SFC $R_T$(OX, 35% methanol+0.1% ammonium hydroxide isocratic elution with Carbon Dioxide, 2.5 min method): 1.391 min, 98.8% purity, 97.7% ee:: $^1$H NMR (400 MHz, DMSO-$d_6$) δ 8.34 (d, J=7.9 Hz, 1H), 7.62 (s, 1H), 7.49 (dd, J=7.6, 2.0 Hz, 1H), 7.39-7.19 (m, 4H), 5.47 (t, J=5.8 Hz, 1H), 4.81 (dt, J=11.4, 7.7 Hz, 1H), 4.55 (dd, J=11.5, 9.9 Hz, 1H), 4.39 (dd, J=9.9, 7.7 Hz, 1H), 3.78 (s, 3H), 3.31 (s, 3H), 2.93 (td, J=6.4, 2.6 Hz, 2H), 2.29 (ddd, J=8.6, 5.2, 3.3 Hz, 1H), 2.12 (dtd, J=14.0, 7.5, 6.6, 3.0 Hz, 1H), 2.03-1.83 (m, 2H). LCMS $R_T$=5.03 min, m/z=384.2 $(M+H)^+$.

LCMS (5 to 95% acetonitrile in water+0.1% formic acid over 10 mins) retention time 5.03 min, ESI+ found [M+H]= 384.2

Analytical data for the fourth eluting isomer (arbitrarily assigned R, S configuration): SFC $R_T$(OX, 35% methanol+0.1% ammonium hydroxide isocratic elution with Carbon Dioxide, 2.5 min method): 1.475 min, 100% purity, 100% ee:: $^1$H NMR (400 MHz, DMSO-$d_6$) δ 8.36 (d, J=8.0 Hz, 1H), 7.50 (dd, J=7.5, 2.0 Hz, 1H), 7.37-7.20 (m, 3H), 4.83 (dt, J=11.4, 7.8 Hz, 1H), 4.58 (dd, J=11.5, 9.8 Hz, 1H), 4.41 (dd, J=9.9, 7.7 Hz, 1H), 4.24 (d, J=13.1 Hz, 1H), 3.31 (s, 3H), 2.84 (q, J=6.1, 5.5 Hz, 2H), 2.19-1.91 (m, 3H), 1.85-1.57 (m, 3H), 1.48-1.29 (m, 2H), 0.92 (t, J=7.3 Hz, 3H). LCMS $R_T$=5.14 min, m/z=384.2 $(M+H)^+$.

LCMS (5 to 95% acetonitrile in water+0.1% formic acid over 10 mins) retention time 5.14 min, ESI+ found [M+H]= 384.2

Example 417

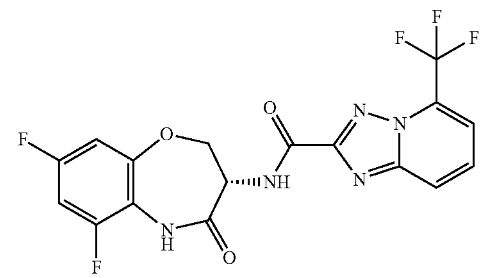 [SMILES: O=C(N[C@H]1COc2cc(F)cc(F)c2NC1=O)c1nc2cccc(C(F)(F)F)n2n1]

(S)—N-(6,8-difluoro-4-oxo-2,3,4,5-tetrahydrobenzo[b][1,4]oxazepin-3-yl)-5-(trifluoromethyl)-[1,2,4]triazolo[1,5-a]pyridine-2-carboxamide (S)—N-(6,8-difluoro-4-oxo-2,3,4,5-tetrahydrobenzo[b][1,4]oxazepin-3-yl)-5-(trifluoromethyl)-[1,2,4]triazolo[1,5-a]pyridine-2-carboxamide was prepared corresponding from (S)-3-amino-6,8-difluoro-2,3-dihydrobenzo[b][1,4]oxazepin-4(5H)-one, and 5-(trifluoromethyl)-[1,2,4]triazolo[1,5-a]pyridine-2-carboxylic acid according to Method GZ5. The residue was purified by preparative RP-HPLC (20-60% acetonitrile in water+0.1% formic acid) instead. Yield of final step: 123 mg, 78.0%. $^1$H NMR (400 MHz, DMSO-$d_6$) δ 10.12 (s, 1H), 8.88 (d, J=7.6 Hz, 1H), 8.31 (dd, J=8.3, 1.9 Hz, 1H), 8.01-7.90 (m, 2H), 7.25 (ddd, J=10.4, 9.1, 2.9 Hz, 1H), 7.06 (dt, J=9.3, 2.3 Hz, 1H), 5.00 (dt, J=10.9, 7.3 Hz, 1H), 4.72 (t, J=10.6 Hz, 1H), 4.60 (dd, J=10.2, 7.1 Hz, 1H). LC-MS $R_T$=4.72 min, m/z=428 $(M+H)^+$.

LCMS (5 to 95% acetonitrile in water+0.1% formic acid over 10 mins) retention time 4.72 min, ESI+ found [M+H]= 428

Example 418

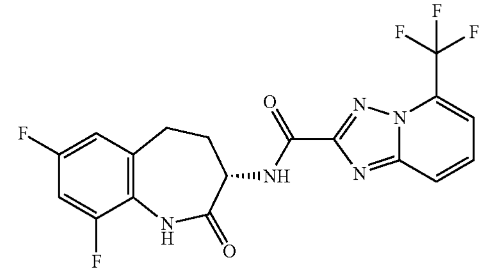

(S)—N-(7,9-difluoro-2-oxo-2,3,4,5-tetrahydro-1H-benzo[b]azepin-3-yl)-5-(trifluoromethyl)-[1,2,4]triazolo[1,5-a]pyridine-2-carboxamide (S)—N-(7,9-difluoro-2-oxo-2,3,4,5-tetrahydro-1H-benzo[b]azepin-3-yl)-5-(trifluoromethyl)-[1,2,4]triazolo[1,5-a]pyridine-2-carboxamide was prepared corresponding from (S)-3-amino-7,9-difluoro-1,3,4,5-tetrahydro-2H-benzo[b]azepin-2-one, and 5-(trifluoromethyl)-[1,2,4]triazolo[1,5-a]pyridine-2-carboxylic acid according to Method GZ5. The residue was purified by preparative RP-HPLC (20-60% acetonitrile in water+0.1% formic acid) instead. Yield of final step: 80.9 mg, 51.7%. $^1$H NMR (400 MHz, DMSO-$d_6$) δ 10.02 (s, 1H), 8.72 (d, J=7.4 Hz, 1H), 8.30 (dd, J=8.2, 2.1 Hz, 1H), 8.00-7.89 (m, 2H), 7.29 (ddd, J=10.0, 8.9, 2.8 Hz, 1H), 7.21-7.13 (m, 1H), 4.43 (dt, J=11.5, 7.8 Hz, 1H), 3.37-3.22 (m, 3H), 2.87-2.74 (m, 2H), 2.39-2.25 (m, 1H). LC-MS $R_T$=4.69 min, m/z=426 $(M+H)^+$.

LCMS (5 to 95% acetonitrile in water+0.1% formic acid over 10 mins) retention time 4.69 min, ESI+ found [M+H]=426

Example 419

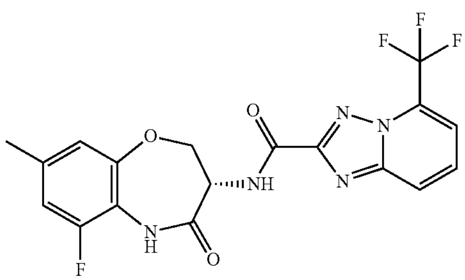 [SMILES: Cc1cc(F)c2c(c1)OC[C@H](NC(=O)c1nc3cccc(C(F)(F)F)n3n1)C(=O)N2]

(S)—N-(6-fluoro-8-methyl-4-oxo-2,3,4,5-tetrahydrobenzo[b][1,4]oxazepin-3-yl)-5-(trifluoromethyl)-[1,2,4]triazolo[1,5-a]pyridine-2-carboxamide (S)—N-(6-fluoro-8-methyl-4-oxo-2,3,4,5-tetrahydrobenzo[b][1,4]oxazepin-3-yl)-5-(trifluoromethyl)-[1,2,4]triazolo[1,5-a]pyridine-2-carboxamide was prepared corresponding from (S)-3-amino-6-fluoro-8-methyl-2,3-dihydrobenzo[b][1,4]oxazepin-4(5H)-one, and 5-(trifluoromethyl)-[1,2,4]triazolo[1,5-a]pyridine-2-carboxylic acid according to Method GZ5. The residue was purified by preparative RP-HPLC (20-60% acetonitrile in water+0.1% formic acid) instead. Yield of final step: 86.2 mg, 55%. $^1$H NMR (400 MHz, DMSO-$d_6$) δ 10.06 (s, 1H), 8.86 (d, J=7.7 Hz, 1H), 8.31 (dd, J=8.3, 1.9 Hz, 1H), 8.01-7.90 (m, 2H), 7.00 (dd, J=10.7, 1.8 Hz, 1H), 6.92 (s, 1H), 4.94 (dt, J=11.0, 7.4 Hz, 1H), 4.67 (t, J=10.7 Hz, 1H), 4.54 (dd, J=10.2, 7.3 Hz, 1H), 2.31 (s, 3H). LC-MS $R_T$=4.98 min, m/z=424.1 $(M+H)^+$.

LCMS (5 to 95% acetonitrile in water+0.1% formic acid over 10 mins) retention time 4.98 min, ESI+ found [M+H]=424.1

Example 420

Method GZ12

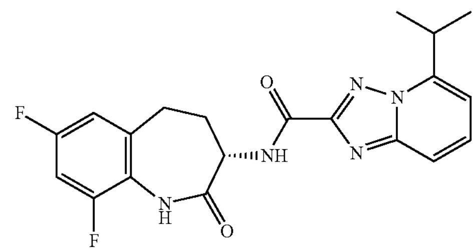 [SMILES: CC(C)c1cccc2nc(C(=O)N[C@H]3CCc4cc(F)cc(F)c4NC3=O)nn12]

(S)—N-(7,9-difluoro-2-oxo-2,3,4,5-tetrahydro-1H-benzo[b]azepin-3-yl)-5-isopropyl-[1,2,4]triazolo[1,5-a]pyridine-2-carboxamide

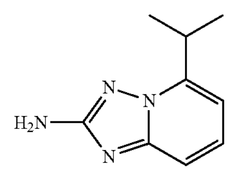

Step 1: 5-isopropyl-[1,2,4]triazolo[1,5-a]pyridin-2-amine

A suspension of 5-bromo-[1,2,4]triazolo[1,5-a]pyridin-2-amine (700 mg, 3.29 mmol) in dioxane (12 mL) was degassed, cooled to ice bath, added 1,3-bis(diphenylphosphino)propane nickel (II) chloride (178 mg, 0.329 mmol) under nitrogen, followed by diisopropyl zinc (1M solution in toluene) via syringe over 10 mins. Removed the ice bath, heated up to 95° C. for overnight. The reaction mixture was poured into isopropyl alcohol, and concentrated to dryness in vacuo. The residue was diluted with saturated Ammonium chloride (50 mL) and extracted with isopropyl acetate (3×75 mL). The combined organics were dried over sodium sulfate, filtered, and concentrated to dryness in vacuo to afford 5-isopropyl-[1,2,4]triazolo[1,5-a]pyridin-2-amine (424 mg, 73%) as a tan solid, which was used in the next step without further purification. LCMS $R_T$=0.90 min, m/z=177.2 $[M+H]^+$.

LCMS (5 to 95% acetonitrile in water+0.1% formic acid over 2 mins) retention time 0.90 min, ESI+ found [M+H]=177.2.

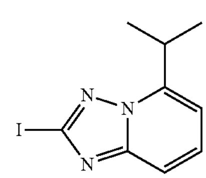

Step 2: 2-iodo-5-isopropyl-[1,2,4]triazolo[1,5-a]pyridine

To a solution of 5-isopropyl-[1,2,4]triazolo[1,5-a]pyridin-2-amine (800 mg, 4.54 mmol) and p-toluene sulphonic acid (3.32 g, 17.43 mmol) in acetonitrile (40 mL) was added a solution of potassium iodide (2.49 g, 14.98 mmol) and sodium nitrite (786 mg, 11.40 mmol) in water (5 mL) at 24° C. After 18 h, isopropyl acetate was added to the reaction mixture. The resulting solution was washed with water (2×100 mL) and saturated aqueous sodium chloride solution. The organic was dried over magnesium sulfate, filtered, and concentrated. The residue was purified by column chromatography (silica gel, 100-200 mesh, 0 to 100% isopropyl acetate in heptane) affording 2-iodo-5-isopropyl-[1,2,4]triazolo[1,5-a]pyridine (534 mg, 41%) as a light yellow solid. LCMS $R_T$=1.38 min, m/z=288.0 $[M+H]^+$.

LCMS (5 to 95% acetonitrile in water+0.1% formic acid over 2 mins) retention time 1.38 min, ESI+ found [M+H]=288.0.

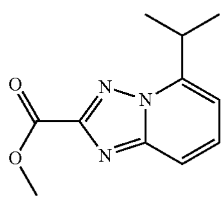 [SMILES: COC(=O)c1nc2cccc(C(C)C)n2n1]

Step 3: methyl 5-isopropyl-[1,2,4]triazolo[1,5-a]pyridine-2-carboxylate

To a solution of 2-iodo-5-isopropyl-[1,2,4]triazolo[1,5-a]pyridine (1000 mg, 3.48 mmol) in MeOH (20 mL)) in an Easy Max autoclave was added [1,1'-bis(diphenylphosphino)ferrocene]dichloropalladium(II) (260 mg, 0.348 mmol), trimethylamine (4.85 mL, 34.83 mmol). The autoclave was sealed, purged with CO twice, and pressured at 120 psi. The reaction mixture was stirred vigorously and heated at 80° C. for 15 h, concentrated to dryness in vacuo. The residue was purified by column chromatography (silica gel, 100-200 mesh, 0 to 15% methanol in dichloromethane) affording methyl 5-isopropyl-[1,2,4]triazolo[1,5-a]pyridine-2-carboxylate (710 mg, 93%) as an off white solid. LCMS $R_T$=1.14 min, m/z=220.1 $[M+H]^+$.

LCMS (5 to 95% acetonitrile in water+0.1% formic acid over 2 mins) retention time 1.14 min, ESI+ found [M+H]=220.1.

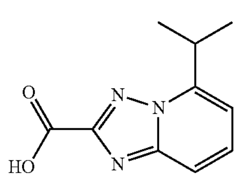

Step 4: 5-isopropyl-[1,2,4]triazolo[1,5-a]pyridine-2-carboxylic acid

To a solution of methyl 5-isopropyl-[1,2,4]triazolo[1,5-a]pyridine-2-carboxylate (806 mg, 3.68 mmol) in tetrahydrofuran (20 mL) and methanol (7 mL) was added lithiumhydroxide (1 mol/L) in water (7 mL, 7.0 mmol). The reaction mixture was stirred at RT for 1 h. After this time, the mixture was concentrated to dryness in vacuo. The residue was diluted with water (2 mL) and then adjusted to pH=1 by addition of 1 N hydrochloric acid. The solution was extracted with isopropyl acetate (3×75 mL). The combined organic layers were dried over sodium sulfate and concentrated to dryness in vacuo to afford 5-isopropyl-[1,2,4]triazolo[1,5-a]pyridine-2-carboxylic acid (716 mg, 95% yield) as a white solid used in the next step without further purification. LCMS $R_T$=0.96 min, m/z=206.2 $[M+H]^+$.

LCMS (5 to 95% acetonitrile in water+0.1% formic acid over 2 mins) retention time 0.96 min, ESI+ found [M+H]=206.2.

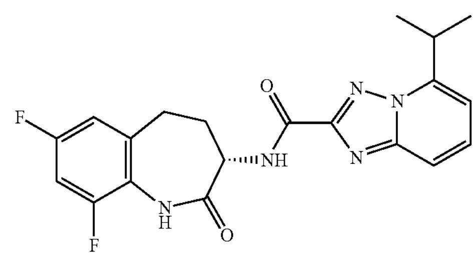 [SMILES: CC(C)c1cccc2nc(C(=O)N[C@H]3CCc4cc(F)cc(F)c4NC3=O)nn12]

Step 5: (S)—N-(7,9-difluoro-2-oxo-2,3,4,5-tetrahydro-1H-benzo[b]azepin-3-yl)-5-isopropyl-[1,2,4]triazolo[1,5-a]pyridine-2-carboxamide To a solution of (S)-3-amino-7,9-difluoro-1,3,4,5-tetrahydro-2H-benzo[b]azepin-2-one (132 mg, 0.532 mmol) and 5-isopropyl-[1,2,4]triazolo[1,5-a]pyridine-2-carboxylic acid (95 mg, 0.460 mmol) in N,N-dimethylformamide (1.5 mL) was added HATU (215 mg, 0.560 mmol), and N,N-diisopropylethylamine (0.24 mL, 1.39 mmol. The reaction mixture was stirred overnight at RT, then was purified by preparative RP-HPLC (20-60% acetonitrile in water+0.1% formic acid) to afford as tan solid (103.7 mg, 56%) as a mixture of 64% (S)—N-(7,9-difluoro-2-oxo-2,3,4,5-tetrahydro-1H-benzo[b]azepin-3-yl)-5-isopropyl-[1,2,4]triazolo[1,5-a]pyridine-2-carboxamide and 36% (S)—N-(7,9-difluoro-2-oxo-2,3,4,5-tetrahydro-1H-benzo[b]azepin-3-yl)-5-propyl-[1,2,4]triazol o[1,5-a]pyridine-2-carboxamide. This final compound was observed as single peak by LC-MS, was confirmed by $^1H$ NMR which showed purity was 64%. $^1H$ NMR (400 MHz, DMSO-$d_6$) δ 10.00 (s, 1H), 8.63 (dd, J=7.5, 3.0 Hz, 1H), 7.85-7.68 (m, 3H), 7.29 (ddd, J=10.2, 8.9, 2.8 Hz, 1H), 7.18 (ddt, J=11.0, 8.7, 1.9 Hz, 3H), 4.43 (dt, J=11.6, 7.7 Hz, 1H), 3.77 (h, J=6.8 Hz, 1H), 3.39-3.25 (m, 1H), 2.83 (dd, J=11.1, 5.5 Hz, 2H), 2.30 (ddt, J=12.4, 9.3, 4.0 Hz, 1H), 1.39 (d, J=6.9 Hz, 6H). LC-MS $R_T$=4.92 min, m/z=400.1 $(M+H)^+$.

LCMS (5 to 95% acetonitrile in water+0.1% formic acid over 10 mins) retention time 4.92 min, ESI+ found [M+H]=400.1

Example 421

Method GZ15

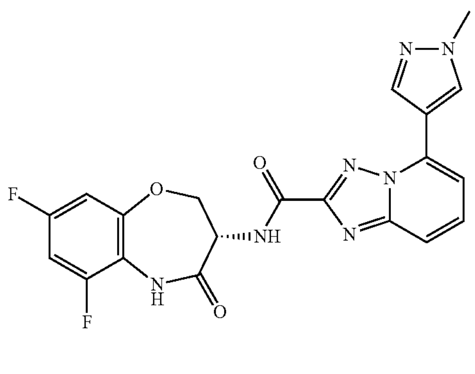 [SMILES: Cn1cc(-c2cccc3nc(C(=O)N[C@H]4COc5cc(F)cc(F)c5NC4=O)nn23)cn1]

(S)—N-(6,8-difluoro-4-oxo-2,3,4,5-tetrahydrobenzo[b][1,4]oxazepin-3-yl)-5-(1-methyl-1H-pyrazol-4-yl)-[1,2,4]triazolo[1,5-a]pyridine-2-carboxamide

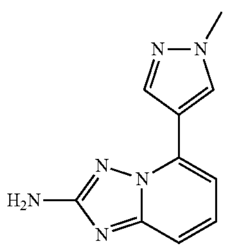 [SMILES: Cn1cc(-c2cccc3nc(N)nn23)cn1]

Step 1: 5-(1-methyl-1H-pyrazol-4-yl)-[1,2,4]triazolo[1,5-a]pyridin-2-amine

A mixture of 5-bromo-[1,2,4]triazolo[1,5-a]pyridin-2-amine (500 mg, 2.347 mmol), 1-methyl-4-(4,4,5,5-tetramethyl-1,3,2-dioxaborolan-2-yl)pyrazole (977 mg, 4.694 mmol), tripotassium phosphate (1541 mg, 7.041 mmol) in tetrahydrofuran (16 mL) and water (4 mL) was degassed, then 2-Dicyclohexylphosphino-2',4',6'-triisopropylbiphenyl (67 mg, 0.141 mmol) and X-Phos aminobiphenyl palladium chloride precatalyst, XPhos-Pd-G2 (63 mg, 0.071 mmol) was added under nitrogen. The microwave vial was capped and heated to 85° C. for 45 minutes. The reaction mixture was cooled down, diluted with saturated aqueous sodium bicarbonate (50 mL) and extracted with isopropyl acetate (3×75 mL). The combined organics were dried over sodium sulfate, filtered, and concentrated to dryness in vacuo, triturated with isopropyl acetate, filtered out the solid to afford 5-(1-methyl-1H-pyrazol-4-yl)-[1,2,4]triazolo[1,5-a]pyridin-2-amine (385 mg, 76.7%) as a brown solid. LC-MS $R_T$=1.10 min, m/z=215.0 $(M+H)^+$.

LCMS (5 to 95% acetonitrile in water+0.1% formic acid over 5 mins) retention time 1.10 min, ESI+ found [M+H]=215.0.

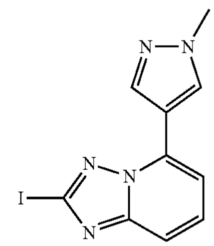 [SMILES: Cn1cc(-c2cccc3nc(I)nn23)cn1]

Step 2: 2-iodo-5-(1-methyl-1H-pyrazol-4-yl)-[1,2,4]triazolo[1,5-a]pyridine

To a solution of 5-(1-methyl-1H-pyrazol-4-yl)-[1,2,4]triazolo[1,5-a]pyridin-2-amine (1011 mg, 4.719 mmol) and p-toluene sulphonic acid (3.45 g, 18.122 mmol) in acetonitrile (30 mL) was added a solution of potassium iodide (2590 mg, 15.573 mmol) and sodium nitrite (817 mg, 11.845 mmol) in water (5 mL) at 24° C. After 18 h, isopropyl acetate was added to the reaction mixture. The resulting solution was washed with water (2×150) and saturated aqueous sodium chloride solution. The organic was dried over magnesium sulfate, filtered, and concentrated. The residue was purified by column chromatography (silica gel, 100-200 mesh, 0 to 100% iPrOAc in heptane) affording 2-iodo-5-(1-methyl-1H-pyrazol-4-yl)-[1,2,4]triazolo[1,5-a]pyridine (800 mg, 52%) as a light yellow solid. LC-MS $R_T$=2.04 min, m/z=325.9 $(M+H)^+$.

LCMS (5 to 95% acetonitrile in water+0.1% formic acid over 5 mins) retention time 2.04 min, ESI+ found [M+H]=325.9.

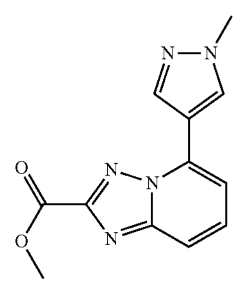 [SMILES: COC(=O)c1nc2cccc(-c3cnn(C)c3)n2n1]

Step 3: methyl 5-(1-methyl-1H-pyrazol-4-yl)-[1,2,4]triazolo[1,5-a]pyridine-2-carboxylate To a solution of 2-iodo-5-(1-methyl-1H-pyrazol-4-yl)-[1,2,4]triazolo[1,5-a]pyridine (800 mg, 2.461 mmol) in MeOH (20 mL)) in an Easy Max autoclave was added [1,1'-bis(diphenylphosphino)ferrocene]dichloropalladium(II) (184 mg, 0.246 mmol), trimethylamine (3.43 mL, 24.607 mmol). The autoclave was sealed, purged with CO twice, and pressured at 120 psi. The reaction mixture was stirred vigorously and heated at 80° C. for 15 h, concentrated to dryness in vacuo. The residue was purified by column chromatography (silica gel, 100-200 mesh, 0 to 15% methanol in dichloromethane) affording methyl 5-(1-methyl-1H-pyrazol-4-yl)-[1,2,4]triazolo[1,5-a]pyridine-2-carboxylate (574 mg, 91%) as a brown solid. LC-MS $R_T$=0.97 min, m/z=258.1 $(M+H)^+$.

LCMS (5 to 95% acetonitrile in water+0.1% formic acid over 2 mins) retention time 0.97 min, ESI+ found [M+H]=258.1.

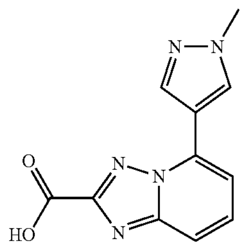 [SMILES: Cn1cc(-c2cccc3nc(C(=O)O)nn23)cn1]

Step 4: 5-(1-methyl-1H-pyrazol-4-yl)-[1,2,4]triazolo[1,5-a]pyridine-2-carboxylic acid To a solution of methyl 5-(1-methyl-1H-pyrazol-4-yl)-[1,2,4]triazolo[1,5-a]pyridine-2-carboxylate (574 mg, 2.231 mmol) in tetrahydrofuran (12 mL) and methanol (3 mL) was added lithiumhydroxide (1 mol/L) in water (4 mL, 1.0 mmol). The reaction mixture was stirred at RT for 1 h. After this time, the mixture was concentrated to dryness in vacuo. The residue was diluted with water (15 mL) and then adjusted to pH=1 by addition of 1 N hydrochloric acid. The solution was extracted with isopropyl acetate (3×100 mL). The combined organic layers were dried over sodium sulfate and concentrated to dryness in vacuo to afford 5-(1-methyl-1H-pyrazol-4-yl)-[1,2,4]triazolo[1,5-a]pyridine-2-carboxylic acid (381 mg, 70% yield) as a brown solid used in the next step without further purification. LCMS $R_T$=0.92 min, m/z=244.1 $[M+H]^+$.

LCMS (5 to 95% acetonitrile in water+0.1% formic acid over 2 mins) retention time 0.92 min, ESI+ found [M+H]=244.1.

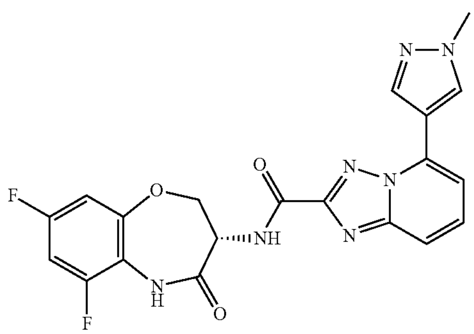 [SMILES: Cn1cc(-c2cccc3nc(C(=O)N[C@H]4COc5cc(F)cc(F)c5NC4=O)nn23)cn1]

Step 5: (S)—N-(6,8-difluoro-4-oxo-2,3,4,5-tetrahydrobenzo[b][1,4]oxazepin-3-yl)-5-(1-methyl-1H-pyrazol-4-yl)-[1,2,4]triazolo[1,5-a]pyridine-2-carboxamide To a solution of (S)-3-amino-6,8-difluoro-2,3-dihydrobenzo[b][1,4]oxazepin-4(5H)-one (95 mg, 0.378 mmol) and 5-(1-methyl-1H-pyrazol-4-yl)-[1,2,4]triazolo[1,5-a]pyridine-2-carboxylic acid (80 mg, 0.329 mmol) in N,N-dimethylformamide (1.5 mL) was added HATU (153 mg, 0.395 mmol), and N,N-diisopropylethylamine (0.23 mL, 1.316 mmol. The reaction mixture was stirred overnight at RT, then was purified by preparative RP-HPLC (5-50% acetonitrile in water+0.1% formic acid) to afford (S)—N-(6,8-difluoro-4-oxo-2,3,4,5-tetrahydrobenzo[b][1,4]oxazepin-3-yl)-5-(1-methyl-1H-pyrazol-4-yl)-[1,2,4]triazolo[1,5-a]pyridine-2-carboxamide as tan solid (2 mg, 1.4% yield). 1H NMR (400 MHz, DMSO-d6) δ 10.12 (s, 2H), 8.96-8.89 (m, 4H), 8.53 (s, 2H), 7.88-7.73 (m, 6H), 7.26 (ddd, J=10.3, 9.0, 2.9 Hz, 2H), 7.07 (dt, J=9.1, 2.2 Hz, 2H), 5.02 (dt, J=11.1, 7.5 Hz, 2H), 4.78 (t, J=10.7 Hz, 2H), 4.62 (dd, J=10.2, 7.2 Hz, 2H), 4.00 (s, 6H), 3.32-3.22 (m, 1H), 2.47 (s, 1H). LC-MS $R_T$=4.31 min, m/z=440.1 $(M+H)^+$.

LCMS (5 to 95% acetonitrile in water+0.1% formic acid over 10 mins) retention time 4.31 min, ESI+ found [M+H]=440.1

Example 422

Method GZ16

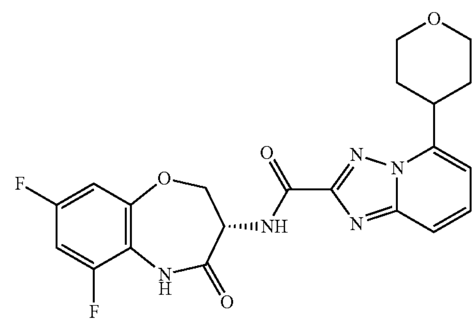 [SMILES: O=C(N[C@H]1COc2cc(F)cc(F)c2NC1=O)c1nc2cccc(C3CCOCC3)n2n1]

(S)—N-(6,8-difluoro-4-oxo-2,3,4,5-tetrahydrobenzo[b][1,4]oxazepin-3-yl)-5-(tetrahydro-2H-pyran-4-yl)-[1,2,4]triazolo[1,5-a]pyridine-2-carboxamide

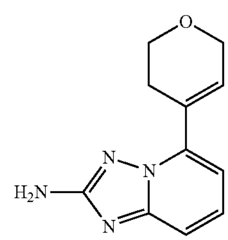 [SMILES: Nc1nc2cccc(C3=CCOCC3)n2n1]

Step 1: 5-(3,6-dihydro-2H-pyran-4-yl)-[1,2,4]triazolo[1,5-a]pyridin-2-amine

A mixture of 5-bromo-[1,2,4]triazolo[1,5-a]pyridin-2-amine (600 mg, 2.82 mmol), 3,6-dihydro-2H-pyran-4-boronic acid pinacol ester (915 mg, 4.22 mmol), tripotassium phosphate (1793 mg, 8.45 mmol) in tetrahydrofuran (16 mL) and water (4 mL) was degassed, then 2-Dicyclohexylphosphino-2',4',6'-triisopropylbiphenyl (80 mg, 0.17 mmol) and X-Phos aminobiphenyl palladium chloride precatalyst, XPhos-Pd-G2 (80 mg, 0.08 mmol) was added under nitrogen. The microwave vial was capped and heated to 85° C. for 45 minutes. The reaction mixture was cooled down, diluted with saturated aqueous sodium bicarbonate (50 mL) and extracted with isopropyl acetate (3×75 mL). The combined organics were dried over sodium sulfate, filtered, and concentrated to dryness in vacuo, triturated with isopropyl acetate, filtered out the solid to afford 5-(3,6-dihydro-2H-pyran-4-yl)-[1,2,4]triazolo[1,5-a]pyridin-2-amine (502 mg, 83%) as a tan solid. 1H NMR (400 MHz, DMSO-d6) δ 7.43

(dd, J=8.7, 7.4 Hz, 1H), 7.30 (dd, J=8.7, 1.3 Hz, 1H), 7.18 (tt, J=2.9, 1.5 Hz, 1H), 6.86 (dd, J=7.4, 1.3 Hz, 1H), 6.00 (s, 2H), 4.32 (q, J=2.8 Hz, 2H), 3.85 (t, J=5.4 Hz, 2H), 2.62 (dddd, J=6.6, 5.2, 3.3, 1.9 Hz, 2H). LCMS $R_T$=1.08 min, m/z=217.2 $(M+H)^+$.

LCMS (5 to 95% acetonitrile in water+0.1% formic acid over 5 mins) retention time 1.08 min, ESI+ found [M+H]=217.2.

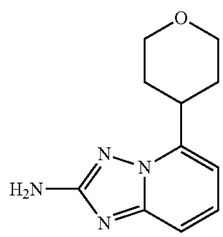 [SMILES: Nc1nc2cccc(C3CCOCC3)n2n1]

Step 2: 5-(tetrahydro-2H-pyran-4-yl)-[1,2,4]triazolo[1,5-a]pyridin-2-amine

To a solution of 5-(3,6-dihydro-2H-pyran-4-yl)-[1,2,4]triazolo[1,5-a]pyridin-2-amine (870 mg, 4.02 mmol) in ethanol (15 mL), added acetic acid (15 mL), then added platinum (iv) oxide (45 mg, 0.20 mmol). The reaction mixture stirred under a balloon of hydrogen gas for 16 h at RT, then was filtered through Celite and concentrated to dryness in vacuo. The residue was diluted with saturated aqueous sodium bicarbonate (50 mL) and extracted with isopropyl acetate (3×75 mL). The combined organics were dried over sodium sulfate, filtered, and concentrated to dryness in vacuo affording 5-(tetrahydro-2H-pyran-4-yl)-[1,2,4]triazolo[1,5-a]pyridin-2-amine (755 mg, 86%) as an off white solid. LC-MS $R_T$=1.15 min, m/z=219.1 $(M+H)^+$.

LCMS (5 to 95% acetonitrile in water+0.1% formic acid over 5 mins) retention time 1.15 min, ESI+ found [M+H]=219.1

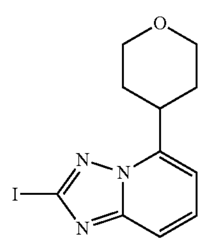 [SMILES: Ic1nc2cccc(C3CCOCC3)n2n1]

Step 3: 2-iodo-5-(tetrahydro-2H-pyran-4-yl)-[1,2,4]triazolo[1,5-a]pyridine

To a solution of 5-(tetrahydro-2H-pyran-4-yl)-[1,2,4]triazolo[1,5-a]pyridin-2-amine (750 mg, 3.44 mmol) and p-toluene sulphonic acid (2.51 g, 13.2 mmol) in acetonitrile (45 mL) was added a solution of potassium iodide (1.88 g, 11.34 mmol) and sodium nitrite (595 mg, 8.62 mmol) in water (5 mL) at 24° C. After 18 h, isopropyl acetate was added to the reaction mixture. The resulting solution was washed with water (2×100) and saturated aqueous sodium chloride solution. The organic was dried over magnesium sulfate, filtered, and concentrated. The residue was purified by column chromatography (silica gel, 100-200 mesh, 0 to 100% iPrOAc in heptane) affording 2-iodo-5-(tetrahydro-2H-pyran-4-yl)-[1,2,4]triazolo[1,5-a]pyridine (645 mg, 57%) as a light yellow solid. LC-MS $R_T$=1.76 min, m/z=330.0 $(M+H)^+$.

LCMS (5 to 95% acetonitrile in water+0.1% formic acid over 5 mins) retention time 1.76 min, ESI+ found [M+H]=330.0.

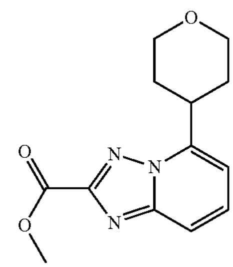 [SMILES: COC(=O)c1nc2cccc(C3CCOCC3)n2n1]

Step 3: methyl 5-(tetrahydro-2H-pyran-4-yl)-[1,2,4]triazolo[1,5-a]pyridine-2-carboxylate To a solution of 2-iodo-5-(tetrahydro-2H-pyran-4-yl)-[1,2,4]triazolo[1,5-a]pyridine (144 mg, 0.438 mmol) in MeOH (15 mL)) in an Easy Max autoclave was added [1,1'-bis(diphenylphosphino)ferrocene]dichloropalladium(II) (33 mg, 0.0438 mmol), trimethylamine (0.61 mL, 4.375 mmol). The autoclave was sealed, purged with CO twice, and pressured at 120 psi. The reaction mixture was stirred vigorously and heated at 80° C. for 15 h, concentrated to dryness in vacuo. The residue was purified by column chromatography (silica gel, 100-200 mesh, 0 to 15% methanol in dichloromethane) affording methyl 5-(1-methyl-1H-pyrazol-4-yl)-[1,2,4]triazolo[1,5-a]pyridine-2-carboxylate (79 mg, 79%) as a brown solid. $^1$H NMR (400 MHz, DMSO-d6) δ 7.85 (d, J=8.9 Hz, 1H), 7.78 (dd, J=9.0, 7.1 Hz, 1H), 7.25 (d, J=7.1 Hz, 1H), 4.07-3.97 (m, 2H), 3.95 (d, J=1.3 Hz, 3H), 3.72 (tt, J=12.1, 3.7 Hz, 1H), 3.58 (t, J=11.6 Hz, 2H), 2.07-1.94 (m, 2H), 1.82 (qd, J=12.3, 4.3 Hz, 2H). LC-MS $R_T$=1.10 min, m/z=262.2 $(M+H)^+$.

LCMS (5 to 95% acetonitrile in water+0.1% formic acid over 2 mins) retention time 1.10 min, ESI+ found [M+H]=262.2.

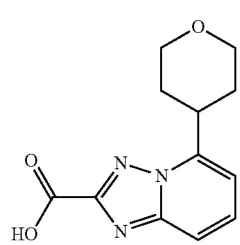 [SMILES: O=C(O)c1nc2cccc(C3CCOCC3)n2n1]

Step 4: 5-(tetrahydro-2H-pyran-4-yl)-[1,2,4]triazolo[1,5-a]pyridine-2-carboxylic acid To a solution of methyl 5-(tetrahydro-2H-pyran-4-yl)-[1,2,4]triazolo[1,5-a]pyridine-2-carboxylate (143 mg, 0.547 mmol) in tetrahydrofuran (12 mL) and methanol (3 mL) was added lithiumhydroxide (1 mol/L) in water (3 mL, 3.010 mmol). The reaction mixture was stirred at RT for 1 h. After this time, the mixture was concentrated to dryness in vacuo.

The residue was diluted with water (15 mL) and then adjusted to pH=1 by addition of 1 N hydrochloric acid. The solution was extracted with isopropyl acetate (3×100 mL). The combined organic layers were dried over sodium sulfate and concentrated to dryness in vacuo to afford 5-(tetrahydro-2H-pyran-4-yl)-[1,2,4]triazolo[1,5-a]pyridine-2-carboxylic acid (65 mg, 48% yield) as a tan solid used in the next step without further purification. LCMS $R_T$=0.72 min, m/z=248.1 $[M+H]^+$.

LCMS (5 to 95% acetonitrile in water+0.1% formic acid over 2 mins) retention time 0.72 min, ESI+ found [M+H]=248.1.

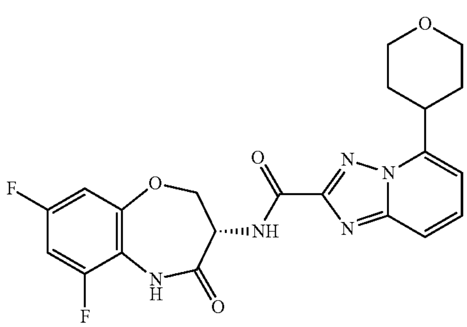 [SMILES: O=C(N[C@H]1COc2cc(F)cc(F)c2NC1=O)c1nc2cccc(C3CCOCC3)n2n1]

Step 5: (S)—N-(6,8-difluoro-4-oxo-2,3,4,5-tetrahydrobenzo[b][1,4]oxazepin-3-yl)-5-(tetrahydro-2H-pyran-4-yl)-[1,2,4]triazolo[1,5-a]pyridine-2-carboxamide To a solution of (S)-3-amino-6,8-difluoro-2,3-dihydrobenzo[b][1,4]oxazepin-4(5H)-one (112 mg, 0.447 mmol) and 5-(tetrahydro-2H-pyran-4-yl)-[1,2,4]triazolo[1,5-a]pyridine-2-carboxylic acid (85 mg, 0.343 mmol) in N,N-dimethylformamide (1.5 mL) was added HATU (160 mg, 0.412 mmol), and N,N-diisopropylethylamine (0.18 mL, 1.031 mmol. The reaction mixture was stirred overnight at RT, then was purified by preparative RP-HPLC (5-50% acetonitrile in water+0.1% formic acid) to afford (S)—N-(6,8-difluoro-4-oxo-2,3,4,5-tetrahydrobenzo[b][1,4]oxazepin-3-yl)-5-(tetrahydro-2H-pyran-4-yl)-[1,2,4]triazolo[1,5-a]pyridine-2-carboxamide as a white solid (15.2 mg, 10.0%). $^1$H NMR (400 MHz, DMSO-d6) δ 10.12 (s, 1H), 8.81 (d, J=7.6 Hz, 1H), 7.88-7.74 (m, 2H), 7.30-7.20 (m, 2H), 7.06 (dt, J=9.3, 2.3 Hz, 1H), 4.99 (dt, J=11.0, 7.3 Hz, 1H), 4.71 (t, J=10.7 Hz, 1H), 4.59 (dd, J=10.2, 7.2 Hz, 1H), 4.06-3.97 (m, 2H), 3.74 (m, 1H), 3.58 (m, 2H), 2.10-1.96 (m, 2H), 1.82 (m, 2H). LC-MS $R_T$=4.44 min, m/z=444.1 $(M+H)^+$.

LCMS (5 to 95% acetonitrile in water+0.1% formic acid over 10 mins) retention time 4.44 min, ESI+ found [M+H]=444.1

Example 423

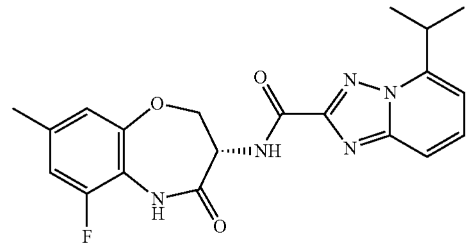 [SMILES: Cc1cc(F)c2c(c1)OC[C@H](NC(=O)c1nc3cccc(C(C)C)n3n1)C(=O)N2]

(S)—N-(6-fluoro-8-methyl-4-oxo-2,3,4,5-tetrahydrobenzo[b][1,4]oxazepin-3-yl)-5-isopropyl-[1,2,4]triazolo[1,5-a]pyridine-2-carboxamide (S)—N-(6-fluoro-8-methyl-4-oxo-2,3,4,5-tetrahydrobenzo[b][1,4]oxazepin-3-yl)-5-isopropyl-[1,2,4]triazolo[1,5-a]pyridine-2-carboxamide was prepared corresponding from (S)-3-amino-6-fluoro-8-methyl-2,3-dihydrobenzo[b][1,4]oxazepin-4(5H)-one, and 5-isopropyl-[1,2,4]triazolo[1,5-a]pyridine-2-carboxylic acid according to Method GZ12. The residue was purified by SFC (5-40% methanol elution with Carbon Dioxide, Column: Pyridyl Amide 150×30 mm) to afford (S)—N-(6-fluoro-8-methyl-4-oxo-2,3,4,5-tetrahydrobenzo[b][1,4]oxazepin-3-yl)-5-isopropyl-[1,2,4]triazolo[1,5-a]pyridine-2-carboxamide which showed 64% purity by $^1$H NMR, single peak for LC-MS. Yield of final step: 74 mg, 40%. $^1$H NMR (400 MHz, DMSO-d6) δ 10.04 (s, 1H), 8.76 (dd, J=7.8, 2.6 Hz, 1H), 7.86-7.70 (m, 2H), 7.21 (dt, J=6.9, 1.8 Hz, 1H), 7.00 (dd, J=10.8, 1.8 Hz, 1H), 6.91 (s, 1H), 4.94 (dt, J=11.2, 7.4 Hz, 1H), 4.65 (t, J=10.6 Hz, 1H), 4.54 (ddd, J=9.3, 7.4, 1.6 Hz, 1H), 3.77 (p, J=6.9 Hz, 1H), 2.31 (s, 3H), 1.39 (d, J=6.9 Hz, 6H). LC-MS $R_T$=5.21 min, m/z=398.1 $(M+H)^+$.

LCMS (5 to 95% acetonitrile in water+0.1% formic acid over 10 mins) retention time 5.21 min, ESI+ found [M+H]=398.1

Example 424

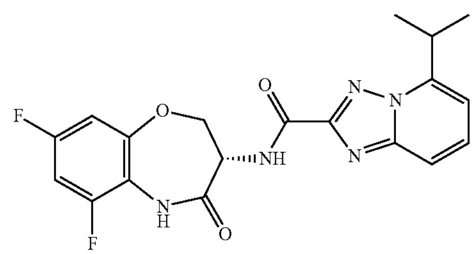

(S)—N-(6,8-difluoro-4-oxo-2,3,4,5-tetrahydrobenzo[b][1,4]oxazepin-3-yl)-5-isopropyl-[1,2,4]triazolo[1,5-a]pyridine-2-carboxamide (S)—N-(6,8-difluoro-4-oxo-2,3,4,5-tetrahydrobenzo[b][1,4]oxazepin-3-yl)-5-isopropyl-[1,2,4]triazolo[1,5-a]pyridine-2-carboxamide was prepared corresponding from (S)-3-amino-6,8-difluoro-2,3-dihydrobenzo[b][1,4]oxazepin-4(5H)-one, and 5-isopropyl-[1,2,4]triazolo[1,5-a]pyridine-2- carboxylic acid according to Method GZ12. The residue was purified by preparative RP-HPLC (20-60% acetonitrile in water+0.1% formic acid) to afford (S)—N-(6,8-difluoro-4-oxo-2,3,4,5-tetrahydrobenzo[b][1,4]oxazepin-3-yl)-5-isopropyl-[1,2,4]triazolo[1,5-a]pyridine-2-carboxamide which showed 64% purity by $^1$H NMR, single peak for LC-MS. Yield of final step: 69.8 mg, 37.6%. $^1$H NMR (400 MHz, DMSO-d6) δ 10.12 (s, 1H), 8.78 (dd, J=7.6, 2.7 Hz, 1H), 7.86-7.70 (m, 2H), 7.30-7.17 (m, 2H), 7.06 (dt, J=9.4, 2.3 Hz, 1H), 5.05-4.93 (m, 1H), 4.71 (t, J=10.7 Hz, 1H), 4.59 (ddd, J=10.2, 7.1, 1.5 Hz, 1H), 3.77 (p, J=6.9 Hz, 1H), 3.38-3.23 (m, 1H), 1.39 (d, J=6.9 Hz, 6H). LC-MS $R_T$=5.01 min, m/z=402.1 (M+H)$^+$.

LCMS (5 to 95% acetonitrile in water+0.1% formic acid over 10 mins) retention time 5.01 min, ESI+ found [M+H]= 402.1

Examples 425 and 426

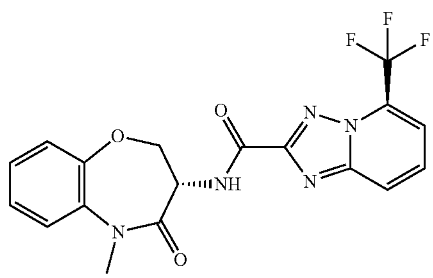

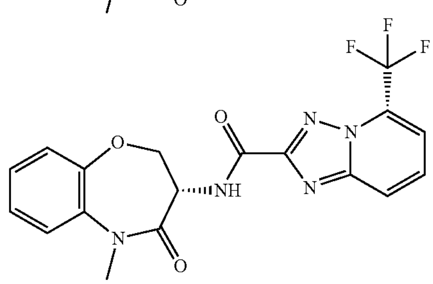

(R)—N—((S)-5-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide and (S)—N—((S)-5-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (1:1)

N—((S)-5-methyl-4-oxo-2,3,4,5-tetrahydrobenzo[b][1,4]oxazepin-3-yl)-5-(trifluoromethyl)-5, 6,7,8-tetrahydro-[1,2,4]triazolo[1,5-a]pyridine-2-carboxamide was prepared from (S)—N-(5-methyl-4-oxo-2,3,4,5-tetrahydrobenzo[b][1,4]oxazepin-3-yl)-5-(trifluoromethyl)-[1, 2,4]triazolo[1,5-a]pyridine-2-carboxamide according to Method GZ2. The residue was further purified by chiral SFC (Cellulose-1; 155×21.2 mm, 5 um; 20% methanol isocratic elution with Carbon Dioxide) affording arbitrarily assigned diastereomers (R)—N—((S)-5-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (15 mg, 13%) and (S)—N—((S)-5-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (16.5 mg, 14.5%) as white solids:

Analytical data for the first eluting diastereomer (arbitrarily assigned R, S configuration): SFC $R_T$ (Cel-1, 15% methanol+0.1% ammonium hydroxide isocratic elution with Carbon Dioxide, 2.5 min method): 0.989 min, 100% ee: $^1$H NMR (400 MHz, DMSO-d6) δ 8.50 (d, J=7.9 Hz, 1H), 7.51 (dd, J=7.5, 1.9 Hz, 1H), 7.37-7.20 (m, 3H), 5.41 (h, J=6.8 Hz, 1H), 4.83 (dt, J=11.5, 7.8 Hz, 1H), 4.61 (dd, J=11.6, 9.8 Hz, 1H), 4.42 (dd, J=9.8, 7.7 Hz, 1H), 3.42-3.18 (m, 3H), 3.07-2.87 (m, 2H), 2.39-2.15 (m, 2H), 2.02-1.87 (m, 2H). LCMS $R_T$=4.760 min, m/z=410.1 (M+H)$^+$.

LCMS (5 to 95% acetonitrile in water+0.1% formic acid over 10 mins) retention time 4.760 min, ESI+ found [M+H]= 410.1

Analytical data for the second eluting diastereomer (arbitrarily assigned S, S configuration): SFC $R_T$(Cel-1, 15% methanol+0.1% ammonium hydroxide isocratic elution with Carbon Dioxide, 2.5 min method): 1.372 min, 100% ee: $^1$H NMR (400 MHz, DMSO-d6) δ 8.50 (d, J=7.9 Hz, 1H), 7.51 (dd, J=7.5, 1.9 Hz, 1H), 7.37-7.20 (m, 3H), 5.41 (h, J=6.8 Hz, 1H), 4.83 (dt, J=11.5, 7.8 Hz, 1H), 4.61 (dd, J=11.6, 9.8 Hz, 1H), 4.42 (dd, J=9.8, 7.7 Hz, 1H), 3.42-3.18 (m, 3H), 3.07-2.87 (m, 2H), 2.39-2.15 (m, 2H), 2.02-1.87 (m, 2H). LCMS $R_T$=4.81 min, m/z=410.1 (M+H)$^+$.

LCMS (5 to 95% acetonitrile in water+0.1% formic acid over 10 mins) retention time 4.81 min, ESI+ found [M+H]= 410.1

Examples 427 and 428

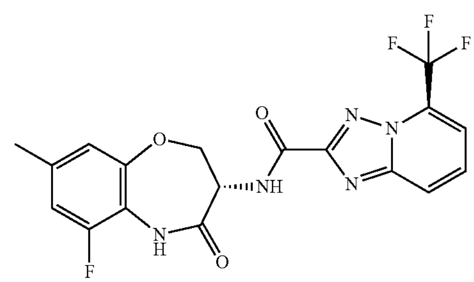

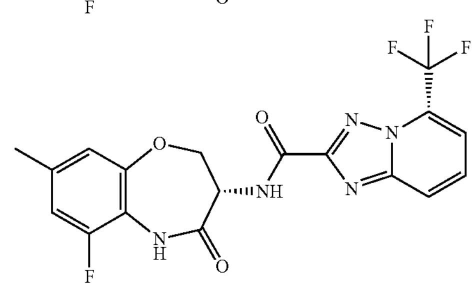

(R)—N—((S)-6-fluoro-8-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide and (S)—N—((S)-6-fluoro-8-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (1:1)

N—((S)-6-fluoro-8-methyl-4-oxo-2,3,4,5-tetrahydrobenzo[b][1,4]oxazepin-3-yl)-5-(trifluoromethyl)-5,6,7,8- tetrahydro-[1,2,4]triazolo[1,5-a]pyridine-2-carboxamide was prepared from (S)—N-(6-fluoro-8-methyl-4-oxo-2,3,4,5-tetrahydrobenzo[b][1,4]oxazepin-3-yl)-5-(trifluoromethyl)-[1,2,4]triazolo[1,5-a]pyridine-2-carboxamide according to Method GZ2. The crude residue was further purified by chiral SFC (Chiralpak AD; 152×21.2 mm, 5 um; 30% methanol isocratic elution with Carbon Dioxide) affording arbitrarily assigned diastereomers (R)—N—((S)-6-fluoro-8-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (27.2 mg, 32%) and (S)—N—((S)-6-fluoro-8-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (26.6 mg, 32.5%) as white solids:

Analytical data for the first eluting diastereomer (arbitrarily assigned R, S configuration): SFC $R_T$ (AD, 25% methanol+0.1% ammonium hydroxide isocratic elution with Carbon Dioxide, 2.5 min method): 0.624 min, 98.5% purity, 97% ee: $^1$H NMR (400 MHz, DMSO-d6) δ 10.00 (s, 1H), 8.47 (d, J=7.7 Hz, 1H), 6.99 (dd, J=10.8, 1.8 Hz, 1H), 6.89 (s, 1H), 5.41 (h, J=6.8 Hz, 1H), 4.85 (dt, J=11.1, 7.4 Hz, 1H), 4.61 (t, J=10.7 Hz, 1H), 4.47 (dd, J=10.1, 7.2 Hz, 1H), 3.07-2.87 (m, 2H), 2.30 (m, 5H), 1.96 (h, J=6.7 Hz, 2H). LCMS $R_T$=4.44 min, m/z=428.1 $(M+H)^+$.

LCMS (5 to 95% acetonitrile in water+0.1% formic acid over 10 mins) retention time 4.44 min, ESI+ found [M+H]=428.1

Analytical data for the second eluting diastereomer (arbitrarily assigned S, S configuration): SFC $R_T$(AD, 25% methanol+0.1% ammonium hydroxide isocratic elution with Carbon Dioxide, 2.5 min method): 1.200 min, 100% ee: $^1$H 1H NMR (400 MHz, DMSO-d6) δ 10.00 (s, 1H), 8.47 (d, J=7.7 Hz, 1H), 6.99 (dd, J=10.8, 1.8 Hz, 1H), 6.89 (s, 1H), 5.41 (h, J=6.8 Hz, 1H), 4.85 (dt, J=11.1, 7.4 Hz, 1H), 4.61 (t, J=10.7 Hz, 1H), 4.47 (dd, J=10.1, 7.2 Hz, 1H), 3.07-2.87 (m, 2H), 2.30 (m, 5H), 1.96 (h, J=6.7 Hz, 2H). LCMS $R_T$=4.50 min, m/z=428.1 $(M+H)^+$.

LCMS (5 to 95% acetonitrile in water+0.1% formic acid over 10 mins) retention time 4.50 min, ESI+ found [M+H]=428.1

Examples 429 and 430

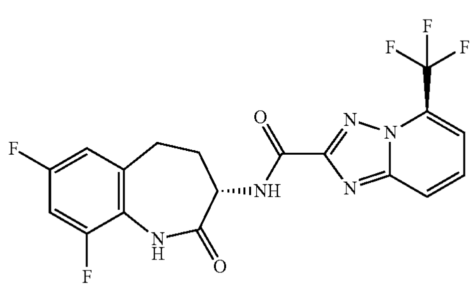

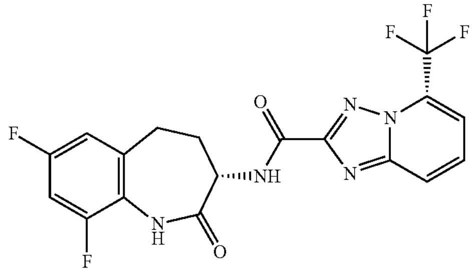

(R)—N—((S)-7,9-difluoro-2-oxo-2,3,4,5-tetrahydro-1H-benzo[b]azepin-3-yl)-5-(trifluoromethyl)-5,6,7,8-tetrahydro-[1,2,4]triazolo[1,5-a]pyridine-2-carboxamide and (S)—N—((S)-7,9-difluoro-2-oxo-2,3,4,5-tetrahydro-1H-benzo[b]azepin-3-yl)-5-(trifluoromethyl)-5,6,7,8-tetrahydro-[1,2,4]triazolo[1,5-a]pyridine-2-carboxamide (1:1)

N—((S)-7,9-difluoro-2-oxo-2,3,4,5-tetrahydro-1H-benzo[b]azepin-3-yl)-5-(trifluoromethyl)-5, 6,7,8-tetrahydro-[1,2,4]triazolo[1,5-a]pyridine-2-carboxamide was prepared from (S)—N-(7,9-difluoro-2-oxo-2,3,4,5-tetrahydro-1H-benzo[b]azepin-3-yl)-5-(trifluoromethyl)-[1,2,4]triazolo[1,5-a]pyridine-2-carboxamide according to Method GZ2. The crude residue was further purified by chiral SFC (Chiralpak AD; 151×21.2 mm, 5 um; 30% methanol isocratic elution with Carbon Dioxide) affording arbitrarily assigned diastereomers (R)—N—((S)-7,9-difluoro-2-oxo-2,3,4,5-tetrahydro-1H-benzo[b]azepin-3-yl)-5-(trifluoromethyl)-5,6,7,8-tetrahydro-[1,2,4]triazolo[1,5-a]pyridine-2-carboxamide (23.5 mg, 29.7%) and (S)—N—((S)-7,9-difluoro-2-oxo-2,3,4,5-tetrahydro-1H-benzo[b]azepin-3-yl)-5-(trifluoromethyl)-5,6,7,8-tetrahydro-[1,2,4]triazolo[1,5-a]pyridine-2-carboxamide (20.6 mg, 26.0%) as white solids:

Analytical data for the first eluting diastereomer (arbitrarily assigned R, S configuration): SFC $R_T$ (AD, 25% methanol+0.1% ammonium hydroxide isocratic elution with Carbon Dioxide, 2.5 min method): 0.568 min, 100% purity, 100% ee: $^1$H NMR (400 MHz, DMSO-d6) δ 9.96 (s, 1H), 8.33 (d, J=7.5 Hz, 1H), 7.27 (ddd, J=10.2, 8.9, 2.8 Hz, 1H), 7.18-7.10 (m, 1H), 5.40 (h, J=6.8 Hz, 1H), 4.34 (dt, J=11.5, 7.8 Hz, 1H), 3.06-2.71 (m, 4H), 2.50-2.15 (m, 4H), 1.94 (m, 2H). LCMS $R_T$=4.16 min, m/z=430.1 $(M+H)^+$.

LCMS (5 to 95% acetonitrile in water+0.1% formic acid over 10 mins) retention time 4.16 min, ESI+ found [M+H]=430.1

Analytical data for the second eluting diastereomer (arbitrarily assigned S, S configuration): SFC $R_T$(AD, 25% methanol+0.1% ammonium hydroxide isocratic elution with Carbon Dioxide, 2.5 min method): 0.873 min, 98.07% purity, 96.14% ee: $^1$H NMR (400 MHz, DMSO-d6) δ 9.96 (s, 1H), 8.33 (d, J=7.5 Hz, 1H), 7.27 (ddd, J=10.2, 8.9, 2.8 Hz, 1H), 7.18-7.10 (m, 1H), 5.40 (h, J=6.8 Hz, 1H), 4.34 (dt, J=11.5, 7.8 Hz, 1H), 3.06-2.71 (m, 4H), 2.50-2.15 (m, 4H), 1.94 (m, 2H). LCMS $R_T$=4.22 min, m/z=430.1 $(M+H)^+$.

LCMS (5 to 95% acetonitrile in water+0.1% formic acid over 10 mins) retention time 4.22 min, ESI+ found [M+H]=430.1

Examples 431 and 432

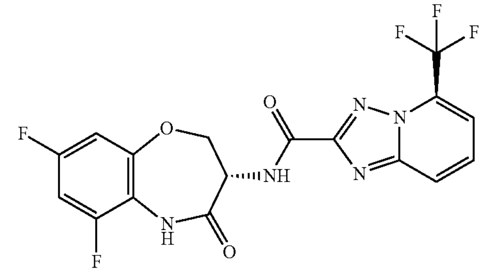

-continued

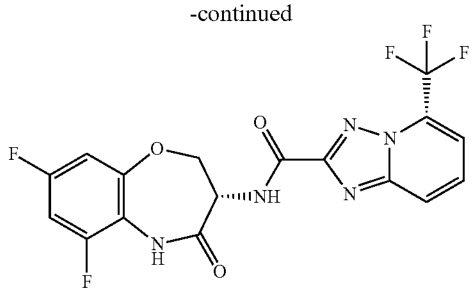

(R)—N—((S)-6,8-difluoro-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide and (S)—N—((S)-6,8-difluoro-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (1:1)

N—((S)-6,8-difluoro-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide was prepared from (S)—N-(6,8-difluoro-4-oxo-2,3,4,5-tetrahydrobenzo[b][1,4]oxazepin-3-yl)-5-(trifluoromethyl)-[1,2,4]triazolo[1,5-a]pyridine-2-carboxamide according to Method GZ2. The crude residue was further purified by chiral SFC (Chiralpak AD; 150×21.2 mm, 5 um; 30% methanol isocratic elution with Carbon Dioxide) affording arbitrarily assigned diastereomers (R)—N—((S)-6,8-difluoro-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (19.8 mg, 17.9%) and (S)—N—((S)-6,8-difluoro-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide (21.0 mg, 20.2%) as white solids:

Analytical data for the first eluting diastereomer (arbitrarily assigned R, S configuration): SFC $R_T$ (AD, 25% methanol+0.1% ammonium hydroxide isocratic elution with Carbon Dioxide, 2.5 min method): 0.535 min, 100% purity, 100% ee: $^1$H NMR (400 MHz, DMSO-d6) δ 10.08 (s, 1H), 8.50 (d, J=7.6 Hz, 1H), 7.23 (ddd, J=10.3, 9.0, 2.9 Hz, 1H), 7.03 (dt, J=9.4, 2.3 Hz, 1H), 5.42 (h, J=6.8 Hz, 1H), 4.90 (dt, J=11.1, 7.3 Hz, 1H), 4.67 (t, J=10.7 Hz, 1H), 4.53 (dd, J=10.1, 7.1 Hz, 1H), 3.07-2.87 (m, 2H), 2.40-2.16 (m, 2H), 1.96 (h, J=6.6 Hz, 2H). LCMS $R_T$=4.24 min, m/z=432.1 $(M+H)^+$.

LCMS (5 to 95% acetonitrile in water+0.1% formic acid over 10 mins) retention time 4.24 min, ESI+ found [M+H]=432.1

Analytical data for the second eluting diastereomer (arbitrarily assigned S, S configuration): SFC $R_T$(AD, 25% methanol+0.1% ammonium hydroxide isocratic elution with Carbon Dioxide, 2.5 min method): 0.849 min, 100% purity, 100% ee: $^1$H NMR (400 MHz, DMSO-d6) δ 10.08 (s, 1H), 8.50 (d, J=7.6 Hz, 1H), 7.23 (ddd, J=10.3, 9.0, 2.9 Hz, 1H), 7.03 (dt, J=9.4, 2.3 Hz, 1H), 5.42 (h, J=6.8 Hz, 1H), 4.90 (dt, J=11.1, 7.3 Hz, 1H), 4.67 (t, J=10.7 Hz, 1H), 4.53 (dd, J=10.1, 7.1 Hz, 1H), 3.07-2.87 (m, 2H), 2.40-2.16 (m, 2H), 1.96 (h, J=6.6 Hz, 2H). LCMS $R_T$=4.29 min, m/z=432.1 $(M+H)^+$.

LCMS (5 to 95% acetonitrile in water+0.1% formic acid over 10 mins) retention time 4.29 min, ESI+ found [M+H]=432.1.

Example 433

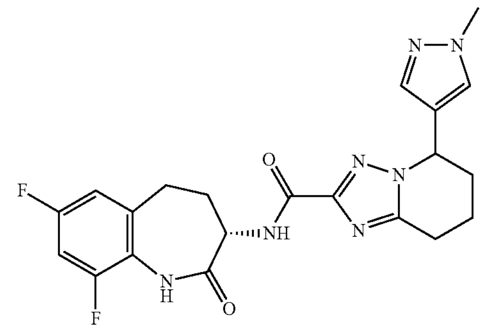 [SMILES: Cn1cc(C2CCCc3nc(C(=O)N[C@H]4CCc5cc(F)cc(F)c5NC4=O)nn32)cn1]

N—((S)-7,9-difluoro-2-oxo-2,3,4,5-tetrahydro-H-benzo[b]azepin-3-yl)-5-(1-methyl-1H-pyrazol-4-yl)-5,6,7,8-tetrahydro-[1,2,4]triazolo[1,5-a]pyridine-2-carboxamide N—((S)-7,9-difluoro-2-oxo-2,3,4,5-tetrahydro-1H-benzo[b]azepin-3-yl)-5-(1-methyl-1H-pyrazol-4-yl)-5,6,7,8-tetrahydro-[1,2,4]triazolo[1,5-a]pyridine-2-carboxamide was prepared from (S)—N-(7,9-difluoro-2-oxo-2,3,4,5-tetrahydro-1H-benzo[b]azepin-3-yl)-5-(1-methyl-1H-pyrazol-4-yl)-[1,2,4]triazolo[1,5-a]pyridine-2-carboxamide according to Method GZ2. The residue was purified by preparative RP-HPLC (5-60% acetonitrile in water+0.1% formic acid) to afford final product (7.3 mg, 10.3%) as a white. $^1$H NMR (400 MHz, DMSO-d6) δ 9.95 (s, 1H), 8.19 (dd, J=7.6, 4.1 Hz, 1H), 7.62 (s, 1H), 7.37 (s, 1H), 7.26 (td, J=9.6, 2.8 Hz, 1H), 7.14 (dd, J=8.2, 2.7 Hz, 1H), 5.46 (t, J=5.8 Hz, 1H), 4.32 (dt, J=11.4, 7.8 Hz, 1H), 4.08 (q, J=5.3 Hz, 1H), 3.78 (s, 3H), 3.17 (d, J=5.3 Hz, 3H), 2.92 (dt, J=10.0, 5.4 Hz, 2H), 2.82-2.71 (m, 2H), 2.33-2.17 (m, 2H), 2.12 (m, 1H), 1.92 (dd, J=20.0, 10.3 Hz, 2H). LC-MS $R_T$=3.85 min, m/z=442.1 $(M+H)^+$.

LCMS (5 to 95% acetonitrile in water+0.1% formic acid over 10 mins) retention time 3.85 min, ESI+ found [M+H]=442.1

Examples 434-437

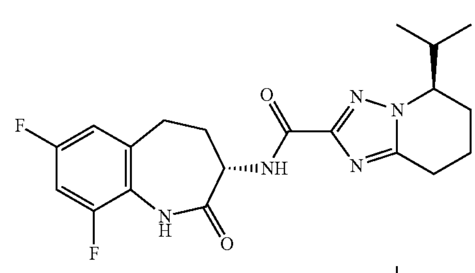

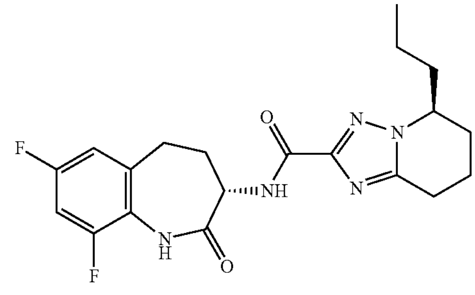

-continued

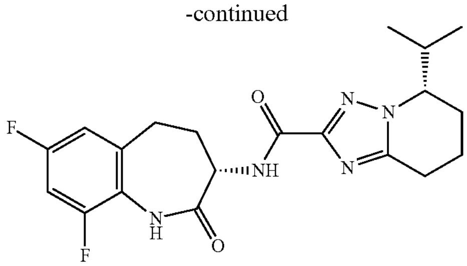

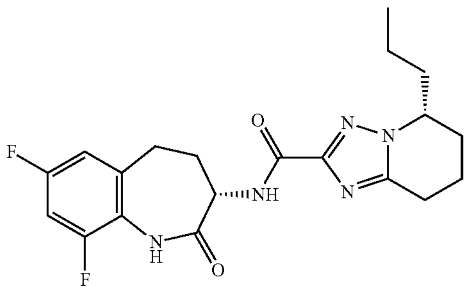

(R)—N—((S)-7,9-difluoro-2-oxo-2,3,4,5-tetrahydro-1H-benzo[b]azepin-3-yl)-5-isopropyl-5, 6,7,8-tetra-hydro-[1,2,4]triazolo[1,5-a]pyridine-2-carboxamide (S)—N—((S)-7,9-difluoro-2-oxo-2,3,4,5-tetrahydro-1H-benzo[b]azepin-3-yl)-5-propyl-5,6,7, 8-tetra-hydro-[1,2,4]triazolo[1,5-a]pyridine-2-carboxamide (S)—N—((S)-7,9-difluoro-2-oxo-2,3,4,5-tetrahydro-H-benzo[b]azepin-3-yl)-5-isopropyl-5, 6,7,8-tetra-hydro-[1,2,4]triazolo[1,5-a]pyridine-2-carboxamide (R)—N—((S)-7,9-difluoro-2-oxo-2,3,4,5-tetrahydro-1-benzo[b]azepin-3-yl)-5-propyl-5,6,7,8-tetrahydro-[1,2,4]triazolo[1,5-a]pyridine-2-carboxamide Mixture of 64% (S)—N-(7,9-difluoro-2-oxo-2,3,4,5-tetrahydro-1H-benzo[b]azepin-3-yl)-5-isopropyl-[1,2,4]triazolo[1,5-a]pyridine-2-carboxamide and 36% (S)—N-(7,9-difluoro-2-oxo-2,3,4,5-tetrahydro-1H-benzo[b]azepin-3-yl)-5-propyl-[1,2,4]triazol o[1,5-a]pyridine-2-carboxamide was reduced according to Method GZ2. The crude residue was further purified by chiral SFC was purified by chiral SFC (Chiralpak ID; 150×21.2 mm, 5 um; 30% methanol isocratic elution with Carbon Dioxide) affording four isomers (structural isomers were assigned based on 1H NMR; diastereomers were arbitrarily assigned):

(R)—N—((S)-7,9-difluoro-2-oxo-2,3,4,5-tetrahydro-1H-benzo[b]azepin-3-yl)-5-isopropyl-5,6,7, 8-tetrahydro-[1,2,4]triazolo[1,5-a]pyridine-2-carboxamide (19.6 mg, 19.8%) as white solids (S)—N—((S)-7,9-difluoro-2-oxo-2,3,4,5-tetrahydro-1H-benzo[b]azepin-3-yl)-5-propyl-5,6,7,8-tetrahydro-[1,2,4]triazolo[1,5-a]pyridine-2-carboxamide (8.8 mg, 8.2%) as white solids (S)—N—((S)-7,9-difluoro-2-oxo-2,3,4,5-tetrahydro-1H-benzo[b]azepin-3-yl)-5-isopropyl-5,6,7, 8-tetrahydro-[1,2,4]triazolo[1,5-a]pyridine-2-carboxamide (19 mg, 18.6%) as white solids (R)—N—((S)-7,9-difluoro-2-oxo-2,3,4,5-tetrahydro-1H-benzo[b]azepin-3-yl)-5-propyl-5,6,7,8-tetrahydro-[1,2,4]triazolo[1,5-a]pyridine-2-carboxamide (8.1 mg, 8.2%) as white solids.

Analytical data for the first eluting isomer (arbitrarily assigned R, S configuration): SFC $R_T$(OX, 35% methanol+0.1% ammonium hydroxide isocratic elution with Carbon Dioxide, 2.5 min method): 0.719 min, 100% purity, 100% ee: $^1$H NMR (400 MHz, DMSO-d6) δ 9.95 (s, 1H), 8.21 (d, J=7.6 Hz, 1H), 7.27 (ddd, J=10.1, 8.9, 2.8 Hz, 1H), 7.19-7.10 (m, 1H), 4.34 (dt, J=11.5, 7.8 Hz, 1H), 4.15 (p, J=4.4 Hz, 1H), 2.95-2.85 (m, 1H), 2.72 (dtd, J=59.4, 7.0, 6.5, 4.0 Hz, 5H), 2.50-2.37 (m, 1H), 2.30-2.16 (m, 1H), 2.10-1.96 (m, 2H), 1.73 (ddd, J=10.7, 8.2, 5.2 Hz, 2H), 0.98 (d, J=7.0 Hz, 3H), 0.68 (d, J=6.8 Hz, 3H). LCMS $R_T$=4.72 min, m/z=404.1 $(M+H)^+$.

LCMS (5 to 95% acetonitrile in water+0.1% formic acid over 10 mins) retention time 4.72 min, ESI+ found [M+H]=404.1

Analytical data for the second eluting isomer (arbitrarily assigned S, S configuration): SFC $R_T$(OX, 35% methanol+0.1% ammonium hydroxide isocratic elution with Carbon Dioxide, 2.5 min method): 0.950 min, 99.6% purity, 99.2% ee: $^1$H NMR (400 MHz, DMSO-d6) δ 9.95 (s, 1H), 8.20 (d, J=7.6 Hz, 1H), 7.27 (ddd, J=10.1, 8.9, 2.8 Hz, 1H), 7.18-7.10 (m, 1H), 4.34 (dt, J=11.5, 7.9 Hz, 1H), 4.21 (d, J=7.5 Hz, 1H), 2.93-2.71 (m, 4H), 2.50-2.36 (m, 1H), 2.30-1.91 (m, 4H), 1.86-1.57 (m, 3H), 1.38 (m, 2H), 0.93 (t, J=7.3 Hz, 3H). LCMS $R_T$=4.85 min, m/z=404.1 $(M+H)^+$.

LCMS (5 to 95% acetonitrile in water+0.1% formic acid over 10 mins) retention time 4.85 min, ESI+ found [M+H]=404.1

Analytical data for the third eluting isomer (arbitrarily assigned S, S configuration): SFC $R_T$(OX, 35% methanol+0.1% ammonium hydroxide isocratic elution with Carbon Dioxide, 2.5 min method): 1.368 min, 100% purity, 100% ee: $^1$H NMR (400 MHz, DMSO-d6) δ 9.95 (s, 1H), 8.21 (d, J=7.6 Hz, 1H), 7.27 (ddd, J=10.1, 8.9, 2.8 Hz, 1H), 7.19-7.10 (m, 1H), 4.34 (dt, J=11.5, 7.8 Hz, 1H), 4.15 (p, J=4.4 Hz, 1H), 2.95-2.85 (m, 1H), 2.72 (dtd, J=59.4, 7.0, 6.5, 4.0 Hz, 5H), 2.50-2.37 (m, 1H), 2.30-2.16 (m, 1H), 2.10-1.96 (m, 2H), 1.73 (ddd, J=10.7, 8.2, 5.2 Hz, 2H), 0.98 (d, J=7.0 Hz, 3H), 0.68 (d, J=6.8 Hz, 3H). LCMS $R_T$=4.78 min, m/z=404.1 $(M+H)^+$.

LCMS (5 to 95% acetonitrile in water+0.1% formic acid over 10 mins) retention time 4.78 min, ESI+ found [M+H]=404.1

Analytical data for the fourth eluting isomer (arbitrarily assigned R, S configuration): SFC $R_T$(OX, 35% methanol+0.1% ammonium hydroxide isocratic elution with Carbon Dioxide, 2.5 min method): 1.439 min, 100% purity, 100% ee: $^1$H NMR (400 MHz, DMSO-d6) δ 9.95 (s, 1H), 8.20 (d, J=7.6 Hz, 1H), 7.27 (ddd, J=10.1, 8.9, 2.8 Hz, 1H), 7.18-7.10 (m, 1H), 4.34 (dt, J=11.5, 7.9 Hz, 1H), 4.21 (d, J=7.5 Hz, 1H), 2.93-2.71 (m, 4H), 2.50-2.36 (m, 1H), 2.30-1.91 (m, 4H), 1.86-1.57 (m, 3H), 1.38 (m, 2H), 0.93 (t, J=7.3 Hz, 3H). LCMS $R_T$=4.88 min, m/z=404.1 $(M+H)^+$.

LCMS (5 to 95% acetonitrile in water+0.1% formic acid over 10 mins) retention time 4.88 min, ESI+ found [M+H]=404.1

Examples 438-441

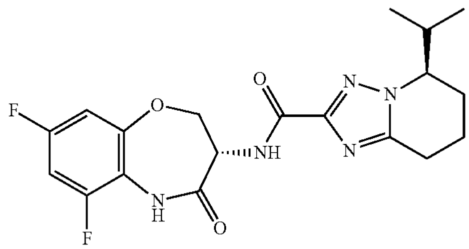

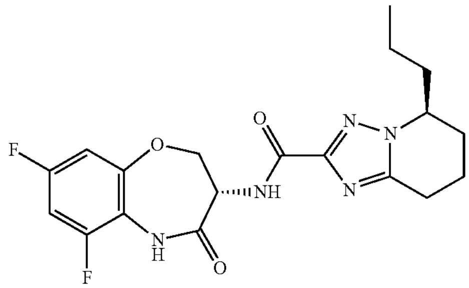

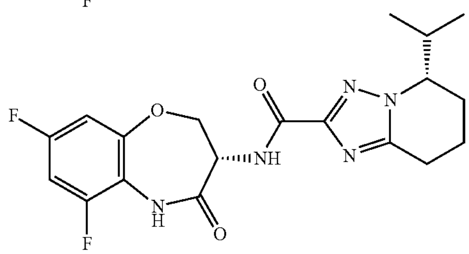

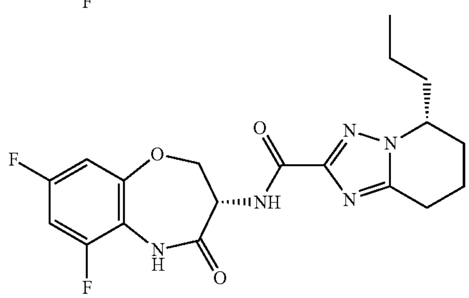

(R)—N—((S)-6-fluoro-8-methyl-4-oxo-2,3,4,5-tetrahydrobenzo[b][1,4]oxazepin-3-yl)-5-isopropyl-5,6,7,8-tetrahydro-[1,2,4]triazolo[1,5-a]pyridine-2-carboxamide (S)—N—((S)-6-fluoro-8-methyl-4-oxo-2,3,4,5-tetrahydrobenzo[b][1,4]oxazepin-3-yl)-5-isopropyl-5,6,7,8-tetrahydro-[1,2,4]triazolo[1,5-a]pyridine-2-carboxamide (S)—N—((S)-6-fluoro-8-methyl-4-oxo-2,3,4,5-tetrahydrobenzo[b][1,4]oxazepin-3-yl)-5-propyl-5,6,7,8-tetrahydro-[1,2,4]triazolo[1,5-a]pyridine-2-carboxamide (S)—N—((S)-6-fluoro-8-methyl-4-oxo-2,3,4,5-tetrahydrobenzo[b][1,4]oxazepin-3-yl)-5-isopropyl-[1,2,4]triazolo[1,5-a]pyridine-2-carboxamide (R)—N—((S)-6-fluoro-8-methyl-4-oxo-2,3,4,5-tetrahydrobenzo[1,4]oxazepin-3-yl)-5-propyl-5,6,7,8-tetrahydro-[1,2,4][triazolo[1,5-a]pyridine-2-carboxamide Mixture of 64% (S)—N-(6-fluoro-8-methyl-4-oxo-2,3,4,5-tetrahydrobenzo[b][1,4]oxazepin-3-yl)-5-isopropyl-[yl-5,6,7,8-tetrahydro-[1,2,4]triazolo[b[1,5][1,5-a]pyridine-2-carboxamide and 36(3.5 g, 5.0%) as white (S)—N-(6-fluoro-8-methyl-4-oxo-2,3,4,5-tetrahydrobenzo[b][1,4]oxazepin-3-yl)-5-propyl-[1,2,4]triazolo[1,5-a]pyridine-2-carboxamide was reduced according to Method GZ2. The crude residue was further purified by chiral SFC was purified by chiral SFC (Chiralpak TD; 150×21.2 mm, Sum; 35% methanol isocratic elution with Carbon Dioxide) affording four isomers (structural isomers were assigned based on 1H NMR; diastereomers arbitrarily assigned):

(R)—N—((S)-6-fluoro-8-methyl-4-oxo-2,3,4,5-tetrahydrobenzo[b][1,4]oxazepin-3-yl)-5-isopropyl-5,6,7,8-tetrahydro-[1,2,4]triazolo[1,5-a]pyridine-2-carboxamide (3.5 mg, 5.0%) as white solids (S)—N—((S)-6-fluoro-8-methyl-4-oxo-2,3,4,5-tetrahydrobenzo[b][1,4]oxazepin-3-yl)-5-propyl-5,6,7,8-tetrahydro-[1,2,4]triazolo[1,5-a]pyridine-2-carboxamide (1.6 mg, 2.1%) as white solids (S)—N—((S)-6-fluoro-8-methyl-4-oxo-2,3,4,5-tetrahydrobenzo[b][1,4]oxazepin-3-yl)-5-isopropyl-5,6,7,8-tetrahydro-[1,2,4]triazolo[1,5-a]pyridine-2-carboxamide (4.1 mg, 5.8%) as white solids (R)—N—((S)-6-fluoro-8-methyl-4-oxo-2,3,4,5-tetrahydrobenzo[b][1,4]oxazepin-3-yl)-5-propyl-5,6,7,8-tetrahydro-[1,2,4]triazolo[1,5-a]pyridine-2-carboxamide (1.8 mg, 2.4%) as white solids.

Analytical data for the first eluting isomer (arbitrarily assigned R, S configuration): SFC $R_T$(AD, 25% methanol+0.1% ammonium hydroxide isocratic elution with Carbon Dioxide, 2.5 min method): 0.874 min, 99.3% purity, 98.5% ee: $^1$H NMR (400 MHz, DMSO-d6) δ 10.00 (s, 1H), 8.35 (d, J=7.8 Hz, 1H), 7.03-6.94 (m, 1H), 6.89 (s, 1H), 4.84 (dt, J=11.1, 7.5 Hz, 1H), 4.59 (t, J=10.7 Hz, 1H), 4.46 (dd, J=10.1, 7.3 Hz, 1H), 4.16 (dt, J=8.6, 4.6 Hz, 1H), 2.96-2.85 (m, 1H), 2.79 (ddd, J=17.7, 9.9, 5.3 Hz, 1H), 2.72-2.59 (m, 1H), 2.30 (s, 3H), 2.07-1.98 (m, 2H), 1.73 (ddd, J=10.8, 8.5, 5.7 Hz, 2H), 0.98 (d, J=7.0 Hz, 3H), 0.69 (d, J=6.8 Hz, 3H). LCMS $R_T$=4.94 min, m/z=402.1 $(M+H)^+$.

LCMS (5 to 95% acetonitrile in water+0.1% formic acid over 10 mins) retention time 4.94 min, ESI+ found [M+H]=402.1

Analytical data for the second eluting isomer (arbitrarily assigned S, S configuration): SFC $R_T$(AD, 25% methanol+0.1% ammonium hydroxide isocratic elution with Carbon Dioxide, 2.5 min method): 1.019 min, 94.3% purity, 88.6% ee: LCMS $R_T$=5.05 min, m/z=402.1 $(M+H)^+$.

LCMS (5 to 95% acetonitrile in water+0.1% formic acid over 10 mins) retention time 5.05 min, ESI+ found [M+H]=402.1

Analytical data for the third eluting isomer (arbitrarily assigned S, S configuration): SFC $R_T$(AD, 25% methanol+0.1% ammonium hydroxide isocratic elution with Carbon Dioxide, 2.5 min method): 1.220 min, 98.3% purity, 96.6% ee: $^1$H NMR (400 MHz, DMSO-d6) δ 10.00 (s, 1H), 8.35 (d, J=7.8 Hz, 1H), 7.03-6.94 (m, 1H), 6.89 (s, 1H), 4.84 (dt, J=11.1, 7.5 Hz, 1H), 4.59 (t, J=10.7 Hz, 1H), 4.46 (dd, J=10.1, 7.3 Hz, 1H), 4.16 (dt, J=8.6, 4.6 Hz, 1H), 2.96-2.85 (m, 1H), 2.79 (ddd, J=17.7, 9.9, 5.3 Hz, 1H), 2.72-2.59 (m, 1H), 2.30 (s, 3H), 2.07-1.98 (m, 2H), 1.73 (ddd, J=10.8, 8.5, 5.7 Hz, 2H), 0.98 (d, J=7.0 Hz, 3H), 0.69 (d, J=6.8 Hz, 3H). LCMS $R_T$=4.91 min, m/z=402.1 $(M+H)^+$.

LCMS (5 to 95% acetonitrile in water+0.1% formic acid over 10 mins) retention time 4.91 min, ESI+ found [M+H]=402.1

Analytical data for the fourth eluting isomer (arbitrarily assigned R, S configuration): SFC $R_T$(AD, 25% methanol+0.1% ammonium hydroxide isocratic elution with Carbon Dioxide, 2.5 min method): 1.513 min, 95.8% purity, 91.6% ee: LCMS $R_T$=5.08 min, m/z=402.1 $(M+H)^+$.

LCMS (5 to 95% acetonitrile in water+0.1% formic acid over 10 mins) retention time 5.08 min, ESI+ found [M+H]=402.1.

Example 442

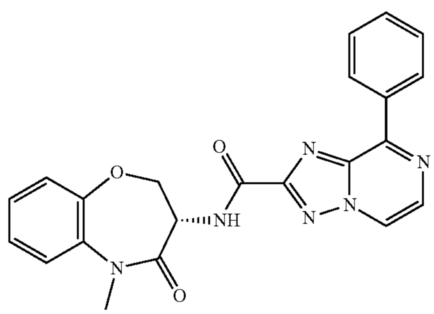 [SMILES: CN1C(=O)[C@@H](NC(=O)c2nc3c(-c4ccccc4)nccn3n2)COc2ccccc21]

(S)—N-(5-methyl-4-oxo-2,3,4,5-tetrahydrobenzo[b][1,4]oxazepin-3-yl)-8-phenyl-[1,2,4]triazolo[1,5-a]pyrazine-2-carboxamide Utilizing 3-phenylpyrazin-2-amine to replace 6-(trifluoromethyl)pyridin-2-amine in step 1 of Method GZ5, follow the steps. (S)—N-(5-methyl-4-oxo-2,3,4,5-tetrahydrobenzo[b][1,4]oxazepin-3-yl)-8-phenyl-[1,2,4]triazol o[1,5-a]pyrazine-2-carboxamide was prepared corresponding from (S)-3-amino-5-methyl-2,3-dihydrobenzo[b][1,4]oxazepin-4(5H)-one, and 8-phenyl-[1,2,4]triazolo[1,5-a]pyrazine-2-carboxylic acid according to Method GZ5. The residue was purified by preparative RP-HPLC (20-60% acetonitrile in water+0.1% formic acid) instead. Yield of final step: 35.5 mg, 22.9%. $^1$H NMR (400 MHz, DMSO-d6) δ 9.15-9.03 (m, 2H), 8.84-8.75 (m, 2H), 8.47 (d, J=4.5 Hz, 1H), 7.70-7.58 (m, 3H), 7.55 (dd, J=7.6, 1.9 Hz, 1H), 7.40-7.23 (m, 3H), 4.98 (dt, J=11.5, 7.8 Hz, 1H), 4.73 (dd, J=11.6, 9.8 Hz, 1H), 4.51 (dd, J=9.8, 7.7 Hz, 1H), 3.35 (s, 3H). LC-MS $R_T$=5.04 min, m/z=415.1 $(M+H)^+$.

LCMS (5 to 95% acetonitrile in water+0.1% formic acid over 10 mins) retention time 5.04 min, ESI+ found [M+H]=415.1

Example 443

Method GZ7

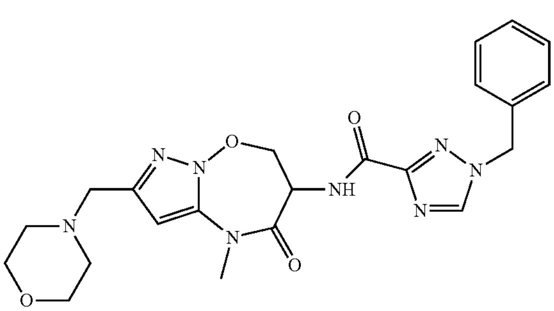 [SMILES: CN1C(=O)C(NC(=O)c2ncn(Cc3ccccc3)n2)COn2nc(CN3CCOCC3)cc21]

1-benzyl-N-(4-methyl-2-(morpholinomethyl)-5-oxo-5,6,7,8-tetrahydro-4H-pyrazolo[1,5-a][1,3]diazepin-6-yl)-1H-1,2,4-triazole-3-carboxamide

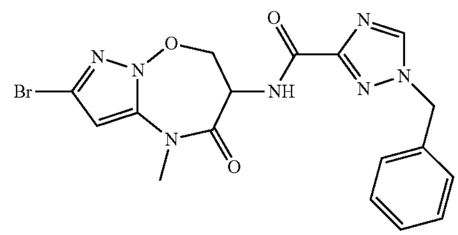 [SMILES: CN1C(=O)C(NC(=O)c2ncn(Cc3ccccc3)n2)COn2nc(Br)cc21]

Step 1: 1-benzyl-N-(2-bromo-4-methyl-5-oxo-5,6,7,8-tetrahydro-4H-pyrazolo[1,5-a][1,3]diazepin-6-yl)-1H-1,2,4-triazole-3-carboxamide The title compound was prepared from 5-bromo-1H-pyrazol-3-amine and 1-benzyl-1H-1,2,4-triazole-3-carboxylic acid according to Method Z(Wuxi). $^1$H NMR (400 MHz, DMSO-$d_6$) δ 8.82 (s, 1H), 8.62-8.57 (m, 1H), 7.39-7.30 (m, 5H), 6.57 (s, 1H), 5.48 (s, 2H), 4.39-4.31 (m, 2H), 4.26-4.19 (m, 1H), 3.22 (s, 3H), 2.65-2.56 (m, 1H), 2.44-2.36 (m, 1H). LCMS $R_T$=1.23 min, m/z=444.0 $[M+H]^+$.

LCMS (5 to 95% acetonitrile in water+0.1% formic acid over 2 mins) retention time 1.23 min, ESI+ found [M+H]=444.0.

Examples 444-447

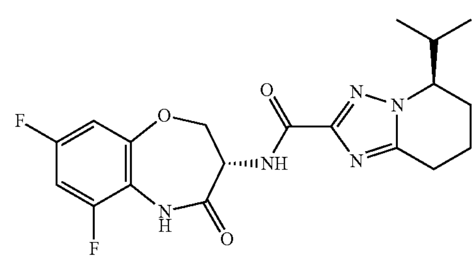

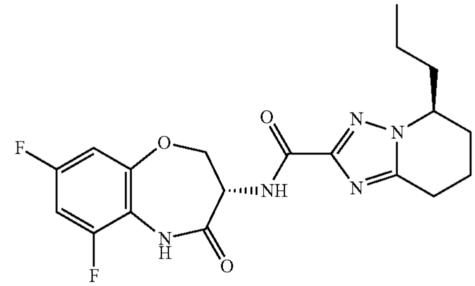

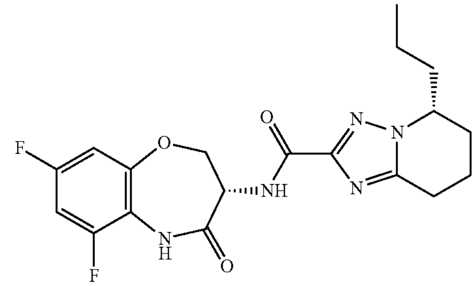

-continued

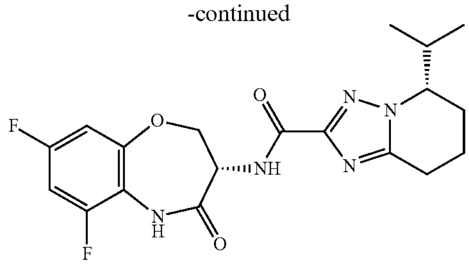

(R)—N—((S)-6,8-difluoro-4-oxo-2,3,4,5-tetrahydrobenzo[b][1,4]oxazepin-3-yl)-5-isopropyl-5,6,7,8-tetrahydro-[1,2,4]triazolo[1,5-a]pyridine-2-carboxamide (S)—N—((S)-6,8-difluoro-4-oxo-2,3,4,5-tetrahydrobenzo[b][1,4]oxazepin-3-yl)-5-propyl-5,6,7,8-tetrahydro-[1,2,4]triazolo[1,5-a]pyridine-2-carboxamide (R)—N—((S)-6,8-difluoro-4-oxo-2,3,4,5-tetrahydrobenzo[b][1,4]oxazepin-3-yl)-5-propyl-5, 6,7,8-tetrahydro-[1,2,4]triazolo[1,5-a]pyridine-2-carboxamide (S)—N—((S)-6,8-difluoro-4-oxo-2,3,4,5-tetrahydrobenzo[b][1,4]oxazepin-3-yl)-5-isopropyl-5,6,7,8-tetrahydro-[1,2,4]triazolo[1,5-a]pyridine-2-carboxamide Mixture of 64% (S)—N-(6,8-difluoro-4-oxo-2,3,4,5-tetrahydrobenzo[b][1,4]oxazepin-3-yl)-5-isopropyl-[1,2,4]triazolo[1,5-a]pyridine-2-carboxamide and 36(S)—N-(6,8-difluoro-4-oxo-2,3,4,5-tetrahydrobenzo[b][1,4]oxazepin-3-yl)-5-propyl-[1,2,4]triazolo[1,5-a]pyridine-2-carboxamide was reduced according to Method GZ2. The crude residue was further purified by chiral SFC was purified by chiral SFC (Chiralpak ID; 150×21.2 mm, 5 um; 30% methanol isocratic elution with Carbon Dioxide) affording four isomers (structural isomers were assigned based on 1H NMR; diastereomers were arbitrarily assigned):

(R)—N—((S)-6,8-difluoro-4-oxo-2,3,4,5-tetrahydrobenzo[b][1,4]oxazepin-3-yl)-5-isopropyl-5,6,7,8-tetrahydro-[1,2,4]triazolo[1,5-a]pyridine-2-carboxamide (3 mg, 4.3%) as white solids (S)—N—((S)-6,8-difluoro-4-oxo-2,3,4,5-tetrahydrobenzo[b][1,4]oxazepin-3-yl)-5-propyl-5,6,7, 8-tetrahydro-[1,2,4]triazolo[1,5-a]pyridine-2-carboxamide (1.1 mg, 1.7%) as white solids (R)—N—((S)-6,8-difluoro-4-oxo-2,3,4,5-tetrahydrobenzo[b][1,4]oxazepin-3-yl)-5-propyl-5,6,7, 8-tetrahydro-[1,2,4]triazolo[1,5-a]pyridine-2-carboxamide (1.4 mg, 2.1%) as white solids (S)—N—((S)-6,8-difluoro-4-oxo-2,3,4,5-tetrahydrobenzo[b][1,4]oxazepin-3-yl)-5-isopropyl-5,6,7,8-tetrahydro-[1,2,4]triazolo[1,5-a]pyridine-2-carboxamide (3.6 mg, 5.5%) as white solids.

Analytical data for the first eluting diastereomer (arbitrarily assigned R, S configuration): SFC $R_T$ (Whelkol s,s, 35% methanol+0.1% ammonium hydroxide isocratic elution with Carbon Dioxide, 2.5 min method): 0.626 min, 100% purity, 100% ee: $^1$H NMR (400 MHz, DMSO-d6) δ 10.07 (s, 1H), 8.38 (d, J=7.7 Hz, 1H), 7.23 (ddd, J=10.4, 9.0, 2.9 Hz, 1H), 7.03 (dt, J=9.4, 2.2 Hz, 1H), 4.90 (dt, J=11.1, 7.4 Hz, 1H), 4.65 (t, J=10.7 Hz, 1H), 4.52 (dd, J=10.2, 7.1 Hz, 1H), 4.17 (dt, J=8.8, 4.6 Hz, 1H), 2.90 (d, J=16.6 Hz, 1H), 2.79 (td, J=12.3, 10.8, 5.0 Hz, 1H), 2.68-2.59 (m, 1H), 2.10-1.98 (m, 2H), 1.84-1.65 (m, 2H), 0.98 (d, J=7.1 Hz, 3H), 0.69 (d, J=6.8 Hz, 3H). LCMS $R_T$=4.58 min, m/z=406.1 $(M+H)^+$.

LCMS (5 to 95% acetonitrile in water+0.1% formic acid over 10 mins) retention time 4.58 min, ESI+ found [M+H]=406.1

Analytical data for the second eluting diastereomer (arbitrarily assigned S, S configuration): SFC $R_T$ (Whelkol s,s, 35% methanol+0.1% ammonium hydroxide isocratic elution with Carbon Dioxide, 2.5 min method): 0.675 min, 100% purity, 100% ee:). LCMS $R_T$=4.68 min, m/z=406.1 $(M+H)^+$.

LCMS (5 to 95% acetonitrile in water+0.1% formic acid over 10 mins) retention time 4.68 min, ESI+ found [M+H]=406.1

Analytical data for the third eluting diastereomer (arbitrarily assigned R, S configuration): SFC $R_T$ (Whelkol s,s, 35% methanol+0.1% ammonium hydroxide isocratic elution with Carbon Dioxide, 2.5 min method): 0.918 min, 93.4% purity, 86.8% ee:). LCMS $R_T$=4.68 min, m/z=406.1 $(M+H)^+$.

LCMS (5 to 95% acetonitrile in water+0.1% formic acid over 10 mins) retention time 4.68 min, ESI+ found [M+H]=406.1

Analytical data for the fourth eluting diastereomer (arbitrarily assigned S, S configuration SFC $R_T$ (Whelkol s,s, 35% methanol+0.1% ammonium hydroxide isocratic elution with Carbon Dioxide, 2.5 min method): 0.975 min, 100% purity, 100% ee: $^1$H NMR (400 MHz, DMSO-d6) δ 10.07 (s, 1H), 8.38 (d, J=7.7 Hz, 1H), 7.23 (ddd, J=10.4, 9.0, 2.9 Hz, 1H), 7.03 (dt, J=9.4, 2.2 Hz, 1H), 4.90 (dt, J=11.1, 7.4 Hz, 1H), 4.65 (t, J=10.7 Hz, 1H), 4.52 (dd, J=10.2, 7.1 Hz, 1H), 4.17 (dt, J=8.8, 4.6 Hz, 1H), 2.90 (d, J=16.6 Hz, 1H), 2.79 (td, J=12.3, 10.8, 5.0 Hz, 1H), 2.68-2.59 (m, 1H), 2.10-1.98 (m, 2H), 1.84-1.65 (m, 2H), 0.98 (d, J=7.1 Hz, 3H), 0.69 (d, J=6.8 Hz, 3H). LCMS $R_T$=4.60 min, m/z=406.1 $(M+H)^+$.

LCMS (5 to 95% acetonitrile in water+0.1% formic acid over 10 mins) retention time 4.60 min, ESI+ found [M+H]=406.1

Example 448

Method GZ8

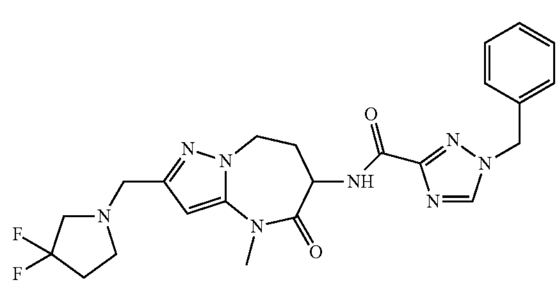 [SMILES: CN1C(=O)C(NC(=O)c2ncn(Cc3ccccc3)n2)CCn2nc(CN3CCC(F)(F)C3)cc21]

1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide

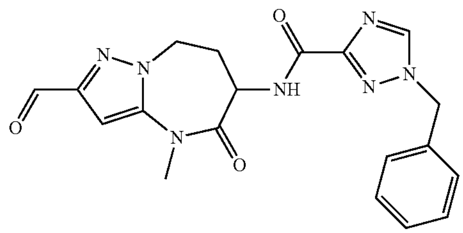 [SMILES: CN1C(=O)C(NC(=O)c2ncn(Cc3ccccc3)n2)CCn2nc(C=O)cc21]

Step 1: 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide The title compound was prepared from 5-bromo-1H-pyrazol-3-amine and 1-benzyl-1H-1,2,4-triazole-3-carboxylic acid according to Method GZ7 following step 1 to step 3. LCMS $R_T$=1.08 min [2 min method], m/z=394 $[M+H]^+$.

LCMS (5 to 95% acetonitrile in water+0.1% formic acid over 2 mins) retention time 1.08 min, ESI+ found [M+H]=394.0.

Step 2: 1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide To a solution of 3,3-difluoropyrrolidine hydrochloride (40 mg, 0.102 mmol) in dichloroethane (1 mL) was added triethylamine (0.04 mL, 0.305 mmol) and allowed to stir for 10 mins. Added 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide (40 mg, 0.102 mmol) as one portion, sodium triacetoxyborohydride (88 mg, 0.408 mmol) was added and allowed to stir overnight. The reaction was quenched with the addition of saturated aq. $NaHCO_3$ solution (10 mL) and stirring for 20 min. Extracted with isopropyl acetate (3×30 mL). The combined organics were dried over sodium sulfate, filtered, and concentrated to dryness in vacuo, The crude residue was purified by flash column chromatography (silica gel, 0% to 10% methanol in dichloromethane) to afford 1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide (69 mg, 72% Yield) as a tan solid: $^1$H NMR (400 MHz, DMSO-$d_6$) δ 8.81 (s, 1H), 8.52 (d, J=7.8 Hz, 1H), 7.42-7.26 (m, 5H), 6.28 (s, 1H), 5.48 (s, 2H), 4.31 (qd, J=7.9, 2.4 Hz, 2H), 4.15 (ddd, J=14.5, 12.6, 6.6 Hz, 1H), 3.57 (q, J=13.4 Hz, 2H), 3.23 (s, 3H), 2.91 (t, J=13.4 Hz, 2H), 2.73 (t, J=7.0 Hz, 2H), 2.67-2.54 (m, 1H), 2.43-2.10 (m, 3H). LC-MS $R_T$=2.88 min, m/z=485.2 $(M+H)^+$.

LCMS (5 to 95% acetonitrile in water+0.1% formic acid over 10 mins) retention time 2.88 min, ESI+ found [M+H]=485.2

Example 449

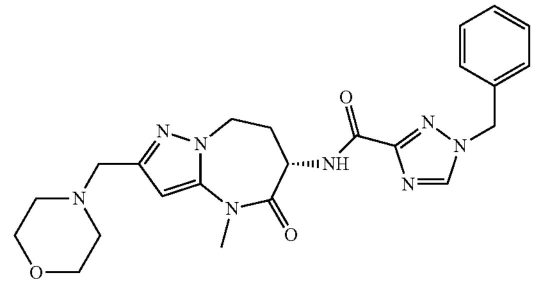 [SMILES: CN1C(=O)[C@@H](NC(=O)c2ncn(Cc3ccccc3)n2)CCn2nc(CN3CCOCC3)cc21]

Prepared according to Method GZ8.

$^1$H NMR (400 MHz, DMSO-$d_6$) δ 8.81 (s, 1H), 8.51 (d, J=7.7 Hz, 1H), 7.42-7.26 (m, 5H), 6.26 (s, 1H), 5.48 (s, 2H), 4.36-4.24 (m, 2H), 4.14 (ddd, J=14.5, 12.5, 6.6 Hz, 1H), 3.57 (t, J=4.6 Hz, 4H), 3.48-3.32 (m, 2H), 3.23 (s, 3H), 2.59 (m, 1H), 2.50-2.29 (m, 5H). m/z=465.2 $(M+H)^+$.

Example 450

Method GZ8

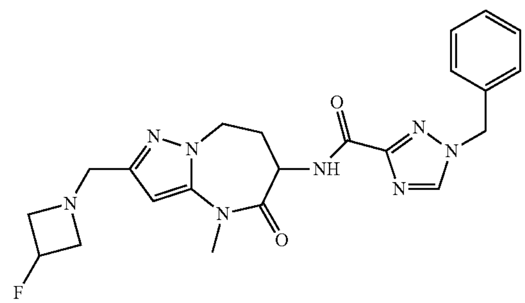 [SMILES: CN1C(=O)C(NC(=O)c2ncn(Cc3ccccc3)n2)CCn2nc(CN3CC(F)C3)cc21]

1-benzyl-N-(2-((3-fluoroazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide 1-benzyl-N-(2-((3-fluoroazetidin-1-yl)methyl)-4-methyl-5-oxo-5,6,7,8-tetrahydro-4H-pyrazol o[1,5-a][1,3]diazepin-6-yl)-1H-1,2,4-triazole-3-carboxamide was prepared from 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide and 3-fluoroazetidine hydrochloride according to Method GZ8 to afford final product (49 mg, 85%) as a white. $^1$H NMR (400 MHz, DMSO-$d_6$) δ 8.81 (s, 1H), 8.52 (d, J=7.8 Hz, 1H), 7.42-7.26 (m, 6H), 6.23 (s, 1H), 5.48 (s, 2H), 5.26-4.98 (m, 1H), 4.35-4.23 (m, 2H), 4.14 (ddd, J=14.4, 12.5, 6.6 Hz, 1H), 3.67-3.44 (m, 5H), 3.26-3.12 (m, 6H), 2.58 (tt, J=13.5, 8.5 Hz, 1H), 2.41-2.28 (m, 1H). LC-MS $R_T$=2.58 min, m/z=453.2 $(M+H)^+$.

LCMS (5 to 95% acetonitrile in water+0.1% formic acid over 10 mins) retention time 2.58 min, ESI+ found [M+H]=453.2

Example 451

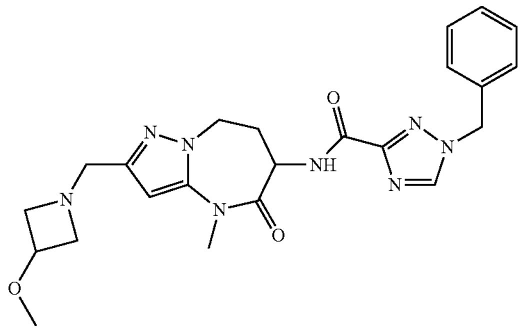 [SMILES: COC1CN(Cc2cc3n(n2)CCC(NC(=O)c2ncn(Cc4ccccc4)n2)C(=O)N3C)C1]

1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide 1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide was prepared from 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide and 3-methoxyazetidine hydrochloride according to Method GZ8 to afford final product (36 mg, 61%) as a white. $^1$H NMR (400 MHz, DMSO-d6) δ 8.81 (s, 1H), 8.51 (d, J=7.8 Hz, 1H), 7.42-7.23 (m, 5H), 6.21 (s, 1H), 5.48 (s, 2H), 4.29 (ddd, J=15.8, 8.1, 2.4 Hz, 2H), 4.13 (ddd, J=14.5, 12.6, 6.6 Hz, 1H), 3.94 (p, J=5.8 Hz, 1H), 3.48 (dt, J=21.7, 13.2 Hz, 4H), 3.22 (s, 3H), 3.14 (s, 3H), 2.92-2.81 (m, 2H), 2.57 (ddd, J=12.7, 8.0, 4.9 Hz, 1H), 2.41-2.28 (m, 1H). LC-MS $R_T$=2.66 min, m/z=465.2 (M+H)$^+$.

LCMS (5 to 95% acetonitrile in water+0.1% formic acid over 10 mins) retention time 2.66 min, ESI+ found [M+H]=465.2

Example 452

Method GZ6

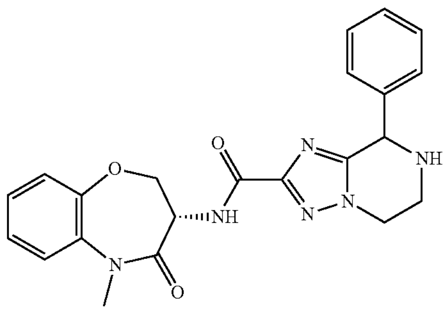

-continued

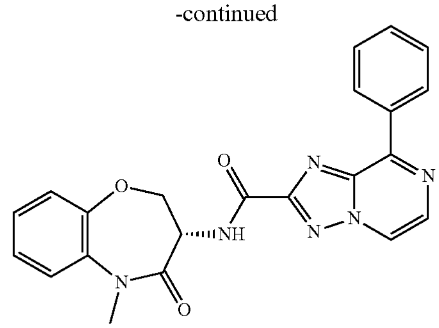

Step 1: (S)—N-(5-methyl-4-oxo-2,3,4,5-tetrahydrobenzo[b][1,4]oxazepin-3-yl)-8-phenyl-[1,2,4]triazolo[1,5-a]pyrazine-2-carboxamide Utilizing 3-phenylpyrazin-2-amine to replace 6-(trifluoromethyl)pyridin-2-amine in step 1 of Method GZ5, follow the steps. (S)—N-(5-methyl-4-oxo-2,3,4,5-tetrahydrobenzo[b][1,4]oxazepin-3-yl)-8-phenyl-[1,2,4]triazol o[1,5-a]pyrazine-2-carboxamide was prepared corresponding from (S)-3-amino-5-methyl-2,3-dihydrobenzo[b][1,4]oxazepin-4(5H)-one, and 8-phenyl-[1,2,4]triazolo[1,5-a]pyrazine-2-carboxylic acid according to Method GZ5. The residue was purified by preparative RP-HPLC (20-60% acetonitrile in water+0.1% formic acid) instead. Yield of final step: 35.5 mg, 22.9%. $^1$H NMR (400 MHz, DMSO-d6) δ 9.15-9.03 (m, 2H), 8.84-8.75 (m, 2H), 8.47 (d, J=4.5 Hz, 1H), 7.70-7.58 (m, 3H), 7.55 (dd, J=7.6, 1.9 Hz, 1H), 7.40-7.23 (m, 3H), 4.98 (dt, J=11.5, 7.8 Hz, 1H), 4.73 (dd, J=11.6, 9.8 Hz, 1H), 4.51 (dd, J=9.8, 7.7 Hz, 1H), 3.35 (s, 3H). LC-MS $R_T$=5.04 min, m/z=415.1 (M+H)$^+$.

LCMS (5 to 95% acetonitrile in water+0.1% formic acid over 10 mins) retention time 5.04 min, ESI+ found [M+H]=415.1

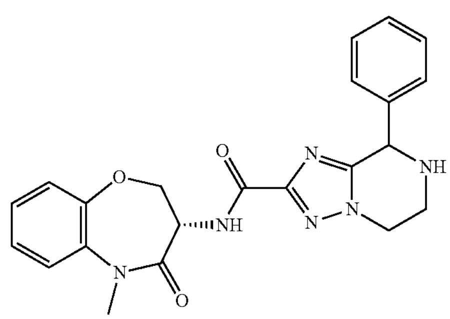 [SMILES: CN1C(=O)[C@@H](NC(=O)c2nc3n(n2)CCNC3c2ccccc2)COc2ccccc21]

Step 2: N—((S)-5-methyl-4-oxo-2,3,4,5-tetrahydrobenzo[b][1,4]oxazepin-3-yl)-8-phenyl-5,6,7,8-tetrahydro-[1,2,4]triazolo[1,5-a]pyrazine-2-carboxamide To a solution of (S)—N-(5-methyl-4-oxo-2,3,4,5-tetrahydrobenzo[b][1,4]oxazepin-3-yl)-8-phenyl-[1,2,4]triazol o[1,5-a]pyrazine-2-carboxamide (368 mg, 0.88 mmol) in tetrahydrofuran (20 mL) and methanol (20 mL) was added platinum(iv) oxide (20.2 mg, 0.088 mmol). The reaction mixture stirred under a balloon of hydrogen gas for 16 h at RT, then was filtered through Celite and concentrated to dryness in vacuo. The crude residue was purified by flash column chromatography (silica gel, 0% to 15% methanol in dichloromethane) to afford N—((S)-5-methyl-4-oxo-2,3,4,5-tetrahydrobenzo[b][1,4]oxazepin-3-yl)-8-phenyl-5,6,7,8-tetra hydro-[1,2,4]triazolo[1,5-a]pyrazine-2-carboxamide (216 mg, 52% Yield) as a tan solid: $^1$H NMR (400 MHz, DMSO-$d_6$) δ 8.34 (dd, J=8.1, 1.9 Hz, 1H), 7.49 (dt, J=7.5, 1.5 Hz, 1H), 7.44-7.11 (m, 9H), 5.20 (t, J=5.0 Hz, 1H), 4.91-4.75 (m, 1H), 4.56 (ddd, J=11.5, 9.9, 4.1 Hz, 1H), 4.37 (ddd, J=9.9, 7.6, 6.0 Hz, 1H), 4.32-4.15 (m, 2H), 3.37 (q, J=5.3 Hz, 1H), 3.32-3.11 (m, 4H). LC-MS $R_T$=3.26 min, m/z=419.1 $(M+H)^+$.

LCMS (5 to 95% acetonitrile in water+0.1% formic acid over 10 mins) retention time 3.26 min, ESI+ found [M+H]=419.1

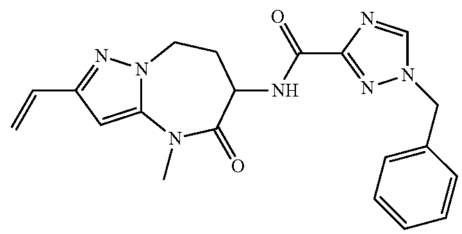 [SMILES: C=Cc1cc2n(n1)CCC(NC(=O)c1ncn(Cc3ccccc3)n1)C(=O)N2C]

Step 2: 1-benzyl-N-(4-methyl-5-oxo-2-vinyl-5,6,7,8-tetrahydro-4H-pyrazolo[1,5-a][1,3]diazepin-6-yl)-1H-1,2,4-triazole-3-carboxamide To a suspension of 1-benzyl-N-(2-bromo-4-methyl-5-oxo-7,8-dihydro-6H-pyrazolo[1,5-a][1,3]diazepin-6-yl)-1,2,4-triazole-3-carboxamide (3860 mg, 8.69 mmol, 1.0 equiv) in tetrahydrofuran (80 mL) and water (20 mL) was added potassium vinyltrifluoroborate (2450 mg, 17.38 mmol, 2.0 equiv) and cesium fluoride (3959 mg, 26.06 mmol, 3.0 equiv). The mixture was then degassed for 30 mins with a nitrogen stream. To the mixture was added bis(di-tert-butyl(4-dimethylaminophenyl)phosphine)dichloropalladium(II) (647.5 mg, 0.8688 mmol, 0.10 equiv). The vessel was capped, and the reaction mixture was heated to 70° C. for 4 days. After this time the mixture was diluted with dichloromethane (100 mL) and water (150 mL). The layers were separated, and the aqueous was extracted two more times with dichloromethane (2×100 mL). The combined organics were dried over sodium sulfate, filtered and evaporated to dryness in vacuo. The residue was purified by column chromatography (silica gel, 100-200 mesh, 0 to 5% methanol in dichloromethane) affording 1-benzyl-N-(4-methyl-5-oxo-2-vinyl-5,6,7,8-tetrahydro-4H-pyrazolo[1,5-a][1,3]diazepin-6-yl)-1H-1,2,4-triazole-3-carboxamide (1070 mg, 32% yield) as a dark brown solid. LCMS $R_T$=1.17 min [2 min method], m/z=392 $[M+H]^+$.

LCMS (5 to 95% acetonitrile in water+0.1% formic acid over 2 mins) retention time 1.17 min, ESI+ found [M+H]=392.0.

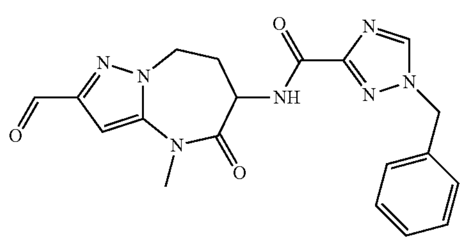 [SMILES: CN1C(=O)C(NC(=O)c2ncn(Cc3ccccc3)n2)CCn2nc(C=O)cc21]

Step 3: 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide Ozone was bubbled through a solution of 1-benzyl-N-(4-methyl-5-oxo-2-vinyl-5,6,7,8-tetrahydro-4H-pyrazolo[1,5-a][1,3]diazepin-6-yl)-1H-1,2,4-triazole-3-carboxamide (1070 mg, 2.73 mmol, 1.0 equiv) in methanol (20 mL) cooled to −78° C. for 45 mins. The reaction was quenched with dimethyl sulfide (1.01 mL, 849 mg, 13.7 mmol, 5.0 equiv) and allowed to warm to RT. The mixture was evaporated to dryness in vacuo, and the resulting residue was purified by column chromatography (silica gel, 100-200 mesh, 0 to 5% methanol in dichloromethane) affording 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide (600 mg, 56% yield) as a yellow solid. LCMS $R_T$=1.08 min [2 min method], m/z=394 $[M+H]^+$.

LCMS (5 to 95% acetonitrile in water+0.1% formic acid over 2 mins) retention time 1.08 min, ESI+ found [M+H]=394.0.

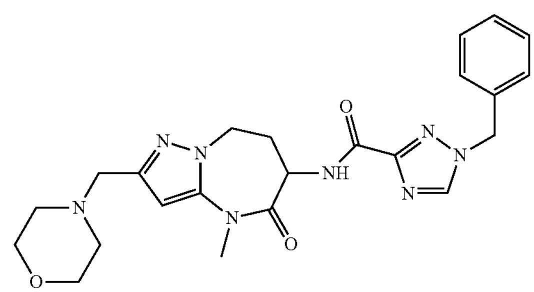 [SMILES: CN1C(=O)C(NC(=O)c2ncn(Cc3ccccc3)n2)CCn2nc(CN3CCOCC3)cc21]

Step 4: 1-benzyl-N-(4-methyl-2-(morpholinomethyl)-5-oxo-5,6,7,8-tetrahydro-4H-pyrazolo[1,5-a][1,3]diazepin-6-yl)-1H-1,2,4-triazole-3-carboxamide To a solution of 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide (40 mg, 0.102 mmol) and morpholine (0.026 mL, 0.305 mmol) in dichloroethane (1 mL) was added acetic acid (0.01 mL, 0.203 mmol) and allowed to stir for 30 min. Sodium triacetoxyborohydride (65 mg, 0.305 mmol) was added and allowed to stir overnight. The reaction was made basic with the addition of saturated aq. $NaHCO_3$ solution (10 mL) and stirring for 20 min. Extracted with isopropyl acetate (3×10 mL). The combined organics were dried over sodium sulfate, filtered, and concentrated to dryness in vacuo, The crude residue was purified by flash column chromatography (silica gel, 0% to 15% methanol in dichloromethane) to afford 1-benzyl-N-(4-methyl-2-(morpholinomethyl)-5-oxo-5,6,7,8-tetrahydro-4H-pyrazolo[1,5-a][1, 3]diazepin-6-yl)-1H-1,2,4-triazole-3-carboxamide (40 mg, 85% Yield) as a tan solid: $^1$H NMR (400 MHz, DMSO-$d_6$) δ 8.81 (s, 1H), 8.51 (d, J=7.7 Hz, 1H), 7.42-7.26 (m, 5H), 6.26 (s, 1H), 5.48 (s, 2H), 4.36-4.24 (m, 2H), 4.14 (ddd, J=14.5, 12.5, 6.6 Hz, 1H), 3.57 (t, J=4.6 Hz, 4H), 3.48-3.32 (m, 2H), 3.23 (s, 3H), 2.59 (m, 1H), 2.50-2.29 (m, 5H). LC-MS $R_T$=2.56 min, m/z=465.2 $(M+H)^+$.

LCMS (5 to 95% acetonitrile in water+0.1% formic acid over 10 mins) retention time 2.56 min, ESI+ found [M+H]=465.2

Example 453

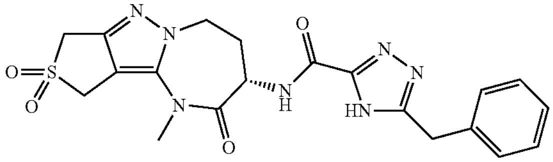 [SMILES: CN1C(=O)[C@@H](NC(=O)c2nnc(Cc3ccccc3)[nH]2)CCn2nc3c(c21)CS(=O)(=O)C3]

(S)-5-Benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-4H-1,2,4-triazole-3-carboxamide Method AA (10.5 mg, 38% yield for the chiral separation step)

$^{1}$H NMR (400 MHz, DMSO-d6) δ 8.47 (bs, 1H), 7.40-7.17 (m, 5H), 4.56-4.33 (m, 6H), 4.33-4.20 (m, 1H), 4.10 (s, 2H), 3.20 (s, 3H), 2.75-2.59 (m, 1H), 2.41-2.29 (m, 1H); LCMS $R_T$=3.40 min; m/z=456.1 $[M+H]^+$.

Chiral SFC separation condition: 20% Methanol (containing 0.1% Ammonium Hydroxide) in Carbon dioxide; ChiralPak OJ (250×21.2 mm); 70 mL/min; 40° C.

LCMS (2 to 98% acetonitrile in water+0.1% formic acid over 10 mins) retention time 3.40 min, ESI+ found [M+H]=456.1.

Example 454

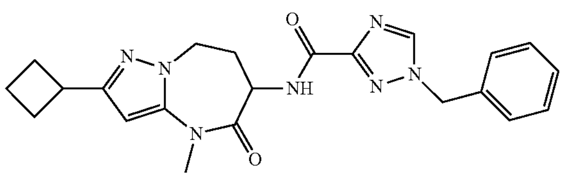 [SMILES: CN1C(=O)C(NC(=O)c2ncn(Cc3ccccc3)n2)CCn2nc(C3CCC3)cc21]

1-Benzyl-N-(2-cyclobutyl-4-methyl-5-oxo-5,6,7,8-tetrahydro-4H-pyrazolo[1,5-a][13]diazepin-6-yl)-1H-1,2,4-triazole-3-carboxamide Method Z (68 mg, 73% yield)

$^{1}$H NMR (400 MHz, DMSO-d6) δ 8.81 (s, 1H), 8.49 (d, J=7.8 Hz, 1H), 7.46-7.27 (m, 5H), 6.23 (s, 1H), 5.48 (s, 2H), 4.38-4.23 (m, 2H), 4.17-4.05 (m, 1H), 3.52-3.38 (m, 1H), 3.23 (s, 3H), 2.39-2.06 (m, 5H), 2.02-1.76 (m, 3H); LCMS $R_T$=4.58 min; m/z=420.2 $[M+H]^+$.

LCMS (2 to 98% acetonitrile in water+0.1% formic acid over 10 mins) retention time 4.58 min, ESI+ found [M+H]=420.2.

Example 455

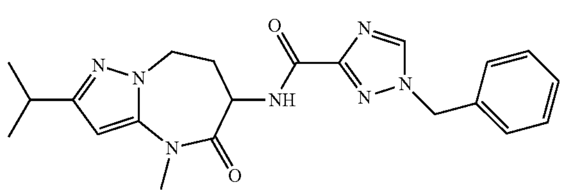 [SMILES: CC(C)c1cc2n(n1)CCC(NC(=O)c1ncn(Cc3ccccc3)n1)C(=O)N2C]

1-Benzyl-N-(2-isopropyl-4-methyl-5-oxo-5,6,7,8-tetrahydro-4H-pyrazol[1,5-a][1,3]diazepin-6-yl)-1H-1,2,4-triazole-3-carboxamide Method Z (52 mg, 55% yield)

$^{1}$H NMR (400 MHz, DMSO-d6) δ 8.81 (s, 1H), 8.49 (d, J=7.8 Hz, 1H), 7.43-7.26 (m, 5H), 6.18 (s, 1H), 5.48 (s, 2H), 4.39-4.23 (m, 2H), 4.20-4.03 (m, 1H), 3.22 (s, 3H), 2.86 (hept, J=7.0 Hz, 1H), 2.40-2.24 (m, 2H), 1.21 (d, J=6.9 Hz, 6H); LCMS $R_T$=4.08 min; m/z=408.2 $[M+H]^+$.

LCMS (2 to 98% acetonitrile in water+0.1% formic acid over 10 mins) retention time 4.08 min, ESI+ found [M+H]=408.2.

Example 456

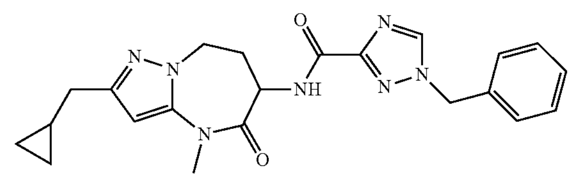 [SMILES: CN1C(=O)C(NC(=O)c2ncn(Cc3ccccc3)n2)CCn2nc(CC3CC3)cc21]

1-Benzyl-N-(2-(cyclopropylmethyl)-4-methyl-5-oxo-5,6,7,8-tetrahydro-4H-pyrazol[1,5-a][1,3]diazepin-6-yl)-1H-1,2,4-triazole-3-carboxamide Method Z (65 mg, 69% yield)

$^{1}$H NMR (400 MHz, DMSO-d6) δ 8.81 (s, 1H), 8.50 (d, J=7.8 Hz, 1H), 7.45-7.24 (m, 5H), 6.21 (s, 1H), 5.48 (s, 2H), 4.37-4.04 (m, 3H), 3.23 (s, 3H), 2.47-2.29 (m, 4H), 1.06-0.89 (m, 1H), 0.52-0.41 (m, 2H), 0.24-0.10 (m, 2H); LCMS $R_T$=4.51 min; m/z=420.2 $[M+H]^+$.

LCMS (2 to 98% acetonitrile in water+0.1% formic acid over 10 mins) retention time 4.51 min, ESI+ found [M+H]=420.2

Example 457

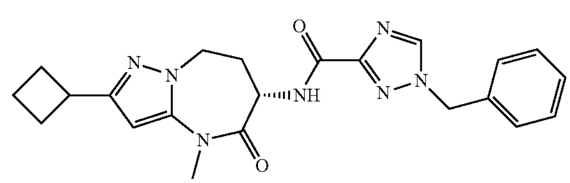 [SMILES: CN1C(=O)[C@@H](NC(=O)c2ncn(Cc3ccccc3)n2)CCn2nc(C3CCC3)cc21]

(S)-1-Benzyl-N-(2-cyclobutyl-4-methyl-5-oxo-5,6,7,8-tetrahydro-4H-pyrazolo[1,5-a][1,3]diazepin-6-yl)-1H-1,2,4-triazole-3-carboxamide Method Z (68 mg, 73% yield)

$^{1}$H NMR (400 MHz, DMSO-d6) δ 8.81 (s, 1H), 8.49 (d, J=7.8 Hz, 1H), 7.46-7.27 (m, 5H), 6.23 (s, 1H), 5.48 (s, 2H), 4.38-4.23 (m, 2H), 4.17-4.05 (m, 1H), 3.52-3.38 (m, 1H), 3.23 (s, 3H), 2.39-2.06 (m, 5H), 2.02-1.76 (m, 3H); LCMS $R_T$=4.60 min; m/z=420.2 $[M+H]^+$.

Chiral SFC separation condition: 40% Methanol (containing 0.1% Ammonium Hydroxide) in Carbon dioxide; Cellulose-1 (150×21.2 mm); 70 mL/min; 40° C.

LCMS (2 to 98% acetonitrile in water+0.1% formic acid over 10 mins) retention time 4.60 min, ESI+ found [M+H]=420.2.

Example 458

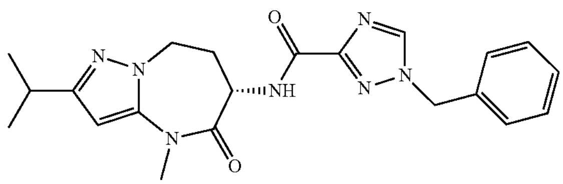 [SMILES: CC(C)c1cc2n(n1)CC[C@H](NC(=O)c1ncn(Cc3ccccc3)n1)C(=O)N2C]

(S)-1-Benzyl-N-(2-isopropyl-4-methyl-5-oxo-5,6,7,8-tetrahydro-4H-pyrazolo[1,5-a][1,3]diazepin-6-yl)-1H-1,2,4-triazole-3-carboxamide Method Z (18 mg, 72% yield for the chiral SFC separation step)

$^1$H NMR (400 MHz, DMSO-d6) δ 8.82 (s, 1H), 8.50 (d, J=7.8 Hz, 1H), 7.45-7.24 (m, 5H), 6.18 (s, 1H), 5.48 (s, 2H), 4.38-4.23 (m, 2H), 4.18-4.03 (m, 1H), 3.22 (s, 3H), 2.86 (hept, J=6.9 Hz, 1H), 2.66-2.53 (m, 1H), 2.41-2.26 (m, 1H), 1.21 (dd, J=6.9, 4.4 Hz, 6H); LCMS $R_T$=4.45 min; m/z=408.2 $[M+H]^+$.

Chiral SFC separation condition: 35% Methanol in Carbon dioxide; Cellulose-1 (150×21.2 mm); 70 mL/min; 40° C.

LCMS (2 to 98% acetonitrile in water+0.1% formic acid over 10 mins) retention time 4.45 min, ESI+ found [M+H]=408.2

Example 459

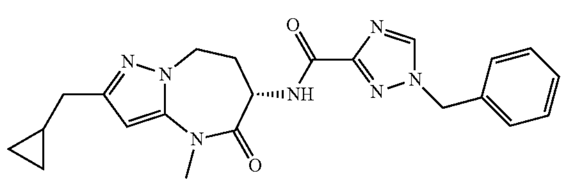 [SMILES: CN1C(=O)[C@@H](NC(=O)c2ncn(Cc3ccccc3)n2)CCn2nc(CC3CC3)cc21]

(S)-1-benzyl-N-(2-(cyclopropylmethyl)-4-methyl-5-oxo-5,6,7,8-tetrahydro-4H-pyrazolo[1,5-a][1,3]diazepin-6-yl)-1H-1,2,4-triazole-3-carboxamide Method Z (27.8 mg)

$^1$H NMR (400 MHz, DMSO-d6) δ 8.82 (s, 1H), 8.51 (d, J=7.8 Hz, 1H), 7.45-7.22 (m, 5H), 6.22 (s, 1H), 5.48 (s, 2H), 4.38-4.22 (m, 2H), 4.20-4.04 (m, 1H), 3.23 (s, 3H), 2.63-2.55 (m, 1H), 2.43 (t, J=6.5 Hz, 2H), 2.39-2.28 (m, 1H), 1.03-0.93 (m, 1H), 0.52-0.42 (m, 2H), 0.25-0.12 (m, 2H); LCMS $R_T$=4.53 min; m/z=420.2 $[M+H]^+$.

Chiral SFC separation condition: 35% Methanol in Carbon dioxide; Cellulose-1 (150×21.2 mm); 70 mL/min; 40° C.

LCMS (2 to 98% acetonitrile in water+0.1% formic acid over 10 mins) retention time 4.53 min, ESI+ found [M+H]=420.2

Example 460

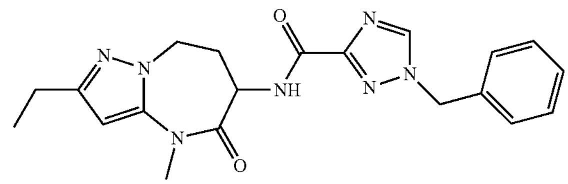 [SMILES: CCc1cc2n(n1)CCC(NC(=O)c1ncn(Cc3ccccc3)n1)C(=O)N2C]

1-Benzyl-N-(2-ethyl-4-methyl-5-oxo-5,6,7,8-tetrahydro-4H-pyrazolo[1,5-a][1,3]diazepin-6-yl)-1H-1,2,4-triazole-3-carboxamide Method Z (10.8 mg, 10% yield)

$^1$H NMR (400 MHz, DMSO-d6) δ 8.81 (s, 1H), 8.49 (d, J=7.8 Hz, 1H), 7.44-7.26 (m, 5H), 6.16 (s, 1H), 5.48 (s, 2H), 4.40-4.23 (m, 2H), 4.15-4.04 (m, 1H), 3.22 (s, 3H), 2.62-2.51 (m, 3H), 2.40-2.25 (m, 1H), 1.18 (t, J=7.6 Hz, 3H); LCMS $R_T$=4.14 min; m/z=394.2 $[M+H]^+$.

LCMS (2 to 98% acetonitrile in water+0.1% formic acid over 10 mins) retention time 4.14 min, ESI+ found [M+H]=394.2

Example 461

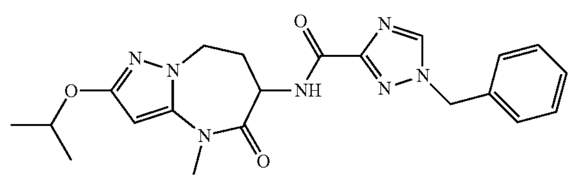 [SMILES: CC(C)Oc1cc2n(n1)CCC(NC(=O)c1ncn(Cc3ccccc3)n1)C(=O)N2C]

1-Benzyl-N-(2-isopropoxy-4-methyl-5-oxo-5,6,7,8-tetrahydro-4H-pyrazolo[1,5-a][1,3]diazepin-6-yl)-1H-1,2,4-triazole-3-carboxamide Method Z (84 mg, 73% yield)

$^1$H NMR (400 MHz, DMSO-d6) δ 8.82 (s, 1H), 8.52 (d, J=7.8 Hz, 1H), 7.43-7.26 (m, 5H), 5.79 (s, 1H), 5.48 (s, 2H), 4.68 (hepta, J=6.1 Hz, 1H), 4.37 (dt, J=11.5, 7.8 Hz, 1H), 4.15-4.02 (m, 2H), 3.20 (s, 3H), 2.64-2.53 (m, 1H), 2.39-2.25 (m, 1H), 1.28 (d, J=6.1 Hz, 3H), 1.26 (d, J=6.1 Hz, 3H); LCMS $R_T$=4.44 min; m/z=424.2 $[M+H]^+$.

LCMS (2 to 98% acetonitrile in water+0.1% formic acid over 10 mins) retention time 4.44 min, ESI+ found [M+H]=424.2

Example 462

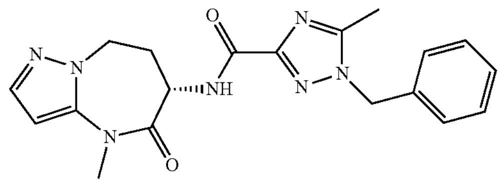 [SMILES: Cc1nc(C(=O)N[C@H]2CCn3nccc3N(C)C2=O)nn1Cc1ccccc1]

(S)-1-Benzyl-5-methyl-N-(4-methyl-5-oxo-5,6,7,8-tetrahydro-4H-pyrazolo[1,5-a][1,3]diazepin-6-yl)-1H-1,2,4-triazole-3-carboxamide Method B (57 mg, 56% yield)

$^1$H NMR (400 MHz, DMSO-d6) δ 8.46 (d, J=7.8 Hz, 1H), 7.49 (d, J=2.0 Hz, 1H), 7.41-7.30 (m, 3H), 7.26-7.18 (m, 2H), 6.34 (d, J=2.0 Hz, 1H), 5.44 (s, 2H), 4.44-4.12 (m, 3H), 3.25 (s, 3H), 2.66-2.53 (m, 1H), 2.46 (s, 3H), 2.43-2.32 (m, 1H); LCMS $R_T$=3.78 min; m/z=380.2 $[M+H]^+$.

LCMS (2 to 98% acetonitrile in water+0.1% formic acid over 10 mins) retention time 3.78 min, ESI+ found [M+H]=380.2

Example 463

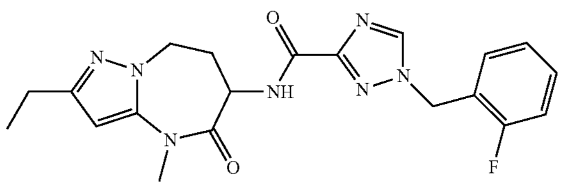 [SMILES: CCc1cc2n(n1)CCC(NC(=O)c1ncn(Cc3ccccc3F)n1)C(=O)N2C]

N-(2-Ethyl-4-methyl-5-oxo-5,6,7,8-tetrahydro-4H-pyrazolo[1,5-a][1,3]diazepin-6-yl)-1-(2-fluorobenzyl)-1H-1,2,4-triazole-3-carboxamide Method Z (159 mg, 61% yield)

$^1$H NMR (400 MHz, DMSO-d6) δ 8.80 (s, 1H), 8.49 (d, J=7.8 Hz, 1H), 7.50-7.15 (m, 4H), 6.16 (s, 1H), 5.55 (s, 2H), 4.39-4.22 (m, 2H), 4.14-4.00 (m, 1H), 3.22 (s, 3H), 2.62-2.52 (m, 3H), 2.41-2.25 (m, 1H), 1.18 (t, J=7.6 Hz, 3H); LCMS $R_T$=4.27 min; m/z=412.2 $[M+H]^+$.

LCMS (2 to 98% acetonitrile in water+0.1% formic acid over 10 mins) retention time 4.27 min, ESI+ found [M+H]=412.2

Example 464

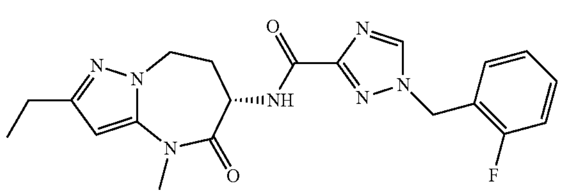 [SMILES: CCc1cc2n(n1)CC[C@H](NC(=O)c1ncn(Cc3ccccc3F)n1)C(=O)N2C]

(S)—N-(2-ethyl-4-methyl-5-oxo-5,6,7,8-tetrahydro-4H-pyrazolo[1,5-a][1,3]diazepin-6-yl)-1-(2-fluorobenzyl)-1H-1,2,4-triazole-3-carboxamide Method Z (78 mg, 97% yield in the chiral separation step)

$^1$H NMR (400 MHz, DMSO-d6) δ 8.80 (s, 1H), 8.50 (d, J=7.8 Hz, 1H), 7.47-7.18 (m, 4H), 6.16 (s, 1H), 5.55 (s, 2H), 4.39-4.23 (m, 2H), 4.19-4.03 (m, 1H), 3.22 (s, 3H), 2.70-2.50 (m, 3H), 2.41-2.21 (m, 1H), 1.18 (t, J=7.6 Hz, 3H).

Example 465

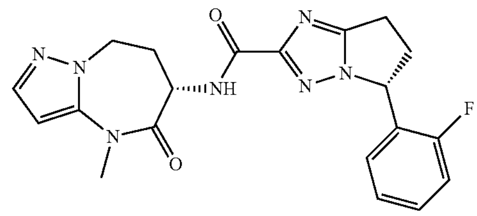 [SMILES: CN1C(=O)[C@@H](NC(=O)c2nc3n(n2)[C@@H](c2ccccc2F)CC3)CCn2nccc21]

(R)-5-(2-fluorophenyl)-N—((S)-4-methyl-5-oxo-5,6,7,8-tetrahydro-4H-pyrazolo[1,5-a][1,3]diazepin-6-yl)-6,7-dihydro-5H-pyrrolo[1,2-b][1,2,4]triazole-2-carboxamide (10.8 mg, 14% yield)

$^1$H NMR (400 MHz, DMSO-d6) δ 8.50 (d, J=7.9 Hz, 1H), 7.48 (d, J=2.0 Hz, 1H), 7.47-7.39 (m, 1H), 7.30-7.20 (m, 3H), 6.33 (d, J=2.0 Hz, 1H), 5.77 (dd, J=8.7, 5.7 Hz, 1H), 4.42-4.09 (m, 3H), 3.28-3.17 (m, 4H), 3.14-2.97 (m, 2H), 2.70-2.53 (m, 2H), 2.43-2.27 (m, 1H).

Example 466

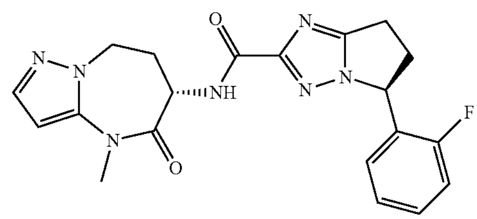 [SMILES: CN1C(=O)[C@@H](NC(=O)c2nc3n(n2)[C@H](c2ccccc2F)CC3)CCn2nccc21]

(S)-5-(2-fluorophenyl)-N—((S)-4-methyl-5-oxo-5,6,7,8-tetrahydro-4H-pyrazolo[1,5-a][1,3]diazepin-6-yl)-6,7-dihydro-5H-pyrrolo[1,2-b][1,2,4]triazole-2-carboxamide (11.1 mg, 14% yield)

$^1$H NMR (400 MHz, DMSO-d6) δ 8.53 (d, J=7.8 Hz, 1H), 7.48 (d, J=2.0 Hz, 1H), 7.47-7.39 (m, 1H), 7.31-7.19 (m, 3H), 6.33 (d, J=2.0 Hz, 1H), 5.78 (dd, J=8.7, 5.7 Hz, 1H), 4.43-4.09 (m, 3H), 3.29-3.17 (m, 4H), 3.11-2.99 (m, 2H), 2.71-2.53 (m, 2H), 2.43-2.28 (m, 1H).

Example 467

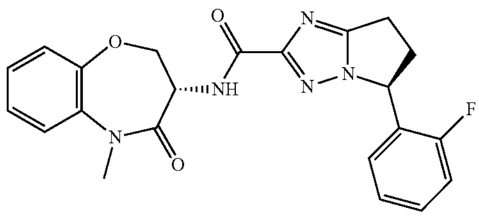 [SMILES: CN1C(=O)[C@@H](NC(=O)c2nc3n(n2)[C@H](c2ccccc2F)CC3)COc2ccccc21]

(S)-5-(2-fluorophenyl)-N—((S)-5-methyl-4-oxo-2,3,4,5-tetrahydrobenzo[b][1,4]oxazepin-3-yl)-6,7-dihydro-5H-pyrrolo[1,2-b][1,2,4]triazole-2-carboxamide (10.8 mg, 14% yield)

$^1$H NMR (400 MHz, DMSO-d6) δ 8.43 (d, J=8.0 Hz, 1H, NH), 7.52-7.47 (m, 1H), 7.47-7.40 (m, 1H), 7.34-7.19 (m, 6H), 5.78 (dd, J=8.6, 5.7 Hz, 1H), 4.81 (dt, J=11.5, 7.8 Hz, 1H), 4.58 (dd, J=11.6, 9.9 Hz, 1H), 4.39 (dd, J=9.9, 7.7 Hz, 1H), 3.30 (s, 3H), 3.27-3.18 (m, 1H), 3.16-2.95 (m, 2H), 2.70-2.54 (m, 1H).

Example 468

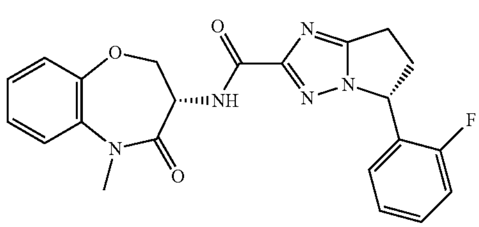 [SMILES: CN1C(=O)[C@@H](NC(=O)c2nc3n(n2)[C@@H](c2ccccc2F)CC3)COc2ccccc21]

(R)-5-(2-fluorophenyl)-N—((S)-5-methyl-4-oxo-2,3,4,5-tetrahydrobenzo[b][1,4]oxazepin-3-yl)-6,7-dihydro-5H-pyrrolo[1,2-b][1,2,4]triazole-2-carboxamide (8.8 mg, 11% yield)

1H NMR (400 MHz, DMSO-d6) δ 8.43 (d, J=8.0 Hz, 1H, NH), 7.53-7.45 (m, 1H), 7.47-7.39 (m, 1H), 7.35-7.19 (m, 6H), 5.78 (dd, J=8.7, 5.7 Hz, 1H), 4.81 (dt, J=11.5, 7.8 Hz, 1H), 4.57 (dd, J=11.5, 9.9 Hz, 1H), 4.39 (dd, J=9.9, 7.7 Hz, 1H), 3.31 (s, 3H), 3.28-3.17 (m, 1H), 3.11-2.98 (m, 2H), 2.68-2.56 (m, 1H).

Example 469

WX Method 135

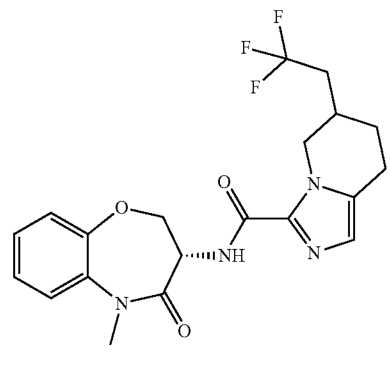 [SMILES: CN1C(=O)[C@@H](NC(=O)c2ncc3n2CC(CC(F)(F)F)CC3)COc2ccccc21]

N-[(3S)-5-methyl-4-oxo-2,3-dihydro-1,5-benzoxazepin-3-yl]-6-(2,2,2-trifluoroethyl)-5,6,7,8-tetrahydroimidazo[1,5-a]pyridine-3-carboxamide

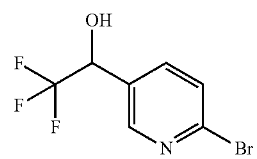

Step 1: 1-(6-bromopyridin-3-yl)-2,2,2-trifluoroethanol

To a solution of 6-bromonicotinaldehyde (3.0 g, 16.13 mmol) in tetrahydrofuran (100 mL) was added (trifluoromethyl)trimethylsilane (467 mg, 3.28 mmol) and tetrabutylammoniumfluoride (0.27 ml, 0.27 mmol) at 0° C. The resulting mixture was warmed to 25° C. and stirred for 48 h. The reaction mixture was poured into water (30 mL) and extracted with ethyl acetate (3×30 mL). The combined organic layers were dried over sodium sulfate and concentrated under reduced pressure. The residue was purified by column chromatography (silica gel, 100-200 mesh, 0 to 30% ethyl acetate in petroleum ether) to afford 1-(6-bromo-3-pyridyl)-2,2,2-trifluoro-ethanol (3.8 g, 92%) as brown solid. $^1$H NMR (400 MHz, $CDCl_3$) δ 8.44 (d, J=2.0 Hz, 1H), 7.77-7.74 (m, 1H), 7.57 (d, J=8.4 Hz, 1H), 5.11 (q, J=6.8 Hz, 1H).

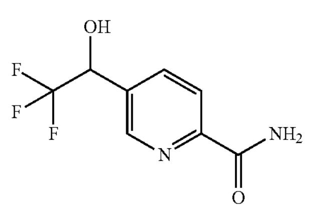 [SMILES: NC(=O)c1ccc(C(O)C(F)(F)F)cn1]

Step 2: 5-(2,2,2-trifluoro-1-hydroxyethyl)picolinamide

A mixture of 1-(6-bromo-3-pyridyl)-2,2,2-trifluoro-ethanol (3.8 g, 14.84 mmol) and copper(I) cyanide (2.66 g, 29.69 mmol) in 1-methyl-2-pyrrolidinone (50 mL) was heated to 130° C. for 10 h. The reaction mixture was poured into 10% ammonium hydroxide (30 mL) and extracted with ethyl acetate (3×30 mL). The combined organic layers were dried over sodium sulfate and concentrated under reduced pressure. The residue was purified by column chromatography (silica gel, 100-200 mesh, 0 to 60% ethyl acetate in petroleum ether) to afford 5-(2,2,2-trifluoro-1-hydroxy-ethyl) pyridine-2-carboxamide (2 g, 61%) as yellow oil. LCMS $R_T$=0.98 min; m/z=221.0 $(M+H)^+$.

LCMS (10-80% acetonitrile in water+0.05% ammonium bicarbonate over 3 mins) retention time 0.98/min, ESI+ found [M+H]=221.0.

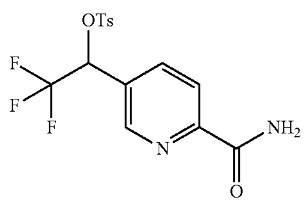 [SMILES: Cc1ccc(S(=O)(=O)OC(c2ccc(C(N)=O)nc2)C(F)(F)F)cc1]

Step 3: 1-(6-carbamoylpyridin-3-yl)-2,2,2-trifluoroethyl 4-methylbenzenesulfonate To a solution of 5-(2,2,2-trifluoro-1-hydroxy-ethyl)pyridine-2-carboxamide (2.0 g, 9.08 mmol) in dichloromethane (50 mL) was added triethylamine (1.84 g, 18.17 mmol), p-toluenesulfonylchloride (2.60 g, 13.63 mmol) and 4-dimethylaminopyridine (222 mg, 1.82 mmol) at 0° C. After addition, the reaction mixture was stirred at 25° C. for 5 h. The reaction mixture was poured into water (5 mL) and extracted with dichloromethane (3×15 mL). The combined organic layers were dried over sodium sulfate and concentrated under reduced pressure. The residue was purified by column chromatography (silica gel, 100-200 mesh, 0 to 40% ethyl acetate in petroleum ether) to afford [1-(6-carbamoyl-3-pyridyl)-2,2,2-trifluoro-ethyl]4-methylbenzenesulfonate (1.8 g, 53%) as white solid. LCMS $R_T$=0.72 min; m/z=374.9 $(M+H)^+$.

LCMS (5 to 95% acetonitrile in water+0.03% trifluoacetic acid over 1.5 mins) retention time 0.72 min, ESI+ found [M+H]=374.9.

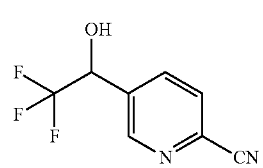 [SMILES: N#Cc1ccc(C(O)C(F)(F)F)cn1]

Step 4:1-(6-cyanopyridin-3-yl)-2,2,2-trifluoroethyl 4-methylbenzenesulfonate

A solution of [1-(6-carbamoyl-3-pyridyl)-2,2,2-trifluoro-ethyl] 4-methylbenzenesulfonate (1.8 g, 4.81 mmol) in tetrahydrofuran (100 mL) was treated with triethylamine (1.46 g, 14.43 mmol) and trifluoroacetic anhydride (1.52 g, 7.21 mmol) at 0° C. The resulting mixture was stirred at 25° C. for 1 h. The reaction mixture was poured into water (50 mL) and extracted with ethyl acetate (3×30 mL). The combined organic layers were dried over sodium sulfate and concentrated under reduced pressure. The residue was purified by column chromatography (silica gel, 100-200 mesh, 0 to 33% ethyl acetate in petroleum ether) to afford [1-(6-cyano-3-pyridyl)-2,2,2-trifluoro-ethyl] 4-methylbenzenesulfonate (1.5 g, 87%) as white solid. $^1$H NMR (400 MHz, $CDCl_3$) δ 8.70 (s, 1H), 7.92-7.90 (m, 1H), 7.74-7.70 (m, 3H), 7.34-7.32 (m, 1H), 5.75 (q, J=6.8 Hz, 1H), 2.46 (s, 3H).

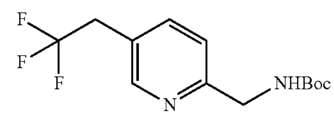 [SMILES: CC(C)(C)OC(=O)NCc1ccc(CC(F)(F)F)cn1]

Step 5: tert-butyl ((5-(2,2,2-trifluoroethyl)pyridin-2-yl)methyl)carbamate

A mixture of [1-(6-cyano-3-pyridyl)-2,2,2-trifluoro-ethyl] 4-methylbenzenesulfonate (1.30 g, 3.65 mmol), Pd/C (10%, 389 mg, 0.37 mmol) and hydrochloric acid (36%, 1.11 g, 10.95 mmol) in methanol (100 mL) was hydrogenated (50 psi) for 24 h. The reaction mixture was filtered and the filtrate was adjusted to pH=10 by addition of 2N sodium hydroxide (1 mL) and then di-tert-butyldicarbonate (1.59 g, 7.30 mmol) was added to the above solution. The reaction mixture was stirred at 25° C. for 10 h and concentrated under reduced pressure. The residue was diluted with water (10 mL) and extracted with ethyl acetate (3×15 mL). The combined organic layer was dried over sodium sulfate and concentrated. The residue was purified by column chromatography (silica gel, 100-200 mesh, 0 to 40% ethyl acetate in petroleum ether) to afford tert-butyl N-[[5-(2,2,2-trifluoroethyl)-2-pyridyl]methyl]carbamate (1.0 g, 94%) as white solid. $^1$H NMR (400 MHz, $CDCl_3$) δ 8.47 (s 1H), 7.64 (d, J=2.0 Hz, 1H), 7.31 (d, J=2.0 Hz, 1H), 5.54 (s, 1H), 4.47-4.45 (m, 2H), 3.40 (q, J=6.8 Hz, 2H), 1.47 (s, 9H).

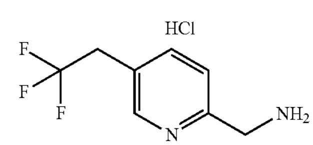 [SMILES: Cl ; NCc1ccc(CC(F)(F)F)cn1]

Step 6: (5-(2,2,2-trifluoroethyl)pyridin-2-yl)methanamine hydrochloride

A solution of tert-butyl N-[[5-(2,2,2-trifluoroethyl)-2-pyridyl]methyl]carbamate (1.0 g, 3.44 mmol) in ethyl acetate (20 mL) was treated with hydrochloric acid (4N in ethyl acetate, 4.0 mL, 16.0 mmol). The resulting mixture was stirred at 25° C. for 1 h and concentrated under reduced pressure to afford crude [5-(2,2,2-trifluoroethyl)-2-pyridyl] methanamine hydrochloride (800 mg, 100%) as white solid, used as is in the next step.

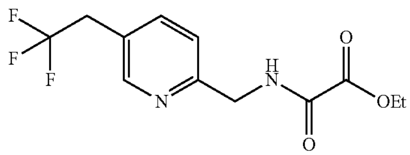 [SMILES: CCOC(=O)C(=O)NCc1ccc(CC(F)(F)F)cn1]

Step 7: Ethyl 2-oxo-2-(((5-(2,2,2-trifluoroethyl) pyridin-2-yl)methyl)amino)acetate A mixture of [5-(2,2,2-trifluoroethyl)-2-pyridyl]methanamine hydrochloride (300 mg, 1.32 mmol) and triethylamine (536 mg, 5.29 mmol) in tetrahydrofuran (20 mL) was treated with ethyl oxalyl chloride (271 mg, 1.99 mmol) at 0° C. After addition, the reaction mixture was stirred to 25° C. for 5 h. The reaction mixture was poured into water (30 mL) and extracted with ethyl acetate (3×30 mL). The combined organic layers were dried over sodium sulfate and concentrated under reduced pressure to afford crude ethyl 2-oxo-2-[[5-(2,2,2-trifluoroethyl)-2-pyridyl]methyl amino]acetate (400 mg, 100%) as a brown solid. LCMS $R_T$=0.53 min; m/z=290.8 $(M+H)^+$. LCMS (5 to 95% acetonitrile in water+0.03% trifluoacetic acid over 1.5 mins) retention time 0.53 min, ESI+ found [M+H]=290.8.

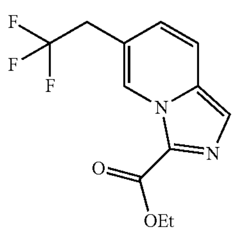 [SMILES: CCOC(=O)c1ncc2ccc(CC(F)(F)F)cn12]

Step 8: Ethyl 6-(2,2,2-trifluoroethyl)imidazo[1,5-a] pyridine-3-carboxylate

A mixture of ethyl 2-oxo-2-[[5-(2,2,2-trifluoroethyl)-2-pyridyl]methylamino]acetate (350 mg, 1.21 mmol) and phosphorus oxychloride (16.88 g, 110.09 mmol) was heated to 110° C. for 10 h. The reaction mixture was poured into water (100 mL) and extracted with ethyl acetate (3×20 mL). The combined organic layers were dried over sodium sulfate and concentrated under reduced pressure. The residue was purified by column chromatography (silica gel, 100-200 mesh, 0 to 30% ethyl acetate in petroleum ether) to afford methyl 6-(2,2,2-trifluoroethyl)imidazo[1,5-a]pyridine-3-carboxylate (150 mg, 48%) as a brown solid.

$^1H$ NMR (400 MHz, $CDCl_3$) δ 9.34 (s, 1H), 7.65 (d, J=2.0 Hz, 1H), 7.31 (d, J=2.0 Hz, 1H), 7.65-7.63 (m, 2H), 7.04-7.02 (m, 1H), 4.52 (q, J=6.8 Hz, 2H), 3.40 (q, J=6.8 Hz, 2H), 1.49 (t, J=4.2 Hz, 2H).

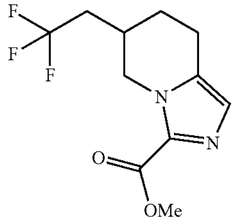 [SMILES: COC(=O)c1ncc2n1CC(CC(F)(F)F)CC2]

Step 9: Ethyl 6-(2,2,2-trifluoroethyl)-5,6,7,8-tetrahydroimidazo[1,5-a]pyridine-3-carboxylate A mixture of ethyl 6-(2,2,2-trifluoroethyl)imidazo[1,5-a] pyridine-3-carboxylate (150 mg, 0.55 mmol) and Pd/C (10%, 30 mg) in methanol (10 mL) was hydrogenated (50 psi) at 50° C. for 10 h and filtered. The filtrate was concentrated under reduced pressure and the residue was purified by preparative TLC (50% ethyl acetate in petroleum ether) to afford methyl 6-(2,2,2-trifluoroethyl)-5,6,7,8-tetrahydroimidazo[1,5-a]pyridine-3-carboxylate (100 mg, 69%) as colorless oil. $^1H$ NMR (400 MHz, $CDCl_3$) δ 6.95 (s, 1H), 4.84-4.79 (m, 1H), 3.94-3.85 (m, 4H), 3.02-2.97 (m, 1H), 2.83-2.82 (m, 1H), 2.38-2.09 (m, 5H).

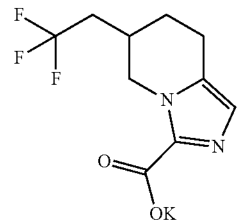

Step 10: Potassium 6-(2,2,2-trifluoroethyl)-5,6,7,8-tetrahydroimidazo[1,5-a]pyridine-3-carboxylate A mixture of methyl 6-(2,2,2-trifluoroethyl)-5,6,7,8-tetrahydroimidazo[1,5-a]pyridine-3-carboxylate (30 mg, 0.11 mmol) in water (1 mL) and tetrahydrofuran (2 mL) was treated with potassium hydroxide (12 mg, 0.23 mmol). The resulting mixture was stirred at 25° C. for 1 hand then concentrated under reduced pressure to afford crude potassium 6-(2,2,2-trifluoroethyl)-5,6,7,8-tetrahydroimidazo[1,5-a]pyridine-3-carboxylate (30 mg, 92%) as a white solid, used is as in the next step.

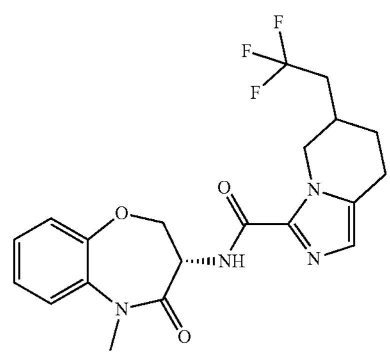 [SMILES: CN1C(=O)[C@@H](NC(=O)c2ncc3n2CC(CC(F)(F)F)CC3)COc2ccccc21]

Step 11: N-[(3S)-5-methyl-4-oxo-2,3-dihydro-1,5-benzoxazepin-3-yl]-6-(2,2,2-trifluoroethyl)-5,6,7,8-tetrahydroimidazo[1,5-a]pyridine-3-carboxamide A mixture of potassium 6-(2,2,2-trifluoroethyl)-5,6,7,8-tetrahydroimidazo[1,5-a]pyridine-3-carboxylate (30 mg, 0.10 mmol), (3S)-3-amino-5-methyl-2,3-dihydro-1,5-benzoxazepin-4-one (24 mg, 0.13 mmol) and (7-Azabenzotriazol-1-yloxy)tripyrrolidinophosphonium hexafluorophosphate (65 mg, 0.13 mmol) in N,N-dimethylformamide (3 mL) was stirred at 25° C. for 10 h. The reaction was concentrated under reduced pressure and the residue was purified by RP-HPLC (40% to 70% acetonitrile/0.05% ammonia hydroxide in water) to afford N-[(3S)-5-methyl-4-oxo-2,3-dihydro-1,5-benzoxazepin-3-yl]-6-(2,2,2-trifluoroethyl)-5,6,7,8-tetrahydroimidazo[1,5-a]pyridine-3-carboxamide (6.6 mg, 15%) as white solid. $^1H$ NMR (400 MHz, $CD_3OD$) δ7.44-7.41 (m, 1H), 7.32-7.29 (m, 2H), 7.24-7.22 (m, 1H), 6.83 (s, 1H), 4.95-4.90 (m, 1H), 4.85-4.80 (m, 1H), 4.60-4.55 (m, 1H), 4.38-4.34 (m, 1H), 3.85-3.83 (m, 1H), 3.41 (s, 3H), 3.01-2.96 (m, 1H), 2.80-2.78 (m, 1H), 2.35-2.30 (m, 3H), 2.08-2.05 (m, 1H), 1.62-1.60 (m, 1H). LCMS $R_T$=2.52 min, m/z=423.1 $(M+H)^+$.

LCMS (0-60% acetonitrile in water+0.05% ammonium bicarbonate over 3 mins) retention time 2.52 min, ESI+ found [M+H]=423.1.

Example 470

WX Method 001

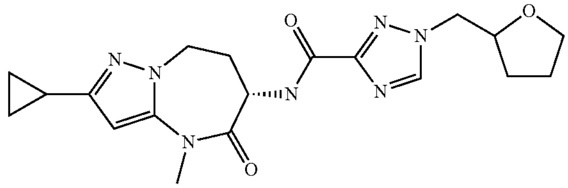 [SMILES: CN1C(=O)[C@@H](NC(=O)c2ncn(CC3CCCO3)n2)CCn2nc(C3CC3)cc21]

N-(6S)-2-cyclopropyl-4-methyl-5-oxo-7,8-dihydro-6H-pyrazolo[1,5-a][1,3]diazepin-6-yl-1-(tetrahydrofuran-2-ylmethyl)-1,2,4-triazole-3-carboxamide A mixture of potassium carbonate (328 mg, 2.38 mmol), N-[(6S)-2-cyclopropyl-4-methyl-5-oxo-7,8-dihydro-6H-pyrazolo[1,5-a][1,3]diazepin-6-yl]-1H-1,2,4-triazole-3-carboxamide (150 mg, 0.48 mmol) and 2-(bromomethyl)tetrahydrofuran (160 mg, 0.97 mmol) in N,N-dimethylformamide (5 mL) was stirred at 25° C. for 15 h. The mixture was filtrated and the filtrate was concentrated under reduced pressure. The residue was purified by RP-HPLC (acetonitrile 13-43%/0.05% ammonia hydroxide in water) to afford N-(6S)-2-cyclopropyl-4-methyl-5-oxo-7,8-dihydro-6H-pyrazolo[1,5-a][1,3]diazepin-6-yl-1-(tetrahydrofuran-2-ylmethyl)-1,2,4-triazole-3-carboxamide (29.1 mg, 15%) as white solids. $^1H$ NMR (400 MHz, $CD_3OD$) δ 8.46 (s, 1H), 6.01 (s, 1H), 4.56-4.51 (m, 1H), 4.38-4.23 (m, 5H), 3.84-3.74 (m, 2H), 3.32 (s, 3H), 2.87-2.85 (m, 1H), 2.27-2.25 (m, 1H), 2.25-2.23 (m, 1H), 1.94-1.87 (m, 3H), 1.83-1.81 (m, 1H), 0.95-0.92 (m, 2H), 0.75-0.73 (m, 2H). LC-MS $R_T$=0.700 min, m/z=400.1 $(M+H)^+$.

LCMS (10 to 80% acetonitrile in water+0.03% trifluoacetic acid over 2.0 mins) retention time 0.700 min, ESI+ found [M+H]=400.1.

Example 471

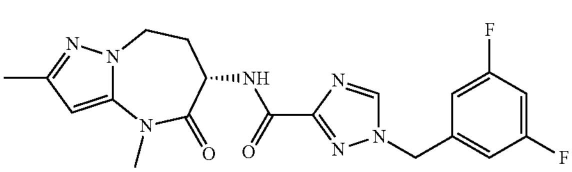 [SMILES: Cc1cc2n(n1)CC[C@H](NC(=O)c1ncn(Cc3cc(F)cc(F)c3)n1)C(=O)N2C]

1-[(3,5-difluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide N-Alkylation prepared in a similar fashion to WX Method 001. The crude was purified by RP-HPLC (methanol 50-80%/0.05% ammonia hydroxide in water) to afford 1-[(3,5-difluorophenyl)methyl]-N-[(6S)-2,4-dimethyl-5-oxo-7,8-dihydro-6H-pyrazolo[1,5][1,5-a][1,3]diazepin-6-yl]-1,2,4-triazole-3-carboxamide (28 mg, 32%) as a white solid. $^1H$ NMR (400 MHz, $CD_3OD$) δ8.61 (s, 1H), 6.96-6.90 (m, 3H), 6.10 (s, 1H), 5.48 (s, 2H), 4.54-4.49 (m, 1H), 4.2-4.27 (m, 1H), 4.24-4.19 (m, 1H), 3.29 (m, 3H), 2.85-2.79 (m, 1H), 2.28-2.21 (m, 4H). LC-MS $R_T$=0.756 min, m/z=416.1 $[M+H]^+$.

LCMS (5 to 95% acetonitrile in water+0.03% trifluoacetic acid over 1.5 mins) retention time 0.756 min, ESI+ found [M+H]=416.1.

Example 472

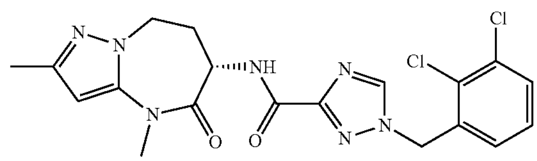 [SMILES: Cc1cc2n(n1)CC[C@H](NC(=O)c1ncn(Cc3cccc(Cl)c3Cl)n1)C(=O)N2C]

A mixture of N-[(6S)-2,4-dimethyl-5-oxo-7,8-dihydro-6H-pyrazolo[1,5-a][1,3]diazepin-6-yl]-1H-1,2,4-triazole-3-carboxamide (60 mg, 0.21 mmol), 1-(bromomethyl)-2,3-dichloro-benzene (59 mg, 0.25 mmol) and potassium carbonate (86 mg, 0.62 mmol) in N,N-dimethylformamide (5 mL) was stirred at 25° C. for 12 h and concentrated under reduced pressure. The residue was purified by RP-HPLC (methanol 55-85%/0.05% ammonia hydroxide in water) to afford (1-[(2,3-dichlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide (19.4 mg, 21%) as a white solid. $^1H$ NMR (400 MHz, $CD_3OD$) δ 8.61 (s, 1H), 7.55-7.53 (m, 1H), 7.33-7.29 (m, 1H), 7.22-7.20 (m, 1H), 6.09 (s, 1H), 5.63 (s, 2H), 4.53-4.48 (m, 1H), 4.29-4.27 (m, 1H), 4.22-4.15 (m, 1H), 3.30 (s, 3H), 2.85-2.78 (m, 1H), 2.27-2.20 (m, 4H). LCMS $R_T$=0.791 min, m/z=448.1 $[M+H]^+$.

LCMS (5 to 95% acetonitrile in water+0.03% trifluoacetic acid over 1.5 mins) retention time 0.791 min, ESI+ found [M+H]=448.1.

Example 473

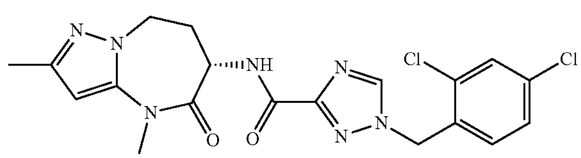 [SMILES: Cc1cc2n(n1)CC[C@H](NC(=O)c1ncn(Cc3ccc(Cl)cc3Cl)n1)C(=O)N2C]

1-[(2,4-dichlorophenyl)methyl]-N-[(6S)-2,4-dimethyl-5-oxo-7,8-dihydro-6H-pyrazolo[1,5-a][1,3]diazepin-6-yl]-1,2,4-triazole-3-carboxamide N-Alkylation prepared in a similar fashion to WX Method 001. The crude was purified by RP-HPLC (methanol 60-90%/0.05% ammonia hydroxide in water) to give 1-[(2,4-dichlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide (16.7 mg, 18%) as a white solid. $^1H$ NMR (400 MHz, $CD_3OD$) δ8.59 (s, 1H), 7.52 (s, 1H), 7.41-7.30 (m, 2H), 5.99 (s, 1H), 5.57 (s, 2H), 4.53-4.48 (m, 1H), 4.28-4.26 (m, 1H), 4.20-4.17 (m, 1H), 3.29 (s, 3H), 2.85-2.78 (m, 1H), 2.27-2.22 (m, 1H), 1.91-1.86 (m, 1H), 0.92-0.91 (m, 2H), 0.77-0.71 (m, 2H). LC-MS $R_T$=0.831 min, m/z=474.1 $[M+H]^+$.

LCMS (5 to 95% acetonitrile in water+0.03% trifluoacetic acid over 1.5 mins) retention time 0.831 min, ESI+ found [M+H]=474.1.

Example 474

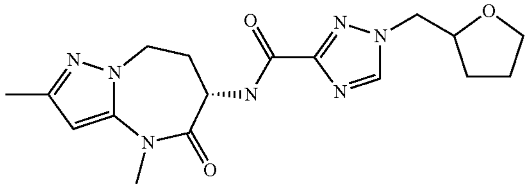 [SMILES: Cc1cc2n(n1)CC[C@H](NC(=O)c1ncn(CC3CCCO3)n1)C(=O)N2C]

N-(6S)-2,4-dimethyl-5-oxo-7,8-dihydro-6H-pyrazolo[1,5-a][1,3]diazepin-6-yl-1-(tetrahydrofuran-2-ylmethyl)-1,2,4-triazole-3-carboxamide N-Alkylation prepared in a similar fashion to WX Method 001. The crude was purified by RP-HPLC (acetonitrile 12-42%/0.05% ammonia hydroxide in water) to afford N-(6S)-2,4-dimethyl-5-oxo-7,8-dihydro-6H-pyrazolo[1,5-a][1,3]diazepin-6-yl-1-(tetrahydrofuran-2-ylmethyl)-1,2,4-triazole-3-carboxamide (68.1 mg, 35%) as a white solid. $^1H$ NMR (400 MHz, $CD_3OD$) δ 8.46 (s, 1H), 6.12 (s, 1H), 4.55-4.53 (m, 1H), 4.41-4.18 (m, 5H), 3.83 (q, J=6.8 Hz, 1H), 3.78-3.71 (m, 1H), 3.33 (s, 3H), 2.91-2.82 (m, 1H), 2.33-2.19 (m, 4H), 2.12-2.05 (m, 1H), 1.94-1.79 (m, 2H), 1.73-1.65 (m, 1H). LC-MS $R_T$=1.114 min, m/z=374.2 $[M+H]^+$.

LCMS (10 to 80% acetonitrile in water+0.03% ammonium bicarbonate over 3.0 mins) retention time 1.114 min, ESI+ found [M+H]=374.2.

Example 475

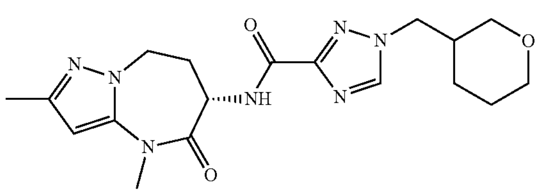 [SMILES: Cc1cc2n(n1)CC[C@H](NC(=O)c1ncn(CC3CCCOC3)n1)C(=O)N2C]

N-(6S)-2,4-dimethyl-5-oxo-7,8-dihydro-6H-pyrazolo[1,5-a][1,3]diazepin-6-yl-1-(tetrahydropyran-3-ylmethyl)-1,2,4-triazole-3-carboxamide N-Alkylation prepared in a similar fashion to WX Method 001. The crude was purified by RP-HPLC (acetonitrile 22-32%/0.05% ammonia hydroxide in water), and the partially epimerized material was further purified by chiral SFC to afford N-(6S)-2,4-dimethyl-5-oxo-7,8-dihydro-6H-pyrazolo[1,5-a][1,3]diazepin-6-yl-1-(tetrahydropyran-3-ylmethyl)-1,2,4-triazole-3-carboxamide (Peak 1, (Retention time=1.699 min) & Peak 2 (Retention time=1.883 min)) (21.2 mg, 52%) as a yellow oil. $^1H$ NMR (400 MHz, $CD_3OD$) δ8.48 (s, 1H), 6.12 (s, 1H), 4.53-4.51 (m, 1H), 4.31-4.19 (m, 4H), 3.76-3.74 (m, 2H), 3.48-3.46 (m, 1H), 3.33 (s, 3H), 3.31-3.25 (m, 1H), 2.85-2.83 (m, 1H), 2.28-2.22 (m, 5H), 1.73-1.70 (m, 2H), 1.60-1.50 (m, 1H), 1.34-1.31 (m, 1H). LC-MS $R_T$=1.176 min, m/z=388.1 $[M+H]^+$.

LCMS (10 to 80% acetonitrile in water+0.03% ammonium bicarbonate over 3.0 mins) retention time 1.176 min, ESI+ found [M+H]=388.1.

SFC condition: column: chiralcel OD-3 50×4.6 mm I.D., 3 um mobile phase: A: CO2; B: ethanol (0.05% DEA) gradient: hold 5% for 0.2 min, then from 5% to 40% of Bin 1.4 min and hold 40% for 1.05 min, then 5% of B for 0.35 min. Flow rate: 2.8 mL/min. Column temperature: 40° C.

Example 476

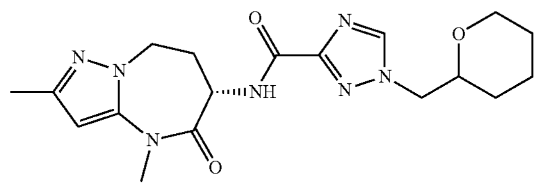 [SMILES: Cc1cc2n(n1)CC[C@H](NC(=O)c1ncn(CC3CCCCO3)n1)C(=O)N2C]

N-(6S)-2,4-dimethyl-5-oxo-7,8-dihydro-6H-pyrazolo[1,5-a][1,3]diazepin-6-yl-1-(tetrahydropyran-2-ylmethyl)-1,2,4-triazole-3-carboxamide N-Alkylation prepared in a similar fashion to WX Method 001. The crude was purified by RP-HPLC (acetonitrile 0-40%/0.05% ammonia hydroxide in water) to give N-(6S)-2,4-dimethyl-5-oxo-7,8-dihydro-6H-pyrazolo[1,5-a][1,3]diazepin-6-yl-1-(tetrahydropyran-2-ylmethyl)-1,2,4-triazole-3-carboxamide (10 mg, 5%) as white solids. $^1H$ NMR (400 MHz, $CD_3OD$) δ 8.41 (s, 1H), 6.11 (s, 1H), 4.54-4.40 (m, 1H), 4.37-4.17 (m, 4H), 3.96-3.87 (m, 1H), 3.76-3.67 (m, 1H), 3.38-3.31 (m, 4H), 2.93-2.78 (m, 1H), 2.26 (s, 4H), 1.86 (s, 1H), 1.67-1.65 (m, 1H), 1.61-1.46 (m, 3H), 1.34-1.20 (m, 1H) LC-MS $R_T$=1.298 min, m/z=388.2 $[M+H]^+$.

LCMS (10 to 80% acetonitrile in water+0.03% ammonium bicarbonate over 3.0 mins) retention time 1.298 min, ESI+ found [M+H]=388.2.

Example 477

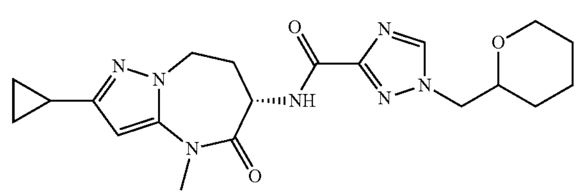 [SMILES: CN1C(=O)[C@@H](NC(=O)c2ncn(CC3CCCCO3)n2)CCn2nc(C3CC3)cc21]

N-(6S)-2-cyclopropyl-4-methyl-5-oxo-7,8-dihydro-6H-pyrazolo[1,5-a][1,3]diazepin-6-yl-1-(tetrahydro-pyran-2-ylmethyl)-1,2,4-triazole-3-carboxamide N-Alkylation prepared in a similar fashion to WX Method 001. The crude was purified by RP-HPLC (acetonitrile 0-40%/0.05% ammonia hydroxide in water) to give N-(6S)-2-cyclopropyl-4-methyl-5-oxo-7,8-dihydro-6H-pyrazolo[1,5-a][1,3]diazepin-6-yl-1-(tetrahydropyran-2-ylmethyl)-1,2,4-triazole-3-carboxamide (38 mg, 19%) as white solids. $^1H$ NMR (400 MHz, $CD_3OD$) δ 8.43 (s, 1H), 6.03 (s, 1H), 4.55-4.53 (m, 1H), 4.37-4.13 (m, 4H), 3.93-3.82 (m, 1H), 3.79-3.67 (m, 1H), 3.44-3.36 (m, 1H), 3.34 (s, 3H), 2.94-2.80 (m, 1H), 2.31-2.23 (m, 1H), 2.00-1.83 (m, 2H), 1.71-1.68 (m, 1H), 1.63-1.48 (m, 3H), 1.39-1.21 (m, 1H), 0.97-0.94 (m, 2H), 0.84-0.68 (m, 2H). LC-MS $R_T$=1.458 min, m/z=414.2 $[M+H]^+$.

LCMS (10 to 80% acetonitrile in water+0.03% ammonium bicarbonate over 3.0 mins) retention time 1.458 min, ESI+ found [M+H]=414.2.

Example 478

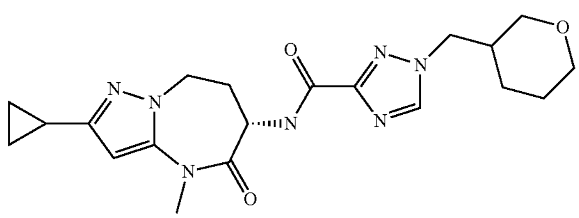 [SMILES: CN1C(=O)[C@@H](NC(=O)c2ncn(CC3CCCOC3)n2)CCn2nc(C3CC3)cc21]

N-(6S-2-cyclopropyl-4-methyl-5-oxo-7,8-dihydro-6H-pyrazolo[1,5-a][1,3]diazepin-6-yl-1-(tetrahydro-pyran-3-ylmethyl)-1,2,4-triazole-3-carboxamide N-Alkylation prepared in a similar fashion to WX Method 001. The crude was purified by RP-HPLC (acetonitrile 20-50%/0.05% ammonia hydroxide in water) to give N-(6S)-2-cyclopropyl-4-methyl-5-oxo-7,8-dihydro-6H-pyrazolo[1,5-a][1,3]diazepin-6-yl-1-(tetrahydropyran-3-ylmethyl)-1,2,4-triazole-3-carboxamide (27.4 mg, 14%) as white solids. $^1H$ NMR (400 MHz, $CD_3OD$) δ8.48 (s, 1H), 6.00 (s, 1H), 4.54-4.53 (m, 1H), 4.30-4.20 (m, 4H), 3.76-3.73 (m, 2H), 3.50-3.46 (m, 1H), 3.31 (s, 3H), 3.28-3.27 (m, 1H), 2.90-2.85 (m, 1H), 2.26-2.21 (m, 2H), 1.91-1.90 (m, 1H), 1.80-1.70 (m, 2H), 1.70-1.65 (m, 1H), 1.40-1.35 (m, 1H), 0.94-0.92 (m, 2H), 0.75-0.70 (m, 2H). LC-MS $R_T$=1.781 min, m/z=414.2 $[M+H]^+$.

LCMS (0 to 60% ammonium hydroxide in water+0.03% trifluoacetic acid over 2.0 mins) retention time 1.781 min, ESI+ found [M+H]=414.2

Example 479

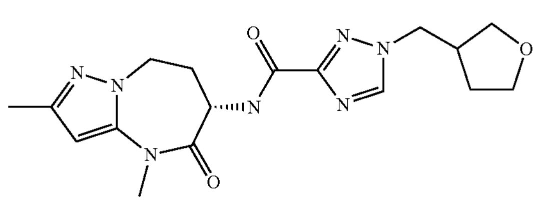 [SMILES: Cc1cc2n(n1)CC[C@H](NC(=O)c1ncn(CC3CCOC3)n1)C(=O)N2C]

N-(6S)-2,4-dimethyl-5-oxo-7,8-dihydro-6H-pyrazolo[1,5-a][1,3]diazepin-6-yl-1-(tetrahydrofuran-3-ylm-ethyl)-1,2,4-triazole-3-carboxamide N-Alkylation prepared in a similar fashion to WX Method 001. The crude was purified by RP-HPLC (acetonitrile 42-62%/0.05% ammonia hydroxide in water) to give N-(6S)-2,4-dimethyl-5-oxo-7,8-dihydro-6H-pyrazolo[1,5-a][1,3]diazepin-6-yl-1-(tetrahydrofuran-3-ylmethyl)-1,2,4-triazole-3-carboxamide (19.1 mg, 10%) as white solids. $^1H$ NMR ($CD_3OD$) δ 8.53 (s, 1H), 6.12 (s, 1H), 4.57-4.54 (m, 1H), 4.36-4.18 (m, 4H), 3.93-3.86 (m, 1H), 3.82-3.71 (m, 2H), 3.62-3.60 (m, 1H), 3.34 (s, 3H), 2.92-2.80 (m, 2H), 2.31-2.22 (m, 4H), 2.11-2.01 (m, 1H), 1.76-1.66 (m, 1H). LC-MS $R_T$=1.383 min, m/z=374.2 $[M+H]^+$.

LCMS (10 to 80% acetonitrile in water+0.03% trifluoacetic acid over 3.0 mins) retention time 1.383 min, ESI+ found [M+H]=374.2

Example 480

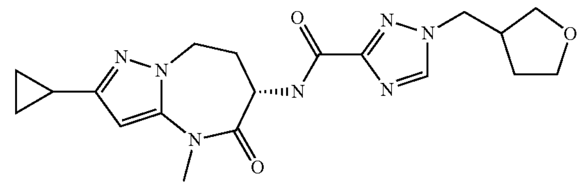 [SMILES: CN1C(=O)[C@@H](NC(=O)c2ncn(CC3CCOC3)n2)CCn2nc(C3CC3)cc21]

N-(6S)-2-cyclopropyl-4-methyl-5-oxo-7,8-dihydro-6H-pyrazolo[1,5-a][1,3]diazepin-6-yl-1-(tetrahydro-furan-3-ylmethyl)-1,2,4-triazole-3-carboxamide N-Alkylation prepared in a similar fashion to WX Method 001. The crude was purified by RP-HPLC (acetonitrile 42-62%/0.05% ammonia hydroxide in water) to give N-(6S)-2-cyclopropyl-4-methyl-5-oxo-7,8-dihydro-6H-pyrazolo[1,5-a][[1,3]diazepin-6-yl-1-(tetrahydrofuran-3-ylmethyl)-1,2,4-triazole-3-carboxamide (20.1 mg, 11%) as white solids. $^1H$ NMR (400 MHz, $CD_3OD$) δ 8.53 (s, 1H), 6.02 (s, 1H), 4.56-4.54 (m, 1H), 4.35-4.15 (m, 4H), 3.95-3.90 (m, 1H), 3.82-3.71 (m, 2H), 3.62-3.60 (m, 1H), 3.32 (s, 3H), 2.92-2.80 (m, 2H), 2.30-2.26 (m, 1H), 2.11-2.01 (m, 1H), 1.95-1.87 (m, 1H), 1.76-1.66 (m, 1H), 0.98-0.91 (m, 2H), 0.78-0.71 (m, 2H). LC-MS $R_T$=0.813 min, m/z=400.3 $[M+H]^+$.

LCMS (10 to 80% acetonitrile in water+0.03% trifluoacetic acid over 3.0 mins) retention time 0.813 min, ESI+ found [M+H]=400.3

Example 481

WX Method 164

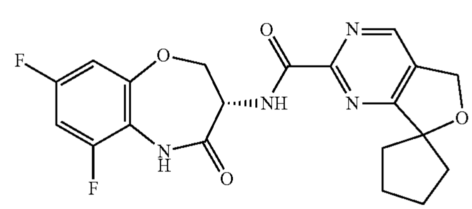 [SMILES: O=C(N[C@H]1COc2cc(F)cc(F)c2NC1=O)c1ncc2c(n1)C1(CCCC1)OC2]

N-[(3S)-6,8-difluoro-4-oxo-3,5-dihydro-2H-1,5-benzoxazepin-3-yl]spiro[5H-furo[3,4-d]p yrimidine-7,1'-cyclopentane]-2-carboxamide

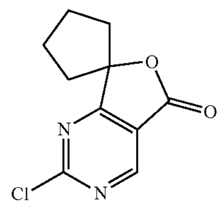 [SMILES: O=C1OC2(CCCC2)c2nc(Cl)ncc21]

Step 1: 2'-chloro-5'H-spiro[cyclopentane-1,7'-furo[3,4-d]pyrimidin]-5'-one

To a solution of 2,2,6,6-tetramethylpiperidine (26.73 g, 189.2 mmol) in tetrahydrofuran (140 mL) was added n-butyllithium (2.5 M in hexanes, 100.0 mL, 250.0 mmol) at −78° C. The reaction mixture was stirred at −78° C. for 1 h and 2-chloropyrimidine-5-carboxylic acid (10.0 g, 63.1 mmol) was added. The reaction mixture was stirred at −78° C. for another 2 h and cyclopentanone (10.61 g, 126.2 mmol) was added. After addition, the reaction mixture was stirred at 25° C. for 16 h and quenched by addition of saturated ammonium chloride (30 mL). The mixture was extracted with ethyl acetate (3×100 mL). The combined organic layers were dried over sodium sulfate and concentrated under reduced pressure. The residue was purified by flash column chromatography (silica gel, 100-200 mesh, 0 to 20% ethyl acetate in petroleum ether) to afford 2'-chloro-5'H-spiro[cyclopentane-1,7'-furo[3,4-d]pyrimidin]-5'-one (2.5 g, 18%) as white solid, used as is in the next step.

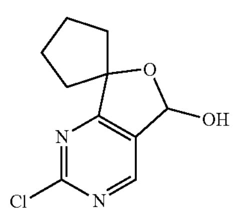 [SMILES: OC1OC2(CCCC2)c2nc(Cl)ncc21]

Step 2: 2-chlorospiro[5H-furo[3,4-d]pyrimidine-7,1'-cyclopentane]-5-ol

To a solution of 2'-chlorospiro[cyclopentane-1,7'-furo[3,4-d]pyrimidin]-5'-one (1.0 g, 4.45 mmol) in toluene (20 mL) was added diisobutylaluminumhydride (13.4 mL, 13.35 mmol, 1.0 M in toluene) at −78° C. The reaction mixture was stirred at −78° C. for 2 h and quenched by addition of saturated ammonium chloride (30 mL). The mixture was extracted with ethyl acetate (3×50 mL). The combined organic layers were washed with water (20 mL), brine (20 mL), dried over sodium sulfate and concentrated under reduced pressure to afford crude 2-chlorospiro[5H-furo[3,4-d]pyrimidine-7,1'-cyclopentane]-5-ol (800 mg, 79%) as yellow oil, used as is in the next step.

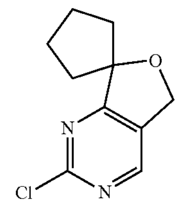 [SMILES: Clc1ncc2c(n1)C1(CCCC1)OC2]

Step 3: 2-chlorospiro[5H-furo[3,4-d]pyrimidine-7,1'-cyclopentane]

To a solution of 2-chlorospiro[5H-furo[3,4-d]pyrimidine-7,1'-cyclopentane]-5-ol (800 mg, 3.53 mmol) and trifluoroacetic acid (4.02 g, 35.30 mmol) in dichloromethane (20 mL) was added triethylsilane (4.10 g, 35.30 mmol) at 0° C. The mixture was stirred at 25° C. for 16 h and concentrated under reduced pressure. The residue was purified by column chromatography (silica gel, 100-200 mesh, 0 to 20% ethyl acetate in petroleum ether) to afford 2-chlorospiro[5H-furo[3,4-d]pyrimidine-7,1'-cyclopentane] (300 mg, 40%) as yellow oil, used as is in the next step.

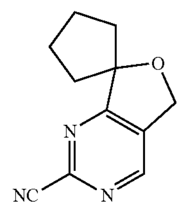 [SMILES: N#Cc1ncc2c(n1)C1(CCCC1)OC2]

Step 4: 5'H-spiro[cyclopentane-1,7'-furo[3,4-d]pyrimidin]-2'-carbonitrile

To a solution of 2-chlorospiro[5H-furo[3,4-d]pyrimidine-7,1'-cyclopentane] (300 mg, 1.42 mmol) in dimethyl sulfoxide (10 mL) and water (5 mL) was added 1,4-diazabicyclo[2.2.2]octane (174 mg, 1.55 mmol) and sodium cyanide (120 mg, 2.45 mmol). The reaction mixture was stirred at 20° C. for 16 h and extracted with ethyl acetate (3×20 mL). The combined organic layers were washed with water (20 mL), birne (20 mL), dried over sodium sulfate and concentrated under reduced pressure. The residue was purified by column chromatography (silica gel, 100-200 mesh, 0 to 20% ethyl acetate in petroleum ether) to afford 5'H-spiro[cyclopentane-1,7'-furo[3,4-d]pyrimidin]-2'-carbonitrile (250 mg, 87%) as yellow oil, used as is in the next step.

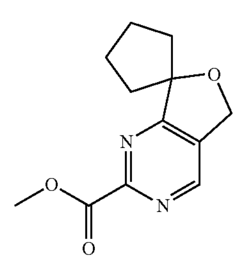 [SMILES: COC(=O)c1ncc2c(n1)C1(CCCC1)OC2]

Step 5: methyl 5'H-spiro[cyclopentane-1,7'-furo[3,4-d]pyrimidine]-2'-carboxylate To a solution of 5'H-spiro[cyclopentane-1,7'-furo[3,4-d]pyrimidine]-2'-carbonitrile (250 mg, 1.24 mmol) in methanol (3 mL) was added HCl (4N in methanol, 1.6 mL). The reaction mixture was heated to 70° C. for 2 h and concentrated under reduced pressure to afford crude methyl 5'H-spiro[cyclopentane-1,7'-furo[3,4-d]pyrimidine]-2'-carboxylate (200 mg, 69%) as yellow oil, used as is in the next step.

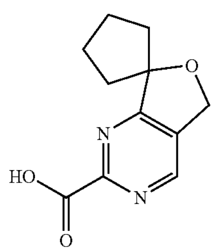 [SMILES: O=C(O)c1ncc2c(n1)C1(CCCC1)OC2]

Step 6: 5'H-spiro[cyclopentane-1,7'-furo[3,4-d]pyrimidine]-2'-carboxylic acid

A mixture of methyl 5'H-spiro[cyclopentane-1,7'-furo[3,4-d]pyrimidine]-2'-carboxylate (200 mg, 0.85 mmol) and lithium hydroxide hydrate (358 mg, 8.54 mmol) in tetrahydrofuran (10 mL) and water (10 mL) was stirred at 20° C. for 2 h. The mixture was quenched by addition of 1N HCl (3 mL) and extracted with ethyl acetate (3×20 mL). The combined organic layers were dried over sodium sulfate and concentrated under reduced pressure to afford crude 5'H-spiro[cyclopentane-1,7'-furo[3,4-d]pyrimidine]-2'-carboxylic acid (120 mg, 64%) as yellow oil, used as is in the next step.

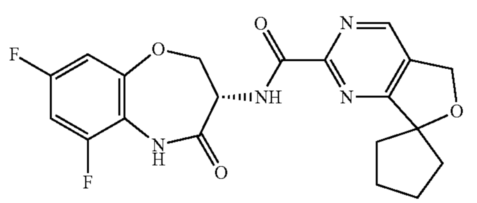 [SMILES: O=C(N[C@H]1COc2cc(F)cc(F)c2NC1=O)c1ncc2c(n1)C1(CCCC1)OC2]

Step 7: N-[(3S)-6,8-difluoro-4-oxo-3,5-dihydro-2H-1,5-benzoxazepin-3-yl]spiro[5H-furo[3,4-d]pyrimidine-7,1'-cyclopentane]-2-carboxamide A mixture of (3S)-3-amino-6,8-difluoro-3,5-dihydro-2H-1,5-benzoxazepin-4-one (30 mg, 0.14 mmol), 5'H-spiro[cyclopentane-1,7'-furo[3,4-d]pyrimidine]-2'-carboxylic acid (36 mg, 0.16 mmol), 1H-benzo[d][1,2,3]triazol-1-ol (25 mg, 0.19 mmol) and $N^1$-((ethylimino)methylene)-$N^3$,$N^3$-dimethylpropane-1,3-diamine hydrochloride (40 mg, 0.21 mmol) in N,N-dimethylformamide (3 mL) was stirred at 25° C. for 16 h. The mixture was concentrated under reduced pressure and the residue was purified by RP-HPLC (acetonitrile 40% to 70%/0.05% ammonium hydroxide in water) to afford N-[(3S)-6,8-difluoro-4-oxo-3,5-dihydro-2H-1,5-benzoxazepin-3-yl]spiro[5H-furo[3,4-d]pyrimidine-7,1'-cyclopentane]-2-carboxamide (19.5 mg, 33%) as a white solid. $^1$H NMR (400 MHz, $CD_3OD$) δ8.80 (s, 1H), 6.97-6.87 (m, 2H), 5.12-5.09 (m, 3H), 4.78-4.73 (m, 1H), 4.57-4.51 (m, 1H), 2.14-2.00 (m, 4H), 1.98-1.87 (m, 4H). LCMS $R_T$=0.718 min, m/z=416.9 [M+H]$^+$.

LCMS (5 to 95% acetonitrile in water+0.05% ammonium hydroxide over 1.5 mins) retention time 0.718 min, ESI+ found [M+H]=416.9.

Example 482

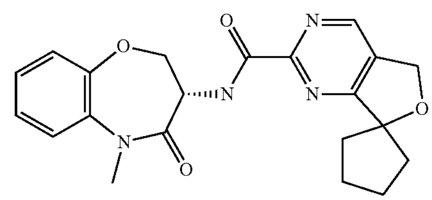 [SMILES: CN1C(=O)[C@@H](NC(=O)c2ncc3c(n2)C2(CCCC2)OC3)COc2ccccc21]

N-[(6S)-4-methyl-5-oxo-7,8-dihydro-6H-pyrazolo[1,5-a][1,3]diazepin-6-yl]spiro[5H-furo[3,4-d]pyrimidine-7,1'-cyclopentane]-2-carboxamide Amide coupling prepared in a similar fashion to WX Method 164. The crude was purified by RP-HPLC (35% to 65% acetonitrile/0.05% ammonia hydroxide in water) to give N-[(6S)-4-methyl-5-oxo-7,8-dihydro-6H-pyrazolo[1,5-a][1,3]diazepin-6-yl]spiro[5H-furo[3,4-d]pyrimidine-7,1'-cyclopentane]-2-carboxamide (25 mg, 55%) as a white solid. $^1$H NMR (400 MHz, $CD_3OD$) δ8.80 (s, 1H), 7.46-7.44 (m, 1H), 7.34-7.32 (m, 2H), 7.27-7.24 (m, 1H), 5.12 (s, 2H), 5.07-5.02 (m, 1H), 4.69-4.68 (m, 1H), 4.46-4.43 (m, 1H), 3.44 (s, 3H), 2.08-2.04 (m, 4H), 1.95-1.93 (m, 4H). LC-MS $R_T$=2.21 min, m/z=395.2 [M+H]$^+$.

LCMS (0 to 60% acetonitrile in water+0.05% ammonium hydroxide over 3 mins) retention time 2.21 min, ESI+ found [M+H]=395.2.

Example 483

WX Method 011

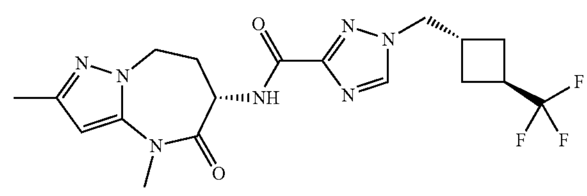 [SMILES: Cc1cc2n(n1)CC[C@H](NC(=O)c1ncn(C[C@H]3C[C@H](C(F)(F)F)C3)n1)C(=O)N2C]

N—(S)-2,4-dimethyl-5-oxo-7,8-dihydro-6H-pyrazolo[1,5-a][1,3]diazepin-6-yl]-1-(((1R,3S)-3-trifluoromethylcyclobutyl)methyl)-1H-1,2,4-triazole-3-carboxamide

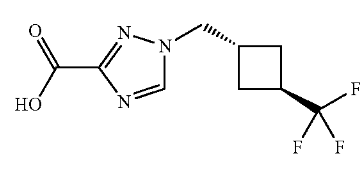 [SMILES: O=C(O)c1ncn(C[C@H]2C[C@H](C(F)(F)F)C2)n1]

Step 1: 1-(((1R,3R)-3-(trifluoromethyl)cyclobutyl) methyl)-1H-1,2,4-triazole-3-carboxylic acid A mixture of methyl 1-(((1R,3R)-3-(trifluoromethyl)cyclobutyl)methyl)-1H-1,2,4-triazole-3-carboxylate (140 mg, 0.53 mmol) and lithium hydroxide hydrate (112 mg, 2.66 mmol) in tetrahydrofuran/methanol/water (5 mL, 2:2:1) was stirred at 25° C. for 1 h. The solution was diluted with water (10 mL) and adjusted to pH=4-5 with addition of 1M HCl. The resulting solid was collected by filtration and dried under reduced pressure to give crude 1-(((1R,3R)-3-(trifluoromethyl)cyclobutyl)methyl)-1H-1,2,4-triazole-3-carboxylic acid (100 mg, 76%) as a white solids, used as is in the next step.

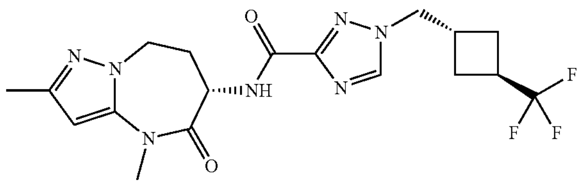 [SMILES: Cc1cc2n(n1)CC[C@H](NC(=O)c1ncn(C[C@H]3C[C@H](C(F)(F)F)C3)n1)C(=O)N2C]

Step 2: N—(S)-2,4-dimethyl-5-oxo-7,8-dihydro-6H-pyrazolo[1,5-a][1,3]diazepin-6-yl]-1-(((1R,3S)-3-trifluoromethylcyclobutyl)methyl)-1H-H-1,2,4-triazole-3-carboxamide A mixture of 1-(((1R,3R)-3-(trifluoromethyl)cyclobutyl) methyl)-1H-1,2,4-triazole-3-carboxylic acid (31 mg, 0.12 mmol), 1-hydroxybenzotriazole (25 mg, 0.19 mmol), 1-(3-dimethylaminopropyl)-3-ethylcarbodiimidehydrochloride (36 mg, 0.19 mmol) and (6S)-6-amino-2,4-dimethyl-7,8-dihydro-6H-pyrazolo[1,5-a][1,3]diazepin-5-one (24 mg, 0.12 mmol) in N,N-dimethylformamide (5 mL) was stirred at 20° C. for 12 h. The solvent was evaporated under reduced pressure and the residue was purified by RP-HPLC (acetonitrile 46-76%/0.05% ammonium hydroxide in water) to afford N—(S)-2,4-dimethyl-5-oxo-7,8-dihydro-6H-pyrazolo[1,5-a][1,3]diazepin-6-yl]-1-(((1R,3 S)-3-trifluoromethylcyclobutyl)methyl)-1H-1,2,4-triazole-3-carboxamide (20.5 mg, 40%) as white solids. $^{1}$H NMR (400 MHz, $CD_3OD$) δ8.51 (s, 1H), 6.12 (s, 1H), 4.57-4.52 (m, 1H), 4.40-4.22 (m, 4H), 3.34 (s, 3H), 2.96-2.83 (m, 3H), 2.30-2.27 (m, 6H), 2.18-2.12 (m, 2H). LC-MS $R_T$=0.940 min, m/z=426.3 $(M+H)^+$.

LCMS (10 to 80% acetonitrile in water+0.03% trifluoacetic acid over 2.0 mins) retention time 0.940 min, ESI+ found [M+H]=426.3.

Example 484

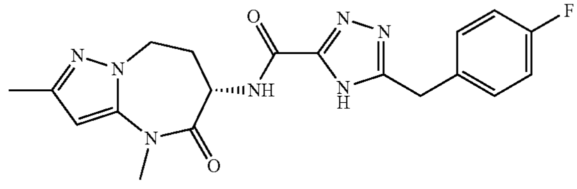 [SMILES: Cc1cc2n(n1)CC[C@H](NC(=O)c1nnc(Cc3ccc(F)cc3)[nH]1)C(=O)N2C]

5-[(4-fluorophenyl)methyl]-N-(6S)-2,4-dimethyl-5-oxo-7,8-dihydro-6H-pyrazolo[1,5-a][1,3]diazepin-6-yl-4H-1,2,4-triazole-3-carboxamide Amide coupling prepared in a similar fashion to WX Method 011. The crude was purified by RP-HPLC (acetonitrile 12-42%/0.05% ammonia hydroxide in water) to afford 5-[(4-fluorophenyl)methyl]-N-(6S)-2,4-dimethyl-5-oxo-7,8-dihydro-6H-pyrazolo[1,5-a][1,3]diazepin-6-yl-4H-1,2,4-triazole-3-carboxamide (10.54 mg, 9%) as a white solid. $^{1}$H NMR (400 MHz, $CD_3OD$) δ7.28 (dd, J=5.2, 8.0 Hz, 2H), 7.02 (t, J=8.8 Hz, 2H), 6.09 (s, 1H), 4.48-4.53 (m, 1H), 4.19-4.34 (m, 2H), 4.05-4.17 (m, 2H), 3.16-3.28 (m, 3H), 2.77-2.85 (m, 1H), 2.14-2.28 (m, 4H). LC-MS $R_T$=0.733 min, m/z=398.1 (M+H).

LCMS (5 to 95% acetonitrile in water+0.03% trifluoacetic acid over 1.5 mins) retention time 0.733 min, ESI+ found [M+H]=398.1.

Example 485

WX Method 147

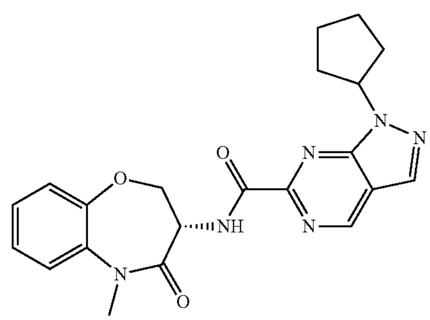 [SMILES: CN1C(=O)[C@@H](NC(=O)c2ncc3cnn(C4CCCC4)c3n2)COc2ccccc21]

1-cyclopentyl-N-[(3S)-5-methyl-4-oxo-2,3-dihydro-1,5-benzoxazepin-3-yl]pyrazolo[3,4-d]pyrimidine-6-carboxamide

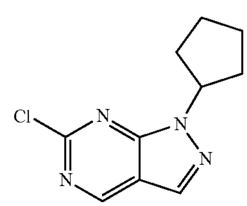 [SMILES: Clc1ncc2cnn(C3CCCC3)c2n1]

Step 1: 6-chloro-1-cyclopentyl-1H-pyrazolo[3,4-d] pyrimidine

A mixture of 6-chloro-1H-pyrazolo[3,4-d]pyrimidine (500 mg, 3.23 mmol), potassium carbonate (894 mg, 6.47 mmol) and cyclopentyl bromide (506 mg, 3.4 mmol) in N,N-dimethylformamide (10 mL) was stirred at 80° C. for 5 h and filtered. The filtrate was concentrated under reduced pressure and the residue was purified by column chromatography (silica gel, 100-200 mesh, 0 to 15% ethyl acetate in petroleum ether) to give 6-chloro-1-cyclopentyl-1H-pyrazolo[3,4-d]pyrimidine (350 mg, 47%) as a colorless oil. LCMS $R_T$=1.064 min; m/z=223.1 $(M+H)^+$.

LCMS (10 to 80% acetonitrile in water+0.03% trifluoacetic acid over 2.0 mins) retention time 1.064 min, ESI+ found [M+H]=223.1.

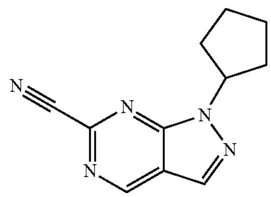 [SMILES: N#Cc1ncc2cnn(C3CCCC3)c2n1]

Step 2: 1-cyclopentyl-1H-pyrazolo[3,4-d]pyrimidine-6-carbonitrile

To a solution of 6-chloro-1-cyclopentyl-1H-pyrazolo[3,4-d]pyrimidine (300 mg, 1.35 mmol) in dimethyl sulfoxide (10 mL) were added 1,4-diazabicyclo[2.2.2]octane (15 mg, 0.13 mmol) and sodium cyanide (132 mg, 2.69 mmol) in water (1 mL). The mixture was stirred at 25° C. for 16 h and diluted with water (20 mL). The mixture was extracted with ethyl acetate (3×25 mL). The combined organic layers were dried over sodium sulfate and concentrated under reduced pressure. The residue was purified by preparative thin-layer chromatography (25% ethyl acetate in petroleum ether) to afford 1-cyclopentyl-1H-pyrazolo[3,4-d]pyrimidine-6-carbonitrile (80 mg, 28%) as a yellow solid. LCMS $R_T$=1.064 min; m/z=214.1 $(M+H)^+$.

LCMS (10 to 80% acetonitrile in water+0.03% trifluoacetic acid over 2.0 mins) retention time 1.064 min, ESI+ found [M+H]=214.1.

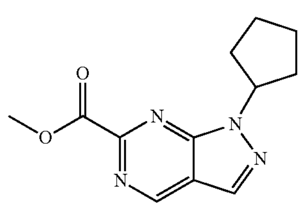 [SMILES: COC(=O)c1ncc2cnn(C3CCCC3)c2n1]

Step 3: methyl 1-cyclopentyl-1H-pyrazolo[3,4-d]pyrimidine-6-carboxylate

A solution of 1-cyclopentyl-1H-pyrazolo[3,4-d]pyrimidine-6-carbonitrile (80 mg, 0.38 mmol) in methanol (5 mL) was added HCl (4N in methanol, 1.5 mL). The mixture was stirred at 20° C. for 20 h and 50° C. for 3 h. The reaction solution was concentrated under reduced pressure to give crude methyl 1-cyclopentyl-1H-pyrazolo[3,4-d]pyrimidine-6-carboxylate (90 mg, 97%) as a yellow solid, used as is in the next step. LCMS $R_T$=0.928 min; m/z=247.1 $(M+H)^+$.

LCMS (10 to 80% acetonitrile in water+0.03% trifluoacetic acid over 2.0 mins) retention time 0.928 min, ESI+ found [M+H]=247.1.

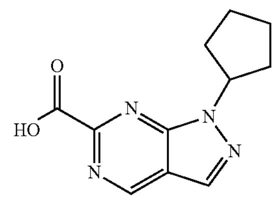 [SMILES: O=C(O)c1ncc2cnn(C3CCCC3)c2n1]

Step 4: 1-cyclopentyl-1H-pyrazolo[3,4-d]pyrimidine-6-carboxylic acid

A mixture of methyl 1-cyclopentyl-1H-pyrazolo[3,4-d]pyrimidine-6-carboxylate (30 mg, 0.12 mmol) and lithium hydroxide hydrate (26 mg, 0.61 mmol) in tetrahydrofuran (5 mL) and water (1 mL) was stirred at 25° C. for 2 h. The organic solvent was removed under reduced pressure and the aqueous phase was adjusted to pH=4 by addition of 1N HCl. The mixture was extracted with ethyl acetate (3×20 mL). The combined organic layers were dried over magnesium sulfate and concentrated under reduced pressure to give crude 1-cyclopentyl-1H-pyrazolo[3,4-d]pyrimidine-6-carboxylic acid (25 mg, 88%) as a yellow solid. LCMS $R_T$=0.978 min; m/z=233.1 $(M+H)^+$.

LCMS (0 to 60% acetonitrile in water+0.03% trifluoacetic acid over 2.0 mins) retention time 0.978 min, ESI+ found [M+H]=233.1.

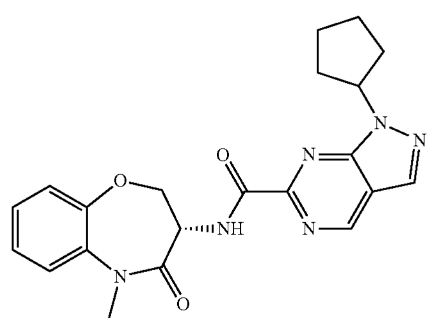 [SMILES: CN1C(=O)[C@@H](NC(=O)c2ncc3cnn(C4CCCC4)c3n2)COc2ccccc21]

Step 5: 1-cyclopentyl-N-[(3S)-5-methyl-4-oxo-2,3-dihydro-1,5-benzoxazepin-3-yl]pyrazolo[3,4-d]pyrimidine-6-carboxamide A mixture of (3S)-3-amino-5-methyl-2,3-dihydro-1,5-benzoxazepin-4-one (23 mg, 0.12 mmol), 1-cyclopentylpyrazolo[3,4-d]pyrimidine-6-carboxylic acid (25 mg, 0.11 mmol), $N^1$-((ethylimino)methylene)-$N^3$,$N^3$-dimethyl-propane-1,3-diamine hydrochloride (25 mg, 0.13 mmol), 1H-benzo[d][1,2,3]triazol-1-ol (17 mg, 0.13 mmol) in N,N-dimethylformamide (4 mL) was stirred at 25° C. for 16 h. The mixture was concentrated under reduced pressure and the residue was purified by RP-HPLC (acetonitrile 35% to 65%/0.05% ammonia hydroxide in water) to give 1-cyclopentyl-N-[(3S)-5-methyl-4-oxo-2,3-dihydro-1,5-benzoxazepin-3-yl]pyrazolo[3,4-d]pyrimidine-6-carboxamide (26.8 mg, 61%) as a white solid. $^1H$ NMR (400 MHz, DMSO-$d_6$) δ9.46 (s, 1H), 9.13 (d, J=8.0 Hz, 1H), 8.51 (s, 1H), 7.54-7.51 (m, 1H), 7.35-7.27 (m, 3H), 5.47-5.41 (m, 1H), 4.93-4.88 (m, 1H), 4.61-4.52 (m, 2H), 3.35 (s, 3H), 2.17-2.14 (m, 2H), 2.00-1.91 (m, 4H), 1.74-1.71 (m, 2H). LCMS $R_T$=0.836 min; m/z=407.1 $(M+H)^+$.

LCMS (5-95% acetonitrile in water+0.05% trifluoacetic acid over 1.5 mins) retention time 0.836 min, ESI+ found [M+H]=407.1.

Example 486

WX Method 153

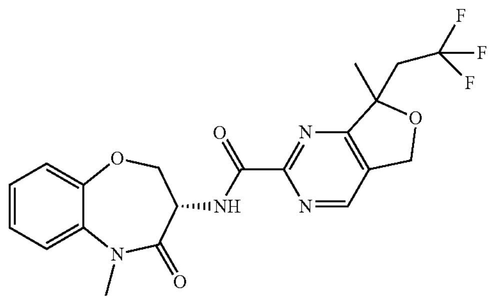 [SMILES: CN1C(=O)[C@@H](NC(=O)c2ncc3c(n2)C(C)(CC(F)(F)F)OC3)COc2ccccc21]

7-methyl-N-[(3S)-5-methyl-4-oxo-2,3-dihydro-1,5-benzoxazepin-3-yl]-7-(2,2,2-trifluoroethyl)-5H-furo[3,4-d]pyrimidine-2-carboxamide

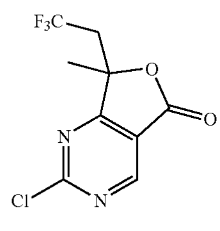 [SMILES: CC1(CC(F)(F)F)OC(=O)c2cnc(Cl)nc21]

Step 1: 2-chloro-7-methyl-7-(2,2,2-trifluoroethyl)furo[3,4-d]pyrimidin-5(7H)-one To a solution of 2,2,6,6-tetramethylpiperidine (13.5 g, 95.6 mmol) in tetrahydrofuran (300 mL) was added n-butyllithium (2.5 M in hexanes, 50.0 mL, 125.0 mmol) at −78° C. The reaction mixture was stirred at −78° C. for 1 h and 2-chloropyrimidine-5-carboxylic acid (5.0 g, 31.7 mmol) was added. The reaction mixture was stirred at −78° C. for another 2 h and 4,4,4-trifluorobutan-2-one (4.0 g, 31.74 mmol) was added. After addition, the reaction mixture was stirred at 25° C. for 16 h and quenched by addition of saturated ammonium chloride (50 mL). The mixture was extracted with ethyl acetate (3×50 mL). The combined organic layers were dried over sodium sulfate and concentrated under reduced pressure. The residue was purified by column chromatography (silica gel, 100-200 mesh, 0 to 50% ethyl acetate in petroleum ether) to afford 2-chloro-7-methyl-7-(2,2,2-trifluoroethyl)furo[3,4-d]pyrimidin-5(7H)-one (1.0 g, 12%) as yellow oil, used as is in the next step.

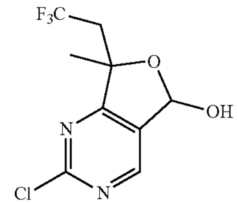 [SMILES: CC1(CC(F)(F)F)OC(O)c2cnc(Cl)nc21]

Step 2: 2-chloro-7-methyl-7-(2,2,2-trifluoroethyl)-5,7-dihydrofuro[3,4-d]pyrimidin-5-ol To a solution of 6-chloro-1-methyl-1-(2,2,2-trifluoroethyl)furo[3,4-c]pyridin-3(1H)-one (1.0 g, 3.75 mmol) in dry toluene (15 mL) was added diisobutylaluminum hydride (7.5 mL, 7.50 mmol, 1.0 M in toluene) at −70° C. The resulting solution was stirred at −70° C. for 2 h and quenched by addition of saturated ammonium chloride (10 mL). The mixture was filtered and the filtrate was extracted with ethyl acetate (3×20 mL). The combined organic layers were w dried over sodium sulfate and concentrated under reduced pressure. The residue was purified by column chromatography (silica gel, 100-200 mesh, 0 to 30% ethyl acetate in petroleum ether) to afford 2-chloro-7-methyl-7-(2,2,2-trifluoroethyl)-5,7-dihydrofuro[3,4-d]pyrimidin-5-ol (450 mg, 45%) as yellow oil, used as is in the next step.

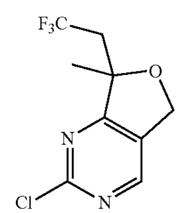 [SMILES: CC1(CC(F)(F)F)OCc2cnc(Cl)nc21]

Step 3: 2-chloro-7-methyl-7-(2,2,2-trifluoroethyl)-5,7-dihydrofuro[3,4-d]pyrimidine To a solution of 2-chloro-7-methyl-7-(2,2,2-trifluoroethyl)-5,7-dihydrofuro [3,4-d]pyrimidin-5-ol (450 mg, 1.68 mmol) in dichloromethane (25 mL) was added trifluoroacetic acid (1.91 g, 16.75 mmol) at 0° C. The mixture was stirred at 0° C. for 30 min, and triethyl silane (974 mg, 8.38 mmol) was added. After addition, the mixture was stirred for 3 hours at 25° C. and quenched by addition of saturated sodium bicarbonate solution (20 mL). The resulting mixture was extracted with dichloromethane (3×20 mL). The combined organic layers were dried over sodium sulfate and concentrated under reduced pressure. The residue was purified by column chromatography (silica gel, 100-200 mesh, 0 to 15% ethyl acetate in petroleum ether) to afford 2-chloro-7-methyl-7-(2,2,2-trifluoroethyl)-5,7-dihydrofuro[3,4-d]pyrimidine (350 mg, 83%) as yellow oil, used as is in the next step.

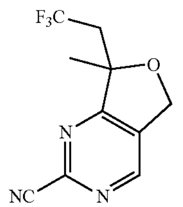 [SMILES: CC1(CC(F)(F)F)OCc2cnc(C#N)nc21]

Step 4: 7-methyl-7-(2,2,2-trifluoroethyl)-5H-furo[3,4-d]pyrimidine-2-carbonitrile To a solution of 2-chloro-7-methyl-7-(2,2,2-trifluoroethyl)-5H-furo[3,4-d]pyrimidine (350 mg, 1.39 mmol) in dimethyl sulfoxide (6 mL) and water (3 mL) was added 1,4-diazabicyclo[2.2.2]octane (155 mg, 1.39 mmol) and sodium cyanide (160 mg, 3.26 mmol). The reaction mixture was stirred at 25° C. for 3 h and extracted with ethyl acetate (3×30 mL). The combined organic layers were washed with water (10 mL), brine (10 mL), dried over sodium sulfate and concentrated under reduced pressure. The residue was purified by column chromatography (silica gel, 100-200 mesh, 0 to 20% ethyl acetate in petroleum ether) to afford 7-methyl-7-(2,2,2-trifluoroethyl)-5H-furo[3,4-d]pyrimidine-2-carbonitrile (130 mg, 39%) as yellow oil, used as is in the next step.

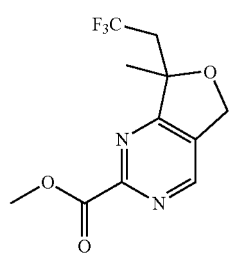 [SMILES: COC(=O)c1ncc2c(n1)C(C)(CC(F)(F)F)OC2]

Step 5: methyl 7-methyl-7-(2,2,2-trifluoroethyl)-5H-furo[3,4-d]pyrimidine-2-carboxylate To a solution of 7-methyl-7-(2,2,2-trifluoroethyl)-5H-furo[3,4-d]pyrimidine-2-carbonitrile (130 mg, 0.53 mmol) in methanol (5 mL) was added HCl (4N in methanol, 5 mL). The reaction mixture was stirred at 25° C. for 16 h and concentrated under reduced pressure to afford crude methyl 7-methyl-7-(2,2,2-trifluoroethyl)-5H-furo[3,4-d]pyrimidine-2-carboxylate (120 mg, 81%) as a white solid, used as is in the next step.

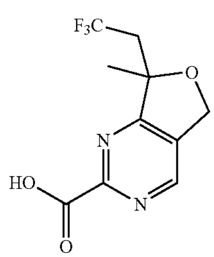 [SMILES: CC1(CC(F)(F)F)OCc2cnc(C(=O)O)nc21]

Step 6: 7-methyl-7-(2,2,2-trifluoroethyl)-5H-furo[3,4-d]pyrimidine-2-carboxylic acid A mixture of methyl 7-methyl-7-(2,2,2-trifluoroethyl)-5H-furo[3,4-d]5 pyrimidine-2-carboxylate (120 mg, 0.43 mmol) and lithium hydroxide hydrate (182 mg, 4.34 mmol) in tetrahydrofuran (5 mL) and water (5 mL) was stirred at 25° C. for 1 h. The organic solvent was evaporated under reduced pressure and the aqueous phase was adjusted to pH=5 by addition of 1N HCl. The mixture was extracted with ethyl acetate (2×20 mL). The combined organic layers were dried as washed with water and brine, dried over sodium sulfate and concentrated under reduced pressure to afford crude 7-methyl-7-(2,2,2-trifluoroethyl)-5H-furo[3,4-d]pyrimidine-2-carboxylic acid (90 mg, 79%) as yellow oil, used as is in the next step.

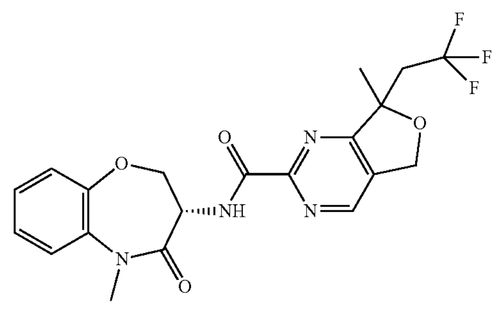 [SMILES: CN1C(=O)[C@@H](NC(=O)c2ncc3c(n2)C(C)(CC(F)(F)F)OC3)COc2ccccc21]

Step 7: 7-methyl-N-[(3S)-5-methyl-4-oxo-2,3-dihydro-1,5-benzoxazepin-3-yl]-7-(2,2,2-trifluoroethyl)-5H-furo[3,4-d]pyrimidine-2-carboxamide A mixture of (3S)-3-amino-5-methyl-2,3-dihydro-1,5-benzoxazepin-4-one (20 mg, 0.10 mmol), 7-methyl-7-(2,2,2-trifluoroethyl)-5H-furo[3,4-d]pyrimidine-2-carboxylic acid (27 mg, 0.10 mmol), 1H-benzo[d][1,2,3]triazol-1-ol (14 mg, 0.10 mmol) and $N^1$-((ethylimino)methylene)-$N^3$,$N^3$-dimethylpropane-1,3-diamine hydrochloride (20 mg, 0.10 mmol) in N,N-dimethylformamide (3 mL) was stirred at 25° C. for 16 h. The mixture was concentrated under reduced pressure and the residue was purified by RP-HPLC (acetonitrile 28% to 58%/0.05% hydrochloric acid in water) to afford 7-methyl-N-[(3S)-5-methyl-4-oxo-2,3-dihydro-1,5-benzoxazepin-3-yl]-7-(2,2,2-trifluoroethyl)-5H-furo[3,4-d]pyrimidine-2-carboxamide (19.4 mg, 42%) as a white solid. $^1H$ NMR (400 MHz, $CD_3OD$) δ 8.88 (s, 1H), 7.45-7.24 (m, 4H), 5.25-5.21 (m, 2H), 5.08-5.02 (m, 1H), 4.69-4.65 (m, 1H), 4.48-4.43 (m, 1H), 3.43 (s, 3H), 2.97-2.85 (m, 2H), 1.57 (s, 3H). LCMS $R_T$=0.806 min, m/z=437.1 $[M+H]^+$.

LCMS (5 to 95% acetonitrile in water+0.03% trifluoacetic acid over 1.5 mins) retention time 0.806 min, ESI+ found [M+H]=437.1.

Example 487

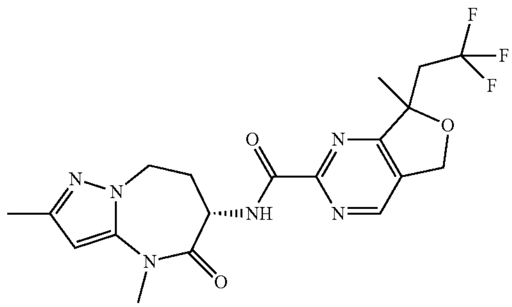 [SMILES: Cc1cc2n(n1)CC[C@H](NC(=O)c1ncc3c(n1)C(C)(CC(F)(F)F)OC3)C(=O)N2C]

7-methyl-N-[(6S)-2,4-dimethyl-5-oxo-7,8-dihydro-6H-pyrazolo[1,5-a][1,3]diazepin-6-yl]-7-(2,2,2-trifluoroethyl)-5H-furo[3,4-d]pyrimidine-2-carboxamide Amide coupling prepared in a similar fashion to WX Method 153. The crude was purified by RP-HPLC (acetonitrile 25% to 55%/0.05% ammonium hydroxide in water) to give 7-methyl-N-[(6S)-2,4-dimethyl-5-oxo-7,8-dihydro-6H-pyrazolo[1,5-a][1,3]diazepin-6-yl]-7-(2,2,2-trifluoroethyl)-5H-furo[3,4-d]pyrimidine-2-carboxamide (22.2 mg, 49%) as a white solid. $^1$H NMR (400 MHz, $CD_3OD$) δ8.50 (s, 1H), 6.12 (s, 1H), 4.57-4.52 (m, 1H), 4.31-4.22 (m, 4H), 3.33 (s, 3H), 3.01-2.83 (m, 3H), 2.28-2.24 (m, 6H), 2.01-1.98 (m, 2H). LCMS $R_T$=0.682 min, m/z=439.2 $[M+H]^+$.

LCMS (5 to 95% acetonitrile in water+0.03% trifluoacetic acid over 1.5 mins) retention time 0.682 min, ESI+ found [M+H]=439.2.

Example 488

WX Method 176

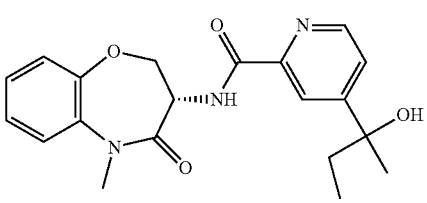 [SMILES: CCC(C)(O)c1ccnc(C(=O)N[C@H]2COc3ccccc3N(C)C2=O)c1]

4-(1-hydroxy-1-methyl-propyl)-N-[(3S)-5-methyl-4-oxo-2,3-dihydro-1,5-benzoxazepin-3-yl]pyridine-2-carboxamide

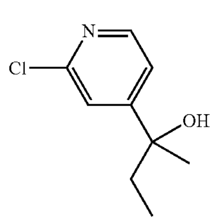

Step 1: 2-(2-chloropyridin-4-yl)butan-2-ol

To a solution of 4-bromo-2-chloropyridine (5.0 g, 26.0 mmol) in tetrahydrofuran (100 mL) was added n-butyllithium (2.5 M in hexanes, 13.5 mL, 33.8 mmol) dropwise at −78° C. The mixture was stirred at −78° C. for 2 h and methyl ethyl ketone (2.81 g, 39.0 mmol) was added dropwise. The resulting mixture was allowed to warm to 25° C. over 15 h and quenched by addition of saturated ammonium chloride. The mixture was extracted with ethyl acetate (3×50 mL). The combined organic layers were dried over sodium sulfate and concentrated under reduced pressure. The residue was purified by column chromatography (silica gel, 100-200 mesh, 0 to 20% ethyl acetate in petroleum ether) to afford 2-(2-chloropyridin-4-yl)butan-2-ol (500 mg, 10%) as colorless oil. LCMS $R_T$=0.584 min; m/z=185.8 $(M+H)^+$.

LCMS (5 to 95% acetonitrile in water+0.03% trifluoacetic acid over 1.5 mins) retention time 0.584 min, ESI+ found [M+H]=185.8.

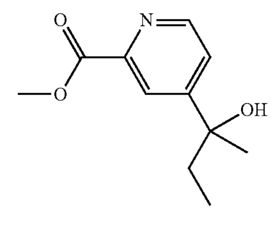

Step 2: methyl 4-(2-hydroxybutan-2-yl)picolinate

A mixture of 2-(2-chloropyridin-4-yl)butan-2-ol (200 mg, 1.1 mmol), triethylamine (327 mg, 3.2 mmol) and 1,1'-bis(diphenylphosphino)ferrocene palladium dichloride) (79 mg, 0.1 mmol) in methanol (50 mL) was heated at 70° C. for 15 h under CO (35 psi) and filtered. The filtrate was concentrated under reduce pressure and the residue was purified by column chromatography (silica gel, 100-200 mesh, 0 to 50% ethyl acetate in petroleum ether) to give methyl 4-(2-hydroxybutan-2-yl)picolinate (100 mg, 44%) as light yellow oil.

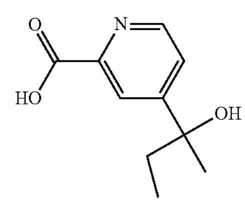

Step 3: 4-(2-hydroxybutan-2-yl)picolinic acid

A mixture of 4-(2-hydroxybutan-2-yl)picolinate (100 mg, 0.48 mmol) and potassium hydroxide (54 mg, 0.96 mmol) in ethanol (5 mL) and water (1 mL) was stirred at 25° C. for 12 h. The solvent was removed under reduced pressure and the residue was diluted with water (10 mL). The solution was adjusted to pH=4 by addition of 2N HCl. The mixture was concentrated under reduced pressure to afford crude 4-(2-hydroxybutan-2-yl)picolinic acid (80 mg, 72%) as a yellow solid, used as is in the next step.

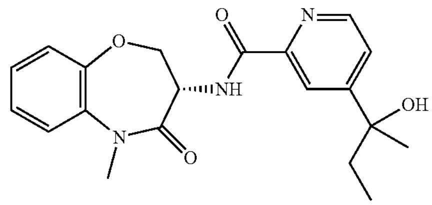 [SMILES: CCC(C)(O)c1ccnc(C(=O)N[C@H]2COc3ccccc3N(C)C2=O)c1]

Step 4: 4-(1-hydroxy-1-methyl-propyl)-N-[(3S)-5-methyl-4-oxo-2,3-dihydro-1,5-benzoxazepin-3-yl]pyridine-2-carboxamide A mixture of (3S)-3-amino-5-methyl-2,3-dihydro-1,5-benzoxazepin-4-one (51 mg, 0.26 mmol), 4-(1-hydroxy-1-methyl-propyl)pyridine-2-carboxylic acid (77 mg, 0.39 mmol), 1H-benzo[d][1,2,3]triazol-1-ol (53 mg, 0.39 mmol) and $N^1$-((ethylimino)methylene)-$N^3$,$N^3$-dimethylpropane-1,3-diamine hydrochloride (76 mg, 0.39 mmol) in N,N-dimethylformamide (5 mL) was stirred at 25° C. for 16 h. The mixture was concentrated under reduced pressure and the residue was purified by RP-HPLC (acetonitrile 28% to 58%/0.05% ammonia hydroxide in water) to give 4-(1-hydroxy-1-methyl-propyl)-N-[(3S)-5-methyl-4-oxo-2,3-dihydro-1,5-benzoxazepin-3-yl]pyridine-2-carboxamide (7.0 mg, 7.2%) as a white solid. $^1$H NMR (400 MHz, $CD_3OD$) δ 8.59 (d, J=4.8 Hz, 1H), 8.11 (s, 1H), 7.65-7.61 (m, 1H), 7.46-7.41 (m, 1H), 7.36-7.29 (m, 2H), 7.27-7.22 (m, 1H), 5.06-4.99 (m, 1H), 4.68-4.62 (m, 1H), 4.59 (s, 1H), 4.44-4.37 (m, 1H), 3.43 (s, 3H), 1.85-1.77 (m, 2H), 1.50 (s, 3H), 0.76 (t, J=4.0 Hz, 3H). LCMS $R_T$=1.00 min; m/z=370.2 $(M+H)^+$.

LCMS (10 to 80% acetonitrile in water+0.03% trifluoacetic acid over 2.0 mins) retention time 1.00 min, ESI+ found [M+H]=370.2

Example 489

WX Method 158

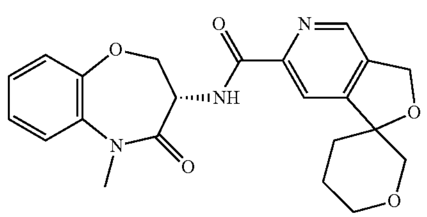 [SMILES: CN1C(=O)[C@@H](NC(=O)c2cc3c(cn2)COC32CCCOC2)COc2ccccc21]

N-[(3S)-5-methyl-4-oxo-2,3-dihydro-1,5-benzoxazepin-3-yl]spiro[3H-furo[3,4-c]pyridine-1,3'-tetrahydropyran]-6-carboxamide

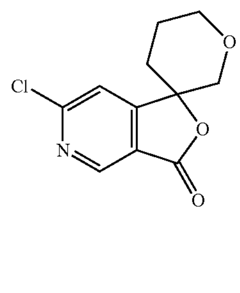 [SMILES: O=C1OC2(CCCOC2)c2cc(Cl)ncc21]

Step 1: 6-chlorospiro[furo[3,4-c]pyridine-1,3'-tetrahydropyran]-3-one

To a solution of 2,2,6,6-tetramethylpiperidine (2.69 g, 19.0 mmol) in tetrahydrofuran (60 mL) was added n-butyllithium (2.5 M in hexanes, 10.2 mL, 25.4 mmol) at −78° C. The reaction mixture was stirred at −78° C. for 1 h and 6-chloronicotinic acid (1.0 g, 6.4 mmol) was added. The reaction mixture was stirred at −78° C. for another 2 h and dihydro-2H-pyran-3(4H)-one (1.27 g, 12.7 mmol) was added. After addition, the reaction mixture was stirred at 25° C. for 16 h and quenched by addition of saturated ammonium chloride (30 mL). The mixture was extracted with ethyl acetate (3×50 mL). The combined organic layers were dried over sodium sulfate and concentrated under reduced pressure. The residue was purified by column chromatography (silica gel, 100-200 mesh, 0 to 50% ethyl acetate in petroleum ether) to afford 6-chlorospiro[furo[3,4-c]pyridine-1,3'-tetrahydropyran]-3-one (1.2 g, 79%) as a light yellow solid. LCMS $R_T$=0.595 min; m/z=240.0 $(M+H)^+$.

LCMS (5 to 95% acetonitrile in water+0.03% trifluoacetic acid over 1.5 mins) retention time 0.595 min, ESI+ found [M+H]=240.0

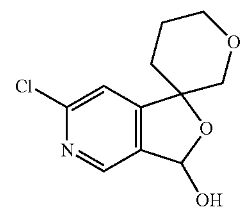 [SMILES: OC1OC2(CCCOC2)c2cc(Cl)ncc21]

Step 2: 6-chlorospiro[3H-furo[3,4-c]pyridine-1,3'-tetrahydropyran]-3-ol

To a mixture of 6-chlorospiro[furo[3,4-c]pyridine-1,3'-tetrahydropyran]-3-one (1.2 g, 5.0 mmol) in toluene (60 mL) was added diisobutylaluminum hydride (12.0 mL, 12.0 mmol, 1.0 M in toluene) at −78° C. The reaction was stirred at −78° C. for 2 h and quenched by addition of saturated ammonium chloride (20 mL). The resulting mixture was extracted with ethyl acetate (3×50 mL). The combined organic layers were washed with water (2×50 mL), brine (50 mL), dried over sodium sulfate and concentrated under reduced pressure to give crude 6-chlorospiro[3H-furo[3,4-c]pyridine-1,3'-tetrahydropyran]-3-ol (1.0 g, 76%) as colorless oil. LCMS $R_T$=0.552 min; m/z=242.0 $(M+H)^+$.

LCMS (5 to 95% acetonitrile in water+0.03% trifluoacetic acid over 1.5 mins) retention time 0.552 min, ESI+ found [M+H]=242.0

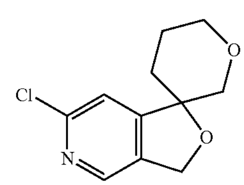 [SMILES: Clc1cc2c(cn1)COC21CCCOC1]

Step 3: 6-chlorospiro[3H-furo[3,4-c]pyridine-1,3'-tetrahydropyran]

To a mixture of 6-chlorospiro[3H-furo[3,4-c]pyridine-1,3'-tetrahydropyran]-3-ol (1.0 g, 4.1 mmol) and 2,2,2-trifluoroacetic acid (2.36 g, 20.7 mmol) in dichloromethane (20 mL) was added triethylsilane (1.44 g, 12.4 mmol) at 0° C. The mixture was stirred for 2 h and then adjusted to pH=8 by addition of 1N sodium hydroxide. The mixture was concentrated under reduced pressure and the residue was diluted with ethyl acetate (50 mL). The solution was washed with water (2×50 mL), brine (40 mL), dried over sodium sulfate and concentrated under reduced pressure. The residue was purified by column chromatography (silica gel, 100-200 mesh, 0 to 10% ethyl acetate in petroleum ether) to afford 6-chlorospiro[3H-furo[3,4-c]pyridine-1,3'-tetrahydropyran] (800 mg, 86%) as yellow oil.

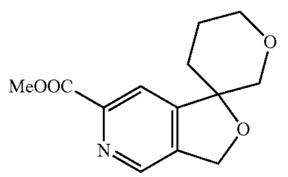 [SMILES: COC(=O)c1cc2c(cn1)COC21CCCOC1]

Step 4: methyl spiro[3H-furo[3,4-c]pyridine-1,3'-tetrahydropyran]-6-carboxylate

A mixture of 6-chlorospiro[3H-furo[3,4-c]pyridine-1,3'-tetrahydropyran] (800 mg, 3.55 mmol), 1,1'-bis(diphenylphosphino)ferrocene palladiumdichloride (259 mg, 0.35 mmol) in methanol (100 mL) was stirred at 80° C. for 16 h under CO (25 psi) and filtered. The filtrate was concentrated under reduced pressure and the residue was purified by column chromatography (silica gel, 100-200 mesh, 0 to 30% ethyl acetate in petroleum ether) to give methyl spiro[3H-furo[3,4-c]pyridine-1,3'-tetrahydropyran]-6-carboxylate (810 mg, 92%) as colorless oil. LCMS $R_T$=0.570 min; m/z=250.1 $(M+H)^+$.

LCMS (5 to 95% acetonitrile in water+0.03% trifluoacetic acid over 1.5 mins) retention time 0.570 min, ESI+ found [M+H]=250.1

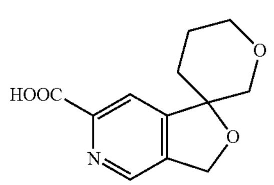 [SMILES: O=C(O)c1cc2c(cn1)COC21CCCOC1]

Step 5: spiro[3H-furo[3,4-c]pyridine-1,3'-tetrahydropyran]-6-carboxylic acid

A mixture of methyl spiro[3H-furo[3,4-c]pyridine-1,3'-tetrahydropyran]-6-carboxylate (200 mg, 0.80 mmol) and lithium hydroxide (58 mg, 2.41 mmol) in tetrahydrofuran (10 mL) and water (5 mL) was stirred at 25° C. for 3 h. The mixture was adjusted to pH=6 by addition of 1N HCl. The resulting solution was concentrated to dryness under reduced pressure. The residue was purified by column chromatography (silica gel, 100-200 mesh, 0 to 10% methanol in dichloromethane) to give spiro[3H-furo[3,4-c]pyridine-1,3'-tetrahydropyran]-6-carboxylic acid (150 mg, 80%) as a white solid, used as is in the next step.

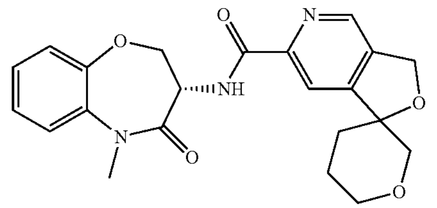 [SMILES: CN1C(=O)[C@@H](NC(=O)c2cc3c(cn2)COC32CCCOC2)COc2ccccc21]

Step 6: N-[(3S)-5-methyl-4-oxo-2,3-dihydro-1,5-benzoxazepin-3-yl]spiro[3H-furo[3,4-c]pyridine-1,3'-tetrahydropyran]-6-carboxamide A mixture of (3S)-3-amino-5-methyl-2,3-dihydro-1,5-benzoxazepin-4-one (20 mg, 0.10 mmol), spiro[3H-furo[3,4-c]pyridine-1,3'-tetrahydropyran]-6-carboxylic acid (37 mg, 0.16 mmol), $N^1$-((ethylimino)methylene)-$N^3$,$N^3$-dimethylpropane-1,3-diamine hydrochloride (21 mg, 0.16 mmol) and 1H-benzo[d][1,2,3]triazol-1-ol (21 mg, 0.16 mmol) in N,N-dimethylformamide (3 mL) was stirred at 25° C. for 16 h. The mixture was concentrated under reduced pressure and the residue was purified by RP-HPLC (acetonitrile 45% to 75%/0.05% formic acid in water) to give N-[(3S)-5-methyl-4-oxo-2,3-dihydro-1,5-benzoxazepin-3-yl]spiro[3H-furo[3,4-c]pyridine-1,3'-tetrahydropyran]-6-carboxamide (3.1 mg, 7%) as a white solid. $^1H$ NMR (400 MHz, $CD_3OD$) δ8.60 (s, 1H), 8.03 (s, 1H), 7.46-7.43 (m, 1H), 7.33-7.32 (m, 2H), 7.26-7.24 (m, 1H), 5.20 (d, J=8.0 Hz, 2H), 5.05-5.00 (m, 1H), 4.67-4.62 (m, 1H), 4.43-4.38 (m, 1H), 3.82 (s, 1H), 3.73-3.72 (m, 1H), 3.65-3.64 (m, 2H), 3.43 (s, 3H), 2.03-2.00 (m, 3H), 1.97-1.74 (m, 1H). LCMS $R_T$=1.722 min; m/z=410.1 $(M+H)^+$.

LCMS (10 to 80% acetonitrile in water+0.03% ammonium hydroxide over 3 mins) retention time 1.722 min, ESI+ found [M+H]=410.1.

Example 490

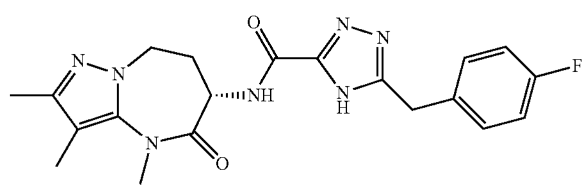 [SMILES: Cc1nn2c(c1C)N(C)C(=O)[C@@H](NC(=O)c1nnc(Cc3ccc(F)cc3)[nH]1)CC2]

5-[(2,3-difluorophenyl)methyl]-N-(6S)-2,3,4-trimethyl-5-oxo-7,8-dihydro-6H-pyrazolo[1, 5-a][1,3]diazepin-6-yl-4H-1,2,4-triazole-3-carboxamide Amide coupling prepared in a similar fashion to WX Method 011. The crude was purified by RP-HPLC (ACN 25-55%/0.05% ammonia hydroxide in water) to afford 5-[(2,3-difluorophenyl)methyl]-N-(6S)-2,3,4-trimethyl-5-oxo-7,8-dihydro-6H-pyrazolo[1,5-a][1,3]diazepin-6-yl-4H-1,2,4-triazole-3-carboxamide (12.03 mg, 12%) as a white solid. $^1H$ NMR (400 MHz, $CD_3OD$) δ7.20-7.10 (m, 3H), 4.43-4.38 (m, 1H), 4.23-4.19 (m, 4H), 3.30 (s, 3H), 2.78-2.71 (m, 1H), 2.20-2.18 (s, 4H), 2.01 (s, 3H). LC-MS $R_T$=0.749 min, m/z=430.1 $(M+H)^+$.

LCMS (5 to 95% acetonitrile in water+0.1% trifluoacetic acid over 1.5 mins) retention time 0.749 min, ESI+ found [M+H]=430.1

Example 491

WX Method 009

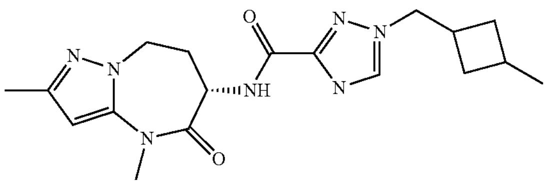

1-[(3-methylcyclobutyl)methyl]-N-(6S)-2,4-dimethyl-5-oxo-7,8-dihydro-6H-pyrazol[1,5-a][1,3]diazepin-6-yl-1,2,4-triazole-3-carboxamide

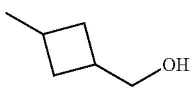

Step 1: (3-methylcyclobutyl)methanol

To a solution of 3-methylcyclobutanecarboxylic acid (500 mg, 4.38 mmol) in tetrahydrofuran (15 mL) was added $LiAlH_4$ (333 mg, 8.76 mmol) at 0° C. The reaction mixture was stirred at 0° C. for 1 h, and then quenched by addition of water (0.2 mL), 15% aqueous NaOH (0.2 mL) and water (0.6 mL). The mixture was diluted with dichloromethane (20 mL), dried over anhydrous sodium sulfate and concentrated under reduced pressure to give (3-methylcyclobutyl)methanol (400 mg, 91%) as a colorless oil which was used in next step without further purification, used as is in the next step.

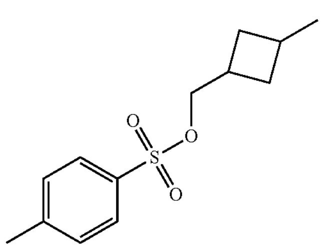

Step 2: (3-methylcyclobutyl)methyl 4-methylbenzenesulfonate

To a solution of (3-methylcyclobutyl)methanol (300 mg, 3.0 mmol) in dichloromethane (6 mL) was added 4-dimethylaminopyridine (642 mg, 5.3 mmol) and p-toluenesulfonylchloride (601 mg, 3.2 mmol). The reaction mixture was stirred at 20° C. for 3 h and then quenched by addition of brine (6 mL). The separated organic layer was dried over anhydrous sodium sulfate and concentrated under reduced pressure. The residue was purified by preparative TLC (10% ethyl acetate in petroleum ether, Rf=0.5) to afford (3-methylcyclobutyl)methyl 4-methylbenzenesulfonate (450 mg, 59%) as a colorless oil, used as is in the next step.

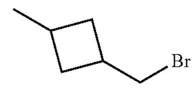

Step 3: 1-(bromomethyl)-3-methylcyclobutane

To a solution of lithium bromide (1229 mg, 14.2 mmol) in acetone (8.0 mL) was added (3-methylcyclobutyl)methyl 4-methylbenzenesulfonate (450 mg, 1.8 mmol). The reaction mixture was heated at 70° C. for 2 h and then concentrated under reduced pressure. The residue was dissolved in ethyl acetate (50 mL) and washed with brine, dried over anhydrous sodium sulfate and concentrated under reduced pressure to give the crude 1-(bromomethyl)-3-methylcyclobutane (288 mg, 80%) as colorless oil, used as is in the next step.

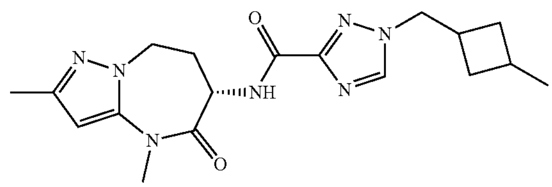

Step 4: 1-[(3-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide A mixture of N-[(6S)-2,4-dimethyl-5-oxo-7,8-dihydro-6H-pyrazolo[1,5-a][1,3]diazepin-6-yl]-1H-1,2,4-triazole-3-carboxamide (45 mg, 0.16 mmol), potassium carbonate (65 mg, 0.47 mmol) and 1-(bromomethyl)-3-methylcyclobutane (51 mg, 0.31 mmol) in N,N-dimethylformamide (5 mL) was stirred at 20° C. for 16 h. The solvent was evaporated under reduced pressure and the residue was purified by RP-HPLC (22-52% acetonitrile in water and 0.05% ammonia hydroxide) to give 1-[(3-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide (11.1 mg, 19%) as white solids. $^1H$ NMR (400 MHz, $CD_3OD$) δ 8.47 (s, 1H), 6.12 (s, 1H), 4.56-4.52 (m, 1H), 4.34-4.22 (m, 5H), 3.33 (s, 3H), 2.89-2.64 (m, 2H), 2.27-2.20 (m, 7H), 1.41-1.39 (m, 1H), 1.13-1.02 (m, 3H). LCMS $R_T$=0.942 min, m/z=372.3 $(M+H)^+$.

LCMS (10 to 80% acetonitrile in water+0.03% trifluoacetic acid over 2.0 mins) retention time 0.942 min, ESI+ found [M+H]=372.3.

Example 492

WX Method 010

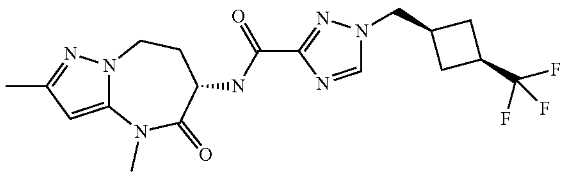 [SMILES: Cc1cc2n(n1)CC[C@H](NC(=O)c1ncn(C[C@H]3C[C@@H](C(F)(F)F)C3)n1)C(=O)N2C]

N—(S)-2,4-dimethyl-5-oxo-7,8-dihydro-6H-pyrazolo[1,5-a][1,3]diazepin-6-yl]-1-(((1S,3R)-3-trifluoromethylcyclobutyl)methyl)-1H-1,2,4-triazole-3-carboxamide

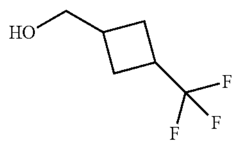

Step 1: (3-(trifluoromethyl)cyclobutyl)methanol

To a solution of 3-(trifluoromethyl)cyclobutanecarboxylic acid (520 mg, 3.09 mmol) in tetrahydrofuran (15 mL) was added $LiAlH_4$ (235 mg, 6.19 mmol) at 0° C. After addition, the reaction mixture was stirred at 0° C. for 2 h and then quenched by addition of water (0.2 mL), 15% aqueous NaOH (0.2 mL) and water (0.6 mL). The mixture was diluted with dichloromethane (20 mL), dried over anhydrous sodium sulfate, and concentrated under reduced pressure to give crude (3-(trifluoromethyl)cyclobutyl)methanol (476 mg, 99%) as a colorless oil, used as is in the next step.

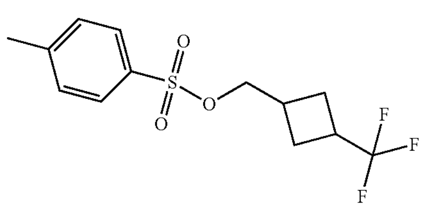 [SMILES: Cc1ccc(S(=O)(=O)OCC2CC(C(F)(F)F)C2)cc1]

Step 2: (3-(trifluoromethyl)cyclobutyl)methyl 4-methylbenzenesulfonate

To a solution of (3-(trifluoromethyl)cyclobutyl)methanol (476 mg, 3.1 mmol) in dichloromethane (20 mL) was added 4-dimethylaminopyridine (755 mg, 6.2 mmol) and p-toluenesulfonylchloride (707 mg, 3.7 mmol). The reaction mixture was stirred at 20° C. for 12 h and concentrated under reduced pressure. The residue was purified by column chromatography (silica gel: 100-200 mesh, 0-30% ethyl acetate in petroleum ether) to afford (3-(trifluoromethyl) cyclobutyl)methyl 4-methylbenzenesulfonate (700 mg, 74%) as a colorless oil, used as is in the next step.

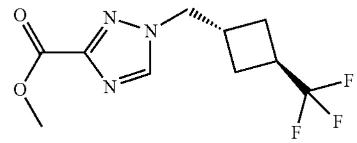

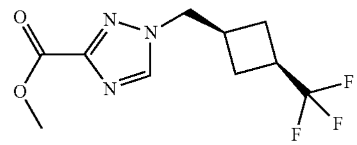

Step 3: methyl 1-(((1R,3R)-3-(trifluoromethyl)cyclobutyl)methyl)-1H-1,2,4-triazole-3-carboxylate & methyl 1-(((1S,3S)-3-(trifluoromethyl)cyclobutyl) methyl)-1H-1,2,4-triazole-3-carboxylate To a solution of methyl 1H-1,2,4-triazole-3-carboxylate (289 mg, 2.3 mmol) and (3-(trifluoromethyl)cyclobutyl) methyl 4-methylbenzenesulfonate (700 mg, 2.27 mmol) in N,N-dimethylformamide (20 mL) was added 4-dimethylaminopyridine (333 mg, 2.7 mmol), cesium carbonate (2219 mg, 6.8 mmol) and sodium iodide (408 mg, 2.7 mmol). The mixture was stirred at 95° C. for 12 h and diluted with water (30 mL). The resulting solution was extracted with ethyl acetate (4×20 mL). The combined organic layers were washed with water (3×20 mL), brine (2×20 mL), dried over anhydrous sodium sulfate and concentrated under reduced pressure. The residue was purified by column chromatography (silica gel: 100-200 mesh, 0-90% ethyl acetate in petroleum ether) to afford methyl 1-((3-(trifluoromethyl) cyclobutyl)methyl)-1H-1,2,4-triazole-3-carboxylate (320 mg, 54%) as a colorless oil. This material was further separated by SFC to give: methyl 1-(((1R,3R)-3-(trifluoromethyl)cyclobutyl)methyl)-1H-1,2,4-triazole-3-carboxylate (Peak 1, Retention time=4.723 min) (140 mg, 43.4%) as white solids. $^1H$ NMR (400 MHz, $CD_3OD$) δ 8.50 (s, 1H), 6.12 (s, 1H), 4.57-4.52 (m, 1H), 4.31-4.22 (m, 4H), 3.33 (s, 3H), 3.01-2.83 (m, 3H), 2.28-2.24 (m, 6H), 2.01-1.98 (m, 2H)

LCMS (5 to 95% acetonitrile in water+0.03% trifluoacetic acid over 1.5 mins) retention time 0.730 min, ESI+ found [M+H]=263.9.

methyl 1-(((1 S,3 S)-3-(trifluoromethyl)cyclobutyl) methyl)-1H-1,2,4-triazole-3-carboxylate (Peak 2, Retention time=5.664 min) (140 mg, 43.4%) as white solids. $^1H$ NMR (400 MHz, $CDCl_3$) δ 8.13 (s, 1H), 4.27 (d, J=7.6 Hz, 2H), 4.01 (s, 1H), 2.94-2.88 (m, 2H), 2.33-2.30 (m, 2H), 2.01-1.84 (m, 2H).

LCMS (5 to 95% acetonitrile in water+0.03% trifluoacetic acid over 1.5 mins) retention time 0.730 min, ESI+ found [M+H]=263.9.

SFC condition: Column: Chiralcel IC-3 150×4.6 mm I.D., 3 um Mobile phase: 40% iso-propanol (0.05% DEA) in $CO_2$ Flow rate: 2.5 mL/min Column temperature: 40° C. SFC condition: column: chiralcel OD-3 100×4.6 mm I.D., 3 um mobile phase: A: $CO_2$; B: ethanol (0.05% DEA) gradient: from 5% to 40% of B in 4.5 min and hold 40% for 2.5 min, then 5% of B for 1 min. Flow rate: 2.8 mL/min. Column temperature: 40° C.

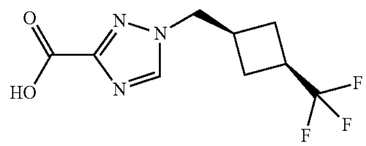 [SMILES: O=C(O)c1ncn(C[C@H]2C[C@@H](C(F)(F)F)C2)n1]

Step 4: 1-(((1S,3S)-3-(trifluoromethyl)cyclobutyl) methyl)-1H-1,2,4-triazole-3-carboxylic acid A mixture of methyl 1-(((1 S,3 S)-3-(trifluoromethyl) cyclobutyl)methyl)-1H-1,2,4-triazole-3-carboxylate (140 mg, 0.53 mmol) and lithium hydroxide hydrate (112 mg, 2.66 mmol) in tetrahydrofuran/Methanol/Water (5 mL, 2:2:1) was stirred at 25° C. for 1 h. The solution was diluted with water (10 mL) and adjusted to pH=4-5 with addition of 1M HCl. The resulting solid was collected by filtration and dried under reduced pressure to give 1-(((1 S,3 S)-3-(trifluoromethyl)cyclobutyl)methyl)-1H-1,2,4-triazole-3-carboxylic acid (100 mg, 76%) as a white solid, used as is in the next step.

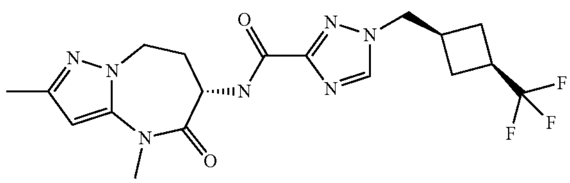 [SMILES: Cc1cc2n(n1)CC[C@H](NC(=O)c1ncn(C[C@H]3C[C@@H](C(F)(F)F)C3)n1)C(=O)N2C]

Step 5: N—(S)-2,4-dimethyl-5-oxo-7,8-dihydro-6H-pyrazolo[1,5-a][1,3]diazepin-6-yl]-1-(((1 S,3R)-3-trifluoromethylcyclobutyl)methyl)-1H-1,2,4-triazole-3-carboxamide A mixture of 1-(((1 S,3 S)-3-(trifluoromethyl)cyclobutyl) methyl)-1H-1,2,4-triazole-3-carboxylic acid (31 mg, 0.12 mmol), 1-hydroxybenzotriazole (25 mg, 0.19 mmol), 1-(3-dimethylaminopropyl)-3-ethylcarbodiimidehydrochloride (36 mg, 0.19 mmol) and (6S)-6-amino-2,4-dimethyl-7,8-dihydro-6H-pyrazolo[1,5-a][1,3]diazepin-5-one (24 mg, 0.12 mmol) in N,N-dimethylformamide (5 mL) was stirred at 20° C. for 12 h. The solvent was evaporated under reduced pressure and the residue was purified by RP-HPLC (acetonitrile 46-76%/0.05% ammonium hydroxide in water) to afford N—(S)-2,4-dimethyl-5-oxo-7,8-dihydro-6H-pyrazolo[1,5-a][1,3]diazepin-6-yl]-1-(((1 S,3R)-3-trifluoromethylcyclobutyl)methyl)-1H-1,2,4-triazole-3-carboxamide (35.7 mg, 68%) as white solids. $^1$H NMR (400 MHz, $CD_3OD$) δ8.50 (s, 1H), 6.12 (s, 1H), 4.57-4.52 (m, 1H), 4.31-4.22 (m, 4H), 3.33 (s, 3H), 3.01-2.83 (m, 3H), 2.28-2.24 (m, 6H), 2.01-1.98 (m, 2H). LC-MS $R_T$=0.927 min, m/z=426.3 $(M+H)^+$.

LCMS (10 to 80% acetonitrile in water+0.03% trifluoacetic acid over 2.0 mins) retention time 0.927 min, ESI+ found [M+H]=426.3.

Example 493

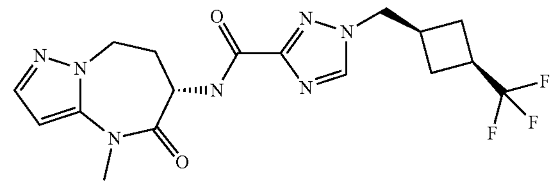 [SMILES: CN1C(=O)[C@@H](NC(=O)c2ncn(C[C@H]3C[C@@H](C(F)(F)F)C3)n2)CCn2nccc21]

N—(S)-4-methyl-5-oxo-7,8-dihydro-6H-pyrazolo[1,5-a][1,3]diazepin-6-yl]-1-(((1S,3R)-3-trifluoromethylcyclobutyl)methyl)-1H-1,2,4-triazole-3-carboxamide Amide coupling prepared in a similar fashion to WX Method 010. The crude was purified by RP-HPLC (acetonitrile 46-76%/0.05% ammonium hydroxide in water) to give N—(S)-4-methyl-5-oxo-7,8-dihydro-6H-pyrazolo[1,5-a][1,3]diazepin-6-yl]-1-(((1 S,3R)-3-trifluoromethylcyclobutyl) methyl)-1H-1,2,4-triazole-3-carboxamide (37.9 mg, 68%) as white solids. $^1$H NMR (400 MHz, $CD_3OD$) δ 8.50 (s, 1H), 7.53 (s, 1H), 6.31 (d, J=2.0 Hz, 1H), 4.55-4.41 (m, 2H), 4.31-4.29 (m, 3H), 3.37 (s, 3H), 3.01-2.85 (m, 3H), 2.30-2.25 (m, 3H), 2.01-1.94 (m, 2H). LC-MS $R_T$=0.891 min, m/z=412.3 $(M+H)^+$.

LCMS (10 to 80% acetonitrile in water+0.03% trifluoacetic acid over 2.0 mins) retention time 0.891 min, ESI+ found [M+H]=412.3.

Example 494

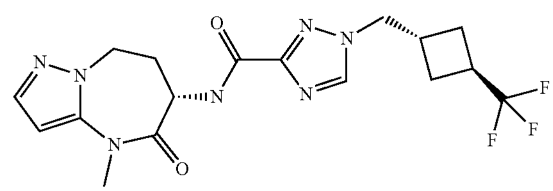 [SMILES: CN1C(=O)[C@@H](NC(=O)c2ncn(C[C@H]3C[C@H](C(F)(F)F)C3)n2)CCn2nccc21]

N—(S)-4-methyl-5-oxo-7,8-dihydro-6H-pyrazolo[1,5-a][1,3]diazepin-6-yl]-1-(((1R,3S)-3-trifluoromethylcyclobutyl)methyl)-1H-1,2,4-triazole-3-carboxamide Amide coupling prepared in a similar fashion to WX Method 011. The crude was purified by RP-HPLC (acetonitrile 46-76%/0.05% ammonium hydroxide in water) to give N—(S)-4-methyl-5-oxo-7,8-dihydro-6H-pyrazolo[1,5-a][1,3]diazepin-6-yl]-1-(((1R,3 S)-3-trifluoromethylcyclobutyl) methyl)-1H-1,2,4-triazole-3-carboxamide (25.4 mg, 45%) as white solids. $^1$H NMR (400 MHz, $CD_3OD$) δ8.51 (s, 1H), 7.53 (d, J=2.0 Hz, 1H), 6.31 (d, J=2.0 Hz, 1H), 4.52-4.29 (m, 5H), 3.37 (s, 3H), 3.07-2.88 (m, 3H), 2.33-2.26 (m, 3H), 2.18-2.14 (m, 2H). LC-MS $R_T$=0.903 min, m/z=412.3 $(M+H)^+$.

LCMS (10 to 80% acetonitrile in water+0.03% trifluoacetic acid over 2.0 mins) retention time 0.903 min, ESI+ found [M+H]=412.3.

Example 495

WX Method 014

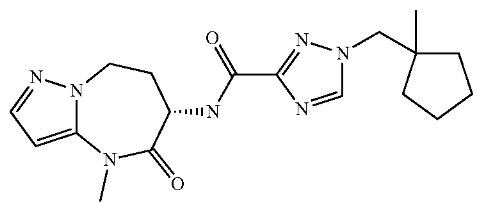 [SMILES: CN1C(=O)[C@@H](NC(=O)c2ncn(CC3(C)CCCC3)n2)CCn2nccc21]

1-[(1-methylcyclopentyl)methyl]-N-(6S)-2,4-dimethyl-5-oxo-7,8-dihydro-6H-pyrazolo[1, 5-a][1,3]diazepin-6-yl-1,2,4-triazole-3-carboxamide

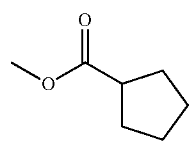

Step 1: methyl cyclopentanecarboxylate

To a solution of cyclopentanecarboxylic acid (5.0 g, 43.8 mmol) in dichloromethane (30 mL) and methanol (10 mL) was added (trimethylsilyl)diazomethane (2.0 M in hexane, 109 mL, 219.0 mmol) at 25° C. After addition, the solution was stirred at 25° C. for 2 h and then concentrated under reduced pressure to give methyl cyclopentanecarboxylate (5 g, 89%) as a yellow oil. $^1$H NMR (400 MHz, $CDCl_3$) δ 3.67 (s, 3H), 2.77-2.71 (m, 1H), 1.90-1.87 (m, 2H), 1.81-1.70 (m, 4H), 1.59-1.57 (m, 2H).

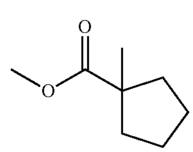

Step 2: methyl 1-methylcyclopentanecarboxylate

To a solution of diisopropylamine (7.9 g, 78.0 mmol) in tetrahydrofuran (80 mL) was added n-butyllithium (2.5 M in hexane, 31.2 mL, 78.0 mmol,) at −70° C. The mixture was stirred at −70° C. for 0.5 h, then methyl cyclopentanecarboxylate (5.0 g, 39.0 mmol) was added. After addition, stirring at −70° C. was continued for another 0.5 h, methyl iodide (7.3 mL, 117.0 mmol) was added. The resulting mixture was stirred at 20° C. for 12 h and quenched by addition of saturated aqueous ammonium chloride (100 mL). The solution was extracted with ethyl acetate (3×50 mL). The combined organic layers were washed with brine (100 mL), dried over anhydrous sodium sulfate and concentrated under reduced pressure to give crude methyl 1-methylcyclopentanecarboxylate (5.5 g, 99%) as a yellow oil. $^1$H NMR (400 MHz, $CDCl_3$) δ 3.67 (s, 3H), 2.11-2.05 (m, 2H), 1.69-1.66 (m, 4H), 1.48-1.45 (m, 2H), 1.24 (s, 3H)

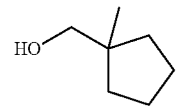

Step 3: (1-methylcyclopentyl)methanol

To a solution of methyl 1-methylcyclopentanecarboxylate (1.0 g, 7.03 mmol) in tetrahydrofuran (15 mL) was added $LiAlH_4$ (533 mg, 14.1 mmol) at 0° C. The reaction mixture was stirred at 0° C. for 1 h and then quenched by addition of water (0.5 mL), 15% aqueous NaOH (0.5 mL) and water (1.5 mL). The mixture was diluted with dichloromethane (20 mL), dried over anhydrous sodium sulfate and concentrated under reduced pressure. The residue was purified by flash column chromatography (silica gel, 100-200 mesh, 0-10% ethyl acetate in petroleum ether) to give (1-methylcyclopentyl)methanol (400 mg, 50%) as a colorless oil.

$^1$H NMR (400 MHz, $CDCl_3$) δ 3.39 (s, 2H), 1.67-1.62 (m, 4H), 1.50-1.47 (m, 2H), 1.32-1.30 (m, 2H), 1.02 (s, 3H).

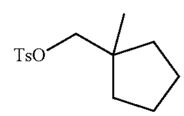 [SMILES: Cc1ccc(S(=O)(=O)OCC2(C)CCCC2)cc1]

Step 4: (1-methylcyclopentyl)methyl 4-methylbenzenesulfonate

To a solution of (1-methylcyclopentyl) methanol (100 mg, 0.88 mmol) in dichloromethane (6 mL) was added 4-dimethylaminopyridine (214 mg, 1.75 mmol) and p-Toluenesulfonylchloride (200 mg, 1.05 mmol). The reaction mixture was stirred at 20° C. for 2 h and then quenched by addition of brine (6 mL). The organic layer was dried over anhydrous sodium sulfate and concentrated under reduced pressure. The residue was purified by preparative TLC (10% ethyl acetate in petroleum ether, $R_f$=0.4) to afford (1-methylcyclopentyl)methyl 4-methylbenzene sulfonate (200 mg, 85%) as a colorless oil. $^1$H NMR (400 MHz, $CDCl_3$) δ 7.80 (d, J=8.0 Hz, 2H), 7.35 (d, J=8.0 Hz, 2H), 3.77 (s, 2H), 2.46 (s, 3H), 1.63-1.55 (m, 4H), 1.45-1.44 (m, 2H), 1.33-1.31 (m, 2H), 0.98 (s, 3H).

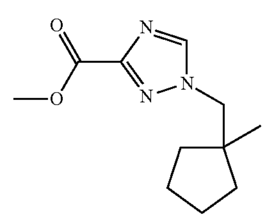

Step 5: methyl 1-((1-methylcyclopentyl)methyl)-1H-1,2,4-triazole-3-carboxylate

To a solution of methyl 1H-1,2,4-triazole-3-carboxylate (50 mg, 0.39 mmol) and (1-methylcyclopentyl)methyl 4-methylbenzenesulfonate (106 mg, 0.39 mmol) in N,N-dimethylformamide (4 mL) was added cesium carbonate (384 mg, 1.18 mmol), sodium iodide (71 mg, 0.47 mmol) and 4-dimethylaminopyridine (58 mg, 0.47 mmol). The mixture was stirred at 100° C. for 12 h and concentrated under reduced pressure. The residue was diluted with ethyl acetate (20 mL) and washed with water (2×10 mL). The separated organic layer was dried over anhydrous sodium sulfate and concentrated under reduced pressure. The residue was purified by preparative TLC (50% ethyl acetate in petroleum ether, $R_f$=0.5) to give methyl 1-[(1-methylcyclopentyl)methyl]-1,2,4-triazole-3-carboxylate (50 mg, 57%) as a colorless oil. LC-MS $R_T$=0.973 min, m/z=223.9 $[M+H]^+$.

LCMS (10 to 80% acetonitrile in water+0.03% trifluoacetic acid over 2.0 mins) retention time 0.973 min, ESI+ found [M+H]=223.9.

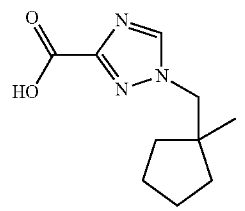

Step 6: 1-((1-methylcyclopentyl)methyl)-1H-1,2,4-triazole-3-carboxylic acid

A mixture of methyl 1-[(1-methylcyclopentyl)methyl]-1,2,4-triazole-3-carboxylate (50 mg, 0.22 mmol) and lithium hydroxide hydrate (47 mg, 1.12 mmol) in tetrahydrofuran/methanol/water (5 mL, 2:2:1) was stirred at 25° C. for 1 h. The solution was diluted with water (10 mL) and adjusted to pH=4-5 by addition of 1M HCl. The resulting mixture was extracted with ethyl acetate (3×15 mL). The combined organic layers were dried over anhydrous sodium sulfate and concentrated under reduced pressure to give crude 1-[(1-methylcyclopentyl)methyl]-1,2,4-triazole-3-carboxylic acid (45 mg, 96%) as a white solid. LC-MS $R_T$=1.055 min, m/z=209.9 $[M+H]^+$.

LCMS (0 to 60% acetonitrile in water+0.03% trifluoacetic acid over 2.0 mins) retention time 1.055 min, ESI+ found [M+H]=209.9.

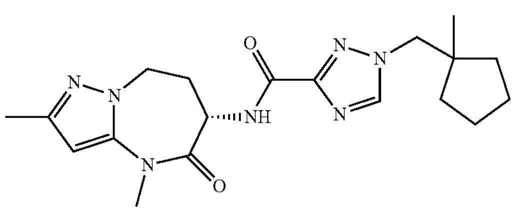 [SMILES: Cc1cc2n(n1)CC[C@H](NC(=O)c1ncn(CC3(C)CCCC3)n1)C(=O)N2C]

Step 7: 1-[(1-methylcyclopentyl)methyl]-N-(6S)-2,4-dimethyl-5-oxo-7,8-dihydro-6H-pyrazolo[1, 5-a][1,3]diazepin-6-yl-1,2,4-triazole-3-carboxamide To a stirred solution of 1-[(1-methylcyclopentyl)methyl]-1,2,4-triazole-3-carboxylic acid (32 mg, 0.15 mmol) in N,N-dimethylformamide (2 mL) was added 1-hydroxybenzotriazole (31 mg, 0.23 mmol), 1-(3-dimethylaminopropyl)-3-ethyl carbodiimidehydrochloride (44 mg, 0.23 mmol) and (6S)-6-amino-2,4-dimethyl-7,8-dihydro-6H-pyrazolo[1,5-a][1,3]diazepin-5-one (30 mg, 0.15 mmol). The resulting mixture was stirred at 25° C. for 2 h and concentrated under reduced pressure. The residue was purified by RP-HPLC (acetonitrile 30-60%/0.05% ammonium hydroxide in water) to afford 1-[(1-methylcyclopentyl)methyl]-N-(6S)-2,4-dimethyl-5-oxo-7,8-dihydro-6H-pyrazolo[1,5-a][1,3]diazepin-6-yl-1,2,4-triazole-3-carboxamide (26.4 mg, 44%) as a white solid. $^1H$ NMR (400 MHz, $CD_3OD$) δ 8.49 (s, 1H), 6.12 (s, 1H), 4.57-4.52 (m, 1H), 4.31-4.22 (m, 2H), 4.18 (s, 2H), 3.34 (s, 3H), 2.90-2.83 (m, 1H), 2.30-2.23 (m, 4H), 1.71-1.65 (m, 6H), 1.39-1.36 (m, 2H), 0.97 (s, 3H). LC-MS $R_T$=0.677 min, m/z=386.2 $[M+H]^+$.

LCMS (5 to 95% acetonitrile in water+0.03% trifluoacetic acid over 1.5 mins) retention time 0.677 min, ESI+ found [M+H]=386.2.

Examples 496 and 497

WX Method 015

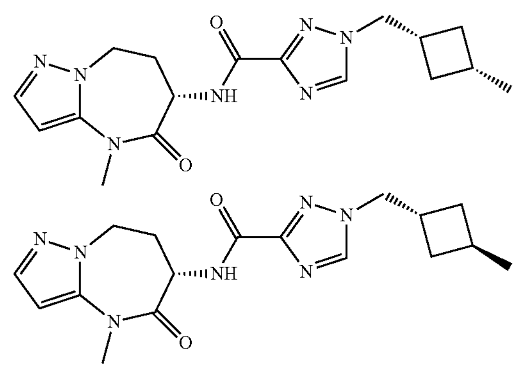

N—((S)-4-methyl-5-oxo-5,6,7,8-tetrahydro-4H-pyrazolo[1,5-a][1,3]diazepin-6-yl)-1-(((1S,3R)-3-methylcyclobutyl)methyl)-1H-1,2,4-triazole-3-carboxamide and N—((S)-4-methyl-5-oxo-5,6,7,8-tetrahydro-4H-pyrazolo[1,5-a][1,3]diazepin-6-yl)-1-(((1R,3S)-3-methylcyclobutyl)methyl)-1H-1,2,4-triazole-3-carboxamide

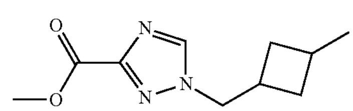

Step 1: methyl 1-[(3-methylcyclobutyl)methyl]-1,2,4-triazole-3-carboxylate

To a solution of methyl 1H-1,2,4-triazole-3-carboxylate (120 mg, 0.94 mmol) and (3-methylcyclobutyl)methyl 4-methylbenzenesulfonate (240 mg, 0.94 mmol) in N,N-dimethylformamide (12 mL) was added 4-dimethylaminopyridine (138 mg, 1.13 mmol), cesium carbonate (923 mg, 2.83 mmol) and sodium iodide (170 mg, 1.13 mmol). The mixture was stirred at 95° C. for 12 h and then concentrated under reduced pressure. The residue was diluted with ethyl acetate (20 mL), washed with water (2×10 mL), dried over anhydrous sodium sulfate and concentrated under reduced pressure. The residue was purified by preparative TLC (50% ethyl acetate in petroleum ether, $R_f$=0.2) to give methyl 1-[(3-methylcyclobutyl)methyl]-1,2,4-triazole-3-carboxylate (70 mg, 35%) as a colorless oil. LC-MS $R_T$=0.730 min, m/z=209.9 $[M+H]^+$.

LCMS (5 to 95% acetonitrile in water+0.03% trifluoacetic acid over 1.5 mins) retention time 0.730 min ESI+ found M+H]=209.9.

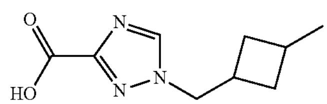

Step 2: 1-((1-methylcyclopentyl)methyl)-1H-1,2,4-triazole-3-carboxylic acid

A mixture of methyl 1-[(3-methylcyclobutyl)methyl]-1,2,4-triazole-3-carboxylate (70 mg, 0.33 mmol) and lithium hydroxide hydrate (84 mg, 2.01 mmol) in tetrahydrofuran/methanol/water (5 mL, 2:2:1) was stirred at 25° C. for 1 h. The solution was diluted with water (10 mL) and adjusted to pH=4-5 by addition of 1M HCl. The mixture was extracted with ethyl acetate (3×15 mL). The combined organic layers were dried over anhydrous sodium sulfate and concentrated under reduced pressure to give the crude 1-[(3-methylcyclobutyl)methyl]-1,2,4-triazole-3-carboxylic acid (60 mg, 92%) as a white solid. LC-MS $R_T$=0.377 min, m/z=195.9 $[M+H]^+$.

LCMS (5 to 95% acetonitrile in water+0.03% trifluoacetic acid over 1.5 mins) retention time 0.377 min, ESI+ found [M+H]=195.9.

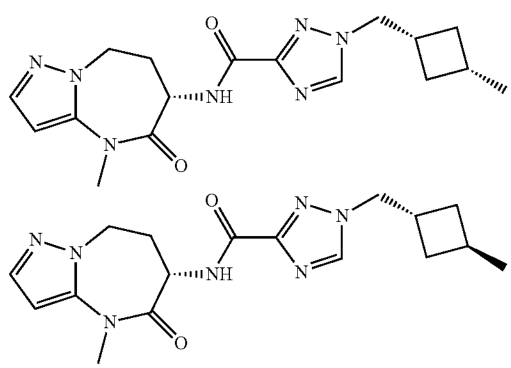

Step 3: N—((S)-4-methyl-5-oxo-5,6,7,8-tetrahydro-4H-pyrazolo[1,5-a][1,3]diazepin-6-yl)-1-(((1S,3R)-3-methylcyclobutyl)methyl)-1H-1,2,4-triazole-3-carboxamide and N—((S)-4-methyl-5-oxo-5,6,7,8-tetrahydro-4H-pyrazolo[1,5-a][1,3]diazepin-6-yl)-1-(((1R,3S)-3-methylcyclobutyl)methyl)-1H-1,2,4-triazole-3-carboxamide To a stirred solution of 1-[(3-methylcyclobutyl)methyl]-1,2,4-triazole-3-carboxylic acid (54 mg, 0.28 mmol) in N,N-dimethylformamide (3 mL) was added 1-hydroxybenzotriazole (56 mg, 0.42 mmol), 1-(3-dimethylaminopropyl)-3-ethyl carbodiimidehydrochloride (80 mg, 0.42 mmol) and (6S)-6-amino-4-methyl-7,8-dihydro-6H-pyrazolo[1,5-a][1,3]diazepin-5-one (50 mg, 0.28 mmol). The mixture was stirred at 25° C. for 2 h and concentrated under reduced pressure. The residue was purified by RP-HPLC (acetonitrile 25-55%/0.05% ammonium hydroxide in water) to afford 1-[(3-methylcyclobutyl)methyl]-N-[(6S)-4-methyl-5-oxo-7,8-dihydro-6H-pyrazolo[1,5-a][1,3]diazepin-6-yl]-1,2,4-triazole-3-carboxamide (75 mg, 74%) as a white solid.

The racemic compound was further separated by chiral SFC to afford:

N—((S)-4-methyl-5-oxo-5,6,7,8-tetrahydro-4H-pyrazolo[1,5-a][1,3]diazepin-6-yl)-1-(((1 S,3R)-3-methylcyclobutyl)methyl)-1H-1,2,4-triazole-3-carboxamide (Peak 1, retention time=4.957 min) (43.8 mg, 58%) as a white solid. $^1H$ NMR (400 MHz, $CD_3OD$) δ 8.45 (s, 1H), 7.53 (d, J=2.0 Hz, 1H), 6.31 (d, J=1.2 Hz, 1H), 4.54-4.40 (m, 2H), 4.43-4.41 (m, 1H), 4.23 (d, J=7.6 Hz, 2H), 3.36 (s, 3H), 2.88-2.83 (m, 1H), 2.68-2.64 (m, 1H), 2.31-2.17 (m, 4H), 1.44-1.36 (m, 2H), 1.03 (d, J=6.4 Hz, 3H). LC-MS $R_T$=0.649 min, m/z=358.2 $[M+H]^+$.

LCMS (5 to 95% acetonitrile in water+0.03% trifluoacetic acid over 1.5 mins) retention time 0.649 min, ESI+ found [M+H]=358.2.

N—((S)-4-methyl-5-oxo-5,6,7,8-tetrahydro-4H-pyrazolo[1,5-a][1,3]diazepin-6-yl)-1-(((1R,3 S)-3-methylcyclobutyl)methyl)-1H-1,2,4-triazole-3-carboxamide (Peak 2, Retention time=5.433 min) (22.7 mg, 30%) as a white solid. $^1H$ NMR (400 MHz, $CD_3OD$) δ 8.48 (s, 1H), 7.53 (d, J=2.0 Hz, 1H), 6.31 (s, 1H), 4.54-4.49 (m, 2H), 4.34-4.29 (m, 3H), 3.36 (s, 3H), 2.87-2.82 (m, 2H), 2.49-2.40 (m, 1H), 2.29-2.20 (m, 1H), 2.01-1.94 (m, 2H), 1.76-1.71 (m, 2H), 1.12 (d, J=6.8 Hz, 3H). LC-MS $R_T$=0.649 min, m/z=358.2 $[M+H]^+$.

LCMS (5 to 95% acetonitrile in water+0.03% trifluoacetic acid over 1.5 mins) retention time 0.649 min, ESI+ found [M+H]=358.2.

SFC condition: column chiralpak AD (250 mm*30 mm, 5 um), 3 um mobile phase: A: CO2; B: MeOH (0.05% DEA) gradient: from 35 to 35 of B in 4.5 min and hold 40% for 2.5 min, then 5% of B for 1 min. Flow rate: 2.8 mL/min. Column temperature: 40° C.

Examples 498 and 499

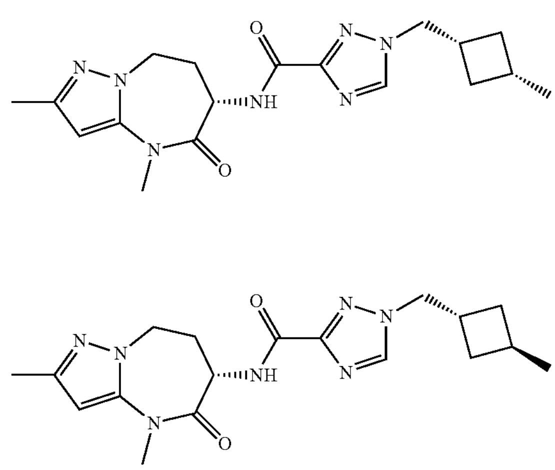

N—((S)-2,4-dimethyl-5-oxo-5,6,7,8-tetrahydro-4H-pyrazolo[1,5-a][1,3]diazepin-6-yl)-1-(((1S,3R)-3-methylcyclobutyl)methyl)-1H-1,2,4-triazole-3-carboxamide and N—((S)-2,4-dimethyl-5-oxo-5,6,7,8-tetrahydro-4H-pyrazolo[1,5-a][1,3]diazepin-6-yl)-1-(((1R,3S)-3-methylcyclobutyl)methyl)-1H-1,2,4-triazole-3-carboxamide The amide coupling prepared in a similar fashion to WX Method 015. The obtained racemic material (110 mg) was purified by chiral to give:

N—((S)-2,4-dimethyl-5-oxo-5,6,7,8-tetrahydro-4H-pyrazolo[1,5-a][1,3]diazepin-6-yl)-1-(((1S,3R)-3-methylcyclobutyl)methyl)-1H-1,2,4-triazole-3-carboxamide (Peak 1, Retention time=3.887 min) (49.1 mg, 44%) as a white solid. $^1$H NMR (400 MHz, $CD_3OD$) δ8.44 (s, 1H), 6.11 (s, 1H), 4.57-4.51 (m, 1H), 4.35-4.29 (m, 1H), 4.23-4.21 (m, 3H), 3.33 (s, 3H), 2.89-2.84 (m, 1H), 2.68-2.64 (m, 1H), 2.28-2.17 (m, 7H), 1.43-1.36 (m, 2H), 1.03 (d, J=6.4 Hz, 3H). LC-MS $R_T$=1.531 min, m/z=372.1 $[M+H]^+$.

LCMS (10 to 80% acetonitrile in water+0.03% ammonium bicarbonate over 3.0 mins) retention time 1.531 min, ESI+ found [M+H]=372.1.

N—((S)-2,4-dimethyl-5-oxo-5,6,7,8-tetrahydro-4H-pyrazolo[1,5-a][1,3]diazepin-6-yl)-1-(((1R,3S)-3-methylcyclobutyl)methyl)-1H-1,2,4-triazole-3-carboxamide (Peak 2 Retention time=4.496 min) (22.8 mg, 21%) as a white solid. $^1$H NMR (400 MHz, $CD_3OD$) δ8.48 (s, 1H), 6.11 (s, 1H), 4.56-4.51 (m, 1H), 4.34-4.29 (m, 3H), 4.24-4.22 (m, 1H), 3.33 (s, 3H), 2.89-2.83 (m, 2H), 2.45-2.43 (m, 1H), 2.25-2.19 (m, 4H), 2.01-1.94 (m, 2H), 1.76-1.69 (m, 2H), 1.12 (d, J=6.4 Hz, 3H). LC-MS $R_T$=1.531 min, m/z=372.0 $[M+H]^+$.

LCMS (10 to 80% acetonitrile in water+0.03% ammonium bicarbonate over 3.0 mins) retention time 1.531 min, ESI+ found [M+H]=372.0.

SFC condition: column: chiralpak AD-3 (100×4.6 mm), 3 um mobile phase: A: CO2; B: MeOH (0.05% DEA) gradient: from 5 to 40 of B in 4.5 min and hold 40% for 2.5 min, then 5% of B for 1 min. Flow rate: 2.8 mL/min. Column temperature: 40° C.

Examples 500 and 501

WX Method 017

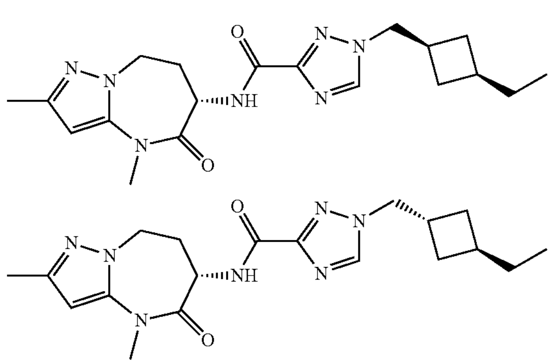

N—((S)-2,4-dimethyl-5-oxo-5,6,7,8-tetrahydro-4H-pyrazolo[1,5-a][1,3]diazepin-6-yl)-1-(((1R,3R)-3-ethylcyclobutyl)methyl)-1H-1,2,4-triazole-3-carboxamide and N—((S)-2,4-dimethyl-5-oxo-5,6,7,8-tetrahydro-4H-pyrazolo[1,5-a][1,3]diazepin-6-yl)-1-(((1S,3S)-3-ethylcyclobutyl)methyl)-1H-1,2,4-triazole-3-carboxamide

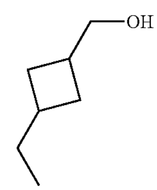

Step 1: (3-ethylcyclobutyl)methanol

To a solution of 3-ethylcyclobutanecarboxylic acid (600 mg, 4.68 mmol) in tetrahydrofuran (10 mL) was added $LiAlH_4$ (355 mg, 9.36 mmol) at 0° C. After addition, the mixture was stirred at 25° C. for 16 h and quenched by addition of water (0.1 mL), 15% aqueous NaOH (0.1 mL) and water (0.3 mL). The mixture was filtered and the filtrate was concentrated under reduced pressure to afford crude (3-ethylcyclobutyl)methanol (535 mg, 110%) as a colorless oil, used as is in the next step, used as is in the next step.

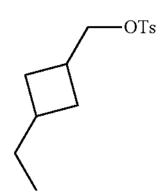 [SMILES: CCC1CC(COS(=O)(=O)c2ccc(C)cc2)C1]

Step 2: (3,3-dimethylcyclobutyl)methyl 4-methylbenzenesulfonate

To a solution of p-toluenesulfonylchloride (1071 mg, 5.62 mmol) in dichloromethane (10 mL) was added (3-ethylcyclobutyl)methanol (535 mg, 4.69 mmol) and 4-dimethylaminopyridine (1144 mg, 9.37 mmol). The reaction mixture was stirred at 20° C. for 16 h. Then the mixture was extracted with ethyl acetate (3×20 mL). The organic layer was washed with water (20 mL), brine (20 mL), dried over anhydrous sodium sulfate and concentrated under reduced pressure. The residue was purified by column chromatography (silica gel, 100-200 mesh, 0 to 30% ethyl acetate in petroleum ether) to afford (3-ethylcyclobutyl)methyl 4-methylbenzenesulfonate (810 mg, 64%) as a colorless oil, used as is in the next step.

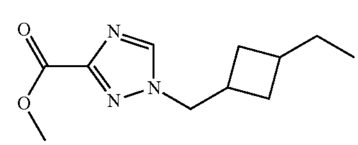 [SMILES: CCC1CC(Cn2cnc(C(=O)OC)n2)C1]

Step 3: methyl 1-[(3-ethylcyclobutyl)methyl]-1,2,4-triazole-3-carboxylate

To a solution of methyl 1H-1,2,4-triazole-3-carboxylate (383 mg, 3.02 mmol) and (3-ethylcyclobutyl)methyl 4-methylbenzenesulfonate (810 mg, 3.02 mmol) in N,N-dimethylformamide (20 mL) was added 4-dimethylamino-pyridine (442 mg, 3.62 mmol), cesium carbonate (2.95 g, 9.05 mmol) and sodium iodide (543 mg, 3.62 mmol). The mixture was stirred at 95° C. for 12 h and quenched by addition of water (30 mL). The mixture was extracted with ethyl acetate (4×20 mL). The combined organic layers were washed with water (3×20 mL), brine (2×20 mL), dried over anhydrous sodium sulfate and concentrated under reduced pressure. The residue was purified by column chromatography (silica gel: 100-200 mesh, 0-90% ethyl acetate in petroleum ether) to afford methyl 1-[(3-ethylcyclobutyl)methyl]-1,2,4-triazole-3-carboxylate (220 mg, 33%) as a colorless oil, used as is in the next step.

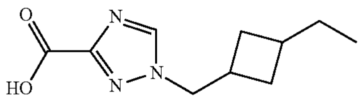

Step 4: 1-[(3-ethylcyclobutyl)methyl]-1,2,4-triazole-3-carboxylic acid

A mixture of methyl 1-[(3-ethylcyclobutyl)methyl]-1,2,4-triazole-3-carboxylate (100 mg, 0.45 mmol) and lithium hydroxide hydrate (94 mg, 2.24 mmol) in tetrahydrofuran/methanol/water (5 mL, 2:2:1) was stirred at 25° C. for 2 h. The solvent was evaporated under reduced pressure. The residue was diluted with water (20 mL) and adjusted to pH=4 by addition of 2N HCl. The resulting solid was collected by filtration and dried to give 1-[(3-ethylcyclobutyl)methyl]-1,2,4-triazole-3-carboxylic acid (74 mg, 79%) as a white solid, used as is in the next step.

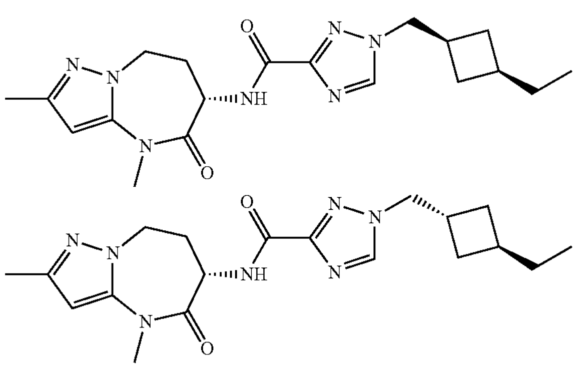

Step 5 N—((S)-2,4-dimethyl-5-oxo-5,6,7,8-tetrahydro-4H-pyrazolo[1,5-a][1,3]diazepin-6-yl)-1-(((1R,3R)-3-ethylcyclobutyl)methyl)-1H-1,2,4-triazole-3-carboxamide and N—((S)-2,4-dimethyl-5-oxo-5,6,7,8-tetrahydro-4H-pyrazolo[1,5-a][1,3]diazepin-6-yl)-1-(((1S,3S)-3-ethylcyclobutyl)methyl)-1H-1,2,4-triazole-3-carboxamide To a stirred solution of (6S)-6-amino-2,4-dimethyl-7,8-dihydro-6H-pyrazolo[1,5-a][1,3]diazepin-5-one (60 mg, 0.31 mmol) in N,N-dimethylformamide (5 mL) was added 1-[(3-ethylcyclobutyl)methyl]-1,2,4-triazole-3-carboxylic acid (71 mg, 0.34 mmol), 1-hydroxybenzotriazole (62 mg, 0.46 mmol) 1-(3-dimethylaminopropyl)-3-ethylcarbodiimide hydrochloride (89 mg, 0.46 mmol). The mixture was stirred at 25° C. for 12 h and concentrated under reduced pressure. The residue was purified by RP-HPLC (acetonitrile 33-53%/0.05% ammonium hydroxide in water) to afford the racemic compound which was separated by SFC to afford: N—((S)-2,4-dimethyl-5-oxo-5,6,7,8-tetrahydro-4H-pyrazolo[1,5-a][1,3]diazepin-6-yl)-1-(((1R,3R)-3-ethylcyclobutyl)methyl)-1H-1,2,4-triazole-3-carboxamide (Peak 1, retention time 4.975 min) (27 mg, 23%) as a white solid. $^1$H NMR (400 MHz, $CD_3OD$) δ 8.45 (s, 1H), 6.12 (s, 1H), 4.56-4.52 (m, 1H), 4.31-4.22 (m, 4H), 3.33 (s, 3H), 2.88-2.83 (m, 1H), 2.72-2.68 (m, 1H), 2.26-2.18 (m, 4H), 2.17-2.09 (m, 4H), 1.39-1.37 (m, 2H), 0.82-0.78 (m, 3H). LC-MS $R_T$=0.804 min, m/z=386.1 $[M+H]^+$.

LCMS (5 to 95% acetonitrile in water+0.1% trifluoacetic acid over 1.5 mins) retention time 0.804 min, ESI+ found [M+H]=386.1.

N—((S)-2,4-dimethyl-5-oxo-5,6,7,8-tetrahydro-4H-pyrazolo[1,5-a][1,3]diazepin-6-yl)-1-(((1S,3 S)-3-ethylcyclobutyl)methyl)-1H-1,2,4-triazole-3-carboxamide (Peak 2, retention time 5.253 min) (6 mg, 5%) as a white solid. $^1$H NMR (400 MHz, $CD_3OD$) δ8.49 (s, 1H), 6.12 (s, 1H), 4.56-4.52 (m, 1H), 4.35-4.22 (m, 4H), 3.33 (s, 3H), 2.86-2.82 (m, 2H), 2.26-2.23 (m, 4H), 1.95-1.91 (m, 2H), 1.80-1.76 (m, 2H), 1.49-1.46 (m, 2H), 0.85-0.80 (m, 3H). LC-MS $R_T$=0.806 min, m/z=386.1 $[M+H]^+$.

LCMS (5 to 95% acetonitrile in water+0.1% trifluoacetic acid over 1.5 mins) retention time 0.806 min, ESI+ found [M+H]=386.1

SFC condition: Column: Chiralcel AD-3 150×4.6 mm I.D., 3 um Mobile phase: A: CO2 B: ethanol (0.05% dethyl acetate), Gradient: from 5% to 40% of B in 5.0 min and hold 40% for 2.5 min, then 5% of B for 2.5 min, Flow rate: 2.5 mL/min Column temperature: 35° C.

Examples 502 and 503

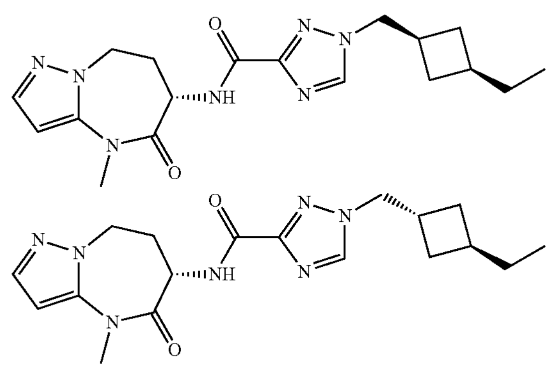

N—((S)-4-methyl-5-oxo-5,6,7,8-tetrahydro-4H-pyrazolo[1,5-a][1,3]diazepin-6-yl)-1-(((1R,3R)-3-ethylcyclobutyl)methyl)-1H-1,2,4-triazole-3-carboxamide and N—((S)-4-methyl-5-oxo-5,6,7,8-tetrahydro-4H-pyrazolo[1,5-a][1,3]diazepin-6-yl)-1-(((1S,3 S)-3-ethylcyclobutyl)methyl)-1H-1,2,4-triazole-3-carboxamide Amide coupling prepared in a similar fashion to WX Method 017. The crude was purified by RP-HPLC (acetonitrile 22 to 52%/0.05% ammonium hydroxide in water) to give N—((S)-4-methyl-5-oxo-5,6,7,8-tetrahydro-4H-pyrazolo[1,5-a][1,3]diazepin-6-yl)-1-((3-ethylcyclobutyl)methyl)-1H-1,2,4-triazole-3-carboxamide (75 mg, 61%) as a white solid. This material was separated by chiral SFC to give:

N—((S)-4-methyl-5-oxo-5,6,7,8-tetrahydro-4H-pyrazolo[1,5-a][1,3]diazepin-6-yl)-1-(((1R,3R)-3-ethylcyclobutyl)methyl)-1H-1,2,4-triazole-3-carboxamide (Peak 1, retention time=5.49 min) (25 mg, 67%) as a white solid. $^1$H NMR (400 MHz, $CD_3OD$) δ8.44 (s, 1H), 7.52 (s, 1H), 6.30 (s, 1H), 4.54-4.38 (m, 2H), 4.33-4.25 (m, 1H), 4.22 (d, J=7.2 Hz, 2H), 3.35 (s, 3H), 2.89-2.87 (m, 1H), 2.67-2.64 (m, 1H), 2.28-2.25 (m, 1H), 2.16-2.07 (m, 3H), 1.42-1.34 (m, 4H), 0.79 (t, J=7.2 Hz, 1H). LCMS $R_T$=1.62 min, m/z=372.2 $[M+H]^+$.

LCMS (10 to 80% acetonitrile in water+0.05% ammonium hydroxide over 3 mins) retention time 1.62 min, ESI+ found [M+H]=372.2.

N—((S)-4-methyl-5-oxo-5,6,7,8-tetrahydro-4H-pyrazolo[1,5-a][1,3]diazepin-6-yl)-1-(((1 S,3 S)-3-ethylcyclobutyl)methyl)-1H-1,2,4-triazole-3-carboxamide (Peak 2, Retention time=5.78 min) (26 mg, 67%) as a white solid. $^1$H NMR (400 MHz, $CD_3OD$) δ 8.48 (s, 1H), 7.52 (s, 1H), 6.30 (s, 1H), 4.53-4.51 (m, 1H), 4.42-4.39 (m, 1H), 4.34-4.27 (m, 3H), 3.35 (s, 3H), 2.89-2.81 (m, 2H), 2.27-2.22 (m, 2H), 1.92-1.89 (m, 2H), 1.79-1.75 (m, 2H), 1.48-1.44 (m, 2H), 0.82 (t, J=7.2 Hz, 1H). LCMS $R_T$=1.62 min, m/z=372.2 $[M+H]^+$.

LCMS (10 to 80% acetonitrile in water+0.05% ammonium hydroxide over 3 mins) retention time 1.62 min, ESI+ found [M+H]=372.2.

SFC conditions: Column: Chiralcel AD-3 150×4.6 mm I.D., 3 um Mobile phase: A: $CO_2$ B: methanol (0.05% ethyl acetate), Gradient: from 5% to 40% of B in 5.0 min and hold 40% for 2.5 min, then 5% of B for 2.5 min, Flow rate: 2.5 mL/min Column temperature: 35° C.

Example 504

WX Method 100

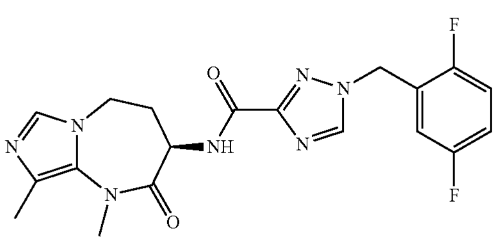 [SMILES: Cc1ncn2c1N(C)C(=O)[C@H](NC(=O)c1ncn(Cc3cc(F)ccc3F)n1)CC2]

1-[(2,5-difluorophenyl)methyl]-N-(3R)-1,9-dimethyl-2-oxo-4,5-dihydro-3H-imidazo[1,5-a][1,3]diazepin-3-yl-1,2,4-triazole-3-carboxamide A mixture of 1-[(2,5-difluorophenyl)methyl]-1,2,4-triazole-3-carboxylic acid (74 mg, 0.31 mmol), 1-(3-dimethylaminopropyl)-3-ethylcarbodiimidehydrochloride (59 mg, 0.31 mmol), 1-hydroxybenzotriazole (42 mg, 0.31 mmol) and 3-amino-1,9-dimethyl-4,5-dihydro-3H-imidazo[1,5-a][1,3]diazepin-2-one (50 mg, 0.26 mmol) in N,N-dimethylformamide (5 mL) was stirred at 25° C. for 16 h. The mixture was concentrated under reduced pressure and the residue was purified by RP-HPLC (5% to 35% acetonitrile/0.05% ammonia hydroxide in water) to afford 1-[(2,5-difluorophenyl)methyl]-N-(1,9-dimethyl-2-oxo-4,5-dihydro-3H-imidazo[1,5-a][1,3]di azepin-3-yl)-1,2,4-triazole-3-carboxamide (70 mg, 66%) as a white solid. The obtained racemic compound was separated by chiral SFC to give:

1-[(2,5-difluorophenyl)methyl]-N-(3R)-1,9-dimethyl-2-oxo-4,5-dihydro-3H-imidazo[1,5-a][1,3]diazepin-3-yl-1,2,4-triazole-3-carboxamide (Peak 2, retention time 3.664 min) (30 mg, 42%) as a white solid. $^1$H NMR (400 MHz, $CD_3OD$) δ8.65 (s, 1H), 8.04 (s, 1H), 7.21-7.14 (m, 3H), 5.56 (s, 2H), 4.63-4.58 (m, 1H), 4.47-4.41 (m, 1H), 4.07-4.03 (m, 1H), 3.32 (s, 3H), 2.73-2.65 (m, 1H), 2.27 (s, 3H), 2.22-2.16 (m, 1H). LCMS $R_T$=0.557 min; m/z=416.0 $(M+H)^+$.

LCMS (5 to 95% acetonitrile in water+0.03% trifluoacetic acid over 1.5 mins) retention time 0.557 min, ESI+ found [M+H]=416.0.

SFC conditions: Column: Chiralcel OJ-3 100×4.6 mm I.D., 3 um, Mobile phase: A: $CO_2$ B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 505

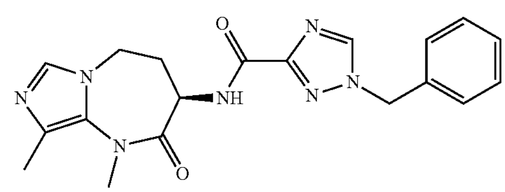 [SMILES: Cc1ncn2c1N(C)C(=O)[C@H](NC(=O)c1ncn(Cc3ccccc3)n1)CC2]

1-benzyl-N-(3R)-1,9-dimethyl-2-oxo-4,5-dihydro-3H-imidazo[1,5-a][1,3]diazepin-3-yl-1, 2,4-triazole-3-carboxamide Amide coupling prepared in a similar fashion to WX Method 100. The racemic material was separated by chiral SFC to give:

1-benzyl-N-[(3R)-1,9-dimethyl-2-oxo-4,5-dihydro-3H-imidazo[1,5-a][1,3]diazepin-3-yl]-1,2, 4-triazole-3-carboxamide (Peak 2, retention time 3.944 min) (57.7 mg, 29%) as a white solid.

$^1$H NMR (400 MHz, $CD_3OD$) δ8.58 (s, 1H), 7.78 (s, 1H), 7.39-7.32 (m, 4H), 5.47 (s, 2H), 4.59-4.54 (m, 1H), 4.41-4.35 (m, 1H), 4.01-3.94 (m, 1H), 3.31 (s, 3H), 2.72-2.66 (m, 1H), 2.24 (s, 3H), 2.15-2.10 (m, 1H). LCMS $R_T$=0.508 min; m/z=380.0 $(M+H)^+$.

LCMS (5 to 95% acetonitrile in water+0.03% trifluoacetic acid over 1.5 mins) retention time 0.508 min, ESI+ found [M+H]=380.0

SFC conditions: Column: Chiralpak OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.8 mL/min Column temp.: 40° C.).

Example 506

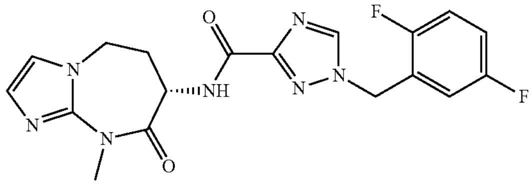 [SMILES: CN1C(=O)[C@@H](NC(=O)c2ncn(Cc3cc(F)ccc3F)n2)CCn2ccnc21]

1-[(2,5-difluorophenyl)methyl]-N-[(7S)-9-methyl-8-oxo-6,7-dihydro-5H-imidazo[1,2-a][1,3]diazepin-7-yl]-1,2,4-triazole-3-carboxamide Amide coupling prepared in a similar fashion to WX Method 100. The racemic material was separated by chiral SFC to give:

1-[(2,5-difluorophenyl)methyl]-N-[(7S)-9-methyl-8-oxo-6,7-dihydro-5H-imidazo[1,2-a][1,3]diazepin-7-yl]-1,2,4-triazole-3-carboxamide (Peak 1, retention time 3.766 min) (15 mg, 18.6%): $^1$H NMR (400 MHz, $CD_3OD$) δ8.61 (s, 1H), 7.19-7.10 (m, 3H), 7.09 (s, 1H), 6.95 (s, 1H), 5.53 (s, 2H), 4.54-4.47 (m, 1H), 4.32-4.25 (m, 1H), 4.09-4.02 (m, 1H), 3.38 (s, 3H), 2.87-2.79 (m, 1H), 2.30-2.24 (m, 1H). LCMS $R_T$=1.324 min; m/z=402.2 $(M+H)^+$.

LCMS (10 to 80% acetonitrile in water+0.05% ammonium bicarbonate over 3 mins) retention time 1.324, ESI+ found [M+H]=402.2.

SFC conditions: Column: Chiralcel OJ-3 250×30 mm I.D., 10 um Mobile phase: A: CO2 B: ethanol (0.05% DEA) Gradient: from 30% to 30%, Flow rate: 80 mL/min, Column temp.: 40° C.

Example 507

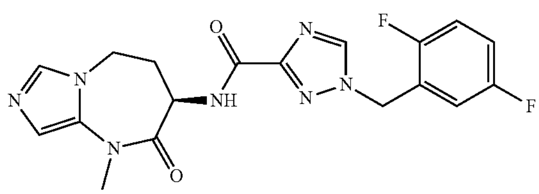 [SMILES: CN1C(=O)[C@H](NC(=O)c2ncn(Cc3cc(F)ccc3F)n2)CCn2cncc21]

1-[(2,5-difluorophenyl)methyl]-N-[(3R)-1-methyl-2-oxo-4,5-dihydro-3H-imidazo[1,5-a][1,3]diazepin-3-yl]-1,2,4-triazole-3-carboxamide Amide coupling prepared in a similar fashion to WX Method 100. The racemic material was separated by chiral SFC to give:

1-[(2,5-difluorophenyl)methyl]-N-[(3R)-1-methyl-2-oxo-4,5-dihydro-3H-imidazo[1,5-a][1,3]diazepin-3-yl]-1,2,4-triazole-3-carboxamide (Peak 2, retention time 4.162 min) (33.8 mg 33%) as white solids. $^1$H NMR (400 MHz, DMSO-$d_6$) δ 8.81 (s, 1H), 8.49 (d, J=8.0 Hz, 1H), 7.58 (s, 1H), 7.39-7.18 (m, 3H), 6.96 (s, 1H), 5.54 (s, 2H), 4.43-4.30 (m, 2H), 3.87-3.78 (m, 1H), 3.23 (s, 3H), 2.44 (s, 1H), 2.28-2.22 (m, 1H). LCMS $R_T$=1.716 min; m/z=402.2 $(M+H)^+$.

LCMS (0 to 60% acetonitrile in water+0.03% ammonium bicarbonate over 3.0 mins) retention time 1.716 min, ESI+ found [M+H]=402.2.

SFC conditions: Column: Chiralcel OJ-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 508

WX Method 162

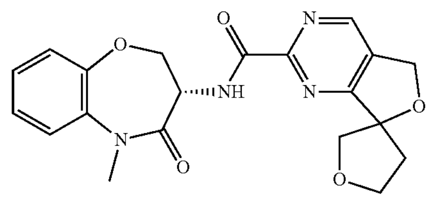 [SMILES: CN1C(=O)[C@@H](NC(=O)c2ncc3c(n2)C2(CCOC2)OC3)COc2ccccc21]

N-[(3S)-5-methyl-4-oxo-2,3-dihydro-1,5-benzoxazepin-3-yl]spiro[5H-furo[3,4-d]pyrimidine-7,3'-tetrahydrofuran]-2-carboxamide

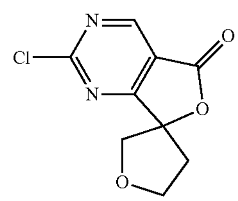 [SMILES: O=C1OC2(CCOC2)c2nc(Cl)ncc21]

Step 1: 2'-chloro-4,5-dihydro-2H,5'H-spiro[furan-3,7'-furo[3,4-d]pyrimidin]-5'-one To a solution of 2,2,6,6-tetramethylpiperidine (13.36 g, 94.6 mmol) in tetrahydrofuran (60 mL) was added n-butyllithium (2.5 M in hexanes, 50.5 mL, 126.2 mmol) at −78° C. The reaction mixture was stirred at −78° C. for 1 h and 2-chloropyrimidine-5-carboxylic acid (5.0 g, 31.5 mmol) was added. The reaction mixture was stirred at −78° C. for another 2 h and dihydrofuran-3(2H)-one (10.61 g, 126.2 mmol) was added. After addition, the reaction mixture was stirred at 25° C. for 16 h and quenched by addition of saturated ammonium chloride (30 mL). The mixture was extracted with ethyl acetate (3×50 mL). The combined organic layers were dried over sodium sulfate and concentrated under reduced pressure. The residue was purified by column chromatography (silica gel 100-200 mesh, eluting 0-30% ethyl acetate in petroleum ether) to afford 2'-chloro-4,5-dihydro-2H,5'H-spiro[furan-3,7'-furo[3,4-d]pyrimidin]-5'-one (700 mg, 10%) as yellow oil, used as is in the next step.

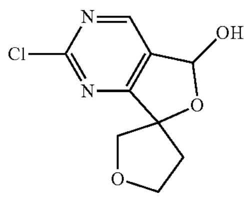 [SMILES: OC1OC2(CCOC2)c2nc(Cl)ncc21]

Step 2: 2'-chloro-4,5-dihydro-2H,5'H-spiro[furan-3, 7'-furo[3,4-d]pyrimidin]-5'-ol To a solution of 2'-chloro-4,5-dihydro-2H,5'H-spiro [furan-3,7'-furo[3,4-d]pyrimidin]-5'-one (700 mg, 3.09 mmol) in toluene (35 mL) was added diisobutylaluminum-hydride (7.67 mL, 7.67 mmol, 1.0 M in toluene) at −78° C. The mixture was stirred at −78° C. for 2 h and quenched by addition of saturated ammonium chloride (15 mL). The solution was extracted with ethyl acetate (3×50 mL). The combined organic layers were washed with water (20 mL), brine (20 mL), dried over sodium sulfate and concentrated under reduced pressure. The residue was purified by column chromatography (silica gel, 100-200 mesh, 0 to 50% ethyl acetate in petroleum ether) to afford 2'-chloro-4,5-dihydro-2H,5'H-spiro [furan-3,7'-furo[3,4-d]pyrimidin]-5'-ol (250 mg, 35%) as light yellow oil, used as is in the next step.

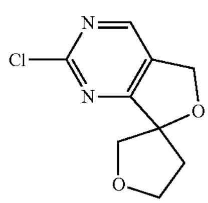 [SMILES: Clc1ncc2c(n1)C1(CCOC1)OC2]

Step 3: 2'-chloro-4,5-dihydro-2H,5'H-spiro[furan-3, 7'-furo[3,4-d]pyrimidine]

A mixture of 2'-chloro-4,5-dihydro-2H,5'H-spiro[furan-3, 7'-furo[3,4-d]pyrimidin]-5'-ol (250 mg, 1.1 mmol) and trifluoroacetic acid (0.41 mL, 5.5 mmol) in dichloromethane (20 mL) was added triethylsilane (0.87 mL, 5.5 mmol) at 0° C. The reaction mixture was stirred at 25° C. for 15 h and concentrated under reduced pressure. The residue was purified by column chromatography (silica gel, 100-200 mesh, 0 to 30% ethyl acetate in petroleum ether) to afford 2'-chloro-4,5-dihydro-2H, 5'H-spiro[furan-3,7'-furo[3,4-d]pyrimidine] (190 mg, 81%) as a yellow oil, used as is in the next step.

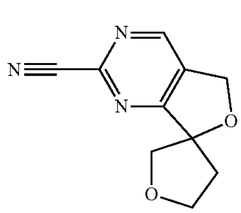 [SMILES: N#Cc1ncc2c(n1)C1(CCOC1)OC2]

Step 4: 4,5-dihydro-2H,5'H-spiro[furan-3,7'-furo[3, 4-d]pyrimidine]-2'-carbonitrile To a solution of 2'-chloro-4,5-dihydro-2H, 5'H-spiro [furan-3,7'-furo[3,4-d]pyrimidine] (190 mg, 0.89 mmol) in dimethyl sulfoxide (10 mL) and water (2 mL) was added 1,4-diazabicyclo[2.2.2]octane (20 mg, 0.18 mmol) and sodium cyanide (189 mg, 3.87 mmol). The reaction mixture was stirred at 25° C. for 7 h and extracted with ethyl acetate (2×20 mL). The combined organic layers were dried over sodium sulfate and concentrated under reduced pressure. The residue was purified by column chromatography (silica gel, 100-200 mesh, 0 to 100% ethyl acetate in petroleum ether) to afford 4,5-dihydro-2H,5'H-spiro[furan-3,7'-furo[3, 4-d]pyrimidine]-2'-carbonitrile (120 mg, 66%) as a colourless oil.

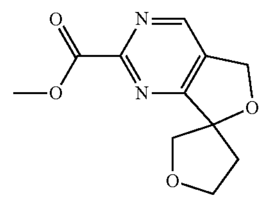 [SMILES: COC(=O)c1ncc2c(n1)C1(CCOC1)OC2]

Step 5: methyl 4,5-dihydro-2H,5'H-spiro[furan-3,7'-furo[3,4-d]pyrimidine]-2'-carboxylate To a solution of 4,5-dihydro-2H,5'H-spiro[furan-3,7'-furo [3,4-d]pyrimidine]-2'-carbonitrile (120 mg, 0.59 mmol) in methanol (5 mL) was added HCl (4N in methanol, 2.4 mL). The reaction mixture was stirred at 25° C. for 15 h and concentrated under reduced pressure to afford crude methyl 4,5-dihydro-2H,5'H-spiro[furan-3,7'-furo[3,4-d]pyrimidine]-2'-carboxylate (130 mg, 93%) as a white solid, used as is in the next step.

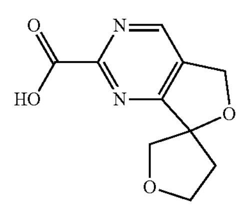 [SMILES: O=C(O)c1ncc2c(n1)C1(CCOC1)OC2]

Step 6: 4,5-dihydro-2H,5'H-spiro[furan-3,7'-furo[3, 4-d]pyrimidine]-2'-carboxylic acid A mixture of methyl 4,5-dihydro-2H,5'H-spiro[furan-3,7'-furo[3,4-d]pyrimidine]-2'-carboxylate (130 mg, 0.55 mmol) and lithium hydroxide hydrate (132 mg, 5.50 mmol) in tetrahydrofuran (12 mL) and water (3 mL) was stirred at 25° C. for 2 h. The mixture was quenched by addition of 1N HCl (3 mL) and extracted with ethyl acetate (2×20 mL). The combined organic layers were dried over sodium sulfate and concentrated under reduced pressure to afford crude 4,5-dihydro-2H,5'H-spiro[furan-3,7'-furo[3,4-d]pyrimidine]-2'-carboxylic acid (100 mg, 82%) as a yellow solid, used as is in the next step.

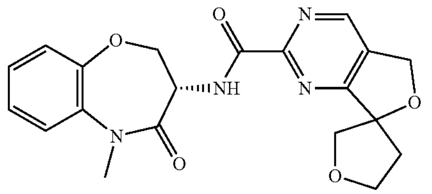 [SMILES: CN1C(=O)[C@@H](NC(=O)c2ncc3c(n2)C2(CCOC2)OC3)COc2ccccc21]

Step 7: N-[(3S)-5-methyl-4-oxo-2,3-dihydro-1,5-benzoxazepin-3-yl]spiro[5H-furo[3,4-d]pyrimidine-7,3'-tetrahydrofuran]-2-carboxamide A mixture of spiro[5H-furo[3,4-d]pyrimidine-7,3'-tetrahydrofuran]-2-carboxylic acid (69 mg, 0.31 mmol), (3S)-3-amino-5-methyl-2,3-dihydro-1,5-benzoxazepin-4-one (50 mg, 0.26 mmol), 1-(3-dimethylaminopropyl)-3-ethylcarbodiimidehydrochloride (60 mg, 0.31 mmol) and 1-hydroxybenzotriazole (42 mg, 0.31 mmol) in N,N-dimethylformamide (5 mL) was stirred at 25° C. for 12 h. The mixture was concentrated under reduced pressure and the residue was purified by RP-HPLC (24% to 54% acetonitrile/0.05% ammonia hydroxide in water) to give N-[(3S)-5-methyl-4-oxo-2,3-dihydro-1,5-benzoxazepin-3-yl]spiro[5H-furo[3,4-d]pyrimidine-7,3'-tetrahydrofuran]-2-carboxamide (41 mg, 40%) as a white solid. $^1$H NMR (400 MHz, $CD_3OD$) δ8.85 (s, 1H), 7.46-7.44 (m, 1H), 7.36-7.29 (m, 2H), 7.27-7.24 (m, 1H), 5.19 (s, 2H), 5.08-5.03 (m, 1H), 4.68-4.64 (m, 1H), 4.49-4.43 (m, 1H), 4.17-4.02 (m, 4H), 3.43 (s, 3H), 2.49-2.40 (m, 1H), 2.34-2.29 (m, 1H). LC-MS $R_T$=0.891 min, m/z=397.1 $(M+H)^+$.

LCMS (10 to 80% acetonitrile in water+0.03% trifluoacetic acid over 2.0 mins) retention time 0.891 min, ESI+ found [M+H]=397.1.

Example 509

WX Method 175

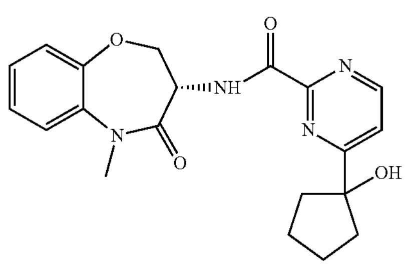 [SMILES: CN1C(=O)[C@@H](NC(=O)c2nccc(C3(O)CCCC3)n2)COc2ccccc21]

4-(1-hydroxycyclopentyl)-N-[(3S)-5-methyl-4-oxo-2,3-dihydro-1,5-benzoxazepin-3-yl]pyrimidine-2-carboxamide

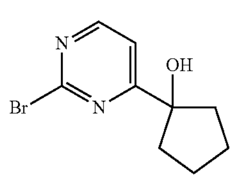 [SMILES: OC1(c2ccnc(Br)n2)CCCC1]

Step 1: 1-(2-bromopyrimidin-4-yl)cyclopentanol

To a solution of 2-bromo-4-iodo-pyrimidine (500 mg, 1.8 mmol) and cyclopentanone (221 mg, 2.6 mmol) in tetrahydrofuran (15 mL) was added isopropylmagnesium chloride (1.0 M in tetrahedron, 2.0 mL, 2.0 mmol) at −70° C. The mixture was stirred at −70° C. for 1 h and quenched by addition of saturated ammonium chloride (10 mL). The mixture was extracted with ethyl acetate (3×20 mL). The combined organic layers were washed with water (3×20 mL), brine (2×20 mL), dried over sodium sulfate and concentration under reduced pressure. The residue was purified by column chromatography (silica gel, 100-200 mesh, 0 to 25% ethyl acetate in petroleum ether) to afford 1-(2-bromopyrimidin-4-yl)cyclopentanol (80 mg, 19%) as colorless oil. $^1$H NMR (400 MHz, $CD_3OD$) δ8.55 (d, J=5.0 Hz, 1H), 7.76 (d, J=5.3 Hz, 1H), 2.21-2.13 (m, 2H), 2.00-1.83 (m, 6H).

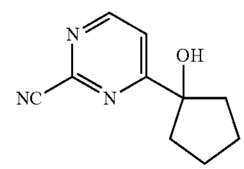 [SMILES: N#Cc1nccc(C2(O)CCCC2)n1]

Step 2: 4-(1-hydroxycyclopentyl)pyrimidine-2-carbonitrile

To a solution of 1-(2-bromopyrimidin-4-yl)cyclopentanol (40 mg, 0.16 mmol) in dimethylsulfoxide (2 mL) and water (1 mL) was added 1,4-diazabicyclo[2.2.2]octane (18 mg, 0.16 mmol) and sodium cyanide (16 mg, 0.33 mmol). The mixture was stirred at 25° C. for 16 h and extracted with ethyl acetate (3×10 mL). The combined organic layers were washed with brine (10 mL), dried over sodium sulfate and concentrated under reduced pressure to afford crude 4-(1-hydroxycyclopentyl)pyrimidine-2-carbonitrile (30 mg, 96%) as yellow oil. $^1$H NMR (400 MHz, $CD_3OD$) δ8.84 (d, J=5.6 Hz, 1H), 7.98 (d, J=5.6 Hz, 1H), 2.19-2.17 (m, 2H), 1.99-1.87 (m, 6H).

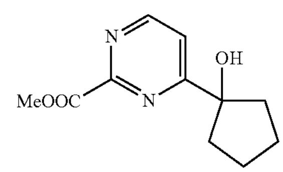 [SMILES: COC(=O)c1nccc(C2(O)CCCC2)n1]

Step 3: methyl 4-(1-hydroxycyclopentyl)pyrimidine-2-carboxylate

To a solution of 4-(1-hydroxycyclopentyl)pyrimidine-2-carbonitrile (25 mg, 0.13 mmol) in methanol (5 mL) was added HCl (4N in methanol, 1.5 mL). The mixture was stirred at 25° C. for 20 h. The mixture was concentrated under reduced pressure and the residue was purified by preparative TLC (50% ethyl acetate in petroleum ether, $R_f$=0.3) to give methyl 4-(1-hydroxycyclopentyl)pyrimidine-2-carboxylate (15 mg, 51%) as colorless oil. $^1$H NMR (400 MHz, $CD_3OD$) δ8.86 (d, J=5.6 Hz, 1H), 7.94 (d, J=5.6

Hz, 1H), 4.00 (s, 3H), 2.27-2.23 (m, 2H), 1.98-1.86 (m, 6H). LCMS $R_T$=0.523 min, m/z=223.0 $[M+H]^+$.

LCMS (5 to 95% acetonitrile in water+0.03% trifluoacetic acid over 1.5 mins) retention time 0.523 min, ESI+ found [M+H]=223.0.

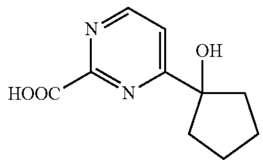 [SMILES: O=C(O)c1nccc(C2(O)CCCC2)n1]

Step 4: 4-(1-hydroxycyclopentyl)pyrimidine-2-carboxylic acid

A mixture of methyl 4-(1-hydroxycyclopentyl)pyrimidine-2-carboxylate (15 mg, 0.07 mmol) and lithium hydroxide hydrate (14 mg, 0.34 mmol) in tetrahydrofuran (2 mL), methanol (2 mL) and water (1 mL) was stirred at 25° C. for 16 h. The solution was adjusted to pH=4-5 by addition of 1N HCl. The mixture was concentrated under reduced pressure to give crude 4-(1-hydroxycyclopentyl)pyrimidine-2-carboxylic acid (11 mg, 78%) as a yellow solid. LCMS $R_T$=0.290 min, m/z=208.9 $[M+H]^+$.

LCMS (5 to 95% acetonitrile in water+0.03% trifluoacetic acid over 1.5 mins) retention time 0.290 min, ESI+ found [M+H]=208.9.

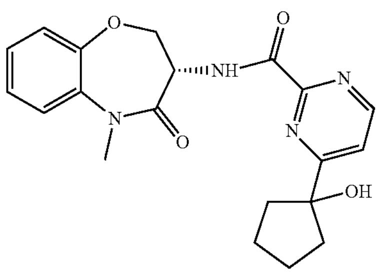 [SMILES: CN1C(=O)[C@@H](NC(=O)c2nccc(C3(O)CCCC3)n2)COc2ccccc21]

Step 5: 4-(1-hydroxycyclopentyl)-N-[(3S)-5-methyl-4-oxo-2,3-dihydro-1,5-benzoxazepin-3-yl]pyrimidine-2-carboxamide A mixture of (3S)-3-amino-5-methyl-2,3-dihydro-1,5-benzoxazepin-4-one (10 mg, 0.05 mmol), 4-(1-hydroxycyclopentyl)pyrimidine-2-carboxylicacid (10 mg, 0.05 mmol), 1H-benzo[d][1,2,3]triazol-1-ol (8 mg, 0.06 mmol) and $N^1$-((ethylimino)methylene)-$N^3$,$N^3$-dimethylpropane-1,3-diamine hydrochloride (11 mg, 0.06 mmol) in N,N-dimethylformamide (3 mL) was stirred at 25° C. for 16 h. The mixture was concentrated under reduced pressure and the residue was purified by RP-HPLC (acetonitrile 25% to 55%/0.05% ammonia hydroxide in water) to give 4-(1-hydroxycyclopentyl)-N-[(3S)-5-methyl-4-oxo-2,3-dihydro-1,5-benzoxazepin-3-yl]pyrimidine-2-carboxamide (10.3 mg, 56%) as a white solid. $^1$H NMR (400 MHz, CD3OD) δ 8.87 (d, J=5.2 Hz, 1H), 7.90 (d, J=4.8 Hz, 1H), 7.47-7.42 (m, 1H), 7.36-7.29 (m, 2H), 7.28-7.23 (m, 1H), 5.05-5.00 (m, 1H), 4.71-4.67 (m, 1H), 4.44-4.39 (m, 1H), 3.44 (s, 3H), 2.28-2.24 (m, 2H), 2.03-1.96 (m, 6H). LC-MS $R_T$=0.664 min, m/z=383.1 $[M+H]^+$.

LCMS (0-60% acetonitrile in water+0.05% ammonium bicarbonate over 3 mins) retention time 2.023 min, ESI+ found [M+H]=383.1.

Example 510

WX Method 160

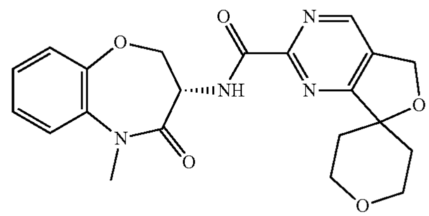 [SMILES: CN1C(=O)[C@@H](NC(=O)c2ncc3c(n2)C2(CCOCC2)OC3)COc2ccccc21]

N-[(6S)-2,4-dimethyl-5-oxo-7,8-dihydro-6H-pyrazolo[1,5-a][1,3]diazepin-6-yl]spiro[5H-furo[3,4-d]pyrimidine-7,3'-tetrahydropyran]-2-carboxamide

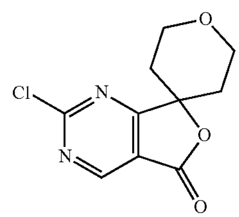 [SMILES: O=C1OC2(CCOCC2)c2nc(Cl)ncc21]

Step 1: 2-chloro-2',3',5',6'-tetrahydro-5H-spiro[furo[3,4-d]pyrimidine-7,4'-pyran]-5-one To a solution of 2,2,6,6-tetramethylpiperidine (13.36 g, 94.6 mmol) in tetrahydrofuran (80 mL) was added n-butyllithium (2.5 M in hexanes, 25.2 mL, 63.0 mmol) at −78° C. The reaction mixture was stirred at −78° C. for 1 h and 2-chloropyrimidine-5-carboxylic acid (5.0 g, 31.5 mmol) was added. The reaction mixture was stirred at −78° C. for another 2 h and dihydro-2H-pyran-4(3H)-one (9.47 g, 94.6 mmol) was added. After addition, the reaction mixture was stirred at 25° C. for 16 h and quenched by addition of saturated ammonium chloride (30 mL). The mixture was extracted with ethyl acetate (3×100 mL). The combined organic layers were dried over sodium sulfate and concentrated under reduced pressure. The residue was purified by flash column chromatography (silica gel, 100-200 mesh, 0 to 30% ethyl acetate in petroleum ether) to afford 2-chloro-2',3',5',6'-tetrahydro-5H-spiro[furo[3,4-d]pyrimidine-7,4'-pyran]-5-one (1.5 g, 20%) as a yellow solid.

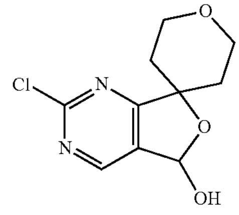 [SMILES: OC1OC2(CCOCC2)c2nc(Cl)ncc21]

Step 2: 2-chloro-2',3',5',6'-tetrahydro-5H-spiro[furo[3,4-d]pyrimidine-7,4'-pyran]-5-ol To a solution of 2-chloro-2',3',5',6'-tetrahydro-5H-spiro[furo[3,4-d]pyrimidine-7,4'-pyran]-5-one (100 mg, 0.42 mmol) in tetrahydrofuran (3 mL) was added diisobutylaluminumhydride (1.66 mL, 1.66 mmol, 1.0 M in toluene). The reaction mixture was stirred at −70° C. for 2 h and quenched by addition of saturated ammonium chloride (10 mL). The mixture was extracted with ethyl acetate (3×10 mL). The combined organic layers were dried over sodium sulfate and concentrated under reduced pressure. The residue was purified by preparative TLC (50% ethyl acetate in petroleum ether, Rf=0.3) to afford 2-chloro-2',3',5',6'-tetrahydro-5H-spiro[furo[3,4-d]pyrimidine-7,4'-pyran]-5-ol (50 mg, 50%) as a colourless oil.

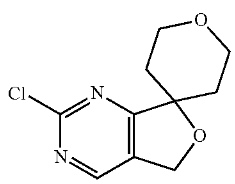 [SMILES: Clc1ncc2c(n1)C1(CCOCC1)OC2]

Step 3: 2-chloro-2',3',5',6'-tetrahydro-5H-spiro[furo[3,4-d]pyrimidine-7,4'-pyran]

To a solution of 2-chloro-2',3',5',6'-tetrahydro-5H-spiro[furo[3,4-d]pyrimidine-7,4'-pyran]-5-ol (50 mg, 0.21 mmol) and trifluoroacetic acid (0.4 g, 3.53 mmol) in dichloromethane (5 mL) was added triethylsilane (118 mg, 1.03 mmol) at 0° C. After addition, the mixture was stirred at 25° C. for 12 h and concentrated under reduced pressure. The residue was purified by preparative TLC (33% ethyl acetate in petroleum ether, Rf=0.4) to afford 2-chloro-2',3',5',6'-tetrahydro-5H-spiro[furo[3,4-d]pyrimidine-7,4'-pyran] (30 mg, 64%) as a light yellow solid.

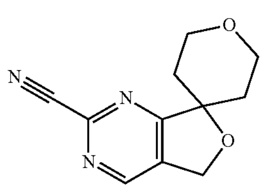 [SMILES: N#Cc1ncc2c(n1)C1(CCOCC1)OC2]

Step 4: 2',3',5',6'-tetrahydro-5H-spiro[furo[3,4-d]pyrimidine-7,4'-pyran]-2-carbonitrile To a solution of 2-chloro-2',3',5',6'-tetrahydro-5H-spiro[furo[3,4-d]pyrimidine-7,4'-pyran] (30 mg, 0.13 mmol) in dimethyl sulfoxide (4 mL) and water (2 mL) was added 1,4-diazabicyclo[2.2.2]octane (8 mg, 0.07 mmol) and sodium cyanide (21 mg, 0.43 mmol). The reaction mixture was stirred at 25° C. for 12 h and extracted with ethyl acetate (3×15 mL). The combined organic layers were dried over sodium sulfate and concentrated under reduced pressure to give crude 2',3',5',6'-tetrahydro-5H-spiro[furo[3,4-d]pyrimidine-7,4'-pyran]-2-carbonitrile (20 mg, 70%) as a light yellow solid.

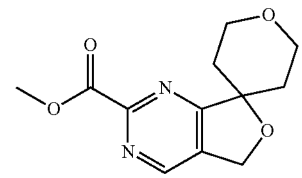 [SMILES: COC(=O)c1ncc2c(n1)C1(CCOCC1)OC2]

Step 5: methyl 2',3',5',6'-tetrahydro-5H-spiro[furo[3,4-d]pyrimidine-7,4'-pyran]-2-carboxylate To a solution of 2',3',5',6'-tetrahydro-5H-spiro[furo[3,4-d]pyrimidine-7,4'-pyran]-2-carbonitrile (20 mg, 0.09 mmol) in methanol (1.5 mL) and was added HCl (4N in methanol, 0.5 mL). The reaction mixture was stirred at 25° C. for 2 h and 35° C. for 15 h. The mixture was concentrated under reduced pressure to afford crude methyl 2',3',5',6'-tetrahydro-5H-spiro[furo[3,4-d]pyrimidine-7,4'-pyran]-2-carboxylate (15 mg, 65%) as a yellow solid.

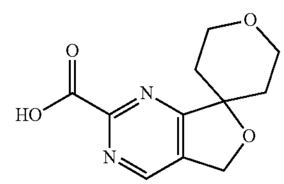 [SMILES: O=C(O)c1ncc2c(n1)C1(CCOCC1)OC2]

Step 6: 2',3',5',6'-tetrahydro-5H-spiro[furo[3,4-d]pyrimidine-7,4'-pyran]-2-carboxylic acid A mixture of methyl 2',3',5',6'-tetrahydro-5H-spiro[furo[3,4-d]pyrimidine-7,4'-pyran]-2-carboxylate (15 mg, 0.06 mmol) and lithium hydroxide hydrate (7 mg, 0.30 mmol) in tetrahydrofuran (1 mL), methanol (1 mL) and water (0.5 mL) was stirred at 25° C. for 16 h. The mixture was quenched by addition of 1N HCl (3 mL) and extracted with ethyl acetate (3×10 mL). The combined organic layers were dried over sodium sulfate and concentrated under reduced pressure to afford crude 2',3',5',6'-tetrahydro-5H-spiro[furo[3,4-d]pyrimidine-7,4'-pyran]-2-carboxylic acid (10 mg, 70%) as a white solid.

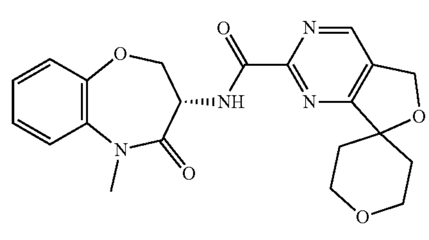 [SMILES: CN1C(=O)[C@@H](NC(=O)c2ncc3c(n2)C2(CCOCC2)OC3)COc2ccccc21]

Step 7: N-[(6S)-2,4-dimethyl-5-oxo-7,8-dihydro-6H-pyrazolo[1,5-a][1,3]diazepin-6-yl]spiro[5H-furo[3,4-d]pyrimidine-7,3'-tetrahydropyran]-2-carboxamide To a solution of (3S)-3-amino-5-methyl-2,3-dihydro-1,5-benzoxazepin-4-one (9 mg, 0.05 mmol), 1-hydroxybenzotriazole (7 mg, 0.05 mmol), 1-(3-dimethylaminopropyl)-3-ethylcarbodiimidehydrochloride (9 mg, 0.05 mmol), and spiro[5H-furo[3,4-d]pyrimidine-7,4'-tetrahydropyran]-2-carboxylic acid (10 mg, 0.04 mmol) in N,N-dimethylformamide (1 mL) was stirred at 25° C. for 16 h. The mixture was concentrate under reduced pressure and the residue was purified by RP-HPLC (25% to 55% acetonitrile/0.05% ammonia hydroxide in water) to afford N-[(6S)-2,4-dimethyl-5-oxo-7,8-dihydro-6H-pyrazolo[1,5-a][1,3]diazepin-6-yl]spiro[5H-furo [3,4-d]pyrimidine-7,3'-tetrahydropyran]-2-carboxamide (4 mg, 21%) as a white solid. $^1$H NMR (400 MHz, $CD_3OD$) δ8.85 (s, 1H), 7.46-7.44 (m, 1H), 7.35-7.31 (m, 2H), 7.26-7.25 (m, 1H), 5.19 (s, 2H), 5.07-5.03 (m, 1H), 4.71-4.68 (m, 1H), 4.66-4.42 (m, 1H), 3.99-3.97 (m, 2H), 3.87-3.82 (m, 2H), 3.44 (s, 3H), 2.24-2.21 (m, 2H), 1.70-1.67 (m, 2H). LC-MS $R_T$=1.923 min, m/z=411.1 $(M+H)^+$.

LCMS (0-60% acetonitrile in water+0.05% ammonium bicarbonate over 3 mins) retention time 1.923 min, ESI+ found [M+H]=411.1.

Example 511

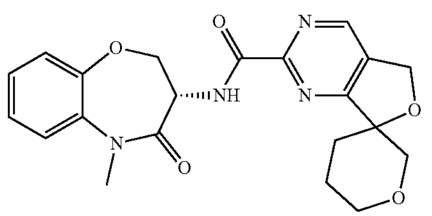 [SMILES: CN1C(=O)[C@@H](NC(=O)c2ncc3c(n2)C2(CCCOC2)OC3)COc2ccccc21]

N-[(3S)-5-methyl-4-oxo-2,3-dihydro-1,5-benzoxazepin-3-yl]spiro[5H-furo[3,4-d]pyrimidine-7,3'-tetrahydropyran]-2-carboxamide Amide coupling prepared in a similar fashion to WX Method 160. The crude was purified by RP-HPLC (20% to 50% acetonitrile/0.05% ammonia hydroxide in water) to afford N-[(3S)-5-methyl-4-oxo-2,3-dihydro-1,5-benzoxazepin-3-yl]spiro[5H-furo[3,4-d]pyrimidine-7,3'-tetrahydropyran]-2-carboxamide (21 mg, 19.2% yield) as a white solid. $^1$H NMR (400 MHz, $CD_3OD$) δ 8.85 (s, 1H), 7.46-7.44 (m, 1H), 7.36-7.30 (m, 2H), 7.27-7.24 (m, 1H), 5.22 (s, 2H), 5.07-5.03 (m, 1H), 4.70-4.66 (m, 1H), 4.47-4.42 (m, 1H), 3.97-3.94 (m, 1H), 3.82-3.74 (m, 2H), 3.69-3.61 (m, 1H), 3.44 (s, 3H), 2.22-2.15 (m, 1H), 2.10-2.01 (m, 1H), 1.94-1.89 (m, 1H), 1.78-1.72 (m, 1H). LCMS $R_T$=0.913 min, m/z=411.2 $[M+H]^+$.

LCMS (10 to 80% acetonitrile in water+0.03% trifluoacetic acid over 2.0 mins) retention time 0.913 min, ESI+ found [M+H]=411.2.

Example 512

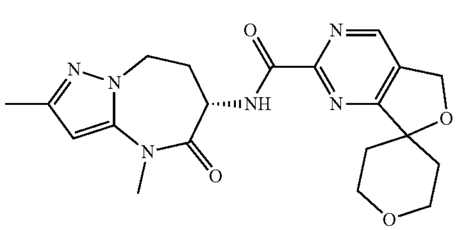 [SMILES: Cc1cc2n(n1)CC[C@H](NC(=O)c1ncc3c(n1)C1(CCOCC1)OC3)C(=O)N2C]

N-[(6S)-2,4-dimethyl-5-oxo-7,8-dihydro-6H-pyrazolo[1,5-a][1,3]diazepin-6-yl]spiro[5H-furo[3,4-d]pyrimidine-7,4'-tetrahydropyran]-2-carboxamide Amide coupling prepared in a similar fashion to WX Method 160. The crude was purified by RP-HPLC (8% to 38% acetonitrile, 0.05% ammonia hydroxide in water) to give N-[(6S)-2,4-dimethyl-5-oxo-7,8-dihydro-6H-pyrazolo [1,5-a][1,3]diazepin-6-yl]spiro[5H-furo [3,4-d]pyrimidine-7,4'-tetrahydropyran]-2-carboxamide (18.1 mg, 33.8%) as a white solid. $^1$H NMR (400 MHz, $CD_3OD$) δ 8.85 (s, 1H), 6.14 (s, 1H), 5.20 (s, 2H), 4.88-4.57 (m, 1H), 4.33-4.26 (m, 2H), 3.98-3.88 (m, 2H), 3.85-3.82 (m, 2H), 3.36 (s, 3H), 2.96-2.91 (m, 1H), 2.30-2.21 (m, 6H), 1.69-1.66 (m, 2H). LC-MS $R_T$=1.052 min, m/z=413.0 $[M+H]^+$.

LCMS (0 to 60% acetonitrile in water+0.03% trifluoacetic acid over 2.0 mins) retention time 1.052 min, ESI+ found [M+H]=413.0.

Example 513

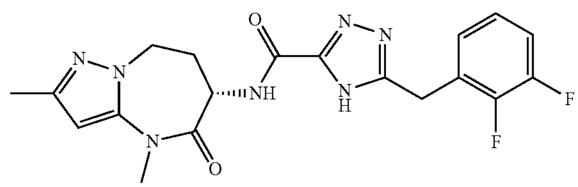

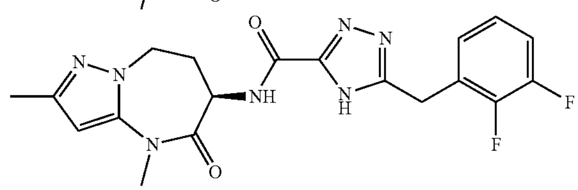

5-[(2,3-difluorophenyl)methyl]-N-(6S)-2,4-dimethyl-5-oxo-7,8-dihydro-6H-pyrazolo[1,5-a][1,3]diazepin-6-yl-4H-1,2,4-triazole-3-carboxamide and 5-[(2,3-difluorophenyl)methyl]-N-(6R)-2,4-dimethyl-5-oxo-7,8-dihydro-6H-pyrazolo[1,5-a][1,3]diazepin-6-yl-4H-1,2,4-triazole-3-carboxamide Amide coupling prepared in a similar fashion to WX Method 011. The crude was purified by RP-HPLC (acetonitrile 28-58%/0.05% ammonium hydroxide in water) to give 5-[(2,3-difluorophenyl)methyl]-N-(2,4-dimethyl-5-oxo-7,8-dihydro-6H-pyrazolo[1,5-a][1,3]diazepin-6-yl)-4H-1,2,4-triazole-3-carboxamide (170 mg, 79%) as a white solid. The racemic material was separated by chiral SFC to give:

5-[(2,3-difluorophenyl)methyl]-N-(6 S)-2,4-dimethyl-5-oxo-7,8-dihydro-6H-pyrazolo[1,5-a][1,3]diazepin-6-yl-4H-1,2,4-triazole-3-carboxamide (Peak 1, Retention time=3.977 min) (77 mg, 48%) as a white solid. $^1$H NMR (400 MHz, $CD_3OD$) δ7.20-7.11 (m, 3H), 6.10 (s, 1H), 4.54-4.49 (m, 1H), 4.30-4.20 (m, 4H), 3.32 (s, 3H), 2.86-2.79 (m, 1H), 2.27-2.21 (m, 4H). LC-MS $R_T$=0.637 min, m/z=416.1 $(M+H)^+$.

LCMS (5 to 95% acetonitrile in water+0.03% trifluoacetic acid over 1.5 mins) retention time 0.637 min, ESI+ found [M+H]=416.1.

5-[(2,3-difluorophenyl)methyl]-N-(6S)-2,4-dimethyl-5-oxo-7,8-dihydro-6H-pyrazolo[1,5-a][1,3]diazepin-6-yl-4H-1,2,4-triazole-3-carboxamide (Peak 2, Retention time=4.582 min) (77.5 mg, 48%) as a white solid. $^1$H NMR (400 MHz, $CD_3OD$) δ7.20-7.11 (m, 3H), 6.10 (s, 1H), 4.54-4.49 (m, 1H), 4.30-4.20 (m, 4H), 3.32 (s, 3H), 2.86-2.79 (m, 1H), 2.27-2.21 (m, 4H). LC-MS $R_T$=0.637 min, m/z=416.1 $(M+H)^+$.

LCMS (5 to 95% acetonitrile in water+0.03% trifluoacetic acid over 1.5 mins) retention time 0.637 min, ESI+ found [M+H]=416.1.

SFC condition: column: chiralpak OD-3 100×4.6 mm I.D., 3 um mobile phase: A: CO2; B: ethanol (0.05% DEA) gradient: from 30% to 30% of B in 4.5 min and hold 40% for 2.5 min, then 5% of B for 1 min. Flow rate: 2.8 mL/min. Column temperature: 40° C.

Example 514

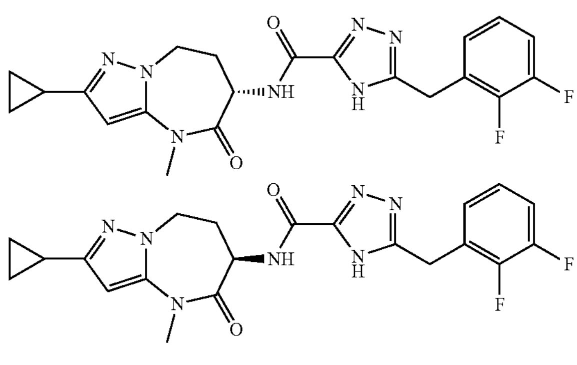

5-[(2,3-difluorophenyl)methyl]-N-(6 S)-2-cyclopropyl-4-methyl-5-oxo-7,8-dihydro-6H-pyrazolo[1,5-a][1,3]diazepin-6-yl-4H-1,2,4-triazole-3-carboxamide and 5-[(2,3-difluorophenyl)methyl]-N-(6R)-2-cyclopropyl-4-methyl-5-oxo-7,8-dihydro-6H-pyrazolo[1,5-a][1,3]diazepin-6-yl-4H-1,2,4-triazole-3-carboxamide Amide coupling prepared in a similar fashion to WX Method 011. The crude was purified by RP-HPLC (acetonitrile 28-58%/0.05% ammonium hydroxide in water) to give 5-[(2,3-difluorophenyl)methyl]-N-2-cyclopropyl-4-methyl-5-oxo-7,8-dihydro-6H-pyrazolo[1, 5-a][1,3]diazepin-6-yl-4H-1,2,4-triazole-3-carboxamide (100 mg, 49%) as a white solid. The racemic material was separated by chiral SFC to give:

5-[(2,3-difluorophenyl)methyl]-N-(6 S)-2-cyclopropyl-4-methyl-5-oxo-7,8-dihydro-6H-pyrazolo[1,5-a][1,3]diazepin-6-yl-4H-1,2,4-triazole-3-carboxamide (Peak 1, Retention time=4.389 min) (42.7 mg, 42%) as a white solid. $^1$H NMR (400 MHz, $CD_3OD$) δ7.26-7.07 (m, 3H), 6.01 (s, 1H), 4.53-4.50 (m, 1H), 4.33-4.16 (m, 4H), 3.35-3.32 (m, 3H), 2.85-2.79 (m, 1H), 2.26-2.22 (m, 1H), 1.92-1.98 (m, 1H), 0.98-0.89 (m, 2H), 0.77-0.69 (m, 2H). LC-MS $R_T$=0.704 min, m/z=442.1 $(M+H)^+$.

LCMS (5 to 95% acetonitrile in water+0.03% trifluoacetic acid over 1.5 mins) retention time 0.704 min, ESI+ found [M+H]=442.1.

5-[(2,3-difluorophenyl)methyl]-N-(6R)-2-cyclopropyl-4-methyl-1-oxo-7,8-dihydro-6H-pyrazolo[1,5-a][1,3]diazepin-6-yl-4H-1,2,4-triazole-3-carboxamide (Peak 2, Retention time=4.804 min) (54.9 mg, 54%) as a white solid. $^1$H NMR (400 MHz, $CD_3OD$) δ7.26-7.07 (m, 3H), 6.01 (s, 1H), 4.53-4.50 (m, 1H), 4.33-4.16 (m, 4H), 3.35-3.32 (m, 3H), 2.85-2.79 (m, 1H), 2.26-2.22 (m, 1H), 1.92-1.98 (m, 1H), 0.98-0.89 (m, 2H), 0.77-0.69 (m, 2H). LC-MS $R_T$=0.704 min, m/z=442.2 $(M+H)^+$.

LCMS (5 to 95% acetonitrile in water+0.03% trifluoacetic acid over 1.5 mins) retention time 0.704 min, ESI+ found [M+H]=442.2.

SFC condition: column: chiralpak OD-3 100×4.6 mm I.D., 3 um mobile phase: A: CO2; B: ethanol (0.05% DEA) gradient: from 30% to 30% of B in 4.5 min and hold 40% for 2.5 min, then 5% of B for 1 min. Flow rate: 2.8 mL/min. Column temperature: 40° C.

Examples 515, 516 and 517

WX Method 121

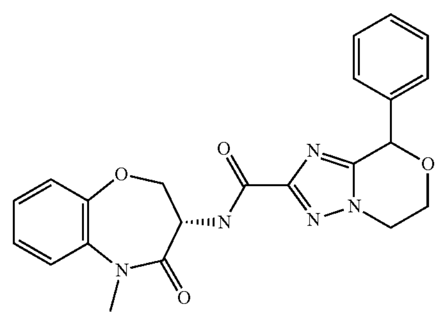

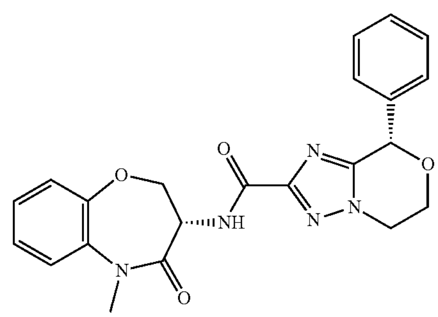

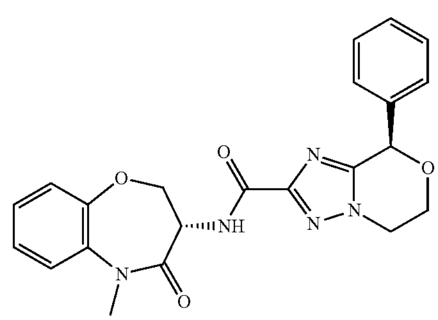

8-phenyl-N-[(3S)-5-methyl-4-oxo-2,3-dihydro-1,5-benzoxazepin-3-yl]-6,8-dihydro-5H-[1, 2,4]triazolo[5,1-c][1,4]oxazine-2-carboxamide and (8S)-8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide and (8R)-8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide

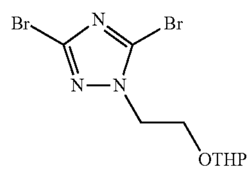

Step 1: 3,5-dibromo-1-(2-tetrahydropyran-2-yloxyethyl)-1,2,4-triazole

To a solution of 3,5-dibromo-1H-1,2,4-triazole (10 g, 44.1 mmol) in acetonitrile (100 mL) was added 2-(2-bromoethoxy)tetrahydro-2H-pyran (8.0 mL, 52.9 mmol) and N,N-diisopropylethylamine (8.45 mL, 48.5 mmol). The mixture was stirred at 90° C. for 3 h and concentrated under reduced pressure. The residue was diluted with ethyl acetate (300 mL), washed saturated sodium bicarbonate (2×50 mL), brine (2×50 mL), dried over sodium sulfate and concentrated under reduced pressure. The residue was purified by column chromatography (silica gel, 100-200 mesh, 0 to 20% ethyl acetate in petroleum ether) to afford 3,5-dibromo-1-(2-tetrahydropyran-2-yloxyethyl)-1,2,4-triazole (13 g, 83%) as a colorless oil, used as is in the next step.

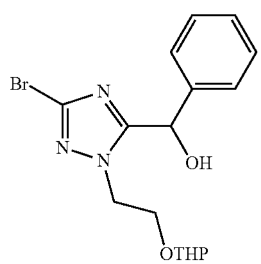

Step 2: [5-bromo-2-(2-tetrahydropyran-2-yloxyethyl)-1,2,4-triazol-3-yl]-phenyl-methanol To a solution of 3,5-dibromo-1-(2-tetrahydropyran-2-yloxyethyl)-1,2,4-triazole (2.0 g, 5.6 mmol) in tetrahydrofuran (20 mL) was added n-butyllithium (2.5 M in hexanes, 2.6 mL, 6.5 mmol) at −78° C. The mixture was stirred at −78° C. for 1 h and then a solution of benzaldehyde (1.2 g, 11.3 mmol) in THF (2 mL) was added. After addition, the mixture was stirred at −78° C. for another 1 h and then quenched by addition of saturated ammonium chloride (10 mL). The resulting mixture was diluted with ethyl acetate (100 mL), washed with water (20 mL), brine (20 mL), dried over sodium sulfate and concentrated under reduced pressure. The residue was purified by column chromatography (silica gel, 100-200 mesh, 0 to 30% ethyl acetate in petroleum ether) to afford [5-bromo-2-(2-tetrahydropyran-2-yloxyethyl)-1,2,4-triazol-3-yl]-phenyl-methanol (1.5 g, 69.7%) as a light yellow oil, used as is in the next step.

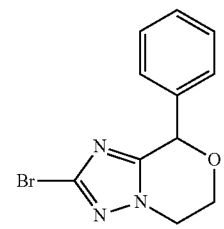 [SMILES: Brc1nc2n(n1)CCOC2c1ccccc1]

Step 3: 2-bromo-8-phenyl-6,8-dihydro-5H-[1,2,4]triazolo[5,1-c][1,4]oxazine

A mixture of [5-bromo-2-(2-tetrahydropyran-2-yloxyethyl)-1,2,4-triazol-3-yl]-phenyl-methanol (1.5 g, 3.92 mmol) and p-toluenesulfonic acid (863 mg, 5.02 mmol) in toluene (50 mL) was heated at reflux for 5 h. After cooled, the reaction was diluted with ethyl acetate (100 mL), washed with sodium hydroxide (1N, 20 mL), brine (20 mL), dried over sodium sulfate and concentrated under reduced pressure. The residue was purified by column chromatography (silica gel, 100-200 mesh, 0 to 40% ethyl acetate in petroleum ether) to afford 2-bromo-8-phenyl-6,8-dihydro-5H-[1,2,4]triazolo[5,1-c][1,4]oxazine (800 mg, 73%) as a yellow oil. LCMS $R_T$=0.642 min, m/z=281.6 $[M+H]^+$.

LCMS (5 to 95% acetonitrile in water+0.03% trifluoacetic acid over 1.5 mins) retention time 0.642 min, ESI+ found [M+H]=281.6

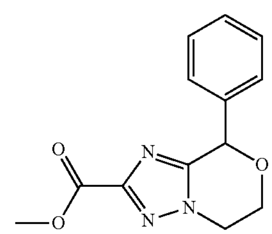 [SMILES: COC(=O)c1nc2n(n1)CCOC2c1ccccc1]

Step 4: methyl 8-phenyl-6,8-dihydro-5H-[1,2,4]triazolo[5,1-c][1,4]oxazine-2-carboxylate A mixture of 1,1'-bis(diphenylphosphino)ferrocene palladium dichloride (13 mg, 0.02 mmol), 2-bromo-8-phenyl-6,8-dihydro-5H-[1,2,4]triazolo[5,1-c][1,4]oxazine (300 mg, 1.07 mmol) and triethylamine(1.45 mL, 10.7 mmol) in methanol (30 mL) was heated at 70° C. for 12 h under CO (40 psi). The mixture was filtered and the filtrate was concentrated under reduced pressure. The residue was purified by column chromatography (silica gel, 100-200 mesh, 0 to 50% ethyl acetate in petroleum ether) to afford methyl 8-phenyl-6,8-dihydro-5H-[1,2,4]triazolo[5,1-c][1,4]oxazine-2-carboxylate (100 mg, 20%) as a brown oil. LCMS $R_T$=0.682 min, m/z=259.9 $[M+H]^+$.

LCMS (5 to 95% acetonitrile in water+0.03% trifluoacetic acid over 1.5 mins) retention time 0.682 min, ESI+ found [M+H]=259.9

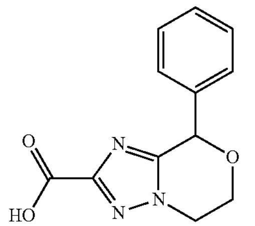 [SMILES: O=C(O)c1nc2n(n1)CCOC2c1ccccc1]

Step 5: 8-phenyl-6,8-dihydro-5H-[1,2,4]triazolo[5,1-c][1,4]oxazine-2-carboxylic acid A mixture of methyl 8-phenyl-6,8-dihydro-5H-[1,2,4]triazolo[5,1-c][1,4]oxazine-2-carboxylate (50 mg, 0.11 mmol) and lithium hydroxide (8 mg, 0.32 mmol) in tetrahydrofuran (4 mL) and water (1 mL) was stirred at 25° C. for 1 h. The mixture was adjusted to pH=3 by addition of 2N HCl and extracted with ethyl acetate (2×10 mL). The combined organic layers were concentrated under reduced pressure to afford crude 8-phenyl-6,8-dihydro-5H-[1,2,4]triazolo[5,1-c][1,4]oxazine-2-carboxylic acid (25 mg, 94% crude yield) as a yellow solid, used as is in the next step.

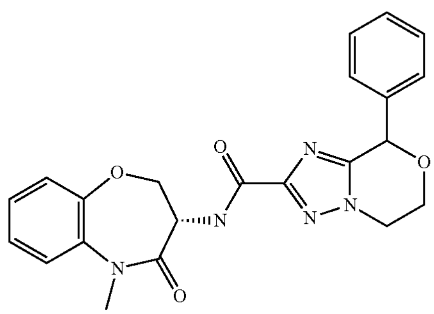

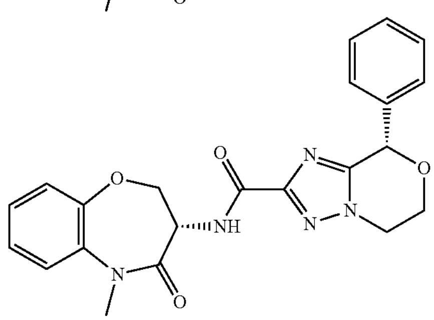

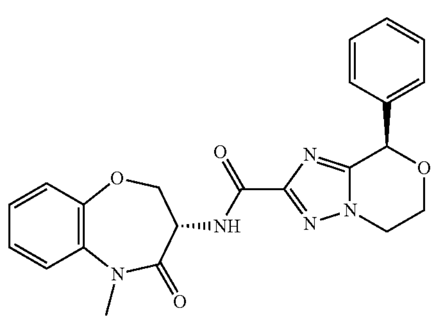

Step 6: 8-phenyl-N-[(3S)-5-methyl-4-oxo-2,3-dihydro 1,5-benzoxazepin-3-yl]-6,8-dihydro-5H-[1,2,4]triazolo[5,1-c][1,4]oxazine-2-carboxamide and (8S)-8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide and (8R)-8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide A mixture of (3S)-3-amino-5-methyl-2,3-dihydro-1,5-benzoxazepin-4-one (23 mg, 0.12 mmol), 1-(3-dimethylaminopropyl)-3-ethylcarbodiimidehydrochlororide (45 mg, 0.24 mmol), 1-hyroxybenzotriazole (30 mg, 0.23 mmol) and 8-phenyl-6,8-dihydro-5H-[1,2,4]triazolo[5,1-c][1,4]oxazine-2-carboxylic acid (25 mg, 0.10 mmol) in N,N-dimethylformamide (3 mL) was stirred at 25° C. for 12 h. The mixture was concentrated under reduced pressure and the residue purified by RP-HPLC (28% to 58% acetonitrile/0.05% ammonia hydroxide in water) to give 8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide (14.5 mg, 33.6%) as a white solid. $^1$H NMR (400 MHz, $CD_3OD$) δ8.80 (s, 1H), 7.46-7.44 (m, 1H), 7.34-7.32 (m, 2H), 7.27-7.24 (m, 1H), 5.12 (s, 2H), 5.07-5.02 (m, 1H), 4.69-4.68 (m, 1H), 4.46-4.43 (m, 1H), 3.44 (s, 3H), 2.08-2.04 (m, 4H), 1.95-1.93 (m, 4H). LCMS $R_T$=1.009 min, m/z=420.2 [M+H]$^+$.

LCMS (10 to 80% acetonitrile in water+0.03% trifluoacetic acid over 2.0 mins) retention time 1.009 min, ESI+ found [M+H]=420.2

Another Batch of Racemic Material was Separated (70 mg) by Chiral SFC to Give:

(8S)-8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide (Peak 1, retention time: 4.182 min) (10.9 mg, 14%), as a light yellow oil. $^1$H NMR (400 MHz, $CD_3OD$) δ7.41-7.38 (m, 6H), 7.30-7.29 (m, 2H), 7.22-7.21 (m, 1H), 5.94 (s, 1H), 5.01-4.96 (m, 1H), 4.58-4.53 (m, 1H), 4.47-4.35 (m, 4H), 4.30-4.25 (m, 1H), 3.38 (s, 3H). LCMS $R_T$=0.809 min, m/z=420.0 [M+H]$^+$.

LCMS (5 to 95% acetonitrile in water+0.03% trifluoacetic acid over 1.5 mins) retention time 0.809 min, ESI+ found [M+H]=420.0

(8R)-8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide (Peak 2, retention time 5.374 min) (10 mg, 14%) as a light yellow oil. $^1$H NMR (400 MHz, $CD_3OD$) δ7.41-7.38 (m, 6H), 7.30-7.29 (m, 2H), 7.22-7.21 (m, 1H), 5.94 (s, 1H), 5.01-4.96 (m, 1H), 4.57-4.47 (m, 2H), 4.40-4.35 (m, 3H), 4.25-4.20 (m, 1H), 3.38 (s, 3H). LCMS $R_T$=0.809 min, m/z=420.0 [M+H]$^+$.

LCMS (5 to 95% acetonitrile in water+0.03% trifluoacetic acid over 1.5 mins) retention time 0.809 min, ESI+ found [M+H]=420.0

SFC condition: Column: Chiralpak AD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 518

WX Method 043

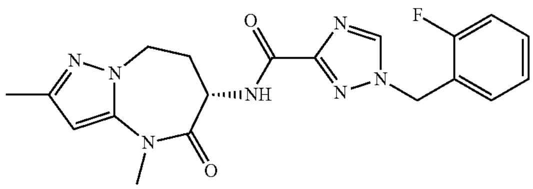 [SMILES: Cc1cc2n(n1)CC[C@H](NC(=O)c1ncn(Cc3ccccc3F)n1)C(=O)N2C]

1-[(2-fluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide

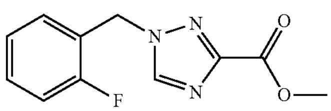 [SMILES: COC(=O)c1ncn(Cc2ccccc2F)n1]

Step 1: methyl 1-[(2-fluorophenyl)methyl]-1,2,4-triazole-3-carboxylate

To a solution of methyl 1H-1,2,4-triazole-3-carboxylate (10.0 g, 78.68 mmol) in N,N-dimethylformamide (200 mL) was added potassium carbonate (21.7 g, 157.36 mmol) and 2-fluorobenzyl bromide (17.9 g, 94.41 mmol). The mixture was stirred at 25° C. for 12 h and then concentrated under reduced pressure. The residue was diluted with brine (30 mL) and extracted with ethyl acetate (3×25 mL). The combined organic layers were dried over anhydrous sodium sulfate and concentrated under reduced pressure. The residue was purified by column chromatography (silica gel, 100-200 mesh, 0 to 100% ethyl acetate in petroleum ether) to afford methyl 1-[(2-fluorophenyl)methyl]-1,2,4-triazole-3-carboxylate (5.0 g, 27% yield) as a white solid, used as is in the next step.

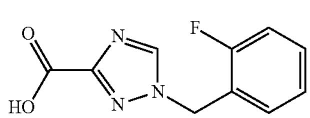 [SMILES: O=C(O)c1ncn(Cc2ccccc2F)n1]

Step 2: 1-[(2-fluorophenyl)methyl]-1,2,4-triazole-3-carboxylic acid

A mixture of methyl 1-[(2-fluorophenyl)methyl]-1,2,4-triazole-3-carboxylate (40.0 g, 170.00 mmol) and potassium hydroxide (19.1 g, 340.12 mmol) in ethanol (800 mL) and water (200 mL) was stirred at 25° C. for 12 h. The ethanol was concentrated under reduced pressure and the aqueous solution was adjusted to pH=4 by addition of 2 N HCl. The resulting solid was collected by filtration and dried to give 1-[(2-fluorophenyl)methyl]-1,2,4-triazole-3-carboxylic acid (33.0 g, 87.7%) as a white solid, used as is in the next step.

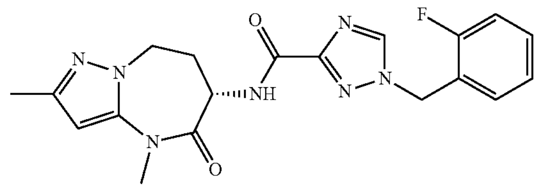

Step 3: 1-[(2-fluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide To a stirred solution of 1-[(2-fluorophenyl)methyl]-1,2,4-triazole-3-carboxylic acid (23.9 g, 108.12 mmol) in N,N-dimethylformamide (6 mL) was added (6S)-6-amino-2,4-dimethyl-7,8-dihydro-6H-pyrazolo[1,5-a][1,3]diazepin-5-one (20.0 g, 102.97 mmol), 1-hydroxybenzotriazole (2.78 g, 20.59 mmol) and 1-(3-dimethylaminopropyl)-3-ethylcarbodiimidehydrochloride (29.61 g, 154.46 mmol). The mixture was stirred at 20° C. for 2 h. The mixture was poured in to sat. brine, then white solid was formed. The cake was collected and washed with ethyl acetate. The solid was recrystallized in ethanol/water to give 1-[(2-fluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide (29.1 g, 71%) as a white solid. $^1$H NMR (400 MHz, $CD_3OD$) δ8.57 (s, 1H), 7.40-7.35 (m, 2H), 7.21-7.12 (m, 2H), 6.10 (s, 1H), 5.54 (s, 2H), 4.54-4.49 (m, 1H), 4.29-4.15 (m, 2H), 3.31 (s, 3H), 2.87-2.79 (m, 1H), 2.27-2.20 (m, 4H). LC-MS $R_T$=1.426 min, m/z=398.2 $(M+H)^+$.

LCMS (10 to 80% ammonium hydroxide in water+0.03% trifluoacetic acid over 1.5 mins) retention time 1.426 min, ESI+ found [M+H]=398.2

Example 519

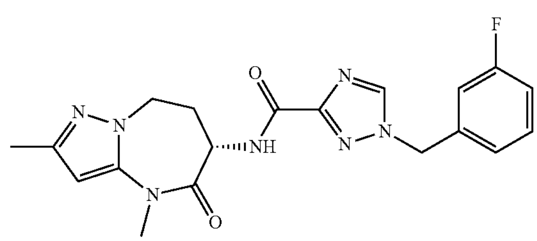 [SMILES: Cc1cc2n(n1)CC[C@H](NC(=O)c1ncn(Cc3cccc(F)c3)n1)C(=O)N2C]

1-[(3-fluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide Amide coupling prepared in a similar fashion to WX Method 049. The crude was purification by RP-HPLC (acetonitrile 42-62%/0.05 ammonium hydroxide in water) to give 1-[(3-fluorophenyl)methyl]-N-(6S)-2,4-dimethyl-5-oxo-7,8-dihydro-6H-pyrazolo[1,5-a][1,3]diazepin-6-yl]-1,2,4-triazole-3-carboxamide (Peak 1, retention time 1.663 min) (44 mg, 43%) as a white solid. $^1$H NMR (400 MHz, $CD_3OD$) δ8.60 (s, 1H), 7.42-7.36 (m, 1H), 7.17-7.06 (m, 3H), 6.11 (s, 1H), 5.49 (s, 2H), 4.56-4.51 (m, 1H), 4.31-4.18 (m, 2H), 3.32 (d, J=5.2 Hz, 3H), 2.87-2.81 (m, 1H), 2.28-2.23 (m, 4H). LCMS $R_T$=0.904 min, m/z=398.2 $[M+H]^+$.

LCMS (10 to 80% acetonitrile in water+0.03% trifluoacetic acid over 2.0 mins) retention time 0.904 min, ESI+ found [M+H]=398.2

Example 520

WX Method 073

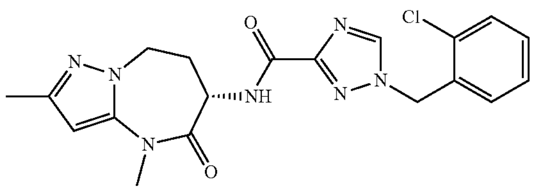 [SMILES: Cc1cc2n(n1)CC[C@H](NC(=O)c1ncn(Cc3ccccc3Cl)n1)C(=O)N2C]

1-[(2-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide

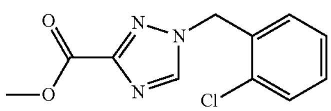 [SMILES: COC(=O)c1ncn(Cc2ccccc2Cl)n1]

Step 1: methyl 1-[(2-chlorophenyl)methyl]-1,2,4-triazole-3-carboxylate

To a solution of methyl 1H-1,2,4-triazole-3-carboxylate (10.0 g, 78.68 mmol) in N,N-dimethylformamide (200 mL) was added potassium carbonate (21.8 g, 157.36 mmol) and 2-chlorobenzyl bromide (19.4 g, 94.41 mmol). The mixture was stirred at 25° C. for 12 h and then filtered. The filtrate was concentrated under reduced pressure and the residue was purified by column chromatography (silica gel, 100-200 mesh, 0 to 100% ethyl acetate in petroleum ether) to afford methyl 1-[(2-chlorophenyl)methyl]-1,2,4-triazole-3-carboxylate (5.0 g, 25%) as a white solid, used as is in the next step, used as is in the next step.

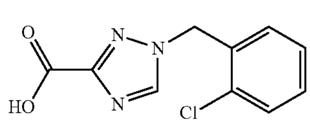 [SMILES: O=C(O)c1ncn(Cc2ccccc2Cl)n1]

Step 2: 1-[(3-fluorophenyl)methyl]-1,2,4-triazole-3-carboxylic acid

A mixture of methyl 1-[(2-chlorophenyl)methyl]-1,2,4-triazole-3-carboxylate (5.0 g, 19.87 mmol) and potassium hydroxide (2.2 g, 39.73 mmol) in ethanol (80 mL) and water (15 mL) was stirred at 25° C. for 12 h. The mixture was concentrated under reduced pressure and diluted with water (20 mL). The solution was adjusted to pH=4 by addition of 2N HCl. The resulting solid was collected by filtration and dried under reduced pressure to obtain 1-[(2-chlorophenyl)methyl]-1,2,4-triazole-3-carboxylic acid (3.0 g, 64%) as white solids. $^1$H NMR (400 MHz, DMSO-d6) δ8.79 (s, 1H), 7.52-7.50 (m, 1H), 7.41-7.37 (m, 2H), 7.37-7.29 (m, 2H), 5.59 (s, 2H).

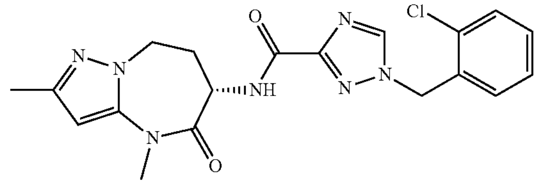

Step 3: 1-[(2-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide A mixture of 1-(3-dimethylaminopropyl)-3-ethylcarbodiimidehydrochloride (74 mg, 0.39 mmol), 1-hydroxybenzotriazole (52 mg, 0.39 mmol), 1-[(2-chlorophenyl)methyl]-1,2,4-triazole-3-carboxylic acid (73 mg, 0.31 mmol) and (6S)-6-amino-2,4-dimethyl-7,8-dihydro-6H-pyrazolo[1,5-a][1,3]diazepin-5-one (50 mg, 0.26 mmol) in N,N-dimethylformamide (5 mL) was stirred at 25° C. for 12 h. The mixture was concentrated under reduced pressure and the residue was purified by RP-HPLC (acetonitrile 28-58%/0.05% ammonia hydroxide in water) to afford 1-[(2-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide (34.6 mg, 32%) as white solids. $^1$H NMR (400 MHz, $CD_3OD$) δ8.57 (s, 1H), 7.46-7.36 (m, 1H), 7.35-7.32 (m, 3H), 6.10 (s, 1H), 5.60 (s, 2H), 4.54-4.49 (m, 1H), 4.33-4.19 (m, 2H), 3.30 (s, 3H), 2.85-2.79 (m, 1H), 2.27-2.21 (m, 4H). LCMS $R_T$=0.763 min, m/z=414.1 $[M+H]^+$.

LCMS (5 to 95% acetonitrile in water+0.1% trifluoacetic acid over 1.5 mins) retention time 0.763 min, ESI+ found [M+H]=414.1

Example 521

WX Method 077

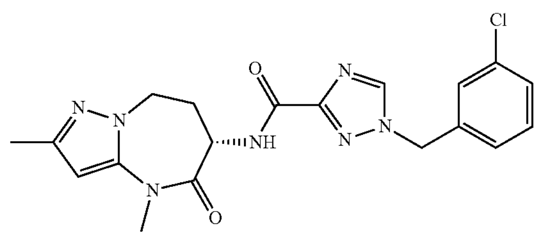

1-[(3-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide

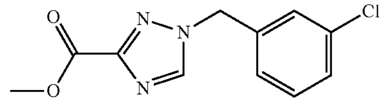 [SMILES: COC(=O)c1ncn(Cc2cccc(Cl)c2)n1]

Step 1: methyl 1-[(3-chlorophenyl)methyl]-1,2,4-triazole-3-carboxylate

To a solution of methyl 1H-1,2,4-triazole-3-carboxylate (10.0 g, 78.68 mmol) in N,N-dimethylformamide (200 mL) was added potassium carbonate (21.8 g, 157.36 mmol) and 3-chlorobenzyl bromide (19.4 g, 94.41 mmol). The mixture was stirred at 25° C. for 12 h and filtered. The filtrate was concentrated under reduced pressure and the residue was purified by column chromatography (silica gel, 100-200 mesh, 0 to 100% ethyl acetate in petroleum ether) to afford methyl 1-[(3-chlorophenyl)methyl]-1,2,4-triazole-3-carboxylate (3.0 g, 15%) as white solids, used as is in the next step.

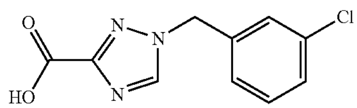 [SMILES: O=C(O)c1ncn(Cc2cccc(Cl)c2)n1]

Step 2: 1-[(3-chlorophenyl)methyl]-1,2,4-triazole-3-carboxylic acid

A mixture of methyl 1-[(3-chlorophenyl)methyl]-1,2,4-triazole-3-carboxylate (3.0 g, 11.92 mmol) and potassium hydroxide (1.3 g, 23.84 mmol) in ethanol (80 mL) and water (15 mL) was stirred at 25° C. for 12 h. The mixture was concentrated under reduced pressure and diluted with water (20 mL). The solution was adjusted to pH=4 by addition of 2N HCl. The resulting solid was collected by filtration and dried under reduced pressure to obtain 1-[(3-chlorophenyl)methyl]-1,2,4-triazole-3-carboxylic acid (2.0 g, 71%) as a white solid. $^1$H NMR (400 MHz, DMSO-d6) δ8.80 (s, 1H), 7.42-7.38 (m, 3H), 7.29-7.26 (m, 1H), 5.50 (s, 2H).

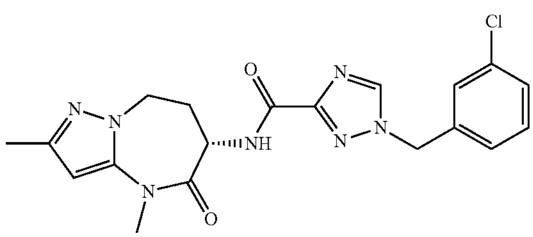

Step 3: 1-[(3-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide A mixture of 1-hydroxybenzotriazole (52 mg, 0.39 mmol), 1-[(3-chlorophenyl)methyl]-1,2,4-triazole-3-carboxylic acid (73 mg, 0.31 mmol), (6S)-6-amino-2,4-dimethyl-7,8-dihydro-6H-pyrazolo[1,5-a][1,3]diazepin-5-one (50 mg, 0.26 mmol) and 1-(3-dimethylaminopropyl)-3-ethylcarbodiimidehydrochloride (74 mg, 0.39 mmol) in N,N-dimethylformamide (5 mL) was stirred at 25° C. for 2 h. The mixture was concentrated under reduced pressure and the residue was purified by RP-HPLC (acetonitrile 28-58%/0.05% ammonia hydroxide in water) to afford 1-[(3-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide (36.01 mg, 34%) as white solids. $^1$H NMR (400 MHz, $CD_3OD$) δ 8.60 (s, 1H), 7.37-7.25 (m, 4H), 6.10 (s, 1H), 5.46 (s, 2H), 4.54-4.49 (m, 1H), 4.29-4.27 (m, 1H), 4.24-4.19 (m, 1H), 3.31-3.29 (m, 3H), 2.85-2.79 (m, 1H), 2.28-2.21 (s, 4H). LC-MS $R_T$=0.755 min, m/z=414.1 $[M+H]^+$.

LCMS (5 to 95% acetonitrile in water+0.1% trifluoacetic acid over 1.5 mins) retention time 0.755 min, ESI+ found [M+H]=414.1

Example 522

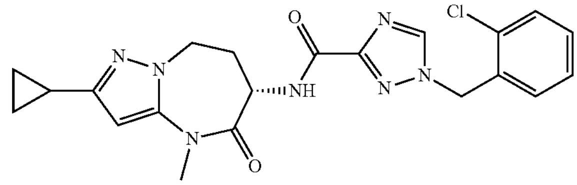

1-[(2-chlorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 073 The crude was purified by RP-HPLC (ACN 45-75%/0.05% ammonia hydroxide in water) to afford 1-[(2-chlorophenyl)methyl]-N-(6 S)-2-cyclopropyl-4-methyl-5-oxo-7,8-dihydro-6H-pyrazolo[1,5-a][1,3]diazepin-6-yl-1,2,4-triazole-3-carboxamide (31.5 mg, 30%) as white solids. $^1$H NMR (400 MHz, $CD_3OD$) δ 8.56 (s, 1H), 7.45-7.30 (m, 4H), 5.98 (s, 1H), 5.59 (s, 2H), 4.52-4.47 (m, 1H), 4.29-4.17 (m, 2H), 3.30 (s, 3H), 2.83-2.78 (m, 1H), 2.24-2.21 (m, 1H), 1.90-1.87 (m, 1H), 0.93-0.90 (m, 2H), 0.73-0.70 (m, 2H). LCMS $R_T$=0.794 min, m/z=440.1 $[M+H]^+$.

LCMS (5 to 95% acetonitrile in water+0.1% trifluoacetic acid over 1.5 mins) retention time 0.794 min, ESI+ found [M+H]=440.1.

Example 523

WX Method 066

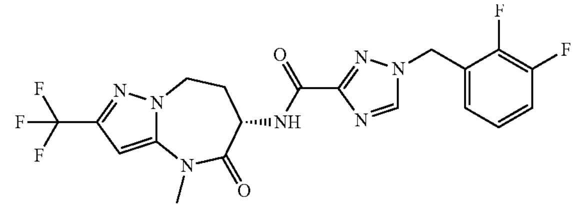 [SMILES: CN1C(=O)[C@@H](NC(=O)c2ncn(Cc3cccc(F)c3F)n2)CCn2nc(C(F)(F)F)cc21]

1-[(2,3-difluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide

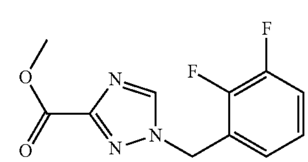 [SMILES: COC(=O)c1ncn(Cc2cccc(F)c2F)n1]

Step 1: methyl 1-(2,3-difluorobenzyl)-1H-1,2,4-triazole-3-carboxylate

To a solution of methyl 1H-1,2,4-triazole-3-carboxylate (10.0 g, 78.68 mmol) in N,N-dimethylformamide (200 mL) was added potassium carbonate (21.8 g, 157.36 mmol) and 2,3-difluorobenzyl bromide (19.6 g, 94.41 mmol). The mixture was stirred at 25° C. for 12 h and then filtered. The filtrate was concentrated under reduced pressure and the residue was purified by column chromatography (silica gel, 100-200 mesh, 0-100% ethyl acetate in petroleum ether) to afford crude methyl 1-(2,3-difluorobenzyl)-1H-1,2, 4-triazole-3-carboxylate (10.2 g, 51%) as white solids, used as is in the next step.

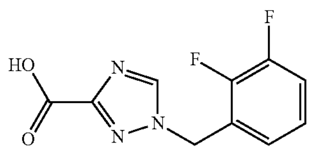 [SMILES: O=C(O)c1ncn(Cc2cccc(F)c2F)n1]

Step 2: 1-(2,3-difluorobenzyl)-1H-1,2,4-triazole-3-carboxylic acid

A mixture of methyl 1-[(2,3-difluorophenyl)methyl]-1,2, 4-triazole-3-carboxylate (2.0 g, 7.9 mmol) and potassium hydroxide (0.9 g, 15.8 mmol) in ethanol (40 mL) and water (5 mL) was stirred at 25° C. for 12 h. The ethanol was evaporated and the residue was diluted with water (20 mL). The mixture was adjusted to pH=4 by addition of 2N HCl. The resulting solid was collected by filtration and dried to give 1-(2,3-difluorobenzyl)-1H-1,2,4-triazole-3-carboxylic acid (1.6 g, 85%) as white solids. $^{1}$H NMR (400 MHz, $CD_3OD$) δ8.68 (s, 1H), 7.31-7.28 (m, 1H), 7.20-7.18 (m, 2H), 5.61 (s, 2H).

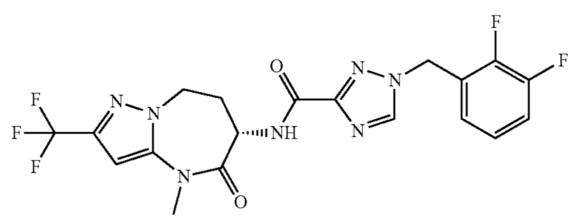 [SMILES: CN1C(=O)[C@@H](NC(=O)c2ncn(Cc3cccc(F)c3F)n2)CCn2nc(C(F)(F)F)cc21]

Step 3: 1-[(2,3-difluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide A mixture of 6-amino-4-methyl-2-(trifluoromethyl)-7,8-dihydro-6H-pyrazolo[1,5-a][1,3]diazepin-5-one (50 mg, 0.20 mmol), 1-hydroxybenzotriazole (27 mg, 0.20 mmol), 1-(3-dimethylaminopropyl)-3-ethylcarbodiimidehydrochloride (39 mg, 0.20 mmol) and 1-[(2,3-difluorophenyl) methyl]-1,2,4-triazole-3-carboxylic acid (48 mg, 0.20 mmol) in N,N-dimethylformamide (4 mL) was stirred at 20° C. for 2 h. The solvent was evaporated under reduced pressure and the residue was purified by RP-HPLC (acetonitrile 30-60%/0.05% ammonium hydroxide in water) to afford the racemic material ((80 mg, 85%), which was separated by chiral SFC to give:

1-[(2,3-difluorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time 5.327 min) (22.8 mg, 29%) as white solids. $^{1}$H NMR (400 MHz, $CD_3OD$) δ 8.58 (s, 1H), 7.48-7.42 (m, 1H), 7.05-6.97 (m, 2H), 6.66 (s, 1H), 5.52 (s, 2H), 4.53-4.44 (m, 2H), 4.39-4.33 (m, 1H), 3.36 (s, 3H), 2.89-2.84 (m, 1H), 2.35-2.29 (m, 1H). LCMS $R_T$=0.812 min, m/z=470.1 $[M+H]^+$.

LCMS (5 to 95% acetonitrile in water+0.03% trifluoacetic acid over 1.5 mins) retention time 0.812 min, ESI+ found [M+H]=470.1.

SFC conditions: Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Example 524

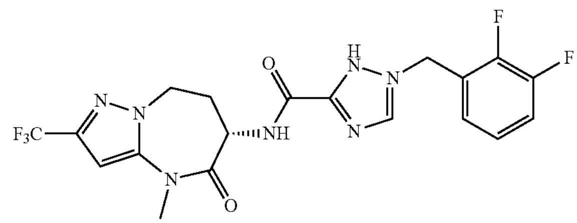

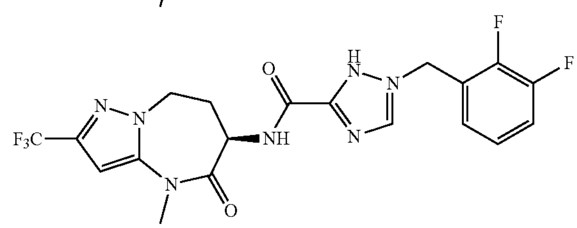

5-[(2,3-difluorophenyl)methyl]-N-(6S)-4-methyl-5-oxo-2-(trifluoromethyl)-7,8-dihydro-6H-pyrazolo[1,5-a][1,3]diazepin-6-yl-4H-1,2,4-triazole-3-carboxamide and 5-[(2,3-difluorophenyl)methyl]-N-(6R)-4-methyl-5-oxo-2-(trifluoromethyl)-7,8-dihydro-6H-pyrazolo[1,5-a][1,3]diazepin-6-yl-4H-1,2,4-triazole-3-carboxamide Amide coupling prepared in a similar fashion to WX Method 011. The crude was separated by chiral SFC to give:

5-[(2,3-difluorophenyl)methyl]-N-(6 S)-4-methyl-5-oxo-2-(trifluoromethyl)-7,8-dihydro-6H-pyrazolo[1,5-a][1,3]diazepin-6-yl-4H-1,2,4-triazole-3-carboxamide (Peak 1, retention time: 2.787 min) (41 mg, 44%). $^{1}$H NMR (400 MHz, DMSO-$d_6$) δ8.69 (s, 1H), 7.37-7.31 (m, 1H), 7.19-7.13 (m, 2H), 6.94 (s, 1H), 4.50-4.44 (m, 1H), 4.36-4.32 (m, 2H), 4.19 (s, 2H), 3.27 (s, 3H), 2.64-2.60 (m, 1H), 2.52-2.48 (m, 1H). LCMS $R_T$=0.808 min, m/z=470.1 $[M+H]^+$.

LCMS (5 to 95% acetonitrile in water+0.03% trifluoacetic acid over 1.5 mins) retention time 0.808 min, ESI+ found [M+H]=470.1

5-[(2,3-difluorophenyl)methyl]-N-(6R)-4-methyl-5-oxo-2-(trifluoromethyl)-7,8-dihydro-6H-pyrazolo[1,5-a][1,3]diazepin-6-yl-4H-1,2,4-triazole-3-carboxamide (Peak 1, retention time: 3.099 min) (29 mg, 31%). $^{1}$H NMR (400 MHz, DMSO-$d_6$) δ8.71 (s, 1H), 7.37-7.31 (m, 1H), 7.19-

7.13 (m, 2H), 6.94 (s, 1H), 4.50-4.44 (m, 1H), 4.36-4.32 (m, 2H), 4.19 (s, 2H), 3.27 (s, 3H), 2.64-2.60 (m, 1H), 2.52-2.48 (m, 1H). LCMS $R_T$=0.808 min, m/z=470.1 $[M+H]^+$.

LCMS (5 to 95% acetonitrile in water+0.03% trifluoacetic acid over 1.5 mins) retention time 0.808 min, ESI+ found [M+H]=470.1.

SFC condition: Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Example 525

WX Method 067

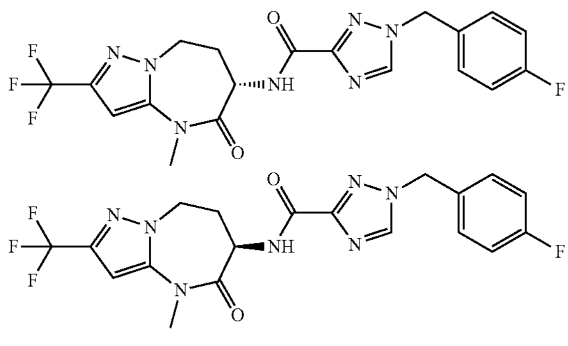

1-[(4-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(4-fluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide

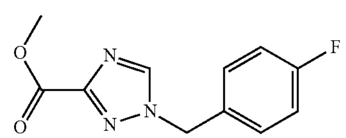 [SMILES: COC(=O)c1ncn(Cc2ccc(F)cc2)n1]

Step 1: methyl 1-(4-fluorobenzyl)-1H-1,2,4-triazole-3-carboxylate

To a solution of methyl 1H-1,2,4-triazole-3-carboxylate (10.0 g, 78.68 mmol) in N,N-dimethylformamide (200 mL) was added potassium carbonate (21.8 g, 157.36 mmol) and 4-fluorobenzyl chloride (13.7 g, 94.41 mmol). The mixture was stirred at 25° C. for 12 h and filtered. The filtrate was concentrated under reduced pressure and the residue was purified by column chromatography (silica gel, 100-200 mesh, 0-100% ethyl acetate in petroleum ether) to afford methyl 1-(4-fluorobenzyl)-1H-1,2,4-triazole-3-carboxylate (7.8 g, 42%) as white solids.

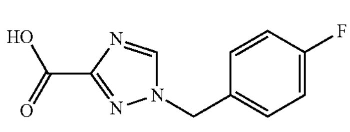 [SMILES: O=C(O)c1ncn(Cc2ccc(F)cc2)n1]

Step 2: 1-(4-fluorobenzyl)-1H-1,2,4-triazole-3-carboxylic acid

A mixture of methyl 1-[(4-fluorophenyl)methyl]-1,2,4-triazole-3-carboxylate (2.0 g, 8.5 mmol) and potassium hydroxide (954 mg, 17.0 mmol) in ethanol (40 mL) and water (5 mL) was stirred at 25° C. for 12 h. The ethanol was evaporated and the residue was diluted with water (20 mL). The mixture was adjusted to pH=4 by addition of 2N HCl. The resulting solid was collected by filtration and dried to give 1-(4-fluorobenzyl)-1H-1,2,4-triazole-3-carboxylic acid (1.5 g, 81%) as white solids. $^1$H NMR (400 MHz, $CD_3OD$) δ8.63 (s, 1H), 7.44-7.40 (m, 2H), 7.14-7.09 (m, 2H), 5.47 (s, 2H).

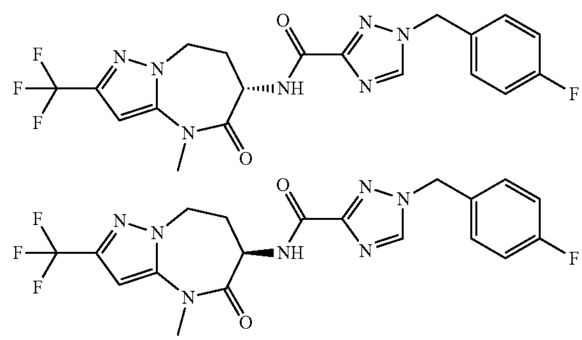

Step 3: 1-[(4-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(4-fluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide To a solution of 6-amino-4-methyl-2-(trifluoromethyl)-7,8-dihydro-6H-pyrazolo[1,5-a][1,3]diazepin-5-one (50 mg, 0.20 mmol) in N,N-dimethylformamide (4 mL) was added 1-(3-dimethyl aminopropyl)-3-ethylcarbodiimidehydrochloride (46 mg, 0.24 mmol), 1-hydroxybenzotriazole (33 mg, 0.24 mmol) and 1-[(4-fluorophenyl)methyl]-1,2,4-triazole-3-carboxylic acid (53 mg, 0.24 mmol). The reaction mixture was stirred at 20° C. for 2 h and concentrated under reduced pressure. The residue was purified by RP-HPLC (acetonitrile 35-65%/0.05% ammonium hydroxide in water) to afford the racemic material which was separated by chiral SFC to give: 1-[(4-fluorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time 5.728 min) (35 mg, 37%) as white solids. $^1$H NMR (400 MHz, DMSO-$d_6$) δ8.82 (s, 1H), 8.66 (d, J=8.0 Hz, 1H), 7.40-7.36 (m, 2H), 7.21 (t, J=8.8 Hz, 2H), 6.94 (s, 1H), 5.47 (s, 2H), 4.48-4.44 (m, 1H), 4.37-4.30 (m, 2H), 3.27 (s, 3H), 2.64-2.60 (m, 1H), 2.52-2.48 (m, 1H). LCMS $R_T$=0.810 min, m/z=452.1 $[M+H]^+$.

LCMS (5 to 95% acetonitrile in water+0.03% trifluoacetic acid over 1.5 mins) retention time 0.810 min, ESI+ found [M+H]=452.1.

1-[(4-fluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide (Peak 2, retention time 7.422 min) (33 mg, 36%) as white solids. $^1$H NMR (400

MHz, DMSO-$d_6$) δ8.82 (s, 1H), 8.66 (d, J=8.0 Hz, 1H), 7.40-7.36 (m, 2H), 7.21 (t, J=8.8 Hz, 2H), 6.94 (s, 1H), 5.47 (s, 2H), 4.48-4.44 (m, 1H), 4.37-4.30 (m, 2H), 3.27 (s, 3H), 2.64-2.60 (m, 1H), 2.52-2.48 (m, 1H). LCMS $R_T$=0.806 min, m/z=452.1 [M+H]$^+$.

LCMS (5 to 95% acetonitrile in water+0.03% trifluoacetic acid over 1.5 mins) retention time 0.806 min, ESI+ found [M+H]=452.1.

SFC condition: Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Example 526

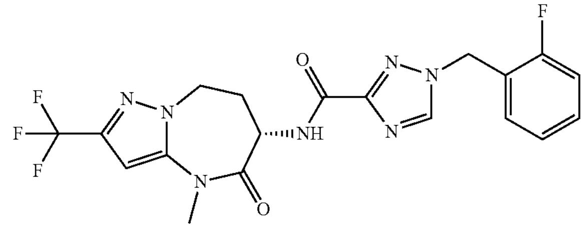

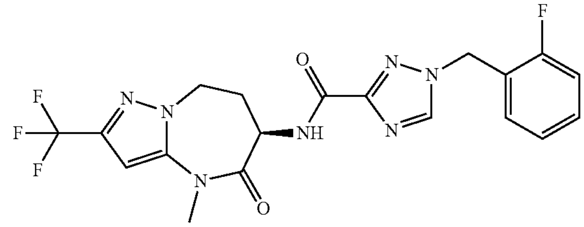

1-[(2-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(2-fluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide Amide coupling prepared in a similar fashion to WX Method 043. The obtained racemic compound was separated by chiral SFC to give:

1-[(2-fluorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time=5.180 min) (24 mg, 25%) as white solids. $^1$H NMR (400 MHz, DMSO-$d_6$) δ8.82 (s, 1H), 8.66 (d, J=8.0 Hz, 1H), 7.43-7.33 (m, 2H), 7.26-7.20 (m, 2H), 6.94 (s, 1H), 5.55 (s, 2H), 4.49-4.44 (m, 1H), 4.36-4.30 (m, 2H), 3.26 (s, 3H), 2.64-2.60 (m, 1H), 2.52-2.48 (m, 1H). LCMS $R_T$=0.803 min, m/z=452.1 [M+H]$^+$.

LCMS (5 to 95% acetonitrile in water+0.03% trifluoacetic acid over 1.5 mins) retention time 0.803 min, ESI+ found [M+H]=452.1.

1-[(2-fluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide (Peak 2, retention time=5.97 min) (18 mg, 20%) as white solids. $^1$H NMR (400 MHz, DMSO-$d_6$) δ8.82 (s, 1H), 8.66 (d, J=8.0 Hz, 1H), 7.43-7.33 (m, 2H), 7.26-7.20 (m, 2H), 6.94 (s, 1H), 5.55 (s, 2H), 4.49-4.44 (m, 1H), 4.36-4.30 (m, 2H), 3.26 (s, 3H), 2.64-2.60 (m, 1H), 2.52-2.48 (m, 1H). LCMS $R_T$=0.806 min, m/z=452.0 [M+H]$^+$.

LCMS (5 to 95% acetonitrile in water+0.03% trifluoacetic acid over 1.5 mins) retention time 0.806 min, ESI+ found [M+H]=452.0.

SFC conditions: Column Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Example 527

WX Method 049

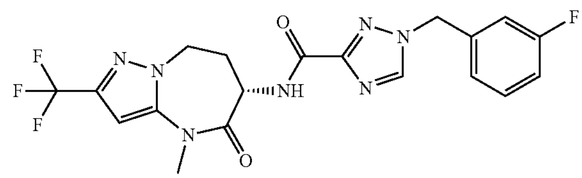

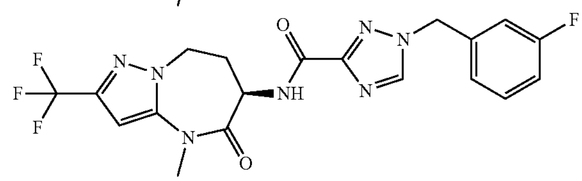

1-[(3-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(3-fluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide

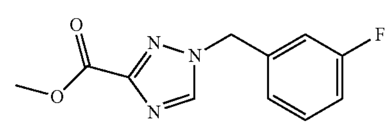 [SMILES: COC(=O)c1ncn(Cc2cccc(F)c2)n1]

Step 1: methyl 1-[(2-fluorophenyl)methyl]-1,2,4-triazole-3-carboxylate

To a solution of methyl 1H-1,2,4-triazole-3-carboxylate (10.0 g, 78.68 mmol) in N,N-dimethylformamide (200 mL) was added potassium carbonate (21.8 g, 157.36 mmol) and 3-fluorobenzyl bromide (17.9 g, 94.41 mmol). The mixture was stirred at 25° C. for 12 h and then concentrated under reduced pressure. The residue was diluted with brine (200 mL) and extracted with ethyl acetate (3×200 mL). The combined organic extracts were dried over anhydrous sodium sulfate and concentrated under reduced pressure. The residue was purified by flash column chromatography (silica gel, 100-200 mesh, 0 to 100% ethyl acetate in petroleum ether) to afford methyl 1-[(3-fluorophenyl)methyl]-1,2,4-triazole-3-carboxylate (5.0 g, 27%) as a white solid.

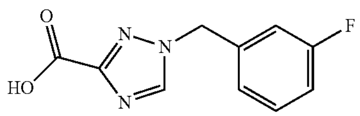 [SMILES: O=C(O)c1ncn(Cc2cccc(F)c2)n1]

Step 2: 1-[(3-fluorophenyl)methyl]-1,2,4-triazole-3-carboxylic acid

A mixture of methyl 1-[(3-fluorophenyl)methyl]-1,2,4-triazole-3-carboxylate (5.0 g, 21.26 mmol) and potassium hydroxide (2.4 g, 42.52 mmol) in ethanol (80 mL) and water (15 mL) was stirred at 25° C. for 12 h. The ethanol was evaporated under reduced pressure and the aqueous residue was adjusted to pH=4 by addition of 2N HCl. The resulting solid was collected by filtration and dried to obtain crude 1-[(3-fluorophenyl)methyl]-1,2,4-triazole-3-carboxylic acid (3.0 g, 64%) as a white solid. $^1$H NMR (400 MHz, DMSO-d6) δ8.81 (s, 1H), 7.47-7.35 (m, 1H), 7.23-7.09 (m, 2H), 5.51 (s, 2H).

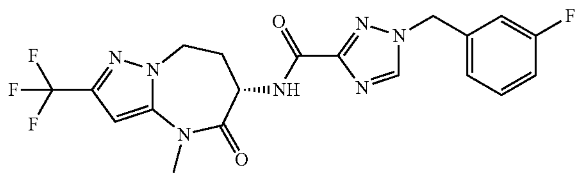

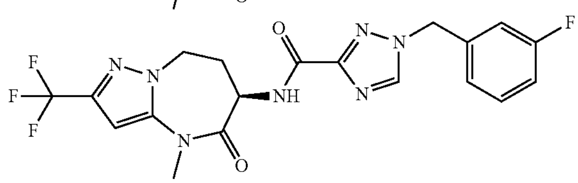

Step 3: 1-[(3-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(3-fluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide To a solution of 6-amino-4-methyl-2-(trifluoromethyl)-7,8-dihydro-6H-pyrazolo[1,5-a][1,3]diazepin-5-one (50 mg, 0.20 mmol) in N,N-dimethylformamide (4 mL) was added 1-hydroxybenzotriazole (27 mg, 0.20 mmol), 1-[(3-fluorophenyl)methyl]-1,2,4-triazole-3-carboxylic acid (44 mg, 0.20 mmol) and 1-(3-dimethylaminopropyl)-3-ethylcarbodiimidehydrochloride (39 mg, 0.20 mmol). The reaction mixture was stirred at 20° C. for 2 h and concentrated under reduced pressure. The residue was purified by RP-HPLC (acetonitrile 30-60%/0.1% ammonia hydroxide in water) to afford 1-(3-fluorobenzyl)-N-(4-methyl-5-oxo-2-(trifluoromethyl)-5,6,7,8-tetrahydro-4H-pyrazolo[1, 5-a][1,3]diazepin-6-yl)-1H-1,2,4-triazole-3-carboxamide (65 mg, 69%). The racemic material was separated by chiral SFC to give:

1-[(3-fluorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time 5.675 min) (28 mg, 30%) as white solids. $^1$H NMR (400 MHz, DMSO-$d_6$) δ8.84 (s, 1H), 8.68 (d, J=8.0 Hz, 1H), 7.46-7.40 (m, 1H), 7.19-7.12 (m, 3H), 6.94 (s, 1H), 5.51 (s, 2H), 4.50-4.44 (m, 1H), 4.37-4.31 (m, 2H), 3.27 (s, 3H), 2.64-2.60 (m, 1H), 2.52-2.48 (m, 1H). LCMS $R_T$=0.807 min, m/z=452.0 [M+H]$^+$.

LCMS (5 to 95% acetonitrile in water+0.03% trifluoacetic acid over 1.5 mins) retention time 0.807 min, ESI+ found [M+H]=452.0.

1-[(3-fluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide (Peak 2, retention time 7.386 min) (29 mg, 31%) as white solids. $^1$H NMR (400 MHz, DMSO-$d_6$) δ8.84 (s, 1H), 8.68 (d, J=8.0 Hz, 1H), 7.46-7.40 (m, 1H), 7.19-7.12 (m, 3H), 6.94 (s, 1H), 5.51 (s, 2H), 4.50-4.44 (m, 1H), 4.37-4.31 (m, 2H), 3.27 (s, 3H), 2.64-2.60 (m, 1H), 2.52-2.48 (m, 1H). LCMS $R_T$=0.811 min, m/z=452.1 [M+H]$^+$.

LCMS (5 to 95% acetonitrile in water+0.03% trifluoacetic acid over 1.5 mins) retention time 0.811 min, ESI+ found [M+H]=452.1.

SFC conditions: Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Example 528

WX Method 076

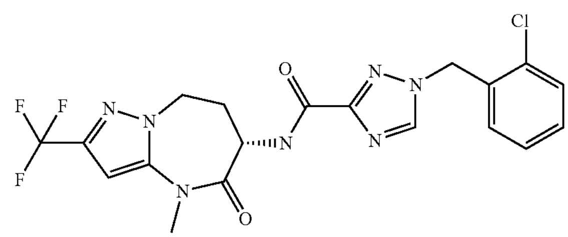

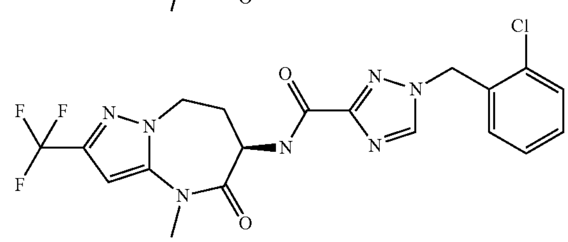

1-[(2-chlorophenyl)methyl]-N-(6S)-4-methyl-5-oxo-2-(trifluoromethyl)-7,8-dihydro-6-pyrazolo[1,5-a][1,3]diazepin-6-yl-1,2,4-triazole-3-carboxamide and 1-1-[(2-chlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide Amide coupling prepared in a similar fashion to WX Method 073 (RIP1K_experimental_3$^{rd}$_WX.doc). The obtained racemic compound was separated by chiral SFC:

1-[(2-chlorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time=4.393 min) (20 mg, 40%) as white solids. $^1$H NMR (400 MHz, $CD_3OD$) δ8.58 (s, 1H), 7.47-7.42 (m, 1H), 7.42-7.28 (m, 3H), 6.68 (s, 1H), 5.61 (s, 2H), 4.56-4.46 (m, 2H), 4.41-4.33 (m, 1H), 3.37 (s, 3H), 2.93-2.86 (m, 1H), 2.36-2.29 (m, 1H). LC-MS $R_T$=1.838 min, m/z=468.1 $[M+H]^+$.

LCMS (10 to 80% acetonitrile in water+0.03% ammonium bicarbonate over 3.0 mins) retention time 1.838 min, ESI+ found [M+H]=468.1.

1-1-[(2-chlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide (Peak 2, retention time=5.055 min) (21 mg, 41%) as white solids. $^1$H NMR (400 MHz, METHANOL-d4) 68.58 (s, 1H), 7.47-7.42 (m, 1H), 7.42-7.28 (m, 3H), 6.68 (s, 1H), 5.61 (s, 2H), 4.56-4.46 (m, 2H), 4.41-4.33 (m, 1H), 3.37 (s, 3H), 2.93-2.86 (m, 1H), 2.36-2.29 (m, 1H). LC-MS $R_T$=1.838 min, m/z=468.1 $[M+H]^+$.

LCMS (10 to 80% acetonitrile in water+0.03% ammonium bicarbonate over 3.0 mins) retention time 1.838 min, ESI+ found [M+H]=468.1.

SFC condition: Column: Chiralcel OD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 529

WX Method 065

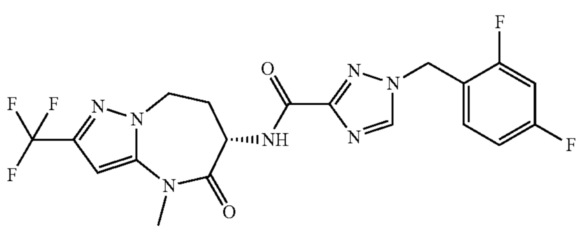

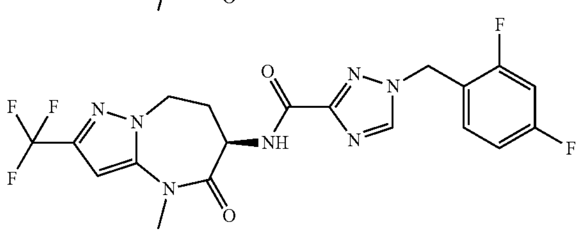

1-[(2,4-difluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(2,4-difluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide

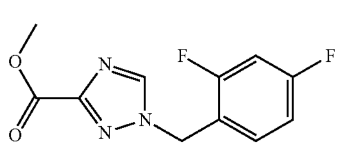 [SMILES: COC(=O)c1ncn(Cc2ccc(F)cc2F)n1]

Step 1: methyl 1-(2,4-difluorobenzyl)-1H-1,2,4-triazole-3-carboxylate

To a solution of methyl 1H-1,2,4-triazole-3-carboxylate (10.0 g, 78.68 mmol) in N,N-dimethylformamide (200 mL) was added potassium carbonate (21.8 g, 157.36 mmol) and 2,4-difluorobenzyl bromide (19.6 g, 94.41 mmol). The mixture was stirred at 25° C. for 12 h and concentrated under reduced pressure. The residue was diluted with brine (200 mL) and extracted with ethyl acetate (3×100 mL). The combined organic extracts were dried over anhydrous sodium sulfate and concentrated. The residue was purified by column chromatography (silica gel, 100-200 mesh, 0-100% ethyl acetate in petroleum ether) to afford methyl 1-(2,4-difluorobenzyl)-1H-1,2,4-triazole-3-carboxylate (7.7 g, 38.6%) as white solids.

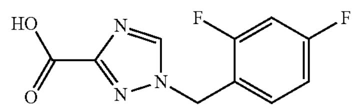 [SMILES: O=C(O)c1ncn(Cc2ccc(F)cc2F)n1]

Step 2: 1-(2,4-difluorobenzyl)-1H-1,2,4-triazole-3-carboxylic acid

A mixture of methyl 1-[(2,4-difluorophenyl)methyl]-1,2,4-triazole-3-carboxylate (2.0 g, 7.9 mmol). and potassium hydroxide (0.9 g, 15.8 mmol) in ethanol (40 mL) and water (5 mL) was stirred at 25° C. for 12 h. The ethanol was evaporated under reduced pressure and the residue was diluted with water (20 mL). The solution was adjusted to pH=4 by addition of 2N HCl. The resulting solid was collected by filtration and dried to give crude 1-[(2,4-difluorophenyl)methyl]-1,2,4-triazole-3-carboxylic acid (1.69 g, 90%) as a white solid.

$^1$H NMR (400 MHz, $CD_3OD$) δ8.64 (s, 1H), 7.51-7.47 (m, 1H), 7.06-7.00 (m, 2H), 5.54-5.49 (m, 2H).

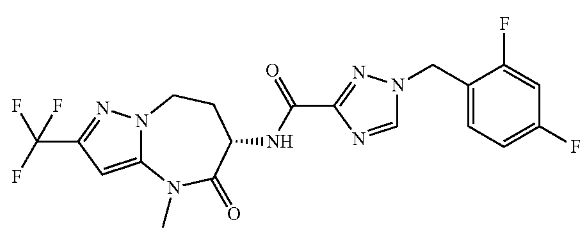

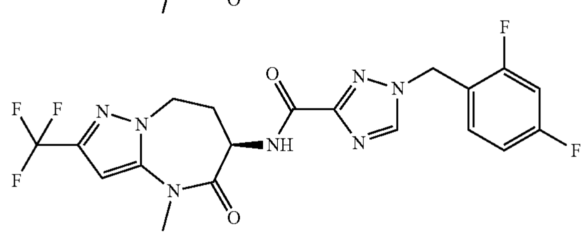

Step 3: 1-[(2,4-difluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(2,4-difluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide A mixture of 1-(3-dimethylaminopropyl)-3-ethylcarbodiimidehydrochloride (42 mg, 0.22 mmol), 1-[(2,4-difluorophenyl)methyl]-1,2,4-triazole-3-carboxylic acid (55 mg, 0.23 mmol), 1-hydroxybenzotriazole (27 mg, 0.20 mmol) and 6-amino-4-methyl-2-(trifluoromethyl)-7,8-dihydro-6H-pyrazolo[1,5-a][1,3]diazepin-5-one (50 mg, 0.20 mmol) in N,N-dimethylformamide (4 mL) was stirred at 25° C. for 12 h and concentrated under reduced pressure. The residue was purified by RP-HPLC (acetonitrile 0-40%/0.05% ammonium hydroxide in water) to afford 1-[(2,4-difluorophenyl) methyl]-N-[4-methyl-5-oxo-2-(trifluoromethyl)-7,8-dihydro-6H-pyrazolo[1,5-a][1,3]diazepin-6-yl]-1,2,4-triazole-3-carboxamide (50 mg, 53%) as white solid. The obtained racemic material was separated by chiral SFC to give:

1-[(2,4-difluorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time=3.802 min) (14 mg, 27%) as white solids. $^1$H NMR (400 MHz, $CD_3OD$) δ 8.58 (s, 1H), 7.48-7.42 (m, 1H), 7.05-6.97 (m, 2H), 6.66 (s, 1H), 5.52 (s, 2H), 4.53-4.44 (m, 2H), 4.39-4.33 (m, 1H), 3.36 (s, 3H), 2.89-2.84 (m, 1H), 2.35-2.29 (m, 1H). LCMS $R_T$=1.805 min; m/z=470.1 $(M+H)^+$.

LCMS (10 to 80% acetonitrile in water+0.03% ammonium bicarbonate over 3.0 mins) retention time 1.805 min, ESI+ found [M+H]=470.1.

1-[(2,4-difluorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide (Peak 2, retention time=4.620 min) (14 mg, 27% yield) as white solids. $^1$H NMR (400 MHz, $CD_3OD$) δ8.59 (s, 1H), 7.50-7.42 (m, 1H), 7.08-6.94 (m, 2H), 6.68 (s, 1H), 5.53 (s, 2H), 4.57-4.47 (m, 2H), 4.41-4.33 (m, 1H), 3.37 (s, 3H), 2.92-2.84 (m, 1H), 2.35-2.29 (m, 1H). LCMS $R_T$=1.805 min; m/z=470.1 $(M+H)^+$.

LCMS (10 to 80% acetonitrile in water+0.03% ammonium bicarbonate over 3.0 mins) retention time 1.805 min, ESI+ found [M+H]=470.1.

SFC condition: Column: Chiralcel OD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 530

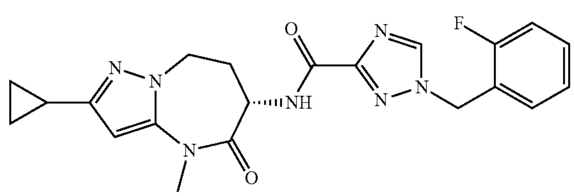 [SMILES: CN1C(=O)[C@@H](NC(=O)c2ncn(Cc3ccccc3F)n2)CCn2nc(C3CC3)cc21]

1-[(2-fluorophenyl)methyl]-N-(6S)-2-cyclopropyl-4-methyl-5-oxo-7,8-dihydro-6H-pyrazolo[1,5-a][1,3] diazepin-6-yl-1,2,4-triazole-3-carboxamide Amide coupling prepared in a similar fashion to WX Method 043. The crude was purified by RP-HPLC (acetonitrile 42-62%/0.05% ammonium hydroxide in water) to give 1-[(2-fluorophenyl)methyl]-N-(6 S)-2-cyclopropyl-4-methyl-5-oxo-7,8-dihydro-6H-pyrazolo[1,5-a][1,3]diazepin-6-yl-1,2,4-triazole-3-carboxamide (38 mg, 33.6%) as a white solid. $^1$H NMR (400 MHz, $CD_3OD$) δ8.58 (s, 1H), 7.41-7.36 (m, 2H), 7.21-7.15 (m, 2H), 6.00 (s, 1H), 5.55 (s, 2H), 4.53-4.48 (m, 1H), 4.32-4.21 (m, 2H), 3.31 (s, 3H), 2.86-2.79 (m, 1H), 2.25-2.23 (m, 1H), 1.91-1.87 (m, 1H), 0.95-0.92 (m, 2H), 0.75-0.72 (m, 2H). LC-MS $R_T$=0.958 min, m/z=424.2 $(M+H)^+$.

LCMS (10 to 80% acetonitrile in water+0.03% trifluoacetic acid over 2.0 mins) retention time 0.958 min, ESI+ found [M+H]=424.2.

Example 531

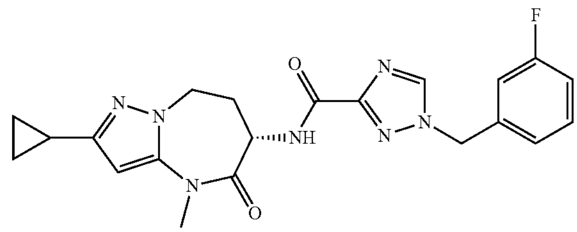 [SMILES: CN1C(=O)[C@@H](NC(=O)c2ncn(Cc3cccc(F)c3)n2)CCn2nc(C3CC3)cc21]

1-[(3-fluorophenyl)methyl]-N-(6S)-2-cyclopropyl-4-methyl-5-oxo-7,8-dihydro-6H-pyrazolo[1,5-a][1,3] diazepin-6-yl-1,2,4-triazole-3-carboxamide Amide coupling prepared in a similar fashion to WX Method 049. The crude was purification by RP-HPLC (acetonitrile 17-47%/0.05 ammonium hydroxide in water) to give 1-[(3-fluorophenyl)methyl]-N-(6 S)-2-cyclopropyl-4-methyl-5-oxo-7,8-dihydro-6H-pyrazolo[1,5-a][1,3]diazepin-6-yl-1,2,4-triazole-3-carboxamide (Peak 1, retention time 1.762 min) (28 mg, 25%) as a white solid. $^1$H NMR (400 MHz, $CD_3OD$) δ8.61 (s, 1H), 7.40-7.36 (m, 1H), 7.17-7.08 (m, 3H), 6.00 (s, 1H), 5.49 (s, 2H), 4.55-4.50 (m, 1H), 4.31-4.19 (m, 2H), 3.31 (s, 3H), 2.87-2.80 (m, 1H), 2.28-2.24 (m, 1H), 1.91-1.88 (m, 1H), 0.95-0.92 (m, 2H), 0.75-0.73 (m, 2H). LCMS $R_T$=0.958 min, m/z=424.2 $[M+H]^+$.

LCMS (10 to 80% acetonitrile in water+0.03% trifluoacetic acid over 2.0 mins) retention time 0.958 min, ESI+ found [M+H]=424.2

Example 532

WX Method 070

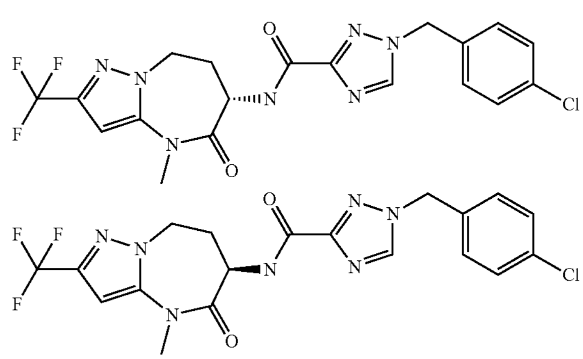

1-[(4-chlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(4-chlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide

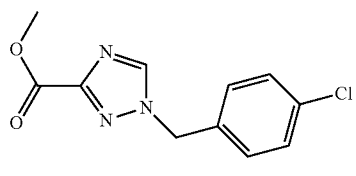 [SMILES: COC(=O)c1ncn(Cc2ccc(Cl)cc2)n1]

Step 1: methyl 1-(4-chlorobenzyl)-1H-1,2,4-triazole-3-carboxylate

To a solution of methyl 1H-1,2,4-triazole-3-carboxylate (3.0 g, 11.92 mmol) in N,N-dimethylformamide (25 mL) was added potassium carbonate (4.9 g, 35.76 mmol) and 1-(bromomethyl)-4-chlorobenzene (2.9 g, 14.3 mmol). The mixture was stirred at 25° C. for 12 h and filtered. The filtrate was concentrated under reduced pressure and the residue was purified by column chromatography (silica gel, 100-200 mesh, 0 to 100% ethyl acetate in petroleum ether) to afford methyl 1-(4-chlorobenzyl)-1H-1,2,4-triazole-3-carboxylate (1.6 g, 54%) as white solids.

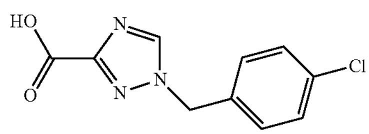 [SMILES: O=C(O)c1ncn(Cc2ccc(Cl)cc2)n1]

Step 2: 1-(4-chlorobenzyl)-1H-1,2,4-triazole-3-carboxylic acid

A mixture of methyl 1-[(4-chlorophenyl)methyl]-1,2,4-triazole-3-carboxylate (1.6 g, 6.41 mmol) and potassium hydroxide (719 mg, 12.82 mmol) in ethanol (40 mL) and water (5 mL) was stirred at 25° C. for 12 h. The ethanol was evaporated and the residue was diluted with water (20 mL). The mixture was adjusted to pH=4 by addition of 2N HCl. The resulting solid was collected by filtration and dried to, obtain 1-(4-chlorobenzyl)-1H-1,2,4-triazole-3-carboxylic acid (1.49 g, 98%) as white solids. $^1$H NMR (400 MHz, $CD_3OD$) δ8.64 (s, 1H), 7.40-7.34 (m, 4H), 5.47 (s, 2H).

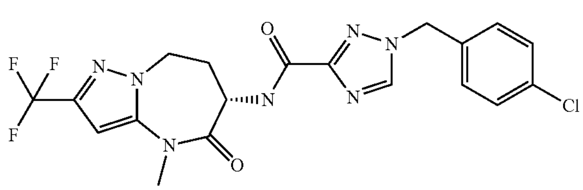

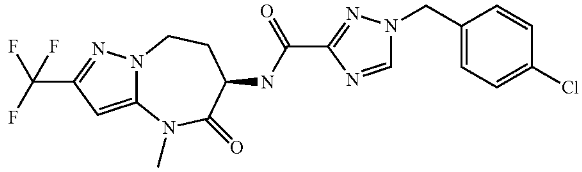

Step 3: 1-[(4-chlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(4-chlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide To a solution of 6-amino-4-methyl-2-(trifluoromethyl)-7,8-dihydro-6H-pyrazolo[1,5-a][1,3]diazepin-5-one (50 mg, 0.20 mmol) in N,N-dimethylformamide (4 mL) was added 1-(3-dimethyl aminopropyl)-3-ethylcarbodiimidehydrochloride (42 mg, 0.22 mmol) 1-[(4-chlorophenyl)methyl]-1,2,4-triazole-3-carboxylic acid (45 mg, 0.20 mmol) 1-hydroxybenzotriazole (27 mg, 0.20 mmol). The reaction mixture was stirred at 25° C. for 12 h and concentrated under reduced pressure. The residue was purified by RP-HPLC (acetonitrile 0-40%/0.05% ammonium hydroxide in water) to afford 1-[(4-chlorophenyl)methyl]-N-[4-methyl-5-oxo-2-(trifluoromethyl)-7,8-dihydro-6H-pyrazolo[1,5-a][1,3]diazepin-6-yl]-1,2,4-triazole-3-carboxamide (50 mg, 53%) as white solid. The obtained racemic compound was separated by chiral SFC to give:

1-[(4-chlorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time=5.006 min) (18 mg, 36%) as white solids. $^1$H NMR (400 MHz, DMSO-$d_6$) δ 8.82 (s, 1H), 8.70-8.68 (m, 1H), 7.41-7.39 (m, 2H), 7.20-7.22 (m, 2H), 6.94 (s, 1H), 5.49 (s, 2H), 4.95-4.44 (m, 1H), 4.38-4.30 (m, 2H), 3.26 (s, 3H), 2.66-2.63 (m, 1H), 2.32-2.29 (m, 1H). LCMS $R_T$=1.889 min, m/z=468.1 $[M+H]^+$.

LCMS (10 to 80% acetonitrile in water+0.03% ammonium bicarbonate over 3.0 mins) retention time 1.889 min, ESI+ found [M+H]=468.1.

1-[(4-chlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide (Peak 2, retention time=6.159 min) (16 mg, 32%) as white solids. $^1$H NMR (400 MHz, DMSO-d6) δ8.82 (s, 1H), 8.70-8.68 (m, 1H), 7.41-7.39 (m, 2H), 7.20-7.22 (m, 2H), 6.94 (s, 1H), 5.49 (s, 2H), 4.95-4.44 (m, 1H), 4.38-4.30 (m, 2H), 3.26 (s, 3H), 2.66-2.63 (m, 1H), 2.32-2.29 (m, 1H). LCMS $R_T$=1.889 min, m/z=468.1 $[M+H]^+$.

LCMS (10 to 80% acetonitrile in water+0.03% ammonium bicarbonate over 3.0 mins) retention time 1.889 min, ESI+ found [M+H]=468.1.

SFC condition: Column: Chiralcel OD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 533

WX Method 079

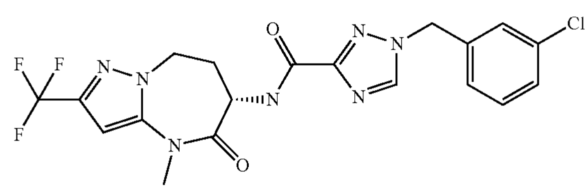

-continued

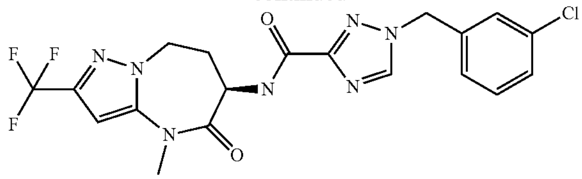

1-[(3-chlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(3-chlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide Amide coupling prepared in a similar fashion to WX Method 077 (RIP1K_experimental_3rd_WX.doc). The obtained racemic compound was separated by SFC to give:

1-[(3-chlorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time=4.658 min) (14 mg, 27%) as white solids. $^1$H NMR (400 MHz, DMSO-$d_6$) δ 8.84 (s, 1H), 8.69-8.67 (m, 1H), 7.46-7.32 (m, 3H), 7.28-7.25 (m, 1H), 6.94 (s, 1H), 5.50 (s, 2H), 4.49-4.44 (m, 1H), 4.37-4.32 (m, 2H), 3.26 (s, 3H), 2.65 (s, 1H), 2.46-2.42 (m, 1H). LC-MS $R_T$=1.883 min, m/z=468.1 $[M+H]^+$.

LCMS (10 to 80% acetonitrile in water+0.03% ammonium bicarbonate over 3.0 mins) retention time 1.883 min, ESI+ found [M+H]=468.1.

1-[(3-chlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide (Peak 2, retention time=5.731 min) (8 mg, 15%) as white solids. $^1$H NMR (400 MHz, METHANOL-d4) δ8.62 (s, 1H), 7.45-7.32 (m, 3H), 7.29-7.28 (m, 1H), 6.68 (s, 1H), 5.48 (s, 2H), 4.58-4.47 (m, 2H), 4.41-4.33 (m, 1H), 3.37 (s, 3H), 2.91-2.86 (m, 1H), 2.36-2.31 (m, 1H). LC-MS $R_T$=1.883 min, m/z=468.1 $[M+H]^+$.

LCMS (10 to 80% acetonitrile in water+0.03% ammonium bicarbonate over 3.0 mins) retention time 1.883 min, ESI+ found [M+H]=468.1.

SFC condition: Column: Chiralcel OD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 534

WX Method 069

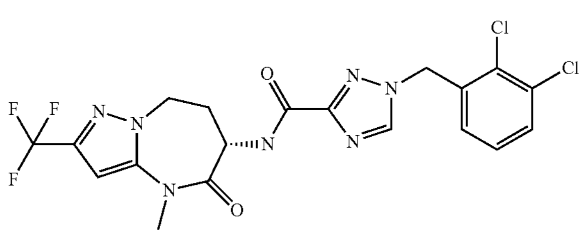

-continued

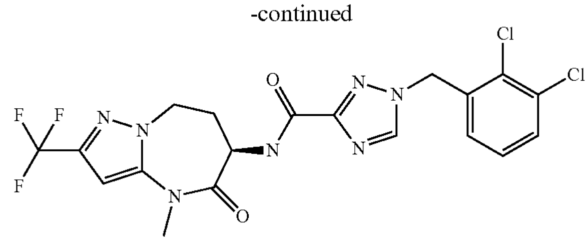

1-[(2,3-dichlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(2,3-dichlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide

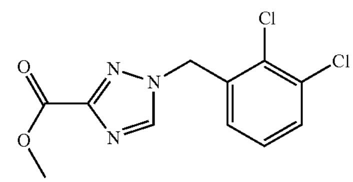 [SMILES: COC(=O)c1ncn(Cc2cccc(Cl)c2Cl)n1]

Step 1: methyl 1-(2,3-dichlorobenzyl)-1H-1,2,4-triazole-3-carboxylate

To a solution of methyl 1H-1,2,4-triazole-3-carboxylate (1.5 g, 11.8 mmol) in N,N-dimethylformamide (25 mL) was added potassium carbonate (3.3 g, 23.6 mmol) and 1-(bromomethyl)-2,3-dichloro-benzene (3.4 g, 14.16 mmol). The mixture was stirred at 25° C. for 12 h and filtered. The filtrate was concentrated under reduced pressure and the residue was purified by column chromatography (silica gel, 100-200 mesh, 0 to 100% ethyl acetate in petroleum ether) to afford methyl 1-(2,3-dichlorobenzyl)-1H-1,2,4-tri azole-3-carboxylate (1.91 g, 57%) as white solids, used as is in the next step.

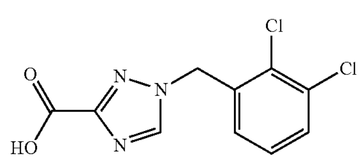 [SMILES: O=C(O)c1ncn(Cc2cccc(Cl)c2Cl)n1]

Step 2: 1-(2,3-dichlorobenzyl)-1H-1,2,4-triazole-3-carboxylic acid

A mixture of solution of methyl 1-[(2,3-dichlorophenyl)methyl]-1,2,4-triazole-3-carboxylate (1.9 g, 6.68 mmol) and potassium hydroxide (749 mg, 13.36 mmol) in ethanol (40 mL) and water (5 mL) was stirred at 25° C. for 12 h. The ethanol was evaporated and the residue was diluted with water (20 mL). The mixture was adjusted to pH=4 by addition of 2 N HCl. The resulting solid was collected by filtration and dried to obtain 1-[(2,3-dichlorophenyl)methyl]-1,2,4-triazole-3-carboxylic acid (1.7 g, 95%) as white solids. $^1H$ NMR (400 MHz, $CD_3OD$) δ8.69 (s, 1H), 7.59-7.57 (m, 1H), 7.37-7.24 (m, 2H), 5.66 (s, 2H).

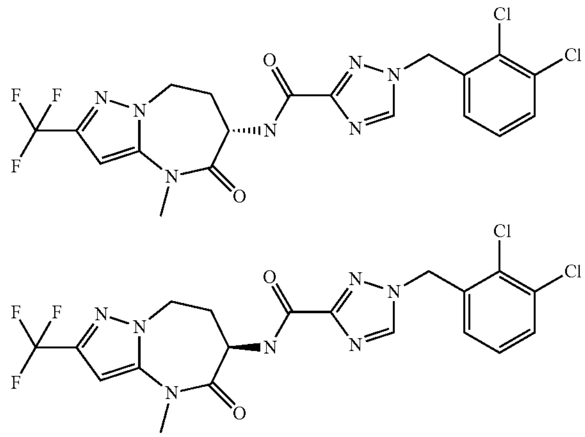

Step 3: 1-[(2,3-dichlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide and 1-[(2,3-dichlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide To a solution of 6-amino-4-methyl-2-(trifluoromethyl)-7,8-dihydro-6H-pyrazolo[1,5-a][1,3]diazepin-5-one (50 mg, 0.20 mmol) in N,N-dimethylformamide (4 mL) was added 1-(3-dimethyl aminopropyl)-3-ethylcarbodiimidehydrochloride (42 mg, 0.22 mmol) 1-hydroxybenzotriazole (27 mg, 0.20 mmol) 1-[(2,3-dichlorophenyl)methyl]-1,2,4-triazole-3-carboxylic acid (54 mg, 0.20 mmol). The reaction mixture was stirred at 25° C. for 12 h and concentrated under reduced pressure. The residue was purified by RP-HPLC (acetonitrile 0-40%/0.05% ammonium hydroxide in water) to afford 1-[(2,3-dichlorophenyl)methyl]-N-[4-methyl-5-oxo-2-(trifluoromethyl)-7,8-dihydro-6H-pyrazolo[1,5-a][1,3]diazepin-6-yl]-1,2,4-triazole-3-carboxamide (50 mg, 49%) as white solid. The obtained racemic material was separated by chiral SFC to give:

1-[(2,3-dichlorophenyl)methyl]-N-(6 S)-4-methyl-5-oxo-2-(trifluoromethyl)-7,8-dihydro-6H-pyrazolo[1,5-a][1,3]diazepin-6-yl-1,2,4-triazole-3-carboxamide (Peak 1, retention time=5.069 min) (14 mg, 27%) as white solids. $^1H$ NMR (400 MHz, DMSO-$d_6$) δ 8.84 (s, 1H), 8.68-8.66 (m, 1H), 7.67-7.64 (m, 1H), 7.41-7.37 (m, 1H), 7.21-7.19 (m, 1H), 6.94 (s, 1H), 5.65 (s, 2H), 4.47-4.38 (m, 1H), 4.38-4.29 (m, 2H), 3.27 (s, 3H), 2.67-2.65 (m, 1H), 2.33-2.31 (m, 1H). LCMS $R_T$=1.954 min, m/z=502.0 $[M+H]^+$.

LCMS (10 to 80% acetonitrile in water+0.03% ammonium bicarbonate over 3.0 mins) retention time 1.954 min, ESI+ found [M+H]=502.0.

1-[(2,3-dichlorophenyl)methyl]-N-(6R)-4-methyl-5-oxo-2-(trifluoromethyl)-7,8-dihydro-6H-pyrazolo[1,5-a][1,3]diazepin-6-yl-1,2,4-triazole-3-carboxamide (Peak 2, retention time=5.870 min) (16 mg, 31%) as white solids. $^1H$ NMR (400 MHz, DMSO-d6) δ8.84 (s, 1H), 8.68-8.66 (m, 1H), 7.67-7.64 (m, 1H), 7.41-7.37 (m, 1H), 7.21-7.19 (m, 1H), 6.94 (s, 1H), 5.65 (s, 2H), 4.47-4.38 (m, 1H), 4.38-4.29 (m, 2H), 3.27 (s, 3H), 2.67-2.65 (m, 1H), 2.33-2.31 (m, 1H). LCMS $R_T$=1.954 min, m/z=502.0 $[M+H]^+$.

LCMS (10 to 80% acetonitrile in water+0.03% ammonium bicarbonate over 3.0 mins) retention time 1.954 min, ESI+ found [M+H]=502.0.

SFC condition: Column: Chiralcel OD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 535

WX Method 091

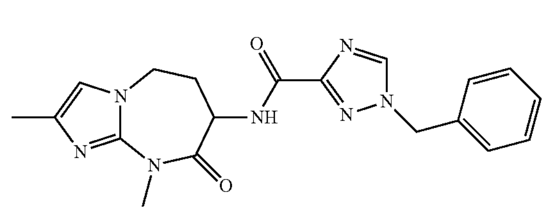 [SMILES: Cc1cn2c(n1)N(C)C(=O)C(NC(=O)c1ncn(Cc3ccccc3)n1)CC2]

1-benzyl-N-(2,9-dimethyl-8-oxo-6,7,8,9-tetrahydro-5H-imidazo[1,2-a][1,3]diazepin-7-yl)-1H-1,2,4-triazole-3-carboxamide

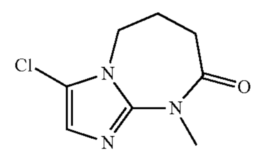

Step 1: 3-chloro-9-methyl-6,7-dihydro-5H-imidazo[1,2-a][1,3]diazepin-8(9H)-one

To a solution of 9-methyl-6,7-dihydro-5H-imidazo[1,2-a][1,3]diazepin-8-one (1.2 g, 7.26 mmol) in N,N-dimethylformamide (20 mL) was added 1-chloropyrrolidine-2,5-dione (776 mg, 5.81 mmol). The reaction mixture was stirred at 25° C. for 15 h and concentrated under reduced pressure. The residue was purified by column chromatography (silica gel, 100-200 mesh, 0 to 50% ethyl acetate in petroleum ether) to afford 3-chloro-9-methyl-6,7-dihydro-5H-imidazo[1,2-a][1,3]diazepin-8-one (700 mg, 48%) as a light yellow oil, used as is in the next step.

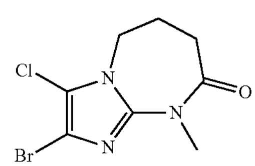

Step 2: 2-bromo-3-chloro-9-methyl-6,7-dihydro-5H-imidazo[1,2-a][1,3]diazepin-8(9H)-one To a solution of 3-chloro-9-methyl-6,7-dihydro-5H-imidazo[1,2-a][1,3]diazepin-8-one (700 mg, 3.51 mmol) in N,N-dimethylformamide (10 mL) was added 1-bromo-2,5- pyrrolidinedione (499 mg, 2.81 mmol). The reaction mixture was stirred at 25° C. for 2 h and then concentrated under reduced pressure. The residue was purified by column chromatography (silica gel, 100-200 mesh, 0 to 50% ethyl acetate in petroleum ether) to afford 2-bromo-3-chloro-9-methyl-6,7-dihydro-5H-imidazo[1,2-a][1,3]diazepin-8-one (670 mg, 68%) as a yellow solid, used as is in the next step. LCMS RT=1.791 min; m/z=278.0 $(M+H)^+$.

LCMS (0 to 60% acetonitrile in water+0.05% ammonium bicarbonate over 3 mins) retention time 1.791 ESI+ found [M+H]=278.0

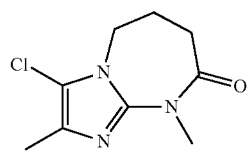

Step 3: 3-chloro-2,9-dimethyl-6,7-dihydro-5H-imidazo[1,2-a][1,3]diazepin-8(9H)-one A mixture of 2-bromo-3-chloro-9-methyl-6,7-dihydro-5H-imidazo[1,2-a][1,3]diazepin-8-one (670 mg, 2.41 mmol), cesium carbonate (784 mg, 2.41 mmol), 2,4,6-trimethyl-1,3,5,2,4,6-trioxatriborinane (302 mg, 2.41 mmol) and [1,1'-Bis(diphenylphosphino) ferrocene]dichloro palladium (II) (176 mg, 0.24 mmol) in 1,4-dioxane (10 mL) and water (1 mL) was heated at 110° C. for 0.5 h under microwave conditions. The reaction mixture was concentrated under reduced pressure and the residue was purified by column chromatography (silica gel, 100-200 mesh, 0 to 100% ethyl acetate in petroleum ether) to afford 3-chloro-2,9-dimethyl-6,7-dihydro-5H-imidazo[1,2-a][1,3]diazepin-8-one (120 mg, 23%) as a yellow oil, used as is in the next step.

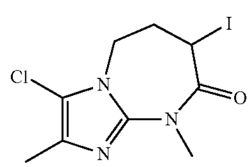

Step 4: 3-chloro-7-iodo-2,9-dimethyl-6,7-dihydro-5H-imidazo[1,2-a][1,3]diazepin-8(9H)-one To a solution of 3-chloro-2,9-dimethyl-6,7-dihydro-5H-imidazo[1,2-a][1,3]diazepin-8-one (250 mg, 1.17 mmol) in dichloromethane (30 mL) was added N1,N1,N3,N3-tetramethylpropane-1,3-diamine (816 mg, 7.02 mmol) and iodotrimethylsilane (1405 mg, 7.02 mmol) at −15° C. The reaction mixture was stirred at −15° C. for 2 h and iodine (891 mg, 3.51 mmol) was added. The mixture was stirred at −15° C. for another 2 h and quenched by addition of saturated aqueous sodium sulfite (10 mL). The solution was extracted with dichloromethane (3×20 mL). The combined organic layers were dried over sodium sulfate and concentrated. The residue was purified by column chromatography (silica gel, 100-200 mesh, 0 to 10% methanol in dichloromethane) to afford 3-chloro-7-iodo-2,9-dimethyl-6,7-dihydro-5H-imidazo[1,2-a][1,3]diazepin-8-one (280 mg, 71%) as a colorless oil, used as is in the next step. LCMS RT=1.848 min; m/z=255.1 $(M+H)^+$.

LCMS (0 to 60% acetonitrile in water+0.05% ammonium bicarbonate over 3 mins) retention time 1.848 ESI+ found [M+H]=255.1

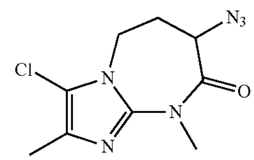 [SMILES: Cc1nc2n(c1Cl)CCC(N=[N+]=[N-])C(=O)N2C]

Step 5: 7-azido-3-chloro-2,9-dimethyl-6,7-dihydro-5H-imidazo[1,2-a][1,3]diazepin-8(9H)-one A mixture of 3-chloro-7-iodo-2,9-dimethyl-6,7-dihydro-5H-imidazo[1,2-a][1,3]diazepin-8-one (280 mg, 0.82 mmol) and sodium azide (380 mg, 5.85 mmol) in N,N-dimethylformamide (5 mL) was stirred at 25° C. for 2 h. The reaction mixture was added to ice water (5 mL) and extracted with ethyl acetate (3×10 mL). The combined organic layers were concentrated under reduced pressure and the residue was purified by preparative TLC (50% ethyl acetate in petroleum ether, $R_f$=0.6) to afford 7-azido-3-chloro-2,9-dimethyl-6,7-dihydro-5H-imidazo[1,2-a][1,3]diazepin-8-one (200 mg, 95%) as a yellow oil, used as is in the next step, used as is in the next step.

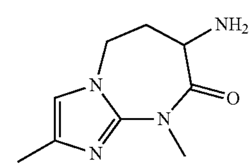

Step 6: 7-amino-2,9-dimethyl-6,7-dihydro-5H-imidazo[1,2-a][1,3]diazepin-8(9H)-one A mixture of 7-azido-3-chloro-2,9-dimethyl-6,7-dihydro-5H-imidazo[1,2-a][1,3]diazepin-8-one (200 mg, 0.79 mmol) and Pd/C (10%, 836 mg, 0.79 mmol) in 1,4-dioxane (5 mL) was hydrogenated (15 psi) for 5 h and filtered. The filtrate was concentrated under reduced pressure and the residue was purified by column chromatography (silica gel, 100-200 mesh, 0 to 10% methanol in dichloromethane) to afford 7-amino-2,9-dimethyl-6,7-dihydro-5H-imidazo[1,2-a][1,3]diazepin-8-one (80 mg, 52%) as a yellow oil, used as is in the next step. LCMS RT=1.074 min; m/z=195.2 $(M+H)^+$.

LCMS (0 to 60% acetonitrile in water+0.05% ammonium bicarbonate over 3 mins) retention time 1.074 ESI+ found [M+H]=195.2

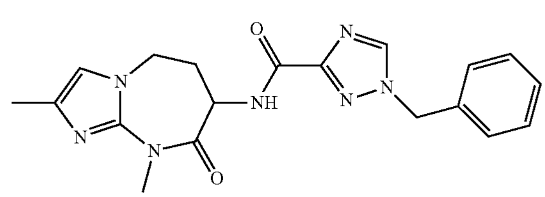 [SMILES: Cc1cn2c(n1)N(C)C(=O)C(NC(=O)c1ncn(Cc3ccccc3)n1)CC2]

Step 7: 1-benzyl-N-(2,9-dimethyl-8-oxo-6,7,8,9-tetrahydro-5H-imidazo[1,2-a][1,3]diazepin-7-yl)-1H-1,2,4-triazole-3-carboxamide To a solution of 1-benzyl-1,2,4-triazole-3-carboxylic acid (83 mg, 0.41 mmol) in N,N-dimethylformamide (5 mL) was added 7-amino-2,9-dimethyl-6,7-dihydro-5H-imidazo[1,2-a][1,3]diazepin-8-one (80 mg, 0.41 mmol), 1-(3-dimethylaminopropyl)-3-ethylcarbodiimidehydrochloride (79 mg, 0.41 mmol) and 1-hydroxybenzotriazole (55 mg, 0.41 mmol). The reaction mixture was stirred at 25° C. for 1 h and concentrated under reduced pressure. The residue was purified by RP-HPLC (13% to 43% acetonitrile/0.05% ammonia hydroxide in water) to afford 1-benzyl-N-(2,9-dimethyl-8-oxo-6,7-dihydro-5H-imidazo[1,2-a][1,3]diazepin-7-yl)-1,2,4-triazole-3-carboxamide (42 mg, 27%) as white solid. $^1H$ NMR (400 MHz, $CD_3OD$) δ8.56 (s, 1H), 7.39-7.32 (m, 5H), 6.78 (s, 1H), 5.47 (s, 2H), 4.55-4.50 (m, 1H), 4.21-4.15 (m, 1H), 4.03-3.98 (m, 1H), 3.36 (s, 3H), 2.85-2.79 (m, 1H), 2.29-2.23 (m, 1H), 2.19 (s, 3H). LCMS $R_T$=1.779 min, m/z=380.2 $(M+H)^+$. LCMS RT=1.779 min; m/z=380.2 $(M+H)^+$.

LCMS (0 to 60% acetonitrile in water+0.05% ammonium bicarbonate over 3 mins) retention time 1.779 min, ESI+ found [M+H]=380.2

Example 536

WX Method 149

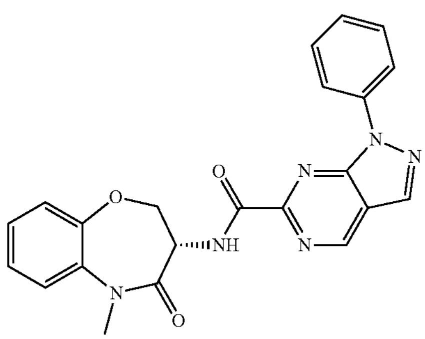 [SMILES: CN1C(=O)[C@@H](NC(=O)c2ncc3cnn(-c4ccccc4)c3n2)COc2ccccc21]

phenyl-N-[(3S)-5-methyl-4-oxo-2,3-dihydro-1,5-benzoxazepin-3-yl]pyrazolo[3,4-d]pyrimidine-6-carboxamide

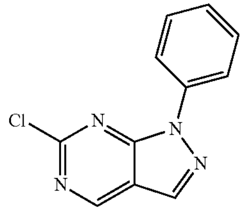 [SMILES: Clc1ncc2cnn(-c3ccccc3)c2n1]

Step 1: 6-chloro-1-phenyl-1H-pyrazolo[3,4-d]pyrimidine

A mixture of 6-chloro-1H-pyrazolo[3,4-d]pyrimidine (200 mg, 1.29 mmol), pyridine (205 mg, 2.59 mmol), copper(II)acetate (470 mg, 2.59 mmol) and phenylboronic acid (237 mg, 1.94 mmol) in dichloromethane (5 mL) was heated at 80° C. for 15 min under microwave conditions. The solution was filtered and the filtrate was concentrated under reduced pressure. The residue was purified by column chromatography (silica gel, 100-200 mesh, 0 to 20% ethyl acetate in petroleum ether) to give 6-chloro-1-phenyl-1H-pyrazolo[3,4-d]pyrimidine (250 mg, 84%) as a pale yellow solid, used as is in the next step.

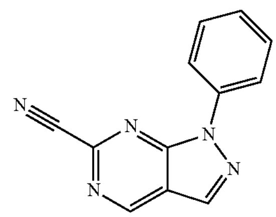 [SMILES: N#Cc1ncc2cnn(-c3ccccc3)c2n1]

Step 2: 1-phenyl-1H-pyrazolo[3,4-d]pyrimidine-6-carbonitrile

To a solution of 6-chloro-1-phenyl-1H-pyrazolo[3,4-d]pyrimidine (200 mg, 0.87 mmol) in dimethyl sulfoxide (10 mL) were added 1,4-diazabicyclo[2.2.2]octane (10 mg, 0.09 mmol) and sodium cyanide (85 mg, 1.73 mmol) in water (1 mL). The mixture was stirred at 25° C. for 3 h and diluted with water (10 mL). The mixture was extracted with ethyl acetate (3×15 mL). The combined organic layers were dried over sodium sulfate and concentrated under reduced pressure. The residue was purified by preparative TLC (40% ethyl acetate in petroleum ether) to afford 1-phenyl-1H-pyrazolo[3,4-d]pyrimidine-6-carbonitrile (80 mg, 42%) as a yellow solid. LCMS $R_T$=1.037 min; m/z=222.1 $(M+H)^+$.

LCMS (10 to 80% acetonitrile in water+0.03% trifluoacetic acid over 2.0 mins) retention time 1.037 min, ESI+ found [M+H]=222.1.

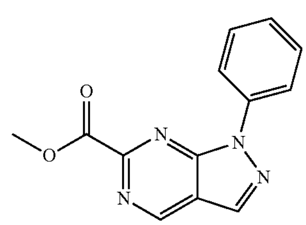 [SMILES: COC(=O)c1ncc2cnn(-c3ccccc3)c2n1]

Step 3: methyl 1-phenyl-1H-pyrazolo[3,4-d]pyrimidine-6-carboxylate

A solution of 1-cyclopentyl-1H-pyrazolo[3,4-d]pyrimidine-6-carbonitrile (80 mg, 0.36 mmol) in methanol (5 mL) was added HCl (4N in methanol, 1.5 mL). The mixture was stirred at 20° C. for 20 h and 50° C. for 3 h. The reaction solution was concentrated under reduced pressure to give crude methyl 1-phenyl-1H-pyrazolo[3,4-d]pyrimidine-6-carboxylate (90 mg, 98%) as a yellow solid. LCMS $R_T$=1.145 min; m/z=255.1 $(M+H)^+$.

LCMS (0 to 60% acetonitrile in water+0.03% trifluoacetic acid over 2.0 mins) retention time 1.145 min, ESI+ found [M+H]=255.1.

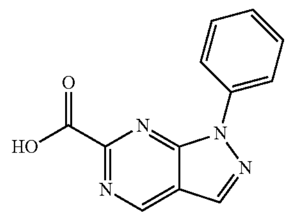 [SMILES: O=C(O)c1ncc2cnn(-c3ccccc3)c2n1]

Step 4: 1-phenyl-1H-pyrazolo[3,4-d]pyrimidine-6-carboxylic acid

A mixture of methyl 1-phenyl-1H-pyrazolo[3,4-d]pyrimidine-6-carboxylate (90 mg, 0.37 mmol) and lithium hydroxide hydrate (77 mg, 1.83 mmol) in tetrahydrofuran (5 mL) and water (1 mL) was stirred at 25° C. for 2 h. The organic solvent was evaporated under reduced pressure and the aqueous phase was adjusted to pH=4 by addition of 2N HCl. The mixture was extracted with ethyl acetate (3×20 mL). The combined organic layers were dried over magnesium sulfate and concentrated under reduced pressure to give crude 1-phenyl-1H-pyrazolo[3,4-d]pyrimidine-6-carboxylic acid (50 mg, 57%) as a yellow solid. LCMS $R_T$=1.015 min; m/z=241.1 $(M+H)^+$.

LCMS (0 to 60% acetonitrile in water+0.03% trifluoacetic acid over 2.0 mins) retention time 1.015 min, ESI+ found [M+H]=241.1.

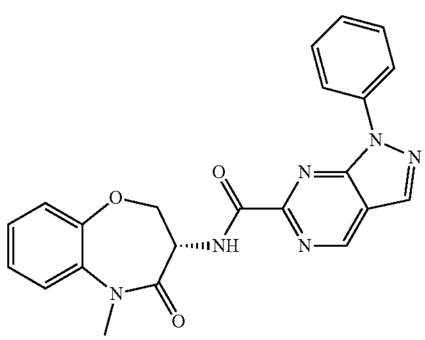

Step 5: phenyl-N-[(3S)-5-methyl-4-oxo-2,3-dihydro-1,5-benzoxazepin-3-yl]pyrazolo[3,4-d]pyrimidine-6-carboxamide A mixture of (3S)-3-amino-5-methyl-2,3-dihydro-1,5-benzoxazepin-4-one (22 mg, 0.11 mmol), 1-phenylpyrazolo[3,4-d]pyrimidine-6-carboxylic acid (25 mg, 0.10 mmol), $N^1$-((ethylimino)methylene)-$N^3$,$N^3$-dimethylpropane-1,3-diamine hydrochloride (24 mg, 0.12 mmol), 1H-benzo[d][1,2,3]triazol-1-ol (17 mg, 0.12 mmol) in N,N-dimethylformamide (3 mL) was stirred at 25° C. for 16 h. The mixture was concentrated under reduced pressure and the residue was purified by RP-HPLC (acetonitrile 35% to 65%/0.05% ammonia hydroxide in water) to give phenyl-N-[(3S)-5-methyl-4-oxo-2,3-dihydro-1,5-benzoxazepin-3-yl]pyrazolo[3,4-d]pyrimidine-6-carboxamide (30.9 mg, 71%) as a white solid. $^1$H NMR (400 MHz, DMSO-d6) δ9.61 (s, 1H), 9.17 (d, J=8.0 Hz, 1H), 8.79 (s, 1H), 8.23 (d, J=8.0 Hz, 2H), 7.65-7.61 (m, 2H), 7.52 (d, J=7.2 Hz, 1H), 7.45-7.40 (m, 1H), 7.35-7.28 (m, 3H), 4.95-4.90 (m, 1H), 4.62-4.54 (m, 2H). LCMS $R_T$=0.846 min; m/z=415.1 $(M+H)^+$.

LCMS (5-95% acetonitrile in water+0.05% trifluoacetic acid over 1.5 mins) retention time 0.846 min, ESI+ found [M+H]=415.1.

Example 537

WX Method 174

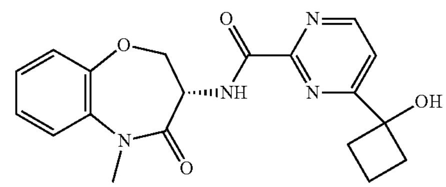 [SMILES: CN1C(=O)[C@@H](NC(=O)c2nccc(C3(O)CCC3)n2)COc2ccccc21]

4-(1-hydroxycyclobutyl)-N-[(3S)-5-methyl-4-oxo-2,3-dihydro-1,5-benzoxazepin-3-yl]pyrimidine-2

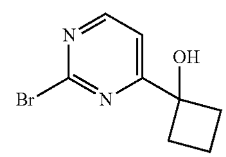 [SMILES: OC1(c2ccnc(Br)n2)CCC1]

Step 1: 1-(2-bromopyrimidin-4-yl)cyclobutanol

To a solution of cyclobutanone (1.48 g, 21.06 mmol) and 2-bromo-4-iodo-pyrimidine (2.0 g, 7.02 mmol) in tetrahydrofuran (60 mL) was added isopropylmagnesiumbromide (1.0 M in tetrahedron, 10.5 mL, 10.5 mmol) at −70° C. The mixture was stirred at −70° C. for 1 h and quenched by addition of saturated ammonium chloride (30 mL). The resulting solution was extracted with ethyl acetate (3×20 mL). The combined organic layers were washed with water (2×10 ml), brine (20 mL), dried over sodium sulfate and concentrated under reduced pressure. The residue was purified by column chromatography (silica gel, 100-200 mesh, 0 to 20% ethyl acetate in petroleum ether) to give 1-(2-bromopyrimidin-4-yl)cyclobutanol (350 mg, 22%) as a yellow oil. LC-MS $R_T$=0.52 min, m/z=228.8 $(M+H)^+$.

LCMS (5-95% acetonitrile in water+0.03% trifluoacetic acid over 1.5 mins) retention time 0.52/min, ESI+ found [M+H]=228.8

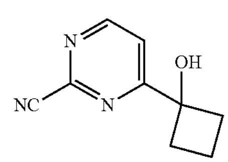 [SMILES: N#Cc1nccc(C2(O)CCC2)n1]

Step 3: 4-(1-hydroxycyclobutyl)pyrimidine-2-carbonitrile

To a solution of 1-(2-bromopyrimidin-4-yl)cyclobutanol (350 mg, 1.53 mmol) in dimethyl sulfoxide (5 mL) was added 1,4-diazabicyclo[2.2.2]octane (86 mg, 0.76 mmol)

and sodium cyanide (149 mg, 3.06 mmol) in water (2.5 mL). The mixture was stirred at 25° C. for 16 h and diluted with water (10 mL). The mixture was extracted with ethyl acetate (3×25 mL). The combined organic layers were concentrated under reduced pressure and the residue was purified by column chromatography (silica gel, 100-200 mesh, 0 to 30% ethyl acetate in petroleum ether) to afford 4-(1-hydroxycyclobutyl)pyrimidine-2-carbonitrile (260 mg, 97%) as a white solid. LC-MS $R_T$=0.60 min, m/z=175.8 $(M+H)^+$.

LCMS (5-95% acetonitrile in water+0.03% trifluoacetic acid over 1.5 mins) retention time 0.60/min, ESI+ found [M+H]=175.8

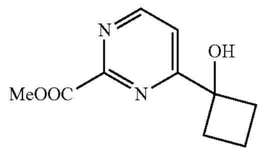 [SMILES: COC(=O)c1nccc(C2(O)CCC2)n1]

Step 4: methyl 4-(1-hydroxycyclobutyl)pyrimidine-2-carboxylate

A solution of 4-(1-hydroxycyclobutyl)pyrimidine-2-carbonitrile (100 mg, 0.57 mmol) in methanol (3 mL) was HCl (4N in methanol, 14.4 mL). The reaction mixture was stirred at 25° C. for 16 h and concentrated under reduced pressure. The residue was purified by preparative TLC (50% ethyl acetate in petroleum ether, $R_f$=0.3) to afford methyl 4-(1-hydroxycyclobutyl)pyrimidine-2-carboxylate (16 mg, 14%) as yellow oil. LC-MS $R_T$=1.77 min, m/z=209.0 $(M+H)^+$.

LCMS (0-60% acetonitrile in water+0.05% trifluoacetic acid over 4 mins) retention time 1.77/min, ESI+ found [M+H]=209.0.

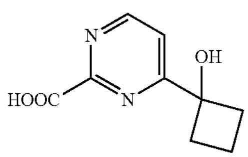 [SMILES: O=C(O)c1nccc(C2(O)CCC2)n1]

Step 5: 4-(1-hydroxycyclobutyl)pyrimidine-2-carboxylic acid

A mixture of methyl 4-(1-hydroxycyclobutyl)pyrimidine-2-carboxylate (16 mg, 0.08 mmol) and lithium hydroxide (9 mg, 0.38 mmol) in tetrahydrofuran (5 mL) and water (1 mL) was stirred at 25° C. for 16 h. The mixture was adjusted to pH=6 by addition of 1N HCl and concentrated under reduced pressure to give crude 4-(1-hydroxycyclobutyl) pyrimidine-2-carboxylic acid (13 mg, 87%) as a yellow solid.

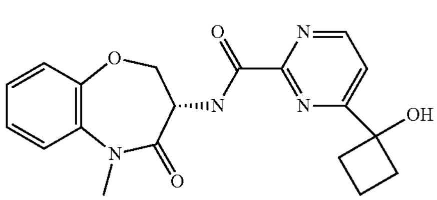 [SMILES: CN1C(=O)[C@@H](NC(=O)c2nccc(C3(O)CCC3)n2)COc2ccccc21]

Step 6: 4-(1-hydroxycyclobutyl)-N-[(3S)-5-methyl-4-oxo-2,3-dihydro-1,5-benzoxazepin-3-yl]pyrimidine-2-carboxamide A mixture of (3S)-3-amino-5-methyl-2,3-dihydro-1,5-benzoxazepin-4-one (22 mg, 0.11 mmol), 4-(1-hydroxycyclobutyl)pyrimidine-2-carboxylic acid (22 mg, 0.11 mmol), 1-(3-dimethylaminopropyl)-3-ethylcarbodiimidehydrochloride (26 mg, 0.14 mmol) and 1-hydroxybenzotriazole (18 mg, 0.14 mmol) in N,N-dimethylformamide (4 mL) was stirred at 25° C. for 16 h. The mixture was concentrated under reduced pressure and the residue was purified by RP-HPLC (20% to 50% acetonitrile/0.05% ammonia hydroxide in water) to give 4-(1-hydroxycyclobutyl)-N-[(3S)-5-methyl-4-oxo-2,3-dihydro-1,5-benzoxazepin-3-yl] pyrimidine-2-carboxamide (11.3 mg, 26%) as a white solid. $^1$H NMR (400 MHz, $CD_3OD$) δ 8.89 (d, J=5.2 Hz, 1H), 7.83 (d, J=5.6 Hz, 1H), 7.46-7.44 (m, 1H), 7.34-7.27 (m, 2H), 7.26-7.25 (m, 1H), 5.06-5.04 (m, 1H), 4.73-4.72 (m, 1H), 4.44-4.42 (m, 1H), 3.45 (s, 3H), 2.72-2.68 (m, 2H), 2.43-2.35 (m, 2H), 2.12-2.07 (m, 2H). LCMS RT=1.938 min; m/z=369.1 $(M+H)^+$.

LCMS (0-60% acetonitrile in water+0.05% ammonium bicarbonate over 3 mins) retention time 1.938 min, ESI+ found [M+H]=369.1.

Example 538

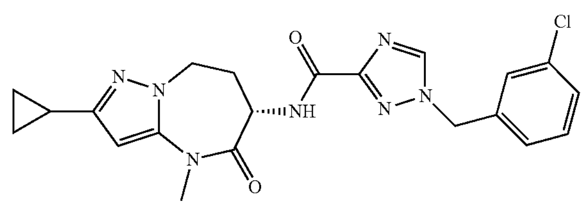 [SMILES: CN1C(=O)[C@@H](NC(=O)c2ncn(Cc3cccc(Cl)c3)n2)CCn2nc(C3CC3)cc21]

1-[(3-chlorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 077. The crude was purified by RP-HPLC (ACN 35-65%/0.05% ammonia hydroxide in water) to afford 1-[(3-chlorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide (41.56 mg, 41%) as a white solid. $^1$H NMR (400 MHz, $CD_3OD$) δ 8.68 (s, 1H), 7.37-7.25 (m, 4H), 6.18 (s, 1H), 5.47 (s, 2H), 4.61-4.58 (m, 1H), 4.40-4.26 (m, 2H), 3.28 (s, 3H), 2.87-2.81 (m, 1H), 2.32-2.30 (m, 1H), 1.97-1.93 (m, 1H), 1.05-1.03 (m, 2H), 0.84-0.81 (m, 2H). LC-MS $R_T$=0.802 min, m/z=440.1 $[M+H]^+$.

LCMS (5 to 95% acetonitrile in water+0.1% trifluoacetic acid over 1.5 mins) retention time 0.802 min, ESI+ found [M+H]=440.1

Example 539

WX Method 142

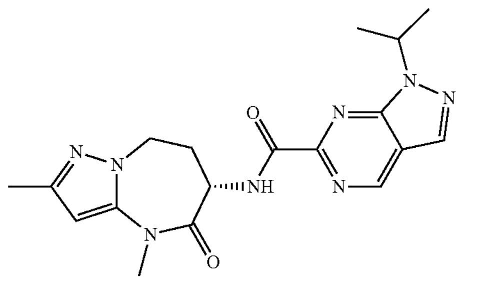 [SMILES: Cc1cc2n(n1)CC[C@H](NC(=O)c1ncc3cnn(C(C)C)c3n1)C(=O)N2C]

1-isopropyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide

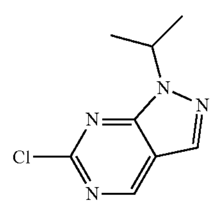

Step 1: 6-chloro-1-isopropyl-1H-pyrazolo[3,4-d]pyrimidine

A mixture of 6-chloro-1H-pyrazolo[3,4-d]pyrimidine (500 mg, 3.25 mmol), 2-iodopropane (553 mg, 3.25 mmol) and potassium carbonate (897 mg, 6.50 mmol) in N,N-dimethylformamide (20 mL) was stirred at 25° C. for 16 h. The reaction mixture was filtered and the filtrate was concentrated under reduced pressure. The residue was purified by column chromatography (silica gel, 100-200 mesh, 0 to 20% ethyl acetate in petroleum ether) to afford 6-chloro-1-isopropyl-1H-pyrazolo[3,4-d]pyrimidine (300 mg, 47%) as yellow solid, used as is in the next step.

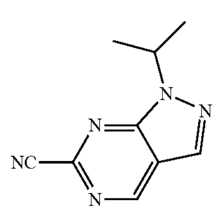

Step 2: 1-isopropyl-1H-pyrazolo[3,4-d]pyrimidine-6-carbonitrile

To a solution of 6-chloro-1-isopropyl-1H-pyrazolo[3,4-d]pyrimidine (300 mg, 1.53 mmol) in dimethyl sulfoxide (5 mL) and water (5 mL) was added 1,4-diazabicyclo[2.2.2]octane (34 mg, 0.21 mmol) and sodium cyanide (150 mg, 3.05 mmol). The reaction mixture was stirred at 25° C. for 3 h and extracted with ethyl acetate (3×20 mL). The combined organic layers were washed with water (30 mL), brine (30 mL), dried over sodium sulfate and concentrated under reduced pressure. The residue was purified by column chromatography (silica gel, 100-200 mesh, 0 to 20% ethyl acetate in petroleum ether) to afford 1-isopropyl-1H-pyrazolo[3,4-d]pyrimidine-6-carbonitrile (140 mg, 49%) as yellow oil, used as is in the next step.

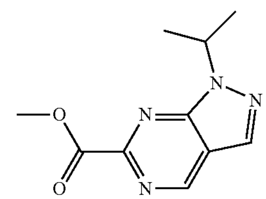 [SMILES: COC(=O)c1ncc2cnn(C(C)C)c2n1]

Step 3: methyl 1-isopropyl-1H-pyrazolo[3,4-d]pyrimidine-6-carboxylate

To a solution of 1-isopropyl-1H-pyrazolo[3,4-d]pyrimidine-6-carbonitrile (140 mg, 0.75 mmol) in methanol (5 mL) was added HCl (4N in methanol, 4 mL). The reaction mixture was stirred at 25° C. for 16 h and concentrated under reduced pressure to afford crude methyl 1-isopropyl-1H-pyrazolo[3,4-d]pyrimidine-6-carboxylate (120 mg, 73%) as yellow oil, used as is in the next step.

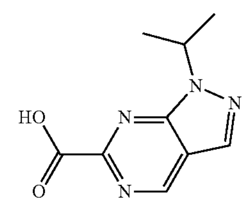

Step 4: 1-isopropyl-1H-pyrazolo[3,4-d]pyrimidine-6-carboxylic acid

A mixture of methyl 1-isopropyl-1H-pyrazolo[3,4-d]pyrimidine-6-carboxylate (120 mg, 0.54 mmol) and lithium hydroxide hydrate (229 mg, 5.45 mmol) in tetrahydrofuran (5 mL) and water (5 mL) was stirred at 25° C. for 2 h. The mixture was adjusted to pH=5 by addition of 1N HCl and extracted with ethyl acetate (3×15 mL). The combined organic layers were concentrated under reduced pressure to afford 1-isopropyl-1H-pyrazolo[3,4-d]pyrimidine-6-carboxylic acid (30 mg, 27%) as a colorless oil, used as is in the next step.

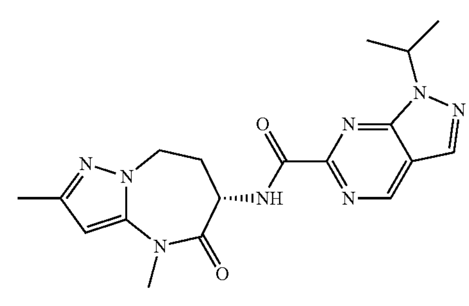 [SMILES: Cc1cc2n(n1)CC[C@H](NC(=O)c1ncc3cnn(C(C)C)c3n1)C(=O)N2C]

Step 5: 1-isopropyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide A mixture of (6S)-6-amino-2,4-dimethyl-7,8-dihydro-6H-pyrazolo[1,5-a][1,3]diazepin-5-one (34 mg, 0.17 mmol), 1H-benzo[d][1,2,3]triazol-1-ol (24 mg, 0.17 mmol), 1-isopropylpyrazolo[3,4-d]pyrimidine-6-carboxylic acid (30 mg, 0.15 mmol) and $N^1$-((ethylimino)methylene)-$N^3$,$N^3$-dimethylpropane-1,3-diamine hydrochloride (33 mg, 0.17 mmol) in N,N-dimethylformamide (3 mL) was stirred at 25° C. for 16 h. The mixture was concentrated under reduced pressure and the residue was purified by RP-HPLC (acetonitrile 30% to 60%, 0.05% ammonium hydroxide in water) to afford 1-isopropyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide (32.8 mg, 58%) as a white solid. $^1$H NMR (400 MHz, $CD_3OD$) δ 9.35 (s, 1H) 8.38 (s, 1H), 6.14 (s, 1H), 5.47-5.42 (m, 1H), 4.65-4.60 (m, 1H), 4.37-4.26 (m, 2H), 3.37 (s, 3H), 3.00-2.94 (m, 1H), 2.35-2.27 (m, 4H), 1.59 (d, J=6.8 Hz, 6H). LCMS $R_T$=0.733 min, m/z=383.1 [M+H]$^+$.

LCMS (5 to 95% acetonitrile in water+0.03% trifluoacetic acid over 1.5 mins) retention time 0.733 min, ESI+ found [M+H]=383.1.

Example 540

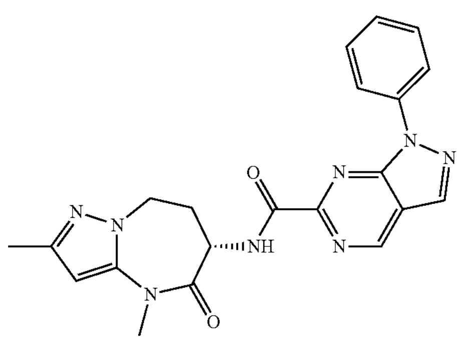 [SMILES: Cc1cc2n(n1)CC[C@H](NC(=O)c1ncc3cnn(-c4ccccc4)c3n1)C(=O)N2C]

1-phenyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide Amide coupling prepared in a similar fashion to WX Method 149. The crude was purified by RP-HPLC (acetonitrile 30% to 60%/0.05% ammonia hydroxide in water) to give 1-phenyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide (20 mg, 46%) as a white solid. $^1$H NMR (400 MHz, DMSO-$d_6$) δ9.58 (s, 1H), 9.20 (d, J=8.0 Hz, 1H), 8.77 (s, 1H), 8.23 (d, J=7.6 Hz, 2H), 7.64-7.59 (m, 2H), 7.46-7.41 (m, 1H), 6.15 (s, 1H), 4.43-4.39 (m, 1H), 4.32-4.27 (m, 1H), 4.18-4.15 (m, 1H), 3.26 (s, 3H), 2.74-2.69 (m, 1H), 2.37-2.34 (m, 1H), 2.18 (s, 3H). LCMS $R_T$=0.792 min; m/z=417.1 (M+H)$^+$.

LCMS (5 to 95% acetonitrile in water+0.03% trifluoacetic acid over 1.5 mins) retention time 0.792 min, ESI+ found [M+H]=417.1.

Example 541

WX Method 071

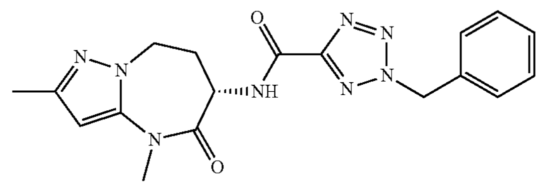 [SMILES: Cc1cc2n(n1)CC[C@H](NC(=O)c1nnn(Cc3ccccc3)n1)C(=O)N2C]

2-benzyl-N-(6S)-2,4-dimethyl-5-oxo-7,8-dihydro-6H-pyrazolo[1,5-a][1,3]diazepin-6-yltetrazole-5-carboxamide

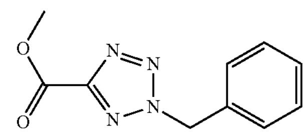 [SMILES: COC(=O)c1nnn(Cc2ccccc2)n1]

Step 1: methyl 2-benzyl-2H-tetrazole-5-carboxylate

To a solution of ethyl 2H-tetrazole-5-carboxylate (1.0 g, 7.04 mmol) in N,N-dimethylformamide (20 mL) was added benzyl bromide (1.2 g, 7.04 mmol) and potassium carbonate (972 mg, 7.04 mmol). The mixture was stirred at 25° C. for 12 h and filtered. The filtrate was concentrated under reduced pressure and the residue was purified by column chromatography (silica gel, 100-200 mesh, 0 to 100% ethyl acetate in petroleum ether) to afford methyl 2-benzyl-2H-tetrazole-5-carboxylate (200 mg, 13%) as a white solid, used as is in the next step.

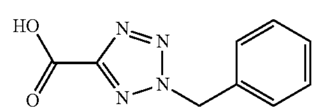 [SMILES: O=C(O)c1nnn(Cc2ccccc2)n1]

Step 2: 2-benzyl-2H-tetrazole-5-carboxylic acid

A mixture of methyl 2-benzyltetrazole-5-carboxylate (200 mg, 0.92 mmol) and triethylamine (185 mg, 1.83 mmol) in ethanol (20 mL) was stirred at 25° C. for 12 h. The mixture was concentrated under reduced pressure and diluted with water (20 mL). The solution was adjusted to pH=4 by addition of 2N HCl. The resulting solid was collected by filtration and dried under reduced pressure to obtain 2-benzyl-2H-tetrazole-5-carboxylic acid (130 mg, 69.5%) as white solids. $^1$H NMR (400 MHz, $CD_3OD$) δ7.44-7.36 (m, 5H), 5.94 (s, 2H).

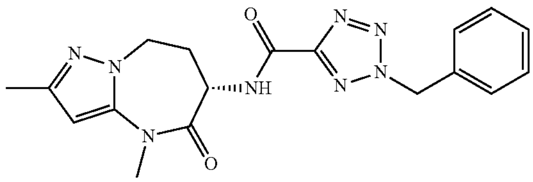 [SMILES: Cc1cc2n(n1)CC[C@H](NC(=O)c1nnn(Cc3ccccc3)n1)C(=O)N2C]

Step 3: 2-benzyl-N-(6S)-2,4-dimethyl-5-oxo-7,8-dihydro-6H-pyrazolo[1,5-a][1,3]diazepin-6-yltetrazole-5-carboxamide A mixture of 1-(3-dimethylaminopropyl)-3-ethylcarbodiimidehydrochloride (37 mg, 0.19 mmol), 2-benzyltetrazole-5-carboxylic acid (31 mg, 0.15 mmol), (6S)-6-amino-2,4-dimethyl-7,8-dihydro-6H-pyrazolo[1,5-a][1,3]diazepin-5-one (25 mg, 0.13 mmol) and 1-hydroxybenzotriazole (26 mg, 0.19 mmol) in N,N-dimethylformamide (5 mL) was stirred at 25° C. for 2 h. The mixture was concentrated under reduced pressure and the residue was purified by RP-HPLC (acetonitrile 20-50%/0.05% ammonium hydroxide in water) to give 2-benzyl-N-(6S)-2,4-dimethyl-5-oxo-7,8-dihydro-6H-pyrazolo[1,5-a][1,3]diazepin-6-yltetrazole-5-carboxamide (11 mg, 12%) as a white solid. $^1$H NMR (400 MHz, $CD_3OD$) δ 7.43-7.37 (m, 5H), 6.12 (s, 1H) 5.94 (s, 2H), 4.58-4.53 (m, 1H), 4.35-4.29 (m, 1H), 4.26-4.22 (m, 1H), 3.32 (s, 3H), 2.84-2.78 (m, 1H), 2.34-2.25 (m, 4H). LCMS $R_T$=0.938 min, m/z=381.2 $[M+H]^+$.

LCMS (10 to 80% acetonitrile in water+0.03% trifluoacetic acid over 2.0 mins) retention time 0.938 min, ESI+ found [M+H]=381.2

Example 542

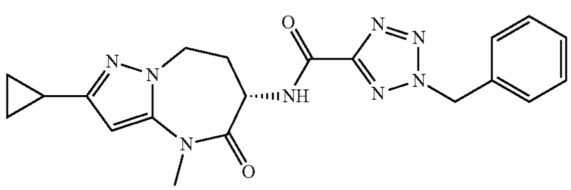 [SMILES: CN1C(=O)[C@@H](NC(=O)c2nnn(Cc3ccccc3)n2)CCn2nc(C3CC3)cc21]

2-benzyl-N-(6S)-2,4-dimethyl-5-oxo-7,8-dihydro-6H-pyrazolo[1,5-a][1,3]diazepin-6-yltetrazole-5-carboxamide Amide coupling prepared in a similar fashion to WX Method 071. The crude was purified by RP-HPLC (acetonitrile 28-58%/0.05% ammonium hydroxide in water) to give 2-benzyl-N-(6S)-2,4-dimethyl-5-oxo-7,8-dihydro-6H-pyrazolo[1,5-a][1,3]diazepin-6-yltetrazole-5-carboxamide (10 mg, 11%) as a white solid. $^1$H NMR (400 MHz, $CD_3OD$) δ7.44-7.34 (m, 5H), 6.00 (s, 1H), 5.93 (s, 2H), 4.57-4.52 (m, 1H), 4.34-4.26 (m, 1H), 4.24-4.14 (m, 1H), 3.30 (s, 3H), 2.86-2.81 (m, 1H), 2.34-2.30 (m, 1H), 1.94-1.85 (m, 1H), 0.96-0.90 (m, 2H), 0.77-0.68 (m, 2H). LCMS $R_T$=1.002 min, m/z=407.2 $[M+H]^+$.

LCMS (10 to 80% acetonitrile in water+0.03% trifluoacetic acid over 2.0 mins) retention time 1.002 min, ESI+ found [M+H]=407.2

Example 543

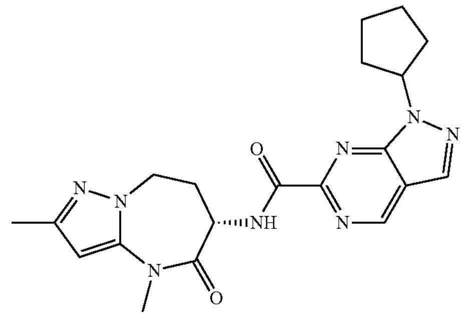 [SMILES: Cc1cc2n(n1)CC[C@H](NC(=O)c1ncc3cnn(C4CCCC4)c3n1)C(=O)N2C]

1-cyclopentyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide Amide coupling prepared in a similar fashion to WX Method 147. The crude was purified by RP-HPLC (acetonitrile 26% to 56%/0.05% ammonia hydroxide in water) to give 1-cyclopentyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide (30.2 mg, 56%) as a white solid: $^1$H NMR (400 MHz, DMSO-$d_6$) δ 9.45 (s, 1H), 9.15 (d, J=8.0 Hz, 1H), 8.51 (s, 1H), 6.16 (s, 1H), 5.49-5.41 (m, 1H), 4.47-4.10 (m, 3H), 3.25 (s, 3H), 2.77-2.66 (m, 1H), 2.38-2.29 (m, 1H), 2.23-2.11 (m, 5H), 2.06-1.86 (m, 4H), 1.80-1.65 (m, 2H). LCMS $R_T$=0.787 min; m/z=409.1 $(M+H)^+$.

LCMS (5 to 95% acetonitrile in water+0.03% trifluoacetic acid over 1.5 mins) retention time 0.787 min, ESI+ found [M+H]=409.1

Example 544

WX Method 161

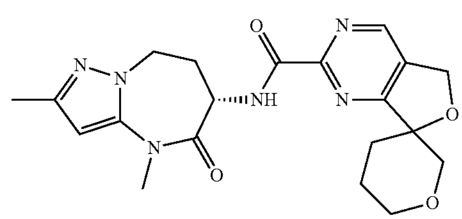 [SMILES: Cc1cc2n(n1)CC[C@H](NC(=O)c1ncc3c(n1)C1(CCCOC1)OC3)C(=O)N2C]

N-[(6S)-2,4-dimethyl-5-oxo-7,8-dihydro-6H-pyrazolo[1,5-a][1,3]diazepin-6-yl]spiro[5H-furo[3,4-d]pyrimidine-7,3'-tetrahydropyran]-2-carboxamide

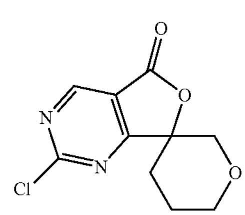 [SMILES: O=C1OC2(CCCOC2)c2nc(Cl)ncc21]

Step 1: 2-chloro-2',4',5',6'-tetrahydro-5H-spiro[furo[3,4-d]pyrimidine-7,3'-pyran]-5-one To a solution of 2,2,6,6-tetramethylpiperidine (13.4 g, 94.6 mmol) in tetrahydrofuran (100 mL) was added n-butyllithium (2.5 M in hexanes, 50.0 mL, 125.0 mmol) at −78° C. The reaction mixture was stirred at −78° C. for 1 h and 2-chloropyrimidine-5-carboxylic acid (5.0 g, 31.5 mmol) was added. The reaction mixture was stirred at −78° C. for another 2 h and dihydro-2H-pyran-3(4H)-one (6.3 g, 63.1 mmol) was added. After addition, the reaction mixture was stirred at 25° C. for 16 h and quenched by addition of saturated ammonium chloride (30 mL). The mixture was extracted with ethyl acetate (3×10 mL). The combined organic layers were dried over sodium sulfate and concentrated under reduced pressure. The residue was purified by column chromatography (silica gel 100-200 mesh, 30% ethyl acetate in petroleum ether) to give 2-chloro-2',4',5',6'-tetrahydro-5H-spiro[furo[3,4-d]pyrimidine-7,3'-pyran]-5-one (900 mg, 12%) as light yellow solid, use as is in the next step.

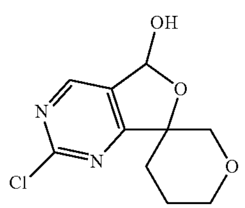 [SMILES: OC1OC2(CCCOC2)c2nc(Cl)ncc21]

Step 2: 2-chloro-2',4',5',6'-tetrahydro-5H-spiro[furo[3,4-d]pyrimidine-7,3'-pyran]-5-ol To a solution of 2-chloro-2',4',5',6'-tetrahydro-5H-spiro[furo[3,4-d]pyrimidine-7,3'-pyran]-5-one (700 mg, 2.90 mmol) in toluene (30 mL) was added diisobutylaluminum hydride (7.3 mL, 7.27 mmol, 1.0 M in toluene) dropwise at −78° C. The mixture was stirred at −78° C. for 2 h and quenched by addition of saturated potassium tartrate tetrahydrate (10 mL). The resulting mixture was stirred at 25° C. for 1 h and extracted with ethyl acetate (3×20 mL). The combined organic layers were dried over sodium sulfate and concentrated under reduced pressure. The residue was purified by column chromatography (silica gel, 100-200 mesh, eluting 50% ethyl acetate in petroleum ether) to afford 2-chloro-2',4',5',6'-tetrahydro-5H-spiro[furo[3,4-d]pyrimidine-7,3'-pyran]-5-ol (260 mg, 37%) as white solid, used as is in the next step.

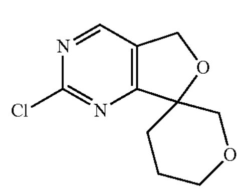 [SMILES: Clc1ncc2c(n1)C1(CCCOC1)OC2]

Step 3: 2-chloro-2',4',5',6'-tetrahydro-5H-spiro[furo[3,4-d]pyrimidine-7,3'-pyran]

To a solution of 2-chloro-2',4',5',6'-tetrahydro-5H-spiro[furo[3,4-d]pyrimidine-7,3'-pyran]-5-ol (260 mg, 1.1 mmol) and 2,2,2-trifluoroacetic acid (1.6 mL, 21.9 mmol) in dichloromethane (25 mL) was added triethylsilane (1.6 mL, 10.20 mmol). The mixture was stirred at 25° C. for 15 h and concentrated under reduced pressure. The residue was diluted with saturated sodium bicarbonate (10 mL) and extracted with ethyl acetate (3×20 mL). The combined organic layers were dried over sodium sulfate and concentrated under reduced pressure to afford crude 2-chloro-2',4',5',6'-tetrahydro-5H-spiro[furo[3,4-d]pyrimidine-7,3'-pyran] (240 mg, 99%) as colorless oil, used as is in the next step.

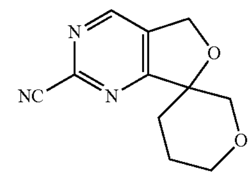 [SMILES: N#Cc1ncc2c(n1)C1(CCCOC1)OC2]

Step 4: 2',4',5',6'-tetrahydro-5H-spiro[furo[3,4-d]pyrimidine-7,3'-pyran]-2-carbonitrile To a solution of 2-chloro-2',4',5',6'-tetrahydro-5H-spiro[furo[3,4-d]pyrimidine-7,3'-pyran](410 mg, 1.80 mmol) in dimethyl sulfoxide (20 mL) was added 1,4-diazabicyclo[2.2.2]octane (41 mg, 0.40 mmol) and sodium cyanide (280 mg, 5.70 mmol) in water (4 mL). The mixture was stirred for 7 h at 25° C. and extracted with ethyl acetate (3×20 mL). The combined organic layers were dried over sodium sulfate and concentrated under reduced pressure. The residue was purified by column chromatography (silica gel 100-200 mesh, eluting 20-40% ethyl acetate in petroleum ether) to afford 2',4',5',6'-tetrahydro-5H-spiro[furo[3,4-d]pyrimidine-7,3'-pyran]-2-carbonitrile (210 mg, 53%) as colorless oil, used as is in the next step.

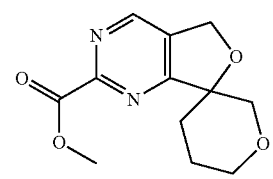 [SMILES: COC(=O)c1ncc2c(n1)C1(CCCOC1)OC2]

Step 5: methyl 2',4'5',6'-tetrahydro-5H-spiro[furo[3,4-d]pyrimidine-7,3'-pyran]-2-carboxylate To a solution of 2',4',5',6'-tetrahydro-5H-spiro[furo[3,4-d]pyrimidine-7,3'-pyran]-2-carbonitrile (210 mg, 1.00 mmol) in methanol (12 mL) was added HCl (4N in methanol, 2.5 mL) at 0° C. The mixture was stirred at 25° C. for 15 h and concentrated under reduced pressure to afford crude methyl 2',4',5',6'-tetrahydro-5H-spiro[furo[3,4-d]pyrimidine-7,3'-pyran]-2-carboxylate (210 mg, 87%) as a white solid, used as is in the next step.

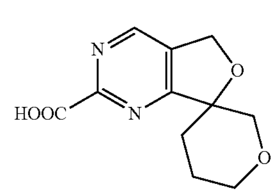 [SMILES: O=C(O)c1ncc2c(n1)C1(CCCOC1)OC2]

Step 6: 2',4',5',6'-tetrahydro-5H-spiro[furo[3,4-d]pyrimidine-7,3'-pyran]-2-carboxylic acid A mixture of methyl 2',4',5',6'-tetrahydro-5H-spiro[furo[3,4-d]pyrimidine-7,3'-pyran]-2-carboxylate (210 mg, 0.8 mmol) and lithium hydroxide (201 mg, 8.4 mmol) in tetrahydrofuran (10 mL) and water (2 mL) was stirred for 2 h at 25° C. The organic solvent was reduced pressure and the aqueous phase was adjusted to pH=4 by addition of 1N HCl. The mixture was concentrated under reduced pressure to give crude to 2',4',5',6'-tetrahydro-5H-spiro[furo[3,4-d]pyrimidine-7,3'-pyran]-2-carboxylic acid (180 mg, 91%) as a light yellow solid, used as is in the next step.

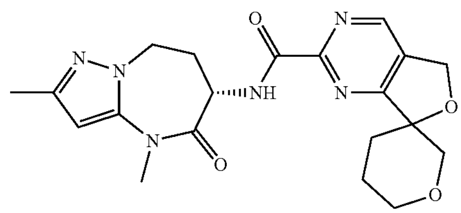

Step 7: N-[(6S)-2,4-dimethyl-5-oxo-7,8-dihydro-6H-pyrazolo[1,5-a][1,3]diazepin-6-yl]spiro[5H-furo[3,4-d]pyrimidine-7,3'-tetrahydropyran]-2-carboxamide Amide coupling prepared in a similar fashion to WX Method 160 (RIP1K_experimental_3$^{rd}$_WX.doc). The crude was purified by RP-HPLC (20% to 50% acetonitrile/0.05% ammonia hydroxide in water) to give N-[(6S)-2,4-dimethyl-5-oxo-7,8-dihydro-6H-pyrazolo[1,5-a][1,3]diazepin-6-yl]spiro[5H-furo [3,4-d]pyrimidine-7,3'-tetrahydropyran]-2-carboxamide (7.7 mg, 12%) as white solid. $^{1}$H NMR (400 MHz, $CD_3OD$) δ8.52 (s, 1H), 6.14 (s, 1H), 5.22 (s, 2H), 4.62-4.56 (m, 1H), 4.34-4.24 (m, 2H), 3.95-3.90 (m, 1H), 3.79-3.65 (m, 3H), 3.35 (s, 3H), 2.96-2.90 (m, 1H), 2.31-2.20 (m, 5H), 2.07-2.03 (m, 1H), 1.94-1.90 (m, 1H), 1.77-1.73 (m, 1H). LCMS $R_T$=0.580 min; m/z=413.1 $(M+H)^+$.

LCMS (5 to 95% acetonitrile in water+0.03% trifluoacetic acid over 2 mins) retention time 0.580 min, ESI+ found [M+H]=413.1.

Example 545

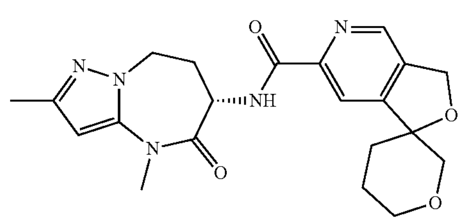

N-[(6S)-2,4-dimethyl-5-oxo-7,8-dihydro-6H-pyrazolo[1,5-a][1,3]diazepin-6-yl]spiro[3H-furo[3,4-c]pyridine-1,3'-tetrahydropyran]-6-carboxamide Amide coupling prepared in a similar fashion to WX Method 158 (RIP1K_experimental_3$^{rd}$_WX.doc). The crude was purified by RP-HPLC (acetonitrile 20% to 50%/0.05% hydrochloric acid in water) to give N-[(6S)-2,4-dimethyl-5-oxo-7,8-dihydro-6H-pyrazolo[1,5-a][1,3]diazepin-6-yl]spiro[3H-furo [3,4-c]pyridine-1,3'-tetrahydropyran]-6-carboxamide (15.5 mg, 18%). $^{1}$H NMR (400 MHz, $CD_3OD$) δ8.59 (s, 1H), 8.03 (s, 1H), 6.12 (s, 1H), 5.24-5.15 (m, 2H), 4.59-4.54 (m, 1H), 4.36-4.19 (m, 2H), 3.87-3.61 (m, 4H), 3.34 (s, 3H), 2.97-2.84 (m, 1H), 2.28-2.19 (m, 4H), 2.07-1.89 (m, 3H), 1.78-1.70 (m, 1H). LCMS $R_T$=0.887 min; m/z=412.2 $(M+H)^+$.

LCMS (10 to 80% acetonitrile in water+0.03% trifluoacetic acid over 2.0 mins) retention time 0.887 min, ESI+ found [M+H]=412.2.

Example 546

WX Method 095

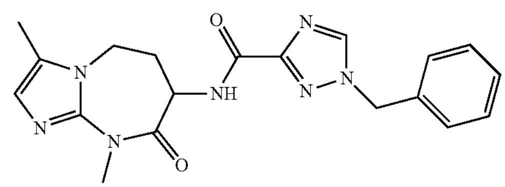 [SMILES: Cc1cnc2n1CCC(NC(=O)c1ncn(Cc3ccccc3)n1)C(=O)N2C]

1-benzyl-N-(3,9-dimethyl-8-oxo-6,7-dihydro-5H-imidazo[1,2-a][1,3]diazepin-7-yl)-1,2,4-triazole-3-carboxamide

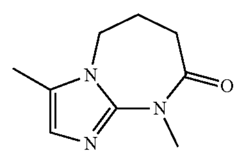

Step 1: 3,9-dimethyl-6,7-dihydro-5H-imidazo[1,2-a][1,3]diazepin-8(9H)-one

A mixture of 2,4,6-trimethyl-1,3,5,2,4,6-trioxatriborinane (500 mg, 4.01 mmol), 3-chloro-9-methyl-6,7-dihydro-5H-imidazo[1,2-a][1,3]diazepin-8-one (400 mg, 2 mmol), bis(1-adamantyl)-butyl-phosphane (36 mg, 0.10 mmol) and potassium carbonate (831 mg, 6.01 mmol) in toluene (3 mL) and water (1 mL) was heated at 110° C. for 2 h under microwave conditions. The mixture was concentrated under reduced pressure and the residue was purified by column chromatography (silica gel, 100-200 mesh, 0 to 100% ethyl acetate in petroleum ether) to afford 3,9-dimethyl-6,7-dihydro-5H-imidazo[1,2-a][1,3]diazepin-8-one (80 mg, 22%) as a yellow oil, used as is in the next step.

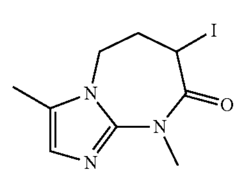

Step 2: 7-iodo-3,9-dimethyl-6,7-dihydro-5H-imidazo[1,2-a][1,3]diazepin-8(9H)-one To a solution of 3,9-dimethyl-6,7-dihydro-5H-imidazo[1,2-a][1,3]diazepin-8(9H)-one (40 mg, 0.22 mmol) in dichloromethane (10 mL) was added N1,N1,N3,N3-tetramethylpropane-1,3-diamine (155 mg, 1.37 mmol) and iodotrimethylsilane (268 mg, 1.34 mmol) at −15° C. The reaction mixture was stirred at −15° C. for 2 h and iodine (170 mg, 0.67 mmol) was added. The mixture was stirred at −15° C. for another 2 h and quenched by addition of saturated aqueous sodium sulfite (10 mL). The resulting mixture was extracted with dichloromethane (3×20 mL). The combined organic layers were dried over sodium sulfate and concentrated under reduced pressure. The residue was purified by column chromatography (silica gel, 100-200 mesh, 0 to 10% methanol in dichloromethane) to afford 7-iodo-3,9-dimethyl-6,7-dihydro-5H-imidazo[1,2-a][1,3]diazepin-8(9H)-one (40 mg, 58%) as a colorless oil, used as is in the next step. LCMS $R_T$=1.491 min; m/z=306.1 $(M+H)^+$.

LCMS (0 to 60% acetonitrile in water+0.05% ammonium bicarbonate over 3 mins) retention time 1.491 ESI+ found [M+H]=306.1

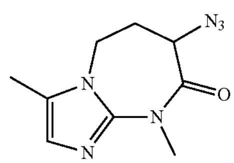 [SMILES: Cc1cnc2n1CCC(N=[N+]=[N-])C(=O)N2C]

Step 3: 7-azido-3,9-dimethyl-6,7-dihydro-5H-imidazo[1,2-a][1,3]diazepin-8(9H)-one A mixture of 7-iodo-3,9-dimethyl-6,7-dihydro-5H-imidazo[1,2-a][1,3]diazepin-8(9H)-one (40 mg, 0.13 mmol) and sodium azide (70 mg, 1.08 mmol) in N,N-dimethylformamide (5 mL) was stirred at 25° C. for 2 h and then concentrated under reduced pressure. The residue was purified by preparative TLC (50% ethyl acetate in petroleum ether, $R_f$=0.6) to afford 7-azido-3,9-dimethyl-6,7-dihydro-5H-imidazo[1,2-a][1,3]diazepin-8(9H)-one (20 mg, 69%) as a yellow oil, used as is in the next step.

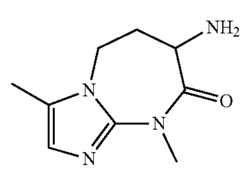

Step 4: 7-amino-3,9-dimethyl-6,7-dihydro-5H-imidazo[1,2-a][1,3]diazepin-8(9H)-one A mixture of 7-azido-3,9-dimethyl-6,7-dihydro-5H-imidazo[1,2-a][1,3]diazepin-8-one (20 mg, 0.09 mmol) and Pd/C (10%, 96 mg, 0.09 mmol) in 1,4-dioxane (5 mL) was hydrogenated (15 psi) for 5 h and filtered. The filtrate was concentrated under reduced pressure to afford 7-amino-3,9-dimethyl-6,7-dihydro-5H-imidazo[1,2-a][1,3]diazepin-8(9H)-one (10 mg, 56%) as a yellow oil, used as is in the next step.

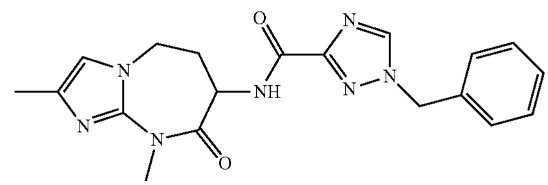 [SMILES: Cc1cn2c(n1)N(C)C(=O)C(NC(=O)c1ncn(Cc3ccccc3)n1)CC2]

Step 5: 1-benzyl-N-(2,9-dimethyl-8-oxo-6,7,8,9-tetrahydro-5H-imidazo[1,2-a][1,3]diazepin-7-yl)-1H-1,2,4-triazole-3-carboxamide A mixture of 1-benzyl-1,2,4-triazole-3-carboxylic acid (10 mg, 0.05 mmol), 7-amino-3,9-dimethyl-6,7-dihydro-5H-imidazo[1,2-a][1,3]diazepin-8-one (10 mg, 0.05 mmol), 1-(3-dimethylaminopropyl)-3-ethylcarbodiimidehydrochloride (10 mg, 0.05 mmol) and 1-hydroxybenzotriazole (7 mg, 0.05 mmol) in N,N-dimethylformamide (5 mL) was stirred at 25° C. for 1 h. The reaction mixture was concentrated under reduced pressure and the residue was purified by RP-HPLC (13% to 43% acetonitrile/0.05% ammonia hydroxide in water) to afford 1-benzyl-N-(3,9-dimethyl-8-oxo-6,7-dihydro-5H-imidazo[1,2-a][1,3]diazepin-7-yl)-1,2,4-triazole-3-carboxamide (3.9 mg, 19%) as white solids. $^1H$ NMR (400 MHz, $CD_3OD$) δ 8.56 (s, 1H), 7.39-7.35 (m, 5H), 6.71 (s, 1H), 5.47 (s, 2H), 4.51-4.46 (m, 1H), 4.22-4.16 (m, 1H), 3.95-3.87 (m, 1H), 3.37 (s, 3H), 2.84-2.74 (m, 1H), 2.29-2.19 (m, 4H). LCMS $R_T$=1.792 min, m/z=380.1 $[M+H]^+$.

LCMS (0 to 60% acetonitrile in water+0.05% ammonium bicarbonate over 3 mins) retention time 1.792 min, ESI+ found [M+H]=380.1.

Examples 547 and 548

WX Method 084

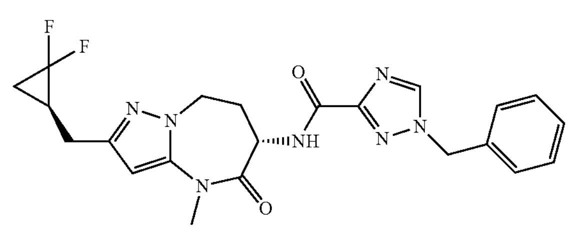

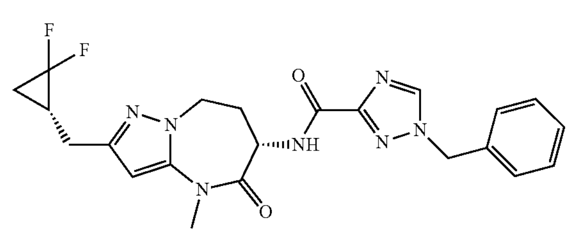

1-benzyl-N-(6S)-4-methyl-5-oxo-2-[(1 S)-2,2-difluorocyclopropylmethyl]-7,8-dihydro-6H-pyrazolo[1,5-a][1,3]diazepin-6-yl-1,2,4-triazole-3-carboxamide and 1-benzyl-N-(6S)-4-methyl-5-oxo-2-[(1R)-2,2-difluorocyclopropylmethyl]-7,8-dihydro-6H-pyrazolo[1,5-a][1,3]diazepin-6-yl-1,2,4-triazole-3-carboxamide

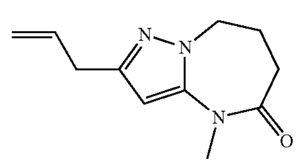

Step 1: 2-allyl-4-methyl-7,8-dihydro-4H-pyrazolo[1,5-a][1,3]diazepin-5(6H)-one

A mixture of 1,1'-bis(diphenylphosphino)ferrocene palladiumdichloride (4.2 g, 5.74 mmol), cesium fluoride (26.14 g, 172.1 mmol), allylboronicacidpinacolester (14.46 g, 86.07 mmol), 2-bromo-4-methyl-7,8-dihydro-6h-pyrazolo[1,5-a][1,3]diazepin-5-one (14.0 g, 53.4 mmol) in tetrahydrofuran (500 mL) was stirred at 70° C. under nitrogen atmosphere for 16 h and then concentrated under reduced pressure. The residue was diluted with dichloromethane (200 mL), washed water (2×100 mL), brine (100 mL), dried over anhydrous magnesium sulfate and concentrated. The residue was purified by column chromatography (silica gel, 100-200 mesh, 0 to 1% methanol in dichloromethane) to give 2-allyl-4-methyl-7,8-dihydro-6H-pyrazolo[1,5-a][1,3]diazepin-5-one (6.55 g, 60%). LCMS $R_T$=0.63 min, m/z=205.8 $[M+H]^+$ LCMS (5 to 95% acetonitrile in water+0.03% trifluoacetic acid over 1.5 mins) retention time 0.63 min, ESI+ found [M+H]=205.8.

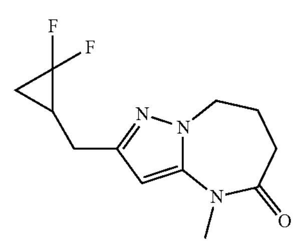 [SMILES: CN1C(=O)CCCn2nc(CC3CC3(F)F)cc21]

Step 2: 2-((2,2-difluorocyclopropyl)methyl)-4-methyl-7,8-dihydro-4H-pyrazolo[1,5-a][1,3]diazepin-5(6H)-one A mixture of 2-allyl-4-methyl-7,8-dihydro-6H-pyrazolo[1,5-a][1,3]diazepin-5-one (5.0 g, 24.4 mmol), tetrabutylammonium bromide (235 mg, 0.7 mmol) and [bromo(difluoro)methyl]-trimethyl-silane (24.7 g, 121.8 mmol) in toluene (50 mL) was heated at 110° C. for 5 h in a sealed tube. The reaction was concentrated under reduced pressure and the residue was purified by column chromatography (silica gel, 100-200 mesh, 0 to 3% methyl in dichloromethane) to give 2-[(2,2-difluorocyclopropyl)methyl]-4-methyl-7,8-dihydro-6H-pyrazolo[1,5-a][1,3]diazepin-5-one (3.3 g, 53%) as a brown oil. LCMS RT=0.63 min, m/z=255.9 $[M+H]^+$.

LCMS (5 to 95% acetonitrile in water+0.03% trifluoacetic acid over 1.5 mins) retention time 0.63 min, ESI+ found [M+H]=255.9.

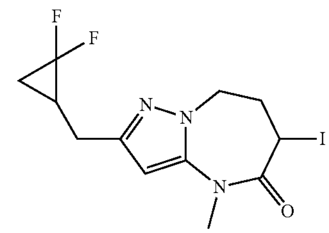 [SMILES: CN1C(=O)C(I)CCn2nc(CC3CC3(F)F)cc21]

Step 3: 2-((2,2-difluorocyclopropyl)methyl)-6-iodo-4-methyl-7,8-dihydro-4H-pyrazolo[1,5-a][1,3]diazepin-5(6H)-one To a solution of 2-((2,2-difluorocyclopropyl)methyl)-4-methyl-7,8-dihydro-4H-pyrazolo[1,5-a][1,3]diazepin-5(6H)-one (3.4 g, 13.32 mmol) in dichloromethane (100 mL) was added N1,N1,N3,N3-tetramethylpropane-1,3-diamine (20.82 g, 159.84 mmol) and iodotrimethylsilane (32.0 g, 159.84 mmol) at −15° C. The mixture was stirred at −15° C. for 1.5 h and iodine (20.28 g, 79.92 mmol) was added in one portion. The mixture was stirred for another 3 h and then quenched by addition of 5% aqueous sodium thiosulfate (200 mL). The solution was extracted with dichloromethane (2×200 mL). The combined organic layers were concentrated and the residue was purified by column chromatography (silica gel, 100-200 mesh, 0 to 50% ethyl acetate in petroleum ether) to give 2-((2,2-difluorocyclopropyl)methyl)-6-iodo-4-methyl-7,8-dihydro-4H-pyrazolo[1,5-a][1,3]di azepin-5(6H)-one (2.2 g, 43%) as a yellow oil. LCMS RT=0.67 min, m/z=381.9 [M+H]+.

LCMS (5 to 95% acetonitrile in water+0.03% trifluoacetic acid over 1.5 mins) retention time 0.67 min, ESI+ found [M+H]=381.9.

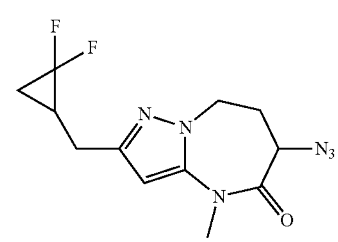 [SMILES: CN1C(=O)C(N=[N+]=[N-])CCn2nc(CC3CC3(F)F)cc21]

Step 4: 6-azido-2-((2,2-difluorocyclopropyl)methyl)-4-methyl-7,8-dihydro-4H-pyrazolo[1,5-a][1,3]diazepin-5(6H)-one A mixture of 2-((2,2-difluorocyclopropyl)methyl)-6-iodo-4-methyl-7,8-dihydro-4H-pyrazolo[1,5-a][1,3]diazepin-5(6H)-one (2.2 g, 5.77 mmol) and sodium azide (0.56 g, 8.66 mmol) in N,N-dimethylformamide (50 mL) was stirred at 25° C. for 16 h and diluted with ethyl acetate (50 mL). The solution was washed with water (2×50 mL), brine (50 mL), dried over anhydrous magnesium sulfate and concentration under reduced pressure. The residue was purified by column chromatography (silica gel, 100-200 mesh, 0 to 30% ethyl acetate in petroleum ether) to give 6-azido-2-((2,2-difluorocyclopropyl)methyl)-4-methyl-7,8-dihydro-4H-pyrazolo[1,5-a][1,3]di azepin-5(6H)-one (1.5 g, 88%) as a white solid. LCMS RT=0.66 min, m/z=296.9 [M+H]+.

LCMS (5 to 95% acetonitrile in water+0.03% trifluoacetic acid over 1.5 mins) retention time 0.66 min, ESI+ found M+H]=296.9.

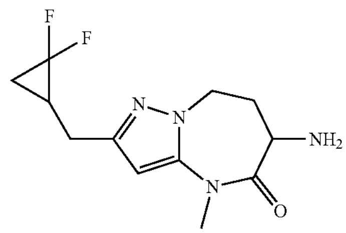 [SMILES: CN1C(=O)C(N)CCn2nc(CC3CC3(F)F)cc21]

Step 5: 6-amino-2-((2,2-difluorocyclopropyl) methyl)-4-methyl-7,8-dihydro-4H-pyrazolo[1,5-a][1,3]diazepin-5(6H)-one A solution of 6-azido-2-[(2,2-difluorocyclopropyl) methyl]-4-methyl-7,8-dihydro-6H-pyrazolo[1,5-a][1,3]diazepin-5-one (1.5 g, 5.06 mmol) in tetrahydrofuran (50 mL) was added water (10 mL) and 80% polymer-bound triphenylphosphine (6.0 g, 18.3 mmol). The mixture was stirred at 25° C. for 16 h and filtered. The filtrate was concentrated under reduced pressure and the residue was purified by column chromatography (silica gel, 100-200 mesh, 0 to 20% methanol in dichloromethane) to give 6-amino-2-[(2,2-difluorocyclopropyl)methyl]-4-methyl-7,8-dihydro-6H-pyrazolo[1,5-a][1,3]diazepin-5-one (1.0 g, 73%) as a yellow oil. LCMS RT=0.54 min, m/z=270.8 [M+H]+.

LCMS (5 to 95% acetonitrile in water+0.03% trifluoacetic acid over 1.5 mins) retention time 0.54 min, ESI+ found [M+H]=270.8.

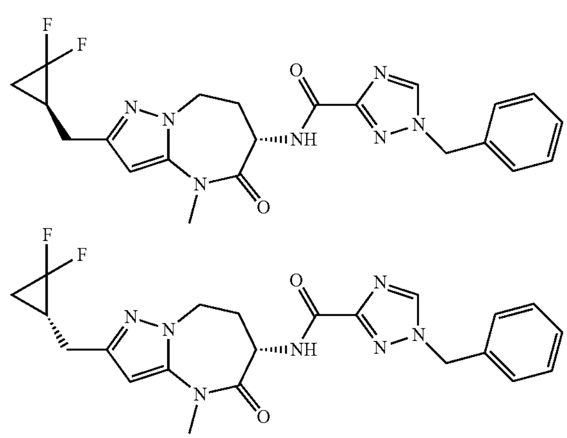

Step 6: 1-benzyl-N-(6S)-4-methyl-5-oxo-2-[(1 S)-2,2-difluorocyclopropylmethyl]-7,8-dihydro-6H-pyrazolo[1,5-a][1,3]diazepin-6-yl-1,2,4-triazole-3-carboxamide and 1-benzyl-N-(6S)-4-methyl-5-oxo-2-[(1R)-2,2-difluorocyclopropylmethyl]-7,8-dihydro-6H-pyrazolo[1,5-a][1,3]diazepin-6-yl-1,2,4-triazole-3-carboxamide A mixture of 6-amino-2-[(2,2-difluorocyclopropyl) methyl]-4-methyl-7,8-dihydro-6H-pyrazolo[1,5-a][1,3]diazepin-5-one (150 mg, 0.56 mmol), 1-hydroxybenzotriazole (112 mg, 0.83 mmol), 1-benzyl-1,2,4-triazole-3-carboxylic acid (112 mg, 0.56 mmol) and 1-(3-dimethylaminopropyl)-3-ethylcarbodiimidehydrochloride (106 mg, 0.56 mmol) in N,N-dimethylformamide (15 mL) was stirred at 25° C. for 16 h. The reaction was concentrated under reduced pressure and the residue was purified by RP-HPLC (33% to 63% acetonitrile, 0.05% ammonia hydroxide in water) to give 1-benzyl-N-[2-[(2,2-difluorocyclopropyl)methyl]-4-methyl-5-oxo-7,8-dihydro-6H-pyrazolo[1,5-a][1,3]diazepin-6-yl]-1,2,4-triazole-3-carboxamide (110 mg, 44%) as a white solid. The racemate was separated by chiral SFC to give:

1-benzyl-N-(6S)-4-methyl-5-oxo-2-[(1 S)-2,2-difluorocyclopropylmethyl]-7,8-dihydro-6H-pyrazolo[1,5-a][1,3]diazepin-6-yl-1,2,4-triazole-3-carboxamide (Peak 1, retention time 4.169 min) (9.1 mg, 8.3%) as a white solid. $^1$H NMR (400 MHz, $CD_3OD$) δ8.58 (s, 1H), 7.48-7.20 (m, 5H), 6.23 (s, 1H), 5.43 (s, 2H), 4.57-4.53 (m, 1H), 4.38-4.34 (m, 1H), 4.26-4.22 (m, 1H), 3.35 (s, 3H), 2.95-2.65 (m, 3H), 2.40-2.20 (m, 1H), 2.05-1.80 (m, 1H), 1.65-1.45 (m, 1H), 1.25-1.10 (m, 1H). LCMS RT=0.684 min, m/z=456.0 $(M+H)^+$.

LCMS (5 to 95% acetonitrile in water+0.03% trifluoacetic acid over 1.5 mins) retention time 0.684 min, ESI+ found [M+H]=456.0.

1-benzyl-N-(6S)-4-methyl-5-oxo-2-[(1R)-2,2-difluorocyclopropylmethyl]-7,8-dihydro-6H-pyrazolo[1,5-a][1,3]diazepin-6-yl-1,2,4-triazole-3-carboxamide (Peak 2, retention time 4.225 min) (8.9 mg, 8.1%) as a white solid. $^1$H NMR (400 MHz, CD3OD) 8.59 (s, 1H), 7.48-7.20 (m, 5H), 6.24 (s, 1H), 5.49 (s, 2H), 4.57-4.53 (m, 1H), 4.37-4.35 (m, 1H), 4.28-4.23 (m, 1H), 3.35 (s, 3H), 2.95-2.65 (m, 3H), 2.40-2.20 (m, 1H), 2.05-1.80 (m, 1H), 1.65-1.45 (m, 1H), 1.25-1.10 (m, 1H).

LCMS RT=0.694 min, m/z=456.1 $[M+H]^+$.

LCMS (5 to 95% acetonitrile in water+0.03% trifluoacetic acid over 1.5 mins) retention time 0.694 min, ESI+ found [M+H]=456.1.

SFC conditions: Method: Column: Chiralpak AY-3, 150×4.6 mm I.D., 3 um Mobile phase: 50% ethanol (0.05% DEA) in CO2 Flow rate: 2.0 mL/min Wavelength: 220 nm.

Example 549

WX Method 173

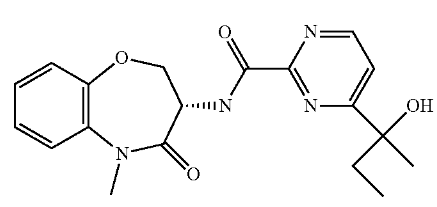 [SMILES: CCC(C)(O)c1ccnc(C(=O)N[C@H]2COc3ccccc3N(C)C2=O)n1]

4-(1-hydroxy-1-methyl-propyl)-N-[(3S)-5-methyl-4-oxo-2,3-dihydro-1,5-benzoxazepin-3-yl]pyrimidine-2-carboxamide

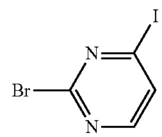

Step 1: 2-bromo-4-iodopyrimidine

To a solution of chloro-(2,2,6,6-tetramethyl-1-piperidyl) magnesium (1.5 M in tetrahedron, 39.0 mL, 58.1 mmol) in tetrahydrofuran (140 mL) was added 2-bromopyrimidine (8.4 g, 52.8 mmol) at −55° C. over 20 min. The resulting mixture was stirred for 1.5 h at −55° C. and zinc dichloride (1 M in tetrahedron, 58.0 mL, 58.0 mmol) was slowly added. After addition, the mixture was warmed up to 25° C. and a solution of iodine (20.1 g, 79.2 mmol) in tetrahydrofuran (20 mL) was added dropwise. The mixture was stirred for 45 min and quenched by addition of saturated ammonium chloride (50 mL) and saturated sodium thiosulfate (150 mL). The mixture was extracted with ethyl acetate (3×300 mL). The combined organic layers were washed with water (2×100 mL), brine (100 mL), dried over magnesium sulfate and concentrated under reduced pressure. The residue was purified by column chromatography (silica gel, 100-200 mesh, 0 to 10% petroleum ether in ethyl acetate) to afford 2-bromo-4-iodopyrimidine (4.0 g, 27%) as a white solid.

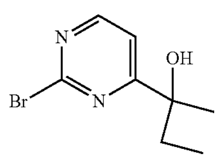

Step 2: 2-(2-bromopyrimidin-4-yl)butan-2-ol

To a solution of methyl ethyl ketone (2.0 g, 28.08 mmol) and 2-bromo-4-iodo-pyrimidine (4.0 g, 14.04 mmol) in tetrahydrofuran (30 mL) was added isopropyl magnesium bromide (1.0 M in tetrahedron, 16.2 mL, 16.2 mmol) at −60° C. The mixture was stirred at −60° C. for 1 h and quenched by addition of saturated ammonium chloride (30 mL). The resulting solution was extracted with ethyl acetate (3×20 mL). The combined organic layers were washed with water (2×10 ml), brine (20 mL), dried over sodium sulfate and concentrated under reduced pressure. The residue was purified by column chromatography (silica gel, 100-200 mesh, 0 to 20% petroleum ether in ethyl acetate) to give the product 2-(2-bromopyrimidin-4-yl)butan-2-ol (1.0 g, 31%) as a yellow oil. LC-MS $R_T$=2.45 min, m/z=231.0 $(M+H)^+$.

LCMS (0-30% acetonitrile in water+0.03% trifluoacetic acid over 4.0 mins) retention time 2.45/min, ESI+ found [M+H]=231.0

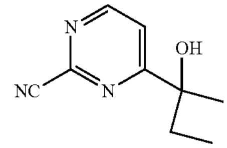

Step 3: 4-(1-hydroxy-1-methyl-propyl)pyrimidine-2-carbonitrile

To a solution of 2-(2-bromopyrimidin-4-yl)butan-2-ol (1.0 g, 4.00 mmol) in dimethyl sulfoxide (5 mL) was added 1,4-diazabicyclo[2.2.2]octane (243 mg, 2.16 mmol) and sodium cyanide (400 mg, 8.16 mmol) in water (2.5 ml). The mixture was stirred at 25° C. for 16 h and extracted with ethyl acetate (3×25 mL). The combined organic layers were concentrated under reduced pressure and the residue was purified by column chromatography (silica gel, 100-200 mesh, 0 to 30% petroleum ether in ethyl acetate) to afford 4-(1-hydroxy-1-methyl-propyl)pyrimidine-2-carbonitrile (600 mg, 78%) as a white solid. LC-MS $R_T$=1.48 min, m/z=178.0 $(M+H)^+$.

LCMS (0-30% acetonitrile in water+0.03% trifluoacetic acid over 4 mins) retention time 1.48/min, ESI+ found [M+H]=178.0

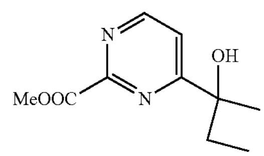

Step 4: 4-(1-hydroxy-1-methyl-propyl)pyrimidine-2-carboxylate

A solution of 4-(1-hydroxycyclobutyl)pyrimidine-2-carbonitrile (600 mg, 3.39 mmol) in methanol (5 mL) was added HCl (1M in methanol, 6.77 mL). The reaction mixture was stirred at 25° C. for 16 h and quenched by addition of saturated sodium bicarbonate (20 mL). The resulting solution was extracted with ethyl acetate (3×15 mL). The combined organic layers were dried over sodium sulfate and concentrated under reduced pressure. The residue was purified by preparative TLC (50% ethyl acetate in petroleum ether, $R_f$=0.3) to afford 4-(1-hydroxy-1-methyl-propyl)pyrimidine-2-carboxylate (300 mg, 42%) as yellow oil. LC-MS $R_T$=2.10 min, m/z=211.0 $(M+H)^+$.

LCMS (0-30% acetonitrile in water+0.03% trifluoacetic acid over 4 mins) retention time 2.10/min, ESI+ found [M+H]=211.0.

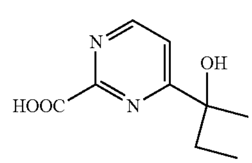

Step 5: 4-(1-hydroxy-1-methyl-propyl)pyrimidine-2-carboxylic acid

A mixture of 4-(1-hydroxy-1-methyl-propyl)pyrimidine-2-carboxylate (50 mg, 0.24 mmol) and lithium hydroxide (29 mg, 1.19 mmol) in tetrahydrofuran (5 mL) and water (1 mL) was stirred at 25° C. for 16 h. The mixture was adjusted to pH=6 by addition of 1N HCl and then extracted with ethyl acetate (3×15 mL). The combined organic layers were dried over sodium sulfate and concentrated under reduced pressure to give crude 4-(1-hydroxy-1-methyl-propyl) pyrimidine-2-carboxylic acid (30 mg, 64%) as a white solid.

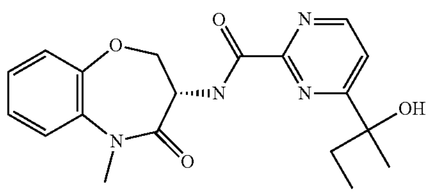 [SMILES: CCC(C)(O)c1ccnc(C(=O)N[C@H]2COc3ccccc3N(C)C2=O)n1]

Step 6: 4-(1-hydroxy-1-methyl-propyl)-N-[(3S)-5-methyl-4-oxo-2,3-dihydro-1,5-benzoxazepin-3-yl] pyrimidine-2-carboxamide A mixture of (3S)-3-amino-5-methyl-2,3-dihydro-1,5-benzoxazepin-4-one (29 mg, 0.15 mmol), 4-(1-hydroxy-1-methyl-propyl)pyrimidine-2-carboxylic acid (30 mg, 0.15 mmol), 1-(3-dimethyl aminopropyl)-3-ethylcarbodiimide-hydrochloride (35 mg, 0.18 mmol) and 1-hydroxybenzotriazole (25 mg, 0.18 mmol) in N,N-dimethylformamide (4 mL) was stirred at 25° C. for 16 h. The mixture was concentrated under reduced pressure and the residue was purified by RP-HPLC (18% to 48% acetonitrile/0.05% ammonia hydroxide in water) to give 4-(1-hydroxy-1-methyl-propyl)-N-[(3S)-5-methyl-4-oxo-2,3-dihydro-1,5-benzoxazepin-3-yl]pyrimidine-2-carboxamide (27 mg, 47%) as a white solid. $^1$H NMR (400 MHz, $CD_3OD$) δ8.89 (d, J=5.6 Hz, 1H), 7.84 (d, J=5.2 Hz, 1H), 7.49-7.41 (m, 1H), 7.34-7.24 (m, 3H), 5.06-5.02 (m, 1H), 4.70-4.66 (m, 1H), 4.47-4.42 (m, 1H), 3.44 (s, 3H), 2.01-1.87 (m, 2H), 1.56 (s, 3H), 0.81-0.77 (m, 3H). LCMS $R_T$=1.971 min; m/z=371.2 $(M+H)^+$.

LCMS (0-60% acetonitrile in water+0.05% ammonium bicarbonate over 3 mins) retention time 1.971 min, ESI+ found [M+H]=371.2.

Example 550

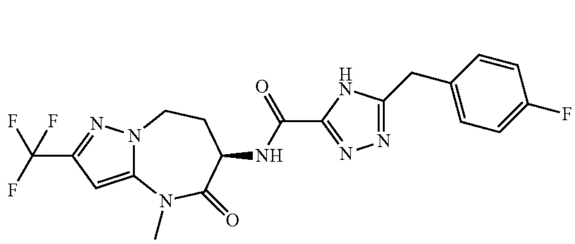

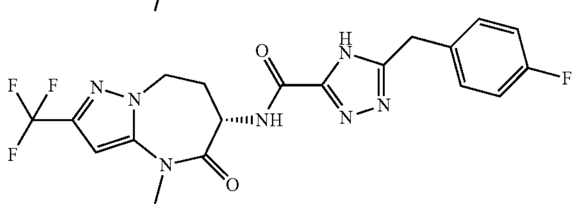

5-[(4-fluorophenyl)methyl]-N-(6R)-4-methyl-5-oxo-2-(trifluoromethyl)-7,8-dihydro-6H-pyrazolo[1,5-a][1,3]diazepin-6-yl]-4H-1,2,4-triazole-3-carboxamide and 5-[(4-fluorophenyl)methyl]-N-(6S)-4-methyl-5-oxo-2-(trifluoromethyl)-7,8-dihydro-6H-pyrazolo[1,5-a][1,3]diazepin-6-yl]-4H-1,2,4-triazole-3-carboxamide Amide coupling prepared in a similar fashion to WX Method 011. The crude was purified by RP-HPLC (acetonitrile 0-40%/0.05% ammonium hydroxide in water) to give 5-1-(4-fluorobenzyl)-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide (50 mg, 53%) as white solid. The racemic material was separated by chiral SFC to give:

5-[(4-fluorophenyl)methyl]-N-(6R)-4-methyl-5-oxo-2-(trifluoromethyl)-7,8-dihydro-6H-pyrazolo[1,5-a][1,3]diazepin-6-yl-4H-1,2,4-triazole-3-carboxamide (Peak 2, Retention time=3.822 min) (14 mg, 27%) as white solid. $^1$H NMR (400 MHz, $CD_3OD$) δ7.33-7.29 (m, 2H), 7.07-7.03 (m, 2H), 6.67 (s, 1H), 4.56-4.47 (m, 2H), 4.42-4.33 (m, 1H), 4.14 (s, 2H), 3.37 (s, 3H), 2.94-2.85 (m, 1H), 2.35-2.28 (m, 1H). LC-MS $R_T$=1.126 min, m/z=452.1 $(M+H)^+$.

LCMS (10 to 80% acetonitrile in water+0.03% ammonium bicarbonate over 3.0 mins) retention time 1.126 min, ESI+ found [M+H]=452.1.

5-[(4-fluorophenyl)methyl]-N-(6 S)-4-methyl-5-oxo-2-(trifluoromethyl)-7,8-dihydro-6H-pyrazolo[1,5-a][1,3]diazepin-6-yl-4H-1,2,4-triazole-3-carboxamide (Peak 1, Retention time=3.495 min) (16 mg, 31%) as white solid. $^1$H NMR (400 MHz, $CD_3OD$) δ7.33-7.29 (m, 2H), 7.07-7.03 (m, 2H), 6.67 (s, 1H), 4.56-4.47 (m, 2H), 4.42-4.33 (m, 1H), 4.14 (s, 2H), 3.37 (s, 3H), 2.94-2.85 (m, 1H), 2.35-2.28 (m, 1H). LC-MS $R_T$=1.128 min, m/z=452.1 $(M+H)^+$.

LCMS (10 to 80% acetonitrile in water+0.03% ammonium bicarbonate over 3.0 mins) retention time 1.128 min, ESI+ found [M+H]=452.1.

SFC conditions: Column Chiralpak AS-H 250×4.6 mm I.D., 5 um Mobile phase: A: CO2 B: ethanol (0.05% DEA) Gradient: from 5% to 40% of B in 5.0 min and hold 40% for 2.5 min, then 5% of B for 2.5 min Flow rate: 2.5 mL/min Column temperature: 35° C.

Example 551

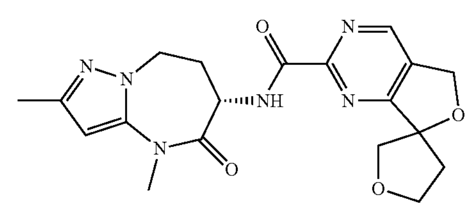 [SMILES: Cc1cc2n(n1)CC[C@H](NC(=O)c1ncc3c(n1)C1(CCOC1)OC3)C(=O)N2C]

N-[(6S)-2,4-dimethyl-5-oxo-7,8-dihydro-6H-pyrazolo[1,5-a][1,3]diazepin-6-yl]spiro[5H-furo[3,4-d]pyrimidine-7,3'-tetrahydrofuran]-2-carboxamide Amide coupling prepared in a similar fashion to WX Method 162 (RIP1K_experimental_3$^{rd}$_WX.doc). The crude was purified by RP-HPLC (6% to 36% acetonitrile/0.05% ammonia hydroxide in water) to afford N-[(6S)-2,4-dimethyl-5-oxo-7,8-dihydro-6H-pyrazolo[1,5-a][1,3]diazepin-6-yl]spiro[5H-furo [3,4-d]pyrimidine-7,3'-tetrahydrofuran]-2-carboxamide (60 mg, 64%). $^1$H NMR (400 MHz, $CD_3OD$) δ 8.85 (s, 1H), 6.13 (s, 1H), 5.19 (s, 2H), 4.62-4.57 (m, 1H), 4.37-4.21 (m, 2H), 4.18-4.00 (m, 4H), 3.35 (s, 3H), 2.99-2.88 (m, 1H), 2.50-2.41 (m, 1H), 2.35-2.27 (m, 5H).

LC-MS $R_T$=1.146 min, m/z=399.2 $(M+H)^+$.

LCMS (10 to 80% acetonitrile in water+0.03% ammonium bicarbonate over 3.0 mins) retention time 1.146 min, ESI+ found [M+H]=399.2.

Example 552

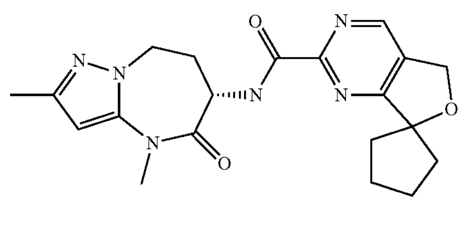 [SMILES: Cc1cc2n(n1)CC[C@H](NC(=O)c1ncc3c(n1)C1(CCCC1)OC3)C(=O)N2C]

N-[(6S)-2,4-dimethyl-5-oxo-7,8-dihydro-6H-pyrazolo[1,5-a][1,3]diazepin-6-yl]spiro[5H-furo[3,4-d]pyrimidine-7,1'-cyclopentane]-2-carboxamide Amide coupling prepared in a similar fashion to WX Method 164 (RIP1K_experimental_3$^{rd}$_WX.doc). The crude was purified by RP-HPLC (17% to 47% acetonitrile/0.05% ammonia hydroxide in water) to give N-[(6S)-2,4-dimethyl-5-oxo-7,8-dihydro-6H-pyrazolo[1,5-a][1,3]diazepin-6-yl]spiro[5H-furo [3,4-d]pyrimidine-7,1'-cyclopentane]-2-carboxamide (42.9 mg, 47%) as a white solid. $^1$H NMR (400 MHz, $CD_3OD$) δ8.79 (s, 1H), 6.13 (s, 1H), 5.11 (s, 2H), 4.59-4.57 (m, 1H), 4.33-4.25 (m, 2H), 3.35 (s, 3H), 2.98-2.91 (m, 1H), 2.31-2.25 (m, 4H), 2.13-1.99 (m, 4H), 1.94-1.91 (m, 4H). LC-MS $R_T$=1.850 min, m/z=397.2 $[M+H]^+$.

LCMS (0 to 60% acetonitrile in water+0.05% ammonium hydroxide over 3 mins) retention time 1.850 min, ESI+ found [M+H]=397.2.

Example 553

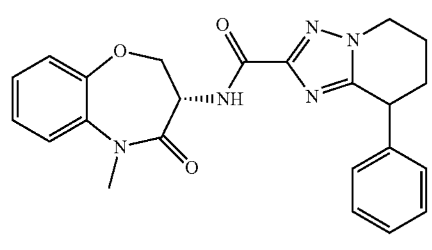 [SMILES: CN1C(=O)[C@@H](NC(=O)c2nc3n(n2)CCCC3c2ccccc2)COc2ccccc21]

8-phenyl-N-[(3S)-5-methyl-4-oxo-2,3-dihydro-1,5-benzoxazepin-3-yl]-5,6,7,8-tetrahydro-[1,2,4]triazolo[1,5-a]pyridine-2-carboxamide Amide coupling prepared in a similar fashion to WX Method 119 (RIP1K_experimental_3$^{rd}$_WX.doc). The crude was purified by PR-HPLC (32% to 62% acetonitrile/0.05% ammonia hydroxide in water) to give 8-phenyl-N-[(3S)-5-methyl-4-oxo-2,3-dihydro-1,5-benzoxazepin-3-yl]-5,6,7,8-tetrahydro-[1, 2,4]triazolo[1,5-a]pyridine-2-carboxamide (4 mg, 33%) as a white solid. $^1$H NMR (400 MHz, $CD_3OD$) δ7.45-7.39 (m, 1H), 7.36-7.20 (m, 6H), 7.16 (d, J=8.0 Hz, 2H), 5.02-4.95 (m, 1H), 4.58-4.51 (m, 1H), 4.40-4.32 (m, 4H), 3.39 (s, 3H), 2.40-2.33 (m, 1H), 2.24-2.03 (m, 3H). LCMS $R_T$=0.831 min, m/z=418.0 $[M+H]^+$.

LCMS (10 to 80% acetonitrile in water+0.05% ammonium bicarbonate over 3 mins) retention time 0.831 min, ESI+ found [M+H]=418.0

Example 554

WX Method 119

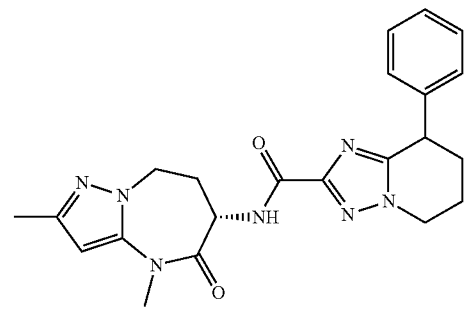 [SMILES: Cc1cc2n(n1)CC[C@H](NC(=O)c1nc3n(n1)CCCC3c1ccccc1)C(=O)N2C]

8-phenyl-N-[(6S)-2,4-dimethyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide

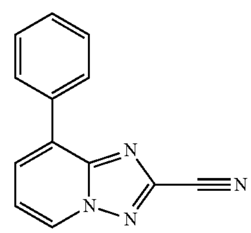 [SMILES: N#Cc1nc2c(-c3ccccc3)cccn2n1]

Step 1: 8-phenyl-[1,2,4]triazolo[1,5-a]pyridine-2-carbonitrile

To a mixture of 8-phenyl-[1,2,4]triazolo[1,5-a]pyridin-2-amine (500 mg, 2.38 mmol) and cuprous cyanide (234 mg, 2.62 mmol) in acetonitrile (30 mL) was added isopentyl nitrite (0.45 mL, 3.33 mmol) at 0° C. The mixture was stirred at 0° C. for 30 min and then heated at 80° C. for 4 h. After cooled to 0° C., the mixture was added aqueous sodium hydroxide (2N, 8 mL), saturated sodium bicarbonate (120 mL) and dichloromethane (150 mL). The mixture was filtered and the organic phase was washed with brine (50 mL) and concentrated under reduced pressure. The residue was purified by column chromatography (silica gel, 100-200 mesh, 0 to 15% ethyl acetate in petroleum ether) to afford 8-phenyl-[1,2,4]triazolo[1,5-a]pyridine-2-carbonitrile (50 mg, 10%) as a white solid. LCMS $R_T$=1.053 min, m/z=221.1 $[M+H]^+$.

LCMS (10 to 80% acetonitrile in water+0.05% ammonium bicarbonate over 3 mins) retention time 1.053 min, ESI+ found [M+H]=221.1

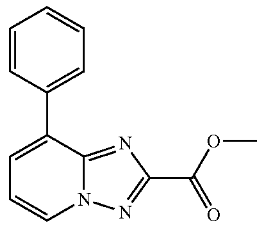 [SMILES: COC(=O)c1nc2c(-c3ccccc3)cccn2n1]

Step 2: methyl 8-phenyl-[1,2,4]triazolo[1,5-a]pyridine-2-carboxylate

A solution of 8-phenyl-[1,2,4]triazolo[1,5-a]pyridine-2-carbonitrile carbonitrile (50 mg, 0.22 mmol) in HCl (2N in methanol, 4.0 mL, 8.0 mmol) was stirred at 20° C. for 20 h and concentrated under reduced pressure to give crude methyl 8-phenyl-[1,2,4]triazolo[1,5-a]pyridine-2-carboxylate (30 mg, 52%) as a white solid. LCMS $R_T$=0.778 & 0.844 min, m/z=253.9 $[M+H]^+$.

LCMS (5 to 95% acetonitrile in water+0.1% trifluoacetic acid over 1.5 mins) retention time 0.778 min, ESI+ found [M+H]=253.9; retention time 0.844 min, ESI+ found [M+H]= 253.9

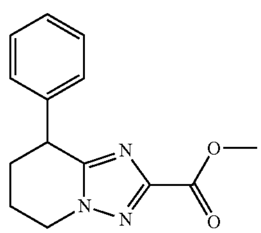 [SMILES: COC(=O)c1nc2n(n1)CCCC2c1ccccc1]

Step 3: methyl 8-phenyl-5,6,7,8-tetrahydro-[1,2,4]triazolo[1,5-a]pyridine-2-carboxylate A mixture of methyl 8-phenyl-[1,2,4]triazolo[1,5-a]pyridine-2-carboxylate (30 mg, 0.12 mmol) and Pd/C (10%, 126 mg, 0.12 mmol) in methanol (10 mL) was hydrogenated (50 psi) for 1 h and filtered. The filtrate was concentrated under reduced pressure to give crude methyl 8-phenyl-5,6,7,8-tetrahydro-[1,2,4]triazolo[1,5-a]pyridine-2-carboxylate (20 mg, 66%) as a white solid. LCMS $R_T$=0.729 min, m/z=257.9 $[M+H]^+$.

LCMS (5 to 95% acetonitrile in water+0.1% trifluoacetic acid over 1.5 mins) retention time 0.729 min, ESI+ found [M+H]=257.9

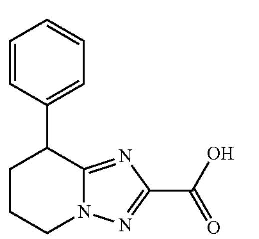 [SMILES: O=C(O)c1nc2n(n1)CCCC2c1ccccc1]

Step 4: 8-phenyl-5,6,7,8-tetrahydro-[1,2,4]triazolo[1,5-a]pyridine-2-carboxylic acid A mixture of methyl 8-phenyl-5,6,7,8-tetrahydro-[1,2,4]triazolo[1,5-a]pyridine-2-carboxylate (20 mg, 0.08 mmol) and lithium hydroxide hydrate (16 mg, 0.39 mmol) in tetrahydrofuran (5 mL) and water (1 mL) was stirred at 25° C. for 4 h. The solution was diluted with water (20 mL) and adjusted to pH=4 by addition of 2N HCl. The resulting solution was extracted with ethyl acetate (3×20 mL). The combined organic layers were dried over sodium sulfate and concentrated under reduced pressure to give crude 8-phenyl-5,6,7,8-tetrahydro-[1,2,4]triazolo [1,5-a]pyridine-2-carboxylic acid (10 mg, 53%), used as is in the next step.

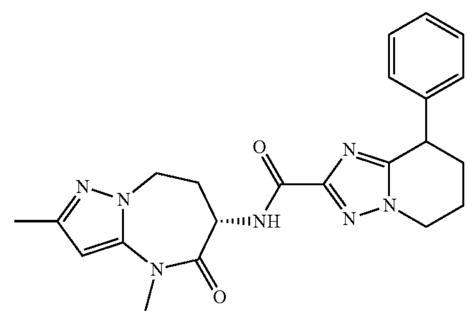 [SMILES: Cc1cc2n(n1)CC[C@H](NC(=O)c1nc3n(n1)CCCC3c1ccccc1)C(=O)N2C]

Step 5: 8-phenyl-N-[(6S)-2,4-dimethyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide A mixture of 8-phenyl-5,6,7,8-tetrahydro-[1,2,4]triazolo[1,5-a]pyridine-2-carboxylic acid (10 mg, 0.04 mmol), 1-hydroxybenzotriazole (7 mg, 0.05 mmol), (6s)-6-amino-2,4-dimethyl-7,8-dihydro-6h-pyrazolo[1,5-a][1,3]diazepin-5-one (9 mg, 0.05 mmol) and 1-(3-dimethylaminopropyl)-3-ethylcarbodiimidehydrochloride (9 mg, 0.05 mmol) in N,N-dimethylformamide (5 mL) was stirred at 25° C. for 1 h. The mixture was concentrated under reduced pressure and the residue was purified by RP-HPLC (36% acetonitrile/0.05% ammonia hydroxide in water) to give 8-phenyl-N-[(6S)-2,4-dimethyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide (4.5 mg, 26%) as a white solid. $^1H$ NMR (400 MHz, $CD_3OD$) δ7.39-7.23 (m, 3H), 7.20-7.08 (m, 2H), 6.10 (s, 1H), 4.53-4.47 (m, 1H), 4.38-4.12 (m, 5H), 3.34-3.31 (m, 3H), 2.83-2.72 (m, 1H), 2.40-2.32 (m, 1H), 2.31-1.99 (m, 7H). LCMS $R_T$=0.769 min, m/z=420.1 $[M+H]^+$.

LCMS (5 to 95% acetonitrile in water+0.1% trifluoacetic acid over 1.5 mins) retention time 0.769 min, ESI+ found [M+H]=420.1

Example 555

WX Method 056

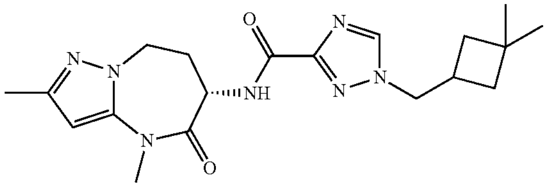

1-[(3,3-dimethylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide

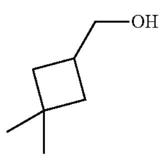

Step 1: (3,3-dimethylcyclobutyl)methanol

To a solution of 3,3-dimethylcyclobutanecarboxylic acid (300 mg, 2.34 mmol) in tetrahydrofuran (10 mL) was added $LiAlH_4$ (178 mg, 4.68 mmol) at 0° C. The mixture was stirred at 25° C. for 16 h and then quenched by addition of water (0.1 mL), 15% aqueous sodium hydroxide (0.1 mL) and water (0.3 mL). The mixture was filtered and the filtrate was concentrated under reduced pressure to afford crude (3,3-dimethylcyclobutyl)methanol (100 mg, 86%) as a colorless oil, used as is in the next step.

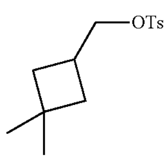 [SMILES: Cc1ccc(S(=O)(=O)OCC2CC(C)(C)C2)cc1]

Step 2: (3,3-dimethylcyclobutyl)methyl 4-methylbenzenesulfonate

To a solution of p-toluenesulfonylchloride (521 mg, 2.73 mmol) in dichloromethane (10 mL) was added (3,3-dimethylcyclobutyl)methanol (260 mg, 2.28 mmol) and 4-dimethylaminopyridine (556 mg, 4.55 mmol). The reaction mixture was stirred at 20° C. for 16 h and then quenched by addition of water (10 mL). The mixture was extracted with ethyl acetate (3×20 mL). The combined organic layers were washed with water (10 mL), brine (10 mL), dried over anhydrous sodium sulfate and concentrated. The residue was purified by column chromatography (silica gel, 100-200 mesh, 0 to 10% ethyl acetate in petroleum ether) to afford (3,3-dimethylcyclobutyl)methyl 4-methylbenzenesulfonate (350 mg, 57%) as colorless oil, used as is in the next step.

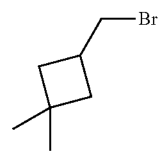

Step 3: 3-(bromomethyl)-1,1-dimethylcyclobutane

To a solution of (3,3-dimethylcyclobutyl)methyl 4-methylbenzenesulfonate (350 mg, 1.30 mmol) in acetone (20 mL) was added lithium bromide (566 mg, 6.52 mmol). The reaction mixture was heated to 70° C. for 2 h and then concentrated under reduced pressure. The residue was diluted with water (20 mL) and extracted with ethyl acetate (3×20 mL). The combined organic layers were washed with water (10 mL), brine (10 mL), dried over anhydrous sodium sulfate and concentrated to afford crude 3-(bromomethyl)-1,1-dimethylcyclobutane (150 mg, 65%) as colorless oil, used as is in the next step.

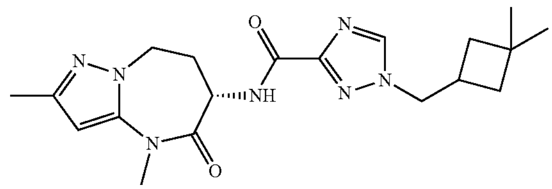

Step 4: 1-[(3,3-dimethylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide A mixture of 3-(bromomethyl)-1,1-dimethyl-cyclobutane (37 mg, 0.21 mmol), N-[(6S)-2,4-dimethyl-5-oxo-7,8-dihydro-6H-pyrazolo[1,5-a][1,3]diazepin-6-yl]-1H-1,2,4-triazole-3-carboxamide (50 mg, 0.17 mmol) and potassium carbonate (72 mg, 0.52 mmol) in N,N-dimethylformamide (5 mL) was stirred at 20° C. for 16 h. The mixture was concentrated under reduced pressure and the residue was purified by RP-HPLC (acetonitrile 40-70%/0.05% ammonium hydroxide in water) to afford 1-[(3,3-dimethylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide (17.2 mg, 26%) as a white solid. $^1H$ NMR (400 MHz, $CD_3OD$) δ8.46 (s, 1H), 6.12 (s, 1H), 4.57-4.52 (m, 1H), 4.32-4.24 (m, 4H), 3.34 (s, 3H), 2.86-2.79 (m, 2H), 2.29-2.23 (m, 4H), 1.87-1.82 (m, 2H), 1.67-1.61 (m, 2H), 1.16 (s, 3H), 1.08 (s, 3H). LCMS $R_T$=0.810 min; m/z=386.1 $(M+H)^+$.

LCMS (5 to 95% acetonitrile in water+0.03% trifluoacetic acid over 1.5 mins) retention time 0.810 min, ESI+ found [M+H]=386.1.

Example 556

WX Method 169

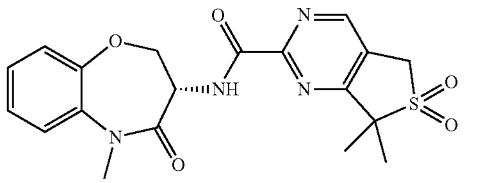 [SMILES: CN1C(=O)[C@@H](NC(=O)c2ncc3c(n2)C(C)(C)S(=O)(=O)C3)COc2ccccc21]

7,7-dimethyl-6,6-dioxo-N-[(3S)-5-methyl-4-oxo-2,3-dihydro-1,5-benzoxazepin-3-yl]-5H-thieno[3,4-d]pyrimidine-2-carboxamide

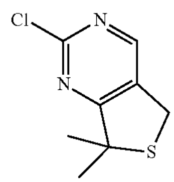

Step: 2-chloro-7,7-dimethyl-5,7-dihydrothieno[3,4-d]pyrimidine

To a mixture of 2,4-dichloro-7,7-dimethyl-5,7-dihydrothieno[3,4-d]pyrimidine (1.0 g, 4.25 mmol) and zinc (834 mg, 12.76 mmol) in water (20 mL) was heated at 100° C. for 12 h. The reaction mixture was extracted with ethyl acetate (3×100 mL). The combined organic layers were washed with water (2×100 mL), brine (1×100 mL), dried with magnesium sulfate and concentrated under reduced pressure. The residue was purified by column chromatography (silica gel, 100-200 mesh, 0 to 10% ethyl acetate in petroleum ether) to give 2-chloro-7,7-dimethyl-5,7-dihydrothieno[3,4-d]pyrimidine (400 mg, 47%) as white solid. $^1H$ NMR (400 MHz, $CD_3OD$) δ8.60 (s, 1H), 4.18 (s, 2H), 1.69 (s, 6H).

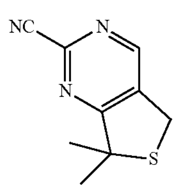

Step 2: 7,7-dimethyl-5,7-dihydrothieno[3,4-d]pyrimidine-2-carbonitrile

To a solution of 2-chloro-7,7-dimethyl-5H-thieno[3,4-d]pyrimidine (250 mg, 1.25 mmol) in dimethyl sulfoxide (10 mL) and water (10 mL) were added sodium cyanide (122 mg, 2.49 mmol) and 1,4-diazabicyclo[2.2.2]octane (28 mg, 0.25 mmol). The reaction mixture was stirred at 30° C. for 12 h and extracted with ethyl acetate (3×20 mL). The combined organic layers were washed with water (2×50 mL), brine (50 mL), dried over sodium sulfate and concentrated under reduced pressure. The residue was purified by column chromatography (silica gel, 100-200 mesh, 0 to 50% ethyl acetate in petroleum ether) to give 7,7-dimethyl-5H-thieno[3,4-d]pyrimidine-2-carbonitrile (150 mg, 63%) as a white solid.

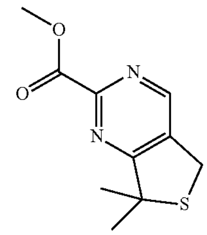

Step 3: methyl 7,7-dimethyl-5,7-dihydrothieno[3,4-d]pyrimidine-2-carboxylate

A solution of 7,7-dimethyl-5H-thieno[3,4-d]pyrimidine-2-carbonitrile (110 mg, 0.58 mmol) in methanol (5 mL) was added HCl (4N in methanol, 5 mL). The mixture was stirred at 25° C. for 12 h and concentrated under reduce pressure. The residue was purified by column chromatography (silica gel 100-200 mesh, 0% to 60% ethyl acetate in petroleum ether) to give methyl 7,7-dimethyl-5,7-dihydrothieno[3,4-d]pyrimidine-2-carboxylate (120 mg, 93%) as a white solid. LCMS $R_T$=0.600 min, m/z=224.9 $[M+H]^+$.

LCMS (5-95% acetonitrile in water+0.1% trifluoroacetic over 1.5 mins) retention time 0.600 min, ESI+ found $[M+H]^+$=224.9

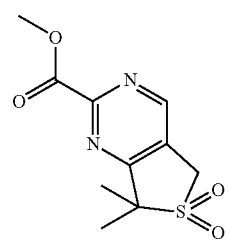 [SMILES: COC(=O)c1ncc2c(n1)C(C)(C)S(=O)(=O)C2]

Step 4: methyl 7,7-dimethyl-5,7-dihydrothieno[3,4-d]pyrimidine-2-carboxylate 6,6-dioxide A mixture of oxone (658 mg, 1.07 mmol) and methyl 7,7-dimethyl-5,7-dihydrothieno[3,4-d]pyrimidine-2-carboxylate (120 mg, 0.54 mmol) in tetrahydrofuran (3 mL) and water (3 mL) was stirred at 20° C. for 12 h and quenched by addition of saturated sodium hydrogen sulfite (5 mL). The mixture was extracted with ethyl acetate (3×20 mL). The combined organic layers were washed with water (2×30 mL), brine (30 mL), dried over sodium sulfate and concentrated under reduced pressure. The residue was purified by column chromatography (silica gel 100-200 mesh, 0% to 60% ethyl acetate in petroleum ether) to give methyl 7,7-dimethyl-5,7-dihydrothieno[3,4-d]pyrimidine-2-carboxylate 6,6-dioxide (120 mg, 88%) as a white solid. LCMS $R_T$=1.226 min, m/z=257.1 $[M+H]^+$.

LCMS (0-60% acetonitrile in water+0.1% trifluoroacetic over 2.0 mins) retention time 1.226 min, ESI+ found $[M+H]^+$=257.1

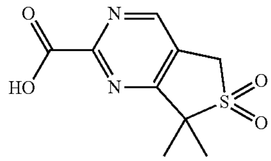 [SMILES: CC1(C)c2nc(C(=O)O)ncc2CS1(=O)=O]

Step 5: 7,7-dimethyl-5,7-dihydrothieno[3,4-d]pyrimidine-2-carboxylic acid 6,6-dioxide A mixture of methyl 7,7-dimethyl-5,7-dihydrothieno[3,4-d]pyrimidine-2-carboxylate 6,6-dioxide (30 mg, 0.12 mmol) and lithium hydroxide (61 mg, 21.9 mmol) in tetrahydrofuran (3 mL) and water (3 mL) was stirred at 25° C. for 16 h. The mixture was adjusted to pH to 5 by addition of hydrochloric acid (1.0 M). The resulting solution was concentrated to dryness under reduced pressure to give crude 7,7-dimethyl-5,7-dihydrothieno[3,4-d]pyrimidine-2-carboxylic acid 6,6-dioxide (28 mg, 97%) as a white solid, used as is in the next step.

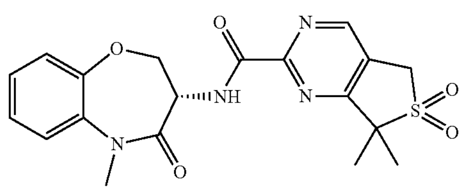 [SMILES: CN1C(=O)[C@@H](NC(=O)c2ncc3c(n2)C(C)(C)S(=O)(=O)C3)COc2ccccc21]

Step 6: 7,7-dimethyl-6,6-dioxo-N-[(3S)-5-methyl-4-oxo-2,3-dihydro-1,5-benzoxazepin-3-yl]-5H-thieno[3,4-d]pyrimidine-2-carboxamide A mixture of (3S)-3-amino-5-methyl-2,3-dihydro-1,5-benzoxazepin-4-one (22 mg, 0.12 mmol), 7,7-dimethyl-6,6-dioxo-5H-thieno[3,4-d]pyrimidine-2-carboxylic acid (28 mg, 0.12 mmol), 1H-benzo[d][1,2,3]triazol-1-ol (17 mg, 0.13 mmol) and $N^1$-((ethylimino)methylene)-$N^3$,$N^3$-dimethylpropane-1,3-diamine hydrochloride (24 mg, 0.13 mmol) in N,N-dimethylformamide (4 mL) was stirred at 25° C. for 16 h. The mixture was concentrated under reduced pressure and the residue was purified by RP-HPLC (acetonitrile 28% to 58%/0.1% ammonia hydroxide in water) to give 7,7-dimethyl-6,6-dioxo-N-[(3S)-5-methyl-4-oxo-2,3-dihydro-1,5-benzoxazepin-3-yl]-5H-thieno[3,4-d]pyrimidine-2-carboxamide (7 mg, 15%) as a white solid. $^1$H NMR (400 MHz, $CD_3OD$) δ8.93 (s, 1H), 7.45-7.43 (m, 1H), 7.36-7.22 (m, 3H), 5.06-5.02 (m, 1H), 4.87-4.86 (m, 2H), 4.66-4.58 (m, 1H), 4.47-4.42 (m, 1H), 3.43 (s, 3H), 1.68 (s, 6H). LCMS $R_T$=1.543 min; m/z=417.1 $(M+H)^+$.

LCMS (10 to 80% acetonitrile in water+0.03% ammonium bicarbonate over 3.0 mins) retention time 1.543 min, ESI+ found [M+H]=417.1.

Example 557

WX Method 085

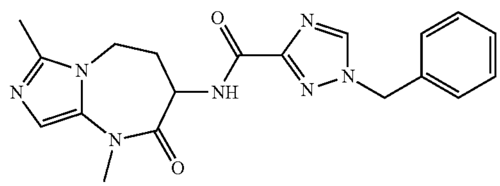 [SMILES: Cc1ncc2n1CCC(NC(=O)c1ncn(Cc3ccccc3)n1)C(=O)N2C]

1-benzyl-N-(1,7-dimethyl-2-oxo-4,5-dihydro-3H-imidazo[1,5-a][1,3]diazepin-3-yl)-1,2,4-triazole-3-carboxamide

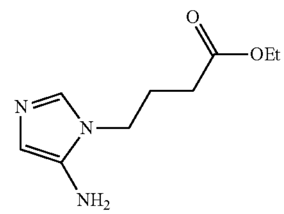 [SMILES: CCOC(=O)CCCn1cncc1N]

Step 1: ethyl 4-(5-amino-1H-imidazol-1-yl)butanoate

A mixture solution of ethyl 4-(5-nitroimidazol-1-yl)butanoate (13.0 g, 57.21 mmol) and Pd/C (10%, 5.0 g, 4.7 mmol) in 1,4-dioxane (200 mL) was hydrogenated (25 psi) for 15 h and filtered. The filtrate was concentrated under reduced pressure to afford crude ethyl 4-(5-aminoimidazol-1-yl)butanoate (10 g, 88%) as a black oil, used as is in the next step.

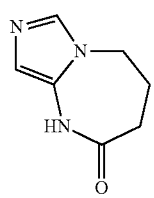 [SMILES: O=C1CCCn2cncc2N1]

Step 2: 4,5-dihydro-1H-imidazo[1,5-a][1,3]diazepin-2(3H)-one

A mixture of ethyl 4-(5-aminoimidazol-1-yl)butanoate (10.0 g, 50.7 mmol) and potassium 2-methylpropan-2-olate (11.38 g, 101.4 mmol) in dimethyl sulfoxide (20 mL) was stirred at 25° C. for 15 h and concentrated under reduced pressure. The residue was purified by column chromatography (silica gel, 100-200 mesh, 0 to 10% methanol in dichloromethane) to afford 1,3,4,5-tetrahydroimidazo[1,5-a][1,3]diazepin-2-one (8.0 g, 100%) as a light yellow oil, used as is in the next step.

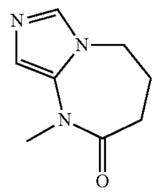

Step 3: 1-methyl-4,5-dihydro-1H-imidazo[1,5-a][1,3]diazepin-2(3H)-one

To a solution of 1,3,4,5-tetrahydroimidazo[1,5-a][1,3]diazepin-2-one (3.0 g, 19.85 mmol) in N,N-dimethylformamide (20 mL) was added cesium carbonate (6.5 g, 19.85 mmol) and iodomethane (2.8 g, 19.85 mmol). The reaction mixture was stirred at 25° C. for 15 h and then filtered. The filtrate was concentrated under reduced pressure and the residue was purified by column chromatography (silica gel, 100-200 mesh, 0 to 10% methanol in dichloromethane) to afford 1-methyl-4,5-dihydro-3H-imidazo[1,5-a][1,3]diazepin-2-one (2.5 g, 76%) as a light yellow oil, used as is in the next step.

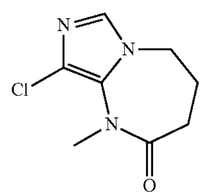

Step 4: 9-chloro-1-methyl-4,5-dihydro-1H-imidazo[1,5-a][1,3]diazepin-2(3H)-one

To a solution of 1-methyl-4,5-dihydro-3H-imidazo[1,5-a][1,3]diazepin-2-one (1.0 g, 6.05 mmol) in chloroform (20 mL) was added 1-chloropyrrolidine-2,5-dione (0.73 g, 5.45 mmol). The reaction mixture was heated at 60° C. for 1 h and concentrated under reduced pressure. The residue was purified by column chromatography (silica gel, 100-200 mesh, 0 to 50% ethyl acetate in petroleum ether) to afford 9-chloro-1-methyl-4,5-dihydro-3H-imidazo[1,5-a][1,3]diazepin-2-one (1.0 g, 83%) as a light yellow solid, used as is in the next step.

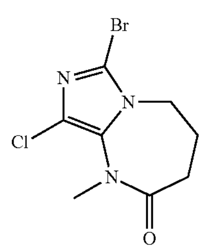

Step 5: 7-bromo-9-chloro-1-methyl-4,5-dihydro-1H-imidazo[1,5-a][1,3]diazepin-2(3H)-one To a solution of 9-chloro-1-methyl-4,5-dihydro-3H-imidazo[1,5-a][1,3]diazepin-2-one (500 mg, 2.5 mmol) in chloroform (20 mL) was added 1-bromo-2,5-pyrrolidinedione (446 mg, 2.5 mmol). The reaction mixture was heated at 60° C. for 4 h and then concentrated under reduced pressure. The residue was purified by column chromatography (silica gel, 100-200 mesh, 0 to 60% ethyl acetate in petroleum ether) to afford 7-bromo-9-chloro-1-methyl-4,5-dihydro-3H-imidazo[1,5-a][1,3]diazepin-2-one (650 mg, 93%) as a yellow solid, used as is in the next step.

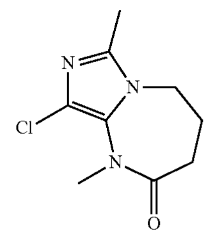

Step 6: 9-chloro-1,7-dimethyl-4,5-dihydro-1H-imidazo[1,5-a][1,3]diazepin-2(3H)-one A mixture of 2,4,6-trimethyl-1,3,5,2,4,6-trioxatriborinane (496 mg, 3.95 mmol) cesium carbonate (1287 mg, 3.95 mmol), $PdCl_2$(dppf) (144 mg, 0.20 mmol) and 7-bromo-9-chloro-1-methyl-4,5-dihydro-3H-imidazo[1,5-a][1,3]diazepin-2-one (550 mg, 1.97 mmol) in 1,4-dioxane (10 mL) and water (2 mL) was heated at 110° C. for 4 h under nitrogen protection. The reaction was concentrated under reduced pressure and the residue was purified by column chromatography (silica gel, 100-200 mesh, 0 to 10% methanol in dichloromethane) to afford 9-chloro-1,7-dimethyl-4,5-dihydro-3H-imidazo[1,5-a][1,3]diazepin-2-one (300 mg, 71%) as a yellow solid, used as is in the next step.

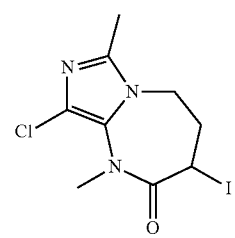

Step 7: 9-chloro-3-iodo-1,7-dimethyl-4,5-dihydro-1H-imidazo[1,5-a][1,3]diazepin-2(3H)-one To a solution of 9-chloro-1,7-dimethyl-4,5-dihydro-3H-imidazo[1,5-a][1,3]diazepin-2-one (250 mg, 1.17 mmol) in dichloromethane (20 mL) was added N1,N1,N3,N3-tetramethylpropane-1,3-diamine (816 mg, 7.02 mmol) and iodotrimethylsilane (1.4 g, 7.02 mmol) at −15° C. The reaction mixture was stirred at −15° C. for 2 h and iodine (3.56 g, 14.04 mmol) was added. The mixture was stirred at −15° C. for another 2 h and then quenched by addition of 5% aqueous sodium thiosulfate (10 mL). The solution was extracted with dichloromethane (3×20 mL).

The combined organic layers were washed with water (10 mL), brine (10 mL), dried over sodium sulfate and concentrated under reduced pressure. The residue was purified by column chromatography (silica gel, 100-200 mesh, 0 to 100% ethyl acetate in petroleum ether) to afford 9-chloro- 3-iodo-1,7-dimethyl-4,5-dihydro-3H-imidazo[1,5-a][1,3]diazepin-2-one (300 mg, 75%) as a colorless solid, used as is in the next step.

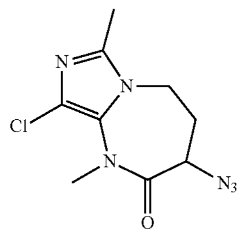 [SMILES: Cc1nc(Cl)c2n1CCC(N=[N+]=[N-])C(=O)N2C]

Step 8: 3-azido-9-chloro-1,7-dimethyl-4,5-dihydro-1H-imidazo[1,5-a][1,3]diazepin-2(3H)-one A mixture of 9-chloro-3-iodo-1,7-dimethyl-4,5-dihydro-3H-imidazo[1,5-a][1,3]diazepin-2-one (300 mg, 0.88 mmol) and sodium azide (500 mg, 7.69 mmol) in N,N-dimethylformamide (5 mL) was stirred at 25° C. for 2 h and then poured into ice water (5 mL). The mixture was extracted with ethyl acetate (3×10 mL). The combined organic layers were concentrated and the residue was purified by preparative TLC (50% ethyl acetate in petroleum ether, $R_f$=0.6) to afford 3-azido-9-chloro-1,7-dimethyl-4,5-dihydro-3H-imidazo[1,5-a][1,3]diazepin-2-one (250 mg, 100%) as a yellow oil, used as is in the next step.

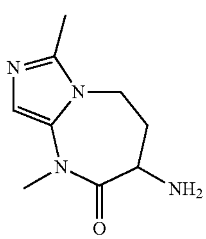

Step 9: 3-amino-1,7-dimethyl-4,5-dihydro-1H-imidazo[1,5-a][1,3]diazepin-2(3H)-one A mixture of 3-azido-9-chloro-1,7-dimethyl-4,5-dihydro-3H-imidazo[1,5-a][1,3]diazepin-2-one (50 mg, 0.20 mmol) and Pd/C (10%, 208 mg, 0.20 mmol) in 1,4-dioxane (5 mL) was hydrogenated (15 psi) for 5 h and filtered. The filtrate was concentrated under reduced pressure to afford 3-amino-1,7-dimethyl-4,5-dihydro-3H-imidazo[1,5-a][1,3]diazepin-2-one (10 mg, 26%) as a colorless oil, used as is in the next step.

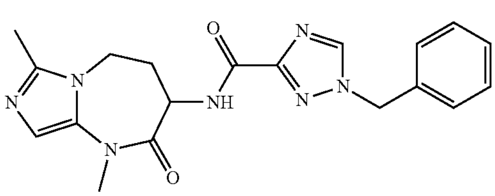 [SMILES: Cc1ncc2n1CCC(NC(=O)c1ncn(Cc3ccccc3)n1)C(=O)N2C]

Step 10: 1-benzyl-N-(1,7-dimethyl-2-oxo-2,3,4,5-tetrahydro-1H-imidazo[1,5-a][1,3]diazepin-3-yl)-1H-1,2,4-triazole-3-carboxamide A mixture of 1-benzyl-1,2,4-triazole-3-carboxylic acid (10.0 mg, 0.05 mmol) 3-amino-1,7-dimethyl-4,5-dihydro-3H-imidazo[1,5-a][1,3]diazepin-2-one (10.0 mg, 0.05 mmol), 1-benzo[d][1,2,3]triazol-1-ol (7.0 mg, 0.05 mmol) and 3-(ethyldiazenyl)-N,N-dimethylpropan-1-amine hydrochloride (9.9 mg, 0.050 mmol) in N,N-dimethylformamide (5 mL) was stirred at 25° C. for 1 h. The reaction was concentrated under reduced pressure and the residue was purified by RP-HPLC (13% to 43% acetonitrile, 0.05% ammonia hydroxide in water) to afford 1-benzyl-N-(1,7-dimethyl-2-oxo-4,5-dihydro-3H-imidazo[1,5-a][1,3]diazepin-3-yl)-1,2,4-triazole-3-carboxamide (6.9 mg, 37%) as white solids. $^1$H NMR (400 MHz, DMSO-$d_6$) δ8.82 (s, 1H), 8.49 (d, J=7.6 Hz, 1H), 7.41-7.27 (m, 5H), 6.80 (s, 1H), 5.48 (s, 2H), 4.40-4.32 (m, 1H), 4.22-4.16 (m, 1H), 3.73-3.71 (m, 1H), 3.24-3.16 (m, 3H), 2.47-2.41 (m, 1H), 2.29 (s, 3H), 2.23-2.20 (m, 1H). LCMS $R_T$=1.705 min, m/z=380.2 $(M+H)^+$.

LCMS (0 to 60% acetonitrile in water+0.05% ammonium bicarbonate over 3 mins) retention time 1.705 ESI+ found [M+H]=380.2.

Example 558

WX Method 151

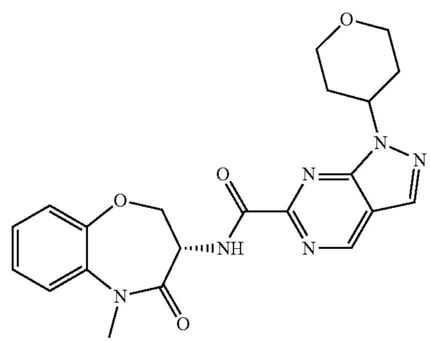 [SMILES: CN1C(=O)[C@@H](NC(=O)c2ncc3cnn(C4CCOCC4)c3n2)COc2ccccc21]

N-[(3S)-5-methyl-4-oxo-2,3-dihydro-1,5-benzoxazepin-3-yl]-1-tetrahydropyran-4-yl-pyrazolo[3,4-d]pyrimidine-6-carboxamide

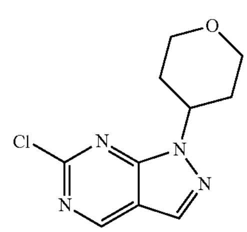 [SMILES: Clc1ncc2cnn(C3CCOCC3)c2n1]

Step 1: 6-chloro-1-(tetrahydro-2H-pyran-4-yl)-1H-pyrazolo[3,4-d]pyrimidine

A mixture of 6-chloro-1H-pyrazolo[3,4-d]pyrimidine (2.0 g, 12.9 mmol), cesium carbonate (8.4 g, 25.9 mmol), 4-bromotetrahydro-2H-pyran (3.2 g, 19.4 mmol) and sodium iodide (193 mg, 1.3 mmol) in N,N-dimethylformamide (40 mL) was heated at 50° C. for 20 h and filtered. The filtrate was concentrated under reduced pressure and the residue was purified by column chromatography (silica gel, 100-200 mesh, 0 to 50% ethyl acetate in petroleum ether) to give 6-chloro-1-(tetrahydro-2H-pyran-4-yl)-1H-pyrazolo[3,4-d] pyrimidine (300 mg, 10%) as a white solid. LCMS $R_T$=1.024 min; m/z=239.1 $(M+H)^+$.

LCMS (0 to 60% acetonitrile in water+0.03% trifluoacetic acid over 2.0 mins) retention time 1.024 min, ESI+ found [M+H]=239.1.

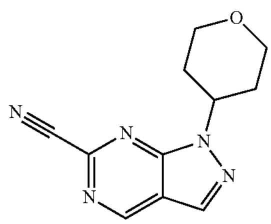 [SMILES: N#Cc1ncc2cnn(C3CCOCC3)c2n1]

Step 2: 1-(tetrahydro-2H-pyran-4-yl)-1H-pyrazolo [3,4-d]pyrimidine-6-carbonitrile To a solution of 6-chloro-1-(tetrahydro-2H-pyran-4-yl)-1H-pyrazolo[3,4-d]pyrimidine (300 mg, 1.26 mmol) in dimethyl sulfoxide (10 mL) was added 1,4-diazabicyclo[2.2.2] octane (14 mg, 0.13 mmol) and sodium cyanide (180 mg, 3.67 mmol) in water (1 mL). The mixture was stirred at 25° C. for 3 h and diluted with water (10 mL). The mixture was extracted with ethyl acetate (3×15 mL). The combined organic layers were dried over sodium sulfate and concentrated under reduced pressure. The residue was purified by preparative TLC (40% ethyl acetate in petroleum ether) to give 1-(tetrahydro-2H-pyran-4-yl)-1H-pyrazolo[3,4-d]pyrimidine-6-carbonitrile (100 mg, 35%) as a yellow solid, used as is in the next step.

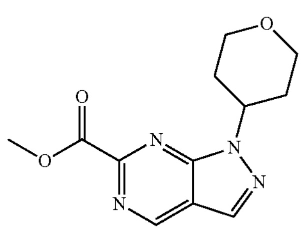 [SMILES: COC(=O)c1ncc2cnn(C3CCOCC3)c2n1]

Step 3: methyl 1-(tetrahydro-2H-pyran-4-yl)-1H-pyrazolo[3,4-d]pyrimidine-6-carboxylate A solution of 1-(tetrahydro-2H-pyran-4-yl)-1H-pyrazolo [3,4-d]pyrimidine-6-carbonitrile (100 mg, 0.44 mmol) in methanol (5 mL) was added HCl (4N in methanol, 1.5 mL). The mixture was stirred at 20° C. for 20 h and 50° C. for 3 h. The reaction solution was concentrated under reduced pressure to give crude methyl 1-(tetrahydro-2H-pyran-4-yl)-1H-pyrazolo[3,4-d]pyrimidine-6-carboxylate (100 mg, 87%) as a yellow solid. LCMS $R_T$=0.930 min; m/z=263.2 $(M+H)^+$.

LCMS (0 to 60% acetonitrile in water+0.03% trifluoacetic acid over 2.0 mins) retention time 0.930 min, ESI+ found [M+H]=263.2.

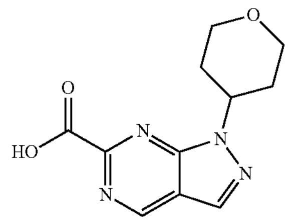 [SMILES: O=C(O)c1ncc2cnn(C3CCOCC3)c2n1]

Step 4: 1-(tetrahydro-2H-pyran-4-yl)-1H-pyrazolo [3,4-d]pyrimidine-6-carboxylic acid A mixture of methyl 1-(tetrahydro-2H-pyran-4-yl)-1H-pyrazolo[3,4-d]pyrimidine-6-carboxylate (100 mg, 0.38 mmol) and lithium hydroxide hydrate (80 mg, 1.91 mmol) in tetrahydrofuran (5 mL) and water (1 mL) was stirred at 25° C. for 2 h. The organic solvent was evaporated under reduced pressure and the aqueous phase was adjusted to pH=4 by addition of 2N HCl. The mixture was extracted with ethyl acetate (3×20 mL). The combined organic layers were dried with magnesium sulfate and concentrated under reduced pressure to give crude 1-(tetrahydro-2H-pyran-4-yl)-1H-pyrazolo[3,4-d]pyrimidine-6-carboxylic acid (60 mg, 63%) as a yellow solid. LCMS $R_T$=0.788 min; m/z=249.2 $(M+H)^+$.

LCMS (0 to 60% acetonitrile in water+0.03% trifluoacetic acid over 2.0 mins) retention time 0.788 min, ESI+ found [M+H]=249.2.

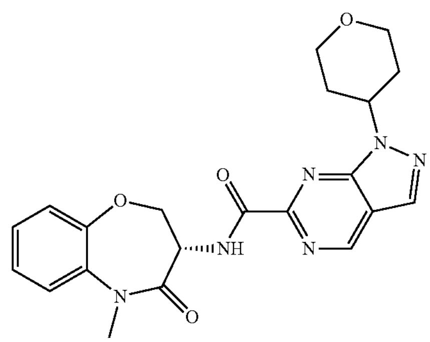 [SMILES: CN1C(=O)[C@@H](NC(=O)c2ncc3cnn(C4CCOCC4)c3n2)COc2ccccc21]

Step 5: N-[(3S)-5-methyl-4-oxo-2,3-dihydro-1,5-benzoxazepin-3-yl]-1-tetrahydropyran-4-yl-pyrazolo [3,4-d]pyrimidine-6-carboxamide A mixture of (3S)-3-amino-5-methyl-2,3-dihydro-1,5-benzoxazepin-4-one (33 mg, 0.17 mmol), 1-tetrahydropyran-4-ylpyrazolo[3,4-d]pyrimidine-6-carboxylic acid (30 mg, 0.12 mmol), $N^1$-((ethylimino)methylene)-$N^3$,$N^3$-dimethylpropane-1,3-diamine hydrochloride (36 mg, 0.19 mmol), 1H-benzo[d][1,2,3]triazol-1-ol (25 mg, 0.19 mmol) in N,N-dimethylformamide (3 mL) was stirred at 25° C. for 16 h. The mixture was concentrated under reduced pressure and the residue was purified by RP-HPLC (acetonitrile 20% to 50%/0.05% ammonia hydroxide in water) to give N-[(3S)-5-methyl-4-oxo-2,3-dihydro-1,5-benzoxazepin-3-yl]-1-tetrahydropyran-4-yl-pyrazol o[3,4-d]pyrimidine-6-carboxamide (37.61 mg, 73%) as a white solid. $^1$H NMR (400 MHz, DMSO-$d_6$) δ9.48 (s, 1H), 9.14 (d, J=6.4 Hz, 1H), 8.54 (s, 1H), 7.54-7.52 (m, 1H), 7.35-7.28 (m, 3H), 5.17-

5.10 (m, 1H), 4.90-4.79 (m, 1H), 4.62-4.50 (m, 2H), 4.03-4.00 (m, 2H), 3.62-3.56 (m, 2H), 3.34 (s, 3H), 2.24-2.15 (m, 2H), 1.94-1.91 (m, 2H). LCMS $R_T$=0.762 min; m/z=423.1 $(M+H)^+$.

LCMS (5-95% acetonitrile in water+0.05% trifluoacetic acid over 1.5 mins) retention time 0.762 min, ESI+ found [M+H]=423.1.

Example 559

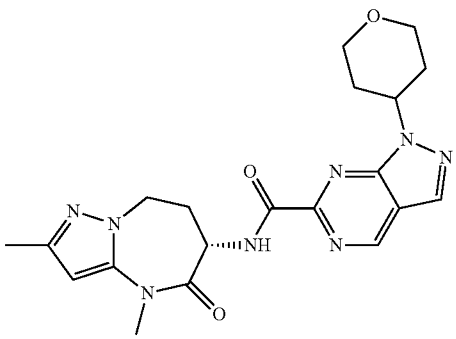 [SMILES: Cc1cc2n(n1)CC[C@H](NC(=O)c1ncc3cnn(C4CCOCC4)c3n1)C(=O)N2C]

N-[(6S)-2,4-dimethyl-5-oxo-7,8-dihydro-6H-pyrazolo[1,5-a][1,3]diazepin-6-yl]-1-tetrahydropyran-4-yl-pyrazolo[3,4-d]pyrimidine-6-carboxamide Amide coupling prepared in a similar fashion to WX Method 149. The crude was purified by RP-HPLC (acetonitrile 17% to 47%/0.05% ammonia hydroxide in water) to give N-[(6S)-2,4-dimethyl-5-oxo-7,8-dihydro-6H-pyrazolo[1,5-a][1,3]diazepin-6-yl]-1-tetrahydro pyran-4-yl-pyrazolo[3,4-d]pyrimidine-6-carboxamide (38.5 mg, 74%) as a white solid. $^1$H NMR (400 MHz, DMSO-d6) δ9.47 (s, 1H), 9.16 (d, J=8.0 Hz, 1H), 8.53 (s, 1H), 6.16 (s, 1H), 5.19-5.15 (m, 1H), 4.43-4.40 (m, 1H), 4.29-4.25 (m, 1H), 4.21-4.11 (m, 1H), 4.04-3.99 (m, 2H), 3.63-3.56 (m, 2H), 3.25 (s, 3H), 2.74-2.69 (m, 1H), 2.50-2.49 (m, 1H), 2.22-2.18 (m, 5H), 1.94-1.91 (m, 2H). LCMS $R_T$=0.705 min; m/z=425.1 $(M+H)^+$.

LCMS (5 to 95% acetonitrile in water+0.03% trifluoacetic acid over 1.5 mins) retention time 0.792 min, ESI+ found [M+H]=425.1.

Example 560

WX Method 057

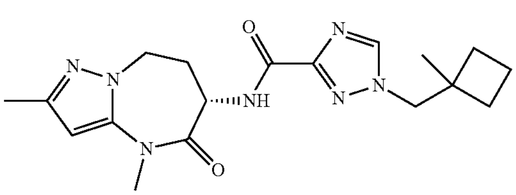 [SMILES: Cc1cc2n(n1)CC[C@H](NC(=O)c1ncn(CC3(C)CCC3)n1)C(=O)N2C]

1-[(1-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide

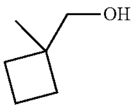

Step 1: (1-methylcyclobutyl)methanol

To a solution of 1-methylcyclobutanecarboxylic acid (300 mg, 2.63 mmol) in tetrahydrofuran (10 mL) was added $LiAlH_4$ (249 mg, 6.57 mmol) at 0° C. The reaction mixture was stirred at 25° C. for 16 h and then quenched by addition of water (1.0 mL) and 15% aqueous sodium hydroxide (0.3 mL). The reaction mixture was filtered and the filtrate was concentrated under reduced pressure to afford crude (1-methylcyclobutyl)methanol (260 mg, 99%) as colorless oil, used as is in the next step.

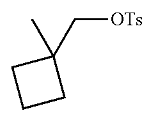 [SMILES: Cc1ccc(S(=O)(=O)OCC2(C)CCC2)cc1]

Step 2: (1-methylcyclobutyl)methyl 4-methylbenzenesulfonate

To a solution of 4-dimethylaminopyridine (634 mg, 5.19 mmol) in dichloromethane (10 mL) was added p-toluenesulfonylchloride (594 mg, 3.12 mmol) and (1-methylcyclobutyl)methanol (260 mg, 2.60 mmol). The reaction mixture was stirred at 20° C. for 16 h and then quenched by addition of water (10 mL). The mixture was extracted with ethyl acetate (3×20 mL). The combined organic layers were washed with water (10 mL), brine (10 mL), dried over anhydrous sodium sulfate and concentrated under reduced pressure. The residue was purified by column chromatography (silica gel, 100-200 mesh, 0 to 10% ethyl acetate in petroleum ether) to afford (1-methylcyclobutyl)methyl 4-methylbenzenesulfonate (500 mg, 76%) as colorless oil, used as is in the next step.

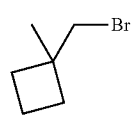

Step 3: 1-(bromomethyl)-1-methylcyclobutane

A mixture of lithium bromide thium (598 mg, 6.88 mmol) and (1-methylcyclobutyl)methyl 4-methylbenzenesulfonate (350 mg, 1.38 mmol) in acetone (15 mL) was heated to 70° C. for 4 h. After cooled, the mixture was diluted with water (20 mL) and extracted with ethyl acetate (3×20 mL). The combined organic layers were washed with water (10 mL), brine (10 ml), dried over anhydrous sodium sulfate and concentrated under reduced pressure to give crude 1-(bromomethyl)-1-methyl-cyclobutane (120 mg, 54%) as yellow oil, used as is in the next step.

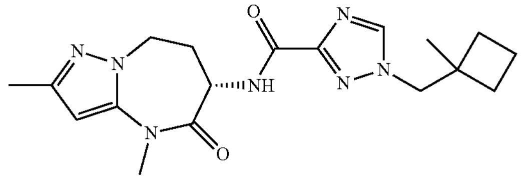 [SMILES: Cc1cc2n(n1)CC[C@H](NC(=O)c1ncn(CC3(C)CCC3)n1)C(=O)N2C]

Step 4: 1-[(1-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide A mixture of N-[(6S)-2,4-dimethyl-5-oxo-7,8-dihydro-6H-pyrazolo[1,5-a][1,3]diazepin-6-yl]-1H-1,2,4-triazole-3-carboxamide (30 mg, 0.10 mmol), 1-(bromomethyl)-1-methyl-cyclobutane (25 mg, 0.16 mmol) and potassium carbonate (43 mg, 0.31 mmol) in N,N-dimethylformamide (5 mL) was stirred at 20° C. for 16 h. The mixture was concentrated under reduced pressure and the residue was purified by RP-HPLC (acetonitrile 30-60%/0.05% ammonium hydroxide in water) to afford 1-[(1-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide (7.5 mg, 13%) as a white solid. $^1$H NMR (400 MHz, $CD_3OD$) δ8.47 (s, 1H), 6.12 (s, 1H), 4.57-4.52 (m, 1H), 4.35-4.23 (m, 4H), 3.34 (s, 3H), 2.91-2.87 (m, 1H), 2.29-2.26 (m, 4H), 2.13-2.08 (m, 2H), 1.96-1.92 (m, 1H), 1.87-1.83 (m, 1H), 1.77-1.72 (m, 2H), 1.10 (s, 3H). LCMS $R_T$=0.637 min; m/z=372.0 $(M+H)^+$.

LCMS (5 to 95% acetonitrile in water+0.03% trifluoacetic acid over 1.5 mins) retention time 0.637 min, ESI+ found [M+H]=372.0.

Example 561

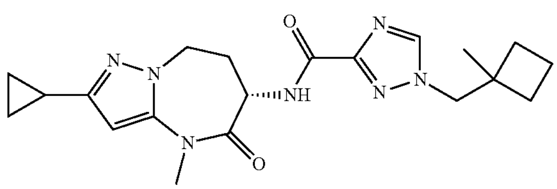 [SMILES: CN1C(=O)[C@@H](NC(=O)c2ncn(CC3(C)CCC3)n2)CCn2nc(C3CC3)cc21]

1-[(1-methylcyclobutyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide N-Alkylation prepared in a similar fashion to WX Method 057. The crude was purified by RP-HPLC (acetonitrile 30-60%/0.05% ammonium hydroxide in water) to give 1-[(1-methylcyclobutyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide (12 mg, 17%) as a white solid. $^1$H NMR (400 MHz, $CD_3OD$) δ8.49 (s, 1H), 6.01 (s, 1H), 4.56-4.51 (m, 1H), 4.32-4.21 (m, 4H), 3.32 (s, 3H), 2.89-2.83 (m, 1H), 2.28-2.24 (m, 1H), 2.12-2.08 (m, 2H), 1.95-1.90 (m, 3H), 1.77-1.73 (m, 2H), 1.10 (s, 3H), 0.95-0.93 (m, 2H), 0.74-0.72 (m, 2H). LCMS $R_T$=0.727 min; m/z=398.0 $(M+H)^+$.

LCMS (5 to 95% acetonitrile in water+0.03% trifluoacetic acid over 1.5 mins) retention time 0.727 min, ESI+ found [M+H]=398.0.

Example 562

WX Method 136

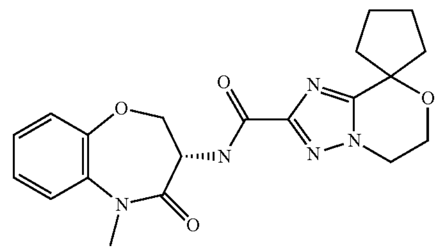 [SMILES: CN1C(=O)[C@@H](NC(=O)c2nc3n(n2)CCOC32CCCC2)COc2ccccc21]

N-[(3S)-5-methyl-4-oxo-2,3-dihydro-1,5-benzoxazepin-3-yl]spiro[5,6-dihydro-[1,2,4]triazolo[5,1-c][1,4]oxazine-8,1'-cyclopentane]-2-carboxamide

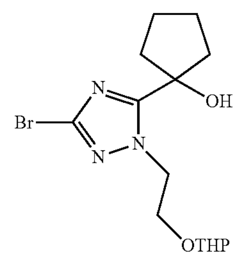

Step 1: 1-[5-bromo-2-(2-tetrahydropyran-2-yloxyethyl)-1,2,4-triazol-3-yl]cyclopentanol To a solution of 3,5-dibromo-1-(2-tetrahydropyran-2-yloxyethyl)-1,2,4-triazole (2 g, 5.6 mmol) in tetrahydrofuran (10 mL) was added n-butyllithium (2.5 M in hexanes, 2.6 mL, 6.5 mmol) at −78° C. The mixture was stirred at −78° C. for 1 h then a solution of cyclopentanone (1.2 g, 14.3 mmol) in tetrahydrofuran (2 mL) was added dropwise. After addition, the reaction mixture was stirred at −78° C. for 1 h and quenched by addition of saturated ammonium chloride (10 mL). The mixture was extracted with ethyl acetate (2×50 mL). The combined organic layers were washed with brine (2×20 mL), dried over sodium sulfate and concentrated under reduced pressure. The residue was purified by column chromatography (silica gel, 100-200 mesh, 0 to 100% ethyl acetate in petroleum ether) to afford 1-[5-bromo-2-(2-tetrahydropyran-2-yloxyethyl)-1,2,4-triazol-3-yl]cyclopentanol (1.5 g, 72%) as a colorless oil. LCMS $R_T$=0.790 min, m/z=361.8 $(M+H)^+$.

LCMS (5 to 95% acetonitrile in water+0.03% trifluoacetic acid over 1.5 mins) retention time 0.790 min, ESI+ found [M+H]=361.8

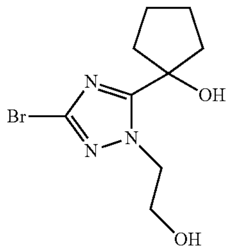 [SMILES: OCCn1nc(Br)nc1C1(O)CCCC1]

Step 2: 1-[5-bromo-2-(2-hydroxyethyl)-1,2,4-triazol-3-yl]cyclopentanol

To a solution of 1-[5-bromo-2-(2-tetrahydropyran-2-yloxyethyl)-1,2,4-triazol-3-yl]cyclopentanol (200 mg, 0.56 mmol) in methanol (10 mL) was added p-toluenesulfonic acid (191 mg, 1.11 mmol). The mixture was stirred at 20° C. for 2 h and concentrated under reduced pressure to afford crude 1-[5-bromo-2-(2-hydroxyethyl)-1,2,4-triazol-3-yl]cyclopentanol (250 mg, 110%) as a colorless oil. LCMS $R_T$=0.423 min, m/z=275.9 (M+H)$^+$.

LCMS (5 to 95% acetonitrile in water+0.03% trifluoacetic acid over 1.5 mins) retention time 0.423 min, ESI+ found [M+H]=275.9

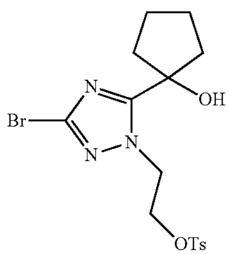 [SMILES: Cc1ccc(S(=O)(=O)OCCn2nc(Br)nc2C2(O)CCCC2)cc1]

Step 3: 2-[3-bromo-5-(1-hydroxycyclopentyl)-1,2,4-triazol-1-yl]ethyl 4-methyl benzenesulfonate A mixture of 1-[5-bromo-2-(2-hydroxyethyl)-1,2,4-triazol-3-yl]cyclopentanol (250 mg, 0.91 mmol), 4-dimethylaminopyridine(11 mg, 0.09 mmol), trimethylamine (0.63 mL, 4.53 mmol) and p-toluenesulfonyl chloride (190 mg, 1 mmol) in dichloromethane (5 mL) was stirred at 19° C. for 4 h. The mixture concentrated under reduced pressure and the residue was purified by preparative TLC (ethyl acetate: petroleum ether=1:3, $R_f$=0.6) to give 2-[3-bromo-5-(1-hydroxycyclopentyl)-1,2,4-triazol-1-yl]ethyl4-methylbenzenesulfonate (180 mg, 46%) as colorless oil, used as is in the next step.

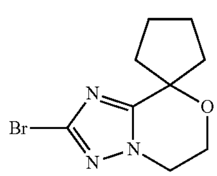 [SMILES: Brc1nc2n(n1)CCOC21CCCC1]

Step 4: 2-bromospiro[5,6-dihydro-[1,2,4]triazolo[5,1-c][1,4]oxazine-8,1'-cyclopentane]

To a solution of 2-[3-bromo-5-(1-hydroxycyclopentyl)-1,2,4-triazol-1-yl]ethyl 4-methylbenzenesulfonate (180 mg, 0.420 mmol) in tetrahydrofuran (40 mL) was added lithium bis(trimethylsilyl)amide (1.0 N in tetrahedron, 0.84 mL, 0.84 mmol) at −70° C. The mixture was stirred at −70° C. for 1 h and then allowed to warm to 20° C. over 12 h. The reaction mixture was quenched by addition of water (5 mL) and extracted with ethyl acetate (3×30 mL). The combined organic layers were washed with brine (3×10 mL), dried over sodium sulfate and concentrated under reduced pressure. The residue was purified by preparative TLC (33% ethyl acetate in petroleum ether, $R_f$=0.5) to afford 2-bromospiro[5,6-dihydro-[1,2,4]triazolo[5,1-c][1,4]oxazine-8,1'-cyclopentane] (70 mg, 65%) as a yellow solid. LCMS $R_T$=0.646 min, m/z=257.7 (M+H)$^+$.

LCMS (5 to 95% acetonitrile in water+0.03% trifluoacetic acid over 1.5 mins) retention time 0.646 min, ESI+ found [M+H]=257.7

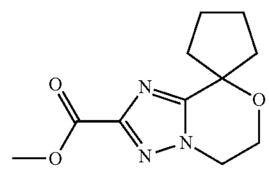 [SMILES: COC(=O)c1nc2n(n1)CCOC21CCCC1]

Step 5: ethyl spiro[5,6-dihydro-[1,2,4]triazolo[5,1-c][1,4]oxazine-8,1'-cyclopentane]-2-carboxylate A mixture of 2-bromospiro[5,6-dihydro-[1,2,4]triazolo[5,1-c][1,4]oxazine-8, 1,1'-cyclopentane](60 mg, 0.23 mmol), 1,1'-bis(diphenylphosphino)ferrocene palladium dichloride (17 mg, 0.02 mmol) and triethylamine (0.26 mL, 2.32 mmol) in methanol (20 mL) was heated at 70° C. under CO (35 psi) for 20 h and filtered. The filtrate was concentrated under reduced pressure and the residue was purified by preparative TLC (ethyl acetate: petroleum ether=1:2, $R_f$=0.3) to afford methyl spiro[5,6-dihydro-[1,2,4]triazolo[5,1-c][1,4]oxazine-8,1'-cyclopentane]-2-carboxylate (52 mg, 89%) as a yellow oil. $^1$H NMR (400 MHz, $CD_3OD$) δ4.30-4.25 (m, 2H), 4.16-4.10 (m, 2H), 3.94 (s, 3H), 2.19-2.07 (m, 4H) 1.95-1.84 (m, 4H). LCMS $R_T$=0.602 min, m/z=237.8 (M+H)$^+$.

LCMS (5 to 95% acetonitrile in water+0.03% trifluoacetic acid over 3 mins) retention time 0.602 min, ESI+ found [M+H]=237.8

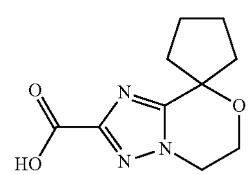 [SMILES: O=C(O)c1nc2n(n1)CCOC21CCCC1]

Step 6: spiro[5,6-dihydro-[1,2,4]triazolo[5,1-c][1,4]oxazine-8,1'-cyclopentane]-2-carboxylic acid A mixture of methyl spiro[5,6-dihydro-[1,2,4]triazolo[5,1-c][1,4]oxazine-8,1'-cyclopentane]-2-carboxylate (52 mg, 0.22 mmol) and lithium hydroxide (16 mg, 0.66 mmol) in tetrahydrofuran (4 mL) and water (1 mL) was stirred at 18° C. for 2 h. The mixture was adjusted to pH=3 by addition of 1N HCl. The mixture was concentrated under reduced pressure to give crude spiro[5,6-dihydro-[1,2,4]triazolo[5,1-c][1,4]oxazine-8, 1'-cyclopentane]-2-carboxylic acid (48 mg, 98%) as a colorless oil. LCMS $R_T$=0.514 min, m/z=223.8 $(M+H)^+$.

LCMS (5 to 95% acetonitrile in water+0.03% trifluoacetic acid over 1.5 mins) retention time 0.514 min, ESI+ found [M+H]=223.8

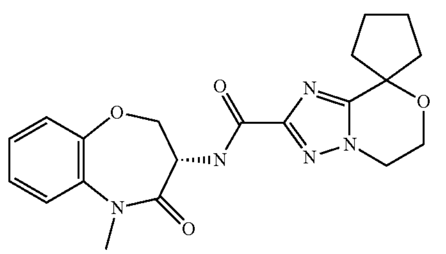 [SMILES: CN1C(=O)[C@@H](NC(=O)c2nc3n(n2)CCOC32CCCC2)COc2ccccc21]

Step 7: N-[(3S)-5-methyl-4-oxo-2,3-dihydro-1,5-benzoxazepin-3-yl]spiro[5,6-dihydro-[1,2,4]triazolo[5,1-c][1,4]oxazine-8,1'-cyclopentane]-2-carboxamide A mixture of spiro[5,6-dihydro-[1,2,4]triazolo[5,1-c][1,4]oxazine-8,1'-cyclopentane]-2-carboxylic acid (24 mg, 0.11 mmol), 1-(3-dimethylaminopropyl)-3-ethylcarbodiimidehydrochloride (33 mg, 0.22 mmol), (3S)-3-amino-5-methyl-2,3-dihydro-1,5-benzoxazepin-4-one (21 mg, 0.11 mmol) and 1-hydroxybenzotriazole (29 mg, 0.22 mmol) in N,N-dimethylformamide (2 mL) was stirred at 20° C. for 12 h. The mixture was concentrated under reduced pressure and the residue was purified by RP-HPLC (40% to 70% acetonitrile/0.05% ammonia hydroxide in water) to afford N-[(3S)-5-methyl-4-oxo-2,3-dihydro-1,5-benzoxazepin-3-yl]spiro[5,6-dihydro-[1,2,4]triazolo[5,1-c][1,4]oxazine-8,1'-cyclopentane]-2-carboxamide (24.2 mg, 57%) as a white solid. $^1$H NMR (400 MHz, $CD_3OD$) δ7.45-7.42 (m, 1H), 7.32-7.30 (m, 2H), 7.25-7.23 (m, 1H), 5.02-5.00 (m, 1H), 4.62-4.58 (m, 1H), 4.45-4.41 (m, 1H), 4.27-4.25 (m, 2H), 4.13-4.11 (m, 2H), 3.42 (s, 3H), 2.16-2.14 (m, 4H), 1.91-1.90 (m, 4H). LCMS $R_T$=0.807 min, m/z=398.1 $(M+H)^+$.

LCMS (5 to 95% acetonitrile in water+0.03% trifluoacetic acid over 1.5 mins) retention time 0.807 min, ESI+ found [M+H]=398.1

Example 563

WX Method 146

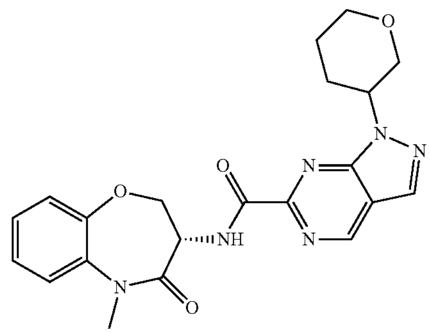 [SMILES: CN1C(=O)[C@@H](NC(=O)c2ncc3cnn(C4CCCOC4)c3n2)COc2ccccc21]

N-[(3S)-5-methyl-4-oxo-2,3-dihydro-1,5-benzoxazepin-3-yl]-1-tetrahydropyran-3-yl-pyrazolo[3,4-d]pyrimidine-6-carboxamide

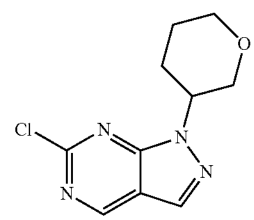 [SMILES: Clc1ncc2cnn(C3CCCOC3)c2n1]

Step 1: 6-chloro-1-(tetrahydro-2H-pyran-3-yl)-1H-pyrazolo[3,4-d]pyrimidine

To a solution of 6-chloro-1H-pyrazolo[3,4-d]pyrimidine (1.0 g, 6.47 mmol), triphenylphosphine (2.5 g, 9.7 mmol) and tetrahydro-2h-pyran-3-ol (661 mg, 6.47 mmol) in tetrahydrofuran (5 ml) was added diisopropyl azodicarboxylate (1.9 g, 9.7 mmol). The mixture was stirred at 25° C. for 16 h and concentrated under reduced pressure. The residue was diluted with ethyl acetate (100 mL), washed with water (100 mL), brine (100 mL), dried over magnesium sulfate and concentration under reduced pressure. The residue was purified by column chromatography (silica gel, 100-200 mesh, 0 to 30% ethyl acetate in petroleum ether) to give 6-chloro-1-(tetrahydro-2H-pyran-3-yl)-1H-pyrazolo[3,4-d]pyrimidine (1.5 g, 97%) as a white solid. LCMS $R_T$=1.07 min, m/z=239.2 $[M+H]^+$.

LCMS (0 to 60% acetonitrile in water+0.03% trifluoacetic acid over 2 mins) retention time 1.07 min, ESI+ found [M+H]=239.2.

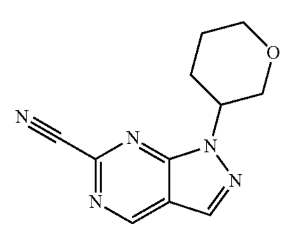 [SMILES: N#Cc1ncc2cnn(C3CCCOC3)c2n1]

Step 2: 1-(tetrahydro-2H-pyran-3-yl)-1H-pyrazolo[3,4-d]pyrimidine-6-carbonitrile To a solution of 6-chloro-1-(tetrahydro-2H-pyran-3-yl)-1H-pyrazolo[3,4-d]pyrimidine (500 mg, 2.09 mmol) in dimethyl sulfoxide (20 mL) was added sodium cyanide (205 mg, 4.19 mmol) in water (10 mL). The mixture was heated at 40° C. for 3 h and diluted with water (100 mL). The solution was extracted with ethyl acetate (3×50 mL). The combined organic layers were washed brine (50 mL), dried over magnesium sulfate and concentration under reduced pressure. The residue was purified by column chromatography (silica gel, 100-200 mesh, 0 to 30% ethyl acetate in petroleum ether) to give 1-(tetrahydro-2H-pyran-3-yl)-1H-pyrazolo[3,4-d]pyrimidine-6-carbonitrile (120 mg, 25%) as a yellow oil, used as is in the next step.

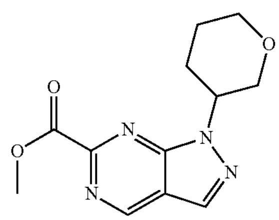 [SMILES: COC(=O)c1ncc2cnn(C3CCCOC3)c2n1]

Step 3: methyl 1-(tetrahydro-2H-pyran-3-yl)-1H-pyrazolo[3,4-d]pyrimidine-6-carboxylate A solution of 1-(tetrahydro-2H-pyran-3-yl)-1H-pyrazolo[3,4-d]pyrimidine-6-carbonitrile (120 mg, 0.52 mmol) in methanol (10 mL) was added HCl (4N in methanol, 3 mL). The mixture was stirred at 50° C. for 24 h and concentrated under reduced pressure to give methyl 1-(tetrahydro-2H-pyran-3-yl)-1H-pyrazolo[3,4-d]pyrimidine-6-carboxylate (110 mg, 80%) as a yellow solid. LCMS $R_T$=0.97 min, m/z=263.3 $[M+H]^+$.

LCMS (0 to 60% acetonitrile in water+0.03% trifluoacetic acid over 2 mins) retention time 0.97 min, ESI+ found [M+H]=263.3.

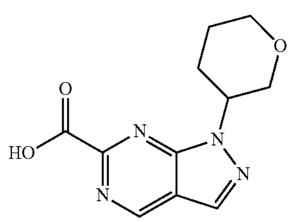 [SMILES: O=C(O)c1ncc2cnn(C3CCCOC3)c2n1]

Step 4: 1-(tetrahydro-2H-pyran-3-yl)-1H-pyrazolo[3,4-d]pyrimidine-6-carboxylic acid A mixture of methyl 1-(tetrahydro-2H-pyran-3-yl)-1H-pyrazolo[3,4-d]pyrimidine-6-carboxylate (100 mg, 0.38 mmol) and lithium hydroxide (46 mg, 1.91 mmol) in tetrahydrofuran (5 mL) and water (5 mL) was stirred at 25° C. for 4 h. The organic solvent was removed under reduced pressure and the aqueous residue was adjusted to pH=2 by addition of 1N HCl. The mixture was extracted with ethyl acetate (2×20 mL). The combined organics were concentrated under reduced pressure to give crude 1-(tetrahydro- 2H-pyran-3-yl)-1H-pyrazolo[3,4-d]pyrimidine-6-carboxylic acid (70 mg, 74%) as a white solid, used as is in the next step. LCMS $R_T$=0.85 min, m/z=249.2 $[M+H]^+$.

LCMS (0 to 60% acetonitrile in water+0.03% trifluoacetic acid over 2 mins) retention time 0.85 min, ESI+ found [M+H]=249.2.

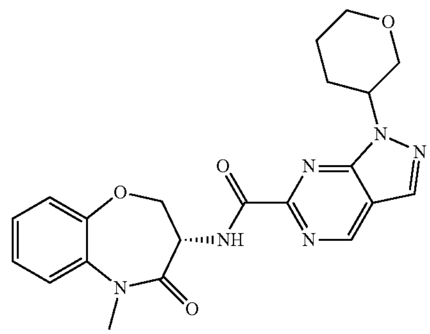 [SMILES: CN1C(=O)[C@@H](NC(=O)c2ncc3cnn(C4CCCOC4)c3n2)COc2ccccc21]

Step 5: N-[(3S)-5-methyl-4-oxo-2,3-dihydro-1,5-benzoxazepin-3-yl]-1-tetrahydropyran-3-yl-pyrazolo[3,4-d]pyrimidine-6-carboxamide A mixture of (3S)-3-amino-5-methyl-2,3-dihydro-1,5-benzoxazepin-4-one (23 mg, 0.12 mmol), 1-tetrahydropyran-3-ylpyrazolo[3,4-d]pyrimidine-6-carboxylic acid (30 mg, 0.12 mmol), $N^1$-((ethylimino)methylene)-$N^3$,$N^3$-dimethylpropane-1,3-diamine hydrochloride (35 mg, 0.18 mmol), 1H-benzo[d][1,2,3]triazol-1-ol (25 mg, 0.19 mmol) in N,N-dimethylformamide (3 mL) was stirred at 25° C. for 16 h. The mixture was concentrated under reduced pressure and the residue was purified by RP-HPLC (acetonitrile 50% to 80%/0.05% ammonia hydroxide in water) to give N-[(3S)-5-methyl-4-oxo-2,3-dihydro-1,5-benzoxazepin-3-yl]-1-tetrahydropyran-3-yl-pyrazol o[3,4-d]pyrimidine-6-carboxamide (14.0 mg, 27%) as a white solid. $^1$H NMR (400 MHz, $CD_3OD$) δ 9.36 (s, 1H), 8.38 (s, 1H), 7.47-7.44 (m, 1H), 7.34-7.27 (m, 3H), 5.17-5.11 (m, 2H), 4.75-4.65 (m, 1H), 4.58-4.40 (m, 1H), 4.15-3.85 (m, 3H), 3.65-3.53 (m, 1H), 3.45 (s, 3H), 2.40-2.33 (m, 1H), 2.25-2.21 (m, 1H), 1.98-1.91 (m, 2H). LCMS $R_T$=0.70 min, m/z=423.0 $[M+H]^+$.

LCMS (5 to 95% acetonitrile in water+0.03% trifluoacetic acid over 1.5 mins) retention time 0.70 min, ESI+ found [M+H]=423.0.

Example 564

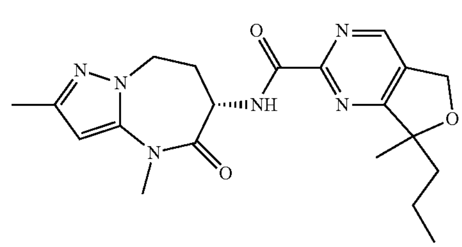 [SMILES: CCCC1(C)OCc2cnc(C(=O)N[C@H]3CCn4nc(C)cc4N(C)C3=O)nc21]

7-methyl-7-propyl-N-[(6S)-2,4-dimethyl-5-oxo-7,8-dihydro-6H-pyrazolo[1,5-a][1,3]diazepin-6-yl]-5H-furo[3,4-d]pyrimidine-2-carboxamide Amide coupling prepared in a similar fashion to WX Method N. The crude was purified by RP-HPLC (acetonitrile 26% to 56%/0.05% ammonia hydroxide in water) 7-methyl-7-propyl-N-[(6S)-2,4-dimethyl-5-oxo-7,8-dihydro-6H-pyrazolo[1,5-a][1,3]diazepin-6-yl]-5H-furo[3,4-d]pyrimidine-2-carboxamide (43 mg, 41%) as a white solid. $^1$H NMR (400 MHz, $CD_3OD$) δ8.82 (s, 1H), 6.13 (s, 1H), 5.20-5.12 (m, 2H), 4.62-4.55 (m, 1H), 4.37-4.21 (m, 2H), 3.36 (s, 3H), 3.00-2.90 (m, 1H), 2.31-2.25 (m, 4H), 1.95-1.79 (m, 2H), 1.49-1.40 (m, 4H), 1.08-0.95 (m, 1H), 0.87 (t, J=6.8 Hz, 3H). LC-MS $R_T$=1.546 min, m/z=395.2 $[M+H]^+$.

LCMS (10 to 80% acetonitrile in water+0.03% ammonium hydroxide over 3.0 mins) retention time 1.546 min, ESI+ found [M+H]=395.2.

Example 565

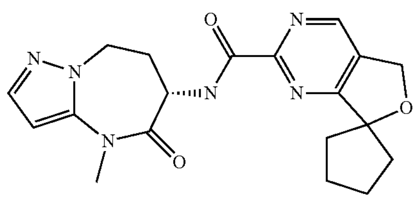 [SMILES: CN1C(=O)[C@@H](NC(=O)c2ncc3c(n2)C2(CCCC2)OC3)CCn2nccc21]

N-[(6S)-4-methyl-5-oxo-7,8-dihydro-6H-pyrazolo[1,5-a][1,3]diazepin-6-yl]spiro[5H-furo [3,4-d]pyrimidine-7,1'-cyclopentane]-2-carboxamide Amide coupling prepared in a similar fashion to WX Method 136. The crude was purified by RP-HPLC (17% to 47% acetonitrile/0.05% ammonia hydroxide in water) to give N-[(6S)-4-methyl-5-oxo-7,8-dihydro-6H-pyrazolo[1,5-a][1,3]diazepin-6-yl]spiro[5H-furo[3,4-d]pyrimidine-7,1'-cyclopentane]-2-carboxamide (35.6 mg, 41%) as a white solid. $^1$H NMR (400 MHz, $CD_3OD$) δ8.79 (s, 1H), 7.54 (s, 1H), 6.32 (s, 1H), 5.11 (s, 2H), 4.59-4.57 (m, 1H), 4.55-4.43 (m, 1H), 4.33-4.31 (m, 1H), 3.38 (s, 3H), 3.00-2.95 (m, 1H), 2.33-2.28 (m, 1H), 2.07-2.03 (m, 4H), 1.94-1.92 (m, 4H). LC-MS $R_T$=0.720 min, m/z=383.1 [M+H].

LCMS (5 to 95% acetonitrile in water+0.03% trifluoacetic acid over 1.5 mins) retention time 0.720 min, ESI+ found [M+H]=383.1.

Example 566

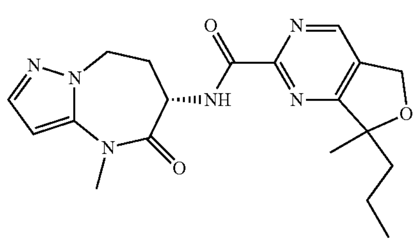 [SMILES: CCCC1(C)OCc2cnc(C(=O)N[C@H]3CCn4nccc4N(C)C3=O)nc21]

7-methyl-7-propyl-N-[(6S)-4-methyl-5-oxo-7,8-dihydro-6H-pyrazolo[1,5-a][1,3]diazepin-6-yl]-5H-furo[3,4-d]pyrimidine-2-carboxamide Amide coupling prepared in a similar fashion to WX Method N. The crude was purified by RP-HPLC (19% to 49% acetonitrile/0.05% ammonia hydroxide in water) to afford 7-methyl-7-propyl-N-[(6S)-4-methyl-5-oxo-7,8-dihydro-6H-pyrazolo[1,5-a][1,3]diazepin-6-yl]-5H-furo[3,4-d]pyrimidine-2-carboxamide (32.6 mg, 30%) as a white solid. $^1$H NMR (400 MHz, $CD_3OD$) δ8.82 (s, 1H), 7.55 (d, J=2.4 Hz, 1H), 6.33 (s, 1H), 5.20-5.12 (m, 2H), 4.60-4.55 (m, 1H), 4.49-4.43 (m, 1H), 4.36-4.28 (m, 1H), 3.39 (s, 3H), 3.03-2.92 (m, 1H), 2.35-2.28 (m, 1H), 1.96-1.79 (m, 2H), 1.49-1.40 (m, 4H), 1.08-0.95 (m, 1H), 0.87 (t, J=6.8 Hz, 3H). LC-MS $R_T$=1.473 min, m/z=385.2 $[M+H]^+$.

LCMS (10 to 80% acetonitrile in water+0.03% ammonium hydroxide over 3.0 mins) retention time 1.473 min, ESI+ found [M+H]=385.2.

Example 567

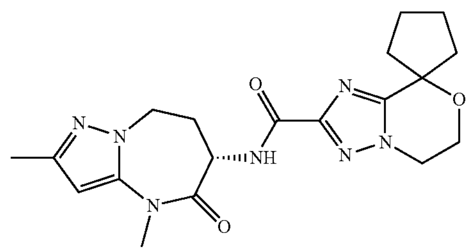 [SMILES: Cc1cc2n(n1)CC[C@H](NC(=O)c1nc3n(n1)CCOC31CCCC1)C(=O)N2C]

N-[(6S)-2,4-dimethyl-5-oxo-7,8-dihydro-6H-pyrazolo[1,5-a][1,3]diazepin-6-yl]spiro[5,6-dihydro-[1,2,4]triazolo[5,1-c][1,4]oxazine-8,1'-cyclopentane]-2-carboxamide Amide coupling prepared in a similar fashion to WX Method 136. The crude was purified by RP-HPLC (13% to 43% acetonitrile/0.05% ammonia hydroxide in water) to afford N-[(6S)-2,4-dimethyl-5-oxo-7,8-dihydro-6H-pyrazolo[1,5-a][1,3]diazepin-6-yl]spiro[5,6-dihydro-[1,2,4]triazolo[5,1-c][1,4]oxazine-8,1'-cyclopentane]-2-carboxamide (32.9 mg, 77%), as a colorless oil. $^1$H NMR (400 MHz, DMSO-$d_6$) δ8.46 (d, J=7.2 Hz, 1H), 6.13 (s, 1H), 4.40-4.20 (m, 4H), 4.16-4.03 (m, 3H), 3.22 (s, 3H), 2.63-2.54 (m, 1H), 2.39-2.30 (m, 1H), 2.17 (s, 3H), 2.11-1.96 (m, 4H), 1.87-1.43 (m, 4H). LCMS $R_T$=0.724 min, m/z=400.1 $(M+H)^+$.

LCMS (5 to 95% acetonitrile in water+0.03% trifluoacetic acid over 3 mins) retention time 0.724 min, ESI+ found [M+H]=400.1

Example 568

WX Method 118

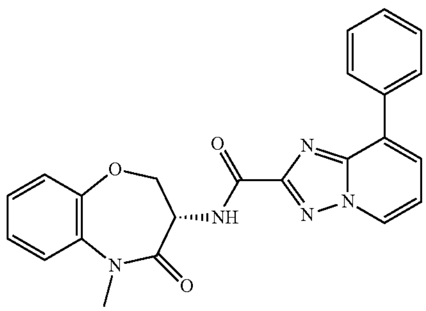 [SMILES: CN1C(=O)[C@@H](NC(=O)c2nc3c(-c4ccccc4)cccn3n2)COc2ccccc21]

8-phenyl-N-[(3S)-5-methyl-4-oxo-2,3-dihydro-1,5-benzoxazepin-3-yl]-[1,2,4]triazolo[1,5-a]pyridine-2-carboxamide

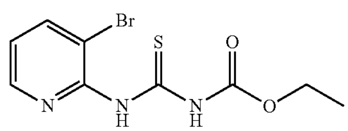 [SMILES: CCOC(=O)NC(=S)Nc1ncccc1Br]

Step 1: ethyl N-[(3-bromo-2-pyridyl)carbamothioyl]carbamate

To a solution of 3-bromo-2-pyridinamine (10.0 g, 57.8 mmol) in 1,4-dioxane (50 mL) was added ethoxycarbonyl isothiocyanate (9.1 g, 69.4 mmol). The reaction mixture was stirred at 25° C. for 12 h and then concentrated under reduced pressure. The resulting solid was triturated in ether, filtered and dried to give crude ethyl N-[(3-bromo-2-pyridyl)carbamothioyl]carbamate (10.6 g, 60%) as a pale yellow solid. LCMS $R_T$=0.728 min, m/z=305.7 $[M+H]^+$.

LCMS (5 to 95% acetonitrile in water+0.03% trifluoacetic acid over 1.5 mins) retention time 0.728 min, ESI+ found [M+H]=305.7

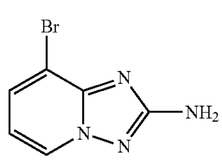 [SMILES: Nc1nc2c(Br)cccn2n1]

Step 2: 8-bromo-[1,2,4]triazolo[1,5-a]pyridin-2-amine

To a solution of N,N-diisopropylethylamine (13.51 g, 104.53 mmol) in methanol (300 mL) and ethanol (30 mL) was added hydroxylamine hydrochloride (12.11 g, 174.27 mmol). The mixture was stirred at 25° C. for 30 min and then ethyl N-[(3-bromo-2-pyridyl)carbamothioyl]carbamate (10.6 g, 34.85 mmol) was added. The resulting mixture was heated at 65° C. for 16 h and concentrated under reduced pressure. The residue was then dissolved in ethyl acetate (30 mL) and filtered. The filtrate was washed with water (30 mL), dried over sodium sulfate and concentrated to give crude 8-bromo-[1,2,4]triazolo[1,5-a]pyridin-2-amine (4.1 g, 55%) as a white solid, used as is in the next step.

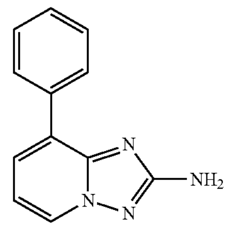 [SMILES: Nc1nc2c(-c3ccccc3)cccn2n1]

Step 3: 8-phenyl-[1,2,4]triazolo[1,5-a]pyridin-2-amine

A mixture of 8-bromo-[1,2,4]triazolo[1,5-a]pyridin-2-amine (4.1 g, 19.25 mmol), phenylboronic acid (3.52 g, 28.87 mmol), tetrakis(triphenylphosphine)palladium(0) (2.22 g, 1.92 mmol) and sodium bicarbonate (4.85 g, 57.73 mmol) in 1,4-dioxane (35 mL) and water (7 mL) was heated at 150° C. for 10 min under microwave conditions. The reaction mixture was concentrated under reduced pressure, diluted with ethyl acetate (300 mL) and filtered. The filtrate was dried over sodium sulfate and concentrated under reduced pressure. The residue was purified by column chromatography (silica gel, 100-200 mesh, 0 to 60% ethyl acetate in petroleum ether) to afford 8-phenyl-[1,2,4]triazolo[1,5-a]pyridin-2-amine (3.0 g, 74%) as a yellow solid, used as is in the next step. LCMS $R_T$=0.593 min, m/z=210.9 $[M+H]^+$.

LCMS (5 to 95% acetonitrile in water+0.03% trifluoacetic acid over 1.5 mins) retention time 0.593 min, ESI+ found [M+H]=210.9.

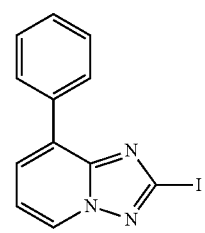 [SMILES: Ic1nc2c(-c3ccccc3)cccn2n1]

Step 4: 2-iodo-8-phenyl-[1,2,4]triazolo[1,5-a]pyridine

To a suspension of 8-phenyl-[1,2,4]triazolo[1,5-a]pyridin-2-amine (100 mg, 0.48 mmol) and p-toluenesulfonic acid monohydrate (343 mg, 1.81 mmol) in acetonitrile (8 mL) was added an solution of potassium iodide (261 mg, 1.57 mmol) and sodium nitrite (82 mg, 1.19 mmol) in water (2 mL) at 13° C. After addition, the reaction mixture was stirred at 13° C. for 10 hand then diluted with ethyl acetate (20 mL). The separated organic layer was washed with water (2×10 mL), brine (10 mL), dried over anhydrous sodium sulfate and concentrated under reduced pressure. The residue which was purified by column chromatography (silica gel, 100-200 mesh, 0-30% ethyl acetate in petroleum ether)

to afford 2-iodo-8-phenyl-[1,2,4]triazolo[1,5-a]pyridine (100 mg, 65%) as a yellow solid, used as is in the next step. LCMS $R_T$=0.845 min, m/z=321.8 $[M+H]^+$.

LCMS (5 to 95% acetonitrile in water+0.03% trifluoacetic acid over 1.5 mins) retention time 0.845 min, ESI+ found [M+H]=321.8

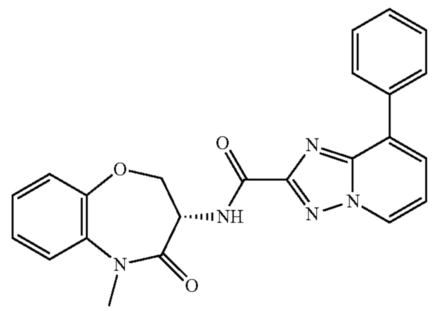 [SMILES: CN1C(=O)[C@@H](NC(=O)c2nc3c(-c4ccccc4)cccn3n2)COc2ccccc21]

Step: 5: 8-phenyl-N-[(3S)-5-methyl-4-oxo-2,3-dihydro-1,5-benzoxazepin-3-yl]-[1,2,4]triazolo[1,5-a]pyridine-2-carboxamide A mixture of 2-iodo-8-phenyl-[1,2,4]triazolo[1,5-a]pyridine (30 mg, 0.09 mmol), (3 s)-3-amino-5-methyl-2,3-dihydro-1,5-benzoxazepin-4-one (18 mg, 0.09 mmol), 4,5-bis(diphenylphosphino)-9,9-dimethylxanthene (8 mg, 0.01 mmol), triethylamine (61 mg, 0.61 mmol) and palladium diacetate (2 mg, 0.01 mmol) in toluene (2 mL) was heated at 80° C. under CO atmosphere (15 psi) for 5 h. The mixture was filtered and the filtrate was concentrated under reduced pressure. The residue was purified by RR-HPLC (40% to 70% acetonitrile/0.05% ammonia hydroxide in water) to give 8-phenyl-N-[(3S)-5-methyl-4-oxo-2,3-dihydro-1,5-benzoxazepin-3-yl]-[1,2,4]triazolo[1,5-a]pyridine-2-carboxamide (5.7 mg, 9%) as a white solid. $^1H$ NMR (400 MHz, $CD_3OD$) δ8.83-8.77 (m, 1H), 8.06 (d, J=7.2 Hz, 2H), 7.94-7.88 (m, 1H), 7.57-7.51 (m, 2H), 7.50-7.42 (m, 2H), 7.40-7.28 (m, 3H), 7.27-7.21 (m, 1H), 5.12-5.04 (m, 1H), 4.67-4.62 (m, 1H), 4.52-4.46 (m, 1H), 3.43 (s, 3H). LCMS $R_T$=0.851 min, m/z=414.1 $[M+H]^+$.

LCMS (5 to 95% acetonitrile in water+0.1% trifluoacetic acid over 1.5 mins) retention time 0.851 min, ESI+ found [M+H]=414.1

Example 569

WX Method 041

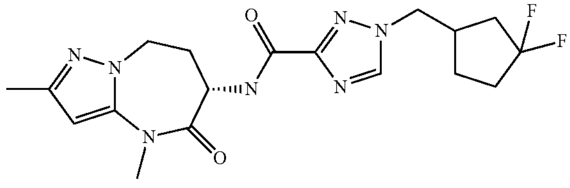 [SMILES: Cc1cc2n(n1)CC[C@H](NC(=O)c1ncn(CC3CCC(F)(F)C3)n1)C(=O)N2C]

1-[(3,3-difluorocyclopentyl)methyl]-N-(6S)-2,4-dimethyl-5-oxo-7,8-dihydro-6H-pyrazolo[1,5-a][1,3]diazepin-6-yl-1,2,4-triazole-3-carboxamide

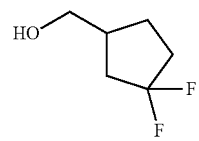

Step 1: (3,3-difluorocyclopentyl)methanol

To a mixture of $LiAlH_4$ (253 mg, 6.66 mmol) in tetrahydrofuran (10 mL) was added 3,3-difluorocyclopentanecarboxylic acid (500 mg, 3.33 mmol) in tetrahydrofuran (4 mL) at 0° C. the reaction mixture was stirred at 25° C. for 18 h and then quenched by addition of water (0.1 mL), 15% aqueous NaOH (0.1 mL) and water (0.3 mL). The resulting mixture was diluted with dichloromethane (20 mL), dried over anhydrous sodium sulfate and concentrated under reduced pressure to give crude (3,3-difluorocyclopentyl)methanol (320 mg, 71%) as a colorless oil, used as is in the next step.

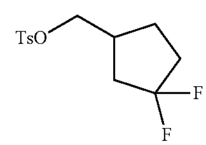 [SMILES: Cc1ccc(S(=O)(=O)OCC2CCC(F)(F)C2)cc1]

Step 2: (3,3-difluorocyclopentyl)methyl 4-methylbenzenesulfonate

To a solution of (3,3-difluorocyclopentyl)methanol (300 mg, 2.20 mmol) in dichloromethane (10 mL) was added 4-dimethylaminopyridine (323 mg, 2.64 mmol) and 4-methylbenzene-1-sulfonyl chloride (504 mg, 2.64 mmol) at 0° C. After addition, the reaction mixture was stirred at 25° C. for 18 h and quenched by addition of water (10 mL). The mixture was extracted with dichloromethane (2×20 ml). The combined organic layers were washed with water (2×20 mL), brine (20 mL), dried over anhydrous sodium sulfate and concentrated under reduced pressure. The residue was purified by column chromatography (silica gel, 100-200 mesh, 0 to 20% ethyl acetate in petroleum ether) to afford (3,3-difluorocyclopentyl)methyl 4-methylbenzenesulfonate (300 mg, 47%) as a colorless oil, used as is in the next step.

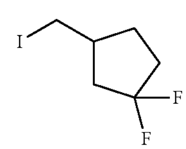

Step 3: 1,1-difluoro-3-(iodomethyl)cyclopentane

A mixture of (3,3-difluorocyclopentyl)methyl 4-methylbenzenesulfonate (100 mg, 0.34 mmol) and sodium iodide (154 mg, 1.03 mmol) in acetone (5 mL) was heated at 40°

C. for 18 h and concentrated under reduce pressure. The residue was diluted with ethyl acetate (30 mL) and washed with water (3×20 mL), brine (2×20 mL), dried over anhydrous sodium sulfate and concentrated to give crude 1,1-difluoro-3-(iodomethyl)cyclopentane (84 mg, 99%) as a 20-colorless oil, used as is in the next step.

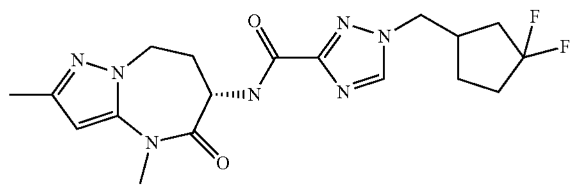 [SMILES: Cc1cc2n(n1)CC[C@H](NC(=O)c1ncn(CC3CCC(F)(F)C3)n1)C(=O)N2C]

Step 4: 1-[(3,3-difluorocyclopentyl)methyl]-N-(6S)-2,4-dimethyl-5-oxo-7,8-dihydro-6H-pyrazolo[1,5-a][1,3]diazepin-6-yl-1,2,4-triazole-3-carboxamide A mixture of 1,1-difluoro-3-(iodomethyl)cyclopentane (76 mg, 0.31 mmol), N-[(6S)-2,4-dimethyl-5-oxo-7,8-dihydro-6H-pyrazolo[1,5-a][1,3]diazepin-6-yl]-1H-1,2,4-triazole-3-carboxamide (45 mg, 0.16 mmol) and potassium carbonate (64 mg, 0.47 mmol) in N,N-dimethylformamide (5 mL) was stirred at 25° C. for 12 h. The reaction was concentrated under reduce pressure and the residue was purified by RP-HPLC (acetonitrile 0-40%/0.05% ammonium hydroxide in water) to afford 1-[(3,3-difluorocyclopentyl)methyl]-N-(6S)-2,4-dimethyl-5-oxo-7,8-dihydro-6H-pyrazolo[1, 5-a][1,3]diazepin-6-yl-1,2,4-triazole-3-carboxamide (14 mg, 22%) as a white solid. $^1$H NMR (400 MHz, $CD_3OD$) δ8.50 (s, 1H), 6.11 (s, 1H), 4.59-4.51 (m, 2H), 4.31-4.27 (m, 2H), 4.26-4.18 (m, 1H), 3.33 (s, 3H), 2.94-2.69 (m, 3H), 2.25 (s, 3H), 2.22-1.84 (m, 5H), 1.63-1.53 (m, 1H). LC-MS $R_T$=1.512 min, m/z=408.2 $(M+H)^+$.

LCMS (10 to 80% acetonitrile in water+0.03% ammonium bicarbonate over 3.0 mins) retention time 1.512 min, ESI+ found [M+H]=408.2.

Example 570

WX Method 083

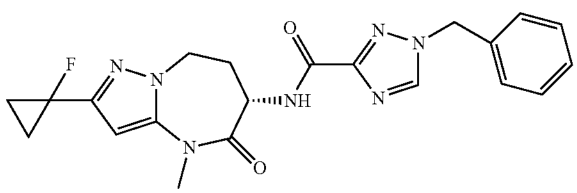 [SMILES: CN1C(=O)[C@@H](NC(=O)c2ncn(Cc3ccccc3)n2)CCn2nc(C3(F)CC3)cc21]

1-benzyl-N-(6S)-2-(1-fluorocyclopropyl)-4-methyl-5-oxo-7,8-dihydro-6H-pyrazolo[1,5-a][1,3]diazepin-6-yl-1,2,4-triazole-3-carboxamide

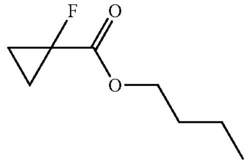

Step 1: butyl 1-fluorocyclopropanecarboxylate

A solution of 1-fluorocyclopropanecarboxylic acid (6.00 g, 57.65 mmol) in acetonitrile (60 mL) was added DBU (9.65 g, 63.41 mmol) and 1-iodobutane (11.67 g, 63.41 mmol) dropwise at 0° C. The resulting mixture was stirred at 25° C. for 12 h and quenched by addition of water (100 mL). The mixture was extracted with ethyl acetate (3×100 mL). The combined organic layers were dried over sodium sulfate and concentrated under reduced pressure to give crude butyl 1-fluorocyclopropanecarboxylate (7.5 g, 81%) as a yellow oil, used as is in the next step.

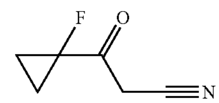

Step 2: 3-(1-fluorocyclopropyl)-3-oxopropanenitrile

To a solution of acetonitrile (3.0 mL, 51.5 mmol) in tetrahydrofuran (80 mL) was added n-butyllithium (2.5 M in hexane, 21.0 mL, 51.5 mmol) dropwise at −78° C. The resulting mixture was stirred at the same temperature for 30 minutes and butyl 1-fluorocyclopropanecarboxylate (7.5 g, 46.8 mmol) was added. After addition, the reaction mixture was stirred at room temperature for 2 h and then quenched by addition of saturated ammonium chloride (50 mL). The mixture was extracted with ethyl acetate (2×100 mL). The combined organic layers were dried over sodium sulfate and concentrated under reduced pressure to give crude 3-(1-fluorocyclopropyl)-3-oxopropanenitrile (3.7 g, 62%) as yellow oil, used as is in the next step.

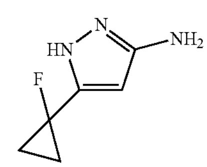

Step 3: 5-(1-fluorocyclopropyl)-1H-pyrazol-3-amine

A mixture of 3-(1-fluorocyclopropyl)-3-oxopropanenitrile (3.7 g, 29.11 mmol) and hydrazine hydrate (50 mL) in propan-2-ol (30 mL) was heated at 80° C. for 12 h and then concentrated under reduced pressure. The residue was purified by column chromatography (silica gel, 100-200 mesh, 0 to 5% methanol in dichloromethane) to give 5-(1-fluorocyclopropyl)-1H-pyrazol-3-amine (0.75 g, 18%) as yellow oil. LCMS $R_T$=0.95 min, m/z=142.1 $[M+H]^+$.

LCMS (0 to 30% acetonitrile in water+0.05% ammonium hydroxide over 3 minutes) retention time 0.95 min, ESI+ found [M+H]=142.1.

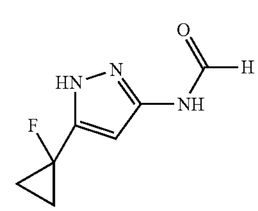 [SMILES: O=CNc1cc(C2(F)CC2)[nH]n1]

Step 4: N-(5-(1-fluorocyclopropyl)-1H-pyrazol-3-yl) formamide

A mixture of 5-(1-fluorocyclopropyl)-1H-pyrazol-3-amine (750 mg, 5.31 mmol) and formic acid (15 mL) was heated at 110° C. for 12 h and then concentrated under reduced pressure. The residue was purified by column chromatography (silica gel, 100-200 mesh, 0 to 5% methanol in dichloromethane) to give N-[5-(1-fluorocyclopropyl)-1H-pyrazol-3-yl]formamide (600 mg, 67%) as a yellow solid. $^1$H NMR (400 MHz, DMSO-d6) δ12.69 (br. s, 1H), 10.56 (br. s, 1H), 8.15 (s, 1H), 6.46 (s, 1H), 1.45-1.36 (m, 2H), 1.09-1.07 (m, 2H).

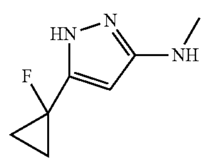

Step 5: 5-(1-fluorocyclopropyl)-N-methyl-1H-pyrazol-3-amine

To a stirred solution of N-[5-(1-fluoocyclopropyl)-1H-pyrazol-3-yl]formamide (600 mg, 3.55 mmol) in tetrahydrofuran (10 mL) was added borane (10 M in $Me_2S$, 1.8 mL, 18.0 mmol) at 0° C. After addition, the mixture was stirred for 2 h at 0° C. and then quenched by addition of methanol (10 mL). The mixture was stirred for 30 min and concentrated under reduced pressure. The residue was purified by column chromatography (silica gel, 100-200 mesh, 0 to 5% methanol in dichloromethane) to obtain 5-(1-fluorocyclopropyl)-N-methyl-1H-pyrazol-3-amine (380 mg, 69%) as a yellow oil. LCMS $R_T$=1.44 min, m/z=156.1 $[M+H]^+$.

LCMS (0 to 30% acetonitrile in water+0.05% ammonium hydroxide over 3.0 mins) retention time 1.44 min, ESI+ found [M+H]=156.1.

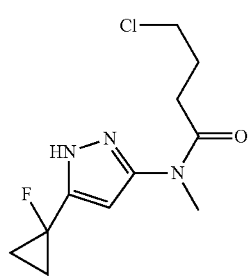 [SMILES: CN(C(=O)CCCCl)c1cc(C2(F)CC2)[nH]n1]

Step 6: 4-chloro-N-(5-(1-fluorocyclopropyl)-1H-pyrazol-3-yl)-N-methylbutanamide

A mixture of 5-(1-fluorocyclopropyl)-N-methyl-1H-pyrazol-3-amine (380 mg, 2.45 mmol) and 4-chlorobutanoyl chloride (2 mL) was heated at 60° C. for 2.5 h and then quenched by addition of methanol (10 mL). The mixture was stirred for 30 min and then concentrated under reduced pressure. The residue was purified by column chromatography (silica gel, 100-200 mesh, 0 to 5% methanol in dichloromethane) to afford 4-chloro-N-[5-(1-fluorocyclopropyl)-1H-pyrazol-3-yl]-N-methyl-butanamide (450 mg, 70%) as a yellow oil. LCMS $R_T$=0.75 min, m/z=259.9 $[M+H]^+$.

LCMS (5 to 95% acetonitrile in water+0.03% trifluoroacetic acid over 1.5 mins) retention time 0.75 min, ESI+ found [M+H]=259.9.

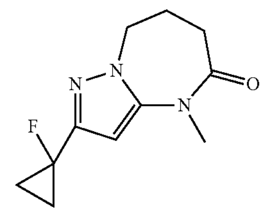 [SMILES: CN1C(=O)CCCn2nc(C3(F)CC3)cc21]

Step 7: 2-(1-fluorocyclopropyl)-4-methyl-7,8-dihydro-4H-pyrazolo[1,5-a][1,3]diazepin-5(6H)-one A mixture of 4-chloro-N-[5-(1-fluorocyclopropyl)-1H-pyrazol-3-yl]-N-methyl-butanamide (400 mg, 1.54 mmol) and cesium carbonate (1.0 g, 3.08 mmol) in N,N-dimethylformamide (5 mL) was stirred at 25° C. for 12 h and filtered. The filtrate was concentrated under reduced pressure and the residue was purified by column chromatography (silica gel, 100-200 mesh, 0 to 5% methanol in dichloromethane) to afford 2-(1-fluorocyclopropyl)-4-methyl-7,8-dihydro-6H-pyrazolo[1,5-a][1,3]diazepin-5-one (180 mg, 52%) as a yellow oil. $^1$H NMR (400 MHz, $CDCl_3$) δ6.09 (s, 1H), 4.19-4.15 (m, 2H), 3.24 (s, 3H), 2.42-2.35 (m, 2H), 2.34-2.25 (m, 2H), 1.41-1.31 (m, 2H), 1.12-1.04 (m, 2H).

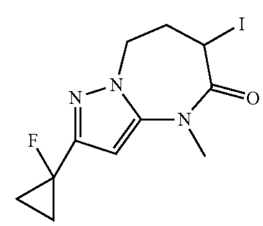 [SMILES: CN1C(=O)C(I)CCn2nc(C3(F)CC3)cc21]

Step 8: 2-(1-fluorocyclopropyl)-6-iodo-4-methyl-7,8-dihydro-4H-pyrazolo[1,5a][1,3]diazepin-5(6H)-one To a stirred solution of 2-(1-fluorocyclopropyl)-4-methyl-7,8-dihydro-6H-pyrazolo[1,5-a][1,3]diazepin-5-one (180 mg, 0.81 mmol) in dichloromethane (15 mL) was added $N^1,N^1,N^2,N^2$-tetramethylethane-1,2-diamine (937 mg, 8.06 mmol) and iodotrimethylsilane (1.6 g, 8.06 mmol) at −15° C. The mixture was stirred at −15° C. for 1.5 h, then iodine (614 mg, 2.42 mmol) was added. The mixture was stirred for another 3 h and then quenched by addition of 50% aqueous sodium thiosulfate (10 mL). The mixture was extracted with dichloromethane (2×30 mL). The combined organic layers were washed with brine (2×20 mL), dried over sodium sulfate and concentrated under reduced pressure. The residue was purified by column chromatography (silica gel, 100-200 mesh, 0 to 5% methanol in dichloromethane) to afford 2-(1-fluorocyclopropyl)-6-iodo-4-methyl-7,8-dihydro-6H-pyrazolo[1,5-a][1,3]diazepin-5-one (150 mg, 53%) as a light yellow oil. $^1$H NMR (400 MHz, $CDCl_3$)

δ6.13 (s, 1H), 4.58-4.54 (m, 1H), 4.19-4.10 (m, 2H), 3.29 (s, 3H), 2.94-2.83 (m, 1H), 2.75-2.65 (m, 1H), 1.39-1.32 (m, 2H), 1.12-1.02 (m, 2H). LCMS $R_T$=2.07 min, m/z=350.0 $[M+H]^+$.

LCMS (0 to 30% acetonitrile in water+0.05% ammonium hydroxide over 3 mins) retention time 2.07 min, ESI+ found [M+H]=350.0.

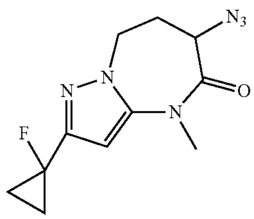 [SMILES: CN1C(=O)C(N=[N+]=[N-])CCn2nc(C3(F)CC3)cc21]

Step 9: 6-azido-2-(1-fluorocyclopropyl)-4-methyl-7,8-dihydro-4H-pyrazolo[1,5-a][1,3]diazepin-5(6H)-one A mixture of 2-(1-fluorocyclopropyl)-6-iodo-4-methyl-7,8-dihydro-6H-pyrazolo[1,5-a][1,3]diazepin-5-one (150 mg, 0.43 mmol) and sodium azide (57 mg, 0.87 mmol) in N,N-dimethylformamide (10 mL) was stirred at 25° C. for 12 h. The reaction mixture was quenched by addition of 20% aqueous sodium hypochlorite (30 mL) and extracted with ethyl acetate (3×30 mL). The combined organic layers were washed with brine (2×20 mL), dried over sodium sulfate and concentrated under reduced pressure to give crude 6-azido-2-(1-fluorocyclopropyl)-4-methyl-7,8-dihydro-6H-pyrazolo[1,5-a][1,3]diazepin-5-one (105 mg, 93%) as a yellow oil.

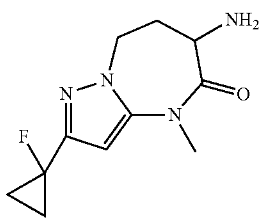 [SMILES: CN1C(=O)C(N)CCn2nc(C3(F)CC3)cc21]

Step 10: 6-amino-2-(1-fluorocyclopropyl)-4-methyl-7,8-dihydro-4H-pyrazolo[1,5-a][1,3]diazepin-5(6H)-one To a solution of 6-azido-2-(1-fluorocyclopropyl)-4-methyl-7,8-dihydro-6H-pyrazolo[1,5-a][1,3]diazepin-5-one (60 mg, 0.23 mmol) in tetrahydrofuran (5 mL) and water (1 mL) was added 80% polymer-bound triphenylphosphine (357 mg). The reaction mixture was stirred at 25° C. for 12 h and filtered. The filtrate was concentrated under reduced pressure and the residue was purified by column chromatography (silica gel, 100-200 mesh, 0 to 10% methanol in dichloromethane) to afford 6-amino-2-(1-fluorocyclopropyl)-4-methyl-7,8-dihydro-6H-pyrazolo[1,5-a][1,3]diazepin-5-one (50 mg, 92%) as a light yellow oil. LCMS $R_T$=1.48 min, m/z=239.1 $[M+H]^+$.

LCMS (0 to 30% acetonitrile in water+0.05% ammonium hydroxide over 3 mins) retention time 1.48 min ESI+ found [M+H]=239.1.

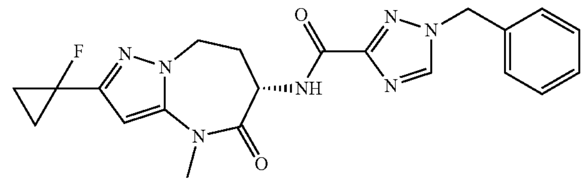 [SMILES: CN1C(=O)[C@@H](NC(=O)c2ncn(Cc3ccccc3)n2)CCn2nc(C3(F)CC3)cc21]

Step 11: 1-benzyl-N-(6S)-2-(1-fluorocyclopropyl)-4-methyl-5-oxo-7,8-dihydro-6H-pyrazolo[1,5-a][1,3]diazepin-6-yl-1,2,4-triazole-3-carboxamide A mixture of 1-benzyl-1,2,4-triazole-3-carboxylic acid (51 mg, 0.25 mmol), 6-amino-2-(1-fluorocyclopropyl)-4-methyl-7,8-dihydro-6H-pyrazolo][1,5-a][1,3]diazepin-5-one (50 mg, 0.21 mmol), N,N-dimethyl-3 (methyliminomethylenethylacetatemino) propan-1-amine hydrochloride (56 mg, 0.31 mmol) and 1-hydroxybenzotrizole (43 mg, 0.31 mmol) in N,N-dimethylformamide (3 mL) was stirred at 25° C. for 12 h. The solvent was removed under reduced pressure and the residue was purified by RP-HPLC (0% to 40% acetonitrile, 0.05% ammonia hydroxide in water) to afford 1-benzyl-N-2-(1-fluorocyclopropyl)-4-methyl-5-oxo-7,8-dihydro-6H-pyrazolo[1,5-a][1,3]diazepin-6-yl-1,2,4-triazole-3-carboxamide (60 mg, 67%) as a white solid. This material was separated by chiral SFC to give:

1-benzyl-N-(6S)-2-(1-fluorocyclopropyl)-4-methyl-5-oxo-7,8-dihydro-6H-pyrazolo[1,5-a][1, 3]diazepin-6-yl-1,2,4-triazole-3-carboxamide (Peak 1, retention time 3.77 min) (8 mg, 13%) as white solids. $^1$H NMR (400 MHz, CD3OD) δ8.56 (s, 1H), 7.41-7.28 (m, 5H), 6.37 (s, 1H), 5.46 (s, 2H), 4.56-4.53 (m, 1H), 4.39-4.31 (m, 1H), 4.29-4.20 (m, 1H), 3.34 (s, 3H), 2.84 (m, 1H), 2.26 (m, 1H), 1.42-1.34 (m, 2H), 1.18-1.07 (m, 2H). LCMS RT=1.672 min, m/z=424.2 (M+H)+.

LCMS (10 to 80% acetonitrile in water+0.05% ammonium bicarbonate over 3 mins) retention time 1.672 min, ESI+ found [M+H]=424.2

SFC conditions: Column: Chiralcel AD-3 50×4.6 mm I.D., 3 um Mobile phase: A: $CO_2$ B: ethanol (0.05% DEA), Gradient: from 5% to 40% of B in 4.5 min and hold 40% for 2.5 min, then 5% to 40% of B in 1.4 min and hold 40% for 1.05 min, then 5% of B for 0.35 min. Flow rate: 4.0 mL/min Column temperature: 40° C.)

Examples 571, 572 and 573

WX Method 115

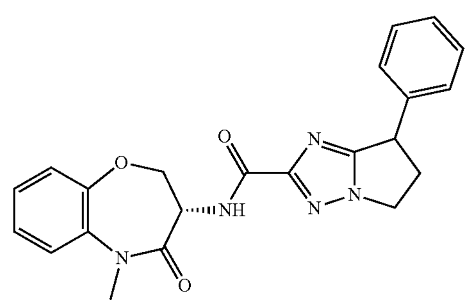

-continued

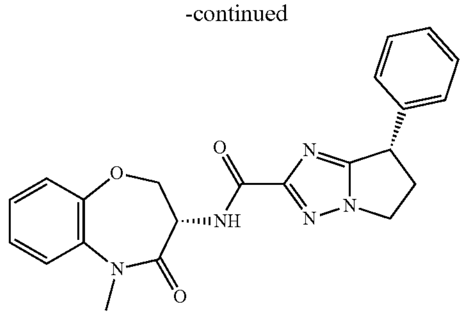

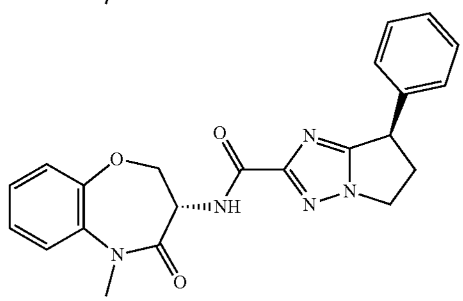

7-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide and (7S)-7-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide and (7R)-7-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide Amide coupling prepared in a similar fashion to WX Method 113 (RIP1K_experimental_3rd_WX.doc). The crude was purified by PR-HPLC (22% to 52% acetonitrile, 0.05% ammonia hydroxide in water) to afford 7-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (5.5 mg, 26%) as white solid. $^1H$ NMR (400 MHz, $CD_3OD$) δ7.45-7.41 (m, 1H), 7.39-7.26 (m, 7H), 7.25-7.21 (m, 1H), 5.02-4.97 (m, 1H), 4.60-4.52 (m, 2H), 4.45-4.35 (m, 2H), 4.32-4.22 (m, 1H), 3.40 (s, 3H), 3.28-3.23 (m, 1H), 2.76-2.67 (m, 1H). LCMS $R_T$=1.017 min, m/z=404.3 $[M+H]^+$.

LCMS (10 to 80% acetonitrile in water+0.03% trifluoacetic acid over 2.0 mins) retention time 1.017 min, ESI+ found [M+H]=404.3.

Another Batch of the Racemic Material (60 mg) was Separated by Chiral SFC to Give:

(7S)-7-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (Peak 1, retention time=3.325 min) (18.3 mg, 30%) as white solids. $^1H$ NMR (400 MHz, $CD_3OD$) δ7.42-7.22 (m, 9H), 5.00-4.87 (m, 1H), 4.61-4.53 (m, 2H), 4.42-4.39 (m, 2H), 4.37-4.28 (m, 1H), 3.40 (s, 3H), 3.28-3.25 (m, 1H), 2.76-2.70 (m, 1H). LCMS $R_T$=1.011 min, m/z=404.4 $[M+H]^+$.

LCMS (10 to 80% acetonitrile in water+0.03% trifluoacetic acid over 2.0 mins) retention time 1.011 min, ESI+ found [M+H]=404.4.

(7R)-7-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (Peak 2, retention time=3.439 min) (16.1 mg, 27%) as white solid. $^1H$ NMR (400 MHz, $CD_3OD$) δ7.41-7.24 (m, 9H), 5.00-4.97 (m, 1H), 4.60-4.54 (m, 2H), 4.42-4.39 (m, 2H), 4.37-4.28 (m, 1H), 3.41 (s, 3H), 3.28-3.25 (m, 1H), 2.76-2.69 (m, 1H). LCMS $R_T$=1.006 min, m/z=404.4 $[M+H]^+$.

LCMS (10 to 80% acetonitrile in water+0.03% trifluoacetic acid over 2.0 mins) retention time 1.006 min, ESI+ found [M+H]=404.4.

SFC condition: Column: Chiralcel IC-3 150×4.6 mm I.D., 3 um Mobile phase: 40% iso-propanol (0.05% DEA) in $CO_2$ Flow rate: 2.5 mL/min Column temperature: 40° C.

Examples 574 and 575

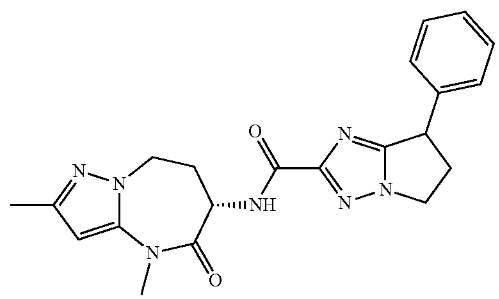

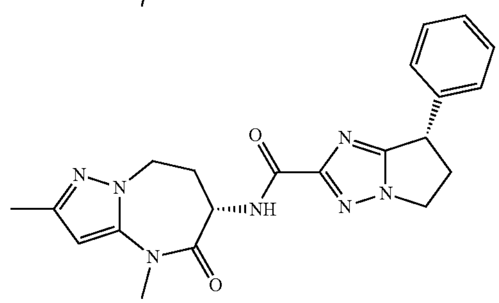

7-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide and (7S)-7-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Amide coupling prepared in a similar fashion to WX Method 113 (RIP1K_experimental_3rd WX.doc). The crude was purified by PR-HPLC (22% to 52% acetonitrile/0.05% ammonia hydroxide in water) to afford 7-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (6.2 mg, 29%) as white solid. $^1H$ NMR (400 MHz, $CD_3OD$) δ7.39-7.25 (m, 5H), 6.11 (s, 1H), 4.57-4.49 (m, 2H), 4.45-4.36 (m, 1H), 4.35-4.15 (m, 3H), 3.32 (s, 3H), 3.30-3.24 (m, 1H), 2.90-2.66 (m, 2H), 2.33-2.14 (m, 4H). LCMS $R_T$=0.920 min, m/z=406.3 $[M+H]^+$.

LCMS (10 to 80% acetonitrile in water+0.03% trifluoacetic acid over 2.0 mins) retention time 0.920 min, ESI+ found [M+H]=406.3.

Another Batch of the Racemic Material (50 mg) was Separated by Chiral SFC to Give:

(7S)-7-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (Peak 1, retention time 3.64 min) (22 mg, 44% yield) as a white solid. $^1H$ NMR (400 MHz, $CD_3OD$) δ9.35 (s, 1H), 8.38 (s, 1H), 7.05-7.00 (m, 2H), 5.45-5.40 (m, 1H), 4.69-4.64 (m, 1H), 3.05-3.02 (m, 1H), 2.89-2.76 (m, 2H), 2.32-2.26 (m, 1H), 1.60 (d, J=6.8 Hz, 6H). LCMS $R_T$=1.95 min, m/z=406.2 $[M+H]^+$.

LCMS (0 to 60% acetonitrile in water+0.03% trifluoacetic acid over 2.0 mins) retention time 1.95 min, ESI+ found [M+H]=406.2.

SFC conditions: Column: Chiralcel AD-3 100×4.6 mm I.D., 3 um Mobile phase: A: $CO_2$ B: ethanol (0.05% dethyl acetate), Gradient: from 5% to 40% of B in 4.5 min and hold 40% for 2.5 min, then 5% of B for 1 min, Flow rate: 2.8 mL/min Column temperature: 40° C.

Example 576

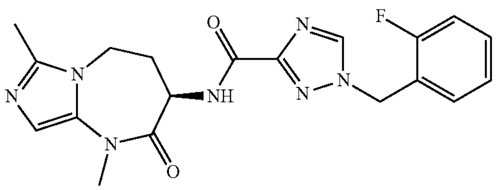 [SMILES: Cc1ncc2n1CC[C@@H](NC(=O)c1ncn(Cc3ccccc3F)n1)C(=O)N2C]

1-[(2-fluorophenyl)methyl]-N-(3R)-1,7-dimethyl-2-oxo-4,5-dihydro-3H-imidazo[1,5-a][1, 3]diazepin-3-yl-1,2,4-triazole-3-carboxamide Amide coupling prepared in a similar fashion to WX Method 085. The crude was purified by RP-HPLC (15% to 45% acetonitrile, 0.05% ammonia hydroxide in water) to afford 1-[(2-fluorophenyl)methyl]-N-1,7-dimethyl-2-oxo-4,5-dihydro-3H-imidazo[1,5-a][1,3]diazepin-3-yl-1,2,4-triazole-3-carboxamide (50 mg, 54%) as a white solid. The racemic compound was separated by chiral SFC to give:

1-[(2-fluorophenyl)methyl]-N-(3R)-1,7-dimethyl-2-oxo-4,5-dihydro-3H-imidazo[1,5-a][1,3]diazepin-3-yl-1,2,4-triazole-3-carboxamide (Peak 2, retention time 4.788 min) (23 mg, 25%) as white solids. $^1H$ NMR (400 MHz, DMSO-$d_6$) δ8.81 (s, 1H), 8.48 (d, J=8.0 Hz, 1H), 7.46-7.39 (m, 1H), 7.38-7.31 (m, 1H), 7.28-7.19 (m, 2H), 6.80 (s, 1H), 5.55 (s, 2H), 4.38-4.33 (m, 1H), 4.23-4.17 (m, 1H), 3.75-3.71 (m, 1H), 3.23-3.17 (m, 3H), 2.47-2.41 (m, 1H), 2.29 (s, 3H), 2.25-2.17 (m, 1H). LCMS $R_T$=1.77 min; m/z=398.1 $(M+H)^+$.

LCMS (0 to 60% acetonitrile in water+0.05% ammonium bicarbonate over 3 mins) retention time 1.77 min, ESI+ found [M+H]=398.1

SFC conditions: Column: Chiralcel OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Example 577

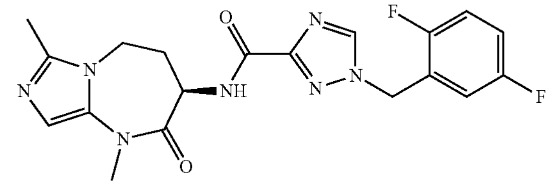 [SMILES: Cc1ncc2n1CC[C@@H](NC(=O)c1ncn(Cc3cc(F)ccc3F)n1)C(=O)N2C]

1-[(2,5-difluorophenyl)methyl]-N-(3R)-1,7-dimethyl-2-oxo-4,5-dihydro-3H-imidazo[1,5-a][1,3]diazepin-3-yl-1,2,4-triazole-3-carboxamide Amide coupling prepared in a similar fashion to WX Method 085. The crude was purified by RP-HPLC (18% to 48% acetonitrile, 0.05% ammonia hydroxide in water) to afford 1-[(2,5-difluorophenyl)methyl]-N-1,7-dimethyl-2-oxo-4,5-dihydro-3H-imidazo[1,5-a][1,3]di azepin-3-yl-1,2,4-triazole-3-carboxamide (50 mg, 52%) as white solids. The racemic compound was separated by chiral SFC to give:

1-[(2,5-difluorophenyl)methyl]-N-(3R)-1,7-dimethyl-2-oxo-4,5-dihydro-3H-imidazo[1,5-a][1,3]diazepin-3-yl-1,2,4-triazole-3-carboxamide (Peak 2, retention time 4.857 min) (17 mg, 17.5%). $^1H$ NMR (400 MHz, DMSO-$d_6$) δ 8.81 (s, 1H), 8.50 (d, J=8.0 Hz, 1H), 7.37-7.22 (m, 3H), 6.80 (s, 1H), 5.54 (s, 2H), 4.40-4.32 (m, 1H), 4.22-4.16 (m, 1H), 3.75-3.69 (m, 1H), 3.21 (s, 3H), 2.47-2.41 (m, 1H), 2.29 (s, 3H), 2.25-2.17 (m, 1H). LCMS $R_T$=1.796 min, m/z=416.1 $(M+H)^+$.

LCMS (0 to 60% acetonitrile in water+0.05% ammonium bicarbonate over 3 mins) retention time 1.796 min, ESI+ found [M+H]=416.1

SFC conditions: Column: Chiralcel OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Example 578

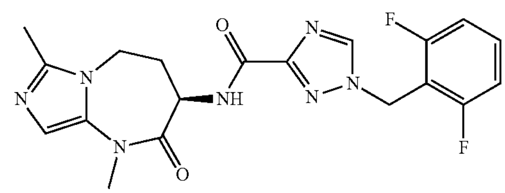 [SMILES: Cc1ncc2n1CC[C@@H](NC(=O)c1ncn(Cc3c(F)cccc3F)n1)C(=O)N2C]

1-[(2,6-difluorophenyl)methyl]-N-[(3R)-1,7-dimethyl-2-oxo-4,5-dihydro-3H-imidazo[1,5-a][1,3]diazepin-3-yl]-1,2,4-triazole-3-carboxamide Amide coupling prepared in a similar fashion to WX Method 085. The crude was purified by RP-HPLC (20% to 50% acetonitrile, 0.05% ammonia hydroxide in water) to afford 1-[(2,6-difluorophenyl)methyl]-N-(1,7-dimethyl-2-oxo-4,5-dihydro-3H-imidazo[1,5-a][1,3]di azepin-3-yl)-1,2,4-triazole-3-carboxamide (50 mg, 47%) as white solids. The racemic compound was separated by chiral SFC to give:

1-[(2,6-difluorophenyl)methyl]-N-[(3R)-1,7-dimethyl-2-oxo-4,5-dihydro-3H-imidazo[1,5-a][1,3]diazepin-3-yl]-1,2,4-triazole-3-carboxamide (Peak 2, retention time 4.519 min) (21 mg, 42%) as a white solid. $^1$H NMR (400 MHz, DMSO-$d_6$) δ8.83 (s, 1H), 8.46 (d, J=8.0 Hz, 1H), 7.54-7.46 (m, 1H), 7.19-7.15 (m, 2H), 6.80 (s, 1H), 5.55 (s, 2H), 4.37-4.30 (m, 1H), 4.21-4.16 (m, 1H), 3.75-3.67 (m, 1H), 3.20 (s, 3H), 2.46-2.40 (m, 1H), 2.29 (s, 3H), 2.24-2.16 (m, 1H). LCMS RT=1.762 min; m/z=416.2 $(M+H)^+$.

LCMS (0 to 60% acetonitrile in water+0.05% ammonium bicarbonate over 3 mins) retention time 1.762 min, ESI+ found [M+H]=416.2

SFC conditions: Column Chiralcel OJ-3 150×4.6 mm I.D., 3 um, Mobile phase: A: $CO_2$ B: ethanol (0.05% DEA) Gradient: from 5% to 40% of B in 5.0 min and hold 40% for 2.5 min, then 5% of B for 2.5 min, Flow rate: 2.5 mL/min Column temperature: 35° C.

Example 579

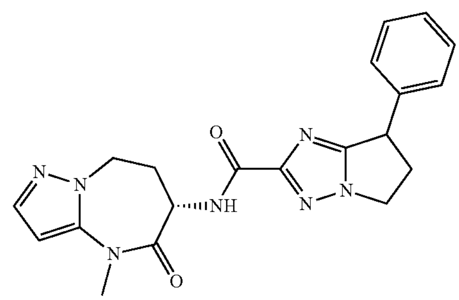 [SMILES: CN1C(=O)[C@@H](NC(=O)c2nc3n(n2)CCC3c2ccccc2)CCn2nccc21]

7-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Amide coupling prepared in a similar fashion to WX Method 113 (RIP1K_experimental_3$^{rd}$_WX.doc). The crude was purified by PR-HPLC (22% to 52% acetonitrile/0.05% ammonia hydroxide in water) to afford 7-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (14.5 mg, 45%) as white solids. $^1$H NMR (400 MHz, $CD_3OD$) δ7.52 (s, 1H), 7.39-7.32 (m, 2H), 7.32-7.25 (m, 3H), 6.30 (s, 1H), 4.57-4.46 (m, 2H), 4.45-4.35 (m, 2H), 4.33-4.20 (m, 2H), 3.35 (s, 3H), 3.30-3.24 (m, 1H), 2.91-2.79 (m, 1H), 2.76-2.66 (m, 1H), 2.32-2.21 (m, 1H). LCMS $R_T$=0.889 min, m/z=392.3 $[M+H]^+$.

LCMS (10 to 80% acetonitrile in water+0.03% trifluoacetic acid over 2.0 mins) retention time 0.889 min, ESI+ found [M+H]=392.3.

Example 580

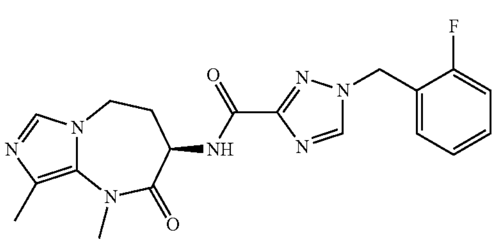 [SMILES: Cc1ncn2c1N(C)C(=O)[C@H](NC(=O)c1ncn(Cc3ccccc3F)n1)CC2]

1-[(2-fluorophenyl)methyl]-N-[(3R)-1,9-dimethyl-2-oxo-4,5-dihydro-3H-imidazo[1,5-a][1,3]diazepin-3-yl]-1,2,4-triazole-3-carboxamide Amide coupling prepared in a similar fashion to WX Method 043. The crude was purified by RP-HPLC (5% to 35% acetonitrile, 0.05% HCl in water) to give N-(1,9-dimethyl-2-oxo-2,3,4,5-tetrahydro-1H-imidazo[1,5-a][1,3]diazepin-3-yl)-1-(2-fluorobenzyl)-1H-1,2,4-triazole-3-carboxamide (70 mg, 68%) as a white solid. This racemic material was separated by chiral SFC to give:

1-[(2-fluorophenyl)methyl]-N-[(3R)-1,9-dimethyl-2-oxo-4, 5-dihydro-3H-imidazo[1,5-a][1,3]diazepin-3-yl]-1,2,4-triazole-3-carboxamide (Peak 2, retention time 3.642 min) (47 mg, 33%). $^1$H NMR (400 MHz, $CD_3OD$) δ8.59 (s, 1H), 7.56 (s, 1H), 7.41-7.38 (m, 2H), 7.22-7.15 (m, 2H), 5.55 (s, 2H), 4.57-4.52 (m, 1H), 4.37-4.31 (m, 1H), 3.96-3.93 (m, 1H), 3.31 (s, 3H), 2.72-2.63 (m, 1H), 2.22 (s, 3H), 2.15-2.09 (m, 1H). LCMS $R_T$=0.447 min; m/z=398.0 $(M+H)^+$.

LCMS (5 to 95% acetonitrile in water+0.03% trifluoacetic acid over 1.5 mins) retention time 0.447 min, ESI+ found [M+H]=398.0

SFC conditions: Column: Chiralpak OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.8 mL/min Column temp.: 40° C.

Example 581

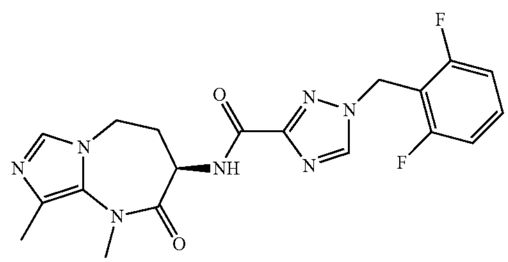 [SMILES: Cc1ncn2c1N(C)C(=O)[C@H](NC(=O)c1ncn(Cc3c(F)cccc3F)n1)CC2]

1-[(2,6-difluorophenyl)methyl]-N-(3R)-1,9-dimethyl-2-oxo-4,5-dihydro-3H-imidazo[1,5-a][1,3]diazepin-3-yl-1,2,4-triazole-3-carboxamide Amide coupling prepared in a similar fashion to WX Method 100 (RIP1K_experimental_3$^{rd}$_WX.doc). The crude was purified by RP-HPLC (5% to 35% acetonitrile, 0.05% HCl in water) to give 1-(2,6-difluorobenzyl)-N-(1,9-dimethyl-2-oxo-2,3,4,5-tetrahydro-1H-imidazo[1,5-a][1,3]diazepin-3-yl)-1H-1,2,4-triazole-3-carboxamide (70 mg, 65%) as a white solid. The racemic material was separated by chiral SFC to give:

1-[(2,6-difluorophenyl)methyl]-N-(3R)-1,9-dimethyl-2-oxo-4,5-dihydro-3H-imidazo[1,5-a][1,3]diazepin-3-yl-1,2,4-triazole-3-carboxamide (Peak 2, retention time 3.397 min) (26 mg, 37%) as a white solid. $^1$H NMR (400 MHz, $CD_3OD$) δ8.65 (s, 1H), 8.33 (s, 1H), 7.50-7.44 (m, 1H), 7.09-7.02 (m, 2H), 5.62 (s, 2H), 4.65-4.60 (m, 1H), 4.50-4.46 (m, 1H), 4.13-4.08 (m, 1H), 3.32 (s, 3H), 2.73-2.65 (m, 1H), 2.32 (s, 3H), 2.26-2.15 (m, 1H). LCMS $R_T$=0.549 min; m/z=416.0 $(M+H)^+$.

LCMS (5 to 95% acetonitrile in water+0.03% trifluoacetic acid over 1.5 mins) retention time 0.549 min, ESI+ found [M+H]=416.0

SFC conditions: Column: Chiralpak OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.8 mL/min Column temp.: 40° C.

Example 582

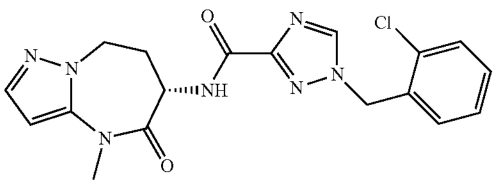 [SMILES: CN1C(=O)[C@@H](NC(=O)c2ncn(Cc3ccccc3Cl)n2)CCn2nccc21]

1-[(2-chlorophenyl)methyl]-N-(6S)-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 073 (RIP1K_experimental_3rd_WX.doc). The crude was purified by RP-HPLC (20% to 50% acetonitrile/0.05% ammonia hydroxide in water) to give 1-[(2-chlorophenyl)methyl]-N-(6S)-4-methyl-5-oxo-7,8-dihydro-6H-pyrazolo[1,5-a][1,3]diazepin-6-yl-1,2,4-triazole-3-carboxamide (42.7 mg, 48%) as a white solid. $^1$H NMR (400 MHz, $CD_3OD$) δ 8.58 (s, 1H), 7.52 (s, 1H), 7.46 (d, J=6.8 Hz, 1H), 7.37-7.32 (m, 3H), 6.30 (s, 1H), 5.61 (s, 2H), 4.50-4.41 (m, 2H), 4.30-4.27 (m, 1H), 3.35 (s, 3H), 2.88-2.82 (m, 1H), 2.29-2.23 (m, 1H). LC-MS $R_T$=0.633 min, m/z=400.0 $[M+H]^+$.

LCMS (5 to 95% acetonitrile in water+0.03% trifluoacetic acid over 1.5 mins) retention time 0.633 min, ESI+ found [M+H]=400.0.

Example 583

WX Method 052

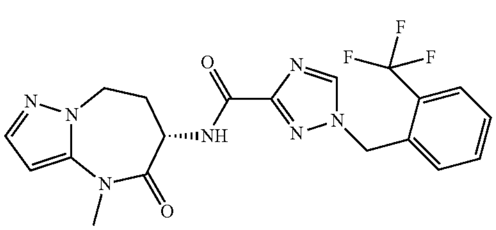 [SMILES: CN1C(=O)[C@@H](NC(=O)c2ncn(Cc3ccccc3C(F)(F)F)n2)CCn2nccc21]

N-(6S)-4-methyl-5-oxo-7,8-dihydro-6H-pyrazolo[1,5-a][1,3]diazepin-6-yl]-1-[[2-(trifluoromethyl)phenyl]methyl-1,2,4-triazole-3-carboxamide

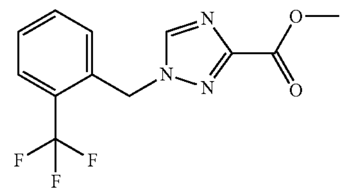 [SMILES: COC(=O)c1ncn(Cc2ccccc2C(F)(F)F)n1]

Step 1: methyl 1-[[2-(trifluoromethyl)phenyl]methyl]-1,2,4-triazole-3-carboxylate To a solution of methyl 1H-1,2,4-triazole-3-carboxylate (50 mg, 0.39 mmol) in N,N-dimethylformamide (3 mL) was added 2-(trifluoromethyl)benzyl bromide (112 mg, 0.47 mmol) and potassium carbonate (81 mg, 0.59 mmol). The mixture was stirred at 40° C. for 2 h and filtered. The filtrate was concentrated under reduced pressure and the residue was purified by preparative TLC (50% ethyl acetate in petroleum ether, $R_f$=0.3) to afford methyl 1-[[2-(trifluoromethyl)phenyl]methyl]-1,2,4-triazole-3-carboxylate (100 mg, 89%) as colorless oil. LCMS $R_T$=0.690 min, m/z=286.0 $[M+H]^+$.

LCMS (5 to 95% acetonitrile in water+0.03% trifluoacetic acid over 1.5 mins) retention time 0.690 min, ESI+ found [M+H=286.0

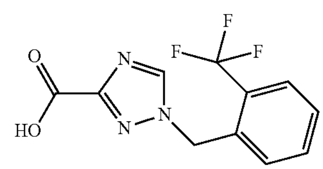 [SMILES: O=C(O)c1ncn(Cc2ccccc2C(F)(F)F)n1]

Step 2: 1-[[2-(trifluoromethyl)phenyl]methyl]-1,2,4-triazole-3-carboxylic acid

A mixture of methyl 1-[[2-(trifluoromethyl)phenyl]methyl]-1,2,4-triazole-3-carboxylate (100 mg, 0.35 mmol) and lithium hydroxide (42 mg, 1.75 mmol) in tetrahydrofuran (5 mL) and water (2 mL) was stirred at 15° C. for 2 h. The mixture was filtered and the filtrate was adjusted to pH=6 by addition of 1N HCl. The solution was extracted with dichloromethane (3×20 mL). The combined organic layers were dried over anhydrous sodium sulfate and concentrated under reduced pressure to afford 1-[[2-(trifluoromethyl)phenyl]methyl]-1,2,4-triazole-3-carboxylic acid (86 mg, 90%) as a colorless oil, used as is in the next step.

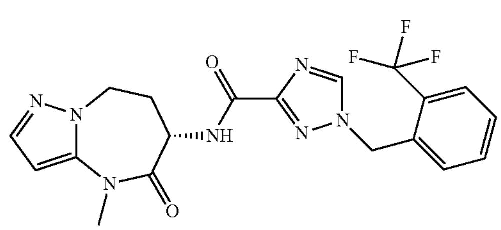 [SMILES: CN1C(=O)[C@@H](NC(=O)c2ncn(Cc3ccccc3C(F)(F)F)n2)CCn2nccc21]

Step 3: N-(6S)-4-methyl-5-oxo-7,8-dihydro-6H-pyrazolo[1,5-a][1,3]diazepin-6-yl]-1-[[2-(trifluoromethyl)phenyl]methyl-1,2,4-triazole-3-carboxamide To a stirred solution of (6S)-6-amino-4-methyl-7,8-dihydro-6H-pyrazolo[1,5-a][1,3]diazepin-5-one (25 mg, 0.14 mmol) in N,N-dimethylformamide (6 mL) was added 1-[[2-(trifluoromethyl)phenyl]methyl]-1,2,4-triazole-3-carboxylic acid (45 mg, 0.17 mmol), 1-hydroxybenzotriazole (28 mg, 0.21 mmol) and 1-(3-dimethylaminopropyl)-3-ethylcarbodiimidehydrochloride (40 mg, 0.21 mmol). The mixture was stirred at 20° C. for 2 h and concentrated under reduced pressure. The residue was purified by RP-HPLC (acetonitrile 17-47%/0.05% ammonium hydroxide in water) to give N-(6S)-4-methyl-5-oxo-7,8-dihydro-6H-pyrazolo[1,5-a][1,3]diazepin-6-yl-1-[[2-(trifluoromethyl)phenyl]methyl]-1,2,4-triazole-3-carboxamide (17 mg, 28%) as a white solid. $^1$H NMR (400 MHz, $CD_3OD$) δ8.55 (s, 1H), 7.77 (d, J=8.0 Hz, 1H), 7.66-7.60 (m, 1H), 7.57-7.49 (m, 2H), 7.28 (d, J=8.0 Hz, 1H), 6.30 (d, J=2.0 Hz, 1H), 5.70 (s, 2H), 4.51-4.49 (m, 1H), 4.45-4.37 (m, 1H), 4.32-4.21 (m, 1H), 3.34 (s, 3H), 2.89-2.83 (m, 1H), 2.32-2.26 (m, 1H). LCMS $R_T$=0.935 min, m/z=434.3 $[M+H]^+$.

LCMS (10 to 80% acetonitrile in water+0.03% trifluoacetic acid over 2.0 mins) retention time 0.935 min, ESI+ found [M+H]=434.3

Example 584

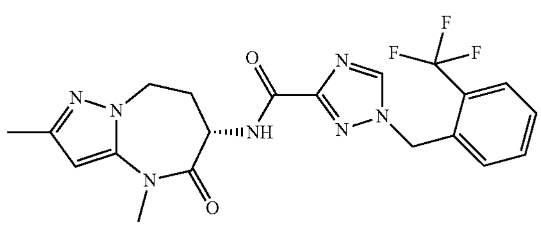 [SMILES: Cc1cc2n(n1)CC[C@H](NC(=O)c1ncn(Cc3ccccc3C(F)(F)F)n1)C(=O)N2C]

N-(6S)-2,4-dimethyl-5-oxo-7,8-dihydro-6H-pyrazolo[1,5-a][1,3]diazepin-6-yl-1-[[2-(trifluoromethyl)phenyl]methyl]-1,2,4-triazole-3-carboxamide Amide coupling prepared in a similar fashion to WX Method 052. The crude was purification by RP-HPLC (acetonitrile 17-47%/0.05 ammonium hydroxide in water) to give N-(6S)-2,4-dimethyl-5-oxo-7,8-dihydro-6H-pyrazolo[1,5-a][1,3]diazepin-6-yl-1-[[2-(trifluoro methyl)phenyl]methyl]-1,2,4-triazole-3-carboxamide (32 mg, 55%) as a white solid. $^1$H NMR (400 MHz, $CD_3OD$) δ8.56 (s, 1H), 7.78 (d, J=8.0 Hz, 1H), 7.66-7.61 (m, 1H), 7.58-7.52 (m, 1H), 7.28 (d, J=8.0 Hz, 1H), 6.11 (s, 1H), 5.71 (s, 2H), 4.56-4.51 (m, 1H), 4.35-4.27 (m, 1H), 4.26-4.15 (m, 1H), 3.32 (s, 3H), 2.87-2.80 (m, 1H), 2.30-2.21 (m, 4H). LCMS $R_T$=0.971 min, m/z=448.3 $[M+H]^+$.

LCMS (10 to 80% acetonitrile in water+0.03% trifluoacetic acid over 2.0 mins) retention time 0.971 min, ESI+ found [M+H]=448.3

Example 585

WX Method 055

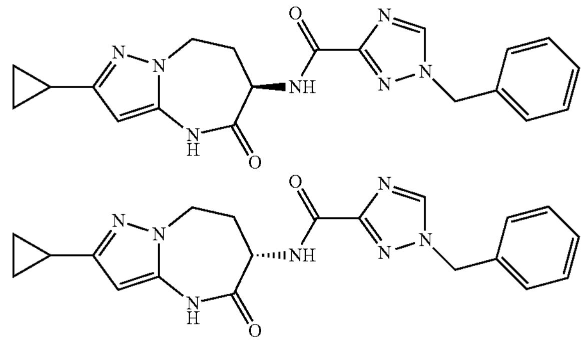

1-benzyl-N-(6S)-2-cyclopropyl-5-oxo-4,6,7,8-tetrahydropyrazolo[1,5-a][1,3]diazepin-6-yl-1,2,4-triazole-3-carboxamide and 1-benzyl-N-(6R)-2-cyclopropyl-5-oxo-4,6,7,8-tetrahydropyrazolo[1,5-a][1,3]diazepin-6-yl-1,2,4-triazole-3-carboxamide

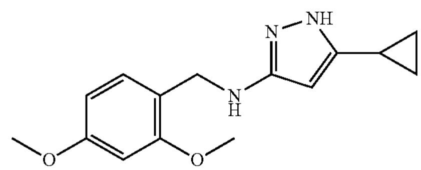 [SMILES: COc1ccc(CNc2cc(C3CC3)[nH]n2)c(OC)c1]

Step 1: 5-cyclopropyl-N-[(2,4-dimethoxyphenyl)methyl]-1H-pyrazol-3-amine

To a solution of 2,4-dimethoxybenzaldehyde (29.7 g, 178.6 mmol) and 5-cyclopropyl-1H-pyrazol-3-amine (20.0 g, 162.4 mmol) in 1,2-dichloroethane (400 mL) was added acetic acid (9.75 g, 162.4 mmol). The reaction solution was stirred at 25° C. for 12 h, then sodium triacetoxyborohydride (51.6 g, 243.6 mmol) was added to the mixture. Stirring was continued for another 24 h and the reaction was quenched by addition of water (300 mL). The resulting mixture was extracted with dichloromethane (3×200 mL). The combined organic layers were dried over anhydrous sodium sulfate and concentrated under reduced pressure. The residue was purified by column chromatography (silica gel, 100-200 mesh, 0 to 100% ethyl acetate in petroleum ether) to afford 5-cyclopropyl-N-[(2,4-dimethoxyphenyl)methyl]-1H-pyrazol-3-amine (8.0 g, 18%) as yellow oil, used as is in the next step.

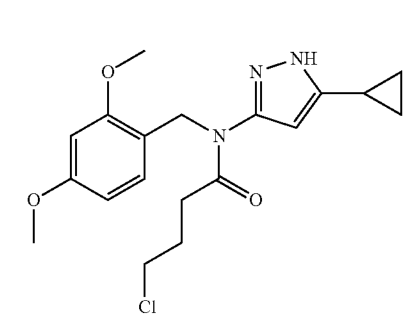 [SMILES: COc1ccc(CN(C(=O)CCCCl)c2cc(C3CC3)[nH]n2)c(OC)c1]

Step 2: 4-chloro-N-(5-cyclopropyl-1H-pyrazol-3-yl)-N-[(2,4-dimethoxyphenyl)methyl]butanamide To a mixture of 5-cyclopropyl-N-[(2,4-dimethoxyphenyl)methyl]-1H-pyrazol-3-amine (8.00 g, 29.3 mmol) and 4-dimethylaminopyridine (0.18 g, 1.5 mmol) in dichloromethane (400 mL) was added N,N-diisopropylethylamine (29.02 mL, 176.0 mmol) and 4-chlorobutanoyl chloride (19.65 mL, 176.0 mmol) at 25° C. The resulting mixture was stirred at 25° C. for 12 h and then quenched by addition of methanol (5 mL). The mixture was stirred for 0.5 h and then concentrated under reduced pressure. The residue was purified by column chromatography (silica gel, 100-200 mesh, 0 to 50% ethyl acetate in petroleum ether) to give 4-chloro-N-(5-cyclopropyl-1H-pyrazol-3-yl)-N-[(2,4-dimethoxyphenyl)methyl]butanamide (4.00 g, 36.2% yield) as yellow oil. LCMS $R_T$=1.07 min, m/z=378.2 $[M+H]^+$.

LCMS (10 to 80% acetonitrile in water+0.03% trifluoacetic acid over 1.5 mins) retention time 1.07 min, ESI+ found [M+H]=378.2

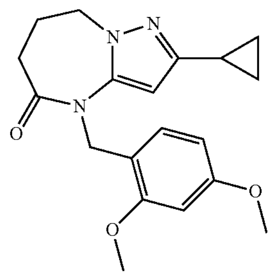 [SMILES: COc1ccc(CN2C(=O)CCCn3nc(C4CC4)cc32)c(OC)c1]

Step 3: 2-cyclopropyl-4-[(3,5-dimethoxyphenyl)methyl]-7,8-dihydro-6H-pyrazolo[1,5-a][1,3]diazepin-5-one A mixture of 4-chloro-N-(5-cyclopropyl-1H-pyrazol-3-yl)-N-[(2,4-dimethoxyphenyl)methyl]butanamide (4.0 g, 10.59 mmol) and potassium carbonate (4.4 g, 31.76 mmol) in N,N-dimethylformamide (80 mL) was stirred at 70° C. for 2 h and then concentrated under reduced pressure. The residue was purified by column chromatography (silica gel, 100-200 mesh, 0-60% ethyl acetate in petroleum ether) to afford 2-cyclopropyl-4-[(3,5-dimethoxyphenyl)methyl]-7,8-dihydro-6H-pyrazolo[1,5-a][1,3]diazepin-5-one (2.0 g, 55.3% yield) as yellow oil. LCMS $R_T$=0.816 min, m/z=342.3$[M+H]^+$.

LCMS (5 to 95% acetonitrile in water+0.03% trifluoacetic acid over 1.5 mins) retention time 0.816 min, ESI+ found [M+H]=342.3

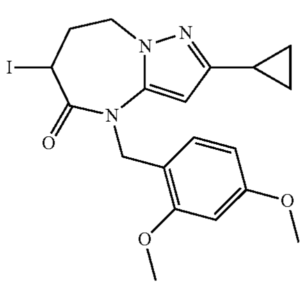 [SMILES: COc1ccc(CN2C(=O)C(I)CCn3nc(C4CC4)cc32)c(OC)c1]

Step 4: 2-cyclopropyl-4-[(2,4-dimethoxyphenyl)methyl]-6-iodo-7,8-dihydro-6H-pyrazolo[1,5-a][1,3]diazepin-5-one 2-cyclopropyl-4-[(2,4-dimethoxyphenyl)methyl]-7,8-dihydro-6H-pyrazolo[1,5-a][1,3]diazepin-5-one (2.0 gg, 5.86 mmol) in dichloromethane (200 mL) was treated with N1,N1,N2,N2-tetramethylethane-1,2-diamine (6.8 g, 58.58 mmol) at −15° C., followed by iodotrimethylsilane (11.7 g, 58.58 mmol). Stirring at −15° C. was continued for 1.5 h, and then iodine (4.46 g, 17.57 mmol) was added. The mixture was stirred for another 3 h and then quenched by addition of saturated sodium sulphite (3 mL) and water (15 mL). The resulting mixture was extracted with ethyl acetate (3×50 mL). The combined organic layers were dried over anhydrous sodium sulfate and concentrated under reduced pressure. The residue was purified by column chromatography (silica gel, 100-200 mesh, 0-50% ethyl acetate in petroleum ether) to afford 2-cyclopropyl-4-[(2,4-dimethoxyphenyl)methyl]-6-iodo-7,8-dihydro-6H-pyrazolo[1,5-a][1,3]diazepin-5-one (1.0 g, 36.5% yield) as a light yellow solid. LCMS $R_T$=0.865 min, m/z=468.0 $[M+H]^+$.

LCMS (5 to 95% acetonitrile in water+0.03% trifluoacetic acid over 1.5 mins) retention time 0.865 min, ESI+ found [M+H]=468.0

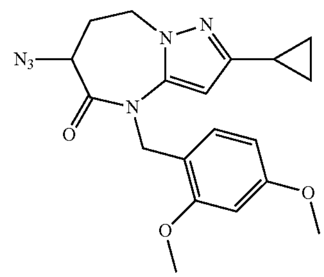 [SMILES: COc1ccc(CN2C(=O)C(N=[N+]=[N-])CCn3nc(C4CC4)cc32)c(OC)c1]

Step 5: 6-azido-2-cyclopropyl-4-[(2,4-dimethoxyphenyl)methyl]-7,8-dihydro-6H-pyrazolo[1,5-a][1,3]diazepin-5-one To a solution of 2-cyclopropyl-4-[(2,4-dimethoxyphenyl)methyl]-6-iodo-7,8-dihydro-6H-pyrazolo[1,5-a][1,3]diazepin-5-one (1.0 g, 2.14 mmol) in N,N-dimethylformamide (20 mL) was added sodium azide (0.3 g, 4.28 mmol). The reaction mixture was stirred at 25° C. for 12 h and diluted with water (15 mL). The solution was extracted with ethyl acetate (3×20 mL). The combined organic layers were dried over anhydrous sodium sulfate and concentrated under reduced pressure. The residue was purified by column chromatography (silica gel, 100-200 mesh, 0-50% ethyl acetate in petroleum ether) to afford 6-azido-2-cyclopropyl-4-[(2,4-dimethoxyphenyl)methyl]-7,8-dihydro-6H-pyrazolo[1,5-a][1,3]diazepin-5-one (600 mg, 73%) as colorless oil. LCMS $R_T$=0.0.853 min, m/z=383.1 $[M+H]^+$.

LCMS (5 to 95% acetonitrile in water+0.03% trifluoacetic acid over 1.5 mins) retention time 0.853 min, ESI+ found [M+H]=383.1

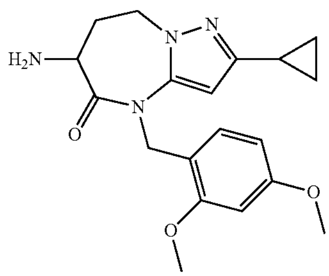 [SMILES: COc1ccc(CN2C(=O)C(N)CCn3nc(C4CC4)cc32)c(OC)c1]

Step 6: 6-amino-2-cyclopropyl-4-[(2,4-dimethoxyphenyl)methyl]-7,8-dihydro-6H-pyrazolo[1,5-a][1,3]diazepin-5-one To a solution of 80% polymer-bound triphenylphosphine (5.1 g) in tetrahydrofuran (25 mL) was added water (5 mL) followed by 6-azido-2-cyclopropyl-4-[(2,4-dimethoxyphenyl)methyl]-7,8-dihydro-6H-pyrazolo[1,5-a][1,3]diazepin-5-one (600 mg, 1.57 mmol). The mixture was stirred at 20° C. for 16 h. The mixture was filtered through Celite and concentrated to dryness. The resulting residue was purified by column chromatography (silica gel, 100-200 mesh, 0 to 20% methanol in dichloromethane) to afford 6-amino-2-cyclopropyl-4-[(2,4-dimethoxyphenyl)methyl]-7,8-dihydro-6H-pyrazolo[1,5-a][1, 3]diazepin-5-one (400 mg, 72%) as yellow oil, used as is in the next step.

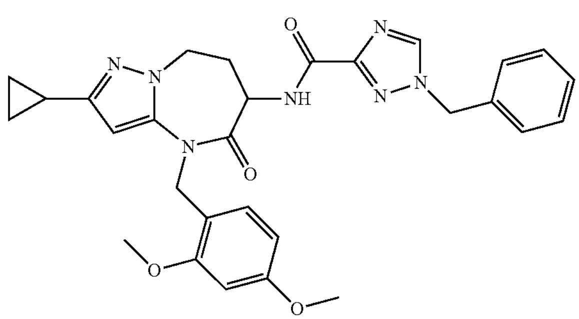 [SMILES: COc1ccc(CN2C(=O)C(NC(=O)c3ncn(Cc4ccccc4)n3)CCn3nc(C4CC4)cc32)c(OC)c1]

Step 7: 1-benzyl-N-[2-cyclopropyl-4-[(2,4-dimethoxyphenyl)methyl]-5-oxo-7,8-dihydro-6H-pyrazolo[1,5-a][1,3]diazepin-6-yl]-1,2,4-triazole-3-carboxamide A mixture of 6-amino-2-cyclopropyl-4-[(2,4-dimethoxyphenyl)methyl]-7,8-dihydro-6H-pyrazolo[1,5-a][1,3]diazepin-5-one (200.0 mg, 0.56 mmol), 1-benzyl-1,2,4-triazole-3-carboxylic acid (136.8 mg, 0.67 mmol), 1-hydroxybenzotriazole (91.0 mg, 0.67 mmol) and 1-(3-dimethylaminopropyl)-3-ethylcarbodiimidehydrochloride (129.1 mg, 0.67 mmol). in N,N-dimethylformamide (6 mL) was stirred for 2 h at 20° C. This reaction mixture was concentrated under reduced pressure and the residue was purified by column chromatography (silica gel: 100-200 mesh, eluting 5% methanol in dichloromethane) to give 1-benzyl-N-[2-cyclopropyl-4-[(2,4-dimethoxyphenyl)methyl]-5-oxo-7,8-dihydro-6H-pyrazol o[1,5-a][1,3]diazepin-6-yl]-1,2,4-triazole-3-carboxamide (150 mg, 49.4% yield) as colorless oil. LCMS $R_T$=1.098 min, m/z=542.3 $[M+H]^+$.

LCMS (10 to 80% acetonitrile in water+0.03% trifluoacetic acid over 1.5 mins) retention time 1.098 min, ESI+ found [M+H]=542.3

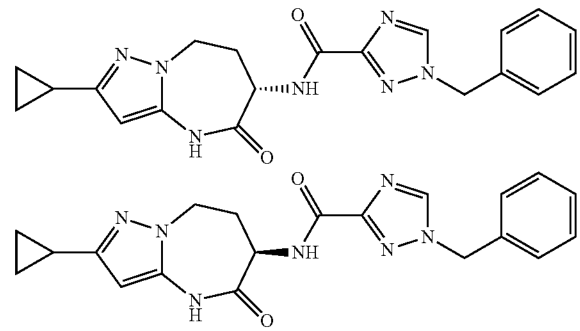

Step 8: 1-benzyl-N-(6S)-2-cyclopropyl-5-oxo-4,6,7,8-tetrahydropyrazolo[1,5-a][1,3]diazepin-6-yl-1,2,4-triazole-3-carboxamide and 1-benzyl-N-(6R)-2-cyclopropyl-5-oxo-4,6,7,8-tetrahydropyrazolo[1,5-a][1,3]diazepin-6-yl-1,2,4-triazole-3-carboxamide A mixture of 1-benzyl-N-[2-cyclopropyl-4-[(2,4-dimethoxyphenyl)methyl]-5-oxo-7,8-dihydro-6H-pyrazol o[1,5-a][1,3]diazepin-6-yl]-1,2,4-triazole-3-carboxamide (150.0 mg, 0.28 mmol) in trifluoroacetic acid (3.0 mL, 40 mmol) was stirred at 60° C. for 12 h and then concentrated under reduced pressure. The residue was purified by RP-HPLC (acetonitrile 17-47%/0.05% HCl in water) to afford 1-benzyl-N-(6S)-2-cyclopropyl-5-oxo-4,6,7,8-tetrahydropyrazolo[1,5-a][1,3]diazepin-6-yl-1, 2,4-triazole-3-carboxamide (80 mg, 73.8% yield) as a white solid. The racemic material was separated by chiral SFC to give:

1-benzyl-N-[(6S)-2-cyclopropyl-5-oxo-4,6,7,8-tetrahydropyrazolo[1,5-a][1,3]diazepin-6-yl]-1,2,4-triazole-3-carboxamide (Peak 1, retention time 3.786 min) (39.2 mg, 48.5% yield) as white solids. $^1$H NMR (400 MHz, DMSO-$d_6$) δ 10.32 (s, 1H), 8.82 (s, 1H), 8.48 (d, J=8.0 Hz, 1H), 7.41-7.26 (m, 5H), 5.66 (s, 1H), 5.48 (s, 2H), 4.38-4.35 (m, 1H), 4.28-4.20 (m, 1H), 4.13-4.02 (m, 1H), 2.59-2.54 (m, 1H), 2.34-2.25 (m, 1H), 1.84-1.75 (m, 1H), 0.85-0.79 (m, 2H), 0.65-0.59 (m, 2H). LCMS $R_T$=0.869 min, m/z=392.0 $[M+H]^+$.

LCMS (10 to 80% acetonitrile in water+0.03% trifluoacetic acid over 2.0 mins) retention time 0.869 min, ESI+ found [M+H]=392.0

1-benzyl-N-[(6R)-2-cyclopropyl-5-oxo-4,6,7,8-tetrahydropyrazolo[1,5-a][1,3]diazepin-6-yl]-1,2,4-triazole-3-carboxamide (Peak 2, retention time 4.390 min) (40.0 mg, 50% yield) as white solids. $^1$H NMR (400 MHz, DMSO-d6) δ10.32 (s, 1H), 8.82 (s, 1H), 8.48 (d, J=7.9 Hz, 1H), 7.41-7.26 (m, 5H), 5.66 (s, 1H), 5.48 (s, 2H), 4.37 (m, 1H), 4.28-4.20 (m, 1H), 4.13-4.02 (m, 1H), 2.59-2.54 (m, 1H), 2.34-2.25 (m, 1H), 1.84-1.75 (m, 1H), 0.85-0.79 (m, 2H), 0.65-0.59 (m, 2H). LCMS $R_T$=0.737 min, m/z=392.0 $[M+H]^+$.

LCMS (5 to 95% acetonitrile in water+0.03% trifluoacetic acid over 1.5 mins) retention time 0.737 min, ESI+ found [M+H]=392.0

SFC condition: Column: Chiralpak AS-3 150×4.6 mm I.D., 3 um Mobile phase: A: $CO_2$ B: methanol (0.05% DEA)

Gradient: from 5% to 40% of B in 5 min and hold 40% for 2.5 min, then 5% of B for 2.5 min Flow rate: 2.5 mL/min Column temp.: 35° C.

Example 586

WX Method 054

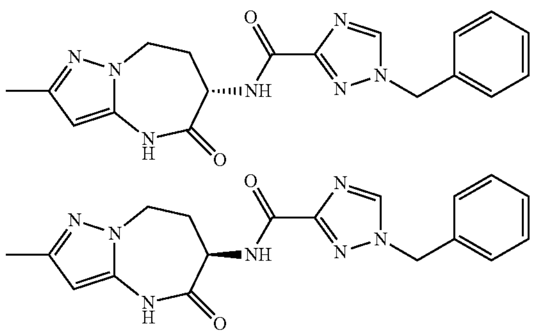

1-benzyl-N-(6S)-2-methyl-5-oxo-4,6,7,8-tetrahydro-pyrazolo[1,5-a][1,3]diazepin-6-yl-1,2, 4-triazole-3-carboxamide and 1-benzyl-N-(6R)-2-methyl-5-oxo-4,6,7,8-tetrahydropyrazolo[1,5-a][1,3]diazepin-6-yl-1,2, 4-triazole-3-carboxamide

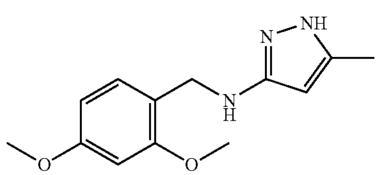

Step 1: N-[(2,4-dimethoxyphenyl)methyl]-5-methyl-1H-pyrazol-3-amine

To a solution of 2,4-dimethoxybenzaldehyde (18.8 g, 113.2 mmol) and 5-methyl-1H-pyrazol-3-amine (10.0 g, 102.9 mmol) in 1,2-dichloroethane (100 mL) was added acetic acid (6.1 g, 102.9 mmol). The reaction solution was stirred at 25° C. for 12 h, then sodium triacetoxyborohydride (32.7 g, 154.4 mmol) was added to the mixture. Stirring was continued for another 24 h and the reaction was quenched by addition of water (200 mL). The resulting mixture was extracted with dichloromethane (3×100 mL). The combined organic layers were dried over anhydrous sodium sulfate and concentrated under reduced pressure. The residue was purified by column chromatography (silica gel, 100-200 mesh, 40 to 100% ethyl acetate in petroleum ether) to give N-[(2,4-dimethoxyphenyl)methyl]-5-methyl-1H-pyrazol-3-amine (3.0 g, 12%) as a brown oil, used as is in the next step. LCMS $R_T$=0.617 min, m/z=248.1 $[M+H]^+$.

LCMS (5 to 95% acetonitrile in water+0.03% trifluoacetic acid over 1.5 mins) retention time 0.617 min, ESI+ found [M+H]=248.1

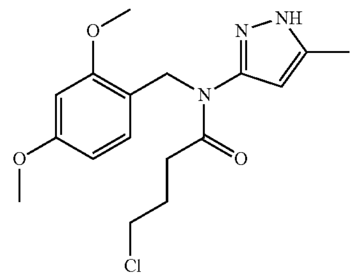 [SMILES: COc1ccc(CN(C(=O)CCCCl)c2cc(C)[nH]n2)c(OC)c1]

Step 2: 4-chloro-N-[(2,4-dimethoxyphenyl)methyl]-N-(5-methyl-1H-pyrazol-3-yl)butanamide To a solution of N-[(2,4-dimethoxyphenyl)methyl]-5-methyl-1H-pyrazol-3-amine (7.00 g, 28.31 mmol) and N,N-diisopropylethylamine (17.42 mL, 169.84 mmol) in dichloromethane (150 mL) was added 4-dimethylaminopyridine (0.35 g, 2.83 mmol) and 4-chlorobutanoyl chloride (11.97 g, 84.92 mmol) at 0° C. After addition, the mixture was stirred at 20° C. for 12 h and then quenched by addition of methanol (10 mL). The mixture was stirred for 0.5 h and then concentrated under reduced pressure. The residue was purified by column chromatography (silica gel, 100-200 mesh, 0 to 50% ethyl acetate in petroleum ether) to afford 4-chloro-N-[(2,4-dimethoxyphenyl)methyl]-N-(5-methyl-1H-pyrazol-3-yl)butanamide (2.5 g, 25.1% yield) as slight yellow oil. LCMS $R_T$=0.875 min, m/z=352.1 $[M+H]^+$.

LCMS (5 to 95% acetonitrile in water+0.03% trifluoacetic acid over 1.5 mins) retention time 0.875 min, ESI+ found [M+H]=352.1

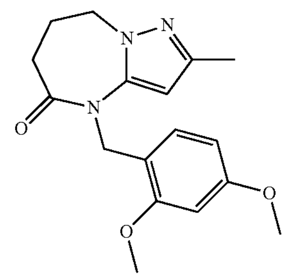 [SMILES: COc1ccc(CN2C(=O)CCCn3nc(C)cc32)c(OC)c1]

Step 3: 4-[(3,5-dimethoxyphenyl)methyl]-2-methyl-7,8-dihydro-6H-pyrazolo[1,5-a][1,3]diazepin-5-one A mixture of 4-chloro-N-[(2,4-dimethoxyphenyl)methyl]-N-(5-methyl-1H-pyrazol-3-yl)butanamide (800 mg, 2.27 mmol) and cesium carbonate (1482 mg, 4.55 mmol) in N,N-dimethylformamide (10 mL) was stirred at 20° C. for 3 h and then concentrated under reduced pressure. The residue was diluted with water (30 mL) and extracted with ethyl acetate (3×50 mL). The combined organic layers were washed with brine (50 mL), dried and concentrated. The residue was purified by column chromatography (silica gel, 100-200 mesh, 0 to 30% ethyl acetate in petroleum ether) to afford 4-[(3,5-dimethoxyphenyl)methyl]-2-methyl-7,8-dihydro-6H-pyrazolo[1,5-a][1,3]diazepin-5-one (400 mg, 55.8%) as a yellow solid. $^1H$ NMR (400 MHz, $CD_3OD$) δ7.00 (d, J=8 Hz, 1H), 6.48 (d, J=2.4 Hz, 1H), 6.48-6.41 (m, 1H), 5.77 (s, 1H), 4.69 (s, 2H), 4.01-3.98 (m, 2H), 3.69 (d, J=8.8 Hz, 6H), 2.26-2.14 (m, 4H), 2.04 (s, 3H).

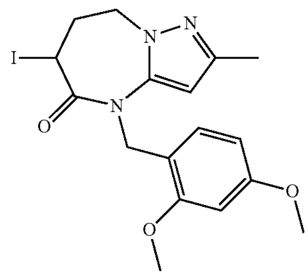 [SMILES: COc1ccc(CN2C(=O)C(I)CCn3nc(C)cc32)c(OC)c1]

Step 4: 4-[(2,4-dimethoxyphenyl)methyl]-6-iodo-2-methyl-7,8-dihydro-6H-pyrazolo[1,5-a][1,3]diazepin-5-one To a solution of 4-[(2,4-dimethoxyphenyl)methyl]-2-methyl-7,8-dihydro-6H-pyrazolo[1,5-a][1,3]diazepin-5-one (50 mg, 0.16 mmol) in dichloromethane (20 mL) was treated with N1,N1,N2,N2-tetramethylethane-1,2-diamine (184 mg, 1.59 mmol) at −15° C., followed by iodotrimethylsilane (317 mg, 1.59 mmol). Stirring at −15° C. was continued for 1.5 h, and then iodine (120 mg, 0.48 mmol) was added. The mixture was stirred for another 3 h and then quenched by addition of saturated sodium sulphite (3 mL) and water (15 mL). The resulting mixture was extracted with ethyl acetate (3×20 mL). The combined organic layers were dried over anhydrous sodium sulfate and concentrated under reduced pressure. The residue was purified by preparative TLC (50% ethyl acetate in petroleum ether, $R_f$=0.5) to afford 4-[(2,4-dimethoxyphenyl)methyl]-6-iodo-2-methyl-7,8-dihydro-6H-pyrazolo[1,5-a][1,3]diazepin-5-one (50 mg, 72%) as a yellow solid, used as is in the next step.

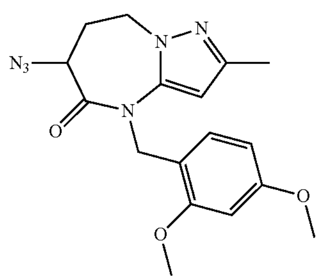 [SMILES: COc1ccc(CN2C(=O)C(N=[N+]=[N-])CCn3nc(C)cc32)c(OC)c1]

Step 5: 6-azido-4-[(2,4-dimethoxyphenyl)methyl]-2-methyl-7,8-dihydro-6H-pyrazolo[1,5-a][1,3]diazepin-5-one To a solution of 4-[(2,4-dimethoxyphenyl)methyl]-6-iodo-2-methyl-7,8-dihydro-6H-pyrazolo[1,5-a][1,3]diazepin-5-one (40 mg, 0.09 mmol) in N,N-dimethylformamide (3 mL) was added sodium azide (147 mg, 2.27 mmol). The reaction mixture was stirred at 25° C. for 12 h and concentrated under reduced pressure. The residue was diluted with water (20 mL) and extracted with ethyl acetate (3×20 mL). The combined organic layers were washed with brine (20 mL), dried over anhydrous sodium sulfate and concentrated. The residue was purified by preparative TLC (50% ethyl acetate in petroleum ether, $R_f$=0.5) to afford 6-azido-4-[(2,4-dimethoxyphenyl)methyl]-2-methyl-7,8-dihydro-6H-pyrazolo[1,5-a][1,3]diazepin-5-one (25 mg, 77%) as a white solid, used as is in the next step.

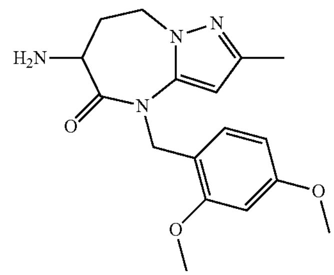 [SMILES: COc1ccc(CN2C(=O)C(N)CCn3nc(C)cc32)c(OC)c1]

Step 6: 6-amino-4-[(2,4-dimethoxyphenyl)methyl]-2-methyl-7,8-dihydro-6H-pyrazolo[1,5-a][1,3]diazepin-5-one A mixture of 6-azido-4-[(2,4-dimethoxyphenyl)methyl]-2-methyl-7,8-dihydro-6H-pyrazolo[1,5-a][1,3]diazepin-5-one (30 mg, 0.08 mmol) and palladium (10% on carbon, 22 mg, 0.02 mmol) in methanol (15 mL) was hydrogenated (15 psi) at 25° C. for 2 h and then filtered. The filtrate was concentrated under reduced pressure to afford 6-amino-4-[(2,4-dimethoxyphenyl)methyl]-2-methyl-7,8-dihydro-6H-pyrazolo[1,5-a][1,3]diazepin-5-one (25 mg, 90%) as a colorless oil. LCMS $R_T$=0.618 min, m/z=331.0 $[M+H]^+$.

LCMS (5 to 95% acetonitrile in water+0.03% trifluoacetic acid over 1.5 mins) retention time 0.618 min, ESI+ found [M+H]=331.0

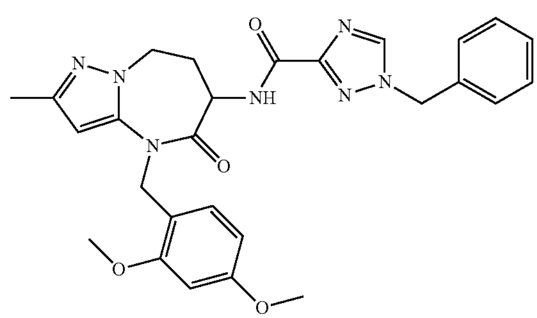 [SMILES: COc1ccc(CN2C(=O)C(NC(=O)c3ncn(Cc4ccccc4)n3)CCn3nc(C)cc32)c(OC)c1]

Step 7: 1-benzyl-N-[4-[(2,4-dimethoxyphenyl)methyl]-2-methyl-5-oxo-7,8-dihydro-6H-pyrazolo[1,5-a][1,3]diazepin-6-yl]-1,2,4-triazole-3-carboxamide A mixture of 6-amino-4-[(2,4-dimethoxyphenyl)methyl]-2-methyl-7,8-dihydro-6H-pyrazolo[1,5-a][1,3]diazepin-5-one (20 mg, 0.06 mmol), 1-benzyl-1,2,4-triazole-3-carboxylic acid (16 mg, 0.08 mmol), 1-hydroxybenzotriazole (12 mg, 0.09 mmol) and 1-(3-dimethyl aminopropyl)-3-ethylcarbodiimidehydrochloride (17 mg, 0.09 mmol). in N,N-dimethylformamide (3 mL) was stirred for 40 min at 40° C. This reaction mixture was concentrated under reduced pressure and the residue was purified by preparative TLC (10% methanol in dichloromethane, $R_f$=0.3) to afford 1-benzyl-N-[4-[(2,4-dimethoxyphenyl)methyl]-2-methyl-5-oxo-7,8-dihydro-6H-pyrazolo[1,5-a][1,3]diazepin-6-yl]-1,2,4-triazole-3-carboxamide (20 mg, 64%) as a white solid. LCMS $R_T$=1.068 min, m/z=515.9 $[M+H]^+$.

LCMS (10 to 80% acetonitrile in water+0.03% trifluoacetic acid over 1.5 mins) retention time 1.068 min, ESI+ found [M+H]=515.9

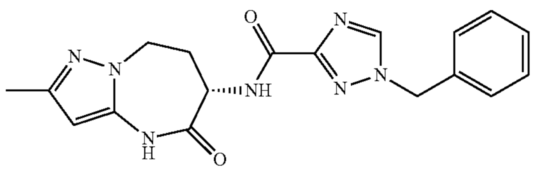

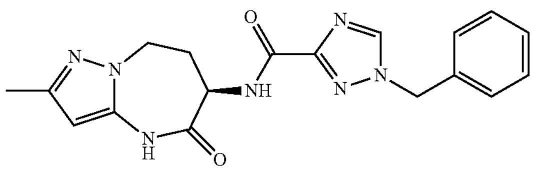

Step 8: 1-benzyl-N-(6S)-2-methyl-5-oxo-4,6,7,8-tetrahydropyrazolo[1,5-a][1,3]diazepin-6-yl-1,2,4-triazole-3-carboxamide and 1-benzyl-N-(6R)-2-methyl-5-oxo-4,6,7,8-tetrahydropyrazolo[1,5-a][1,3]diazepin-6-yl-1,2, 4-triazole-3-carboxamide A mixture of 1-benzyl-N-[4-[(2,4-dimethoxyphenyl)methyl]-2-methyl-5-oxo-7,8-dihydro-6H-pyrazolo[1,5-a][1,3]diazepin-6-yl]-1,2,4-triazole-3-carboxamide (60.0 mg, 0.12 mmol) in trifluoroacetic acid (1.5 mL, 20 mmol) was stirred at 60° C. for 12 h and then concentrated under reduced pressure. The residue was purified by RP-HPLC (acetonitrile 18-48%/0.05% FA in water) to afford 1-benzyl-N-(2-methyl-5-oxo-4,6,7,8-tetrahydropyrazolo[1,5-a][1,3]diazepin-6-yl)-1,2,4-triazole-3-carboxamide (40 mg, 94.1% yield) as a white solid. The racemic material was separated by chiral SFC to give:

1-benzyl-N-(6S)-2-methyl-5-oxo-4,6,7,8-tetrahydropyrazolo[1,5-a][1,3]diazepin-6-yl-1,2,4-triazole-3-carboxamide (Peak 1, retention time 4.974 min) (7 mg, 17%) as white solids. $^1$H NMR (400 MHz, DMSO-$d_6$) δ 8.80 (s, 1H), 8.45 (d, J=7.6 Hz, 1H), 7.38-7.25 (m, 5H), 5.72 (s, 1H), 5.46 (s, 2H), 4.39-4.34 (m, 1H), 4.28-4.19 (m, 1H), 4.13-4.01 (m, 1H), 2.64 (s, 1H), 2.30 (s, 1H), 2.09 (s, 3H). LCMS $R_T$=0.689 min, m/z=366.0 $[M+H]^+$.

LCMS (5 to 95% acetonitrile in water+0.03% trifluoacetic acid over 1.5 mins) retention time 0.689 min, ESI+ found [M+H]=366.0

1-benzyl-N-(6R)-2-methyl-5-oxo-4,6,7,8-tetrahydropyrazolo[1,5-a][1,3]diazepin-6-yl-1,2,4-triazole-3-carboxamide (Peak 2, retention time 5.659 min) (8.9 mg, 22%) as white solids. $^1$H NMR (400 MHz, DMSO-d6) δ 8.80 (s, 1H), 8.45 (d, J=7.5 Hz, 1H), 7.38-7.25 (m, 5H), 5.72 (s, 1H), 5.46 (s, 2H), 4.36 (m, 1H), 4.28-4.19 (m, 1H), 4.13-4.01 (m, 1H), 2.64 (s, 1H), 2.30 (s, 1H), 2.09 (s, 3H). LCMS $R_T$=0.684 min, m/z=366.1 $[M+H]^+$.

LCMS (5 to 95% acetonitrile in water+0.03% trifluoacetic acid over 1.5 mins) retention time 0.684 min, ESI+ found [M+H]=366.1

SFC conditions: Column: Chiralpak AS-H 250×4.6 mm I.D., 5 um Mobile phase: A: CO2 B: ethanol (0.05% DEA) Gradient: from 5% to 40% of B in 5.0 min and hold 40% for 2.5 min, then 5% of B for 2.5 min Flow rate: 2.5 mL/min Column temperature: 35° C.

Example 587

WX Method 034

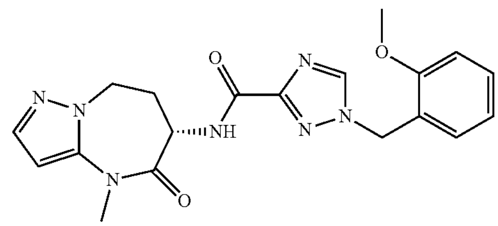 [SMILES: COc1ccccc1Cn1cnc(C(=O)N[C@H]2CCn3nccc3N(C)C2=O)n1]

1-[(2-methoxyphenyl)methyl]-N-(6S)-4-methyl-5-oxo-7,8-dihydro-6H-pyrazolo[1,5-a][1, 3]diazepin-6-yl-1,2,4-triazole-3-carboxamide

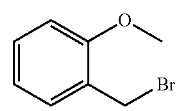

Step 1: 1-(bromomethyl)-2-methoxybenzene

A mixture of 2-methylanisole (2.0 g, 16.37 mmol), NBS (2.91 g, 16.37 mmol) and AIBN (0.05 g, 0.28 mmol) in 1,2-dichloroethane (30 mL) was stirred for 3 h at 88° C. The mixture was concentrated under reduced pressure and the residue was purified by column chromatography (silica gel, 100-200 mesh, 0 to 10% ethyl acetate in petroleum ether) to afford 1-(bromomethyl)-2-methoxy-benzene (1.2 g, 37%) as a white solid. $^1$H NMR (400 MHz, $CDCl_3$) δ 7.33-7.25 (m, 2H), 6.94-6.87 (m, 2H), 4.57 (s, 2H), 3.90 (s, 3H).

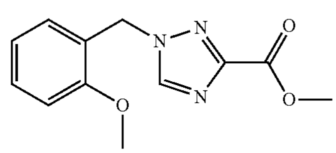 [SMILES: COC(=O)c1ncn(Cc2ccccc2OC)n1]

Step 2: methyl 1-(2-methoxybenzyl)-1H-1,2,4-triazole-3-carboxylate

A mixture of methyl 1H-1,2,4-triazole-3-carboxylate (395 mg, 3.11 mmol), potassium carbonate (859 mg, 6.22 mmol) and 1-(bromomethyl)-2-methoxybenzene (750 mg, 3.73 mmol) in N,N-dimethylformamide (10 mL) was stirred at 25° C. for 12 h and then filtered. The filtrate was concentrated under reduced pressure and the residue was purified by column chromatography (silica gel, 100-200 mesh, 0 to 40% ethyl acetate in petroleum ether) to afford methyl 1-[(2-methoxyphenyl)methyl]-1,2,4-triazole-3-carboxylate (400 mg, 52%) as a white solid. $^1$H NMR (400 MHz, $CDCl_3$) δ 8.10 (s, 1H), 7.38-7.29 (m, 2H), 6.98-6.90 (m, 2H), 5.40 (s, 2H), 3.97 (s, 3H), 3.84 (s, 3H).

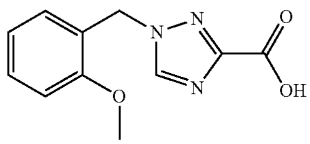 [SMILES: COc1ccccc1Cn1cnc(C(=O)O)n1]

Step 3: 1-(2-methoxybenzyl)-1H-1,2,4-triazole-3-carboxylic acid

A mixture of methyl 1-[(2-methoxyphenyl)methyl]-1,2,4-triazole-3-carboxylate (230 mg, 0.93 mmol) and lithium hydroxide (111 mg, 4.65 mmol) in tetrahydrofuran (4 mL) and water (1 mL) was stirred for 3 h at 25° C. and the organic solvent was evaporated under reduced pressure. The aqueous residue was adjusted to pH=1-2 by addition of 20% aqueous HCl. The resulting solid was collected by filtration and dried to give crude 1-[(2-methoxyphenyl)methyl]-1,2,4-triazole-3-carboxylic acid (150 mg, 69%) as a white solid, used as is in the next step.

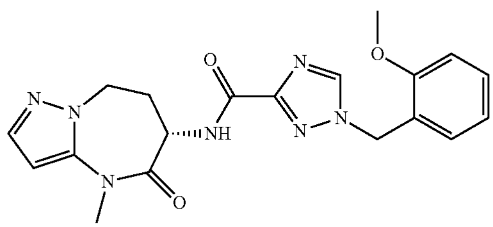 [SMILES: COc1ccccc1Cn1cnc(C(=O)N[C@H]2CCn3nccc3N(C)C2=O)n1]

Step 4: 1-[(2-methoxyphenyl)methyl]-N-(6S)-4-methyl-5-oxo-7,8-dihydro-6H-pyrazolo[1,5-a][1,3]diazepin-6-yl-1,2,4-triazole-3-carboxamide To a stirred solution of 1-[(2-methoxyphenyl)methyl]-1,2,4-triazole-3-carboxylic acid (49 mg, 0.21 mmol) in N,N-dimethylformamide (3 mL) was added (6S)-6-amino-4-methyl-7,8-dihydro-6H-pyrazolo[1,5-a][1,3]diazepin-5-one (32 mg, 0.18 mmol), 1-(3-dimethylaminopropyl)-3-ethylcarbodiimidehydrochloride (51 mg, 0.27 mmol) and 1-hydroxybenzotriazole (36 mg, 0.27 mmol). The mixture was stirred at 25° C. for 12 h and concentrated under reduced pressure. The residue was purified by RP-HPLC (acetonitrile 22-52%/0.05% ammonium hydroxide in water) to afford 1-[(2-methoxyphenyl)methyl]-N-(6 S)-4-methyl-5-oxo-7,8-dihydro-6H-pyrazolo[1,5-a][1,3]diazepin-6-yl-1,2,4-triazole-3-carboxamide (36 mg, 50%) as a white solid.

$^1$H NMR (400 MHz, $CD_3OD$) δ8.44 (s, 1H), 7.51 (s, 1H), 7.36-7.32 (m, 1H), 7.28-7.26 (m, 1H), 7.00 (d, J=8.0 Hz, 1H), 6.96-6.93 (m, 1H), 6.29 (s, 1H), 5.42 (s, 2H), 4.51-4.46 (m, 1H), 4.44-4.38 (m, 1H), 4.30-4.22 (m, 1H), 3.83 (s, 3H), 3.34 (s, 3H), 2.89-2.79 (m, 1H), 2.29-2.21 (m, 1H). LCMS $R_T$=1.48 min, m/z=396.1 $[M+H]^+$.

LCMS (10 to 80% acetonitrile in water+0.05% ammonium hydroxide over 3 mins) retention time 1.48 min, ESI+ found [M+H]=396.1.

Example 588

WX Method 062

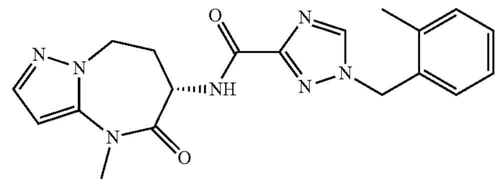 [SMILES: Cc1ccccc1Cn1cnc(C(=O)N[C@H]2CCn3nccc3N(C)C2=O)n1]

1-(o-tolylmethyl)-N-(6S)-4-methyl-5-oxo-7,8-dihydro-6H-pyrazolo[1,5-a][1,3]diazepin-6-yl-1,2,4-triazole-3-carboxamide

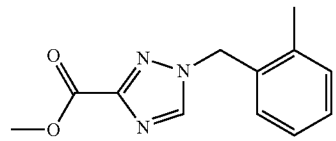 [SMILES: COC(=O)c1ncn(Cc2ccccc2C)n1]

Step 1: methyl 1-(2-methylbenzyl)-1H-1,2,4-triazole-3-carboxylate

To a solution of methyl 1H-1,2,4-triazole-3-carboxylate (200 mg, 1.57 mmol) in N,N-dimethylformamide (6 mL) was added potassium carbonate (435 mg, 3.14 mmol) and 1-(bromomethyl)-2-methylbenzene (349 mg, 1.89 mmol). The mixture was stirred at 25° C. for 2 h and filtered. The filtrate was concentrated under reduced pressure and the residue was purified by column chromatography (silica gel, 100-200 mesh, 0 to 80% ethyl acetate in petroleum ether) to afford methyl 1-(2-methylbenzyl)-1H-1,2,4-triazole-3-carboxylate (240 mg, 66%) as a white solid, used as is in the next step.

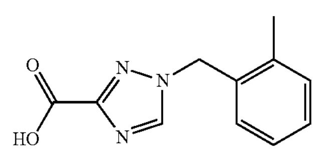 [SMILES: Cc1ccccc1Cn1cnc(C(=O)O)n1]

Step 2: 1-(2-methylbenzyl)-1H-1,2,4-triazole-3-carboxylic acid

A mixture of methyl 1-(2-methylbenzyl)-1H-1,2,4-triazole-3-carboxylate (240 mg, 1.03 mmol) and potassium hydroxide (124 mg, 5.19 mmol) in tetrahydrofuran/methanol/water (5 mL, 2:2:1) was stirred at 25° C. for 2 h. The organic solvents were evaporated under reduced pressure and the mixture was diluted with water (20 mL). The solution was adjusted to pH=4 by addition of 2N HCl. The resulting solid was collected by filtration and dried to give crude 1-(2-methylbenzyl)-1H-1,2,4-triazole-3-carboxylic acid (180 mg, 80%) as a white solid, use as is in the next step.

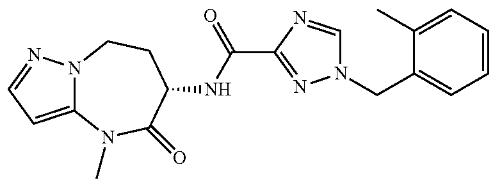 [SMILES: Cc1ccccc1Cn1cnc(C(=O)N[C@H]2CCn3nccc3N(C)C2=O)n1]

Step 3: 1-(o-tolylmethyl)-N-(6S)-4-methyl-5-oxo-7,8-dihydro-6H-pyrazolo[1,5-a][1,3]diazepin-6-yl-1,2,4-triazole-3-carboxamide A mixture of (6S)-6-amino-4-methyl-7,8-dihydro-6H-pyrazolo[1,5-a][1,3]diazepin-5-one (40 mg, 0.22 mmol), 1-(o-tolylmethyl)-1,2,4-triazole-3-carboxylic acid (51 mg, 0.23 mmol), 1-hydroxybenzotriazole (45 mg, 0.33 mmol) and 1-(3-dimethyl aminopropyl)-3-ethylcarbodiimidehydrochloride (64 mg, 0.33 mmol) in N,N-dimethylformamide (3 mL) was stirred at 20° C. for 16 h and concentrated under reduced pressure. The residue was purified by RP-HPLC (acetonitrile 30-60%/0.05% ammonium hydroxide in water) to afford 1-(o-tolylmethyl)-N-(6S)-4-methyl-5-oxo-7,8-dihydro-6H-pyrazolo][1,5-a][1,3]diazepin-6-yl-1,2,4-triazole-3-carboxamide (44 mg, 51%) as a white solid. $^1$H NMR (400 MHz, $CD_3OD$) δ 8.45 (s, 1H), 7.52-7.51 (m, 1H), 7.26-7.15 (m, 4H), 6.31-6.30 (m, 1H), 5.50 (s, 2H), 4.53-4.40 (m, 2H), 4.30-4.25 (m, 1H), 3.35 (s, 3H), 2.89-2.83 (m, 1H), 2.34 (s, 3H), 2.31-2.23 (m, 1H). LCMS $R_T$=1.48 min; m/z=380.2 $(M+H)^+$.

LCMS (10 to 80% acetonitrile in water+0.03% ammonium hydroxide acid over 3 mins) retention time 1.48 min, ESI+ found [M+H]=380.2.

Example 589

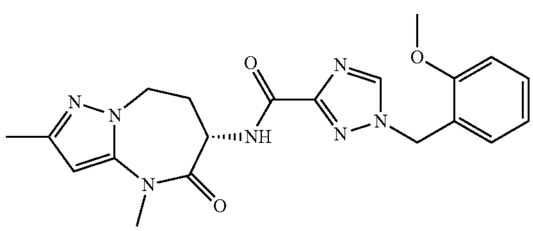 [SMILES: COc1ccccc1Cn1cnc(C(=O)N[C@H]2CCn3nc(C)cc3N(C)C2=O)n1]

1-[(2-methoxyphenyl)methyl]-N-(6S)-2,4-dimethyl-5-oxo-7,8-dihydro-6H-pyrazolo[1,5-a][1,3]diazepin-6-yl-1,2,4-triazole-3-carboxamide Amide coupling prepared in a similar fashion to WX Method 034. The crude was purified by RP-HPLC (acetonitrile 22-52%/0.05% ammonium hydroxide in water) to give 1-[(2-methoxyphenyl)methyl]-N-(6S)-2,4-dimethyl-5-oxo-7,8-dihydro-6H-pyrazolo[1,5-a][1, 3]diazepin-6-yl-1,2,4-triazole-3-carboxamide (47 mg, 60%) as a white solid. $^1$H NMR (400 MHz, $CD_3OD$) δ8.44 (s, 1H), 7.36-7.32 (m, 1H), 7.30-7.26 (m, 1H), 7.00 (d, J=8.4 Hz, 1H), 6.96-6.92 (m, 1H), 6.09 (s, 1H), 5.42 (s, 2H), 4.53-4.48 (m, 1H), 4.32-4.26 (m, 1H), 4.23-4.15 (m, 1H), 3.83 (s, 3H), 3.34 (s, 3H), 2.87-2.76 (m, 1H), 2.24 (s, 3H), 2.26-2.18 (m, 1H). LCMS $R_T$=1.55 min, m/z=410.1 $[M+H]^+$.

LCMS (10 to 80% acetonitrile in water+0.05% ammonium hydroxide over 3 mins) retention time 1.55 min, ESI+ found [M+H]=410.1.

Example 590

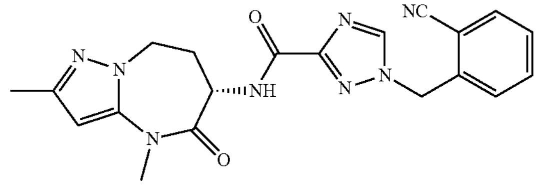 [SMILES: Cc1cc2n(n1)CC[C@H](NC(=O)c1ncn(Cc3ccccc3C#N)n1)C(=O)N2C]

1-[(2-cyanophenyl)methyl]-N-(6S)-2,4-dimethyl-5-oxo-7,8-dihydro-6H-pyrazolo[1,5-a][1, 3]diazepin-6-yl-1,2,4-triazole-3-carboxamide Amide coupling prepared in a similar fashion to WX Method 059. The crude was purified by RP-HPLC (acetonitrile 20-50%/HCl in water) to give 1-[(2-cyanophenyl) methyl]-N-(6S)-2,4-dimethyl-5-oxo-7,8-dihydro-6H-pyrazolo[1,5-a][1,3]diazepin-6-yl-1,2,4-triazole-3-carboxamide (26 mg, 36%) as white solids. $^1$H NMR (400 MHz, $CD_3OD$) δ8.79 (s, 1H), 7.81 (d, J=7.2 Hz, 1H), 7.74-7.68 (m, 1H), 7.59-7.53 (m, 1H), 7.51-7.49 (m, 1H), 6.44 (s, 1H), 5.74 (s, 2H), 4.73-4.68 (m, 1H), 4.51-4.44 (m, 1H), 4.42-4.33 (m, 1H), 3.37 (s, 3H), 2.94-2.82 (m, 1H), 2.46-2.35 (m, 4H). LCMS $R_T$=1.544 min; m/z=405.3 $(M+H)^+$.

LCMS (0 to 60% acetonitrile in water+0.03% trifluoacetic acid over 3 mins) retention time 1.544 min, ESI+ found [M+H]=405.3.

Example 591

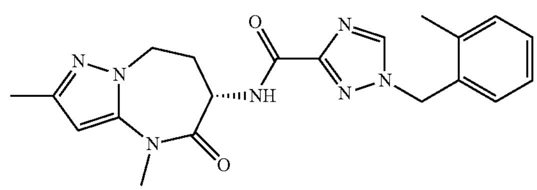 [SMILES: Cc1cc2n(n1)CC[C@H](NC(=O)c1ncn(Cc3ccccc3C)n1)C(=O)N2C]

1-(o-tolylmethyl)-N-(6S)-2,4-dimethyl-5-oxo-7,8-dihydro-6H-pyrazolo[1,5-a][1,3]diazepin-6-yl-1,2,4-triazole-3-carboxamide Amide coupling prepared in a similar fashion to WX Method 062. The crude was purified by RP-HPLC (acetonitrile 30-60%/0.05% ammonium hydroxide in water) to give 1-(o-tolylmethyl)-N-(6S)-2,4-dimethyl-5-oxo-7,8-dihydro-6H-pyrazolo[1,5-a][1,3]diazepin-6-yl-1,2,4-triazole-3-carboxamide (20 mg, 25%) as a white solid. $^1$H NMR (400 MHz, $CD_3OD$) δ8.45 (s, 1H), 7.26-7.22 (m, 2H), 7.20-7.15 (m, 2H), 6.11 (s, 1H), 5.50 (s, 2H), 4.55-4.50 (m, 1H), 4.30-4.28 (m, 1H), 4.23-4.20 (m, 1H), 3.32 (s, 3H), 2.87-2.81 (m, 1H), 2.34 (s, 3H), 2.28-2.20 (m, 4H). LCMS $R_T$=1.565 min; m/z=394.2 $(M+H)^+$.

LCMS (10 to 80% acetonitrile in water+0.03% ammonium hydroxide acid over 3 mins) retention time 1.565 min, ESI+ found [M+H]=394.2.

Example 592

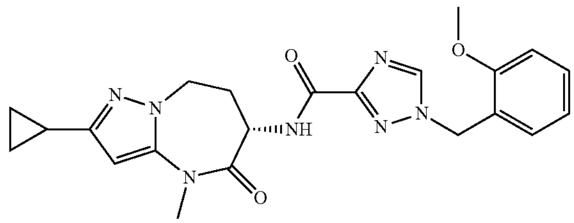 [SMILES: COc1ccccc1Cn1cnc(C(=O)N[C@H]2CCn3nc(C4CC4)cc3N(C)C2=O)n1]

1-[(2-methoxyphenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 034. The crude was purified by RP-HPLC (acetonitrile 22-52%/0.05% ammonium hydroxide in water) to give 1-[(2-methoxyphenyl)methyl]-N-(6 S)-2-cyclopropyl-4-methyl-5-oxo-7,8-dihydro-6H-pyrazol o[1,5-a][1,3]diazepin-6-yl-1,2,4-triazole-3-carboxamide (42 mg, 53%) as a white solid. $^1$H NMR (400 MHz, $CD_3OD$) δ8.44 (s, 1H), 7.36-7.32 (m, 1H), 7.30-7.26 (m, 1H), 7.00 (d, J=8.4 Hz, 1H), 6.96-6.92 (m, 1H), 5.98 (s, 1H), 5.42 (s, 2H), 4.53-4.48 (m, 1H), 4.32-4.26 (m, 1H), 4.23-4.15 (m, 1H), 3.83 (s, 3H), 3.34 (s, 3H), 2.83-2.78 (m, 1H), 2.22-2.20 (m, 1H), 1.91-1.86 (m, 1H), 0.93-0.91 (m, 2H), 0.73-0.71 (m, 2H). LCMS $R_T$=1.68 min, m/z=436.1 $[M+H]^+$.

LCMS (10 to 80% acetonitrile in water+0.05% ammonium hydroxide over 3 mins) retention time 1.68 min, ESI+ found [M+H]=436.1.

Example 593

WX Method 059

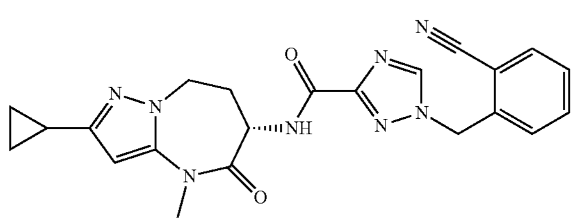 [SMILES: CN1C(=O)[C@@H](NC(=O)c2ncn(Cc3ccccc3C#N)n2)CCn2nc(C3CC3)cc21]

1-[(2-cyanophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide

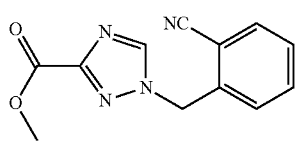 [SMILES: COC(=O)c1ncn(Cc2ccccc2C#N)n1]

Step 1: methyl 1-(2-cyanobenzyl)-1H-1,2,4-triazole-3-carboxylate

To a solution of 2-(bromomethyl)benzonitrile (386 mg, 1.97 mmol) in N,N-dimethylformamide (3 mL) was added methyl 1H-1,2,4-triazole-3-carboxylate (250 mg, 1.97 mmol) and potassium carbonate (408 mg, 2.95 mmol). The mixture was stirred at 25° C. for 2 h and then filtered. The filtrate was concentrated under reduced pressure and the residue was purified by column chromatography (silica gel, 100-200 mesh, 0-50% petroleum ether) to give methyl 1-[(2-cyanophenyl)methyl]-1,2,4-triazole-3-carboxylate (240 mg, 50%) as a white solid, used as is in the next step.

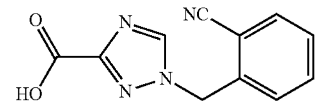 [SMILES: N#Cc1ccccc1Cn1cnc(C(=O)O)n1]

Step 2: 1-(2-cyanobenzyl)-1H-1,2,4-triazole-3-carboxylic acid

A mixture of methyl 1-[(2-cyanophenyl)methyl]-1,2,4-triazole-3-carboxylate (150 mg, 0.62 mmol) and lithium hydroxide (74 mg, 3.1 mmol) in tetrahydrofuran (5 mL) and water (2 mL) was stirred at for 2 h. The organic solvent was evaporated under reduced pressure and the aqueous solution was adjusted to pH=5 by addition of 1N HCl. The resulting mixture was extracted with dichloromethane (3×10 mL). The combined organic layers were concentrated under reduced pressure to afford crude methyl 1-[(2-cyanophenyl)methyl]-1,2,4-triazole-3-carboxylate (150 mg, 85%) as a white solid, used as is in the next step.

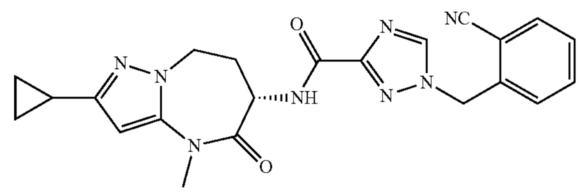 [SMILES: CN1C(=O)[C@@H](NC(=O)c2ncn(Cc3ccccc3C#N)n2)CCn2nc(C3CC3)cc21]

Step 3: 1-[(2-cyanophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide A mixture of (6S)-6-amino-2-cyclopropyl-4-methyl-7,8-dihydro-6H-pyrazolo[1,5-a][1,3]diazepin-5-one (38 mg, 0.18 mmol), 1-(3-dimethylaminopropyl)-3-ethylcarbodiimidehydrochloride (50 mg, 0.26 mmol), 1-hydroxybenzotriazole (35 mg, 0.26 mmol) and 1-[(2-cyanophenyl)methyl]-1,2,4-triazole-3-carboxylic acid (40 mg, 0.18 mmol) in N,N-dimethylformamide (5 mL) was stirred at 20° C. for 2 h and concentrated under reduced pressure. The residue was purified by RP-HPLC (acetonitrile 22-52%/HCl in water) to afford 1-[(2-cyanophenyl)methyl]-N-(6 S)-2-cyclopropyl-4-methyl-5-oxo-7,8-dihydro-6H-pyrazolo[1,5-a][1,3]diazepin-6-yl-1,2,4-triazole-3-carboxamide (46 mg, 61%) as white solids. $^1$H NMR (400 MHz, $CD_3OD$) δ8.84 (s, 1H), 7.81 (d, J=7.6 Hz, 1H), 7.73-7.68 (m, 1H), 7.59-7.48 (m, 2H), 6.38 (s, 1H), 5.75 (s, 2H), 4.75-4.70 (m, 1H), 4.54-4.45

(m, 1H), 4.42-4.33 (m, 1H), 3.36 (s, 3H), 2.94-2.83 (m, 1H), 2.46-2.36 (m, 1H), 2.09-2.01 (m, 1H), 1.20-1.17 (m, 2H), 1.00-0.91 (m, 2H). LCMS $R_T$=1.65 min; m/z=431.3 $(M+H)^+$.

LCMS (5 to 95% acetonitrile in water+0.03% trifluoacetic acid over 1.5 mins) retention time 1.65 min, ESI+ found [M+H]=431.3.

Example 594

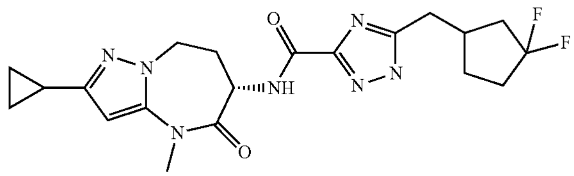 [SMILES: CN1C(=O)[C@@H](NC(=O)c2n[nH]c(CC3CCC(F)(F)C3)n2)CCn2nc(C3CC3)cc21]

1-[(3,3-difluorocyclopentyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide N-Alkylation prepared in a similar fashion to WX Method 041. The crude was purified by RP-HPLC (acetonitrile 0-40%/0.05% ammonium hydroxide in water) to give 1-[(3,3-difluorocyclopentyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide (9.1 mg, 32%). $^1$H NMR (400 MHz, $CD_3OD$) δ8.51 (s, 1H), 6.01 (s, 1H), 4.57-4.50 (m, 1H), 4.35-4.27 (m, 3H), 4.24-4.16 (m, 1H), 3.32 (s, 3H), 2.92-2.70 (m, 3H), 2.29-2.11 (m, 3H), 1.97-1.83 (m, 3H), 1.63-1.55 (m, 1H), 0.99-0.91 (m, 2H), 0.79-0.69 (m, 2H). LC-MS $R_T$=0.945 min, m/z=434.3 $(M+H)^+$.

LCMS (10 to 80% acetonitrile in water+0.03% TFA over 2.0 mins) retention time 0.945 min, ESI+ found [M+H]=434.3

Example 595

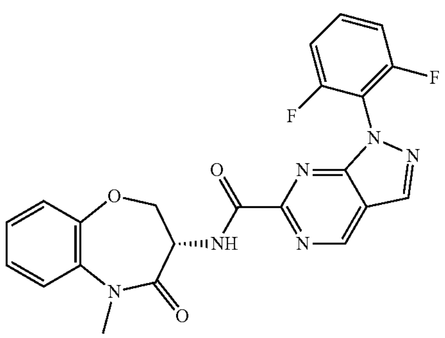 [SMILES: CN1C(=O)[C@@H](NC(=O)c2ncc3cnn(-c4c(F)cccc4F)c3n2)COc2ccccc21]

1-(2,6-difluorophenyl)-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide Amide coupling prepared in a similar fashion to WX Method 140. The crude was purified by RP-HPLC (35% to 65% acetonitrile/0.05% HCl in water) to afford 1-(2,6-difluorophenyl)-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide (19 mg, 27%) as a white solid. $^1$H NMR (400 MHz, $CD_3OD$) δ 9.53 (s, 1H), 9.23 (d, J=7.2 Hz, 1H), 8.70 (s, 1H), 7.74-7.67 (m, 1H), 7.46-7.40 (m, 1H), 7.34-7.28 (m, 3H), 7.26-7.21 (m, 1H), 5.06-5.01 (m, 1H), 4.69-4.65 (m, 1H), 4.45-4.38 (m, 1H), 3.42 (s, 3H). LCMS $R_T$=1.851 min; m/z=451.2 $(M+H)^+$.

LCMS (0 to 60% acetonitrile in water+0.03% trifluoacetic acid over 3.0 mins) retention time 1.851 min, ESI+ found [M+H]=451.2.

Example 596

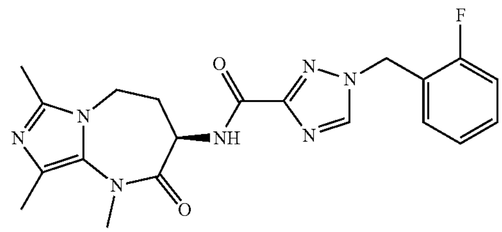 [SMILES: Cc1nc(C)n2c1N(C)C(=O)[C@H](NC(=O)c1ncn(Cc3ccccc3F)n1)CC2]

1-[(2-fluorophenyl)methyl]-N-(3R)-1,7,9-trimethyl-2-oxo-4,5-dihydro-3H-imidazo[1,5-a][1,3]diazepin-3-yl-1,2,4-triazole-3-carboxamide Amide coupling prepared in a similar fashion to WX Method 096. The crude was purified by RP-HPLC (18% to 48% acetonitrile/0.05% ammonia hydroxide in water) to give 1-(2-fluorobenzyl)-N-(1,7,9-trimethyl-2-oxo-2,3,4,5-tetrahydro-1H-imidazo[1,5-a][1,3]diazepin-3-yl)-1H-1,2,4-triazole-3-carboxamide (70 mg, 71%) as a white solid. The racemic compound was separated by chiral SFC to give:

1-[(2-fluorophenyl)methyl]-N-(3R)-1,7,9-trimethyl-2-oxo-4,5-dihydro-3H-imidazo[1,5-a][1,3]diazepin-3-yl-1,2,4-triazole-3-carboxamide (Peak 2, retention time 4.147 min) (18.9 mg, 31.2%) as a white solid. $^1$H NMR (400 MHz, $CD_3OD$) δ8.58 (s, 1H), 7.43-7.36 (m, 2H), 7.22-7.12 (m, 2H), 5.48 (s, 2H), 4.57-4.52 (m, 1H), 4.25-4.19 (m, 1H), 3.83-3.79 (m, 1H), 3.30 (s, 3H), 2.68-2.62 (m, 1H), 2.34 (s, 3H), 2.16 (s, 3H), 2.09-2.05 (m, 1H). LCMS $R_T$=0.724 min, m/z=412.0 $[M+H]^+$.

LCMS (5 to 95% acetonitrile in water+0.03% trifluoacetic acid over 1.5 mins) retention time 0.724 min, ESI+ found [M+H]=412.0

SFC conditions: Column: Chiralpak OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.8 mL/min Column temp.: 40° C.

Example 597

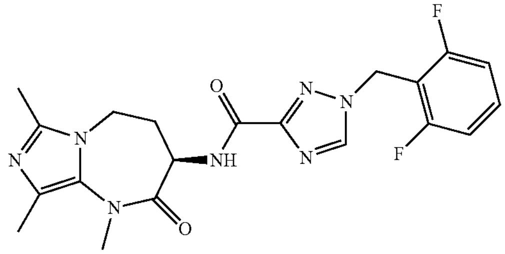 [SMILES: Cc1nc(C)n2c1N(C)C(=O)[C@H](NC(=O)c1ncn(Cc3c(F)cccc3F)n1)CC2]

1-[(2,6-difluorophenyl)methyl]-N-(3R)-1,7,9-trimethyl-2-oxo-4,5-dihydro-3H-imidazo[1, 5-a][1,3]diazepin-3-yl-1,2,4-triazole-3-carboxamide Amide coupling prepared in a similar fashion to WX Method 096. The crude was purified by RP-HPLC (18% to 48% acetonitrile/0.05% ammonia hydroxide in water) to give 1-(2,6-difluorobenzyl)-N-(1,7,9-trimethyl-2-oxo-2,3,4,5-tetrahydro-1H-imidazo[1,5-a][1,3]di azepin-3-yl)-1H-1,2,4-triazole-3-carboxamide (70 mg, 71%) as a white solid. The racemic material was separated by chiral SFC to give:

1-[(2,6-difluorophenyl)methyl]-N-(3R)-1,7,9-trimethyl-2-oxo-4, 5-dihydro-3H-imidazo[1,5-a][1,3]diazepin-3-yl-1,2,4-triazole-3-carboxamide (Peak 2, retention time 3.054 min) (25.1 mg, 41.4%) as a white solid. $^1$H NMR (400 MHz, $CD_3OD$) δ8.61 (s, 1H), 7.50-7.42 (m, 1H), 7.08-7.03 (m, 2H), 5.48 (s, 2H), 4.57-4.52 (m, 1H), 4.25-4.19 (m, 1H), 3.83-3.79 (m, 1H), 3.30 (s, 3H), 2.68-2.62 (m, 1H), 2.34 (s, 3H), 2.16 (s, 3H), 2.09-2.05 (m, 1H). LCMS $R_T$=0.544 min; m/z=430.1 $(M+H)^+$.

LCMS (5 to 95% acetonitrile in water+0.03% trifluoacetic acid over 1.5 mins) retention time 0.544 min, ESI+ found [M+H]=430.1

SFC condition Column: Chiralpak OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.8 mL/min Column temp.: 40° C.

Example 598

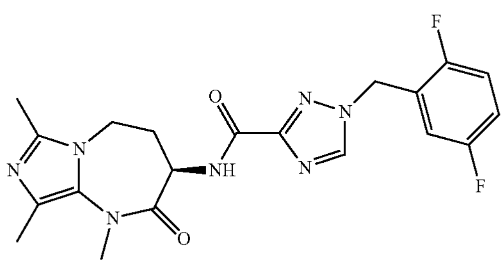 [SMILES: Cc1nc(C)n2c1N(C)C(=O)[C@H](NC(=O)c1ncn(Cc3cc(F)ccc3F)n1)CC2]

1-[(2,5-difluorophenyl)methyl]-N-(3R)-1,7,9-trimethyl-2-oxo-4,5-dihydro-3H-imidazo[1, 5-a][1,3]diazepin-3-yl-1,2,4-triazole-3-carboxamide Amide coupling prepared in a similar fashion to WX Method 096. The crude was purified by RP-HPLC (18% to 48% acetonitrile/0.05% ammonia hydroxide in water) to give 1-(2,5-difluorobenzyl)-N-(1,7,9-trimethyl-2-oxo-2,3,4,5-tetrahydro-1H-imidazo[1,5-a][1,3]di azepin-3-yl)-1H-1,2,4-triazole-3-carboxamide (70 mg, 71%) as a white solid. The racemic material was separated by chiral SFC to give:

1-[(2,5-difluorophenyl)methyl]-N-(3R)-1,7,9-trimethyl-2-oxo-4, 5-dihydro-3H-imidazo[1,5-a][1,3]diazepin-3-yl-1,2,4-triazole-3-carboxamide (Peak 2, retention time 3.240 min) (21.7 mg, 36%). $^1$H NMR (400 MHz, $CD_3OD$) δ 8.62 (s, 1H), 7.19-7.13 (m, 3H), 5.54 (s, 2H), 4.57-4.52 (m, 1H), 4.25-4.19 (m, 1H), 3.83-3.79 (m, 1H), 3.30 (s, 3H), 2.68-2.62 (m, 1H), 2.34 (s, 3H), 2.16 (s, 3H), 2.09-2.05 (m, 1H). LCMS $R_T$=0.540 min; m/z=430.0 $(M+H)^+$.

LCMS (5 to 95% acetonitrile in water+0.03% trifluoacetic acid over 1.5 mins) retention time 0.540 min, ESI+ found [M+H]=430.0

SFC condition: Column: Chiralpak OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.8 mL/min Column temp.: 40° C.

Example 599

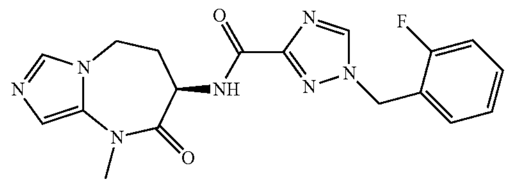 [SMILES: CN1C(=O)[C@H](NC(=O)c2ncn(Cc3ccccc3F)n2)CCn2cncc21]

1-[(2-fluorophenyl)methyl]-N-(3R)-1-methyl-2-oxo-4,5-dihydro-3H-imidazo[1,5-a][1,3]diazepin-3-yl-1,2,4-triazole-3-carboxamide Amide coupling prepared in a similar fashion to WX Method 043. The obtained racemic compound was separated by chiral SFC to give:

1-[(2-fluorophenyl)methyl]-N-(3R)-1-methyl-2-oxo-4,5-dihydro-3H-imidazo[1,5-a][1,3]diazepin-3-yl-1,2,4-triazole-3-carboxamide (Peak 2, retention time=3.432 min) (17.3 mg, 34%) as white solids. $^1$H NMR (400 MHz, DMSO-$d_6$) δ 8.81 (s, 1H), 8.47 (d, J=7.6 Hz, 1H), 7.58 (s, 1H), 7.44-7.33 (m, 2H), 7.27-7.19 (m, 2H), 6.95 (s, 1H), 5.55 (s, 2H), 4.38-4.31 (m, 2H), 3.88-3.81 (m, 1H), 3.23 (s, 3H), 2.44 (s, 1H), 2.27-2.21 (m, 1H). LCMS $R_T$=1.693 min, m/z=384.2 $[M+H]^+$.

LCMS (0 to 60% acetonitrile in water+0.03% ammonium bicarbonate over 3.0 mins) retention time 1.693 min, ESI+ found [M+H]=384.2.

SFC conditions: Column: Chiralcel OJ-3 100×4.6 mm I.D., 3 um Mobile phase: A: CO2 B: methanol (0.05% DEA) Gradient: from 5% to 40% of B in 4.5 min and hold 40% for 2.5 min, then 5% of B for 1 min Flow rate: 2.8 mL/min Column temperature: 40° C.

Example 600

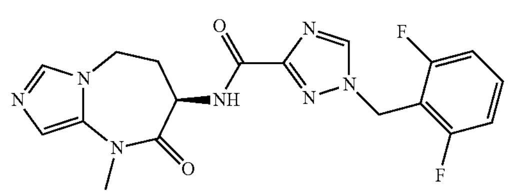 [SMILES: CN1C(=O)[C@H](NC(=O)c2ncn(Cc3c(F)cccc3F)n2)CCn2cncc21]

1-[(2,6-difluorophenyl)methyl]-N-[(3R)-1-methyl-2-oxo-4,5-dihydro-3H-imidazo[1,5-a][1,3]diazepin-3-yl]-1,2,4-triazole-3-carboxamide Amide coupling prepared in a similar fashion to WX Method 096. The obtained racemic compound was separated by chiral SFC to give:

1-[(2,6-difluorophenyl)methyl]-N-[(3R)-1-methyl-2-oxo-4,5-dihydro-3H-imidazo[1,5-a][1,3]diazepin-3-yl]-1,2,4-triazole-3-carboxamide (Peak 2, retention time 4.941 min)

(49.1 mg 49%). $^1$H NMR (400 MHz, DMSO-$d_6$) δ 8.83 (s, 1H), 8.46 (d, J=8.0 Hz, 1H), 7.61-7.43 (m, 2H), 7.20-7.16 (m, 2H), 6.95 (s, 1H), 5.56 (s, 2H), 4.39-4.25 (m, 2H), 3.88-3.78 (m, 1H), 3.22 (s, 3H), 2.48-2.39 (m, 1H), 2.27-2.20 (m, 1H). LCMS $R_T$=1.681 min; m/z=402.1 $(M+H)^+$.

LCMS (0 to 60% acetonitrile in water+0.03% ammonium bicarbonate over 3.0 mins) retention time 1.681 min, ESI+ found [M+H]=402.1

SFC condition: Column: Chiralpak AD-3 100×4.6 mm I.D., 3 um Mobile phase: A: CO2 B: Methanol (0.05% DEA) Gradient: from 5% to 40% of B in 4.5 min and hold 40% for 2.5 min, then 5% of B for 1 min Flow rate: 2.8 mL/min Column temperature: 40° C.

Example 601

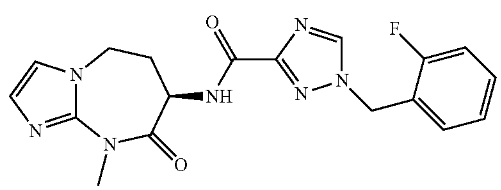 [SMILES: CN1C(=O)[C@H](NC(=O)c2ncn(Cc3ccccc3F)n2)CCn2ccnc21]

1-[(2-fluorophenyl)methyl]-N-(7R)-9-methyl-8-oxo-6,7-dihydro-5H-imidazo[1,2-a][1,3]diazepin-7-yl-1,2,4-triazole-3-carboxamide Amide coupling prepared in a similar fashion to WX Method 043. The obtained racemic compound was separated by chiral SFC to give:

1-[(2-fluorophenyl)methyl]-N-(7R)-9-methyl-8-oxo-6,7-dihydro-5H-imidazo[1,2-a][1,3]diazepin-7-yl-1,2,4-triazole-3-carboxamide (Peak 2, retention time 4.621 min) (19 mg, 47.5%): $^1$H NMR (400 MHz, $CD_3OD$) δ 8.58 (s, 1H), 7.42-7.34 (m, 2H), 7.21-7.11 (m, 2H), 7.08 (s, 1H), 6.95 (s, 1H), 5.54 (s, 2H), 4.54-4.47 (m, 1H), 4.32-4.25 (m, 1H), 4.09-4.02 (m, 1H), 3.38 (s, 3H), 2.87-2.79 (m, 1H), 2.28-2.23 (m, 1H). LCMS $R_T$=1.293 min, m/z=384.2 $[M+H]^+$.

LCMS (10 to 80% acetonitrile in water+0.05% ammonium bicarbonate over 3 mins) retention time 1.293, ESI+ found [M+H]=384.2.

SFC conditions: Column: Chiralcel OJ-3 250×30 mm I.D., 10 um Mobile phase: A: CO2 B: ethanol (0.05% DEA) Gradient: from 25% to 25%, Flow rate: 60 mL/min, Column temp.: 40° C.

Example 602

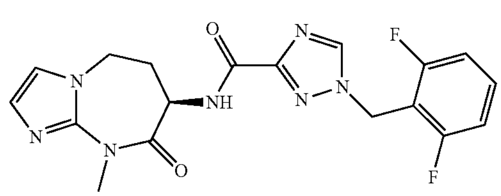 [SMILES: CN1C(=O)[C@H](NC(=O)c2ncn(Cc3c(F)cccc3F)n2)CCn2ccnc21]

1-[(2,6-difluorophenyl)methyl]-N-[(7R)-9-methyl-8-oxo-6,7-dihydro-5H-imidazo[1,2-a][1,3]diazepin-7-yl]-1,2,4-triazole-3-carboxamide Amide coupling prepared in a similar fashion to WX Method 096. The obtained racemic compound was separated by chiral SFC to give:

1-[(2,6-difluorophenyl)methyl]-N-[(7R)-9-methyl-8-oxo-6,7-dihydro-5H-imidazo[1,2-a][1,3]diazepin-7-yl]-1,2,4-triazole-3-carboxamide (Peak 2, retention time 4.289 min) (19 mg, 47.5%) as white solids. $^1$H NMR (400 MHz, DMSO-$d_6$) δ 8.84 (s, 1H), 8.53 (d, J=7.6 Hz, 1H), 7.55-7.46 (m, 1H), 7.17 (t, J=8.0 Hz, 2H), 7.12 (s, 1H), 6.87 (s, 1H), 5.56 (s, 2H), 4.29-4.23 (m, 2H), 3.95-3.87 (m, 1H), 3.24 (s, 3H), 3.51-3.50 (m, 1H), 2.38-2.34 (m, 1H). LCMS $R_T$=1.293 min; m/z=402.1 $(M+H)^+$.

LCMS (10 to 80% acetonitrile in water+0.05% ammonium bicarbonate over 3 mins) retention time 1.293, ESI+ found [M+H]=402.1

SFC condition: Column: Chiralcel OJ-3 250×30 mm I.D., 10 um Mobile phase: A: CO2 B: ethanol (0.05% DEA) Gradient: from 25% to 25%, Flow rate: 60 mL/min, Column temp.: 40° C.

Example 603

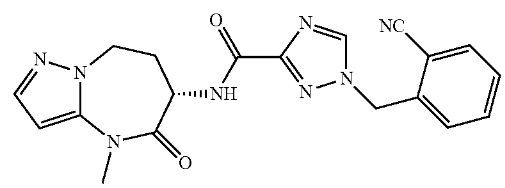 [SMILES: CN1C(=O)[C@@H](NC(=O)c2ncn(Cc3ccccc3C#N)n2)CCn2nccc21]

1-[(2-cyanophenyl)methyl]-N-(6S)-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 059. The crude was purified by RP-HPLC (acetonitrile 14-44%/HCl in water) to give 1-[(2-cyanophenyl)methyl]-N-(6S)-4-methyl-5-oxo-7,8-dihydro-6H-pyrazolo[1,5-a][1,3]diazepin-6-yl-1,2,4-triazole-3-c arboxamide (12 mg, 17%) as white solids. $^1$H NMR (400 MHz, $CD_3OD$) δ8.80 (s, 1H), 7.81 (d, J=8.0 Hz, 1H), 7.74-7.68 (m, 1H), 7.66 (d, J=2.0 Hz, 1H), 7.58-7.53 (m, 1H), 7.49 (d, J=8.0 Hz, 1H), 6.39 (d, J=2.0 Hz, 1H), 5.74 (s, 2H), 4.57-4.52 (m, 1H), 4.50-4.44 (m, 1H), 4.38-4.27 (m, 1H), 3.36 (s, 3H), 2.91-2.81 (m, 1H), 2.35-2.28 (m, 1H). LCMS $R_T$=1.732 min; m/z=391.1 $(M+H)^+$.

LCMS (0 to 60% acetonitrile in water+0.03% ammonium hydroxide acid over 3 mins) retention time 1.732 min, ESI+ found [M+H]=391.1.

Example 604

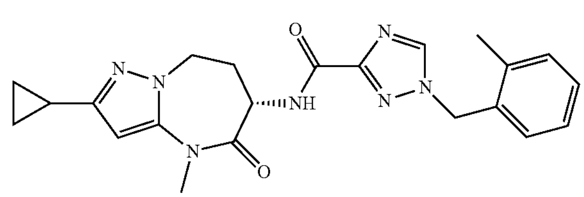 [SMILES: Cc1ccccc1Cn1cnc(C(=O)N[C@H]2CCn3nc(C4CC4)cc3N(C)C2=O)n1]

1-(o-tolylmethyl)-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 062. The crude was purified by RP-HPLC (acetonitrile 30-60%/0.05% ammonium hydroxide in water) to give 1-(o-tolylmethyl)-N-(6S)-2-cyclopropyl-4-methyl-5-oxo-7,8-dihydro-6H-pyrazolo[1,5-a][1,3]diazepin-6-yl-1,2,4-triazole-3-carboxamide (38 mg, 49%) as white solids. $^1$H NMR (400 MHz, $CD_3OD$) δ8.44 (s, 1H), 7.26-7.15 (m, 4H), 6.00 (s, 1H), 5.50 (s, 2H), 4.45-4.49 (m, 1H), 4.28-4.23 (m, 1H), 4.20-4.18 (m, 1H), 3.35 (s, 3H), 2.85-2.80 (m, 1H), 2.34 (s, 3H), 2.24-2.22 (m, 1H), 1.92-1.88 (m, 1H), 0.95-0.92 (m, 2H), 0.75-0.72 (m, 2H). LCMS $R_T$=1.69 min; m/z=420.2 $(M+H)^+$.

LCMS (10 to 80% acetonitrile in water+0.03% ammonium hydroxide acid over 3 mins) retention time 1.69 min, ESI+ found [M+H]=420.2.

Example 605

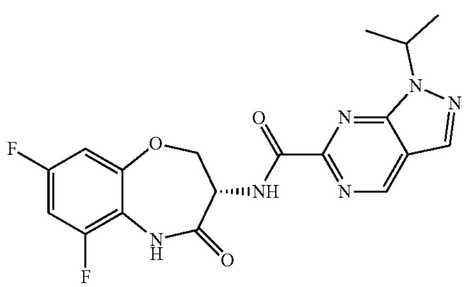

1-isopropyl-N-[(3S)-6,8-difluoro-4-oxo-3,5-dihydro-2H-1,5-benzoxazepin-3-yl]pyrazolo[3,4-d]pyrimidine-6-carboxamide Amide coupling prepared in a similar fashion to WX Method 142. The crude was purified by RP-HPLC (acetonitrile 32% to 62%/0.05% ammonium hydroxide in water) to give 1-isopropyl-N-[(3S)-6,8-difluoro-4-oxo-3,5-dihydro-2H-1,5-benzoxazepin-3-yl]pyrazolo[3,4-d]pyrimidine-6-carboxamide (14.7 mg, 26%) as a white solid. $^1$H NMR (400 MHz, $CD_3OD$) δ9.36 (s, 1H), 8.39 (s, 1H), 6.98-6.88 (m, 2H), 5.46-5.42 (m, 1H), 5.16-5.13 (m, 1H), 4.80-4.76 (m, 1H), 4.58 (t, J=10.4 Hz, 1H), 1.60 (d, J=6.4 Hz, 6H). LCMS $R_T$=0.787 min, m/z=403.0 $[M+H]^+$.

LCMS (5 to 95% acetonitrile in water+0.03% trifluoacetic acid over 1.5 mins) retention time 0.787 min, ESI+ found [M+H]=403.0.

Example 606

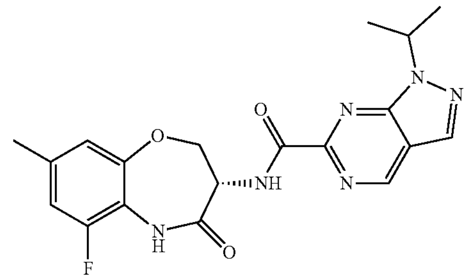 [SMILES: Cc1cc(F)c2c(c1)OC[C@H](NC(=O)c1ncc3cnn(C(C)C)c3n1)C(=O)N2]

1-isopropyl-N-[(3S)-6-fluoro-8-methyl-4-oxo-3,5-dihydro-2H-1,5-benzoxazepin-3-yl]pyrazolo[3,4-d]pyrimidine-6-carboxamide Amide coupling prepared in a similar fashion to WX Method 142. The crude was purified by RP-HPLC (acetonitrile 32% to 62%/0.05% ammonium hydroxide in water) to give 1-isopropyl-N-[(3S)-6-fluoro-8-methyl-4-oxo-3,5-dihydro-2H-1,5-benzoxazepin-3-yl]pyrazolo[3,4-d]pyrimidine-6-carboxamide (19.4 mg, 33%) as a white solid. $^1$H NMR (400 MHz, $CD_3OD$) δ9.36 (s, 1H), 8.39 (s, 1H), 6.91-6.88 (m, 2H), 5.47-5.42 (m, 1H), 5.12-5.09 (m, 1H), 4.76-4.72 (m, 1H), 4.51 (t, J=10.4 Hz, 1H), 2.36 (s, 3H), 1.60 (d, J=6.4 Hz, 6H). LCMS $R_T$=0.787 min, m/z=399.0 $[M+H]^+$.

LCMS (5 to 95% acetonitrile in water+0.03% trifluoacetic acid over 1.5 mins) retention time 0.787 min, ESI+ found [M+H]=399.0.

Example 607

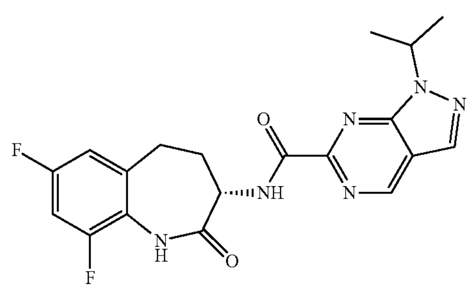 [SMILES: CC(C)n1ncc2cnc(C(=O)N[C@H]3CCc4cc(F)cc(F)c4NC3=O)nc21]

1-isopropyl-N-[(3S)-7,9-difluoro-2-oxo-1,3,4,5-tetrahydro-1-benzazepin-3-yl]pyrazolo[3, 4-d]pyrimidine-6-carboxamide Amide coupling prepared in a similar fashion to WX Method 142. The crude was purified by RP-HPLC (acetonitrile 35% to 65%/0.05% ammonium hydroxide in water) to give 1-isopropyl-N-[(3S)-7,9-difluoro-2-oxo-1,3,4,5-tetrahydro-1-benzazepin-3-yl]pyrazolo[3,4-d]pyrimidine-6-carboxamide (34.7 mg, 60%) as a white solid. $^1$H NMR (400 MHz, $CD_3OD$) δ9.35 (s, 1H), 8.38 (s, 1H), 7.05-7.00 (m, 2H), 5.45-5.40 (m, 1H), 4.69-4.64 (m, 1H), 3.05-3.02 (m, 1H), 2.89-2.76 (m, 2H), 2.32-2.26 (m, 1H), 1.60 (d, J=6.8 Hz, 6H). LCMS $R_T$=0.770 min, m/z=401.0 $[M+H]^+$.

LCMS (5 to 95% acetonitrile in water+0.03% trifluoacetic acid over 1.5 mins) retention time 0.770 min, ESI+ found [M+H]=401.0.

Example 608

WX Method 096

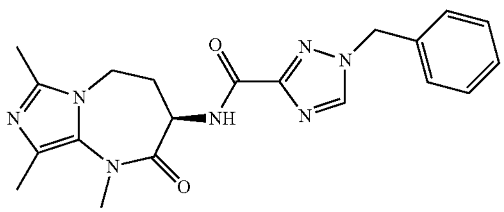 [SMILES: Cc1nc(C)n2c1N(C)C(=O)[C@H](NC(=O)c1ncn(Cc3ccccc3)n1)CC2]

1-benzyl-N-(3R)-1,7,9-trimethyl-2-oxo-4,5-dihydro-3H-imidazo[1,5-a][1,3]diazepin-3-yl-1,2,4-triazole-3-carboxamide

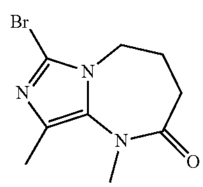

Step 1: 7-bromo-1,9-dimethyl-4,5-dihydro-1H-imidazo[1,5-a][1,3]diazepin-2(3H)-one To a solution of 1,9-dimethyl-4,5-dihydro-3H-imidazo[1,5-a][1,3]diazepin-2-one (500 mg, 2.79 mmol) in chloroform (20 mL) was added 1-bromo-2,5-pyrrolidinedione (596 mg, 3.35 mmol). The reaction mixture was heated at 70° C. for 2 h and concentrated under reduced pressure. The residue was purified by column chromatography (silica gel, 100-200 mesh, 0 to 10% methanol in dichloromethane) to afford 7-bromo-1,9-dimethyl-4,5-dihydro-3H-imidazo[1,5-a][1,3]diazepin-2-one (720 mg, 100%) as a yellow solid, used as is in the next step.

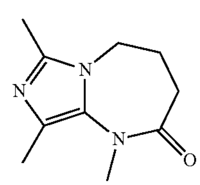

Step 2: 1,7,9-trimethyl-4,5-dihydro-3H-imidazo[1,5-a][1,3]diazepin-2-one

A mixture of 7-bromo-1,9-dimethyl-4,5-dihydro-3H-imidazo[1,5-a][1,3]diazepin-2-one (600 mg, 2.32 mmol), trimethylboroxine (584 mg, 4.65 mmol), 1,1'-bis(diphenylphosphino)ferrocene palladium dichloride (170 mg, 0.23 mmol) and cesium carbonate (1.51 g, 4.65 mmol) in 1,4-dioxane (10 mL) and water (2 mL) was heated at 95° C. for 3 h and then concentrated under reduced pressure. The residue was purified by RP-HPLC (5% to 35% acetonitrile, 0.05% ammonia hydroxide in water) to afford 1,7,9-trimethyl-4,5-dihydro-3H-imidazo[1,5-a][1,3]diazepin-2-one (220 mg, 49%) as a white solid, used as is in the next step.

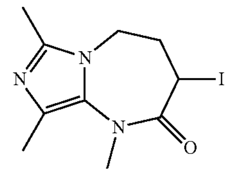

Step 3: 3-iodo-1,7,9-trimethyl-4,5-dihydro-3H-imidazo[1,5-a][1,3]diazepin-2-one

To a solution of 1,7,9-trimethyl-4,5-dihydro-3H-imidazo[1,5-a][1,3]diazepin-2-one (220 mg, 1.14 mmol) in dichloromethane (15 mL) was added N1,N1,N3,N3-tetramethylpropane-1,3-diamine (1.06 g, 9.11 mmol) and iodotrimethylsilane (1.82 g, 9.11 mmol) at −15° C. The reaction mixture was stirred at −15° C. for 2 h and iodine (867 mg, 3.42 mmol) was added. The mixture was stirred at −15° C. for another 2 h and quenched by addition of saturated aqueous sodium sulfite (20 mL). The resulting mixture was extracted with dichloromethane (3×20 mL). The combined organic layers were dried over sodium sulfate and concentrated under reduced pressure. The residue was purified by flash column chromatography (silica gel, 100-200 mesh, 0 to 5% methanol in dichloromethane) to afford 3-iodo-1,7,9-trimethyl-4,5-dihydro-3H-imidazo[1,5-a][1,3]diazepin-2-one (350 mg, 96%) as a white solid, used as is in the next step.

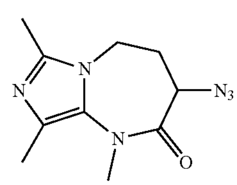 [SMILES: Cc1nc(C)n2c1N(C)C(=O)C(N=[N+]=[N-])CC2]

Step 3: 3-azido-1,9-dimethyl-4,5-dihydro-3H-imidazo[1,5-a][1,3]diazepin-2-one

A mixture of 3-iodo-1,9-dimethyl-4,5-dihydro-3H-imidazo[1,5-a][1,3]diazepin-2-one (350 mg, 1.15 mmol) and sodium azide (500 mg, 7.69 mmol) in N,N-dimethylformamide (5 mL) was stirred at 25° C. for 3 h and then diluted with water (20 mL). The mixture was extracted with ethyl acetate (3×30 mL). The combined organic layers were dried over sodium sulfate and concentrated under reduced pressure to afford crude azido-1,9-dimethyl-4,5-dihydro-3H-imidazo[1,5-a][1,3]diazepin-2-one (250 mg, 99%) as colorless oil, used as is in the next step.

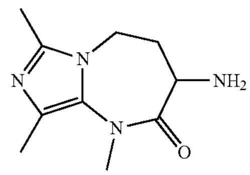

Step 4: 3-amino-1,7,9-trimethyl-4,5-dihydro-3H-imidazo[1,5-a][1,3]diazepin-2-one A mixture of 3-azido-1,7,9-trimethyl-4,5-dihydro-3H-imidazo[1,5-a][1,3]diazepin-2-one (250 mg, 1.07 mmol) and Pd/C (10%, 114 mg, 0.11 mmol) in methanol (30 mL) was hydrogenated (15 psi) for 2 h and filtered. The filtrate was concentrated under reduced pressure to afford crude 3-amino-1,7,9-trimethyl-4,5-dihydro-3H-imidazo[1,5-a][1,3]diazepin-2-one (200 mg, 90%) as a white solid used as is in the next step.

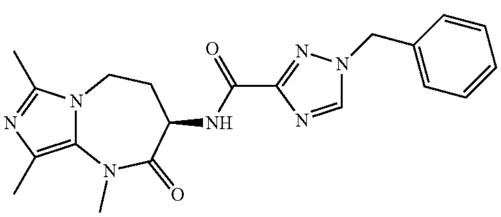 [SMILES: Cc1nc(C)n2c1N(C)C(=O)[C@H](NC(=O)c1ncn(Cc3ccccc3)n1)CC2]

Step 5: 1-benzyl-N-(3R)-1,7,9-trimethyl-2-oxo-4,5-dihydro-3H-imidazo[1,5-a][1,3]diazepin-3-yl-1,2,4-triazole-3-carboxamide A mixture of 3-amino-1,7,9-trimethyl-4,5-dihydro-3H-imidazo[1,5-a][1,3]diazepin-2-one (30 mg, 0.14 mmol), 1-(3-dimethylaminopropyl)-3-ethylcarbodiimidehydrochloride (27 mg, 0.14 mmol), 1-hydroxybenzotriazole (19 mg, 0.14 mmol) and 1-benzyl-1,2,4-triazole-3-carboxylic acid (29 mg, 0.14 mmol) in N,N-dimethylformamide (3 mL) was stirred at 20° C. for 2 h. The mixture was concentrated under reduced pressure and the residue was purified by RP-HPLC (18% to 48% acetonitrile/0.05% ammonia hydroxide in water) to afford 1-benzyl-N-(1,7,9-trimethyl-2-oxo-2,3,4,5-tetrahydro-1H-imidazo[1,5-a][1,3]diazepin-3-yl)-1H-1,2,4-triazole-3-carboxamide (40 mg, 71%) as a white solid. The racemic compound was separated by chiral SFC to give:

1-benzyl-N-(3R)-1,7,9-trimethyl-2-oxo-4,5-dihydro-3H-imidazo[1,5-a][1,3]diazepin-3-yl-1,2,4-triazole-3-carboxamide (Peak 2, retention time 4.482 min) (12.1 mg, 30%) as a white solid. $^1$H NMR (400 MHz, $CD_3OD$) δ8.57 (s, 1H), 7.39-7.35 (m, 5H), 5.48 (s, 2H), 4.57-4.52 (m, 1H), 4.25-4.19 (m, 1H), 3.83-3.79 (m, 1H), 3.30 (s, 3H), 2.68-2.62 (m, 1H), 2.34 (s, 3H), 2.16 (s, 3H), 2.09-2.05 (m, 1H). LCMS $R_T$=1.332 min; m/z=394.2 $(M+H)^+$.

LCMS (10 to 80% acetonitrile in water+0.05% ammonium bicarbonate over 3 mins) retention time 1.332 min, ESI+ found [M+H]=394.2.

SFC conditions: Column: Chiralpak OJ-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.8 mL/min Column temp.: 40° C.

Example 609

WX Method 140

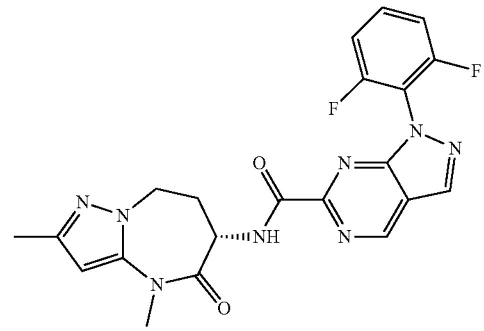 [SMILES: Cc1cc2n(n1)CC[C@H](NC(=O)c1ncc3cnn(-c4c(F)cccc4F)c3n1)C(=O)N2C]

1-(2,6-difluorophenyl)-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide

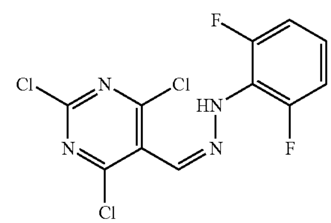 [SMILES: Fc1cccc(F)c1N/N=C\c1c(Cl)nc(Cl)nc1Cl]

Step 1: (Z)-2,4,6-trichloro-5-((2-(2,6-difluorophenyl)hydrazono)methyl)pyrimidine To a solution of 2,4,6-trichloropyrimidine-5-carbaldehyde (1.0 g, 4.73 mmol) in tetrahydrofuran (400 mL) was added (2,6-difluorophenyl)hydrazine (682 mg, 4.73 mmol) at 0° C. The mixture was stirred at 20° C. for 1.5 h and concentrated under reduced pressure. The residue was purified by column chromatography (silica gel, 100-200 mesh, 0 to 10% ethyl acetate in petroleum ether) to give (Z)-2,4,6-trichloro-5-((2-(2,6-difluorophenyl)hydrazono)methyl)pyrimidine (1.2 g, 75%) as a yellow solid, used as is in the next step.

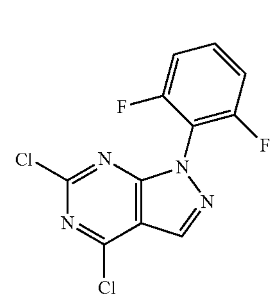 [SMILES: Fc1cccc(F)c1-n1ncc2c(Cl)nc(Cl)nc21]

Step 2: 4,6-dichloro-1-(2,6-difluorophenyl)-1H-pyrazolo[3,4-d]pyrimidine

A solution of 2,6-difluoro-N—[(Z)-(2,4,6-trichloropyrimidin-5-yl) methyleneamino]aniline (600 mg, 1.78 mmol)

in acetonitrile (4 mL) was heated at 150° C. for 1.5 h under microwave conditions. The mixture was filtered and the filtrate was concentrated under reduced pressure to afford 4,6-dichloro-1-(2,6-difluorophenyl)pyrazolo[3,4-d]pyrimidine (500 mg, 93%) as a white solid, used as is in the next step.

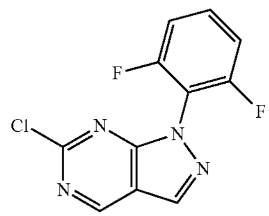 [SMILES: Fc1cccc(F)c1-n1ncc2cnc(Cl)nc21]

Step 3: 6-chloro-1-(2,6-difluorophenyl)-1H-pyrazolo[3,4-d]pyrimidine

A mixture of 4,6-dichloro-1-(2,6-difluorophenyl)pyrazolo[3,4-d]pyrimidine (500 mg, 1.66 mmol), zinc (326 mg, 4.98 mmol) in water (10 mL) and tetrahydrofuran (10 mL) was heated at 100° C. for 1 h. After cooled, the reaction was extracted with ethyl acetate (3×10 mL). The combined organic layers were washed with water (2×10 mL), brine (1×10 mL), dried over magnesium sulfate and concentrated under reduced pressure. The residue was purified by column chromatography (silica gel 100-200 mesh, 0-20% ethyl acetate in petroleum ether) to afford 6-chloro-1-(2,6-difluorophenyl)pyrazolo[3,4-d]pyrimidine (350 mg, 79%) as a white solid, used as is in the next step.

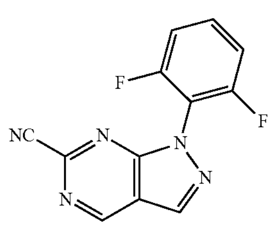 [SMILES: N#Cc1ncc2cnn(-c3c(F)cccc3F)c2n1]

Step 4: 1-(2,6-difluorophenyl)-1H-pyrazolo[3,4-d]pyrimidine-6-carbonitrile

To a solution of 1,4-diazabicyclo[2.2.2]octane (63 mg, 0.56 mmol) and sodium cyanide (110 mg, 2.25 mmol) in dimethyl sulfoxide (8 mL) was added 6-chloro-1-(2,6-difluorophenyl)pyrazolo[3,4-d]pyrimidine (300 mg, 1.13 mmol) in water (4 mL). The reaction mixture was stirred at 25° C. for 12 h and extracted with ethyl acetate (3×20 ml). The combined organic layers were dried over sodium sulfate and concentrated under reduced pressure. The residue was purified by column chromatography (silica gel, 100-200 mesh, 0 to 30% ethyl acetate in petroleum ether) to afford 1-(2,6-difluorophenyl)pyrazolo[3,4-d]pyrimidine-6-carbonitrile (100 mg, 35%) as a yellow solid, used as is in the next step.

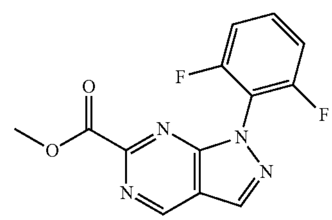 [SMILES: COC(=O)c1ncc2cnn(-c3c(F)cccc3F)c2n1]

Step 5: methyl 1-(2,6-difluorophenyl)-1H-pyrazolo[3,4-d]pyrimidine-6-carboxylate To a solution of 1-(2,6-difluorophenyl)pyrazolo[3,4-d]pyrimidine-6-carbonitrile (100 mg, 0.39 mmol) in methanol (5 mL) was added HCl (4 N in methanol, 5 mL). The reaction mixture was stirred at 20° C. for 3 h and concentrated under reduced pressure to afford crude methyl 1-(2,6-difluorophenyl)pyrazolo[3,4-d]pyrimidine-6-carboxylate (50 mg, 44%) as a yellow oil, used as is in the next step.

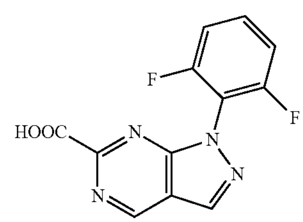 [SMILES: O=C(O)c1ncc2cnn(-c3c(F)cccc3F)c2n1]

Step 6: 1-(2,6-difluorophenyl)-1H-pyrazolo[3,4-d]pyrimidine-6-carboxylic acid

A mixture of methyl 1-(2,6-difluorophenyl)pyrazol o[3,4-d]pyrimidine-6-carboxylate (40 mg, 0.14 mmol) and lithium hydroxide (23 mg, 0.55 mmol) in tetrahydrofuran (5 mL) and water (2 mL) was stirred at 20° C. for 2 h. The organic solvent was concentrated under reduced pressure and the aqueous solution was adjusted to pH=3 by addition of 1N HCl. The mixture was extracted with dichloromethane (2×10 mL). The combined organic layers were concentrated under reduced pressure to afford crude 1-(2,6-difluorophenyl)pyrazolo[3,4-d]pyrimidine-6-carboxylic acid (30 mg, 78%) as a yellow solid, used as is in the next step.

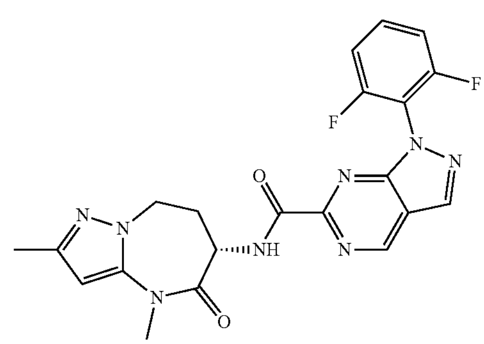 [SMILES: Cc1cc2n(n1)CC[C@H](NC(=O)c1ncc3cnn(-c4c(F)cccc4F)c3n1)C(=O)N2C]

Step 6: 1-(2,6-difluorophenyl)-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide A mixture of (6S)-6-amino-2,4-dimethyl-7,8-dihydro-6H-pyrazolo[1,5-a][1,3]diazepin-5-one (21 mg, 0.11 mmol), 1-hydroxybenzotriazole (35 mg, 0.26 mmol), 1-(2,6-difluorophenyl)pyrazolo[3,4-d]pyrimidine-6-carboxylic acid (30 mg, 0.11 mmol) and 1-(3-dimethyl aminopropyl)-3-ethylcarbodiimidehydrochloride (50 mg, 0.26 mmol) in N,N-dimethylformamide (5 mL) was stirred at 20° C. for 2 h. The mixture was concentrated under reduced pressure and the residue was purified by RP-HPLC (30% to 60% acetonitrile/0.05% HCl in water) to afford 1-(2,6-difluorophenyl)-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide (25 mg, 48%) as a white solid. $^1$H NMR (400 MHz, $CD_3OD$) δ9.58 (s, 1H), 8.76 (s, 1H), 7.77-7.68 (m, 1H), 7.35-7.31 (m, 2H), 6.35 (s, 1H), 4.73-4.71 (m, 1H), 4.47-4.40 (m, 1H), 4.38-4.31 (m, 1H), 3.38 (s, 3H), 3.00-2.92 (m, 1H), 2.42-2.30 (m, 4H). LCMS $R_T$=0.934 min; m/z=453.3 $(M+H)^+$.

LCMS (10 to 80% acetonitrile in water+0.03% trifluoacetic acid over 2.0 mins) retention time 0.934 min, ESI+ found [M+H]=453.3.

Example 610

WX Method 103

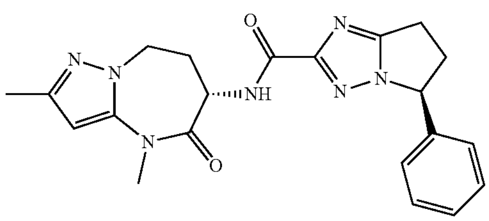 [SMILES: Cc1cc2n(n1)CC[C@H](NC(=O)c1nc3n(n1)[C@H](c1ccccc1)CC3)C(=O)N2C]

(S)—N—((S)-2,4-dimethyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide

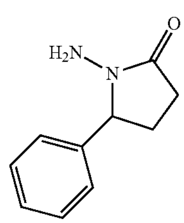 [SMILES: NN1C(=O)CCC1c1ccccc1]

Step 1: 1-amino-5-phenyl-pyrrolidin-2-one

To a solution of tert-butyl N-(2-oxo-5-phenyl-pyrrolidin-1-yl)carbamate (350 mg, 1.3 mmol) in ethyl acetate (3 mL) was added HCl (4N in ethyl acetate, 3.0 mL, 12.0 mmol). The mixture was stirred at 20° C. for 1 h and concentrated under reduced pressure. The residue was quenched by addition of saturated sodium bicarbonate (10 mL) and extracted with ethyl acetate (3×10 mL). The combined organic layers were washed with water (3×20 mL), brine (2×20 mL), dried over sodium sulfate and concentrated under reduced pressure to give crude 1-amino-5-phenyl-pyrrolidin-2-one (190 mg, 85%) as a white solid. $^1$H NMR (400 MHz, $CDCl_3$): δ 7.42-7.32 (m, 3H), 7.24 (d, J=7.6 Hz, 2H), 4.66-4.62 (m, 1H), 3.95 (br. s, 2H), 2.63-2.45 (m, 3H), 1.91-1.88 (m, 1H).

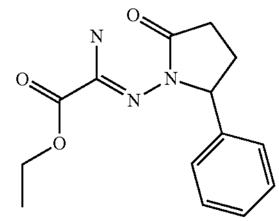 [SMILES: CCOC(=O)/C(N)=N/N1C(=O)CCC1c1ccccc1]

Step 2: ethyl (2Z)-2-amino-2-(2-oxo-5-phenyl-pyrrolidin-1-yl)imino-acetate

To a stirred solution of 1-amino-5-phenyl-pyrrolidin-2-one (270 mg, 1.53 mmol) in ethanol (8.0 mL) was added ethyl amino (thioxo)acetate (224 mg, 1.69 mmol). The mixture was stirred at 90° C. for 4 h and cooled to room temperature. The solution was diluted with ethyl acetate (15 mL), washed with water (2×5 mL), brine (10 mL), dried over sodium sulfate and concentrated under reduced pressure to give crude ethyl (2Z)-2-amino-2-(2-oxo-5-phenyl-pyrrolidin-1-yl)imino-acetate (400 mg, 95%) as a yellow oil. LCMS $R_T$=0.581 min, m/z=275.9 $[M+H]^+$.

LCMS (5 to 95% acetonitrile in water+0.03% trifluoacetic acid over 1.5 mins) retention time 0.581 min, ESI+ found [M+H]=275.9.

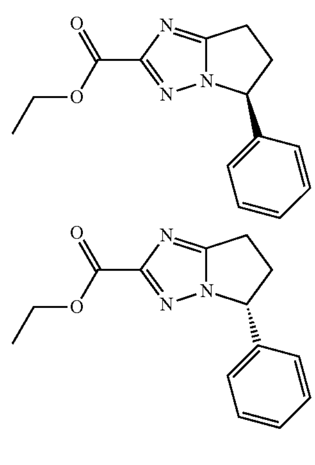

Step 3: (S)-ethyl 5-phenyl-6,7-dihydro-5H-pyrrolo[1,2-b][1,2,4]triazole-2-carboxylate and (R)-ethyl 5-phenyl-6,7-dihydro-5H-pyrrolo[1,2-b][1,2,4]triazole-2-carboxylate A solution of ethyl (2Z)-2-amino-2-(2-oxo-5-phenyl-pyrrolidin-1-yl)imino-acetate (400 mg, 1.45 mmol) in $POCl_3$ (2 mL) was stirred at 120° C. for 1 h. After cooled, the mixture was quenched by addition of saturated sodium bicarbonate (15 mL). The resulting solution was extracted with ethyl acetate (3×10 mL). The combined organic layers were washed with brine (15 mL), dried over sodium sulfate and concentrated under reduced pressure. The residue was purified by column chromatography (silica gel, 100-200 mesh, 0-70% ethyl acetate in petroleum) to afford ethyl 5-phenyl-6,7-dihydro-5H-pyrrolo[1,2-b][1,2,4]triazole-2-carboxylate (310 mg, 81%) as a yellow oil. The racemic material was separated by chiral SFC to give:

(S)-ethyl 5-phenyl-6,7-dihydro-5H-pyrrolo[1,2-b][1,2,4]triazole-2-carboxylate (Peak 1, retention time=4.063 min) (130 mg, 42%) as a yellow oil. LCMS $R_T$=0.629 min, m/z=257.8 $[M+H]^+$.

LCMS (5 to 95% acetonitrile in water+0.03% trifluoacetic acid over 1.5 mins) retention time 0.629 min, ESI+ found [M+H]=257.8.

(R)-ethyl 5-phenyl-6,7-dihydro-5H-pyrrolo[1,2-b][1,2,4]triazole-2-carboxylate (Peak 1, retention time=5.844 min) (135 mg, 43%) as a yellow oil. LCMS $R_T$=0.631 min, m/z=257.8 $[M+H]^+$.

LCMS (5 to 95% acetonitrile in water+0.03% trifluoacetic acid over 1.5 mins) retention time 0.631 min, ESI+ found [M+H]=257.8.

SFC condition: column: Lux Cellulose-2 150×4.6 mm I.D., 3 μm mobile phase: A: CO2; B: MeOH (0.05% DEA) gradient: from 5 to 40 of B in 4.5 min and hold 40% for 2.5 min, then 5% of B for 1 min. Flow rate: 2.8 mL/min. Column temperature: 40° C.

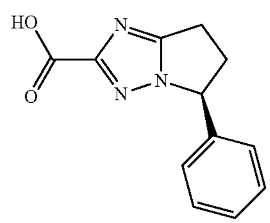 [SMILES: O=C(O)c1nc2n(n1)[C@H](c1ccccc1)CC2]

Step 4: (S)-5-phenyl-6,7-dihydro-5H-pyrrolo[1,2-b][1,2,4]triazole-2-carboxylic acid To a solution of ethyl (5S)-5-phenyl-6,7-dihydro-5H-pyrrolo[1,2-b][1,2,4]triazole-2-carboxylate (130 mg, 0.51 mmol) in tetrahydrofuran (2 mL)/methanol (2 mL)/water (1 mL) was added lithium hydroxide hydrate (127.2 mg, 3.03 mmol). The mixture was stirred at 25° C. for 1 h and diluted with water (10 mL). The solution was adjusted to pH=4-5 by addition of 1N HCl. The mixture was extracted with ethyl acetate (3×15 mL). The combined organic layers were dried over sodium sulfate and concentrated under reduced pressure to give crude (S)-5-phenyl-6,7-dihydro-5H-pyrrolo[1,2-b][1,2,4]triazole-2-carboxylic acid (105 mg, 90%) as a light yellow solid, used as is in the next step.

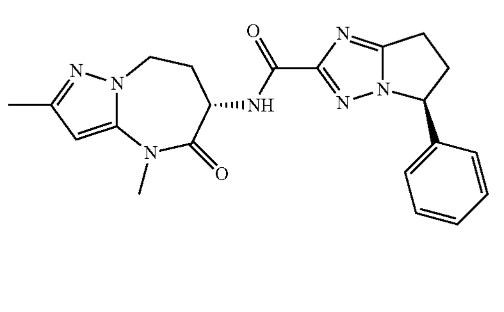 [SMILES: Cc1cc2n(n1)CC[C@H](NC(=O)c1nc3n(n1)[C@H](c1ccccc1)CC3)C(=O)N2C]

Step 5: (S)—N—((S)-2,4-dimethyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide A mixture of (6S)-6-amino-2,4-dimethyl-7,8-dihydro-6H-pyrazolo[1,5-a][1,3]diazepin-5-one (30 mg, 0.15 mmol), (S)-5-phenyl-6,7-dihydro-5H-pyrrolo[1,2-b][1,2,4]triazole-2-carboxylic acid (35 mg, 0.15 mmol), $N^1$-((ethylimino)methyl ene)-$N^3$,$N^3$-di methylpropane-1,3-diamine hydrochloride (44 mg, 0.23 mmol) and 1H-benzo[d][1,2,3]triazol-1-ol (31 mg, 0.23 mmol) in N,N-dimethylformamide (2 mL) was stirred at 25° C. for 16 h. The mixture was concentrated under reduced pressure and the residue was purified by RP-HPLC (26% to 56% acetonitrile/0.05% ammonia hydroxide in water) to give (S)—N—((S)-2,4-dimethyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide (48.3 mg, 76%) as a white solid. $^1$H NMR (400 MHz, $CD_3OD$) δ7.38-7.34 (m, 3H), 7.21-7.20 (m, 2H), 6.10 (s, 1H), 5.55-5.52 (m, 1H), 4.53-4.48 (m, 1H), 4.28-4.26 (m, 1H), 4.21-4.18 (m, 1H), 3.31 (s, 3H), 3.26-3.24 (m, 1H), 3.14-3.12 (m, 1H), 3.06-3.04 (m, 1H), 2.91-2.80 (m, 1H), 2.66-2.64 (m, 1H), 2.24-2.20 (m, 4H). LCMS $R_T$=0.752 min, m/z=406.1 $[M+H]^+$.

LCMS (5 to 95% acetonitrile in water+0.03% trifluoacetic acid over 1.5 mins) retention time 0.752 min, ESI+ found [M+H]=406.1.

Example 611

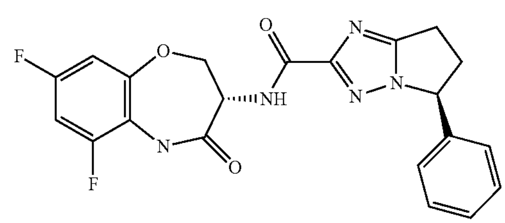 [SMILES: O=C(N[C@H]1COc2cc(F)cc(F)c2NC1=O)c1nc2n(n1)[C@H](c1ccccc1)CC2]

(5S)-5-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide Amide coupling prepared in a similar fashion to WX Method 103. The crude was purified by RP-HPLC (35% to 65% acetonitrile/0.05% ammonia hydroxide in water) to afford (5S)-5-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide (21.9 mg, 34%) as a white solid. $^1$H NMR (400 MHz, $CD_3OD$) δ7.38-7.34 (m, 3H), 7.22-7.20 (m, 2H), 6.94-6.84 (m, 2H), 5.57-5.53 (m, 1H), 5.07-5.02 (m, 1H), 4.66-4.62 (m, 1H), 4.50-4.47 (m, 1H), 3.25-3.15 (m, 1H), 3.13-3.03 (m, 2H), 2.69-2.66 (m, 1H). LCMS $R_T$=0.800 min, m/z=426.0 $[M+H]^+$.

LCMS (5 to 95% acetonitrile in water+0.03% trifluoacetic acid over 1.5 mins) retention time 0.800 min, ESI+ found [M+H]=426.0.

Example 612

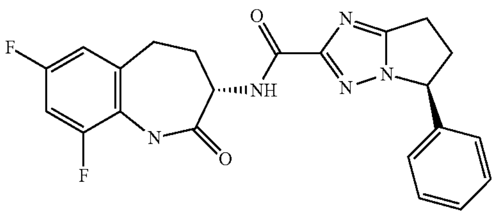 [SMILES: O=C(N[C@H]1CCc2cc(F)cc(F)c2NC1=O)c1nc2n(n1)[C@H](c1ccccc1)CC2]

(5S)-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide Amide coupling prepared in a similar fashion to WX Method 103. The crude was purified by RP-HPLC (40% to 70% acetonitrile/0.05% ammonia hydroxide in water) to afford (5S)-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (36.7 mg, 57%) as a white solid. $^1$H NMR (400 MHz, $CD_3OD$) δ7.40-7.33 (m, 3H), 7.21-7.20 (m, 2H), 7.01-6.97 (m, 2H), 5.55-5.52 (m, 1H), 4.57-4.52 (m, 1H), 3.24-2.95 (m, 4H), 2.82-2.81 (m, 1H), 2.67-2.62 (m, 2H), 2.23-2.17 (m, 1H). LCMS $R_T$=0.798 min, m/z=424.1 $[M+H]^+$.

LCMS (5 to 95% acetonitrile in water+0.03% trifluoacetic acid over 1.5 mins) retention time 0.798 min, ESI+ found [M+H]=424.1.

Example 613

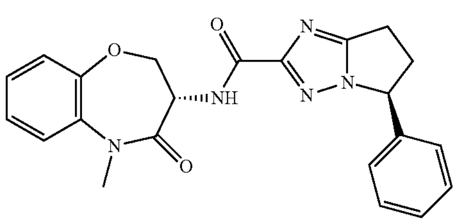 [SMILES: CN1C(=O)[C@@H](NC(=O)c2nc3n(n2)[C@H](c2ccccc2)CC3)COc2ccccc21]

(5S)-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide Amide coupling prepared in a similar fashion to WX Method 103. The crude was purified by RP-HPLC (38% to 68% acetonitrile/0.05% ammonia hydroxide in water) to afford (5S)-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (22.5 mg, 39%) as a white solid. $^1$H NMR (400 MHz, $CD_3OD$) δ7.40-7.30 (m, 6H), 7.29-7.20 (m, 3H), 5.54 (t, J=6.8 Hz, 1H), 4.98-4.95 (m, 1H), 4.58-4.54 (m, 1H), 4.40-4.35 (m, 1H), 3.39 (s, 3H), 3.27-3.24 (m, 1H), 3.14-3.04 (m, 2H), 2.67-2.65 (m, 1H). LCMS $R_T$=0.823 min, m/z=404.1 $[M+H]^+$.

LCMS (5 to 95% acetonitrile in water+0.03% trifluoacetic acid over 1.5 mins) retention time 0.823 min, ESI+ found [M+H]=404.1.

Example 614

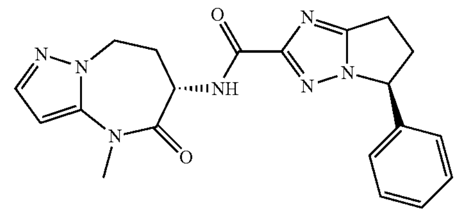 [SMILES: CN1C(=O)[C@@H](NC(=O)c2nc3n(n2)[C@H](c2ccccc2)CC3)CCn2nccc21]

(5S)-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Amide coupling prepared in a similar fashion to WX Method 103. The crude was purified by RP-HPLC (22% to 52% acetonitrile/0.05% ammonia hydroxide in water) to afford (5S)-5-phenyl-N-[(6S)-4-methyl-5-oxo-7,8-dihydro-6H-pyrazolo[1,5-a][1,3]diazepin-6-yl]-6, 7-dihydro-5H-pyrrolo[1,2-b][1,2,4]triazole-2-carboxamide (27.6 mg, 47%) as a white solid. $^1$H NMR (400 MHz, $CD_3OD$) δ7.51 (s, 1H), 7.38-7.34 (m, 3H), 7.22-7.20 (m, 2H), 6.29 (s, 1H), 5.55 (t, J=6.8 Hz, 1H), 4.51-4.38 (m, 2H), 4.26-4.25 (m, 1H), 3.34 (s, 3H), 3.26-3.24 (m, 1H), 3.14-3.04 (m, 2H), 2.88-2.83 (m, 1H), 2.67-2.65 (m, 1H), 2.28-2.23 (m, 1H). LCMS $R_T$=0.753 min, m/z=392.0 $[M+H]^+$. LCMS (5 to 95% acetonitrile in water+0.03% trifluoacetic acid over 1.5 mins) retention time 0.753 min, ESI+ found [M+H]=392.0.

Example 615

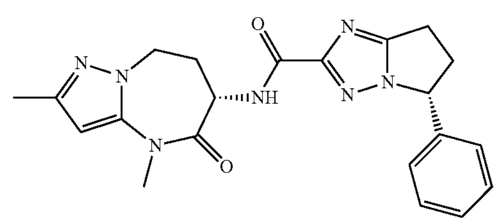 [SMILES: Cc1cc2n(n1)CC[C@H](NC(=O)c1nc3n(n1)[C@@H](c1ccccc1)CC3)C(=O)N2C]

(5R)-5-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Amide coupling prepared in a similar fashion to WX Method 108. The crude was purified by RP-HPLC (23% to 53% acetonitrile/0.05% ammonia hydroxide in water) to afford (5R)-5-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (16 mg, 26%) as white solid. $^1$H NMR (400 MHz, $CD_3OD$) δ7.41-7.23 (m, 3H), 7.23-7.21 (m, 2H), 6.10 (s, 1H), 5.56-5.52 (m, 1H), 4.53-4.48 (m, 1H), 4.29-4.19 (m, 2H), 3.31 (s, 3H), 3.26-3.24 (m, 1H), 3.15-3.05 (m, 2H), 2.85-2.81 (m, 1H), 2.67-2.60 (m, 1H), 2.25-2.21 (m, 4H). LCMS $R_T$=0.759 min; m/z=406.1 $(M+H)^+$.

LCMS (5 to 95% acetonitrile in water+0.1% trifluoacetic acid over 1.5 mins) retention time 0.759 min, ESI+ found [M+H]=406.1.

Example 616

WX Method 155

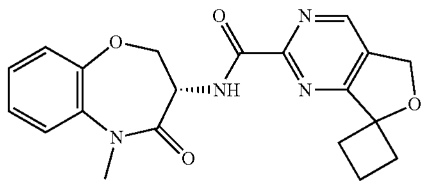 [SMILES: CN1C(=O)[C@@H](NC(=O)c2ncc3c(n2)C2(CCC2)OC3)COc2ccccc21]

N-[(3S)-5-methyl-4-oxo-2,3-dihydro-1,5-benzoxazepin-3-yl]spiro[5H-furo[3,4-d]pyrimidine-7,1'-cyclobutan]-2-carboxamide

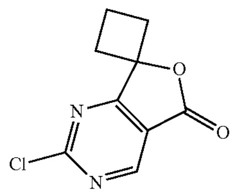 [SMILES: O=C1OC2(CCC2)c2nc(Cl)ncc21]

Step 1: 2'-chloro-5'H-spiro[cyclobutane-1,7'-furo[3,4-d]pyrimidin]-5'-one

To a solution of 2,2,6,6-tetramethylpiperidine (26.7 g, 189.2 mmol) in tetrahydrofuran (300 mL) was added n-butyllithium (2.5 M in hexanes, 76.0 mL, 189.2 mmol) at −78° C. The reaction mixture was stirred at −78° C. for 1 h and 2-chloropyrimidine-5-carboxylic acid (10.0 g, 63.1 mmol) was added. The reaction mixture was stirred at −78° C. for another 2 h and cyclobutanone (13.2 g, 189.2 mmol) was added. After addition, the reaction mixture was stirred at 25° C. for 16 h and quenched by addition of saturated ammonium chloride (50 mL). The mixture was extracted with ethyl acetate (3×200 mL). The combined organic layers were dried over sodium sulfate and concentrated under reduced pressure. The residue was purified by column chromatography (silica gel, 100-200 mesh, 0 to 5% ethyl acetate in petroleum ether) to afford 2'-chlorospiro[cyclobutane-1,7'-furo[3,4-d]pyrimidine]-5'-one (4.2 g, 32%) as a yellow solid. $^1$H NMR (400 MHz, $CDCl_3$) δ 8.97 (s, 1H), 2.84-2.72 (m, 2H), 2.66-2.57 (m, 2H), 2.29-2.16 (m, 1H), 2.15-2.03 (m, 1H).

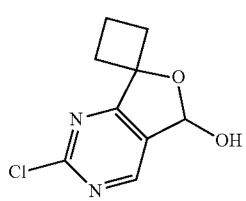 [SMILES: OC1OC2(CCC2)c2nc(Cl)ncc21]

Step 2: 2'-chloro-5'H-spiro[cyclobutane-1,7'-furo[3,4-d]pyrimidin]-5'-ol

To a solution of 2'-chlorospiro[cyclobutane-1,7'-furo[3,4-d]pyrimidine]-5'-one (1.0 g, 4.75 mmol) in toluene (5 mL) was added diisobutylaluminum hydride (14.2 mL, 14.2 mmol, 1.0 M in toluene) at −70° C. The resulting solution was stirred at −70° C. for 0.5 h and quenched by addition of saturated ammonium chloride (20 mL). The mixture was filtered and the filtrate was extracted with ethyl acetate (3×30 mL). The combined organic layers were dried over sodium sulfate to give the crude 2'-chloro-5'H-spiro[cyclobutane-1,7'-furo[3,4-d]pyrimidin]-5'-ol (850 mg, 84%) as a yellow oil. LCMS $R_T$=1.58 min, m/z=213.1 $[M+H]^+$. LCMS (0 to 60% acetonitrile in water+0.05% ammonium hydroxide over 3 mins) retention time 1.58 min, ESI+ found [M+H]=213.1.

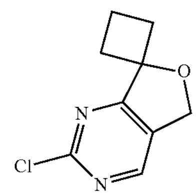 [SMILES: Clc1ncc2c(n1)C1(CCC1)OC2]

Step 3: 2'-chloro-5'H-spiro[cyclobutane-1,7'-furo[3,4-d]pyrimidine]

To a solution of 2'-chloro-5'H-spiro[cyclobutane-1,7'-furo[3,4-d]pyrimidin]-5'-ol (850 mg, 4.0 mol) in dichloromethane (10 mL) was added trifluoroacetic acid (4.6 g, 40.0 mmol) at 0° C. The mixture was stirred for 30 min at 0° C. and triethylsilane (4.6 g, 39.98 mmol) was added. After addition, the mixture was stirred for 12 h at 25° C. and quenched by addition of saturated sodium bicarbonate (20 mL). The resulting solution was extracted with dichloromethane (3×20 mL). The combined organic layers were washed with brine (20 mL), dried over sodium sulfate and concentrated under reduced pressure. The residue was purified by column chromatography (silica gel, 100-200 mesh, 0 to 35% ethyl acetate in petroleum ether to afford 2'-chloro-5'H-spiro[cyclobutane-1,7'-furo[3,4-d]pyrimidine](200 mg, 32%) as a yellow solid. $^1$H NMR (400 MHz, $CDCl_3$) δ 8.37 (s, 1H), 5.00 (s, 2H), 2.50-2.40 (m, 4H), 2.14-2.00 (m, 1H), 1.91-1.79 (m, 1H). LCMS $R_T$=1.94 min, m/z=197.1 $[M+H]^+$.

LCMS (0 to 60% acetonitrile in water+0.05% ammonium hydroxide over 3 mins) retention time 1.94 min, ESI+ found [M+H]=197.1.

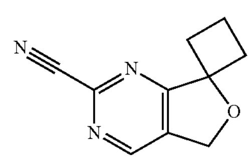 [SMILES: N#Cc1ncc2c(n1)C1(CCC1)OC2]

Step 4: 5'H-spiro[cyclobutane-1,7'-furo[3,4-d]pyrimidine]-2'-carbonitrile

To a solution of 2'-chloro-5'H-spiro[cyclobutane-1,7'-furo[3,4-d]pyrimidine] (200 mg, 1.02 mmol) in dimethyl sulfoxide (2 mL) and water (1 mL) was added 1,4-diazabicyclo[2.2.2]octane (143 mg, 1.27 mmol) and sodium cyanide (150 mg, 3.06 mmol). The reaction mixture was stirred at 25° C. for 16 h and diluted with water (15 mL). The mixture was extracted with ethyl acetate (3×15 mL). The combined organic layers were washed with brine (15 mL), dried over sodium sulfate and concentrated under reduced pressure to afford crude 5'H-spiro[cyclobutane-1,7'-furo[3,4-d]pyrimidine]-2'-carbonitrile (200 mg, 94%) as a yellow oil, used as is in the next step.

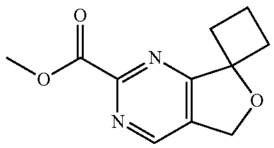 [SMILES: COC(=O)c1ncc2c(n1)C1(CCC1)OC2]

Step 5: methyl 5'H-spiro[cyclobutane-1,7'-furo[3,4-d]pyrimidine]-2'-carboxylate

A mixture of 5'H-spiro[cyclobutane-1,7'-furo[3,4-d]pyrimidine]-2'-carbonitrile (200 mg, 1.07 mmol) in methanol (5 mL) was added HCl (4N in methanol, 5 mL. The mixture was heated at 70° C. for 12 h and concentrated under reduced pressure to ice crude methyl 5'H-spiro[cyclobutane-1,7'-furo[3,4-d]pyrimidine]-2'-carboxylate (225 mg, 98%) as a yellow oil, used as is in the next step.

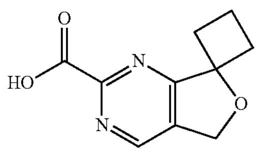 [SMILES: O=C(O)c1ncc2c(n1)C1(CCC1)OC2]

Step 6: 5'H-spiro[cyclobutane-1,7'-furo[3,4-d]pyrimidine]-2'-carboxylic acid

A mixture of methyl 5'H-spiro[cyclobutane-1,7'-furo[3,4-d]pyrimidine]-2'-carboxylate (220 mg, 1 mmol) and lithium hydroxyl hydrate (419 mg, 10 mmol) in tetrahydrofuran (5 mL) and water (5 mL) was stirred at 20° C. for 12 h. The organic solvent was evaporated under reduced pressure and the aqueous layer was adjusted to pH=2-3 by addition of 1N HCl. The mixture was extracted with dichloromethane (3×10 mL). The combined organic layers were dried over sodium sulfate and concentrated under reduced pressure to afford crude 5'H-spiro[cyclobutane-1,7'-furo[3,4-d]pyrimidine]-2'-carboxylic acid (150 mg, 73%) as a yellow solid. LCMS $R_T$=0.40 min, m/z=207.1 $[M+H]^+$.

LCMS (0 to 60% acetonitrile in water+0.05% ammonium hydroxide over 3 mins) retention time 0.40 min, ESI+ found [M+H]=207.1.

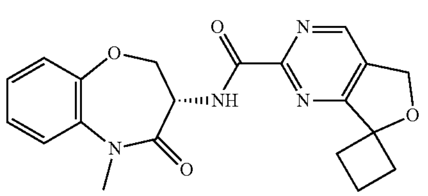 [SMILES: CN1C(=O)[C@@H](NC(=O)c2ncc3c(n2)C2(CCC2)OC3)COc2ccccc21]

Step 7: N-[(3S)-5-methyl-4-oxo-2,3-dihydro-1,5-benzoxazepin-3-yl]spiro[5H-furo[3,4-d]pyrimidine-7,1'-cyclobutane]-2-carboxamide A mixture of (3S)-3-amino-5-methyl-2,3-dihydro-1,5-benzoxazepin-4-one (30 mg, 0.16 mmol), spiro[5H-furo[3,4-d]pyrimidine-7,1'-cyclobutane]-2-carboxylic acid (35 mg, 0.17 mmol), $N^1$-((ethylimino)methylene)-$N^3$,$N^3$-dimethyl-propane-1,3-diamine hydrochloride (45 mg, 0.23 mmol) and 1H-benzo[d][1,2,3]triazol-1-ol (32 mg, 0.23 mmol) in N,N-dimethylformamide (3 mL) was stirred at 25° C. for 16 h. The mixture was concentrated under reduced pressure and the residue was purified by RP-HPLC (acetonitrile 25% to 55%/0.05% ammonium hydroxide in water) to afford N-[(3S)-5-methyl-4-oxo-2,3-dihydro-1,5-benzoxazepin-3-yl]spiro[5H-furo[3,4-d]pyrimidine-7,1'-cyclobutane]-2-carboxamide (25.1 mg, 41.9%) as a white solid. $^1$H NMR (400 MHz, $CD_3OD$) δ8.78 (s, 1H), 7.43 (m, 1H), 7.35-7.20 (m, 3H), 5.13 (s, 2H), 5.08-4.99 (m, 1H), 4.71 (m, 1H), 4.43 (m, 1H), 3.44 (s, 3H), 2.59-2.47 (m, 4H), 2.35-2.20 (m, 1H), 1.92 (m, 1H). LCMS $R_T$=1.65 min, m/z=381.1 $[M+H]^+$.

LCMS (0 to 60% acetonitrile in water+0.05% ammonium hydroxide over 3 mins) retention time 1.65 min, ESI+ found [M+H]=381.1.

Example 617

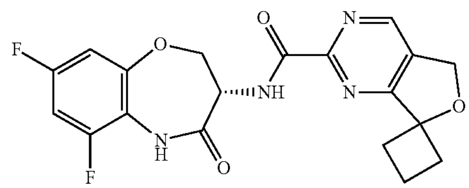 [SMILES: O=C(N[C@H]1COc2cc(F)cc(F)c2NC1=O)c1ncc2c(n1)C1(CCC1)OC2]

N-[(3S)-6,8-difluoro-4-oxo-3,5-dihydro-2H-1,5-benzoxazepin-3-yl]spiro[5H-furo[3,4-d]pyrimidine-7,1'-cyclobutane]-2-carboxamide Amide coupling prepared in a similar fashion to WX Method 155. The crude was purified by RP-HPLC (acetonitrile 25% to 55%/0.05% ammonium hydroxide in water) to give N-[(3S)-6,8-difluoro-4-oxo-3,5-dihydro-2H-1,5-benzoxazepin-3-yl]spiro[5H-furo[3,4-d]pyrimidine-7,1'-cyclobutane]-2-carboxamide (22 mg, 38%) as a white solid. $^1$H NMR (400 MHz, $CD_3OD$) δ8.79 (s, 1H), 6.99-6.80 (m, 2H), 5.22-5.06 (m, 3H), 4.81-4.75 (m, 1H), 4.59-4.47 (m, 1H), 2.61-2.45 (m, 4H), 2.35-2.21 (m, 1H), 1.92 (m, 1H). LCMS $R_T$=1.62 min, m/z=403.1 $[M+H]^+$.

LCMS (0 to 60% acetonitrile in water+0.05% ammonium hydroxide over 3 mins) retention time 1.62 min, ESI+ found [M+H]=403.1.

Example 618

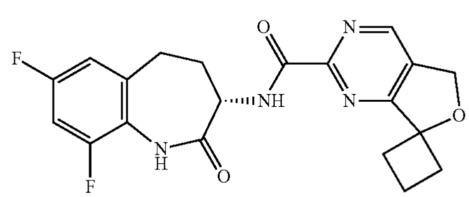 [SMILES: O=C(N[C@H]1CCc2cc(F)cc(F)c2NC1=O)c1ncc2c(n1)C1(CCC1)OC2]

N-[(3S)-7,9-difluoro-2-oxo-1,3,4,5-tetrahydro-1-benzazepin-3-yl]spiro 5H-furo[3,4-d]pyrimidine-7,1'-cyclobutane]-2-carboxamide Amide coupling prepared in a similar fashion to WX Method 155. The crude was purified by RP-HPLC (acetonitrile 22% to 52%/0.05% ammonium hydroxide in water) to give N-[(3S)-7,9-difluoro-2-oxo-1,3,4,5-tetrahydro-1-benzazepin-3-yl]spiro[5H-furo[3,4-d]pyrimidine-7,1'-cyclobutane]-2-carboxamide (17 mg, 30%) as a white solid. $^1$H NMR (400 MHz, $CD_3OD$) δ 8.78 (s, 1H), 7.07-6.98 (m, 2H), 5.13 (s, 2H), 4.70-4.57 (m, 1H), 3.08-2.96 (m, 1H), 2.89-2.75 (m, 2H), 2.59-2.47 (m, 4H), 2.33-2.19 (m, 2H), 1.97-1.87 (m, 1H). LCMS $R_T$=1.60 min, m/z=401.1 $[M+H]^+$.

LCMS (0 to 60% acetonitrile in water+0.05% ammonium hydroxide over 3 mins) retention time 1.60 min, ESI+ found [M+H]=401.1.

Examples 619 and 620

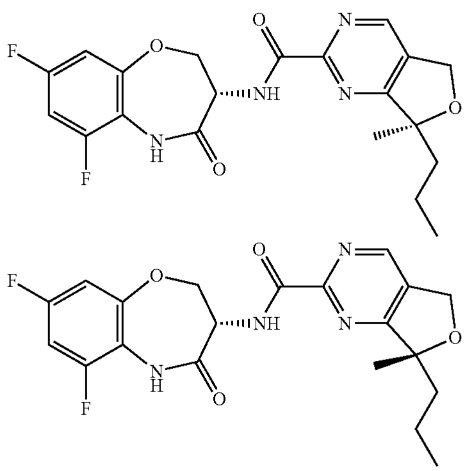

(7S)-7-methyl-7-propyl-N-[(3S)-6,8-difluoro-4-oxo-3,5-dihydro-2H-1,5-benzoxazepin-3-yl]-5H-furo[3,4-d]pyrimidine-2-carboxamide and (7R)-7-methyl-7-propyl-N-[(3S)-6,8-difluoro-4-oxo-3,5-dihydro-2H-1,5-benzoxazepin-3-yl]-5H-furo[3,4-d]pyrimidine-2-carboxamide Amide coupling prepared in a similar fashion to WX Method N. The obtained racemic compound was separated by chiral SFC to give:

(7S)-7-methyl-7-propyl-N-[(3S)-6,8-difluoro-4-oxo-3,5-dihydro-2H-1,5-benzoxazepin-3-yl]-5H-furo[3,4-d]pyrimidine-2-carboxamide (Peak 1, retention time 2.196 min) (11.7 mg, 39%) as a white solid. $^1$H NMR (400 MHz, $CD_3OD$) δ8.83 (s, 1H), 6.97-6.88 (m, 2H), 5.17-5.07 (m, 3H), 4.79-4.74 (m, 1H), 4.58-4.52 (m, 1H), 1.93-1.83 (m, 2H), 1.50-1.40 (m, 4H), 1.07-1.01 (m, 1H), 0.90-0.86 (m, 3H). LCMS $R_T$=0.815 min; m/z=419.0 $(M+H)^+$.

LCMS (5 to 95% acetonitrile in water+0.03% trifluoacetic acid over 2 mins) retention time 0.815 min, ESI+ found [M+H]=419.0.

(7R)-7-methyl-7-propyl-N-[(3S)-6,8-difluoro-4-oxo-3,5-dihydro-2H-1,5-benzoxazepin-3-yl]-5H-furo[3,4-d]pyrimidine-2-carboxamide (Peak 2, retention time 2.316 min), (8.7 mg, 29%) as a white solid. $^1$H NMR (400 MHz, $CD_3OD$) δ8.83 (s, 1H), 6.97-6.88 (m, 2H), 5.17-5.07 (m, 3H), 4.79-4.74 (m, 1H), 4.58-4.52 (m, 1H), 1.93-1.83 (m, 2H), 1.50-1.40 (m, 4H), 1.07-1.01 (m, 1H), 0.89-0.86 (m, 3H). LCMS $R_T$=0.997 min; m/z=419.3 $(M+H)^+$.

LCMS (10 to 80% acetonitrile in water+0.03% trifluoacetic acid over 2 mins) retention time 0.997 min, ESI+ found [M+H]=419.3.

SFC conditions: Column: Chiralcel OJ-3 100×4.6 mm I.D., 3 um Mobile phase: A: $CO_2$ B: methanol (0.05% DEA) Gradient: from 5% to 40% of B in 4.5 min and hold 40% for 2.5 min, then 5% of B for 1 min Flow rate: 2.8 mL/min Column temperature: 40° C.

Example 621

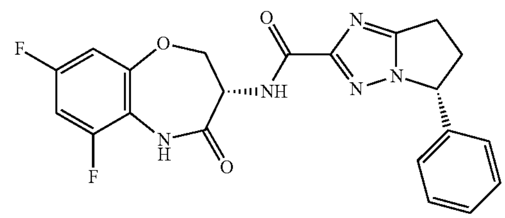 [SMILES: O=C(N[C@H]1COc2cc(F)cc(F)c2NC1=O)c1nc2n(n1)[C@@H](c1ccccc1)CC2]

(5R)-5-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide Amide coupling prepared in a similar fashion to WX Method 108. The crude was purified by RP-HPLC (30% to 60% acetonitrile/0.05% ammonia hydroxide in water) to afford (5R)-5-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide (18 mg, 27%) as white solid. $^1$H NMR (400 MHz, $CD_3OD$) δ7.41-7.35 (m, 3H), 7.23-7.21 (m, 2H), 6.92-6.84 (m, 2H), 5.57-5.53 (m, 1H), 5.07-5.03 (m, 1H), 4.67-4.65 (m, 1H), 4.63-4.48 (m, 1H), 3.27-3.25 (m, 1H), 3.14-3.13 (m, 1H), 3.08-3.06 (m, 1H), 2.70-2.67 (m, 1H). LCMS $R_T$=0.796 min; m/z=426.0 $(M+H)^+$.

LCMS (5 to 95% acetonitrile in water+0.1% trifluoacetic acid over 1.5 mins) retention time 0.796 min, ESI+ found [M+H]=426.0

Example 622

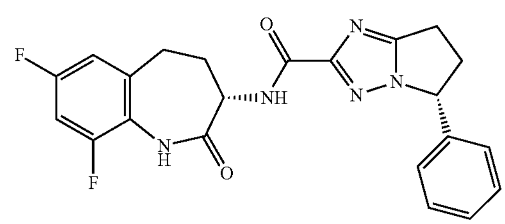 [SMILES: O=C(N[C@H]1CCc2cc(F)cc(F)c2NC1=O)c1nc2n(n1)[C@@H](c1ccccc1)CC2]

(5R)-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide Amide coupling prepared in a similar fashion to WX Method 108. The crude was purified by RP-HPLC (26% to 56% acetonitrile/0.05% ammonia hydroxide in water) to afford (5R)-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (29 mg, 44%) as white solid.

$^1$H NMR (400 MHz, $CD_3OD$) δ7.40-7.34 (m, 3H), 7.22-7.21 (m, 2H), 7.00-6.98 (m, 2H), 5.56-5.52 (m, 1H), 4.60-4.53 (m, 1H), 3.27-3.25 (m, 1H), 3.12-3.10 (m, 1H), 3.07-3.05 (m, 1H), 2.96-2.93 (m, 1H), 2.85-2.82 (m, 1H), 2.66-2.63 (m, 2H), 2.21-2.16 (m, 1H). LCMS $R_T$=0.797 min; m/z=424.0 $(M+H)^+$.

LCMS (5 to 95% acetonitrile in water+0.1% trifluoacetic acid over 1.5 mins) retention time 0.797 min, ESI+ found [M+H]=424.0

Example 623

WX Method 108

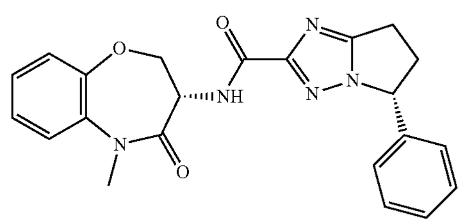 [SMILES: CN1C(=O)[C@@H](NC(=O)c2nc3n(n2)[C@@H](c2ccccc2)CC3)COc2ccccc21]

(5R)-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide

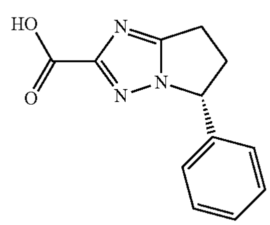 [SMILES: O=C(O)c1nc2n(n1)[C@@H](c1ccccc1)CC2]

Step 1: (5R)-5-phenyl-6,7-dihydro-5H-pyrrolo[1,2-b][1,2,4]triazole-2-carboxylic

To a solution of ethyl (5R)-5-phenyl-6,7-dihydro-5H-pyrrolo[1,2-b][1,2,4]triazole-2-carboxylate (130 mg, 0.51 mmol) in tetrahydrofuran (2 mL)/methanol (2 mL)/water (1 mL) was added lithium hydroxide hydrate (127.2 mg, 3.03 mmol). The mixture was stirred at 25° C. for 1 h and diluted with water (10 mL). The solution was adjusted to pH=4-5 by addition of 1N HCl. The mixture was extracted with ethyl acetate (3×15 mL). The combined organic layers were dried over sodium sulfate and concentrated under reduced pressure to give crude (5S)-5-phenyl-6,7-dihydro-5H-pyrrolo[1,2-b][1,2,4]triazole-2-carboxylic acid (110 mg, 95%) as a light yellow solid, used as is in the next step.

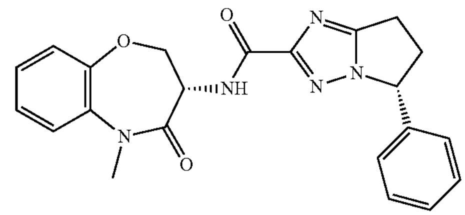 [SMILES: CN1C(=O)[C@@H](NC(=O)c2nc3n(n2)[C@@H](c2ccccc2)CC3)COc2ccccc21]

Step 2: (5R)-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide A mixture of (3S)-3-amino-5-methyl-2,3-dihydro-1,5-benzoxazepin-4-one (30 mg, 0.16 mmol), (5R)-5-phenyl-6,7-dihydro-5H-pyrrolo[1,2-b][1,2,4]triazole-2-carboxylic acid (30 mg, 0.16 mmol), $N^1$-((ethylimino)methyl ene)-$N^3$,$N^3$-di methylpropane-1,3-diamine hydrochloride (30 mg, 0.15 mmol) and 1H-benzo[d][1,2,3]triazol-1-ol (21 mg, 0.16 mmol) in N,N-dimethylformamide (5 mL) was stirred at 25° C. for 16 h. The mixture was concentrated under reduced pressure and the residue was purified by RP-HPLC (35% to 65% acetonitrile, 0.05% ammonia hydroxide in water) to afford (5R)-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide (29 mg, 55%) as a white solid. $^1$H NMR (400 MHz, $CD_3OD$) δ7.41-7.21 (m, 9H), 5.54 (t, J=6.8 Hz, 1H), 5.00-4.96 (m, 1H), 4.59-4.56 (m, 1H), 4.41-4.36 (m, 1H), 3.40 (s, 3H), 3.27-3.24 (m, 1H), 3.15-3.04 (m, 2H), 2.67-2.65 (m, 1H). LCMS $R_T$=0.801 min; m/z=404.1 $(M+H)^+$.

LCMS (5 to 95% acetonitrile in water+0.03% trifluoacetic acid over 1.5 mins) retention time 0.801 min, ESI+ found [M+H]=404.1.

Example 624

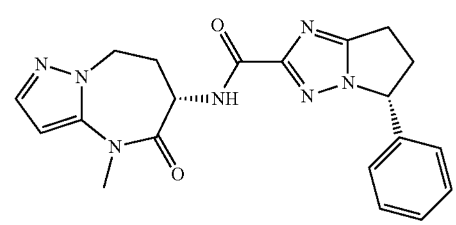 [SMILES: CN1C(=O)[C@@H](NC(=O)c2nc3n(n2)[C@@H](c2ccccc2)CC3)CCn2nccc21]

(5R)-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Amide coupling prepared in a similar fashion to WX Method 108. The crude was purified by RP-HPLC (28% to 58% acetonitrile/0.05% ammonia hydroxide in water) to afford (5R)-5-phenyl-N-[(6S)-4-methy-5-oxo-7,8-dihydro-6H-pyrazolo[4-methyl-5-oxo-[1,5-a][1,3]diazepin-6-yl]-6,7-dihydro-5H-pyrrolo[1,2-b][1,2,4]triazole-2-carboxamide (17.4 mg, 34%) as a white solid. $^1$H NMR (400 MHz, $CD_3OD$) δ7.51 (s, 1H), 7.38-7.34 (m, 3H), 7.22-7.20 (m, 2H), 6.29 (s, 1H), 5.55 (t, J=6.8 Hz, 1H), 4.51-4.38 (m, 2H), 4.26-4.25 (m, 1H), 3.34 (s, 3H), 3.26-3.24 (m, 1H), 3.14-

3.04 (m, 2H), 2.88-2.83 (m, 1H), 2.67-2.65 (m, 1H), 2.28-2.23 (m, 1H). LCMS $R_T$=0.727 min; m/z=392.0 (M+H)+.

LCMS (5 to 95% acetonitrile in water+0.03% trifluoacetic acid over 1.5 mins) retention time 0.727 min, ESI+ found [M+H]=392.0.

Examples 625 and 626

WX Method 113

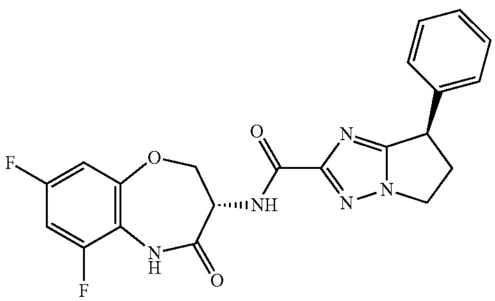

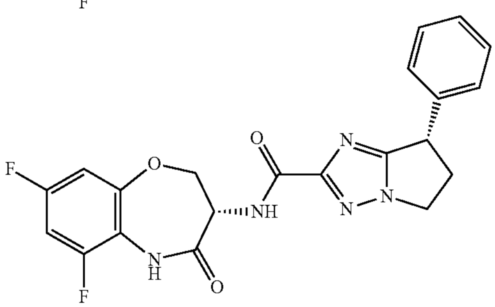

(7S)-7-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide and (7R)-7-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide

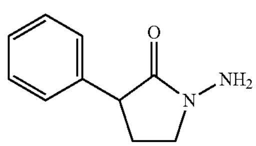 [SMILES: NN1CCC(c2ccccc2)C1=O]

Step 1: 1-amino-3-phenylpyrrolidin-2-one

To a solution of tert-butyl N-(2-oxo-3-phenyl-pyrrolidin-1-yl)carbamate (1.4 g, 5.1 mmol) in ethyl acetate (20 mL) was added HCl (4N in ethyl acetate, 12.0 mL, 48.0 mmol). The mixture was stirred at 20° C. for 3 h and concentrated under reduced pressure. The residue was slowly quenched by addition of saturated sodium bicarbonate (30 mL). The resulting solution was extracted with ethyl acetate (3×50 mL). The combined organic layers were dried over sodium sulfate and concentrated to give crude 1-amino-3-phenyl-pyrrolidin-2-one (590 mg, 66%) as a white solid, used as is in the next step.

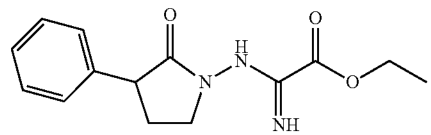 [SMILES: CCOC(=O)C(=N)NN1CCC(c2ccccc2)C1=O]

Step 2: ethyl 2-imino-2-((2-oxo-3-phenylpyrrolidin-1-yl)amino)acetate

To a solution of 1-amino-3-phenyl-pyrrolidin-2-one (590 mg, 3.35 mmol) in ethanol (10 mL) was added ethyl 2-ethoxy-2-imino-acetate (1458 mg, 10.04 mmol). The mixture was stirred at 40° C. for 12 h and concentrated under reduced pressure to obtain crude ethyl (2Z)-2-amino-2-(2-oxo-3-phenyl-pyrrolidin-1-yl)imino-acetate (1370 mg, 100%), used as is in the next step.

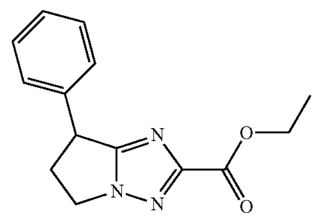 [SMILES: CCOC(=O)c1nc2n(n1)CCC2c1ccccc1]

Step 3: ethyl 7-phenyl-6,7-dihydro-5H-pyrrolo[1,2-b][1,2,4]triazole-2-carboxylate A solution of ethyl (2Z)-2-amino-2-(2-oxo-3-phenyl-pyrrolidin-1-yl)imino-acetate (1370 mg, 4.98 mmol) in phosphorus oxychloride (5 mL) as stirred at 120° C. for 1 h. After cooled, the mixture was slowly quenched by addition of saturated sodium bicarbonate (20 mL) and extracted with dichloromethane (3×20 mL). The combined organic layers were washed with brine (30 mL), dried over sodium sulfate and concentrated under reduced pressure. The residue was purified by column chromatography (silica gel, 100-200 mesh, 0 to 50% ethyl acetate in petroleum ether) to afford ethyl 7-phenyl-6,7-dihydro-5H-pyrrolo[1,2-b][1,2,4]triazole-2-carboxylate (390 mg, 31%) as a light yellow solid. $^1$H NMR (400 MHz, $CDCl_3$) δ 7.40-7.14 (m, 5H), 4.45 (q, J=8.0 Hz, 4H), 4.40-4.36 (m, 1H), 4.26-4.23 (m, 1H), 3.29-3.22 (m, 1H), 2.78-2.70 (m, 1H), 1.40 (t, J=7.2 Hz, 3H). LCMS $R_T$=1.95 min, m/z=258.1 [M+H]+.

LCMS (0 to 60% acetonitrile in water+0.05% ammonium hydroxide over 3 mins) retention time 1.95 min, ESI+ found [M+H]=258.1.

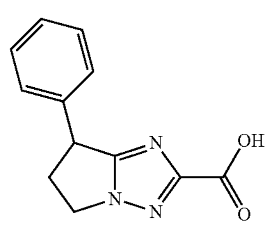 [SMILES: O=C(O)c1nc2n(n1)CCC2c1ccccc1]

Step 4: 7-phenyl-6,7-dihydro-5H-pyrrolo[1,2-b][1,2,4]triazole-2-carboxylic acid

A mixture of ethyl (7S)-7-phenyl-6,7-dihydro-5H-pyrrolo[1,2-b][1,2,4]triazole-2-carboxylate (340 mg, 1.32 mmol) and lithium hydroxide hydrate (555 mg, 13.22 mmol) in tetrahydrofuran (5 mL) and water (5 mL) was stirred at 20° C. for 12 h. The organic solvent was evaporated under reduced pressure and the aqueous residue was adjusted to pH=2-3 by addition of 20% HCl. The mixture was extracted with dichloromethane (5×30 mL). The combined organic layers were dried over sodium sulfate and concentrated under reduced pressure to afford the crude 7-phenyl-6,7-dihydro-5H-pyrrolo[1,2-b][1,2,4]triazole-2-carboxylic acid (260 mg, 85%) as a yellow solid used as is in the next step.

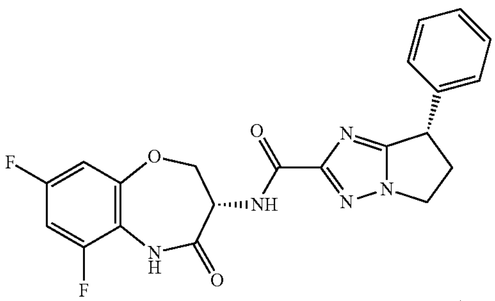

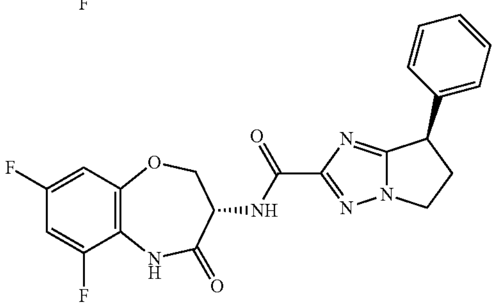

Step 5: (7S)-7-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide and (7R)-7-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide A mixture of 7-phenyl-6,7-dihydro-5H-pyrrolo[1,2-b][1,2,4]triazole-2-carboxylic acid (33 mg, 0.14 mmol), 1-(3-dimethylaminopropyl)-3-ethyl carbodiimidehydrochloride (33 mg, 0.17 mmol), 1-hydroxybenzotriazole (29 mg, 0.21 mmol) and (3s)-3-amino-6,8-difluoro-3,5-dihydro-2H-1,5-benzoxazepin-4-one (28 mg, 0.13 mmol) in N,N-dimethylformamide (3 mL) was stirred at 25° C. for 12 h. The mixture was concentrated under reduced pressure and the residue was purified by RP-HPLC (22% to 52% acetonitrile/0.05% ammonia hydroxide in water) to afford N-[(3S)-6,8-difluoro-4-oxo-3,5-dihydro-2H-1,5-benzoxazepin-3-yl]-7-phenyl-6,7-dihydro-5H-pyrrolo[1,2-b][1,2,4]triazole-2-carboxamide (40 mg, 72%) as a white solid.

The racemic material was separated by chiral SFC to give:

(7S)-7-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide (Peak 1, retention time 6.694 min) (20 mg, 50%) as white solids. $^1$H NMR (400 MHz, $CD_3OD$) δ 7.38-7.33 (m, 2H), 7.31-7.26 (m, 3H), 6.96-6.89 (m, 1H), 6.88-685 (m, 1H), 5.08-5.04 (m, 1H), 4.68-4.64 (m, 1H), 4.56-4.37 (m, 3H), 4.32-4.23 (m, 1H), 3.26-3.25 (m, 1H), 2.78-2.66 (m, 1H). LCMS $R_T$=2.22 min, m/z=426.1 $[M+H]^+$.

LCMS (0 to 60% acetonitrile in water+0.03% ammonium bicarbonate over 3.0 mins) retention time 2.22 min, ESI+ found [M+H]=426.1.

(7R)-7-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide (Peak 2, retention time 7.313 min) (19 mg, 48%) as a white solid. $^1$H NMR (400 MHz, $CD_3OD$) δ7.29-7.22 (m, 2H), 7.21-7.14 (m, 3H), 6.87-6.79 (m, 1H), 6.78-6.75 (m, 1H), 4.98-4.94 (m, 1H), 4.58-4.56 (m, 1H), 4.48-4.27 (m, 3H), 4.32-4.19 (m, 1H), 3.18-3.14 (m, 1H), 2.67-2.56 (m, 1H). LCMS RT=2.23 min, m/z=426.2 $[M+H]^+$.

LCMS (0 to 60% acetonitrile in water+0.03% ammonium bicarbonate over 3.0 mins) retention time 2.23 min, ESI+ found [M+H]=426.2.

SFC conditions: Column: Chiralcel AD-3 100×4.6 mm I.D., 3 um Mobile phase: A: $CO_2$ B: ethanol (0.05% dethyl acetate), Gradient: from 5% to 40% of B in 4.5 min and hold 40% for 2.5 min, then 5% of B for 1 min, Flow rate: 2.8 mL/min Column temperature: 40° C.

Examples 627 and 628

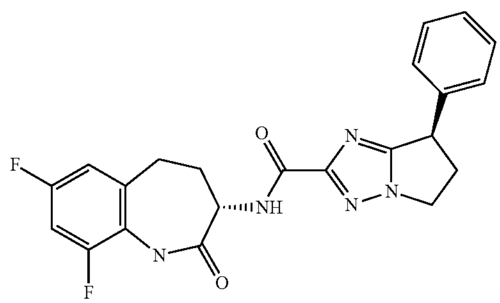

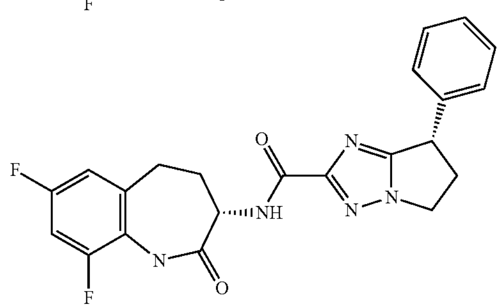

(7S)-7-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide and (7R)-7-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide Amide coupling prepared in a similar fashion to WX Method 113. The racemic material (70 mg) was separated by chiral SFC to give:

(7S)-7-phenyl-N-[(3S)-7,9-difluoro-2-oxo-1,3,4,5-tetrahydro-1-benzazepin-3-yl]-6,7-dihydro-5H-pyrrolo[1,2-b][1, 2,4]triazole-2-carboxamide (Peak 1, retention time=6.794 min) (34.1 mg, 48.2%) as a white solid. $^1H$ NMR (400 MHz, $CD_3OD$) δ7.37-7.26 (m, 5H), 7.02-6.98 (m, 2H), 4.60-4.51 (m, 2H), 4.43-4.40 (m, 1H), 4.30-4.27 (m, 1H), 3.30-3.27 (m, 1H), 2.98-2.96 (m, 1H), 2.83-2.81 (m, 1H), 2.71-2.63 (m, 2H), 2.21-2.19 (m, 1H). LCMS $R_T$=1.730 min, m/z=424.1 $[M+H]^+$.

LCMS (10 to 80% acetonitrile in water+0.03% ammonium bicarbonate over 3.0 mins) retention time 1.730 min, ESI+ found [M+H]=424.1.

(7R)-7-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide (Peak 2, retention time=7.082 min) (32.5 mg, 46%) as a white solid. $^1H$ NMR (400 MHz, $CD_3OD$) δ7.37-7.33 (m, 2H), 7.32-7.26 (m, 3H), 7.01-6.98 (m, 2H), 4.59-4.50 (m, 2H), 4.45-4.40 (m, 1H), 4.27-4.25 (m, 1H), 3.30-3.27 (m, 1H), 2.98-2.96 (m, 1H), 2.83-2.81 (m, 1H), 2.71-2.63 (m, 2H), 2.22-2.19 (m, 1H). LCMS $R_T$=1.730 min, m/z=424.1 $[M+H]^+$. LCMS (10 to 80% acetonitrile in water+0.03% ammonium bicarbonate over 3.0 mins) retention time 1.730 min, ESI+ found [M+H]=424.1.

SFC condition: column: chiralpak AD-3 (250 mm*30 mm, 5 um), 3 um mobile phase: A: CO2; B: EtOH (0.05% DEA) gradient: from 5 to 40 of B in 4.5 min and hold 40% for 2.5 min, then 5% of B for 1 min. Flow rate: 2.8 mL/min. Column temperature: 40° C.

Example 629

WX Method 125

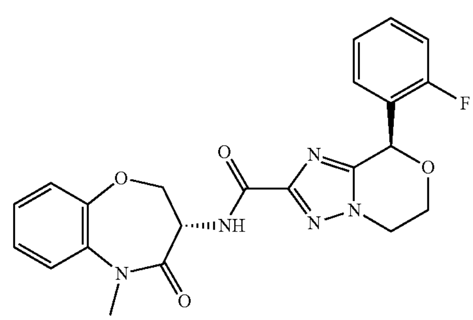 [SMILES: CN1C(=O)[C@@H](NC(=O)c2nc3n(n2)CCO[C@@H]3c2ccccc2F)COc2ccccc21]

(8R)-8-(2-fluorophenyl)-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide

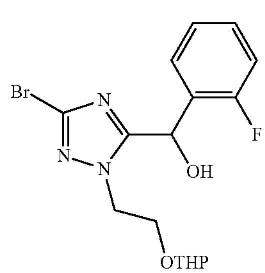

Step 1: (3-bromo-1-(2-((tetrahydro-2H-pyran-2-yl)oxy)ethyl)-1H-H-1,2,4-triazol-5-yl)(2-fluorophenyl)methanol To a solution of 3,5-dibromo-1-(2-tetrahydropyran-2-yloxyethyl)-1,2,4-triazole (2.0 g, 5.6 mmol) in tetrahydrofuran (20 mL) was added n-butyllithium (2.5 M in hexanes, 2.6 mL, 6.5 mmol) at −78° C. The mixture was stirred at −78° C. for 1 h and then a solution of 2-fluorobenzaldehyde (1.4 g, 11.27 mmol) in THF (2 mL) was added. After addition, the mixture was stirred at −78° C. for another 1 h and then quenched by addition of saturated ammonium chloride (10 mL). The resulting mixture was diluted with ethyl acetate (100 mL), washed with water (20 mL), brine (20 mL), dried over sodium sulfate and concentrated under reduced pressure. The residue was purified by column chromatography (silica gel, 100-200 mesh, 0 to 20% ethyl acetate in petroleum ether) to afford [5-bromo-2-(2-tetrahydropyran-2-yloxyethyl)-1,2,4-triazol-3-yl]-(2-fluorophenyl)methanol (1.0 g, 44%) as a light yellow oil. LCMS $R_T$=0.64 min, m/z=401.7 $[M+H]^+$. LCMS (5 to 95% acetonitrile in water+0.03% trifluoacetic acid over 1.5 mins) retention time 0.64 min, ESI+ found [M+H]=401.7.

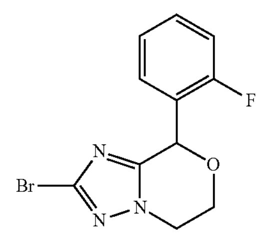 [SMILES: Fc1ccccc1C1OCCn2nc(Br)nc21]

Step 2: 2-bromo-8-(2-fluorophenyl)-6,8-dihydro-5H-[1,2,4]triazolo[5,1-c][1,4]oxazine A mixture of [5-bromo-2-(2-tetrahydropyran-2-yloxyethyl)-1,2,4-triazol-3-yl]-(2-fluorophenyl)methanol (1000 mg, 2.5 mmol) and p-toluenesulfonic acid (546 mg, 3.17 mmol) in toluene (20 mL) was heated at reflux for 3 h. The mixture was concentrated under reduced pressure, and the residue was purified by column chromatography (silica gel, 100-200 mesh, 0 to 30% ethyl acetate in petroleum ether) to give 2-bromo-8-(2-fluorophenyl)-6,8-dihydro-5H-[1,2,4]triazolo[5,1-c][1,4]oxazine (300 mg, 40.3%) as yellow solid, used as is in the next step.

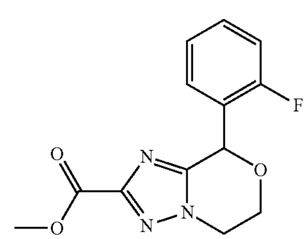 [SMILES: COC(=O)c1nc2n(n1)CCOC2c1ccccc1F]

Step 3: Methyl 8-(2-fluorophenyl)-6,8-dihydro-5H-[1,2,4]triazolo[5,1-c][1,4]oxazine-2-carboxylate A mixture of 2-bromo-8-(2-fluorophenyl)-6,8-dihydro-5H-[1,2,4]triazolo[5,1-c][1,4]oxazine (290 mg, 0.97 mmol), 1,1'-bis(diphenylphosphino)ferrocene palladium dichloride (13 mg, 0.02 mmol). and triethylamine (1.31 mL, 9.73 mmol) in methanol (10 mL) was heated at 80° C. for 16 h under CO (25 psi) and filtered. The filtrate was concentrated under reduced pressure and the residue was purified by column chromatography (silica gel, 100-200 mesh, 100% dichloromethane) to give methyl 8-(2-fluorophenyl)-6,8-dihydro-5H-[1,2,4]triazolo[5,1-c][1,4]oxazine-2-carboxylate (200 mg, 74%) as colorless oil. LCMS $R_T$=0.59 min, m/z=277.8 $[M+H]^+$.

LCMS (5 to 95% acetonitrile in water+0.03% trifluoacetic acid over 1.5 mins) retention time 0.59 min, ESI+ found [M+H]=277.8.

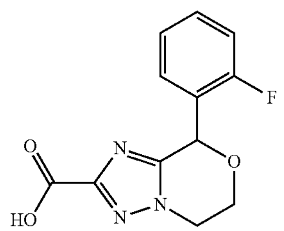 [SMILES: O=C(O)c1nc2n(n1)CCOC2c1ccccc1F]

Step 4: 8-(2-fluorophenyl)-6,8-dihydro-5H-[1,2,4]triazolo[5,1-c][1,4]oxazine-2-carboxylic acid A mixture of methyl 8-(2-fluorophenyl)-6,8-dihydro-5H-[1,2,4]triazolo[5,1-c][1,4]oxazine-2-carboxylate (200 mg, 0.72 mmol) and potassium hydroxide (80 mg, 1.44 ml) in ethanol (20 mL) and water (5 mL) was stirred at 25° C. for 1 h. The ethanol was evaporated under reduced pressure and the aqueous residue was adjusted to pH=3 by addition of 2N HCl. The solution was extracted with ethyl acetate (2×10 mL). The combined organic layers were concentrated to give crude 8-(2-fluorophenyl)-6,8-dihydro-5H-[1,2,4]triazolo[5,1-c][1,4]oxazine-2-carboxylic acid (180 mg, 94%) as a yellow solid, used as is in the next step.

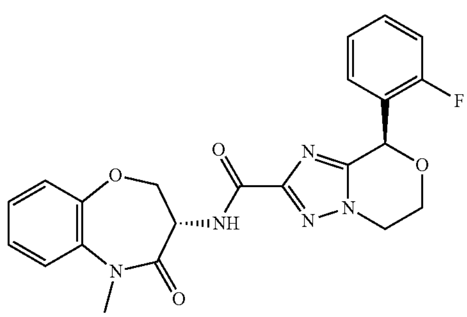 [SMILES: CN1C(=O)[C@@H](NC(=O)c2nc3n(n2)CCO[C@@H]3c2ccccc2F)COc2ccccc21]

Step 5: (8R)-8-(2-fluorophenyl)-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide A mixture of (3S)-3-amino-5-methyl-2,3-dihydro-1,5-benzoxazepin-4-one (50 mg, 0.26 mmol), 8-(2-fluorophenyl)-6,8-dihydro-5H-[1,2,4]triazolo[5,1-c][1,4]oxazine-2-carboxylic acid (102 mg, 0.39 mmol), 1-(3-dimethylaminopropyl)-3-ethyl carbodiimide hydrochloride (49 mg, 0.26 mmol) and 1-hydroxybenzotriazole (7 mg, 0.05 mmol) in N,N-dimethylformamide (10 mL) was stirred at 25° C. for 16 h. The mixture was concentrated under reduced pressure and the residue was purified by RP-HPLC (36% to 66% acetonitrile/0.05% ammonia hydroxide in water) to give 8-(2-fluorophenyl)-N-[(3S)-5-methyl-4-oxo-2,3-dihydro-1,5-benzoxazepin-3-yl]-6, 8-dihydro-5H-[1,2,4]triazolo[5,1-c][1,4]oxazine-2-carboxamide (60 mg, 53%) as a white solid. The racemic material was separated by chiral SFC to give:

(8R)-8-(2-fluorophenyl)-N-[(3S)-5-methyl-4-oxo-2,3-dihydro-1,5-benzoxazepin-3-yl]-6,8-di hydro-5H-[1,2,4]triazolo[5,1-c][1,4]oxazine-2-carboxamide (Peak 2, retention time 1.825 min) (33 mg, 54.3%) as a white solid. $^1H$ NMR (400 MHz, DMSO-$d_6$) δ 8.43 (d, J=8.0 Hz, 1H), 7.52-7.45 (m, 2H), 7.45-7.39 (m, 1H), 7.34-7.20 (m, 5H), 6.18 (s, 1H), 4.86-4.77 (m, 1H), 4.61-4.55 (m, 1H), 4.45-4.32 (m, 4H), 4.25-4.17 (m, 1H), 3.29 (s, 3H). LCMS $R_T$=0.80 min, m/z=438.1 $[M+H]^+$.

LCMS (5 to 95% acetonitrile in water+0.1% trifluoacetic acid over 1.5 mins) retention time 0.80 min, ESI+ found [M+H]=438.1.

SFC: Column: Chiralcel AD-3 50×4.6 mm I.D., 3 um Mobile phase: A: CO2 B: ethanol (0.05% DEA) Gradient: from 5% to 40% of B in 5 min and hold 5% for 0.2 min, then from 5% to 40% of B in 1.4 min and hold 40% for 1.05 min, then 5% of B for 0.35 min Column temp.: 40° C.

Example 630

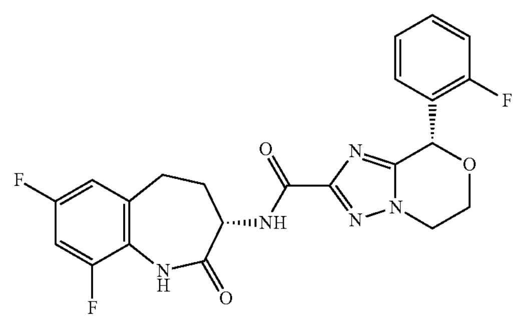 [SMILES: O=C(N[C@H]1CCc2cc(F)cc(F)c2NC1=O)c1nc2n(n1)CCO[C@H]2c1ccccc1F]

(8S)-8-(2-fluorophenyl)-N-[(3S)-7,9-difluoro-2-oxo-1,3,4,5-tetrahydro-1-benzazepin-3-yl]-6,8-dihydro-5H-[1,2,4]triazolo[5,1-c][1,4]oxazine-2-carboxamide Amide coupling prepared in a similar fashion to WX Method 125. The crude was purified by RP-HPLC (35% to 75% acetonitrile/0.05% ammonia hydroxide in water) to give N—((S)-7,9-difluoro-2-oxo-2,3,4,5-tetrahydro-1H-benzo[b]azepin-3-yl)-8-(2-fluorophenyl)-6, 8-dihydro-5H-[1,2,4]triazolo[5,1-c][1,4]oxazine-2-carboxamide (60 mg, 53%) as a white solid. The racemic material (30 mg) was separated by chiral SFC to give:

(8S)-8-(2-fluorophenyl)-N-[(3S)-7,9-difluoro-2-oxo-1,3,4,5-tetrahydro-1-benzazepin-3-yl]-6, 8-dihydro-5H-[1,2,4]triazolo[5,1-c][1,4]oxazine-2-carboxamide (Peak 2, retention time 1.588 min) (30 mg, 49.5%) as a white solid. $^1H$ NMR (400 MHz, $CD_3OD$) δ7.47-7.41 (m, 1H), 7.37-7.32 (m, 1H), 7.23-7.12 (m, 2H), 7.01-6.94 (m, 3H), 6.13 (s, 1H), 4.57-4.33 (m, 4H), 4.27-4.18 (m, 1H), 3.00-2.89 (m, 1H), 2.72-2.75 (m, 1H), 2.64-2.53 (m, 1H), 2.23-2.15 (m, 1H). LCMS $R_T$=0.79 min, m/z=458.1 $[M+H]^+$.

LCMS (5 to 95% acetonitrile in water+0.03% trifluoacetic acid over 1.5 mins) retention time 0.79 min, ESI+ found [M+H]=458.1.

SFC conditions: Column: Chiralcel AD-3 50×4.6 mm I.D., 3 um Mobile phase: A: CO2 B: ethanol (0.05% DEA) Gradient: from 5% to 40% of B in 5 min and hold 5% for 0.2 min, then from 5% to 40% of B in 1.4 min and hold 40% for 1.05 min, then 5% of B for 0.35 min Column temp.: 40° C.

Example 631

WX Method 138

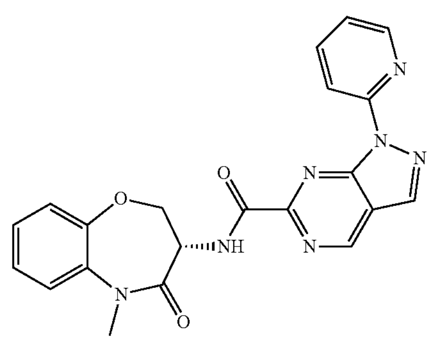 [SMILES: CN1C(=O)[C@@H](NC(=O)c2ncc3cnn(-c4ccccn4)c3n2)COc2ccccc21]

1-(2-pyridyl)-N-[(3S)-5-methyl-4-oxo-2,3-dihydro-1,5-benzoxazepin-3-yl]pyrazolo[3,4-d]pyrimidine-6-carboxamide

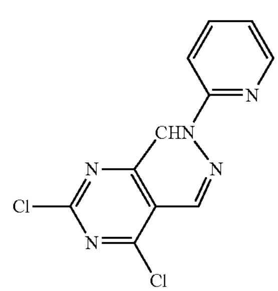

Step 1: N—[(Z)-(2,4,6-trichloropyrimidin-5-yl) methyleneamino]pyridin-2-amine

To a solution of 2,4,6-trichloro-5-pyrimidinecarboxaldehyde (1.0 g, 4.73 mmol) in N,N-dimethylformamide (5 mL) was added 2-hydrazinopyridine (530 mg, 4.86 mmol). The mixture was stirred at 20° C. for 12 h and added water (20 mL), saturated sodium bicarbonate (10 mL). The resulting solid was collected by filtration and dried under reduced pressure to afford N—[(Z)-(2,4,6-trichloropyrimidin-5-yl) methyleneamino]pyridin-2-amine (900 mg, 63%) as a brown solid, used as is in the next step.

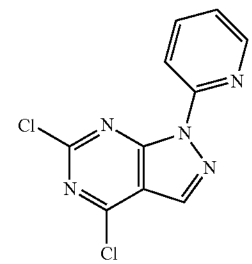 [SMILES: Clc1nc(Cl)c2cnn(-c3ccccn3)c2n1]

Step 2: 4,6-dichloro-1-(2-pyridyl)pyrazolo[3,4-d] pyrimidine

A solution of N—[(Z)-(2,4,6-trichloropyrimidin-5-yl) methyleneamino]pyridin-2-amine (820 mg, 2.71 mmol) in acetonitrile (30 mL) was stirred at 110° C. for 6 h under microwave conditions. The reaction mixture was concentrated under reduced pressure and the residue was purified by column chromatography (silica gel, 100-200 mesh, 0 to 40% ethyl acetate in petroleum ether) to afford 4,6-dichloro-1-(2-pyridyl)pyrazolo[3,4-d]pyrimidine (550 mg, 76%) as a white solid, used as is in the next step.

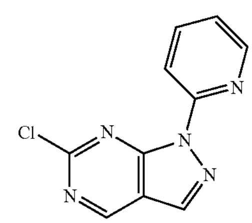 [SMILES: Clc1ncc2cnn(-c3ccccn3)c2n1]

Step 3: 6-chloro-1-(2-pyridyl)pyrazolo[3,4-d]pyrimidine

To a mixture of 4,6-dichloro-1-(2-pyridyl)pyrazolo[3,4-d]pyrimidine (550 mg, 2.07 mmol) and zinc (418 mg, 6.39 mmol) in tetrahydrofuran (20 mL) was added ammonium hydroxide (20 mL) at 0° C. The reaction mixture was stirred for 1.5 h and adjusted to pH=9 by addition of saturated sodium bicarbonate. The mixture was filtered and the filtrate was extracted with ethyl acetate (2×50 mL). The combined organic layers were dried over sodium sulfate and concentrated under reduced pressure. The residue was purified by preparative TLC (petroleum ether: ethyl acetate=1:1, $R_f$=0.2) to afford 6-chloro-1-(2-pyridyl)pyrazolo[3,4-d]pyrimidine (270 mg, 56%) as a light yellow solid, used as is in the next step.

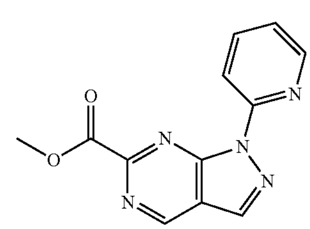 [SMILES: COC(=O)c1ncc2cnn(-c3ccccn3)c2n1]

Step 4: methyl 1-(2-pyridyl)pyrazolo[3,4-d]pyrimidine-6-carboxylate

A mixture of 6-chloro-1-(2-pyridyl)pyrazolo[3,4-d]pyrimidine (180 mg, 0.78 mmol), triethylamine (0.88 mL, 6.32 mmol), 1,1'-bis(diphenylphosphino)ferrocene palladium dichloride (57 mg, 0.08 mmol) in methanol (20 mL) was heated at 70° C. under CO (35 psi) for 20 h and filtered. The filtrate was evaporated under reduced pressure and the residue was purified by preparative TLC (ethyl acetate, $R_f$=0.2) to afford methyl 1-(2-pyridyl)pyrazolo[3,4-d]pyrimidine-6-carboxylate (120 mg, 61%) as a brown oil, used as is in the next step.

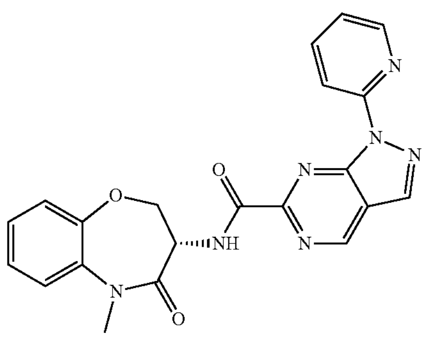 [SMILES: CN1C(=O)[C@@H](NC(=O)c2ncc3cnn(-c4ccccn4)c3n2)COc2ccccc21]

Step 6: 1-(2-pyridyl)-N-[(3S)-5-methyl-4-oxo-2,3-dihydro-1,5-benzoxazepin-3-yl]pyrazolo[3,4-d]pyrimidine-6-carboxamide To a solution of (3S)-3-amino-5-methyl-2,3-dihydro-1,5-benzoxazepin-4-one (23 mg, 0.12 mmol), methyl 1-(2-pyridyl)pyrazolo[3,4-d]pyrimidine-6-carboxylate (30 mg, 0.12 mmol) in toluene (10 mL) was added trimethylaluminum (0.2 mL, 0.40 mol) in toluene (10 mL). The mixture was heated at 110° C. for 12 h and then quenched by addition of methanol (5 mL). The mixture was concentrated under reduced pressure and the residue was purified by preparative TLC (dichloromethane methane=10:1, $R_f$=0.5) to afford 1-(2-pyridyl)-N-[(3S)-5-methyl-4-oxo-2,3-dihydro-1,5-benzoxazepin-3-yl]pyrazolo[3,4-d]pyrimidine-6-carboxamide (5 mg, 9.8%) as a yellow oil. $^1$H NMR (400 MHz, $CD_3OD$) δ 9.53 (s, 1H), 8.68 (s, 1H), 8.65 (d, J=4.0 Hz, 1H), 8.49 (d, J=8.4 Hz, 1H), 8.19-8.12 (m, 1H), 7.54-7.50 (m, 1H), 7.48-7.44 (m, 1H), 7.36-7.30 (m, 2H), 7.28-7.25 (m, 1H), 5.12-5.07 (m, 1H), 4.73-4.69 (m, 1H), 4.55-4.47 (m, 1H), 3.45 (s, 3H). LC-MS $R_T$=0.757 min, m/z=416.0 $(M+H)^+$ LCMS (5 to 95% acetonitrile in water+0.03% trifluoacetic acid over 2 mins) retention time 0.757 min, ESI+ found [M+H]=416.0.

Examples 632 and 633

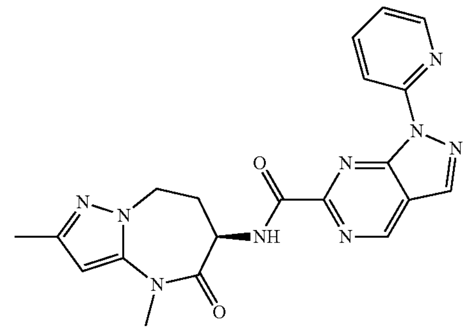

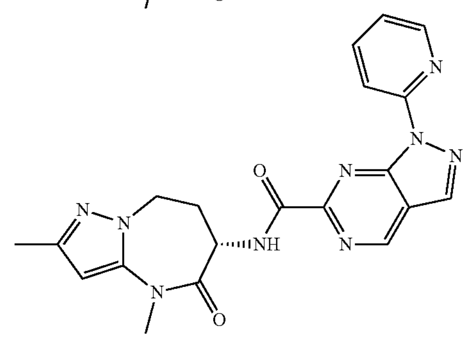

1-(2-pyridyl)-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide and 1-(2-pyridyl)-N-[(6R)-2,4-dimethyl-5-oxo-7,8-dihydro-6H-pyrazolo[1,5-a][1,3]diazepin-6-yl]pyrazolo[3,4-d]pyrimidine-6-carboxamide Ester-amide exchange prepared in a similar fashion to WX Method 138. The racemic compound was separated by chiral SFC to give arbitrarily assigned enantiomers:

1-(2-pyridyl)-N-[1(6S)-2,4-dimethyl-5-oxo-7,8-dihydro-6H-pyrazolo[1,5-a][1,3]diazepin-6-yl]pyrazolo[3,4-d]pyrimidine-6-carboxamide (Peak 1, retention time 1.70 min) (14.5 mg, 47%) as a light yellow oil. $^1$H NMR (400 MHz, $CD_3OD$) δ9.53 (s, 1H), 8.68 (s, 1H), 8.64 (d, J=4.0 Hz, 1H), 8.50 (d, J=8.4 Hz, 1H), 8.18-8.11 (m, 1H), 7.55-7.50 (m, 1H), 6.14 (s, 1H), 4.66-4.59 (m, 1H), 4.36-4.27 (m, 2H), 3.37 (s, 3H), 3.02-2.92 (m, 1H), 2.39-2.31 (m, 1H), 2.27 (s, 3H). LC-MS $R_T$=0.712 min, m/z=418.0 $(M+H)^+$.

LCMS (5 to 95% acetonitrile in water+0.03% trifluoacetic acid over 1.5 mins) retention time 0.712 min, ESI+ found [M+H]=418.0.

1-(2-pyridyl)-N-[(6R)-2,4-dimethyl-5-oxo-7,8-dihydro-6H-pyrazolo[1,5-a][1,3]diazepin-6-yl]pyrazolo[3,4-d]pyrimidine-6-carboxamide (Peak 2, retention time 2.07 min) (5.0 mg, 16%) as a yellow oil. $^1$H NMR (400 MHz, $CD_3OD$) δ9.52 (s, 1H), 8.68 (s, 1H), 8.64 (s, 1H), 8.48 (d, J=8.4 Hz, 1H), 8.14 (t, J=7.2 Hz, 1H), 7.56-7.49 (m, 1H), 6.14 (s, 1H), 4.67-4.59 (m, 1H), 4.41-4.25 (m, 2H), 3.37 (s, 3H), 3.01-2.93 (m, 1H), 2.38-2.29 (m, 1H), 2.27 (s, 3H).

LC-MS $R_T$=0.709 min, m/z=418.0 $(M+H)^+$. LCMS (5 to 95% acetonitrile in water+0.03% trifluoacetic acid over 1.5 mins) retention time 0.709 min, ESI+ found [M+H]=418.0.

SFC condition: Column: Chiralpak AD-3 50*4.6 mm I.D., 3 um Mobile phase: A: $CO_2$ B: ethanol (0.05% DEA) Gradient: hold 5% for 0.2 min, then from 5% to 40% of B in 1.4 min and hold 40% for 1.05 min, then 5% of B for 0.35 min Flow rate: 4 mL/min Column temp: 40° C.

Example 634

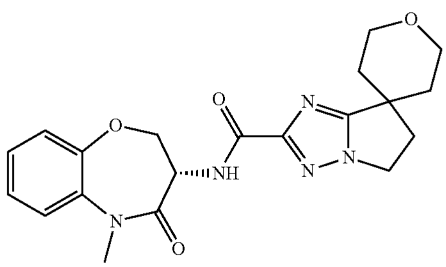 [SMILES: CN1C(=O)[C@@H](NC(=O)c2nc3n(n2)CCC32CCOCC2)COc2ccccc21]

N-[(3S)-5-methyl-4-oxo-2,3-dihydro-1,5-benzoxazepin-3-yl]spiro[5,6-dihydropyrrol[1,2-b][1,2,4]triazole-7,4'-tetrahydropyran]-2-carboxamide Amide coupling prepared in a similar fashion to WX Method 129. The crude was purified by RP-HPLC (22% to 52% acetonitrile/0.05% ammonia hydroxide in water) to afford N-[(3S)-5-methyl-4-oxo-2,3-dihydro-1,5-benzoxazepin-3-yl]spiro[5,6-dihydropyrrolo[1,2-b][1,2,4]triazole-7,4'-tetrahydropyran]-2-carboxamide (15 mg, 56%) as a white solid. $^1$H NMR (400 MHz, $CD_3OD$) δ7.46-7.40 (m, 1H), 7.36-7.27 (m, 2H), 7.25-7.21 (m, 1H), 5.03-4.98 (m, 1H), 4.62-4.58 (m, 1H), 4.45-4.39 (m, 1H), 4.27-4.23 (m, 2H), 4.08-4.00 (m, 2H), 3.79-3.70 (m, 2H), 3.42 (s, 3H), 2.71-2.67 (m, 2H), 1.97-1.87 (m, 2H), 1.82-1.70 (m, 2H). LCMS $R_T$=1.58 min, m/z=398.3 $[M+H]^+$. LCMS (10 to 80% acetonitrile in water+0.05% ammonium hydroxide over 3 mins) retention time 1.58 min, ESI+ found [M+H]=398.3.

Example 635

WX Method 131

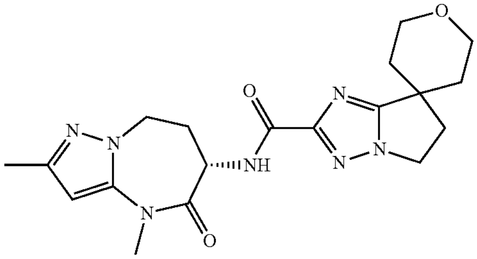 [SMILES: Cc1cc2n(n1)CC[C@H](NC(=O)c1nc3n(n1)CCC31CCOCC1)C(=O)N2C]

N-[(6S)-2,4-dimethyl-5-oxo-7,8-dihydro-6H-pyrazolo[1,5-a][1,3]diazepin-6-yl]spiro[5,6-dihydropyrrolo[1,2-b][1,2,4]triazole-7,4'-tetrahydropyran]-2-carboxamide

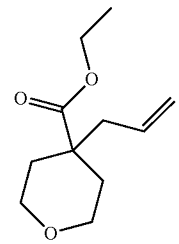

Step 1: ethyl 4-allyltetrahydropyran-4-carboxylate

To a solution of ethyl tetrahydropyran-4-carboxylate (10.0 g, 63.22 mmol) in tetrahydrofuran (200 mL) was added lithium diisopropylazanide (2N in tetrahedron, 32.91 mL, 65.81 mmol) at −78° C. The reaction mixture was stirred at −78° C. for 30 min and then allyl bromide (9.2 g, 75.86 mmol) was added. The reaction mixture was stirred at 20° C. for 16 h and quenched by addition of saturated ammonium chloride (20 mL). The resulting mixture was extracted with ethyl acetate (3×200 mL). The combined organic layers were washed with water (100 mL), brine (100 mL), dried over sodium sulfate and concentrated under reduced pressure to afford crude ethyl 4-allyltetrahydropyran-4-carboxylate (9.0 g, 72%) as a yellow oil, used as is in the next step.

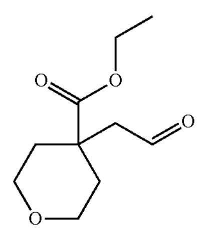

Step 2: ethyl 4-(2-oxoethyl)tetrahydropyran-4-carboxylate

A mixture of ethyl 4-allyltetrahydropyran-4-carboxylate (9.0 g, 45.39 mmol), osmium tetroxide (500 mg, 1.97 mmol) and sodium periodate (14.5 g, 68.09 mmol) in tetrahydrofuran (100 mL) and water (100 mL) was stirred at 20° C. for 2 h. The mixture was quenched by addition of water (300 mL) and extracted with ethyl acetate (3×200 mL). The combined organic layers were washed with water (100 mL), brine (100 mL), dried over sodium sulfate and concentrated under reduced pressure. The residue was purified by column chromatography (silica gel, 100-200 mesh, 0 to 50% ethyl acetate in petroleum ether) to afford ethyl 4-(2-oxoethyl)tetrahydropyran-4-carboxylate (4.0 g, 44%) as a yellow oil, used as is in the next step.

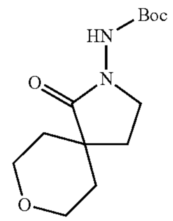 [SMILES: CC(C)(C)OC(=O)NN1CCC2(CCOCC2)C1=O]

Step 3: tert-butyl N-(1-oxo-8-oxa-2-azaspiro[4.5]decan-2-yl)carbamate

To a solution of ethyl 4-(2-oxoethyl)tetrahydropyran-4-carboxylate (4.0 g, 19.98 mmol) in acetic acid (20 mL) and tetrahydrofuran (40 mL) was added tert-butyl hydrazinecarboxylate (3.17 g, 23.97 mmol). The reaction mixture was stirred at 20° C. for 2 h and sodium cynoborohydride (3.77 g, 59.93 mmol) was added. The reaction mixture was heated at 50° C. for 6 h and concentrated under reduced pressure. The residue was purified by RP-HPLC (17% to 47% acetonitrile/0.05% ammonia hydroxide in water) to afford tert-butyl N-(1-oxo-8-oxa-2-azaspiro[4.5]decan-2-yl)carbamate (1.0 g, 18%) as a white solid, used as is in the next step.

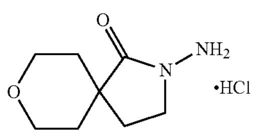 [SMILES: NN1CCC2(CCOCC2)C1=O ; Cl]

Step 4: 2-amino-8-oxa-2-azaspiro[4.5]decan-1-one hydrochloride

To a solution of tert-butyl N-(1-oxo-8-oxa-2-azaspiro[4.5]decan-2-yl)carbamate (200 mg, 0.74 mmol) in ethyl acetate (5 mL) was added HCl (4N in ethyl acetate, 10.0 mL, 40.0 mmol). The mixture was stirred at 35° C. for 12 h and concentrated under reduced pressure to afford crude 2-amino-8-oxa-2-azaspiro[4.5]decan-1-one (120 mg, 95%) as a yellow oil, used as is in the next step.

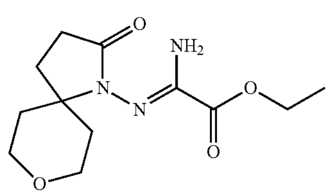 [SMILES: CCOC(=O)/C(N)=N/N1C(=O)CCC12CCOCC2]

Step 5: (Z)-ethyl 2-amino-2-((2-oxo-8-oxa-1-azaspiro[4.5]decan-1-yl)imino)acetate To a solution of 2-amino-8-oxa-2-azaspiro[4.5]decan-1-one hydrochloride (100 mg, 0.59 mmol) in ethanol (10 mL) was added ethyl 2-ethoxy-2-imino-acetate (256 mg, 1.76 mmol). The mixture was stirred at 30° C. for 12 h and concentrated under reduced pressure to give crude ethyl (2Z)-2-amino-2-[(2-oxo-8-oxa-1-azaspiro[4.5]decan-1-yl)imino]acetate (130 mg, 82%) as a yellow oil. LCMS $R_T$=1.43 min, m/z=270.1 $[M+H]^+$. LCMS (0 to 60% acetonitrile in water+0.05% ammonium hydroxide over 3 mins) retention time 1.43 min, ESI+ found [M+H]=270.1

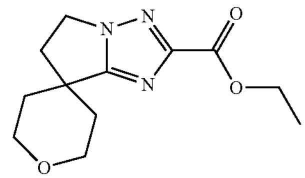 [SMILES: CCOC(=O)c1nc2n(n1)CCC21CCOCC1]

Step 6: ethyl 2,3,5,5',6,6'-hexahydrospiro[pyran-4,7'-pyrrolo[1,2-b][1,2,4]triazole]-2'-carboxylate A mixture of (Z)-2-amino-2-[(2-oxo-8-oxa-1-azaspiro[4.5]decan-1-yl)imino]acetate (180 mg, 0.67 mmol) and phosphorus oxychloride (5 mL, 53.28 mmol) in ethyl acetate (10 mL) was heated at 120° C. for 1 h and cooled. The mixture was slowly quenched by addition of water (20 mL) and extracted with dichloromethane (3×20 mL). The combined organic layers were washed with 20% sodium bicarbonate (20 mL), brine (30 mL), dried over sodium sulfate and concentrated under reduced pressure. The residue was purified by column chromatography (silica gel, 100-200 mesh, 0 to 60% ethyl acetate in petroleum ether) to afford ethyl spiro[5,6-dihydropyrrolo[1,2-b][1,2,4]triazole-7,4'-tetrahydropyran]-2-carboxylate (85 mg, 51%) as a light yellow oil, used as is in the next step.

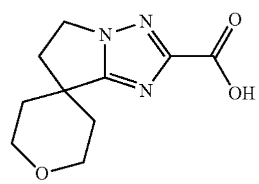 [SMILES: O=C(O)c1nc2n(n1)CCC21CCOCC1]

Step 7: 2,3,5,5',6,6'-hexahydrospiro[pyran-4,7'-pyrrolo[1,2-b][1,2,4]triazole]-2'-carboxylic acid A mixture of ethyl spiro[5,6-dihydropyrrolo[1,2-b][1,2,4]triazole-7,4'-tetrahydropyran]-2-carboxylate (80 mg, 0.32 mmol) and lithium hydroxide (153 mg, 6.37 mmol) in tetrahydrofuran (5 mL) and water (5 mL) was stirred at 20° C. for 12 h. After evaporation of the organic solvent, the mixture was adjusted to pH=6 by addition of 1N HCl. The mixture was extracted with ethyl acetate (3×10 mL). The combined organic layers were concentrated under reduced pressure to give crude spiro[5,6-dihydropyrrolo[1,2-b][1,2,4]triazole-7,4'-tetrahydropyran]-2-carboxylic acid (60 mg, 84%) as a yellow oil, used as is in the next step.

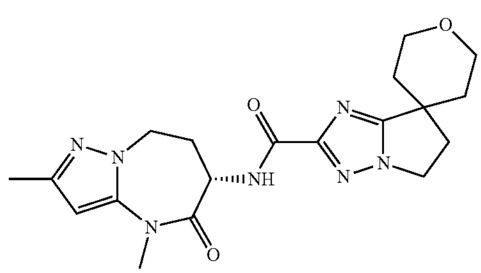 [SMILES: Cc1cc2n(n1)CC[C@H](NC(=O)c1nc3n(n1)CCC31CCOCC1)C(=O)N2C]

Step 8: N-[(6S)-2,4-dimethyl-5-oxo-7,8-dihydro-6H-pyrazolo[1,5-a][1,3]diazepin-6-yl]spiro[5,6-dihydropyrrolo[1,2-b][1,2,4]triazole-7,4'-tetrahydropyran]-2-carboxamide Amide coupling prepared in a similar fashion to WX Method 129. The crude was purified by RP-HPLC (22% to 52% acetonitrile/0.05% ammonia hydroxide in water) to afford N-[(6S)-2,4-dimethyl-5-oxo-7,8-dihydro-6H-pyrazolo[1,5-a][1,3]diazepin-6-yl]spiro[5,6-dihydropyrrolo[1,2-b][1,2,4]triazole-7,3'-tetrahydrofuran]-2-carboxamide (6.7 mg, 18.5%) as a white solid. $^1H$ NMR (400 MHz, $CD_3OD$) δ6.11 (s, 1H), 4.59-4.49 (m, 1H), 4.37-4.16 (m, 4H), 4.06-4.02 (m, 2H), 3.80-3.68 (m, 2H), 3.33 (s, 3H), 2.86-2.84 (m, 1H), 2.74-2.65 (m, 2H), 2.30-2.21 (m, 4H), 1.99-1.88 (m, 2H), 1.82-1.71 (m, 2H). LCMS $R_T$=1.13 min, m/z=400.2 $[M+H]^+$.

LCMS (10 to 80% acetonitrile in water+0.05% ammonium hydroxide over 3 mins) retention time 1.13 min, ESI+ found [M+H]=400.2.

Example 636

WX Method 134

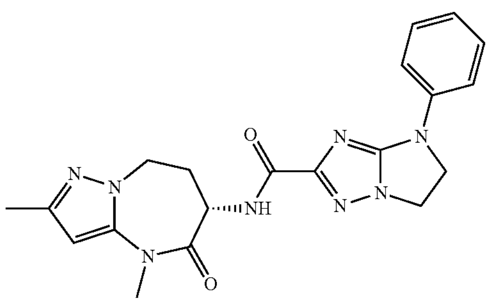 [SMILES: Cc1cc2n(n1)CC[C@H](NC(=O)c1nc3n(n1)CCN3c1ccccc1)C(=O)N2C]

4-phenyl-N-[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide

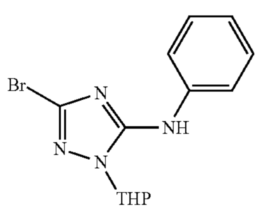

Step 1: 3-bromo-N-phenyl-1-(tetrahydro-2H-pyran-2-yl)-1H-1,2,4-triazol-5-amine

To a solution of aniline (329 mg, 3.54 mmol) in tetrahydrofuran (5 mL) was added lithium bis(trimethylsilyl)amide (1N in tetrahedron, 12.86 mL, 12.86 mmol), and then 3,5-dibromo-1-tetrahydropyran-2-yl-1,2,4-triazole (500 mg, 1.61 mmol) at 0° C. The reaction mixture was stirred at 0° C. for 15 h and quenched by addition of saturate ammonium chloride (10 mL). The mixture was extracted with dichloromethane (2×20 mL). The combined organic layers were concentrated under reduced pressure and the residue was purified by column chromatography (silica gel, 100-200 mesh, 0-20% ethyl acetate in petroleum ether) to afford 3-bromo-N-phenyl-1-(tetrahydro-2H-pyran-2-yl)-1H-1,2,4-triazol-5-amine (500 mg, 96%) as a yellow solid, used as is in the next step.

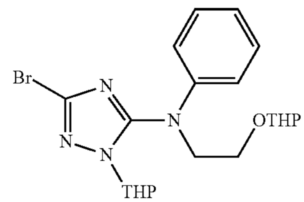

Step 2: 3-bromo-N-phenyl-1-(tetrahydro-2H-pyran-2-yl)-N-(2-((tetrahydro-2H-pyran-2-yl)oxy)ethyl)-1H-1,2,4-triazol-5-amine To a solution of sodium iodide (232 mg, 1.55 mmol) and 3-bromo-N-phenyl-1-(tetrahydro-2H-pyran-2-yl)-1H-1,2,4-triazol-5-amine (500 mg, 1.55 mmol) in N,N-dimethylformamide (10 mL) was added sodium hydride (60%, 62 mg, 1.55 mmol). The reaction mixture was stirred at 50° C. for 0.5 hour, then 2-(2-bromoethoxy)tetrahydro-2H-pyran (408 mg, 1.95 mmol) was added. After addition, the mixture was stirred at 50° C. for another 15 h and then diluted with ice water (5 mL). The resulting mixture was extracted with ethyl acetate (3×10 mL). The combined organic layers were concentrated under reduced pressure and the residue was purified by column chromatography (silica gel, 100-200 mesh, 0-20% ethyl acetate in petroleum ether) to give 3-bromo-N-phenyl-1-(tetrahydro-2H-pyran-2-yl)-N-(2-((tetrahydro-2H-pyran-2-yl)oxy)ethyl)-1H-1,2,4-triazol-5-amine (500 mg, 72%) as yellow oil, used as is in the next step.

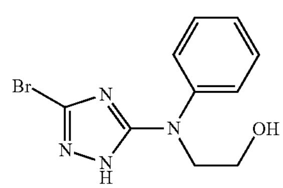 [SMILES: OCCN(c1ccccc1)c1nc(Br)n[nH]1]

Step 3: 2-((3-bromo-1H-1,2,4-triazol-5-yl)(phenyl)amino)ethanol

A mixture of 3-bromo-N-phenyl-1-(tetrahydro-2H-pyran-2-yl)-N-(2-((tetrahydro-2H-pyran-2-yl)oxy)ethyl)-1H-1,2,4-triazol-5-amine (500 mg, 1.11 mmol) and 2,2,2-trifluoroacetic acid (126 mg, 1.11 mmol) in dichloromethane (10 mL) was stirred at 15° C. for 15 h and concentrated under reduced pressure to afford crude 2-(N-(3-bromo-1H-1,2,4-triazol-5-yl)-2,6-difluoro-anilino)ethanol (200 mg, 64%) as a brown oil. LCMS $R_T$=1.315 min, m/z=283.2 $[M+H]^+$. LCMS (0 to 60% acetonitrile in water+0.03% trifluoacetic acid over 3.0 mins) retention time 1.315 min, ESI+ found [M+H]=283.2.

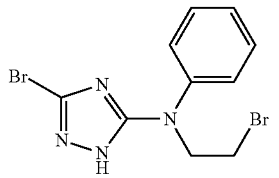 [SMILES: BrCCN(c1ccccc1)c1nc(Br)n[nH]1]

Step 4: 3-bromo-N-(2-bromoethyl)-N-phenyl-1H-1,2,4-triazol-5-amine

A mixture of 2-(N-(3-bromo-1H-1,2,4-triazol-5-yl)-2,6-difluoro-anilino)ethanol (100 mg, 0.35 mmol) and phosphoryl tribromide (101 mg, 0.35 mmol) in acetonitrile (5 mL) was heated at 50° C. for 15 h and concentrated under reduced pressure. The residue was purified by column chromatography (silica gel, 100-200 mesh, 0-20% ethyl acetate in petroleum ether) to afford 3-bromo-N-(2-bromoethyl)-N-(2,6-difluorophenyl)-1H-1,2,4-triazol-5-amine (100 mg, 82%) as a brown oil. LCMS $R_T$=0.719 min, m/z=346.8 $[M+H]^+$. LCMS (5 to 95% acetonitrile in water+0.03% trifluoacetic acid over 1.5 mins) retention time 0.719 min, ESI+ found [M+H]=346.8.

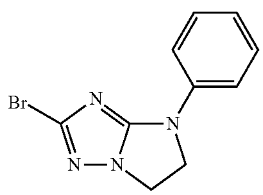 [SMILES: Brc1nc2n(n1)CCN2c1ccccc1]

Step 5: 2-bromo-4-phenyl-5,6-dihydro-4H-imidazo[1,2-b][1,2,4]triazole

A mixture of 3-bromo-N-(2-bromoethyl)-N-(2,6-difluorophenyl)-1H-1,2,4-triazol-5-amine (90 mg, 0.26 mmol) and potassium carbonate (36 mg, 0.26 mmol) in N,N-dimethylformamide (5 mL) was stirred at 20° C. for 15 h and then diluted with ice water (3 mL). The mixture was extracted with ethyl acetate (2×10 mL). The combined organic layers were concentrated under reduced pressure and the residue was purified by column chromatography (silica gel, 100-200 mesh, 0-50% ethyl acetate in petroleum ether) to afford 2-bromo-4-phenyl-5,6-dihydro-4H-imidazo[1,2-b][1,2,4]triazole (50 mg, 73%) as a white solid, used as is in the next step.

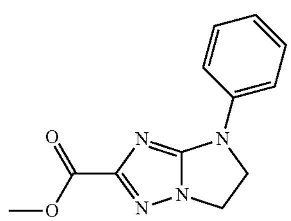 [SMILES: COC(=O)c1nc2n(n1)CCN2c1ccccc1]

Step 6: methyl 4-phenyl-5,6-dihydro-4H-imidazo[1,2-b][1,2,4]triazole-2-carboxylate A mixture of 2-bromo-4-phenyl-5,6-dihydro-4H-imidazo[1,2-b][1,2,4]triazole (50 mg, 0.19 mmol), 1,1'-bis(diphenylphosphino)ferrocene palladium dichloride (13 mg, 0.02 mmol) and triethylamine (191 mg, 1.88 mmol) in methanol (40 mL) was heated at 70° C. for 12 h under CO (40 psi) and filtered. The filtrate was concentrated under reduced pressure and the residue was purified by column chromatography (silica gel, 100-200 mesh, 0 to 20% ethyl acetate in petroleum ether) to afford methyl 4-phenyl-5,6-dihydro-4H-imidazo[1,2-b][1,2,4]triazole-2-carboxylate (45 mg, 98%) as a yellow solid. LCMS $R_T$=1.535 min, m/z=245.3 $[M+H]^+$. LCMS (0 to 60% acetonitrile in water+0.03% trifluoacetic acid over 3.0 mins) retention time 1.535 min, ESI+ found [M+H]=245.3.

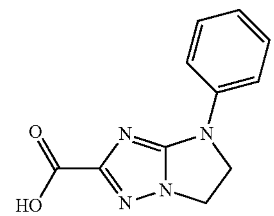 [SMILES: O=C(O)c1nc2n(n1)CCN2c1ccccc1]

Step 7: 4-phenyl-5,6-dihydro-4H-imidazo[1,2-b][1,2,4]triazole-2-carboxylic acid

A mixture of methyl 4-phenyl-5,6-dihydro-4H-imidazo[1,2-b][1,2,4]triazole-2-carboxylate (40 mg, 0.16 mmol) and lithium hydroxide (20 mg, 0.82 mmol) in tetrahydrofuran (10 mL) and water (2 mL) was stirred at 25° C. for 15 h. The reaction mixture was adjusted to pH=3 by addition of 1N HCl and concentrated under reduced pressure to afford crude 4-phenyl-5,6-dihydro-4H-imidazo[1,2-b][1,2,4]triazole-2-carboxylic acid (40 mg, 93%) as a yellow solid. LCMS $R_T$=1.309 min, m/z=230.9 $[M+H]^+$. LCMS (0 to 60% acetonitrile in water+0.03% trifluoacetic acid over 3.0 mins) retention time 1.309 min, ESI+ found [M+H]=230.9.

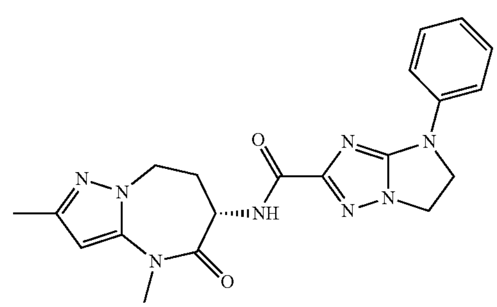

Step 8: 4-phenyl-N-1[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide A mixture of 4-phenyl-5,6-dihydroimidazo[1,2-b][1,2,4]triazole-2-carboxylic acid (40 mg, 0.17 mmol), (6S)-6-amino-2,4-dimethyl-7,8-dihydro-6H-pyrazolo[1,5-a][1,3]diazepin-5-one (33 mg, 0.17 mmol), 1-hydroxybenzotriazole (56 mg, 0.42 mmol) and 1-(3-dimethyl aminopropyl)-3-ethylcarbodiimidehydrochloride (80 mg, 0.42 mmol) in N,N-dimethylformamide (5 mL) was stirred at 20° C. for 2 h. The mixture was concentrated under reduced pressure and the residue was purified by RP-HPLC (35% to 65% acetonitrile/0.05% HCl in water) to afford 4-phenyl-N-[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide (3.5 mg, 5%) as a white solid. $^1$H NMR (400 MHz, $CD_3OD$) δ7.58 (d, J=8.0 Hz, 2H), 7.41-7.37 (m, 2H), 7.06-7.02 (m, 1H), 6.15 (s, 1H), 4.63-4.51 (m, 3H), 4.48-4.41 (m, 2H), 4.33 (s, 1H), 4.29-4.23 (m, 1H), 3.35 (s, 3H), 2.91-2.84 (m, 1H), 2.38-2.21 (m, 4H). LCMS $R_T$=0.752 min, m/z=407.1 [M+H]$^+$.

LCMS (5 to 95% acetonitrile in water+0.03% trifluoacetic acid over 1.5 mins) retention time 0.752 min, ESI+ found [M+H]=407.1

Example 637

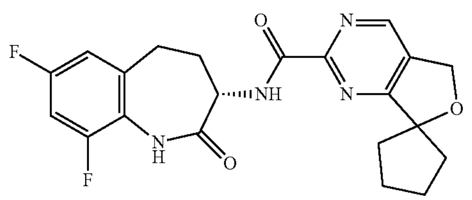 [SMILES: O=C(N[C@H]1CCc2cc(F)cc(F)c2NC1=O)c1ncc2c(n1)C1(CCCC1)OC2]

N-[(3S)-7,9-difluoro-2-oxo-1,3,4,5-tetrahydro-1-benzazepin-3-yl]spiro[5H-furo[3,4-d]pyrimidine-7,1'-cyclopentane]-2-carboxamide Amide coupling prepared in a similar fashion to WX Method 164. The crude was purified by RP-HPLC (acetonitrile 38% to 68%/0.05% ammonium hydroxide in water) to give N-[(3S)-7,9-difluoro-2-oxo-1,3,4,5-tetrahydro-1-benzazepin-3-yl]spiro[5H-furo[3,4-d]pyrimidine-7,1'-cyclopentane]-2-carboxamide (30.3 mg, 51%) as a white solid. $^1$H NMR (400 MHz, $CD_3OD$) δ 8.79 (s, 1H), 7.06-7.00 (m, 2H), 5.11 (s, 2H), 4.65-4.60 (m, 1H), 3.07-2.98 (m, 1H), 2.86-2.76 (m, 2H), 2.27-2.22 (m, 1H), 2.10-2.00 (m, 4H), 1.98-1.87 (m, 4H). LCMS $R_T$=0.714 min, m/z=414.9 [M+H]$^+$.

LCMS (5 to 95% acetonitrile in water+0.05% ammonium hydroxide over 1.5 mins) retention time 0.714 min, ESI+ found [M+H]=414.9.

Examples 638 and 639

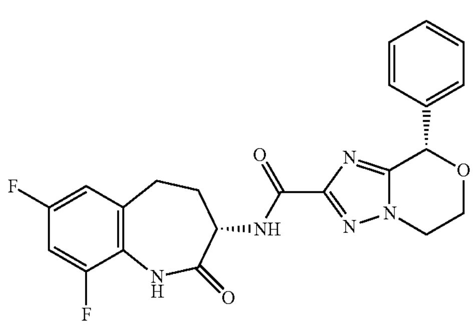

-continued

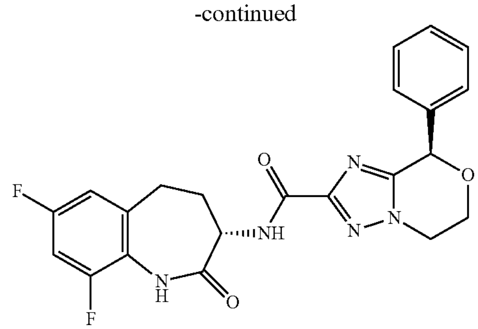

(8S)-8-phenyl-N-[(3S)-7,9-difluoro-2-oxo-1,3,4,5-tetrahydro-1-benzazepin-3-yl]-6,8-dihydro-5H-[1,2,4]triazolo[5,1-c][1,4]oxazine-2-carboxamide and (8R)-8-phenyl-N-[(3S)-7,9-difluoro-2-oxo-1,3,4,5-tetrahydro-1-benzazepin-3-yl]-6,8-dihydro-5H-[1,2,4]triazolo[5,1-c][1,4]oxazine-2-carboxamide Amide coupling prepared in a similar fashion to WX Method 121. The racemic material (30 mg) was separated by chiral SFC to give:

(8S)-8-phenyl-N-[(3S)-7,9-difluoro-2-oxo-1,3,4,5-tetrahydro-1-benzazepin-3-yl]-6,8-dihydro-5H-[1,2,4]triazolo[5,1-c][1,4]oxazine-2-carboxamide (Peak 1, retention time 4.962 min) (9.4 mg, 31%) as a light yellow oil. $^1$H NMR (400 MHz, $CD_3OD$) δ 7.46-7.34 (m, 5H), 7.04-6.96 (m, 2H), 5.94 (s, 1H), 4.59-4.52 (m, 1H), 4.50-4.43 (m, 1H), 4.40-4.33 (m, 2H), 4.25-4.17 (m, 1H), 3.01-2.91 (m, 1H), 2.84-2.76 (m, 1H), 2.66-2.55 (m, 1H), 2.26-2.14 (m, 1H). LCMS $R_T$=0.955 min, m/z=440.2 [M+H]$^+$.

LCMS (10 to 80% acetonitrile in water+0.03% trifluoacetic acid over 2 mins) retention time 0.955 min, ESI+ found [M+H]=440.2

(8R)-8-phenyl-N-[(3S)-7,9-difluoro-2-oxo-1,3,4,5-tetrahydro-1-benzazepin-3-yl]-6,8-dihydro-5H-[1,2,4]triazolo[5,1-c][1,4]oxazine-2-carboxamide (Peak 2, retention time 5.392 min) (8.8 mg, 29%) as a yellow oil. $^1$H NMR (400 MHz, $CD_3OD$) δ 7.46-7.34 (m, 5H), 7.03-6.95 (m, 2H), 5.94 (s, 1H), 4.60-4.52 (m, 1H), 4.50-4.43 (m, 1H), 4.40-4.32 (m, 2H), 4.25-4.16 (m, 1H), 3.01-2.91 (m, 1H), 2.84-2.76 (m, 1H), 2.66-2.54 (m, 1H), 2.24-2.13 (m, 1H). LCMS $R_T$=0.955 min, m/z=440.2 [M+H]$^+$.

LCMS (10 to 80% acetonitrile in water+0.03% trifluoacetic acid over 2 mins) retention time 0.955 min, ESI+ found [M+H]=440.2

SFC condition: Column: Chiralpak AD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Examples 640 and 641

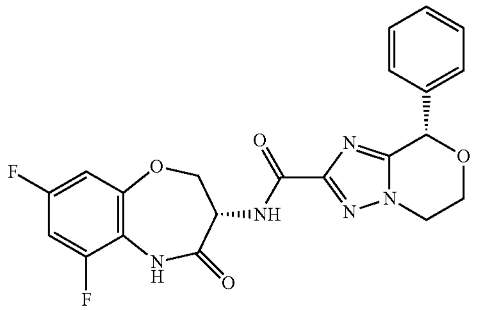

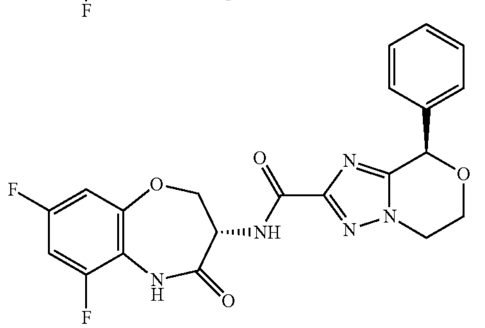

(8S)-8-phenyl-N-[(3S)-6,8-difluoro-4-oxo-3,5-dihydro-2H-1,5-benzoxazepin-3-yl]-6,8-dihydro-5H-[1,2,4]triazolo[5,1-c][1,4]oxazine-2-carboxamide and (8R)-8-phenyl-N-[(3S)-6,8-difluoro-4-oxo-3,5-dihydro-2H-1,5-benzoxazepin-3-yl]-6,8-dihydro-5H-[1,2,4]triazolo[5,1-c][1,4]oxazine-2-carboxamide Amide coupling prepared in a similar fashion to WX Method 121. The crude was purified by RP-HPLC (17% to 47% acetonitrile/0.05% ammonia hydroxide in water) to afford N—((S)-6,8-difluoro-4-oxo-2,3,4,5-tetrahydrobenzo[b][1,4]oxazepin-3-yl)-8-phenyl-6,8-dihydro-5H-[1,2,4]triazolo[5,1-c][1,4]oxazine-2-carboxamide (40 mg, 42%). The racemic material was separated by chiral SFC to give:

(8S)-8-phenyl-N-[(3S)-6,8-difluoro-4-oxo-3,5-dihydro-2H-1,5-benzoxazepin-3-yl]-6,8-dihydro-5H-[1,2,4]triazolo[5,1-c][1,4]oxazine-2-carboxamide (Peak 1, retention time 4.810 min) (7.7 mg, 19%) as a light yellow oil. $^1$H NMR (400 MHz, $CD_3OD$) δ7.45-7.35 (m, 5H), 6.96-6.89 (m, 1H), 6.88-6.82 (m, 1H), 5.95 (s, 1H), 5.09-5.01 (m, 1H), 4.68-4.60 (m, 1H), 4.51-4.46 (m, 2H), 4.42-4.33 (m, 2H), 4.26-4.17 (m, 1H). LCMS $R_T$=0.956 min, m/z=442.1 [M+H]$^+$.

LCMS (10 to 80% acetonitrile in water+0.03% trifluoacetic acid over 2 mins) retention time 0.956 min, ESI+ found [M+H]=442.1.

(8R)-8-phenyl-N-[(3S)-6,8-difluoro-4-oxo-3,5-dihydro-2H-1,5-benzoxazepin-3-yl]-6,8-dihydro-5H-[1,2,4]triazolo[5,1-c][1,4]oxazine-2-carboxamide (Peak 2, retention time 5.392 min) (7.9 mg, 19%) as a yellow oil. $^1$H NMR (400 MHz, $CD_3OD$) δ7.47-7.33 (m, 5H), 6.97-6.89 (m, 1H), 6.85 (d, J=9.6 Hz, 1H), 5.95 (s, 1H), 5.09-5.01 (m, 1H), 4.66-4.59 (m, 1H), 4.52-4.44 (m, 2H), 4.40-4.33 (m, 2H), 4.26-4.17 (m, 1H). LCMS $R_T$=0.961 min, m/z=442.1 [M+H]$^+$.

LCMS (10 to 80% acetonitrile in water+0.03% trifluoacetic acid over 2 mins) retention time 0.961 min, ESI+ found [M+H]=442.1

SFC condition: Column: Chiralpak AD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Examples 42 rd 43

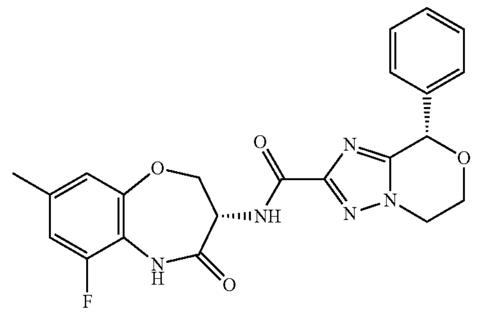

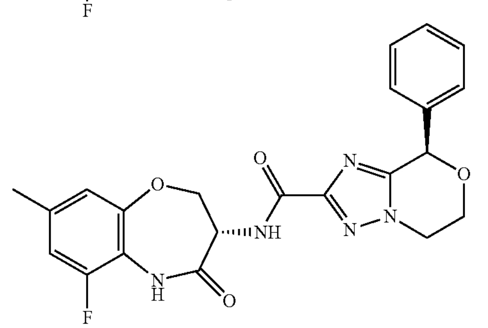

(8S)-8-phenyl-N-[(3S)-6-fluoro-8-methyl-4-oxo-3,5-dihydro-2H-1,5-benzoxazepin-3-yl]-6,8-dihydro-5H-[1,2,4]triazolo[5,1-c][1,4]oxazine-2-carboxamide and (8R)-8-phenyl-N-[(3S)-6-fluoro-8-methyl-4-oxo-3,5-dihydro-2H-1,5-benzoxazepin-3-yl]-6,8-dihydro-5H-[1,2,4]triazolo[5,1-c][1,4]oxazine-2-carboxamide Amide coupling prepared in a similar fashion to WX Method 121. The racemic material (30 mg) was separated by chiral SFC to give:

(8S)-8-phenyl-N-[(3S)-6-fluoro-8-methyl-4-oxo-3,5-dihydro-2H-1,5-benzoxazepin-3-yl]-6,8-dihydro-5H-[1,2,4]triazolo[5,1-c][1,4]oxazine-2-carboxamide (Peak 1, retention time 5.076 min) (10.9 mg, 36%) as a light yellow oil. $^1$H NMR (400 MHz, $CD_3OD$) δ7.44-7.36 (m, 5H), 6.89-6.83 (m, 2H), 5.94 (s, 1H), 5.06-4.98 (m, 1H), 4.63-4.56 (m, 1H), 4.52-4.33 (m, 5H), 4.25-4.17 (m, 1H), 2.33 (s, 3H). LCMS $R_T$=0.988 min, m/z=438.2 [M+H]$^+$.

LCMS (10 to 80% acetonitrile in water+0.03% trifluoacetic acid over 2 mins) retention time 0.988 min, ESI+ found [M+H]=438.2

(8R)-8-phenyl-N-[(3S)-6-fluoro-8-methyl-4-oxo-3,5-dihydro-2H-1,5-benzoxazepin-3-yl]-6,8-dihydro-5H-[1,2,4]triazolo[5,1-c][1,4]oxazine-2-carboxamide (Peak 2, retention time 5.374 min) (11 mg, 37%) as a yellow oil. $^1$H NMR (400 MHz, $CD_3OD$) δ7.44-7.36 (m, 5H), 6.90-6.82 (m, 2H), 5.95 (s, 1H), 5.06-4.98 (m, 1H), 4.62-4.55 (m, 1H), 4.52-4.33 (m, 5H), 4.25-4.17 (m, 1H), 2.33 (s, 3H). LCMS $R_T$=0.994 min, m/z=438.1 [M+H]$^+$. LCMS (10 to 80% acetonitrile in water+0.03% trifluoacetic acid over 2 mins) retention time 0.994 min, ESI+ found [M+H]=438.1

SFC condition: Column: Chiralpak AD-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 644

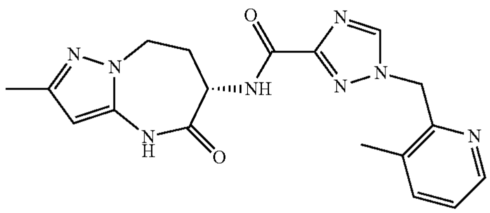 [SMILES: Cc1cc2n(n1)CC[C@H](NC(=O)c1ncn(Cc3ncccc3C)n1)C(=O)N2]

1-[(3-methyl-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide Amide coupling prepared in a similar fashion to WX Method 019. The crude was purified by RP-HPLC (acetonitrile 13-43%/0.05% ammonium hydroxide in water) to give 1-[(3-methyl-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide (8.0 mg, 15%) as a white solid. $^1H$ NMR (400 MHz, $CD_3OD$) δ8.57 (s, 1H), 8.32 (s, 1H), 7.68 (d, J=7.6 Hz, 1H), 7.28-7.27 (m, 1H), 6.10 (s, 1H), 5.63 (s, 2H), 4.54-4.49 (m, 1H), 4.33-4.20 (m, 2H), 3.30 (s, 3H), 2.85-2.83 (m, 1H), 2.46 (s, 3H), 2.25-2.23 (m, 4H). LC-MS $R_T$=1.258 min, m/z=395.1 $[M+H]^+$. LCMS (10 to 80% acetonitrile in water+0.03% ammonium bicarbonate over 3.0 mins) retention time 1.258 min, ESI+ found [M+H]=395.1.

Example 645

WX Method 129

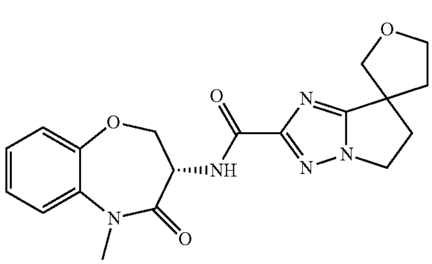 [SMILES: CN1C(=O)[C@@H](NC(=O)c2nc3n(n2)CCC32CCOC2)COc2ccccc21]

N-[(3S)-5-methyl-4-oxo-2,3-dihydro-1,5-benzoxazepin-3-yl]spiro[5,6-dihydropyrrolo[1,2-b][1,2,4]triazole-7,3'-tetrahydrofuran]-2-carboxamide

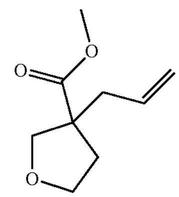

Step 1: methyl 3-allyltetrahydrofuran-3-carboxylate

To a solution of methyl tetrahydrofuran-3-carboxylate (2.6 g, 19.98 mmol) in tetrahydrofuran (10 mL) was added sodium bis(trimethylsilyl)azanide (1N in tetrahydrofuran, 20.0 mL, 20.0 mmol) at −78° C. The reaction mixture was stirred at −78° C. for 30 min and then allyl iodide (5.0 g, 29.77 mmol) was added. The reaction mixture was stirred at −78° C. for another 15 min and then quenched by addition of saturated ammonium chloride (20 mL). The mixture was extracted with ethyl acetate (3×30 mL). The combined organic layers were washed with water (20 mL), brine (20 mL), dried over sodium sulfate and concentrated under reduced pressure to afford methyl 3-allyltetrahydrofuran-3-carboxylate (1.9 g, 56%) as yellow oil, used in the next step as is.

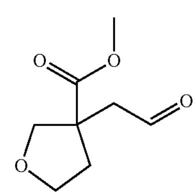

Step 2: methyl 3-(2-oxoethyl)tetrahydrofuran-3-carboxylate

A mixture of methyl 3-allyltetrahydrofuran-3-carboxylate (1.9 g, 11.16 mmol), osmium tetroxide (100 mg, 0.39 mmol) and sodium periodate (4.77 g, 22.33 mmol) in tetrahydrofuran (30 mL) and water (30 mL) was stirred at 20° C. for 2 h. The mixture was diluted with water (30 mL) and extracted with ethyl acetate (3×20 mL). The combined organic layers were washed with water (20 mL), brine (20 mL), dried over sodium sulfate and concentrated under reduced pressure. The residue was purified by column chromatography (silica gel, 100-200 mesh, 0 to 50% ethyl acetate in petroleum ether) to afford methyl 3-(2-oxoethyl)tetrahydrofuran-3-carboxylate (1.0 g, 57%) as yellow oil, used in the next step as is.

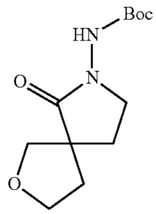 [SMILES: CC(C)(C)OC(=O)NN1CCC2(CCOC2)C1=O]

Step 3: tert-butyl (6-oxo-2-oxa-7-azaspiro[4.4]nonan-7-yl)carbamate

To a solution of methyl 3-(2-oxoethyl)tetrahydrofuran-3-carboxylate (1.1 g, 6.39 mmol) in acetic acid (7.5 mL) and tetrahydrofuran (15 mL) was added tert-butyl hydrazinecarboxylate (1.01 g, 7.67 mmol). The reaction mixture was stirred at 20° C. for 2 h and sodium cyanoborohydride (1.2 g, 19.17 mmol) was added. The reaction mixture was heated at 50° C. for 16 h and concentrated under reduced pressure. The residue was purified by RP-HPLC (acetonitrile 17-47%/0.05% ammonium hydroxide in water) to afford tert-butyl N-(1-oxo-7-oxa-2-azaspiro[4.4]nonan-2-yl)carbamate (500 mg, 31%) as white solids, used in the next step as is.

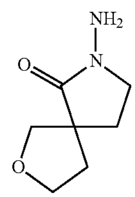 [SMILES: NN1CCC2(CCOC2)C1=O]

Step 4: 7-amino-2-oxa-7-azaspiro[4.4]nonan-6-one

To a solution of tert-butyl N-(1-oxo-7-oxa-2-azaspiro[4.4]nonan-2-yl)carbamate (500 mg, 1.95 mmol) in ethyl acetate (10 mL) was added HCl (4N in ethyl acetate, 5.0 mL, 20 mmol). The reaction mixture was stirred at 15° C. for 4 h and concentrated under reduced pressure. The residue was dissolved in water (10 mL) and adjusted to pH=10 by addition of saturated sodium bicarbonate (10 mL). The mixture was extracted with dichloromethane (8×20 mL). The combined organic layers were washed with water (20 mL), brine (20 mL), dried over sodium sulfate and concentrated under reduced pressure to afford 2-amino-7-oxa-2-azaspiro[4.4]nonan-1-one (200 mg, 66%) as a yellow oil, used in the next step as is.

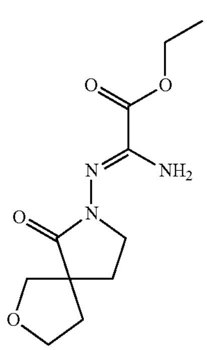 [SMILES: CCOC(=O)/C(N)=N/N1CCC2(CCOC2)C1=O]

Step 5: (Z)-ethyl 2-amino-2-((6-oxo-2-oxa-7-azaspiro[4.4]nonan-7-yl)imino)acetate To a solution of 2-amino-7-oxa-2-azaspiro[4.4]nonan-1-one (200 mg, 1.28 mmol) in ethanol (10 mL) was added ethyl 2-ethoxy-2-imino-acetate (929 mg, 6.40 mmol). The mixture was heated at 40° C. for 12 h and concentrated under reduced pressure to afford crude ethyl (2Z)-2-amino-2-[(2-oxo-7-oxa-1-azaspiro[4.4]nonan-1-yl)imino]acetate (150 mg, 46%) as yellow oil, used in the next step as is.

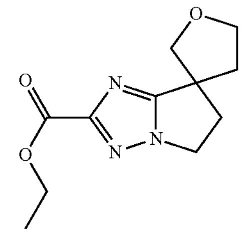 [SMILES: CCOC(=O)c1nc2n(n1)CCC21CCOC1]

Step 6: ethyl spiro[5,6-dihydropyrrolo[1,2-b][1,2,4]triazole-7,3'-tetrahydrofuran]-2-carboxylate A solution of ethyl (2Z)-2-amino-2-[(2-oxo-7-oxa-1-azaspiro[4.4]nonan-1-yl)imino]acetate (150 mg, 0.59 mmol) in phosphorus oxychloride (5 mL, 56.09 mmol) was heated at 120° C. for 1 h and cooled. The mixture was slowly quenched by addition of water (20 mL) and extracted with dichloromethane (3×20 mL). The combined organic layers were washed with 20% sodium bicarbonate (20 mL), brine (30 mL), dried over sodium sulfate and concentrated under reduced pressure. The residue was purified by column chromatography (silica gel, 100-200 mesh, 0 to 60% ethyl acetate in petroleum ether) to afford ethyl spiro[5,6-dihydropyrrolo[1,2-b][1,2,4]triazole-7,3'-tetrahydrofuran]-2-carboxylate (80 mg, 57%) as light yellow oil, used in the next step as is.

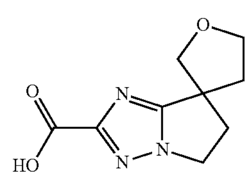 [SMILES: O=C(O)c1nc2n(n1)CCC21CCOC1]

Step 7: spiro[5,6-dihydropyrrolo[1,2-b][1,2,4]triazole-7,3'-tetrahydrofuran]-2-carboxylic acid A mixture of ethyl spiro[5,6-dihydropyrrolo[1,2-b][1,2,4]triazole-7,3'-tetrahydrofuran]-2-carboxylate (80 mg, 0.34 mmol) and lithium hydroxide monohydrate (141 mg, 3.37 mmol) in tetrahydrofuran (5 mL) and water (3 mL) was stirred at 20° C. for 2 h. The mixture was concentrated under reduced pressure and diluted with water (10 mL). The solution was adjusted to pH=5 by addition of 1N HCl (5 mL) and then extracted with ethyl acetate (3×10 mL). The combined organic layers were concentrated under reduced pressure to afford crude spiro[5,6-dihydropyrrolo[1,2-b][1,2,4]triazole-7,3'-tetrahydrofuran]-2-carboxylic acid (40 mg, 57%) as a yellow solid, used in the next step as is.

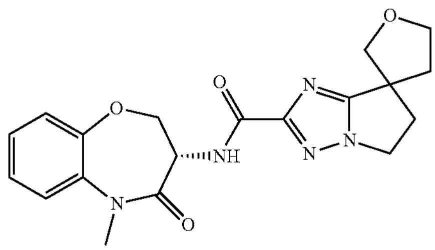 [SMILES: CN1C(=O)[C@@H](NC(=O)c2nc3n(n2)CCC32CCOC2)COc2ccccc21]

Step 8: N-[(3S)-5-methyl-4-oxo-2,3-dihydro-1,5-benzoxazepin-3-yl]spiro[5,6-dihydropyrrolo[1,2-b][1,2,4]triazole-7,3'-tetrahydrofuran]-2-carboxamide A mixture of spiro[5,6-dihydropyrrolo[1,2-b][1,2,4]triazole-7,3'-tetrahydrofuran]-2-carboxylic acid (20 mg, 0.10 mmol), 1-hydroxybenzotriazole (25 mg, 0.19 mmol), 1-(3-dimethylaminopropyl)-3-ethylcarbodiimidehydrochloride (40 mg, 0.21 mmol), and (3S)-3-amino-5-methyl-2,3-dihydro-1,5-benzoxazepin-4-one (18 mg, 0.10 mmol) in N,N-Dimethylformamide (5 mL) was stirred at 15° C. for 2 h. The mixture was concentrated under reduced pressure and the residue was purified by RP-HPLC (acetonitrile 32-62%/0.05% ammonium hydroxide in water) to afford N-[(3S)-5-methyl-4-oxo-2,3-dihydro-1,5-benzoxazepin-3-yl]spiro[5,6-dihydropyrrolo[1,2-b][1,2,4]triazole-7,3'-tetrahydrofuran]-2-carboxamide (8.6 mg, 23%) as a white solid. $^1$H NMR (400 MHz, $CD_3OD$) δ7.43 (d, J=6.8 Hz, 1H), 7.33-7.30 (m, 2H), 7.23 (d, J=6.0 Hz, 1H), 5.00-4.84 (m, 1H), 4.61-4.57 (m, 1H), 4.43-4.40 (m, 1H), 4.26 (t, J=6.8 Hz, 2H), 4.13-4.09 (m, 1H), 4.03-4.00 (m, 1H), 3.95-3.91 (m, 1H), 3.88-3.85 (m, 1H), 3.42 (s, 3H), 2.85-2.79 (m, 2H), 2.40-2.35 (m, 1H), 2.21-2.18 (m, 1H). LCMS $R_T$=0.713 min; m/z=384.0 $(M+H)^+$. LCMS (5 to 95% acetonitrile in water+0.03% trifluoacetic acid over 1.5 mins) retention time 0.713 min, ESI+ found [M+H]=384.0.

Example 646

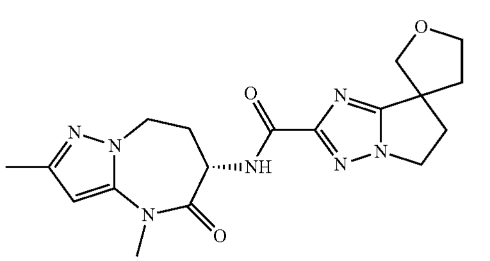 [SMILES: Cc1cc2n(n1)CC[C@H](NC(=O)c1nc3n(n1)CCC31CCOC1)C(=O)N2C]

N-[(6S)-2,4-dimethyl-5-oxo-7,8-dihydro-6H-pyrazolo[1,5-a][1,3]diazepin-6-yl]spiro[5,6-dihydropyrrolo[1,2-b][1,2,4]triazole-7,3'-tetrahydrofuran]-2-carboxamide Amide coupling prepared in a similar fashion to WX Method 129. The crude was purified by RP-HPLC (28% to 58% acetonitrile/0.05% ammonia hydroxide in water) to afford N-[(6S)-2,4-dimethyl-5-oxo-7,8-dihydro-6H-pyrazolo[1,5-a][1,3]diazepin-6-yl]spiro[5,6-dihydropyrrolo[1,2-b][1,2,4]triazole-7,3'-tetrahydrofuran]-2-carboxamide (5.9 mg, 16%) as a white solid. $^1$H NMR (400 MHz, $CD_3OD$) δ6.11 (s, 1H), 4.54-4.52 (m, 1H), 4.53-4.24 (m, 4H), 4.15-4.10 (m, 1H), 4.05-4.01 (m, 1H), 3.94-3.92 (m, 1H), 3.89-3.86 (m, 1H), 3.33 (s, 3H), 2.85-2.79 (m, 3H), 2.40-2.35 (m, 1H), 2.26 (s, 3H), 2.24-2.19 (m, 2H). LCMS $R_T$=0.626 min; m/z=386.0 $(M+H)^+$.

LCMS (5 to 95% acetonitrile in water+0.03% trifluoacetic acid over 1.5 mins) retention time 0.626 min, ESI+ found [M+H]=386.0.

Example 647

WX Method 019

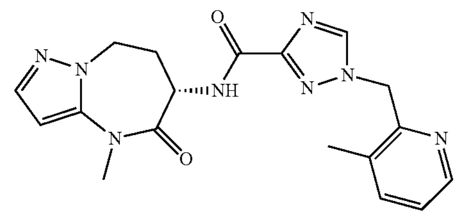 [SMILES: Cc1cccnc1Cn1cnc(C(=O)N[C@H]2CCn3nccc3N(C)C2=O)n1]

1-[(3-methyl-2-pyridyl)methyl]-N-(6S)-4-methyl-5-oxo-7,8-dihydro-6H-pyrazolo[1,5-a][1,3]diazepin-6-yl-1,2,4-triazol-3-carboxamide

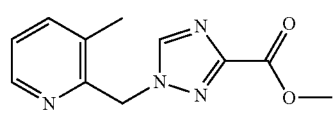 [SMILES: COC(=O)c1ncn(Cc2ncccc2C)n1]

Step 1: methyl 1-[(3-methyl-2-pyridyl)methyl]-1,2,4-triazole-3-carboxylate

To a solution of methyl 1H-1,2,4-triazole-3-carboxylate (200 mg, 1.57 mmol) in N,N-dimethylformamide (4 mL) was added potassium carbonate (435 mg, 3.15 mmol) and 2-(chloromethyl)-3-methylpyridine (223 mg, 1.57 mmol). The mixture was stirred at 25° C. for 12 h and then filtered. The filtrate was concentrated under reduced pressure and the residue was purified by column chromatography (silica gel, 100-200 mesh, 0 to 50% ethyl acetate in petroleum ether) to give methyl 1-[(3-methyl-2-pyridyl)methyl]-1,2,4-triazole-3-carboxylate (150 mg, 41%) as a colorless oil. LC-MS $R_T$=0.302 min, m/z=232.9 $[M+H]^+$.

LCMS (5 to 95% acetonitrile in water+0.03% trifluoacetic acid over 1.5 mins) retention time 0.302 min, ESI+ found M+H 232.9.

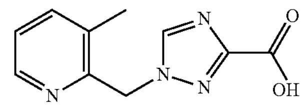 [SMILES: Cc1cccnc1Cn1cnc(C(=O)O)n1]

Step 2: 1-[(3-methyl-2-pyridyl)methyl]-1,2,4-triazole-3-carboxylic acid

A mixture of methyl 1-[(3-methyl-2-pyridyl)methyl]-1,2,4-triazole-3-carboxylate (100 mg, 0.43 mmol) and lithium hydroxide hydrate (90 mg, 2.15 mmol) in tetrahydrofuran/methanol/water (5 mL, 2:2:1) was stirred at 25° C. for 2 h. The solution was diluted with water (10 mL) and adjusted to pH=4-5 by addition of 1M HCl. The resulting solid was collected by filtration and dried under reduced pressure to give crude 1-[(3-methyl-2-pyridyl)methyl]-1,2,4-triazole-3-carboxylic acid (90 mg, 96%) as a light yellow solid, used as is in the next step.

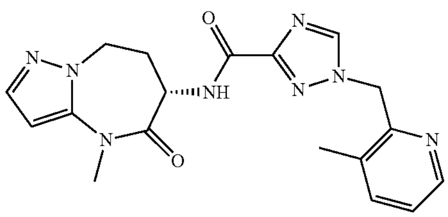 [SMILES: Cc1cccnc1Cn1cnc(C(=O)N[C@H]2CCn3nccc3N(C)C2=O)n1]

Step 3: 1-[(3-methyl-2-pyridyl)methyl]-N-(6S)-4-methyl-5-oxo-7,8-dihydro-6H-pyrazolo[1,5-a][1,3]diazepin-6-yl-1,2,4-triazole-3-carboxamide To a stirred solution of (6S)-6-amino-4-methyl-7,8-dihydro-6H-pyrazolo[1,5-a][1,3]diazepin-5-one (25 mg, 0.14 mmol) in N,N-dimethylformamide (3 mL) was added 1-hydroxybenzotriazole (29 mg, 0.21 mmol), 1-(3-dimethylaminopropyl)-3-ethylcarbodiimidehydrochloride (39 mg, 0.21 mmol) and 1-[(3-methyl-2-pyridyl)methyl]-1,2,4-triazole-3-carboxylic acid (30 mg, 0.14 mmol). The mixture was stirred at 20° C. for 12 h and concentrated under reduced pressure. The residue was purified by RP-HPLC (acetonitrile 10-40%/0.05% ammonium hydroxide in water) to afford N-[(6S)-4-methyl-5-oxo-7,8-dihydro-6H-pyrazolo[1,5-a][1,3]diazepin-6-yl]-1-[(3-methyl-2-pyridyl)methyl]-1,2,4-triazole-3-carboxamide (7 mg, 13%) as a white solid. $^1H$ NMR (400 MHz, $CD_3OD$) δ8.57 (s, 1H), 8.32 (d, J=4.8 Hz, 1H), 7.68 (d, J=7.6 Hz, 1H), 7.52 (d, J=2.0 Hz, 1H), 7.30-7.26 (m, 1H), 6.30 (d, J=2.0 Hz, 1H), 5.63 (s, 2H), 4.52-4.39 (m, 2H), 4.32-4.28 (m, 1H), 3.35 (s, 3H), 2.89-2.84 (m, 1H), 2.45 (s, 3H), 2.28-2.24 (m, 1H). LC-MS $R_T$=1.135 min, m/z=381.2 $[M+H]^+$.

LCMS (10 to 80% acetonitrile in water+0.03% ammonium bicarbonate over 3.0 mins) retention time 1.135 min, ESI+ found [M+H]=381.2.

Example 648

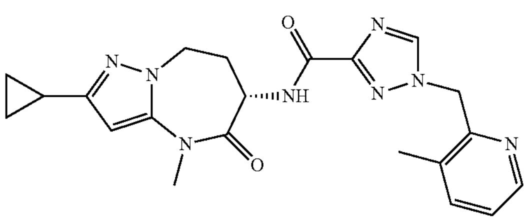 [SMILES: Cc1cccnc1Cn1cnc(C(=O)N[C@H]2CCn3nc(C4CC4)cc3N(C)C2=O)n1]

1-[(3-methyl-2-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 019. The crude was purified by RP-HPLC (acetonitrile 18-48%/0.05% ammonium hydroxide in water) to give 1-[(3-methyl-2-pyridyl)methyl]-N-(6 S)-2-cyclopropyl-4-methyl-5-oxo-7,8-dihydro-6H-pyrazolo[1,5-a][1,3]diazepin-6-yl-1,2,4-triazole-3-carboxamide (7.4 mg, 13%) as a white solid. $^1H$ NMR (400 MHz, $CD_3OD$) δ8.58 (s, 1H), 8.33 (d, J=4.4 Hz, 1H), 7.68 (d, J=8.0 Hz, 1H), 7.30-7.27 (m, 1H), 6.00 (s, 1H), 5.63 (s, 2H), 4.53-4.48 (m, 1H), 4.31-4.26 (m, 1H), 4.24-4.20 (m, 1H), 3.32 (s, 3H), 2.86-2.80 (m, 1H), 2.46 (s, 3H), 2.25-2.21 (m, 1H), 1.91-1.87 (m, 1H), 0.94-0.92 (m, 2H), 0.75-0.73 (m, 2H). LC-MS $R_T$=1.357 min, m/z=421.2 $[M+H]^+$.

LCMS (10 to 80% acetonitrile in water+0.03% ammonium bicarbonate over 3.0 mins) retention time 1.357 min, ESI+ found [M+H]=421.2.

Example 649

WX Method 133

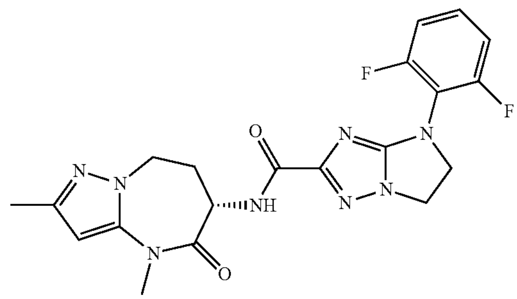 [SMILES: Cc1cc2n(n1)CC[C@H](NC(=O)c1nc3n(n1)CCN3c1c(F)cccc1F)C(=O)N2C]

4-(2,6-difluorophenyl)-N-[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide

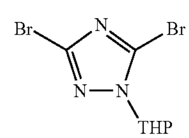

Step 1: 3,5-dibromo-1-(tetrahydro-2H-pyran-2-yl)-1H-1,2,4-triazole

A mixture of 3,4-dihydro-2H-pyran (13.19 g, 156.85 mmol), 4-methylbenzenesulfonic acid (1.35 g, 7.84 mmol) and 3,5-dibromo-1H-1,2,4-triazole (10.0 g, 44.08 mmol) in tetrahydrofuran (50 mL) was heated at 25° C. for 2 h. The mixture was filtered and the filtrate was concentrated under reduced pressure to afford 3,5-dibromo-1-tetrahydropyran-2-yl-1,2,4-triazole (11 g, 80%) as a white solid, used as is in the next step as is.

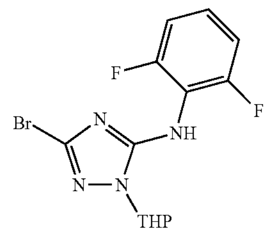

Step 2: 3-bromo-N-(2,6-difluorophenyl)-1-(tetrahydro-2H-pyran-2-yl)-1H-1,2,4-triazol-5-amine To a solution of 2,6-difluoroaniline (1.83 g, 14.15 mmol) in tetrahydrofuran (5 mL) was added lithium bis(trimethylsilyl)amide (1N in tetrahedron, 12.86 mL, 12.86 mmol), then 3,5-dibromo-1-tetrahydropyran-2-yl-1,2,4-triazole (2.0 g, 6.43 mmol) at 0° C. The mixture was stirred at 0° C. for 15 h and quenched by addition of saturated ammonium chloride (10 mL). The resulting mixture was extracted with dichloromethane (2×20 mL). The combined organic layers were concentrated under reduced pressure and the residue was purified by column chromatography (silica gel, 100-200 mesh, 0-20% ethyl acetate in petroleum ether) to afford 5-bromo-N-(2,6-difluorophenyl)-2-tetrahydropyran-2-yl-1,2,4-triazol-3-amine (1.2 g, 52%) as a yellow solid, used in the next step as is.

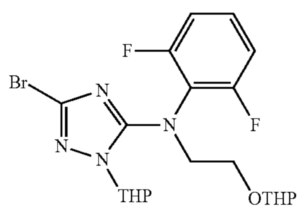

Step 3: 3-bromo-N-(2,6-difluorophenyl)-1-(tetrahydro-2H-pyran-2-yl)-N-(2-((tetrahydro-2H-pyran-2-yl)oxy)ethyl)-1H-1,2,4-triazol-5-amine To a solution of and 5-bromo-N-(2,6-difluorophenyl)-2-tetrahydropyran-2-yl-1,2,4-triazol-3-amine (700 mg, 1.95 mmol) in N,N-dimethylformamide (10 mL) was added sodium hydride (60%, 78 mg, 1.95 mmol). The reaction mixture was stirred at 50° C. for 0.5 h, then 2-(2-bromoethoxy)tetrahydro-2H-pyran (408 mg, 1.95 mmol) and sodium iodide (292 mg, 1.95 mmol) was added. The reaction mixture was stirred at 50° C. for 15 h and poured onto ice water (5 mL). The mixture was extracted with ethyl acetate (2×10 mL). The combined organic layers were concentrated under reduced pressure. The residue was purified by column chromatography (silica gel, 100-200 mesh, 0-20% ethyl acetate in petroleum ether) to give 5-bromo-N-(2,6-difluorophenyl)-2-tetrahydropyran-2-yl-N-(2-tetrahydropyran-2-yloxyethyl)-1,2,4-triazol-3-amine (800 mg, 84%) as yellow oil. LCMS $R_T$=0.893 min, m/z=508.9 $[M+H]^+$.

LCMS (5 to 95% acetonitrile in water+0.03% trifluoacetic acid over 1.5 mins) retention time 0.893 min, ESI+ found M+H]=508.9.

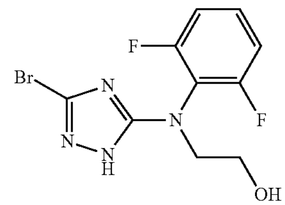 [SMILES: OCCN(c1nc(Br)n[nH]1)c1c(F)cccc1F]

Step 4: 2-((3-bromo-1H-1,2,4-triazol-5-yl)(2,6-difluorophenyl)amino)ethanol

A mixture of 5-bromo-N-(2,6-difluorophenyl)-2-tetrahydropyran-2-yl-N-(2-tetrahydropyran-2-yloxyethyl)-1,2,4-triazol-3-amine (300 mg, 0.62 mmol) and 2,2,2-trifluoroacetic acid (70 mg, 0.62 mmol) in dichloromethane (10 mL) was stirred at 15° C. for 15 h and then concentrated under reduced pressure to afford crude 2-(N-(3-bromo-1H-1,2,4-triazol-5-yl)-2,6-difluoro-anilino)ethanol (160 mg, 81%) as a brown oil without other purification. LCMS $R_T$=0.551 min, m/z=318.9 $[M+H]^+$. LCMS (5 to 95% acetonitrile in water+0.03% trifluoacetic acid over 1.5 mins) retention time 0.551 min, ESI+ found $[M+H]^+$=318.9.

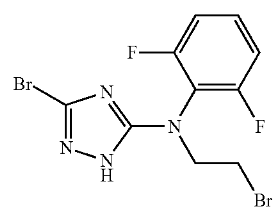 [SMILES: Fc1cccc(F)c1N(CCBr)c1nc(Br)n[nH]1]

Step 5: 3-bromo-N-(2-bromoethyl)-N-(2,6-difluorophenyl)-1H-1,2,4-triazol-5-amine A mixture of 2-(N-(3-bromo-1H-1,2,4-triazol-5-yl)-2,6-difluoro-anilino)ethanol (160 mg, 0.50 mmol) and phosphoryl tribromide (144 mg, 0.50 mmol) in acetonitrile (5 mL) was heated at 50° C. for 15 h. The reaction mixture was concentrated under reduced pressure and the residue was purified by column chromatography (silica gel, 100-200 mesh, 0-20% ethyl acetate in petroleum ether) to afford 3-bromo-N-(2-bromoethyl)-N-(2,6-difluorophenyl)-1H-1,2,4-triazol-5-amine (100 mg, 52%) as a brown oil. LCMS $R_T$=1.149 min, m/z=382.9 $[M+H]^+$. LCMS (5 to 95% acetonitrile in water+0.03% trifluoacetic acid over 1.5 mins) retention time 1.149 min, ESI+ found [M+H]=382.9.

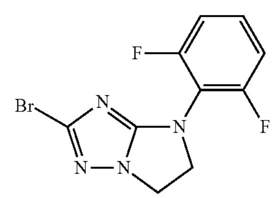 [SMILES: Fc1cccc(F)c1N1CCn2nc(Br)nc21]

Step 6: 2-bromo-4-(2,6-difluorophenyl)-5,6-dihydro-4H-imidazo[1,2-b][1,2,4]triazole A mixture of 3-bromo-N-(2-bromoethyl)-N-(2,6-difluorophenyl)-1H-1,2,4-triazol-5-amine (100 mg, 0.26 mmol)

and potassium carbonate (36 mg, 0.26 mmol) in N,N-dimethylformamide (5 mL) was stirred at 20° C. for 15 hours. The reaction mixture was diluted with ice water (3 mL) and extracted with ethyl acetate (2×10 mL). The combined organic layers were concentrated and the residue was purified by column chromatography (silica gel, 100-200 mesh, 0-50% ethyl acetate in petroleum ether) to afford 2-bromo-4-(2,6-difluorophenyl)-5,6-dihydroimidazo[1,2-b][1,2,4]triazole (65 mg, 83%) as a white solid. LCMS $R_T$=0.612 min, m/z=300.1 [M+H]$^+$. LCMS (5 to 95% acetonitrile in water+0.03% trifluoacetic acid over 1.5 mins) retention time 0.612 min, ESI+ found [M+H]=300.1.

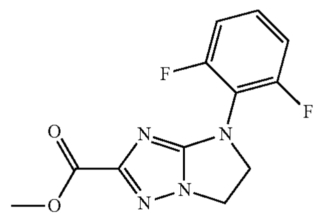 [SMILES: COC(=O)c1nc2n(n1)CCN2c1c(F)cccc1F]

Step 7: methyl 4-(2,6-difluorophenyl)-5,6-dihydro-4H-imidazo[1,2-b][1,2,4]triazole-2-carboxylate A mixture of 2-bromo-4-(2,6-difluorophenyl)-5,6-dihydroimidazo[1,2-b][1,2,4]triazole (60.0 mg, 0.20 mmol), 1,1'-bis(diphenylphosphino)ferrocene palladium dichloride (13 mg, 0.02 mmol) and triethylamine (0.27 mL, 1.99 mmol) in methanol (40 mL) was heated at 70° C. for 12 h under CO (40 psi) and filtered. The filtrate was concentrated under reduced pressure and the residue was purified by column chromatography (silica gel, 100-200 mesh, 0-50% ethyl acetate in petroleum ether) to afford methyl 4-(2,6-difluorophenyl)-5,6-dihydroimidazo [1,2-b][1,2,4]triazole-2-carboxylate (30 mg, 53%) as a yellow solid. LCMS $R_T$=0.566 min, m/z=280.8 [M+H]$^+$, LCMS (5 to 95% acetonitrile in water+0.03% trifluoacetic acid over 1.5 mins) retention time 0.566 min, ESI+ found [M+H]=280.8.

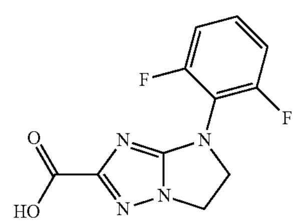 [SMILES: O=C(O)c1nc2n(n1)CCN2c1c(F)cccc1F]

Step 8: 4-(2,6-difluorophenyl)-5,6-dihydro-4H-imidazo[1,2-b][1,2,4]triazole-2-carboxylic acid A mixture of methyl 4-(2,6-difluorophenyl)-5,6-dihydroimidazo[1,2-b][1,2,4]triazole-2-carboxylate (30 mg, 0.11 mmol) and lithium hydroxide (13 mg, 0.54 mmol) in tetrahydrofuran (10 mL) and water (2 mL) was stirred at 25° C. for 15 h. The reaction mixture was adjusted to pH=3 by addition of 1N HCl and concentrated under reduced pressure to afford crude methyl 4-(2,6-difluorophenyl)-5,6-dihydroimidazo[1,2-b][1,2,4]triazole-2-carboxylate (30 mg, 100%) as a yellow solid. LCMS $R_T$=0.263 min, m/z=267.0 [M+H]$^+$. LCMS (5 to 95% acetonitrile in water+0.03% trifluoacetic acid over 1.5 mins) retention time 0.263 min, ESI+ found [M+H]=267.0.

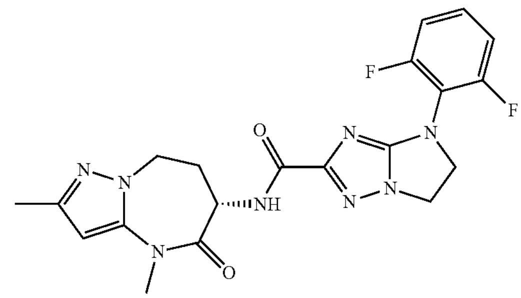 [SMILES: Cc1cc2n(n1)CC[C@H](NC(=O)c1nc3n(n1)CCN3c1c(F)cccc1F)C(=O)N2C]

Step 9: 4-(2,6-difluorophenyl)-N-[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide A mixture of 4-(2,6-difluorophenyl)-5,6-dihydroimidazo[1,2-b][1,2,4]triazole-2-carboxylic acid (25 mg, 0.09 mmol), (6S)-6-amino-2,4-dimethyl-7,8-dihydro-6H-pyrazolo[1,5-a][1,3]diazepin-5-one (17 mg, 0.09 mmol), 1-(3-dimethylaminopropyl)-3-ethylcarbodiimidehydrochloride (40 mg, 0.21 mmol) and 1-hydroxybenzotriazole (28 mg, 0.21 mmol) in N,N-dimethylformamide (5 mL) was added stirred at 20° C. for 2 h. The mixture was concentrated under reduced pressure and the residue was purified by RP-HPLC (35% to 65% acetonitrile/0.05% HCl in water acetonitrile) to afford 4-(2,6-difluorophenyl)-N-[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide (6.5 mg, 18% yield) as a white solid. $^1$H NMR (400 MHz, $CD_3OD$) δ7.52-7.43 (m, 1H), 7.21-7.17 (m, 2H), 6.46 (s, 1H), 4.72-4.60 (m, 3H), 4.60-4.53 (m, 2H), 4.51-4.45 (m, 1H), 4.43-4.35 (m, 1H), 3.38 (s, 3H), 2.91-2.82 (m, 1H), 2.45-2.35 (m, 4H). LCMS $R_T$=0.745 min, m/z=443.0 [M+H]$^+$.

LCMS (5 to 95% acetonitrile in water+0.03% trifluoacetic acid over 1.5 mins) retention time 0.745 min, ESI+ found [M+H]=443.0

Example 650

WX Method 028

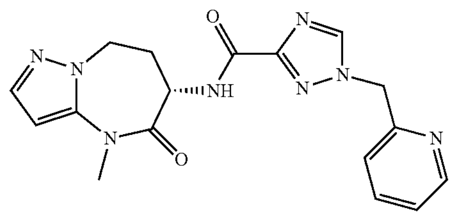 [SMILES: CN1C(=O)[C@@H](NC(=O)c2ncn(Cc3ccccn3)n2)CCn2nccc21]

1-(2-pyridylmethyl)-N-(6S)-4-methyl-5-oxo-7,8-dihydro-6H-pyrazolo[1,5-a][1,3]diazepin-6-yl-1,2,4-triazole-3-carboxamide

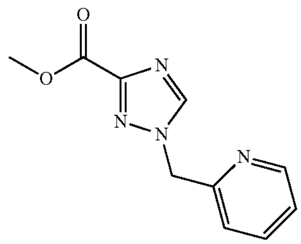 [SMILES: COC(=O)c1ncn(Cc2ccccn2)n1]

Step 1: methyl 1-(2-pyridylmethyl)-1,2,4-triazole-3-carboxylate

A mixture of methyl 1H-1,2,4-triazole-3-carboxylate (2.0 g, 15.7 mmol), potassium carbonate (4.35 g, 31.5 mmol) and 2-(bromomethyl)pyridine (2.71 g, 15.7 mmol) in N,N-dimethylformamide (10 mL) was stirred at 25° C. for 16 h and filtered. The filtrate was concentrated under reduced pressure and the residue was purified by column chromatography (silica gel, 100-200 mesh, 0 to 100% ethyl acetate in petroleum ether) to afford methyl 1-(2-pyridylmethyl)-1,2,4-triazole-3-carboxylate (1.6 g, 47%) as a light-yellow solid. $^1$H NMR (400 MHz, DMSO-d6) δ8.85 (s, 1H), 8.52 (br. s, 1H), 7.83 (t, J=7.3 Hz, 1H), 7.38-7.31 (m, 2H), 5.62 (s, 2H), 3.82 (s, 3H).

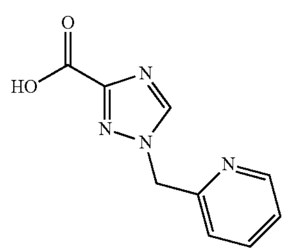 [SMILES: O=C(O)c1ncn(Cc2ccccn2)n1]

Step 2: 1-(2-pyridylmethyl)-1,2,4-triazole-3-carboxylic acid

A mixture of methyl 1-(2-pyridylmethyl)-1,2,4-triazole-3-carboxylate (500 mg, 2.29 mmol) and potassium hydroxide (0.26 g, 4.58 mmol) in ethanol (8 mL) and water (2 mL) was stirred for 2 h at 25° C. The solvent was removed under reduced pressure. The residue was dissolved in water (5 mL) and adjusted to pH=6 by addition of 2 N HCl and concentrated under reduced pressure to give crude 1-(2-pyridylmethyl)-1,2,4-triazole-3-carboxylic acid (0.70 g, 149%) as a yellow solid, used as is in the next step.

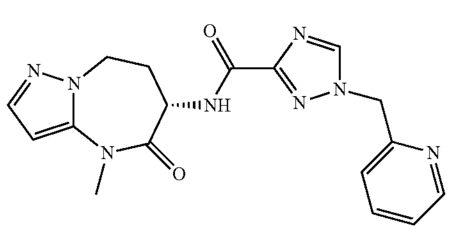 [SMILES: CN1C(=O)[C@@H](NC(=O)c2ncn(Cc3ccccn3)n2)CCn2nccc21]

Step 3: 1-(2-pyridylmethyl)-N-(6S)-4-methyl-5-oxo-7,8-dihydro-6H-pyrazolo[1,5-a][1,3]diazepin-6-yl-1,2,4-triazole-3-carboxamide To a solution of 1-hydroxybenzotriazole (7.5 mg, 0.06 mmol) in N,N-dimethylformamide (2.5 mL) was added 1-(3-dimethylaminopropyl)-3-ethylcarbodiimidehydrochloride (79 mg, 0.42 mmol), (6S)-6-amino-4-methyl-7,8-dihydro-6H-pyrazolo[1,5-a][1,3]diazepin-5-one (50 mg, 0.28 mmol) and 1-(2-pyridylmethyl)-1,2,4-triazole-3-carboxylic acid (56 mg, 0.28 mmol). The mixture was stirred at 20° C. for 12 h and concentrated under reduced pressure. The residue was purified by RP-HPLC (acetonitrile 17-47/0.05% ammonium hydroxide in water) to afford N-[(6S)-4-methyl-5-oxo-7,8-dihydro-6H-pyrazolo[1,5-a][1,3]diazepin-6-yl]-1-(2-pyridylmethyl)-1,2,4-triazole-3-carboxamide (95.6 mg, 89.9%) as white solids. $^1$H NMR (400 MHz, $CD_3OD$) δ8.66 (s, 1H), 8.55 (d, J=4.4 Hz, 1H), 7.86 (t, J=7.6 Hz, 1H), 7.54 (s, 1H), 7.42-7.38 (m, 2H), 6.32 (s, 1H), 5.62 (s, 2H), 4.55-4.42 (m, 2H), 4.31-4.29 (m, 1H), 3.38 (s, 3H), 2.91-2.81 (m, 1H), 2.36-2.28 (m, 1H). LCMS $R_T$=1.25 min, m/z=367.2 $[M+H]^+$. LCMS (0 to 60% acetonitrile in water+0.03% trifluoacetic acid over 3 mins) retention time 1.25 min, ESI+ found [M+H]=367.2

Example 651

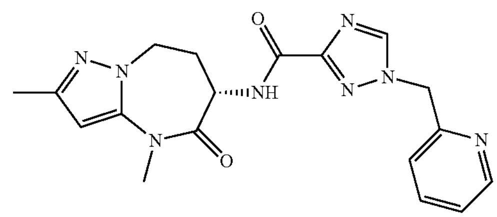 [SMILES: Cc1cc2n(n1)CC[C@H](NC(=O)c1ncn(Cc3ccccn3)n1)C(=O)N2C]

1-(2-pyridylmethyl)-N-(6S)-2,4-dimethyl-5-oxo-7,8-dihydro-6H-pyrazolo[1,5-a][1,3]diazepin-6-yl-1,2,4-triazole-3-carboxamide Amide coupling prepared in a similar fashion to WX Method 028. The crude was purified by RP-HPLC (acetonitrile 17-47%/0.05% ammonium hydroxide in water) to give 1-(2-pyridylmethyl)-N-(6S)-2,4-dimethyl-5-oxo-7,8-dihydro-6H-pyrazolo[1,5-a][1,3]diazepin-6-yl-1,2,4-triazole-3-carboxamide (64.3 mg, 63%) as a light-yellow semi-solid. $^1$H NMR (400 MHz, $CD_3OD$) δ8.64 (s, 1H), 8.52 (d, J=4.4 Hz, 1H), 7.89-7.80 (m, 1H), 7.43-7.32 (m, 2H), 6.10 (s, 1H), 5.60 (s, 2H), 4.57-4.48 (m, 1H), 4.36-4.27 (m, 1H), 4.26-4.14 (m, 1H), 3.32 (s, 3H), 2.90-2.77 (m, 1H), 2.30-2.20 (m, 4H). LCMS $R_T$=0.652 min, m/z=381.2 $[M+H]^+$. LCMS (10 to 80% acetonitrile in water+0.03% trifluoacetic acid over 2 mins) retention time 0.652 min, ESI+ found [M+H]=381.2.

Example 652

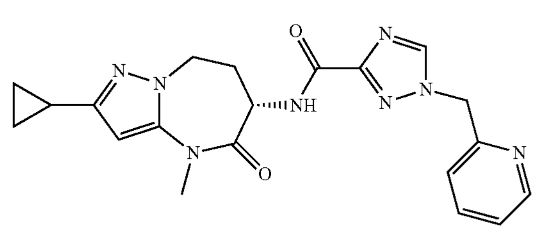 [SMILES: CN1C(=O)[C@@H](NC(=O)c2ncn(Cc3ccccn3)n2)CCn2nc(C3CC3)cc21]

1-(2-pyridylmethyl)-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 028. The crude was purified by RP-HPLC (acetonitrile 17-47%/0.05% ammonium hydroxide in water) to give 1-(2-pyridylmethyl)-N-(6 S)-2-cyclopropyl-4-methyl-5-oxo-7,8-dihydro-6H-pyrazolo[1,5-a][1,3]diazepin-6-yl-1,2,4-triazole-3-carboxamide (70.3 mg, 75%) as a white solid. $^1$H NMR (400 MHz, $CD_3OD$) δ8.65 (s, 1H), 8.53 (d, J=4.8 Hz, 1H), 7.87-7.84 (m, 1H), 7.40-7.37 (m, 2H), 6.00 (s, 1H), 5.60 (s, 2H), 4.56-4.51 (m, 1H), 4.30-4.28 (m, 1H), 4.23-4.18 (m, 1H), 3.32 (s, 3H), 2.88-2.81 (m, 1H), 2.29-2.24 (m, 1H), 1.93-1.90 (m, 1H), 0.96-0.93 (m, 2H), 0.76-0.74 (m, 2H). LCMS $R_T$=0.747 min, m/z=407.2 [M+H]$^+$.

LCMS (10 to 80% acetonitrile in water+0.03% trifluoacetic acid over 2 mins) retention time 0.747 min, ESI+ found [M+H]=407.2.

Example 653

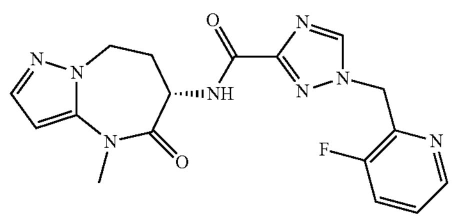 [SMILES: CN1C(=O)[C@@H](NC(=O)c2ncn(Cc3ncccc3F)n2)CCn2nccc21]

1-[(3-fluoro-2-pyridyl)methyl]-N-(6 S)-4-methyl-5-oxo-7,8-dihydro-6H-pyrazolo[1,5-a][1, 3]diazepin-6-yl-1,2,4-triazole-3-carboxamide Amide coupling prepared in a similar fashion to WX Method 025. The crude was purified by RP-HPLC (acetonitrile 22-52%/0.05% ammonium hydroxide in water) to give 1-[(3-fluoro-2-pyridyl)methyl]-N-(6S)-4-methyl-5-oxo-7,8-dihydro-6H-pyrazolo[1,5-a][1,3]diazepin-6-yl-1,2,4-triazole-3-carboxamide (16 mg, 30%) as a white solid. $^1$H NMR (400 MHz, $CD_3OD$) δ8.65 (s, 1H), 8.35 (d, J=5.2 Hz, 1H), 7.71-7.60 (m, 1H), 7.51 (s, 1H), 7.46-7.43 (m, 1H), 6.29 (s, 1H), 5.70 (s, 2H), 4.52-4.38 (m, 2H), 4.29-4.26 (m, 1H), 3.34 (s, 3H), 2.87-2.81 (m, 1H), 2.36-2.21 (m, 1H). LCMS $R_T$=1.05 min, m/z=385.1 [M+H]$^+$. LCMS (10 to 80% acetonitrile in water+0.05% ammonium hydroxide over 3 mins) retention time 1.05 min, ESI+ found [M+H]=385.1.

Example 654

WX Method 025

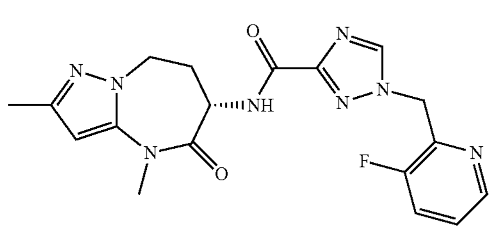 [SMILES: Cc1cc2n(n1)CC[C@H](NC(=O)c1ncn(Cc3ncccc3F)n1)C(=O)N2C]

1-[(3-fluoro-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide

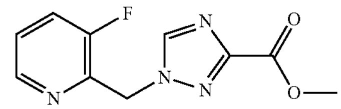 [SMILES: COC(=O)c1ncn(Cc2ncccc2F)n1]

Step 1: methyl 1-((3-fluoropyridin-2-yl)methyl)-1H-1,2,4-triazole-3-carboxylate

To a solution of methyl 1H-1,2,4-triazole-3-carboxylate (128 mg, 1.01 mmol) in N,N-dimethylformamide (5 mL) was added potassium carbonate (1746 mg, 12.63 mmol) and 2-(bromomethyl)-3-fluoro-pyridine (240 mg, 1.26 mmol). The reaction mixture was stirred at 25° C. for 12 h and filtered. The filtrate was concentrated under reduced pressure and the residue was purified by column chromatography (silica gel, 100-200 mesh, 0 to 100% ethyl acetate in petroleum ether) to afford methyl 1-[(3-fluoro-2-pyridyl)methyl]-1,2,4-triazole-3-carboxylate (120 mg, 40% yield) as a white solid. $^1$H NMR (400 MHz, $CDCl_3$) δ 8.32 (s, 2H), 7.42-7.38 (m, 1H), 7.28-7.26 (m, 1H), 5.58 (s, 2H), 3.91 (s, 3H).

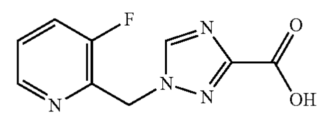 [SMILES: O=C(O)c1ncn(Cc2ncccc2F)n1]

Step 2: 1-((3-fluoropyridin-2-yl)methyl)-1H-1,2,4-triazole-3-carboxylic acid

A mixture of methyl 1-[(3-fluoro-2-pyridyl)methyl]-1,2,4-triazole-3-carboxylate (120 mg, 0.51 mmol) and lithium hydroxide (114 mg, 4.75 mmol) in tetrahydrofuran (8 mL) and water (4 mL) was stirred at 25° C. for 16 h. The mixture was adjusted to pH=6 by addition of 1N hydrochloric acid. The solid was collected by filtration and the dried to give crude 1-[(3-fluoro-2-pyridyl)methyl]-1,2,4-triazole-3-carboxylic acid (80 mg, 71%) as a white solid, used as is in the next step.

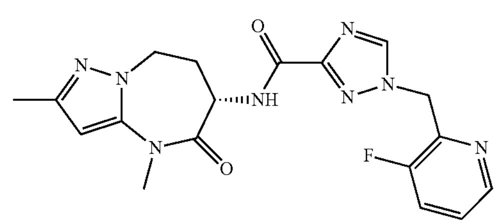 [SMILES: Cc1cc2n(n1)CC[C@H](NC(=O)c1ncn(Cc3ncccc3F)n1)C(=O)N2C]

Step 3: 1-[(3-fluoro-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide To a stirred solution of (6S)-6-amino-2,4-dimethyl-7,8-dihydro-6H-pyrazolo[1,5-a][1,3]diazepin-5-one (26 mg, 0.14 mmol) in N,N-dimethylformamide (3 mL) was added 1-hydroxybenzotriazole (27 mg, 0.20 mmol), 1-(3-dimethylaminopropyl)-3-ethylcarbodiimidehydrochloride (38 mg, 0.20 mmol) and 1-[(3-fluoro-2-pyridyl)methyl]-1,2,4-triazole-3-carboxylic acid (30 mg, 0.14 mmol). The mixture was stirred at 25° C. for 12 h and concentrated under reduced pressure. The residue was purified by RP-HPLC (acetonitrile 22-52%/0.05% ammonium hydroxide in water) to afford 1-[(3-fluoro-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide (31 mg, 56%) as a white solid. $^1$H NMR (400 MHz, $CD_3OD$) δ8.65 (s, 1H), 8.35 (d, J=4.8 Hz, 1H), 7.70-7.62 (m, 1H), 7.46-7.42 (m, 1H), 6.09 (s, 1H), 5.70 (s, 2H), 4.53-4.49 (m, 1H), 4.34-4.26 (m, 1H), 4.24-4.12 (m, 1H), 3.31 (s, 3H), 2.87-2.77 (m, 1H), 2.27-2.18 (m, 1H), 2.24 (s, 3H). LCMS $R_T$=1.17 min, m/z=399.2 [M+H]$^+$. LCMS (10 to 80% acetonitrile in water+0.05% ammonium hydroxide over 3 mins) retention time 1.17 min, ESI+ found [M+H]=399.2.

Example 655

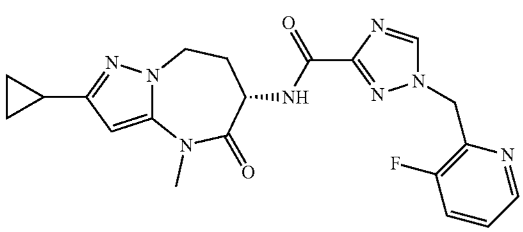 [SMILES: CN1C(=O)[C@@H](NC(=O)c2ncn(Cc3ncccc3F)n2)CCn2nc(C3CC3)cc21]

1-[(3-fluoro-2-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 025. The crude was purified by RP-HPLC (acetonitrile 22-52%/0.05% ammonium hydroxide in water) to give 1-[(3-fluoro-2-pyridyl)methyl]-N-(6 S)-2-cyclopropyl-4-methyl-5-oxo-7,8-dihydro-6H-pyrazolo[1,5-a][1,3]diazepin-6-yl-1,2,4-triazole-3-carboxamide (38 mg, 65%) as a white solid. $^1$H NMR (400 MHz, $CD_3OD$) δ 8.65 (s, 1H), 8.35 (d, J=4.4 Hz, 1H), 7.69-7.60 (m, 1H), 7.45-7.43 (m, 1H), 5.99 (s, 1H), 5.70 (s, 2H), 4.52-4.47 (m, 1H), 4.33-4.24 (m, 1H), 4.23-4.12 (m, 1H), 3.29 (s, 3H), 2.85-2.78 (m, 1H), 2.28-2.17 (m, 1H), 1.94-1.85 (m, 1H), 0.97-0.88 (m, 2H), 0.75-0.69 (m, 2H). LCMS $R_T$=1.35 min, m/z=425.2 [M+H]$^+$. LCMS (10 to 80% acetonitrile in water+0.05% ammonium hydroxide over 3 mins) retention time 1.35 min, ESI+ found [M+H]=425.2.

Example 656

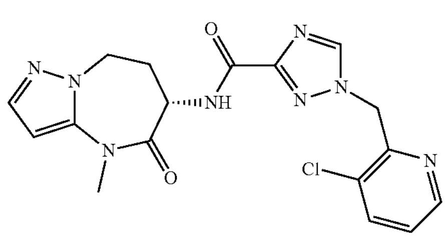 [SMILES: CN1C(=O)[C@@H](NC(=O)c2ncn(Cc3ncccc3Cl)n2)CCn2nccc21]

1-[(3-chloro-2-pyridyl)methyl]-N-[rac-(6S)-4-methyl-5-oxo-7,8-dihydro-6H-pyrazolo[1,5-a][1,3]diazepin-6-yl]-1,2,4-triazole-3-carboxamide Amide coupling prepared in a similar fashion to WX Method 022. The crude was purified by RP-HPLC (acetonitrile 22-52%/0.05% ammonium hydroxide in water) to give 1-[(3-chloro-2-pyridyl)methyl]-N-(6S)-4-methyl-5-oxo-7,8-dihydro-6H-pyrazolo[1,5-a][1,3]diazepin-6-yl-1,2,4-triazole-3-carboxamide (44 mg, 73%) as a white solid. $^1$H NMR (400 MHz, $CD_3OD$) δ8.62 (s, 1H), 8.43-8.41 (m, 1H), 7.91-7.89 (m, 1H), 7.51 (d, J=1.8 Hz, 1H), 7.39-7.35 (m, 1H), 6.29 (d, J=1.8 Hz, 1H), 5.78 (s, 2H), 4.52-4.47 (m, 1H), 4.46-4.38 (m, 1H), 4.31-4.22 (m, 1H), 3.34 (s, 3H), 2.81-2.80 (m, 1H), 2.30-2.22 (m, 1H). LCMS $R_T$=1.21 min, m/z=401.1 [M+H]$^+$. LCMS (10 to 80% acetonitrile in water+0.05% ammonium hydroxide over 3 mins) retention time 1.21 min, ESI+ found [M+H]=401.1.

Example 657

WX Method 022

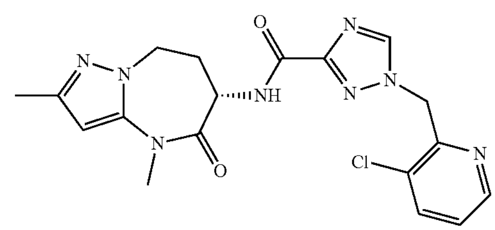 [SMILES: Cc1cc2n(n1)CC[C@H](NC(=O)c1ncn(Cc3ncccc3Cl)n1)C(=O)N2C]

1-[(3-chloro-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide

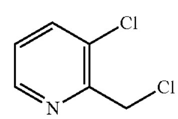

Step 1: 3-chloro-2-(chloromethyl)pyridine

To a stirred solution of (3-chloro-2-pyridyl)methanol (120 mg, 0.84 mmol) in dichloromethane (15 mL) was added thionylchloride (497 mg, 4.18 mmol) at 25° C. After addition, the mixture was stirred for 2 h and then quenched by addition of water (10 mL). The solution was adjusted to pH=11 by addition of saturated aqueous sodium bicarbonate and then extracted with dichloromethane (2×50 mL). The combined organic layers were washed with brine (30 mL), dried over anhydrous sodium sulfate and concentrated under reduced pressure to afford crude 3-chloro-2-(chloromethyl)pyridine (130 mg, 96%) as a yellow oil, used as is in the next step.

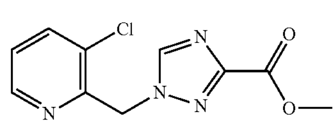

Step 2: methyl 1-((3-chloropyridin-2-yl)methyl)-1H-1,2,4-triazole-3-carboxylate

To a solution of methyl 1H-1,2,4-triazole-3-carboxylate (102 mg, 0.80 mmol) in N,N-dimethylformamide (5 mL) was added 3-chloro-2-(chloromethyl)pyridine (130 mg, 0.80 mmol) and potassium carbonate (333 mg, 2.41 mmol). The reaction mixture was stirred at 25° C. for 16 h and filtered. The filtrate was concentrated under reduced pressure and the residue was purified by column chromatography (silica gel, 100-200 mesh, 0 to 100% ethyl acetate in petroleum ether) to afford methyl 1-[(3-chloro-2-pyridyl)methyl]-1,2,4-triazole-3-carboxylate (125 mg, 62%) as a white solid. $^1$H NMR (400 MHz, $CDCl_3$) δ 8.38 (dd, J=1.4, 4.5 Hz, 1H), 8.26 (s, 1H), 7.68 (dd, J=1.3, 8.2 Hz, 1H), 7.22-7.18 (m, 1H), 5.65 (s, 2H), 3.92 (s, 3H).

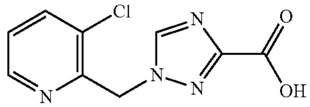

Step 3: 1-((3-chloropyridin-2-yl)methyl)-1H-1,2,4-triazole-3-carboxylic acid

A mixture of methyl 1-[(3-chloro-2-pyridyl)methyl]-1,2,4-triazole-3-carboxylate (125 mg, 0.50 mmol) and lithium hydroxide (104 mg, 4.35 mmol) in tetrahydrofuran (5 mL) and water (2 mL) was stirred for 16 h at 25° C. The mixture was adjusted to pH=6 by addition of 1N HCl. The resulting solid was collected by filtration and dried under reduced pressure to give crude 1-[(3-chloro-2-pyridyl)methyl]-1,2,4-triazole-3-carboxylic acid (110 mg, 87%) as a white solid, used as is in the next step.

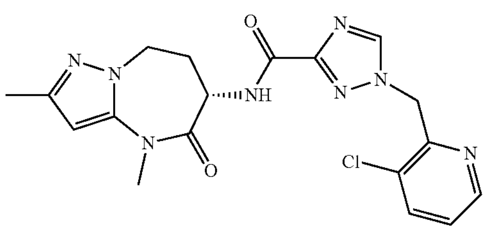 [SMILES: Cc1cc2n(n1)CC[C@H](NC(=O)c1ncn(Cc3ncccc3Cl)n1)C(=O)N2C]

Step 4: 1-[(3-chloro-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide To a stirred solution of 1-[(3-chloro-2-pyridyl)methyl]-1,2,4-triazole-3-carboxylic acid (35 mg, 0.15 mmol) in N,N-dimethylformamide (3 mL) was added 1-hydroxybenzotriazole (29 mg, 0.22 mmol), 1-(3-dimethylaminopropyl)-3-ethyl carbodiimidehydrochloride (42 mg, 0.22 mmol) and (6S)-6-amino-2,4-dimethyl-7,8-dihydro-6H-pyrazolo[1,5-a][1,3]diazepin-5-one (31 mg, 0.16 mmol). The mixture was stirred at 25° C. for 12 h and concentrated under reduced pressure. The residue was purified by RP-HPLC (acetonitrile 22-52%/0.05% ammonium hydroxide in water) to give 1-[(3-chloro-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide (45 mg, 72%) as a white solid. $^1$H NMR (400 MHz, $CD_3OD$) δ8.62 (s, 1H), 8.43-8.41 (m, 1H), 7.91-7.89 (m, 1H), 7.39-7.35 (m, 1H), 6.09 (s, 1H), 5.78 (s, 2H), 4.54-4.50 (m, 1H), 4.35-4.27 (m, 1H), 4.25-4.14 (m, 1H), 3.31 (s, 3H), 2.88-2.78 (m, 1H), 2.29-2.18 (m, 1H), 2.24 (s, 3H). LCMS $R_T$=1.26 min, m/z=415.1 [M+H]$^+$.

LCMS (10 to 80% acetonitrile in water+0.05% ammonium hydroxide over 3 mins) retention time 1.26 min, ESI+ found [M+H]=415.1.

Example 658

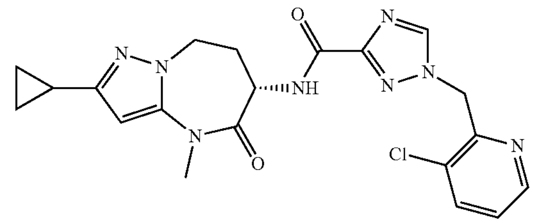 [SMILES: CN1C(=O)[C@@H](NC(=O)c2ncn(Cc3ncccc3Cl)n2)CCn2nc(C3CC3)cc21]

1-[(3-chloro-2-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 022. The crude was purified by RP-HPLC (acetonitrile 22-52%/0.05% ammonium hydroxide in water) to give 1-[(3-chloro-2-pyridyl)methyl]-N-(6 S)-2-cyclopropyl-4-methyl-5-oxo-7,8-dihydro-6H-pyrazolo[1,5-a][1,3]diazepin-6-yl-1,2,4-triazole-3-carboxamide (37 mg, 56%) as a white solid. $^1$H NMR (400 MHz, $CD_3OD$) δ8.62 (s, 1H), 8.43-8.41 (m, 1H), 7.91-7.89 (m, 1H), 7.51 (s, 1H), 7.39-7.35 (m, 1H), 6.29 (s, 1H), 5.78 (s, 2H), 4.52-4.47 (m, 1H), 4.46-4.38 (m, 1H), 4.31-4.22 (m, 1H), 3.34 (s, 3H), 2.81-2.80 (m, 1H), 2.30-2.22 (m, 1H). LCMS $R_T$=1.44 min, m/z=441.1 [M+H]$^+$. LCMS (10 to 80% acetonitrile in water+0.05% ammonium hydroxide over 3 mins) retention time 1.44 min, ESI+ found [M+H]=441.1.

Example 659

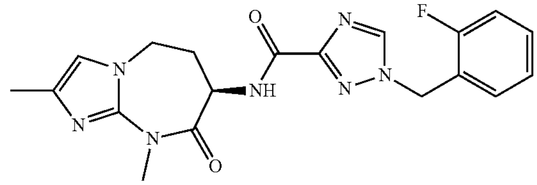 [SMILES: Cc1cn2c(n1)N(C)C(=O)[C@H](NC(=O)c1ncn(Cc3ccccc3F)n1)CC2]

1-[(2-fluorophenyl)methyl]-N-(7R)-2,9-dimethyl-8-oxo-6,7-dihydro-5H-imidazo[1,2-a][1, 3]diazepin-7-yl-1,2,4-triazole-3-carboxamide Amide coupling prepared in a similar fashion to WX Method 091. The crude was purified by RP-HPLC (20% to 50% acetonitrile/0.05% ammonia hydroxide in water) to afford N-(2,9-dimethyl-8-oxo-6,7-dihydro-5H-imidazo[1,2-a][1,3]diazepin-7-yl)-1-[(2-fluorophenyl)methyl]-1,2,4-triazole-3-carboxamide (35 mg, 52% yield) as a white solid. The racemic material was separated by chiral SFC to give:

1-[(2-fluorophenyl)methyl]-N-(7R)-2,9-dimethyl-8-oxo-6,7-dihydro-5H-imidazo[1,2-a][1,3]diazepin-7-yl-1,2,4-triazole-3-carboxamide (Peak 2, retention time 3.433 min) (15.5 mg, 22%) as a white solid. $^1$H NMR (400 MHz, $CD_3OD$) δ8.57 (s, 1H), 7.45-7.33 (m, 2H), 7.24-7.11 (m, 2H), 6.77 (s, 1H), 5.55 (s, 2H), 4.54-4.49 (m, 1H), 4.21-4.15 (m, 1H), 4.04-3.95 (m, 1H), 3.36 (s, 3H), 2.87-2.78 (m, 1H), 2.28-2.14 (m, 4H). LCMS RT=1.819 min; m/z=398.1 $(M+H)^+$. LCMS (0 to 60% acetonitrile in water+0.05% ammonium bicarbonate over 3 mins) retention time 1.819 min, ESI+ found [M+H]=398.1

SFC conditions: Column: Chiralpak AD-3 150×4.6 mm I.D., 3 um Mobile phase: 40% of ethanol (0.05% DEA) in $CO_2$ Flow rate: 2.5 mL/min Column temp.: 35° C.

Example 660

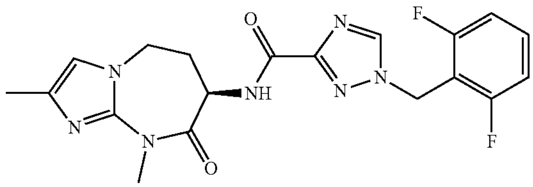 [SMILES: Cc1cn2c(n1)N(C)C(=O)[C@H](NC(=O)c1ncn(Cc3c(F)cccc3F)n1)CC2]

1-[(2,6-difluorophenyl)methyl]-N-(7R)-2,9-dimethyl-8-oxo-6,7-dihydro-5H-imidazo[1,2-a][1,3]diazepin-7-yl-1,2,4-triazole-3-carboxamide Amide coupling prepared in a similar fashion to WX Method 091. The crude was purified by RP-HPLC (20% to 50% acetonitrile/0.05% ammonia hydroxide in water) to afford 1-[(2,6-difluorophenyl)methyl]-N-(2,9-dimethyl-8-oxo-6,7-dihydro-5H-imidazo[1,2-a][1,3]di azepin-7-yl)-1,2,4-triazole-3-carboxamide (35 mg, 50%) as a white solid. The racemic material was separated by chiral SFC to give: 1-[(2,6-difluorophenyl)methyl]-N-(7R)-2,9-dimethyl-8-oxo-6,7-dihydro-5H-imidazo[1,2-a][1,3]diazepin-7-yl-1,2,4-triazole-3-carboxamide (Peak 2, retention time 4.195 min) (18.7 mg, 26%) as a white solid. $^1$H NMR (400 MHz, $CD_3OD$) δ8.60 (s, 1H), 7.50-7.42 (m, 1H), 7.07-7.03 (m, 2H), 6.77 (s, 1H), 5.60 (s, 2H), 4.53-4.48 (m, 1H), 4.21-4.15 (m, 1H), 4.03-3.95 (m, 1H), 3.36 (s, 3H), 2.84-2.76 (m, 1H), 2.26-2.16 (m, 4H). LCMS RT=1.817 min; m/z=416.2 $(M+H)^+$. LCMS (0 to 60% acetonitrile in water+0.05% ammonium bicarbonate over 3 mins) retention time 1.817 min, ESI+ found [M+H]=416.2.

SFC conditions: Column: Chiralcel OJ-3 100×4.6 mm I.D., 3 um Mobile phase: A: $CO_2$ B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 661

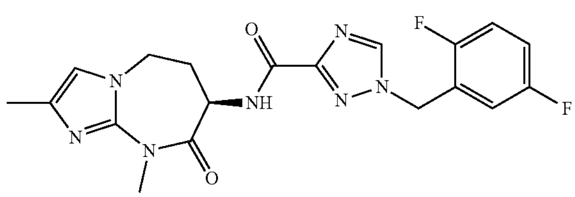 [SMILES: Cc1cn2c(n1)N(C)C(=O)[C@H](NC(=O)c1ncn(Cc3cc(F)ccc3F)n1)CC2]

1-[(2,5-difluorophenyl)methyl]-N-(7R)-2,9-dimethyl-8-oxo-6,7-dihydro-5H-imidazo[1,2-a][1,3]diazepin-7-yl-1,2,4-triazole-3-carboxamide Amide coupling prepared in a similar fashion to WX Method 091. The crude was purified by RP-HPLC (20% to 50% acetonitrile/0.05% ammonia hydroxide in water) to afford 1-[(2,5-difluorophenyl)methyl]-N-(2,9-dimethyl-8-oxo-6,7-dihydro-5H-imidazo[1,2-a][1,3]di azepin-7-yl)-1,2,4-triazole-3-carboxamide (50 mg, 71%) as a white solid. The racemic mixture was separated by chiral SFC to give:

1-[(2,5-difluorophenyl)methyl]-N-(7R)-2,9-dimethyl-8-oxo-6,7-dihydro-5H-imidazo[1,2-a][1,3]diazepin-7-yl-1,2,4-triazole-3-carboxamide (Peak 2, retention time 4.786 min) (21.5 mg, 47%) as a white solid. $^1$H NMR (400 MHz, $CD_3OD$) δ8.61 (s, 1H), 7.22-7.11 (m, 3H), 6.78 (s, 1H), 5.54 (s, 2H), 4.55-4.48 (m, 1H), 4.21-4.16 (m, 1H), 4.05-3.98 (m, 1H), 3.36 (s, 3H), 2.86-2.76 (m, 1H), 2.31-2.15 (m, 4H). LCMS $R_T$=1.852 min; m/z=416.1 $(M+H)^+$.

LCMS (0 to 60% acetonitrile in water+0.05% ammonium bicarbonate over 3 mins) retention time 1.852 min, ESI+ found [M+H]=416.1

SFC conditions: Column: Chiralcel OD-3 100×4.6 mm I.D., 3 um Mobile phase: A: $CO_2$ B: ethanol (0.05% DEA) Gradient: from 5% to 40% of B in 4.5 min and hold 40% for 2.5 min, then 5% of B for 1 min Flow rate: 2.8 mL/min Column temperature: 40° C.

Example 662

WX Method 082

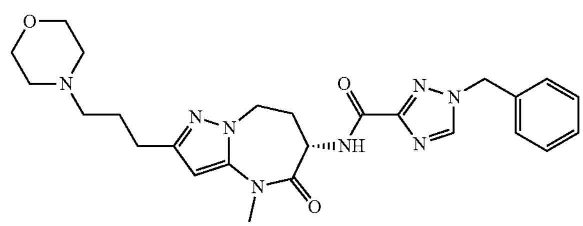

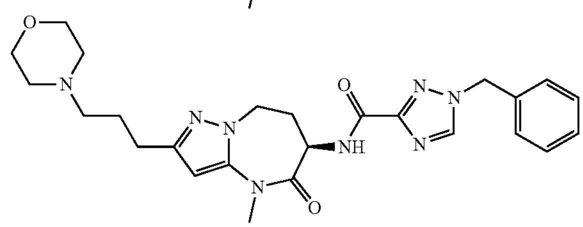

1-benzyl-N-(6S)-4-methyl-2-(3-morpholinopropyl)-5-oxo-7,8-dihydro-6H-pyrazolo[1,5-a][1,3]diazepin-6-yl]-1,2,4-triazole-3-carboxamide and 1-benzyl-N-(6R)-4-methyl-2-(3-morpholinopropyl)-5-oxo-7,8-dihydro-6H-pyrazolo[1,5-a][1,3]diazepin-6-yl]-1,2,4-triazole-3-carboxamide

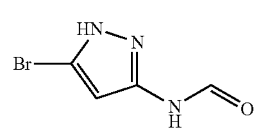

Step 1: N-(5-bromo-1H-pyrazol-3-yl)formamide

The solution of compound 5-bromo-1H-pyrazol-3-amine (500 g, 3.1 mol) in formic acid (1.5 L) was refluxed at 110° C. for 3 hr. TLC (dichloromethane: methanol=10:1, $R_f$=0.35) showed the reaction was completed. The reaction mixture was concentrated under reduced pressure and the residue was washed with 2-methoxy-2-methylpropane (1 L) two times to afford N-(5-bromo-1H-pyrazol-3-yl)formamide (538 g, 92% yield) as a white solid, used as is in the next step.

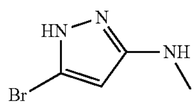

Step 2: 5-bromo-N-methyl-1H-pyrazol-3-amine

With two reactions carried out in parallel, to the solution of lithium aluminum hydride (105 g, 2.8 mol) in tetrahydrofuran (2.6 L) was added compound N-(5-bromo-1H-pyrazol-3-yl)formamide (265 g, 1.4 mol) at 0° C. and the reaction mixture was stirred at 10° C. for 16 hr. Two reactions were combined and the reaction mixture was quenched with water (106 mL) and 15% NaOH solution (106 mL). The resulting solid was filtered and washed with tetrahydrofuran (2×2 L). The filtrate was concentrated under reduced pressure and the crude product was purified by silica column chromatography (petroleum ether:ethyl acetate=50:1~3:1) to afford 5-bromo-N-methyl-1H-pyrazol-3-amine (200 g, 41% yield) as a yellow oil. $^1$H NMR (400 MHz, $CD_3OD$) δ 4.85 (s, 2H), 2.70-2.79 (m, 3H).

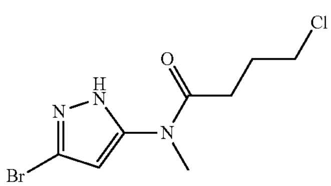

Step 3: N-(3-bromo-1H-pyrazol-5-yl)-4-chloro-N-methylbutanamide

The solution of compound 5-bromo-N-methyl-1H-pyrazol-3-amine (175 g, 1.0 mol) and compound 4-chlorobutanoyl chloride (661 g, 4.7 mol) was stirred at 60° C. for 1 hr. The reaction mixture was quenched with methanol (800 mL) at −30° C. and allowed to warm to 0° C. and stirred for 1 h. Then the mixture was neutralized with aq. NaOH (10M) to pH 6, the mixture was concentrated, extracted with dichloromethane (3×300 mL) and the combined filtrate was concentrated under reduced pressure. The crude product was purified by column chromatography (dichloromethane: methanol=1:0~30:1) to afford N-(3-bromo-1H-pyrazol-5-yl)-4-chloro-N-methylbutanamide (180 g, 64% yield) as a yellow oil, used as is in the next step.

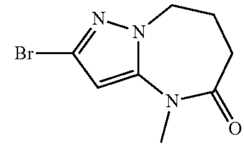

Step 4: 2-bromo-4-methyl-7,8-dihydro-4H-pyrazolo[1,5-a][1,3]diazepin-5(6H)-one

With two reactions carried out in parallel a solution of compound N-(3-bromo-1H-pyrazol-5-yl)-4-chloro-N-methylbutanamide (100 g, 356 mmol) in acetonitrile (1 L) was added cesium carbonate (232 g, 713 mmol) and stirred at 30° C. for 16 hr. The two reactions were combined for workup, filtered the $Cs_2CO_3$ and concentrated under reduced pressure. The residue was purified by column chromatography (petroleum ether: ethyl acetate=50:1~1:1) to afford 2-bromo-4-methyl-7,8-dihydro-4H-pyrazolo[1,5-a][1,3]diazepin-5(6H)-one (110 g, 63% yield) as a yellow oil, used as is in the next step.

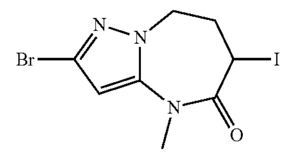

Step 5: 2-bromo-6-iodo-4-methyl-7,8-dihydro-4H-pyrazolo[1,5-a][1,3]diazepin-5(6H)

To the solution of compound 2-bromo-4-methyl-7,8-dihydro-4H-pyrazolo[1,5-a][1,3]diazepin-5(6H)-one (100 g, 410 mmol) in dichloromethane (2 L) was added N,N,N',N'-tetramethylethane-1,2-diamine (143 g, 1.23 mol), stirred at −15° C. for 0.5 hr, followed addition of iodo(trimethyl) silane (246 g, 1.23 mol) drop wise at −15° C. for 1.5 hr. Subsequently iodine (312 g, 1.23 mol) was added and the reaction mixture was stirred at −15° C. 3 hr. The reaction mixture was quenched with aq. $Na_2SO_3$ (10M, 1 L), filtered, washed with brine (1 L), extracted with dichloromethane (2×3 L), dried over sodium sulfate, filtered and the filtrate was concentrated under reduced pressure to afford compound 2-bromo-6-iodo-4-methyl-7,8-dihydro-4H-pyrazolo[1,5-a][1,3]diazepin-5(6H)-one (170 g, crude) as a brown solid, which was used in next step without further purification.

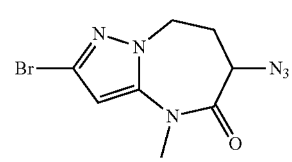 [SMILES: CN1C(=O)C(N=[N+]=[N-])CCn2nc(Br)cc21]

Step 6: 6-azido-2-bromo-4-methyl-7,8-dihydro-4H-pyrazolo[1,5-a][1,3]diazepin-5(6H)-one The solution of compound 2-bromo-6-iodo-4-methyl-7,8-dihydro-4H-pyrazolo[1,5-a][1,3]diazepin-5(6H)-one (170 g, 460 mmol) in dimethylformamide (500 mL) was added sodium azide (45 g, 670 mol) and stirred at 30° C. for 2 hr. The reaction mixture was diluted with water (500 mL) and extracted with dichloromethane (2×2 L), the combined organic layers were washed with brine (200 mL), dried over sodium sulfate, filtered and the filtrate was concentrated under reduced pressure to afford 6-azido-2-bromo-4-methyl-7,8-dihydro-4H-pyrazolo[1,5-a][1,3]diazepin-5(6H)-one (100 g, crude) as a yellow oil, which was used in next step without further purification.

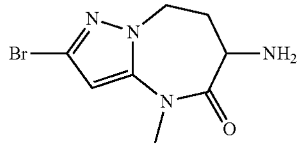

Step 7: 6-amino-2-bromo-4-methyl-7,8-dihydro-4H-pyrazolo[1,5-a][1,3]diazepin-5(6H)-one The solution of compound 6-azido-2-bromo-4-methyl-7,8-dihydro-4H-pyrazolo[1,5-a][1,3]diazepin-5(6H)-one (100 g, 350 mmol) in methanol (1 L) was added Pd/C (15 g), the mixture was stirred at 30° C. for 16 hr under $H_2$ (30 psi). Pd/C was filtered and the filtrate was concentrated under reduced pressure. The residue was purified by flash silica column (petroleum ether: ethyl acetate=50:1~0:1) to afford 6-amino-2-bromo-4-methyl-7,8-dihydro-4H-pyrazolo[1,5-a][1,3]diazepin-5(6H)-one (50 g, yield: 54%) as a white solid. $^1H$ NMR (400 MHz, DMSO-d6) δ 6.43 (s, 1H), 4.17-4.27 (m, 1H), 4.05 (ddd, J=14.6, 12.7, 6.7 Hz, 1H), 3.19 (s, 3H), 3.13-3.17 (m, 1H), 2.44-2.50 (m, 1H), 1.73-1.83 (m, 1H).

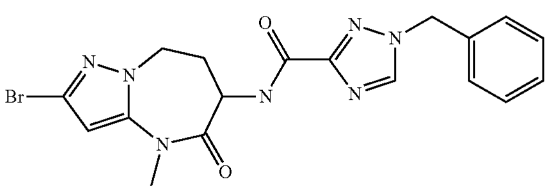 [SMILES: CN1C(=O)C(NC(=O)c2ncn(Cc3ccccc3)n2)CCn2nc(Br)cc21]

Step 8: 1-benzyl-N-(2-bromo-4-methyl-5-oxo-5,6,7,8-tetrahydro-4H-pyrazolo[1,5-a][1,3]diazepin-6-yl)-1H-1,2,4-triazole-3-carboxamide A mixture of 6-amino-2-bromo-4-methyl-7,8-dihydro-6H-pyrazolo[1,5-a][1,3]diazepin-5-one (4.0 g, 15.44 mmol), 1-hydroxybenzotriazole (3.1 g, 23.16 mmol), 1-(3-dimethylaminopropyl)-3-ethylcarbodiimidehydrochloride (4.4 g, 23.16 mmol) and 1-benzyl-1,2,4-triazole-3-carboxylic acid (3.8 g, 18.53 mmol) in N,N-dimethylformamide (20 mL) was stirred at 20° C. for 16 h. The reaction mixture was poured into water (100 mL) and stirred for 20 min. The resulting solid was collected by filtration and dried to give 1-benzyl-N-(2-bromo-4-methyl-5-oxo-5,6,7,8-tetrahydro-4H-pyrazolo[1,5-a][1,3]diazepin-6-yl)-1H-1,2,4-triazole-3-carboxamide (6.8 g, 99% yield) as white solids, used as is in the next step.

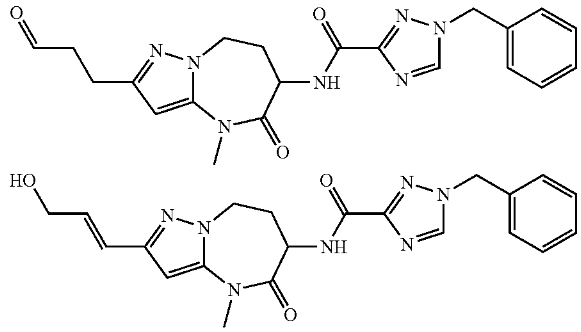

Step 9: 1-benzyl-N-[4-methyl-5-oxo-2-(3-oxopropyl)-7,8-dihydro-6H-pyrazolo[1,5-a][1,3]diazepin-6-yl]-1,2,4-triazole-3-carboxamide and (E)-1-benzyl-N-(2-(3-hydroxyprop-1-en-1-yl)-4-methyl-5-oxo-5,6,7,8]tetrahydro-4H-pyrazolo[1,5-a][1,3]diazepin-6-yl)-1H-1,2,4-triazole-3-carboxamide A mixture of 1-benzyl-N-(2-bromo-4-methyl-5-oxo-7,8-dihydro-6H-pyrazolo[1,5-a][1,3]diazepin-6-yl)-1,2,4-triazole-3-carboxamide (300 mg, 0.68 mmol), N,N-di isopropylethylamine (262 mg, 2.03 mmol), allyl alcohol (118 mg, 2.03 mmol) and bis(tri-tert-butylphosphine)palladium (34 mg, 0.07 mmol) in 1,4-dioxane (10 mL) was stirred at 80° C. for 12 h under $N_2$ atmosphere. The reaction mixture was concentrated under reduced pressure and the residue was purified by column chromatography (silica gel, 100-200 mesh, 0 to 10% methanol in dichloromethane) to give a mixture of 1-benzyl-N-[4-methyl-5-oxo-2-(3-oxopropyl)-7,8-dihydro-6H-pyrazolo[1,5-a][1,3]diazepin-6-yl]-1,2,4-triazole-3-carboxamide and (E)-1-benzyl-N-(2-(3-hydroxyprop-1-en-1-yl)-4-methyl-5-oxo-5,6,7,8-tetrahydro-4H-pyrazol o[1,5-a][1,3]diazepin-6-yl)-1H-1,2,4-triazole-3-carboxamide (250 mg, 88%, 3:7 ratio) as a yellow solid, used as is in the next step.

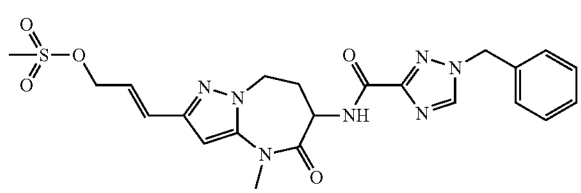 [SMILES: CN1C(=O)C(NC(=O)c2ncn(Cc3ccccc3)n2)CCn2nc(/C=C/COS(C)(=O)=O)cc21]

Step 10: [(E)-3-[6-[(1-benzyl-1,2,4-triazole-3-carbonyl)amino]-4-methyl-5-oxo-7,8-dihydro-6H-pyrazolo[1,5-a][1,3]diazepin-2-yl]allyl]methanesulfonate To a solution of (E)-1-benzyl-N-(2-(3-hydroxyprop-1-en-1-yl)-4-methyl-5-oxo-5,6,7,8-tetrahydro-4H-pyrazolo[1,5-a][1,3]diazepin-6-yl)-1H-1,2,4-triazole-3-carboxamide (40 mg, 0.09 mmol) in dichloromethane (5 mL) was added triethylamine (38 mg, 0.30 mmol) and methanesulfonyl chloride (16 mg, 0.14 mmol). The reaction mixture was stirred at 15° C. for 12 h. The mixture was washed with brine (5 mL), dried with anhydrous sodium sulfate and concentrated under reduced pressure to give crude [(E)-3-[6-[(1-benzyl-1,2,4-triazole-3-carbonyl)amino]-4-methyl-5-oxo-7,8-dihydro-6H-pyrazolo[1,5-a][1,3]diazepin-2-yl]allyl] methanesulfonate (35 mg, 74%) as a yellow oil, used as is in the next step.

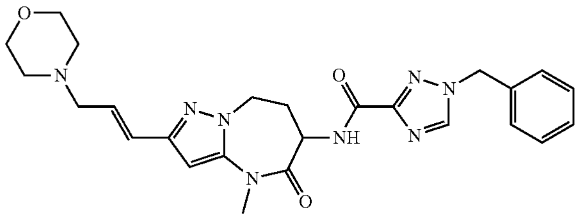 [SMILES: CN1C(=O)C(NC(=O)c2ncn(Cc3ccccc3)n2)CCn2nc(/C=C/CN3CCOCC3)cc21]

Step 11: 1-benzyl-N-[4-methyl-2-[(E)-3-morpholinoprop-1-enyl]-5-oxo-7,8-dihydro-6H-pyrazolo[1,5-a][1,3]diazepin-6-yl]-1,2,4-triazole-3-carboxamide To a solution of [(E)-3-[6-[(1-benzyl-1,2,4-triazole-3-carbonyl)amino]-4-methyl-5-oxo-7,8-dihydro-6H-pyrazolo[1,5-a][1,3]diazepin-2-yl]allyl]methanesulfonate (35 mg, 0.07 mmol) in N,N-dimethylformamide (3 mL) was added potassium carbonate (48 mg, 0.35 mmol) and morpholine (18 mg, 0.21 mmol). The reaction mixture was stirred at 35° C. for 1 h and then poured into water (15 mL). The mixture was extracted with ethyl acetate (3×10 mL). The combined organic layers were washed with brine (10 mL), dried with sodium sulfate and concentrated under reduced pressure to give crude 1-benzyl-N-[4-methyl-2-[(E)-3-morpholinoprop-1-enyl]-5-oxo-7,8-dihydro-6H-pyrazolo[1,5-a][1,3]diazepin-6-yl]-1,2,4-triazole-3-carboxamide (30 mg, 87%) as a yellow oil, used as is in the next step.

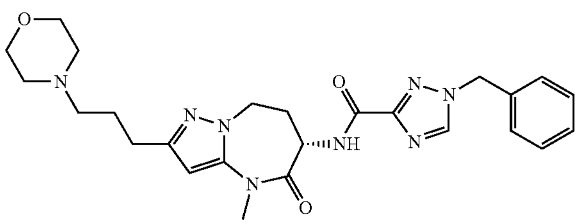

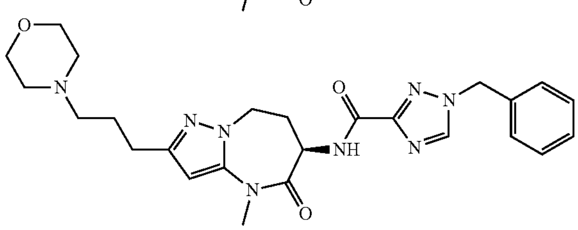

Step 12: 1-benzyl-N-(6S)-4-methyl-2-(3-morpholinopropyl)-5-oxo-7,8-dihydro-6H-pyrazolo[1,5-a][1,3]diazepin-6-yl]-1,2,4-triazole-3-carboxamide and 1-benzyl-N-(6R)-4-methyl-2-(3-morpholinopropyl)-5-oxo-7,8-dihydro-6H-pyrazolo[1,5-a][1,3]diazepin-6-yl]-1,2,4-triazole-3-carboxamide A mixture of 1-benzyl-N-[4-methyl-2-[(E)-3-morpholinoprop-1-enyl]-5-oxo-7,8-dihydro-6H-pyrazolo[1,5-a][1,3]diazepin-6-yl]-1,2,4-triazole-3-carboxamide (30 mg, 0.06 mmol) and Pd/C (10%, 19 mg, 0.02 mmol) in ethyl acetate (10 mL) was hydrogenated (15 psi) for 12 h and then filtered. The filtrate was concentrated under reduced pressure and the residue was purified by RP-HPLC ((acetonitrile 20-50%/0.05% $NH_3.H_2O$ in water)) to give 1-benzyl-N-[4-methyl-2-(3-morpholinopropyl)-5-oxo-7,8-dihydro-6H-pyrazolo[1,5-a][1,3]di azepin-6-yl]-1,2,4-triazole-3-carboxamide (15 mg, 50%) as a white solid.

Two batches of the racemic material (40 mg) were separated by chiral SFC to give:

1-benzyl-N-(6S)-4-methyl-2-(3-morpholinopropyl)-5-oxo-7,8-dihydro-6H-pyrazolo[1,5-a][1, 3]diazepin-6-yl]-1,2,4-triazole-3-carboxamide (Peak 1, Retention time=4.402 min) (18.3 mg, 44%) as a white solid. $^1$H NMR (400 MHz, $CD_3OD$) δ8.57 (s, 1H), 7.38-7.32 (m, 5H), 6.17 (s, 1H), 5.47 (s, 2H), 4.54-4.49 (m, 1H), 4.33-4.30 (m, 1H), 4.27-4.23 (m, 1H), 3.72 (t, J=4.4 Hz, 4H), 3.32 (s, 3H), 2.83-2.80 (m, 1H), 2.66-2.48 (m, 8H), 2.26-2.24 (m, 1H), 1.92-1.88 (m, 2H). LC-MS $R_T$=1.449 min, m/z=493.3 [M+H]$^+$.

LCMS (10 to 80% acetonitrile in water+0.03% ammonium bicarbonate over 3.0 mins) retention time 1.449 min, ESI+ found [M+H]=493.3.

1-benzyl-N-(6R)-4-methyl-2-(3-morpholinopropyl)-5-oxo-7,8-dihydro-6H-pyrazolo[1,5-a][1, 3]diazepin-6-yl]-1,2,4-triazole-3-carboxamide (Peak 2, Retention time=4.483 min) (18.8 mg, 45%) as a white solid. $^1$H NMR (400 MHz, $CD_3OD$) δ8.56 (s, 1H), 7.38-7.32 (m, 5H), 6.17 (s, 1H), 5.47 (s, 2H), 4.54-4.49 (m, 1H), 4.33-4.30 (m, 1H), 4.27-4.21 (m, 1H), 3.69 (t, J=4.8 Hz, 4H), 3.33 (s, 3H), 2.83-2.80 (m, 1H), 2.66-2.62 (m, 2H), 2.48-2.40 (m, 6H), 2.26-2.24 (m, 1H), 1.89-1.86 (m, 2H). LC-MS $R_T$=1.449 min, m/z=493.3 [M+H]$^+$.

LCMS (10 to 80% acetonitrile in water+0.03% ammonium bicarbonate over 3.0 mins) retention time 1.449 min, ESI+ found [M+H]=493.3.

SFC condition: column: chiralpak AD-3 (100×4.6 mm), 3 um mobile phase: A: CO2; B: MeOH (0.05% DEA) gradient: from 5 to 40 of B in 4.5 min and hold 40% for 2.5 min, then 5% of B for 1 min. Flow rate: 2.8 mL/min. Column temperature: 40° C.

Example 663

WX Method 031

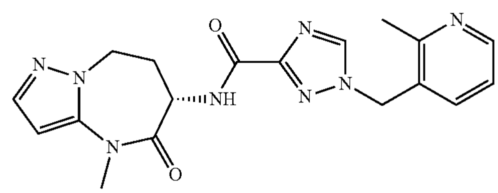 [SMILES: Cc1ncccc1Cn1cnc(C(=O)N[C@H]2CCn3nccc3N(C)C2=O)n1]

1-[(2-methyl-3-pyridyl)methyl]-N-(6S)-4-methyl-5-oxo-7,8-dihydro-6H-pyrazolo[1,5-a][1,3]diazepin-6-yl-1,2,4-triazole-3-carboxamide

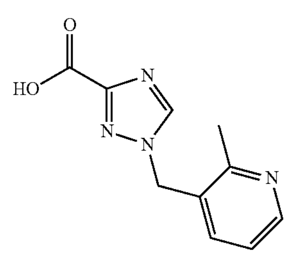 [SMILES: Cc1ncccc1Cn1cnc(C(=O)O)n1]

Step 1: 1-[(2-methyl-3-pyridyl)methyl]-1,2,4-triazole-3-carboxylic acid

A mixture of methyl 1H-1,2,4-triazole-3-carboxylate (239 mg, 1.88 mmol), potassium carbonate (520 mg, 3.76 mmol) and 3-(bromomethyl)-2-methyl-pyridine (350 mg, 1.88 mmol) in N,N-dimethylformamide (5 mL) was stirred at 25° C. for 16 h and filtered. The filtrate was concentrated under reduced pressure to afford crude methyl 1-[(2-methyl-3-pyridyl)methyl]-1,2,4-triazole-3-carboxylate (0.30 g, 69%) as a yellow oil. The above crude was diluted with water (5 mL) and stirred for 10 min at 25° C. The mixture was adjusted to pH=6 by addition of 2N HCl. The resulting mixture was concentrated under reduced pressure to give crude 1-[(2-methyl-3-pyridyl)methyl]-1,2,4-triazole-3-carboxylic acid (260 mg, 92%) as yellow solid, used as is in the next step.

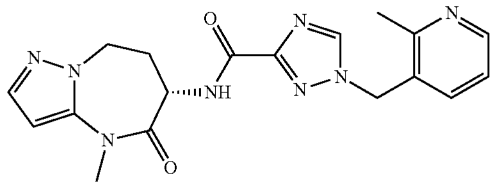 [SMILES: Cc1ncccc1Cn1cnc(C(=O)N[C@H]2CCn3nccc3N(C)C2=O)n1]

Step 2: 1-[(2-methyl-3-pyridyl)methyl]-N-(6S)-4-methyl-5-oxo-7,8-dihydro-6H-pyrazolo[1,5-a][1,3]diazepin-6-yl-1,2,4-triazole-3-carboxamide A mixture of 1-(3-dimethylaminopropyl)-3-ethylcarbodiimidehydrochloride (79 mg, 0.41 mmol), (6S)-6-amino-4-methyl-7,8-dihydro-6H-pyrazolo[1,5-a][1,3]diazepin-5-one (49 mg, 0.27 mmol), 1-hydroxybenzotriazole (7 mg, 0.05 mmol) and 1-[(2-methyl-3-pyridyl)methyl]-1,2,4-triazole-3-carboxylic acid (60 mg, 0.27 mmol) in N,N-dimethylformamide (2.5 mL) was stirred at 20° C. for 12 h and concentrated under reduced pressure. The residue was purified by RP-HPLC (acetonitrile 17-47/0.05% ammonium hydroxide in water to afford 1-[(2-methyl-3-pyridyl)methyl]-N-(6S)-4-methyl-5-oxo-7,8-dihydro-6H-pyrazolo[1,5-a][1,3]diazepin-6-yl-1,2,4-triazole-3-carboxamide (36.1 mg, 34%) as a white solid. $^1$H NMR (400 MHz, $CD_3OD$) δ8.63 (s, 1H), 8.41 (d, J=4.4 Hz, 1H), 7.60 (d, J=7.6 Hz, 1H), 7.56-7.52 (m, 1H), 7.32-7.29 (m, 1H), 6.33-6.31 (m, 1H), 5.60 (s, 2H), 4.55-4.42 (m, 2H), 4.35-4.24 (m, 1H), 3.37 (s, 3H), 2.95-2.82 (m, 1H), 2.61 (s, 3H), 2.35-2.25 (m, 1H). LCMS $R_T$=1.068 min, m/z=381.2 $[M+H]^+$. LCMS (0 to 60% acetonitrile in water+0.03% trifluoacetic acid over 3 mins) retention time 1.068 min, ESI+ found [M+H]=381.2.

Example 664

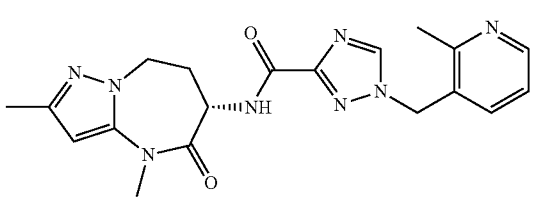 [SMILES: Cc1cc2n(n1)CC[C@H](NC(=O)c1ncn(Cc3cccnc3C)n1)C(=O)N2C]

1-[(2-methyl-3-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide Amide coupling prepared in a similar fashion to WX Method 031. The crude was purified by RP-HPLC (acetonitrile 17-47%/0.05% ammonium hydroxide in water) to give 1-[(2-methyl-3-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide (28.6 mg, 26%) as a light-yellow semi-solid. $^1$H NMR (400 MHz, $CD_3OD$) δ8.61 (s, 1H), 8.39 (d, J=4.8 Hz, 1H), 7.59 (d, J=7.6 Hz, 1H), 7.30-7.27 (m, 1H), 6.11 (s, 1H), 5.58 (s, 2H), 4.55-4.50 (m, 1H), 4.35-4.27 (m, 1H), 4.26-4.16 (m, 1H), 3.32 (s, 3H), 2.90-2.78 (m, 1H), 2.59 (s, 3H), 2.30-2.20 (m, 4H). LCMS $R_T$=1.165 min, m/z=395.2 $[M+H]^+$.

LCMS (0 to 60% acetonitrile in water+0.03% trifluoacetic acid over 3 mins) retention time 1.165 min, ESI+ found [M+H]=395.2.

Example 665

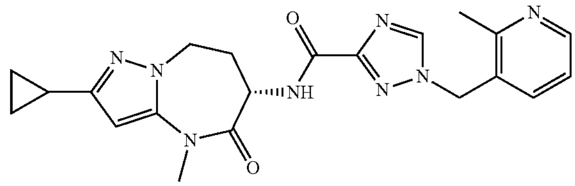 [SMILES: Cc1ncccc1Cn1cnc(C(=O)N[C@H]2CCn3nc(C4CC4)cc3N(C)C2=O)n1]

1-[(2-methyl-3-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide Amide coupling prepared in a similar fashion to WX Method 031. The crude was purified by RP-HPLC (acetonitrile 17-47%/0.05% ammonium hydroxide in water) to give 1-[(2-methyl-3-pyridyl)methyl]-N-(6 S)-2-cyclopropyl-4-methyl-5-oxo-7,8-dihydro-6H-pyrazolo[1,5-a][1,3]diazepin-6-yl-1,2,4-triazole-3-carboxamide (37 mg, 30%) as a white solid. $^1$H NMR (400 MHz, $CD_3OD$) δ8.62 (s, 1H), 8.40 (d, J=4.0 Hz, 1H), 7.59 (d, J=7.6 Hz, 1H), 7.31-7.28 (m, 1H), 6.01 (s, 1H), 5.59 (s, 2H), 4.55-4.50 (m, 1H), 4.35-4.27 (m, 1H), 4.25-4.15 (m, 1H), 3.33-3.32 (m, 3H), 2.90-2.78 (m, 1H), 2.60 (s, 3H), 2.33-2.19 (m, 1H), 1.96-1.87 (m, 1H), 0.98-0.91 (m, 2H), 0.78-0.70 (m, 2H). LCMS $R_T$=1.287 min, m/z=421.3 $[M+H]^+$. LCMS (0 to 60% acetonitrile in water+0.03% trifluoacetic acid over 3 mins) retention time 1.287 min, ESI+ found [M+H]=421.3.

Examples 666 and 667

WX Method 127

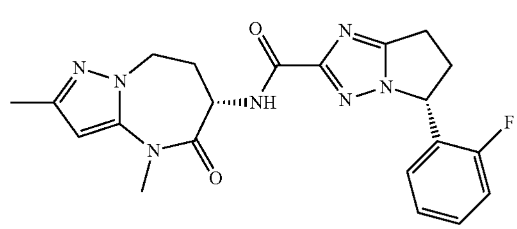

-continued

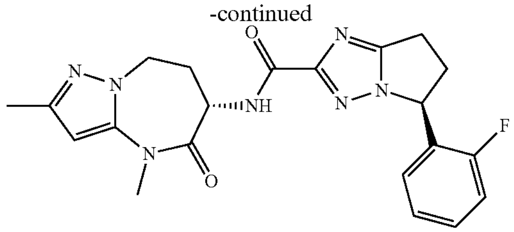

(5R)-5-(2-fluorophenyl)-N-[(6S)-2,4-dimethyl-5-oxo-7,8-dihydro-6H-pyrazol-[1,5-a][1,3]diazepin-6-yl]-6,7-dihydro-5H-pyrrolo[1,2-b][1,2,4]triazole-2-carboxamide and (5S)-5-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide

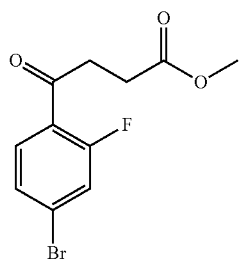 [SMILES: COC(=O)CCC(=O)c1ccc(Br)cc1F]

Step 1: methyl 4-(4-bromo-2-fluorophenyl)-4-oxobutanoate

To a solution of 1-bromo-3-fluorobenzene (5.0 g, 28.57 mmol) in 1,2-dichloroethane (100 mL) was added aluminum chloride (15.2 g, 114.29 mmol) and methyl 4-chloro-4-oxobutyrate (8.6 g, 57.14 mmol). The mixture was heated at 70° C. for 12 h and cooled. The reaction was slowly quenched by addition of water (20 mL) and extracted with dichloromethane (2×100 mL). The combined organic layers were concentrated under reduced pressure and the residue was purified by column chromatography (silica gel, 100-200 mesh, 0 to 20% ethyl acetate in petroleum ether) to afford methyl 4-(4-bromo-2-fluoro-phenyl)-4-oxo-butanoate (2.0 g, 24%) as a yellow solid. LCMS $R_T$=0.995 min, m/z=291.1 $[M+H]^+$.

LCMS (10 to 80% acetonitrile in water+0.03% trifluoacetic acid over 2.0 mins) retention time 0.995 min, ESI+ found [M+H]=291.1

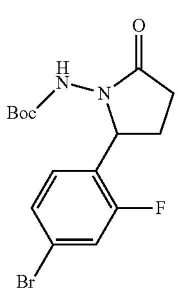 [SMILES: CC(C)(C)OC(=O)NN1C(=O)CCC1c1ccc(Br)cc1F]

Step 2: tert-butyl (2-(4-bromo-2-fluorophenyl)-5-oxopyrrolidin-1-yl)carbamate

To a solution of methyl 4-(4-bromo-2-fluoro-phenyl)-4-oxo-butanoate (2.0 g, 6.91 mmol) in tetrahydrofuran (10 mL) and acetic acid (5 mL) was added tert-butyl hydrazinecarboxylate (1.3 g, 10.38 mmol). The mixture was stirred at 40° C. for 12 h and then sodiumcyanoborohydride (652 mg, 10.38 mmol) was added. Stirring was continued for another 6 h and the mixture was concentrated under reduced pressure. The residue was diluted with ethyl acetate (50 mL), washed with water (2×20 mL), brine (20 mL), dried over sodium sulfate and concentrated under reduced pressure. The residue was purified by column chromatography (silica gel, 100-200 mesh, 0 to 100% ethyl acetate in petroleum ether) to afford tert-butyl N-[2-(2-fluorophenyl)-5-oxo-pyrrolidin-1-yl]carbamate (800 mg, 78%) as yellow oil. LCMS $R_T$=1.067 min, m/z=319.0 $[M+H]^+$.

LCMS (10 to 80% acetonitrile in water+0.03% trifluoacetic acid over 2.0 mins) retention time 1.067 min, ESI+ found [M−55]=319.0

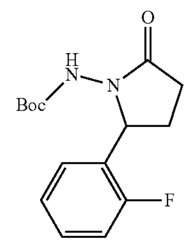 [SMILES: CC(C)(C)OC(=O)NN1C(=O)CCC1c1ccccc1F]

Step 3: tert-butyl (2-(2-fluorophenyl)-5-oxopyrrolidin-1-yl)carbamate

A mixture of tert-butyl N-[2-(4-bromo-2-fluoro-phenyl)-5-oxo-pyrrolidin-1-yl]carbamate (800 mg, 2.14 mmol) and Pd/C (10%, 228 mg, 0.21 mmol) in methanol (10 mL) was hydrogenated (15 psi) at 25° C. for 4 h and then filtered. The filtrate was concentrated under reduced pressure to afford crude tert-butyl N-[2-(2-fluorophenyl)-5-oxo-pyrrolidin-1-yl]carbamate (500 mg, 79%) as a white solid. LCMS $R_T$=0.972 min, m/z=239.1 $[M+H]^+$.

LCMS (10 to 80% acetonitrile in water+0.03% trifluoacetic acid over 2.0 mins) retention time 0.972 min, ESI+ found [M−55]=239.1

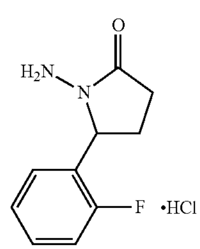 [SMILES: NN1C(=O)CCC1c1ccccc1F ; Cl]

Step 4: 1-amino-5-(2-fluorophenyl)pyrrolidin-2-one hydrochloride

A solution of tert-butyl (2-(2-fluorophenyl)-5-oxopyrrolidin-1-yl)carbamate (400 mg, 1.36 mmol) in ethyl acetate (5 mL) was added HCl (4N in ethyl acetate, 1.0 mL, 4.0 mmol).

The mixture was stirred at 25° C. for 4 h and then concentrated under reduced pressure to afford crude 1-amino-5-(2-fluorophenyl)pyrrolidin-2-one hydrochloride (400 mg, 100%) as white solid, used as is in the next step.

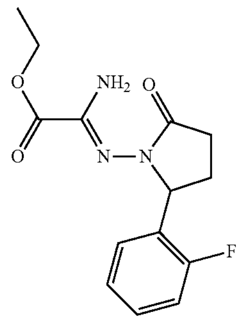 [SMILES: CCOC(=O)/C(N)=N/N1C(=O)CCC1c1ccccc1F]

Step 5: (Z)-ethyl 2-amino-2-((2-(2-fluorophenyl)-5-oxopyrrolidin-1-yl)imino)acetate To a solution of 1-amino-5-(2-fluorophenyl)pyrrolidin-2-one hydrochloride (400 mg, 2.06 mmol) in ethanol (10 mL) was added ethyl 2-ethoxy-2-imino-acetate (1.8 g, 12.36 mmol). The mixture was stirred at 40° C. for 12 h and concentrated under reduced pressure to afford crude ethyl (2Z)-2-amino-2-[2-(2-fluorophenyl)-5-oxo-pyrrolidin-1-yl]imino-acetate (500 mg, 82%) as a yellow oil, used as is in the next step.

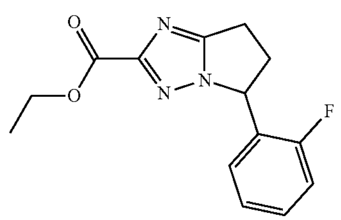 [SMILES: CCOC(=O)c1nc2n(n1)C(c1ccccc1F)CC2]

Step 6: methyl 7-methyl-5,6,7,8-tetrahydroimidazo[1,5-a]pyridine-1-carboxylate

A solution of ethyl (2Z)-2-amino-2-[2-(2-fluorophenyl)-5-oxo-pyrrolidin-1-yl]imino-acetate (500 mg, 1.7 mmol) in phosphorus oxychloride (5.0 mL, 135.9 mmol) was heated at 120° C. for 1 h. After cooled, the mixture was slowly quenched by addition of water (20 mL) and extracted with dichloromethane (3×20 mL). The combined organic layers were washed with 20% sodium bicarbonate (20 mL), brine (30 mL), dried over sodium sulfate and concentrated under reduced pressure. The residue was purified by column chromatography (silica gel, 100-200 mesh, 0 to 60% ethyl acetate in petroleum ether) to afford ethyl 5-(2-fluorophenyl)-6,7-dihydro-5H-pyrrolo[1,2-b][1,2,4]triazole-2-carboxylate (400 mg, 85%) as a light yellow oil. LCMS $R_T$=0.760 min, m/z=275.9 $[M+H]^+$.

LCMS (5 to 95% acetonitrile in water+0.03% trifluoacetic acid over 1.5 mins) retention time 0.760 min, ESI+ found [M+H]=275.9

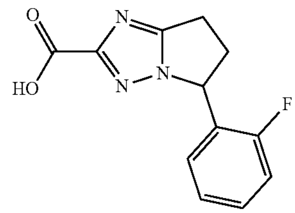 [SMILES: O=C(O)c1nc2n(n1)C(c1ccccc1F)CC2]

Step 7: 5-(2-fluorophenyl)-6,7-dihydro-5H-pyrrolo[1,2-b][1,2,4]triazole-2-carboxylic acid A mixture of ethyl 5-(2-fluorophenyl)-6,7-dihydro-5H-pyrrolo[1,2-b][1,2,4]triazole-2-carboxylate (400 mg, 1.45 mmol) and potassium hydroxide in ethanol (20 mL) and water (5 mL) was stirred at 25° C. for 12 h. The ethanol was removed under reduced pressure. The residue was diluted with water (20 mL) and adjusted to pH=4 by addition of 2N HCl. The mixture was extracted with ethyl acetate (3×20 mL). The combined organic layers were concentrated under reduced pressure to afford crude 5-(2-fluorophenyl)-6,7-dihydro-5H-pyrrolo[1,2-b][1,2,4]triazole-2-carboxylic acid (200 mg, 55%) as a yellow solid, used as is in the next step.

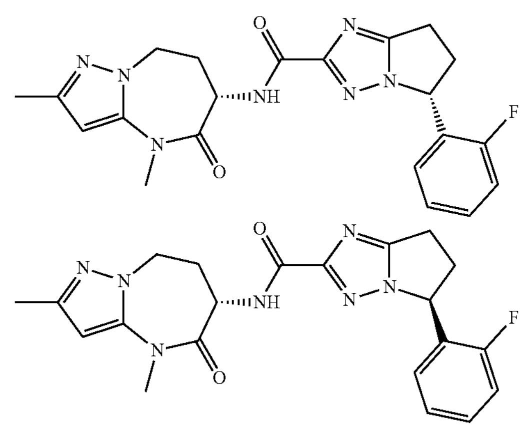

Step 8: (5R)-5-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide and (5S)-5-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide A mixture of (6S)-6-amino-2,4-dimethyl-7,8-dihydro-6H-pyrazolo[1,5-a][1,3]diazepin-5-one (40 mg, 0.21 mmol), 1-(3-dimethylaminopropyl)-3-ethylcarbodiimide hydrochloride (59 mg, 0.31 mmol), 1-hydroxybenzotriazole (31 mg, 0.21 mmol). and 5-(2-fluorophenyl)-6,7-dihydro-5H-pyrrolo[1,2-b][1,2,4]triazole-2-carboxylic acid (50 mg, 0.21 mmol) in N,N-dimethylformamide (5 mL) was stirred at 25° C. for 12 h. The mixture was concentrated under reduced pressure and the residue was purified by preparative TLC (0-2% methanol in dichloromethane, $R_f$=0.5) to afford N—((S)-2,4-dimethyl-5-oxo-5,6,7,8-tetrahydro-4H-pyrazolo[1,5-a][1,3]diazepin-6-yl)-5-(2-fluorophenyl)-6,7-dihydro-5H-pyrrolo[1,2-b][1,2,4]triazole-2-carboxamide (60 mg, 69%) as a white solid. The racemic material was separated by chiral SFC to give:

(5R)-5-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (Peak 1, retention time 2.561 min) (25 mg, 41.7%) as white solids. $^{1}H$ NMR (400 MHz, $CD_3OD$) δ7.45-7.38 (m, 1H), 7.24-7.14 (m, 3H), 6.12 (s, 1H), 5.79-5.75 (m, 1H), 4.53-4.49 (m, 1H), 4.35-4.28 (m, 1H), 4.26-4.16 (m, 1H), 3.37-3.33 (m, 3H), 3.32-3.27 (m, 1H), 3.19-3.05 (m, 2H), 2.88-2.79 (m, 1H), 2.78-2.68 (m, 1H), 2.26 (s, 3H), 2.25-2.17 (m, 1H). LCMS $R_T$=0.91 min, m/z=424.2 $[M+H]^+$. LCMS (10 to 80% acetonitrile in water+0.1% trifluoacetic acid over 2.0 mins) retention time 0.91 min, ESI+ found [M+H]=424.2.

(5S)-5-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (Peak 2, retention time 2.779 min) (25 mg, 41.7%) white solids. $^{1}H$ NMR (400 MHz, $CD_3OD$) δ7.45-7.38 (m, 1H), 7.24-7.14 (m, 3H), 6.12 (s, 1H), 5.80-5.76 (m, 1H), 4.54-4.49 (m, 1H), 4.35-4.28 (m, 1H), 4.26-4.16 (m, 1H), 3.37-3.33 (m, 3H), 3.32-3.27 (m, 1H), 3.19-3.05 (m, 2H), 2.88-2.79 (m, 1H), 2.78-2.68 (m, 1H), 2.26 (s, 3H), 2.25-2.17 (m, 1H). LCMS $R_T$=0.92 min, m/z=424.2 $[M+H]^+$. LCMS (10 to 80% acetonitrile in water+0.1% trifluoacetic acid over 2.0 mins) retention time 0.92 min, ESI+ found [M+H]=424.2.

SFC conditions: Column: Chiralcel OJ-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min, Column temp.: 40° C.

Examples 668 and 669

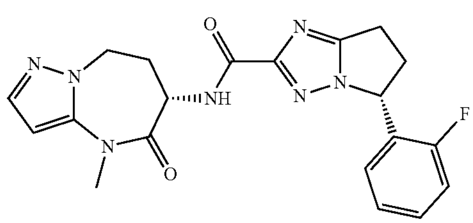

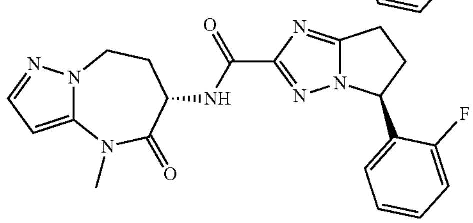

(5R)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide and (5S)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide Amide coupling prepared in a similar fashion to WX Method 127. The crude was purified by RP-HPLC (acetonitrile 22-52%/0.05% ammonium hydroxide in water) to afford 5-(2-fluorophenyl)-N—((S)-4-methyl-5-oxo-5,6,7,8-tetrahydro-4H-pyrazolo[1,5-a][1,3]diazepin-6-yl)-6,7-dihydro-5H-pyrrolo[1,2-b][1,2,4]triazole-2-carboxamide (60 mg, 66%). The racemic material was separated by chiral SFC to give:

(5R)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (Peak 1, retention time 2.784 min) (25 mg, 41.2%)$^{1}H$ NMR (400 MHz, CD3OD) δ 7.51 (d, J=2.0 Hz, 1H), 7.43-7.37 (m, 1H), 7.22-7.13 (m, 3H), 6.29 (d, J=2.0 Hz, 1H), 5.77 (dd, J=8.0, 12.0 Hz, 1H), 4.52-4.38 (m, 2H), 4.30-4.22 (m, 1H), 3.34 (s, 3H), 3.30-3.25 (m, 1H), 3.19-3.03 (m, 2H), 2.88-2.80 (m, 1H), 2.74-2.68 (m, 1H), 2.30-2.21 (m, 1H). LCMS $R_T$=0.76 min, m/z=410.0 $[M+H]^+$.

LCMS (5 to 95% acetonitrile in water+0.1% trifluoacetic acid over 1.5 mins) retention time 0.76 min, ESI+ found [M+H]=410.0.

(5S)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide (Peak 2, retention time 2.950 min) (24 mg, 39.6%) as a white solid. $^{1}H$ NMR (400 MHz, $CD_3OD$) δ7.52 (s, 1H), 7.43-7.37 (m, 1H), 7.22-7.12 (m, 3H), 6.30 (s, 1H), 5.80-5.76 (m, 1H), 4.53-4.38 (m, 2H), 4.30-4.22 (m, 1H), 3.35 (s, 3H), 3.30-3.25 (m, 1H), 3.19-3.03 (m, 2H), 2.90-2.79 (m, 1H), 2.76-2.67 (m, 1H), 2.30-2.21 (m, 1H). LCMS $R_T$=0.75 min, m/z=410.0 $[M+H]^+$.

LCMS (5 to 95% acetonitrile in water+0.1% trifluoacetic acid over 1.5 mins) retention time 0.75 min, ESI+ found [M+H]=410.0.

SFC conditions: Column: Chiralcel OJ-3 100×4.6 mm I.D., 3 um Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min, Column temp.: 40° C.

Examples 670-697 ("Chiral Table 1")

In each example below, Solvent A is $CO_2$ and Solvent B is 0.1% $NH_4OH$/Methanol. Column temperature is 40° C. in each example.

| Ex # | Instrument | Initial % B | Final % B | Wavelength | column type | column dimension | flow rate |
|---|---|---|---|---|---|---|---|
| 670 | PIC 100 Chiral | 30 | | 220 | Chiralpak AD | 150 × 21.2 mm | 70 |
| 671 | Thar 100 Chiral | | | 220 | Cellulose-1 | 150 × 30 mm | 100 |
| 672 | PIC 100 Chiral | 30 | | 220 | Whelko-01 | 150 × 21.2 mm | 70 |
| 673 | PIC 100 Chiral | 20 | | 220 | Chiralpak AS | 150 × 21.2 mm | 70 |
| 674 | Thar 100 Chiral | | | 220 | Cellulose-1 | 150 × 30 mm | 100 |

-continued

| Ex # | Instrument | Initial % B | Final % B | Wavelength | column type | column dimension | flow rate |
|---|---|---|---|---|---|---|---|
| 675 | Thar 100 Chiral | | | 220 | Cellulose-1 | 150 × 30 mm | 100 |
| 676 | PIC 100 Chiral | 30 | | 220 | Chiralpak AD | 150 × 21.2 mm | 70 |
| 677 | Thar 100 Chiral | | | 220 | Cellulose-1 | 150 × 30 mm | 100 |
| 678 | Thar 100 Chiral | | | 220 | Cellulose-1 | 150 × 30 mm | 100 |
| 679 | Thar 100 Chiral | | | 220 | Cellulose-1 | 150 × 30 mm | 100 |
| 680 | Thar 100 Chiral | | | 220 | Cellulose-1 | 150 × 30 mm | 100 |
| 681 | Thar 100 Chiral | | | 220 | Cellulose-1 | 150 × 30 mm | 100 |
| 682 | Jasco 150 | 30 | 30 | 240 nm | Chiralpak OX | 250 × 21.2 mm, 5 um | 70 |
| 683 | Jasco 150 | 35 | 35 | 240 nm | Chiralpak OX | 250 × 21.2 mm, 5 um | 70 |
| 684 | Jasco 150 | 35 | 35 | 240 nm | Chiralpak OX | 250 × 21.2 mm, 5 um | 70 |
| 685 | Jasco 150 | 30 | 30 | 240 nm | Chiralpak OX | 250 × 21.2 mm, 5 um | 70 |
| 686 | PIC 100 Chiral | 35 | 35 | 230 | Whelko-01 | 150 × 21.2 mm | 70 |
| 687 | PIC 100 Chiral | 20 | 20 | 230 | Cellulose-1 | 150 × 21.2 mm | 70 |
| 688 | PIC 100 Chiral | 20 | 20 | 230 | Chiralpak AD | 150 × 21.2 mm | 70 |
| 689 | PIC 100 Chiral | 35 | 35 | 230 | Whelko-01 | 150 × 21.2 mm | 70 |
| 690 | PIC 100 Chiral | 20 | 20 | 230 | Cellulose-1 | 150 × 21.2 mm | 70 |
| 691 | PIC 100 Chiral | 20 | 20 | 230 | Chiralpak AD | 150 × 21.2 mm | 70 |
| 692 | PIC 100 Chiral | | | 254 nm | Chiralpak AS | 150 × 21.2 mm | 70 |
| 693 | PIC 100 Chiral | | | 254 nm | Cellulose-3 | 150 × 21.2 mm | 70 |
| 694 | PIC 100 Chiral | | | 254 nm | Chiralpak AD | 150 × 21.2 mm | 70 |
| 695 | Thar 100 Chiral | | | 254 nm | Chiralpak AD | 150 × 30 mm | 100 |
| 696 | PIC 100 Chiral | | | 254 nm | Chiralpak AS | 150 × 21.2 mm | 70 |
| 697 | PIC 100 Chiral | | | 254 nm | Chiralpak AD | 150 × 21.2 mm | 70 |

Example 698: Suzuki Method 1

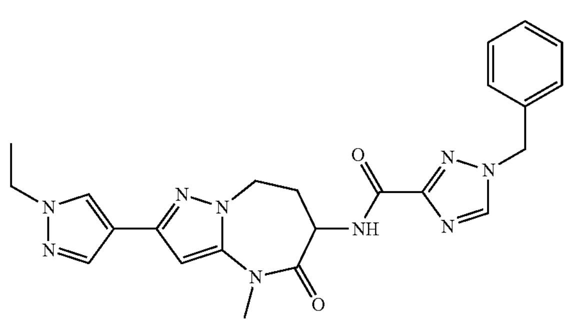 [SMILES: CCn1cc(-c2cc3n(n2)CCC(NC(=O)c2ncn(Cc4ccccc4)n2)C(=O)N3C)cn1]

1-benzyl-N-[2-(1-ethylpyrazol-4-yl)-4-methyl-5-oxo-7,8-dihydro-6H-pyrazolo[1,5-a][1,3]diazepin-6-yl]-1,2,4-triazole-3-carboxamide To a microwave vial was charged 1-benzyl-N-(2-bromo-4-methyl-5-oxo-7,8-dihydro-6H-pyrazolo[1,5-a][1,3]diazepin-6-yl)-1,2,4-triazole-3-carboxamide (100 mg, 0.2251 mmol), 1-ethyl-4-(4,4,5,5-tetramethyl-1,3,2-dioxaborolan-2-yl)-1H-pyrazole, (61.21 mg, 0.27 mmol), and [1,1'-bis(diphenylphosphino)ferrocene]dichloropalladium(II) (1:1) (17.34 mg, 0.023 mmol). The solids were dissolved in a mixture of acetonitrile (0.6431 mL) and 1N potassium carbonate (0.6431 mL, 0.6431 mmol), the vial was sealed and irradiated in a microwave at 110° C. for 10 min. The reaction mixture was diluted with ethyl acetate (10 mL), washed with water (2×5 mL), brine and dried over sodium sulphate. The filtrate was concentrated to dryness in vacuo and the residue was purified by reverse phase HPLC to afford 1-benzyl-N-[2-(1-ethylpyrazol-4-yl)-4-methyl-5-oxo-7,8-dihydro-6H-pyrazolo[1,5-a][1,3]diazepin-6-yl]-1,2,4-triazole-3-carboxamide as a white solid (30 mg, 29% yield). $^1$H NMR (400 MHz, DMSO-$d_6$) δ 8.82 (s, 1H), 8.54 (d, J=7.8 Hz, 1H), 8.04 (d, J=0.7 Hz, 1H), 7.72 (d, J=0.7 Hz, 1H), 7.55-7.21 (m, 5H), 6.50 (s, 1H), 5.48 (s, 2H), 4.45-4.28 (m, 2H), 4.24-4.09 (m, 3H), 3.26 (s, 3H), 2.69-2.57 (m, 1H), 2.43-2.30 (m, 1H), 1.39 (t, J=7.3 Hz, 3H). LC-MS $R_T$=4.04 min, m/z=460.2 [M+H]$^+$. LCMS (2 to 98% acetonitrile in water+0.1% formic acid over 10 mins) retention time 4.04 min, ESI+ found [M+H]=460.2.

SFC condition: Column: Cellulose-1 150×21.2 mm, 3 μm Mobile phase: A: CO2 B: Methanol (0.1% NH4OH), Isocratic Gradient: 40% B for 37.5 min. Flow rate: 70 mL/min Column temperature: 40° C., BPR: 120 bar.

Example 699

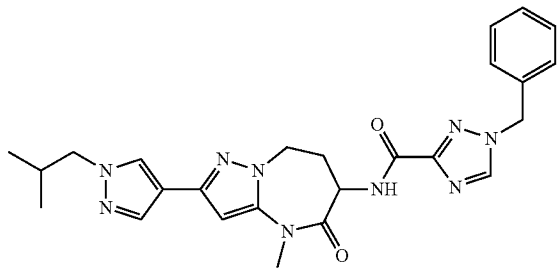 [SMILES: CC(C)Cn1cc(-c2cc3n(n2)CCC(NC(=O)c2ncn(Cc4ccccc4)n2)C(=O)N3C)cn1]

1-benzyl-N-[2-(1-isobutylpyrazol-4-yl)-4-methyl-5-oxo-7,8-dihydro-6H-pyrazolo[1,5-a][1,3]diazepin-6-yl]-1,2,4-triazole-3-carboxamide Suzuki Method 1. (20 mg, 41% Yield)

$^1$H NMR (400 MHz, DMSO-$d_6$) δ 8.82 (s, 1H), 8.54 (d, J=7.7 Hz, 1H), 8.00 (d, J=0.7 Hz, 1H), 7.73 (d, J=0.7 Hz, 1H), 7.44-7.23 (m, 5H), 6.51 (s, 1H), 5.48 (s, 2H), 4.46-4.29 (m, 2H), 4.25-4.11 (m, 1H), 3.93 (d, J=7.2 Hz, 2H), 3.26 (s, 3H), 2.71-2.58 (m, 1H), 2.43-2.32 (m, 1H), 2.19-2.05 (m, 1H), 0.85 (d, J=6.7 Hz, 6H). LC-MS $R_T$=4.51 min, m/z=488.2 $[M+H]^+$.

LCMS (2 to 98% acetonitrile in water+0.1% formic acid over 10 mins) retention time 4.51 min, ESI+ found [M+H]=488.2.

Example 700

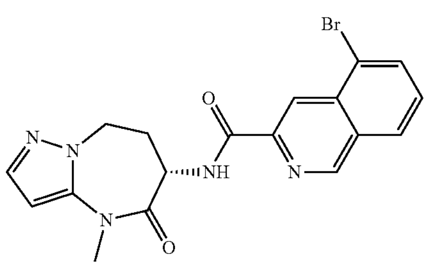 [SMILES: CN1C(=O)[C@@H](NC(=O)c2cc3c(Br)cccc3cn2)CCn2nccc21]

5-bromo-N-[rac-(6S)-4-methyl-5-oxo-7,8-dihydro-6H-pyrazolo[1,5-a][1,3]diazepin-6-yl]isoquinoline-3-carboxamide Method B. (74 mg, 90% yield)

$^1$H NMR (400 MHz, DMSO-$d_6$) δ 9.49 (d, J=0.8 Hz, 1H), 9.13 (d, J=7.7 Hz, 1H), 8.58 (t, J=0.9 Hz, 1H), 8.35 (d, J=8.3 Hz, 1H), 8.26 (dd, J=7.5, 1.0 Hz, 1H), 7.77 (dd, J=8.2, 7.5 Hz, 1H), 7.52 (d, J=2.0 Hz, 1H), 6.37 (d, J=2.0 Hz, 1H), 4.50-4.37 (m, 2H), 4.33-4.19 (m, 1H), 3.29 (s, 3H), 2.81-2.71 (m, 1H), 2.46-2.35 (m, 1H). LC-MS $R_T$=5.10 min, m/z=414.0 $[M+H]^+$.

LCMS (2 to 98% acetonitrile in water+0.1% formic acid over 10 mins) retention time 5.10 min, ESI+ found [M+H]=414.0.

Example 701

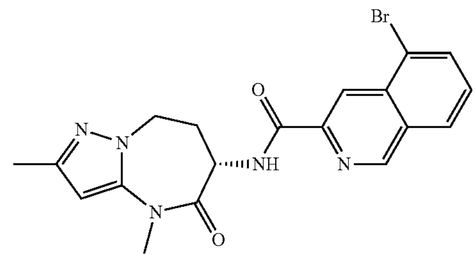 [SMILES: Cc1cc2n(n1)CC[C@H](NC(=O)c1cc3c(Br)cccc3cn1)C(=O)N2C]

5-bromo-N-[rac-(6S)-2,4-dimethyl-5-oxo-7,8-dihydro-6H-pyrazolo[1,5-a][1,3]diazepin-6-yl]isoquinoline-3-carboxamide Method B. (74 mg, 88% yield)

$^1$H NMR (400 MHz, DMSO-$d_6$) δ 9.49 (d, J=0.9 Hz, 1H), 9.11 (d, J=7.8 Hz, 1H), 8.58 (t, J=0.9 Hz, 1H), 8.40-8.31 (m, 1H), 8.26 (dd, J=7.5, 1.0 Hz, 1H), 7.77 (dd, J=8.2, 7.5 Hz, 1H), 6.15 (s, 1H), 4.54-4.38 (m, 1H), 4.38-4.25 (m, 1H), 4.24-4.08 (m, 1H), 3.26 (s, 3H), 2.89 (d, J=0.4 Hz, 1H), 2.80-2.66 (m, 2H), 2.42-2.31 (m, 1H), 2.19 (d, J=0.5 Hz, 3H). LC-MS $R_T$=5.32 min, m/z=428.0 $[M+H]^+$. LCMS (2 to 98% acetonitrile in water+0.1% formic acid over 10 mins) retention time 5.32 min, ESI+ found [M+H]=428.0.

Example 702

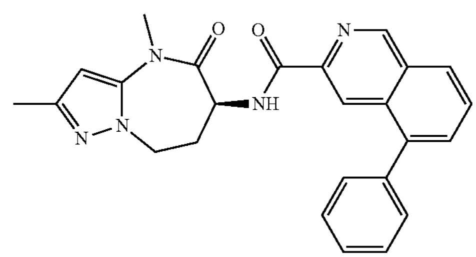 [SMILES: Cc1cc2n(n1)CC[C@H](NC(=O)c1cc3c(-c4ccccc4)cccc3cn1)C(=O)N2C]

5-phenyl-N-[rac-(6S)-2,4-dimethyl-5-oxo-7,8-dihydro-6H-pyrazolo[1,5-a][1,3]diazepin-6-yl]isoquinoline-3-carboxamide Method B and Subsequently Suzuki Method 1. (32 mg, 36% Yield)

$^1$H NMR (400 MHz, DMSO-$d_6$) δ 9.50 (d, J=0.9 Hz, 1H), 9.06 (d, J=7.7 Hz, 1H), 8.44-8.18 (m, 2H), 7.97-7.79 (m, 2H), 7.66-7.46 (m, 5H), 6.12 (s, 1H), 4.45-4.34 (m, 1H), 4.34-4.22 (m, 1H), 4.22-4.08 (m, 1H), 3.24 (s, 3H), 2.75-2.62 (m, 1H), 2.39-2.27 (m, 1H), 2.17 (s, 3H). LC-MS $R_T$=7.20 min, m/z=426.1 $[M+H]^+$.

LCMS (2 to 98% acetonitrile in water+0.1% formic acid over 10 mins) retention time 7.20 min, ESI+ found [M+H]=426.1.

Example 703

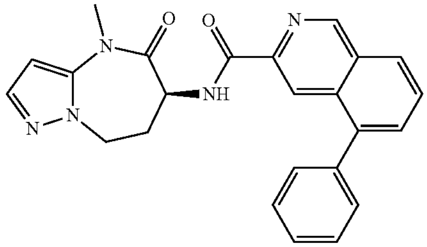 [SMILES: CN1C(=O)[C@@H](NC(=O)c2cc3c(-c4ccccc4)cccc3cn2)CCn2nccc21]

5-phenyl-N-[rac-(6S)-4-methyl-5-oxo-7,8-dihydro-6H-pyrazolo[1,5-a][1,3]diazepin-6-yl]isoquinoline-3-carboxamide Method B and Subsequently Suzuki Method 1. (18 mg, 21% Yield)

$^1$H NMR (400 MHz, DMSO-$d_6$) δ 9.51 (d, J=0.9 Hz, 1H), 9.08 (d, J=7.7 Hz, 1H), 8.40-8.25 (m, 2H), 7.97-7.79 (m, 2H), 7.66-7.46 (m, 6H), 6.33 (d, J=2.0 Hz, 1H), 4.45-4.32 (m, 2H), 4.32-4.17 (m, 1H), 3.27 (s, 3H), 2.78-2.64 (m, 1H), 2.44-2.31 (m, 1H). LC-MS $R_T$=6.97 min, m/z=412.1 $[M+H]^+$.

LCMS (2 to 98% acetonitrile in water+0.1% formic acid over 10 mins) retention time 6.97 min, ESI+ found [M+H]=412.1.

Example 704

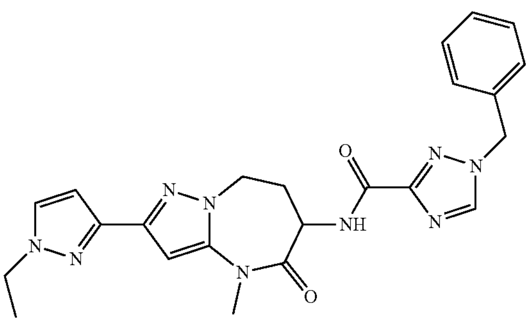 [SMILES: CCn1ccc(-c2cc3n(n2)CCC(NC(=O)c2ncn(Cc4ccccc4)n2)C(=O)N3C)n1]

1-benzyl-N-[2-(1-ethylpyrazol-3-yl)-4-methyl-5-oxo-7,8-dihydro-6H-pyrazolo[1,5-a][1,3]diazepin-6-yl]-1,2,4-triazole-3-carboxamide Suzuki Method 1 (38 mg, 61% Yield)

$^1$H NMR (400 MHz, DMSO-$d_6$) δ 8.82 (s, 1H), 8.54 (d, J=7.8 Hz, 1H), 7.75 (d, J=2.3 Hz, 1H), 7.46-7.25 (m, 5H), 6.59 (s, 1H), 6.50 (d, J=2.2 Hz, 1H), 5.48 (s, 2H), 4.44-4.33 (m, 2H), 4.28-4.19 (m, 1H), 4.15 (q, J=7.2 Hz, 2H), 3.28 (s, 3H), 2.69-2.60 (m, 1H), 2.42-2.33 (m, 1H), 1.39 (t, J=7.3 Hz, 3H). LC-MS $R_T$=5.45 min, m/z=460.2 $[M+H]^+$.

LCMS (2 to 98% acetonitrile in water+0.1% formic acid over 10 mins) retention time 5.45 min, ESI+ found [M+H]=460.2.

Example 705

Method GH5

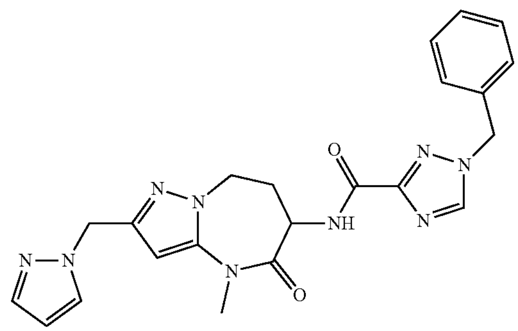 [SMILES: CN1C(=O)C(NC(=O)c2ncn(Cc3ccccc3)n2)CCn2nc(Cn3cccn3)cc21]

1-benzyl-N-[4-methyl-1-oxo-1-(pyrazol-1-ylmethyl)-7,8-dihydro-6H-pyrazolo[1,5-a][1,3]diazepin-6-yl]-1,2,4-triazole-3-carboxamide

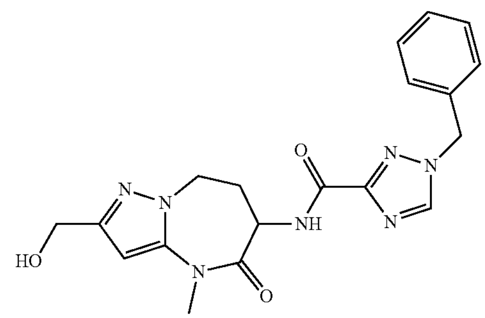 [SMILES: CN1C(=O)C(NC(=O)c2ncn(Cc3ccccc3)n2)CCn2nc(CO)cc21]

Step 1: 1-benzyl-N-(2-(hydroxymethyl)-4-methyl-5-oxo-5,6,7,8-tetrahydro-4H-pyrazolo[1,5-a][1,3]diazepin-6-yl)-1H-1,2,4-triazole-3-carboxamide To a solution of 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide (678 mg, 1.725 mmol, 1.0 equiv) in methanol (15 mL) cooled to 0° C. was added sodium borohydride (131 mg, 3.45 mmol, 2.0 equiv). The reaction mixture was warmed to RT and stirred 2 h. The reaction was quenched with 5% aqueous citric acid (50 mL) and extracted with dichloromethane (3×50 mL). The combined organics were dried over sodium sulfate, filtered and concentrated to dryness in vacuo. The resulting residue was purified by column chromatography (silica gel, 100-200 mesh, 0 to 15% methanol in dichloromethane) affording 1-benzyl-N-[2-(hydroxymethyl)-4-methyl-5-oxo-7,8-dihydro-6H-pyrazolo[1,5-a][1,3]diazepin-6-yl]-1,2,4-triazole-3-carboxamide (350 mg, 51% yield). LCMS $R_T$=0.97 min [2 min method], m/z=396 $[M+H]^+$.

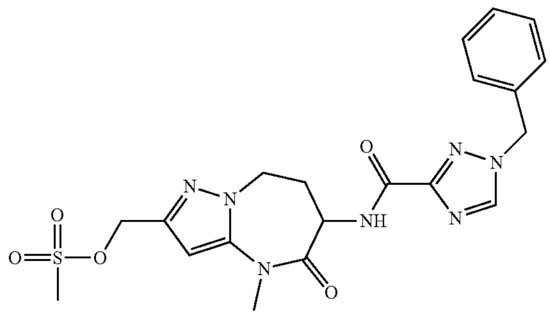 [SMILES: CN1C(=O)C(NC(=O)c2ncn(Cc3ccccc3)n2)CCn2nc(COS(C)(=O)=O)cc21]

Step 2: (6-(1-benzyl-1H-1,2,4-triazole-3-carboxamido)-4-methyl-5-oxo-5,6,7,8-tetrahydro-4H-pyrazolo[1,5-a][1,3]diazepin-2-yl)methyl methanesulfonate To a solution of 1-benzyl-N-[2-(hydroxymethyl)-4-methyl-5-oxo-7,8-dihydro-6H-pyrazolo[1,5-a][1,3]diazepin-6-yl]-1,2,4-triazole-3-carboxamide (350 mg, 0.885 mmol, 1.0 equiv) in dichloromethane (10 mL) cooled to 0° C. was added triethylamine (0.370 mL, 2.66 mmol, 3.0 equiv) and methanesulfonyl chloride (0.137 mL, 1.77 mmol, 2.0 equiv). The reaction mixture was allowed to warm slowly to RT over 1 h. The reaction was quenched with saturated aqueous sodium bicarbonate (50 mL) and extracted with dichloromethane (3×50 mL). The combined organics were washed with water and brine, dried over sodium sulfate and concentrated to dryness in vacuo affording (6-(1-benzyl-1H-1,2,4-triazole-3-carboxamido)-4-methyl-5-oxo-5,6,7,8-tetrahydro-4H-pyrazolo[1,5-a][1,3]diazepin-2-yl)methyl methanesulfonate (405 mg, 97% yield) which was used without further purification. LCMS $R_T$=1.13 min [2 min method], m/z=474 $[M+H]^+$.

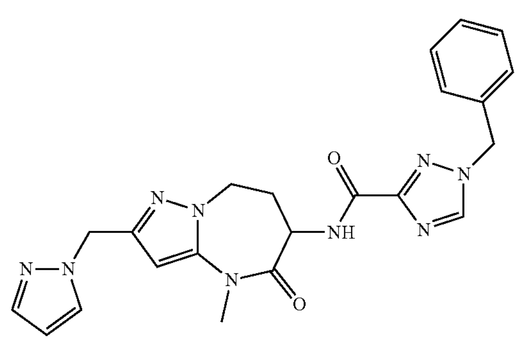 [SMILES: CN1C(=O)C(NC(=O)c2ncn(Cc3ccccc3)n2)CCn2nc(Cn3cccn3)cc21]

Step 3: 1-benzyl-N-[4-methyl-5-oxo-2-(pyrazol-1-ylmethyl)-7,8-dihydro-6H-pyrazolo[1,5-a][1,3]diazepin-6-yl]-1,2,4-triazole-3-carboxamide To a solution of (6-(1-benzyl-1H-1,2,4-triazole-3-carboxamido)-4-methyl-5-oxo-5,6,7,8-tetrahydro-4H-pyrazolo[1,5-a][1,3]diazepin-2-yl)methyl methanesulfonate (60 mg, 0.126 mmol, 1.0 equiv) in acetonitrile (1 mL) was added pyrazole (17 mg, 0.252 mmol, 2.0 equiv) and cesium carbonate (82 mg, 0.252 mmol, 2.0 equiv). The resulting mixture was stirred for 16 hr at RT. The mixture was then filtered through Celite and concentrated to dryness in vacuo. The resulting residue was purified by column chromatography (silica gel, 100-200 mesh, 0 to 10% methanol in dichloromethane) affording 1-benzyl-N-[4-methyl-5-oxo-2-(pyrazol-1-ylmethyl)-7,8-dihydro-6H-pyrazolo[1,5-a][1,3]diazepin-6-yl]-1,2,4-triazole-3-carboxamide (31 mg, 55% yield) as a white solid. 1H NMR (400 MHz, DMSO-d6) δ 8.81 (s, 1H), 8.53 (d, J=7.8 Hz, 1H), 7.78 (dd, J=2.3, 0.7 Hz, 1H), 7.44 (dd, J=1.9, 0.7 Hz, 1H), 7.41-7.27 (m, 5H), 6.25 (dd, J=2.3, 1.8 Hz, 1H), 6.21 (s, 1H), 5.48 (s, 2H), 5.32-5.20 (m, 2H), 4.38-4.25 (m, 2H), 4.16 (ddd, J=14.5, 12.6, 6.6 Hz, 1H), 3.20 (s, 3H), 2.65-2.53 (m, 1H), 2.42-2.30 (m, 1H). LCMS $R_T$=3.70 min [10 min method], m/z=446.2 $[M+H]^+$.

Example 706

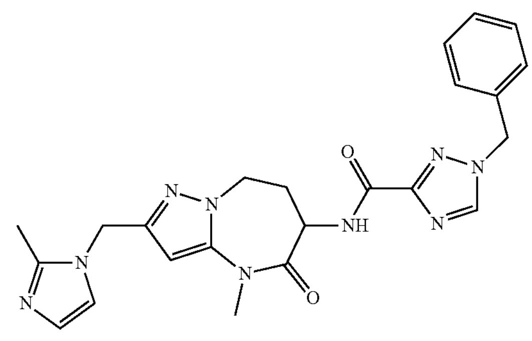 [SMILES: Cc1nccn1Cc1cc2n(n1)CCC(NC(=O)c1ncn(Cc3ccccc3)n1)C(=O)N2C]

1-benzyl-N-[4-methyl-2-[(2-methylimidazol-1-yl)methyl]-5-oxo-7,8-dihydro-6H-pyrazolo[1,5-a][1,3]diazepin-6-yl]-1,2,4-triazole-3-carboxamide The title compound was prepared from 2-methylimidazole according to Method GH5. Yield of final step: 37 mg, 64%, obtained as a white solid. 1H NMR (400 MHz, DMSO-d6) δ 8.81 (s, 1H), 8.53 (d, J=7.8 Hz, 1H), 7.44-7.25 (m, 5H), 7.08 (d, J=1.3 Hz, 1H), 6.71 (d, J=1.3 Hz, 1H), 6.23 (s, 1H), 5.48 (s, 2H), 5.12-4.96 (m, 2H), 4.39-4.23 (m, 2H), 4.16 (ddd, J=14.5, 12.6, 6.6 Hz, 1H), 3.20 (s, 3H), 2.68-2.52 (m, 1H), 2.44-2.34 (m, 1H), 2.31 (s, 3H).

LCMS RT=2.66 min [10 min method], m/z=460.2 $[M+H]^+$.

Example 707

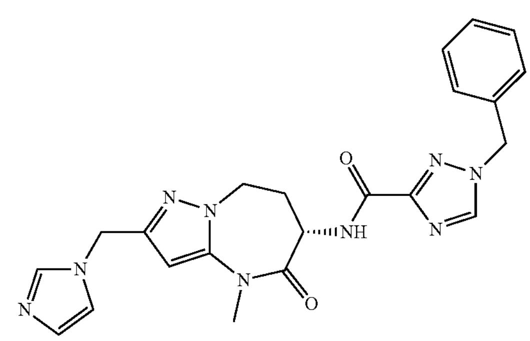 [SMILES: CN1C(=O)[C@@H](NC(=O)c2ncn(Cc3ccccc3)n2)CCn2nc(Cn3ccnc3)cc21]

(S)-1-benzyl-N-[2-(imidazol-1-ylmethyl)-4-methyl-5-oxo-7,8-dihydro-6H-pyrazolo[1,5-a][1, 3]diazepin-6-yl]-1,2,4-triazole-3-carboxamide The title compound was prepared from imidazole according to Method GH5 and chiral separation of the resulting racemate. Yield of final step: 12 mg, 22% (including the chiral separation), obtained as white solid. SFC conditions: Column: Phenomenex Lux Amylose-1, 50×4.6 mm I.D., 3 μm Mobile phase: A: CO2 B: Methanol (0.1% NH4OH) Isocratic: 35% B in 2.5 min Flow rate: 4 mL/min Column temperature: 40° C., BPR: 120 bar. Analytical SFC $R_T$(Amylose-1 column, 35% methanol+0.1% ammonium hydroxide isocratic elution, 2.5 min method): 0.63 min, 100% ee (First eluting enantiomer). 1H NMR (400 MHz, DMSO-d6) δ 8.81 (s, 1H), 8.53 (d, J=7.8 Hz, 1H), 7.70 (t, J=1.1 Hz, 1H), 7.42-7.26 (m, 5H), 7.19 (t, J=1.2 Hz, 1H), 6.89 (t, J=1.1 Hz, 1H), 6.29 (s, 1H), 5.48 (s, 2H), 5.20-5.07 (m, 2H), 4.37-4.25 (m, 2H), 4.17 (ddd, J=14.6, 12.7, 6.7 Hz, 1H), 3.22-3.19 (m, 3H), 2.65-2.54 (m, 1H), 2.42-2.31 (m, 1H). LCMS RT=2.58 min [10 min method], m/z=446.1 $[M+H]^+$.

Example 708

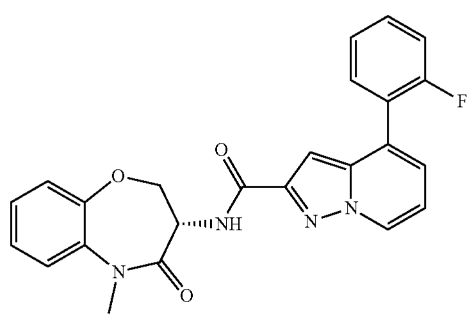 [SMILES: CN1C(=O)[C@@H](NC(=O)c2cc3c(-c4ccccc4F)cccn3n2)COc2ccccc21]

4-(2-fluorophenyl)-N-[(3S)-5-methyl-4-oxo-2,3-dihydro-1,5-benzoxazepin-3-yl]pyrazolo[1,5-a]pyridine-2-carboxamide The title compound was prepared from 2-fluorophenylboronic acid according to METHOD GH6. Yield of final step: 95 mg, 69%. 1H NMR (400 MHz, DMSO-d6) δ 8.83 (dt, J=7.0, 1.0 Hz, 1H), 8.52 (d, J=8.1 Hz, 1H), 7.64 (td, J=7.6, 1.8 Hz, 1H), 7.56 (dddd, J=8.4, 7.2, 5.3, 1.8 Hz, 1H), 7.53-7.48 (m, 1H), 7.46-7.36 (m, 3H), 7.36-7.26 (m, 2H), 7.26-7.23 (m, 1H), 7.19 (t, J=7.0 Hz, 1H), 6.80 (dd, J=2.0, 1.0 Hz, 1H), 4.91 (dt, J=11.6, 7.9 Hz, 1H), 4.59 (dd, J=11.6, 9.9 Hz, 1H), 4.44 (dd, J=9.9, 7.7 Hz, 1H), 3.33 (s, 3H). LCMS RT=5.64 min [10 min method], m/z=431.1 $[M+H]^+$.

Examples 709 and 710

Method GH8

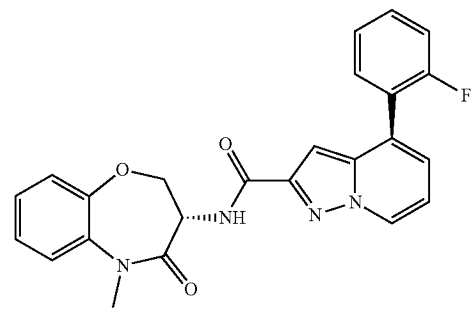

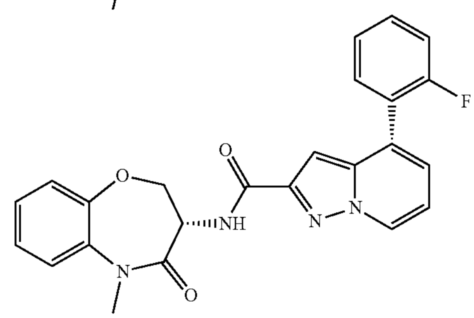

(4R)-4-(2-fluorophenyl)-N-[(3S)-5-methyl-4-oxo-2,3-dihydro-1,5-benzoxazepin-3-yl]-4,5, 6,7-tetrahydropyrazolo[1,5-a]pyridine-2-carboxamide and (4S)-4-(2-fluorophenyl)-N-[(3S)-5-methyl-4-oxo-2,3-dihydro-1,5-benzoxazepin-3-yl]-4,5, 6,7-tetrahydropyrazolo[1,5-a]pyridine-2-carboxamide To a solution of 4-(2-fluorophenyl)-N-[(3S)-5-methyl-4-oxo-2,3-dihydro-1,5-benzoxazepin-3-yl]pyrazolo[1,5-a]pyridine-2-carboxamide (88 mg, 0.20 mmol, 1.0 equiv) in acetic acid (2 mL) was added platinum(IV) oxide (5 mg, 0.020 mmol, 0.10 equiv). The reaction mixture was stirred under a balloon of hydrogen for 48 h. After this time, the mixture was filtered through Celite and concentrated to dryness in vacuo. The resulting residue was purified by chiral SFC (SFC conditions: Column: CHIRALPAK IC 50×4.6 mm I.D., 3 μm Mobile phase: A: CO2 B: Methanol (0.1% NH4OH) Isocratic: 45% B in 2.5 min Flow rate: 4 mL/min Column temperature: 40° C., BPR: 120 bar) affording arbitrarily assigned diastereomers (4R)-4-(2-fluorophenyl)-N-[(3S)-5-methyl-4-oxo-2,3-dihydro-1,5-benzoxazepin-3-yl]-4,5,6,7-tetrahydropyrazolo[1,5-a]pyridine-2-carboxamide (23 mg, 26%) and (4S)-4-(2-fluorophenyl)-N-[(3S)-5-methyl-4-oxo-2,3-dihydro-1,5-benzoxazepin-3-yl]-4,5,6,7-tetrahydropyrazolo[1,5-a]pyridine-2-carboxamide (17 mg, 19%).

Analytical data for the first eluting diastereomer (arbitrarily assigned S,R configuration): SFC $R_T$ (CHIRALPAK IC column, 45% methanol+0.1% ammonium hydroxide isocratic elution, 2.5 min method): 0.96 min, 100% ee: 1H NMR (400 MHz, DMSO-d6) δ 8.08 (d, J=8.1 Hz, 1H), 7.51-7.46 (m, 1H), 7.37-7.24 (m, 3H), 7.24-7.11 (m, 4H), 6.03 (d, J=1.0 Hz, 1H), 4.81 (dt, J=11.5, 7.9 Hz, 1H), 4.53 (dd, J=11.6, 9.9 Hz, 1H), 4.42 (dd, J=9.5, 4.7 Hz, 1H), 4.36 (dd, J=9.9, 7.7 Hz, 1H), 4.32-4.14 (m, 2H), 3.30 (s, 3H), 2.20-1.99 (m, 3H), 1.99-1.84 (m, 1H). LCMS $R_T$=5.70 min [10 min method], m/z=435.1 $[M+H]^+$.

Analytical data for the second eluting diastereomer (arbitrarily assigned S,S configuration): SFC $R_T$ 1.18 min, 99% ee. 1H NMR (400 MHz, DMSO-d6) δ 8.06 (d, J=8.1 Hz, 1H), 7.53-7.45 (m, 1H), 7.38-7.24 (m, 3H), 7.24-7.12 (m, 4H), 6.04 (d, J=0.9 Hz, 1H), 4.81 (dt, J=11.5, 7.9 Hz, 1H), 4.51 (dd, J=11.5, 9.9 Hz, 1H), 4.42 (dd, J=9.6, 4.8 Hz, 1H), 4.36 (dd, J=9.9, 7.7 Hz, 1H), 4.33-4.14 (m, 2H), 3.30 (s, 3H), 2.19-2.00 (m, 3H), 1.90 (q, J=10.1 Hz, 1H). LCMS $R_T$=5.70 min [10 min method], m/z=435.1 $[M+H]^+$.

Example 711

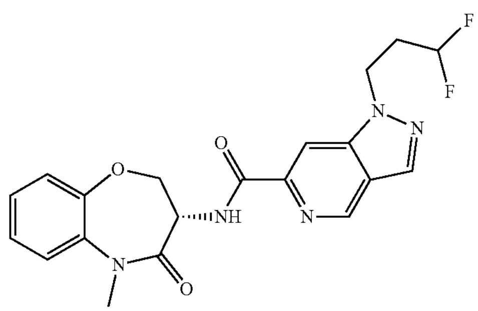 [SMILES: CN1C(=O)[C@@H](NC(=O)c2cc3c(cn2)cnn3CCC(F)F)COc2ccccc21]

1-(3,3-difluoropropyl)-N-[(3S)-5-methyl-4-oxo-2,3-dihydro-1,5-benzoxazepin-3-yl]pyrazolo[4,3-c]pyridine-6-carboxamide The title compound was prepared according to Method GH7 carrying on the isomer isopropyl 1-(3,3-difluoroallyl) pyrazolo[4,3-c]pyridine-6-carboxylate obtained in Step 2. Yield of final step: 59 mg, 70%. 1H NMR (400 MHz, DMSO-d6) δ 9.20 (d, J=1.1 Hz, 1H), 9.03 (d, J=7.8 Hz, 1H), 8.48 (d, J=1.0 Hz, 1H), 8.34 (t, J=1.1 Hz, 1H), 7.55-7.50 (m, 1H), 7.40-7.24 (m, 3H), 6.15 (tt, J=56.2, 4.4 Hz, 1H), 4.93 (dt, J=10.5, 8.2 Hz, 1H), 4.70 (t, J=6.8 Hz, 2H), 4.60-4.49 (m, 2H), 3.35 (s, 3H), 2.47-2.36 (m, 2H). LCMS RT=5.00 min [10 min method], m/z=416.1 $[M+H]^+$.

Example 712

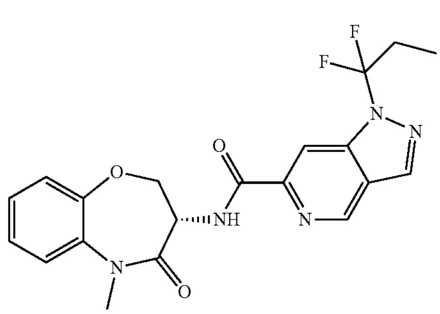 [SMILES: CCC(F)(F)n1ncc2cnc(C(=O)N[C@H]3COc4ccccc4N(C)C3=O)cc21]

1-(1,1-difluoropropyl)-N-[(3S)-5-methyl-4-oxo-2,3-dihydro-1,5-benzoxazepin-3-yl]pyrazolo[4,3-c]pyridine-6-carboxamide

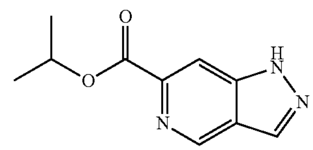

Step 1: isopropyl 1H-pyrazolo[4,3-c]pyridine-6-carboxylate

To a solution of 6-bromo-1H-pyrazolo[4,3-c]pyridine (3000 mg, 15.150 mmol, 1.0 equiv) in 2-propanol (20 mL) was added triethylamine (6.33 mL, 45 mmol, 3.0 equiv) and [1,1'-bis(diphenylphosphino)ferrocene]dichloropalladium (II) (1131 mg, 1.51 mmol, 0.10 equiv). The reaction vessel was pressurized with carbon monoxide to 120 psi. The reaction mixture was then heated to 80° C. for 16 h with stirring. After this time, the mixture was filtered through Celite and concentrated to dryness in vacuo. The resulting residue was purified by column chromatography (silica gel, 100-200 mesh, 0 to 10% isopropyl alcohol in dichloromethane) affording isopropyl 1H-pyrazolo[4,3-c]pyridine-6-carboxylate (1250 mg, 40% yield) as a red solid. LCMS RT=0.79 min [2 min method], m/z=206 $[M+H]^+$.

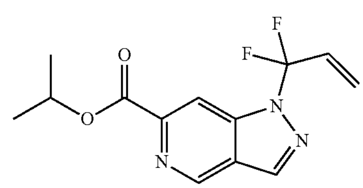

and

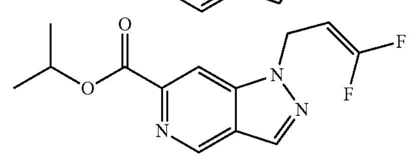

Step 2: isopropyl 1-(1,1-difluoroallyl)-1H-pyrazolo[4,3-c]pyridine-6-carboxylate and isopropyl 1-(3,3-difluoroallyl)-1H-pyrazolo[4,3-c]pyridine-6-carboxylate To a solution of isopropyl 1H-pyrazolo[4,3-c]pyridine-6-carboxylate (1250 mg, 6.09 mmol, 1.0 equiv) in acetonitrile (20 mL) was added cesium carbonate (3970 mg, 12.2 mmol, 2.0 equiv) and 3-bromo-3,3-difluoropropene (0.6481 mL, 1000 mg, 6.37117 mmol, 1.05 equiv). The reaction vessel was sealed and stirred at RT for 72 hr. The mixture was filtered through Celite and concentrated to dryness in vacuo. The resulting residue was purified by column chromatography (silica gel, 100-200 mesh, 0 to 100% isopropyl acetate in heptane) affording isopropyl 1-(1,1-difluoroallyl)pyrazolo[4,3-c]pyridine-6-carboxylate (first to elute, 170 mg, 10% yield) (LCMS RT=1.37 min [2 min method], m/z=282 [M+H]+) and isopropyl 1-(3,3-difluoroallyl)pyrazolo[4,3-c]pyridine-6-carboxylate (second to elute, 300 mg, 18% yield) (LCMS RT=1.19 min [2 min method], m/z=282 [M+H]+) as white solids.

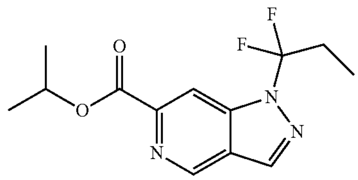 [SMILES: CCC(F)(F)n1ncc2cnc(C(=O)OC(C)C)cc21]

Step 3: isopropyl 1-(1,1-difluoropropyl)-1H-pyrazolo[4,3-c]pyridine-6-carboxylate To a solution of isopropyl 1-(1,1-difluoroallyl)pyrazolo[4,3-c]pyridine-6-carboxylate (170 mg, 0.6043 mmol, 1.0 equiv) in ethanol (3 mL) was added 10% palladium on carbon (64 mg, 0.06043 mmol, 0.10 equiv). The reaction vessel was placed under a balloon of hydrogen for 16 h with stirring. The reaction mixture was filtered through Celite and concentrated to dryness in vacuo. The resulting residue was purified by column chromatography (silica gel, 100-200 mesh, 0 to 60% isopropyl acetate in heptane) affording isopropyl 1-(1,1-difluoropropyl)-1H-pyrazolo[4,3-c]pyridine-6-carboxylate (109 mg, 64% yield) as a colorless oil. LCMS RT=1.44 min [2 min method], m/z=284 $[M+H]^+$.

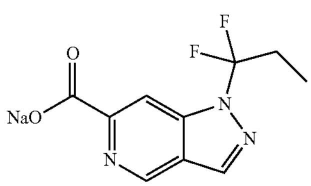

Step 4: sodium 1-(1,1-difluoropropyl)-1H-pyrazolo[4,3-c]pyridine-6-carboxylate

To a solution of isopropyl 1-(1,1-difluoropropyl)-1H-pyrazolo[4,3-c]pyridine-6-carboxylate (109 mg, 0.385 mmol, 1.0 equiv) in tetrahydrofuran (2 mL) was added 1M sodium hydroxide (0.42 mL, 0.42 mmol, 1.1 equiv). The reaction mixture was stirred for 2 h at 50° C. After this time, the mixture was concentrated to dryness in vacuo affording sodium 1-(1,1-difluoropropyl)-1H-pyrazolo[4,3-c]pyridine-6-carboxylate as a brown residue which was used directly in the next reaction. LCMS RT=0.94 min [2 min method], m/z=242 $[M+H]^+$.

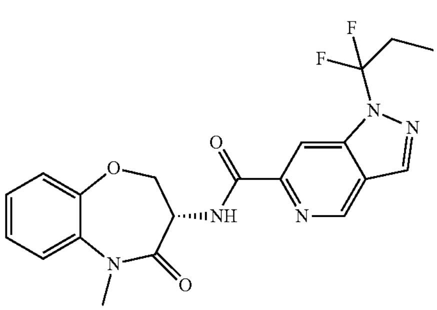 [SMILES: CCC(F)(F)n1ncc2cnc(C(=O)N[C@H]3COc4ccccc4N(C)C3=O)cc21]

Step 5: 1-(1,1-difluoropropyl)-N-[(3S)-5-methyl-4-oxo-2,3-dihydro-1,5-benzoxazepin-3-yl]pyrazolo[4,3-c]pyridine-6-carboxamide To a solution of [(3S)-5-methyl-4-oxo-2,3-dihydro-1,5-benzoxazepin-3-yl]ammonium chloride (88 mg, 0.385 mmol, 1.0 equiv) in N,N-dimethylformamide (2 mL) was added sodium 1-(1,1-difluoropropyl)-1H-pyrazolo[4,3-c]pyridine-6-carboxylate (101 mg, 0.385 mmol, 1.0 equiv), N,N-diisopropylethylamine (0.201 mL, 1.15 mmol, 3.0 equiv), and (7-Azabenzotriazol-1-yloxy)tripyrrolidinophosphonium hexafluorophosphate (251 mg, 0.46 mmol, 1.2 equiv). The reaction mixture was stirred for 16 h at RT. After this time, the crude mixture was loaded directly on a silica column and purified by chromatography (silica gel, 100-200 mesh, 0 to 80% isopropyl acetate in heptane) affording 1-(1,1-difluoropropyl)-N-[(3S)-5-methyl-4-oxo-2,3-dihydro-1,5-benzoxazepin-3-yl]pyrazolo[4,3-c]pyridine-6-carboxamide (101 mg, 63% yield). 1H NMR (400 MHz, DMSO-d6) δ 9.35 (d, J=1.1 Hz, 1H), 9.08 (d, J=7.8 Hz, 1H), 8.74 (d, J=0.9 Hz, 1H), 8.25 (p, J=1.3 Hz, 1H), 7.58-7.48 (m, 1H), 7.38-7.25 (m, 3H), 4.92 (dt, J=11.2, 7.8 Hz, 1H), 4.65-4.46 (m, 2H), 3.35 (s, 3H), 2.86-2.70 (m, 2H), 1.10 (t, J=7.4 Hz, 3H). LCMS RT=5.75 min [10 min method], m/z=416.1 $[M+H]^+$.

Example 713

Method GH6

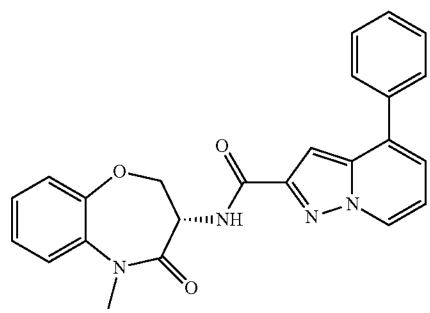 [SMILES: CN1C(=O)[C@@H](NC(=O)c2cc3c(-c4ccccc4)cccn3n2)COc2ccccc21]

4-phenyl-N-[(3S)-5-methyl-4-oxo-2,3-dihydro-1,5-benzoxazepin-3-yl]pyrazolo[1,5-a]pyri dine-2-carboxamide

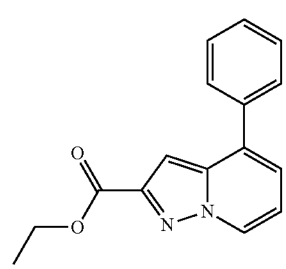 [SMILES: CCOC(=O)c1cc2c(-c3ccccc3)cccn2n1]

Step 1: ethyl 4-phenylpyrazolo[1,5-a]pyridine-2-carboxylate

To a solution of ethyl 4-bromopyrazolo[1,5-a]pyridine-2-carboxylate (200 mg, 0.74 mmol, 1.0 equiv) in toluene (8 ml) was added phenylboronic acid (136 mg, 1.11 mmol, 1.5 equiv), potassium phosphate tribasic (483 mg, 2.23 mmol, 3.0 equiv), and 2-(dicyclohexylphosphino)-2',4',6'-triisopropylbiphenyl (22 mg, 0.045 mmol, 0.06 equiv). The mixture was degassed for 15 mins with a nitrogen stream, then to it was added chloro(2-dicyclohexylphosphino-2',4',6'-triisopropyl-1,1'-biphenyl)[2-(2'-amino-1,1'-biphenyl)]palladium (II) (18 mg, 0.022 mmol, 0.03 equiv). The reaction vessel was sealed and heated to 80° C. with vigorous stirring for 1 h. The mixture was cooled to RT, filtered through Celite, and concentrated to dryness in vacuo. The resulting residue was purified by column chromatography (silica gel, 100-200 mesh, 0 to 70% isopropyl acetate in heptane) affording ethyl 4-phenylpyrazolo[1,5-a]pyridine-2-carboxylate (187 mg, 95% yield) as an off white solid. LCMS $R_T$=1.53 min [2 min method], m/z=267 $[M+H]^+$.

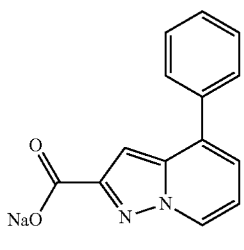

Step 2: sodium 4-phenylpyrazolo[1,5-a]pyridine-2-carboxylate

To a solution of ethyl 4-phenylpyrazolo[1,5-a]pyridine-2-carboxylate (187 mg, 0.70 mmol, 1.0 equiv) in tetrahydrofuran (4 mL) was added 1M sodium hydroxide (0.8427 mL, 0.8427 mmol, 1.2 equiv). The reaction mixture was stirred overnight at RT, then was concentrated to dryness in vacuo affording sodium 4-phenylpyrazolo[1,5-a]pyridine-2-carboxylate as a white solid which was used directly in the next step. LCMS $R_T$=1.22 min [2 min method], m/z=239 $[M+H]^+$.

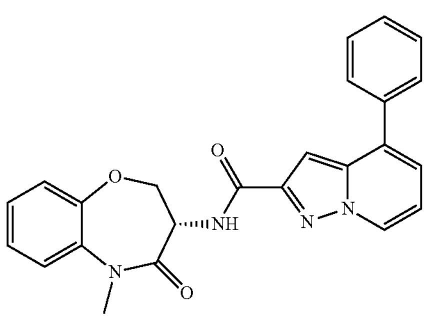 [SMILES: CN1C(=O)[C@@H](NC(=O)c2cc3c(-c4ccccc4)cccn3n2)COc2ccccc21]

Step 3: 4-phenyl-N-[(3S)-5-methyl-4-oxo-2,3-dihydro-1,5-benzoxazepin-3-yl]pyrazolo[1,5-a]pyridine-2-carboxamide To a solution of [(3S)-5-methyl-4-oxo-2,3-dihydro-1,5-benzoxazepin-3-yl]ammonium chloride (80 mg, 0.35 mmol, 1.0 equiv) in DMF (2 mL) was added sodium 4-phenylpyrazolo[1,5-a]pyridine-2-carboxylate (91 mg, 0.35 mmol, 1.0 equiv), N,N-diisopropylethylamine (0.18 mL, 1.1 mmol, 3.0 equiv), and (7-Azabenzotriazol-1-yloxy)tripyrrolidinophosphonium hexafluorophosphate (230 mg, 0.42 mmol, 1.2 equiv). The reaction mixture was stirred for 16 h at RT. After this time, the crude mixture was loaded directly on a silica column and purified by chromatography (silica gel, 100-200 mesh, 0 to 80% isopropyl acetate in heptane) affording 4-phenyl-N-[(3S)-5-methyl-4-oxo-2,3-dihydro-1,5-benzoxazepin-3-yl]pyrazolo[1,5-a]pyridine-2-carboxamide (76 mg, 53% yield). 1H NMR (400 MHz, DMSO-d6) δ 8.77 (dt, J=7.0, 1.0 Hz, 1H), 8.53 (d, J=8.1 Hz, 1H), 7.76-7.67 (m, 2H), 7.61-7.45 (m, 4H), 7.41 (dd, J=7.1, 0.9 Hz, 1H), 7.38-7.22 (m, 3H), 7.22-7.13 (m, 1H), 7.07 (d, J=1.0 Hz, 1H), 4.92 (dt, J=11.4, 7.9 Hz, 1H), 4.59 (dd, J=11.6, 9.9 Hz, 1H), 4.45 (dd, J=9.9, 7.7 Hz, 1H), 3.33 (s, 3H). LCMS RT=5.70 min [10 min method], m/z=413.1 $[M+H]^+$.

Example 714

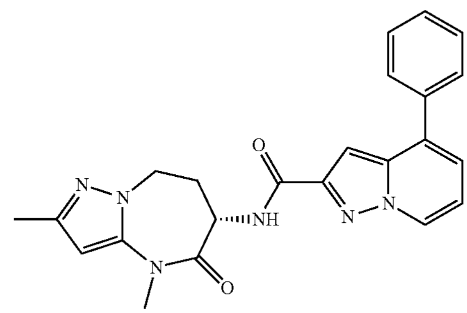 [SMILES: Cc1cc2n(n1)CC[C@H](NC(=O)c1cc3c(-c4ccccc4)cccn3n1)C(=O)N2C]

(S)—N-(2,4-dimethyl-5-oxo-5,6,7,8-tetrahydro-4H-pyrazolo[1,5-a][1,3]diazepin-6-yl)-4-phenylpyrazolo[1,5-a]pyridine-2-carboxamide The title compound was prepared from (S)-6-amino-2,4-dimethyl-7,8-dihydro-4H-pyrazolo[1,5-a][1,3]diazepin-5(6H)-one according to Method GH6. Yield of final step: 94%. 1H NMR (400 MHz, DMSO-d6) δ 8.76 (dt, J=7.0, 1.0 Hz, 1H), 8.58 (d, J=7.9 Hz, 1H), 7.77-7.69 (m, 2H), 7.62-7.53 (m, 2H), 7.53-7.45 (m, 1H), 7.40 (dd, J=7.1, 1.0 Hz, 1H), 7.17 (t, J=7.0 Hz, 1H), 7.08 (d, J=1.0 Hz, 1H), 6.14 (s, 1H), 4.41 (dt, J=11.6, 7.9 Hz, 1H), 4.29 (dd, J=14.5, 7.9 Hz, 1H), 4.20-4.05 (m, 1H), 3.23 (s, 3H), 2.68-2.56 (m, 1H), 2.41-2.30 (m, 1H), 2.18 (s, 3H). LCMS RT=4.86 min [10 min method], m/z=415.1 $[M+H]^+$.

Examples 715-718 Prepared According to Method GH_Chiral_1 (See, e.g. Examples 352 and 354)

Examples 719-722 Prepared According to Method GZ9 (See, e.g. Example 391)

Example 723

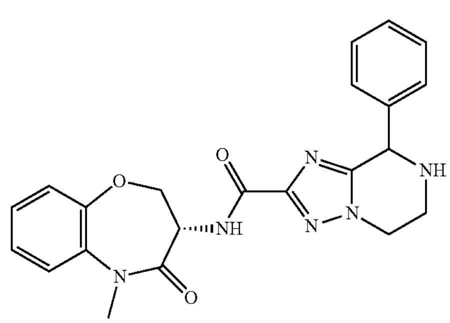 [SMILES: CN1C(=O)[C@@H](NC(=O)c2nc3n(n2)CCNC3c2ccccc2)COc2ccccc21]

N-[(3S)-5-methyl-4-oxo-2,3-dihydro-1,5-benzoxazepin-3-yl]-8-phenyl-5,6,7,8-tetrahydro-[1,2,4]triazolo[1,5-a]pyrazine-2-carboxamide Method GZ6. $^1$H NMR (400 MHz, DMSO-$d_6$) δ 8.34 (dd, J=8.1, 1.9 Hz, 1H), 7.49 (dt, J=7.5, 1.5 Hz, 1H), 7.44-7.11 (m, 9H), 5.20 (t, J=5.0 Hz, 1H), 4.91-4.75 (m, 1H), 4.56 (ddd, J=11.5, 9.9, 4.1 Hz, 1H), 4.37 (ddd, J=9.9, 7.6, 6.0 Hz, 1H), 4.32-4.15 (m, 2H), 3.37 (q, J=5.3 Hz, 1H), 3.32-3.11 (m, 4H). LCMS RT=3.26 min [10 min method], m/z=419.1 $[M+H]^+$.

Example 724

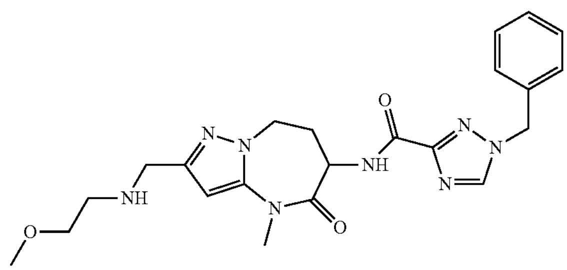 [SMILES: COCCNCc1cc2n(n1)CCC(NC(=O)c1ncn(Cc3ccccc3)n1)C(=O)N2C]

1-benzyl-N-[2-[(2-methoxyethylamino)methyl]-4-methyl-5-oxo-7,8-dihydro-6H-pyrazolo[1,5-a][1,3]diazepin-6-yl]-1,2,4-triazole-3-carboxamide Method GZ9. $^1$H NMR (400 MHz, DMSO-d6) δ 8.82 (s, 1H), 8.51 (d, J=7.8 Hz, 1H), 7.43-7.26 (m, 5H), 6.26 (s, 1H), 5.48 (s, 2H), 4.31 (m, 2H), 4.21-4.07 (m, 1H), 3.66 (d, J=2.1 Hz, 2H), 3.46-3.31 (m, 2H), 3.23 (s, 6H), 2.72 (t, J=5.7 Hz, 2H), 2.58 (m, 1H), 2.41-2.28 (m, 1H). LCMS: m/z=419.1 $[M+H]^+$.

Example 725

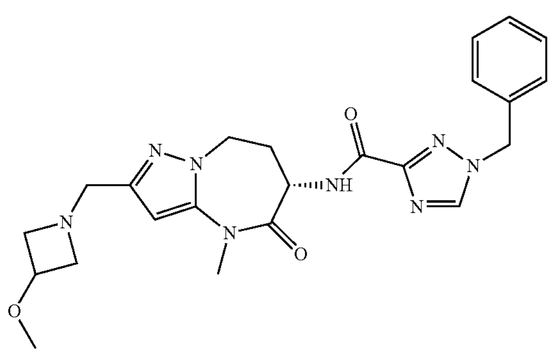 [SMILES: COC1CN(Cc2cc3n(n2)CC[C@H](NC(=O)c2ncn(Cc4ccccc4)n2)C(=O)N3C)C1]

(S)-1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide Method GZ9. $^1$H 1H NMR (400 MHz, DMSO-d6) δ 8.81 (s, 1H), 8.51 (d, J=7.7 Hz, 1H), 7.42-7.26 (m, 5H), 6.21 (s, 1H), 5.48 (s, 2H), 4.35-4.23 (m, 2H), 4.13 (m, 1H), 3.94 (p, J=5.8 Hz, 1H), 3.57-3.32 (m, 4H), 3.18 (ds, 6H), 2.86 (m, 2H), 2.58 (m, 1H), 2.41-2.28 (m, 1H). LCMS: m/z=465.2.

Example 726

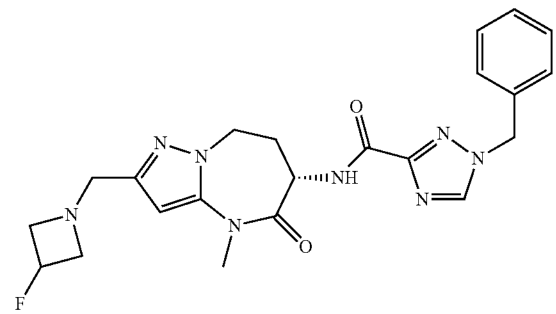 [SMILES: CN1C(=O)[C@@H](NC(=O)c2ncn(Cc3ccccc3)n2)CCn2nc(CN3CC(F)C3)cc21]

(S)-1-benzyl-N-(2-((3-fluoroazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide Method GZ9. $^1$H NMR (400 MHz, DMSO-$d_6$) δ 8.81 (s, 1H), 8.52 (d, J=7.8 Hz, 1H), 7.42-7.26 (m, 5H), 6.23 (s, 1H), 5.48 (s, 2H), 5.26-5.01 (m, 1H), 4.35-4.23 (m, 2H), 4.14 (m, 1H), 3.63-3.50 (m, 4H), 3.27-3.06 (m, 5H), 2.58 (m, 1H), 2.41-2.28 (m, 1H). LCMS: m/z=453.2.

Example 727

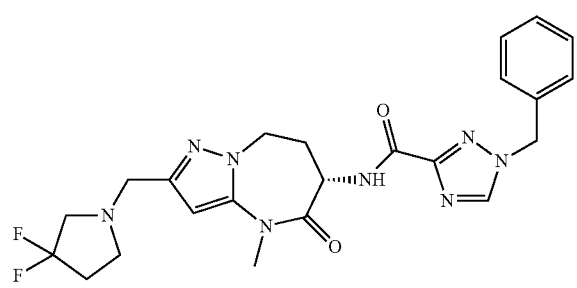 [SMILES: CN1C(=O)[C@@H](NC(=O)c2ncn(Cc3ccccc3)n2)CCn2nc(CN3CCC(F)(F)C3)cc21]

(S)-1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide 1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide was further purified by chiral SFC (Cellulose-1; 150×21.2 mm, 5 um; 35% methanol isocratic elution with Carbon Dioxide) affording arbitrarily assigned (S)-1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide (25.2 mg, 34.7%) as a white solid:

Analytical data for (S)-1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide: SFC $R_T$ (Cellulose-1, 25% methanol+0.1% ammonium hydroxide isocratic elution with Carbon Dioxide, 2.5 min method): 0.876 min, 100% purity, 100% ee. $^1$H NMR (400 MHz, DMSO-$d_6$) δ 8.81 (s, 1H), 8.52 (d, J=7.8 Hz, 1H), 7.42-7.26 (m, 5H), 6.28 (s, 1H), 5.48 (s, 2H), 4.31 (qd, J=7.9, 2.4 Hz, 2H), 4.15 (ddd, J=14.5, 12.6, 6.6H, 1H), 3.57 (q, J=13.4 Hz, 2H), 3.23 (s, 3H), 2.91 (t, J=13.4 Hz, 2H), 2.73 (t, J=7.0 Hz, 2H), 2.67-2.54 (m, 1H), 2.43-2.10 (m, 3H). LC-MS $R_T$=2.86 min, m/z=485.2 $(M+H)^+$.

LCMS (5 to 95% acetonitrile in water+0.1% formic acid over 10 mins) retention time 2.86 min, ESI+ found [M+H]=485.2.

Example 728

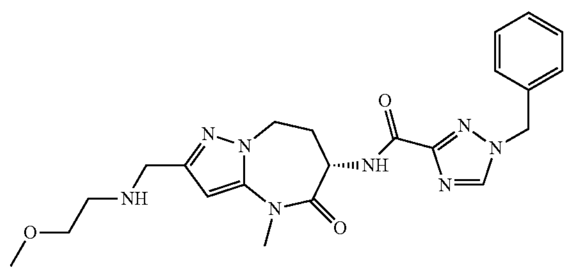 [SMILES: COCCNCc1cc2n(n1)CC[C@H](NC(=O)c1ncn(Cc3ccccc3)n1)C(=O)N2C]

(S)-1-benzyl-N-(2-(((2-methoxyethyl)amino)methyl)-4-methyl-5-oxo-5,6,7,8-tetrahydro-4H-pyrazolo[1,5-a][1,3]diazepin-6-yl)-1H-1,2,4-triazole-3-carboxamide 1-benzyl-N-(2-(((2-methoxyethyl)amino)methyl)-4-methyl-5-oxo-5, 6,7,8-tetrahydro-4H-pyrazolo[1,5-a][1,3]diazepin-6-yl)-1H-1,2,4-triazole-3-carboxamide was further purified by chiral SFC (Cellulose-1; 150×21.2 mm, 5 um; 30% methanol isocratic elution with Carbon Dioxide) affording (S)-1-benzyl-N-(2-(((2-methoxyethyl)amino)methyl)-4-methyl-5-oxo-5,6,7,8-tetrahydro-4H-pyrazolo[1,5-a][1,3]diazepin-6-yl)-1H-1,2,4-triazole-3-carboxamide (7.4 mg, 18.5%) as a white solid:

Analytical data for (S)-1-benzyl-N-(2-(((2-methoxyethyl)amino)methyl)-4-methyl-5-oxo-5,6,7,8-tetrahydro-4H-pyrazolo[1,5-a][1,3]diazepin-6-yl)-1H-1,2,4-triazole-3-carboxamide: SFC $R_T$ (Cellulose-1, 25% methanol+0.1% ammonium hydroxide isocratic elution with Carbon Dioxide, 2.5 min method): 0.805 min, 99.7% purity, 99.4% ee: $^1$H NMR (400 MHz, DMSO-d6) δ 8.82 (s, 1H), 8.51 (d, J=7.8 Hz, 1H), 7.43-7.26 (m, 5H), 6.26 (s, 1H), 5.48 (s, 2H), 4.31 (m, 2H), 4.21-4.07 (m, 1H), 3.66 (d, J=2.1 Hz, 2H), 3.46-3.31 (m, 2H), 3.23 (s, 6H), 2.72 (t, J=5.7 Hz, 2H), 2.58 (m, 1H), 2.41-2.28 (m, 1H). LC-MS $R_T$=2.65 min, m/z=453.2 $(M+H)^+$. LCMS (5 to 95% acetonitrile in water+0.1% formic acid over 10 mins) retention time 2.65 min, ESI+ found [M+H]=453.2.

Example 729

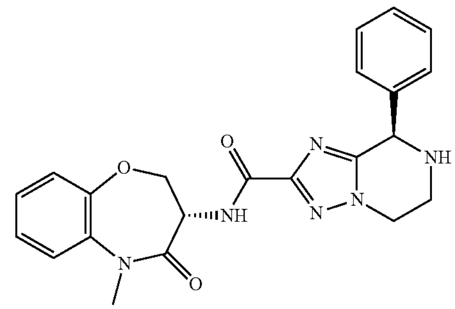 [SMILES: CN1C(=O)[C@@H](NC(=O)c2nc3n(n2)CCN[C@@H]3c2ccccc2)COc2ccccc21]

(8R)—N-[(3S)-5-methyl-4-oxo-2,3-dihydro-1,5-benzoxazepin-3-yl]-8-phenyl-5,6,7,8-tetrahydr o-[1,2,4]triazolo[1,5-a]pyrazine-2-carboxamide Further purification of Example 723. $^1$H NMR (400 MHz, DMSO-d6) δ 8.34 (d, J=8.0 Hz, 1H), 7.49 (dd, J=7.6, 1.9 Hz, 1H), 7.42-7.18 (m, 9H), 5.20 (d, J=5.3 Hz, 1H), 4.81 (dt, J=11.4, 7.8 Hz, 1H), 4.56 (dd, J=11.6, 9.8 Hz, 1H), 4.36 (dd, J=9.9, 7.7 Hz, 1H), 4.32-4.15 (m, 2H), 3.37 (q, J=5.1 Hz, 1H), 3.32-3.11 (m, 4H). LCMS: m/z=419.1 (3.26 min).

Example 730

Method GZ17

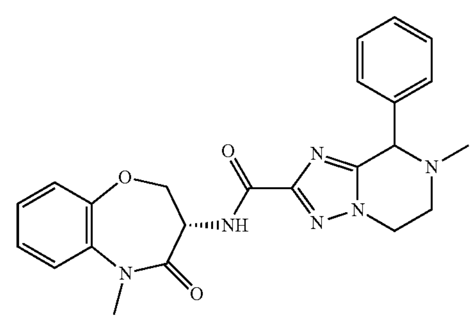 [SMILES: CN1C(=O)[C@@H](NC(=O)c2nc3n(n2)CCN(C)C3c2ccccc2)COc2ccccc21]

7-methyl-N—((S)-5-methyl-4-oxo-2,3,4,5-tetrahydrobenzo[b][1,4]oxazepin-3-yl)-8-phenyl-5,6,7,8-tetrahydro-[1,2,4]triazolo[1,5-a]pyrazine-2-carboxamide

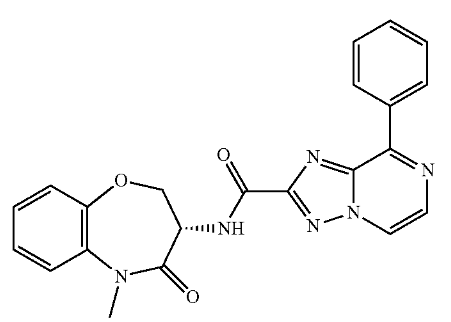 [SMILES: CN1C(=O)[C@@H](NC(=O)c2nc3c(-c4ccccc4)nccn3n2)COc2ccccc21]

Step 1: (S)—N-(5-methyl-4-oxo-2,3,4,5-tetrahydrobenzo[b][1,4]oxazepin-3-yl)-8-phenyl-[1,2,4]triazolo[1,5-a]pyrazine-2-carboxamide (S)—N-(5-methyl-4-oxo-2,3,4,5-tetrahydrobenzo[b][1,4]oxazepin-3-yl)-8-phenyl-[1,2,4]triazol o[1,5-a]pyrazine-2-carboxamide was prepared from (S)-3-amino-5-methyl-2,3-dihydrobenzo[b][1,4]oxazepin-4(5H)-one and 3-phenylpyrazin-2-amine according to Method GZ5. The residue was purified by preparative RP-HPLC (20-60% acetonitrile in water+0.1% formic acid). Yield of final step: 35.5 mg, 22.9%. $^{1}$H NMR (400 MHz, DMSO-d6) δ 9.15-9.03 (m, 2H), 8.84-8.75 (m, 2H), 8.47 (d, J=4.5 Hz, 1H), 7.70-7.58 (m, 3H), 7.55 (dd, J=7.6, 1.9 Hz, 1H), 7.40-7.23 (m, 3H), 4.98 (dt, J=11.5, 7.8 Hz, 1H), 4.73 (dd, J=11.6, 9.8 Hz, 1H), 4.51 (dd, J=9.8, 7.7 Hz, 1H), 3.35 (s, 3H). LC-MS $R_T$=5.04 min, m/z=415.1 $(M+H)^+$. LCMS (5 to 95% acetonitrile in water+0.1% formic acid over 10 mins) retention time 5.04 min, ESI+ found [M+H]=415.1

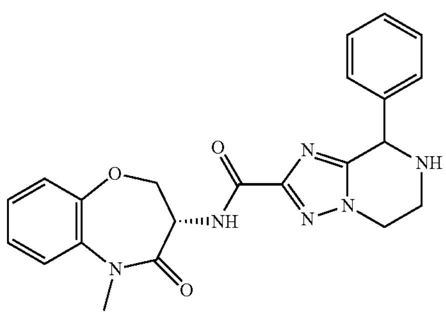 [SMILES: CN1C(=O)[C@@H](NC(=O)c2nc3n(n2)CCNC3c2ccccc2)COc2ccccc21]

Step 2: N—((S)-5-methyl-4-oxo-2,3,4,5-tetrahydrobenzo[b][1,4]oxazepin-3-yl)-8-phenyl-5,6,7,8-tetrahydro-[1,2,4]triazolo[1,5-a]pyrazine-2-carboxamide To a solution of (S)—N-(5-methyl-4-oxo-2,3,4,5-tetrahydrobenzo[b][1,4]oxazepin-3-yl)-8-phenyl-[1,2,4]triazol o[1,5-a]pyrazine-2-carboxamide (368 mg, 0.88 mmol) in tetrahydrofuran (20 mL) and methanol (20 mL) was added platinum(iv) oxide (20.2 mg, 0.088 mmol). The reaction mixture stirred under a balloon of hydrogen gas for 16 h at RT, then was filtered through Celite and concentrated to dryness in vacuo. The crude residue was purified by flash column chromatography (silica gel, 0% to 15% methanol in dichloromethane) to afford N—((S)-5-methyl-4-oxo-2,3,4,5-tetrahydrobenzo[b][1,4]oxazepin-3-yl)-8-phenyl-5,6,7,8-tetra hydro-[1,2,4]triazolo[1,5-a]pyrazine-2-carboxamide (216 mg, 52% Yield) as a tan solid: $^{1}$H NMR (400 MHz, DMSO-$d_6$) δ 8.34 (dd, J=8.1, 1.9 Hz, 1H), 7.49 (dt, J=7.5, 1.5 Hz, 1H), 7.44-7.11 (m, 9H), 5.20 (t, J=5.0 Hz, 1H), 4.91-4.75 (m, 1H), 4.56 (ddd, J=11.5, 9.9, 4.1 Hz, 1H), 4.37 (ddd, J=9.9, 7.6, 6.0 Hz, 1H), 4.32-4.15 (m, 2H), 3.37 (q, J=5.3 Hz, 1H), 3.32-3.11 (m, 4H). LC-MS $R_T$=3.26 min, m/z=419.1 $(M+H)^+$. LCMS (5 to 95% acetonitrile in water+0.1% formic acid over 10 mins) retention time 3.26 min, ESI+ found [M+H]=419.1

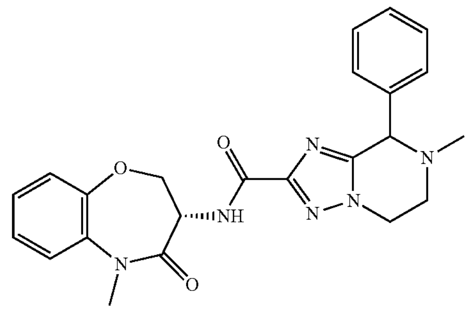 [SMILES: CN1C(=O)[C@@H](NC(=O)c2nc3n(n2)CCN(C)C3c2ccccc2)COc2ccccc21]

Step 3: 7-methyl-N—((S)-5-methyl-4-oxo-2,3,4,5-tetrahydrobenzo[b][1,4]oxazepin-3-yl)-8-phenyl-5,6,7,8-tetrahydro-[1,2,4]triazolo[1,5-a]pyrazine-2-carboxamide To a solution of N—((S)-5-methyl-4-oxo-2,3,4,5-tetrahydrobenzo[b][1,4]oxazepin-3-yl)-8-phenyl-5,6,7,8-tetra hydro-[1,2,4]triazolo[1,5-a]pyrazine-2-carboxamide (83 mg, 0.198 mmol) in dichloroethane (1.5 mL) was added formaldehyde (13.31 mol/L) in water (0.05 mL, 0.595 mmol), then added acetic acid (0.04 mL, 0.595 mmol), then added sodium triacetoxyborohydride (168 mg, 0.793 mmol) and allowed to stir for overnight. The reaction mixture was made basic with the addition of saturated aq. $NaHCO_3$ solution (10 mL) and stirring for 20 min. Extracted with DCM (3×30 mL). The combined organics were dried over sodium sulfate, filtered, and concentrated to dryness in vacuo, The crude residue was further purified by preparative RP-HPLC (20-60% acetonitrile in water+0.1% formic acid, column: Gemini-NX C18 10 um, 50×30 mm) to afford 7-methyl-N—((S)-5-methyl-4-oxo-2,3,4,5-tetrahydrobenzo[b][1,4]oxazepin-3-yl)-8-phenyl-5,6,7,8-tetrahydro-[1,2,4]triazolo[1,5-a]pyrazine-2-carboxamide (14.7 mg, 17%) as a tan solid. $^{1}$H NMR (400 MHz, DMSO-d6) δ 8.28 (dd, J=8.0, 5.5 Hz, 1H), 7.48 (dt, J=7.6, 2.0 Hz, 1H), 7.42-7.17 (m, 9H), 4.85-4.72 (m, 1H), 4.61-4.49 (m, 2H), 4.45-4.27 (m, 3H), 3.28 (d, J=1.9 Hz, 4H), 3.00-2.87 (m, 1H), 2.21 (s, 3H). LC-MS $R_T$=4.29 min, m/z=433.2 $(M+H)^+$.

LCMS (5 to 95% acetonitrile in water+0.1% formic acid over 10 mins) retention time 4.29 min, ESI+ found [M+H]=433.2.

Example 731

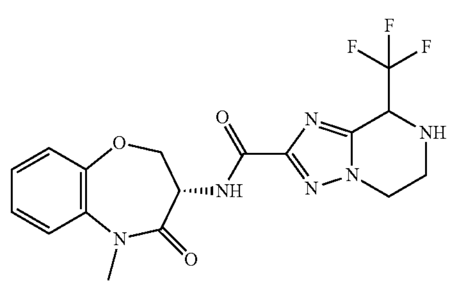 [SMILES: CN1C(=O)[C@@H](NC(=O)c2nc3n(n2)CCNC3C(F)(F)F)COc2ccccc21]

N—((S)-5-methyl-4-oxo-2,3,4,5-tetrahydrobenzo[b][1,4]oxazepin-3-yl)-8-(trifluoromethyl)-5,6,7,8-tetrahydro-[1,2,4]triazolo[1,5-a]pyrazine-2-carboxamide N—((S)-5-methyl-4-oxo-2,3,4,5-tetrahydrobenzo[b][1,4]oxazepin-3-yl)-8-(trifluoromethyl)-5, 6,7,8-tetrahydro-[1,2, 4]triazolo[1,5-a]pyrazine-2-carboxamide was prepared from 3-(trifluoromethyl)pyrazin-2-amine according to Method GZ6. Yield of final step: 6 mg, 86%, isolated as a white solid. $^1$H NMR (400 MHz, DMSO-$d_6$) δ 8.44 (dd, J=7.9, 2.3 Hz, 1H), 7.57-7.45 (m, 1H), 7.39-7.16 (m, 4H), 5.16-4.99 (m, 1H), 4.85 (dtd, J=11.5, 7.8, 3.8 Hz, 1H), 4.60 (dt, J=11.5, 9.7 Hz, 1H), 4.43 (ddd, J=9.9, 7.6, 6.8 Hz, 1H), 4.25 (m, 1H), 4.21-4.04 (m, 1H), 3.68 (m, 1H), 3.31 (s, 3H), 3.27-3.19 (m, 1H). LC-MS $R_T$=3.87 min, m/z=411.1 $(M+H)^+$. LCMS (5 to 95% acetonitrile in water+0.1% formic acid over 10 mins) retention time 3.87 min, ESI+ found [M+H]=411.1

Example 732

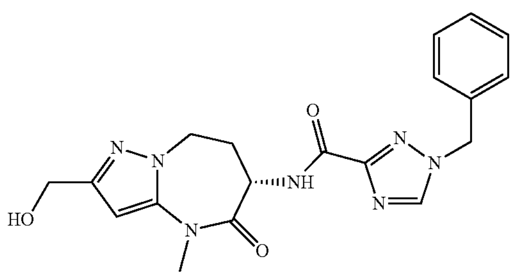 [SMILES: CN1C(=O)[C@@H](NC(=O)c2ncn(Cc3ccccc3)n2)CCn2nc(CO)cc21]

(S)-1-benzyl-N-(2-(hydroxymethyl)-4-methyl-5-oxo-5,6,7,8-tetrahydro-4H-pyrazolo[1,5-a][1,3]diazepin-6-yl)-1H-1,2,4-triazole-3-carboxamide 1-benzyl-N-(2-(hydroxymethyl)-4-methyl-5-oxo-5,6,7,8-tetrahydro-4H-pyrazolo[1,5-a][1,3]diazepin-6-yl)-1H-1,2,4-triazole-3-carboxamide was further purified by chiral SFC (Chiralpak AD, 150×21.2 mm, 30% methanol isocratic elution with Carbon Dioxide) affording (S)-1-benzyl-N-(2-(hydroxymethyl)-4-methyl-5-oxo-5,6,7,8-tetrahydro-4H-pyrazolo[1,5-a][1,3]diazepin-6-yl)-1H-1,2,4-triazole-3-carboxamide (11.6 mg, 46%) as a white solid.

Analytical data (S)-1-benzyl-N-(2-(hydroxymethyl)-4-methyl-5-oxo-5,6,7,8-tetrahydro-4H-pyrazolo[1,5-a][1,3]diazepin-6-yl)-1H-1,2,4-triazole-3-carboxamide: SFC $R_T$ (Chiralpak AD, 30% methanol+0.1% ammonium hydroxide isocratic elution with Carbon Dioxide, 2.5 min method): 0.824 min, 99.8% purity, 99.6% ee: $^1$H NMR (400 MHz, DMSO-d6) δ 8.82 (s, 1H), 8.51 (d, J=7.8 Hz, 1H), 7.42-7.26 (m, 5H), 6.28 (s, 1H), 5.48 (s, 2H), 5.10 (t, J=5.8 Hz, 1H), 4.45-4.24 (m, 4H), 4.15 (m, 1H), 3.24 (s, 3H), 2.58 (m, 1H), 2.41-2.28 (m, 1H). LC-MS $R_T$=3.14 min, m/z=396.1 $(M+H)^+$. LCMS (5 to 95% acetonitrile in water+0.1% formic acid over 10 mins) retention time 3.14 min, ESI+ found [M+H]=396.1.

Example 733

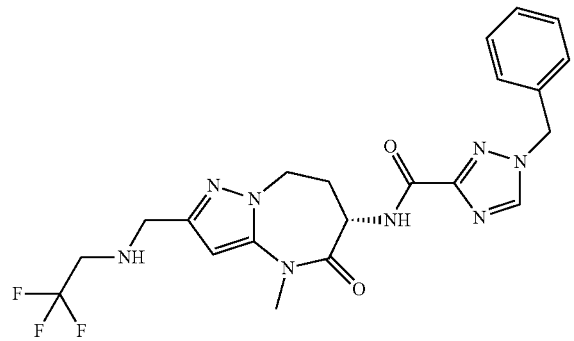 [SMILES: CN1C(=O)[C@@H](NC(=O)c2ncn(Cc3ccccc3)n2)CCn2nc(CNCC(F)(F)F)cc21]

(S)-1-benzyl-N-(4-methyl-5-oxo-2-(((2,2,2-trifluoroethyl)amino)methyl)-5,6,7,8-tetrahydro-4H-pyrazolo[1,5-a][1,3]diazepin-6-yl)-1H-1,2,4-triazole-3-carboxamide 1-benzyl-N-(4-methyl-5-oxo-2-(((2,2,2-trifluoroethyl)amino)methyl)-5,6,7,8-tetrahydro-4H-pyrazolo[1,5-a][1,3]diazepin-6-yl)-1H-1,2,4-triazole-3-carboxamide was prepared from 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide and 2,2,2-trifluoroethanamine; hydrochloride according to Method GZ8. The crude residue was further purified by chiral SFC (Chiralpak OX; 150×21.2 mm, 5 um; 40% methanol isocratic elution with Carbon Dioxide) affording (S)-1-benzyl-N-(4-methyl-5-oxo-2-(((2,2-trifluoroethyl)amino)methyl)-5,6,7,8-tetrahydro-4H-pyrazolo[1,5-a][1,3]diazepin-6-yl)-1H-1,2,4-triazole-3-carboxamide (5 mg, 8.3%) as a white solid:

Analytical data for (S)-1-benzyl-N-(4-methyl-5-oxo-2-(((2,2,2-trifluoroethyl)amino)methyl)-5,6,7,8-tetrahydro-4H-pyrazolo[1,5-a][1,3]diazepin-6-yl)-1H-1,2,4-triazole-3-carboxamide: SFC $R_T$ (Chiralpak OX, 35% methanol+0.1% ammonium hydroxide isocratic elution with Carbon Dioxide, 2.5 min method): 1.177 min, 100% purity, 100% ee. $^1$H NMR (400 MHz, DMSO-d6) δ 8.82 (s, 1H), 8.52 (d, J=7.8 Hz, 1H), 7.42-7.26 (m, 5H), 6.28 (s, 1H), 5.48 (s, 2H), 4.31 (m, 2H), 4.15 (m, 1H), 3.79-3.64 (m, 2H), 3.33-3.15 (m, 4H), 2.77 (p, J=6.9 Hz, 1H), 2.59 (m, 1H), 2.50-2.29 (m, 1H). LCMS $R_T$=3.18 min, m/z=477.2 $(M+H)^+$.

LCMS (5 to 95% acetonitrile in water+0.1% formic acid over 10 mins) retention time 3.18 min, ESI+ found [M+H]=477.2.

Examples 734 and 735

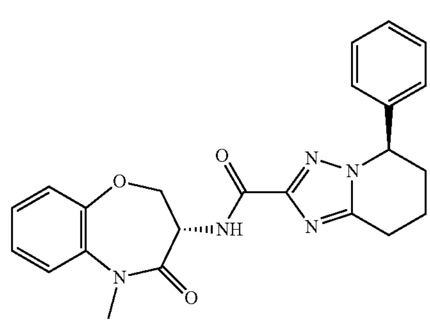

-continued

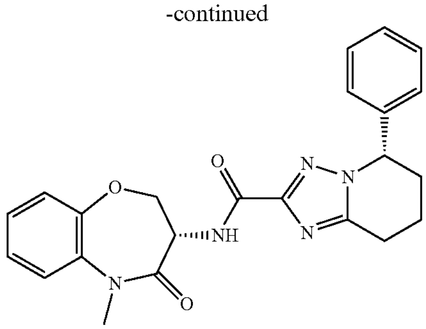

(R)—N—((S)-5-methyl-4-oxo-2,3,4,5-tetrahydrobenzo[b][1,4]oxazepin-3-yl)-5-phenyl-5,6,7, 8-tetrahydro-[1,2,4]triazolo[1,5-a]pyridine-2-carboxamide and (S)—N—((S)-5-methyl-4-oxo-2,3,4,5-tetrahydrobenzo[b][1,4]oxazepin-3-yl)-5-phenyl-5,6,7, 8-tetrahydro-[1,2,4]triazolo[1,5-a]pyridine-2-carboxamide (1:1)

N—((S)-5-methyl-4-oxo-2,3,4,5-tetrahydrobenzo[b][1,4]oxazepin-3-yl)-5-phenyl-5,6,7,8-tetra hydro-[1,2,4]triazolo[1,5-a]pyridine-2-carboxamide was further purified by chiral SFC (Cellulose-3; 151×21.2 mm, 5 um; 15% methanol isocratic elution with Carbon Dioxide) affording arbitrarily assigned diastereomers (R)—N—((S)-5-methyl-4-oxo-2,3,4,5-tetrahydrobenzo[b][1,4]oxazepin-3-yl)-5-phenyl-5,6,7,8-tetrahydro-[1,2,4]triazolo[1,5-a]pyridine-2-carboxamide (14.7 mg, 9.4%) and (S)—N—((S)-5-methyl-4-oxo-2,3,4,5-tetrahydrobenzo[b][1,4]oxazepin-3-yl)-5-phenyl-5,6,7,8-tetrahydro-[1,2,4]triazolo[1,5-a]pyridine-2-carboxamide (10 mg, 6.4%) as white solids:

Analytical data for the first eluting diastereomer (arbitrarily assigned R, S configuration): SFC $R_T$ (Cellulose-3, 15% methanol+0.1% ammonium hydroxide isocratic elution with Carbon Dioxide, 2.5 min method): 0.603 min, 100% purity, 100% ee: $^1$H NMR (400 MHz, DMSO-d6) δ 8.40 (d, J=7.9 Hz, 1H), 7.49 (dd, J=7.6, 2.0 Hz, 1H), 7.40-7.18 (m, 6H), 7.09-7.01 (m, 2H), 5.57 (t, J=5.9 Hz, 1H), 4.80 (dt, J=11.5, 7.8 Hz, 1H), 4.57 (dd, J=11.6, 9.9 Hz, 1H), 4.38 (dd, J=9.9, 7.6 Hz, 1H), 3.30 (s, 3H), 3.11-2.89 (m, 2H), 2.49-2.32 (m, 1H), 2.11-1.98 (m, 1H), 1.87 (h, J=5.9, 5.4 Hz, 2H). LCMS $R_T$=11.60 min, m/z=418.2 $(M+H)^+$.

LCMS (5 to 95% acetonitrile in water+0.1% formic acid over 30 mins) retention time 11.60 min, ESI+ found [M+H]=418.2

Analytical data for the second eluting diastereomer (arbitrarily assigned S, S configuration): SFC $R_T$ (Cellulose-3, 15% methanol+0.1% ammonium hydroxide isocratic elution with Carbon Dioxide, 2.5 min method): 0.746 min, 99.4% purity, 98.8% ee: $^1$H NMR (400 MHz, DMSO-d6) δ 8.38 (d, J=8.0 Hz, 1H), 7.49 (dd, J=7.5, 2.0 Hz, 1H), 7.40-7.19 (m, 6H), 7.09-7.01 (m, 2H), 5.57 (t, J=5.9 Hz, 1H), 4.80 (dt, J=11.5, 7.8 Hz, 1H), 4.56 (dd, J=11.5, 9.9 Hz, 1H), 4.38 (dd, J=9.9, 7.7 Hz, 1H), 3.44-3.20 (s, 3H), 3.10-2.90 (m, 2H), 2.38 (dt, J=11.5, 6.4 Hz, 1H), 2.10-1.98 (m, 1H), 1.86 (p, J=6.3 Hz, 2H). LCMS $R_T$=11.72 min, m/z=418.1 $(M+H)^+$.

LCMS (5 to 95% acetonitrile in water+0.1% formic acid over 30 mins) retention time 11.72 min, ESI+ found [M+H]=418.1.

Example 736

Method GZ20

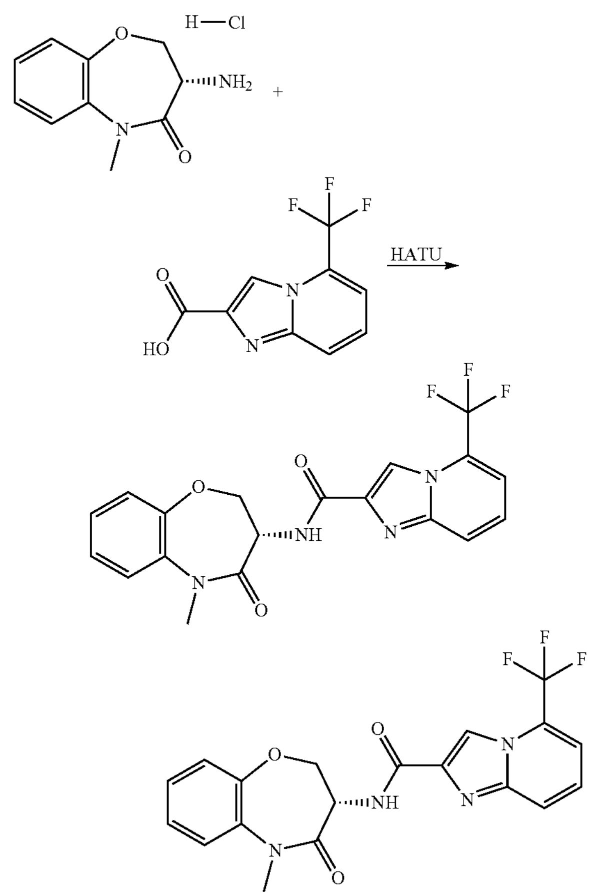

(S)—N-(5-methyl-4-oxo-2,3,4,5-tetrahydrobenzo[b][1,4]oxazepin-3-yl)-5-(trifluoromethyl) imidazo[1,2-a]pyridine-2-carboxamide To a solution of (3S)-3-amino-5-methyl-2,3-dihydro-1,5-benzoxazepin-4-one (100 mg, 0.520 mmol) and 5-(trifluoromethyl)imidazo[1,2-a]pyridine-2-carboxylic acid (126 mg, 0.546 mmol) in N,N-dimethylformamide (2 mL) was added HATU (224 mg, 0.752 mmol), and N,N-diisopropylethylamine (0.28 mL, 1.56 mmol. The reaction mixture was stirred overnight at RT, then was purified by preparative RP-HPLC (20-60% acetonitrile in water+0.1% formic acid) to afford (S)—N-(5-methyl-4-oxo-2,3,4,5-tetrahydrobenzo[b][1,4]oxazepin-3-yl)-5-(trifluoromethyl)imidazo[1,2-a]pyridine-2-carboxamide (169 mg, 80%) as tan solid. $^1$H NMR (400 MHz, DMSO-d6) δ 8.58 (d, J=8.0 Hz, 1H), 8.30 (q, J=1.8 Hz, 1H), 8.05 (d, J=9.2 Hz, 1H), 7.70 (d, J=7.1 Hz, 1H), 7.60-7.48 (m, 2H), 7.30 (m, 3H), 4.91 (dt, J=11.4, 7.9 Hz, 1H), 4.60 (dd, J=11.5, 9.9 Hz, 1H), 4.47 (dd, J=9.9, 7.7 Hz, 1H), 3.34 (s, 3H). LCMS $R_T$=6.00 min, m/z=405.0 $(M+H)^+$. LCMS (5 to 95% acetonitrile in water+0.1% formic acid over 10 mins) retention time 6.00 min, ESI+ found [M+H]=405.0.

Example 737

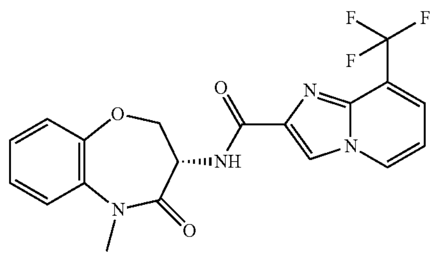 [SMILES: CN1C(=O)[C@@H](NC(=O)c2cn3cccc(C(F)(F)F)c3n2)COc2ccccc21]

(S)—N-(5-methyl-4-oxo-2,3,4,5-tetrahydrobenzo[b][1,4]oxazepin-3-yl)-8-(trifluoromethyl) imidazo[1,2-a]pyridine-2-carboxamide (S)—N-(5-methyl-4-oxo-2,3,4,5-tetrahydrobenzo[b][1,4]oxazepin-3-yl)-8-(trifluoromethyl)imidazo[1,2-a]pyridine-2-carboxamide was prepared corresponding from (S)-3-amino-5-methyl-2,3-dihydrobenzo[b][1,4]oxazepin-4(5H)-one hydrochloride, and 8-(trifluoromethyl)imidazo[1,2-a]pyridine-2-carboxylic acid according to Method GZ20. The residue was purified by preparative RP-HPLC (20-60% acetonitrile in water+0.1% formic acid). Yield of final step: 175 mg, 83%. $^1$H NMR (400 MHz, DMSO-d6) δ 8.82 (d, J=6.8 Hz, 1H), 8.57 (s, 1H), 8.30 (d, J=7.8 Hz, 1H), 7.86 (dt, J=7.3, 1.2 Hz, 1H), 7.55-7.46 (m, 1H), 7.39-7.23 (m, 3H), 7.14 (t, J=7.0 Hz, 1H), 4.91 (dt, J=11.3, 7.7 Hz, 1H), 4.64-4.45 (m, 2H), 3.35 (s, 3H). LC-MS $R_T$=4.81 min, m/z=405.1 $(M+H)^+$.

LCMS (5 to 95% acetonitrile in water+0.1% formic acid over 10 mins) retention time 4.81 min, ESI+ found [M+H]=405.1.

Example 738

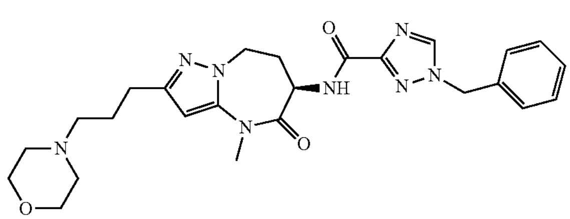 [SMILES: CN1C(=O)[C@H](NC(=O)c2ncn(Cc3ccccc3)n2)CCn2nc(CCCN3CCOCC3)cc21]

1-benzyl-N-[(6R)-4-methyl-2-(3-morpholinopropyl)-5-oxo-7,8-dihydro-6H-pyrazolo[1,5-a][1,3]diazepin-6-yl]-1,2,4-triazole-3-carboxamide Further purification of Example 662. 1H NMR (400 MHz, CD3OD) δ 8.56 (s, 1H), 7.38-7.32 (m, 5H), 6.17 (s, 1H), 5.47 (s, 2H), 4.54-4.49 (m, 1H), 4.33-4.30 (m, 1H), 4.27-4.21 (m, 1H), 3.69 (t, J=4.8 Hz, 4H), 3.33 (s, 3H), 2.83-2.80 (m, 1H), 2.66-2.62 (m, 2H), 2.48-2.40 (m, 6H), 2.26-2.24 (m, 1H), 1.89-1.86 (m, 2H).

Example 739

WX Method 211

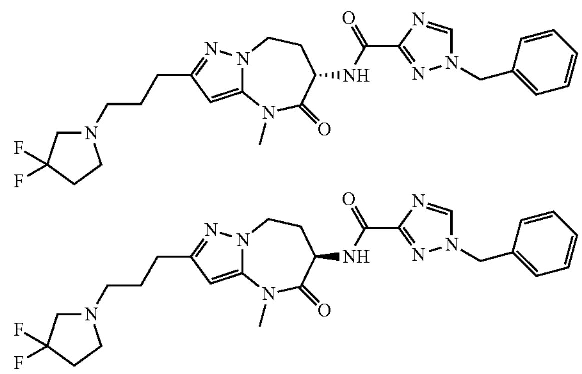

1-benzyl-N-[(6S)-2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide

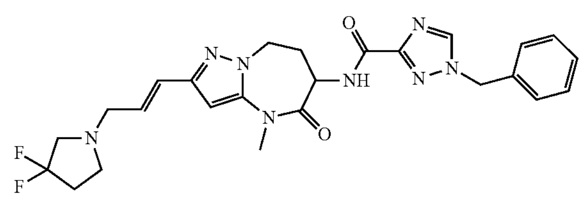 [SMILES: CN1C(=O)C(NC(=O)c2ncn(Cc3ccccc3)n2)CCn2nc(/C=C/CN3CCC(F)(F)C3)cc21]

Step 1: 1-benzyl-N-[2-[(E)-3-(3,3-difluoropyrrolidin-1-yl)prop-1-enyl]-4-methyl-5-oxo-7,8-dihydro-6H-pyrazolo[1,5-a][1,3]diazepin-6-yl]-1,2,4-triazole-3-carboxamide To a solution of [(E)-3-[6-[(1-benzyl-1,2,4-triazole-3-carbonyl)amino]-4-methyl-5-oxo-7,8-dihydro-6H-pyrazolo[1,5-a][1,3]diazepin-2-yl]allyl]methanesulfonate (20 mg, 0.04 mmol) in N,N-dimethylformamide (3 mL) was added potassium carbonate (28 mg, 0.20 mmol) and 3,3-difluoropyrrolidine hydrochloride (17 mg, 0.12 mmol). The reaction mixture was stirred at 35° C. for 12 h and then poured into water (15 mL). The mixture was extracted with ethyl acetate (3×10 mL). The combined organic layers were washed with brine (2×10 mL), dried over sodium sulfate and concentrated under reduced pressure to give crude 1-benzyl-N-[2-[(E)-3-(3,3-difluoropyrrolidin-1-yl)prop-1-enyl]-4-methyl-5-oxo-7,8-dihydro-6H-pyrazolo[1,5-a][1,3]diazepin-6-yl]-1,2,4-triazole-3-carboxamide (18 mg, 88%) as a yellow oil. LC-MS $R_T$=0.579 min, m/z=511.1 $[M+H]^+$. LCMS (5 to 95% acetonitrile in water+0.03% trifluoacetic acid over 1.5 mins) retention time 0.579 min, ESI+ found [M+H]=511.1.

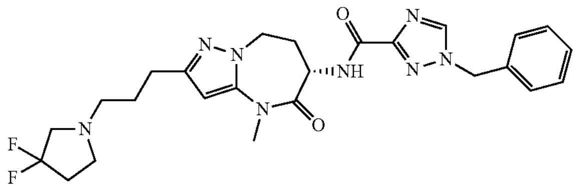

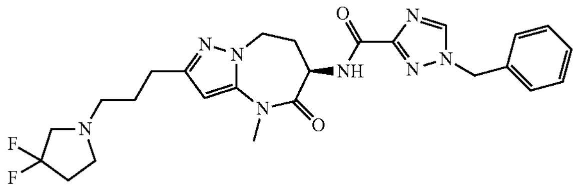

Step 2: 1-benzyl-N-[(6S)-2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide A mixture of 1-benzyl-N-[2-[(E)-3-(3,3-difluoropyrrolidin-1-yl)prop-1-enyl]-4-methyl-5-oxo-7,8-dihydro-6H-pyrazolo[1,5-a][1,3]diazepin-6-yl]-1,2,4-triazole-3-carboxamide (18 mg, 0.04 mmol) and *Pallidium* on carbon (10%, 19 mg) in ethyl acetate (10 mL) was hydrogenated (15 psi) for 12 h and then filtered. The filtrate was concentrated under reduced pressure and the residue was purified by RP-HPLC (acetonitrile 30-60%/0.05% $NH_3.H_2O$ in water) to give 1-benzyl-N-[2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide (13 mg, 72%) as a white solid. The racemic material (50 mg, from 2 batches) was further separated by chiral SFC to give: 1-benzyl-N-[(6S)-2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide (Peak 1, Retention time 4.500 min) (8.1 mg, 16%) as a white solid. $^1$H NMR (400 MHz, $CD_3OD$) δ 8.58 (s, 1H), 7.39-7.33 (m, 5H), 6.17 (s, 1H), 5.48 (s, 2H), 4.54-4.49 (m, 1H), 4.32-4.30 (m, 1H), 4.26-4.21 (m, 1H), 3.33 (s, 3H), 3.07-3.03 (m, 2H), 2.91-2.83 (m, 3H), 2.68-2.65 (m, 4H), 2.36-2.27 (m, 3H), 1.91-1.87 (m, 2H). LC-MS $R_T$=1.639 min, m/z=513.2 $[M+H]^+$. LCMS (10 to 80% acetonitrile in water+0.03% ammonium bicarbonate over 3.0 mins) retention time 1.639 min, ESI+ found [M+H]= 513.2.

1-benzyl-N-[(6R)-2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide (Peak 2, Retention time=5.268 min) (7.7 mg, 15%) as a white solid. $^1$H NMR (400 MHz, $CD_3OD$) δ 8.59 (br. s, 1H), 7.39-7.33 (m, 5H), 6.17 (s, 1H), 5.48 (s, 2H), 4.54-4.49 (m, 1H), 4.32-4.30 (m, 1H), 4.25-4.22 (m, 1H), 3.33 (s, 3H), 3.23-3.20 (m, 2H), 3.07 (br. s, 2H), 2.83-2.80 (m, 3H), 2.68 (t, J=7.2 Hz, 2H), 2.40-2.37 (m, 2H), 2.35-2.25 (m, 1H), 1.95-1.91 (m, 2H). LC-MS $R_T$=1.647 min, m/z=513.2 $[M+H]^+$.

LCMS (10 to 80% acetonitrile in water+0.03% ammonium bicarbonate over 3.0 mins) retention time 1.647 min, ESI+ found [M+H]=513.2.

SFC condition: column: chiralcel OD-3 (100×4.6 mm), 3 um mobile phase: A: CO2; B: ethanol (0.05% DEA) gradient: from 5 to 40 of B in 4.5 min and hold 40% for 2.5 min, then 5% of B for 1 min. Flow rate: 2.8 mL/min. Column temperature: 40° C.

Example 740

WX Method 182

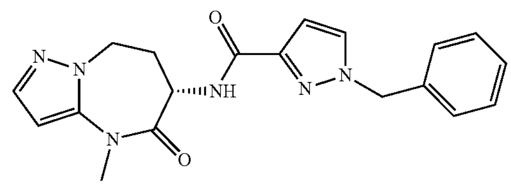 [SMILES: CN1C(=O)[C@@H](NC(=O)c2ccn(Cc3ccccc3)n2)CCn2nccc21]

1-benzyl-N-[(6S)-4-methyl-5-oxo-7,8-dihydro-6H-pyrazolo[1,5-a][1,3]diazepin-6-yl]pyrazole-3-carboxamide

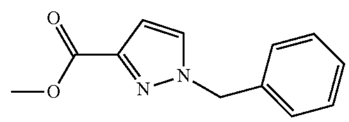 [SMILES: COC(=O)c1ccn(Cc2ccccc2)n1]

Step 1: methyl 1-benzylpyrazole-3-carboxylate

To a solution of methyl 1H-pyrazole-3-carboxylate (200 mg, 1.59 mmol) in N,N-dimethylformamide (5 mL) was added potassium carbonate (658 mg, 4.76 mmol) and benzyl bromide (326 mg, 1.9 mmol). The mixture was stirred at 25° C. for 12 h and then filtered. The filtrate was concentrated under reduced pressure and the residue was purified by column chromatography (silica gel, 100-200 mesh, 0 to 50% ethyl acetate in petroleum ether) to give methyl 1-benzylpyrazole-3-carboxylate (240 mg, 70%) as a white solid, used as is in the next step.

LCMS (10 to 80% acetonitrile in water+0.03% ammonium bicarbonate over 3.0 mins) retention time 1.495 min, ESI+ found [M+H]=217.1.

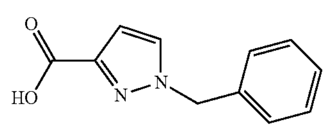 [SMILES: O=C(O)c1ccn(Cc2ccccc2)n1]

Step 2: 1-benzylpyrazole-3-carboxylic acid

A mixture of methyl 1-benzylpyrazole-3-carboxylate (240 mg, 1.11 mmol) and lithium hydroxide hydrate (133 mg, 5.55 mmol) in ethanol/water (13 mL, 8:1) was stirred at 25° C. for 12 h. The solution was diluted with water (10 mL) and adjusted to pH=4-5 by addition of 2M HCl. The resulting solid was collected by filtration and dried under reduced pressure to give crude 1-benzylpyrazole-3-carboxylic acid (170 mg, 76%) as a white solid, used in the next step without further purification.

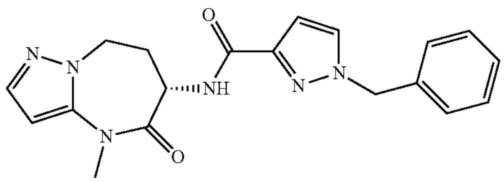 [SMILES: CN1C(=O)[C@@H](NC(=O)c2ccn(Cc3ccccc3)n2)CCn2nccc21]

Step 3: 1-benzyl-N-[(6S)-4-methyl-5-oxo-7,8-dihydro-6H-pyrazolo[1,5-a][1,3]diazepin-6-yl]pyrazole-3-carboxamide A mixture of 1-benzylpyrazole-3-carboxylic acid (60 mg, 0.28 mmol), (6S)-6-amino-4-methyl-7,8-dihydro-6H-pyrazolo[1,5-a][1,3]diazepin-5-one (50 mg, 0.28 mmol), 1-hydroxybenzotriazole (56 mg, 0.42 mmol) and 1-(3-dimethyl aminopropyl)-3-ethylcarbodiimidehydrochloride (80 mg, 0.42 mmol) in N,N-dimethylformamide (5 mL) was stirred at 25° C. for 12 h and concentrated under reduced pressure. The residue was purified by RP-HPLC (acetonitrile 27-57%/0.05% ammonium hydroxide in water) to afford 1-benzyl-N-[(6S)-4-methyl-5-oxo-7,8-dihydro-6H-pyrazolo[1,5-a][1,3]diazepin-6-yl]pyrazole-3-carboxamide (66.9 mg, 66%) as a white solid. $^1$H NMR (400 MHz, $CD_3OD$) δ 7.71 (d, J=2.4 Hz, 1H), 7.66 (d, J=2.0 Hz, 1H), 7.35-7.26 (m, 5H), 6.74 (d, J=2.8 Hz, 1H), 6.39 (d, J=2.0 Hz, 1H), 5.40 (s, 2H), 4.57-4.52 (m, 1H), 4.46-4.44 (m, 1H), 4.34-4.31 (m, 1H), 3.36 (s, 3H), 2.89-2.82 (m, 1H), 2.34-2.28 (m, 1H). LC-MS $R_T$=0.755 min, m/z=365.0 [M+H]$^+$.

LCMS (5 to 95% acetonitrile in water+0.03% trifluoacetic acid over 1.5 mins) retention time 0.755 min, ESI+ found [M+H]=365.0.

Example 741

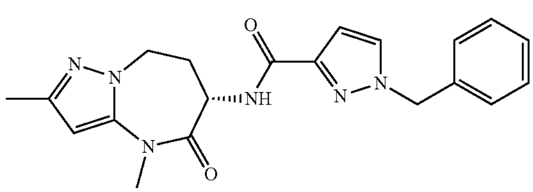 [SMILES: Cc1cc2n(n1)CC[C@H](NC(=O)c1ccn(Cc3ccccc3)n1)C(=O)N2C]

1-benzyl-N-[(6S)-2,4-dimethyl-5-oxo-7,8-dihydro-6H-pyrazolo[1,5-a][1,3]diazepin-6-yl]pyrazole-3-carboxamide Amide coupling prepared in a similar fashion to WX Method 182. The crude was purified by RP-HPLC (acetonitrile 27-57%/0.05% ammonium hydroxide in water) to give 1-benzyl-N-[(6S)-2,4-dimethyl-5-oxo-7,8-dihydro-6H-pyrazolo[1,5-a][1,3]diazepin-6-yl]pyrazole-3-carboxamide (66.6 mg, 68%) as a white solid. $^1$H NMR (400 MHz, $CD_3OD$) δ 7.71 (s, 1H), 7.36-7.25 (m, 5H), 6.75 (s, 1H), 6.39-6.34 (m, 1H), 5.40 (s, 2H), 4.66-4.65 (m, 1H), 4.44-4.34 (m, 2H), 3.36 (s, 3H), 2.92-2.81 (m, 1H), 2.39-2.37 (m, 4H). LC-MS $R_T$=0.764 min, m/z=379.0 [M+H]$^+$.

LCMS (5 to 95% acetonitrile in water+0.03% trifluoacetic acid over 1.5 mins) retention time 0.764 min, ESI+ found [M+H]=379.0.

Examples 742 and 744

WX Method 186

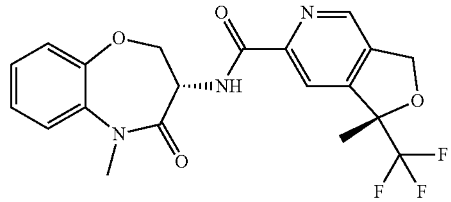

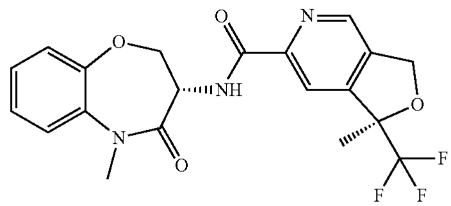

(1S)-1-methyl-N-[(3S)-5-methyl-4-oxo-2,3-dihydro-1,5-benzoxazepin-3-yl]-1-(trifluoromethyl)-3H-furo[3,4-c]pyridine-6-carboxamide and (1R)-1-methyl-N-[(3S)-5-methyl-4-oxo-2,3-dihydro-1,5-benzoxazepin-3-yl]-1-(trifluoromethyl)-3H-furo[3,4-c]pyridine-6-carboxamide

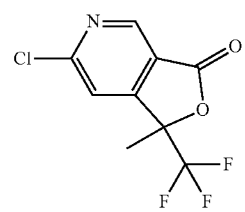 [SMILES: CC1(C(F)(F)F)OC(=O)c2cnc(Cl)cc21]

Step 1: 6-chloro-1-methyl-1-(trifluoromethyl)furo[3,4-c]pyridin-3(1H)-one

To a solution of 2,2,6,6-tetramethylpiperidine (13.5 g, 95.2 mmol) in tetrahydrofuran (100 mL) was added n-butyllithium (2.5 M in hexanes, 38.0 mL, 95.0 mmol) at −78° C. The reaction mixture was stirred at −78° C. for 1 h and 6-chloronicotinic acid (5.0 g, 31.7 mmol) was added. The reaction mixture was stirred at −78° C. for another 2 h and 1,1,1-trifluoroacetone (10.7 g, 95 mmol) was added. After addition, the reaction mixture was stirred at 25° C. for 24 h and quenched by addition of saturated ammonium chloride (30 mL). The mixture was extracted with ethyl acetate (3×100 mL). The combined organic layers were dried over sodium sulfate and concentrated under reduced pressure. The residue was then purified by flash column chromatography (silica gel, 100-200 mesh, 0 to 20% ethyl acetate in petroleum ether) to afford 6-chloro-1-methyl-1-(trifluoromethyl)furo[3,4-c]pyridin-3(1H)-one (6.0 g, 75%) as yellow oil, used as is in the next step.

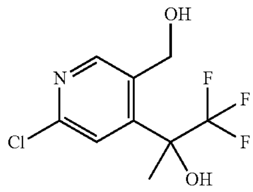 [SMILES: CC(O)(c1cc(Cl)ncc1CO)C(F)(F)F]

Step 2: 2-(2-chloro-5-(hydroxymethyl)pyridin-4-yl)-1,1,1-trifluoropropan-2-ol

To a solution of 6-chloro-1-methyl-1-(trifluoromethyl) furo[3,4-c]pyridin-3(1H)-one (3.0 g, 11.9 mmol) in tetrahydrofuran (60 mL) was added lithium aluminium hydride (881 mg, 24 mmol) in portions at −78° C. After addition, the mixture was slowly warmed to 0° C. and stirred at 0° C. for 30 min. The mixture was quenched with addition of water (0.05 mL), 10% NaOH (0.05 mL) and followed by water (0.15 mL). The resulting mixture was added anhydrous sodium sulphate (20 g) and stirred for 30 min. The mixture was filtered and the filtrate was concentrated under reduced pressure. The residue was purified by flash column chromatography (silica gel, 100-200 mesh, 0 to 50% ethyl acetate in petroleum ether) to afford 2-(2-chloro-5-(hydroxymethyl) pyridin-4-yl)-1,1,1-trifluoropropan-2-ol (400 mg, 13%) as white solid, used as is in the next step.

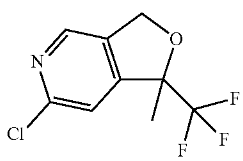

Step 3: 6-chloro-1-methyl-1-(trifluoromethyl)-1,3-dihydrofuro[3,4-c]pyridine

To a solution of N1,N1,N2,N2-tetramethyldiazene-1,2-dicarboxamide (808 mg, 4.7 mmol) in toluene (40 mL) was added tri-n-butylphosphine (950 mg, 4.7 mmol) and 2-[2-chloro-5-(hydroxymethyl)-4-pyridyl]-1,1,1-trifluoro-propan-2-ol (400 mg, 1.6 mmol) under nitrogen atmosphere. The mixture was stirred at 25° C. for 2 h and then concentrated under reduced pressure. The residue was purified by flash column chromatography (silica gel, 100-200 mesh, 0 to 20% ethyl acetate in petroleum ether) to afford 6-chloro-1-methyl-1-(trifluoromethyl)-1,3-dihydrofuro[3,4-c]pyridine (200 mg, 54%). LC-MS $R_T$=1.5 min, m/z=238.1 $[M+H]^+$.

LCMS (10 to 80% acetonitrile in water+0.03% trifluoacetic acid over 1.5 mins) retention time 0.98 min, ESI+ found [M+H]=238.1.

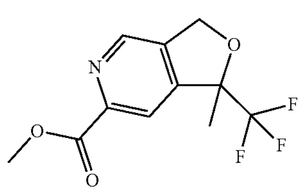 [SMILES: COC(=O)c1cc2c(cn1)COC2(C)C(F)(F)F]

Step 4: methyl 1-methyl-1-(trifluoromethyl)-1,3-dihydrofuro[3,4-c]pyridine-6-carboxylate A mixture of 1,1'-bis(diphenylphosphino)ferrocene palladium dichloride (55 mg, 0.08 mmol), 6-chloro-1-methyl-1-(trifluoromethyl)-1,3-dihydrofuro[3,4-c]pyridine (180 mg, 0.76 mmol) and triethylamine (230 mg, 2.27 mmol) in methanol (50 mL) was heated at 70° C. under the atmosphere of CO (35 psi) for 15 h. After cooling to room temperature, the reaction mixture was filtered and the filtrated was concentrated under reduced pressure. The residue was purified by flash column chromatography (silica gel, 100-200 mesh, 0 to 100% ethyl acetate in petroleum ether) to afford methyl 1-methyl-1-(trifluoromethyl)-1,3-dihydrofuro[3,4-c]pyridine-6-carboxylate (150 mg, 76%) as a light yellow oil, used as is in the next step. LC-MS $R_T$=0.78 min, m/z=261.9 $[M+H]^+$.

LCMS (5 to 95% acetonitrile in water+0.03% trifluoacetic acid over 1.5 mins) retention time 0.78 min, ESI+ found [M+H]=261.9.

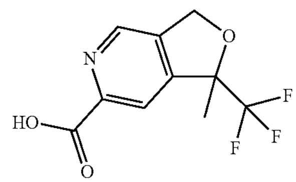 [SMILES: CC1(C(F)(F)F)OCc2cnc(C(=O)O)cc21]

Step 5: 1-methyl-1-(trifluoromethyl)-1,3-dihydrofuro[3,4-c]pyridine-6-carboxylic acid A mixture of methyl 1-methyl-1-(trifluoromethyl)-1,3-dihydrofuro[3,4-c]pyridine-6-carboxylate (140 mg, 0.54 mmol) and potassium hydroxide (60 mg, 1.07 mmol) in ethanol (4 mL) and water (1 mL) was stirred at 25° C. for 12 h. The mixture was added 1N HCl (3 mL) and concentrated under reduced pressure. The crude was dissolved in methanol (20 mL) and filtered. The filtrate was concentrated under reduced pressure to afford the crude 1-methyl-1-(trifluoromethyl)-1,3-dihydrofuro[3,4-c]pyridine-6-carboxylic acid (120 mg, 91%) as a yellow solid, used in the next step without further purification.

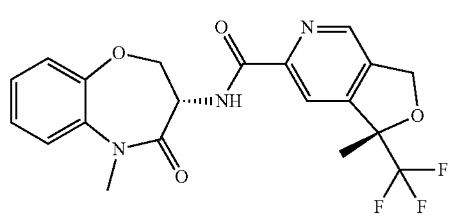

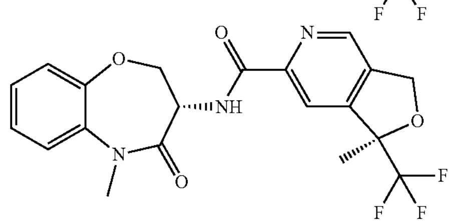

Step 6: (1S)-1-methyl-N-[(3S)-5-methyl-4-oxo-2,3-dihydro-1,5-benzoxazepin-3-yl]-1-(trifluoromethyl)-3H-furo[3,4-c]pyridine-6-carboxamide and (1R)-1-methyl-N-[(3S)-5-methyl-4-oxo-2,3-dihydro-1,5-benzoxazepin-3-yl]-1-(trifluoromethyl)-3H-furo[3,4-c]pyridine-6-carboxamide A mixture of (3S)-3-amino-5-methyl-2,3-dihydro-1,5-benzoxazepin-4-one (40 mg, 0.21 mmol), 1H-benzo[d][1,2,3]triazol-1-ol (5.6 mg, 0.04 mmol), 1-methyl-1-(trifluoromethyl)-1,3-dihydrofuro[3,4-c]pyridine-6-carboxylic acid (51 mg, 0.21 mmol) and $N^1$-((ethylimino)methylene)-$N^3$,$N^3$-dimethylpropane-1,3-diamine hydrochloride (40 mg, 0.21 mmol) in N,N-dimethylformamide (5 mL) was stirred at 25° C. for 16 h. The mixture was concentrated under reduced pressure and the residue was purified by RP-HPLC (acetonitrile 48% to 78%/0.05% ammonium hydroxide in water) to afford 1-methyl-N—((S)-5-methyl-4-oxo-2,3,4,5-tetrahydrobenzo[1,4]oxazepin-3-yl)-1-(trifluoro methyl)-1,3-dihydrofuro[3,4-c]pyridine-6-carboxamide (55 mg, 63%) as a white solid. This racemic material was further separated by chiral SFC to afford:

(1S)-1-methyl-N-[(3S)-5-methyl-4-oxo-2,3-dihydro-1,5-benzoxazepin-3-yl]-1-(trifluoromethyl)-3H-furo[3,4-c]pyridine-6-carboxamide (Peak 1, retention time 4.376 min) (17.9 mg, 31%) as a white solid. $^1$H NMR (400 MHz, $CDCl_3$) δ 8.89 (d, J=8.0 Hz, 1H), 8.59 (s, 1H), 8.08 (s, 1H), 7.27-7.26 (m, 3H), 5.31 (s, 2H), 5.14-5.05 (m, 1H), 4.79 (t, J=8.0 Hz, 1H), 4.36-4.27 (m, 1H), 3.46 (s, 3H), 1.71 (s, 3H). LC-MS $R_T$=1.084 min, m/z=422.2 $[M+H]^+$.

LCMS (10 to 80% acetonitrile in water+0.05% ammonium hydroxide over 2 mins) retention time 1.084 min, ESI+ found [M+H]=422.2.

(1R)-1-methyl-N-[(3S)-5-methyl-4-oxo-2,3-dihydro-1,5-benzoxazepin-3-yl]-1-(trifluoromethyl)-3H-furo[3,4-c]pyridine-6-carboxamide (Peak 2, retention time 5.736 min) (19.1 mg, 34%) as a white solid. $^1$H NMR (400 MHz, $CDCl_3$) δ 8.89 (d, J=7.2 Hz, 1H), 8.59 (s, 1H), 8.08 (s, 1H), 7.26 (s, 3H), 5.31 (s, 2H), 5.15-5.05 (m, 1H), 4.79 (t, J=8.0 Hz, 1H), 4.33-4.27 (m, 1H), 3.46 (s, 3H), 1.71 (s, 3H). LC-MS $R_T$=1.092 min, m/z=422.2 $[M+H]^+$.

LCMS (10 to 80% acetonitrile in water+0.05% ammonium hydroxide over 2 mins) retention time 1.092 min, ESI+ found [M+H]=422.2.

SFC condition: Column: Chiralpak AD (250 mm*30 mm, 10 um) Mobile phase: A: $CO_2$ B: methanol (0.10% $NH_3H_2O$), supercritical $CO_2$/EtOH+$NH_3H_2O$=45/45; 80 mL/min.

Examples 743 and 745

WX Method 188

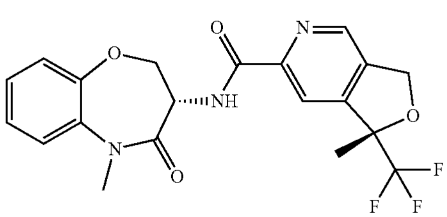

-continued

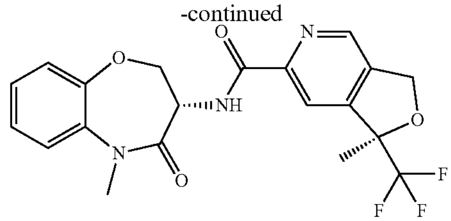

(7S)-7-methyl-N-[(3S)-5-methyl-4-oxo-2,3-dihydro-1,5-benzoxazepin-3-yl]-7-(trifluoromethyl)-5H-furo[3,4-d]pyrimidine-2-carboxamide and (7R)-7-methyl-N-[(3S)-5-methyl-4-oxo-2,3-dihydro-1,5-benzoxazepin-3-yl]-7-(trifluoromethyl)-5H-furo[3,4-d]pyrimidine-2-carboxamide

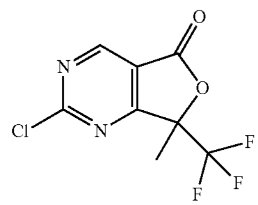 [SMILES: CC1(C(F)(F)F)OC(=O)c2cnc(Cl)nc21]

Step 1: 2-chloro-7-methyl-7-(trifluoromethyl)furo[3,4-d]pyrimidin-5(7H)-one

To a solution of 2,2,6,6-tetramethylpiperidine (27.0 g, 190.4 mmol) in tetrahydrofuran (200 mL) was added n-butyllithium (2.5 M in hexanes, 76.0 mL, 190.0 mmol) at −78° C. The reaction mixture was stirred at −78° C. for 1 h and 2-chloropyrimidine-5-carboxylic acid (10.0 g, 63.3 mmol) in THF (100 mL) was added. The reaction mixture was stirred at −78° C. for another 2.5 h and 1,1,1-trifluoroacetone (21.4 g, 190.0 mmol) was added. After addition, the reaction mixture was stirred at 25° C. for 24 h and quenched by addition of saturated ammonium chloride (100 mL). The mixture was adjusted to pH=2-3 by addition of 2 M HCl (200 mL) and then extracted with ethyl acetate (3×100 mL). The combined organic layers were dried over sodium sulfate and concentrated under reduced pressure. The residue was then purified by flash column chromatography (silica gel, 100-200 mesh, 0 to 20% ethyl acetate in petroleum ether) to afford 2-chloro-7-methyl-7-(trifluoromethyl)furo[3,4-d]pyrimidin-5(7H)-one (2.5 g, 16%) as yellow oil, used as is in the next step.

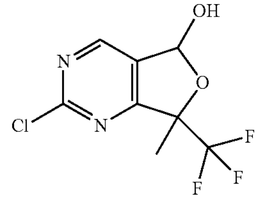 [SMILES: CC1(C(F)(F)F)OC(O)c2cnc(Cl)nc21]

Step 2: 2-chloro-7-methyl-7-(trifluoromethyl)-5,7-dihydrofuro[3,4-d]pyrimidin-5-ol To a solution of 2-chloro-7-methyl-7-(trifluoromethyl)furo[3,4-d]pyrimidin-5(7H)-one (2.5 g, 9.9 mmol) in toluene (60 mL) was added diisobutylaluminum hydride (1.0 M in toluene, 20.0 mL, 20.0 mmol) dropwise at −78° C. After addition, the mixture was stirred at −78° C. for 2 h and then quenched by addition of water (0.05 mL), 10% NaOH (0.05 mL) and followed by $H_2O$ (0.15 mL). The mixture was dried with $Na_2SO_4$ and filtered. The filtrate was concentrated under reduced pressure and the residue was purified by flash column chromatography (silica gel, 100-200 mesh, 0 to 50% ethyl acetate in petroleum ether) to afford 2-chloro-7-methyl-7-(trifluoromethyl)-5,7-dihydrofuro[3,4-d]pyrimidin-5-ol (1.2 g, 48%) as a yellow oil. LCMS $R_T$=0.622 min, m/z=254.9 $[M+H]^+$.

LCMS (5 to 95% acetonitrile in water+0.03% trifluoacetic acid over 1.5 mins) retention time 0.622 min, ESI+ found [M+H]=254.9.

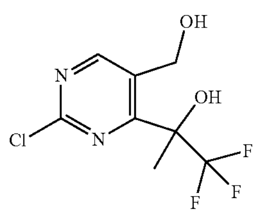 [SMILES: CC(O)(c1nc(Cl)ncc1CO)C(F)(F)F]

Step 3: 2-(2-chloro-5-(hydroxymethyl)pyrimidin-4-yl)-1,1,1-trifluoropropan-2-ol A mixture of 2-chloro-7-methyl-7-(trifluoromethyl)-5H-furo[3,4-d]pyrimidin-5-ol (600 mg, 2.36 mmol) in trifluoroacetic acid (2.69 g, 23.57 mmol) was stirred at 0° C. for 30 min and then triethylsilane (2.74 g, 23.57 mmol) was added. The reaction mixture was stirred at 50° C. for 16 h and concentrated under reduced pressure. The residue was purified by flash column chromatography (silica gel, 100-200 mesh, 0 to 50% ethyl acetate in petroleum ether) to afford 2-[2-chloro-5-(hydroxymethyl)pyrimidin-4-yl]-1,1,1-trifluoro-propan-2-ol (300 mg, 50%) as a yellow oil.

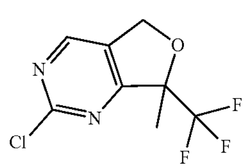

Step 4: 2-chloro-7-methyl-7-(trifluoromethyl)-5H-furo[3,4-d]pyrimidine

To a solution of 2-[2-chloro-5-(hydroxymethyl)pyrimidin-4-yl]-1,1,1-trifluoro-propan-2-ol (300 mg, 1.17 mmol) in toluene (5 mL) was added tri-n-butylphosphine (355 mg, 1.75 mmol) and N1,N1,N2,N2-tetramethyldiazene-1,2-dicarboxamide (302 mg, 1.75 mmol). The reaction mixture was stirred at 20° C. for 2 h and then concentrated under reduced pressure. The residue was purified by flash column chromatography (silica gel, 100-200 mesh, 0 to 20% ethyl acetate in petroleum ether) to afford 2-chloro-7-methyl-7-(trifluoromethyl)-5H-furo[3,4-d]pyrimidine (120 mg, 43%). LCMS $R_T$=0.692 min, m/z=239.0 $[M+H]^+$.

LCMS (5 to 95% acetonitrile in water+0.03% trifluoacetic acid over 1.5 mins) retention time 0.692 min, ESI+ found [M+H]=239.0.

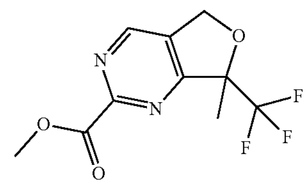 [SMILES: COC(=O)c1ncc2c(n1)C(C)(C(F)(F)F)OC2]

Step 5: methyl 7-methyl-7-(trifluoromethyl)-5H-furo[3,4-d]pyrimidine-2-carboxylate A mixture of 2-chloro-7-methyl-7-(trifluoromethyl)-5H-furo[3,4-d]pyrimidine (100 mg, 0.42 mmol), 1,1'-bis(diphenylphosphino)ferrocene palladium dichloride (31 mg, 0.04 mmol) and triethylamine (212 mg, 2.1 mmol) in methanol (20 mL) was heated to 80° C. for 8 h under CO (45 psi). After cooled, the reaction mixture was filtered and the filtrate was concentrated under reduced pressure. The residue was then purified by flash column chromatography (silica gel, 100-200 mesh, 0 to 100% ethyl acetate in petroleum ether) to afford methyl 7-methyl-7-(trifluoromethyl)-5H-furo[3,4-d]pyrimidine-2-carboxylate (80 mg, 73%) as a light yellow oil, used as is in the next step.

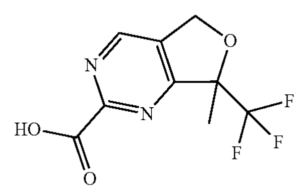 [SMILES: CC1(C(F)(F)F)OCc2cnc(C(=O)O)nc21]

Step 6:7-methyl-7-(trifluoromethyl)-5H-furo[3,4-d]pyrimidine-2-carboxylicacid A mixture of methyl 7-methyl-7-(trifluoromethyl)-5H-furo[3,4-d]pyrimidine-2-carboxylate (80 mg, 0.31 mmol) and lithium hydroxide monohydrate (128 mg, 3.05 mmol) in tetrahydrofuran (5 mL)/water (3 mL) was stirred at 20° C. for 2 h. The mixture was acidified by addition of 1N HCl (3 mL) and concentrated under reduced pressure. The residue was dissolved in methanol (20 mL) and filtered. The filtrate was concentrated under reduced pressure to afford the crude 7-methyl-7-(trifluoromethyl)-5H-furo[3,4-d]pyrimidine-2-carboxylic acid (60 mg, 79%) as a yellow solid, used as is in the next step.

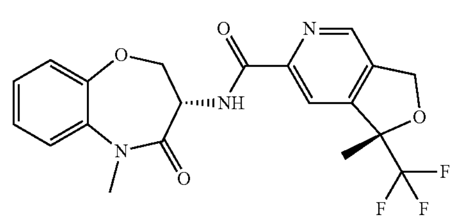

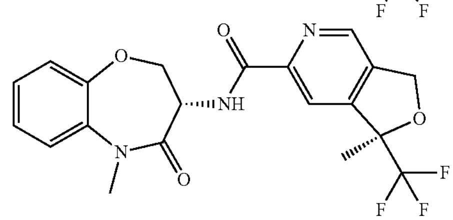

Step 7: (7S)-7-methyl-N-[(3S)-5-methyl-4-oxo-2,3-dihydro-1,5-benzoxazepin-3-yl]-7-(trifluoromethyl)-5H-furo[3,4-d]pyrimidine-2-carboxamide and (7R)-7-methyl-N-[(3S)-5-methyl-4-oxo-2,3-dihydro-1,5-benzoxazepin-3-yl]-7-(trifluoromethyl)-5H-furo[3,4-d]pyrimidine-2-carboxamide A mixture of (3S)-3-amino-5-methyl-2,3-dihydro-1,5-benzoxazepin-4-one (28 mg, 0.15 mmol), 7-methyl-7-(trifluoromethyl)-5H-furo[3,4-d]pyrimidine-2-carboxylic acid (30 mg, 0.12 mmol), 1-hydroxybenzotriazole (20 mg, 0.15 mmol) and 1-(3-dimethyl aminopropyl)-3-ethylcarbodiimidehydrochloride (28 mg, 0.15 mmol) in N,N-dimethylformamide (5 mL) was stirred at 20° C. for 2 h and then concentrated under reduced pressure. The residue was purified by RP-HPLC (acetonitrile 32% to 62%/0.05% ammonium hydroxide in water) to afford 7-methyl-N—((S)-5-methyl-4-oxo-2,3,4,5-tetrahydrobenzo[b][1,4]oxazepin-3-yl)-7-(trifluoro methyl)-5,7-dihydrofuro[3,4-d]pyrimidine-2-carboxamide (30 mg, 59%) as a white solid. The racemic material was further separated by chiral SFC to give:

(7S)-7-methyl-N-[(3S)-5-methyl-4-oxo-2,3-dihydro-1,5-benzoxazepin-3-yl]-7-(trifluoromethyl)-5H-furo[3,4-d]pyrimidine-2-carboxamide (Peak 1, retention time 5.298 min) (10.7 mg, 36%) as a white solid. $^1$H NMR (400 MHz, $CD_3OD$) δ 9.00 (s, 1H), 7.46-7.43 (m, 1H), 7.34-7.24 (m, 3H), 5.32 (s, 2H), 5.04-4.96 (m, 1H), 4.72-4.67 (m, 1H), 4.48-4.42 (m, 1H), 3.44 (s, 3H), 1.76 (s, 3H). LCMS $R_T$=0.817 min, m/z=423.0 $[M+H]^+$.

LCMS (5 to 95% acetonitrile in water+0.03% trifluoacetic acid over 1.5 mins) retention time 0.817 min, ESI+ found [M+H]=423.0.

(7R)-7-methyl-N-[(3S)-5-methyl-4-oxo-2,3-dihydro-1,5-benzoxazepin-3-yl]-7-(trifluoromethyl)-5H-furo[3,4-d]pyrimidine-2-carboxamide (Peak 2, retention time 6.174 min) (11.7 mg, 39%) as a white solid. $^1$H NMR (400 MHz, $CD_3OD$) δ 9.00 (s, 1H), 7.46-7.43 (m, 1H), 7.34-7.24 (m, 3H), 5.32 (s, 2H), 5.04-4.96 (m, 1H), 4.72-4.67 (m, 1H), 4.48-4.42 (m, 1H), 3.44 (s, 3H), 1.76 (s, 3H). LCMS $R_T$=0.824 min, m/z=423.0 $[M+H]^+$.

LCMS (5 to 95% acetonitrile in water+0.03% trifluoacetic acid over 1.5 mins) retention time 0.824 min, ESI+ found [M+H]=423.0.

SFC condition: Column: ChiralCel (OD-H 150×4.6 mm I.D., 5 um) Mobile phase: A: $CO_2$ B: Ethanol (0.05% DEA) Gradient: from 5% to 40% of B in 5.5 min and hold 40% for 3 min, then 5% of B for 1.5 min, Flow rate: 2.5 mL/min Column temperature: 40° C.

Examples 746 and 748

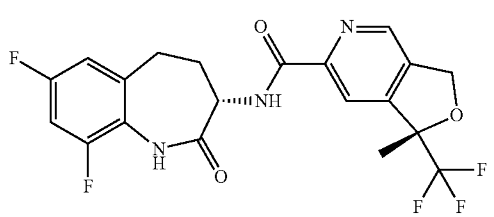

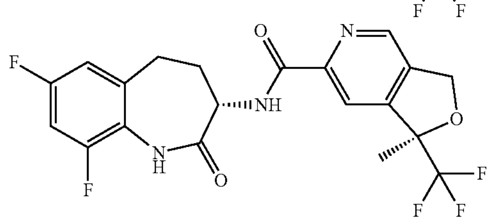

(1S)-1-methyl-N-[(3S)-7,9-difluoro-2-oxo-1,3,4,5-tetrahydro-1-benzazepin-3-yl]-1-(trifluoromethyl)-3H-furo[3,4-c]pyridine-6-carboxamide and (1R)-1-methyl-N-[(3S)-7,9-difluoro-2-oxo-1,3,4,5-tetrahydro-1-benzazepin-3-yl]-1-(trifluoromethyl)-3H-furo[3,4-c]pyridine-6-carboxamide Amide coupling prepared in a similar fashion to WX Method 184. The crude was purified by RP-HPLC (acetonitrile 48-78%/0.05% ammonia hydroxidein water) to give 1-methyl-N-[(3S)-7,9-difluoro-2-oxo-1,3,4,5-tetrahydro-1-benzazepin-3-yl]-1-(trifluoromethyl)-3H-furo[3,4-c]pyridine-6-carboxamide (55 mg, 63%) as a white solid. The racemate was further separated by chiral SFC to afford:

(1S)-1-methyl-N-[(3S)-7,9-difluoro-2-oxo-1,3,4,5-tetrahydro-1-benzazepin-3-yl]-1-(trifluoro methyl)-3H-furo[3,4-c]pyridine-6-carboxamide (Peak 1, retention time 3.756 min) (18.7 mg, 34%) as a white solid. $^1$H NMR (400 MHz, $CDCl_3$) δ 8.84 (d, J=6.8 Hz, 1H), 8.59 (s, 1H), 8.11 (s, 1H), 7.17 (s, 1H), 6.91-6.82 (m, 2H), 5.31 (s, 2H), 4.79-4.70 (m, 1H), 3.12-3.01 (m, 1H), 2.96-2.85 (m, 1H), 2.80-2.72 (m, 1H), 2.21-2.10 (m, 1H), 1.72 (s, 3H). LC-MS $R_T$=1.056 min, m/z=442.2 $[M+H]^+$.

LCMS (10 to 80% acetonitrile in water+0.05% ammonium hydroxide over 2 mins) retention time 1.056 min, ESI+ found [M+H]=442.2.

(1R)-1-methyl-N-[(3S)-7,9-difluoro-2-oxo-1,3,4,5-tetrahydro-1-benzazepin-3-yl]-1-(trifluoro methyl)-3H-furo[3,4-c]pyridine-6-carboxamide (Peak 2, retention time 5.978 min) (15.6 mg, 28%) as white solid. $^1$H NMR (400 MHz, $CDCl_3$) δ 8.84 (d, J=7.2 Hz, 1H), 8.59 (s, 1H), 8.11 (s, 1H), 7.17 (s, 1H), 6.91-6.82 (m, 2H), 5.31 (s, 2H), 4.79-4.70 (m, 1H), 3.12-3.01 (m, 1H), 2.96-2.85 (m, 1H), 2.80-2.72 (m, 1H), 2.21-2.10 (m, 1H), 1.72 (s, 3H). LC-MS $R_T$=1.068 min, m/z=442.2 $[M+H]^+$.

LCMS (10 to 80% acetonitrile in water+0.05% ammonium hydroxide over 2 mins) retention time 1.068 min, ESI+ found [M+H]=442.2.

SFC conditions: Column: Chiralpak AD 150×4.6 mm I.D., 3 um, Mobile phase: 25% methanol (0.05% DEA) in $CO_2$, Flow rate: 2.4 mL/min, Column temp.: 40° C.

Examples 747 and 749

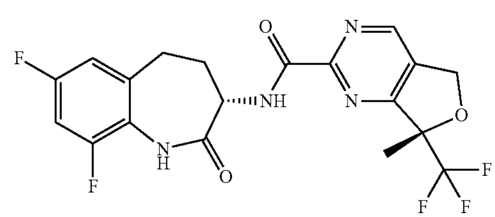

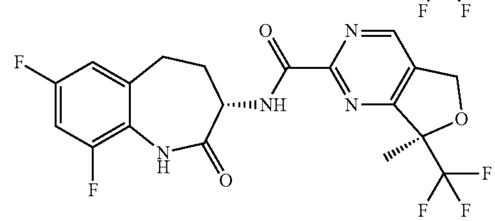

(7S)-7-methyl-N-[(3S)-7,9-difluoro-2-oxo-1,3,4,5-tetrahydro-1-benzazepin-3-yl]-7-(trifluoromethyl)-5H-furo[3,4-d]pyrimidine-2-carboxamide and (7R)-7-methyl-N-[(3S)-7,9-difluoro-2-oxo-1,3,4,5-tetrahydro-1-benzazepin-3-yl]-7-(trifluoromethyl)-5H-furo[3,4-d]pyrimidine-2-carboxamide Amide coupling prepared in a similar fashion to WX Method 188. The crude was purified by RP-HPLC (acetonitrile 32% to 62%/0.05% ammonium hydroxide in water) to give N—((S)-7,9-difluoro-2-oxo-2,3,4,5-tetrahydro-1H-benzo[b]azepin-3-yl)-7-methyl-7-(trifluoromethyl)-5,7-dihydrofuro[3,4-d]pyrimidine-2-carboxamide (30 mg, 56%) as a white solid. The racemate was separated by chiral SFC to afford:

(7S)-7-methyl-N-[(3S)-7,9-difluoro-2-oxo-1,3,4,5-tetrahydro-1-benzazepin-3-yl]-7-(trifluoro methyl)-5H-furo[3,4-d]pyrimidine-2-carboxamide (Peak 1, retention time 3.801 min) (9.1 mg, 30%) as a white solid. $^1$H NMR (400 MHz, $CD_3OD$) δ 8.99 (s, 1H), 7.04-6.99 (m, 2H), 5.32 (s, 2H), 4.66-4.61 (m, 1H), 3.04-2.98 (m, 1H), 2.87-2.75 (m, 2H), 2.28-2.23 (m, 1H), 1.76 (s, 3H). LCMS $R_T$=0.799 min, m/z=443.0 $[M+H]^+$. LCMS (5 to 95% acetonitrile in water+0.03% trifluoacetic acid over 1.5 mins) retention time 0.799 min, ESI+ found [M+H]=443.0.

(7R)-7-methyl-N-[(3S)-7,9-difluoro-2-oxo-1,3,4,5-tetrahydro-1-benzazepin-3-yl]-7-(trifluoro methyl)-5H-furo[3,4-d]pyrimidine-2-carboxamide (Peak 2, retention time 4.334 min) (9.9 mg, 33%) as a white solid. $^1$H NMR (400 MHz, $CD_3OD$) δ 8.99 (s, 1H), 7.04-6.99 (m, 2H), 5.32 (s, 2H), 4.66-4.61 (m, 1H), 3.04-2.98 (m, 1H), 2.87-2.75 (m, 2H), 2.28-2.23 (m, 1H), 1.76 (s, 3H). LCMS $R_T$=0.803 min, m/z=443.0 $[M+H]^+$. LCMS (5 to 95% acetonitrile in water+0.03% trifluoacetic acid over 1.5 mins) retention time 0.803 min, ESI+ found [M+H]=443.0.

SFC condition: Column: ChiralPak (AD-3 150×4.6 mm I.D., 3 um) Mobile phase: A: CO2 B: Methanol (0.05% DEA) Gradient: from 5% to 40% of B in 5.5 min and hold 40% for 3 min, then 5% of B for 1.5 min, Flow rate: 2.5 mL/min Column temperature: 40° C.

Example 750

WX Method 184

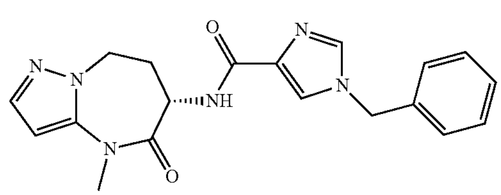 [SMILES: CN1C(=O)[C@@H](NC(=O)c2cn(Cc3ccccc3)cn2)CCn2nccc21]

1-benzyl-N-[(6S)-4-methyl-5-oxo-7,8-dihydro-6H-pyrazolo[1,5-a][1,3]diazepin-6-yl]imidazole-4-carboxamide

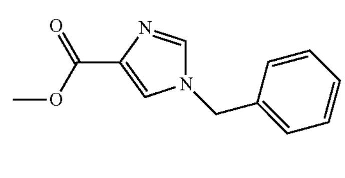 [SMILES: COC(=O)c1cn(Cc2ccccc2)cn1]

Step 1: methyl 1-benzylimidazole-4-carboxylate

To a solution of methyl 4-imidazolecarboxylate (500 mg, 3.96 mmol) in acetonitrile (10 mL) was added triethylamine (482 mg, 4.76 mmol) and benzyl bromide (678 mg, 3.96 mmol). The mixture was stirred at 25° C. for 12 h and then concentrated under reduced pressure. The residue was purified by RP-HPLC (acetonitrile 20-50%/0.05% ammonium hydroxide in water) to give methyl 1-benzylimidazole-4-carboxylate (118 mg, 14%) as a white solid, used as is in the next step. LC-MS $R_T$=1.273 min, m/z=217.1 $[M+H]^+$. LCMS (10 to 80% acetonitrile in water+0.03% ammonium bicarbonate over 3.0 mins) retention time 1.273 min, ESI+ found [M+H]=217.1.

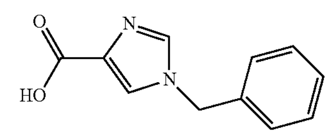 [SMILES: O=C(O)c1cn(Cc2ccccc2)cn1]

Step 2: 1-benzylimidazole-4-carboxylic acid

A mixture of methyl 1-benzylimidazole-4-carboxylate (90 mg, 0.42 mmol) and lithium hydroxide hydrate (50 mg, 2.08 mmol) in ethanol/water (9 mL, 8:1) was stirred at 25° C. for 12 h. The solution was diluted with water (10 mL) and adjusted to pH=4-5 by addition of 2M HCl. The resulting solid was collected by filtration and dried under reduced pressure to give crude 1-benzylimidazole-4-carboxylic acid (60 mg, 71%) as a white solid, used in the next step without further purification.

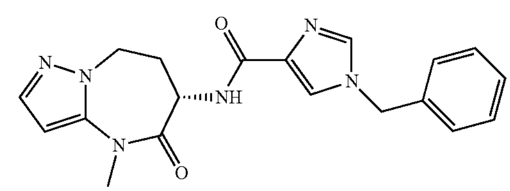 [SMILES: CN1C(=O)[C@@H](NC(=O)c2cn(Cc3ccccc3)cn2)CCn2nccc21]

Step 3: 1-benzyl-N-[(6S)-4-methyl-5-oxo-7,8-dihydro-6H-pyrazolo[1,5-a][1,3]diazepin-6-yl]imidazole-4-carboxamide A mixture of 1-benzylimidazole-4-carboxylic acid (34 mg, 0.17 mmol), (6S)-6-amino-4-methyl-7,8-dihydro-6H-pyrazolo[1,5-a][1,3]diazepin-5-one (30 mg, 0.17 mmol), 1-hydroxybenzotriazole (34 mg, 0.25 mmol) and 1-(3-dimethyl aminopropyl)-3-ethylcarbodiimidehydrochloride (48 mg, 0.25 mmol) in N,N-dimethylformamide (5 mL) was stirred at 25° C. for 16 h and concentrated under reduced pressure. The residue was purified by RP-HPLC (acetonitrile 7-37%/0.05% ammonium hydroxide in water) to afford 1-benzyl-N-[(6S)-4-methyl-5-oxo-7,8-dihydro-6H-pyrazolo[1,5-a][1,3]diazepin-6-yl]imidazole-4-carboxamide (14.5 mg, 24%) as a yellow solid. $^1$H NMR (400 MHz, $CD_3OD$) δ 9.16 (s, 1H), 8.10 (s, 1H), 7.53 (d, J=2.0 Hz, 1H), 7.42-7.41 (m, 5H), 6.29 (d, J=2.0 Hz, 1H), 5.44 (s, 2H), 4.44-4.37 (m, 2H), 4.25-4.22 (m, 1H), 3.25 (s, 3H), 2.70-2.65 (m, 1H), 2.27-2.22 (m, 1H). LC-MS $R_T$=0.679 min, m/z=365.1 $[M+H]^+$.

LCMS (5 to 95% acetonitrile in water+0.03% trifluoacetic acid over 1.5 mins) retention time 0.679 min, ESI+ found [M+H]=365.1.

Example 751

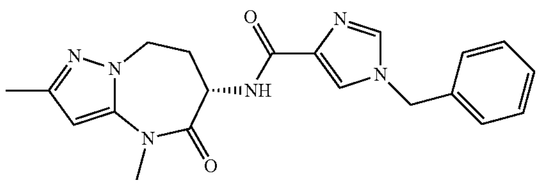 [SMILES: Cc1cc2n(n1)CC[C@H](NC(=O)c1cn(Cc3ccccc3)cn1)C(=O)N2C]

1-benzyl-N-[(6S)-2,4-dimethyl-5-oxo-7,8-dihydro-6H-pyrazolo[1,5-a][1,3]diazepin-6-yl]imidazole-4-carboxamide Amide coupling prepared in a similar fashion to WX Method 184. The crude was purified by RP-HPLC (acetonitrile 10-40%/0.05% ammonium hydroxide in water) to give 1-benzyl-N-[(6S)-2,4-dimethyl-5-oxo-7,8-dihydro-6H-pyrazolo[1,5-a][1,3]diazepin-6-yl]imidazole-4-carboxamide (21.5 mg, 37%) as a yellow solid. $^1H$ NMR (400 MHz, $CD_3OD$) δ 9.21 (s, 1H), 8.16 (s, 1H), 7.47-7.42 (m, 5H), 6.28 (s, 1H), 5.48 (s, 2H), 4.58-4.53 (m, 1H), 4.39-4.27 (m, 2H), 3.30 (s, 3H), 2.77-2.71 (m, 1H), 2.32-2.28 (m, 4H). LC-MS $R_T$=0.709 min, m/z=379.1 $[M+H]^+$.

LCMS (5 to 95% acetonitrile in water+0.03% trifluoacetic acid over 1.5 mins) retention time 0.709 min, ESI+ found [M+H]=379.1

Example 752

WX Method 199

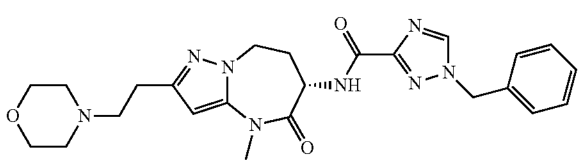

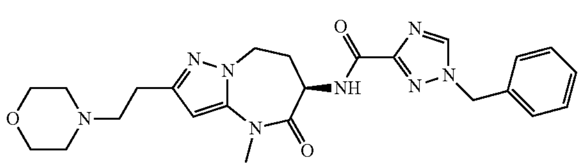

1-benzyl-N-[(6S)-4-methyl-2-(2-morpholinoethyl)-5-oxo-7,8-dihydro-6H-pyrazolo[1,5-a][1,3]diazepin-6-yl]-1,2,4-triazole-3-carboxamide and 1-benzyl-N-[(6R)-4-methyl-2-(2-morpholinoethyl)-5-oxo-7,8-dihydro-6H-pyrazolo[1,5-a][1,3]diazepin-6-yl]-1,2,4-triazole-3-carboxamide

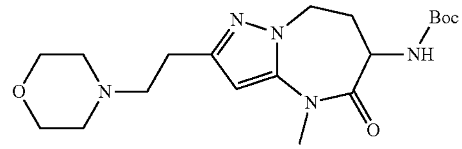 [SMILES: CN1C(=O)C(NC(=O)OC(C)(C)C)CCn2nc(CCN3CCOCC3)cc21]

Step 1: tert-butyl (4-methyl-2-(2-morpholinoethyl)-5-oxo-5,6,7,8-tetrahydro-4H-pyrazolo[1,5-a][1,3]diazepin-6-yl)carbamate A mixture of 2-[6-(tert-butoxycarbonylamino)-4-methyl-5-oxo-7,8-dihydro-6H-pyrazolo[1,5-a][1,3]diazepin-2-yl]ethyl methanesulfonate (200 mg, 0.50 mmol) and morpholine (216 mg, 2.48 mmol) in N,N-dimethylformamide (10 mL) was heated to 50° C. for 6 h and then concentrated under reduced pressure. The residue was purified by flash column chromatography (silica gel, 100-200 mesh, 0 to 10% methanol in dichloromethane) to afford tert-butyl N-[4-methyl-2-(2-morpholinoethyl)-5-oxo-7,8-dihydro-6H-pyrazolo[1,5-a][1,3]diazepin-6-yl]carbamate (150 mg, 77%) as a colorless oil, used as is in the next step.

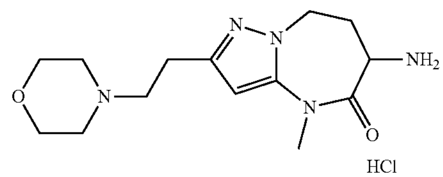 [SMILES: CN1C(=O)C(N)CCn2nc(CCN3CCOCC3)cc21 ; Cl]

Step 2: 6-amino-4-methyl-2-(2-morpholinoethyl)-7,8-dihydro-4H-pyrazolo[1,5-a][1,3]diazepin-5(6H)-one hydrochloride To a solution of tert-butyl N-[4-methyl-2-(2-morpholinoethyl)-5-oxo-7,8-dihydro-6H-pyrazolo[1,5-a][1,3]diazepin-6-yl]carbamate (150 mg, 0.38 mmol) in ethyl acetate (5 mL) was added hydrochloric acid (4.0 M in ethyl acetate, 4.0 mL, 16.0 mmol). The reaction mixture was stirred at 20° C. for 2 h and concentrated under reduced pressure to afford crude 6-amino-4-methyl-2-(2-morpholinoethyl)-7,8-dihydro-4H-pyrazolo[1,5-a][1,3]diazepin-5(6H)-one hydrochloride (120 mg, 96%) as a white solid, used in the next step without further purification.

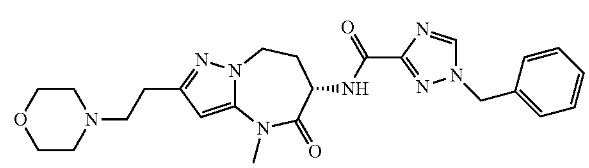

-continued

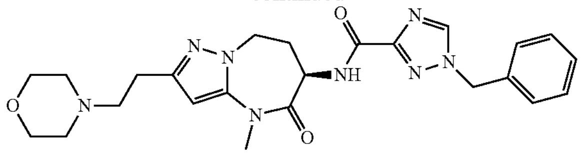

Step 3: 1-benzyl-N-[(6S)-4-methyl-2-(2-morpholinoethyl)-5-oxo-7,8-dihydro-6H-pyrazolo[1,5-a][1,3]diazepin-6-yl]-1,2,4-triazole-3-carboxamide and 1-benzyl-N-[(6R)-4-methyl-2-(2-morpholinoethyl)-5-oxo-7,8-dihydro-6H-pyrazolo[1,5-a][1,3]diazepin-6-yl]-1,2,4-triazole-3-carboxamide A mixture of 1-benzyl-1,2,4-triazole-3-carboxylic acid (40 mg, 0.20 mmol), 6-amino-4-methyl-2-(2-morpholinoethyl)-7,8-dihydro-4H-pyrazolo[1,5-a][1,3]diazepin-5(6H)-one hydrochloride (60 mg, 0.18 mmol), 1-hydroxybenzotriazole (27 mg, 0.20 mmol) and 1-(3-dimethyl aminopropyl)-3-ethylcarbodiimidehydrochloride (38 mg, 0.20 mmol) in N,N-dimethylformamide (5 mL) was stirred at 15° C. for 2 h. The mixture was concentrated under reduced pressure and the residue was purified by RP-HPLC (acetonitrile 35-65%/0.05% $NH_4OH$ in water) to afford 1-benzyl-N-[4-methyl-2-(2-morpholinoethyl)-5-oxo-7,8-dihydro-6H-pyrazolo[1,5-a][1,3]diazepin-6-yl]-1,2,4-triazole-3-carboxamide (70 mg, 81%) as a white solid. The racemic material was further separated by chiral SFC to give:

1-benzyl-N-[(6S)-4-methyl-2-(2-morpholinoethyl)-5-oxo-7,8-dihydro-6H-pyrazolo[1,5-a][1,3]diazepin-6-yl]-1,2,4-triazole-3-carboxamide (Peak 1, retention time 5.064 min) (23 mg, 32%) as a white solid. $^1H$ NMR (400 MHz, $CD_3OD$) δ 8.56 (s, 1H), 7.37-7.34 (m, 5H), 6.20 (s, 1H), 5.48 (s, 2H), 4.53-4.50 (m, 1H), 4.33-4.31 (m, 1H), 4.23-4.21 (m, 1H), 3.73-3.71 (m, 4H), 3.33 (s, 3H), 2.86-2.81 (m, 3H), 2.72-2.67 (m, 2H), 2.58-2.52 (m, 4H), 2.26-2.24 (m, 1H). LCMS $R_T$=0.653 min, m/z=479.2 $[M+H]^+$. LCMS (5 to 95% acetonitrile in water+0.03% trifluoacetic acid over 1.5 mins) retention time 0.653 min, ESI+ found [M+H]=479.2.

1-benzyl-N-[(6R)-4-methyl-2-(2-morpholinoethyl)-5-oxo-7,8-dihydro-6H-pyrazolo[1,5-a][1, 3]diazepin-6-yl]-1,2,4-triazole-3-carboxamide (Peak 2, retention time 6.035 min) (22.7 mg, 32%) as a white solid. $^1H$ NMR (400 MHz, $CD_3OD$) δ 8.56 (s, 1H), 7.37-7.34 (m, 5H), 6.20 (s, 1H), 5.48 (s, 2H), 4.53-4.50 (m, 1H), 4.34-4.31 (m, 1H), 4.24-4.21 (m, 1H), 3.73 (m, 4H), 3.33 (s, 3H), 2.86-2.80 (m, 3H), 2.72-2.67 (m, 2H), 2.58-2.52 (m, 4H), 2.26-2.24 (m, 1H). LCMS $R_T$=0.651 min, m/z=479.2 $[M+H]^+$.

LCMS (5 to 95% acetonitrile in water+0.03% trifluoacetic acid over 1.5 mins) retention time 0.651 min, ESI+ found [M+H]=479.2.

SFC condition: Column: Chiralcel (OD-3 100×4.6 mm I.D., 3 um) Mobile phase: A: CO2 B: ethanol (0.05% DEA), Gradient: from 5% to 40% of B in 4.5 min and hold 40% for 2.5 min, then 5% of B for 1 min, Flow rate: 2.8 mL/min, Column temperature: 40° C.

Example 753

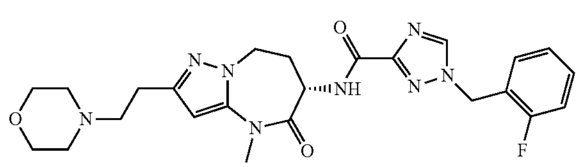

-continued

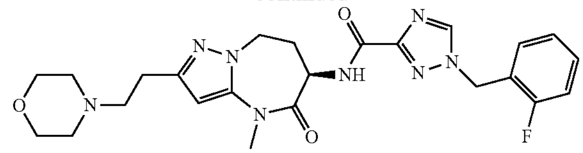

1-[(2-fluorophenyl)methyl]-N-[(6S)-4-methyl-2-(2-morpholinoethyl)-5-oxo-7,8-dihydro-6H-pyrazolo[1,5-a][1,3]diazepin-6-yl]-1,2,4-triazole-3-carboxamide and 1-[(2-fluorophenyl)methyl]-N-[(6R)-4-methyl-2-(2-morpholinoethyl)-5-oxo-7,8-dihydro-6H-pyrazolo[1,5-a][1,3]diazepin-6-yl]-1,2,4-triazole-3-carboxamide Amide coupling prepared in a similar fashion to WX Method 199. The racemic material was separated by chiral SFC to afford:

1-[(2-fluorophenyl)methyl]-N-[(6 S)-4-methyl-2-(2-morpholinoethyl)-5-oxo-7,8-dihydro-6H-pyrazolo[1,5-a][1,3]diazepin-6-yl]-1,2,4-triazole-3-carboxamide (Peak 1, retention time 4.621 min) (17.4 mg, 24%) as a white solid. $^1H$ NMR (400 MHz, $CD_3OD$) δ 8.58 (s, 1H), 7.41-7.38 m, 2H), 7.22-7.15 (m, 2H), 6.19 (s, 1H), 5.55 (s, 2H), 4.55-4.50 (m, 1H), 4.33-4.31 (m, 1H), 4.23-4.21 (m, 1H), 3.73-3.71 (m, 4H), 3.33 (s, 3H), 2.86-2.81 (m, 3H), 2.72-2.67 (m, 2H), 2.58-2.52 (m, 4H), 2.26-2.23 (m, 1H). LCMS $R_T$=0.668 min, m/z=497.2 $[M+H]^+$.

LCMS (5 to 95% acetonitrile in water+0.03% trifluoacetic acid over 1.5 mins) retention time 0.668 min, ESI+ found [M+H]=497.2.

1-[(2-fluorophenyl)methyl]-N-[(6R)-4-methyl-2-(2-morpholinoethyl)-5-oxo-7,8-dihydro-6H-pyrazolo[1,5-a][1,3]diazepin-6-yl]-1,2,4-triazole-3-carboxamide (Peak 2, retention time 6.349 min) (19.8 mg, 27%) as a white solid. $^1H$ NMR (400 MHz, $CD_3OD$) δ 8.58 (s, 1H), 7.42-7.38 (m, 2H), 7.22-7.15 (m, 2H), 6.19 (s, 1H), 5.55 (s, 2H), 4.54-4.52 (m, 1H), 4.33-4.30 (m, 1H), 4.24-4.21 (m, 1H), 3.73-3.70 (m, 4H), 3.33 (s, 3H), 2.86-2.81 (m, 3H), 2.72-2.68 (m, 2H), 2.58-2.52 (m, 4H), 2.26-2.24 (m, 1H). LCMS $R_T$=0.665 min, m/z=497.2 $[M+H]^+$.

LCMS (5 to 95% acetonitrile in water+0.03% trifluoacetic acid over 1.5 mins) retention time 0.665 min, ESI+ found [M+H]=497.2.

SFC condition: Column: Chiralcel (OD-3 100×4.6 mm I.D., 3 um) Mobile phase: A: CO2 B: ethanol (0.05% DEA), Gradient: from 5% to 40% of B in 4.5 min and hold 40% for 2.5 min, then 5% of B for 1 min, Flow rate: 2.8 mL/min, Column temperature: 40° C.

Example 754

WX Method 213

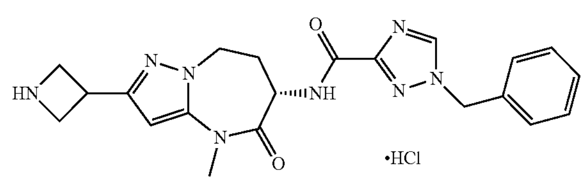

-continued

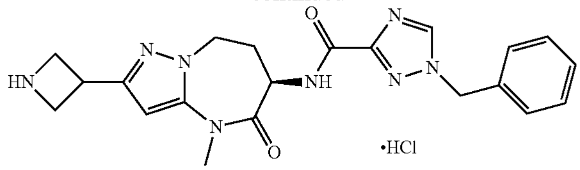

1-benzyl-N-[(6S)-2-(azetidin-3-yl)-4-methyl-5-oxo-7,8-dihydro-6H-pyrazolo[1,5-a][1,3]diazepin-6-yl]-1,2,4-triazole-3-carboxamide hydrochloride and 1-benzyl-N-[(6R)-2-(azetidin-3-yl)-4-methyl-5-oxo-7,8-dihydro-6H-pyrazolo[1,5-a][1,3]diazepin-6-yl]-1,2,4-triazole-3-carboxamide hydrochloride To a stirred mixture solution of tert-butyl 3-[6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate (60 mg, 0.12 mmol) in dichloromethane (5 mL) was added trifluoroacetic acid (120 mg, 1.05 mmol). The resulting mixture was stirred at 25° C. for 12 h and then quenched by addition of saturated aqueous sodium bicarbonate (10 mL). The mixture was extracted with dichloromethane (3×20 mL). The combined organic layers were washed with brine (30 mL), dried over sodium sulfate and concentrated under reduced pressure. The residue was purified by RP-HPLC (acetonitrile 5-35%/0.05% HCl in water) to afford N-[2-(azetidin-3-yl)-4-methyl-5-oxo-7,8-dihydro-6H-pyrazolo[1,5-a][1,3]diazepin-6-yl]-1-benzyl-1,2,4-triazole-3-carboxamide (35 mg, 41%) as a white solid.

The racemic material was separated by chiral SFC and then purified by RP-HPLC (acetonitrile 5-35%/0.05% HCl in water) to give:

1-benzyl-N-[(6S)-2-(azetidin-3-yl)-4-methyl-5-oxo-7,8-dihydro-6H-pyrazolo[1,5-a][1,3]diazepin-6-yl]-1,2,4-triazole-3-carboxamide hydrochloride (Peak 1, retention time 2.254 min) (11.0 mg, 31%) as a white solid. $^1$H NMR (400 MHz, $CD_3OD$) δ 8.90 (s, 1H), 7.41-7.30 (m, 5H), 6.36 (s, 1H), 5.52 (s, 2H), 4.53-4.50 (m, 1H), 4.47-4.14 (m, 7H), 3.34 (s, 3H), 2.88-2.78 (m, 1H), 2.35-2.27 (m, 1H). LCMS $R_T$=2.187 min; m/z=421.2 $(M+H)^+$. LCMS (10 to 80% acetonitrile in water+0.03% ammonia water over 3.0 mins) retention time 2.187 min, ESI+ found [M+H]=421.2.

1-benzyl-N-[(6R)-2-(azetidin-3-yl)-4-methyl-5-oxo-7,8-dihydro-6H-pyrazolo[1,5-a][1,3]diazepin-6-yl]-1,2,4-triazole-3-carboxamide hydrochloride (Peak 2 retention time 3.065 min) (11.1 mg, 32%) as a white solid.

$^1$H NMR (400 MHz, $CD_3OD$) δ 8.82 (s, 1H), 7.43-7.30 (m, 5H), 6.37 (s, 1H), 5.53 (s, 2H), 4.55-4.50 (m, 1H), 4.48-4.14 (m, 7H), 3.37 (s, 3H), 2.89-2.78 (m, 1H), 2.37-2.29 (m, 1H). LCMS $R_T$=2.195 min; m/z=421.2 $(M+H)^+$.

LCMS (10 to 80% acetonitrile in water+0.03% ammonia water over 3.0 mins) retention time 2.195 min, ESI+ found [M+H]=421.2.

SFC conditions: Column: Chiralcel OD-3 150×4.6 mm I.D., 3 um Mobile phase: 40% of methanol (0.1% ethanolamine) in $CO_2$. Flow rate: 2.5 mL/min. Column temp: 35° C.

Example 755

WX Method 192

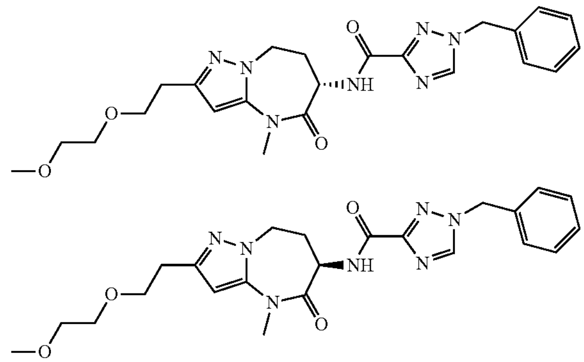

1-benzyl-N-[(6S)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide

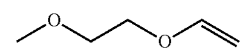

Step 1: (2-methoxyethoxy)ethane

A mixture of iodomethane (7.7 mL, 124.0 mmol), ethylene glycol monovinyl ether (5.0 g, 56.8 mmol) and potassium hydroxide (3.8 g, 68.1 mmol) was stirred at 0° C. for 30 min and then at 20° C. for 3 h. The reaction mixture was diluted with water (20 mL) and extracted with dichloromethane (3×20 mL). The combined organic layers were washed with water (20 mL), brine (20 mL), dried over sodium sulfate and concentrated under reduced pressure to give crude (2-methoxyethoxy)ethane (2 g, 35%) as a colorless oil. $^1$H NMR ($CDCl_3$, 400 MHz) δ 6.52-6.47 (m, 1H), 4.19-4.02 (m, 1H), 4.01-3.99 (m, 1H), 3.82 (t, J=4.4 Hz, 2H), 3.62 (t, J=2.4 Hz, 2H), 3.37 (s, 3H).

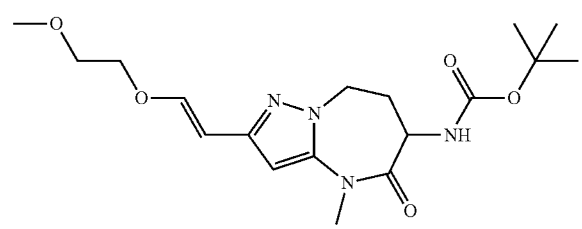 [SMILES: COCCO/C=C/c1cc2n(n1)CCC(NC(=O)OC(C)(C)C)C(=O)N2C]

Step 2: (E)-tert-butyl (2-(2-(2-methoxyethoxy)vinyl)-4-methyl-5-oxo-5,6,7,8-tetrahydro-4H-pyrazolo[1,5-a][1,3]diazepin-6-yl)carbamate A mixture of tert-butyl N-(2-bromo-4-methyl-5-oxo-7,8-dihydro-6H-pyrazolo[1,5-a][1,3]diazepin-6-yl)carbamate (500 mg, 1.39 mmol), N,N-diisopropylethylamine (540 mg, 4.18 mmol), 1-methoxy-2-vinyloxy-ethane (142 mg, 1.39 mmol) and bis(tri-tert-butylphosphine)palladium(0) (71 mg, 0.14 mmol) in 1,4-dioxane (15 mL) was heated at 80° C. for 12 h under nitrogen protection. The reaction was concentrated under reduced pressure and the residue was purified by flash column chromatography (silica gel, 100-200 mesh, 0 to 10% methanol in dichloromethane) to afford (E)-tert-butyl (2-(2-(2-methoxyethoxy)vinyl)-4-methyl-5-oxo-5,6,7,8-tetrahydro-4H-pyrazolo[1,5-a][1,3]diazepin-6-yl)carbamate (140 mg, 26%) as a yellow solid, used as is in the next step. LC-MS $R_T$=1.535 min, m/z=381.2 $[M+H]^+$. LCMS (10 to 80% acetonitrile in water+0.03% ammonium bicarbonate over 3.0 mins) retention time 1.535 min, ESI+ found [M+H]= 381.2.

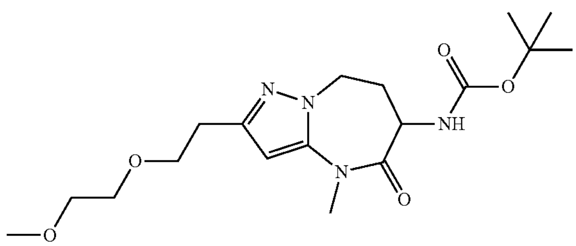 [SMILES: COCCOCCc1cc2n(n1)CCC(NC(=O)OC(C)(C)C)C(=O)N2C]

Step 3: tert-butyl (2-(2-(2-methoxyethoxy)ethyl)-4-methyl-5-oxo-5,6,7,8-tetrahydro-4H-pyrazolo[1,5-a][1,3]diazepin-6-yl)carbamate A mixture of (E)-tert-butyl (2-(2-(2-methoxyethoxy)vinyl)-4-methyl-5-oxo-5,6,7,8-tetrahydro-4H-pyrazolo[1,5-a][1,3]diazepin-6-yl)carbamate (140 mg, 0.37 mmol) and palladium on carbon (10%, 0.1 g) in methanol (10 mL) was hydrogenated (50 psi) at 25° C. for 1.5 h and then filtered. The filtrate was concentrated under reduced pressure and the residue was purified by flash column chromatography (silica gel, 100-200 mesh, 0 to 50% ethyl acetate in petroleum ether) to afford tert-butyl (2-(2-(2-methoxyethoxy)ethyl)-4-methyl-5-oxo-5, 6,7,8-tetrahydro-4H-pyrazolo[1,5-a][1,3]di azepin-6-yl)carbamate (140 mg, 99%) as a colorless oil. LC-MS $R_T$=1.39 min, m/z=383.2 [M+H]+. LCMS (10 to 80% acetonitrile in water+0.03% ammonium bicarbonate over 3.0 mins) retention time 1.39 min, ESI+ found [M+H]= 383.2.

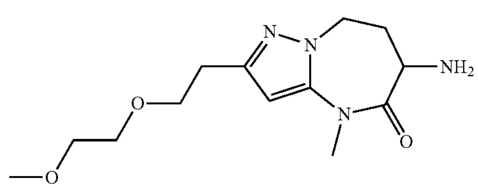 [SMILES: COCCOCCc1cc2n(n1)CCC(N)C(=O)N2C]

Step 4: 6-amino-2-(2-(2-methoxyethoxy)ethyl)-4-methyl-7,8-dihydro-4H-pyrazolo[1,5-a][1,3]diazepin-5(6H)-one To a stirred mixture solution of tert-butyl (2-(2-(2-methoxyethoxy)ethyl)-4-methyl-5-oxo-5,6,7,8-tetrahydro-4H-pyrazolo[1,5-a][1,3]di azepin-6-yl)carbamate (110 mg, 0.29 mmol) in dichloromethane (5 mL) was added trifluoroacetic acid (656 mg, 5.75 mmol). The resulting mixture was stirred 12 h at 25° C. and then quenched by addition of saturated aqueous sodium bicarbonate (10 mL). The mixture was extracted with dichloromethane (3×20 mL). The combined organic layers were washed with brine (30 mL), dried over sodium sulfate and concentrated under reduce pressure to afford the crude 6-amino-2-[2-(2-methoxyethoxy)ethyl]-4-methyl-7,8-dihydro-6H-pyrazolo[1,5-a][1,3]diazepin-5-one (80 mg, 98%) as a yellow oil. LC-MS $R_T$=1.256 min, m/z=283.2 [M+H]+.

LCMS (0 to 60% acetonitrile in water+0.03% ammonium bicarbonate over 3.0 mins) retention time 1.256 min, ESI+ found [M+H]=283.2.

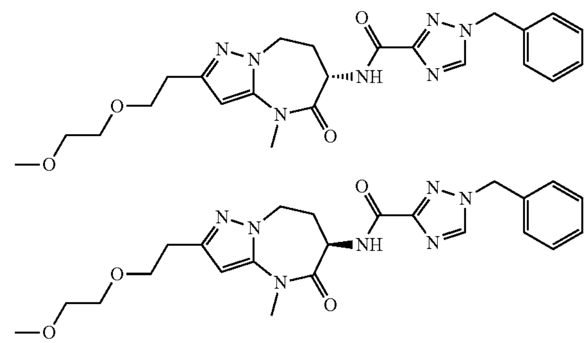

Step 5: 1-benzyl-N-[(6S)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide A mixture of 1-benzyl-1,2,4-triazole-3-carboxylic acid (17 mg, 0.09 mmol), 1-(3-dimethyl aminopropyl)-3-ethylcarbodiimidehydrochloride (27 mg, 0.14 mmol), 6-amino-2-[2-(2-methoxyethoxy)ethyl]-4-methyl-7,8-dihydro-6H-pyrazolo[1,5-a][1,3]diazepin-5-one (20 mg, 0.07 mmol) and 1-hydroxybenzotriazole (27 mg, 0.20 mmol) in N,N-dimethylformamide (3 mL) was stirred at 20° C. for 12 h. The mixture was concentrated under reduce pressure and the residue was purified by RP-HPLC (acetonitrile 25-45%/0.05% $NH_3.H_2O$ in water) to afford 1-benzyl-N-[2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide (20 mg, 60%) as a white solid. The racemic material was further separated by chiral SFC to give:

1-benzyl-N-[(6S)-2-(2-ethoxyethyl)-4-methyl-5-oxo-7,8-dihydro-6H-pyrazolo[1,5-a][1,3]diazepin-6-yl]-1,2,4-triazole-3-carboxamide (Peak 1, retention time 4.593 min) (6 mg, 30%) as a white solid. $^1H$ NMR (400 MHz, $CD_3OD$) δ 8.46 (s, 1H), 7.30-7.22 (m, 5H), 6.11 (s, 1H), 5.37 (s, 2H), 4.44-4.40 (m, 1H), 4.27-4.20 (m, 1H), 4.16-4.07 (m, 1H), 3.65 (t, J=6.8 Hz, 2H), 3.54-3.51 (m, 2H), 3.46-3.42 (m, 2H), 3.25 (s, 3H), 3.23 (s, 3H), 2.79-2.71 (m, 3H), 2.16-2.13 (m, 1H). LC-MS $R_T$=1.355 min, m/z=468.2 $[M+H]^+$. LCMS (10 to 80% acetonitrile in water+0.03% ammonium bicarbonate over 3.0 mins) retention time 1.355 min, ESI+ found [M+H]=468.2.

1-benzyl-N-[(6R)-2-(2-ethoxyethyl)-4-methyl-5-oxo-7,8-dihydro-6H-pyrazolo[1,5-a][1,3]diazepin-6-yl]-1,2,4-triazole-3-carboxamide (Peak 2, retention time 5.435 min) (2 mg, 10%) as a white solid. $^1H$ NMR (400 MHz, $CD_3OD$) δ

8.46 (s, 1H), 7.30-7.23 (m, 5H), 6.11 (s, 1H), 5.38 (s, 2H), 4.44-4.40 (m, 1H), 4.27-4.20 (m, 1H), 4.16-4.07 (m, 1H), 3.65 (t, J=6.8 Hz, 2H), 3.54-3.51 (m, 2H), 3.46-3.42 (m, 2H), 3.26 (s, 3H), 3.23 (s, 3H), 2.79-2.73 (m, 3H), 2.18-2.14 (m, 1H). LC-MS $R_T$=1.400 min, m/z=468.2 [M+H]+. LCMS (10 to 80% acetonitrile in water+0.03% ammonium bicarbonate over 3.0 mins) retention time 1.400 min, ESI+ found [M+H]=468.2.

SFC condition: column: chiralcel OD-3 100×4.6 mm I.D., 3 um mobile phase: A: $CO_2$; B: ethanol (0.05% DEA) gradient: hold 5% for 1.0 min, then from 5% to 40% of B in 4.5 min and hold 40% for 2.5 min, then 5% of B for 1.0 min. Flow rate: 2.8 mL/min. Column temperature: 40° C.

Example 756

WX Method 198

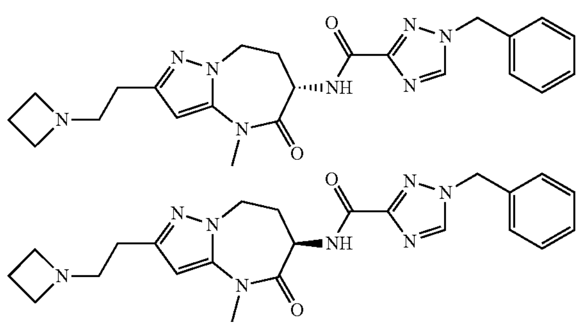

1-benzyl-N-[(6S)-2-[2-(azetidin-1-yl)ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(azetidin-1-yl)ethyl]-4-methyl-5-oxo-7,8-dihydro-6H-pyrazolo[1,5-a][1,3]diazepin-6-yl]-1,2,4-triazole-3-carboxamide

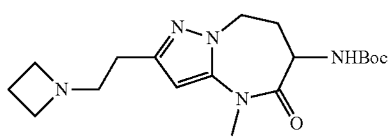 [SMILES: CN1C(=O)C(NC(=O)OC(C)(C)C)CCn2nc(CCN3CCC3)cc21]

Step 1: tert-butyl (2-(2-(azetidin-1-yl)ethyl)-4-methyl-5-oxo-5,6,7,8-tetrahydro-4H-pyrazolo[1,5-a][1,3]diazepin-6-yl)carbamate To a solution of azetidine hydrochloride (186 mg, 1.99 mmol) in acetonitrile (5 mL) was added potassium carbonate (549 mg, 3.98 mmol). The mixture was stirred at 25° C. for 3 h. Then the solid was removed by filtration and the filtrate was concentrated under reduced pressure. The residue was added to a mixture of 2-(6-((tert-butoxycarbonyl)amino)-4-methyl-5-oxo-5,6,7,8-tetrahydro-4H-pyrazolo[1,5-a][1,3]diazepin-2-yl)ethyl methanesulfonate (160 mg, 0.40 mmol), N,N-diisopropylethylamine (308 mg, 2.39 mmol) and sodium iodide (60 mg, 0.40 mmol) in N,N-dimethylformamide (4 mL). The mixture was heated at 50° C. for 16 h and concentrated under reduced pressure. The residue was purified by flash column chromatography (silica gel, 100-200 mesh, 0 to 20% ethyl acetate in petroleum ether) to afford tert-butyl (2-(2-(azetidin-1-yl)ethyl)-4-methyl-5-oxo-5,6,7,8-tetrahydro-4H-pyrazolo[1,5-a][1,3]diazepin-6-yl)carbamate (110 mg, 76%) as a yellow solid, used as is in the next step.

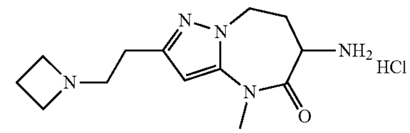 [SMILES: CN1C(=O)C(N)CCn2nc(CCN3CCC3)cc21 ; Cl]

Step 2: 6-amino-2-(2-(azetidin-1-yl)ethyl)-4-methyl-7,8-dihydro-4H-pyrazolo[1,5-a][1,3]diazepin-5(6H)-one hydrochloride To a solution of tert-butyl (2-(2-(azetidin-1-yl)ethyl)-4-methyl-5-oxo-5,6,7,8-tetrahydro-4H-pyrazolo[1,5-a][1,3]diazepin-6-yl)carbamate (110 mg, 0.30 mmol) in ethyl acetate (20 mL) was added hydrochloric acid (4M in ethyl acetate, 12.0 mL, 48.0 mmol. The reaction mixture was stirred at 25° C. for 15 h and concentrated under reduced pressure to afford crude 6-amino-2-(2-(azetidin-1-yl)ethyl)-4-methyl-7,8-dihydro-4H-pyrazolo[1,5-a][1,3]diazepin-5(6H)-one hydrochloride (90 mg, 99%) as a white solid, used in the next step without further purification.

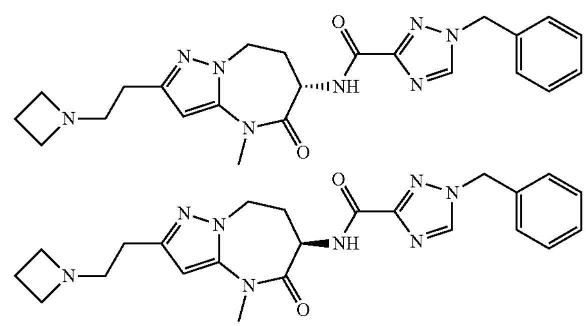

Step 3: 1-benzyl-N-[(6S)-2-[2-(azetidin-1-yl)ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(azetidin-1-yl)ethyl]-4-methyl-5-oxo-7,8-dihydro-6H-pyrazolo[1,5-a][1,3]diazepin-6-yl]-1,2,4-triazole-3-carboxamide A mixture of 6-amino-2-(2-(azetidin-1-yl)ethyl)-4-methyl-7,8-dihydro-4H-pyrazolo[1,5-a][1,3]diazepin-5(6H)-one hydrochloride (60 mg, 0.20 mmol), 1-benzyl-1,2,4-triazole-3-carboxylic acid (41 mg, 0.20 mmol), 1-hydroxybenzotriazole (41 mg, 0.30 mmol) and 1-(3-dimethyl aminopropyl)-3-ethylcarbodiimidehydrochloride (58 mg, 0.30 mmol) in N,N-dimethylformamide (5 mL) was stirred at 15° C. for 12 h. The solvent was evaporated under reduced pressure and the residue was purified by RP-HPLC (3-33% acetonitrile in water and 0.05% hydrochloric acid) to afford N-(2-(2-(azetidin-1-yl)ethyl)-4-methyl-5-oxo-5,6,7,8-tetrahydro-4H-pyrazolo[1,5-a][1,3]diazepin-6-yl)-1-benzyl-1H-1,2,4-triazole-3-carboxamide (40 mg, 45%) as a white solid. The racemic compound was further separated by chiral SFC to afford:

1-benzyl-N-[(6S)-2-[2-(azetidin-1-yl)ethyl]-4-methyl-5-oxo-7,8-dihydro-6H-pyrazolo[1,5-a][1,3]diazepin-6-yl]-1,2,4-triazole-3-carboxamide (Peak 1, retention time 4.941 min) (4.2 mg, 5%) as a white solid. $^1H$ NMR (400 MHz, $CD_3OD$) δ 8.57 (s, 1H), 7.39-7.31 (m, 5H), 6.17 (s, 1H), 5.47 (s, 2H), 4.57-4.52 (m, 1H), 4.33-4.31 (m, 1H), 4.24-4.21 (m, 1H), 3.36-3.34 (m, 2H), 3.33 (s, 3H), 3.32-3.30 (m, 2H), 2.87-2.78 (m, 3H), 2.67-2.63 (m, 2H), 2.25-2.22 (m, 1H), 2.15-2.10 (m, 2H). LC-MS $R_T$=0.603 min, m/z=449.1 $(M+H)^+$. LCMS (5 to 95% acetonitrile in water+0.03% trifluoacetic acid over 1.5 mins) retention time 0.603 min, ESI+ found [M+H]=449.1.

1-benzyl-N-[(6R)-2-[2-(azetidin-1-yl)ethyl]-4-methyl-5-oxo-7,8-dihydro-6H-pyrazolo[1,5-a][1,3]diazepin-6-yl]-1,2,4-triazole-3-carboxamide (Peak 2, retention time 5.372 min) (4.1 mg, 5%) as a white solid. $^1H$ NMR (400 MHz, CD30D) δ 8.57 (s, 1H), 7.40-7.32 (m, 5H), 6.16 (s, 1H), 5.47 (s, 2H), 4.57-4.51 (m, 1H), 4.33-4.31 (m, 1H), 4.25-4.16 (m, 1H), 3.33 (s, 3H), 3.32-3.30 (m, 2H), 3.29-3.28 (m, 2H), 2.87-2.82 (m, 1H), 2.77 (t, J=8.0 Hz, 2H), 2.66-2.61 (m, 2H), 2.29-2.21 (m, 1H), 2.16-2.08 (m, 2H). LC-MS $R_T$=0.604 min, m/z=449.1 $(M+H)^+$.

LCMS (5 to 95% acetonitrile in water+0.03% trifluoacetic acid over 1.5 mins) retention time 0.604 min, ESI+ found [M+H]=449.1.

SFC condition: column chiralpak AD-3 (100 mm*4.6 mm I.D), 3 um mobile phase: A: CO2; B: EtOH (0.05% DEA) gradient: from 5% to 40% of B in 4.5 min and hold 40% for 2.5 min, then 5% of B for 1 min, Flow rate: 2.8 mL/min, Column temperature: 40° C.

Example 757

WX Method 194

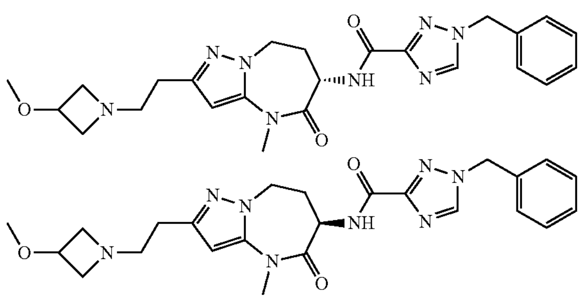

1-benzyl-N-[(6S)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide

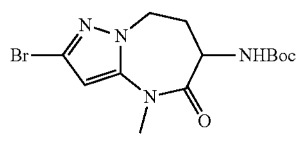 [SMILES: CN1C(=O)C(NC(=O)OC(C)(C)C)CCn2nc(Br)cc21]

Step 1: tert-butyl (2-bromo-4-methyl-5-oxo-5,6,7,8-tetrahydro-4H-pyrazolo[1,5-a][1,3]diazepin-6-yl) carbamate To a solution of 6-amino-2-bromo-4-methyl-7,8-dihydro-6H-pyrazolo[1,5-a][1,3]diazepin-5-one (9.0 g, 34.7 mmol) in dichloromethane (10 mL) was added triethylamine (14.5 mL, 104.2 mmol) and di-tert-butyldicarbonate (11.4 g, 52.1 mmol) at 0° C. The reaction mixture was stirred at 20° C. for 16 h and concentrated to dryness under reduced pressure. The residue was purified by flash column chromatography (silica gel, 100-200 mesh, 0 to 50% ethyl acetate in petroleum ether) to afford tert-butyl (2-bromo-4-methyl-5-oxo-5,6,7,8-tetrahydro-4H-pyrazolo[1,5-a][1,3]diazepin-6-yl)carbamat e (10.5 g, 84%) as a white solid, used as is in the next step.

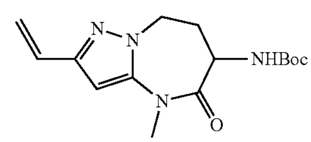 [SMILES: C=Cc1cc2n(n1)CCC(NC(=O)OC(C)(C)C)C(=O)N2C]

Step 2: tert-butyl (4-methyl-5-oxo-2-vinyl-5,6,7,8-tetrahydro-4H-pyrazolo[1,5-a][1,3]diazepin-6-yl) carbamate A mixture of tert-butyl (2-bromo-4-methyl-5-oxo-5,6,7,8-tetrahydro-4H-pyrazolo[1,5-a][1,3]diazepin-6-yl)carbamate (6.0 g, 16.70 mmol), cesium fluoride (7.6 g, 50.11 mmol), bis(di-tert-butyl(4-dimethylaminophenyl)phosphine)dichloropalladium(II) (1.2 g, 1.67 mmol) and potassium vinyltrifluoroborate (4.5 g, 33.40 mmol) in 1,4-dioxane (100 mL)/water (10 mL) was heated at 90° C. for 16 h under nitrogen protection. After cooled, the solvent was removed under reduced pressure and the residue was purified by flash column chromatography (silica gel, 100-200 mesh, 0 to 20% ethyl acetate in petroleum ether) to afford tert-butyl (4-methyl-5-oxo-2-vinyl-5,6,7,8-tetrahydro-4H-pyrazolo[1,5-a][1,3]diazepin-6-yl)carbamate (4.2 g, 82%) as a yellow solid, used as is in the next step. LC-MS $R_T$=0.687 min, m/z=250.8 $[M-56]^+$.

LCMS (5 to 95% acetonitrile in water+0.03% trifluoacetic acid over 1.5 mins) retention time 0.687 min, ESI+ found [M−56]=250.8.

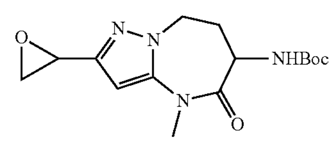 [SMILES: CN1C(=O)C(NC(=O)OC(C)(C)C)CCn2nc(C3CO3)cc21]

Step 3: tert-butyl (4-methyl-2-(oxiran-2-yl)-5-oxo-5,6,7,8-tetrahydro-4H-pyrazolo[1,5-a][1,3]diazepin-6-yl)carbamate To a solution of tert-butyl (4-methyl-5-oxo-2-vinyl-5,6,7,8-tetrahydro-4H-pyrazolo[1,5-a][1,3]diazepin-6-yl)carbamate (3.7 g, 12.08 mmol) in dichloromethane (15 mL) was added 3-chloroperoxybenzoicacid (2.1 g, 12.08 mmol) at 0° C. The reaction mixture was stirred at 0° C. for 3 h and then quenched by addition of saturated aqueous sodium thiosulfate (5 mL). The organic layer was separated, washed with brine (5 mL), dried over sodium sulfate and concentrated under reduced pressure. The residue was purified by flash column chromatography (silica gel, 100-200 mesh, 0 to 50% ethyl acetate in petroleum ether) to afford tert-butyl (4-methyl-2-(oxiran-2-yl)-5-oxo-5,6,7,8-tetrahydro-4H-pyrazolo[1,5-a][1,3]diazepin-6-yl)carbamate (1.1 g, 28%) as a colorless solid. LC-MS $R_T$=0.704 min, m/z=266.8 [M−56]+.

LCMS (5 to 95% acetonitrile in water+0.03% trifluoacetic acid over 1.5 mins) retention time 0.704 min, ESI+ found [M−56]=266.8.

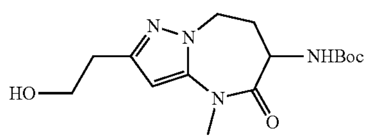 [SMILES: CN1C(=O)C(NC(=O)OC(C)(C)C)CCn2nc(CCO)cc21]

Step 4: tert-butyl (2-(2-hydroxyethyl)-4-methyl-5-oxo-5,6,7,8-tetrahydro-4H-pyrazolo[1,5-a][1,3]diazepin-6-yl)carbamate A mixture of tert-butyl (4-methyl-2-(oxiran-2-yl)-5-oxo-5,6,7,8-tetrahydro-4H-pyrazolo[1,5-a][1,3]diazepin-6-yl) carbamate (1.6 g, 4.96 mmol), palladium on carbon (10%, 528 mg) and ammonium formate (3.2 g, 49.63 mmol) in methanol (15 mL) was hydrogenated (15 psi) at 20° C. for 16 h and then filtered. The filtrate was concentrated under reduced pressure to give crude tert-butyl (2-(2-hydroxyethyl)-4-methyl-5-oxo-5,6,7,8-tetrahydro-4H-pyrazolo[1,5-a][1,3]diazepin-6-yl)carbamate (1.4 g, 87%) as a white solid. LC-MS $R_T$=0.704 min, m/z=268.9 [M−56]+. LCMS (5 to 95% acetonitrile in water+0.03% trifluoacetic acid over 1.5 mins) retention time 0.704 min, ESI+ found [M−56]=268.9.

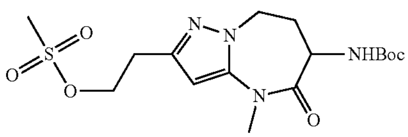 [SMILES: CN1C(=O)C(NC(=O)OC(C)(C)C)CCn2nc(CCOS(C)(=O)=O)cc21]

Step 5: 2-(6-((tert-butoxycarbonyl)amino)-4-methyl-5-oxo-5,6,7,8-tetrahydro-4H-pyrazolo[1,5-a][1,3]diazepin-2-yl)ethyl methanesulfonate To a solution of tert-butyl (2-(2-hydroxyethyl)-4-methyl-5-oxo-5,6,7,8-tetrahydro-4H-pyrazolo[1,5-a][1,3]diazepin-6-yl)carbamate (600 mg, 1.85 mmol) in dichloromethane (20 mL) was added triethylamine (0.77 mL, 5.55 mmol) and methanesulfonyl chloride (600 mg, 5.24 mmol). The reaction mixture was stirred at 20° C. for 2 h and then concentrated under reduced pressure. The residue was purified by flash column chromatography (silica gel, 100-200 mesh, 0 to 80% ethyl acetate in petroleum ether) to afford 2-(6-((tert-butoxycarbonyl)amino)-4-methyl-5-oxo-5,6,7,8-tetrahydro-4H-pyrazolo[1,5-a][1,3]diazepin-2-yl)ethyl methanesulfonate (632 mg, 85%) as a white solid, used as is in the next step.

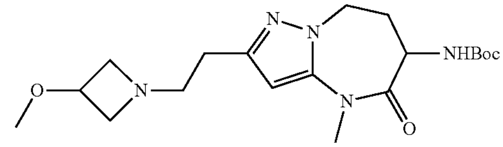 [SMILES: COC1CN(CCc2cc3n(n2)CCC(NC(=O)OC(C)(C)C)C(=O)N3C)C1]

Step 6: tert-butyl (2-(2-(3-methoxyazetidin-1-yl)ethyl)-4-methyl-5-oxo-5,6,7,8-tetrahydro-4H-pyrazolo[1,5-a][1,3]diazepin-6-yl)carbamate To a solution of 3-methoxyazetidinehydrochloride (246 mg, 1.99 mmol) in acetonitrile (5 mL) was added potassium carbonate (549 mg, 3.98 mmol). The mixture was stirred at 25° C. for 3 h and filtered. The filtrate was concentrated under reduced pressure. The residue was added to a mixture of 2-(6-((tert-butoxycarbonyl)amino)-4-methyl-5-oxo-5,6,7,8-tetrahydro-4H-pyrazolo[1,5-a][1,3]diazepin-2-yl)ethyl methanesulfonate (160 mg, 0.40 mmol), N,N-diisopropylethylamine (54 mg, 0.40 mmol) and sodium iodide (60 mg, 0.40 mmol) in N,N-dimethylformamide (4 mL) was heated at 50° C. for 16 h and concentrated under reduced pressure. The residue was purified by flash column chromatography (silica gel, 100-200 mesh, 0 to 20% ethyl acetate in petroleum ether) to give tert-butyl (2-(2-(3-methoxyazetidin-1-yl)ethyl)-4-methyl-5-oxo-5,6,7,8-tetrahydro-4H-pyrazolo[1,5-a][1,3]diazepin-6-yl)carbamate (150 mg, 96%) as a yellow solid, used as is in the next step. LC-MS $R_T$=0.551 min, m/z=394.0 [M−56]+. LCMS (5 to 95% acetonitrile in water+0.03% trifluoacetic acid over 1.5 mins) retention time 0.551 min, ESI+ found [M−56]=394.0.

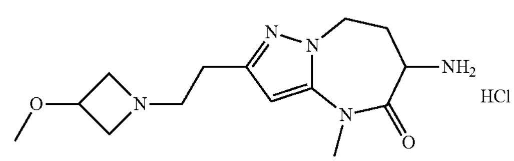 [SMILES: COC1CN(CCc2cc3n(n2)CCC(N)C(=O)N3C)C1 ; Cl]

Step 7: 6-amino-2-(2-(3-methoxyazetidin-1-yl)ethyl)-4-methyl-7,8-dihydro-4H-pyrazolo[1,5-a][1,3]diazepin-5(6H)-one hydrochloride To a solution of tert-butyl (2-(2-(3-methoxyazetidin-1-yl)ethyl)-4-methyl-5-oxo-5,6,7,8-tetrahydro-4H-pyrazolo[1,5-a][1,3]diazepin-6-yl)carbamate (150 mg, 0.38 mmol) in ethyl acetate (20 mL) was added hydrochloric acid (4 M in ethyl acetate, 15.0 mL, 60.0 mmol). The reaction mixture was stirred at 25° C. for 15 h and concentrated under reduced pressure to give crude 6-amino-2-(2-(3-methoxyazetidin-1-yl)ethyl)-4-methyl-7,8-dihydro-4H-pyrazolo[1,5-a][1,3]diazepin-5(6H)-one hydrochloride (125 mg, 99%) as a white solid, used in the next step without further purification.

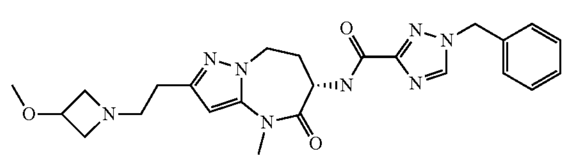

-continued

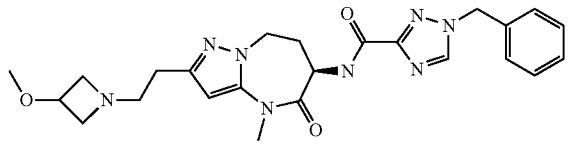

Step 8: 1-benzyl-N-[(6S)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide A mixture of 6-amino-2-[2-(3-methoxyazetidin-1-yl)ethyl]-4-methyl-7,8-dihydro-6H-pyrazolo[1,5-a][1,3]diazepin-5-one hydrochloride (80 mg, 0.24 mmol), 1-benzyl-1,2,4-triazole-3-carboxylic acid (49 mg, 0.24 mmol), 1-hydroxybenzotriazole (49 mg, 0.36 mmol) and 1-(3-dimethyl aminopropyl)-3-ethylcarbodiimidehydrochloride (70 mg, 0.36 mmol) in N,N-dimethylformamide (5 mL) was stirred at 15° C. for 12 h. The solvent was evaporated under reduced pressure and the residue was purified by RP-HPLC (5-35% acetonitrile in water and 0.05% hydrochloric acid) to afford 1-benzyl-N-(2-(2-(3-methoxyazetidin-1-yl)ethyl)-4-methyl-5-oxo-5,6,7,8-tetrahydro-4H-pyrazolo[1,5-a][1,3]diazepin-6-yl)-1H-1,2,4-triazole-3-carboxamide (40 mg, 34%) as a white solid. The racemic compound was further separated by chiral SFC to afford:

1-benzyl-N-[(6 S)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide (Peak 1, retention time 1.696 min) (3.5 mg, 3%) as a white solid. $^1$H NMR (400 MHz, $CD_3OD$) δ 8.56 (s, 1H), 7.35 (s, 5H), 6.17 (s, 1H), 5.47 (s, 2H), 4.57-4.52 (m, 1H), 4.37-4.31 (m, 1H), 4.26-4.19 (m, 1H), 4.06-4.00 (m, 1H), 3.63 (t, J=6.8 Hz, 2H), 3.33 (s, 3H), 3.25 (s, 3H), 3.02 (t, J=6.4 Hz, 2H), 2.84-2.80 (m, 3H), 2.67 (t, J=7.2 Hz, 2H), 2.29-2.21 (m, 1H). LC-MS $R_T$=0.556 min, m/z=479.1 $(M+H)^+$.

LCMS (5 to 95% acetonitrile in water+0.03% trifluoacetic acid over 1.5 min) retention time 0.556 min, ESI+ found [M+H]=479.1. 1-benzyl-N-[(6R)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide (Peak 2, retention time 1.995 min) (3.5 mg, 3%) as a white solid. $^1$H NMR (400 MHz, $CD_3OD$) δ 8.56 (s, 1H), 7.38-7.32 (m, 5H), 6.17 (s, 1H), 5.47 (s, 2H), 4.57-4.52 (m, 1H), 4.36-4.31 (m, 1H), 4.26-4.17 (m, 1H), 4.06-4.02 (m, 1H), 3.63 (t, J=7.0 Hz, 2H), 3.33 (s, 3H), 3.25 (s, 3H), 3.02 (t, J=6.6 Hz, 2H), 2.84-2.80 (m, 3H), 2.67 (t, J=7.4 Hz, 2H), 2.29-2.21 (m, 1H). LC-MS $R_T$=0.550 min, m/z=479.1 $(M+H)^+$.

LCMS (5 to 95% acetonitrile in water+0.03% trifluoacetic acid over 1.5 mins) retention time 0.550 min, ESI+ found [M+H]=479.1.

SFC condition: column chiralpak AD-3 (50 mm*4.6 mm I.D), 3 um mobile phase: A: CO2; B: EtOH (0.05% DEA) gradient: hold 5% for 0.2 min, then from 5% to 40% of B in 1.4 min and hold 40% for 1.05 min, then 5% of B for 0.35 min. Flow rate: 4 mL/min. Column temperature: 40° C.

Example 758

WX Method 190

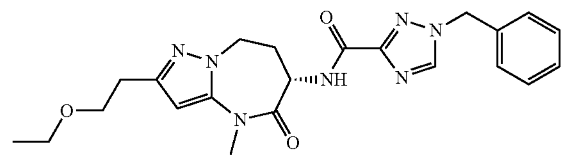

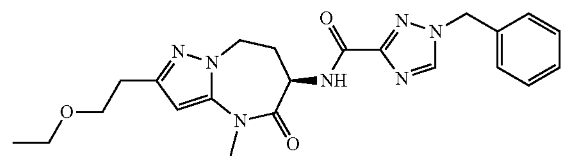

1-benzyl-N-[(6S)-2-(2-ethoxyethyl)-4-methyl-5-oxo-7,8-dihydro-6H-pyrazolo[1,5-a][1,3]diazepin-6-yl]-1,2,4-triazole-3-carboxamide and 1-benzyl-N-[(6R)-2-(2-ethoxyethyl)-4-methyl-5-oxo-7,8-dihydro-6H-pyrazolo[1,5-a][1,3]diazepin-6-yl]-1,2,4-triazole-3-carboxamide

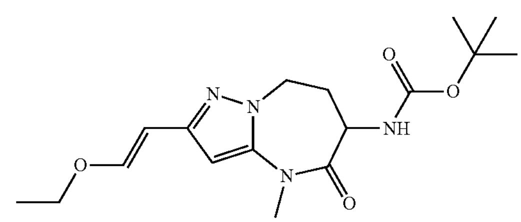 [SMILES: CCO/C=C/c1cc2n(n1)CCC(NC(=O)OC(C)(C)C)C(=O)N2C]

Step 1: tert-butyl N-[2-[(E)-2-ethoxyvinyl]-4-methyl-5-oxo-7,8-dihydro-6H-pyrazolo[1,5-a][1,3]diazepin-6-yl]carbamate A mixture of ethyl vinyl ether (40 mg, 0.56 mmol), N,N-diisopropylethylamine (216 mg, 1.67 mmol), bis(tri-tert-butylphosphine)palladium (28 mg, 0.06 mmol) and tert-butyl N-(2-bromo-4-methyl-5-oxo-7,8-dihydro-6H-pyrazolo[1,5-a][1,3]diazepin-6-yl) carbamate (200 mg, 0.56 mmol) in 1,4-dioxane (15 mL) was heated at 80° C. for 12 h under nitrogen protection. After cooled, the reaction mixture was concentrated under reduced pressure and the residue was purified by flash column chromatography (silica gel, 100-200 mesh, 0 to 10% methanol in dichloromethane) to afford tert-butyl N-[2-[(E)-2-ethoxyvinyl]-4-methyl-5-oxo-7,8-dihydro-6H-pyrazolo[1,5-a][1,3]diazepin-6-yl]carbamate (100 mg, 51%) as a yellow solid. LCMS $R_T$=2.13 min, m/z=351.2 $[M+H]^+$.

LCMS (0 to 60% acetonitrile in water+0.03% ammonium bicarbonate over 3.0 mins) retention time 2.13 min, ESI+ found [M+H]=351.2.

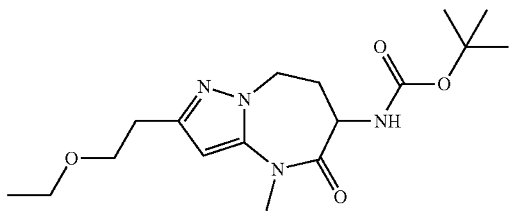 [SMILES: CCOCCc1cc2n(n1)CCC(NC(=O)OC(C)(C)C)C(=O)N2C]

Step 2: tert-butyl (2-(2-ethoxyethyl)-4-methyl-5-oxo-5,6,7,8-tetrahydro-4H-pyrazolo[1,5-a][1,3]diazepin-6-yl)carbamate A mixture of tert-butyl N-[2-[(E)-2-ethoxyvinyl]-4-methyl-5-oxo-7,8-d8-dihydro-6H-pyrazolo[1,5-a][1,3]diazepin-6-yl]carbamate (100 mg, 0.29 mmol) and palladium on carbon (10%, 0.1 g) in methanol (50 mL) was hydrogenated (50 psi) at 25° C. for 1.5 h and then filtered. The filtrate was concentrated under reduced pressure. The residue was purified by flash column chromatography (silica gel, 100-200 mesh, 0 to 50% ethyl acetate in petroleum ether) to give tert-butyl (2-(2-ethoxyethyl)-4-methyl-5-oxo-5,6,7,8-tetrahydro-4H-pyrazolo[1,5-a][1,3]diazepin-6-yl) carbamate (60 mg, 60%) as a yellow oil. LCMS $R_T$=0.779 min, m/z=353.1 [M+H].

LCMS (5 to 95% acetonitrile in water+0.03% trifluoacetic acid over 1.5 mins) retention time 0.779 min, ESI+ found [M+H]=353.1.

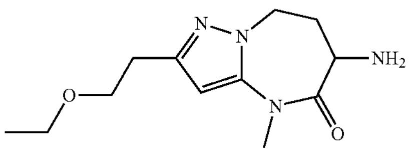 [SMILES: CCOCCc1cc2n(n1)CCC(N)C(=O)N2C]

Step 3: 6-amino-2-(2-ethoxyethyl)-4-methyl-7,8-dihydro-4H-pyrazolo[1,5-a][1,3]diazepin-5(6H)-one To a solution of tert-butyl (2-(2-ethoxyethyl)-4-methyl-5-oxo-5,6,7,8-tetrahydro-4H-pyrazolo[1,5-a][1,3]diazepin-6-yl) carbamate (90 mg, 0.26 mmol) in dichloromethane (5 mL) was added trifluoroacetic acid (874 mg, 7.66 mmol). The resulting mixture was stirred at 25° C. for 12 h and then quenched by addition of saturated aqueous sodium bicarbonate (10 mL). The mixture was extracted with dichloromethane (3×20 mL). The combined organic layers were washed with brine (30 mL), dried over sodium sulfate and concentrated under reduce pressure to give the crude 6-amino-2-(2-ethoxyethyl)-4-methyl-7,8-dihydro-6H-pyrazolo[1,5-a][1,3]diazepin-5-one (50 mg, 78%) as a yellow oil, used in the next step without further purification.

LCMS (0 to 60% acetonitrile in water+0.03% ammonium bicarbonate over 3.0 mins) retention time 1.325 min, ESI+ found [M+H]=253.2.

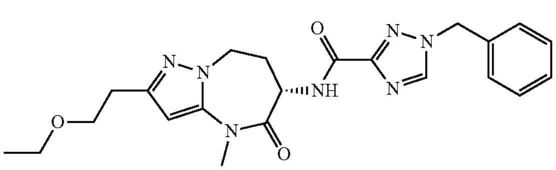

-continued

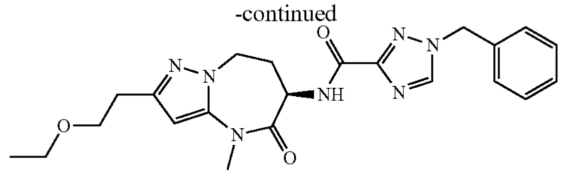

Step 4: 1-benzyl-N-[(6S)-2-(2-ethoxyethyl)-4-methyl-5-oxo-7,8-dihydro-6H-pyrazolo[1,5-a][1,3]diazepin-6-yl]-1,2,4-triazole-3-carboxamide and 1-benzyl-N-[(6R)-2-(2-ethoxyethyl)-4-methyl-5-oxo-7,8-dihydro-6H-pyrazolo[1,5-a][1,3]diazepin-6-yl]-1,2,4-triazole-3-carboxamide A mixture of 1-benzyl-1,2,4-triazole-3-carboxylic acid (24 mg, 0.12 mmol), 1-(3-dimethyl aminopropyl)-3-ethylcarbodiimidehydrochloride (38 mg, 0.20 mmol), 6-amino-2-(2-ethoxyethyl)-4-methyl-7,8-dihydro-6H-pyrazolo[1,5-a][1,3]diazepin-5-one (25 mg, 0.10 mmol) and 1-hydroxybenzotriazole (27 mg, 0.20 mmol) in N,N-dimethylformamide (3 mL) was stirred at 20° C. for 12 h. The mixture was concentrated under reduce pressure and the residue was purified by RP-HPLC (acetonitrile 22-52%/0.05% $NH_3.H_2O$ in water) to afford 1-benzyl-N-[2-(2-ethoxyethyl)-4-methyl-5-oxo-7,8-dihydro-6H-pyrazolo[1,5-a][1,3]diazepin-6-yl]-1,2,4-triazole-3-carboxamide (25 mg, 58%) as a white solid. The racemic material was further separated by chiral SFC to give:

1-benzyl-N-[(6S)-2-(2-ethoxyethyl)-4-methyl-5-oxo-7,8-dihydro-6H-pyrazolo[1,5-a][1,3]diazepin-6-yl]-1,2,4-triazole-3-carboxamide (Peak 1, retention time 4.421 min) (4.3 mg, 17%) as a white solid. $^1H$ NMR (400 MHz, $CD_3OD$) δ 8.46 (s, 1H), 7.27-7.24 (m, 5H), 6.09 (s, 1H), 5.38 (s, 2H), 4.44-4.41 (m, 1H), 4.36-4.30 (m, 1H), 4.24-4.19 (m, 1H), 3.61 (t, J=6.8 Hz, 2H), 3.45-3.43 (m, 2H), 3.23 (s, 3H), 2.78-2.74 (m, 3H), 2.17-2.13 (m, 1H), 1.09 (t, J=7.2 Hz, 3H). LC-MS RT=1.482 min, m/z=438.2 $[M+H]^+$. LCMS (10 to 80% acetonitrile in water+0.03% ammonium bicarbonate over 3.0 mins) retention time 1.482 min, ESI+ found [M+H]= 438.2.

1-benzyl-N-[(6R)-2-(2-ethoxyethyl)-4-methyl-5-oxo-7,8-dihydro-6H-pyrazolo[1,5-a][1,3]diazepin-6-yl]-1,2,4-triazole-3-carboxamide (Peak 2, retention time 5.225 min) (7.5 mg, 30%) as a white solid. $^1H$ NMR (400 MHz, $CD_3OD$) δ 8.46 (s, 1H), 7.27-7.24 (m, 5H), 6.09 (s, 1H), 5.38 (s, 2H), 4.44-4.41 (m, 1H), 4.30-4.20 (m, 1H), 4.19-4.10 (m, 1H), 3.61 (t, J=6.8 Hz, 2H), 3.45-3.43 (m, 2H), 3.23 (s, 3H), 2.78-2.74 (m, 3H), 2.19-2.13 (m, 1H), 1.09 (t, J=7.2 Hz, 3H). LC-MS RT=1.483 min, m/z=438.2 $[M+H]^+$.

LCMS (10 to 80% acetonitrile in water+0.03% ammonium bicarbonate over 3.0 mins) retention time 1.483 min, ESI+ found [M+H]=438.2.

SFC condition: column: chiralcel OD-3 50×4.6 mm I.D., 3 um mobile phase: A: $CO_2$; B: ethanol (0.05% DEA) gradient: hold 5% for 0.2 min, then from 5% to 40% of Bin 1.4 min and hold 40% for 1.05 min, then 5% of B for 0.35 min. Flow rate: 2.8 mL/min. Column temperature: 40° C.

Example 759

WX Method 212

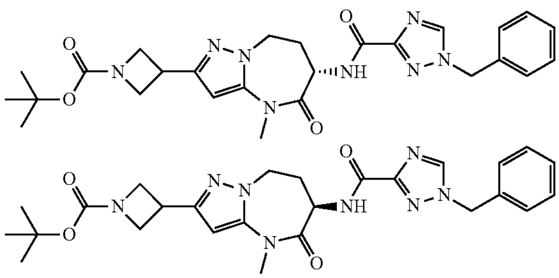

tert-butyl 3-[(6S)-6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate and tert-butyl 3-[(6R)-6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate

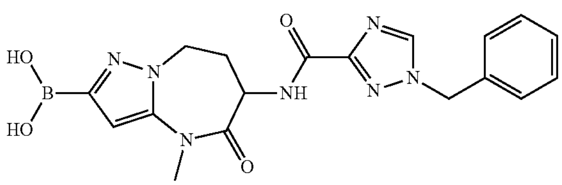 [SMILES: CN1C(=O)C(NC(=O)c2ncn(Cc3ccccc3)n2)CCn2nc(B(O)O)cc21]

Step 1: (6-(1-benzyl-1H-1,2,4-triazole-3-carboxamido)-4-methyl-5-oxo-5,6,7,8-tetrahydro-4H-pyrazolo[1,5-a][1,3]diazepin-2-yl)boronic acid A mixture of 1-benzyl-N-(2-bromo-4-methyl-5-oxo-7,8-dihydro-6H-pyrazolo[1,5-a][1,3]diazepin-6-yl)-1,2,4-triazole-3-carboxamide (2.5 g, 5.63 mmol), 4,4,4',4',5,5,5',5'-octamethyl-2,2'-bi(1,3,2-dioxaborolane) (2.1 g, 8.44 mmol), 1,1-bis(diphenylphosphino) ferrocene palladium dichloride (0.4 g, 0.56 mmol) and potassium acetate (1.7 g, 16.88 mmol) in 1,4-dioxane (20 mL) was heated at 90° C. for 12 h and filtered. The filtrate was concentrated under reduced pressure and the residue was purified by RP-HPLC (acetonitrile 18-28/0.05% ammonia in water) to give [6-[(1-benzyl-1,2,4-triazole-3-carbonyl)amino]-4-methyl-5-oxo-7,8-dihydro-6H-pyrazolo[1,5-a][1,3]diazepin-2-yl]boronic acid (1.0 g, 43%) as a white solid. LCMS (5 to 95% acetonitrile in water+0.03% trifluoacetic acid over 1.5 mins) retention time 0.687 min, ESI+ found [M+H]=410.1.

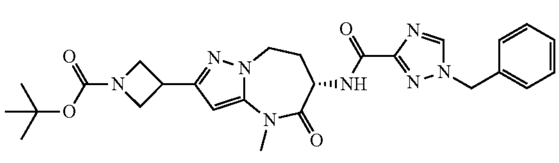

-continued

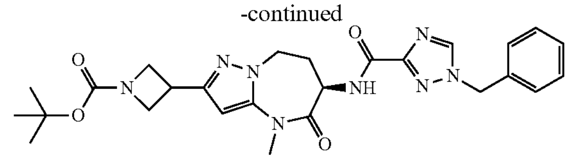

Step 2: tert-butyl 3-[(6S)-6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate and tert-butyl 3-[(6R)-6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate A mixture of tert-butyl 3-iodoazetidine-1-carboxylate (276 mg, 0.98 mmol), [6-[(1-benzyl-,2,4-triazole-3-carbonyl)amino]-4-methyl-1-oxo-7,8-dihydro-6H-pyrazolo[1,5-a][1,3]diazepin-2-yl]boronic acid (200 mg, 0.49 mmol), cesium carbonate (159 mg, 0.49 mmol) and cyclopentyl (diphenyl)phosphane dichloromethane dichloropalladium iron (399 mg, 0.49 mmol) in 1,4-dioxane (15 mL) and water (3 mL) was stirred at 90° C. for 0.5 h under microwave conditions. The reaction mixture was concentrated under reduced pressure and the residue was purified by flash column chromatography (silica gel, 100-200 mesh, 0 to 5% methanol in dichloromethane) to afford tert-butyl 3-[6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate (60 mg, 24%) as a white solid. The racemic material (25 mg) was further separated by chiral SFC to give:

tert-butyl 3-[(6S)-6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate (Peak 1 retention time 5.537 min) (7.5 mg, 30%) as a white solid. $^1H$ NMR (400 MHz, $CD_3OD$) δ 8.56 (s, 1H), 7.41-7.31 (m, 5H), 6.30 (s, 1H), 5.47 (s, 2H), 4.58-4.49 (m, 1H), 4.44-4.19 (m, 4H), 4.09-3.98 (m, 2H), 3.85-3.76 (m, 1H), 3.39 (s, 3H), 2.92-2.79 (m, 1H), 2.32-2.22 (s, 1H), 1.46 (s, 9H). LCMS $R_T$=1.747 min; m/z=421.2 $(M-100)^+$. LCMS (10 to 80% acetonitrile in water+0.03% ammonia water over 3.0 mins) retention time 1.747 min, ESI+ found [M−100]=421.2. tert-butyl 3-[(6R)-6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate (Peak 2 retention time 6.650 min) (10.0 mg, 40%) as a white solid. $^1H$ NMR (400 MHz, $CD_3OD$) δ 8.56 (s, 1H), 7.41-7.31 (m, 5H), 6.30 (s, 1H), 5.47 (s, 2H), 4.58-4.48 (m, 1H), 4.45-4.19 (m, 4H), 4.09-3.98 (m, 2H), 3.85-3.76 (m, 1H), 3.39 (s, 3H), 2.92-2.79 (m, 1H), 2.32-2.22 (s, 1H), 1.46 (s, 9H). LCMS $R_T$=1.747 min; m/z=421.2 $(M-100)^+$. LCMS (10 to 80% acetonitrile in water+0.03% ammonia water over 3.0 mins) retention time 1.747 min, ESI+ found [M−100]=421.2.

SFC condition Column: ChiralPak AD-3 150×4.6 mm I.D., 3 um Mobile phase: A: CO2 B: Ethanol (0.05% DEA). Gradient: from 5% to 40% of B in 5.5 min and hold 40% for 3 min, then 5% of B for 1.5 min. Flow rate: 2.5 mL/min. Column temperature: 40° C.

Example 760

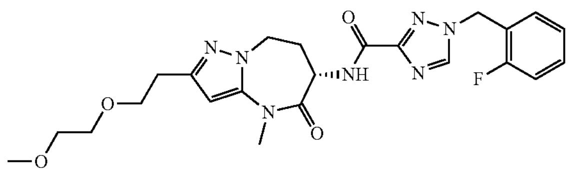

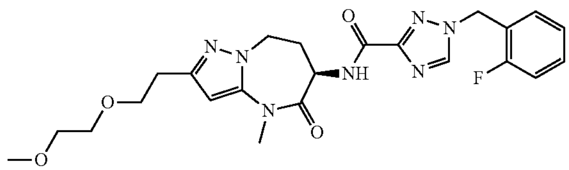

1-[(2-fluorophenyl)methyl]-N-[(6S)-2-[2-(2-methoxyethoxy)ethyl]-4-methyl-5-oxo-7,8-di hydro-6H-pyrazolo[1,5-a][1,3]diazepin-6-yl]-1,2,4-triazole-3-carboxamide and 1-[(2-fluorophenyl)methyl]-N-[(6R)-2-[2-(2-methoxyethoxy)ethyl]-4-methyl-5-oxo-7,8-di hydro-6H-pyrazolo[1,5-a][1,3]diazepin-6-yl]-1,2,4-triazole-3-carboxamide Amide coupling prepared in a similar fashion to WX Method 192. The racemic material was separated by chiral SFC to afford:

1-[(2-fluorophenyl)methyl]-N-[(6S)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide (Peak 1, retention time 4.167 min) (17 mg, 56%) as a white solid. $^1$H NMR (400 MHz, $CD_3OD$) δ 8.47 (s, 1H), 7.30-7.26 (m, 2H), 7.11-7.02 (m, 2H), 6.11 (s, 1H), 5.45 (s, 2H), 4.43-4.40 (m, 1H), 4.25-4.22 (m, 1H), 4.15-4.10 (m, 1H), 3.64 (t, J=6.8 Hz, 2H), 3.52-3.51 (m, 2H), 3.49-3.45 (m, 2H), 3.25 (s, 3H), 3.22 (s, 3H), 2.78-2.75 (m, 3H), 2.19-2.14 (m, 1H). LC-MS $R_T$=0.748 min, m/z=508.2.2 $[M+Na]^+$. LCMS (5 to 95% acetonitrile in water+0.03% trifluoacetic acid over 1.5 mins) retention time 0.748 min, ESI+ found [M+Na]=508.2.

1-[(2-fluorophenyl)methyl]-N-[(6R)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide (Peak 2, retention time 4.878 min) (11.4 mg, 38%) as a white solid. $^1$H NMR (400 MHz, $CD_3OD$) δ 8.47 (s, 1H), 7.30-7.26 (m, 2H), 7.11-7.02 (m, 2H), 6.11 (s, 1H), 5.45 (s, 2H), 4.43-4.40 (m, 1H), 4.26-4.22 (m, 1H), 4.16-4.10 (m, 1H), 3.64 (t, J=6.8 Hz, 2H), 3.52-3.51 (m, 2H), 3.49-3.44 (m, 2H), 3.25 (s, 3H), 3.22 (s, 3H), 2.78-2.75 (m, 3H), 2.19-2.14 (m, 1H). LC-MS $R_T$=0.744 min, m/z=508.2 $[M+H]^+$.

LCMS (5 to 95% acetonitrile in water+0.03% trifluoacetic acid over 1.5 mins) retention time 0.744 min, ESI+ found [M+Na]=508.2.

SFC conditions: (Column: Chiralcel OD-3 100×4.6 mm I.D., 3 um Mobile phase: A: $CO_2$ B: ethanol (0.05% dethyl acetate), Gradient: from 5% to 40% of B in 4.5 min and hold 40% for 2.5 min, then 5% of B for 1 min, Flow rate: 2.8 mL/min Column temperature: 40° C.

Example 761

WX Method 203

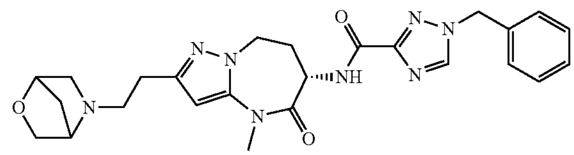

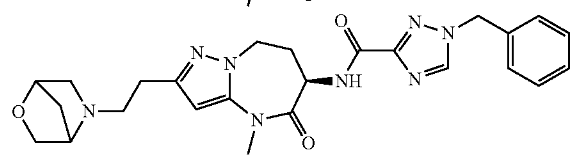

1-benzyl-N-[(6S)-4-methyl-2-[2-(2-oxa-5-azabicyclo[2.2.1]heptan-5-yl)ethyl]-5-oxo-7,8-di hydro-6H-pyrazolo[1,5-a][1,3]diazepin-6-yl]-1,2,4-triazole-3-carboxamide and 1-benzyl-N-[(6R)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide

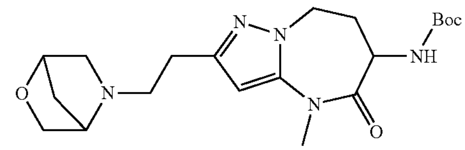 [SMILES: CN1C(=O)C(NC(=O)OC(C)(C)C)CCn2nc(CCN3CC4CC3CO4)cc21]

Step 1: tert-butyl (2-(2-(2-oxa-5-azabicyclo[2.2.1]heptan-5-yl)ethyl)-4-methyl-5-oxo-5,6,7,8-tetrahydro-4H-pyrazolo[1,5-a][1,3]diazepin-6-yl)carbamate A mixture of 2-[6-(tert-butoxycarbonylamino)-4-methyl-5-oxo-7,8-dihydro-6H-pyrazolo[1,5-a][1,3]diazepin-2-yl]ethyl methanesulfonate (230 mg, 0.57 mmol), 2-oxa-5-azabicyclo[2.2.1]heptane hydrochloride (232 mg, 1.71 mmol) and potassium carbonate (237 mg, 1.71 mmol) in N,N-dimethylformamide (10 mL) was heated at 50° C. for 6 h and concentrated under reduced pressure. The residue was purified by RP-HPLC (acetonitrile 25-55%/0.05% $NH_4OH$ in water) to afford tert-butyl (2-(2-(2-oxa-5-azabicyclo[2.2.1]heptan-5-yl)ethyl)-4-methyl-5-oxo-5,6,7,8-tetrahydro-4H-pyrazolo[1,5-a][1,3]diazepin-6-yl)carbamate (100 mg, 43%) as a colorless oil, used as is in the next step.

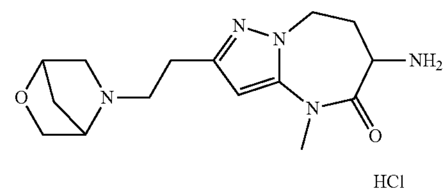 [SMILES: CN1C(=O)C(N)CCn2nc(CCN3CC4CC3CO4)cc21 ; Cl]

HCl

Step 2: 2-(2-(2-oxa-5-azabicyclo[2.2.1]heptan-5-yl)ethyl)-6-amino-4-methyl-7,8-dihydro-4H-pyrazolo[1,5-a][1,3]diazepin-5(6H)-one hydrochloride To a solution of tert-butyl (2-(2-(2-oxa-5-azabicyclo[2.2.1]heptan-5-yl)ethyl)-4-methyl-5-oxo-5,6,7,8-tetrahydro-4H-pyrazolo[1,5-a][1,3]diazepin-6-yl)carbamate (100 mg, 0.25 mmol) in ethyl acetate (5 mL) was added hydrochloric acid (4 M in ethyl acetate, 4.0 mL, 16.0 mmol). The reaction mixture was stirred at 20° C. for 2 h and concentrated under reduced pressure to afford crude 2-(2-(2-oxa-5-azabicyclo[2.2.1]heptan-5-yl)ethyl)-6-amino-4-methyl-7,8-dihydro-4H-pyrazol o[1,5-a][1,3]diazepin-5(6H)-one hydrochloride (80 mg, 95%) as a white solid, used in the next step without further purification.

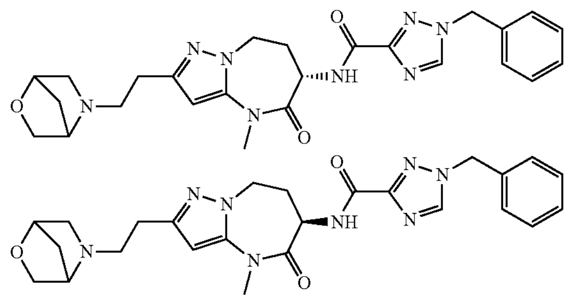

Step 3: 1-benzyl-N-[(6S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide and 1-benzyl-N-[(6R)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide A mixture of 1-benzyl-1,2,4-triazole-3-carboxylic acid (30 mg, 0.15 mmol), 2-(2-(2-oxa-5-azabicyclo[2.2.1]heptan-5-yl)ethyl)-6-amino-4-methyl-7,8-dihydro-4H-pyrazol o[1,5-a][1,3]diazepin-5(6H)-one hydrochloride (40 mg, 0.12 mmol), 1-(3-dimethylaminopropyl)-3-ethylcarbodiimidehydrochloride (23 mg, 0.12 mmol) and 1-hydroxybenzotriazole (16 mg, 0.12 mmol) in N,N-dimethylformamide (5 mL) was stirred at 20° C. for 2 h. The mixture was concentrated under reduced pressure and the residue was purified by RP-HPLC (acetonitrile 18-48%/0.05% $NH_4OH$ in water) to afford 1-benzyl-N-[4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide (30 mg, 52%) as a white solid. The racemic material was separated by chiral SFC to give:

1-benzyl-N-[(6S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide (Peaks 1 and 2, retention time 5.386 min, 5.502 min) (10.7 mg, 36%) as a white solid. $^1H$ NMR (400 MHz, $CD_3OD$) δ 8.57 (s, 1H), 7.39-7.33 (m, 5H), 6.20 (s, 1H), 5.47 (s, 2H), 4.55-4.52 (m, 1H), 4.33-4.31 (m, 1H), 4.30-4.25 (m, 1H), 4.24-4.15 (m, 1H), 4.06-4.03 (m, 1H), 3.64-3.61 (m, 2H), 3.33 (s, 3H), 2.93-2.77 (m, 6H), 2.62-2.59 (m, 1H), 2.26-2.20 (m, 1H), 1.92-1.89 (m, 1H), 1.78-1.75 (m, 1H). LCMS $R_T$=0.670 min, m/z=491.2 $[M+H]^+$. LCMS (5 to 95% acetonitrile in water+0.03% trifluoacetic acid over 1.5 mins) retention time 0.670 min, ESI+ found [M+H]=491.2.

1-benzyl-N-[(6R)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide (peak 3, retention time 6.674 min) (9.8 mg, 33%) as a white solid. $^1H$ NMR (400 MHz, $CD_3OD$) 8.57 (s, 1H), 7.39-7.33 (m, 5H), 6.20 (s, 1H), 5.47 (s, 2H), 4.55-4.52 (m, 1H), 4.34-4.30 (m, 1H), 4.30-4.24 (m, 1H), 4.25-4.15 (m, 1H), 4.06-4.03 (m, 1H), 3.64-3.61 (m, 2H), 3.33 (s, 3H), 2.93-2.77 (m, 6H), 2.62-2.59 (m, 1H), 2.26-2.20 (m, 1H), 1.92-1.89 (m, 1H), 1.78-1.74 (m, 1H). LCMS $R_T$=0.669 min, m/z=491.2 $[M+H]^+$.

LCMS (5 to 95% acetonitrile in water+0.03% trifluoacetic acid over 1.5 mins) retention time 0.669 min, ESI+ found [M+H]=491.2.

SFC condition: Column: Chiralcel (OD-3 100×4.6 mm I.D., 3 um) Mobile phase: A: CO2 B: ethanol (0.05% DEA) Gradient: from 5% to 40% of B in 4.5 min and hold 40% for 2.5 min, then 5% of B for 1 min, Flow rate: 2.8 mL/min Column temperature: 40° C.

Example 762

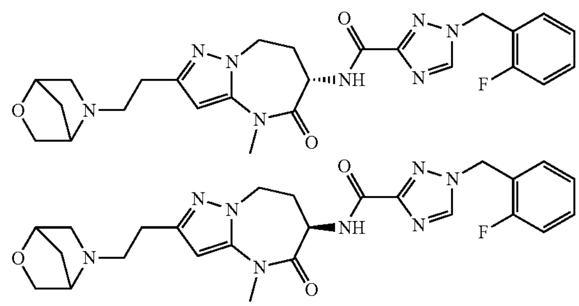

1-[(2-fluorophenyl)methyl]-N-[(6S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide and 1-[(2-fluorophenyl)methyl]-N-[(6R)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide Amide coupling prepared in a similar fashion to WX Method 203. The racemic material was separated by chiral SFC to afford:

1-[(2-fluorophenyl)methyl]-N-[(6 S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide (Peaks 1 and 2, retention time 4.939, 5.026 min) (15.5 mg, 39%) as a white solid. $^1H$ NMR (400 MHz, $CD_3OD$) δ 8.58 (s, 1H), 7.41-7.36 (m, 2H), 7.21-7.14 (m, 2H), 6.20 (s, 1H), 5.47 (s, 2H), 4.55-4.52 (m, 1H), 4.33-4.31 (m, 1H), 4.30-4.25 (m, 1H), 4.24-4.15 (m, 1H), 4.06-4.03 (m, 1H), 3.64-3.61 (m, 2H), 3.33 (s, 3H), 2.93-2.77 (m, 6H), 2.62-2.59 (m, 1H), 2.26-2.20 (m, 1H), 1.92-1.89 (m, 1H), 1.78-1.75 (m, 1H). LCMS $R_T$=0.680 min, m/z=509.2 $[M+H]^+$. LCMS (5 to 95% acetonitrile in water+0.05% ammonium hydroxide over 1.5 mins) retention time 0.680 min, ESI+ found [M+H]=509.2.

1-[(2-fluorophenyl)methyl]-N-[(6 S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole- 3-carboxamide (Peaks 3, retention time 5.812 min) (13.9 mg, 35%) as a white solid. $^1$H NMR (400 MHz, $CD_3OD$) δ 8.58 (s, 1H), 7.41-7.36 (m, 2H), 7.21-7.14 (m, 2H), 6.20 (s, 1H), 5.55 (s, 2H), 4.55-4.52 (m, 1H), 4.33-4.31 (m, 1H), 4.30-4.25 (m, 1H), 4.24-4.15 (m, 1H), 4.06-4.03 (m, 1H), 3.64-3.61 (m, 2H), 3.33 (s, 3H), 2.93-2.77 (m, 6H), 2.62-2.59 (m, 1H), 2.26-2.20 (m, 1H), 1.92-1.89 (m, 1H), 1.78-1.75 (m, 1H). LCMS $R_T$=0.685 min, m/z=509.2 $[M+H]^+$. LCMS (5 to 95% acetonitrile in water+0.03% trifluoacetic acid over 1.5 mins) retention time 0.685 min, ESI+ found [M+H]=509.2.

SFC condition: Column: Chiralcel (OD-3 100×4.6 mm I.D., 3 um) Mobile phase: A: CO2 B: ethanol (0.05% DEA), Gradient: from 5% to 40% of B in 4.5 min and hold 40% for 2.5 min, then 5% of B for 1 min, Flow rate: 2.8 mL/min Column temperature: 40° C.

Example 763

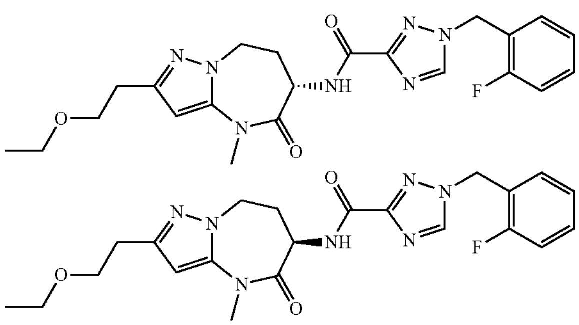

1-[(2-fluorophenyl)methyl]-N-[(6S)-2-(2-ethoxyethyl)-4-methyl-5-oxo-7,8-dihydro-6H-pyrazolo[1,5-a][1,3]diazepin-6-yl]-1,2,4-triazole-3-carboxamide and 1-[(2-fluorophenyl)methyl]-N-[(6R)-2-(2-ethoxyethyl)-4-methyl-5-oxo-7,8-dihydro-6H-pyrazolo[1,5-a][1,3]diazepin-6-yl]-1,2,4-triazole-3-carboxamide Amide coupling prepared in a similar fashion to WX Method 190. The racemic material was separated by chiral SFC to afford:

1-[(2-fluorophenyl)methyl]-N-[(6S)-2-(2-ethoxyethyl)-4-methyl-5-oxo-7,8-dihydro-6H-pyrazolo[1,5-a][1,3]diazepin-6-yl]-1,2,4-triazole-3-carboxamide (Peak 1, retention time 4.003 min) (6.8 mg, 26%) as a white solid. $^1$H NMR (400 MHz, $CD_3OD$) δ 8.47 (s, 1H), 7.34-7.22 (m, 2H), 7.12-7.00 (m, 2H), 6.08 (s, 1H), 5.45 (s, 2H), 4.45-4.40 (m, 1H), 4.27-4.19 (m, 1H), 4.16-4.07 (m, 1H), 3.60 (t, J=6.8 Hz, 2H), 3.43 (q, J=6.8 Hz, 2H), 3.23 (s, 3H), 2.78-2.70 (m, 3H), 2.19-2.11 (m, 1H), 1.08 (t, J=7.2 Hz, 3H). LC-MS RT=0.760 min, m/z=456.1 $[M+H]^+$. LCMS (5 to 95%5% acetonitrile in water+0.03% trifluoacetic acid over 1.5 mins) retention time 0.760 min, ESI+ found [M+H]=456.1.

1-[(2-fluorophenyl)methyl]-N-[1-(6R)-2-(2-ethoxyethyl)-4-methyl-5-oxo-7,8-dihydro-H-pyrazolo[[1,5-a][1,3] diazepin-6-yl]-1,2,4-triazole-3-carboxamide (Peak 2, retention time 4.673 min) for 2.5 (9.5 mg, 360) as a white solid. $^1$H NMR (400 MHz, $CD_3OD$) δ 8.47 (s, 1H), 7.33-7.22 (m, 2H), 7.13-7.00 (m, 2H), 6.08 (s, 1H), 5.45 (s, 2H), 4.44-4.40 (m, 1H), 4.27-4.19 (m, 1H), 4.16-4.07 (m, 1H), 3.60 (t, J=6.8 Hz, 2H), 3.43 (q, J=6.8 Hz, 2H), 3.23 (s, 3H), 2.78-2.70 (min, 3H), 2.19%-2.11 (m, for 1H), 1.09 (t, J=7.2 Hz, 3H). LC-MS RT=0.760 min. m/z=456.1 $[M+H]^+$.

LCMS (5 to 95% acetonitrile in water+0.03% trifluoacetic acid over 1.5 mins) retention time 0.760 min, ESI+ found [M+H]=456.1.

SFC condition: (Column: Chiralcel OD-3 100×4.6 mm I.D., 3 um Mobile phase: A: $CO_2$ B: ethanol (0.05% dethyl acetate), Gradient: from 50 to 40% of B in 4.5 min and hold 40% for 2.5 min, then 50 of B for 1.0 min, Flow rate: 2.8 mL/min Column temperature: 40° C.

Example 764

WX Method 209

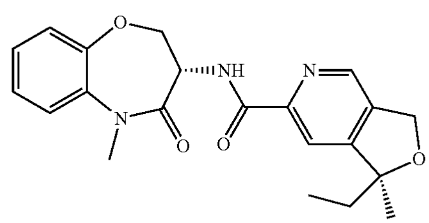 [SMILES: CC[C@]1(C)OCc2cnc(C(=O)N[C@H]3COc4ccccc4N(C)C3=O)cc21]

(1S)-1-ethyl-1-methyl-N-[(3S)-5-methyl-4-oxo-2,3-dihydro-1,5-benzoxazepin-3-yl]-3H-furo[3,4-c]pyridine-6-carboxamide A mixture of 1-hydroxybenzotriazole (35 mg, 0.26 mmol), 1-(3-dimethyl aminopropyl)-3-ethylcarbodiimide-hydrochloride (374 mg, 1.95 mmol), (3S)-3-amino-5-methyl-2,3-dihydro-1,5-benzoxazepin-4-one (250 mg, 1.30 mmol) and (1S)-1-ethyl-1-methyl-3H-furo[3,4-c]pyridine-6-carboxylic acid (270 mg, 1.30 mmol) in N,N-dimethylformamide (10 mL) was stirred at 15° C. for 12 h and poured into ice water (50 mL). The resulting solid was collected by filtration and dried under reduced pressure to give (1 S)-1-ethyl-1-methyl-N-[(3S)-5-methyl-4-oxo-2,3-dihydro-1,5-benzoxazepin-3-yl]-3H-furo[3,4-c]pyridine-6-carboxamide (406 mg, 82%) as a white solid. $^1$H NMR (400 MHz, DMSO-$d_6$) δ 8.88 (d, J=7.6 Hz, 1H), 8.64 (s, 1H), 7.88 (s, 1H), 7.51 (d, J=7.2 Hz, 1H), 7.36-7.24 (m, 3H), 5.15 (s, 2H), 4.91-4.85 (m, 1H), 4.59-4.46 (m, 2H), 3.35-3.34 (m, 3H), 1.87-1.73 (m, 2H), 1.40 (s, 3H), 0.68 (t, J=7.2 Hz, 3H). LCMS $R_T$=0.841 min; m/z=382.1 $(M+H)^+$.

LCMS (5 to 95% acetonitrile in water+0.03% trifluoacetic acid over 1.5 mins) retention time 0.841 min, ESI+ found [M+H]=382.1.

Chiral HPLC retention time: 3.978 min (Column: Chiralpak AD-3 100×4.6 mm I.D., 3 um. Mobile phase: A: CO2 B: ethanol (0.05% DEA). Gradient: from 5% to 40% of B in 4.5 min and hold 40% for 2.5 min, then 5% of B for 1 min. Flow rate: 2.8 mL/min. Column temperature: 40° C.)

Example 765

WX Method 208

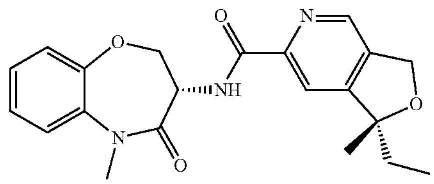 [SMILES: CC[C@@]1(C)OCc2cnc(C(=O)N[C@H]3COc4ccccc4N(C)C3=O)cc21]

(1R)-1-ethyl-1-methyl-N-[(3S)-5-methyl-4-oxo-2,3-dihydro-1,5-benzoxazepin-3-yl]-3H-furo[3,4-c]pyridine-6-carboxamide A mixture of 1-hydroxybenzotriazole (35 mg, 0.26 mmol), 1-(3-dimethyl aminopropyl)-3-ethylcarbodiimide-hydrochloride (374 mg, 1.95 mmol), (3S)-3-amino-5-methyl-2,3-dihydro-1,5-benzoxazepin-4-one (250 mg, 1.30 mmol) and (1R)-1-ethyl-1-methyl-3H-furo[3,4-c]pyridine-6-carboxylic acid (270 mg, 1.30 mmol) in N,N-dimethylformamide (10 mL) was stirred at 25° C. for 12 h and poured into ice water (100 mL). The resulting solid was collected by filtration and dried under reduced pressure to give (1R)-1-ethyl-1-methyl-N-[(3S)-5-methyl-4-oxo-2,3-dihydro-1,5-benzoxazepin-3-yl]-3H-furo[3,4-c]pyridine-6-carboxamide (404 mg, 81%) as a white solid. $^1$H NMR (400 MHz, $CD_3OD$) δ 8.57 (s, 1H), 7.85 (s, 1H), 7.45-7.42 (m, 1H), 7.33-7.31 (m, 2H), 7.30-7.23 (m, 1H), 5.16 (s, 2H), 5.15-5.12 (m, 1H), 4.66-4.62 (m, 1H), 4.42-4.37 (m, 1H), 3.42 (s, 3H), 1.87-1.82 (m, 2H), 1.45 (s, 3H), 0.76 (t, J=7.6 Hz, 3H). LCMS $R_T$=0.850 min; m/z=382.1 $(M+H)^+$.

LCMS (10 to 80% acetonitrile in water+0.03% ammonium bicarbonate over 1.5 mins) retention time 0.850 min, ESI+ found [M+H]=382.1.

Chiral HPLC retention time: 3.478 min (Column: Chiralcel OD-3 100×4.6 mm I.D., 3 um. Mobile phase: A: CO2 B: ethanol (0.05% DEA). Gradient: from 5% to 40% of B in 4.5 min and hold 40% for 2.5 min, then 5% of B for 1 min. Flow rate: 2.8 mL/min. Column temperature: 40° C.

Example 766

WX Method 207

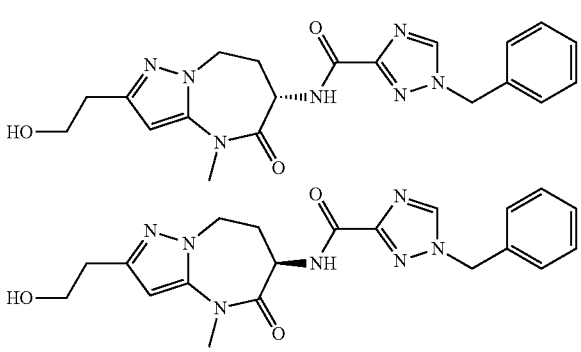

1-benzyl-N-[(6S)-2-(2-hydroxyethyl)-4-methyl-5-oxo-7,8-dihydro-6H-pyrazolo[1,5-a][1,3]diazepin-6-yl]-1,2,4-triazole-3-carboxamide and 1-benzyl-N-[(6R)-2-(2-hydroxyethyl)-4-methyl-5-oxo-7,8-dihydro-6H-pyrazolo[1,5-a][1, 3]diazepin-6-yl]-1,2,4-triazole-3-carboxamide

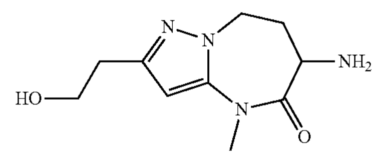 [SMILES: CN1C(=O)C(N)CCn2nc(CCO)cc21]

Step 1: 6-amino-2-(2-hydroxyethyl)-4-methyl-7,8-dihydro-4H-pyrazolo[1,5-a][1,3]diazepin-5(6H)-one To a solution of tert-butyl N-[2-(2-hydroxyethyl)-4-methyl-5-oxo-7,8-dihydro-6H-pyrazolo[1,5-a][1,3]diazepin-6-yl]carbamate (200 mg, 0.62 mmol) in dichloromethane (10 mL) was added trifluoroacetic acid (703 mg, 6.17 mmol). The reaction mixture was stirred at 20° C. for 3 h and concentrated under reduced pressure. The residue was dissolved in acetonitrile (10 mL), added potassium carbonate (1.38 g, 10 mmol) and stirred for 30 min. The solid was removed by filtration and the residue was purified by flash column chromatography (silica gel, 100-200 mesh, 0 to 50% methanol in dichloromethane) to afford 6-amino-2-(2-hydroxyethyl)-4-methyl-7,8-dihydro-6H-pyrazolo[1,5-a][1,3]diazepin-5-one (120 mg, 87%) as a yellow oil, used as is in the next step.

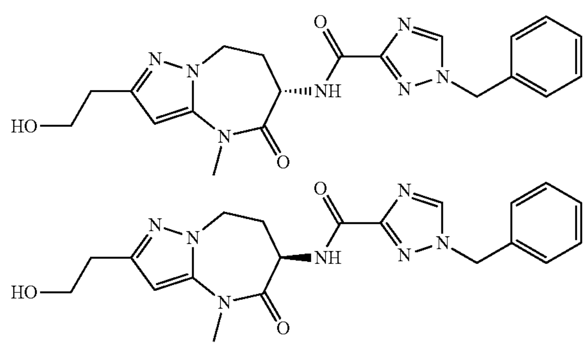

Step 2: 1-benzyl-N-[(6S)-2-(2-hydroxyethyl)-4-methyl-5-oxo-7,8-dihydro-6H-pyrazolo[1,5-a][1,3]diazepin-6-yl]-1,2,4-triazole-3-carboxamide and 1-benzyl-N-[(6R)-2-(2-hydroxyethyl)-4-methyl-5-oxo-7,8-dihydro-6H-pyrazolo[1,5-a][1, 3]diazepin-6-yl]-1,2,4-triazole-3-carboxamide A mixture of 1-benzyl-1,2,4-triazole-3-carboxylic acid (63 mg, 0.31 mmol), 6-amino-2-(2-hydroxyethyl)-4-methyl-7,8-dihydro-6H-pyrazolo[1,5-a][1,3]diazepin-5-one (70 mg, 0.31 mmol), 1-hydroxybenzotriazole (42 mg, 0.31 mmol) and 1-(3-dimethyl aminopropyl)-3-ethylcarbodiimidehydrochloride (60 mg, 0.31 mmol) in N,N-dimethylformamide (6 mL) was stirred at 20° C. for 2 h. The reaction mixture was concentrated under reduced pressure and the residue was purified by RP-HPLC (acetonitrile 10-40/0.05% HCl in water) to afford 1-benzyl-N-[2-(2-hydroxyethyl)-4-methyl-5-oxo-7,8-dihydro-6H-pyrazolo[1,5-a][1,3]diazepin-6-yl]-1,2,4-triazole-3-carboxamide (30 mg, 24%) as a white solid. The racemic material was further separated by chiral SFC to give:

1-benzyl-N-[(6S)-2-(2-hydroxyethyl)-4-methyl-5-oxo-7,8-dihydro-6H-pyrazolo[1,5-a][1,3]diazepin-6-yl]-1,2,4-triazole-3-carboxamide (Peak 1, retention time 4.640 min) (11.5 mg, 38%) as a white solid. $^1$H NMR (400 MHz, $CD_3OD$) δ 8.57 (s, 1H), 7.41-7.29 (m, 5H), 6.19 (s, 1H), 5.48 (s, 2H), 4.58-4.53 (m, 1H), 4.39-4.31 (m, 1H), 4.28-4.17 (m, 1H), 3.82 (t, J=6.8 Hz, 2H), 3.35-3.33 (m, 3H), 2.92-2.77 (m, 3H), 2.29-2.21 (m, 1H). LCMS $R_T$=0.992 min; m/z=410.2 $(M+H)^+$.

LCMS (0 to 60% acetonitrile in water+0.03% formic acid over 2.0 mins) retention time 0.992 min, ESI+ found [M+H]= 410.2.

1-benzyl-N-[(6R)-2-(2-hydroxyethyl)-4-methyl-5-oxo-7,8-dihydro-6H-pyrazolo[1,5-a][1,3]di azepin-6-yl]-1,2,4-triazole-3-carboxamide (Peak 2, retention time 5.416 min) (10.2 mg, 33%) as a white solid. $^1$H NMR (400 MHz, $CD_3OD$) δ 8.57 (s, 1H), 7.41-7.29 (m, 5H), 6.19 (s, 1H), 5.47 (s, 2H), 4.58-4.53 (m, 1H), 4.39-4.31 (m, 1H), 4.28-4.17 (m, 1H), 3.82 (t, J=6.8 Hz, 2H), 3.37-3.33 (m, 3H), 2.92-2.76 (m, 3H), 2.29-2.20 (m, 1H). LCMS $R_T$=0.992 min; m/z=410.2 $(M+H)^+$.

LCMS (0 to 60% acetonitrile in water+0.03% formic acid over 2.0 mins) retention time 0.992 min, ESI+ found [M+H]= 410.2.

SFC condition: Column: Chiralcel OD-3 100×4.6 mm I.D., 3 um Mobile phase: A: $CO_2$ B: ethanol (0.05% DEA) Gradient: from 5% to 40% of B in 4.5 min and hold 40% for 2.5 min, then 5% of B for 1 min, Flow rate: 2.8 mL/min Column temperature: 40° C.

Example 767

WX Method 196

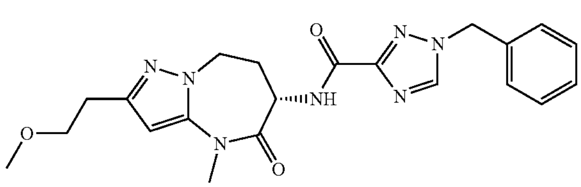

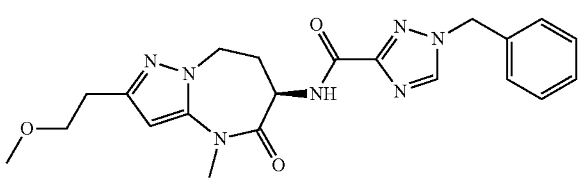

1-benzyl-N-[(6S)-2-(2-methoxyethyl)-4-methyl-5-oxo-7,8-dihydro-6H-pyrazolo[1,5-a][1,3]diazepin-6-yl]-1,2,4-triazole-3-carboxamide and 1-benzyl-N-[(6R)-2-(2-methoxyethyl)-4-methyl-5-oxo-7,8-dihydro-6H-pyrazolo[1,5-a][1, 3]diazepin-6-yl]-1,2,4-triazole-3-carboxamide

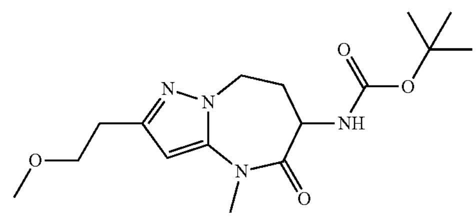 [SMILES: COCCc1cc2n(n1)CCC(NC(=O)OC(C)(C)C)C(=O)N2C]

Step 1: tert-butyl (2-(2-methoxyethyl)-4-methyl-5-oxo-5,6,7,8-tetrahydro-4H-pyrazolo[1,5-a][1,3]diazepin-6-yl)carbamate A mixture of tert-butyl N-[2-(2-hydroxyethyl)-4-methyl-5-oxo-7,8-dihydro-6H-pyrazolo[1,5-a][1,3]diazepin-6-yl] carbamate (250 mg, 0.77 mmol), iodomethane (2 mL, 32.13 mmol) and silver(II) oxide (893 mg, 3.85 mmol) was stirred at 20° C. for 14 h and then filtered. The filtrate was concentrated under reduced pressure and the residue was purified by flash column chromatography (silica gel, 100-200 mesh, 0 to 40% ethyl acetate in petroleum ether) to afford tert-butyl N-[2-(2-methoxyethyl)-4-methyl-5-oxo-7,8-dihydro-6H-pyrazolo[1,5-a][1,3]diazepin-6-yl]carbamate (200 mg, 77%) as a white solid. $^1$H NMR (400 MHz, $CDCl_3$) δ 5.93 (s, 1H), 5.39 (d, J=7.8 Hz, 1H), 4.36-4.23 (m, 2H), 4.07-3.98 (m, 1H), 3.65-3.61 (m, 2H), 3.37 (s, 3H), 3.30 (s, 3H), 2.94-2.87 (m, 1H), 2.84 (d, J=8.0 Hz, 2H), 1.94-1.86 (m, 1H), 1.39 (s, 9H). LC-MS $R_T$=0.653 min, m/z=338.9 $(M+H)^+$.

LCMS (5 to 95% acetonitrile in water+0.03% trifluoacetic acid over 1.5 mins) retention time 0.653 min, ESI+ found [M+H]=338.9.

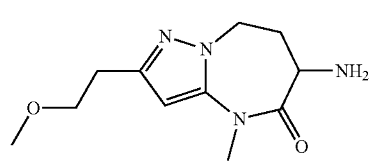 [SMILES: COCCc1cc2n(n1)CCC(N)C(=O)N2C]

Step 2: 6-amino-2-(2-methoxyethyl)-4-methyl-7,8-dihydro-4H-pyrazolo[1,5-a][1,3]diazepin-5(6H)-one To a stirred mixture solution of tert-butyl N-[2-(2-methoxyethyl)-4-methyl-5-oxo-7,8-dihydro-6H-pyrazolo[1,5-a][1,3]diazepin-6-yl]carbamate (200 mg, 0.59 mmol) in dichloromethane (5 mL) was added trifluoroacetic acid (3 mL, 5.91 mmol). The resulting mixture was stirred 12 h at 25° C. and then quenched by addition of saturated aqueous sodium bicarbonate (10 mL). The resulting mixture was extracted with dichloromathane (5×20 mL). The combined organic layers were washed with brine (30 mL), dried over sodium sulfate and concentrated under reduce pressure to give the crude 6-amino-2-(2-methoxyethyl)-4-methyl-7,8- dihydro-6H-pyrazolo[1,5-a][1,3]diazepin-5-one (120 mg, 85%) as a yellow oil. LC-MS $R_T$=1.147 min, m/z=239.2 $(M+H)^+$.

LCMS (0 to 60% acetonitrile in water+0.03% ammonium bicarbonate over 3.0 mins) retention time 1.147 min, ESI+ found [M+H]=239.2.

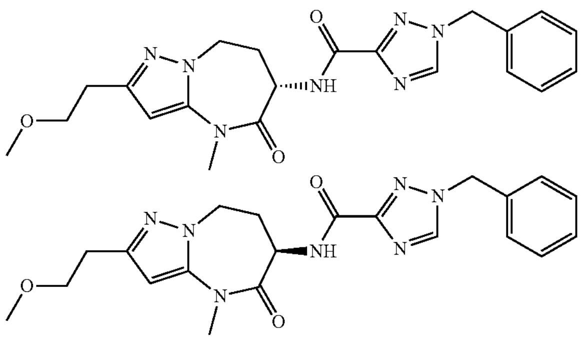

Step 3: 1-benzyl-N-[(6S)-2-(2-methoxyethyl)-4-methyl-5-oxo-7,8-dihydro-6H-pyrazolo[1,5-a][1,3]diazepin-6-yl]-1,2,4-triazole-3-carboxamide and 1-benzyl-N-[(6R)-2-(2-methoxyethyl)-4-methyl-5-oxo-7,8-dihydro-6H-pyrazolo[1,5-a][1, 3]diazepin-6-yl]-1,2,4-triazole-3-carboxamide A mixture of 1-benzyl-1,2,4-triazole-3-carboxylic acid (23 mg, 0.12 mmol), 1-(3-dimethyl aminopropyl)-3-ethyl-carbodiimidehydrochloride (40 mg, 0.21 mmol), 6-amino-2-(2-methoxyethyl)-4-methyl-7,8-dihydro-6H-pyrazolo[1,5-a][1,3]diazepin-5-one (25 mg, 0.10 mmol) and 1-hydroxybenzotriazole (28 mg, 0.21 mmol) in N,N-dimethylformamide (3 mL) was stirred at 20° C. for 12 h. The reaction mixture was concentrated under reduce pressure and the residue was purified by RP-HPLC (acetonitrile 20-45%/0.225% formic acid in water) to afford 1-benzyl-N-[2-(2-methoxyethyl)-4-methyl-5-oxo-7,8-dihydro-6H-pyrazolo[1,5-a][1,3]diazepin-6-yl]-1,2,4-triazole-3-carboxamide (40 mg, 90%) as a white solid. The racemic material was separated by chiral SFC to afford: 1-benzyl-N-[(6S)-2-(2-methoxyethyl)-4-methyl-5-oxo-7,8-dihydro-6H-pyrazolo[1,5-a][1,3]di azepin-6-yl]-1,2,4-triazole-3-carboxamide (Peak 1, retention time 4.453 min) (11 mg, 27%) as a white solid. $^1H$ NMR (400 MHz, $CD_3OD$) δ 8.55 (s, 1H), 7.38-7.31 (m, 5H), 6.18 (s, 1H), 5.47 (s, 2H), 4.58-4.52 (m, 1H), 4.34-4.30 (m, 1H), 4.25-4.22 (m, 1H), 3.66 (t, J=6.8 Hz, 2H), 3.35 (s, 3H), 3.31 (s, 3H), 2.87-2.83 (m, 3H), 2.27-2.21 (m, 1H). LC-MS $R_T$=1.429 min, m/z=424.2 $[M+H]^+$. LCMS (10 to 80% acetonitrile in water+0.03% ammonium bicarbonate over 3.0 mins) retention time 1.429 min, ESI+ found [M+H]=424.2.

1-benzyl-N-[(6R)-2-(2-methoxyethyl)-4-methyl-5-oxo-7,8-dihydro-6H-pyrazolo[1,5-a][1,3]diazepin-6-yl]-1,2,4-triazole-3-carboxamide (Peak 2, retention time 5.281 min) (19.2 mg, 47%) as a white solid. $^1H$ NMR (400 MHz, $CD_3OD$) δ 8.47 (s, 1H), 7.31-7.20 (m, 5H), 6.09 (s, 1H), 5.38 (s, 2H), 4.45-4.41 (m, 1H), 4.26-4.21 (m, 1H), 4.15-4.09 (m, 1H), 3.57 (t, J=6.8 Hz, 2H), 3.26 (s, 3H), 3.23 (s, 3H), 2.78-2.71 (m, 3H), 2.18-2.13 (m, 1H). LC-MS RT=1.361 min, m/z=424.2. LCMS (10 to 80% acetonitrile in water+0.03% ammonium bicarbonate over 3.0 mins) retention time 1.361 min, ESI+ found [M+H]=424.2.

SFC condition: (Column: Chiralcel AD-3 100×4.6 mm I.D., 3 um Mobile phase: A: $CO_2$ B: ethanol (0.05% dethyl acetate), Gradient: from 5% to 40% of B in 4.5 min and hold 40% for 2.5 min, then 5% of B for 1 min, Flow rate: 2.8 mL/min Column temperature: 40° C.

Example 768

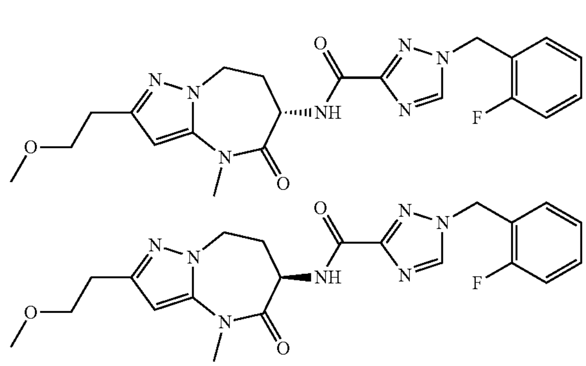

1-[(2-fluorophenyl)methyl]-N-[(6S)-2-(2-methoxyethyl)-4-methyl-5-oxo-7,8-dihydro-6H-pyrazolo[1,5-a][1,3]diazepin-6-yl]-1,2,4-triazole-3-carboxamide and 1-[(2-fluorophenyl)methyl]-N-[(6R)-2-(2-methoxyethyl)-4-methyl-5-oxo-7,8-dihydro-6H-pyrazolo[1,5-a][1,3]diazepin-6-yl]-1,2,4-triazole-3-carboxamide Amide coupling prepared in a similar fashion to WX Method 196. The racemic material was separated by chiral SFC to afford:

1-[(2-fluorophenyl)methyl]-N-[(6S)-2-(2-methoxyethyl)-4-methyl-5-oxo-7,8-dihydro-6H-pyrazolo[1,5-a][1,3]diazepin-6-yl]-1,2,4-triazole-3-carboxamide (Peak 1, retention time 4.028 min) (11 mg, 27%) as a white solid. $^1H$ NMR (400 MHz, $CD_3OD$) δ 8.56 (s, 1H), 7.42-7.33 (m, 2H), 7.22-7.09 (m, 2H), 6.17 (s, 1H), 5.54 (s, 2H), 4.58-4.51 (m, 1H), 4.36-4.29 (m, 1H), 4.26-4.16 (m, 1H), 3.65 (t, J=6.8 Hz, 2H), 3.35 (s, 3H), 3.31 (s, 3H), 2.86-2.77 (m, 3H), 2.28-2.20 (m, 1H). LC-MS $R_T$=1.446 min, m/z=442.2 $[M+H]^+$. LCMS (10 to 80% acetonitrile in water+0.03% ammonium bicarbonate over 3.0 mins) retention time 1.446 min, ESI+ found [M+H]=442.2.

1-[(2-fluorophenyl)methyl]-N-[(6R)-2-(2-methoxyethyl)-4-methyl-5-oxo-7,8-dihydro-6H-pyrazolo[1,5-a][1,3]diazepin-6-yl]-1,2,4-triazole-3-carboxamide (Peak 2, retention time 4.447 min) (25.1 mg, 61%) as a white solid. $^1H$ NMR (400 MHz, $CD_3OD$) δ 8.57 (s, 1H), 7.44-7.35 (m, 2H), 7.22-7.11 (m, 2H), 6.17 (s, 1H), 5.54 (s, 2H), 4.54-4.50 (m, 1H), 4.36-4.30 (m, 1H), 4.25-4.17 (m, 1H), 3.66 (t, J=6.8 Hz, 2H), 3.35 (s, 3H), 3.32 (s, 3H), 2.85 (t, J=6.6 Hz, 2H), 2.83-2.77 (m, 1H), 2.26-2.20 (m, 1H). LC-MS RT=1.379 min, m/z=442.2 $[M+H]^+$. LCMS (10 to 80% acetonitrile in water+0.03% ammonium bicarbonate over 3.0 mins) retention time 1.379 min, ESI+ found [M+H]=442.2.

SFC conditions: (Column: Chiralcel AD-3 100×4.6 mm I.D., 3 um Mobile phase: A: $CO_2$ B: ethanol (0.05% dethyl acetate), Gradient: from 5% to 40% of B in 4.5 min and hold 40% for 2.5 min, then 5% of B for 1 min, Flow rate: 2.8 mL/min Column temperature: 40° C.

Example 769

WX Method 201

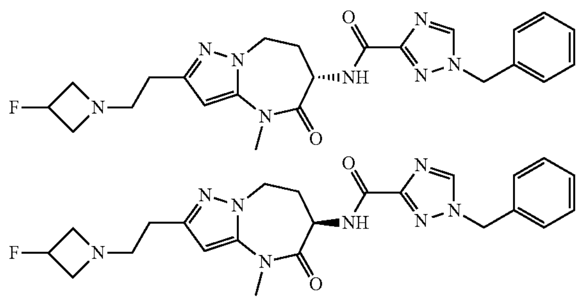

1-benzyl-N-[(6S)-2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide

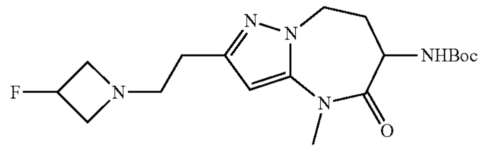 [SMILES: CN1C(=O)C(NC(=O)OC(C)(C)C)CCn2nc(CCN3CC(F)C3)cc21]

Step 1: tert-butyl (2-(2-(3-fluoroazetidin-1-yl)ethyl)-4-methyl-5-oxo-5,6,7,8-tetrahydro-4H-pyrazolo[1,5-a][1,3]diazepin-6-yl)carbamate A mixture of 2-[6-(tert-butoxycarbonylamino)-4-methyl-5-oxo-7,8-dihydro-6H-pyrazolo[1,5-a][1,3]diazepin-2-yl]ethyl methanesulfonate (200 mg, 0.50 mmol), potassium carbonate (155 mg, 1.12 mmol), 3-fluoroazetidine (50 mg, 0.67 mmol) and sodium iodide (56 mg, 0.37 mmol) in N,N-dimethylformamide (10 mL) was heated at 50° C. for 6 h and then concentrated under reduced pressure. The residue was purified by column chromatography (silica gel, 100-200 mesh, solvent gradient: 0-10% methanol in dichloromethane) to afford tert-butyl N-[2-[2-(3-fluoroazetidin-1-yl)ethyl]-4-methyl-5-oxo-7,8-dihydro-6H-pyrazolo[1,5-a][1,3]di azepin-6-yl]carbamate (120 mg, 63%) as a yellow solid, used as is in the next step.

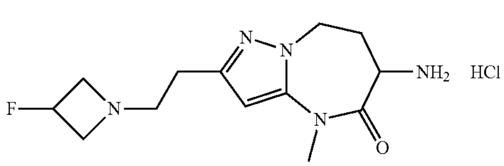 [SMILES: CN1C(=O)C(N)CCn2nc(CCN3CC(F)C3)cc21 ; Cl]

Step 2: 6-amino-2-[2-(3-fluoroazetidin-1-yl)ethyl]-4-methyl-7,8-dihydro-6H-pyrazolo[1,5-a][1,3]diazepin-5-one hydrochloride To a solution of tert-butyl N-[2-[2-(3-fluoroazetidin-1-yl)ethyl]-4-methyl-5-oxo-7,8-dihydro-6H-pyrazolo[1,5-a][1,3]di azepin-6-yl]carbamate (120 mg, 0.31 mmol) in ethyl acetate (10 mL) was added hydrochloric acid (4.0 M in ethyl acetate, 1.0 mL, 4.0 mmol). The mixture was stirred at 25° C. for 4 h and concentrated under reduced pressure to afford 6-amino-2-[2-(3-fluoroazetidin-1-yl)ethyl]-4-methyl-7,8-dihydro-6H-pyrazolo[1,5-a][1,3]diazepin-5-one hydrochloride (80 mg, 80%) as a white solid, used in the next step without further purification.

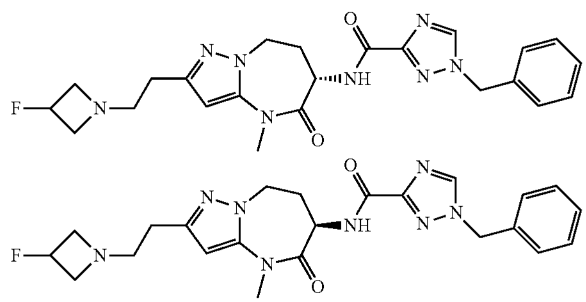

Step 3: 1-benzyl-N-[(6S)-2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide To a solution of A mixture of 1-benzyl-1,2,4-triazole-3-carboxylic acid (26 mg, 0.13 mmol), 6-amino-2-[2-(3-fluoroazetidin-1-yl)ethyl]-4-methyl-7,8-dihydro-6H-pyrazolo[1,5-a][1,3]diazepin-5-one hydrochloride (40 mg, 0.13 mmol), 1-hydroxybenzotriazole (26 mg, 0.19 mmol) and 1-(3-dimethylaminopropyl)-3-ethylcarbodiimidehydrochloride (36 mg, 0.19 mmol) in N,N-dimethylformamide (5 mL) was stirred at 15° C. for 2 h. The reaction mixture was concentrated under reduced pressure and the residue was purified by RP-HPLC (acetonitrile 3-33/0.05% HCl in water) to afford 1-benzyl-N-[2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide (15 mg, 26%) as a white solid. The racemic material was further separated by chiral SFC to give: 1-benzyl-N-[(6 S)-2-[2-(3-fluoroazetidin-1-yl)ethyl]-4-methyl-5-oxo-7,8-dihydro-6H-pyrazol o[1,5-a][1,3]diazepin-6-yl]-1,2,4-triazole-3-carboxamide (Peak 1, retention time 4.263 min) (3.6 mg, 23%) as a white solid. $^1$H NMR (400 MHz, $CD_3OD$) δ 8.57 (s, 1H), 7.41-7.30 (m, 5H), 6.18 (s, 1H), 5.48 (s, 2H), 5.24-5.18 (m, 0.5H), 5.09-5.04 (m, 0.5H), 4.57-4.52 (m, 1H), 4.38-4.30 (m, 1H), 4.26-4.17 (m, 1H), 3.76-3.66 (m, 2H), 3.39-3.32 (m, 5H), 2.91-2.81 (m, 3H), 2.71-2.64 (m, 2H), 2.30-2.21 (m, 1H). LCMS $R_T$=1.472 min; m/z=467.2 $(M+H)^+$.

LCMS (10 to 80% acetonitrile in water+0.03% ammonia water over 3.0 mins) retention time 1.472 min, ESI+ found [M+H]=467.2.

1-benzyl-N-[(6R)-2-[2-(3-fluoroazetidin-1-yl)ethyl]-4-methyl-5-oxo-7,8-dihydro-6H-pyrazol o[1,5-a][1,3]diazepin-6-yl]-1,2,4-triazole-3-carboxamide (Peak 1, retention time 5.366 min) (1.8 mg, 11%) as a white solid. $^1$H NMR (400 MHz, $CD_3OD$) δ 8.57 (s, 1H), 7.41-7.30 (m, 5H), 6.18 (s, 1H), 5.48 (s, 2H), 5.24-5.18 (m, 0.5H), 5.09-5.04 (m, 0.5H), 4.57-4.52 (m, 1H), 4.38-4.30 (m, 1H), 4.26-4.17 (m, 1H), 3.76-3.66 (m, 2H), 3.39-3.32 (m, 5H), 2.91-2.81 (m, 3H), 2.71-2.64 (m, 2H), 2.30-2.21 (m, 1H). LCMS $R_T$=1.466 min; m/z=467.2 $(M+H)^+$. LCMS (10 to 80% acetonitrile in water+0.03% ammonia water over 3.0 mins) retention time 1.466 min, ESI+ found [M+H]=467.2.

SFC condition: Column: Chiralpak AD-3 100×4.6 mm I.D., 3 um Mobile phase: A: CO2 B: iso-propanol (0.05% DEA), Gradient: from 5% to 40% of B in 4.5 min and hold 40% for 2.5 min, then 5% of B for 1 min, Flow rate: 2.8 mL/min Column temperature: 40° C.

Example 770

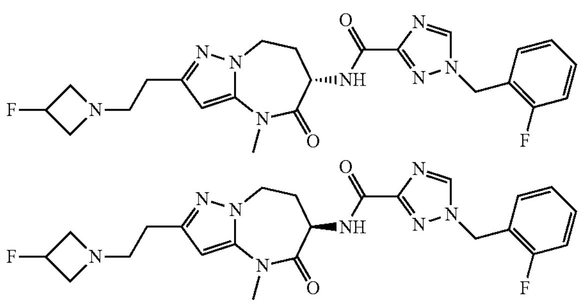

1-[(2-fluorophenyl)methyl]-N-[(6S)-2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide and 1-[(2-fluorophenyl)methyl]-N-[(6R)-2-[2-(3-fluoroazetidin-1-yl)ethyl]-4-methyl-5-oxo-7, 8-dihydro-6H-pyrazolo[1,5-a][1,3]diazepin-6-yl]-1,2,4-triazole-3-carboxamide Amide coupling prepared in a similar fashion to WX Method 201. The racemic material was separated by chiral SFC to afford:

1-benzyl-N-[(6 S)-2-[2-(3-fluoroazetidin-1-yl)ethyl]-4-methyl-5-oxo-7,8-dihydro-6H-pyrazol o[1,5-a][1,3]diazepin-6-yl]-1,2,4-triazole-3-carboxamide (Peak 1, retention time 4.021 min) (4.7 mg, 29%) as a white solid. $^1$H NMR (400 MHz, $CD_3OD$) δ 8.59 (s, 1H), 7.40-7.37 (m, 2H), 7.22-7.13 (m, 2H), 6.20 (s, 1H), 5.56 (s, 2H), 5.33-5.25 (m, 0.5H), 5.22-5.18 (m, 0.5H), 4.58-4.49 (m, 1H), 4.36-4.33 (m, 1H), 4.25-4.22 (m, 1H), 4.15-4.06 (m, 2H), 3.85-3.76 (m, 2H), 3.33 (s, 3H), 3.21-3.18 (m, 2H), 2.86-2.79 (m, 3H), 2.29-2.25 (m, 1H). LCMS $R_T$=1.486 min; m/z=485.2 $(M+H)^+$.

LCMS (10 to 80% acetonitrile in water+0.03% ammonia water over 3.0 mins) retention time 1.486 min, ESI+ found [M+H]=485.2.

1-benzyl-N-[(6R)-2-[2-(3-fluoroazetidin-1-yl)ethyl]-4-methyl-5-oxo-7,8-dihydro-6H-pyrazol o[1,5-a][1,3]diazepin-6-yl]-1,2,4-triazole-3-carboxamide (Peak 2, retention time 5.051 min) (3.3 mg, 21%) as a white solid. $^1$H NMR (400 MHz, $CD_3OD$) δ 8.58 (s, 1H), 7.42-7.36 (m, 2H), 7.23-7.15 (m, 2H), 6.18 (s, 1H), 5.56 (s, 2H), 5.22-5.19 (m, 0.5H), 5.08-5.04 (m, 0.5H), 4.56-4.51 (m, 1H), 4.35-4.31 (m, 1H), 4.25-4.17 (m, 1H), 3.72-3.66 (m, 2H), 3.35-3.29 (m, 5H), 2.89-2.84 (m, 3H), 2.70-2.66 (m, 2H), 2.26-2.21 (m, 1H). LCMS $R_T$=1.482 min; m/z=485.2 $(M+H)^+$.

LCMS (10 to 80% acetonitrile in water+0.03% ammonia water over 3.0 mins) retention time 1.486 min, ESI+ found [M+H]=485.2.

SFC condition: Column: Chiralpak AD-3 100×4.6 mm I.D., 3 um Mobile phase: A: $CO_2$ B: iso-propanol (0.05% DEA), Gradient: from 5% to 40% of B in 4.5 min and hold 40% for 2.5 min, then 5% of B for 1 min, Flow rate: 2.8 mL/min Column temperature: 40° C.

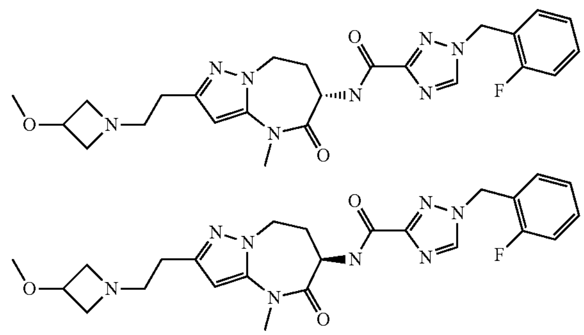

Example 771: 1-[(2-fluorophenyl)methyl]-N-(6S)-2-[2-(3-methoxyazetidin-1-yl)ethyl]-4-methyl-1-oxo-7, 8-dihydro-6H-pyrazolo[1,5-a][1,3]diazepin-6-yl]-1, 2,4-triazole-3-carboxamide and 1-[(2-fluorophenyl) methyl]-N-[(6R)-2-[2-(3-methoxyazetidin-1-yl) ethyl]-4-methyl-5-oxo-7,8-dihydro-6H-pyrazolo[1,5-a][1,3]diazepin-6-yl]-1,2,4-triazole-3-carboxamide Amide coupling prepared in a similar fashion to WX Method 194. The residue was purified by RP-HPLC (5-35% acetonitrile in water and 0.05% hydrochloric acid) to afford 1-(2-fluorobenzyl)-N-(2-(2-(3-methoxyazetidin-1-yl)ethyl)-4-methyl-5-oxo-5,6,7,8-tetrahydro-4H-pyrazolo[1,5-a][1,3] diazepin-6-yl)-1H-1,2,4-triazole-3-carboxamide (40 mg, 33%) as a white solid. The racemic compound was further separated by chiral SFC to afford:

1-[(2-fluorophenyl)methyl]-N-[(6 S)-2-[2-(3-methoxyazetidin-1-yl)ethyl]-4-methyl-5-oxo-7, 8-dihydro-6H-pyrazolo[1,5-a][1,3]diazepin-6-yl]-1,2,4-triazole-3-carboxamide (Peak 1, retention time 1.653 min) (5.5 mg, 5%) as a white solid. $^1$H NMR (400 MHz, $CD_3OD$) δ 8.57 (s, 1H), 7.40-7.36 (m, 2H), 7.22-7.13 (m, 2H), 6.16 (s, 1H), 5.55 (s, 2H), 4.56-4.51 (m, 1H), 4.36-4.31 (m, 1H), 4.25-4.17 (m, 1H), 4.06-4.04 (m, 1H), 3.65-3.61 (m, 2H), 3.32 (s, 3H), 3.25 (s, 3H), 3.03-3.00 (m, 2H), 2.87-2.80 (m, 3H), 2.68-2.66 (m, 2H), 2.28-2.20 (m, 1H). LC-MS $R_T$=0.567 min, m/z=497.1 $(M+H)^+$.

LCMS (5 to 95% acetonitrile in water+0.03% trifluoacetic acid over 1.5 mins) retention time 0.567 min, ESI+ found [M+H]=497.1.

1-[(2-fluorophenyl)methyl]-N-[(6R)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide (Peak 2, retention time 1.912 min) (4.5 mg, 4%) as a white solid. $^1$H NMR (400 MHz, $CD_3OD$) δ 8.57 (s, 1H), 7.43-7.36 (m, 2H), 7.22-7.12 (m, 2H), 6.16 (s, 1H), 5.55 (s, 2H), 4.56-4.51 (m, 1H), 4.34-4.30 (m, 1H), 4.25-4.20 (m, 1H), 4.05-4.02 (m, 1H), 3.64-3.60 (m, 2H), 3.32 (s, 3H), 3.25 (s, 3H), 3.00 (t, J=7.0 Hz, 2H), 2.87-2.78 (m, 3H), 2.68-2.64 (m, 2H), 2.28-2.21 (m, 1H). LC-MS $R_T$=0.574 min, m/z=497.2 $(M+H)^+$.

LCMS (5 to 95% acetonitrile in water+0.03% trifluoacetic acid over 1.5 mins) retention time 0.574 min, ESI+ found [M+H]=497.2.

SFC condition: column chiralpak AD-3 (50 mm*4.6 mm I.D), 3 um mobile phase: A: $CO_2$; B: EtOH (0.05% DEA) gradient: hold 5% for 0.2 min, then from 5% to 40% of B in 1.4 min and hold 40% for 1.05 min, then 5% of B for 0.35 min. Flow rate: 4 mL/min. Column temperature: 40° C.

Example 772

WX Method 205

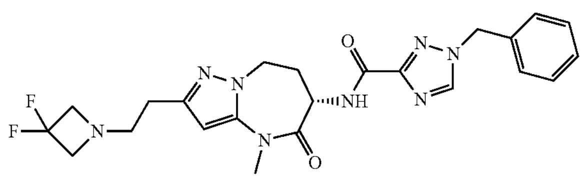

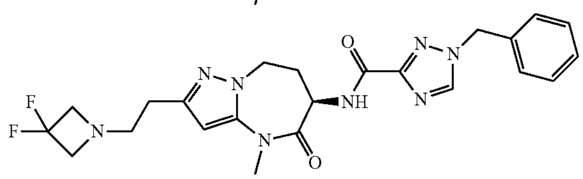

1-benzyl-N-[(6S)-2-[2-(3,3-difluoroazetidin-1-yl) ethyl]-4-methyl-5-oxo-7,8-dihydro-6H-pyrazolo[1,5-a][1,3]diazepin-6-yl]-1,2,4-triazole-3-carboxamide and 1-benzyl-N-[(6R)-2-[2-(3,3-difluoroazetidin-1-yl)ethyl]-4-methyl-5-oxo-7,8-dihydro-6H-pyrazolo [1,5-a][1,3]diazepin-6-yl]-1,2,4-triazole-3-carboxamide

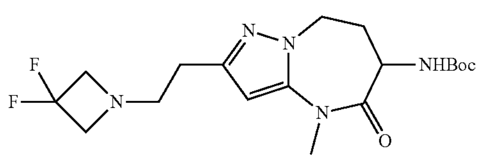 [SMILES: CN1C(=O)C(NC(=O)OC(C)(C)C)CCn2nc(CCN3CC(F)(F)C3)cc21]

Step 1: tert-butyl (2-(2-(3,3-difluoroazetidin-1-yl) ethyl)-4-methyl-5-oxo-5,6,7,8-tetrahydro-4H-pyrazolo[1,5-a][1,3]diazepin-6-yl)carbamate To a solution of 3,3-difluoroazetidine hydrochloride (241 mg, 1.86 mmol) in acetonitrile (5 mL) was added potassium carbonate (513 mg, 3.72 mmol). The mixture was stirred at 25° C. for 3 h and filtered. The filtrate was concentrated under reduced pressure. The residue was added to a mixture of sodium iodide (59 mg, 0.37 mmol), 2-[6-(tert-butoxycarbonylamino)-4-methyl-5-oxo-7,8-dihydro-6H-pyrazolo[1,5-a][1,3]diazepin-2-yl]ethyl methanesulfonate (150 mg, 0.37 mmol) and N,N-diisopropylethylamine (241 mg, 1.86 mmol) in N,N-dimethylformamide (2 mL). The reaction mixture was heated at 60° C. for 4 h and concentrated under reduced pressure. The residue was purified by column chromatography (silica gel, 100-200 mesh, solvent gradient: 0-10% methanol in dichloromethane) to give tert-butyl (2-(2-(3,3-difluoroazetidin-1-yl)ethyl)-4-methyl-5-oxo-5,6,7,8-tetrahydro-4H-pyrazolo[1,5-a][1,3]diazepin-6-yl)carbamate (100 mg, 67%). LCMS $R_T$=0.547 min, m/z=400.0 $[M+H]^+$.

LCMS (5 to 95% acetonitrile in water+0.03% trifluoacetic acid over 1.5 mins) retention time 0.547 min, ESI+ found [M+H]=400.0.

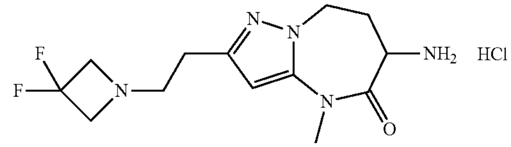 [SMILES: CN1C(=O)C(N)CCn2nc(CCN3CC(F)(F)C3)cc21 ; Cl]

Step 2: 6-amino-2-(2-(3,3-difluoroazetidin-1-yl) ethyl)-4-methyl-7,8-dihydro-4H-pyrazolo[1,5-a][1,3] diazepin-5(6H)-one hydrochloride To a solution of tert-butyl (2-(2-(3,3-difluoroazetidin-1-yl)ethyl)-4-methyl-5-oxo-5,6,7,8-tetrahydro-4H-pyrazolo [1,5-a][1,3]diazepin-6-yl)carbamate (100 mg, 0.25 mmol) in ethyl acetate (5 mL) was added hydrochloric acid (4 M in ethyl acetate, 5.0 mL, 20.0 mmol). The mixture was stirred at 25° C. for 3 h and concentrated under reduced pressure to give the crude 6-amino-2-[2-(3,3-difluoroazetidin-1-yl) ethyl]-4-methyl-7,8-dihydro-6H-pyrazolo[1,5-a][1,3]diazepin-5-one hydrochloride (84 mg, 99.9%) as a white solid, used in the next step without further purification.

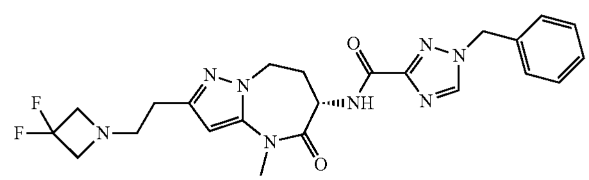

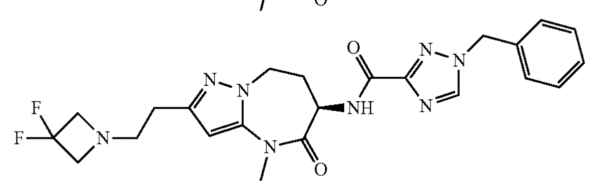

Step 3: 1-benzyl-N-[(6S)-2-[2-(3,3-difluoroazetidin-1-yl)ethyl]-4-methyl-5-oxo-7,8-dihydro-6H-pyrazolo [1,5-a][1,3]diazepin-6-yl]-1,2,4-triazole-3-carboxamide and 1-benzyl-N-[(6R)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide A mixture of 1-benzyl-1,2,4-triazole-3-carboxylic acid (12 mg, 0.06 mmol), 6-amino-2-[2-(3,3-difluoroazetidin-1-yl)ethyl]-4-methyl-7,8-dihydro-6H-pyrazolo[1,5-a][1,3]diazepin-5-one hydrochloride (20 mg, 0.06 mmol), 1-hydroxybenzotriazole (12 mg, 0.09 mmol) and 1-(3-dimethylaminopropyl)-3-ethyl carbodiimidehydrochloride (11 mg, 0.06 mmol) in N,N-Dimethylformamide (5 mL) was stirred at 25° C. for 2 h. The mixture was concentrated under reduced pressure and the residue was purified by PR-HPLC (acetonitrile 5-30%/0.05% HCl in water) to give 1-benzyl-N-[(6S)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide (10 mg, 7.5%) as a white solid. The racemic material was separated by chiral SFC (AD (250 mm*30 mm, 10 um), 0.1% $NH_4OH$ in EtOH, 50%, 80 mL/min), and further purified by RP-HPLC (acetonitrile 27-57%/0.05% ammonia hydroxide in water) to give:

1-benzyl-N-[(6S)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide (Peak 1, retention time 4.921 min) (3.1 mg, 11%) as a white solid. $^1$H NMR (400 MHz, $CD_3OD$) δ 8.58 (s, 1H), 7.42-7.35 (m, 5H), 6.21 (s, 1H), 5.50 (s, 2H), 4.59-4.52 (m, 1H), 4.36-4.32 (m, 1H), 4.26-4.22 (m, 1H), 3.67 (t, J=12.0 Hz, 4H), 3.35 (s, 3H), 2.97-2.82 (m, 3H), 2.75-2.65 (m, 2H), 2.29-2.23 (m, 1H). LCMS $R_T$=0.660 min, m/z=485.2 $[M+H]^+$.

LCMS (5 to 95% acetonitrile in water+0.03% trifluoacetic acid over 1.5 mins) retention time 0.66 min, ESI+ found [M+H]=485.2.

1-benzyl-N-[(6R)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide (Peak 2, retention time 6.833 min) (3.0 mg, 10%) as a white solid. $^1$H NMR (400 MHz, $CD_3OD$) δ 8.58 (s, 1H), 7.42-7.35 (m, 5H), 6.20 (s, 1H), 5.50 (s, 2H), 4.58-4.52 (m, 1H), 4.36-4.32 (m, 1H), 4.26-4.21 (m, 1H), 3.67 (t, J=12.0 Hz, 4H), 3.35 (s, 3H), 2.97-2.82 (m, 3H), 2.75-2.65 (m, 2H), 2.30-2.23 (m, 1H). LCMS $R_T$=0.660 min, m/z=485.2 $[M+H]^+$.

LCMS (5 to 95% acetonitrile in water+0.03% trifluoacetic acid over 1.5 mins) retention time 0.66 min, ESI+ found [M+H]=485.2.

SFC condition: Column: Chiralpak AD-3 100×4.6 mm I.D., 3 um Mobile phase: A: $CO_2$ B: ethanol (0.05% DEA), Gradient: from 5% to 40% of B in 4.5 min and hold 40% for 2.5 min, then 5% of B for 1 min, Flow rate: 2.8 mL/min Column temperature: 40° C.

Example 773

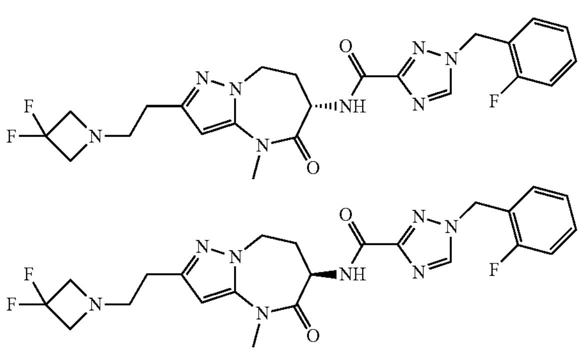

1-[(2-fluorophenyl)methyl]-N-[(6S)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide and 1-[(2-fluorophenyl)methyl]-N-[(6R)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide Amide coupling prepared in a similar fashion to WX Method 205. The racemic material was separated by chiral SFC to give:

1-[(2-fluorophenyl)methyl]-N-[(6 S)-2-[2-(3,3-difluoroazetidin-1-yl)ethyl]-4-methyl-5-oxo-7, 8-dihydro-6H-pyrazolo[1,5-a][1,3]diazepin-6-yl]-1,2,4-triazole-3-carboxamide (Peak 1, retention time 4.665 min) (2.2 mg, 22%) as a white solid. $^1$H NMR (400 MHz, $CD_3OD$) δ 8.58 (s, 1H), 7.42-7.35 (m, 2H), 7.20-7.12 (m, 2H), 6.19 (s, 1H), 5.50 (s, 2H), 4.57-4.52 (m, 1H), 4.36-4.32 (m, 1H), 4.24-4.20 (m, 1H), 3.65 (t, J=12.0 Hz, 3H), 3.30 (s, 3H), 2.97-2.82 (m, 3H), 2.75-2.67 (m, 2H), 2.29-2.23 (m, 1H). LCMS $R_T$=0.670 min, m/z=503.2 $[M+H]^+$.

LCMS (5 to 95% acetonitrile in water+0.03% trifluoacetic acid over 1.5 mins) retention time 0.67 min, ESI+ found [M+H]=503.2.

1-[(2-fluorophenyl)methyl]-N-[(6R)-2-[2-(3,3-difluoroazetidin-1-yl)ethyl]-4-methyl-5-oxo-7, 8-dihydro-6H-pyrazolo[1,5-a][1,3]diazepin-6-yl]-1,2,4-triazole-3-carboxamide (Peak 1, retention time 6.242 min) (3.0 mg, 30%) as a white solid. $^1$H NMR (400 MHz, $CD_3OD$) δ 8.59 (s, 1H), 7.42-7.35 (m, 2H), 7.20-7.12 (m, 2H), 6.19 (s, 1H), 5.57 (s, 2H), 4.57-4.52 (m, 1H), 4.36-4.32 (m, 1H), 4.24-4.20 (m, 1H), 3.64 (t, J=12.0 Hz, 3H), 3.30 (s, 3H), 2.93-2.82 (m, 3H), 2.75-2.67 (m, 2H), 2.29-2.23 (m, 1H). LCMS $R_T$=0.675 min, m/z=503.2 $[M+H]^+$.

LCMS (5 to 95% acetonitrile in water+0.03% trifluoacetic acid over 1.5 mins) retention time 0.67 min, ESI+ found [M+H]=503.2.

SFC conditions: Column: Chiralpak AD-3 100×4.6 mm I.D., 3 um Mobile phase: A: $CO_2$ B: ethanol (0.05% DEA). Gradient: from 5% to 40% of B in 4.5 min and hold 40% for 2.5 min, then 5% of B for 1 min. Flow rate: 2.8 mL/min. Column temperature: 40° C.

Example 774

WX Method 210

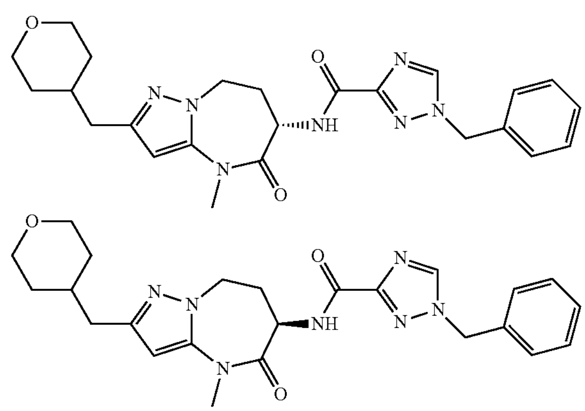

1-benzyl-N-[(6S)-4-methyl-5-oxo-2-(tetrahydropyran-4-ylmethyl)-7,8-dihydro-6H-pyrazolo[1,5-a][1,3]diazepin-6-yl]-1,2,4-triazole-3-carboxamide and 1-benzyl-N-[(6R)-4-methyl-5-oxo-2-(tetrahydropyran-4-ylmethyl)-7,8-dihydro-6H-pyrazolo[1,5-a][1,3]diazepin-6-yl]-1,2,4-triazole-3-carboxamide

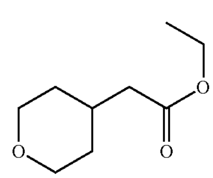

Step 1: ethyl 2-tetrahydropyran-4-ylacetate

A solution of 2-tetrahydropyran-4-ylacetic acid (5.0 g, 34.68 mmol) and cesium carbonate (22.6 g, 69.36 mmol) in N,N-dimethylformamide (60 mL) was added iodoethane (10.8 g, 69.36 mmol) over 10 min at 0° C. The resulting mixture was stirred at 15° C. for 60 h and quenched by addition of water (100 mL). The mixture was extracted with ethyl acetate (3×300 mL). The combined organic layers were dried over sodium sulfate and concentrated under reduced pressure to give crude ethyl 2-tetrahydropyran-4-ylacetate (5.8 g, 97%) as a yellow oil. $^1$H NMR (400 MHz, $CDCl_3$) δ 4.21-4.08 (m, 2H), 4.00-3.90 (m, 2H), 3.47-3.35 (m, 2H), 2.24 (d, J=8.0 Hz, 1H), 2.09-1.96 (m, 1H), 1.70-1.58 (m, 2H), 1.42-1.31 (m, 2H), 1.26 (t, J=8.0 Hz, 3H).

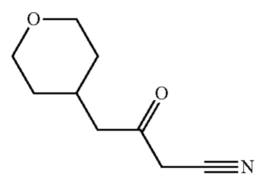 [SMILES: N#CCC(=O)CC1CCOCC1]

Step 2: 3-oxo-4-tetrahydropyran-4-yl-butanenitrile

To a solution of acetonitrile (2 mL, 37.69 mmol) in tetrahydrofuran (60 mL) was added n-butyllithium (2.5 M in Hexanes, 15.1 mL, 37.69 mmol) dropwise at −78° C. After addition, the mixture was stirred at −78° C. for 30 min, then ethyl 2-tetrahydropyran-4-ylacetate (5.8 g, 33.68 mmol) was added dropwise. The mixture was warmed up to room temperature and stirred at 25° C. for another 2 h. The reaction mixture was quenched by addition of saturated aqueous ammonium chloride (50 mL) and extracted with ethyl acetate (2×200 mL). The combined organic layers were dried over sodium sulfate and concentrated under reduced pressure to give 3-oxo-4-tetrahydropyran-4-yl-butanenitrile (4.4 g, 76%) as a brown oil, used in the next step without further purification.

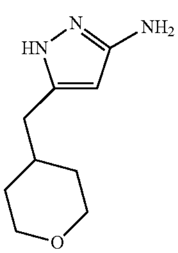 [SMILES: Nc1cc(CC2CCOCC2)[nH]n1]

Step 3: 5-(tetrahydropyran-4-ylmethyl)-1H-pyrazol-3-amine

A mixture of 3-oxo-4-tetrahydropyran-4-yl-butanenitrile (4.4 g, 26.31 mmol) and hydrazine hydrate (30 mL) in propan-2-ol (30 mL) was heated at 60° C. for 12 h and concentrated under reduced pressure. The residue was purified by flash column chromatography (silica gel, 100-200 mesh, 0 to 7% methanol in dichloromethane) to give 5-(tetrahydropyran-4-ylmethyl)-1H-pyrazol-3-amine (3.2 g, 67%) as a yellow oil, used as is in the next step. LCMS $R_T$=1.084 min; m/z=182.2 $(M+H)^+$. LCMS (10 to 80% acetonitrile in water+0.05% ammonium hydroxide over 3 minutes) retention time 1.084 min, ESI+ found [M+H]= 182.2.

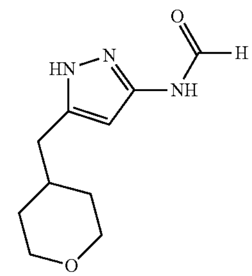 [SMILES: O=CNc1cc(CC2CCOCC2)[nH]n1]

Step 4: N-[5-(tetrahydropyran-4-ylmethyl)-1H-pyrazol-3-yl]formamide

A mixture of 5-(tetrahydropyran-4-ylmethyl)-1H-pyrazol-3-amine (3.2 g, 17.66 mmol) and formic acid (30 mL) was heated at 110° C. for 12 h and concentrated under reduced pressure. The residue was purified by flash column chromatography (silica gel, 100-200 mesh, 0 to 5% methanol in dichloromethane) to give N-[5-(tetrahydropyran-4-ylmethyl)-1H-pyrazol-3-yl]formamide (3.4 g, 92%) as a yellow solid, used as is in the next step. LCMS $R_T$=1.241 min; m/z=210.2 $(M+H)^+$. LCMS (0 to 60% acetonitrile in water+0.05% ammonium hydroxide over 3.0 mins) retention time 1.241 min, ESI+ found [M+H]=210.2.

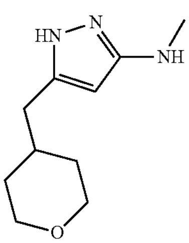

Step 5: N-methyl-5-(tetrahydropyran-4-ylmethyl)-1H-pyrazol-3-amine

To a stirred solution of N-[5-(tetrahydropyran-4-ylmethyl)-1H-pyrazol-3-yl]formamide (3.4 g, 16.25 mmol) in tetrahydrofuran (100 mL) was added borane (1M in tetrahedron, 49.0 mL, 49.0 mmol) dropwise at 0° C. After addition, the mixture was stirred for 2 h at 0° C. and then quenched by addition of methanol (10 mL). The resulting mixture was stirred for another 30 min at 15° C. and concentrated under reduced pressure. The residue was purified by flash column chromatography (silica gel, 100-200 mesh, 0 to 5% methanol in dichloromethane) to obtain N-methyl-5-(tetrahydropyran-4-ylmethyl)-1H-pyrazol-3-amine (1.9 g, 60%) as a light yellow oil, used as is in the next step. LCMS $R_T$=1.316 min; m/z=196.2 $(M+H)^+$. LCMS (0 to 60% acetonitrile in water+0.05% ammonium hydroxide over 3.0 mins) retention time 1.316 min, ESI+ found [M+H]= 196.2.

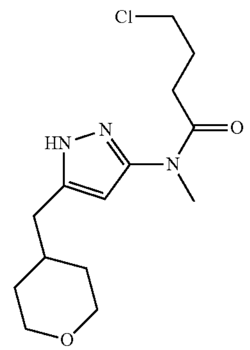 [SMILES: CN(C(=O)CCCCl)c1cc(CC2CCOCC2)[nH]n1]

Step 6: 4-chloro-N-methyl-N-[5-(tetrahydropyran-4-ylmethyl)-1H-pyrazol-3-yl]butanamide A mixture of 4-chlorobutanoyl chloride (10 mL) and N-methyl-5-(tetrahydropyran-4-ylmethyl)-1H-pyrazol-3-amine (1.5 g, 7.68 mmol) was heated at 60° C. for 1 h and quenched by slow addition of methanol (10 mL). The resulting mixture was stirred for 15 min and concentrated under reduced pressure. The residue was purified by flash column chromatography (silica gel, 100-200 mesh, 0 to 5% methanol in dichloromethane) to afford 4-chloro-N-[5-(1-fluorocyclopropyl)-1H-pyrazol-3-yl]-N-methyl-butanamide (1.72 g, 75%) as a yellow oil, used as is in the next step. LCMS $R_T$=0.633 min; m/z=299.8 $(M+H)^+$. LCMS (5 to 95% acetonitrile in water+0.03% trifluoroacetic acid over 1.5 mins) retention time 0.633 min, ESI+ found [M+H]=299.8.

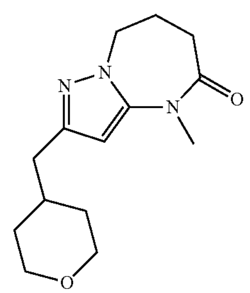 [SMILES: CN1C(=O)CCCn2nc(CC3CCOCC3)cc21]

Step 7: 4-methyl-2-(tetrahydropyran-4-ylmethyl)-7,8-dihydro-6H-pyrazolo[1,5-a][1,3]diazepin-5-one A mixture of cesium carbonate (3.7 g, 11.4 mmol) and 4-chloro-N-methyl-N-[5-(tetrahydropyran-4-ylmethyl)-1H-pyrazol-3-yl]butanamide (1.72 g, 5.73 mmol) in N,N-dimethylformamide (20 mL) was stirred at 25° C. for 15 h and filtered. The filtrate was concentrated under reduced pressure and the residue was purified by flash column chromatography (silica gel, 100-200 mesh, 0 to 5% methanol in dichloromethane) to afford 4-methyl-2-(tetrahydropyran-4-ylmethyl)-7,8-dihydro-6H-pyrazolo[1,5-a][1,3]diazepin-5-one (1.1 g, 52%) as a yellow oil, used as is in the next step. LCMS $R_T$=0.583 min; m/z=263.8 $(M+H)^+$. LCMS (5 to 95% acetonitrile in water+0.03% trifluoroacetic acid over 1.5 mins) retention time 0.583 min, ESI+ found [M+H]=263.8.

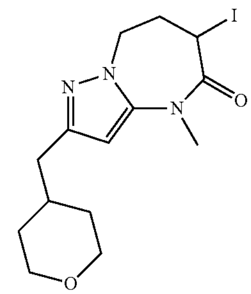 [SMILES: CN1C(=O)C(I)CCn2nc(CC3CCOCC3)cc21]

Step 8: 6-iodo-4-methyl-2-(tetrahydropyran-4-ylmethyl)-7,8-dihydro-6H-pyrazolo[1,5-a][1,3]di azepin-5-one To a stirred solution of 4-methyl-2-(tetrahydropyran-4-ylmethyl)-7,8-dihydro-6H-pyrarazolo[1,5-a][1,3]diazepin-5-one (200 mg, 0.76 mmol) in dichloromethane (60 mL) was slowly added $N^1,N^1,N^1,N^2$-tetramethylethane-1,2-diamine (1.14 mL, 7.59 mmol) and iodotrimethylsilane (1.08 mL, 7.59 mmol) at −15° C. under nitrogen protection. The mixture was stirred at −15° C. for 1.5 h, and then iodine (578 mg, 2.28 mmol) was added. The reaction mixture was stirred for another 2 h, and then quenched by addition of 50% aqueous sodium thiosulfate (10 mL). The resulting mixture was extracted with dichloromethane (2×80 mL). The combined organic layers were washed with brine (2×20 mL), dried over sodium sulfate and concentrated under reduced pressure to give the crude 6-iodo-4-methyl-2-(tetrahydropyran-4-ylmethyl)-7,8-dihydro-6H-pyrazolo[1,5-a][1,3]diazepin-5-one (150 mg, 53%) as a yellow oil, used in the next step without further purification. LCMS $R_T$=1.839 min, m/z=390.0 $[M+H]^+$. LCMS (0 to 60% acetonitrile in water+0.05% ammonium hydroxide over 3 mins) retention time 1.839 min, ESI+ found [M+H]=390.0.

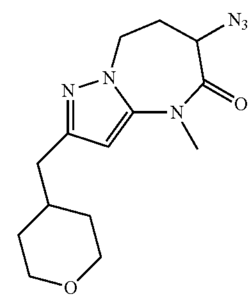

Step 9: 6-azido-4-methyl-2-(tetrahydropyran-4-ylmethyl)-7,8-dihydro-6H-pyrazolo[1,5-a][1,3]di azepin-5-one A mixture of 6-iodo-4-methyl-2-(tetrahydropyran-4-ylmethyl)-7,8-dihydro-6H-pyrazolo[1,5-a][1,3]diazepin-5-one (295 mg, 0.76 mmol) and sodium azide (120 mg, 1.85 mmol) in N,N-dimethylformamide (5 mL) was stirred at 25° C. for 12 h. The reaction mixture was quenched by addition of 20% aqueous sodium hypochlorite (30 mL) and extracted with ethyl acetate (3×50 mL). The combined organic layers were washed with brine (2×20 mL), dried over sodium sulfate and concentrated under reduced pressure to give crude 6-azido-4-methyl-2-(tetrahydropyran-4-ylmethyl)-7,8-dihydro-6H-pyrazolo[1,5-a][1,3]diazepin-5-one (230 mg, 99%) as a yellow oil, used in the next step without further purification.

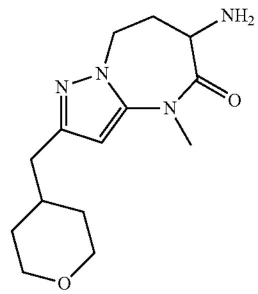 [SMILES: CN1C(=O)C(N)CCn2nc(CC3CCOCC3)cc21]

Step 10: 6-amino-4-methyl-2-(tetrahydropyran-4-ylmethyl)-7,8-dihydro-6H-pyrazolo[1,5-a][1,3]diazepin-5-one A mixture of 6-azido-4-methyl-2-(tetrahydropyran-4-ylmethyl)-7,8-dihydro-6H-pyrazolo[1,5-a][1,3]diazepin-5-one (230 mg, 0.76 mmol) and palladium on carbon (10%, 10 mg) in methanol (10 mL) was hydrogenated (15 psi) at 20° C. for 12 h and filtered. The filtrate was concentrated under reduced pressure and the residue was purified by preparative TLC (10% methanol in dichloromethane, $R_f$=0.4) to afford 6-amino-4-methyl-2-(tetrahydropyran-4-ylmethyl)-7,8-dihydro-6H-pyrazolo[1,5-a][1,3]diazepin-5-one (140 mg, 66%) as a yellow oil, used as is in the next step.

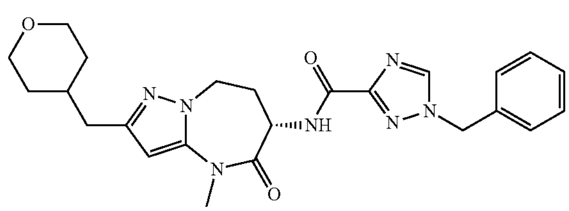

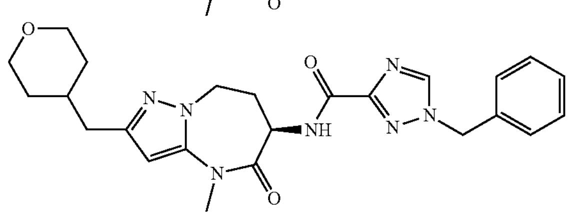

Step 11: 1-benzyl-N-[(6S)-4-methyl-5-oxo-2-(tetrahydropyran-4-ylmethyl)-7,8-dihydro-6H-pyrazolo[1,5-a][1,3]diazepin-6-yl]-1,2,4-triazole-3-carboxamide and 1-benzyl-N-[(6R)-4-methyl-5-oxo-2-(tetrahydropyran-4-ylmethyl)-7,8-dihydro-6H-pyrazolo[1,5-a][1,3]diazepin-6-yl]-1,2,4-triazole-3-carboxamide A mixture of 1-benzyl-1,2,4-triazole-3-carboxylic acid (102 mg, 0.5 mmol), 6-amino-4-methyl-2-(tetrahydropyran-4-ylmethyl)-7,8-dihydro-6H-pyrazolo[1,5-a][1,3]diazepin-5-one (140 mg, 0.5 mmol), N,N-dimethyl-3 (methyliminomethylenethyl acetatemino)propan-1-amine hydrochloride (144 mg, 0.75 mmol) and 1-hydroxybenzotrizole (101 mg, 0.75 mmol) in N,N-dimethylformamide (5 mL) was stirred at 25° C. for 12 h. The mixture was concentrated under reduced pressure and the residue was and purified by RP-HPLC (25% to 50% acetonitrile, 0.225% formic acid in water) to afford 1-benzyl-N-[4-methyl-5-oxo-2-(tetrahydropyran-4-ylmethyl)-7,8-dihydro-6H-pyrazolo[1,5-a][1,3]diazepin-6-yl]-1,2,4-triazole-3-carboxamide (130 mg, 55%) as a white solid. The racemic material was further purified by chiral SFC to give:

1-benzyl-N-[(6S)-4-methyl-5-oxo-2-(tetrahydropyran-4-ylmethyl)-7,8-dihydro-6H-pyrazolo[1,5-a][1,3]diazepin-6-yl]-1,2,4-triazole-3-carboxamide (Peak 1, retention time 1.543 min) (19.7 mg, 15.2%) as a white solid. $^1$H NMR (400 MHz, $CD_3OD$) δ 8.57 (s, 1H), 7.40-7.33 (m, 5H), 6.16 (s, 1H), 5.48 (s, 2H), 4.54-4.48 (m, 1H), 4.37-4.30 (m, 1H), 4.27-4.17 (m, 1H), 3.96-3.90 (m, 2H), 3.44-3.36 (m, 2H), 3.33 (s, 3H), 2.90-2.80 (m, 1H), 2.57-2.53 (m, 2H), 2.30-2.22 (m, 1H), 1.92-1.82 (m, 1H), 1.68-1.62 (m, 2H), 1.35-1.31 (m, 2H). LCMS $R_T$=0.754 min, m/z=464.2 [M+H]$^+$.

LCMS (5 to 95% acetonitrile in water+0.03% trifluoroacetic acid over 1.5 mins) retention time 0.754 min, ESI+ found [M+H]=464.2.

1-benzyl-N-[(6S)-4-methyl-5-oxo-2-(tetrahydropyran-4-ylmethyl)-7,8-dihydro-6H-pyrazolo[1,5-a][1,3]diazepin-6-yl]-1,2,4-triazole-3-carboxamide (Peak 2, retention time 1.875 min) (26.0 mg, 20.0%) as a white solid. $^1$H NMR (400 MHz, $CD_3OD$) δ 8.57 (s, 1H), 7.40-7.33 (m, 5H), 6.16 (s, 1H), 5.48 (s, 2H), 4.54-4.48 (m, 1H), 4.38-4.30 (m, 1H), 4.27-4.17 (m, 1H), 3.96-3.90 (m, 2H), 3.44-3.36 (m, 2H), 3.33 (s, 3H), 2.90-2.81 (m, 1H), 2.57-2.53 (m, 2H), 2.30-2.22 (m, 1H), 1.93-1.82 (m, 1H), 1.69-1.62 (m, 2H), 1.35-1.31 (m, 2H). LCMS $R_T$=0.752 min, m/z=464.2 [M+H]$^+$.

LCMS (5 to 95% acetonitrile in water+0.03% trifluoroacetic acid over 1.5 mins) retention time 0.752 min, ESI+ found [M+H]=464.2.

SFC condition: Column: Chiralpak AD-3 50*4.6 mm I.D., 3 um Mobile phase: A: $CO_2$ B: methanol (0.05% DEA) Gradient: hold 5% for 0.2 min, then from 5% to 40% of B in 1.4 min and hold 40% for 1.05 min, then 5% of B for 0.35 min. Flow rate: 4 mL/min Column temp: 40° C.

Example 775: Suzuki Method 2

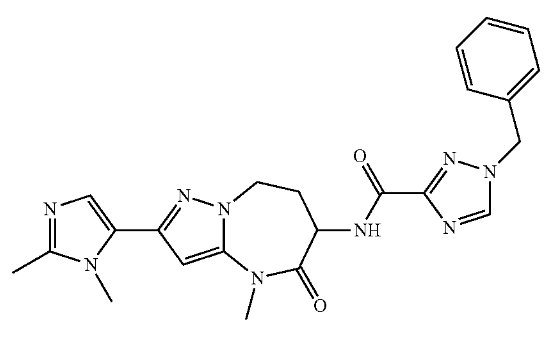 [SMILES: Cc1ncc(-c2cc3n(n2)CCC(NC(=O)c2ncn(Cc4ccccc4)n2)C(=O)N3C)n1C]

1-benzyl-N-(2-(1,2-dimethyl-1H-imidazol-5-yl)-4-methyl-5-oxo-5,6,7,8-tetrahydro-4H-pyrazolo[1,5-a][1,3]diazepin-6-yl)-1H-1,2,4-triazole-3-carboxamide To a microwave vial was charged 1-benzyl-N-(2-bromo-4-methyl-5-oxo-7,8-dihydro-6H-pyrazolo[1,5-a][1,3]diazepin-6-yl)-1,2,4-triazole-3-carboxamide (66 mg, 0.15 mmol), potassium acetate (30 mg, 0.31 mmol), 4,4,5,5-tetramethyl-2-(4,4,5,5-tetramethyl-1,3,2-dioxaborolan-2- yl)-1,3,2-dioxaborolane (72 mg, 0.28 mmol) and [1,1'-bis(diphenylphosphino)ferrocene]dichloropalladium(II) (1:1) (9.5 mg, 0.0129 mmol)

The solids were dissolved in anhydrous acetonitrile (2 mL) and the vial was sealed and irradiated in a microwave at 140° C. for 15 min. To reaction mixture was added 5-bromo-1,2-dimethyl-imidazole (57 mg, 0.257 mmol), an additional [1,1'-bis(diphenylphosphino)ferrocene]dichloropalladium(II) (1:1) (9.5 mg, 0.0129 mmol) and diluted with 1 M potassium carbonate (2 mL). The vial was sealed and irradiated in a microwave at 110° C. for 10 min. The reaction mixture was diluted with ethyl acetate (10 mL), washed with water (2×5 mL), brine and dried over sodium sulphate. The filtrate was concentrated to dryness in vacuo and the residue was purified by reverse phase HPLC to afford 1-benzyl-N-(2-(1,2-dimethyl-1H-imidazol-5-yl)-4-methyl-5-oxo-5,6,7,8-tetrahydro-4H-pyrazolo[1,5-a][1,3]diazepin-6-yl)-1H-1,2,4-triazole-3-carboxamide as(8 mg, 12% yield) a white solid. $^1$H NMR (400 MHz, DMSO-d6) δ 8.82 (s, 1H), 8.58 (d, J=7.8 Hz, 1H), 8.34 (s, 2H), 7.45-7.24 (m, 5H), 7.05 (s, 1H), 6.60 (s, 1H), 5.49 (s, 2H), 3.76 (s, 3H), 3.27 (s, 3H), 2.81 (dd, J=63.8, 0.6 Hz, 1H), 2.71-2.56 (m, 1H), 2.32 (s, 3H). LC-MS $R_T$=2.76 min, m/z=460.2 [M+H]$^+$. LCMS (2 to 98% acetonitrile in water+0.1% formic acid over 10 mins) retention time 2.76 min, ESI+ found [M+H]=460.2.

Example 776

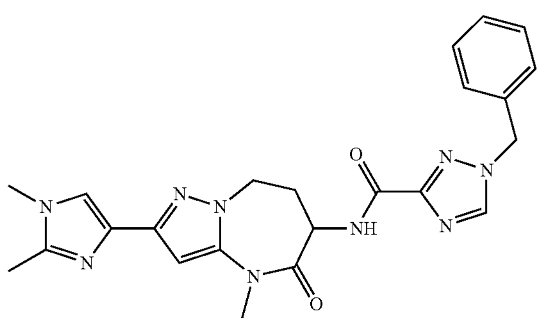 [SMILES: Cc1nc(-c2cc3n(n2)CCC(NC(=O)c2ncn(Cc4ccccc4)n2)C(=O)N3C)cn1C]

1-benzyl-N-(2-(1,2-dimethyl-1H-imidazol-4-yl)-4-methyl-5-oxo-5,6,7,8-tetrahydro-4H-pyrazolo[1,5-a][1,3]diazepin-6-yl)-1H-1,2,4-triazole-3-carboxamide Suzuki_Method_2 (7 mg, 10%) as a white solid. $^1$H NMR (400 MHz, DMSO-d6) δ 8.82 (s, 1H), 8.52 (d, J=7.8 Hz, 1H), 8.32 (s, 2H), 7.46-7.23 (m, 5H), 6.46 (s, 1H), 5.48 (s, 2H), 3.56 (s, 3H), 3.26 (s, 3H), 2.73-2.57 (m, 1H), 2.29 (s, 3H). LC-MS $R_T$=2.27 min, m/z=460.2 [M+H]$^+$. LCMS (2 to 98% acetonitrile in water+0.1% formic acid over 10 mins) retention time 2.72 min, ESI+ found [M+H]=460.2.

Example 777

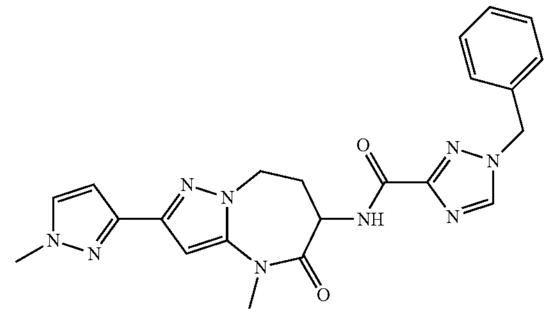 [SMILES: CN1C(=O)C(NC(=O)c2ncn(Cc3ccccc3)n2)CCn2nc(-c3ccn(C)n3)cc21]

1-benzyl-N-(4-methyl-2-(1-methyl-1H-pyrazol-3-yl)-5-oxo-5,6,7,8-tetrahydro-4H-pyrazolo[1,5-a][1,3]diazepin-6-yl)-1H-1,2,4-triazole-3-carboxamide Suzuki_Method_2. (9 mg, 20%) as a white solid. $^1$H NMR (400 MHz, DMSO-d6) δ 8.82 (s, 1H), 8.54 (d, J=7.8 Hz, 1H), 7.70 (dd, J=2.2, 0.4 Hz, 1H), 7.45-7.20 (m, 5H), 6.58 (s, 1H), 6.50 (d, J=2.2 Hz, 1H), 5.48 (s, 2H), 4.37 (s, 1H), 4.11-3.98 (m, 1H), 3.86 (s, 3H), 3.17 (d, J=5.2 Hz, 4H). LC-MS $R_T$=3.67 min, m/z=446.2 [M+H]$^+$. LCMS (2 to 98% acetonitrile in water+0.1% formic acid over 10 mins) retention time 3.67 min, ESI+ found [M+H]=446.2.

Example 778

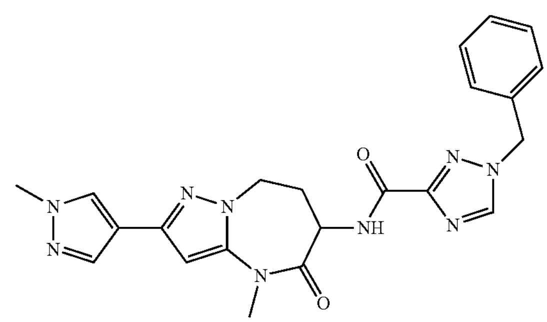 [SMILES: CN1C(=O)C(NC(=O)c2ncn(Cc3ccccc3)n2)CCn2nc(-c3cnn(C)c3)cc21]

1-benzyl-N-(4-methyl-2-(1-methyl-1H-pyrazol-4-yl)-5-oxo-5,6,7,8-tetrahydro-4H-pyrazolo[1,5-a][1,3]diazepin-6-yl)-1H-1,2,4-triazole-3-carboxamide Suzuki_Method_1 (13 mg, 29%). 1H NMR (400 MHz, DMSO-d6) δ 8.82 (s, 1H), 8.54 (d, J=7.8 Hz, 1H), 7.98 (d, J=0.9 Hz, 1H), 7.70 (d, J=0.8 Hz, 1H), 7.47-7.19 (m, 4H), 6.50 (s, 1H), 5.48 (s, 2H), 4.45-4.08 (m, 2H), 3.86 (s, 3H), 3.26 (s, 4H), 2.44-2.24 (m, 1H). LC-MS $R_T$=3.63 min, m/z=446.2 [M+H]$^+$.

Example 779

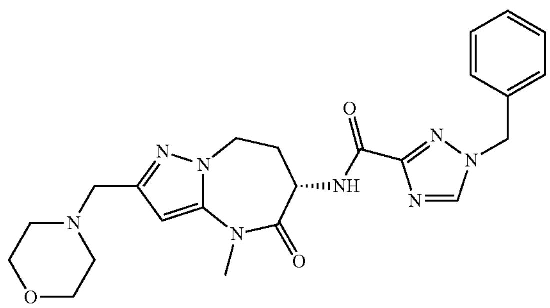 [SMILES: CN1C(=O)[C@@H](NC(=O)c2ncn(Cc3ccccc3)n2)CCn2nc(CN3CCOCC3)cc21]

(S)-1-benzyl-N-(4-methyl-2-(morpholinomethyl)-5-oxo-5,6,7,8-tetrahydro-4H-pyrazolo[1,5-a][1,3]diazepin-6-yl)-1H-1,2,4-triazole-3-carboxamide 1-benzyl-N-(4-methyl-2-(morpholinomethyl)-5-oxo-5,6,7,8-tetrahydro-4H-pyrazolo[1,5-a][1, 3]diazepin-6-yl)-1H-1,2,4-triazole-3-carboxamide (Example 443) was further purified by chiral SFC (Chiralpak AD; 150×21.2 mm, 5 um; 30% methanol isocratic elution with Carbon Dioxide) affording (S)-1-benzyl-N-(4-methyl-2-(morpholinomethyl)-5-oxo-5, 6,7,8-tetrahydro-4H-pyrazolo[1,5-a][1,3]diazepin-6-yl)-1H-1,2,4-triazole-3-carboxamide (13.4 mg, 28.4%) as a white solid:

Analytical data for (S)-1-benzyl-N-(4-methyl-2-(morpholinomethyl)-5-oxo-5,6,7,8-tetrahydro-4H-pyrazolo[1,5-a][1,3]diazepin-6-yl)-1H-1,2,4-triazole-3-carboxamide: SFC $R_T$ (AD, 25% methanol+0.1% ammonium hydroxide isocratic elution with Carbon Dioxide, 2.5 min method): 0.838 min, 100% purity, 100% ee: $^1$H NMR (400 MHz, DMSO-d6) δ 8.81 (s, 1H), 8.51 (d, J=7.7 Hz, 1H), 7.42-7.26 (m, 5H), 6.26 (s, 1H), 5.48 (s, 2H), 4.36-4.24 (m, 2H), 4.14 (m, 1H), 3.57 (m, 4H), 3.48-3.21 (m, 5H), 2.59 (m, 1H), 2.43-2.29 (m, 5H). LCMS $R_T$=2.55 min, m/z=465.2 $(M+H)^+$. LCMS (5 to 95% acetonitrile in water+0.1% formic acid over 10 mins) retention time 2.55 min, ESI+ found [M+H]=465.2.

Example 780

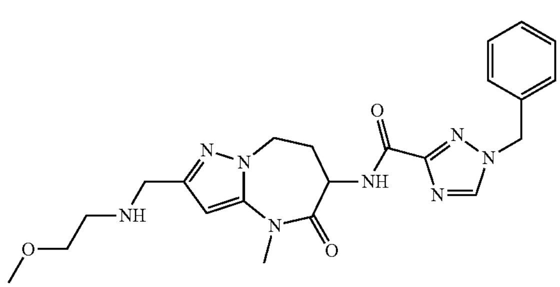 [SMILES: COCCNCc1cc2n(n1)CCC(NC(=O)c1ncn(Cc3ccccc3)n1)C(=O)N2C]

1-benzyl-N-(2-(((2-methoxyethyl)amino)methyl)-4-methyl-5-oxo-5,6,7,8-tetrahydro-4H-pyrazolo[1,5-a][1,3]diazepin-6-yl)-1H-1,2,4-triazole-3-carboxamide 1-benzyl-N-(2-(((2-methoxyethyl)amino)methyl)-4-methyl-5-oxo-5,6,7,8-tetrahydro-4H-pyrazolo[1,5-a][1,3]diazepin-6-yl)-1H-1,2,4-triazole-3-carboxamide was prepared from 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide and 2-methoxyethan-1-amine according to Method GZ7. The crude residue was purified by flash column chromatography (silica gel, 0% to 15% DCM in MeOH) to afford 1-benzyl-N-(2-(((2-methoxyethyl)amino)methyl)-4-methyl-5-oxo-5,6,7,8-tetrahydro-4H-pyrazolo[1,5-a][1,3]diazepin-6-yl)-1H-1,2,4-triazole-3-carboxamide (49 mg, 85% Yield) as a tan solid: $^1$H NMR (400 MHz, DMSO-d6) δ 8.82 (s, 1H), 8.51 (d, J=7.8 Hz, 1H), 7.43-7.26 (m, 5H), 6.26 (s, 1H), 5.48 (s, 2H), 4.31 (m, 2H), 4.21-4.07 (m, 1H), 3.66 (d, J=2.1 Hz, 2H), 3.46-3.31 (m, 2H), 3.23 (s, 6H), 2.72 (t, J=5.7 Hz, 2H), 2.58 (m, 1H), 2.41-2.28 (m, 1H). LC-MS $R_T$=2.62 min, m/z=453.2 $(M+H)^+$. LCMS (5 to 95% acetonitrile in water+0.1% formic acid over 10 mins) retention time 2.62 min, ESI+ found [M+H]=453.2.

Example 781

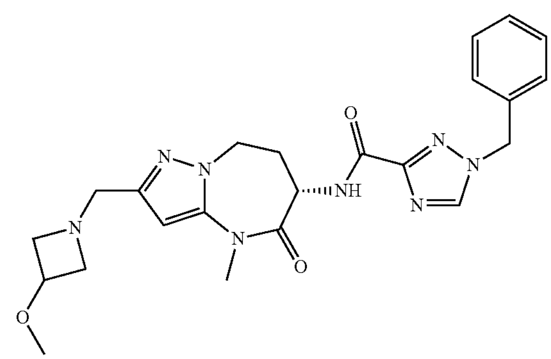 [SMILES: COC1CN(Cc2cc3n(n2)CC[C@H](NC(=O)c2ncn(Cc4ccccc4)n2)C(=O)N3C)C1]

(S)-1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide 1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide was further purified by chiral SFC (Cellulose-1; 150×21.2 mm, 5 um; 25% methanol isocratic elution with Carbon Dioxide) affording (S)-1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide (12.7 mg, 34.7%) as a white solid:

Analytical data for (S)-1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide: SFC $R_T$ (Cellulose-1, 25% methanol+0.1% ammonium hydroxide isocratic elution with Carbon Dioxide, 2.5 min method): 0.883 min, 100% purity, 100% ee: $^1$H 1H NMR (400 MHz, DMSO-d6) δ 8.81 (s, 1H), 8.51 (d, J=7.7 Hz, 1H), 7.42-7.26 (m, 5H), 6.21 (s, 1H), 5.48 (s, 2H), 4.35-4.23 (m, 2H), 4.13 (m, 1H), 3.94 (p, J=5.8 Hz, 1H), 3.57-3.32 (m, 4H), 3.18 (ds, 6H), 2.86 (m, 2H), 2.58 (m, 1H), 2.41-2.28 (m, 1H). LCMS $R_T$=2.62 min, m/z=465.2 $(M+H)^+$. LCMS (5 to 95% acetonitrile in water+0.1% formic acid over 10 mins) retention time 2.62 min, ESI+ found [M+H]=465.2

Example 782

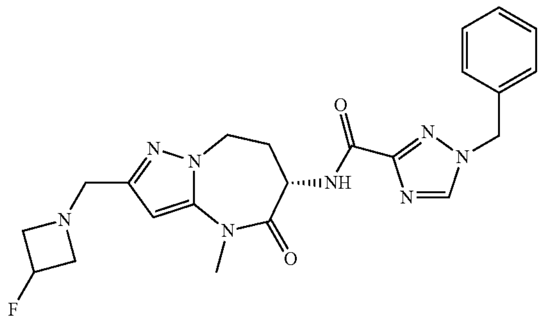 [SMILES: CN1C(=O)[C@@H](NC(=O)c2ncn(Cc3ccccc3)n2)CCn2nc(CN3CC(F)C3)cc21]

(S)-1-benzyl-N-(2-((3-fluoroazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide 1-benzyl-N-(2-((3-fluoroazetidin-1-yl)methyl)-4-methyl-5-oxo-5,6,7,8-tetrahydro-4H-pyrazol o[1,5-a][1,3]diazepin-6-yl)-1H-1,2,4-triazole-3-carboxamide was prepared from 1-benzyl-N-(2-formyl-4-methyl-5-oxo-5,6,7,8-tetrahydro-4H-pyrazolo[1,5-a][1,3]diazepin-6-yl)-1H-1,2,4-triazole-3-carboxamide was further purified by chiral SFC (Cellulose-1; 150×21.2 mm, 5 um; 35% methanol isocratic elution with Carbon Dioxide) affording (S)-1-benzyl-N-(2-((3-fluoroazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide (16.6 mg, 32.8%) as a white solid:

Analytical data for (S)-1-benzyl-N-(2-((3-fluoroazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide: SFC $R_T$ (Cellulose-1, 25% methanol+0.1% ammonium hydroxide isocratic elution with Carbon Dioxide, 2.5 min method): 0.879 min, 100% purity, 100% ee. $^1$H NMR (400 MHz, DMSO-$d_6$) δ 8.81 (s, 1H), 8.52 (d, J=7.8 Hz, 1H), 7.42-7.26 (m, 5H), 6.23 (s, 1H), 5.48 (s, 2H), 5.26-5.01 (m, 1H), 4.35-4.23 (m, 2H), 4.14 (m, 1H), 3.63-3.50 (m, 4H), 3.27-3.06 (m, 5H), 2.58 (m, 1H), 2.41-2.28 (m, 1H). LCMS $R_T$=2.59 min, m/z=453.2 $(M+H)^+$. LCMS (5 to 95% acetonitrile in water+0.1% formic acid over 10 mins) retention time 2.59 min, ESI+ found [M+H]=453.2.

Examples 783-793 are Chiral Separations of Previous Examples as Provided Above

Example 794: RIP1 Kinase Inhibition Assays (Biochemical Assay)

The compounds of the present invention were tested for their capacity to inhibit RIP1K activity as described below.

Enzyme Assay:

The ability of the receptor interacting protein kinase (RIPK1) to catalyze the hydrolysis of adenosine-5'-triphosphate (ATP) is monitored using the Transcreener ADP (adenosine-5'-diphosphate) assay (BellBrook Labs). Purified human RIP1 kinase domain (2-375) (50 nM) derived from a baculovirus-infected insect cell expression system is incubated with test compounds for 2 hours in 50 mM Hepes buffer (pH 7.5) containing 30 mM $MgCl_2$, 1 mM dithiothreitol, 50 uM ATP, 0.002% Brij-35, and 0.5% dimethyl sulfoxide (DMSO). Reactions are quenched by the addition of 1× Bell Brooks Stop buffer B (20 mM Hepes (ph7.5), 40 mM ethylenediaminetetraacetic acid and 0.02% Brij-35) containing an additional 12 mM EDTA and 55 ug/mL ADP2 antibody and 4 nM ADP-AlexaFluor® 633 tracer. The tracer bound to the antibody is displaced by the ADP generated during the RIP1K reaction, which causes a decrease in fluorescence polarization that is measured by laser excitation at 633 nm with a FP microplate reader M1000. Fractional activity was plotted against test article concentration. Using Genedata Screener software (Genedata; Basel, Switzerland), the data were fit to the tight-binding apparent inhibition constant ($K_i^{app}$) Morrison equation [Williams, J. W. and Morrison, J. F. (1979) The kinetics of reversible tight-binding inhibition. *Methods Enzymol* 63: 437-67]. The following equation was used to calculate fractional activity and $K_i^{app}$:

Fractional activity =

$$\frac{v_i}{v_o} = 1 - \frac{([E]_T + [I]_T + K_i^{app}) - \sqrt{([E]_T + [I]_T + K_i^{app})^2 - 4[E]_T[I]_T}}{2[E]_T}$$

where $[E]_T$ and $[I]_T$ are the total concentrations of active enzyme and test article, respectively.

Exemplary compounds of the present invention are provided in the following Tables along with their physiochemical characterization and in vitro RIP1 kinase inhibitory activity data. "Method" in the first column of each table refers to the synthetic method(s) used to prepare each compound as shown in the Examples above. In certain examples, chiral column retention times (min) are provided for certain stereoisomers.

TABLE 1

| Compound Example # Method | RIP1 Ki (μM) | Structure and Name | $^1$H NMR Data | MS (m/z) |
|---|---|---|---|---|
| Example 1 Method A | 4.7 | 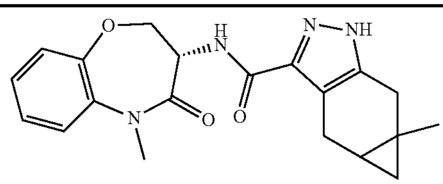 5a-methyl-N-((S)-5-methyl-4- | $^1$H NMR (400 MHz, DMSO-d6) δ 12.88 (s, 1H), 7.96-7.87 (m, 1H), 7.52-7.44 (m, 1H), 7.35-7 26 (m, 2H), 7.25-7.21 (m, 1H), 4.88-4.75 (m, 1H),4.53-4 44 (m, 1H), 4.43-4.36 (m, 1H), 3.11-3.02 (m, 1H), 2.98-2.90 (m, 1H), 2.79-2.70 (m, 1H), 2.70-2.60 (m, 1H), 1.19 (s, 3H), 1.03-0.93 (m, 1H), | 367.2 |

TABLE 1-continued

| Compound Example # Method | RIP1 Ki (μM) | Structure and Name | $^1H$ NMR Data | MS (m/z) |
|---|---|---|---|---|
| | | oxo-2,3,4,5-tetrahydrobenzo[b][1,4]oxazepin-3-yl)-1,4,4a,5,5a,6-hexahydrocyclopropa[f]indazole 3-carboxamide | 0.35-0.26 (m, 1H), 0.09-0.00 (m, 1H). | |
| Example 2 Method A' | 6.5 | 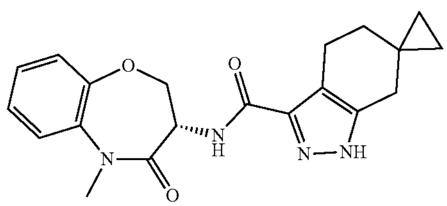 [SMILES: CN1C(=O)[C@@H](NC(=O)c2n[nH]c3c2CCC2(CC2)C3)COc2ccccc21] (S)-N-(5-methyl-4-oxo-2,3,4,5-tetrahydrobenzo[b][1,4]oxazepin-3-yl)-1',4',5',7'-tetrahydrospiro[cyclopropane-1,6'-indazole] 3'-carboxamide | $^1H$ NMR (400 MHz, DMSO-d6) δ 12.84 (s, 1H), 7.91 (d, J = 8 0 Hz, 1H), 7.52-7.45 (m, 1H), 7.35-7.26 (m, 2H), 7.25-7.21 (m, 1H), 4.90-4.76 (m, 1H), 4.56-4.32 (m, 2H), 2.68-2.55 (m, 2H), 2.48-2.42 (m, 2H), 1.53-1.37 (m, 2H), 0.42-0.33 (m, 4H). | 367.2 |
| Example 3 Method B | 0.0688 | 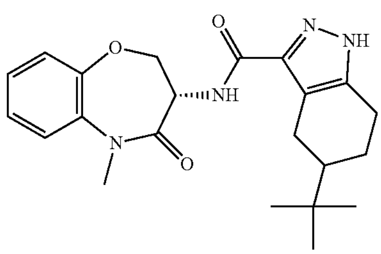 [SMILES: CN1C(=O)[C@@H](NC(=O)c2n[nH]c3c2CC(C(C)(C)C)CC3)COc2ccccc21] 5-(tert-butyl)-N-((S)-5-methyl-4-oxo-2,3,4,5-tetrahydrobenzo[b][1,4]oxazepin-3-yl)-4,5,6,7-tetrahydro-1H-indazole-3-carboxamide | $^1H$ NMR (400 MHz, DMSO-d6) δ 12.88-12.77 (m, 1H), 7.91 (d, J = 7.9 Hz, 1H), 7.51-7.46 (m, 1H), 7.35-7.26 (m, 2H), 7.27-7.19 (m, 1H), 4.88-4.77 (m, 1H), 4.55-4.35 (m, 2H), 2.86-2.65 (m, 2H), 2.19-2.05 (m, 1H), 2.01-1.91 (m, 1H), 1.37-1.17 (m, 2H), 0.89 (s, 9H). | 397.2 |
| Example 4 Method B' | 5.5 | 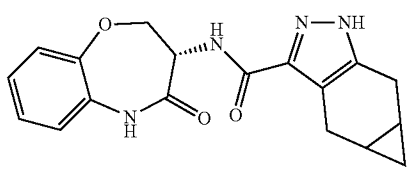 [SMILES: O=C(N[C@H]1COc2ccccc2NC1=O)c1n[nH]c2c1CC1CC1C2] N-((S)-4-oxo-2,3,4,5-tetrahydrobenzo[b][1,4]oxazepin-3-yl)-1,4,4a,5,5a,6-hexahydrocyclopropa[f]indazole-3-carboxamide | $^1H$ NMR (400 MHz, DMSO-d6) δ 12.87 (s, 1H), 10.12 (s, 1H), 8.02-7.87 (m, 1H), 7.22-7.05 (m, 4H), 4.87-4.66 (m, 1H), 4.55-4.32 (m, 2H), 3.23-3.09 (m, 1H), 3.00-2.62 (m, 4H), 2.15-2.01 (m, 1H), 1.32-1.09 (m, 2H), 0.62-0.40 (m, 1H), −0.05-−0.14 (m, 1H). | 339.1 |
| Example 5 Method C | 1.5 | 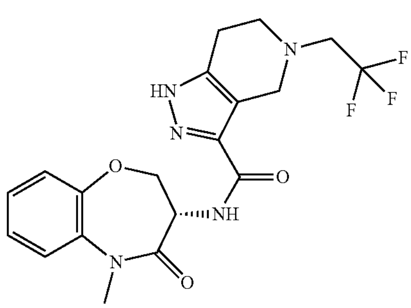 [SMILES: CN1C(=O)[C@@H](NC(=O)c2n[nH]c3c2CN(CC(F)(F)F)CC3)COc2ccccc21] (S)-N-(5-methyl-4-oxo-2,3,4,5-tetrahydrobenzo[b][1,4]oxazepin-3-yl)-5-(2,2,2-trifluoroethyl)-4,5,6,7-tetrahydro-1H-pyrazolo[4.3-c]pyridine-3-carboxamide | $^1H$ NMR (400 MHz, DMSO-d6) δ 13.03 (s, 1H), 8.01 (d, J = 8.0 Hz, 1H), 7.52-7.44 (m, 1H), 7.35-7.26 (m, 2H), 7.26-7.19 (m, 1H), 4.87-4.75 (m, 1H), 4.58-4.47 (m, 1H), 4.44-4.35 (m, 1H), 3.74 (s, 2H), 2.93-2.86 (m, 2H), 2.73-2.65 (m, 2H). | 424.1 |

TABLE 1-continued

| Compound Example # Method | RIP1 Ki (μM) | Structure and Name | $^1H$ NMR Data | MS (m/z) |
|---|---|---|---|---|
| Example 6 Method D | 0.375 | 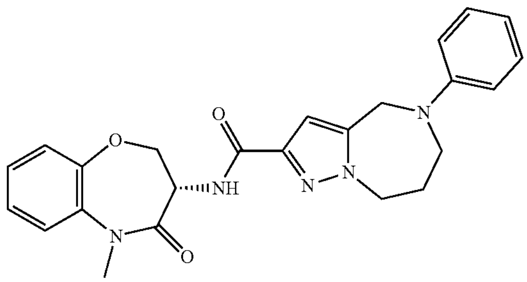 [SMILES: CN1C(=O)[C@@H](NC(=O)c2cc3n(n2)CCCN(c2ccccc2)C3)COc2ccccc21] N-[(3S)-5-methyl-4-oxo-2,3-dihydro-1,5-benzoxazepin-3-yl]-5-phenyl-4,6,7,8-tetrahydropyrazolo[1,5-a][1,4]diazepine-2-carboxamide | $^1H$ NMR (400 MHz, DMSO-d6) δ 7.93 (d, J = 8.0 Hz, 1H), 7.51-7.44 (m, 1H), 7.35-7.18 (m, 3H), 7.10 (t, J = 8.0 Hz, 2H), 6.86 (d, J= 8.4 Hz, 2H), 6.73 (s, 1H), 6.58 (t, J = 7.2 Hz, 1H), 4.83-4.64 (m, 3H), 4.54-4.40 (m, 3H), 4.37-4.34 (m, 1H), 3.93-3.79 (m, 2H), 3.29 (s, 3H), 1.84-1.82 (m, 2H) | 432.2 |
| Example 7 Method E | 3 | 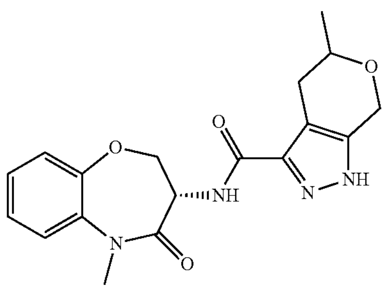 [SMILES: CC1Cc2c(C(=O)N[C@H]3COc4ccccc4N(C)C3=O)n[nH]c2CO1] 5-methyl-N-((S)-5-methyl-4-oxo-2,3-dihydro-1,5-benzoxazepin-3-yl)-1,4,5,7-tetrahydropyrano[3,4-c]pyrazole-3-carboxamide | $^1H$ NMR (400 MHz, CD3OD) δ 7.44-7.40 (m, 1H), 7.35-7.26 (m, 2H), 7.25-7.20 (m, 1H), 5.01-4.97 (m, 1H), 4.82-4.77 (m, 1H), 4.72-4.70 (m, 1H), 4.61-4.57 (m, 1H), 4.41-4.33 (m, 1H), 3.70-3.66 (m, 1H), 3.41 (s, 3H), 2.87-2.82 (m, 1H), 2.50-2 44 (m, 1H), 1.32 (d, J = 6.0 Hz, 3H) | 357.0 |
| Example 7 Method E | >10 | 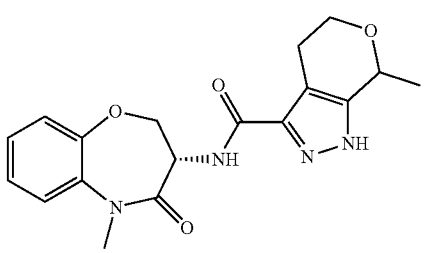 [SMILES: CC1OCCc2c(C(=O)N[C@H]3COc4ccccc4N(C)C3=O)n[nH]c21] 7-methyl-N-((S)-5-methyl-4-oxo-2,3-dihydro-1,5-benzoxazepin-3-yl)-2,4,5,7-tetrahydropyrano[3,4-c]pyrazole-3-carboxamide | $^1H$ NMR (400 MHz, $CD_3OD$) δ 7.42-7.39 (m, 1H), 7.30-7.26 (m, 2H), 7.25-7.20 (m, 1H), 4.99-4.91 (m, 1H), 4.77-4.75 (m, 1H), 4.62-4.57 (m, 1H), 4.41-4.33 (m, 1H), 4.19-4.12 (m, 1H), 3.62-3.60 (m, 1H), 3.41 (s, 3H), 2.80-2.73 (m, 2H), 1.47 (d, J = 6.8 Hz, 3H) | 357.0 |
| Example 8 Method F | 0.469 | 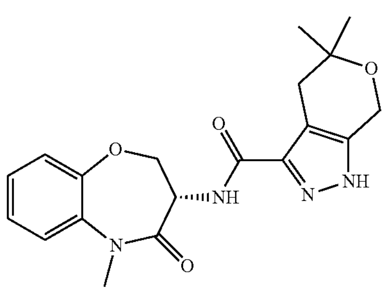 [SMILES: CN1C(=O)[C@@H](NC(=O)c2n[nH]c3c2CC(C)(C)OC3)COc2ccccc21] 5,5-dimethyl-N-[(3S)-5-methyl-oxo-2,3-dihydro-1,5-benzoxazpin-3-yl]-4,7-dihydro-1H-pyrano[3,4-c]pyrazole-3-carboxamide | $^1H$ NMR (400 MHz, $CD_3OD$) δ 7.44-7.40 (m, 1H), 7.35-7.26 (m, 2H), 7.25-7.20 (m, 1H), 5.01-4.97 (m, 1H), 4.71 (s, 2H), 4.62-4.57 (m, 1H),4.39-4.36 (m, 1H), 3.42 (s, 3H), 2.68 (s, 2H), 1.25 (s, 6H) | 371.0 |

TABLE 1-continued

| Compound Example # Method | RIP1 Ki (μM) | Structure and Name | $^1$H NMR Data | MS (m/z) |
| --- | --- | --- | --- | --- |
| Example 9 Method G | 0.282 | 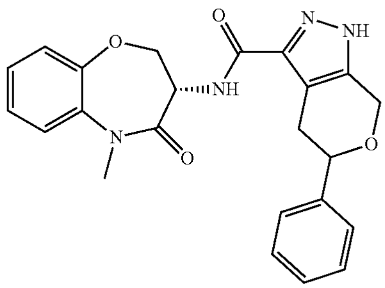 [SMILES: CN1C(=O)[C@@H](NC(=O)c2n[nH]c3c2CC(c2ccccc2)OC3)COc2ccccc21] N-((S)-5-methyl-4-oxo-2,3-dihydro-1,5-benzoxazepin-3-yl)-5-phenyl-1,4,5,7-tetrahydropyrano[3,4-c]pyrazole-3-carboxamide | $^1$H NMR (400 MHz, DMSO-d6) δ 13.10 (br. s, 1H), 8 04 (br. s, 1H), 7.47-7.23 (m, 9H), 4.96-4.92 (m, 1H), 4.85-4.82 (m, 2H), 4.60-4.54 (m, 2H), 4.43-4.38 (m, 1H), 3.33 (s, 3H), 3.05-3.01 (m, 1H), 2.67-2.57 (m, 1H) | 419.2 |
| Example 10 Method H | 2.6 | 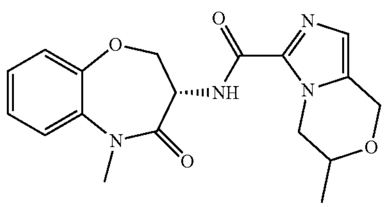 [SMILES: CC1Cn2c(cnc2C(=O)N[C@H]2COc3ccccc3N(C)C2=O)CO1] 6-methyl-N-((S)-5-methyl-4-oxo-2,3-dihydro-1,5-benzoxazepin-3-yl)-6,8-dihydro-5H-imidazo[5,1-c][1,4]oxazine-3-carboxamide | $^1$H NMR (400 MHz, DMSO-d6): δ 8.39-8.36 (m, 1H),7.50-7.48 (m, 1H), 7.32-7.30 (m, 2H), 7.29-7.24 (m, 1H), 6.89 (s, 1H), 4.99-4.95 (m, 1H), 4.78-4.73 (m, 2H), 4.60-4.56 (m, 2H), 4 52-4.39 (m, 1H), 3.84-3.83 (m, 1H), 3.65-3.62 (m, 1H), 3.31 (s, 3H), 1.23 (d, J = 6.4 Hz, 3H) | 357.2 |
| Example 11 Method I | 0.329 | 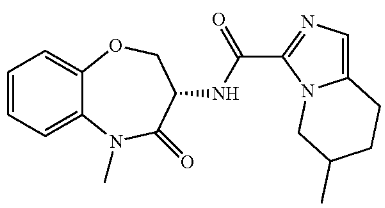 [SMILES: CC1CCc2cnc(C(=O)N[C@H]3COc4ccccc4N(C)C3=O)n2C1] 6-methyl-N-((S)-5-methyl-4-oxo-2,3-dihydro-1,5-benzoxazepin-3-yl)-5,6,7,8-tetrahydroimidazo[1,5-a]pyridine-3-carboxamide | $^1$H NMR (400 MHz, DMSO-d6): δ 8.28-8.25 (m, 1H), 7.50-7.47 (m, 1H), 7.33-7.29 (m, 2H), 7.24-7.23 (m, 1H), 6.82 (s, 1H), 4.80-4.76 (m, 1H), 4.57-4.52 (m, 2H), 4.42-4.40 (m, 1H), 3.55-3.49 (m, 1H), 3.31 (s, 3H), 2.86-2.85 (m, 1H), 2.72-2.64 (m, 1H), 2.53-2.51 (m, 1H), 1.83-1.80 (m, 1H), 1.38-1.32 (m, 1H), 0.99 (d, J = 6.4 Hz, 3H) | 355.2 |
| Example 12 Method J | >3.1 | 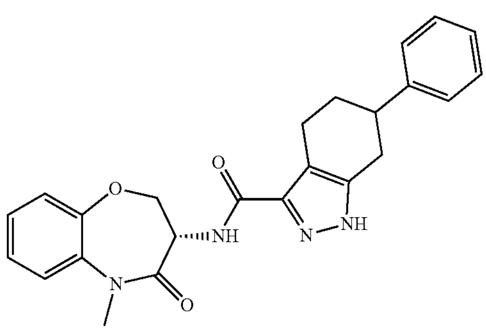 [SMILES: CN1C(=O)[C@@H](NC(=O)c2n[nH]c3c2CCC(c2ccccc2)C3)COc2ccccc21] N-((S)-5-methyl-4-oxo-2,3-dihydro-1,5-benzoxazepin-3-yl)-6-phenyl-4,5,6,7-tetrahydro-1H-indazole-3-carboxamide | $^1$H NMR (400 MHz, DMSO-d6): δ 12.94 (s, 1H), 7.96 (d, J = 8.0, 1H), 7.49 (d, J = 7.6 Hz, 1H), 7.32-7.29 (m, 6H), 7.25-7.22 (m, 2H), 4.88-4.83 (m, 1H), 4.52-4 48 (m, 1H), 4.44-4.41 (m, 1H), 3.32 (s, 3H), 2.93-2.69 (m, 4H), 2.58-2.55 (m, 1H), 1.93-1.90 (m, 1H), 1.81-1.78 (m, 1H) | 417.2 |

TABLE 1-continued

| Compound Example # Method | RIP1 Ki (μM) | Structure and Name | $^1$H NMR Data | MS (m/z) |
|---|---|---|---|---|
| Example 14 Method K, Method L | 0.167 | 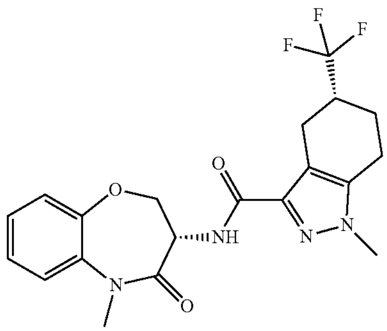 [SMILES: CN1C(=O)[C@@H](NC(=O)c2nn(C)c3c2C[C@H](C(F)(F)F)CC3)COc2ccccc21] (R)-1-methyl-N-((S)-5-methyl-4-oxo-2,3,4,5-tetrahydrobenzo[b][1,4]oxazepin-3-yl)-5-(trifluromethyl)-4,5,6,7-tetrahydro-1H-indazole-3-carboxamide | $^1$H NMR (400 MHz, $CD_3OD$) δ 7.44-7.41 (m, 1H), 7.33-7.22 (m, 3H), 4.97-4.94 (m, 1H), 4.60-4.56 (m, 1H), 4.37-4.31 (m, 1H), 3.77 (s, 3H), 3.42 (s, 3H), 3.12-3.07 (m, 1H), 2.85-2.81 (m, 1H), 2.68-2.45 (m, 3H), 2.26-2.21 (m, 1H), 1.76-1.63 (m, 1H) | 423.2 |
| Example 14 Method K, Method L | >10 | 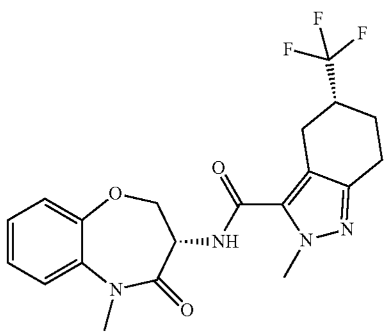 [SMILES: CN1C(=O)[C@@H](NC(=O)c2c3c(nn2C)CC[C@@H](C(F)(F)F)C3)COc2ccccc21] (R)-2-methyl-N-((S)-5-methyl-4-oxo-2,3,4,5-tetrahydrobenzo[b][1,4]oxazepin-3-yl)-5-(trifluoromethyl)-4,5,6,7-tetrahydro-2H-indazole-3-carboxamide | $^1$H NMR (400 MHz, $CD_3OD$) δ 7.45-7.41 (m, 1H), 7.35-7.18 (m, 3H), 5.03-4.97 (m, 1H), 4.60-4.55 (m, 1H), 4.43-4.37 (m, 1H), 3.91 (s, 3H), 3.42 (s, 3H), 3.12-3.05 (m, 1H), 2.87-2.30 (m, 4H), 2.26-2.22 (m, 1H), 1.77-1.71 (m, 1H) | 423.2 |
| Example 15 Method K, Method M | 0.0626 | 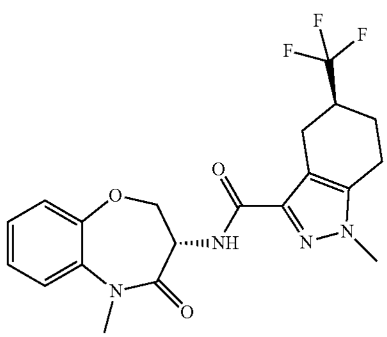 [SMILES: CN1C(=O)[C@@H](NC(=O)c2nn(C)c3c2C[C@@H](C(F)(F)F)CC3)COc2ccccc21] (S)-1-methyl-N-((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, $CD_3OD$) δ 7.46-7.40 (m, 1H), 7.36-7.20 (m, 3H), 4.99-4.94 (m, 1H), 4.60-4.56 (m, 1H), 4.38-4.33 (m, 1H), 3.79 (s, 3H), 3.41 (s, 3H), 3.11-3.06 (m, 1H), 2.85-2.81 (m, 1H), 2.67-2.46 (m, 3H), 2.25-2.21 (m, 1H), 1.75-1.67 (m, 1H) | 423.2 |
| Example 15 Method K, Method M | 8.8 | 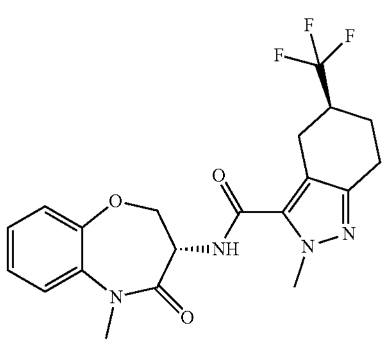 [SMILES: CN1C(=O)[C@@H](NC(=O)c2c3c(nn2C)CC[C@H](C(F)(F)F)C3)COc2ccccc21] | $^1$H NMR (400 MHz, CD3OD) δ 7.45-7.41 (m, 1H), 7.36-7.17 (m, 3H), 4.98-4.94 (m, 1H), 4.60-4.55 (m, 1H), 4.44-4.37 (m, 1H), 3.90 (s, 3H), 3.42 (s, 3H), 3.09-3.04 (m, 1H), 2.83-2.60 (m, 4H), 2.28-2.19 (m, 1H), 1.75-1.65 (m, 1H) | 423.2 |

TABLE 1-continued

| Compound Example # Method | RIP1 Ki (μM) | Structure and Name | $^1$H NMR Data | MS (m/z) |
|---|---|---|---|---|
| | | (S)-2-methyl-N-((S)-5-methyl-4-oxo-2,3,4,5-tetrahydrobenzo[b][1,4]oxazepin-3-yl)-5-(trifluoromethyl)-4,5,6,7-tetrahydro-2H-indazole-3-carboxamide | | |
| Example 16 Method N | >10 | 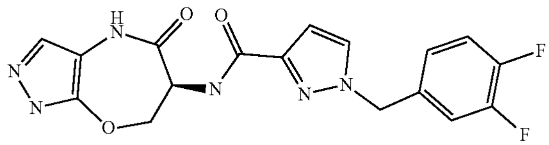 [SMILES: O=C(N[C@H]1COc2[nH]ncc2NC1=O)c1ccn(Cc2ccc(F)c(F)c2)n1] 1-[(3,4-difluorophenyl)methyl]-N-[(6S)-5-oxo-1,4,6,7-tetrahydropyrazolo[3,4-b][1,4]oxazepin-6-yl]pyrazole-3-carboxamide | $^1$H NMR (400 MHz, $CD_3OD$) δ 7.78 (d, J = 2.4 Hz, 1H), 7.36 (s, 1H), 7.26-7.20 (m, 2H), 7.14-7.10 (m, 1H), 6.80 (d, J = 2.0 Hz, 1H), 5.41 (s, 2H), 4.89-4 85 (m, 1H), 4.53-4.50 (m, 1H), 4.33-4.28 (m, 1H) | 389.0 |
| Example 17 Method O | >10 | 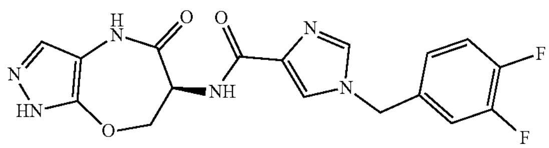 [SMILES: O=C(N[C@H]1COc2[nH]ncc2NC1=O)c1cn(Cc2ccc(F)c(F)c2)cn1] 1-[(3,4-difluorophenyl)methyl]-N-[(6S)-5-oxo-1,4,6,7-tetrahydropyrazolo[3,4-b][1,4]oxazepin-6-yl]imidazole-4-carboxamide | $^1$H NMR (400 MHz, $CD_3OD$) δ 7.79 (s, 1H), 7.74 (s, 1H), 7.36 (s, 1H), 7.32-7.24 (m, 2H), 7.14-7.05 (m, 1H), 5.26 (s, 2H), 4.82-4.50 (m, 1H), 4.51-4.48 (m, 1H), 4.31-4.26 (m, 1H) | 389.1 |
| Example 18 Method P | 0.415 | 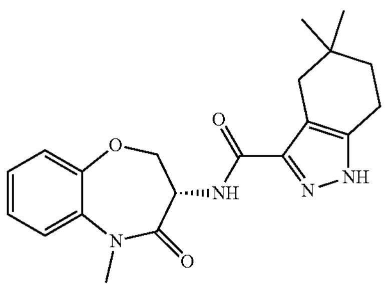 [SMILES: CN1C(=O)[C@@H](NC(=O)c2n[nH]c3c2CC(C)(C)CC3)COc2ccccc21] 5,5-dimethyl-N-[(3S)-5-methyl-4-oxo-2.3-dihydro-1,5-benzoxazepin-3-yl]-1,4,6,7-tetrahydroindazole-3-carboxamide | $^1$H NMR (400 MHz, DMSO-d6) δ 7.90 (d, J = 8.0 Hz, 1H),7.49-7.45 (m, 1H), 7.31-7.19 (m, 3H), 4.82-4.77 (m, 1H),4.51-4 34 (m, 2H), 3.29 (s, 3H), 2.57-2.52 (m, 2H), 2.32 (s, 2H), 1.45 (t, J = 6.4 Hz, 2H), 0.88 (s, 6H) | 369.0 |
| Example 19 Method Q | 3.3 | 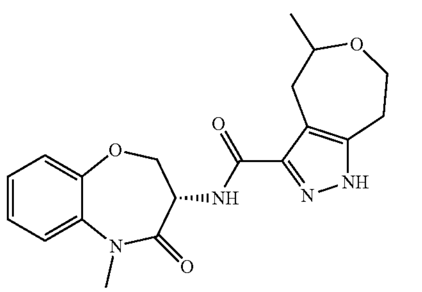 [SMILES: CC1Cc2c(C(=O)N[C@H]3COc4ccccc4N(C)C3=O)n[nH]c2CCO1] 5-methyl-N-((S)-5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide | $^1$H NMR (400 MHz, DMSO-d6) δ 12.94 (s, 1H), 8.01-7.99 (m, 1H), 7.49-7.47 (m, 1H), 7.32-7.28 (m, 2H), 7.24-7.21 (m, 1H), 4.82-4.79 (m, 1H), 4.42-4.39 (m, 1H), 4.37-4.35 (m, 1H), 4.07-4.04 (m, 1H), 3.49-3.45 (m, 3H), 3.31 (s, 3H), 2.87-2 80 (m, 2H), 2.49-2.35 (m, 1H), 1.13 (d, J = 6.0 Hz, 3H). | 371.0 |
| Example 19 Method Q | >10 | 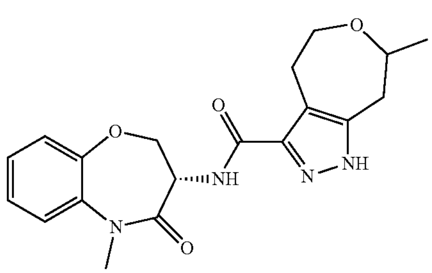 [SMILES: CC1Cc2[nH]nc(C(=O)N[C@H]3COc4ccccc4N(C)C3=O)c2CCO1] 7-methyl-N-((S)-5-methyl-4-oxo-2,3,4,5-tetrahvdrobenzo[b][1,4] | $^1$H NMR (400 MHz, DMSO-d6) δ 12.92 (s, 1H), 8.00-7.97 (m, 1H), 7.49-7.47 (m, 1H), 7.32-7.28 (m, 2H), 7.24-7.23 (m, 1H), 4.84-4.79 (m, 1H), 4.50-4.44 (m, 1H), 4.42-4.39 (m, 1H), 4.05-4.01 (m, 1H), 3.61-3.58 (m, 1H), 3.38-3.36 (m, 1H), 3.31 (s, 3H), 3.30-3.26 (m, 1H), 2.87-2.83 (m, 1H), 2.71-2.65 (m, 1H), 2.61-2.50 (m, 1H), 1.19 (d, J = 6.4 Hz, 3H). | 371.0 |

TABLE 1-continued

| Compound Example # Method | RIP1 Ki (μM) | Structure and Name | $^1$H NMR Data | MS (m/z) |
|---|---|---|---|---|
| | | oxazepin-3-yl)-4,5,7,8-tetrahydro-1H-oxepino[4,5-c]pyrazole-3-carboxamide | | |
| Example 19 Method Q | >10 | 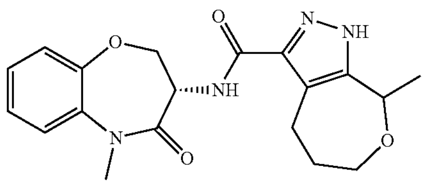 [SMILES: CC1OCCCc2c(C(=O)N[C@H]3COc4ccccc4N(C)C3=O)n[nH]c21] 8-methyl-N-((S)-5-methyl-4-oxo-2,3,4,5-tetrahydrobenzo[b][1,4] oxazepin-3-yl)-4,5,6,8-tetrtrahydro-1H-oxcpino[3,4-c]pyrazole-3-carboxamide | $^1$H NMR (400 MHz, DMSO-d6) δ 12.90 (s, 1H), 8.00 (br. s, 1H), 7.50-7.47 (m, 1H), 7.33-7.28 (m, 2H), 7.26-7.24 (m, 1H), 4.84-4.81 (m, 1H), 4.63-4.60 (m, 1H), 4.48-4.39 (m, 2H), 4.09-4.07 (m, 1H), 3.73-3.70 (m, 1H), 3.32 (s, 3H), 3.20-3.17 (m, 1H), 2.70-2.65 (m, 1H), 1.78-1.70 (m, 1H), 1.62-1.59 (m, 1H), 1.48 (d, J = 6.8 Hz, 3H). | 371.0 |
| Example 19 Method Q | 8.2 | 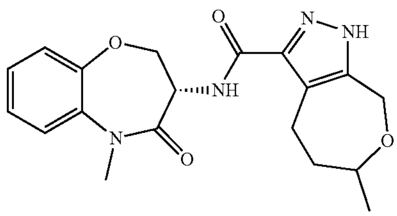 [SMILES: CC1CCc2c(C(=O)N[C@H]3COc4ccccc4N(C)C3=O)n[nH]c2CO1] 6-methyl-N-((S)-5-methyl-4-oxo-2,3,4,5-tetrahydrobenzo[b][1,4] oxazepin-3-yl)-4,5,6,8-tetrahydro-1H-oxepino[3,4-c]pyrazole-3-carboxamide | $^1$H NMR (400 MHz, DMSO-d6) δ 8.05-8.03 (m, 1H), 7.50-7.47 (m, 1H), 7.33-7.23 (m, 3H), 4.84-4.80 (m, 1H), 4.70(d, J = 14.8 Hz, 1H), 4 49-4.40 (m, 3H), 3.78-3.74 (m, 1H), 3.31 (s, 3H), 3.30-3.24 (m, 1H), 2.49-2.47 (m, 1H), 1.83-1.78 (m, 1H), 1.41-1.32 (m, 1H), 1.15 (d, J = 6.0 Hz, 3H). | 371.1 |
| Example 20 Method R | 0.745 | 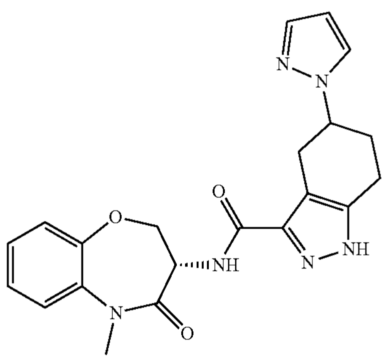 [SMILES: CN1C(=O)[C@@H](NC(=O)c2n[nH]c3c2CC(n2cccn2)CC3)COc2ccccc21] N-((S)-5-methyl-4-oxo-2,3,4,5-tetrahydrobenzo[b][1,4]oxazepin-3-yl)-5-(1H-pyrazol-1-yl)-4,5,6,7-tetrahydro-1H-indazole-3-carboxamide | $^1$H NMR (400 MHz, DMSO-d6) δ 13.00 (br. s, 1H), 7.99 (d, J = 8.4 Hz, 1H), 7.73 (d, J = 2.0 Hz, 1H), 7.50-7.42 (m, 2H), 7.35-7.19 (m, 3H), 6.26-6.18 (m, 1H), 4.87-4.77 (m, 1H), 4.62-4.46 (m, 2H), 4.44-4.36 (m, 1H), 3.31 (s, 3H), 3.20-3.10 (m, 1H), 2.98-2.65 (m, 3H), 2.25-2.09 (m, 2H). | 407.1 |
| Example 21 METHOD S | 5.9 | 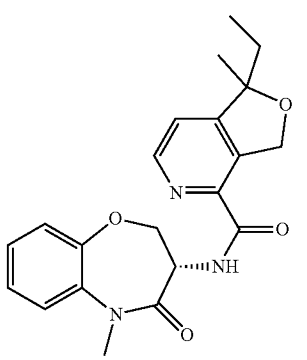 [SMILES: CCC1(C)OCc2c1ccnc2C(=O)N[C@H]1COc2ccccc2N(C)C1=O] 1-ethyl-1-methyl-N-((S)-5-methyl-4-oxo-2,3,4,5-tetrahydrobezo [b][1,4]oxazepin-3-yl)-1,3-dihydrofuro[3,4-c]pyridine-4-carboxamide | $^1$H NMR (400 MHz, $CD_3OD$) δ 8.60 (d, J = 5.6 Hz, 1H), 7.45-7.42 (m, 2H), 7.34-7.24 (m, 3H), 5.33-5.28 (m, 2H), 5.02-4.97 (m, 1H), 5.16 (d, J = 3 6 Hz, 2H), 5.05-5.00 (m, 1H), 4.63 (t, J = 10.0 Hz, 1H), 4.41 (t, J = 9.6 Hz, 1H), 3.43 (s, 3H), 1.87-1.81 (m, 2H), 1.45 (s, 3H), 0.75 (t, J = 7.6 Hz, 3H). | 382.3 |

TABLE 1-continued

| Compound Example # Method | RIP1 Ki (μM) | Structure and Name | ¹H NMR Data | MS (m/z) |
|---|---|---|---|---|
| Example 21 Method S | 0.349 | 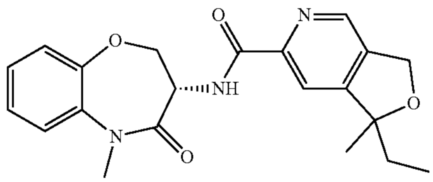 [SMILES: CCC1(C)OCc2cnc(C(=O)N[C@H]3COc4ccccc4N(C)C3=O)cc21] 1-ethyl-1-methyl-N-((S)-5-methyl-4-oxo-2,3,4,5-tetrahydrobenzo[b][1,4]oxazepin-3-yl)-1,3-dihydrofluro[3,4-c]pyridine-6-carboxamide | $^1$H NMR (400 MHz, $CD_3OD$) δ 8.57 (s, 1H), 7.86 (s, 1H), 7.45-7.43 (m, 1H), 7.39-7.29 (m, 2H), 7.26-7.25 (m, 1H), 5.16 (d, J = 3.6 Hz, 2H), 5.05-5.00 (m, 1H), 4.67-4.62 (m, 1H), 4.41 (t, J = 9.6, 1H), 3.43 (s, 3H), 1.88-1.82 (m, 2H), 1.46 (s, 3H), 0.77 (t, J = 7.2, 3H). | 382.0 |
| Example 22 Method T | 0.898 | 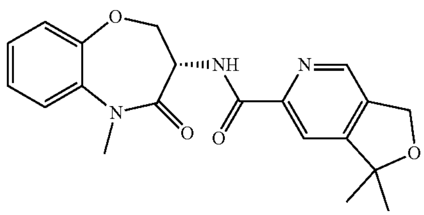 [SMILES: CN1C(=O)[C@@H](NC(=O)c2cc3c(cn2)COC3(C)C)COc2ccccc21] (S)-1,1-dimethyl-N-(5-methyl-4-oxo-2,3,4,5-tetrahydrobenzo[b][1,4]oxazepin-3-yl)-1,3-dihydrofuoro[3,4-c]pyridine-6-carboxamide | $^1$H NMR (400 MHz, $CD_3OD$) δ 8.57 (s, 1H), 7.91 (s, 1H), 7.44-7.43 (m, 1H), 7.34-7.31 (m, 2H), 7.26-7.25 (m, 1H), 5.15(s, 2H), 5.05-5.00 (m, 1H), 4.65-4.62 (m 1H), 4.43-3.98 (m, 1H), 3.43 (s, 3H), 1.49 (s, 6H). | 368.0 |
| Example 23 Method U | 2 | 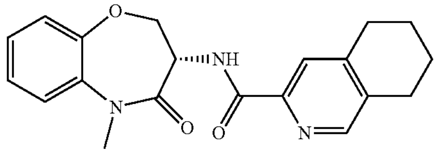 [SMILES: CN1C(=O)[C@@H](NC(=O)c2cc3c(cn2)CCCC3)COc2ccccc21] (S)-N-(5-methyl-4-oxo-2,3,4,5-tetrahydrobenzo[b][1,4]oxazepin-3-yl)-5,6,7,8-tetrahydroisoquinoline-3-carboxamide | $^1$H NMR (400 MHz, $CD_3OD$) δ 8.32 (s, 1H), 7.71 (s, 1H), 7.43 (d, J = 6.0 Hz, 1H), 7.37-7.19 (m, 3H), 5.02-4.97 (m, 1H), 4.64-4.60 (m, 1H), 4.37 (t, J = 10.8 Hz, 1H), 3.42 (s, 3H), 2.83-2.81 (m, 4H), 1.87-1.82 (m, 4H). | 352.2 |
| Example 24 Method V | 0.0279 | 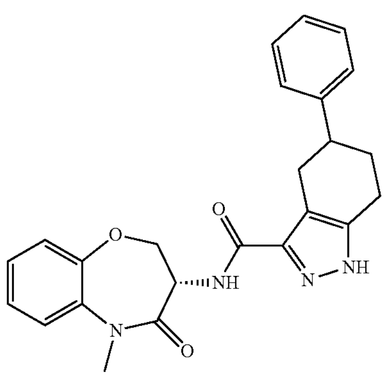 [SMILES: CN1C(=O)[C@@H](NC(=O)c2n[nH]c3c2CC(c2ccccc2)CC3)COc2ccccc21] N-((S)-5-methyl-4-oxo-2,3,4,5-tetrahydrobenzo[b][1,4]oxazepin-3-yl)-5-phenyl-4,5,6,7-tetrahydro-1H-indazole-3-carboxamide | $^1$H NMR (400 MHz, DMSO-d6) δ 12.95 (s, 1H), 7.97-7.95 (m, 1H), 7.48-7.45 (m, 1H), 7.33-7.25 (m, 6H), 7.23-7.17 (m, 2H), 4.85-4 78 (m, 1H), 4.54-4.47 (m, 1H), 4.42-4.37 (m, 1H), 3.31 (s, 3H), 2.98-2.92 (m, 1H), 2.88-2.83 (m, 1H), 2.72-2.67 (m, 2H), 2.56-2.53 (m, 1H), 1.98-1.89 (m, 2H). | 417.3 |
| Example 25 Method W | >10 | 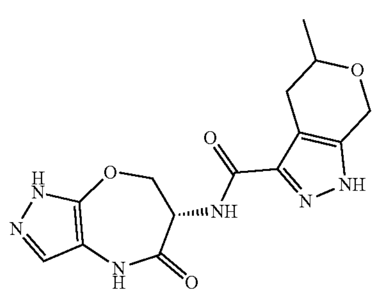 [SMILES: CC1Cc2c(C(=O)N[C@H]3COc4[nH]ncc4NC3=O)n[nH]c2CO1] | $^1$H NMR (400 MHz, $CD_3OD$) δ 7.52 (s, 1 H), 4.91-4.74 (m, 3 H), 4.58-4.54 (m, 1 H), 4.39-4.35 (m, 1 H), 3.75-3.71 (m, 1 H), 3.00-2.88 (m, 1 H), 2.55-2.51 (m, 1 H), 1.36 (d, J = 3.2 Hz, 3 H). | 333.0 |

TABLE 1-continued

| Compound Example # Method | RIP1 Ki (μM) | Structure and Name | $^1$H NMR Data | MS (m/z) |
|---|---|---|---|---|
| | | 5-methyl-N-((S)-5-oxo-4,5,6,7-tetrahydro-1H-pyrazolo[3,4-b][1,4]oxazepin-6-yl)-1,4,5,7-tetrahydropyrano[3,4-c]pyrazole-3-carboxamide | | |
| Example 26 Method X | 1.5 | 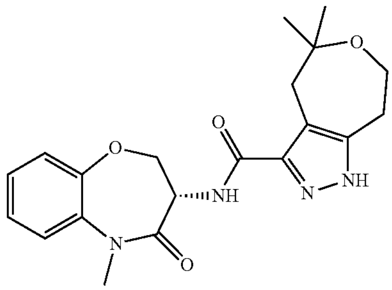 [SMILES: CN1C(=O)[C@@H](NC(=O)c2n[nH]c3c2CC(C)(C)OCC3)COc2ccccc21] (S)-5,5-dimethyl-N-(5-methyl-4-oxo-2,3,4,5-tetrahydrobenzo[b][1,4]oxazepin-3-yl)-4,5,7,8-tetrahydro-1H-oxepino[4,5-c]pyrazole-3-carboxamide | $^1$H NMR (400 MHz, DMSO-d6) δ 12.93 (s, 1H), 8.00 (d, J = 8.0 Hz, 1H), 7.49-7.47 (m, 1H), 7.35-7.19 (m, 3H), 4.85-4.78 (m, 1H), 4.52-4.46 (m, 1H), 4.41-4.37 (m, 1H), 3.77-3.75 (m, 2H), 3.31 (s, 3H), 3.01 (s, 2H), 2.82-2.79 (m, 2H), 1.04 (s, 6H). | 385.1 |
| Example 26 Method X | >10 | 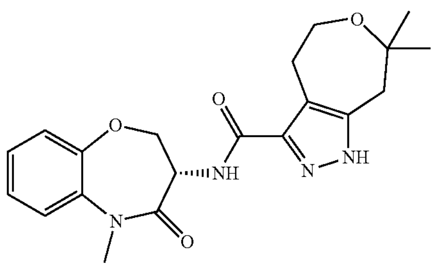 [SMILES: CN1C(=O)[C@@H](NC(=O)c2n[nH]c3c2CCOC(C)(C)C3)COc2ccccc21] (S)-7,7-dimethyl-N-(5-methyl-4-oxo-2,3,4,5-tetrahydrobenzo[b][1,4]oxazepin-3-yl)-4.5,7,8-tetrahydro-1H-oxepino[4,5-c]pyrazole-3-carboxamide | $^1$H NMR (400 MHz, DMSO-d6) δ 12.91 (s, 1H), 7.98 (d, J = 8.0 Hz, 1H), 7.50-7.48 (m, 1H), 7.36-7.19(m, 3H), 4.85-4.78 (m, 1H), 4.54-4.37 (m, 2H), 3.73-3.71 (m, 2H), 3.31 (s, 3H), 2.89-2.79 (m, 4H), 1.12 (s, 3H), 1.11 (s, 3H). | 385.1 |
| Example 26 Method X | 9.6 | 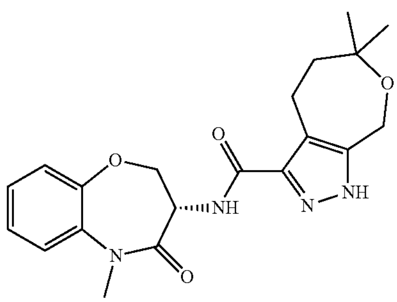 [SMILES: CN1C(=O)[C@@H](NC(=O)c2n[nH]c3c2CCC(C)(C)OC3)COc2ccccc21] (S)-6,6-dimethyl-N-(5-methyl-4-oxo-2,3,4,5-tetrahydrobenzo[b][1,4]oxazepin-3-yl)-4,5,6,8-tetrahydro-1H-oxepino[3,4-c]pyrazole-3-carboxamide | $^1$H NMR (400 MHz, DMSO-d6) δ 12.93 (br. s, 1H), 7.97 (d, J = 7.2 Hz, 1H), 7.48 (d, J = 7.2 Hz, 1H), 7.39-7.16 (m, 3H), 4.83-4.81 (m, 1H), 4.61-4.33 (m, 4H), 3.31 (s, 3H), 2.80-2.70 (m, 2H), 1.85-1.70 (m, 2H), 1.20 (s, 6H). | 385.1 |
| Example 27 Method Y | 0.0841 | 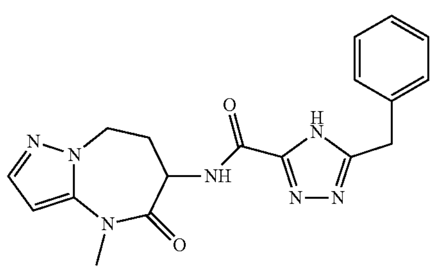 [SMILES: CN1C(=O)C(NC(=O)c2nnc(Cc3ccccc3)[nH]2)CCn2nccc21] 5-benzyl-N-(4-methyl-5-oxo-5,6,7,8-tetrahvdro-4H-pyrazolo[1,5-a][1,3]diazepin-6-yl)-4H-1,2,4-triazole-3-carboxamide | $^1$H NMR (400 MHz, DMSO-d6) δ 14.42 (s, 1H), 8.56 (s, 1H), 7.49 (d, J = 2.0 Hz, 1H), 7.38-7.16 (m, 5H), 6.34 (d, J = 2.0 Hz, 1H), 4.42-4.13 (m, 3H), 4.11 (s, 2H), 3.24 (s, 3H), 2.69-2.53 (m, 1H), 2.47-2.32 (m, 1H). | 366.2 |

TABLE 1-continued

| Compound Example # Method | RIP1 Ki (μM) | Structure and Name | $^1$H NMR Data | MS (m/z) |
|---|---|---|---|---|
| Example 27 Method Y | 0.0454 | 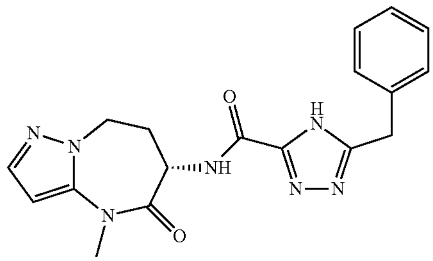 [SMILES: CN1C(=O)[C@@H](NC(=O)c2nnc(Cc3ccccc3)[nH]2)CCn2nccc21] (S)-5-benzyl-N-(4-methyl-5-oxo-5,6,7,8-tetrahydro-4H-pyrazolo [1,5-a][1,3]diazepin-6-yl)-4H-1,2,4-triazole-3-carboxamide | $^1$H NMR (400 MHz, DMSO-d6) δ 14.44 (s, 1H), 8.54 (s, 1H), 7.49 (d, J = 2.0 Hz, 1H), 7.35-7.20 (m, 5H), 6.34 (d, J = 2.0 Hz, 1H), 4.42-4.13 (m, 3H), 4.10 (s, 2H), 3.24 (s, 3H), 2.65-2.53 (m, 1H), 2.44-2.30 (m, 1H). | 366.2 |
| Example 27 Method Y | >10 | 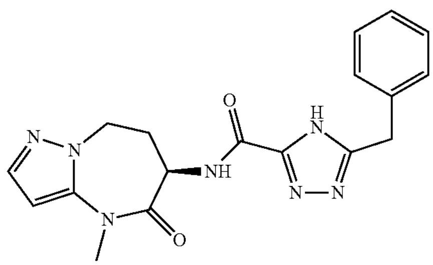 [SMILES: CN1C(=O)[C@H](NC(=O)c2nnc(Cc3ccccc3)[nH]2)CCn2nccc21] (R)-5-benzyl-N-(4-methyl-5-oxo-5,6,7,8-tetrahydro-4H-pyrazolo [1,5-a][1,3]diazepin-6-yl)-4H-1,2.4-triazole-3-carboxamide | $^1$H NMR (400 MHz, DMSO-d6) δ 14.43 (s, 1H), 8.54 (s, 1H), 7.49 (d, J = 2.0 Hz, 1H), 7.43-7.13 (m, 5H), 6.34 (d, J = 2.0 Hz, 1H), 4.42-4.13 (m, 3H), 4.10 (s, 2H), 2.67-2.52 (m, 1H), 2.46-2.29 (m, 1H). | 366.2 |
| Example 28 Method Z | 0.137 | 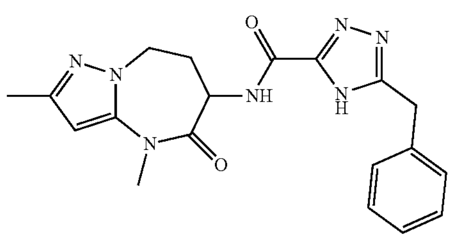 [SMILES: Cc1cc2n(n1)CCC(NC(=O)c1nnc(Cc3ccccc3)[nH]1)C(=O)N2C] 5-benzyl-N-(2,4-dimethyl-5-oxo-5,6,7,8-tetrahydro-4H-pyrazolo [1,5-a][1,3]diazepin-6-yl)-4H-1,2,4-triazole-3-carboxamide | $^1$H NMR (400 MHz, DMSO-d6) δ 14.39 (s, 1H), 8.53 (s, 1H), 7.36-7.21 (m, 6H), 6.13 (s, 1H), 4.39-4.21 (m, 2H), 4.18-4.01 (m, 4H), 3.22 (s, 3H), 2.57 (ddd, J = 12.8, 8.0, 4.9 Hz, 1H), 2.41-2.29 (m, 1H), 2.17 (s, 3H). | 380.2 |
| Example 29 Method AA | 0.117 | 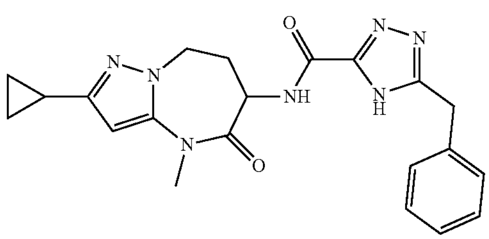 [SMILES: CN1C(=O)C(NC(=O)c2nnc(Cc3ccccc3)[nH]2)CCn2nc(C3CC3)cc21] 5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, DMSO-d6) δ 8.51 (d, J = 7.8 Hz, 1H), 7.36-7.19 (m, 5H), 6.06 (s, 1H), 4.37-4.20 (m, 2H), 4.16-4.02 (m, 3H), 3.20 (s, 3H), 2.65-2.53 (m, 1H), 2.40-2.27 (m, 1H), 1.91-1.80 (m, 1H), 0.92-0.81 (m, 2H), 0.73-0.60 (m, 2H). | 406.2 |

TABLE 1-continued

| Compound Example # Method | RIP1 Ki (μM) | Structure and Name | $^1$H NMR Data | MS (m/z) |
|---|---|---|---|---|
| Example 30 Method BB | 0.208 | 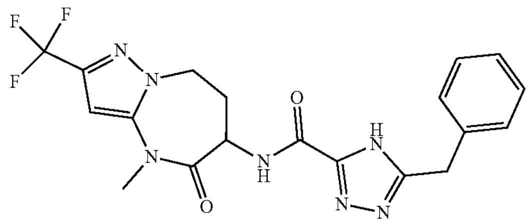 [SMILES: CN1C(=O)C(NC(=O)c2nnc(Cc3ccccc3)[nH]2)CCn2nc(C(F)(F)F)cc21] 5-benzyl-N-(4-methyl-5-oxo-2-(trifluoromethyl)-5,6,7,8-tetrahydro-4H-pyrazolo[1,5-a][1,3]diazepin-6-yl)-4H-l,2,4-triazole-3-carboxamide | $^1$H NMR (400 MHz, DMSO-d6) δ 14.42 (s, 1H), 8.64 (s, 1H), 7.47-7.13 (m, 5H), 6.93 (s, 1H), 4.53-4.41 (m, 1H), 4.41-4.26 (m, 2H), 4.11 (s, 2H), 3.27 (s, 3H), 2.74-2.57 (m, 1H). | 434.1 |
| Example 31 Method CC | 0.140 | 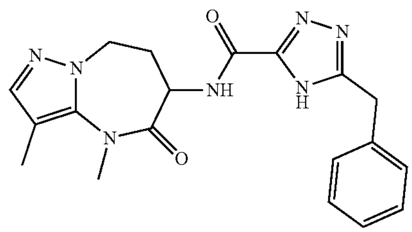 [SMILES: Cc1cnn2c1N(C)C(=O)C(NC(=O)c1nnc(Cc3ccccc3)[nH]1)CC2] 5-benzyl-N-(3,4-dimethyl-5-oxo-5,6,7,8-tetrahydro-4H-pyrazolo [1,5-a][1,3]diazepin-6-yl)-4H-1,2,4-triazolc-3-carboxamide | $^1$H NMR (400 MHz, DMSO-d6) δ 14.41 (s, 1H), 8.45 (d, J = 7.6 Hz, 1H), 7.39-7.12 (m, 6H), 4.40-3.99 (m, 5H), 3.21 (s, 3H), 2.62-2.51 (m, 1H), 2.36-2.21 (m, 1H), 2.01 (s, 3H). | 380.2 |
| Example 32 Method DD | 3.4 | 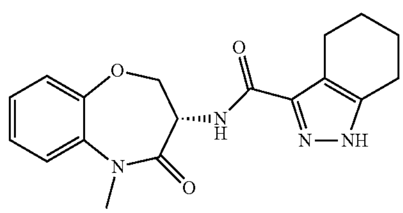 [SMILES: CN1C(=O)[C@@H](NC(=O)c2n[nH]c3c2CCCC3)COc2ccccc21] (S)-N-(5-methyl-4-oxo-2,3,4,5-tetrahydrobenzo[b][1,4]oxazepin-3-yl)-4,5,6,7-tetrahydro-1H-indazole-3-carboxamide | $^1$H NMR (400 MHz, DMSO-d6) δ 12.83 (s, 1H), 7.90 (d, J = 8.0 Hz, 1H), 7.52-7.46 (m, 1H), 7.37-7.20 (m, 3H), 4.82 (dt, J = 11.3, 7.8 Hz, 1H), 4.49 (dd, J = 11.4, 9.8 Hz, 1H), 4.40 (dd, J = 9.8, 7.7 Hz, 1H), 3.31 (s, 3H), 2.62-2.53 (m, 4H), 1.75-1.57 (m, 4H). | 341.2 |
| Example 33 Method EE | 3.5 | 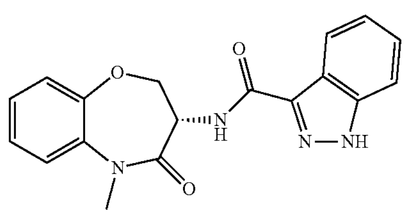 [SMILES: CN1C(=O)[C@@H](NC(=O)c2n[nH]c3ccccc23)COc2ccccc21] (S)-N-(5-methyl-4-oxo-2,3,4,5-tetrahydrobenzo[b][1,4]oxazepin-3-yl)-1H-indazole-3-carboxamide | $^1$H NMR (400 MHz, DMSO-d6) δ 13.71 (s, 1H), 8.39 (d, J = 8.1 Hz, 1H), 8.06 (dt, J = 8.2, 1.0 Hz, 1H), 7.63 (dt, J = 8.5, 0.9 Hz, 1H), 7.56-7.49 (m, 1H), 7.42 (ddd, J = 8.4, 6.9, 1.1 Hz, 1H), 7.38-7.19 (m, 4H), 4.95 (dt, J = 11.6, 7.9 Hz, 1H), 4.63 (dd, J = 11.6, 9.9 Hz, 1H), 4.47 (dd. J = 9.9, 7.7 Hz, 1H), 3.34 (s, 3H). | 337.1 |
| Example 34 Method FF | 0.0152 | 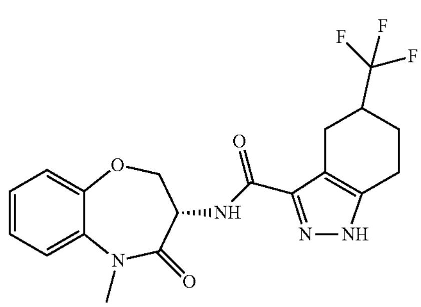 [SMILES: CN1C(=O)[C@@H](NC(=O)c2n[nH]c3c2CC(C(F)(F)F)CC3)COc2ccccc21] N-((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, DMSO-d6) δ 13.01 (s, 1H), 8.00 (d, J = 8.0 Hz, 1H), 7.53-7.45 (m, 1H), 7.37-7.20 (m, 3H), 4.83 (dt, J = 11.5, 8.1 Hz, 1H), 4.52 (ddd, J = 11.3, 10.7, 3.9 Hz, 1H), 4.40 (ddd, J = 10.0, 7.7, 2.5 Hz, 1H), 3.31 (s, 3H), 2.98 (dt, J = 16.0, 4.4 Hz, 1H), 2.85-2.54 (m, 3H), 2.49-2.38 (m, 1H), 2.15-2.01 (m, 1H), 1.71-1.53 (m, 1H). | 409.1 |

TABLE 1-continued

| Compound Example # Method | RIP1 Ki (μM) | Structure and Name | $^1$H NMR Data | MS (m/z) |
|---|---|---|---|---|
| Example 34 Method FF | 0.00768 | 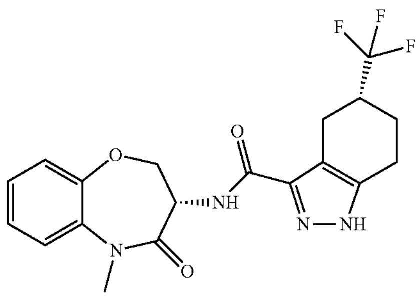 [SMILES: CN1C(=O)[C@@H](NC(=O)c2n[nH]c3c2C[C@H](C(F)(F)F)CC3)COc2ccccc21] (R)-N-((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, DMSO-d6) δ 13.00 (s, 1H), 8 01 (d, J = 8.0 Hz, 1H), 7.63-7.39 (m, 1H), 7.43-7.11 (m, 3H), 4.83 (dt, J = 11.4, 7.8 Hz, 1H), 4.52 (dd, J = 11.5, 9.8 Hz, 1H), 4.41 (dd, J = 9.9, 7.7 Hz, 1H), 3.31 (s, 3H), 2.99 (dd, J = 16.0, 5.1 Hz, 1H), 2.85-2.74 (m, 1H), 2.74-2.58 (m, 2H), 2.48-2.38 (m, 1H), 2.16-2.03 (m, 1H), 1.71-1.53 (m, 1H). | 409.1 |
| Example 34 Method FF | 0.0454 | 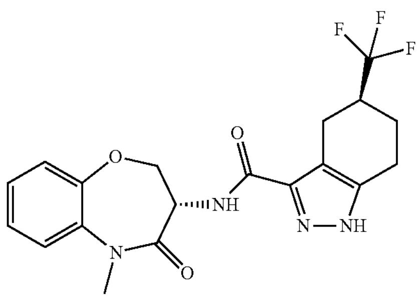 [SMILES: CN1C(=O)[C@@H](NC(=O)c2n[nH]c3c2C[C@@H](C(F)(F)F)CC3)COc2ccccc21] (S)-N-((S)-5-methyl-4-oxo-2,3,4,5-tetrahydrobenzo[b][1,4]oxazepin-3-yl)-5-(tritluoromethyl)-4,5,6,7-tetrahydro-1H-indazole-3-carboxamide | $^1$H NMR (400 MHz, DMSO-d6) δ 12.97 (s, 1H), 8 00 (d, J = 8.0 Hz, 1H), 7.68-7.41 (m, 1H), 7.41-7.06 (m, 3H), 4.83 (dt, J = 11.4, 7.7 Hz, 1H), 4.51 (dd, J = 11.5, 9.8 Hz, 1H), 4.40 (dd, J = 9.8, 7.7 Hz, 1H), 3.31 (s, 3H), 2.98 (dd, J = 16.0, 5.1 Hz, 1H), 2.86-2.74 (m, 1H), 2.74-2.57 (m, 2H), 2.47-2.37 (m, 1H), 2.16-2.02 (m, 1H), 1.72-1.51 (m, 1H). | 409.1 |
| Example 35 Method GG | 0.00874 | 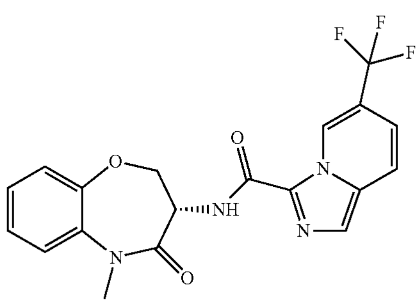 [SMILES: CN1C(=O)[C@@H](NC(=O)c2ncc3ccc(C(F)(F)F)cn23)COc2ccccc21] (S)-N-(5-methyl-4-oxo-2,3,4,5-tetrahydrobenzo[b][1,4]oxazepin-3-yl)-6-(trifluoromethyl)imidazo[1,5-a]pyridine-3-carboxamide | $^1$H NMR (400 MHz, DMSO-d6) δ 9.66 (p, J = 1.2 Hz, 1H), 8.78 (d, J = 8.0 Hz, 1H), 8.03 (dt, J = 9.6, 0.9 Hz, 1H), 7.81 (d, J = 0.8 Hz, 1H), 7 58-7.46 (m, 1H), 7.41-7.19 (m, 4H), 4.91 (dt, J = 11.6, 7.8 Hz. 1H), 4.69 (dd, J = 11.6, 9.9 Hz, 1H), 4.46 (dd, J = 9.9, 7.7 Hz, 1H), 3.33 (s, 3H). | 405.1 |
| Example 36 Method HH | 0.185 | 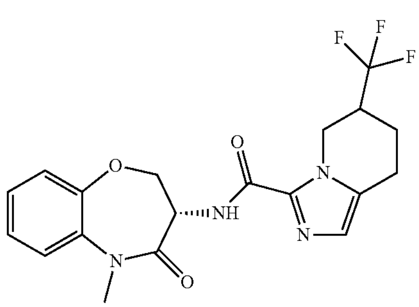 [SMILES: CN1C(=O)[C@@H](NC(=O)c2ncc3n2CC(C(F)(F)F)CC3)COc2ccccc21] N-((S)-5-methyl-4-oxo-2,3,4,5-tetrahydrobenzo[b][1,4]oxazepin-3-yl)-6-(trifluoromethyl)-5,6,7,8-tetrahydroimidazo[1,5-a]pyridine-3-carboxamide | $^1$H NMR (400 MHz, DMSO-d6) δ 8.35 (d, J = 8.0 Hz, 1H), 7.54-7.45 (m, 1H), 7.37-7.19 (m, 3H), 6.89 (d, J = 0.8 Hz, 1H), 4.91-4.69 (m, 2H), 4.57 (ddd, J = 11.6, 9.8. 3.6 Hz, 1H), 4.40 (ddd, J = 9.8, 7.6, 2.0 Hz, 1H), 4.12-4.01 (m, 2H), 3.31 (s, 3H), 3.04-2.92 (m, 1H), 2.84-2.69 (m, 1H), 2.15-2.04 (m, 1H), 1.83-1.67 (m, 1H). | 409.1 |

TABLE 1-continued

| Compound Example # Method | RIP1 Ki (μM) | Structure and Name | $^1$H NMR Data | MS (m/z) |
|---|---|---|---|---|
| Example 37 Method II | 0.00508 | 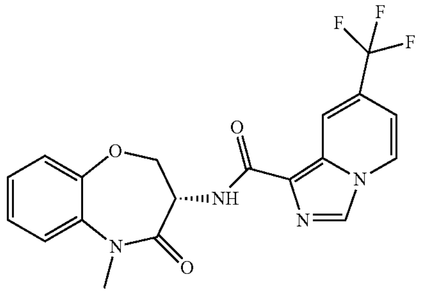 [SMILES: CN1C(=O)[C@@H](NC(=O)c2ncn3ccc(C(F)(F)F)cc23)COc2ccccc21] (S)-N-(5-methyl-4-oxo-2,3,4,5-tetrahydrobenzo[b][1,4]oxazepin-3-yl)-7-(trifluoromethyl)imidazo[1,5-a]pyridine-1-carboxamide | $^1$H NMR (400 MHz, DMSO-d6) δ 8.71-8.66 (m, 2H), 8.36-8.25 (m, 2H), 7.55-7.47 (m, 1H), 7.39-7.21 (m, 3H), 7.12 (dd, J = 7.4, 1.9 Hz, 1H), 4.92 (dt, J = 11.5, 7.8 Hz, 1H), 4.60 (dd, J = 11.5, 9.8 Hz, 1H), 4.47 (dd, J = 9.8, 7.7 Hz, 1H), 3.33 (s, 3H). | 405.1 |
| Example 38 Method JJ | 0.0874 | 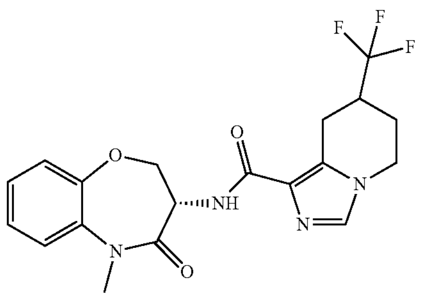 [SMILES: CN1C(=O)[C@@H](NC(=O)c2ncn3c2CC(C(F)(F)F)CC3)COc2ccccc21] N-((S)-5-methyl-4-oxo-2,3,4,5-tetrahydrobenzo[b][1,4]oxazepin-3-yl)-7-(trifluoromethyl)-5,6,7,8-tetrahydroimidazo[1,5-a]pyridine-1-carboxamide | $^1$H NMR (400 MHz, DMSO-d6) δ 7.88 (d, J = 8.0 Hz, 1H), 7.69 (s, 1H), 7.53-7.45 (m, 1H), 7.36-7.20 (m, 3H), 4.81 (dt, J = 11.2, 7 9 Hz, 1H), 4.54-4.36 (m, 2H), 4.33-4.23 (m, 1H), 3.95 (tt, J = 12.4, 4.4 Hz, 1H), 3.39-3.33 (m, 1H), 3.31 (s, 3H), 3.05-2.86 (m, 1H), 2.80-2 64 (m, 1H), 2.26-2.12 (m, 1H), 1.95-1.78 (m, 1H). | 409.1 |
| Example 39 Method KK | 3.9 | 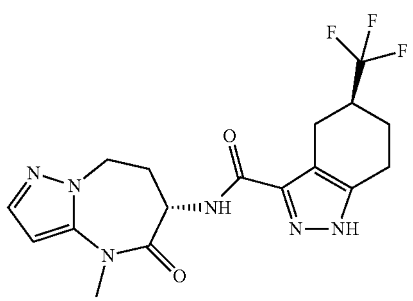 [SMILES: CN1C(=O)[C@@H](NC(=O)c2n[nH]c3c2C[C@@H](C(F)(F)F)CC3)CCn2nccc21] (S)-N-((S)-4-methyl-5-oxo-5,6,7,8-tetrahydro-4H-pyrazolo[1,5-a][l,3]diazepin-6-yl)-5-(trifluoromethyl)-4,5,6,7-tetrahydro-1H-indazole-3-carboxamide | $^1$H NMR (400 MHz, DMSO-d6) δ 12.98 (s, 1H), 8.08 (d, J = 7.9 Hz, 1H), 7.50 (d, J = 2.0 Hz, 1H), 6.33 (d, J = 2.0 Hz, 1H), 4.45-4.09 (m, 3H), 3.25 (s, 3H), 3.01 (dd, J = 16.0, 5.1 Hz, 1H), 2.87-2.56 (m, 4H), 2.47-2.25 (m, 2H), 2.18-2.02 (m, 1H), 1.74- 1.52 (m, 1H). | 397.1 |
| Example 39 Method KK | 0.504 | 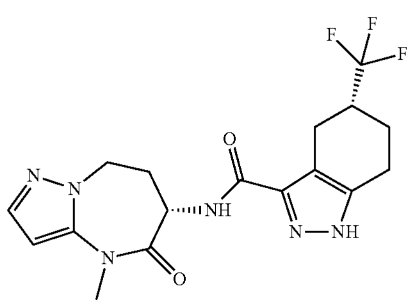 [SMILES: CN1C(=O)[C@@H](NC(=O)c2n[nH]c3c2C[C@H](C(F)(F)F)CC3)CCn2nccc21] (R)-N-((S)-4-methyl-5-oxo-5,6,7,8-tetrahydro-4H-pyrazolo[1,5-a][1,3]diazepin-6-yl)-5-(trifluoromethyl)-4,5,6,7-tetrahydro-1H-indazole-3-carboxamide | $^1$H NMR (400 MHz, DMSO-d6) δ 12.97 (s, 1H), 8.07 (d, J = 7 9 Hz, 1H), 7.49 (d, J = 2.1 Hz, 1H), 6.32 (d, J = 2.0 Hz, 1H), 4.42-4.24 (m, 2H), 4.23-4.12 (m, 1H), 3.25 (s, 3H), 3.05-2.93 (m, 2H), 2.84-2.74 (m, 1H), 2.74-2.54 (m, 3H), 2.39-2.25 (m, 1H), 2.15-2.04 (m, 1H), 1.72-1.55 (m, 1H) | 397.1 |

TABLE 1-continued

| Compound Example # Method | RIP1 Ki (μM) | Structure and Name | $^1$H NMR Data | MS (m/z) |
|---|---|---|---|---|
| Example 44 Method B | 3 | 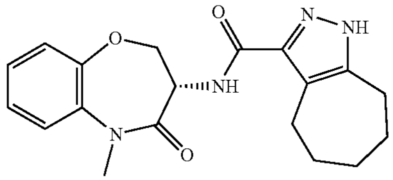 [SMILES: CN1C(=O)[C@@H](NC(=O)c2n[nH]c3c2CCCCC3)COc2ccccc21] (S)-N-(5-methyl-4-oxo-2,3,4,5-tetrahydrobenzo[b][1,4]oxazepin-3-yl)-1,4,5,6,7,8-hexahydrocyclohepta[c]pyrazole-3-carboxamide | $^1$H NMR (400 MHz, DMSO-d6) δ 12.81 (s, 1H), 7.93 (d, J = 7.9 Hz, 1H), 7.52-7.46 (m, 1H), 7.35-7.26 (m, 2H), 7.25-7.21 (m, 1H), 4.88-4.73 (m, 1H), 4 52-4.33 (m, 2H), 2 87-2.78 (m, 2H), 2.72-2.64 (m, 2H), 1.83-1.69 (m, 2H), 1.64-1.42 (m, 4H). | 355.2 |
| Example 45 Method B | 0.0626 | 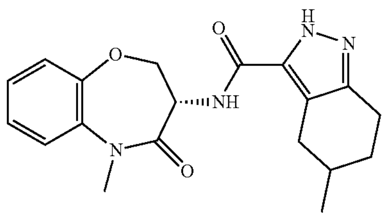 [SMILES: CC1CCc2n[nH]c(C(=O)N[C@H]3COc4ccccc4N(C)C3=O)c2C1] 5-methyl-N-((S)-5-methyl-4-oxo-2,3,4,5-tetrahydrobenzo[b][1,4]oxazepin-3-yl)-4,5,6,7-tetrahydro-2H-indazole-3-carboxamide | $^1$H NMR (400 MHz, DMSO-d6) δ 12.83 (s, 1H), 7.89 (d, J = 8.0 Hz, 1H), 7.51-7.46 (m, 1H), 7.35-7.26 (m, 2H), 7.25-7.21 (m, 1H), 4.88-4.75 (m, 1H), 4.55-4.34 (m, 2H), 2.82-2.61 (m, 2H), 2.11-1.98 (m, 1H), 1.84- 1.76 (m, 1H), 1.76-1.62 (m, 1H), 1.39-1.26 (m, 1H), 0.98 (d, J = 6.5 Hz, 3H). | 355.2 |
| Example 46 Method B | 0.135 | 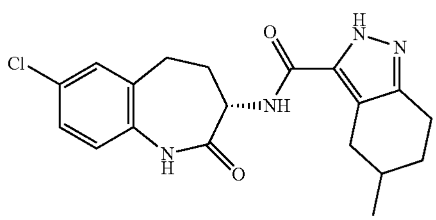 [SMILES: CC1CCc2n[nH]c(C(=O)N[C@H]3CCc4cc(Cl)ccc4NC3=O)c2C1] N-((S)-7-chloro-2-oxo-2,3,4,5-tetrahydro-1H-benzo[b]azepin-3-yl)-5-methyl-4,5,6,7-tetrahydro-2H-indazole-3-carboxamide | $^1$H NMR (400 MHz, DMSO-d6) δ 12.78 (s, 1H), 10.02 (s, 1H), 7.77 (d, J = 7.9 Hz, 1H), 7.44 (d, J = 2.5 Hz, 1H), 7.34 (dd, J = 8.4, 2.5 Hz, 1H), 7.04 (d, J = 8.4 Hz, 1H), 4.40-4.24 (m, 1H), 2.86-2.58 (m, 5H), 2.48-2.35 (m, 1H), 2.20-1.99 (m, 2H), 1.86-1.62 (m, 2H), 1.42-1.25 (m, 1H), 0.99 (d, J = 6.6 Hz, 3H). | 373.1 |
| Example 47 Method B | 0.35 | 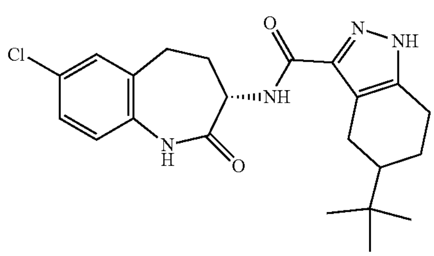 [SMILES: CC(C)(C)C1CCc2[nH]nc(C(=O)N[C@H]3CCc4cc(Cl)ccc4NC3=O)c2C1] 5-(tert-butyl)-N-((S)-7-chloro-2-oxo-2,3,4,5-tetrahydro-1H-benzo[b]azepin-3-yl)-4,5,6,7-tetrahydro-1H-indazole-3-carboxamide | $^1$H NMR (400 MHz, DMSO-d6) δ 12.77 (s, 1H), 10.01 (s, 1H), 7.78 (d, J = 7.7 Hz, 1H), 7.44 (d, J = 2.5 Hz, 1H), 7.35 (dd, J = 8.4, 2.5 Hz, 1H), 7.04 (d, J = 8.4 Hz, 1H), 4.37-4.26 (m, 1H), 2.86-2.65 (m, 4H), 2.47-2.38 (m, 1H), 2.24-2.06 (m, 2H), 2.03-1.89 (m, 1H), 1.36-1.12 (m, 2H), 0.89 (s, 9H). | 415.2 |
| Example 48 Method B | 8.6 | 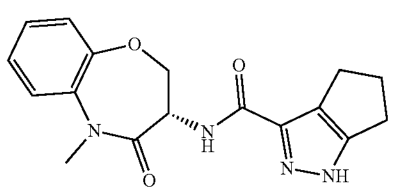 [SMILES: CN1C(=O)[C@@H](NC(=O)c2n[nH]c3c2CCC3)COc2ccccc21] (S)-N-(5-methyl-4-oxo-2,3,4,5-tetrahydrobenzo[b][1,4]oxazepin-3-yl)-1,4,5,6-tetrahydrocyclopenta[c]pyra7.ole-3-carboxamide | $^1$H NMR (400 MHz, DMSO-d6) δ 12.88 (s, 1H), 7.97-7.89 (m, 1H), 7.55-7.44 (m, 1H), 7.35-7.27 (m, 2H), 7.26-7.22 (m, 1H), 4.89-4.75 (m, 1H), 4.56-4.35 (m, 2H), 3.32 (s, 3H), 2.69-2.54 (m, 4H), 2.46-2.41 (m, 2H). | 327.1 |

TABLE 1-continued

| Compound Example # Method | RIP1 Ki (μM) | Structure and Name | ¹H NMR Data | MS (m/z) |
|---|---|---|---|---|
| Example 49 Method B | 7.6 | 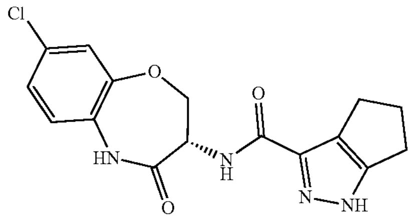 [SMILES: O=C(N[C@H]1COc2cc(Cl)ccc2NC1=O)c1n[nH]c2c1CCC2] (S)-N-(7-chloro-2-oxo-2,3,4,5-tetrahydro-1H-benzo[b]azepin-3-yl)-1,4,5,6-tetrahydrocyclopenta [c]pyrazole-3-carboxamide | $^1$H NMR (400 MHz, DMSO-d6) δ 12.82 (s, 1H), 10.06-10.01 (m, 1H), 7.85-7.72 (m, 1H), 7.46-7.42 (m, 1H), 7.37-7.32 (m, 1H), 7.10-7.00 (m, 1H), 4.43-4.20 (m, 1H), 2.77-2.70 (m, 3H), 2.69-2.64 (m, 1H), 2.60-2.54 (m, 2H), 2.45 (d, J = 8.8 Hz, 2H), 2.21-2.11 (m, 1H), 2.08 (s, 1H). | 345.1 |
| Example 50 Method A | 3.9 | 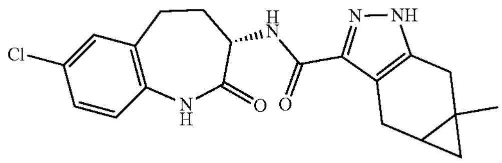 [SMILES: CC12Cc3[nH]nc(C(=O)N[C@H]4CCc5cc(Cl)ccc5NC4=O)c3CC1C2] N-((S)-7-chloro-2-oxo-2,3,4,5-tetrahydro-1H-benzo[b]azepin-3-yl)-5a-methyl-1,4,4a,5,5a,6-hexahydrocyclopropa[f]indazole-3-carboxamide | $^1$H NMR (400 MHz, DMSO-d6) δ 12.82 (s, 1H), 10.01 (s, 1H), 7.84-7.69 (m, 1H), 7.44-7.42 (m, 1H), 7.38-7.29 (m, 1H), 7.09-6.99 (m, 1H), 4.39-4.24 (m, 1H), 3.13-3.03 (m, 1H), 3.00-2.89 (m, 1H), 2.80-2.70 (m, 3H), 2.64 (d, J = 16.8 Hz, 1H), 2.47-2.37 (m, 1H), 2.22-2.06 (m, 1H), 1.19 (s, 3H), 1.05-0.92 (m, 1H), 0.35-0.25 (m, 1H), 0.10-0.01 (m, 1H). | 385.1 |
| Example 51 Method B | 8.9 | 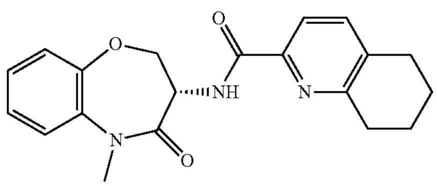 [SMILES: CN1C(=O)[C@@H](NC(=O)c2ccc3c(n2)CCCC3)COc2ccccc21] (S)-N-(5-methyl-4-oxo-2,3,4.5-tetrahydrobenzo[b][1,4]oxazepin-3-yl)-5,6,7,8-tetrahydroquinoline-2-carboxamide | $^1$H NMR (400 MHz, DMSO-d6) δ 8.70 (d, J = 7.8 Hz, 1H), 7.75-7.67 (m, 1H), 7.6 7.60 (m, 1H), 7.53-7.47 (m, 1H), 7.37-7.23 (m, 3H), 4.93-4.80 (m, 1H), 4.58-4.42 (m, 2H), 3.34 (s, 3H), 2.96-2.87 (m, 2H), 2.86-2.77 (m, 2H), 1.93-1.82 (m, 2H), 1.82-1.71 (m, 2H). | 352.2 |
| Example 52 Method B | 1.2 | 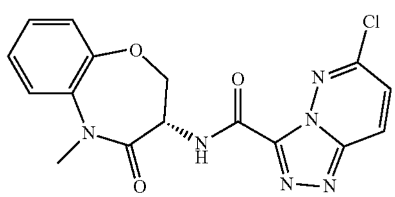 [SMILES: CN1C(=O)[C@@H](NC(=O)c2nnc3ccc(Cl)nn23)COc2ccccc21] (S)-6-chloro-N-(5-methyl-4-oxo-2,3,4,5-tetrahydrobenzo[b][1,4]oxazepin-3-yl)-[l,2,4]triazolo [4,3-b]pyridazinc-3-carboxamide | $^1$H NMR (400 MHz, DMSO-d6) δ 9.29-9.21 (m, 1H), 8.61 (d, J = 9.7 Hz, 1H), 7.67 (d, J = 9.7 Hz, 1H), 7.56-7.49 (m, 1H), 7.38-7.29 (m, 2H), 7.29-7.25 (m, 1H), 4.97-4.87 (m, 1H), 4.67-4.48 (m, 2H), 3.35 (s, 3H). | 373.1 |
| Example 53 Method A' | 4.5 | 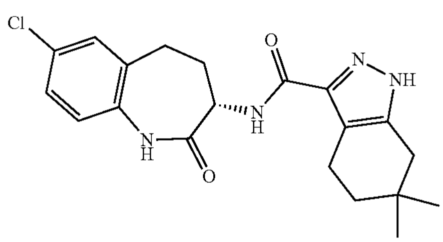 [SMILES: CC1(C)CCc2c(C(=O)N[C@H]3CCc4cc(Cl)ccc4NC3=O)n[nH]c2C1] (S)-N-(7-chloro-2-oxo-2,3,4,5-tetrahydro-1H-benzo[b]azepin-3-yl)-6,6-dimethyl-4,5,6,7-tetrahydro-1H-indazole-3-carboxamide | $^1$H NMR (400 MHz, DMSO-d6) δ 12.75 (s, 1H), 10.02 (s, 1H), 7.77 (d, J = 7.7 Hz, 1H), 7.44 (d, J = 2.5 Hz, 1H), 7.35 (dd, J = 8.4, 2.5 Hz, 1H), 7.05 (d, J = 8.4 Hz, 1H), 4.41-4.25 (m, 1H), 2 80-2.69 (m, 2H), 2.61-2.53 (m, 2H), 2.36 (s, 2H), 2.23-2.11 (m, 1H), 1.49-1.37 (m, 2H), 0.94 (s, 6H). | 387.1 |

TABLE 1-continued

| Compound Example # Method | RIP1 Ki (μM) | Structure and Name | $^1$H NMR Data | MS (m/z) |
|---|---|---|---|---|
| Example 54 Method B' | 7.7 | 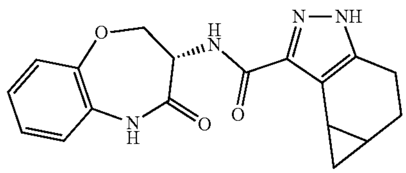 [SMILES: O=C(N[C@H]1COc2ccccc2NC1=O)c1n[nH]c2c1C1CC1CC2] N-((S)-4-oxo-2,3,4,5-tetrahydrobenzo [b][1,4]oxazepin-3-yl)-3,4,5,5a,6,6a-hexahydrocyclopropa [e]indazole-1-carboxamide | $^1$H NMR (400 MHz, DMSO-d6) δ 12.83 (s, 1H), 10.14 (s, 1H), 7.94 (d, J = 7.5 Hz, 1H), 7.17-7.05 (m, 4H), 4 88-4.72 (m, 1H), 4.53-4.37 (m, 2H), 2.74-2.56 (m, 1H), 2.31-2.14 (m, 2H), 2.16-1.99 (m, 1H), 1.77-1.53 (m, 1H), 1.38 (s, 1H), 0.98-0.74 (m, 1H), 0.41 (s, 1H) | 339.1 |
| Example 55 Method B' | 0.103 | 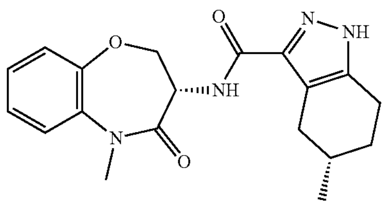 [SMILES: C[C@H]1CCc2[nH]nc(C(=O)N[C@H]3COc4ccccc4N(C)C3=O)c2C1] (S)-5-methyl-N-((S)-5-methyl-4-oxo-2,3,4,5-tetrahydrobenzo [b][1,4]oxazepin-3-yl)-4,5,6,7-tetrahydro-1H-indazole-3-carboxamide | $^1$H NMR (400 MHz, DMSO-d6) δ 12.83 (s, 1H), 7.89 (d, J = 80 Hz, 1H), 7.54-7.43 (m, 1H), 7.40-7.14 (m, 3H), 4.91-4.75 (m, 1H), 4.57-4.33 (m, 2H), 2.86-2.59 (m, 2H), 2.12-1.92 (m, 1H), 1.85-1.61 (m, 2H), 1.40-1.25 (m, 1H), 0.99 (d, J = 6.6 Hz, 3H). | 355.2 |
| Example 56 Method B' | 0.922 | 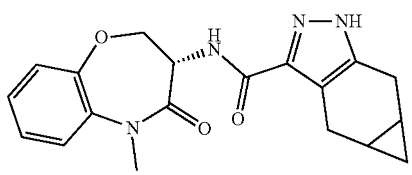 [SMILES: CN1C(=O)[C@@H](NC(=O)c2n[nH]c3c2CC2CC2C3)COc2ccccc21] N-((S)-5-methyl-4-oxo-2,3,4,5-tetrahydrobenzo[b][1,4]oxazepin-3-yl)-1,4,4a,5,5a,6-hexahydrocyclopropa [f]indazole-3-carboxamide | $^1$H NMR (400 MHz, DMSO-d6) δ 12.88 (s, 1H), 7.91 (t, J = 7.3 Hz, 1H), 7.60-7.44 (m, 1H), 7.40-7.05 (m, 3H), 4.97-4.72 (m, 1H), 4.60-4.25 (m, 2H), 3.21-2.63 (m, 4H), 1.35-1.00 (m, 2H), 0.59-0.40 (m, 1H), −0.01-−0.18 (m, 1H). | 353.2 |
| Example 57 Method B' | 0.276 | 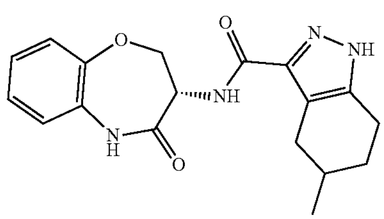 [SMILES: CC1CCc2[nH]nc(C(=O)N[C@H]3COc4ccccc4NC3=O)c2C1] 5-methyl-N-((S)-4-oxo-2,3,4,5-tetrahydrobenzo[b][1,4]oxazepin-3-yl)-4,5,6,7-tetrahydro-1H-indazole-3-carboxamide | $^1$H NMR (400 MHz, DMSO-d6) δ 12.83 (s, 1H), 10.12 (s, 1H), 7.92 (d, J = 7.6 Hz, 1H), 7.25-6.97 (m, 4H), 4.95-4.62 (m, 1H), 4.54-4.32 (m, 2H), 2.94-2.57 (m, 2H), 2.07 (dd, J = 16.2, 9.6 Hz, 1H), 1.92-1.57 (m, 3H), 1.49-1.23 (m, 1H), 1.00 (d, J = 6.5 Hz, 3H). | 341.2 |
| Example 58 Method B' | 0.121 | 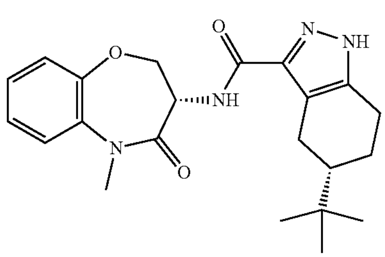 [SMILES: CN1C(=O)[C@@H](NC(=O)c2n[nH]c3c2C[C@@H](C(C)(C)C)CC3)COc2ccccc21] (S)-5-(tert-butyl)-N-((S)-5-methyl-4-oxo-2,3,4,5-tetrahydrobenzo [b][1,4]oxazepin-3-yl)-4,5,6,7-tetrahydro-1H-indazole-3-carboxamide | $^1$H NMR (400 MHz. DMSO-d6) δ 12.82 (s, 1H), 7.92 (d, J = 8.0 Hz, 1H), 7.60-7.45 (m, 1H), 7.39-7.17 (m, 3H), 4.96-4.71 (m, 1H), 4.62-4.30 (m, 2H), 2.89-2.62 (m, 2H), 2.21-1.87 (m, 3H), 1.39-1.10 (m, 2H), 0.89 (s, 9H). | 397.2 |

TABLE 1-continued

| Compound Example # Method | RIP1 Ki (μM) | Structure and Name | $^1$H NMR Data | MS (m/z) |
| --- | --- | --- | --- | --- |
| Example 59 Method B' | 1.7 | 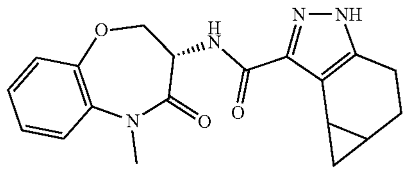 [SMILES: CN1C(=O)[C@@H](NC(=O)c2n[nH]c3c2C2CC2CC3)COc2ccccc21] N-((S)-5-methyl-4-oxo-2,3,4,5-tetrahydrobenzo[b][1,4]oxazepin-3-yl)-3,4,5,5a,6,6a-hexahydrocyclopropa[e]indazole-1-carboxamide | $^1$H NMR (400 MHz, DMSO-d6) δ 12.83 (s, 1H), 7.91 (d, J = 8 2 Hz, 1H), 7.58-7.42 (m, 1H), 7.42-7.14 (m, 3H), 5.00-4.73 (m, 1H), 4.60-4.26 (m, 2H), 2.77-2.59 (m, 1H), 2.31-1.99 (m, 3H), 1.66 (dd, J = 8.5, 4.9 Hz, 1H), 1.37 (s, 1H). 0.91-0.71 (m, 1H), 0.40 (s, 1H). | 353.1 |
| Example 60 Method B' | 0.0156 | 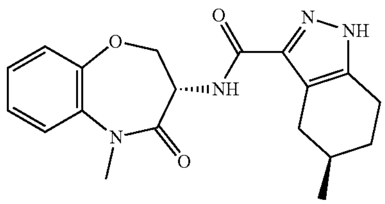 [SMILES: C[C@@H]1CCc2[nH]nc(C(=O)N[C@H]3COc4ccccc4N(C)C3=O)c2C1] (R)-5-methyl-N-((S)-5-methyl-4-oxo-2,3,4,5-tetrahydrobenzo[b][1,4]oxazepin-3-yl)-4,5,6,7-tetrahydro-1H-indazole-3-carboxamide | $^1$H NMR (400 MHz. DMSO-d6) δ 12.83 (s, 1H), 7.89 (d, J = 7.9 Hz, 1H), 7.56-7.43 (m, 1H), 7.39-7.16 (m, 3H), 4.94-4.67 (m, 1H), 4.58-4.30 (m, 2H), 2.84-2.58 (m, 3H), 2.15-1.94 (m, 1H), 1.89-1.57 (m, 2H), 1.44-1.22 (m, 1H), 0.98 (d, J = 6.6 Hz, 3H). | 355.2 |
| Example 61 Method B' | 0.048 | 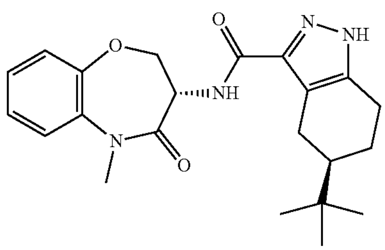 [SMILES: CN1C(=O)[C@@H](NC(=O)c2n[nH]c3c2C[C@H](C(C)(C)C)CC3)COc2ccccc21] (R)-5-(tert-butyl)-N-((S)-5-methyl-4-oxo-2,3,4,5-tetrahydrobenzo[b][1,4]oxazepin-3-yl)-4,5,6,7-tetrahydro-1H-indazole-3-carboxamide | $^1$H NMR (400 MHz, DMSO-d6) δ 12.82 (s, 1H), 7.91 (d, J = 7.9 Hz, 1H), 7.62-7.13 (m, 4H), 4.82 (dt, J = 11.4, 7.8 Hz, 1H), 4.60-4.27 (m, 2H), 2.75 (ddd, J = 28 3, 16.0, 4.4 Hz, 2H), 2.23-1.83 (m, 2H), 1.41-1.11 (m, 2H), 0.89 (s, 9H). | 397.2 |
| Example 62 Method B' | 0.254 | 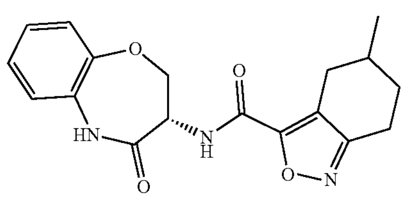 [SMILES: CC1CCc2noc(C(=O)N[C@H]3COc4ccccc4NC3=O)c2C1] 5-methyl-N-((S)-4-oxo-2,3,4,5-tetrahydrobenzo[b][1,4]oxazepin-3-yl)-4,5,6,7-tetrahydrobenzo[c]isoxazole-3-carboxamide | $^1$H NMR (400 MHz, DMSO-d6) δ 10.10 (s, 1H), 8 69 (dd, J = 7.9, 2.8 Hz, 1H), 7.26-7.03 (m, 4H), 4.95-4.71 (m, 1H), 4.58-4 28 (m, 2H), 2.93-2.60 (m, 3H), 2.17-1.93 (m, 1H), 1.93-1.66 (m, 2H), 1.53-1.32 (m, 1H), 1.02 (d, J = 6.6 Hz, 3H). | 342.1 |
| Example 63 Method B' | 0.74 | 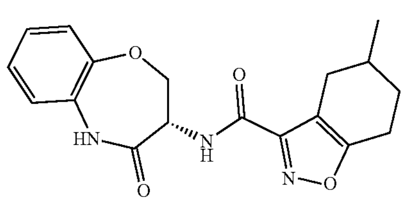 [SMILES: CC1CCc2onc(C(=O)N[C@H]3COc4ccccc4NC3=O)c2C1] 5-methyl-N-((S)-4-oxo-2,3,4,5-tetrahydrobenzo[b][1,4]oxazepin-3-yl)-4,5,6,7-tetrahydrobenzo[d]isoxazole-3-carboxamide | $^1$H NMR (400 MHz, DMSO-d6) δ 10.08 (s, 1H), 8 89 (dd, J = 8.1, 3.1 Hz, 1H), 7.20-6.97 (m, 4H), 4.87-4.70 (m, 1H), 4.66-4 47 (m, 1H), 4.46-4.35 (m, 1H), 2.97-2.77 (m, 2H), 2.74-2.56 (m, 1H), 2.27-2.01 (m, 1H), 1.93-1.67 (m, 2H), 1.43-1.26 (m, 1H), 1.07-0.93 (m, 3H). | 342.1 |

TABLE 1-continued

| Compound Example # Method | RIP1 Ki (μM) | Structure and Name | $^1$H NMR Data | MS (m/z) |
|---|---|---|---|---|
| Example 64 Method B' | 0.0735 | 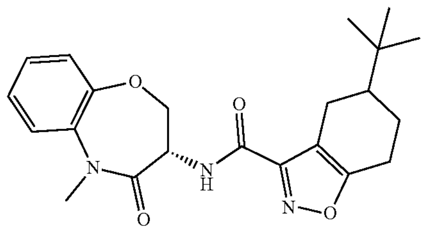 [SMILES: CN1C(=O)[C@@H](NC(=O)c2noc3c2CC(C(C)(C)C)CC3)COc2ccccc21] 5-(tert-butyl)-N-((S)-5-methyl-4-oxo-2,3,4,5-tetrahydrobenzo[b][1,4]oxazepin-3-yl)-4,5,6,7-tetrahydrobenzo[d]isoxazole-3-carboxamide | $^1$H NMR (400 MHz, DMSO-d6) δ 8.94 (dd, J = 8.1, 4.6 Hz, 1H), 7.57-7.44 (m, 1H), 7.37-7.16 (m, 3H), 4.92-4.72 (m, 1H), 4.72- 4.52 (m, 1H), 4.48-4.27 (m, 1H), 3.10-2.78 (m, 2H), 2.64-2.52 (m, 1H), 2.29-2.12 (m, 1H), 2.09-1.92 (m, 1H), 1.41-1.11 (m, 2H), 0.89 (s, 9H) | 398.2 |
| Example 65 Method B' | 0.404 | 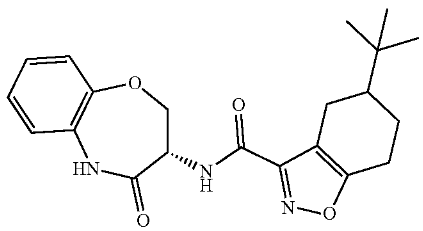 [SMILES: CC(C)(C)C1CCc2onc(C(=O)N[C@H]3COc4ccccc4NC3=O)c2C1] 5-(tert-butyl)-N-((S)-4-oxo-2,3,4,5-tetrahydrobenzo[b][1,4]oxazepin-3-yl)-4,5,6,7-tetrahydrobenzo[d]isoxazole-3-carboxamide | $^1$H NMR (400 MHz. DMSO-d6) δ 10.08 (d, J = 2.0 Hz, 1H), 8.96-8.80 (m, 1H), 7.20-7.01 (m, 4H), 4.89-4.71 (m, 1H), 4.63-4.48 (m, 1H), 4.48-4.34 (m, 1H), 3.03-2.82 (m, 2H), 2.66-2.52 (m, 0H), 2.32-2.14 (m, 1H), 2.13-1.94 (m, 1H), 1.45-1.13 (m, 1H), 0.91 (s, 9H). | 384.2 |
| Example 66 Method B' | 0.0374 | 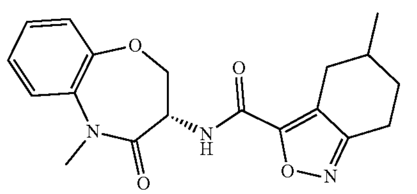 [SMILES: CC1CCc2noc(C(=O)N[C@H]3COc4ccccc4N(C)C3=O)c2C1] 5-methyl-N-((S)-5-methyl-4-oxo-2,3,4,5-tetrahydrobenzo[b][1,4]oxazepin-3-yl)-4,5,6,7-tetrahydrobenzo[c]isoxazole-3-carboxamide | $^1$H NMR (400 MHz, DMSO-d6) δ 8.81-8.67 (m, 1H), 7.58-7.42 (m, 1H), 7.39-7.09 (m, 3H), 4.93-4.73 (m, 1H), 4.65-4.53 (m, 1H), 4.47-4.28 (m, 1H), 2.89-2.56 (m, 3H), 2.12-1.93 (m, 1H), 1.93-1.70 (m, 2H), 1.50-1.34 (m, 1H), 1.09-0.92 (m, 3H). | 356.2 |
| Example 67 Method B' | 0.107 | 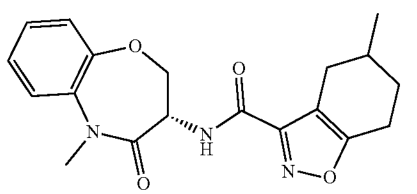 [SMILES: CC1CCc2onc(C(=O)N[C@H]3COc4ccccc4N(C)C3=O)c2C1] 5-methyl-N-((S)-5-methyl-4-oxo-2,3,4,5-tetrahydrobenzo[b][1,4]oxazepin-3-yl)-4,5,6,7-tetrahydrobenzo[d]isoxazole-3-carboxamide | $^1$H NMR (400 MHz, DMSO-d6) δ 8.99-8.77 (m, 1H),7.56-7.44 (m, 1H), 7.38-7.10 (m, 3H), 4.90-4.73 (m, 1H), 4.71-4.55 (m, 1H), 4.44-4.29 (m, 1H), 2.94-2.75 (m, 2H), 2.70-2.55 (m, 1H), 2.21-2.03 (m, 1H), 1.91-1.64 (m, 2H), 1.46-1.23 (m, 1H), 1.00 (dd, J = 6.7, 1.1 Hz, 3H). | 356.2 |
| Example 68 Method B' | 0.0538 | 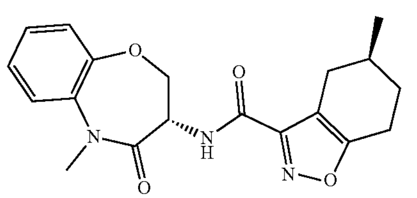 [SMILES: C[C@H]1CCc2onc(C(=O)N[C@H]3COc4ccccc4N(C)C3=O)c2C1] (S)-5-methyl-N-((S)-5-methyl-4-oxo-2,3,4,5-tetrahydrobenzo[b][1,4]oxazepin-3-yl)-4,5,6,7-tetrahydrobenzo[d]isoxazole-3-carboxamide | $^1$H NMR (400 MHz, DMSO-d6) δ 8.91 (s, 1H), 7.57-7.44 (m, 1H), 7.39-7.10 (m, 2H), 4 96-4.72 (m, 1H), 4.72-4.53 (m, 1H), 4.47-4.29 (m, 1H), 2.96-2.75 (m, 2H), 2.75-2.58 (m, 1H), 2.23-1.99 (m, 1H), 1.93-1.66 (m, 2H), 1.45-1.16 (m, 1H), 1.00 (d, J = 6.6 Hz, 3H). | 356.2 |

TABLE 1-continued

| Compound Example # Method | RIP1 Ki (μM) | Structure and Name | $^1$H NMR Data | MS (m/z) |
|---|---|---|---|---|
| Example 69 Method B' | 0.0845 | 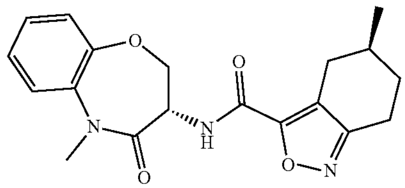 [SMILES: C[C@H]1CCc2noc(C(=O)N[C@H]3COc4ccccc4N(C)C3=O)c2C1] (S)-5-methyl-N-((S)-5-methyl-4-oxo-2,3,4,5-tetrahydrobenzo[b][1,4]oxazepin-3-yl)-4,5,6,7-tetrahydrobenzo[c]isoxazole-3-carboxamide | $^1$H NMR (400 MHz, DMSO-d6) δ 8.72 (d, J = 7.8 Hz, 1H), 7.57-7.45 (m, 1H), 7.41-7.11 (m, 3H), 4.96-4.74 (m, 1H), 4.67-4.51 (m, 1H), 4.49-4.29 (m, 1H), 2.93-2.57 (m, 3H), 2.18-1.95 (m, 1H), 1.97-1.66 (m, 2H), 1.53-1.31 (m, 1H), 1.00 (d, J = 6.6 Hz, 3H). | 356.1 |
| Example 70 Method B' | 0.219 | 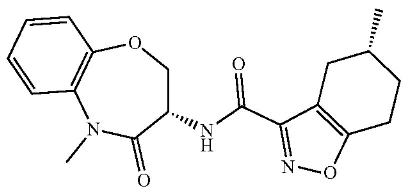 [SMILES: C[C@@H]1CCc2onc(C(=O)N[C@H]3COc4ccccc4N(C)C3=O)c2C1] (R)-5-methyl-N-((S)-5-methyl-4-oxo-2,3,4,5-tetrahydrobenzo[b][l,4]oxazepin-3-yl)-4,5,6,7-tetrahydrobenzo[d]isoxazole-3-carboxamide | $^1$H NMR (400 MHz, DMSO-d6) δ 8.90 (d, J = 6.3 Hz, 1H), 7.58-7.42 (m, 1H), 7.41-7.12 (m, 3H), 4.82 (q, J = 8.6, 6.6 Hz, 1H), 4.73-4.53 (m, 1H), 4.48-4.25 (m, 1H), 2.95-2.81 (m, 2H), 2.77-2.56 (m, 1H), 2.20-2.01 (m, 1H), 1.92-1.65 (m, 2H), 1.50-1.13 (m, 1H), 1.00 (d, J = 6.6 Hz, 3H). | 356.2 |
| Example 71 Method B' | 0.0192 | 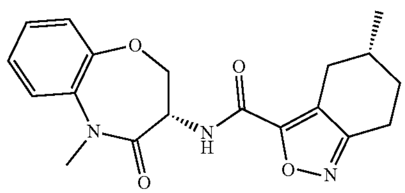 [SMILES: C[C@@H]1CCc2noc(C(=O)N[C@H]3COc4ccccc4N(C)C3=O)c2C1] (R)-5-methyl-N-((S)-5-methyl-4-oxo-2,3,4,5-tetrahydrobenzo[b][1,4]oxazepin-3-yl)-4,5,6,7-tetrahydrobenzo[c]isoxazole-3-carboxamide | $^1$H NMR (400 MHz, DMSO-d6) δ 8.72 (d, J = 7.7 Hz, 1H), 7.57-7.41 (m, 1H), 7 40-7.10 (m, 3H), 4.01-4.74 (m, 1H), 4 68-4.52 (m, 1H), 4.50-4.31 (m, 1H), 2.86-2.58 (m, 3H), 2.13-1.94 (m, 1H), 1.92-1.69 (m, 2H), 1.52-1.33 (m, 1H), 1 00 (d, J = 6.6 Hz, 3H). | 356.2 |
| Example 72 Method B or Method G1 | 0.068 | 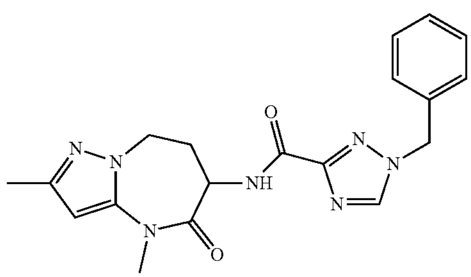 [SMILES: Cc1cc2n(n1)CCC(NC(=O)c1ncn(Cc3ccccc3)n1)C(=O)N2C] 1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-d6) δ 8.82 (s, 1H), 8.50 (d, J = 7.8 Hz, 1H), 7.44-7.24 (m, 5H), 6.12 (s, 1H), 5.48 (s, 2H), 4.38-4.19 (m, 2H), 4.10 (ddd, J = 14.5, 12.6, 6.6 Hz, 1H), 3.21 (s, 3H), 2.64-2.53 (m, 1H), 2.38-2.27 (m, 1H), 2.16 (d, J = 0.5 Hz, 3H). | 380.2 3.69 min |
| Example 73 Method B or Method G1 | 0.027 | 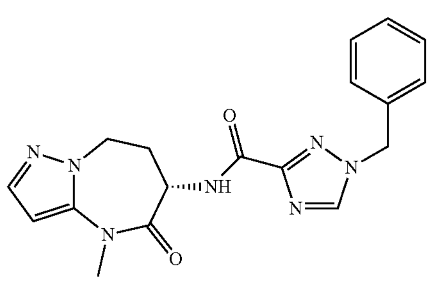 [SMILES: CN1C(=O)[C@@H](NC(=O)c2ncn(Cc3ccccc3)n2)CCn2nccc21] (S)-1-benzyl-N-(4-methyl-5-oxo-5,6,7,8-tetrahydro-4H-pyrazolo | $^1$H NMR (400 MHz, DMSO-d6) δ 8.82 (s, 1H), 8.53 (d, J = 7.8 Hz, 1H), 7.48 (d, J = 2.0 Hz, 1H), 7.42-7.27 (m, 5H), 6.34 (d, J = 2.0 Hz, 1H), 5.48 (s, 2H), 4.42-4.11 (m, 3H), 3.24 (s, 3H), 2.68-2.52 (m, 1H), 2.43-2.30 (m, 1H). | 366.1 3.47 min |

TABLE 1-continued

| Compound Example # Method | RIP1 Ki (μM) | Structure and Name | $^1$H NMR Data | MS (m/z) |
|---|---|---|---|---|
| | | [1,5-a][1,3]diazepin-6-yl)-1H-1,2,4-triazole-3-carboxamide | | |
| Example 74 Method B | 0.013 | 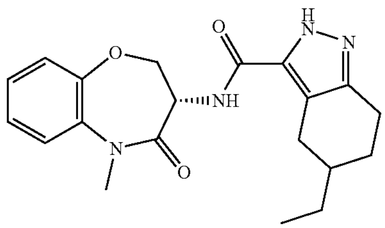 [SMILES: CCC1CCc2n[nH]c(C(=O)N[C@H]3COc4ccccc4N(C)C3=O)c2C1] 5-ethyl-N-((S)-5-methyl-4-oxo-2,3,4,5-tetrahydrobenzo[b][1,4]oxazepin-3-yl)-4,5,6,7-tetrahydro-2H-indazole-3-carboxamide | $^1$H NMR (400 MHz, DMSO-d6) δ 12.83 (s, 1H), 7 90 (d, J = 8 0 Hz, 1H), 7.51-7.45 (m, 1H), 7.35-7.26 (m, 2H), 7.25-7.21 (m, 1H), 4.90-4.76 (m, 1H), 4.55-4.45 (m, 1H), 4.45-4.36 (m, 1H), 2.87-2.76 (m, 1H), 2.72-2.60 (m, 1H), 2.11-1.97 (m, 1H), 1.92-1.78 (m, 1H), 1.53-1.42 (m, 1H), 1.40-1.25 (m, 3H), 0.90 (t, J = 7.4 Hz, 3H). | 369.2 5.17 min |
| Example 75 Scheme 33 & Method B or Method G4 | 0.231 | 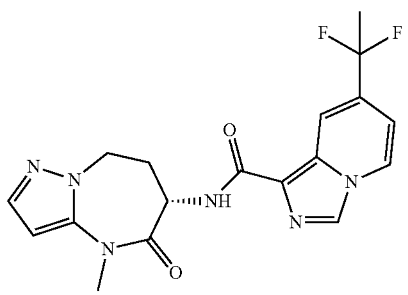 [SMILES: CN1C(=O)[C@@H](NC(=O)c2ncn3ccc(C(C)(F)F)cc23)CCn2nccc21] (S)-N-(4-methyl-5-oxo-5,6,7,8-tetrahydro-4H-pyrazolo[1,5-a][1,3]diazepin-6-yl)-7-(trifluoro methyl)imidazo[1,5-a]pyridine-1-carboxamide | $^1$H NMR (400 MHz, DMSO-d6) δ 8.74-8.63 (m, 2H), 8.40 (d, J = 7.9 Hz, 1H), 8.37-8.29 (m, 1H), 7.51 (d, J = 2.0 Hz, 1H), 7.11 (dd, J = 7.4, 1.9 Hz, 1H), 6.35 (d, J = 2.0 Hz, 1H), 4.44-4.33 (m, 2H), 4.22 (ddd, J = 14.5, 12.6, 6.6 Hz, 1H), 3.26 (s, 3H), 2.71-2.56 (m, 1H), 2.46-2.35 (m, 1H). | 393.1 4.03 min |
| Example 76 Scheme 33 & Method B or Method G4 | 0.536 | 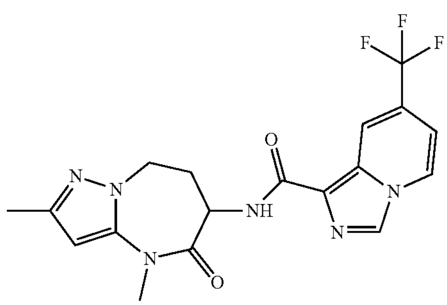 [SMILES: Cc1cc2n(n1)CCC(NC(=O)c1ncn3ccc(C(F)(F)F)cc13)C(=O)N2C] N-(2,4-dimethyl-5-oxo-5,6,7,8-tetrahydro-4H-pyrazolo[1,5-a][1,3]diazepin-6-yl)-7-(trifluoro methyl)imidazo[1,5-a]pyridine-1-carboxamide | $^1$H NMR (400 MHz, DMSO-d6) δ 8.72-8.63 (m, 2H), 8.37 (d, J = 7.9 Hz, 1H), 8.35-8.30 (m, 1H), 7.11 (dd, J = 7.4, 1.9 Hz, 1H), 6.13 (s, IH), 4.41 (dt, J = 11.6, 7.9 Hz, 1H), 4.29 (dd, J = 14.4, 8.1 Hz, 1H), 4.13 (ddd, J = 14.5, 12.6, 6.5 Hz, 1H), 3.23 (s, 3H), 2.70-2.56 (m, 1H), 2.42-2.30 (m, 1H), 2.18 (s, 3H) | 407.1 4.25 min |
| Example 77 SFC purification of Ex. 28 | 0.058 | 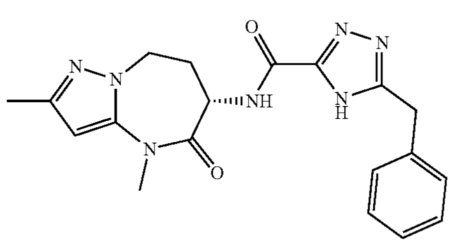 [SMILES: Cc1cc2n(n1)CC[C@H](NC(=O)c1nnc(Cc3ccccc3)[nH]1)C(=O)N2C] (S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, DMSO-d6) δ 14.30 (s, 2H), 8.44-8.37 (m, 2H), 7 38-7.23 (m, 12H), 6.12 (s, 2H), 4.38-4.21 (m, 5H), 4.16-4.00 (m, 7H), 3.71 (s, 2H), 3.07-2.93 (m, 1H), 2.63-2.51 (m, 2H), 2.50-2.25 (m, 2H), 1.84 (s, 1H). | 380.2 3.60 min |

TABLE 1-continued

| Compound Example # Method | RIP1 Ki (μM) | Structure and Name | $^1$H NMR Data | MS (m/z) |
|---|---|---|---|---|
| Example 78 Method B | 0.021 | 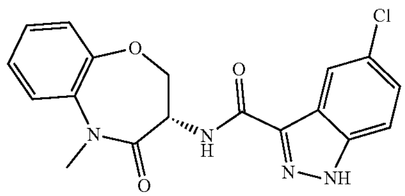 [SMILES: CN1C(=O)[C@@H](NC(=O)c2n[nH]c3ccc(Cl)cc23)COc2ccccc21] (S)-5-chloro-N-(5-methyl-4-oxo-2,3,4,5-tetrahydrobenzo[b][1,4]oxazepin-3-yl)-1H-indazole-3-carboxamide | $^1$H NMR (400 MHz, DMSO-d6) δ 13.92 (s, 1H), 8 48 (d, J = 8.1 Hz, 1H), 8.04 (dd, J = 2.1, 0.7 Hz, 1H), 7.69 (dd, J = 8 9, 0.7 Hz, 1H), 7.55-7.49 (m, 1H), 7 44 (dd, J = 8.9, 2.0 Hz, 1H), 7.39-7.22 (m, 3H), 4.94 (dt, J = 11.5, 7.9 Hz, 1H), 4.64 (dd, J = 11.6, 9.9 Hz, 1H), 4.47 (dd, J = 9.9, 7.7 Hz, 1H), 3.33 (s, 3H). | 371.1 5.12 min |
| Example 79 SFC purification of Ex. 29 | 0.034 | 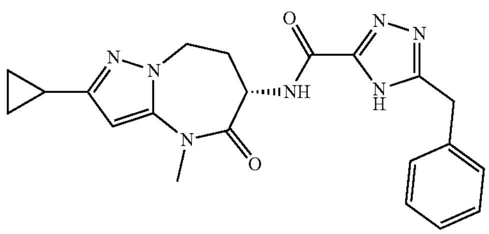 [SMILES: CN1C(=O)[C@@H](NC(=O)c2nnc(Cc3ccccc3)[nH]2)CCn2nc(C3CC3)cc21] (S)-5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, DMSO-d6) δ 7.40-7.21 (m, 5H), 6.06 (s, 1H), 4.17 (d, J = 48.9 Hz, 3H), 3.20 (s, 4H), 1.96-1.66 (m, 1H), 0.95-0.48 (m, 4H). | 406.2 3.99 min |
| Example 80 SFC purification of Ex. 30 | 0.064 | 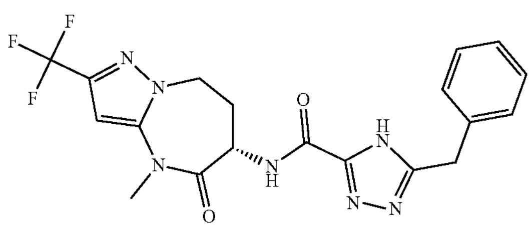 [SMILES: CN1C(=O)[C@@H](NC(=O)c2nnc(Cc3ccccc3)[nH]2)CCn2nc(C(F)(F)F)cc21] (S)-5-benzyl-N-(4-methyl-5-oxo-2-(trifluoromethyl)-5,6,7,8-tetrahydro-4H-pyrazolo[1,5-a][1,3]diazepin-6-yl)-4H-1,2,4-triazole-3-carboxamide | $^1$H NMR (400 MHz, DMSO-d6) δ 7.43-7.16 (m, 5H), 6.93 (s, 1H), 4.56-4.25 (m, 3H), 4.11 (s, 2H), 2.74-2.56 (m, 1H). | 434.1 4.38 min |
| Example 81 Scheme 34 & Method B or Method G4 | 0.567 | 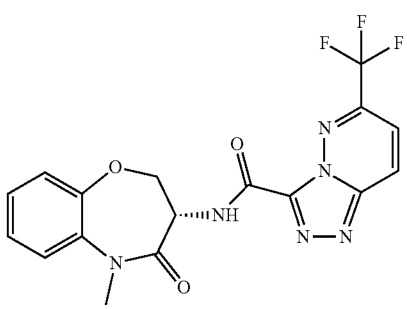 [SMILES: CN1C(=O)[C@@H](NC(=O)c2nnc3ccc(C(F)(F)F)nn23)COc2ccccc21] (S)-N-(5-methyl-4-oxo-2,3,4,5-tetrahydrobenzo[b][1,4]oxazepin-3-yl)-6-(trifluoromethyl)-[1,2,4]triazolo[4,3-b]pyridazine-3-carboxamide | $^1$H NMR (400 MHz, DMSO-d6) δ 9.34 (d, J = 7.8 Hz, 1H), 8.84 (dt, J = 9.8, 0.7 Hz, 1H), 7.96 (d, J = 9.7 Hz, 1H), 7.58-7.48 (m, 1H), 7.43-7.22 (m, 3H), 4.96 (dt, J = 11.4, 7.8 Hz, 1H), 4.67-4 49 (m, 2H), 3.35 (s, 3H) | 407.1 4.25 min |

TABLE 1-continued

| Compound Example # Method | RIP1 Ki (μM) | Structure and Name | $^1H$ NMR Data | MS (m/z) |
|---|---|---|---|---|
| Example 82 Scheme 35, Method B and Method G4 | 0.393 | 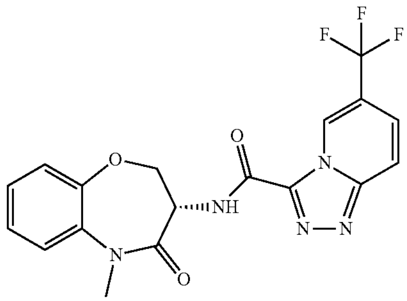 [SMILES: CN1C(=O)[C@@H](NC(=O)c2nnc3ccc(C(F)(F)F)cn23)COc2ccccc21] (S)-N-(5-methyl-4-oxo-2,3,4,5-tetrahydrobenzo[b][1,4]oxazepin-3-yl)-6-(trifluoromethyl)-[1,2,4]triazolo[4,3-a]pyridine-3-carboxamide | $^1H$ NMR (400 MHz, DMSO-d6) δ 9.49-9.40 (m, 2H), 8.25-8.14 (m, 1H), 7.83 (dd, J = 9.6, 18 Hz, 1H), 7.58-7.49 (m, 1H), 7.40-7.19 (m, 3H), 4.95 (dt, J = 11.6, 7.8 Hz, 1H), 4.76 (dd, J = 11.7, 9.9 Hz, 1H), 4.47 (dd, J = 9.9, 7.7 Hz, 1H), 3.34 (s, 3H). | 406.1 4.90 min |

TABLE 2

| Compound Example # Method | RIP1 Ki (μM) | Structure and Name | $^1H$ NMR Data | MS (m/z) |
|---|---|---|---|---|
| Example 83 Method B | 0.167 | 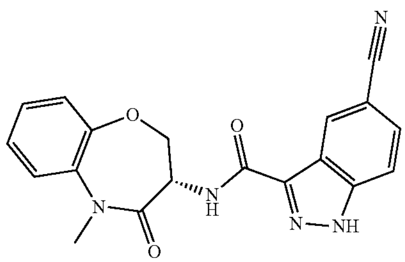 [SMILES: CN1C(=O)[C@@H](NC(=O)c2n[nH]c3ccc(C#N)cc23)COc2ccccc21] (S)-5-cyano-N-(5-methyl-4-oxo-2,3,4,5-tetrahydrobenzo[b][1,4]oxazepin-3-yl)-1H-indazole-3-carboxamide | $^1H$ NMR (400 MHz, DMSO-$d_6$) δ 14.23 (s, 1H), 8.68-8.59 (m, 1H), 8.52-8.43 (m, 1H), 7.87-7.74 (m, 2H), 7.58-7.48 (m, 1H), 7.42-7.18 (m, 3H), 5.00-4.88 (m, 1H), 4.73-4.60 (m, 1H), 4.53-4.41 (m, 1H), 3.33 (s, 3H). | 362.1 4.57 min |
| Example 84 Similar to Method A | 1.4 | 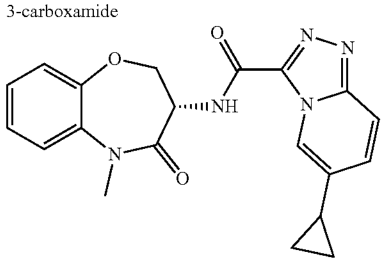 (S)-6-cyclopropyl-N-(5-methyl-4-oxo-2,3,4,5-tetrahydrobenzo[b][1,4]oxazepin-3-yl)-[1,2,4]triazolo[4,3-a]pyridine-3-carboxamide | $^1H$ NMR (400 MHz, DMSO-$d_6$) δ 9.31 (d, J = 8.0 Hz, 1H), 9.25-9.20 (m, 1H), 7.99 (dd, J = 9.7, 1.0 Hz, 1H), 7.72 (dd, J = 9.7, 1.8 Hz, 1H), 7.59-7.49 (m, 1H), 7.42-7.22 (m, 3H), 5.02-4.87 (m, 1H), 4.81-4.67 (m, 1H), 4.54-4.41 (m, 1H), 1.79-1.69 (m, 1H), 1.03-0.93 (m, 2H), 0.80-0.69 (m, 2H) | 378.1 4.66 min |
| Example 85 Method B | 0.0768 | 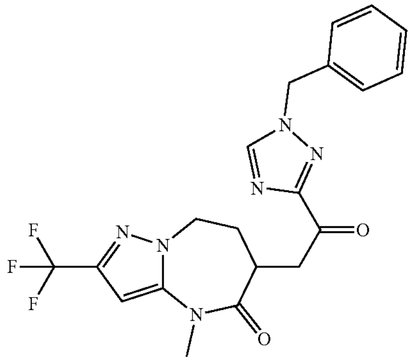 [SMILES: CN1C(=O)C(CC(=O)c2ncn(Cc3ccccc3)n2)CCn2nc(C(F)(F)F)cc21] | $^1H$ NMR (400 MHz, DMSO-$d_6$) δ 8.82 (s, 1H), 8.63 (d, J = 7.6 Hz, 1H), 7.49-7.19 (m, 5H), 6.93 (s, 1H), 5.49 (s, 2H), 4.51-4.42 (m, 1H), 4.39-4.27 (m, 2H), 3.27 (s, 3H), 2.72-2.59 (m, 1H), 2.48-2.42 (m, 1H). | 434.1 4.60 min |

TABLE 2-continued

| Compound Example # Method | RIP1 Ki (μM) | Structure and Name | $^1$H NMR Data | MS (m/z) |
|---|---|---|---|---|
| | | 1-benzyl-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide | | |
| Example 86 Arbitrarily assigned CF3 chirality Method B | 0.0208 | 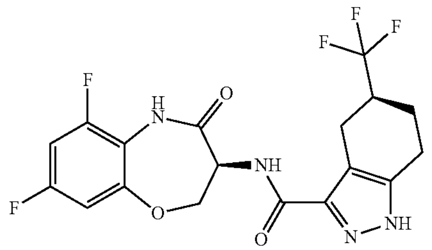 [SMILES: O=C(N[C@H]1COc2cc(F)cc(F)c2NC1=O)c1n[nH]c2c1C[C@@H](C(F)(F)F)CC2] (S)-N-((S)-6,8-difluoro-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, DMSO-$d_6$) δ 13.02 (s, 1H), 10.03 (s, 1H), 8.03 (d, J = 7.6 Hz, 1H), 7.31-7.16 (m, 1H), 7.12-6.96 (m, 1H), 4.95-4.81 (m, 1H), 4.69-4.56 (m, 1H), 4.56-4.44 (m, 1H), 3.10-2.95 (m, 1H), 2.87-2.58 (m, 3H), 2.17-2.03 (m, 1H), 1.72-1.55 (m, 1H). | 431.1 5.03 min |
| Example 87 Arbitrarily assigned CF3 chirality Method B | 0.104 | 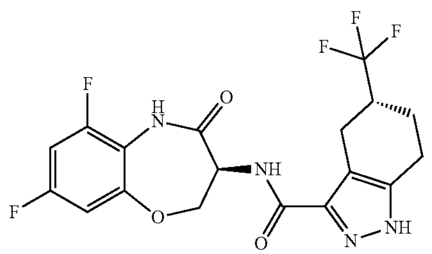 [SMILES: O=C(N[C@H]1COc2cc(F)cc(F)c2NC1=O)c1n[nH]c2c1C[C@H](C(F)(F)F)CC2] (R)-N-((S)-6,8-difluoro-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, DMSO-$d_6$) δ 13.02 (s, 1H), 10.03 (s, 1H), 8.02 (d, J = 7.7 Hz, 1H), 7.49-7.12 (m, 1H), 7.12-6.87 (m, 1H), 5.06-4.81 (m, 1H), 4.67-4.55 (m, 1H), 4.55-4.45 (m, 1H), 3.08-2.95 (m, 1H), 2.87-2.59 (m, 3H), 2.20-2.02 (m, 1H), 1.76-1.56 (m, 1H). | 431.1 5.01 min |
| Example 88 Method B | 0.0167 | 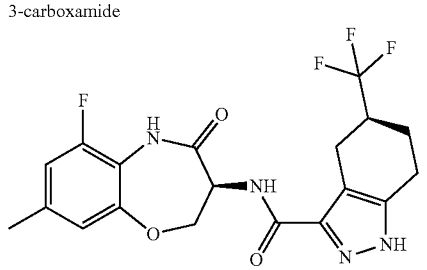 (S)-N-((S)-6-fluoro-8-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, DMSO-$d_6$) δ 13.01 (s, 1H), 9.95 (s, 1H), 8.00 (d, J = 7.8 Hz, 1H), 7.05-6.93 (m, 1H), 6.93-6.83 (m, 1H), 4.90-4.77 (m, 1H), 4.60-4.51 (m, 1H), 4.49-4.41 (m, 1H), 3.06-2.95 (m, 1H), 2.85-2.74 (m, 1H), 2.74-2.58 (m, 2H), 2.47-2.42 (m, 1H), 2.30 (s, 3H), 2.14-2.09 (m, 1H), 1.70-1.56 (m, 1H). | 427.1 5.20 min |
| Example 89 Method B | 0.0554 | 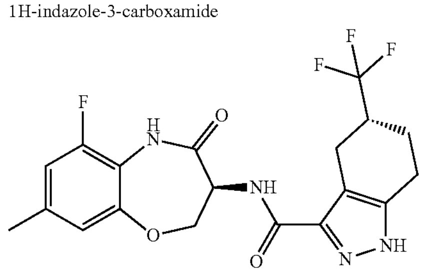 (R)-N-((S)-6-fluoro-8-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, DMSO-$d_6$) δ 13.01 (s, 1H), 9.95 (s, 1H), 7.99 (d, J = 7.8 Hz, 1H), 7.07-6.92 (m, 1H), 6.92-6.80 (m, 1H), 4.97-4.74 (m, 1H), 4.63-4.49 (m, 1H), 4.49-4.37 (m, 1H), 3.07-2.94 (m, 1H), 2.87-2.74 (m, 1H), 2.74-2.59 (m, 2H), 2.48-2.42 (m, 1H), 2.30 (s, 3H), 2.18-2.02 (m, 1H), 1.72-1.55 (m, 1H). | 427.1 5.19 min |

TABLE 2-continued

| Compound Example # Method | RIP1 Ki (μM) | Structure and Name | $^1$H NMR Data | MS (m/z) |
|---|---|---|---|---|
| Example 90 Method B | 0.0186 | 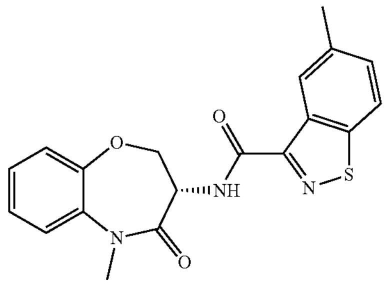 [SMILES: Cc1ccc2snc(C(=O)N[C@H]3COc4ccccc4N(C)C3=O)c2c1] (S)-5-methyl-N-(5-methyl-4-oxo-2,3,4,5-tetrahydrobenzo[b][1,4]oxazepin-3-yl)benzo[d]isothiazole-3-carboxamide | $^1$H NMR (400 MHz, DMSO-$d_6$) δ 8.89 (d, J = 8.0 Hz, 1H), 8.48-8.40 (m, 1H), 8.23-8.14 (m, 1H), 7.59-7.46 (m, 2H), 7.40-7.20 (m, 3H), 4.99-4.86 (m, 1H), 4.72-4.62 (m, 1H), 4.54-4.42 (m, 1H), 3.34 (s, 3H), 2.46 (s, 3H). | 368.1 5.97 min |
| Example 91 Method B | 0.0271 | 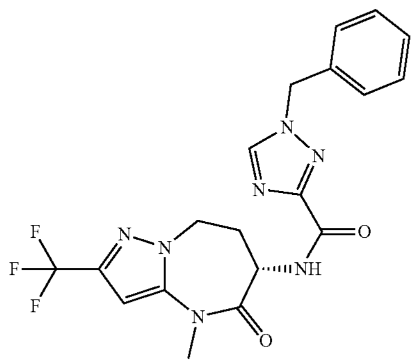 [SMILES: CN1C(=O)[C@@H](NC(=O)c2ncn(Cc3ccccc3)n2)CCn2nc(C(F)(F)F)cc21] (S)-1-benzyl-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.82 (s, 1H), 8.63 (d, J = 7.6 Hz, 1H), 7.46-7.17 (m, 5H), 6.93 (s, 1H), 5.49 (s, 2H), 4.52-4.43 (m, 1H), 4.39-4.27 (m, 2H), 3.27 (s, 3H), 2.70-2.58 (m, 1H), 2.47-2.42 (m, 1H). | 434.1 4.63 min |
| Example 92 Method B | 0.0129 | 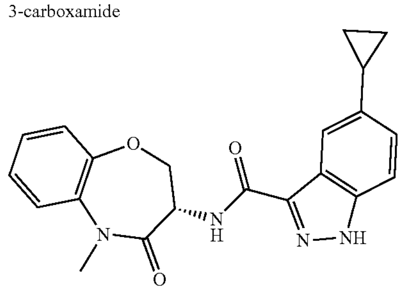 (S)-5-cyclopropyl-N-(5-methyl-4-oxo-2,3,4,5-tetrahydrobenzo[b][1,4]oxazepin-3-yl)-1H-indazole-3-carboxamide | $^1$H NMR (400 MHz, DMSO-$d_6$) δ 13.58 (s, 1H), 8.34 (d, J = 8.0 Hz, 1H), 7.78-7.70 (m, 1H), 7.58-7.46 (m, 2H), 7.39-7.22 (m, 3H), 7.16 (dd, J = 8.7, 1.7 Hz, 1H), 5.03-4.83 (m, 1H), 4.67-4.57 (m, 1H), 4.52-4.42 (m, 1H), 2.10-1.96 (m, 1H), 1.00-0.91 (m, 2H), 0.68-0.59 (m, 2H). | 377.1 5.36 min |
| Example 93 Method B | 0.381 | 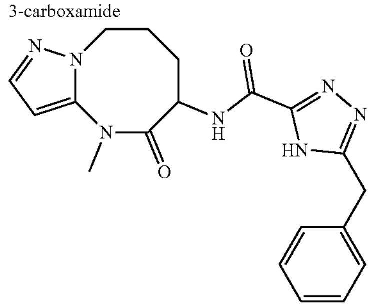 5-benzyl-N-(4-methyl-5-oxo-4,5,6,7,8,9-hexahydropyrazolo[1,5-a][1,3]diazocin-6-yl)-4H-1,2,4-triazole-3-carboxamide | $^1$H NMR (400 MHz, DMSO-$d_6$) δ 8.27 (s, 1H), 7.56 (d, J = 2.0 Hz, 1H), 7.36-7.28 (m, 2H), 7.29-7.21 (m, 3H), 6.36 (d, J = 2.0 Hz, 1H), 4.42-4.29 (m, 1H), 4.09 (s, 2H), 3.97-3.80 (m, 2H), 3.21 (s, 3H), 2.07-1.96 (m, 1H), 1.93-1.77 (m, 2H), 1.66-1.53 (m, 1H). | 380.2 3.61 min |

TABLE 2-continued

| Compound Example # Method | RIP1 Ki (μM) | Structure and Name | $^1$H NMR Data | MS (m/z) |
|---|---|---|---|---|
| Example 94 Method B | 0.0925 | 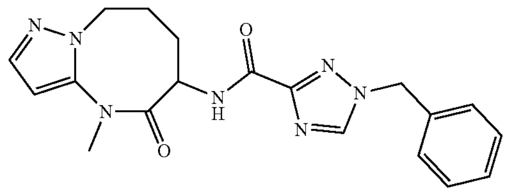 [SMILES: CN1C(=O)C(NC(=O)c2ncn(Cc3ccccc3)n2)CCCn2nccc21] 1-benzyl-N-(4-methyl-5-oxo-4, 5,6,7,8,9-hexahydropyrazolo[1,5-a] [1,3]diazocin-6-yl)-1H-1,2,4- triazole-3-carboxamide | $^1$H NMR (400 MHz, DMSO-$d_6$) δ 8.80 (s 1H) 8 24 (d J = 7.0 Hz, 1H), 7.56 (d, J = 2.0 Hz, 1H), 7.39-7.27 (m, 5H), 6.36 (d, J = 2.0 Hz, 1H), 5.47 (s, 2H), 4.42-4.28 (m, 1H), 3.98-3.77 (m, 2H), 3.21 (s, 3H), 2.08-1.95 (m, 1H), 1.92-1.76 (m, 2H), 1.67-1.54 (m, 1H). | 380.2 3.72 min |
| Example 95 Method B | 4.3 | 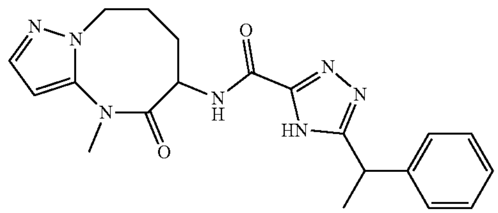 [SMILES: CC(c1ccccc1)c1nnc(C(=O)NC2CCCn3nccc3N(C)C2=O)[nH]1] N-(4-methyl-5-oxo-4,5,6,7,8,9- hexahydropyrazolo[1,5-a][1,3] diazocin-6-yl)-5-(1-phenylethyl)- 4H-1,2,4-triazole-3-carboxamide | $^1$H NMR (400 MHz, DMSO-$d_6$) δ 8.31-8.20 (m, 1H), 7.59-7.54 (m, 1H), 7.36-7.17 (m, 6H), 6.41-6.32 (m, 1H), 4.47-4.24 (m, 2H), 4.02-3.76 (m, 2H), 3.22 (d, J = 2.4 Hz, 3H), 2.05-1.97 (m, 1H), 1.92-1.76 (m, 2H), 1.64-1.58 (m, 4H). | 394.2 3.85 min |
| Example 96 Method B | 0.801 | 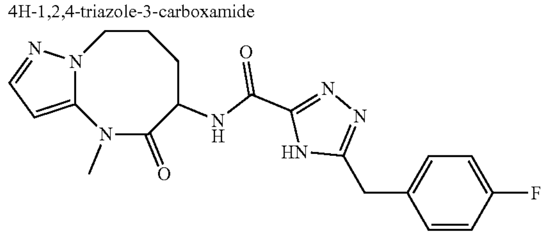 5-(4-fluorobenzyl)-N-(4-methyl- 5-oxo-4,5,6,7,8,9-hexahydropyrazolo[1,5-a] [1,3]diazocin-6- yl)-4H-1,2,4-triazole-3-carboxamide | $^1$H NMR (400 MHz, DMSO-$d_6$) δ 8.32-8.22 (m, 1H), 7.61-3.72 7.49 (m, 1H), 7.34-7.25 (m, 2H), 7.18-7.09 (m, 2H), 6.41-6.31 (m, 1H), 4.41-4.28 (m, 1H), 4.09 (s, 2H), 3.98-3.79 (m, 2H), 3.21 (s, 3H), 2.08-1.96 (m, 1H), 1.94-1.77 (m, 2H), 1.68-1.52 (m, 1H). | 398.1 3.72 min |
| Example 97 Method B | 0.215 | 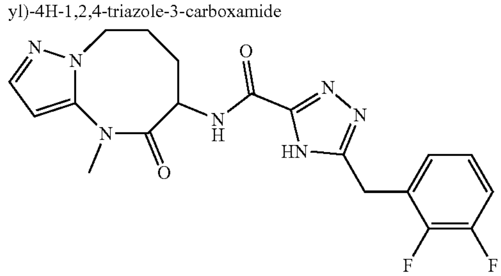 5-(2,3-difluorobenzyl)-N-(4-methyl- 5-oxo-4,5,6,7,8,9-hexahydropyrazolo[1,5-a] [1,3]diazocin- 6-yl)-4H-1,2,4-triazole-3-carboxamide | $^1$H NMR (400 MHz, DMSO-$d_6$) δ 8.34-8.25 (m, 1H), 7.56 (d, J = 2.0 Hz, 1H), 7.39-7.27 (m, 1H), 7.23-7.10 (m, 2H), 6.35 (d, J = 2.0 Hz, 1H), 4.41-4.29 (m, 1H), 4.17 (s, 2H), 3.97-3.78 (m, 2H), 3.21 (s, 3H), 2.07 1.97 (m, 1H), 1.96-1.77 (m, 2H), 1.67-1.53 (m, 1H). | 416.2 3.81 min |
| Example 98 Method B | 0.0704 | 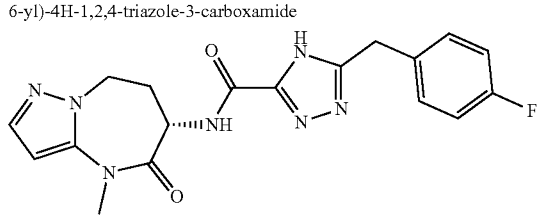 (S)-5-(4-fluorobenzyl)-N-(4-m ethyl-5-oxo-5,6,7,8-tetrahydro- 4H-pyrazolo[1,5-a][1,3]diazepin- 6-yl)-4H-1,2,4-triazole-3-carboxamide | $^1$H NMR (400 MHz, DMSO-$d_6$) δ 8.57-8.50 (m, 1H), 7.49 (d, J = 2.0 Hz, 1H), 7.38-7.24 (m, 2H), 7.20-7.08 (m, 2H), 6.34 (d, J = 2.1 Hz, 1H), 4.42-4.25 (m, 2H), 4.24-4.13 (m, 1H), 4.09 (s, 2H), 3.25 (s, 3H), 2.67-2.53 (m, 1H), 2.44-2.29 (m, 1H). | 384.1 3.63 |

TABLE 2-continued

| Compound Example # Method | RIP1 Ki (μM) | Structure and Name | $^1$H NMR Data | MS (m/z) |
|---|---|---|---|---|
| Example 99 Method B | 0.0346 | 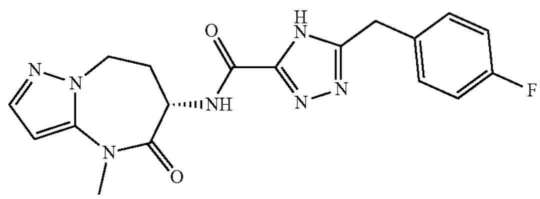 [SMILES: CN1C(=O)[C@@H](NC(=O)c2nnc(Cc3ccc(F)cc3)[nH]2)CCn2nccc21] (S)-5-(2,3-difluorobenzyl)-N-(4-methyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, DMSO-$d_6$) δ 8.62-8.51 (m, 1H), 7.49 (d, J = 2.0 Hz, 1H), 7.39-7.28 (m, 1H), 7.23-7.09 (m, 2H), 6.34 (d, J = 2.0 Hz, 1H), 4.41-4.26 (m, 2H), 4.23-4.14 (m, 3H), 3.24 (s, 3H), 2.62-2.55 (m, 1H), 2.44-2.33 (m, 1H). | 402.1 3.71 min |
| Example 100 Method B | 0.189 | 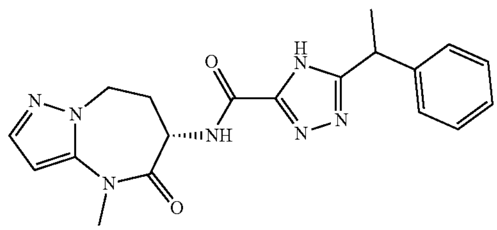 [SMILES: CC(c1ccccc1)c1nnc(C(=O)N[C@H]2CCn3nccc3N(C)C2=O)[nH]1] N-((S)-4-methyl-5-oxo-5,6,7,8-tetrahydro-4H-pyrazolo[1,5-a][1,3]diazepin-6-yl)-5-(1-phenylethyl)-4H-1,2,4-triazole-3-carboxamide | $^1$H NMR (400 MHz, DMSO-$d_6$) δ 8.52 (s, 1H), 7.49 (d, J = 2.0 Hz, 1H), 7.36-7.18 (m, 6H), 6.34 (d, J = 2.0 Hz, 1H), 4.42-4.26 (m, 4H), 4.24-4.13 (m, 1H), 3.25 (s, 3H), 1.63 (d, J = 7.3 Hz, 3H). | 380.2 3.75 min |
| Example 101 Method B | 0.189 | 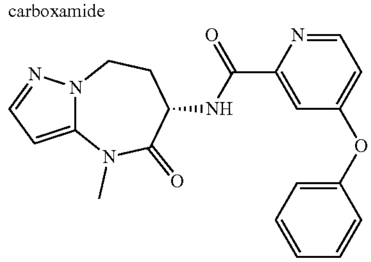 (S)-N-(4-methyl-5-oxo-5,6,7,8-tetrahydro-4H-pyrazolo[1,5-a][1,3]diazepin-6-yl)-4-phenoxypicolinamide | $^1$H NMR (400 MHz, DMSO-$d_6$) δ 8.92 (d, J = 7.8 Hz, 1H), 8.62-8.54 (m, 1H), 7.57-7.45 (m, 3H), 7.39-7.30 (m, 2H), 7.27-7.17 (m, 3H), 6.33 (d, J = 2.0 Hz, 1H), 4.44-4.14 (m, 3H), 3.25 (s, 3H), 2.74-2.61 (m, 1H), 2.41-2.27 (m, 1H). | 378.2 4.59 min |
| Example 102 Method B | 0.335 | 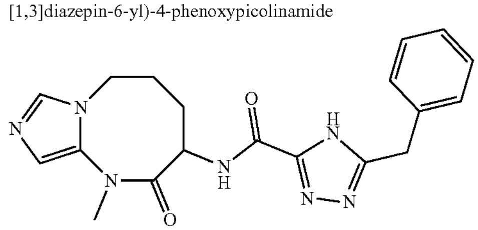 5-benzyl-N-(1-methyl-2-oxo-1,2,3,4,5,6-hexahydroimidazo[1,5-a][1,3]diazocin-3-yl)-4H-1,2,4-triazole-3-carboxamide | $^1$H NMR (400 MHz, DMSO-$d_6$) δ 8.31-8.21 (m, 1H), 7.56 (d, J = 2.0 Hz, 1H), 7.37-7.18 (m, 5H), 6.59 (s, 0H), 6.36 (d, J = 2.0 Hz, 1H), 4.41-4.29 (m, 1H), 4.09 (s, 2H), 3.98-3.76 (m, 2H), 3.21 (s, 3H), 2.06-1.98 (m, 1H), 1.93-1.79 (m, 2H), 1.68-1.52 (m, 1H). | 380.2 3.46 min |
| Example 103 Method B | 0.124 | 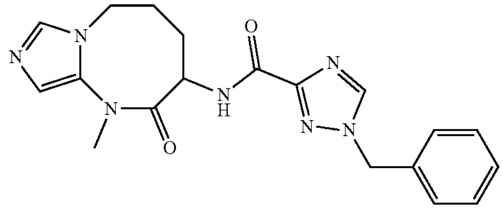 1-benzyl-N-(1-methyl-2-oxo-1,2,3,4,5,6-hexahydroimidazo[1,5-a][1,3]diazocin-3-yl)-1H-1,2,4-triazole-3-carboxamide | $^1$H NMR (400 MHz, DMSO-$d_6$) δ 8.80 (s, 1H), 8.24 (d, J = 7.1 Hz, 1H), 7.56 (d, J = 2.0 Hz, 1H), 7.42-7.26 (m, 6H), 6.36 (d, J = 2.0 Hz, 1H), 5.47 (s, 2H), 4.42-4.29 (m, 1H), 3.97-3.76 (m, 2H), 3.21 (s, 3H), 2.07-1.97 (m, 1H), 1.92-1.77 (m, 2H), 1.68-1.53 (m, 1H). | 380.2 3.55 min |

TABLE 2-continued

| Compound Example # Method | RIP1 Ki (μM) | Structure and Name | $^1$H NMR Data | MS (m/z) |
|---|---|---|---|---|
| Example 104 Method B | 0.149 | 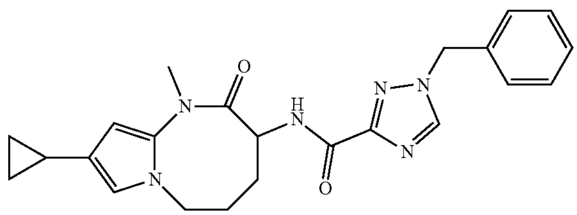 [SMILES: CN1C(=O)C(NC(=O)c2ncn(Cc3ccccc3)n2)CCCn2cc(C3CC3)cc21] 1-benzyl-N-(2-cyclopropyl-4-methyl-5-oxo-4,5,6,7,8,9-hexahydropyrazolo[1,5-a][1,3]diazocin-6-yl)-1H-1,2,4-triazole-3-carboxamide | $^1$H NMR (400 MHz, DMSO-$d_6$) δ 8.80 (s, 1H), 8.21 (d, J = 7.1 Hz, 1H), 7.39-7.24 (m, 5H), 6.07 (s, 1H), 5.47 (s, 2H), 4.32-4.15 (m, 1H), 3.98-3.67 (m, 2H), 3.17 (s, 3H), 2.03-1.72 (m, 4H), 1.67-1.50 (m, 1H), 0.93-0.79 (m, 2H), 0.77-0.53 (m, 2H). | 378.2 4.59 min |
| Example 105 Method B | 0.262 | 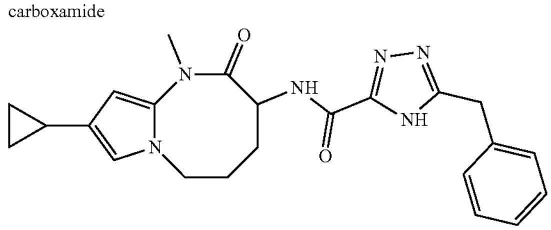 5-benzyl-N-(2-cyclopropyl-4-methyl-5-oxo-4,5,6,7,8,9-hexahydropyrazolo[1,5-a][1,3]diazocin-6-yl)-4H-1,2,4-triazole-3-carboxamide | $^1$H NMR (400 MHz, DMSO-$d_6$) δ 8.44 (s, OH), 8.28-8.17 (m, 1H), 7.42-7.18 (m, 4H), 6.68 (s, 1H), 6.07 (s, 1H), 4.29-4.18 (m, 1H), 4.09 (s, 2H), 3.93-3.72 (m, 2H), 3.17 (s, 3H), 2.03-1.74 (m, 4H), 1.65-1.50 (m, 1H), 0.91-0.81 (m, 2H), 0.71-0.56 (m, 2H). | 420.2 3.97 min |
| Example 106 Method B | 0.834 | 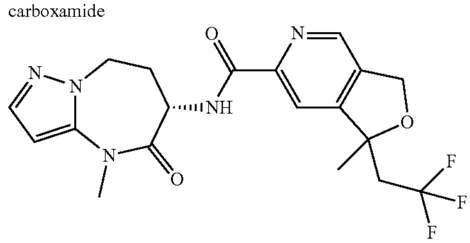 1-methyl-N-((S)-4-methyl-5-oxo-5,6,7,8-tetrahydro-4H-pyrazolo[1,5-a][1,3]diazepin-6-yl)-1-(2,2,2-trifluoroethyl)-1,3-dihydrofuro[3,4-c]pyridine-6-carboxamide | $^1$H NMR (400 MHz, DMSO-$d_6$) δ 8.94-8.88 (m, 1H), 8.67 (s, 1H), 8.14 (s, 1H), 7.51 (d, J = 2.0 Hz, 1H), 6.35 (d, J = 2.0 Hz, 1H), 5.19-5.11 (m, 2H), 4.45-4.33 (m, 2H), 4.31-4.16 (m, 1H), 3.27 (s, 3H), 3.14-3.03 (m, 1H), 2.99-2.87 (m, 1H), 2.78-2.62 (m, 1H), 2.41-2.29 (m, 1H), 1.50 (s, 3H). | 424.1 4.22 min |
| Example 107 Method B | 0.0697 | 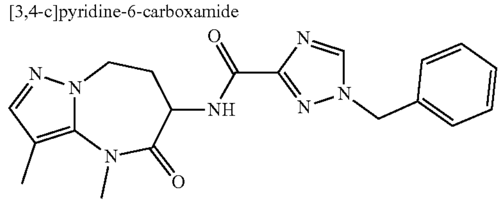 1-benzyl-N-(3,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.81 (s, 1H), 8.41 (d, J = 7.7 Hz, 1H), 7.44-7.25 (m, 6H), 5.48 (s, 2H), 4.34-4.12 (m, 3H), 3.21 (s, 3H), 2.61-2.53 (m, 1H), 2.29-2.19 (m, 1H), 2.01 (s, 3H). | 380.2 3.71 min |
| Example 108 Methods Z and G1 | 0.133 | 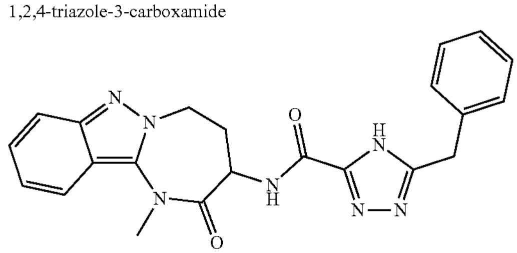 5-benzyl-N-(1-methyl-2-oxo-2,3,4,5-tetrahydro-1H-[1,3]diazepino[1,2-b]indazol-3-yl)-4H-1,2,4-triazole-3-carboxamide | $^1$H NMR (400 MHz, DMSO-$d_6$) δ 7.76 (dt, J = 8.5, 1.0 Hz, 1H), 7.62 (dt, J = 8.8, 0.9 Hz, 1H), 7.38-7.18 (m, 6H), 7.12 (ddd, J = 8.5, 6.6, 0.9 Hz, 1H), 4.61 (dd, J = 10.7, 4.1 Hz, 2H), 4.22 (dt, J = 11.4, 8.0 Hz, 1H), 4.11 (s, 2H), 3.47 (s, 3H), 2.18 (t, J = 7.4 Hz, 1H), 1.47 (d, J = 7.5 Hz, 1H). | 416.2 4.08 min |

TABLE 2-continued

| Compound Example # Method | RIP1 Ki (μM) | Structure and Name | $^1$H NMR Data | MS (m/z) |
|---|---|---|---|---|
| Example 109 Method G2 | 0.124 | 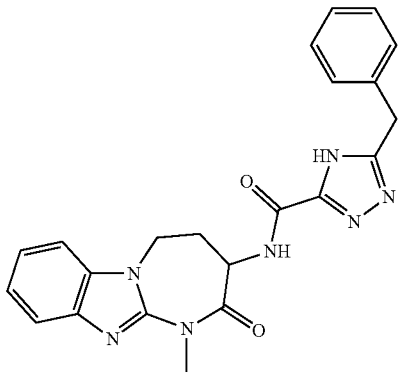 [SMILES: CN1C(=O)C(NC(=O)c2nnc(Cc3ccccc3)[nH]2)CCn2c1nc1ccccc12] 5-benzyl-N-(1-methyl-2-oxo-2,3,4,5-tetrahydro-1H-benzo[4,5]imidazo[1,2-a][1,3]diazepin-3-yl)-4H-1,2,4-triazole-3-carboxamide | $^1$H NMR (400 MHz, DMSO-$d_6$) δ 14.32 (s, 1H), 8.61 (s, 1H), 7.67-7.58 (m, 2H), 7.36-7.19 (m, 7H), 4.72-4.61 (m, 1H), 4.49 (dt, J = 11.5, 7.8 Hz, 1H), 4.19-3.98 (m, 3H), 3.42 (s, 3H), 2.76-2.60 (m, 1H), 2.61-2.51 (m, 1H). | 416.2 3.97 min |
| Example 110 Methods Z and G1 | 0.0652 | 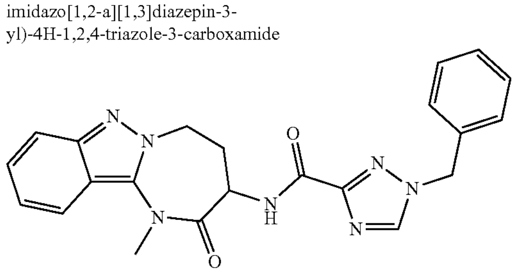 1-benzyl-N-(1-methyl-2-oxo-2,3,4,5-tetrahydro-1H-[1,3]diazepino[1,2-b]indazol-3-yl)-1H-1,2,4-triazole-3-carboxamide | $^1$H NMR (400 MHz, DMSO-$d_6$) δ 8.81 (s, 1H), 8.57 (d, J = 7.7 Hz, 1H), 7.76 (dt, J = 8.5, 1.0 Hz, 1H), 7.62 (dt, J = 8.8, 0.9 Hz, 1H), 7.43-7.25 (m, 6H), 7.12 (ddd, J = 8.5, 6.6, 0.9 Hz, 1H), 5.47 (s, 2H), 4.65 -4.56 (m, 2H), 4.22 (dt, J = 11.5, 7.9 Hz, 1H), 3.47 (s, 3H), 2.79-2.65 (m, 1H), 2.61-2.51 (m, 1H). | 416.2 4.26 min |
| Example 111 Method G1 | 0.126 | 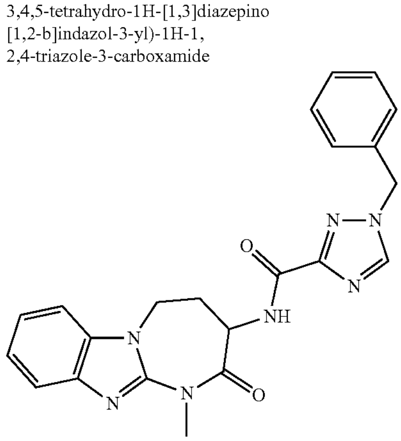 1-benzyl-N-(1-methyl-2-oxo-2,3,4,5-tetrahydro-1H-benzo[4,5]imidazo[1,2-a][1,3]diazepin-3-yl)-1H-1,2,4-triazole-3-carboxamide | $^1$H NMR (400 MHz, DMSO-$d_6$) δ 8.83 (s, 1H), 8.69 (d, J = 7.6 Hz, 1H), 7.68-7.56 (m, 2H), 7.43-7.17 (m, 8H), 5.49 (s, 2H), 4.71-4.60 (m, 1H), 4.48 (dt, J = 11.5, 7.7 Hz, 1H), 4.05 (ddd, J = 14.6, 12.8, 6.5 Hz, 1H), 3.42 (s, 3H), 2.76-2.62 (m, 1H), 2.56-2.45 (m, 1H). | 416.2 4.08 min |
| Example 112 Method G3 | 0.139 | 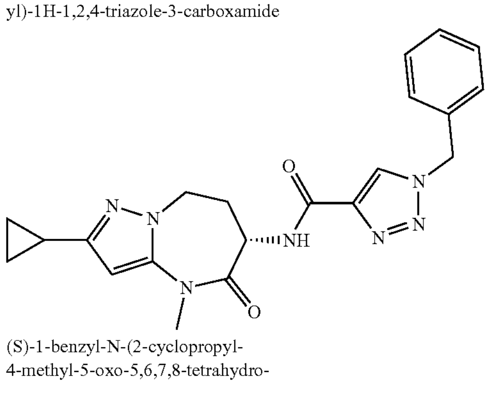 (S)-1-benzyl-N-(2-cyclopropyl-4-methyl-5-oxo-5,6,7,8-tetrahydro- | $^1$H NMR (400 MHz, DMSO-$d_6$) δ 8.66 (s, 1H), 8.60 (d, J = 7.9 Hz, 1H), 7.56-7.18 (m, 5H), 6.05 (s, 1H), 5.65 (s, 2H), 4.46-4.16 (m, 2H), 4.16-3.97 (m, 1H), 3.19 (s, 3H), 2.62-2.52 (m, 1H), 2.42-2.28 (m, 1H), 1.85 (tt, J = 8.4, 5.0 Hz, 1H), 0.91-0.80 (m, 2H), 0.73-0.59 (m, 2H). | 406.2 4.46 min |

TABLE 2-continued

| Compound Example # Method | RIP1 Ki (μM) | Structure and Name | $^1H$ NMR Data | MS (m/z) |
| --- | --- | --- | --- | --- |
| | | 4H-pyrazolo[1,5-a][1,3]diazepin-6-yl)-1H-1,2,3-triazole-4-carboxamide | | |
| Example 113 Methods G4 & G5 | 1.7 | 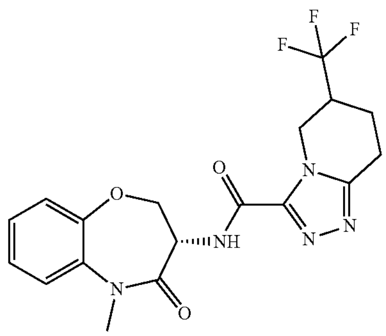 [SMILES: CN1C(=O)[C@@H](NC(=O)c2nnc3n2CC(C(F)(F)F)CC3)COc2ccccc21] N-((S)-5-methyl-4-oxo-2,3,4,5-tetrahydrobenzo[b][1,4]oxazepin-3-yl)-6-(trifluoromethyl)-5,6,7,8-tetrahydro-[1,2,4]triazolo[4,3-a]pyridine-3-carboxamide | $^1H$ NMR (400 MHz, DMSO-$d_6$) δ 8.96 (d, J = 8.0 Hz, 1H), 7.55-7.47 (m, 1H), 7.37-7.20 (m, 3H), 4.89-4.79 (m, 1H), 4.72-4.54 (m, 2H), 4.41 (ddd, J = 9.8, 7.6, 3.4 Hz, 1H), 4.06 (dd, J = 13.3, 10.4 Hz, 1H), 3.31 (s, 3H), 3.23-3.05 (m, 2H), 3.00-2.86 (m, 1H), 2.22-2.10 (m, 1H), 1.99-1.83 (m, 1H). | 410.1 4.56 min |
| Example 114 Method G6 | 0.0683 | 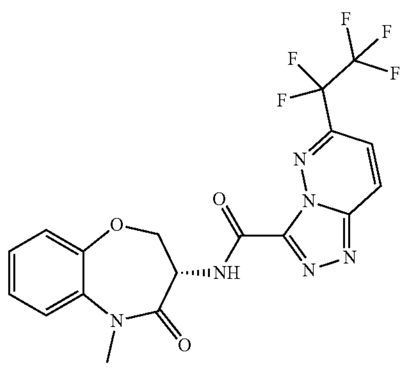 [SMILES: CN1C(=O)[C@@H](NC(=O)c2nnc3ccc(C(F)(F)C(F)(F)F)nn23)COc2ccccc21] (S)-N-(5-methyl-4-oxo-2,3,4,5-tetrahydrobenzo[b][1,4]oxazepin-3-yl)-6-(perfluoroethyl)-[1,2,4]triazolo[4,3-b]pyridazine-3-carboxamide | $^1H$ NMR (400 MHz, DMSO-$d_6$) δ 9.30 (d, J = 7.8 Hz, 1H), 8.90-8.79 (m, 1H), 7.93 (d, J = 9.8 Hz, 1H), 7.57-7.49 (m, 1H), 7.41-7.23 (m, 3H), 4.97 (dt, J = 11.4, 7.8 Hz, 1H), 4.62 (dd, J = 11.5, 9.9 Hz, 1H), 4.52 (dd, J = 9.9, 7.8 Hz, 1H), 3.35 (s, 3H). | 457.1 4.81 min |
| Example 115 Method G7 | 0.0049 | 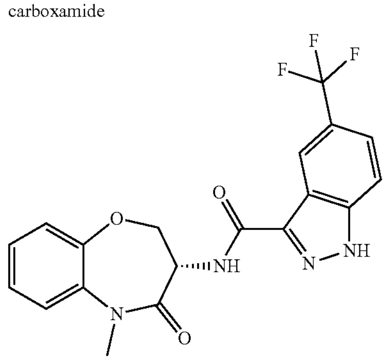 (S)-N-(5-methyl-4-oxo-2,3,4,5-tetrahydrobenzo[b][1,4]oxazepin-3-yl)-5-(trifluoromethyl)-1H-indazole-3-carboxamide | $^1H$ NMR (400 MHz, DMSO-$d_6$) δ 14.15 (s, 1H), 8.62 (d, J = 8.0 Hz, 1H), 8.55-8.28 (m, 1H), 7.91-7.83 (m, 1H), 7.75-7.68 (m, 1H), 7.56-7.49 (m, 1H), 7.40-7.22 (m, 3H), 4.96 (dt, J = 11.6, 7.8 Hz, 1H), 4.66 (dd, J = 11.6, 9.9 Hz, 1H), 4.48 (dd, J = 9.9, 7.7 Hz, 1H), 3.34 (s, 3H). | 405.1 5.43 min |

TABLE 2-continued

| Compound Example # Method | RIP1 Ki (μM) | Structure and Name | $^1$H NMR Data | MS (m/z) |
|---|---|---|---|---|
| Example 116 Method G13 | 0.371 | 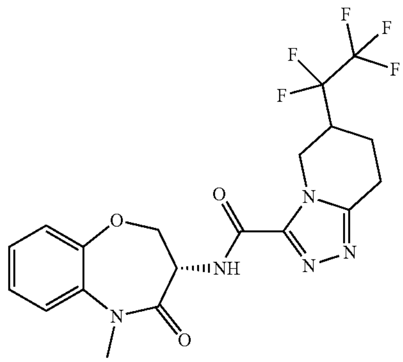 [SMILES: CN1C(=O)[C@@H](NC(=O)c2nnc3n2CC(C(F)(F)C(F)(F)F)CC3)COc2ccccc21] N-((S)-5-methyl-4-oxo-2,3,4,5-tetrahydrobenzo[b][1,4]oxazepin-3-yl)-6-(perfluoroethyl)-5,6,7,8-tetrahydro-[1,2,4]triazolo[4,3-a]pyridine-3-carboxamide | $^1$H NMR (400 MHz, DMSO-$d_6$) δ 8.95 (dd, J = 8.1, 1.3 Hz, 1H), 7.50 (ddd, J = 7.3, 1.9, 0.9 Hz, 1H), 7.38-7.26 (m, 2H), 7.26-7.20 (m, 1H), 4.89-4.78 (m, 1H), 4.72-4.59 (m, 2H), 4.40 (ddd, J = 9.8, 7.6, 3.3 Hz, 1H), 4.13-4.02 (m, 1H), 3.32 (s, 3H), 3.17-3.08 (m, 1H), 3.00-2.88 (m, 1H), 2.26-2.15 (m, 1H), 2.01-1.83 (m, 1H). | 460.1 5.00 min |
| Example 117 Method G8 | 0.0056 | 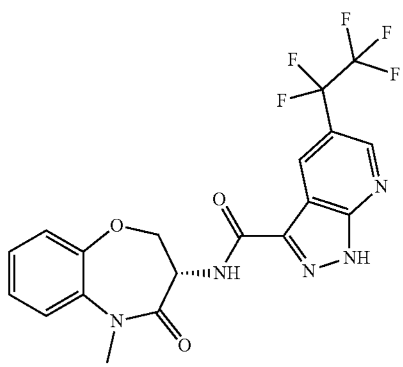 [SMILES: CN1C(=O)[C@@H](NC(=O)c2n[nH]c3ncc(C(F)(F)C(F)(F)F)cc23)COc2ccccc21] (S)-N-(5-methyl-4-oxo-2,3,4,5-tetrahydrobenzo[b][1,4]oxazepin-3-yl)-5-(perfluoroethyl)-1H-pyrazolo[3,4-b]pyridine-3-carboxamide | $^1$H NMR (400 MHz, DMSO-$d_6$) δ 14.87 (s, 1H), 8.92 (d, J = 2.2 Hz, 1H), 8.82 (d, J = 8.0 Hz, 1H), 8.68 (d, J = 2.2 Hz, 1H), 7.54-7.50 (m, 1H), 7.38-7.22 (m, 3H), 4.95 (dt, J = 11.6, 7.9 Hz, 1H), 4.69 (dd, J = 11.6, 9.9 Hz, 1H), 4.47 (dd, J = 9.9, 7.7 Hz, 1H), 3.33 (s, 3H). | 456.1 5.43 min |
| Example 118 Method G9 | 0.0504 | 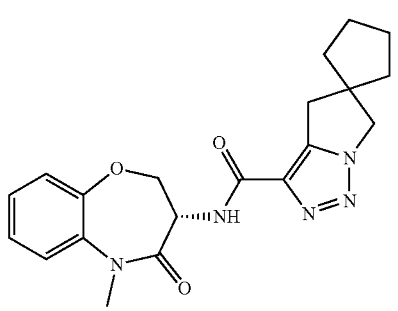 [SMILES: CN1C(=O)[C@@H](NC(=O)c2nnn3c2CC2(CCCC2)C3)COc2ccccc21] (S)-N-(5-methyl-4-oxo-2,3,4,5-tetrahydrobenzo[b][1,4]oxazepin-3-yl)-4'H,6'H-spiro[cyclopentane-1,5'-pyrrolo[1,2-c][1,2,3]triazole]-3'-carboxamide | $^1$H NMR (400 MHz, DMSO-$d_6$) δ 8.39 (d, J = 8.0 Hz, 1H), 7.53 7.46 1H), 7.38-7.19 (m, 3H), 4.84 (dt, J = 11.6, 7.9 Hz, 1H), 4.61 (dd, J = 11.6, 9.9 Hz, 1H), 4.40 (dd, J = 9.9, 7.7 Hz, 1H), 4.25 (d, J = 0.9 Hz, 2H), 3.31 (s, 3H), 2.88 (s, 2H), 1.80-1.62 (m, 8H). | 382.2 4.82 min |

TABLE 2-continued

| Compound Example # Method | RIP1 Ki (μM) | Structure and Name | $^1$H NMR Data | MS (m/z) |
| --- | --- | --- | --- | --- |
| Example 119 Method G9 | 0.201 | 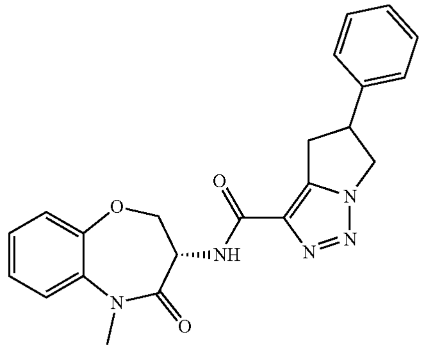 [SMILES: CN1C(=O)[C@@H](NC(=O)c2nnn3c2CC(c2ccccc2)C3)COc2ccccc21] N-((S)-5-methyl-4-oxo-2,3,4,5-tetrahydrobenzo[b][1,4]oxazepin-3-yl)-5-phenyl-5,6-dihydro-4H-pyrrolo[1,2-c][1,2,3]triazole-3-carboxamide | $^1$H NMR (400 MHz, DMSO-$d_6$) δ 8.45 (d, J = 8.1 Hz, 1H), 7.53-7.45 (m, 1H), 7.42-7.20 (m, 8H), 4.91-4.81 (m, 2H), 4.63 (ddd, J = 11.6, 9.9, 1.5 Hz, 1H), 4.49-4.31 (m, 3H), 3.48-3.38 (m, 1H), 3.32 (s, 3H), 3.00 (dd, J = 16.3, 8.4 Hz, 1H). | 404.1 4.93 min |
| Example 120 Method G9 | 2.1 | 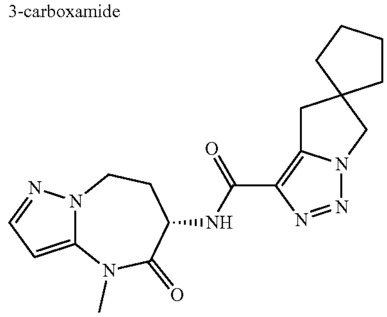 (S)-N-(4-methyl-5-oxo-5,6,7,8-tetrahydro-4H-pyrazolo[1,5-a][1,3]diazepin-6-yl)-4'H,6'H-spiro[cyclopentane-1,5'-pyrrolo[1,2-c][1,2,3]triazole]-3'-carboxamide | $^1$H NMR (400 MHz, DMSO-$d_6$) δ 8.49 (d, J = 7.9 Hz, 1H), 7.49 (d, J = 2.0 Hz, 1H), 6.32 (d, J = 2.0 Hz, 1H), 4.43-4.27 (m, 2H), 4.25 (d, J = 1.0 Hz, 2H), 4.19 (ddd, J = 14.6, 12.7, 6.6 Hz, 1H), 3.25 (s, 3H), 2.89 (s, 2H), 2.58 (ddd, J = 12.9, 8.0, 5.0 Hz, 1H), 2.47-2.35 (m, 1H), 1.81-1.59 (m, 8H). | 370.2 3.80 min |
| Example 121 Method G9 | 8.7 | 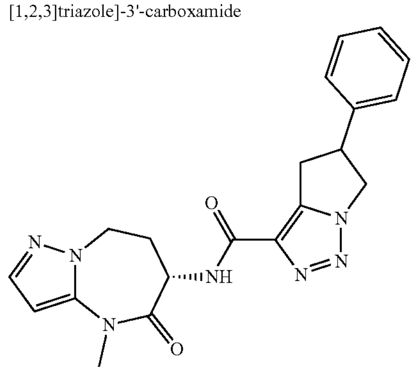 N-((S)-4-methyl-5-oxo-5,6,7,8-tetrahydro-4H-pyrazolo[1,5-a][1,3]diazepin-6-yl)-5-phenyl-5,6-dihydro-4H-pyrrolo[1,2-c][1,2,3]triazole-3-carboxamide | $^1$H NMR (400 MHz, DMSO-$d_6$) δ 8.55 (d, J = 7.8 Hz, 1H), 7.49 (d, J = 2.0 Hz, 1H), 7.42-7.32 (m, 4H), 7.32-7.24 (m, 1H), 6.32 (d, J = 2.0 Hz, 1H), 4.85 (ddd, J = 11.3, 8.1, 3.6 Hz, 1H), 4.50-4.27 (m, 3H), 4.20 (ddd, J = 14.6, 12.6, 6.6 Hz, 1H), 3.48-3.38 (m, 1H), 3.25 (d, J = 1.6 Hz, 3H), 3.01 (dd, J = 16.4, 8.3 Hz, 1H), 2.66-2.54 (m, 1H), 2.48-2.37 (m, 1H). | 392.2 3.97 min |
| Example 122 Method G10 | 0.0195 | 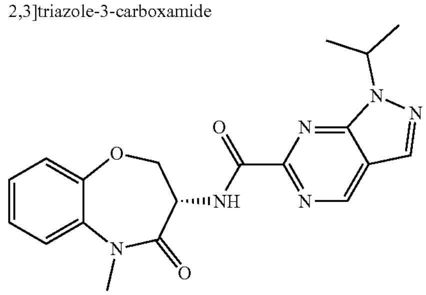 (S)-1-isopropyl-N-(5-methyl-4-oxo-2,3,4,5-tetrahydrobenzo[b] | $^1$H NMR (400 MHz, DMSO-$d_6$) δ 9.46 (s, 1H), 9.13 (d, J = 7.8 Hz, 1H), 8.51 (s, 1H), 7.58-7.49 (m, 1H), 7.39-7.24 (m, 3H), 5.27 (p, J = 6.7 Hz, 1H), 4.92 (dt, J = 11.1, 7.9 Hz, 1H), 4.65-4.49 (m, 2H), 3.35 (s, 3H), 1.53 (dd, J = 6.7, 0.8 Hz, 6H). | 381.1 4.44 min |

TABLE 2-continued

| Compound Example # Method | RIP1 Ki (μM) | Structure and Name | $^1$H NMR Data | MS (m/z) |
|---|---|---|---|---|
| | | [1,4]oxazepin-3-yl)-1H-pyrazolo [3,4-d]pyrimidine-6-carboxamide | | |
| Example 123 Method G11 | 0.268 | 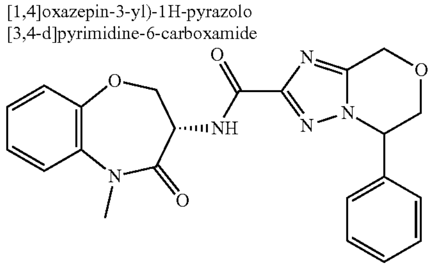 N-((S)-5-methyl-4-oxo-2,3,4,5-tetrahydrobenzo[b][1,4]oxazepin-3-yl)-5-phenyl-5,6-dihydro-8H-[1,2,4]triazolo[5,1-c][1,4] oxazine-2-carboxamide | $^1$H NMR (400 MHz, DMSO-$d_6$) δ 8.48 (d, J = 8.0 Hz, 1H), 7.54-7.46 (m, 1H), 7.43-7.16 (m, 8H), 5.65 (t, J = 4.5 Hz, 1H), 5.13 (d, J = 15.7 Hz, 1H), 5.04-4.96 (m, 1H), 4.81 (dt, J = 11.5, 7.9 Hz, 1H), 4.59 (dd, J = 11.6, 9.9 Hz, 1H), 4.44-4.31 (m, 2H), 3.30 (s, 3H). | 420.1 4.57 min |
| Example 124 Method G11 | 0.0768 | 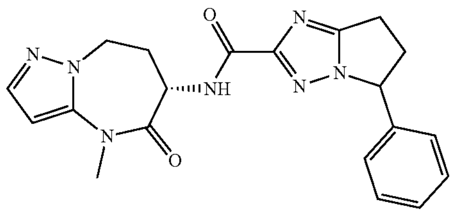 [SMILES: CN1C(=O)[C@@H](NC(=O)c2nc3n(n2)[C@@H](c2ccccc2)CC3)CCn2nccc21] N-((S)-4-methyl-5-oxo-5,6,7,8-tetrahydro-4H-pyrazolo[1,5-a] [1,3]diazepin-6-yl)-5-phenyl-6,7-dihydro-5H-pyrrolo[1,2-b][1,2,4] triazole-2-carboxamide | $^1$H NMR (400 MHz, DMSO-$d_6$) δ 8.50 (t, J = 7.5 Hz, 1H), 7.48 (d, J = 2.0 Hz, 1H), 7.44-7.32 (m, 3H), 7.27-7.20 (m, 2H), 6.33 (dd, J = 2.0, 1.0 Hz, 1H), 5.57 (dd, J = 8.2, 5.9 Hz, 1H), 4.41-4.24 (m, 2H), 4.24-4.12 (m, 1H), 3.24 (d, J = 1.1 Hz, 3H), 3.22-3.06 (m, 2H), 3.05-2.94 (m, 1H), 2.61-2.52 (m, 2H), 2.44-2.30 (m, 1H). | 392.2 3.73 min |
| Example 125 Method G12 | 0.891 | 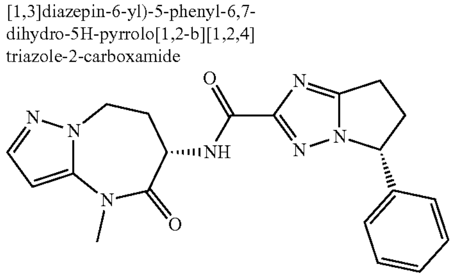 (R)-N-((S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b] [1,2,4]triazole-2-carboxamide | $^1$H NMR (400 MHz, DMSO-$d_6$) δ 8.51 (d, J = 7.8 Hz, 1H), 7.48 (d, J = 2.0 Hz, 1H), 7.44-7.32 (m, 3H), 7.28-7.20 (m, 2H), 6.33 (d, J = 2.0 Hz, 1H), 5.57 (dd, J = 8.2, 5.9 Hz, 1H), 4.41-4.32 (m, 1H), 4.32-4.23 (m, 1H), 4.23-4.13 (m, 1H), 3.24 (s, 3H), 3.21-3.14 (m, 1H), 3.14-3.04 (m, 1H), 3.04-2.93 (m, 1H), 2.63-2.52 (m, 2H), 2.37 (td, J = 12.5, 6.6 Hz, 1H). | 392.2 3.76 min |
| Example 126 Method G12 | 0.0241 | 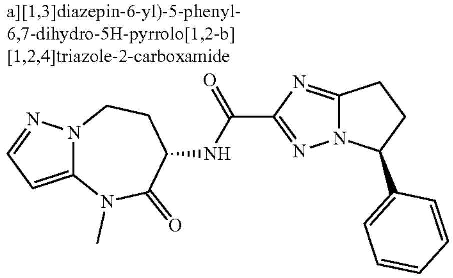 (S)-N-(S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide | $^1$H NMR (400 MHz, DMSO-$d_6$) δ 8.49 (d, J = 7.7 Hz, 1H), 7.48 (d, J = 2.0 Hz, 1H), 7.43-7.32 (m, 3H), 7.26-7.21 (m, 2H), 6.33 (d, J = 2.0 Hz, 1H), 5.57 (dd, J = 8.3, 5.8 Hz, 1H), 4.41-4.24 (m, 2H), 4.24-4.12 (m, 1H), 3.24 (s, 3H), 3.22-3.06 (m, 2H), 3.05-2.94 (m, 1H), 2.61-2.52 (m, 2H), 2.42-2.31 (m, 1H). | 392.2 3.76 min |
| Example 127 Method C1 | 0.237 | 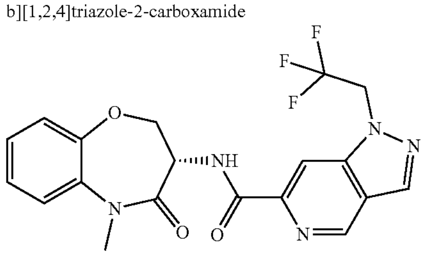 N-[(3S)-5-methyl-4-oxo-2,3-dihydro-1,5-benzoxazepin-3-yl]- | $^1$H NMR (400 MHz, DMSO-$d_6$) δ 9.26 (d, J = 1.2 Hz, 1H), 9.06 (d, J = 8.0 Hz, 1H), 8.59 (d, J = 0.8 Hz, 1H), 8.52 (bs, 1H), 7.57-7.47 (m, 1H), 7.40-7.24 (m, 3H), 5.75-5.60 (m, 2H), 4.93 (dt, J = 10.8, 8.0 Hz, 1H), 4.62-4.48 (m, 2H), 3.35 (s, 3H). | 420.1 5.04 min |

TABLE 2-continued

| Compound Example # Method | RIP1 Ki (μM) | Structure and Name | $^1$H NMR Data | MS (m/z) |
|---|---|---|---|---|
| | | 1-(2,2,2-trifluoroethyl)pyrazolo [4,3-c]pyridine-6-carboxamide | | |
| Example 128 Method C2 | 0.0614 | 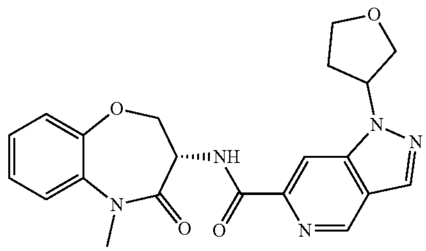 [SMILES: CN1C(=O)[C@@H](NC(=O)c2cc3c(cn2)cnn3C2CCOC2)COc2ccccc21] N-((S)-5-methyl-4-oxo-2,3,4,5-tetrahydrobenzo[b][1,4]oxazepin-3-yl)-1-(tetrahydrofuran-3-yl)-1H-pyrazolo[4,3-c]pyridine-6-carboxamide | $^1$H NMR (400 MHz, DMSO-d$_6$) δ 9.20 (d, J = 0.8 Hz, 1H), 9.02 (d, J = 8.0 Hz, 1H), 8.47-8.46 (m, 1H), 8.40-8.36 (m, 1H), 7.57-7.47 (m, 1H), 7.39-7.24 (m, 3H), 5.73-5.66 (m, 1H), 4.96-4.89 (m, 1H), 4.61-4.50 (m, 2H), 4.14-4.01 (m, 2H), 3.96-3.82 (m, 2H), 3.35 (s, 3H), 2.51-2.39 (m, 1H), 2.34-2.19 (m, 1H). | 408.2 4.49 min |
| Example 129 Method C3 | 0.388 | 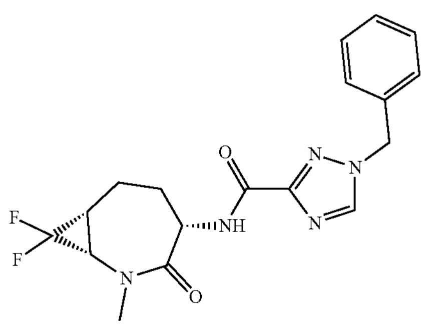 [SMILES: CN1C(=O)[C@@H](NC(=O)c2ncn(Cc3ccccc3)n2)CC[C@@H]2[C@H]1C2(F)F] 1-benzyl-N-((1S,4S,7R)-8,8-difluoro-2-methyl-3-oxo-2-azabicyclo [5.1.0]octan-4-yl)-1H-1,2,4-triazole-3-carboxamide | $^1$H NMR (400 MHz, DMSO-d$_6$) δ 8.81 (s, 1H), 8.19 (m, 2H), 7.45-7.20 (m, 5H), 5.49 (s, 2H), 5.00 (dt, J = 10.8, 7.2 Hz, 1H), 3.72-3.49 (m, 1H), 2.90 (s, 3H), 2.43-1.96 (m, 4H), 1.61 (m, 1H), 1.27 (m, 1H). | 376.1 4.18 min |
| Example 130 Method C3 | > 10 | 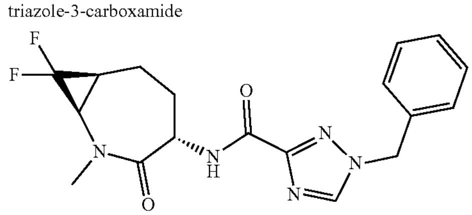 1-benzyl-N-((1R,4S,7S)-8,8-difluoro-2-methyl-3-oxo-2-azabicyclo [5.1.0]octan-4-yl)-1H-1,2,4-triazole-3-carboxamide | $^1$H NMR (400 MHz, DMSO-d$_6$) δ 8.82 (s, 1H), 8.58 (d, J = 4.4 Hz, 1H), 7.43-7.27 (m, 5H), 5.48 (s, 2H), 4.43-4.33 (m, 1H), 3.27-3.14 (m, 1H), 2.80 (s, 3H), 2.55-2.43 (m, 1H), 2.10-2.00 (m, 3H), 1.30-1.10 (m, 1H). | 376.1 3.90 min |
| Example 131 Methods C3 and C4 | 1.3 | 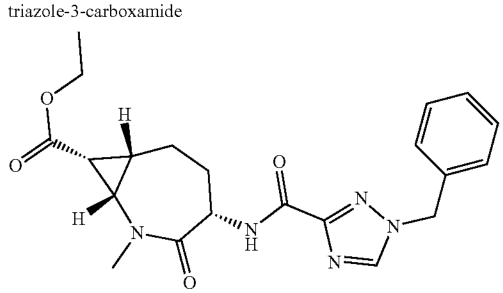 ethyl (1S,4S,7S,8R)-4-(1-benzyl-1H-1,2,4-triazole-3-carboxamido)-2-methyl-3-oxo-2-azabicyclo-[5.1.0]octane-8-carboxylate | $^1$H NMR (400 MHz, DMSO-d$_6$) δ 8.81 (s, 1H), 8.15 (d, J = 7.6 Hz, 1H), 7.46-7.19 (m, 4H), 5.49 (s, 2H), 5.07 (dt, J = 10.8, 7.2 Hz, 1H), 4.09 (m, 2H), 3.41-3.20 (m, 1H), 2.85 (s, 3H), 2.30-2.12 (m, 2H), 2.01-1.77 (m, 2H), 1.60-1.43 (m, 1H), 1.21 (t, J = 7.2 Hz, 3H), 1.15-0.95 (m, 1H). | 412.2 4.19 min |

TABLE 2-continued

| Compound Example # Method | RIP1 Ki (μM) | Structure and Name | $^{1}$H NMR Data | MS (m/z) |
|---|---|---|---|---|
| Example 132 Methods C3 and C4 | 5 | 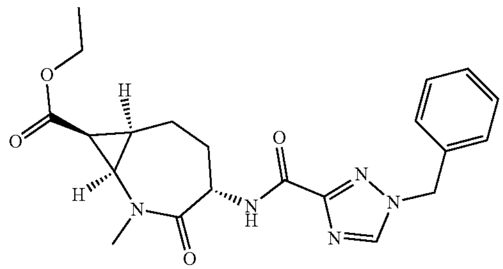 [SMILES: CCOC(=O)[C@H]1[C@H]2CC[C@H](NC(=O)c3ncn(Cc4ccccc4)n3)C(=O)N(C)[C@H]21] ethyl (1R,4S,7R,8S)-4-(1-benzyl-1H-1,2,4-triazole-3-carboxamido)-2-methyl-3-oxo-2-azabicyclo-[5.1.0]octane-8-carboxylate | $^{1}$H NMR (400 MHz, DMSO-$d_6$) δ 8.81 (s, 1H), 8.19 (d, J = 7.6 Hz, 1H), 7.43-7.27 (m, 5H), 5.49 (s, 2H), 4.98 (dt, J = 11.2, 7.6 Hz, 1H), 4.16-4.02 (m, 2H), 3.38-3.27 (m, 1H), 2.74 (s, 3H), 2.30-2.22 (m, 1H), 2.16-1.94 (m, 2H), 1.97-1.83 (m, 2H), 1.80-1.74 (m, 1H), 1.68-1.61 (m, 1H), 1.20 (t, J = 7.2 Hz, 3H). | 412.2 4.22 min |
| Example 133 Method X1 | 0.127 | 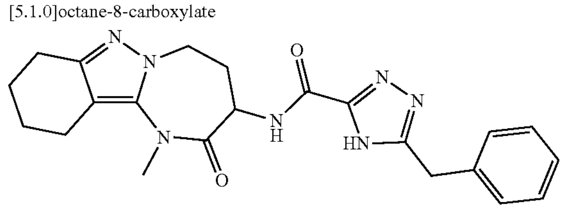 5-benzyl-N-(1-methyl-2-oxo-2,3,4,5,8,9,10,11-octahydro-1H-[1,3]diazepino[1,2-b]indazol-3-yl)-4H-1,2,4-triazole-3-carboxamide | $^{1}$H NMR (400 MHz, DMSO-$d_6$) δ 8.30 (d, J = 7.7 Hz, 1H), 7.38-7.16 5H), 4.35-4.08 (m, 3H), 4.06 (s, 2H), 3.19 (s, 3H), 2.65-2.51 (m, 3H), 2.49-2.40 (m, 2H), 2.27-2.16 (m, 1H), 1.87-1.59 (m, 4H). | 420.2 4.15 min |
| Example 134 Method X2 | 0.0736 | 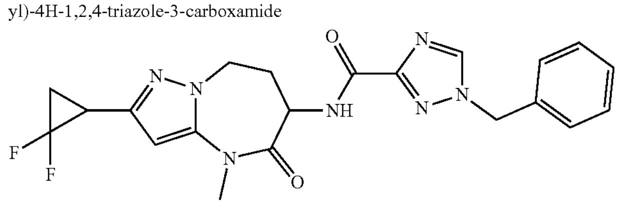 1-benzyl-N-(2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^{1}$H NMR (400 MHz, DMSO-$d_6$) δ 8.82 (s, 1H), 8.54 (d, J = 7.8 Hz, 1H), 7.44-7.25-(m, 5H), 6.34-6.23 (m, 1H), 5.48 (s, 2H), 4.36-4.25 (m, 2H), 4.23-4.09 (m, 1H), 3.22 (d, J = 2.1 Hz, 3H), 2.99-2.78 (m, 1H), 2.67-2.53 (m, 1H), 2.44-2.31 (m, 1H), 2.02-1.80 (m, 2H). | 442.2 4.36 min |
| Example 135 Method X3 | 0.39 | 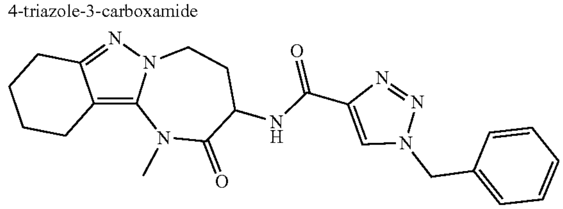 1-benzyl-N-(1-methyl-2-oxo-2,3,4,5,8,9,10,11-octahydro-1H-[1,3]diazepino[1,2-b]indazol-3-yl)-1H-1,2,3-triazole-4-carboxamide | $^{1}$H NMR (400 MHz, DMSO-$d_6$) δ 8.65 (s, 1H), 8.49 (d, J = 7.7 Hz, 1H), 7.46-7.25 (m, 5H), 5.65 (s, 2H), 4.41-4.03 (m, 3H), 3.18 (s, 3H), 2.59-2.51 (m, 3H), 2.48-2.40 (m, 2H), 2.35-2.22 (m, 1H), 1.86-1.57 (m, 4H). | 420.2 4.55 min |
| Example 136 Method X3 | 0.11 | 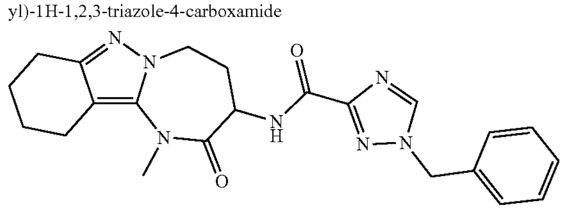 1-benzyl-N-(1-methyl-2-oxo-2,3,4,5,8,9,10,11-octahydro-1H-[1,3]diazepino[1,2-b]indazol-3-yl)-1H-1,2,4-triazole-3-carboxamide | $^{1}$H NMR (400 MHz, DMSO-$d_6$) δ 8.82 (s, 1H), 8.38 (d, J = 7.7 Hz, 1H), 7.46-7.24 (m, 5H), 5.48 (s, 2H), 4.37-4.06 (m, 3H), 3.19 (s, 3H), 2.66-2.52 (m, 3H), 2.48-2.39 (m, 2H), 2.32-2.17 (m, 1H), 1.87-1.59 (m, 4H). | 420.2 4.35 min |

TABLE 2-continued

| Compound Example # Method | RIP1 Ki (μM) | Structure and Name | $^1$H NMR Data | MS (m/z) |
|---|---|---|---|---|
| Example 137 Method X3 | 1.8 | 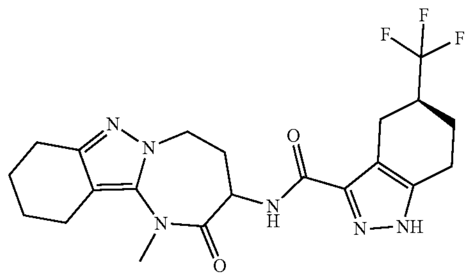 [SMILES: CN1C(=O)C(NC(=O)c2n[nH]c3c2C[C@@H](C(F)(F)F)CC3)CCn2nc3c(c21)CCCC3] (5S)-N-(1-methyl-2-oxo-2,3,4,5,8,9,10,11-octahydro-1H-[1,3]diazepino[1,2-b]indazol-3-yl)-5-(trifluoromethyl)-4,5,6,7-tetrahydro-1H-indazole-3-carboxamide | $^1$H NMR (400 MHz, DMSO-$d_6$) δ 12.97 (s, 1H), 7.97 (d, J = 7.8 Hz, 1H), 4.37-4.03 (m, 3H), 3.19 (s, 3H), 3.06-2.95 (m, 1H), 2.84-2.74 (m, 1H), 2.72-2.52 (m, 5H), 2.50-2.40 (m, 3H), 2.28-2.16 (m, 1H), 2.14-2.08 (m, 1H), 1.88-1.55 (m, 5H). | 451.2 4.84 min |
| Example 138 Method X4 | 3.7 | 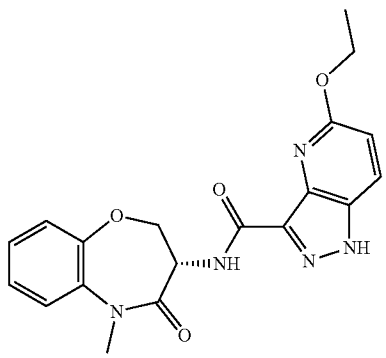 [SMILES: CCOc1ccc2[nH]nc(C(=O)N[C@H]3COc4ccccc4N(C)C3=O)c2n1] (S)-5-ethoxy-N-(5-methyl-4-oxo-2,3,4,5-tetrahydrobenzo[b][1,4]oxazepin-3-yl)-1H-pyrazolo[4,3-b]pyridine-3-carboxamide | $^1$H NMR (400 MHz, DMSO-$d_6$) δ 13.90 (bs, 1H), 9.15 (d, J = 7.1 Hz, 1H), 8.06 (d, J = 9.1 Hz, 1H), 7.54-7.46 (m, 1H), 7.40-7.23 (m, 3H), 6.92 (d, J = 9.1 Hz, 1H), 5.10-4.95 (m, 1H), 4.72-4.57 (m, 3H), 4.31 (dd, J = 11.3, 9.8 Hz, 1H), 3.37 (s, 3H), 1.44 (t, J = 7.0 Hz, 3H). | 382.1 4.80 min |
| Example 139 Method X5 | 0.0292 | 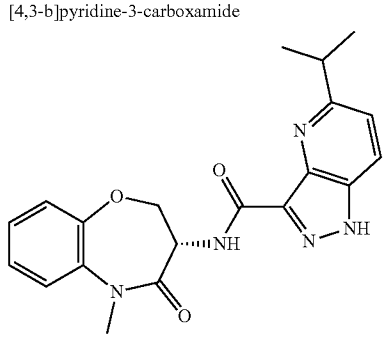 (S)-5-isopropyl-N-(5-methyl-4-oxo-2,3,4,5-tetrahydrobenzo[b][1,4]oxazepin-3-yl)-1H-pyrazolo[4,3-b]pyridine-3-carboxamide | $^1$H NMR (400 MHz, DMSO-$d_6$) δ 13.88 (bs, 1H), 9.65 (d, J = 7.2 Hz, 1H), 8.09 (d, J = 8.8 Hz, 1H), 7.55-7.48 (m, 1H), 7.46 (d, J = 8.8 Hz, 1H), 7.38-7.26 (m, 3H), 5.04 (dt, J = 11.3, 7.3 Hz, 1H), 4.66 (dd, J = 9.8, 7.4 Hz, 1H), 4.32 (dd, J = 11.3, 9.8 Hz, 1H), 3.37 (s, 3H), 3.30-3.24 (m, 1H), 1.41 (d, J = 6.8 Hz, 6H). | 380.2 4.92 min |
| Example 140 Method X6 | 0.316 | 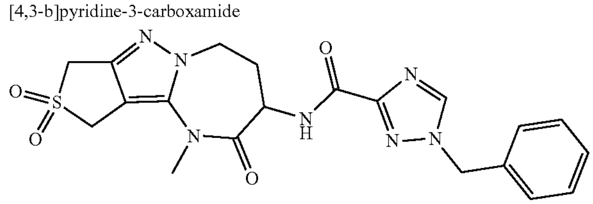 1-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-1H-1,2,4-triazole-3-carboxamide | $^1$H NMR (400 MHz, DMSO-$d_6$) δ 8.82 (s, 1H), 8.49 (d, J = 7.7 Hz, 1H), 7.46-7.23 (m, 5H), 5.49 (s, 2H), 4.56-4.33 (m, 6H), 4.34-4.19 (m, 1H), 3.20 (s, 3H), 2.73-2.60 (m, 1H), 2.41-2.28 (m, 1H). | 456.1 3.47 min |

TABLE 2-continued

| Compound Example # Method | RIP1 Ki (μM) | Structure and Name | $^1$H NMR Data | MS (m/z) |
|---|---|---|---|---|
| Example 141 Method X6 | 0.544 | 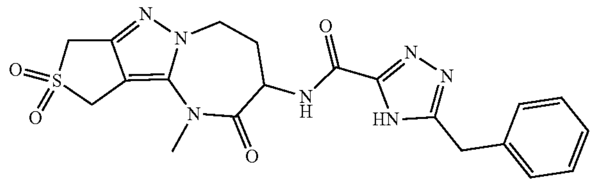 [SMILES: CN1C(=O)C(NC(=O)c2nnc(Cc3ccccc3)[nH]2)CCn2nc3c(c21)CS(=O)(=O)C3] 5-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-4H-1,2,4-triazole-3-carboxamide | $^1$H NMR (400 MHz, DMSO-$d_6$) δ 8.47 (bs, 1H), 7.40-7.17 (m, 5H), 4.56-4.33 (m, 6H), 4.33-4.20 (m, 1H), 4.10 (s, 2H), 3.20 (s, 3H), 2.75-2.59 (m, 1H), 2.41-2.29 (m, 1H). | 456.1 3.42 min |
| Example 142 Method X7 | 0.0658 | 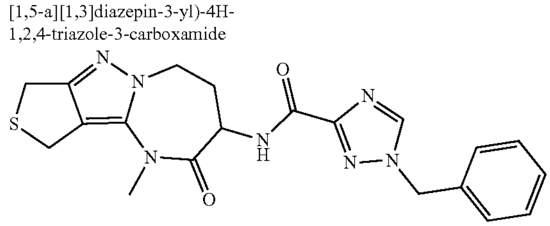 1-benzyl-N-(1-methyl-2-oxo-1,2,3,4,5,10-hexahydro-8H-thieno[3',4':3,4]pyrazolo[1,5-a][1,3]diazepin-3-yl)-1H-1,2,4-triazole-3-carboxamide | $^1$H NMR (400 MHz, DMSO-$d_6$) δ 8.82 (s, 1H), 8.45 (d, J = 7.7 Hz, 1H, NH), 7.44-7.26 (m, 5H), 5.48 (s, 2H), 4.40 (dt, J = 11.4, 7.8 Hz, 1H), 4.31-4.12 (m, 2H), 3.99-3.78 (m, 4H), 3.19 (s, 3H), 2.73-2.56 (m, 1H), 2.37-2.21 (m, 1H). | 424.1 3.99 min |
| Example 143 Method X8 | 0.0515 | 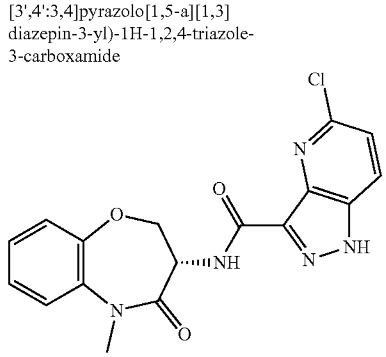 (S)-5-chloro-N-(5-methyl-4-oxo-2,3,4,5-tetrahydrobenzo[b][1,4]oxazepin-3-yl)-1H-pyrazolo[4,3-b]pyridine-3-carboxamide | $^1$H NMR (400 MHz, DMSO-$d_6$) δ 14.22 (bs, 1H), 8.75 (d, J = 7.3 Hz, 1H), 8.24 (d, J = 8.8 Hz, 1H), 7.54 (d, J = 8.8 Hz, 1H), 7.52 (dd, J = 6.9, 2.5 Hz, 1H), 7.39-7.24 (m, 3H), 4.97 (dt, J = 11.4, 7.4 Hz, 1H), 4.59 (dd, J = 9.9, 7.5 Hz, 1H), 4.44 (dd, J = 11.4, 9.9 Hz, 1H), 3.36 (s, 3H). | 372.1 4.37 min |
| Example 144 Method X9 | 0.248 | 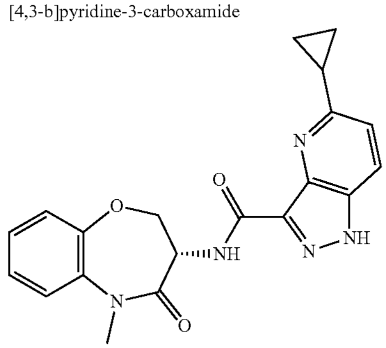 (S)-5-cyclopropyl-N-(5-methyl-4-oxo-2,3,4,5-tetrahydrobenzo[b][1,4]oxazepin-3-yl)-1H-pyrazolo[4,3-b]pyridine-3-carboxamide | $^1$H NMR (400 MHz, DMSO-$d_6$) δ 13.87 (s, 1H), 9.50 (d, J = 7.2 Hz, 1H), 8.03 (d, J = 8.7 Hz, 1H), 7.58-7.43 (m, 2H), 7.39-7.24 (m, 3H), 5.01 (dt, J = 11.2, 7.3 Hz, 1H), 4.64 (dd, J = 9.8, 7.4 Hz, 1H), 4.29 (dd, J = 11.3, 9.9 Hz, 1H), 3.38 (s, 3H), 2.34 (tt, J = 8.1, 4.8 Hz, 1H), 1.44-1.33 (m, 1H), 1.28-1.17 (m, 1H), 1.09 (dd, J = 8.1, 3.7 Hz, 2H). | 378.2 4.73 min |
| Example 145 Method X7 | 0.0786 | 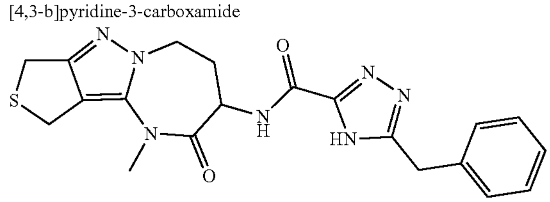 5-benzyl-N-(1-methyl-2-oxo-1,2,3,4,5,10-hexahydro-8H-thieno | $^1$H NMR (400 MHz, DMSO-$d_6$) δ 8.45 (s, 1H), 7.39-7.17 (m, 5H), 4.40 (dt, J = 11.4, 7.8 Hz, 1H), 4.31-4.13 (m, 2H), 4.10 (s, 2H), 4.00-3.80 (m, 4H), 3.19 (s, 3H), 2.74-2.56 (m, 1H), 2.35-2.24 (m, 1H). | 424.1 3.87 min |

TABLE 2-continued

| Compound Example # Method | RIP1 Ki (μM) | Structure and Name | $^1$H NMR Data | MS (m/z) |
|---|---|---|---|---|
| | | [3',4':3,4]pyrazolo[1,5-a][1,3]diazepin-3-yl)-4H-1,2,4-triazole-3-carboxamide | | |
| Example 146 Method KK and Method B | 0.301 | 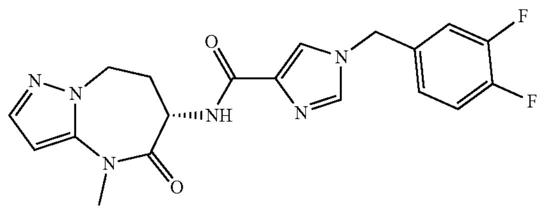 [SMILES: CN1C(=O)[C@@H](NC(=O)c2cn(Cc3ccc(F)c(F)c3)cn2)CCn2nccc21] (S)-1-(3,4-difluorobenzyl)-N-(4-methyl-5-oxo-5,6,7,8-tetrahydro-4H-pyrazolo[1,5-a][1,3]diazepin-6-yl)-1H-imidazole-4-carboxamide | $^1$H NMR (400 MHz, DMSO-$d_6$) δ 8.17 (d, J = 7.9 Hz, 1H), 7.95 (d, J = 2.3 Hz, 1H), 7.57-7.27 (m, 1H), 7.18-7.00 (m, 1H), 6.67 (d, J = 2.4 Hz, 1H), 6.33 (d, J = 2.0 Hz, 1H), 5.42 (s, 2H), 4.49-4.04 (m, 1H), 3.24 (s, 3H), 2.57 (d, J = 12.9 Hz, 2H), 2.41-2.21 (m, 1H), 2.07 (s, 1H). | 401.1 4.24 min |
| Example 147 CHIRAL METHODS | 0.0462 | 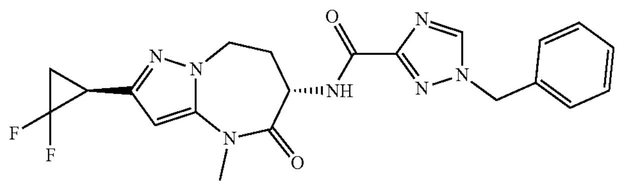 [SMILES: CN1C(=O)[C@@H](NC(=O)c2ncn(Cc3ccccc3)n2)CCn2nc([C@@H]3CC3(F)F)cc21] 1-benzyl-N-((S)-2-((S)-2,2-difluoro-cyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.82 (s, 1H), 8.54 (d, J = 7.7 Hz, 1H), 7.45-7.24 (m, 5H), 6.27 (d, J = 0.7 Hz, 1H), 5.48 (s, 2H), 4.39-4.22 (m, 2H), 4.16 (dd, J = 13.7, 6.9 Hz, 1H), 3.22 (s, 3H), 2.97-2.78 (m, 1H), 2.69-2.54 (m, 1H), 2.37-2.25 (m, 1H), 2.05-1.63 (m, 2H). | 442.1 4.36 min |
| Example 148 CHIRAL METHODS | 0.04 | 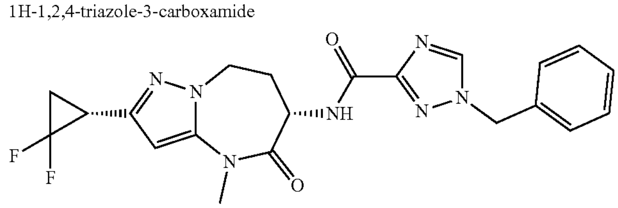 1-benzyl-N-((S)-2-((R)-2,2-difluoro-cyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.17 (d, J = 7.9 Hz, 1H), 7.95 (d, J = 2.3 Hz, 1H), 7.54-7.29 (m, 2H), 7.15-7.03 (m, 1H), 6.67 (d, J = 2.4 Hz, 1H), 6.33 (d, J = 2.0 Hz, 1H), 5.42 (s, 2H), 4.47-4.02 (m, 2H), 3.24 (s, 3H), 2.63-2.28 (m, 1H), 2.12-2.02 (m, 1H). | 442.2 4.38 min |
| Example 149 CHIRAL METHODS | 0.0643 | 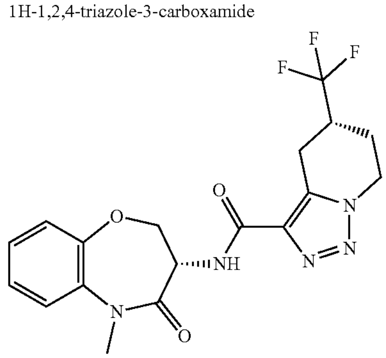 (R)-N-((S)-5-methyl-4-oxo-2,3,4,5-tetrahydrobenzo[b][1,4]oxazepin-3-yl)-5-(trifluoromethyl)-4,5,6,7-tetrahydro-[1,2,3]triazolo[1,5-a]pyridine-3-carboxamide | $^1$H NMR (400 MHz, DMSO-$d_6$) δ 8.50 (d, J = 8.0 Hz, 1H), 7.53-7.46 (m, 1H), 7.37-7.20 (m, 2H), 4.86 (dt, J = 11.5, 7.8 Hz, 1H), 4.64 (dd, J = 11.6, 9.9 Hz, 1H), 4.45-4.26 (m, 2H), 3.31 (s, 2H), 3.45-3.17 (m, 3H), 3.10 (s, 1H), 2.84 (dd, J = 17.2, 10.8 Hz, 1H), 2.34-2.25 (m, 1H), 2.13-1.97 (m, 1H). | 410 4.90 min |

TABLE 2-continued

| Compound Example # Method | RIP1 Ki (μM) | Structure and Name | $^1$H NMR Data | MS (m/z) |
|---|---|---|---|---|
| Example 150 CHIRAL METHODS | 0.125 | 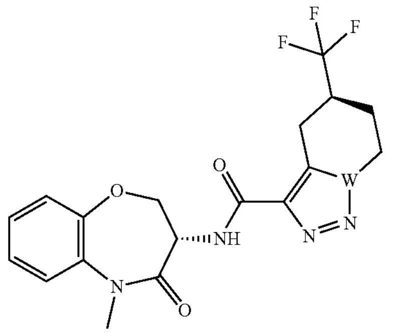 (S)-N-((S)-5-methyl-4-oxo-2,3,4,5-tetrahydrobenzo[b][1,4]oxazepin-3-yl)-5-(trifluoromethyl)-4,5,6,7-tetrahydro-[1,2,3]triazolo[1,5-a]pyridine-3-carboxamide | $^1$H NMR (400 MHz, DM50-$d_6$) δ 8.50 (d, J = 8.1 Hz, 1H), 7.53-7.46 (m, 1H), 7.37-7.20 (m, 3H), 4.86 (dt, J = 11.5, 7.8 Hz, 1H), 4.68-4.57 (m, 2H), 4.40 (dd, J = 9.9, 7.7 Hz, 1H), 4.37-4.24 (m, 1H), 3.47-3.16 (m, 3H), 3.07 (s, 2H), 2.84 (dd, J = 17.3, 10.8 Hz, 1H), 2.34-2.26 (m, 1H), 2.15-1.99 (m, 1H). | 410.1 4.86 min |
| Example 151 CHIRAL METHODS | 0.0266 | 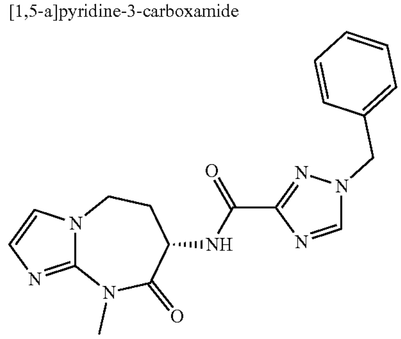 (S)-1-benzyl-N-(9-methyl-8-oxo-6,7,8,9-tetrahydro-5H-imidazo-[1,2-a][1,3]diazepin-7-yl)-1H-1,2,4-triazole-3-carboxamide | $^1$H NMR (400 MHz, DMSO-$d_6$) δ 8.82 (s, 1H), 8.53 (d, J = 7.8 Hz, 1H), 7.43-7.35 (m, 1H), 7.40-7.26 (m, 4H), 7.13 (d, J = 1.4 Hz, 1H), 6.88 (d, J = 1.4 Hz, 1H), 5.48 (s, 2H), 4.34-4.20 (m, 2H), 4.00-3.84 (m, 1H), 3.25 (s, 3H), 2.64-2.50 (m, 1H), 2.41-2.28 (m, 1H). | 366.2 2.83 min |
| Example 152 CHIRAL METHODS | 0.106 | 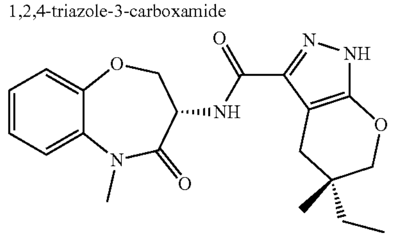 (R)-5-ethyl-5-methyl-N-((S)-5-methyl-4-oxo-2,3,4,5-tetrahydro-benzo[b][1,4]oxazepin-3-yl)-1,4,5,7-tetrahydropyrano[3,4-c]pyrazole-3-carboxamide | $^1$H NMR (400 MHz, DMSO-$d_6$) δ 12.99 (s, 1H), 7.99 (d, J = 8.0 Hz, 1H), 7.49 (dd, J = 7.5, 2.1 Hz, 1H), 7.37-7.19 (m, 2H), 4.89-4.77 (m, 1H), 4.61 (s, 2H), 4.57-4.47 (m, 1H), 4.46-4.36 (m, 1H), 2.52 (s, 2H), 1.60-1.39 (m, 1H), 1.08 (s, 3H), 0.91-0.82 (m, 3H). | 385.2 4.65 min |
| Example 153 CHIRAL METHODS | 0.414 | 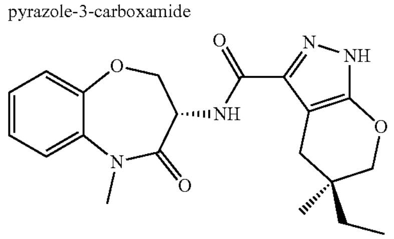 (S)-5-ethyl-5-methyl-N-((S)-5-methyl-4-oxo-2,3,4,5-tetrahydro-benzo[b][1,4]oxazepin-3-yl)-1,4,5,7-tetrahydropyrano[3,4-c]pyrazole-3-carboxamide | $^1$H NMR (400 MHz, DMSO-$d_6$) δ 12.99 (s, 1H), 7.99 (d, J = 8.0 Hz, 1H), 7.52-7.45 (m, 1H), 7.37-7.27 (m, 1H), 7.31-7.19 (m, 1H), 4.89-4.77 (m, 1H), 4.68-4.48 (m, 2H), 4.51-4.36 (m, 1H), 3.32 (s, 2H), 3.45-3.19 (m, 2H), 2.54 (s, 1H), 1.60-1.38 (m, 1H), 1.08 (s, 2H), 0.91-0.82 (m, 2H). | 385.2 4.66 min |

TABLE 2-continued

| Compound Example # Method | RIP1 Ki (μM) | Structure and Name | $^1$H NMR Data | MS (m/z) |
|---|---|---|---|---|
| Example 154 CHIRAL METHODS | 0.0415 | 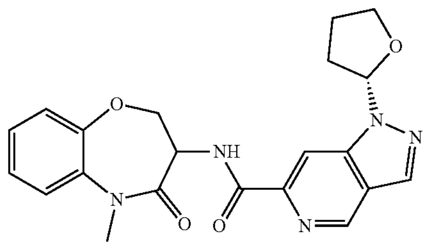 [SMILES: CN1C(=O)C(NC(=O)c2cc3c(cn2)cnn3[C@@H]2CCCO2)COc2ccccc21] N-(5-methyl-4-oxo-2,3,4,5-tetrahydro-benzo[b][1,4]oxazepin-3-yl)-1-((R)-tetrahydrofuran-3-yl)-1H-pyrazolo[4,3-c]pyridine-6-carboxamide | $^1$H NMR (400 MHz, DMSO-$d_6$) δ 9.20 (d, J = 1.1 Hz, 1H), 9.02 (d, J = 7.8 Hz, 1H), 8.52-8.41 (m, 1H), 8.37 (t, J = 1.1 Hz, 1H), 7.58-7.45 (m, 1H), 7.38-7.19 (m, 4H), 5.70 (dt, J = 6.8, 3.9 Hz, 1H), 5.01-4.80 (m, 1H), 4.62-4.41 (m, 2H), 4.13-3.99 (m, 3H), 3.97-3.81 (m, 3H), 2.47-2.37 (m, 1H), 2.35-2.13 (m, 1H). | 408.2 4.38 min |
| Example 155 CHIRAL METHODS | 0.0382 | 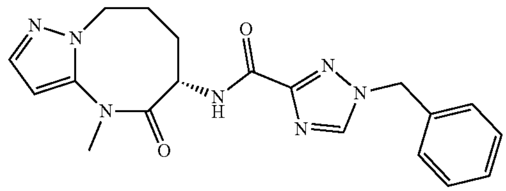 [SMILES: CN1C(=O)[C@@H](NC(=O)c2ncn(Cc3ccccc3)n2)CCCn2nccc21] (S)-1-benzyl-N-(4-methyl-5-oxo-4,5,6,7,8,9-hexahydropyrazolo[1,5-a][1,3]diazocin-6-yl)-1H-1,2,4-triazole-3-carboxamide | $^1$H NMR (400 MHz, DMSO-$d_6$) δ 8.80 (s, 1H), 8.23 (d, J = 7.0 Hz, 1H), 7.56 (d, J = 2.0 Hz, 1H), 7.42-7.18 (m, 5H), 6.35 (d, J = 2.0 Hz, 1H), 5.47 (s, 2H), 4.35 (dd, J = 14.5, 5.5 Hz, 1H), 3.99-3.74 (m, 3H), 3.21 (s, 3H), 2.09-1.48 (m, 3H). | 380.2 3.56 min |
| Example 156 CHIRAL METHODS | 0.0683 | 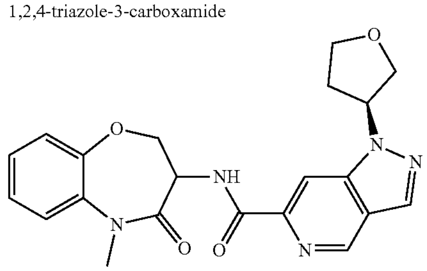 N-(5-methyl-4-oxo-2,3,4,5-tetra-hydrobenzo[b][1,4]oxazepin-3-yl)-1-((S)-tetrahydrofuran-3-yl)-1H-pyrazolo[4,3-c]pyridine-6-carboxamide | $^1$H NMR (400 MHz, DMSO-$d_6$) δ 9.20 (d, J = 1.1 Hz, 1H), 9.02 (d, J = 7.9 Hz, 1H), 8.54-8.42 (m, 1H), 8.37 (t, J = 1.1 Hz, 1H), 7.57-7.44 (m, 1H), 7.41-7.18 (m, 4H), 5.76-5.57 (m, 1H), 4.91 (dd, J = 10.2, 8.0 Hz, 1H), 4.61-4.46 (m, 3H), 4.16-3.99 (m, 3H), 3.97-3.74 (m, 3H), 2.41-2.00 (m, 1H). | 408.1 4.41 min |
| Example 157 CHIRAL METHODS | 0.0562 | 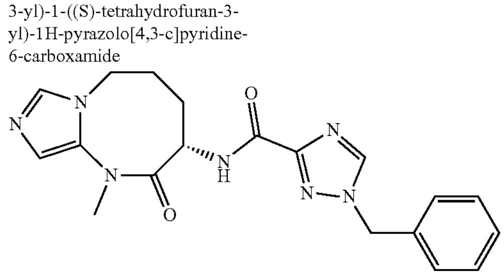 (S)-1-benzyl-N-(1-methyl-2-oxo-1,2,3,4,5,6-hexahydroimidazo[1,5-a][1,3]diazocin-3-yl)-1H-1,2,4-triazole-3-carboxamide | $^1$H NMR (400 MHz, DMSO-$d_6$) δ 8.80 (s, 1H), 8.24 (d, J = 7.0 Hz, 1H), 7.56 J = 2.0 Hz, 1H), 7.45-7.14 (m, 5H), 6.36 (d, J = 2.0 Hz, 1H), 5.47 (s, 2H), 4.08-3.71 (m, 3H), 3.21 (s, 4H), 2.01 (dd, J = 14.8, 4.8 Hz, 1H), 1.86 (d, J = 3.9 Hz, 1H), 1.61 (dd, J = 16.0, 11.2 Hz, 1H). | 380.2 3.85 min |
| Example 158 CHIRAL METHODS | 0.9855 | 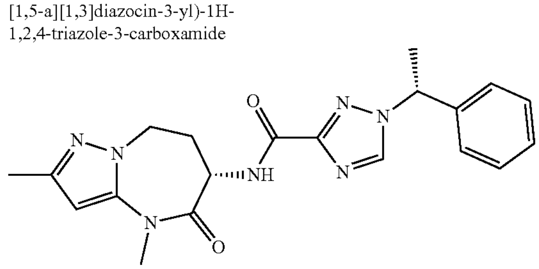 N-((S)-2,4-dimethyl-5-oxo-5,6,7,8-tetrahydro-4H-pyrazolo[1,5-a][1,3]diazepin-6-yl)-1-((R)-1-phenylethyl)-1H-1,2,4-triazole-3-carboxamide | $^1$H NMR (400 MHz, DMSO-$d_6$) δ 8.86 (s, 1H), 8.49 (d, J = 7.8 Hz, 1H), 7.42-7.26 (m, 4H), 6.12 (s, 1H), 5.86-5.76 (m, 1H), 4.38-4.21 (m, 2H), 4.17-4.03 (m, 1H), 3.38-3.23 (m, 2H), 3.21 (s, 2H), 2.66-2.50 (m, 1H), 2.39-2.26 (m, 1H), 2.16 (d, J = 0.5 Hz, 2H), 1.85 (d, J = 7.0 Hz, 3H). | 394.2 3.95 min |

TABLE 2-continued

| Compound Example # Method | RIP1 Ki (μM) | Structure and Name | $^1$H NMR Data | MS (m/z) |
|---|---|---|---|---|
| Example 159 CHIRAL METHODS Spiro is arbitrarily assigned | 0.3267 | 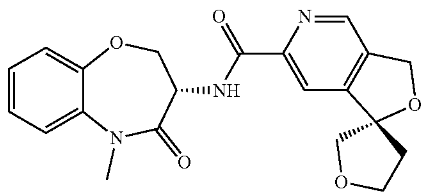 [SMILES: CN1C(=O)[C@@H](NC(=O)c2cc3c(cn2)CO[C@@]32CCOC2)COc2ccccc21] (S)-N-((S)-5-methyl-4-oxo-2,3,4,5-tetrahydrobenzo[b][1,4]oxazepin-3-yl)-4,5-dihydro-2H,3'H-spiro[furan-3,1'-furo[3,4-c]pyridine]-6'-carboxamide | $^1$H NMR (400 MHz, DMSO-$d_6$) δ 8.88 (d, J = 7.9 Hz, 1H), 8.74-8.63 (m, 1H), 8.00 (d, J = 1.0 Hz, 1H), 7.56-7.45 (m, 1H), 7.40-7.15 (m, 3H), 5.14 (d, J = 1.2 Hz, 2H), 5.02-4.79 (m, 1H), 4.65-4.40 (m, 2H), 4.09-3.73 (m, 4H), 3.21 (s, 3H), 2.42-2.03 (m, 2H). | 396.1 4.29 min |
| Example 160 CHIRAL METHODS | 0.0245 | 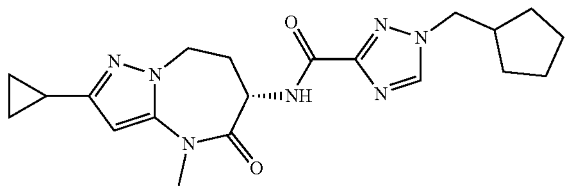 [SMILES: CN1C(=O)[C@@H](NC(=O)c2ncn(CC3CCCC3)n2)CCn2nc(C3CC3)cc21] (S)-1-(cyclopentylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.67 (s, 1H), 8.47 (d, J = 7.8 Hz, 1H), 6.06 (s, 1H), 4.38-4.19 (m, 2H), 4.16 (d, J = 7.5 Hz, 2H), 3.39-3.16 (m, 4H), 3.21 (s, 3H), 2.67-2.51 (m, 1H), 2.45-2.26 (m, 2H), 1.91-1.79 (m, 1H), 1.65-1.47 (m, 2H), 1.28-1.18 (m, 2H), 0.92-0.80 (m, 2H), 0.75-0.60 (m, 2H). | 398.2 4.35 min |
| Example 161 CHIRAL METHODS | 0.0089 | 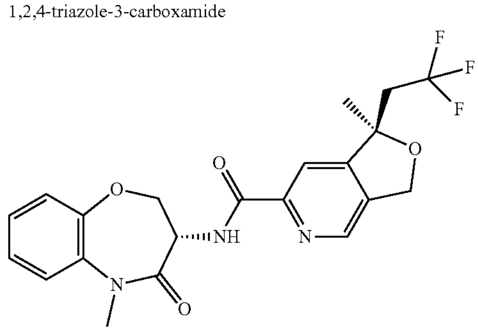 (R)-1-methyl-N-((S)-5-methyl-4-oxo-2,3,4,5-tetrahydrobenzo[b][1,4]oxazepin-3-yl)-1-(2,2,2-trifluoroethyl)-1,3-dihydrofuro[3,4-c]pyridine-6-carboxamide | $^1$H NMR (400 MHz, DMSO-$d_6$) δ 8.89 (d, J = 7.9 Hz, 1H), 8.68 (q, J = 0.8 Hz, 1H), 8.14 (d, J = 1.0 Hz, 1H), 7.55-7.48 (m, 1H), 7.39-7.23 (m, 3H), 5.22-5.12 (m, 2H), 4.94-4.83 (m, 1H), 4.62-4.52 (m, 1H), 4.54-4.45 (m, 1H), 3.34 (s, 3H), 3.18-3.01 (m, 1H), 3.03-2.85 (m, 1H), 1.50 (s, 3H). | 436.1 5.29 min |
| Example 162 S lactam CHIRAL METHODS | 0.0363 | 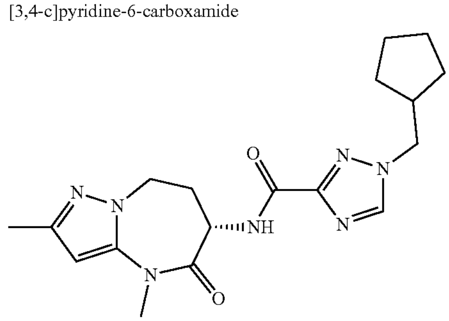 (S)-1-(cyclopentylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.67 (s, 1H), 8.47 (d, J = 7.8 Hz, 1H), 6.13 (s, 1H), 4.43-3.97 (m, 5H), 3.22 (s, 3H), 2.72-2.52 (m, 1H), 2.44-2.24 (m, 2H), 2.17 (d, J = 0.5 Hz, 3H), 1.73-1.42 (m, 6H), 1.32-1.11 (m, 2H). | 372.2 3.95 min |

TABLE 2-continued

| Compound Example # Method | RIP1 Ki (μM) | Structure and Name | $^1H$ NMR Data | MS (m/z) |
|---|---|---|---|---|
| Example 163 CHIRAL METHODS | 0.0223 | 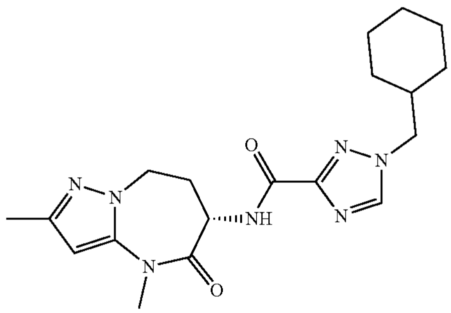 [SMILES: Cc1cc2n(n1)CC[C@H](NC(=O)c1ncn(CC3CCCCC3)n1)C(=O)N2C] (S)-1-(cyclohexylmethyl)-N-(2,4-dimethyl-5-oxo-5,6,7,8-tetrahydro-4H-pyrazolo[1,5-a][1,3] diazepin-6-yl)-1H-1,2,4-triazole-3-carboxamide | $^1H$ NMR (400 MHz, DM50-$d_6$) δ 8.63 (s, 1H), 8.47 (d, J = 7.8 Hz, 1H), 4.39-4.21 (m, 2H), 4.15-4.05 (m, 3H), 3.56-3.40 (m, 1H), 3.22 (s, 3H), 2.67-2.51 (m, 1H), 2.43-2.27 (m, 1H), 2.17 (s, 3H), 1.63 (dd, J = 23.2, 10.8 Hz, 3H), 1.50 (d, J = 12.6 Hz, 2H), 1.23-1.12 (m, 3H), 1.01-0.87 (m, 2H). | 386.2 4.27 min |
| Example 164 S-enantiomer CHIRAL METHODS | 0.0245 | 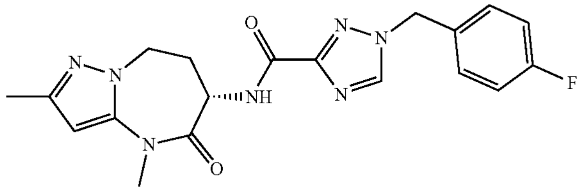 [SMILES: Cc1cc2n(n1)CC[C@H](NC(=O)c1ncn(Cc3ccc(F)cc3)n1)C(=O)N2C] (S)-N-(2,4-dimethyl-5-oxo-5,6,7,8-tetrahydro-4H-pyrazolo [1,5-a][1,3]diazepin-6-yl)-1-(4-fluorobenzyl)-1H-1,2,4-triazole-3-carboxamide | $^1H$ NMR (400 MHz, DMSO-$d_6$) δ 8.80 (s, 1H), 8.49 (d, J = 7.8 Hz, 1H), 7.43-7.33 (m, 2H), 7.26-7.15 (m, 2H), 6.12 (s, 1H), 5.47 (s, 2H), 4.37-4.20 (m, 2H), 4.17-4.03 (m, 1H), 3.21 (s, 3H), 2.65-2.51 (m, 1H), 2.38-2.26 (m, 1H), 2.16 (d, J = 0.5 Hz, 3H). | 398.2 3.81 min |
| Example 165 CHIRAL METHODS | 0.0474 | 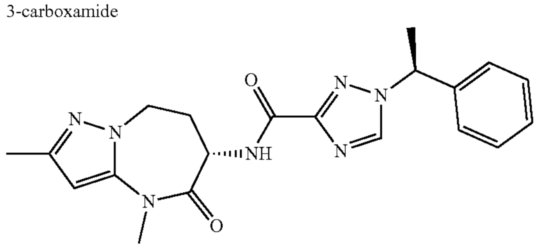 N-((S)-2,4-dimethyl-5-oxo-5,6,7,8-tetrahydro-4H-pyrazolo[1,5-a][1,3]diazepin-6-yl)-1-((S)-1-phenylethyl)-1H-1,2,4-triazole-3-carboxamide | $^1H$ NMR (400 MHz, DMSO-$d_6$) δ 8.86 (s, 1H), 8.49 (d, J = 7.8 Hz, 1H), 7.42-7.26 (m, 5H), 6.12 (s, 1H), 5.81 (q, J = 7.1 Hz, 1H), 4.38-4.21 (m, 2H), 4.17-4.03 (m, 1H), 3.21 (s, 3H), 2.66-2.50 (m, 1H), 2.43-2.24 (m, 1H), 2.16 (d, J = 0.5 Hz, 3H), 1.86 (d, J = 7.1 Hz, 3H). | 394.2 3.95 min |
| Example 166 CHIRAL METHODS | 0.0200 | 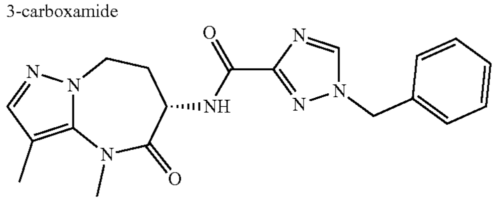 (S)-1-benzyl-N-(3,4-dimethyl-5-oxo-5,6,7,8-tetrahydro-4H-pyrazolo[1,5-a][1,3]diazepin-6-yl)-1H-1,2,4-triazole-3-carboxamide | $^1H$ NMR (400 MHz, DMSO-$d_6$) δ 8.81 (s, 1H), 8.42 (d, J = 7.6 Hz, 1H), 7.42-7.26 (m, 5H), 5.48 (s, 2H), 4.33-4.10 (m, 2H), 3.38-3.24 (m, 2H), 3.21 (s, 3H), 2.61-2.50 (m, 1H), 2.31-2.14 (m, 1H), 2.01 (d, J = 0.6 Hz, 3H). | 380.2 3.74 min |
| Example 167 S-enantiomer CHIRAL METHODS | 7.6824 | 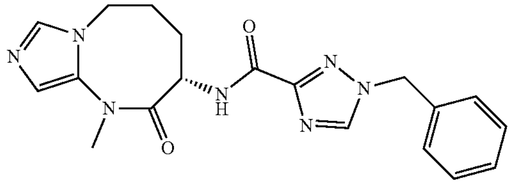 [SMILES: CN1C(=O)[C@@H](NC(=O)c2ncn(Cc3ccccc3)n2)CCCn2cncc21] (S)-1-benzyl-N-(1-methyl-2-oxo-1,2,3,4,5,6-hexahydroimidazo [1,5-a][1,3]diazocin-3-yl)-1H-1,2,4-triazole-3-carboxamide | $^1H$ NMR (400 MHz, DM50-$d_6$) δ 8.80 (s, 1H), 8.24 (d, J = 7.1 Hz, 1H), 7.56 (d, J = 2.0 Hz, 1H), 7.42-7.25 (m, 4H), 6.36 (d, J = 2.0 Hz, 1H), 5.47 (s, 2H), 4.40-4.30 (m, 1H), 3.96-3.80 (m, 2H), 3.44-3.27 (m, 1H), 3.21 (s, 2H), 2.10-1.96 (m, 1H), 1.91-1.74 (m, 2H), 1.60-1.55 (m, 1H). | 380.2 3.59 min |

TABLE 2-continued

| Compound Example # Method | RIP1 Ki (μM) | Structure and Name | $^1$H NMR Data | MS (m/z) |
|---|---|---|---|---|
| Example 168 CHIRAL METHODS | 0.2692 | 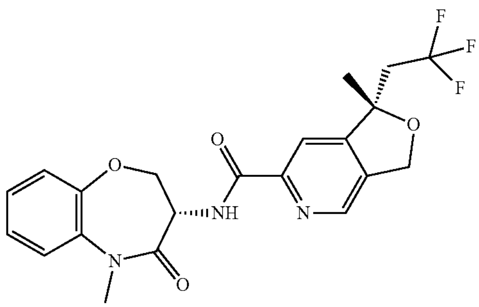 [SMILES: CN1C(=O)[C@@H](NC(=O)c2cc3c(cn2)CO[C@@]3(C)CC(F)(F)F)COc2ccccc21] (S)-1-methyl-N-((S)-5-methyl-4-oxo-2,3,4,5-tetrahydrobenzo[b][1,4]oxazepin-3-yl)-1-(2,2,2-trifluoroethyl)-1,3-dihydrofuro[3,4-c]pyridine-6-carboxamide | $^1$H NMR (400 MHz, DMSO-$d_6$) δ 8.89 (d, J = 8.0 Hz, 1H), 8.72-8.65 (m, 1H), 8.14 (d, J = 1.0 Hz, 1H), 7.55-7.46 (m, 1H), 7.39-7.23 (m, 3H), 5.22-5.09 (m, 2H), 4.94-4.83 (m, 1H), 4.56 (dd, J = 11.3, 9.9 Hz, 1H), 4.49 (dd, J = 9.9, 7.8 Hz, 1H), 3.34 (s, 3H), 3.15-2.85 (m, 2H), 1.50 (s, 3H). | 436.1 5.30 min |
| Example 169 CHIRAL METHODS | 0.0193 | 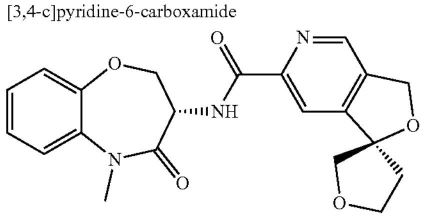 (R)-N-((S)-5-methyl-4-oxo-2,3,4,5-tetrahydrobenzo[b][1,4]oxazepin-3-yl)-4,5-dihydro-2H,3'H-spiro[furan-3,1'-furo[3,4-c]pyridine]-6'-carboxamide | $^1$H NMR (400 MHz, DMSO-$d_6$) δ 8.88 (d, J = 7.9 Hz, 1H), 8.71-8.62 (m, 1H), 8.00 (d, J = 1.0 Hz, 1H), 7.56-7.43 (m, 1H), 7.41-7.21 (m, 3H), 5.14 (s, 2H), 5.01-4.76 (m, 1H), 4.65-4.40 (m, 2H), 4.12-3.73 (m, 4H), 3.33 (s, 3H), 2.35-2.10 (m, 2H). | 396.1 4.32 min |
| Example 170 S-enantiomer CHIRAL METHODS | 0.0132 | 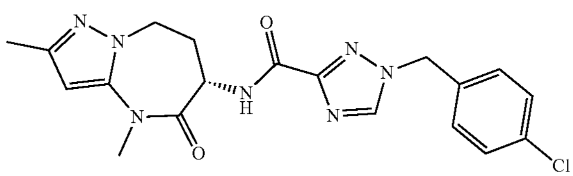 [SMILES: Cc1cc2n(n1)CC[C@H](NC(=O)c1ncn(Cc3ccc(Cl)cc3)n1)C(=O)N2C] (S)-1-(4-chlorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.81 (s, 1H), 8.50 (d, J = 7.8 Hz, 1H), 7.48-7.41 (m, 2H), 7.37-7.30 (m, 2H), 6.12 (s, 1H), 5.49 (s, 2H), 4.37-4.21 (m, 2H), 4.19-4.03 (m, 1H), 3.21 (s, 3H), 2.65-2.51 (m, 1H), 2.41-2.26 (m, 1H), 2.16 (d, J = 0.5 Hz, 3H). | 414.1 4.12 min |
| Example 171 WX Method ZZZ | 0.0162 | 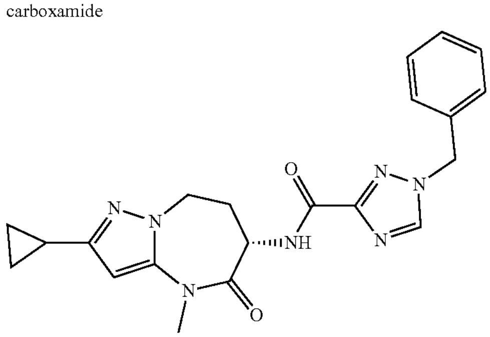 (S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.83 (s, 1H), 8.54 (d, J = 8.0 Hz, 1H), 7.41-7.28 (m, 5H), 6.06 (s, 1H), 5.48 (s, 2H), 4.34-4.22 (m, 2H), 4.12-4.04 (m, 1H), 3.19 (s, 3H), 2.61-2.54 (m, 1H), 2.37-2.29 (m, 1H), 1.88-1.81 (m, 1H), 0.89-0.81 (m, 2H), 0.70-0.61 (m, 2H). | 406.2 |

TABLE 2-continued

| Compound Example # Method | RIP1 Ki (μM) | Structure and Name | $^1$H NMR Data | MS (m/z) |
|---|---|---|---|---|
| Example 172 WX Method PP | 0.0229 | 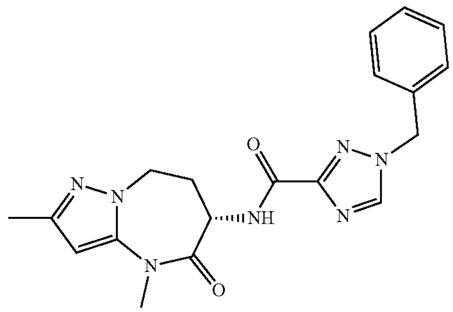 [SMILES: Cc1cc2n(n1)CC[C@H](NC(=O)c1ncn(Cc3ccccc3)n1)C(=O)N2C] (S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.85 (s, 1H), 8.54 (d, J = 8.0 Hz, 1H), 7.39-7.29 (m, 5H), 6.13 (s, 1H), 5.49 (s, 2H), 4.15-4.10 (m, 2H), 4.08-4.06 (m, 1H), 3.21 (s, 3H), 2.59-2.54 (m, 1H), 2.35-2.29 (m, 1H), 2.16 (s, 3H). | 380.4 |
| Example 173 WX Method D | 0.0391 | 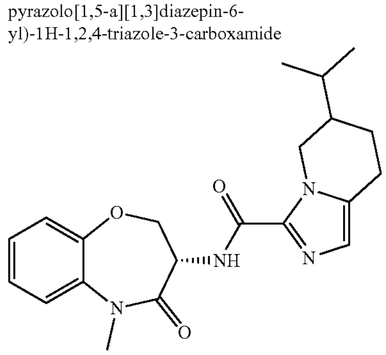 6-isopropyl-N-((S)-5-methyl-4-oxo-2,3,4,5-tetrahydrobenzo[b][1,4]oxazepin-3-yl)-5,6,7,8-tetrahydroimidazo[1,5-a]pyridine-3-carboxamide | $^1$H NMR (400MHz, DMSO-$d_6$) δ 8.27 (d, J = 8.0 Hz, 1H), 7.49 (d, J = 6.8 Hz, 1H), 7.35-7.26 (m, 2H), 7.25-7.21 (m, 1H), 6.81 (s, 1H), 4.83-4.75 (m, 1H), 4.63-4.51 (m, 2H), 4.43-4.37 (m, 1H), 3.69-3.62 (m, 1H), 3.31 (s, 3H), 2.95-2.87 (m, 1H), 2.67-2.58 (m, 1H), 1.93-1.85 (m, 1H), 1.68-1.54 (m, 2H), 1.41-1.28 (m, 1H), 0.92-0.88 (m, 6H). | 383.1 |
| Example 174 WX Method FF | 0.166 | 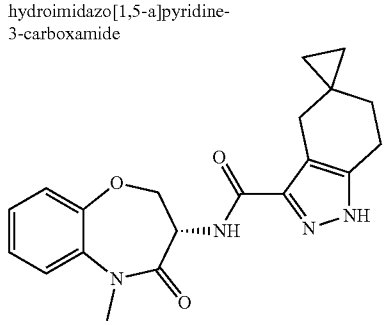 (S)-N-(5-methyl-4-oxo-2,3,4,5-tetrahydrobenzo[b][1,4]oxazepin-3-yl)-1',4',6',7'-tetrahydrospiro[cyclopropane-1,5'-indazole]-3'-carboxamide | $^1$H NMR (400 MHz, DMSO-$d_6$) δ 12.90 (s, 1H), 7.92 (d, J = 7.6 Hz, 1H), 7.48 (d, J = 6.0 Hz, 1H), 7.37-7.16 (m, 3H), 4.85-4.75 (m, 1H), 4.53-4.44 (m, 1H), 4.42-4.35 (m, 1H), 3.31 (s, 3H), 2.63 (t, J = 5.6 Hz, 2H), 2.41 (s, 2H), 1.49 (t, J = 5.6 Hz, 2H), 0.46-0.20 (m, 4H). | 367.1 |
| Example 175 WX Method RRRRRR | 0.212 | 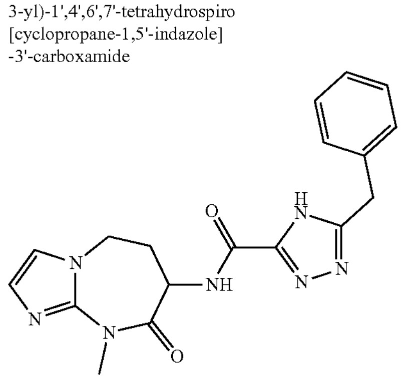 5-benzyl-N-(9-methyl-8-oxo-6,7,8,9-tetrahydro-5H-imidazo[1,2-a][1,3]diazepin-7-yl)-4H-1,2,4-triazole-3-carboxamide | $^1$H NMR (400 MHz, $CD_3OD$) δ 7.34-7.22 (m, 5H), 7.09 (s, 1H), 6.96 (s, 1H), 4.53-4.48 (m, 1H), 4.32-4.26 (m, 1H), 4.16 (s, 2H), 4.10-4.02 (m, 1H), 3.38 (s, 3H), 2.77-2.90 (m, 1H), 2.29-2.21 (m, 1H). | 366.1 |

TABLE 2-continued

| Compound Example # Method | RIP1 Ki (μM) | Structure and Name | $^1$H NMR Data | MS (m/z) |
|---|---|---|---|---|
| Example 176 WX Method SSSSSS | 1.4 | 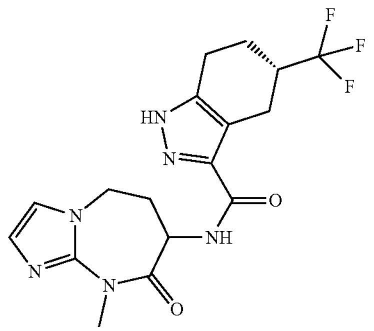 [SMILES: CN1C(=O)C(NC(=O)c2n[nH]c3c2C[C@@H](C(F)(F)F)CC3)CCn2ccnc21] (5S)-N-(9-methyl-8-oxo-6,7,8,9-tetrahydro-5H-imidazo[1,2-a][1,3]diazepin-7-yl)-5-(trifluoromethyl)-4,5,6,7-tetrahydro-1H-indazole-3-carboxamide | $^1$H NMR (400 MHz, $CD_3OD$) δ 7.09 (d, J = 1.2 Hz, 1H), 6.96 (d, J = 1.2 Hz, 1H), 4.52-4.47 (m, 1H), 4.32-4.26 (m, 1H), 4.07-4.05 (m, 1 H), 3.39 (s, 3H), 3.14-3.10 (m, 1H), 2.88-2.84 (m, 2H), 2.76-2.70 (m, 1H), 2.64-2.48 (m, 2H), 2.21-2.20 (m, 2H), 1.74-1.69 (m, 1H). | 397.0 |
| Example 177 WX Method TTTTTT | 1.9 | 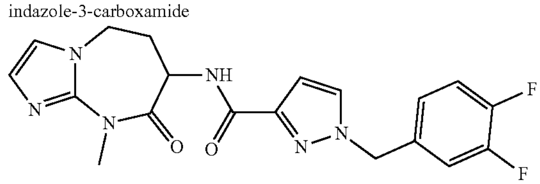 1-(3,4-difluorobenzyl)-N-(9-methyl-8-oxo-6,7,8,9-tetrahydro-5H-imidazo[1,2-a][1,3]diazepin-7-yl)-1H-pyrazole-3-carboxamide | $^1$H NMR (400 MHz, $CD_3OD$) δ 7.75 (d, J = 2.4 Hz, 1H), 7.27-7.21 (m, 2H), 7.09-7.01 (m, 2H), 6.95 (d, J = 1.2 Hz, 1H), 6.75-6.74 (m, 1H), 5.38 (s, 2H), 4.53-4.48 (m, 1H), 4.31-4.26 (m, 1H), 4.06-4.03 (m, 1H), 3.38 (s, 3H) 2.85-2.79 (m, 1H), 2.29-2.23 (m, 1H). | 401.1 |
| Example 178 WX Method UUUUUU | 0.477 | 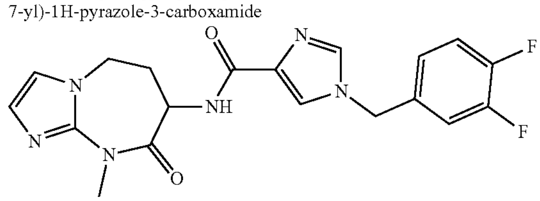 1-(3,4-difluorobenzyl)-N-(9-methyl-8-oxo-6,7,8,9-tetrahydro-5H-imidazo[1,2-a][1,3]diazepin-7-yl)-1H-imidazole-4-carboxamide | $^1$H NMR (400 MHz, $CD_3OD$) δ 7.78 (s, 1H), 7.67 (s, 1H), 7.28-7.23 (m, 2H), 7.11-7.08 (m, 2H), 6.94 (d, J = 1.6 Hz, 1H), 5.23 (s, 2H), 4.50-4.46 (m, 1H), 4.31-4.26 (m, 1H), 4.07-4.02 (m, 1H), 3.38 (s, 3H), 2.86-2.80 (m, 1H), 2.25-2.19 (m, 1H). | 401.1 |
| Example 179 WX Method DDDDDD | 0.254 | 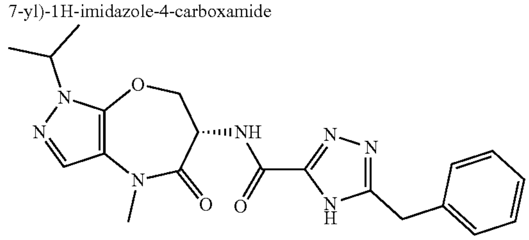 (S)-5-benzyl-N-(1-isopropyl-4-methyl-5-oxo-4,5,6,7-tetrahydro-1H-pyrazolo[3,4-b][1,4]oxazepin-6-yl)-4H-1,2,4-triazole-3-carboxamide | $^1$H NMR (400 MHz, $CD_3OD$) δ 7.48 (s, 1H), 7.35-7.21 (m, 5H), 4.67-4.64 (m, 1H), 4.60-4.53 (m, 2H), 4.45-4.40 (m, 1H), 4.18 (s, 2H), 3.37 (s, 3H), 1.45-1.40 (m, 6H) | 410.3 |
| Example 180 WX Method FFFFFF | 8.5 | 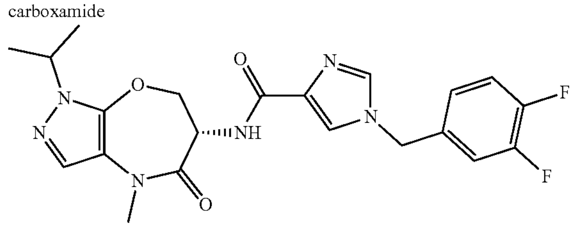 (S)-1-(3,4-difluorobenzyl)-N-(1-isopropyl-4-methyl-5-oxo-4,5,6,7-tetrahydro-1H-pyrazolo[3,4-b][1,4]oxazepin-6-yl)-1H-imidazole-4-carboxamide | $^1$H NMR (400 MHz, $CD_3OD$) δ 7.78 (d, J = 2.4 Hz, 1H), 7.48 (s, 1H), 7.29-7.18 (m, 2H), 7.12-7.10 (m, 1H), 6.80 (d, J = 2.4 Hz, 1H), 5.39 (s, 2H), 4.67-4.53 (m, 3H), 4.44-4.39 (m, 1H), 3.37 (s, 3H), 1.46-1.40 (m, 6H). | 445.3 |

TABLE 2-continued

| Compound Example # Method | RIP1 Ki (μM) | Structure and Name | $^1$H NMR Data | MS (m/z) |
|---|---|---|---|---|
| Example 181 WX Method IIIIII | 0.0936 | 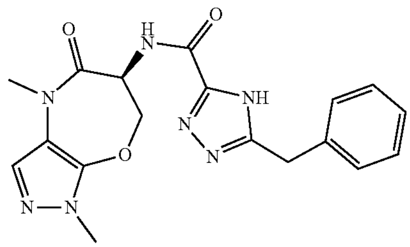 [SMILES: CN1C(=O)[C@@H](NC(=O)c2nnc(Cc3ccccc3)[nH]2)COc2c1cnn2C] (S)-5-benzyl-N-(1,4-dimethyl-5-oxo-4,5,6,7-tetrahydro-1H-pyrazolo[3,4-b][1,4]oxazepin-6-yl)-4H-1,2,4-triazole-3-carboxamide | $^1$H NMR (400 MHz, $CD_3OD$) δ 7.69 (s, 1H), 7.38-7.31 (m, 5H), 4.98-4.93 (m, 1H), 4.72-4.69 (m, 1H), 4.58-4.53 (m, 1H), 4.34 (s, 2H), 3.72 (s, 3H), 3.37 (s, 3H). | 382.1 |
| Example 182 WX Method JJJJJJ | 2.3 | 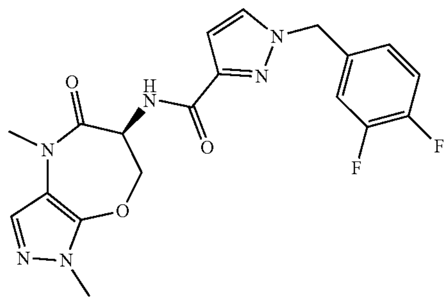 [SMILES: CN1C(=O)[C@@H](NC(=O)c2ccn(Cc3ccc(F)c(F)c3)n2)COc2c1cnn2C] (S)-1-(3,4-difluorobenzyl)-N-(1,4-dimethyl-5-oxo-4,5,6,7-tetrahydro-1H-pyrazolo[3,4-b][1,4]oxazepin-6-yl)-1H-pyrazole-3-carboxamide | $^1$H NMR (400 MHz, $CD_3OD$) δ 7.79 (s 1H) 7.65 (s 1H) 7.26-7.21 (m, 2H), 7.12-7.10 (m, 1H), 6.79 (d, J = 2.0 Hz, 1H), 5.39 (s, 2H), 4.81-4.78 (m, 1H), 4.68-4.65 (m, 1H), 4.50-4.45 (m, 1H), 3.71 (s, 3H), 3.37 (s, 3H). | 417.1 |
| Example 183 WX Method KKKKKK | 1.6 | 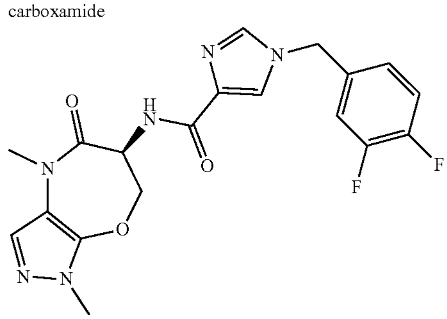 (S)-1-(3,4-difluorobenzyl)-N-(1,4-dimethyl-5-oxo-4,5,6,7-tetrahydro-1H-pyrazolo[3,4-b][1,4]oxazepin-6-yl)-1H-imidazole-4-carboxamide | $^1$H NMR (400 MHz, $CD_3OD$) δ 9.24 (s, 1H), 8.24 (s, 1H), 7.62 (s, 1H), 7.52-7.50 (m, 1H), 7.40-7.35 (m, 2H), 5.50 (d, J = 6.0 Hz, 2H), 5.00-4.93 (m, 1H), 4.65-4.57 (m, 2H), 3.70 (s, 3H), 3.35 (s, 3H). | 417.1 |
| Example 184 Method K (acid) & WX Method C | 0.407 | 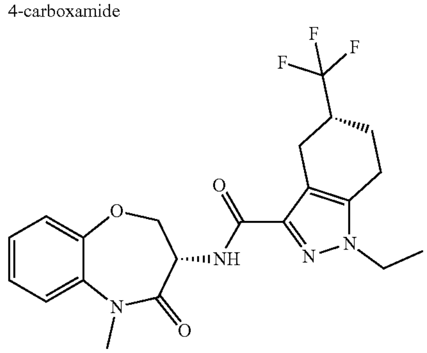 (R)-1-ethyl-N4S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, $CD_3OD$) δ 7.46-7.41 (m, 1H), 7.35-7.23 (m, 3H), 4.96-4.89 (m, 1H), 4.62-4.56 (m, 1H), 4.39-4.36 (m, 1H), 4.12-4.08 (m, 2H), 3.41 (s, 3H), 3.11-3.06 (m, 1H), 2.92-2.86 (m, 1H), 2.72-2.46 (m, 3H), 2.23-2.13 (m, 1H), 1.74-1.71 (m, 1H), 1.41 (t, J = 7.2 Hz, 3H). | 437.2 |

TABLE 2-continued

| Compound Example # Method | RIP1 Ki (μM) | Structure and Name | $^1$H NMR Data | MS (m/z) |
|---|---|---|---|---|
| Example 185 Method K (acid) & WX Method C | 0.825 | 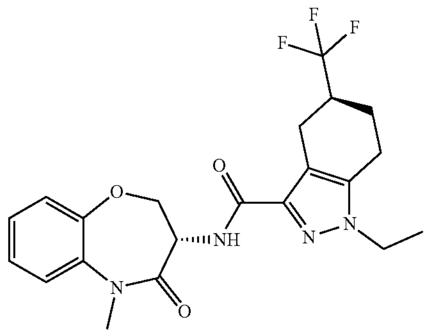 [SMILES: CCn1nc(C(=O)N[C@H]2COc3ccccc3N(C)C2=O)c2c1CC[C@H](C(F)(F)F)C2] (S)-1-ethyl-N-((S)-5-methyl-4-oxo-2,3,4,5-tetrahydrobenzo[b][1,4]oxazepin-3-yl)-5-(trifluoromethyl)-4,5,6,7-tetrahydro-1H-indazole-3-carboxamide | $^1$H NMR (400 MHz, $CD_3OD$) δ 7.43-7.41 (m, 1H), 7.32-7.23 (m, 3H), 4.97-4.93 (m, 1H), 4.60-4.55 (m, 1H), 4.37-4.32 (m, 1H), 4.11-4.07 (m, 2H), 3.41 (s, 3H), 3.12-3.07 (m, 1H), 2.84-2.78 (m, 1H), 2.72-2.41 (m, 3H), 2.27-2.15 (m, 1H), 1.73-1.70 (m, 1H), 1.40 (t, J = 7.2 Hz, 3H). | 437.1 |
| Example 186 WX Method BB | 0.135 | 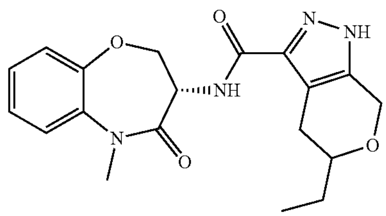 [SMILES: CCC1Cc2c(C(=O)N[C@H]3COc4ccccc4N(C)C3=O)n[nH]c2CO1] 5-ethyl-N-((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide | $^1$H NMR (400 MHz, $CD_3OD$) δ 7.42-7.40 (m, 1H), 7.30-7.28 (m, 2H), 7.24-7.21 (m, 1H), 5.00-4.94 (m, 1H), 4.82-4.67 (m, 1H), 4.60-4.58 (m, 2H), 4.36-4.35 (m, 1H), 3.42-3.41 (m, 4H), 2.85-2.80 (m, 1H), 2.52-2.32 (m, 1H), 1.70-1.60 (m, 2H), 1.01 (t, J = 7.2 Hz, 3H). | 371.2 |
| Example 187 WX Method F | 0.21 | 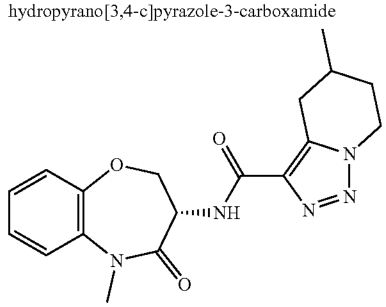 5-methyl-N-((S)-5-methyl-4-oxo-2,3,4,5-tetrahydrobenzo[b][1,4]oxazepin-3-yl)-4,5,6,7-tetrahydro-[1,2,3]triazolo[1,5-a]pyridine-3-carboxamide | $^1$H NMR (400 MHz, DMSO-$d_6$) δ 8.42-8.39 (m, 1H), 7.51-7.47 (m, 1H), 7.33-7.26 (m, 2H), 7.25-7.21 (m, 1H), 4.88-4.81 (m, 1H), 4.65-4.57 (m, 1H), 4.55-4.47 (m, 1H), 4.42-4.36 (m, 1H), 4.24-4.20 (m, 1H), 3.31 (s, 3H), 3.15-3.07 (m, 1H), 2.44-2.31 (m, 2H), 2.01-1.95 (m, 1H), 1.72-1.63 (m, 1H), 1.04 (d, J = 6.4 Hz, 3H). | 356.1 |
| Example 188 WX Method HHHHHH | 4.5 | 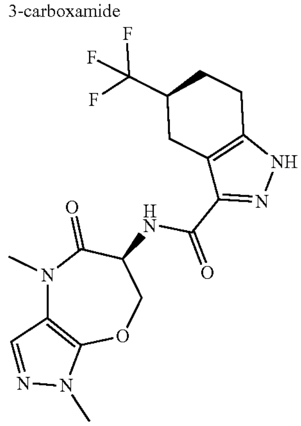 (S)-N-((S)-1,4-dimethyl-5-oxo-4,5,6,7-tetrahydro-1H-pyrazolo | $^1$H NMR (400 MHz, $CD_3OD$) δ 7.65 (s, 1H), 5.06-4.95 (m, 1H), 4.68-4.65 (m, 1H), 4.49-4.44 (m, 1H), 3.72 (s, 3H), 3.37 (s, 3H), 3.20-3.15 (m, 1H), 2.94-2.84 (m, 1H), 2.79-2.49 (m, 3H), 2.27-2.18 (m, 1H), 1.82-1.67 (m, 1H). | 413.0 |

| Compound Example # Method | RIP1 Ki (μM) | Structure and Name | $^1$H NMR Data | MS (m/z) |
|---|---|---|---|---|
| | | [3,4-b][1,4]oxazepin-6-yl)-5-(trifluoromethyl)-4,5,6,7-tetrahydro-1H-indazole-3-carboxamide | | |
| Example 189 WX Method S | 0.26 | 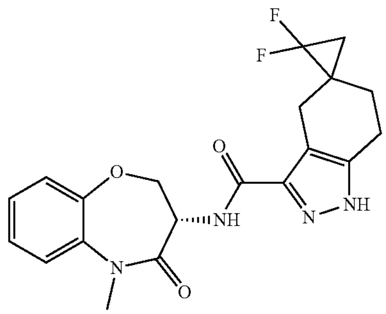 [SMILES: CN1C(=O)[C@@H](NC(=O)c2n[nH]c3c2CC2(CC3)CC2(F)F)COc2ccccc21] 2,2-difluoro-N-((S)-5-methyl-4-oxo-2,3,4,5-tetrahydrobenzo[b][1,4]oxazepin-3-yl)-1',4',6',7'-tetrahydrospiro[cyclopropane-1,5'-indazole]-3'-carboxamide | $^1$H NMR (400 MHz, DMSO-$d_6$) δ 13.04 (s, 1H), 8.00 (d, J = 8.0 Hz, 1H), 7.47 (d, J = 7.2 Hz, 1H), 7.32-7.28 (m, 2H), 7.24-7.22 (m, 1H), 4.85-4.80 (m, 1H), 4.51-4.47 (m, 1H), 4.42-4.38 (m, 1H), 3.31 (s, 3H), 2.79 -2.74 (m, 1H), 2.70-2.67 (m, 2H), 2.59-2.55 (m, 1H), 1.80-1.78 (m, 2H), 1.38-1.32 (m, 1H), 1.28-1.23 (m, 1H). | 403.1 |
| Example 190 WX Method B | 0.262 | 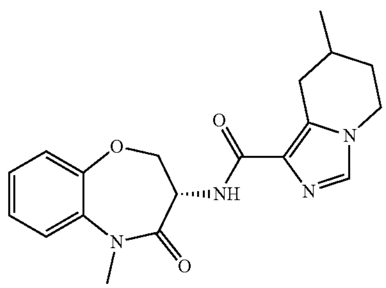 [SMILES: CC1CCn2cnc(C(=O)N[C@H]3COc4ccccc4N(C)C3=O)c2C1] 7-methyl-N4S)-5-methyl-4-oxo-2,3,4,5-tetrahydrobenzo[b][1,4]oxazepin-3-yl)-5,6,'7,8-tetrahydroimidazo[1,5-a]pyridine-1-carboxamide | $^1$H NMR (400 MHz, $CD_3OD$) δ 7.55-7.53 (m, 1H), 7.43-7.41 (m, 1H), 7.32-7.29 (m, 2H), 7.11-6.92 (m, 1H), 4.97-4.96 (m, 1H), 4.59-4.55 (m, 1H), 4.35-4.21 (m, 2H), 3.94-3.93 (m, 1H), 3.42-3.41 (m, 3H), 3.31-3.24 (m, 1H), 2.41-2.34 (m, 1H), 2.01-1.98 (m, 2H), 1.63-1.59 (m, 1H), 1.12-1.09 (m, 3H). | 355.0 |
| Example 191 WX Method GG | 0.022 | 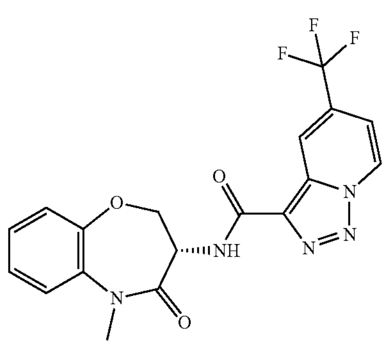 [SMILES: CN1C(=O)[C@@H](NC(=O)c2nnn3ccc(C(F)(F)F)cc23)COc2ccccc21] (S)-N-(5-methyl-4-oxo-2,3,4,5-tetrahydrobenzo[b][1,4]oxazepin-3-yl)-5-(trifluoromethyl)-[1,2,3]triazolo[1,5-a]pyridine-3-carboxamide | $^1$H NMR (400 MHz, DMSO-$d_6$) δ 9.47 (d, J = 7.6 Hz, 1H), 9.01 (d, J = 8.0 Hz, 1H), 8.43 (s, 1H), 7.67-7.61 (m, 1H), 7.56-7.49 (m, 1H), 7.38-7.22 (m, 3H), 5.00-4.91 (m, 1H), 4.77-4.70 (m, 1H), 4.48-4.43 (m, 1H), 3.33 (s, 3H). | 406.0 |

TABLE 2-continued

| Compound Example # Method | RIP1 Ki (μM) | Structure and Name | $^1$H NMR Data | MS (m/z) |
|---|---|---|---|---|
| Example 192 WX Method HH | 0.105 | 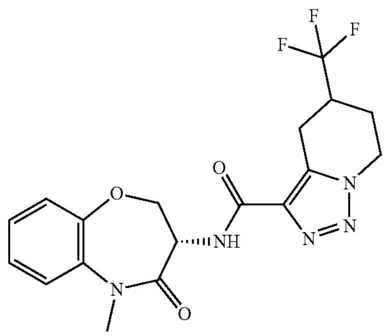 [SMILES: CN1C(=O)[C@@H](NC(=O)c2nnn3c2CC(C(F)(F)F)CC3)COc2ccccc21] N-((S)-5-methyl-4-oxo-2,3,4,5-tetrahydrobenzo[b][1,4]oxazepin-3-yl)-5-(trifluoromethyl)-4,5,6,7-tetrahydro-[1,2,3]triazolo[1,5-a]pyridine-3-carboxamide | $^1$H NMR (400 MHz, DMSO-$d_6$) δ 8.56-8.49 (m, 1H), 7.53-7.46 (m, 1H), 7.40-7.15 (m, 3H), 4.91-4.80 (m, 1H), 4.68-4.60 (m, 2H), 4.44-4.23 (m, 2H), 3.31 (s, 3H), 3.15-3.02 (m, 1H), 2.89-2.79 (m, 1H), 2.53-2.51 (m, 1H), 2.34-2.26 (m, 1H), 2.13-1.99 (m, 1H). | 410.0 |
| Example 193 WX Method L | 0.0575 | 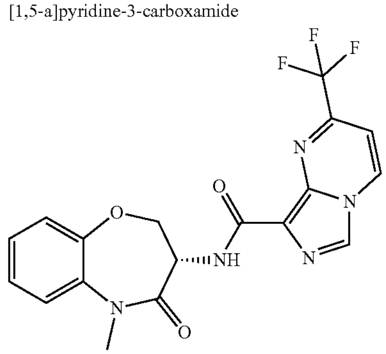 (S)-N-(5-methyl-4-oxo-2,3,4,5-tetrahydrobenzo[b][1,4]oxazepin-3-yl)-2-(trifluoromethyl)imidazo[1,5-a]pyrimidine-8-carboxamide | $^1$H NMR (400 MHz, DMSO-$d_6$) δ 9.14 (d, J = 6.8 Hz, 1H), 8.68 (s, 1H), 8.38 (d, J = 7.2 Hz, 1H), 7.52-7.50 (m, 1H), 7.40 (d, J = 7.6 Hz, 1H), 7.36-7.25 (m, 3H), 4.95-4.88 (m, 1H), 4.55-4.44 (m, 2H), 3.34 (s, 3H). | 406.1 |
| Example 194 WX Method G | 0.167 | 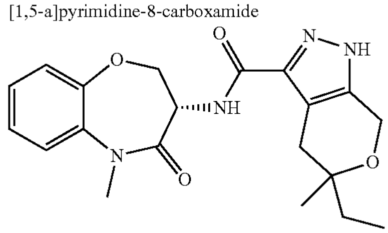 5-ethyl-5-methyl-N-((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide | $^1$H NMR (400 MHz, DMSO-$d_6$) δ 13.01 (s, 1H), 8.01 (s, 1H), 7.52-7.45 (m, 1H), 7.35-7.20 (m, 3H), 4.88-4.78 (m, 1H), 4.61 (s, 2H), 4.57-4.50 (m, 1H), 4.42-4.38 (m, 1H), 3.31 (s, 3H), 2.50 (s, 2H), 1.58-1.39 (m, 2H), 1.08 (s, 3H), 0.86 (t, J = 7.1 Hz, 3H). | 385 |
| Example 195 WX Method VVVVVV | 0.123 | 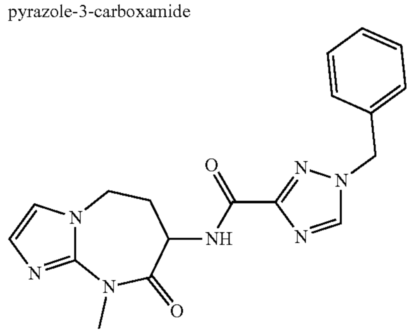 1-benzyl-N-(9-methyl-8-oxo-6,7,8,9-tetrahydro-5H-imidazo[1,2-a][1,3]diazepin-7-yl)-1H-1,2,4-triazole-3-carboxamide | $^1$H NMR (400 MHz, DMSO-$d_6$) δ 8.83 (s, 1H), 8.56 (d, J = 7.6 Hz, 1H), 7.39-7.30 (m, 5H), 7.13 (s, 1H), 6.88 (s, 1H), 5.48 (s, 2H), 4.32-4.22 (m, 2H), 3.95-3.90 (m, 1H), 3.25 (s, 3H), 2.67-2.65 (m, 1H), 2.39-2.33 (m, 1H). | 366.1 |

TABLE 2-continued

| Compound Example # Method | RIP1 Ki (μM) | Structure and Name | $^1$H NMR Data | MS (m/z) |
|---|---|---|---|---|
| Example 196 WX Method WWWWWW | 0.341 | 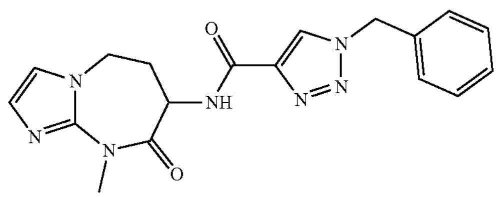 [SMILES: CN1C(=O)C(NC(=O)c2cn(Cc3ccccc3)nn2)CCn2ccnc21] 1-benzyl-N-(9-methyl-8-oxo-6,7,8,9-tetrahydro-5H-imidazo[1,2-a][1,3]diazepin-7-yl)-1H-1,2,3-triazole-4-carboxamide | $^1$H NMR (400 MHz, DMSO-$d_6$) δ 8.68 (s, 1H), 8.66 (s, 1H), 7.38-7.33 (m, 5H), 7.12 (s, 1H), 6.88 (s, 1H), 5.65 (s, 2H), 4.32-4.23 (m, 2H), 3.94-3.90 (m, 1H), 3.25 (s, 3H), 2.67 (s, 1H), 2.37-2.33 (m, 1H). | 366.1 |
| Example 197 WX Method GGGGGG | 5.1 | 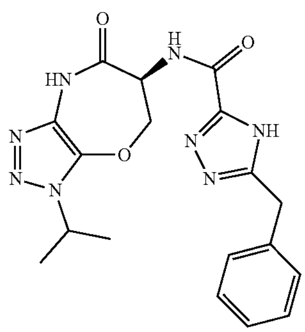 [SMILES: CC(C)n1nnc2c1OC[C@H](NC(=O)c1nnc(Cc3ccccc3)[nH]1)C(=O)N2] (S)-5-benzyl-N-(1-isopropyl-5-oxo-4,5,6,7-tetrahydro-1H-pyrazolo[3,4-b][1,4]oxazepin-6-yl)-4H-1,2,4-triazole-3-carboxamide | $^1$H NMR (400 MHz, $CD_3OD$) δ 7.34-7.26 (m, 5H), 7.25-7.20 (m, 1H), 4.87-4.68 (m, 1H), 4.67-4.64 (m, 1H), 4.55-4.51 (m, 1H), 4.41-4.36 (m, 1H), 4.18 (s, 2H), 1.41 (d, J = 7.2 Hz, 6H). | 396.2 |
| Example 198 WX Method YYYYYY | 0.232 | 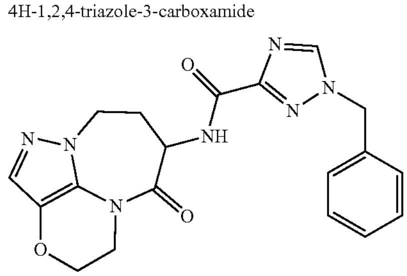 1-benzyl-N-(6-oxo-4,5,6,7,8,9-hexahydro-3-oxa-1,5a,9a-triazabenzo[cd]azulen-7-yl)-1H-1,2,4-triazole-3-carboxamide | $^1$H NMR (400 MHz, DMSO-$d_6$) δ 8.84 (s, 1H), 8.71 (d, J = 6.8 Hz, 1H), 7.40-7.31 (m, 5H), 7.27 (s, 1H), 5.50 (s, 2H), 4.76 (t, J = 8.0 Hz, 1H), 4.41-4.29 (m, 4H), 3.96 (t, J = 8.0 Hz, 1H), 3.32-3.28 (m, 1H), 2.50-2.27 (m, 2H). | 394.2 |
| Example 199 WX Method XXXXXX | 0.766 | 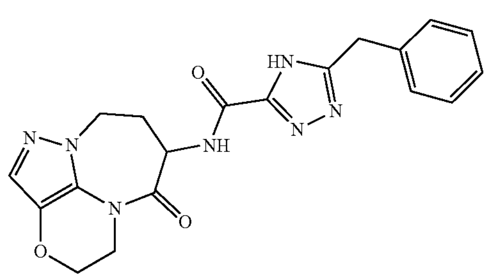 [SMILES: O=C(NC1CCn2ncc3c2N(CCO3)C1=O)c1nnc(Cc2ccccc2)[nH]1] 5-benzyl-N-(6-oxo-4,5,6,7,8,9-hexahydro-3-oxa-1,5a,9a-triazabenzo[cd]azulen-7-yl)-4H-1,2,4-triazole-3-carboxamide | $^1$H NMR (400 MHz, DMSO-$d_6$) δ 14.48 (br. s., 1H), 8.75 (s, 1H), 7.36-7.22 (m, 6H), 4.80-4.72 (m, 1H), 4.39-4.24 (m, 4H), 4.13 (s, 2H), 4.00-3.92 (m, 1H), 3.30-3.27 (m, 1H), 2.50-2.27 (m, 2H). | 394.2 |

TABLE 2-continued

| Compound Example # Method | RIP1 Ki (μM) | Structure and Name | $^1$H NMR Data | MS (m/z) |
|---|---|---|---|---|
| Example 200 WX Method T | 1.7 | 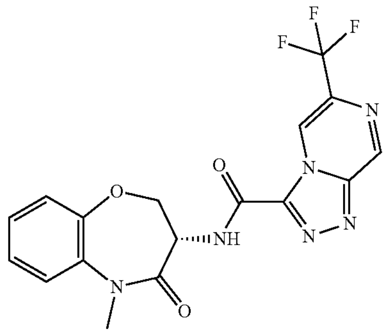 [SMILES: CN1C(=O)[C@@H](NC(=O)c2nnc3cnc(C(F)(F)F)cn23)COc2ccccc21] (S)-N-(5-methyl-4-oxo-2,3,4,5-tetrahydrobenzo[b][1,4]oxazepin-3-yl)-6-(trifluoromethyl)-[1,2,4]triazolo[4,3-a]pyrazine-3-carboxamide | $^1$H NMR (400 MHz, DMSO-$d_6$) δ 9.74 (s, 1H), 9.67 (s, 1H), 9.31 (s, 1H), 7.55-7.52 (m, 1H), 7.35-7.26 (m, 3H), 4.96-4.92 (m, 1H), 4.81-4.74 (m, 1H), 4.49-4.44 (m, 1H), 3.33 (s, 3H). | 407.0 |
| Example 201 WX Method Y | 0.411 | 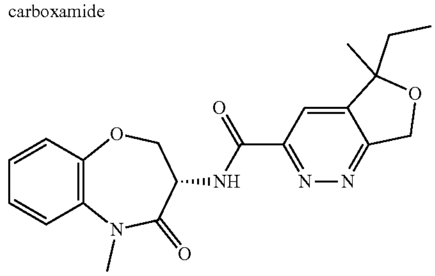 5-ethyl-5-methyl-N-((S)-5-methyl-4-oxo-2,3,4,5-tetrahydrobenzo[b][1,4]oxazepin-3-yl)-5,7-dihydrofuro[3,4-c]pyridazine-3-carboxamide | $^1$H NMR (400 MHz, DMSO-$d_6$) δ 9.28 (d, J = 4.4 Hz, 1H), 8.14 (s, 1H) , 7.52 (d, J = 6.8 Hz, 1H), 7.34-7.25 (m, 3H), 5.26 (s, 2H), 4.97-4.92 (m, 1H), 4.72-4.67 (m, 1H), 4.51-4.46 (m, 1H), 3.34 (s, 3H), 1.90-1.78 (s, 2H), 1.46 (s, 3H), 0.74-0.71 (m, 3H). | 383.1 |
| Example 202 WX Method II | 0.0576 | 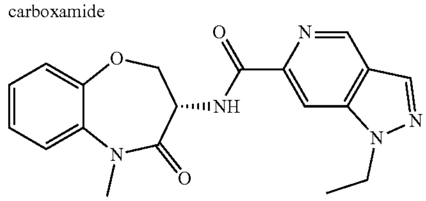 (S)-1-ethyl-N-(5-methyl-4-oxo-2,3,4,5-tetrahydrobenzo[b][1,4]oxazepin-3-yl)-1H-pyrazolo[4,3-c]pyridine-6-carboxamide | $^1$H NMR (400 MHz, DMSO-$d_6$) δ 9.18 (s, 1H), 9.03 (d, J = 8.0 Hz, 1H), 8.44 (s, 1H), 8.31 (s, 1H), 7.57-7.47 (m, 1H), 7.41-7.23 (m, 3H), 4.97-4.88 (m, 1H), 4.61-4.49 (m, 4H), 3.34 (s, 3H), 1.39 (t, J = 7.2 Hz, 3H). | 366.0 |
| Example 203 WX Method EEEEEE | 0.912 | 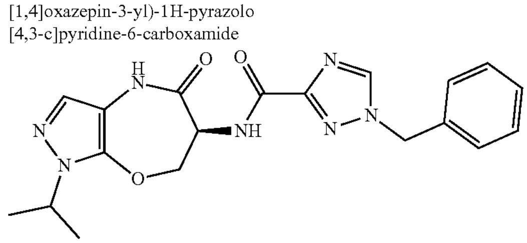 (S)-1-benzyl-N-(1-isopropyl-5-oxo-4,5,6,7-tetrahydro-1H-pyrazolo[3,4-b][1,4]oxazepin-6-yl)-1H-1,2,4-triazole-3-carboxamide | $^1$H NMR (400 MHz, $CD_3OD$) δ 8.60 (s, 1H), 7.37 (s, 5H), 7.20 (s, 1H), 5.49 (s, 2H), 4.83 (s, 1H), 4.67-4.64 (m, 1H), 4.56-4.48 (m, 1H), 4.40-4.36 (m, 1H), 1.43-1.40 (m, 6H). | 396.2 |
| Example 204 WX Method LLLLLL | 0.0843 | 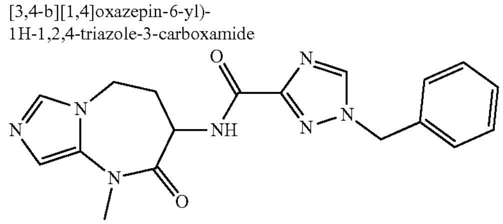 1-benzyl-N-(1-methyl-2-oxo-2,3,4,5-tetrahydro-1H-imidazo[1,5-a][1,3]diazepin-3-yl)-1H-1,2,4-triazole-3-carboxamide | $^1$H NMR (400 MHz, $CD_3OD$) δ 8.56 (s, 1H), 7.62 (s, 1H), 7.37-7.33 (m, 5H), 6.99 (s, 1H), 5.47 (s, 2H), 4.85-4.59 (m, 1H), 4.45-4.39 (m, 1H), 4.03-3.97 (m, 1H), 3.35 (s, 3H), 2.79-2.72 (m, 1H), 2.20-2.15 (m, 1H). | 366.1 |

TABLE 2-continued

| Compound Example # Method | RIP1 Ki (μM) | Structure and Name | $^1H$ NMR Data | MS (m/z) |
|---|---|---|---|---|
| Example 205 WX Method I | 0.0983 | 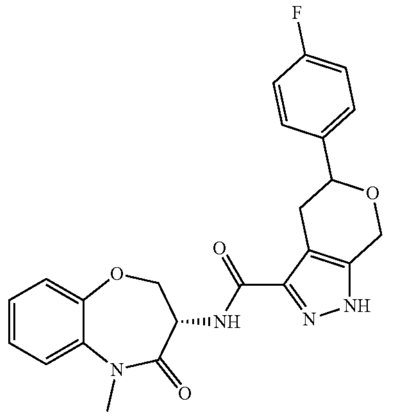 [SMILES: CN1C(=O)[C@@H](NC(=O)c2n[nH]c3c2CC(c2ccc(F)cc2)OC3)COc2ccccc21] 5-(4-fluorophenyl)-N-((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide | $^1H$ NMR (400 MHz, $CD_3OD$) δ 7.48-7.38 (m, 3H), 7.30-7.28 (m, 3H), 7.09-7.06 (m, 2H), 4.98-4.93 (m, 2H), 4.88-4.83 (m, 1H), 4.61-4.58 (m, 2H), 4.57-4.33 (m, 1H), 3.40 (s, 3H), 3.13-3.08 (m, 1H), 2.80-2.74 (m, 1H). | 437.2 |
| Example 206 WX Method J | 0.131 | 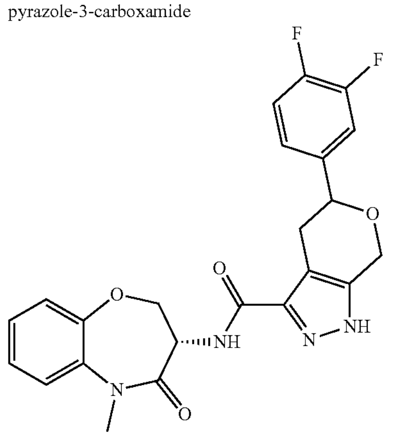 5-(3,4-difluorophenyl)-N-((S)-5-methyl-4-oxo-2,3,4,5-tetrahydrobenzo[b][1,4]oxazepin-3-yl)-1,4,5,7-tetrahydropyrano[3,4-c]pyrazole-3-carboxamide | $^1H$ NMR (400 MHz, $CD_3OD$) δ 7.40-7.21 (m, 7H), 5.00-4.95 (m, 2H), 4.86-4.82 (m, 1H), 4.60-4.56 (m, 2H), 4.37-4.33 (m, 1H), 3.31 (s, 3H), 3.16-3.12 (m, 1H), 2.75-2.67 (m,1H). | 455.2 |
| Example 207 WX Method K | 0.0617 | 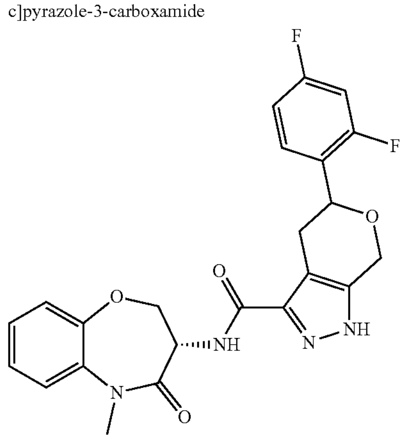 5-(2,4-difluorophenyl)-N-((S)-5-methy1-4-oxo-2,3,4,5-tetrahydrobenzo[b][1,4]oxazepin-3-yl)-1,4,5,7-tetrahydropyrano[3,4-c]pyrazole-3-carboxamide | $^1H$ NMR (400 MHz, $CD_3OD$) δ 7.57-7.21 (m, 6H), 6.97-6.94 (m, 1H), 4.99-4.86 (m, 3H), 4.60-4.58 (m, 2H), 4.40-4.36 (m, 1H), 3.41 (s, 3H), 3.16-3.08 (m, 1H), 2.81-2.70 (m, 1H). | 455.2 |

TABLE 2-continued

| Compound Example # Method | RIP1 Ki (μM) | Structure and Name | $^1$H NMR Data | MS (m/z) |
|---|---|---|---|---|
| Example 208 WX Method RRRR | 0.12 | 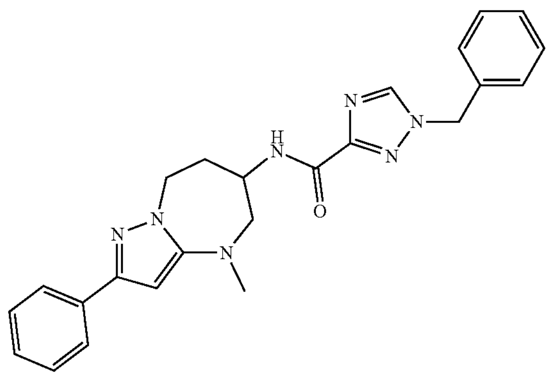 [SMILES: CN1CC(NC(=O)c2ncn(Cc3ccccc3)n2)CCn2nc(-c3ccccc3)cc21] 1-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.57 (s, 1H), 7.82 (d, J = 7.2 Hz, 2H), 7.45-7.35 (m, 8H), 6.71 (s, 1H), 5.49 (s, 2H), 4.67-4.32 (m, 3H), 3.42 (s, 3H), 2.97*-2.88 (m, 1H), 2.38-2.29 (m, 1H). | 442.0 |
| Example 209 WX Method SSSS | 0.0756 | 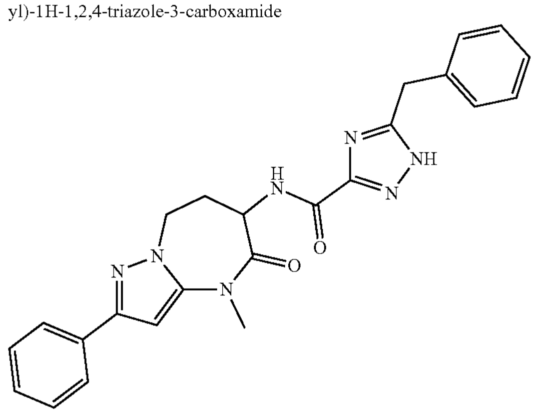 5-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 7.82 (d, J = 6.8 Hz, 2H), 7.45-7.30 (m, 8H), 6.71 (s, 1H), 4.64-4.34 (m, 3H), 4.17 (s, 2H), 3.42 (s, 3H), 2.93-2.87 (m, 1 H), 2.33-2.31 (m, 1H). | 442.0 |
| Example 210 WX Method H | 0.193 | 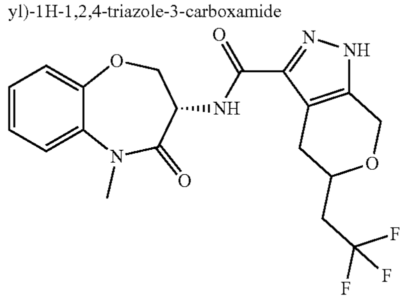 N-((S)-5-methyl-4-oxo-2,3,4,5-tetrahydrobenzo[b][1,4]oxazepin-3-yl)-5-(2,2,2-trifluoroethyl)-1,4,5,7-tetrahydropyrano[3,4-c]pyrazole-3-carboxamide | $^1$H NMR (400 MHz, DMSO-$d_6$) δ 13.06 (s, 1H), 8.05-8.02 (m, 1H), 7.49 (d, J = 7.2 Hz, 1H), 7.32-7.22 (m, 3H), 4.84 (m, 2H), 4.71-4.54 (m, 1H), 4.43-4.42 (m, 1H), 4.42-4.40 (m, 1H), 3.81 (s, 1H), 3.31 (s. 3H), 2.84-2.80 (m, 1H), 2.67-2.63 (m. 2H), 2.61-2.50 (m, 1H). | 425.2 |
| Example 211 WX Method M | 0.156 | 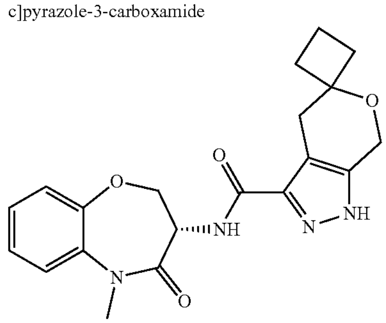 | $^1$H NMR (400 MHz, DMSO-$d_6$): δ 12.99 (s, 1H), 8.02 (d, J = 8.0 Hz, 1H), 7.50-7.48 (m, 1H), 7.35-7.27 (m, 2H), 7.25-7.22 (m, 1H), 4.87-4.80 (m, 1H), 4.65 (s, 2H), 4.55-4.50 (m, 1H), 4.43-4.39 (m, 1H), 3.32 (s, 3H), 2.74 (s, 2H), 2.12-2.05 (m, 2H), 1.79-1.64 (m, 4H). | 383.2 |

TABLE 2-continued

| Compound Example # Method | RIP1 Ki (μM) | Structure and Name | $^1$H NMR Data | MS (m/z) |
|---|---|---|---|---|
| | | (S)-N-(5-methyl-4-oxo-2,3,4,5-tetrahydrobenzo[b][1,4]oxazepin-3-yl)-4',7'-dihydro-1'H-spiro [cyclobutane-1,5'-pyrano[3,4-c] pyrazole]-3'-carboxamide | | |
| Example 212 WX Method DDDDDDD | 0.573 | 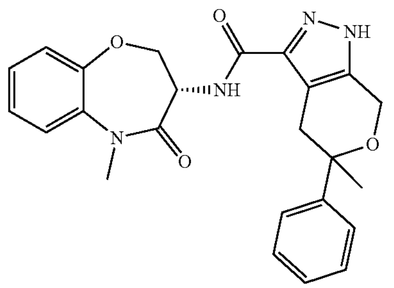 [SMILES: CN1C(=O)[C@@H](NC(=O)c2n[nH]c3c2CC(C)(c2ccccc2)OC3)COc2ccccc21] 5-methyl-N4S)-5-methyl-4-oxo-2,3,4,5-tetrahydrobenzo[b] [1,4]oxazepin-3-yl)-5-phenyl-41,,5,7-tetrahydropyrano[3,4-c]pyrazole-3-carboxamide | $^1$H NMR (400MHz, CD30D) δ 7.42-7.23 (m, 9H), 5.05-5.00 (m, 1H), 4.73-4.69 (m, 1H), 4.61-4.59 (m, 1H), 4.39-4.35 (m, 2H), 3.53-3.48 (m, 1H), 3.40 (s, 3H), 2.96-2.91 (m, 1H), 1.51 (s, 3H). | 433.4 |
| Example 213 WX Method JJ | 0.0123 | 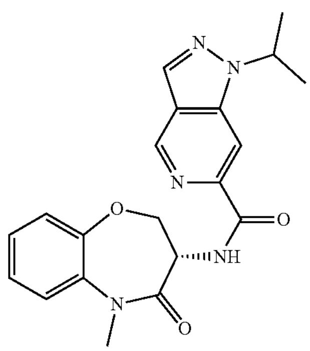 [SMILES: CC(C)n1ncc2cnc(C(=O)N[C@H]3COc4ccccc4N(C)C3=O)cc21] (S)-1-isopropyl-N-(5-methyl-4-oxo-2,3,4,5-tetrahydrobenzo[b] [1,4]oxazepin-3-yl)-1H-pyrazolo [4,3-c]pyridine-6-carboxamide | $^1$H NMR (400 MHz, DMSO-$d_6$) δ 9.17 (s, 1 H), 9.02 (d, J = 8.0 Hz, 1H), 8.44 (s, 1H), 8.30 (s, 1H), 7.53-7.47 (m, 1 H), 7.37-7.24 (m, 3 H), 5.23-5.11 (m, 1H), 4.97-4.87 (m, 1H), 4.89-4.49 (m, 2H), 3.34 (s, 3H), 1.52-1.41 (m, 6H) | 380.0 |
| Example 214 (deleted) | | | | |
| Example 215 WX Method MMMMMM | 0.106 | 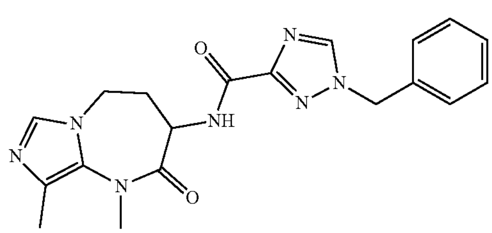 [SMILES: Cc1ncn2c1N(C)C(=O)C(NC(=O)c1ncn(Cc3ccccc3)n1)CC2] 1-benzyl-N-(1,9-dimethyl-2-oxo-2,3,4,5-tetrahydro-1H-imidazo [1,5-a][1,3]diazepin-3-yl)-1H-1,2,4-triazole-3-carboxamide | $^1$H NMR (400 MHz, $CD_3OD$) δ 8.57 (s, 1H), 7.55 (s, 1H), 7.41-7.33 (m, 5H), 5.47 (s, 2H), 4.87-4.54 (m, 1H), 4.36-4.31 (m, 1H), 3.98-3.91 (m, 1H), 3.35 (s, 3H), 2.75-2.63 (m, 1H), 2.22 (s, 3H), 2.15-2.07 (m, 1H). | 380.3 |

TABLE 2-continued

| Compound Example # Method | RIP1 Ki (μM) | Structure and Name | $^1$H NMR Data | MS (m/z) |
|---|---|---|---|---|
| Example 216 WX Method TTTT | 0.0972 | 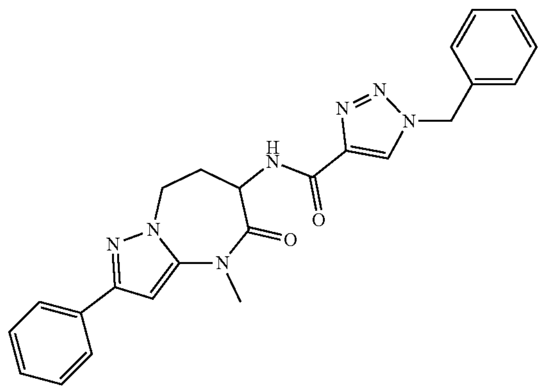 [SMILES: CN1C(=O)C(NC(=O)c2cn(Cc3ccccc3)nn2)CCn2nc(-c3ccccc3)cc21] 1-benzyl-N-(4-methyl-5-oxo-2-phenyl-5,6,7,8-tetrahydro-4H-pyrazolo[1,5-a][1,3]diazepin-6-yl)-1H-1,2,3-triazole-4-carboxamide | $^1$H NMR (400 MHz, $CDCl_3$) δ 7.95-7.92 (m, 2H), 7.76 (d, J = 7.2, 2H), 7.44-7.28 (m, 8H), 6.41 (s, 1H), 5.58 (s, 2H), 4.81-4.76 (m, 1H), 4.55-4.49 (m, 1H), 4.25-4.20 (m, 1H), 3.42 (s, 3H), 3.16-3.09 (m, 1H), 2.16-2.08 (m, 1H). | 442.0 |
| Example 217 WX Method CC | 0.0617 | 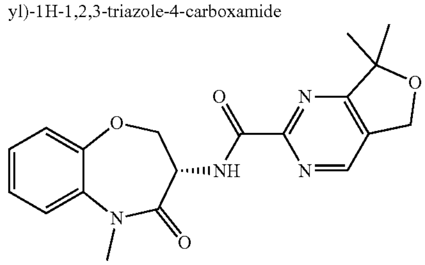 (S)-7,7-dimethyl-N-(5-methyl-4-oxo-2,3,4,5-tetrahydrobenzo[b][1,4]oxazepin-3-yl)-5,7-dihydrofuro[3,4-d]pyrimidine-2-carboxamide | $^1$H NMR (400 MHz, $CD_3OD$) δ 8.36 (s, 1H), 7.47-7.45 (m, 1H), 7.35-7.32 (m, 2H), 7.28-7.27 (m, 1H), 5.16 (s, 2H), 5.06-5.04 (m, 1H), 4.69-4.68 (m, 1H), 4.52-4.47 (m, 1H), 3.45 (s, 3H), 1.54 (s, 6H). | 369.1 |
| Example 218 WX Method P | 0.0254 | 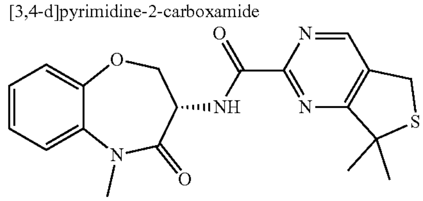 (S)-7,7-dimethyl-N-(5-methyl-4-oxo-2,3,4,5-tetrahydrobenzo[b][1,4]oxazepin-3-yl)-5,7-dihydrothieno[3,4-d]pyrimidine-2-carboxamide | $^1$H NMR (400 MHz, $CD_3OD$) δ 8.81 (s, 1H), 7.45-7.41 (m, 1H), 7.34-7.28 (m, 2H), 7.25-7.22 (m, 1H), 4.69-4.63 (m, 2H), 4.44-4.39 (m, 1H), 4.23 (s, 2H), 3.42 (s, 3H), 1.71 (s, 6H). | 385.2 |
| Example 219 WX Method QQ | 0.0297 | 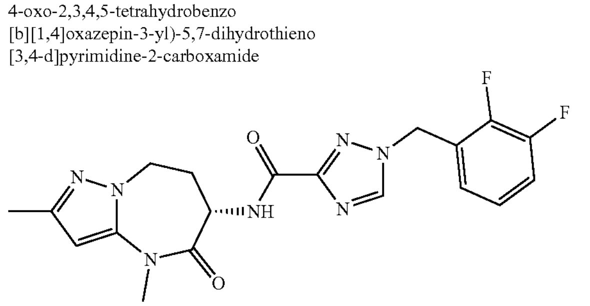 (S)-1-(2,3-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.83 (s, 1H), 8.52 (d, J = 8.0 Hz, 1H), 7.48-7.41 (m, 1H), 7.27-7.15 (m, 2H), 6.12 (s, 1H), 5.61 (s, 2H), 4.34-4.23 (m, 2H), 4.11-4.04 (m, 1H), 3.21 (s, 3H), 2.62-2.54 (m, 1H), 2.36-2.28 (m, 1H), 2.16 (s, 3H). | 416.3 |
| Example 220 WX Method RR | 0.0471 | 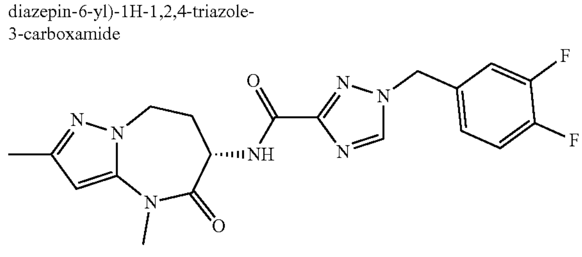 | $^1$H NMR (400 MHz, DMSO-$d_6$) δ 8.80 (s, 1H), 8.52 (d, J = 8.0 Hz, 1H), 7.49-7.41 (m, 2H), 7.19-7.17 (m, 1H), 6.12 (s, 1H), 5.48 (s, 2H), 4.35-4.23 (m, 2H), 4.11-4.04 (m, 1H), 3.21 (s, 3H), 2.62-2.54 (m, 1H), 2.36-2.28 (m, 1H), 2.16 (s, 3H). | 416.3 |

TABLE 2-continued

| Compound Example # Method | RIP1 Ki (μM) | Structure and Name | $^1$H NMR Data | MS (m/z) |
|---|---|---|---|---|
| | | (S)-1-(3,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | | |
| Example 221 WX Method WW | 0.0377 | 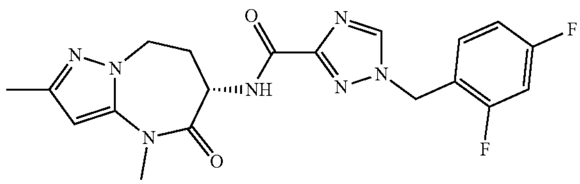 [SMILES: Cc1cc2n(n1)CC[C@H](NC(=O)c1ncn(Cc3ccc(F)cc3F)n1)C(=O)N2C] (S)-1-(2,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.59 (s, 1H), 7.48-7.45 (m, 1H), 7.05-7.00 (m, 2H), 6.11 (s, 1H), 5.52 (s, 2H), 4.54-4.49 (m, 1H), 4.33-4.23 (m, 2H), 3.32 (s, 3H), 2.85-2.83 (m, 1H), 2.25-2.24 (m, 4H). | 416.1 |
| Example 222 WX Method XX | 0.0259 | 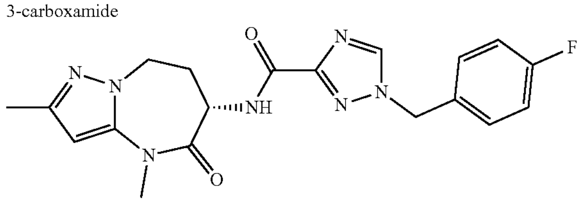 (S)-N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide | $^1$H NMR (400 MHz, $CD_3OD$) δ 8.57 (s, 1H), 7.42-7.38 (m, 2H), 7.12-7.08 (m, 2H), 6.11 (s, 1H), 5.46 (s, 2H), 4.55-4.50 (m, 1H), 4.30-4.22 (m, 2H), 3.32 (s, 3H), 2.86-2.80 (m, 1H), 2.29-2.23 (m, 4H). | 398.0 |
| Example 223 Method AAAA | 0.0319 | 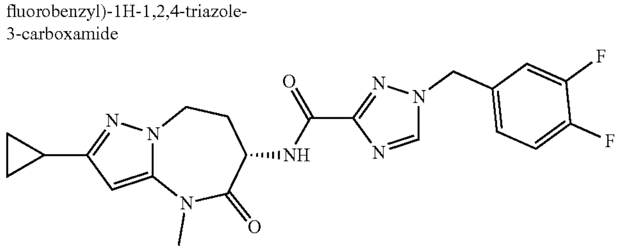 (S)-N-(2-cyclopropyl-4-methyl-5-oxo-5,6,7,8-tetrahydro-4H-pyrazolo[1,5-a][1,3]diazepin-6-yl)-1-(3,4-difluorobenzyl)-1H-1,2,4-triazole-3-carboxamide | $^1$H NMR (400 MHz, $CD_3OD$) δ 8.78 (s, 1H), 7.36-7.20 (m, 3H), 6.29 (s, 1H), 5.49 (s, 2H), 4.71-4.67 (m, 1H), 4.45-4.35 (m, 2H), 3.21 (s, 3H), 2.88-2.86 (m, 1H), 2.40-2.38 (m, 1H), 1.12-1.11 (m, 2H), 0.90-0.88 (m, 2H). | 442.2 |
| Example 224 WX Method EEEE | 0.0219 | 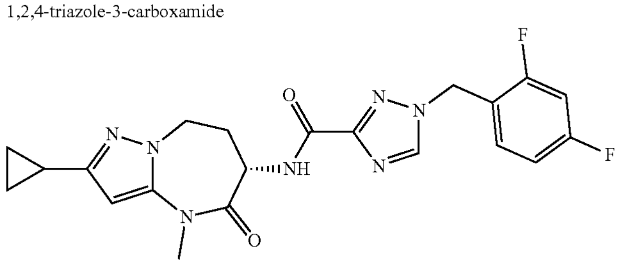 (S)-N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide | $^1$H NMR (400 MHz, $CD_3OD$) δ 8.59 (s, 1H), 7.50-7.46 (m, 1H), 7.06-6.99 (m, 2H), 6.00 (s, 1H), 5.53 (s, 2H), 4.52-4.49 (m, 1H), 4.29-4.19 (m, 2H), 3.18 (s, 3H), 2.85-2.80 (m, 1H), 2.25-2.23 (m, 1H), 1.92-1.89 (m, 1H), 0.95-0.92 (m, 2H), 0.75-0.72 (m, 2H). | 442.1 |
| Example 225 WX Method GGGG | 0.021 | 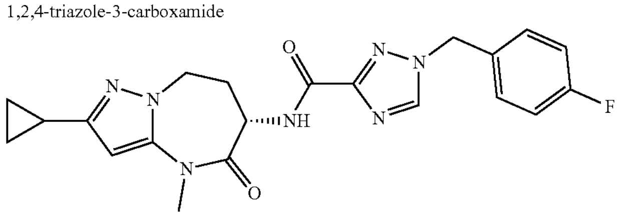 (S)-N-(2-cyclopropyl-4-methyl-5-oxo-5,6,7,8-tetrahydro-4H-pyrazolo | $^1$H NMR (400 MHz, $CD_3OD$) δ 8.55 (s, 1H), 7.40-7.36 (m, 2H), 7.10-7.06 (m, 2H), 5.98 (s, 1H), 5.44 (s, 2H), 4.51-4.47 (m, 1H), 4.27-4.18 (m, 2H), 3.29 (s, 3H), 2.84-2.78 (m, 1H), 2.24-2.21 (m, 1H), 1.90-1.85 (m, 1H), 0.92-0.90 (m, 2H), 0.72-0.70 (m, 2H) | 424.1 |

TABLE 2-continued

| Compound Example # Method | RIP1 Ki (μM) | Structure and Name | $^1$H NMR Data | MS (m/z) |
|---|---|---|---|---|
| | | [1,5-a][1,3]diazepin-6-yl)-1-(4-fluorobenzyl)-1H-1,2,4-triazole-3-carboxamide | | |
| Example 226 WX Method NNNNNN | 0.183 | 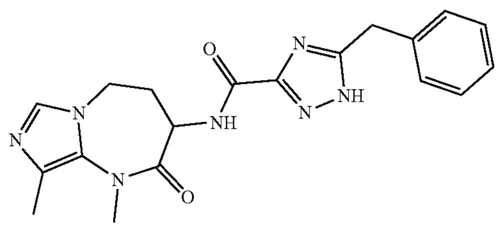 [SMILES: Cc1ncn2c1N(C)C(=O)C(NC(=O)c1n[nH]c(Cc3ccccc3)n1)CC2] 5-benzyl-N-(1,9-dimethyl-2-oxo-2,3,4,5-tetrahydro-1H-imidazo[1,5-a][1,3]diazepin-3-yl)-1H-1,2,4-triazole-3-carboxamide | $^1$H NMR (400 MHz, $CD_3OD$) δ 7.55 (s, 1H), 7.34-7.24 (m, 5H), 4.57-4.55 (m, 1H), 4.37-4.31 (m, 1H), 4.18-4.16 (m, 2H), 3.97-3.91 (m, 1H), 3.31 (s, 3H), 2.72-2.65 (m, 1H), 2.22 (s, 3H), 2.11-2.07 (m, 1H). | 380.2 |
| Example 227 WX Method OOOOOO | 0.419 | 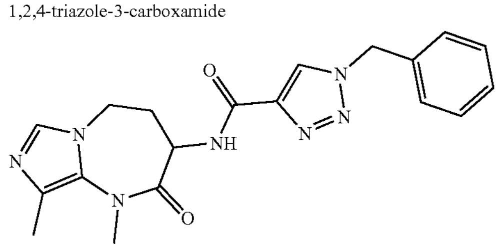 1-benzyl-N-(1,9-dimethyl-2-oxo-2,3,4,5-tetrahydro-1H-imidazo[1,5-a][1,3]diazepin-3-yl)-1H-1,2,3-triazole-4-carboxamide | $^1$H NMR (400 MHz, $CD_3OD$) δ 8.36 (s, 1H), 7.55 (s, 1H),7.40-7.33 (m, 5H), 5.64 (s, 2H), 4.58-4.53 (m, 1H), 4.37-4.32 (m, 1H), 3.97-3.92 (m, 1H), 3.31 (s, 3H), 2.70-2.64 (m, 1H), 2.22 (s, 3H), 2.17-2.12 (m, 1H). | 380.1 |
| Example 228 WX Method KK | 0.005 | 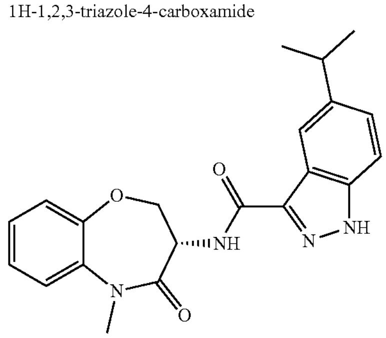 (S)-5-isopropyl-N-(5-methyl-4-oxo-2,3,4,5-tetrahydrobenzo[b][1,4]oxazepin-3-yl)-1H-indazole-3-carboxamide | $^1$H NMR (400 MHz, DMSO-$d_6$) δ 13.65 (br.s, 1H), 8.38 (d, J = 8.0 Hz, 1H), 7.89 (s, 1H), 7.60-7.49 (m, 2H), 7.40-7.23 (m, 4H), 4.99-4.89 (m, 1H), 4.68-4.58 (m, 1H), 4.52-4.43 (m, 1H), 3.34 (s, 3H), 3.04-2.93 (m, 1H), 1.22 (d, J = 6.8 Hz, 6H). | 379.1 |
| Example 229 WX Method Z | 0.0446 | 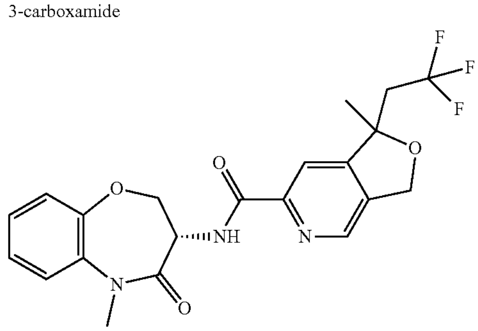 1-methyl-N-((S)-5-methyl-4-oxo-2,3,4,5-tetrahydrobenzo[b][1,4]oxazepin-3-yl)-1-(2,2,2-trifluoroethyl)-1,3-dihydrofuro[3,4-c]pyridine-6-carboxamide | $^1$H NMR (400 MHz, $CD_3OD$) δ 8.62 (s, 1H), 8.05 (s, 1H), 7.46-7.43 (m, 1H), 7.34-7.31 (m, 2H), 7.27-7.24 (m, 1H), 5.21 (s, 2H), 5.04-5.01 (m, 1H), 4.67-4.62 (m, 1H), 4.44-4.41 (m, 1H), 3.43 (s, 3H), 2.90-2.79 (m, 2H), 1.57 (s, 3H). | 436.1 |

TABLE 2-continued

| Compound Example # Method | RIP1 Ki (μM) | Structure and Name | $^1$H NMR Data | MS (m/z) |
|---|---|---|---|---|
| Example 230 WX Method U | 0.0217 | 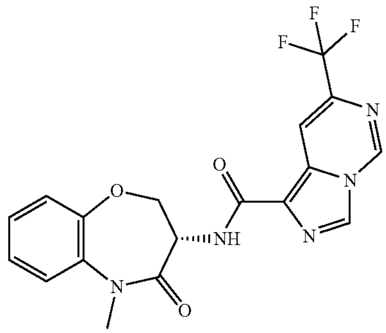 [SMILES: CN1C(=O)[C@@H](NC(=O)c2ncn3cnc(C(F)(F)F)cc23)COc2ccccc21] (S)-N-(5-methyl-4-oxo-2,3,4,5-tetrahydrobenzo[b][1,4]oxazepin-3-yl)-7-(trifluoromethyl)imidazo[1,5-c]pyrimidine-1-carboxamide | $^1$H NMR (400 MHz, DMSO-$d_6$) δ 9.51 (s, 1H), 8.82 (s, 1H), 8.47 (d, J = 8.0 Hz, 1H), 8.17 (s, 1H), 7.50 (d, J = 2.0 Hz, 1H), 7.34-7.25 (m, 3H), 4.95-4.89 (m, 1H), 4.66-4.61 (m, 1H), 4.47-4.29 (m, 1H), 3.33 (s, 3H). | 406.0 |
| Example 231 WX Method DD | 0.511 | 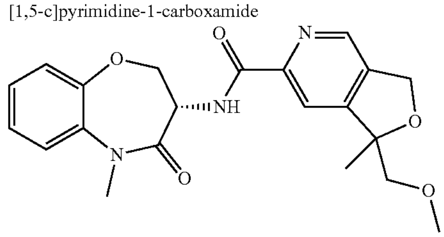 1-(methoxymethyl)-1-methyl-N-((S)-5-methyl-4-oxo-2,3,4,5-tetrahydrobenzo[b][1,4]oxazepin-3-yl)-1,3-dihydrofuro[3,4-c]pyridine-6-carboxamide | $^1$H NMR (400 MHz, $CD_3OD$) δ 8.57 (s, 1H), 7.93 (s, 1H), 7.45-7.43 (m, 1H), 7.34-7.32 (m, 2H), 7.26-7.24 (m, 1H), 5.18 (s, 2H), 5.05-5.00 (m, 1H), 4.67-4.65 (m, 2H), 4.43-4.40 (m, 1H), 3.57-3.51 (m, 2H), 3.43 (s, 3H), 3.27 (s, 3H), 1.46 (s, 3H). | 398.1 |
| Example 232 WX Method Q | 0.0887 | 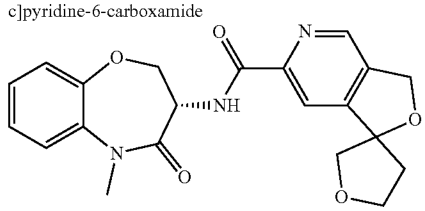 N-((S)-5-methyl-4-oxo-2,3,4,5-tetrahydrobenzo[b][1,4]oxazepin-3-yl)-4,5-dihydro-2H,3'H-spiro[furan-3,1'-furo[3,4-c]pyridine]-6'-carboxamide | $^1$H NMR (400 MHz, $CD_3OD$): δ 8.60 (s, 1H), 7.99 (s, 1H), 7.47-7.41 (m, 1H), 7.37-7.28 (m, 2H), 7.27-7.21 (m, 1H), 5.18 (s, 2H), 5.00-5.05 (m, 1H), 4.67-4.61 (m, 1H), 4.44-4.36 (m, 1H), 4.15-4.02 (m, 2H), 3.96-3.99 (m, 1H), 3.90-3.83 (m, 1H), 3.43 (s, 3H), 2.38-2.23 (m, 2H). | 396.0 |
| Example 233 WX Method QQQQQQ | 2 | 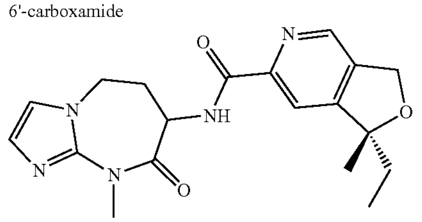 (1R)-1-ethyl-1-methyl-N-(9-methyl-8-oxo-6,7,8,9-tetrahydro-5H-imidazo[1,2-a][1,3]diazepin-7-yl)-1,3-dihydrofuro[3,4-c]pyridine-6-carboxamide | $^1$H NMR (400 MHz, $CD_3OD$) δ 8.57 (s, 1H), 7.87 (s, 1H), 7.13 (s, 1H), 7.00-6.99 (m, 1H), 5.21-5.13 (m, 2H), 4.58-4.55 (m, 1H), 4.35-4.30 (m, 1H), 4.12-4.10 (m, 1H), 3.41 (s, 3H), 2.95-2.92 (m, 1H), 2.32-2.26 (m,1H), 1.89-1.83 (m, 2H), 1.47 (s, 3H), 0.80-0.76 (m, 3H). | 370.1 |
| Example 234 WX Method WWWW | 0.199 | 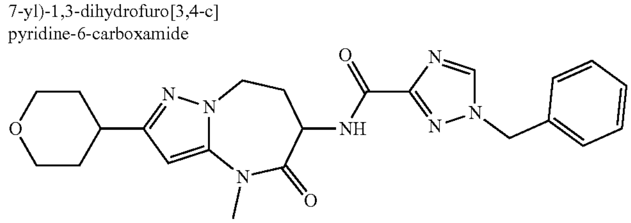 1-benzyl-N-(4-methyl-5-oxo-2-(tetrahydro-2H-pyran-4-yl)-5,6,7,8-tetrahydro-4H-pyrazolo[ | $^1$H NMR (400MHz, $CD_3OD$) δ 8.56 (s, 1H), 7.36-7.32 (m, 5H), 6.19 (s, 1H), 5.47 (s, 2H), 4.53-4.51 (m, 1H), 4.50-4.48 (m, 1H), 4.33-4.31 (m, 1H), 4.01-3.99 (m, 2H), 3.57-3.51 (m, 2H), 3.33 (s, 3H), 2.89-2.84 (m, 2H), 2.26-2.25 (m, 1H), 1.90-1.85 (m, 2H), 1.79-1.75 (m, 2H). | 450.2 |

TABLE 2-continued

| Compound Example # Method | RIP1 Ki (μM) | Structure and Name | $^1$H NMR Data | MS (m/z) |
|---|---|---|---|---|
| | | 1,5-a][1,3]diazepin-6-yl)-1H-1,2,4-triazole-3-carboxamide | | |
| Example 235 WX Method XXXX | 0.226 | 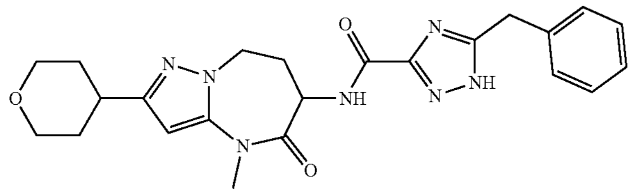 [SMILES: CN1C(=O)C(NC(=O)c2n[nH]c(Cc3ccccc3)n2)CCn2nc(C3CCOCC3)cc21] 5-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 7.30-7.20 (m, 5H), 6.19 (s, 1H), 4.30-4.28 (m, 2H), 4.25-4.22 (m, 3H), 3.87-3.84 (m, 2H), 3.30-3.26 (m, 2H), 3.18 (s, 3H), 2.78-2.73 (m, 1H), 2.42-2.40 (m, 2H), 1.80-1.56 (m, 4H). | 450.2 |
| Example 236 WX Method ZZZZ | 8 | 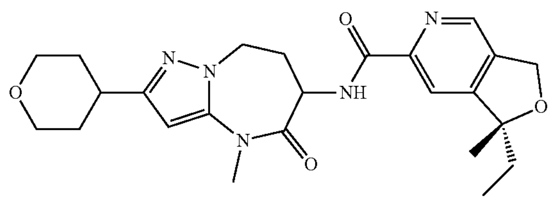 [SMILES: CC[C@@]1(C)OCc2cnc(C(=O)NC3CCn4nc(C5CCOCC5)cc4N(C)C3=O)cc21] (1R)-1-ethyl-1-methyl-N-(4-methyl-5-oxo-2-(tetrahydro-2H-pyran-4-yl)-5,6,7,8-tetrahydro-4H-pyrazolo[1,5-a][1,3]diazepin-6-yl)-1,3-dihydrofuro[3,4-c]pyridine-6-carboxamide | $^1$H NMR (400 MHz, $CD_3OD$) δ 8.56 (s, 1H), 7.86 (s, 1H), 6.20 (s, 1H), 5.16-5.15 (m, 2H), 4.59-4.52 (m, 1H), 4.36-4.34 (m, 1H), 4.29-4.25 (m, 1H), 4.02-4.00 (m, 2H), 3.58-3.53 (m, 2H), 3.35 (s, 3H), 2.94-2.87 (m, 2H), 2.30-2.21 (m, 1H), 1.89-1.81 (m, 6H), 1.46 (s, 3H), 0.77 (t, J = 7.2 Hz, 3H). | 454.2 |
| Example 237 WX Method YYYY | 1.4 | 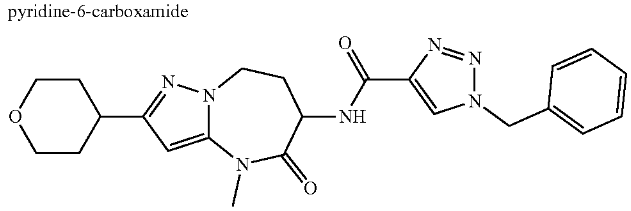 1-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,3-triazole-4-carboxamide | $^1$H NMR (400 MHz, $CD_3OD$) δ 8.34 (s, 1H), 7.37-7.32 (m, 5H), 6.18 (s, 1H), 5.63 (s, 2H), 4.53-4.48 (m, 1H), 4.34-4.32 (m, 1H), 4.26-4.17 (m, 1H), 4.01-3.98 (m, 2H), 3.57-3.51 (m, 2H), 3.33 (s, 3H), 2.88-2.82 (m, 2H), 2.28-2.21 (m, 1H), 1.87-1.76 (m, 4H). | 450.1 |
| Example 238 WX Method V | 0.0547 | 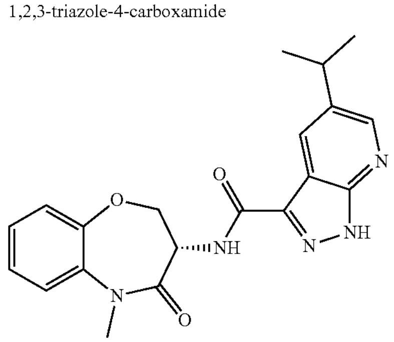 (S)-5-isopropyl-N-(5-methyl-4-oxo-2,3,4,5-tetrahydrobenzo[b][1,4]oxazepin-3-yl)-1H-pyrazolo[3,4-b]pyridine-3-carboxamide | $^1$H NMR (400 MHz, DMSO-$d_6$) δ 14.22 (s, 1H), 8.57-8.54 (m, 2H), 8.22 (d, J = 1.6 Hz, 1H), 7.53-7.52 (m, 1H), 7.51-7.26 (m, 3H), 4.96-4.91 (m, 1H), 4.69-4.63 (m, 1H), 4.48-4.43 (m, 1H), 3.33 (s, 3H), 3.14-3.07 (m, 1H), 1.26 (d, J = 7.2 Hz, 6H). | 380.1 |

TABLE 2-continued

| Compound Example # Method | RIP1 Ki (μM) | Structure and Name | $^1$H NMR Data | MS (m/z) |
|---|---|---|---|---|
| Example 239 WX Method W | 0.289 | 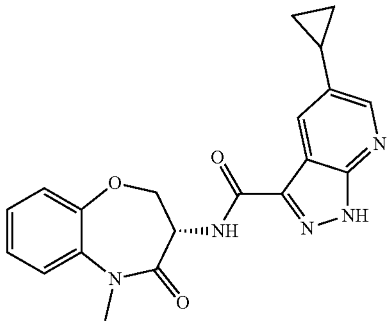 [SMILES: CN1C(=O)[C@@H](NC(=O)c2n[nH]c3ncc(C4CC4)cc23)COc2ccccc21] (S)-5-cyclopropyl-N-(5-methyl-4-oxo-2,3,4,5-tetrahydrobenzo[b][1,4]oxazepin-3-yl)-1H-pyrazolo[3,4-b]pyridine-3-carboxamide | $^1$H NMR (400 MHz, DMSO-$d_6$) δ 14.20 (s, 1H), 8.54 (d, J = 8.0 Hz, 1H), 8.46 (s, 1H), 7.98 (s, 1H), 7.52-7.50 1H), 7.34-7.25 (m, 3H), 4.94-4.90 (m, 1H), 4.68-4.62 (m, 1H), 4.47-4.42 (m, 1H), 3.32 (s, 3H), 2.15-2.09 (m, 1H), 1.04-1.00 (m, 2H), 0.74-0.71 (m, 2H). | 378.1 |
| Example 240 WX Method SS | 0.0846 | 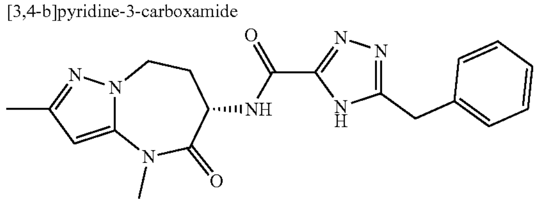 (S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, $CD_3OD$): δ 7.41-7.31 (m, 5H), 6.43 (s, 1H), 4.73-4.68 (m, 1H), 4.52-4.47 (m, 1H), 4.43-4.38 (m, 3H), 3.38 (s, 3H), 2.93-2.83 (m, 1H), 2.48-2.41 (m, 4H). | 380.1 |
| Example 241 WX Method TT | 8.9 | 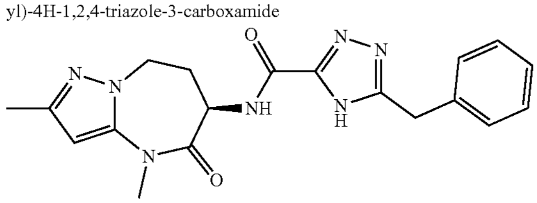 (R)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, $CD_3OD$): δ 7.41-7.33 (m, 5H), 6.39 (s, 1H), 4.70-4.63 (m, 1H), 4.49-4.39 (m, 2H), 4.36 (s, 2H), 3.37 (s, 3H), 2.92-2.82 (m, 1H), 2.46-2.41 (m, 1H), 2.39 (s, 3H). | 380.1 |
| Example 242 WX Method UUU | 5.7 | 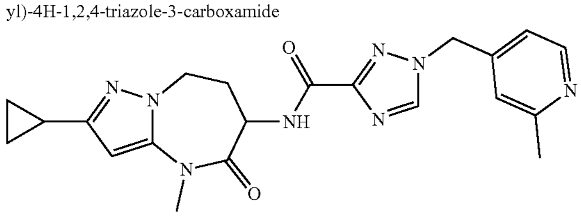 N-(2-cyclopropyl-4-methyl-5-oxo-5,6,7,8-tetrahydro-4H-pyrazolo[1,5-a][1,3]diazepin-6-yl)-1-((2-methylpyridin-4-yl)methyl)-1H-1,2,4-triazole-3-carboxamide | $^1$H NMR (400MHz, $CD_3OD$) δ 8.66 (s, 1H), 8.38 (d, J = 5.2 Hz, 1H), 7.20 (s, 1H), 7.11 (d, J = 5.2 Hz, 1H), 6.01 (s, 1H), 5.54 (s, 2H), 4.55-4.51 (m, 1H), 4.32-4.28 (m, 1H), 4.23-4.19 (m, 1H), 2.87-2.80 (m, 1H), 2.51 (s, 3H), 2.28-2.21 (m, 1H), 1.93-1.87 (m, 1H), 0.97-0.90 (m, 2H), 0.77-0.70 (m, 2H). | 421.2 |
| Example 243 WX Method BBBBB | 0.27 | 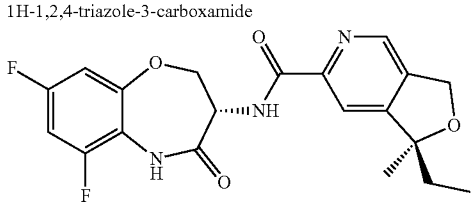 (S)-N-((S)-6,8-difluoro-4-oxo-2,3,4,5-tetrahydrobenzo[b][1,4]oxazepin-3-yl)-1-ethyl-1-methyl-1,3-dihydrofuro[3,4-c]pyridine-6-carboxamide | $^1$H NMR (400MHz, $CD_3OD$) δ 8.57 (s,1H), 7.90 (s, 1H), 6.99-6.84 (m, 2H), 5.22-5.13 (m, 2H), 5.09-5.05 (m, 1H), 4.72-4.68 (m, 1H), 4.55-4.48 (m, 1H), 1.89-1.83 (m, 2H), 1.47 (s, 3H), 0.78 (t, J = 7.2 Hz, 3H). | 404.1 |

TABLE 2-continued

| Compound Example # Method | RIP1 Ki (μM) | Structure and Name | $^1$H NMR Data | MS (m/z) |
|---|---|---|---|---|
| Example 244 WX Method AAAAA | 0.0368 | 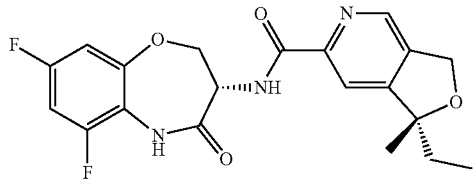 [SMILES: CC[C@@]1(C)OCc2cnc(C(=O)N[C@H]3COc4cc(F)cc(F)c4NC3=O)cc21] (R)-N-((S)-6,8-difluoro-4-oxo-2,3,4,5-tetrahydrobenzo[b][1,4]oxazepin-3-yl)-1-ethyl-1-methyl-1,3-dihydrofuro[3,4-c]pyridine-6-carboxamide | $^1$H NMR (400 MHz, $CD_3OD$) δ 8.57 (s,1H), 7.90 (s, 1H), 6.99-6.84 (m, 2H), 5.17-5.13 (m, 2H), 5.09-5.05 (m, 1H), 4.72-4.68 (m, 1H), 4.55-4.48 (m, 1H), 1.89-1.83 (m, 2H), 1.47 (s, 3H), 0.78 (t, J = 7.6 Hz, 3H). | 404.1 |
| Example 245 WX Method BBBB | 0.782 | 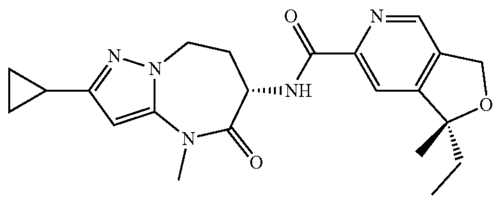 [SMILES: CC[C@@]1(C)OCc2cnc(C(=O)N[C@H]3CCn4nc(C5CC5)cc4N(C)C3=O)cc21] (R)-N-((S)-2-cyclopropyl-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide | $^1$H NMR (400 MHz, $CD_3OD$) δ 8.61 (s, 1H), 7.92 (s, 1H), 6.06 (s 1H), 5.25-5.21 (m, 2H), 4.63-4.59 (m, 1H), 4.38-4.23 (m, 2H), 3.38 (s, 3H), 3.02-2.93 (m, 1H), 2.31-2.30 (m, 1H), 1.96-1.88 (m, 3H), 1.51 (s, 3H), 1.00-0.98 (m, 2H), 0.84-0.79 (m, 5H). | 410.2 |
| Example 246 WX Method ZZ | 0.695 | 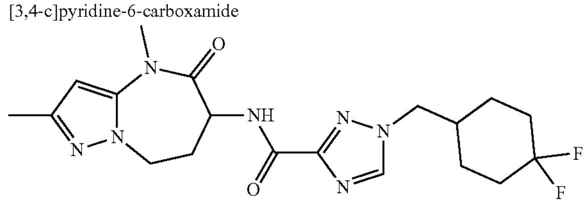 1((4,4-difluorocyclohexyl)methyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.47 (s, 1H), 6.10 (s, 1H), 4.52-4.49 (m, 1H), 4.29-4.17 (m, 4H), 3.29 (s, 3H), 2.85-2.80 (m, 1H), 2.27-2.22 (m, 4H), 2.20-2.04 (m, 4H), 1.78-1.67 (m, 3H), 1.34-1.27 (m, 2H). | 422.1 |
| Example 247 WX Method AAA | 0.221 | 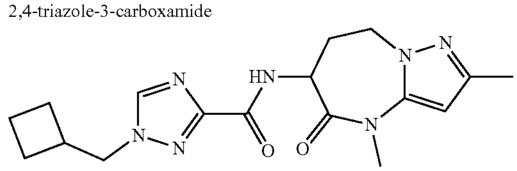 1-(cyclobutylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz $CD_3OD$) δ 8.44 (s, 1H), 6.09 (s, 1H), 4.51-4.48 (m, 1H), 4.29-4.19 (m, 4H), 3.28 (s, 3H), 2.87-2.83 (m, 2H), 2.23-2.04 (m, 4H), 2.05-2.03 (m, 2H), 1.92-1.90 (m, 2H), 1.84-1.80 (m, 2H). | 358.1 |
| Example 248 WX Method BBB | 1.1 | 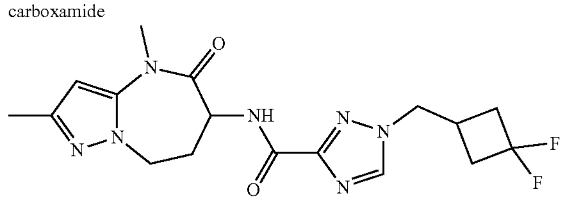 1-((3,3-difluorocyclobutyl)methyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.53 (s, 1H), 6.12 (s, 1H), 4.54-4.52 (m, 1H), 4.41 (d, J = 6.8 Hz, 2H), 4.32-4.22 (m, 2H), 3.31 (s, 3H), 2.85-2.68 (m, 2H), 2.66-2.64 (m, 2H), 2.48-2.44 (m, 2H), 2.30-2.26 (m, 4H). | 394.1 |
| Example 249 WX Method DDD | 0.0921 | 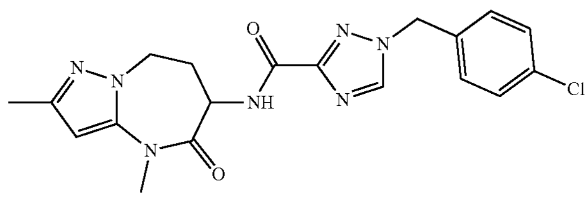 [SMILES: Cc1cc2n(n1)CCC(NC(=O)c1ncn(Cc3ccc(Cl)cc3)n1)C(=O)N2C] | $^1$H NMR (400 MHz, $CD_3OD$) δ 8.70 (s, 1H), 7.37-7.32 (m, 4H), 6.32 (s, 1H), 5.46 (s, 2H), 4.63-4.61 (m, 1H), 4.40-4.30 (m, 2H), 3.29 (s, 3H), 2.88-2.82 (m, 1H), 2.38-2.32 (m, 4H). | 414.1 |

TABLE 2-continued

| Compound Example # Method | RIP1 Ki (μM) | Structure and Name | $^1$H NMR Data | MS (m/z) |
|---|---|---|---|---|
| | | 1-(4-chlorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | | |
| Example 250 WX Method EEE | 1 | 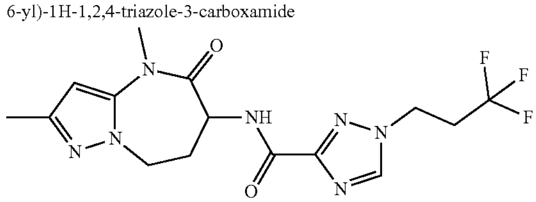 N-(2,4-dimethyl-5-oxo-5,6,7,8-tetrahydro-4H-pyrazolo[1,5-a][1,3]diazepin-6-yl)-1-(3,3,3-trifluoropropyl)-1H-1,2,4-triazole-3-carboxamide | $^1$H NMR (400 MHz, $CD_3OD$) δ 8.52 (s, 1H), 6.10 (s, 1H), 4.56-4.52 (m, 3H), 4.29-4.20 (m, 2H), 3.29 (s, 3H), 2.90-2.83 (m, 3H), 2.29-2.24 (m, 4H). | 386.0 |
| Example 251 WX Method GGG | 0.136 | 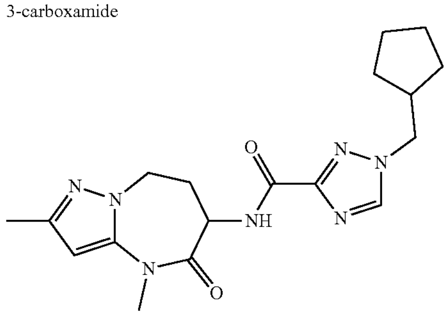 1-(cyclopentylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.50 (s, 1H), 6.12 (s, 1H), 4.57-4.52 (m, 1H), 4.35-4.15 (m, 4H), 3.34 (s, 3H), 2.91-2.81 (m, 1H), 2.53-2.44 (m, 1H), 2.30-2.23 (m, 4H), 1.70-1.58 (m, 6H), 1.34-1.28 (m, 2H). | 372.2 |
| Example 252 WX Method LL | 0.0707 | 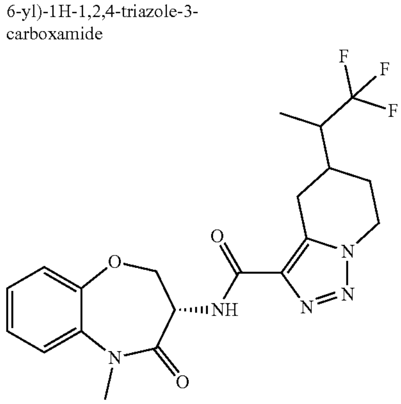 N-((S)-5-methyl-4-oxo-2,3,4,5-tetrahydrobenzo[b][1,4]oxazepin-3-yl)-5-(1,1,1-trifluoropropan-2-yl)-4,5,6,7-tetrahydro-[1,2,3]triazolo[1,5-a]pyridine-3-carboxamide | $^1$H NMR (400 MHz, DMSO-$d_6$) δ 8.43 (d, J = 6.4 Hz, 1H), 7.52-7.45 (m, 1H), 7.36-7.19 (m, 3H), 4.90-4.78 (m, 1H), 4.65-4.53 (m, 2H), 4.39 (t, J = 8.4 Hz, 1H), 4.31-4.17 (m, 1H), 3.30 (s, 3H), 3.21-3.04 (m, 1H), 2.79-2.59 (m, 2H), 2.35-2.18 (m, 1H), 2.14-1.99 (m, 1H), 1.97-1.77 (m, 1H), 1.16-1.02 (m, 3H). | 438.1 |
| Example 253 WX Method FFF | 0.171 | 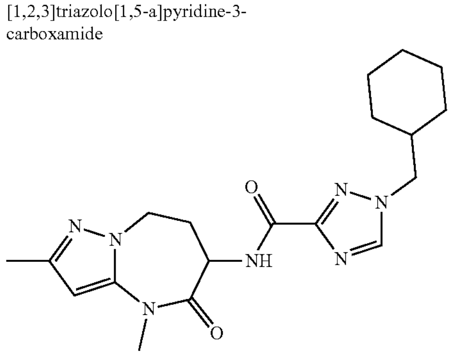 1-(cyclohexylmethyl)-N-(2,4-dimethyl-5-oxo-5,6,7,8- | $^1$H NMR (400 MHz, $CD_3OD$): δ 8.46 (s, 1H), 6.12 (s, 1H), 4.57-4.52 (m, 1H), 4.35-4.18 (m, 2H), 2H), 4.11 (d, J = 8.0, 2H), 3.34 (s, 3H), 2.91-2.81 (m, 1H), 2.30-2.23 (m, 4H), 1.96-1.91 (m, 1H), 1.76-1.68 (m, 3H), 1.63-1.56 (m, 2H), 1.33-1.19 (m, 3H), 1.06-0.97 (m, 2H). | 386.2 |

TABLE 2-continued

| Compound Example # Method | RIP1 Ki (μM) | Structure and Name | $^1$H NMR Data | MS (m/z) |
|---|---|---|---|---|
| | | tetrahydro-4H-pyrazolo[1,5-a][1,3] diazepin-6-yl)-1H-1,2,4-triazole-3-carboxamide | | |
| Example 254 WX Method NNN | 2.2 | 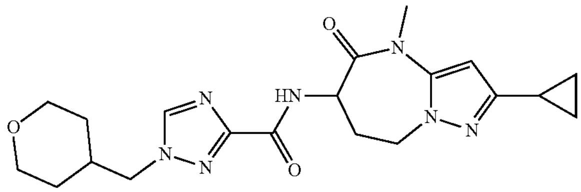 [SMILES: CN1C(=O)C(NC(=O)c2ncn(CC3CCOCC3)n2)CCn2nc(C3CC3)cc21] N-(2-cyclopropyl-4-methyl-5-oxo-5,6,7,8-tetrahydro-4H-pyrazolo [1,5-41,3]diazepin-6-yl)-1-((tetrahydro-2H-pyran-4-yl) methyl)-1H-1,2,4-triazole-3-carboxamide | $^1$H NMR (400 MHz, $CD_3OD$) δ 8.05 (s, 1H), 6.03 (s, 1H), 4.60-4.56 (m, 2H), 4.34-4.30 (m, 1H), 4.18-4.16 (m, 2H), 4.00-3.94 (m, 2H), 3.44-3.40 (m, 2H), 3.38-3.34 (m, 3H), 2.87-2.86 (m, 1H), 2.28-2.26 (m, 2H), 1.92-1.91 (m, 1H), 1.50-1.41 (m, 2H), 1.39-1.28 (m, 2H), 0.97-0.94 (m, 2H), 0.78-0.75 (m, 2H). | 414.2 |
| Example 255 WX Method OOO | 0.421 | 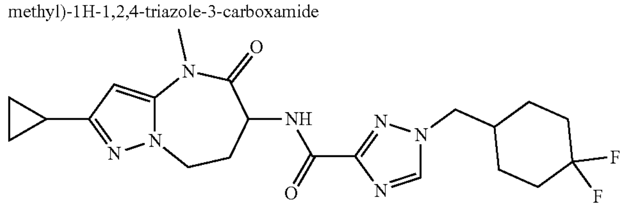 N-(2-cyclopropyl-4-methyl-5-oxo-5,6,7,8-tetrahydro-4H-pyrazolo[1,5-41,3]diazepin-6-yl)-1((4,4-difluorocyclohexyl)methyl)-1H-1,2,4-triazole-3-carboxamide | $^1$H NMR (400 MHz, $CD_3OD$) δ 8.48 (s, 1H), 6.00 (s, 1H), 4.55-4.50 (m, 1H), 4.29-4.18 (m, 4H), 3.33 (s, 3H), 2.88-2.83 (m, 1H), 2.27-2.22 (m, 1H), 2.05-2.04 (m, 3H), 1.90-1.66 (m, 5H), 1.35-1.32 (m, 2H), 0.95-0.92 (m, 2H), 0.75-0.72 (m, 2H). | 448.2 |
| Example 256 WX Method PPP | 0.21 | 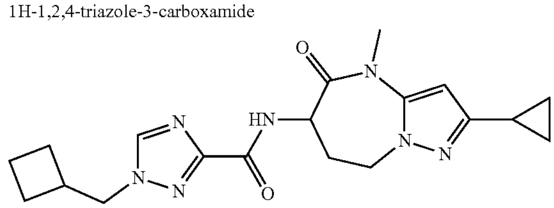 1-(cyclobutylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.47 (s, 1H), 6.01 (s, 1H), 4.55-4.50 (m, 1H), 4.34-4.28 (m, 4H), 3.32 (s, 3H), 2.90-2.84 (m, 2H), 2.26-2.08 (m, 1H), 1.95-1.93 (m, 2H), 1.92-1.83 (m, 5H), 0.99-0.93 (m, 2H), 0.76-0.73 (m, 2H). | 384.2 |
| Example 257 Method QQQ | 0.0829 | 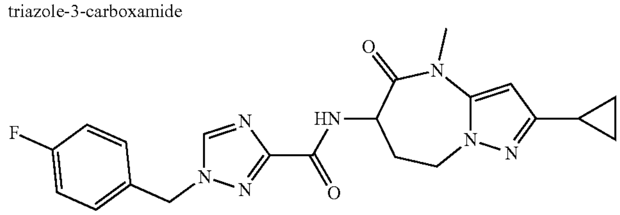 N-(2-cyclopropyl-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide | $^1$H NMR (400 MHz, $CDCl_3$) δ 8.02 (s, 1H), 7.31-7.27 (m, 2H), 7.10-7.06 (m, 2H), 5.78 (s, 1H), 5.36 (s, 2H), 4.78-4.74 (m, 1H), 4.40-4.34 (m, 1H), 4.13-4.06 (m, 1H), 3.34 (s, 3H), 3.19-3.14 (m, 1H), 2.04-2.01 (m, 1H), 2.00-1.88 (m, 1H), 0.95-0.93 (m, 2H), 0.75-0.74 (m, 2H). | 424.2 |
| Example 258 WX Method RRR | 1.6 | 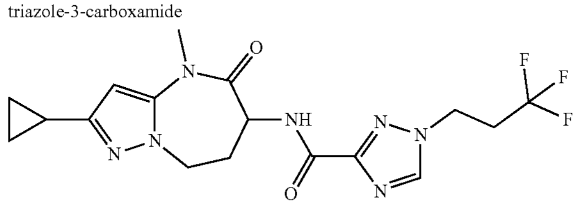 N-(2-cyclopropyl-4-methyl-5-oxo-5,6,7,8-tetrahydro-4H-pyrazolo[1,5-a][1,3]diazepin-6-yl)-1-(3,3,3-trifluoropropyl)-1H-1,2,4-triazole-3-carboxamide | $^1$H NMR (400 MHz, DMSO-$d_6$) δ 8.72 (s, 1H), 8.55 (d, J = 7.6 Hz, 1H), 6.05 (s, 1H), 4.52 (t, J = 6.8 Hz, 2H), 4.31-4.22 (m, 2H), 4.20-4.07 (m, 1H), 3.18 (s, 3H), 3.00-2.90 (m, 2H), 2.57-2.55 ( m, 1H), 2.33-2.30 (m, 1H), 1.85-1.81 (m, 1H), 0.85-0.82 (m, 2H), 0.66-0.63 (m, 2H). | 412.1 |

TABLE 2-continued

| Compound Example # Method | RIP1 Ki (μM) | Structure and Name | $^1$H NMR Data | MS (m/z) |
|---|---|---|---|---|
| Example 259 WX Method SSS | 0.789 | 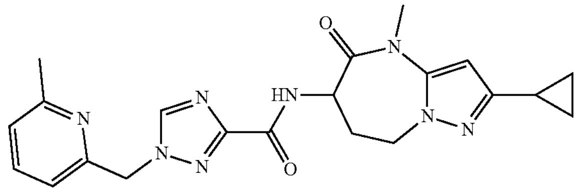 [SMILES: Cc1cccc(Cn2cnc(C(=O)NC3CCn4nc(C5CC5)cc4N(C)C3=O)n2)n1] N-(2-cyclopropyl-4-methyl-5-oxo-5,6,7,8-tetrahydro-4H-pyrazolo[1,5-a][1,3]diazepin-6-yl)-1-((6-methylpyridin-2-yl)methyl)-1H-1,2,4-triazole-3-carboxamide | $^1$H NMR (400 MHz, DMSO-$d_6$) δ 8.79 (s, 1H), 8.52 (d, J = 7.6 Hz, 1H), 7.67 (t, J = 7.6 Hz, 1H), 7.18 (d, J = 8.0 Hz, 1H), 7.04 (d, J = 8.0 Hz, 1H), 6.03 (s, 1H), 5.51 (s, 2H), 4.34-4.19 (m, 2H), 4.12-4.07 (m, 1H), 3.17 (s, 3H), 2.54-2.52 (m, 1H), 2.40 (s, 3H), 2.35-2.30 (m, 1H), 1.88-1.80 (m, 1H), 0.84-0.82 (m, 2H), 0.65-0.62 (m, 2H). | 421.2 |
| Example 260 WX Method XXX | 1.9 | 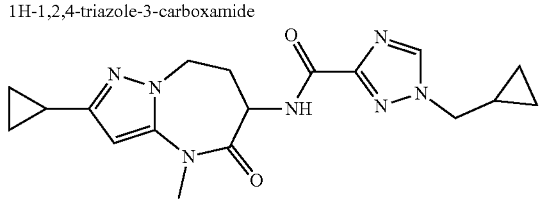 N-(2-cyclopropyl-4-methyl-5-oxo-5,6,7,8-tetrahydro-4H-pyrazolo [1,5-a][1,3]diazepin-6-yl)-4-1-(cyclopropylmethyl)-1H-1,2, triazole-3-carboxamide | $^1$H NMR (400 MHz, DMSO-$d_6$) δ 8.68 (s, 1H), 8.51 (d, J = 8.0 Hz, 1H), 6.07 (s, 1H), 4.33-4.22 (m, 2H), 4.12-4.08 (m, 3H), 3.20 (s, 3H), 2.58-2.55 (m, 1H), 2.34-2.30 (m, 1H), 1.86-1.83 (m, 1H), 1.30-1.26 (m, 1H), 0.87-0.84 (m, 2H), 0.68-0.65 (m, 2H), 0.56-0.53 (m, 2H), 0.41-0.38 (m, 2H). | 370.1 |
| Example 261 WX Method WWW | 0.104 | 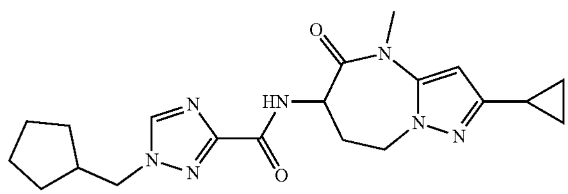 [SMILES: CN1C(=O)C(NC(=O)c2ncn(CC3CCCC3)n2)CCn2nc(C3CC3)cc21] 1-(cyclopentylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.47 (s, 1H), 5.99 (s, 1H), 4.53-4.48 (m, 1H), 4.27-4.17 (m, 4H), 3.28 (s, 3H), 2.85-2.80 (m, 1H), 2.48-2.47 (m, 1H), 2.22-2.10 (m, 1H), 1.88-1.78 (m, 1H), 1.75-1.66 (m, 6H), 1.28-1.25 (m, 2H), 0.93-0.90 (m, 2H), 0.73-0.71 (m, 2H). | 398.1 |
| Example 262 WX Method III | 0.511 | 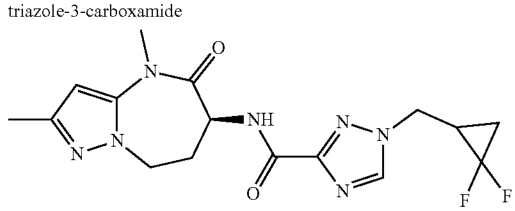 1-((2,2-((2,2-difluorocyclopropyl)methyl)-N-((S)-2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.50 (s, 1H), 6.10 (s, 1H), 4.55-4.43 (m, 2H), 4.33-4.20 (m, 3H), 3.29 (s, 3H), 2.87-2.80 (m, 1H), 2.29-2.24 (m, 5H), 1.64-1.60 (m, 1H), 1.48-1.42 (m, 1H). | 380.1 |
| Example 263 WX Method PPPPPP | 0.854 | 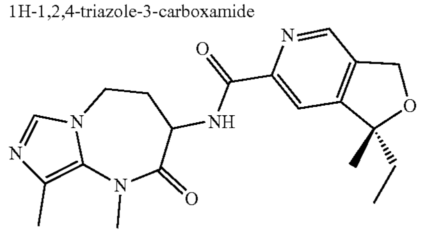 (1R)-N-(1,9-dimethyl-2-oxo-2,3,4,5-tetrahydro-1H-imidazo [1,5-a][1,3]diazepin-3-yl)-1-ethyl-1-methyl-1,3-dihydrofuro[3,4-c]pyridine-6-carboxamide | $^1$H NMR (400 MHz, $CD_3OD$) δ 8.57 (s, 1H), 7.88 (s, 1H), 7.58 (s, 1H), 5.21-5.16 (m, 2H), 4.87-4.57 (m, 1H), 4.39-4.33 (m, 1H), 4.00-3.96 (m, 1H), 3.34 (s, 3H), 2.78-2.76 (m, 1H), 2.23 (s, 3H), 2.15-2.11 (m, 1H), 1.89-1.83 (m, 2H), 1.47 (s, 3H), 0.80-0.76 (m, 3H). | 384.2 |

TABLE 2-continued

| Compound Example # Method | RIP1 Ki (μM) | Structure and Name | $^1$H NMR Data | MS (m/z) |
|---|---|---|---|---|
| Example 264 WX Method UUUU | 0.232 | 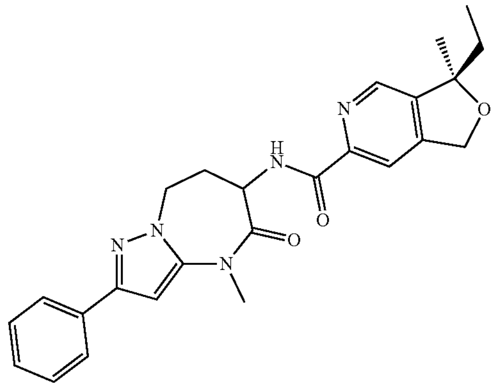 [SMILES: CC[C@@]1(C)OCc2cc(C(=O)NC3CCn4nc(-c5ccccc5)cc4N(C)C3=O)ncc21] (3R)-3-ethyl-3-methyl-N-(4-methyl-5-oxo-2-phenyl-5,6,7,8-tetrahydro-4H-pyrazolo[1,5-a][1,3]diazepin-6-yl)-1,3-dihydrofuro[3,4-c]pyridine-6-carboxamide | $^1$H NMR (400 MHz, $CD_3OD$) δ 8.55 (s, 1H), 7.86-7.80 (m, 3H), 7.43-7.31 (m, 3H), 6.70 (s, 1H), 5.19-5.12 (m, 2H), 4.68-4.36 (m, 3H), 3.42 (s, 3H), 3.02-2.94 (m, 1H), 2.35-2.27 (m, 1H), 1.87-1.82 (m, 2H), 1.45 (s, 3H), 0.78-0.74 (m, 3H). | 446.1 |
| Example 265 WX Method VVVV | 4.9 | 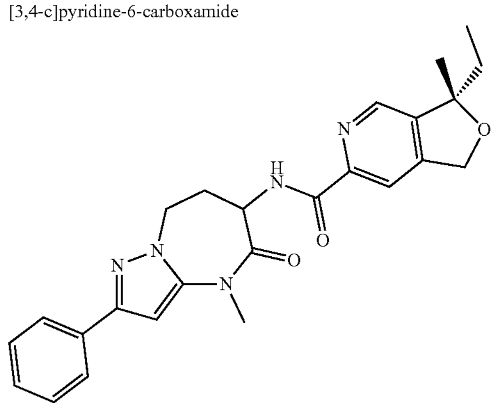 (3S)-3-ethyl-3-methyl-N-(4-methyl-5-oxo-2-phenyl-5,6,7,8-tetrahydro-4H-pyrazolo[1,5-a][1,3]diazepin-6-yl)-1,3-dihydrofuro[3,4-c]pyridine-6-carboxamide | $^1$H NMR (400 MHz, $CD_3OD$) δ 8.55 (s, 1H), 7.86-7.80 (m, 3H), 7.43-7.31 (m, 3H), 6.70 (s, 1H), 5.19-5.12 (m, 2H), 4.68-4.36 (m, 3H), 3.42 (s, 3H), 3.02-2.94 (m, 1H), 2.35-2.29 (m, 1H), 1.87-1.82 (m, 2H), 1.45 (s, 3H), 0.78-0.74 (m, 3H). | 446.1 |
| Example 266 WX Method UU | 1.3 | 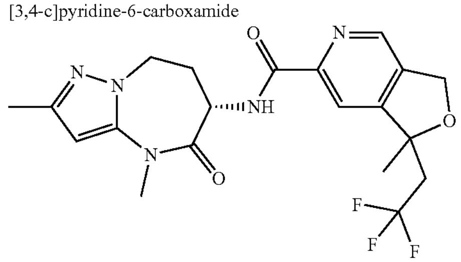 N-((S)-2,4-dimethyl-5-oxo-5,6,7,8-tetrahydro-4H-pyrazolo[1,5-a][1,3]diazepin-6-yl)-1-methyl-1-(2,2,2-trifluoroethyl)-1,3-dihydrofuro[3,4-c]pyridine-6-carboxamide | $^1$H NMR (400 MHz, $CD_3OD$): δ 8.61 (s 1H) 8.03 (s 1H) 6.13 (s, 1H), 5.20 (s, 2H), 4.63-4.57 (m, 1H), 4.35-4.24 (m, 2H), 3.35 (s, 3H), 2.92-2.81 (m, 3H), 2.32-2.25 (m, 4H), 1.57 (s, 3H). | 438.2 |
| Example 267 WX Method A | 0.0374 | 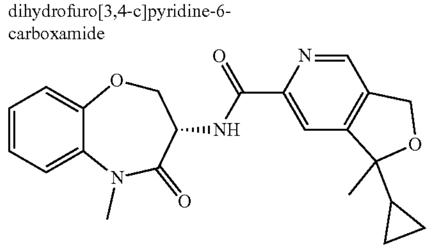 1-cyclopropyl-1-methyl-N-((S)-5-methyl-4-oxo-2,3,4,5-tetrahydrobenzo[b][1,4]oxazepin-3-yl)- | $^1$H NMR (400 MHz, $CD_3OD$) δ 8.58 (s, 1H), 7.95 (s, 1H), 7.47-7.28 (m, 4H), 5.17-5.03 (m, 3H), 4.69-4.65 (m, 1H), 4.45-4.40 (m, 1H), 3.45 (s, 3H), 1.52 (s, 3H), 1.31-1.26 (m, 1H), 0.50-0.28 (m, 4H). | 394.0 |

TABLE 2-continued

| Compound Example # Method | RIP1 Ki (μM) | Structure and Name | $^1$H NMR Data | MS (m/z) |
|---|---|---|---|---|
| | | 1,3-dihydrofuro[3,4-c] pyridine-6-carboxamide | | |
| Example 268 WX Method CCC | 0.0977 | 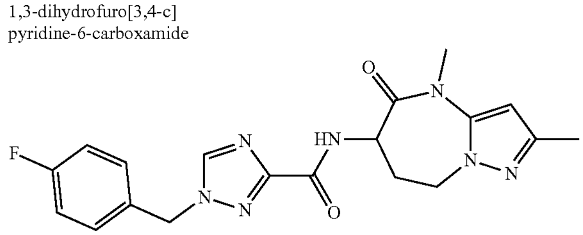 N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide | $^1$H NMR (400 MHz, DMSO-$d_6$) δ 8.81 (s, 1H), 8.53 (d, J = 8.0 Hz, 1H), 7.40-7.36 (m, 2H), 7.23-7.19 (m, 2H), 6.12 (s, 1H), 5.47 (s, 2H), 4.32-4.26 (m, 2H), 4.12-4.09 (m, 1H), 3.21 (s, 3H), 2.50-2.44 (m, 2H), 2.16 (s, 3H). | 398.1 |
| Example 269 WX Method VVV | 0.811 | 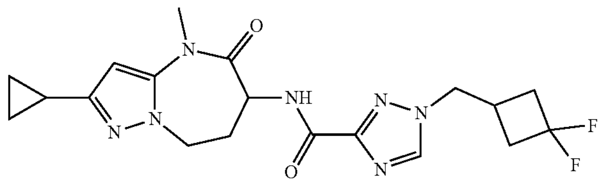 [SMILES: CN1C(=O)C(NC(=O)c2ncn(CC3CC(F)(F)C3)n2)CCn2nc(C3CC3)cc21] N-(2-cyclopropyl-4-methyl-5-oxo-5,6,7,8-tetrahydro-4H-pyrazolo[1,5-a][1,3]diazepin-6-yl)-1((3,3-difluorocyclobutyl) methyl)-1H-1,2,4-triazole-3-carboxamide | $^1$H NMR (400 MHz, $CDCl_3$) δ 8.08 (s, 1H), 8.01 (d, J = 6.4 Hz, 1H), 5.76 (s, 1H), 4.76-4.73 (m, 1H), 4.39-4.30 (m, 3H), 4.11-4.05 (m, 1H), 3.33 (s, 3H), 3.20-3.12 (m, 1H), 2.78-2.70 (m, 3H), 2.39-2.33 (m, 2H), 1.90-1.87 (m, 2H), 0.94-0.91 (m, 2H), 0.75-0.72 (m, 2H). | 420.2 |
| Example 270 WX Method HHH | 0.0885 | 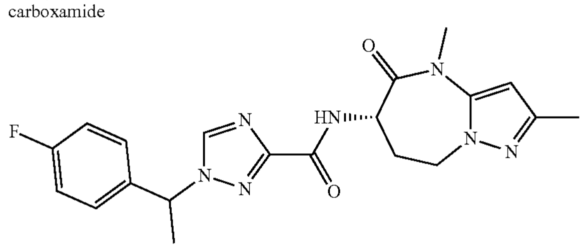 N-((S)-2,4-dimethyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide | $^1$H NMR (400 MHz, DMSO-$d_6$) δ 8.51 (s, 1H), 8.53(d, J = 7.6 Hz, 1H), 7.40-7.37 (m, 2H), 7.22-7.18 (m, 2H), 6.13 (s, 1H), 5.86-5.81 (m, 1H), 4.32-4.25 (m, 2H), 4.12-4.07 (m, 1H), 3.21 (s, 3H), 2.67-2.50 (m, 2H), 2.16 (s, 3H), 1.84 (d, J = 7.2 Hz, 3H). | 412.3 |
| Example 271 WX Method KKK | 0.0936 | 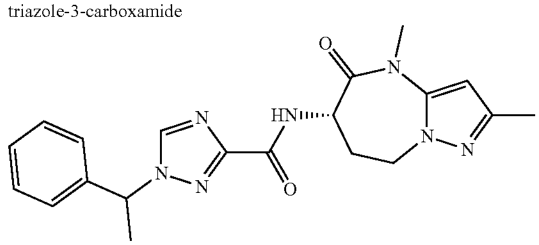 N-((S)-2,4-dimethyl-5-oxo-5,6,7,8-tetrahydro-4H-pyrazolo[1,5-a][1,3]diazepin-6-yl)-1-(1-phenylethyl)-1H-1,2,4-triazole-3-carboxamide | $^1$H NMR (400 MHz, DMSO-$d_6$) δ 8.87 (s, 1H), 8.53 (d, J = 8.0 Hz, 1H), 7.38-7.30 (m, 5H), 6.13 (s, 1H), 5.84-5.78 (m, 1H), 4.33-4.23 (m, 2H), 4.12-4.09 (m, 1H), 3.21 (s, 3H), 2.59 2.57 (m, 1H), 2.37-2.34 (m, 1H), 2.16 (s, 3H), 1.85 (d, J = 7.2 Hz, 3H). | 394.1 |
| Example 272 WX Method FFFFF | 0.0452 | 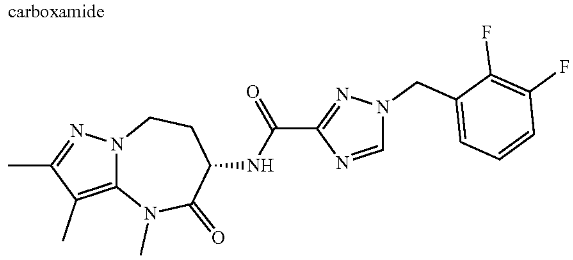 (S)-1-(2,3-difluorobenzyl)-N-(2,3,4-trimethyl-5-oxo-5,6,7,8-tetrahydro-4H-pyrazolo[1,5-a] | $^1$H NMR (400 MEL, $CD_3OD$) δ 8.61 (s, 1H), 7.29-7.26 (m, 1H), 7.18-7.15 (m, 2H), 5.59 (s, 2H), 4.43-4.38 (m, 1H), 4.24-4.18 (m, 2H), 3.30 (s, 3H), 2.78-2.70 (m, 1H), 2.19 (m, 4H), 2.00 (s, 3H). | 430.2 |

TABLE 2-continued

| Compound Example # Method | RIP1 Ki (μM) | Structure and Name | $^1$H NMR Data | MS (m/z) |
|---|---|---|---|---|
| | | [1,3]diazepin-6-yl)-1H-1,2,4-triazole-3-carboxamide | | |
| Example 273 WX Method GGGGG | 0.0467 | 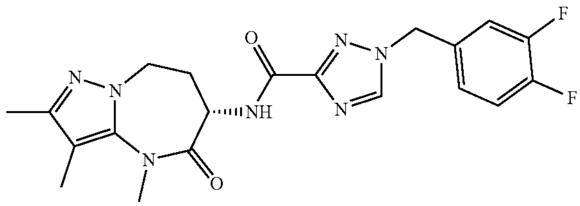 (S)-1-(3,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.60 (s, 1H), 7.32-7.24 (m, 2H), 7.18-7.17 (m, 1H), 5.45 (s, 2H), 4.39-4.39 (m, 1H), 4.24-4.18 (m, 2H), 3.30 (s, 3H), 2.81-2.73 (m, 1H), 2.20-2.16 (m, 4H), 2.00 (s, 3H). | 430.2 |
| Example 274 WX Method DDDDD | 0.0395 | 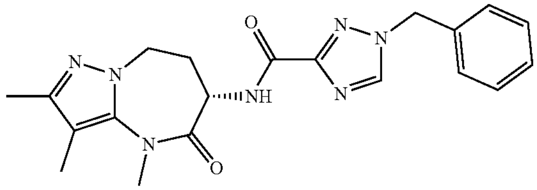 [SMILES: Cc1nn2c(c1C)N(C)C(=O)[C@@H](NC(=O)c1ncn(Cc3ccccc3)n1)CC2] (S)-1-benzyl-N-(2,3,4-trimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.55 (s, 1H), 7.38-7.32 (m, 5H), 5.46 (s, 2H), 4.44-4.39 (m, 1H) 4.24-4.18 (m, 2H), 3.30 (s, 3H), 2.81-2.73 (m, 1H), 2.21-2.18 (m, 4H), 2.00 (s, 3H). | 394.2 |
| Example 275 WX Method VV | 1.1 | 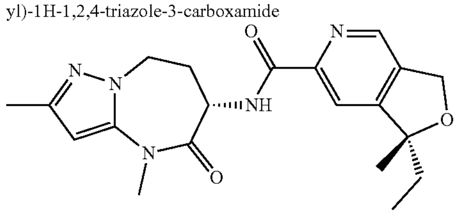 (R)-N-((S)-2,4-dimethyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide | $^1$H NMR (400 MHz, $CD_3OD$) δ 8.57 (s, 1H), 7.87 (s, 1H), 6.13 (s, 1H), 5.21-5.16 (m, 2H), 4.59-4.55 (m, 1H), 4.33-4.24 (m, 2H), 3.35 (s, 3H), 2.95-2.88 (m, 1H), 2.29-2.22 (m, 4H), 1.89-1.83 (m, 2H), 1.47 (s, 3H), 0.77 (t, J = 7.6 Hz, 3H). | 384.2 |
| Example 276 WX Method CCCCC | 0.0936 | 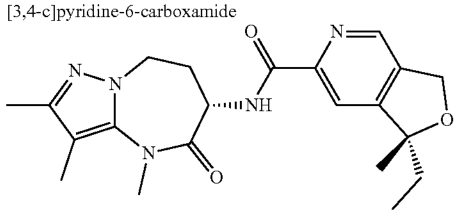 (R)-1-ethyl-1-methyl-N-((S)-2,3,4-trimethyl-5-oxo-5,6,7,8-tetrahydro-4H-pyrazolo[1,5-a][1,3]diazepin-6-yl)-1,3-dihydrofuro[3,4-c]pyridine-6-carboxamide | $^1$H NMR (400 MHz, $CD_3OD$) δ 8.55 (s, 1H) 7.86 (s 1H) 5.20-5.12 (m, 2H), 4.48-4.44 (m, 1H), 4.26-4.21 (m, 2H), 3.34 (s, 3H), 2.87-2.81 (m, 1H), 2.19-2.16 (m, 4H), 2.02 (s, 3H), 1.87-1.82 (m, 2H), 1.46 (s, 3H), 0.76 (t, J = 7.6 Hz, 3H). | 398.2 |
| Example 277 WX Method R | 0.0239 | 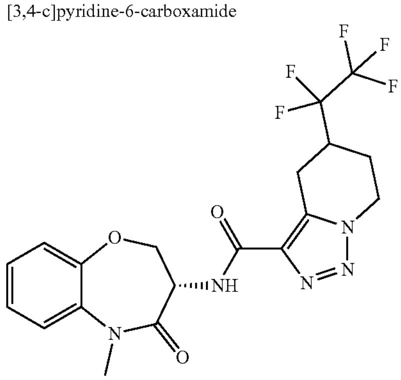 N-((S)-5-methyl-4-oxo-2,3,4,5-tetrahydrobenzo[b][1,4] | $^1$H NMR (400 MHz, $CD_3OD$) δ 7.46-7.40 (m, 1H), 7.36-7.26 (m, 2H), 7.26-7.20 (m, 1H), 5.00-4.97 (m, 1H), 4.72-4.68 (m, 1 H), 4.62-4.57 (m, 1H), 4.43-4.39 (m, 1H), 4.38-4.29 (m, 1H), 3.54-3.45 (m, 1H), 3.42 (s, 3H), 3.05-2.93 (m, 2H), 2.48-2.44 (m, 1H), 2.19-2.07 (m, 1H). | 460.1 |

TABLE 2-continued

| Compound Example # Method | RIP1 Ki (μM) | Structure and Name | $^1$H NMR Data | MS (m/z) |
|---|---|---|---|---|
| | | oxazepin-3-yl)-5-(perfluoroethyl)-4,5,6,7-tetrahydro-[1,2,3]triazolo[1,5-a]pyridine-3-carboxamide | | |
| Example 278 WX Method YYY | 0.516 | 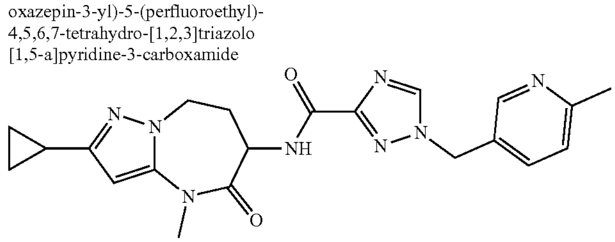 N-(2-cyclopropyl-4-methyl-5-oxo-5,6,7,8-tetrahydro-4H-pyrazolo[1,5-a][1,3]diazepin-6-yl)-1-((6-methylpyridin-3-yl)methyl)-1H-1,2,4-triazole-3-carboxamide | $^1$H NMR (400 MHz, $CD_3OD$) δ 8.63 (s, 1H), 8.47 (d, J = 1.6 Hz, 1H), 7.75-7.73 (m, 1H), 7.32 (d, J = 8.8 Hz, 1H), 6.00 (s, 1H), 5.51 (s, 2H), 4.54-4.49 (m, 1H), 4.29-4.15 (m, 2H), 3.31 (s, 3H), 2.86-2.80 (m, 1H), 2.53 (s, 3H), 2.28-2.23 (m, 1H), 1.92-1.87 (m, 1H), 0.95-0.92 (m, 2H), 0.75-0.72 (m, 2H). | 421.1 |
| Example 279 WX Method X | 0.0981 | 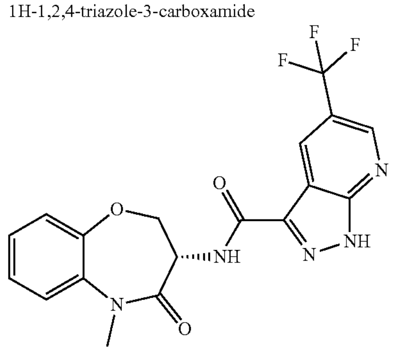 (S)-N-(5-methyl-4-oxo-2,3,4,5-tetrahydrobenzo[b][1,4]oxazepin-3-yl)-5-(trifluoromethyl)-1H-pyrazolo[3,4-b]pyridine-3-carboxamide | $^1$H NMR (400 MHz, DMSO-$d_6$) δ 8.96 (d, J = 2.0 Hz, 1H), 8.80 (d, J = 8.4 Hz, 1H), 8.69 (d, J = 1.2 Hz, 1H), 7.53-7.51 (m, 1H), 7.35-7.26 (m, 3H), 4.98-4.93 (m, 1H), 4.71-4.66 (m, 1H), 4.48-4.44 (m, 1H), 3.33 (s, 3H). | 406.0 |
| Example 280 WX Method HHHHH | 0.0509 | 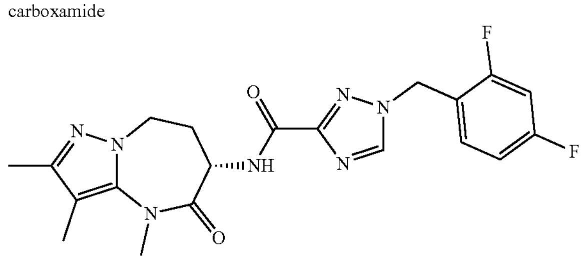 (S)-1-(2,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.59 (s, 1H), 7.49-7.43 (m, 1H), 7.05-6.98 (m, 2H), 5.52 (s, 2H), 4.44-4.40 (m, 1H), 4.24-4.19 (m, 2H), 3.31 (s, 3H), 2.81-2.73 (m, 1H), 2.22-2.19 (s, 4H), 2.01 (s, 3H). | 430.1 |
| Example 281 Method IIIII | 0.0387 | 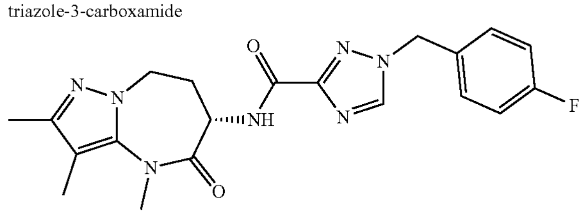 (S)-1-(4-fluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.81 (s, 1H), 8.42 (d, J = 7.6 Hz, 1H), 7.40-7.36 (m, 2H), 7.23-7.19 (m, 2H), 5.47 (s, 2H), 4.25-4.09 (m, 3H), 3.19 (s, 3H), 2.50-2.49 (m, 1H), 2.25-2.10 (m, 1H), 2.09 (s, 3H), 1.93 (s, 3H). | 412.1 |
| Example 282 WX Method HHHH | 0.0594 | 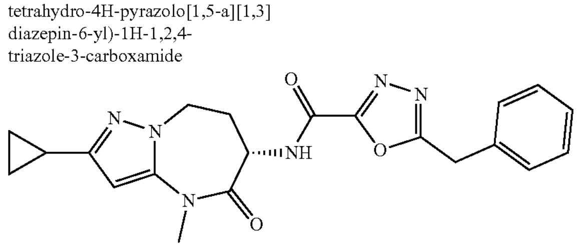 | $^1$H NMR (400 MHz, $CD_3OD$) δ 7.35-7.28 (m, 5H), 6.02 (s, 1H), 4.50-4.45 (m, 1H), 4.33-4.21 (m, 4H), 3.32 (s, 3H), 2.81-2.75 (m, 1H), 2.35-2.31 (m, 1H), 1.92-1.88 (m, 1H), 0.95-0.92 (m, 2H), 0.75-0.72 (m, 2H). | 407.1 |

TABLE 2-continued

| Compound Example # Method | RIP1 Ki (μM) | Structure and Name | $^1$H NMR Data | MS (m/z) |
|---|---|---|---|---|
| | | (S)-5-benzyl-N-(2-cyclopropyl-4-methyl-5-oxo-5,6,7,8-tetrahydro-4H-pyrazolo[1,5-a][1,3]diazepin-6-yl)-1,3,4-oxadiazole-2-carboxamide | | |
| Example 283 WX Method KKKKK | 0.0722 | 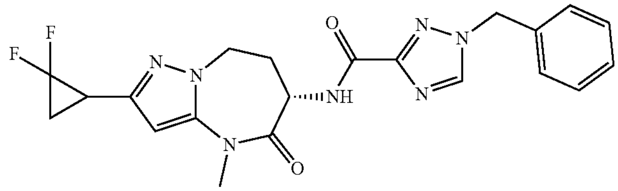 [SMILES: CN1C(=O)[C@@H](NC(=O)c2ncn(Cc3ccccc3)n2)CCn2nc(C3CC3(F)F)cc21] 1-benzyl-N-((6S)-2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.82 (s, 1H), 8.56 (d, J = 7.6 Hz, 1H), 7.41-7.28 (m, 5H), 6.29 (d, J = 8.8 Hz, 1H), 5.48 (s, 2H), 4.35-4.26 (m, 2H), 4.19-4.07 (m, 1H), 3.22 (d, J = 1.6 Hz, 3H), 2.94-2.87 (m, 1H), 2.41-2.32 (m, 2H), 2.00-1.93 (m, 1H), 1.89-1.81 (m, 1H). | 442.2 |
| Example 284 WX Method NNNNN | 0.0864 | 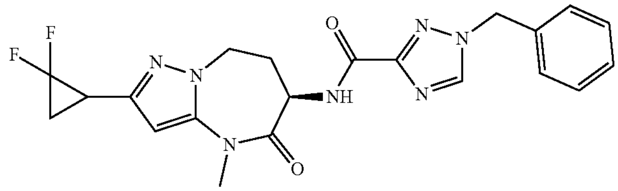 [SMILES: CN1C(=O)[C@H](NC(=O)c2ncn(Cc3ccccc3)n2)CCn2nc(C3CC3(F)F)cc21] 1-benzyl-N-((6R)-2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.82 (s, 1H), 8.55 (d, J = 8.0 Hz, 1H), 7.40-7.29 (m, 5H), 6.28 (d, J = 8.8 Hz, 1H), 5.48 (s, 2H), 4.33-4.29 (m, 2H), 4.17-4.16 (m, 1H), 3.321 (s, 3H), 2.93-2.88 (m, 1H), 2.59-2.50 (m, 1H), 2.37-2.36 (m, 1H), 1.96-1.84 (m, 2H). | 442.2 |
| Example 285 WX Method LLLLL | 0.219 | 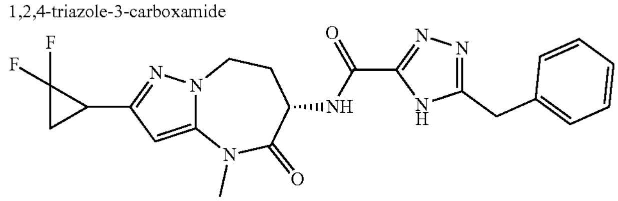 5-benzyl-N-((6S)-2-(2,2-difluorocyclopropyl)-4-methyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, DMSO-$d_6$) δ 7.34-7.21 (m, 5H), 6.29 (d, J = 8.4 Hz, 1H), 4.35-4.26 (m, 2H), 4.20-4.15 (m, 1H), 4.11 (s, 2H), 3.22 (d, J = 1.6 Hz, 3H), 2.93-2.88 (m, 1H), 2.59-2.57 (m, 1H), 2.44-2.35 (m, 1H), 2.01-1.93 (m, 1H), 1.90-1.81 (m, 1H). | 442.2 |
| Example 286 WX Method MMMMM | 0.0924 | 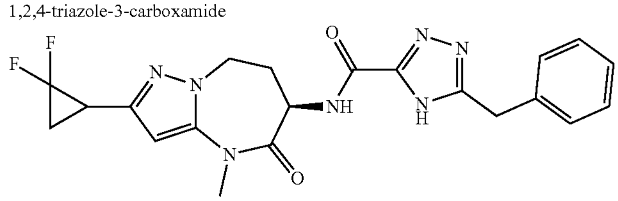 5-benzyl-N-((6R)-2-(2,2-difluorocyclopropyl)-4-methyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, DMSO-$d_6$) δ 7.32-7.20 (m, 5H), 6.26 (d, J = 8.0 Hz, 1H), 4.32-4.27 (m, 2H), 4.15-4.09 (m, 3H), 3.19 (s, 3H), 2.89-2.86 (m, 1H), 2.66-2.63 (m, 1H) 2.56-2.55 (m, 1H), 1.95-1.85 (m, 1H), 1.84-1.82 (m, 1H). | 442.2 |
| Example 287 WX Method NN | 1.4 | 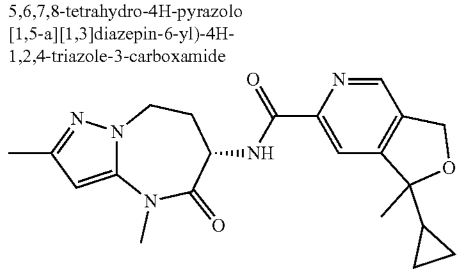 1-cyclopropyl-N-((S)-2,4-dimethyl-5-oxo-5,6,7,8-tetrahydro-4H-pyrazolo[1,5-a][1,3]diazepin-6-yl)-1-methyl-1,3-dihydrofuro[3,4-c]pyridine-6-carboxamide | $^1$H NMR (400 MHz, $CD_3OD$) δ 8.53 (s 1H) 7.92 (s 1H) 6.10 (s, 1H), 5.13-5.04 (m, 2H), 4.58-4.55 (m, 1H), 4.35-4.22 (m, 2H), 3.33 (s, 3H), 2.92-2.85 (m, 1H), 2.27-2.21 (m, 4H), 1.48 (s, 3H), 1.28-1.23 (m, 1H), 0.47-0.25 (m, 4H). | 396.0 |

TABLE 2-continued

| Compound Example # Method | RIP1 Ki (μM) | Structure and Name | $^1$H NMR Data | MS (m/z) |
|---|---|---|---|---|
| Example 288 WX Method TTT | 0.0623 | 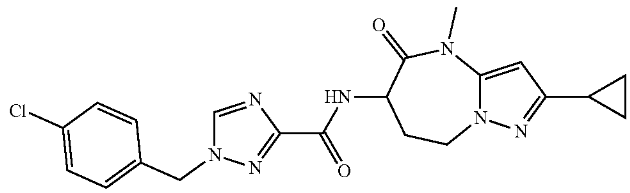 [SMILES: CN1C(=O)C(NC(=O)c2ncn(Cc3ccc(Cl)cc3)n2)CCn2nc(C3CC3)cc21] 1-(4-chlorobenzyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, DMSO-$d_6$) δ 8.80 (s, 1H), 8.52 (d, J = 8.0 Hz, 1H), 7.42 (d, J = 8.0 Hz, 2H), 7.31 (d, J = 8.0 Hz, 2H), 6.04 (s, 1H), 5.47 (s, 2H), 4.29-4.21 (m, 2H), 4.19-4.05 (m, 1H), 3.17 (s, 3H), 2.57-2.45 (m, 2H), 1.86-1.80 (m, 1H), 0.84-0.82 (m, 2H), 0.65-0.59 (m, 2H). | 440.1 |
| Example 289 WX Method JJJ | 0.395 | 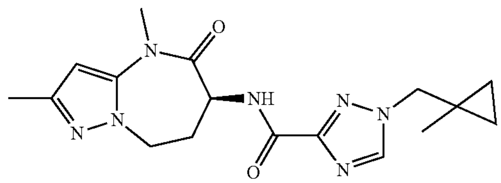 [SMILES: Cc1cc2n(n1)CC[C@H](NC(=O)c1ncn(CC3(C)CC3)n1)C(=O)N2C] (S)-N-(2,4-dimethyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide | $^1$H NMR (400 MHz, $CD_3OD$) δ 8.55 (s, 1H), 6.14 (s, 1H), 4.88-4.54 (m, 1H), 4.34-4.32 (m, 1H), 4.27-4.24 (m, 1H), 4.15 (s, 2H), 3.35 (s, 3H), 2.92-2.85 (m, 1H), 2.32-2.26 (m, 4H), 1.05 (s, 3H), 0.76-0.73 (m, 2H), 0.50-0.47 (m, 2H). | 358.2 |
| Example 290 WX Method JJJJ | 0.117 | 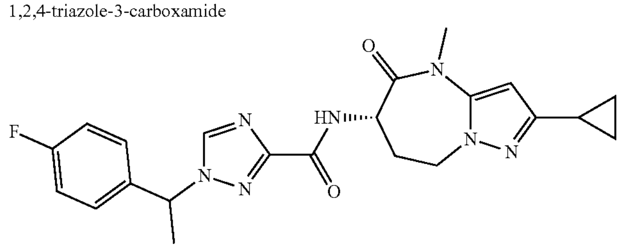 N-((S)-2-cyclopropyl-4-methyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide | $^1$H NMR (400 MHz, DMSO-$d_6$) δ 8.85 (s, 1H), 8.52 (d, J = 7.6 Hz, 1H), 7.40-7.37 (m, 2H), 7.22-7.18 (m, 2H), 6.06 (s, 1H), 5.86-5.81 (m, 1H), 4.32-4.21 (m, 2H), 4.09-4.08 (m, 1H), 3.19 (s, 3H), 2.59-2.55 (m, 1H), 2.40-2.32 (m, 1H), 1.87-1.83 (m, 4H), 0.87-0.84 (m, 2H), 0.67-0.64 (m, 2H). | 438.2 |
| Example 291 WX Method KKKK | 0.82 | 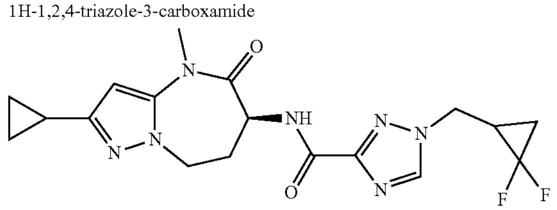 N-((S)-2-cyclopropyl-4-methyl-5-oxo-5,6,7,8-tetrahydro-4H-pyrazolo[1,5-a][1,3]diazepin-6-yl)-1-((2,2-difluorocyclopropyl)methyl)-1H-1,2,4-triazole-3-carboxamide | $^1$H NMR (400 MHz, DMSO-$d_6$) δ 8.70 (s, 1H), 8.56 (d, J = 8.0 Hz, 1H), 6.07 (s, 1H), 4.45-4.30 (m, 4H), 4.24-4.09 (m, 1H), 3.20 (s, 3H), 2.61-2.58 (m, 1H), 2.34-2.32 (m, 2H), 1.87-1.85 (m, 1H), 1.83-1.80 (m, 1H), 1.77-1.67 (m, 1H), 0.86-0.84 (m, 2H), 0.69-0.64 (m, 2H). | 406.1 |
| Example 292 WX Method LLLL | 0.1 | 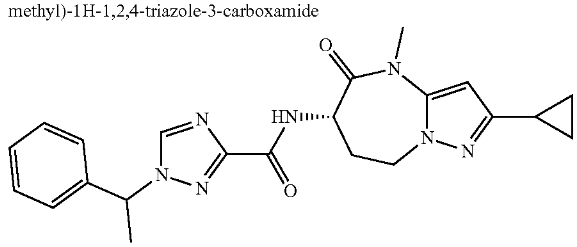 N-((S)-2-cyclopropyl-4-methyl-5-oxo-5,6,7,8-tetrahydro-4H-pyrazolo[1,5-a][1,3]diazepin-6-yl)-1-(1-phenylethyl)-1H-1,2,4-triazole-3-carboxamide | $^1$H NMR (400 MHz, DMSO-$d_6$) δ 8.87 (s, 1H), 8.54 (d, J = 7.6 Hz, 1H), 7.36-7.32 (m, 5H), 6.06 (s, 1H), 5.82-5.80 (m, 1H), 4.32-4.21 (m, 2H), 4.12-4.08 (m, 1H), 3.19 (s, 3H), 2.57-2.50 (m, 1H), 2.37-2.33 (m, 1H), 1.86-1.84 (m, 4H), 0.86-0.84 (m, 2H), 0.67-0.65 (m, 2H). | 420.1 |

TABLE 2-continued

| Compound Example # Method | RIP1 Ki (μM) | Structure and Name | $^1$H NMR Data | MS (m/z) |
|---|---|---|---|---|
| Example 293 WX Method BBBBBBB | 0.0728 | 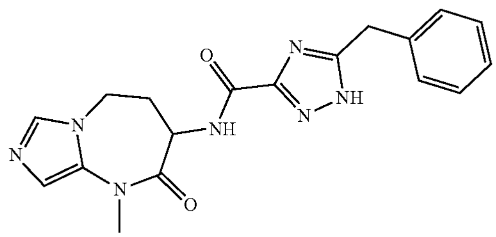 [SMILES: CN1C(=O)C(NC(=O)c2n[nH]c(Cc3ccccc3)n2)CCn2cncc21] 5-benzyl-N-(1-methyl-2-oxo-2,3,4,5-tetrahydro-1H-imidazo[1,5-a][1,3]diazepin-3-yl)-1H-1,2,4-triazole-3-carboxamide | $^1$H NMR (400 MHz, $CD_3OD$) δ 7.66 (s, 1H), 7.31-7.24 (m, 5H), 7.01 (s, 1H), 4.45-4.41 (m, 2H), 4.16 (s, 2H), 4.04-3.96 (m, 1H), 3.35 (s, 3H), 2.80-2.72 (m, 1H), 2.21-2.13 (m, 1H). | 366.1 |
| Example 294 WX Method ZZZZZZ | 0.557 | 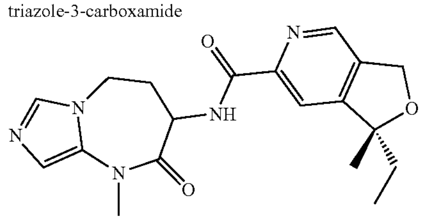 (1R)-1-ethyl-1-methyl-N-(1-methyl-2-oxo-2,3,4,5-tetrahydro-1H-imidazo[1,5-a][1,3]diazepin-3-yl)-1,3-dihydrofuro[3,4-c] pyridine-6-carboxamide | $^1$H NMR (400 MHz, $CD_3OD$) δ 8.55 (s, 1H), 7.87 (s, 1H), 7.65 (s, 1H), 7.01 (s, 1H), 5.16-5.15 (m, 2H), 4.65-4.60 (m, 1H), 4.66-4.41 (m, 1H), 4.05-3.98 (m, 1H), 3.37 (s, 3H), 2.84-2.80 (m, 1H), 2.21-2.17 (m, 1H), 1.88-1.82 (m, 2H), 1.46 (s, 3H), 0.77 (t, J = 7.2 Hz, 3H). | 370.2 |
| Example 295 WX Method AAAAAAA | 0.118 | 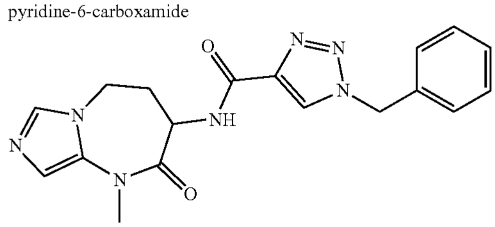 1-benzyl-N(1-methyl-2-oxo-2,3,4,5-tetrahydro-1H-imidazo[1,5-a][1,3]diazepin-3-yl)-1H-1,2,3-triazole-4-carboxamide | $^1$H NMR (400 MHz, $CD_3OD$) δ 8.34 (s, 1H), 7.61 (s, 1H), 7.36-7.32 (m, 5H), 6.98 (s, 1H), 5.63 (s, 2H), 4.61-4.56 (m, 1H), 4.44-4.38 (m, 1H), 4.03-3.98 (m, 1H), 3.34 (s, 3H), 2.75-2.69 (m, 1H), 2.24-2.18 (m, 1H). | 366.2 |
| Example 296 WX Method MM | 0.0612 | 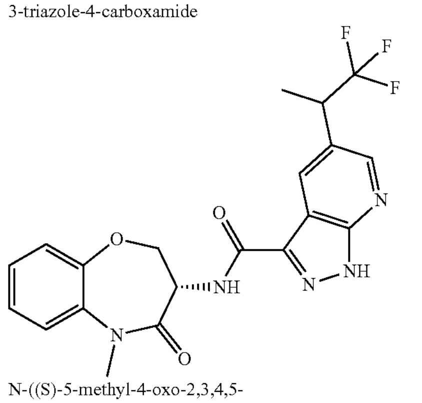 N-((S)-5-methyl-4-oxo-2,3,4,5-tetrahydrobenzo[b][1,4]oxazepin-3-yl)-5-(1,1,1-trifluoropropan-2-yl)-1H-pyrazolo[3,4-b] pyridine-3-carboxamide | $^1$H NMR (400 MHz, DMSO-$d_6$) δ 14.35 (br. s, 1H), 8.72-8.57 (m, 2H), 8.44 (s, 1H), 7.56-7.47 (m, 1H), 7.40-7.19 (m, 3H), 4.98-4.89 (m, 1H), 4.71-4.63 (m, 1H), 4.50-4.43 (m, 1H), 4.17-4.06 (m, 1 H), 3.34 (m, 3H), 1.51 (d, J = 7.2 Hz, 3H). | 434.1 |
| Example 297 WX Method CCCCCCC | 0.0208 | 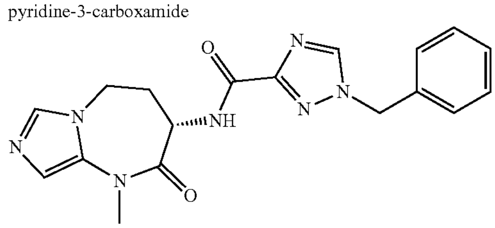 (S)-1-benzyl-N-(1-methyl-2-oxo-2,3,4,5-tetrahydro-1H-imidazo | $^1$H NMR (400 MHz, $CD_3OD$) δ 8.56 (s, 1H), 7.63 (s, 1H), 7.39-7.33 (m, 5H), 7.00 (s, 1H), 5.47 (s, 2H), 4.62-4.57 (m, 1H), 4.43-4.39 (m, 1H), 4.02-3.97 (m, 1H), 3.36 (s, 3H), 2.79-2.72 (m, 1H), 2.22-2.16 (m, 1H). | 366.1 |

TABLE 2-continued

| Compound Example # Method | RIP1 Ki (μM) | Structure and Name | $^1$H NMR Data | MS (m/z) |
|---|---|---|---|---|
| | | [1,5-a][1,3]diazepin-3-yl)-1H-1,2,4-triazole-3-carboxamide | | |
| Example 298 WX Method FFFF | 2.5579 | 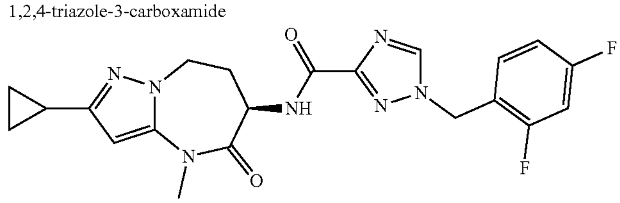 (R)-N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide | $^1$H NMR (400 MHz, $CD_3OD$) δ 8.57 (s, 1H), 7.46-7.44 (m, 1H), 7.04-6.97 (m, 2H), 5.99 (s, 1H), 5.51 (s, 2H), 4.52-4.47 (m, 1H), 4.28-4.26 (m, 1H), 4.22-4.17 (m, 1H), 3.29 (s, 3H), 2.83-2.78 (m, 1H), 2.23-2.20 (m, 1H), 1.91-1.86 (m, 1H), 0.93-0.91 (m, 2H), 0.72-0.70 (m, 2H). | 442.1 |
| Example 299 WX Method EE 0.0740 0.0740 | 0.0740 | 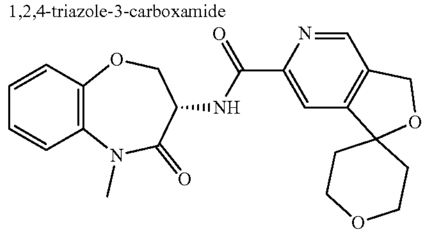 (S)-N-(5-methyl-4-oxo-2,3,4,5-tetrahydrobenzo[b][1,4]oxazepin-3-yl)-2',3',5',6'-tetrahydro-3H-spiro[furo[3,4-c]pyridine-1,4'-pyran]-6-carboxamide | $^1$H NMR (400 MHz, $CD_3OD$) δ 8.60 (s, 1H), 7.93 (s, 1H), 7.44-7.43 (m, 1H), 7.34-7.31 (m, 2H), 7.26-7.25 (m, 1H), 5.20 (s, 2H), 5.05-5.02 (m, 1H), 4.67-4.64 (m, 1H), 4.43-4.40 (m, 1H), 3.92-3.41 (m, 4H), 3.31 (s, 3H), 2.09-2.01 (m, 2H), 1.68-1.65 (m, 2H). | 410.1 |
| Example 300 WX Method EEEEE | 0.0504 | 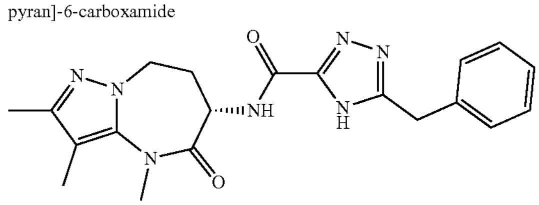 (S)-5-benzyl-N-(2,3,4-trimethyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, $CD_3OD$) δ 7.31-7.23 (m, 5H), 4.44-4.39 (m, 1H), 4.22-4.18 (m, 2H), 4.15 (s, 2H), 3.30 (s, 3H), 2.81-2.72 (m, 1H), 2.18-2.16 (m, 4H), 2.00 (s, 3H). | 394.1 |
| Example 301 WX Method MMM | 0.0104 | 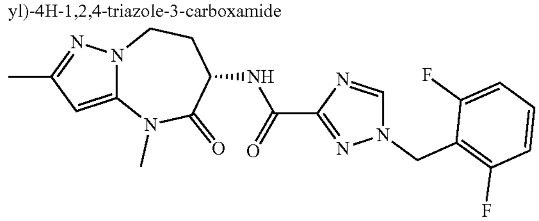 (S)-1-(2,6-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.58 (s, 1H), 7.45-7.42 (m, 1H), 7.05-7.01 (m, 2H), 6.08 (s, 1H), 5.57 (s, 2H), 4.48-4.46 (m, 1H), 4.27-4.25 (m, 1H), 4.24-4.19 (m, 1H), 3.29 (s, 3H), 2.83-2.77 (m, 1H), 2.25-2.21 (m, 4H). | 416.1 |
| Example 302 WX Method MMMM | 0.0268 | 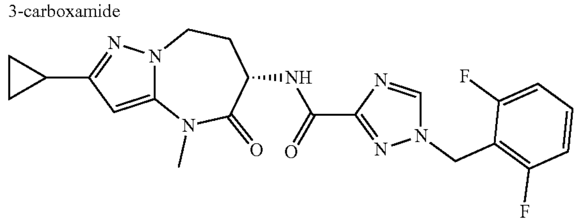 (S)-N-(2-cyclopropyl-4-methyl-5-oxo-5,6,7,8-tetrahydro-4H-pyrazolo[1,5-a][1,3]diazepin-6-yl)-1-(2,6-difluorobenzyl)-1H-1,2,4-triazole-3-carboxamide | $^1$H NMR (400 MHz, $CD_3OD$) δ 8.60 (s, 1H), 7.49-7.42 (m, 1H), 7.08-7.02 (m, 2H), 5.99 (s, 1H), 5.59 (s, 2H), 4.52-4.47 (m, 1H), 4.28-4.24 (m, 1H), 4.22-4.18 (m, 1H), 3.31 (s, 3H), 2.85-2.78 (m, 1H), 2.24-2.22 (m, 1H), 1.91-1.88 (m, 1H), 0.94-0.91 (m, 2H), 0.74-0.72 (m, 2H). | 442.2 |

TABLE 2-continued

| Compound Example # Method | RIP1 Ki (μM) | Structure and Name | $^1H$ NMR Data | MS (m/z) |
|---|---|---|---|---|
| Example 303 WX Method NNNN | 0.0185 | 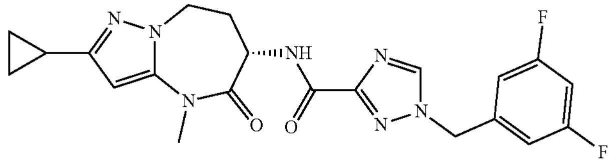 [SMILES: CN1C(=O)[C@@H](NC(=O)c2ncn(Cc3cc(F)cc(F)c3)n2)CCn2nc(C3CC3)cc21] (S)-N-(2-cyclopropyl-4-methyl-5-oxo-5,6,7,8-tetrahydro-4H-pyrazolo[1,5-a][1,3]diazepin-6-yl)-1-(3,5-difluorobenzyl)-1H-1,2,4-triazole-3-carboxamide | $^1H$ NMR (400 MHz, $CD_3OD$) δ 8.62 (s, 1H), 6.97-6.91 (m, 3H), 5.99 (s, 1H), 5.49 (s, 2H), 4.54-4.50 (m, 1H), 4.28-4.26 (m, 1H), 4.21-4.14 (m, 1H), 3.30 (s, 3H), 2.86-2.80 (m, 1H), 2.29-2.24 (m, 1H), 1.91-1.87 (m, 1H), 0.94-0.91 (m, 2H), 0.74-0.71 (m, 2H). | 442.1 |
| Example 304 WX Method OOOO | 0.0103 | 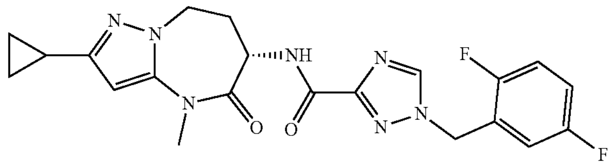 [SMILES: CN1C(=O)[C@@H](NC(=O)c2ncn(Cc3cc(F)ccc3F)n2)CCn2nc(C3CC3)cc21] (S)-N-(2-cyclopropyl-4-methyl-5-oxo-5,6,7,8-tetrahydro-4H-pyrazolo[1,5-a][1,3]diazepin-6-yl)-1-(2,5-difluorobenzyl)-1H-1,2,4-triazole-3-carboxamide | $^1H$ NMR (400 MHz, DMSO-$d_6$) δ 8.81 (s, 1H), 8.54 (d, J = 8.0 Hz, 1H), 7.31-7.25 (m, 3H), 6.06 (s, 1H), 5.54 (s, 2H), 4.30-4.26 (m, 2H), 4.25-4.21 (m, 1H), 3.19 (s, 3H), 2.54-2.52 (m, 1H), 2.50-2.33 (m, 1H), 1.85-1.83 (m, 1H), 0.86-0.84 (m, 2H), 0.68-0.64 (m, 2H). | 442.1 |
| Example 305 WX Method LLL | 0.015 | 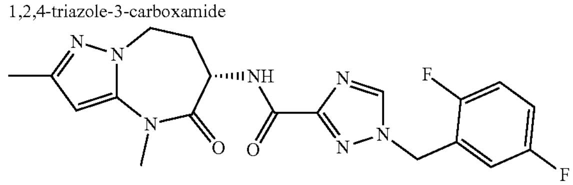 (S)-1-(2,5-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide | $^1H$ NMR (400 MHz, $CD_3OD$) δ 8.60 (s, 1H), 7.18-7.11 (m, 3H), 6.09 (s, 1H), 5.53 (s, 2H), 4.53-4.48 (m, 1H), 4.30-4.27 (m, 1H), 4.25-4.19 (m, 1H), 3.30 (s, 3H), 2.84-2.78 (m, 1H), 2.28-2.22 (m, 4H). | 416.1 |
| Example 306 WX Method PPPP | 0.0146 | 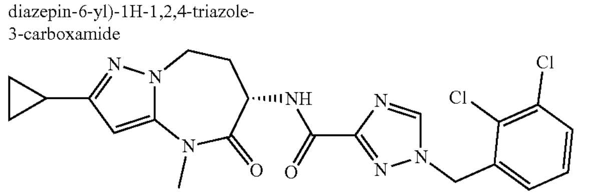 (S)-N-(2-cyclopropyl-4-methyl-5-oxo-5,6,7,8-tetrahydro-4H-pyrazolo[1,5-a][1,3]diazepin-6-yl)-1-(2,3-dichlorobenzyl)-1H-1,2,4-triazole-3-carboxamide | $^1H$ NMR (400 MHz, DMSO-$d_6$) δ 8.84 (s, 1H), 8.55 (d, J = 8.0 Hz, 1H), 7.66 (d, J = 8.0 Hz, 1H), 7.42-7.38 (m, 1H), 7.21 (d, J = 8.0 Hz, 1H), 6.06 (s, 1H), 5.64 (s, 2H), 4.31-4.23 (m, 2H), 4.21-4.07 (m, 1H), 3.19 (s, 3H), 2.58-2.50 (m, 1H), 2.44-2.32 (m, 1H), 1.85-1.83 (m, 1H), 0.86-0.84 (m, 2H), 0.68-0.64 (m, 2H). | 474.1 |
| Example 307 WX Method QQQQ | 0.0085 | 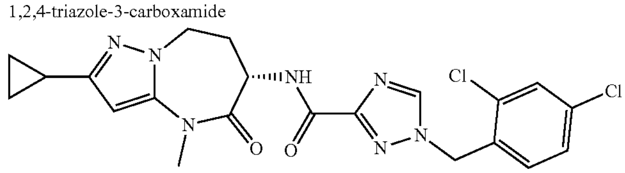 (S)-N-(2-cyclopropyl-4-methyl-5-oxo-5,6,7,8-tetrahydro-4H-pyrazolo[1,5-a][1,3]diazepin-6-yl)-1-(2,4-dichlorobenzyl)-1H-1,2,4-triazole-3-carboxamide | $^1H$ NMR (400 MHz, $CD_3OD$) δ 8.59 (s, 1H), 7.52 (d, J = 1.6 Hz, 1H), 7.41-7.30 (m, 2H), 5.99 (s, 1H), 5.57 (s, 2H), 4.53-4.48 (m, 1H), 4.28-4.26 (m, 1H), 4.20-4.17 (m, 1H), 3.29 (s, 3H), 2.85-2.78 (m, 1H), 2.27-2.22 (m, 1H), 1.91-1.86 (m, 1H), 0.93-0.91 (m, 2H), 0.77-0.71 (m, 2H). | 474.1 |
| Example 308 WX Method IIII | 0.1715 | 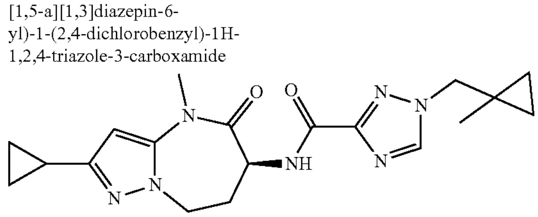 (S)-N-(2-cyclopropyl-4-methyl-5-oxo-5,6,7,8-tetrahydro-4H-pyrazolo | $^1H$ NMR (400 MHz, $CD_3OD$) δ 8.51 (s, 1H), 6.00 (s, 1H), 4.55-4.51 (m, 1H), 4.30-4.24 (m, 1H), 4.22-4.19 (m, 1H), 4.12 (s, 2H), 3.30 (s, 3H), 2.89-2.83 (m, 1H), 2.27-2.24 (m, 1H), 1.92-1.87 (m, 1H), 1.03 (s, 3H), 0.94-0.91 (m, 2H), 0.75-0.71 (m, 4H), 0.47-0.44 (m,2H). | 384.3 |

TABLE 2-continued

| Compound Example # Method | RIP1 Ki (μM) | Structure and Name | $^1$H NMR Data | MS (m/z) |
|---|---|---|---|---|
| | | [1,5-a][1,3]diazepin-6-yl)-1-((1-methylcyclopropyl)methyl)-1H-1,2,4-triazole-3-carboxamide | | |
| Example 309 WX Method N | 0.0528 | 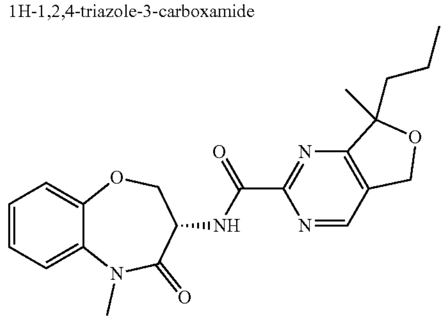 7-methyl-N-((S)-5-methyl-4-oxo-2,3,4,5-tetrahydrobenzo[b][1,4]oxazepin-3-yl)-7-propyl-5,7-dihydrofuro[3,4-d]pyrimidine-2-carboxamide | $^1$H NMR (400 MHz, $CD_3OD$) δ 8.82 (s, 1H), 7.46-7.44 (m, 1H), 7.36-7.24 (m, 3H), 5.20-5.12 (m, 2H), 5.08-5.03 (m, 1H), 4.71-4.66 (m, 1H), 4.48-4.42 (m, 1H), 3.44 (s, 3H), 1.96-1.79 (m, 2H), 1.54-1.38 (m, 4H), 1.08-0.95 (m, 1H), 0.89-0.85 (m, 3H). | 397.2 |
| Example 310 WX Method AA | 0.0372 | 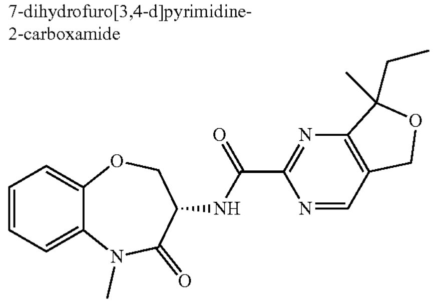 7-ethyl-7-methyl-N-((S)-5-methyl-4-oxo-2,3,4,5-tetrahydrobenzo[b][1,4]oxazepin-3-yl)-5,7-dihydrofuro[3,4-d]pyrimidine-2-carboxamide | $^1$H NMR (400 MHz, $CD_3OD$) δ 8.83 (s, 1H), 7.46-7.43 (m, 1H), 7.34-7.32 (m, 2H), 7.27-7.24 (m, 1H), 5.19-5.15 (m, 2H), 5.08-5.03 (m, 1H), 4.71-4.66 (m, 1H), 4.47-4.44 (m, 1H), 3.44 (s, 3H), 2.01-1.85 (m, 2H), 1.49 (s, 3H), 0.80 (t, J = 7.2 Hz, 3H). | 383.1 |
| Example 311 WX Method YYYYY | 5.247 | 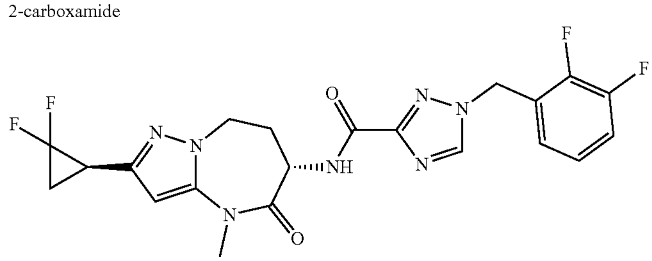 1-(2,3-difluorobenzyl)-N((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.62 (s, 1H), 7.29-7.25 (m, 1H), 7.17-7.12 (m, 2H), 6.20 (s, 1H), 5.58 (s, 2H), 4.53-4.48 (m, 1H), 4.36-4.23 (m, 2H), 3.31 (s, 3H), 2.84-2.79 (m, 2H), 2.26-2.21 (m, 1H), 1.87-1.80 (m, 2H). | 478.2 |
| Example 312 WX Method SSSSS | 0.0178 | 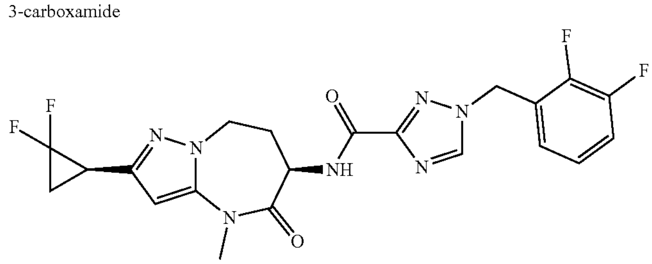 1-(2,3-difluorobenzyl)-N-((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.63 (s, 1H), 7.32-7.27 (m, 1H), 7.19-7.16 (m, 2H), 6.21 (s, 1H), 5.60 (s, 2H), 4.55-4.50 (m, 1H), 4.36-4.34 (m, 1H), 4.27-4.24 (m, 1H), 3.33 (s, 3H), 2.88-2.80 (m, 2H), 2.28-2.26 (m, 1H), 1.90-1.78 (m, 2H). | 478.1 |

TABLE 2-continued

| Compound Example # Method | RIP1 Ki (μM) | Structure and Name | $^1H$ NMR Data | MS (m/z) |
|---|---|---|---|---|
| Example 313 WX Method ZZZZZ | 5.94 | 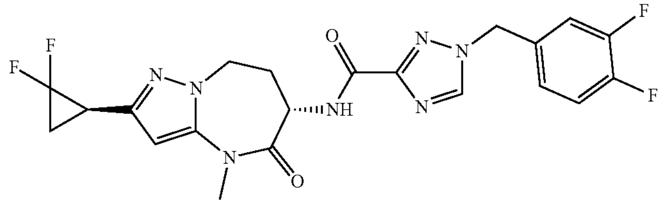 [SMILES: CN1C(=O)[C@@H](NC(=O)c2ncn(Cc3ccc(F)c(F)c3)n2)CCn2nc([C@H]3CC3(F)F)cc21] 1-(3,4-difluorobenzyl)-N-((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1H$ NMR (400 MHz, $CD_3OD$) δ 8.59 (s, 1H), 7.34-7.26 (m, 2H), 7.25-7.18 (m, 1H), 6.20 (s, 1H), 5.45 (s, 2H), 4.55-4.50 (m, 1H), 4.36-4.34 (m, 1H), 4.26-4.23 (m, 1H), 3.30 (s, 3H), 2.85-2.80 (m, 2H), 2.27-2.26 (m, 1H), 1.89-1.77 (m, 2H). | 478.1 |
| Example 314 WX Method TTTTT | 0.0435 | 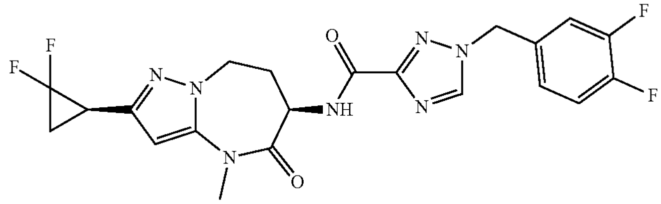 [SMILES: CN1C(=O)[C@H](NC(=O)c2ncn(Cc3ccc(F)c(F)c3)n2)CCn2nc([C@H]3CC3(F)F)cc21] 1-(3,4-difluorobenzyl)-N((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1H$ NMR (400 MHz, $CD_3OD$) δ 8.60 (s, 1H), 7.35-7.26 (m, 2H), 7.20-7.19 (m, 1H), 6.21 (s, 1H), 5.46 (s, 2H), 4.55-4.50 (m, 1H), 4.37-4.35 (m, 1H), 4.27-4.24 (m, 1H), 3.33 (s, 3H), 2.88-2.80 (m, 2H), 2.28-2.27 (m, 1H), 1.90-1.78 (m, 2H). | 478.1 |
| Example 315 WX Method AAAAAA | 9.5 | 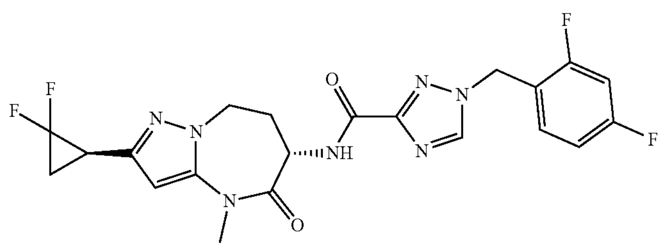 [SMILES: CN1C(=O)[C@@H](NC(=O)c2ncn(Cc3ccc(F)cc3F)n2)CCn2nc([C@H]3CC3(F)F)cc21] 1-(2,4-difluorobenzyl)-N-((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1H$ NMR (400 MHz, $CD_3OD$) δ 8.58 (s, 1H), 7.44 (s, 1H), 7.01-7.00 (m, 2H), 6.20 (s, 1H), 5.51 (s, 2H), 4.52-4.50 (m, 1H), 4.35-4.22 (m, 2H), 3.31 (s, 3H), 2.82-2.80 (m, 2H), 2.26-2.23 (m, 1H), 1.87-1.80 (m, 2H). | 478.1 |
| Example 316 WX Method UUUUU | 0.0318 | 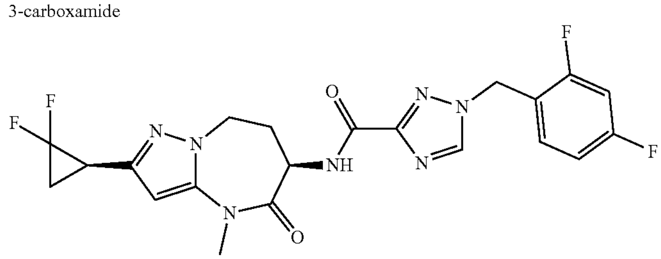 1-(2,4-difluorobenzyl)-N-((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1H$ NMR (400 MHz, $CD_3OD$) δ 8.59 (s, 1H), 7.49-7.43 (m, 1H), 7.06-6.98 (m, 2H), 6.21 (s, 1H), 5.53 (s, 2H), 4.54-4.49 (m, 1H), 4.38-4.34 (m, 1H), 4.27-4.24 (m, 1H), 3.33 (s, 3H), 2.87-2.77 (m, 2H), 2.27-2.26 (m, 1H), 1.90-1.78 (m, 2H). | 478.2 |
| Example 317 WX Method BBBBBB | 6.609 | 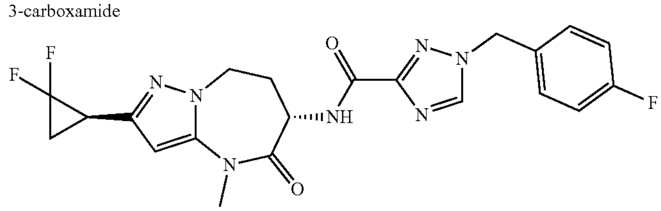 | $^1H$ NMR (400 MHz, $CD_3OD$) δ 8.56 (s, 1H), 7.41-7.37 (m, 2H), 7.11-7.07 (m, 2H), 6.20 (s, 1H), 5.45 (s, 2H), 4.54-4.49 (m, 1H), 4.35-4.33 (m, 1H), 4.26-4.23 (m, 1H), 3.30 (s, 3H), 2.84-2.78 (m, 2H), 2.27-2.25 (m, 1H), 1.89-1.78 (m, 2H). | 460.1 |

TABLE 2-continued

| Compound Example # Method | RIP1 Ki (μM) | Structure and Name | $^1H$ NMR Data | MS (m/z) |
|---|---|---|---|---|
| | | N-((S)-2-((R)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide | | |
| Example 318 WX Method VVVVV | 0.0253 | 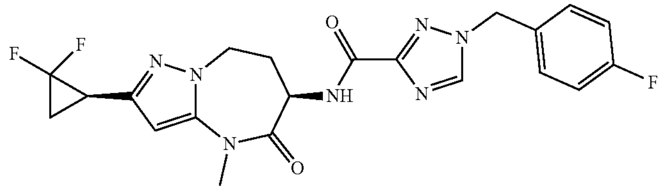 [SMILES: CN1C(=O)[C@H](NC(=O)c2ncn(Cc3ccc(F)cc3)n2)CCn2nc([C@H]3CC3(F)F)cc21] N-((R)-2-((R)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide | $^1H$ NMR (400 MHz, $CD_3OD$) δ 8.58 (s, 1H), 7.42-7.39 (m, 2H), 7.11 (t, J = 8.4 Hz, 2H), 6.21 (s, 1H), 5.46 (s, 2H), 4.55-4.51 (m, 1H), 4.37-4.35 (m, 1H), 4.27-4.24 (m, 1H), 3.33 (s, 3H), 2.88-2.80 (m, 2H), 2.28-2.27 (m, 1H), 1.97-1.80 (m, 2H). | 460.1 |
| Example 319 WX Method CCCCCC | > 10 | 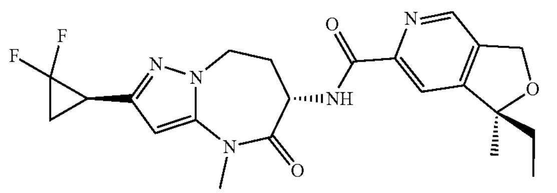 [SMILES: CC[C@]1(C)OCc2cnc(C(=O)N[C@H]3CCn4nc([C@H]5CC5(F)F)cc4N(C)C3=O)cc21] (S)-N-((S)-2-((R)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide | $^1H$ NMR (400 MHz, $CD_3OD$) δ 8.55 (s, 1H), 7.86 (s, 1H), 6.21 (s, 1H), 5.19-5.15 (m, 2H), 4.55-4.39 (m, 1H), 4.38-4.35 (m, 1H), 4.30-4.26 (m, 1H), 3.30 (s, 3H), 2.92-2.81 (m, 2H), 2.26-2.25 (m, 1H), 1.94-1.78 (m, 4H), 1.45 (s, 3H), 0.78-0.74 (m, 3H). | 446.1 |
| Example 320 WX Method PPPPP | 0.0164 | 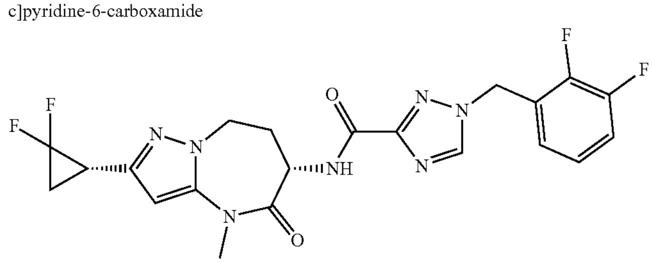 1-(2,3-difluorobenzyl)-N-((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1H$ NMR (400 MHz, $CD_3OD$) δ 8.62 (s, 1H), 7.33-7.24 (m, 1H), 7.22-7.13 (m, 2H), 6.19 (s, 1H), 5.60 (s, 2H), 4.54-4.49 (m, 1H), 4.42-4.33 (m, 1H), 4.30-4.19 (m, 1H), 3.33 (s, 3H), 2.90-2.75 (m, 2H), 2.28-2.24 (m, 1H), 1.94-1.85 (m, 1H), 1.82-1.74 (m, 1H). | 478.2 |
| Example 321 WX Method OOOOO | 0.067 | 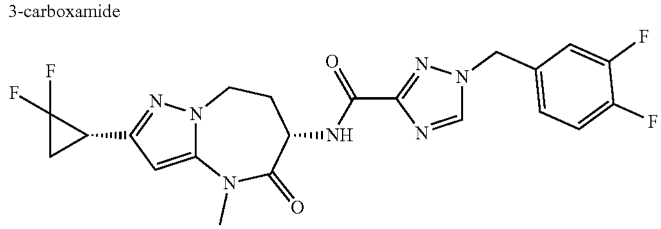 1-(3,4-difluorobenzyl)-N-((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1H$ NMR (400 MHz, $CD_3OD$) δ 8.60 (s, 1H), 7.36-7.23 (m, 2H), 7.21-7.19 (m, 1H), 6.20 (s, 1H), 5.46 (s, 2H), 4.54-4.49 (m, 1H), 4.42-4.34 (m, 1H), 4.30-4.20 (m, 1H), 3.33 (s, 3H), 2.91-2.75 (m, 2H), 2.31-2.22 (m, 1H), 1.92-1.88 (m, 1H), 1.83-1.74 (m, 1H). | 478.2 |

TABLE 2-continued

| Compound Example # Method | RIP1 Ki (μM) | Structure and Name | $^1$H NMR Data | MS (m/z) |
|---|---|---|---|---|
| Example 322 WX Method QQQQQ | 0.0286 | 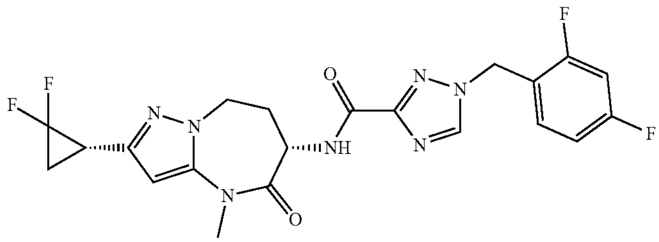 [SMILES: CN1C(=O)[C@@H](NC(=O)c2ncn(Cc3ccc(F)cc3F)n2)CCn2nc([C@@H]3CC3(F)F)cc21] 1-(2,4-difluorobenzyl)-N-((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide | $^1$H NMR (400 MHz, $CD_3OD$) δ 8.58 (s, 1H), 7.50-7.42 (m, 1H), 7.06-6.96 (m, 2H), 6.19 (s, 1H), 5.52 (s, 2H), 4.53-4.48 (m, 1H), 4.41-4.33 (m, 1H), 4.28-4.17 (m, 1H), 3.33 (s, 3H), 2.90-2.76 (m, 2H), 2.30-2.19 (m, 1H), 1.95-1.84 (m, 1H), 1.83-1.73 (m, 1H). | 478.2 |
| Example 323 WX Method RRRRR | 0.0578 | 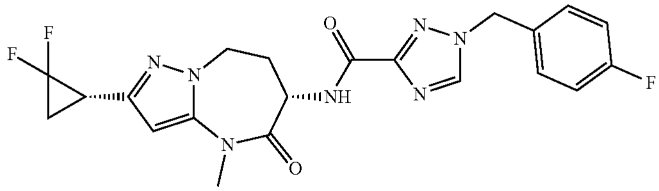 [SMILES: CN1C(=O)[C@@H](NC(=O)c2ncn(Cc3ccc(F)cc3)n2)CCn2nc([C@@H]3CC3(F)F)cc21] N-((S)-2-((S)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide | $^1$H NMR (400 MHz, $CD_3OD$) δ 8.57 (s, 1H), 7.40 (dd, J = 6.0, 8.4 Hz, 2H), 7.10 (t, J = 8.8 Hz, 2H), 6.19 (s, 1H), 5.46 (s, 2H), 4.53-4.45 (m, 1H), 4.41-4.34 (m, 1H), 4.30-4.20 (m, 1H), 3.33 (s, 3H), 2.90-2.75 (m, 2H), 2.29-2.14 (m, 1H), 1.95-1.85 (m, 1H), 1.83-1.73 (m, 1H). | 460.2 |
| Example 324 WX Method WWWWW | 1.2895 | 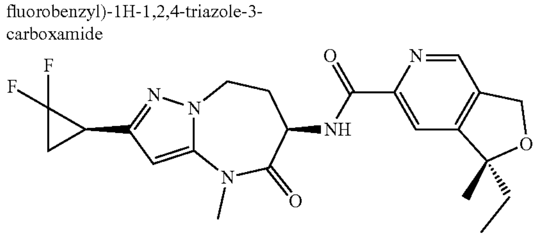 (R)-N-((R)-2-((R)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide | $^1$H NMR (400 MHz, $CD_3OD$) δ 8.57 (s, 1H), 7.87 (s, 1H), 6.23 (s, 1H), 5.21-5.16 (m, 2H), 4.59-4.55 (m, 1H), 4.39-4.37 (m, 2H), 3.36 (s, 3H), 2.94-2.79 (m, 2H), 2.28-2.26 (m, 1H), 1.92-1.78 (m, 4H), 1.47 (s, 3H), 0.78 (t, J = 6.8 Hz, 3H). | 446.2 |
| Example 325 WX Method XXXXX | 3.338 | 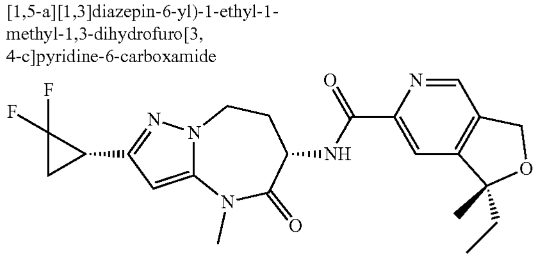 (R)-N-((S)-2-((S)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide | $^1$H NMR (400 MHz, $CD_3OD$) δ 8.56 (s, 1H), 7.87 (s, 1H), 6.21 (s, 1H), 5.20-5.16 (m, 2H), 4.58-4.53 (m, 1H), 4.38-4.27 (m, 2H), 3.35 (s, 3H), 2.98-2.78 (m, 2H), 2.27-2.17 (m, 1H), 1.92-1.78 (m, 4H), 1.46 (s, 3H), 0.76 (t, J = 3.6 Hz, 3H). | 446.3 |
| Example 326 WX Lactam synthesis Method Z & WX; Method OO | 0.6185 | 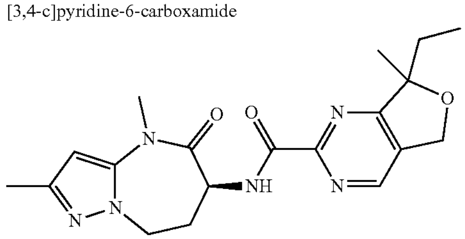 N-((S)-2,4-dimethyl-5-oxo-5,6,7,8-tetrahydro-4H-pyrazolo[1,5- | $^1$H NMR (400 MHz, $CD_3OD$) δ 8.82 (s, 1H), 6.13 (s, 1H), 5.18-5.12 (m, 2H), 4.62-4.57 (m, 1H), 4.34-4.25 (m, 2H), 3.35 (s, 3H), 2.97-2.92 (m, 1H), 2.32-2.27 (m, 4H), 1.99-1.85 (m, 2H), 1.49 (s, 3H), 0.80 (t, J = 7.6 Hz, 3H). | 385.1 |

TABLE 2-continued

| Compound Example # Method | RIP1 Ki (μM) | Structure and Name | $^1$H NMR Data | MS (m/z) |
|---|---|---|---|---|
| | | a][1,3]diazepin-6-yl)-7-ethyl-7-methyl-5,7-dihydrofuro[3,4-d]pyrimidine-2-carboxamide | | |
| Example 327 WX Method O | 1.37 | 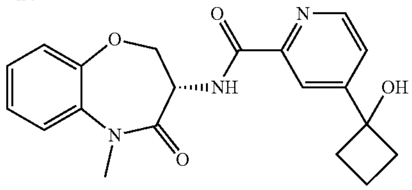 [SMILES: CN1C(=O)[C@@H](NC(=O)c2cc(C3(O)CCC3)ccn2)COc2ccccc21] (S)-4-(1-hydroxycyclobutyl)-N-(5-methyl-4-oxo-2,3,4,5-tetrahydrobenzo[b][1,4]oxazepin-3-yl)picolinamide | $^1$H NMR (400 MHz, $CD_3OD$): δ 8.63 (d, J = 5.6 Hz, 1H), 8.20 (d, J = 1.2 Hz, 1H), 7.72-7.70 (m, 1H), 7.46-7.44 (m, 1H), 7.35-7.24 (m, 3H), 5.06-4.99 (m, 1H), 4.67-4.63 (m, 1H), 4.43-4.38 (m, 1H), 3.43 (s, 3H), 2.52-2.36 (m, 4H), 2.14-2.01 (m, 1H), 1.89-1.78 (m, 1H). | 368.2 |
| Example 328 Method E | 0.99 | 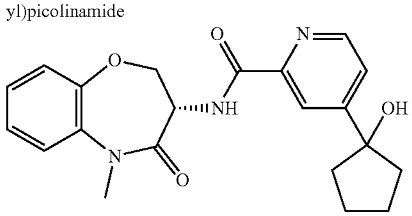 (S)-4-(1-hydroxycyclopentyl)-N-(5-methyl-4-oxo-2,3,4,5-tetrahydrobenzo[b][1,4]oxazepin-3-yl)picolinamide | $^1$H NMR (400 MHz, $CD_3OD$) δ 8.58 (d, J = 5.2 Hz, 1H), 8.15 (s, 1H), 7.67-7.65 (m, 1H), 7.46-7.41 (m, 1H), 7.35-7.29 (m, 2H), 7.27-7.22 (m, 1H), 5.05-4.96 (m, 1H), 4.67-4.58 (m, 1H), 4.43-4.36 (m, 1H), 3.43 (s, 3H), 2.03-1.84 (m, 8H). | 382.2 |
| Example 329 WX Method YY | 3.806 | 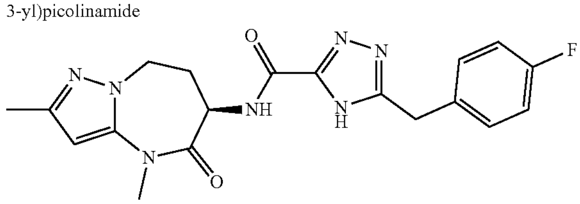 (R)-N-(2,4-dimethyl-5-oxo-5,6,7,8-tetrahydro-4H-pyrazolo[1,5-a][1,3]diazepin-6-yl)-5-(4-fluorobenzyl)-4H-1,2,4-triazole-3-carboxamide | $^1$H NMR (400 MHz, $CD_3OD$) δ 7.31-7.27 (m, 2H), 7.06-6.99 (m, 2H), 6.10 (s, 1H), 4.54-4.49 (m, 1H), 4.30-4.28 (m, 2H), 4.13 (s, 2H), 3.30 (s, 3H), 2.86-2.80 (m, 1H), 2.27-2.21 (m, 4H). | 398.1 |
| Example 330 WX Method JJJJJ | 0.103 | 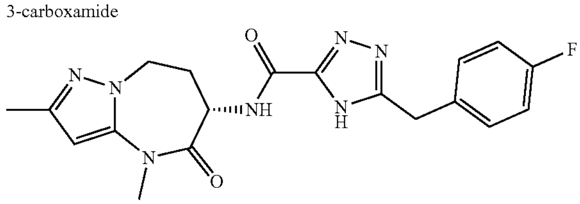 (S)-5-(4-fluorobenzyl)-N-(2,3,4-trimethyl-5-oxo-5,6,7,8-tetrahydro-4H-pyrazolo[1,5-a][1,3]diazepin-6-yl)-4H-1,2,4-triazole-3-carboxamide | $^1$H NMR (400 MHz, $CD_3OD$) δ 7.28-7.27 (m, 2H), 7.05-7.01 (m, 2H), 4.43-4.38 (m, 1H), 4.22-4.20 (m, 2H), 4.13 (s, 2H), 3.30 (s, 3H), 2.80-2.73 (m, 1H), 2.19-2.17 (m, 4H), 2.00 (s, 3H). | 412.1 |
| Example 331 WX Method CCCC | 0.013 | 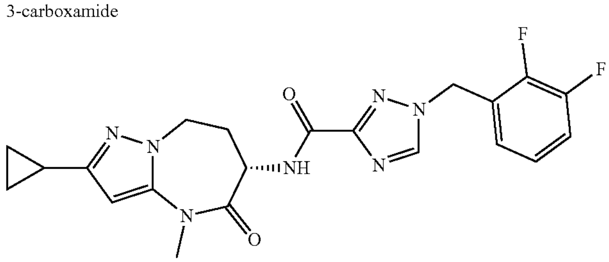 (S)-N-(2-cyclopropyl-4-methyl-5-oxo-5,6,7,8-tetrahydro-4H-pyrazolo[1,5-a][1,3]diazepin-6-yl)-1-(2,3-difluorobenzyl)-1H-1,2,4-triazole-3-carboxamide | $^1$H NMR (400 MHz, $CD_3OD$) δ 8.82 (s, 1H), 7.33-7.26 (m, 1H), 7.19-7.18 (m, 2H), 6.34 (s, 1H), 5.63 (s, 2H), 4.73-4.69 (m, 1H), 4.48-4.36 (m, 2H), 3.31 (s, 3H), 2.90-2.84 (m, 1H), 2.41 (m, 1H), 2.03-2.01 (m, 1H), 1.16-1.14 (m, 2H), 0.93-0.91 (m, 2H). | 442.1 |

TABLE 2-continued

| Compound Example # Method | RIP1 Ki (μM) | Structure and Name | $^1H$ NMR Data | MS (m/z) |
|---|---|---|---|---|
| Example 332 WX Method DDDD | 0.088 | 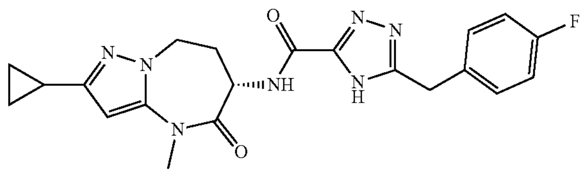 [SMILES: CN1C(=O)[C@@H](NC(=O)c2nnc(Cc3ccc(F)cc3)[nH]2)CCn2nc(C3CC3)cc21] (S)-N-(2-cyclopropyl-4-methyl-5-oxo-5,6,7,8-tetrahydro-4H-pyrazolo[1,5-a][1,3]diazepin-6-yl)-5-(4-fluorobenzyl)-4H-1,2,4-triazole-3-carboxamide | $^1H$ NMR (400 MHz, $CD_3OD$): 7.35-7.32 (m, 2H), 7.11-7.07 (m, 2H), 6.16 (s, 1H), 4.62-4.57 (m, 1H), 4.41-4.23 (m, 4H), 3.33 (s, 3H), 2.90-2.79 (m, 1H), 2.37-2.29 (m, 1H), 1.99-1.93 (m, 1H), 1.05-1.03 (m, 2H), 0.87-0.78 (m, 2H). | 424.1 |

The compounds of Tables 3, 4 and 5 below were prepared according to the methods described above. References to specific Methods of the specification are provided as non-limiting examples of how these compounds were prepared.

TABLE 3

| Example Ki (μM) Method(s) | Structure | $^1H$ NMR | MS (m/z) |
|---|---|---|---|
| Example 333 0.068 METHOD B | 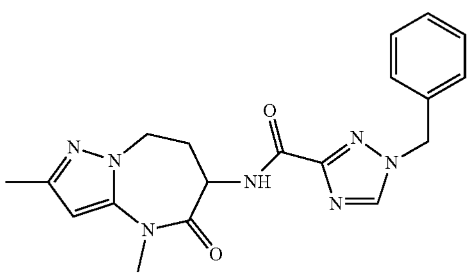 [SMILES: Cc1cc2n(n1)CCC(NC(=O)c1ncn(Cc3ccccc3)n1)C(=O)N2C] 1-benzyl-N-(2,4-dimethyl-5-oxo-5,6,7,8-tetrahydro-4H-pyrazo lo [1,5-a][1,3]diazepin-6-yl)-1H-1,2,4-triazole-3-carboxamide | 1H NMR (400 MHz, DMSO-d6) δ 8.82 (s, 1H), 8.50 (d, J = 7.8 Hz, 1H), 7.44-7.24 (m, 5H), 6.12 (s, 1H), 5.48 (s, 2H), 4.38-4.19 (m, 2H), 4.10 (ddd, J = 14.5, 12.6, 6.6 Hz, 1H), 3.21 (s, 3H), 2.64-2.53 (m, 1H), 2.38-2.27 (m, 1H), .16 (d, J = 0.5 Hz, 3H). | 380.2 3.69 min |
| Example 334 0.027 METHOD B | 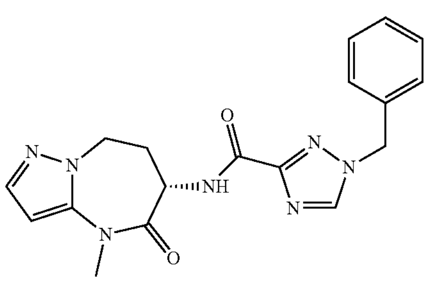 [SMILES: CN1C(=O)[C@@H](NC(=O)c2ncn(Cc3ccccc3)n2)CCn2nccc21] (S)-1-benzyl-N-(4-methyl-5-oxo-5,6,7,8-tetrahydro-4H-pyrazolo [1,5-a][1,3]diazepin-6-yl)-1H-1,2,4-triazole-3-carboxamide | 1H NMR (400 MHz, DMSO-d6) δ 8.82 (s, 1H), 8.53 (d, J = 7.8 Hz, 1H), 7.48 (d, J = 2.0 Hz, 1H), 7.42-7.27 (m, 5H), 6.34 (d, J = 2.0 Hz, 1H), 5.48 (s, 2H), 4.42-4.11 (m, 3H), 3.24 (s, 3H), 2.68-2.52 (m, 1H), 2.43-2.30 (m, 1H). | 366.1 3.47 min |

TABLE 3-continued

| Example<br>Ki (μM)<br>Method(s) | Structure | $^1$H NMR | MS (m/z) |
| --- | --- | --- | --- |
| Example 335<br>0.013<br>METHOD B | 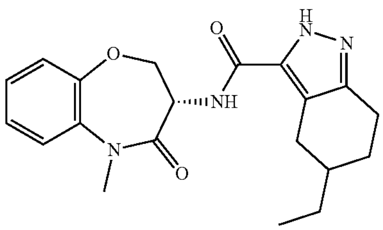 [SMILES: CCC1CCc2n[nH]c(C(=O)N[C@H]3COc4ccccc4N(C)C3=O)c2C1]<br>5-ethyl-N-((S)-5-methyl-4-oxo-2,3,4,5-tetrahydrobenzo[b][1,4]oxazepin-3-yl)-4,5,6,7-tetrahydro-2H-indazole-3-carboxamide | 1H NMR (400 MHz, DMSO-d6) δ 12.83 (s, 1H), 7.90 (d, J = 8.0 Hz, 1H), 7.51-7.45 (m, 1H), 7.35-7.26 (m, 2H), 7.25-7.21 (m, 1H), 4.90-4.76 (m, 1H), 4.55-4.45 (m, 1H), 4.45-4.36 (m, 1H), 2.87-2.76 (m, 1H), 2.72-2.60 (m, 1H), 2.11-1.97 (m, 1H), 1.92-1.78 (m, 1H), 1.53-1.42 (m, 1H), 1.40-1.25 (m, 3H), 0.90 (t, J = 7.4 Hz, 3H). | 369.2<br>5.17 min |
| Example 336<br>0.231<br>METHOD II | 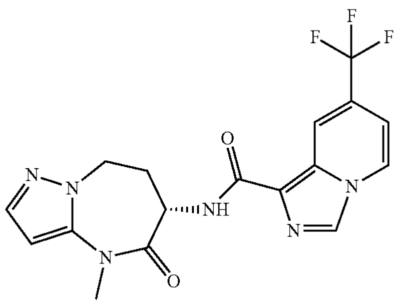 [SMILES: CN1C(=O)[C@@H](NC(=O)c2ncn3ccc(C(F)(F)F)cc23)CCn2nccc21]<br>(S)-N-(4-methyl-5-oxo-5,6,7,8-tetrahydro-4H-pyrazolo[1,5-a][1,3]diazepin-6-yl)-7-(trifluoromethyl)imidazo[1,5-a]pyridine-1-carboxamide | $^1$H NMR (400 MHz, DMSO-d6) δ 8.74-8.63 (m, 2H), 8.40 (d, J = 7.9 Hz, 1H), 8.37-8.29 (m, 1H), 7.51 (d, J = 2.0 Hz, 1H), 7.11 (dd, J = 7.4, 1.9 Hz, 1H), 6.35 (d, J = 2.0 Hz, 1H), 4.44-4.33 (m, 2H), 4.22 (ddd, J = 14.5, 12.6, 6.6 Hz, 1H), 3.26 (s, 3H), 2.71-2.56 (m, 1H), 2.46 -2.35 (m, 1H). | 393.1<br>4.03 min |
| Example 337<br>0.536<br>METHOD II | 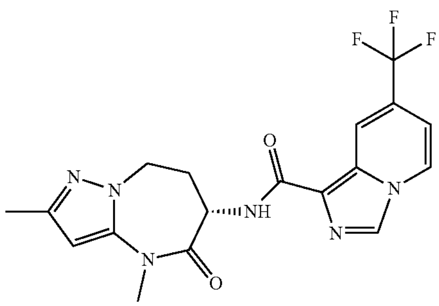 [SMILES: Cc1cc2n(n1)CC[C@H](NC(=O)c1ncn3ccc(C(F)(F)F)cc13)C(=O)N2C]<br>N-(2,4-dimethyl-5-oxo-5,6,7,8-tetrahydro-4H-pyrazolo[1,5-a][1,3]diazepin-6-yl)-7-(trifluoromethyl)imidazo[1,5-a]pyridine-1-carboxamide | $^1$H NMR (400 MHz, DMSO-d6) δ 8.72-8.63 (m, 2H), 8.37 (d, J = 7.9 Hz, 1H), 8.35-8.30 (m, 1H),7.11 (dd, J = 7.4, 1.9 Hz, 1H), 6.13 (s, 1H), 4.41 (dt, J = 11.6, 7.9 Hz, 1H), N-(2,4-dimethyl-5-oxo-5,6,7,8-4.29 (dd, J = 14.4, 8.1 Hz, 1H), 4.13 (ddd, J = 14.5, 12.6, 6.5 Hz, 1H), 3.23 (s, 3H), 2.70-2.56 (m, 1H), 2.42-2.30 (m, 1H), 2.18 (s, 3H) | 407.1<br>4.25 min |
| Example 338<br>0.021<br>METHOD B | 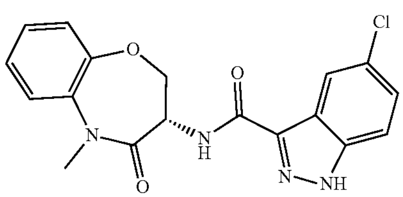 [SMILES: CN1C(=O)[C@@H](NC(=O)c2n[nH]c3ccc(Cl)cc23)COc2ccccc21]<br>(S)-5-chloro-N-(5-methyl-4-oxo-2,3,4,5-tetrahydrobenzo[b][1,4]oxazepin-3-yl)-1H-indazole-3-carboxamide | $^1$H NMR (400 MHz, DMSO-d6) δ 13.92 (s, 1H), 8.48 (d, J = 8.1 Hz, 1H), 8.04 (dd, J = 2.1, 0.7 Hz, 1H), 7.69 (dd, J = 8.9, 0.7 Hz, 1H), 7.55-2.0 Hz, 1H), 7.39-7.22 (m, 3H), 4.94 (dt, J = 11.5, 7.9 Hz, 1H), 4.64 (dd, J = 11.6, 9.9 Hz, 1H), 4.47 (dd, J = 9.9, 7.7 Hz, 1H), 3.33 (s, 3H). | 371.1<br>5.12 min |

TABLE 4

| Example<br>Ki (μM)<br>METHOD | Structure | Stereo | $^1$H NMR | MS (m/z) R.T. |
|---|---|---|---|---|
| Example 339<br>0.0282<br>METHOD B | 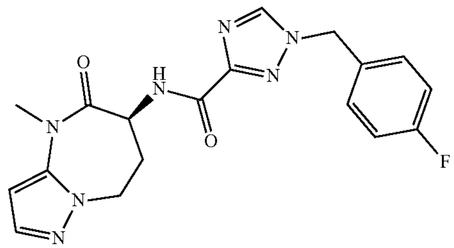 [SMILES: CN1C(=O)[C@@H](NC(=O)c2ncn(Cc3ccc(F)cc3)n2)CCn2nccc21]<br>1-[(4-fluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide | Single Known Stereoisomer | $^1$H NMR (400 MHz, DMSO-$d_6$) δ 8.80 (s, 1H), 8.52 (d, J = 7.8 Hz, 1H), 7.48 (d, J = 2.0 Hz, 1H), 7.45-7.33 (m, 2H), 7.28-7.14 (m, 2H), 6.34 (d, J = 3.62 2.0 Hz, 1H), 5.47 (s, 2H), 4.40-4.11 (m, 3H), 3.24 (s, 3H), 2.64-2.56 (m, 1H), 2.42-2.30 (m, 1H). | 384.2<br>3.62 min |
| Example 340<br>0.0128<br>METHOD B | 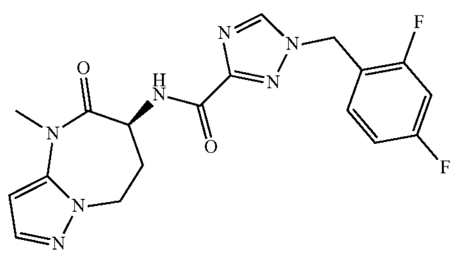 [SMILES: CN1C(=O)[C@@H](NC(=O)c2ncn(Cc3ccc(F)cc3F)n2)CCn2nccc21]<br>1-[(2,4-difluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide | Single Known Stereoisomer | $^1$H NMR (400 MHz, DMSO-$d_6$ δ 8.79 (s, 1H), 8.52 (d, J = 7.8 Hz, 1H), 7.54-7.40 (m, 2H), 7.38-7.25 (m, 1H), 7.20-7.04 (m, 1H), 6.34 (d, J = 2.0 Hz, 1H), 5.52 (s, 1H), 4.46-4.09 (m, 3H), 3.24 (s, 3H), 2.66-2.54 (m, 1H), 2.43-2.30 (m, 1H). | 402.1<br>3.69 min |

TABLE 4-continued

| Example<br>Ki (μM)<br>METHOD | Structure | Stereo | $^1$H NMR | MS (m/z) R.T. |
|---|---|---|---|---|
| Example 341<br>0.0170<br>METHOD B | 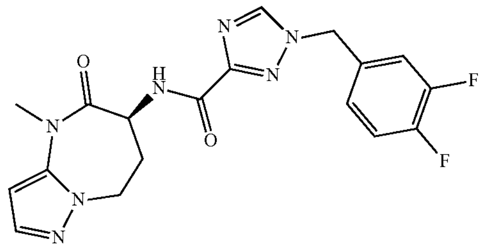 [SMILES: CN1C(=O)[C@@H](NC(=O)c2ncn(Cc3ccc(F)c(F)c3)n2)CCn2nccc21]<br>1-[(3,4-difluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide | Single Known Stereoisomer | $^1$H NMR (400 MHz, DMSO-$d_6$) δ 8.83 (s, 1H), 8.55 (d, J = 7.8 Hz, 1H), 7.53-7.39 (m, 2H), 7.30-7.11 (m, 2H), 6.34 (d, J = 2.0 Hz, 1H), 5.61 (s, 2H), 4.42-4.13 (m, 3H), 3.24 (s, 3H), 2.65-2.54 (m, 1H), 2.44-2.29 (m, 1H). | 40.1.1<br>3.77 min |
| Example 342<br>0.0109<br>METHOD B | 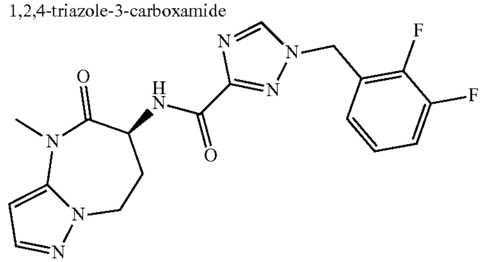<br>1-[(2,3-difluorophenyl)methyl]-N-[rac-(6S)-4-methyl-5-oxo-7,8-dihydro-6H-pyrazol[1,5-a][1,3]diazepin-6-yl]-1,2,4-triazole-3-carboxamide | Single Known Stereoisomer | $^1$H NMR (400 MHz, DMSO-$d_6$) δ 8.80 (s, 1H), 8.55 (d, J = 7.8 Hz, 1H), 7.58-7.35 (m, 3H), 7.30-7.04 (m, 1H), 6.34 (d, J = 2.1 Hz, 1H), 5.48 (s, 2H), 4.43-4.12 (m, 3H), 3.24 (s, 3H), 2.63-2.56 (m, 1H), 2.44-2.30 (m, 1H). | 402.2<br>3.69 min |
| Example 343<br>0.00973<br>METHOD GH1 | 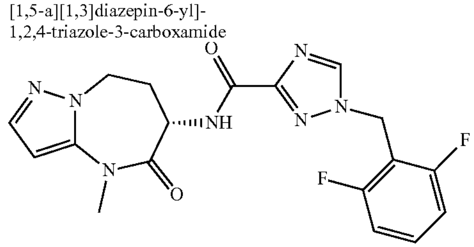<br>1-[(2,6-difluorophenyl)methyl]-N-[(6S)-4-methyl-5-oxo-7,8-dihydro-6H-pyrazolo[1,5-a][1,3]diazepin-6-yl]-1,2,4-triazole-3-carboxamide | Single Known Stereoisomer | 1H NMR (400 MHz, DMSO-d6) δ 8.83 (s, 1H), 8.51 (d, J = 7.8 Hz, 1H), 7.57-7.44 (m, 2H), 7.23-7.10 (m, 2H), 6.33 (d, J = 3.67 2.0 Hz, 1H), 5.56 (s, 2H), 4.42-4.09 (m, 3H), 3.24 (s, 3H), 2.65-2.53 (m, 1H), 2.42-2.30 (m, 1H). | 402.2<br>3.67 min |

TABLE 4-continued

| Example Ki (μM) METHOD | Structure | Stereo | $^1$H NMR | MS (m/z) R.T. |
|---|---|---|---|---|
| Example 344 0.226 METHOD GH1 | 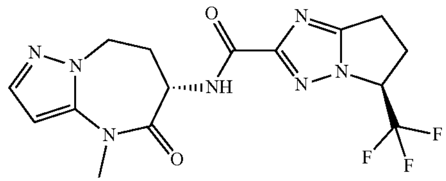 [SMILES: CN1C(=O)[C@@H](NC(=O)c2nc3n(n2)[C@H](C(F)(F)F)CC3)CCn2nccc21] (5S)-N-[(6S)-4-methyl-5-oxo-7,8-dihydro-6H-pyrazolo[1,5-a][1,3]diazepin-6-yl]-5-(trifluoromethyl)-6,7-dihydro-5H-pyrrolo[1,2-b][1,2,4]triazole-2-carboxamide | Single Known Stereoisomer | 1H NMR (400 MHz, DMSO-d6) δ 8.60 (d, J = 7.9 Hz, 1H), 7.49 (d, J = 2.0 Hz, 1H), 6.34 (d, J = 2.0 Hz, 1H), 5.49 (td, J = 7.8, 6.9, 3.4 Hz, 1H), 4.44-4.26 (m, 2H), 4.20 (ddd, J = 14.5, 12.7, 6.6 Hz, 1H), 3.25 (s, 3H), 3.15-2.92 (m, 3H), 2.82-2.70 (m, 1H), 2.65-2.54 (m, 1H), 2.44-2.32 (m, 1H). | 384.1 3.38 min |
| Example 345 0.020 METHOD GH2 | 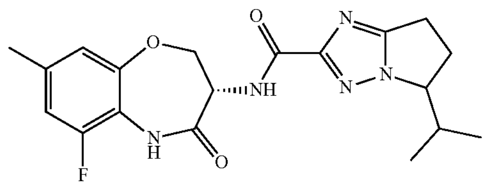 [SMILES: Cc1cc(F)c2c(c1)OC[C@H](NC(=O)c1nc3n(n1)C(C(C)C)CC3)C(=O)N2] N-[(3S)-6-fluoro-8-methyl-4-oxo-3,5-dihydro-2H-1,5-benzoxazepin-3-yl]-5-isopropyl-6,7-dihydro-5H-pyrrolo[1,2-b][1,2,4]triazole-2-carboxamide | Mixture of Diastereomers | 1H NMR (400 MHz, DMSO-d6) δ 10.00 (s, 1H), 8.35 (dd, J = 7.7, 5.2 Hz, 1H), 6.99 (dd, J = 10.7, 1.8 Hz, 1H), 6.89 (s, 1H), 4.90-4.80 (m, 1H), 4.63-4.53 (m, 1H), 4.47 (dd, J = 10.1, 7.3 Hz, 1H), 4.34 (dt, J = 9.1, 4.9 Hz, 1H), 2.92-2.83 (m, 2H), 2.79-2.65 (m, 1H), 2.48-2.35 (m, 1H), 2.30 (s, 3H), 2.23-2.09 (m, 1H), 0.95 (dd, J = 6.9, 1.5 Hz, 3H), 0.81 (dd, J = 6.9, 0.9 Hz, 3H). | 388.1 4.76 min |
| Example 346 0.175 METHOD GH2 | 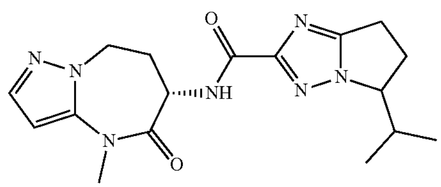 [SMILES: CC(C)C1CCc2nc(C(=O)N[C@H]3CCn4nccc4N(C)C3=O)nn21] 5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Mixture of Diastereomers | 1H NMR (400 MHz, DMSO-d6) δ 8.45 (dd, J = 11.1, 7.8 Hz, 1H), 7.49 (dd, J = 2.0, 0.6 Hz, 1H), 6.34 (dd, J = 2.0, 1.2 Hz, 1H), 4.45-4.24 (m, 3H), 4.24-4.11 (m, 1H), 3.25 (d, J = 1.5 Hz, 3H), 2.92-2.81 (m, 2H), 2.78-2.54 (m, 2H), 2.46-2.28 (m, 2H), 2.15 (pd, J = 6.8, 4.7 Hz, 1H), 0.94 (d, J = 6.8 Hz, 3H), 0.81 (dd, J = 6.8, 1.6 Hz, 3H). | 358.2 3.72 min |

TABLE 4-continued

| Example Ki (μM) METHOD | Structure | Stereo | $^1$H NMR | MS (m/z) R.T. |
|---|---|---|---|---|
| Example 347 0.00491 METHOD GH1 | 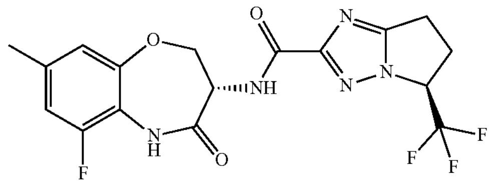 [SMILES: Cc1cc(F)c2c(c1)OC[C@H](NC(=O)c1nc3n(n1)[C@H](C(F)(F)F)CC3)C(=O)N2] (5S)-N-[(3 S)-6-fluoro-8-methyl-4-oxo-3,5-dihydro-2H-1,5-benzoxazepin-3-yl]-5-(trifluoromethyl)-6,7-dihydro-5H-pyrrolo[1,2-b][1,2,4]triazole-2-carboxamide | Single Known Stereoisomer | 1H NMR (400 MHz, DMSO-d6) δ 10.01 (s, 1H), 8.49 (d, J = 7.8 Hz, 1H), 6.99 (ddd, J = 10.7, 1.8, 0.8 Hz, 1H), 6.90 (s, 1H), 5.58-5.43 (m, 1H), 4.86 (dt, J = 11.1, 7.5 Hz, 1H), 4.60 (dd, J = 11.2, 10.1 Hz, 1H), 4.46 (dd, J = 10.1, 7.3 Hz, 1H), 3.16-2.96 (m, 3H), 2.84-2.70 (m, 1H), 2.35-2.27 (m, 3H). | 414.1 4.60 min |
| Example 348 0.0138 METHOD G11 | 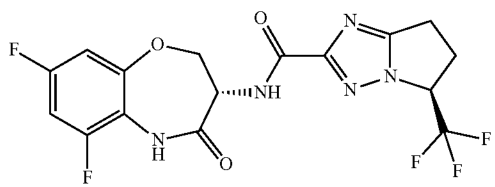 [SMILES: O=C(N[C@H]1COc2cc(F)cc(F)c2NC1=O)c1nc2n(n1)[C@H](C(F)(F)F)CC2] (5S)-N-[(3S)-6,8-difluoro-4-oxo-3,5-dihydro-2H-1,5-benzoxazepin-3-yl]-5-(trifluoromethyl)-6,7-dihydro-5H-pyrrolo[1,2-b][1,2,4]triazole-2-carboxamide | Single Known Stereoisomer | 1H NMR (400 MHz, DMSO-d6) δ 8.52 J = 7.7 Hz, 1H), 7.24 (ddd, J = 10.4, 9.1, 2.9 Hz, 1H), 7.04 (ddd, J = 9.4, 2.9, 1.8 Hz, 1H), 5.57-5.44 (m, 1H), 4.92 (dt, J = 11.1, 7.4 Hz, 1H), 4.66 (dd, J = 11.1, 10.2 Hz, 1H), 4.52 (dd, J = 10.2, 7.1 Hz, 1H), 3.15-2.97 (m, 4H), 2.83-2.71 (m, 1H). | 418.1 4.34 min |
| Example 349 0.0335 METHOD GH2 | 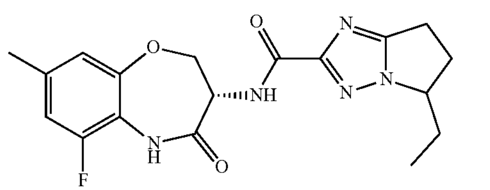 [SMILES: CCC1CCc2nc(C(=O)N[C@H]3COc4cc(C)cc(F)c4NC3=O)nn21] 5-ethyl-N-[(3S)-6-fluoro-8-methyl-4-oxo-3,5-dihydro-2H-1,5-benzoxazepin-3-yl]-6,7-dihydro-5H-pyrrolo[1,2-b][1,2,4]triazole-2-carboxamide | Mixture of Diastereomers | 1H NMR (400 MHz, DMSO-d6) δ 10.00 (s, 1H), 8.35 (dd, J = 7.8, 2.7 1H), 6.98 (ddd, J = 10.7, 1.8, 0.8 Hz, 1H), 6.89 (s, 1H), 4.90-4.79 (m, 1H), 4.58 (ddd, J = 11.2, 10.1, 5.5 Hz, 1H), 4.46 (ddd, J = 10.1, 7.3, 1.8 Hz, 1H), 4.43-4.34 (m, 1H), 2.93-2.76 (m, 3H), 2.37-2.31 (m, 1H), hydrogen atom of the alkyl group is replaced by halogen (e.g, yl). In some em | 374.1 4.44 min |

TABLE 4-continued

| Example Ki (μM) METHOD | Structure | Stereo | $^1$H NMR | MS (m/z) R.T. |
|---|---|---|---|---|
| Example 350 0.0194 METHOD G11 | 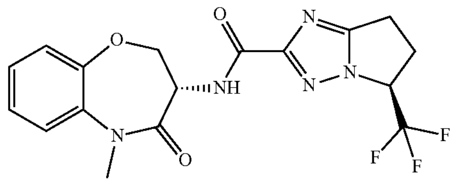 [SMILES: CN1C(=O)[C@@H](NC(=O)c2nc3n(n2)[C@H](C(F)(F)F)CC3)COc2ccccc21] (5S)-N-[(3 S)-5-methyl-4-oxo-2,3-dihydro-1,5-benzoxazepin-3-yl]-5-(trifluoromethyl)-6,7-dihydro-5H-pyrrolo[1,2-b][1,2,4]triazole-2-carboxamide | Single Known Stereoisomer | 1H NMR (400 MHz, DMSO-d6) δ 8.52 (d, J = 8.0 Hz, 1H), 7.55-7.47 (m, 1H), 7.38-7.20 (m, 3H), 5.56-5.44 (m, 1H), 4.84 (dt, J = 11.5, 7.8 Hz, 1H), 4.59 (dd, J = 11.5, 9.9 Hz, 1H), 4.42 (dd, J = 9.9, 7.7 Hz, 1H), 3.32 (s, 3H), 3.12-2.97 (m, 3H), 2.81-2.71 (m, 1H). | 396.1 4.86 min |
| Example 351 0.394 METHOD GH2 | 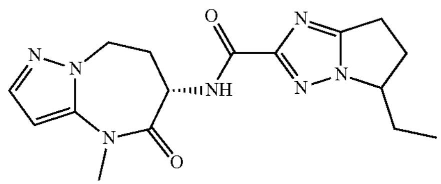 [SMILES: CCC1CCc2nc(C(=O)N[C@H]3CCn4nccc4N(C)C3=O)nn21] 5-ethyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Mixture of Diastereomers | 1H NMR (400 MHz, DMSO-d6) δ 8.44 (t, J = 7.5 Hz, 1H), 7.49 (dd, J = 2.0, 0.5 Hz, 1H), 6.34 (dd, J = 2.1, 0.8 Hz, 1H), 4.43-4.12 (m, 4H), 3.25 (d, J = 1.5 Hz, 3H), 2.94-2.76 (m, 3H), 2.69-2.54 (m, 1H), 2.45-2.27 (m, 2H), 1.95-1.83 (m, 1H), 1.78-1.63 (m, 1H), 0.91 (td, J = 7.4, 1.0 Hz, 3H). | 344.2 3.87 min |
| Example 352 0.0969 GH_chiral_1 | 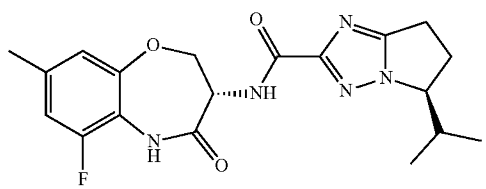 [SMILES: Cc1cc(F)c2c(c1)OC[C@H](NC(=O)c1nc3n(n1)[C@H](C(C)C)CC3)C(=O)N2] (5S)-5-isopropyl-N-[(3S)-6-fluoro-8-methyl-4-oxo-3,5-dihydro-2H-1,5-benzoxazepin-3-yl]-6,7-dihydro-5H-pyrrolo[1,2-b][1,2,4]triazole-2-carboxamide | Single Known Stereoisomer | 1H NMR (400 MHz, DMSO-d6) δ 10.00 (s, 1H), 8.36 (d, J = 7.7 Hz, 1H), 6.99 (dd, J = 10.9, 1.8 1H), 6.89 (d, J = 1.8 Hz, 1H),4.85 (dt, J = 11.1, 7.5 Hz, 1H), 4.58 (t, J = 10.7 Hz, 1H), 4.47 (dd, J = 10.1, 7.3 Hz, 1H), 4.34 (dt, J = 9.0, 4.8 Hz, 1H), 2.92-2.82 (m, 2H), 2.79-2.64 (m, 1H), 2.42 (dtd, J = 15.0, 8.7, 8.2, 4.8 Hz, 1H), 2.30 (s, 3H), 2.22-2.08 (m, 1H), 0.95 (d, J = 6.8 Hz, 3H), 0.81 (d, J = 6.8 Hz, 3H). | 388.2 5.12 min |

TABLE 4-continued

| Example Ki (μM) METHOD | Structure | Stereo | $^1$H NMR | MS (m/z) R.T. |
|---|---|---|---|---|
| Example 353 0.0498 GH_chiral_2 | 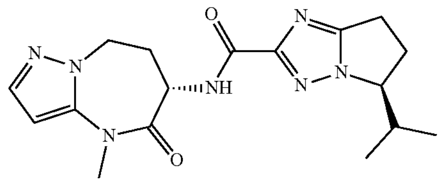 [SMILES: CC(C)[C@@H]1CCc2nc(C(=O)N[C@H]3CCn4nccc4N(C)C3=O)nn21] (5S)-5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Known Stereoisomer | 1H NMR (400 MHz, DMSO-d6) δ 8.43 (d, J = 7.8 Hz, 1H), 7.49 (d, J = 1.9 Hz, 1H), 6.34 (d, J = 2.0 Hz, 1H), 4.44-4.14 (m, 4H), 3.25 (s, 3H), 2.86 (t, J = 7.5 Hz, 2H), 2.77-4.17 2.56 (m, 2H), 2.46-2.30 (m, 2H), 2.22-2.09 (m, 1H), 0.94 (d, J = 6.8 Hz, 3H), 0.81 (d, J = 6.8 Hz, 3H). | 358.2 4.17 min |
| Example 354 0.0045 GH_chiral_1 | 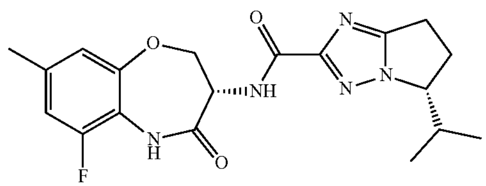 [SMILES: Cc1cc(F)c2c(c1)OC[C@H](NC(=O)c1nc3n(n1)[C@@H](C(C)C)CC3)C(=O)N2] (5R)-5-isopropyl-N-[(3S)-6-fluoro-8-methyl-4-oxo-3,5-dihydro-2H-1,5-benzoxazepin-3-yl]-6,7-dihydro-5H-pyrrolo[1,2-b][1,2,4]triazole-2-carboxamide | Single Known Stereoisomer | 1H NMR (400 MHz, DMSO-d6) δ 10.01 (s, 1H), 8.35 (d, J = 7.7 Hz, 1H), 6.99 (ddd, J = 10.8, 1.9, 0.8 Hz, 1H), 6.89 (dt, J = 1.9, 1.0 Hz, 1H), 4.85 (dt, J = 11.0, 7.5 Hz, 1H), 4.57 (dd, J = 11.1, 10.1 Hz, 1H), 4.47 (dd, J = 10.1, 7.3 Hz, 1H), 4.34 (dt, J = 8.4, 4.9 Hz, 1H), 2.87 (t, J = 7.5 Hz, 2H), 2.78-2.65 (m, 1H), 2.47-2.36 (m, 1H), 2.33 -2.28 (m, 3H), 2.21-2.09 (m, 1H), 0.94 (d, J = 6.8 Hz, 3H), 0.81 (d, J = 6.8 Hz, 3H) | 388.2 5.14 min |
| Example 355 0.0521 METHOD GH2 | 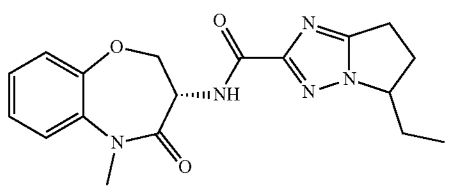 5-ethyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Mixture of Diastereomers | 1H NMR (400 MHz, DMSO-d6) δ 8.37 (dd, J= 8.0, 3.9 Hz, 1H), 7.54-7.47 (m, 1H), 7.37-7.21 (m, 3H), 4.88-4.77 (m, 1H), 4.56 (ddd, J = 11.5, 9.9, 7.0 Hz, 1H), 4.46-4.34 (m, 2H), 3.31 (s, 3H), 2.93 -2.75 (m, 3H), 2.39-2.27 (m, 1H), 1.96-1.82 (m, 1H), 1.77-1.63 (m, 1H), 0.91 (td, J = 7.5, 1.1 Hz, 3H). | 356.1 4.28 min |

TABLE 4-continued

| Example Ki (μM) METHOD | Structure | Stereo | $^{1}$H NMR | MS (m/z) R.T. |
|---|---|---|---|---|
| Example 356 0.00702 METHOD GH3 | 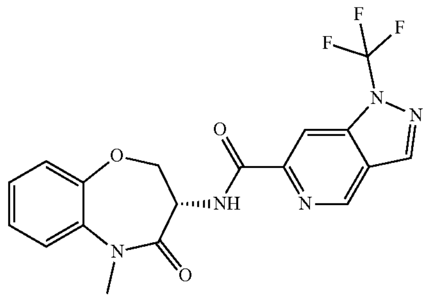 [SMILES: CN1C(=O)[C@@H](NC(=O)c2cc3c(cn2)cnn3C(F)(F)F)COc2ccccc21] (S)-N-(5-methyl-4-oxo-2,3,4,5-tetrahydrobenzo[b][1,4]oxazepin-3-yl)-1-(trifluoromethyl)-1H-pyrazolo[4,3-c]pyridine-6-carboxamide | Single Known Stereoisomer | 1H NMR (400 MHz, DMSO-d6) δ 9.41 (d, J = 1.1 Hz, 1H), 9.12 (d, J = 7.8 Hz, 1H), 8.94 (s, 1H), 8.21 (p, J = 1.3 Hz, 1H), 7.52 (dd, J = 7.4, 2.1 Hz, 1H), 7.39-7.23 (m, 3H), 4.93 (dt, J = 11.3, 7.8 Hz, 1H), 4.66-4.48 (m, 2H), 3.35 (s, 3H). | 406.1 5.53 min |
| Example 357 0.0461 METHOD G11 | 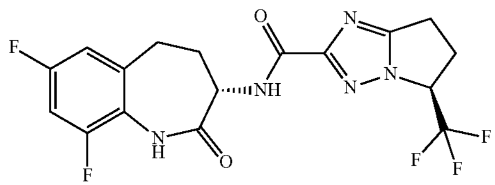 (5S)-N-[(3S)-7,9-difluoro-2-oxo-1,3,4,5-tetrahydro-1-benzazepin-3-yl]-5-(trifluoromethyl)-6,7-dihydro-5H-pyrrolo[1,2-b][1,2,4]triazole-2-carboxamide | Single Known Stereoisomer | 1H NMR (400 MHz, DMSO-d6) δ 9.97 (s, 1H), 8.34 (d, J = 7.5 Hz, 1H), 7.27 (ddd, J = 10.1, 9.0, 2.8 Hz, 1H), 7.20-7.10 (m, 1H), 5.55-5.43 (m, 1H), 4.36 (dt, J = 11.5, 7.8 Hz, 1H), 3.12-2.97 (m, 3H), 2.85-2.70 (m, 3H), 2.48 -2.38 (m, 1H), 2.31-2.18 (m, 1H). | 416.1 4.30 min |
| Example 358 0.0090 GH_chiral_3 | 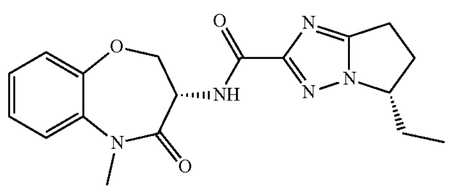 [SMILES: CC[C@H]1CCc2nc(C(=O)N[C@H]3COc4ccccc4N(C)C3=O)nn21] (5S)-5-ethyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Single Unknown Stereoisomer | 1H NMR (400 MHz, DMSO-d6) δ 8.36 (d, J = 8.0 Hz, 1H), 7.54-7.46 (m, 1H), 7.38-7.20 (m, 3H), 4.83 (dt, J = 11.5, 7.8 Hz, 1H), 4.55 (dd, J = 11.4, 9.9 Hz, 1H), 4.46-4.33 (m, 2H), 3.32 (s, 3H), 2.92-2.76 (m, 3H), 2.38-2.25 (m, 1H), 1.88 (dtd, J = 14.9, 7.4, 5.1 Hz, 1H), 1.70 (dt, J = 14.0, 7.2 Hz, 1H), 0.91 (t, J = 7.4 Hz, 3H). | 356.1 4.47 min |

TABLE 4-continued

| Example Ki (μM) METHOD | Structure | Stereo | $^1$H NMR | MS (m/z) R.T. |
|---|---|---|---|---|
| Example 359<br>0.303<br>GH_chiral_3 | 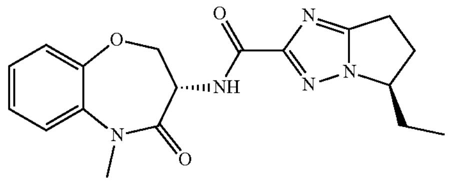 [SMILES: CC[C@@H]1CCc2nc(C(=O)N[C@H]3COc4ccccc4N(C)C3=O)nn21]<br>(5R)-5-ethyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Single Unknown Stereoisomer | 1H NMR (400 MHz, DMSO-d6) δ 8.37 (d, J = 8.0 Hz, 1H), 7.50 (dd, J = 7.6, 2.0 Hz, 1H), 7.38-7.16 (m, 3H), 4.82 (dt, J = 11.5, 7.8 Hz, 1H), 4.57 (dd, J-11.5, 9.9 Hz, 1H), 4.47-4.33 (m, 2H), 3.32 (s, 3H), 2.97-2.75 (m, 3H), 2.39-2.26 (m, 1H), 1.89 (ddd, J = 13.9, 7.4, 5.2 Hz, 1H), 1.78-1.63 (m, 1H), 0.91 (t, J = 7.4 Hz, 3H). | 356.1<br>4.45 min |
| Example 360<br>0.0104<br>METHOD GH4 &<br>METHOD GH3 | 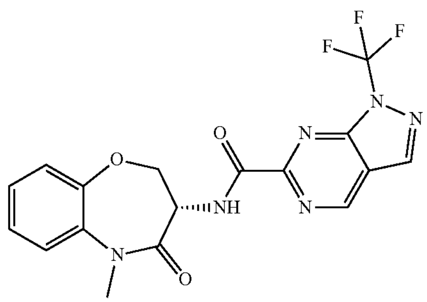<br>N-[(3S)-5-methyl-4-oxo-2,3-dihydro-1,5-benzoxazepin-3-yl]-1-(trifluoromethyl)pyrazolo[3,4-d]pyrimidine-6-carboxamide | Single Known Stereoisomer | 1H NMR (400 MHz, DMSO-d6) δ 9.67 (s, 1H), 9.15 (d, J = 7.7 Hz, 1H), 8.92 (s, 1H), 7.57-7.50 (m, 1H), 7.39-7.24 (m, 3H), 4.91 (dt, J = 10.9, Hz, 1H), 4.64-4.50 (m, 2H), 3.35 (s, 3H). | 407.1<br>4.84 min |
| Example 361<br>0.511<br>METHOD GH5 &<br>METHOD GH2 | 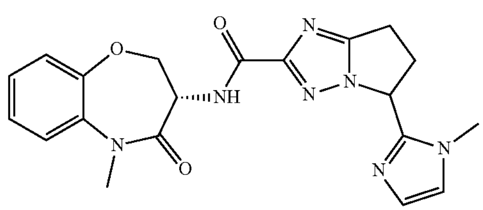 [SMILES: CN1C(=O)[C@@H](NC(=O)c2nc3n(n2)C(c2nccn2C)CC3)COc2ccccc21]<br>5-(1-methylimidazol-2-yl)-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Mixture of Diastereomers | 1H NMR (400 MHz, DMSO-d6) δ 8.39 (dd, J = 8.0, 5.7 Hz, 1H), 7.54-7.45 (m, 1H), 7.36-7.18 (m, 4H), 6.84 (d, J = 1.1 Hz, 1H), 5.91-5.80 (m, 1H), 4.80 (dt, J = 11.4, 7.8 Hz, 1H), 4.55 (ddd, J = 11.7, 9.9, 2.2 Hz, 1H), 4.39 (ddd, J = 9.9, 7.7, 4.4 Hz, 1H), 3.79 (d, J = 0.8 Hz, 3H), 3.31 (s, 3H), 3.19-2.95 (m, 4H). | 408.1<br>2.70 |

TABLE 4-continued

| Example Ki (μM) METHOD | Structure | Stereo | $^1$H NMR | MS (m/z) R.T. |
|---|---|---|---|---|
| Example 362 0.896 | 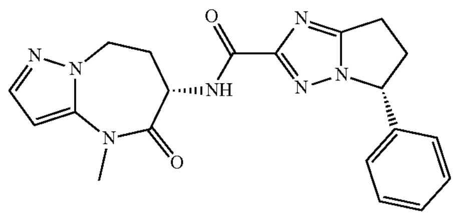 [SMILES: CN1C(=O)[C@@H](NC(=O)c2nc3n(n2)[C@@H](c2ccccc2)CC3)CCn2nccc21] (5R) -N-[(6S)-4-methyl-5-oxo-7,8-dihydro-6H-pyrazolo[1,5-a][1,3]diazepin-6-yl]-5-phenyl-6,7-dihydro-5H-pyrrolo[1,2-b][1,2,4]triazole-2-carboxamide | Single Unknown Stereoisomer | $^1$H NMR (400 MHz, DMSO-d6) δ 8.51 (d, J = 7.8 Hz, 1H), 7.48 (d, J = 2.0 Hz, 1H), 7.44-7.32 (m, 3H), 7.28-7.20 (m, 2H), 6.33 (d, J = 2.0 Hz, 1H), 5.57 (dd, J = 8.2, 5.9 Hz, 1H), 4.41-4.32 (m, 1H), 4.23-4.23 (m, 1H), 4.23-4.13 (m, 1H), 3.24 (s, 3H), 3.21-3.14 (m, 1H), 3.14-3.04 (m, 1H), 3.04-2.93 (m, 1H), 2.63-2.52 (m, 2H), 2.37 (td, J = 12.5, 6.6 Hz, 1H). LCMS $R_T$ = 3.76 min, m/z = 392.2 $(M + H)^+$. | 392.2 3.76 min |
| Example 363 0.0212 | 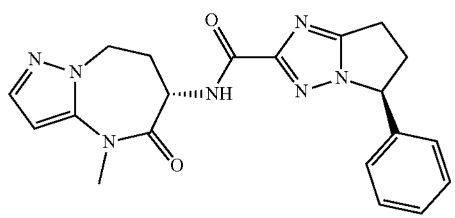 [SMILES: CN1C(=O)[C@@H](NC(=O)c2nc3n(n2)[C@H](c2ccccc2)CC3)CCn2nccc21] (5S)-N-[(6S)-4-methyl-5-oxo-7,8-dihydro-6H-pyrazolo[1,5-a][1,3]diazepin-6-yl]-5-phenyl-6,7-dihydro-5H-pyrrolo[1,2-b][1,2,4]triazole-2-carboxamide | Single Unknown Stereoisomer | $^1$H NMR (400 MHz, DMSO-d6) δ 8.49 (d, J = 7.7 Hz, 1H), 7.48 (d, J = 2.0 Hz, 1H), 7.43-7.32 (m, 3H), 7.26-7.21 (m, 2H), 6.33 (d, J = 2.0 Hz, 1H), 5.57 (dd, J = 8.3, 5.8 Hz, 1H), 4.41-4.24 (m, 2H), 4.24 -4.12 (m, 1H), 3.24 (s, 3H), 3.22-3.06 (m, 2H), 3.05-2.94 (m, 1H), 2.61-2.52 (m, 2H), 2.42-2.31 (m, 1H). | 392.2 3.76 min |

TABLE 4-continued

| Example Ki (μM) METHOD | Structure | Stereo | $^1$H NMR | MS (m/z) R.T. |
|---|---|---|---|---|
| Example 364<br>0.450<br>Method CS1 | 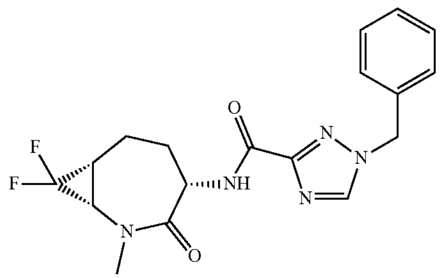 [SMILES: CN1C(=O)[C@@H](NC(=O)c2ncn(Cc3ccccc3)n2)CC[C@@H]2[C@H]1C2(F)F]<br>1-benzyl-N-[(1R,45,7S)-8,8-difluoro-6-methyl-5-oxo-6-azabicyclo[5.1.0]octan-4-yl]-1,2,4-triazole-3-carboxamide | Single Known Stereoisomer | $^1$H NMR (400 MHz, DMSO-d6) δ 8.82 (s, 1H), 8.58 (d, J = 4.4 Hz, 1H), 7.43-7.27 (m, 5H), 5.48 (s, 2H), 4.43-4.33 (m, 1H), 3.27-3.14 (m, 1H), 4.26 2.80 (s, 3H), 2.55-2.43 (m, 1H), 2.10-2.00 (m, 3H), 1.30- 1.10 (m, 1H). | 376.2<br>4.26 min |
| Example 365<br>0.0311<br>Method CS2 | 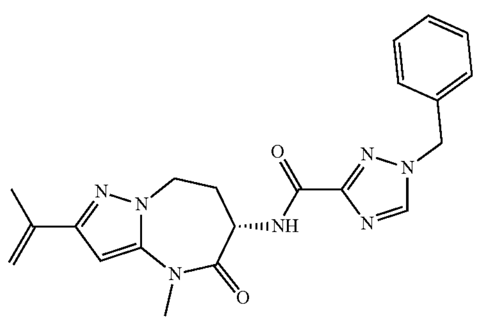 [SMILES: C=C(C)c1cc2n(n1)CC[C@H](NC(=O)c1ncn(Cc3ccccc3)n1)C(=O)N2C]<br>1-benzyl-N-(2-isopropenyl-4-methyl-5-oxo-7,8-dihydro-6H-pyrazolo[1,5-a][1,3]diazepin-6-yl)-1,2,4-triazole-3-carboxamide | Mixture of Enantiomers | $^1$H NMR (400.33 MHz, DMSO-d6) δ 8.82 (s, 1H), 8.54 (d, J = 7.9 Hz, 1H), 7.47-7.18 (m, 5H), 6.59 (s, 1H), 5.56-5.43 (m, 3H), 5.06 (t, J = 1.7 Hz, 1H), 4.42-4.28 (m, 2H), 4.28-4.09 (m, 1H), 3.25 | 406.2<br>4.47 min |

TABLE 4-continued

| Example<br>Ki (μM)<br>METHOD | Structure | Stereo | $^{1}H$ NMR | MS (m/z) R.T. |
|---|---|---|---|---|
| Example 366<br>0.0173<br>Method CS3 | 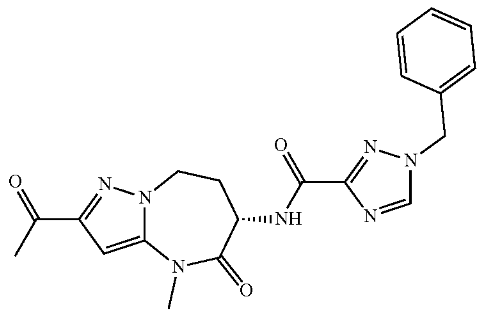 [SMILES: CC(=O)c1cc2n(n1)CC[C@H](NC(=O)c1ncn(Cc3ccccc3)n1)C(=O)N2C]<br>(S)-N-(2-acetyl-4-methyl-5-oxo-5,6,7,8-tetrahydro-4H-pyrazolo[1,5-a][1,3]diazepin-6-yl)-1-benzyl-1H-1,2,4-triazole-3-carboxamide | Single<br>Known<br>Stereoisomer | $^{1}H$ NMR (400.33 MHz, DMSO-d6) δ 8.82 (s, 1H), 8.59 (d, J = 7.7 Hz, 1H), 7.43-7.26 (m, 5H), 6.83 (s, 1H), 5.48 (s, 2H), 4.48 (dd, J = 14.5, 7.9 Hz, 1H), 4.41-4.26 (m, 2H), 3.26 (s, 3H), 2.72-2.57 (m, 1H), 2.48 (s, 3H), 2.52-2.40 (m, 1H). | 408.2<br>3.84 min |
| Example 367<br>0.161<br>Method CS4 | 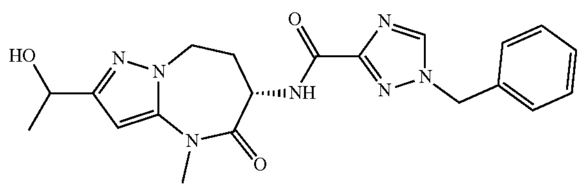 [SMILES: CC(O)c1cc2n(n1)CC[C@H](NC(=O)c1ncn(Cc3ccccc3)n1)C(=O)N2C]<br>1-benzyl-N-((6S)-2-(1-hydroxyethyl)-4-methyl-5-oxo-5,6,7,8-tetrahydro-4H-pyrazolo[1,5-a][1,3]diazepin-6-yl)-1H-1,2,4-triazole-3-carboxamide | Single<br>Unknown<br>Stereoisomer | $^{1}H$ NMR (400.33 MHz, DMSO-d6) δ 8.82 (s, 1H), 8.52 (d, J = 7.8 Hz, 1H), 7.43-7.27 (m, 5H), 6.26 (s, 1H), 5.48 (s, 2H), 5.08 (d, J = 5.1 Hz, 1H), 4.69-4.58 (m, 1H), 4.38-4.24 (m, 2H), 4.20-4.07 1H), 3.23 (s, 3H), 2.64-2.45 (m, 1H), 2.39-2.29 (m, 1H), 1.38 (d, J = 6.5 Hz, 3H). | 410.2<br>3.44 min |
| Example 368<br>0.154<br>Method CS4 | 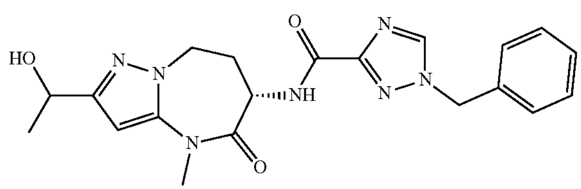 [SMILES: CC(O)c1cc2n(n1)CC[C@H](NC(=O)c1ncn(Cc3ccccc3)n1)C(=O)N2C]<br>1-benzyl-N-((6S)-2-(1-hydroxyethyl)-4-methyl-5-oxo-5,6,7,8-tetrahydro-4H-pyrazolo[1,5-a][1,3]diazepin-6-yl)-1H-1,2,4-triazole-3-carboxamide | Single<br>Unknown<br>Stereoisomer | $^{1}H$ NMR (400.33 MHz, DMSO-d6) δ 8.82 (s, 1H), 8.51 (d, J = 7.9 Hz, 1H), 7.43-7.26 (m, 5H), 6.27 s, 1H), 5.48 (s, 2H), 5.16 (d, J = 4.5 Hz, 1H), 4.72-4.61 (m, 1H), 4.40-4.23 (m, 2H), 4.21-4.07 (m, 1H), 3.24 (s, 3H), 2.64-2.50 (m, 1H), 2.39-2.29 (m, 1H), 1.34 (d, J = 6.5 Hz, 3H). | 410.2<br>3.48 min |

TABLE 4-continued

| Example Ki (μM) METHOD | Structure | Stereo | $^1$H NMR | MS (m/z) R.T. |
|---|---|---|---|---|
| Example 369 0.345 Method CS5 | 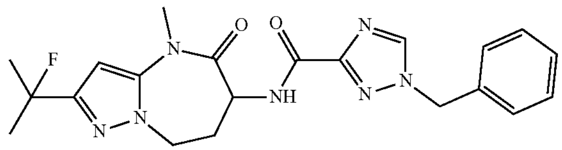 [SMILES: CN1C(=O)C(NC(=O)c2ncn(Cc3ccccc3)n2)CCn2nc(C(C)(C)F)cc21] Not draw with arbitrary assignment I don't know absolute stereochem 1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 .33 MHz, DMSO-d6) δ 8.82 (s, 1H), 8.55 (d, J = 7.8 Hz, 1H), 7.43-7.27 (m, 5H), 6.48 (s, 1H), 5.48 (s, 2H), 4.40-4.24 (m, 2H), 4.25-4.13 (m, 1H), 3.25 (s, 3H), 2.66-2.54 (m, 1H), 2.44-2.32 (m, 1H), 1.71 (d, 7.7 Hz, 3H), 1.66 (d, 7.7 Hz, 3H). | 426.3 4.47 min |
| Example 370 0.555 Method CS5 | 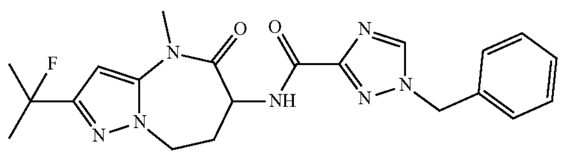 [SMILES: CN1C(=O)C(NC(=O)c2ncn(Cc3ccccc3)n2)CCn2nc(C(C)(C)F)cc21] Not draw with arbitrary assignment I don't know absolute stereochem 1-benzyl-N-[2-(1-fluoro-1-methyl-ethyl)-4-methyl-5-oxo-7,8-dihydro-6H-pyrazolo-[1,5-a][1,3]diazepin-6-yl]-1,2,4-triazole-3-carboxamide | Single Unknown Stereoisomer | $^1$H NMR (400.33 MHz, DMSO-d6) δ 8.82 (s, 1H), 8.55 (d, J = 7.8 Hz, 1H), 7.43-7.27 (m, 5H), 6.48 (s, 1H), 5.48 (s, 2H), 4.40-4.27 (m, 2H), 4.25-4.13 (m, 1H), 3.25 (s, 3H), 2.66-2.53 (m, 1H), 2.44-2.32 (m, 1H), 1.71 (d, 7.7 Hz, 3H), 1.66 (d, 7.7 Hz, 3H). | 426.3 4.47 min |
| Example 371 0.100 Method CS6 | 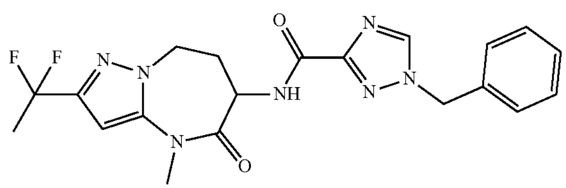 [SMILES: CN1C(=O)C(NC(=O)c2ncn(Cc3ccccc3)n2)CCn2nc(C(C)(F)F)cc21] 1-benzyl-N-[2-(1,1-difluoroethyl)-4-methyl-5-oxo-7,8-dihydro-6H-pyrazolo[1,5-a][1,3]diazepin-6-yl]-1,2,4-triazole-3-carboxamide | Mixture of Enantiomers | $^1$H NMR (400.33 MHz, DMSO-d6) δ 8.82 (s, 1H), 8.59 (d, J = 7.7 Hz, 1H), 7.43-7.26 (m, 5H), 6.65 (s, 1H), 5.48 (s, 2H), 4.45-4.19 (m, 3H), 3.26 (s, 3H), 2.71-2.54 (m, 1H), 2.51-2.36 (m, 1H), 2.00 (t, J = 18.8 Hz, 3H). | 430.2 4.55 min |

TABLE 4-continued

| Example Ki (μM) METHOD | Structure | Stereo | $^1$H NMR | MS (m/z) R.T. |
| --- | --- | --- | --- | --- |
| Example 372<br>0.488<br>Method CS7 | 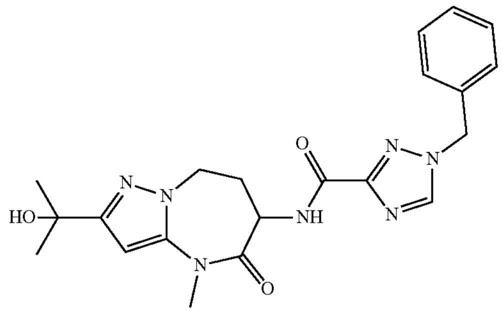 [SMILES: CN1C(=O)C(NC(=O)c2ncn(Cc3ccccc3)n2)CCn2nc(C(C)(C)O)cc21]<br>1-benzyl-N-[2-(1-hydroxy-1-methyl-ethyl)-4-methyl-5-oxo-7,8-dihydro-6H-pyrazolo [1,5-a][1,3]diazepin-6-yl]-1,2,4-triazole-3-carboxamide | Mixture of Enantiomers | $^1$H NMR (400.33 MHz, DMSO-d6) δ 8.82 (s, 1H), 8.52 (d, J = 7.9 Hz, 1H), 7.43-7.25 (m, 5H), 6.28 (s, 1H), 5.48 (s, 2H), 4.97 (s, 1H), 4.39-4.25 (m, 2H), 4.20-4.07 (m, 1H), 3.23 (s, 3H), 2.60 (ddd, J = 20.6, 7.8, 5.2 Hz, 1H), 2.34 (td, J = 12.6, 6.6 Hz, 1H), 1.45 (s, 3H), 1.40 (s, 3H). | 406.2<br>3.56 min |
| Example 373<br>0.0043<br>METHOD GZ1 | 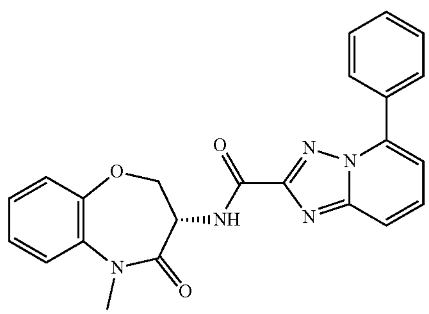 [SMILES: CN1C(=O)[C@@H](NC(=O)c2nc3cccc(-c4ccccc4)n3n2)COc2ccccc21]<br>5-ethyl-N-[rac-(6S)-4-methyl-5-oxo-7,8-dihydro-6H-pyrazolo[1,5-a] [1,3]diazepin-6-[1,2,4]triazolo[1,5-a] pyridine-2-carboxamide | Single Known Stereoisomer | $^1$H NMR (400 MHz, DMSO-d6) δ 8.79 (d, J = 7.8 Hz, 1H), 8.03-7.91 (m, 3H), 7.88 (m, 1H), 7.65-7.55 (m, 3H), 7.50 (ddd, J = 14.5, 7.3, 1.7 Hz, 2H), 7.41-7.22 (m, 3H), 4.90 (dt, J = 11.4, 7.8 Hz, 1H), 4.63 (dd, J = 11.5, 9.9 Hz, 1H), 4.48 (dd, J = 9.9, 7.7 Hz, 1H), 3.34 (s, 3H) | 414.1<br>5.10 min |

TABLE 4-continued

| Example<br>Ki (μM)<br>METHOD | Structure | Stereo | $^1$H NMR | MS (m/z) R.T. |
|---|---|---|---|---|
| Example 374<br>0.269<br>METHOD GZ10 | 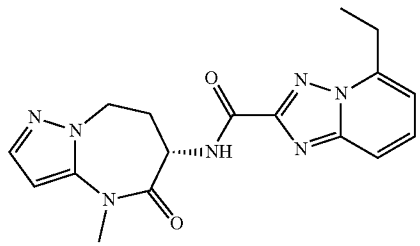 [SMILES: CCc1cccc2nc(C(=O)N[C@H]3CCn4nccc4N(C)C3=O)nn12]<br>5-ethyl-N-[rac-(6S)-4-methyl-5-oxo-7,8-dihydro-6H-pyrazolo[1,5-a][1,3]diazepin-6-yl]-[1,2,4]triazolo[1,5-a]pyridine-2-carboxamide | Single Known Stereoisomer | %: $^1$H NMR (400 MHz, DMSO-d6) δ 8.87 (d, J = 7.8 Hz, 1H), 7.85-7.71 (m, 2H), 7.51 (d, J = 2.0 Hz, 1H), 7.20 (dq, J = 7.3, 1.2 Hz, 1H), 6.37 (d, J = 2.0 Hz, 1H), 4.46-4.33 (m, 2H), 4.23 (ddd, J = 14.5, 12.6, 6.6 Hz, 1H), 3.45-3.23 (m, 3H), 3.25-3.11 (m, 2H), 2.67 (tt, J = 12.9, 8.1 Hz, 1H), 2.44 (td, J = 12.3, 6.5 Hz, 1H), 1.37 (t, J = 7.5 Hz, 3H) | 354.2<br>3.51 min |
| Example 375<br>0.0280<br>Method GZ1 | 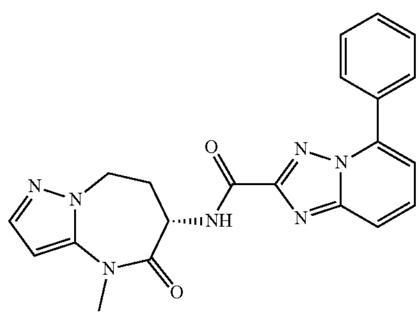 [SMILES: CN1C(=O)[C@@H](NC(=O)c2nc3cccc(-c4ccccc4)n3n2)CCn2nccc21]<br>N-[(6S)-4-methyl-5-oxo-7,8-dihydro-6H-pyrazolo[1,5-a][1,3]diazepin-6-yl]-5-phenyl-[1,2,4]triazolo[1,5-a]pyridine-2-carboxamide | Single Known Stereoisomer | $^1$H NMR (400 MHz, DMSO-d6) δ 8.89 (d, J = 7.7 Hz, 1H), 8.04-7.83 (m, 4H), 7.65-7.54 (m, 3H), 7.53-7.44 (m, 2H), 6.36 (d, J = 2.0 Hz, 1H), 4.45-4.31 (m, 2H), 4.22 (ddd, J = 14.5, 12.6, 6.6 Hz, 1H), 3.39-3.19 (m, 3H), 2.76-2.59 (m, 1H), 2.42 (m, 1H) | 402.1<br>4.12 min |

TABLE 4-continued

| Example Ki (μM) METHOD | Structure | Stereo | $^1$H NMR | MS (m/z) R.T. |
|---|---|---|---|---|
| Example 376<br>0.0423<br>METHOD GZ2 | 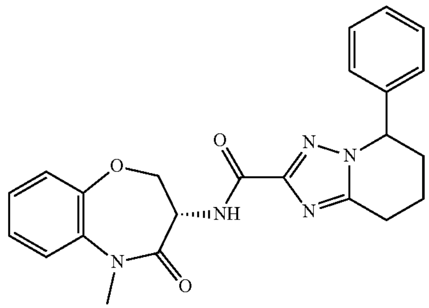 [SMILES: CN1C(=O)[C@@H](NC(=O)c2nc3n(n2)C(c2ccccc2)CCC3)COc2ccccc21]<br>5-phenyl-N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Mixture of Diastereomers | $^1$H NMR (400 MHz, DMSO-d6) δ 8.39 (t, J = 8.0 Hz, 1H), 7.49 (dt, J = 7.5, 1.7 Hz, 1H), 7.40-7.18 (m, 6H), 7.09-7.01 (m, 2H), 5.57 (t, J = 5.8 Hz, 1H), 4.80 (dtd, J = 11.6, 7.8, 2.3 Hz, 1H), 4.57 (ddd, J = 11.5, 9.9, 8.0 Hz, 1H), 4.38 (dd, J= 9.9, 7.7 Hz, 1H), 3.44-3.17 (m, 3H), 3.01 (m, 2H), 2.45-2.32 (m, 1H), 2.10-1.99 (m, 1H), 1.92-1.82 (m, 2H) | 4.18.2<br>4.87 min |
| Example 377<br>0.0108<br>METHOD GZ3 | 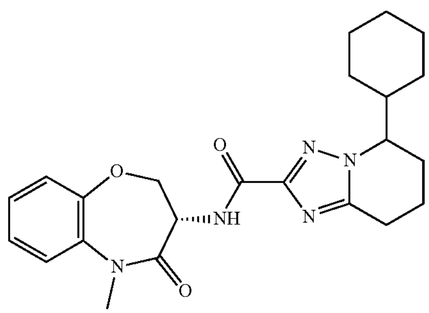 [SMILES: CN1C(=O)[C@@H](NC(=O)c2nc3n(n2)C(C2CCCCC2)CCC3)COc2ccccc21]<br>5-cyclohexyl-N-[rac-(3S)-5-methyl-4-oxo-2,3-dihydro-1,5-benzoxazepin-3-yl]-5,6,7,8-tetrahydro-[1,2,4 ]triazolo[1,5-a]pyridine-2-carboxamide | Mixture of Diastereomers | $^1$H NMR (400 MHz, DMSO-d6) δ 8.37 (m, 1H), 7.55-7.47 (m, 1H), 7.37-7.20 (m, 3H), 4.83 (dtd, J = 11.2, 7.9, 3.1 Hz, 1H), 4.57 (ddd, J = 17.1, 11.5, 9.8 Hz, 1H), 4.42 (dd, J = 9.9, 7.7 Hz, 1H), 4.14 (dt, J = 9.0, 4.3 Hz, 1H), 3.42-3.23 (m, 3H), 2.94-2.72 (m, 2H), 2.26 (ms, 1H), 2.00 (m, 2H), 1.90-1.57 (m, 6H), 1.32-1.21 (m, 1H), 1.11 (m, 5H) | 424.2<br>5.60 min |

TABLE 4-continued

| Example Ki (µM) METHOD | Structure | Stereo | $^1$H NMR | MS (m/z) R.T. |
|---|---|---|---|---|
| Example 378<br>0.00668<br>Method GZ10 | 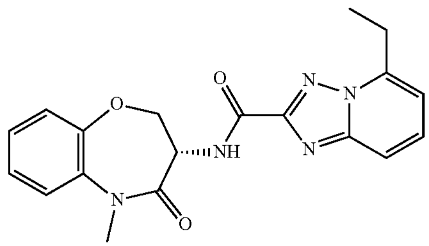 [SMILES: CCc1cccc2nc(C(=O)N[C@H]3COc4ccccc4N(C)C3=O)nn12]<br>5-ethyl-N-[(3 S)-5-methyl-4-oxo-2,3-dihydro-1,5-benzoxazepin-3-yl]-[1,2,4]triazolo[1,5-a]pyridine-2-carboxamide | Single Known Stereoisomer | 1H NMR (400 MHz, DMSO-d6) δ 8.78 (d, J = 7.9 Hz, 1H), 7.86-7.71 (m, 2H), 7.53 (dd, J = 7.5, 2.0 Hz, 1H), 7.39-7.17 (m, 4H), 4.91 (dt, J = 11.5, 7.8 Hz, 1H), 4.64 (dd, J = 11.5, 9.9 Hz, 1H), 4.49 (dd, J = 9.9, 7.7 Hz, 1H), 3.34 (s, 3H), 3.32-3.12 (m, 2H), 1.36 (t, J = 7.5 Hz, 3H) | 366.1<br>4.57 min |
| Example 379<br>0.374<br>Method GZ2 | 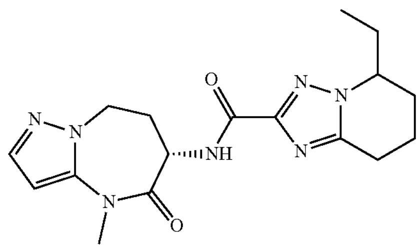 [SMILES: CCC1CCCc2nc(C(=O)N[C@H]3CCn4nccc4N(C)C3=O)nn21]<br>5-ethyl-N-[(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide | Mixture of Diastereomers | $^1$H NMR (400 MHz, DMSO-d6) δ 8.43 (dd, J = 10.8, 7.9 Hz, 1H), 7.49 (d, J = 2.0 Hz, 1H), 6.34 (d, J = 2.0 Hz, 1H), 4.42-4.12 (m, 3H), 3.25 (d, J = 1.9 Hz, 3H), 2.94-2.74 (m, 2H), 2.67-2.52 (m, 1H), 2.37 (dt, J = 13.3, 8.2 Hz, 1H), 2.20-1.91 (m, 3H), 1.87-1.65 (m, 4H), 1.24 (s, 2H), 0.91 (t, J = 7.4 Hz, 3H) | 358.2<br>3.50 min |
| Example 380<br>0.154<br>Method GZ2 | 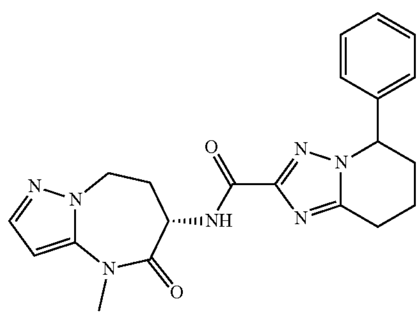<br>5-phenyl-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide | Mixture of Diastereomers | $^1$H NMR (400 MHz, DMSO-d6) δ 8.47 (m, 1H), 7.48 (s, 1H), 7.40-7.26 (m, 3H), 7.09-7.02 (m, 2H), 6.33 (t, J = 1.8 Hz, 1H), 5.57 (t, J = 5.8 Hz, 1H), 4.26 3H), 3.23 (s, 3H), 3.11-2.87 (m, 2H), 2.57 (ddt, J = 12.5, 8.2, 4.3 Hz, 1H), 2.37 (tq, J = 11.8, 5.6 Hz, 2H), 2.05 (ddd, J= 14.6, 7.5, 4.8 Hz, 1H), 1.86 (p, J = 6.4 Hz, 2H) | No LC/MS in SMDI |

TABLE 4-continued

| Example Ki (μM) METHOD | Structure | Stereo | $^1$H NMR | MS (m/z) R.T. |
|---|---|---|---|---|
| Example 381 0.282 Method GZ3 | 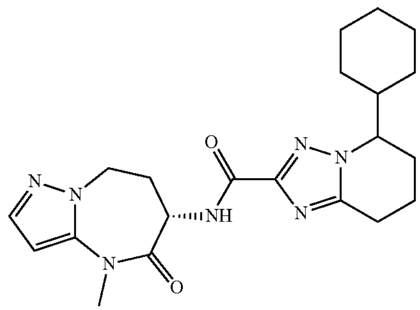 [SMILES: CN1C(=O)[C@@H](NC(=O)c2nc3n(n2)C(C2CCCCC2)CCC3)CCn2nccc21] 5-cyclohexyl-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide | Mixture of Diastereomers | $^1$H NMR (400 MHz, DMSO-$d_6$) δ 8.55-8.35 (m, 1H), 7.50 (d, J = 1.9 Hz, 1H), 6.35 (d, J = 2.2 Hz, 1H), 4.41-4.31 (m, 1H), 4.26-4.10 (m, 2H), 3.45 (s, 3H), 2.94-2.84 (m, 1H), 2.00 (m, 2H), 1.76 (t, J = 6.2 Hz, 2H), 1.68 (s, 10H), 1.43 (m, 2H), 1.24 (s, 4H), 1.12 (m, 4H) | 412.2 4.71 min |
| Example 382 0.0131 Method GZ1 | 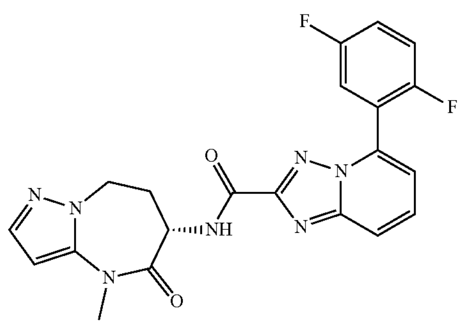 [SMILES: CN1C(=O)[C@@H](NC(=O)c2nc3cccc(-c4cc(F)ccc4F)n3n2)CCn2nccc21] 5-(2,5-difluorophenyl)-N-[(6S)-4-methyl-5-oxo-7,8-dihydro-6H-pyrazolo[1,5-a][1,3]diazepin-6-yl]-1,2,4]triazolo[1,5-a]pyridine-2-carboxamide | Single Known Stereoisomer | $^1$H NMR (400 MHz, DMSO-$d_6$) δ 8.89 (d, J = 7.7 Hz, 1H), 8.05 (dd, J = 9.0, 1.2 Hz, 1H), 7.90 (dd, J = 9.0, 7.1 Hz, 1H), 7.71 (tt, J = 6.1, 2.1 Hz, 1H), 7.59-7.47 (m, 4H), 6.35 4.29 (m, 2H), 4.21 (ddd, J = 14.4, 12.6, 6.6 Hz, 1H), 3.26 (s, 3H), 2.76-2.57 (m, 1H), 2.42 (m, 1H) | 438.1 4.26 min |

TABLE 4-continued

| Example Ki (μM) METHOD | Structure | Stereo | $^1$H NMR | MS (m/z) R.T. |
|---|---|---|---|---|
| Example 383 0.0295 Method GZ2 | 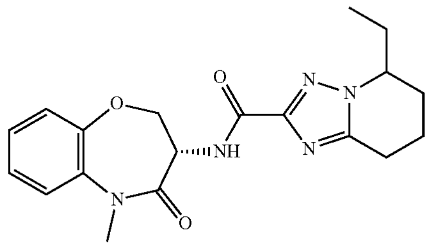 [SMILES: CCC1CCCc2nc(C(=O)N[C@H]3COc4ccccc4N(C)C3=O)nn21] 5-ethyl -N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Mixture of Diastereomers | $^1$H NMR (400 MHz, DMSO-$d_6$) δ 8.36 (t, J = 7.5 Hz, 1H), 7.50 (dd, J = 7.5, 1.9 Hz, 1H), 7.37-7.20 (m, 3H), 4.83 (dtd, J = 11.5, 7.8, 2.0 Hz, 1H), 4.56 (dt, J = 11.4, 9.7 Hz, 1H), 4.41 (ddd, J = 9.5, 7.7, 1.3 Hz, 1H), 4.17 (d, J = 8.5 Hz, 1H), 2.95-2.76 (m, 2H), 2.18-1.91 (m, 3H), 1.86-1.65 (m, 3H), 0.91 (td, J = 7.5, 1.4 Hz, 3H) | 370.2 4.52 min |
| Example 384 2.1 Method GZ2 | 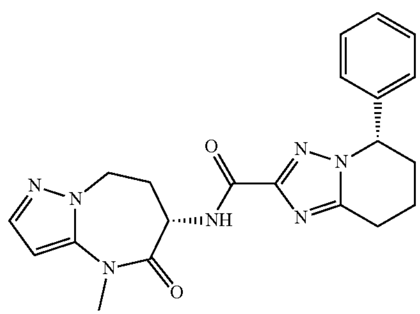 [SMILES: CN1C(=O)[C@@H](NC(=O)c2nc3n(n2)[C@H](c2ccccc2)CCC3)CCn2nccc21] (S)-N-((S)-4-methyl-5-oxo-5,6,7,8-tetrahydro-4H-pyrazolo[1,5-a][1,3]diazepin-6-yl)-5-phenyl-5,6,7,8-tetrahydro-[1,2,4]triazolo[1,5-a]pyridine-2-carboxamide | | $^1$H NMR (400 MHz, DMSO-$d_6$) δ 8.46 (d, J = 7.9 Hz, 1H), 7.48 (d, J = 2.0 Hz, 1H), 7.40-7.26 (m, 3H), 7.09-7.01 (m, 2H), 6.33 (d, J = 2.0 Hz, 1H), 5.57 (t, J = 5.8 Hz, 1H), 4.41-4.11 (m, 3H), 3.24 (s, 3H), 3.10-2.90 (m, 2H), 2.57 (ddd, J = 12.9, 8.0, 5.0 Hz, 1H), 2.37 (tq, J = 12.4, 5.9 Hz, 2H), 2.11-1.98 (m, 1H), 1.86 (p, J = 6.3 Hz, 2H) | 406.2 4.001 min |

TABLE 4-continued

| Example<br>Ki (μM)<br>METHOD | Structure | Stereo | $^1$H NMR | MS (m/z) R.T. |
|---|---|---|---|---|
| Example 385<br>0.0244<br>Method GZ2 | 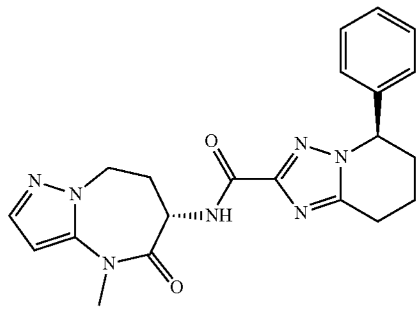 [SMILES: CN1C(=O)[C@@H](NC(=O)c2nc3n(n2)[C@@H](c2ccccc2)CCC3)CCn2nccc21]<br>rac-(5R)-5-phenyl-N-[rac-(6S)-4-methyl-5-oxo-7,8-dihydro-6H-pyrazolo[1,5-a][1,3]diazepin-6-yl]-5,6,7,8-tetrahydro-[1,2,4]triazp;p[1,5-a]pyridine-2-carboxamide | Single<br>Unknown<br>Stereoisomer | : $^1$H NMR (400 MHz, DMSO-$d_6$) δ 8.49 (d, J = 7.9 Hz, 1H), 7.47 (d, J = 2.0 Hz, 1H), 7.41-7.26 (m, 3H), 7.05 (dd, J = 7.0, 1.8 Hz, 2H), 6.33 (d, J = 2.0 Hz, 1H), 5.57 (t, J = 5.9 Hz, 1H), 4.41-4.11 (m, 3H), 3.23 (s, 3H), 3.00 (qt, J = 17.2, 6.3 Hz, 2H), 2.56 (ddd, J = 12.9, 8.0, 5.0 Hz, 1H), 2.43-2.32 (m, 2H), 2.11-1.98 (m, 1H), 1.87 (q, J = 6.2 Hz, 2H) | 406.2<br>4.00 min |
| Example 386<br>0.0148<br>Method GZ1 | 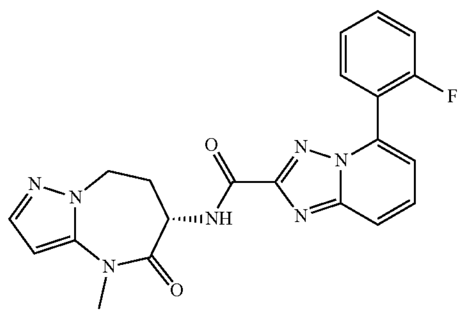 [SMILES: CN1C(=O)[C@@H](NC(=O)c2nc3cccc(-c4ccccc4F)n3n2)CCn2nccc21]<br>5-(2-fluorophenyl)-N-[(6S)-4-methyl-5-oxo-7,8-dihydro-6H-pyrazolo[1,5-a][1,3]diazepin-6-yl]-[1,2,4]triazolo[1,5-a]pyridine-2-carboxamide | Single<br>Known<br>Stereoisomer | $^1$H NMR (400 MHz, DMSO-$d_6$) δ 8.87 (d, J = 7.7 Hz, 1H), 8.07-7.85 (m, 2H), 7.80-7.62 (m, 2H), 7.52-7.32 (m, 4H), 6.35 (d, J = 2.0 Hz, 1H), 4.44-4.28 (m, 2H), 4.21 (ddd, J = 14.5, 12.6, 6.6 Hz, 1H), 3.26 (s, 3H), 2.65 (tt, J = 12.9, 8.1 Hz, 1H), 2.41 (td, J = 12.4, 6.4 Hz, 1H) | 420.1<br>4.19 min |

TABLE 4-continued

| Example<br>Ki (μM)<br>METHOD | Structure | Stereo | $^1$H NMR | MS (m/z) R.T. |
|---|---|---|---|---|
| Example 387<br>0.10<br>Method GZ2 | 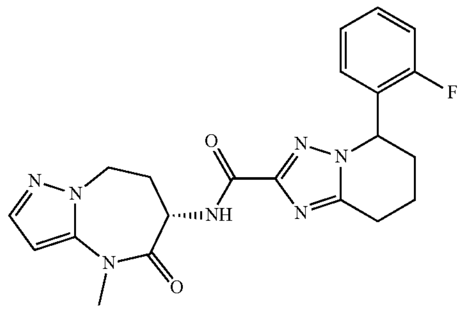 [SMILES: CN1C(=O)[C@@H](NC(=O)c2nc3n(n2)C(c2ccccc2F)CCC3)CCn2nccc21]<br>5-(2-fluorophenyl)-N-[rac-(6S)-4-methyl-5-oxo-7,8-dihydro-6H-pyrazolo[1,5-a][1,3]dizepin-6-yl]-5,6,7,8-tetrahydro-[1,2,4]triazolo[1,5-a]pyridine-2-carboxamide | Mixture of Diastereoers | $^1$H NMR (400 MHz, DMSO-$d_6$) δ 8.36 (t, J = 7.5 Hz, 1H), 7.50 (dd, J = 7.5, 1.9 Hz, 1H), 7.37-7.20 (m, 3H), 4.83 (dtd, J = 11.5, 7.8, 2.0 Hz, 1H), 4.56 (dt, J = 11.4, 9.7 Hz, 1H), 4.41 (ddd, J = 9.5, 7.7, 1.3 Hz, 1H), 4.17 (d, J = 8.5 Hz, 1H), 2.95-2.76 (m, 2H), 2.18-1.91 (m, 3H), 1.86-1.65 (m, 3H), 0.91 (td, J = 7.5, 1.4 Hz, 3H) | 424.2<br>4.13 min |
| Example 388<br>0.124<br>Method GZ2 | 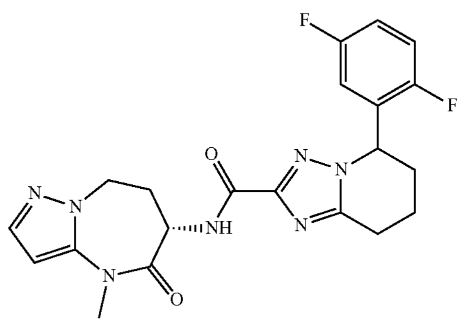 [SMILES: CN1C(=O)[C@@H](NC(=O)c2nc3n(n2)C(c2cc(F)ccc2F)CCC3)CCn2nccc21]<br>5-(2,5-difluorophenyl)-N-[rac-(6S)-4-methyl-S-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide | Mixture of Diastereoers | $^1$H NMR (400 MHz, DMSO-$d_6$) δ 8.50 (dd, J = 12.8, 7.8 Hz, 1H), 7.48 (d, J = 2.0 Hz, 1H), 7.37-7.19 (m, 2H), 6.93 (dt, J = 8.6, 4.2 Hz, 1H), 6.33 (t, J = 1.7 Hz, 1H), 5.75-5.66 (m, 1H), 4.41-4.11 (m, 3H), 3.35 (d, J = 16.9 Hz, 1H), 3.24 (d, J = 1.7 Hz, 3H), 3.08-2.87 (m, 2H), 2.57 (ddt, J = 16.7, 8.6, 3.8 Hz, 1H), 2.38 (dt, J = 12.3, 6.2 Hz, 2H), 2.09 (q, J = 11.1, 10.3 Hz, 1H), 1.95 (d, J = 7.9 Hz, 2H) | 442.2<br>4.19 min |

TABLE 4-continued

| Example<br>Ki (μM)<br>METHOD | Structure | Stereo | $^1$H NMR | MS (m/z) R.T. |
|---|---|---|---|---|
| Example 389<br>0.1735<br>METHOD GZ14 | 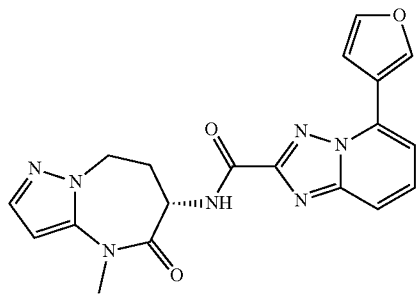 [SMILES: CN1C(=O)[C@@H](NC(=O)c2nc3cccc(-c4ccoc4)n3n2)CCn2nccc21]<br>5-(3-furyl)-N-[rac-(6S)-4-methyl-5-oxo-7,8-dihydro-6H-pyrazolo[1,5-a][1,3]diazepin-6-yl]-[1,2,4]triazolo[1,5-a]pyridine-2-carboxamide | Single Known Stereoisomer | $^1$H NMR (400 MHz, DMSO-$d_6$) δ 9.21 (d, J = 1.4 Hz, 1H), 9.11 (d, J = 7.9 Hz, 1H), 7.97 (t, J = 1.8 Hz, 1H), 7.94 7.77 (m, 3H), 7.52 (d, J = 2.0 Hz, 1H), 7.43 (d, J = 2.0 Hz, 1H), 6.38 (d, J = 2.0 Hz, 1H), 4.50-4.38 (m, 2H), 4.24 (ddd, J = 14.4, 12.6, 6.6 Hz, 1H), 3.29 (s, 3H), 2.76 -2.50 (m, 2H) | 392.1<br>3.95 min |
| Example 390<br>3<br>Method HZ2 | 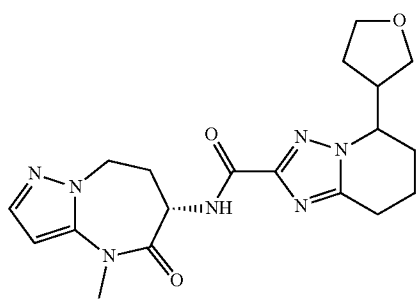 [SMILES: CN1C(=O)[C@@H](NC(=O)c2nc3n(n2)C(C2CCOC2)CCC3)CCn2nccc21]<br>N-[(6S)-4-methyl-5-oxo-7,8-dihydro-6H-pyrazolo[1,5-a][1,3]diazepin-6-yl]-5-tetrahydrofuran-3-yl-5,6,7,8-tetrahydro-[1,2,4]triazolo[1,5-a] | Mixture of Diastereomers | NO NMR since only 0.8 mg final. NMR was confirmed in the previous step. | 400.2<br>3.21 min |

TABLE 4-continued

| Example Ki (μM) METHOD | Structure | Stereo | $^1H$ NMR | MS (m/z) R.T. |
|---|---|---|---|---|
| Example 391 0.0658 METHOD GZ9 | 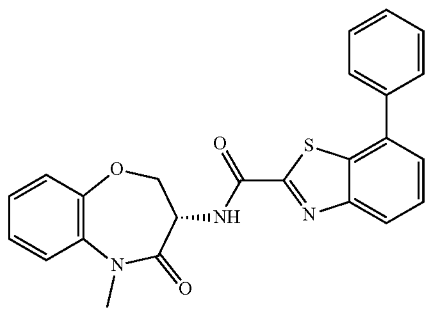 [SMILES: CN1C(=O)[C@@H](NC(=O)c2nc3cccc(-c4ccccc4)c3s2)COc2ccccc21] 7-phenyl-N-[rac-(3S)-5-mehyl-4-oxo-2,3-dihydro-1,5-benzoxazepin-3-yl]-1,3-benzothiazole-2-carboxamide | Single Known Stereoisomer | : $^1H$ NMR (400 MHz, DMSO-$d_6$) δ 9.26 (d, J = 8.0 Hz, 1H), 8.22 (dd, J = 8.1, 1.0 Hz, 1H), 7.83-7.68 (m, 4H), 7.62-7.45 (m, 4H), 7.30 (dddd, J = 23.0, 15.6, 7.5, 1.9 Hz, 3H), 4.89 (dt, J = 11.4, 7.8 Hz, 1H), 4.75 (dd, J = 11.6, 9.7 Hz, 1H), 4.48 (dd, J = 9.8, 7.6 Hz, 1H), 3.33 (s, 3H) | 430.1 6.75 min |
| Example 392 0.0963 Method GZ9 | 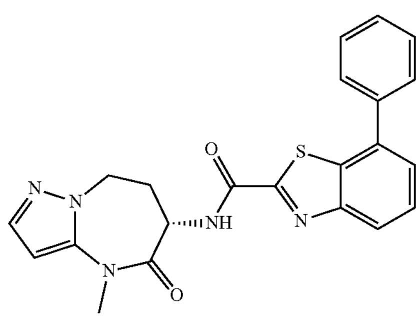 [SMILES: CN1C(=O)[C@@H](NC(=O)c2nc3cccc(-c4ccccc4)c3s2)CCn2nccc21] 7-phenyl-N-[rac-(6S)-4-methyl-5-oxo-7,8-dihydro-6H-pyrazolo[1,5-a][1,3]diazepin-6-yl]-1,3-benzothiazole-2-carboxamide | Single Known Stereoisomer | $^1H$ NMR (400 MHz, DMSO-$d_6$) δ 9.38 (d, J = 7.7 Hz, 1H), 8.21 (dd, J = 8.3, 1.1 Hz, 1H), 7.83-7.67 (m, 4H), 7.62-7.45 (m, 4H), 6.36 (d, J = 2.0 Hz, 1H), 4.47-4.17 (m, 3H), 3.27 (s, 3H), 2.65 (m, 2H) | 418.1 5.70 min |

TABLE 4-continued

| Example Ki (μM) METHOD | Structure | Stereo | $^1H$ NMR | MS (m/z) R.T. |
|---|---|---|---|---|
| Example 393<br>0.463<br>Method GZ14 | 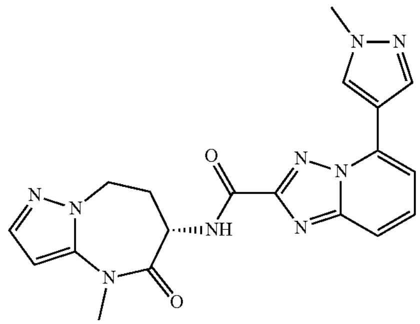 [SMILES: CN1C(=O)[C@@H](NC(=O)c2nc3cccc(-c4cnn(C)c4)n3n2)CCn2nccc21]<br>N-[(6S)-4-methyl-5-oxo-7,8-dihydro-6H-pyrazolo[1,5-a][1,3] diazepin-6-yl]-5-(1-methylpyrazol-4-yl)-[1,2,4] triazolo[1,5-a]pyridine-2-carboxamide | Single Known Stereoisomer | $^1H$ NMR (400 MHz, DMSO-$d_6$) δ 9.03 (d, J = 7.8 Hz, 1H), 8.94 (s, 1H), 8.51 (s, 1H), 7.87-7.72 (m, 3H), 7.52 (d, J = 2.0 Hz, 1H), 6.38 (d, J = 2.0 Hz, 1H), 4.49-4.36 (m, 2H), 4.24 (ddd, J = 14.5, 12.6, 6.6 Hz, 1H), 4.00 (s, 3H), 3.29 (s, 3H), 2.76-2.61 (m, 1H), 2.58-2.44 (m, 1H) | 406.2<br>3.49 min |
| Example 394<br>0.00604<br>Method GZ13 | 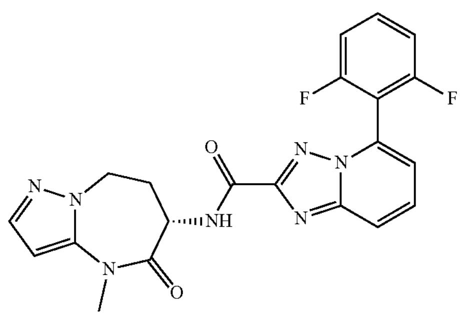 [SMILES: CN1C(=O)[C@@H](NC(=O)c2nc3cccc(-c4c(F)cccc4F)n3n2)CCn2nccc21]<br>5-(2,6-difluorophenyl)-N-[(6S)-4-methyl-5-oxo-7,8-dihydro-6H-pyrazolo[1,5-a][1,3]diazepin-6-yl]-[1,2,4] triazolo[1,5-a]pyridine-2-carboxamide | Single Known Stereoisomer | $^1H$ NMR (400 MHz, DMSO-$d_6$) δ 8.90 (d, J = 7.7 Hz, 1H), 8.10 (dd, J = 9.0, 1.2 Hz, 1H), 7.93 (dd, J = 9.0, 7.1 Hz, 1H), 7.76 (tt, J = 8.5, 6.6 Hz, 1H), 7.59 (dd, J = 7.1, 1.2 Hz, 1H), 7.49 (d, J = 2.0 Hz, 1H), 7.39 (t, J = 8.4 Hz, 2H), 6.35 (d, J = 2.0 Hz, H), 4.44-4.14 (m, 3H), 3.26 (s, 3H), 2.64 (tt, J = 12.9, 8.1 Hz, 1H), 2.50-2.35 (m, 1H) | 438.2<br>4.29 min |

TABLE 4-continued

| Example Ki (μM) METHOD | Structure | Stereo | $^1$H NMR | MS (m/z) R.T. |
|---|---|---|---|---|
| Example 395 0.104 Method GZ14 | 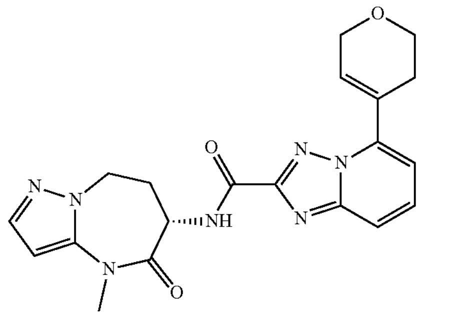 [SMILES: CN1C(=O)[C@@H](NC(=O)c2nc3cccc(C4=CCOCC4)n3n2)CCn2nccc21] 5-(3,6-dihydro-2H-pyran-4-yl)-N-[(6S)-4-methyl-5-oxo-7,8-dihydro-6H-pyrazolo[1,5-a][1,3]diazepin-6-yl]-[1,2,4]triazolo[1,5-a]pyridine-2-carboxamide | Single Known Stereoisomer | NO NMR | 408.2 3.61 min |
| Example 396 0.152 Method GZ2 | 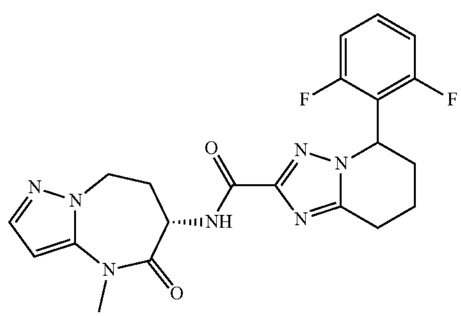 [SMILES: CN1C(=O)[C@@H](NC(=O)c2nc3n(n2)C(c2c(F)cccc2F)CCC3)CCn2nccc21] 5-(2,6-difluorophenyl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide | Mixture of Diastereomers | $^1$H NMR (400 MHz, DMSO-$d_6$) δ 8.48 (dd, J = 20.1, 7.8 Hz, 1H), 7.54-7.39 (m, 2H), 7.14 (t, J = 9.2 Hz, 2H), 6.32 (t, J = 1.9 Hz, 1H), 5.85-5.70 (m, 1H), 4.41-4.10 (m, 3H), 3.23 (d, J = 1.9 Hz, 3H), 3.09-2.85 (m, 2H), 2.64-2.50 (m, 1H), 2.48-2.29 (m, 2H), 2.20-1.97 (m, 3H) | 442.2 4.25 min |

TABLE 4-continued

| Example Ki (μM) METHOD | Structure | Stereo | $^1$H NMR | MS (m/z) R.T. |
|---|---|---|---|---|
| Example 397<br>0.709<br>Method GZ2 | 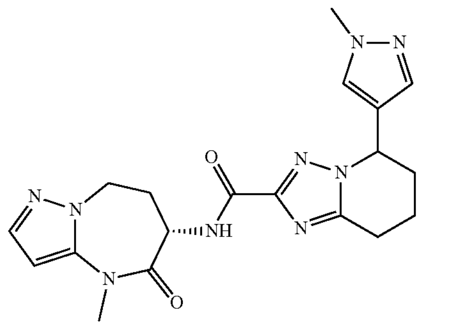 [SMILES: CN1C(=O)[C@@H](NC(=O)c2nc3n(n2)C(c2cnn(C)c2)CCC3)CCn2nccc21]<br>5-(1-methylpyrazol-4-yl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-apyridine-2- | Mixture of Diastereomers | $^1$H NMR (400 MHz, DMSO-$d_6$) δ 8.52-8.38 (m, 1H), 7.65-7.59 (m, 1H), 7.48 (d, J = 2.0 Hz, 1H), 7.37 (s, 1H), 6.33 (d, J = 2.0 Hz, 1H), 5.47 (t, J = 5.8 Hz, 1H), 4.42-4.12 (m, 3H), 3.79 (s, 3H), 3.24 (d, J = 2.8 Hz, 3H), 3.02-2.83 (m, 2H), 2.66-2.52 (m, 1H), 2.43-2.24 (m, 2H), 2.19-2.05 (m, 1H), 1.93 (m, 2H) | 410.2<br>3.11 min |
| Example 398<br>0.036<br>Method GZ14 | 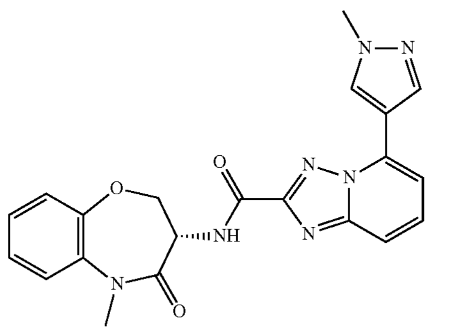 [SMILES: CN1C(=O)[C@@H](NC(=O)c2nc3cccc(-c4cnn(C)c4)n3n2)COc2ccccc21]<br>5-(1-methylpyrazol-4-yl)-N-[rac-(3S)-5-methyl-4-oxo-2,3-dihydro-1,5-benzoxazepin-3-yl]-[1,2,4]triazolo[1,5-a] pyridine-2-carboxzmide | Single Known Stereoisomer | $^1$H NMR (400 MHz, DMSO-$d_6$) δ 9.01-8.90 (m, 2H), 8.53 (s, 1H), 7.88-7.73 (m, 3H), 7.55 (dd, J = 7.7, 1.8 Hz, 1H), 7.40-7.21 (m, 3H), 4.96 (dt, J = 11.5, 7.9 Hz, 1H), 4.73 (dd, J = 11.6, 9.8 Hz, 1H), 4.51 (dd, J = 9.9, 7.8 Hz, 1H), 4.00 (s, 3H), 3.35 (s, 3H) | 418.2<br>4.29 min |

TABLE 4-continued

| Example<br>Ki (μM)<br>METHOD | Structure | Stereo | $^1$H NMR | MS (m/z) R.T. |
|---|---|---|---|---|
| Example 399<br>0.0045<br>Method GZ14 | 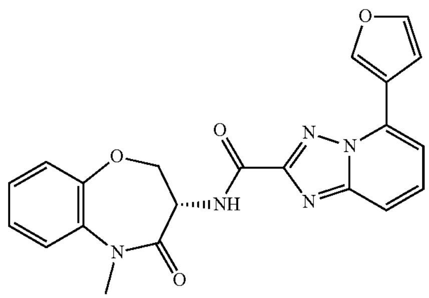 [SMILES: CN1C(=O)[C@@H](NC(=O)c2nc3cccc(-c4ccoc4)n3n2)COc2ccccc21]<br>5-(3-furyl)-N-[rac-(3S)-5-methyl-4-oxo-2,3-dihydro-1,5-benzoxazepin-3-yl]-[1,2,4]triazolo[1,5-a]pyridine-2-carboxamide | Single<br>Known<br>Stereoisomer | %. $^1$H NMR (400 MHz, DMSO-$d_6$) δ 9.23 (s, 1H), 9.07 (d, J = 8.2 Hz, 1H), 7.99 (t, J = 1.9 Hz, 1H), 7.95-7.81 (m, 3H), 7.59-7.52 (m, 1H), 7.44 (d, J = 2.0 Hz, 1H), 7.40-7.24 (m, 3H), 4.99 (dt, J = 11.8, 7.9 Hz, 1H), 4.74 (t, J = 10.7 Hz, 1H), 4.49 (dd, J = 9.9, 7.8 Hz, 1H), 3.35 (s, 3H) | 404.1<br>4.93 min |
| Example 400<br>0.834<br>GZ_chiral_1 | 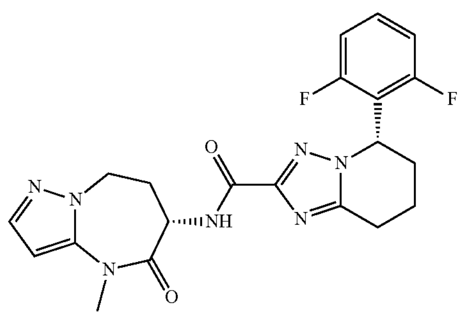<br>rac-(5S)-5-(2,6-difluorophenyl)-N-[rac-(6S)-4-methyl-5-oxo-7,8-dihydro-6H-pyrazolo[1,5-][1,3]diazepin-6-yl]-5,6,7,8-tetrahydro-[1,2,4]triazolo[1,5-a]pyridine-2-carboxamide | Single<br>Unknown<br>Stereoisomer | $^1$H NMR (400 MHz, DMSO-$d_6$) δ 8.50 (d, J = 7.8 Hz, 1H), 7.54-7.41 (m, 2H), 7.14 (t, J = 9.0 Hz, 2H), 6.33 (d, J = 2.0 Hz, 1H), 5.81 (dd, J = 9.3, 5.5 Hz, 1H), 4.41-4.10 (m, 3H), 3.23 (s, 3H), 3.09-2.86 (m, 2H), 2.56 (m, 1H), 2.49-2.32 (m, 3H), 2.21-1.94 (m, 3H) | 442.2<br>4.22 min |

TABLE 4-continued

| Example Ki (μM) METHOD | Structure | Stereo | $^1H$ NMR | MS (m/z) R.T. |
|---|---|---|---|---|
| Example 401 0.0879 GZ_chiral_1 | 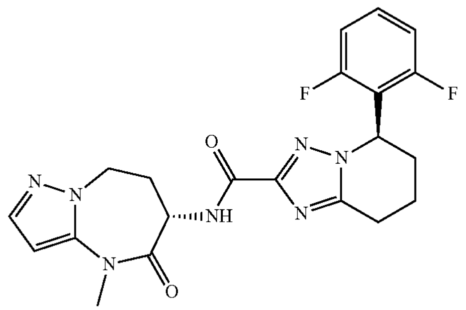 [SMILES: CN1C(=O)[C@@H](NC(=O)c2nc3n(n2)[C@@H](c2c(F)cccc2F)CCC3)CCn2nccc21] rac-(5R)-5-(2,6-difluorophenyl)-N-[rac-(6S)-4-methyl-5-oxo-7,8-dihydro-6H-pyrazolo[1,5-][1,3]diazepin-6-yl]-5,6,7,8-tetrahydro-[1,2,4]triazolo[1,5-a]pyridine-2-carboxamide | Single Unknown Stereoisomer | $^1H$ NMR (400 MHz, DMSO-$d_6$) δ 8.45 (d, J = 7.9 Hz, 1H), 7.54-7.41 (m, 2H), 7.14 (t, J = 9.2 Hz, 2H), 6.32 (d, J = 2.0 Hz, 1H), 5.81 (dd, J = 9.2, 5.4 Hz, 1H), 4.41-4.11 (m, 3H), 3.23 (s, 3H), 3.12-2.87 (m, 2H), 2.57 (m, 1H), 2.38 (m, 3H), 2.20-1.98 (m, 3H) | 442.2 4.23 min |
| Example 402 0.0087 GZ_chiral_2 | 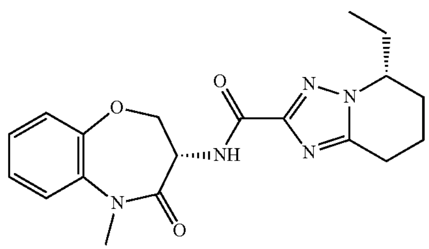 rac-(5R)-5-ethyl-N-[rac-3S)-5-methyl-4-oxo-2,3-dihydro-1,5-benzoxazepin-3-yl]-5,6,7,8-trtrahydro-[1,2,4]triazolo[1,5-a] pyridine-2-carboxamide | Single Unknown Stereoisomer | $^1H$ NMR (400 MHz, DMSO-$d_6$) δ 8.42 (d, J = 8.1 Hz, 1H), 7.51 (dd, J = 7.6, 1.9 Hz, 1H), 7.38-7.20 (m, 3H), 4.82 (dt, J = 11.5, 7.8 Hz, 1H), 4.60 (dd, J = 11.6, 9.8 Hz, 1H), 4.40 (dd, J = 9.8, 7.7 Hz, 1H), 4.18 (s, 1H), 3.31 (s, 3H), 2.85 (q, J = 6.9, 6.0 Hz, 2H), 2.18-1.91 (m, 3H), 1.86-1.65 (m, 3H), 0.91 (t, J = 7.4 Hz, 3H) | 370.1 4.72 min |
| Example 403 0.0819 GZ_chiral_2 | 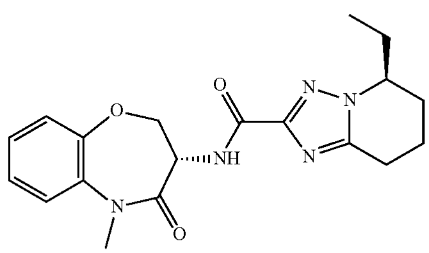 [SMILES: CC[C@H]1CCCc2nc(C(=O)N[C@H]3COc4ccccc4N(C)C3=O)nn21] rac-(5S)-5-ethyl-N-[rac-3S)-5-methyl-4-oxo-2,3-dihydro-1,5-benzoxazepin-3-yl]-5,6,7,8-trtrahydro-[1,2,4]triazolo[1,5-a] pyridine-2-carboxamide | Single Unknown Stereoisomer | $^1H$ NMR (400 MHz, DMSO-$d_6$) δ 8.40 (d, J = 8.1 Hz, 1H), 7.51 (dd, J = 7.6, 1.9 H, 1H), 7.38-7.20 (m, 3H), 4.83 (dt, J = 11.4, 7.8 Hz, 1H), 4.57 (dd, J = 11.5, 9.9 Hz, 1H), 4.40 (dd, J = 9.8, 7.7 Hz, 1H), 4.18 (dt, J = 12.0, 5.2 Hz, 1H), 3.34 (s, 3H), 2.92-2.79 (m, 2H), 2.18-2.02 (m, 2H), 1.98 (q, J = 6.9 Hz, 1H), 1.86-1.66 (m, 3H), 0.90 (t, J = 7.5 Hz, 3H) | 370.1 4.70 min |

TABLE 4-continued

| Example Ki (μM) METHOD | Structure | Stereo | $^1$H NMR | MS (m/z) R.T. |
| --- | --- | --- | --- | --- |
| Example 404 0.318 GZ_chiral_3 | 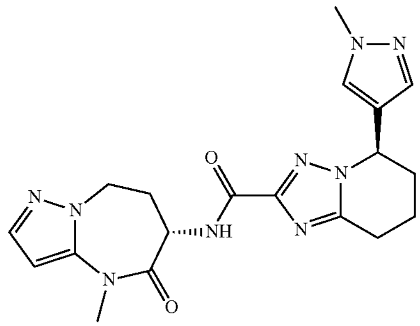 [SMILES: CN1C(=O)[C@@H](NC(=O)c2nc3n(n2)[C@@H](c2cnn(C)c2)CCC3)CCn2nccc21] rac-(5R)-5-(1-methylpyrazol-4-yl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide | Single Unknown Stereoisomer | : $^1$H NMR (400 MHz, DMSO-$d_6$) δ 8.49 (d, J = 7.9 Hz, 1H), 7.63 (s, 1H), 7.49 (d, J = 1.9 Hz, 1H), 7.38 (s, 1H), 6.35 (d, J = 2.0 Hz, 1H), 5.47 (t, J = 5.8 Hz, 1H), 4.42-4.12 (m, 3H), 3.79 (s, 3H), 3.24 (s, 3H), 2.93 (td, J = 6.3, 3.2 Hz, 2H), 2.43-2.24 (m, 1H), 2.18-2.05 (m, 1H), 2.01-1.82 (m, 2H) | 410.2 3.16 min |
| Example 405 0.0356 METHOD GZ4 | 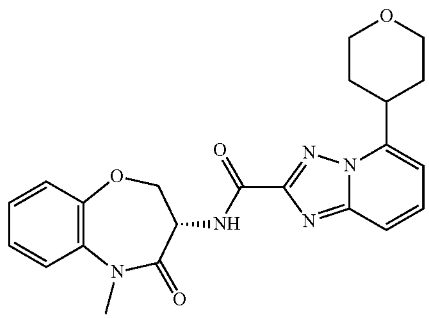 [SMILES: CN1C(=O)[C@@H](NC(=O)c2nc3cccc(C4CCOCC4)n3n2)COc2ccccc21] N-[rac-(3S)-5-methyl-4-oxo-2,3-dihydro-1,5-benzoxazepin-3-yl]-5-tetrahydropyran-4-yl-[1,2,4]triazolo[1,5-a] pyridine-2-carboxamide | Single Known Stereoisomer | $^1$H NMR (400 MHz, DMSO-$d_6$) δ 8.80 (d, J = 7.9 Hz, 1H), 7.88-7.74 (m, 2H), 7.53 (dd, J = 7.6, 1.9 Hz, 1H), 7.46-7.13 (m, 5H),4.91 (dt, J = 11.4, 7.8 Hz, 1H), 4.64 (dd, J = 11.5, 9.9 Hz, 1H), 4.49 (dd, J = 9.9, 7.7 Hz, 1H), 4.05-3.96 (m, 2H), 3.73 (tt, J = 11.9, 3.6 Hz, 1H), 3.57 (td, J = 11.8, 2.0 Hz, 2H), 3.30 (s, 3H), 2.05-1.96 (m, 2H), 1.89-1.72 (m, 2H) | 422.1 4.37 min |

TABLE 4-continued

| Example Ki (μM) METHOD | Structure | Stereo | $^1$H NMR | MS (m/z) R.T. |
|---|---|---|---|---|
| Example 406 0.00472 Method GZ11 | 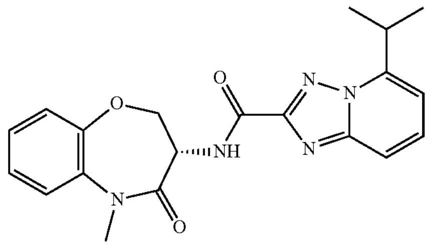 [SMILES: CC(C)c1cccc2nc(C(=O)N[C@H]3COc4ccccc4N(C)C3=O)nn12] 5-isopropyl-N-[(3S)-5-methyl-4-oxo-2,3-dihydro-1,5-benzoxazepin-3-yl]-[1,2,4]triazolo[1,5-a]pyridine-2-carboxamide | Single Known Stereoisomer | % $^1$H NMR (400 MHz, DMSO-$d_6$) δ 8.79 (d, J = 3.3 Hz, 1H), 7.85-7.79 (m, 2H), 7.54 (d, J = 2.0 Hz, 1H), 7.38-7.30 (m, 3H), 7.23-7.21 (s, 1H), 4.91 (m, 1H), 4.64 (m, 1H), 4.49 (m, 1H), 3.76 (p, J = 6.8 Hz, 1H), 3.33 (s, 3H), 1.38 (dd, J = 6.9, 0.9 Hz, 6H) | 380.1 5.13 min |
| Example 407 0.0549 | 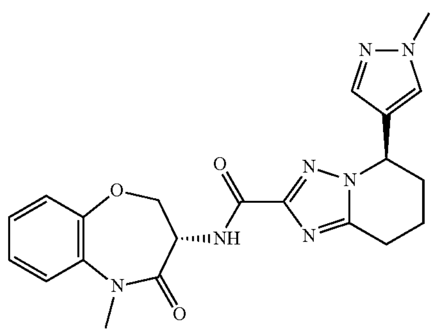 [SMILES: CN1C(=O)[C@@H](NC(=O)c2nc3n(n2)[C@@H](c2cnn(C)c2)CCC3)COc2ccccc21] rac-(5R)-5-(1-methylpyrazol-4-yl)-N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 8.34 (d, J = 7.9 Hz, 1H), 7.62 (s, 1H), 7.49 (dd, J = 7.6, 2.0 Hz, 1H), 7.39-7.19 (m, 4H), 5.47 (t, J = 5.8 Hz, 1H), 4.81 (dt, J = 11.4, 7.7 Hz, 1H), 4.55 (dd, J = 11.5, 9.9 Hz, 1H), 4.39 (dd, J = 9.9, 7.7 Hz, 1H), 3.78 (s, 3H), 3.31 (s, 3H), 2.93 (td, J = 6.4, 2.6 Hz, 2H), 2.29 (ddd, J = 8.6, 5.2, 3.3 Hz, 1H), 2.12 (dtd, J = 14.0, 7.5, 6.6, 3.0 Hz, 1H), 2.03-1.83 (m, 2H) | 422.1 3.91 min |

TABLE 4-continued

| Example Ki (μM) METHOD | Structure | Stereo | $^1$H NMR | MS (m/z) R.T. |
|---|---|---|---|---|
| Example 408 0.147 | 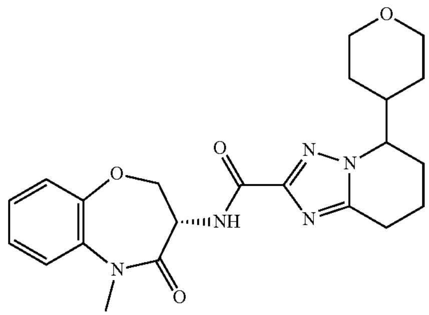 [SMILES: CN1C(=O)[C@@H](NC(=O)c2nc3n(n2)C(C2CCOCC2)CCC3)COc2ccccc21] N-[rac-(3S)-5-methyl-4-oxo-2,3-dihydro-1,5-benzoxazepin-3-yl]-5-tetrahydropyran-4-yl-5,6,7,8-tetrahydro-[1,2,4] triazolo[1,5-a]pyridine--2-carboxamide | Mixture of Diastereomers | $^1$H NMR (400 MHz, DMSO-$d_6$) δ 8.37 (dd, J = 14.1, 8.0 Hz, 1H), 7.50 (dd, J = 7.5, 2.0 Hz, 1H), 7.37-7.20 (m, 3H), 4.89-4.77 (m, 1H), 4.57 (ddd, J = 16.0, 11.5, 9.9 Hz, 1H), 4.41 (dd, J = 9.9, 7.7 Hz, 1H), 4.19 (dt, J = 9.1, 4.8 1H), 3.94-3.79 (m, 2H), 3.42-3.17 (m, 4H), 2.84 (dtt, J = 21.9, 13.8, 5.0 Hz, 2H), 2.45 (m,1H), 2.02 (dh, J = 12.7, 7.2 Hz, 2H), 1.93-1.79 (m, 1H), 1.80-1.68 (m, 1H), 1.56 (d, J = 13.4 Hz, 1H), 1.40 (dqd, J = 16.1, 12.5, 4.2 Hz, 2H), 1.10 (d, J = 13.3 Hz, 1H) | 426.2 4.20 min |
| Example 409 0.565 | 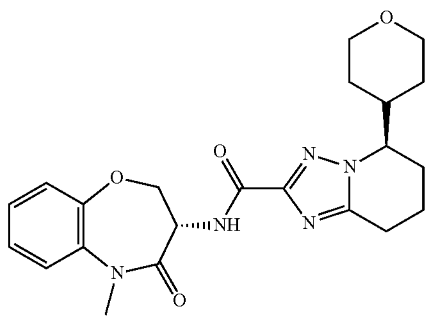 [SMILES: CN1C(=O)[C@@H](NC(=O)c2nc3n(n2)[C@@H](C2CCOCC2)CCC3)COc2ccccc21] rac-(5R)-N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Single Unknown Stereoisome | $^1$H NMR (400 MHz, DMSO-$d_6$) δ 8.37 (dd, J = 14.1, 8.0 Hz, 1H), 7.50 (dd, J = 7.5, 2.0 Hz, 1H), 7.37-7.20 (m, 3H), 4.89-4.77 (m, 1H), 4.57 (ddd, J 16.0, 11.5, 9.9 Hz, 1H), 4.41 (dd, J = 9.9, 7.7 Hz, 1H), 4.19 (dt, J = 9.1, 4.8 Hz, 1H), 3.94-3.79 (m, 2H), 3.42-3.17 (m, 4H), 2.84 (dtt, J = 21.9, 13.8, 5.0 Hz, 2H), 2.45 (m, 1H), 2.02 (dh, J = 12.7, 7.2 Hz, 2H), 1.93-1.79 (m, 1H), 1.80-1.68 (m, 1H), 1.56 (d, J = 13.4 Hz, 1H), 1.40 (dqd, J= 16.1, 12.5, 4.2 Hz, 2H), 1.10 (d, J = 13.3 Hz, 1H). | 426.2 4.18 min |

TABLE 4-continued

| Example Ki (μM) METHOD | Structure | Stereo | $^1$H NMR | MS (m/z) R.T. |
| --- | --- | --- | --- | --- |
| Example 410 0.121 | 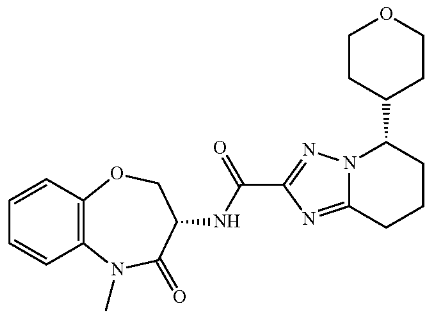 rac-(5S)-N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 8.37 (dd, J = 14.1, 8.0 Hz, 1H), 7.50 (dd, J = 7.5, 2.0 Hz, 1H), 7.37-7.20 (m, 3H), 4.89-4.77 (m, 1H), 4.57 (ddd, J = 16.0, 11.5, 9.9 Hz, 1H), 4.41 (dd, J = 9.9, 7.7 Hz, 1H), 4.19 (dt, J = 9.1, 4.8 Hz, 1H), 3.94-3.79 (m, 2H), 3.42-3.17 (m, 4H), 2.84 (dtt, J = 21.9, 13.8, 5.0 Hz, 2H) 2.45 (m, 1H), 2.02 (dh, J = 12.7, 7.2 Hz, 2H), 1.93-1.79 (m, 1H), 1.80-1.68 (m, 1H), 1.56 (d, J = 13.4 Hz, 1H), 1.40 (dqd, J = 16.1, 12.5, 4.2 Hz, 2H), 1.10 (d, J = 13.3 Hz, 1H) | 426.2 4.20 min |
| Example 411 6.5 | 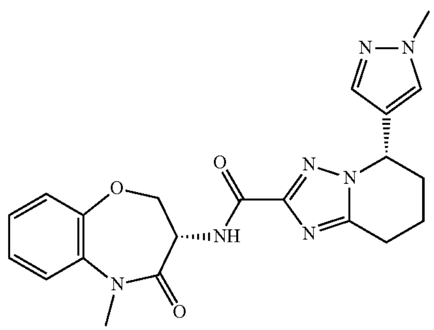 [SMILES: CN1C(=O)[C@@H](NC(=O)c2nc3n(n2)[C@H](c2cnn(C)c2)CCC3)COc2ccccc21] rac-(5S)-5-(1-methylpyrazol-4-yl)-N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 8.34 (d, J = 7.9 Hz, 1H), 7.62 (s, 1H), 7.49 (dd, J = 7.6, 2.0 Hz, 1H), 7.39-7.19 (m, 4H), 5.47 (t, J = 5.8 Hz, 1H), 4.81 (dt, J = 11.4, 7.7 Hz, 1H),4.55 (dd, J = 11.5, 9.9 Hz, 1H), 4.39 (dd, J = 9.9, 7.7 Hz, 1H), 3.78 (s, 3H), 3.31 (s, 3H), 2.93 (td, J = 6.4, 2.6 Hz, 2H), 2.29 (ddd, J = 8.6, 5.2, 3.3 Hz, 1H), 2.12 (dtd, J = 14.0, 7.5, 6.6, 3.0 Hz, 1H), 2.03-1.83 (m, 2H) | 422.1 3.89 min |

TABLE 4-continued

| Example Ki (μM) METHOD | Structure | Stereo | $^1$H NMR | MS (m/z) R.T. |
| --- | --- | --- | --- | --- |
| Example 412 METHOD GZ5 | 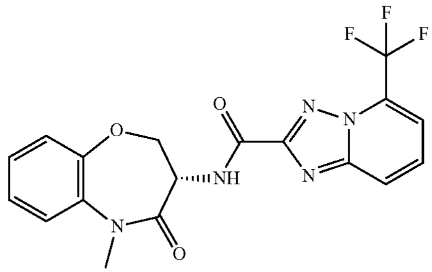 [SMILES: CN1C(=O)[C@@H](NC(=O)c2nc3cccc(C(F)(F)F)n3n2)COc2ccccc21] N-[(3S)-5-methyl-4-oxo-dihydro-1,5-benzoxazepin-3-yl]-5-(trifluoromethyl)-[1,2,4]triazolo[1,5-a]pyridine-2-carboxamide | Single Known Stereoisomer | $^1$H NMR (400 MHz, DMSO-$d_6$) δ 8.88 (d, J = 7.8 Hz, 1H), 8.30 (dd, J = 8.3, 2.0 Hz, 1H), 8.00-7.89 (m, 2H), 7.53 (dd, J = 7.6, 2.0 Hz, 1H), 7.31 (dddd, J = 21.7, 14.5, 7.4, 2.0 Hz, 3H), 4.92 (dt, J = 11.4, 7.8 Hz, 1H), 4.66 (dd, J = 11.6, 9.9 Hz, 1H), 4.49 (dd, J = 9.9, 7.7 Hz, 1H), 3.34 (s, 3H) | 406 4.90 min |
| Example 413 0.227 Method GZ2 | 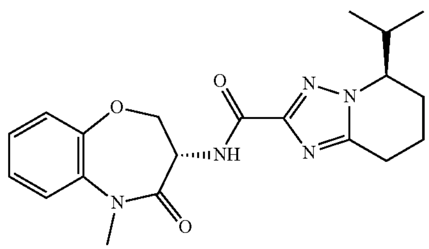 [SMILES: CC(C)[C@H]1CCCc2nc(C(=O)N[C@H]3COc4ccccc4N(C)C3=O)nn21] (R)-5-isopropyl-N-((S)-5-methyl-4-oxo-2,3,4,5-tetrahydrobenzo[b][1,4]oxazepin-3-yl)-5,6,7,8-tetrahydro-[1,2,4]triazolo[1,5-a]pyridine-2-carboxamide | | $^1$H NMR (400 MHz, DMSO-$d_6$) δ 8.34 (d, J = 7.9 Hz, 1H), 7.62 (s, 1H), 7.49 (dd, J = 7.6, 2.0 Hz, 1H), 7.39-7.19 (m, 4H), 5.47 (t, J = 5.8 Hz, 1H), 4.81 (dt, J = 11.4, 7.7 Hz, 1H), 4.55 (dd, J = 11.5, 9.9 Hz, 1H), 4.39 (dd, J = 9.9, 7.7 Hz, 1H), 3.78 (s, 3H), 3.31 (s, 3H), 2.93 (td, J = 6.4, 2.6 Hz, 2H), 2.29 (ddd, J = 8.6, 5.2, 3.3 Hz, 1H), 2.12 (dtd, J = 14.0, 7.5, 6.6, 3.0 Hz, 1H), 2.03-1.83 (m, 2H) | 384.2 5.026 min |
| Example 414 0.0136 Method GZ2 | 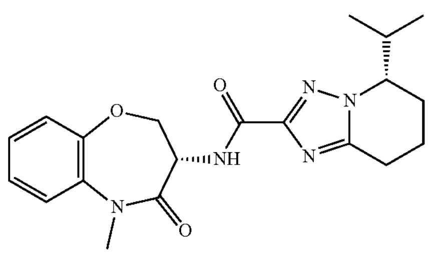 [SMILES: CC(C)[C@@H]1CCCc2nc(C(=O)N[C@H]3COc4ccccc4N(C)C3=O)nn21] rac-(5S)-5-isopropyl-N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 8.36 (d, J = 8.0 Hz, 1H), 7.50 (dd, J = 7.5, 2.0 Hz, 1H), 7.37-7.20 (m, 3H), 4.83 (dt, J = 11.4, 7.8 Hz, 1H), 4.58 (dd, J = 11.5, 9.8 Hz, 1H), 4.41 (dd, J = 9.9, 7.7 Hz, 1H), 4.24 (d, J = 13.1 Hz, 1H), 3.31 (s, 3H), 2.84 (q, J = 6.1, 5.5 Hz, 2H), 2.19-1.91 (m, 3H), 1.85-1.57 (m, 3H), 1.48-1.29 (m, 2H), 0.92 (t, J = 7.3 Hz, 3H) | 384.2 5.03 min |

TABLE 4-continued

| Example Ki (μM) METHOD | Structure | Stereo | $^1H$ NMR | MS (m/z) R.T. |
|---|---|---|---|---|
| Example 415 0.0126 Method GZ2 | 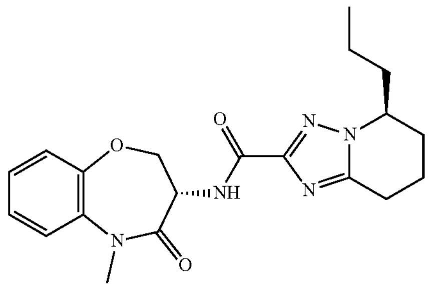 [SMILES: CCC[C@H]1CCCc2nc(C(=O)N[C@H]3COc4ccccc4N(C)C3=O)nn21] rac-(5S)-5-propyl-N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Single Unknown Stereoisomer | : $^1H$ NMR (400 MHz, DMSO-$d_6$) δ 8.34 (d, J = 7.9 Hz, 1H), 7.62 (s, 1H), 7.49 (dd, J = 7.6, 2.0 Hz, 1H), 7.39-7.19 (m, 4H), 5.47 (t, J = 5.8 Hz, 1H), 4.81 (dt, J = 11.4, 7.7 Hz, 1H), 4.55 (dd, J = 11.5, 9.9 Hz, 1H), 4.39 (dd, J = 9.9, 7.7 Hz, 1H), 3.78 (s, 3H), 3.31 (s, 3H), 2.93 (td, J = 6.4, 2.6 Hz, 2H), 2.29 (ddd, J = 8.6, 5.2, 3.3 Hz, 1H), 2.12 (dtd, J = 14.0, 7.5, 6.6, 3.0 Hz, 1H), 2.03-1.83 (m, 2H) | 384.2 5.12 min |
| Example 416 0.00463 Method GZ2 | 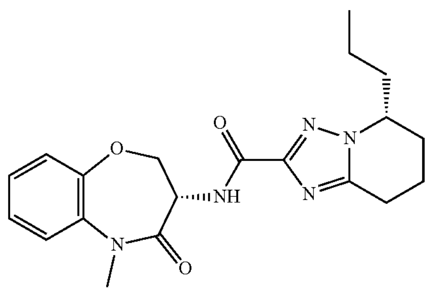 [SMILES: CCC[C@@H]1CCCc2nc(C(=O)N[C@H]3COc4ccccc4N(C)C3=O)nn21] rac-(5R)-5-propyl-N-[rac-(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Single Unknown Stereoisomer | $^1H$ NMR (400 MHz, DMSO-$d_6$) δ 8.36 (d, J = 8.0 Hz, 1H), 7.50 (dd, J = 7.5, 2.0 Hz, 1H), 7.37-7.20 (m, 3H), 4.83 (dt, J = 11.4, 7.8 Hz, 1H), 4.58 (dd, J = 11.5, 9.8 Hz, 1H), 4.41 (dd, J = 9.9, 7.7 Hz, 1H), 4.24 (d, J = 13.1 Hz, 1H), 3.31 (s, 3H), 2.84 (q, J = 6.1, 5.5 Hz, 2H), 2.19-1.91 (m, 3H), 1.85-1.57 (m, 3H), 1.48-1.29 (m, 2H), 0.92 (t, J = 7.3 Hz, 3H) | 384.2 5.14 min |

TABLE 4-continued

| Example Ki (μM) METHOD | Structure | Stereo | $^1$H NMR | MS (m/z) R.T. |
|---|---|---|---|---|
| Example 417 0.0365 Method GZ5 | 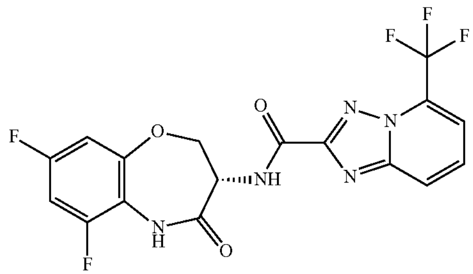 N-[(3S)-6,8-difluoro-4-oxo-3,5-dihydro-2H-1,5-benzoxazepin-3-yl]-5-(trifluoromethyl)-[1,2,4]triazolo[1,5-a]pyridine-2-carboxamide | Single Known Stereoisomer | $^1$H NMR (400 MHz, DMSO-$d_6$) δ 10.12 (s, 1H), 8.88 (d, J = 7.6 Hz, 1H), 8.31 (dd, J = 8.3, 1.9 Hz, 1H), 8.01-7.90 (m, 2H), 7.25 (ddd, J = 10.4, 9.1, 2.9 Hz, 1H), 7.06 (dt, J = 9.3, 2.3 Hz, 1H), 5.00 (dt, J = 10.9, 7.3 Hz, 1H), 4.72 (t, J = 10.6 Hz, 1H), 4.60 (dd, J = 10.2, 7.1 Hz, 1H) | 428 4.72 min |
| Example 418 0.0343 Method GZ5 | 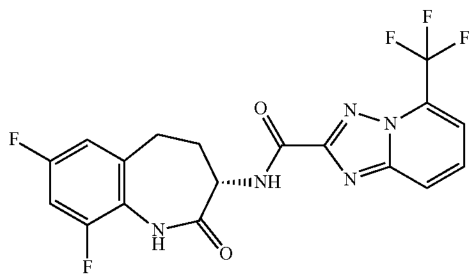 [SMILES: O=C(N[C@H]1CCc2cc(F)cc(F)c2NC1=O)c1nc2cccc(C(F)(F)F)n2n1] N-[(3S)-7,9-difluoro-2-oxo-1,3,4,5-tetrahydro-1-benzazepin-3-yl]-5-(trifluoromethyl)-[1,2,4]triazolo[1,5-a]pyridine-2-carboxamide | Single Known Stereoisomer | $^1$H NMR (400 MHz, DMSO-$d_6$) δ 10.02 (s, 1H), 8.72 (d, J = 7.4 Hz, 1H), 8.30 (dd, J = 8.2, 2.1 Hz, 1H), 8.00-7.89 (m, 2H), 7.29 (ddd, J = 10.0, 8.9, 2.8 Hz, 1H), 7.21-7.13 (m, 1H), 4.43 (dt, J = 11.5, 7.8 Hz, 1H), 3.37-3.22 (m, 3H), 2.87-2.74 (m, 2H), 2.39-2.25 (m, 1H) | 426 4.69 min |
| Example 419 0.0094 Method GZ5 | 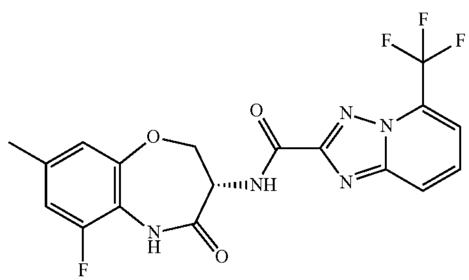 [SMILES: Cc1cc(F)c2c(c1)OC[C@H](NC(=O)c1nc3cccc(C(F)(F)F)n3n1)C(=O)N2] N-[(3S)-6-fluoro-8-methyl-4-oxo-3,5-dihydro-2H-1,5-benzoxazepin-3-yl]-5-(trifluoromethyl)-[1,2,4]triazolo[1,5-a]pyridine-2-carboxamide | Single Known Stereoisomer | $^1$H NMR (400 MHz, DMSO-$d_6$) δ 10.06 (s, 1H), 8.86 (d, J = 7.7 Hz, 1H), 8.31 (dd, J = 8.3, 1.9 Hz, 1H), 8.01-7.90 (m, 2H), 7.00 (dd, J = 10.7, 1.8 Hz, 1H), 6.92 (s, 1H), 4.94 (dt, J = 11.0, 7.4 Hz, 1H), 4.67 (t, J = 10.7 Hz, 1H), 4.54 (dd, J = 10.2, 7.3 Hz, 1H), 2.31 (s, 3H) | 424.1 4.98 min |

TABLE 4-continued

| Example Ki (μM) METHOD | Structure | Stereo | $^1$H NMR | MS (m/z) R.T. |
|---|---|---|---|---|
| Example 420<br>0.00471<br>Method GZ12 | 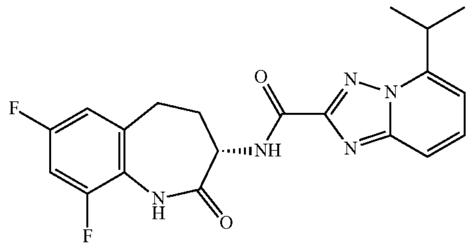<br>5-isopropyl-N-[rac-(3S)-7,9-difluoro-2-oxo-1,3,4,5-tetrahydro-l-benzazepin-3-yl]-[1,2,4]triazolo[1,5-a] pyridine-2-carboxamide | Single Known Stereoisomer | $^1$H NMR (400 MHz, DMSO-$d_6$) δ 10.00 (s, 1H), 8.63 (dd, J = 7.5, 3.0 Hz, 1H), 7.85-7.68 (m, 3H), 7.29 (ddd, J = 10.2, 8.9, 2.8 Hz, 1H), 7.18 (ddt, J = 11.0, 8.7, 1.9 Hz, 3H), 4.43 (dt J = 11.6, 7.7 Hz, 1H), 3.77 (h, J = 6.8 Hz, 1H), 3.39-3.25 (m, 1H), 2.83 (dd, J = 11.1, 5.5 Hz, 2H), 2.30 (ddt, J = 12.4, 9.3, 4.0 Hz, 1H), 1.39 (d, J = 6.9 Hz, 6H) | 400.1<br>4.92 min |
| Example 421<br>0.0159<br>Method GZ15 | 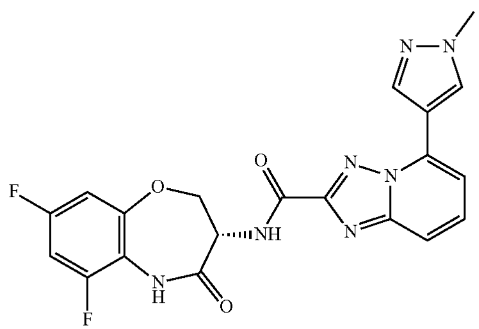 [SMILES: Cn1cc(-c2cccc3nc(C(=O)N[C@H]4COc5cc(F)cc(F)c5NC4=O)nn23)cn1]<br>5-(1-methylpyrazol-4-yl)-N-[rac-(3S)-6,8-difluoro-4-oxo-3,5-dihydro-2H-1,5-benzoxazepin-3-yl]-[1,2,4]triazolo[1,5-a] pyridine-2-carboxamide | Single Known Stereoisomer | 1H NMR (400 MHz, DMSO-$d_6$) δ 10.12 (s, 2H), 8.96-8.89 (m, 4H), 8.53 (s, 2H), 7.88-7.73 (m, 6H), 7.26 (ddd, J = 10.3, 9.0, 2.9 Hz, 2H), 7.07 (dt, J = 9.1, 2.2 Hz, 2H), 5.02 (dt, J = 11.1,7.5 Hz, 2H), 4.78 (t, J = 10.7 Hz, 2H), 4.62 (dd, J = 10.2, 7.2 Hz, 2H), 4.00 (s, 6H), 3.32-3.22 (m, 1H), 2.47 (s, 1H) | 440.1<br>4.31 min |

TABLE 4-continued

| Example Ki (μM) METHOD | Structure | Stereo | $^1$H NMR | MS (m/z) R.T. |
|---|---|---|---|---|
| Example 422 0.0274 Method GZ16 | 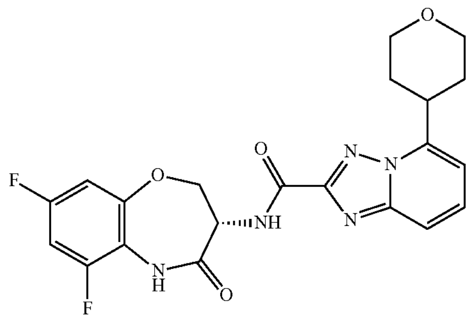 [SMILES: O=C(N[C@H]1COc2cc(F)cc(F)c2NC1=O)c1nc2cccc(C3CCOCC3)n2n1] N-[(3S)-6,8-difluoro-4-oxo-3,5-dihydro-2H-1,5-benzoxazepin-3-yl]-5-tetrahydropyran-4-yl-[1,2,4]triazolo[1,5-a]pyridine-2-carboxamide | Single Known Stereoisomer | 1H NMR (400 MHz, DMSO-$d_6$) δ 10.12 (s, 1H), 8.81 (d, J = 7.6 Hz, 1H), 7.88-7.74 (m, 2H), 7.30-7.20 (m, 2H), 7.06 (dt, J = 9.3, 2.3 Hz, 1H), 4.99 (dt, J = 11.0, 7.3 Hz, 1H), 4.71 (t, J = 10.7 Hz, 1H), 4.59 (dd, J = 10.2, 7.2 Hz, 1H), 4.06-3.97 (m, 2H), 3.74 (tt, J = 11.9, 3.5 Hz, 1H), 3.58 (td, J = 11.8, 2.0 Hz, 2H), 2.10-1.96 (m, 2H), 1.82 (qt, J = 12.4, 4.6 Hz, 2H) | 444.1 4.44 min |
| Example 423 0.0034 Method GZ12 | 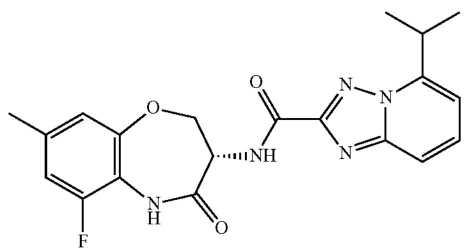 [SMILES: Cc1cc(F)c2c(c1)OC[C@H](NC(=O)c1nc3cccc(C(C)C)n3n1)C(=O)N2] N-[(3S)-6-fluoro-8-methyl-4-oxo-3,5-dihydro-2H-1,5-benzoxazepin-3-yl]-5-isopropyl-[1,2,4]triazolo[1,5-a]pyridine-2-carboxamide | Single Known Stereoisomer | 1H NMR (400 MHz, DMSO-$d_6$) δ 10.04 (s, 1H), 8.76 (dd, J = 7.8, 2.6 Hz, 1H), 7.86-7.70 (m, 2H), 7.21 (dt, J = 6.9, 1.8 Hz, 1H), 7.00 (dd, J = 10.8, 1.8 Hz, 1H), 6.91 (s, 1H), 4.94 (dt, J = 11.2, 7.4 Hz, 1H), 4.65 (t, J = 10.6 Hz, 1H), 4.54 (ddd, J = 9.3, 7.4, 1.6 Hz, 1H), 3.77 (p, J = 6.9 Hz, 1H),2.31 (s, 3H), 1.39 (d, J = 6.9 Hz, 6H) | 398.1 5.21 min |
| Example 424 0.0030 Method GZ12 | 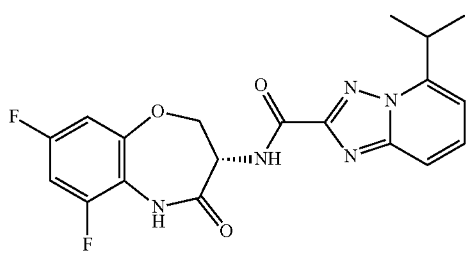 [SMILES: CC(C)c1cccc2nc(C(=O)N[C@H]3COc4cc(F)cc(F)c4NC3=O)nn12] N-[(3S)-6,8-difluoro-4-oxo-3,5-dihydro-2H-1,5-benzoxazepin-3-yl]-5-isopropyl-[1,2,4]triazolo[1,5-a]pyridine-2-carboxamide | Single Known Stereoisomer | 1H NMR (400 MHz, DMSO-$d_6$) δ 10.12 (s, 1H), 8.78 (dd, J = 7.6, 2.7 Hz, 1H), 7.86-7.70 (m, 2H), 7.30-7.17 (m, 2H), 7.06 (dt, J = 9.4, 2.3 Hz, 1H), 5.05-4.93 (m, 1H), 4.71 (t, J = 10.7 Hz, 1H), 4.59 (ddd, J = 10.2, 7.1, 1.5 Hz, 1H), 3.77 (p, J = 6.9 Hz, 1H), 3.38-3.23 (m, 1H), 1.39 (d, J = 6.9 Hz, 6H) | 402.1 5.01 min |

TABLE 4-continued

| Example Ki (μM) METHOD | Structure | Stereo | $^1$H NMR | MS (m/z) R.T. |
|---|---|---|---|---|
| Example 425 0.471 Method GZ2 | 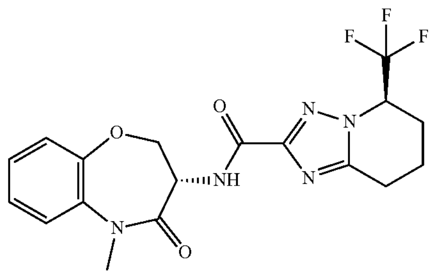 [SMILES: CN1C(=O)[C@@H](NC(=O)c2nc3n(n2)[C@@H](C(F)(F)F)CCC3)COc2ccccc21] (R)-N-((S)-5-methyl-4-oxo-2,3,4,5-tetrahydrobenzo[b][1,4]oxazepin-3-yl)-5-(trifluoromethyl)-5,6,7,8-tetrahydro-[1,2,4]triazolo[1,5-a]pyridine-2-carboxamide | | $^1$H NMR (400 MHz, DMSO-$d_6$) δ 8.50 (d, J = 7.9 Hz, 1H), 7.51 (dd, J = 7.5, 1.9 Hz, 1H), 7.37-7.20 (m, 3H), 5.41 (h, J = 6.8 Hz, 1H), 4.83 (dt, J = 11.5, 7.8 Hz, 1H), 4.61 (dd, J = 11.6, 9.8 Hz, 1H), 4.42 (dd, J = 9.8, 7.7 Hz, 1H), 3.42-3.18 (m, 3H), 3.07-2.87 (m, 2H), 2.39-2.15 (m, 2H), 2.02-1.87 (m, 2H) | 410.1 4.760 min |
| Example 426 0.0137 Method GZ2 | 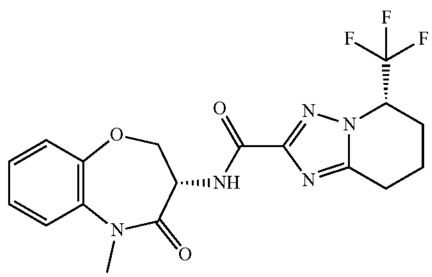 [SMILES: CN1C(=O)[C@@H](NC(=O)c2nc3n(n2)[C@H](C(F)(F)F)CCC3)COc2ccccc21] rac-(5S)-N-[rac-(3S)-5-met hyl-4-oxo-2,3-dihydro-1,5-benzoxazepin-3-yl]-5-(trifluoromethyl)-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 8.50 (d, J = 7.9 Hz, 1H), 7.51 (dd, J = 7.5, 1.9 Hz, 1H), 7.37-7.20 (m, 3H), 5.41 (h, J = 6.8 Hz, 1H), 4.83 (dt, J = 11.5, 7.8 Hz, 1H), 4.61 (dd, J = 11.6, 9.8 Hz, 1H), 4.42 (dd, J = 9.8, 7.7 Hz, 1H), 3.42-3.18 (m, 3H), 3.07-2.87 (m, 2H), 2.39-2.15 (m, 2H), 2.02-1.87 (m, 2H) | 410.1 4.81 min |
| Example 427 0.210 Method GZ2 | 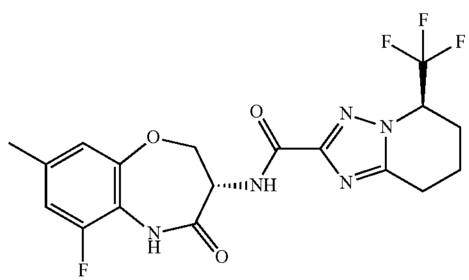 [SMILES: Cc1cc(F)c2c(c1)OC[C@H](NC(=O)c1nc3n(n1)[C@@H](C(F)(F)F)CCC3)C(=O)N2] (5R)-N-[(3S)-6-fluoro-8-methyl-4-oxo-3,5-dihydro-2H-1,5-benzoxazepin-3-yl]-5-(trifluoromethyl)-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 10.00 (s, 1H), 8.47 (d, J = 7.7 Hz, 1H), 6.99 (dd, J = 10.8, 1.8 Hz, 1H), 6.89 (s, 1H), 5.41 (h, J = 6.8 Hz, 1H), 4.85 (dt, J = 11.1, 7.4 Hz, 1H), 4.61 (t, J = 10.7 Hz, 1H), 4.47 (dd, J = 10.1, 7.2 Hz, 1H), 3.07-2.87 (m, 2H), 2.30 (m, 5H), 1.96 (h, J = 6.7 Hz, 2H) | 428.1 4.44 min |

TABLE 4-continued

| Example Ki (μM) METHOD | Structure | Stereo | $^1H$ NMR | MS (m/z) R.T. |
|---|---|---|---|---|
| Example 428 0.00814 Method GZ2 | 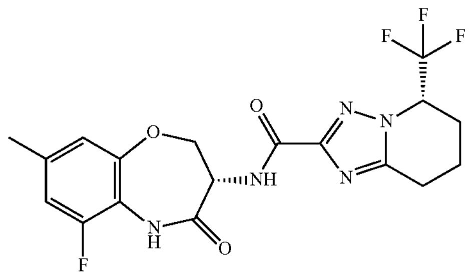 [SMILES: Cc1cc(F)c2c(c1)OC[C@H](NC(=O)c1nc3n(n1)[C@H](C(F)(F)F)CCC3)C(=O)N2] (5S)-N-[(3S)-6-fluoro-8-methyl-4-oxo-3,5-dihydro-2H-1,5-benzoxazepin-3-yl]-5-(trifluoromethyl)-5,6,7,8-tetrahydro-[1,2,4]triazolo[1,5-a]pyridine-2-carboxamide | Single Unknown Stereoisomer | $^1H$ NMR (400 MHz, DMSO-$d_6$) δ 10.00 (s, 1H), 8.47 (d, J = 7.7 Hz, 1H), 6.99 (dd, J = 10.8, 1.8 Hz, 1H), 6.89 (s, 1H), 5.41 (h, J = 6.8 Hz, 1H), 4.85 (dt, J = 11.1, 7.4 Hz, 1H), 4.61 (t, J = 10.7 Hz, 1H), 4.47 (dd, J = 10.1, 7.2 Hz, 1H), 3.07-2.87 (m, 2H), 2.30 (m, 5H), 1.96 (h, J = 6.7 Hz, 2H) | 428.1 4.50 min |
| Example 429 0.213 Method GZ2 | 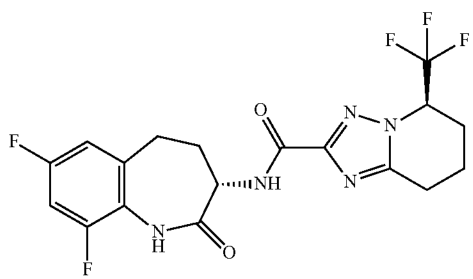 [SMILES: O=C(N[C@H]1CCc2cc(F)cc(F)c2NC1=O)c1nc2n(n1)[C@@H](C(F)(F)F)CCC2] (5R)-N-[(3S)-7,9-difluoro-2-oxo-1,3,4,5-tetrahydro-l-benzazepin-3-yl]-5-(trifluoromethyl)-5,6,7,8-tetrahydro-[1,2,4]triazolo[1,5-a]pyridine-2-carboxamide | Single Unknown Stereoisomer | $^1H$ NMR (400 MHz, DMSO-$d_6$) δ 9.96 (s, 1H), 8.33 (d, J = 7.5 Hz, 1H), 7.27 (ddd, J = 10.2, 8.9, 2.8 Hz, 1H), 7.18-7.10 (m, 1H), 5.40 (h, J = 6.8 Hz, 1H), 4.34 (dt, J = 11.5, 7.8 Hz, 1H), 3.06-2.71 (m, 4H), 2.50-2.15 (m, 4H), 1.94 (m, 2H) | 430.1 4.16 min |

TABLE 4-continued

| Example Ki (μM) METHOD | Structure | Stereo | $^1$H NMR | MS (m/z) R.T. |
|---|---|---|---|---|
| Example 430<br>0.0210<br>Method GZ2 | 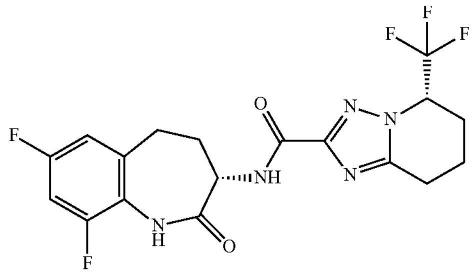 [SMILES: O=C(N[C@H]1CCc2cc(F)cc(F)c2NC1=O)c1nc2n(n1)[C@H](C(F)(F)F)CCC2]<br>(5S)-N-[(3S)-7,9-difluoro-2-oxo-1,3,4,5-tetrahydro-1-benzazepin-3-yl]-5-(trifluoromethyl)-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 9.96 (s, 1H), 8.33 (d, J = 7.5 Hz, 1H), 7.27 (ddd, J = 10.2, 8.9, 2.8 Hz, 1H), 7.18-7.10 (m, 1H), 5.40 (h, J = 6.8 Hz, 1H), 4.34 (dt, J = 11.5, 7.8 Hz, 1H), 3.06-2.71 (m, 4H), 2.50-2.15 (m, 4H), 1.94 (m, 2H) | 430.1<br>4.22 min |
| Example 431<br>0.434<br>Method GZ2 | 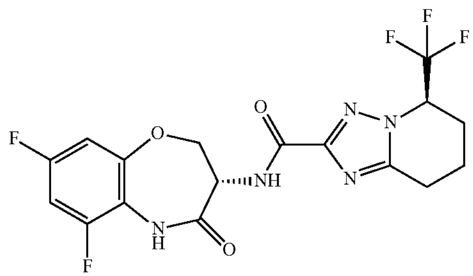 [SMILES: O=C(N[C@H]1COc2cc(F)cc(F)c2NC1=O)c1nc2n(n1)[C@@H](C(F)(F)F)CCC2]<br>(5R)-N-[(3S)-6,8-difluoro-4-oxo-3,5-dihydro-2H-1,5-benzoxazepin-3-yl]-5-(trifluoromethyl)-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 10.08 (s, 1H), 8.50 (d, J = 7.6 Hz, 1H), 7.23 (ddd, J = 10.3, 9.0, 2.9 Hz, 1H), 7.03 (dt, J = 9.4, 2.3 Hz, 1H), 5.42 (h, J = 6.8 Hz, 1H), 4.90 (dt, J = 11.1, 7.3 Hz, 1H), 4.67 (t, J = 10.7 Hz, 1H), 4.53 (dd, J = 10.1, 7.1 Hz, 1H), 3.07-2.87 (m, 2H), 2.40-2.16 (m, 2H), 1.96 (h, J = 6.6 Hz, 2H) | 432.1<br>4.24 min |

TABLE 4-continued

| Example Ki (μM) METHOD | Structure | Stereo | $^1$H NMR | MS (m/z) R.T. |
|---|---|---|---|---|
| Example 432 0.0127 Method GZ2 | 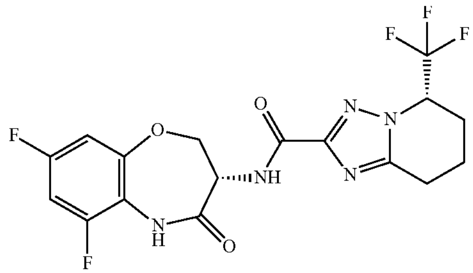 [SMILES: O=C(N[C@H]1COc2cc(F)cc(F)c2NC1=O)c1nc2n(n1)[C@H](C(F)(F)F)CCC2] (5S)-N-R35)-6,8-difluoro-4-oxo-3,5-dihydro-2H-1,5-benzoxazepin-3-yl]-5-(trifluoromethyl)-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 10.08 (s, 1H), 8.50 (d, J = 7.6 Hz, 1H), 7.23 (ddd, J = 10.3, 9.0, 2.9 Hz, 1H), 7.03 (dt, J = 9.4, 2.3 Hz, 1H), 5.42 (h, J = 6.8 Hz, 1H), 4.90 (dt, J = 11.1, 7.3 Hz, 1H), 4.67 (t, J = 10.7 Hz, 1H), 4.53 (dd, J = 10.1, 7.1 Hz, 1H), 3.07-2.87 (m, 2H), 2.40-2.16 (m, 2H), 1.96 (h, J = 6.6 Hz, 2H) | 432.1 4.29 min |
| Example 433 0.143 Method GZ2 | 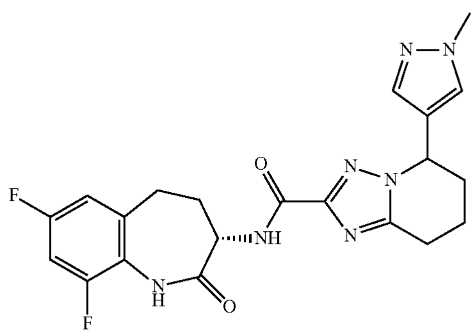 [SMILES: Cn1cc(C2CCCc3nc(C(=O)N[C@H]4CCc5cc(F)cc(F)c5NC4=O)nn32)cn1] 5-(1-methylpyrazol-4-yl)-N-[rac-(3S)-7,9-difluoro-2-oxo-1,3,4,5-tetrahydro-1-benzazepin-3-yl]-5,6,7,8-tetrahydro-[1,2,4triazolo[1,5-a]pyridine-2-carboxamide | Mixture of Diastereomers | $^1$H NMR (400 MHz, DMSO-$d_6$) δ 9.95 (s, 1H), 8.19 (dd, J = 7.6, 4.1 Hz, 1H), 7.62 (s, 1H), 7.37 (s, 1H), 7.26 (td, J = 9.6, 2.8 Hz, 1H), 7.14 (dd, J = 8.2, 2.7 Hz, 1H), 5.46 (t, J = 5.8 Hz, 1H), 4.32 (dt, J = 11.4, 7.8 Hz, 1H), 4.08 (q, J = 5.3 Hz, 1H), 3.78 (s, 3H), 3.17 (d, J = 5.3 Hz, 3H), 2.92 (dt, J = 10.0, 5.4 Hz, 2H), 2.82-2.71 (m, 2H), 2.33-2.17 (m, 2H), 2.12 (m, 1H), 1.92 (dd, J = 20.0, 10.3 Hz, 2H) | 442.1 3.85 min |

TABLE 4-continued

| Example Ki (μM) METHOD | Structure | Stereo | $^1H$ NMR | MS (m/z) R.T. |
| --- | --- | --- | --- | --- |
| Example 434 0.174 Method GZ2 | 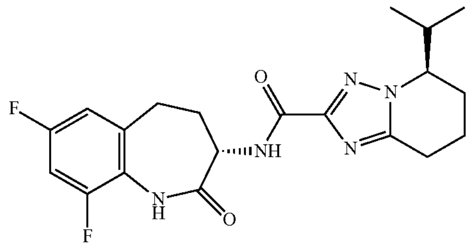 [SMILES: CC(C)[C@H]1CCCc2nc(C(=O)N[C@H]3CCc4cc(F)cc(F)c4NC3=O)nn21] (5R)-N-[(3S)-7,9-difluoro-2-oxo-1,3,4,5-tetrahydro-1-benzazepin-3-yl]-5-isopropyl-5,6,7,8-tetrahydro-[1,2,4]triazolo[1,5-a]pyridine-2-carboxamide | Single Unknown Stereoisomer | $^1H$ NMR (400 MHz, DMSO-$d_6$) δ 9.95 (s, 1H), 8.21 (d, J = 7.6 Hz, 1H), 7.27 (ddd, J = 10.1, 8.9, 2.8 Hz, 1H), 7.19-7.10 (m, 1H), 4.34 (dt, J = 11.5, 7.8 Hz, 1H), 4.15 (p, J = 4.4 Hz, 1H), 2.95-2.85 (m, 1H), 2.72 (dtd, J = 59.4, 7.0, 6.5, 4.0 Hz, 5H), 2.50-2.37 (m, 1H), 2.30-2.16 (m, 1H), 2.10-1.96 (m, 2H), 1.73 (ddd, J = 10.7, 8.2, 5.2 Hz, 2H), 0.98 (d, J = 7.0 Hz, 3H), 0.68 (d, J = 6.8 Hz, 3H) | 404.1 4.72 min |
| Example 435 0.0252 Method GZ2 | 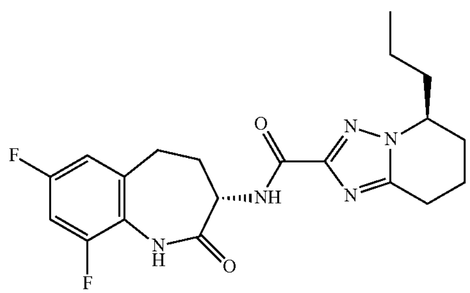 [SMILES: CCC[C@H]1CCCc2nc(C(=O)N[C@H]3CCc4cc(F)cc(F)c4NC3=O)nn21] (5S)-N-[(3S)-7,9-difluoro-2-oxo-1,3,4,5-tetrahydro-1-benzazepin-3-yl]-5-propyl-5,6,7,8-tetrahydro-[1,2,4]triazolo[1,5-a]pyridine-2-carboxamide | Single Unknown Stereoisomer | $^1H$ NMR (400 MHz, DMSO-$d_6$) δ 9.95 (s, 1H), 8.20 (d, J = 7.6 Hz, 1H), 7.27 (ddd, J = 10.1, 8.9, 2.8 Hz, 1H), 7.18-7.10 (m, 1H), 4.34 (dt, J = 11.5, 7.9 Hz, 1H), 4.21 (d, J = 4.85 7.5 Hz, 1H), 2.93-2.71 (m, 4H), 2.50-2.36 (m, 1H), 2.30-1.91 (m, 4H), 1.86-1.57 (m, 3H), 1.38 (m, 2H), 0.93 (t, J = 7.3 Hz, 3H) | 404.1 4.85 min |

TABLE 4-continued

| Example<br>Ki (μM)<br>METHOD | Structure | Stereo | $^1$H NMR | MS (m/z) R.T. |
|---|---|---|---|---|
| Example 436<br>0.0203<br>Method GZ2 | 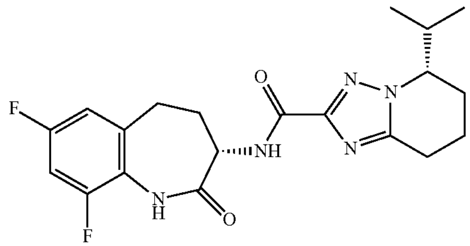 [SMILES: CC(C)[C@@H]1CCCc2nc(C(=O)N[C@H]3CCc4cc(F)cc(F)c4NC3=O)nn21]<br>(5S)-N-R35)-7,9-difluoro-2-oxo-1,3,4,5-tetrahydro-1-benzazepin-3-yl]-5-isopropyl-5,6,7, 8-tetrahydro-[1,2,4] triazolo[1,5-a]pyridine-2-carboxamide | Single Unknown Stereoisomer | $^1$H NMR (400 MHz, DMSO-$d_6$) δ 9.95 (s, 1H), 8.21 (d, J = 7.6 Hz, 1H), 7.27 (ddd, J = 10.1, 8.9, 2.8 Hz, 1H), 7.19-7.10 (m, 1H), 4.34 (dt, J = 11.5, 7.8 Hz, 1H), 4.15 (p, J = 4.4 Hz, 1H), 2.95-2.85 (m, 1H), 2.72 (dtd, J = 59.4, 7.0, 6.5, 4.0 Hz, 5H), 2.50-2.37 (m, 1H), 2.30-2.16 (m, 1H), 2.10-1.96 (m, 2H), 1.73 (ddd, J = 10.7, 8.2, 5.2 Hz, 2H), 0.98 (d, J = 7.0 Hz, 3H), 0.68 (d, J = 6.8 Hz, 3H) | 404.1<br>4.78 min |
| Example 437<br>0.00843<br>Method GZ2 | 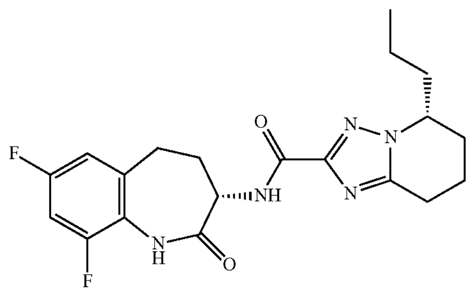 [SMILES: CCC[C@@H]1CCCc2nc(C(=O)N[C@H]3CCc4cc(F)cc(F)c4NC3=O)nn21]<br>(5R)-N-[(3S)-7,9-difluoro-2-oxo-1,3,4,5-tetrahydro-1-benzazepin-3 -yl]-5-propyl-5,6,7,8-tetrahydro-[1,2,4] triazolo[1,5-a]pyridine-2-carboxamide | Single Unknown Stereoisomer | $^1$H NMR (400 MHz, DMSO-$d_6$) δ 9.95 (s, 1H), 8.20 (d, J = 7.6 Hz, 1H), 7.27 (ddd, J = 10.1, 8.9, 2.8 Hz, 1H), 7.18-7.10 (m, 1H), 4.34 (dt, J = 11.5, 7.9 Hz, 1H), 4.21 (d, J = 7.5 Hz, 1H), 2.93-2.71 (m, 4H), 2.50-2.36 (m, 1H), 2.30-1.91 (m, 4H), 1.86-1.57 (m, 3H), 1.38 (m, 2H), 0.93 (t, J = 7.3 Hz, 3H) | 404.1<br>4.88 min |

TABLE 4-continued

| Example Ki (μM) METHOD | Structure | Stereo | $^1$H NMR | MS (m/z) R.T. |
|---|---|---|---|---|
| Example 438 0.150 Mwthod GZ2 | 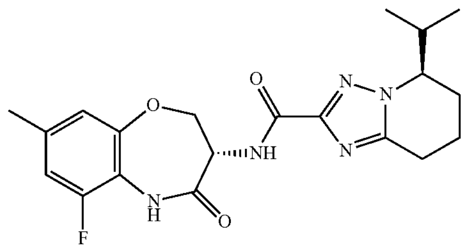 [SMILES: Cc1cc(F)c2c(c1)OC[C@H](NC(=O)c1nc3n(n1)[C@@H](C(C)C)CCC3)C(=O)N2] (5R)-N-[(3S)-6-fluoro-8-me thyl-4-oxo-3,5-dihydro-2H-1,5-benzoxazepin-3-yl]-5-isopropyl-5,6,7,8-tetrahydro-[1,2,4]triazolo[1,5-apyridine-2-carboxamide | Single Unknown Stereoisomer | $^1$H NMR (400 MHz, DMSO-$d_6$) δ 10.00 (s, 1H), 8.35 (d, J = 7.8 Hz, 1H), 7.03-6.94 (m, 1H), 6.89 (s, 1H), 4.84 (dt, J = 11.1, 7.5 Hz, 1H), 4.59 (t, J = 10.7 Hz, 1H), 4.46 (dd, J = 10.1, 7.3 Hz, 1H), 4.16 (dt, J = 8.6, 4.6 Hz, 1H), 2.96-2.85 (m, 1H), 2.79 (ddd, J = 17.7, 9.9, 5.3 Hz, 1H), 2.72-2.59 (m, 1H), 2.30 (s, 3H), 2.07-1.98 (m, 2H), 1.73 (ddd, J = 10.8, 8.5, 5.7 Hz, 2H), 0.98 (d, J = 7.0 Hz, 3H), 0.69 (d, J = 6.8 Hz, 3H) | 402.1 4.94 min |
| Example 439 0.00662 Method GZ2 | 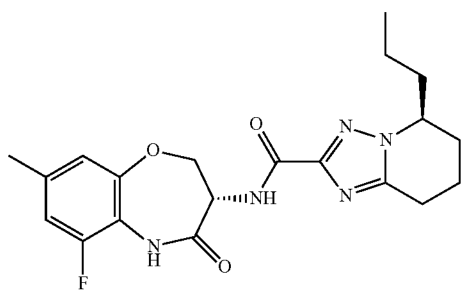 [SMILES: CCC[C@H]1CCCc2nc(C(=O)N[C@H]3COc4cc(C)cc(F)c4NC3=O)nn21] (5S)-N-[(3S)-6-fluoro-8-methyl-4-oxo-3,5-dihydro-2H-1,5-benzoxazepin-3-yl]-5-propyl-5,6,7,8-tetrahydro-[1,2,4]triazolo[1,5-a]pyridine-2-carboxamide | Single Unknown Stereoisomer | NO NMR | 402.1 5.05 min |

TABLE 4-continued

| Example Ki (µM) METHOD | Structure | Stereo | $^1$H NMR | MS (m/z) R.T. |
|---|---|---|---|---|
| Example 440 0.00346 Method GZ2 | 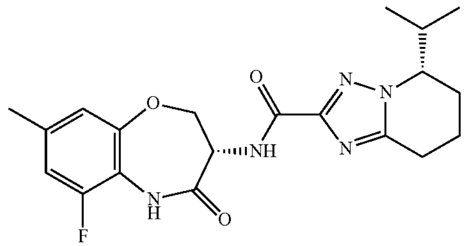 [SMILES: Cc1cc(F)c2c(c1)OC[C@H](NC(=O)c1nc3n(n1)[C@H](C(C)C)CCC3)C(=O)N2] (5S)-N-[(3S)-6-fluoro-8-methyl-4-oxo-3,5-dihydro-2H-1,5-benzoxazepin-3-yl]-5-isopropyl-5,6,7,8-tetrahydro-[1,2,4]triazolo]1,5-a]pyridine-2-carboxamide | Single Unknown Stereoisomer | $^1$H NMR (400 MHz, DMSO-$d_6$) δ 10.00 (s, 1H), 8.35 (d, J = 7.8 Hz, 1H), 7.03-6.94 (m, 1H), 6.89 (s, 1H), 4.84 (dt, J = 11.1, 7.5 Hz, 1H), 4.59 (t, J = 10.7 Hz, 1H), 4.46 (dd, J = 10.1, 7.3 Hz, 1H), 4.16 (dt, J = 8.6, 4.6 Hz, 1H), 2.96-2.85 (m, 1H), 2.79 (ddd, J = 17.7, 9.9, 5.3 Hz, 1H), 2.72-2.59 (m, 1H), 2.30 (s, 3H), 2.07-1.98 (m, 2H), 1.73 (ddd, J = 10.8, 8.5, 5.7 Hz, 2H), 0.98 (d, J = 7.0 Hz, 3H), 0.69 (d, J = 6.8 Hz, 3H) | 402.1 4.91 min |
| Example 441 0.00929 Method GZ2 | 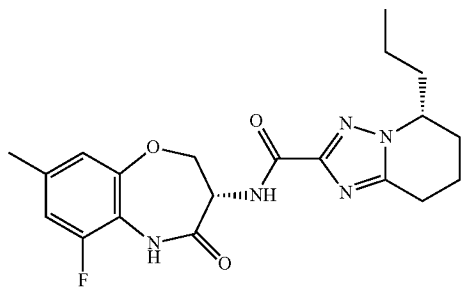 [SMILES: CCC[C@@H]1CCCc2nc(C(=O)N[C@H]3COc4cc(C)cc(F)c4NC3=O)nn21] (5R)-N-[(3S)-6-fluoro-8-methyl-4-oxo-3,5-dihydro-2H-1,5-benzoxazepin-3-yl]-5-propyl-5,6,7,8-tetrahydro-[1,2,4]triazolo[1,5-a]pyridine-2-carboxamide | Single Unknown Stereoisomer | NO NMR | 402.1 5.08 min |

TABLE 4-continued

| Example Ki (μM) METHOD | Structure | Stereo | $^1$H NMR | MS (m/z) R.T. |
|---|---|---|---|---|
| Example 442<br>0.00783<br>Method GZ5 | 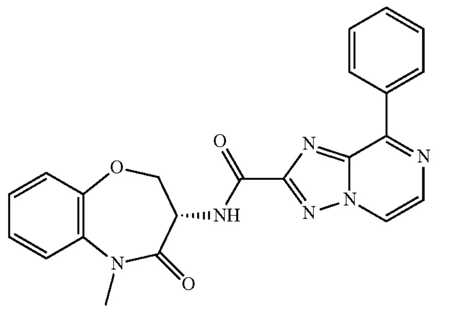 [SMILES: CN1C(=O)[C@@H](NC(=O)c2nc3c(-c4ccccc4)nccn3n2)COc2ccccc21]<br>N-[(3S)-5-methyl-4-oxo-2,3-dihydro-1,5-benzoxazepin-3-yl]-8-phenyl-[1,2,4]triazolo[1,5-a]pyrazine-2-carboxamide | Single Known Stereoisomer | $^1$H NMR (400 MHz, DMSO-$d_6$) δ 9.15-9.03 (m, 2H), 8.84-8.75 (m, 2H), 8.47 (d, J = 4.5 Hz, 1H), 7.70-7.58 (m, 3H), 7.55 (dd, J = 7.6, 1.9 Hz, 1H), 7.40-7.23 (m, 3H), 4.98 (dt, J = 11.5, 7.8 Hz, 1H), 4.73 (dd, J = 11.6, 9.8 Hz, 1H), 4.51 (dd, J = 9.8, 7.7 Hz, 1H), 3.35 (s, 3H) | 415.1<br>5.04 min |
| Example 443<br>0.299<br>METHOD GZ7 | 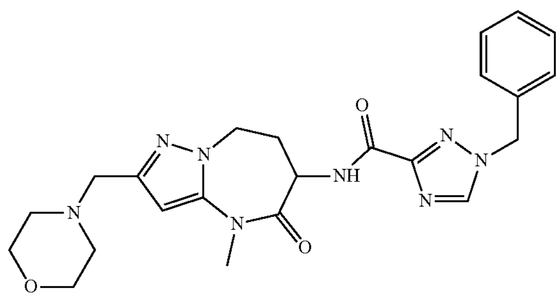<br>1-benzyl-N-[4-methyl-2-(morpholinomethyl)-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-$d_6$) δ 8.81 (s, 1H), 8.51 (d, J = 7.7 Hz, 1H), 7.42-7.26 (m, 5H), 6.26 (s, 1H), 5.48 (s, 2H), 4.36-4.24 (m, 2H), 4.14 (ddd, J = 14.5, 12.5, 6.6 Hz, 1H), 3.57 (t, J = 4.6 Hz, 4H), 3.48-3.32 (m, 2H), 3.23 (s, 3H), 2.59 (m, 1H), 2.50-2.29 (m, 5H) | 465.2<br>2.56 min |

TABLE 4-continued

| Example Ki (μM) METHOD | Structure | Stereo | $^1$H NMR | MS (m/z) R.T. |
|---|---|---|---|---|
| Example 444<br>0.00467<br>Method GZ2 | 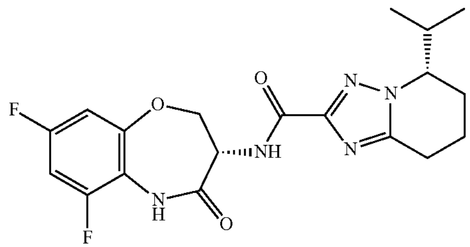 [SMILES: CC(C)[C@@H]1CCCc2nc(C(=O)N[C@H]3COc4cc(F)cc(F)c4NC3=O)nn21]<br>(5S)-N-[(3S)-6,8-difluoro-4-oxo-3,5-dihydro-2H-1,5-benzoxazepin-3-yl]-5-isopropyl-5,6,7,8-tetrahydro-[1,2,4]triazolo[1,5-a]pyridine-2-carboxamide | Single Unknown Stereoisomer | $^1$H NMR (400 MHz, DMSO-$d_6$) δ 10.07 (s, 1H), 8.38 (d, J = 7.7 Hz, 1H), 7.23 (ddd, J = 10.4, 9.0, 2.9 Hz, 1H), 7.03 (dt, J = 9.4, 2.2 Hz, 1H), 4.90 (dt, J = 11.1, 7.4 Hz, 1H), 4.65 (t, J = 10.7 Hz, 1H), 4.52 (dd, J = 10.2, 7.1 Hz, 1H), 4.17 (dt, J = 8.8, 4.6 Hz, 1H), 2.90 (d, J = 16.6 Hz, 1H), 2.79 (td, J = 12.3, 10.8, 5.0 Hz, 1H), 2.68-2.59 (m, 1H), 2.10-1.98 (m, 2H), 1.84-1.65 (m, 2H), 0.98 (d, J = 7.1 Hz, 3H), 0.69 (d, J = 6.8 Hz, 3H) | 406.1<br>4.60 min |
| Example 445<br>0.00347<br>Method GZ2 | 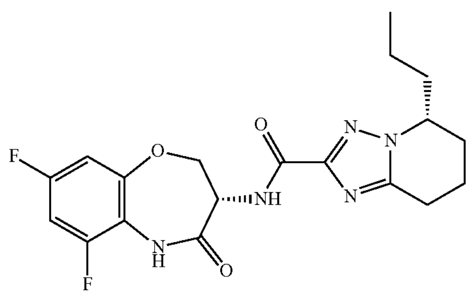 [SMILES: CCC[C@@H]1CCCc2nc(C(=O)N[C@H]3COc4cc(F)cc(F)c4NC3=O)nn21]<br>(5R)-N-[(3 S)-6,8-difluoro-4-oxo-3,5-dihydro-2H-1,5-benzoxazepin-3-yl]-5-propyl-5,6,7,8-tetrahydro-[1,2,4] triazolo[1,5-a]pyridine-2-carboxamide | Single Unknown Stereoisomer | NO NMR | 406.1<br>4.68 min |

TABLE 4-continued

| Example<br>Ki (µM)<br>METHOD | Structure | Stereo | $^1$H NMR | MS (m/z) R.T. |
|---|---|---|---|---|
| Example 446<br>0.00706<br>Method GZ2 | 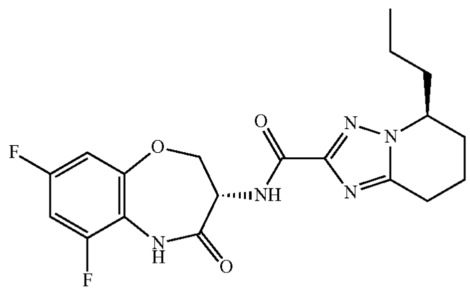 [SMILES: CCC[C@H]1CCCc2nc(C(=O)N[C@H]3COc4cc(F)cc(F)c4NC3=O)nn21]<br>(5S)-N-[(3S)-6,8-difluoro-4-oxo-3,5-dihydro-2H-1,5-benzoxazepin-3-yl]-5-propyl-5,6,7,8-tetrahydro-[1,2,4]triazolo[1,5-a]pyridine-2-carboxamide | Single<br>Unknown<br>Stereoisomer | NO NMR | 406.1<br>4.68 min |
| Example 447<br>0.207<br>Method GZ2 | 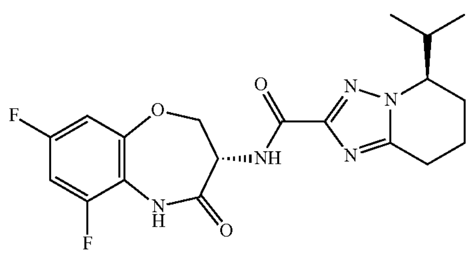 [SMILES: CC(C)[C@H]1CCCc2nc(C(=O)N[C@H]3COc4cc(F)cc(F)c4NC3=O)nn21]<br>(5R)-N-[(3S)-6,8-difluoro-4-oxo-3,5-dihydro-2H-1,5-benzoxazepin-3-yl]-5-isopropyl-5,6,7,8-tetrahydro-[1,2,4]triazolo[1,5-a]pyridine-2-carboxamide | Single<br>Unknown<br>Stereoisomer | $^1$H NMR (400 MHz, DMSO-$d_6$) δ 10.07 (s, 1H), 8.38 (d, J = 7.7 Hz, 1H), 7.23 (ddd, J = 10.4, 9.0, 2.9 Hz, 1H), 7.03 (dt, J = 9.4, 2.2 Hz, 1H), 4.90 (dt, J = 11.1, 7.4 Hz, 1H), 4.65 (t, J = 10.7 Hz, 1H), 4.52 (dd, J = 10.2, 7.1 Hz, 1H), 4.17 (dt, J = 8.8, 4.6 Hz, 1H), 2.90 (d, J = 16.6 Hz, 1H), 2.79 (td, J = 12.3, 10.8, 5.0 Hz, 1H), 2.68-2.59 (m, 1H), 2.10-1.98 (m, 2H), 1.84-1.65 (m, 2H), 0.98 (d, J = 7.1 Hz, 3H), 0.69 (d, J = 6.8 Hz, 3H) | 406.1<br>4.58 min |

TABLE 4-continued

| Example<br>Ki (µM)<br>METHOD | Structure | Stereo | $^1$H NMR | MS (m/z) R.T. |
|---|---|---|---|---|
| Example 448<br>0.214<br>METHOD GZ8 | 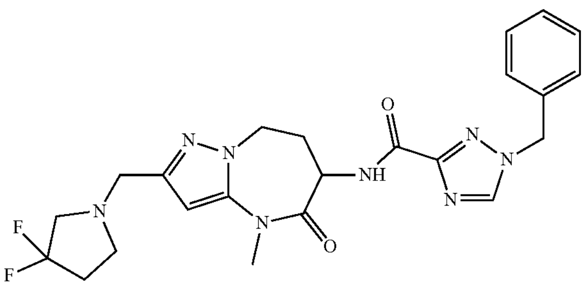 [SMILES: CN1C(=O)C(NC(=O)c2ncn(Cc3ccccc3)n2)CCn2nc(CN3CCC(F)(F)C3)cc21]<br>1-benzyl-N-[2-[(3,3-difluoropyrrolidin-1-yl)methyl]-4-methyl-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-$d_6$) δ 8.81 (s, 1H), 8.52 (d, J = 7.8 Hz, 1H), 7.42-7.26 (m, 5H), 6.28 (s, 1H), 5.48 (s, 2H), 4.31 (qd, J = 7.9, 2.4 Hz, 2H), 4.15 (ddd, J = 14.5, 12.6, 6.6 Hz, 1H), 3.57 (q, J = 13.4 Hz, 2H), 3.23 (s, 3H), 2.91 (t, J = 13.4 Hz, 2H), 2.73 (t, J = 7.0 Hz, 2H), 2.67-2.54 (m, 1H), 2.43-2.10 (m, 3H) | 485.2<br>2.88 min |
| Example 449<br>0.115<br>Method GZ8 | 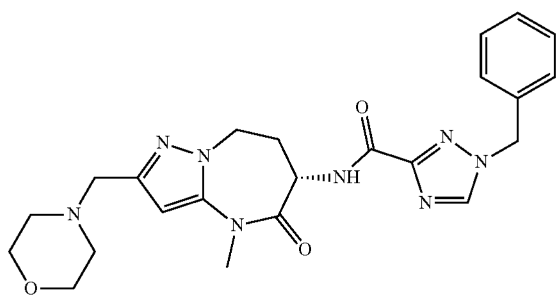 [SMILES: CN1C(=O)[C@@H](NC(=O)c2ncn(Cc3ccccc3)n2)CCn2nc(CN3CCOCC3)cc21]<br>1-benzyl-N-[(6S)-4-methyl-2-(morpholinomethyl)-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-$d_6$) δ 8.81 (s, 1H), 8.51 (d, J = 7.7 Hz, 1H), 7.42-7.26 (m, 5H), 6.26 (s, 1H), 5.48 (s, 2H), 4.36-4.24 (m, 2H), 4.14 (ddd, J = 14.5, 12.5, 6.6 Hz, 1H), 3.57 (t, J = 4.6 Hz, 4H), 3.48-3.32 (m, 2H), 3.23 (s, 3H), 2.59 (m, 1H), 2.50-2.29 (m, 5H). | 4.65.2<br>2.55 min |

TABLE 4-continued

| Example Ki (μM) METHOD | Structure | Stereo | $^1$H NMR | MS (m/z) R.T. |
|---|---|---|---|---|
| Example 450 0.355 Method GZ8 | 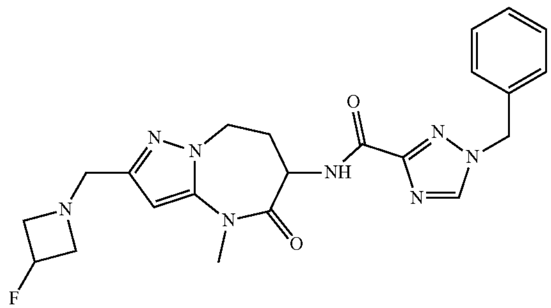 [SMILES: CN1C(=O)C(NC(=O)c2ncn(Cc3ccccc3)n2)CCn2nc(CN3CC(F)C3)cc21] 1-benzyl-N-[2-[(3-fluoroazetidin-1-yl)methyl]-4-methyl-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-$d_6$) δ 8.81 (s, 1H), 8.52 (d, J = 7.8 Hz, 1H), 7.42-7.26 (m, 6H), 6.23 (s, 1H), 5.48 (s, 2H), 5.26-4.98 (m, 1H), 4.35-4.23 (m, 2H), 4.14 (ddd, J = 14.4, 12.5, 6.6 Hz, 1H), 3.67-3.44 (m, 5H), 3.26-3.12 (m, 6H), 2.58 (tt, J = 13.5, 8.5 Hz, 1H), 2.41-2.28 (m, 1H) | 453.2 2.58 min |
| Example 451 0.444 Method GZ8 | 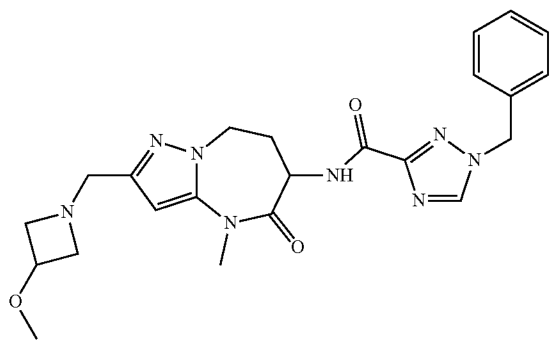 [SMILES: COC1CN(Cc2cc3n(n2)CCC(NC(=O)c2ncn(Cc4ccccc4)n2)C(=O)N3C)C1] 1-benzyl-N-[2-[(3-methoxyazetidin-1-yl)methyl]-4-methyl-5-oxo-7,8-dihydro-6H-prazolo[1,5-a][1,3]diazepin-6-yl]-1,2,4-triazole-3-carboxamide | Mixture of Enantiomers | $^1$H NMR (400 MHz, DMSO-$d_6$) δ 8.81 (s, 1H), 8.51 (d, J = 7.8 Hz, 1H), 7.42-7.23 (m, 5H), 6.21 (s, 1H), 5.48 (s, 2H), 4.29 (ddd, J = 15.8, 8.1, 2.4 Hz, 2H), 4.13 (ddd, J = 14.5, 12.6, 6.6 Hz, 1H), 3.94 (p, J = 5.8 Hz, 1H), 3.48 (dt, J = 21.7, 13.2 Hz, 4H), 3.22 (s, 3H), 3.14 (s, 3H), 2.92-2.81 (m, 2H), 2.57 (ddd, J = 12.7, 8.0, 4.9 Hz, 1H), 2.41 -2.28 (m, 1H) | 465.2 2.66 min |

TABLE 4-continued

| Example Ki (μM) METHOD | Structure | Stereo | $^1$H NMR | MS (m/z) R.T. |
|---|---|---|---|---|
| Example 452 0.206 METHOD GZ6 | 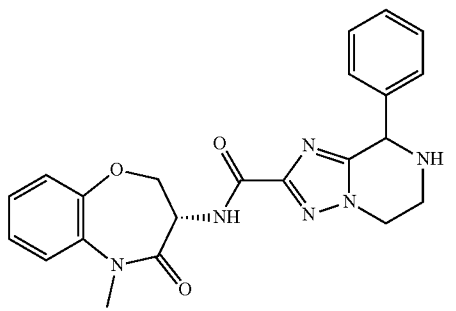 [SMILES: CN1C(=O)[C@@H](NC(=O)c2nc3n(n2)CCNC3c2ccccc2)COc2ccccc21] 8-phenyl-N-[rac-(3S)-5-methyl-4-oxo-2,3-dihydro-1,5-benzoxazepin-3-yl]-5,6,7,8-tetrahydro-[1,2,4]triazolo[1,5-a] pyrazine-2-carboxamide | Mixture of Diastereomers | $^1$H NMR (400 MHz, DMSO-$d_6$) δ 8.34 (dd, J = 8.1, 1.9 Hz, 1H), 7.49 (dt, J = 7.5, 1.5 Hz, 1H), 7.44-7.11 (m, 9H), 5.20 (t, J = 5.0 Hz, 1H), 4.91-4.75 (m, 1H), 4.56 (ddd, J = 11.5, 9.9, 4.1 Hz, 1H), 4.37 (ddd, J = 9.9, 7.6, 6.0 Hz, 1H), 4.32-4.15 (m, 2H), 3.37 (q, J = 5.3 Hz, 1H), 3.32-3.11 (m, 4H) | 419.1 3.26 min |
| Example 453 0.301 Method AA | 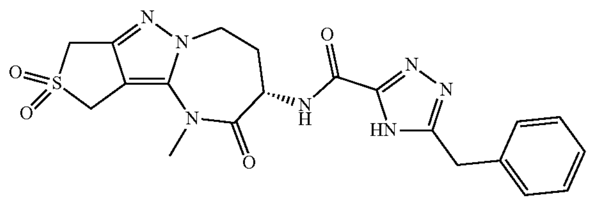 [SMILES: CN1C(=O)[C@@H](NC(=O)c2nnc(Cc3ccccc3)[nH]2)CCn2nc3c(c21)CS(=O)(=O)C3] (S)-5-benzyl-N-(1-methyl-9,9-dioxido-2-oxo-1,2,3,4,5,10-hexahydro-8H-thieno[3',4':3,4]pyrazolo[1,5-a][1,3] diazepin-3-yl)-4H-1,2,4-triazole-3-carboxamide | | $^1$H NMR (400 MHz, DMSO-$d_6$) δ 8.47 (bs, 1H), 7.40-7.17 (m, 5H), 4.56-4.33 (m, 6H), 4.33-4.20 (m, 1H), 4.10 (s, 2H), 3.20 (s, 3H), 2.75-2.59 (m, 1H), 2.41-2.29 (m, 1H). | 456.1 3.40 min |
| Example 454 0.046 Method Z | 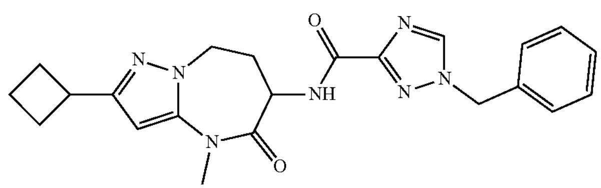 [SMILES: CN1C(=O)C(NC(=O)c2ncn(Cc3ccccc3)n2)CCn2nc(C3CCC3)cc21] 1-benzyl-N-(2-cyclobutyl-4-methyl-5-oxo-5,6,7,8-tetrahydro-4H-pyrazolo[1,5-a][1,3]diazepin-6-yl)-1H-1,2,4-triazole-3-carboxamide | | $^1$H NMR (400 MHz, DMSO-$d_6$) δ 8.81 (s, 1H), 8.49 (d, J = 7.8 Hz, 1H), 7.46-7.27 (m, 5H), 6.23 (s, 1H), 5.48 (s, 2H), 4.38-4.23 (m, 2H), 4.17-4.05 (m, 1H), 3.52-3.38 (m, 1H), 3.23 (s, 3H), 2.39-2.06 (m, 5H), 2.02-1.76 (m, 3H). | 420.2 4.58 min |

TABLE 4-continued

| Example Ki (µM) METHOD | Structure | Stereo | $^1$H NMR | MS (m/z) R.T. |
| --- | --- | --- | --- | --- |
| Example 455 0.060 Method Z | 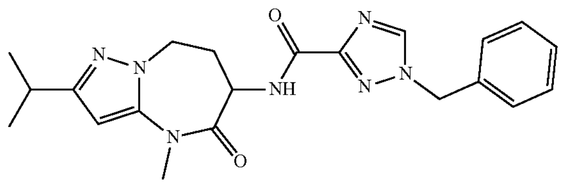 [SMILES: CC(C)c1cc2n(n1)CCC(NC(=O)c1ncn(Cc3ccccc3)n1)C(=O)N2C] 1-benzyl-N-(2-isopropyl-4-methyl-5-oxo-5,6,7,8-tetrahydro-4H-pyrazolo[1,5-a][1,3]diazepin-6-yl)-1H-1,2,4-triazole-3-carboxamide | | $^1$H NMR (400 MHz, DMSO-$d_6$) δ 8.81 (s, 1H), 8.49 (d, J = 7.8 Hz, 1H), 7.43-7.26 (m, 5H), 6.18 (s, 1H), 5.48 (s, 2H), 4.39-4.23 (m, 2H), 4.20-4.03 (m, 1H), 3.22 (s, 3H), 2.86 (hept, J = 7.0 Hz, 1H), 2.40-2.24 (m, 2H), 1.21 (d, J = 6.9 Hz, 6H) | 408.2 4.42 min |
| Example 456 0.051 Method Z | 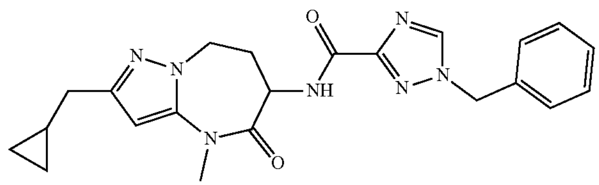 [SMILES: CN1C(=O)C(NC(=O)c2ncn(Cc3ccccc3)n2)CCn2nc(CC3CC3)cc21] 1-benzyl-N-(2-(cyclopropyl methyl)-4-methyl-5-oxo-5,6,7,8-tetrahydro-4H-pyrazolo[1,5-a][1,3]diazepin-6-yl)-1H-1,2,4-triazole-3-carboxamide | | $^1$H NMR (400 MHz, DMSO-$d_6$) δ 8.81 (s, 1H), 8.50 (d, J = 7.8 Hz, 1H), 7.45-7.24 (m, 5H), 6.21 (s, 1H), 5.48 (s, 2H), 4.37-4.04 (m, 3H), 3.23 (s, 3H), 2.47-2.29 (m, 4H), 1.06-0.89 (m, 1H), 0.52-0.41 (m, 2H), 0.24-0.10 (m, 2H). | 420.2 4.51 min |
| Example 457 Method Z | 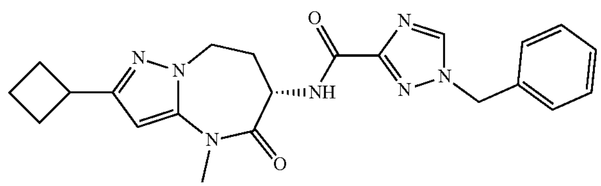 [SMILES: CN1C(=O)[C@@H](NC(=O)c2ncn(Cc3ccccc3)n2)CCn2nc(C3CCC3)cc21] (S)-1-benzyl-N-(2-cyclobutyl-4-methyl-5-oxo-5,6,7,8-tetrahydro-4H-pyrazolo[1,5-a][1,3]diazepin-6-yl)-1H-1,2,4-triazole-3-carboxamide | | $^1$H NMR (400 MHz, DMSO-$d_6$) δ 8.81 (s, 1H), 8.49 (d, J = 7.8 Hz, 1H), 7.46-7.27 (m, 5H), 6.23 (s, 1H), 5.48 (s, 2H), 4.38-4.23 (m, 2H), 4.17-4.05 (m, 1H), 3.52-3.38 (m, 1H), 3.23 (s, 3H), 2.39-2.06 (m, 5H), 2.02-1.76 (m, 3H). | 420.2 4.60 min |
| Example 458 0.010 Method Z | 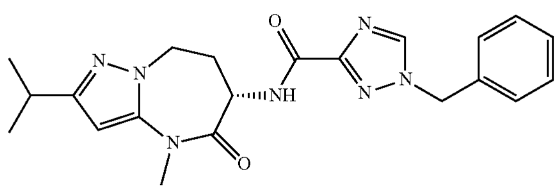 [SMILES: CC(C)c1cc2n(n1)CC[C@H](NC(=O)c1ncn(Cc3ccccc3)n1)C(=O)N2C] (S)-1-benzyl-N-(2-isopropyl -4-methyl-5-oxo-5,6,7,8-tetrahydro-4H-pyrazolo[1,5-a][1,3]diazepin-6-yl)-1H-1,2,4-triazole-3-carboxamide | | $^1$H NMR (400 MHz, DMSO-$d_6$) δ 8.82 (s, 1H), 8.50 (d, J = 7.8 Hz, 1H), 7.45-7.24 (m, 5H), 6.18 (s, 1H), 5.48 (s, 2H), 4.38-4.23 (m, 2H), 4.18-4.03 (m, 1H), 3.22 (s, 3H), 2.86 (hept, J = 6.9 Hz, 1H), 2.66-2.53 (m, 1H), 2.41-2.26 (m, 1H), 1.21 (dd, J = 6.9, 4.4 Hz, 6H). | 408.2 4.45 min |

TABLE 4-continued

| Example<br>Ki (μM)<br>METHOD | Structure | Stereo | $^1$H NMR | MS (m/z) R.T. |
|---|---|---|---|---|
| Example 459<br>0.007<br>Method Z | 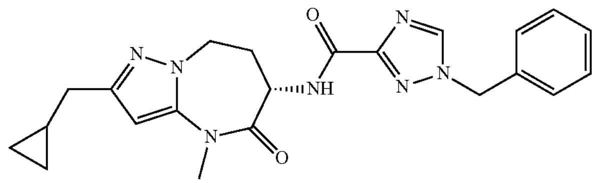 [SMILES: CN1C(=O)[C@@H](NC(=O)c2ncn(Cc3ccccc3)n2)CCn2nc(CC3CC3)cc21]<br>(S)-1-benzyl-N-(2-(cyclopropylmethyl)-4-methyl-5-oxo-5,6,7,8-tetrahydro-4H-pyrzolo[1,5-a][1,3]diazepin-6-yl)-1H-1,2,4-triazole-3-carbamide | | $^1$H NMR (400 MHz, DMSO-$d_6$) δ 8.82 (s, 1H), 8.51 (d, J = 7.8 Hz, 1H), 7.45-7.22 (m, 5H), 6.22 (s, 1H), 5.48 (s, 2H), 4.38-4.22 (m, 2H), 4.20-4.04 (m, 1H), 3.23 (s, 3H), 2.63-2.55 (m, 1H), 2.43 (t, J = 6.5 Hz, 2H), 2.39-2.28 (m, 1H), 1.03-0.93 (m, 1H), 0.52-0.42 (m, 2H), 0.25-0.12 (m, 2H). | 420.2<br>4.53 min |
| Example 460<br>0.041<br>Method Z | 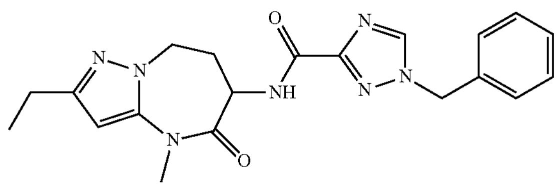 [SMILES: CCc1cc2n(n1)CCC(NC(=O)c1ncn(Cc3ccccc3)n1)C(=O)N2C]<br>1-benzyl-N-(2-ethyl-4-methyl-5-oxo-5,6,7,8-tetrahydro-4H-pyrazolo[1,5-a][1,3]diazepin-6-yl)-1H-1,2,4-triazole-3-carboxamide | | $^1$H NMR (400 MHz, DMSO-$d_6$) δ 8.81 (s, 1H), 8.49 (d, J = 7.8 Hz, 1H), 7.44-7.26 (m, 5H), 6.16 (s, 1H), 5.48 (s, 2H), 4.40-4.23 (m, 2H), 4.15-4.04 (m, 1H), 3.22 (s, 3H), 2.62-2.51 (m, 3H), 2.40-2.25 (m, 1H), 1.18 (t, J = 7.6 Hz, 3H). | 394.2<br>4.14 min |
| Example 461<br>0.050<br>Method Z | 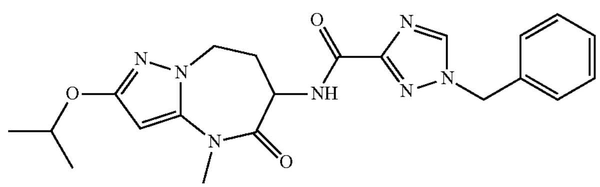 [SMILES: CC(C)Oc1cc2n(n1)CCC(NC(=O)c1ncn(Cc3ccccc3)n1)C(=O)N2C]<br>1-benzyl-N-(2-isopropoxy-4-methyl-5-oxo-5,6,7,8-tetrahydro-4H-pyrazolo[1,5-a][1,3]diazepin-6-yl)-1H-1,2,4-triazole-3-carboxamide | | $^1$H NMR (400 MHz, DMSO-$d_6$) δ 8.82 (s, 1H), 8.52 (d, J = 7.8 Hz, 1H), 7.43-7.26 (m, 5H), 5.79 (s, 1H), 5.48 (s, 2H), 4.68 (hepta, J = 6.1 Hz, 1H), 4.37 (dt, J = 11.5, 7.8 Hz, 1H), 4.15-4.02 (m, 2H), 3.20 (s, 3H), 2.64-2.53 (m, 1H), 2.39-2.25 (m, 1H), 1.28 (d, J = 6.1 Hz, 3H), 1.26 (d, J = 6.1 Hz, 3H). | 424.2<br>4.44 min |

TABLE 4-continued

| Example<br>Ki (μM)<br>METHOD | Structure | Stereo | $^1$H NMR | MS (m/z) R.T. |
|---|---|---|---|---|
| Example 462<br>0.033<br>Method B | 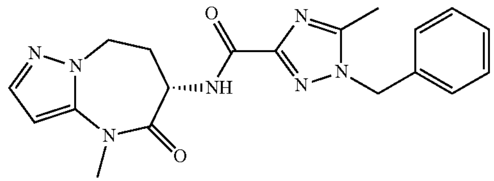 [SMILES: Cc1nc(C(=O)N[C@H]2CCn3nccc3N(C)C2=O)nn1Cc1ccccc1]<br>(S)-1-benzyl-5-methyl-N-(4-methyl-5-oxo-5,6,7,8-tetrahydro-4H-pyrazolo[1,5-a][1,3]diazepin-6-yl)-1H-1,2,4-triazole-3-carboxamide | | $^1$H NMR (400 MHz, DMSO-$d_6$) δ 8.46 (d, J = 7.8 Hz, 1H), 7.49 (d, J = 2.0 Hz, 1H), 7.41-7.30 (m, 3H), 7.26-7.18 (m, 2H), 6.34 (d, J = 2.0 Hz, 1H), 5.44 (s, 2H), 4.44-4.12 (m, 3H), 3.25 (s, 3H), 2.66-2.53 (m, 1H), 2.46 (s, 3H), 2.43-2.32 (m, 1H). | 380.2<br>3.78 min |
| Example 463<br>0.045<br>Method Z | 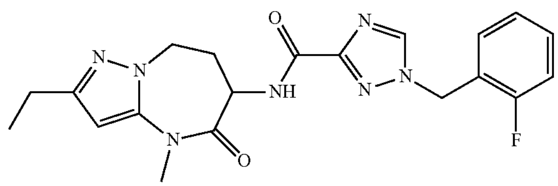 [SMILES: CCc1cc2n(n1)CCC(NC(=O)c1ncn(Cc3ccccc3F)n1)C(=O)N2C]<br>N-(2-ethyl-4-methyl-5-oxo-5,6,7,8-tetrahydro-4H-pyrazolo[1,5-a][1,3]diazepin-6-yl)-1-(2-fluorobenzyl)-1H-1,2,4-triazole-3-carboxamide | | $^1$H NMR (400 MHz, DMSO-$d_6$) δ 8.80 (s, 1H), 8.49 (d, J = 7.8 Hz, 1H), 7.50-7.15 (m, 4H), 6.16 (s, 1H), 5.55 (s, 2H), 4.39-4.22 (m, 2H), 4.14-4.00 (m, 1H), 3.22 (s, 3H), 2.62-2.52 (m, 3H), 2.41-2.25 (m, 1H), 1.18 (t, J = 7.6 Hz, 3H). | 412.2<br>4.27 min |
| Example 464<br>0.014<br>Method Z | 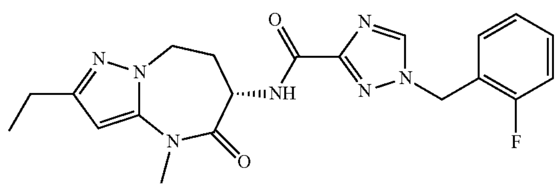 [SMILES: CCc1cc2n(n1)CC[C@H](NC(=O)c1ncn(Cc3ccccc3F)n1)C(=O)N2C]<br>(S)-N-(2-ethyl-4-methyl-5-oxo-5,6,7,8-tetrahydro-4H-pyrazolo[1,5-a][1,3]diazepin-6-yl)-1-(2-fluorobenzyl)-1H-1,2,4-triazole-3-carboxamide | | $^1$H NMR (400 MHz, DMSO-$d_6$) δ 8.80 (s, 1H), 8.50 (d, J = 7.8 Hz, 1H), 7.47-7.18 (m, 4H), 6.16 (s, 1H), 5.55 (s, 2H), 4.39-4.23 (m, 2H), 4.19-4.03 (m, 1H), 3.22 (s, 3H), 2.70-2.50 (m, 3H), 2.41-2.21 (m, 1H), 1.18 (t, J = 7.6 Hz, 3H). | 412.2<br>4.16 min |

TABLE 4-continued

| Example<br>Ki (μM)<br>METHOD | Structure | Stereo | $^1$H NMR | MS (m/z) R.T. |
|---|---|---|---|---|
| Example 465<br>0.009<br>METHOD G11 | 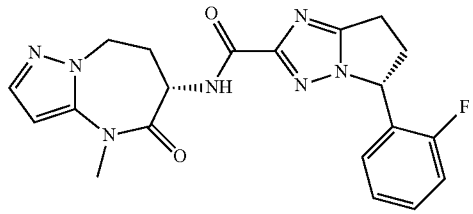 [SMILES: CN1C(=O)[C@@H](NC(=O)c2nc3n(n2)[C@@H](c2ccccc2F)CC3)CCn2nccc21]<br>(R)-5-(2-fluorophenyl)-N-((S)-4-methyl-5-oxo-5,6,7,8-tetrahydro-4H-pyrazolo[1,5-a][1,3]diazepin-6-yl)-6,7-dihydro-5H-pyrrolo[1,2-b][1,2,4]triazole-2-carboxamide | | $^1$H NMR (400 MHz, DMSO-$d_6$) δ 8.50 (d, J = 7.9 Hz, 1H), 7.48 (d, J = 2.0 Hz, 1H), 7.47-7.39 (m, 1H), 7.30-7.20 (m, 3H), 6.33 (d, J = 2.0 Hz, 1H), 5.77 (dd, J = 8.7, 5.7 Hz, 1H), 4.42-4.09 (m, 3H), 3.28-3.17 (m, 4H), 3.14-2.97 (m, 2H), 2.70-2.53 (m, 2H), 2.43-2.27 (m, 1H). | 410.2<br>3.90 min |
| Example 466<br>0.803<br>METHOD G11 | 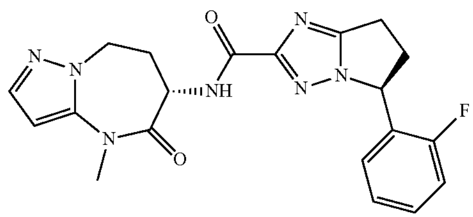 [SMILES: CN1C(=O)[C@@H](NC(=O)c2nc3n(n2)[C@H](c2ccccc2F)CC3)CCn2nccc21]<br>(S)-5-(2-fluorophenyl)-N-((S)-4-methyl-5-oxo-5,6,7,8-ttrahydro-4H-pyrazolo[1,5-a][1,3]diazepin-6-yl)-6,7-dihydro-5H-pyrrolo[1,2-b][1,2,4]triazole-2-carboxamide | | $^1$H NMR (400 MHz, DMSO-$d_6$) δ 8.53 (d, J = 7.8 Hz, 1H), 7.48 (d, J = 2.0 Hz, 1H), 7.47-7.39 (m, 1H), 7.31-7.19 (m, 3H), 6.33 (d, J = 2.0 Hz, 1H), 5.78 (dd, J = 8.7, 5.7 Hz, 1H), 4.43-4.09 (m, 3H), 3.29-3.17 (m, 4H), 3.11-2.99 (m, 2H), 2.71-2.53 (m, 2H), 2.43-2.28 (m, 1H). | 410.2<br>3.90 min |
| Example 467<br>0.057<br>METHOD G11 | 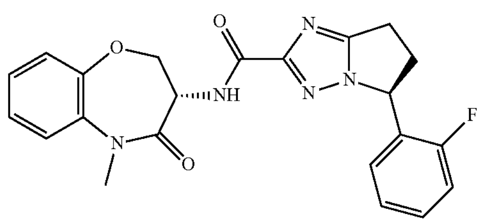 [SMILES: CN1C(=O)[C@@H](NC(=O)c2nc3n(n2)[C@H](c2ccccc2F)CC3)COc2ccccc21]<br>(S)-5-(2-fluorophenyl)-N-(( S)-5-methyl-4-oxo-2,3,4,5-tetrahydrobenzo[b][1,4]oxazepin-3-yl)-6,7-dihydro-5H-pyrrolo[1,2-b][1,2,4]triazole-2-carboxamide | | 1H NMR (400 MHz, DMSO-d6) δ 8.43 (d, J = 8.0 Hz, 1H, NH), 7.52-7.47 (m, 1H), 7.47-7.40 (m, 1H), 7.34-7.19 (m, 6H), 5.78 (dd, J = 8.6, 5.7 Hz, 1H), 4.81 (dt, J = 11.5, 7.8 Hz, 1H), 4.58 (dd, J = 11.6, 9.9 Hz, 1H), 4.39 (dd, J = 9.9, 7.7 Hz, 1H), 3.30 (s, 3H), 3.27-3.18 (m, 1H), 3.16-2.95 (m, 2H), 2.70-2.54 (m, 1H). | 422.2<br>4.90 min |

TABLE 4-continued

| Example Ki (μM) METHOD | Structure | Stereo | $^1$H NMR | MS (m/z) R.T. |
|---|---|---|---|---|
| Example 468<br>0.004<br>METHOD G11 | 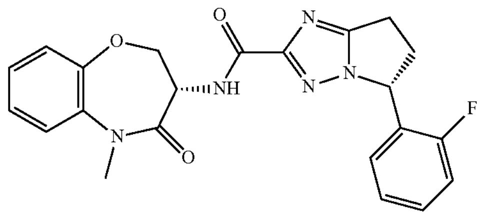 [SMILES: CN1C(=O)[C@@H](NC(=O)c2nc3n(n2)[C@@H](c2ccccc2F)CC3)COc2ccccc21]<br>(R)-5-(2-fluorophenyl)-N-((S)-5-methyl-4-oxo-2,3,4,5-tetrahydrobenzo[b][1,4]oxazepin-3-yl)-6,7-dihydro-5H-pyrrolo[1,2-b][1,2,4]triazole-2-carboxamide | | 1H NMR (400 MHz, DMSO-d6) δ 8.43 (d, J = 8.0 Hz, 1H, NH), 7.53-7.45 (m, 1H), 7.47-7.39 (m, 1H), 7.35-7.19 (m, 6H), 5.78 (dd, J = 8.7, 5.7 Hz, 1H), 4.81 (dt, J = 11.5, 7.8 Hz, 1H), 4.57 (dd, J = 11.5, 9.9 Hz, 1H), 4.39 (dd, J = 9.9, 7.7 Hz, 1H), 3.31 (s, 3H), 3.28-3.17 (m, 1H), 3.11-2.98 (m, 2H), 2.68-2.56 (m, 1H). | 422.2<br>4.94 min |
| Example 469<br>1<br>WX Method 135 | 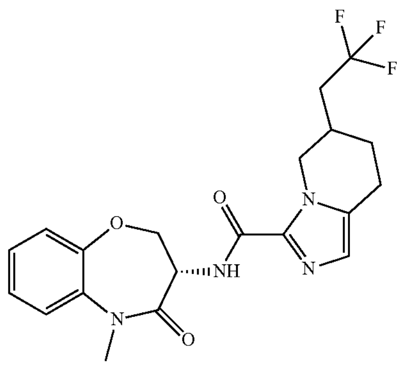 [SMILES: CN1C(=O)[C@@H](NC(=O)c2ncc3n2CC(CC(F)(F)F)CC3)COc2ccccc21]<br>N-[(3S)-5-methyl-4-oxo-2,3-dihydro-1,5-benzoxazepin-3-yl]-6-(2,2,2-trifluoroethyl)-5,6,7,8-tetrahydroimidazo[1,5-a]pyridine-3-carboxamide | Mixture of Diastereomers | $^1$H NMR (400 MHz, $CD_3OD$) δ 7.44-7.41 (m, 1H), 7.32-7.29 (m, 2H), 7.24-7.22 (m, 1H), 6.83 (s, 1H), 4.95-4.90 (m, 1H), 4.85-4.80 (m, 1H), 4.60-4.55 (m, 1H), 4.38-4.34 (m, 1H), 3.85-3.83 (m, 1H), 3.41 (s, 3H), 3.01-2.96 (m, 1H), 2.80-2.78 (m, 1H), 2.35-2.30 (m, 3H), 2.08-2.05 (m, 1H), 1.62-1.60 (m, 1H). | $R_T$ = 2.52 min,<br>m/z = 423.1 |
| Example 470<br>2.4<br>WX Method 001 | 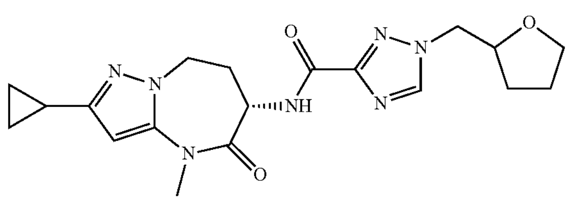 [SMILES: CN1C(=O)[C@@H](NC(=O)c2ncn(CC3CCCO3)n2)CCn2nc(C3CC3)cc21]<br>N-(6S)-2-cyclopropyl-4-methyl-5-oxo-7,8-dihydro-6H-pyrazolo[1,5-a][1,3]diazepin-6-yl-1-(tetrahydrofuran-2-ylmethyl)-1,2,4-triazole-3-carboxamide | Mixture of Diastereomers | $^1$H NMR (400 MHz, $CD_3OD$) δ 8.46 (s, 1H), 6.01 (s, 1H), 4.56-4.51 (m, 1H), 4.38-4.23 (m, 5H), 3.84-3.74 (m, 2H), 3.32 (s, 3H), 2.87-2.85 (m, 1H), 2.27-2.25 (m, 1H), 2.25-2.23 (m, 1H), 1.94-1.87 (m, 3H), 1.83-1.81 (m, 1H), 0.95-0.92 (m, 2H), 0.75-0.73 (m, 2H). | $R_T$ = 0.700 min,<br>m/z = 400.1. |

TABLE 4-continued

| Example Ki (µM) METHOD | Structure | Stereo | $^1$H NMR | MS (m/z) R.T. |
|---|---|---|---|---|
| Example 471<br>0.021<br>WX Method 001 | 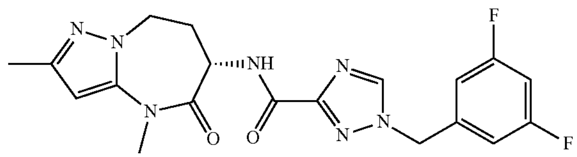 [SMILES: Cc1cc2n(n1)CC[C@H](NC(=O)c1ncn(Cc3cc(F)cc(F)c3)n1)C(=O)N2C]<br>1-[(3,5-difluorophenyl)methyl]-N-[rac-(6S)-2,4-dimethyl-5-oxo-7,8-dihydro-6H-pyrazolo[1,5-a][1,3]diazepin-6-yl]-1,2,4-triazole-3-carboxamide | Single Known Stereoisomer | $^1$H NMR (400 MHz, $CD_3OD$) δ 8.61 (s, 1H), 6.96-6.90 (m, 3H), 6.10 (s, 1H), 5.48 (s, 2H), 4.54-4.49 (m, 1H), 4.2-4.27 (m, 1H), 4.24-4.19 (m, 1H), 3.29 (m, 3H), 2.85-2.79 (m, 1H), 2.28-2.21 (m, 4H). | $R_T$ = 0.756 min, m/z = 416.1 |
| Example 472<br>0.0051<br>WX Method 001 | 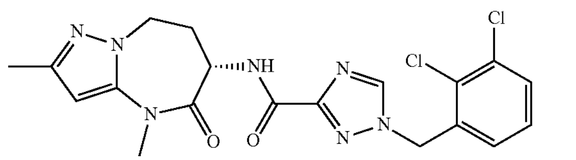 [SMILES: Cc1cc2n(n1)CC[C@H](NC(=O)c1ncn(Cc3cccc(Cl)c3Cl)n1)C(=O)N2C]<br>1-[(2,3-dichlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.61 (s, 1H), 7.55-7.53 (m, 1H), 7.33-7.29 (m, 1H), 7.22-7.20 (m, 1H), 6.09 (s, 1H), 5.63 (s, 2H), 4.53-4.48 1H), 4.29-4.27 (m, 1H), 4.22-4.15 (m, 1H), 3.30 (s, 3H), 2.85-2.78 (m, 1H), 2.27-2.20 (m, 4H). | $R_T$ = 0.791 min, m/z = 448.1 |
| Example 473<br>0.0078<br>WX Method 001 | 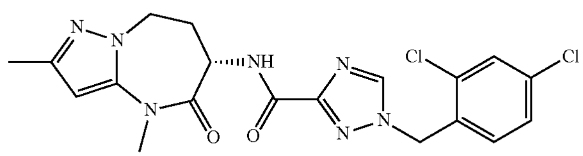<br>1-[(2,4-dichlorophenyl)methyl]-N-(6S)-2,4-dimethyl-5-oxo-7,8-dihydro-6H-pyrazolo[1,5-a][1,3] diazepin-6-yl-1,2,4-triazole-3-carboxamide | Single Known Stereoisomer | $^1$H NMR (400 MHz, $CD_3OD$) δ 8.59 (s, 1H), 7.52 (s, 1H), 7.41-7.30 (m, 2H), 5.99 (s, 1H), 5.57 (s, 2H), 4.53-4.48 (m, 1H), 4.28-4.26 (m, 1H), 4.20-4.17 (m, 1H), 3.29 (s, 3H), 2.85-2.78 (m, 1H), 2.27-2.22 (m, 1H), 1.91-1.86 (m, 1H), 0.92-0.91 (m, 2H), 0.77-0.71 (m, 2H). | $R_T$ = 0.831 min, m/z = 474.1 |
| Example 474<br>1.3<br>WX Method 001 | 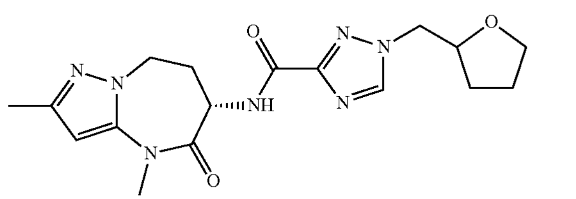 [SMILES: Cc1cc2n(n1)CC[C@H](NC(=O)c1ncn(CC3CCCO3)n1)C(=O)N2C]<br>N-(6S)-2,4-dimethyl-5-oxo-7,8-dihydro-6H-pyrazolo[1,5-a][1,3] diazepin-6-yl-1-(tetrahydrofuran-2-ylmethyl)-1,2,4-triazole-3-carboxamide | Mixture of Diastereomers | $^1$H NMR (400 MHz, $CD_3OD$) δ 8.46 (s, 1H), 6.12 (s, 1H), 4.55-4.53 (m, 1H), 4.41-4.18 (m, 5H), 3.83 (q, J = 6.8 Hz, 1H), 3.78-3.71 (m, 1H), 3.33 (s, 3H), 2.91-2.82 (m, 1H), 2.33-2.19 (m, 4H), 2.12-2.05 (m, 1H), 1.94-1.79 (m, 2H), 1.73-1.65 (m, 1H). | $R_T$ = 1.114 min, m/z = 374.2. |

TABLE 4-continued

| Example Ki (μM) METHOD | Structure | Stereo | $^1$H NMR | MS (m/z) R.T. |
|---|---|---|---|---|
| Example 475<br>0.36<br>WX Method 001 | 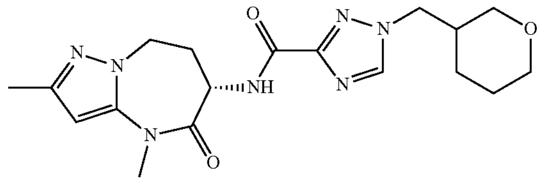 [SMILES: Cc1cc2n(n1)CC[C@H](NC(=O)c1ncn(CC3CCCOC3)n1)C(=O)N2C]<br>N-(6S)-2,4-dimethyl-5-oxo-7,8-dihydro-6H-pyrazolo[1,5-a][1,3]diazepin-6-yl-1-(tetrahydropyran-3-ylmethyl)-1,2,4-triazole-3-carboxamide | Mixture of Diastereomers | $^1$H NMR (400 MHz, $CD_3OD$) δ 8.48 (s, 1H), 6.12 (s, 1H), 4.53-4.51(m, 1H), 4.31-4.19 (m, 4H), 3.76-3.74 (m, 2H), 3.48-3.46 (m, 1H), 3.33 (s, 3H), 3.31-3.25 (m, 1H), 2.85-2.83 (m, 1H), 2.28-2.22 (m, 5H), 1.73-1.70 (m, 2H), 1.60-1.50 (m, 1H), 1.34-1.31 (m, 1H). | $R_T$ = 1.176 min, m/z = 388.1. |
| Example 476<br>0.31<br>WX Method 001 | 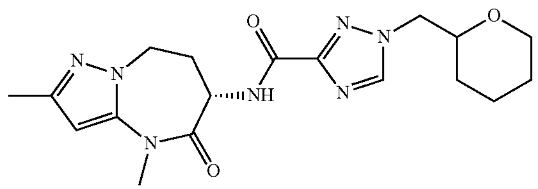 [SMILES: Cc1cc2n(n1)CC[C@H](NC(=O)c1ncn(CC3CCCCO3)n1)C(=O)N2C]<br>N-(6S)-2,4-dimethyl-5-oxo-7,8-dihydro-6H-pyrazolo[1,5-a][1,3]diazepin-6-yl-1-(tetrahydropyran-2-ylmethyl)-1,2,4-triazole-3-carboxamide | Mixture of Diastereomers | $^1$H NMR (400 MHz, $CD_3OD$) δ 8.41 (s, 1H), 6.11 (s, 1H), 4.54-4.40 (m, 1H), 4.37-4.17 (m, 4H), 3.96-3.87 (m, 1H), 3.76-3.67 (m, 1H), 3.38-3.31 (m, 4H), 2.93-2.78 (m, 1H), 2.26 (s, 4H), 1.86 (s, 1H), 1.67-1.65 (m, 1H), 1.61-1.46 (m, 3H), 1.34-1.20 (m, 1H) | $R_T$ = 1.298 min, m/z = 388.2. |
| Example 477<br>0.29<br>WX Method 001 | 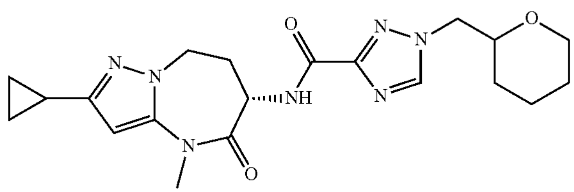 [SMILES: CN1C(=O)[C@@H](NC(=O)c2ncn(CC3CCCCO3)n2)CCn2nc(C3CC3)cc21]<br>N-(6S)-2-cyclopropyl-4-methyl-5-oxo-7,8-dihydro-6H-pyrazolo[1,5-a][1,3]diazepin-6-yl-1-(tetrahydropyran-2-ylmethyl)-1,2,4-triazole-3-carboxamide | Mixture of Diastereomers | $^1$H NMR (400 MHz, $CD_3OD$) δ 8.43 (s, 1H), 6.03 (s, 1H), 4.55-4.53 (m, 1H), 4.37-4.13 (m, 4H), 3.93-3.82 (m, 1H), 3.79-3.67 (m, 1H), 3.44-3.36 (m, 1H), 3.34 (s, 3H), 2.94-2.80 (m, 1H), 2.31-2.23 (m, 1H), 2.00-1.83 (m, 2H), 1.71-1.68 (m, 1H), 1.63-1.48 (m, 3H), 1.39-1.21 (m, 1H), 0.97-0.94 (m, 2H), 0.84-0.68 (m, 2H). | $R_T$ =1.458 min, m/z = 414.2. |
| Example 478<br>0.29<br>WX Method 001 | 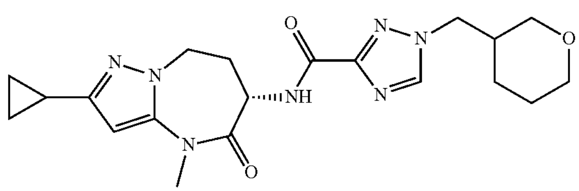 [SMILES: CN1C(=O)[C@@H](NC(=O)c2ncn(CC3CCCOC3)n2)CCn2nc(C3CC3)cc21]<br>N-(6S)-2-cyclopropyl-4-methyl-5-oxo-7,8-dihydro-6H-pyrazolo[1,5-a][1,3]diazepin-6-yl-1-(tetrahydropyran-3-ylmethyl)-1,2,4-triazole-3-carboxamide | Mixture of Diastereomers | $^1$H NMR (400 MHz, $CD_3OD$) δ 8.48 (s, 1H), 6.00 (s, 1H), 4.54-4.53 (m, 1H), 4.30-4.20 (m, 4H), 3.76-3.73 (m, 2H), 3.50-3.46 (m, 1H), 3.31 (s, 3H), 3.28-3.27 (m, 1H), 2.90-2.85 (m, 1H), 2.26-2.21 (m, 2H), 1.91-1.90 (m, 1H), 1.80-1.70 (m, 2H), 1.70-1.65 (m, 1H), 1.40-1.35 (m, 1H), 0.94-0.92 (m, 2H), 0.75-0.70 (m, 2H). | $R_T$ = 1.781 min, m/z = 414.2. |

TABLE 4-continued

| Example Ki (μM) METHOD | Structure | Stereo | $^1$H NMR | MS (m/z) R.T. |
|---|---|---|---|---|
| Example 479 2.8 WX Method 001 | 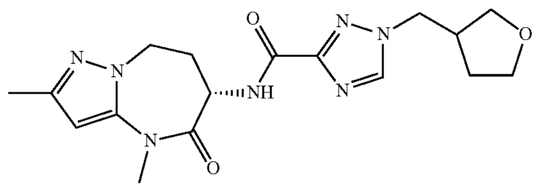 [SMILES: Cc1cc2n(n1)CC[C@H](NC(=O)c1ncn(CC3CCOC3)n1)C(=O)N2C] N-(6S)-2,4-dimethyl-5-oxo-7,8-dihydro-6H-pyrazolo[1,5-a][1,3]diazepin-6-yl-1-(tetrahydrofuran-3-ylmethyl)-1,2,4-triazole-3-carboxamide | Mixture of Diastereomers | $^1$H NMR ($CD_3OD$) δ 8.53 (s, 1H), 6.12 (s, 1H), 4.57-4.54 (m, 1H), 4.36-4.18 (m, 4H), 3.93-3.86 (m, 1H), 3.82-3.71 (m, 2H), 3.62-3.60 (m, 1H), 3.34 (s, 3H), 2.92-2.80 (m, 2H), 2.31-2.22 (m, 4H), 2.11-2.01 (m, 1H), 1.76-1.66 (m, 1H). | $R_T$ = 1.383 min, m/z = 374.2. |
| Example 480 2.6 WX Method 001 | 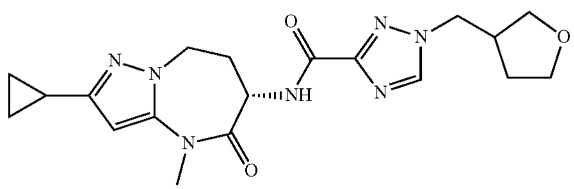 [SMILES: CN1C(=O)[C@@H](NC(=O)c2ncn(CC3CCOC3)n2)CCn2nc(C3CC3)cc21] N-(6S)-2-cyclopropyl-4-methyl-5-oxo-7,8-dihydro-6H-pyrazolo[1,5-a][1,3]diazepin-6-yl-1-(tetrahydrofuran-3-ylmethyl)-1,2,4-triazole-3-carboxamide | Mixture of Diastereomers | $^1$H NMR (400 MHz, $CD_3OD$) δ 8.53 (s, 1H), 6.02 (s, 1H), 4.56-4.54 (m, 1H), 4.35-4.15 (m, 4H), 3.95-3.90 (m, 1H), 3.82-3.71 (m, 2H), 3.62-3.60 (m, 1H), 3.32 (s, 3H), 2.92-2.80 (m, 2H), 2.30-2.26 (m, 1H), 2.11-2.01 (m, 1H), 1.95-1.87 (m, 1H), 1.76-1.66 (m, 1H), 0.98-0.91 (m, 2H), 0.78-0.71 (m, 2H). | $R_T$ = 1.813 min, m/z = 400.3. |
| Example 481 0.0049 WX Method 164 | 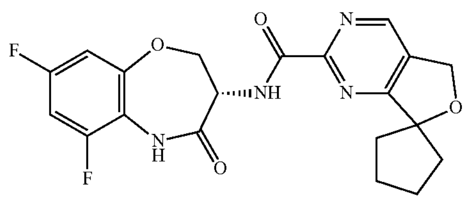 [SMILES: O=C(N[C@H]1COc2cc(F)cc(F)c2NC1=O)c1ncc2c(n1)C1(CCCC1)OC2] N-[(3S)-6,8-difluoro-4-oxo-3,5-dihydro-2H-1,5-benzoxazepin-3-yl]spiro[5H-furo[3,4-d]pyrimidine-7,1'-cyclopentane]-2-carboxamide | Single Known Stereoisomer | $^1$H NMR (400 MHz, $CD_3OD$) δ 8.80 (s, 1H), 6.97-6.87 (m, 2H), 5.12-5.09 (m, 3H), 4.78-4.73 (m, 1H), 4.57-4.51 (m, 1H), 2.14-2.00 (m, 4H), 1.98- 1.87 (m, 4H). | $R_T$ = 0.718 min, m/z = 416.9. |

TABLE 4-continued

| Example Ki (μM) METHOD | Structure | Stereo | $^1$H NMR | MS (m/z) R.T. |
|---|---|---|---|---|
| Example 482 0.0057 WX Method 164 | 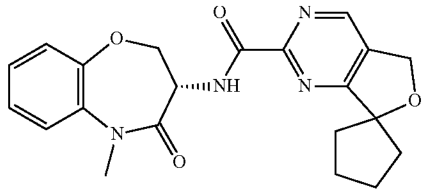 N-[(3S)-5-methyl-4-oxo-2,3-dihydro-1,5-benzoxazepin-3-yl]spiro[5H-furo[3,4-d]pyrimidine-7,1'-cyclopentane]-2-carboxamide | Single Known Stereoisomer | $^1$H NMR (400 MHz, $CD_3OD$) δ 8.80 (s, 1H), 7.46-7.44 (m, 1H), 7.34-7.32 (m, 2H), 7.27-7.24 (m, 1H), 5.12 (s, 2H), 5.07-5.02 (m, 1H), 4.69-4.68 (m, 1H), 4.46-4.43 (m, 1H), 3.44 (s, 3H), 2.08-2.04 (m, 4H), 1.95-1.93 (m, 4H). | $R_T$ = 2.21 min, m/z = 395.2. |
| Example 483 0.11 WX Method 011 | 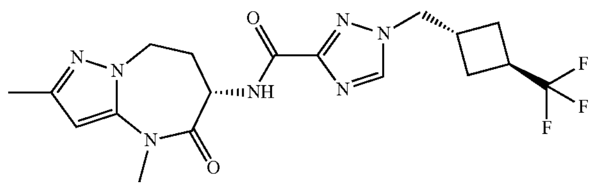 [SMILES: Cc1cc2n(n1)CC[C@H](NC(=O)c1ncn(C[C@H]3C[C@H](C(F)(F)F)C3)n1)C(=O)N2C] N-(S)-2,4-dimethyl-5-oxo-7,8-dihydro-6H-pyrazolo[1,5-a][1,3]diazepin-6-yl]-1-(((1R,3S)-3-trifluoromethylcyclobutyl)methyl)-1H-1,2,4-triazole-3-carboxamide | Single Known Stereoisomer | $^1$H NMR (400 MHz, CD3OD) δ 8.51 (s, 1H), 6.12 (s, 1H), 4.57-4.52 (m, 1H), 4.40-4.22 (m, 4H), 3.34 (s, 3H), 2.96-2.83 (m, 3H), 2.30-2.27 (m, 6H), 2.18-2.12 (m, 2H). | $R_T$ = 0.940 min, m/z = 426.3. |
| Example 484 0.082 WX Method 011 | 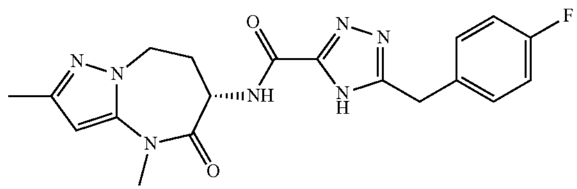 5-[(4-fluorophenyl)methyl]-N-(6S)-2,4-dimethyl-5-oxo-7,8-dihydro-6H-pyrazolo[1,5-a][1,3]diazepin-6-yl-4H-1,2,4-triazole-3-carboxamide | Single Known Stereoisomer | $^1$H NMR (400 MHz, $CD_3OD$) δ 67.28 (dd, J = 5.2, 8.0 Hz, 2H), 7.02 (t, J = 8.8 Hz, 2H), 6.09 (s, 1H), 4.48-4.53 (m, 1H), 4.19-4.34 (m, 2H), 4.05-4.17 (m, 2H), 3.16-3.28 (m, 3H), 2.77-2.85 (m, 1H), 2.14-2.28 (m, 4H). | $R_T$ = 0.733 min, m/z = 398.1. |

TABLE 4-continued

| Example Ki (μM) METHOD | Structure | Stereo | $^1$H NMR | MS (m/z) R.T. |
|---|---|---|---|---|
| Example 485<br>0.0042<br>WX 147 | 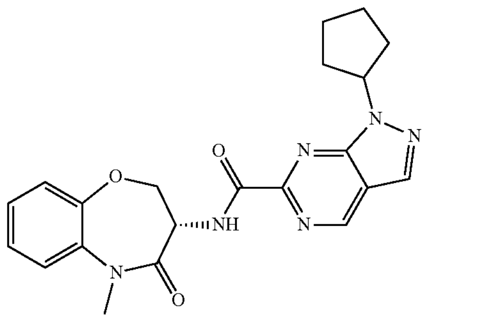 [SMILES: CN1C(=O)[C@@H](NC(=O)c2ncc3cnn(C4CCCC4)c3n2)COc2ccccc21]<br>1-cyclopentyl-N-[(3S)-5-methyl-4-oxo-2,3-dihydro-1,5-benzoxazepin-3-yl]pyrazolo[3,4-d]pyrimidine-6-carboxamide | Single Known Stereoisomer | $^1$H NMR (400 MHz, DMSO-$d_6$) δ 9.46 (s, 1H), 9.13 (d, J = 8.0 Hz, 1H), 8.51 (s, 1H), 7.54-7.51 (m, 1H), 7.35-7.27 (m, 3H), 5.47-5.41 (m, 1H), 4.93-4.88 (m, 1H), 4.61-4.52 (m, 2H), 3.35 (s, 3H), 2.17-2.14 (m, 2H), 2.00-1.91 (m, 4H), 1.74-1.71 (m, 2H). | $R_T$ = 0.836 min, m/z = 407.1. |
| Example 486<br>WX Method 153 | 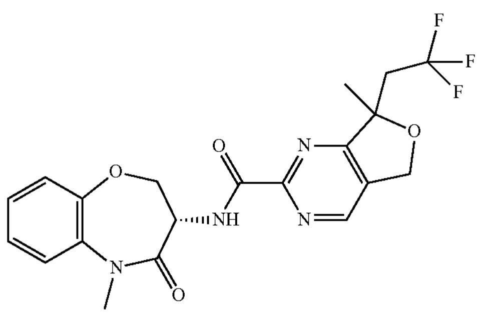 [SMILES: CN1C(=O)[C@@H](NC(=O)c2ncc3c(n2)C(C)(CC(F)(F)F)OC3)COc2ccccc21]<br>7-methyl-N-[(3S)-5-methyl-4-oxo-2,3-dihydro-1,5-benz oxazepin-3-yl]-7-(2,2,2-trifluoroethyl)-5H-furo[3,4-d] pyrimidine-2-carboxamide | Mixture of Diastereomers | $^1$H NMR (400 MHz, $CD_3OD$) δ 8.88 (s, 1H), 7.45-7.24 (m, 4H), 5.25-5.21 (m, 2H), 5.08-5.02 (m 1H) 4.69-4.65 (m, 1H), 4.48-4.43 (m, 1H), 3.43 (s, 3H), 2.97-2.85 (m, 2H), 1.57 (s, 3H). | $R_T$ = 0.806 min, m/z = 437.1. |

TABLE 4-continued

| Example Ki (μM) METHOD | Structure | Stereo | $^1$H NMR | MS (m/z) R.T. |
|---|---|---|---|---|
| Example 487<br>0.37<br>WX Method 153 | 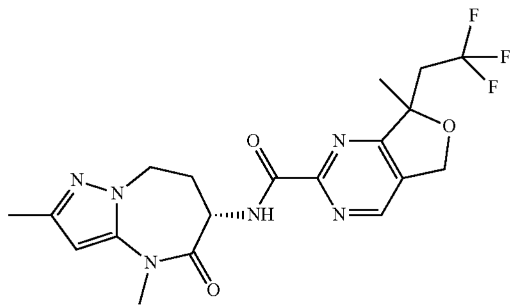<br>7-methyl-N-[(6S)-2,4-dimethyl-5-oxo-7,8-dihydro-6H-pyrazolo[1,5-a][1,3]diazepin-6-yl]-7-(2,2,2-trifluoroethyl)-5H-furo[3,4-d]pyrimidine-2-carboxamide | Mixture of Diastereomers | $^1$H NMR (400 MHz, $CD_3OD$) δ 8.50 (s, 1H), 6.12 (s, 1H), 4.57-4.52 (m, 1H), 4.31-4.22 (m, 4H), 3.33 (s, 3H), 3.01-2.83 (m, 3H), 2.28-2.24 (m, 6H), 2.01-1.98 (m, 2H). | $R_T$ = 0.682 min, m/z = 439.2. |
| Example 488<br>1.8<br>WX Method 176 | 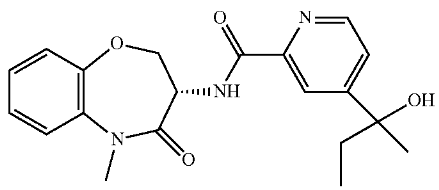 [SMILES: CCC(C)(O)c1ccnc(C(=O)N[C@H]2COc3ccccc3N(C)C2=O)c1]<br>4-(1-hydroxy-1-methyl-propyl)-N-[(3S)-5-methyl-4-oxo-2,3-dihydro-1,5-benzoxazpin-3-yl]pyridine-2-carboxamide | Mixture of Diastereomers | $^1$H NMR (400 MHz, $CD_3OD$) δ 8.59 (d, J = 4.8 Hz, 1H), 8.11 (s, 1H), 7.65-7.61 (m, 1H), 7.46-7.41 (m, 1H), 7.36-7.29 (m, 2H), 7.27-7.22 (m, 1H), 5.06-4.99 (m, 1H), 4.68-4.62 (m, 1H), 4.59 (s, 1H), 4.44-4.37 (m, 1H), 3.43 (s, H), 1.85-1.77 (m, 2H) , 1.50 (s, 3H), 0.76 (t, J = 4.0 Hz, 3H). | $R_T$ = 1.00 min; m/z = 370.2 |
| Example 489<br>0.094<br>WX Method 158 | 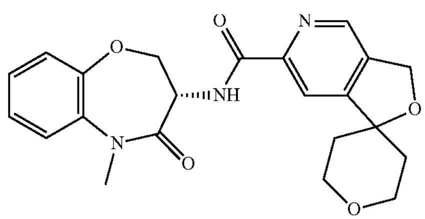 [SMILES: CN1C(=O)[C@@H](NC(=O)c2cc3c(cn2)COC32CCOCC2)COc2ccccc21]<br>N-[(3S)-5-methyl-4-oxo-2,3-dihydro-1,5-benzoxazepin-3-yl]spiro[3H-furo[3,4-c]pyridine-1,3'-tetrahydropyran]-6-carboxamide | Mixture of Diastereomers | $^1$H NMR (400 MHz, $CD_3OD$) δ 8.60 (s, 1H), 8.03 (s, 1H), 7.46-7.43 (m, 1H), 7.33-7.32 (m, 2H), 7.26-7.24 (m, 1H), 5.20 (d, J = 8.0 Hz, 2H), 5.05-5.00 (m, 1H), 4.67-4.62 (m, 1H), 4.43-4.38 (m, 1H), 3.82 (s, 1H), 3.73-3.72 (m, 1H), 3.65-3.64 (m, 2H), 3.43 (s, 3H), 2.03-2.00 (m, 3H), 1.97-1.74 (m, 1H). | $R_T$ = 1.722 min; m/z = 410.1 |

TABLE 4-continued

| Example Ki (μM) METHOD | Structure | Stereo | $^1$H NMR | MS (m/z) R.T. |
| --- | --- | --- | --- | --- |
| Example 490 0.04 WX Method 011 | 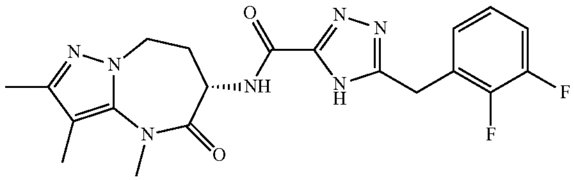 [SMILES: Cc1nn2c(c1C)N(C)C(=O)[C@@H](NC(=O)c1nnc(Cc3cccc(F)c3F)[nH]1)CC2] 5-[(2,3-difluorophenyl)methyl]-N-(6S)-2,3,4-trimethyl-5-oxo-7,8-dihydro-6H-pyrazolo[1,5-a][1,3]diazepin-6-yl-4H-1,2,4-triazole-3-carboxamide | Single Known Stereoisomer | $^1$H NMR (400 MHz, $CD_3OD$) δ 7.20-7.10 (m, 3H), 4.43-4.38 (m, 1H), 4.23-4.19 (m, 4H), 3.30 (s, 3H), 2.78-2.71 (m, 1H), 2.20-2.18 (s, 4H), 2.01 (s, 3H). | $R_T$ = 0.749 min, m/z = 430.1 |
| Example 491 0.037 WX Method 009 | 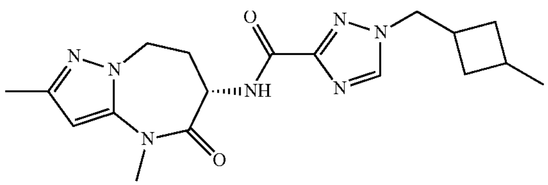 1-[(3-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide | Mixture of Diastereomers | $^1$H NMR (400 MHz, $CD_3OD$) δ 8.47 (s, 1H), 6.12, (s, 1H), 4.56-4.52 (m, 1H), 4.34-4.22 (m, 5H), 3.33 (s, 3H), 2.89-2.64 (m, 2H), 2.27-2.20 (m, 7H), 1.41-1.39 (m, 1H), 1.13-1.02 (m, 3H). | $R_T$ = 0.942 min, m/z = 372.3. |
| Example 492 0.18 WX Method 010 | 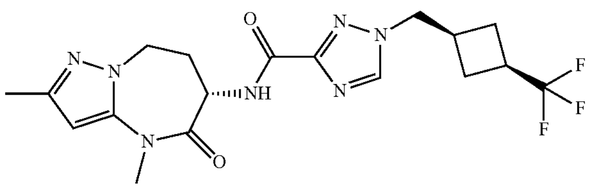 [SMILES: Cc1cc2n(n1)CC[C@H](NC(=O)c1ncn(C[C@H]3C[C@@H](C(F)(F)F)C3)n1)C(=O)N2C] N-(S)-2,4-dimethyl-5-oxo-7,8-dihydro-6H-pyrazolo[1,5-a][1,3] diazepin-6-yl]-1-(((1S,3R)-3-trifluoromethylcyclobutyl)methyl)-1H-1,2,4-triazole-3-carboxamide | Single Known Stereoisomer | $^1$H NMR (400 MHz, $CD_3OD$) δ 8.50 (s, 1H), 6.12 (s, 1H) 4.57-4.52 (m, 1H), 4.31-4.22 (m, 4H), 3.33 (s, 3H), 3.01-2.83 (m, 3H), 2.28-2.24 (m, 6H), 2.01-1.98 (m, 2H) | $R_T$ = 0.927 min, m/z = 426.3. |
| Example 493 0.092 WX Method 010 | 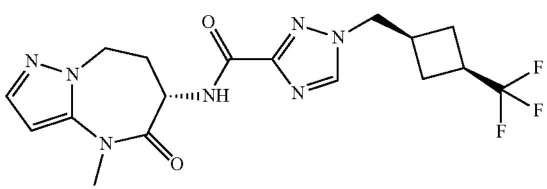 [SMILES: CN1C(=O)[C@@H](NC(=O)c2ncn(C[C@H]3C[C@@H](C(F)(F)F)C3)n2)CCn2nccc21] N-(S)-4-methyl-5-oxo-7,8-dihydro-6H-pyrazolo[1,5-a] [1,3diazepin-6-yl]-1-(((1S,3R)-3-trifluoromethylcyclobutyl) methyl)-1H-1,2,4-triazole-3-carboxamide | Single Known Stereoisomer | $^1$H NMR (400 MHz, $CD_3OD$) δ 8.50 (s, 1H), 7.53 (s, 1H), 6.31 (d, J = 2.0 Hz, 1H), 4.55-4.41 (m, 2H), 4.31-4.29 (m, 3H), 3.37 (s, 3H), 3.01-2.85 (m, 3H), 2.30-2.25 (m, 3H), 2.01-1.94 (m, 2H). | $R_T$ = 0.891 min, m/z = 412.3. |

TABLE 4-continued

| Example Ki (μM) METHOD | Structure | Stereo | $^1$H NMR | MS (m/z) R.T. |
|---|---|---|---|---|
| Example 494 0.11 WX Method 011 | 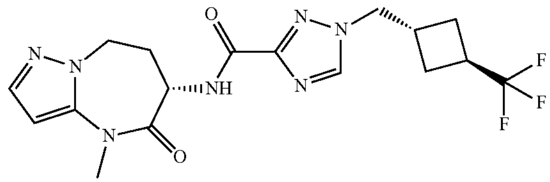 [SMILES: CN1C(=O)[C@@H](NC(=O)c2ncn(C[C@H]3C[C@H](C(F)(F)F)C3)n2)CCn2nccc21] N-(S)-4-methyl-5-oxo-7,8-d ihydro-6H-pyrazolo[1,5-a][1,3]diazepin-6-yl]-1-(((1R,3S)-3-trifluoromethylcyclobutyl)methyl)-1H-1,2,4-triazole-3-carboxamide | Single Known Stereoisomer | $^1$H NMR (400 MHz, $CD_3OD$) δ 8.51 (s, 1H), 7.53 (d, J = 2.0 Hz, 1H), 6.31 (d, J = 2.0 Hz, 1H), 4.52-4.29 (m, 5H), 3.37 (s, 3H), 3.07-2.88 (m, 3H), 2.33-2.26 (m, 3H), 2.18-2.14 (m, 2H). | $R_T$ = 0.903 min, m/z = 412.3. |
| Example 495 0.13 WX Method 014 | 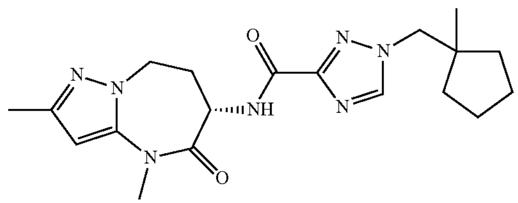 [SMILES: Cc1cc2n(n1)CC[C@H](NC(=O)c1ncn(CC3(C)CCCC3)n1)C(=O)N2C] 1-[(1-methylcyclopentyl)me thyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.49 (s, 1H), 6.12 (s, 1H), 4.57-4.52 (m, 1H), 4.31-4.22 (m, 2H), 4.18 (s, 2H), 3.34 (s, 3H), 2.90-2.83 (m, 1H), 2.30-2.23 (m, 4H), 1.71-1.65 (m, 6H), 1.39-1.36 (m, 2H), 0.97 (s, 3H). | $R_T$ = 0.677 min, m/z = 386.2. |
| Example 496 0.052 WX Method 015 | 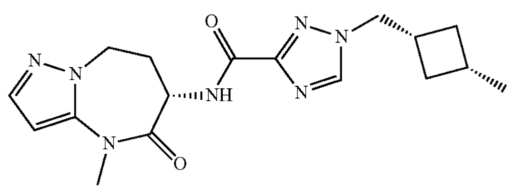 [SMILES: CN1C(=O)[C@@H](NC(=O)c2ncn(C[C@H]3C[C@@H](C)C3)n2)CCn2nccc21] N-((S)-4-methyl-5-oxo-5,6,7,8-tetrahydro-4H-pyrazolo[1,5-a][1,3]diazepin-6-yl)-1-(((lS,3R)-3-methylcyclobutyl)methyl)-1H-1,2,4-triazole-3-carboxamide | Single Known Stereoisomer | $^1$H NMR (400 MHz, $CD_3OD$) δ 8.45 (s, 1H), 7.53 (d, J = 2.0 Hz, 1H), 6.31 (d, J = 1.2 Hz, 1H), 4.54-4.40 (m, 2H), 4.43-4.41 (m, 1H)), 4.23 (d, J = 7.6 Hz, 2H) 3.36 (s, 3H), 2.88-2.83 (m, 1H), 2.68-2.64 (m, 1H), 2.31-2.17 (m, 4H), 1.44-1.36 (m, 2H) 1.03 (d, J = 6.4 Hz, 3H). | $R_T$ = 0.649 min, m/z = 358.2. |
| Example 497 0.041 WX Method 015 | 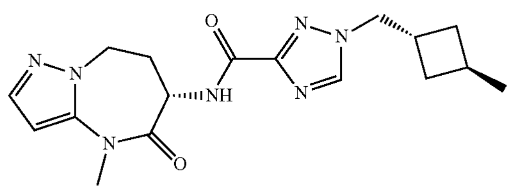 [SMILES: CN1C(=O)[C@@H](NC(=O)c2ncn(C[C@H]3C[C@H](C)C3)n2)CCn2nccc21] N-((S)-4-methyl-5-oxo-5,6,7,8-tetrahydro-4H-pyrazolo[1,5-a][1,3]diazepin-6-yl)-1-(((1R,35)-3-methylcyclobutyl)methyl)-1H-1,2,4-triazole-3-carboxamide | Single Known Stereoisomer | $^1$H NMR (400 MHz, $CD_3OD$) δ 8.48 (s, 1H), 7.53 (d, J = 2.0 Hz, 1H), 6.31 (s, 1H), 4.54-4.49 (m, 2H), 4.34-4.29 (m, 3H), 3.36 (s, 3H), 2.87-2.82 (m, 2H), 2.49-2.40 (m, 1H), 2.29-2.20 (m, 1H), 2.01-1.94 (m, 2H), 1.76-1.71 (m, 2H), 1.12 (d, J = 6.8 Hz, 3H). | $R_T$ = 0.649 min, m/z = 358.2. |

TABLE 4-continued

| Example Ki (μM) METHOD | Structure | Stereo | ¹H NMR | MS (m/z) R.T. |
|---|---|---|---|---|
| Example 498<br>0.40<br>WX Method 015 | 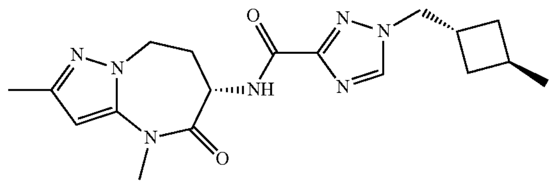<br>N((S)-2,4-dimethyl-5-oxo-5,6,7,8-tetrahydro-4H-pyrazolo [1,5-a][1,3]diazepin-6-yl)-1-(((1R,3S)-3-methylcyclobutyl) methyl)-1H-1,2,4-triazole-3-carboxamideylcyclobutyl)methyl)-1H-1,2,4-triazole-3-carboxamide | Single Known Stereoisomer | ¹H NMR (400 MHz, $CD_3OD$) δ 8.48 (s, 1H), 6.11 (s, 1H), 4.56-4.51 (m, 1H), 4.34-4.29 (m, 3H), 4.24-4.22 (m, 1H), 3.33 (s, 3H), 2.89-2.83 (m, 2H), 2.45-2.43 (m, 1H), 2.25-2.19 (m, 4H), 2.01-1.94 (m, 2H), 1.76-1.69 (m, 2H), 1.12 (d, J = 6.4 Hz, 3H). | $R_T$ = 1.531 min, m/z = 372.0. |
| Example 499<br>0.87<br>WX Method 015 | 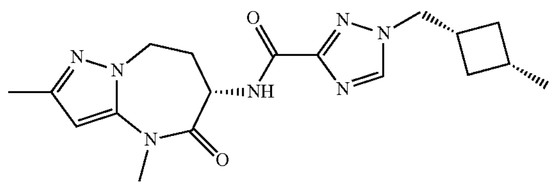<br>N-((S)-2,4-dimethyl-5-oxo-5,6,7,8-tetrahydro-4H-pyrazolo [1,5-a][1,3]diazepin-6-yl)-1-(((lS,3R)-3-methylcyclobutyl)methyl)-1H-1,2,4-triazole-3-carboxamide | Single Known Stereoisomer | ¹H NMR (400 MHz, $CD_3OD$) δ 8.44 (s, 1H), 6.11 (s, 1H), 4.57-4.51 (m, 1H), 4.35-4.29 (m 1H), 4.23-4.21 (m, 3H), 3.33 (s, 3H), 2.89-2.84 (m, 1H), 2.68-2.64 (m, 1H), 2.28-2.17 (m, 7H), 1.43-1.36 (m, 2H), 1.03 (d, J = 6.4 Hz, 3H). | $R_T$ = 1.531 min, m/z = 372.1. |
| Example 500<br>0.036<br>WX Method 017 | 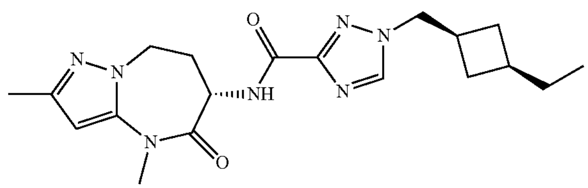 [SMILES: CC[C@H]1C[C@@H](Cn2cnc(C(=O)N[C@H]3CCn4nc(C)cc4N(C)C3=O)n2)C1]<br>N-((S)-2,4-dimethyl-5-oxo-5,6,7,8-tetrahydro-4H-pyrazolo [1,5-a][1,3]diazepin-6-yl)-1-(((1R,3R)-3-ethylcyclobutyl)methyl)-1H-1,2,4-triazole-3-carboxamide | Single Known Stereoisomer | ¹H NMR (400 MHz, $CD_3OD$) δ 8.45 (s, 1H), 6.12 (s, 1H), 4.56-4.52 (m, 1H), 4.31 4.22 (m, 4H), 3.33 (s, 3H), 2.88-2.83 (m, 1H), 2.72-2.68 (m, 1H), 2.26-2.18 (m, 4H), 2.17-2.09 (m, 4H), 1.39-1.37 (m, 2H), 0.82-0.78 (m, 3H). | $R_T$ = 0.0804 min, m/z = 386.1. |

TABLE 4-continued

| Example Ki (μM) METHOD | Structure | Stereo | $^1$H NMR | MS (m/z) R.T. |
|---|---|---|---|---|
| Example 501<br>0.067<br>WX Method 017 | 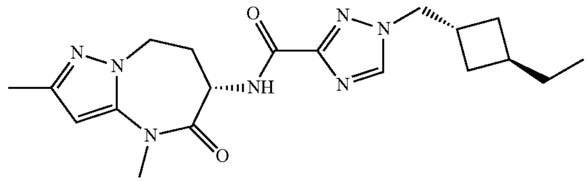 [SMILES: CC[C@H]1C[C@H](Cn2cnc(C(=O)N[C@H]3CCn4nc(C)cc4N(C)C3=O)n2)C1]<br>N-((S)-2,4-dimethyl-5-oxo-5,6,7,8-tetrahydro-4H-pyrazolo [1,5-a][1,3]diazepin-6-yl)-1-(((1S,35)-3-ethylcyclobutyl) methyl)-1H-1,2,4-triazole-3-carboxamide | Single Known Stereoisomer | $^1$H NMR (400 MHz, $CD_3OD$) δ 8.49 (s, 1 H), 6.12 (s, 1H), 4.56-4.52 (m, 1 H), 4.35-4.22 (m, 4 H), 3.33 (s, 3 H), 2.86-2.82 (m, 2 H), 2.26-2.23 (m, 4 H), 1.95-1.91 (m, 2H), 1.80- 1.76 (m, 2H), 1.49-1.46 (m, 2 H), 0.85-0.80 (m, 3H). | $R_T$ = 0.806 min, m/z = 386.1. |
| Example 502<br>0.027<br>WX Method 017 | 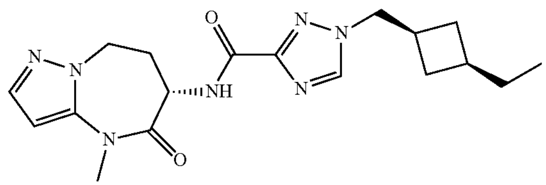 [SMILES: CC[C@H]1C[C@@H](Cn2cnc(C(=O)N[C@H]3CCn4nccc4N(C)C3=O)n2)C1]<br>N-((S)-4-methyl-5-oxo-5,6,7,8-tetrahydro-4H-pyrazolo [1,5-a][1,3]diazepin-6-yl)-1-(((1R,3R)-3-ethylcyclobutyl)methyl)-1H-1,2,4-triazole-3-carboxamide | Single Known Stereoisomer | $^1$H NMR (400 MHz, $CD_3OD$) δ 8.44 (s, 1H), 7.52 (s, 1H), 6.30 (s, 1H), 4.54-4.38 (m, 2H), 4.33-4.25 (m, 1H), 4.22 (d, J = 7.2 Hz, 2H), 3.35 (s, 3H), 2.89-2.87 (m, 1H), 2.67-2.64 (m, 1H), 2.28 -2.25 (m, 1H), 2.16-2.07 (m, 3H), 1.42-1.34 (m, 4H), 0.79 (t, J = 7.2 Hz, 1H). | $R_T$ = 1.62 min, m/z = 372.2. |
| Example 503<br>0.023<br>WX Method 017 | 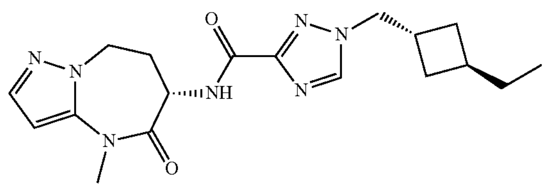 [SMILES: CC[C@H]1C[C@H](Cn2cnc(C(=O)N[C@H]3CCn4nccc4N(C)C3=O)n2)C1]<br>N-((S)-4-methyl-5-oxo-5,6,7,8-tetrahydro-4H-pyrazolo [1,5-a][1,3]diazepin-6-yl)-1-(((1S,3S)-3-ethylcyclobuty1) methyl)-1H-1,2,4-triazole-3-carboxamide | Single Known Stereoisomer | $^1$H NMR (400 MHz, $CD_3OD$) δ 8.48 (s, 1H), 7.52 (s, 1H), 6.30 (s, 1H), 4.53-4.51 (m, 1H), 4.42-4.39 (m, 1H), 4.34-4.27 (m, 3H), 3.35 (s, 3H), 2.89-2.81 (m, 2H), 2.27-2.22 (m, 2H), 1.92-1.89 (m, 2H), 1.79- 1.75 (m, 2H), 1.48-1.44 (m, 2H), 0.82 (t, J = 7.2 Hz, 1H). | $R_T$ = 1.62 min, m/z = 372.2 |

TABLE 4-continued

| Example<br>Ki (μM)<br>METHOD | Structure | Stereo | $^1$H NMR | MS (m/z) R.T. |
|---|---|---|---|---|
| Example 504<br>0.05<br>WX Method 100 | 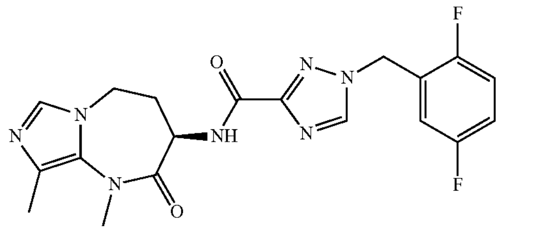 [SMILES: Cc1ncn2c1N(C)C(=O)[C@H](NC(=O)c1ncn(Cc3cc(F)ccc3F)n1)CC2]<br>1-[(2,5-difluorophenyl)methyl]-N-(3R)-1,9-dimethyl-2-oxo-4,5-dihydro-3H-imidazo[1,5-a][1,3]diazepin-3-yl-1,2,4-triazole-3-carboxamide | Single<br>Known<br>Stereoisomer | $^1$H NMR (400 MHz, $CD_3OD$) δ 8.65 (s, 1H), 8.04 (s, 1H), 7.21-7.14 (m, 3H), 5.56 (s, 2H), 4.63-4.58 (m, 1H), 4.47-4.41 (m, 1H), 4.07-4.03 (m, 1H), 3.32 (s, 3H), 2.73-2.65 (m, 1H), 2.27 (s, 3H), 2.22-2.16 (m, 1H). | $R_T$ = 0.557 min;<br>m/z = 416.0 |
| Example 505<br>0.036<br>WX Method 100 | 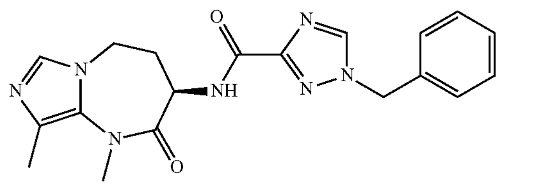 [SMILES: Cc1ncn2c1N(C)C(=O)[C@H](NC(=O)c1ncn(Cc3ccccc3)n1)CC2]<br>1-benzyl-N-(3R)-1,9-dimethyl-2-oxo-4,5-dihydro-3H-imidazo[1,5-a][1,3]diazepin-3-yl-1,2,4-triazole-3-carboxamide | Single<br>Known<br>Stereoisomer | $^1$H NMR (400 MHz, $CD_3OD$) δ 8.58 (s, 1H), 7.78 (s, 1H), 7.39-7.32 (m, 4H), 5.47 (s, 2H), 4.59-4.54 (m, 1H), 4.41-4.35 (m, 1H), 4.01 -3.94 (m, 1H), 3.31 (s, 3H), 2.72-2.66 (m, 1H), 2.24 (s, 3H), 2.15-2.10 (m, 1H). | $R_T$ = 0.508 min;<br>m/z = 380.0 |
| Example 506<br>0.019<br>WX Method 100 | 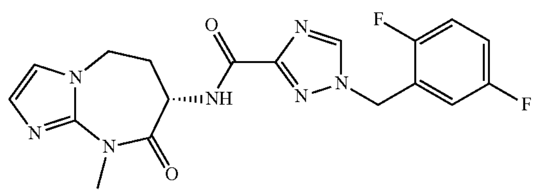 [SMILES: CN1C(=O)[C@@H](NC(=O)c2ncn(Cc3cc(F)ccc3F)n2)CCn2ccnc21]<br>1-[(2,5-difluorophenyl)methyl]-N-[(7S)-9-methyl-8-oxo-6,7-dihydro-5H-imidazo[1,2-a][1,3]diazepin-7-yl]-1,2,4-triazole-3-carboxamide | Single<br>Unknown<br>Stereoisomer | $^1$H NMR (400 MHz, $CD_3OD$) δ 8.61 (s, 1H), 7.19-7.10 (m, 3H), 7.09 (s, 1H), 6.95 (s, 1H), 5.53 (s, 2H), 4.54-4.47 (m, 1H), 4.32-4.25 (m, 1H), 4.09-2.01 (m, 1H), 3.38 (s, 3H), 2.87-2.79 (m, 1H), 2.30-2.24 (m, 1H). | $R_T$ = 1.324 min;<br>m/z = 402.2 |
| Example 507<br>0.026<br>WX Method 100 | 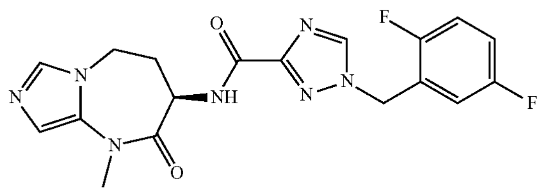 [SMILES: CN1C(=O)[C@H](NC(=O)c2ncn(Cc3cc(F)ccc3F)n2)CCn2cncc21]<br>1-[(2,5-difluorophenyl)methyl]-N-[(3R)-1-methyl-2-oxo-4,5-dihydro-3H-imidazo[1,5-a][1,3]diazepin-3-yl]1,2,4-triazole-3-carboxamide | Single<br>Unknown<br>Stereoisome | $^1$H NMR (400 MHz, DMSO-$d_6$) δ 8.81 (s, 1H), 8.49 (d, J = 8.0 Hz, 1H), 7.58 (s, 1H), 7.39-7.18 (m, 3H), 6.96 (s, 1H), 5.54 (s, 2H), 4.43-4.30 (m, 2H), 3.87-3.78 (m, 1H), 3.23 (s, 3H), 2.44 (s, 1H), 2.28-2.22 (m, 1H) | $R_T$ = 1.716 min;<br>m/z = 402.2 |

TABLE 4-continued

| Example Ki (μM) METHOD | Structure | Stereo | $^1$H NMR | MS (m/z) R.T. |
|---|---|---|---|---|
| Example 508 0.09 WX Method 162 | 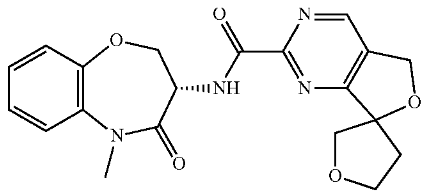 [SMILES: CN1C(=O)[C@@H](NC(=O)c2ncc3c(n2)C2(CCOC2)OC3)COc2ccccc21] N-[(3S)-5-methyl-4-oxo-2,3-dihydro-1,5-benzoxazepin-3-yl]spiro[5H-furo[3,4-d]pyrimidine-7,3'-tetrahydrofuran]-2-carboxamide | Mixture of Diastereomers | $^1$H NMR (400 MHz, $CD_3OD$) δ 8.85 (s, 1H), 7.46-7.44 (m, 1H), 7.36-7.29 (m, 2H), 7.27-7.24 (m, 1H), 5.19 (s, 2H), 5.08-5.03 (m, 1H), 4.68-4.64 (m, 1H), 4.49-4.43 (m, 1H), 4.17-4.02 (m, 4H), 3.43 (s, 3H), 2.49-2.40 (m, 1H), 2.34-2.29 (m, 1H). | $R_T$ = 0.891 min, m/z = 397.1 |
| Example 509 0.44 WX Method 175 | 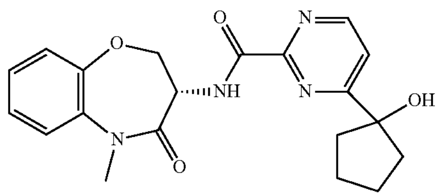 [SMILES: CN1C(=O)[C@@H](NC(=O)c2nccc(C3(O)CCCC3)n2)COc2ccccc21] 4-(1-hydroxycyclopentyl)-N-[(3S)-5-methyl-4-oxo-2,3-. dihydro-1,5-benzoxazepin-3-yl]pyrimidine-2-carboxamide | Single Known Stereoisomer | $^1$H NMR (400 MHz, CD3OD) δ 8.87 (d, J = 5.2 Hz, 1H), 7.90 (d, J = 4.8 Hz, 1H), 7.47-7.42 (m, 1H), 7.36-7.29 (m, 2H), 7.28-7.23 (m, 1H), 5.05-5.00 (m, 1H), 4.71-4.67 (m, 1H), 4.44-4.39 (m, 1H), 3.44 (s, 3H), 2.28-2.24 (m, 2H), 2.03-1.96 (m, 6H). | $R_T$ = 0.664 min, m/z = 383.1 |
| Example 510 0.33 WX Method 160 | 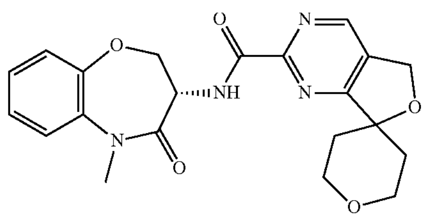 [SMILES: CN1C(=O)[C@@H](NC(=O)c2ncc3c(n2)C2(CCOCC2)OC3)COc2ccccc21] N-[(3S)-5-methyl-4-oxo-2,3-dihydro-1,5-benzoxazepin-3-yl]spiro[5H-furo[3,4-d]pyrimidine-7,4'-tetrahydropyran]-2-carboxamide | Single Known Stereoisomer | $^1$H NMR (400 MHz, $CD_3OD$) δ 8.85 (s, 1H), 7.46-7.44 (m, 7.35-7.31 (m, 2H), 7.26-7.25 (m, 1H), 5.19 (s, 2H) 5.07-5.03 (m, 1H), 4.71-4.68 (m, 1H), 4.66-4.42 (m, 1H), 3.99-3.97 (m, 2H), 3.87-3.82 (m, 2H), 3.44 (s, 3H), 2.24-2.21 (m, 2H), 1.70-1.67 (m, 2H). | $R_T$ = 1.923 min, m/z = 411.1 |
| Example 511 0.083 WX Method 160 | 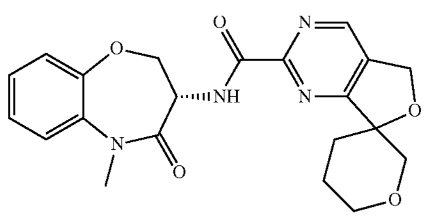 [SMILES: CN1C(=O)[C@@H](NC(=O)c2ncc3c(n2)C2(CCCOC2)OC3)COc2ccccc21] N-[(3S)-5-methyl-4-oxo-2,3-dihydro-1,5-benzoxazepin-3-yl]spiro[5H-furo[3,4-d]pyrimidine-7,3'-tetrahydropyran]-2-carboxamide | Mixture of Diastereomers | $^1$H NMR (400 MHz, $CD_3OD$) δ 8.85 (s, 1H), 7.46-7.44 (m, 1H), 7.36-7.30 (m, 2H), 7.27-7.24 (m, 1H), 5.22 (s, 2H), 5.07-5.03 (m, 1H), 4.70-4.66 (m, 1H), 4.47-4.42 (m, 1H), 3.97-3.94 (m, 1H), 3.82-3.74 (m, 2H), 3.69-3.61 (m, 1H), 3.44 (s, 3H), 2.22-2.15 (m, 1H), 2.10-2.01 (m, 1H), 1.94-1.89 (m, 1H), 1.78-1.72 (m, 1H). | $R_T$ = 0.913 min, m/z = 411.2 |

TABLE 4-continued

| Example Ki (μM) METHOD | Structure | Stereo | $^1$H NMR | MS (m/z) R.T. |
|---|---|---|---|---|
| Example 512<br>0.84<br>WX Method 160 | 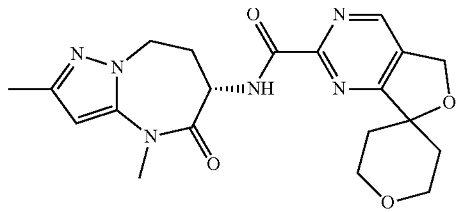 [SMILES: Cc1cc2n(n1)CC[C@H](NC(=O)c1ncc3c(n1)C1(CCOCC1)OC3)C(=O)N2C]<br>N-[(6S)-2,4-dimethyl-5-oxo-7,8-dihydro-6H-pyrazolo[1,5-a][1,3]diazepin-6-yl]spiro[5H-furo[3,4-d]pyrimidine-7,4'-tetrahydropyran]-2-carboxamide | Single Known Stereoisomer | $^1$H NMR (400 MHz, $CD_3OD$) δ 8.85 (s, 1H), 6.14 (s, 1H), 5.20 (s, 2H), 4.88-4.57 (m, 1H), 4.33-4.26 (m, 2H), 3.98-3.88 (m, 2H), 3.85-3.82 (m, 2H), 3.36 (s, 3H), 2.96-2.91 (m, 1H), 2.30-2.21 (m, 6H), 1.69-1.66 (m, 2H). | $R_T$ = 1.052 min, m/z = 413.0 |
| Exampe 513<br>0.029<br>WX Method 011 | 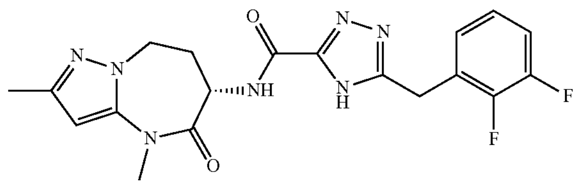 [SMILES: Cc1cc2n(n1)CC[C@H](NC(=O)c1nnc(Cc3cccc(F)c3F)[nH]1)C(=O)N2C]<br>5-[(2,3-difluorophenyl)methyl]-N-(6S)-2,4-dimethyl-5-oxo-7,8-dihydro-6H-pyrazolo[1,5-a][1,3]diazepin-6-yl-4H-1,2,4-triazole-3-carboxamide | Single Known Stereoisomer | $^1$H NMR (400 MHz, $CD_3OD$) δ 7.20-7.11 (m, 3H), 6.10 (s, 1H), 4.54-4.49 (m, 1H), 4.30-4.20 (m, 4H), 3.32 (s, 3H), 2.86-2.79 (m, 1H), 2.27-2.21 (m, 4H). | $R_T$ = 0.637 min, m/z = 416.1 |
| Example 514<br>0.017<br>WX Method 011 | 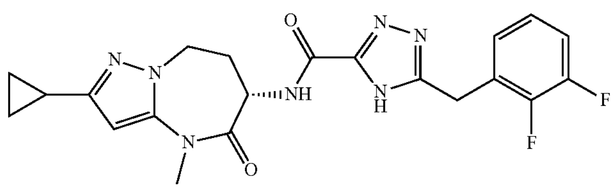 [SMILES: CN1C(=O)[C@@H](NC(=O)c2nnc(Cc3cccc(F)c3F)[nH]2)CCn2nc(C3CC3)cc21]<br>5-[(2,3-difluorophenyl)methyl]-N-(6S)-2-cyclopropyl-4-methyl-5-oxo-7,8-dihydro-6H-pyrazolo[1,5-a][1,3]diazepin-6-yl-4H-1,2,4-triazole-3-carboxamide | Single Known Stereoisomer | $^1$H NMR (400 MHz, $CD_3OD$) δ 7.26-7.07 (m, 3H), 6.01 (s, 1H), 4.53-4.50 (m, 1H), 4.33-4.16 (m, 4H), 3.35-3.32 (m, 3H), 2.85-2.79 (m, 1H), 2.26-2.22 (m, 1H), 1.92-1.98 (m, 1H), 0.98-0.89 (m, 2H), 0.77-0.69 (m, 2H). | $R_T$ = 0.704 min, m/z = 442.1 |

TABLE 4-continued

| Example Ki (μM) METHOD | Structure | Stereo | $^1$H NMR | MS (m/z) R.T. |
|---|---|---|---|---|
| Example 515 0.029 WX Method 121 | 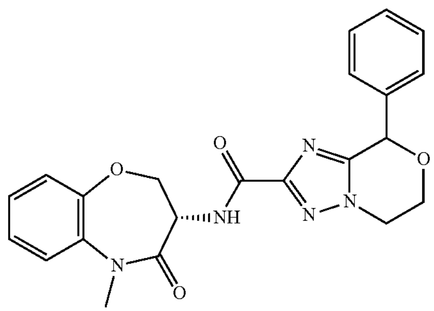 [SMILES: CN1C(=O)[C@@H](NC(=O)c2nc3n(n2)CCOC3c2ccccc2)COc2ccccc21] 8-phenyl-N-[(3S)-5-methyl-4-oxo-2,3-dihydro-1,5-benzoxazepin-3-yl]-6,8-dihydro-5H-[1,2,4]triazole[5,1-c][1,4]oxazine-2-carboxamide | Mixture of Diastereomers | $^1$H NMR (400 MHz, $CD_3OD$) δ 8.80 (s, 1H), 7.46-7.44 (m, 1H), 7.34-7.32 (m, 2H), 7.27-7.24 (m, 1H), 5.12 (s, 2H), 5.07-5.02 (m, 1H), 4.69-4.68 (m, 1H), 4.46-4.43 (m, 1H), 3.44 (s, 3H), 2.08-2.04 (m, 4H), 1.95-1.93 (m, 4H). | $R_T$ = 1.009 min, m/z = 420.2 |
| Example 516 0.018 WX Method 121 | 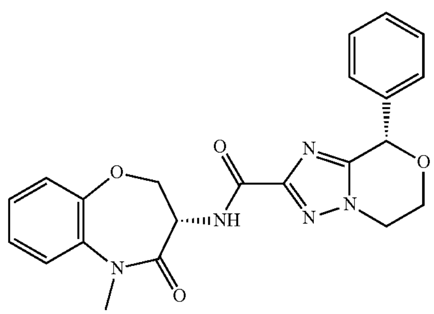 [SMILES: CN1C(=O)[C@@H](NC(=O)c2nc3n(n2)CCO[C@H]3c2ccccc2)COc2ccccc21] (8S)-8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide | Single Unknown Stereoisomer | $^1$H NMR (400 MHz, $CD_3OD$) δ 7.41-7.38 (m, 6H), 7.30-7.29 (m, 2H), 7.22-7.21 (m, 1H), 5.94 (s, 1H), 5.01-4.96 (m, 1H), 4.58-4.53 (m, 1H), 4.47-4.35 (m, 4H), 4.30-4.25 (m, 1H), 3.38 (s, 3H). | $R_T$ = 0.809 min, m/z = 420.0 |

TABLE 4-continued

| Example Ki (μM) METHOD | Structure | Stereo | $^1$H NMR | MS (m/z) R.T. |
| --- | --- | --- | --- | --- |
| Example 517 0.66 WX Method 121 | 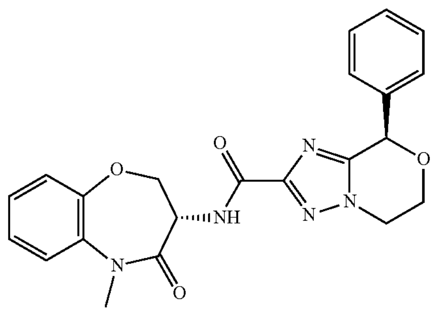 [SMILES: CN1C(=O)[C@@H](NC(=O)c2nc3n(n2)CCO[C@@H]3c2ccccc2)COc2ccccc21] (8R)-8-phenyl-N-[(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide | Single Unknown Stereoisomer | $^1$H NMR (400 MHz, $CD_3OD$) δ 7.41-7.38 (m, 6H), 7.30-7.29 (m, 2H), 7.22-7.21 (m, 1 H), 5.94 (s, 1H), 5.01-4.96 (m, 1H), 4.57-4.47 (m, 2H), 4.40-4.35 (m, 3H), 4.25-4.20 (m, 1H), 3.38 (s, 3H). | $R_T$ = 0.809 min, m/z = 420.0 |
| Example 518 0.0075 WX Method 043 | 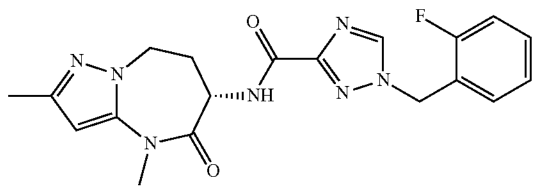 [SMILES: Cc1cc2n(n1)CC[C@H](NC(=O)c1ncn(Cc3ccccc3F)n1)C(=O)N2C] 1[(2-fluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.57 (s, 1H), 7.40-7.35 (m, 2H), 7.21-7.12 (m, 2H), 6.10 (s, 1H), 5.54 (s, 2H), 4.54-4.49 (m, 1H), 4.29-4.15 (m, 2H), 3.31 (s, 3H), 2.87-2.79 (m, 1H), 2.27-2.20 (m, 4H). | $R_T$ = 1.426 min, m/z = 398.2 |
| Example 519 0.011 WX Method 049 | 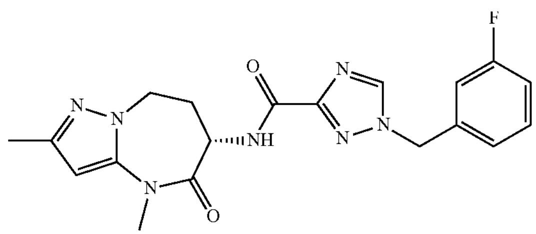 [SMILES: Cc1cc2n(n1)CC[C@H](NC(=O)c1ncn(Cc3cccc(F)c3)n1)C(=O)N2C] 1[(3-fluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.60 (s, 1H), 7.42-7.36 (m, 1H), 7.17-7.06 (m, 3H), 6.11 (s, 1H), 5.49 (s, 2H), 4.56-4.51 (m, 1H), 4.31-4.18 (m, 2H), 3.32 (d, J = 5.2 Hz, 3H), 2.87-2.81 (m, 1H), 2.28-2.23 (m, 4H). | $R_T$ = 0.904 min, m/z = 398.2 |

TABLE 4-continued

| Example<br>Ki (μM)<br>METHOD | Structure | Stereo | $^1$H NMR | MS (m/z) R.T. |
|---|---|---|---|---|
| Example 520<br>0.006<br>WX Method 073 | 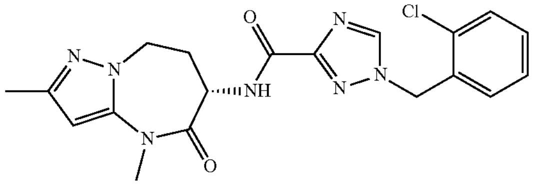 [SMILES: Cc1cc2n(n1)CC[C@H](NC(=O)c1ncn(Cc3ccccc3Cl)n1)C(=O)N2C]<br>1[(2-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.57 (s, 1H), 7.46-7.36 (m, 1H), 7.35-7.32 (m, 3H) 6.10 (s, 1H), 5.60 (s, 2H), 4.54-4.49 (m, 1H), 4.33-4.19 (m, 2H), 3.30 (s, 3H), 2.85-2.79 (m, 1H), 2.27-2.21 (m, 4H). | $R_T$ = 0.763 min, m/z = 414.1 |
| Example 521<br>0.0069<br>WX Method 077 | 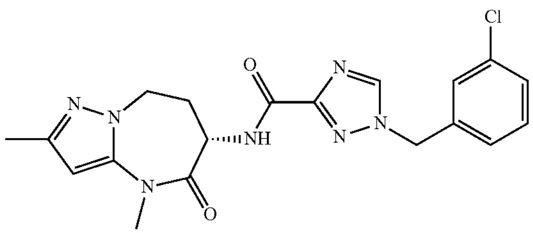<br>1-[(3-chlorophenyl)methyl]- N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.60 (s, 1H), 7.37-7.25 (m, 4H), 6.10 (s, 1H), 5.46 (s, 2H), 4.54-4.49 (m, 1H), 4.29-4.27 (m, 1H), 4.24-4.19 (m, 1H), 3.31-3.29 (m, 3H), 2.85-2.79 (m, 1H), 2.28-2.21 (s, 4H). | $R_T$ = 0.755 min, m/z = 414.1 |
| Example 522<br>0.0035<br>GNT_E425_464<br>WX Method 073 | 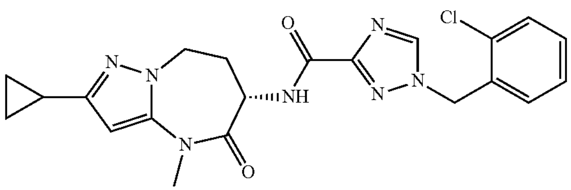 [SMILES: CN1C(=O)[C@@H](NC(=O)c2ncn(Cc3ccccc3Cl)n2)CCn2nc(C3CC3)cc21]<br>1-[(2-chlorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.56 (s, 1H), 7.45-7.30 (m, 4H), 5.98 (s, 1H), 5.59 (s, 2H), 4.52-4.47 (m, 1H), 4.29-4.17 (m, 2H), 3.30 (s, 3H), 2.83-2.78 (m, 1H), 2.24-2.21 (m, 1H), 1.90-1.87 (m, 1H), 0.93-0.90 (m, 2H), 0.73-0.70 (m, 2H). | $R_T$ = 0.794 min, m/z = 440.1 |

TABLE 4-continued

| Example<br>Ki (μM)<br>METHOD | Structure | Stereo | $^1$H NMR | MS (m/z) R.T. |
|---|---|---|---|---|
| Example 523<br>0.013<br>WX Method 066 | 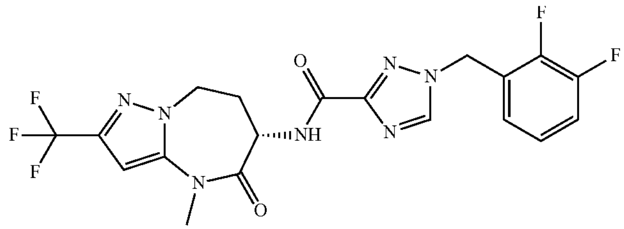 [SMILES: CN1C(=O)[C@@H](NC(=O)c2ncn(Cc3cccc(F)c3F)n2)CCn2nc(C(F)(F)F)cc21]<br>1-[(2,3-difluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.58 (s, 1H), 7.48-7.42 (m, 1H), 7.05-6.97 (m, 2H), 6.66 (s, 1H), 5.52 (s, 2H), 4.53-4.44 (m, 2H), 4.39-4.33 (m, 1H), 3.36 (s, 3H), 2.89-2.84 (m, 1H), 2.35-2.29 (m, 1H). | $R_T$ = 0.812 min, m/z = 470.1 |
| Example 524<br>0.072<br>WX Method 011 | 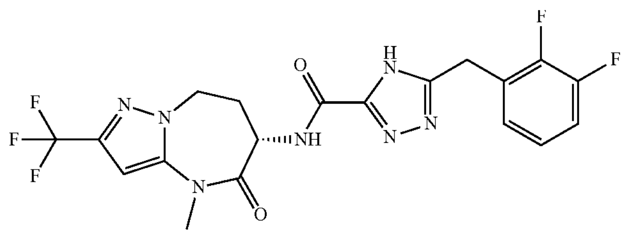 [SMILES: CN1C(=O)[C@@H](NC(=O)c2nnc(Cc3cccc(F)c3F)[nH]2)CCn2nc(C(F)(F)F)cc21]<br>5-[(2,3-difluorophenyl)methyl]-N-(6S)-4-methyl-5-oxo-2-(trifluoromethyl)-7,8-dihydro-6H-pyrazolo[1,5-a][1,3]diazepin-6-yl-4H-1,2,4-triazole-3-carboxamide | Single Known Stereoisomer | $^1$H NMR (400 MHz, $CD_3OD$) δ 8.69 (s, 1H), 7.37-7.31 (m, 1H), 7.19-7.13 (m, 2H), 6.94 (s, 1H), 4.50-4.44 (m, 1H), 4.36-4.32 (m, 2H), 4.19 (s, 2H), 3.27 (s, 3H), 2.64-2.60 (m, 1H), 2.52-2.48 (m, 1H). | $R_T$ = 0.808 min, m/z = 470.1 |
| Example 525<br>0.046<br>WX Method 067 | 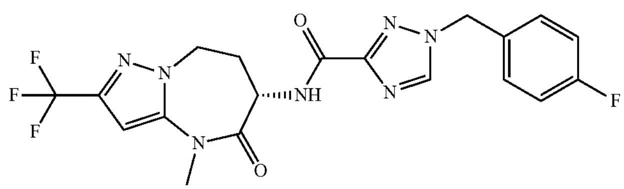 [SMILES: CN1C(=O)[C@@H](NC(=O)c2ncn(Cc3ccc(F)cc3)n2)CCn2nc(C(F)(F)F)cc21]<br>1-[(4-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.82 (s, 1H), 8.66 (d, J = 8.0 Hz, 1H), 7.40-7.36 (m, 2H), 7.21 (t, J = 8.8 Hz, 2H), 6.94 (s, 1H), 5.47 (s, 2H), 4.48-4.44 (m, 1H), 4.37-4.30 (m, 2H), 3.27 (s, 3H), 2.64-2.60 (m, 1H), 2.52-2.48 (m, 1H). | $R_T$ = 0.810 min, m/z = 452.1 |

TABLE 4-continued

| Example<br>Ki (μM)<br>METHOD | Structure | Stereo | $^1$H NMR | MS (m/z) R.T. |
|---|---|---|---|---|
| Example 526<br>0.02<br>WX Method 043 | 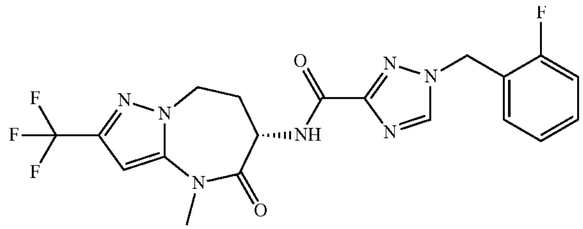 [SMILES: CN1C(=O)[C@@H](NC(=O)c2ncn(Cc3ccccc3F)n2)CCn2nc(C(F)(F)F)cc21]<br>1-[(2-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, DMSO-$d_6$) δ 8.82 (s, 1H), 8.66 (d, J = 8.0 Hz, 1H), 7.43-7.33 (m, 2H), 7.26 7.20 (m, 2H), 6.94 (s, 1H), 5.55 (s, 2H), 4.49-4.44 (m, 1H), 4.36-4.30 (m, 2H), 3.26 (s, 3H), 2.64-2.60 (m, 1H), 2.52 -2.48 (m, 1H). | $R_T$ = 0.803 min, m/z = 452.1 |
| Example 527<br>0.023<br>WX Method 049 | 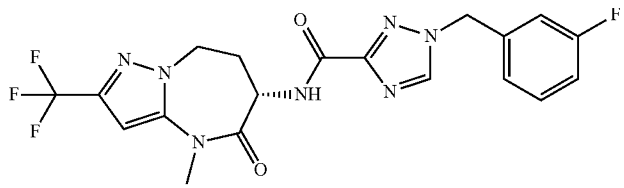 [SMILES: CN1C(=O)[C@@H](NC(=O)c2ncn(Cc3cccc(F)c3)n2)CCn2nc(C(F)(F)F)cc21]<br>1-[(3-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, DMSO-$d_6$) δ 8.84 (s, 1H), 8.68 (d, J = 8.0 Hz, 1H), 7.46-7.40 (m, 1H), 7.19-7.12 (m, 3H), 6.94 (s, 1H), 5.51 (s, 2H), 4.50-4.44 (m, 1H), 4.37-4.31 (m, 2H), 3.27 (s, 3H), 2.64-2.60 (m, 1H), 2.52-2.48 (m, 1H). | $R_T$ = 0.807 min, m/z = 452.0 |
| Example 528<br>0.0048<br>WX Method 076 | 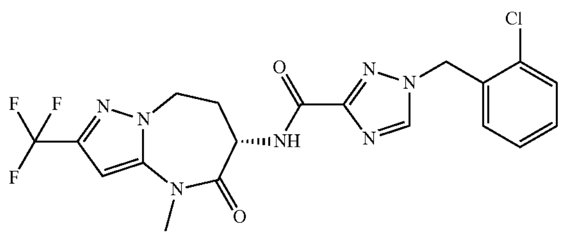 [SMILES: CN1C(=O)[C@@H](NC(=O)c2ncn(Cc3ccccc3Cl)n2)CCn2nc(C(F)(F)F)cc21]<br>1-[(2-chlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.58 (s, 1H), 7.47-7.42 (m, 1H), 7.42-7.28 (m, 3H), 6.68 (s, 1H), 5.61 (s, 2H), 4.56 4.46 (m, 2H), 4.41-4.33 (m, 1H), 3.37 (s, 3H), 2.93-2.86 (m, 1H), 2.36-2.29 (m, 1H) | $R_T$ = 1.838 min, m/z = 468.1 |

TABLE 4-continued

| Example Ki (µM) METHOD | Structure | Stereo | $^1$H NMR | MS (m/z) R.T. |
|---|---|---|---|---|
| Example 529<br>0.028<br>WX Method 065 | 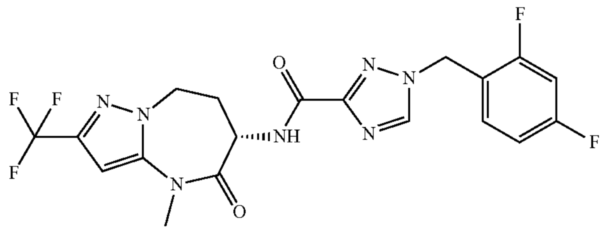 [SMILES: CN1C(=O)[C@@H](NC(=O)c2ncn(Cc3ccc(F)cc3F)n2)CCn2nc(C(F)(F)F)cc21]<br>1-[(2,4-difluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.58 (s, 1H), 7.48-7.42 (m, 1H), 7.05-6.97 (m, 2H), 6.66 (s, 1H), 5.52 (s, 2H), 4.53-4.44 (m, 2H), 4.39-4.33 (m, 1H), 3.36 (s, 3H), 2.89-2.84 (m, 1H), 2.35-2.29 (m, 1H). | $R_T$ = 1.805 min; m/z = 470.1 |
| Example 530<br>0.011<br>WX Method 043 | 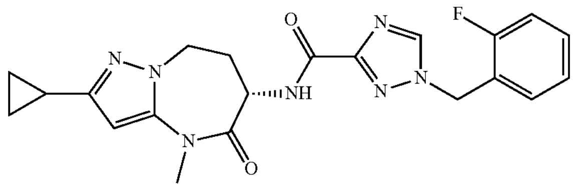 [SMILES: CN1C(=O)[C@@H](NC(=O)c2ncn(Cc3ccccc3F)n2)CCn2nc(C3CC3)cc21]<br>1-[(2-fluorophenyl)methyl]-N-[rac-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.58 (s, 1H), 7.41-7.36 (m, 2H), 7.21-7.15 (m, 2H), 6.00 (s, 1H), 5.55 (s, 2H), 4.53-4.48 (m, 1H), 4.32-4.21 (m, 2H), 3.31 (s, 3H), 2.86-2.79 (m, 1H), 2.25-2.23 (m, 1H), 1.91-1.87 (m, 1H), 0.95-0.92 (m, 2H), 0.75-0.72 (m, 2H). | $R_T$ = 0.958 min, m/z = 424.2 |
| Example 531<br>0.014<br>WX Method 049 | 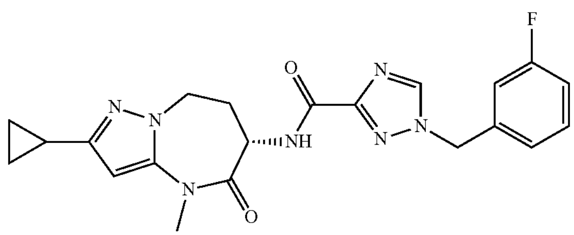 [SMILES: CN1C(=O)[C@@H](NC(=O)c2ncn(Cc3cccc(F)c3)n2)CCn2nc(C3CC3)cc21]<br>1-[(3-fluorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.61 (s, 1H), 7.40-7.36 (m, 1H), 7.17-7.08 (m, 3H), 6.00 (s, 1H), 5.49 (s, 2H), 4.55-4.50 (m, 1H), 4.31-4.19 (m, 2H), 3.31 (s, 3H), 2.87-2.80 (m, 1H), 2.28-2.24 (m, 1H), 1.91-1.88 (m, 1H), 0.95-0.92 (m, 2H), 0.75-0.73 (m, 2H). | $R_T$ = 0.958 min, m/z = 424.2 |

TABLE 4-continued

| Example Ki (μM) METHOD | Structure | Stereo | $^1$H NMR | MS (m/z) R.T. |
|---|---|---|---|---|
| Example 532<br>0.024<br>WX Method 070 | 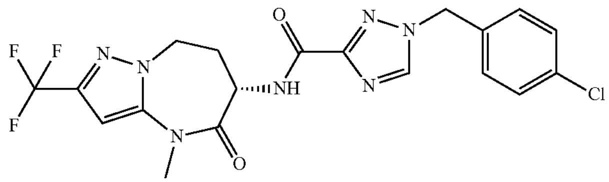 [SMILES: CN1C(=O)[C@@H](NC(=O)c2ncn(Cc3ccc(Cl)cc3)n2)CCn2nc(C(F)(F)F)cc21]<br>1-[(4-chlorophenyl)methyl]- N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, DMSO-$d_6$) δ 8.82 (s, 1H), 8.70-8.68 (m, 1H), 7.41-7.39 (m, 2H), 7.20-7.22 (m, 2H), 6.94 (s, 1H), 5.49 (s, 2H), 4.95-4.44 (m, 1H), 4.38-4.30 (m, 2H), 3.26 (s, 3H), 2.66-2.63 (m, 1H), 2.32-2.29 (m, 1H). | $R_T$ = 1.889 min, m/z = 468.1 |
| Example 533<br>0.045<br>WX Method 079 | 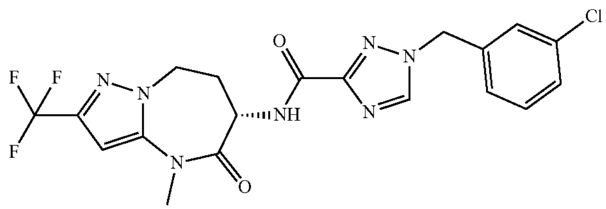 [SMILES: CN1C(=O)[C@@H](NC(=O)c2ncn(Cc3cccc(Cl)c3)n2)CCn2nc(C(F)(F)F)cc21]<br>1-[(3-chlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, DMSO-$d_6$) δ 8.84 (s, 1H), 8.69-8.67 (m, 1H), 7.46-7.32 (m, 3H), 7.28-7.25 (m, 1H), 6.94 (s, 1H), 5.50 (s, 2H), 4.49-4.44 (m, 1H), 4.37-4.32 (m, 2H), 3.26 (s, 3H), 2.65 (s, 1H), 2.46-2.42 (m, 1H). | $R_T$ = 1.883 min, m/z = 468.1 |
| Example 534<br>0.0076<br>WX Method 069 | 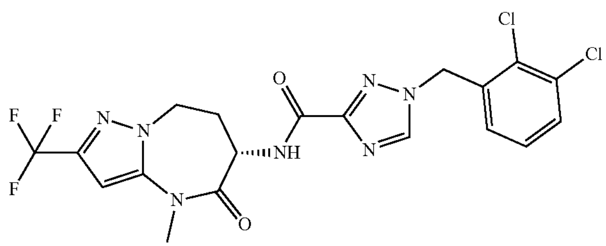 [SMILES: CN1C(=O)[C@@H](NC(=O)c2ncn(Cc3cccc(Cl)c3Cl)n2)CCn2nc(C(F)(F)F)cc21]<br>1-[(2,3-dichlorophenyl)met hyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide | Single Known Stereoisomer | $^1$H NMR (400 MHz, DMSO-$d_6$) δ 8.84 (s, 1H), 8.68-8.66 (m, 1H), 7.67-7.64 (m, 1H), 7.41-7.37 (m, 1H), 7.21-7.19 (m, 1H), 6.94 (s, 1H), 5.65 (s, 2H), 4.47-4.38 (m, 1H), 4.38-4.29 (m, 2H), 3.27 (s, 3H), 2.67-2.65 (m, 1H), 2.33-2.31 (m, 1H). | $R_T$ = 1.954 min, m/z = 502.0 |

TABLE 4-continued

| Example Ki (μM) METHOD | Structure | Stereo | $^1$H NMR | MS (m/z) R.T. |
|---|---|---|---|---|
| Example 535<br>0.13<br>WX Method 091 | 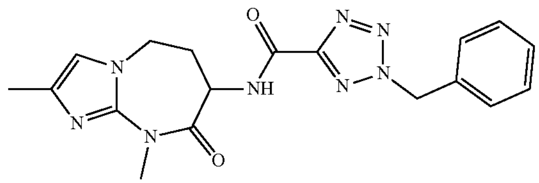 [SMILES: Cc1cn2c(n1)N(C)C(=O)C(NC(=O)c1nnn(Cc3ccccc3)n1)CC2]<br>1-benzyl-N-(2,9-dimethyl-8-oxo-6,7-dihydro-5H-imidazo[1,2-a][1,3]diazepin-7-yl)-1,2,4-triazole-3-carboxamide | Mixture of Enantiomers | $^1$H NMR (400 MHz, $CD_3OD$) δ 8.56 (s, 1H), 7.39-7.32 (m, 5H), 6.78 (s, 1H), 5.47 (s, 2H), 4.55-4.50 (m, 1H), 4.21-4.15 (m, 1H), 4.03-3.98 (m, 1H), 3.36 (s, 3H), 2.85-2.79 (m, 1H), 2.29-2.23 (m, 1H), 2.19 (s, 3H). | $R_T$ = 1.779 min, m/z = 380.2 |
| Example 536<br>0.0035<br>WX Method 149 | 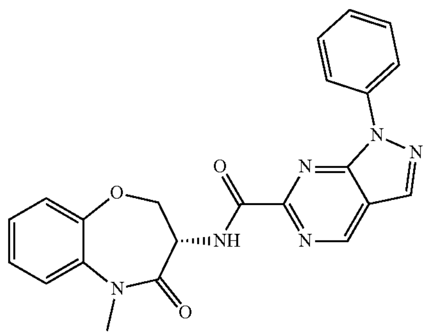 [SMILES: CN1C(=O)[C@@H](NC(=O)c2ncc3cnn(-c4ccccc4)c3n2)COc2ccccc21]<br>1-phenyl-N-[(3S)-5-methyl-4-oxo-2,3-dihydro-1,5-benzoxazepin-3-yl] pyrazolo[3,4-d]pyrimidine-6-carboxamide | Single Known Stereoisomer | $^1$H NMR (400 MHz, DMSO-$d_6$) δ 9.61 (s, 1H), 9.17 (d, J = 8.0 Hz, 1H), 8.79 (s, 1H), 8.23 (d, J = 8.0 Hz, 2H), 7.65-7.61 (m, 2H), 7.52 (d, J = 7.2 Hz, 1H), 7.45-7.40 (m, 1H), 7.35-7.28 (m, 3H), 4.95-4.90 (m, 1H), 4.62-4.54 (m, 2H). | $R_T$ = 0.846 min; m/z = 415.1 |
| Example 537<br>2.1<br>WX Method 174 | 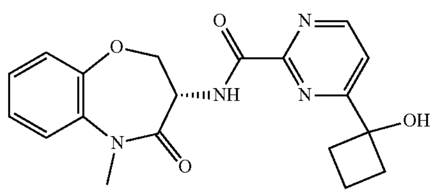 [SMILES: CN1C(=O)[C@@H](NC(=O)c2nccc(C3(O)CCC3)n2)COc2ccccc21]<br>4-(1-hydroxycyclobutyl)-N-(3S)-5-methyl-4-oxo-2,3-dihydro-1,5-benzoxazepin-3-yl]pyrimidine-2-carboxamide | Single Known Stereoisomer | $^1$H NMR (400 MHz, $CD_3OD$) δ 8.89 (d, J = 5.2 Hz, 1H), 7.83 (d, J = 5.6 Hz, 1H), 7.46-7.44 (m, 1H), 7.34-7.27 (m, 2H), 7.26-7.25 (m, 1H), 5.06-5.04 (m, 1H), 4.73-4.72 (m, 1H), 4.44-4.42(m, 1H), 3.45 (s, 3H), 2.72-2.68 (m, 2H), 2.43-2.35 (m, 2H), 2.12-2.07 (m, 2H). | $R_T$ = 1.938 min; m/z = 369.1 |

TABLE 4-continued

| Example Ki (μM) METHOD | Structure | Stereo | $^1$H NMR | MS (m/z) R.T. |
|---|---|---|---|---|
| Example 538<br>0.019<br>WX Method 077 | 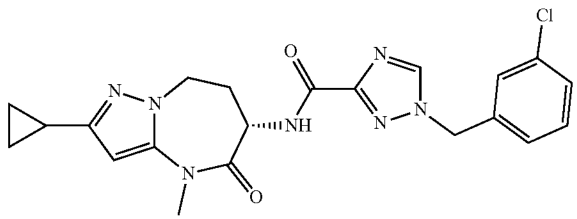 [SMILES: CN1C(=O)[C@@H](NC(=O)c2ncn(Cc3cccc(Cl)c3)n2)CCn2nc(C3CC3)cc21]<br>1-[(3-chlorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.68 (s, 1H), 7.37-7.25 (m, 4H), 6.18 (s, 1H), 5.47 (s, 2H), 4.61-4.58 (m, 1H), 4.40-4.26 (m, 2H), 3.28 (s, 3H), 2.87-2.81 (m, 1H), 2.32-2.30 (m, 1H), 1.97-1.93 (m, 1H), 1.05-1.03 (m, 2H), 0.84-0.81 (m, 2H). | $R_T$ = 0.802 min, m/z = 440.1 |
| Example 539<br>0.15<br>WX Method 142 | 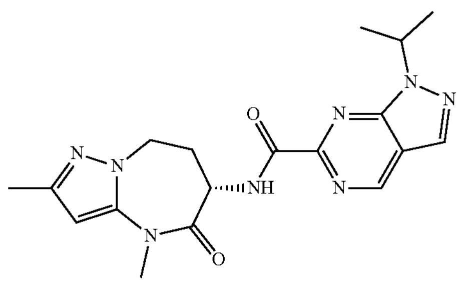 [SMILES: Cc1cc2n(n1)CC[C@H](NC(=O)c1ncc3cnn(C(C)C)c3n1)C(=O)N2C]<br>1-isopropyl-N-[(6S)-2,4-dimethyl-5-oxo-7,8-dihydro-6 H-pyrazolo[1,5-a][1,3]diazepin-6-yl]pyrazolo[3,4-d]pyrimidine-6-carboxamide | Single Known Stereoisomer | $^1$H NMR (400 MHz, $CD_3OD$) δ 9.35 (s, 1H) 8.38 (s, 1H), 6.14 (s, 1H), 5.47-5.42 (m, 1H), 4.65-4.60 (m, 1H), 4.37-4.26 (m, 2H), 3.37 (s, 3H), 3.00-2.94 (m, 1H), 2.35-2.27 (m, 4H), 1.59 (d, J = 6.8 Hz, 6H). | $R_T$ = 0.733 min, m/z = 383.1 |
| Example 540<br>0.057<br>WX Method 148 | 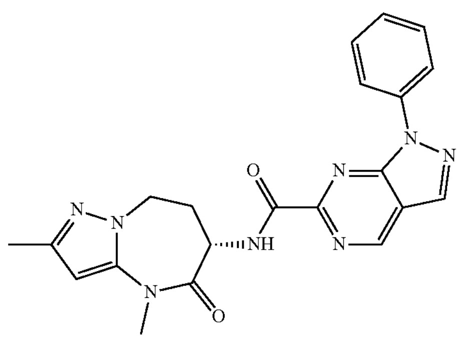 [SMILES: Cc1cc2n(n1)CC[C@H](NC(=O)c1ncc3cnn(-c4ccccc4)c3n1)C(=O)N2C]<br>1-phenyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide | Single Known Stereoisomer | $^1$H NMR (400 MHz, DMSO-$d_6$) δ 9.58 (s, 1H), 9.20 (d, J = 8.0 Hz, 1H), 8.77 (s, 1H), 8.23 (d, J = 7.6 Hz, 2H), 7.64-7.59 (m, 2H), 7.46-7.41 (m, 1H), 6.15 (s, 1H), 4.43-4.39 (m, 1H), 4.32-4.27 (m, 1H), 4.18-4.15 (m, 1H), 3.26 (s, 3H), 2.74-2.69 (m, 1H), 2.37-2.34 (m, 1H), 2.18 (s, 3H). | $R_T$ = 0.792 min; m/z = 417.1 |

TABLE 4-continued

| Example<br>Ki (μM)<br>METHOD | Structure | Stereo | $^{1}$H NMR | MS (m/z) R.T. |
|---|---|---|---|---|
| Example 541<br>0.005<br>WX Method 071 | 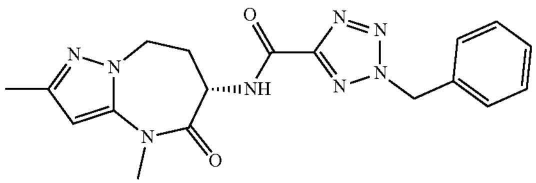 [SMILES: Cc1cc2n(n1)CC[C@H](NC(=O)c1nnn(Cc3ccccc3)n1)C(=O)N2C]<br>2-benzyl-N-(6S)-2,4-dimethyl-5-oxo-7,8-dihydro-6H-pyrazolo[1,5-a][1,3]diazepin-6-yltetrazole-5-carboxamide | Single Known Stereoisomer | $^{1}$H NMR (400 MHz, $CD_3OD$) δ 7.43-7.37 (m, 5H), 6.12 (s, 1H) 5.94 (s, 2H), 4.58-4.53 (m, 1H), 4.35-4.29 (m, 1H), 4.26-4.22 (m, 1H), 3.32 (s, 3H), 2.84-2.78 (m, 1H), 2.34-2.25 (m, 4H). | $R_T$ = 0.938 min, m/z = 381.2 |
| Example 542<br>0.0064<br>WX Method 071 | 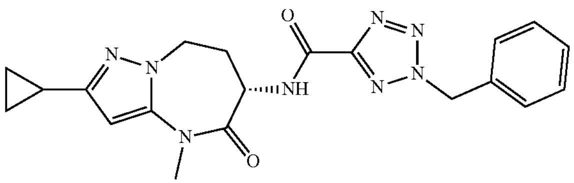 [SMILES: CN1C(=O)[C@@H](NC(=O)c2nnn(Cc3ccccc3)n2)CCn2nc(C3CC3)cc21]<br>2-benzyl-N-(6S)-2,4-dimetyl-5-oxo-7,8-dihydro-6H-pyrazolo[1,5-a][1,3]diazepin-6-yltetrazole-5-carboxamide | Single Known Stereoisomer | $^{1}$H NMR (400 MHz, $CD_3OD$) δ 7.44 7.34 5H), 6.00 (s, 1H), 5.93 (s, 2H), 4.57-4.52 (m, 1H), 4.34-4.26 (m, 1H), 4.24-4.14 (m, 1H), 3.30 (s, 3H), 2.86-2.81 (m, 1H), 2.34-2.30 (m, 1H), 1.94-1.85 (m, 1H), 0.96-0.90 (m, 2H), 0.77-0.68 (m, 2H). | $R_T$ = 1.002 min, m/z = 407.2 |
| Example 543<br>0.068<br>WX Method 147 | 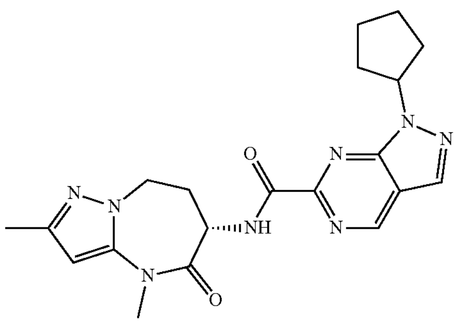 [SMILES: Cc1cc2n(n1)CC[C@H](NC(=O)c1ncc3cnn(C4CCCC4)c3n1)C(=O)N2C]<br>1-cyclopentyl-N-[(6S)-2,4-dimethyl-5-oxo-7,8-dihydro-6H-pyrazolo[1,5-a][1,3]diazepin-6-yl]pyrazolo[3,4-d] pyrimidine-6-carboxamide | Single Known Stereoisomer | $^{1}$H NMR (400 MHz, DMSO-$d_6$) δ 9.45 (s, 1H), 9.15 (d, J = 8.0 Hz, 1H), 8.51 (s, 1H), 6.16 (s, 1H), 5.49-5.41 (m, 1H), 4.47-4.10 (m, 3H), 3.25 (s, 3H), 2.77-2.66 (m, 1H), 2.38-2.29 (m, 1H), 2.23-2.11 (m, 5H), 2.06-1.86 (m, 4H), 1.80-1.65 (m, 2H). | $R_T$ = 0.787 min; m/z = 409.1 |

TABLE 4-continued

| Example Ki (μM) METHOD | Structure | Stereo | $^1$H NMR | MS (m/z) R.T. |
|---|---|---|---|---|
| Example 544<br>1.2<br>WX Method 161 | 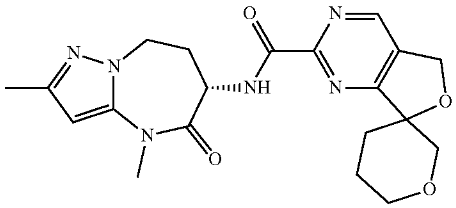 [SMILES: Cc1cc2n(n1)CC[C@H](NC(=O)c1ncc3c(n1)C1(CCCOC1)OC3)C(=O)N2C]<br>N-[(6S)-2,4-dimethyl-5-oxo-7,8-dihydro-6H-pyrazolo[1,5-a][1,3]diazepin-6-yl]spiro[5H-furo[3,4-d]pyrimidine-7,3'-tetrahydropyran]-2-carboxamide | Mixture of Diastereomers | $^1$H NMR (400 MHz, $CD_3OD$) δ 8.52 (s, 1H), 6.14 (s, 1H), 5.22 (s, 2H), 4.62-4.56 (m, 1H), 4.34 4.24 2H), 3.95-3.90 (m, 1H), 3.79-3.65 (m, (3H), 3.35 (s, 3H), 2.96-2.90 (m, 1H), 2.31-2.20 (m, 5H), 2.07-2.03 (m,1H), 1.94-1.90 (m, 1H), 1.77-1.73 (m, 1H). | $R_T$ = 0.580 min; m/z = 413.1 |
| Example 545<br>2.1<br>WX Method 158 | 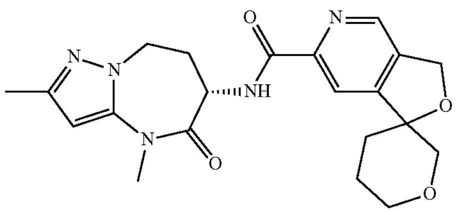 [SMILES: Cc1cc2n(n1)CC[C@H](NC(=O)c1cc3c(cn1)COC31CCCOC1)C(=O)N2C]<br>N-[(6S)-2,4-dimethyl-5-oxo-7,8-dihydro-6H-pyrazolo[1,5-a][1,3]diazepin-6-yl]spiro[3H-furo[3,4-c]pyridine-1,3'-tetrahydropyran]-6-carboxamide | Mixture of Diastereomers | $^1$H NMR (400 MHz, $CD_3OD$) δ 8.59 (s, 1H), 8.03 (s, 1H), 6.12 (s, 1H), 5.24-5.15 (m, 2H), 4.59-4.54 (m, 1H), 4.36-4.19 (m,2H), 3.87-3.61 (m, 4H), 3.34 (s,3H), 2.97-2.84 (m, 4H) 19 (m 28-2 2 1H), 2.07-1.89 (m,3H), 1.78-1.70 (m,1H). | $R_T$ = 0.887 min; m/z = 412.2 |
| Example 546<br>0.22<br>WX Method 095 | 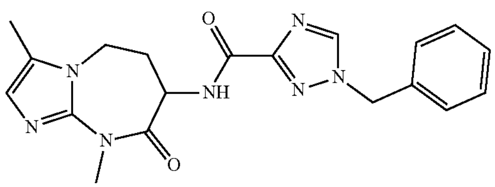 [SMILES: Cc1cnc2n1CCC(NC(=O)c1ncn(Cc3ccccc3)n1)C(=O)N2C]<br>1-benzyl-N-(3,9-dimethyl-8-oxo-6,7-dihydro-5H-imidazo[1,2-a][1,3]diazepin-7-yl)-1,2,4-triazole-3-carboxamide | Mixture of Enantiomers | $^1$H NMR (400 MHz, $CD_3OD$) δ 8.56 (s, 1H), 7.39-7.35 (m, 5H), 6.71 (s, 1H), 5.47 (s, 2H), 4.51-4.46 (m, 1H), 4.22-4.16 (m, 1H), 3.95-3.87 (m, 1H), 3.37 (s, 3H), 2.84-2.74 (m, 1H), 2.29-2.19 (m, 4H). | $R_T$ = 1.792 min, m/z = 380.1 |

TABLE 4-continued

| Example Ki (μM) METHOD | Structure | Stereo | $^1$H NMR | MS (m/z) R.T. |
|---|---|---|---|---|
| Example 547<br>0.0085<br>WX Method 084 | 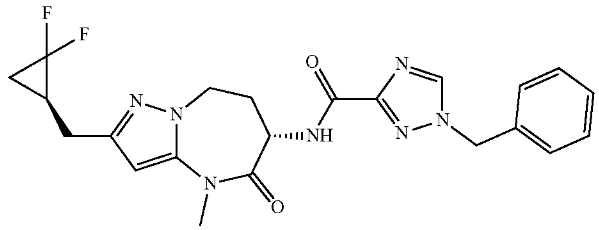 [SMILES: CN1C(=O)[C@@H](NC(=O)c2ncn(Cc3ccccc3)n2)CCn2nc(C[C@H]3CC3(F)F)cc21]<br>1-benzyl-N-(6S)-4-methyl-5-oxo-2-[(1S)-2,2-difluorocyclopropylmethyl]-7,8-dihydro-6H-pyrazolo [1,5-a][1,3]diazepin-6-yl-1,2,4-triazole-3-carboxamide | Single Unknown Stereoisomer | $^1$H NMR (400 MHz, $CD_3OD$) δ 8.58 (s, 1H), 7.48-7.20 (m, 5H), 6.23 (s, 1H), 5.43 (s, 2H), 4.57-4.53 (m, 1H), 4.38-4.34 (m, 1H), 4.26-4.22 (m, 1H), 3.35 (s, 3H), 2.95-2.65 (m, 3H), 2.40-2.20 (m, 1H), 2.05-1.80 (m, 1H), 1.65-1.45 (m, 1H), 1.25-1.10 (m, 1H). | $R_T$ = 0.684 min, m/z = 456.0. |
| Example 548<br>0.0097<br>WX Method 084 | 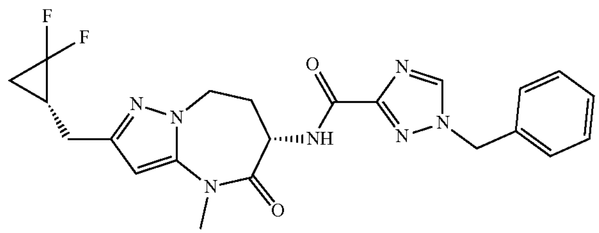 [SMILES: CN1C(=O)[C@@H](NC(=O)c2ncn(Cc3ccccc3)n2)CCn2nc(C[C@@H]3CC3(F)F)cc21]<br>1-benzyl-N-(6S)-4-methyl-5-oxo-2-[(1R)-2,2-difluorocyclopropylmethyl]-7,8-dihydro-6H-pyrazolo[1,5-a][1,3] diazepin-6-yl-1,2,4-triazole-3-carboxamide | Single Unknown Stereoisomer | $^1$H NMR (400 MHz, CD3OD) δ 8.59 (s, 1H), 7.48-7.20 (m, 5H), 6.24 (s, 1H), 5.49 (s, 2H), 4.57-4.53 (m, 1H), 4.37-4.35 (m, 1H), 4.28-4.23 (m, 1H), 3.35 (s, 3H), 2.95-2.65 (m, 3H), 2.40-2.20 (m, 1H), 2.05-1.80 (m, 1H), 1.65-1.45 (m, 1H), 1.25-1.10 (m, 1H). | $R_T$ = 0.694 min, m/z = 456.1. |
| Example 549<br>3.7<br>WX Method 173 | 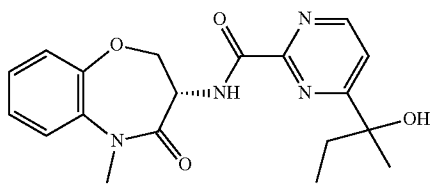 [SMILES: CCC(C)(O)c1ccnc(C(=O)N[C@H]2COc3ccccc3N(C)C2=O)n1]<br>4-(1-hydroxy-1-methyl-propyl)-N-[(3S)-5-methyl-4-oxo-2,3-dihydro-1,5-benzoxaz epin-3-yl]pyrimidine-2-caroxamide | Mixture of Diastereomers | $^1$H NMR (400 MHz, $CD_3OD$) δ .89 (d, J = 5.6 Hz, 1H), 7.84 (d, J = 5.2 Hz, 1H), 7.49-7.41 (m, 1H), 7.34-7.24 (m, 3H), 5.06-5.02 (m, 1H), 4.70-4.66 (m, 1H), 4.47-4.42 (m, 1H), 3.44 (s, 3H), 2.01-1.87 (m, 2H), 1.56 (s, 3H), 0.81-0.77 (m, 3H). | $R_T$ = 1.971 min; m/z = 371.2 |

TABLE 4-continued

| Example Ki (μM) METHOD | Structure | Stereo | $^1$H NMR | MS (m/z) R.T. |
|---|---|---|---|---|
| Example 550<br>0.21<br>WX Method 011 | 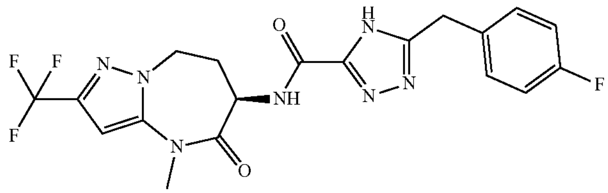 [SMILES: CN1C(=O)[C@H](NC(=O)c2nnc(Cc3ccc(F)cc3)[nH]2)CCn2nc(C(F)(F)F)cc21]<br>5-[(4-fluorophenyl)methyl]-N-(6R)-4-methyl-5-oxo-2-(trifluoromethyl)-7,8-dihydro-6H-pyrazolo[1,5-a][1,3]diazepin-6-yl-4H-1,2,4-triazole-3-carboxamide | Single Known Stereoisomer | $^1$H NMR (400 MHz, $CD_3OD$) δ 7.33-7.29 (m, 2H), 7.07-7.03 (m, 2H), 6.67 (s, 1H), 4.56-4.47 (m, 2H), 4.42-4.33 (m, 1H), 4.14 (s, 2H), 3.37 (s, 3H), 2.94-2.85 (m, 1H), 2.35-2.28 (m, 1H). | $R_T$ = 1.126 min, m/z = 452.1 |
| Example 551<br>0.96<br>WX Method 162 | 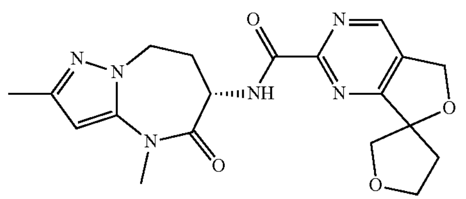 [SMILES: Cc1cc2n(n1)CC[C@H](NC(=O)c1ncc3c(n1)C1(CCOC1)OC3)C(=O)N2C]<br>N-[(6S)-2,4-dimethyl-5-oxo -7,8-dihydro-6H-pyrazolo[1,5-a][1,3]diazepin-6-yl]spiro[5H-furo[3,4-d]pyrimidine-7,3'-tetrahydrofuran]-2-carboxamide | Mixture of Diastereomers | $^1$H NMR (400 MHz, $CD_3OD$) δ 8.85 (s, 1H), 6.13 (s, 1H), 5.19 (s, 2H), 4.62-4.57 (m, 1H), 4.37-4.21 (m, 2H), 4.18-4.00 (m, 4H), 3.35 (s, 3H), 2.99-2.88 (m, 1H), 2.50-2.41 (m, 1H), 2.35-2.27 (m, 5H). | $R_T$ = 1.146 min, m/z = 399.2 |
| Example 552<br>0.11<br>WX Method 164 | 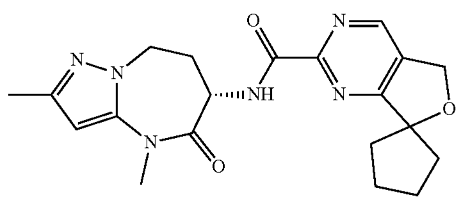 [SMILES: Cc1cc2n(n1)CC[C@H](NC(=O)c1ncc3c(n1)C1(CCCC1)OC3)C(=O)N2C]<br>N-[(6S)-2,4-dimethyl-5-oxo-7,8-dihydro-6H-pyrazolo[1,5-a][1,3]diazepin-6-yl]spiro[5H-furo[3,4-d]pyrimidine-7,1'-cyclopentane]-2-carboxamide | Single Known Stereoisomer | $^1$H NMR (400 MHz, $CD_3OD$) δ 8.79 (s, 1H), 6.13 (s, 1H), 5.11 (s, 2H), 4.59-4.57 (m, 1H), 4.33-4.25 (m, 2H), 3.35 (s, 3H), 2.98-2.91 (m, 1H), 2.31-2.25 (m, 4H), 2.13-1.99 (m, 4H), 1.94-1.91 4H). | $R_T$ = 1.850 min, m/z = 397.2 |

TABLE 4-continued

| Example Ki (μM) METHOD | Structure | Stereo | $^1$H NMR | MS (m/z) R.T. |
| --- | --- | --- | --- | --- |
| Example 553 0.0087 WX Method 119 | 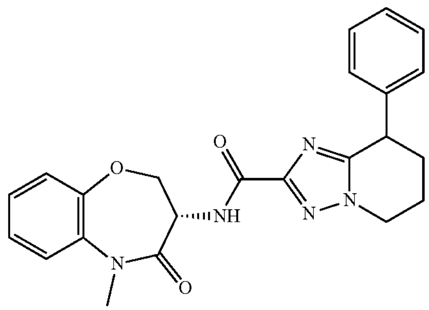 [SMILES: CN1C(=O)[C@@H](NC(=O)c2nc3n(n2)CCCC3c2ccccc2)COc2ccccc21] 8-phenyl-N-[(3S)-5-methyl-4-oxo-2,3-dihydro-1,5-benzoxazepin-3-yl]-5,6,7,8-tetrahydro-[1,2,4]triazolo[1,5-a]pyridine-2-carboxamide | Mixture of Diastereomers | $^1$H NMR (400 MHz, $CD_3OD$) δ 7.45-7.39 (m, 1H), 7.36-7.20 (m, 6H), 7.16 (d, J = 8.0 Hz, 2H), 5.02-4.95 (m, 1H), 4.58-4.51 (m, 1H), 4.40-4.32 (m, 4H), 3.39 (s, 3H), 2.40-2.33 (m, 1H), 2.24-2.03 (m, 3H). | $R_T$ = 1.831 min, m/z = 418.0 |
| Example 554 0.33 WX Method 119 | 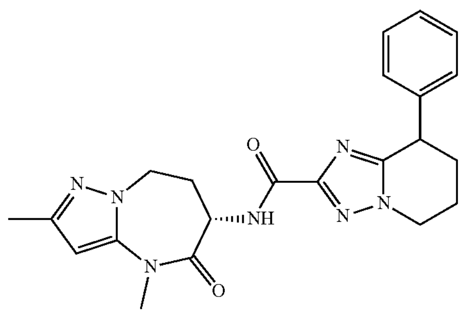 [SMILES: Cc1cc2n(n1)CC[C@H](NC(=O)c1nc3n(n1)CCCC3c1ccccc1)C(=O)N2C] 8-phenyl-N-[(6S)-2,4-dimethyl-5-oxo-7,8-dihydro-6H-pyrazolo[1,5-a][1,3]diazepin-6-yl]-5,6,7,8-tetrahydro-[1,2,4]triazole[1,5-a]pyridine-2-carboxamide | Mixture of Diastereomers | $^1$H NMR (400 MHz, $CD_3OD$) δ 7.39-7.23 (m, 3H), 7.20-7.08 (m, 2H), 6.10 (s, 1H) 4.53-4.47 (m, 1H), 4.38-4.12 (m, 5H), 3.34-3.31 (m, 3H), 2.83-2.72 (m, 1H), 2.40-2.32 (m, 1H), 2.31-1.99 (m, 7H). | $R_T$ = 0.769 min, m/z = 420.1 |
| Example 555 0.043 WX Method 056 | 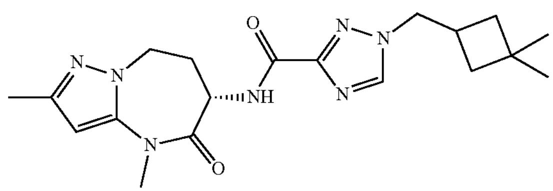 1-[(3,3-dimethylcyclobutylmethyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.46 (s, 1H), 6.12 (s, 1H), 4.57-4.52 (m, 1H), 4.32-4.24 (m, 4H), 3.34 (s, 3H), 2.86-2.79 (m, 2H), 2.29-2.23 (m, 4H), 1.87-1.82 (m, 2H), 1.67-1.61 (m, 2H), 1.16 (s, 3H), 1.08 (s, 3H). | $R_T$ = 1.810 min; m/z = 386.1 |

TABLE 4-continued

| Example Ki (μM) METHOD | Structure | Stereo | $^1$H NMR | MS (m/z) R.T. |
|---|---|---|---|---|
| Example 556<br>2.7<br>WX Method 169 | 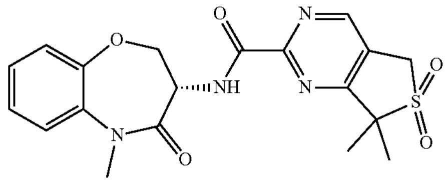 [SMILES: CN1C(=O)[C@@H](NC(=O)c2ncc3c(n2)C(C)(C)S(=O)(=O)C3)COc2ccccc21]<br>7,7-dimethyl-6,6-dioxo-N-[(3S5-methyl-4-oxo-2,3-dihydro-1,5-benzoxazepin-3-yl]-5H-thieno[3,4-d]pyrimidine-2-carboxamide | Single Known Stereoisomer | $^1$H NMR (400 MHz, $CD_3OD$) δ 8.93 (s, 1H), 7.45-7.43 (m, 1H), 7.36-7.22 (m, 3H), 5.06-5.02 (m, 1H), 4.87-4.86 (m, 2H), 4.66-4.58 (m, 1H), 4.47-4.42 (m, 1H), 3.43 (s, 3H), 1.68 (s, 6H). | $R_T$ = 1.543 min; m/z = 417.1 |
| Example 557<br>0.13<br>WX Method 085 | 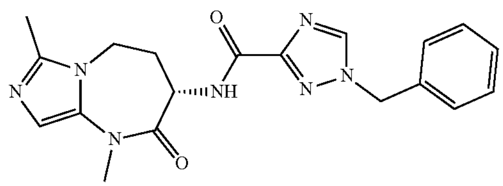 [SMILES: Cc1ncc2n1CC[C@H](NC(=O)c1ncn(Cc3ccccc3)n1)C(=O)N2C]<br>1-benzyl-N-(1,7-dimethyl-2-oxo-4,5-dihydro-3H-imidazo[1,5-a][1,3]diazepin-3-yl)-1,2,4-triazole-3-carboxamide | Mixture of Enantiomers | $^1$H NMR (400 MHz, DMSO-$d_6$) δ 8.82 (s, 1H), 8.49 (d, J = 7.6 Hz, 1H), 7.41-7.27 (m, 5H), 6.80 (s, 1H), 5.48 (s, 2H), 4.40-4.32 (m, 1H), 4.22-4.16 (m, 1H), 3.73-3.71 (m, 1H), 3.24-3.16 (m, 3H), 2.47-2.41 (m, 1H), 2.29 (s, 3H), 2.23-2.20 (m, 1H). | $R_T$ = 1.705 min, m/z = 380.2. |
| Example 588<br>0.039<br>WX Method 151 | 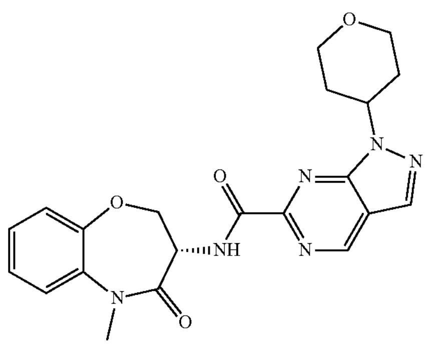 [SMILES: CN1C(=O)[C@@H](NC(=O)c2ncc3cnn(C4CCOCC4)c3n2)COc2ccccc21]<br>N-[(3S)-5-methyl-4-oxo-2,3-dihydro-1,5-benzoxazepin-3-yl]-1-tetrahydropyran-4-yl-pyrazolo[3,4-d]pyrimidine-6-carboxamide | Single Known Stereoisomer | $^1$H NMR (400 MHz, DMSO-$d_6$) δ 9.48 (s, 1H), 9.14 (d, J = 6.4 Hz, 1H), 8.54 (s, 1H), 7.54-7.52 (m, 1H), 7.35-7.28 (m, 3H), 5.17-5.10 (m, 1H), 4.90 -4.79 (m, 1H), 4.62-4.50 (m, 2H), 4.03-4.00 (m, 2H), 3.62-3.56 (m, 2H), 3.34 (s, 3H), 2.24-2.15 (m, 2H), 1.94-1.91 (m, 2H). | $R_T$ = 0.762 min; m/z = 423.1 |

TABLE 4-continued

| Example Ki (μM) METHOD | Structure | Stereo | $^1$H NMR | MS (m/z) R.T. |
|---|---|---|---|---|
| Example 559 0.57 WX Method 152 | 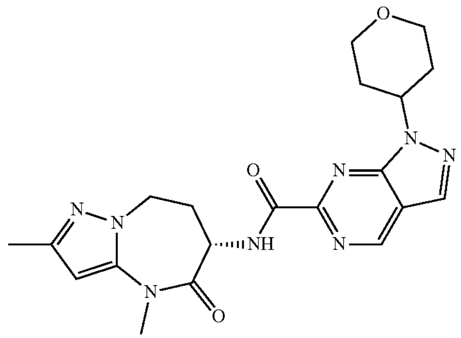 [SMILES: Cc1cc2n(n1)CC[C@H](NC(=O)c1ncc3cnn(C4CCOCC4)c3n1)C(=O)N2C] N-[(6S)-2,4-dimethyl-5-oxo7,8-dihydro-6H-pyrazolo [1,5-a][1,3]diazepin-6-yl]-1-tetrahydropyran-4-yl-pyrazolo [3,4-d]pyrimidine-6-carboxamide | Single Known Stereoisomer | $^1$H NMR (400 MHz, DMSO-d6) δ 9.47 (s, 1H), 9.16 (d, J = 8.0 Hz, 1H), 8.53 (s, 1H), 6.16 (s, 1H), 5.19-5.15 (m, 1H), 4.43-4.40 (m, 1H), 4.29 -4.25 (m, 1H), 4.21-4.11 (m, 1H), 4.04-3.99 (m, 2H), 3.63-3.56 (m, 2H), 3.25 (s, 3H), 2.74-2.69 (m, 1H), 2.50-2.49 (m, 1H), 2.22-2.18 (m, 5H), 1.94-1.91 (m, 2H). | $R_T$ = 0.705 min; m/z = 425.1 |
| Example 560 0.14 WX Method 057 | 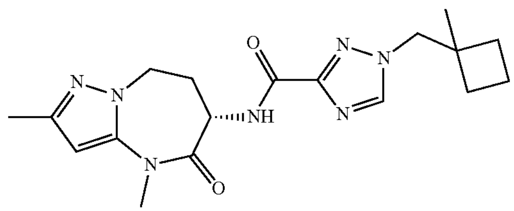 [SMILES: Cc1cc2n(n1)CC[C@H](NC(=O)c1ncn(CC3(C)CCC3)n1)C(=O)N2C] 1-[(1-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.47 (s, 1H), 6.12 (s, 1H), 4.57-4.52 (m, 1H), 4.35-4.23 (m, 4H), 3.34 (s, 3H), 2.91-2.87 (m, 1H), 2.29-2.26 (m, 4H), 2.13-2.08 (m, 2H), 1.96-1.92 (m, 1H), 1.87-1.83 (m, 1H), 1.77-1.72 (m, 2H), 1.10 (s, 3H). | $R_T$ = 0.637 min; m/z = 372.0 |
| Example 561 0.1 WX Method 057 | 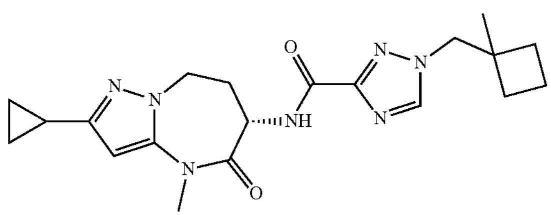 [SMILES: CN1C(=O)[C@@H](NC(=O)c2ncn(CC3(C)CCC3)n2)CCn2nc(C3CC3)cc21] 1-[(1-methylcyclobutyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.49 (s, 1H), 6.01 (s, 1H), 4.56-4.51 (m, 1H), 4.32-4.21 (m, 4H), 3.32 (s, 3H), 2.89-2.83 (m, 1H), 2.28-2.24 (m, 1H), 2.12-2.08 (m, 2H), 1.95-1.90 (m, 3H), 1.77-1.73 (m, 2H), 1.10 (s, 3H), 0.95-0.93 (m, 2H), 0.74-0.72 (m, 2H). | $R_T$ = 0.727 min; m/z = 398.0 |

TABLE 4-continued

| Example Ki (μM) METHOD | Structure | Stereo | $^1$H NMR | MS (m/z) R.T. |
|---|---|---|---|---|
| Example 562<br>0.02<br>WX Method 136 | 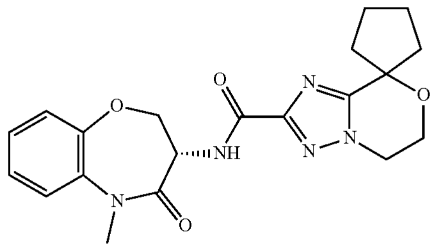 [SMILES: CN1C(=O)[C@@H](NC(=O)c2nc3n(n2)CCOC32CCCC2)COc2ccccc21]<br>N-[(3S)-5-methyl-4-oxo-2,3-dihydro-1,5-benzoxazepin-3-yl]spiro[5,6-dihydro-[1,2,4]triazolo[5,1-c][1,4]oxazine-8,1'-cyclopentane]-2-carboxamide | Single Known Stereoisomer | $^1$H NMR (400 MHz, $CD_3OD$) δ 7.45-7.42 (m, 1H), 7.32-7.30 (m, 2H), 7.25-7.23 (m, 1H), 5.02-5.00 (m, 1H), 4.62-4.58 (m, 1H), 4.45-4.41 (m, 1H), 4.27-4.25 (m, 2H), 4.13-4.11 (m, 2H), 3.42 (s, 3H), 2.16-2.14 (m, 4H), 1.91-1.90 (m, 4H). | $R_T$ = 0.807 min, m/z = 398.1 |
| Example 563<br>0.054<br>WX Method 146 | 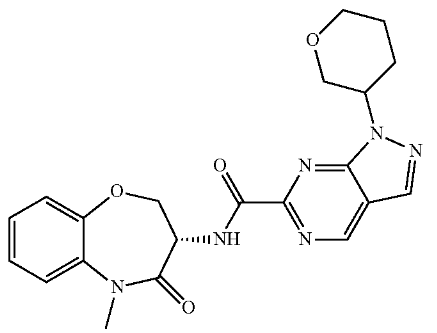 [SMILES: CN1C(=O)[C@@H](NC(=O)c2ncc3cnn(C4CCCOC4)c3n2)COc2ccccc21]<br>N-[(3S)-5-methyl-4-oxo-2,3-dihyfro-1,5-benzoxazepin-3-yl]-1-tetrahydropyran-3-yl-pyrazolo[3,4-d]pyrimidine-6-carboxamide | Mixture of Diastereomers | $^1$H NMR (400 MHz, $CD_3OD$) δ 9.36 (s, 1H) 8.38 (s, 1H), 7.27 (m, 3H), 5.17-5.11 (m, 2H), 4.75-4.65 (m, 1H), 4.58 4.40 (m, 1H), 4.15-3.85 (m, 3H), 3.65-3.53 (m, 1H), 3.45 (s, 3H), 2.40-2.33 (m, 1H), 2.25-2.21 (m, 1H), 1.98-1.91 (m, 2H). | $R_T$ = 0.70 min, m/z = 423.0 |
| Example 564<br>0.59<br>WX Method N | 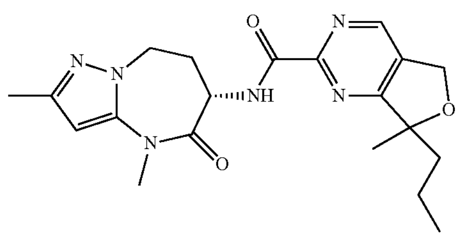<br>7-methyl-7-propyl-N-[(6S)-2,4-dimethyl-5-oxo-7,8-dihydro-6H-pyrazolo[1,5-a][1,3]diazepin-6-yl]-5H-furo[3,4-d]pyrimidine-2-carboxamide | Mixture of Diastereomers | $^1$H NMR (400 MHz, $CD_3OD$) δ 8.82 (s, 1H), 6.13 (s, 1H), 5.20-5.12 (m, 2H), 4.62-4.55 (m, 1H), 4.37-4.21 (m, 2H), 3.36 (s, 3H), 3.00-2.90 (m, 1H), 2.31-2.25 (m, 4H), 1.95-1.79 (m, 2H), 1.49-1.40 (m, 4H), 1.08-0.95 (m, 1H), 0.87 (t, J = 6.8 Hz, 3H). | $R_T$ = 1.546 min, m/z = 395.2 |

TABLE 4-continued

| Example<br>Ki (μM)<br>METHOD | Structure | Stereo | $^1$H NMR | MS (m/z) R.T. |
|---|---|---|---|---|
| Example 565<br>0.07<br>WX Method 136 | 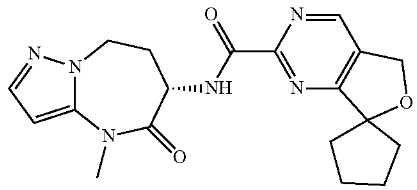 [SMILES: CN1C(=O)[C@@H](NC(=O)c2ncc3c(n2)C2(CCCC2)OC3)CCn2nccc21]<br>N-[rac-(6S)-4-methyl-5-oxo-7,8-dihydro-6H-pyrazolo[1,5-a][1,3]diazepin-6-yl]spiro[5H-furo[3,4-d]pyrimidine-7,1'-cyclopentane]-2-carboxamide | Single<br>Known Stereoisomer | $^1$H NMR (400 MHz, $CD_3OD$) δ 8.79 (s, 1H), 7.54 (s, 1H), 6.32 (s, 1H), 5.11 (s, 2H), 4.59-4.57 (m, 1H), 4.55-4.43 (m, 1H), 4.33-4.31 (m, 1H), 3.38 (s, 3H), 3.00-2.95 (m, 1H), 2.33-2.28 (m, 1H), 2.07-2.03 (m, 4H), 1.94-1.92 (m, 4H). | $R_T$ = 0.720 min, m/z = 383.1 |
| Example 566<br>0.48<br>WX Method N | 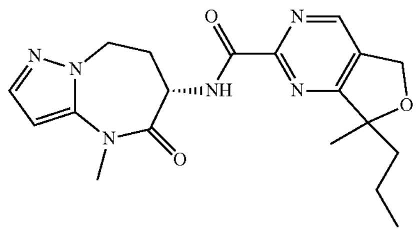 [SMILES: CCCC1(C)OCc2cnc(C(=O)N[C@H]3CCn4nccc4N(C)C3=O)nc21]<br>7-methyl-7-propyl-N-[(6S)-4-methyl-5-oxo-7,8-dihydro-6H-pyrazolo[1,5-a][1,3]diazepin-6-yl]-5H-furo[3,4-d]pyrimidine-2-carboxamide | Mixture of Diastereomers | $^1$H NMR (400 MHz, $CD_3OD$) δ 8.82 (s, 1H), 7.55 (d, J = 2.4 Hz, 1H), 6.33 (s, 1H), 5.20-5.12 (m, 2H), 4.60-4.55 (m, 1H), 4.49-4.43 (m, 1H), 4.36-4.28 (m, 1H), 3.39 (s, 3H), 3.03-2.92 (m, 1H), 2.35-2.28 (m, 1H), 1.96-1.79 (m, 2H), 1.49-1.40 (m, 4H), 1.08-0.95 (m, 1H), 0.87 (t, J = 6.8 Hz, 3H). | $R_T$ = 1.473 min, m/z = 385.2 |
| Example 567<br>0.41<br>WX Method 136 | 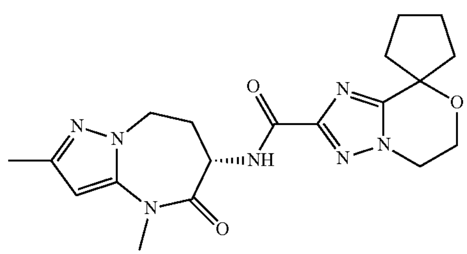 [SMILES: Cc1cc2n(n1)CC[C@H](NC(=O)c1nc3n(n1)CCOC31CCCC1)C(=O)N2C]<br>N-[(6S)-2,4-dimethyl-5-oxo-7,8-dihydro-6H-pyrazolo[1,5-a][1,3]diazepin-6-yl]spiro[5,6-dihydro-[1,2,4]triazolo[5,1-c][1,4]oxazine-8,1'-cyclopentane]-2-carboxamide | Single<br>Known Stereoisomer | $^1$H NMR (400 MHz, DMSO-$d_6$) δ 8.46 (d, J = 7.2 Hz, 1H), 6.13 (s, 1H), 4.40-4.20 (m, 4H), 4.16-4.03 (m, 3H), 3.22 (s, 3H), 2.63-2.54 (m, 1H), 2.39-2.30 (m, 1H), 2.17 (s, 3H), 2.11-1.96 (m, 4H), 1.87-1.43 (m, 4H). | $R_T$ = 0.724 min, m/z = 400.1 |

TABLE 4-continued

| Example Ki (μM) METHOD | Structure | Stereo | $^1$H NMR | MS (m/z) R.T. |
|---|---|---|---|---|
| Example 568<br>0.0081<br>WX Method 118 | 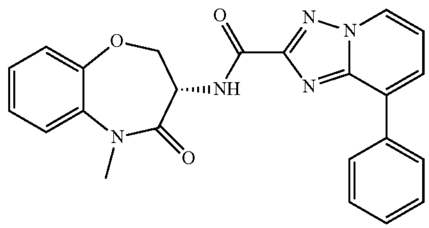 [SMILES: CN1C(=O)[C@@H](NC(=O)c2nc3c(-c4ccccc4)cccn3n2)COc2ccccc21]<br>8-phenyl-N-[(3 S)-5-methyl-4-oxo-2,3-dihydro-1,5-benzoxazepin-3-yl]-[1,2,4]triazolo[1,5-a]pyridine-2-carboxamide | Single<br>Known Stereoisomer | $^1$H NMR (400 MHz, $CD_3OD$) δ 8.83-8.77 (m, 1H), 8.06 (d, J = 7.2 Hz, 2H), 7.94-7.88 (m, 1H), 7.57-7.51 (m, 2H), 7.50-7.42 (m, 2H), 7.40-7.28 (m, 3H), 7.27-7.21 (m, 1H), 5.12-5.04 (m, 1H), 4.67-4.62 (m, 1H), 4.52-4.46 (m, 1H), 3.43 (s, 3H). | $R_T$ = 0.851 min, m/z = 414.1 |
| Example 569<br>0.58<br>WX Method 041 | 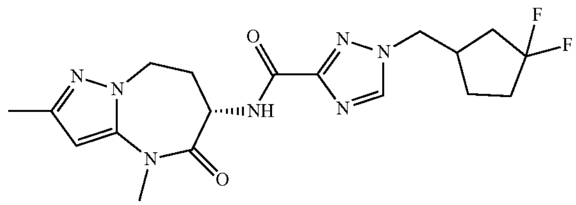 [SMILES: Cc1cc2n(n1)CC[C@H](NC(=O)c1ncn(CC3CCC(F)(F)C3)n1)C(=O)N2C]<br>1-[(3,3-difluorocyclopentyl)methyl]-N-(6S)-2,4-dimethyl-5-oxo-7,8-dihydro-6H-pyrazolo[1,5-a][1,3] diazepin-6-yl-1,2,4-triazole-3-carboxamide | Mixture of Diastereomers | $^1$H NMR (400 MHz, $CD_3OD$) δ 8.50 (s, 1H), 6.11 (s, 1H), 4.59-4.51 (m, 2H), 4.31-4.27 (m, 2H), 4.26-4.18 (m, 1H), 3.33 (s, 3H), 2.94-2.69 (m, 3H), 2.25 (s, 3H), 2.22-1.84 (m, 5H), 1.63-1.53 (m, 1H). | $R_T$ = 1.512 min, m/z = 408.2 |
| Example 570<br>0.024<br>WX Method 083 | 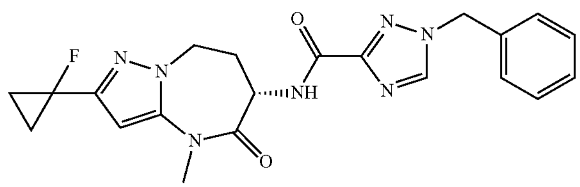 [SMILES: CN1C(=O)[C@@H](NC(=O)c2ncn(Cc3ccccc3)n2)CCn2nc(C3(F)CC3)cc21]<br>1-benzyl-N-(6S)-2-(1-fluorocyclopropyl)-4-methyl-5-oxo-7,8-dihydro-6H-pyrazolo[1,5-a][1,3]diazepin-6-yl-1,2,4-triazole-3-carboxamide | Single<br>Unknown Stereoisomer | $^1$H NMR (400 MHz, CD3OD) δ 8.56 (s, 1H), 7.41-7.28 (m, 5H), 6.37 (s, 1H), 5.46 (s, 2H), 4.56-4.53 (m, 1H), 4.39-4.31 (m, 1H), 4.29-4.20 (m, 1H), 3.34 (s, 3H), 2.84 (m, 3H), 2.26 (m, 1H), 1.42-1.34 (m, 2H), 1.18-1.07 (m, 2H). | $R_T$ = 1.672 min, m/z = 424.2 |

TABLE 4-continued

| Example Ki (μM) METHOD | Structure | Stereo | $^1$H NMR | MS (m/z) R.T. |
|---|---|---|---|---|
| Example 571 G030757750.023 WX Method 115 | 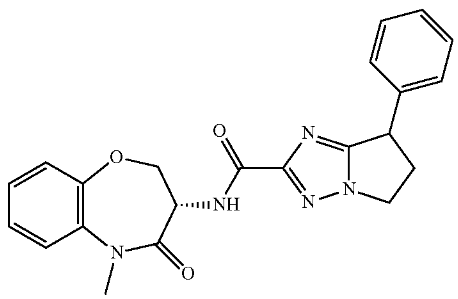 [SMILES: CN1C(=O)[C@@H](NC(=O)c2nc3n(n2)CCC3c2ccccc2)COc2ccccc21] 7-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Mixture of Diastereomers | $^1$H NMR (400 MHz, $CD_3OD$) δ 7.45-7.41 (m, 1H), 7.39-7.26 (m, 7H), 7.25-7.21 (m, 1H), 5.02-4.97 (m, 1H), 4.60-4.52 (m, 2H), 4.45 -4.35 (m, 2H), 4.32-4.22 (m, 1H), 3.40 (s, 3H), 3.28-3.23 (m, 1H), 2.76 -2.67 (m, 1H). | $R_T$ = 1.017 min, m/z = 404.3 |
| Example 572 0.45 WX Method 115 | 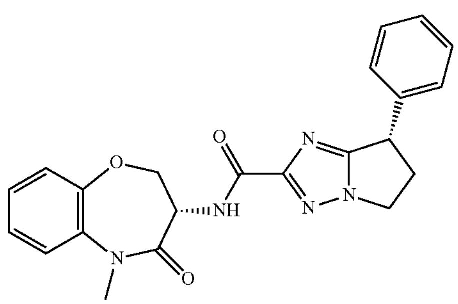 [SMILES: CN1C(=O)[C@@H](NC(=O)c2nc3n(n2)CC[C@H]3c2ccccc2)COc2ccccc21] (7S)-7-phenyl-N-R35)-5-methyl-4-oxo-2,3-dihydro-1,5-benzoxazepin-3-yl]-6,7-dihydro-5H-pyrrolo[1,2-b][1,2,4] triazole-2-carboxamide | Single Unknown Stereoisomer | $^1$H NMR (400 MHz, $CD_3OD$) δ 7.42-7.22 (m, 9H), 5.00-4.87 (m, 1H), 4.61 -4.53 (m, 2H), 4.42-4.39 (m, 2H), 4.37-4.28 (m, 1H), 3.40 (s, 3H), 3.28-3.25 (m, 1H), 2.76-2.70 (m, 1H). | $R_T$ = 1.011 min, m/z = 404.4 |

TABLE 4-continued

| Example Ki (μM) METHOD | Structure | Stereo | $^1$H NMR | MS (m/z) R.T. |
|---|---|---|---|---|
| Example 573 0.017 WX Method 115 | 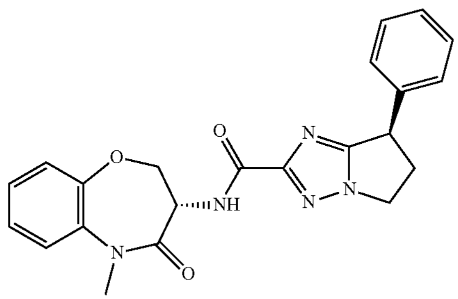 [SMILES: CN1C(=O)[C@@H](NC(=O)c2nc3n(n2)CC[C@@H]3c2ccccc2)COc2ccccc21] (7R)-7-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Single Unknown Stereoisomer | $^1$H NMR (400 MHz, $CD_3OD$) δ 7.41-7.24 (m, 9H), 5.00-4.97 (m, 1H), 4.60-4.54 (m, 2H), 4.42-4.39 (m, 2H), 4.37-4.28 (m, 1H), 3.41 (s, 3H), 3.28-3.25 (m, 1H), 2.76-2.69 (m, 1H). | $R_T$ = 1.006 min, m/z = 404.4 |
| Example 574 0.058 WX Method 113 | 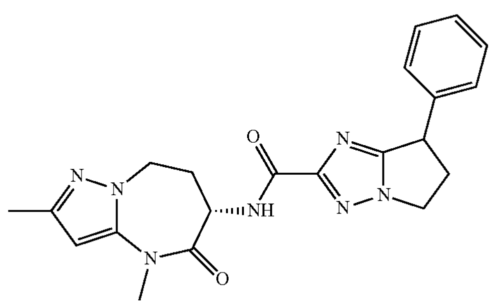 [SMILES: Cc1cc2n(n1)CC[C@H](NC(=O)c1nc3n(n1)CCC3c1ccccc1)C(=O)N2C] 7-phenyl-N-[(6S)-2,4-dimethyl-5-oxo-7,8-dihydro-6H-pyrazolo[1,5-a][1,3]diaepin-6-yl]-6,7-dihydro-5H-pyrrolo[1,2-b][1,2,4]triazole-2-carboxamide | Mixture of Diastereomers | $^1$H NMR (400 MHz, $CD_3OD$) δ 7.39-7.25 (m, 5H), 6.11 (s, 1H), 4.57-4.49 (m, 2H), 4.45-4.36 (m, 1H), 4.35-4.15 (m, 3H), 3.32(s, 3H), 3.30-3.24 (m,1H), 2.90-2.66 (m, 2H), 2.33 -2.14 (m, 4H). | $R_T$ = 0.920 min, m/z = 406.3 |

TABLE 4-continued

| Example<br>Ki (μM)<br>METHOD | Structure | Stereo | $^1$H NMR | MS (m/z) R.T. |
|---|---|---|---|---|
| Example 575<br>0.028<br>WX Method 113 | 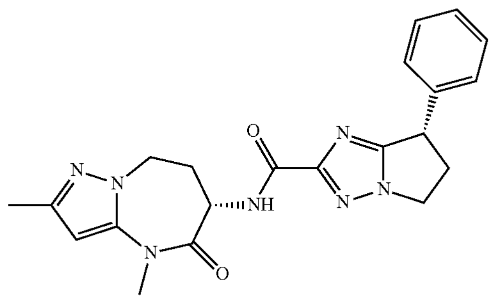 [SMILES: Cc1cc2n(n1)CC[C@H](NC(=O)c1nc3n(n1)CC[C@H]3c1ccccc1)C(=O)N2C]<br>rac-(7S)-7-phenyl-N-[rac-(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single<br>Unknown Stereoisomer | $^1$H NMR (400 MHz, $CD_3OD$) δ 9.35 (s, 1H), 8.38 (s, 1H), 7.05-7.00 (m, 2H), 5.45-1.95 5.40 (m 1H), 4.69-4.64 (m, 1H), 3.05-3.02 (m, 1H), 2.89-2.76 (m, 2H), 2.32-2.26 (m, 1H), 1.60 (d, J = 6.8 Hz, 6H). | $R_T$ = 1.95 min, m/z = 406.2 |
| Example 576<br>0.04<br>WX Method 085 | 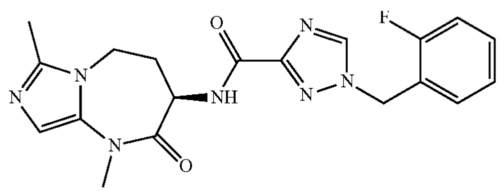 [SMILES: Cc1ncc2n1CC[C@@H](NC(=O)c1ncn(Cc3ccccc3F)n1)C(=O)N2C]<br>1-[(2-fluorophenyl)methyl]-N-[(3R)-1,7-dimethyl-2-oxo-4,5-dihydro-3H-imidazo[1,5-a][1,3diazepin-3-yl]-1,2,4-triazole-3-carboxamide | Single<br>Unknown Stereoisomer | $^1$H NMR (400 MHz, DMSO-$d_6$) δ 8.81 (s, 1H), 8.48 (d, J = 8.0Hz, 1H), 7.46-7.39 (m, 1H), 7.38-7.31 (m, 1H), 7.28-7.19 (m, 2H), 6.80 (s 1H), 5.55 (s, 2H), 4.38-4.33 (m, 1H), 4.23-4.17 (m, 1H), 3.75-3.71 (m, 1H), 3.23-3.17 (m, 3H), 2.47-2.41 (m, 1H), 2.29 (s, 3H), 2.25-2.17 (m, 1H). | $R_T$ = 1.77 min; m/z = 398.1. |
| Example 577<br>0.08<br>WX Method 085 | 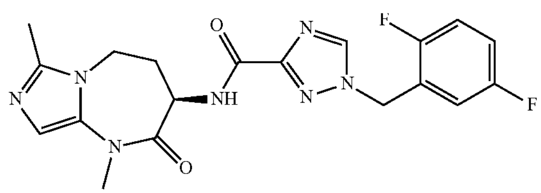 [SMILES: Cc1ncc2n1CC[C@@H](NC(=O)c1ncn(Cc3cc(F)ccc3F)n1)C(=O)N2C]<br>1-[(2,5-difluorophenyl)methyl]-N-[(3R)-1,7-dimethyl-2-oxo-4,5-dihydro-3H-imidazo[1,5-a][1,3]diazepin-3-yl]-1,2,4-triazole-3-carboxamide | Single<br>Unknown Stereoisomer | $^1$H NMR (400 MHz, DMSO-$d_6$) δ 8.81 (s, 1H), 8.50 (d, J = 8.0 Hz, 1H), 7.37-7.22 (m, 3H), 6.80 (s, 1H), 5.54 (s, 2H), 4.40-4.32 (m, 1H), 4.22-4.16 (m, 1H), 3.75-3.69 (m, 1H), 3.21 (s, 3H), 2.47-2.41 (m, 1H), 2.29 (s, 3H), 2.25-2.17 (m, 1H). | $R_T$ = 1.796 min, m/z = 416.1. |

TABLE 4-continued

| Example Ki (μM) METHOD | Structure | Stereo | $^1$H NMR | MS (m/z) R.T. |
|---|---|---|---|---|
| Example 578 0.04 WX Method 085 | 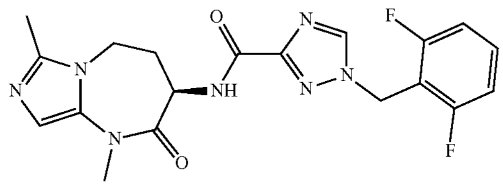 1-[(2,6-difluorophenyl)methyl]-N-[(3R)-1,7-dimethyl-2-oxo-4,5-dihydro-3H-imidazo[1,5-a][1,3]diazepin-3-yl-1,2,4-triazole-3-carboxamide | Single Unknown Stereoisomer | $^1$H NMR (400 MHz, DMSO-$d_6$) δ 8.83 (s, 1H), 8.46 (d, J = 8.0 Hz, 1H), 7.54-7.46 (m, 1H), 7.19-7.15 (m, 2H), 6.80 (s, 1H), 5.55 (s, 2H), 4.37-4.30 (m, 1H), 5.55 (s, 2H), 4.37 1H), 3.75-3.67 (m, 1H), 3.20 (s, 3H), 2.46-2.40 (m, 1H), 2.29 (s, 3H), 2.24-2.16 (m, 1H). | $R_T$ = 1.762 min; m/z = 416.2. |
| Example 579 0.037 WX Method 113 | 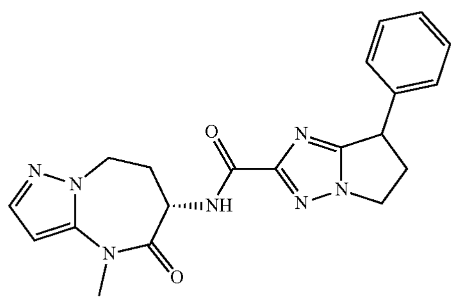 [SMILES: CN1C(=O)[C@@H](NC(=O)c2nc3n(n2)CCC3c2ccccc2)CCn2nccc21] 7-phenyl-N-[rac-(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Mixture of Diastereomers | $^1$H NMR (400 MHz, $CD_3OD$) δ 7.52 (s,1H), 7.39-7.32 (m, 2H), 7.32-7.25 (m, 3H), 6.30 (s, 1H), 4.57-4.46 (m, 2H), 4.45-4.35 (m, 2H), 4.33-4.20 (m, 2H), 3.35 (s, 3H), 3.30-3.24 (m, 1H), 2.91-2.79 (m, 1H), 2.76-2.66 (m, 1H), 2.32-2.21 (m, 1H). | $R_T$ = 0.889 min, m/z = 392.3 |
| Example 580 0.054 WX Method 043 | 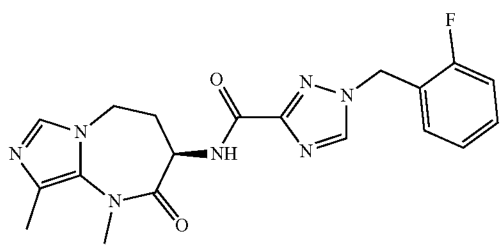 [SMILES: Cc1ncn2c1N(C)C(=O)[C@H](NC(=O)c1ncn(Cc3ccccc3F)n1)CC2] 1-[(2-fluorophenyl)methyl]-N-(3R)-1,9-dimethyl-2-oxo-4,5-dihydro-3H-imidazo[1,5-a][1,3]diazepin-3-yl-1,2,4-triazole-3-carboxamide | Single Unknown Stereoisomer | $^1$H NMR (400 MHz, $CD_3OD$) δ 8.59 (s, 1H), 7.56 (s, 1H), 7.41-7.38 (m, 2H), 7.22-7.15 (m, 2H), 5.55 (s, 2H), 4.57-4.52 (m, 1H), 4.37-4.31 (m, 1H), 3.96-3.93 (m, 1H), 3.31 (s, 3H), 2.72-2.63 (m, 1H), 2.22 (s, 3H), 2.15-2.09 (m, 1H). | $R_T$ = 0.447 min; m/z = 398.0 |

TABLE 4-continued

| Example Ki (μM) METHOD | Structure | Stereo | $^1$H NMR | MS (m/z) R.T. |
|---|---|---|---|---|
| Example 581<br>0.047<br>WX Method 100 | 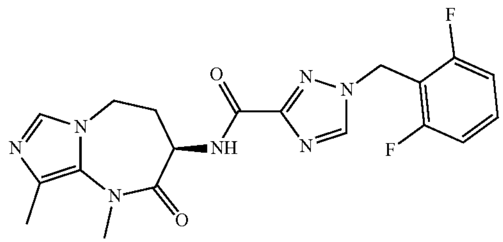 [SMILES: Cc1ncn2c1N(C)C(=O)[C@H](NC(=O)c1ncn(Cc3c(F)cccc3F)n1)CC2]<br>1-[(2,6-difluorophenyl)methyl]-N-(3R)-1,9-dimethyl-2-oxo-4,5-dihydro-3H-imidazo[1,5-a][1,3diazepin-3-yl-1,2,4-triazole-3-carboxamide | Single<br>Unknown Stereoisomer | $^1$H NMR (400 MHz, $CD_3OD$) δ 8.65 (s, 1H), 8.33 (s, 1H), 7.50-7.44 (m, 1H), 7.09-7.02 (m, 2H), 5.62 (s, 2H), 4.65-4.60 (m, 1H), 4.50-4.46 (m, 1H), 4.13-4.08 (m, 1H), 3.32 (s, 3H), 2.73-2.65 (m, 1H), 2.32 (s, 3H), 2.26-2.15 (m, 1H). | $R_T$ = 0.549 min; m/z = 416.0 |
| Example 582<br>0.0076<br>WX Method 073 | 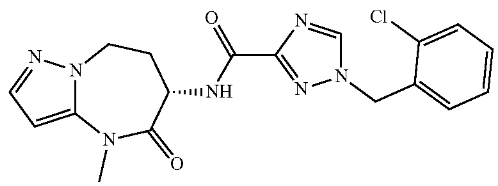 [SMILES: CN1C(=O)[C@@H](NC(=O)c2ncn(Cc3ccccc3Cl)n2)CCn2nccc21]<br>1-[(2-chlorophenyl)methyl]-N-(6S)-4-methyl-5-oxo-7,8-dihydro-6H-pyrazolo[1,5-a][1,3]diazepin-6-yl-1,2,4-triazole-3-carboxamide | Single<br>Known Stereoisomer | $^1$H NMR (400 MHz, $CD_3OD$) δ 8.58 (s, 1H), 7.52 (s, 1H), 7.46 (d, J = 6.8 Hz, 1H), 7.37-7.32 (m, 3H), 6.30 (s, 1H), 5.61 (s, 2H), 4.50-4.41 (m, 2H), 4.30-4.27 (m, 1H), 3.35 (s, 3H), 2.88-2.82 (m, 1H), 2.29-2.23 (m, 1H). | $R_T$ = 0.633 min, m/z = 400.0 |
| Example 583<br>0.024<br>WX Method 052 | 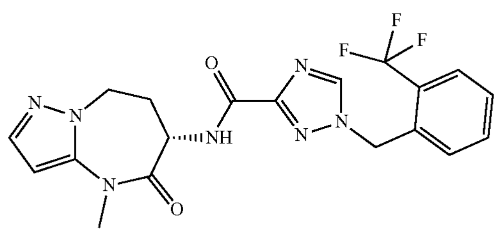 [SMILES: CN1C(=O)[C@@H](NC(=O)c2ncn(Cc3ccccc3C(F)(F)F)n2)CCn2nccc21]<br>N-(6S)-4-methyl-5-oxo-7,8-dihydro-6H-pyrazolo[1,5-a][1,3]diazepin-6-yl-1-[[2-(trifluoromethyl)phenyl]methyl]-1,2,4-triazole-3-carboxamide | Single<br>Known Stereoisomer | $^1$H NMR (400 MHz, $CD_3OD$) δ 8.55 (s, 1H), 7.77 (d, J = 8.0 Hz, 1H), 7.66-7.60 (m, 1H), 7.57-7.49 (m, 2H), 7.28 (d, J = 8.0 Hz, 1H), 6.30 (d, J = 2.0 Hz, 1H), 5.70 (s, 2H), 4.51-4.49 (m, 1H), 4.45-4.37 (m, 1H), 4.32-4.21 (m, 1H), 3.34 (s, 3H), 2.89-2.83 (m, 1H), 2.32-2.26 (m, 1H). | $R_T$ = 0.935 min, m/z = 434.3 |

TABLE 4-continued

| Example Ki (μM) METHOD | Structure | Stereo | $^1$H NMR | MS (m/z) R.T. |
|---|---|---|---|---|
| Example 584 0.025 WX Method 052 | 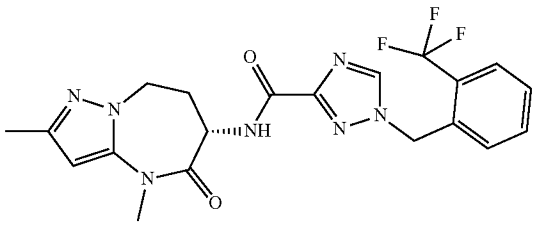 [SMILES: Cc1cc2n(n1)CC[C@H](NC(=O)c1ncn(Cc3ccccc3C(F)(F)F)n1)C(=O)N2C] N-(6S)-2,4-dimethyl-5-oxo-7,8-dihydro-6H-pyrazolo[ 1-[[2-(trifluoromethyl)phenyl]methyl]-1,2,4-triazole-3-carboxamide | Single Known Stereoisomer | $^1$H NMR (400 MHz, $CD_3OD$) δ 8.56 (s, 1H), 7.78 (d, J = 8.0 Hz, 1H), 7.66-7.61 (m, 1H), 7.58-7.52 (m, 1H), 7.28 (d, J = 8.0 Hz, 1H), 6.11 (s, 1H), 5.71 (s, 2H), 4.56-4.51 (m, 1H), 4.35-4.27 (m, 1H), 4.26-4.15 (m, 1H), 3.32 (s, 3H), 2.87-2.80 (m, 1H), 2.30-2.21 (m, 4H). | $R_T$ = 0.971 min, m/z = 448.3 |
| Example 582 0.043 WX Method 055 | 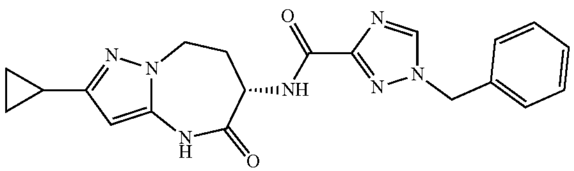 [SMILES: O=C(N[C@H]1CCn2nc(C3CC3)cc2NC1=O)c1ncn(Cc2ccccc2)n1] 1-benzyl-N-(6S)-2-cyclopropyl-5-oxo-4,6,7,8-tetrahydropyrazolo[1,5-a][1,3]diazepin-6-yl-1,2,4-triazole-3-carboxamide | Single Known Stereoisomer | $^1$H NMR (400 MHz, DMSO-$d_6$) δ 10.32 (s, 1H), RT = 8.82 (s, 1H), 8.48 (d, J = 8.0 Hz, 1H), 7.41-7.26 (m, 5H), 5.66 (s, 1H), 5.48 (s, 2H), 4.38-4.35 (m,1H), 4.28-4.20 (m, 1H), 4.13-4.02 (m, 1H), 2.59-2.54 (m, 1H0, 2.34-2.25 (m, 1H), 1.84-1.75 (m, 1H), 0.85-0.79 (m, 2H), 0.65-0.59 (m, 2H). | $R_T$ = 0.869 min, m/z = 392.0. |
| Example 586 0.063 WX Method 054 | 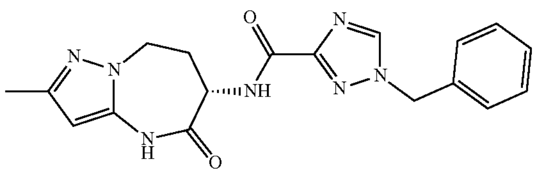 [SMILES: Cc1cc2n(n1)CC[C@H](NC(=O)c1ncn(Cc3ccccc3)n1)C(=O)N2] 1-benzyl-N-(6S)-2-methyl-5-oxo-4,6,7,8-tetrahydropyrazolo[1,5-a][1,3]diazepin-6-yl-1,2,4-triazole-3-carboxamide | Single Known Stereoisomer | $^1$H NMR (400 MHz, DMSO-$d_6$) δ 8.80 (s, 1H), 8.45 (d, J = 7.6 Hz, 1H), 7.38-7.25 (m, 5H), 5.72 (s, 1H), 5.46 (s, 2H), 4.39-4.34 (m, 1H), 4.28-4.19 (m, 1H(, 4.13-4.01 (m, 1H), 2.64 (s, 1H), 2.30 (s, 1H), 2.09 (s, 3H). | $R_T$ = 0.689 min, m/z = 366.0 |

TABLE 4-continued

| Example<br>Ki (μM)<br>METHOD | Structure | Stereo | $^1H$ NMR | MS (m/z) R.T. |
|---|---|---|---|---|
| Example 587<br>0.047<br>WX Method 034 | 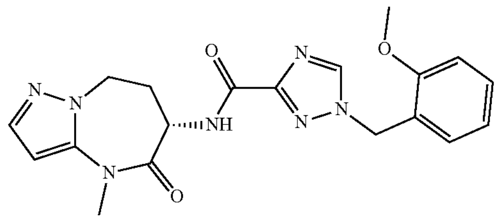 [SMILES: COc1ccccc1Cn1cnc(C(=O)N[C@H]2CCn3nccc3N(C)C2=O)n1]<br>1-[(2-methoxyphenyl)methyl]-N-(6S)-4-methyl-5-oxo-7,8-dihydro-6H-pyrazolo[1,5-a][1,3]diazepin-6-yl-1,2,4-triazole-3-carboxamide | Single<br>Known Stereoisomer | $^1H$ NMR (400 MHz, $CD_3OD$) δ 8.44 (s, 1H), 7.51 (s, 1H), 7.36-7.32 (m, 1H), 7.28-7.26 (m, 1H), 7.00 (d, J = 8.0 Hz, 1H), 6.96-6.93 (m, 1H), 6.29 (s, 1H), 5.42 (s, 2H), 4.51-4.46 (m, 1H), 4.44-4.38 (m, 1H), 4.30-4.22 (m, 1H), 3.83 (s, 3H), 3.34 (s, 3H), 2.89-2.79 (m, 1H), 2.29-2.21 (m, 1H). | $R_T$ = 1.48 min, m/z = 396.1. |
| Example 588<br>0.013<br>WX Method 062 | 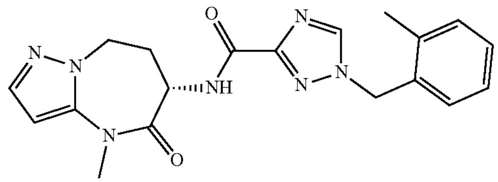 [SMILES: Cc1ccccc1Cn1cnc(C(=O)N[C@H]2CCn3nccc3N(C)C2=O)n1]<br>1-(o-tolylmethyl)-N-(6S)-4-methyl-5-oxo-7,8-dihydro-6H-pyrazolo[1,5-a][1,3]diazepin-6-yl-1,2,4-triazole-3-carboxamide | Single<br>Known Stereoisomer | $^1H$ NMR (400 MHz, $CD_3OD$) δ 8.45 (s, 1H), 7.52-7.51 (m, 1H), 7.26-7.15 (m, 4H), 6.31-6.30 (m, 1H), 5.50 (s, 2H), 4.53-4.40 (m, 2H), 4.30-4.25 (m, 1H), 3.35 (s, 3H), 2.89-2.83 (m, 1H), 2.34 (s, 3H), 2.31-2.23 (m, 1H). | $R_T$ = 1.48 min; m/z = 380.2 |
| Example 589<br>0.048<br>WX Method 034 | 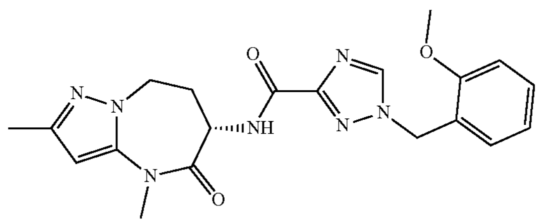 [SMILES: COc1ccccc1Cn1cnc(C(=O)N[C@H]2CCn3nc(C)cc3N(C)C2=O)n1]<br>1-[(2-methoxyphenyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single<br>Known Stereoisomer | $^1H$ NMR (400 MHz, $CD_3OD$) δ 8.44 (s, 1H), 7.36-7.32 (m, 1H), 7.30-7.26 (m, 1H), 7.00 (d, J = 8.4 Hz, 1H), 6.96-6.92 (m, 1H), 6.09 (s, 1H), 5.42 (s, 2H), 4.53-4.48 (m, 1H), 4.32-4.26 (m, 1H), 4.23-4.15 (m, 1H), 3.83 (s, 3H), 3.34 (s, 3H), 2.87-2.76 (m, 1H), 2.24 (s, 3H), 2.26-2.18 (m, 1H). | $R_T$ = 1.55 min, m/z = 410.1. |

TABLE 4-continued

| Example Ki (μM) METHOD | Structure | Stereo | $^1$H NMR | MS (m/z) R.T. |
|---|---|---|---|---|
| Example 590 0.7 WX Method 059 | 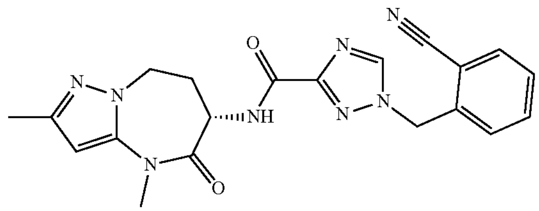 [SMILES: Cc1cc2n(n1)CC[C@H](NC(=O)c1ncn(Cc3ccccc3C#N)n1)C(=O)N2C] 1-[(2-cyanophenyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.79 (s, 1H), 7.81 (d, J = 7.2 Hz, 1H), 7.74-7.68 (m, 1H), 7.59-7.53 (m, 1H), 7.51-7.49 (m, 1H), 6.44 (s, 1H), 5.74 (s, 2H), 4.73-4.68 (m, 1H), 4.51-4.44 (m, 1H), 4.42-4.33 (m, 1H), 3.37 (s, 3H), 2.94-2.82 (m, 1H), 2.46-2.35 (m, 4H). | $R_T$ = 1.544 min; m/z = 405.3. |
| Example 591 0.017 WX Method 062 | 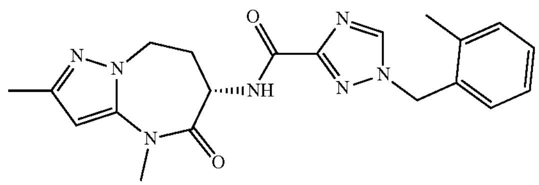 [SMILES: Cc1cc2n(n1)CC[C@H](NC(=O)c1ncn(Cc3ccccc3C)n1)C(=O)N2C] 1-(o-tolylmethyl)-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.45 (s, 1H), 7.26-7.22 (m, 2H), 7.20-7.15 (m, 2H), 6.11 (s, 1H), 5.50 (s, 2H), 4.55-4.50 (m, 1H), 4.30-4.28 (m 1H), 4.23-4.20 (m, 1H), 3.32 s, 3H), 2.87-2.81 (m, 1H), 2.34 (s, 3H), 2.28-2.20 (m, 4H). | $R_T$ = 1.565 min; m/z = 394.2. |
| Example 592 0.048 WX Method | 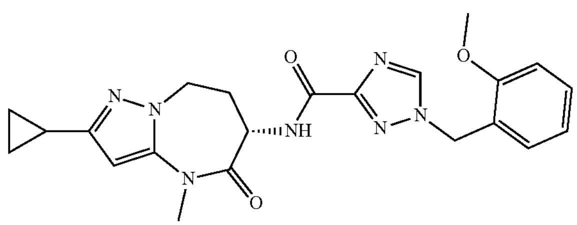 [SMILES: COc1ccccc1Cn1cnc(C(=O)N[C@H]2CCn3nc(C4CC4)cc3N(C)C2=O)n1] 1-[(2-methoxyphenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.44 (s, 1H), 7.36-7.32 (m, 1H), 7.30-7.26 (m, 1H), 7.00 (d, J = 8.4 Hz, 1H), 6.96-6.92 (m, 1H), 5.98 (s, 1H), 5.42 (s, 2H), 4.53-4.48 (m, 1H), 4.32-4.26 (m, 1H), 4.23-4.15 (m, 1H), 3.83 (s, 3H), 3.34 (s, 3H), 2.83-2.78 (m, 1H), 2.22-2.20 (m, 1H), 1.91-1.86 (m, 1H), 0.93-0.91 (m, 2H), 0.73-0.71 (m, 2H). | $R_T$ = 1.68 min, m/z = 436.1 |

TABLE 4-continued

| Example Ki (μM) METHOD | Structure | Stereo | $^{1}$H NMR | MS (m/z) R.T. |
|---|---|---|---|---|
| Example 593 0.079 WX Method 059 | 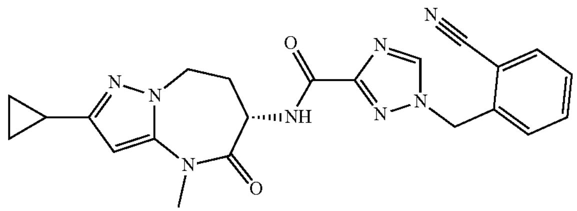 [SMILES: CN1C(=O)[C@@H](NC(=O)c2ncn(Cc3ccccc3C#N)n2)CCn2nc(C3CC3)cc21] 1-[(2-cyanophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^{1}$H NMR (400 MHz, $CD_3OD$) δ 8.84 (s, 1H), 7.81 (d, J = 7.6 Hz, 1H), 7.73-7.68 (m, 1H), 7.59-7.48 (m, 2H), 6.38 (s, 1H), 5.75 (s, 2H), 4.75-4.70 (m, 1H), 4.54-4.45 (m, 1H), 4.42-4.33 (m, 1H), 3.36 (s, 3H), 2.94-2.83 (m, 1H), 2.46-2.36 (m, 1H), 2.09-2.01 (m, 1H), 1.20-1.17 (m, 2H), 1.00-0.91 (m, 2H). | $R_T$ = 1.65 min; m/z = 431.3 |
| Example 594 0.42 WX Method 041 | 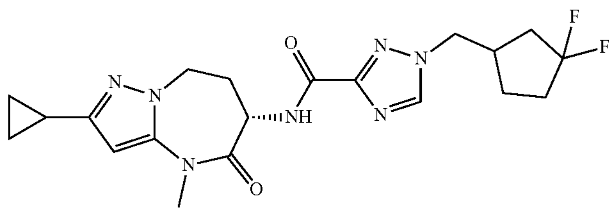 [SMILES: CN1C(=O)[C@@H](NC(=O)c2ncn(CC3CCC(F)(F)C3)n2)CCn2nc(C3CC3)cc21] 1-[(3,3-difluorocyclopentyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Mixture of Diastereomers | $^{1}$H NMR (400 MHz, $CD_3OD$) δ 8.51 (s, 1H), 6.01 (s, 1H), 4.57-4.50 (m, 1H), 4.35-4.27 (m, 3H), 4.24-4.16 (m, 1H), 3.32 (s, 3H), 2.92-2.70 (m, 3H), 2.29-2.11 (m, 3H), 1.97-1.83 (m, 3H), 1.63-1.55 (m, 1H), 0.99-0.91 (m, 2H), 0.79-0.69 (m, 2H). | $R_T$ = 0.945 min, m/z = 434.3 |
| Example 595 0.0047 WX Method 140 | 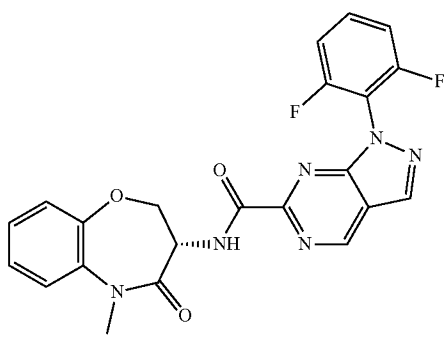 [SMILES: CN1C(=O)[C@@H](NC(=O)c2ncc3cnn(-c4c(F)cccc4F)c3n2)COc2ccccc21] 1-(2,6-difluorophenyl)-N-[(3S)-5-methyl-4-oxo-2,3-dihydro-1,5-benzoxazepin-3-yl]pyrazolo[3,4-d]pyrimidine-6-carboxamide | Single Known Stereoisomer | $^{1}$H NMR (400 MHz, $CD_3OD$) δ 9.53 (s, 1H), 9.23 (d, J = 7.2 Hz, 1H), 8.70 (s, 1H), 7.74-7.67 (m, 1H), 7.46-7.40 (m, 1H), 7.34-7.28 (m, 3H), 7.26-7.21 (m, 1H), 5.06-5.01 (m, 1H), 4.69-4.65 (m, 1H), 4.45-4.38 (m, 1H), 3.42 (s, 3H). | $R_T$ = 1.851 min; m/z = 451.2 |

TABLE 4-continued

| Example Ki (μM) METHOD | Structure | Stereo | $^1H$ NMR | MS (m/z) R.T. |
|---|---|---|---|---|
| Example 596<br>0.1<br>WX Method 096 | 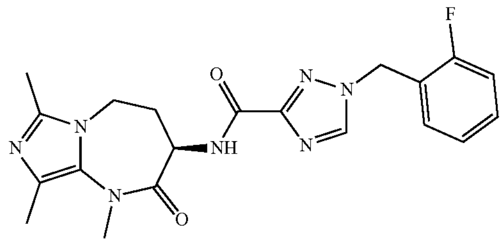 [SMILES: Cc1nc(C)n2c1N(C)C(=O)[C@H](NC(=O)c1ncn(Cc3ccccc3F)n1)CC2]<br>1-[(2-fluorophenyl)methyl]-N-(3R)-1,7,9-trimethyl-2-oxo-4,5-dihydro-3H-imidazo[1,5-a][1,3]diazepin-3-yl-1,2,4-triazole-3-carboxamide | Single<br>Unknown Stereoisomer | $^1H$ NMR (400 MHz, $CD_3OD$) δ 8.58 (s, 1H), 7.43-7.36 (m, 2H), 7.22-7.12 (m, 2H), 5.48 (s, 2H), 4.57-4.52 (m, 1H), 4.25-4.19 (m, 1H), 3.83-3.79 (m, 1H), 3.30 (s, 3H), 2.68-2.62 (m, 1H), 2.34 (s, 3H), 2.16 (s, 3H), 2.09-2.05 (m, 1H). | $R_T$ = 0.724 min, m/z = 412.0 |
| Example 597<br>0.13<br>WX Method 096 | 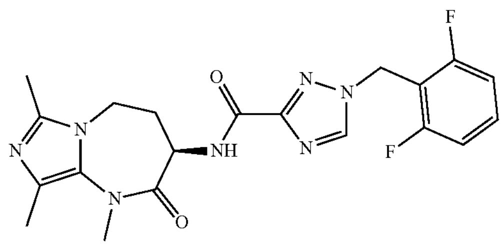 [SMILES: Cc1nc(C)n2c1N(C)C(=O)[C@H](NC(=O)c1ncn(Cc3c(F)cccc3F)n1)CC2]<br>1-[(2,6-difluorophenyl)methyl]-N-(3R)-1,7,9-trimethyl-2-oxo-4,5-dihydro-3H-imidazo[1,5-a][1,3diazepin-3-yl-1,2,4-triazole-3-carboxamide | Single<br>Unknown Stereoisomer | $^1H$ NMR (400 MHz, $CD_3OD$) δ 8.61 (s, 1H), 7.50-7.42 (m, 1H), 7.08-7.03 (m, 2H), 5.48 (s, 2H), 4.57-4.52 (m, 1H), 4.25-4.19 (m, 1H), 3.83-3.79 (m, 1H), 3.30 (s, 3H), 2.68-2.62 (m, 1H), 2.34 (s, 3H), 2.16 (s, 3H), 2.09-2.05 (m, 1H). | $R_T$ = 0.544 min; m/z = 430.1 |
| Example 598<br>0.13<br>WX Method 099 | 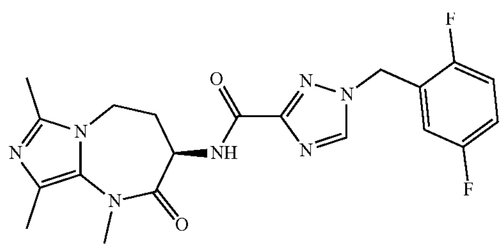 [SMILES: Cc1nc(C)n2c1N(C)C(=O)[C@H](NC(=O)c1ncn(Cc3cc(F)ccc3F)n1)CC2]<br>1-[(2,5-difluorophenyl)methyl]-N-(3R)-1,7,9-trimethyl-2-oxo-4,5-dihydro-3H-imidazo[1,5-a][1,3]diazepin-3-yl-1,2,4-triazole-3-carboxamide | Single<br>Unknown Stereoisomer | $^1H$ NMR (400 MHz, $CD_3OD$) δ 8.62 (s, 1H), 7.19-7.13 (m, 3H), 5.54 (s, 2H), 4.57-4.52 (m, 1H), 4.25-4.19 (m, 1H), 3.83-3.79 (m, 1H), 3.30 (s, 3H), 2.68-2.62 (m, 1H), 2.34 (s, 3H), 2.16 (s, 3H), 2.09-2.05 (m, 1H). | $R_T$ = 0.540 min; m/z = 430.0 |

TABLE 4-continued

| Example<br>Ki (μM)<br>METHOD | Structure | Stereo | $^1$H NMR | MS (m/z) R.T. |
|---|---|---|---|---|
| Example 599<br>0.035<br>WX Method 043 | 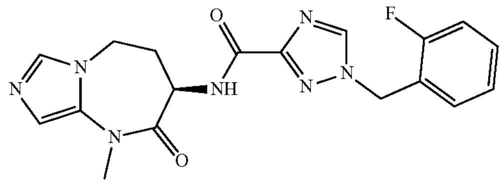 [SMILES: CN1C(=O)[C@H](NC(=O)c2ncn(Cc3ccccc3F)n2)CCn2cncc21]<br>1-[(2-fluorophenyl)methyl]-N-(3R)-1-methyl-2-oxo-4,5-dihydro-3H-imidazo[1,5-a][1,3]diazepin-3-yl-1,2,4-triazole-3-carboxamide | Single<br>Unknown Stereoisomer | $^1$H NMR (400 MHz, DMSO-$d_6$) δ 8.81 (s, 1H), 8.47 (d, J = 7.6 Hz, 1H), 7.58 (s, 1H), 7.44-7.33 2H), 7.27-7.19 (m, 2H), 6.95 (s, 1H), 5.55 (s, 2H), 4.38-4.31 (m, 2H), 3.88-3.81 (m, 1H), 3.23 (s, 3H), 2.44 (s, 1H), 2.27-2.21 (m, 1H). | $R_T$ = 1.693 min, m/z = 384.2$^+$ |
| Example 600<br>0.05<br>WX Method 96 | 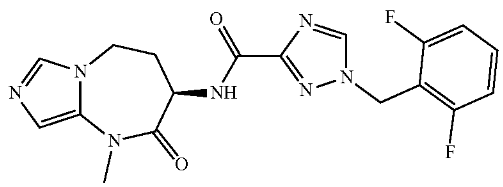 [SMILES: CN1C(=O)[C@H](NC(=O)c2ncn(Cc3c(F)cccc3F)n2)CCn2cncc21]<br>1-[(2,6-difluorophenyl)methyl]-N-[(3R)-1-methyl-2-oxo-4,5-dihydro-3H-imidazo[1,5-a][1,3]diazepin-3-yl-1,2,4-triazole-3-carboxamide | Single<br>Unknown Stereoisomer | $^1$H NMR (400 MHz, DMSO-$d_6$) δ 8.83 (s, 1H), 8.46 (d, J = 8.0 Hz, 1H), 7.61-7.43 (m, 2H), 7.20-7.16 (m, 2H), 6.95 (s, 1H), 5.56 (s, 2H), 4.39-4.25 (m, 2H), 3.88-3.78 (m, 1H), 3.22 (s, 3H), 2.48-2.39 (m, 1H), 2.27-2.20 (m, 1H) | $R_T$ = 1.681 min; m/z = 402.1 |
| Example 601<br>0.043<br>WX Method 043 | 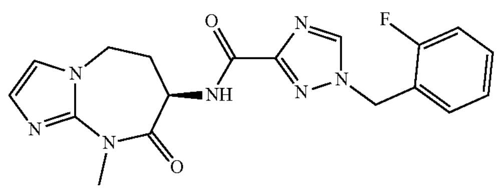 [SMILES: CN1C(=O)[C@H](NC(=O)c2ncn(Cc3ccccc3F)n2)CCn2ccnc21]<br>1-[(2-fluorophenyl)methyl]-N-(7R)-9-methyl-8-oxo-6,7-dihydro-5H-imidazo[1,2-a][1,3]diazepin-7-yl-1,2,4-triazole-3-carboxamide | Single<br>Unknown Stereoisomer | $^1$H NMR (400 MHz, $CD_3OD$) δ 8.58 (s, 1H), 7.42-7.34 (m, 2H), 7.21-7.11 (m, 2H), 7.08 (s, 1H), 6.95 (s, 1H), 5.54 (s, 2H), 4.54-4.47 (m, 1H), 4.32-4.25 (m, 1H), 4.09-4.02 (m, 1H), 3.38 (s, 3H), 2.87-2.79 (m, 1H), 2.28-2.23 (m, 1H). | $R_T$ = 1.293 min, m/z = 384.2 |
| Example 602<br>0.031<br>WX Method 96<br>(chirally assigned as R) | 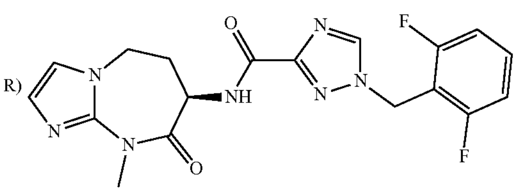<br>1-[(2,6-difluorophenyl)methyl]-N-[(7R)-9-methyl-8-oxo-6,7-dihydro-5H-imidazo[1,2-a][1,3]diazepin-7-yl]-1,2,4-triazole-3-carboxamide | Single<br>Unknown Stereoisomer | $^1$H NMR (400 MHz, DMSO-$d_6$) δ 8.84 (s, 1H), 8.53 (d, J = 7.6 Hz, 1H), 7.55-7.46 (m, 1H), 7.17 (t, J = 8.0 Hz 2H), 7.12 (s, 1H), 6.87 (s, 1H), 5.56 (s, 2H), 4.29-4.23 (m, 2H), 3.95-3.87 (m, 1H), 3.24 (s, 3H), 3.51-3.50 (m, 1H), 2.38-2.34 (m, 1H). | $R_T$ = 1.293 min; m/z = 402.1 |

TABLE 4-continued

| Example<br>Ki (μM)<br>METHOD | Structure | Stereo | $^1H$ NMR | MS (m/z) R.T. |
|---|---|---|---|---|
| Example 603<br>0.37<br>WX Method 059 | 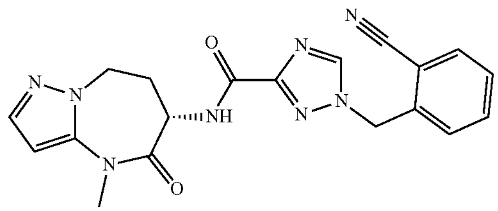 [SMILES: CN1C(=O)[C@@H](NC(=O)c2ncn(Cc3ccccc3C#N)n2)CCn2nccc21]<br>1-[(2-cyanophenyl)methyl]-N-(6S)-4-methyl-5-oxo-7,8-dihydro-6H-pyrazolo[1,5-a][1,3]dizepin-6-yl-1,2,4-triazole-3-carboxamide | Single<br>Known Stereoisomer | $^1H$ NMR (400 MHz, $CD_3OD$) δ 8.80 (s, 1H), 7.81 (d, J = 8.0 Hz, 1H), 7.74-7.68 (m, 1H), 7.66 (d, J=2.0 Hz, 1H), 7.58-7.53 (m, 1H), 7.49 (d, J = 8.0 Hz, 1H), 6.39 (d, J = 2.0 Hz, 1H), 5.74 (s, 2H), 4.57-4.52 (m, 1H), 4.50-4.44 (m, 1H), 4.38-4.27 (m, 1H), 3.36 (s, 3H), 2.91-2.81 (m, 1H), 2.35-2.28 (m, 1H). | $R_T$ = 1.732 min; m/z = 391.1 |
| Example 604<br>0.021<br>WX Method 062 | 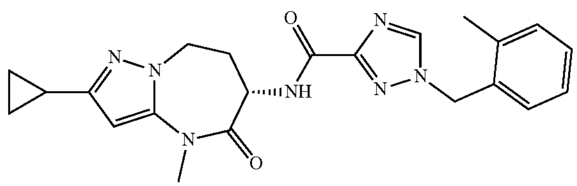 [SMILES: Cc1ccccc1Cn1cnc(C(=O)N[C@H]2CCn3nc(C4CC4)cc3N(C)C2=O)n1]<br>1-(o-tolylmethyl)-N-(6S)-2-cyclopropyl-4-methyl-5-oxo-7,8-dihydro-6H-pyrazolo[1,5-a][1,3]diazepin-6-yl-1,2,4-triazole-3-carboxamide | Single<br>Known Stereoisomer | $^1H$ NMR (400 MHz, $CD_3OD$) δ 8.44 (s, 1H), 7.26-7.15 (m, 4H), 6.00 (s, 1H), 5.50 (s, 2H), 4.45-4.49 (m, 1H), 4.28-4.23 (m, 1H), 4.20-4.18 (m, 1H), 3.35 (s, 3H), 2.85-2.80 (m, 1H), 2.34 (s, 3H), 2.24-2.22 (m, 1H), 1.92-1.88 (m, 1H), 0.95-0.92 (m, 2H), 0.75-0.72 (m, 2H). | $R_T$ = 1.69 min; m/z = 420.2 |
| Example 605<br>0.0095<br>WX Method 142 | 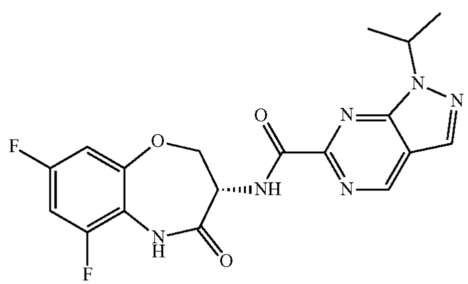 [SMILES: CC(C)n1ncc2cnc(C(=O)N[C@H]3COc4cc(F)cc(F)c4NC3=O)nc21]<br>1-isopropyl-N-[(3S)-6,8-difluoro-4-oxo-3,5-dihydro-2H-1,5-benzoxazepin-3-yl]pyrazolo[3,4-d]pyrimidine-6-carboxamide | Single<br>Known Stereoisomer | $^1H$ NMR (400 MHz, $CD_3OD$) δ 9.36 (s, 1H), 8.39 (s, 1H), 6.98-6.88 (m, 2H), 5.46-5.42 (m, 1H), 5.16-5.13 (m, 1H), 4.80-4.76 (m, 1H), 4.58 (t, J = 10.4 Hz, 1H), 1.60 (d, J = 6.4 Hz, 6H). | $R_T$ = 0.787 min, m/z = 403.0 |

TABLE 4-continued

| Example Ki (μM) METHOD | Structure | Stereo | $^1$H NMR | MS (m/z) R.T. |
| --- | --- | --- | --- | --- |
| Example 606<br>0.0048<br>WX Method 142 | 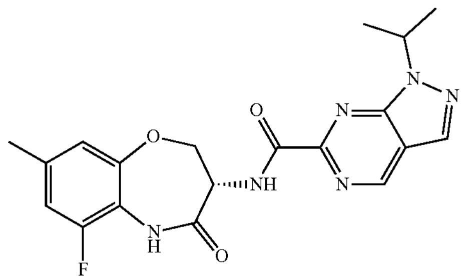 [SMILES: Cc1cc(F)c2c(c1)OC[C@H](NC(=O)c1ncc3cnn(C(C)C)c3n1)C(=O)N2]<br>1-isopropyl-N-R3S)-6-fluoro-8-methyl-4-oxo-3,5-dihydro-2H-1,5-benzoxazepin-3-yl]pyrazolo[3,4-d] pyrimidine-6-carboxam | Single<br>Known Stereoisomer | $^1$H NMR (400 MHz, $CD_3OD$) δ 9.36 (s, 1H), 8.39 (s, 1H), 6.91-6.88 (m, 2H), 5.47-5.42 (m, 1H), 5.12-5.09 (m, 1H), 4.76-4.72 (m, 1H), 4.51 (t, J = 10.4 Hz, 1H), 2.36 (s, 3H), 1.60 (d, J = 6.4 Hz, 6H). | $R_T$ = 0.787 min, m/z = 399.0 |
| Example 607<br>G030786100.028<br>WX Method 142 | 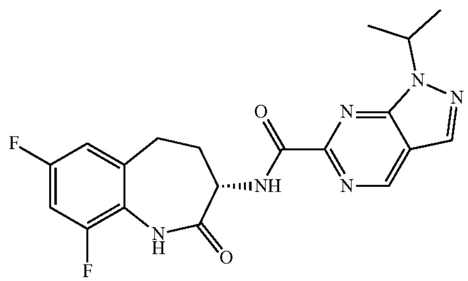<br>1-isopropyl-N-[(3S)-7,9-difluoro-2-oxo-1,3,4,5-tetrahydro-1-benzazepin-3-yl]pyrazolo[3,4-d] pyrimidine-6-carboxamide | Single<br>Known Stereoisomer | $^1$H NMR (400 MHz, $CD_3OD$) δ 9.35 (s, 1H), 8.38 (s, 1H), 7.05-7.00 (m, 2H), 5.45-5.40 (m, 1H), 4.69-4.64 (m, 1H), 3.05-3.02 (m, 1H), 2.89-2.76 (m, 2H),2.32-2.26 (m, 1H), 1.60 (d, J = 6.8 Hz, 6H). | $R_T$ = 0.770 min, m/z = 401.0 |
| Example 608<br>0.19<br>WX Method<br>(Chirally assigned as R) | 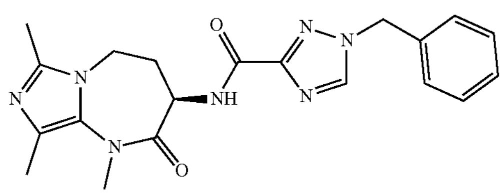 [SMILES: Cc1nc(C)n2c1N(C)C(=O)[C@H](NC(=O)c1ncn(Cc3ccccc3)n1)CC2]<br>1-benzyl-N-(3R)-1,7,9-trimethyl-2-oxo-4,5-dihydro-3H-imidazo[1,5-a][1,3]diazepin-3-yl-1,2,4-triazole-3-carboxamide | Single<br>Unknown Stereoisomer | $^1$H NMR (400 MHz, $CD_3OD$) δ 8.57 (s, 1H), 7.39-7.35 (m, 5H), 5.48 (s, 2H), 4.57-4.52 (m, 1H), 4.25-4.19 (m, 1H), 3.83-3.79 (m, 1H), 3.30 (s, 3H), 2.68-2.62 (m, 1H), 2.34 (s, 3H), 2.16 (s, 3H), 2.09-2.05 (m, 1H). | $R_T$ = 1.332 min; m/z = 394.2 |

TABLE 4-continued

| Example Ki (μM) METHOD | Structure | Stereo | $^{1}$H NMR | MS (m/z) R.T. |
|---|---|---|---|---|
| Example 609<br>0.071<br>WX Method 140 | 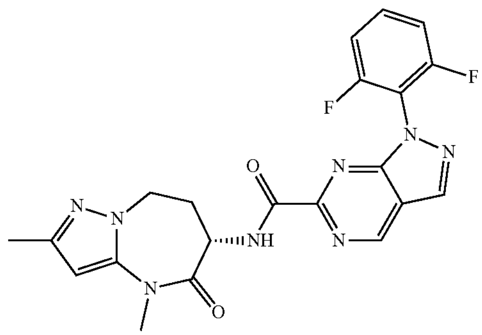 [SMILES: Cc1cc2n(n1)CC[C@H](NC(=O)c1ncc3cnn(-c4c(F)cccc4F)c3n1)C(=O)N2C]<br>1-(2,6-difluorophenyl)-N-[(6S)-2,4-dimethyl-5-oxo-7,8-dihydro-6H-pyrazolo[1,5-a][1,3]diazepin-6-yl]pyrazolo[2,3-d]pyrimidine-6-carboxamide | Single<br>Known Stereoisomer | $^{1}$H NMR (400 MHz, $CD_3OD$) δ 9.58 (s, 1H), 8.76 (s, 1H), 7.77-7.68 (m, 1H), 7.35-7.31 (m, 2H), 6.35 (s, 1H), 4.73-4.71 (m, 1H), 4.47-4.40 (m, 1H), 4.38-4.31 (m, 1H), 3.38 (s, 3H), 3.00-2.92 (m, 1H), 2.42-2.30 (m, 4H). | $R_T$ = 0.934 min; m/z = 453.3 |
| Example 610<br>0.92<br>WX Method 103 | 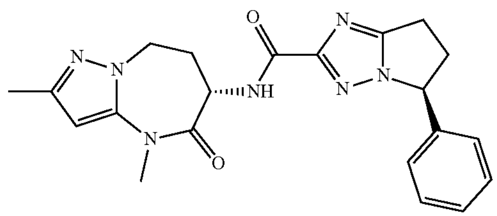 [SMILES: Cc1cc2n(n1)CC[C@H](NC(=O)c1nc3n(n1)[C@H](c1ccccc1)CC3)C(=O)N2C]<br>(S)-N-((S)-2,4-dimethyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]trizole-2-carboxamide | Single<br>Unknown Stereoisomer | $^{1}$H NMR (400 MHz, $CD_3OD$) δ 7.38-7.34 (m, 3H), 7.21-7.20 (m, 2H), 6.10 (s, 1H), 5.55-5.52 (m, 1H), 4.53-4.48 (m, 1H), 4.28-4.26 (m, 1H), 4.21-4.18 (m, 1H), 3.31 (s, 3H), 3.26-3.24 (m, 1H), 3.14-3.12 (m, 1H), 3.06-3.04 (m, 1H), 2.91-2.80 (m, 1H), 2.66-2.64 (m, 1H), 2.24-2.20 (m, 4H). | $R_T$ = 0.752 min, m/z = 406.1 |
| Example 611<br>WX Method 10 | 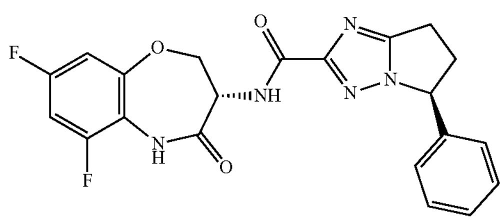 [SMILES: O=C(N[C@H]1COc2cc(F)cc(F)c2NC1=O)c1nc2n(n1)[C@H](c1ccccc1)CC2]<br>(5S)-5-phenyl-N-[(3S)-6,8-difluoro-4-oxo-3,5-dihydro-H-1,5-benzoxazepin-3-yl]-6,7-dihydro-5H-pyrrolo[1,2-b][1,2,4]triazole-2-carboxamide | Single<br>Unknown Stereoisomer | $^{1}$H NMR (400 MHz, $CD_3OD$) δ 7.38-7.34 (m, 3H), 7.22-7.20 (m, 2H), 6.94-6.84 (m, 2H), 5.57-5.53 (m, 1H), 5.07-5.02 (m, 1H), 4.66-4.62 (m, 1H), 4.50-4.47 (m, 1H), 3.25-3.15 (m, 1H), 3.13-3.03 (m, 2H), 2.69-2.66 (m, 1H). | $R_T$ = 0.080 min, m/z = 426.0 |

TABLE 4-continued

| Example Ki (μM) METHOD | Structure | Stereo | $^{1}$H NMR | MS (m/z) R.T. |
|---|---|---|---|---|
| Example 612<br>0.071<br>WX Method 103 | 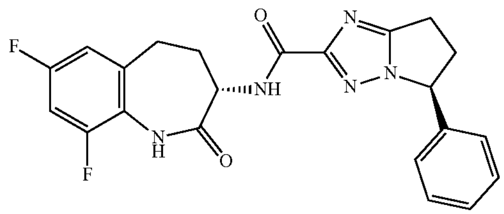 [SMILES: O=C(N[C@H]1CCc2cc(F)cc(F)c2NC1=O)c1nc2n(n1)[C@H](c1ccccc1)CC2]<br>(5S)-5-phenyl-N-[(3S)-7,9-difluoro-2-oxo-1,3,4,5-tetrahydro-l-benzazepin-3-yl]-6,7-dihydro-5H-pyrrolo[1,2-b][1,2,4]triazole-2-carboxamide | Single Unknown Stereoisomer | $^{1}$H NMR (400 MHz, $CD_3OD$) δ 7.40-7.33 (m, 3H), 7.21-7.20 (m, 2H), 7.01-6.97 (m, 2H), 5.55-5.52 (m, 1H), 4.57-4.52 (m, 1H), 3.24-2.95 (m, 4H), 2.82-2.81 (m, 1H), 2.67-2.62 (m, 2H), 2.23-2.17 (m, 1H). | $R_T$ = 0.798 min, m/z = 424.1 |
| Example 613<br>0.071<br>WX Method 103 | 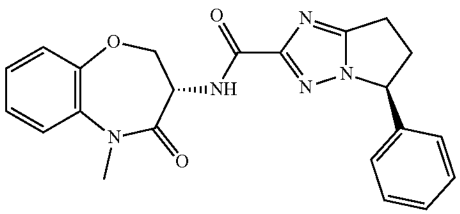 [SMILES: CN1C(=O)[C@@H](NC(=O)c2nc3n(n2)[C@H](c2ccccc2)CC3)COc2ccccc21]<br>rac-(5S)-5-phenyl-N-[rac-(3S)-5-methyl-4-oxo-2,3-dihydro-1,5-benzoxazepin-3-yl]-6,7-dihydro-5H-pyrrolo[1,2-b][1,2,4]triazole-2-carboxamide | Single Unknown Stereoisomer | $^{1}$H NMR (400 MHz, $CD_3OD$) δ 7.40-7.30 (m, 6H), 7.29-7.20 (m, 3H), 5.54 (t, J = 6.8 Hz, 1H), 4.98-4.95 (m, 1H), 4.58-4.54 (m, 1H), 4.40-4.35 (m, 1H), 3.39 (s, 3H), 3.27-3.24 (m, 1H), 3.14-3.04 (m, 2H), 2.67-2.65 (m, 1H). | $R_T$ = 0.823 min, m/z = 404.1 |
| Example 614<br>0.79<br>WX Method 103 | 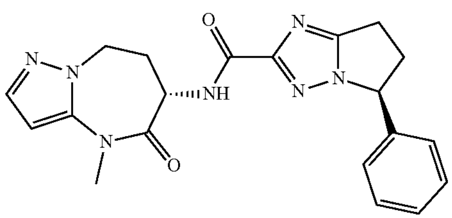 [SMILES: CN1C(=O)[C@@H](NC(=O)c2nc3n(n2)[C@H](c2ccccc2)CC3)CCn2nccc21]<br>rac-(5S)-5-phenyl-N-[rac-(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereoisomer | $^{1}$H NMR (400 MHz, $CD_3OD$) δ 7.51 (s, 1H), 7.38-7.34 (m, 3H), 7.22-7.20 (m, 2H), 6.29 (s, 1H), 5.55 (t, J = 6.8 Hz, 1H), 4.51-4.38 (m, 2H), 4.26-4.25 (m, 1H), 3.34 (s, 3H), 3.26-3.24 (m, 1H), 3.14-3.04 (m, 2H), 2.88-2.83 (m, 1H), 2.67-2.65 (m, 1H), 2.28-0.23 (m, 1H). | $R_T$ = 0.753 min, m/z = 392.0 |

TABLE 4-continued

| Example Ki (μM) METHOD | Structure | Stereo | $^1$H NMR | MS (m/z) R.T. |
|---|---|---|---|---|
| Example 615 0.011 WX Method 108 | 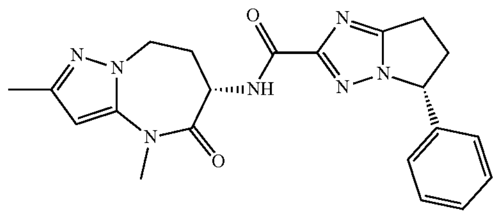 [SMILES: Cc1cc2n(n1)CC[C@H](NC(=O)c1nc3n(n1)[C@@H](c1ccccc1)CC3)C(=O)N2C] (5R)-5-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Known Stereoisomer | $^1$H NMR (400 MHz, $CD_3OD$) δ 7.41-7.23 (m, 3H), 7.23-7.21 (m, 2H), 6.10 (s, 1H), 5.56-5.52 (m, 1H), 4.53-4.48 (m, 1H), 4.29-4.19 (m, 2H), 3.31 (s, 3H), 3.26-3.24 (m, 1H), 3.15-3.05 (m, 2H), 2.85-2.81 (m, 1H), 2.67-2.60 (m, 1H), 2.25-2.21 (m, 4H). | $R_T$ = 0.759 min, m/z = 406.1 |
| Example 616 0.0057 WX Method 155 | 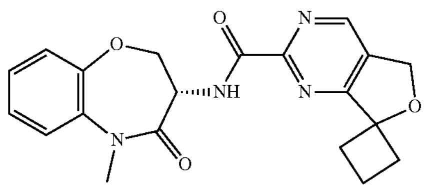 [SMILES: CN1C(=O)[C@@H](NC(=O)c2ncc3c(n2)C2(CCC2)OC3)COc2ccccc21] N-[(3S)-5-methyl-4-oxo-2,3-dihydro-1,5-benzoxazepin-3-yl]spiro[5H-furo[3,4-d]pyrimidine-7,1'-cyclobutane]-2-carboxamide | Single Known Stereoisomer | $^1$H NMR (400 MHz, $CD_3OD$) δ 8.78 (s, 1H), 7.43 (m, 1H), 7.35-7.20 (m, 3H), 5.13 (s, 2H), 5.08-4.99 (m, 1H), 4.71 (m, 1H), 4.43 (m, 1H), 3.44 (s, 3H), 2.59-2.47 (m, 4H), 2.35-2.20 (m, 1H), 1.92 (m, 1H). | $R_T$ = 1.65 min, m/z = 381.1 |
| Example 617 0.011 WX Method 155 | 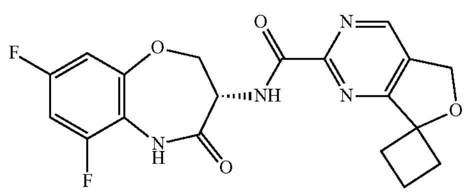 [SMILES: O=C(N[C@H]1COc2cc(F)cc(F)c2NC1=O)c1ncc2c(n1)C1(CCC1)OC2] N-[(3S)-6,8-difluoro-4-oxo-3,5-dihydro-2H-1,5-benzoxazepin-3-yl]spiro[5H-furo[3,4-d]pyrimide-7,1'-cyclobutane]-2-carboxamide | Single Known Stereoisomer | $^1$H NMR (400 MHz, $CD_3OD$) δ 8.79 (s, 1H), 6.99-6.80 (m, 2H), 5.22-5.06 (m, 3H), 4.81-4.75 (m, 1H), 4.59-4.47 (m, 1H), 2.61-2.45 (m, 4H), 2.35-2.21 (m, 1H), 1.92 (m, 1H). | $R_T$ = 1.62 min, m/z = 403.1 |

TABLE 4-continued

| Example Ki (μM) METHOD | Structure | Stereo | $^1$H NMR | MS (m/z) R.T. |
|---|---|---|---|---|
| Example 618 0.024 WX Method 155 | 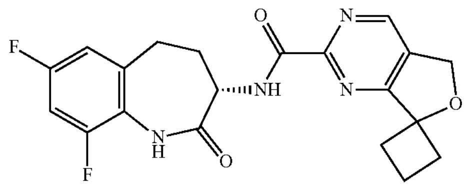 [SMILES: O=C(N[C@H]1CCc2cc(F)cc(F)c2NC1=O)c1ncc2c(n1)C1(CCC1)OC2] N-[(3S)-7,9-difluoro-2-oxo-1,3,4,5-tetrahydro-1-benzazepin-3-yl]spiro[5H-furo[3,-d]pyrimidine-7,1'-cyclobutane]-2-carboxamide | Single Known Stereoisomer | $^1$H NMR (400 MHz, $CD_3OD$) δ 8.78 (s, 1H), 7.07-6.98 (m, 2H), 5.13 (s, 2H), 4.70-4.57 (m, 1H), 3.08-2.96 (m, 1H), 2.89-2.75 (m, 2H), 2.59-2.47 (m, 4H), 2.33-2.19 (m, 2H), 1.97-1.87 (m, 1H). | $R_T$ = 1.60 min, m/z = 401.1 |
| Example 619 0.18 WX Method N | 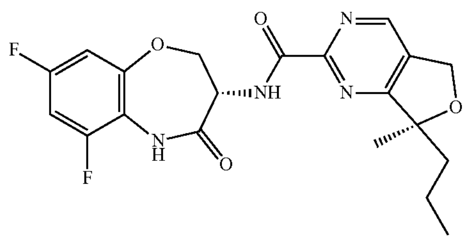 [SMILES: CCC[C@]1(C)OCc2cnc(C(=O)N[C@H]3COc4cc(F)cc(F)c4NC3=O)nc21] (7S)-7-methyl-7-propyl-N-[(3S)-6,8-difluoro-4-oxo-3,5-dihydro-2H-1,5-benzoxazepin-3-yl]-5H-furo[3,4-d]pyrimidine-2-carboxamide | Single Unknown Stereoisomer | $^1$H NMR (400 MHz, $CD_3OD$) δ 8.83 (s, 1H), 6.97-6.88 (m, 2H), 5.17-5.07 (m, 3H), 4.79-4.74 (m, 1H), 4.58-4.52 (m, 1H), 1.93-1.83 (m, 2H), 1.50-1.40 (m, 4H), 1.07-1.01 (m, 1H), 0.90-0.86 (m, 3H). | $R_T$ = 0.815 min; m/z = 419.0 |
| Example 620 0.014 WX Method N | 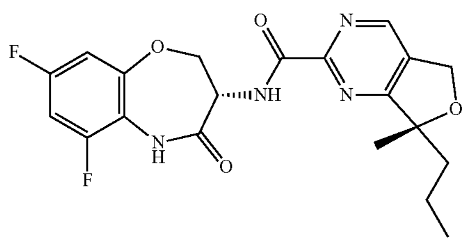 [SMILES: CCC[C@@]1(C)OCc2cnc(C(=O)N[C@H]3COc4cc(F)cc(F)c4NC3=O)nc21] (7R)-7-methyl-7-propyl-N-[(3S)-6,8-difluoro-4-oxo-3,5-dihydro-2H-1,5-benzoxazepin-3-yl]-5H-furo[3,4-d]pyrimidine-2-carboxamide | Single Unknown Stereoisomer | $^1$H NMR (400 MHz, $CD_3OD$) δ 8.83 (s, 1H), 6.97-6.88 (m, 2H), 5.17-5.07 (m, 3H), 4.79 4.74 (m, 1H), 4.58-4.52 (m, 1H), 1.93-1.83 (m, 2H), 1.50-1.40 (m, 4H), 1.07-1.01 (m, 1H), 0.90-0.86 (m, 3H). | $R_T$ = 0.815 min; m/z = 419.0 |

TABLE 4-continued

| Example Ki (μM) METHOD | Structure | Stereo | $^1$H NMR | MS (m/z) R.T. |
|---|---|---|---|---|
| Example 621<br>0.0031<br>WX Method 108 | 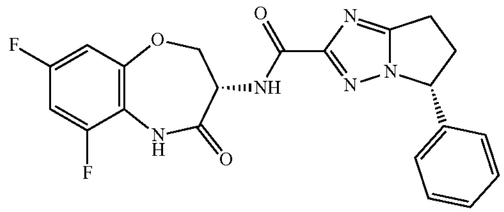 [SMILES: O=C(N[C@H]1COc2cc(F)cc(F)c2NC1=O)c1nc2n(n1)[C@@H](c1ccccc1)CC2]<br>(5R)-5-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide | Single Known Stereoisomer | $^1$H NMR (400 MHz, $CD_3OD$) δ 7.41-7.35 (m, 3H), 7.23-7.21 (m, 2H), 6.92-6.84 (m, 2H), 5.57-5.53 (m, 1H), 5.07-5.03 (m, 1H), 4.67-4.65 (m, 1H), 4.63-4.48 (m, 1H), 3.27-3.25 (m, 1H), 3.14-3.13 (m, 1H), 3.08-3.06 (m, 1H), 2.70-2.67 (m, 1H). | $R_T$ = 0.796 min; m/z = 426.0 |
| Example 622<br>0.005<br>WX Method 108 | 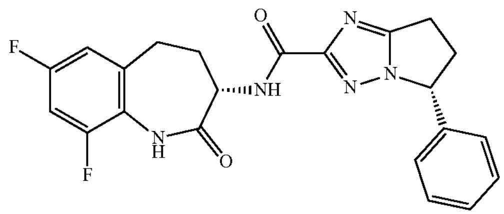 [SMILES: O=C(N[C@H]1CCc2cc(F)cc(F)c2NC1=O)c1nc2n(n1)[C@@H](c1ccccc1)CC2]<br>(5R)-5-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide | Single Known Stereoisomer | $^1$H NMR (400 MHz, $CD_3OD$) δ 7.40-7.34 (m, 3H), 7.22-7.21 (m, 2H), 7.00-6.98 (m, 2H), 5.56-5.52 (m, 1H), 4.60-4.53 (m, 1H), 3.27-3.25 (m, 1H), 3.12-3.10 (m, 1H), 3.07-3.05 (m, 1H), 2.96-2.93 (m, 1H), 2.85-2.82 (m, 1H), 2.66-2.63 (m, 2H), 2.21-2.16 (m, 1H). | $R_T$ = 0.797 min; m/z = 424.0 |
| Example 623<br>0.0034<br>WX Method 108 | 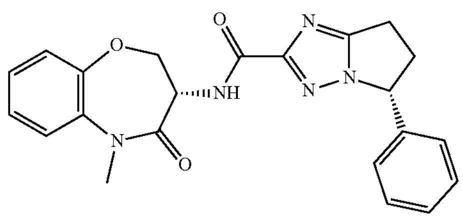 [SMILES: CN1C(=O)[C@@H](NC(=O)c2nc3n(n2)[C@@H](c2ccccc2)CC3)COc2ccccc21]<br>(5R)-5-phenyl-N-[(3S)-5-methyl-4-oxo-2,3-dihydro-1,5-benzoxazepin-3-yl]-6,7-dihydro-5H-pyrrolo[1,2-b][1,2,4]triazole-2-carboxamide | Single Known Stereoisomer | $^1$H NMR (400 MHz, $CD_3OD$) δ 7.41-7.21 (m, 9H), 5.54 (t, J = 6.8 Hz, 1H), 5.00-4.96 (m, 1H), 4.59-4.56 (m, 1H), 4.41-4.36 (m, 1H), 3.40 (s, 3H), 3.27-3.24 (m, 1H), 3.15-3.04 (m, 2H), 2.67-2.65 (m, 1H). | $R_T$ = 0.801 min; m/z = 404.1 |

TABLE 4-continued

| Example Ki (μM) METHOD | Structure | Stereo | $^1$H NMR | MS (m/z) R.T. |
|---|---|---|---|---|
| Example 624 0.02 WX Method 108 | 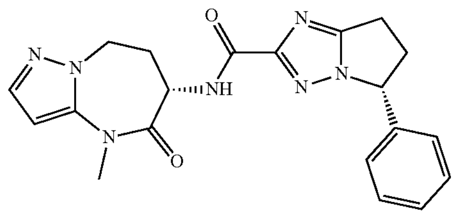 [SMILES: CN1C(=O)[C@@H](NC(=O)c2nc3n(n2)[C@@H](c2ccccc2)CC3)CCn2nccc21] (5R)-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Known Stereoisomer | $^1$H NMR (400 MHz, $CD_3OD$) δ 7.51 (s, 1H), 7.38-7.34 (m, 3H), 7.22-7.20 (m, 2H), 6.29 (s, 1H), 5.55 (t, J = 6.8 Hz, 1H), 4.51-4.38 (m, 2H), 4.26-4.25 (m, 1H), 3.34 (s, 3H), 3.26-3.24 (m, 1H), 3.14-3.04 (m, 2H), 2.88-2.83 (m, 1H), 2.67-2.65 (m, 1H), 2.28-2.23 (m, 1H). | $R_T$ = 0.727 min; m/z = 392.0 |
| Example 625 0.45 WX Method 113 | 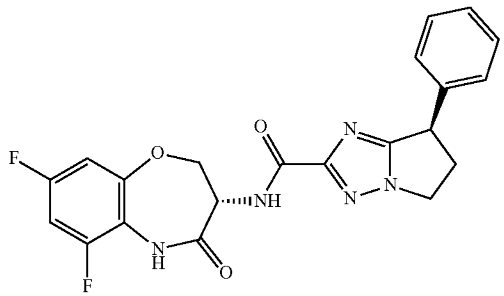 [SMILES: O=C(N[C@H]1COc2cc(F)cc(F)c2NC1=O)c1nc2n(n1)CC[C@@H]2c1ccccc1] (7R)-7-phenyl-N-[(3S)-6,8-difluoro-4-oxo-3,5-dihydro-2H-1,5-benzoxazepin-3-yl]-6,7-dihydro-5H-pyrrolo[1,2-b][1,2,4]triazole-2-carboxamide | Single Unknown Stereoisomer | $^1$H NMR (400 MHz, $CD_3OD$) δ 7.29-7.22 (m, 2H), 7.21-7.14 (m, 3H), 6.87-6.79 (m, 1H), 6.78-6.75 (m, 1H), 4.98-4.94 (m, 1H), 4.58-4.56 (m, 1H), 4.48-4.27 (m, 3H), 4.32-4.19 (m, 1H), 3.18-3.14 (m, 1H), 2.67-2.56 (m, 1H). | $R_T$ = 2.23 min, m/z = 426.2 |
| Example 626 0.014 WX Method 113 | 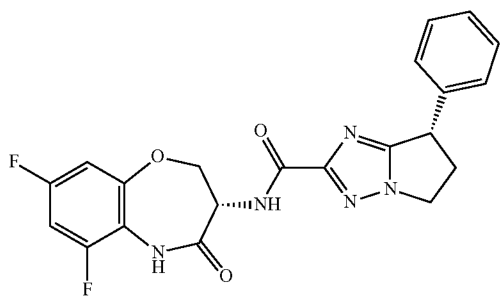 [SMILES: O=C(N[C@H]1COc2cc(F)cc(F)c2NC1=O)c1nc2n(n1)CC[C@H]2c1ccccc1] (7S)-7-phenyl-N-R35)-6,8-difluoro-4-oxo-3,5-dihydro-2H-1,5-benzoxazepin-3-yl]-6,7-dihydro-5H-pyrrolo[1,2-b][1,2,4]triazole-2-carboxamide | Single Unknown Stereoisomer | $^1$H NMR (400 MHz, $CD_3OD$) δ 7.38-7.33 (m, 2H), 7.31-7.26 (m, 3H), 6.96-6.89 (m, 1H), 6.88-685 (m, 1H), 5.08-5.04 (m, 1H), 4.68-6.46 (m, 1H), 4.56-4.37 (m, 3H), 4.32-4.23 (m, 1H), 3.26-3.25 (m, 1H), 2.78-2.66 (m, 1H). | $R_T$ = 2.22 min, m/z = 426.1 |

TABLE 4-continued

| Example Ki (μM) METHOD | Structure | Stereo | $^1$H NMR | MS (m/z) R.T. |
|---|---|---|---|---|
| Example 627<br>0.16<br>WX Method 114 | 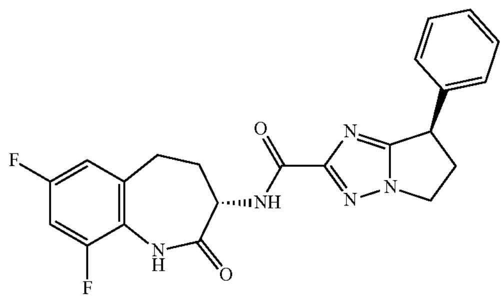 [SMILES: O=C(N[C@H]1CCc2cc(F)cc(F)c2NC1=O)c1nc2n(n1)CC[C@@H]2c1ccccc1]<br>(7R)-7-phenyl-N-[(3S)-7,9-difluoro-2-oxo-1,3,4,5-tetra hydro-1-benzazepin-3-yl]-6,7-dihydro-5H-pyrrolo[1,2-b][1,2,4]triazole-2-carboxamide | Single<br>Unknown Stereoisomer | $^1$H NMR (400 MHz, $CD_3OD$) δ 7.37-7.33 (m, 2H), 7.32-7.26 (m, 3H), 7.01-6.98 (m, 2H), 4.59-4.50 (m, 2H), 4.45-4.40 (m, 1H), 4.27-4.25 (m, 1H), 3.30-3.27 (m, 1H), 2.98-2.96 (m, 1H), 2.83-2.81 (m, 1H), 2.71-2.63 (m, 2H), 2.22-2.19 (m, 1H). | $R_T$ = 1.730 min, m/z = 424.1 |
| Example 628<br>0.005<br>WX Method 114 | 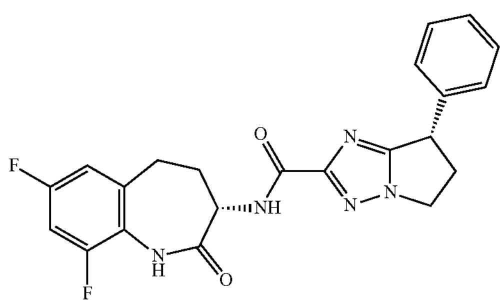 [SMILES: O=C(N[C@H]1CCc2cc(F)cc(F)c2NC1=O)c1nc2n(n1)CC[C@H]2c1ccccc1]<br>(7S)-7-phenyl-N-[(3S)-7,9-difluoro-2-oxo-1,3,4,5-tetrahydro-1-benzazepin-3-yl]-6,7-dihydro-5H-pyrrolo[1,2-b][1,2,4]triazole-2-carboxamide | Single<br>Unknown Stereoisomer | $^1$H NMR (400 MHz, $CD_3OD$) δ 7.37-7.26 (m, 5H), 7.02-6.98 (m, 2H), 4.60-4.51 (m, 2H), 4.43-4.40 (m, 1H), 4.30-4.27 (m, 1H), 3.30-3.27 (m, 1H), 2.98-2.96 (m, 1H), 2.83-2.81 (m, 1H), 2.71-2.63 (m, 2H), 2.21-2.19 (m, 1H). | $R_T$ = 1.730 min, m/z = 424.1 |

TABLE 4-continued

| Example Ki (μM) METHOD | Structure | Stereo | $^1$H NMR | MS (m/z) R.T. |
|---|---|---|---|---|
| Example 629 0.014 WX Method 125 | 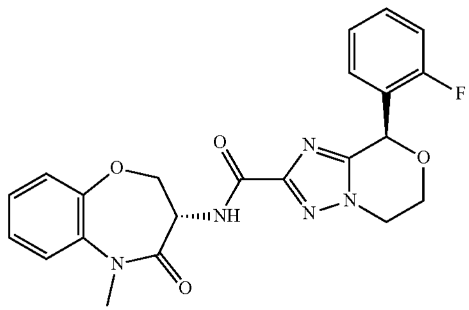 [SMILES: CN1C(=O)[C@@H](NC(=O)c2nc3n(n2)CCO[C@@H]3c2ccccc2F)COc2ccccc21] (8R)-8-(2-fluorophenyl)-N-[(3S)-5-methyl-4-oxo-2,3-di hydro-1,5-benzoxazepin-3-yl]-6,8-dihydro-5H-[1,2,4]triazolo[5,1-c][1,4]oxazine-2-carboxamide | Single Unknown Stereoisomer | $^1$H NMR (400 MHz, DMSO-$d_6$) δ 8.43 (d, J = 8.0 Hz, 1H), 7.52-7.45 (m, 2H), 7.45-7.39 (m, 1H), 7.34-7.20 (m, 5H), 6.18 (s, 1H), 4.86-4.77 (m, 1H), 4.61-4.55 (m, 1H), 4.45-4.32 (m, 4H), 4.25-4.17 (m, 1H), 3.29 (s, 3H). | $R_T$ = 0.80 min, m/z = 438.1 |
| Example 630 0.03 WX Method 125 | 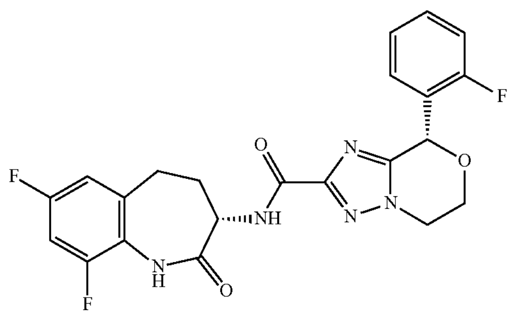 [SMILES: O=C(N[C@H]1CCc2cc(F)cc(F)c2NC1=O)c1nc2n(n1)CCO[C@H]2c1ccccc1F] (8S)-8-(2-fluorophenyl)-N-[(3S)-7,9-difluoro-2-oxo-1,3,4,5-tetrahydro-1-benzazepin-3-yl]-6,8-dihydro-5H-[1,2,4]triazolo[5,1-c][1,4]oxazine-2-carboxamide | Single Unknown Stereoisomer | $^1$H NMR (400 MHz, $CD_3OD$) δ 7.47-7.41 (m, 1H), 7.37-7.32 (m, 1H), 7.23-7.12 (m, 2H), 7.01 -6.94 (m, 3H), 6.13 (s, 1H), 4.57-4.33 (m, 4H), 4.27-4.18 (m, 1H), 3.00-2.89 (m, 1H), 2.72-2.75 (m, 1H), 2.64-2.53 (m, 1H), 2.23-2.15 (m, 1H). | $R_T$ = 0.79 min, m/z = 458.1 |

TABLE 4-continued

| Example Ki (μM) METHOD | Structure | Stereo | $^1$H NMR | MS (m/z) R.T. |
|---|---|---|---|---|
| Example 631<br>0.16<br>WX Method 138 | 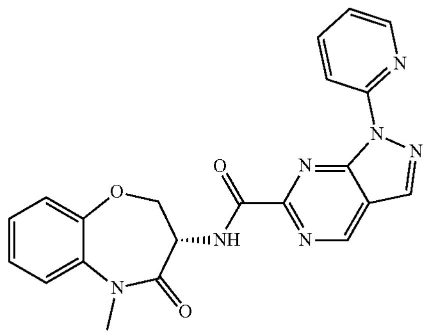 [SMILES: CN1C(=O)[C@@H](NC(=O)c2ncc3cnn(-c4ccccn4)c3n2)COc2ccccc21]<br>1-(2-pyridyl)-N-[(3S)-5-methyl-4-oxo-2,3-dihydro-1,5-benzoxazepin-3-yl]pyrazolo[3,4-d]pyrimidine-6-carboxamide | Single Known Stereoisomer | $^1$H NMR (400 MHz, $CD_3OD$) δ 9.53 (s, 1H), 8.68 (s, 1H), 8.65 (d, J = 4.0 Hz, 1H), 8.49 (d, J = 8.4 Hz, 1H), 8.19-8.12 (m, 1H), 7.54-7.50 (m, 1H), 7.48-7.44 (m, 1H), 7.36-7.30 (m, 2H), 7.28-7.25 (m, 1H), 5.12-5.07 (m, 1H), 4.73-4.69 (m, 1H), 4.55-4.47 (m, 1H), 3.45 (s, 3H). | $R_T$ = 0.757 min, m/z = 416.0 |
| Example 632<br>3.1<br>WX Method 138 | 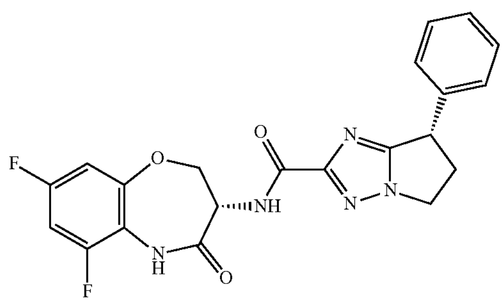 [SMILES: O=C(N[C@H]1COc2cc(F)cc(F)c2NC1=O)c1nc2n(n1)CC[C@H]2c1ccccc1]<br>1-(2-pyridyl)-N-R65)-2,4-dimethyl-5-oxo-7,8-dihydro-6H-pyrazolo[1,5-a][1,3]diazepin-6-yl]pyrazolo[3,4-d] pyrimidine-6-carboxamide | Single Known Stereoisomer | $^1$H NMR (400 MHz, $CD_3OD$) δ 9.53 (s, 1H), 8.68 (s, 1H), 8.64 (d, J = 4.0 Hz, 1H), 8.50 (d, J = 8.4 Hz, 1H), 8.18-8.11 (m, 1H), 7.55-7.50 (m, 1H), 6.14 (s, 1H), 4.66-4.59 (m, 1H), 4.36-4.27 (m, 2H), 3.37 (s, 3H), 3.02-2.92 (m, 1H), 2.39-2.31 (m, 1H), 2.27 (s, 3H). | $R_T$ = 0.712 min, m/z = 418.0 |

TABLE 4-continued

| Example Ki (μM) METHOD | Structure | Stereo | $^1$H NMR | MS (m/z) R.T. |
|---|---|---|---|---|
| Example 633<br>3.8<br>WX Method 138 | 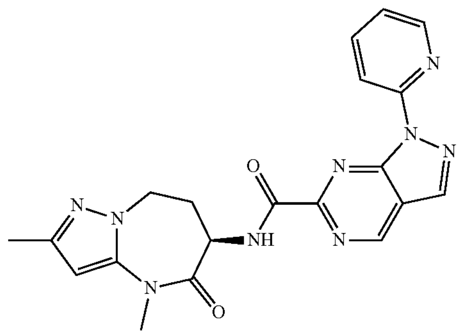 [SMILES: Cc1cc2n(n1)CC[C@@H](NC(=O)c1ncc3cnn(-c4ccccn4)c3n1)C(=O)N2C]<br>1-(2-pyridyl)-N-[(6R)-2,4-dimethyl-5-oxo-7,8-dihydro-6H-pyrazolo[1,5-a][1,3-d]pyepin-6-yl]pyrazolo[3,4-d]pyrimidine-6-carboxamide | Single<br>Known Stereoisomer | $^1$H NMR (400 MHz, $CD_3OD$) δ 9.52 (s, 1H), 8.68 (s, 1H), 8.64 (s, 1H), 8.48 (d, J = 8.4 Hz, 1H), 8.14 (t, J = 7.2 Hz, 1H), 7.56-7.49 (m, 1H), 6.14 (s, 1H), 4.67-4.59 (m, 1H), 4.41-4.25 (m, 2H), 3.37 (s, 3H), 3.01-2.93 (m, 1H), 2.38-2.29 (m, 1H), 2.27 (s, 3H). | $R_T$ = 0.709 min, m/z = 418.0 |
| Example 634<br>0.24<br>WX Method 129 | 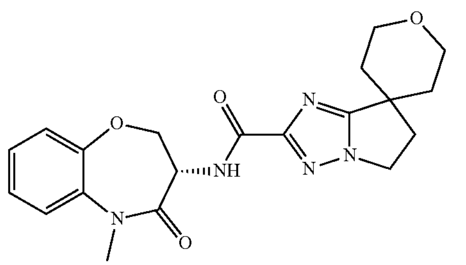 [SMILES: CN1C(=O)[C@@H](NC(=O)c2nc3n(n2)CCC32CCOCC2)COc2ccccc21]<br>N-[(3S)-5-methyl-4-oxo-2,3-dihydro-1,5-benzoxazepin-3-yl]spiro[5,6-dihydropyrrolo[1,2-b][1,2,4]triazole-7,4'-tetrahydropyran]-2-carboxamide | Single<br>Known Stereoisomer | $^1$H NMR (400 MHz, $CD_3OD$) δ 7.46-7.40 (m, 1H), 7.36-7.27 (m, 2H), 7.25-7.21 (m, 1H), 5.03-4.98 (m, 1H), 4.62-4.58 (m, 1H), 4.45-4.39 (m, 1H), 4.27-4.23 (m, 2H), 4.08-4.00 (m, 2H), 3.79-3.70 (m, 2H), 3.42 (s, 3H), 2.71-2.67 (m, 2H), 1.97-1.87 (m, 2H), 1.82-1.70 (m, 2H). | $R_T$ = 1.58 min, m/z = 3.98.3 |

TABLE 4-continued

| Example Ki (μM) METHOD | Structure | Stereo | $^1$H NMR | MS (m/z) R.T. |
|---|---|---|---|---|
| Example 635<br>7.3<br>WX Method 131 | 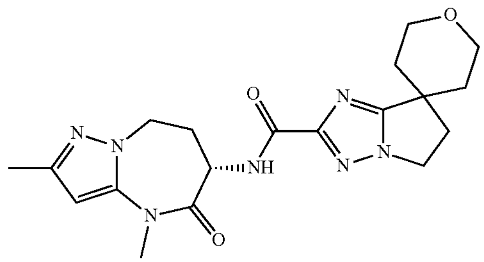<br>N-[(6S)-2,4-dimethyl-5-oxo-7,8-dihydro-6H-pyrazolo [1,5-a][1,3]diazepin-6-yl]spiro[5,6-dihydropyrrolo[1,2-b] [1,2,4]triazole-7,4'-trtrahydropyran]-2-carboxamide | Single Known Stereoisomer | $^1$H NMR (400 MHz, $CD_3OD$) δ 6.11 (s, 1H), 4.59-4.49 (m, 1H), 4.37-4.16 (m, 4H), 4.06-4.02 (m, 2H), 3.80-3.68 (m, 2H), 3.33 (s, 3H), 2.86-2.84 (m, 1H), 2.74-2.65 (m, 2H), 2.30-2.21 (m, 4H), 1.99-1.88 (m, 2H), 1.82-1.71 (m, 2H). | $R_T$ = 0.752 min, m/z = 407.1 |
| Example 636<br>0.13<br>WX Method 134 | 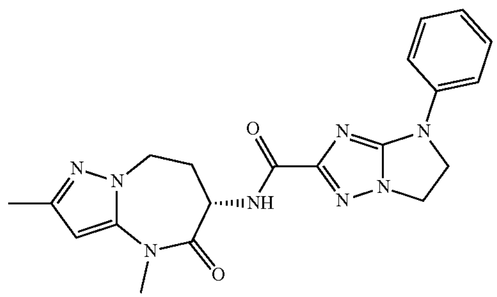<br>4-phenyl-N-[(6S)-2,4-dimethyl-5-oxo-7,8-dihydro-6H-pyrazolo[1,5-a][1,3]diazepin-6-yl]-5,6-dihdroimidazo [1,2-b][1,2,4]triazole-2-carboxamide | Single Known Stereoisomer | $^1$H NMR (400 MHz, $CD_3OD$) δ 7.58 (d, J = 8.0 Hz, 2H), 7.41-7.37(m, 2H), 7.06-7.02 (m, 1H), 6.15 (s, 1H), 4.63-4.51 (m, 3H), 4.48-4.41 (m, 2H), 4.33 (s, 1H), 4.29-4.23 (m, 1H), 3.35 (s, 3H), 2.91-2.84 (m, 1H), 2.38-2.21 (m, 4H). | $R_T$ = 0.714 min, m/z = 414.9 |
| Example 637<br>0.018<br>WX Method 164 | 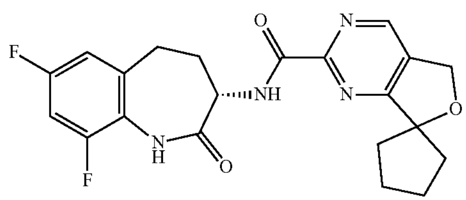 [SMILES: O=C(N[C@H]1CCc2cc(F)cc(F)c2NC1=O)c1ncc2c(n1)C1(CCCC1)OC2]<br>N-[(3S)-7,9-difluoro-2-oxo-1,3,4,5-tetrahydro-1-benzazepin-3-yl]spiro[5H-furo[3,4-d]pyrimidine-7,1'-cyclopentane]-2-carboxamide | Single Known Stereoisomer | $^1$H NMR (400 MHz, $CD_3OD$) δ 8.79 (s, 1H), 7.06-7.00 (m, 2H), 5.11 (s, 2H), 4.65-4.60 (m, 1H), 3.07-2.98 (m, 1H), 2.86-2.76 (m, 2H), 2.27-2.22 (m, 1H), 2.10-2.00 (m, 4H), 1.98-1.87 (m, 4H). | $R_T$ = 0.714 min, m/z = 414.9 |

TABLE 4-continued

| Example Ki (μM) METHOD | Structure | Stereo | $^1$H NMR | MS (m/z) R.T. |
| --- | --- | --- | --- | --- |
| Example 638 0.038 WX Method 121 | 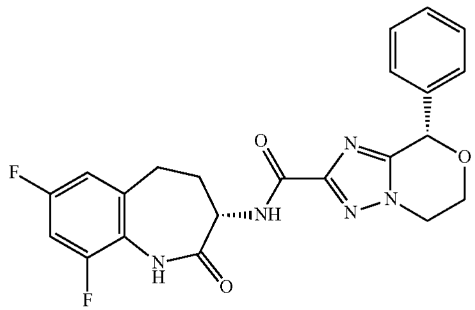 (8S)-8-phenyl-N-[(3S)-7,9-difluoro-2-oxo-1,3,4,5-tetrahydro-1-benzazepin-3-yl]-6,8-dihydro-5H-[1,2,4]triazolo[5,1-c][1,4]oxazine-2-carboxamide | Single Unknown Stereoisomer | $^1$H NMR (400 MHz, $CD_3OD$) δ 7.46-7.34 (m, 5H), 7.04-6.96 (m, 2H), 5.94 (s, 1H), 4.59-4.52 (m, 1H), 4.50-4.43 (m, 1H), 4.40-4.33 (m, 2H), 4.25-4.17 (m, 1H), 3.01-2.91 (m, 1H), 2.84-2.76 (m, 1H), 2.66-2.55 (m, 1H), 2.26-2.14 (m, 1H). | $R_T$ = 0.955 min, m/z = 440.2 |
| Example 639 0.42 WX Method 121 | 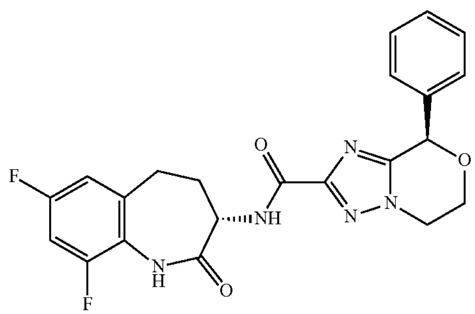 [SMILES: O=C(N[C@H]1CCc2cc(F)cc(F)c2NC1=O)c1nc2n(n1)CCO[C@@H]2c1ccccc1] (8R)-8-phenyl-N-[(3S)-7,9-difluoro-2-oxo-1,3,4,5-tetrahydro-1-benzazepin-3-yl]-6,8-dihydro-5H-[1,2,4]triazolo[5,1-c][1,4]oxamide | Single Unknown Stereoisomer | $^1$H NMR (400 MHz, $CD_3OD$) δ 7.46-7.34 (m, 5H), 7.03-6.95 (m, 2H), 5.94 (s, 1H), 4.60-4.52 (m, 1H), 4.50-4.43 (m, 1H), 4.40-4.32 (m, 2H), 4.25-4.16 (m, 1H), 3.01-2.91 (m, 1H), 2.84-2.76 (m, 1H), 2.66-2.54 (m, 1H), 2.24-2.13 (m, 1H). | $R_T$ = 0.955 min, m/z = 440.2 |

TABLE 4-continued

| Example<br>Ki (μM)<br>METHOD | Structure | Stereo | $^1$H NMR | MS (m/z) R.T. |
|---|---|---|---|---|
| Example 640<br>0.0094<br>WX Method 121 | 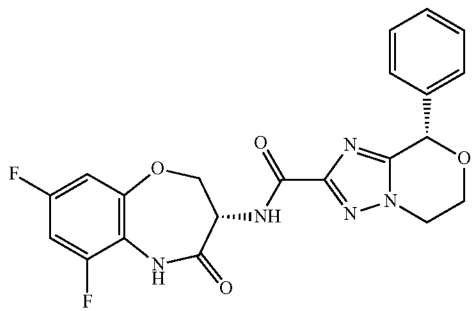 [SMILES: O=C(N[C@H]1COc2cc(F)cc(F)c2NC1=O)c1nc2n(n1)CCO[C@H]2c1ccccc1]<br>(8S)-8-phenyl-N-[(3S)-6,8-difluoro-4-oxo-3,5-dihydro-2H-1,5-benzoxazepin-3-yl]-6,8-dihydro-5H-[1,2,4]triazolo[5,1-c][1,4]oxazine-2-carboxamide | Single<br>Unknown<br>Stereoisomer | $^1$H NMR (400 MHz, $CD_3OD$) δ 7.45-7.35 (m, 5H), 6.96-6.89 (m, 1H), 6.88-6.82 (m, 1H), 5.95 (s, 1H), 5.09-5.01 (m, 1H), 4.68-4.60 (m, 1H), 4.51-4.46 (m, 2H), 4.42-4.33 (m, 2H), 4.26-4.17 (m, 1H). | $R_T$ = 0.956 min, m/z = 442.1 |
| Example 641<br>0.47<br>WX Method 121 | 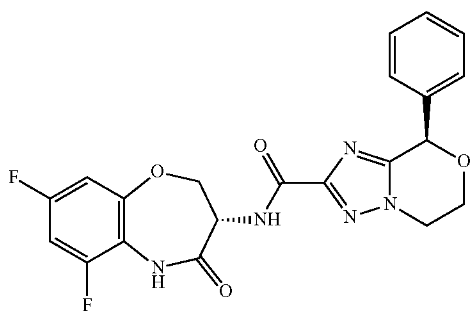<br>(8R)-8-phenyl-N-[(3S)-6,8-difluoro-4-oxo-3,5-dihydro-2H-1,5-benzoxazepin-3-yl]-6,8-dihydro-5H-[1,2,4]triazolo[5,1-c][1,4]oxazine-2-carboxamide | Single<br>Unknown<br>Stereoisomer | $^1$H NMR (400 MHz, $CD_3OD$) δ 7.47-7.33 (m, 5H), 6.97-6.89 (m, 1H), 6.85 (d, J = 9.6 Hz, 1H), 5.95 (s, 1H), 5.09-5.01 (m, 1H), 4.66-4.59 (m, 1H), 4.52-4.44 (m, 2H), 4.40-4.33 (m, 2H), 4.26-4.17 (m, 1H). | $R_T$ = 0.961 min, m/z = 442.1 |

TABLE 4-continued

| Example<br>Ki (μM)<br>METHOD | Structure | Stereo | $^1$H NMR | MS (m/z) R.T. |
|---|---|---|---|---|
| Example 642<br>0.012<br>WX Method 121 | 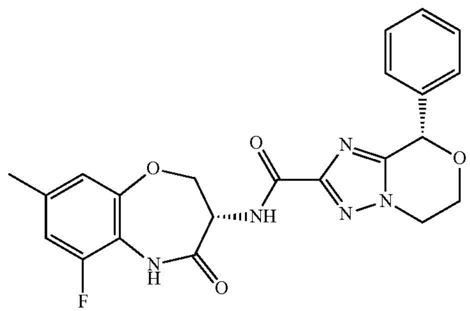 [SMILES: Cc1cc(F)c2c(c1)OC[C@H](NC(=O)c1nc3n(n1)CCO[C@H]3c1ccccc1)C(=O)N2]<br>(8S)-8-phenyl-N-[(3S)-6-fluoro-8-methyl-4-oxo-3,5-dihydro-2H-1,5-benzoxazepin-3-yl]-6,8-dihydro-5H-[1,2,4]triazolo[5,1-c][1,4]oxazine-2-carboxamide | Single Unknown Stereoisomer | $^1$H NMR (400 MHz, $CD_3OD$) δ 7.44-7.36 (m, 5H), 6.89-6.83 (m, 2H), 5.94 (s, 1H), 5.06-4.98 (m, 1H), 4.63-4.56 (m, 1H), 4.52-4.33 (m, 5H), 4.25-4.17 (m, 1H), 2.33 (s, 3H). | $R_T$ = 0.988 min, m/z = 438.2 |
| Example 643<br>0.36<br>WX Method 121 | 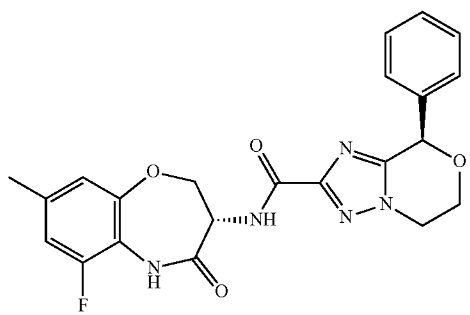 [SMILES: Cc1cc(F)c2c(c1)OC[C@H](NC(=O)c1nc3n(n1)CCO[C@@H]3c1ccccc1)C(=O)N2]<br>(8R)-8-phenyl-N-[(3 S)-6-fluoro-8-methyl-4-oxo-3,5-dihydro-2H-1,5-benzoxazepin-3-yl]-6,8-dihydro-5H-[1,2,4]triazolo[5,1-c][1,4]oxazine-2-carboxamide | Single Unknown Stereoisomer | $^1$H NMR (400 MHz, $CD_3OD$) δ 7.44-7.36 (m, 5H), 6.90-6.82 (m, 2H), 5.95 (s, 1H), 5.06-4.98 (m, 1H), 4.62-4.55 (m, 1H), 4.52-4.33 (m, 5H), 4.25-4.17 (m, 1H),2.33 (s, 3H). | $R_T$ = 0.994 min, m/z = 438.1 |

TABLE 4-continued

| Example Ki (µM) METHOD | Structure | Stereo | $^1$H NMR | MS (m/z) R.T. |
|---|---|---|---|---|
| Example 644 0.31 WX Method 0.19 | 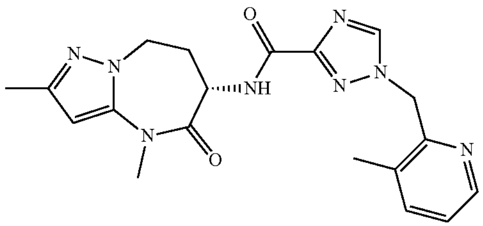 [SMILES: Cc1cc2n(n1)CC[C@H](NC(=O)c1ncn(Cc3ncccc3C)n1)C(=O)N2C] 1-[(3-methyl-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.57 (s, 1H), 8.32 (s, 1H), 7.68 (d, J = 7.6 Hz, 1H), 7.28-7.27 (m, 1H), 6.10 (s, 1H), 5.63 (s, 2H), 4.54-4.49 (m, 1H), 4.33-4.20 (m, 2H), 3.30 (s, 3H), 2.85-2.83 (m, 1H), 2.46 (s, 3H), 2.25-2.23 (m, 4H). | $R_T$ = 1.258 min, m/z = 395.1 |
| Example 645 1.2 WX Method 129 | 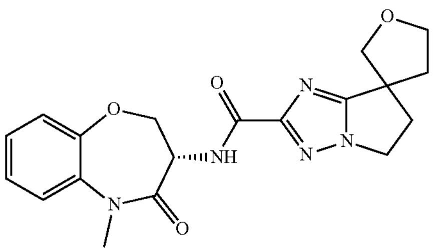 [SMILES: CN1C(=O)[C@@H](NC(=O)c2nc3n(n2)CCC32CCOC2)COc2ccccc21] N-[(3S)-5-methyl-4-oxo-2,3-dihydro-1,5-benzoxazepin-3-yl]spiro[5,6-dihydropyrrolo[1,2-b][1,2,4]triazole-7,3'-tetrahydrofuran]-2-carboxamide | Mixture of Diastereomers | $^1$H NMR (400 MHz, $CD_3OD$) δ 7.43 (d, J = 6.8 Hz, 1H), 7.33-7.30 (m, 2H), 7.23 (d, J = 6.0 Hz, 1H), 5.00-4.84 (m, 1H), 4.61-4.57 (m, 1H), 4.43-4.40 (m, 1H), 4.26 (t, J = 6.8 Hz, 2H), 4.13-4.09 (m, 1H), 4.03-4.00 (m, 1H), 3.95-3.91 (m, 1H), 3.88-3.85 (m, 1H), 3.42 (s, 3H), 2.85-2.79 (m, 2H), 2.40-2.35 (m, 1H), 2.21-2.18 (m, 1H). | $R_T$ = 0.713 min, m/z = 384.0 |
| Example 646 9.3 WX Method 129 | 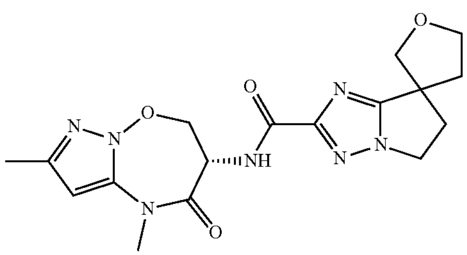 [SMILES: Cc1cc2n(n1)OC[C@H](NC(=O)c1nc3n(n1)CCC31CCOC1)C(=O)N2C] N-[(6S)-2,4-dimethyl-5-oxo-7,8-dihydro-6H-pyrazolo[1,5-a][1,3]diazepin-6-yl]spiro[5,6-dihydropyrrolo[1,2-b][1,2,4]triazole-7,3'-tetrahydrofuran]-2-carboxamide | Mixture of Diastereomers | $^1$H NMR (400 MHz, $CD_3OD$) δ 6.11 (s, 1H), 4.54-4.52 (m, 1H), 4.53-4.24 (m, 4H), 4.15-4.10 (m, 1H), 4.05-4.01 (m, 1H), 3.94-3.92 (m, 1H), 3.89-3.86 (m, 1H), 3.33 (s, 3H), 2.85-2.79 (m, 3H), 2.40-2.35 (m, 1H), 2.26 (s, 3H), 2.24-2.19 (m, 2H). | $R_T$ = 0.626 min; m/z = 386.0 |

TABLE 4-continued

| Example Ki (μM) METHOD | Structure | Stereo | $^1H$ NMR | MS (m/z) R.T. |
|---|---|---|---|---|
| Example 647 0.16 WX Method 019 | 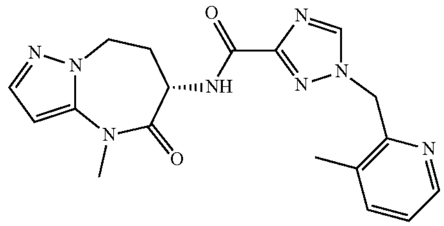 [SMILES: Cc1cccnc1Cn1cnc(C(=O)N[C@H]2CCn3nccc3N(C)C2=O)n1] 1-[(3-methyl-2-pyridyl)methyl]-N-(6S)-4-methyl-5-oxo-7,8-dihydro-6H-pyrazolo[1,5-a][1,3]diazepin-6-yl-1,2,4-triazole-3-carboxamide | Single Known Stereoisomer | $^1H$ NMR (400 MHz, $CD_3OD$) δ 8.57 (s, 1H), 8.32 (d, J = 4.8 Hz, 1H), 7.68 (d, J = 7.6 Hz, 1H), 7.52 (d, J = 2.0 Hz, 1H), 7.30-7.26 (m, 1H), 6.30 (d, J = 2.0 Hz, 1H), 5.63 (s, 2H), 4.52-4.39 (m, 2H), 4.32-4.28 (m, 1H), 3.35 (s, 3H), 2.89-2.84 (m, 1H), 2.45 (s, 3H), 2.28-2.24 (m, 1H). | $R_T$ = 1.135 min, m/z = 381.2 |
| Example 648 0.28 WX Method 019 | 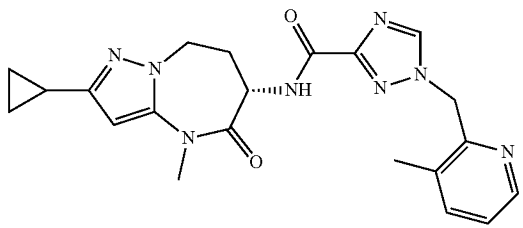 [SMILES: Cc1cccnc1Cn1cnc(C(=O)N[C@H]2CCn3nc(C4CC4)cc3N(C)C2=O)n1] 1-[(3-methyl-2-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1H$ NMR (400 MHz, $CD_3OD$) δ 8.58 (s, 1H), 8.33 (d, J = 4.4 Hz, 1H), 7.68 (d, J = 8.0 Hz, 1H), 7.30-7.27 (m, 1H), 6.00 (s, 1H), 5.63 (s, 2H), 4.53-4.48 (m, 1H), 4.31-4.26 (m, 1H), 4.24-4.20 (m, 1H), 3.32 (s, 3H), 2.86-2.80 (m, 1H), 2.46 (s, 3H), 2.25-2.21 (m, 1H), 1.91-1.87 (m, 1H), 0.94-0.92 (m, 2H), 0.75-0.73 (m, 2H). | $R_T$ = 1.357 min, m/z = 421.2 |
| Example 649 0.14 WX Method 133 | 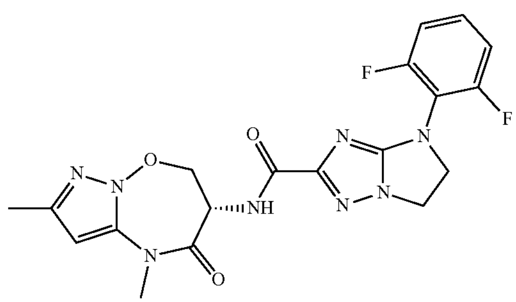 [SMILES: Cc1cc2n(n1)OC[C@H](NC(=O)c1nc3n(n1)CCN3c1c(F)cccc1F)C(=O)N2C] 4-(2,6-difluorophenyl)-N-[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide | Single Known Stereoisomer | $^1H$ NMR (400 MHz, $CD_3OD$) δ 7.52-7.43 (m, 1H), 7.21-7.17 (m, 2H), 6.46 (s, 1H), 4.72-4.60 (m, 3H), 4.60-4.53 (m, 2H), 4.51-4.45 (m, 1H), 4.43-4.35 (m, 1H), 3.38 (s, 3H), 2.91-2.82 (m, 1H), 2.45-2.35 (m, 4H). | $R_T$ = 0.745 min, m/z = 443.0 |

TABLE 4-continued

| Example Ki (μM) METHOD | Structure | Stereo | $^1$H NMR | MS (m/z) R.T. |
|---|---|---|---|---|
| Example 650 0.19 WX Method 028 | 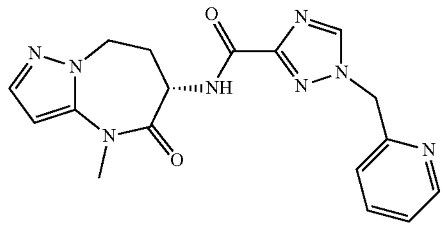 [SMILES: CN1C(=O)[C@@H](NC(=O)c2ncn(Cc3ccccn3)n2)CCn2nccc21] 1-(2-pyridylmethyl)-N-(6S)-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.66 (s, 1H), 8.55 (d, J = 4.4 Hz, 1H), 7.86 (t, J = 7.6 Hz, 1H), 7.54 (s, 1H), 7.42-7.38 (m, 2H), 6.32 (s, 1H), 5.62 (s, 2H), 4.55-4.42 (m, 2H), 4.31-4.29 4.29 (m, 1H), 3.38 (s, 3H), 2.91-2.81 (m, 1H), 2.36-2.28 (m, 1H). | $R_T$ = 1.25 min, m/z = 367.2 |
| Example 651 0.29 WX Method 028 | 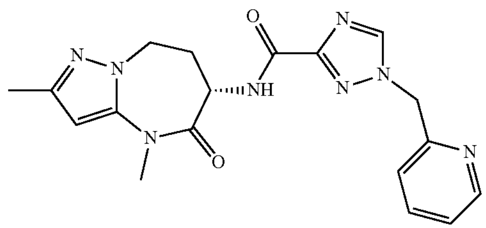 [SMILES: Cc1cc2n(n1)CC[C@H](NC(=O)c1ncn(Cc3ccccn3)n1)C(=O)N2C] 1-(2-pyridylmethyl)-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.64 (s, 1H), 8.52 (d, J = 4.4 Hz, 1H), 7.89-7.80 (m, 1H), 7.43-7.32 (m, 2H), 6.10 (s, 1H), 5.60 (s, 2H), 4.57-4.48 (m, 1H), 4.36-4.27 (m, 1H), 4.26-4.14 (m, 1H), 3.32 (s, 3H), 2.90-2.77 (m, 1H), 2.30-2.20 (m, 4H). | $R_T$ = 0.652 min, m/z = 381.2 |
| Example 652 0.19 WX Method 028 | 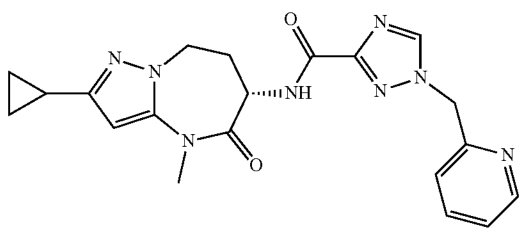 [SMILES: CN1C(=O)[C@@H](NC(=O)c2ncn(Cc3ccccn3)n2)CCn2nc(C3CC3)cc21] 1-(2-pyridylmethyl)-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.65 (s, 1H), 8.53 (d, J = 4.8 Hz, 1H), 7.87-7.84 (m, 1H), 7.40-7.37 (m, 2H), 6.00 (s, 1H), 5.60 (s, 2H), 4.56-4.51 (m, 1H), 4.30-4.28 (m, 1H), 4.23-4.18 (m, 1H), 3.32 (s, 3H), 2.88-2.81 (m, 1H), 2.29-2.24 (m, 1H), 1.93-1.90 (m, 1H), 0.96-0.93 (m, 2H), 0.76-0.74 (m, 2H). | $R_T$ = 0.747 min, m/z = 407.2. |

TABLE 4-continued

| Example Ki (μM) METHOD | Structure | Stereo | $^1$H NMR | MS (m/z) R.T. |
|---|---|---|---|---|
| Example 653 0.11 WX Method 025 | 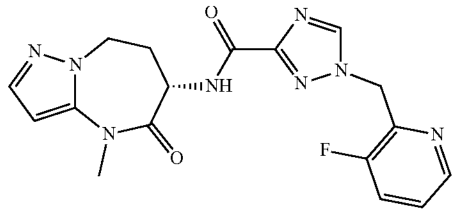 [SMILES: CN1C(=O)[C@@H](NC(=O)c2ncn(Cc3ncccc3F)n2)CCn2nccc21] 1-[(3-fluoro-2-pyridyl)methyl]-N-(6S)-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.65 (s, 1H), 8.35 (d, J = 5.2 Hz, 1H), 7.71-7.60 (m, 1H), 7.51 (s, 1H), 7.46-7.43 (m, 1H), 6.29 (s, 1H), 5.70 (s, 2H), 4.52-4.38 (m, 2H), 4.29-4.26 (m, 1H), 3.34 (s, 3H), 2.87-2.81 (m, 1H), 2.36-2.21 (m, 1H). | $R_T$ = 1.05 min, m/z = 385.1 |
| Example 654 0.11 WX Method 025 | 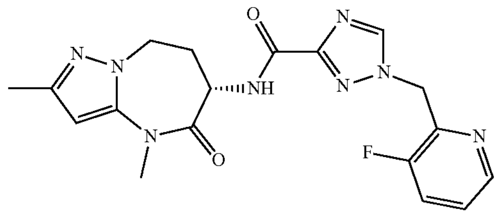 1-[(3-fluoro-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.65 (s, 1H), 8.35 (d, J = 4.8 Hz, 1H), 7.70-7.62 (m, 1H), 7.46-7.42 (m, 1H), 6.09 (s, 1H), 5.70 (s, 2H), 4.53-4.49 (m, 1H), 4.34-4.26 (m, 1H), 4.24-4.12 (m, 1H), 3.31 (s, 3H), 2.87-2.77 (m, 1H), 2.27-2.18 (m, 1H), 2.24 (s, 3H). | $R_T$ = 1.17 min, m/z = 399.2 |
| Example 655 0.14 WX Method 025 | 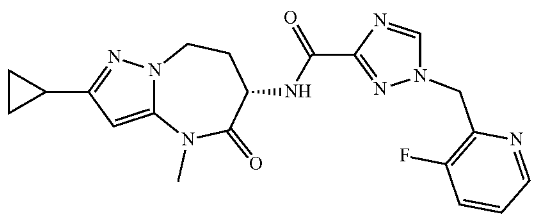 [SMILES: CN1C(=O)[C@@H](NC(=O)c2ncn(Cc3ncccc3F)n2)CCn2nc(C3CC3)cc21] 1-[(3-fluoro-2-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.65 (s, 1H), 8.35 (d, J = 4.4 Hz, 1H), 7.69-7.60 (m, 1H), 7.45-7.43 (m, 1H), 5.99 (s, 1H), 5.70 (s, 2H), 4.52-4.47 (m, 1H), 4.33-4.24 (m, 1H), 4.23-4.12 (m, 1H), 3.29 (s, 3H), 2.85-2.78 (m, 1H), 2.28-2.17 (m, 1H), 1.94-1.85 1H), 0.97-0.88 (m, 2H), 0.75-0.69 (m, 2H). | $R_T$ = 1.35 min, m/z = 425.2 |

TABLE 4-continued

| Example Ki (μM) METHOD | Structure | Stereo | $^1$H NMR | MS (m/z) R.T. |
| --- | --- | --- | --- | --- |
| Example 656<br>0.061<br>WX Method 022 | 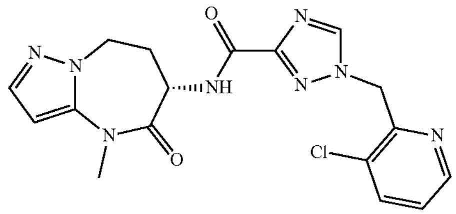<br>1-[(3-chloro-2-pyridyl)methyl]-N-(6S)-4-methyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.62 (s, 1H), 8.43-8.41 (m, 1H), 7.91-7.89 (m, 1H), 7.51 (d, J = 1.8 Hz, 1H), 7.39-7.35 (m, 1H), 6.29 (d, J = 1.8 Hz, 1H), 5.78 (s, 2H), 4.52-4.47 (m,1H), 4.46-4.38 (m, 1H), 4.31-4.22 (m, 1H), 3.34 (s, 3H), 2.81-2.80 (m, 1H), 2.30-2.22 (m, 1H). | $R_T$ = 1.21 min,, m/z = 401.1 |
| Example 657<br>0.074<br>WX Method 022 | 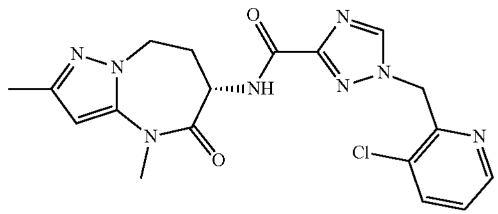 [SMILES: Cc1cc2n(n1)CC[C@H](NC(=O)c1ncn(Cc3ncccc3Cl)n1)C(=O)N2C]<br>1-[(3-chloro-2-pyridyl)methyl]-N-(6S)-2,4-dimethyl-5-oxo-7,8-dihydro-6H-pyrazolo [1,5-a][1,3]diazepin-6-yl-1,2,4-triazole-3-carboxamide | Single Known Stereoisomer | $^1$H NMR (400 MHz, $CD_3OD$) δ 8.62 (s, 1H), 8.43-8.41 (m, 1H), 7.91-7.89 (m, 1H), 7.39-7.35 (m, 1H), 6.09 (s, 1H), 5.78 (s, 2H), 4.54-4.50 (m, 1H), 4.35-4.27 (m, 1H), 4.25-4.14 (m, 1H), 3.31 (s, 3H), 2.88-2.78 (m, 1H), 2.29-2.18 (m, 1H), 2.24 (s, 3H). | $R_T$ = 1.26 min, m/z = 415.1 |
| Example 658<br>0.054<br>GNT_E425_651<br>WX Method 024 | 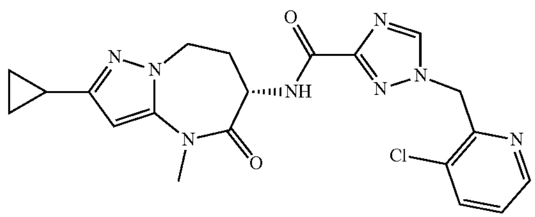<br>1-[(3-chloro-2-pyridyl)methyl]-N-(6S)-2-cyclopropyl-4-methyl-5-oxo-7,8-dihydro-6H-pyrazolo[1,5-a][1,3] diazepin-6-yl-1,2,4-triazole-3-carboxamide | Single Known Stereoisomer | $^1$H NMR (400 MHz, $CD_3OD$) δ 8.62 (s, 1H), 8.43-8.41 (m, 1H), 7.91-7.89 (m, 1H), 7.51 (s, 1H), 7.39-7.35 (m, 1H), 6.29 (s, 1H), 5.78 (s, 2H), 4.52 4.47 (m, 1H), 4.46-4.38 (m, 1H), 4.31-4.22 (m, 1H), 3.34 (s, 3H), 2.81-2.80 (m, 1H), 2.30-2.22 (m, 1H). | $R_T$ = 1.44 min, m/z = 441.1 |

TABLE 4-continued

| Example<br>Ki (μM)<br>METHOD | Structure | Stereo | $^{1}$H NMR | MS (m/z) R.T. |
|---|---|---|---|---|
| Example 659<br>0.035<br>WX Method 091 | 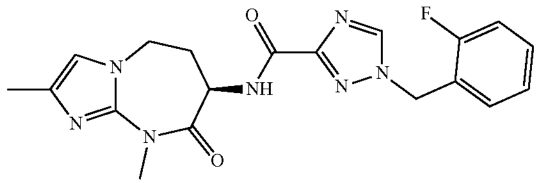<br>1-[(2-fluorophenyl)methyl]-N-(7R)-2,9-dimethyl-8-oxo-6,7-dihydro-5H-imidazo[1,2-a][1,3]diazepin-7-yl-1,2,4-triazole-3-carboxamide | Single<br>Unknown<br>Stereoisomer | $^{1}$H NMR (400 MHz, $CD_3OD$) δ 8.57 (s, 1H), 7.45-7.33 (m, 2H), 7.24-7.11 (m, 2H), 6.77 (s, 1H), 5.55 (s, 2H), 4.54-4.49 (m, 1H), 4.21-4.15 (m, 1H), 4.04-3.95 (m, 1H), 3.36 (s, 3H), 2.87-2.78 (m, 1H), 2.28-2.14 (m, 4H). | RT = 1.819 min;<br>m/z = 398.1 |
| Example 660<br>0.062<br>WX Method 091 | 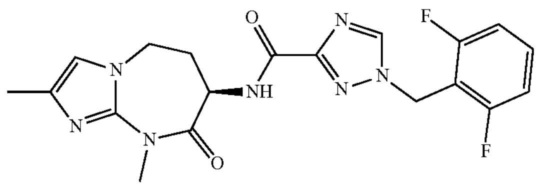 [SMILES: Cc1cn2c(n1)N(C)C(=O)[C@H](NC(=O)c1ncn(Cc3c(F)cccc3F)n1)CC2]<br>1-[(2,6-difluorophenyl)methyl]-N-(7R)-2,9-dimethyl-8-oxo-6,7-dihydro-5H-imidazo[1,2-a][1,3]diazepin-7-yl-1,2,4-triazole-3-carboxamide | Single<br>Unknown<br>Stereoisomer | $^{1}$H NMR (400 MHz, $CD_3OD$) δ 8.60 (s, 1H), 7.50-7.42 (m, 1H), 7.07-7.03 (m, 2H), 6.77-(s, 1H), 5.60 (s, 2H), 4.53-4.48 (m, 1H), 4.21-4.15 (m, 1H), 4.03-3.95 (m, 1H), 3.36 (s, 3H), 2.84-2.76 (m, 1H), 2.26-2.16 (m, 4H). | RT = 1.817 min;<br>m/z = 416.2 |
| Example 661<br>0.057<br>WX Method 091 | 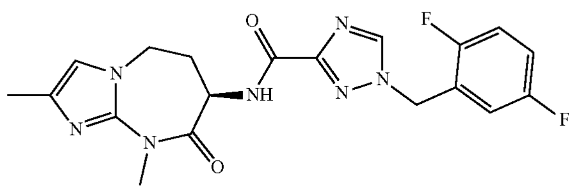 [SMILES: Cc1cn2c(n1)N(C)C(=O)[C@H](NC(=O)c1ncn(Cc3cc(F)ccc3F)n1)CC2]<br>1-[(2,5-difluorophenyl)methyl]-N-(7R)-2,9-dimethyl-8-oxo-6,7-dihydro-5H-imidazo[1,2-a][1,3]diazepin-7-yl-1,2,4-triazole-3-carboxamide | Single<br>Unknown<br>Stereoisomer | $^{1}$H NMR (400 MHz, $CD_3OD$) δ 8.61 (s, 1H), 7.22-7.11 (m, 3H), 6.78 (s, 1H), 5.54 (s, 2H), 4.55-4.48 (m, 1H), 4.21-4.16 (m, 1H), 4.05-3.98 1H), 3.36 (s, 3H), 2.86-2.76 (m, 1H), 2.31-2.15 (m, 4H). | $R_T$ = 1.852 min;<br>m/z = 416.1 |

TABLE 4-continued

| Example Ki (μM) METHOD | Structure | Stereo | $^1$H NMR | MS (m/z) R.T. |
| --- | --- | --- | --- | --- |
| Example 662 0.063 WX Method 082 | 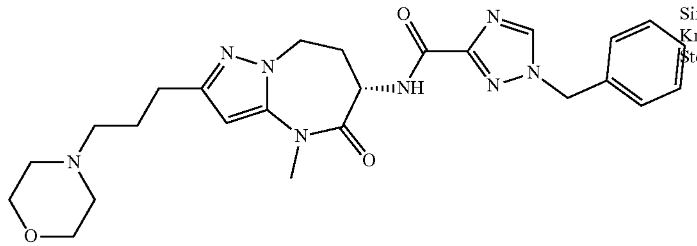 1-benzyl-N-(6S)-4-methyl-2-(3-morpholinopropyl)-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.57 (s, 1H), 7.38-7.32 (m, 5H), 6.17 (s, 1H), 5.47 (s, 2H), 4.54-4.49 (m, 1H), 4.33-4.30 (m, 1H), 4.27-4.23 (m, 1H), 3.72 (t, J = 4.4 Hz, 4H), 3.32 (s, 3H), 2.83-2.80 (m, 1H), 2.66-2.48 (m, 8H), 2.26-2.24 (m, 1H), 1.92-1.88 (m, 2H). | $R_T$ = 1.449 min, m/z = 493.3 |
| Example 663 0.42 WX Method 031 | 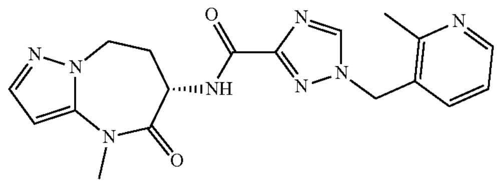 [SMILES: Cc1ncccc1Cn1cnc(C(=O)N[C@H]2CCn3nccc3N(C)C2=O)n1] 1[(2-methyl-3-pyridyl)methyl]-N-(6S)-4-methyl-5-oxo-7,8-dihydro-6H-pyrazolo[1,5-a][1,3diazepin-6-yl-1,2,4-triazole-3-carboxamide | Single Known Stereoisomer | $^1$H NMR (400 MHz, $CD_3OD$) δ 8.63 (s, 1H), 8.41 (d, J = 4.4 1H), 7.60 (d, J = 7.6 Hz, 1H), 7.56-7.52 (m, 1H), 7.32-7.29 (m, 1H), 6.33-6.31 (m, 1H), 5.60 (s, 2H), 4.55-4.42 (m, 2H), 4.35-4.24 (m, 1H), 3.37 (s, 3H), 2.95-2.82 (m, 1H), 2.61 (s, 3H), 2.35-2.25 (m, 1H). | $R_T$ = 1.068 min, m/z = 381.2 |
| Example 664 0.73 WX Method 031 | 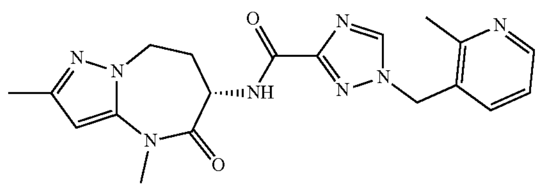 [SMILES: Cc1cc2n(n1)CC[C@H](NC(=O)c1ncn(Cc3cccnc3C)n1)C(=O)N2C] 1-[(2-[(2-3-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide | Single Known Stereoisomer | $^1$H NMR (400 MHz, $CD_3OD$) δ 8.61 (s, 1H), 8.39 (d, J = 4.8 Hz, 1H), 7.59 (d, J = 7.6 Hz, 1H), 7.30-7.27 (m, 1H), 6.11 (s, 1H), 5.58 2H), 4.55-4.50 (m, 1H), 4.35-4.27 (m, 1H), 4.26-4.16 (m, 1H), 3.32 (s., 3H), 2.90-2.78 (m, 1H), 2.59 (s, 3H), 2.30-2.20 (m, 4H). | $R_T$ = 1.165 min, m/z = 395.2 |

TABLE 4-continued

| Example Ki (μM) METHOD | Structure | Stereo | $^1$H NMR | MS (m/z) R.T. |
|---|---|---|---|---|
| Example 665 0.74 WX Method 031 | 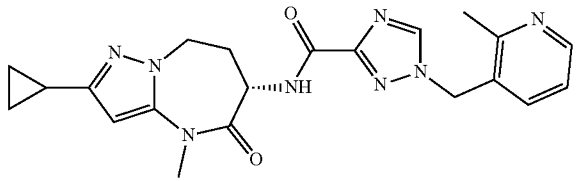 [SMILES: Cc1ncccc1Cn1cnc(C(=O)N[C@H]2CCn3nc(C4CC4)cc3N(C)C2=O)n1] 1-[(2-methyl-3-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide | Single Unknown Stereoisomer | $^1$H NMR (400 MHz, $CD_3OD$) δ 8.62 (s, 1H), 8.40 (d, J = 4.0 Hz, 1H), 7.59 (d, J = 7.6 Hz, 1H), 7.31-7.28 (m, 1H), 6.01 (s, 1H), 5.59 (s, 2H), 4.55-4.50 (m, 1H), 4.35-4.27 (m, H), 4.25-4.15 (m, 1H), 3.33-3.32 (m, 3H), 2.90-2.78 (m, 1H), 2.60 (s, 3H), 2.33-2.19 (m, 1H), 1.96-1.87 (m, 1H), 0.98-0.91 (m, 2H), 0.78-0.70 (m, 2H). | $R_T$ = 1.287 min, m/z = 421.3 |
| Example 666 0.04 WX Mwthod 127 | 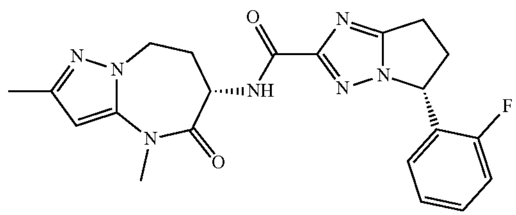 [SMILES: Cc1cc2n(n1)CC[C@H](NC(=O)c1nc3n(n1)[C@@H](c1ccccc1F)CC3)C(=O)N2C] (5R)-S-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereoisomer | $^1$H NMR (400 MHz, $CD_3OD$) δ 7.45-7.38 (m, 1H), 7.24-7.14 (m, 3H), 6.12 (s, 1H), 5.79-5.75 (m, 1H), 4.53-4.49 (m, 1H), 4.35-4.28 (m, 1H), 4.26-4.16 (m, 1H), 3.37-3.33 (m, 3H), 3.32-3.27 (m, 1H), 3.19-3.05 (m, 2H), 2.88-2.79 (m, 1H), 2.78-2.68 (m, 1H), 2.26 (s, 3H), 2.25-2.17 (m, 1H). | $R_T$ = 0.91 min, m/z = 424.2 |
| Example 667 0.53 WX Method 127 | 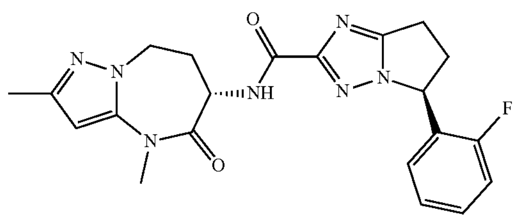 [SMILES: Cc1cc2n(n1)CC[C@H](NC(=O)c1nc3n(n1)[C@H](c1ccccc1F)CC3)C(=O)N2C] (5S)-S-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single Unknown Stereoisomer | $^1$H NMR (400 MHz, $CD_3OD$) δ 7.45-7.38 (m, 1H), 7.24-7.14 (m, 3H), 6.12 (s, 1H), 5.80-5.76 (m, 1H), 4.54-4.49 (m, 1H), 4.35-4.28 (m, 1H), 4.26-4.16 ( m, 1H), 3.37-3.33 (m, 3H), 3.32-3.27 (m, 1H), 3.19-3.05 (m, 2H), 2.88-2.79 (m, 1H), 2.78-2.68 (m, 1H), 2.26 (s, 3H), 2.25-2.17 (m, 1H). | $R_T$ = 0.92 min, m/z = 424.2 |

TABLE 4-continued

| Example<br>Ki (μM)<br>METHOD | Structure | Stereo | $^1$H NMR | MS (m/z) R.T. |
|---|---|---|---|---|
| Example 668<br>0.022<br>WX Method 128 | 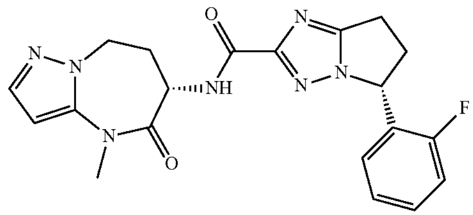 [SMILES: CN1C(=O)[C@@H](NC(=O)c2nc3n(n2)[C@@H](c2ccccc2F)CC3)CCn2nccc21]<br>(5R)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single<br>Unknown<br>Stereoisomer | $^1$H NMR (400 MHz, CD3OD) δ 7.51 (d, J = 2.0 Hz, 1H), 7.43-7.37 (m, 1H), 7.22-7.13 (m, H), 6.29 (d, J = 2.0 Hz, 1H), 5.77 (dd, J = 8.0, 12.0 Hz, 1H), 4.52-4.38 (m, 2H), 4.30-4.22 (m, 1H), 3.34 (s, 3H), 3.30-3.25 (m, 1H), 3.19-3.03 (m, 2H), 2.88-2.80 (m, 1H), 2.74-2.68 (m, 1H), 2.30-2.21 (m, 1H). | $R_T$ = 0.76 min,<br>m/z = 410.0 |
| Example 669<br>0.61<br>WX Method 128 | 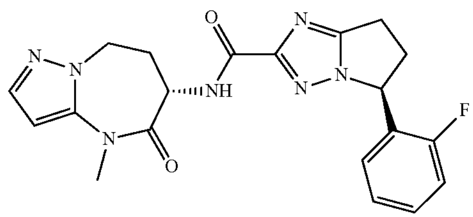 [SMILES: CN1C(=O)[C@@H](NC(=O)c2nc3n(n2)[C@H](c2ccccc2F)CC3)CCn2nccc21]<br>(5S)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide | Single<br>Unknown<br>Stereoisomer | $^1$H NMR (400 MHz, $CD_3OD$) δ 7.52 (s, 1H), 7.43-7.37 (m,1H), 7.22-7.12 (m, 3H), 6.30 (s, 1H), 5.80-5.76 (m, 1H), 4.53-4.38 (m, 2H), 4.30-4.22 (m, 1H), 3.35 (s, 3H), 3.30-3.25 (m, 1H), 3.19-3.03 (m, 2H), 2.90-2.79 (m, 1H), 2.76-2.67 (m, 1H), 2.30-2.21 (m, 1H). | $R_T$ = 0.75 min,<br>m/z = 410.0 |
| Example 670<br>0.0266<br>Chiral table 1 | 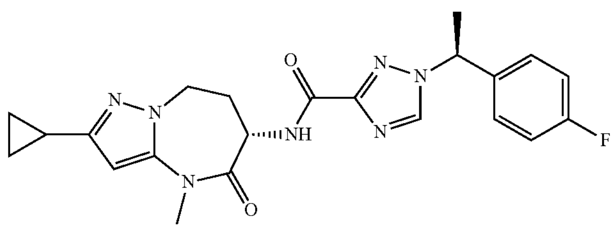 [SMILES: C[C@@H](c1ccc(F)cc1)n1cnc(C(=O)N[C@H]2CCn3nc(C4CC4)cc3N(C)C2=O)n1]<br>N-[rac-(6S)-2-cyclopropyl-4-methyl-5-oxo-7,8-dihydro-6H-pyrazolo[1,5-a][1,3]diazepin-6-yl]-1-[rac-(1S)-1-(4-fluorophenyl)ethyl]-1,2,4-triazole-3-carboxamide | Single<br>Unknown<br>Stereoisomer | $^1$H NMR (400 MHz, DMSO-d6) δ 8.84 (s, 1H), 7.39 (ddd, J = 9.0, 5.4, 0.5 Hz, 2H), 7.28-7.11 (m, 2H), 6.06 (s, 1H), 5.83 (d, J = 7.0 Hz, 1H), 4.23 (s, 0H), 3.21 (d, J = 6.9 Hz, 3H), 2.33 (s, 0H), 1.94-1.67 (m, 4H), 0.96-0.50 (m, 3H). | 438.2 |

TABLE 4-continued

| Example Ki (μM) METHOD | Structure | Stereo | $^1$H NMR | MS (m/z) R.T. |
|---|---|---|---|---|
| Example 671<br>8.2<br>Chiral table 1 | 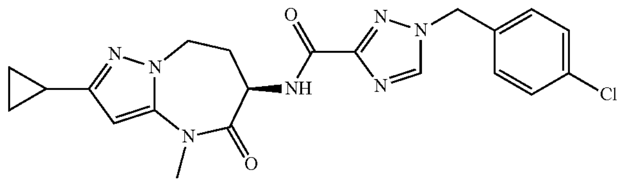 [SMILES: CN1C(=O)[C@H](NC(=O)c2ncn(Cc3ccc(Cl)cc3)n2)CCn2nc(C3CC3)cc21]<br>(R)-1-(4-chlorobenzyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide | Single Unknown Stereoisomer | $^1$H NMR (400 MHz, DMSO-d6) δ 8.81 (s, 1H), (d, J = 7.8 Hz, 1H), 7.49-7.22 (m, 4H), 6.06 (s, 1H), 5.49 (s, 2H), 4.27 (dd, J = 21.5, 13.3 Hz, 1H), 3.20 (s, 3H), 2.01-1.68 (m, 1H), 1.05-0.47 (m, 2H). | 440.1<br>4.55 min |
| Example 672<br>0.056<br>Chiral table 1 | 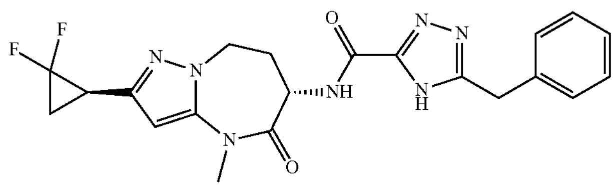 [SMILES: CN1C(=O)[C@@H](NC(=O)c2nnc(Cc3ccccc3)[nH]2)CCn2nc([C@H]3CC3(F)F)cc21]<br>5-benzyl-N-[rac-(6S)-4-methyl-5-oxo-2-[rac-(1R)-2,2-difluorocyclopropyl]-7,8-dihydro-6H-pyrazolo[1,5-a][1,3]diazepin-6-yl]-4H-1,2,4-triazole-3-carboxamide | Mixture of Diastereomers | $^1$H NMR (400 MHz, DMSO-d6) δ 7.37-7.10 (m, 5H), 6.27 (s, 1H), 4.39-4.23 (m, 1H), 4.23-4.01 (m, 3H), 3.22 (s, 4H), 3.00-2.76 (m, 1H), 2.68-2.53 (m, 1H), 2.09-1.69 (m, 1H). | 442.1<br>4.19 min |
| Example 673<br>0.0412<br>Chiral table 1 | 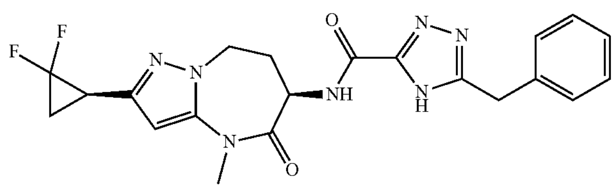 [SMILES: CN1C(=O)[C@H](NC(=O)c2nnc(Cc3ccccc3)[nH]2)CCn2nc([C@H]3CC3(F)F)cc21]<br>5-benzyl-N-[rac-(6R)-4-methyl-5-oxo-2-[rac-(1R)-2,2-difluorocyclopropyl]-7,8-dihydro-6H-pyrazolo[1,5-a][1,3]diazepin-6-yl]-4H-1,2,4-triazole-3-carboxamide | Single Unknown Stereoisomer | $^1$H NMR (400 MHz, DMSO-d6) δ 7.45-7.14 (m, 5H), 6.30 (s, 1H), 4.43-4.21 (m, 2H), 4.15 (d, J = 31.7 Hz, 3H), 3.23 (s, 3H), 2.93 (td, J = 12.0, 8.0 Hz, 1H), 2.59 (s, 0H), 2.39 (d, J = 6.0 Hz, 1H). | 442.2<br>4.20 min |
| Example 674<br>3.981599331<br>Chiral table 1 | 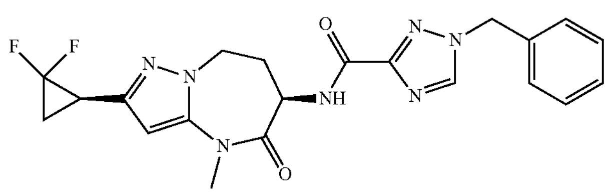 [SMILES: CN1C(=O)[C@H](NC(=O)c2ncn(Cc3ccccc3)n2)CCn2nc([C@H]3CC3(F)F)cc21]<br>1-benzyl-N-[rac-(6R)-4-methyl-5-oxo-2-[rac-(1R)-2,2-difluorocyclopropyl]-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-d6) δ 8.82 (s, 1H), 8.54 (d, J = 7.8 Hz, 1H), 7.46 -7.21 (m, 5H), 6.27 (d, J = 0.6 Hz, 1H), 5.48 (s, 2H), 4.40-4.05 (m, 1H), 3.22 (s, 3H), 2.89 (d, J = 8.1 Hz, 0H), 2.13-1.42 (m, 1H). | 442.2<br>4.32 min |

TABLE 4-continued

| Example Ki (μM) METHOD | Structure | Stereo | $^1$H NMR | MS (m/z) R.T. |
|---|---|---|---|---|
| Example 675<br>0.0164<br>Chiral table 1 | 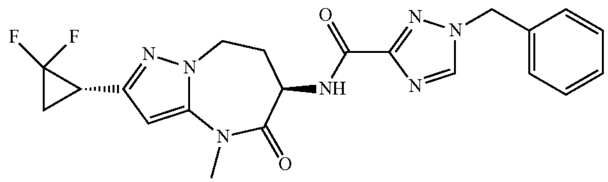 [SMILES: CN1C(=O)[C@H](NC(=O)c2ncn(Cc3ccccc3)n2)CCn2nc([C@@H]3CC3(F)F)cc21]<br>1-benzyl-N-[rac-(6R)-4-methyl-5-oxo-2-[rac-(1S)-2,2-difluorocyclopropyl]-7,8-dihydro-6H-pyrazolo[1,5-a][1,3]diazepin-6-yl]-1,2,4-triazole-3-carcoxamide | Single Unknown Stereoisomer | $^1$H NMR (400 MHz, DMSO-d6) δ 8.82 (s, 1H), 8.54 (d, J = 7.8 Hz, 1H), 7.46-7.21 (m, 5H), 6.29 (s, 1H), 5.48 2H), 4.41-4.07 (m, 2H), 3.22 (s, 3H), 3.02-2.70 (m, 1H), 2.59 (s, 0H), 2.44-2.28 (m, 1H), 2.09-1.70 (m, 2H). | 442.2<br>4.33 min |
| Example 676<br>3.1<br>Chiral table | 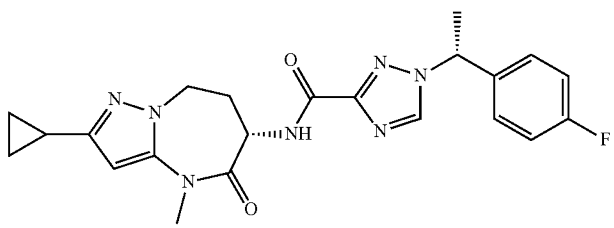 [SMILES: C[C@H](c1ccc(F)cc1)n1cnc(C(=O)N[C@H]2CCn3nc(C4CC4)cc3N(C)C2=O)n1]<br>N-[rac-(6S)-2-cyclopropyl-4-methyl-5-oxo-7,8-dihydro-6H-pyrazolo[1,5-a][1,3]diazepin-6-yl]-1-[rac-(1R)-1-(4-fluorophenypethyl]-1,2,4-triazole-3-carboxamide | Single Unknown Stereoisomer | $^1$H NMR (400 MHz, DMSO-d6) δ 8.84 (s, 1H), 8.49 (d, J = 7.4 Hz, 1H), 7.46 -7.33 (m, 2H), 7.25-7.06 (m, 2H), 6.06 (s, 1H), 5.83 (q, J = 7.0 Hz, 1H), 4.40-4.16 (m, 3H), 4.15-3.98 (m, 1H), 3.24-3.10 (m, 5H), 2.57 (tt, J = 12.8, 8.1 Hz, 1H), 2.32 (td, J = 12.1, 6.2 Hz, 1H), 0.94-0.78 (m, 2H), 0.71-0.58 (m, 2H). | 438.2<br>4.47 min |
| Example 677<br>0.00758<br>Chiral table | 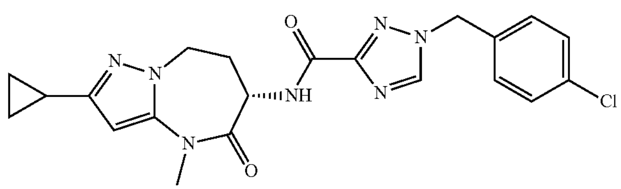 [SMILES: CN1C(=O)[C@@H](NC(=O)c2ncn(Cc3ccc(Cl)cc3)n2)CCn2nc(C3CC3)cc21]<br>1-[(4-chlorophenyl)methyl]-N-[rac-(6S)-2-cyclopropyl-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-d6) δ 8.81 (s, 1H), 8.51 (d, J = 7.8 Hz, 1H), 7.55-7.20 (m, 4H), 6.06 (s, 1H), 5.49 (s, 2H), 4.40-3.99 (m, 3H), 3.26-3.13 (m, 4H), 2.43 -2.24 (m, 1H), 1.99-1.70 (m, 1H), 0.98-0.51 (m, 4H). | 440.1<br>4.55 min |

TABLE 4-continued

| Example Ki (µM) METHOD | Structure | Stereo | $^1$H NMR | MS (m/z) R.T. |
|---|---|---|---|---|
| Example 678<br>5.3<br>Chiral table | 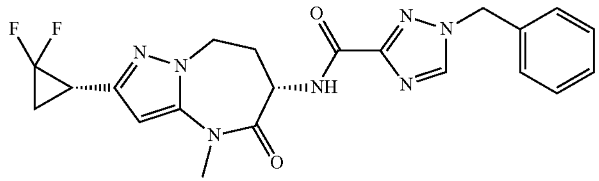 [SMILES: CN1C(=O)[C@@H](NC(=O)c2ncn(Cc3ccccc3)n2)CCn2nc([C@@H]3CC3(F)F)cc21]<br>1-[(4-chlorophenyl)methyl]-N-[rac-(6S)-2-cyclopropyl-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-d6) δ 8.82 (s, 1H), 8.54 (d, J = 7.8 Hz, 1H), 7.43-7.26 (m, 5H), 6.29 (s, 1H), 5.48 (s, 2H), 4.36-4.24 (m, 2H), 4.23-4.09 (m, 1H), 3.22 (s, 3H), 2.98-2.85 (m, 1H), 2.67-2.51 (m, 1H), 2.43-2.30 (m, 1H), 2.04- 1.79 (m, 2H). | 442.1<br>4.34 min |
| Example 679<br>0.0216<br>Chiral table 1 | 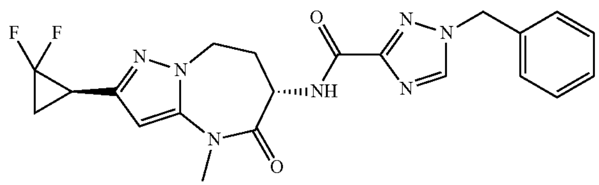 [SMILES: CN1C(=O)[C@@H](NC(=O)c2ncn(Cc3ccccc3)n2)CCn2nc([C@H]3CC3(F)F)cc21]<br>1-benzyl-N-[rac-(6S)-4-methyl-5-oxo-2-[rac-(1R)-2,2-difluorocyclopropyl]-7,8-dihydro-6H-pyrazolo[1,5-a][1,3diazepin-6-yl]-1,2,4-triazole-3-carboxamide | Single Unknown Stereoisomer | $^1$H NMR (400 MHz, DMSO-d6) δ 8.82 (s, 1H), 8.54 (d, J = 7.8 Hz, 1H), 7.42-7.26 (m, 5H), 6.27 (s, 1H), 5.48 (s, 2H), 4.37-4.24 (m, 2H), 4.23-4.10 (m, 1H), 3.22 (s, 3H), 2.95-2.82 (m, 1H), 2.66-2.50 (m, 1H), 2.43-2.32 (m, 1H), 2.10-1.90 (m, 1H), 1.91-1.78 (m, 1H). | 442.2<br>4.33 min |
| Example 680<br>9.2<br>Chiral table 1 | 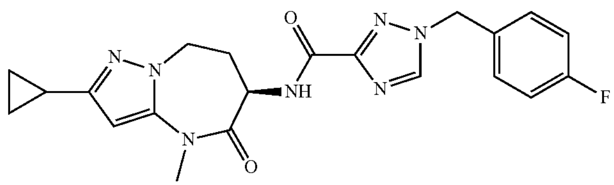 [SMILES: CN1C(=O)[C@H](NC(=O)c2ncn(Cc3ccc(F)cc3)n2)CCn2nc(C3CC3)cc21]<br>1-[(4-fluorophenyl)methyl]-N-[rac-(6R)-2-cyclopropyl-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-d6) δ 8.80 (s, 1H), 8.50 (d, 7.15 (m, 2H), 6.05 (s, 1H), 5.47 (s, 2H), 4.36-4.18 (m, 2H), 4.15-4.02 (m, 1H), 3.19 (s, 3H), 2.64-2.51 (m, 1H), 2.38-2.25 (m, 1H), 1.90-1.79 (m, 1H), 0.92-0.79 (m, 2H), 0.74-0.59 (m, 2H). | 424.2<br>4.25 min |

TABLE 4-continued

| Example<br>Ki (μM)<br>METHOD | Structure | Stereo | $^1$H NMR | MS (m/z) R.T. |
|---|---|---|---|---|
| Example 681<br>0.0237<br>Chiral table 1 | 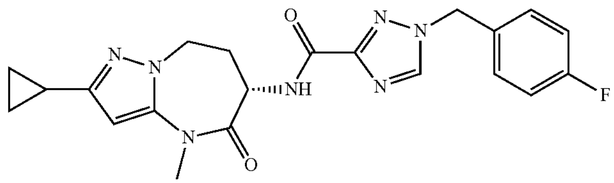 [SMILES: CN1C(=O)[C@@H](NC(=O)c2ncn(Cc3ccc(F)cc3)n2)CCn2nc(C3CC3)cc21]<br>1-[(4-fluorophenyl)methyl]-N-[rac-(6S)-2-cyclopropyl-4-methyl-5-oxo-7,8-dihydro-6H-pyrazolo[1,5-a][1,3]diazepin-6-yl]-1,2,4-triazole-3-carboxamide | Single<br>Unknown<br>Stereoisomer | $^1$H NMR (400 MHz, DMSO-d6) δ 8.80 (s, 1H), 8.50 (d, J = 7.8 Hz, 1H), 7.4-7.33 (m, 2H), 7.26-7.15 (m, 2H), 6.05 (s, 1H), 5.47 (s, 2H), 4.36-1H), 3.19 (s, 3H), 2.64-2.51 (m, 1H), 2.36-2.25 (m, 1H), 1.90-1.79 (m, 1H), 0.92-0.79 (m, 2H), 0.74-0.59 (m, 2H). | 424.2<br>4.25 min |
| Example 682<br>0.0738<br>81604618<br>Chiral table 1 | 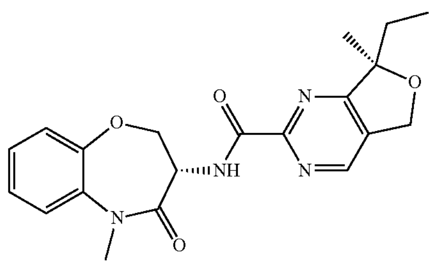 [SMILES: CC[C@@]1(C)OCc2cnc(C(=O)N[C@H]3COc4ccccc4N(C)C3=O)nc21]<br>(7R)-7-ethyl-7-methyl-N-[rac-(3S)-5-methyl-4-oxo-2,3-dihydro-1,5-benzoxazepin-3-yl]-5H-furo[3,4-d]pyrimidine-2-carboxamide | Single<br>Unknown<br>Stereoisomer | $^1$H NMR (400 MHz, DMSO-d6) δ 8.99-8.86 (m, 1H), 7.59-7.46 (m, 1H), 7.43-7.18 (m, 3H), 5.12 (dd, J = 2.2, 1.0 Hz, 2H), 4.88 (dt, J = 11.2, 7.6 Hz, 1H), 4.68-4.41 (m, 2H), 3.34 (s, 4H), 1.93-1.67 (m, 2H), 1.41 (s, 3H), 0.73 (t, J = 7.4 Hz, 3H). | 383.1<br>4.45 min |
| Example 683<br>0.0109<br>Chiral table 1 | 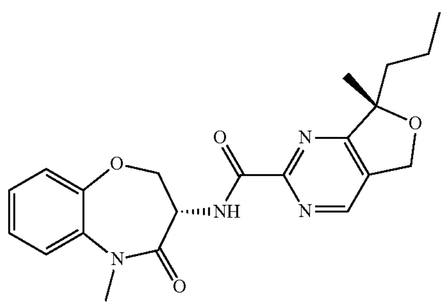 [SMILES: CCC[C@]1(C)OCc2cnc(C(=O)N[C@H]3COc4ccccc4N(C)C3=O)nc21]<br>(7S)-7-methyl-7-propyl-N-[rac-(3S)-5-methyl-4-oxo-2,3-dihydro-1,5-benzoxazepin-3-yl]-5H-furo[3,4-d]pyrimidine-2-carboxamide | Single<br>Unknown<br>Stereoisomer | $^1$H NMR (400 MHz, DMSO-d6) δ 9.00-8.89 (m, 2H), 7.56-7.47 (m, 1H), 7.39-7.23 (m, 3H), 5.18-5.05 (m, 2H), 4.88 (dt, J = 11.1, 7.8 Hz, 1H), 4.62-4.46 (m, 2H), 3.34 (s, 3H), 1.83-1.69 (m, 2H), 1.41 (s, 3H), 0.97 (s, 0H), 1.05-0.88 (m, 0H), 0.82 (t, J = 7.3 Hz, 3H). | 397.2<br>4.88 min |

TABLE 4-continued

| Example Ki (μM) METHOD | Structure | Stereo | $^1$H NMR | MS (m/z) R.T. |
|---|---|---|---|---|
| Example 684 0.163 Chiral table 1 | 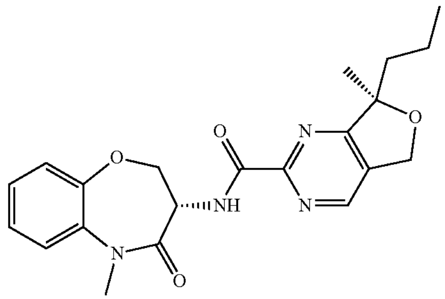 rac-(7R)-7-methyl-7-propyl-N-[rao-(3S)-5-methyl-4-ox o-2,3-dihydro-1,5-benzoxazepin-3-yl]-5H-furo[3,4-d]pyrimidine-2-carboxamide | Single Unknown Stereoisomer | $^1$H NMR (400 MHz, DMSO-d6) δ 9.03-8.80 (m, 1H), 7.58-7.44 (m, 0H), 7.43-7.20 (m, 2H), 5.20-5.00 (m, 1H), 5.01-4.79 (m, 1H), 4.68-4.36 (m, 1H), 1.99-1.63 (m, 1H), 1.40 (s, 2H), 0.97 (d, J = 7.1 Hz, 0H), 0.88-0.70 (m, 2H). | 397.2 4.86 min |
| Example 685 0.0214 Chiral table 1 | 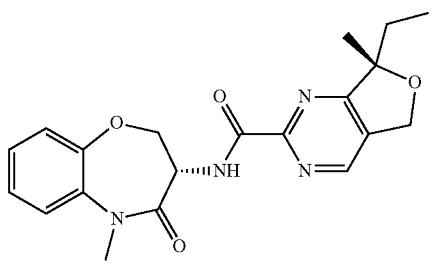 [SMILES: CC[C@]1(C)OCc2cnc(C(=O)N[C@H]3COc4ccccc4N(C)C3=O)nc21] rac-(7S)-7-ethyl-7-methyl-N-[rac-(3S)-5-methyl-4-oxo-2,3-dihydro-1,5-benzoxazepin-3-yl]-5H-furo[3,4-d] pyrimidine-2-carboxamide | Single Unknown Stereoisomer | $^1$H NMR (400 MHz, DMSO-d6) δ 9.00-8.84 (m, 1H), 7.64-7.45 (m, 1H), 7.45-7.20 (m, 2H), 5.12 (dd, J = 2.5, 1.0 Hz, 1H), 4.99-4.77 (m, 0H), 4.71-4.38 (m, 1H), 3.34 (s, 2H), 1.96-1.66 (m, 1H), 1.41 (s, 2H), 0.73 (t, J = 7.4 Hz, 2H). | 383.2 4.45 min |

TABLE 4-continued

| Example Ki (μM) METHOD | Structure | Stereo | $^1$H NMR | MS (m/z) R.T. |
|---|---|---|---|---|
| Example 686<br>1.1<br>Chiral table 1 | 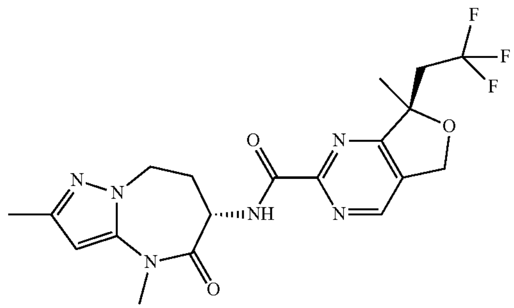 [SMILES: Cc1cc2n(n1)CC[C@H](NC(=O)c1ncc3c(n1)[C@@](C)(CC(F)(F)F)OC3)C(=O)N2C]<br>rac-(7R)-7-methyl-N-[rac-(6S)-2,4-dimethyl-5-oxo-7,8-dihydro-6H-pyrazolo[1,5-a][1,3]diazepin-6-yl]-7-(2,2,2-trifluoroethyl)-5H-furo[3,4-d]pyrimidine-2-carboxamide | Single Unknown Stereoisomer | $^1$H NMR (400 MHz, DMSO-d6) δ 9.08-8.95 (m, 2H), 6.15 (s, 1H), 5.24-5.10 (m, 2H), 4.45-4.33 (m, 1H), 4.30 (dd, J = 14.6, 7.9 Hz, 1H), 4.21-4.08 (m, 1H), 3.24 (s, 3H), 3.03-2.86 (m, 2H), 2.75-2.59 (m, 1H), 2.40-2.27 (m, 1H), 2.18 (s, 3H), 1.52 (s, 3H). | 439.2<br>4.02 min |
| Example 687<br>0.251<br>Chiral table 1 | 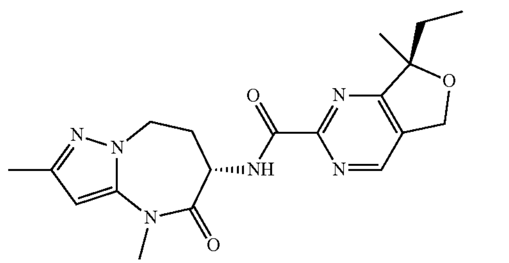 [SMILES: CC[C@@]1(C)OCc2cnc(C(=O)N[C@H]3CCn4nc(C)cc4N(C)C3=O)nc21]<br>rac-(7R)-7-ethyl-7-methyl-N-[rac-(6S)-2,4-dimethyl-5-oxo-7,8-dihydro-6H-pyrazolo[1,5-a][1,3]diazepin-6-yl]-5H-furo[3,4-d]pyrimidine-2-carboxamide | Single Unknown Stereoisomer | $^1$H NMR (400 MHz, DMSO-d6) δ 8.99 (d, J = 7.3 Hz, 1H), 8.91 (d, J = 0.8 Hz, 1H), 6.15 1H), 5.18-5.05 (m, 2H), 4.44-4.32 (m, 1H), 4.29 (dd, J = 14.6, 8.0 Hz, 1H), 4.21-4.08 (m, 1H), 3.24 (s, 3H), 2.77-2.61 (m, 1H), 2.31 (dt, J = 12.3, 6.1 Hz, 1H), 2.18 (s, 3H), 1.91-1.72 (m, 2H), 1.41 (s, 3H), 0.74 (t, 7.4 Hz, 3H). | 385.2<br>3.73 min |

TABLE 4-continued

| Example Ki (μM) METHOD | Structure | Stereo | $^1$H NMR | MS (m/z) R.T. |
|---|---|---|---|---|
| Example 688 0.0437 Chiral table 1 | 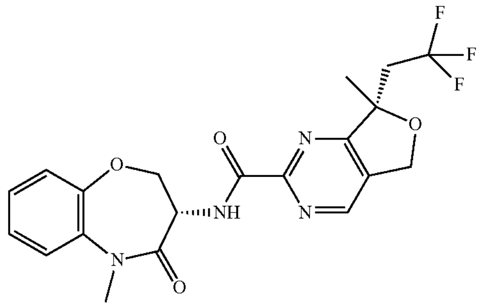 rac-(7S)-7-methyl-N-[rac-(3 S)-5-methyl-4-oxo-2,3-dihydro-1,5-benzoxazepin-3-yl]-7-(2,2,2-trifluoroethyl)-5H-furo[3,4-d]pyrimidine-2-carboxamide | Single Unknown Stereoisomer | $^1$H NMR (400 MHz, DMSO-d6) δ 9.06-8.97 (m, 2H), 7.56-7.49 (m, 1H), 7.39-7.23 (m, 3H), 5.25-5.10 (m, 2H), 4.95-4.84 (m, 1H), 4.58 (dd, J = 11.3, 9.9 Hz, 1H), 4.50 (dd, J = 9.9, 7.8 Hz, 1H), 3.34 (s, 3H), 3.42-3.22 (m, 1H), 3.06-2.86 (m, 2H), 1.51 (s, 3H). | 437.1 4.79 min |
| Example 689 0.176 Chiral table 1 | 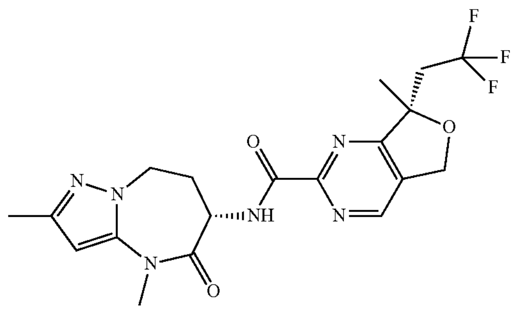 [SMILES: Cc1cc2n(n1)CC[C@H](NC(=O)c1ncc3c(n1)[C@](C)(CC(F)(F)F)OC3)C(=O)N2C] rac-(75)-7-methyl-N-[rac-(6S)-2,4-dimethyl-5-oxo-7,8- dihydro-6H-pyrazolo[1,5-a][1,3diazepin-6-yl]-7-(2,2,2-trifluoroethyl)-5H-furo[3,4-d] pyrimidine-2-carboxamide | Single Unknown Stereoisomer | $^1$H NMR (400 MHz, DMSO-d6) δ 9.07-8.96 (m, 2H), 6.15 (s, 1H), 5.24-5.10 (m, 2H), 4.45-4.33 (m, 1H), 4.35-4.25 (m, 1H), 4.21-4.08 (m, 1H), 3.24 (s, 3H), 3.03-2.86 (m, 2H), 2.76-2.61 (m, 1H), 2.40-2.27 (m, 1H), 2.18 (s, 3H), 1.51 (s, 3H). | 439.2 4.02 min |

TABLE 4-continued

| Example Ki (µM) METHOD | Structure | Stereo | $^1$H NMR | MS (m/z) R.T. |
|---|---|---|---|---|
| Example 690<br>1.181618025<br>Chiral table 1 | 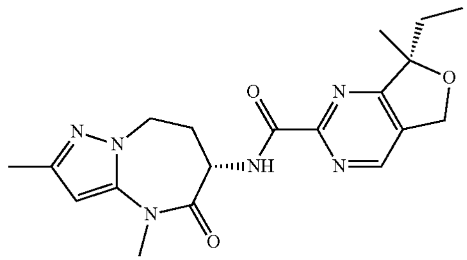 [SMILES: CC[C@]1(C)OCc2cnc(C(=O)N[C@H]3CCn4nc(C)cc4N(C)C3=O)nc21]<br>rac-(7S)-7-ethyl-7-methyl-N-[rac-(6S)-2,4-dimethyl-5-oxo-7,8-dihydro-6H-pyrazolo[1,5-a][1,3]diapepin-6-yl]-5H-furo[3,4-d]pyrimidine-2-carboxamide | Single Unknown Stereoisomer | $^1$H NMR (400 MHz, DMSO-d6) δ 9.03-8.64 (m, 1H), 6.15 (s, 0H), 5.12 (dd, J = 2.1, 1.0 Hz, 1H), 4.50-3.97 (m, 1H), 3.24 (s, 1H), 2.67 (d, J = 8.0 Hz, 0H), 2.33 (dd, J = 12.2, 6.6 Hz, 0H), 2.18 (s, 1H), 1.96-1.70 (m, 1H), 1.41 (s, 1H), 0.74 (t, J = 7.4 Hz, 2H). | 385.2<br>3.73 min |
| Example 691<br>0.0228<br>Chiral table 1 | 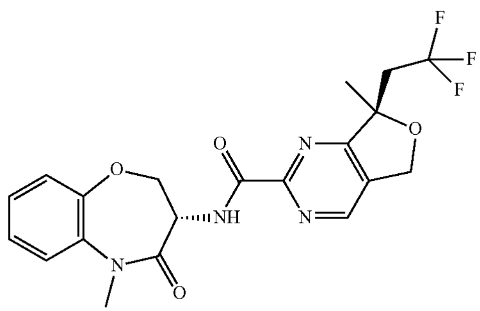 [SMILES: CN1C(=O)[C@@H](NC(=O)c2ncc3c(n2)[C@@](C)(CC(F)(F)F)OC3)COc2ccccc21]<br>rac-(7R)-7-methyl-N-[rac-(3S)-5-methyl-4-oxo-2,3-dihydro-1,5-benzoxazepin-3-yl]-7-(2,2,2-trifluoroethyl)-5H-furo[3,4-d]pyrimidine-2-carboxamide | Single Unknown Stereoisomer | $^1$H NMR (400 MHz, DMSO-d6) δ 9.06-8.97 (m, 2H), 7.56-7.49 (m, 1H), 7.39-7.23 (m, 3H), 5.25-5.10 (m, 2H), 4.95-4.83 (m, 1H), 4.59 (dd, J = 11.3, 9.9 Hz, 1H), 4.50 (dd, 3H), 3.03-2.86 (m, 2H), 1.51 (s, 3H). | 437.1<br>4.80 min |

TABLE 4-continued

| Example Ki (μM) METHOD | Structure | Stereo | $^{1}H$ NMR | MS (m/z) R.T. |
|---|---|---|---|---|
| Example 692 0.113 Chiral table 1 | 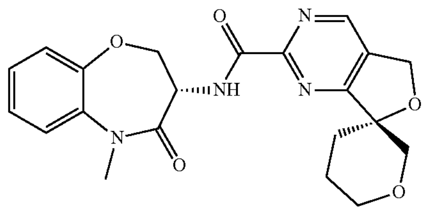 rac-(7R)-N-[rac-(3S)-5-methyl-4-oxo-2,3-dihydro-1,5-benzoxazepin-3-yl]spiro[5H-furo[3,4-d]pyrimidine-7,3'-tetrahydropyran]-2-carboxamide | Single Unknown Stereoisomer | $^{1}H$ NMR (400 MHz, DMSO-d6) δ 9.10-8.84 (m, 1H), 7.65-7.45 (m, 0H), 7.42-7.15 (m, 2H), 5.15 (d, J = 1.0 Hz, 1H), 4.87 (s, 0H), 4.67-4.31 (m, 1H), 3.96-3.41 (m, 1H), 3.34 (s, 1H), 2.17-1.52 (m, 1H). | 411.2 4.07 min |
| Example 693 0.0305 Chiral table | 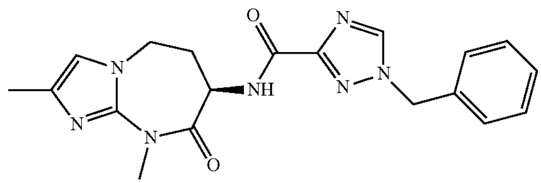 [SMILES: Cc1cn2c(n1)N(C)C(=O)[C@H](NC(=O)c1ncn(Cc3ccccc3)n1)CC2] 1-benzyl-N-[rac-(7R)-2,9-dimethyl-8-oxo-6,7-dihydro-5H-imidazo[1,2-a][1,3]diazepin-7-yl]-1,2,4-triazole-3-carboxamide | Single Unknown Stereoisomer | $^{1}H$ NMR (400 MHz, DMSO-d6) δ8.82 (s, 1H), 8.51 (d, J = 7.8 Hz, 1H), 7.43-7.26 (m, 3H), 6.84-6.77 (m, 1H), 5.48 (s, 1H), 4.35-4.24 (m, 1H), 4.15 (dd, J = 14.3, 7.8 Hz, 1H), 3.86 (ddd, J = 14.3, 12.8, 6.6 Hz, 1H), 3.35-3.26 (m, 1H), 3.23 (s, 2H), 2.62-2.50 (m, 0H), 2.38-2.23 (m, 1H), 2.10 (d, J = 1.0 Hz, 2H). | 380.2 2.81 min |
| Example 694 0.1722 Chiral table 1 | 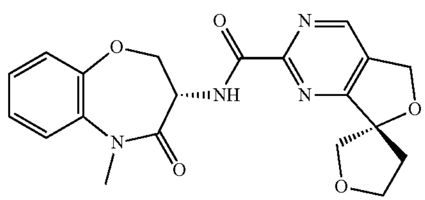 [SMILES: CN1C(=O)[C@@H](NC(=O)c2ncc3c(n2)[C@]2(CCOC2)OC3)COc2ccccc21] rac-(7S)-N-[rac-(3S)-5-methyl-4-oxo-2,3-dihydro-1,5-benzoxazepin-3-yl]spiro[5H-furo[3,4-d]pyrimidine-7,3'-tetrahydrofuran]-2-carboxamide | Single Unknown Stereoisomer | $^{1}H$ NMR (400 MHz, DMSO-d6) δ 9.03-8.92 (m, 2H), 7.56-7.48 (m, 1H), 7.39-7.23 (m, 3H), 5.15 (d, J = 1.0 Hz, 2H), 4.89 (dt, J = 11.2, 7.8 Hz, 1H), 4.63-4.45 (m, 2H), 4.10-3.84 (m, 4H), 3.34 (s, 3H), 3.36-3.25 (m, 2H), 2.31-2.22 (m, 2H). | 397.1 3.92 min |

TABLE 4-continued

| Example Ki (μM) METHOD | Structure | Stereo | $^1$H NMR | MS (m/z) R.T. |
|---|---|---|---|---|
| Example 695 0.694 Chiral table 1 | 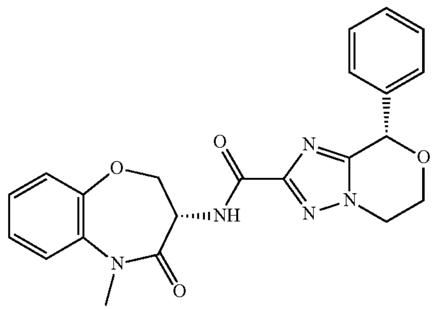 rac-(8S)-8-phenyl-N-[rac-(3S)-5-methyl-4-oxo-2,3-dihydro-1,5-benzoxazepin-3-yl]-6,8-dihydro-5H-[1,2,4]triazolo[5,1-c][1,4]oxazine-2-carboxamide | Single Unknown Stereoisomer | No NMR <2.9 mg isolated | 420.2 4.82 min |
| Example 696 0.120 Chiral table 1 | 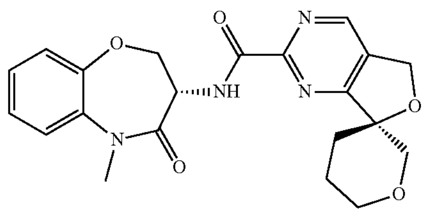 [SMILES: CN1C(=O)[C@@H](NC(=O)c2ncc3c(n2)[C@]2(CCCOC2)OC3)COc2ccccc21] rac-(75)-N-[rac-(3S)-5-methyl-4-oxo-2,3-dihydro-1,5-benzoxazepin-3-yl]spiro[5H-furo[3,4-d]pyrimidine-7,3'-tetrahydropyran]-2-carboxamide | Single Unknown Stereoisomer | $^1$H NMR (400 MHz, DMSO-d6) δ 9.00-8.91 (m, 2H), 7.56-7.47 (m, 1H), 7.39-7.23 (m, 3H), 5.15 (d, J = 1.0 Hz, 2H), 4.94-4.82 (m, 1H), 4.62-4.45 (m, 2H), 3.90-3.82 (m, 1H), 3.70 (dd, J = 11.9, 1.9 Hz, 1H), 3.61-3.47 (m, 1H), 3.34 (s, 3H), 3.39-3.23 (m, 2H), 2.12-1.95 (m, 1H), 1.86 (s, 1H), 1.73-1.64 (m, 1H). | 411.1 4.07 min |
| Example 697 Chiral table 1 | 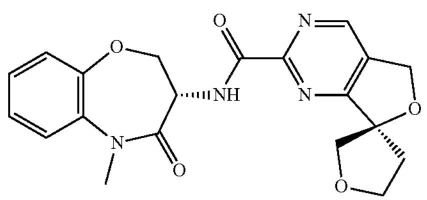 [SMILES: CN1C(=O)[C@@H](NC(=O)c2ncc3c(n2)[C@@]2(CCOC2)OC3)COc2ccccc21] rac-(7R)-N-[rac-(3S)-5-methyl-4-oxo-2,3-dihydro-1,5-benzoxazepin-3-yl]spiro[5H-furo[3,4-d]pyrimidine-7,3'-tetrahydrofuran]-2-carboxamide | Single Unknown Stereoisomer | $^1$H NMR (400 MHz, DMSO-d6) δ 9.08-8.80 (m, 1H), 7.70-7.42 (m, 0H), 7.41-7.16 (m, 2H), 5.15 (d, J = 1.0 Hz, 1H), 5.01-4.79 (m, 0H), 4.73-4.37 (m, 1H), 4.20-3.81 (m, 2H), 3.34 (s, 2H), 2.27 (ddd, J = 7.1, 6.3, 3.6 Hz, 1H). | 397.1 3.92 min |

TABLE 5

| Example Ki (uM) Method(s) | Structure | Stereo | $^1$H-NMR | MS (m/z) |
|---|---|---|---|---|
| Example 698 0.027 Suzuki Method 1 | 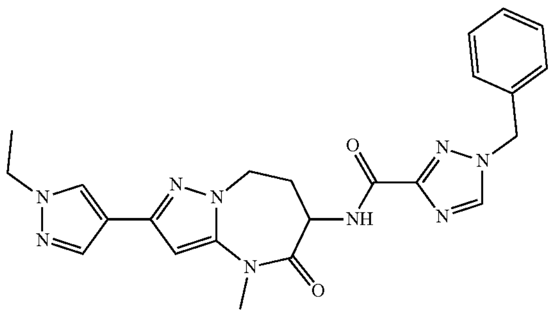 [SMILES: CCn1cc(-c2cc3n(n2)CCC(NC(=O)c2ncn(Cc4ccccc4)n2)C(=O)N3C)cn1] 1-benzyl-N-[2-(1-ethylpyrazol-4-yl)-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-$d_6$ δ 8.82 (s, 1H), 8.54 (d, J = 7.8 Hz, 1H), 8.04 (d, J = 0.7 Hz, 1H), 7.7 (d, J = 0.7 Hz, 1H), 7.55-7.21 (m, 5H), 6.50 (s, 1H), 5.48 (s, 2H), 4.45-4.28 (m, 2H), 4.24-4.09 (m, 3H), 3.26 (s, 3H), 2.69-2.57 (m, 1H), 2.43-2.30 (m, 1H), 1.39 (t, J = 7.3 Hz, 3H). | 460.2 4.04 min |
| Example 699 0.053 Suzuki Method 1 | 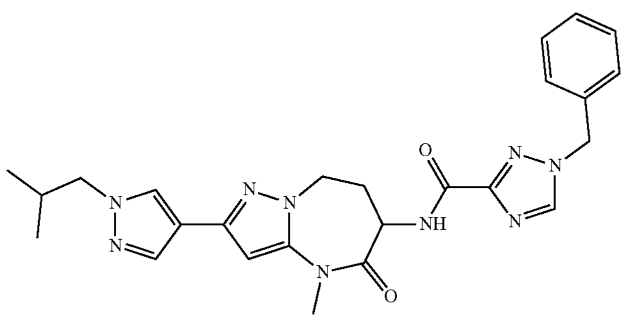 [SMILES: CC(C)Cn1cc(-c2cc3n(n2)CCC(NC(=O)c2ncn(Cc4ccccc4)n2)C(=O)N3C)cn1] 1-benzyl-N-[2-(1-isobutylpyrazol-4-methyl-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-$d_6$ δ 8.82 (s, 1H), 8.54 (d, J = 7.7 Hz, 1H), 8.00 (d, J = 0.7 Hz, 1H), 7.73 (d, J = 0.7 Hz, 1H), 7.44-7.23 (m, 5H), 6.51 (s, 1H), 5.48 (s, 2H), 4.46-4.29 (m, 2H), 4.25-4.11 (m, 1H), 3.93 (d, J = 7.2 Hz, 2H), 3.26 (s, 3H), 2.71-2.58 (m, 1H), 2.43-2.32 (m, 1H), 2.19-2.05 (m, 1H), 0.85 (d, J = 6.7 Hz, 6H). | 488.2 451 min |

TABLE 5-continued

| Example Ki (uM) Method(s) | Structure | Stereo | $^1$H-NMR | MS (m/z) |
|---|---|---|---|---|
| Example 700<br>0.448<br>Method B | 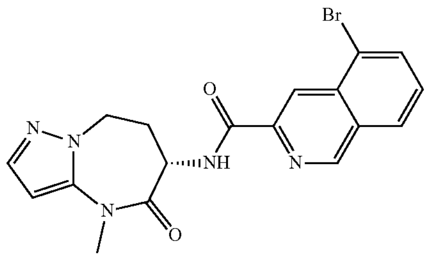 [SMILES: CN1C(=O)[C@@H](NC(=O)c2cc3c(Br)cccc3cn2)CCn2nccc21]<br>5-bromo-N-[(6S)-4-methyl-5-oxo-7,8-dihydro-6H-pyrazolo[1,5-a][1,3]diazepin-6-yl]isoquinoline-3-carboxamide | Single Known Stereoisomer | $^1$H NMR (400 MHz, DMSO-$d_6$ δ 9.94 (d, J = 0.8 Hz, 1H), 9.13 (d, J = 7.7 Hz, 1H), 8.58 (t, J = 0.9 Hz, 1H), 8.35 (d, J = 8.3 Hz, 1H), 8.26 (dd, J = 7.5, 1.0 Hz, 1H), 7.77 (dd, J = 8.2, 7.5 Hz, 1H), 7.52 (d, J = 2.0 Hz, 1H), 6.37 (d, J = 2.0 Hz, 1H), 4.50-4. 37 (m, 2H), 4.33-4.19 (m, 1H), 3.29 (s, 3H), 2.81-2.71 (m, 1H), 2.46-2.35 (m, 1H). | 414.0<br>510 min |
| Example 701<br>0.618<br>Method B | 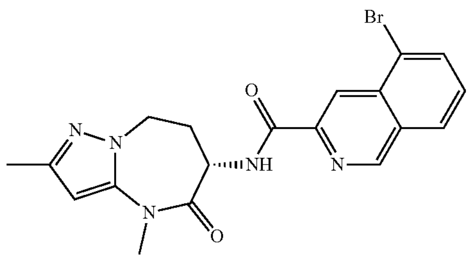 [SMILES: Cc1cc2n(n1)CC[C@H](NC(=O)c1cc3c(Br)cccc3cn1)C(=O)N2C]<br>5-bromo-N-[(6S)-2,4-dimethyl-5-oxo-7,8-dihydro-6H-pyrazolo[1,5-a][1,3]diazepin-6-yl]isoquiniline-3-carboxamide | Single Known Stereoisomer | $^1$H NMR (400 MHz, DMSO-$d_6$) δ 9.49 (d, J = 0.9 Hz, 1H), 9.11 (d, J = 7.8 Hz, 1H), 8.58 (t, J = 0.9 Hz, 1H), 8.40-8.31 (m 1H), 8.26 (dd, J = 7.5, 1.0 Hz, 1H), 7.77 (dd, J = 8.2, 7.5 Hz, 1H), 6.15 (s, 1H), 4.54-4.38 (m, 1H), 4.38-4.25 (m, 1H), 4.24-4.08 (m, 1H), 3.26 (s, 3H), 2.89 (d, J = 0.4 Hz 0H), 2.80-2.66 (m, 2H), (m, 1H), 2.19 (d, J = 0.5 Hz, 3H). | 428.0<br>532 min |
| Example 702<br>0.033<br>Method B and Suzuki Method 1 | 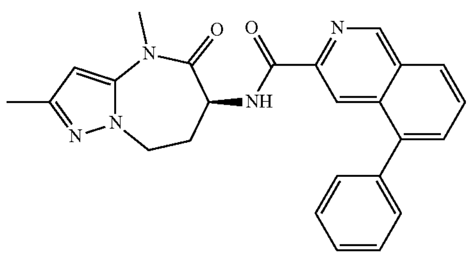 [SMILES: Cc1cc2n(n1)CC[C@H](NC(=O)c1cc3c(-c4ccccc4)cccc3cn1)C(=O)N2C]<br>5-phenyl-N-[(6S)-2,4-dimethyl-5-oxo-7,8-dihydro-6H-pyrazolo[1,5-a][1,3]diazepin-6-yl]isoquinoline-3-carboxamide | Single Known Stereoisomer | $^1$H NMR (400 MHz, DMSO-$d_6$) δ 9.50 (d, J = 0.9 Hz, 1H), 9.06 (d, J = 7.7 Hz, 1H), 8.44-8.18 (m, 2H), 7.97-7.79 (m, 2H), 7.66-7.46 (m, 5H), 6.12 (s, 1H), 4.45-4.34 (m, 1H), 4.34-4.22 (m, 1H), 4.22-4.08 (m, 1H), 3.24 (s, 3H), 2.75-2.62 (m, 1H), 2.39-2.27 (m, 1H), 2.17 (s, 3H). | 426.1<br>7.20 min |

TABLE 5-continued

| Example Ki (uM) Method(s) | Structure | Stereo | $^1$H-NMR | MS (m/z) |
|---|---|---|---|---|
| Example 703 0.024 Method B and Suzuki Method 1 | 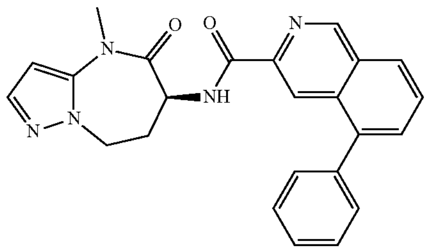 [SMILES: CN1C(=O)[C@@H](NC(=O)c2cc3c(-c4ccccc4)cccc3cn2)CCn2nccc21] 5-phenyl-N-[(6S)-4-methyl-5-oxo-7,8-dihydro-6H-pyrazolo[1,5-a][1,3]diazepin-6-yl]isoquinoline-3-carboxamide | Single Known Stereoisomer | $^1$H NMR (400 MHz, DMSO-$d_6$) δ 9.51 (d, J = 0.9 Hz, 1H), 9.08 (d, J = 7.7 Hz, 1H) 8.40-8.25 (m, 2H), 7.97-7.79 (m, 2H), 7.66-7.46 (m, 6H), 6.33 (d, J = 2.0 Hz, 1H), 4.45-4.32 (m, 2H), 4.32-4.17 (m, 1H), 3.27 (s, 3H), 3.78-2.64 (m, 1H), 2.44-2.31 (m, 1H). | 412.1 6.97 min |
| Example 704 0.095 Suzuki Method 1 | 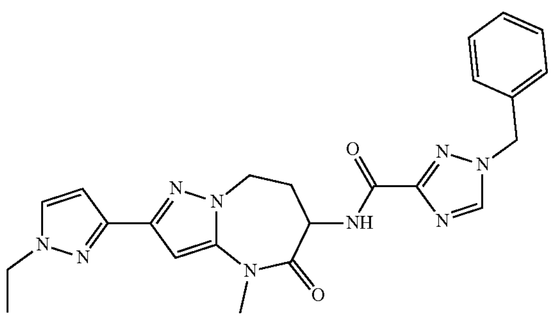 [SMILES: CCn1ccc(-c2cc3n(n2)CCC(NC(=O)c2ncn(Cc4ccccc4)n2)C(=O)N3C)n1] 1-benzyl-N-[2-(1-ethylpyrazol-3-yl)-4-methyl-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-$d_6$) δ 8.82 (s, 1H), 8.54 (d, J = 7.8 Hz, 1H), 7.75 (d, J = 2.3 Hz, 1H), 7.46-7.25 (m, 5H, 6.59 (s, 1H), 6.50 (d, J = 2.2 Hz, 1H), 5.48 (s, 2H), 4.44-4.33 (m, 2H), 4.28-4.19 (m, 1H), 4.15 (q, J = 7.2 Hz, 2H), 3.28 (s, 3H), 2.69-2.60 (m, 1H), 2.42-2.33 (m, 1H), 1.39 (t, J = 7.3 Hz, 3H). | 460.2 5.45 min |

TABLE 5-continued

| Example Ki (uM) Method(s) | Structure | Stereo | $^1$H-NMR | MS (m/z) |
|---|---|---|---|---|
| Example 705 0.114 METHOD GHS | 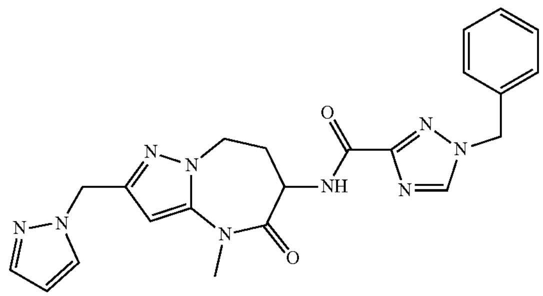 [SMILES: CN1C(=O)C(NC(=O)c2ncn(Cc3ccccc3)n2)CCn2nc(Cn3cccn3)cc21] 1-benzyl-N-[4-methyl-5-oxo-2-(pyrazol-1-ylmethyl)-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-d6) δ 8.81 (s, 1H), 8.53 (d, J = 7.8 Hz, 1H), 7.78 (dd, J = 2.3, 0.7 Hz, 1H), 7.44 (dd, J = 1.9, 0.7 Hz, 1H), 7.41-7.27 (m, 5H), 6.25 (dd, J = 2.3, 1.8 Hz, 1H), 6.21 (s, 1H), 5.48 (s, 2H), 5.32-5.20 (m, 2H) 4.38-4.25 (m, 2H), 4.16 (ddd, J = 14.5, 12.6, 6.6 Hz, 1H), 3.20 (s, 3H), 2.65-2.53 (m, 1H), 2.42-2.30 (m, 1H). | |
| Example 706 0.413 METHOD GH5 | 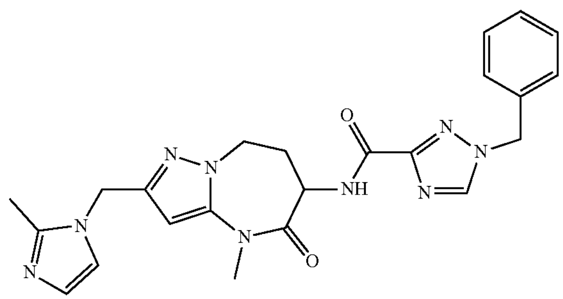 [SMILES: Cc1nccn1Cc1cc2n(n1)CCC(NC(=O)c1ncn(Cc3ccccc3)n1)C(=O)N2C] 1-benzyl-N-[4-methyl-2-[(2-methylimidazol-1-yl)methyl]-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-d6) δ 8.81 (s, 1H), 8.53 (d, J = 7.8 Hz, 1H), 7.44-7.25 (m, 5H), 7.08 (d, J = 1.3 Hz, 1H), 6.71 (d, J = 1.3 Hz, 1H), 6.23 (s, 1H), 5.48 (s, 2H), 5.12-4.96 (m, 2H, 4.16 (ddd, J = 14.5, 12.6, 6.6 Hz, 1H), 3.20 (s, 3H), 2.68-2.52 ( m, 1H), 2.44-2.34 (m, 1H), 2.31 (s, 3H). LCMS RT = 2.66 min [10 min method], m/z = 460.2 [M + H]+. | |

TABLE 5-continued

| Example Ki (uM) Method(s) | Structure | Stereo | $^1$H-NMR | MS (m/z) |
| --- | --- | --- | --- | --- |
| Example 707 0.53 METHOD GH5 | 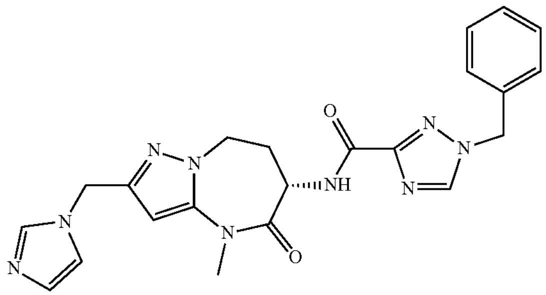 [SMILES: CN1C(=O)[C@@H](NC(=O)c2ncn(Cc3ccccc3)n2)CCn2nc(Cn3ccnc3)cc21] (S)-1-benzyl-N-[2-(imidazol-1-ylmethyl)-4-methyl-5-oxo-7,8-dihydro-6H-pyrazolo[1,5-a][1,3]diazepin-6-yl]-1,2,4-triazole-3-carboxamide | Single Known Stereoisomer | $^1$H NMR (400 MHz, DMSO-d6) δ 8.81 (s, 1H), 8.53 (d, J = 7.8 Hz, 1H), 7.70 (t, J = 1.1 Hz, 1H), 7.42-7.26 (m, 5H), 7.19 (t, J = 1.2 Hz, 1H), 6.89 (t, J = 1.1 Hz, 1H), 6.29 (s, 2H), 5.20-5.07 (m, 2H), 4.37-4.25 (m, 2H), 4.17 (ddd, J = 14.6, 12.7, 6.7 Hz, 1H), 3.22-3.19 (m, 3H), 2.65-2.54 (m, 1H), 2.42-2.31 (m, 1H). | |
| Example 708 0.004 METHOD GH6 | 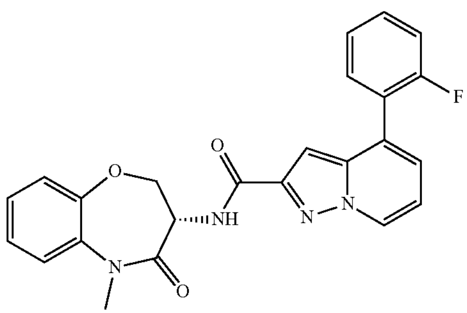 [SMILES: CN1C(=O)[C@@H](NC(=O)c2cc3c(-c4ccccc4F)cccn3n2)COc2ccccc21] 4-(2-fluorophenyl)-N-[(3S)-5-methyl-4-oxo-2,3-dihydro-1,5-benzoxazepin-3-yl]pyrazolo[1,5-a]pyridine-2-carboxamide | Single Known Stereoisomer | $^1$H NMR (400 MHz, DMSO-d6) δ 8.83 (dt, J = 7.0, 1.0 Hz, 1H), 8.52 (d, J = 8.1 Hz, 1H), 7.64 (td, J = 7.6, 1.8 Hz, 1H), 7.56 (dddd, J = 8.4, 7.2, 5.3, 1.8 Hz, 1H), 7.53-7.48 (m, 1H), 7.46-7.36 (m, 3H), 7.36-7.26 (m, 2H), 7.26-7.23 (m, 1H), 7.19 (t, J = 7.0 Hz, 1H), 6.80 (dd, J = 2.0, 1.0 Hz, 1H), 4.91 (dt, J = 11.6, 7.9 Hz, 1H), 4.59 (dd, J = 11.6, 9.9 Hz, 1H), 4.44 (dd, J = 9.9, 7.7 Hz, 1H), 3.3 (s, 3H). | |

TABLE 5-continued

| Example<br>Ki (uM)<br>Method(s) | Structure | Stereo | $^1$H-NMR | MS (m/z) |
|---|---|---|---|---|
| Example 709<br>0.034<br>METHOD GH8 | 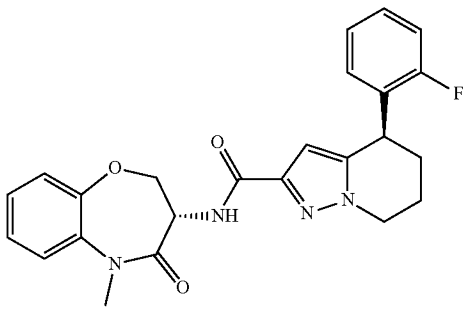 [SMILES: CN1C(=O)[C@@H](NC(=O)c2cc3n(n2)CCC[C@@H]3c2ccccc2F)COc2ccccc21]<br>(4R)-4-(2-flurophenyl)-N-[(3S)-5-methyl-4-oxo-2,3-dihydro-1,5-benzoxazepin-3-yl]-4,5,6,7-trtrahydropyrazolo[1,5-a]pyridine-2-carboxamide | Single<br>Unknown<br>Stereoisomer | $^1$H NMR (400 MHz, DMSO-d6) δ 8.08 (d, J = 8.1 Hz, 1H), 7.51-7.46 (m, 1H), 7.37-7.24 (m, 3H), 7.24-7.11 (m, 4H) 6.03 (d, J = 1.0 Hz, 1H), 4.81 (dt, J = 11.5, 7.9 Hz, 1H), 4.53 (dd, J = 11.6, 9.9 Hz, 1H), 4.42 (dd, J = 9.5, 4.7 Hz, 1H), 4.36 (dd, J = 9.9, 7.7 Hz, 1H), 4.32-4.14 (m, 2H), 3.30 (s, 3H), 2.20-1.99 (m, 3H), 2.20-1.99 (m, 3H), 1.99-1.84 (m, 1H). | |
| Example 710<br>0.009<br>METHOD GH8 | 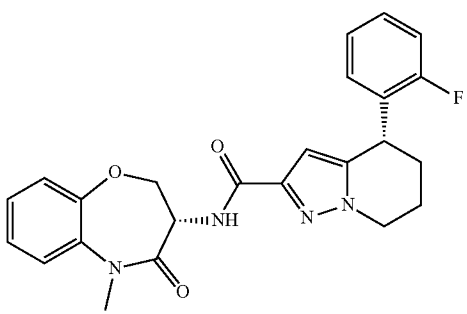 [SMILES: CN1C(=O)[C@@H](NC(=O)c2cc3n(n2)CCC[C@H]3c2ccccc2F)COc2ccccc21]<br>(4S)-4-(2-flurophenyl)-N-[(3S)-5-methyl-4-oxo-2,3-dihydro-1,5-benzoxazepin-3-yl]-4,5,6,7-trtrahydropyrazolo[1,5-a]pyridine-2-carboxamide | Single<br>Unknown<br>Stereoisimer | $^1$H NMR (400 MHz, DMSO-d6) δ 8.06 (d, J = 8.1Hz, 1H), 7.53-7.45 (m, 1H), 7.38-7.24 (m, 3H), 7.24-7.12 (m, 4H), 6.04 (d, J = 0.9 Hz, 1H), 4.81 (dt, J = 11.5, 7.9 Hz, 1H), 4.51 (dd, J = 11.5, 9.9 Hz, 1H, 4.42 (dd, J= 9.6, 4.8 Hz, 1H), 4.36 (dd, J = 9.9, 7.7 Hz, 1H), 4.33-4.14 (m, 2H), 3.30 (s, 3H), 2.19-2.00 (m, 3H), 1.90 (q, J = 10.1 Hz, 1H). | |

TABLE 5-continued

| Example Ki (uM) Method(s) | Structure | Stereo | $^1$H-NMR | MS (m/z) |
|---|---|---|---|---|
| Example 711 0.073 METHOD GH7 | 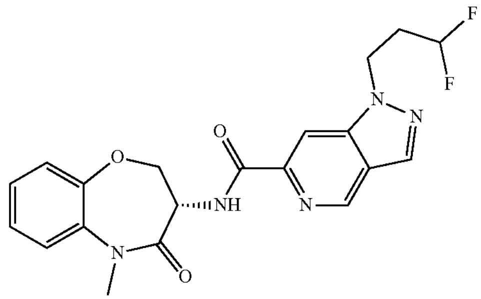 [SMILES: CN1C(=O)[C@@H](NC(=O)c2cc3c(cn2)cnn3CCC(F)F)COc2ccccc21] 1-(3,3-difluoropropyl)-N-[(3S)-5-methyl-4-oxo-2,3-dihydro-1,5-benzoxazepin-3-yl] pyrazolo[4,3-c]pyridine-6-carboxamide | Single Known Stereoisomer | $^1$H NMR (400 MHz, DMSO-d6) δ 9.20 (d, J = 1.1 Hz, 1H), 9.03 (d, J = 7.8 Hz, 1H), 8.48 (d, J = 1.0 Hz, 1H), 8.34 (t, J = 1.1 Hz, 1H), 7.55-7.50 (m, 1H), 7.40-7.24 (m, 3H), 6.15 (tt, J = 56.2, 4.4 Hz, 1H), 4.93 (dt, J = 10.5, 8.2 Hz, 1H), 4.70 (t, J = 6.8 Hz, 2H), 4.60-4.49 (m, 2H), 3.35 (s, 3H), 2.47-2.36 (m, 2H). | |
| Example 713 0.005 METHOD GH6 | 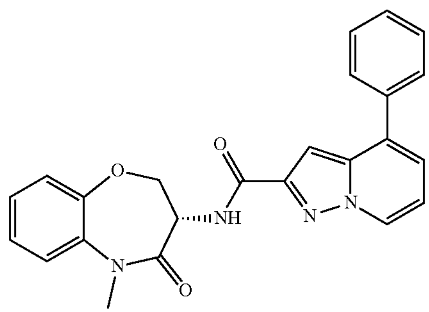 [SMILES: CN1C(=O)[C@@H](NC(=O)c2cc3c(-c4ccccc4)cccn3n2)COc2ccccc21] 4-phenyl-N-[(3S)-5-methyl-4-oxo-2,3-dihydro-1,5-benzoxazepin-3-yl]pyrazolo [1,5-a]pyridine-2-carboxamide | Single Known Stereoisomer | $^1$H NMR (400 MHz, DMSO-d6) δ 8.77 (dt, J = 7.0, 1.0 Hz, 1H), 8.53 (d, J = 8.1 Hz, 1H), 7.76-7.67 (m, 2H), 7.61-7.45 (m, 4H), 7.41 (dd, J = 7.1, 0.9 Hz, 1H), 7.38-7.22(m, 3H), 7.22-7.13 (m, 1H), 7.07 (d, J = 1.0 Hz, 1H), 4.92 (dt, J = 1.0 Hz, 1H), 4.59 (dd, J = 11.6, 9.9 Hz, 1H), 4.45 (dd, J = 9.9, 7.7 Hz, 1H), 3.33 (s, 3H). | |

TABLE 5-continued

| Example Ki (uM) Method(s) | Structure | Stereo | $^1$H-NMR | MS (m/z) |
|---|---|---|---|---|
| Example 714<br>0.013<br>METHOD GH6 | 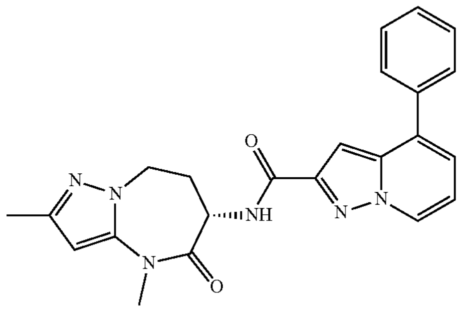 [SMILES: Cc1cc2n(n1)CC[C@H](NC(=O)c1cc3c(-c4ccccc4)cccn3n1)C(=O)N2C]<br>(S)-N-(2,4-dimethyl-5-oxo-5,6,7,8-tetrahydro-4H-pyrazolo[1,5-a][1,3]diazepin-6-yl)-4-phenylpyrazolo[1,5-a]pyridine-2-carboxamide | Single Known Stereoisomer | $^1$H NMR (400 MHz, DMSO-d6) δ 8.76 (dt, J = 7.0, 1.0 Hz, 1H), 8.58 (d, J = 7.9 Hz, 1H), 7.77-7.69 (m, 2H), 7.62-7.53 (m, 2H), 7.53-7.45 (m, 1H), 7.40 (dd, J = 7.1, 1.0 Hz, 1H), 7.17 (t, J = 7.0 Hz, 1H), 7.08 (d, J = 1.0 Hz, 1H) 6.14 (s, 1H), 4.41 (dt, J = 11.6, 7.9 Hz, 1H), 4.29 (dd, J = 14.5, 7.9 Hz, 1H), 4.20-4.05 (m, 1H), 3.23 (s, 3H), 2.68-2.56 (m, 1H), 2.41-2.30 (m, 1H), 2.18 (s, 3H). | |
| Example 715<br>0.005<br>GZ-chiral_1 | 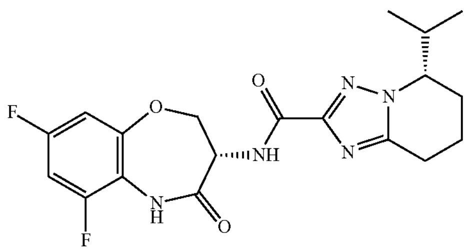 [SMILES: CC(C)[C@@H]1CCCc2nc(C(=O)N[C@H]3COc4cc(F)cc(F)c4NC3=O)nn21]<br>(5S)-N-[(3S)-6,8-difkuoro-4-oxo-3,5-dihydro-2H-1,5-benzoxazepin-3-yl]-5-isopropyl-5,6,7,8-tetrahydro-[1,2,4]triazolo[1,5-a]pyridine-2-carboxamide | Single Unknown Stereoisomer | $^1$H NMR (400 MHz, DMSO-d6) δ 10.07 (s, 1H), 8.38 (d, J = 7.7 Hz, 1H), 7.23 (ddd, J = 10.4, 9.0, 2.9 Hz, 1H), 7.03 (dt, J = 9.4 2.2 Hz, 1H), 4.90 (dt, J = 11.1, 7.4 Hz, 1H), 4.65 (t, J = 10.7 Hz, 1H), 4.52 (dd, J = 10.2, 7.1 Hz, 1H), 4.17 (dt, J = 8.8, 4.6 Hz, 1H), 2.90 (m, 1H), 2.79 (m, 1H), 2.68-2.59 (m, 1H), 2.10-1.98 (m, 2H), 1.84-4.65 (m, 2H), 0.98 (d, J = 7.1 Hz, 3H), 0.69 (d, J = 6.8 GHz, 3H). | 406.1<br>4.60 min |

TABLE 5-continued

| Example Ki (uM) Method(s) | Structure | Stereo | $^1$H-NMR | MS (m/z) |
|---|---|---|---|---|
| Example 716<br>0.003<br>GZ_chiral_1 | 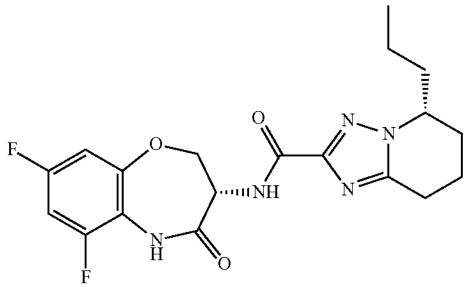 [SMILES: CCC[C@@H]1CCCc2nc(C(=O)N[C@H]3COc4cc(F)cc(F)c4NC3=O)nn21]<br>(5R)-N-[(3S)-6,8-difluoro-4-oxo-3,5-dihydro-2H-1,5-benzoxazepin-3-yl]-5-propyl-5,6,7,8-tetrahydro-[1,2,4]triazolo[1,5-a]pyrodine-2-carboxamide | Single Unknown Stereoisomer | None | 406.1<br>4.68 min |
| Example 717<br>0.207<br>GZ_chiral_1 | 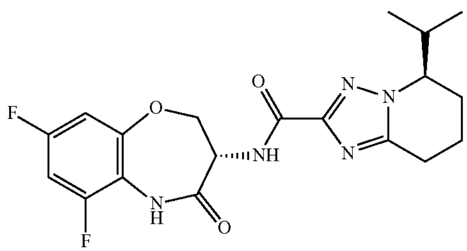 [SMILES: CC(C)[C@H]1CCCc2nc(C(=O)N[C@H]3COc4cc(F)cc(F)c4NC3=O)nn21]<br>(5R)-N-[(3S)-6,8-difluoro-4-oxo-3,5-dihydro-2H-1,5-benzoxazepin-3-yl]-5-isopropyl-5,6,7,8-tetrahydro-[1,2,4]triazolo[1,5-a]pyrodine-2-carboxamide | Single Unknown Stereoisomer | $^1$H NMR (400 MHz, DMSO-d6) δ 10.07 (s, 1H), 8.38 (d, J = 7.7 Hz, 1H), 7.23 (ddd, J = 10.4, 9.0, 2.9 Hz, 1H), 7.03 (dt, J = 9.4, 2.2 Hz, 1H), 4.90 (dt, J = 11.1, 7.4 Hz, 1H), 4.65 (t, J = 10.7 Hz, 1H), 4.52 (dd, J = 10.2, 7.1 Hz, 1H), 4.17 (dt, J = 8.8, 4.6 Hz, 1H), 2.90 (m, 1H), 2.79 (m, 1H), 2.68-2.59 (m, 1H), 2.10-1.98 (m, 2H), 1.84-1.65 (m, 2H), 0.98 (d, J = 7.1 Hz, 3H), 0.69 (d, J = 6.8 Hz, 3H). | 406.1<br>4.58 min |

TABLE 5-continued

| Example<br>Ki (uM)<br>Method(s) | Structure | Stereo | $^1$H-NMR | MS (m/z) |
|---|---|---|---|---|
| Example 718<br>0.00<br>GZ_chiral_1 | 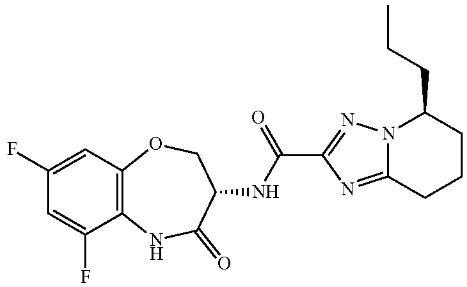 [SMILES: CCC[C@H]1CCCc2nc(C(=O)N[C@H]3COc4cc(F)cc(F)c4NC3=O)nn21]<br>(5R)-(S)-N-((S)-6,8-difluoro-4-oxo-2,3,4,5-tetrahydrobenzo[b][1,4]oxazepin-3-yl)-5-propyl-5,6,7,8-tetrahydro-[1,2,4]triazolo[1,5-a]pyridine-2-carboxamide | Single Unknown Stereoisomer | None | 406.1<br>4.48 min |
| Example 719<br>0.214<br>METHOD GZ9 | 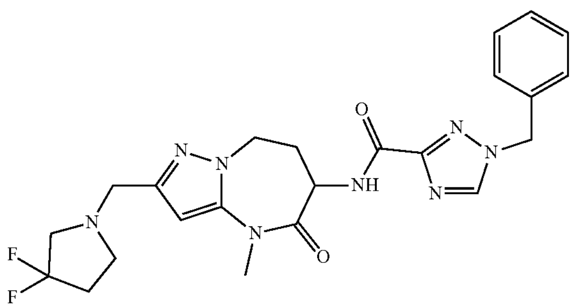 [SMILES: CN1C(=O)C(NC(=O)c2ncn(Cc3ccccc3)n2)CCn2nc(CN3CCC(F)(F)C3)cc21]<br>1-benzyl-N-[2-[(3,3-difluoropyrrplidin-1-yl)methyl]-4-methyl-5-oxo-7,8-dihydro-6H-pyrazolo[1,5-a][1,3]diazepin-6-yl]-1,2,4-triazole-3-carboxamide | Mixture of Enantiomer | $^1$H NMR (400 MHz, DMSO-$d_6$) δ 8.81 (s,1H), 8.52 (d, J = 7.8 Hz, 1H), 7.42-7.26 (m,5H), 6.28 (s, 1H), 5.48 (s, 2H), 4.31 (qd, J = 7.9, 2.4 Hz, 2H), 4.15 (ddd, J = 14.5, 12.6, 6.6 Hz, 1H), 3.57 (q, J = 13.4 Hz, 2H), 3.23 (s, 3H), 2.91 (t, J = 13.4 Hz, 2H), 2.73 (t, J = 7.0 Hz, 2H), 2.67-2.54 (m, 1H), 2.43-2.10 (m, 3H) | 485.2<br>2.88 min |

TABLE 5-continued

| Example Ki (uM) Method(s) | Structure | Stereo | $^1$H-NMR | MS (m/z) |
|---|---|---|---|---|
| Example 720 0.155 Method GZ9 | 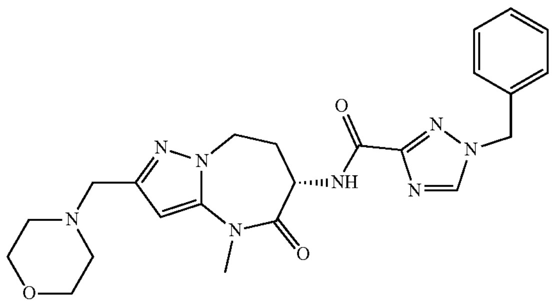 [SMILES: CN1C(=O)[C@@H](NC(=O)c2ncn(Cc3ccccc3)n2)CCn2nc(CN3CCOCC3)cc21] 1-benzyl-N-[(6S)-4-methyl-2-(morpholinomethyl)-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-$d_6$) δ 8.81 (s, 1H), 8.51 (d, J = 7.7 Hz, 1H), 7.42-7.26 (m, 5H), 6.26 (s, 1H), 5.48 (s, 2H), 4.36-4.24 (m, 2H), 4.14 (m, 1H), 3.57 (m, 4H), 3.48-3.21 (m, 5H), 2.59 (m, 1H), 2.43-2.29 (m, 5H). | 465.2 2.55 min |
| Example 721 0.355 Method GZ9 | 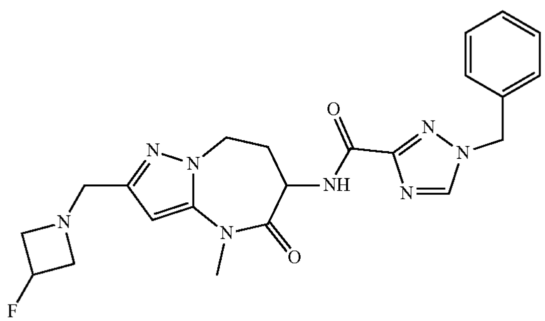 [SMILES: CN1C(=O)C(NC(=O)c2ncn(Cc3ccccc3)n2)CCn2nc(CN3CC(F)C3)cc21] 1-benzyl-N-[2-[(3-fluoroazetidin-1-yl)methyl]-4-methyl-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-$d_6$) δ 8.81 (s, 1H), 8.52 (d, J = 7.8 Hz, 1H), 7.42-7.26 (m, 5H), 5.23 (s, 1H), 5.48 (s, 2H), 5.26-5.01 (m, 1H), 4.35-4.23 (m, 2H), 4.4 (m, 1H), 3.63-3.50 (m, 4H), 3.27-3.06 (m, 5H), 2.58 (m, 1H), 2.41-2.28 (m, 1H). | 453.2 2.58 min |

TABLE 5-continued

| Example Ki (uM) Method(s) | Structure | Stereo | $^1$H-NMR | MS (m/z) |
|---|---|---|---|---|
| Example 722 0.444 Method GZ9 | 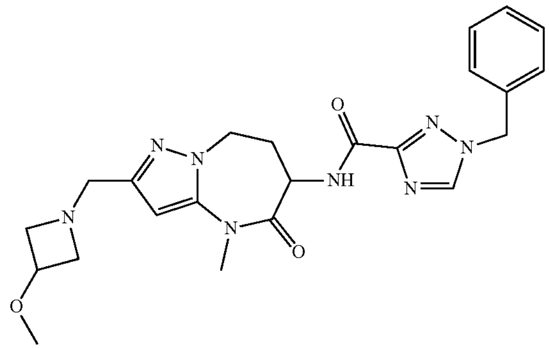 [SMILES: COC1CN(Cc2cc3n(n2)CCC(NC(=O)c2ncn(Cc4ccccc4)n2)C(=O)N3C)C1] 1-benzyl-N-[2-[(3-methoxyazetidin-1-yl) methyl]-4-methyl-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-$d_6$) δ 8.81 (s, 1H), 8.51 (d, J = 7.8 Hz, 1H), 7.42-7.23 (m, 5H), 6.21 (s, 1H), 5.48 (s, 2H), 4.29 (m, 2H), 4.13 (m, 1H), 3.94 (m, 1H), 3.48 (m, 4H), 3.22 (s, 3H), 3.14 (s, 3H), 2.92-2.81 (m, 2H), 2.57 (m, 1H), 2.41-2.28 (m, 1H). | 465.2 2.66 min |
| Example 723 0.206 METHOD GZ6 | 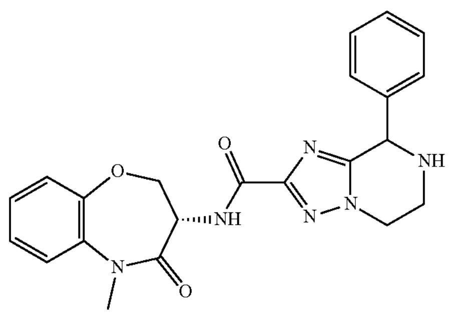 [SMILES: CN1C(=O)[C@@H](NC(=O)c2nc3n(n2)CCNC3c2ccccc2)COc2ccccc21] N-[(3S)-5-methyl-4-oxo-2,3-dihydro-1,5-benzoxazepin-3-yl]-8-phenyl-5,6,7,8-tetrahydro-[1,2,4]triazolo[1,5-a]pyrazine-2-carboxamide | Mixture of Diastereomers | $^1$H NMR (400 MHz, DMSO-$d_6$) δ 8.34 (dd, J = 8.1, 1.9 Hz, 1H), 7.49 (dt, J = 7.5, 1.5 Hz, 1H), 7.44-7.11 (m, 9H), 5.20 (t, J = 5.0 Hz, 1H), 4.91-4.75 (, 1H), 4.56 (ddd, J = 11.5, 9.9, 4.1 Hz, 1H), 4.37 (ddd, J = 9.9, 7.6, 6.0 Hz, 1H), 4.32-4.15 (m, 2H), 3.37 (q, J = 5.3 Hz, 1H), 3.32-3.11 (m, 4H). | 419.1 3.26 min |

TABLE 5-continued

| Example Ki (uM) Method(s) | Structure | Stereo | $^1$H-NMR | MS (m/z) |
|---|---|---|---|---|
| Example 724 0.598 Method GZ9 | 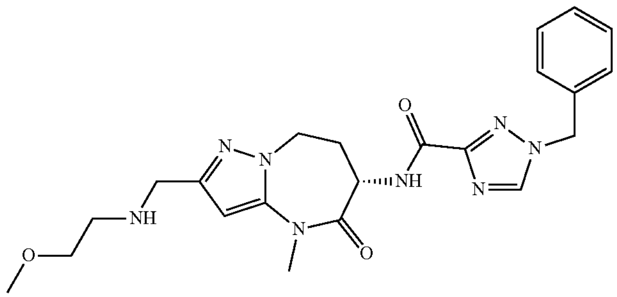 [SMILES: COCCNCc1cc2n(n1)CC[C@H](NC(=O)c1ncn(Cc3ccccc3)n1)C(=O)N2C] 1-benzyl-N-[2-[(2-methoxyethylamino) methyl]-4-methyl-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-$d_6$) δ 8.82 (s, 1H), 8.51 (d, J = 7.8 Hz, 1H), 7.43-7.26 (m, 5H), 6.26 (s, 1H), 5.48 (s, 2H), 4.31 (m, 2H), 4.21-4.07 (m, 1H), 3.66 (d, J = 2.1 Hz, 2H), 3.46-3.31 (m, 2H), 3.23 (s, 6H), 2.72 *t J = 5.7 Hz, 2H), 2.58 (m, 1H), 2.41-2.28 (m, 1H). | 453.2 2.62 min |
| Example 725 0.172 Method GZ9 | 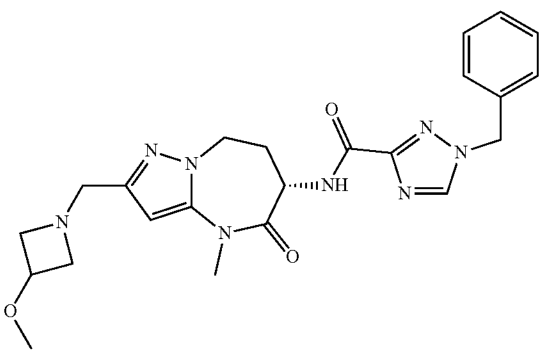 [SMILES: COC1CN(Cc2cc3n(n2)CC[C@H](NC(=O)c2ncn(Cc4ccccc4)n2)C(=O)N3C)C1] (S)-1-benzyl-N-(2-((3-methoxyazetidin-1-yl)methyl)-4-methyl-5-oxo-5,6,7,8-tetrahydro-4H-pyrazolo[1,5-a][1,3] diazepin-6-yl)-1H-1,2,4-triazole-3-carboxamide | Single unknown Stereoisomer | $^1$H NMR (400 MHz, DMSO-$d_6$) δ 8.81 (s, 1H), 8.51 (d, J = 7.7 Hz, 1H), 7.42-7.26 (m, 5H), 6.21 (s, 1H), 5.48 (s, 2H), 4.35-4.23 (m, 2H), 4.13 (m, 1H), 3.94 (p, J = 5.8 Hz, 1H), 3.57-3.32 (m, 4H), 3.18 (ds, 6H), 2.86 (m, 2H), 2.58 (m, 1H), 2.41-2.28 (m, 1H). | 465.2 2.62 min |

TABLE 5-continued

| Example Ki (uM) Method(s) | Structure | Stereo | $^1$H-NMR | MS (m/z) |
|---|---|---|---|---|
| Example 726<br>0.142<br>Method GZ9 | 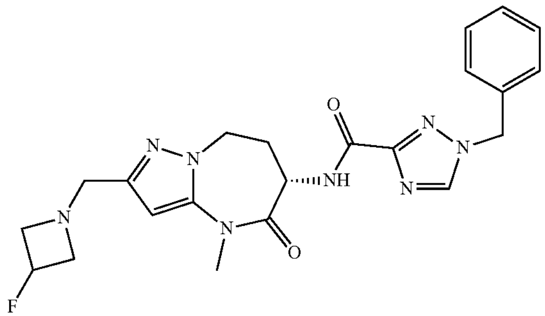 [SMILES: CN1C(=O)[C@@H](NC(=O)c2ncn(Cc3ccccc3)n2)CCn2nc(CN3CC(F)C3)cc21]<br>(S)-1-benzyl-N-(2-((3-fluoroazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide | Single unknown Stereoisomer | $^1$H NMR (400 MHz, DMSO-$d_6$) δ 8.81 (s, 1H), 8.52 (d, J = 7.8 Hz, 1H), 7.42-7.26 (m, 5H), 6.23 (s, 1H), 5.48 (s, 2H), 5.26-5.01 (m, 1H) 4.35-4.23 (m, 2H), 4.14 (m, 1H), 3.63-3.50 (m, 4H), 3.27-3.06 (m, 5H), 2.58 (m, 1H), 2.41-2.28 (m, 1H). | 4.53.2<br>2.59 min |
| Example 727<br>0.059<br>Method GZ9 | 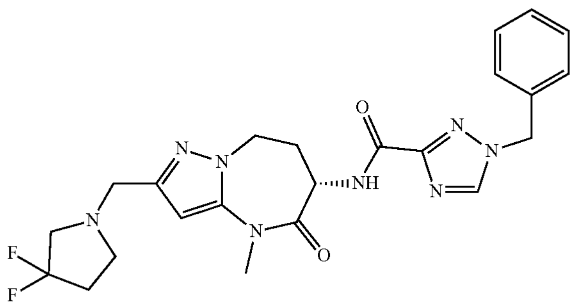 [SMILES: CN1C(=O)[C@@H](NC(=O)c2ncn(Cc3ccccc3)n2)CCn2nc(CN3CCC(F)(F)C3)cc21]<br>(S)-1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide | Single Unknown Stereoisomer | $^1$H NMR (400 MHz, DMSO-$d_6$) δ 8.81 (s, 1H), 8.52 (d, J = 7.8 Hz, 1h), 7.42-7.26 (m, 5H), 6.28 (s, 1H), 5.48 (s, 2H), 4.31 (qd, J = 7.9, 2.4 Hz, 2H), 4.15 (ddd, J = 14.5, 12.6, 6.6 Hz, 1H), 3.57 (q, J = 13.4 Hz, 2H), 3.23 (s, 3H), 2.91 (t, J = 13.4 Hz, 2H), 2.73 (t, J = 7.0 Hz, 2H), 2.67-2.54 (m, 1H), 2.43-2.10 (m, 3H). | 4.82<br>2.86 min |

TABLE 5-continued

| Example Ki (uM) Method(s) | Structure | Stereo | $^1$H-NMR | MS (m/z) |
|---|---|---|---|---|
| Example 728 0.225 | 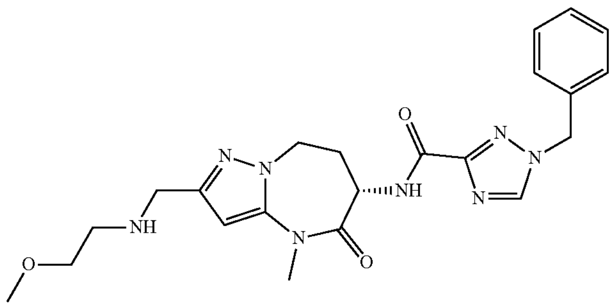 [SMILES: COCCNCc1cc2n(n1)CC[C@H](NC(=O)c1ncn(Cc3ccccc3)n1)C(=O)N2C] (S)-1-benzyl-N-(2-(((2-methoxyethyl) amino)methyl)-4-methyl-5-oxo-5,6,7,8-tetrahydro-4H-pyrazolo[1,5-a][1,3] diazepin-6-yl)-1H-1,2,4-triazole-3-carboxamide | Single Unknown Stereoisomer | $^1$H NMR (400 MHz, DMSO-$d_6$) δ 8.82 (s, 1H), 8.51 (d, J = 7.8 Hz, 1H), 7.43-7.26 (m, 5H), 6.26 (s, 1H), 5.48 (s, 2H), 4.31 (m, 2H), 4.21-4.07 (m, 1H), 3.66 (d, J = 2.1 Hz, 3.46-3.31 (m, 2H), 3.23 (s, 6H), 2.72 (t, J = 5.7 Hz, 2H), 2.58 (m, 1H), 2.41-2.28 (m, 1H). | 453.2 2.65 min |
| Example 729 0.074 (purification of Ex. 723) | 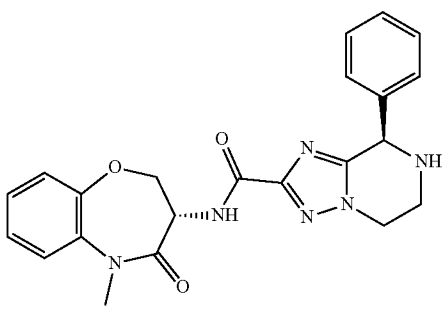 [SMILES: CN1C(=O)[C@@H](NC(=O)c2nc3n(n2)CCN[C@@H]3c2ccccc2)COc2ccccc21] (8R)-N-[(3S)-5-methyl-4-oxo-2,3-dihydro-1,5-benzoxazepin-3-yl]-8-phenyl-5,6,7,8-tetrehydro-[1,5-a] pyrazine-2-carboxamide | Single Unknown Stereoisomer | $^1$H NMR (400 MHz, DMSO-$d_6$) δ 8.34 (d, J = 8.0 Hz, 1H), 7.49 (dd, J = 7.6, 1.9 Hz, 1H), 7.42-7.18 (m,9H), 5.20 (d, J = 5.3 Hz, 1H), 4.81 (dt, J = 11.4, 7.8 Hz, 1H), 4.56 (dd, J = 11.6, 9.8 Hz, 1H), 4.36 (dd, J = 9.9 7.7 Hz, 1H), 4.32-4.15 (m, 2H), (q, J = 5.1 Hz, 1H), 3.32-3.11 (m, 4H). | 419.1 3.26 min |

TABLE 5-continued

| Example Ki (uM) Method(s) | Structure | Stereo | $^1$H-NMR | MS (m/z) |
|---|---|---|---|---|
| Example 730<br>0.112<br>Method GZ17 | 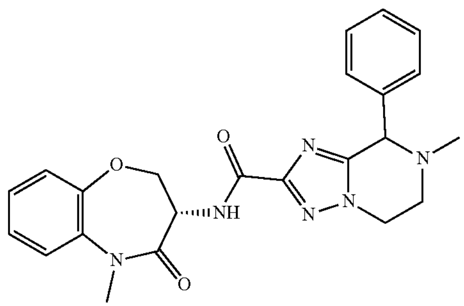 [SMILES: CN1C(=O)[C@@H](NC(=O)c2nc3n(n2)CCN(C)C3c2ccccc2)COc2ccccc21]<br>7-methyl-N-[(3S)-5-methyl-4-oxo-2,3-dihydro-1,5-benzoxazepin-3-yl]-8-phenyl-6,8-dihydro-5H-[1,2,4]triazolo[1,5-a]pyrazine-2-carboxamide | Single Unknown Stereoisomer | $^1$H NMR (400 MHz, DMSO-$d_6$) δ 8.28 (dd, J = 8.0, 5.5 Hz, 1H), 7.48 (dt, J = 7.6, 2.0 Hz, 1H), 7.42-7.17 (m, 9H), 4.85-4.72 (m, 1H), 4.61-4.49 (m, 2H), 4.45-4.27 (m, 3H), 3.28 (d, J = 1.9 Hz, 4H), 3.00-2.87 (m, 1H), 2.21 (s, 3H) | 433.2<br>4.29 min |
| Example 731<br>0.30 | 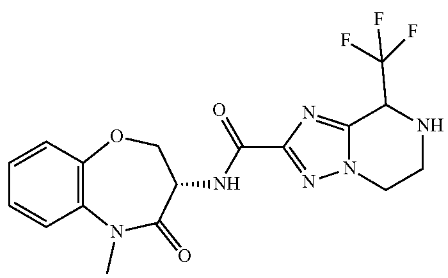 [SMILES: CN1C(=O)[C@@H](NC(=O)c2nc3n(n2)CCNC3C(F)(F)F)COc2ccccc21]<br>N-[(3S)-5-methyl-4-oxo-2,3-dihydro-1,5-benzoxazepin-3-yl]-8-(trifluoromethyl)-5,6,7,8-tetrahydro-[1,2,4]triazolo[1,5-a]pyrazine-2-carboxamide | Mixture of Diastereomers | $^1$H NMR (400 MHz, DMSO-$d_6$) δ 8.44 (dd, J = 7.9, 23. Hz, 1H), 7.57-7.45 (m, 1H), 7.39-7.16 (m, 4H) 5.16-4.99 (m, 1H), 4.85 (dtd, J = 11.5, 7.8 3.8 Hz, 1H), 4.60 (dt, J = 11.5, 9.7 Hz, 1H), 4.43 (ddd, J = 9.9, 7.6, 6.8 Hz, 1H), 4.25 (m, 1H), 4.21-4.04 (m, 1H), 3.68 (m, 1H), 3.31 (s, 3H), 3.27-3.19 (m, 1H). | 411.1<br>3.87 min |

TABLE 5-continued

| Example Ki (uM) Method(s) | Structure | Stereo | $^1$H-NMR | MS (m/z) |
|---|---|---|---|---|
| Example 732 0.061 | 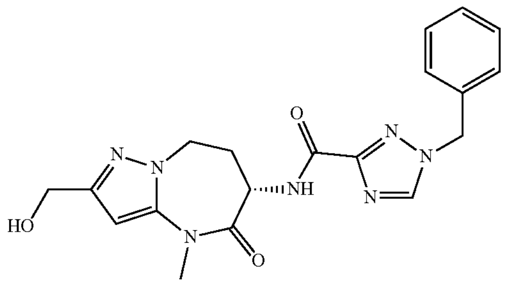 [SMILES: CN1C(=O)[C@@H](NC(=O)c2ncn(Cc3ccccc3)n2)CCn2nc(CO)cc21] 1-benzyl-N-[(6S)-2-(hydroxymethyl)-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-$d_6$) δ 8.82 (s, 1H), 8.51 (d, J = 7.8 Hz, 1H), 7.42-7.26 (m, 5H), 6.28 (s, 1H), 5.48 (s, 2H), 5.10 (t, J = 5.8 Hz, 1H), 4.45-4.24 (m, 4H), 4.15 (m, 1H), 3.24 (s, 3H), 2.58 (m, 1H), 2.41-2.28 (m, 1H) | 396.1 3.14 min |
| Example 733 0.068 | 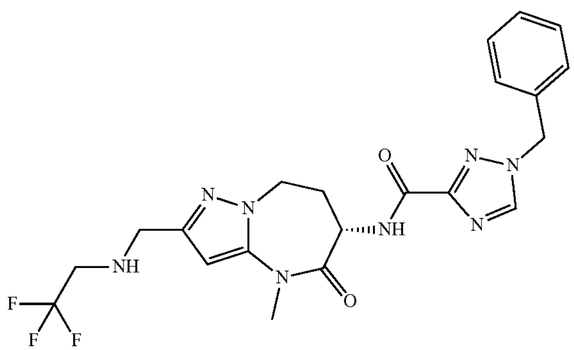 [SMILES: CN1C(=O)[C@@H](NC(=O)c2ncn(Cc3ccccc3)n2)CCn2nc(CNCC(F)(F)F)cc21] 1-benzyl-N-[(6S)-4-methyl-5-oxo-2-[(2,2,2-trifluoroethylamino)methyl]-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-$d_6$) δ 8.82 (s, 1H), 8.52 (d, J = 7.8 Hz, 1H), 7.42-7.26 (m, 5H), 6.28 (s, 1H), 5.48 (s, 2H), 4.31 (m, 2H), 4.15 (m, 1H), 3.79-3.64 (m, 2H), 3.33-3.15 (m, 4H), 2.77 (p, J = 6.9 Hz, 1H), 2.59 (m, 1H), 2.50-2.29 (m, 1H) | 477.2 3.18 min |

TABLE 5-continued

| Example<br>Ki (uM)<br>Method(s) | Structure | Stereo | $^1$H-NMR | MS (m/z) |
|---|---|---|---|---|
| Example 734<br>0.149 | 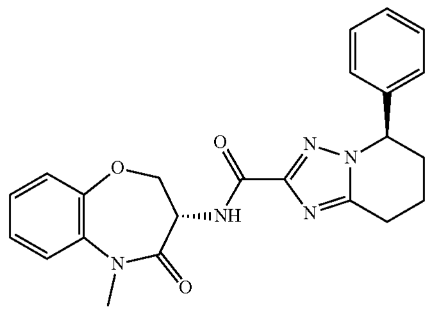 [SMILES: CN1C(=O)[C@@H](NC(=O)c2nc3n(n2)[C@@H](c2ccccc2)CCC3)COc2ccccc21]<br>(5R)-N-[3S)-5-methyl-4-oxo-2,3-dihydro-1,5-benzoxazepin-3-yl]-5-phenyl-5,6,7,8-tetrahydro-[1,2,4]triazolo[1,5-a]pyridine-2-carboxamide | Single<br>Unknown<br>Stereoisomer | $^1$H NMR (400 MHz, DMSO-$d_6$) δ 8.40 (d, J = 7.9 Hz, 1H), 7.49 (dd, J = 7.6, 2.0 Hz, 1H), 7.40-7.18 (m, 6H), 7.09-7.01 (m, 2H), 5.57 (t, J = 5.9 Hz, 1H), 4.80 (dt, J = 11.5, 7.8 Hz, 1H), 4.547 (dd, J = 11.6, 9.9 Hz, 1H), 4.38 (dd, J = 9.9, 7.6 Hz, 1H), 3.30 (s, 3H), 3.11-2.89 (m, 2H), 2.49-2.32 (m, 1H), 2.11-1.98 (m, 1H), 1.87 (h, J = 5.9 5.4 Hz, 2H). | 418.2<br>11.60 |
| Example 735<br>0.013 | 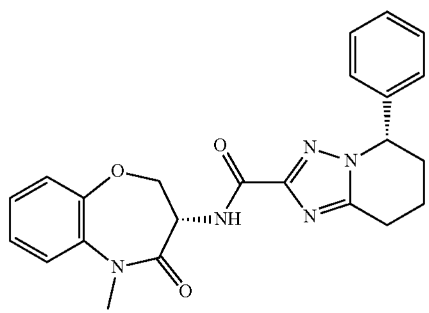<br>(5S)-N-[3S)-5-methyl-4-oxo-2,3-dihydro-1,5-benzoxazepin-3-yl]-5-phenyl-5,6,7,8-tetrahydro-[1,2,4]triazolo[1,5-a]pyridine-2-carboxamide | Single<br>Unknown<br>Stereoisomer | $^1$H NMR (400 MHz, DMSO-$d_6$) δ 8.38 (d, J = 8.0 Hz, 1H), 7.49 (dd, J = 7.5, 2.0 Hz, 1H), 7.40-7.19 (m, 6H), 7.09-7.01 (m, 2H), 5.57 (t, J = 5.9 Hz, 1H), 4.80 (dt, J = 11.5, 7.8 Hz, 1H), 4.56 (dd, J = 11.5, 9.9,7.7 Hz, 1H), 3.44-3.20 (s, 3H), 3.10-2.90 (m, 2H), 2.38 (dt, J = 11.5, 6.4 Hz, 1H), 2.10-1.98 (m, 1H), 1.86 (p, J = 6.3 Hz, 2H) | 418.1<br>11.72 |

TABLE 5-continued

| Example Ki (uM) Method(s) | Structure | Stereo | $^1$H-NMR | MS (m/z) |
|---|---|---|---|---|
| Example 736 0.070 Method GZ20 | 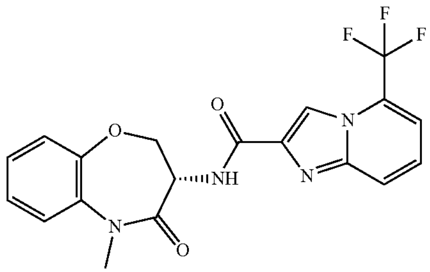 [SMILES: CN1C(=O)[C@@H](NC(=O)c2cn3c(C(F)(F)F)cccc3n2)COc2ccccc21] N-[3S)-5-methyl-4-oxo-2,3-dihydro-1,5-benzoxazepin-3-yl]-5-(trifluoromethyl)imidazo [1,2-a]pyridine-2-carboxamide | Single Known Stereoisomer | $^1$H NMR (400 MHz, DMSO-$d_6$) δ 8.58 (d, J = 8.0 Hz, 1H), 8.30 (q, J = 1.8 Hz, 1H), 8.05 (d, J = 9.2 Hz 1H), 7.70 (d, J = 7.1 Hz, 1H), 7.60-7.48 (m, 2H), 7.30 (m, 3H), 4.91 (dt, J = 11.4, 7.9 Hz, 1H), 4.60 (dd, J = 11.5, 9.9 Hz, 1H), 4.47 (dd, J = 9.9, 7.7 Hz, 1H), 3.34 (s, 3H) | 405.0 6.00 |
| Example 737 TBD Method GZ20 | 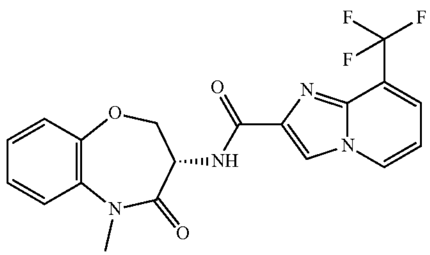 [SMILES: CN1C(=O)[C@@H](NC(=O)c2cn3cccc(C(F)(F)F)c3n2)COc2ccccc21] (S)-N-(5-methyl-4-oxo-2,3,4,4-tetrahydrobenzo [b][1,4]oxazepin-3-yl)-8-trifluoromethyl)imidazo[1,2-a] pyridine-2-carboxamide | Single Known Stereoisomer | $^1$H NMR (400 MHz, DMSO-$d_6$) δ 8.82 (d, J = 6.8 Hz, 1H), 8.57 (s, 1H), 8.30 (d, J = 7.8 Hz, 1H), 7.86 (dt, J = 7.3, 1.2 Hz, 1H), 7.55-7.46 (m, 1H), 7.39-7.23 (m, 3H), 7.14 (t, J = 7.0 Hz, 1H), 4.91 (dt, J = 11.3, 7.7 Hz, 1H), 4.64-4.45 (m, 2H), 3.35 (s, 3H) | 405.0 4.81 |
| Example 738 4.018 (Purification of Ex 662) | 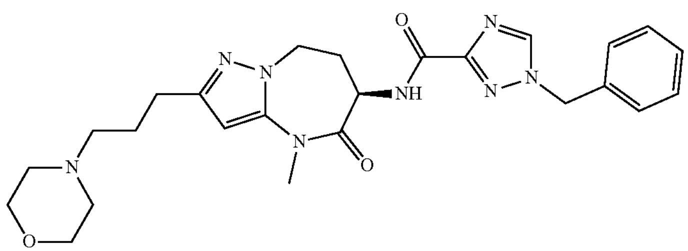 [SMILES: CN1C(=O)[C@H](NC(=O)c2ncn(Cc3ccccc3)n2)CCn2nc(CCCN3CCOCC3)cc21] 1-benzyl-N-[(6R)-4-methyl-2-(3-morpholinopropyl)-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, CD3OD) δ 8.56 (s, 1H), 7.38-7.32 (m, 5H), 6.17 (s, 1H), 5.47 (s, 2H), 4.54-4.49 (m, 1H), 4.33-4.30 (m, 1H), 4.27-4.21 (m, 1H), 3.69 (t, J = 4.8 Hz, 4H), 3.33 (s,3H), 2.83-2.80 (m, 1H), 2.66-2.62 (m, 2H), 2.18-2.40 (m, 6H), 2.26-2.24 (m, 1H), 1.89-1.86 (m, 2H). | 493.3 |

TABLE 5-continued

| Example<br>Ki (uM)<br>Method(s) | Structure | Stereo | $^{1}$H-NMR | MS (m/z) |
|---|---|---|---|---|
| Example 739<br>0.036<br>WX Method<br>211 | 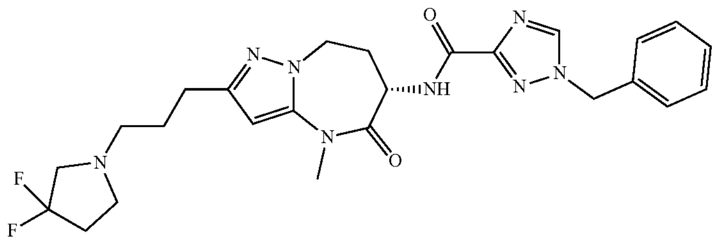 [SMILES: CN1C(=O)[C@@H](NC(=O)c2ncn(Cc3ccccc3)n2)CCn2nc(CCCN3CCC(F)(F)C3)cc21]<br>1-benzyl-N-[(6S)-2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide | Single<br>Unknown<br>Stereoisomer | $^{1}$H NMR (400 MHz, CD3OD) δ 8.58 (s, 1H), 7.39-7.33 (m, 5H), 6.17 (s, 1H), 5.48 (s, 2H), 4.54-4.49 (m, 1H), 4.32-4.30 (m, 1H), 4.26-4.21 (m, 1H), 3.33 (s, 3H), 3.07-3.03 (m, 2H), 2.91-2.83 (m, 3H), 2.68-2.65 (m, 4H), 2.36-2.27 (m, 3H), 1.91-1.87 (m, 2H). | 513.2 |
| Example 740<br>0.137<br>WX Method<br>182 | 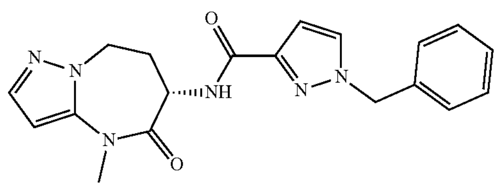 [SMILES: CN1C(=O)[C@@H](NC(=O)c2ccn(Cc3ccccc3)n2)CCn2nccc21]<br>1-benzyl-N-[(6S)-4-methyl-5-oxo-7,8-dihydro-6H-pyrazolo[1,5-a][1,3]diazepin-6-yl]pyrazole-3-carboxamide | Single<br>Known<br>Stereoisomer | $^{1}$H NMR (400 MHz, CD3OD) δ 7.71 (d, J = 2.4 Hz, 1H), 7.66 (d, J = 2.0 Hz, 1H), 7.35-7.26 (m, 5H), 6.74 (d, J = 2.8 Hz, 1H), 6.39 (d, J = 2.0 Hz, 1H), 5.40 (s, 2H), 4.57-4.52 (m, 1H), 4.46-4.44 (m, 1H), 4.34-4.31 (m, 1H), 3.36 (s, 3H), 2.89-2.82 (m, 1H), 2.34-2.28 (m, 1H). | 365.0 |
| Example 741<br>0.14<br>WX Method<br>182 | 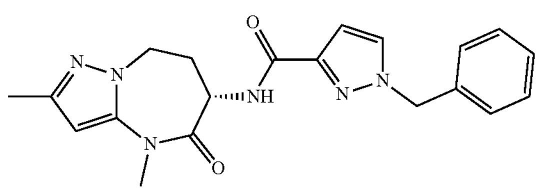 [SMILES: Cc1cc2n(n1)CC[C@H](NC(=O)c1ccn(Cc3ccccc3)n1)C(=O)N2C]<br>1-benzyl-N-[(6S)-2,4-dimethyl-5-oxo-7,8-dihydro-6H-pyrazolo[1,5-a][1,3]diazepin-6-yl]pyrazole-3-carboxamide | Single<br>Known<br>Stereoisomer | $^{1}$H NMR (400 MHz, CD3OD) δ 7.71 (s, 1H), 7.36-7.25 (m, 5H), 6.75 (s, 1H), 6.39-6.34 (m, 1H), 5.40 (s, 2H), 4.66-4.65 (m, 1H), 4.44-4.34 (m, 2H), 3.36 (s, 3H), 2.92-2.81 (m, 1H), 2.39-2.37 (m, 4H) | 379.0 |
| Example 742<br>0.01<br>WX Method<br>186 | 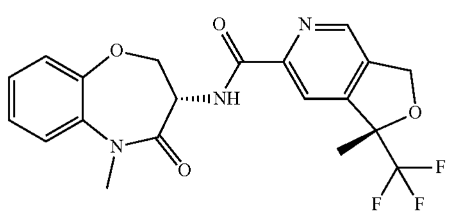 [SMILES: CN1C(=O)[C@@H](NC(=O)c2cc3c(cn2)CO[C@]3(C)C(F)(F)F)COc2ccccc21]<br>(1S)-1-methyl-N-[(3S)-5-methyl-4-oxo2,3-dihydro-1,5-benzoxazepin-3H-furo[3,4-c]pyridine-6-carboxamide | Single<br>Unknown<br>Stereoisomer | 1H NMR (400 MHz,CDCl3) δ 8.89 (d, J = 8.0 Hz, 1H), 8.59 (s, 1H), 8.08 (s, 1H), 7.27-7.26 (m, 3H), 5.31 (s, 2H), 5.14-5.05 (m, 1H), 4.79 (t, J = 8.0 Hz, 1H), 4.36-4.27 (m, 1H), 3.46 (s, 3H), 1.71 (s, 3H) | 422.2 |

TABLE 5-continued

| Example Ki (uM) Method(s) | Structure | Stereo | $^1$H-NMR | MS (m/z) |
| --- | --- | --- | --- | --- |
| Example 743 0.017 WX Method 188 | 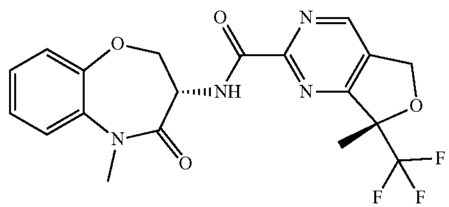 [SMILES: CN1C(=O)[C@@H](NC(=O)c2ncc3c(n2)[C@@](C)(C(F)(F)F)OC3)COc2ccccc21] (7S)-7-methyl-N-[(3S)-5-methyl-4-oxo-2,3-dihydro-1,5-benzoxazepin-3-yl]-7-(trifluoromethyl)-5H-furo[3,4-d]pyrimidine-2-carboxamide | Single Unknown Stereoisomer | $^1$H NMR (400 MHz, CD3OD) δ 9.00 (s 1H), 7.46-7.43 (m, 1H), 7.34-7.24 (m, 3H), 5.32 9s, 2H), 5.04-4.96 (m, 1H), 4.72-4.67 (m, 1H), 4.48-4.42 (m, 1H), 3.44 (s, 3H), 1.76 (s, 3H). | 423.0 |
| Example 744 0.01 WX Method | 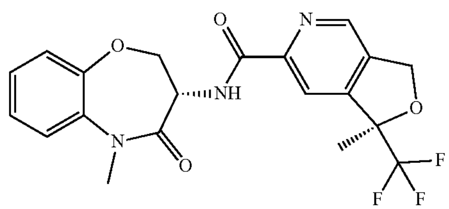 [SMILES: CN1C(=O)[C@@H](NC(=O)c2cc3c(cn2)CO[C@@]3(C)C(F)(F)F)COc2ccccc21] (1R)-1-methyl-N-[(3S-5-methyl-4-oxo-2,3-dihydro-1,5-benzoxazepin-3-yl]-1-(trifluoromethyl)-3H-furo[3,4-c]pyridine-6-carboxamide | Single Unknown Stereoisomer | $^1$H NMR (400 MHz, CDCl3) δ 8.89 (d, J = 7.2 Hz, 1H), 8.59 (s, 1H), 8.08 (s, 1H), 7.26 (s, 3H), 5.31 (s, 2H), 5.148-5.08 (m, 1H), 4.79 (t, J = 8.0 Hz, 1H), 4.33-4.27 (m, 1H), 3.46 (s, 3H), 1.71 (s, 3H) | 422.2 |
| Example 745 0.012 WX Method 188 | 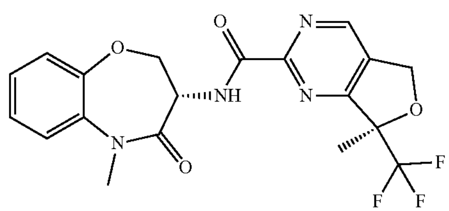 [SMILES: CN1C(=O)[C@@H](NC(=O)c2ncc3c(n2)[C@](C)(C(F)(F)F)OC3)COc2ccccc21] (7R)-7-methyl-N-[(3S)-5-methyl-4-oxo-2,3-dihydro-1,2-benzoxazepin-3-yl]-7-trifluoromethyl)-5H-furo[3,4-d]pyrimidine-2-carboxamide | Single Unknown Stereoisomer | $^1$H NMR (400 MHz, CD3OD) δ 9.00 (s, 1H), 7.46-7.43 (m, 1H), 7.34-7.24 (m, 3H), 5.32 (s, 2H), 5.04-4.96 (m, 1H), 4.72-4.67 (m, 1H), 4.48-4.42 (m, 1H), 3.44 (s, 3H), 1.76 (s, 3H). | 423.0 |

TABLE 5-continued

| Example Ki (uM) Method(s) | Structure | Stereo | $^1$H-NMR | MS (m/z) |
|---|---|---|---|---|
| Example 746 0.023 WX Method 184 | 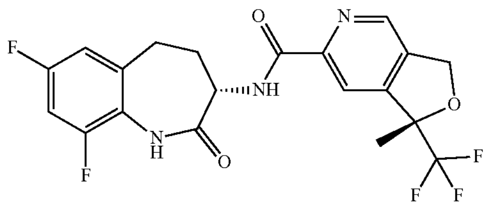 [SMILES: C[C@]1(C(F)(F)F)OCc2cnc(C(=O)N[C@H]3CCc4cc(F)cc(F)c4NC3=O)cc21] (1S)-1-methyl-N-[(S)-7,9-difluoro-2-oxo-1,3,4,5-tetrahydro-1-benzazepin-3-yl]-1-(trifluoromethyl)-3H-furo[3,4-c]pyridine-6-carboxamide | Single Unknown Stereoisomer | $^1$H NMR (400 MHz, CDCl3) δ 8.84 (d, J = 6.8 Hz, 1H), 8.59 (s, 1H), 8.11 (s, 1H), 7.17 (s, 1H), 6.91-6.82 (m, 2H), 5.31 (s, 2H), 4.79-4.70 (m, 1H), 3.12-3.01 (m, 1H), 2.96-2.85 (m, 1H0, 2.80-2.72 (m, 1H), 2.21-2.10 (m, 1H), 1.72 (s, 3H) | 442.2 |
| Example 747 0.042 EX Method 188 | 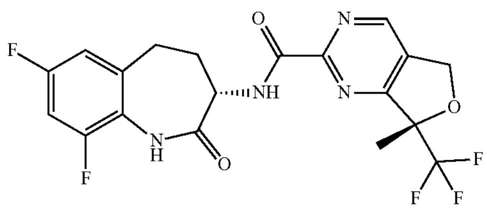 [SMILES: C[C@]1(C(F)(F)F)OCc2cnc(C(=O)N[C@H]3CCc4cc(F)cc(F)c4NC3=O)nc21] (7S)-7-methyl-N-[(3S)-7,9-difluorp-2-oxo-1,3,4,5-tetrahydro-1-benzazepin-3-yl]-7-(trifluoromethyl)-5H-furo[3,4-d]pyrimidine-2-carboxamide | Single Unknown Stereoisomer | $^1$H NMR (400 MHz, CD3OD) δ 8.99 (s, 1H), 7.04-6.99 (m, 2H), 5.32 (s, 2H), 4.66-4.61 (m, 1H), 3.04-2.98 (m, 1H), 2.87-2.75 (m, 2H), 2.28-2.23 (m, 1H), 1.76 (s, 3H). | 443.0 |
| Example 748 0.014 WX MEthod 184 | 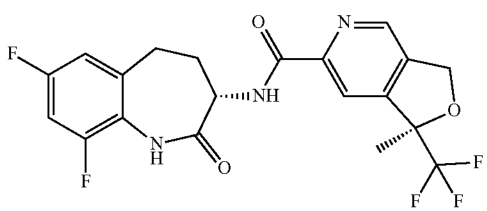 [SMILES: C[C@@]1(C(F)(F)F)OCc2cnc(C(=O)N[C@H]3CCc4cc(F)cc(F)c4NC3=O)cc21] (1R)-1-methyl-N-[(3S)-7,9-difluoro-2-oxo-1,3,4,5-tetrahydro-1-benzazepin-3-yl]-1-(trifluoromethyl)-3H-furo[3,4-c]pyridine-6-carboxamide | Single Unknown Stereoisomer | $^1$H NMR (400 MHz, CDCl3) δ 8.84 (d, J = 7.2 Hz, 1H), 8.59 (s, 1H), 8.11 (s, 1H), 7.17 (s, 1H), 6.91-6.82 (m, 2H), 5.31 (s, 2H), 4.79-4.70 (m, 1H), 3.12-3.01 (m, 1H0, 2.96-2.85 (m, 1H), 2.80-2.72 (m, 1H), 2.21-2.10 (m, 1H), 1.72 (s, 3H) | 442.2 |

TABLE 5-continued

| Example Ki (uM) Method(s) | Structure | Stereo | $^1$H-NMR | MS (m/z) |
|---|---|---|---|---|
| Example 749 0.012 WX Method 188 | 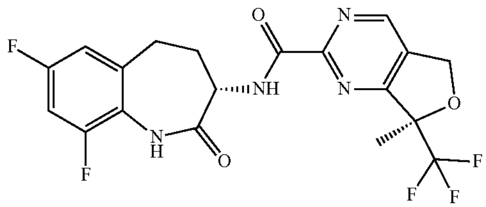 [SMILES: C[C@@]1(C(F)(F)F)OCc2cnc(C(=O)N[C@H]3CCc4cc(F)cc(F)c4NC3=O)nc21] (7R)-7-methyl-N-[(3S)-7,9-difluoro-2-oxo-1,3,4,5-tetrahydro-2-oxo-1,3,4,5-tetrahydro-1-benzazepin-3-yl]-7-trifluoromethyl)-5H-furo[3,4-d]pyrimidine-2-carboxamide | Single Unknown Stereoisomer | $^1$H NMR (400 MHz, CD3OD) δ 8.99 (s, 1H), 7.04-6.99 (m, 2H), 5.32 (s, 2H), 4.66-4.61 (m, 1H), 3.04-2.98 (m, 1H), 2.87-2.75 (m, 2H), 2.28-2.23 (m, 1H), 1.76 (s, 3H). | 443.0 |
| Example 750 0.066 WX Method 184 | 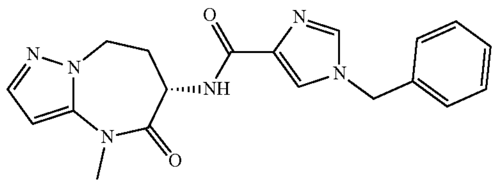 [SMILES: CN1C(=O)[C@@H](NC(=O)c2cn(Cc3ccccc3)cn2)CCn2nccc21] 1-benzyl-N-[(6S)-4-methyl-5-oxo-7,8-dihydro-6H-pyrazolo[1,5-a[1,3]diazepin-6-yl]imidazole-4-carboxamide | Single Unknown Stereoisomer | $^1$H NMR (400 MHz, CD3OD) δ 9.16 (s, 1H), 8.10 (s, (s, 1H), 7.53 (d,J = 2.0 Hz, 1H), 7.42-7.41 (m, 5H), 6.29 (d, J = 2.0 Hz, 1H), 5.44 (s, 2H), 4.44-4.37 (m, 2H), 4.25-4.22 (m, 1H), 3.25 (s, 3H), 2.70-2.65 (m, 1H), 2.27-2.22 (m, 1H). | 365.1 |
| Example 751 0.044 WX Method 184 | 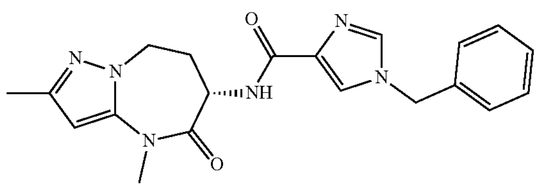 [SMILES: Cc1cc2n(n1)CC[C@H](NC(=O)c1cn(Cc3ccccc3)cn1)C(=O)N2C] 1-benzyl-N-[(6S)-2,4-dimethyl-5-oxo-7,8-dihydro-6H-pyrazolo[1,5-a][1,3]diazepin-6-yl] imidazole-4-carboxamide | Single Known Stereoisomer | $^1$H NMR (400 MHz, CD3OD) δ 9.21 (s, 1H), 8.16 (s, 1H), 7.47-7.42 (m, 5H), 6.28 (s, 1H), 5.48 (s, 2H), 4.58-4.53 (m, 1H), 4.39-4.27 (m, 2H), 3.30 (s, 3H), 2.77-2.71 (m, 1H), 2.32-2.28 (m, 4H) | 379.1 |

TABLE 5-continued

| Example Ki (uM) Method(s) | Structure | Stereo | $^1$H-NMR | MS (m/z) |
|---|---|---|---|---|
| Example 752 0.116 WX Method 199 | 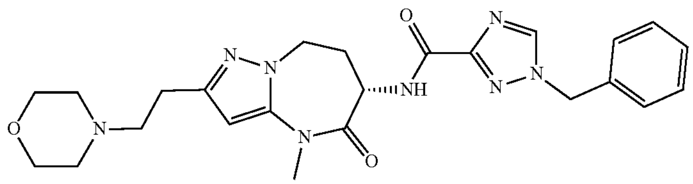 [SMILES: CN1C(=O)[C@@H](NC(=O)c2ncn(Cc3ccccc3)n2)CCn2nc(CCN3CCOCC3)cc21] 1-benzyl-N-[6S)-4-methyl-2-(2-morpholinoethyl)-5-oxo-7,8-dihydro-6H-pyrazolo[1,5-a][1,3]diapepin-6-yl]-1,2,4-triazole-3-carboxamide | Single Unknown Stereoisomer | $^1$H NMR (400 MHz, CD3OD) δ 8.56 (s, 1H), 7.37-7.34 (m, 5H), 6.20 (s, 1H), 5.48 (s, 2H), 4.53-4.50 (m, 1H), 4.33-4.31 (m, 1H), 4.23-4.24 (m, 1H), 3.73-3.71 (m, 4H), 3.33 (s, 3H), 2.72-2.67 (m, 2H), 2.58-2.52 (m, 4H), 2.26-2.24 (m, 1H). | 479.2 |
| Example 753 0.074 WX Method 199 | 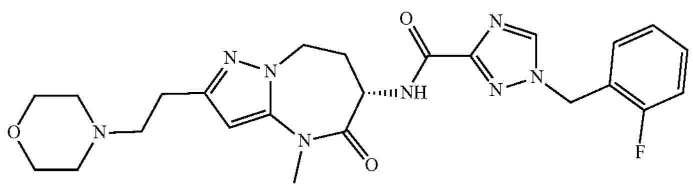 [SMILES: CN1C(=O)[C@@H](NC(=O)c2ncn(Cc3ccccc3F)n2)CCn2nc(CCN3CCOCC3)cc21] 1-[(2-fluorophenyl)methyl]-N-[(6S)-4-methyl-2-(2-morpholonoethyl)-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, CD3OD) δ 8.58 (s, 1H), 7.41-7.38 (m, 2H), 6.19 (s, 1H), 5.55 (s, 2H), 4.55-4.50 (m, 1H), 4.33-4.31 (m, 1H), 4.23-4.21 (m, 1H), 3.73-3.71 (m, 4H), 3.33 (s, 3H), 2.86-2.81 (m, 3H), 2.72-2.67 (m, 2H), 2.58-2.52 (m, 4H), 2.26-2.23 (m, 1H). | 497.2 |
| Example 754 0.411 WX Method 213 | 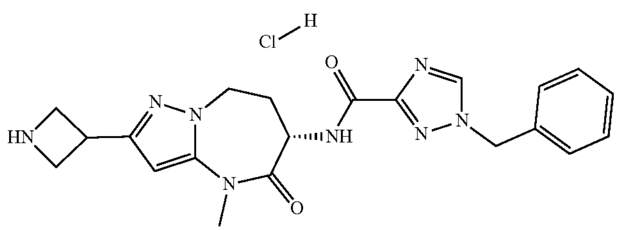 1-benzyl-N-[(6S)-2-(azetidin-3-yl)-4-methyl-5-oxo-7,8-dihydro-6H-pyrazolo[1,5-a][1,3] diazepin-6-yl]-1,2,4-triazole-3-carboxamide; hydrochloride | Single Unknown Stereoisomer | $^1$H NMR (400 MHz, CD3OD) δ 8.90 (s, 1H), 7.41-7.30 (m, 5H), 6.36 (s, 1H), 5.52 (s, 2H), 4.53-4.50 (m, 1H), 4.47-4.14 (m, 7H), 3.34 (s, 3H), 2.88-2.78 (m, 1H), 2.35-2.27 (m, 1H) | 421.2 |

TABLE 5-continued

| Example Ki (uM) Method(s) | Structure | Stereo | $^1$H-NMR | MS (m/z) |
|---|---|---|---|---|
| Example 755 0.124 WX Method 192 | 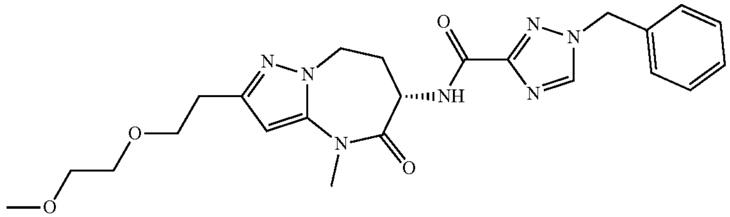 [SMILES: COCCOCCc1cc2n(n1)CC[C@H](NC(=O)c1ncn(Cc3ccccc3)n1)C(=O)N2C] 1-benzyl-N-[(6S)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, CD3OD) δ 8.46 (s, 1H), 7.30-7.22 (m, 5H), 6.11 (s, 1H), 5.37 (s, 2H), 4.44-4.40 (m, 1H), 4.27-4.20 (m, 1H), 4.16-4.07 (m, 1H), 3.65 (t, J = 6.8 Hz, 2H), 3.54-3.51 (m, 2H) 3.46-3.42 (m, 2H), 3.25 (s, 3H) 3.23 (s, 3H), 2.78-2.71 (m, 3H), 2.16-2.13 (m, 1H). | 468.2 |
| Example 756 0.623 WX Method 198 | 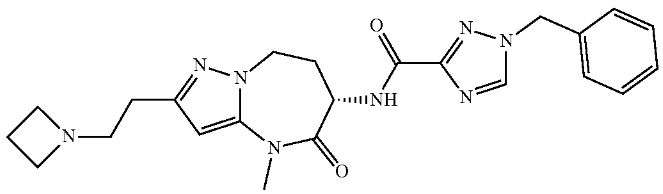 [SMILES: CN1C(=O)[C@@H](NC(=O)c2ncn(Cc3ccccc3)n2)CCn2nc(CCN3CCC3)cc21] 1-benzyl-N-[(6S)-2-[2-(aazetidin-1-yl)ethyl]-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, CD3OD) δ 8.57 (s, 1H), 7.39-7.31 (m, 5H), 6.17 (s, 1H), 5.47 (s, 2H), 4.57-4.52 (m, 1H), 4.33-4.31 (m, 1H), 4.24-4.21 (m, 1H), 3.36-3.34 (m, 2H), 3.33 (s, 3H), 3.32-3.30 (m, 2H), 2.87-2.78 (m, 3H), 2.67-2.63 (m, 2H), 2.25-2.22 (m, 1H), 2.15-2.10 (m, 2H). | 449.0 |
| Example 757 0.168 WX Method 194 | 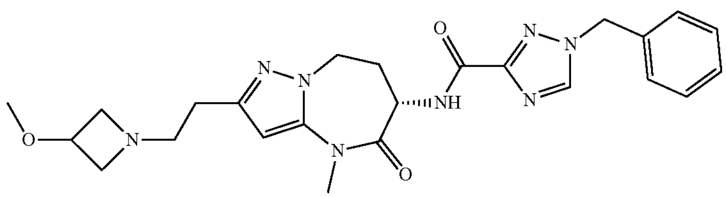 [SMILES: COC1CN(CCc2cc3n(n2)CC[C@H](NC(=O)c2ncn(Cc4ccccc4)n2)C(=O)N3C)C1] 1-benzyl-N-[(6S)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxzmide | Single Unknown Stereoisomer | $^1$H NMR (400 MHz, CD3OD) δ 8.56 (s, 1H), 7.35 (s, 5H), 6.17 (s, 1H), 5.47 (s, 2H), 4.57-4.52 (m, 1H), 4.37-4.31 (m, 1H), 4.26-4.17 (m, 1H), 4.06-4.00 (m, 1H), 3.63 (t, J = 6.8 Hz, 2H), 2.84-2.80 (m, 3H), 2.67 (t, J = 7.2 Hz, 2H), 2.29-2.21 (m, 1H) | 479.1 |

TABLE 5-continued

| Example Ki (uM) Method(s) | Structure | Stereo | $^1$H-NMR | MS (m/z) |
|---|---|---|---|---|
| Example 758<br>0.086<br>WX Method<br>190 | 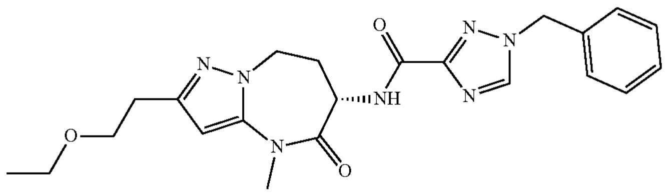 [SMILES: CCOCCc1cc2n(n1)CC[C@H](NC(=O)c1ncn(Cc3ccccc3)n1)C(=O)N2C]<br>1-benzyl-N-[6S)-2-(2-ethoxyethyl)-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, CD3OD) δ 8.46 (s, 1H), 7.27-7.24 (m, 5H), 6.09 (s, 1H), 5.38 (s, 2H), 4.44-4.41 (m, 1H), 4.36-4.30 (m, 1H), 4.24-4.19 (m, 1H), 3.61 (t, J = 6.8 Hz, 2H), 3.45-3.43 (m, 2H), 3.23 (s, 3H), 2.78-2.74 (m 3H), 2.17-2.13 (m, 1H), 1.09 (t, J = 7.2 Hz, 3H) | 438.2 |
| Example 759<br>0.024<br>WX Method<br>212 | 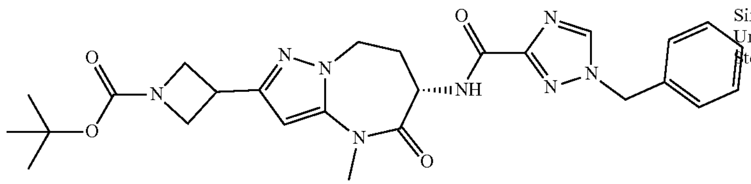<br>tert-butyl-3-[(6S)-6-[(1-nenzyl-1,2,4-triazole-3-carbonyl)amino]-4-methyl-5-oxo-7,8-dihydro-6H-pyrazolo[1,5-a][1,3]diazepin-2-yl]azetidine-1-caboxylate | Single Unknown Stereoisomer | $^1$H NMR (400 MHz, CD3OD) δ 8.56 (s, 1H), 7.41-7.31 (m, 5H), 6.30 (s, 1H), 5.47 (s, 2H), 4.58-4.49 (m, 1H), 4.44-4.19 (m, 4H), 4.09-3.98 (m, 2H), 3.85-3.76 (m, 1H), 3.39 (s, 3H), 2.92-2.79 (m, 1H), 2.32-2.22 (s, 1H), 1.46 (s, 9H) | 421.2<br>(M − 100 + 1) |
| Example 760<br>G03086942<br>0.077<br>WX Method<br>192 | 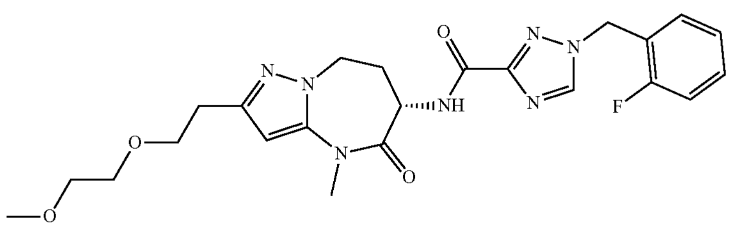 [SMILES: COCCOCCc1cc2n(n1)CC[C@H](NC(=O)c1ncn(Cc3ccccc3F)n1)C(=O)N2C]<br>1-[(2-fluorophenyl)methyl]-N-[(6S)-2-[2(2-methoxyethoxy)ethyl]-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, CD3OD) δ 8.47 (s, 1H), 7.30-7.26 (m, 2H), 7.11-7.02 (m, 2H), 6.11 (s, 1H), 5.45 (s, 2H), 4.43-4.40 (m, 1H), 4.25-4.22 (m, 1H), 4.15-4.10 (m, 1H), 3.64 (t, J = 6.8 Hz, 2H), 3.52-3.51 (m, 2H), 3.49-3.45 (m, 2H), 3.25 (s, 3H), 3.22 (s, 3H), 2.78-2.75 (m, 3H), 2.19-2.14 (m, 1H). | 508.2<br>(M + Na)+ |

TABLE 5-continued

| Example Ki (uM) Method(s) | Structure | Stereo | $^1$H-NMR | MS (m/z) |
|---|---|---|---|---|
| Example 761 0.159 WX Method 203 | 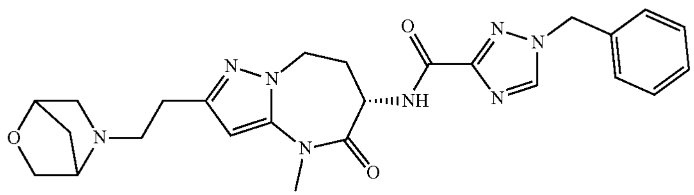 [SMILES: CN1C(=O)[C@@H](NC(=O)c2ncn(Cc3ccccc3)n2)CCn2nc(CCN3CC4CC3CO4)cc21] 1-benzyl-N-[(6S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide | Mixture of Diastereomers | $^1$H NMR (400 MHz, CD3OD) δ 8.57 (s, 1H), 7.39-7.33 (m, 5H), 6.20 (s, 1H), 5.47 (s, 2H), 4.55-4.52 (m, 1H), 4.33-4.31 (m, 1H), 4.30-4.25 (m, 1H), 4.24-4.15 (m, 1H), 4.06-4.03 (m, 1H), 3.64-3.61 (m, 2H), 3.33 (s, 3H), 2.93-2.77 (m, 6H), 2.62-2.59 (m, 21H), 2.26-2.20 (m, 1H), 1.92-1.89 (m, 1H), 1.78-1.75 (m, 1H). | 491.2 |
| Example 762 0.182 WX Method 203 | 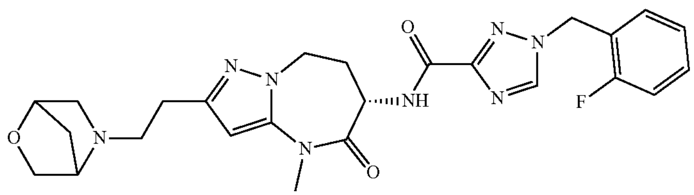 [SMILES: CN1C(=O)[C@@H](NC(=O)c2ncn(Cc3ccccc3F)n2)CCn2nc(CCN3CC4CC3CO4)cc21] 1-[(2-fluorophenyl)methyl]-N-[(6S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxzmide | Mixture of Diastereomers | $^1$H NMR (400 MHz, CD3OD) δ 8.58 (s, 1H), 7.41-7.36 (m, 2H), 7.21-7.14 (m, 2H), 6.20 (s, 1H), 5.47 (s, 2H), 4.22-4.52 (m, 1H), 4.33-4.31 (m, 1H), 4.30-4.25 (m, 1H), 4.24-4.15 (m, 1H), 4.06-4.03 (m, 1H), 3.64-3.61 (m, 2H), 3.33 (s, 3H), 2.93-2.77 (m, 6H), 2.62-2.59 (m, 1H), 2.26-2.20 (m, 1H), 1.92-1.89 (m, 1H), 1.78-1.75 (m, 1H). | 509.2 |
| Example 763 0.073 WX Method 190 | 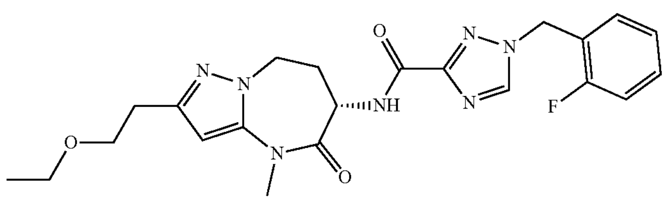 [SMILES: CCOCCc1cc2n(n1)CC[C@H](NC(=O)c1ncn(Cc3ccccc3F)n1)C(=O)N2C] 1-[(2-fluorophenyl)methyl]-N-[6S)-2-(2-ethoxyethyl)-4-methyl-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, CD3OD) δ 8.47 (s, 1H), 7.34-7.22 (m, 2H), 7.12-7.00 (m, 2H), 6.08 (s, 1H), 5.45 (s, 2H), 4.45-4.40 (m, 1H), 4.27-4.19 (m, 1H), 4.16-4.07 (m, 1H), 3.60 (t, J = 6.8 Hz, 2H), 3.43 (q, J = 6.8 Hz, 2H), 3.23 (s, 3H), (s, 3H), 2.78-2.70 (m, 3H), 2.19-2.11 (m, 1H), 1.08 (t, J = 7.2 Hz, 3H). | 456.1 |

TABLE 5-continued

| Example Ki (uM) Method(s) | Structure | Stereo | $^{1}$H-NMR | MS (m/z) |
|---|---|---|---|---|
| Example 764 0.267 WX Method 209 | 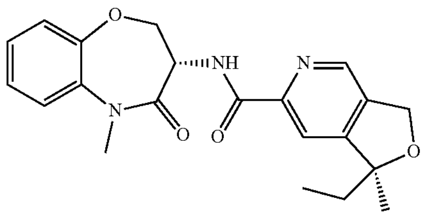 [SMILES: CC[C@]1(C)OCc2cnc(C(=O)N[C@H]3COc4ccccc4N(C)C3=O)cc21] (1S)-1-ethyl-1-methyl-N-1[(3S)-5-methyl-4-oxo-2,3-dihydro-1,2-benzoxazepin-3-yl]-3H-furo-1,2-benzoxazepin-3-yl]-3H-furo[3,4-c] pyridibe-6-carboxamide | Single Unknown Stereoisomer | 1H NMR (400 MHz, DMSO-d6) δ 8.88 (d, J = 7.6 Hz, 1H), 8.64 (s, 1H), 7.88 (s, 1H), 7.51 (d, J = 7.2 Hz, 1H), 7.36-7.24 (m, 3H), 5.15 (s, 2H), 4.91-4.85 (m, 1H), 4.59-4.46 (m, 2H), 3.35-3.34 (m, 3H), 1.87-1.73 (m, 2H), 1.40 (s, 3H), 0.68 (t, J = 7.2 Hz, 3H) | 382.1 |
| Example 765 0.015 WX Method 208 | 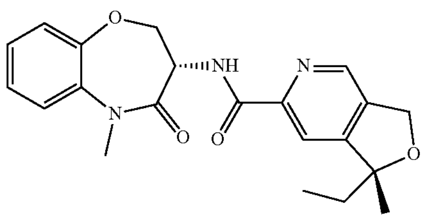 (1R)-1-ethyl-1-methyl-N-[(3S)-5-methyl-4-oxo-2,3-dihydro-1,5-benzoxazepin-3-yl]-3H-furo[3,4-c] pyridine-6-carboxamide | Single Unknown Stereoisomer | 1H NMR (400 MHz, CD3OD) δ 8.57 (s, 1H), 7.85 (s, 1H), 7.45-7.42 (m, 1H), 7.33-7.31 (m, 2H), 5.15-5.12 (m, 1H), 4.66-4.62 (m, 1H), 4.42-4.37 (m, 1H), 3.42 (s, 3H), 1.87-1.82 (m, 2H), 1.45 (s, 3H), 0.76 (t, J = 7.6 Hz, 3H). | 382.1 |
| Example 766 0.084 WX Method 207 | 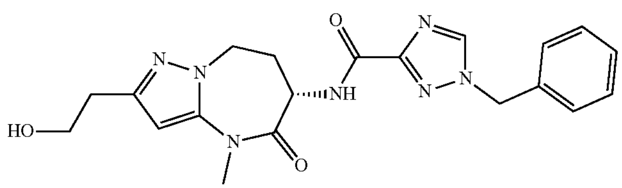 [SMILES: CN1C(=O)[C@@H](NC(=O)c2ncn(Cc3ccccc3)n2)CCn2nc(CCO)cc21] 1-benzyl-N-[(6S)-2-(2-hydroxyethyl)-4-methyl-5-oxo-7,8-dihydro-6H-pyrazolo[1,5-a][1,3]diazepin-6-yl]-1,2,4-triazole-3-carboxamide | Single Unknown Stereoisomer | 1H NMR (400 MHz, CD3OD) δ 8.57 (s, 1H), 7.41-7.29 (m, 5H), 6.19 (s, 1H), 5.48 (s, 2H), 4.58-4.53 (m, 1H), 4.39-4.31 (m, 1H), 4.28-4.17 (m, 1H), 3.82 (t, J = 6.8 Hz, 2H), 3.35-3.33 (m, 3H), 2.92-2.77 (m, 3H), 2.29-2.21 (m, 1H) | 410.2 |

TABLE 5-continued

| Example Ki (uM) Method(s) | Structure | Stereo | $^1$H-NMR | MS (m/z) |
|---|---|---|---|---|
| Example 767 0.064 WX Method 196 | 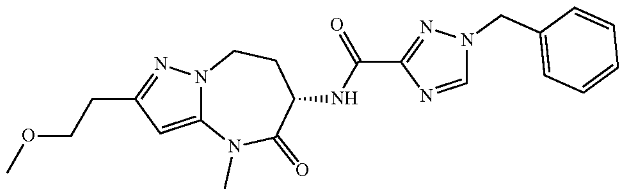 [SMILES: COCCc1cc2n(n1)CC[C@H](NC(=O)c1ncn(Cc3ccccc3)n1)C(=O)N2C] 1-benzyl-N-[(6S)-2-(2-methoxyethyl)-4-methyl-5-oxo-7,8-dihydro-6H-pyrazolo [1,5-a][1,3]diazepin-6-yl]-1,2,4-triazole-3-carboxamide | Single Unknown Stereoisomer | 1H NMR (400 MHz, CD3OD) δ 8.55 (s, 1H), 7.38-7.31 (m, 5H), 6.18 (s, 1H), 5.47 (s, 2H), 4.58-4.52 (m, 1H), 4.34-4.30 (m, 1H), 4.25-4.22 (m, 1H), 3.66 (t, J = 6.8 Hz, 2H), 3.35 (s, 3H), 3.31 (s, 3H), 2.87-2.83 (m, 3H), 2.27-2.21 (m, 1H). | 424.2 |
| Example 768 0.051 WX Method 196 | 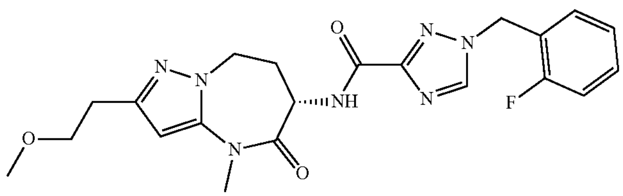 [SMILES: COCCc1cc2n(n1)CC[C@H](NC(=O)c1ncn(Cc3ccccc3F)n1)C(=O)N2C] 1-[(2-fluorpphenyl)methyl]-N-[(6S)-2-(2-methoxyethyl)-4-methyl-5-oxo-7,8-dihydro-6H-pyrazolo[1,5-a][1,3]diazepin-6-yl]-1,2,4-triazole-3-carboxamide | Single Unknown Stereoisomer | 1H NMR (400 MHz, CD3OD) δ 8.56 (s, 1H), 7.42-7.33 (m, 2H), 7.22-7.09 (m, 2H), 6.17 (s, 1H), 5.54 (s, 2H), 4.58-4.51 (m, 1H), 4.36-4.29 (m, 1H), 4.26-4.16 (m, 1H), 3.65 (t, J = 6.8 Hz, 2H), 3.35 (s, 3H), 3.31 (s, 3H) 2.86-2.77 (m, 3H), 2.28-2.20 (m, 1H). | 442.2 |
| Example 769 0.233 WX MEthod 201 | 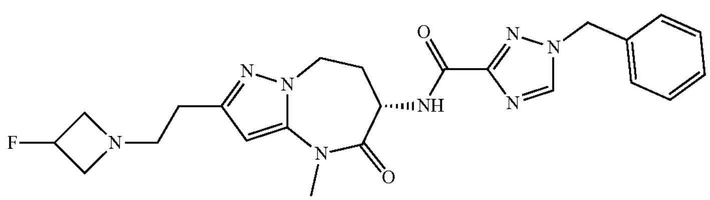 [SMILES: CN1C(=O)[C@@H](NC(=O)c2ncn(Cc3ccccc3)n2)CCn2nc(CCN3CC(F)C3)cc21] 1-benzyl-N-[(6S)-2-[2-(3-fluoroazetidin-1-yl)ethyl]-4-methyl-5-oxo-7,8-dihydro-6H-pyrazole[1,5-a][1,3]diazepin-6-yl]-1,2,4-triazole-3-carboxamide | Single Unknown Stereoisomer | 1H NMR (400 MHz, CD3OD) δ 8.57 (s, 1H), 7.41-7.30 (m, 5H), 6.18 (s, 1H), 5.48 (s, 2H), 5.24-5.18 (m, 0.5H), 5.09-5.04 (m, 0.5m), 4.57-4.52 (m, 1H), 4.38-4.30 (m, 1H), 4.26-4.17 (m, 1H), 3.76-3.66 (m, 2H), 3.39-3.32 (m, 5H), 2.91-2.81 (m, 3H), 2.71-2.64 (m, 2H), 2.30-2.21 (m, 1H) | 467.2 |

TABLE 5-continued

| Example Ki (uM) Method(s) | Structure | Stereo | $^1$H-NMR | MS (m/z) |
|---|---|---|---|---|
| Example 770 0.337 WX Method 201 | 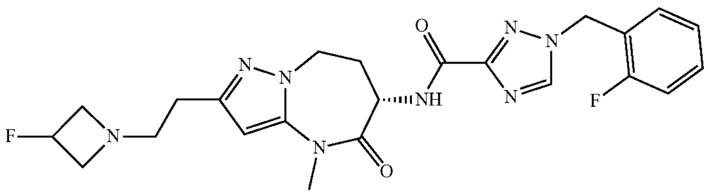 [SMILES: CN1C(=O)[C@@H](NC(=O)c2ncn(Cc3ccccc3F)n2)CCn2nc(CCN3CC(F)C3)cc21] 1-[(2-fluorophenyl)methyl]-N-[(6S)-2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide | Single Unknown Stereoisomer | 1H NMR (400 MHz, CD3OD) δ 8.59 (s, 1H), 7.40-7.37 (m, 2H), 7.22-7.13 (m, 2H), 6.20 (s, 1H), 5.56 (s, 2H), 5.33-5.25 (m, 0.5H), 5.22-5.18 (m, 0.5H), 4.58-4.49 (m, 1H), 4.36-4.33 (m, 1H), 4.25-4.22 (m, 1H) 4.15-4.06 (m, 2H), 3.85-3.76 (m, 2H), 3.33 (s, 3H), 3.21-3.18 (m, 2H), 2.86-2.79 (m, 3H), 2.29-2.25 (m, 1H). | 485.2 |
| Example 771 0.172 WX Method 194 | 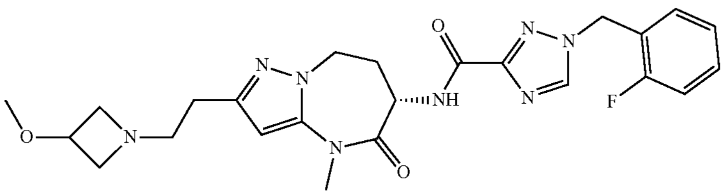 [SMILES: COC1CN(CCc2cc3n(n2)CC[C@H](NC(=O)c2ncn(Cc4ccccc4F)n2)C(=O)N3C)C1] 1-[(2-fluorophenyl)methyl]-N-[(6S)-2-[-(3-methoxyazetidin-1-yl)ethyl]-4-methyl-5-oxo-7,8-dihydro-6H-pyrazolo[1,5-a][1,3] diazepin-6-yl]-1,2,4-triazole-3-carboxamide | Single Unknown Stereoisomer | 1H NMR (400 MHz, CD3OD) δ 8.57 (s, 1H), 7.40-7.36 (m, 2H), 7.22-7.13 (m, 2H), 6.16 (s, 1H), 5.55 (s, 2H), 4.56-4.51 (m, 1H), 4.36-4.31 (m, 1H), 4.25-4.17 (m, 1H), 4.06-4.04 (m, 1H, 3.65-3.61 (m, 2H), 3.32 (s, 3H), 3.25 (s, 3H), 3.03-3.00 (m, 2H), 2.87-2.80 (m, 3H), 2.68-2.66 (m, 2H), 2.28-2.20 (m, 1H). | 497.1 |
| Example 772 0.115 WX Method 205 | 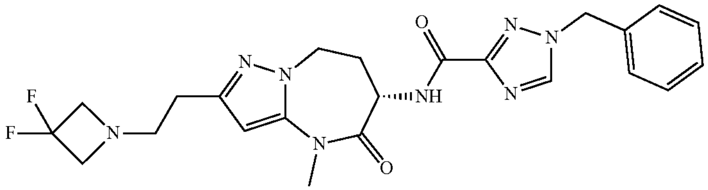 [SMILES: CN1C(=O)[C@@H](NC(=O)c2ncn(Cc3ccccc3)n2)CCn2nc(CCN3CC(F)(F)C3)cc21] 1-benzyl-N-[(6S)-2-[2-2(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide | Single Unknown Stereoisomer | 1H NMR (400 MHz, CD3OD) δ 8.58 (s, 1H), 7.42-7.35 (m, 5H), 6.21 (s, 1H), 5.50 (s, 2H), 4.59-4.52 (m, 1H) 4.36-4.32 (m, 1H), 4.26-4.22 (m, 1H), 3.37 (t, J = 12.0 Hz, 4H), 3.35 (s, 3H), 2.97-2.82 (m, 3H), 2.75-2.65 (m, 2H), 2.29-2.23 (m, 1H). | 485.2 |

TABLE 5-continued

| Example<br>Ki (uM)<br>Method(s) | Structure | Stereo | $^{1}$H-NMR | MS (m/z) |
|---|---|---|---|---|
| Example 773<br>0.189<br>WX Method<br>205 | 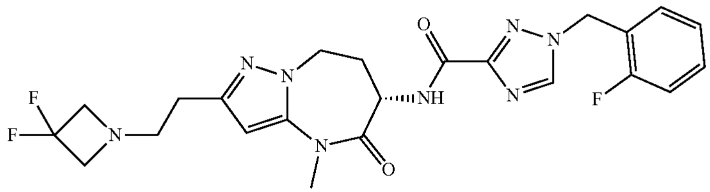<br>1-[(2-fluorophenyl)methyl]-N-[(6S)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide | Single<br>Unknown<br>Stereoisomer | 1H NMR (400 MHz, CD3OD) δ 8.58 (s 1H), 7.42-7.35 (m, 2H), 7.20-7.12 (m, 2H), 6.19 (s, 1H), 5.50 (s, 2H), 4.57-4.52 (m, 1H), 4.36-4.32 (m, 1H) 4.24-4.20 (m, 1H), 3.65 (t, J = 12.0 Hz, 3H), 3.30 (s, 3H), 2.97-2.82 (m, 3H), 2.75-2.67 (m, 2H), 2.29-2.23 (m, 1H). | 503.2 |
| Example 774<br>0.037<br>WX Method<br>210 | 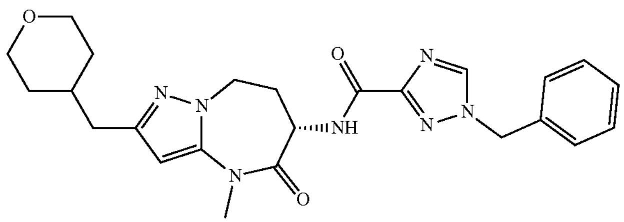 [SMILES: CN1C(=O)[C@@H](NC(=O)c2ncn(Cc3ccccc3)n2)CCn2nc(CC3CCOCC3)cc21]<br>1-benzyl-N-[(6S)-4methyl-5-oxo-2-(tetrahydropyran-4-ylmethyl)-7,8-dihydro-6H-pyrazolo[1,5-a][1,3]diazepin-6-yl]-1,2,4-triazole-3-carboxamide | Single<br>Unknown<br>Stereoisomer | 1H NMR (400 MHz, CD3OD) δ 8.57 (s, 1H), 7.40-7.33 (m, 5H), 6.16 (s, 1H), 5.48 (s, 2H), 4.54-4.48 (m, 1H), 4.37-4.30 (m, 1H), 2.27-4.17 (m, 1H), 3.96-3.90 (m, 2H), 3.44-3.36 (m, 2H), 3.33 (s, 3H), 2.90-2.80 (m, 1H), 5.57-2.53 (m, 2H), 2.30-2.22 (m, 1H), 1.92-1.82 (m, 1H), 1.68-1.62 (m, 2H), 1.35-1.31 (m, 2H). | 464.2 |
| Example 775<br>0.182<br>Suzuki_Method_2 | 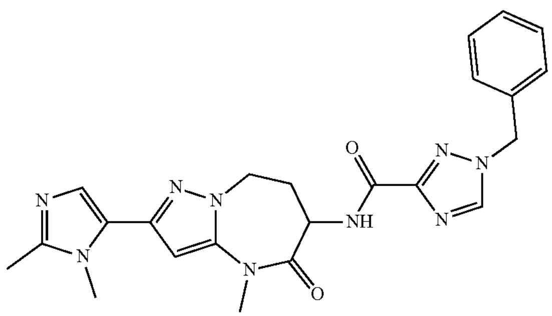 [SMILES: Cc1ncc(-c2cc3n(n2)CCC(NC(=O)c2ncn(Cc4ccccc4)n2)C(=O)N3C)n1C]<br>1-benzyl-N-(2-1,2-dimethyl-1H-imidazol-5-yl)-4-methyl-5-oxo-5,6,7,8-tetrahydro-4H-pyrazolo[1,5-a][1,3]diazepin-6-yl)-1H-1,2,4-triazole-3-carboxamide | Mixture<br>of<br>Enantiomers | $^{1}$H NMR (400 MHz, DMSO-d6) δ 8.82 (s, 1H), 8.58 (d, J = 7.8 Hz, 1H), 8.34 (s, 2H), 7.45-7.24 (m, 5H), 7.05 (s, 1H), 6.60 (s, 1H), 5.49 (s, 2H), 3.76 (s, 3H), 3.27 (s, 3H), 2.81 (dd, J = 63.8, 0.6 Hz, 1H), 2.71-2.56 (m, 1H), 2.32 (s, 3H) | 460.2<br>2.76 min |

TABLE 5-continued

| Example<br>Ki (uM)<br>Method(s) | Structure | Stereo | $^1$H-NMR | MS (m/z) |
|---|---|---|---|---|
| Example 776<br>0.212<br>Suzuki_Method_2 | 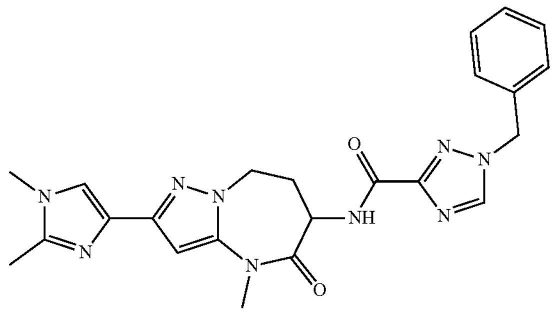 [SMILES: Cc1nc(-c2cc3n(n2)CCC(NC(=O)c2ncn(Cc4ccccc4)n2)C(=O)N3C)cn1C] | Mixture<br>of<br>Enantiomers | $^1$H NMR (400 MHz, DMSO-d6) δ 8.82 (s, 1H), 8.52 (d, J = 7.8 Hz, 1H), 8.32 (s, 2H), 7.46-7.23 (m, 5H), 6.46 (s, 1H), 5.48 (s, 2H), 3.56 (s, 3H), 3.26 (s, 3H), 2.73-2.57 (m, 1H), 2.29 (s, 3H) | 460.2<br>2.72 min |
| Example 777<br>0.070<br>Suzuki_Method_2 | 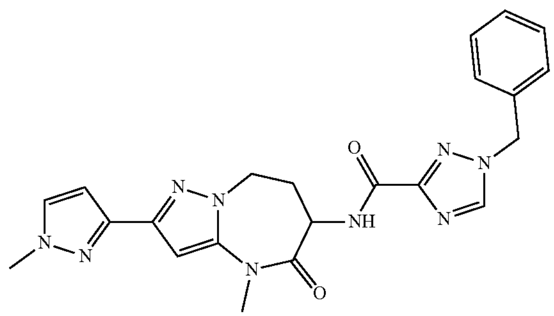 [SMILES: CN1C(=O)C(NC(=O)c2ncn(Cc3ccccc3)n2)CCn2nc(-c3ccn(C)n3)cc21]<br>1-benzyl-N-(4-methyl-2-(-methyl-1H)-pyrazol-3-yl)-5-oxo-5,6,7,8-tetrahydro-4H-pyrazolo[1,5-a][1,3]diazepin-6-yl)-1H-1,2,4-triazole-3-carboxzmide | Mixture<br>of<br>Enantiomers | $^1$H NMR (400 MHz, DMSO-d6) δ 8.85 (s, 1H), 8.54 (d, J = 7.8 Hz, 1H), 7.70 (dd, J = 22, 0.4 Hz, 1H), 7.45-7.20 (m, 5H), 6.58 (s, 1H), 6.50 (d, J = 2.2 Hz, 1H), 5.48 (s, 2H), 4.37 (s, 1H), 4.11-3.98 (m, 1H), 3.86 (s, 3H), 3.17 (d, J = 5.2 Hz, 4H). | 446.2<br>3.67 min |

TABLE 5-continued

| Example Ki (uM) Method(s) | Structure | Stereo | $^1$H-NMR | MS (m/z) |
|---|---|---|---|---|
| Example 778 0.171 Suzuki_Method_2 | 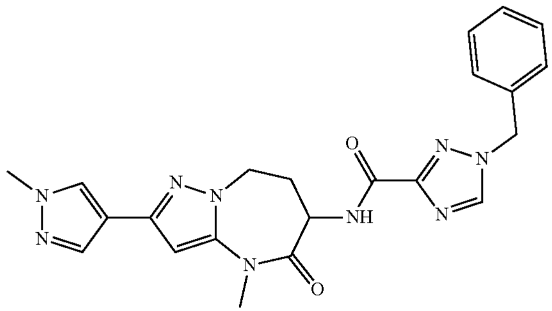 [SMILES: CN1C(=O)C(NC(=O)c2ncn(Cc3ccccc3)n2)CCn2nc(-c3cnn(C)c3)cc21] 1-benzyl-N-(4-methyl-2-(1-methyl-1H-pyrazol-4-yl)-5-oxo-5,6,7,8-tretrahydro-4H-pyrazolo[1,5-a][1,3] diazepin-6-yl)-1H-1,2,4-triazole-3-carboxamide | Mixture of Enantiomers | $^1$H NMR (400 MHz, DMSO-d6) δ 8.82 (s, 1H), 8.54 (d, J = 7.8 Hz, 1H), 7.98 (d, J = 0.9 Hz, 1H), 7.70 (d, J = 0.8 Hz, 1H), 7.47-7.19 (m, 4H), 6.50 (s, 1H), 5.48 (s, 2H), 4.45-4.08 (m, 2H), 3.86 (s, 3H), 3.26 (s, 4H), 2.44-2.24 (m, 1H) | 446.2 3.63 min |
| Example 779 0.155 (chiral seperation of Ex. 443) | 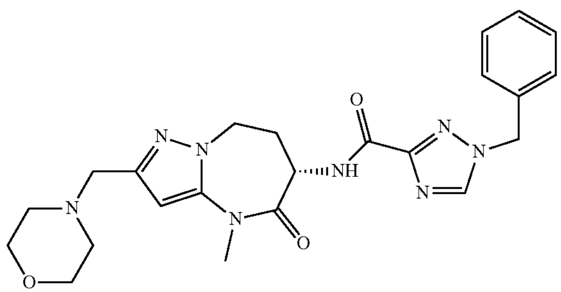 [SMILES: CN1C(=O)[C@@H](NC(=O)c2ncn(Cc3ccccc3)n2)CCn2nc(CN3CCOCC3)cc21] 1-benzyl-N-[(6S)-4-methyl-2-(morpholinomethyl)-5-oxo-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-d6) δ 8.81 (s, 1H), 8.51 (d, J = 7.7 Hz, 1H, 1H), 7.42-7.26 (m, 5H), 6.26 (s, 1H), 5.48 (s, 2H), 4.36-4.24 (m, 2H), 4.14 (m, 1H), 3.57 (m, 4H), 3.48-3.21 (m, 5H), 2.59 (m, 1H), 2.49-2.29 (m, 5H). | 465.2 2.55 min |

TABLE 5-continued

| Example Ki (uM) Method(s) | Structure | Stereo | $^1$H-NMR | MS (m/z) |
|---|---|---|---|---|
| Example 780 0.598 METHOD GZ7 | 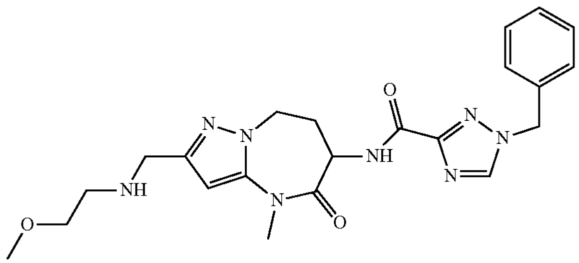 [SMILES: COCCNCc1cc2n(n1)CCC(NC(=O)c1ncn(Cc3ccccc3)n1)C(=O)N2C] 1-benzyl-N-[2-[(2-methoxyethylamino)methyl]-4-methly-5-oxo-7,8-dihydro-6H-pyrazolo[1,5-a][1,3]diazepin-6-yl]-1,2,4-triazole-3-carboxamide | Mixture of Enantiomers | $^1$H NMR (400 MHz, DMSO-d6) δ 8.82 (s, 1H), 8.51 (d, J = 7.8 Hz, 1H), 7.43-7.26 (m, 5H), 6.26 (s, 1H), 5.48 (s, 2H), 4.31 (m, 2H), 4.21-4.07 (m, 1H), 3.66 (d, J = 2.1 Hz, 2H), 3.46-3.31 (m, 2H), 3.23 (s, 6H), 2.72 (t, J = 5.7 Hz, 2H), 2.58 (m, 1H), 2.41-2.28 (m, 1H). | 453.2 2.62 min |
| Example 781 0.172 CHIRAL SEP | 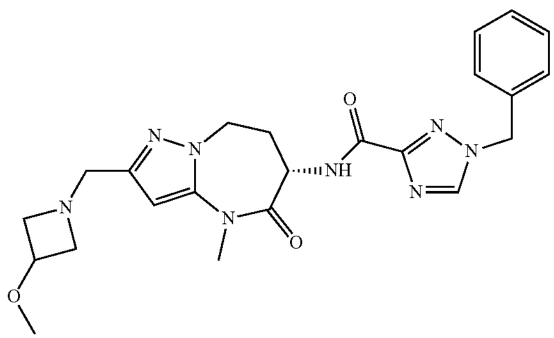 [SMILES: COC1CN(Cc2cc3n(n2)CC[C@H](NC(=O)c2ncn(Cc4ccccc4)n2)C(=O)N3C)C1] (S)-1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide | Single Unknown Stereoisomer | $^1$H NMR (400 MHz, DMSO-d6) δ 8.81 (s, 1H), 8.51 (d, J = 7.7 Hz, 1H), 7.42-7.26 (m, 5H), 6.21 (s, 1H), 5.48 (s, 2H), 4.35-4.23 (m, 2H), 4.13 (m, 1H), 3.94 (p, J = 5.8 Hz, 1H), 3.57-3.32 (m, 4H), 3.18 (ds, 6H), 2.86 (m, 2H), 5.58 (m, 1H), 2.41-2.28 (m, 1H). | 465.2 2.62 min |
| Example 782 0.142 CHIRAL SEP | (S)-1-benzyl-N-(2-((3-fluoroazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide | Single Unknown Stereoisomer | $^1$H NMR (400 MHz, DMSO-$d_6$) δ 8.81 (s, 1H), 8.52 (d, J = 7.8 Hz, 1H), 7.42-7.26 (m, 5H), 6.23 (s, 1H), 5.48 (s, 2H), 5.26-5.01 (m, 1H), 4.35-4.23 (m, 2H), 4.14 (m, 1H), 3.36-350 (m, 4H), 3.27-3.06 (m, 5H), 2.58 (m, 1H), 2.41-2.28 (m, 1H). | 453.2 2.59 min |

TABLE 5-continued

| Example Ki (uM) Method(s) | Structure | Stereo | $^1$H-NMR | MS (m/z) |
|---|---|---|---|---|
| Example 783 0.0.59 CHIRAL SEP | 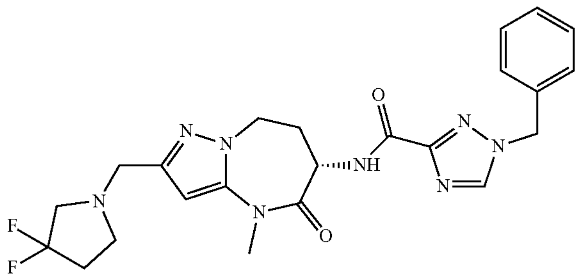 [SMILES: CN1C(=O)[C@@H](NC(=O)c2ncn(Cc3ccccc3)n2)CCn2nc(CN3CCC(F)(F)C3)cc21] (S)-1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide | Single Unknown Stereoisomer | $^1$H NMR (400 MHz, DMSO-$d_6$) δ 8.81 (s, 1H), 8.52 (d, J = 7.8 Hz, 1H), 7.42-7.26 (m, 5H) 6.28 (s, 1H), 5.48 (s, 2H), 4.31 (qd, J = 7.9, 2.4 Hz, 2H), 4.15 (ddd, J = 14.5, 12.6, 6.6 Hz, 1H), 3.57 (q, J = 13.4 Hz, 2H), 3.23 (s, 3H), 2.91 (t, J = 13.4 Hz, 2H), 2.73 (t, J = 7.0 Hz, 2H), 2.67-2.54 (m, 1H), 2.43-2.10 (m, 3H). | 485.2 2.86 min |
| Example 784 0.225 CHIRAL SEP | 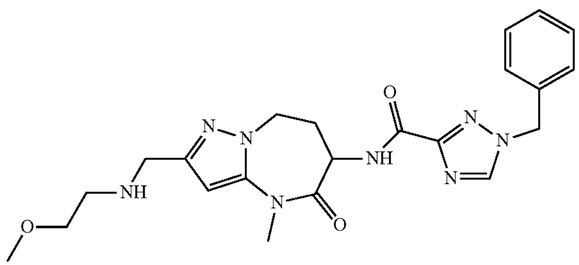 [SMILES: COCCNCc1cc2n(n1)CCC(NC(=O)c1ncn(Cc3ccccc3)n1)C(=O)N2C] (S)-1-benzyl-N-(2-(((2-methoxyethyl)amino)methyl-5-oxo-5,6,7,8-tetrahydro-4H-pyrazolo[1,5-a][1,3]diazepin-6-yl)-1H-1,2,4-triazole-3-carboxamide | Single Unknown Stereoisomer | $^1$H NMR (400 MHz, DMSO-$d_6$) δ 8.82 (s, 1H), 8.51 (d, J = 7.8 Hz, 1H), 7.43-7.26 (m, 5H), 6.26 (s, 1H), 5.48 (s, 2H), 4.31 (m, 2H), 4.21-4.07 (m, 1H), 3.66 (d, J = 2.1 Hz, 2H), 3.46-3.31 (m, 2H), 3.23 (s, 6H), 2.72 (t, J = 5.7 Hz, 2H), 2.58 (m, 1H), 2.41-2.28 (m, 1H). | 453.2 2.65 min |

TABLE 5-continued

| Example<br>Ki (uM)<br>Method(s) | Structure | Stereo | $^1$H-NMR | MS (m/z) |
|---|---|---|---|---|
| Example 785<br>0.074<br>CHIRAL<br>SEP | 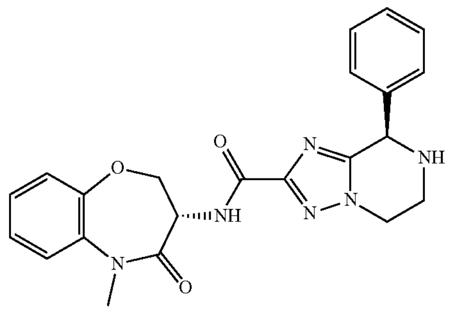 [SMILES: CN1C(=O)[C@@H](NC(=O)c2nc3n(n2)CCN[C@@H]3c2ccccc2)COc2ccccc21]<br>(8R)-N-[(3S)-5-methyl-4-oxo-2,3-dihydro-1,5-benzoxazepin-3-yl]-8-phenyl-5,6,7,8-tetrahydro-[1,2,4]triazolo[1,5-a]pyrazine-2-carboxamide | Single<br>Unknown<br>Stereoisomer | $^1$H NMR (400 MHz, DMSO-$d_6$) δ 8.34 (d, J = 8.0 Hz, 1H), 7.49 (dd, J = 7.6, 1.9 Hz, 1H), 7.42-7.18 (m, 9H), 5.20 (d, J = 5.3 Hz, 1H), 4.81 (dt, J = 11.4, 7.8 Hz, 1H), 4.56 (dd, J = 11.6, 9.8 Hz, 1H), 4.36(dd, J = 9.9, 7.7 Hz, 1H), 4.32-4.15 (m, 2H), 3.37 (q, J = 5.1 Hz, 1H), 3.32-3.11 (m, 4H). | 419.1<br>3.26 min |
| Example 786<br>0.112<br>METHOD GZ17 | 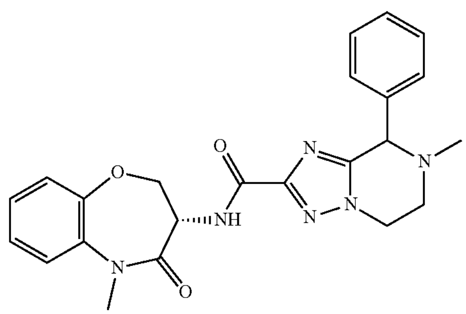 [SMILES: CN1C(=O)[C@@H](NC(=O)c2nc3n(n2)CCN(C)C3c2ccccc2)COc2ccccc21]<br>7-methyl-N-[(3S)-5-methyl-4-oxo-2,3-dihydro-1,5-benzoxazepin-3-yl]-8-phenyl-6,8-dihydro-5H-[1,2,4]trizolo[1,5-a]pyrazine-2-carboxamide | Mixture of<br>Diastereomers | $^1$H NMR (400 MHz, DMSO-d6) δ | 433.2<br>4.29 min |

TABLE 5-continued

| Example Ki (uM) Method(s) | Structure | Stereo | $^1$H-NMR | MS (m/z) |
|---|---|---|---|---|
| Example 787 0.309 METHOD GZ6 | 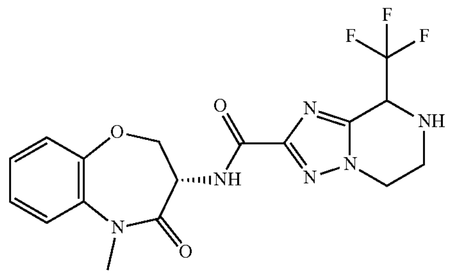 [SMILES: CN1C(=O)[C@@H](NC(=O)c2nc3n(n2)CCNC3C(F)(F)F)COc2ccccc21] N-[(3S)-5-methyl-4-oxo-2,3-dihydro-1,5-benzoxazepin-3-yl]-8-(trifluoromethyl)-5,6,7,8-tetrahydro-[1,2,4]triazolo[1,5-a]pyrazine-2-carboxamide | Mixture of Diastereomers | $^1$H NMR (400 MHz, DMSO-$d_6$) δ 8.44 (dd, J = 7.9, 2.3 Hz, 1H), 7.57-7.45 (m, 1H), 7.39-7.16 (m, 4H), 5.16-4.99 (m, 1H), 4.85 (dtd, J = 11.5, 7.8, 3.8 Hz, 1H), 4.60 (dt, J = 11.5, 9.7 Hz, 1H), 4.43 (ddd, J = 9.9, 7.6, 6.8 Hz, 1H), 4.25 (m, 1H), 4.21-4.04 (m, 1H), 3.68 (m, 1H), 3.31 (s, 3H), 3.27-3.19 (m, 1H). | 411.1 3.87 min |
| Example 788 0.061 CHIRAL SEP | 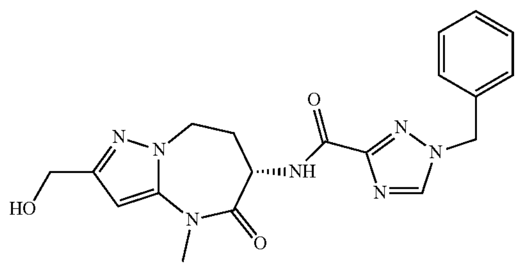 [SMILES: CN1C(=O)[C@@H](NC(=O)c2ncn(Cc3ccccc3)n2)CCn2nc(CO)cc21] 1-benzyl-N-[(6S)-2-(hydroxymethyl)-4-methyl-5-oxo-7,8-dihydro-6H-pyrazolo[1,5-a][1,3]diazepin-6-yl]-1,2,4-triazole-3-carboxamde | Single Unknown Stereoisomer | $^1$H NMR (400 MHz, DMSO-d6) δ 8.82 (s, 1H), 8.51 (d, J = 7.8 Hz, 1H), 7.42-7.26 (m, 5H), 6.28 (s, 2H), 5.10 (t, J = 5.8 Hz, 1H), 4.45-4.24 (m, 4H), 4.15 (m, 1H), 3.24 (s, 3H), 2.58 (m, 1H), 2.41-2.28 (m, 1H) | 396.1 3.14 min |

TABLE 5-continued

| Example Ki (uM) Method(s) | Structure | Stereo | $^1$H-NMR | MS (m/z) |
|---|---|---|---|---|
| Example 789 0.068 METHOD GZ8 | 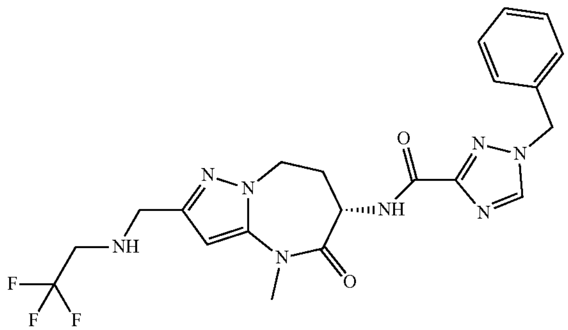 [SMILES: CN1C(=O)[C@@H](NC(=O)c2ncn(Cc3ccccc3)n2)CCn2nc(CNCC(F)(F)F)cc21] 1-benzyl-N-[(6S)-4-methyl-5-oxo-2-[(2,2,2-trifluoroethylamino)methyl]-7,8-dihydro-6H-pyrazolo[1,5-a][1,3]diazepin-6-yl]-1,2,4-triazole-3-carboxamide | Single Unknown Stereoisomer | $^1$H NMR (400 MHz, DMSO-d6) δ 8.82 (s, 1H), 8.52 (d, J = 7.8, 1H), 7.42-7.26 (m, 5H), 6.28 (s, 1H), 5.48 (s, 2H), 4.31 (m, 2H), 4.15 (m, 1H), 3.79-3.64 (m, 2H), 3.33 | 477.2 3.18 min |
| Example 790 0.149 CHIRAL SEP | 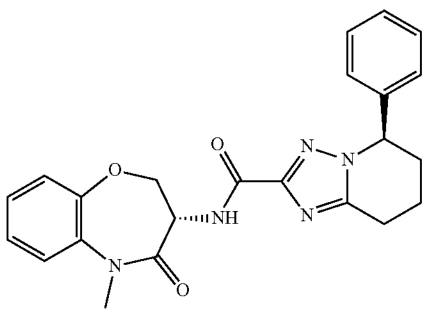 [SMILES: CN1C(=O)[C@@H](NC(=O)c2nc3n(n2)[C@@H](c2ccccc2)CCC3)COc2ccccc21] (5R)-N-[(3S)-5-methyl-4-oxo-2,3-dihydro-1,5-benzoxazepin-3-yl]-5-phenyl-5,6,7,8-tetrahydro-[1,2,4]tetrahydro-[1,2,4]triazolo [1,5-a]pyridine-2-carboxamide | Single Unknown Stereoisomer | $^1$H NMR (400 MHz, DMSO-d6) δ 8.40 (d, J = 7.9 Hz, 1H), 7.49 (dd, J = 7.6, 2.0 Hz, 1H), 7.40-7.18 (m, 6H), 7.09-7.01 (m, 2H), 5.57 (t, J = 5.9 Hz, 1H), 4.80 (dt, J = 11.5, 7.8 Hz, 1H), 4.57 (dd, J = 11.6, 9.9Hz, 1H), 4.38 (dd, J = 9.9, 7.6 Hz, 1H), 3.30 (s, 3H), 3.11-2.89 (m, 2H), 2.49-2.32 (m, 1H), 2.11-1.98 (m, 1H), 1.87 (h, J = 5.9, 5.4 Hz, 2H) | 418.2 11.60 |

TABLE 5-continued

| Example Ki (uM) Method(s) | Structure | Stereo | $^1$H-NMR | MS (m/z) |
|---|---|---|---|---|
| Example 791 0.013 CHIRAL SEP | 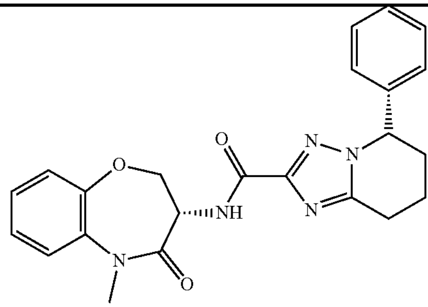 (5S)-N-[(3S)-5-methyl-4-oxo-2,3-dihydro-1,5-benzoxazepin-3-yl]-5-phenyl-5,6,7,8-tetrahydro-[1,2,4]triazolo[1,5-a]pyridine-2-carboxamide | Single Unknown Stereoisomer | $^1$H NMR (400 MHz, DMSO-d6) δ 8.38 (d, J = 8.0 Hz, 1H), 7.49 (dd, J = 7.5, 2.0 Hz, 1H), 7.40-7.19 (m, 6H), 7.09-7.01 (m, 2H), 5.57 (t, J = 5.9 Hz, 1H), 4.80 (dt, J = 11.5, 7.8 Hz, 1H), 4.56 (dd, J = 11.5,9.9 Hz, 1H), 4.38 (dd, J = 9.9, 7.7 Hz, 1H), 3.44-3.20 (s, 3H), 3.10-2.90 (m, 2H), 2.38 (dt, J = 11.5, 6.4 Hz, 1H), 2.10-1.98 (m, 1H), 1.86 (p, J = 6.3 Hz, 2H) | 418.1 11.72 |
| Example 792 0.070 METHOD GZ20 | 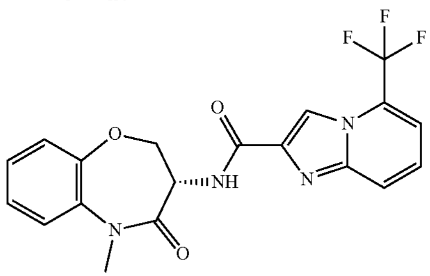 [SMILES: CN1C(=O)[C@@H](NC(=O)c2cn3c(C(F)(F)F)cccc3n2)COc2ccccc21] N-[(3S)-5-methyl-4-oxo-2,3-dihydro-1,5-benzoxazepin-3-yl]-5-(trifluoromethyl)imidazo[1,2-a]pyridine-2-carboxamide | Single Unknown Stereoisomer | $^1$H NMR (400 MHz, DMSO-d6) δ 8.58 (d, J = 8.0 Hz, 1H), 8.30 (q, J = 1.8 Hz, 1H), 8.05 (d, J = 9.2, 1H), 7.70 (d, J = 7.1 Hz, 1H), 7.60-7.48 (m, 2H), 7.30 (m, 3H),4.91 (dt, J = 11.4, 7.9 Hz, 1H), 4.60 (dd, J = 11.5, 9.9 Hz, 1H), 4.47 (dd, J = 9.9, 7.7 Hz, 1H), 3.34 (s, 3H) | 405.0 6.00 |
| Example 793 TBD METHOD GZ20 | 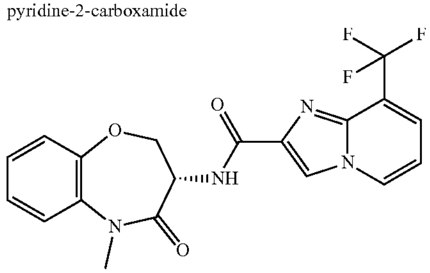 (S)-N-(5-methyl-4-oxo-2,3,4,5-tetrahydrodenzo[b][1,4]oxazepin-3-yl)-8-(trifluoromethyl)imidazo[1,2-a]pyridine-2-carboxamide | Single Unknown Stereoisomer | $^1$H NMR (400 MHz, DMSO-d6) δ 8.82 (d, J = 6.8 Hz, 1H), 8.57 (s, 1H), 8.30 (d, J = 7.8 Hz, 1H), 7.86 (dt, J = 7.3, 1.2 Hz, 1H), 7.55-7.46 (m, 1H), 7.39-7.23 (m, 3H), 7.14 (t, J = 7.0 Hz, 1H), 4.91 (dt, J = 11.3, 7.7 Hz, 1H), 4.64-4.45 (m, 2H), 3.35 (s, 3H) | 405.0 4.81 |

The following methods exemplify scaled-up processes for the synthesis of compounds provided herein.

Example A

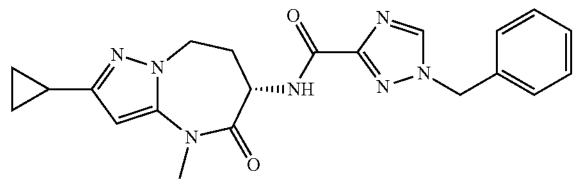 [SMILES: CN1C(=O)[C@@H](NC(=O)c2ncn(Cc3ccccc3)n2)CCn2nc(C3CC3)cc21]

(S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide

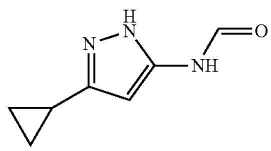 [SMILES: O=CNc1cc(C2CC2)n[nH]1]

Step 1: N-(3-cyclopropyl-1H-pyrazol-5-yl)formamide

A mixture of 5-cyclopropyl-1H-pyrazol-3-amine (10.0 g, 81.2 mmol) and formic acid (31 mL) was heated at 110° C. for 12 h and subsequently concentrated under reduced pressure. The residue was purified by column chromatography (silica gel, 100-200 mesh, 0 to 10% methanol in dichloromethane) to give N-(3-cyclopropyl-1H-pyrazol-5-yl)formamide (8.0 g, 65%) as a yellow solid, used in the next step as is.

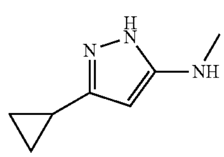

Step 2: 3-cyclopropyl-N-methyl-1H-pyrazol-5-amine

To a stirred solution of N-(3-cyclopropyl-1H-pyrazol-5-yl)formamide (8.0 g, 52.9 mmol) in tetrahydrofuran (200 mL) was added lithium aluminumhydride (4.0 g, 105.8 mmol) in small portions at 0° C. After addition, the mixture was stirred for 15 h at 25° C. and subsequently slowly quenched by addition of water (4 mL), aqueous sodium hydroxide (10%, 4 mL) and water (12 mL). To the mixture was added anhydrous sodium sulfate (50 g) and stirred for 30 min. The resulting mixture was filtered and the filtrate was concentrated under reduced pressure to afford crude 3-cyclopropyl-N-methyl-1H-pyrazol-5-amine (6.0 g, 83%) as a colorless oil, used in the next step without further purification.

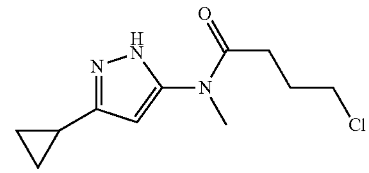 [SMILES: CN(C(=O)CCCCl)c1cc(C2CC2)n[nH]1]

Step 3: 4-chloro-N-(3-cyclopropyl-1H-pyrazol-5-yl)-N-methylbutanamide

A mixture of 3-cyclopropyl-N-methyl-1H-pyrazol-5-amine (6.0 g, 43.7 mmol) and 4-chlorobutanoyl chloride (49 mL) was heated at 60° C. for 5 h and cooled to room temperature. The reaction was quenched by slow addition of methanol (100 mL). The resulting mixture was stirred for 30 min and concentrated under reduced pressure. The residue was purified by column chromatography (silica gel, 100-200 mesh, 0 to 10% methanol in dichloromethane) to afford 4-chloro-N-(3-cyclopropyl-1H-pyrazol-5-yl)-N-methylbutanamide (6.5 g, 62%) as a white solid, used as is in the next step.

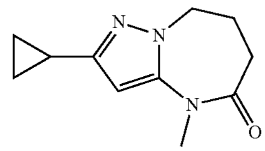

Step 4: 2-cyclopropyl-4-methyl-7,8-dihydro-4H-pyrazolo[1,5-a][1,3]diazepin-5(6H)-one A mixture of 4-chloro-N-(3-cyclopropyl-1H-pyrazol-5-yl)-N-methylbutanamide (6.0 g, 24.9 mmol) and cesium carbonate (16.2 g, 49.8 mmol) in N,N-dimethylformamide (100 mL) was stirred at 25° C. for 12 h and filtered. The filtrate was concentrated under reduced pressure and the residue was purified by column chromatography (silica gel, 100-200 mesh, 0 to 10% methanol in dichloromethane) to afford 2-cyclopropyl-4-methyl-7,8-dihydro-4H-pyrazolo[1,5-a][1,3]diazepin-5(6H)-one (3.7 g, 72%) as yellow oil, used as is in the next step. LCMS RT=1.61 min, m/z=206.1 $[M+H]^+$.

LCMS (0 to 60% acetonitrile in water+0.05% ammonium hydroxide over 3 mins) retention time 1.61 min, ESI+ found [M+H]=206.1.

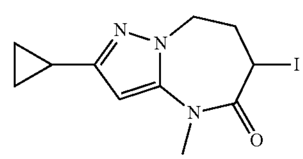 [SMILES: CN1C(=O)C(I)CCn2nc(C3CC3)cc21]

Step 5: 2-cyclopropyl-6-iodo-4-methyl-7,8-dihydro-4H-pyrazolo[1,5-a][1,3]diazepin-5(6H)-one To a stirred solution of 2-cyclopropyl-4-methyl-7,8-dihydro-4H-pyrazolo[1,5-a][1,3]diazepin-5(6H)-one (3.7 g, 18.0 mmol) in dichloromethane (200 mL) was added $N^1$,$N^1$, $N^2$,$N^2$-tetramethylethane-1,2-diamine (16.8 g, 144.2 mmol) and iodotrimethylsilane (28.9 g, 144.2 mmol) at −15° C. The mixture was stirred at −15° C. for 1.5 h and subsequently iodine (13.7 g, 54.0 mmol) was added. The mixture was stirred for another 3 h and quenched by addition of 50% aqueous sodium thiosulfate (50 mL). The mixture was extracted with dichloromethane (3×50 mL). The combined organic layers were washed with brine (2×20 mL), dried over sodium sulfate and concentrated under reduced pressure. The residue was purified by column chromatography (silica gel, 100-200 mesh, 0 to 10% methanol in dichloromethane) to afford 2-cyclopropyl-6-iodo-4-methyl-7,8-dihydro-4H-pyrazolo[1,5-a][1,3]diazepin-5(6H)-one (4.5 g, 75%) as colorless oil, used as is in the next step.

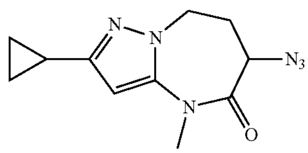 [SMILES: CN1C(=O)C(N=[N+]=[N-])CCn2nc(C3CC3)cc21]

Step 6: 6-azido-2-cyclopropyl-4-methyl-7,8-dihydro-4H-pyrazolo[1,5-a][1,3]diazepin-5(6H)-one A mixture of 2-cyclopropyl-6-iodo-4-methyl-7,8-dihydro-4H-pyrazolo[1,5-a][1,3]diazepin-5(6H)-one (4.5 g, 13.6 mmol) and sodium azide (1.3 g, 20.4 mmol) in N,N-dimethylformamide (20 mL) was stirred at 25° C. for 2 h. To the reaction mixture was added ice water (5 mL) and extracted with ethyl acetate (3×100 mL). The combined organic layers were washed with brine (2×20 mL), dried over sodium sulfate and concentrated under reduced pressure to give crude 6-azido-2-cyclopropyl-4-methyl-7,8-dihydro-4H-pyrazolo[1,5-a][1,3]diazepin-5(6H)-one (3.0 g, 90%) as a yellow solid, used as is in the next step. LCMS RT=1.84 min, m/z=247.1 [M+H]+.

LCMS (0 to 60% acetonitrile in water+0.05% ammonium hydroxide over 3 mins) retention time 1.84 min, ESI+ found [M+H]=247.1.

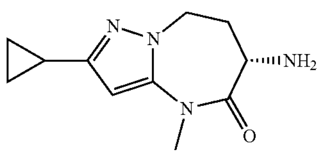 [SMILES: CN1C(=O)[C@@H](N)CCn2nc(C3CC3)cc21]

Step 7: (S)-6-amino-2-cyclopropyl-4-methyl-7,8-dihydro-4H-pyrazolo[1,5-a][1,3]diazepin-5(6H)-one 6-azido-2-cyclopropyl-4-methyl-7,8-dihydro-4H-pyrazolo[1,5-a][1,3]diazepin-5(6H)-one (3.0 g, 12.2 mmol) and palladium on carbon (10%, 1.3 g, 1.22 mmol) in methyl alcohol (100 mL) was hydrogenated (15 psi) at 25° C. for 12 h and subsequently filtered. The filtrate was concentrated under reduced pressure and the residue was purified by column chromatography on silica (solvent gradient: 0-10% methanol in dichloromethane) to afford crude 6-amino-2-cyclopropyl-4-methyl-7,8-dihydro-4H-pyrazolo[1,5-a][1,3] diazepin-5(6H)-one, which was further separated by chiral SFC (SFC80; Chiralpak OD (250 mm*30 mm, 5 um); Supercritical $CO_2$/MeOH+$NH_3$.$H_2O$=20/20; 50 mL/min) to give:

Peak 1 (Rt=3.113 min):

(S)-6-amino-2-cyclopropyl-4-methyl-7,8-dihydro-4H-pyrazolo[1,5-a][1,3]diazepin-5(6H)-one (600 mg, 22%) as colorless oil. LCMS RT=1.65 min, m/z=221.2 $[M+H]^+$.

Peak 2 (Rt=3.525 min)

(R)-6-amino-2-cyclopropyl-4-methyl-7,8-dihydro-4H-pyrazolo[1,5-a][1,3]diazepin-5(6H)-one (700 mg, 26%) as colorless oil. LCMS RT=1.65 min, m/z=221.2 $[M+H]^+$.

LCMS (0 to 30% acetonitrile in water+0.05% ammonium hydroxide over 3 mins) retention time 1.65 min, ESI+ found [M+H]=221.2.

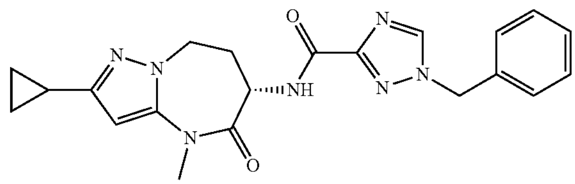 [SMILES: CN1C(=O)[C@@H](NC(=O)c2ncn(Cc3ccccc3)n2)CCn2nc(C3CC3)cc21]

Step 8: (S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide A mixture of 1-benzyl-1,2,4-triazole-3-carboxylic acid (185 mg, 0.91 mmol), (S)-6-amino-2-cyclopropyl-4-methyl-7,8-dihydro-4H-pyrazolo[1,5-a][1,3]diazepin-5 (6H)-one (200 mg, 0.91 mmol), 1-(3-dimethylaminopropyl)-3-ethylcarbodiimidehydrochloride (261 mg, 1.36 mmol) and 1-hydroxybenzotrizole (184 mg, 1.36 mmol) in N,N-dimethylformamide (20 mL) was stirred at 25° C. for 12 h. The solvent was removed under reduced pressure and the residue was purified by RP-HPLC (30% to 60% acetonitrile, 0.05% HCl) to afford (S)-1-benzyl-N-(2-cyclopropyl-4-methyl-5-oxo-5,6,7,8-tetrahydro-4H-pyrazolo[1,5-a][1,3]di azepin-6-yl)-1H-1,2,4-triazole-3-carboxamide (123 mg, 33%) as a white solid.

$^1H$ NMR (400 MHz, DMSO-$d_6$) δ 8.83 (s, 1H), 8.54 (d, J=7.8 Hz, 1H), 7.40-7.28 (m, 5H), 6.06 (s, 1H), 5.48 (s, 2H), 4.34-4.24 (m, 2H), 4.10-4.03 (m, 1H), 3.19 (s, 3H), 2.61-2.54 (m, 1H), 2.37-2.29 (m, 1H), 1.87-1.81 (m, 1H), 0.88-0.81 (m, 2H), 0.70-0.61 (m, 2H) LCMS RT=0.978 min, m/z=406.2 [M+H]+.

LCMS (10 to 80% acetonitrile in water+0.05% ammonium bicarbonate over 3 mins) retention time 0.978 min, ESI+ found [M+H]=406.2.

SFC conditions: Column: Chiralcel AD-3 100×4.6 mm I.D., 3 um Mobile phase: A: $CO_2$ B: ethanol (0.05% DEA), Gradient: from 5% to 40% of B in 4.5 min and hold 40% for 2.5 min, then 5% of B for 1 min. Flow rate: 2.8 mL/min. Column temperature: 40° C.

Example B

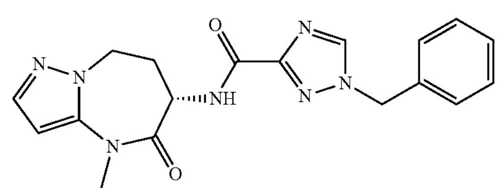

(S)-1-benzyl-N-(4-methyl-5-oxo-5,6,7,8-tetrahydro-4H-pyrazolo[1,5-a][1,5-a[1,3]diazepin-6-yl)-1H-1,2,4-triazole-3-carboxamide

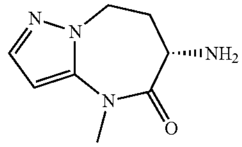

Step 1: (S)-6-amino-4-methyl-7,8-dihydro-4H-pyrazolo[1,5-a][1,3]diazepin-5(6H)-one A mixture of 6-amino-4-methyl-7,8-dihydro-6H-pyrazolo[1,5-a][1,3]diazepin-5-one (5.2 g, 29.0 mmol), 2-hydroxy-5-nitrobenzaldehyde (146 mg, 0.87 mmol) and (2R,3R)-2,3-dihydroxybutanedioic acid (4.36 g, 29.0 mmol) in ethanol (162 mL) was heated to 60° C. for 48 hours and cooled to room temperature. The solid was collected by filtration, washed with ethanol and dried under reduced pressure to afford crude (S)-6-amino-4-methyl-7,8-dihydro-6H-pyrazolo[1,5-a][1,3]diazepin-5-one (2R,3R)-2,3-dihydroxybutanedioic acid as a pale yellow solid.

This crude was recrystallized three times from ethanol/$H_2O$ (9:1, 50 mL/g) to afford fine needle crystals (7.0 g, 73%). The crystals (900 mg, 2.7 mmol) were added to a solution of concentrated aqueous ammonia (31 mL) and dichloromethane (75 mL), and stirred at 25° C. for 30 min. The layers were separated and the aqueous layer was extracted with dichloromethane (2×25 mL). The combined organic layers were washed with brine (2×20 mL), dried over sodium sulfate and concentrated under reduced pressure to give crude (6S)-6-amino-4-methyl-7,8-dihydro-6H-pyrazolo[1,5-a][1,3]diazepin-5-one (400 mg, 82%) as a colorless oil, used as is in the next step.

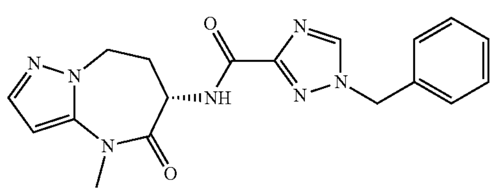 [SMILES: CN1C(=O)[C@@H](NC(=O)c2ncn(Cc3ccccc3)n2)CCn2nccc21]

Step 2: (S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide A mixture of 1-benzyl-1,2,4-triazole-3-carboxylic acid (23 mg, 0.11 mmol), (S)-6-amino-4-methyl-7,8-dihydro-6H-pyrazolo[1,5-a][1,3]diazepin-5-one (20 mg, 0.11 mmol), 1-hydroxybenzotriazole (15 mg, 0.11 mmol) and 1-(3-dimethyl aminopropyl)-3-ethylcarbodiimidehydrochloride (32 mg, 0.17 mmol) in N,N-dimethylformamide (5 mL) was stirred at 25° C. for 12 h. The solvent was removed under reduced pressure and the residue was purified by RP-HPLC (acetonitrile 12-42%/0.05% ammonia hydroxide in water) to afford (S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide (23 mg, 50%) as a white solid. $^1H$ NMR (400 MHz, DMSO-$d_6$) δ 8.82 (s, 1H), 8.54 (d, J=8.0 Hz, 1H), 7.49 (d, J=2.4 Hz, 1H), 7.40-7.27 (m, 5H), 6.34 (d, J=1.6 Hz, 1H), 5.48 (s, 2H), 4.40-4.27 (m, 2H), 4.23-4.14 (m, 1H), 3.24 (s, 3H), 2.64-2.55 (m, 1H), 2.43-2.31 (m, 1H). LC-MS $R_T$=0.702 min, m/z=366.0 $[M+H]^+$.

LCMS (5 to 95% acetonitrile in water+0.03% trifluoacetic acid over 3.0 mins) retention time 0.702 min, ESI+ found [M+H]=366.0.

SFC conditions: Column: Chiralcel AD-3 150×4.6 mm I.D., 3 um Mobile phase: A: $CO_2$ B: ethanol (0.05% DEA), Gradient: from 5% to 40% of B in 5.0 min and hold 40% for 2.5 min, then 5% of B for 2.5 min. Flow rate: 2.5 mL/min Column temperature: 35° C.

Example C

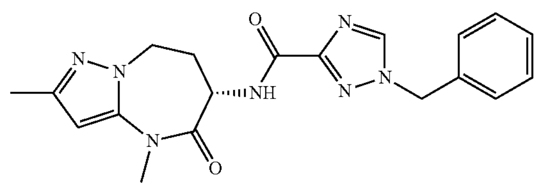 [SMILES: Cc1cc2n(n1)CC[C@H](NC(=O)c1ncn(Cc3ccccc3)n1)C(=O)N2C]

(S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide

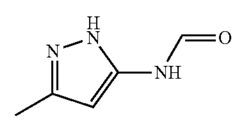

Step 1: N-(3-methyl-1H-pyrazol-5-yl)formamide

A mixture of 5-methyl-1H-pyrazol-3-amine (20.0 g, 206 mmol) and formic acid (100 mL) was heated at 110° C. for 3 h in a sealed vessel and then concentrated under reduced pressure. The residue was purified by column chromatography (silica gel, 100-200 mesh, O to 10% methanol in dichloromethane) to give N-(3-methyl-1H-pyrazol-5-yl)formamide (22.5 g, 87%) as a yellow solid, used as is in the next step.

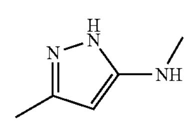

Step 2: N,3-dimethyl-1H-pyrazol-5-amine

To a stirred solution of N-(3-methyl-1H-pyrazol-5-yl)formamide (10.0 g, 80 mmol) in tetrahydrofuran (400 mL) was added lithium aluminumhydride (6.0 g, 160 mmol) in small portions at 0° C. After addition, the mixture was stirred for 15 h at 25° C. and subsequently slowly quenched by addition of water (6 mL), aqueous sodium hydroxide (10%, 6 mL) and water (18 mL). To the mixture was added anhydrous sodium sulfate (60 g) and stirred for 30 min. The reaction mixture was filtered and the filtrate was concentrated to afford crude N,3-dimethyl-1H-pyrazol-5-amine (8.0 g, 90%) as colorless oil, used without further purification in the next step.

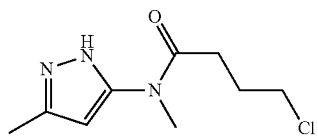

Step 3: 4-chloro-N-methyl-N-(3-methyl-1H-pyrazol-5-yl)butanamide

A mixture of N,3-dimethyl-1H-pyrazol-5-amine (10.0 g, 90 mmol) and 4-chlorobutanoyl chloride (20 mL) was heated at 60° C. for 5 h. After cooling to room temperature, the reaction mixture was quenched by addition of methanol (5 mL) and stirred for 30 min. The mixture was concentrated under reduced pressure and the residue was purified by column chromatography (silica gel, 100-200 mesh, 0 to 5% methanol in dichloromethane) to afford 4-chloro-N-methyl-N-(3-methyl-1H-pyrazol-5-yl)butanamide (6.0 g, 31%) as a yellow oil, used as is in the next step.

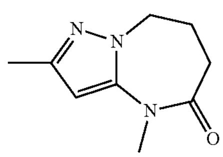

Step 4: 2,4-dimethyl-7,8-dihydro-4H-pyrazolo[1,5-a][1,3]diazepin-5(6H)-one

A mixture of 4-chloro-N-methyl-N-(3-methyl-1H-pyrazol-5-yl)butanamide (6.0 g, 27.8 mmol) and cesium carbonate (18.1 g, 55.6 mmol) in N,N-dimethylformamide (100 mL) was stirred at 25° C. for 15 h and filtered. The filtrate was concentrated under reduced pressure and the residue was purified by column chromatography (silica gel, 100-200 mesh, 0 to 10% methanol in dichloromethane) to afford 2,4-dimethyl-7,8-dihydro-4H-pyrazolo[1,5-a][1,3]diazepin-5(6H)-one (4.0 g, 80%) as yellow oil, used as is in the next step.

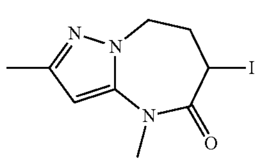

Step 5: 6-iodo-2,4-dimethyl-7,8-dihydro-4H-pyrazolo[1,5-a][1,3]diazepin-5(6H)-one To a stirred solution of 2,4-dimethyl-7,8-dihydro-4H-pyrazolo[1,5-a][1,3]diazepin-5(6H)-one (2.7 g, 15.1 mmol) in dichloromethane (200 mL) was added $N^1,N^1,N^1,N^2$-tetramethylethane-1,2-diamine (14.0 g, 120.0 mmol) and iodotrimethylsilane (24.0 g, 120.0 mmol) at −15° C. The mixture was stirred at −15° C. for 1.5 h and subsequently iodine (11.5 g, 41.2 mmol) was added. The reaction mixture was stirred for another 3 h and subsequently quenched by addition of 5% aqueous sodium thiosulfate (20 mL). The mixture was extracted with dichloromethane (3×50 mL). The combined organic layers were washed with brine (2×20 mL), dried over sodium sulfate and concentrated under reduced pressure. The residue was purified by column chromatography (silica gel, 100-200 mesh, 0 to 10% methanol in dichloromethane) to afford 6-iodo-2,4-dimethyl-7,8-dihydro-4H-pyrazolo[1,5-a][1,3]diazepin-5(6H)-one (3.0 g, 65%) as a colorless oil, used as is in the next step.

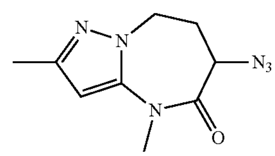 [SMILES: Cc1cc2n(n1)CCC(N=[N+]=[N-])C(=O)N2C]

Step 6: 6-azido-2,4-dimethyl-7,8-dihydro-4H-pyrazolo[1,5-a][1,3]diazepin-5(6H)-one A mixture of 6-iodo-2,4-dimethyl-7,8-dihydro-4H-pyrazolo[1,5-a][1,3]diazepin-5(6H)-one (3.0 g, 9.8 mmol) and sodium azide (959 mg, 14.8 mmol) in N,N-dimethylformamide (30 mL) was stirred at 25° C. for 2 h. To the reaction mixture was added ice water (30 mL) and extracted with dichloromethane (3×30 mL). The combined organic layers were washed with brine (2×20 mL), dried over sodium sulfate and concentrated under reduced pressure to give crude 6-azido-2,4-dimethyl-7,8-dihydro-4H-pyrazolo[1,5-a][1,3]diazepin-5(6H)-one (2.0 g, 92%) as yellow oil. LCMS RT=1.85 min, m/z=221.2 $[M+H]^+$.

LCMS (0 to 30% acetonitrile in water+0.05% ammonium hydroxide over 3 mins) retention time 1.85 min, ESI+ found [M+H]=221.2.

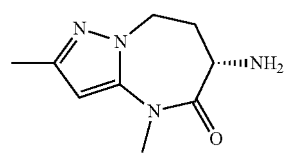

Step 7: (S)-6-amino-2,4-dimethyl-7,8-dihydro-4H-pyrazolo[1,5-a][1,3]diazepin-5(6H)-one A mixture of 6-azido-2,4-dimethyl-7,8-dihydro-4H-pyrazolo[1,5-a][1,3]diazepin-5(6H)-one (2.0 g, 9.1 mmol) and palladium on carbon (10%, 966 mg) in methyl alcohol (100 mL) was hydrogenated (15 psi) at 25° C. for 12 h and filtered. The filtrate was concentrated and the residue was purified by column chromatography on silica (solvent gradient: 0-10% methanol in dichloromethane) to afford the crude 6-amino-2,4-dimethyl-7,8-dihydro-4H-pyrazolo[1,5-a][1,3]diazepin-5(6H)-one (1.5 g). The crude was purified by SFC (SFC80; Chiralpak OD (250 mm*30 mm, 5 um); Supercritical $CO_2$/MeOH+$NH_3$*$H_2O$=20/20; 50 mL/min) to give:

Peak 1 (Rt=2.516 min):

(S)-6-amino-2,4-dimethyl-7,8-dihydro-4H-pyrazolo[1,5-a][1,3]diazepin-5(6H)-one (400 mg, 27%) as a yellow solid, used as is in the next step.

Peak 2 (Rt=2.757 min)

(R)-6-amino-2,4-dimethyl-7,8-dihydro-4H-pyrazolo[1,5-a][1,3]diazepin-5(6H)-one (350 mg, 23%) as a yellow solid.

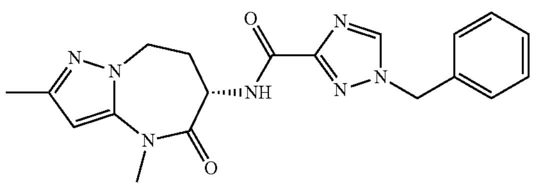 [SMILES: Cc1cc2n(n1)CC[C@H](NC(=O)c1ncn(Cc3ccccc3)n1)C(=O)N2C]

Step 8: (S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide A mixture of 1-benzyl-1,2,4-triazole-3-carboxylic acid (251 mg, 1.24 mmol), (S)-6-amino-2,4-dimethyl-7,8-dihydro-4H-pyrazolo[1,5-a][1,3]diazepin-5(6H)-one (200 mg, 1.03 mmol), 1-(3-dimethylaminopropyl)-3-ethylcarbodiimidehydrochloride (296 mg, 1.54 mmol) and 1-hydroxybenzotrizole (209 mg, 1.54 mmol) in N,N-dimethylformamide (10 mL) was stirred at 25° C. for 12 h. The solvent was removed under reduced pressure and the residue was purified by RP-HPLC (acetonitrile 17-47/0.05% HCl in water) to afford (S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide (221 mg, 56%) as a white solid.

$^1$H NMR (400 MHz, DMSO-$d_6$) δ 8.83 (s, 1H), 8.54 (d, J=8.0 Hz, 1H), 7.39-7.29 (m, 5H), 6.12 (s, 1H), 5.48 (s, 2H), 4.34-4.25 (m, 2H), 4.23-4.06 (m, 1H), 3.21 (s, 3H), 2.59-2.54 (m, 1H), 2.36-2.33 (m, 1H), 2.16 (s, 3H). LCMS RT=0.916 min, m/z=380.4 [M+H]$^+$.

LCMS (10 to 80% acetonitrile in water+0.05% ammonium bicarbonate over 3 mins) retention time 0.910 min, ESI+ found [M+H]=380.4.

SFC conditions: Column: Chiralcel AS-H 150×4.6 mm I.D., 3 um Mobile phase: A: $CO_2$ B: ethanol (0.05% DEA), Gradient: hold 5% for 0.5 min, then from 5% to 40% of B in 3.5 min and hold 40% for 2.5 min, then 5% of B for 1.5 min. Flow rate: 3 mL/min Column temperature: 40° C.

Data Based on the Above Scale-Up Experiments:

| Example Ki (μM) | Ex | Structure | Stereo | $^1$H NMR | MS (m/z) R.T. |
|---|---|---|---|---|---|
| Example A 0.016 | | 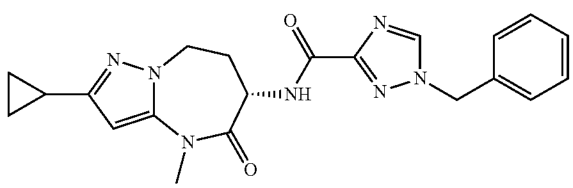 (S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide | Single Known Stereo-isomer | $^1$H NMR (400 MHz, DMSO-$d_6$) δ 8.83 (s, 1H), 8.54 (d, J = 7.8 Hz, 1H), 7.40-7.28 (m, 5H), 6.06 (s, 1H), 5.48 (s, 2H), 4.34-4.24 (m, 2H), 4.10-4.03 (m, 1H), 3.19 (s, 3H), 2.61-2.54 (m, 1H), 2.37-2.29 (m, 1H), 1.87-1.81 (m, 1H), 0.88-0.81 (m, 2H), 0.70-0.61 (m, 2H). | 406.2 0.978 min |
| Example B 0.013 | | 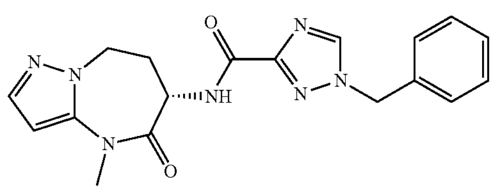 (S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide | Single Known Stereo-isomer | $^1$H NMR (400 MHz, DMSO-$d_6$) δ 8.82 (s, 1H), 8.54 (d, J = 8.0 Hz, 1H), 7.49 (d, J = 2.4 Hz, 1H), 7.40-7.27 (m, 5H), 6.34 (d, J = 1.6 Hz, 1H), 5.48 (s, 2H), 4.40-4.27 (m, 2H), 4.23-4.14 (m, 1H), 3.24 (s, 3H), 2.64-2.55 (m, 1H), 2.43-2.31 (m, 1H). | 366.0 0.702 min |
| Example C 0.022 | | 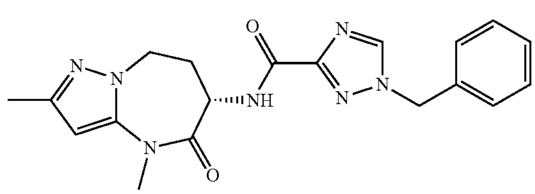 (S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide | Single Known Stereo-isomer | $^1$H NMR (400 MHz, DMSO-$d_6$) δ 8.83(s, 1H), 8.54 (d, J = 8.0 Hz, 1H), 7.39-7.29 (m, 5H), 6.12 (s, 1H), 5.48 (s, 2H), 4.34-4.25 (m, 2H), 4.23-4.06 (m, 1H), 3.21 (s, 3H), 2.59-2.54 (m, 1H), 2.36-2.33 (m, 1H), 2.16 (s, 3H). | 380.4 0.910 min |

All of the U.S. patents, U.S. patent application publications, U.S. patent applications, foreign patents, foreign patent applications and non patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:

1. A compound of formula I(a):

(I(a))

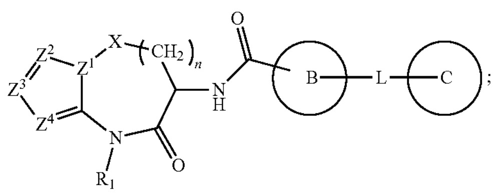

or a pharmaceutically acceptable salt thereof, wherein:

$R^1$ is selected from the group consisting of H and unsubstituted $C_1$-$C_4$ alkyl;

X is selected from the group consisting of $CH_2$, $C(CH_3)_2$, $CF_2$ and $CHCF_3$;

$Z^1$ is N;

n is 1;

$Z^2$, $Z^3$, and $Z^4$ are each independently selected from the group consisting of $CR^Z$ and N;

each $R^Z$ is independently selected from the group consisting of H, halogen, $C_1$-$C_6$ alkyl, $C_3$-$C_6$ cycloalkyl, $CH_2$($C_3$-$C_6$ cycloalkyl), $C_1$-$C_6$ haloalkyl, $C_1$-$C_6$ alkoxy, $C_1$-$C_6$ thioalkyl, phenyl and benzyl, wherein at least one of $Z^2$, $Z^3$ or $Z^4$ is $CR^Z$;

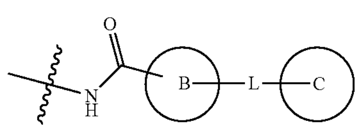

is selected from the group consisting of:

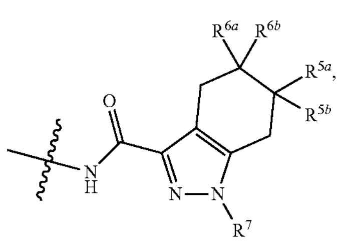

-continued

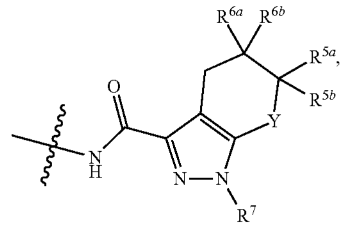

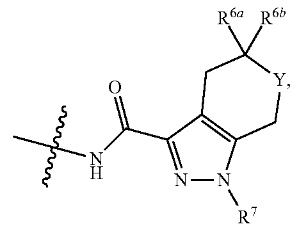

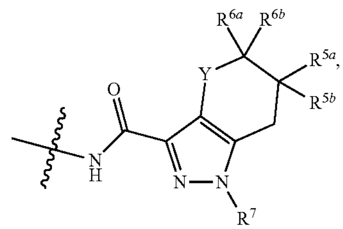

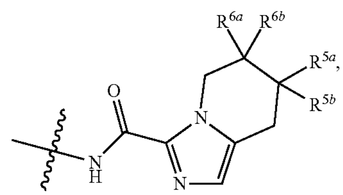

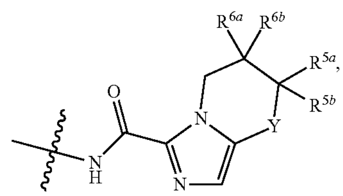

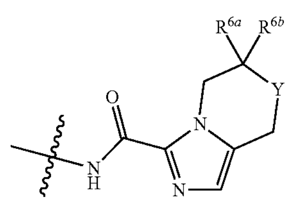

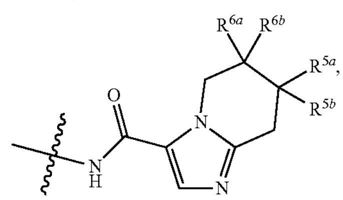

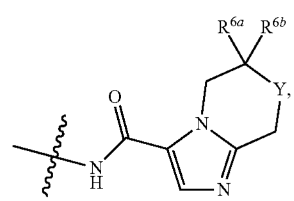

-continued
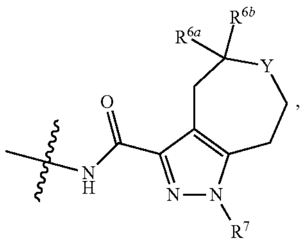
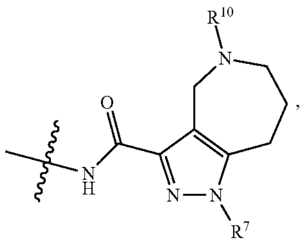
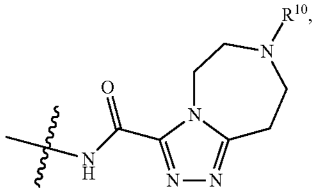
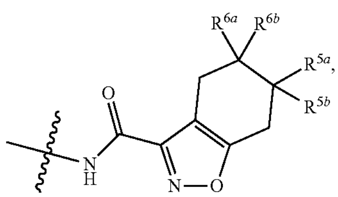
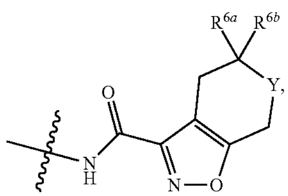
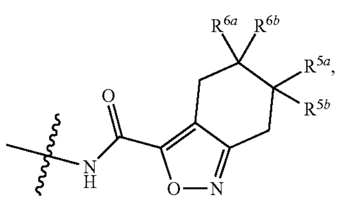
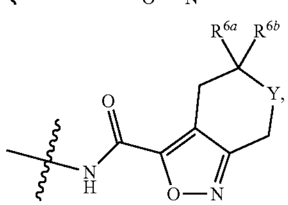
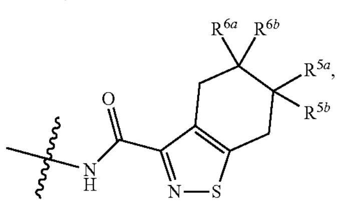
-continued
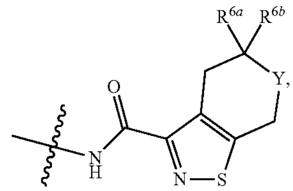
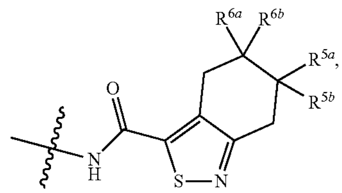
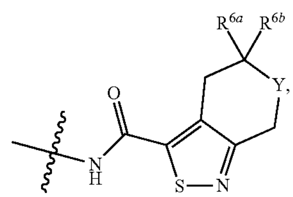
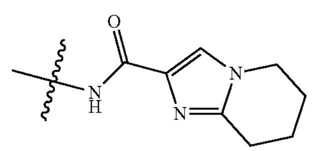
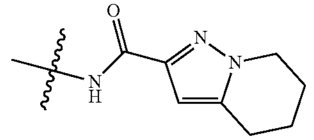
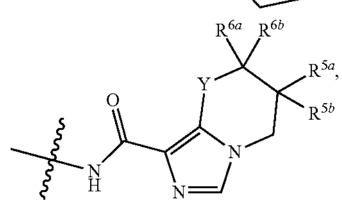
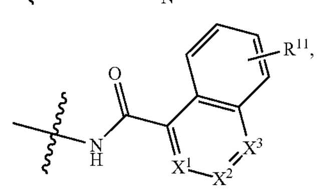
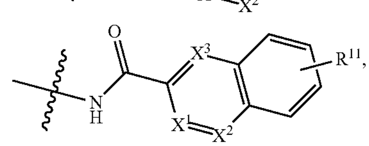
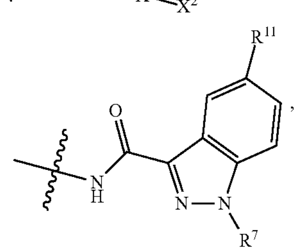

-continued
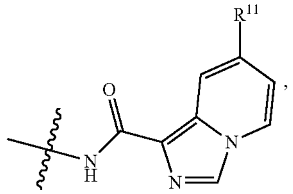
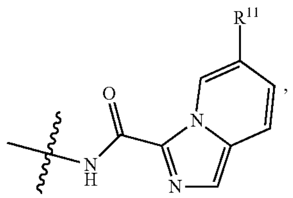
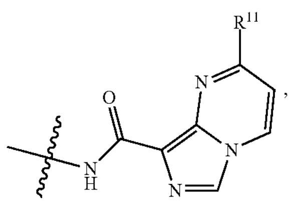
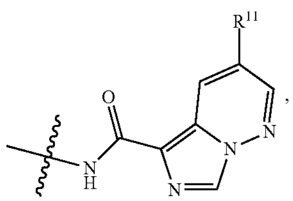
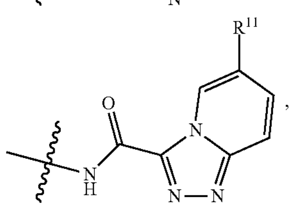
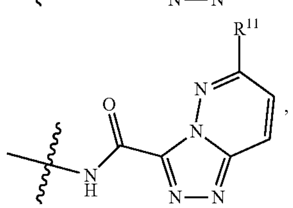
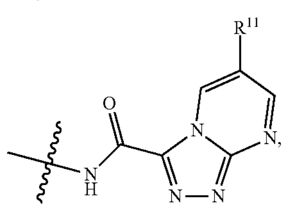
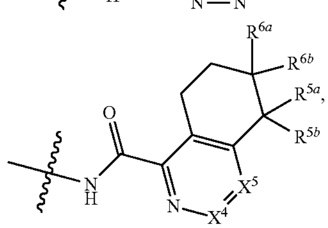
-continued
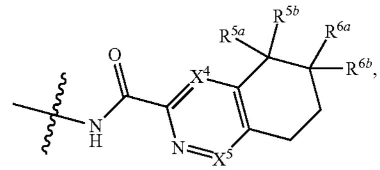
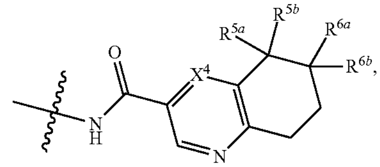
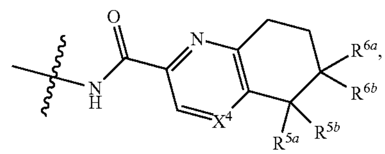
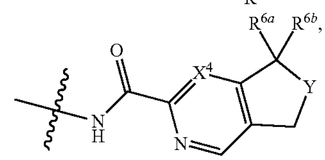
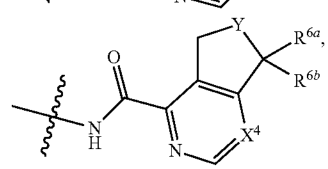
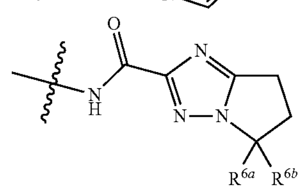
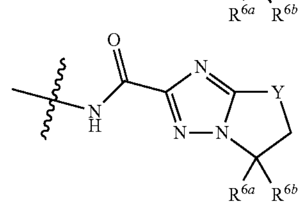
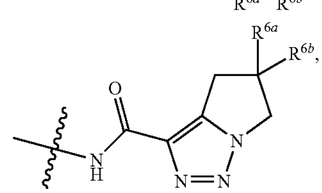
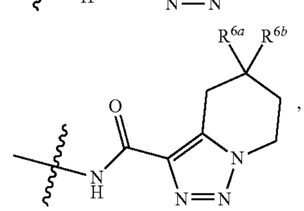
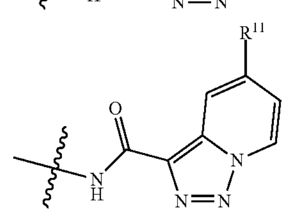

-continued
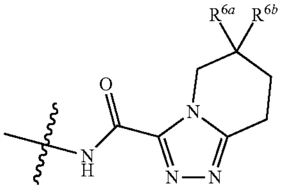
,
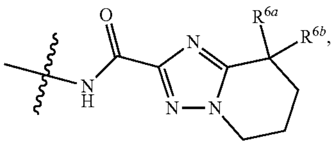
,
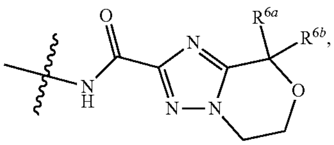
,
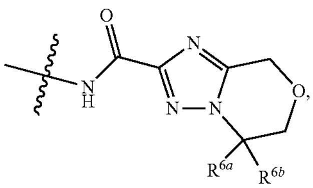
,
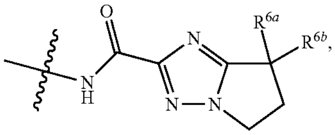
,
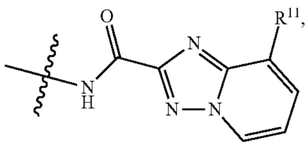
,
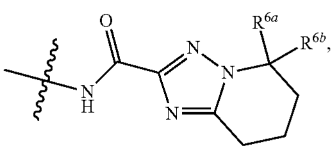
,
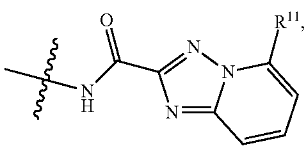
,
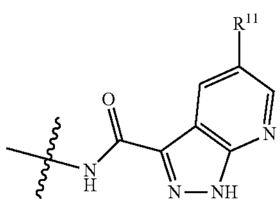
,
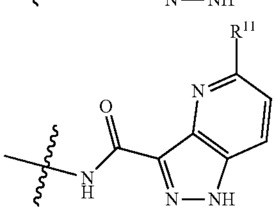
,
-continued
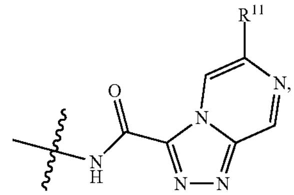
,
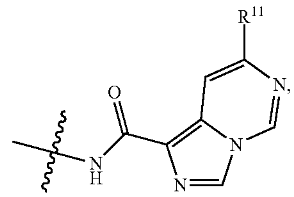
,
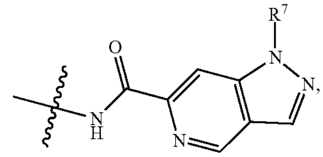
,
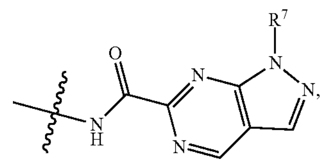
,
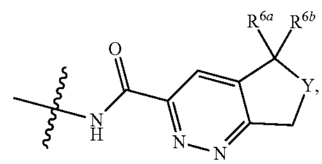
,
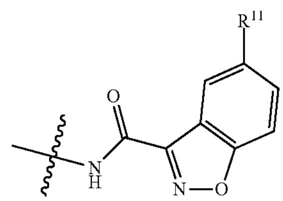
,
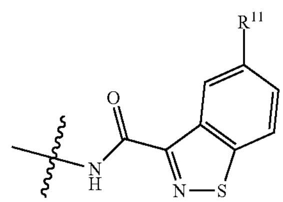
;
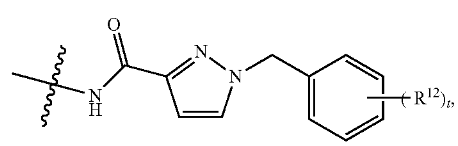
,
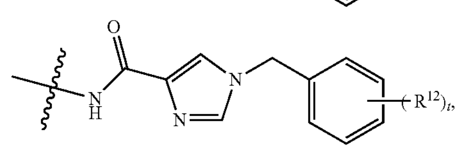
,
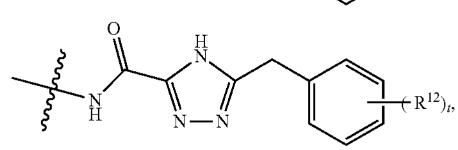
, -continued

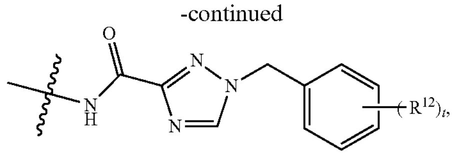

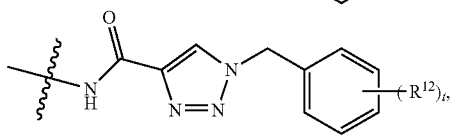

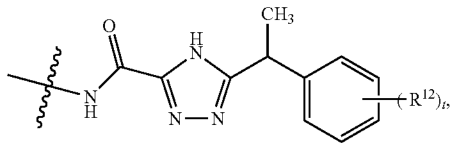

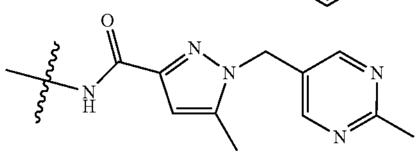

;

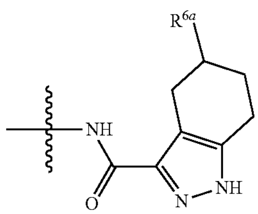

,

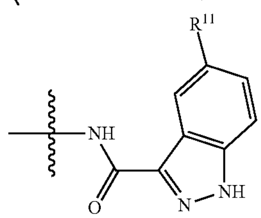

,

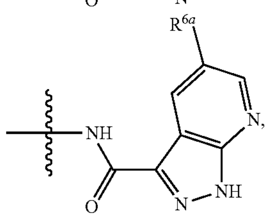

,

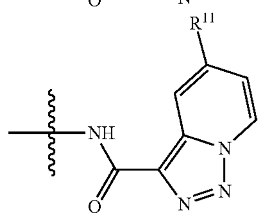

,

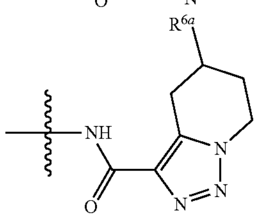

and

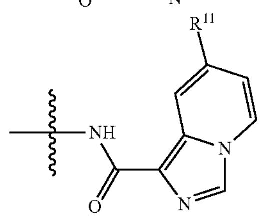

;

Y is selected from the group consisting of O, S, SO and $SO_2$;

$X^1$ is N, $X^2$ and $X^3$ are each independently N or CH, wherein 1 or 2 of $X^1$, $X^2$ and $X^3$ is N;

$X^4$ and $X^5$ are each independently N or CH;

$R^{5a}$ and $R^{5b}$ are each independently selected from the group consisting of H, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, phenyl, benzyl, —$CH_2$($C_3$-$C_6$ cycloalkyl) and 5 to 6 membered heteroaryl, wherein $R^{5a}$ and $R^{5b}$ together with the carbon to which they are attached may form a 4 membered cycloalkyl;

$R^{6a}$ and $R^{6b}$ are each independently selected from the group consisting of H, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, phenyl, benzyl, —$CH_2$($C_3$-$C_6$ cycloalkyl) and 5 to 6 membered heteroaryl, wherein $R^{6a}$ and $R^{6b}$ together with the carbon to which they are attached may form a 4 membered cycloalkyl, wherein when $R^{5a}$ and $R^{6a}$ are each H, $R^{5b}$ and $R^{6b}$ may together form a 4 membered cycloalkyl, and wherein only two of $R^{5a}$, $R^{5b}$, $R^{6a}$ and $R^{6b}$ may be other than H in each instance;

$R^7$ is selected from the group consisting of H and $C_1$-$C_4$ alkyl;

$R^{10}$ is selected from the group consisting of H, $C_1$-$C_6$ alkyl, $C_3$-$C_6$ cycloalkyl, $C_1$-$C_6$ haloalkyl, phenyl and benzyl;

$R^{11}$ is selected from the group consisting of H, halogen, $C_1$-$C_4$ alkyl and $C_1$-$C_4$ haloalkyl;

t is 0, 1 or 2; and $R^{12}$ is selected from the group consisting of halogen and methyl.

2. The compound of claim 1, or a pharmaceutically acceptable salt thereof, wherein:

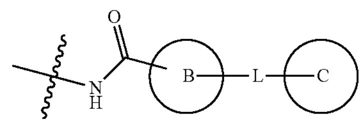

is selected from the group consisting of:

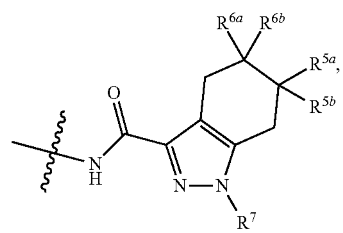

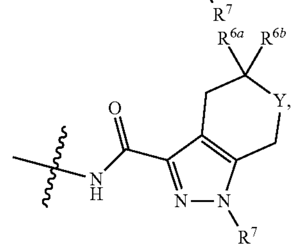

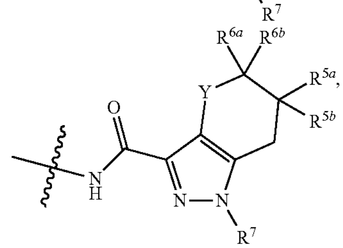

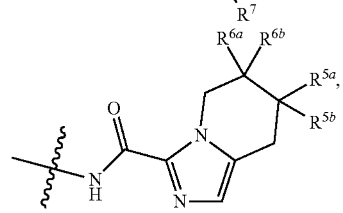

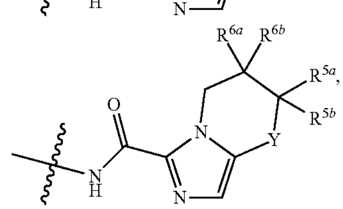

-continued
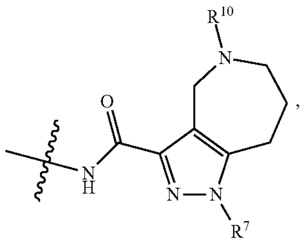
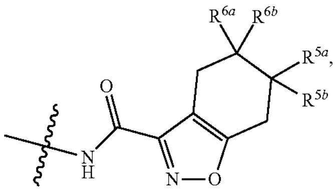
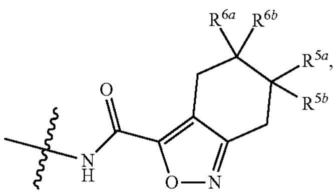
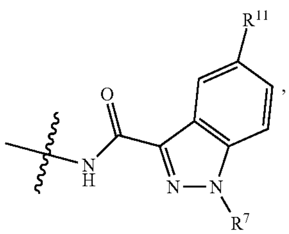
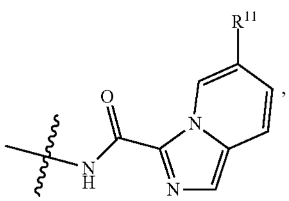
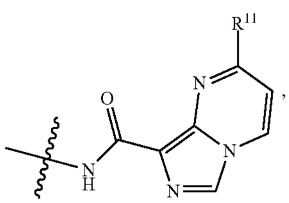
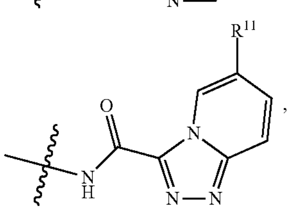
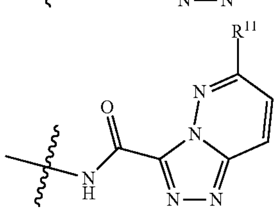
and
-continued
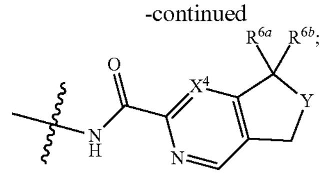
and
$R^{5a}$ and $R^{5b}$ are each H.
3. The compound of claim 1, or a pharmaceutically acceptable salt thereof, wherein Y is O.
4. The compound of claim 1, or a pharmaceutically acceptable salt thereof, wherein:
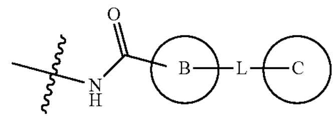
is selected from the group consisting of:
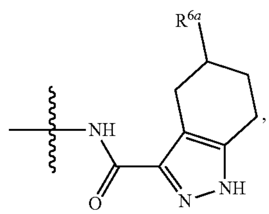
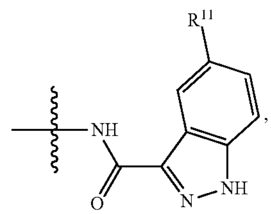
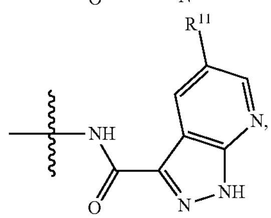
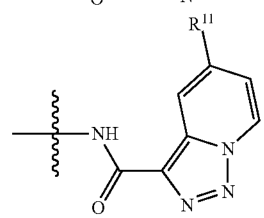
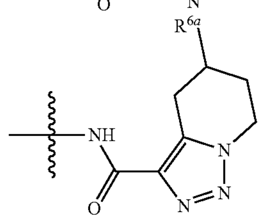
and
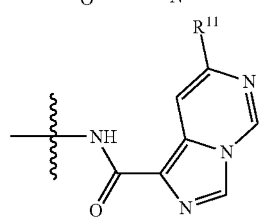
5. The compound of claim 1, or a pharmaceutically acceptable salt thereof, wherein:
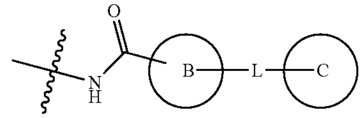
is
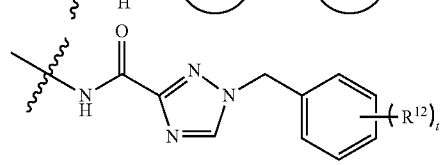

6. A compound of the formula:

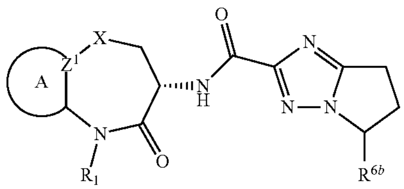

or

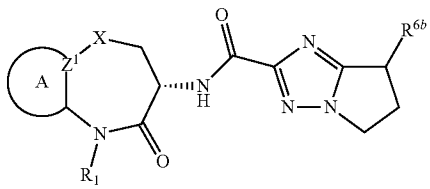

;

or a pharmaceutically acceptable salt thereof, wherein:

the A ring is 5 to 6 membered heteroaryl having 1 to 3 heteroatoms selected from the group consisting of nitrogen, oxygen and sulfur, wherein the A ring is optionally substituted with:

(a) 1 to 3 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl) and $CH_2CH_2$—($C_3$-$C_6$ cycloalkyl), wherein if a nitrogen atom in the A ring is substituted, the substituent is not halogen, $C_1$-$C_6$ alkoxy, $C_1$-$C_6$ haloalkoxy, $C_1$-$C_6$ thioalkyl or cyano;

(b) 1 substituent selected from the group consisting of $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2$—($C_5$-$C_6$ heteroaryl) and $CH_2CH_2$—($C_5$-$C_6$ heteroaryl), and optionally a second substituent selected from the group consisting of $C_1$-$C_6$ alkyl, $C_1$-$C_6$ haloalkyl, $C_1$-$C_6$ alkoxy and $C_1$-$C_6$ haloalkoxy; or (c) two adjacent substituents which together form phenyl, $C_5$-$C_6$ heteroaryl, $C_4$-$C_6$ heterocyclyl or $C_4$-$C_6$ cycloalkyl;

X is selected from the group consisting of $CH_2$, $C(CH_3)_2$, $CF_2$ and $CHCF_3$;

$Z^1$ is N;

$R^1$ is selected from the group consisting of H and unsubstituted $C_1$-$C_4$ alkyl; and $R^{6b}$ is selected from the group consisting of H, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, phenyl, mono- or di-fluorophenyl, benzyl, —$CH_2$($C_3$-$C_6$ cycloalkyl) and 5 to 6 membered heteroaryl.

7. A compound of the formula:

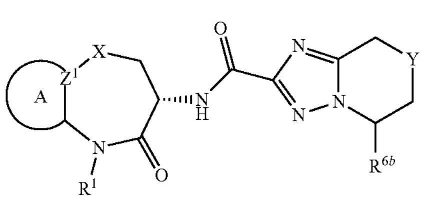

or

-continued

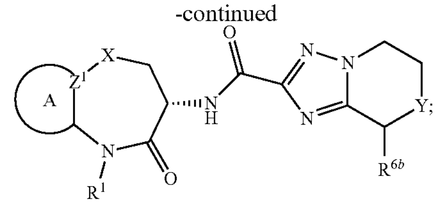

;

or a pharmaceutically acceptable salt thereof, wherein:

the A ring is 5 to 6 membered heteroaryl having 1 to 3 heteroatoms selected from the group consisting of nitrogen, oxygen and sulfur, wherein the A ring is optionally substituted with:

(a) 1 to 3 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl) and $CH_2CH_2$—($C_3$-$C_6$ cycloalkyl), wherein if a nitrogen atom in the A ring is substituted, the substituent is not halogen, $C_1$-$C_6$ alkoxy, $C_1$-$C_6$ haloalkoxy, $C_1$-$C_6$ thioalkyl, or cyano;

(b) 1 substituent selected from the group consisting of $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2$—($C_5$-$C_6$ heteroaryl) and $CH_2CH_2$—($C_5$-$C_6$ heteroaryl), and optionally a second substituent selected from the group consisting of $C_1$-$C_6$ alkyl, $C_1$-$C_6$ haloalkyl, $C_1$-$C_6$ alkoxy and $C_1$-$C_6$ haloalkoxy; or (c) two adjacent substituents which together form phenyl, $C_5$-$C_6$ heteroaryl, $C_4$-$C_6$ heterocyclyl or $C_4$-$C_6$ cycloalkyl;

X is selected from the group consisting of $CH_2$, $C(CH_3)_2$, $CF_2$ and $CHCF_3$;

$Z^1$ is N;

$R^1$ is selected from the group consisting of H and unsubstituted $C_1$-$C_4$ alkyl;

Y is NH or O; and $R^{6b}$ is selected from the group consisting of H, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, phenyl, mono- or di-fluorophenyl, benzyl, —$CH_2$($C_3$-$C_6$ cycloalkyl) and 5 to 6 membered heteroaryl.

8. The compound of claim 6, or a pharmaceutically acceptable salt thereof, wherein $R^1$ is H or methyl; and the A ring is 5 membered heteroaryl.

9. The compound of claim 7, or a pharmaceutically acceptable salt thereof, wherein $R^1$ is H or methyl; and the A ring is 5 membered heteroaryl.

10. A compound, or a pharmaceutically acceptable salt thereof, wherein the compound is selected from the group consisting of:

5-benzyl-N-(4-methyl-5-oxo-5,6,7,8-tetrahydro-4H-pyrazolo[1,5-a][1,3]diazepin-6-yl)-4H-1,2,4-triazole-3-carboxamide;

(S)-5-benzyl-N-(4-methyl-5-oxo-5,6,7,8-tetrahydro-4H-pyrazolo[1,5-a][1,3]diazepin-6-yl)-4H-1,2,4-triazole-3-carboxamide;

5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide;

5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide;

5-benzyl-N-(4-methyl-5-oxo-2-(trifluoromethyl)-5,6,7,8-tetrahydro-4H-pyrazolo[1,5-a][1,3]diazepin-6-yl)-4H-1,2,4-triazole-3-carboxamide;

5-benzyl-N-(3,4-dimethyl-5-oxo-5,6,7,8-tetrahydro-4H-pyrazolo[1,5-a][1,3]diazepin-6-yl)-4H-1,2,4-triazole-3-carboxamide;

(S)—N—((S)-4-methyl-5-oxo-5,6,7,8-tetrahydro-4H-pyrazolo[1,5-a][1,3]diazepin-6-y)-5-(trifluoromethyl)-4,5,6,7-tetrahydro-1H-indazole-3-carboxamide;

(R)—N—((S)-4-methyl-5-oxo-5,6,7,8-tetrahydro-4H-pyrazolo[1,5-a][1,3]diazepin-6-yl)-5-(trifluoromethyl)-4,5,6,7-tetrahydro-1H-indazole-3-carboxamide;

1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide;

(S)—N-(4-methyl-5-oxo-5,6,7,8-tetrahydro-4H-pyrazolo[1,5-a][1,3]diazepin-6-y)-7-(trifluoromethyl)imidazo[1,5-a]pyridine-1-carboxamide;

N-(2,4-dimethyl-5-oxo-5,6,7,8-tetrahydro-4H-pyrazolo[1,5-a][1,3]diazepin-6-y)-7-(trifluoromethyl)imidazo[1,5-a]pyridine-1-carboxamide;

(S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide;

(S)-5-benzyl-N-(2-cyclopropyl-4-methyl-5-oxo-5,6,7,8-tetrahydro-4H-pyrazolo[1,5-a][1,3]diazepin-6-yl)-4H-1,2,4-triazole-3-carboxamide;

(S)-5-benzyl-N-(4-methyl-5-oxo-2-(trifluoromethyl)-5,6,7,8-tetrahydro-4H-pyrazolo[1,5-a][1,3]diazepin-6-yl)-4H-1,2,4-triazole-3-carboxamide;

1-benzyl-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide;

(S)-1-benzyl-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide;

(S)-5-(4-fluorobenzyl)-N-(4-methyl-5-oxo-5,6,7,8-tetrahydro-4H-pyrazolo[1,5-a][1,3]diazepin-6-yl)-4H-1,2,4-triazole-3-carboxamide;

(S)-5-(2,3-difluorobenzyl)-N-(4-methyl-5-oxo-5,6,7,8-tetrahydro-4H-pyrazolo[1,5-a][1,3]diazepin-6-yl)-4H-1,2,4-triazole-3-carboxamide;

N—((S)-4-methyl-5-oxo-5,6,7,8-tetrahydro-4H-pyrazolo[1,5-a][1,3]diazepin-6-yl)-5-(1-phenylethyl)-4H-1,2,4-triazole-3-carboxamide;

(S)—N-(4-methyl-5-oxo-5,6,7,8-tetrahydro-4H-pyrazolo[1,5-a][1,3]diazepin-6-yl)-4-phenoxypicolinamide;

1-methyl-N—((S)-4-methyl-5-oxo-5,6,7,8-tetrahydro-4H-pyrazolo[1,5-a][1,3]diazepin-6-yl)-1-(2,2,2-trifluoroethyl)-1,3-dihydrofuro[3,4-c]pyridine-6-carboxamide;

1-benzyl-N-(3,4-dimethyl-5-oxo-5,6,7,8-tetrahydro-4H-pyrazolo[1,5-a][1,3]diazepin-6-yl)-1H-1,2,4-triazole-3-carboxamide;

5-benzyl-N-(1-methyl-2-oxo-2,3,4,5-tetrahydro-1H-[1,3]diazepino[1,2-b]indazol-3-yl)-4H-1,2,4-triazole-3-carboxamide;

5-benzyl-N-(1-methyl-2-oxo-2,3,4,5-tetrahydro-1H-benzo[4,5]imidazo[1,2-a][1,3]diazepin-3-yl)-4H-1,2,4-triazole-3-carboxamide;

1-benzyl-N-(1-methyl-2-oxo-2,3,4,5-tetrahydro-1H-[1,3]diazepino[1,2-b]indazol-3-yl)-1H-1,2,4-triazole-3-carboxamide;

1-benzyl-N-(1-methyl-2-oxo-2,3,4,5-tetrahydro-1H-benzo[4,5]imidazo[1,2-a][1,3]diazepin-3-yl)-1H-1,2,4-triazole-3-carboxamide;

(S)-1-benzyl-N-(2-cyclopropyl-4-methyl-5-oxo-5,6,7,8-tetrahydro-4H-pyrazolo[1,5-a][1,3]diazepin-6-yl)-1H-1,2,3-triazole-4-carboxamide;

(S)—N-(4-methyl-5-oxo-5,6,7,8-tetrahydro-4H-pyrazolo[1,5-a][1,3]diazepin-6-yl)-4'H,6'H-spiro[cyclopentane-1,5'-pyrrolo[1,2-c][1,2,3]triazole]-3'-carboxamide;

N—((S)-4-methyl-5-oxo-5,6,7,8-tetrahydro-4H-pyrazolo[1,5-a][1,3]diazepin-6-y)-5-phenyl-6,7-dihydro-5H-pyrrolo[1,2-b][1,2,4]triazole-2-carboxamide;

(R)—N—((S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide;

(S)—N—((S)-4-methyl-5-oxo-5,6,7,8-tetrahydro-4H-pyrazolo[1,5-a][1,3]diazepin-6-y)-5-phenyl-6,7-dihydro-5H-pyrrolo[1,2-b][1,2,4]triazole-2-carboxamide;

5-benzyl-N-(1-methyl-2-oxo-2,3,4,5,8,9,10,11-octahydro-1H-[1,3]diazepino[1,2-b]indazol-3-yl)-4H-1,2,4-triazole-3-carboxamide;

1-benzyl-N-(2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-(1-methyl-2-oxo-2,3,4,5,8,9,10,11-octahydro-1H-[1,3]diazepino[1,2-b]indazol-3-yl)-1H-1,2,3-triazole-4-carboxamide;

1-benzyl-N-(1-methyl-2-oxo-2,3,4,5,8,9,10,11-octahydro-1H-[1,3]diazepino[1,2-b]indazol-3-yl)-1H-1,2,4-triazole-3-carboxamide;

(5S)—N-(1-methyl-2-oxo-2,3,4,5,8,9,10,11-octahydro-1H-[1,3]diazepino[1,2-b]indazol-3-yl)-5-(trifluoromethyl)-4,5,6,7-tetrahydro-1H-indazole-3-carboxamide;

1-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-1H-1,2,4-triazole-3-carboxamide;

5-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-4H-1,2,4-triazole-3-carboxamide;

1-benzyl-N-(1-methyl-2-oxo-1,2,3,4,5,10-hexahydro-8H-thieno[3',4':3,4]pyrazolo[1,5-a][1,3]diazepin-3-yl)-1H-1,2,4-triazole-3-carboxamide;

5-benzyl-N-(1-methyl-2-oxo-1,2,3,4,5,10-hexahydro-8H-thieno[3',4':3,4]pyrazolo[1,5-a][1,3]diazepin-3-yl)-4H-1,2,4-triazole-3-carboxamide;

(S)-1-(3,4-difluorobenzyl)-N-(4-methyl-5-oxo-5,6,7,8-tetrahydro-4H-pyrazolo[1,5-a][1,3]diazepin-6-yl)-1H-imidazole-4-carboxamide;

1-benzyl-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(9-methyl-8-oxo-6,7,8,9-tetrahydro-5H-imidazo[1,2-a][1,3]diazepin-7-yl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-((R)-1-phenylethyl)-1H-1,2,4-triazole-3-carboxamide;

(S)-1-(cyclopentylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide;

(S)-1-(cyclopentylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-(cyclohexylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)—N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-((S)-1-phenylethyl)-1H-1,2,4-triazole-3-carboxamide;

(S)-1-benzyl-N-(3,4-dimethyl-5-oxo-5,6,7,8-tetrahydro-4H-pyrazolo[1,5-a][1,3]diazepin-6-yl)-1H-1,2,4-triazole-3-carboxamide;

(S)-1-(4-chlorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide;

5-benzyl-N-(9-methyl-8-oxo-6,7,8,9-tetrahydro-5H-imidazo[1,2-a][1,3]diazepin-7-yl)-4H-1,2,4-triazole-3-carboxamide;

(5S)—N-(9-methyl-8-oxo-6,7,8,9-tetrahydro-5H-imidazo[1,2-a][1,3]diazepin-7-y)-5-(trifluoromethyl)-4,5,6,7-tetrahydro-1H-indazole-3-carboxamide;

1-(3,4-difluorobenzyl)-N-(9-methyl-8-oxo-6,7,8,9-tetrahydro-5H-imidazo[1,2-a][1,3]diazepin-7-yl)-1H-pyrazole-3-carboxamide;

1-(3,4-difluorobenzyl)-N-(9-methyl-8-oxo-6,7,8,9-tetrahydro-5H-imidazo[1,2-a][1,3]diazepin-7-yl)-1H-imidazole-4-carboxamide;

1-benzyl-N-(9-methyl-8-oxo-6,7,8,9-tetrahydro-5H-imidazo[1,2-a][1,3]diazepin-7-yl)-1H-1,2,4-triazole-3-carboxamide;

1-benzyl-N-(9-methyl-8-oxo-6,7,8,9-tetrahydro-5H-imidazo[1,2-a][1,3]diazepin-7-yl)-1H-1,2,3-triazole-4-carboxamide;

1-benzyl-N-(1-methyl-2-oxo-2,3,4,5-tetrahydro-1H-imidazo[1,5-a][1,3]diazepin-3-yl)-1H-1,2,4-triazole-3-carboxamide;

1-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide;

5-benzyl-N-(4-methyl-5-oxo-2-phenyl-5,6,7,8-tetrahydro-4H-pyrazolo[1,5-a][1,3]diazepin-6-yl)-1H-1,2,4-triazole-3-carboxamide;

1-benzyl-N-(1,9-dimethyl-2-oxo-2,3,4,5-tetrahydro-1H-imidazo[1,5-a][1,3]diazepin-3-yl)-1H-1,2,4-triazole-3-carboxamide;

1-benzyl-N-(4-methyl-5-oxo-2-phenyl-5,6,7,8-tetrahydro-4H-pyrazolo[1,5-a][1,3]diazepin-6-yl)-1H-1,2,3-triazole-4-carboxamide;

(S)-1-(2,3-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-(3,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-(2,4-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)—N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(3,4-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

1-benzyl-N-(1,9-dimethyl-2-oxo-2,3,4,5-tetrahydro-1H-imidazo[1,5-a][1,3]diazepin-3-yl)-1H-1,2,3-triazole-4-carboxamide;

(1R)-1-ethyl-1-methyl-N-(9-methyl-8-oxo-6,7,8,9-tetrahydro-5H-imidazo[1,2-a][1,3]diazepin-7-yl)-1,3-dihydrofuro[3,4-c]pyridine-6-carboxamide;

1-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,4-triazole-3-carboxamide;

5-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,4-triazole-3-carboxamide;

(1R)-1-ethyl-1-methyl-N-(4-methyl-5-oxo-2-(tetrahydro-2H-pyran-4-yl)-5,6,7,8-tetrahydro-4H-pyrazolo[1,5-a][1,3]diazepin-6-yl)-1,3-dihydrofuro[3,4-c]pyridine-6-carboxamide;

1-benzyl-N-(4-methyl-5-oxo-2-(tetrahydro-2H-pyran-4-yl)-5,6,7,8-tetrahydro-4H-pyrazolo[1,5-a][1,3]diazepin-6-yl)-1H-1,2,3-triazole-4-carboxamide;

(S)-5-benzyl-N-(2,4-dimethyl-5-oxo-5,6,7,8-tetrahydro-4H-pyrazolo[1,5-a][1,3]diazepin-6-yl)-4H-1,2,4-triazole-3-carboxamide;

N-(2-cyclopropyl-4-methyl-5-oxo-5,6,7,8-tetrahydro-4H-pyrazolo[1,5-a][1,3]diazepin-6-yl)-1-((2-methylpyridin-4-yl)methyl)-1H-1,2,4-triazole-3-carboxamide;

(R)—N—((S)-2-cyclopropyl-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide;

1-((4,4-difluorocyclohexyl)methyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

1-(cyclobutylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

1-((3,3-difluorocyclobutyl)methyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

1-(4-chlorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

N-(2,4-dimethyl-5-oxo-5,6,7,8-tetrahydro-4H-pyrazolo[1,5-a][1,3]diazepin-6-yl)-1-(3,3,3-trifluoropropyl)-1H-1,2,4-triazole-3-carboxamide;

1-(cyclopentylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

1-(cyclohexylmethyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

N-(2-cyclopropyl-4-methyl-5-oxo-5,6,7,8-tetrahydro-4H-pyrazolo[1,5-a][1,3]diazepin-6-yl)-1-((tetrahydro-2H-pyran-4-yl)methyl)-1H-1,2,4-triazole-3-carboxamide;

N-(2-cyclopropyl-4-methyl-5-oxo-5,6,7,8-tetrahydro-4H-pyrazolo[1,5-a][1,3]diazepin-6-yl)-1-((4,4-difluorocyclohexyl)methyl)-1H-1,2,4-triazole-3-carboxamide;

1-(cyclobutylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide;

N-(2-cyclopropyl-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

N-(2-cyclopropyl-4-methyl-5-oxo-5,6,7,8-tetrahydro-4H-pyrazolo[1,5-a][1,3]diazepin-6-yl)-1-(3,3,3-trifluoropropyl)-1H-1,2,4-triazole-3-carboxamide;

N-(2-cyclopropyl-4-methyl-5-oxo-5,6,7,8-tetrahydro-4H-pyrazolo[1,5-a][1,3]diazepin-6-yl)-1-((6-methylpyridin-2-yl)methyl)-1H-1,2,4-triazole-3-carboxamide;

N-(2-cyclopropyl-4-methyl-5-oxo-5,6,7,8-tetrahydro-4H-pyrazolo[1,5-a][1,3]diazepin-6-yl)-1-(cyclopropylmethyl)-1H-1,2,4-triazole-3-carboxamide;

1-(cyclopentylmethyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide;

1-((2,2-difluorocyclopropyl)methyl)-N—((S)-2,4-dimethyl-5-oxo-5,6,7,8-tetrahydro-4H-pyrazolo[1,5-a][1,3]diazepin-6-yl)-1H-1,2,4-triazole-3-carboxamide;

(1R)—N-(1,9-dimethyl-2-oxo-2,3,4,5-tetrahydro-1H-imidazo[1,5-a][1,3]diazepin-3-yl)-1-ethyl-1-methyl-1,3-dihydrofuro[3,4-c]pyridine-6-carboxamide;

(3R)-3-ethyl-3-methyl-N-(4-methyl-5-oxo-2-phenyl-5,6,7,8-tetrahydro-4H-pyrazolo[1,5-a][1,3]diazepin-6-yl)-1,3-dihydrofuro[3,4-c]pyridine-6-carboxamide;

(3S)-3-ethyl-3-methyl-N-(4-methyl-5-oxo-2-phenyl-5,6,7,8-tetrahydro-4H-pyrazolo[1,5-a][1,3]diazepin-6-yl)-1,3-dihydrofuro[3,4-c]pyridine-6-carboxamide;

N—((S)-2,4-dimethyl-5-oxo-5,6,7,8-tetrahydro-4H-pyrazolo[1,5-a][1,3]diazepin-6-yl)-1-methyl-1-(2,2,2-trifluoroethyl)-1,3-dihydrofuro[3,4-c]pyridine-6-carboxamide;

N-(2,4-dimethyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

N-(2-cyclopropyl-4-methyl-5-oxo-5,6,7,8-tetrahydro-4H-pyrazolo[1,5-a][1,3]diazepin-6-yl)-1-((3,3-difluorocyclobutyl)methyl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-(1-phenylethyl)-1H-1,2,4-triazole-3-carboxamide;

(S)-1-(2,3-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

(S)-1-(3,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

(R)—N—((S)-2,4-dimethyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide;

(R)-1-ethyl-1-methyl-N—((S)-2,3,4-trimethyl-5-oxo-5,6,7,8-tetrahydro-4H-pyrazolo[1,5-a][1,3]diazepin-6-yl)-1,3-dihydrofuro[3,4-c]pyridine-6-carboxamide;

N-(2-cyclopropyl-4-methyl-5-oxo-5,6,7,8-tetrahydro-4H-pyrazolo[1,5-a][1,3]diazepin-6-yl)-1-((6-methylpyridin-3-yl)methyl)-1H-1,2,4-triazole-3-carboxamide;

(S)-1-(2,4-difluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

(S)-1-(4-fluorobenzyl)-N-(2,3,4-trimethyl-5-oxo-5,6,7,8-tetrahydro-4H-pyrazolo[1,5-a][1,3]diazepin-6-yl)-1H-1,2,4-triazole-3-carboxamide;

(S)-5-benzyl-N-(2-cyclopropyl-4-methyl-5-oxo-5,6,7,8-tetrahydro-4H-pyrazolo[1,5-a][1,3]diazepin-6-yl)-1,3,4-oxadiazole-2-carboxamide;

1-benzyl-N-((6S)-2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-((6R)-2-(2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

5-benzyl-N-((6S)-2-(2,2-difluorocyclopropyl)-4-methyl-5-oxo-5,6,7,8-tetrahydro-4H-pyrazolo[1,5-a][1,3]diazepin-6-yl)-4H-1,2,4-triazole-3-carboxamide;

5-benzyl-N-((6R)-2-(2,2-difluorocyclopropyl)-4-methyl-5-oxo-5,6,7,8-tetrahydro-4H-pyrazolo[1,5-a][1,3]diazepin-6-yl)-4H-1,2,4-triazole-3-carboxamide;

1-cyclopropyl-N—((S)-2,4-dimethyl-5-oxo-5,6,7,8-tetrahydro-4H-pyrazolo[1,5-a][1,3]diazepin-6-yl)-1-methyl-1,3-dihydrofuro[3,4-c]pyridine-6-carboxamide;

1-(4-chlorobenzyl)-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide;

(S)—N-(2,4-dimethyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide;

N—((S)-2-cyclopropyl-4-methyl-5-oxo-5,6,7,8-tetrahydro-4H-pyrazolo[1,5-a][1,3]diazepin-6-yl)-1-(1-(4-fluorophenyl)ethyl)-1H-1,2,4-triazole-3-carboxamide;

N—((S)-2-cyclopropyl-4-methyl-5-oxo-5,6,7,8-tetrahydro-4H-pyrazolo[1,5-a][1,3]diazepin-6-yl)-1-((2,2-difluorocyclopropyl)methyl)-1H-1,2,4-triazole-3-carboxamide;

N—((S)-2-cyclopropyl-4-methyl-5-oxo-5,6,7,8-tetrahydro-4H-pyrazolo[1,5-a][1,3]diazepin-6-yl)-1-(1-phenylethyl)-1H-1,2,4-triazole-3-carboxamide;

5-benzyl-N-(1-methyl-2-oxo-2,3,4,5-tetrahydro-1H-imidazo[1,5-a][1,3]diazepin-3-yl)-1H-1,2,4-triazole-3-carboxamide;

(1R)-1-ethyl-1-methyl-N-(1-methyl-2-oxo-2,3,4,5-tetrahydro-1H-imidazo[1,5-a][1,3]diazepin-3-yl)-1,3-dihydrofuro[3,4-c]pyridine-6-carboxamide;

1-benzyl-N-(1-methyl-2-oxo-2,3,4,5-tetrahydro-1H-imidazo[1,5-a][1,3]diazepin-3-yl)-1H-1,2,3-triazole-4-carboxamide;

(S)-1-benzyl-N-(1-methyl-2-oxo-2,3,4,5-tetrahydro-1H-imidazo[1,5-a][1,3]diazepin-3-yl)-1H-1,2,4-triazole-3-carboxamide;

(R)—N-(2-cyclopropyl-4-methyl-5-oxo-5,6,7,8-tetrahydro-4H-pyrazolo[1,5-a][1,3]diazepin-6-yl)-1-(2,4-difluorobenzyl)-1H-1,2,4-triazole-3-carboxamide;

(S)-5-benzyl-N-(2,3,4-trimethyl-5-oxo-5,6,7,8-tetrahydro-4H-pyrazolo[1,5-a][1,3]diazepin-6-yl)-4H-1,2,4-triazole-3-carboxamide;

(S)-1-(2,6-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,6-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(3,5-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,5-difluorobenzyl)-1H-1,2,4-triazole-3-carboxamide;

(S)-1-(2,5-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,3-dichlorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,4-dichlorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-((1-methylcyclopropyl)methyl)-1H-1,2,4-triazole-3-carboxamide;

1-(2,3-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(2,3-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(3,4-difluorobenzyl)-N—((S)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(3,4-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(2,4-difluorobenzyl)-N—((R)-2-((R)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

N—((S)-2-((R)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

N—((R)-2-((R)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

1-(2,3-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(3,4-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

1-(2,4-difluorobenzyl)-N—((S)-2-((S)-2,2-difluorocyclopropyl)-4-methyl-5-oxo-5,6,7,8-tetrahydro-4H-pyrazolo[1,5-a][1,3]diazepin-6-yl)-1H-1,2,4-triazole-3-carboxamide;

N—((S)-2-((S)-2,2-difluorocyclopropyl)-4-methyl-5-oxo-5,6,7,8-tetrahydro-4H-pyrazolo[1,5-a][1,3]diazepin-6-yl)-1-(4-fluorobenzyl)-1H-1,2,4-triazole-3-carboxamide;

(R)—N—((R)-2-((R)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide;

(R)—N—((S)-2-((S)-2,2-difluorocyclopropyl)-4-methyl-5-oxo-5,6,7,8-tetrahydro-4H-pyrazolo[1,5-a][1,3]diazepin-6-yl)-1-ethyl-1-methyl-1,3-dihydrofuro[3,4-c]pyridine-6-carboxamide;

N—((S)-2,4-dimethyl-5-oxo-5,6,7,8-tetrahydro-4H-pyrazolo[1,5-a][1,3]diazepin-6-yl)-7-ethyl-7-methyl-5,7-dihydrofuro[3,4-d]pyrimidine-2-carboxamide;

(R)—N-(2,4-dimethyl-5-oxo-5,6,7,8-tetrahydro-4H-pyrazolo[1,5-a][1,3]diazepin-6-y)-5-(4-fluorobenzyl)-4H-1,2,4-triazole-3-carboxamide;

(S)-5-(4-fluorobenzyl)-N-(2,3,4-trimethyl-5-oxo-5,6,7,8-tetrahydro-4H-pyrazolo[1,5-a][1,3]diazepin-6-yl)-4H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-1-(2,3-difluorobenzyl)-1H-1,2,4-triazole-3-carboxamide;

(S)—N-(2-cyclopropyl-4-methyl-5-oxo-5,6,7,8-tetrahydro-4H-pyrazolo[1,5-a][1,3]diazepin-6-yl)-5-(4-fluorobenzyl)-4H-1,2,4-triazole-3-carboxamide;

1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide;

(S)—N-(4-methyl-5-oxo-5,6,7,8-tetrahydro-4H-pyrazolo[1,5-a][1,3]diazepin-6-y)-7-(trifluoromethyl)imidazo[1,5-a]pyridine-1-carboxamide;

N-(2,4-dimethyl-5-oxo-5,6,7,8-tetrahydro-4H-pyrazolo[1,5-a][1,3]diazepin-6-y)-7-(trifluoromethyl)imidazo[1,5-a]pyridine-1-carboxamide;

1-[(4-fluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide;

1-[(2,4-difluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide;

1-[(3,4-difluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide;

1-[(2,3-difluorophenyl)methyl]-N-[rac-(6S)-4-methyl-5-oxo-7,8-dihydro-6H-pyrazolo[1,5-a][1,3]diazepin-6-yl]-1,2,4-triazole-3-carboxamide;

1-[(2,6-difluorophenyl)methyl]-N-[(6S)-4-methyl-5-oxo-7,8-dihydro-6H-pyrazolo[1,5-a][1,3]diazepin-6-yl]-1,2,4-triazole-3-carboxamide;

(5S)—N-[(6S)-4-methyl-5-oxo-7,8-dihydro-6H-pyrazolo[1,5-a][1,3]diazepin-6-yl]-5-(trifluoromethyl)-6,7-dihydro-5H-pyrrolo[1,2-b][1,2,4]triazole-2-carboxamide;

5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

5-ethyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

(5S)-5-isopropyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

(5R)—N-[(6S)-4-methyl-5-oxo-7,8-dihydro-6H-pyrazolo[1,5-a][1,3]diazepin-6-yl]-5-phenyl-6,7-dihydro-5H-pyrrolo[1,2-b][1,2,4]triazole-2-carboxamide;

(5S)—N-[(6S)-4-methyl-5-oxo-7,8-dihydro-6H-pyrazolo[1,5-a][1,3]diazepin-6-yl]-5-phenyl-6,7-dihydro-5H-pyrrolo[1,2-b][1,2,4]triazole-2-carboxamide;

1-benzyl-N-(2-isopropenyl-4-methyl-5-oxo-7,8-dihydro-6H-pyrazolo[1,5-a][1,3]diazepin-6-yl)-1,2,4-triazole-3-carboxamide;

(S)—N-(2-acetyl-4-methyl-5-oxo-5,6,7,8-tetrahydro-4H-pyrazolo[1,5-a][1,3]diazepin-6-yl)-1-benzyl-1H-1,2,4-triazole-3-carboxamide;

1-benzyl-N-((6S)-2-(1-hydroxyethyl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-((6S)-2-(1-hydroxyethyl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide;

1-benzyl-N-[2-(1-fluoro-1-methyl-ethyl)-4-methyl-5-oxo-7,8-dihydro-6H-pyrazolo[1,5-a][1,3]diazepin-6-yl]-1,2,4-triazole-3-carboxamide;

1-benzyl-N-[2-(1,1-difluoroethyl)-4-methyl-5-oxo-7,8-dihydro-6H-pyrazolo[1,5-a][1,3]diazepin-6-yl]-1,2,4-triazole-3-carboxamide;

1-benzyl-N-[2-(1-hydroxy-1-methyl-ethyl)-4-methyl-5-oxo-7,8-dihydro-6H-pyrazolo[1,5-a][1,3]diazepin-6-yl]-1,2,4-triazole-3-carboxamide;

5-ethyl-N-[rac-(6S)-4-methyl-5-oxo-7,8-dihydro-6H-pyrazolo[1,5-a][1,3]diazepin-6-yl]-[1,2,4]triazolo[1,5-a]pyridine-2-carboxamide;

N-[(6S)-4-methyl-5-oxo-7,8-dihydro-6H-pyrazolo[1,5-a][1,3]diazepin-6-yl]-5-phenyl-[1,2,4]triazolo[1,5-a]pyridine-2-carboxamide;

5-ethyl-N-[(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

5-phenyl-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

5-cyclohexyl-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

5-(2,5-difluorophenyl)-N-[(6S)-4-methyl-5-oxo-7,8-dihydro-6H-pyrazolo[1,5-a][1,3]diazepin-6-yl]-[1,2,4]triazolo[1,5-a]pyridine-2-carboxamide;

(S)—N—((S)-4-methyl-5-oxo-5,6,7,8-tetrahydro-4H-pyrazolo[1,5-a][1,3]diazepin-6-y)-5-phenyl-5,6,7,8-tetrahydro-[1,2,4]triazolo[1,5-a]pyridine-2-carboxamide;

rac-(5R)-5-phenyl-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

5-(2-fluorophenyl)-N-[(6S)-4-methyl-5-oxo-7,8-dihydro-6H-pyrazolo[1,5-a][1,3]diazepin-6-yl]-[1,2,4]triazolo[1,5-a]pyridine-2-carboxamide;

5-(2-fluorophenyl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

5-(2,5-difluorophenyl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

5-(3-furyl)-N-[rac-(6S)-4-methyl-5-oxo-7,8-dihydro-6H-pyrazolo[1,5-a][1,3]diazepin-6-yl]-[1,2,4]triazolo[1,5-a]pyridine-2-carboxamide;

N-[(6S)-4-methyl-5-oxo-7,8-dihydro-6H-pyrazolo[1,5-a][1,3]diazepin-6-yl]-5-tetrahydrofuran-3-yl-5,6,7,8-tetrahydro-[1,2,4]triazolo[1,5-a]pyridine-2-carboxamide;

7-phenyl-N-[rac-(6S)-4-methyl-5-oxo-7,8-dihydro-6H-pyrazolo[1,5-a][1,3]diazepin-6-yl]-1,3-benzothiazole-2-carboxamide;

N-[(6S)-4-methyl-5-oxo-7,8-dihydro-6H-pyrazolo[1,5-a][1,3]diazepin-6-yl]-5-(1-methylpyrazol-4-yl)-[1,2,4]triazolo[1,5-a]pyridine-2-carboxamide;

5-(2,6-difluorophenyl)-N-[(6S)-4-methyl-5-oxo-7,8-dihydro-6H-pyrazolo[1,5-a][1,3]diazepin-6-yl]-[1,2,4]triazolo[1,5-a]pyridine-2-carboxamide;

5-(3,6-dihydro-2H-pyran-4-yl)-N-[(6S)-4-methyl-5-oxo-7,8-dihydro-6H-pyrazolo[1,5-a][1,3]diazepin-6-yl]-[1,2,4]triazolo[1,5-a]pyridine-2-carboxamide;

5-(2,6-difluorophenyl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

5-(1-methylpyrazol-4-yl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

rac-(5S)-5-(2,6-difluorophenyl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

rac-(5R)-5-(2,6-difluorophenyl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

rac-(5R)-5-(1-methylpyrazol-4-yl)-N-[rac-(6S)-4-methyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

1-benzyl-N-[4-methyl-2-(morpholinomethyl)-5-oxo-7,8-dihydro-6H-pyrazolo[1,5-a][1,3]diazepin-6-yl]-1,2,4-triazole-3-carboxamide;

1-benzyl-N-[2-[(3,3-difluoropyrrolidin-1-yl)methyl]-4-methyl-5-oxo-7,8-dihydro-6H-pyrazolo[1,5-a][1,3]diazepin-6-yl]-1,2,4-triazole-3-carboxamide;

1-benzyl-N-[(6S)-4-methyl-2-(morpholinomethyl)-5-oxo-7,8-dihydro-6H-pyrazolo[1,5-a][1,3]diazepin-6-yl]-1,2,4-triazole-3-carboxamide;

1-benzyl-N-[2-[(3-fluoroazetidin-1-yl)methyl]-4-methyl-5-oxo-7,8-dihydro-6H-pyrazolo[1,5-a][1,3]diazepin-6-yl]-1,2,4-triazole-3-carboxamide;

1-benzyl-N-[2-[(3-methoxyazetidin-1-yl)methyl]-4-methyl-5-oxo-7,8-dihydro-6H-pyrazolo[1,5-a][1,3]diazepin-6-yl]-1,2,4-triazole-3-carboxamide;

(S)-5-benzyl-N-(1-methyl-9,9-dioxido-2-oxo-1,2,3,4,5,10-hexahydro-8H-thieno[3',4':3,4]pyrazolo[1,5-a][1,3]diazepin-3-yl)-4H-1,2,4-triazole-3-carboxamide;

1-benzyl-N-(2-cyclobutyl-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-(2-isopropyl-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-(2-(cyclopropylmethyl)-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2-isopropyl-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2-(cyclopropylmethyl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-(2-ethyl-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-(2-isopropoxy-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-5-methyl-N-(4-methyl-5-oxo-5,6,7,8-tetrahydro-4H-pyrazolo[1,5-a][1,3]diazepin-6-yl)-1H-1,2,4-triazole-3-carboxamide;

N-(2-ethyl-4-methyl-5-oxo-5,6,7,8-tetrahydro-4H-pyrazolo[1,5-a][1,3]diazepin-6-yl)-1-(2-fluorobenzyl)-1H-1,2,4-triazole-3-carboxamide;

(S)—N-(2-ethyl-4-methyl-5-oxo-5,6,7,8-tetrahydro-4H-pyrazolo[1,5-a][1,3]diazepin-6-yl)-1-(2-fluorobenzyl)-1H-1,2,4-triazole-3-carboxamide;

(R)-5-(2-fluorophenyl)-N—((S)-4-methyl-5-oxo-5,6,7,8-tetrahydro-4H-pyrazolo[1,5-a][1,3]diazepin-6-yl)-6,7-dihydro-5H-pyrrolo[1,2-b][1,2,4]triazole-2-carboxamide;

(S)-5-(2-fluorophenyl)-N—((S)-4-methyl-5-oxo-5,6,7,8-tetrahydro-4H-pyrazolo[1,5-a][1,3]diazepin-6-yl)-6,7-dihydro-5H-pyrrolo[1,2-b][1,2,4]triazole-2-carboxamide;

N-(6S)-2-cyclopropyl-4-methyl-5-oxo-7,8-dihydro-6H-pyrazolo[1,5-a][1,3]diazepin-6-yl-1-(tetrahydrofuran-2-ylmethyl)-1,2,4-triazole-3-carboxamide;

1-[(3,5-difluorophenyl)methyl]-N-[rac-(6S)-2,4-dimethyl-5-oxo-7,8-dihydro-6H-pyrazolo[1,5-a][1,3]diazepin-6-yl]-1,2,4-triazole-3-carboxamide;

1-[(2,3-dichlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-[(2,4-dichlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide;

N-(6S)-2,4-dimethyl-5-oxo-7,8-dihydro-6H-pyrazolo[1,5-a][1,3]diazepin-6-yl-1-(tetrahydrofuran-2-ylmethyl)-1,2,4-triazole-3-carboxamide;

N-(6S)-2,4-dimethyl-5-oxo-7,8-dihydro-6H-pyrazolo[1,5-a][1,3]diazepin-6-yl-1-(tetrahydropyran-3-ylmethyl)-1,2,4-triazole-3-carboxamide;

N-(6S)-2,4-dimethyl-5-oxo-7,8-dihydro-6H-pyrazolo[1,5-a][1,3]diazepin-6-yl-1-(tetrahydropyran-2-ylmethyl)-1,2,4-triazole-3-carboxamide;

N-(6S)-2-cyclopropyl-4-methyl-5-oxo-7,8-dihydro-6H-pyrazolo[1,5-a][1,3]diazepin-6-yl-1-(tetrahydropyran-2-ylmethyl)-1,2,4-triazole-3-carboxamide;

N-(6S)-2-cyclopropyl-4-methyl-5-oxo-7,8-dihydro-6H-pyrazolo[1,5-a][1,3]diazepin-6-yl-1-(tetrahydropyran-3-ylmethyl)-1,2,4-triazole-3-carboxamide;

N-(6S)-2,4-dimethyl-5-oxo-7,8-dihydro-6H-pyrazolo[1,5-a][1,3]diazepin-6-yl-1-(tetrahydrofuran-3-ylmethyl)-1,2,4-triazole-3-carboxamide;

N-(6S)-2-cyclopropyl-4-methyl-5-oxo-7,8-dihydro-6H-pyrazolo[1,5-a][1,3]diazepin-6-yl-1-(tetrahydrofuran-3-ylmethyl)-1,2,4-triazole-3-carboxamide;

N—[(S)-2,4-dimethyl-5-oxo-7,8-dihydro-6H-pyrazolo[1,5-a][1,3]diazepin-6-yl]-1-(((1R,3S)-3-trifluoromethylcyclobutyl)methyl)-1H-1,2,4-triazole-3-carboxamide;

5-[(4-fluorophenyl)methyl]-N-(6S)-2,4-dimethyl-5-oxo-7,8-dihydro-6H-pyrazolo[1,5-a][1,3]diazepin-6-yl-4H-1,2,4-triazole-3-carboxamide;

7-methyl-N-[(6S)-2,4-dimethyl-5-oxo-7,8-dihydro-6H-pyrazolo[1,5-a][1,3]diazepin-6-yl]-7-(2,2,2-trifluoroethyl)-5H-furo[3,4-d]pyrimidine-2-carboxamide;

5-[(2,3-difluorophenyl)methyl]-N-(6S)-2,3,4-trimethyl-5-oxo-7,8-dihydro-6H-pyrazolo[1,5-a][1,3]diazepin-6-yl-4H-1,2,4-triazole-3-carboxamide;

1-[(3-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide;

N—[(S)-2,4-dimethyl-5-oxo-7,8-dihydro-6H-pyrazolo[1,5-a][1,3]diazepin-6-yl]-1-(((1S,3R)-3-trifluoromethylcyclobutyl)methyl)-1H-1,2,4-triazole-3-carboxamide;

N—[(S)-4-methyl-5-oxo-7,8-dihydro-6H-pyrazolo[1,5-a][1,3]diazepin-6-yl]-1-(((1S,3R)-3-trifluoromethylcyclobutyl)methyl)-1H-1,2,4-triazole-3-carboxamide;

N—[(S)-4-methyl-5-oxo-7,8-dihydro-6H-pyrazolo[1,5-a][1,3]diazepin-6-yl]-1-(((1R,3S)-3-trifluoromethylcyclobutyl)methyl)-1H-1,2,4-triazole-3-carboxamide;

1-[(1-methylcyclopentyl)methyl]-N-(6S)-2,4-dimethyl-5-oxo-7,8-dihydro-6H-pyrazolo[1,5-a][1,3]diazepin-6-yl-1,2,4-triazole-3-carboxamide;

N—((S)-4-methyl-5-oxo-5,6,7,8-tetrahydro-4H-pyrazolo[1,5-a][1,3]diazepin-6-yl)-1-(((1S,3R)-3-methylcyclobutyl)methyl)-1H-1,2,4-triazole-3-carboxamide;

N—((S)-4-methyl-5-oxo-5,6,7,8-tetrahydro-4H-pyrazolo[1,5-a][1,3]diazepin-6-yl)-1-(((1R,3S)-3-methylcyclobutyl)methyl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-(((1R,3S)-3-methylcyclobutyl)methyl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-(((1S,3R)-3-methylcyclobutyl)methyl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-(((1R,3R)-3-ethylcyclobutyl)methyl)-1H-1,2,4-triazole-3-carboxamide;

N—((S)-2,4-dimethyl-5-oxo-5,6,7,8-tetrahydro-4H-pyrazolo[1,5-a][1,3]diazepin-6-yl)-1-(((1S,3S)-3-ethylcyclobutyl)methyl)-1H-1,2,4-triazole-3-carboxamide;

N—((S)-4-methyl-5-oxo-5,6,7,8-tetrahydro-4H-pyrazolo[1,5-a][1,3]diazepin-6-yl)-1-(((1R,3R)-3-ethylcyclobutyl)methyl)-1H-1,2,4-triazole-3-carboxamide;

N—((S)-4-methyl-5-oxo-5,6,7,8-tetrahydro-4H-pyrazolo[1,5-a][1,3]diazepin-6-yl)-1-(((1S,3S)-3-ethylcyclobutyl)methyl)-1H-1,2,4-triazole-3-carboxamide;

1-[(2,5-difluorophenyl)methyl]-N-(3R)-1,9-dimethyl-2-oxo-4,5-dihydro-3H-imidazo[1,5-a][1,3]diazepin-3-yl-1,2,4-triazole-3-carboxamide;

1-benzyl-N-(3R)-1,9-dimethyl-2-oxo-4,5-dihydro-3H-imidazo[1,5-a][1,3]diazepin-3-yl-1,2,4-triazole-3-carboxamide;

1-[(2,5-difluorophenyl)methyl]-N-[(7S)-9-methyl-8-oxo-6,7-dihydro-5H-imidazo[1,2-a][1,3]diazepin-7-yl]-1,2,4-triazole-3-carboxamide;

1-[(2,5-difluorophenyl)methyl]-N-[(3R)-1-methyl-2-oxo-4,5-dihydro-3H-imidazo[1,5-a][1,3]diazepin-3-yl]-1,2,4-triazole-3-carboxamide;

N-[(6S)-2,4-dimethyl-5-oxo-7,8-dihydro-6H-pyrazolo[1,5-a][1,3]diazepin-6-yl]spiro[5H-furo[3,4-d]pyrimidine-7,4'-tetrahydropyran]-2-carboxamide;

5-[(2,3-difluorophenyl)methyl]-N-(6S)-2,4-dimethyl-5-oxo-7,8-dihydro-6H-pyrazolo[1,5-a][1,3]diazepin-6-yl-4H-1,2,4-triazole-3-carboxamide;

5-[(2,3-difluorophenyl)methyl]-N-(6S)-2-cyclopropyl-4-methyl-5-oxo-7,8-dihydro-6H-pyrazolo[1,5-a][1,3]diazepin-6-yl-4H-1,2,4-triazole-3-carboxamide;

1-[(2-fluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-[(3-fluorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-[(2-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-[(3-chlorophenyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-[(2-chlorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;

1-[(2,3-difluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

5-[(2,3-difluorophenyl)methyl]-N-(6S)-4-methyl-5-oxo-2-(trifluoromethyl)-7,8-dihydro-6H-pyrazolo[1,5-a][1,3]diazepin-6-yl-4H-1,2,4-triazole-3-carboxamide;

1-[(4-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

1-[(2-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

1-[(3-fluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

1-[(2-chlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

1-[(2,4-difluorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

1-[(2-fluorophenyl)methyl]-N-[rac-(6S)-2-cyclopropyl-4-methyl-5-oxo-7,8-dihydro-6H-pyrazolo[1,5-a][1,3]diazepin-6-yl]-1,2,4-triazole-3-carboxamide;

1-[(3-fluorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;

1-[(4-chlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

1-[(3-chlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

1-[(2,3-dichlorophenyl)methyl]-N-(6S)-4-methyl-5-oxo-2-(trifluoromethyl)-7,8-dihydro-6H-pyrazolo[1,5-a][1,3]diazepin-6-yl-1,2,4-triazole-3-carboxamide;

1-benzyl-N-(2,9-dimethyl-8-oxo-6,7-dihydro-5H-imidazo[1,2-a][1,3]diazepin-7-yl)-1,2,4-triazole-3-carboxamide;

1-[(3-chlorophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;

1-isopropyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide;

1-phenyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide;

2-benzyl-N-(6S)-2,4-dimethyl-5-oxo-7,8-dihydro-6H-pyrazolo[1,5-a][1,3]diazepin-6-yltetrazole-5-carboxamide;

1-cyclopentyl-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide;

N-[(6S)-2,4-dimethyl-5-oxo-7,8-dihydro-6H-pyrazolo[1,5-a][1,3]diazepin-6-yl]spiro[5H-furo[3,4-d]pyrimidine-7,3'-tetrahydropyran]-2-carboxamide;

N-[(6S)-2,4-dimethyl-5-oxo-7,8-dihydro-6H-pyrazolo[1,5-a][1,3]diazepin-6-yl]spiro[3H-furo[3,4-c]pyridine-1,3'-tetrahydropyran]-6-carboxamide;

1-benzyl-N-(3,9-dimethyl-8-oxo-6,7-dihydro-5H-imidazo[1,2-a][1,3]diazepin-7-yl)-1,2,4-triazole-3-carboxamide;

1-benzyl-N-(6S)-4-methyl-5-oxo-2-[(1S)-2,2-difluorocyclopropylmethyl]-7,8-dihydro-6H-pyrazolo[1,5-a][1,3]diazepin-6-yl-1,2,4-triazole-3-carboxamide;

1-benzyl-N-(6S)-4-methyl-5-oxo-2-[(1R)-2,2-difluorocyclopropylmethyl]-7,8-dihydro-6H-pyrazolo[1,5-a][1,3]diazepin-6-yl-1,2,4-triazole-3-carboxamide;

5-[(4-fluorophenyl)methyl]-N-(6R)-4-methyl-5-oxo-2-(trifluoromethyl)-7,8-dihydro-6H-pyrazolo[1,5-a][1,3]diazepin-6-yl-4H-1,2,4-triazole-3-carboxamide;

N-[(6S)-2,4-dimethyl-5-oxo-7,8-dihydro-6H-pyrazolo[1,5-a][1,3]diazepin-6-yl]spiro[5H-furo[3,4-d]pyrimidine-7,3'-tetrahydrofuran]-2-carboxamide;

N-[(6S)-2,4-dimethyl-5-oxo-7,8-dihydro-6H-pyrazolo[1,5-a][1,3]diazepin-6-yl]spiro[5H-furo[3,4-d]pyrimidine-7,1'-cyclopentane]-2-carboxamide;

8-phenyl-N-[(6S)-2,4-dimethyl-5-oxo-7,8-dihydro-6H-pyrazolo[1,5-a][1,3]diazepin-6-yl]-5,6,7,8-tetrahydro-[1,2,4]triazolo[1,5-a]pyridine-2-carboxamide;

1-[(3,3-dimethylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-benzyl-N-(1,7-dimethyl-2-oxo-4,5-dihydro-3H-imidazo[1,5-a][1,3]diazepin-3-yl)-1,2,4-triazole-3-carboxamide;

N-[(6S)-2,4-dimethyl-5-oxo-7,8-dihydro-6H-pyrazolo[1,5-a][1,3]diazepin-6-yl]-1-tetrahydropyran-4-yl-pyrazolo[3,4-d]pyrimidine-6-carboxamide;

1-[(1-methylcyclobutyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-[(1-methylcyclobutyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;

7-methyl-7-propyl-N-[(6S)-2,4-dimethyl-5-oxo-7,8-dihydro-6H-pyrazolo[1,5-a][1,3]diazepin-6-yl]-5H-furo[3,4-d]pyrimidine-2-carboxamide;

N-[rac-(6S)-4-methyl-5-oxo-7,8-dihydro-6H-pyrazolo[1,5-a][1,3]diazepin-6-yl]spiro[5H-furo[3,4-d]pyrimidine-7,1'-cyclopentane]-2-carboxamide;

7-methyl-7-propyl-N-[(6S)-4-methyl-5-oxo-7,8-dihydro-6H-pyrazolo[1,5-a][1,3]diazepin-6-yl]-5H-furo[3,4-d]pyrimidine-2-carboxamide;

N-[(6S)-2,4-dimethyl-5-oxo-7,8-dihydro-6H-pyrazolo[1,5-a][1,3]diazepin-6-yl]spiro[5,6-dihydro-[1,2,4]triazolo[5,1-c][1,4]oxazine-8,1'-cyclopentane]-2-carboxamide;

1-[(3,3-difluorocyclopentyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-benzyl-N-(6S)-2-(1-fluorocyclopropyl)-4-methyl-5-oxo-7,8-dihydro-6H-pyrazolo[1,5-a][1,3]diazepin-6-yl-1,2,4-triazole-3-carboxamide;

7-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

rac-(7S)-7-phenyl-N-[rac-(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

1-[(2-fluorophenyl)methyl]-N-[(3R)-1,7-dimethyl-2-oxo-4,5-dihydro-3H-imidazo[1,5-a][1,3]diazepin-3-yl]-1,2,4-triazole-3-carboxamide;

1-[(2,5-difluorophenyl)methyl]-N-[(3R)-1,7-dimethyl-2-oxo-4,5-dihydro-3H-imidazo[1,5-a][1,3]diazepin-3-yl]-1,2,4-triazole-3-carboxamide;

1-[(2,6-difluorophenyl)methyl]-N-[(3R)-1,7-dimethyl-2-oxo-4,5-dihydro-3H-imidazo[1,5-a][1,3]diazepin-3-yl]-1,2,4-triazole-3-carboxamide;

7-phenyl-N-[rac-(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

1-[(2-fluorophenyl)methyl]-N-(3R)-1,9-dimethyl-2-oxo-4,5-dihydro-3H-imidazo[1,5-a][1,3]diazepin-3-yl-1,2,4-triazole-3-carboxamide;

1-[(2,6-difluorophenyl)methyl]-N-(3R)-1,9-dimethyl-2-oxo-4,5-dihydro-3H-imidazo[1,5-a][1,3]diazepin-3-yl-1,2,4-triazole-3-carboxamide;

1-[(2-chlorophenyl)methyl]-N-(6S)-4-methyl-5-oxo-7,8-dihydro-6H-pyrazolo[1,5-a][1,3]diazepin-6-yl-1,2,4-triazole-3-carboxamide;

N-(6S)-4-methyl-5-oxo-7,8-dihydro-6H-pyrazolo[1,5-a][1,3]diazepin-6-yl-1-[[2-(trifluoromethyl)phenyl]methyl]-1,2,4-triazole-3-carboxamide;

N-(6S)-2,4-dimethyl-5-oxo-7,8-dihydro-6H-pyrazolo[1,5-a][1,3]diazepin-6-yl-1-[[2-(trifluoromethyl)phenyl]methyl]-1,2,4-triazole-3-carboxamide;

1-benzyl-N-(6S)-2-cyclopropyl-5-oxo-4,6,7,8-tetrahydropyrazolo[1,5-a][1,3]diazepin-6-yl-1,2,4-triazole-3-carboxamide;

1-benzyl-N-(6S)-2-methyl-5-oxo-4,6,7,8-tetrahydropyrazolo[1,5-a][1,3]diazepin-6-yl-1,2,4-triazole-3-carboxamide;

1-[(2-methoxyphenyl)methyl]-N-(6S)-4-methyl-5-oxo-7,8-dihydro-6H-pyrazolo[1,5-a][1,3]diazepin-6-yl-1,2,4-triazole-3-carboxamide;

1-(o-tolylmethyl)-N-(6S)-4-methyl-5-oxo-7,8-dihydro-6H-pyrazolo[1,5-a][1,3]diazepin-6-yl-1,2,4-triazole-3-carboxamide;

1-[(2-methoxyphenyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-[(2-cyanophenyl)methyl]-N-(6S)-2,4-dimethyl-5-oxo-7,8-dihydro-6H-pyrazolo[1,5-a][1,3]diazepin-6-yl-1,2,4-triazole-3-carboxamide;

1-(o-tolylmethyl)-N-(6S)-2,4-dimethyl-5-oxo-7,8-dihydro-6H-pyrazolo[1,5-a][1,3]diazepin-6-yl-1,2,4-triazole-3-carboxamide;

1-[(2-methoxyphenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;

1-[(2-cyanophenyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;

1-[(3,3-difluorocyclopentyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;

1-[(2-fluorophenyl)methyl]-N-(3R)-1,7,9-trimethyl-2-oxo-4,5-dihydro-3H-imidazo[1,5-a][1,3]diazepin-3-yl-1,2,4-triazole-3-carboxamide;

1-[(2,6-difluorophenyl)methyl]-N-(3R)-1,7,9-trimethyl-2-oxo-4,5-dihydro-3H-imidazo[1,5-a][1,3]diazepin-3-yl-1,2,4-triazole-3-carboxamide;

1-[(2,5-difluorophenyl)methyl]-N-(3R)-1,7,9-trimethyl-2-oxo-4,5-dihydro-3H-imidazo[1,5-a][1,3]diazepin-3-yl-1,2,4-triazole-3-carboxamide;

1-[(2-fluorophenyl)methyl]-N-(3R)-1-methyl-2-oxo-4,5-dihydro-3H-imidazo[1,5-a][1,3]diazepin-3-yl-1,2,4-triazole-3-carboxamide;

1-[(2,6-difluorophenyl)methyl]-N-[(3R)-1-methyl-2-oxo-4,5-dihydro-3H-imidazo[1,5-a][1,3]diazepin-3-yl]-1,2,4-triazole-3-carboxamide;

1-[(2-fluorophenyl)methyl]-N-(7R)-9-methyl-8-oxo-6,7-dihydro-5H-imidazo[1,2-a][1,3]diazepin-7-yl-1,2,4-triazole-3-carboxamide;

1-[(2,6-difluorophenyl)methyl]-N-[(7R)-9-methyl-8-oxo-6,7-dihydro-5H-imidazo[1,2-a][1,3]diazepin-7-yl]-1,2,4-triazole-3-carboxamide;

1-[(2-cyanophenyl)methyl]-N-(6S)-4-methyl-5-oxo-7,8-dihydro-6H-pyrazolo[1,5-a][1,3]diazepin-6-yl-1,2,4-triazole-3-carboxamide;

1-(o-tolylmethyl)-N-(6S)-2-cyclopropyl-4-methyl-5-oxo-7,8-dihydro-6H-pyrazolo[1,5-a][1,3]diazepin-6-yl-1,2,4-triazole-3-carboxamide;

1-benzyl-N-(3R)-1,7,9-trimethyl-2-oxo-4,5-dihydro-3H-imidazo[1,5-a][1,3]diazepin-3-yl-1,2,4-triazole-3-carboxamide;

1-(2,6-difluorophenyl)-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide;

(S)—N—((S)-2,4-dimethyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide;

rac-(5S)-5-phenyl-N-[rac-(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

(5R)-5-phenyl-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

(5R)-5-phenyl-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;

1-(2-pyridyl)-N-[(6S)-2,4-dimethyl-5-oxo-7,8-dihydro-6H-pyrazolo[1,5-a][1,3]diazepin-6-yl]pyrazolo[3,4-d]pyrimidine-6-carboxamide;

1-(2-pyridyl)-N-[(6R)-2,4-dimethyl-5-oxo-7,8-dihydro-6H-pyrazolo[1,5-a][1,3]diazepin-6-yl]pyrazolo[3,4-d]pyrimidine-6-carboxamide;

N-[(6S)-2,4-dimethyl-5-oxo-7,8-dihydro-6H-pyrazolo[1,5-a][1,3]diazepin-6-yl]spiro[5,6-dihydropyrrolo[1,2-b][1,2,4]triazole-7,4'-tetrahydropyran]-2-carboxamide;

4-phenyl-N-[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide;

1-[(3-methyl-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide;

N-[(6S)-2,4-dimethyl-5-oxo-7,8-dihydro-6H-pyrazolo[1,5-a][1,3]diazepin-6-yl]spiro[5,6-dihydropyrrolo[1,2-b][1,2,4]triazole-7,3'-tetrahydrofuran]-2-carboxamide;

1-[(3-methyl-2-pyridyl)methyl]-N-(6S)-4-methyl-5-oxo-7,8-dihydro-6H-pyrazolo[1,5-a][1,3]diazepin-6-yl-1,2,4-triazole-3-carboxamide;

1-[(3-methyl-2-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;
4-(2,6-difluorophenyl)-N-[(6S)-2,4-dimethyl-5-oxo-7,8-dihydro-6H-pyrazolo[1,5-a][1,3]diazepin-6-yl]-5,6-dihydroimidazo[1,2-b][1,2,4]triazole-2-carboxamide;
1-(2-pyridylmethyl)-N-(6S)-4-methyl-5-oxo-7,8-dihydro-6H-pyrazolo[1,5-a][1,3]diazepin-6-yl-1,2,4-triazole-3-carboxamide;
1-(2-pyridylmethyl)-N-(6S)-2,4-dimethyl-5-oxo-7,8-dihydro-6H-pyrazolo[1,5-a][1,3]diazepin-6-yl-1,2,4-triazole-3-carboxamide;
1-(2-pyridylmethyl)-N-(6S)-2-cyclopropyl-4-methyl-5-oxo-7,8-dihydro-6H-pyrazolo[1,5-a][1,3]diazepin-6-yl-1,2,4-triazole-3-carboxamide;
1-[(3-fluoro-2-pyridyl)methyl]-N-(6S)-4-methyl-5-oxo-7,8-dihydro-6H-pyrazolo[1,5-a][1,3]diazepin-6-yl-1,2,4-triazole-3-carboxamide;
1-[(3-fluoro-2-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide;
1-[(3-fluoro-2-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;
1-[(3-chloro-2-pyridyl)methyl]-N-(6S)-4-methyl-5-oxo-7,8-dihydro-6H-pyrazolo[1,5-a][1,3]diazepin-6-yl-1,2,4-triazole-3-carboxamide;
1-[(3-chloro-2-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;
1-[(2-fluorophenyl)methyl]-N-(7R)-2,9-dimethyl-8-oxo-6,7-dihydro-5H-imidazo[1,2-a][1,3]diazepin-7-yl-1,2,4-triazole-3-carboxamide;
1-[(2,6-difluorophenyl)methyl]-N-(7R)-2,9-dimethyl-8-oxo-6,7-dihydro-5H-imidazo[1,2-a][1,3]diazepin-7-yl-1,2,4-triazole-3-carboxamide;
1-[(2,5-difluorophenyl)methyl]-N-(7R)-2,9-dimethyl-8-oxo-6,7-dihydro-5H-imidazo[1,2-a][1,3]diazepin-7-yl-1,2,4-triazole-3-carboxamide;
1-benzyl-N-(6S)-4-methyl-2-(3-morpholinopropyl)-5-oxo-7,8-dihydro-6H-pyrazolo[1,5-a][1,3]diazepin-6-yl-1,2,4-triazole-3-carboxamide;
1-[(2-methyl-3-pyridyl)methyl]-N-(6S)-4-methyl-5-oxo-7,8-dihydro-6H-pyrazolo[1,5-a][1,3]diazepin-6-yl-1,2,4-triazole-3-carboxamide;
1-[(2-methyl-3-pyridyl)methyl]-N-(6S)-2,4-dimethyl-5-oxo-7,8-dihydro-6H-pyrazolo[1,5-a][1,3]diazepin-6-yl-1,2,4-triazole-3-carboxamide;
1-[(2-methyl-3-pyridyl)methyl]-N-(6S)-2-cyclopropyl-4-methyl-5-oxo-7,8-dihydro-6H-pyrazolo[1,5-a][1,3]diazepin-6-yl-1,2,4-triazole-3-carboxamide;
(5R)-5-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
(5S)-5-(2-fluorophenyl)-N-[(6S)-2,4-dimethyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
(5R)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
(5S)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide;
N-[rac-(6S)-2-cyclopropyl-4-methyl-5-oxo-7,8-dihydro-6H-pyrazolo[1,5-a][1,3]diazepin-6-yl]-1-[rac-(1S)-1-(4-fluorophenyl)ethyl]-1,2,4-triazole-3-carboxamide;
5-benzyl-N-[rac-(6S)-4-methyl-5-oxo-2-[rac-(1R)-2,2-difluorocyclopropyl]-7,8-dihydro-6H-pyrazolo[1,5-a][1,3]diazepin-6-yl]-4H-1,2,4-triazole-3-carboxamide;
5-benzyl-N-[rac-(6R)-4-methyl-5-oxo-2-[rac-(1R)-2,2-difluorocyclopropyl]-7,8-dihydro-6H-pyrazolo[1,5-a][1,3]diazepin-6-yl]-4H-1,2,4-triazole-3-carboxamide;
1-benzyl-N-[rac-(6R)-4-methyl-5-oxo-2-[rac-(1R)-2,2-difluorocyclopropyl]-7,8-dihydro-6H-pyrazolo[1,5-a][1,3]diazepin-6-yl]-1,2,4-triazole-3-carboxamide;
1-benzyl-N-[rac-(6R)-4-methyl-5-oxo-2-[rac-(1S)-2,2-difluorocyclopropyl]-7,8-dihydro-6H-pyrazolo[1,5-a][1,3]diazepin-6-yl]-1,2,4-triazole-3-carboxamide;
N-[rac-(6S)-2-cyclopropyl-4-methyl-5-oxo-7,8-dihydro-6H-pyrazolo[1,5-a][1,3]diazepin-6-yl]-1-[rac-(1R)-1-(4-fluorophenyl)ethyl]-1,2,4-triazole-3-carboxamide;
1-[(4-chlorophenyl)methyl]-N-[rac-(6S)-2-cyclopropyl-4-methyl-5-oxo-7,8-dihydro-6H-pyrazolo[1,5-a][1,3]diazepin-6-yl]-1,2,4-triazole-3-carboxamide;
1-benzyl-N-[rac-(6S)-4-methyl-5-oxo-2-[rac-(1R)-2,2-difluorocyclopropyl]-7,8-dihydro-6H-pyrazolo[1,5-a][1,3]diazepin-6-yl]-1,2,4-triazole-3-carboxamide;
1-[(4-fluorophenyl)methyl]-N-[rac-(6S)-2-cyclopropyl-4-methyl-5-oxo-7,8-dihydro-6H-pyrazolo[1,5-a][1,3]diazepin-6-yl]-1,2,4-triazole-3-carboxamide;
rac-(7R)-7-methyl-N-[rac-(6S)-2,4-dimethyl-5-oxo-7,8-dihydro-6H-pyrazolo[1,5-a][1,3]diazepin-6-yl]-7-(2,2,2-trifluoroethyl)-5H-furo[3,4-d]pyrimidine-2-carboxamide;
rac-(7R)-7-ethyl-7-methyl-N-[rac-(6S)-2,4-dimethyl-5-oxo-7,8-dihydro-6H-pyrazolo[1,5-a][1,3]diazepin-6-yl]-5H-furo[3,4-d]pyrimidine-2-carboxamide;
rac-(7S)-7-methyl-N-[rac-(6S)-2,4-dimethyl-5-oxo-7,8-dihydro-6H-pyrazolo[1,5-a][1,3]diazepin-6-yl]-7-(2,2,2-trifluoroethyl)-5H-furo[3,4-d]pyrimidine-2-carboxamide;
rac-(7S)-7-ethyl-7-methyl-N-[rac-(6S)-2,4-dimethyl-5-oxo-7,8-dihydro-6H-pyrazolo[1,5-a][1,3]diazepin-6-yl]-5H-furo[3,4-d]pyrimidine-2-carboxamide;
1-benzyl-N-[rac-(7R)-2,9-dimethyl-8-oxo-6,7-dihydro-5H-imidazo[1,2-a][1,3]diazepin-7-yl]-1,2,4-triazole-3-carboxamide;
1-benzyl-N-[2-(1-ethylpyrazol-4-yl)-4-methyl-5-oxo-7,8-dihydro-6H-pyrazolo[1,5-a][1,3]diazepin-6-yl]-1,2,4-triazole-3-carboxamide;
1-benzyl-N-[2-(1-isobutylpyrazol-4-yl)-4-methyl-5-oxo-7,8-dihydro-6H-pyrazolo[1,5-a][1,3]diazepin-6-yl]-1,2,4-triazole-3-carboxamide;
5-bromo-N-[(6S)-4-methyl-5-oxo-7,8-dihydro-6H-pyrazolo[1,5-a][1,3]diazepin-6-yl]isoquinoline-3-carboxamide;
5-bromo-N-[(6S)-2,4-dimethyl-5-oxo-7,8-dihydro-6H-pyrazolo[1,5-a][1,3]diazepin-6-yl]isoquinoline-3-carboxamide;
5-phenyl-N-[(6S)-2,4-dimethyl-5-oxo-7,8-dihydro-6H-pyrazolo[1,5-a][1,3]diazepin-6-yl]isoquinoline-3-carboxamide;
5-phenyl-N-[(6S)-4-methyl-5-oxo-7,8-dihydro-6H-pyrazolo[1,5-a][1,3]diazepin-6-yl]isoquinoline-3-carboxamide;
1-benzyl-N-[2-(1-ethylpyrazol-3-yl)-4-methyl-5-oxo-7,8-dihydro-6H-pyrazolo[1,5-a][1,3]diazepin-6-yl]-1,2,4-triazole-3-carboxamide;

1-benzyl-N-[4-methyl-5-oxo-2-(pyrazol-1-ylmethyl)-7,8-dihydro-6H-pyrazolo[1,5-a][1,3]diazepin-6-yl]-1,2,4-triazole-3-carboxamide;

1-benzyl-N-[4-methyl-2-[(2-methylimidazol-1-yl)methyl]-5-oxo-7,8-dihydro-6H-pyrazolo[1,5-a][1,3]diazepin-6-yl]-1,2,4-triazole-3-carboxamide;

(S)-1-benzyl-N-[2-(imidazol-1-ylmethyl)-4-methyl-5-oxo-7,8-dihydro-6H-pyrazolo[1,5-a][1,3]diazepin-6-yl]-1,2,4-triazole-3-carboxamide;

(S)—N-(2,4-dimethyl-5-oxo-5,6,7,8-tetrahydro-4H-pyrazolo[1,5-a][1,3]diazepin-6-yl)-4-phenylpyrazolo[1,5-a]pyridine-2-carboxamide;

1-benzyl-N-[2-[(3,3-difluoropyrrolidin-1-yl)methyl]-4-methyl-5-oxo-7,8-dihydro-6H-pyrazolo[1,5-a][1,3]diazepin-6-yl]-1,2,4-triazole-3-carboxamide;

1-benzyl-N-[2-[(2-methoxyethylamino)methyl]-4-methyl-5-oxo-7,8-dihydro-6H-pyrazolo[1,5-a][1,3]diazepin-6-yl]-1,2,4-triazole-3-carboxamide;

(S)-1-benzyl-N-(2-((3-methoxyazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2-((3-fluoroazetidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2-((3,3-difluoropyrrolidin-1-yl)methyl)-4-methyl-5-oxo-5,6,7,8-tetrahydro-4H-pyrazolo[1,5-a][1,3]diazepin-6-yl)-1H-1,2,4-triazole-3-carboxamide;

(S)-1-benzyl-N-(2-(((2-methoxyethyl)amino)methyl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-[(6S)-2-(hydroxymethyl)-4-methyl-5-oxo-7,8-dihydro-6H-pyrazolo[1,5-a][1,3]diazepin-6-yl]-1,2,4-triazole-3-carboxamide;

1-benzyl-N-[(6S)-4-methyl-5-oxo-2-[(2,2,2-trifluoroethylamino)methyl]-7,8-dihydro-6H-pyrazolo[1,5-a][1,3]diazepin-6-yl]-1,2,4-triazole-3-carboxamide;

1-benzyl-N-[(6R)-4-methyl-2-(3-morpholinopropyl)-5-oxo-7,8-dihydro-6H-pyrazolo[1,5-a][1,3]diazepin-6-yl]-1,2,4-triazole-3-carboxamide;

1-benzyl-N-[(6S)-2-[3-(3,3-difluoropyrrolidin-1-yl)propyl]-4-methyl-5-oxo-7,8-dihydro-6H-pyrazolo[1,5-a][1,3]diazepin-6-yl]-1,2,4-triazole-3-carboxamide;

1-benzyl-N-[(6S)-4-methyl-5-oxo-7,8-dihydro-6H-pyrazolo[1,5-a][1,3]diazepin-6-yl]pyrazole-3-carboxamide;

1-benzyl-N-[(6S)-2,4-dimethyl-5-oxo-7,8-dihydro-6H-pyrazolo[1,5-a][1,3]diazepin-6-yl]pyrazole-3-carboxamide;

1-benzyl-N-[(6S)-4-methyl-5-oxo-7,8-dihydro-6H-pyrazolo[1,5-a][1,3]diazepin-6-yl]imidazole-4-carboxamide;

1-benzyl-N-[(6S)-2,4-dimethyl-5-oxo-7,8-dihydro-6H-pyrazolo[1,5-a][1,3]diazepin-6-yl]imidazole-4-carboxamide;

1-benzyl-N-[(6S)-4-methyl-2-(2-morpholinoethyl)-5-oxo-7,8-dihydro-6H-pyrazolo[1,5-a][1,3]diazepin-6-yl]-1,2,4-triazole-3-carboxamide;

1-[(2-fluorophenyl)methyl]-N-[(6S)-4-methyl-2-(2-morpholinoethyl)-5-oxo-7,8-dihydro-6H-pyrazolo[1,5-a][1,3]diazepin-6-yl]-1,2,4-triazole-3-carboxamide;

1-benzyl-N-[(6S)-2-(azetidin-3-yl)-4-methyl-5-oxo-7,8-dihydro-6H-pyrazolo[1,5-a][1,3]diazepin-6-yl]-1,2,4-triazole-3-carboxamide;

1-benzyl-N-[(6S)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide;

1-benzyl-N-[(6S)-2-[2-(azetidin-1-yl)ethyl]-4-methyl-5-oxo-7,8-dihydro-6H-pyrazolo[1,5-a][1,3]diazepin-6-yl]-1,2,4-triazole-3-carboxamide;

1-benzyl-N-[(6S)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide;

1-benzyl-N-[(6S)-2-(2-ethoxyethyl)-4-methyl-5-oxo-7,8-dihydro-6H-pyrazolo[1,5-a][1,3]diazepin-6-yl]-1,2,4-triazole-3-carboxamide;

tert-butyl-3-[(6S)-6-[(1-benzyl-1,2,4-triazole-3-carbonyl)amino]-4-methyl-5-oxo-7,8-dihydro-6H-pyrazolo[1,5-a][1,3]diazepin-2-yl]azetidine-1-carboxylate;

1-[(2-fluorophenyl)methyl]-N-[(6S)-2-[2-(2-methoxyethoxy)ethyl]-4-methyl-5-oxo-7,8-dihydro-6H-pyrazolo[1,5-a][1,3]diazepin-6-yl]-1,2,4-triazole-3-carboxamide;

1-benzyl-N-[(6S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide;

1-[(2-fluorophenyl)methyl]-N-[(6S)-4-methyl-2-[2-(2-oxa-5-azabicyclo[2.2.1]heptan-5-yl)ethyl]-5-oxo-7,8-dihydro-6H-pyrazolo[1,5-a][1,3]diazepin-6-yl]-1,2,4-triazole-3-carboxamide;

1-[(2-fluorophenyl)methyl]-N-[(6S)-2-(2-ethoxyethyl)-4-methyl-5-oxo-7,8-dihydro-6H-pyrazolo[1,5-a][1,3]diazepin-6-yl]-1,2,4-triazole-3-carboxamide;

1-benzyl-N-[(6S)-2-(2-hydroxyethyl)-4-methyl-5-oxo-7,8-dihydro-6H-pyrazolo[1,5-a][1,3]diazepin-6-yl]-1,2,4-triazole-3-carboxamide;

1-benzyl-N-[(6S)-2-(2-methoxyethyl)-4-methyl-5-oxo-7,8-dihydro-6H-pyrazolo[1,5-a][1,3]diazepin-6-yl]-1,2,4-triazole-3-carboxamide;

1-[(2-fluorophenyl)methyl]-N-[(6S)-2-(2-methoxyethyl)-4-methyl-5-oxo-7,8-dihydro-6H-pyrazolo[1,5-a][1,3]diazepin-6-yl]-1,2,4-triazole-3-carboxamide;

1-benzyl-N-[(6S)-2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide;

1-[(2-fluorophenyl)methyl]-N-[(6S)-2-[2-(3-fluoroazetidin-1-yl)ethyl]-4-methyl-5-oxo-7,8-dihydro-6H-pyrazolo[1,5-a][1,3]diazepin-6-yl]-1,2,4-triazole-3-carboxamide;

1-[(2-fluorophenyl)methyl]-N-[(6S)-2-[2-(3-methoxyazetidin-1-yl)ethyl]-4-methyl-5-oxo-7,8-dihydro-6H-pyrazolo[1,5-a][1,3]diazepin-6-yl]-1,2,4-triazole-3-carboxamide;

1-benzyl-N-[(6S)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide;

1-[(2-fluorophenyl)methyl]-N-[(6S)-2-[2-(3,3-difluoroazetidin-1-yl)ethyl]-4-methyl-5-oxo-7,8-dihydro-6H-pyrazolo[1,5-a][1,3]diazepin-6-yl]-1,2,4-triazole-3-carboxamide;

1-benzyl-N-[(6S)-4-methyl-5-oxo-2-(tetrahydropyran-4-ylmethyl)-7,8-dihydro-6H-pyrazolo[1,5-a][1,3]diazepin-6-yl]-1,2,4-triazole-3-carboxamide;

1-benzyl-N-(2-(1,2-dimethyl-1H-imidazol-5-yl)-4-methyl-5-oxo-5,6,7,8-tetrahydro-4H-pyrazolo[1,5-a][1,3]diazepin-6-yl)-1H-1,2,4-triazole-3-carboxamide;

1-benzyl-N-(4-methyl-2-(1-methyl-1H-pyrazol-3-yl)-5-oxo-5,6,7,8-tetrahydro-4H-pyrazolo[1,5-a][1,3]diazepin-6-yl)-1H-1,2,4-triazole-3-carboxamide; and 1-benzyl-N-(4-methyl-2-(1-methyl-1H-pyrazol-4-yl)-5-oxo-5,6,7,8-tetrahydro-4H-pyrazolo[1,5-a][1,3]diazepin-6-yl)-1H-1,2,4-triazole-3-carboxamide.

11. The compound of claim 10, or a pharmaceutically acceptable salt thereof, wherein the compound is (S)-1-benzyl-N-(4-methyl-5-oxo-5,6,7,8-tetrahydro-4H-pyrazolo[1,5-a][1,3]diazepin-6-yl)-1H-1,2,4-triazole-3-carboxamide.

12. The compound of claim 10, or a pharmaceutically acceptable salt thereof, wherein the compound is (S)-1-benzyl-N-(4-methyl-5-oxo-2-(trifluoromethyl)-5,6,7,8-tetrahydro-4H-pyrazolo[1,5-a][1,3]diazepin-6-yl)-1H-1,2,4-triazole-3-carboxamide.

13. The compound of claim 10, or a pharmaceutically acceptable salt thereof, wherein the compound is (S)—N—((S)-4-methyl-5-oxo-5,6,7,8-tetrahydro-4H-pyrazolo[1,5-a][1,3]diazepin-6-yl)-5-phenyl-6,7-dihydro-5H-pyrrolo[1,2-b][1,2,4]triazole-2-carboxamide.

14. The compound of claim 10, or a pharmaceutically acceptable salt thereof, wherein the compound is (S)-1-benzyl-N-(2-cyclopropyl-4-methyl-5-oxo-5,6,7,8-tetrahydro-4H-pyrazolo[1,5-a][1,3]diazepin-6-yl)-1H-1,2,4-triazole-3-carboxamide.

15. The compound of claim 10, wherein the compound is (S)-1-benzyl-N-(2,4-dimethyl-5-oxo-5,6,7,8-tetrahydro-4H-pyrazolo[1,5-a][1,3]diazepin-6-yl)-1H-1,2,4-triazole-3-carboxamide.

16. The compound of claim 10, or a pharmaceutically acceptable salt thereof, wherein the compound is (S)-1-(2,6-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide.

17. The compound of claim 10, or a pharmaceutically acceptable salt thereof, wherein the compound is (S)—N-(2-cyclopropyl-4-methyl-5-oxo-5,6,7,8-tetrahydro-4H-pyrazolo[1,5-a][1,3]diazepin-6-yl)-1-(2,6-difluorobenzyl)-1H-1,2,4-triazole-3-carboxamide.

18. The compound of claim 10, or a pharmaceutically acceptable salt thereof, wherein the compound is (S)—N-(2-cyclopropyl-4-methyl-5-oxo-5,6,7,8-tetrahydro-4H-pyrazolo[1,5-a][1,3]diazepin-6-yl)-1-(3,5-difluorobenzyl)-1H-1,2,4-triazole-3-carboxamide.

19. The compound of claim 10, or a pharmaceutically acceptable salt thereof, wherein the compound is (S)—N-(2-cyclopropyl-4-methyl-5-oxo-5,6,7,8-tetrahydro-4H-pyrazolo[1,5-a][1,3]diazepin-6-yl)-1-(2,5-difluorobenzyl)-1H-1,2,4-triazole-3-carboxamide.

20. The compound of claim 10, or a pharmaceutically acceptable salt thereof, wherein the compound is (S)-1-(2,5-difluorobenzyl)-N-(2,4-dimethyl-5-oxo-5,6,7,8-tetrahydro-4H-pyrazolo[1,5-a][1,3]diazepin-6-yl)-1H-1,2,4-triazole-3-carboxamide.

21. The compound of claim 10, or a pharmaceutically acceptable salt thereof, wherein the compound is (S)—N-(2-cyclopropyl-4-methyl-5-oxo-5,6,7,8-tetrahydro-4H-pyrazolo[1,5-a][1,3]diazepin-6-yl)-1-(2,3-dichlorobenzyl)-1H-1,2,4-triazole-3-carboxamide.

22. The compound of claim 10, or a pharmaceutically acceptable salt thereof, wherein the compound is (S)—N-(2-cyclopropyl-4-methyl-5-oxo-5,6,7,8-tetrahydro-4H-pyrazolo[1,5-a][1,3]diazepin-6-yl)-1-(2,4-dichlorobenzyl)-1H-1,2,4-triazole-3-carboxamide.

23. The compound of claim 10, or a pharmaceutically acceptable salt thereof, wherein the compound is (S)-1-benzyl-N-(2-isopropyl-4-methyl-5-oxo-5,6,7,8-tetrahydro-4H-pyrazolo[1,5-a][1,3]diazepin-6-yl)-1H-1,2,4-triazole-3-carboxamide.

24. The compound of claim 10, or a pharmaceutically acceptable salt thereof, wherein the compound is (S)—N-(2-ethyl-4-methyl-5-oxo-5,6,7,8-tetrahydro-4H-pyrazolo[1,5-a][1,3]diazepin-6-yl)-1-(2-fluorobenzyl)-1H-1,2,4-triazole-3-carboxamide.

25. The compound of claim 10, or a pharmaceutically acceptable salt thereof, wherein the compound is (R)-5-(2-fluorophenyl)-N—((S)-4-methyl-5-oxo-5,6,7,8-tetrahydro-4H-pyrazolo[1,5-a][1,3]diazepin-6-yl)-6,7-dihydro-5H-pyrrolo[1,2-b][1,2,4]triazole-2-carboxamide.

26. The compound of claim 10, or a pharmaceutically acceptable salt thereof, wherein the compound is (5R)-5-phenyl-N-[(6S)-2,4-dimethyl-5-oxo-7,8-dihydro-6H-pyrazolo[1,5-a][1,3]diazepin-6-yl]-6,7-dihydro-5Hpyrrolo[1,2-b][1,2,4]triazole-2-carboxamide.

27. The compound of claim 10, or a pharmaceutically acceptable salt thereof, wherein the compound is (5R)-5-(2-fluorophenyl)-N-[(6S)-4-methyl-5-oxo-7,8-dihydro-6H-pyrazolo[1,5-a][1,3]diazepin-6-yl]-6,7-dihydro-5H-pyrrolo[1,2-b][1,2,4]triazole-2-carboxamide.

28. A pharmaceutical composition comprising a compound of claim 1, or a pharmaceutically acceptable salt thereof, and a therapeutically inert carrier.

29. A pharmaceutical composition comprising a compound of claim 6, or a pharmaceutically acceptable salt thereof, and a therapeutically inert carrier.

30. A pharmaceutical composition comprising a compound of claim 7, or a pharmaceutically acceptable salt thereof, and a therapeutically inert carrier.

31. A pharmaceutical composition comprising a compound of claim 10, or a pharmaceutically acceptable salt thereof, and a therapeutically inert carrier.

* * * * *